(12) United States Patent
Mainolfi et al.

(10) Patent No.: US 12,150,995 B2
(45) Date of Patent: Nov. 26, 2024

(54) IRAK DEGRADERS AND USES THEREOF

(71) Applicant: Kymera Therapeutics, Inc., Watertown, MA (US)

(72) Inventors: Nello Mainolfi, Belmont, MA (US); Nan Ji, Arlington, MA (US); Matthew M. Weiss, Boston, MA (US); Xiaozhang Zheng, Lexington, MA (US); Yi Zhang, Belmont, MA (US); Paul R. Fleming, Lexington, MA (US); Xiao Zhu, Winchester, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/646,556

(22) Filed: Dec. 30, 2021

(65) Prior Publication Data

US 2023/0101353 A1 Mar. 30, 2023

Related U.S. Application Data

(60) Provisional application No. 63/132,332, filed on Dec. 30, 2020.

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
CPC ..................................................... A61K 47/55
See application file for complete search history.

(56) References Cited

U.S. PATENT DOCUMENTS

| | | | |
|---|---|---|---|
| 4,045,485 A | 8/1977 | Fried et al. | |
| 4,650,750 A | 3/1987 | Giese | |
| 4,709,016 A | 11/1987 | Giese | |
| 5,217,866 A | 6/1993 | Summerton et al. | |
| 5,360,811 A | 11/1994 | Tegeler et al. | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 5,721,246 A | 2/1998 | Yoshino et al. | |
| 6,306,663 B1 | 10/2001 | Kenten et al. | |
| 6,552,065 B2 | 4/2003 | Remiszewski et al. | |
| 6,559,280 B2 | 5/2003 | Kenten et al. | |
| 6,627,754 B2 | 9/2003 | Blumenkopf et al. | |
| 6,949,537 B2 | 9/2005 | Garlich et al. | |
| 7,041,298 B2 | 5/2006 | Deshaies et al. | |
| 7,071,189 B2 | 7/2006 | Kawashima et al. | |
| 7,074,620 B2 | 7/2006 | Kenten et al. | |
| 7,173,015 B2 | 2/2007 | Schreiber et al. | |
| 7,208,157 B2 | 4/2007 | Dashaies et al. | |
| 7,273,920 B2 | 9/2007 | Kenten et al. | |
| 7,307,077 B2 | 12/2007 | Kawashima et al. | |
| 7,390,799 B2 | 6/2008 | Bruncko et al. | |
| 7,402,325 B2 | 7/2008 | Addington | |
| 7,449,458 B2 | 11/2008 | Bhamidipati et al. | |
| 7,501,496 B1 | 3/2009 | Endl et al. | |
| 7,514,444 B2 | 4/2009 | Honigberg et al. | |
| 7,528,143 B2 | 5/2009 | Noronha et al. | |
| 7,557,210 B2 | 7/2009 | Singh et al. | |
| 7,598,257 B2 | 10/2009 | Rodgers et al. | |
| 7,622,496 B2 | 11/2009 | Larsen et al. | |
| 7,667,039 B2 | 2/2010 | Garcia-Echeverria et al. | |
| 7,713,943 B2 | 5/2010 | Klippel-Giese et al. | |
| 7,781,433 B2 | 8/2010 | Chuckowree et al. | |
| 7,932,260 B2 | 4/2011 | Fowler et al. | |
| 7,989,622 B2 | 8/2011 | Bajalieh et al. | |
| 8,138,347 B2 | 3/2012 | Knight et al. | |
| 8,185,616 B2 | 5/2012 | Nagata et al. | |
| 8,217,035 B2 | 7/2012 | Burger et al. | |
| 8,338,439 B2 | 12/2012 | Singh et al. | |
| 8,486,941 B2 | 7/2013 | Burns et al. | |
| 8,906,682 B2 | 12/2014 | June et al. | |
| 9,334,320 B2 | 5/2016 | Okun et al. | |
| 9,500,653 B2 | 11/2016 | Crews et al. | |
| 9,632,089 B2 | 4/2017 | Crews et al. | |
| 9,694,084 B2 | 7/2017 | Bradner et al. | |
| 9,750,816 B2 | 9/2017 | Bradner et al. | |
| 9,770,512 B2 | 9/2017 | Bradner et al. | |
| 9,821,068 B2 | 11/2017 | Bradner et al. | |
| 9,969,710 B2 | 5/2018 | Jorand-Lebrun et al. | |
| 10,125,114 B2 | 11/2018 | Bradner et al. | |
| 10,294,229 B2 * | 5/2019 | Gardner | A61P 25/28 |
| 10,336,744 B2 | 7/2019 | Harling et al. | |
| 10,874,743 B2 | 12/2020 | Mainolfi et al. | |
| 11,065,231 B2 | 7/2021 | Crew et al. | |
| 11,117,889 B1 | 9/2021 | Mainolfi et al. | |
| 11,292,792 B2 | 4/2022 | Ji et al. | |
| 11,318,205 B1 | 5/2022 | Mainolfi et al. | |
| 11,352,350 B2 * | 6/2022 | Mainolfi | A61K 45/06 |
| 11,358,948 B2 | 6/2022 | Mainolfi et al. | |
| 11,512,080 B2 | 11/2022 | Mainolfi et al. | |
| 11,542,261 B2 * | 1/2023 | Starczynowski | A61K 31/496 |
| 11,591,332 B2 | 2/2023 | Weiss et al. | |
| 11,685,750 B2 | 6/2023 | Zheng et al. | |
| 11,707,457 B2 | 7/2023 | Weiss | |
| 11,723,980 B2 | 8/2023 | Mainolfi et al. | |

(Continued)

FOREIGN PATENT DOCUMENTS

| | | |
|---|---|---|
| CN | 105085620 B | 5/2018 |
| EA | 201691428 A1 | 12/2016 |

(Continued)

OTHER PUBLICATIONS

Tinworth, Med. Chem. Commun., 2016, 7, 2206-2216.*

(Continued)

*Primary Examiner* — Nizal S Chandrakumar
(74) *Attorney, Agent, or Firm* — Dechert LLP; Andrea L.C. Reid; Todd K. Macklin

(57) ABSTRACT

The present invention provides compounds, compositions thereof, and methods of using the same.

15 Claims, No Drawings

(56) References Cited

U.S. PATENT DOCUMENTS

| | | |
|---|---|---|
| 11,773,103 B2 | 10/2023 | Rong et al. |
| 11,807,636 B2 | 11/2023 | Mainolfi et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2003/0045552 A1 | 3/2003 | Robarge et al. |
| 2003/0136944 A1 | 7/2003 | Takehara et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0234377 A1 | 9/2010 | Aicher et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0196150 A1 | 8/2011 | Man et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | McElroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0025093 A1 | 1/2015 | Romero et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225410 A1 | 8/2015 | Castro et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Kelley et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008896 A1 | 1/2017 | Dahmann et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0152263 A1 | 6/2017 | Gummadi et al. |
| 2017/0152273 A1 | 6/2017 | Merchant et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 5/2018 | Harling et al. |
| 2018/0127432 A1 | 5/2018 | Trzupek et al. |
| 2018/0134684 A1 | 5/2018 | Bradner et al. |
| 2018/0147202 A1 | 5/2018 | Crew et al. |
| 2018/0169097 A1 | 6/2018 | Hammerman et al. |
| 2018/0186799 A1 | 7/2018 | Gardner et al. |
| 2018/0194724 A1 | 7/2018 | Kemp et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2018/0298015 A1 | 10/2018 | Bryan et al. |
| 2018/0327419 A1 | 11/2018 | Bradner et al. |
| 2018/0353501 A1 | 12/2018 | Crew et al. |
| 2018/0370988 A1 | 12/2018 | Gummadi et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0105322 A1 | 4/2019 | Macdonald et al. |
| 2019/0151295 A1 | 5/2019 | Crew et al. |
| 2019/0151457 A1 | 5/2019 | Bradner et al. |
| 2019/0192532 A1 | 6/2019 | Bradner et al. |
| 2019/0192668 A1 | 6/2019 | Mainolfi et al. |
| 2019/0276474 A1 | 9/2019 | Chan et al. |
| 2019/0374528 A1 | 12/2019 | Gray et al. |

(56) References Cited

U.S. PATENT DOCUMENTS

| | | |
|---|---|---|
| 2020/0010468 A1 | 1/2020 | Ji et al. |
| 2020/0103418 A1 | 4/2020 | Hackney et al. |
| 2020/0306273 A1 | 10/2020 | Yang et al. |
| 2020/0347045 A1 | 11/2020 | Mainolfi et al. |
| 2020/0377469 A1 | 12/2020 | Mainolfi et al. |
| 2021/0002296 A1 | 1/2021 | Mainolfi et al. |
| 2021/0147382 A1 | 5/2021 | Bellenie et al. |
| 2021/0228562 A1 | 7/2021 | Weiss |
| 2021/0323952 A1 | 10/2021 | Mainolfi et al. |
| 2021/0395273 A1 | 12/2021 | Zheng et al. |
| 2022/0054453 A1 | 2/2022 | Walker |
| 2022/0273668 A1 | 9/2022 | Gollob et al. |
| 2022/0274993 A1 | 9/2022 | Rong et al. |
| 2022/0306631 A1 | 9/2022 | Ji et al. |
| 2022/0324854 A1 | 10/2022 | Mainolfi et al. |
| 2022/0340570 A1 | 10/2022 | Weiss et al. |
| 2023/0038512 A1 | 2/2023 | Mainolfi et al. |
| 2023/0069104 A1 | 3/2023 | Mainolfi et al. |
| 2023/0089916 A1 | 3/2023 | Mainolfi et al. |
| 2023/0096599 A1* | 3/2023 | Zheng .................. A61K 47/545 514/230.5 |
| 2023/0106066 A1 | 4/2023 | Mainolfi et al. |
| 2023/0122219 A1 | 4/2023 | Weiss et al. |
| 2023/0132715 A1 | 5/2023 | Ji et al. |
| 2023/0144292 A1 | 5/2023 | Weiss |
| 2023/0190940 A1 | 6/2023 | Zhang et al. |
| 2023/0219945 A1 | 7/2023 | Mainolfi et al. |
| 2023/0234936 A1 | 7/2023 | Feng et al. |
| 2023/0234950 A1 | 7/2023 | Mainolfi et al. |
| 2023/0234953 A1 | 7/2023 | Weiss et al. |
| 2023/0241075 A1 | 8/2023 | Campbell et al. |
| 2023/0250110 A1 | 8/2023 | Zheng |
| 2023/0257399 A1 | 8/2023 | Leong et al. |
| 2023/0277519 A1 | 9/2023 | Gollob et al. |
| 2023/0303526 A1 | 9/2023 | Mainolfi et al. |
| 2023/0365562 A1 | 11/2023 | Mainolfi et al. |

FOREIGN PATENT DOCUMENTS

| | | |
|---|---|---|
| WO | WO-1996007655 A1 | 3/1996 |
| WO | WO0110858 A1 | 2/2001 |
| WO | WO-2001042246 A2 | 6/2001 |
| WO | WO-2002020740 A2 | 3/2002 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |
| WO | WO-2006105021 A2 | 10/2006 |
| WO | WO-2006122806 A2 | 11/2006 |
| WO | WO-2007005874 A2 | 1/2007 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2008132601 A1 | 11/2008 |
| WO | WO-2009009116 A2 | 1/2009 |
| WO | WO-2009044273 A2 | 4/2009 |
| WO | WO-2009073620 A2 | 6/2009 |
| WO | WO-2009114512 A1 | 9/2009 |
| WO | WO-2009132238 A3 | 10/2009 |
| WO | WO-2010019570 A2 | 2/2010 |
| WO | WO-2010077634 A1 | 7/2010 |
| WO | WO-2011028683 A1 | 3/2011 |
| WO | WO-2011043371 A1 | 4/2011 |
| WO | WO-2011056652 A1 | 5/2011 |
| WO | WO-2011070024 A1 | 6/2011 |
| WO | WO-2011090760 A1 | 7/2011 |
| WO | WO-2011107553 A1 | 9/2011 |
| WO | WO-2011109400 A2 | 9/2011 |
| WO | WO-2011131407 A1 | 10/2011 |
| WO | WO-2011140249 A2 | 11/2011 |
| WO | WO-2012003281 A3 | 1/2012 |
| WO | WO-2012007375 A1 | 1/2012 |
| WO | WO-2012032433 A1 | 3/2012 |
| WO | WO-2012068546 A1 | 5/2012 |
| WO | WO-2012078559 A2 | 6/2012 |
| WO | WO-2012084704 A1 | 6/2012 |
| WO | WO-2012097013 A1 | 7/2012 |
| WO | WO-2012129258 | 9/2012 |
| WO | WO-2012142237 A1 | 10/2012 |
| WO | WO-2012145493 A1 | 10/2012 |
| WO | WO-2013042137 A1 | 3/2013 |
| WO | WO-2013066729 A1 | 5/2013 |
| WO | WO-2013079174 A1 | 6/2013 |
| WO | WO-2013087699 A1 | 6/2013 |
| WO | WO-2013106535 A1 | 7/2013 |
| WO | WO-2013106612 A1 | 7/2013 |
| WO | WO-2013106614 A1 | 7/2013 |
| WO | WO-2013106641 A1 | 7/2013 |
| WO | WO-2013106643 A2 | 7/2013 |
| WO | WO-2013106646 A2 | 7/2013 |
| WO | WO-2013119716 A1 | 8/2013 |
| WO | WO-2013132044 A1 | 9/2013 |
| WO | WO-2013169264 A1 | 11/2013 |
| WO | WO-2014008218 A1 | 1/2014 |
| WO | WO-2014008992 A1 | 1/2014 |
| WO | WO-2014011902 A1 | 1/2014 |
| WO | WO-2014011906 A2 | 1/2014 |
| WO | WO-2014011911 A2 | 1/2014 |
| WO | WO-2014036357 A1 | 3/2014 |
| WO | WO-2014044622 A1 | 3/2014 |
| WO | WO-2014058685 A1 | 4/2014 |
| WO | WO-2014058691 A1 | 4/2014 |
| WO | WO-2014063061 A1 | 4/2014 |
| WO | WO-2014074660 A1 | 5/2014 |
| WO | WO-2014074675 A1 | 5/2014 |
| WO | WO-2014108452 A1 | 7/2014 |
| WO | WO-2014121931 A1 | 8/2014 |
| WO | WO-2014121942 A1 | 8/2014 |
| WO | WO-2014143672 A1 | 9/2014 |
| WO | WO-2015048281 A1 | 4/2015 |
| WO | WO-2015068856 A1 | 5/2015 |
| WO | WO-2015071393 A1 | 5/2015 |
| WO | WO-2015091426 A1 | 6/2015 |
| WO | WO-2015103453 A1 | 7/2015 |
| WO | WO-2015104662 A1 | 7/2015 |
| WO | WO-2015104688 A1 | 7/2015 |
| WO | WO-2015150995 A1 | 10/2015 |
| WO | WO-2015160845 A3 | 10/2015 |
| WO | WO-2015164374 A1 | 10/2015 |
| WO | WO-2015193846 A1 | 12/2015 |
| WO | WO-2016011390 A1 | 1/2016 |
| WO | WO-2016053769 A1 | 4/2016 |
| WO | WO-2016053770 A1 | 4/2016 |
| WO | WO-2016053771 A1 | 4/2016 |
| WO | WO-2016053772 A1 | 4/2016 |
| WO | WO-2016081679 A1 | 5/2016 |
| WO | WO-2016105518 A1 | 6/2016 |
| WO | WO-2016118666 A1 | 7/2016 |
| WO | WO-2016144844 A1 | 9/2016 |
| WO | WO-2016144846 A1 | 9/2016 |
| WO | WO-2016144847 A1 | 9/2016 |
| WO | WO-2016144848 A1 | 9/2016 |
| WO | WO-2016144849 A1 | 9/2016 |
| WO | WO-2016149668 A1 | 9/2016 |
| WO | WO-2016169989 A1 | 10/2016 |
| WO | WO-2016172560 A1 | 10/2016 |
| WO | WO-2016174183 A1 | 11/2016 |
| WO | WO-2016197032 A1 | 12/2016 |
| WO | WO-2016197114 A1 | 12/2016 |
| WO | WO-2016210034 A1 | 12/2016 |
| WO | WO-2017004133 A1 | 1/2017 |
| WO | WO-2017004134 | 1/2017 |

(56) References Cited

FOREIGN PATENT DOCUMENTS

| | | |
|---|---|---|
| WO | WO-2017007612 A1 | 1/2017 |
| WO | WO-2017009798 A1 | 1/2017 |
| WO | WO-2017009806 A1 | 1/2017 |
| WO | WO-2017011371 A1 | 1/2017 |
| WO | WO-2017011590 A1 | 1/2017 |
| WO | WO-2017030814 A1 | 2/2017 |
| WO | WO-2017033093 A1 | 3/2017 |
| WO | WO2017046036 A1 | 3/2017 |
| WO | WO-2017049068 A1 | 3/2017 |
| WO | WO-2017059280 A1 | 4/2017 |
| WO | WO-2017079267 A1 | 5/2017 |
| WO | WO-2017108723 A2 | 6/2017 |
| WO | WO-2017117473 A1 | 7/2017 |
| WO | WO-2017117474 A1 | 7/2017 |
| WO | WO-2017127430 A1 | 7/2017 |
| WO | WO-2017161119 A1 | 9/2017 |
| WO | WO-2017176708 A1 | 10/2017 |
| WO | WO-2017176957 A1 | 10/2017 |
| WO | WO-2017176958 A1 | 10/2017 |
| WO | WO-2017197036 A1 | 11/2017 |
| WO | WO-2017197046 A1 | 11/2017 |
| WO | WO-2017197051 A1 | 11/2017 |
| WO | WO-2017197055 A1 | 11/2017 |
| WO | WO-2017197056 A1 | 11/2017 |
| WO | WO-2017201449 A1 | 11/2017 |
| WO | WO-2017205762 A1 | 11/2017 |
| WO | WO-2017205766 A1 | 11/2017 |
| WO | WO-2017207385 A1 | 12/2017 |
| WO | WO-2017211924 A1 | 12/2017 |
| WO | WO-2018052058 A1 | 3/2018 |
| WO | WO-2018089736 A1 | 5/2018 |
| WO | WO-2018098367 A1 | 5/2018 |
| WO | WO-2018119441 A1 | 6/2018 |
| WO | WO2018140809 A1 | 8/2018 |
| WO | WO-2018144649 A1 | 8/2018 |
| WO | WO-2018209012 A1 | 11/2018 |
| WO | WO-2018237026 A1 | 12/2018 |
| WO | WO-2019043214 A1 | 3/2019 |
| WO | WO-2019060693 A1 | 3/2019 |
| WO | WO-2019060742 A1 | 3/2019 |
| WO | WO-2019084026 A1 | 5/2019 |
| WO | WO-2019084030 A1 | 5/2019 |
| WO | WO-2019099868 A1 | 5/2019 |
| WO | WO-2019099926 A1 | 5/2019 |
| WO | WO2019111218 A1 | 6/2019 |
| WO | WO-2019133531 A1 | 7/2019 |
| WO | WO-2019140380 A1 | 7/2019 |
| WO | WO-2019140387 A1 | 7/2019 |
| WO | WO-2019160915 A1 | 8/2019 |
| WO | WO-2019165229 A1 | 8/2019 |
| WO | WO-2019236483 | 12/2019 |
| WO | WO-2020010177 A1 | 1/2020 |
| WO | WO-2020010210 A1 | 1/2020 |
| WO | WO-2020010227 A1 | 1/2020 |
| WO | WO-2020018788 A1 | 1/2020 |
| WO | WO2020092907 A1 | 5/2020 |
| WO | WO2020113233 A1 | 6/2020 |
| WO | WO2020150626 A1 | 7/2020 |
| WO | WO-2020251969 A1 | 12/2020 |
| WO | WO-2020251971 A1 | 12/2020 |
| WO | WO-2020251972 A1 | 12/2020 |
| WO | WO-2020251974 A1 | 12/2020 |
| WO | WO-2020264490 A1 | 12/2020 |
| WO | WO-2020264499 A1 | 12/2020 |
| WO | WO-2021011631 A1 | 1/2021 |
| WO | WO-2021011634 A1 | 1/2021 |
| WO | WO-2021011868 A1 | 1/2021 |
| WO | WO-2021011871 A1 | 1/2021 |
| WO | WO2021018118 A1 | 2/2021 |
| WO | WO-2021053555 A1 | 3/2021 |
| WO | WO-2021119159 A1 | 6/2021 |
| WO | WO-2021127190 A1 | 6/2021 |
| WO | WO-2021127278 A1 | 6/2021 |
| WO | WO-2021127283 A2 | 6/2021 |
| WO | WO2021158634 A1 | 8/2021 |
| WO | WO2021222366 A1 | 11/2021 |
| WO | WO2021247897 A1 | 12/2021 |
| WO | WO2021247899 A1 | 12/2021 |
| WO | WO2021257914 A1 | 12/2021 |
| WO | WO2022028547 A1 | 2/2022 |
| WO | WO2022087216 A1 | 4/2022 |
| WO | WO2022125790 A1 | 6/2022 |
| WO | WO2022147465 A1 | 7/2022 |
| WO | WO2022174268 A1 | 8/2022 |
| WO | WO2022174269 A1 | 8/2022 |
| WO | WO2022236339 A1 | 11/2022 |
| WO | WO2023076556 A1 | 5/2023 |
| WO | WO2023137439 A1 | 7/2023 |
| WO | WO2023147594 A2 | 8/2023 |
| WO | WO2023192586 A1 | 10/2023 |

OTHER PUBLICATIONS

Venkatesh, J. Pharm. Sci. 89, 145-154 (2000).*
J. G. Cannon, Chapter Nineteen in Burger's Medicinal Chemistry and Drug Discovery, Fifth Edition, vol. I: Principles and Practice, Wiley-Interscience 1995, pp. 783-802.*
Tinworth, Med. Chem. Commun., 2016, 7, 2206.*
Collins, Biochemical Journal (2017) 474 1127-1147.*
Dorwald F. A. Side Reactions in Organic Synthesis, 2005, Wiley: VCH, Weinheim p. IX of Preface p. 1-15.*
PCT International Search Report and Written Opinion from PCT/US2020/042109, dated Dec. 10, 2020.
CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).
Matyskiela et al., "A Cereblon Modulator (CC-220) with Improved Degradation of Ikaros and Aiolos," J Med Chem. 2018;61(2):535-542.
Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, (3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.
Seitz et al., "Sulfenylation and Halogenation of Di-and Trianions Derived from Substituted Glutarimides," Synthetic Communications. 1977;7(6):367-374.
Xia and Chen, "Iron-catalyzed N-alkylation of azoles via cleavage of an sp3 C-H bond adjacent to a nitrogen atom," J Org Chem. 2012;77(20):9366-73.
Zinc 170596280, Date Added Aug. 8, 2015, https://zinc.docking.org/substances/ZINC000170596280/. Date Accessed: Jan. 10, 2022.
PCT International Search Report and Written Opinion from PCT/US2023/060645, dated Mar. 31, 2023.
Adams et al., "Big opportunities for small molecules in immuno-oncology," Nat Rev Drug Discov. 2015;14(9):603-22.
Aruri et al., "Metal-free Cross-Dehydrogenative Coupling of HN-azoles with a-C(sp3)-H Amides via C-H Activation and Its Mechanistic and Application Studies," J Org Chem. 2017;82(2):1000-1012.
Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.

(56) References Cited

OTHER PUBLICATIONS

Berge et al., "Pharmaceutical salts," J Pharm Sci. Jan. 1977;66(1):1-19.
Berndsen et al., "New insights into ubiquitin E3 ligase mechanism," Nat Struct Mol Biol. 2014;21(4):301-7.
Boichenko et al., "A FRET-Based Assay for the Identification and Characterization of Cereblon Ligands," J Med Chem. 2016;59(2):770-4.
Buckley et al., "IRAK-4 inhibitors. Part 1: a series of amides," Bioorg Med Chem Lett. 2008;18(11):3211-4.
Buckley et al., "IRAK-4 inhibitors. Part II: a structure-based assessment of imidazo[1,2-a]pyridine binding," Bioorg Med Chem Lett. 2008;18(11):3291-5.
Buckley et al., "IRAK-4 inhibitors. Part III: A series of imidazo[1,2-a]pyridines," Bioorg Med Chem Lett. 2008;18(12):3656-60.
Cameron et al., "Loss of Interleukin Receptor-Associated Kinase 4 Signaling Suppresses Amyloid Pathology and Alters Microglial Phenotype in a Mouse Model of Alzheimer's Disease," J Neurosci. 2012;32(43):15112-23.
Cario, "Therapeutic Impact of Toll-like Receptors on Inflammatory Bowel Diseases: A Multiple-edged Sword," Inflamm Bowel Dis. 2008;14(3):411-21.
Chang et al., "What is the functional role of the thalidomide binding protein cereblon?" Int J Biochem Mol Biol. 2011;2(3):287-94.
Charrier et al., "Desulfonylative Radical Ring Closure onto Aromatics. A Modular Route to Benzazepin-2-ones and 5-Arylpiperidin-2-ones," Org. Lett. 2012, 14(8): 2018-2021.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem. 2015;58(1):96-110.
Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol. 2011; 186(2):1279-88.
Cohen, "Targeting protein kinases for the development of anti-inflammatory drugs," Curr Opin Cell Biol. 2009;21(2):17-24.
Connolly et al., "Complexities of TGF-beta Targeted Cancer Therapy," Int J Biol Sci. 2012;8(7):964-978.
Contino-Pepin et al., "Preliminary biological evaluations of new thalidomide analogues for multiple sclerosis application," Bioorg Med Chem Lett. 2009;19(3):878-81.
Crews, "Targeting the Undruggable Proteome: The Small Molecules of My Dreams," Chem Biol. 2010;17(6):551-5.
Cushing et al., "IRAK4 kinase controls Toll-like receptor induced inflammation through the transcription factor IRF5 in primary human monocytes," J Biol Chem. 2017;292(45):18689-18698.
Dalbeth et al., "Hyperuricaemia and gout: state of the art and future perspectives," Ann Rheum Dis. 2014;73(9):1598-600.
Degorce et al., "Optimization of permeability in a series of pyrrolotriazine inhibitors of IRAK4," Bioorg Med Chem. 2018;26(4):913-924.
Deshaies and Joazeiro, "Ring domain E3 ubiquitin ligases," Annu Rev Biochem. 2009;78:399-434.
Devi et al., "Medicinal Attributes of Imidazo[1,2-a]pyridine Derivatives: An Update," Curr Top Med Chem, 2016, 16(26):2963-2994.
Dinarello, "IL-1: Discoveries, controversies and future directions," Eur J Immunol. 2010:40(3):599-606.
Dinarello, "Interleukin 1 and interleukin 18 as mediators of inflammation and the aging process," Am J Clin Nutr. 2006;83(suppl):447S-55S.
Dinarello, "Interleukin-18 and the Pathogenesis of Inflammatory Diseases," Semin Nephrol. 2007;27(1):98-114.
Dudhgaonkar et al., "Selective IRAK4 Inhibition Attenuates Disease in Murine Lupus Models and Demonstrates Steroid Sparing Activity," J Immunol. 2017;198(3):1308-1319.
Dunne et al., "IRAK1 and IRAK4 Promote Phosphorylation, Ubiquitation, and Degradation of MyD88 Adaptor-like (Mal)," J Biol Chem. 2010;285(24):18276-82.

El-Gamal et al., "Recent Advances of Colony-Stimulating Factor-1 Receptor (CSF-1R) Kinase and Its Inhibitors," J Med Chem. 2018;61(13):5450-5466.
Fischer et al., "Structure of the DDB1-CRBN E3 ubiquitin ligase in complex with thalidomide," Nature. 2014;512(7512):49-53.
Flannery et al., "The interleukin-1 receptor-associated kinases: Critical regulators of innate immune signaling," Biochem Pharmacol. 2010;80(12):1981-91.
Gearing, "Targeting toll-like receptors for drug development: a summary of commercial approaches," Immunol Cell Biol. 2007;85(6):490-4.
Geyer and Müller-Ladner, "Actual status of antiinterleukin-1 therapies in rheumatic diseases," Curr Opin Rheumatol. 2010;22(3):246-51.
Gottipati et al., "IRAK1: A critical signaling mediator of innate immunity," Cell Signal. 2008;20(2):269-76.
Hagner et al., "CC-122, a pleiotropic pathway modifier, mimics an interferon response and has antitumor activity in DLBCL," Blood. 2015;126(6):779-89.
Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction," J. Med. Chem., 2019, 62(9): 4683-4702.
Hennessy et al., "Targeting Toll-like receptors: emerging therapeutics?" Nat Rev Drug Discov. 2010;9(4):293-307.
Hines et al., "MDM2-Recruiting PROTAC Offers Superior, Synergistic Antiproliferative Activity via Simultaneous Degradation of BRD4 and Stabilization of p53," Cancer Res. 2019;79(1):251-262.
Hoffman et al., "Efficacy and Safety of Rilonacept (Interleukin-1 Trap) in Patients with Cryopyrin-Associated Periodic Syndromes," Arthritis Rheum. 2008;58(8):2443-5.
Iannello et al., "Role of Interleukin-18 in the Development and Pathogenesis of Aids," Aids Rev. 2009;11(3):115-25.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science. 2010;327(5971):1345-50.
Kargbo, "Protac Degradation of IRAK4 for the Treatment of Cancer," ACS Med. Chem. Lett., 2019, 10(10):1370-1371.
Kelly et al., "Selective interleukin-1 receptor-associated kinase 4 inhibitors for the treatment of autoimmune disorders and lymphoid malignancy," J Exp Med. 2015;212(13):2189-201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Kim et al., "A critical role for IRAK4 kinase activity in Toll-like receptor-mediated innate immunity," J Exp Med. 2007;204(5):1025-36.
Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol. 2014;387(10):909-19.
Kou et al., "Effects of RuPeng15 Powder (RPP15) on Monosodium Urate Crystal-Induced Gouty Arthritis in Rats," Evid Based Complement Alternat Med. 2015;2015:527019.
Koziczak-Holbro et al., "IRAK-4 Kinase Activity Is Required for Interleukin-1 (IL-1) Receptor- and Toll-like Receptor 7-mediated Signaling and Gene Expression," J Biol Chem. 2007;282(18):13552-60.
Krönke et al., "Lenalidomide causes selective degradation of IKZF1 and IKZF3 in multiple myeloma cells" Science. 2014;343(6168):301-305.
Ku et al., "Selective predisposition to bacterial infections in IRAK-4-deficient children: IRAK-4-dependent TLRs are otherwise redundant in protective immunity," J Exp Med. 2007;204(10):2407-2422.

(56) References Cited

OTHER PUBLICATIONS

Kubo-Murai et al., "IRAK-4-dependent Degradation of IRAK-1 is a Negative Feedback Signal for TLR-mediated NF-kB Activation," J Biochem. 2008;143(3):295-302.

Küppers, "IRAK inhibition to shut down TLR signaling in autoimmunity and MyD88-dependent lymphomas," J Exp Med. 2015;212(13):2184.

Lebakken et al., "A Fluorescence Lifetime Based Binding Assay to Characterize Kinase Inhibitors," J Biomol Screen. 2007;12(6):828-41.

Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," J Med Chem. 2017;60(13):5521-5542.

Li et al., "Genome-wide and functional annotation of human E3 ubiquitin ligases identifies MULAN, a mitochondrial E3 that regulates the organelle's dynamics and signaling," PLoS One. 2008;3(1):e1487.

Li et al., "IRAK-4: A novel member of the IRAK family with the properties of an IRAK-kinase," Proc Natl Acad Sci USA. 2002;99(8):5567-72.

Li et al., "Targeting interleukin-1 receptor-associated kinase for human hepatocellular carcinoma," J Exp Clin Cancer Res. 2016;35(1):140.

Li, "IRAK4 in TLR/IL-1R signaling: Possible clinical applications," Eur J Immunol. 2008;38(3):614-8.

Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015;6(6):683-688.

Lin et al., "Helical assembly in the MyD88-IRAK4-IRAK2 complex in TLR /IL-1R signalling," Nature. 2010:465(7300):885-90.

Lu et al., "Discovery of a Keap1-dependent peptide PROTAC to knockdown Tau by ubiquitination-proteasome degradation pathway," Euro J Med Chem. 2018;46:251-9.

Lu et al., "Hijacking the E3 Ubiquitin Ligase Cereblon to Efficiently Target BRD4," Chem Biol. 2015;2(6):755-63.

Lu et al., "The myeloma drug lenalidomide promotes the cereblon-dependent destruction of Ikaros proteins," Science. 2014;343(6168):305-309.

Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clin Proc. 2009;84(2):114-22.

Martinon et al., "Gout-associated uric acid crystals activate the NALP3 inflammasome," Nature. 2006;440(7081):237-41.

Maschera et al., "Overexpression of an enzymatically inactive interleukin-1-receptor-associated kinase activates nuclear factor-kB," Biochem J. 1999;339(Pt2):227-31.

McElroy et al., "Discovery and hit-to-lead optimization of 2,6-diaminopyrimidine Inhibitors of interleukin-1 receptor-associated kinase 4," Bioorg Med Chem Lett. 2015;25(9):1836-41.

McElroy et al., "Potent and Selective Amidopyrazole Inhibitors of IRAK4 That Are Efficacious in a Rodent Model of Inflammation," ACS Med Chem Lett. 2015;6(6):677-682.

Moynagh, "The Pellino Family: IRAK E3 ligases with emerging roles in innate immune signalling," Trends Immunol. 2009, 30(1): 33-42.

Muller et al., "Amino-Substituted Thalidomide Analogs: Potent Inhibitors of TNF-? Production," Bioorg Med Chem Lett. 1999;9(11):1625-30.

Ngo et al., "Oncogenically active MYD88 mutations in human lymphoma," Nature. 2011;470(7332):115-9.

Nunes et al., "Targeting IRAK4 for Degradation with PROTACTSs," ACS Med Chem Lett. 2019;10(7):1081-1085.

Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556-4570.

Ohoka et al., "Development of Small Molecule Chimeras That Recruit AhR E3 Ligase to Target Proteins, "ACS Chem. Biol. 2019, 14(12):2822-2832.

Okazaki et al., "A rheostat for immune responses: the unique properties of PD-1 and their advantages for clinical application," Nat. Immunol. 2013; 14(12): 1212-1218.

PCT International Preliminary Report on Patentability from PCT/US2018/067304, dated Jun. 30, 2020.

PCT International Preliminary Report on Patentability from PCT/US2019/040462, dated Jan. 21, 2021.

PCT International Search Report and Written Opinion from PCT/US2018/052181, dated Feb. 26, 2019.

PCT International Search Report and Written Opinion from PCT/US2018/052242, dated Jan. 30, 2019.

PCT International Search Report and Written Opinion from PCT/US2018/067304, dated Apr. 30, 2019.

PCT International Search Report and Written Opinion from PCT/US2019/013481, dated Mar. 15, 2019.

PCT International Search Report and Written Opinion from PCT/US2019/013491, dated Mar. 18, 2019.

PCT International Search Report and Written Opinion from PCT/US2019/040462, dated Sep. 20, 2019.

PCT International Search Report and Written Opinion from PCT/US2019/040520, dated Nov. 13, 2019.

PCT International Search Report and Written Opinion from PCT/US2019/040545, dated Oct. 21, 2019.

PCT International Search Report and Written Opinion from PCT/US2019/064070, dated Apr. 6, 2020.

PCT International Search Report and Written Opinion from PCT/US2020/026869, dated Jul. 27, 2020.

PCT International Search Report and Written Opinion from PCT/US2020/036913, dated Oct. 26, 2020.

PCT International Search Report and Written Opinion from PCT/US2020/036916, dated Oct. 26, 2020.

PCT International Search Report and Written Opinion from PCT/US2020/036918, dated Oct. 26, 2020.

PCT International Search Report and Written Opinion from PCT/US2020/036921, dated Oct. 26, 2020.

PCT International Search Report and Written Opinion from PCT/US2020/040101, dated Nov. 10, 2020.

PCT International Search Report and Written Opinion from PCT/US2020/040125, dated Nov. 13, 2020.

PCT International Search Report and Written Opinion from PCT/US2020/042105, dated Nov. 20, 2020.

PCT International Search Report and Written Opinion from PCT/US2020/042530, dated Oct. 16, 2020.

PCT International Search Report and Written Opinion from PCT/US2020/042534, dated Oct. 26, 2020.

PCT International Search Report and Written Opinion from PCT/US2020/064061, dated Apr. 9, 2021.

PCT International Search Report and Written Opinion from PCT/US2020/065628, dated May 28, 2021.

PCT International Search Report and Written Opinion from PCT/US2020/065752, dated Mar. 25, 2021.

PCT International Search Report and Written Opinion from PCT/US2020/065757, dated May 28, 2021.

PCT International Search Report and Written Opinion from PCT/US2020/066859, dated May 4, 2021.

PCT International Search Report and Written Opinion from PCT/US2021/062640, dated Feb. 8, 2022.

Picard et al., "Clinical features and outcome of patients with IRAK-4 and MyD88 deficiency," Medicine (Baltimore). 2010;89(6):403-425.

Picard et al., "Inherited human IRAK-4 deficiency: an update," Immunol Res. 2007;38(1-3):347-52.

Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood. 2016; 126(23): 675-676.

Powers et al., "Discovery and initial SAR of inhibitors of interleukin-1 receptor-associated kinase-4," Bioorg Med Chem Lett. 2006;16(11):2842-5.

(56) References Cited

OTHER PUBLICATIONS

Priyadarshini et al., "Copper catalyzed oxidative cross-coupling of aromatic amines with 2-pyrrolidinone: a facile synthesis of N-aryl-r-amino-r-lactams," Tetrahedron. 2014;70(36):6068-6074.
Pubmed Compound Summary for CID 101524675, "(2R)-3-Fluoro-2-(2-methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-yl)piperidine-2,6-dione, U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 5426, "Thalidomide," created Mar. 25, 2005.
Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," U.S. National Library of Medicine, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, U.S. Library of Medicine, created Oct. 20, 2014, https://pubchem.ncbi.nlm.nih.gov/compound/84036945. Date Accessed: Feb. 25, 2020 (7 pages).
Raina et al., "Chemical Inducers of Targeted Protein Degradation," J Biol Chem. 2010;285(15):11057-60.

Ramirez et al., "Defining causative factors contributing in the activiation of hedgehog signaling in diffuse large B-cell lymphoma," Leuk Res. 2012;36(10):1267-73.
Rokosz et al., "Kinase inhibitors as drugs for chronic inflammatory and immunological diseases: progress and challenges," Expert Opin Ther Targets. 2008;12(7):883-903.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS One. 2017; 12(8): e0183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002;41(14):2596-9.
Rusnac et al., "Recognition of the Diglycine C-End Degron by CRL2 KLHDC2 Ubiquitin Ligase," Mol. Cell. 2018, 72(5):813-822.e4.
Schnekloth et al., "Chemical approaches to controlling intracellular protein degradation," Chembiochem. 2005;6(1):40-46.
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017;60(24):10071-10091.
Seganish et al., "Discovery and Structure Enabled Synthesis of 2,6-diaminopyrimidine-4-one IRAK4 Inhibitors," ACS Med Chem Lett. 2015;6(8):942-947.
Seganish et al., "Initial optimization and series evolution of diaminopyrimidine inhibitors of interleukin-1 receptor associated kinase 4," Bioorg Med Chem Lett. 2015;25(16):3203-3207.
Sen et al., "Transcriptional signaling by double-stranded RNA: role of TLR3," Cytokine Growth Factor Rev. 2005;16(1):1-14.
Shanmugasundaram et al., "A modular PROTAC design for target destruction using a degradation signal based on a single amino acid," J Biol Chem. 2019;294(41):15172-15175.
Smith et al., "Identification of quinazoline based inhibitors of IRAK4 for the treatment of inflammation," Bioorg Med Chem Lett. 2017;27(12):2721-2726.
So et al., "A pilot study of IL-1 inhibition by anakinra in acute gout," Arthritis Res Ther. 2007;9(2):R28.
Song et al., "The kinase activities of interleukin-e receptor associated kinase (IRAK)-1 and 4 are redundant in the control of inflammatory cytokine expression in human cells," Mol Immunol. 2009;46(7):1458-66.
Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.
Spratt et al., "RBR E3 ubiquitin ligases: new structures, new insights, new question," Biochem J. 2014;458(3);421-37.
Stewart et al., "Efforts toward elucidating Thalidomide's molecular target: an expedient synthesis of the first Thalidomide biotin analogue," Organic & Biomolecular Chemistry. 2010;8(18): 4059-4062.
Sun et al., "Carbohydrate and protein immobilization onto solid surfaces by sequential Diels-Alder and azide-alkyne cycloadditions," Bioconjug Chem. 2006;17(1):52-7.
Suzuki et al., "IRAK-4 as the central TIR signaling mediator in innate immunity," Trends Immunol. 2002;23(10):503-6.
Suzuki et al., "Severe impairment of interleukin-1 and Toll-like receptor signalling in mice lacking IRAK-4," Nature. 2002;416(6882):750-6.
Swantek et al., "IL-1 Receptor-Associated Kinase Modulates Host Responsiveness to Endotoxin," Journal of Immunology 164: 4301-4306, J Immunol. 2000;164(8):4301-6.
Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009;68(10):1613-7.
Terkeltaub, "Update on gout: new therapeutic strategies and options," Nat Rev Rheumatol. 2010;6(1):30-8.
Tong et al., "Targeted Protein Degradation via a Covalent Reversible Degrader Based on Bardoxolone", ChemRxiv. First Posted Online: Apr. 2, 2020.

(56) References Cited

OTHER PUBLICATIONS

Toogood, "Small molecule immuno-oncology therapeutic agents," Bioorg. Med. Chem. Lett. 2018;28(3):319-329.
Torres et al., "Hyperalgesia, synovitis and multiple biomarkers of inflammation are suppressed by interleukin 1 inhibition in a novel animal model of gouty arthritis," Ann Rheum Dis. 2009;68(10):1602-8.
Toure and Crews, "Small-Molecule PROTACS: New Approaches to Protein Degradation," Angew Chem Int Ed Engl. 2016;55(6):1966-73.
Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].
Trøseid et al., "The role of interleukin-18 in the metabolic syndrome," Cardiovasc Diabetol. 2010;9:11.
Tumey et al., "Identification and optimization of indolo[2,3-c]quinoline inhibitors of IRAK4," Bioorg Med Chem Lett. 2014;24(9):2066-72.
Uehara et al., "Selective degradation of splicing factor CAPERɑ by anticancer sulfonamides," Nat Chem Biol. 2017;13(6):675-680.
Varfolomeev et al., "IAP antagonists induce autoubiquitination of c-IAPs, NF-kappaB activation, and TNFalpha-dependent apoptosis," Cell. 2007;131(4):669-81.
Vollmer et al., "The mechanism of activation of IRAK1 and IRAK4 by interleukin-1 and Toll-like receptor agonists," Biochem J. 2017;474(12):2027-2038.
Wang et al., "Crystal Structure of IRAK-4 Kinase in Complex with Inhibitors: Serine/Threonine Kinase with Tyrosine as a Gatekeeper," Structure. 2006;14(12):1835-44.
Wang et al., "Discovery of potent, selective, and orally bioavailable inhibitors of interleukin-1 receptor-associated kinase 4," Bioorg Med Chem Lett. 2015;25(23):5546-5550.
Wang et al., "IRAK-4 Inhibitors for Inflammation," Curr Top Med Chem. 2009;9(8):724-37.
Wang et al., "Roles of F-box proteins in cancer," Nat Rev Cancer. 2014;14(4):233-47.
Ward et al., "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med. 2008;75 Suppl 5:S9-12.
Winter et al., "Selective Target Protein Degradation via Phthalimide Conjugation," Science. 2015;348(6241):1376-1381.
Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., "Disruption of MYD88 pathway signaling leads to loss of constitutive IRAK1, Nk-kB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Yang et al., "Exploiting synthetic lethality for the therapy of ABC diffuse large B cell lymphoma," Cancer Cell. 2012;21(6):723-37.
Zhang et al., "Constitutive IRAK4 Activation Underlies Poor Prognosis and Chemoresistance in Pancreatic Ductal Adenocarcinoma," Clin Cancer Res. 2017;23(7):1748-1759.
Zhang et al., "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.
Zhou et al., "Targets of curcumin," Curr Drug Targets. 2011;12(3):332-347.
Zou et al., "PD-L1 (B7-H1) and PD-1 pathway blockade for cancer therapy: Mechanisms, response biomarkers, and combinations," Sci. Transl. Med. 2016;8(328):328rv4.

"Acute Leukemia", Merck Manual (Online Edition), 2013, 6 pages.
Ali et al., "Design, synthesis, molecular modelling and biological evaluation of novel 3-(2-naphthyl)-1-phenyl-1H-pyrazole derivatives as potent antioxidants and 15-Lipoxygenase inhibitors", J Enzyme Inhib Med Chem., 2020, 35(1):847-863.
Bastin et al.: "Salt selection and Optimisation Procedures for Pharmaceutical New Chemical Entities", Organic Process Research & Development, 2000, 4:427-435.
Blake et al., "Studies with deuterated drugs," J Pharm Sci., 1975,64(3):367-391.
Chou and Talalay, "Quantitative analysis of dose-effect relationships: the combined effects of multiple drugs or enzyme inhibitors," Adv Enzyme Regul., 1984, 22:27-55.
Cushing et al., "Interleukin 1/Toll-like receptor-induced autophosphorylation activates interleukin 1 receptor-associated kinase 4 and controls cytokine induction in a cell type-specific manner," J Biol Chem, 2014,289(15):10865-10875.
Cyrus et al., "Impact of linker length on the activity of PROTACs", Molecular BioSystems, 2011, 7(2):359-364.
Damasio, "Alzheimer's Disease and related dementias", Cecil Textbook of Medicine, 20th Edition, 1996, vol. 2, pp. 1992-1996.
De Nardo et al. "Interleukin-1 receptor-associated kinase 4 (IRAK4) plays a dual role in myddosome formation and Toll-like receptor signaling," J Biol Chem., 2018, 293(39):15195-15207.
Field et al., "Novel highly specific anti-periostin antibodies uncover the functional importance of the fasciclin 1-1 domain and highlight preferential expression of periostin in aggressive breast cancer", Int J Cancer., Apr. 15, 2016, 138(8):1959-1970.
Fisher et al., "The complexities inherent in attempts to decrease drug clearance by blocking sites of CYP-mediated metabolism," Curr Opin Drug Discov Devel., 2006, 9(1):101-109.
Foster, "Deuterium isotope effects in the metabolism of drugs and xenobiotics: implications for drug design," Advances in Drug Research, 1985, 14:1-40.
Fukuto et al., "Determination of the mechanism of demethylenation of (methylenedioxy)phenyl compounds by cytochrome P450 using deuterium isotope effects," J Med Chem., 1991, 34(9):2871-2876.
Gura T., "Systems for identifying new drugs are often faulty," Science, 1997, 278(5340):1041-1042.
Harvey, et al., "Management of organic impurities in small molecule medicinal products: Deriving safe limits for use in early development", Regulatory Toxicology and Pharmacology, 2017, 84:116-123.
Huang et al., "A Chemoproteomic Approach to Query the Degradable Kinome Using a Multi-kinase Degrader", Cell Chem Biol., 2018, 25(1):88-99.
Johnson et al., "Relationships between drug activity in NCI preclinical in vitro and in vivo models and early clinical trials," British Journal of Cancer, 2001, 84(10):1424-1431.
Kummerer, "Pharmaceuticals in the environment", Annual Review of Environment and Resources, 2010, 35:57-75.
Kushner et al., "Pharmacological uses and perspectives of heavy water and deuterated compounds," Can J Physiol Pharmacol., 1999, 77(2):79-88.
Kyutoku et al., "Role of periostin in cancer progression and metastasis: inhibition of breast cancer progression and metastasis by anti-periostin antibody in a murine model", Int J Mol Med., Aug. 2011, 28(2):181-186.
Layzer, Robert B., "Degenerative diseases of the nervous system", Cecil Textbook of Medicine, 20th Edition, 1996, vol. 2, pp. 2050-2057.
Naito et al., "Chemical protein knockdown: Development of SNIPER compounds that induce degradation of target proteins", Medchem News, 2018, 28(1):29-35.
Ohoka Nobumichi "Development of Protein Knockdown Technology as Emerging Drug Discovery Strategy", Pharmaceutical Magazine, Sep. 1, 2018, 138(9):1135-1143.
Orecchia et al., "Identification of a novel cell binding site of periostin involved in tumour growth", Eur J Cancer, Sep. 2011, 47(14):2221-2229.
Patra and Choi, "Recent Progress in the Molecular Recognition and Therapeutic Importance of Interleukin-1 Receptor-Associated Kinase 4," Molecules, 2016, 21(11):1529.

(56) References Cited

OTHER PUBLICATIONS

Pearce et al., "Failure modes in anticancer drug discovery and development," Cancer Drug Design and Discovery, Edited by Stephen Neidle, Chapter 18, 2008, pp. 424-435.
Simone, "Oncology: Introduction", Cecil Textbook of Medicine, 20th Edition, 1996, vol. 1, pp. 1004-1010.
Slavin et al., "Identification of highly potent and selective Interlukin-1 receptor associated kinase 4 (IRAK4) degraders for the treatment suppurativa", Feb. 2020, 1 page. Retrived from https://www.kymeratx.com/wp-content/uploads/2020/07/EHSF_Kymera_2020_Final.pdf.
Steinebach et al., "A MedChem toolbox for cereblon-directed PROTACs", Med. Chem. Commun., 2019, 10(6):1037-1041.
Stieger et al., "Recrystallization of Active Pharmaceutical Ingredients", Crystallization—Science and Technology, 2012, pp. 183-201.
Troup, "Current strategies for the design of PROTAC linkers: a critical review", Explor Target Antitumor Ther., 2020, 1(5):273-312.
PCT International Preliminary Report on Patentability from PCT/US2018/052181, dated Apr. 2, 2020, 8 pages.
PCT International Preliminary Report on Patentability from PCT/US2019/013491, dated Jul. 23, 2020, 7 pages.
PCT International Preliminary Report on Patentability from PCT/US2019/064070, dated Jun. 10, 2021, 7 pages.
PCT International Preliminary Report on Patentability from PCT/US2020/040101, dated Jan. 6, 2022, 8 pages.
PCT International Preliminary Report on Patentability from PCT/US2020/040125, dated Jan. 6, 2022, 8 pages.
PCT International Preliminary Report on Patentability from PCT/US2020/042530, dated Jan. 27, 2022, 6 pages.
PCT International Preliminary Report on Patentability from PCT/US2020/064061, dated Jun. 23, 2022, 13 pages.
PCT International Preliminary Report on Patentability from PCT/US2020/065752, dated Jun. 30, 2022, 7 pages.
PCT International Preliminary Report on Patentability from PCT/US2020/065757 dated Jun. 30, 2022, 9 pages.
PCT International Preliminary Report on Patentability from PCT/US2021/016377, dated Aug. 18, 2022, 8 pages.
PCT International Preliminary Report on Patentability from PCT/US2021/029578, dated Nov. 10, 2022, 7 pages.
PCT International Preliminary Report on Patentability from PCT/US2021/035745, dated Dec. 15, 2022, 6 pages.
PCT International Preliminary Report on Patentability from PCT/US2021/035747, dated Dec. 15, 2022, 6 pages.
PCT International Preliminary Report on Patentability from PCT/US2021/037952, dated Dec. 29, 2022, 9 pages.
PCT International Preliminary Report on Patentability from PCT/US2021/055971, dated May 4, 2023, 06 pages.
PCT International Preliminary Report on Patentability from PCT/US2021/062640, dated Jun. 22, 2023, 06 pages.
PCT International Preliminary Report on Patentability from PCT/US2021/071048, dated Feb. 9, 2023, 07 pages.
PCT International Preliminary Report on Patentability from PCT/US2021/073186, dated Jul. 13, 2023, 12 pages.
PCT International Preliminary Report on Patentability from PCT/US2022/070662, dated Aug. 24, 2023, 6 pages.
PCT International Preliminary Report on Patentability from PCT/US2022/070664, dated Aug. 24, 2023, 7 pages.
PCT International Preliminary Report on Patentability from PCT/US2020/065628, dated Jun. 30, 2022, 9 pages.
PCT International Search Report and Written Opinion from PCT/US2021/029578, dated Aug. 6, 2021, 09 pages.
PCT International Search Report and Written Opinion from PCT/US2021/035745, dated Sep. 27, 2021.
PCT International Search Report and Written Opinion from PCT/US2021/035747, dated Sep. 27, 2021.
PCT International Search Report and Written Opinion from PCT/US2021/037952, dated Sep. 29, 2021, 11 pages.
PCT International Search Report and Written Opinion from PCT/US2021/055971, dated Feb. 2, 2022, 08 pages.
PCT International Search Report and Written Opinion from PCT/US2021/071048, dated Nov. 5, 2021, 09 pages.
PCT International Search Report and Written Opinion from PCT/US2021/073186, dated May 3, 2022, 16 pages.
PCT International Search Report and Written Opinion from PCT/US2022/048163, dated Mar. 10, 2021.
PCT International Search Report and Written Opinion from PCT/US2022/070662, dated Apr. 18, 2022.
PCT International Search Report and Written Opinion from PCT/US2022/070664, dated May 3, 2022.
PCT International Search Report and Written Opinion from PCT/US2022/072194, dated Sep. 6, 2022, 10 pages.
PCT International Search Report and Written Opinion from PCT/US2023/017087, dated Jun. 12, 2023, 08 pages.
PCT International Search Report and Written Opinion received from PCT/US2021/016377, dated Jun. 15, 2021.
PCT International Search Report and Written Opinion received from PCT/US2023/061673, dated Jul. 25, 2023, 9 pages.

* cited by examiner

IRAK DEGRADERS AND USES THEREOF

CROSS-REFERENCE TO RELATED APPLICATIONS

This application claims the benefit of U.S. Provisional Appl. No. 63/132,332, filed Dec. 30, 2020, the entirety of which is herein incorporated by reference.

TECHNICAL FIELD OF THE INVENTION

The present invention relates to compounds and methods useful for the modulation of one or more interleukin-1 receptor-associated kinases ("IRAK") via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17(6):551-555; Schnnekloth J S Jr., Chembiochem, 2005, 6(1):40-46).

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage E3 ligase mediated protein degradation to target cancer-associated proteins such as interleukin-1 receptor-associated kinases ("IRAK") hold promise as therapeutic agents. Accordingly, there remains a need to find compounds that are IRAK degraders useful as therapeutic agents.

SUMMARY OF THE INVENTION

The present application relates novel bifunctional compounds, which function to recruit IRAK kinases to E3 Ubiquitin Ligase for degradation, and methods of preparation and uses thereof. In particular, the present disclosure provides bifunctional compounds, which find utility as modulators of targeted ubiquitination of IRAK kinases, which are then degraded and/or otherwise inhibited by the bifunctional compounds as described herein. Also provided are monovalent compounds, which find utility as inducers of targeted ubiquitination of IRAK kinases, which are then degraded and/or otherwise inhibited by the monovalent compounds as described herein. An advantage of the compounds provided herein is that a broad range of pharmacological activities is possible, consistent with the degradation/inhibition of IRAK kinases. In addition, the description provides methods of using an effective amount of the compounds as described herein for the treatment or amelioration of a disease condition, such as cancer, e.g., multiple myeloma.

The present application further relates to targeted degradation of IRAK kinases through the use of bifunctional molecules, including bifunctional molecules that link a degradation inducing moiety to a ligand that binds IRAK kinases having the following general formula I:

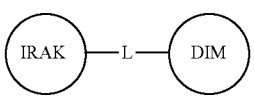

or a pharmaceutically acceptable salt thereof, wherein each variable is as defined and described herein.

It has now been found that compounds of this invention, and pharmaceutically acceptable compositions thereof, are effective for the modulation of targeted ubiquitination. Such compounds have the formula I-a:

I-a

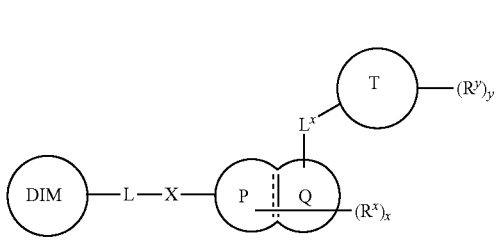

or a pharmaceutically acceptable salt thereof, wherein each variable is as defined and described herein.

The present invention further relates to bifunctional compounds that not only degrade IRAK, but also degrade IMiD substrates, such as Ikaros, Aiolos, or Ikaros and Aiolos.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of IRAK enzymes in biological and pathological phenomena; the study of intracellular signal transduction pathways occurring in bodily tissues; and the comparative evaluation of new IRAK inhibitors or IRAK degraders or other regulators of kinases, signaling pathways, and cytokine levels in vitro or in vivo.

DETAILED DESCRIPTION OF CERTAIN EMBODIMENTS

1. General Description of Certain Embodiments of the Invention

Compounds of the present invention, and compositions thereof, are useful as degraders and/or inhibitors of one or more IRAK protein kinases. In some embodiments, a provided compound degrades and/or inhibits IRAK-1/2/3/4. In some embodiments, a provided compound degrades IRAK4 and IMiD substrates, such as Ikaros, Aiolos, or Ikaros and Aiolos.

In certain embodiments, the present invention provides a compound of formula I:

I

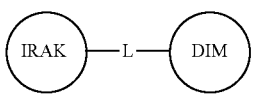

or a pharmaceutically acceptable salt thereof, wherein:
IRAK is an IRAK binding moiety capable of binding to one or more of IRAK-1, -2, -3, or -4;
L is a bivalent moiety that connects IRAK to DIM; and
DIM is a degradation inducing moiety.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

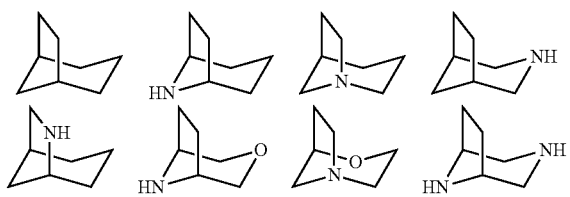

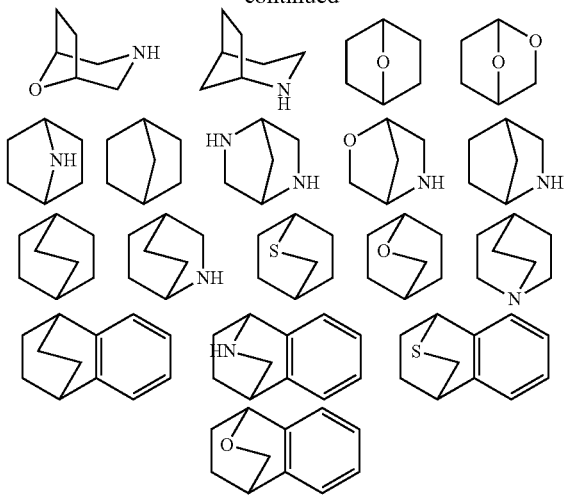

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

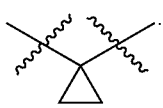 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, bridged bicyclic, or spirocyclic. A heterocyclyl group may contain one or more oxo (C=O) or thioxo (S=O) group. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$); —(CH$_2$)$_{0-4}$CH(OR$^\circ$)$_2$; —(CH$_2$)$_{0-4}$ SR$^\circ$); —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$C(O)OR$^\circ$; —N(R$^\circ$)N(R$^\circ$)C(O)R$^\circ$); —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$ SR$^\circ$); —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —SC(S)SR$^\circ$, —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$); —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched)alkylene)O—N(R$^\circ$)$_2$; or —(C$_{1-4}$ straight or branched)alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —C(O)R$^\dagger$$_2$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of IV, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "provided compound" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention As used herein, the term "inhibitor" is defined as a compound that binds to and/or inhibits an IRAK kinase with measurable affinity. In certain embodiments, an inhibitor has an IC$_{50}$ and/or binding constant of less than about 50 µM, less than about 1 µM, less than about 500 nM, less than about 100 nM, less than about 10 nM, or less than about 1 nM.

As used herein, the term "degrader" is defined as a heterobifunctional or monovalent compound that binds to and/or inhibits both an IRAK kinase and an E3 ligase with measurable affinity resulting in the ubiqitination and subsequent degradation of the IRAK kinase. In certain embodiments, a degrader has an DC$_{50}$ of less than about 50 µM, less than about 1 µM, less than about 500 nM, less than about 100 nM, less than about 10 nM, or less than about 1 nM. As used herein, the term "monovalent" refers to a degrader compound without an appended E3 ligase binding moiety.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof.

3. Description of Exemplary Embodiments

As described above, in certain embodiments, the present invention provides a compound of formula I:

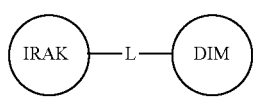

I or a pharmaceutically acceptable salt thereof, wherein:
  IRAK is an IRAK binding moiety capable of binding to one or more of IRAK-1, -2, -3, or -4;
  L is a bivalent moiety that connects IRAK to DIM; and
  DIM is a degradation inducing moiety.

In some embodiments, the present invention provides a compound of formula I:

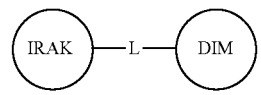

I or a pharmaceutically acceptable salt thereof, wherein:
  IRAK is an IRAK4 binding moiety;
  L is a bivalent moiety that connects IRAK to DIM; and
  DIM is an E3 ubiquitin ligase binding moiety (LBM), a lysine mimetic, or a hydrogen atom.

IRAK Binding Moiety (IRAK)

In certain embodiments, the present invention provides a compound of formula I, where IRAK is a IRAK4 binding moiety thereby forming a compound of formulae I-a:

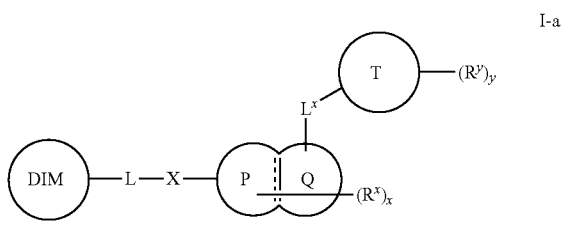

I-a or a pharmaceutically acceptable salt thereof, wherein DIM and L are as defined and described herein, and wherein:

each $R^x$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP(O)R$_2$, —OP(O)(OR)$_2$, —OP(O)(OR)NR$_2$, —OP(O)(NR$_2$)$_2$, —P(O)R$_2$, —SiR$_3$, —Si(OR)R$_2$, or

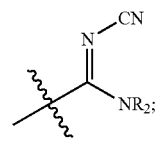

or
  two $R^x$ groups are optionally taken together to form an optionally substituted 5-6 membered partially unsaturated or aryl fused ring having 0-3 heteroatoms independently selected from nitrogen, oxygen, or sulfur, or a 3-5 membered saturated or partially unsaturated carbocyclic or heterocyclic spiro fused ring having 0-3 heteroatoms independently selected from nitrogen, oxygen, or sulfur, each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same atom are optionally taken together with their intervening atoms to form a 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;
each $R^y$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —SiR$_3$, —SF$_5$, or

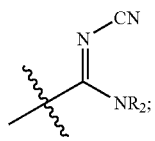

or
  a single $R^y$ and a single $R^x$ are optionally taken together with their intervening atoms to form a 8-20 membered saturated or partially unsaturated carbocyclic or heterocyclic monocyclic or bicyclic ring having 1-10 heteroatoms, independently selected from nitrogen, oxygen, and sulfur;
each $R^z$ is independently an optionally substituted group selected from C$_{1-6}$ aliphatic, phenyl, a 4-9 membered saturated or partially unsaturated carbocyclic or heterocyclic monocyclic, bicyclic, bridged bicyclic, or spirocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
Ring P and Ring Q are optionally fused rings independently selected from phenyl or benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P and Ring Q are independently and optionally substituted with 1-2 oxo groups;
Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;
$L^x$ is a covalent bond or a C$_{1-3}$ bivalent straight or branched saturated or unsaturated hydrocarbon chain wherein 1-2 methylene units of the chain are independently and optionally replaced with -Cy$^x$-, —O—, —S—, —C(O)—, —C(S)—, —CR$_2$—, —CRF—, —CF$_2$—, —NR—, —N=CR—, —CR=CR—, or —S(O)$_2$—, wherein R of —CR$_2$—, —CRF—, —NR—, —N=CR—, or —CR=CR— can combine with $R^x$ or $R^y$ to form a 4-7 membered saturated or partially unsaturated carbocyclic or heterocyclic ring having 1-3 heteroatoms independently selected from nitrogen, oxygen, and sulfur;
-Cy$^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -Cy$^x$- is optionally substituted with 1-2 oxo groups;
X is a covalent bond or a 4-6 membered saturated or partially unsaturated carbocyclic or heterocyclic ring having 1-2 heteroatoms independently selected from nitrogen, oxygen, and sulfur;
---- is a single or double bond;
each x is 0, 1, 2, 3 or 4; and
each y is 0, 1, 2, 3 or 4.
As described herein, a core structure depicted as

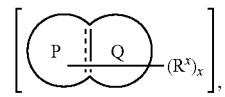

includes for example, structures

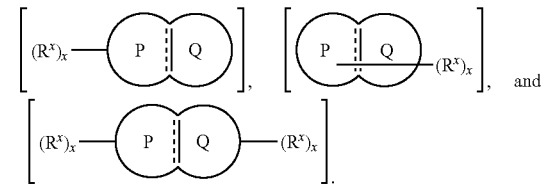

As defined generally above, each $R^x$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP(O)R$_2$, —OP(O)(OR)$_2$, —OP(O)(OR)NR$_2$, —OP(O)(NR$_2$)$_2$, —P(O)R$_2$, —SiR$_3$, —Si(OR)R$_2$, or

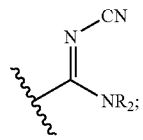

or two $R^x$ groups are optionally taken together to form an optionally substituted 5-6 membered partially unsaturated or aryl fused ring having 0-3 heteroatoms independently selected from nitrogen, oxygen, or sulfur, or a 3-5 membered saturated or partially unsaturated carbocyclic or heterocyclic spiro fused ring having 0-3 heteroatoms independently selected from nitrogen, oxygen, or sulfur.

In some embodiments, $R^x$ is hydrogen. In some embodiments, $R^x$ is deuterium. In some embodiments, $R^x$ is $R^z$. In some embodiments, $R^x$ is halogen. In some embodiments, $R^x$ is —CN. In some embodiments, each $R^x$ is independently —NO$_2$. In some embodiments, $R^x$ is —OR. In some embodiments, each $R^x$ is independently —SR. In some embodiments, $R^x$ is —NR$_2$. In some embodiments, $R^x$ is —S(O)$_2$R. In some embodiments, $R^x$ is —S(O)$_2$NR$_2$. In some embodiments, $R^x$ is —S(O)R. In some embodiments, $R^x$ is —CFR$_2$. In some embodiments, $R^x$ is —CF$_2$R. In some embodiments, $R^x$ is —CF$_3$. In some embodiments, $R^x$ is —CR$_2$(OR). In some embodiments, $R^x$ is —CR$_2$(NR$_2$). In some embodiments, $R^x$ is —C(O)R. In some embodiments, $R^x$ is —C(O)OR. In some embodiments, $R^x$ is —C(O)NR$_2$. In some embodiments, $R^x$ is —N$^+$(O$^-$)R$_2$. In some embodiments, $R^x$ is —OP(O)R$_2$. In some embodiments, $R^x$ is —OP(O)(OR)$_2$. In some embodiments, $R^x$ is —OP(O)(OR)NR$_2$. In some embodiments, $R^x$ is —OP(O)(NR$_2$)$_2$. In some embodiments $R^x$ is —P(O)R$_2$. In some embodiments, $R^x$ is —SiR$_3$. In some embodiments, $R^x$ is —Si(OR)R$_2$. In some embodiments, $R^x$ is —SF$_5$. In some embodiments, $R^x$ is

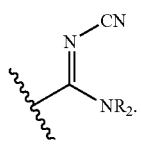

In some embodiments, two $R^x$ groups are optionally taken together to form an optionally substituted 5-6 membered partially unsaturated or aryl fused ring having 0-3 heteroatoms independently selected from nitrogen, oxygen, or sulfur. In some embodiments, two $R^x$ groups are optionally taken together to form an optionally substituted 3-5 membered saturated or partially unsaturated carbocyclic or heterocyclic spiro fused ring having 0-3 heteroatoms independently selected from nitrogen, oxygen, or sulfur, In some embodiments, $R^x$ is

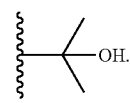

In some embodiments, $R^x$ is fluoro. In some embodiments, $R^x$ is chloro. In some embodiments, $R^x$ is —CF$_2$H. In some embodiments, $R^x$ is —OMe. In some embodiments, $R^x$ is —OEt. In some embodiments, $R^x$ is —OiPr. In some embodiments, $R^x$ is —NMe$_2$. In some embodiments, $R^x$ is —SMe. In some embodiments, $R^x$ is —S(O)Me. In some embodiments, $R^x$ is —S(O)$_2$Me. In some embodiments, $R^x$ is -Me. In some embodiments, $R^x$ is -Et. In some embodiments, $R^x$ is -iPr. In some embodiments, $R^x$ is cyclopropyl. In some embodiments, $R^x$ is —Ac. In some embodiments, $R^x$ is —CO$_2$Me. In some embodiments, $R^x$ is —CO$_2$H. In some embodiments, $R^x$ is —OCF$_2$H. In some embodiments, $R^x$ is —OCF$_3$. In some embodiments, $R^x$ is

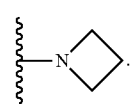

In some embodiments, $R^x$ is

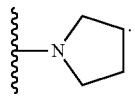

In some embodiments, $R^x$ is

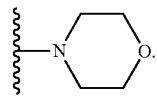

In some embodiments, $R^x$ is

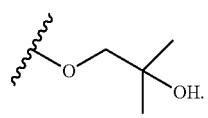 [SMILES: *OCC(C)(C)O]

In some embodiments, $R^x$ is

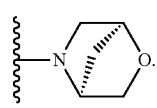

In some embodiments, $R^x$ is

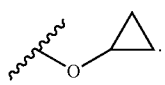

In some embodiments, $R^x$ is

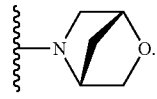 [SMILES: *N1C[C@H]2C[C@@H]1CO2]

In some embodiments, $R^x$ is

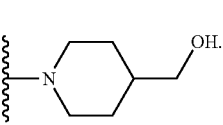

In some embodiments, $R^x$ is

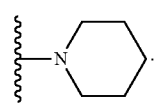

In some embodiments, R$^x$ is

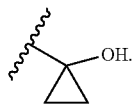 [SMILES: *C1(O)CC1]

In some embodiments, R$^x$ is

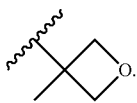 [SMILES: *C1(C)COC1]

In some embodiments, R$^x$ is

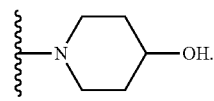

In some embodiments, R$^x$ is

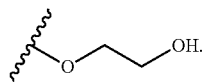 [SMILES: *OCCO]

In some embodiments, R$^x$ is

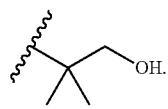 [SMILES: *C(C)(C)CO]

In some embodiments, R$^x$ is

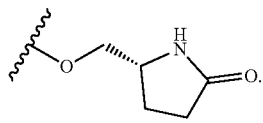 [SMILES: *OC[C@H]1CCC(=O)N1]

In some embodiments, R$^x$ is

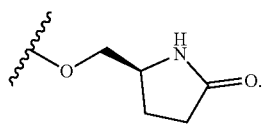 [SMILES: *OC[C@@H]1CCC(=O)N1]

In some embodiments, R$^x$ is

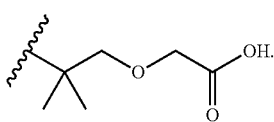 [SMILES: *C(C)(C)COCC(=O)O]

In some embodiments, R$^x$ is

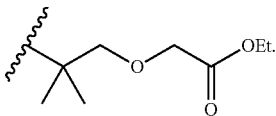 [SMILES: *C(C)(C)COCC(=O)OCC]

In some embodiments, R$^x$ is

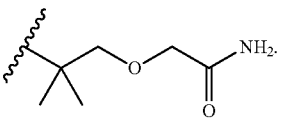 [SMILES: *C(C)(C)COCC(N)=O]

In some embodiments, each R$^x$ is selected from those depicted in Table 1, below.

As generally defined above, each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same atom are optionally taken together with their intervening atom to form a 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur.

In some embodiments, each R is independently hydrogen. In some embodiments, each R is an optionally substituted group selected from C$_{1-6}$ aliphatic. In some embodiments, each R is an optionally substituted phenyl. In some embodiments, each R is an optionally substituted 4-7 membered saturated or partially unsaturated heterocyclic having 1-2 heteroatoms independently selected from nitrogen, oxygen, and sulfur. In some embodiments, each R is an optionally substituted 5-6 membered heteroaryl ring having 1-4 heteroatoms independently selected from nitrogen, oxygen, and sulfur. In some embodiments, two R groups on the same atom are optionally taken together with their intervening atom to form a 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur.

In some embodiments, each R is selected from those depicted in Table 1, below.

As defined generally above, each R$^y$ is independently hydrogen, deuterium, R$^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP(O)R$_2$, —OP(O)(OR)$_2$, —OP(O)(OR)NR$_2$, —OP(O)(NR$_2$)$_2$, —P(O)R$_2$, —SiR$_3$, —Si(OR)R$_2$, —SF$_5$, or

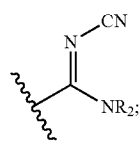

or two $R^y$ groups are optionally taken together to form an optionally substituted 5-6 membered partially unsaturated or aryl fused ring having 0-3 heteroatoms independently selected from nitrogen, oxygen, or sulfur; or a single $R^y$ and a single $R^x$ are optionally taken together with their intervening atoms to form a 8-20 membered saturated or partially unsaturated carbocyclic or heterocyclic monocyclic or bicyclic ring having 1-10 heteroatoms, independently selected from nitrogen, oxygen, and sulfur.

In some embodiments, $R^y$ is hydrogen. In some embodiments, $R^y$ is deuterium. In some embodiments, $R^y$ is $R^z$. In some embodiments, $R^y$ is halogen. In some embodiments, $R^y$ is —CN. In some embodiments, $R^y$ is —NO$_2$. In some embodiments, $R^y$ is —OR. In some embodiments, $R^y$ is —SR. In some embodiments, $R^y$ is —NR$_2$. In some embodiments, $R^y$ is —S(O)$_2$R. In some embodiments, $R^y$ is —S(O)$_2$NR$_2$. In some embodiments, $R^y$ is —S(O)R. In some embodiments, $R^y$ is —CFR$_2$. In some embodiments, $R^y$ is —CF$_2$R. In some embodiments, $R^y$ is —CF$_3$. In some embodiments, $R^y$ is —CR$_2$(OR). In some embodiments, $R^y$ is —CR$_2$(NR$_2$). In some embodiments, $R^y$ is —C(O)R. In some embodiments, $R^y$ is —C(O)OR. In some embodiments, $R^y$ is —C(O)NR$_2$. In some embodiments, $R^y$ is —N$^+$(O$^-$)R$_2$. In some embodiments, $R^y$ is —OP(O)R$_2$. In some embodiments, $R^y$ is —OP(O)(OR)$_2$. In some embodiments, $R^y$ is —OP(O)(OR)NR$_2$. In some embodiments, $R^y$ is —OP(O)(NR$_2$)$_2$. In some embodiments, $R^y$ is —P(O)R$_2$. In some embodiments, $R^y$ is —SiR$_3$. In some embodiments, $R^y$ is —Si(OR)R$_2$. In some embodiments, $R^y$ is —SF$_5$. In some embodiments, $R^y$ is

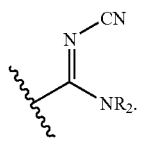

In some embodiments, two $R^y$ groups are optionally taken together to form an optionally substituted 5-6 membered partially unsaturated or aryl fused ring having 0-3 heteroatoms independently selected from nitrogen, oxygen, or sulfur. In some embodiments, a single $R^y$ and a single $R^x$ are optionally taken together with their intervening atoms to form a 8-20 membered saturated or partially unsaturated carbocyclic or heterocyclic monocyclic or bicyclic ring having 1-10 heteroatoms, independently selected from nitrogen, oxygen, and sulfur.

In some embodiments, $R^y$ is fluoro. In some embodiments, $R^y$ is chloro. In some embodiments, $R^y$ is —CN. In some embodiments, $R^y$ is —CF$_2$Me. In some embodiments, $R^y$ is —CFMe$_2$. In some embodiments, $R^y$ is -Me. In some embodiments, $R^y$ is —OMe. In some embodiments, $R^y$ is —OCF$_3$. In some embodiments, $R^y$ is fluoro. In some embodiments, $R^y$ is cyclopropyl. In some embodiments, $R^y$ is

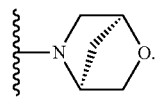

In some embodiments, $R^y$ is

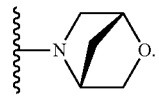

In some embodiments, $R^y$ and $R^x$ taken together is

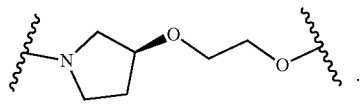 [SMILES: *OCCO[C@H]1CCN(*)C1]

In some embodiments, $R^y$ and $R^x$ taken together is

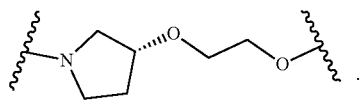 [SMILES: *OCCO[C@@H]1CCN(*)C1]

In some embodiments, $R^y$ and $R^x$ taken together is

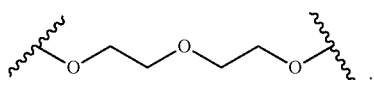 [SMILES: *OCCOCCO*]

In some embodiments, $R^y$ and $R^x$ taken together is

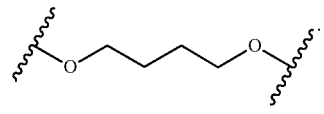 [SMILES: *OCCCCO*]

In some embodiments, $R^y$ and $R^x$ taken together is

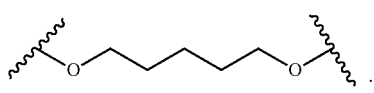 [SMILES: *OCCCCCO*]

In some embodiments, each $R^y$ is selected from those depicted in Table 1, below.

As generally defined above, each $R^z$ is independently an optionally substituted group selected from $C_{1-6}$ aliphatic, phenyl, a 4-9 membered saturated or partially unsaturated carbocyclic or heterocyclic monocyclic, bicyclic, bridged bicyclic, or spirocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^z$ is an optionally substituted group selected from $C_{1-6}$ aliphatic. In some embodiments, $R^z$ is an optionally substituted phenyl. In some embodiments, $R^z$ is an optionally substituted 4-9 membered saturated or partially unsaturated carbocyclic or heterocyclic monocyclic, bicyclic, bridged bicyclic, or spirocyclic ring having 1-2 heteroatoms independently selected from nitrogen, oxygen, and sulfur. In some embodiments, $R^z$ is an optionally substituted 5-6 membered heteroaryl ring having 1-4 heteroatoms independently selected from nitrogen, oxygen, and sulfur.

In some embodiments, each $R^z$ is selected from those depicted in Table 1, below.

As generally defined above, Ring P and Ring Q are optionally fused rings independently selected from phenyl or benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P and Ring Q are independently and optionally substituted with 1-2 oxo groups.

In some embodiments, Ring P phenyl or benzo. In some embodiments, Ring P is a 4-7 membered saturated or partially unsaturated carbocyclic or heterocyclic ring having 1-3 heteroatoms independently selected from nitrogen, oxygen, and sulfur. In some embodiments, Ring P is a 5-6 membered heteroaryl ring having 1-4 heteroatoms independently selected from nitrogen, oxygen, and sulfur. In some embodiments, Ring P is optionally substituted with 1-2 oxo groups. In some embodiments, Ring Q is phenyl or benzo. In some embodiments, Ring Q is a 4-7 membered saturated or partially unsaturated carbocyclic or heterocyclic ring having 1-3 heteroatoms independently selected from nitrogen, oxygen, and sulfur. In some embodiments, Ring Q is a 5-6 membered heteroaryl ring having 1-4 heteroatoms independently selected from nitrogen, oxygen, and sulfur. In some embodiments, Ring Q is optionally substituted with 1-2 oxo groups.

In some embodiments, Ring P and Ring Q are

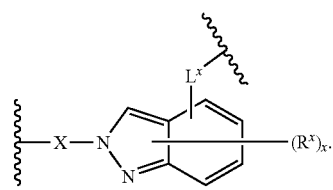

In some embodiments, Ring P and Ring Q are

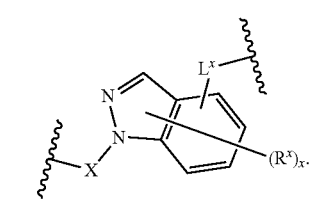

In some embodiments, Ring P and Ring Q are

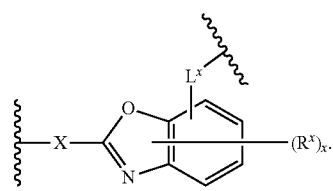

In some embodiments, Ring P and Ring Q are

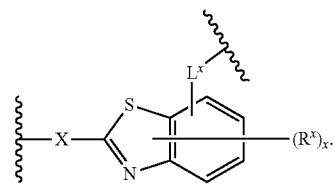

In some embodiments, Ring P and Ring Q are

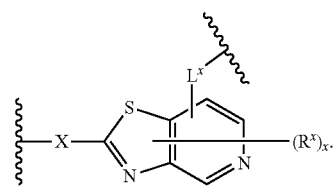

In some embodiments, Ring P and Ring Q are

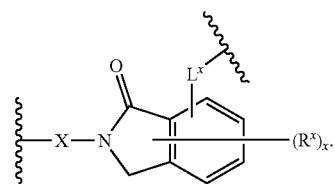

In some embodiments, Ring P and Ring Q are

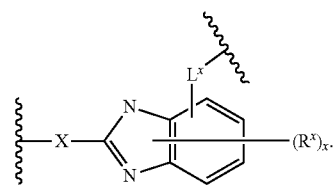

In some embodiments, Ring P and Ring Q are

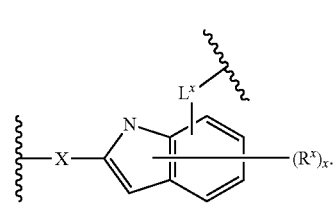

In some embodiments, Ring P and Ring Q are

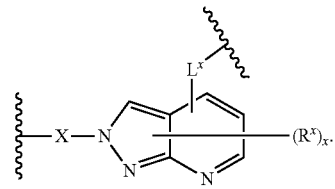

In some embodiments, Ring P and Ring Q are

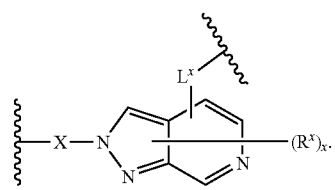

In some embodiments, Ring P and Ring Q are

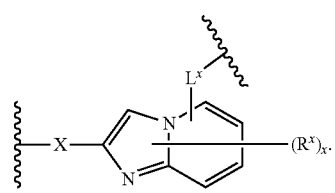

In some embodiments, Ring P and Ring Q are

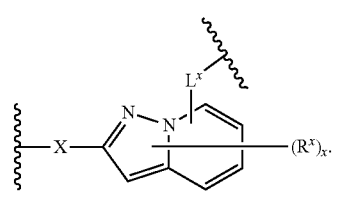

In some embodiments, Ring P and Ring Q are selected from those depicted in Table 1, below.

As generally defined above, Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups.

In some embodiments, Ring T is from phenyl. In some embodiments, Ring T is a 4-7 membered saturated or partially unsaturated carbocyclic or heterocyclic ring having 1-3 heteroatoms independently selected from nitrogen, oxygen, and sulfur. In some embodiments, Ring T is a 5-9 membered mono- or bicyclic heteroaryl ring having 1-4 heteroatoms independently selected from nitrogen, oxygen, and sulfur. In some embodiments, Ring T is further optionally substituted with 1-2 oxo groups.

In some embodiments, Ring T is

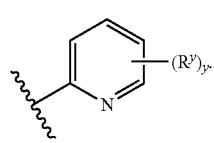

In some embodiments, Ring T is

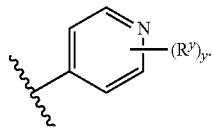

In some embodiments, Ring T is

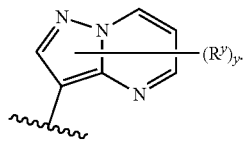

In some embodiments, Ring T is

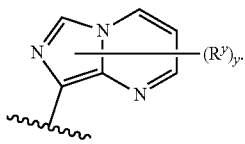

In some embodiments, Ring T is

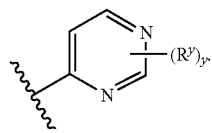

In some embodiments, Ring T is

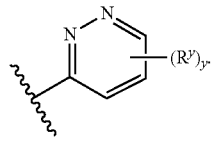

In some embodiments, Ring T is phenyl. In some embodiments, Ring T is

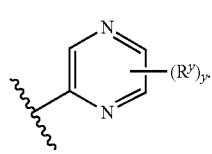

In some embodiments, Ring T is

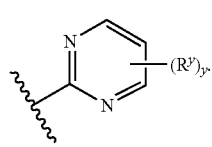

In some embodiments, Ring T is

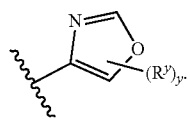

In some embodiments, Ring T is

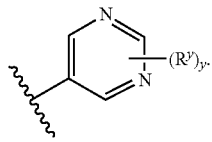

In some embodiments, Ring T is

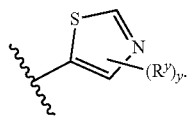

In some embodiments, Ring T is

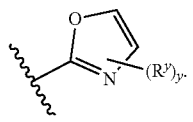

In some embodiments, Ring T is

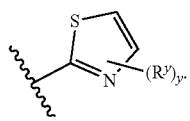

In some embodiments, Ring T is

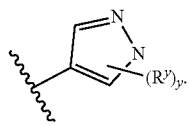

In some embodiments, Ring T is selected from those depicted in Table 1, below.

As generally defined above, $L^x$ is a covalent bond or a $C_{1-3}$ bivalent straight or branched saturated or unsaturated hydrocarbon chain wherein 1-2 methylene units of the chain are independently and optionally replaced with -Cy$^x$-, —O—, —S—, —C(O)—, —C(S)—, —CR$_2$—, —CRF—, —CF$_2$—, —NR—, —N=CR—, —CR=CR—, or —S(O)$_2$—, wherein R of —CR$_2$—, —CRF—, —NR—, —N=CR—, or —CR=CR— can combine with R$^x$ or R$^y$ to form a 4-7 membered saturated or partially unsaturated carbocyclic or heterocyclic ring having 1-3 heteroatoms independently selected from nitrogen, oxygen, and sulfur.

In some embodiments, $L^x$ is a covalent bond. In some embodiments, $L^x$ is a $C_{1-3}$ bivalent straight or branched saturated or unsaturated hydrocarbon chain wherein 1-2 methylene units of the chain are independently and optionally replaced with -Cy$^x$-, —O—, —S—, —C(O)—, —C(S)—, —CR$_2$—, —CRF—, —CF$_2$—, —NR—, —N=CR—, —CR=CR—, or —S(O)$_2$—. In some embodiments, R of —CR$_2$—, —CRF—, —NR—, —N=CR—, or —CR=CR— can combine with R$^x$ or R$^y$ to form a 4-7 membered saturated or partially unsaturated carbocyclic or heterocyclic ring having 1-3 heteroatoms independently selected from nitrogen, oxygen, and sulfur.

In some embodiments, Ring $L^x$ is —C(O)N(H)—. In some embodiments, Ring $L^x$ is —CH$_2$C(O)N(H)—. In some embodiments, Ring $L^x$ is

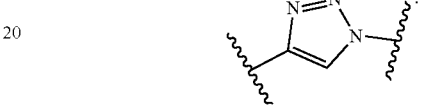

In some embodiments, $L^x$ combines with R$^y$ to form

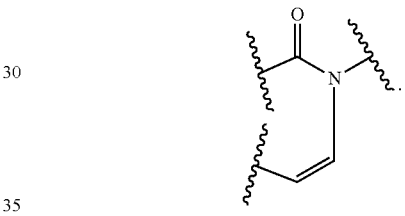

In some embodiments, $L^x$ combines with R$^y$ to form

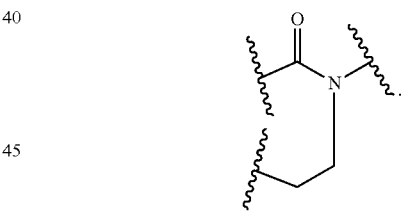

In some embodiments, Ring $L^x$ is selected from those depicted in Table 1, below.

As generally defined above, -Cy$^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -Cy$^x$- is optionally substituted with 1-2 oxo groups.

In some embodiments, -Cy$^x$- is an optionally substituted ring selected from a 3-5 membered saturated or partially unsaturated carbocyclic or heterocyclic ring having 0-3 heteroatoms independently selected from nitrogen, oxygen, and sulfur. In some embodiments, -Cy$^x$- is a 5 membered heteroaryl ring having 1-4 heteroatoms independently selected from nitrogen, oxygen, and sulfur. In some embodiments, -Cy$^x$- is optionally substituted with 1-2 oxo groups.

In some embodiments, Ring -Cy$^x$- is selected from those depicted in Table 1, below.

As described above, X is a covalent bond or a 4-6 membered saturated or partially unsaturated carbocyclic or heterocyclic ring having 1-2 heteroatoms independently selected from nitrogen, oxygen, and sulfur.

In some embodiments, X is a covalent bond. In some embodiments, X is a 4-6 membered saturated or partially unsaturated carbocyclic or heterocyclic ring having 1-2 heteroatoms independently selected from nitrogen, oxygen, and sulfur.

In some embodiments, X is

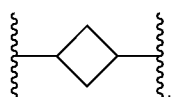

In some embodiments, X is

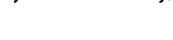

In some embodiments, X is

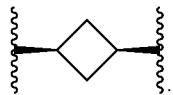 [SMILES: *[C@H]1C[C@@H](*)C1]

In some embodiments, X is


In some embodiments, X is

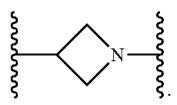 [SMILES: *C1CN(*)C1]

In some embodiments, X is

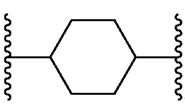

In some embodiments, X is

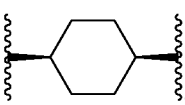

In some embodiments, X is

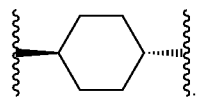

In some embodiments, X is

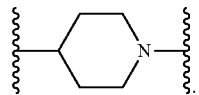

In some embodiments, X is selected from those depicted in Table 1, below.

As generally defined above, ==== is a single or double bond.

In some embodiments, ==== is a single. In some embodiments, ==== is a double bond.

In some embodiments, Ring ==== is selected from those depicted in Table 1, below.

As generally defined above, each x and y are independently 0, 1, 2, 3 or 4.

In some embodiments, each x and y are independently 0. In some embodiments, each x and y are independently 1. In some embodiments, each x and y are independently 2. In some embodiments, each x and y are independently 3. In some embodiments, each x and y are independently 4.

In some embodiments, each x and y are selected from those depicted in Table 1, below.

In some embodiments, the present invention provides a compound of formula I-a, wherein Ring P and Ring Q form an indazole ring as shown, to provide a compound of formula I-d-1:

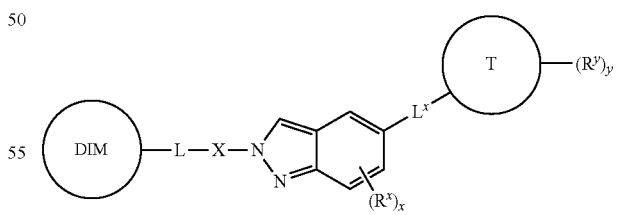

I-d-1 or a pharmaceutically acceptable salt thereof, wherein each of DIM, L, L$^x$, X, R$^x$, R$^y$, Ring T, x, and y is as defined above and described in embodiments herein, both singly and in combination.

In some embodiments, the present invention provides a compound of formula I-a, wherein Ring P and Ring Q form a 6-azaindazole ring as shown, to provide a compound of formula I-d-2:

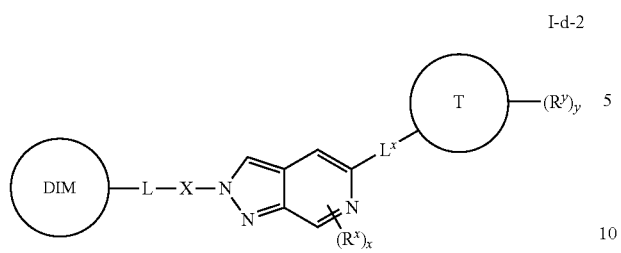

I-d-2

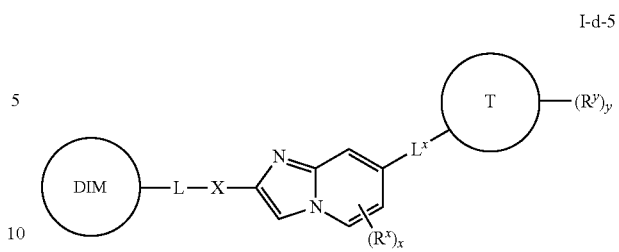

I-d-5 or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form an indazole ring as shown, to provide a compound of formula I-d-3:

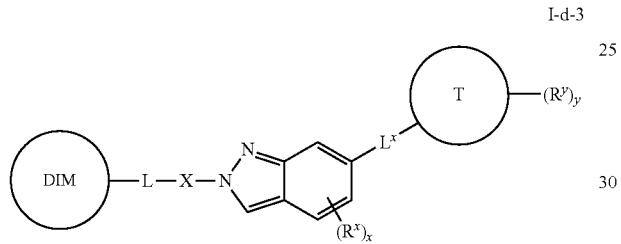

I-d-3 or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form a pyrazolopyridine ring as shown, to provide a compound of formula I-d-4:

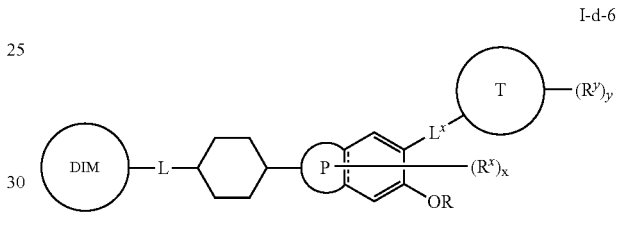

I-d-4 or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring P and Ring Q form an imidazo[1,2-a]pyridine ring as shown, to provide a compound of formula I-d-5:

or a pharmaceutically acceptable salt thereof, wherein each of DIM, L, $L^x$, X, $R^x$, $R^y$, Ring T, x, and y is as defined above and described in embodiments herein, both singly and in combination.

In some embodiments, the present invention provides a compound of formula I-a, wherein Ring Q is benzo, a single $R^x$ is —OR, and X is cyclohexyl as shown, to provide a compound of formula I-d-6:

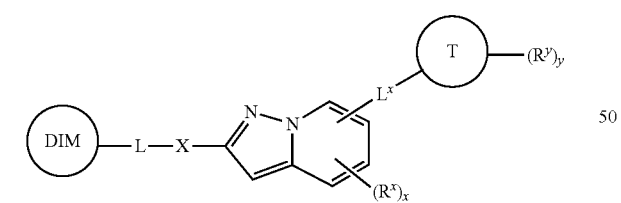

I-d-6 or a pharmaceutically acceptable salt thereof, wherein each of DIM, L, $L^x$, $R^x$, $R^y$, Ring P, Ring T, x, and y is as defined above and described in embodiments herein, both singly and in combination.

In some embodiments, the present invention provides a compound of formula I-a, wherein Ring P and Ring Q form an indazole ring, a single $R^x$ is —OR, and X is cyclohexyl as shown, to provide a compound of formula I-d-7:

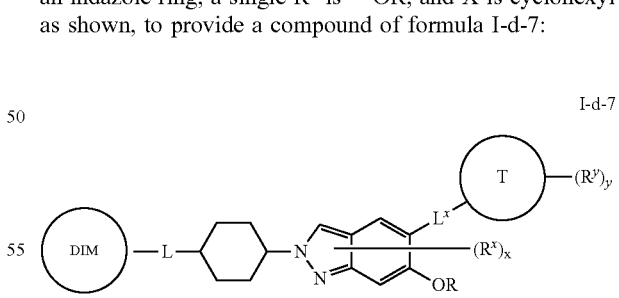

I-d-7 or a pharmaceutically acceptable salt thereof, wherein each of DIM, L, $L^x$, $R^x$, $R^y$, Ring T, x, and y is as defined above and described in embodiments herein, both singly and in combination.

In some embodiments, IRAK is
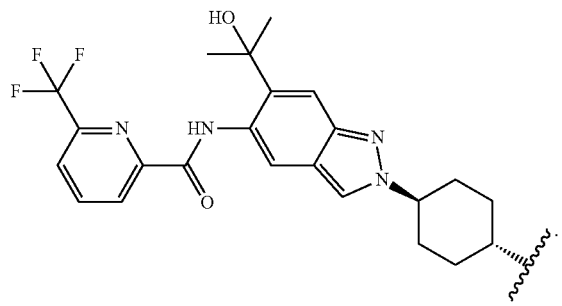 [SMILES: *[C@H]1CC[C@H](n2cc3cc(NC(=O)c4cccc(C(F)(F)F)n4)c(C(C)(C)O)cc3n2)CC1]
In some embodiments, IRAK is
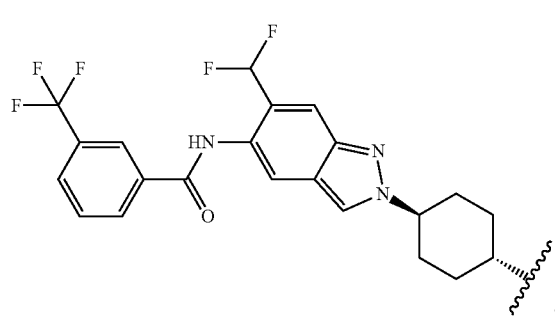 [SMILES: *[C@H]1CC[C@H](n2cc3cc(NC(=O)c4cccc(C(F)(F)F)c4)c(C(F)F)cc3n2)CC1]
In some embodiments, IRAK is
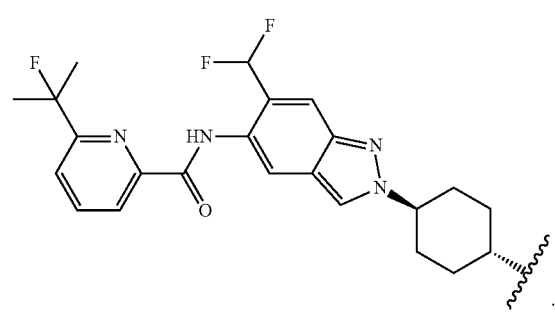 [SMILES: *[C@H]1CC[C@H](n2cc3cc(NC(=O)c4cccc(C(C)(C)F)n4)c(C(F)F)cc3n2)CC1]
In some embodiments, IRAK is
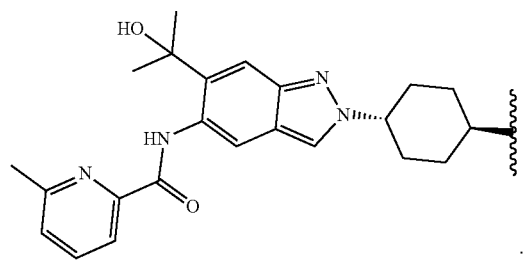 [SMILES: *[C@H]1CC[C@H](n2cc3cc(NC(=O)c4cccc(C)n4)c(C(C)(C)O)cc3n2)CC1]
In some embodiments, IRAK is
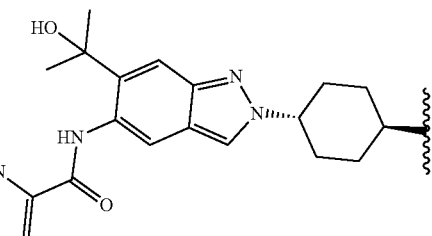
In some embodiments, IRAK is
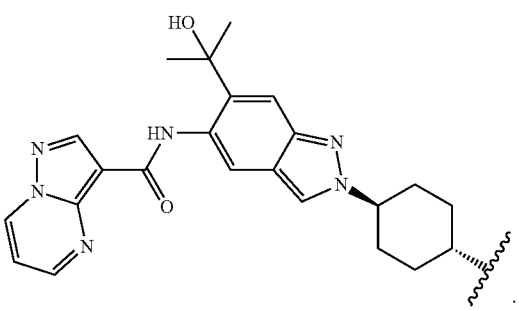 [SMILES: *[C@H]1CC[C@H](n2cc3cc(NC(=O)c4cnn5cccnc45)c(C(C)(C)O)cc3n2)CC1]
In some embodiments, IRAK is
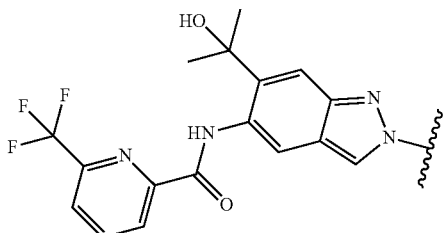
In some embodiments, IRAK is
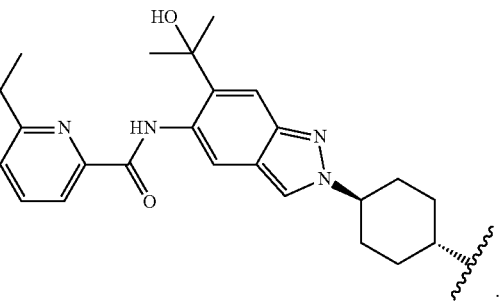

In some embodiments, IRAK is
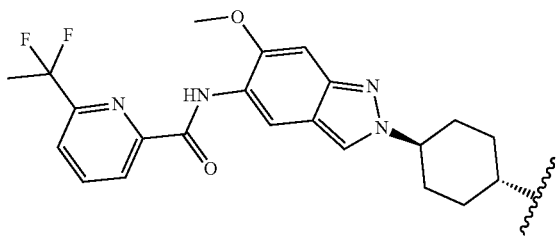
In some embodiments, IRAK is
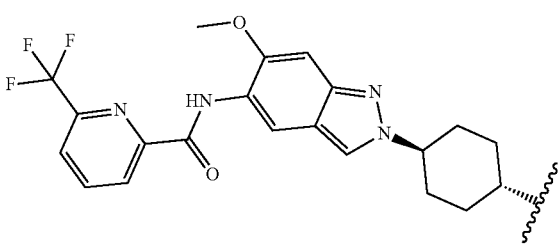
In some embodiments, IRAK is
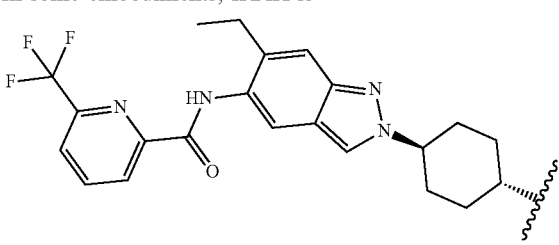
In some embodiments, IRAK is
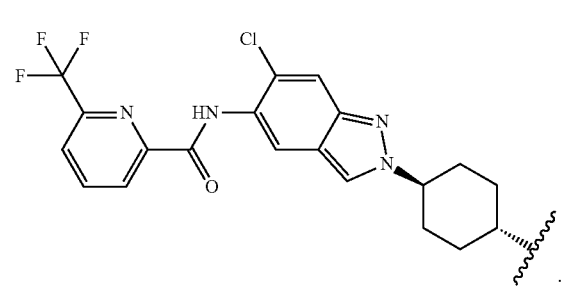
In some embodiments, IRAK is
In some embodiments, IRAK is
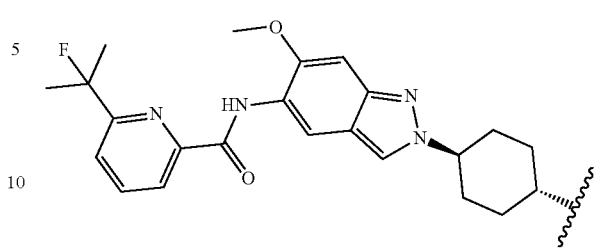
In some embodiments, IRAK is
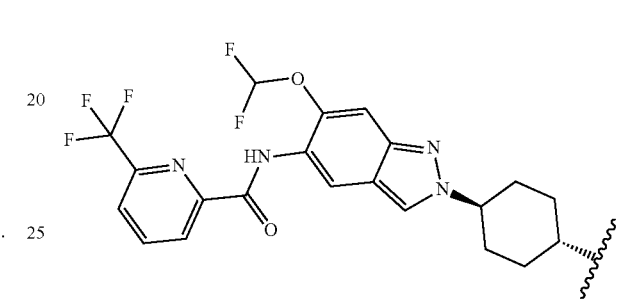
In some embodiments, IRAK is
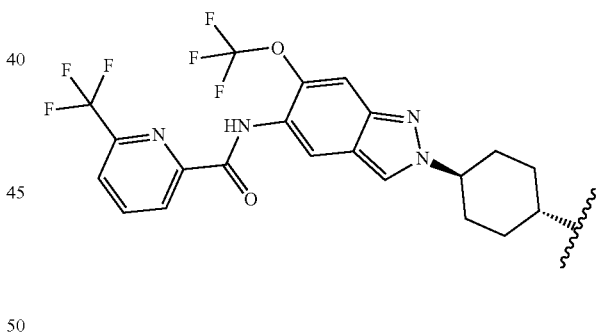
In some embodiments, IRAK is
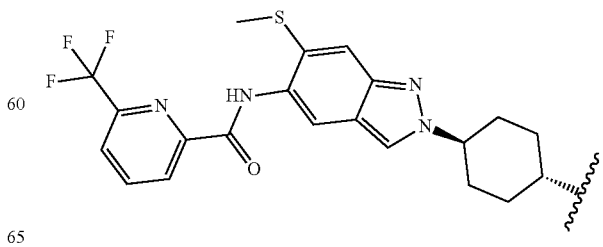

In some embodiments, IRAK is
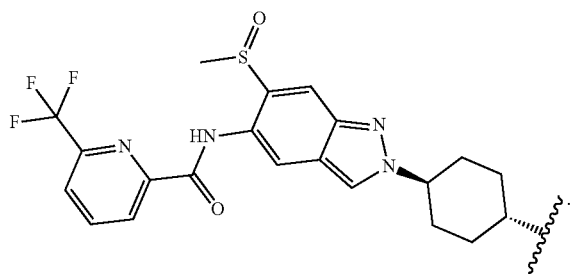 [SMILES: *[C@H]1CC[C@H](n2cc3cc(NC(=O)c4cccc(C(F)(F)F)n4)c(S(C)=O)cc3n2)CC1]
In some embodiments, IRAK is
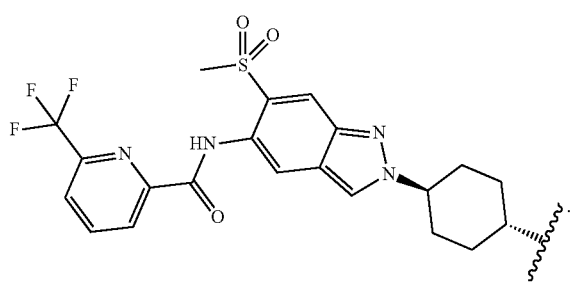 [SMILES: *[C@H]1CC[C@H](n2cc3cc(NC(=O)c4cccc(C(F)(F)F)n4)c(S(C)(=O)=O)cc3n2)CC1]
In some embodiments, IRAK is
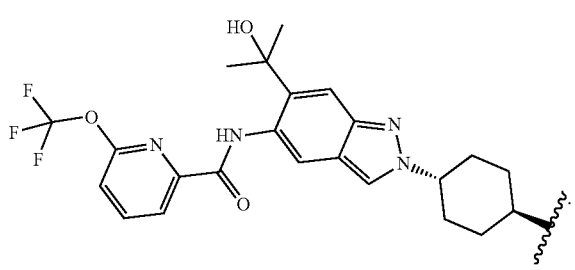
In some embodiments, IRAK is
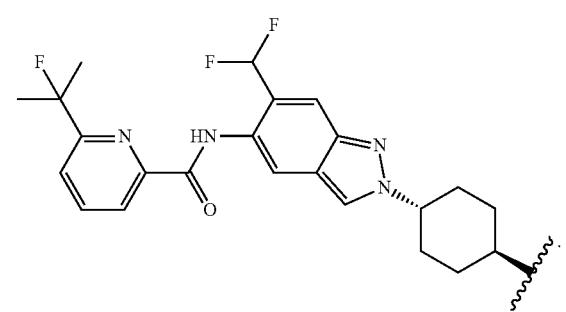 [SMILES: *[C@H]1CC[C@H](n2cc3cc(NC(=O)c4cccc(C(C)(C)F)n4)c(C(F)F)cc3n2)CC1]
In some embodiments, IRAK is
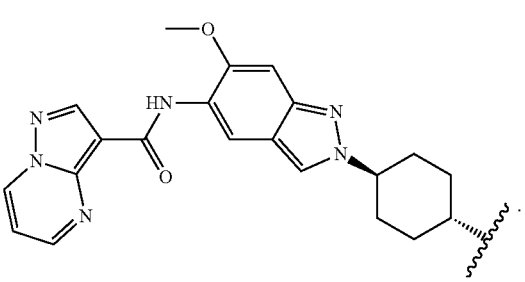 [SMILES: *[C@H]1CC[C@H](n2cc3cc(NC(=O)c4cnn5cccnc45)c(OC)cc3n2)CC1]
In some embodiments, IRAK is
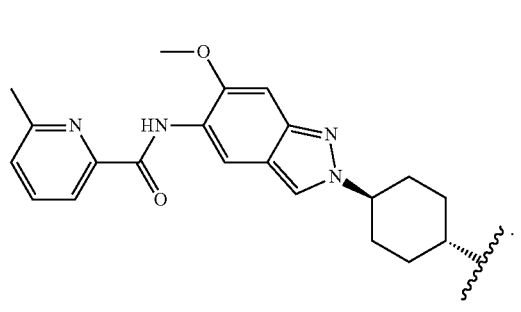 [SMILES: *[C@H]1CC[C@H](n2cc3cc(NC(=O)c4cccc(C)n4)c(OC)cc3n2)CC1]
In some embodiments, IRAK is In some embodiments, IRAK is
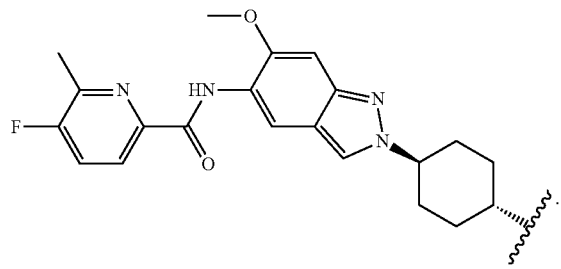 [SMILES: *[C@H]1CC[C@H](n2cc3cc(NC(=O)c4ccc(F)c(C)n4)c(OC)cc3n2)CC1]
In some embodiments, IRAK is
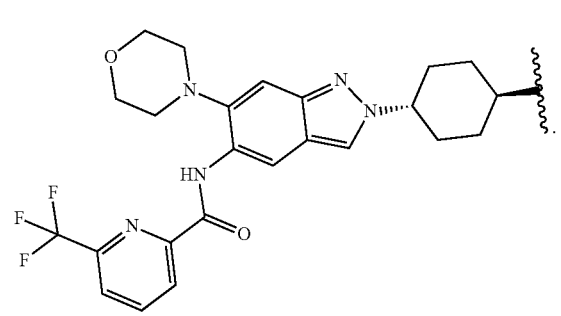 [SMILES: *[C@H]1CC[C@H](n2cc3cc(NC(=O)c4cccc(C(F)(F)F)n4)c(N4CCOCC4)cc3n2)CC1]
In some embodiments, IRAK is
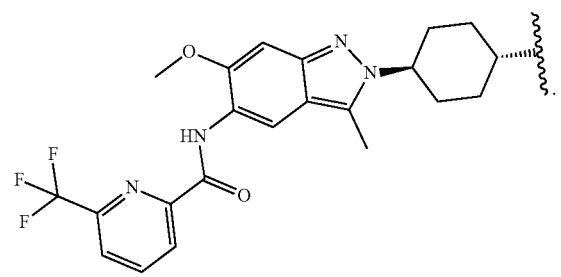 [SMILES: *[C@H]1CC[C@H](n2nc3cc(OC)c(NC(=O)c4cccc(C(F)(F)F)n4)cc3c2C)CC1]
In some embodiments, IRAK is
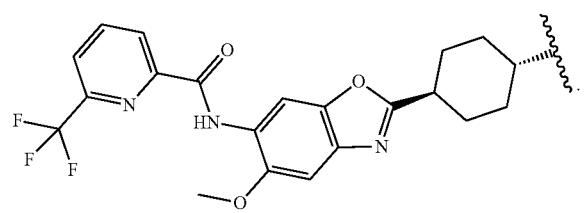 [SMILES: *[C@H]1CC[C@H](c2nc3cc(OC)c(NC(=O)c4cccc(C(F)(F)F)n4)cc3o2)CC1]
In some embodiments, IRAK is
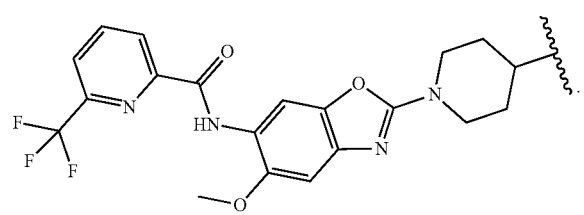 [SMILES: *C1CCN(c2nc3cc(OC)c(NC(=O)c4cccc(C(F)(F)F)n4)cc3o2)CC1]
In some embodiments, IRAK is
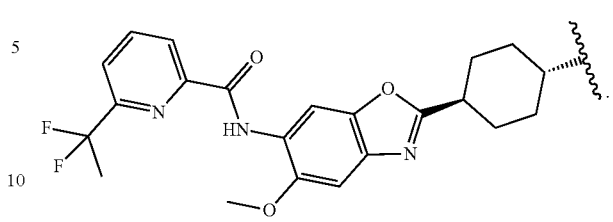
In some embodiments, IRAK is
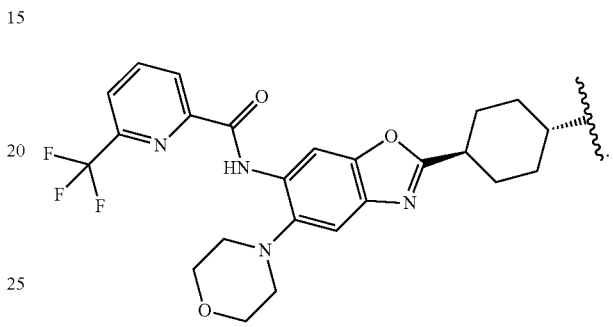
In some embodiments, IRAK is
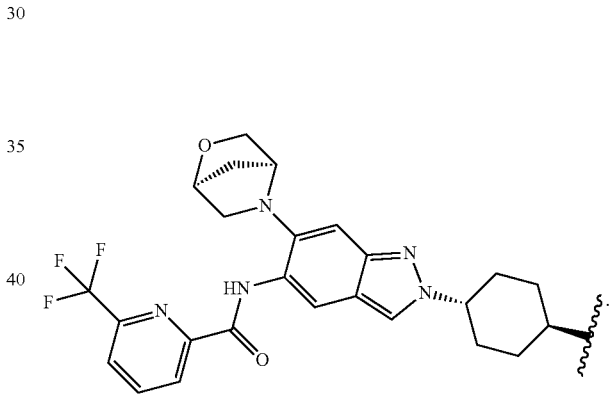
In some embodiments, IRAK is
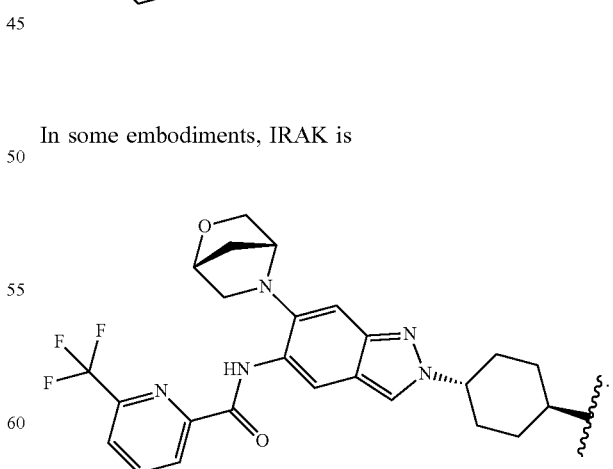

In some embodiments, IRAK is
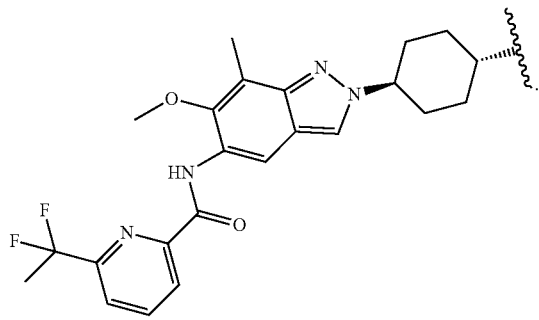 [SMILES: *[C@H]1CC[C@H](n2cc3cc(NC(=O)c4cccc(C(C)(F)F)n4)c(OC)c(C)c3n2)CC1]
In some embodiments, IRAK is
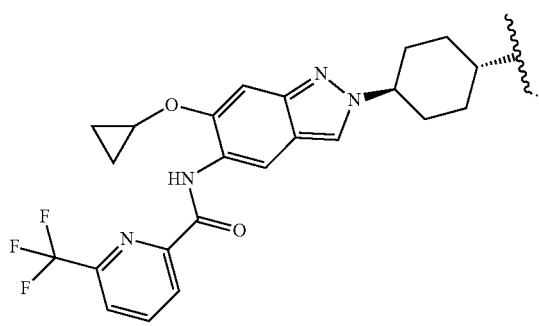 [SMILES: *[C@H]1CC[C@H](n2cc3cc(NC(=O)c4cccc(C(C)(F)F)n4)c(OC4CC4)cc3n2)CC1]
In some embodiments, IRAK is
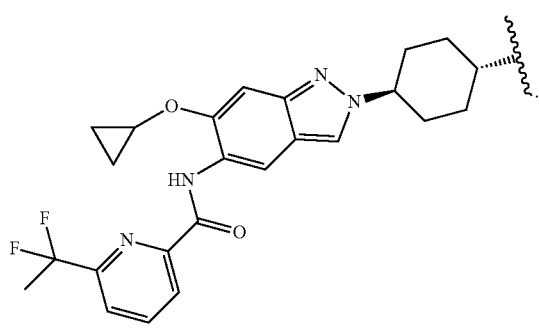
In some embodiments, IRAK is
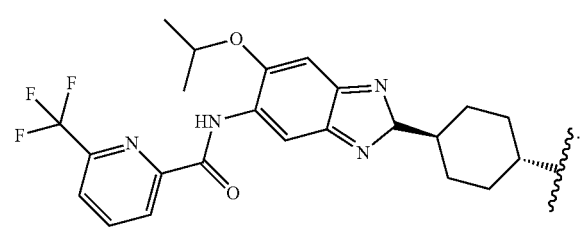 [SMILES: *[C@H]1CC[C@H](C2N=c3cc(NC(=O)c4cccc(C(F)(F)F)n4)c(OC(C)C)cc3=N2)CC1]
In some embodiments, IRAK is
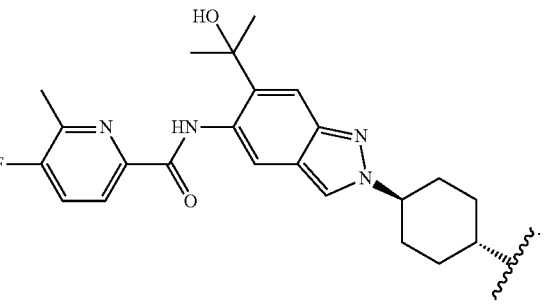
In some embodiments, IRAK is
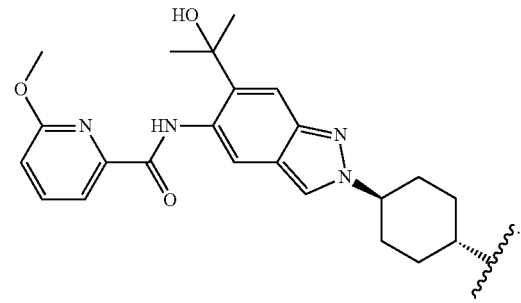 [SMILES: *[C@H]1CC[C@H](n2cc3cc(NC(=O)c4cccc(OC)n4)c(C(C)(C)O)cc3n2)CC1]
In some embodiments, IRAK is
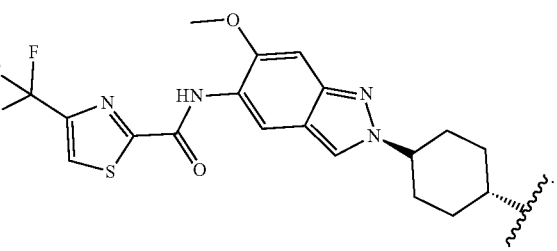
In some embodiments, IRAK is
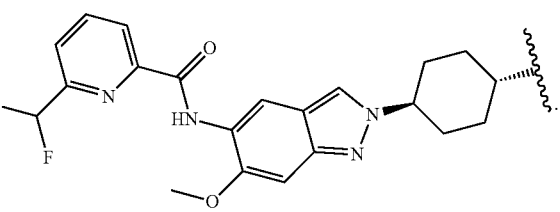

In some embodiments, IRAK is
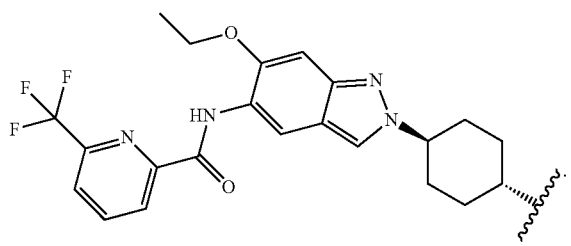 [SMILES: *[C@H]1CC[C@H](n2cc3cc(NC(=O)c4cccc(C(F)(F)F)n4)c(OCC)cc3n2)CC1]
In some embodiments, IRAK is
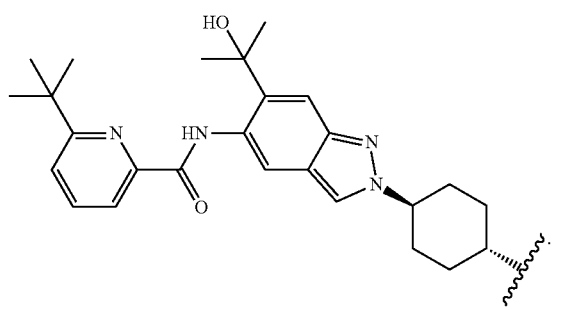 [SMILES: *[C@H]1CC[C@H](n2cc3cc(NC(=O)c4cccc(C(C)(C)C)n4)c(C(C)(C)O)cc3n2)CC1]
In some embodiments, IRAK is
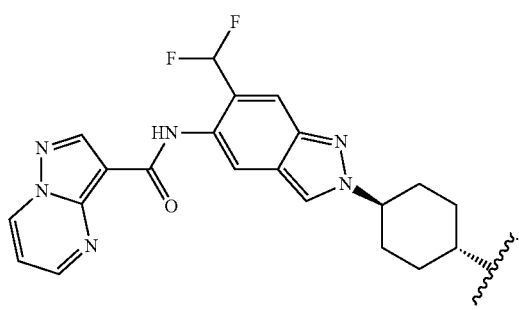 [SMILES: *[C@H]1CC[C@H](n2cc3cc(NC(=O)c4cnn5cccnc45)c(C(F)F)cc3n2)CC1]
In some embodiments, IRAK is
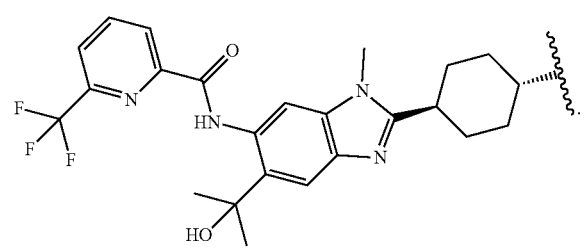 [SMILES: *[C@H]1CC[C@H](c2nc3cc(C(C)(C)O)c(NC(=O)c4cccc(C(F)(F)F)n4)cc3n2C)CC1]
In some embodiments, IRAK is
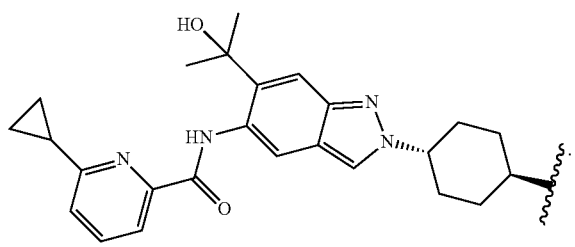 [SMILES: *[C@H]1CC[C@H](n2cc3cc(NC(=O)c4cccc(C5CC5)n4)c(C(C)(C)O)cc3n2)CC1]
In some embodiments, IRAK is
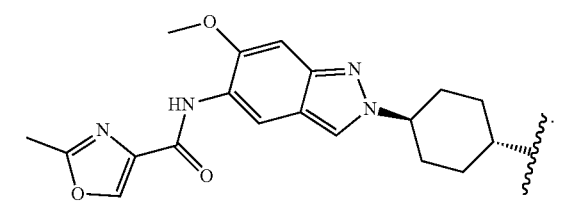 [SMILES: *[C@H]1CC[C@H](n2cc3cc(NC(=O)c4coc(C)n4)c(OC)cc3n2)CC1]
In some embodiments, IRAK is
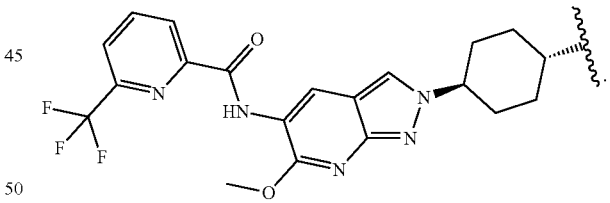
In some embodiments, IRAK is
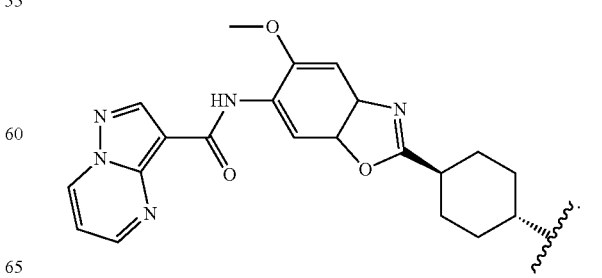

In some embodiments, IRAK is
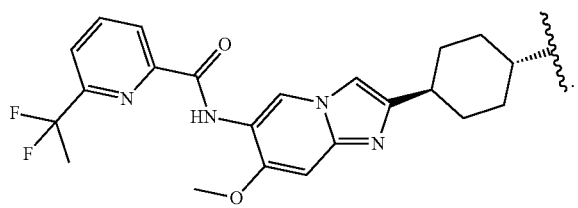 [SMILES: *[C@H]1CC[C@H](c2cn3cc(NC(=O)c4cccc(C(C)(F)F)n4)c(OC)cc3n2)CC1]
In some embodiments, IRAK is
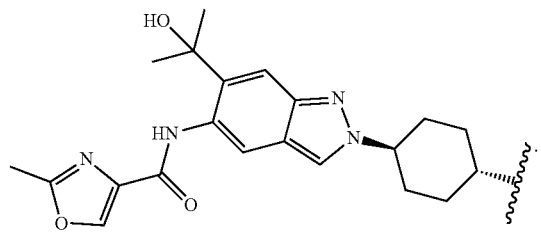 [SMILES: *[C@H]1CC[C@H](n2cc3cc(NC(=O)c4coc(C)n4)c(C(C)(C)O)cc3n2)CC1]
In some embodiments, IRAK is
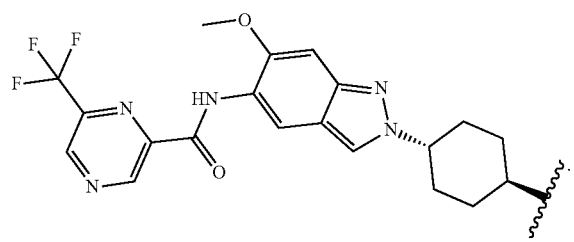 [SMILES: *[C@H]1CC[C@H](n2cc3cc(NC(=O)c4cncc(C(F)(F)F)n4)c(OC)cc3n2)CC1]
In some embodiments, IRAK is
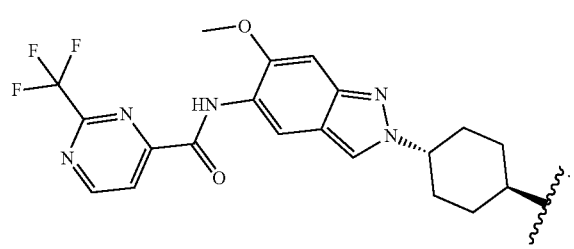 [SMILES: *[C@H]1CC[C@H](n2cc3cc(NC(=O)c4ccnc(C(F)(F)F)n4)c(OC)cc3n2)CC1]
In some embodiments, IRAK is
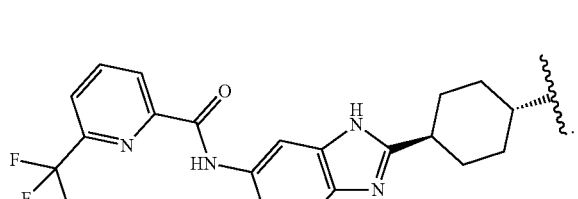
In some embodiments, IRAK is
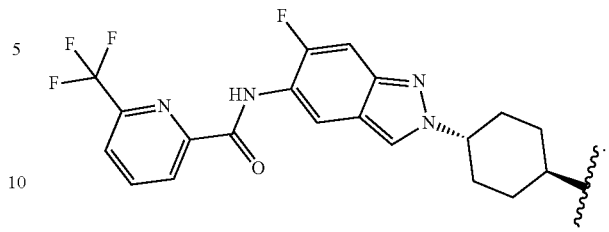
In some embodiments, IRAK is
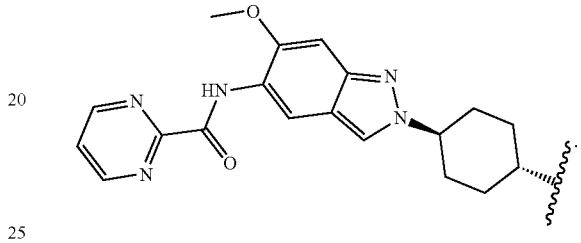
In some embodiments, IRAK is
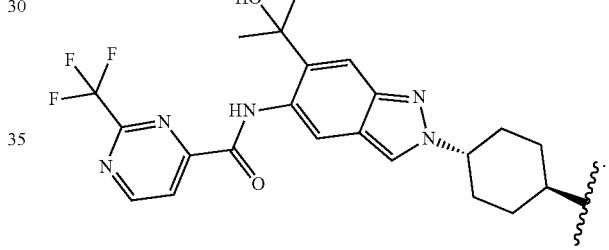
In some embodiments, IRAK is
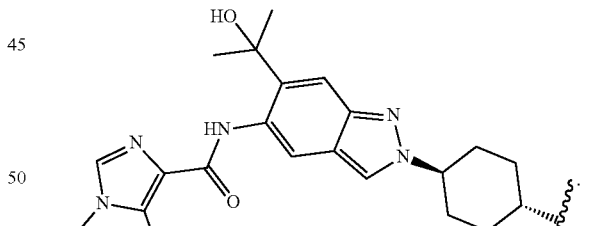
In some embodiments, IRAK is
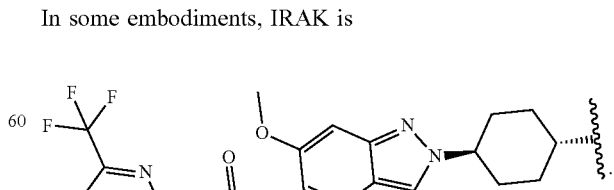

In some embodiments, IRAK is
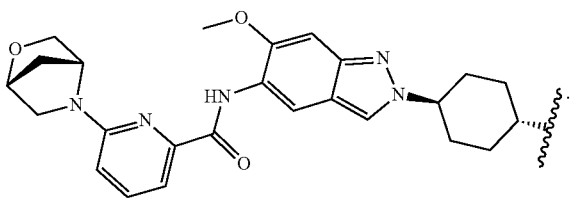 [SMILES: *[C@H]1CC[C@H](n2cc3cc(NC(=O)c4cccc(N5C[C@H]6C[C@@H]5CO6)n4)c(OC)cc3n2)CC1]
In some embodiments, IRAK is
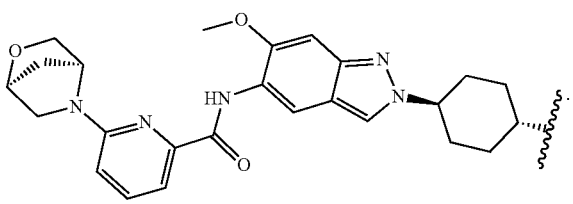 [SMILES: *[C@H]1CC[C@H](n2cc3cc(NC(=O)c4cccc(N5C[C@@H]6C[C@H]5CO6)n4)c(OC)cc3n2)CC1]
In some embodiments, IRAK is
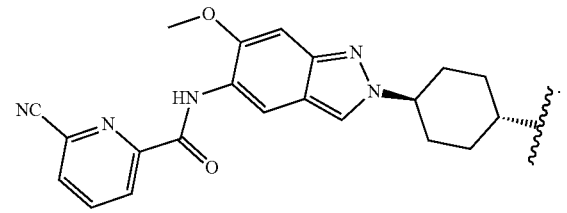 [SMILES: *[C@H]1CC[C@H](n2cc3cc(NC(=O)c4cccc(C#N)n4)c(OC)cc3n2)CC1]
In some embodiments, IRAK is
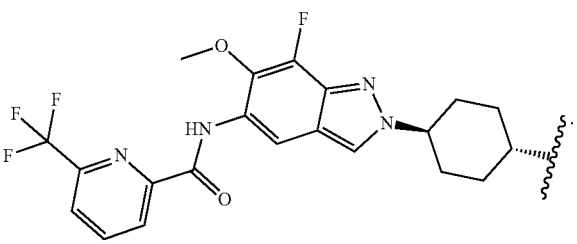 [SMILES: *[C@H]1CC[C@H](n2cc3cc(NC(=O)c4cccc(C(F)(F)F)n4)c(OC)c(F)c3n2)CC1]
In some embodiments, IRAK is
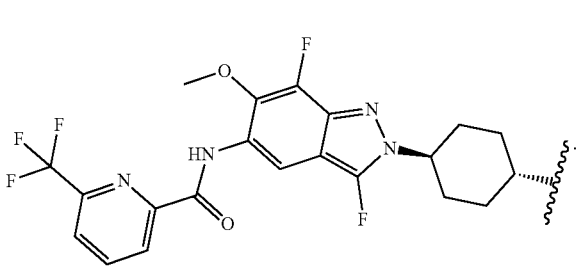 [SMILES: *[C@H]1CC[C@H](n2nc3c(F)c(OC)c(NC(=O)c4cccc(C(F)(F)F)n4)cc3c2F)CC1]
In some embodiments, IRAK is
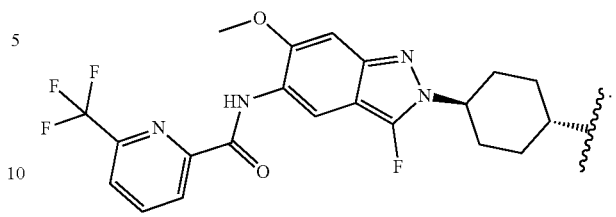
In some embodiments, IRAK is
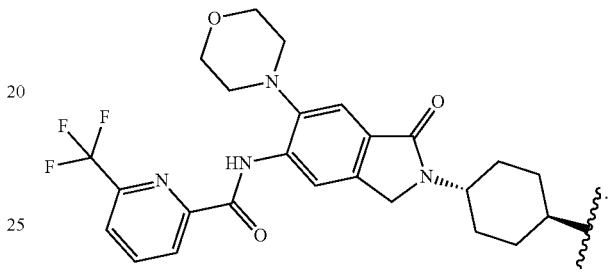
In some embodiments, IRAK is
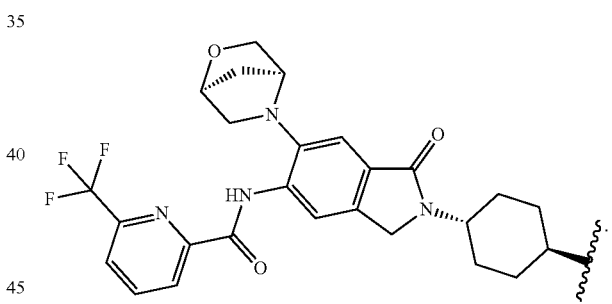
In some embodiments, IRAK is
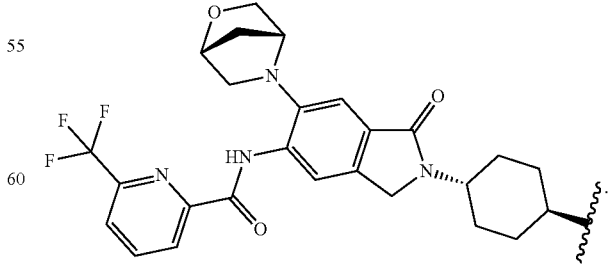

In some embodiments, IRAK is
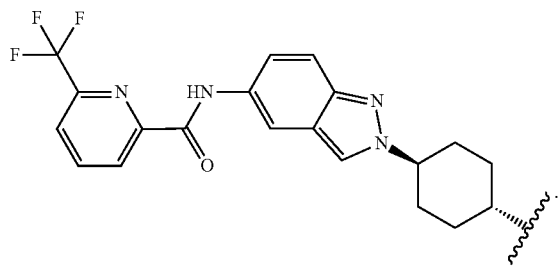 [SMILES: *[C@H]1CC[C@H](n2cc3cc(NC(=O)c4cccc(C(F)(F)F)n4)ccc3n2)CC1]
In some embodiments, IRAK is
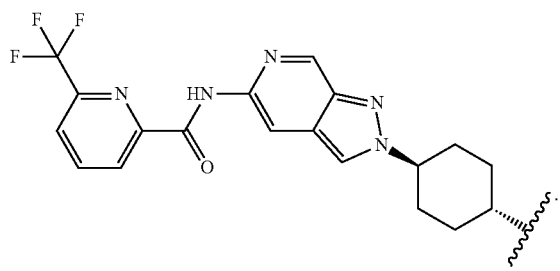 [SMILES: *[C@H]1CC[C@H](n2cc3cc(NC(=O)c4cccc(C(F)(F)F)n4)ncc3n2)CC1]
In some embodiments, IRAK is
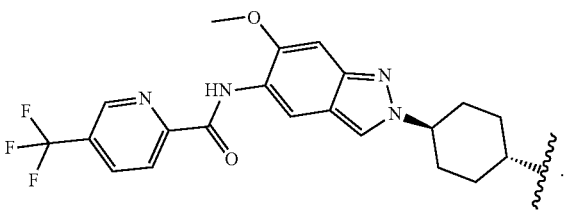 [SMILES: *[C@H]1CC[C@H](n2cc3cc(NC(=O)c4ccc(C(F)(F)F)cn4)c(OC)cc3n2)CC1]
In some embodiments, IRAK is
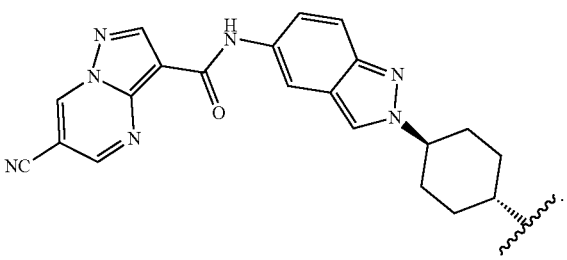 [SMILES: *[C@H]1CC[C@H](n2cc3cc(NC(=O)c4cnn5cc(C#N)cnc45)ccc3n2)CC1]
In some embodiments, IRAK is
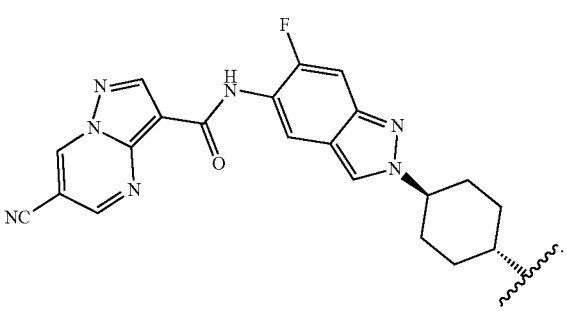 [SMILES: *[C@H]1CC[C@H](n2cc3cc(NC(=O)c4cnn5cc(C#N)cnc45)c(F)cc3n2)CC1]
In some embodiments, IRAK is
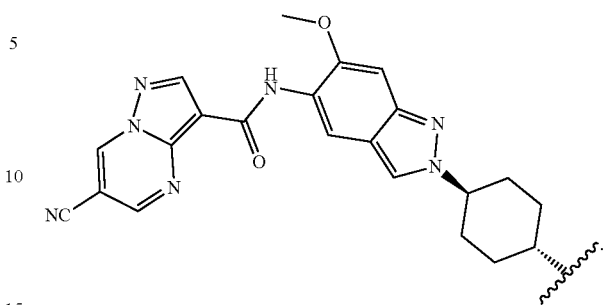
In some embodiments, IRAK is
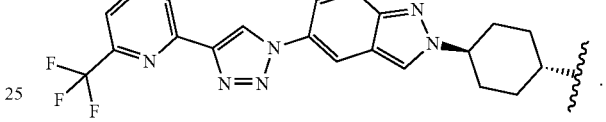
In some embodiments, IRAK is
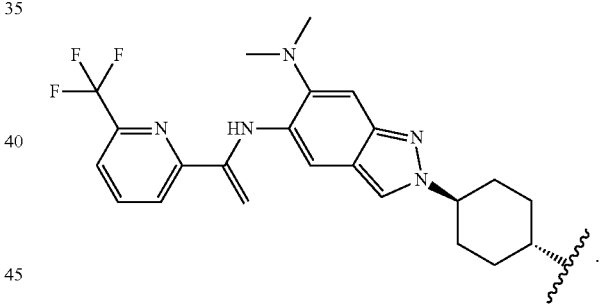
In some embodiments, IRAK is
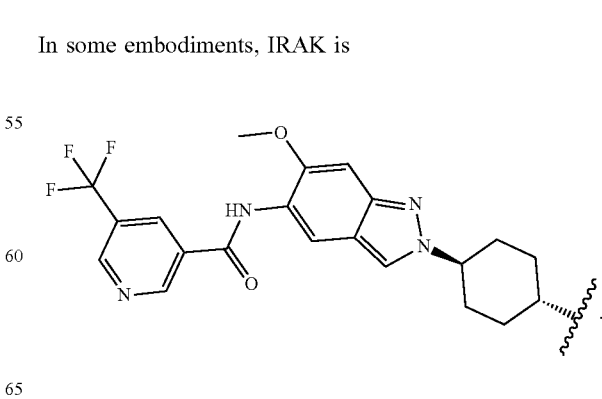

In some embodiments, IRAK is
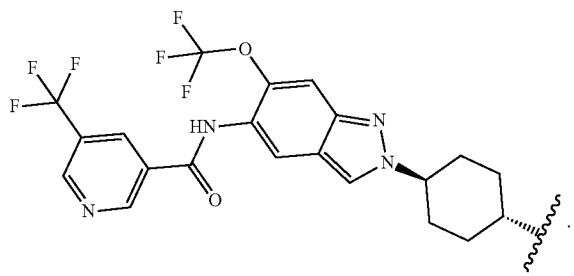 [SMILES: *[C@H]1CC[C@H](n2cc3cc(NC(=O)c4cncc(C(F)(F)F)c4)c(OC(F)(F)F)cc3n2)CC1]
In some embodiments, IRAK is
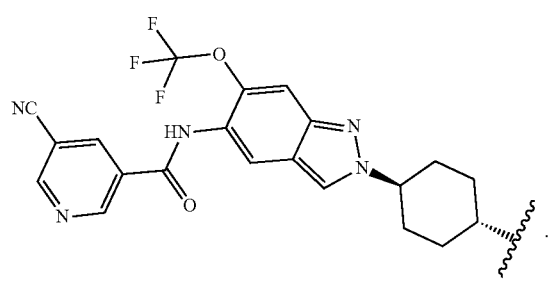 [SMILES: *[C@H]1CC[C@H](n2cc3cc(NC(=O)c4cncc(C#N)c4)c(OC(F)(F)F)cc3n2)CC1]
In some embodiments, IRAK is
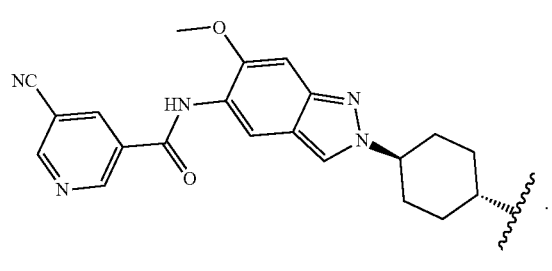 [SMILES: *[C@H]1CC[C@H](n2cc3cc(NC(=O)c4cncc(C#N)c4)c(OC)cc3n2)CC1]
In some embodiments, IRAK is
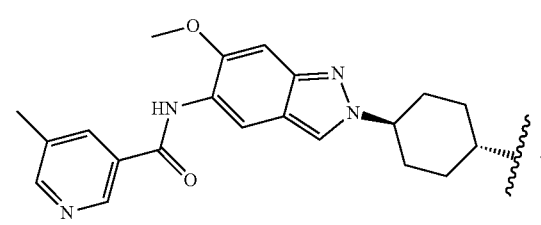 [SMILES: *[C@H]1CC[C@H](n2cc3cc(NC(=O)c4cncc(C)c4)c(OC)cc3n2)CC1]
In some embodiments, IRAK is
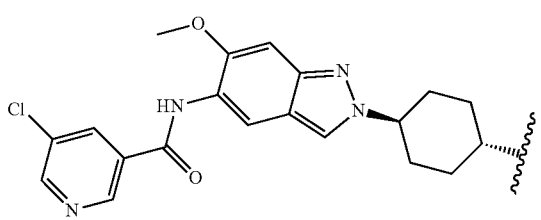
In some embodiments, IRAK is
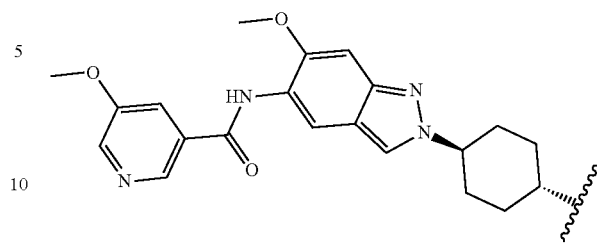
In some embodiments, IRAK is
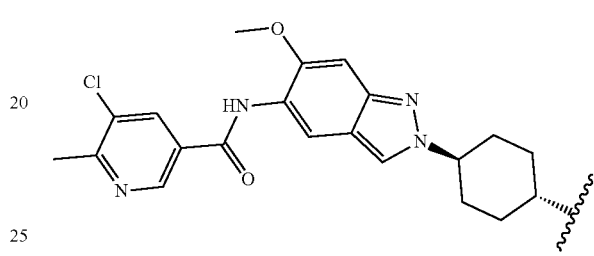
In some embodiments, IRAK is

In some embodiments, IRAK is
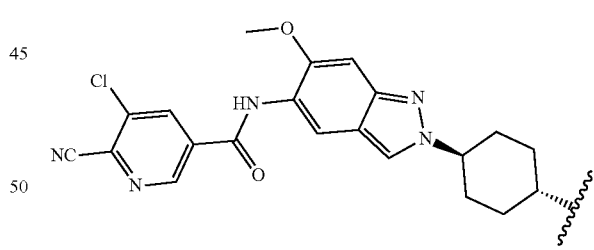
In some embodiments, IRAK is
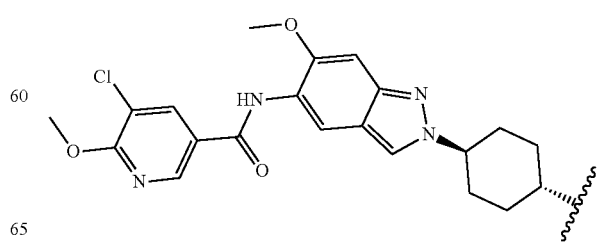

In some embodiments, IRAK is
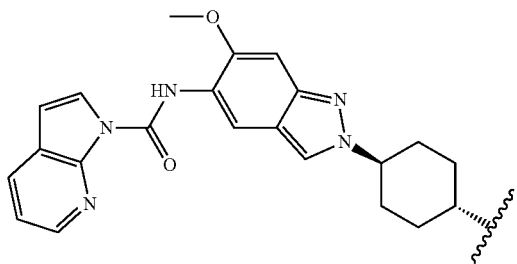
In some embodiments, IRAK is
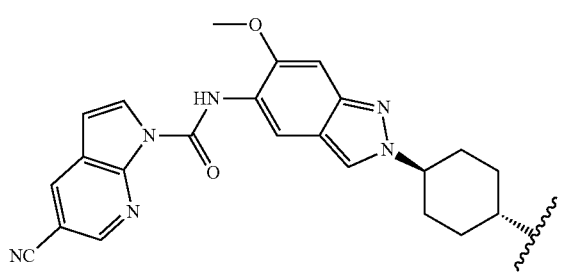
In some embodiments, IRAK is
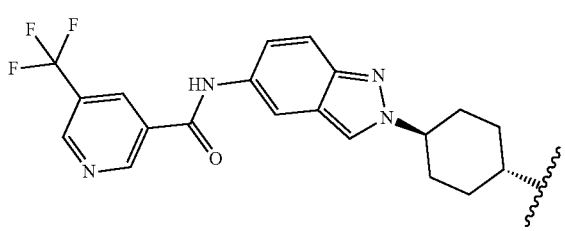 [SMILES: *[C@H]1CC[C@H](n2cc3cc(NC(=O)c4cncc(C(F)(F)F)c4)ccc3n2)CC1]
In some embodiments, IRAK is
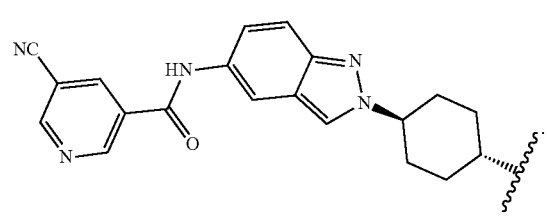 [SMILES: *[C@H]1CC[C@H](n2cc3cc(NC(=O)c4cncc(C#N)c4)ccc3n2)CC1]
In some embodiments, IRAK is
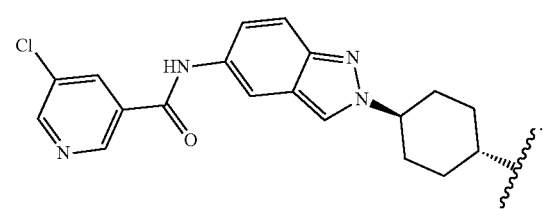 [SMILES: *[C@H]1CC[C@H](n2cc3cc(NC(=O)c4cncc(Cl)c4)ccc3n2)CC1]
In some embodiments, IRAK is
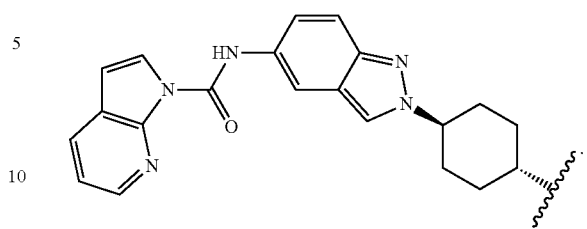
In some embodiments, IRAK is
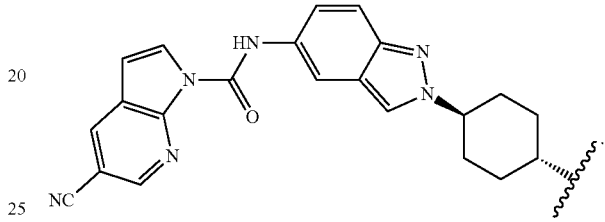
In some embodiments, IRAK is
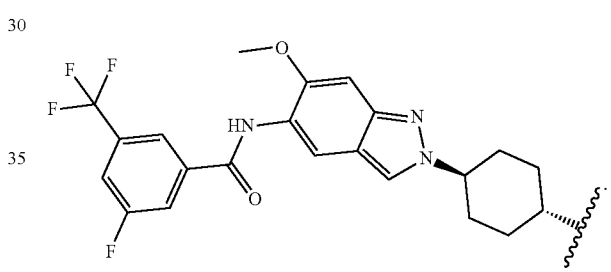
In some embodiments, IRAK is
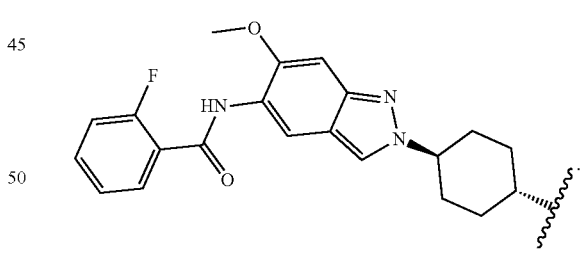
In some embodiments, IRAK is
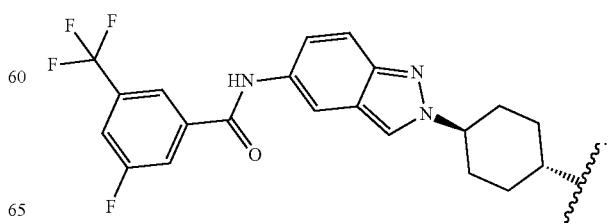

In some embodiments, IRAK is
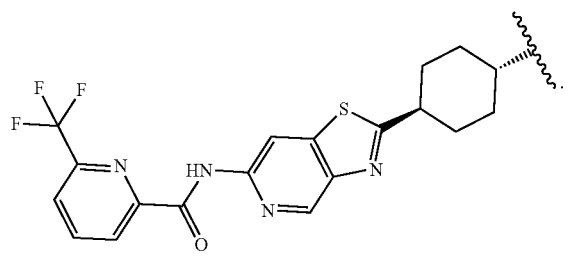 [SMILES: *[C@H]1CC[C@H](c2nc3cnc(NC(=O)c4cccc(C(F)(F)F)n4)cc3s2)CC1]
In some embodiments, IRAK is

In some embodiments, IRAK is
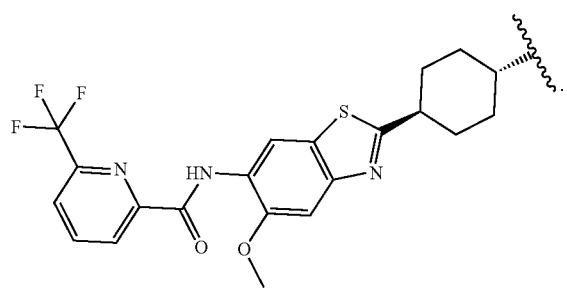 [SMILES: *[C@H]1CC[C@H](c2nc3cc(OC)c(NC(=O)c4cccc(C(F)(F)F)n4)cc3s2)CC1]
In some embodiments, IRAK is
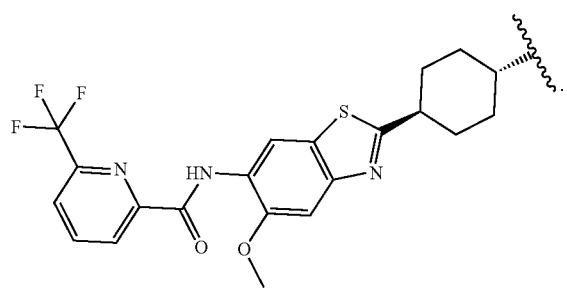 [SMILES: *[C@H]1CC[C@H](c2nc3cc(OC)c(NC(=O)c4cccc(C(F)(F)F)n4)cc3s2)CC1]
In some embodiments, IRAK is
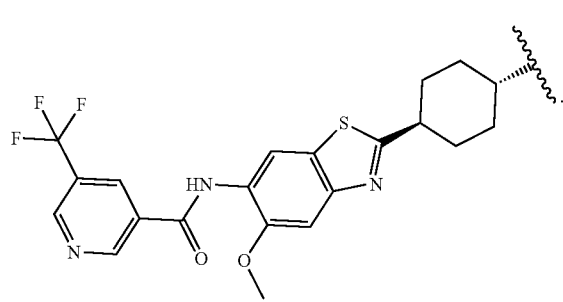 [SMILES: *[C@H]1CC[C@H](c2nc3cc(OC)c(NC(=O)c4cncc(C(F)(F)F)c4)cc3s2)CC1]
In some embodiments, IRAK is
In some embodiments, IRAK is
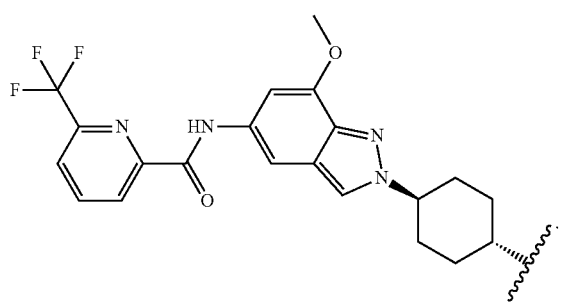 [SMILES: *[C@H]1CC[C@H](n2cc3cc(NC(=O)c4cccc(C(F)(F)F)n4)cc(OC)c3n2)CC1]
In some embodiments, IRAK is
In some embodiments, IRAK is
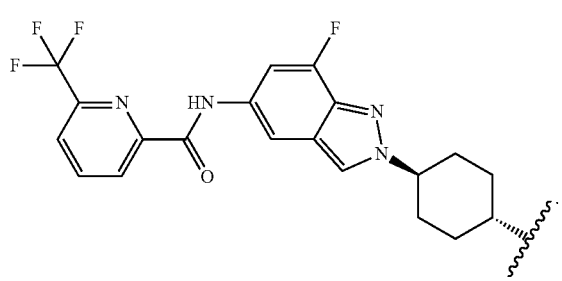 [SMILES: *[C@H]1CC[C@H](n2cc3cc(NC(=O)c4cccc(C(F)(F)F)n4)cc(F)c3n2)CC1]
In some embodiments, IRAK is
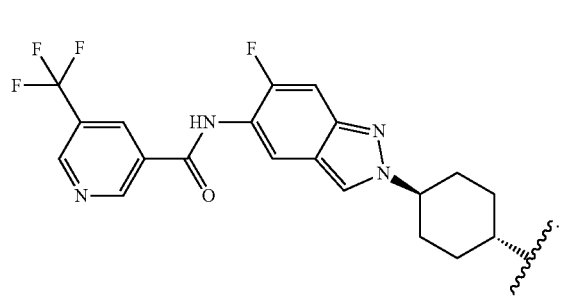 [SMILES: *[C@H]1CC[C@H](n2cc3cc(NC(=O)c4cncc(C(F)(F)F)c4)c(F)cc3n2)CC1]

In some embodiments, IRAK is
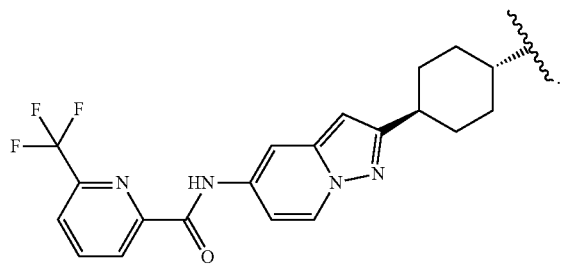 [SMILES: *[C@H]1CC[C@H](c2cc3cc(NC(=O)c4cccc(C(F)(F)F)n4)ccn3n2)CC1]
In some embodiments, IRAK is
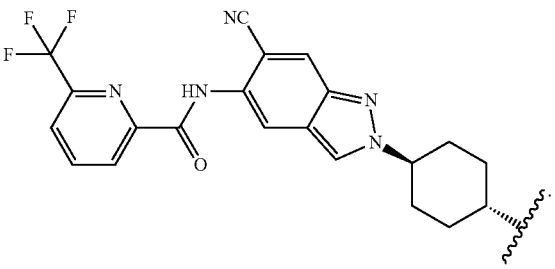
In some embodiments, IRAK is
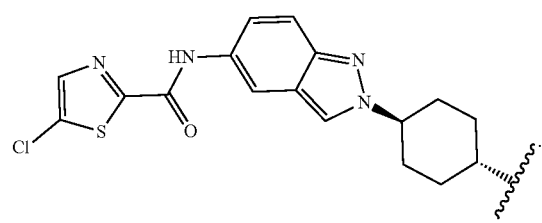 [SMILES: *[C@H]1CC[C@H](n2cc3cc(NC(=O)c4ncc(Cl)s4)ccc3n2)CC1]
In some embodiments, IRAK is
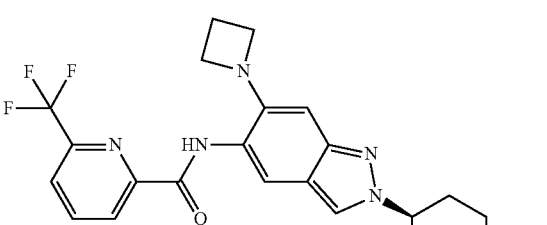
In some embodiments, IRAK is
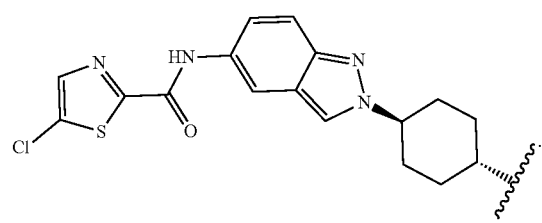
In some embodiments, IRAK is
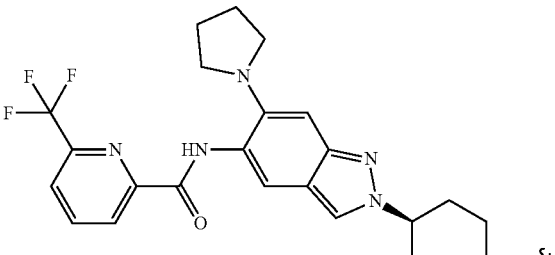
In some embodiments, IRAK is
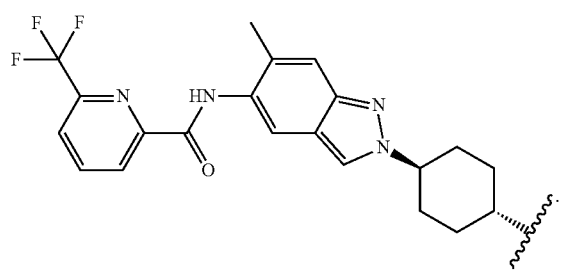 [SMILES: *[C@H]1CC[C@H](n2cc3cc(NC(=O)c4cccc(C(F)(F)F)n4)c(C)cc3n2)CC1]
In some embodiments, IRAK is
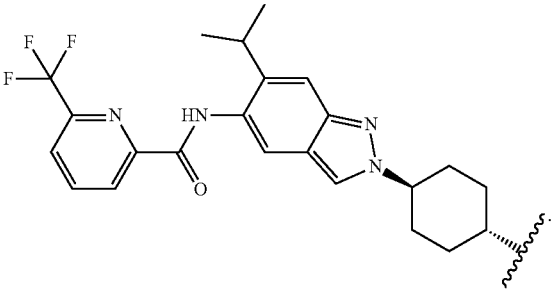
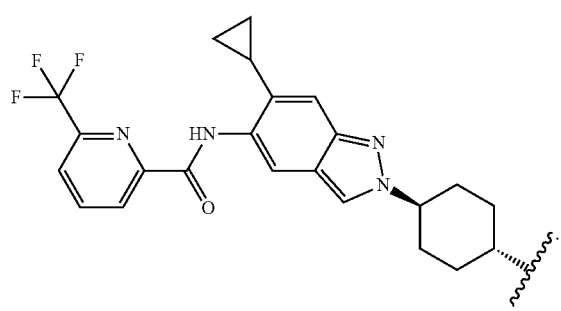 [SMILES: *[C@H]1CC[C@H](n2cc3cc(NC(=O)c4cccc(C(F)(F)F)n4)c(C4CC4)cc3n2)CC1]

In some embodiments, IRAK is
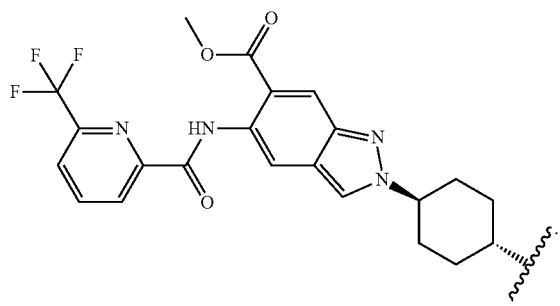 [SMILES: *[C@H]1CC[C@H](n2cc3cc(NC(=O)c4cccc(C(F)(F)F)n4)c(C(=O)OC)cc3n2)CC1]
In some embodiments, IRAK is
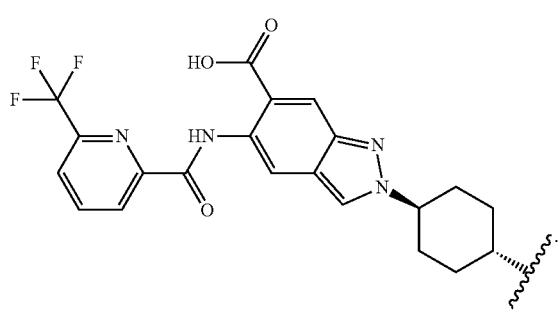 [SMILES: *[C@H]1CC[C@H](n2cc3cc(NC(=O)c4cccc(C(F)(F)F)n4)c(C(=O)O)cc3n2)CC1]
In some embodiments, IRAK is
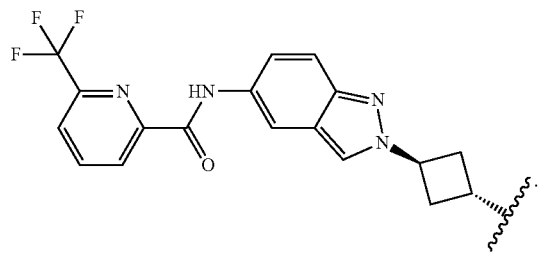 [SMILES: *[C@H]1C[C@H](n2cc3cc(NC(=O)c4cccc(C(F)(F)F)n4)ccc3n2)C1]
In some embodiments, IRAK is
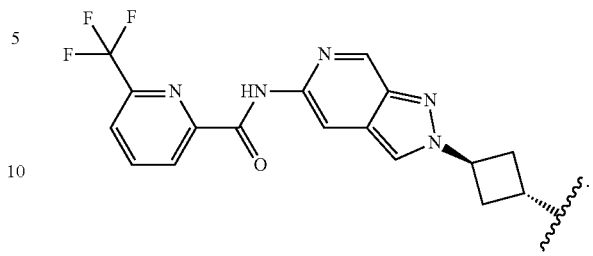
In some embodiments, IRAK is
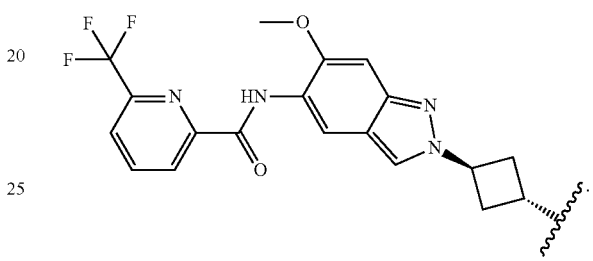
In some embodiments, IRAK is
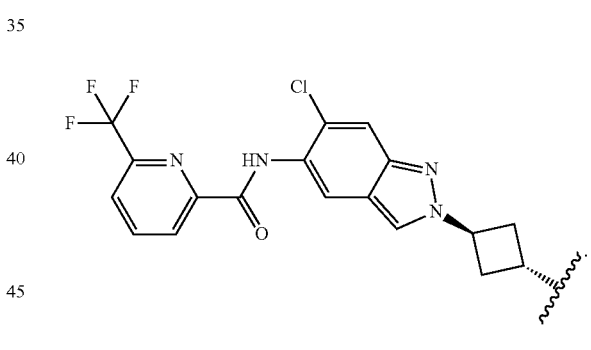
In some embodiments, IRAK is
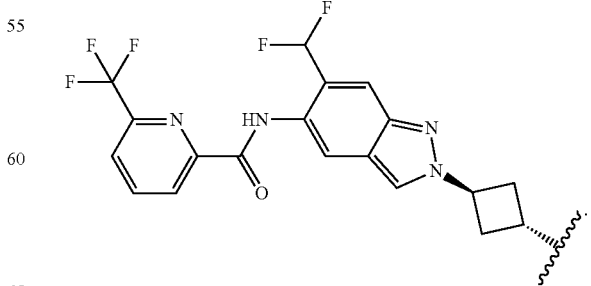

In some embodiments, IRAK is

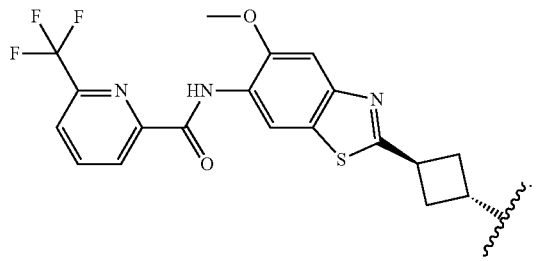 [SMILES: *[C@H]1C[C@H](c2nc3cc(OC)c(NC(=O)c4cccc(C(F)(F)F)n4)cc3s2)C1]

In some embodiments, IRAK is

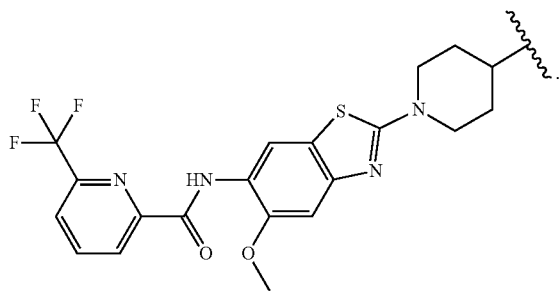 [SMILES: *C1CCN(c2nc3cc(OC)c(NC(=O)c4cccc(C(F)(F)F)n4)cc3s2)CC1]

In some embodiments, IRAK is

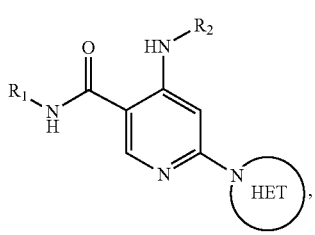

In some embodiments, IRAK is selected from those depicted in Table 1, below.

In some embodiments, the present invention provides a compound of formula I, wherein IRAK is IRAK4 inhibitor

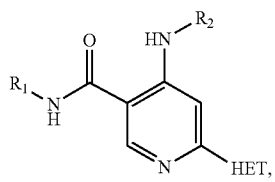

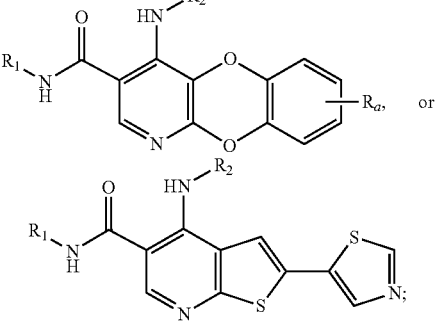

thereby forming a compound of formula I-b, I-b-1, I-b-2, or I-b-3:

I-b

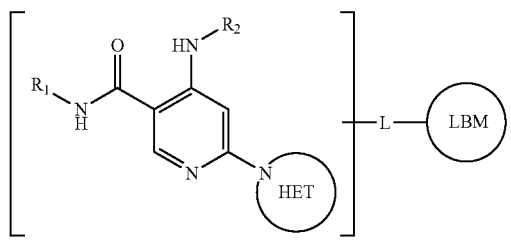

I-b-1

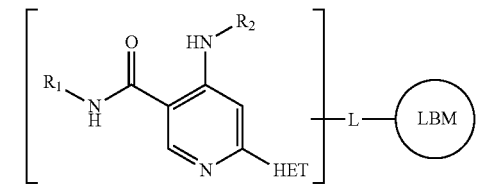

I-b-2

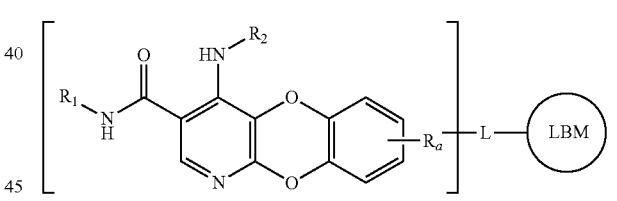

I-b-3

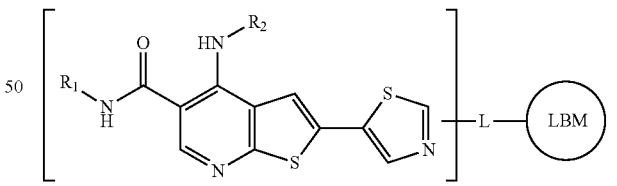

or a pharmaceutically acceptable salt thereof, wherein L and LBM are as defined above and described in embodiments herein, and wherein HET is a heteroaryl selected from pyrazolyl, indolyl, pyrrolo[1,2-b]pyridazine, pyrrolo[2,3-b]pyridinyl, pyrrolo[2,3-d]pyrimidinyl, pyrazolo[3,4-b]pyridinyl, pyrazolo[3,4-d]pyrimidinyl, 2,3-dihydro-1H-pyrrolo[2,3-b]pyridinyl, imidazo[4,5-b]pyridinyl, and purinyl, wherein said heteroaryl is substituted with $R_a$ and $R_b$;

$R_a$ is H, F, Cl, Br, —CN, —OH, $C_{1-4}$ alkyl, $C_{1-4}$ fluoroalkyl, $C_{1-4}$ hydroxyalkyl, $C_{1-4}$ alkoxy, —NH$_2$, —NH($C_{1-4}$ alkyl), —N($C_{1-4}$ alkyl)$_2$, —NH($C_{1-4}$ hydroxyalkyl), —NH($C_{1-4}$ fluoroalkyl), —NH($C_{1-6}$ hydroxy-fluoroalkyl), —C(O)NH$_2$, —CH$_2$NHC(O)($C_{1-6}$ alkyl), —CH$_2$NHC(O)($C_{1-6}$hydroxyalkyl), —CH$_2$NHC(O)NH($C_{1-6}$ alkyl), —CH$_2$NHC(O)NHCH$_2$(phenyl), —CH$_2$NHC(O)N($C_{1-4}$alkyl)$_2$, —CH$_2$NHC(O)O($C_{1-4}$ alkyl), —CH$_2$NHC(O)($C_{3-6}$ cycloalkyl), —CH$_2$NHC(O)(tetrahydrofuranyl), —CH$_2$NHC(O)CH$_2$($C_{3-6}$ cycloalkyl), —CH$_2$NHC(O)CH$_2$(tetrahydropyranyl), —CH$_2$NHC(O)CH$_2$(phenyl), —NHC(O)($C_{1-4}$ alkyl), pyrrolidinyl, hydroxypyrrolidinyl, or pyridazinyl;

$R_b$ is H or —NH$_2$;

$R_1$ is:
(i) $C_{1-6}$ alkyl, $C_{1-6}$ alkyl$C_{3-6}$ cycloalkyl, $C_{1-6}$ fluoroalkyl, $C_{1-6}$ hydroxyalkyl, $C_{1-8}$ hydroxy-fluoroalkyl, —($C_{1-6}$ alkylenyl)O($C_{1-4}$ alkyl), —($C_{1-6}$ alkylenyl)O($C_{1-4}$ fluoroalkyl), —($C_{1-6}$ fluoroalkylenyl)O($C_{1-4}$ alkyl), —($C_{1-6}$ fluoroalkylenyl)O($C_{1-4}$ deuteroalkyl), —($C_{1-6}$ fluoroalkylenyl)O($C_{1-4}$ fluoroalkyl), —($C_{1-4}$ fluoroalkylenyl)C($C_{3-6}$ cycloalkyl)$_2$(OH), —($C_{1-4}$ alkylenyl)NHC(O)($C_{1-4}$ alkylenyl)OC(O)($C_{1-3}$ alkyl), —($C_{1-6}$ alkylenyl)NHS(O)$_2$($C_{1-4}$ alkyl), —($C_{1-6}$ alkylenyl)P(O)($C_{1-4}$ alkoxy)$_2$, —($C_{1-6}$ fluoroalkylenyl)NH($C_{1-4}$ alkyl), —($C_{1-6}$ alkylenyl)C(O)NH($C_{1-4}$ alkyl), —($C_{1-6}$ fluoroalkylenyl)C(O)NH ($C_{1-4}$ alkyl), —($C_{1-6}$fluoroalkylenyl)C(O)NH($C_{1-4}$ hydroxyalkyl), or —($C_{1-6}$ fluoroalkylenyl)OP(O)(OH)$_2$;

(ii) —($C_{1-3}$ alkylenyl)$R_x$, —($C_{1-3}$ fluoroalkylenyl)$R_x$, —($C_{1-3}$alkylenyl)C(O)$R_x$, —($C_{1-3}$ alkylenyl)C(O)NH$R_x$, —($C_{1-3}$fluoroalkylenyl)C(O)$R_x$, or —CH$_2$CF=(tetrahydropyranyl), wherein $R_x$ is a cyclic group selected from $C_{3-6}$ cycloalkyl, tetrazolyl, 1,1-dioxidotetrahydrothiophenyl, 1,1-dioxidothiomorpholinyl, oxadiazolyl, piperidinyl, piperazinyl, pyrrolidinyl, oxetanyl, tetrahydrofuranyl, tetrahydropyranyl, pyridinyl, imidazolyl, morpholinyl, phenyl, and triazinyl, wherein each cyclic group is substituted with zero to 3 substituents independently selected from F, —OH, —CH$_3$, —C(CH$_2$)$_2$OH, —OCH$_3$, —C(O)CH$_2$CN, —S(O)$_2$CH$_3$, —S(O)$_2$NH$_2$, —NHC(O)CH$_3$, —N(S(O)$_2$CH$_3$)$_2$, —CH$_2$CH$_2$(acetamidophenyl), —CH$_2$CH$_2$(methoxyphenyl), —CH$_2$CH$_2$(sulfamoylphenyl), oxetanyl, benzyl, and morpholinyl;

(iii) $C_{3-6}$ cycloalkyl or $C_{4-6}$ cycloalkenyl, each substituted with zero to 3 substituents independently selected from F, —OH, —CN, $C_{1-3}$ alkyl, $C_{1-3}$ alkoxy, —S($C_{1-3}$ alkyl), —NO$_2$, —S(O)$_2$($C_{1-3}$ alkyl), $C_{1-4}$ hydroxyalkyl, —C($C_{1-3}$ alkyl)(OH)($C_{3-6}$ cycloalkyl), —CH$_2$C(O)NH($C_{1-3}$ alkyl), —NHC(O)($C_{1-3}$ alkyl), —NHC(O)($C_{1-4}$hydroxyalkyl), —C(O)NH($C_{1-3}$ alkyl), —C(O)NH($C_{1-3}$ deuteroalkyl), —C(O)NH($C_{3-6}$ cycloalkyl), —NHC(O)O($C_{1-3}$ alkyl), —NHS(O)$_2$($C_{1-3}$alkyl), pyridinyl, imidazolyl, pyrazolyl, methylimidazolyl, methylpyrazolyl, and thiazolyl;

(iv) tetrahydropyranyl, piperidinyl, pyrazolyl, phenyl, pyridinyl, or pyrimidinyl, each substituted with zero to 1 substituent selected from —OH, $C_{1-3}$ alkyl, $C_{1-3}$ fluoroalkyl, $C_{1-4}$ hydroxyalkyl, $C_{1-3}$alkoxy, —C(O)($C_{1-4}$ alkyl), —S(O)$_2$($C_{1-4}$ alkyl), —S(O)$_2$NH($C_{1-4}$ alkyl), —NH($C_{1-3}$ alkyl), —N($C_{1-3}$ alkyl)$_2$, —O($C_{1-4}$ alkylenyl)N($C_{1-3}$ alkyl)$_2$, —CH$_2$(morpholinyl), azetidinyl, oxetanyl, tetrahydropyranyl, morpholinyl, piperazinyl, piperidinyl, methylpiperazinyl, methoxypiperidinyl, pyridinyl, pyrimidinyl, methylsulfonyl azetidinyl, and —C(O)(methylsulfonyl azetidinyl); or (v) pyrrolo[2,3-c]pyridinyl, bicyclo[2.2.1]heptan-1-ol, tetrahydrobenzo[d]thiazol-2-amine, or 1,3-diazaspiro[4.5]decane-2,4-dione; and $R_2$ is:
(i) $C_{1-7}$ alkyl or $C_{2-6}$ alkenyl, each substituted with zero to three substituents independently selected from F, —OH, and —CN; —($C_{1-4}$ alkylenyl)O($C_{1-4}$ alkyl), —($C_{1-4}$ alkylenyl)O($C_{1-4}$ fluoroalkyl), —($C_{1-6}$ alkylenyl)NH$_2$, —($C_{1-6}$ alkylenyl)S(O)$_2$($C_{1-3}$ alkyl), —($C_{1-6}$fluoroalkylenyl)NH($C_{1-3}$ alkyl), or —($C_{1-6}$ alkylenyl)NHC(O)($C_{1-4}$ fluoroalkyl);

(ii) —($C_{1-4}$ alkylenyl)$R_y$, wherein $R_y$ is $C_{3-6}$ cycloalkyl, azetidinyl, oxetanyl, oxazolyl, pyridinyl, tetrahydropyranyl, or morpholinyl, each substituted with zero to 2 substituents independently selected from F, —OH, and $C_{1-3}$ alkyl;

(iii) $C_{3-6}$ cycloalkyl, azetidinyl, oxetanyl, furanyl, tetrahydrofuranyl, pyrrolidinyl, piperidinyl, or tetrahydropyranyl, each substituted with zero to 3 substituents independently selected from F, —OH, $C_{1-3}$alkyl, $C_{1-3}$ hydroxyalkyl, —C(O)($C_{1-3}$ alkyl), —C(O)($C_{1-3}$ fluoroalkyl), —C(O)($C_{1-3}$ cyanoalkyl), —C(O)O($C_{1-3}$ alkyl), —C(O)NH$_2$, —C(O)NH($C_{1-3}$ alkyl), —C(O)(difluorophenyl), —NH$_2$, —NH($C_{1-3}$ alkyl), —NH($C_{1-3}$ fluoroalkyl), —NH(oxetanyl), —NHC(O)($C_{1-3}$ alkyl), —NHC(O)($C_{1-3}$ fluoroalkyl), —NHC(O)($C_{3-6}$ cycloalkyl), —NHC(O)(fluorophenyl), —S(O)$_2$($C_{1-3}$ alkyl), imidazolyl, phenyl, pyrimidinyl, fluoropyrimidinyl, chloropyrimidinyl, and methoxypyrimidinyl;

(iv) adamantanyl, hydroxyadamantanyl, benzo[d]imidazolyl, benzo[d]oxazolyl, benzo[d]triazolyl, benzothiazolyl, bicyclo[1.1.1]pentanyl, or hydroxy-bicyclo[2.2.1]heptanyl; or (v) phenyl, pyrazolyl, thiazolyl, thiadiazolyl, or indazolyl, each substituted with 0 to 2 substituents independently selected from F, Cl, —OH, —CN, $C_{1-4}$ alkyl, $C_{1-4}$ hydroxyalkyl, $C_{1-4}$ fluoroalkyl, $C_{1-4}$ cyanoalkyl, $C_{1-3}$ alkoxy, $C_{3-6}$ cycloalkyl, —($C_{1-3}$ alkylenyl)O($C_{1-3}$alkyl), —($C_{1-3}$ alkylenyl)O($C_{1-3}$ fluoroalkyl), —C(O)NH$_2$, —C(O)NH($C_{1-3}$ alkyl), —NHC(O)($C_{1-3}$ alkyl), —NHC(O)S(O)$_2$($C_{1-3}$alkyl), —S(O)$_2$NH$_2$, —S(O)$_2$($C_{1-3}$ alkyl), pyrazolyl, methyl pyrazolyl, imidazolyl, triazolyl, methyl tetrazolyl, ethyl tetrazolyl, phenyl, pyrimidinyl, fluoropyrimidinyl, and tetrahydropyranyl;

as defined and described in WO 2015/103453 and US 2015/0191464, the entirety of each of which is herein incorporated by reference.

In certain embodiments, the present invention provides a compound of formula I, wherein IRAK is an IRAK4 inhibitor

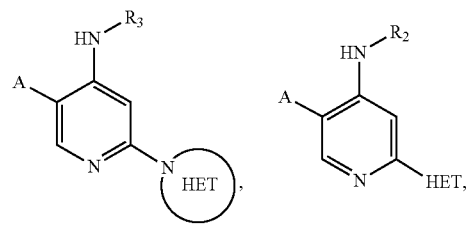

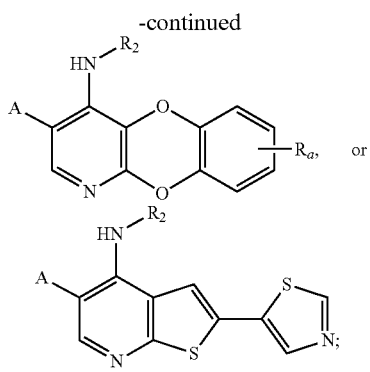

thereby forming a compound of formula I-c, I-c-1, I-c-2, or I-c-3:

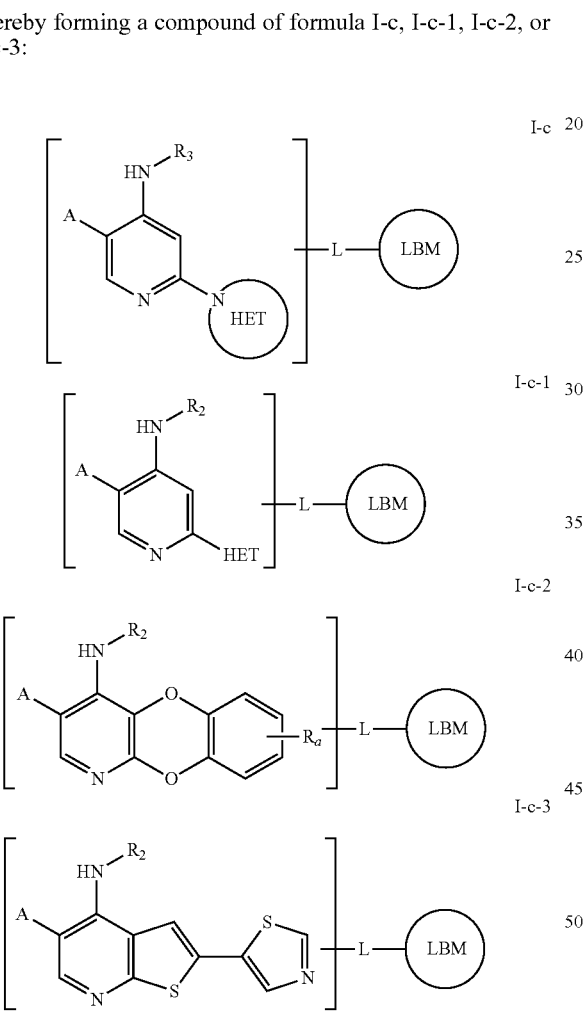

or a pharmaceutically acceptable salt thereof, wherein L and LBM are as defined above and described in embodiments herein, and wherein:

HET is a heteroaryl selected from pyrrolo[2,3-b]pyridinyl, pyrrolo[2,3-d]pyrimidinyl, pyrazolo[3,4-b]pyridinyl, pyrazolo[3,4-d]pyrimidinyl, imidazolo[4,5-b]pyridinyl, and imidazolo[4,5-d]pyrimidinyl, wherein said heteroaryl is attached to the pyridinyl group in the compound of Formula (I) by a nitrogen ring atom in said heteroaryl and wherein said heteroaryl is substituted with zero to 2 $R_b$;

A is pyrazolyl, imidazolyl, triazolyl, isoxazolyl, oxadiazolyl or dihydroisoxazolyl, each substituted with $R_a$;

$R_3$ is $C_{2-3}$ alkyl, $C_{2-3}$ fluoroalkyl, $C_{3-4}$ hydroxyalkyl, or a cyclic group selected from $C_{3-6}$ cycloalkyl, oxetanyl, tetrahydrofuranyl, tetrahydropyranyl, and pyrazolyl, wherein said cyclic group is substituted with zero to 2 substituents independently selected from F, —OH, $C_{1-2}$ alkyl, and —$CH_2CHF_2$;

$R_a$ is:

(i) H, F, $C_l$, —OH, —CN, $C_{1-6}$ alkyl, $C_{1-6}$ fluoroalkyl, $C_{1-4}$ cyanoalkyl, $C_{1-6}$ hydroxyalkyl, $C_{1-5}$ hydroxy-fluoroalkyl, $C_{2-4}$ alkenyl, $C_{1-6}$ aminoalkyl, —$(CH_2)_{1-3}NHR_y$, —$(CH_2)_{1-3}NR_yR_y$, —$CH_2CH(OH)$(phenyl), —$CH(CH_2OH)$(phenyl), —$CH_2CH(OH)$$CH_2$(phenyl), —$CH_2CH(OH)CH_2O$(methoxyphenyl), —$CH_2CH(NH_2)CH_2$(phenyl), —$(CH_2CH_2O)_4H$, —$(CH_2)_{1-3}O(C_{1-3}$ alkyl), —$CH_2CH(OH)$$CH_2O(C_{1-3}$alkyl), —$CH_2C(O)(C_{1-3}$ alkyl), —$CH_2C(O)NR_yR_y$, —$(CH_2)_{1-3}NR_yC(O)(C_{1-3}$ alkyl), —$CH_2C(O)O(C_{1-3}$ alkyl), —$C(O)NH_2$, —$CH_2NR_yC(O)NH_2$, —$(CH_2)_{1-2}NR_yC(O)O(C_{1-2}$ alkyl), —$(CR_yR_y)_{1-5}OC(O)CH_2NR_yR_y$, —$CH_2CH_2S(O)_2CH_3$, —$CH_2S(O)_2$$(C_{1-3}$ alkyl), —$CH_2S(O)_2$(phenyl), or —NH(aminocyclohexyl); or (ii) —$(CH_2)_{0-3}R_z$ or —$(CH_2)_{0-1}C(O)R_z$, wherein $R_z$ is $C_{3-6}$ cycloalkyl, azetidinyl, oxetanyl, tetrahydrofuranyl, tetrahydropyranyl, piperidinyl, piperazinyl, pyrrolyl, pyrrolidinonyl, morpholinyl, pyrrolidinyl, phenyl, pyrazolyl, imidazolyl, pyridinyl, pyrimidinyl, dioxopyrimidinyl, benzo[d]imidazolyl, benzo[d]thiazolyl, 1,3-dioxolanyl, or 8-azabicyclo[3.2.1]octanyl, each substituted with zero to 4 substituents independently from F, —CN, —OH, —$NR_yR_y$, $C_{1-3}$ alkyl, $C_{1-3}$ fluoroalkyl, $C_{1-3}$ hydroxyalkyl, —$CH$(phenyl)$_2$, —$O(C_{1-4}$ alkyl), —$C(O)(C_{1-4}$ alkyl), —$C(O)(C_{1-4}$ deuteroalkyl), —$C(O)(C_{1-5}$ hydroxyalkyl), —$C(O)(C_{1-3}$ fluoroalkyl), —$C(O)(C_{3-6}$cycloalkyl), —$C(O)O(C_{1-3}$ alkyl), —$C(O)NR_yR_y$, —$C(O)$(phenyl), —$C(O)$(pyridinyl), —$C(O)CH_2(C_{3-6}$ cycloalkyl), —$C(O)O(C_{1-4}$ alkyl), —NH$(C_{1-4}$ alkyl), —NH$(C_{1-3}$ fluoroalkyl), —NHC(O)CH$_3$, —NHC(O)O$(C_{1-3}$alkyl), —NHC(O)OC(CH$_3$)$_3$, —S(O)$_2$$(C_{1-3}$alkyl), —OS(O)$_2$$(C_{1-3}$ alkyl), methyl oxadiazolyl, and pyrimidinyl;

each $R_b$ is independently selected from H, Cl, —CN, —$NH_2$, and —$C(O)NH_2$, wherein said heteroaryl is attached to the pyridinyl group by a nitrogen atom in said heteroaryl; and each $R_y$ is independently H or $C_{1-2}$ alkyl;

as defined and described in WO 2016/210034 and US 2018/0186799, the entirety of each of which is herein incorporated by reference.

In some embodiments, IRAK is

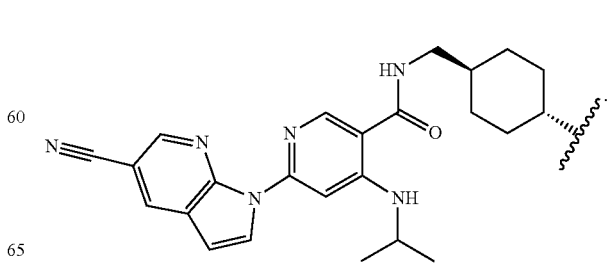

In some embodiments, IRAK is
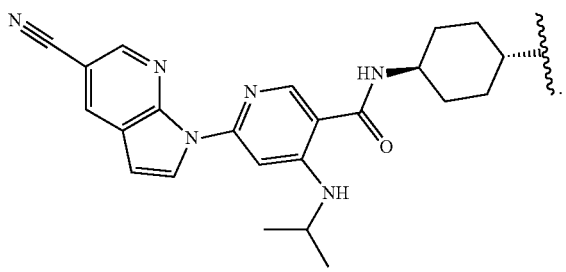 [SMILES: *[C@H]1CC[C@H](NC(=O)c2cnc(-n3ccc4cc(C#N)cnc43)cc2NC(C)C)CC1]
In some embodiments, IRAK is
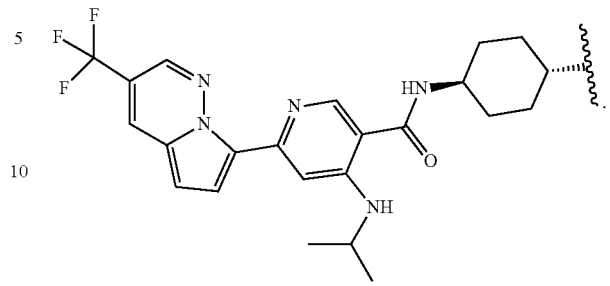
In some embodiments, IRAK is
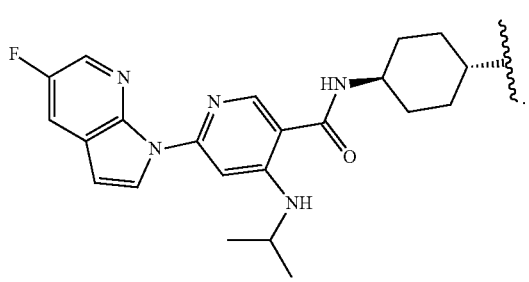 [SMILES: *[C@H]1CC[C@H](NC(=O)c2cnc(-n3ccc4cc(F)cnc43)cc2NC(C)C)CC1]
In some embodiments, IRAK is
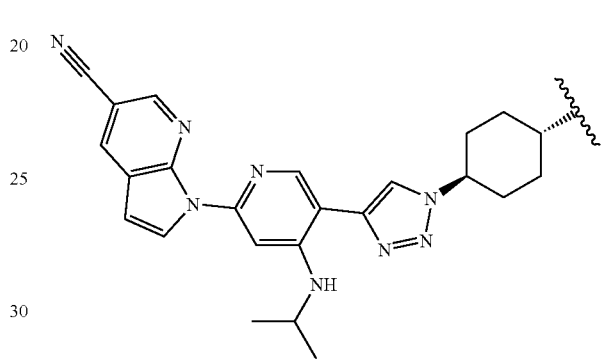
In some embodiments, IRAK is
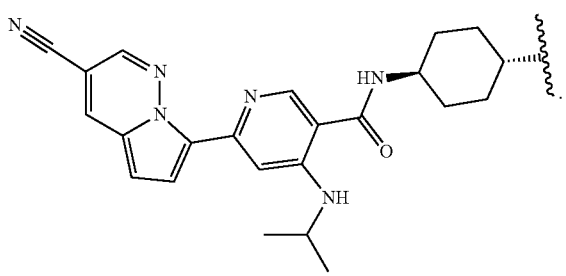 [SMILES: *[C@H]1CC[C@H](NC(=O)c2cnc(-c3ccc4cc(C#N)cnn34)cc2NC(C)C)CC1]
In some embodiments, IRAK is
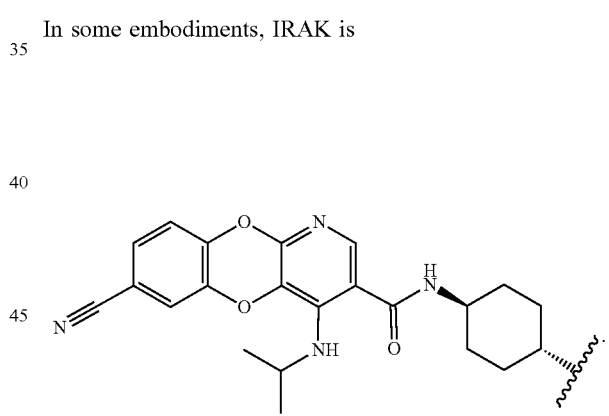
In some embodiments, IRAK is
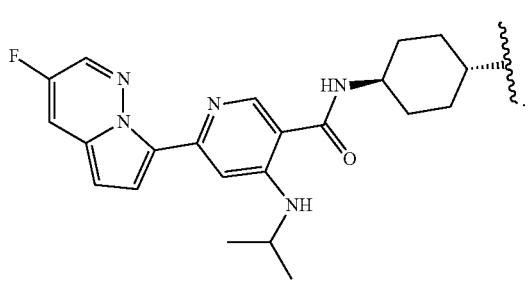 [SMILES: *[C@H]1CC[C@H](NC(=O)c2cnc(-c3ccc4cc(F)cnn34)cc2NC(C)C)CC1]
In some embodiments, IRAK is
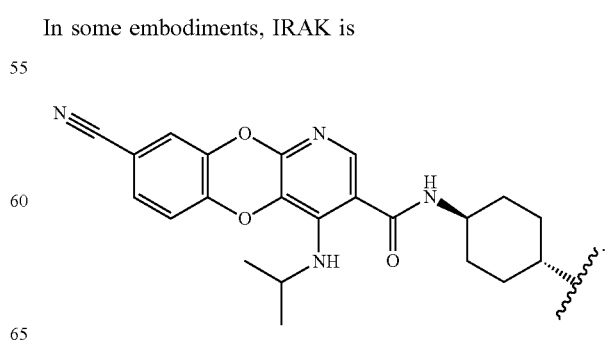

In some embodiments, IRAK is

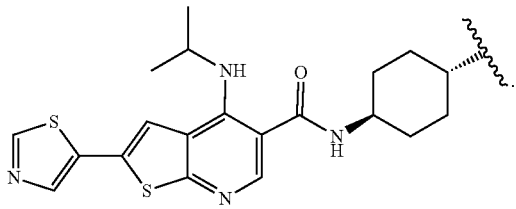 [SMILES: *[C@H]1CC[C@H](NC(=O)c2cnc3sc(-c4cncs4)cc3c2NC(C)C)CC1]

In some embodiments, IRAK is

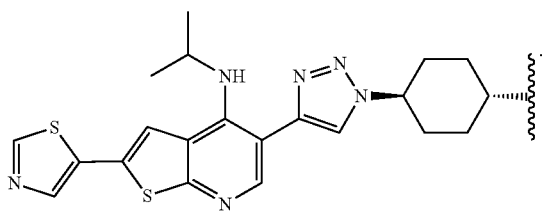

Ligase Binding Moiety (LBM)

As defined herein and described below, wherein a formula is depicted using square brackets, e.g.,

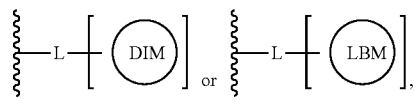

L is attached to a modifiable carbon, oxygen, or nitrogen atom within DIM or LBM including substitution or replacement of a defined group in DIM or LBM.

In some embodiments, DIM is LBM. In certain embodiments, the present invention provides a compound of formula I, wherein LBM is an E3 ubiquitin ligase (cereblon) binding moiety thereby forming a compound of formula I-aa:

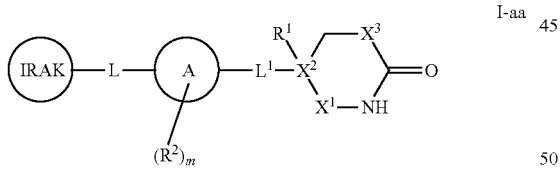

I-aa or a pharmaceutically acceptable salt thereof, wherein L and IRAK are as defined above and described herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

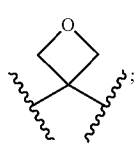 [SMILES: *C1(*)COC1]

$X^2$ is a carbon atom or silicon atom;

$X^3$ is a bivalent moiety selected from —CR$_2$—, —NR—, —O—, —S—, or —Si(R$_2$)—;

$R^1$ is hydrogen, deuterium, halogen, —CN, —OR, —SR, —S(O)R, —S(O)$_2$R, —N(R)$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;

each $R^2$ is independently hydrogen, deuterium, —R$^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

Ring A is a bi- or tricyclic ring selected from

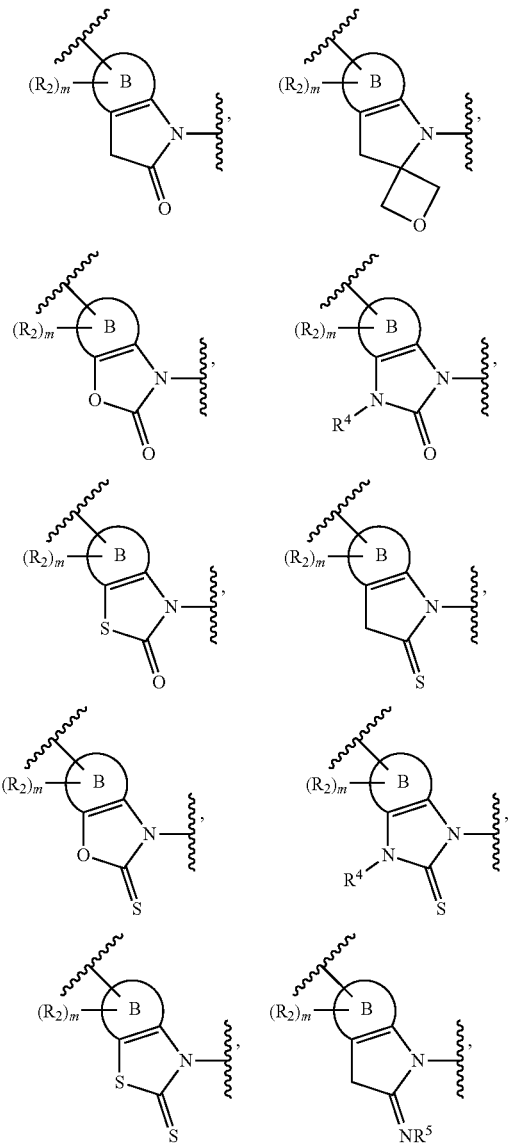

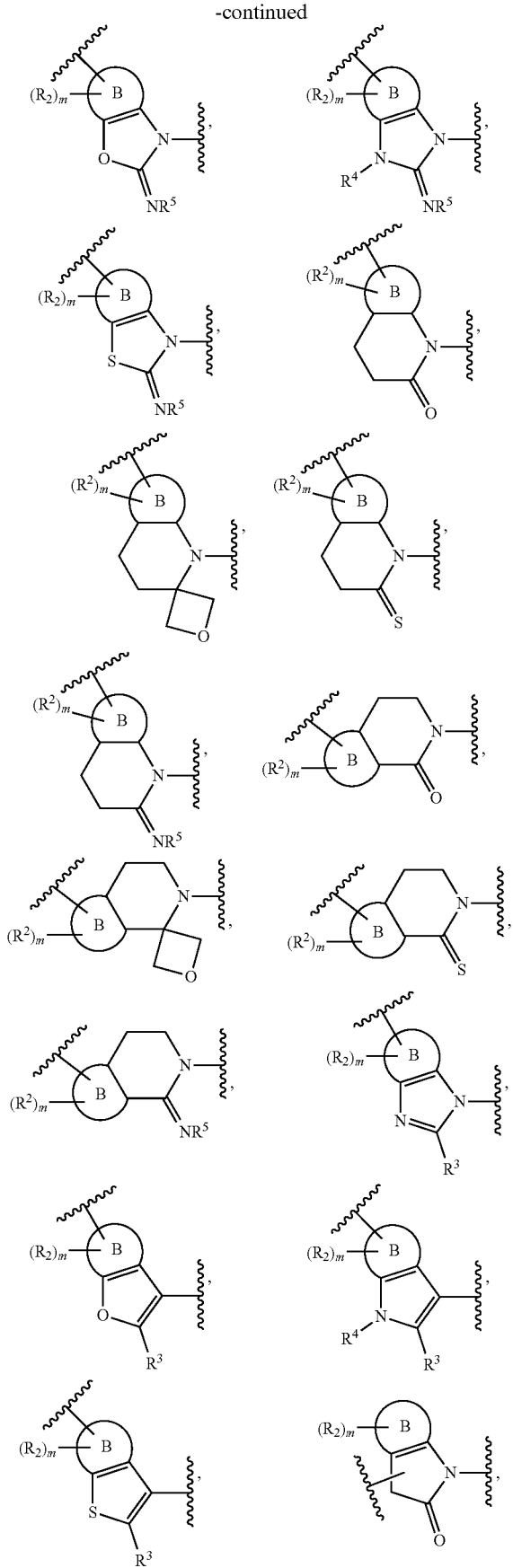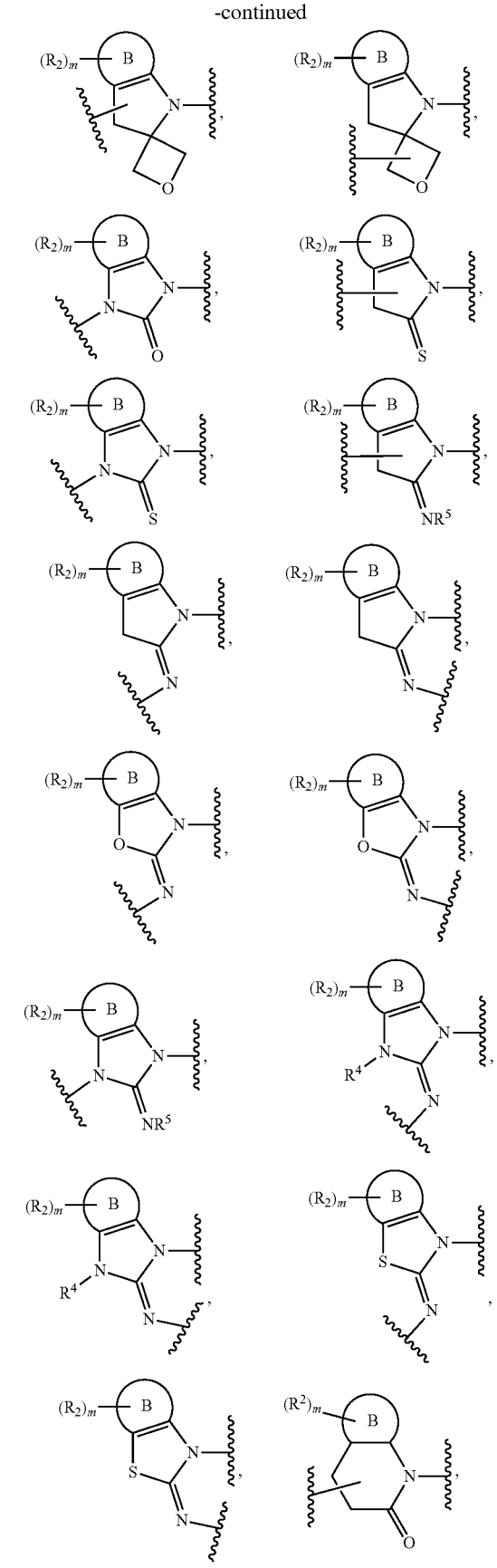

-continued

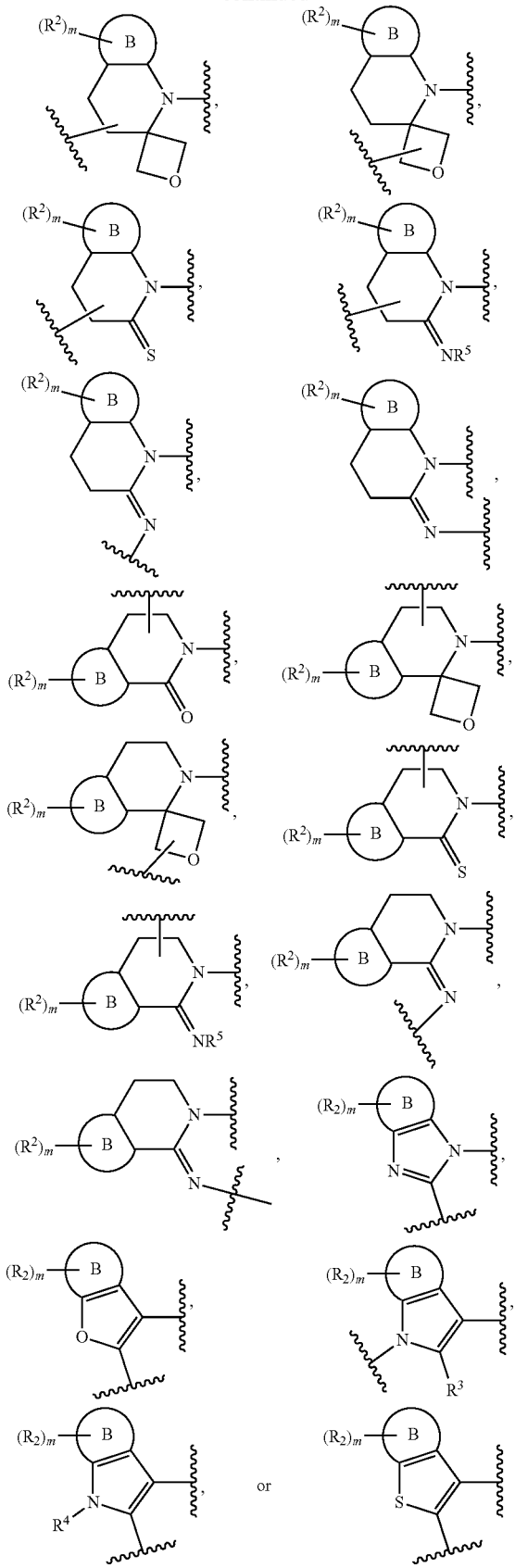

wherein
Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

m is 0, 1, 2, 3 or 4;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_m$ is depicted on Ring B, it is intended, and one of ordinary skill in the art would appreciate, that the point of attachment of —(R$^2$)$_m$ may be on Ring A and may also be at any available carbon or nitrogen atom on Ring A including the ring to which Ring B is fused. Where —R$^2$ is attached to a nitrogen atom bound to $R^4$ or $R^5$, $R^4$ or $R^5$ is absent and —R$^2$ takes the place of the $R^4$ or $R^5$ group. Where —R$^2$ is attached to a carbon atom bound to $R^3$, $R^3$ is absent and —R$^2$ takes the place of the $R^3$ group.

In some embodiments, a compound of formula I-aa above is provided as a compound of formula I-aa' or formula I-aa'':

I-aa'

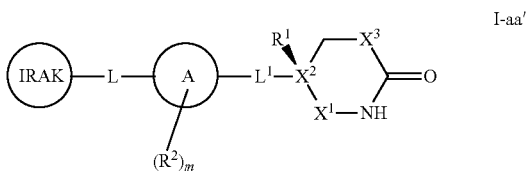

-continued

I-aa″

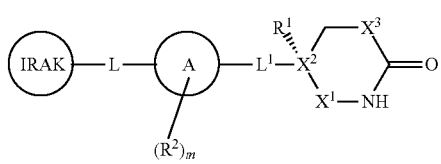

or a pharmaceutically acceptable salt thereof, wherein:
each of IRAK, Ring A, L, L¹, R¹, R², X², X³, and m is as defined above.

In certain embodiments, the present invention provides a compound of Formula I, wherein LBM is an E3 ubiquitin ligase (cereblon) binding moiety thereby forming a compound of formula I-cc:

I-cc

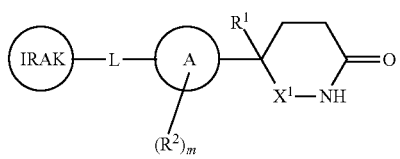

or a pharmaceutically acceptable salt thereof, wherein L and IRAK are as defined above and described in embodiments herein, and wherein:

X¹ is a bivalent moiety selected from a covalent bond, —CH₂—, —C(O)—, —C(S)—, or

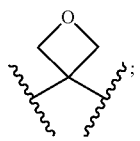 [SMILES: *C1(*)COC1]

R¹ is hydrogen, deuterium, halogen, —CN, —OR, —SR, —S(O)R, —S(O)₂R, —NR₂, or an optionally substituted C₁₋₄ aliphatic;

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring A is a bi- or tricyclic ring selected from

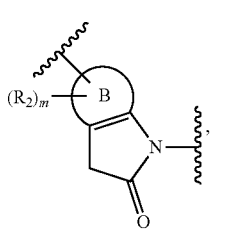 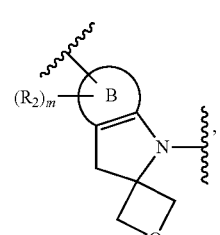

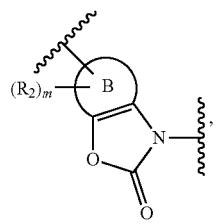 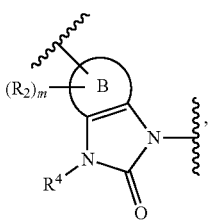

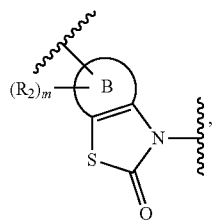 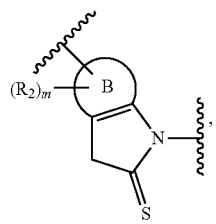

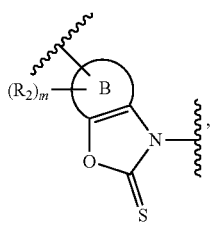 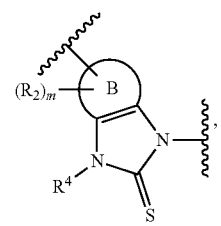

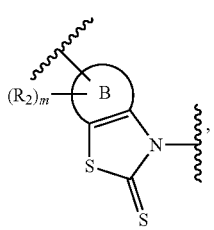 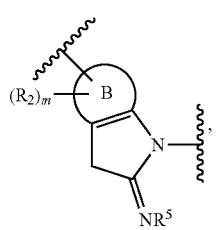

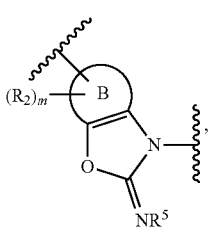 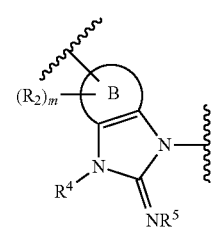

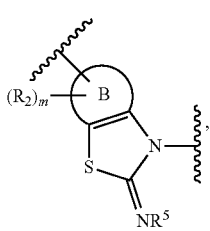 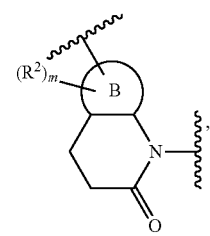

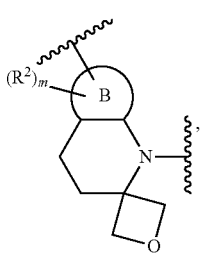 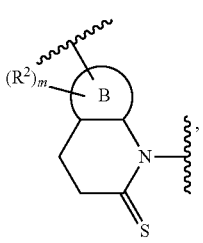

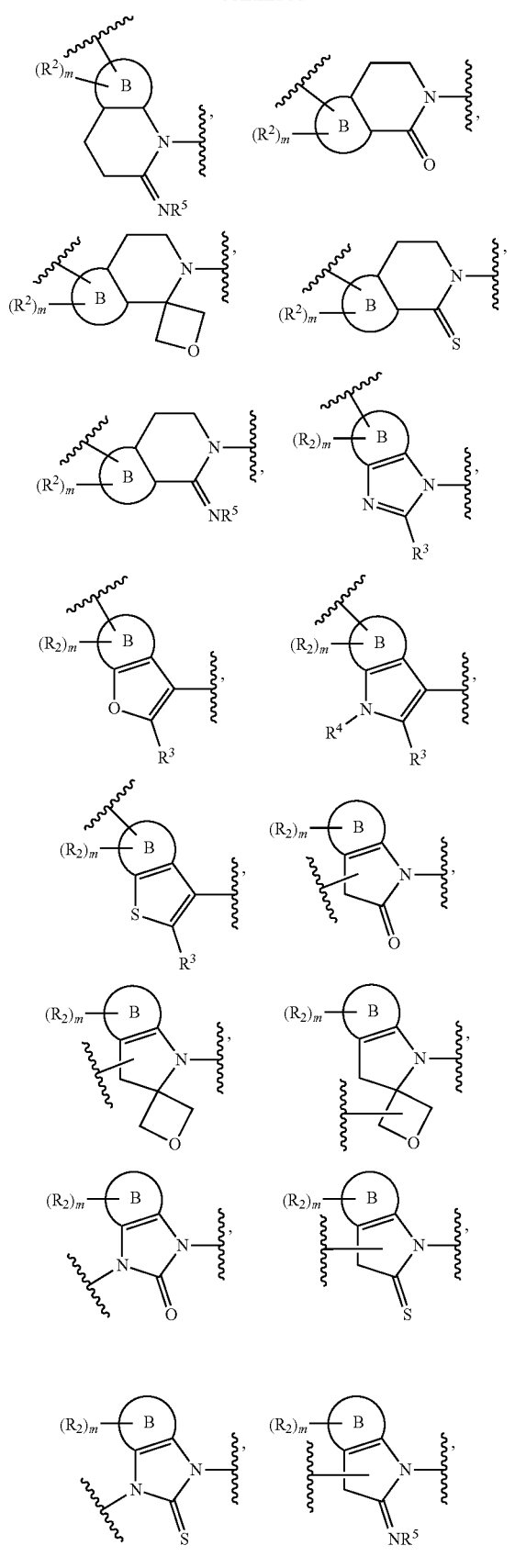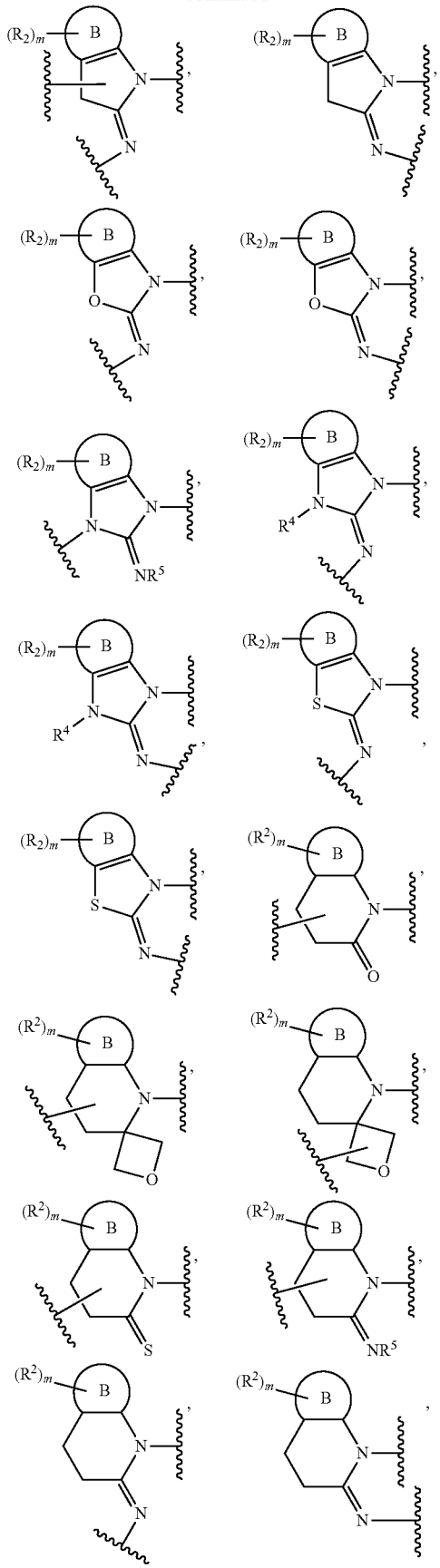

-continued

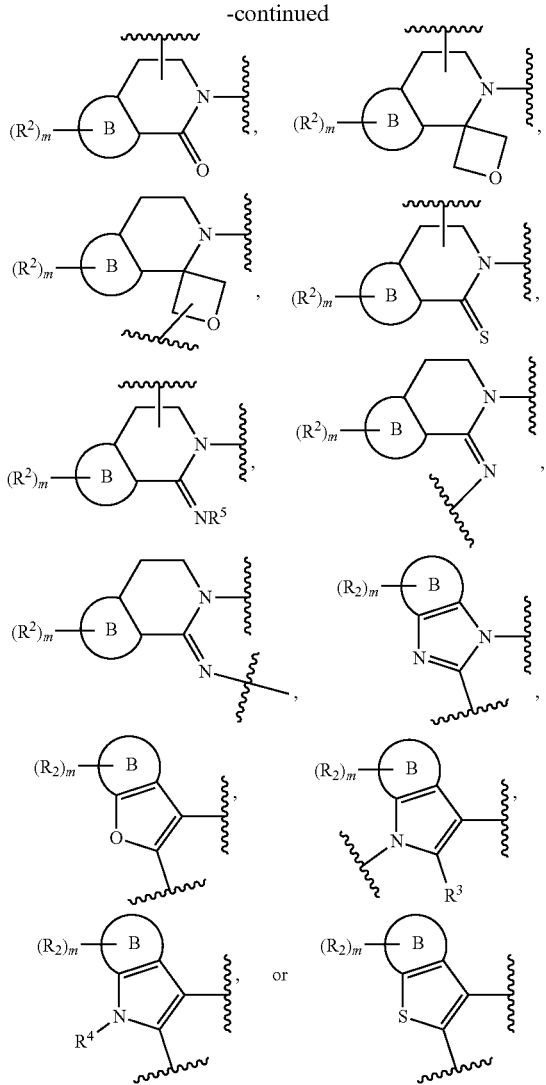

wherein
Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_m$ is depicted on Ring B, it is intended, and one of ordinary skill in the art would appreciate, that the point of attachment of —(R$^2$)$_m$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In some embodiments, the compound of formula I-cc above is provided as a compound of formula I-cc' or formula I-cc":

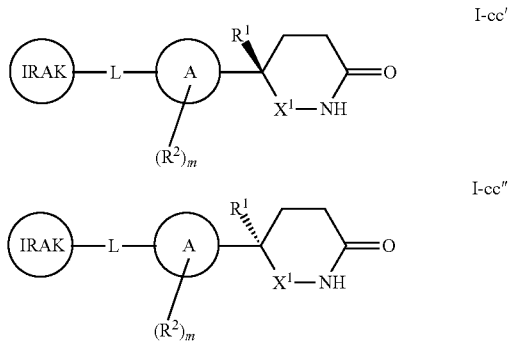

I-cc'

I-cc"

or a pharmaceutically acceptable salt thereof, wherein:
each of IRAK, Ring A, L, R$^1$, R$^2$, X$^1$, and m is as defined above.

In certain embodiments, the present invention provides a compound of formula I, wherein LBM is an E3 ubiquitin ligase (cereblon) binding moiety thereby forming a compound of formula I-dd:

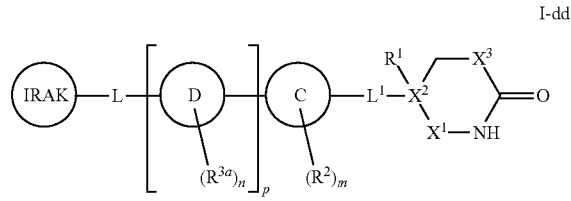

I-dd or a pharmaceutically acceptable salt thereof, wherein, L and IRAK are as defined above and described in embodiments herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

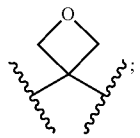 [SMILES: *C1(*)COC1]

$X^2$ is a carbon atom or silicon atom;
$X^3$ is a bivalent moiety selected from —CR$_2$—, —NR—, —O—, —S—, or —Si(R$_2$)—;
$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;
Ring C is a mono- or bicyclic ring selected from

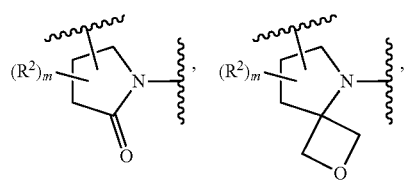
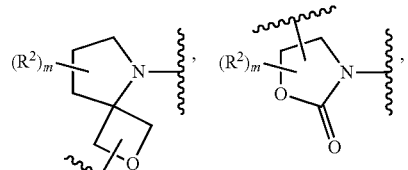

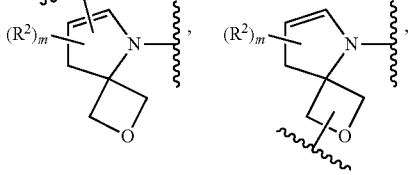
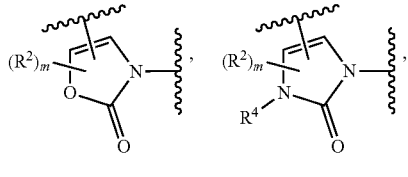

-continued

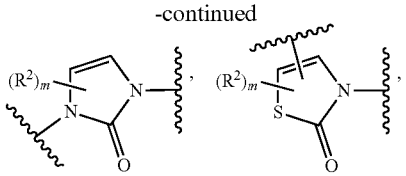
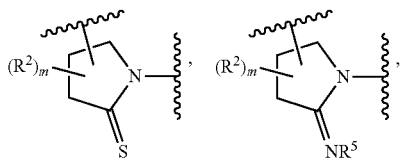
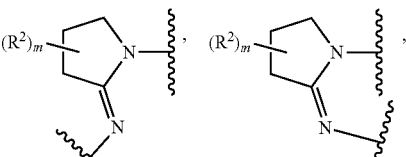
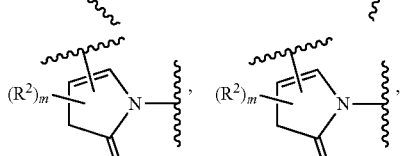
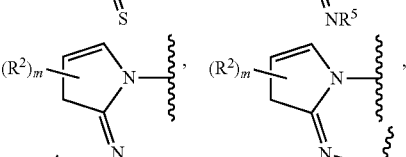
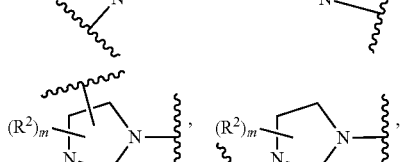
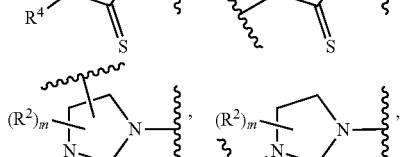
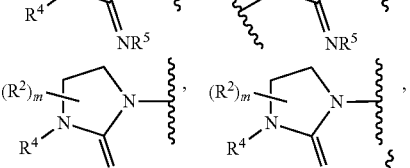
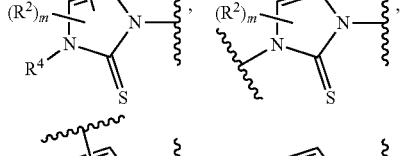
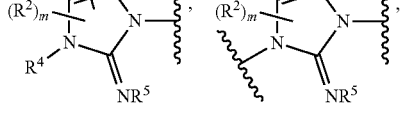

-continued

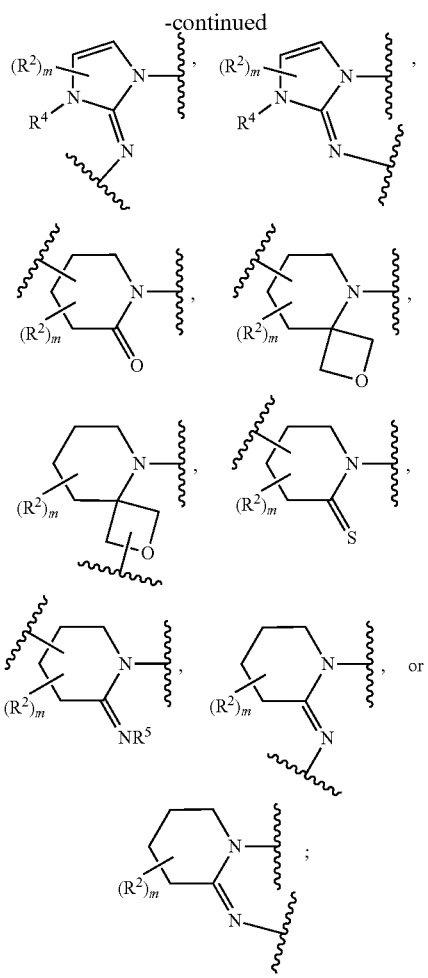

each of $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —$S(O)R$, —$C(O)R$, —$C(O)OR$, —$C(O)N(R)_2$, —$C(O)N(R)OR$, —$C(R)_2N(R)C(O)R$, —$C(R)_2N(R)C(O)N(R)_2$, —$OC(O)R$, —$OC(O)N(R)_2$, —$OP(O)R_2$, —$OP(O)(OR)_2$, —$OP(O)(OR)(NR_2)$, —$OP(O)(NR_2)_2$, —$N(R)C(O)OR$, —$N(R)C(O)R$, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

Ring D is selected from a 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)═CH—;

m is 0, 1, 2, 3 or 4;

n is 0, 1, 2, 3 or 4;

p is 0 or 1, wherein when p is 0, the bond connecting Ring C and Ring D is connected to

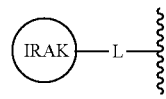

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-dd above is provided as a compound of formula I-dd' or formula I-dd":

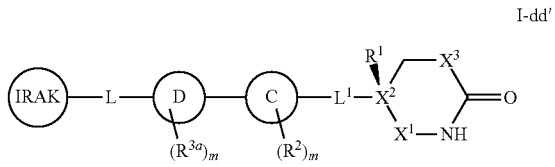

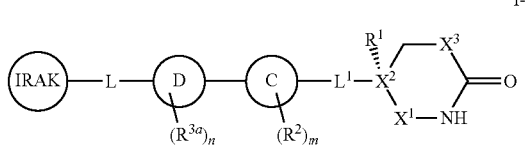

or a pharmaceutically acceptable salt thereof, wherein:

each of IRAK, Ring C, Ring D, L, $L^1$, $R^1$, $R^2$, $R^{3a}$, $X^1$, $X^2$, $X^3$, n, m, and p is as defined above.

In certain embodiments, the present invention provides a compound of Formula I, wherein LBM is an E3 ubiquitin ligase (cereblon) binding moiety thereby forming a compound of formula I-ee:

I-ee

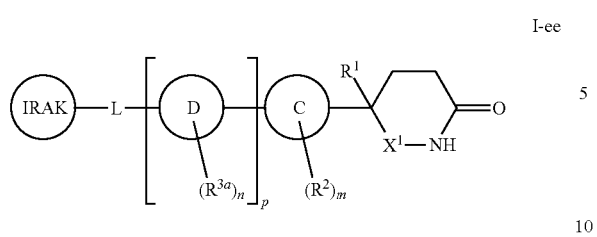

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

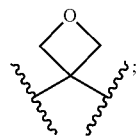 [SMILES: *C1(*)COC1];

$R^1$ is hydrogen, deuterium, halogen, —CN, —OR, —SR, —S(O)R, —S(O)$_2$R, —NR$_2$, or an optionally substituted $C_{1-4}$ aliphatic;

Ring C is a mono- or bicyclic ring selected from

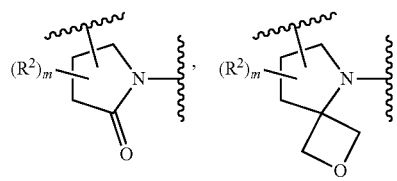

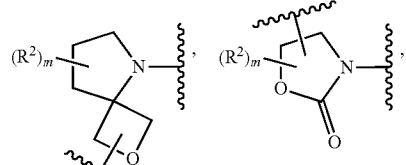

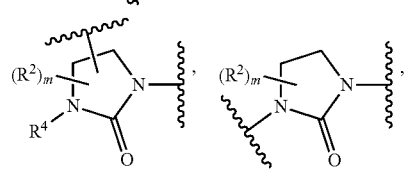

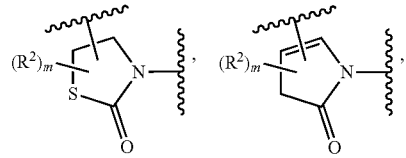

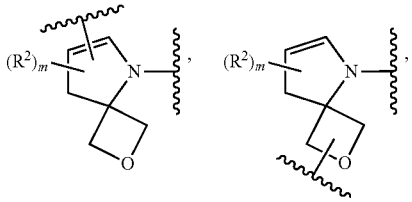

-continued

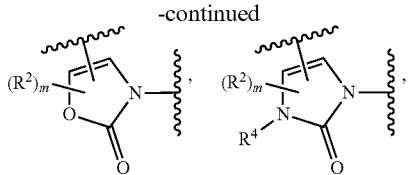

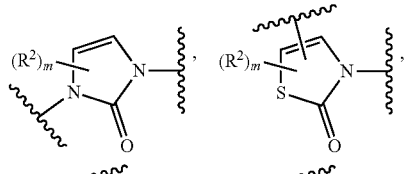

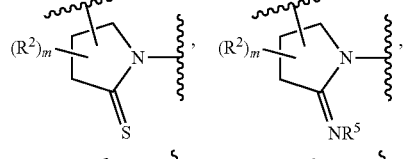

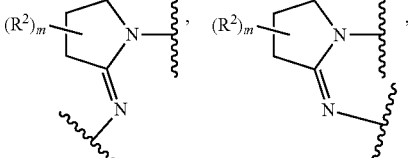

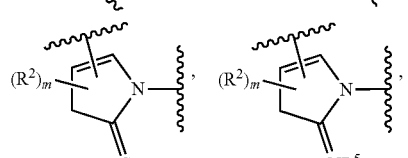

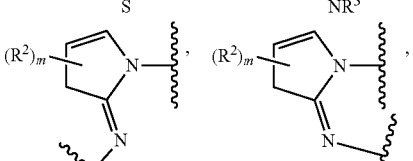

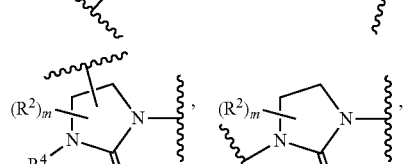

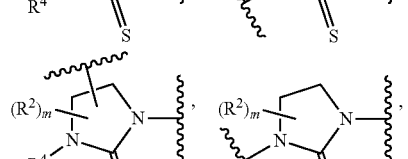

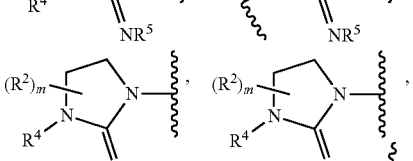

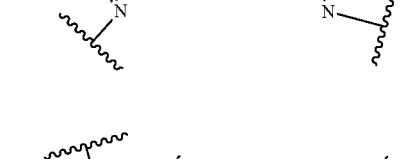

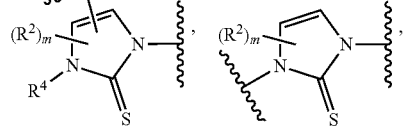

-continued

[Structures with (R²)ₘ, R⁴, NR⁵ groups shown]

each of R² and R³ᵃ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3 or 4;

p is 0 or 1, wherein when p is 0, the bond connecting Ring C and Ring D is connected to

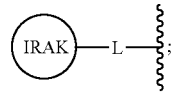

and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ee above is provided as a compound of formula I-ee' or formula I-ee":

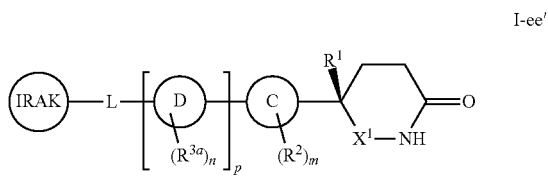

I-ee'

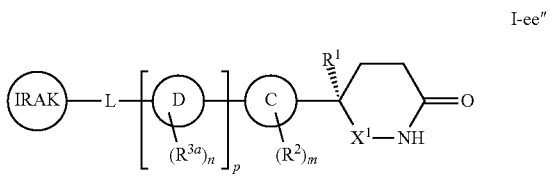

I-ee"

or a pharmaceutically acceptable salt thereof, wherein:
each of IRAK, Ring C, Ring D, L, R¹, R², R³ᵃ, X¹, n, m, and p is as defined above.

In certain embodiments, the present invention provides a compound of formula I, wherein LBM is an E3 ubiquitin ligase (cereblon) binding moiety thereby forming a compound of formula I-ff:

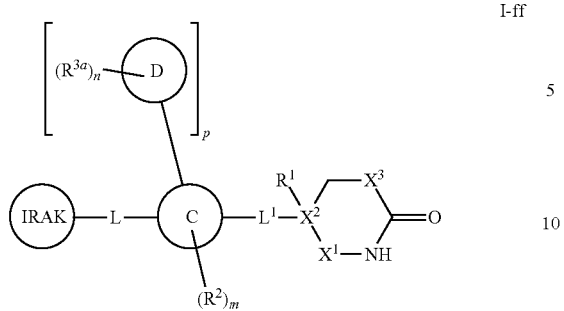

I-ff or a pharmaceutically acceptable salt thereof, wherein L and IRAK are as defined above and described in embodiments herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

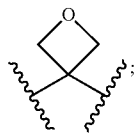

$X^2$ is a carbon atom or silicon atom;
$X^3$ is a bivalent moiety selected from —CR$_2$—, —NR—, —O—, —S—, or —Si(R$_2$)—;
$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;
Ring C is a mono- or bicyclic ring selected from

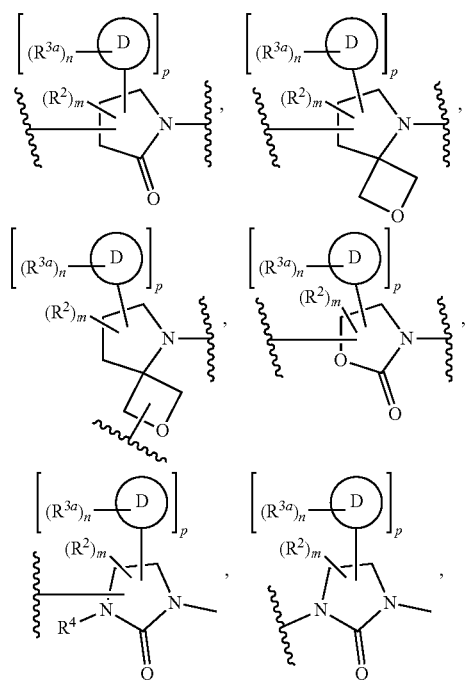

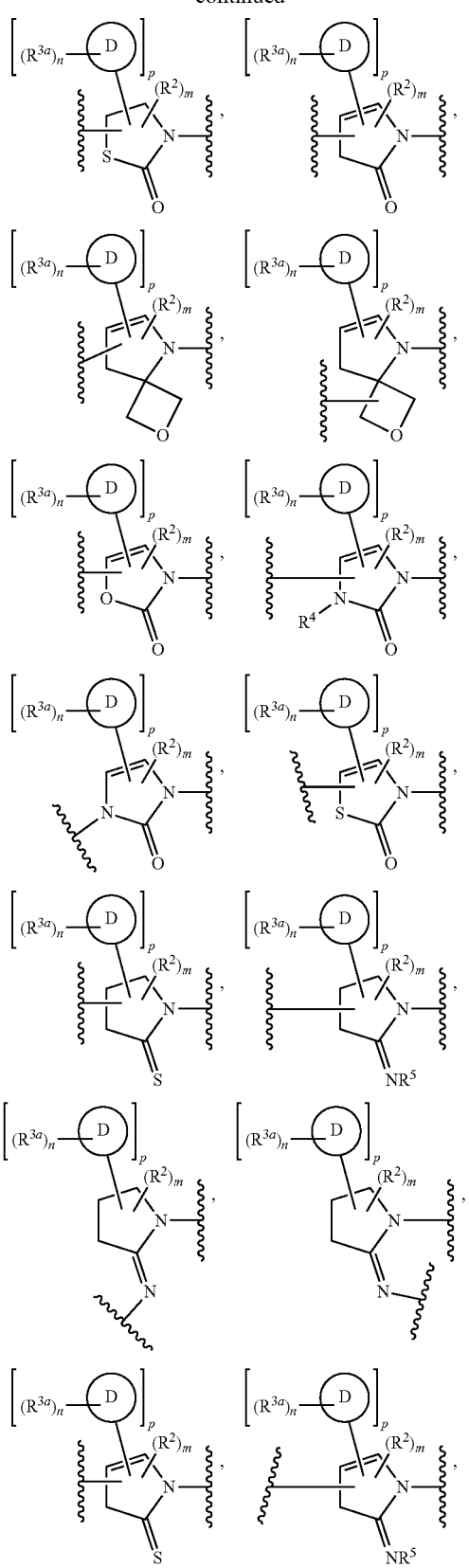

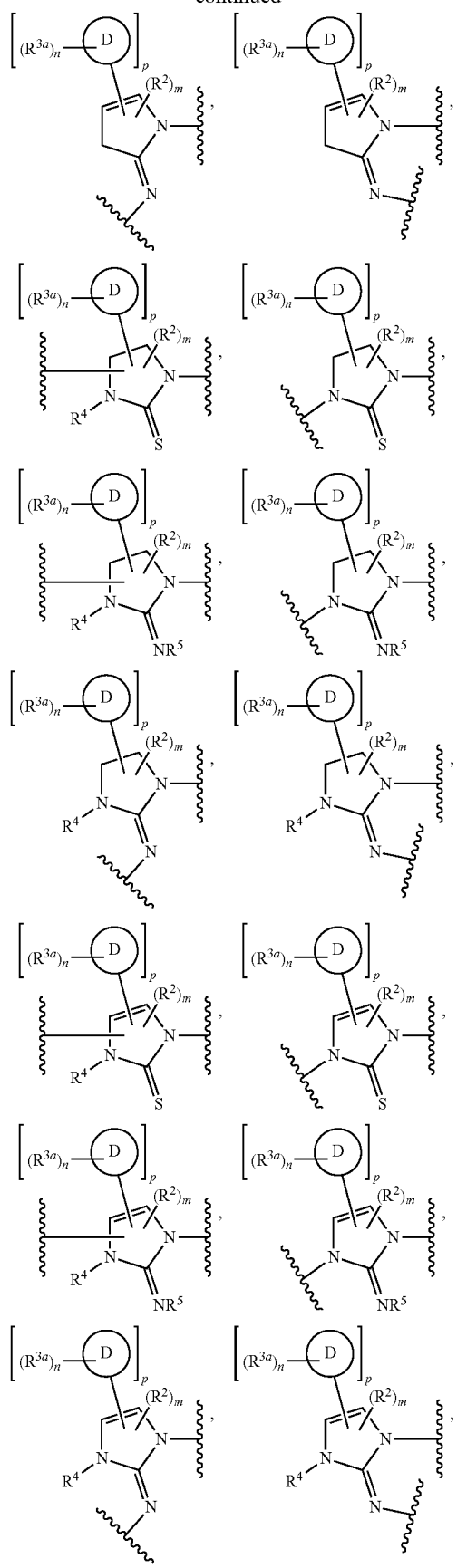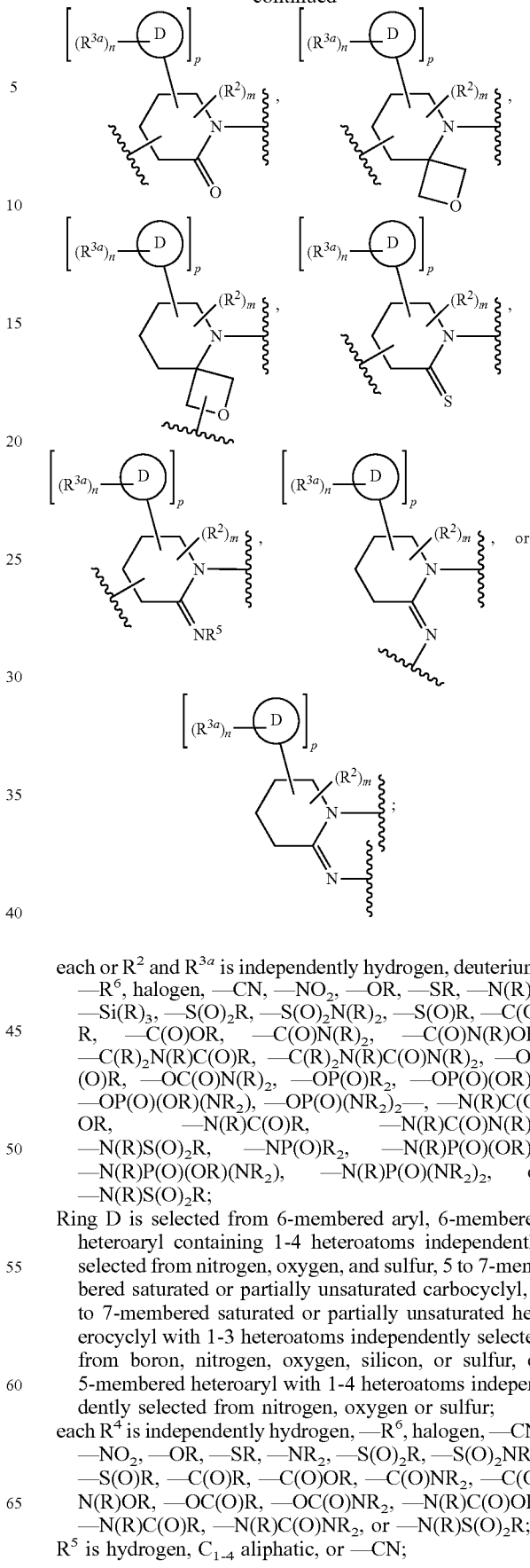

each or $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —$C(O)N(R)_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —OP(O)(OR)$_2$, —$OP(O)(OR)(NR_2)$, —$OP(O)(NR_2)_2$—, —N(R)C(O)OR, —N(R)C(O)R, —$N(R)C(O)N(R)_2$, —$N(R)S(O)_2R$, —$NP(O)R_2$, —$N(R)P(O)(OR)_2$, —$N(R)P(O)(OR)(NR_2)$, —$N(R)P(O)(NR_2)_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

m is 0, 1, 2, 3 or 4;

n is 0, 1, 2, 3 or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ff above is provided as a compound of formula I-ff' or formula I-ff":

I-ff'

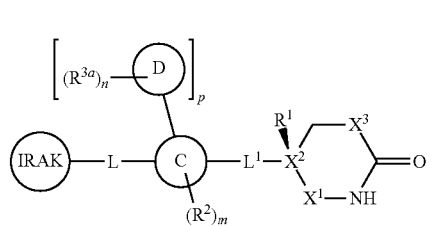

I-ff"

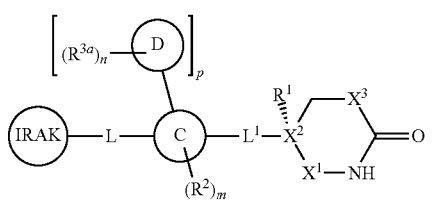

or a pharmaceutically acceptable salt thereof, wherein:

each of IRAK, Ring C, Ring D, L, $L^1$, $R^1$, $R^2$, $R^{3a}$, $X^1$, $X^2$, $X^3$, m, n, and p is as defined above.

In certain embodiments, the present invention provides a compound of Formula I, wherein LBM is an E3 ubiquitin ligase (cereblon) binding moiety thereby forming a compound of formula I-gg:

I-gg

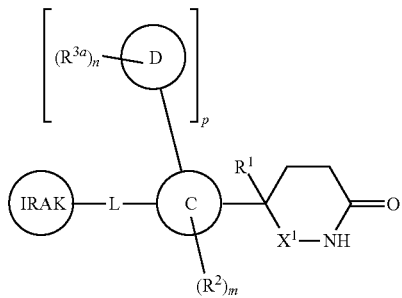

or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

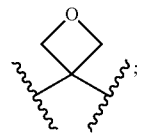

$R^1$ is hydrogen, deuterium, halogen, —CN, —OR, —SR, —S(O)R, —S(O)$_2$R, —NR$_2$, or an optionally substituted $C_{1-4}$ aliphatic;

Ring C is a mono- or bicyclic ring selected from

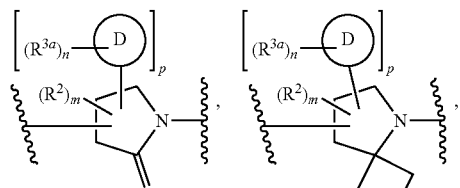

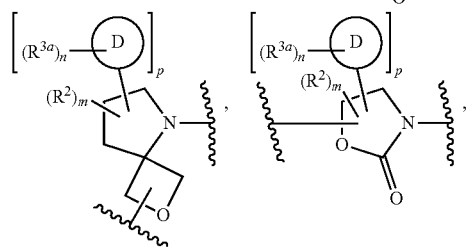

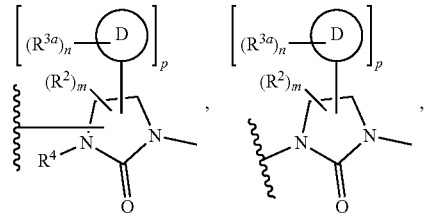

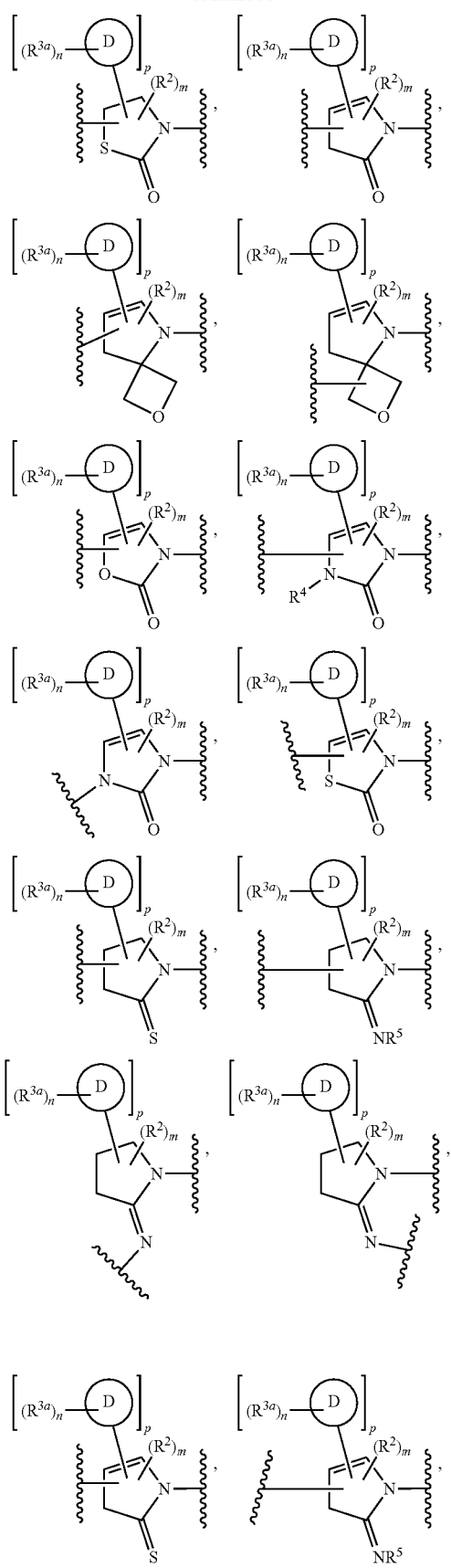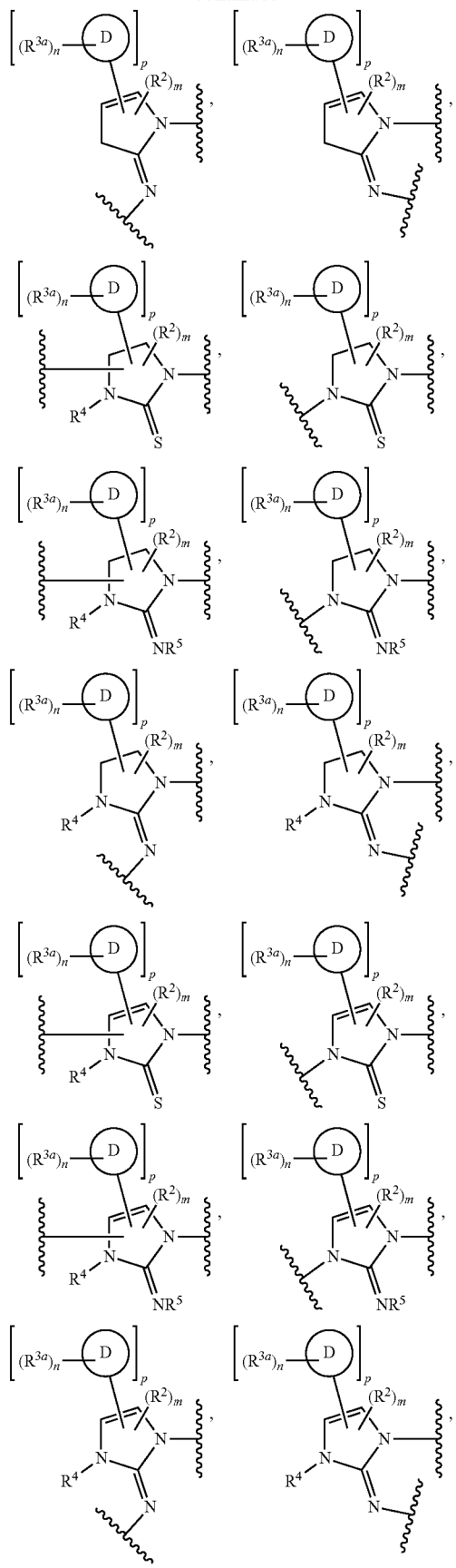

-continued

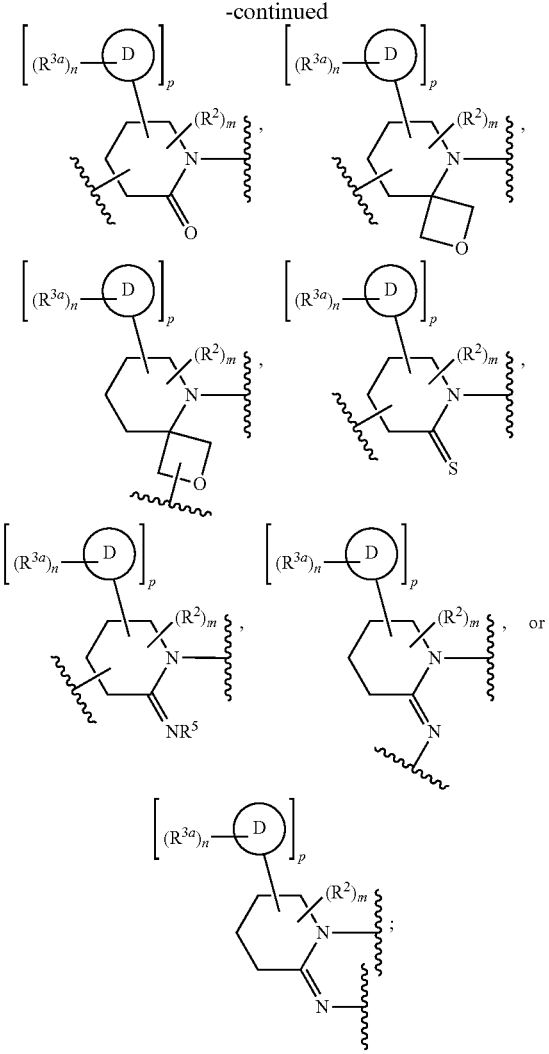

each of $R^2$, $R^{3a}$, and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-gg above is provided as a compound of formula I-gg' or formula I-gg":

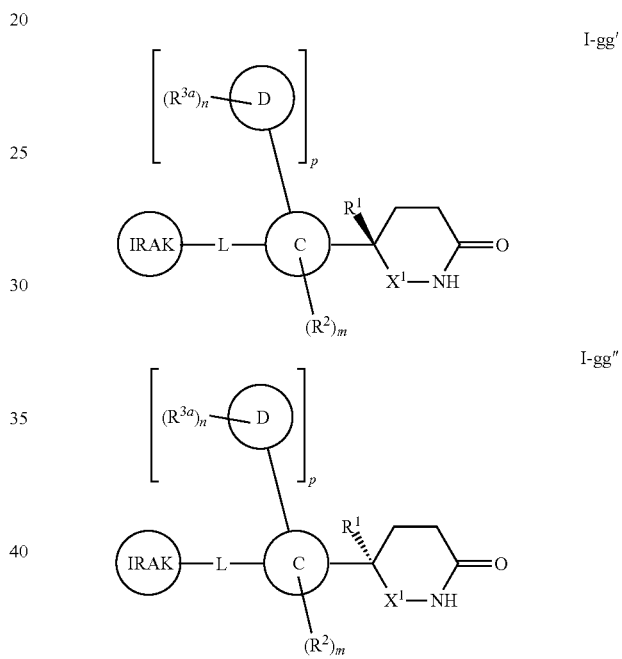

or a pharmaceutically acceptable salt thereof, wherein:
each of IRAK, Ring C, Ring D, L, $R^1$, $R^2$, $R^{3a}$, $X^1$, m, n, and p is as defined above.

In certain embodiments, the present invention provides a compound of Formula I, wherein LBM is an E3 ubiquitin ligase (cereblon) binding moiety thereby forming a compound of formula I-hh:

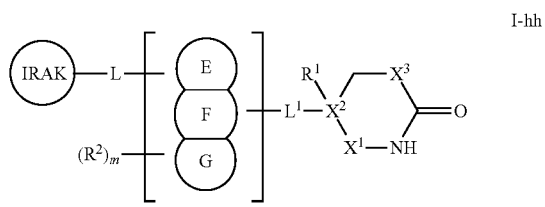

or a pharmaceutically acceptable salt thereof, wherein L and IRAK are as defined above and described in embodiments herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

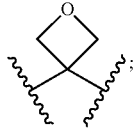 [SMILES: *C1(*)COC1]

$X^2$ is a carbon atom, nitrogen atom, or silicon atom;

$X^3$ is a bivalent moiety selected from a covalent bond, —CR$_2$—, —NR—, —O—, —S—, or —SiR$_2$—;

$R^1$ is absent, hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)R$_2$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —R$^6$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)NR$_2$, —OP(O)(NR$_2$)$_2$—, —N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups;

$L^1$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—; and m is 0, 1, 2, 3, 4, 5, 6, 7, 8, 9, 10, 11, 12, 13, 14, 15, or 16.

Where a point of attachment of

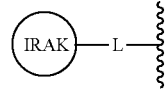

is depicted on Ring E, Ring F, or Ring G, it is intended, and one of ordinary skill in the art would appreciate, that the point of attachment of

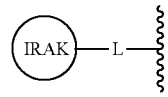

may be on any available carbon or nitrogen atom on Ring E, Ring F, or Ring G, including the ring to which Ring E or Ring G is fused to Ring F.

Where a point of attachment of —(R$^2$)$_m$ is depicted on Ring E, Ring F, or Ring G, it is intended, and one of ordinary skill in the art would appreciate, that the point of attachment of —(R$^2$)$_m$ may be at any available carbon or nitrogen atom on Ring E, Ring F, or Ring G including the carbon atom to which Ring E or Ring G is fused to Ring F.

Where a point of attachment of

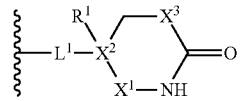

is depicted on Ring E, Ring F, or Ring G, it is intended, and one of ordinary skill in the art would appreciate, that the point of attachment of

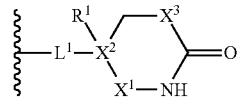

may be on any available carbon or nitrogen atom on Ring E, Ring F, or Ring G, including the carbon atom to which Ring E or Ring G is fused to Ring F.

In some embodiments, a compound of formula I-hh above is provided as a compound of formula I-hh' or formula I-hh":

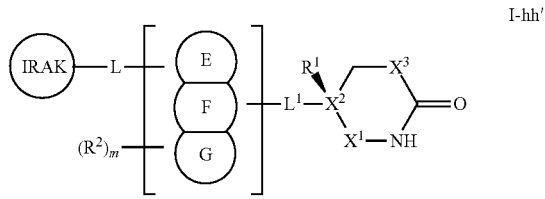

I-hh'

-continued

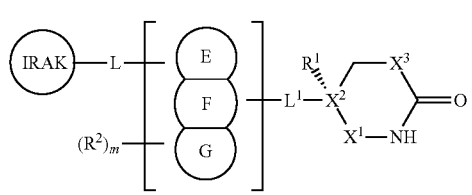

I-hh″ or a pharmaceutically acceptable salt thereof, wherein:
each of IRAK, Ring E, Ring F, Ring G, L, L$^1$, R$^1$, R$^2$, X$^1$, X$^2$, X$^3$, and m is as defined above.

In certain embodiments, the present invention provides a compound of Formula I, wherein LBM is an E3 ubiquitin ligase (cereblon) binding moiety thereby forming a compound of formula I-hh-1 or I-hh-2:

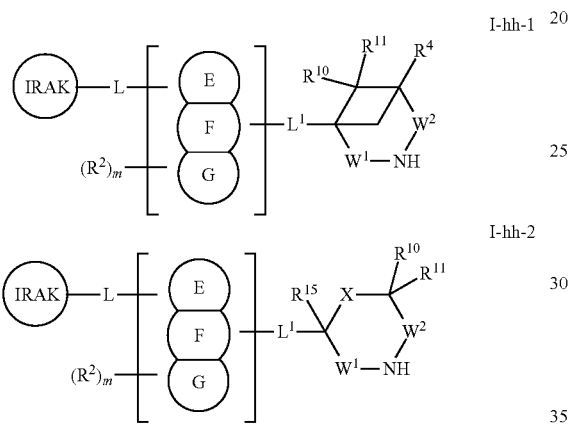

or a pharmaceutically acceptable salt thereof, wherein L and IRAK are as defined above and described in embodiments herein, and wherein:
each R$^2$ is independently hydrogen, deuterium, —R$^6$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)NR$_2$, —OP(O)(NR$_2$)$_2$—, —N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R;
each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups;
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
L$^1$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)═CH—;
m is 0, 1, 2, 3, 4, 5, 6, 7, 8, 9, 10, 11, 12, 13, 14, 15, or 16; and
R$^4$, R$^{10}$, R$^{11}$, R$^{15}$, W$^1$, W$^2$, and X is as defined in WO 2019/099868, the entirety of each of which is herein incorporated by reference.

Where a point of attachment of

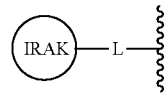

is depicted on Ring E, Ring F, or Ring G, it is intended, and one of ordinary skill in the art would appreciate, that the point of attachment of

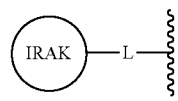

may be on any available carbon or nitrogen atom on Ring E, Ring F, or Ring G, including the ring to which Ring E or Ring G is fused to Ring F.

Where a point of attachment of —(R$^2$)$_m$ is depicted on Ring E, Ring F, or Ring G, it is intended, and one of ordinary skill in the art would appreciate, that the point of attachment of —(R$^2$)$_m$ may be at any available carbon or nitrogen atom on Ring E, Ring F, or Ring G including the carbon atom to which Ring E or Ring G is fused to Ring F.

Where a point of attachment of

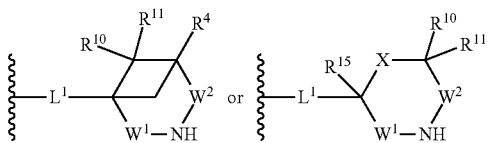

is depicted on Ring E, Ring F, or Ring G, it is intended, and one of ordinary skill in the art would appreciate, that the point of attachment of

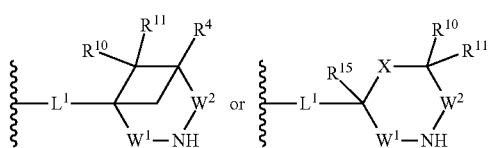

may be on any available carbon or nitrogen atom on Ring E, Ring F, or Ring G, including the carbon atom to which Ring E or Ring G is fused to Ring F.

In certain embodiments, the present invention provides a compound of Formula I, wherein LBM is an E3 ubiquitin ligase (cereblon) binding moiety thereby forming a compound of formula I-ii:

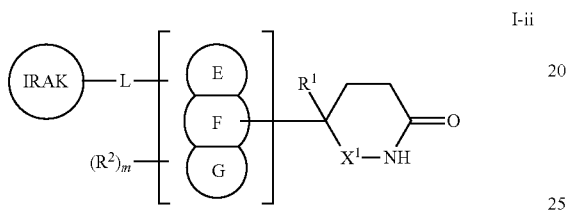

I-ii or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

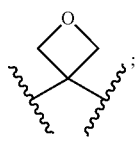 [SMILES: *C1(*)COC1]

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl containing 0-3 nitrogens, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur, wherein Ring E, Ring F, and Ring G is independently and optionally substituted with 1-2 oxo groups; and m is 0, 1, 2, 3, or 4.

Where a point of attachment of

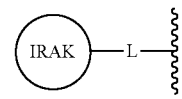

is depicted on Ring E, Ring F, or Ring G, it is intended, and one of ordinary skill in the art would appreciate, that the point of attachment of

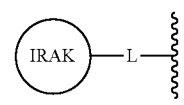

may be on any available carbon or nitrogen atom on Ring E, Ring F, or Ring G, including the ring to which Ring E or Ring G is fused to Ring F.

Where a point of attachment of —(R$^2$)$_m$ is depicted on Ring E, Ring F, or Ring G, it is intended, and one of ordinary skill in the art would appreciate, that the point of attachment of —(R$^2$)$_m$ may be at any available carbon or nitrogen atom on Ring E, Ring F, or Ring G including the carbon atom to which Ring E or Ring G is fused to Ring F.

In some embodiments, a compound of formula I-ii above is provided as a compound of formula I-ii' or formula I-ii":

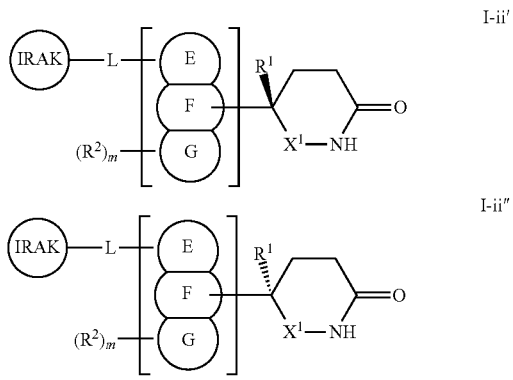

or a pharmaceutically acceptable salt thereof, wherein:
each of IRAK, L, Ring E, Ring F, Ring G, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-jj:

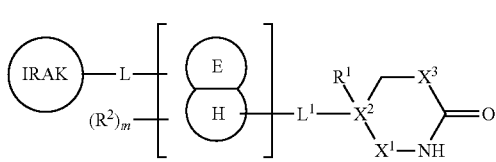

I-jj or a pharmaceutically acceptable salt thereof, wherein L and IRAK are as defined above and described in embodiments herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

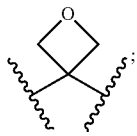 [SMILES: *C1(*)COC1]

$X^2$ is a carbon atom, nitrogen atom, or silicon atom;

$X^3$ is a bivalent moiety selected from a covalent bond, —CR$_2$—, —NR—, —O—, —S—, or —SiR$_2$—;

$R^1$ is absent, hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)R$_2$, —SiR$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

m is 0, 1, 2, 3, or 4.

Where a point of attachment of

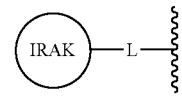

is depicted on Ring E or Ring H, it is intended, and one of ordinary skill in the art would appreciate, that the point of attachment of

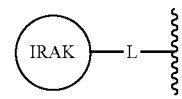

may be on any available carbon or nitrogen atom on Ring E or Ring H including the carbon atom to which Ring E and Ring H are fused.

Where a point of attachment of —(R$^2$)$_m$ is depicted on Ring E and Ring H, it is intended, and one of ordinary skill in the art would appreciate, that the point of attachment of —(R$^2$)$_m$ may be on any available carbon or nitrogen atom on Ring E or Ring H including the carbon atom to which Ring E and Ring H are fused.

Where a point of attachment of

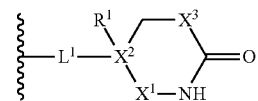

is depicted on Ring E and Ring H, it is intended, and one of ordinary skill in the art would appreciate, that the point of attachment of

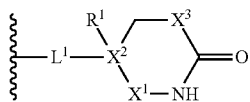

may be on any available carbon or nitrogen atom on Ring E or Ring H including the carbon atom to which Ring E and Ring H are fused.

In some embodiments, a compound of formula I-jj above is provided as a compound of formula I-jj' or formula I-jj":

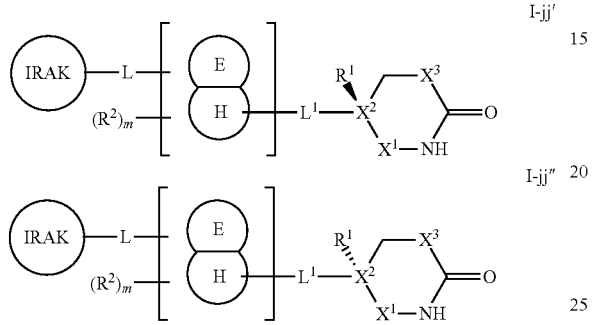

or a pharmaceutically acceptable salt thereof, wherein:
each of IRAK, Ring E, Ring H, L, $L^1$, $R^1$, $R^2$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-kk:

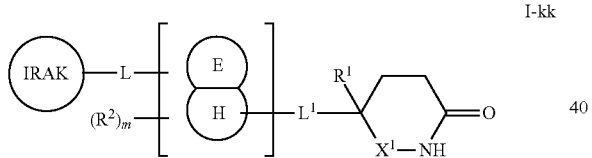

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

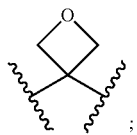 [SMILES: *C1(*)COC1]

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups; and m is 0, 1, 2, 3, or 4.

Where a point of attachment of

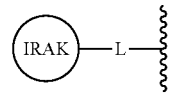

is depicted on Ring E or Ring H, it is intended, and one of ordinary skill in the art would appreciate, that the point of attachment of

may be on any available carbon or nitrogen atom on Ring E or Ring H including the carbon atom to which Ring E and Ring H are fused.

Where a point of attachment of —$(R^2)_m$ is depicted on Ring E and Ring H, it is intended, and one of ordinary skill in the art would appreciate, that the point of attachment of —$(R^2)_m$ may be on any available carbon or nitrogen atom on Ring E or Ring H including the carbon atom to which Ring E and Ring H are fused.

Where a point of attachment of

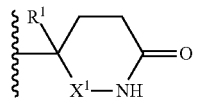

is depicted on Ring E and Ring H, it is intended, and one of ordinary skill in the art would appreciate, that the point of attachment of

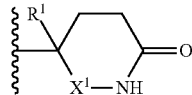

may be on any available carbon or nitrogen atom on Ring E or Ring H including the carbon atom to which Ring E and Ring H are fused.

In some embodiments, a compound of formula I-kk above is provided as a compound of formula I-kk' or formula I-kk":

I-kk'

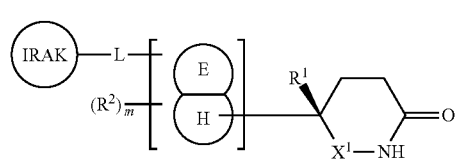

I-kk"

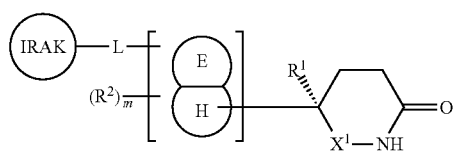

or a pharmaceutically acceptable salt thereof, wherein:
each of IRAK, Ring E, Ring H, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-ll:

I-ll

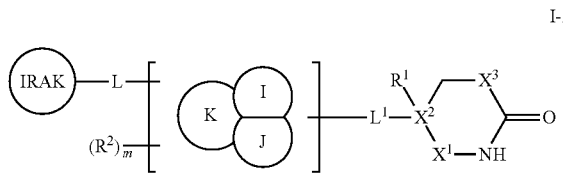

or a pharmaceutically acceptable salt thereof, wherein L and IRAK are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

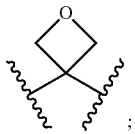 [SMILES: *C1(*)COC1]

$X^2$ is a carbon atom, nitrogen atom, or silicon atom;
$X^3$ is a bivalent moiety selected from a covalent bond, —$CR_2$—, —NR—, —O—, —S—, or —$SiR_2$—;
$R^1$ is absent, hydrogen, deuterium, halogen, —CN, —OR, —SR, —S(O)R, —S(O)$_2$R, —$NR_2$, —P(O)(OR)$_2$, —P(O)(NR$_2$)OR, —P(O)(NR$_2$)$_2$, —Si(OH)$_2$R, —Si(OH)R$_2$, —SiR$_3$, or an optionally substituted $C_{1-4}$ aliphatic;
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each $R^2$ is independently hydrogen, deuterium, —$R^6$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;
each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
each of Ring I and J is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;
Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;
$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)₂—, —CH(R)—, —C(F)₂—, —N(R)—, —S—, —S(O)₂— or —(C)=CH—; and m is 0, 1, 2, 3, or 4.

Where a point of attachment of

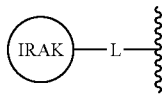

is depicted on Ring I, Ring J, and Ring K, it is intended, and one of ordinary skill in the art would appreciate, that the point of attachment of

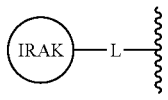

may be on any available carbon or nitrogen atom on Ring I, Ring J, or Ring K, including the carbon atom to which Ring I, Ring J, and Ring K are fused.

Where a point of attachment of —(R²)ₘ is depicted on Ring I, Ring J, and Ring K, it is intended, and one of ordinary skill in the art would appreciate, that the point of attachment of —(R²)ₘ may be on any available carbon or nitrogen atom on Ring I, Ring J, or Ring K, including the carbon atom to which Ring I, Ring J, and Ring K are fused.

Where a point of attachment of

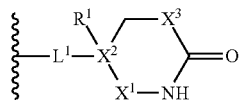

is depicted on Ring I, Ring J, and Ring K, it is intended, and one of ordinary skill in the art would appreciate, that the point of attachment of

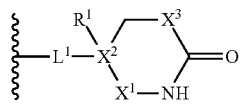

may be on any available carbon or nitrogen atom on Ring I, Ring J, or Ring K, including the carbon atom to which Ring I, Ring J, and Ring K are fused.

In some embodiments, a compound of formula I-ll above is provided as a compound of formula I-ll' or formula I-ll":

I-ll'

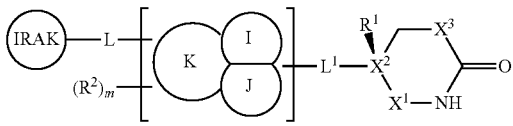

I-ll"

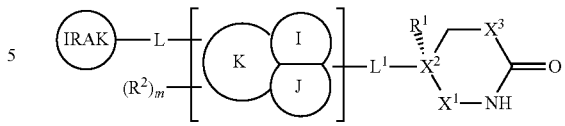

or a pharmaceutically acceptable salt thereof, wherein:
each of IRAK, Ring I, Ring J, Ring K, L, L¹, R¹, R², X¹, X², X³, and m is as defined above.

In certain embodiments, the present invention provides a compound of formula I-mm:

I-mm

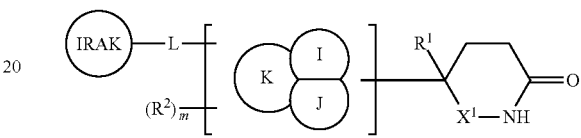

or a pharmaceutically acceptable salt thereof, wherein L and IRAK are as defined above and described in embodiments herein, and wherein:
X¹ is a bivalent moiety selected from a covalent bond, —CH₂—, —C(O)—, —C(S)—, or

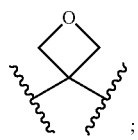 [SMILES: *C1(*)COC1]

R¹ is hydrogen, deuterium, halogen, —CN, —OR, —SR, —S(O)R, —S(O)₂R, —N(R)₂, —Si(R)₃, or an optionally substituted C₁₋₄ aliphatic;

each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, deuterium, —R⁶, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups; and m is 0, 1, 2, 3, or 4.

Where a point of attachment of

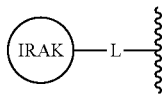

is depicted on Ring I, Ring J, and Ring K, it is intended, and one of ordinary skill in the art would appreciate, that the point of attachment of

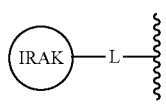

may be on any available carbon or nitrogen atom on Ring I, Ring J, or Ring K, including the carbon atom to which Ring I, Ring J, and Ring K are fused.

Where a point of attachment of $-(R^2)_m$ is depicted on Ring I, Ring J, and Ring K, it is intended, and one of ordinary skill in the art would appreciate, that the point of attachment of $-(R^2)_m$ may be on any available carbon or nitrogen atom on Ring I, Ring J, or Ring K, including the carbon atom to which Ring I, Ring J, and Ring K are fused.

Where a point of attachment of

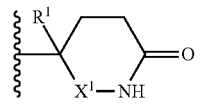

is depicted on Ring I, Ring J, and Ring K, it is intended, and one of ordinary skill in the art would appreciate, that the point of attachment of

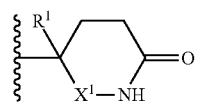

may be on any available carbon or nitrogen atom on Ring I, Ring J, or Ring K, including the carbon atom to which Ring I, Ring J, and Ring K are fused.

In some embodiments, a compound of formula I-mm above is provided as a compound of formula I-mm' or formula I-mm":

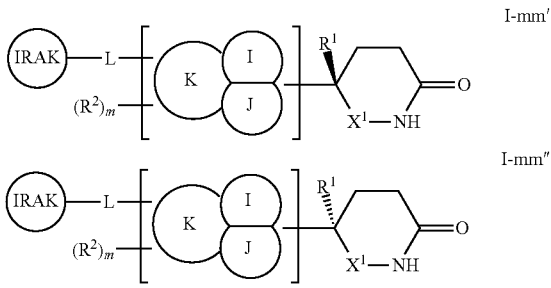

or a pharmaceutically acceptable salt thereof, wherein:
each of IRAK, Ring I, Ring J, Ring K, L, $R^1$, $R^2$, $X^1$, and m is as defined above.

As described above, in another aspect, the present invention provides a compound of Formula I-nn:

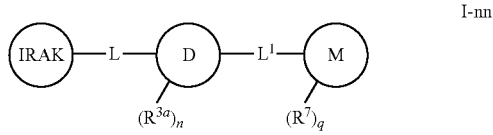

or a pharmaceutically acceptable salt thereof, wherein:
Ring M is selected from

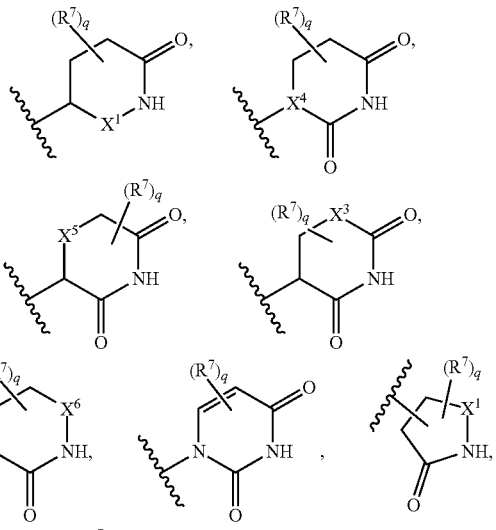

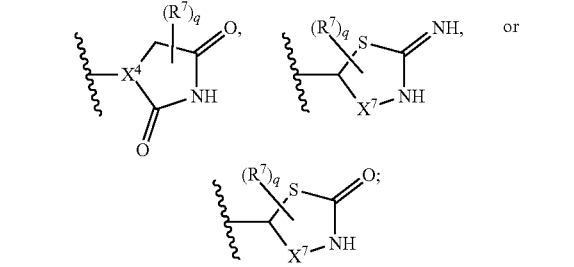

each of $X^1$, $X^6$, and $X^7$ is independently a bivalent moiety selected from a covalent bond, —$CH_2$—, —$CHCF_3$—, —$SO_2$—, —$S(O)$—, —$P(O)R$—, —$P(O)OR$—, —$P(O)NR_2$—, —$C(O)$—, —$C(S)$—, or

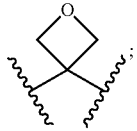 [SMILES: *C1(*)COC1]

each of $X^3$ and $X^5$ is independently a bivalent moiety selected from a covalent bond, —$CR_2$—, —$NR$—, —$O$—, —$S$—, or —$SiR_2$—;

$X^4$ is a trivalent moiety selected from

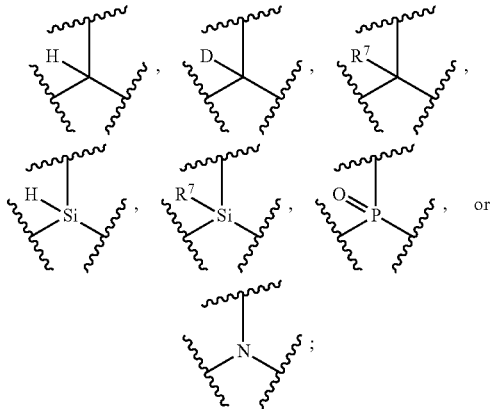

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^{3a}$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —$S(O)R$, —$C(O)R$, —$C(O)OR$, —$C(O)NR_2$, —$C(O)N(R)OR$, —$C(R)_2N(R)C(O)R$, —$C(R)_2N(R)C(O)N(R)_2$, —$OC(O)R$, —$OC(O)N(R)_2$, —$OP(O)R_2$, —$OP(O)(OR)_2$, —$OP(O)(OR)NR_2$, —$OP(O)(NR_2)_2$—, —$N(R)C(O)OR$, —$N(R)C(O)R$, —$N(R)C(O)NR_2$, —$N(R)S(O)_2R$, —$NP(O)R_2$, —$N(R)P(O)(OR)_2$, —$N(R)P(O)(OR)NR_2$, —$N(R)P(O)(NR_2)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each $R^7$ is independently hydrogen, deuterium, halogen, —CN, —OR, —SR, —$S(O)R$, —$S(O)_2R$, —$NR_2$, —$P(O)(OR)_2$, —$P(O)(NR_2)OR$, —$P(O)(NR_2)_2$, —$Si(OH)R_2$, —$Si(OH)_2R$, —$SiR_3$, or an optionally substituted $C_{1-4}$ aliphatic; or $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur;

two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur; two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur;

Ring D is selected from 6 to 10-membered aryl or heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —(C)=CH—;

n is 0, 1, 2, 3, or 4; and q is 0, 1, 2, 3, or 4.

As defined above and described herein, each of $X^1$, $X^6$, and $X^7$ is independently a bivalent moiety selected from a covalent bond, —$CH_2$—, —$C(R)_2$—, —C(O)—, —C(S)—, —CH(R)—, —$CH(CF_3)$—, —P(O)(OR)—, —P(O)(R)—, —$P(O)(NR_2)$—, —S(O)—, —$S(O)_2$—, or

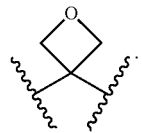

In some embodiments, each of $X^1$, $X^6$, and $X^7$ is independently a covalent bond. In some embodiments, each of $X^1$, $X^6$, and $X^7$ is independently —$CH_2$—. In some embodiments, each of $X^1$, $X^6$, and $X^7$ is independently —$CR_2$—. In some embodiments, each of $X^1$, $X^6$, and $X^7$ is independently —C(O)—. In some embodiments, each of $X^1$, $X^6$, and $X^7$ is independently —C(S)—. In some embodiments, each of $X^1$, $X^6$, and $X^7$ is independently —CH(R)—. In some embodiments, each of $X^1$, $X^6$, and $X^7$ is independently —$CH(CF_3)$—. In some embodiments, each of $X^1$, $X^6$, and $X^7$ is independently —P(O)(OR)—. In some embodiments, each of $X^1$, $X^6$, and $X^7$ is independently —P(O)(R)—. In some embodiments, each of $X^1$, $X^6$, and $X^7$ is independently —P(O)NR$_2$—. In some embodiments, each of $X^1$, $X^6$, and $X^7$ is independently —S(O)—. In some embodiments, each of $X^1$, $X^6$, and $X^7$ is independently —S(O)$_2$—. In some embodiments, each of $X^1$, $X^6$, and $X^7$ is independently

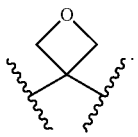 [SMILES: *C1(*)COC1]

In some embodiments, each of $X^1$, $X^6$, and $X^7$ is independently selected from those depicted in Table 1 below.

As defined above and described herein, $X^2$ is a carbon atom, nitrogen atom, or silicon atom.

In some embodiments, $X^2$ is a carbon atom. In some embodiments, $X^2$ is a nitrogen atom. In some embodiments, $X^2$ is a silicon atom.

In some embodiments, $X^2$ is selected from those depicted in Table 1 below.

As defined above and described herein, $X^3$ is a bivalent moiety selected from —CH$_2$—, —CR$_2$—, —NR—, —CF$_2$—, —CHF—, —S—, —CH(R)—, —SiR$_2$—, or —O—.

In some embodiments, each of $X^3$ and $X^5$ is independently —CH$_2$—. In some embodiments, each of $X^3$ and $X^5$ is independently —CR$_2$—. In some embodiments, each of $X^3$ and $X^5$ is independently —NR—. In some embodiments, each of $X^3$ and $X^5$ is independently —CF$_2$—. In some embodiments, each of $X^3$ and $X^5$ is independently —CHF—. In some embodiments, each of $X^3$ and $X^5$ is independently —S—. In some embodiments, each of $X^3$ and $X^5$ is independently —CH(R)—. In some embodiments, each of $X^3$ and $X^5$ is independently —SiR$_2$—. In some embodiments, each of $X^3$ and $X^5$ is independently —O—.

In some embodiments, each of $X^3$ and $X^5$ is independently selected from those depicted in Table 1 below.

As defined above and described herein, $X^4$ is a trivalent moiety selected from

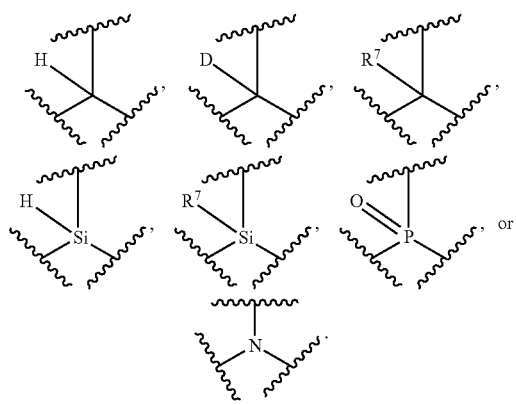

In some embodiments, $X^4$ is

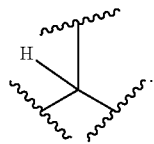 [SMILES: *C(*)*]

In some embodiments, $X^4$ is

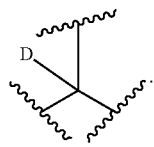 [SMILES: *C(*)(*)[2H]]

In some embodiments, $X^4$ is

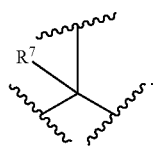

In some embodiments, $X^4$ is

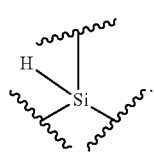 [SMILES: *[SiH](*)*]

In some embodiments, $X^4$ is

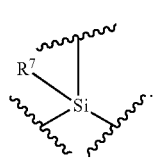

In some embodiments, $X^4$ is

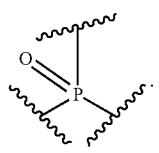 [SMILES: *P(*)(*)=O]

In some embodiments, $X^4$ is

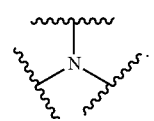

In some embodiments, $X^4$ is selected from those depicted in Table 1 below.

As defined above and described herein, $R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)R$_2$, —SiR$_3$, an optionally substituted $C_{1-4}$ aliphatic, or $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —S(O)$_2$R. In some embodiments, $R^1$ is —NR$_2$. In some embodiments, $R^1$ is —P(O)(OR)$_2$. In some embodiments, $R^1$ is —P(O)(NR$_2$)OR. In some embodiments, $R^1$ is —P(O)(NR$_2$)$_2$. In some embodiments, $R^1$ is —Si(OH)$_2$R. In some embodiments, $R^1$ is —Si(OH)R$_2$. In some embodiments, $R^1$ is —SiR$_3$. In some embodiments, $R^1$ is an optionally substituted $C_{1-4}$ aliphatic. In some embodiments, $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is selected from those depicted in Table 1 below.

As defined above and described herein, each R is independently hydrogen, deuterium, or an optionally substituted group selected from $C_{1-6}$ aliphatic, phenyl, a 4-7 membered saturated or partially unsaturated heterocyclic having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is hydrogen. In some embodiments, R is deuterium. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-3 heteroatoms independently selected from boron, nitrogen, oxygen, silicon, and sulfur. In some embodiments, R is optionally substituted 5-6 membered heteroaryl ring having 1-4 heteroatoms independently selected from boron, nitrogen, oxygen, silicon, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is selected from those depicted in Table 1 below.

As defined above and described herein, each of $R^2$ and $R^{3a}$ is independently hydrogen, deuterium, —$R^6$, halogen, —CN, —NO$_2$, —OR, —Si(OH)$_2$R, —Si(OH)R$_2$, —SR, —NR$_2$, —SiR$_3$, —S(O)$_2$R, —S(O)$_2$NR$_2$, —S(O)R, —C(O)R, —C(O)OR, —C(O)NR$_2$, —C(O)N(R)OR, —C(R)$_2$N(R)C(O)R, —C(R)$_2$N(R)C(O)NR$_2$, —OC(O)R, —OC(O)NR$_2$, —OP(O)R$_2$, —OP(O)(OR)$_2$, —OP(O)(OR)NR$_2$, —OP(O)(NR$_2$)$_2$—, —N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R.

In some embodiments, $R^2$ and/or $R^{3a}$ is hydrogen. In some embodiments, $R^2$ and/or $R^{3a}$ is deuterium. In some embodiments, $R^2$ and/or $R^{3a}$ is —$R^6$. In some embodiments, $R^2$ and/or $R^{3a}$ is halogen. In some embodiments, $R^2$ and/or $R^{3a}$ is —CN. In some embodiments, $R^2$ and/or $R^{3a}$ is —NO$_2$. In some embodiments, $R^2$ and/or $R^{3a}$ is —OR. In some embodiments, $R^2$ and/or $R^{3a}$ is —Si(OH)$_2$R. In some embodiments, $R^2$ and/or $R^{3a}$ is —Si(OH)R$_2$. In some embodiments, $R^2$ and/or $R^{3a}$ is —SR. In some embodiments, $R^2$ and/or $R^{3a}$ is —NR$_2$. In some embodiments, $R^2$ and/or $R^{3a}$ is —SiR$_3$. In some embodiments, $R^2$ and/or $R^{3a}$ is —S(O)$_2$R. In some embodiments, $R^2$ and/or $R^{3a}$ is —S(O)$_2$NR$_2$. In some embodiments, $R^2$ and/or $R^{3a}$ is —S(O)R. In some embodiments, $R^2$ and/or $R^{3a}$ is —C(O)R. In some embodiments, $R^2$ and/or $R^{3a}$ is —C(O)OR. In some embodiments, $R^2$ and/or $R^{3a}$ is —C(O)NR$_2$. In some embodiments, $R^2$ and/or $R^{3a}$ is —C(O)N(R)OR. In some embodiments, $R^2$ and/or $R^{3a}$ is —C(R)$_2$N(R)C(O)R. In some embodiments, $R^2$ and/or $R^{3a}$ is —C(R)$_2$N(R)C(O)NR$_2$. In some embodiments, $R^2$ and/or $R^{3a}$ is —OC(O)R. In some embodiments, $R^2$ and/or $R^{3a}$ is —OC(O)NR$_2$. In some embodiments, $R^2$ and/or $R^{3a}$ is —OP(O)R$_2$. In some embodiments, $R^2$ and/or $R^{3a}$ is —OP(O)(OR)$_2$. In some embodiments, $R^2$ and/or $R^{3a}$ is —OP(O)(OR)NR$_2$. In some embodiments, $R^2$ and/or $R^{3a}$ is —OP(O)(NR$_2$)$_2$—. In some embodiments, $R^2$ and/or $R^{3a}$ is —N(R)C(O)OR. In some embodiments, $R^2$ and/or $R^{3a}$ is —N(R)C(O)R. In some embodiments, $R^2$ and/or $R^{3a}$ is —N(R)C(O)NR$_2$. In some embodiments, $R^2$ and/or $R^{3a}$ is —NP(O)R$_2$. In some embodiments, $R^2$ and/or $R^{3a}$ is —N(R)P(O)(OR)$_2$. In some embodiments, $R^2$ and/or $R^{3a}$ is —N(R)P(O)(OR)NR$_2$. In some embodiments, $R^2$ and/or $R^{3a}$ is —N(R)P(O)(NR$_2$)$_2$. In some embodiments, $R^2$ and/or $R^{3a}$ is —N(R)S(O)$_2$R.

In some embodiments, $R^2$ and/or $R^{3a}$ is —OH. In some embodiments, $R^2$ and/or $R^{3a}$ is —NH$_2$. In some embodiments, $R^2$ and/or $R^{3a}$ is —CH$_2$NH$_2$. In some embodiments, $R^2$ and/or $R^{3a}$ is —CH$_2$NHCOMe. In some embodiments, $R^2$ and/or $R^{3a}$ is —CH$_2$NHCONHMe. In some embodiments, $R^2$ and/or $R^{3a}$ is —NHCOMe. In some embodiments, $R^2$ and/or $R^{3a}$ is —NHCONHEt. In some embodiments, $R^2$ and/or $R^{3a}$ is —SiMe$_3$. In some embodiments, $R^2$ and/or $R^{3a}$ is —SiMe$_2$OH. In some embodiments, $R^2$ and/or $R^{3a}$ is —SiMe(OH)$_2$. In some embodiments $R^2$ and/or $R^{3a}$ is

In some embodiments, $R^2$ and/or $R^{3a}$ is Br. In some embodiments, $R^2$ and/or $R^{3a}$ is Cl. In some embodiments, $R^2$ and/or $R^{3a}$ is F. In some embodiments, $R^2$ and/or $R^{3a}$ is Me. In some embodiments, $R^2$ and/or $R^{3a}$ is —NHMe. In some embodiments, $R^2$ and/or $R^{3a}$ is —NMe$_2$. In some embodiments, $R^2$ and/or $R^{3a}$ is —NHCO$_2$Et. In some embodiments, $R^2$ and/or $R^{3a}$ is —CN. In some embodiments, $R^2$ and/or $R^{3a}$ is —CH$_2$Ph. In some embodiments, $R^2$ and/or $R^{3a}$ is —NHCO$_2$tBu. In some embodiments, $R^2$ and/or $R^{3a}$ is —CO$_2$tBu. In some embodiments, $R^2$ and/or $R^{3a}$ is —OMe. In some embodiments, $R^2$ and/or $R^{3a}$ is —CF$_3$.

In some embodiments, $R^2$ and $R^{3a}$ is selected from those depicted in Table 1 below.

As defined above and described herein, $R^3$ is hydrogen, deuterium, halogen, —CN, —NO$_2$, —OR, —NR$_2$, —SR, —S(O)$_2$R, —S(O)$_2$NR$_2$, —S(O)R, —C(O)R, —C(O)OR, —C(O)NR$_2$, —C(O)NR(OR), —OC(O)R, —OC(O)NR$_2$, —OP(O)(OR)$_2$, —OP(O)(NR$_2$)$_2$, —OP(O)(OR)NR$_2$, —N(R)C(O)R, —N(R)C(O)OR, —N(R)C(O)NR$_2$, —N(R)S(O)$_2$R, —N(R)S(O)$_2$NR$_2$, —N(R)P(O)(OR)$_2$, —N(R)P(O)(OR)NR$_2$, —P(O)(OR)$_2$, —P(O)(NR$_2$)OR, —P(O)(NR$_2$)$_2$, —Si(OH)$_2$R, —Si(OH)(R)$_2$, or —Si(R)$_3$.

In some embodiments, $R^3$ is hydrogen. In some embodiments, $R^3$ is deuterium. In some embodiments, $R^3$ is halogen. In some embodiments, $R^3$ is —CN. In some embodiments, $R^3$ is —NO$_2$. In some embodiments, $R^3$ is —OR. In some embodiments, $R^3$ is —NR$_2$. In some embodiments, $R^3$ is —SR. In some embodiments, $R^3$ is —S(O)$_2$R. In some embodiments, $R^3$ is —S(O)$_2$NR$_2$. In some embodiments, $R^3$ is —S(O)R. In some embodiments, $R^3$ is —C(O)R. In some embodiments, $R^3$ is —C(O)OR. In some embodiments, $R^3$ is —C(O)NR$_2$. In some embodiments, $R^3$ is —C(O)NR(OR). In some embodiments, $R^3$ is —OC(O)R. In some embodiments, $R^3$ is —OC(O)NR$_2$. In some embodiments, $R^3$ is —OP(O)(OR)$_2$. In some embodiments, $R^3$ is —OP(O)(NR$_2$)$_2$. In some embodiments, $R^3$ is —OP(O)(OR)NR$_2$. In some embodiments, $R^3$ is —N(R)C(O)R. In some embodiments, $R^3$ is —N(R)C(O)OR. In some embodiments, $R^3$ is —N(R)C(O)NR$_2$. In some embodiments, $R^3$ is —N(R)S(O)$_2$R. In some embodiments, $R^3$ is —N(R)S(O)$_2$NR$_2$. In some embodiments, $R^3$ is —N(R)P(O)(OR)$_2$. In some embodiments, $R^3$ is —N(R)P(O)(OR)NR$_2$. In some embodiments, $R^3$ is —P(O)(OR)$_2$. In some embodiments, $R^3$ is —P(O)(NR$_2$)OR. In some embodiments, $R^3$ is —P(O)(NR$_2$)$_2$. In some embodiments, $R^3$ is —Si(OH)$_2$R. In some embodiments, $R^3$ is —Si(OH)(R)$_2$. In some embodiments, $R^3$ is —Si(R)$_3$.

In some embodiments, $R^3$ is methyl. In some embodiments, $R^3$ is —OCH$_3$. In some embodiments, $R^3$ is chloro.

In some embodiments, $R^3$ is selected from those depicted in Table 1.

As defined above and described herein, each $R^4$ is independently hydrogen, deuterium, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)NR$_2$, —N(R)S(O)$_2$R, —P(O)(OR)$_2$, —P(O)(NR$_2$)OR, or —P(O)(NR$_2$)$_2$.

In some embodiments, $R^4$ is hydrogen. In some embodiments, $R^4$ is —$R^6$. In some embodiments, $R^4$ is halogen. In some embodiments, $R^4$ is —CN. In some embodiments, $R^4$ is —NO$_2$. In some embodiments, $R^4$ is —OR. In some embodiments, $R^4$ is —SR. In some embodiments, $R^4$ is —NR$_2$. In some embodiments, $R^4$ is —S(O)$_2$R. In some embodiments, $R^4$ is —S(O)$_2$NR$_2$. In some embodiments, $R^4$ is —S(O)R. In some embodiments, $R^4$ is —C(O)R. In some embodiments, $R^4$ is —C(O)OR. In some embodiments, $R^4$ is —C(O)NR$_2$. In some embodiments, $R^4$ is —C(O)N(R)OR. In some embodiments, $R^4$ is —OC(O)R. In some embodiments, $R^4$ is —OC(O)NR$_2$. In some embodiments, $R^4$ is —N(R)C(O)OR. In some embodiments, $R^4$ is —N(R)C(O)R. In some embodiments, $R^4$ is —N(R)C(O)NR$_2$. In some embodiments, is —N(R)S(O)$_2$R. In some embodiments, $R^4$ is —P(O)(OR)$_2$. In some embodiments, $R^4$ is —P(O)(NR$_2$)OR. In some embodiments, $R^4$ is —P(O)(NR$_2$)$_2$.

In some embodiments, $R^4$ is methyl. In some embodiments, $R^4$ is ethyl. In some embodiments, $R^4$ is cyclopropyl.

In some embodiments, $R^4$ is selected from those depicted in Table 1.

As defined above and described herein, $R^5$ is hydrogen, deuterium, an optionally substitute C$_{1-4}$ aliphatic, or —CN.

In some embodiments, $R^5$ is hydrogen. In some embodiments, $R^5$ is deuterium. In some embodiments, $R^5$ is an optionally substituted C$_{1-4}$ aliphatic. In some embodiments, $R^5$ is —CN.

In some embodiments, $R^5$ is selected from those depicted in Table 1.

As defined above and described herein, each $R^6$ is independently an optionally substituted group selected from C$_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, $R^6$ is an optionally substituted C$_{1-6}$ aliphatic. In some embodiments, $R^6$ is an optionally substituted phenyl. In some embodiments, $R^6$ is an optionally substituted 4-7 membered saturated or partially unsaturated heterocyclic ring having 1-3 heteroatoms independently selected from boron, nitrogen, oxygen, silicon, and sulfur. In some embodiments, $R^6$ is an optionally substituted 5-6 membered heteroaryl ring having 1-4 heteroatoms independently selected from boron, nitrogen, oxygen, silicon, and sulfur.

In some embodiments, $R^6$ is selected from those depicted in Table 1.

As defined generally above, each $R^7$ is independently hydrogen, deuterium, halogen, —CN, —OR, —SR, —S(O)R, —S(O)$_2$R, —N(R)$_2$, —P(O)(R)$_2$, —P(O)(OR)$_2$, —P(O)(NR$_2$)OR, —P(O)(NR$_2$)$_2$, —Si(OH)R$_2$, —Si(OH)$_2$R, —SiR$_3$, or an optionally substituted C$_{1-4}$ aliphatic, or $R^1$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur, or two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur, or two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, $R^7$ is hydrogen. In some embodiments, $R^7$ is deuterium. In some embodiments, $R^7$ is halogen. In some embodiments, $R^7$ is —CN. In some embodiments, $R^7$ is —OR. In some embodiments, $R^7$ is —SR. In some embodiments, $R^7$ is —S(O)R. In some embodiments, $R^7$ is —S(O)$_2$R. In some embodiments, $R^7$ is —NR$_2$. In some embodiments, $R^7$ is —Si(R)$_3$. In some embodiments, $R^7$ is —P(O)(R)$_2$. In some embodiments, $R^7$ is —P(O)(OR)$_2$. In some embodiments, $R^7$ is —P(O)(NR$_2$)OR. In some embodiments, $R^7$ is —P(O)(NR$_2$)$_2$. In some embodiments, $R^7$ is —Si(OH)R$_2$. In some embodiments, $R^7$ is —Si(OH)$_2$R. In some embodiments, $R^7$ is an optionally substituted C$_{1-4}$ aliphatic. In some embodiments, $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur. In some embodiments, two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur. In some embodiments, two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur. In some embodiments, two $R^7$ groups on adjacent carbon atoms are optionally taken together with their intervening atoms to form a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, $R^7$ is selected from hydrogen, halogen, —CN, —OR, —NR$_2$, or C$_{1-4}$ alkyl. In some embodiments, $R^7$ is selected from hydrogen, halogen, —CN, or C$_{1-4}$ alkyl. In some embodiments, $R^7$ is fluoro. In some embodiments, two $R^7$ groups on the same carbon are optionally taken together with their intervening atoms to form a 3- or 4-membered spiro fused ring.

In some embodiments, $R^7$ is selected from those depicted in Table 1 below.

As defined above and described herein, Ring A is a bi- or tricyclic ring selected from

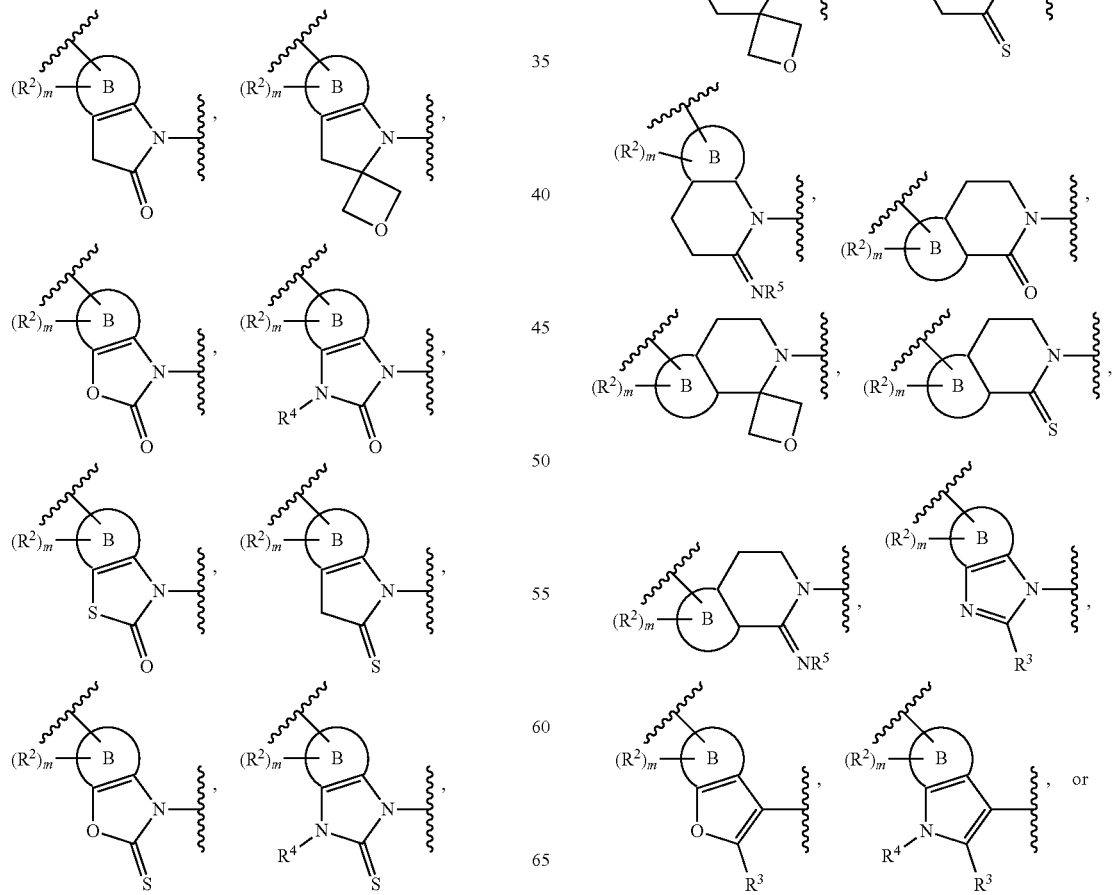

-continued
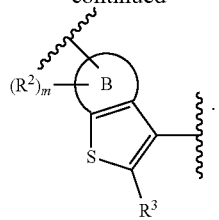
In some embodiments, Ring A is
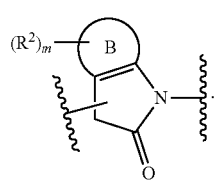
In some embodiments, Ring A is
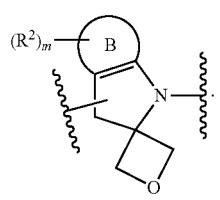
In some embodiments, Ring A is
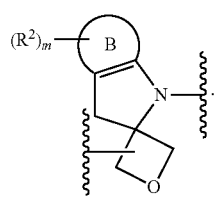
In some embodiments, Ring A is
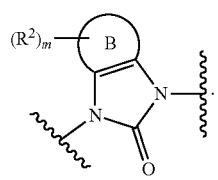
In some embodiments, Ring A is
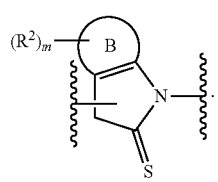
In some embodiments, Ring A is
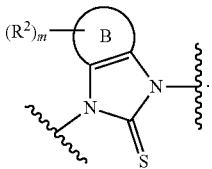
In some embodiments, Ring A is
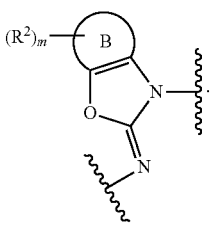
In some embodiments, Ring A is
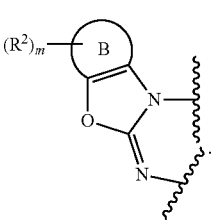
In some embodiments, Ring A is
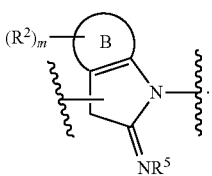
In some embodiments, Ring A is
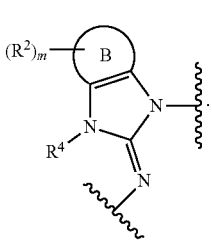

In some embodiments, Ring A is
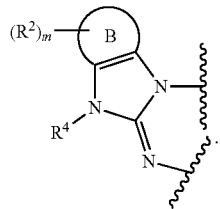
In some embodiments, Ring A is
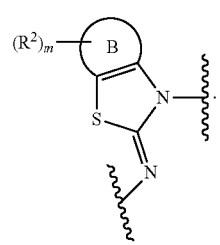
In some embodiments, Ring A is
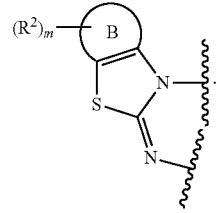
In some embodiments, Ring A is
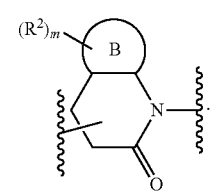
In some embodiments, Ring A is
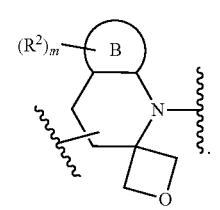
In some embodiments, Ring A is
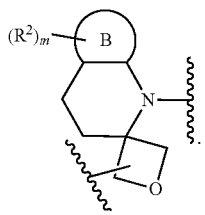
In some embodiments, Ring A is
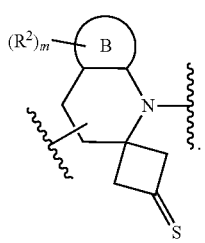
In some embodiments, Ring A is
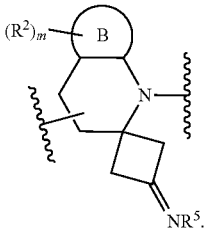
In some embodiments, Ring A is
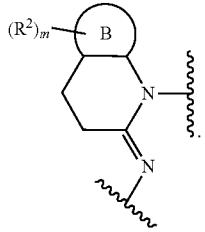
In some embodiments, Ring A is
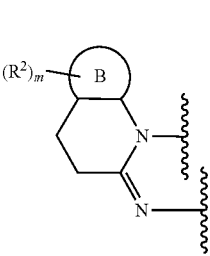

In some embodiments, Ring A is
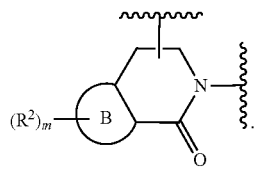
In some embodiments, Ring A is
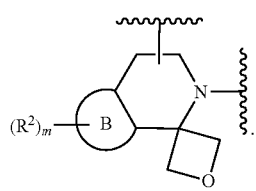
In some embodiments, Ring A is
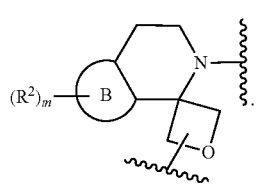
In some embodiments, Ring A is
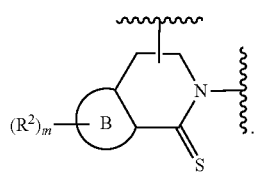
In some embodiments, Ring A is
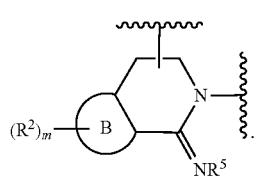
In some embodiments, Ring A is
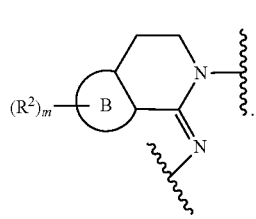
In some embodiments, Ring A is
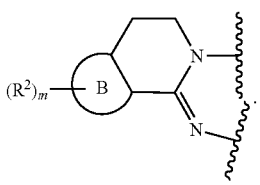
In some embodiments, Ring A is
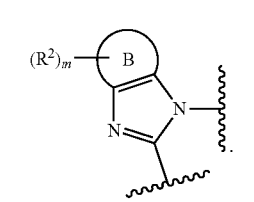
In some embodiments, Ring A is
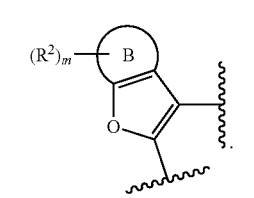
In some embodiments, Ring A is
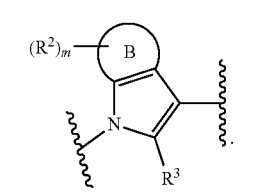
In some embodiments, Ring A is
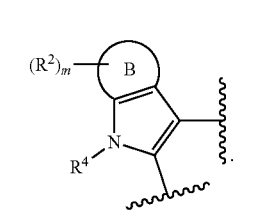
In some embodiments, Ring A is
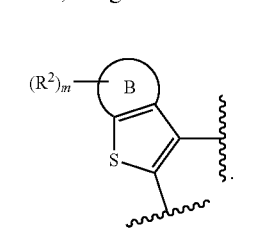

In some embodiments, Ring A is selected from those depicted in Table 1 below.

As defined above and described herein, Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring B is a fused 6-membered aryl. In some embodiments, Ring B is a fused 6-membered heteroaryl containing 1-4 heteroatoms independently selected from nitrogen, oxygen, or sulfur. In some embodiments, Ring B is a fused 5 to 7-membered saturated or partially unsaturated carbocyclyl. In some embodiments, Ring B is fused 5 to 7-membered saturated or partially saturated heterocyclyl with 1-3 heteroatoms independently selected from boron, nitrogen, oxygen, silicon, or sulfur. In some embodiments, Ring B is fused 5-membered heteroaryl with 1-4 heteroatoms independently selected from boron, nitrogen, oxygen, silicon, or sulfur.

In some embodiments, Ring B is

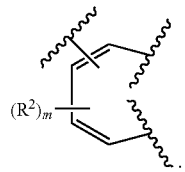

In some embodiments, Ring B is

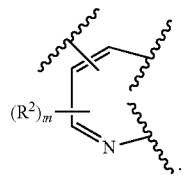

In some embodiments, Ring B is

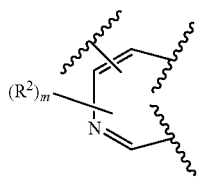

In some embodiments, Ring B is selected from those depicted in Table 1 below.

As defined above and described herein, Ring C is a mono- or bicyclic ring selected from

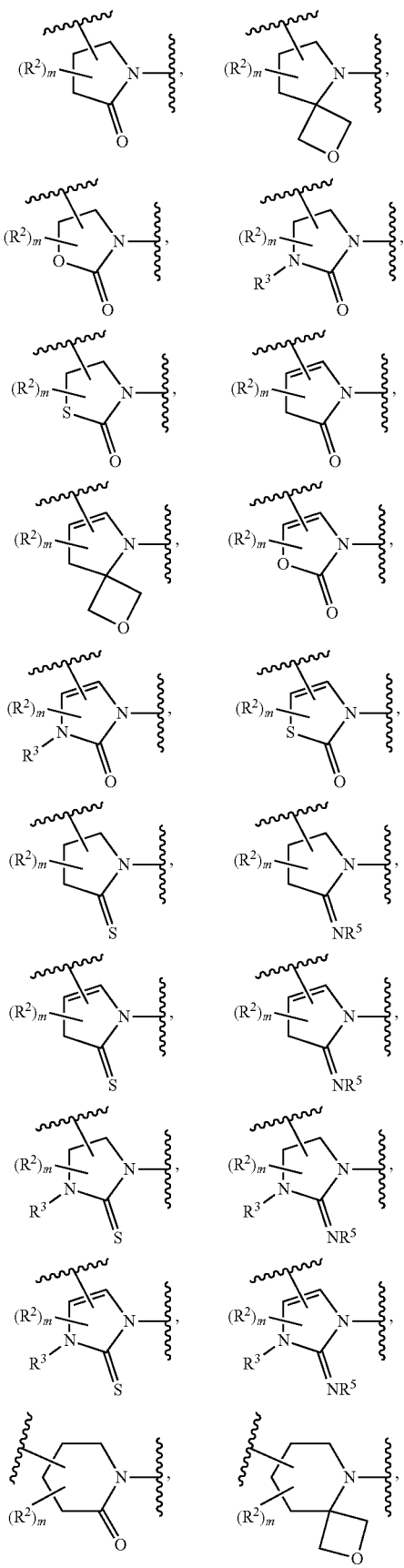

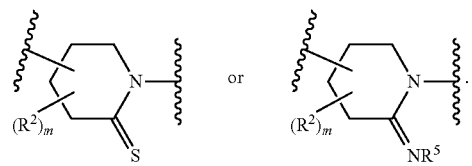 or 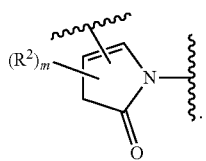
In some embodiments, Ring C is
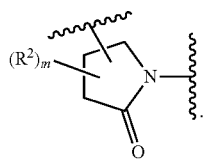
In some embodiments, Ring C is
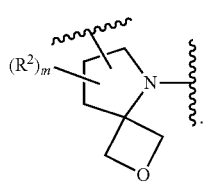
In some embodiments, Ring C is
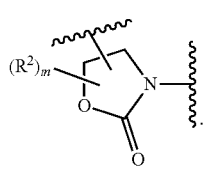
In some embodiments, Ring C is
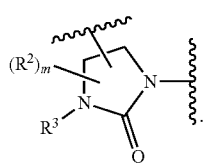
In some embodiments, Ring C is
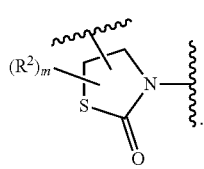
In some embodiments, Ring C is
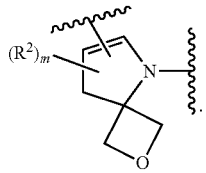
In some embodiments, Ring C is
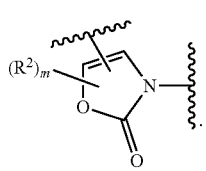
In some embodiments, Ring C is
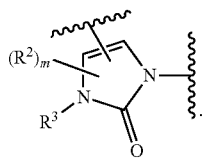
In some embodiments, Ring C is
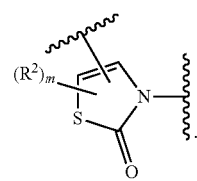
In some embodiments, Ring C is
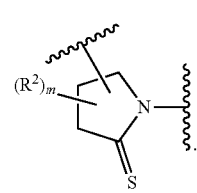

In some embodiments, Ring C is
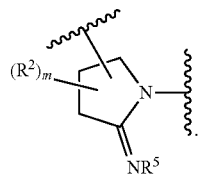
In some embodiments, Ring C is
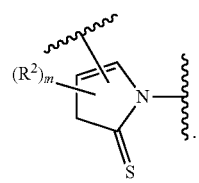
In some embodiments, Ring C is
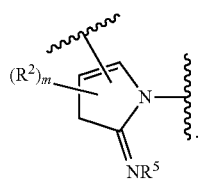
In some embodiments, Ring C is
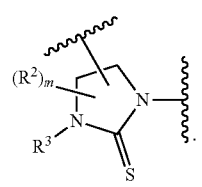
In some embodiments, Ring C is
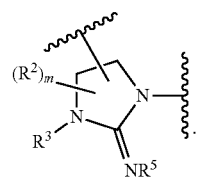
In some embodiments, Ring C is
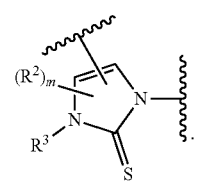
In some embodiments, Ring C is
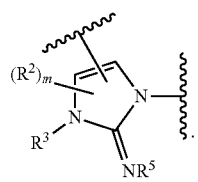
In some embodiments, Ring C is
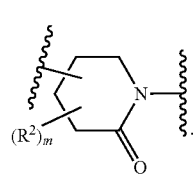
In some embodiments, Ring C is
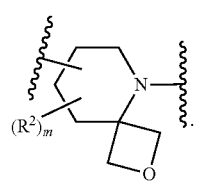
In some embodiments, Ring C is
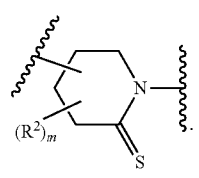
In some embodiments, Ring C is
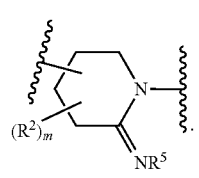
In some embodiments, Ring C is
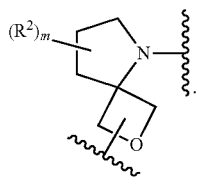

In some embodiments, Ring C is
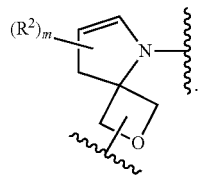
In some embodiments, Ring C is
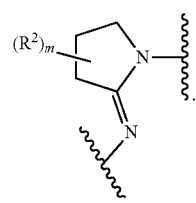
In some embodiments, Ring C is
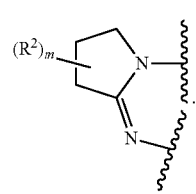
In some embodiments, Ring C is
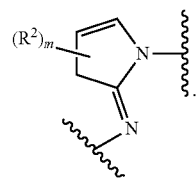
In some embodiments, Ring C is
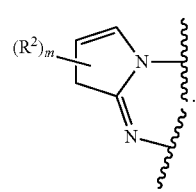
In some embodiments, Ring C is
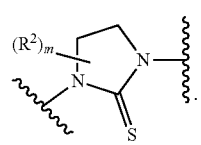
In some embodiments, Ring C is
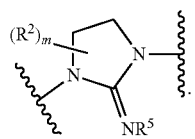
In some embodiments, Ring C is
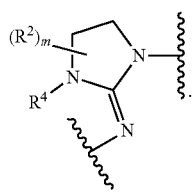
In some embodiments, Ring C is
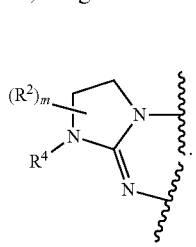
In some embodiments, Ring C is
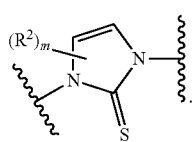
In some embodiments, Ring C is
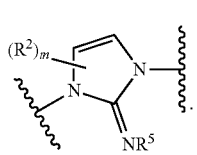
In some embodiments, Ring C is
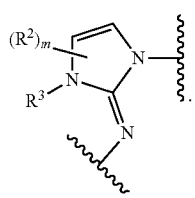

In some embodiments, Ring C is
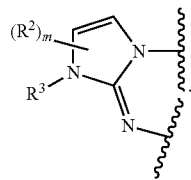
In some embodiments, Ring C is
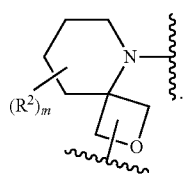
In some embodiments, Ring C is
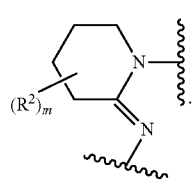
In some embodiments, Ring C is
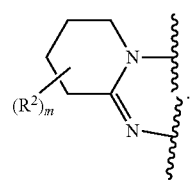
In some embodiments, Ring C is a mono- or bicyclic ring selected from
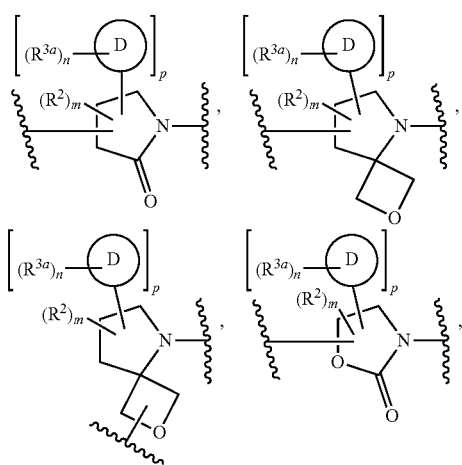
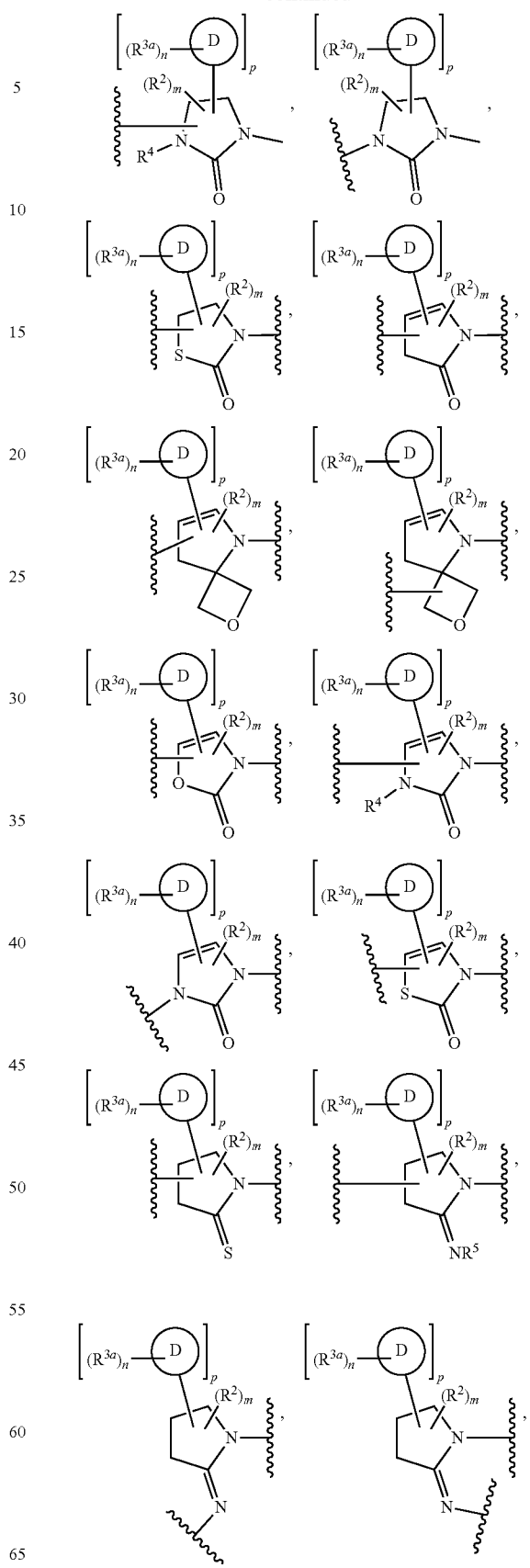

-continued

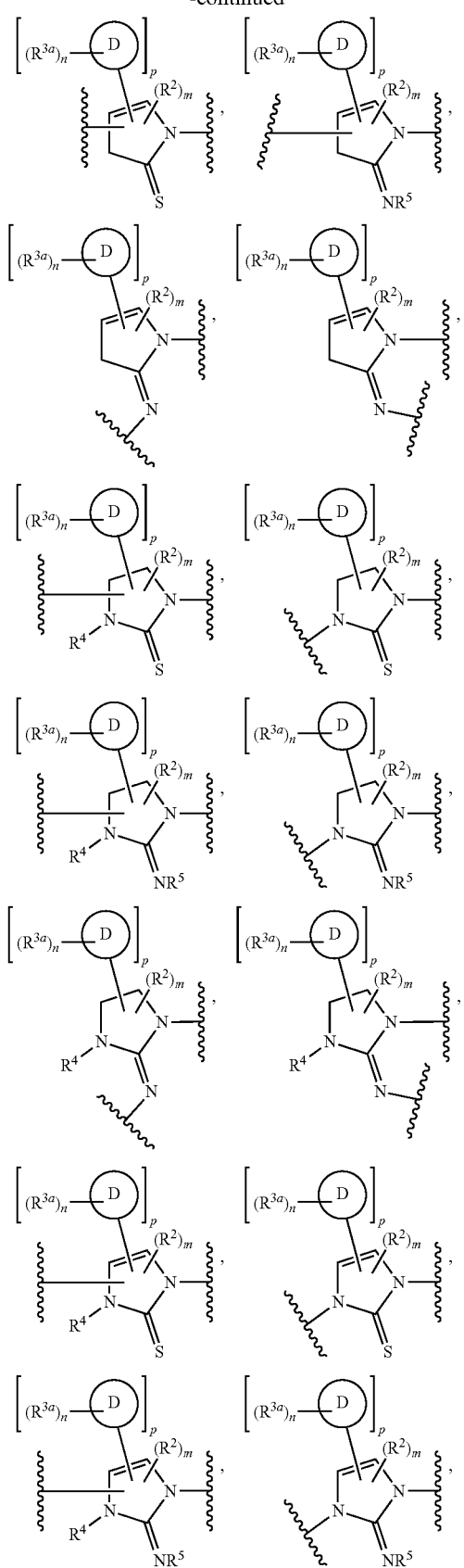

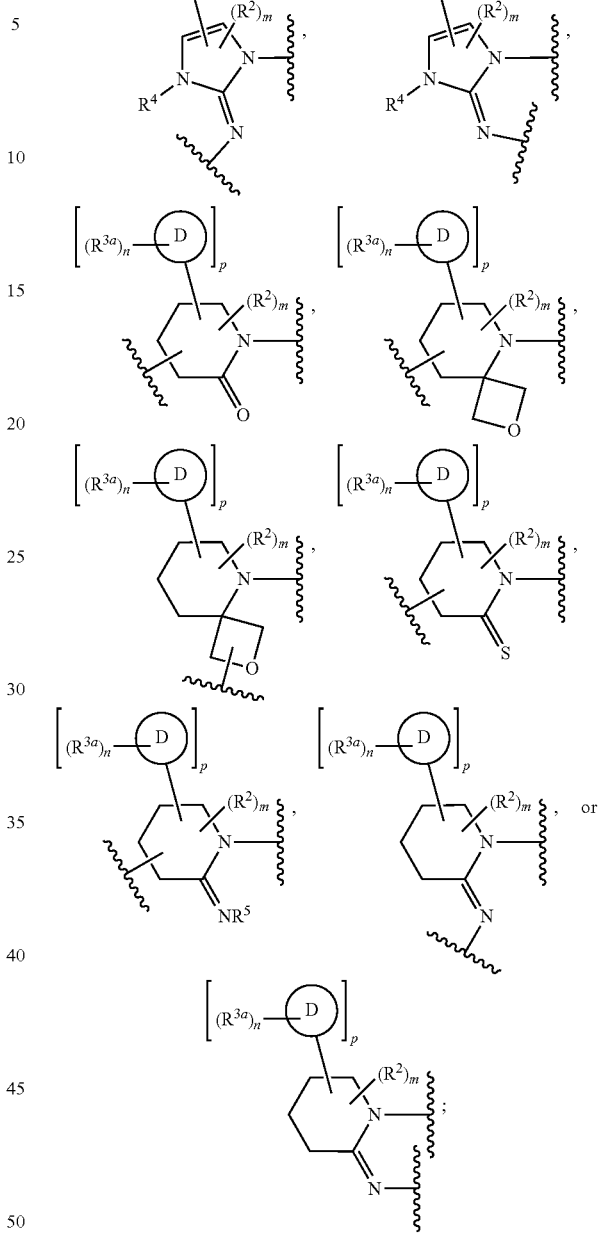

In some embodiments, Ring C is selected from those depicted in Table 1 below.

As defined above and described herein, Ring D is a ring selected from 6 to 10-membered aryl or heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring D is a 6 to 10-membered aryl. In some embodiments, Ring D is a 6 to 10-membered heteroaryl containing 1-4 heteroatoms independently selected from nitrogen, oxygen, or sulfur. In some embodiments, Ring D is a 5 to 7-membered saturated or partially unsaturated carbocyclyl. In some embodiments, Ring D is 5 to 7-membered saturated or partially saturated heterocyclyl with 1-3 heteroatoms independently selected from boron, nitrogen, oxygen, silicon, or sulfur. In some embodiments, Ring D is 5-membered heteroaryl with 1-4 heteroatoms independently selected from boron, nitrogen, oxygen, silicon, or sulfur. In some embodiments, Ring D in phenyl. In some embodiments, Ring D is pyridinyl.

In some embodiments, Ring D is selected from those depicted in Table 1 below.

As defined above and described herein, each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur, wherein Ring E, Ring F, and Ring G is independently and optionally substituted with 1-2 oxo groups.

In some embodiments, each of Ring E, Ring F, and Ring G is independently a fused ring selected from 6-membered aryl. In some embodiments, each of Ring E, Ring F, and Ring G is independently a fused ring selected from 6-membered heteroaryl containing 1-4 heteroatoms independently selected from nitrogen, oxygen, or sulfur. In some embodiments, each of Ring E, Ring F, and Ring G is independently a fused ring selected from a 5 to 7-membered saturated or partially unsaturated carbocyclyl. In some embodiments, each of Ring E, Ring F, and Ring G is independently a fused ring selected from a 5 to 7-membered saturated or partially unsaturated heterocyclyl with 1-3 heteroatoms independently selected from boron, nitrogen, oxygen, silicon, or sulfur. In some embodiments, each of Ring E, Ring F, and Ring G is independently a fused ring selected from a 5-membered heteroaryl with 1-4 heteroatoms independently selected from nitrogen, oxygen or sulfur. In some embodiments, Ring E, Ring F, and Ring G is independently and optionally substituted with 1-2 oxo groups.

In some embodiments, Ring F is

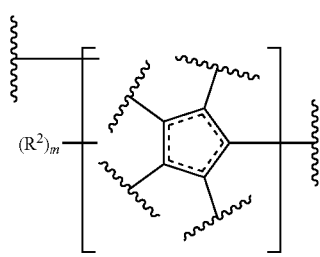

In some embodiments, each of Ring E and Ring G is independently

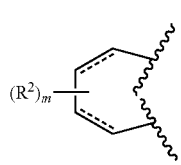

In some embodiments, each of Ring E and Ring G is independently

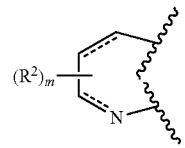

In some embodiments, each of Ring E and Ring G is independently

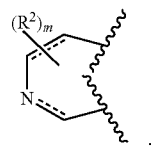

In some embodiments, each of Ring E and Ring G is independently

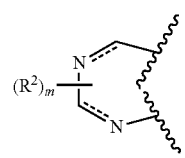

In some embodiments, each of Ring E and Ring G is independently

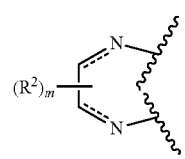

In some embodiments, Ring E, Ring F, and Ring G is

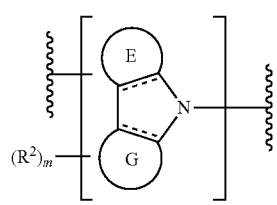

In some embodiments, Ring E, Ring F, and Ring G is

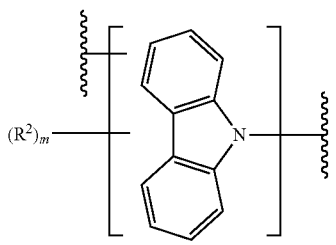

In some embodiments, Ring E, Ring F, and Ring G is

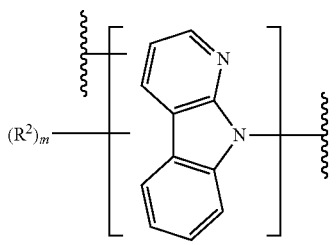

In some embodiments, Ring E, Ring F, and Ring G is selected from those depicted in Table 1, below.

As defined above and described herein, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

As defined above and described herein, each of Ring I and Ring J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring I and Ring J is independently a 6-membered aryl. In some embodiments, each of Ring I and Ring J is independently a 6-membered heteroaryl containing 1-4 heteroatoms independently selected from nitrogen, oxygen, or sulfur. In some embodiments, each of Ring I and Ring J is independently a 5 to 7-membered saturated or partially unsaturated carbocyclyl. In some embodiments, each of Ring I and Ring J is independently a 5 to 7-membered saturated or partially unsaturated heterocyclyl with 1-3 heteroatoms independently selected from boron, nitrogen, oxygen, silicon, or sulfur. In some embodiments, each of Ring I and Ring J is independently a 5-membered heteroaryl with 1-3 heteroatoms independently selected from nitrogen, oxygen or sulfur.

In some embodiments, Ring I and Ring J is selected from those depicted in Table 1, below.

As defined above and described herein, Ring K is a fused ring selected from a 7-12 membered saturated or partially unsaturated carbocyclyl or heterocyclyl with 1-3 heteroatoms independently selected from boron, nitrogen, oxygen, silicon, or sulfur, wherein Ring H is optionally further substituted with 1-2 oxo groups.

In some embodiments, Ring K is a fused ring selected from a 7-12 membered saturated or partially unsaturated carbocyclyl. In some embodiments, Ring K is a 7-12 membered saturated or partially unsaturated heterocyclyl ring with 1-3 heteroatoms independently selected from boron, nitrogen, oxygen, silicon, or sulfur. In some embodiments, Ring K is optionally further substituted with 1-2 oxo groups.

In some embodiments, Ring K is selected from those depicted in Table 1 below.

As defined above and described herein, Ring M is selected from

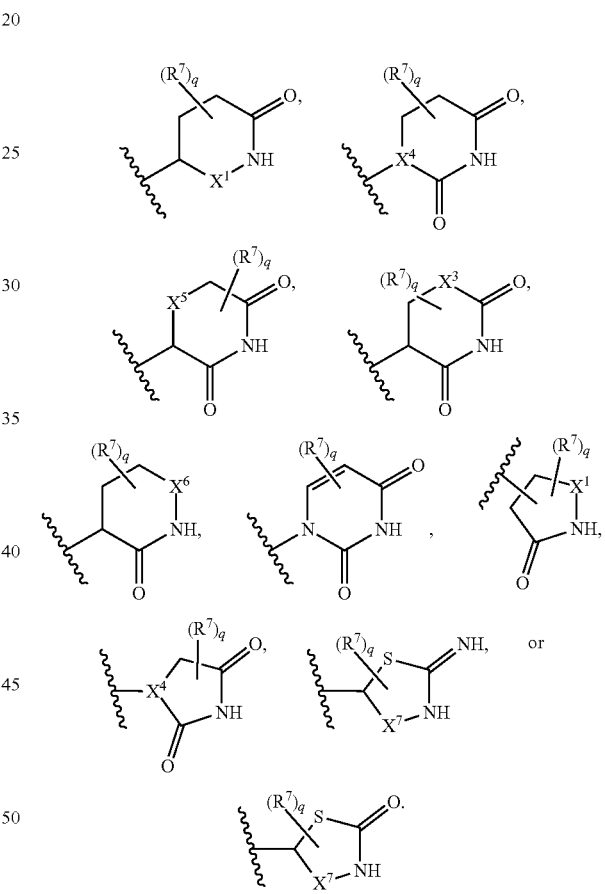

In some embodiments, Ring M is

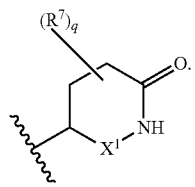

In some embodiments, Ring M is

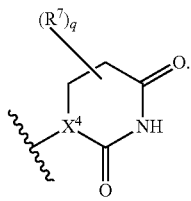

In some embodiments, Ring M is

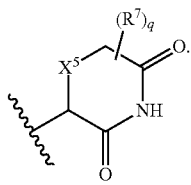

In some embodiments, Ring M is

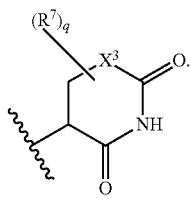

In some embodiments, Ring M is

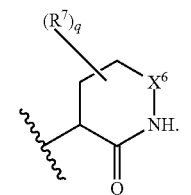

In some embodiments, Ring M is

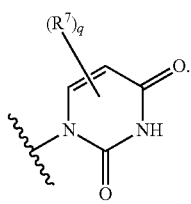

In some embodiments, Ring M is

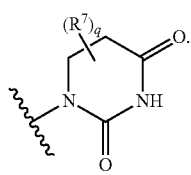

In some embodiments, Ring M is

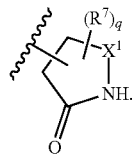

In some embodiments, Ring M is

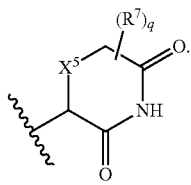

In some embodiments, Ring M is

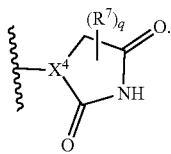

In some embodiments, Ring M is

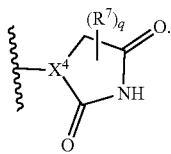

In some embodiments, Ring M is selected from those depicted in Table 1 below.

As defined above and described here, $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —(C)=CH—;

In some embodiments, $L^1$ is a covalent bond. In some embodiments, $L^1$ is a $C_{1-3}$ aliphatic. In some embodiments, $L^1$ is —CH$_2$—. In some embodiments, $L^1$ is —C(D)(H)—. In some embodiments, $L^1$ is —C(D)$_2$-. In some embodiments, $L^1$ is —CH$_2$CH$_2$—. In some embodiments, $L^1$ is —NR—. In some embodiments, $L^1$ is —CH$_2$NR—. In some embodiments, $L^1$ is or —O—. In some embodiments, $L^1$ is —CH$_2$O—. In some embodiments, $L^1$ is —S—. In some embodiments, $L^1$ is —OC(O)—. In some embodiments, $L^1$ is —C(O)O—. In some embodiments, $L^1$ is —C(O)—. In some embodiments, $L^1$ is —S(O)—. In some embodiments, $L^1$ is —S(O)$_2$—. In some embodiments, $L^1$ is —NRS(O)$_2$—. In some embodiments, $L^1$ is —S(O)$_2$NR—. In some embodiments, $L^1$ is —NRC(O)—. In some embodiments, $L^1$ is —C(O)NR—.

In some embodiments, Ring $L^1$ is selected from those depicted in Table 1 below.

As defined above and described herein, ═══ is a single or double bond.

In some embodiments, ═══ is a single bond. In some embodiments, ═══ is a double bond.

In some embodiments, ▬▬▬ is selected from those depicted in Table 1 below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1 below.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In some embodiments, n is selected from those depicted in Table 1 below.

As defined above and described herein, p is 0 or 1.

In some embodiments, p is 0. In some embodiments, p is 1.

In some embodiments, p is selected from those depicted in Table 1 below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1 below.

In some embodiments, LBM is

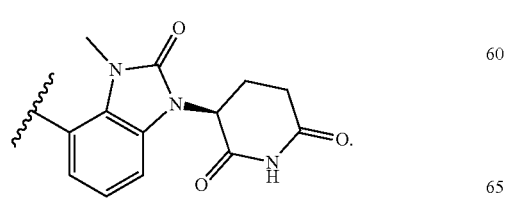

In some embodiments, LBM is

In some embodiments, LBM is

In some embodiments, LBM is

In some embodiments, LBM is

In some embodiments, LBM is

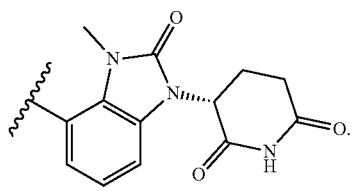

In some embodiments, LBM is

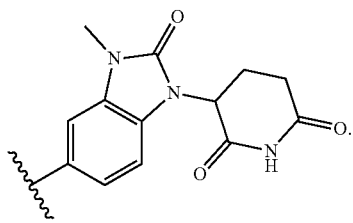 [SMILES: *c1ccc2c(c1)n(C)c(=O)n2C1CCC(=O)NC1=O]

In some embodiments, LBM is

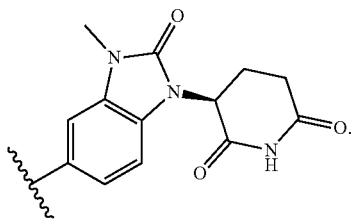 [SMILES: *c1ccc2c(c1)n(C)c(=O)n2[C@H]1CCC(=O)NC1=O]

In some embodiments, LBM is

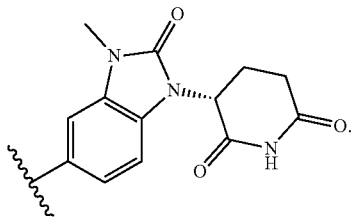 [SMILES: *c1ccc2c(c1)n(C)c(=O)n2[C@@H]1CCC(=O)NC1=O]

In some embodiments, LBM is

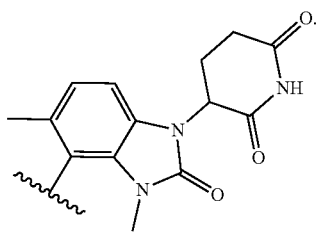 [SMILES: *c1c(C)ccc2c1n(C)c(=O)n2C1CCC(=O)NC1=O]

In some embodiments, LBM is
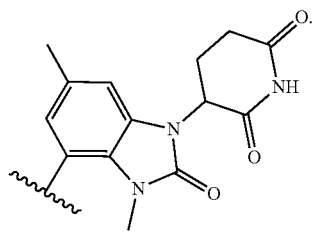 [SMILES: *c1cc(C)cc2c1n(C)c(=O)n2C1CCC(=O)NC1=O]
In some embodiments, LBM is
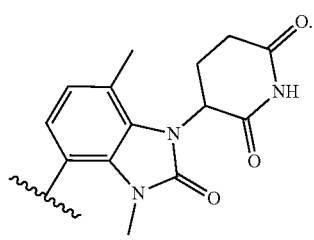 [SMILES: *c1ccc(C)c2c1n(C)c(=O)n2C1CCC(=O)NC1=O]
In some embodiments, LBM is
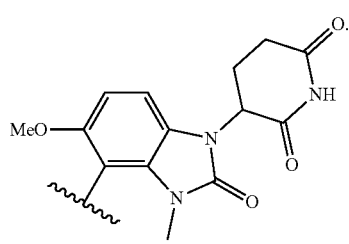 [SMILES: *c1c(OC)ccc2c1n(C)c(=O)n2C1CCC(=O)NC1=O]
In some embodiments, LBM is
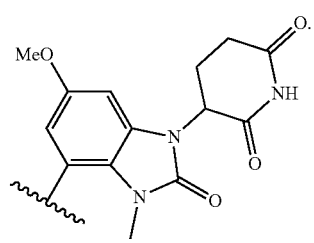 [SMILES: *c1cc(OC)cc2c1n(C)c(=O)n2C1CCC(=O)NC1=O]
In some embodiments, LBM is
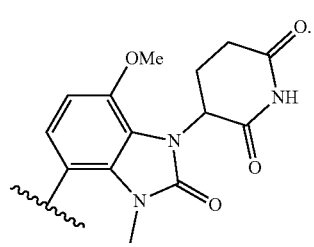 [SMILES: *c1ccc(OC)c2c1n(C)c(=O)n2C1CCC(=O)NC1=O]
In some embodiments, LBM is
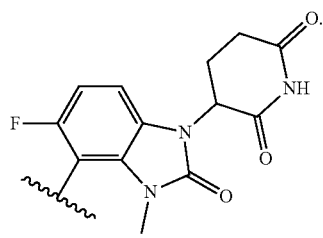 [SMILES: *c1c(F)ccc2c1n(C)c(=O)n2C1CCC(=O)NC1=O]
In some embodiments, LBM is
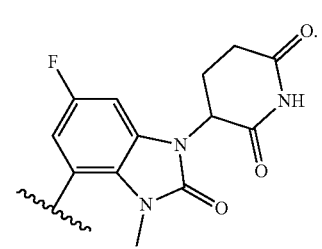 [SMILES: *c1cc(F)cc2c1n(C)c(=O)n2C1CCC(=O)NC1=O]
In some embodiments, LBM is
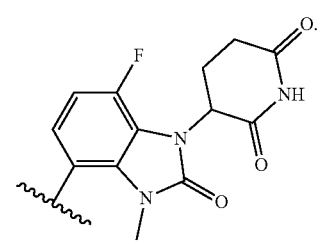 [SMILES: *c1ccc(F)c2c1n(C)c(=O)n2C1CCC(=O)NC1=O]
In some embodiments, LBM is
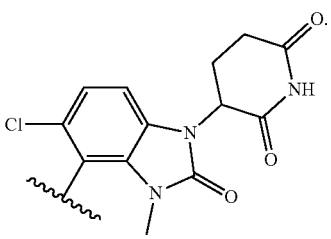 [SMILES: *c1c(Cl)ccc2c1n(C)c(=O)n2C1CCC(=O)NC1=O]
In some embodiments, LBM is
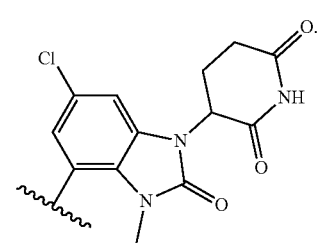 [SMILES: *c1cc(Cl)cc2c1n(C)c(=O)n2C1CCC(=O)NC1=O]

In some embodiments, LBM is
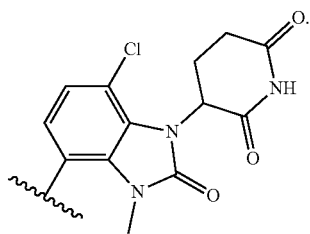 [SMILES: *c1ccc(Cl)c2c1n(C)c(=O)n2C1CCC(=O)NC1=O]
In some embodiments, LBM is
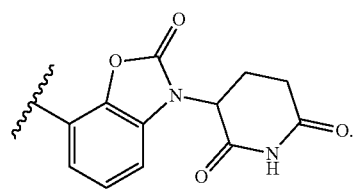 [SMILES: *c1cccc2c1oc(=O)n2C1CCC(=O)NC1=O]
In some embodiments, LBM is
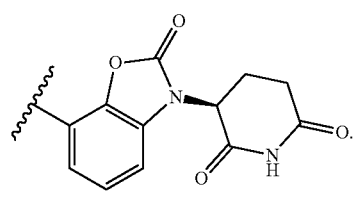 [SMILES: *c1cccc2c1oc(=O)n2[C@H]1CCC(=O)NC1=O]
In some embodiments, LBM is
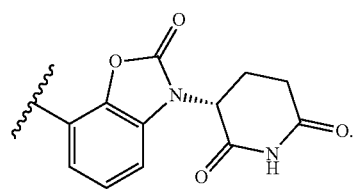 [SMILES: *c1cccc2c1oc(=O)n2[C@@H]1CCC(=O)NC1=O]
In some embodiments, LBM is
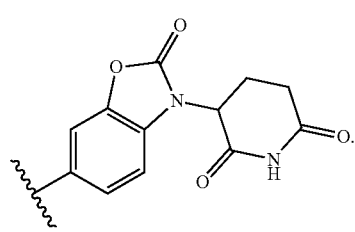 [SMILES: *c1ccc2c(c1)oc(=O)n2C1CCC(=O)NC1=O]
In some embodiments, LBM is
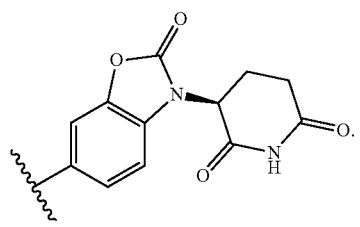 [SMILES: *c1ccc2c(c1)oc(=O)n2[C@H]1CCC(=O)NC1=O]
In some embodiments, LBM is
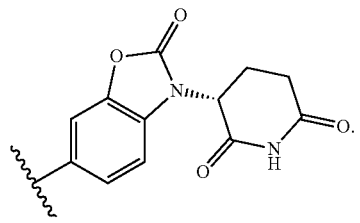 [SMILES: *c1ccc2c(c1)oc(=O)n2[C@@H]1CCC(=O)NC1=O]
In some embodiments, LBM is
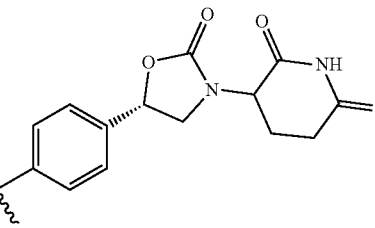
In some embodiments, LBM is
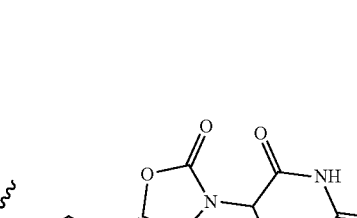
In some embodiments, LBM is
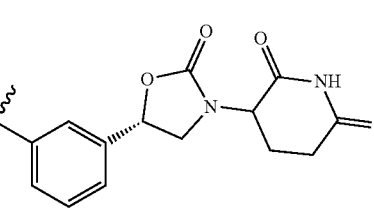

In some embodiments, LBM is
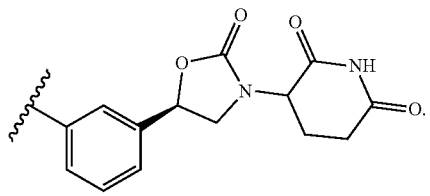 [SMILES: *c1cccc([C@@H]2CN(C3CCC(=O)NC3=O)C(=O)O2)c1]
In some embodiments, LBM is
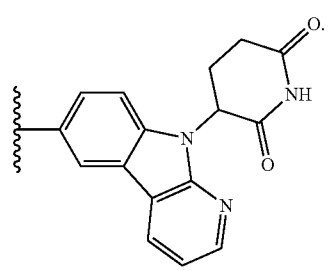 [SMILES: *c1ccc2c(c1)c1cccnc1n2C1CCC(=O)NC1=O]
In some embodiments, LBM is
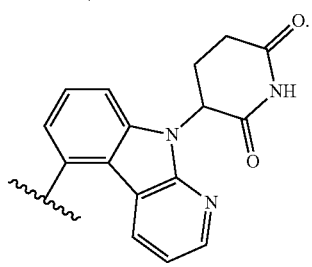
In some embodiments, LBM is
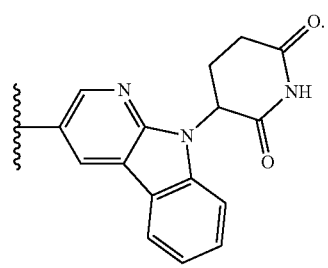 [SMILES: *c1cnc2c(c1)c1ccccc1n2C1CCC(=O)NC1=O]
In some embodiments, LBM is
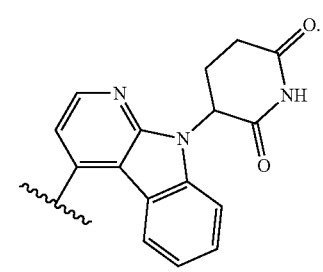 [SMILES: *c1ccnc2c1c1ccccc1n2C1CCC(=O)NC1=O]
In some embodiments, LBM is
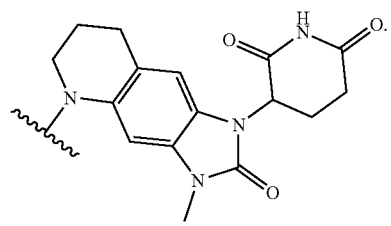 [SMILES: *N1CCCc2cc3c(cc21)n(C)c(=O)n3C1CCC(=O)NC1=O]
In some embodiments, LBM is
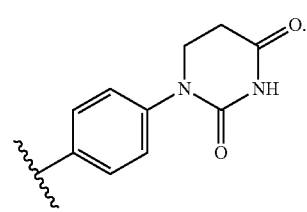 [SMILES: *c1ccc(N2CCC(=O)NC2=O)cc1]
In some embodiments, LBM is
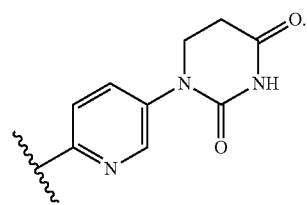 [SMILES: *c1ccc(N2CCC(=O)NC2=O)cn1]
In some embodiments, LBM is
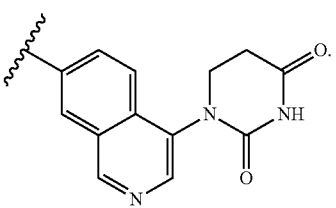 [SMILES: *c1ccc2c(N3CCC(=O)NC3=O)cncc2c1]
In some embodiments, LBM is
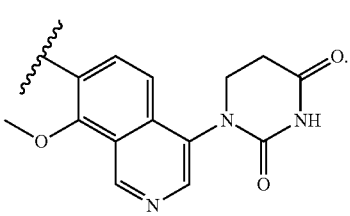 [SMILES: *c1ccc2c(N3CCC(=O)NC3=O)cncc2c1OC]

In some embodiments, LBM is

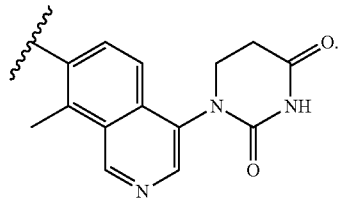 [SMILES: *c1ccc2c(N3CCC(=O)NC3=O)cncc2c1C]

In some embodiments, LBM is

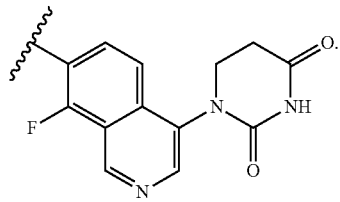 [SMILES: *c1ccc2c(N3CCC(=O)NC3=O)cncc2c1F]

In some embodiments, LBM is

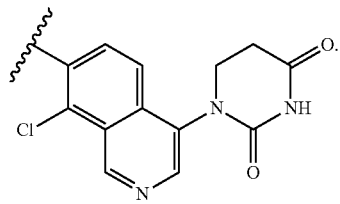 [SMILES: *c1ccc2c(N3CCC(=O)NC3=O)cncc2c1Cl]

In some embodiments, LBM is

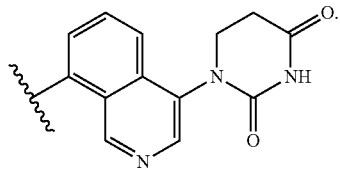 [SMILES: *c1cccc2c(N3CCC(=O)NC3=O)cncc12]

In some embodiments, LBM is selected from those in Table 1 below.

In some embodiments, the present invention provides the compound of formula I-a, wherein LBM is

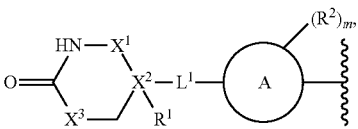

Ring Q and Ring P form an indazole ring, and X is cyclohexyl as shown, to provide a compound of formula I-e-1:

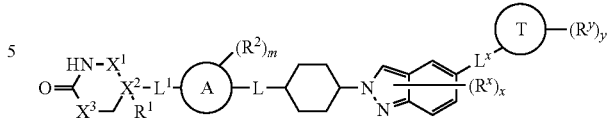

I-e-1 or a pharmaceutically acceptable salt thereof, wherein each of $X^1$, $X^2$, $X^3$, $R^1$, $R^2$, $L^1$, Ring A, and m of the LBM, L, and $L^x$, Ring T, $R^x$, $R^y$, x, and y of the IRAK moiety is as defined above and described in embodiments herein, both singly and in combination.

In some embodiments, the present invention provides the compound of formula I-a, wherein LBM is

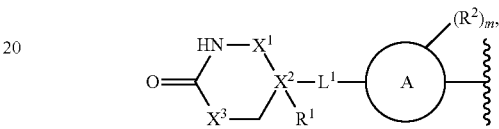

Ring Q and Ring P form a 6-azaindazole ring, and X is cyclohexyl as shown, to provide a compound of formula I-e-2:

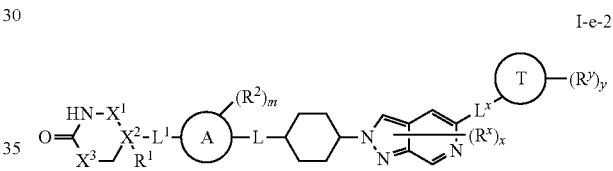

I-e-2 or a pharmaceutically acceptable salt thereof, wherein each of $X^1$, $X^2$, $X^3$, $R^1$, $R^2$, $L^1$, Ring A, and m of the LBM, L, and $L^x$, Ring T, $R^x$, $R^y$, x, and y of the IRAK moiety is as defined above and described in embodiments herein, both singly and in combination.

In some embodiments, the present invention provides the compound of formula I-a, wherein LBM is

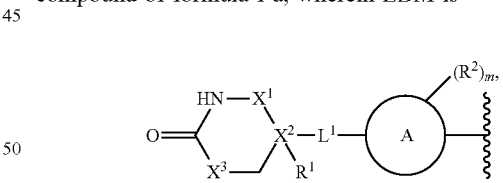

m is 1 and $R^2$ is —$OC_{1-6}$ alkyl, x is 0, Ring Q and Ring P form an indazole ring, and X is cyclohexyl as shown, to provide a compound of formula I-f-1:

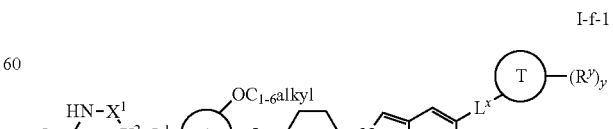

I-f-1 or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

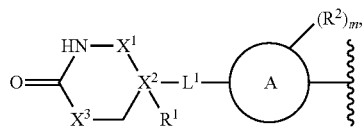

m is 1 and $R^2$ is —OMe, x is 0, Ring Q and Ring P form an indazole ring, and X is cyclohexyl as shown, to provide a compound of formula I-f-2:

I-f-2

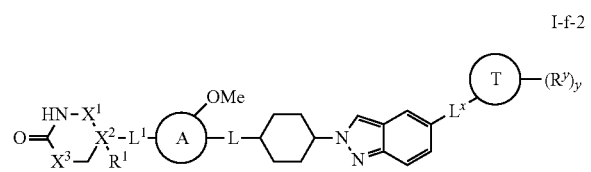

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

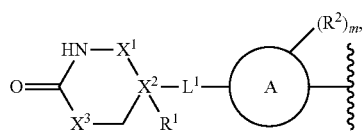

L is

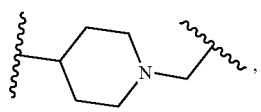 [SMILES: *CN1CCC(*)CC1]

x is 0, Ring Q and Ring P form an indazole ring, and X is cyclohexyl as shown, to provide a compound of formula I-f-3:

I-f-3

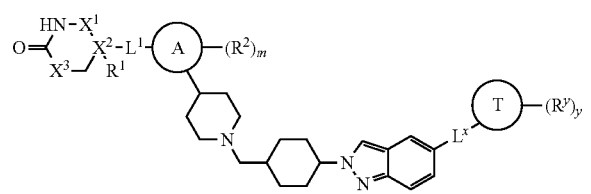

or a pharmaceutically acceptable salt thereof, wherein each of $X^1$, $X^2$, $X^3$, $R^1$, $R^2$, $L^1$, Ring A, and m of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

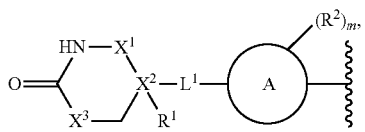

m is 1 and $R^2$ is —OC$_{1-6}$alkyl, L is

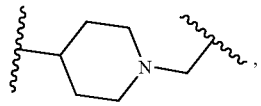 [SMILES: *CN1CCC(*)CC1]

x is 0, Ring Q and Ring P form an indazole ring, and X is cyclohexyl as shown, to provide a compound of formula I-f-4:

I-f-4

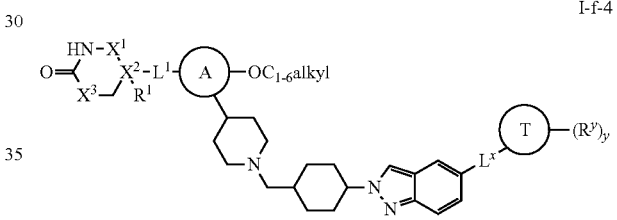

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

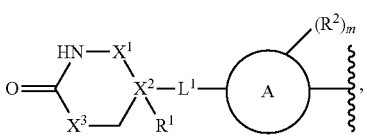

m is 1 and $R^2$ is —OMe, L is

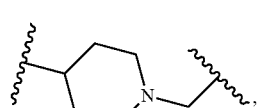

x is 0, Ring Q and Ring P form an indazole ring, and X is cyclohexyl as shown, to provide a compound of formula I-f-5:

I-f-5

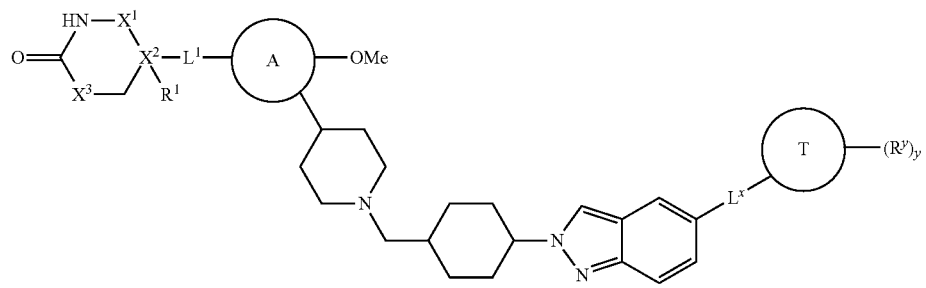

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

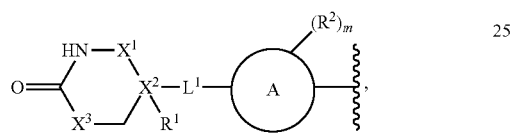

m is 1 and $R^2$ is —$OC_{1-6}$ alkyl, x is 0, Ring Q and Ring P form a 6-azaindazole ring, and X is cyclohexyl as shown, to provide a compound of formula I-f-6:

I-f-6

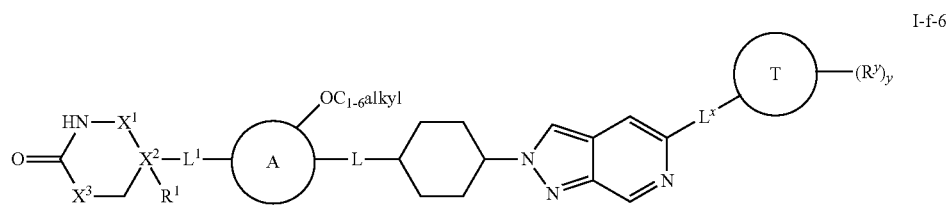

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

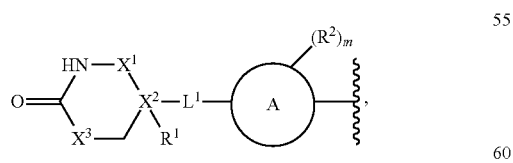

m is 1 and $R^2$ is —OMe, x is 0, Ring Q and Ring P form a 6-azaindazole ring, and X is cyclohexyl as shown, to provide a compound of formula I-f-7:

I-f-7

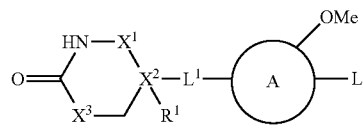 

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

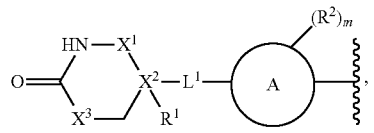

L is

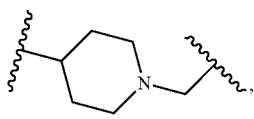 [SMILES: *CN1CCC(*)CC1]

x is 0, Ring Q and Ring P forma 6-azaindazole ring, and X is cyclohexyl as shown, to provide a compound of formula I-f-8:

or a pharmaceutically acceptable salt thereof, wherein each of $X^1$, $X^2$, $X^3$, $R^1$, $R^2$, $L^1$, Ring A, and m of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

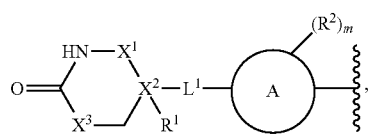

m is 1 and $R^2$ is —$OC_{1-6}$alkyl, L is

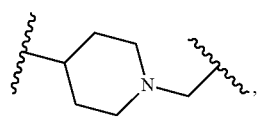 [SMILES: *CN1CCC(*)CC1]

x is 0, Ring Q and Ring P form a 6-azaindazole ring, and X is cyclohexyl as shown, to provide a compound of formula I-f-9:

I-f-8

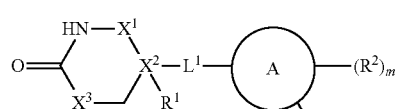

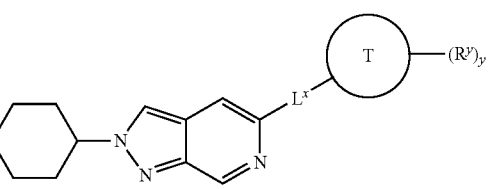

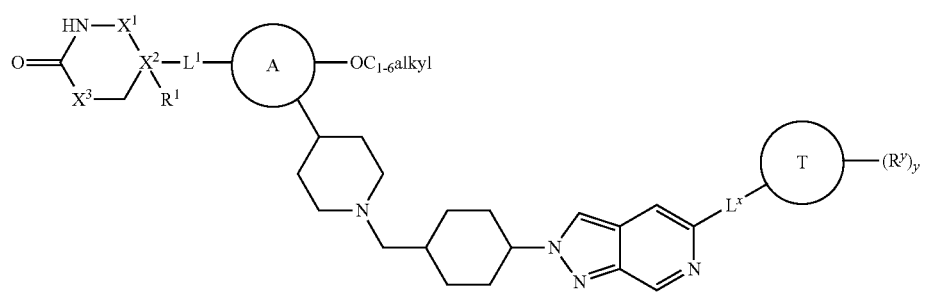

I-f-9 or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

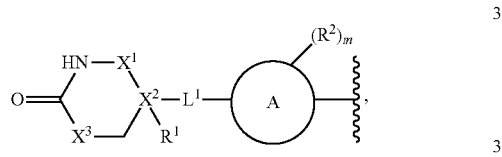

m is 1 and $R^2$ is —OMe, L is

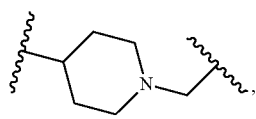 [SMILES: *CN1CCC(*)CC1]

x is 0, Ring Q and Ring P form a 6-azaindazole ring, and X is cyclohexyl as shown, to provide a compound of formula I-f-10:

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

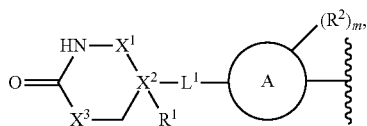

x is 1 and $R^x$ is methyl, Ring Q and Ring P form an indazole ring, and X is cyclohexyl as shown, to provide a compound of formula I-f-11:

I-f-10

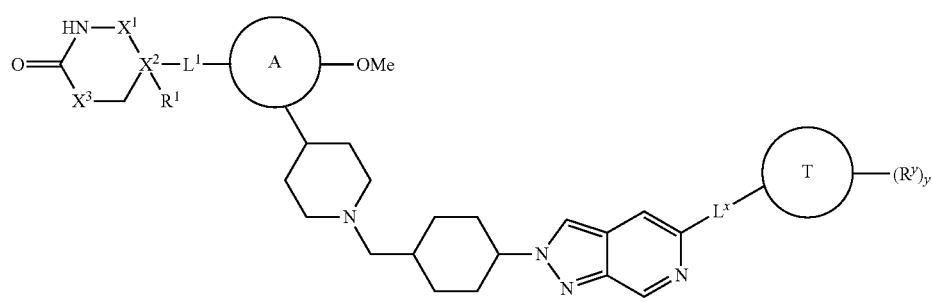

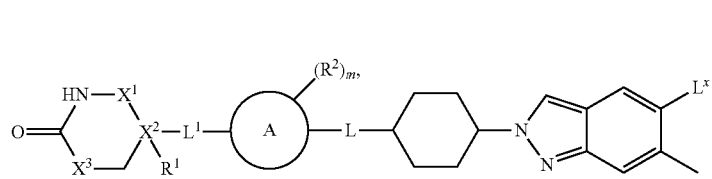
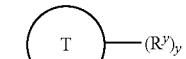

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

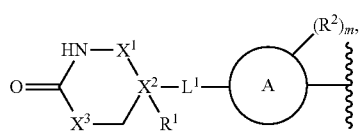

L is

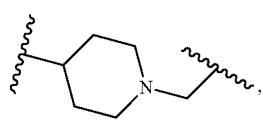 [SMILES: *CN1CCC(*)CC1]

x is 1 and $R^x$ is methyl, Ring Q and Ring P form an indazole ring, and X is cyclohexyl as shown, to provide a compound of formula I-f-12:

or a pharmaceutically acceptable salt thereof, wherein each of $X^1$, $X^2$, $X^3$, $R^1$, $R^2$, $L^1$, Ring A, and m of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

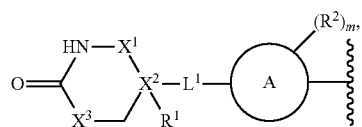

L is

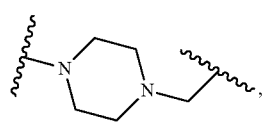 [SMILES: *CN1CCN(*)CC1]

x is 1 and $R^x$ is methyl, Ring Q and Ring P form an indazole ring, and X is cyclohexyl as shown, to provide a compound of formula I-f-13:

I-f-12

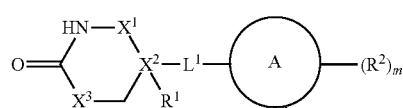

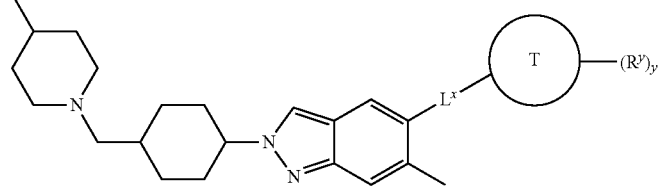

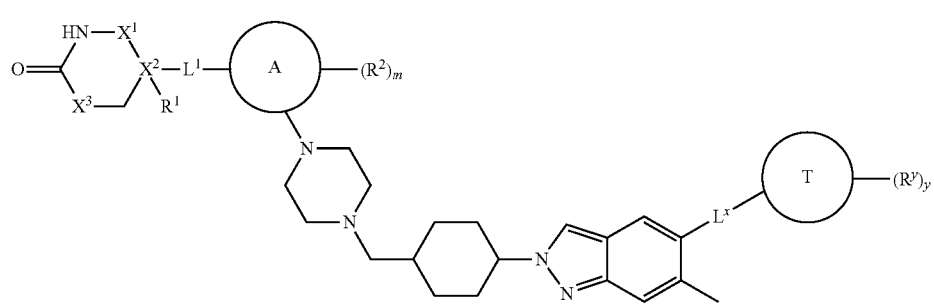

I-f-13 or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

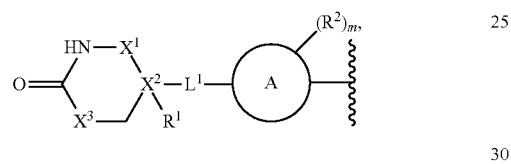

m is 1 and $R^2$ is —$C_{1-6}$ alkyl, x is 0, Ring Q and Ring P form a 6-azaindazole ring, and X is cyclohexyl as shown, to provide a compound of formula I-f-14:

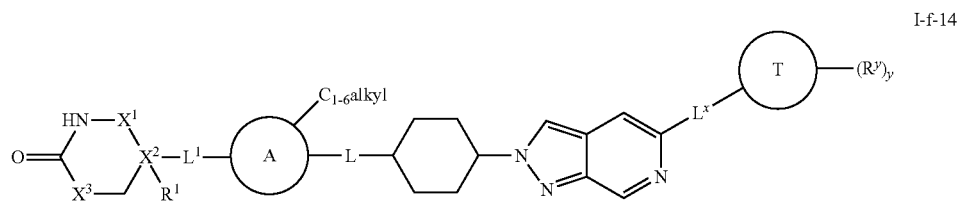

I-f-14 or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

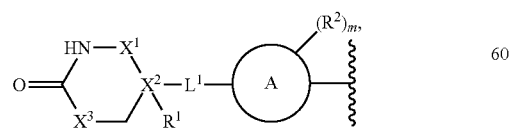

m is 1 and $R^2$ is methyl, x is 0, Ring Q and Ring P form a 6-azaindazole ring, and X is cyclohexyl as shown, to provide a compound of formula I-f-15:

I-f-15

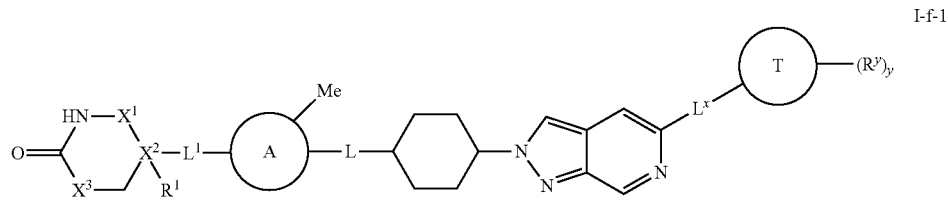

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

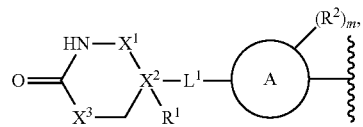

m is 1 and $R^2$ is —$C_{1-6}$alkyl, L is

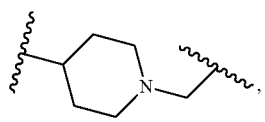 [SMILES: *CN1CCC(*)CC1]

x is 0, Ring Q and Ring P form a 6-azaindazole ring, and X is cyclohexyl as shown, to provide a compound of formula I-f-16:

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

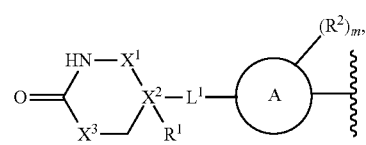

m is 1 and $R^2$ is methyl, L is

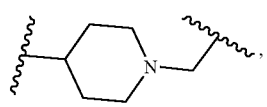 [SMILES: *CN1CCC(*)CC1]

x is 0, Ring Q and Ring P form a 6-azaindazole ring, and X is cyclohexyl as shown, to provide a compound of formula I-f-17:

I-f-16

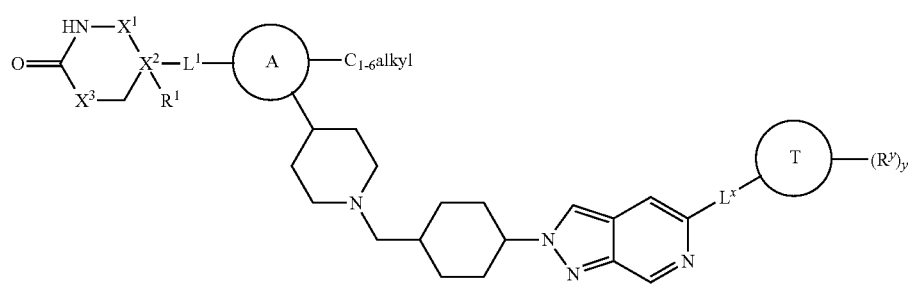

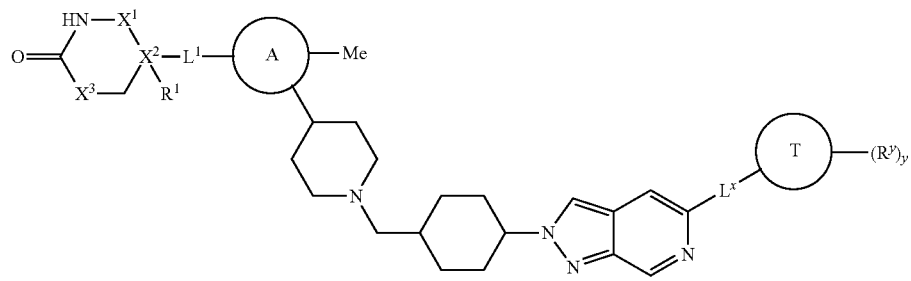

I-f-17 or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

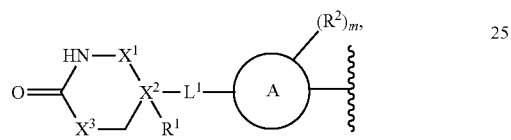

m is 1 and $R^2$ is halo, x is 0, Ring Q and Ring P form a 6-azaindazole ring, and X is cyclohexyl as shown, to provide a compound of formula I-f-18:

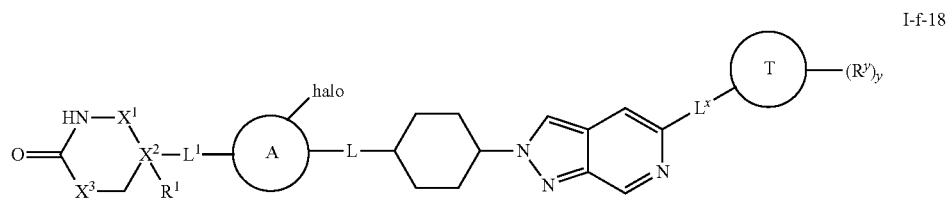

I-f-18 or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

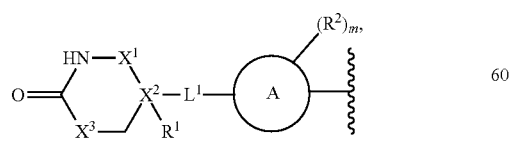

m is 1 and $R^2$ is fluoro, x is 0, Ring Q and Ring P form a 6-azaindazole ring, and X is cyclohexyl as shown, to provide a compound of formula I-f-19:

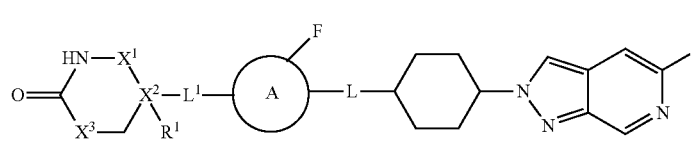

I-f-19 or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

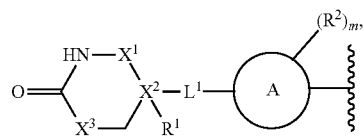

m is 1 and $R^2$ is halo, L is

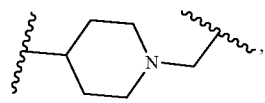 [SMILES: *CN1CCC(*)CC1]

x is 0, Ring Q and Ring P form a 6-azaindazole ring, and X is cyclohexyl as shown, to provide a compound of formula I-f-20:

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

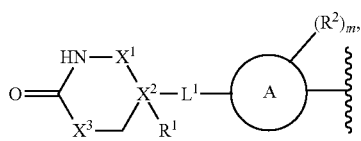

m is 1 and $R^2$ is fluoro, L is

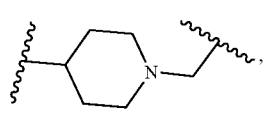

x is 0, Ring Q and Ring P form a 6-azaindazole ring, and X is cyclohexyl as shown, to provide a compound of formula I-f-21:

I-f-20

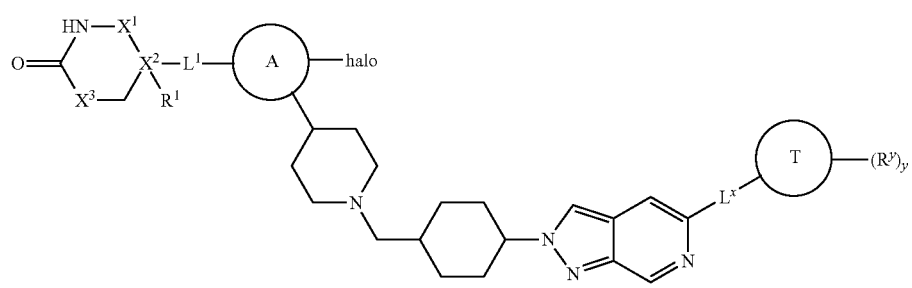

I-f-21

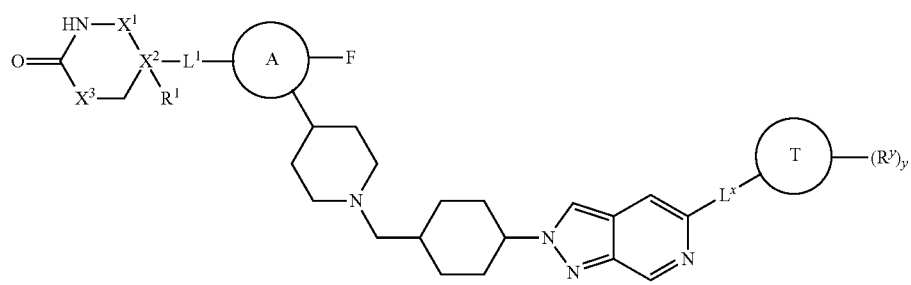

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

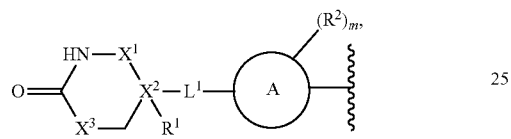

x is 1 and $R^x$ is chloro, Ring Q and Ring P form an indazole ring, and X is cyclohexyl as shown, to provide a compound of formula I-f-22:

I-f-22

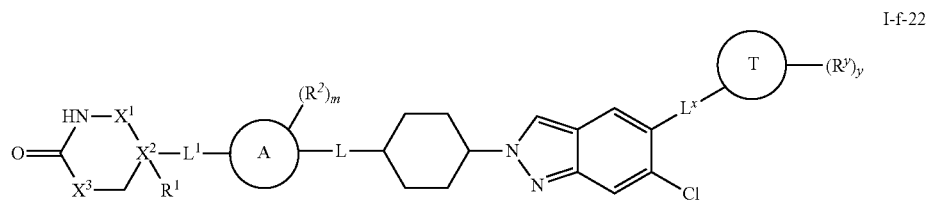

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

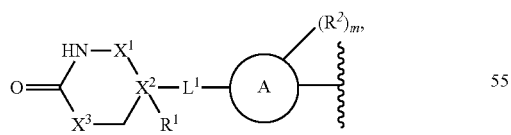

L is

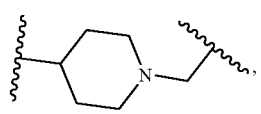 [SMILES: *CN1CCC(*)CC1]

x is 1 and R$^x$ is chloro, Ring Q and Ring P form an indazole ring, and X is cyclohexyl as shown, to provide a compound of formula I-f-23:

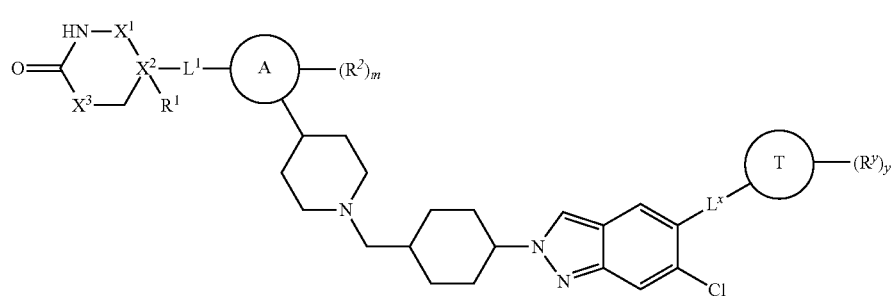

I-f-23 or a pharmaceutically acceptable salt thereof, wherein each of X$^1$, X$^2$, X$^3$, R$^1$, R$^2$, L$^1$, Ring A, and m of the LBM, and L$^x$, Ring T, R$^y$, and y of the IRAK moiety is as defined above and described in embodiments herein, both singly and in combination.

In some embodiments, the present invention provides the compound of formula I-a, wherein LBM is

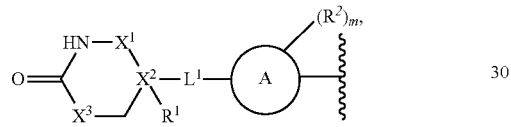

x is 1 and R$^x$ is —OMe, Ring Q and Ring P form an indazole ring, and X is cyclohexyl as shown, to provide a compound of formula I-f-24:

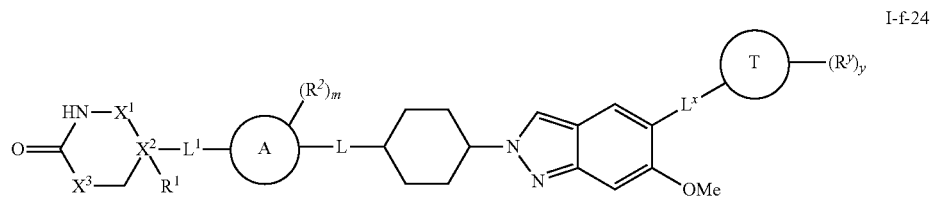

I-f-24 or a pharmaceutically acceptable salt thereof, wherein each of X$^1$, X$^2$, X$^3$, R$^1$, R$^2$, L$^1$, and Ring A of the LBM, L, and L$^x$, Ring T, R$^y$, and y of the IRAK moiety is as defined above and described in embodiments herein, both singly and in combination.

In some embodiments, the present invention provides the compound of formula I-a, wherein LBM is

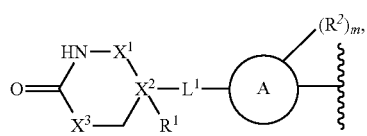

L is

x is 1 and R$^x$ is —OMe, Ring Q and Ring P form an indazole ring, and X is cyclohexyl as shown, to provide a compound of formula I-f-25:

I-f-25

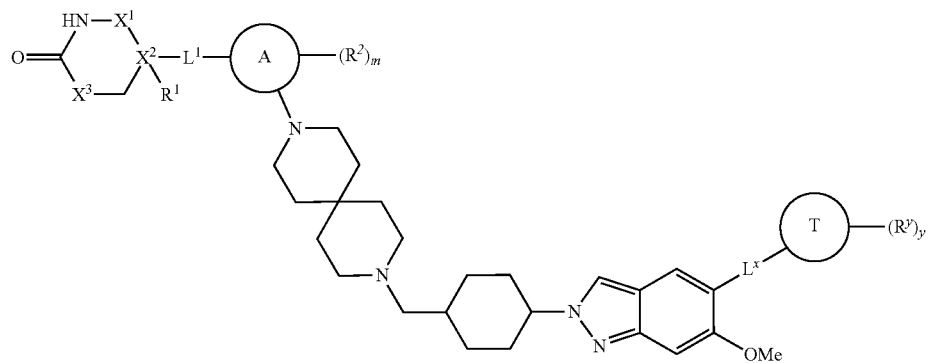

or a pharmaceutically acceptable salt thereof, wherein each of $X^1$, $X^2$, $X^3$, $R^1$, $R^2$, $L^1$, Ring A, and m of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

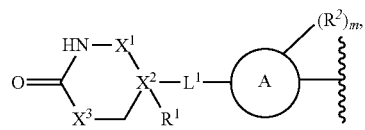

x is 1 and $R^x$ is —OMe, Ring Q and Ring P form an indazole ring, and X is cyclohexyl as shown, to provide a compound of formula I-f-26:

I-f-26

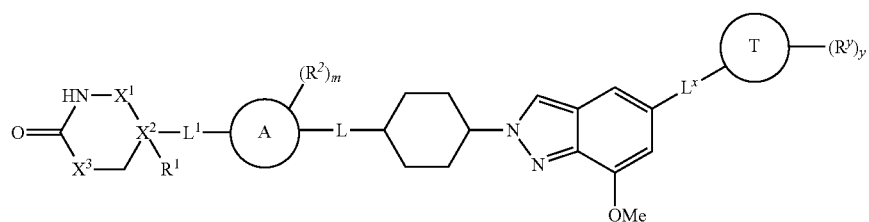

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is L is

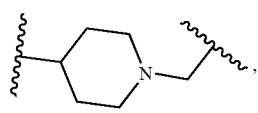

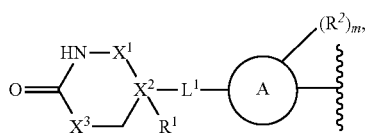

x is 1 and $R^x$ is —OMe, Ring Q and Ring P form an indazole ring, and X is cyclohexyl as shown, to provide a compound of formula I-f-27:

I-f-27

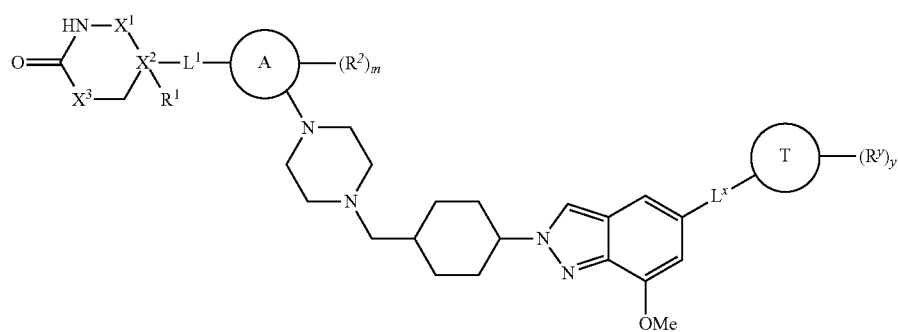

or a pharmaceutically acceptable salt thereof, wherein each of $X^1$, $X^2$, $X^3$, $R^1$, $R^2$, $L^1$, Ring A, and m of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

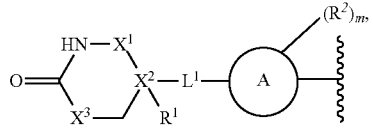

x is 1 and $R^x$ is —S(O)Me, Ring Q and Ring P form an indazole ring, and X is cyclohexyl as shown, to provide a compound of formula I-f-28:

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

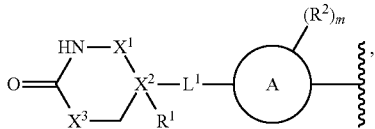

L is

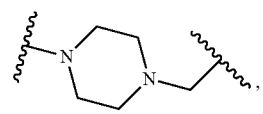 [SMILES: *CN1CCN(*)CC1]

x is 1 and $R^x$ is —S(O)Me, Ring Q and Ring P form an indazole ring, and X is cyclohexyl as shown, to provide a compound of formula I-f-29:

I-f-28

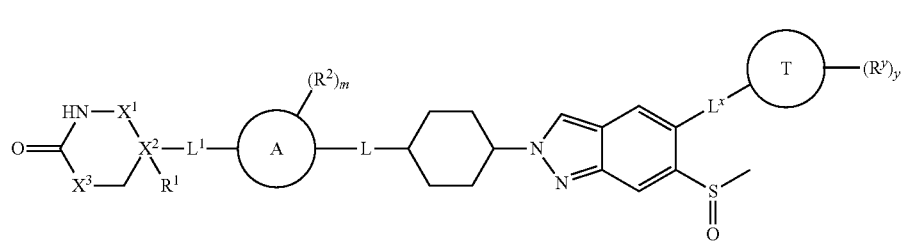

I-f-29

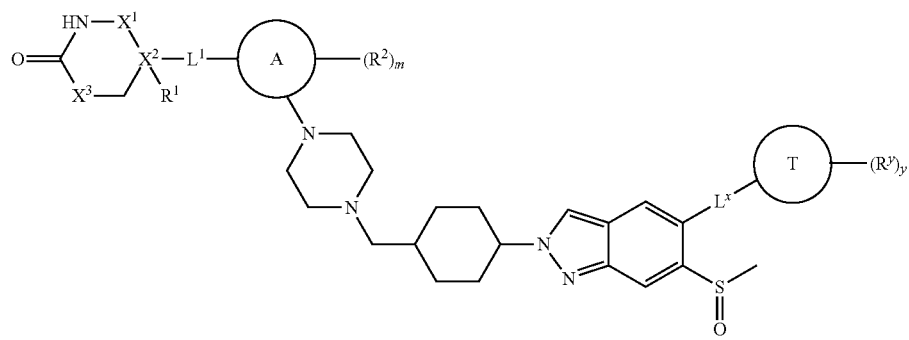

or a pharmaceutically acceptable salt thereof, wherein each of $X^1$, $X^2$, $X^3$, $R^1$, $R^2$, $L^1$, Ring A, and m of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

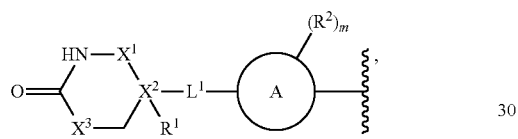

m is 1 and $R^2$ is halo, x is 1 and $R^x$ is —OMe, Ring Q and Ring P form a 6-azaindazole ring, and X is cyclobutyl as shown, to provide a compound of formula I-f-30:

I-f-30

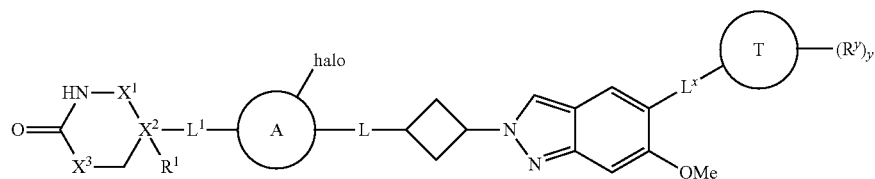

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

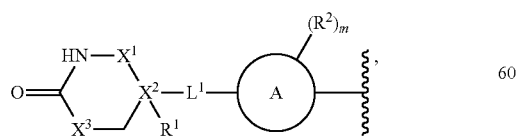

m is 1 and $R^2$ is fluoro, x is 1 and $R^x$ is —OMe, Ring Q and Ring P form a 6-azaindazole ring, and X is cyclobutyl as shown, to provide a compound of formula I-f-31:

I-f-31

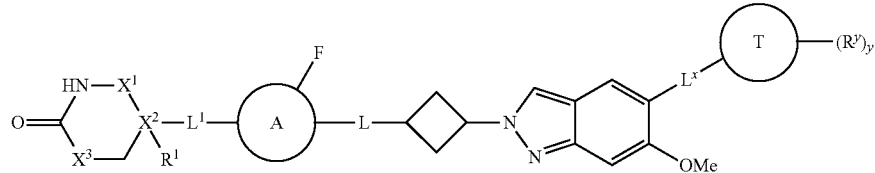

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

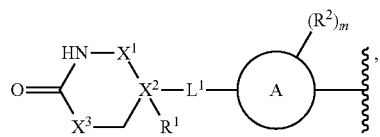

m is 1 and $R^2$ is halo, L is

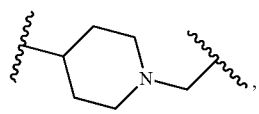 [SMILES: *CN1CCC(*)CC1]

x is 1 and $R^x$ is —OMe, Ring Q and Ring P form a 6-azaindazole ring, and X is cyclobutyl as shown, to provide a compound of formula I-f-32:

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

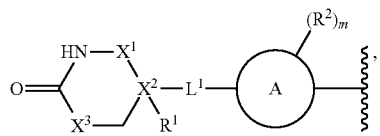

m is 1 and $R^2$ is fluoro, L is

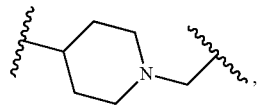 [SMILES: *CN1CCC(*)CC1]

x is 1 and $R^x$ is —OMe, Ring Q and Ring P form a 6-azaindazole ring, and X is cyclobutyl as shown, to provide a compound of formula I-f-33:

I-f-32

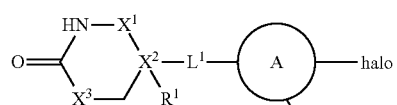
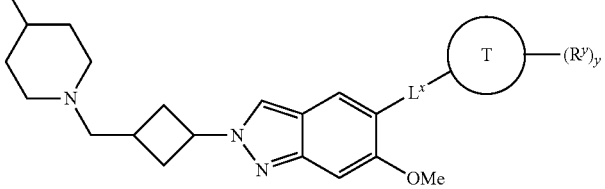

I-f-33

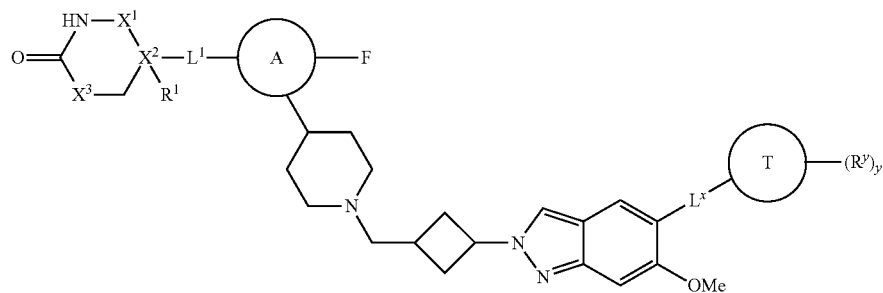

or a pharmaceutically acceptable salt thereof, wherein each of $X^1$, $X^2$, $X^3$, $R^1$, $R^2$, $L^1$, and Ring A of the LBM, and $L^x$, Ring T, $R^y$, and y of the IRAK moiety is as defined above and described in embodiments herein, both singly and in combination.

In some embodiments, the present invention provides the compound of formula I-a, wherein LBM is

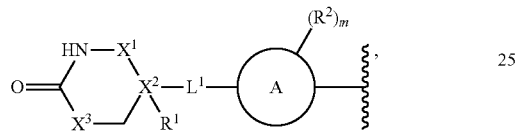

x is 1 and $R^x$ is —$SO_2Me$, Ring Q and Ring P form an indazole ring, and X is cyclohexyl as shown, to provide a compound of formula I-f-34:

I-f-34

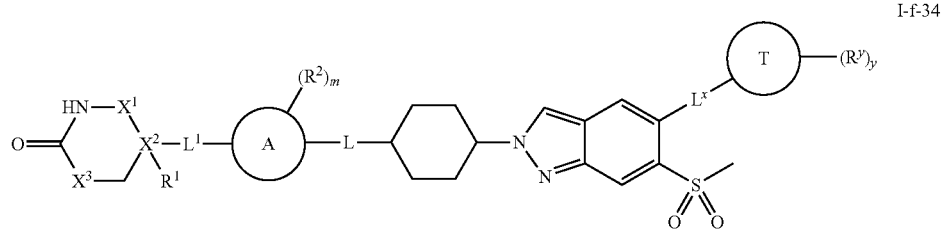

or a pharmaceutically acceptable salt thereof, wherein each of $X^1$, $X^2$, $X^3$, $R^1$, $R^2$, $L^1$, and Ring A of the LBM, L, and $L^x$, Ring T, $R^y$, and y of the IRAK moiety is as defined above and described in embodiments herein, both singly and in combination.

In some embodiments, the present invention provides the compound of formula I-a, wherein LBM is

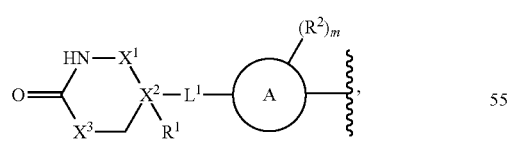

L is

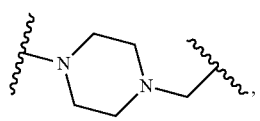 [SMILES: *CN1CCN(*)CC1]

x is 1 and $R^x$ is —SO$_2$Me, Ring Q and Ring P form an indazole ring, and X is cyclohexyl as shown, to provide a compound of formula I-f-35:

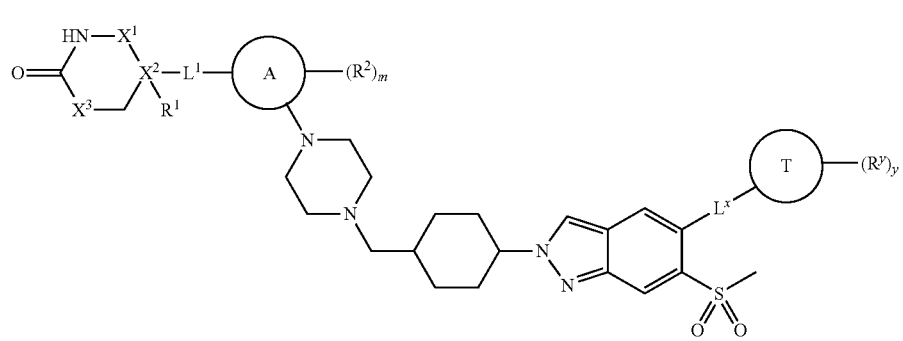

I-f-35 or a pharmaceutically acceptable salt thereof, wherein each of $X^1$, $X^2$, $X^3$, $R^1$, $R^2$, $L^1$, Ring A, and m of the LBM, and $L^x$, Ring T, $R^y$, and y of the IRAK moiety is as defined above and described in embodiments herein, both singly and in combination.

In some embodiments, the present invention provides the compound of formula I-b', wherein LBM is

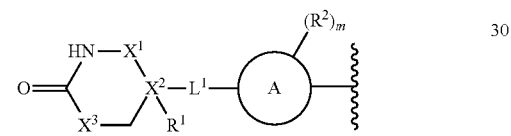

and $R^1$ is cyclohexyl as shown, to provide a compound of formula I-f-36:

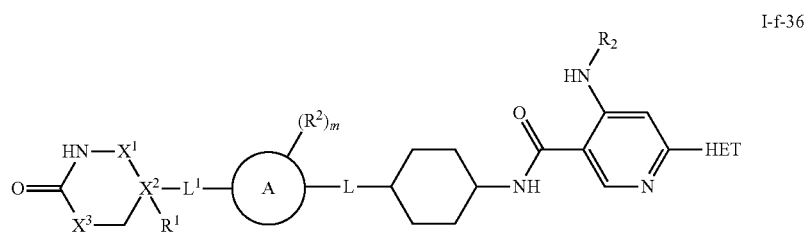

I-f-36 or a pharmaceutically acceptable salt thereof, wherein each of $X^1$, $X^2$, $X^3$, $R^1$, $R^2$, $L^1$, and Ring A of the LBM, L, and, $R_2$ and HET of the IRAK moiety is as defined above and described in embodiments herein, both singly and in combination.

In some embodiments, the present invention provides the compound of formula I-b', wherein LBM is

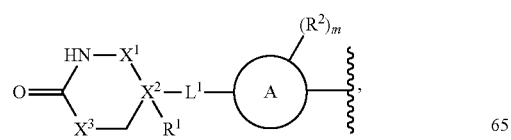

L is

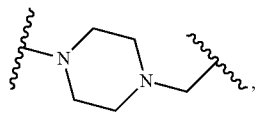 [SMILES: *CN1CCN(*)CC1]

and R¹ is cyclohexyl as shown, to provide a compound of formula I-f-37:

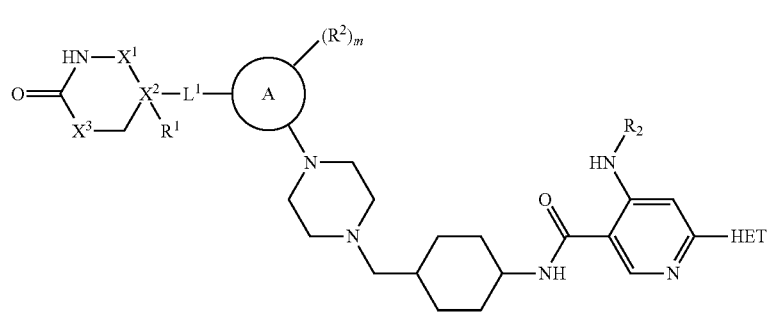

I-f-37 or a pharmaceutically acceptable salt thereof, wherein each of $X^1$, $X^2$, $X^3$, $R^1$, $R^2$, $L^1$, and Ring A of the LBM, and, $R_2$ and HET of the IRAK moiety is as defined above and described in embodiments herein, both singly and in combination.

In some embodiments, the present invention provides the compound of formula I-a, wherein LBM is

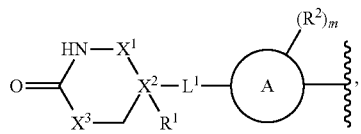

Ring Q and Ring P form an imidazo[1,2-a]pyridine ring, and X is cyclohexyl as shown, to provide a compound of formula I-e-3:

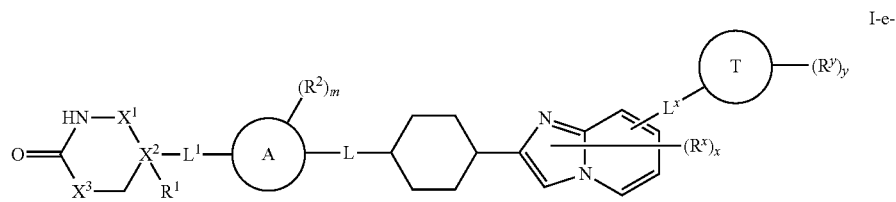

I-e-3 or a pharmaceutically acceptable salt thereof, wherein each of $X^1$, $X^2$, $X^3$, $R^1$, $R^2$, $L^1$, Ring A, and m of the LBM, L, and $L^x$, Ring T, R, $R^x$, $R^y$, x, and y of the IRAK moiety is as defined above and described in embodiments herein, both singly and in combination.

In some embodiments, the present invention provides the compound of formula I-a, wherein LBM is

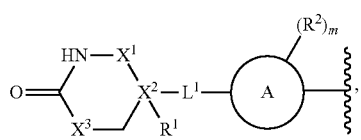

Ring Q is benzo, a single $R^x$ is —OR, and X is cyclohexyl as shown, to provide a compound of formula I-e-4:

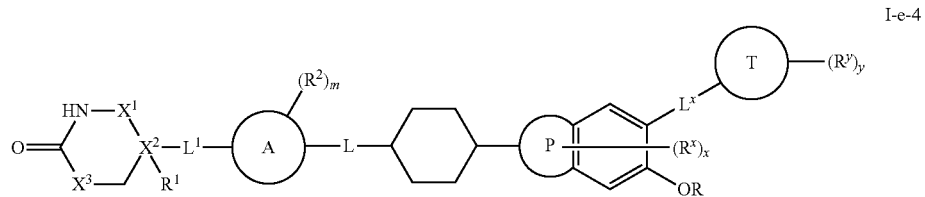

I-e-4 or a pharmaceutically acceptable salt thereof, wherein each of $X^1$, $X^2$, $X^3$, $R^1$, $R^2$, $L^1$, Ring A, and m of the LBM, L, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a, wherein LBM is

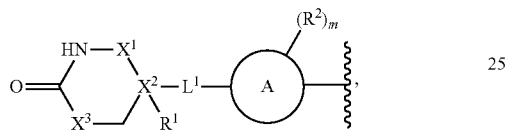

Ring Q and Ring P form an indazole ring, a single $R^x$ is —OR, and X is cyclohexyl as shown, to provide a compound of formula I-e-5:

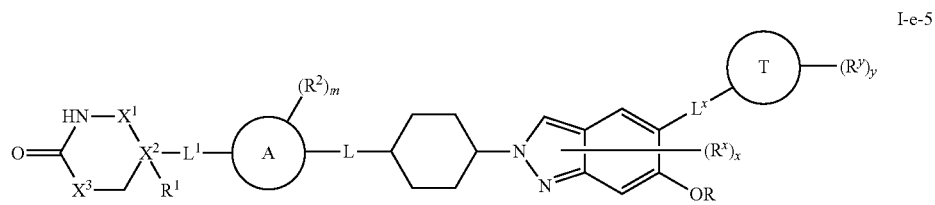

I-e-5 or a pharmaceutically acceptable salt thereof, wherein each of $X^1$, $X^2$, $X^3$, $R^1$, $R^2$, $L^1$, Ring A, and m of the LBM, L, and $L^x$, Ring T, R, $R^x$, $R^y$, x, and y of the IRAK moiety is as defined above and described in embodiments herein, both singly and in combination.

In some embodiments, the present invention provides the compound of formula I-a, wherein LBM is

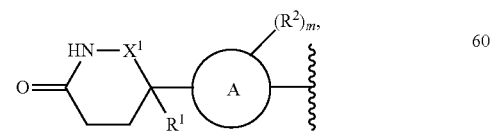

Ring Q is benzo, a single $R^x$ is —OR, and X is cyclohexyl as shown, to provide a compound of formula I-e-6:

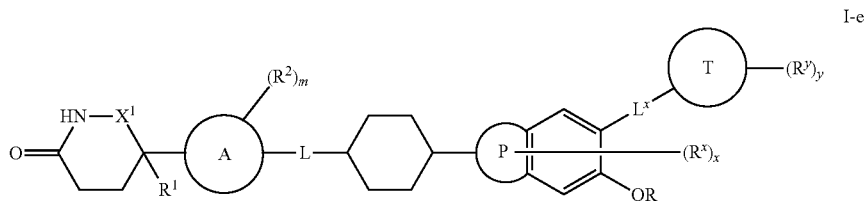

I-e-6 or a pharmaceutically acceptable salt thereof, wherein each of $X^1$, $R^1$, $R^2$, Ring A, and m of the LBM, L, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a, wherein LBM is

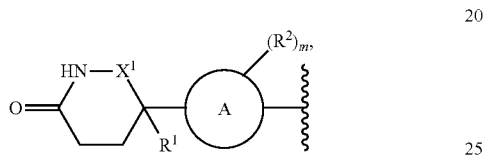

Ring Q and Ring P form an indazole ring, a single $R^x$ is —OR, and X is cyclohexyl as shown, to provide a compound of formula I-e-7:

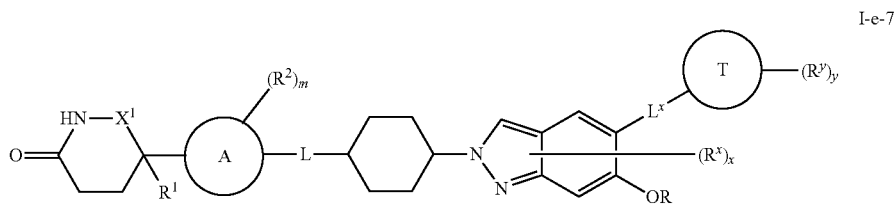

I-e-7 or a pharmaceutically acceptable salt thereof, wherein each of $X^1$, $R^1$, $R^2$, Ring A, and m of the LBM, L, and $L^x$, Ring T, R, $R^x$, $R^y$, x, and y of the IRAK moiety is as defined above and described in embodiments herein, both singly and in combination.

In some embodiments, the present invention provides the compound of formula I-a, wherein LBM is

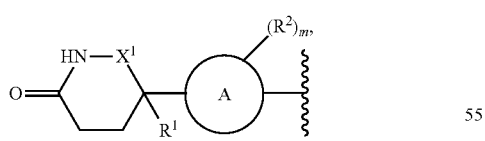

L is

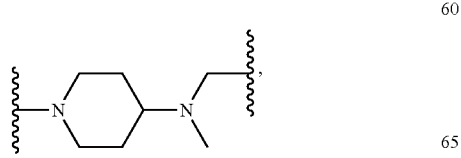

Ring Q is benzo, a single $R^x$ is —OR, and X is cyclohexyl as shown, to provide a compound of formula as a compound of formula I-e-8:

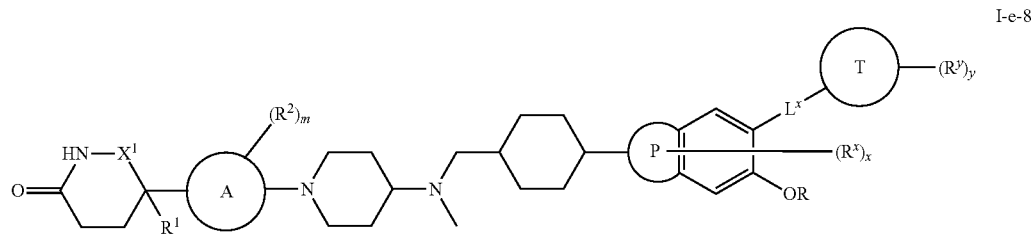

I-e-8 or a pharmaceutically acceptable salt thereof, wherein each of $X^1$, $R^1$, $R^2$, Ring A, and m of the LBM, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a, wherein LBM is

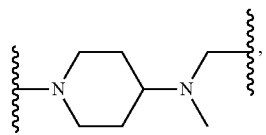 [SMILES: *CN(C)C1CCN(*)CC1]

L is

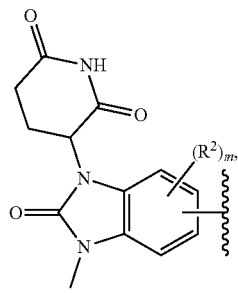

or a pharmaceutically acceptable salt thereof, wherein each of $X^1$, $R^1$, $R^2$, Ring A, and m of the LBM, and $L^x$, Ring T, R, $R^x$, $R^y$, x, and y of the IRAK moiety is as defined above and described in embodiments herein, both singly and in combination.

In some embodiments, the present invention provides the compound of formula I-a, wherein LBM is Ring Q and Ring P form an indazole ring, a single $R^x$ is —OR, and X is cyclohexyl as shown, to provide a compound of formula as a compound of formula I-e-9:

Ring Q is benzo, a single $R^x$ is —OR, and X is cyclohexyl as shown, to provide a compound of formula as a compound of formula I-e-10:

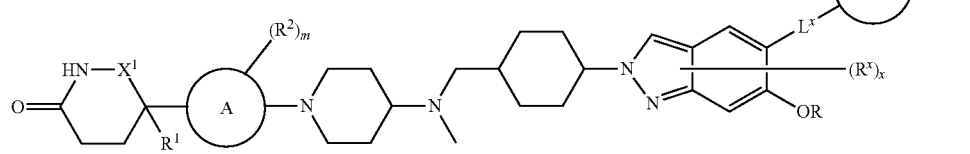

I-e-9

I-e-10

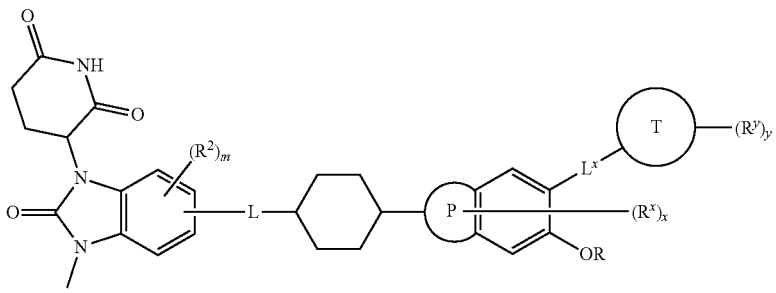

or a pharmaceutically acceptable salt thereof, wherein each of $R^2$ and m of the LBM, L, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a, wherein LBM is

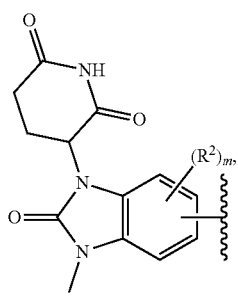

Ring Q and Ring P form an indazole ring, a single $R^x$ is —OR, and X is cyclohexyl as shown, to provide a compound of formula as a compound of formula I-e-11:

I-e-11

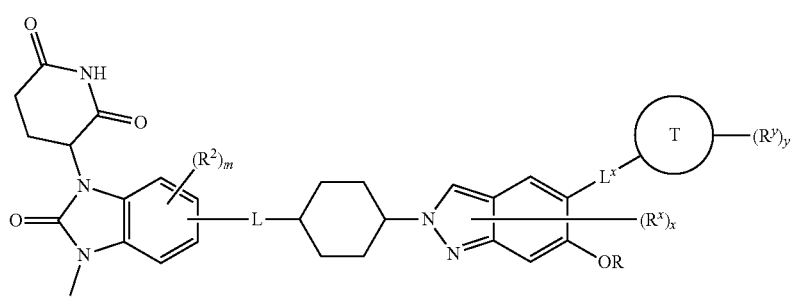

or a pharmaceutically acceptable salt thereof, wherein each of $R^2$ and m of the LBM, L, and $L^x$, Ring T, R, $R^x$, $R^y$, x, and y of the IRAK moiety is as defined above and described in embodiments herein, both singly and in combination.

In some embodiments, the present invention provides a compound of formula I-a, wherein LBM is

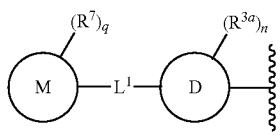

and Ring P and Ring Q form an indazole ring as shown, to provide a compound of formula I-e-12:

I-e-12

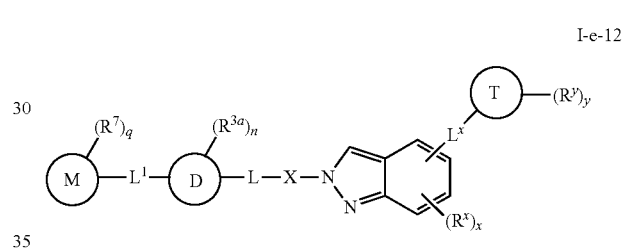

or a pharmaceutically acceptable salt thereof, wherein each of Ring M, Ring D, L, $L^1$, $R^{3a}$, $R^7$, n, q, X, $L^x$, Ring T, $R^x$, $R^y$, x, and y is as defined above and described in embodiments herein, both singly and in combination.

In some embodiments, the present invention provides a compound of formula I-a, wherein LBM is

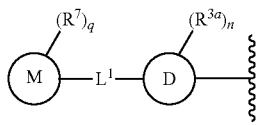

and Ring P and Ring Q form an 6-azaindazole ring as shown, to provide a compound of formula I-e-13:

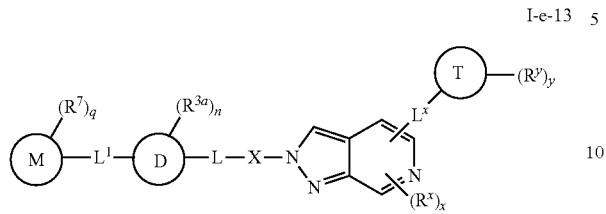

I-e-13 or a pharmaceutically acceptable salt thereof, wherein each of Ring M, Ring D, L, $L^1$, $R^{3a}$, $R^7$, n, q, X, $L^x$, Ring T, $R^x$, $R^y$, x, and y is as defined above and described in embodiments herein, both singly and in combination.

In some embodiments, the present invention provides a compound of formula I-a, wherein LBM is

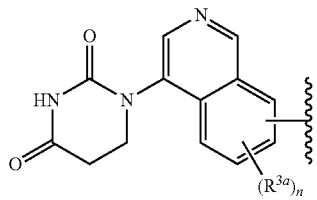

and Ring P and Ring Q form an indazole ring as shown, to provide a compound of formula I-e-14:

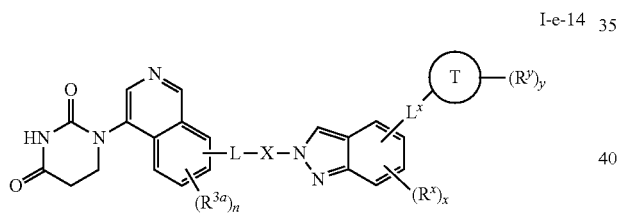

I-e-14 or a pharmaceutically acceptable salt thereof, wherein each of L, $R^{3a}$, n, X, $L^x$, Ring T, $R^x$, $R^y$, x, and y is as defined above and described in embodiments herein, both singly and in combination.

In some embodiments, the present invention provides a compound of formula I-a, wherein LBM is

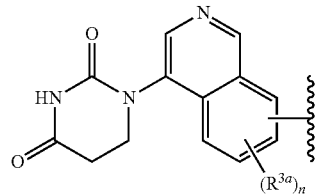

and Ring P and Ring Q form an 6-azaindazole ring as shown, to provide a compound of formula I-e-15:

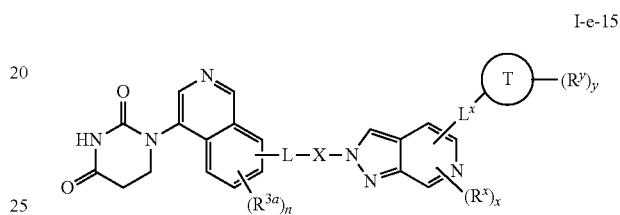

I-e-15 or a pharmaceutically acceptable salt thereof, wherein each of L, $R^{3a}$, n, X, $L^x$, Ring T, $R^x$, $R^y$, x, and y is as defined above and described in embodiments herein, both singly and in combination.

In some embodiments, the present invention provides the compound of formula I-a, wherein LBM is

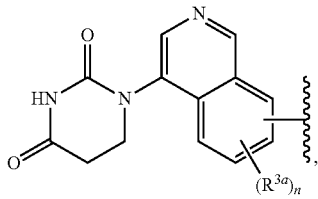

Ring Q is benzo, a single $R^x$ is —OR, and X is cyclohexyl as shown, to provide a compound of formula as a compound of formula I-e-16:

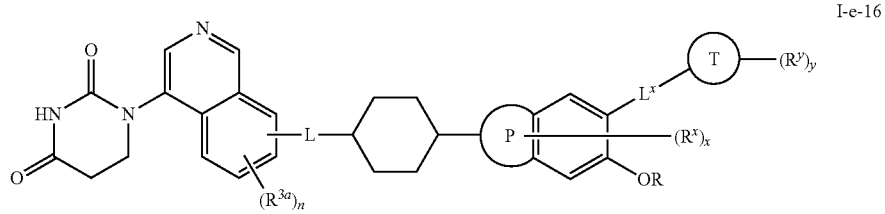

I-e-16 or a pharmaceutically acceptable salt thereof, wherein each of $R^{3a}$ and n of the LBM, L, and $L^x$, Ring P, Ring T, R, $R^x$, $R^y$, x, and y of the IRAK moiety is as defined above and described in embodiments herein, both singly and in combination.

In some embodiments, the present invention provides the compound of formula I-a, wherein LBM is

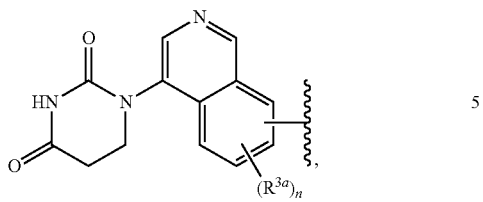

Ring Q and Ring P form an indazole ring, a single $R^x$ is —OR, and X is cyclohexyl as shown, to provide a compound of formula as a compound of formula I-e-17:

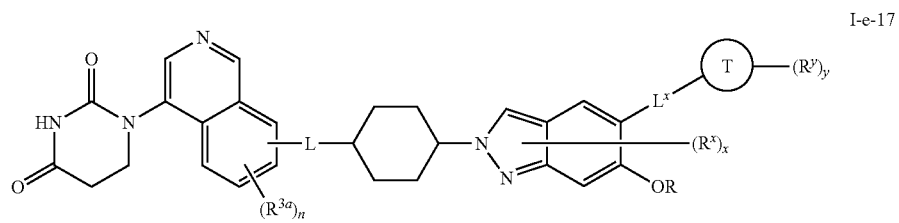

I-e-17 or a pharmaceutically acceptable salt thereof, wherein each of $R^{3a}$ and n of the LBM, L, and $L^x$, Ring T, R, $R^x$, $R^y$, x, and y of the IRAK moiety is as defined above and described in embodiments herein, both singly and in combination.

In some embodiments, the present invention provides the compound of formula I-a, wherein LBM is

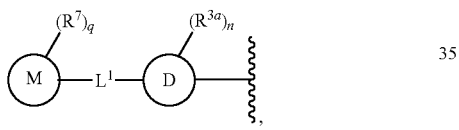

Ring Q and Ring P form an indazole ring, n is 1 and $R^{3a}$ is —$OC_{1-6}$alkyl, x is 1 and $R^x$ is —OMe, and X is cyclohexyl as shown, to provide a compound of formula I-e-18:

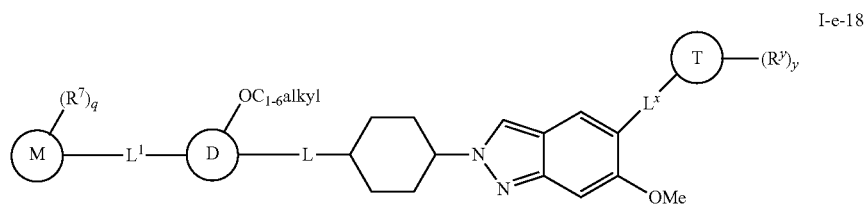

I-e-18 or a pharmaceutically acceptable salt thereof, wherein each of Ring M, Ring D, L, $L^1$, $R^7$, q, $L^x$, Ring T, $R^y$, and y is as defined above and described in embodiments herein, both singly and in combination.

In some embodiments, the present invention provides the compound of formula I-a, wherein LBM is

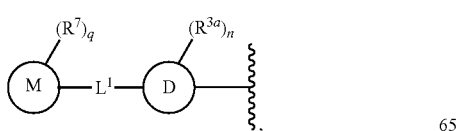

Ring Q and Ring P form an indazole ring, n is 1 and $R^{3a}$ is —OMe, x is 1 and $R^x$ is —OMe, and X is cyclohexyl as shown, to provide a compound of formula I-e-19:

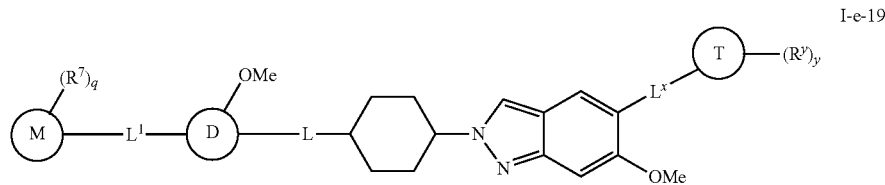

I-e-19 or a pharmaceutically acceptable salt thereof, wherein each of Ring M, Ring D, L, $L^1$, $R^7$, q, $L^x$, Ring T, $R^y$, and y is as defined above and described in embodiments herein, both singly and in combination.

In some embodiments, the present invention provides the compound of formula I-a, wherein LBM is

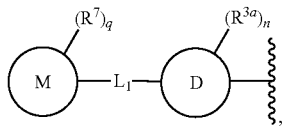

L is

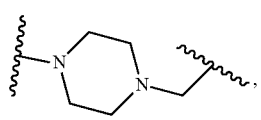 [SMILES: *CN1CCN(*)CC1]

Ring Q and Ring P form an indazole ring, n is 1 and $R^{3a}$ is —OC$_{1-6}$ alkyl, x is 1 and $R^x$ is —OMe, and X is cyclohexyl as shown, to provide a compound of formula I-e-20:

I-e-20

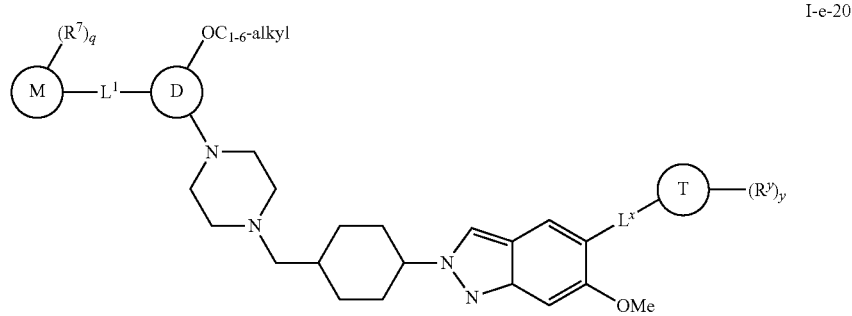

or a pharmaceutically acceptable salt thereof, wherein each of Ring M, Ring D, L, $L^1$, $R^7$, q, $L^x$, Ring T, $R^y$, and y is as defined above and described in embodiments herein, both singly and in combination.

In some embodiments, the present invention provides the compound of formula I-a, wherein LBM is

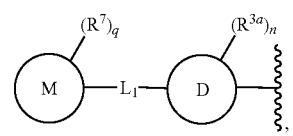

L is

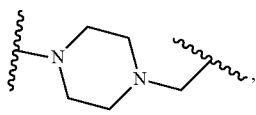 [SMILES: *CN1CCN(*)CC1]

Ring Q and Ring P form an indazole ring, n is 1 and $R^{3a}$ is —OMe, x is 1 and $R^x$ is —OMe, and X is cyclohexyl as shown, to provide a compound of formula I-e-21:

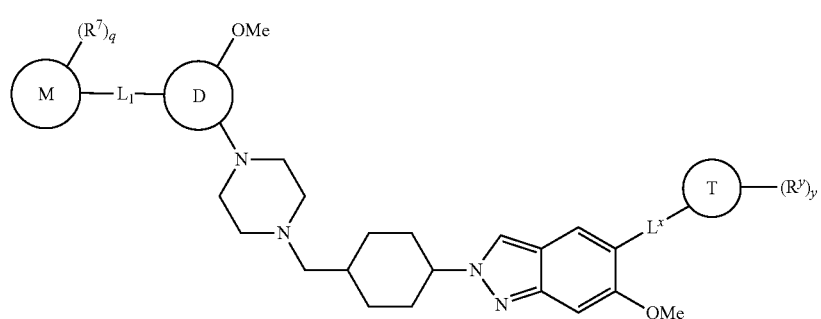

I-e-21 or a pharmaceutically acceptable salt thereof, wherein each of Ring M, Ring D, L, $L^1$, $R^7$, q, $L^x$, Ring T, $R^y$, and y is as defined above and described in embodiments herein, both singly and in combination.

In some embodiments, LBM is an E3 ligase ligand well known to one of ordinary skill in the art including those described in M. Toure, C. M. Crews, *Angew. Chem. Int. Ed.* 2016, 55, 1966, T. Uehara et al. *Nature Chemical Biology* 2017, 13, 675, WO 2017/176708, US 2017/0281784, WO 2017/161119, WO 2017/176957, WO 2017/176958, WO 2015/160845, US 2015/0291562, WO 2016/197032, WO 2016/105518, US 2018/0009779, WO 2017/007612, 2018/0134684, WO 2013/106643, US 2014/0356322, WO 2002/020740, US 2002/0068063, WO 2012/078559, US 2014/0302523, WO 2012/003281, US 2013/0190340, US 2016/0022642, WO 2014/063061, US 2015/0274738, WO 2016/118666, US 2016/0214972, WO 2016/149668, US 2016/0272639, WO 2016/169989, US 2018/0118733, WO 2016/197114, US 2018/0147202, WO 2017/011371, US 2017/0008904, WO 2017/011590, US 2017/0037004, WO 2017/079267, US 2017/0121321, WO 2017/117473, WO 2017/117474, WO 2013/106646, WO 2014/108452, WO 2017/197036, US 2019/0076540, WO 2017/197046, US 2019/0076542, WO 2017/197051, US 2019/0076539, WO 2017/197055, US 2019/0076541, and WO 2017/197056, the entirety of each of which is herein incorporated by reference.

In certain embodiments, the present invention provides a compound of Formula I, wherein LBM is an E3 ubiquitin ligase (cereblon) binding moiety thereby forming a compound of formula I-oo-1, I-oo-2, I-oo-3, I-oo-4, I-oo-5, I-oo-6, I-oo-7, I-oo-8, I-oo-9, or I-oo-10 respectively:

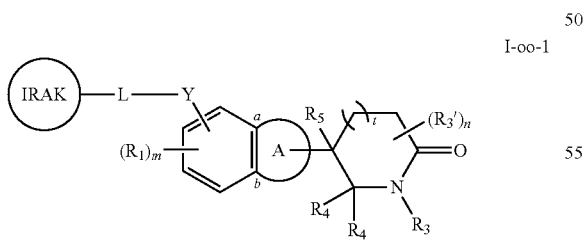

I-oo-1

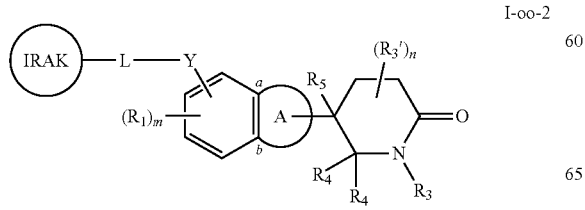

I-oo-2

-continued

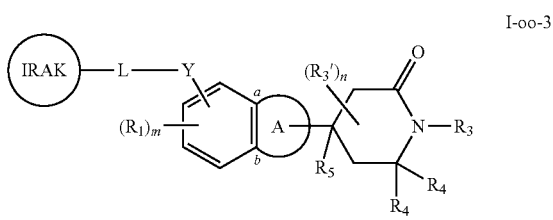

I-oo-3

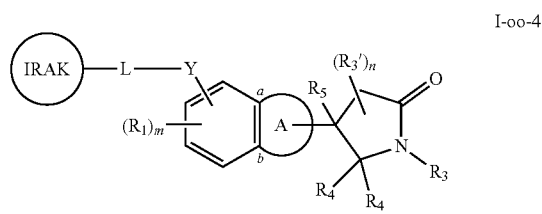

I-oo-4

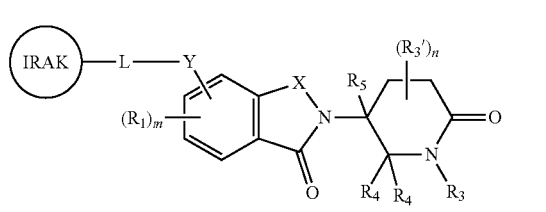

I-oo-5

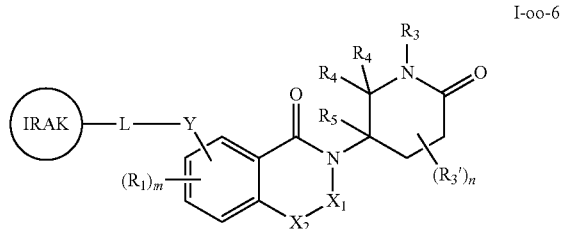

I-oo-6

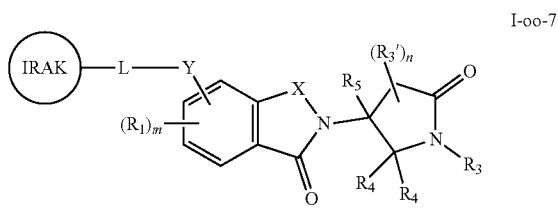

I-oo-7

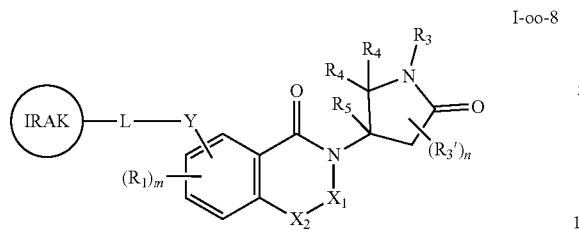
I-oo-8
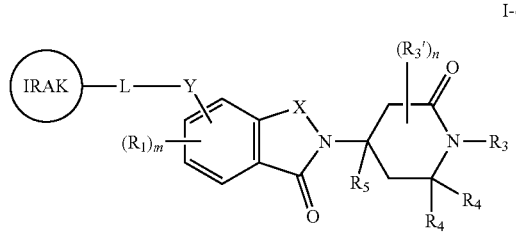
I-oo-9
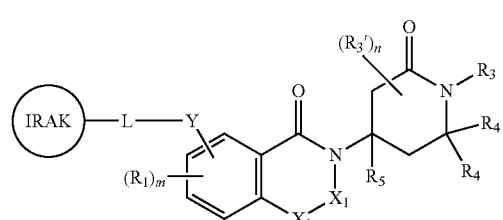
I-oo-10
or a compound of formula I-oo'-1, I-oo'-2, I-oo'-3, I-oo'-4, I-oo'-5, I-oo'-6, I-oo'-7, I-oo'-8, I-oo'-9, or I-oo'-10 respectively:
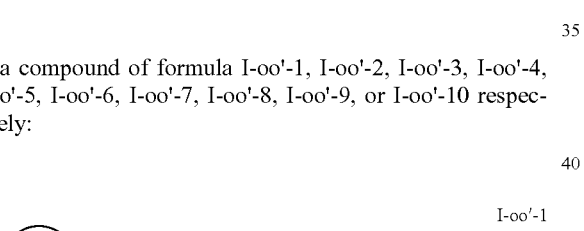
I-oo'-1

I-oo'-2
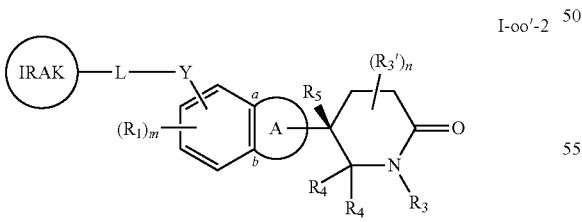
I-oo'-3
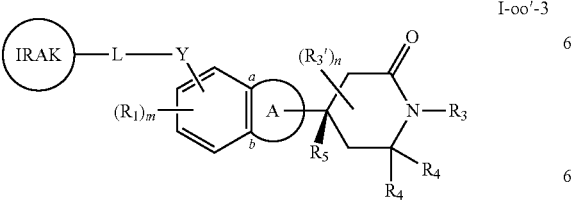
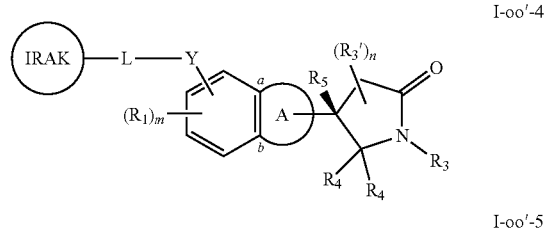
I-oo'-4
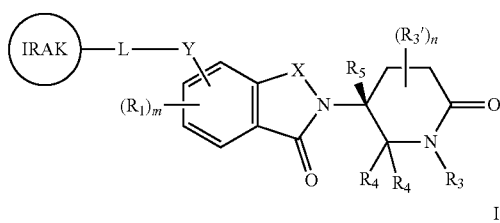
I-oo'-5
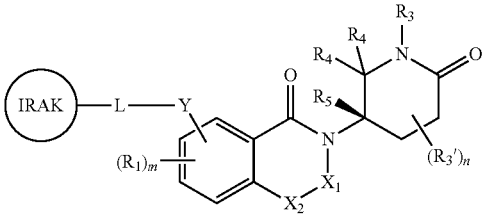
I-oo'-6
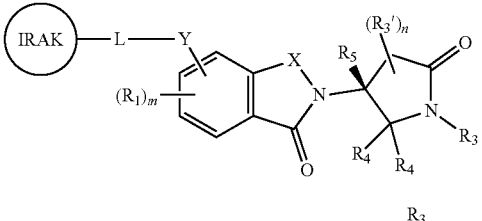
I-oo'-7
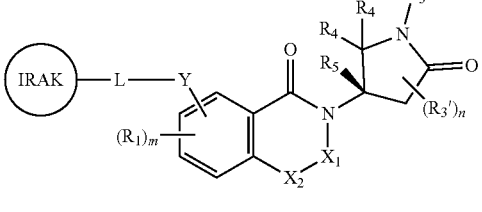
I-oo'-8
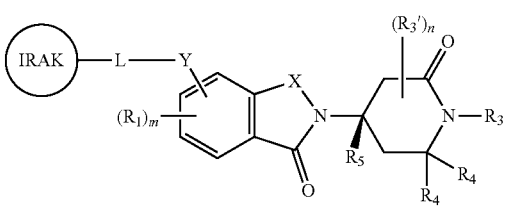
I-oo'-9
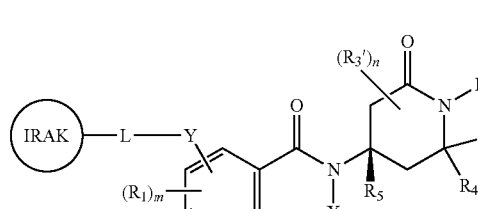
I-oo'-10
or a compound of formula I-oo''-1, I-oo''-2, I-oo''-3, I-oo''-4, I-oo''-5, I-oo''-6, I-oo''-7, I-oo''-8, I-oo''-9, or I-oo''-10 respectively:

I-oo"-1
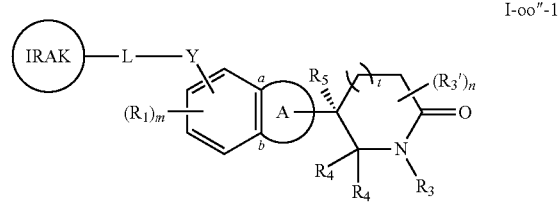

I-oo"-2
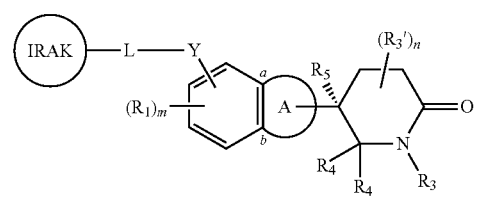

I-oo"-3
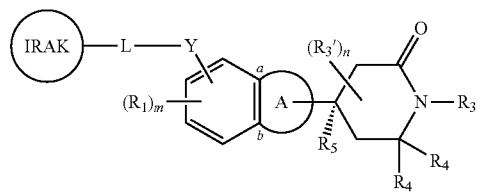

I-oo"-4
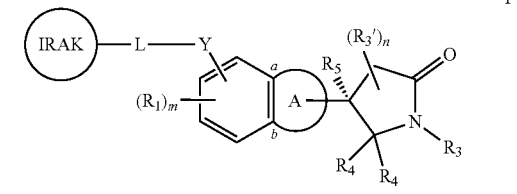

I-oo"-5
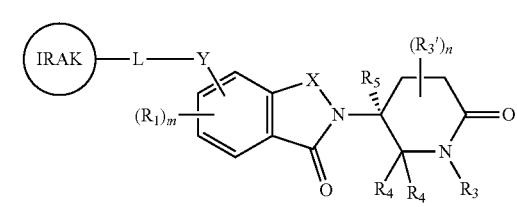

I-oo"-6
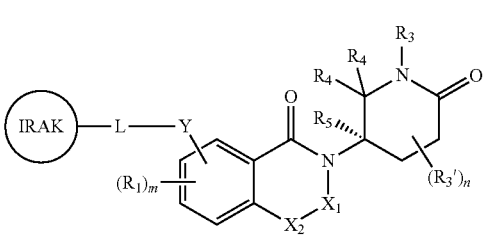

I-oo"-7
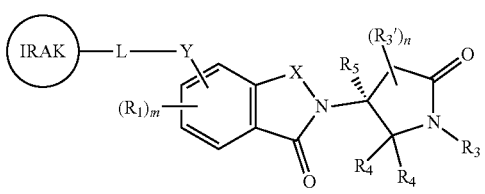

I-oo"-8
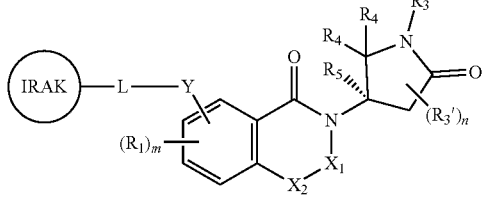

I-oo"-9
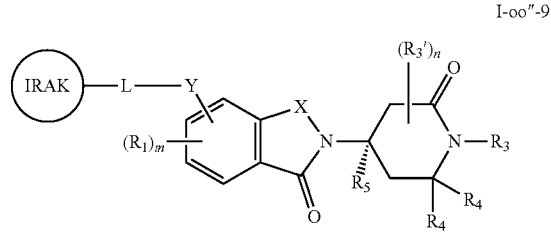

I-oo"-10
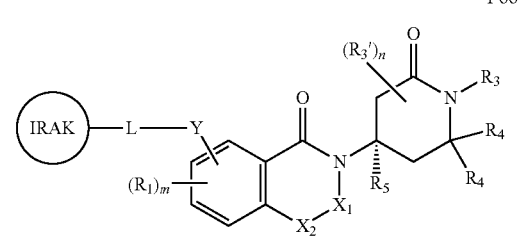

or a pharmaceutically acceptable salt thereof, wherein L and IRAK are as defined above and described in embodiments herein, and wherein each of the variable

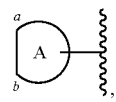

$X, X_1, X_2, Y, R_1, R_3, R_3', R_4, R_5$, t, m and n is as defined and described in WO 2017/007612 and US 2018/0134684, the entirety of each of which is herein incorporated by reference.

Accordingly in some embodiments, the present invention provides a compound of formula I-oo-1, I-oo-2, I-oo-3, I-oo-4, I-oo-5, I-oo-6, I-oo-7, I-oo-8, I-oo-9, I-oo-10, I-oo'-1, I-oo'-2, I-oo'-3, I-oo'-4, I-oo'-5, I-oo'-6, I-oo'-7, I-oo'-8, I-oo'-9, I-oo'-10, I-oo"-1, I-oo"-2, I-oo"-3, I-oo"-4, I-oo"-5, I-oo"-6, I-oo"-7, I-oo"-8, I-oo"-9, or I-oo"-10, or a pharmaceutically acceptable salt thereof, wherein:

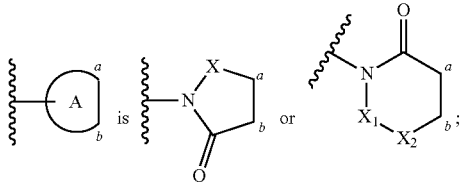

Y is a bond, $Y_1$, O, NH, $NR_2$, C(O)O, OC(O), C(O)$NR_2'$, $NR_2'$C(O), $Y_1$—O, $Y_1$—NH, $Y_1$—$NR_2$, $Y_1$—C(O), $Y_1$—C(O)O, $Y_1$—OC(O), $Y_1$—C(O)$NR_2'$, or $Y_1$—$NR_2'$C(O), wherein $Y_1$ is $C_1$-$C_6$ alkylene, $C_2$-$C_6$ alkenylene, or $C_2$-$C_6$ alkynylene;

X is C(O) or C($R_3$)$_2$;

$X_1$—$X_2$ is $C(R_3)$=N or $C(R_3)_2$—$C(R_3)_2$;

each $R_1$ is independently halogen, nitro, $NH_2$, OH, C(O)OH, $C_1$-$C_6$ alkyl, or $C_1$-$C_6$ alkoxy;

$R_2$ is $C_1$-$C_6$ alkyl, $C_2$-$C_6$ alkenyl, $C_3$-$C_8$ cycloalkyl, 3- to 8-membered heterocycloalkyl, C(O)—$C_1$-$C_6$ alkyl, C(O)—$C_2$-$C_6$ alkenyl, C(O)—$C_3$-$C_8$ cycloalkyl, or C(O)-3- to 8-membered heterocycloalkyl, and $R_2$ is optionally substituted with one or more of halogen, $N(R_a)_2$, $NHC(O)R_a$, $NHC(O)OR_a$, $OR_b$, $C_3$-$C_8$ cycloalkyl, 3- to 8-membered heterocycloalkyl, $C_6$-$C_{10}$ aryl, or 5- to 10-membered heteroaryl, wherein each of the $C_3$-$C_8$ cycloalkyl, 3- to 8-membered heterocycloalkyl, $C_6$-$C_{10}$ aryl or 5- to 10-membered heteroaryl is optionally further substituted with one or more of halogen, $NH_2$, CN, nitro, OH, C(O)OH, $C_1$-$C_6$ alkyl, $C_1$-$C_6$ haloalkyl, $C_1$-$C_6$ alkoxy, or $C_1$-$C_6$ haloalkoxy;

$R_2'$ is H, $C_1$-$C_6$ alkyl, $C_2$-$C_6$ alkenyl, $C_3$-$C_8$ cycloalkyl, or 3- to 8-membered heterocycloalkyl, and $R_2'$, when not being H, is optionally substituted with one or more of halogen, $N(R_a)_2$, $NHC(O)R_a$, $NHC(O)OR_a$, $OR_b$, $C_3$-$C_8$ cycloalkyl, 3- to 8-membered heterocycloalkyl, $C_6$-$C_{10}$ aryl, or 5- to 10-membered heteroaryl, wherein each of the $C_3$-$C_8$ cycloalkyl, 3- to 8-membered heterocycloalkyl, $C_6$-$C_{10}$ aryl or 5- to 10-membered heteroaryl is optionally further substituted with one or more of halogen, $NH_2$, CN, nitro, OH, C(O)OH, $C_1$-$C_6$ alkyl, $C_1$-$C_6$ haloalkyl, $C_1$-$C_6$ alkoxy, or $C_1$-$C_6$ haloalkoxy;

each $R_3$ is independently H or $C_1$-$C_3$ alkyl optionally substituted with $C_6$-$C_{10}$ aryl or 5- to 10-membered heteroaryl;

each $R_3'$ is independently $C_1$-$C_3$ alkyl;

each $R_4$ is independently H or $C_1$-$C_3$ alkyl; or two $R_4$, together with the carbon atom to which they are attached, form C(O), a $C_3$-$C_6$ carbocycle, or a 4-, 5-, or 6-membered heterocycle comprising 1 or 2 heteroatoms selected from N and O;

$R_5$ is H, $C_1$-$C_3$ alkyl, F, or Cl;

each $R_a$ independently is H or $C_1$-$C_6$ alkyl;

$R_b$ is H or tosyl;

t is 0 or 1;

m is 0, 1, 2 or 3; and n is 0, 1 or 2.

In certain embodiments, the present invention provides a compound of Formula I, wherein LBM is an E3 ubiquitin ligase (cereblon) binding moiety thereby forming a compound of formula I-pp-1, I-pp-2, I-pp-3, I-pp-4, I-pp-5, or I-pp-6 respectively:

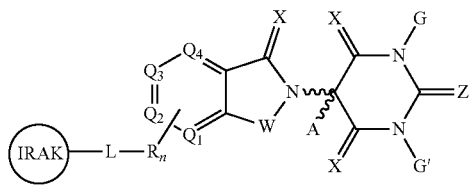

I-pp-1

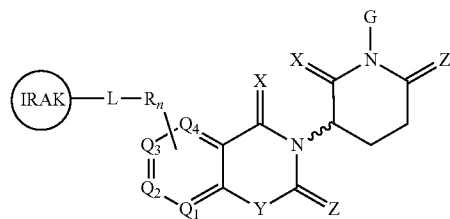

I-pp-2

I-pp-3


I-pp-4

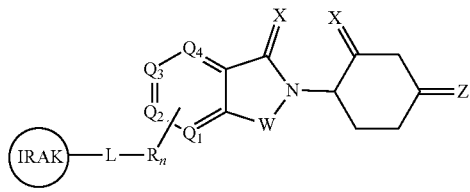

I-pp-5

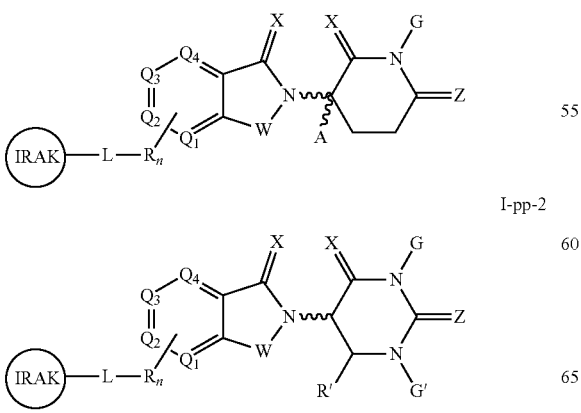

I-pp-6 or a pharmaceutically acceptable salt thereof, wherein L and IRAK are as defined above and described in embodiments herein, and wherein each of the variables A, G, G', $Q_1$, $Q_2$, $Q_3$, $Q_4$, R, $R^1$, W, X, Y, Z, ⁓, and n is as defined and described in WO 2016/197114 and US 2018/0147202, the entirety of each of which is herein incorporated by reference.

In some embodiments, LBM is

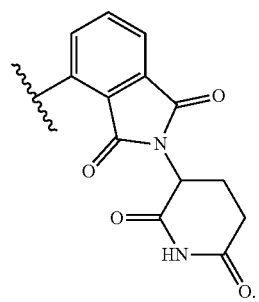 [SMILES: *c1cccc2c1C(=O)N(C1CCC(=O)NC1=O)C2=O]

In some embodiments, LBM is

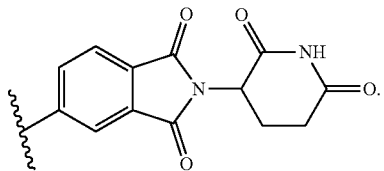 [SMILES: *c1ccc2c(c1)C(=O)N(C1CCC(=O)NC1=O)C2=O]

In some embodiments, LBM is

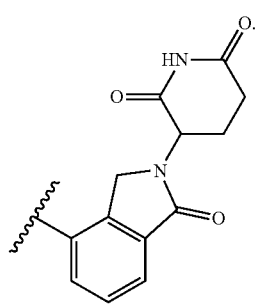 [SMILES: *c1cccc2c1CN(C1CCC(=O)NC1=O)C2=O]

In some embodiments, LBM is

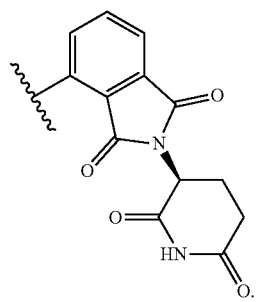 [SMILES: *c1cccc2c1C(=O)N([C@H]1CCC(=O)NC1=O)C2=O]

In some embodiments, LBM is

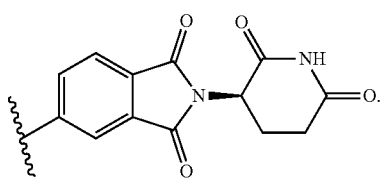 [SMILES: *c1ccc2c(c1)C(=O)N([C@@H]1CCC(=O)NC1=O)C2=O]

In some embodiments, LBM is

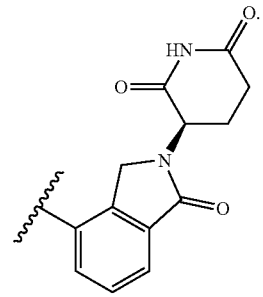 [SMILES: *c1cccc2c1CN([C@@H]1CCC(=O)NC1=O)C2=O]

In some embodiments, LBM is

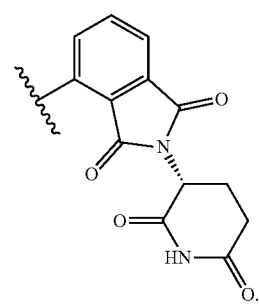 [SMILES: *c1cccc2c1C(=O)N([C@@H]1CCC(=O)NC1=O)C2=O]

In some embodiments, LBM is

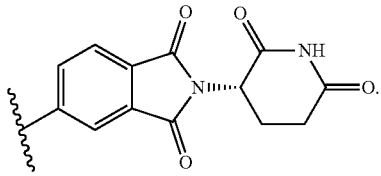 [SMILES: *c1ccc2c(c1)C(=O)N([C@H]1CCC(=O)NC1=O)C2=O]

In some embodiments, LBM is

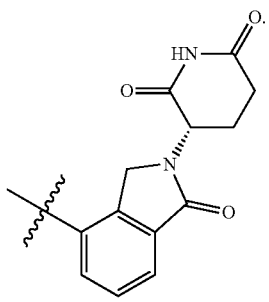 [SMILES: *c1cccc2c1CN([C@H]1CCC(=O)NC1=O)C2=O]

In some embodiments, LBM is selected from those in Table 1 below.

In some embodiments, the present invention provides a compound of formula I-a, wherein LBM is thalidomide and Ring P and Ring Q form a benzoxazole ring as shown, to provide a compound of formula I-j-1:

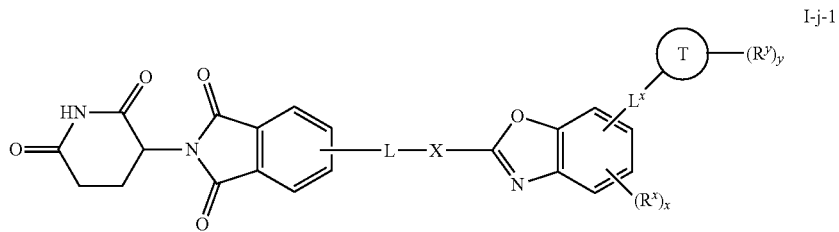

I-j-1 or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a, wherein LBM is thalidomide and Ring P and Ring Q form an indazole ring as shown, to provide a compound of formula I-j-3:

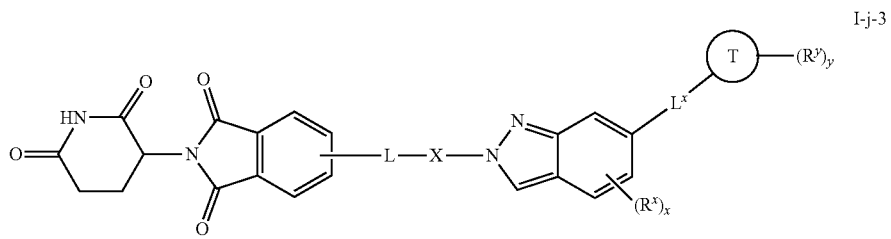

I-j-3 or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a, wherein LBM is thalidomide and Ring P and Ring Q form a imidazo[1,2-a]pyridine ring as shown, to provide a compound of formula I-j-4:

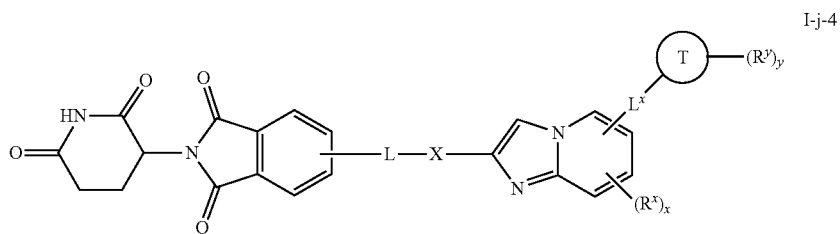

I-j-4 or a pharmaceutically acceptable salt thereof, wherein each of L, $L^x$, X, $R^x$, $R^y$, Ring T, x, and y is as defined above and described in embodiments herein, both singly and in combination.

In some embodiments, the present invention provides a compound of formula I-a, wherein LBM is thalidomide or

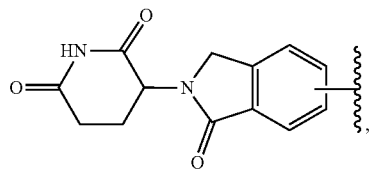

Ring Q is

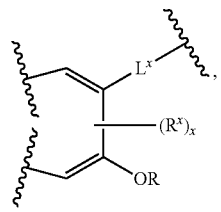

a single $R^x$ is —OR, and X is cyclohexyl as shown, to provide a compound of formula I-k-2 or I-k-3:

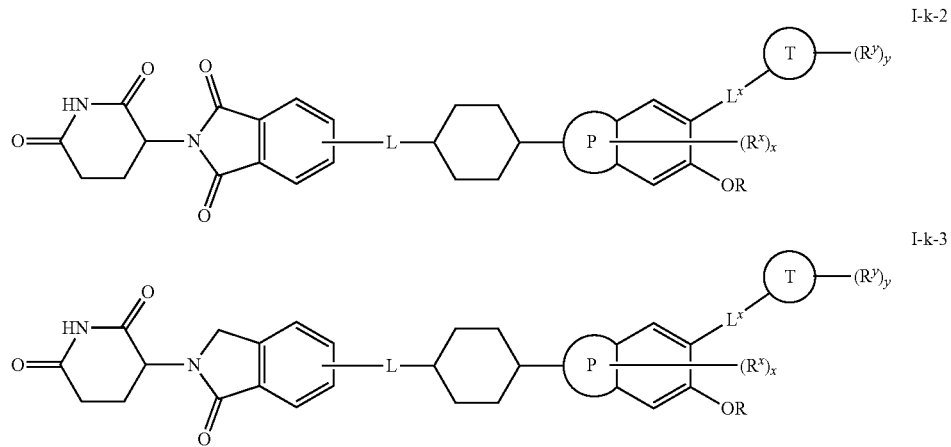

or a pharmaceutically acceptable salt thereof, wherein L is as defined and described herein, and wherein:

each $R^x$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP(O)R$_2$, —OP(O)(OR)$_2$, —OP(O)(OR)NR$_2$, —OP(O)(NR$_2$)$_2$, —P(O)R$_2$, —SiR$_3$, —Si(OR)R$_2$, or

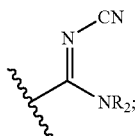

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —SiR$_3$, —SF$_5$, or

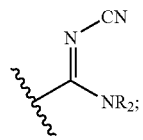

each $R^z$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring P is selected from benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P is optionally substituted with 1-2 oxo groups;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

$L^x$ is a covalent bond or a $C_{1-3}$ bivalent straight or branched saturated or unsaturated hydrocarbon chain wherein 1-2 methylene units of the chain are independently and optionally replaced with -Cy$^x$-, —O—, —S—, —C(O)—, —C(S)—, —CR$_2$—, —CRF—, —CF$_2$—, —NR—, —N═CR—, —CR═CR—, or —S(O)$_2$—, wherein R of —CR$_2$—, —CRF—, —NR—, —N═CR—, or —CR═CR— can combine with R$^x$ or R$^y$ to form a 4-7 membered saturated or partially unsaturated carbocyclic or heterocyclic ring having 1-3 heteroatoms independently selected from nitrogen, oxygen, and sulfur;

-Cy$^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -Cy$^x$- is optionally substituted with 1-2 oxo groups;

each x is 0, 1, 2, 3 or 4; and each y is 0, 1, 2, 3 or 4.

In certain embodiments, the present invention provides a compound of formula I-k-2 or I-k-3 above, wherein $L^x$ is amide, Ring P is pyrazolyl, Ring T is pyridyl, R is Me, and R$^y$ is —CF$_3$.

In some embodiments, the present invention provides a compound of formula I-a, wherein LBM is thalidomide or

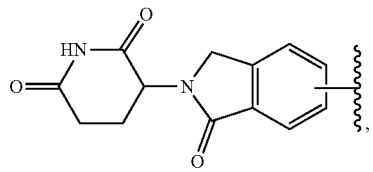

Ring P and Ring Q form an indazole ring, a single R$^x$ is —OR, and X is cyclohexyl as shown, to provide a compound of formula I-k-4 or I-k-5:

I-k-4

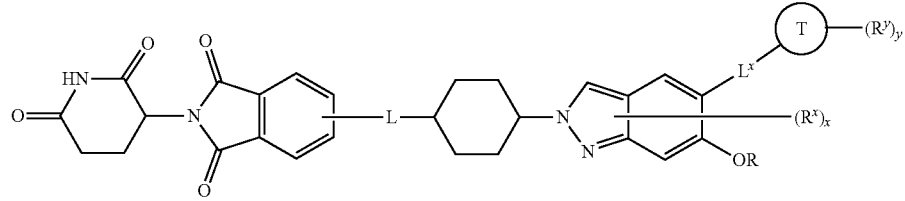

I-k-5

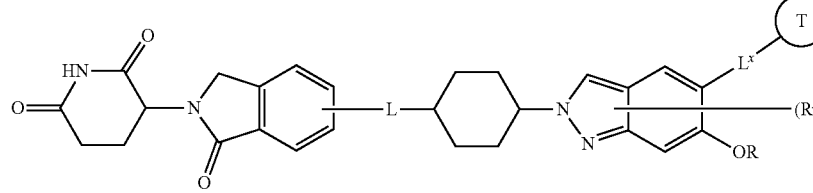

or a pharmaceutically acceptable salt thereof, wherein L is as defined and described herein, and wherein:

each R$^x$ is independently hydrogen, deuterium, R$^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP(O)R$_2$, —OP(O)(OR)$_2$, —OP(O)(OR)NR$_2$, —OP(O)(NR$_2$)$_2$, —P(O)R$_2$, —SiR$_3$, —Si(OR)R$_2$, or

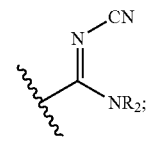

or two R$^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each R$^y$ is independently hydrogen, deuterium, R$^z$, halogen, —CN, —NO$_2$, —OR, SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —SiR$_3$, —SF$_5$, or

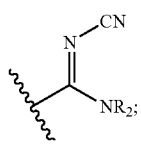

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

$L^x$ is a covalent bond or a $C_{1-3}$ bivalent straight or branched saturated or unsaturated hydrocarbon chain wherein 1-2 methylene units of the chain are independently and optionally replaced with -Cy$^x$-, —O—, —S—, —C(O)—, —C(S)—, —CR$_2$—, —CRF—, —CF$_2$—, —NR—, —N=CR—, —CR=CR—, or —S(O)$_2$—, wherein R of —CR$_2$—, —CRF—, —NR—, —N=CR—, or —CR=CR— can combine with $R^x$ or $R^y$ to form a 4-7 membered saturated or partially unsaturated carbocyclic or heterocyclic ring having 1-3 heteroatoms independently selected from nitrogen, oxygen, and sulfur;

-Cy$^x$- is an optionally substituted ring selected from a 3-5 membered saturated or partially unsaturated carbocyclic or heterocyclic ring having 0-3 heteroatoms independently selected from nitrogen, oxygen, and sulfur, or a 5 membered heteroaryl ring having 1-4 heteroatoms independently selected from nitrogen, oxygen, and sulfur, wherein -Cy$^x$- is optionally substituted with 1-2 oxo groups;

each x is 0, 1, 2, 3 or 4; and
each y is 0, 1, 2, 3 or 4.

In certain embodiments, the present invention provides a compound of formula I-k-6 or I-k-7 above, wherein $L^x$ is amide, Ring T is pyridyl, R is Me, and $R^y$ is —CF$_3$.

In some embodiments, the present invention provides a compound of formula I-a, wherein LBM is thalidomide or

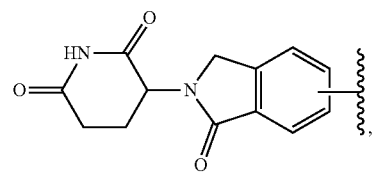

Ring Q is

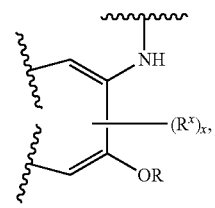

a, $L^x$ is amide, a single $R^x$ is —OR, and X is cyclohexyl as shown, to provide a compound of formula I-k-6 or I-k-7:

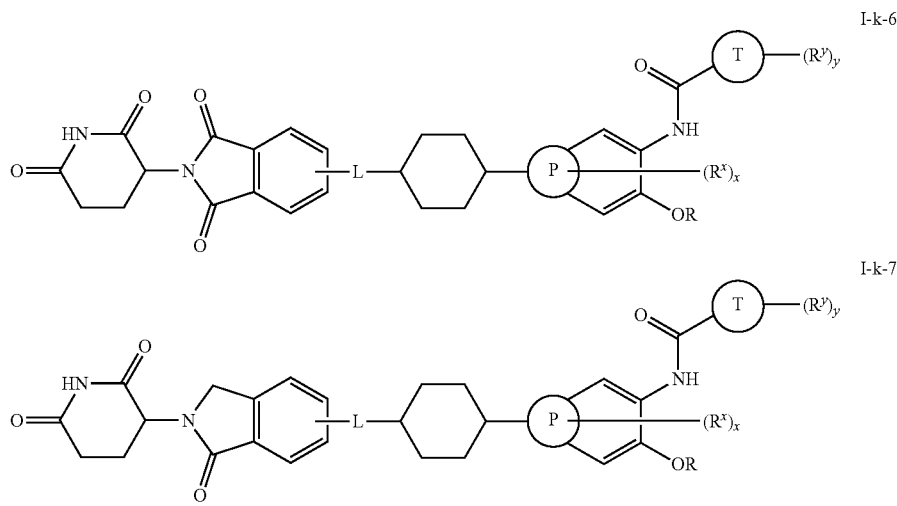

or a pharmaceutically acceptable salt thereof, wherein L is as defined and described herein, and wherein:

each $R^x$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP (O)R$_2$, —OP(O)(OR)$_2$, —OP(O)(OR)NR$_2$, —OP(O)(NR$_2$)$_2$, —P(O)R$_2$, —SiR$_3$, —Si(OR)R$_2$, or

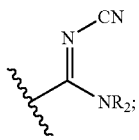

or two R$^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each R$^y$ is independently hydrogen, deuterium, R$^z$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —SiR$_3$, —SF$_5$, or

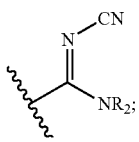

each R$^z$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring P is selected from benzo, a 4-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring P is optionally substituted with 1-2 oxo groups;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

each x is 0, 1, 2, 3 or 4; and each y is 0, 1, 2, 3 or 4.

In certain embodiments, the present invention provides a compound of formula I-k-6 or I-k-7 above, wherein Ring P is pyrazolyl, Ring T is pyridyl, R is Me, and R$^y$ is —CF$_3$.

In some embodiments, the present invention provides a compound of formula I-a, wherein LBM is thalidomide or

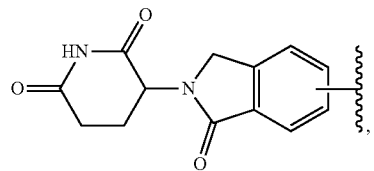

Ring P and Ring Q form an indazole ring, L$^x$ is amide, a single R$^x$ is —OR, and X is cyclohexyl as shown, to provide a compound of formula I-k-8 or I-k-9:

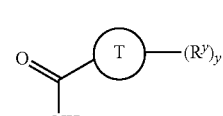

I-k-8

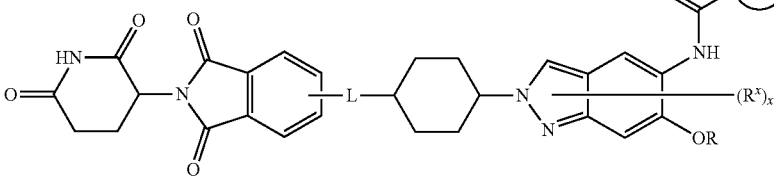

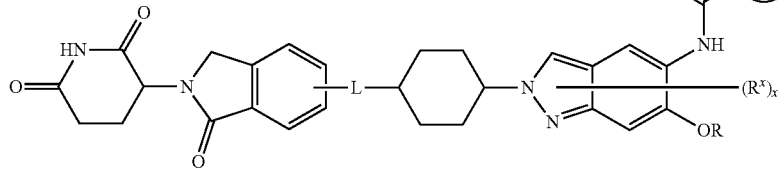

I-k-9 or a pharmaceutically acceptable salt thereof, wherein L is as defined and described herein, and wherein:

each $R^x$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP(O)R$_2$, —OP(O)(OR)$_2$, —OP(O)(OR)NR$_2$, —OP(O)(NR$_2$)$_2$, —P(O)R$_2$, —SiR$_3$, —Si(OR)R$_2$, or

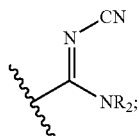

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(S)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —SiR$_3$, —SF$_5$, or

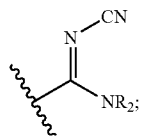

each $R^z$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring T is selected from phenyl, a 4-7 membered saturated or partially unsaturated carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur, wherein Ring T is further optionally substituted with 1-2 oxo groups;

each x is 0, 1, 2, 3 or 4; and each y is 0, 1, 2, 3 or 4.

In certain embodiments, the present invention provides a compound of formula I-k-8 or I-k-9 above, wherein Ring T is pyridyl, R is Me, and $R^y$ is —CF$_3$.

In some embodiments, the present invention provides a compound of formula I-a, wherein LBM is thalidomide or

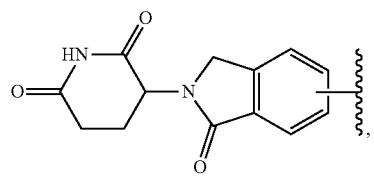

Ring P and Ring Q form an indazole ring, Ring T is pyridyl, $L^x$ is amide, a single $R^x$ is —OR, and X is cyclohexyl as shown, to provide a compound of formula I-k-10 or I-k-11:

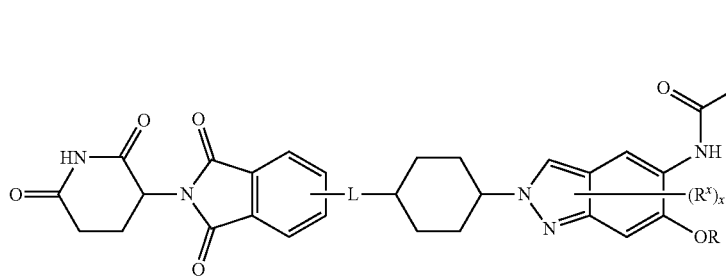

I-k-10

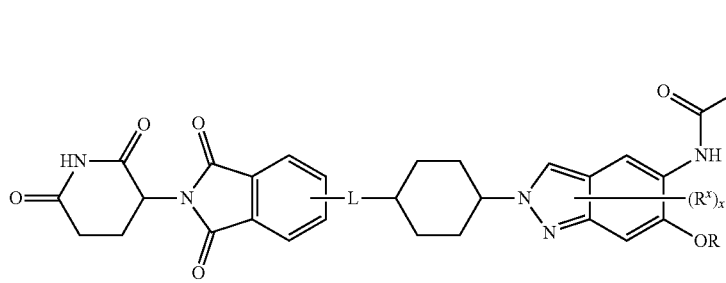

I-k-11 or a pharmaceutically acceptable salt thereof, wherein L is as defined and described herein, and wherein:

each $R^x$ is independently hydrogen, deuterium, $R^z$, halogen, —CN, —NO₂, —OR, —SR, —NR₂, —S(O)₂R, —S(O)₂NR₂, —S(O)R, —CFR₂, —CF₂R, —CF₃, —CR₂(OR), —CR₂(NR₂), —C(O)R, —C(O)OR, —C(O)NR₂, —C(S)NR₂, —C(O)N(R)OR, —OC(O)R, —OC(O)NR₂, —N(R)C(O)OR, —N(R)C(O)R, —N(R)C(O)NR₂, —N(R)S(O)₂R, —N⁺(O⁻)R₂, —OP(O)R₂, —OP(O)(OR)₂, —OP(O)(OR)NR₂, —OP(O)(NR₂)₂, —P(O)R₂, —SiR₃, —Si(OR)R₂, or

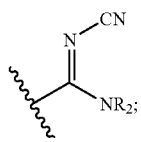

or two $R^x$ groups are optionally taken together to form an optionally substituted 5-6 membered partially unsaturated or aryl fused ring having 0-3 heteroatoms independently selected from nitrogen, oxygen, or sulfur;

each R is independently hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form a 4-7 membered saturated, partially unsaturated, or heteroaryl ring having 0-3 heteroatoms, in addition to the carbon or nitrogen, independently selected from nitrogen, oxygen, and sulfur;

each $R^y$ is independently hydrogen, deuterium, $R^z$, halogen, —CN, —NO₂, —OR, SR, —NR₂, —S(O)₂R, —S(O)₂NR₂, —S(O)R, —CF₂R, —CF₃, —CR₂(OR), —CR₂(NR₂), —C(O)R, —C(O)OR, —C(O)NR₂, —C(S)NR₂, —C(O)N(R)OR, —OC(O)R, —OC(O)NR₂, —N(R)C(O)OR, —N(R)C(O)R, —N(R)C(O)NR₂, —N(R)S(O)₂R, —OP(O)R₂, —OP(O)(OR)₂, —OP(O)(OR)NR₂, —OP(O)(NR₂)₂, —SiR₃, —SF₅, or

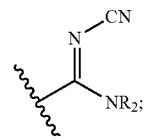

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each x is 0, 1, 2, 3 or 4; and each y is 0, 1, 2, 3 or 4.

In certain embodiments, the present invention provides a compound of formula I-k-10 or I-k-11 above, wherein R is Me and $R^y$ is —CF₃.

In some embodiments, the present invention provides a compound of formula I-a, wherein LBM is

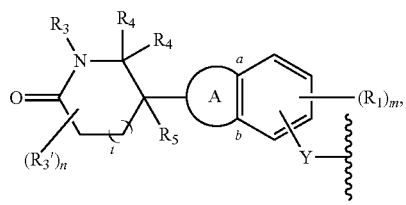

Ring Q is

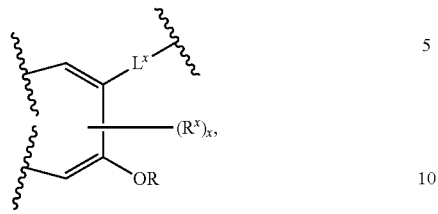

a single $R^x$ is —OR, and X is cyclohexyl as shown, to provide a compound of formula I-k-12:

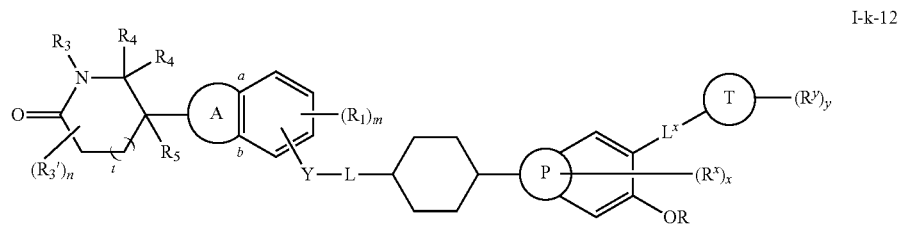

I-k-12 or a pharmaceutically acceptable salt thereof, wherein each of variables

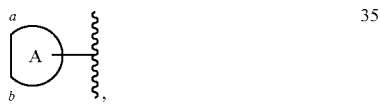

Y, $R_1$, $R_3$, $R_3'$, $R_4$, $R_5$, t, m, n, Ring P, Ring T, L, $L^x$, $R^x$, $R^y$, x, and y is as defined above and described in embodiments herein, both singly and in combination.

In some embodiments, the present invention provides a compound of formula I-a, wherein LBM is

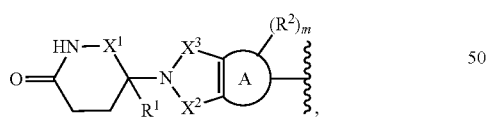

Ring Q is

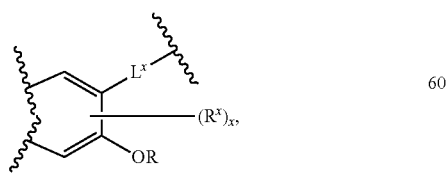

a single $R^x$ is —OR, and X is cyclohexyl as shown, to provide a compound of formula I-k-13:

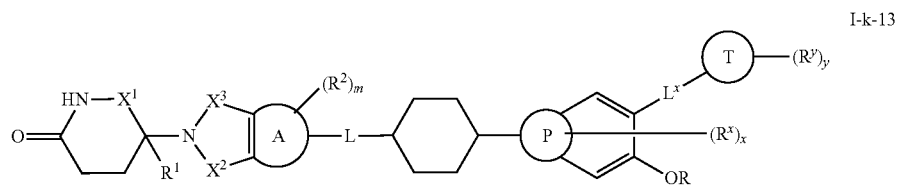

or a pharmaceutically acceptable salt thereof, wherein each of variables $X^1$, $X^2$, $X^3$, $R^1$, $R^2$, Ring A, m, Ring P, Ring T, L, $L^x$, $R^x$, $R^y$, x, and y is as defined above and described in embodiments herein, both singly and in combination.

In some embodiments, the present invention provides a compound of formula I-a, wherein LBM is

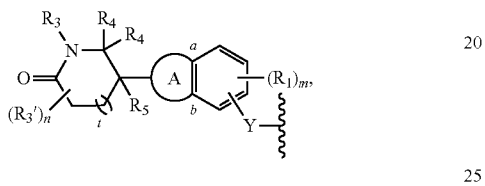

Ring P and Ring Q form an indazole ring, a single $R^x$ is —OR, and X is cyclohexyl as shown, to provide a compound of formula I-k-14:

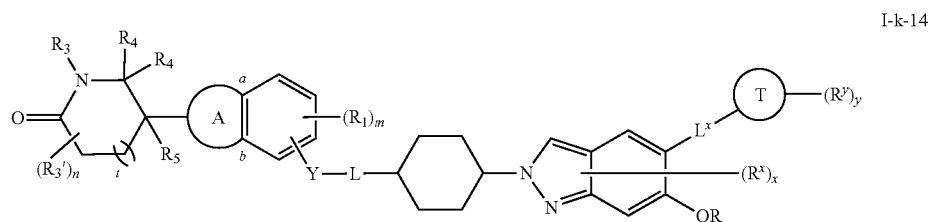

or a pharmaceutically acceptable salt thereof, wherein each of variables

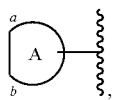

Y, $R_1$, $R_3$, $R_3'$, $R_4$, $R_5$, t, m, n, Ring T, L, $L^x$, $R^x$, $R^y$, x, and y is as defined above and described in embodiments herein, both singly and in combination.

In some embodiments, the present invention provides a compound of formula I-a, wherein LBM is

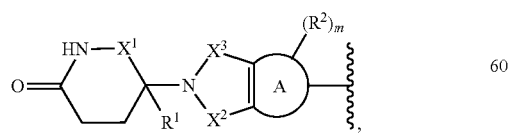

Ring P and Ring Q form an indazole ring, a single $R^x$ is —OR, and X is cyclohexyl as shown, to provide a compound of formula I-k-15:

I-k-15

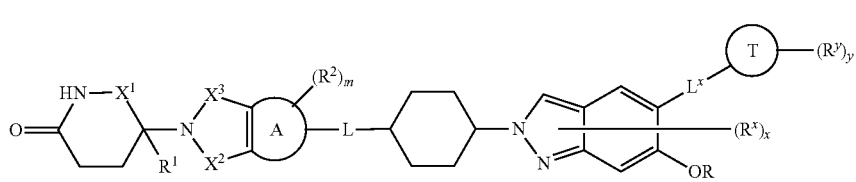

or a pharmaceutically acceptable salt thereof, wherein each of variables $X^1$, $X^2$, $X^3$, $R_1$, $R^2$, Ring A, m, Ring T, L, $L^x$, $R^x$, $R^y$, x, and y is as defined above and described in embodiments herein, both singly and in combination.

In certain embodiments, the present invention provides a compound of Formula I, wherein LBM is an E3 ubiquitin ligase (cereblon) binding moiety thereby forming a compound of formula I-qq-1, I-qq-2, or I-qq-3 respectively:

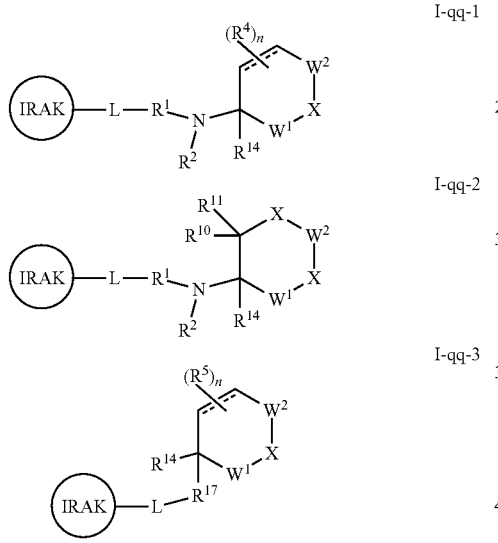

or a pharmaceutically acceptable salt thereof, wherein L and IRAK are as defined above and described herein, and wherein each of the variables $R^1$, $R^2$, $R^4$, $R^5$, $R^{10}$, $R^{11}$, $R^{14}$, $R^{12}$, $W^1$, X, ═══, and n is as defined in WO 2017/197051 which is herein incorporated by reference in its entirety and wherein

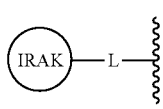

is attached to $R^1$, the ring formed by combining $R^1$ and $R^2$, or $R^{17}$ at the site of attachment of $R^{12}$ as defined in WO 2017/197051 such that

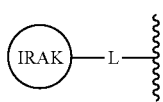

takes the place of the $R^{12}$ substituent.

In some embodiments, the present invention provides a compound of formula I, wherein LBM is an E3 ubiquitin ligase (cereblon) binding moiety thereby forming a compound of formula I-rr-1, I-rr-2, I-rr-3, or I-rr-4, respectively:

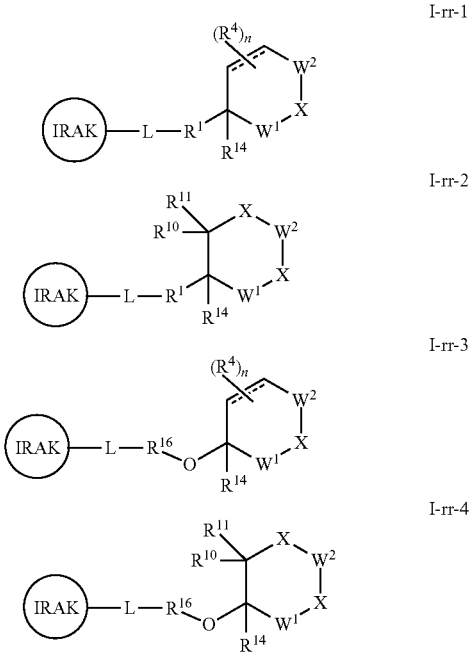

or a pharmaceutically acceptable salt thereof, wherein L and IRAK are as defined above and described herein, and wherein each of the variables $R^1$, $R^4$, $R^{10}$, $R^{11}$, $R^{14}$, $R^{16}$, $W^1$, $W^2$, X, ════, and n is as defined in WO 2018/237026, the entirety of each of which is herein incorporated by reference, and wherein

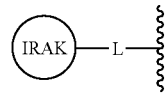

is attached to $R^1$ or $R^{16}$ at the site of attachment of $R^{12}$ as defined in WO 2018/237026, such that

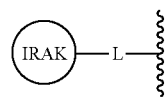

takes the place of the $R^{12}$ substituent.

In some embodiments, the present invention provides a compound of formula I, wherein LBM is an E3 ubiquitin ligase (cereblon) binding moiety thereby forming a compound of formula I-ss-1 or I-ss-3, respectively:

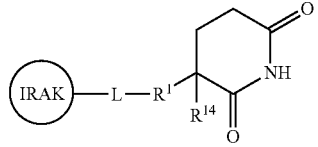

I-ss-1

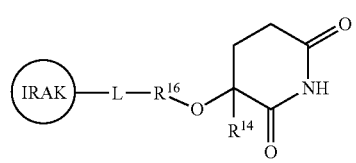

I-ss-3 or a pharmaceutically acceptable salt thereof, wherein L and IRAK are as defined above and described herein, and wherein each of the variables $R^1$, $R^{14}$, and $R^{16}$ is as defined in WO 2018/237026, the entirety of each of which is herein incorporated by reference, and wherein

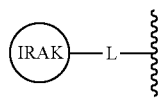

is attached to $R^1$ or $R^{16}$ at the site of attachment of $R^{12}$ as defined in WO 2018/237026, such that

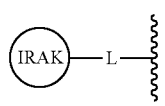

takes the place of the $R^{12}$ substituent.

In certain embodiments, the present invention provides a compound of formula I, wherein LBM is an E3 ubiquitin ligase (cereblon) binding moiety thereby forming a compound of formula I-tt-1, I-tt-2, I-tt-3, I-tt-4, I-tt-5, I-tt-6, I-tt-7, or I-tt-8:

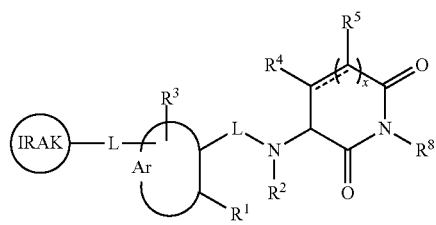

I-tt-1

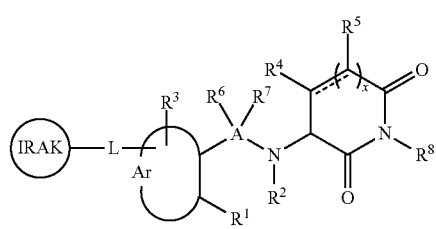

I-tt-2

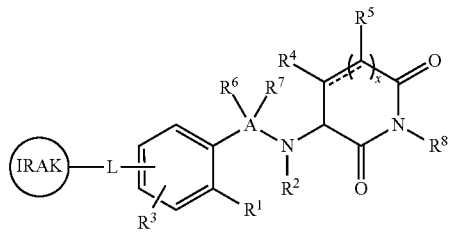

I-tt-3

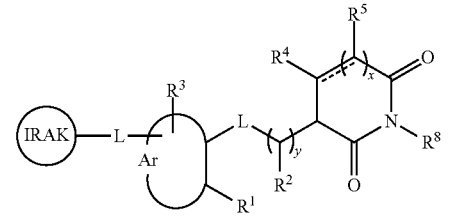

I-tt-4

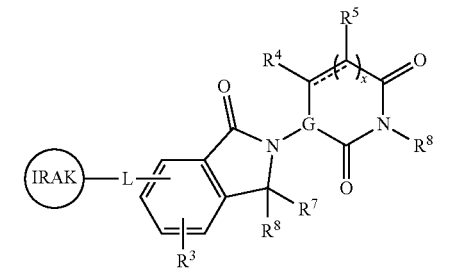

I-tt-5

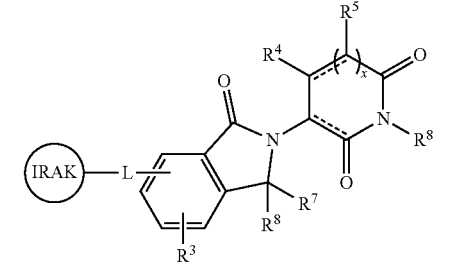

I-tt-6

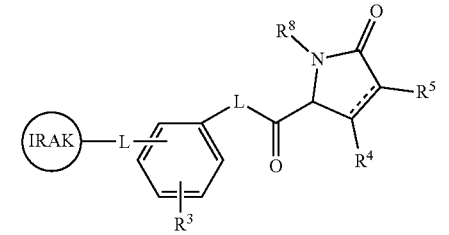

I-tt-7

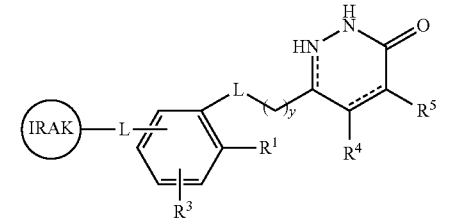

I-tt-8 or a pharmaceutically acceptable salt thereof, wherein L and IRAK are as defined above and described in embodiments herein, and wherein each of the variables Ar, $R^1$, $R^2$, $R^3$, $R^4$, $R^5$, $R^6$, $R^7$, $R^8$, A, L, x, y, and ═══ is as described and defined in WO 2017/161119, the entirety of each of which is herein incorporated by reference.

In certain embodiments, the present invention provides a compound of formula I, wherein LBM is an E3 ubiquitin ligase (cereblon) binding moiety thereby forming a compound of formula I-uu:

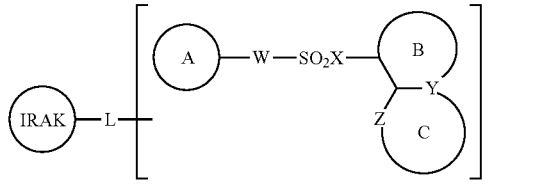

I-uu or a pharmaceutically acceptable salt thereof, wherein L and IRAK are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of formula I, wherein LBM is an E3 ubiquitin ligase (cereblon) binding moiety thereby forming a compound of formula I-vv:

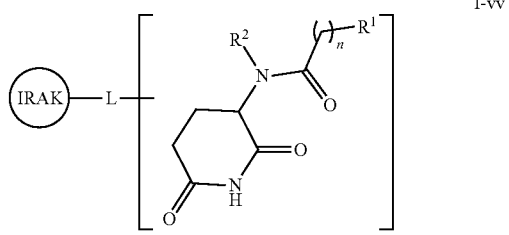

I-vv or a pharmaceutically acceptable salt thereof, wherein L and IRAK are as defined above and described in embodiments herein, and wherein each of the variables $R_1$, $R_2$, and n is as described and defined in WO 2019/043214, the entirety of each of which is herein incorporated by reference.

In some embodiments, LBM is a IAP E3 Ubiquitin ligase binding moiety recited in Varfolomeev, E. et al., *IAP Antagonists Induce Autoubiquitination of c-IAPs, NF-κB activation, and TNFα-Dependent Apoptosis*, Cell, 2007, 131(4): 669-81, such as, for example:

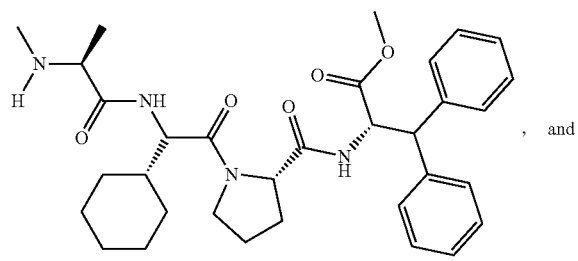

MV1

, and

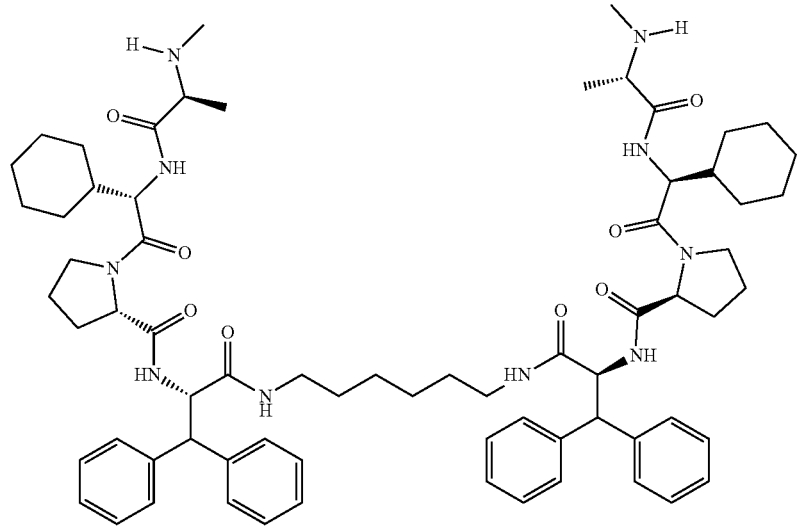

BV6 wherein

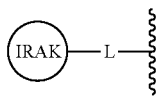

is attached to a modifiable carbon, oxygen, nitrogen or sulfur atom.

In certain embodiments, the present invention provides a compound of Formula I, wherein LBM is a VHL E3 ubiquitin ligase binding moiety thereby forming a compound of formula I-ww-1, I-ww-2, I-ww-3, I-ww-4, or I-ww-5 respectively:

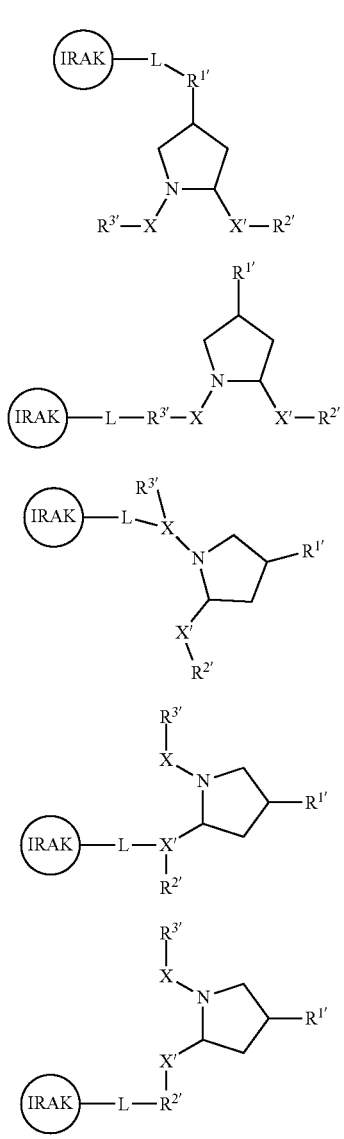

or a pharmaceutically acceptable salt thereof, wherein L and IRAK are as defined above and described in embodiments herein, and wherein each of the variables $R^{1'}$, $R^{2'}$, $R^{3'}$, X, and X' is as defined and described in WO 2013/106643 and US 2014/0356322, the entirety of each of which is herein incorporated by reference.

In certain embodiments, the present invention provides a compound of Formula I, wherein LBM is a VHL E3 ubiquitin ligase binding moiety thereby forming a compound of formula I-xx-1, I-xx-2, I-xx-3, I-xx-4, I-xx-5 or I-xx-6 respectively:

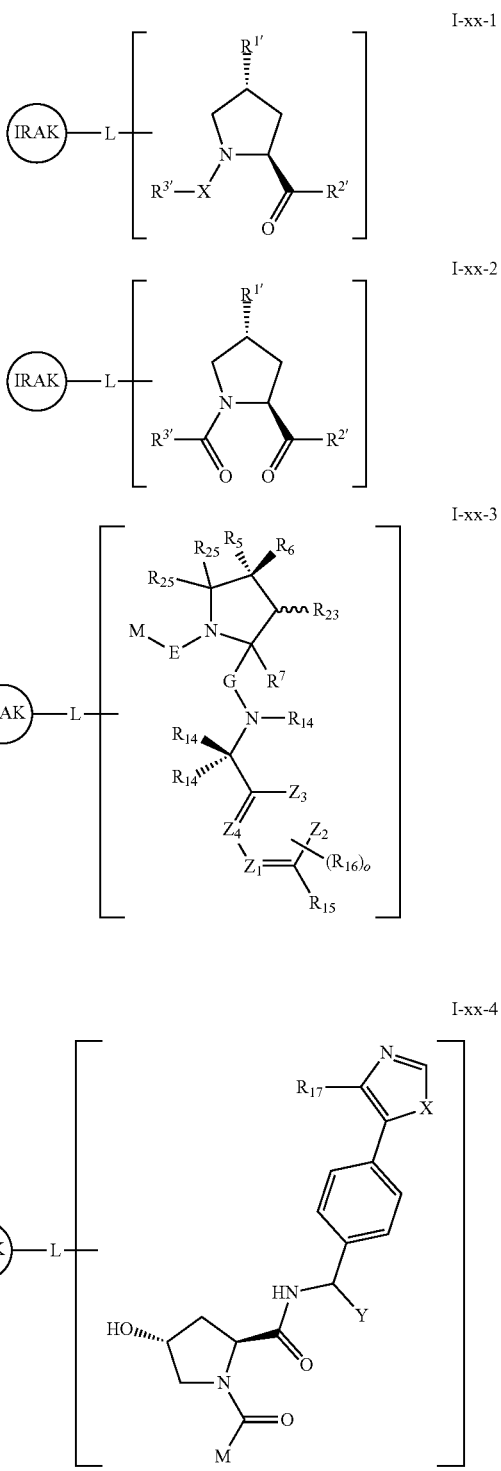

243

-continued

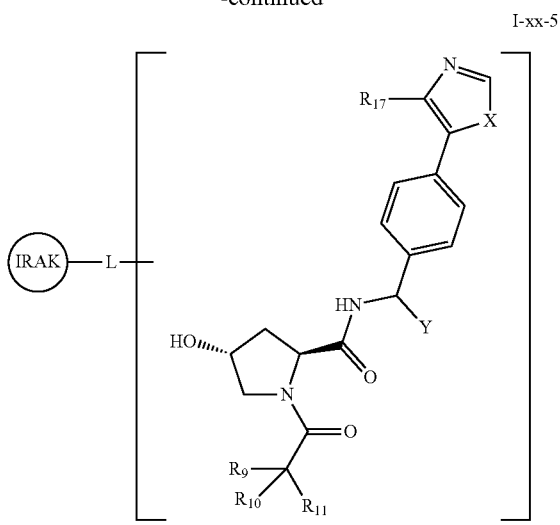

I-xx-5

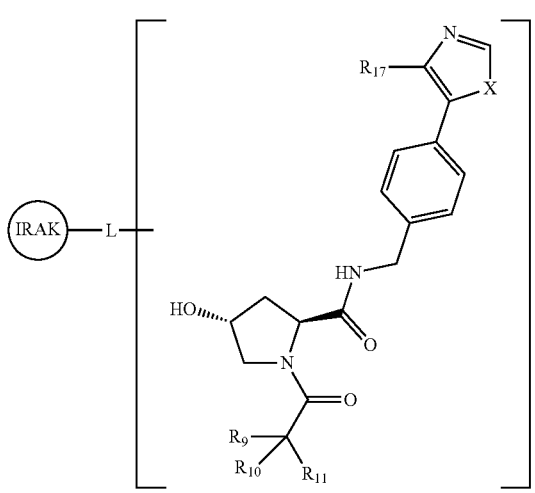

I-xx-6 or a pharmaceutically acceptable salt thereof, wherein L and IRAK are as defined above and described in embodiments herein, and wherein each of the variables $R^{1'}$, $R^{2'}$, $R^{3'}$, $R_5$, $R_6$, $R_7$, $R_9$, $R_{10}$, $R_{11}$, $R_{14}$, $R_{15}$, $R_{16}$, $R_{17}$, $R_{23}$, $R_{25}$, E, G, M, X, X', Y, $Z_1$, $Z_2$, $Z_3$, $Z_4$, and o is as defined and described in WO 2016/149668 and US 2016/0272639, the entirety of each of which is herein incorporated by reference.

As used herein, depiction of brackets around any LBM

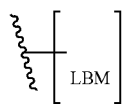

means that the

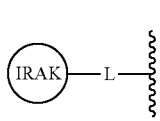

moiety is covalently attached to said LBM at any available modifiable carbon, nitrogen, oxygen, or sulfur atom. For

244 purposes of clarity and by way of example, such available modifiable carbon, nitrogen, oxygen, or sulfur atoms in the following LBM compound structure are depicted below, wherein each wavy bond defines the point of attachment to said

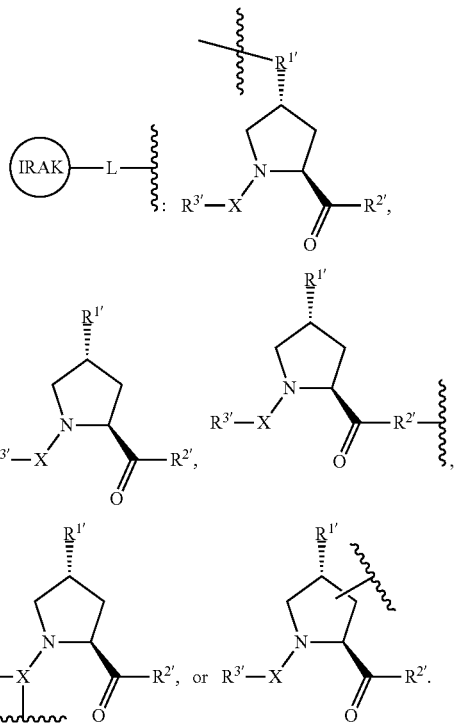

In certain embodiments, the present invention provides a compound of Formula I, wherein LBM is a VHL E3 ubiquitin ligase binding moiety thereby forming a compound of formula I-yy-1, I-yy-2, or I-yy-3 respectively:

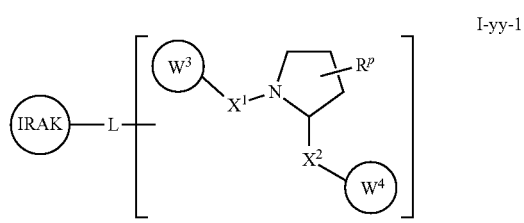

I-yy-1

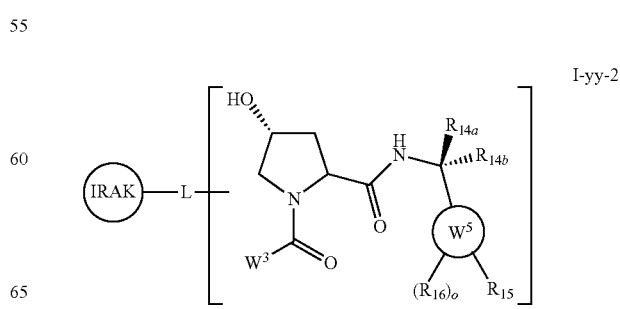

I-yy-2

I-yy-3

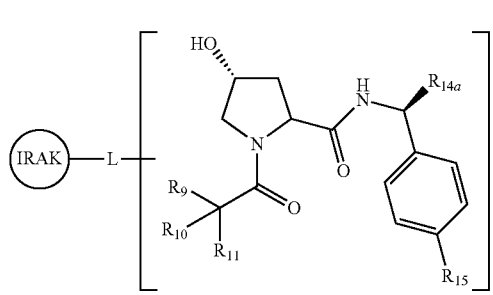

I-zz-5

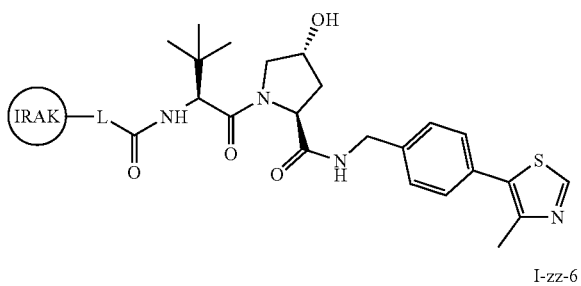

I-zz-6


I-zz-7

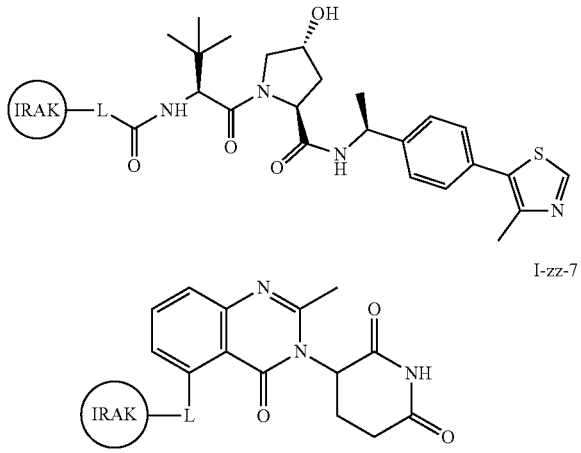

or a pharmaceutically acceptable salt thereof, wherein L and IRAK are as defined above and described in embodiments herein, and wherein each of the variables RP, $R_9$, $R_{10}$, $R_{11}$, $R_{14a}$, $R_{14b}$, $R_{15}$, $R_{16}$, $W^3$, $W^4$, $W^5$, $X^1$, $X^2$, and o is as defined and described in WO 2016/118666 and US 2016/0214972, the entirety of each of which is herein incorporated by reference.

In certain embodiments, the present invention provides a compound of Formula I, wherein LBM is a CRBN or VHL E3 ubiquitin ligase binding moiety thereby forming a compound of formula I-zz-1, I-zz-2, I-zz-3, I-zz-4, I-zz-5, I-zz-6, or I-zz-7 respectively:

I-zz-1

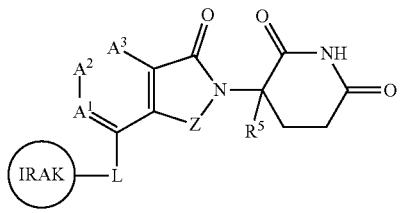

I-zz-2

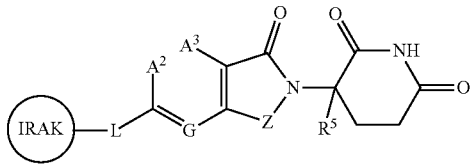

I-zz-3

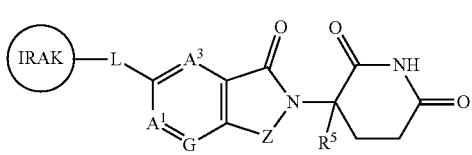

I-zz-4

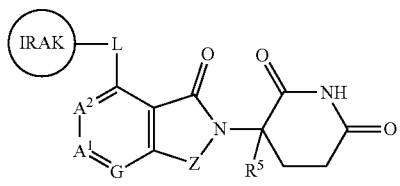

or a pharmaceutically acceptable salt thereof, wherein L and IRAK are as defined above and described in embodiments herein, and wherein each of the variables $A^1$, $A^2$, $A^3$, $R^5$, G and Z is as defined and described in WO 2017/176958.

In certain embodiments, the present invention provides a compound of Formula I, wherein LBM is a CRBN E3 ubiquitin ligase binding moiety thereby forming a compound of formula I-zz'-1, I-zz"-1, I-zz'-2, I-zz'-2, I-zz'-3, I-zz"-3, I-zz'-4, I-zz"-4, I-zz'-7 or I-zz"-7 respectively:

I-zz'-1

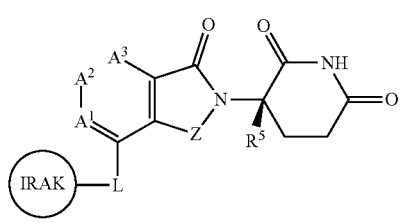

I-zz"-1

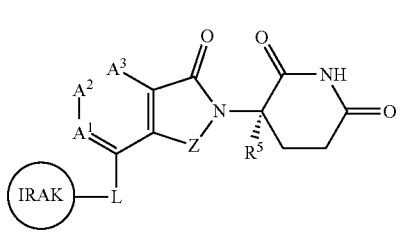

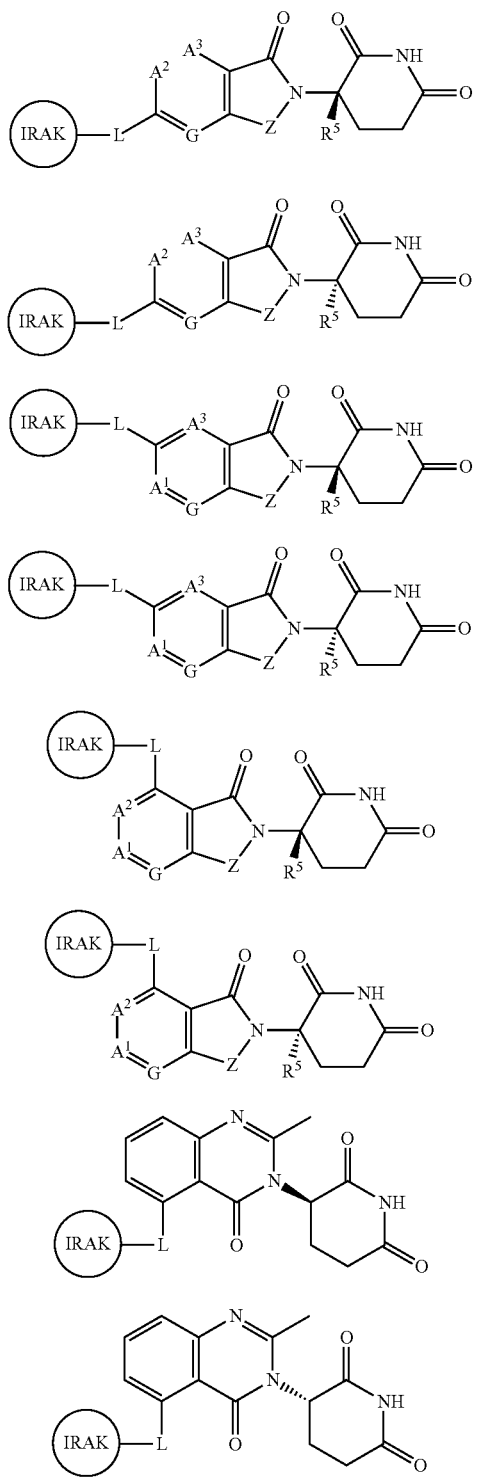

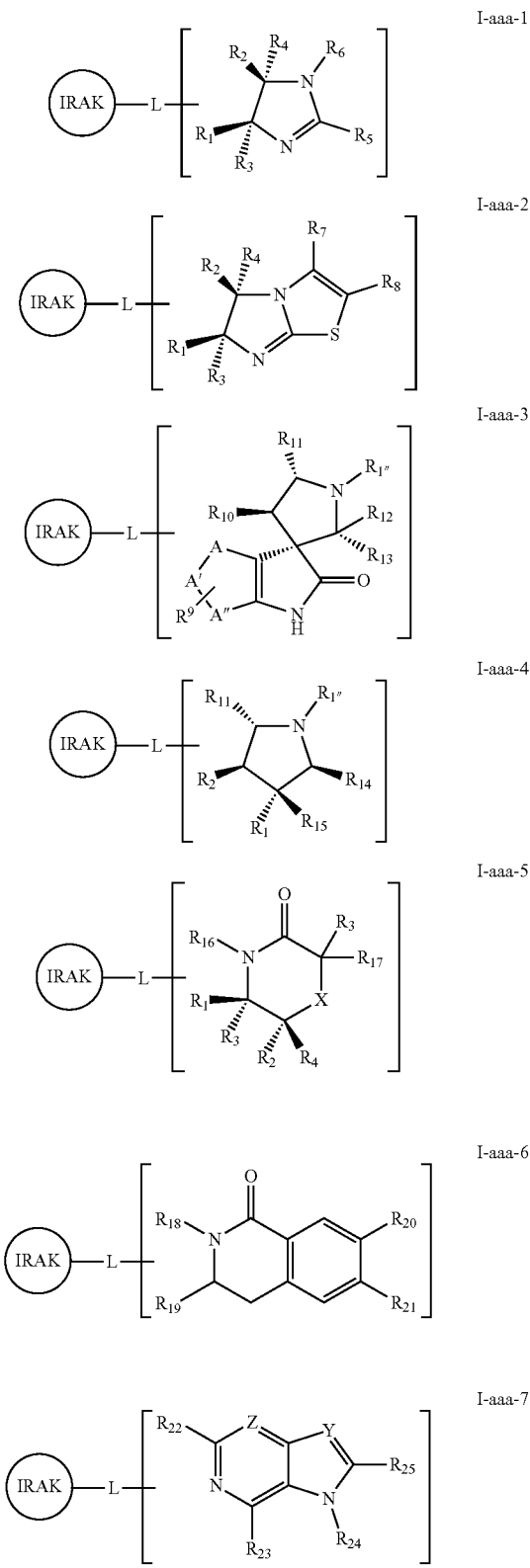

thereby forming a compound of formula I-aaa-1, I-aaa-2, I-aaa-3, I-aaa-4, I-aaa-5, I-aaa-6, I-aaa-7, I-aaa-8, I-aaa-9, I-aaa-10, I-aaa-11, I-aaa-12, I-aaa-13, I-aaa-14, I-aaa-15, I-aaa-16, I-aaa-17, or I-aaa-18 respectively:

or a pharmaceutically acceptable salt thereof, wherein L and IRAK are as defined above and described in embodiments herein, and wherein each of the variables $A^1$, $A^2$, $A^3$, $R^5$, G and Z is as defined and described in WO 2017/176958, the entirety of which is herein incorporated by reference.

In certain embodiments, the present invention provides a compound of Formula I, wherein LBM is a MDM2 (i.e. human double minute 2 or HDM2) E3 ligase binding moiety

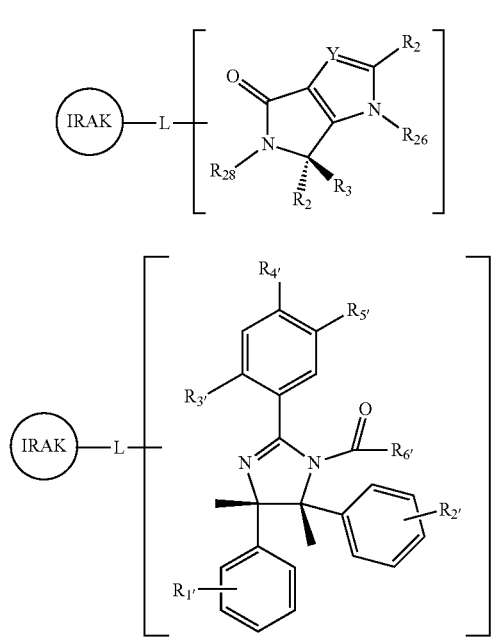
I-aaa-8
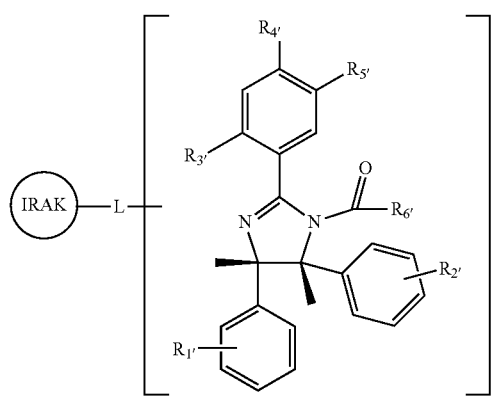
I-aaa-9
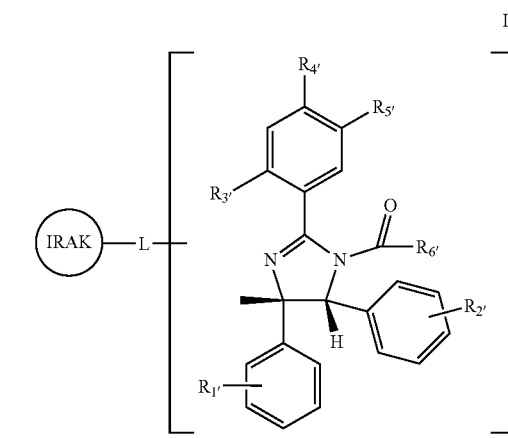
I-aaa-10
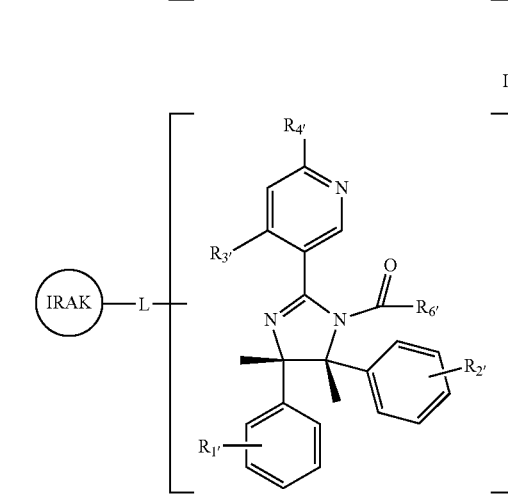
I-aaa-11
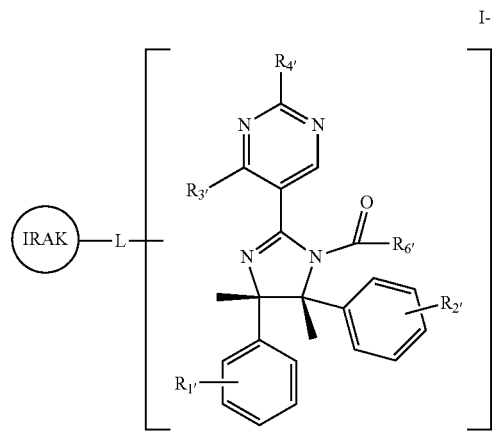
I-aaa-12
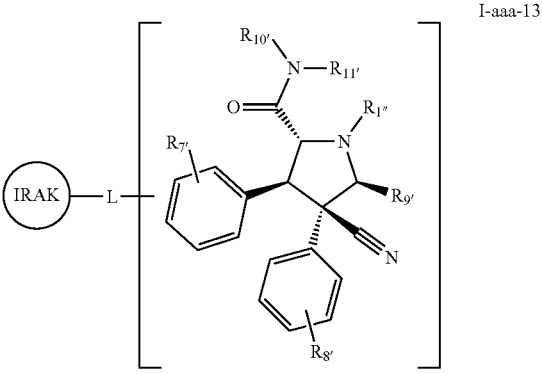
I-aaa-13
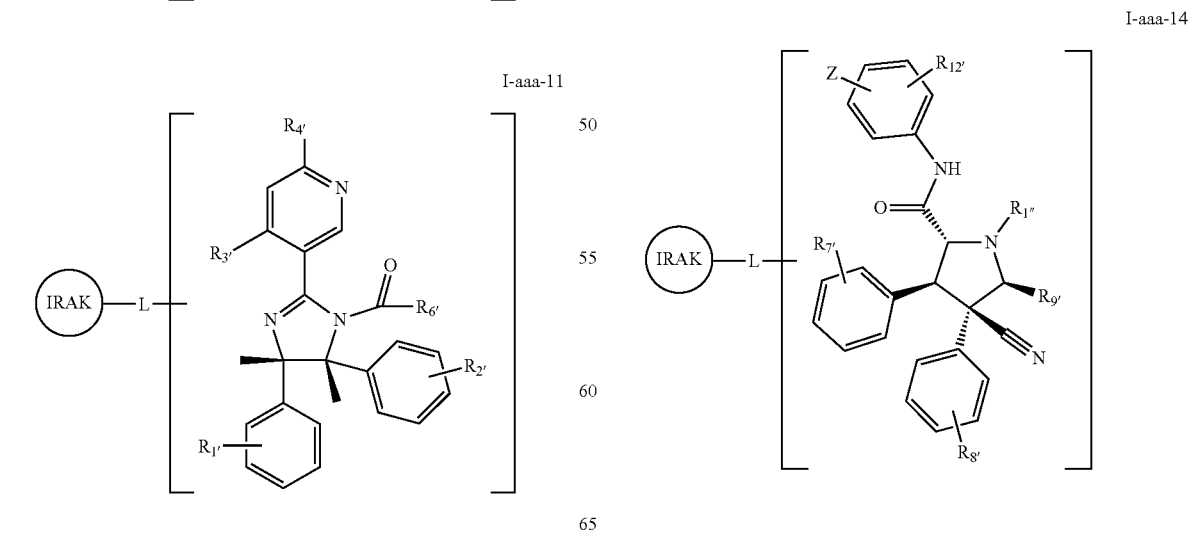
I-aaa-14

I-aaa-15

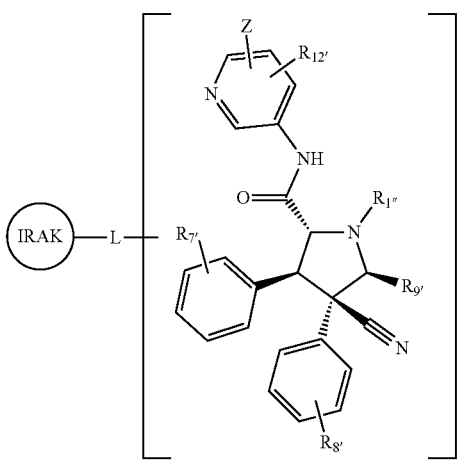

I-aaa-16

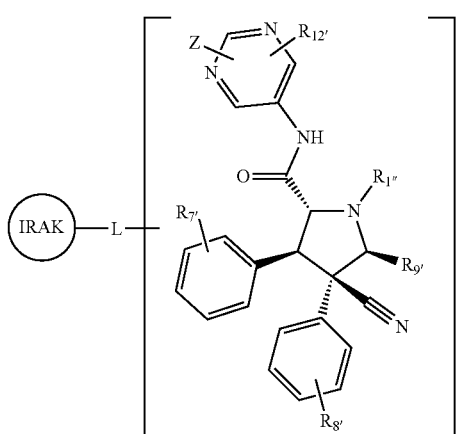

I-aaa-17

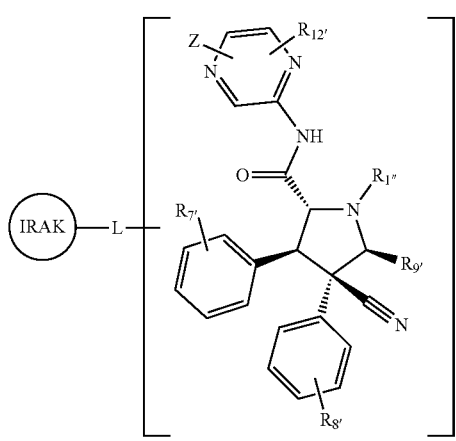

I-aaa-18

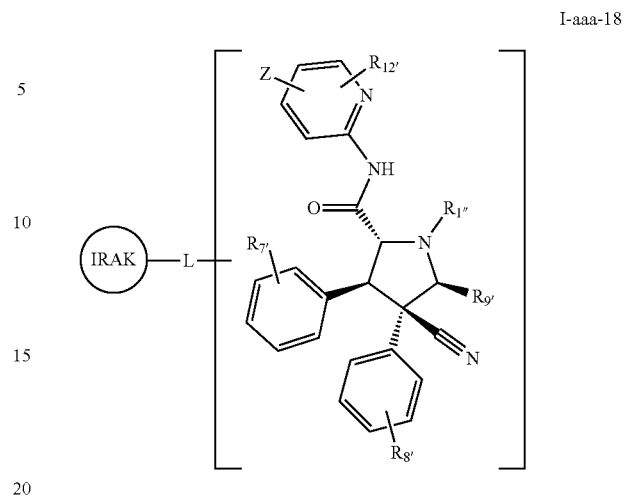

or a pharmaceutically acceptable salt thereof, wherein L and IRAK are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_1'$, $R_2'$, $R_3'$, $R_4'$, $R_5'$, $R_6'$, $R_7'$, $R_8'$, $R_9'$, $R_{10'}$, $R_{11'}$, $R_{12'}$, $R_1''$, A, A', A", X, Y, and Z is as defined and described in WO 2017/011371 and US 2017/0008904, the entirety of each of which is herein incorporated by reference.

In certain embodiments, the present invention provides a compound of Formula I, wherein LBM is an IAP E3 ubiquitin ligase binding moiety thereby forming a compound of formula I-bbb-1, I-bbb-2, I-bbb-3, or I-bbb-4 respectively:

I-bbb-1

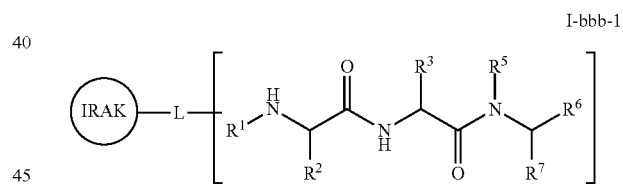

I-bbb-2

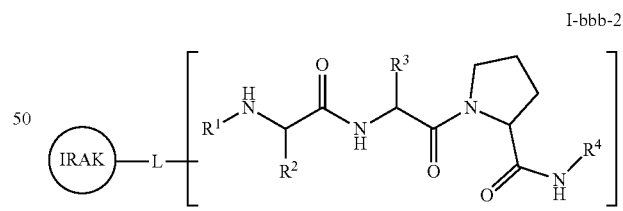

I-bbb-3

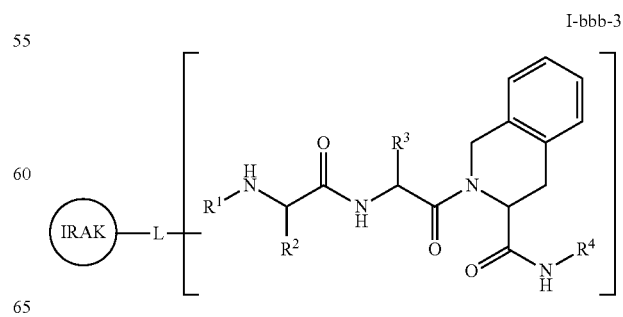

I-bbb-4

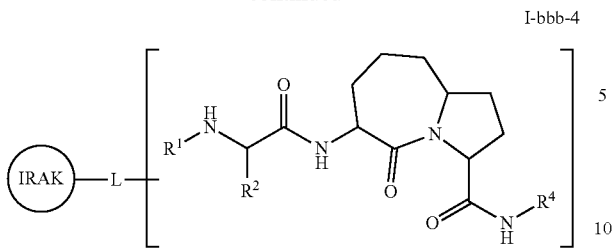

or a pharmaceutically acceptable salt thereof, wherein L and IRAK are as defined above and described in embodiments herein, and wherein each of the variables $R^1$, $R^2$, $R^3$, $R^4$, $R^5$, $R^6$, and $R^7$, is as defined and described in WO 2017/011590 and US 2017/0037004, the entirety of each of which is herein incorporated by reference.

In certain embodiments, the present invention provides a compound of Formula I, wherein LBM is an E3 ubiquitin ligase (cereblon) binding moiety, a DCAF15 E3 ubiquitin ligase binding moiety, or a VHL E3 ubiquitin ligase binding moiety; thereby forming a compound of formula I-ccc-1, I-ccc-2, or I-ccc-3:

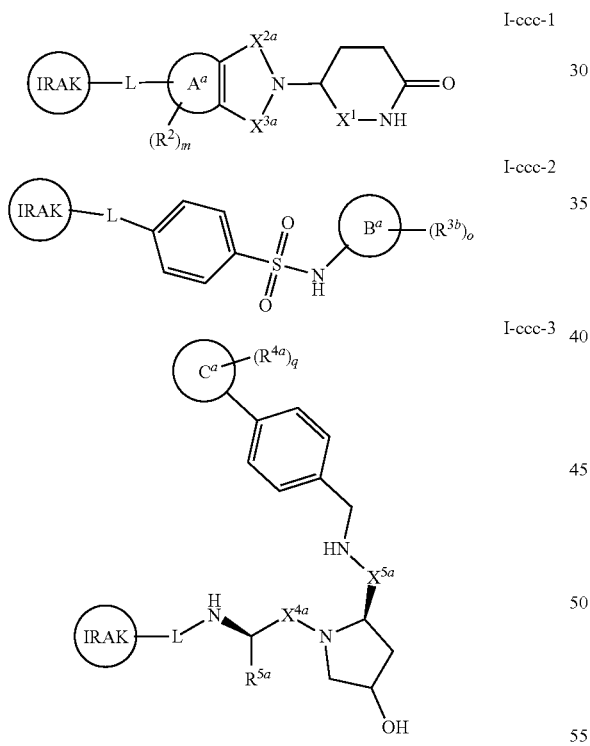

or a pharmaceutically acceptable salt thereof, wherein L and IRAK is as defined above and described in embodiments herein, and wherein:

each of $X^1$, $X^{2a}$, and $X^{3a}$ is independently a bivalent moiety selected from a covalent bond, —CH$_2$—, —C(O)—, —C(S)—, or

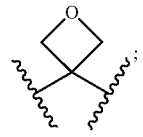 [SMILES: *C1(*)COC1]

each of $X^4$ and $X^{5a}$ is independently a bivalent moiety selected from —CH$_2$—, —C(O)—, —C(S)—, or

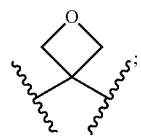 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

each of $R^2$, $R^{3b}$, and $R^1$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^{5a}$ is hydrogen or $C_{1-6}$ aliphatic;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring $B^a$ is selected from 6-membered aryl containing 0-2 nitrogen atoms or a 8-10 membered bicyclic heteroaryl having 1-5 heteroatoms independently selected from nitrogen, oxygen, or sulfur;

Ring $C^a$ is a selected from 6-membered aryl containing 0-2 nitrogen atoms or a 5-membered heteroaryl with 1-3 heteroatoms independently selected from nitrogen, oxygen or sulfur;

m is 0, 1, 2, 3 or 4;

is 0, 1, 2, 3 or 4;

q is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I-ccc-1, wherein LBM is an E3 ubiquitin ligase (cereblon) binding moiety thereby forming a compound of formula I-ccc'-1 or I-ccc''-1:

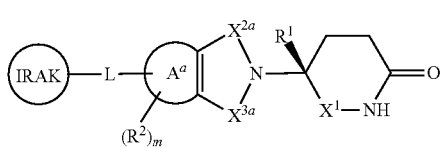

I-ccc'-1

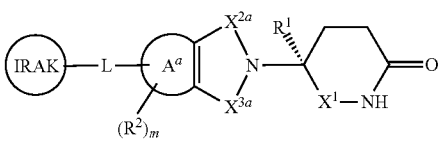

I-ccc''-1 or a pharmaceutically acceptable salt thereof, wherein IRAK, L, Ring $A^a$, $X^1$, $X^{2a}$, $X^{3a}$, $R^1$, $R^2$ and m are as described above.

As defined above and described herein, each of $X^1$, $X^{2a}$, and $X^{3a}$ is independently a bivalent moiety selected from a covalent bond, —CH$_2$—, —C(O)—, —C(S)—, or

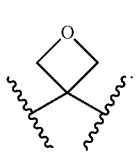

In some embodiments, $X^1$ is a covalent bond, —CH$_2$—, —C(O)—, —C(S)—, or

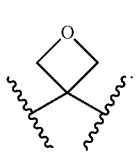

In some embodiments, $X^1$ is selected from those depicted in Table 1, below.

In some embodiments, $X^{2a}$ is a covalent bond, —CH$_2$—, —C(O)—, —C(S)—, or

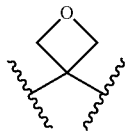

In some embodiments, $X^{2a}$ is selected from those depicted in Table 1, below.

In some embodiments, $X^a$a is a covalent bond, —CH$_2$—, —C(O)—, —C(S)—, or

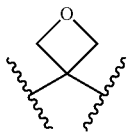

In some embodiments, $X^{3a}$ is selected from those depicted in Table 1, below.

As defined above and described herein, each of $X^4$ and $X^5$ is independently a bivalent moiety selected from —CH$_2$—, —C(O)—, —C(S)—, or

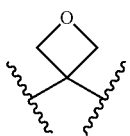

In some embodiments, $X^{4a}$ is —CH$_2$—, —C(O)—, —C(S)—, or

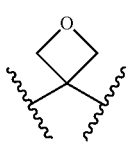

In some embodiments, $X^{4a}$ is selected from those depicted in Table 1, below.

In some embodiments, $X^{5a}$ is —CH$_2$—, —C(O)—, —C(S)—, or

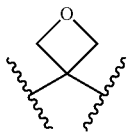

In some embodiments, $X^{5a}$ is selected from those depicted in Table 1, below.

As defined above and described herein, $R^1$ is hydrogen, deuterium, halogen, —CN, —OR, —SR, —S(O)R, —S(O)$_2$R, —NR$_2$, or an optionally substituted C$_{1-4}$ aliphatic.

In some embodiments, $R^1$ is hydrogen, deuterium, halogen, —CN, —OR, —SR, —S(O)R, —S(O)$_2$R, —NR$_2$, or an optionally substituted C$_{1-4}$ aliphatic.

In some embodiments, $R^1$ is selected from those depicted in Table 1, below.

As defined above and described herein, each of $R^2$, $R^{3b}$, and $R^{4a}$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^2$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O) OR, —N(R)C(O)R, —N(R)C(O)NR$_2$, or —N(R)S(O)$_2$R.

In some embodiments, $R^2$ is selected from those depicted in Table 1, below.

In some embodiments, $R^{3b}$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$.

In some embodiments, $R^{3b}$ is methyl.

In some embodiments, $R^{3b}$ is selected from those depicted in Table 1, below.

In some embodiments, $R^{4a}$ is hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$.

In some embodiments, $R^{4a}$ is methyl.

In some embodiments, $R^{4a}$ is selected from those depicted in Table 1, below.

As defined above and described herein, $R^{5a}$ is hydrogen or $C_{1-6}$ aliphatic.

In some embodiments, $R^{5a}$ is t-butyl.

In some embodiments, $R^{5a}$ is selected from those depicted in Table 1, below.

As defined above and described herein, each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^6$ is an optionally substituted $C_{1-6}$ aliphatic group. In some embodiments, $R^6$ is an optionally substituted phenyl. In some embodiments, $R^6$ is an optionally substituted 4-7 membered saturated or partially unsaturated heterocyclic ring having 1-2 heteroatoms independently selected from nitrogen, oxygen, and sulfur. In some embodiments, $R^6$ is an optionally substituted 5-6 membered heteroaryl ring having 1-4 heteroatoms independently selected from nitrogen, oxygen, and sulfur.

In some embodiments, $R^6$ is selected from those depicted in Table 1, below.

As defined above and described herein, Ring Aa is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments Ring $A^a$ is a fused 6-membered aryl containing 0-2 nitrogen atoms. In some embodiments Ring Aa is a fused 5 to 7-membered partially saturated carbocyclyl. In some embodiments Ring Aa is a fused 5 to 7-membered partially saturated heterocyclyl with 1-2 heteroatoms independently selected from nitrogen, oxygen or sulfur. In some embodiments Ring Aa is a fused 5-membered heteroaryl with 1-3 heteroatoms independently selected from nitrogen, oxygen or sulfur.

In some embodiments, Ring Aa is a fused phenyl.

In some embodiments, Ring Aa is selected from those depicted in Table 1, below.

As defined above and described herein, Ring $B^a$ is selected from 6-membered aryl containing 0-2 nitrogen atoms or a 8-10 membered bicyclic heteroaryl having 1-5 heteroatoms independently selected from nitrogen, oxygen, or sulfur.

In some embodiments, Ring $B^a$ is a 6-membered aryl containing 0-2 nitrogen atoms. In some embodiments, Ring $B^a$ is a 8-10 membered bicyclic heteroaryl having 1-5 heteroatoms independently selected from nitrogen, oxygen, or sulfur.

In some embodiments, Ring $B^a$ is

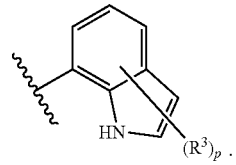

In some embodiments, Ring $B^a$ is selected from those depicted in Table 1, below.

As defined above and described herein, Ring $C^a$ is selected from 6-membered aryl containing 0-2 nitrogen atoms or a 5-membered heteroaryl with 1-3 heteroatoms independently selected from nitrogen, oxygen or sulfur.

In some embodiments, Ring $C^a$ is a 6-membered aryl containing 0-2 nitrogen atoms. In some embodiments, Ring $C^a$ is a 5-membered heteroaryl with 1-3 heteroatoms independently selected from nitrogen, oxygen or sulfur.

In some embodiments, Ring $C^a$ is

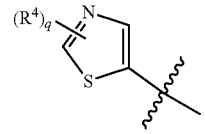

In some embodiments, Ring $C^a$ is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

In some embodiments, o is selected from those depicted in Table 1, below.

As defined above and described herein, o is 0, 1, 2, 3 or 4.

In some embodiments, o is 0. In some embodiments, o is 1. In some embodiments, o is 2. In some embodiments, o is 3. In some embodiments, o is 4.

In some embodiments, o is selected from those depicted in Table 1, below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

In certain embodiments, the present invention provides a compound of formula I, wherein LBM is a VHL binding moiety thereby forming a compound of formula I-ddd:

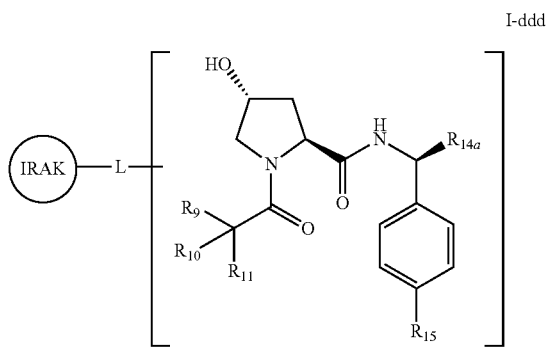

I-ddd or a pharmaceutically acceptable salt thereof, wherein L and IRAK are as defined above and described in embodiments herein, and wherein each of the variables $R_9$, $R_{10}$, $R_{11}$, $R_{14a}$, and $R_{15}$ is as described and defined in WO 2017/030814, WO 2016/118666, and US 2017/0327469, the entirety of each of which is herein incorporated by reference.

In certain embodiments, the present invention provides a compound of formula I, wherein LBM is a VHL binding moiety thereby forming a compound of formula I-eee-1 or I-eee-2:

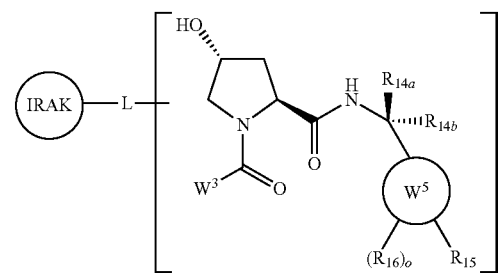

I-eee-1

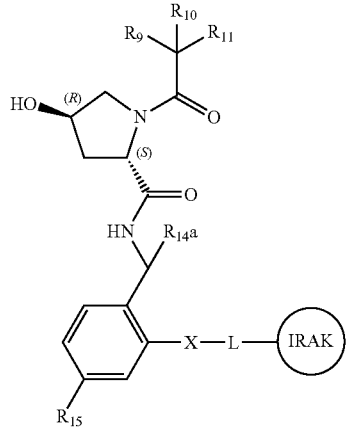

I-eee-2 or a pharmaceutically acceptable salt thereof, wherein L and IRAK are as defined above and described in embodiments herein, and wherein each of the variables X, W, $R_9$, $R_{10}$, $R_{11}$, $R_{14a}$, and $R_{14b}$, $R_{15}$, $R^{16}$, and o is as described and defined in WO 2017/030814, WO 2016/118666, and US 2017/0327469, the entirety of each of which is herein incorporated by reference.

In certain embodiments, the present invention provides a compound of formula I, wherein LBM is an IAP binding moiety thereby forming a compound of formula I-fff:

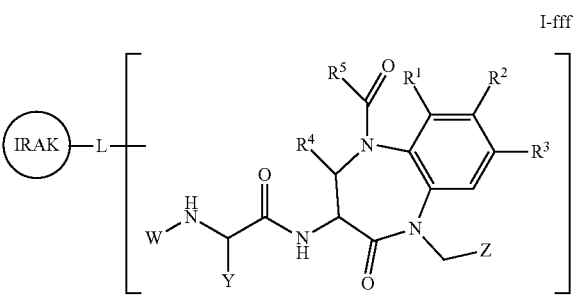

I-fff or a pharmaceutically acceptable salt thereof, wherein L and IRAK are as defined above and described in embodiments herein, and wherein each of the variables W, Y, Z, $R^1$, $R^2$, $R^3$, $R^4$, and $R^5$ is as described and defined in WO 2014/044622, US 2015/0225449. WO 2015/071393, and US 2016/0272596, the entirety of each of which is herein incorporated by reference.

In certain embodiments, the present invention provides a compound of formula I, wherein LBM is a MDM2 binding moiety thereby forming a compound of formula I-ggg:

I-ggg

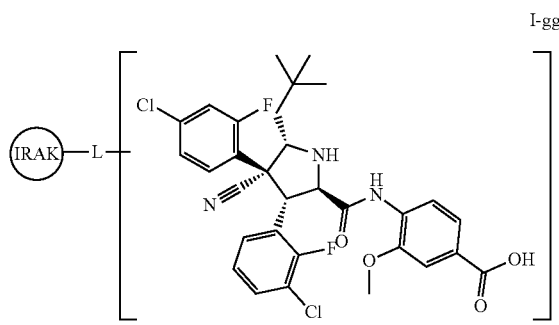

or a pharmaceutically acceptable salt thereof, wherein L and IRAK are as defined above and described in embodiments herein, as described and defined in Hines, J. et al., *Cancer Res.* (DOI: 10.1158/0008-5472.CAN-18-2918), the entirety of each of which is herein incorporated by reference.

In certain embodiments, the present invention provides a compound of formula I, wherein LBM is a DCAF16 binding moiety thereby forming a compound of formula I-hhh:

I-hhh

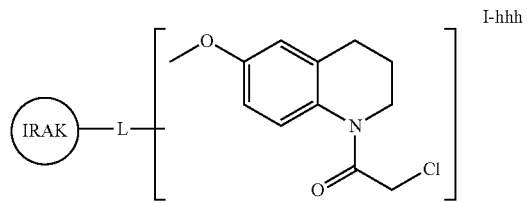

or a pharmaceutically acceptable salt thereof, wherein L and IRAK are as defined above and described in embodiments herein, as described and defined in Zhang, X. et al., *bioRxiv* (doi: https://doi.org/10.1101/443804), the entirety of each of which is herein incorporated by reference.

In certain embodiments, the present invention provides a compound of formula I, wherein LBM is a RNF114 binding moiety thereby forming a compound of formula I-iii:

I-iii

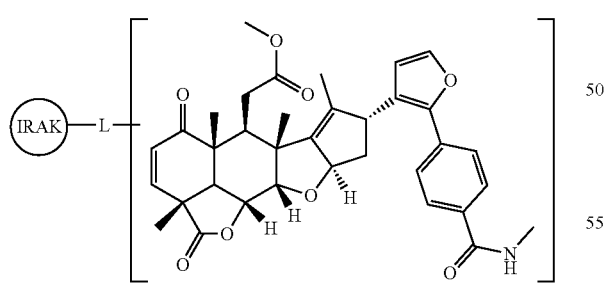

or a pharmaceutically acceptable salt thereof, wherein L and IRAK are as defined above and described in embodiments herein, as described and defined in Spradin, J. N. et al., *bioRxiv* (doi: https://doi.org/10.1101/436998), the entirety of each of which is herein incorporated by reference.

In certain embodiments, the present invention provides a compound of formula I, wherein LBM is a RNF4 binding moiety thereby forming a compound of formula I-jjj:

I-jjj

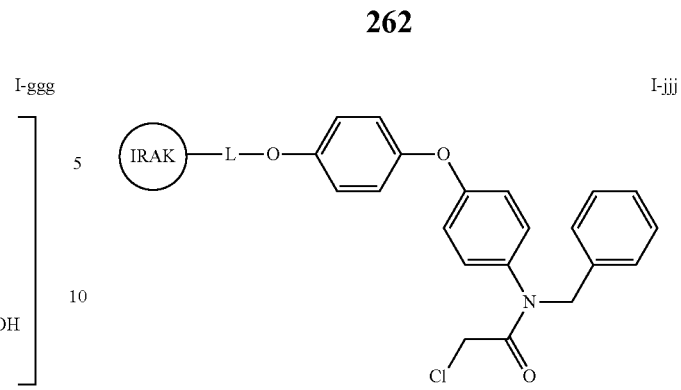

or a pharmaceutically acceptable salt thereof, wherein L and IRAK are as defined above and described in embodiments herein, as described and defined in Ward, C. C., et al., *bioRxiv* (doi: https://doi.org/10.1101/439125), the entirety of each of which is herein incorporated by reference.

In certain embodiments, the present invention provides a compound of formula I, wherein LBM is a VHL binding moiety thereby forming a compound of formula I-nnn-1 or I-nnn-2:

I-nnn-1

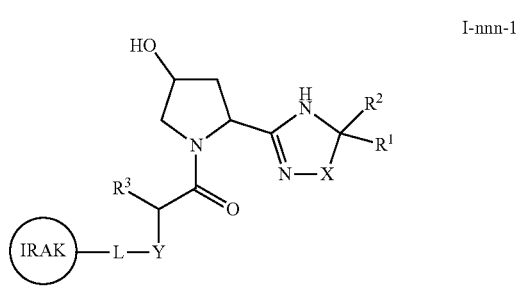

I-nnn-2

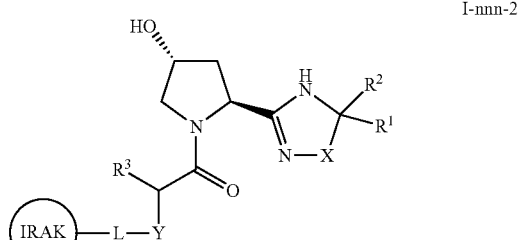

or a pharmaceutically acceptable salt thereof, wherein L and IRAK are as defined above and described in embodiments herein, and wherein each of the variables $R^1$, $R^2$, $R^3$, X, and Y is as defined and described in WO 2019/084026, the entirety of each of which is herein incorporated by reference.

In certain embodiments, the present invention provides a compound of formula I, wherein LBM is a VHL binding moiety thereby forming a compound of formula I-ooo-1 or I-ooo-2:

I-ooo1


I-ooo-2

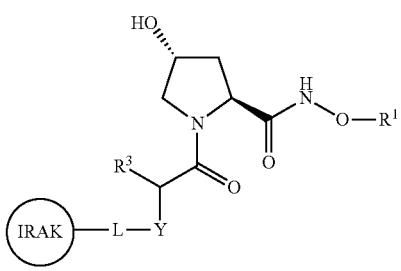

or a pharmaceutically acceptable salt thereof, wherein L and IRAK are as defined above and described in embodiments herein, and wherein each of the variables $R^1$, $R^3$, and Y is as defined and described in WO 2019/084030, the entirety of each of which is herein incorporated by reference.

In certain embodiments, the present invention provides a compound of formula I, wherein LBM is a E3 ubiquitin ligase (cereblon) binding moiety thereby forming a compound of formula I-ppp-1, I-ppp-2, I-ppp-3, or I-ppp-4:

I-ppp-1

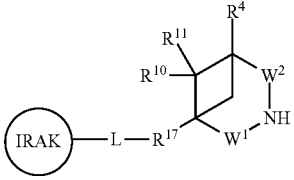

I-ppp-2

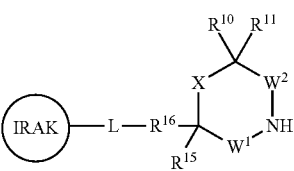

I-ppp-3

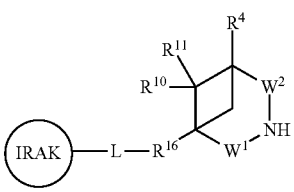

I-ppp-4

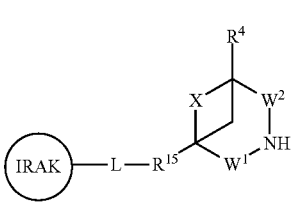

or a pharmaceutically acceptable salt thereof, wherein L and IRAK are as defined above and described herein, and wherein each of the variables $R^4$, $R^{10}$, $R^{11}$, $R^{15}$, $R^{16}$, $R^{17}$, $W^1$, $W^2$, and X is as defined in WO 2019/099868 which is herein incorporated by reference in its entirety, and wherein

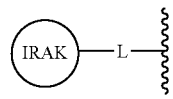

is attached to $R^{17}$ or $R^{16}$ at the site of attachment of $R^{12}$ as defined in WO 2018/237026, such that

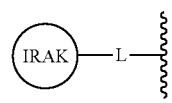

takes the place of the $R^{12}$ substituent.

In some embodiments, LBM is

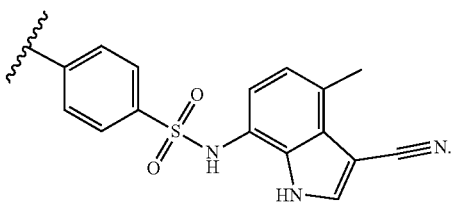 [SMILES: *c1ccc(S(=O)(=O)Nc2ccc(C)c3c(C#N)c[nH]c23)cc1]

In some embodiments, LBM is

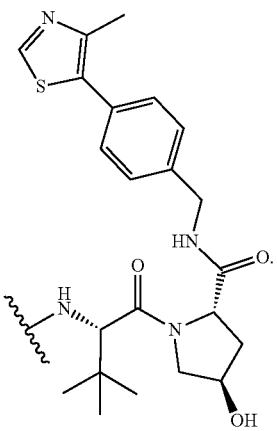 [SMILES: *N[C@H](C(=O)N1C[C@H](O)C[C@H]1C(=O)NCc1ccc(-c2scnc2C)cc1)C(C)(C)C]

In some embodiments, LBM is
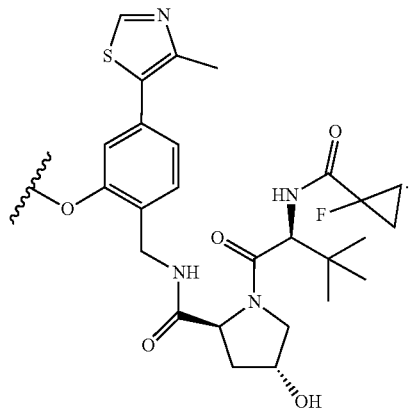 [SMILES: *Oc1cc(-c2scnc2C)ccc1CNC(=O)[C@@H]1C[C@@H](O)CN1C(=O)[C@@H](NC(=O)C1(F)CC1)C(C)(C)C]
In some embodiments, LBM is
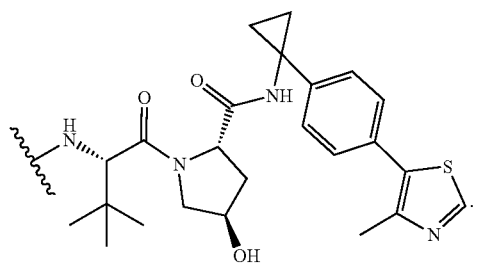 [SMILES: *N[C@H](C(=O)N1C[C@H](O)C[C@H]1C(=O)NC1(c2ccc(-c3scnc3C)cc2)CC1)C(C)(C)C]
In some embodiments, LBM is
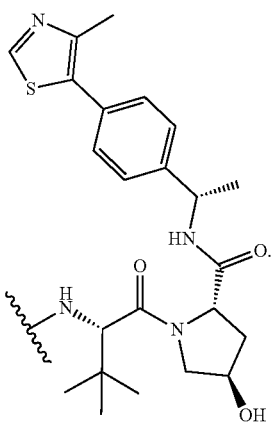 [SMILES: *N[C@H](C(=O)N1C[C@H](O)C[C@H]1C(=O)N[C@@H](C)c1ccc(-c2scnc2C)cc1)C(C)(C)C]
In some embodiments, LBM
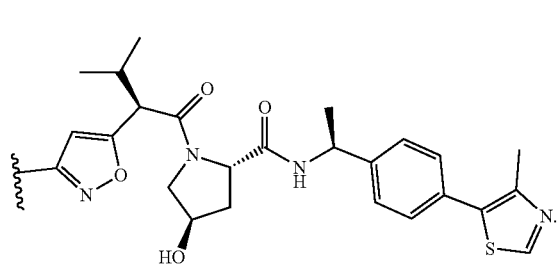 [SMILES: *c1cc([C@H](C(=O)N2C[C@H](O)C[C@H]2C(=O)N[C@@H](C)c2ccc(-c3scnc3C)cc2)C(C)C)on1]
In some embodiments, LBM is
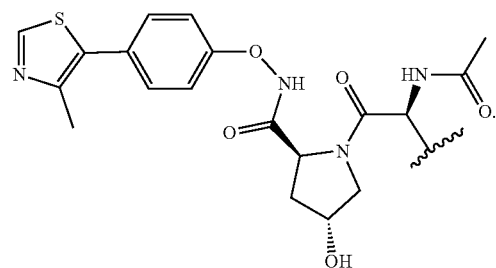 [SMILES: *[C@H](NC(C)=O)C(=O)N1C[C@H](O)C[C@H]1C(=O)NOc1ccc(-c2scnc2C)cc1]
In some embodiments, LBM is
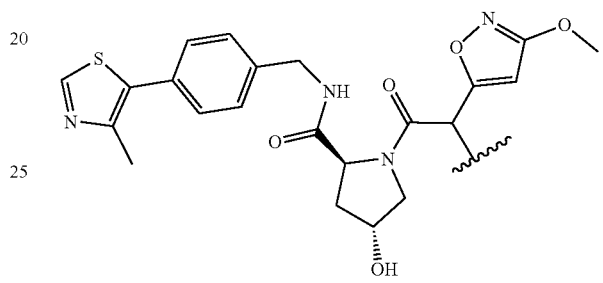
In some embodiments, LBM is
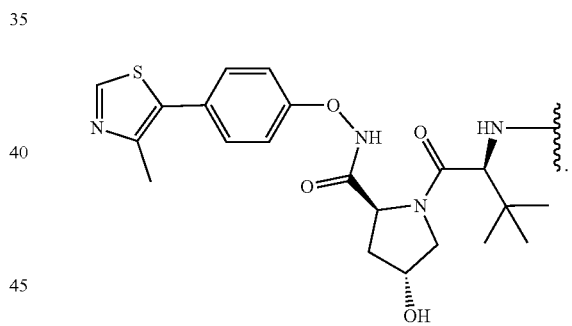
In some embodiments, LBM is
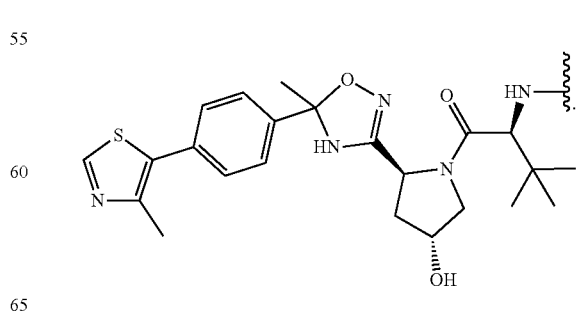

In some embodiments, LBM is
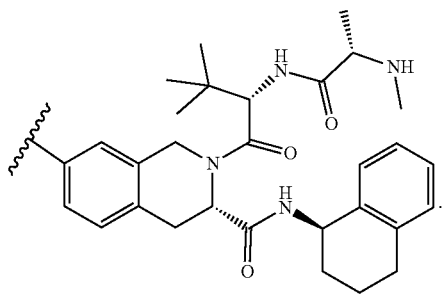 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
In some embodiments, LBM is
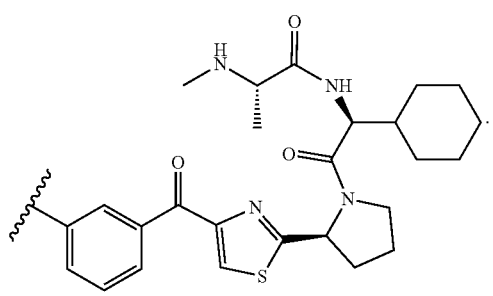 [SMILES: *c1cccc(C(=O)c2csc([C@@H]3CCCN3C(=O)[C@@H](NC(=O)[C@H](C)NC)C3CCCCC3)n2)c1]
In some embodiments, LBM is
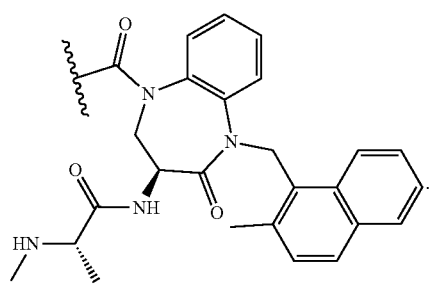 [SMILES: *C(=O)N1C[C@H](NC(=O)[C@H](C)NC)C(=O)N(Cc2c(C)ccc3ccccc23)c2ccccc21]
In some embodiments, LBM is
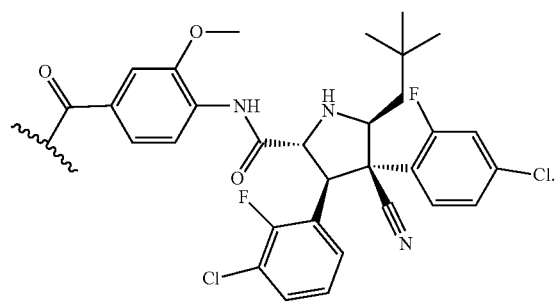 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
In some embodiments, LBM is
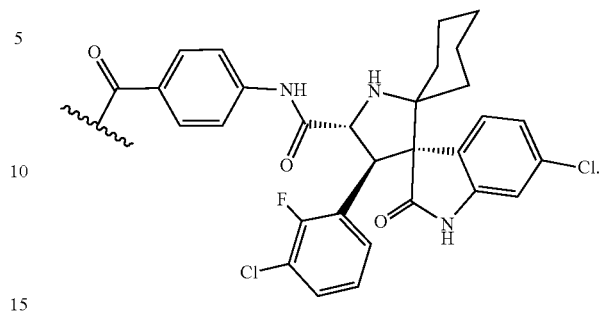
In some embodiments, LBM is
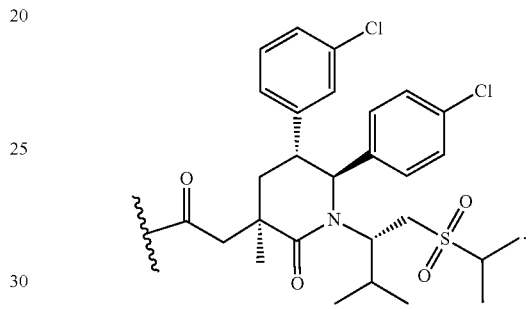
In some embodiments, LBM is
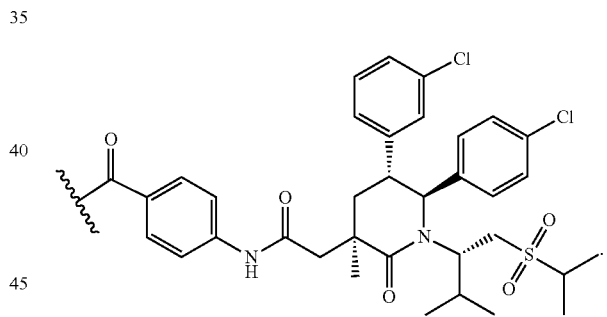
In some embodiments, LBM is
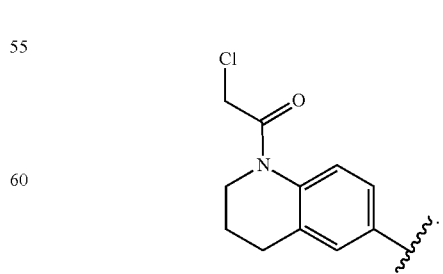

In some embodiments, LBM is
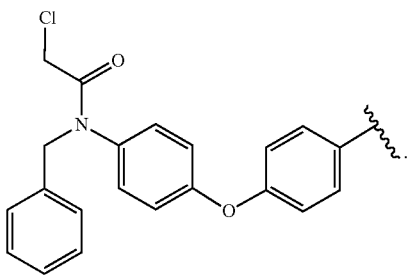 [SMILES: *c1ccc(Oc2ccc(N(Cc3ccccc3)C(=O)CCl)cc2)cc1]
In some embodiments, LBM is
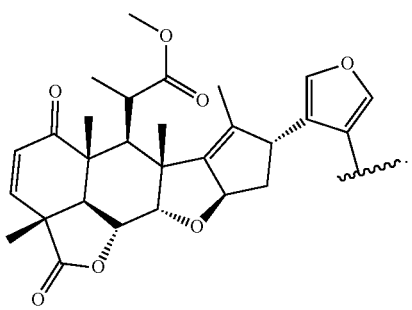 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45]
In some embodiments, LBM is
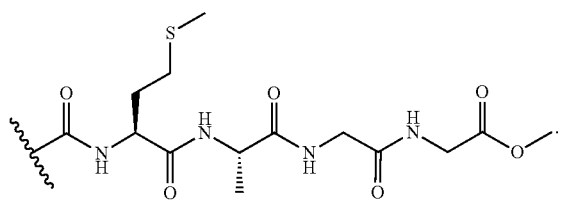 [SMILES: *C(=O)N[C@@H](CCSC)C(=O)N[C@@H](C)C(=O)NCC(=O)NCC(=O)OC]
In some embodiments, LBM is
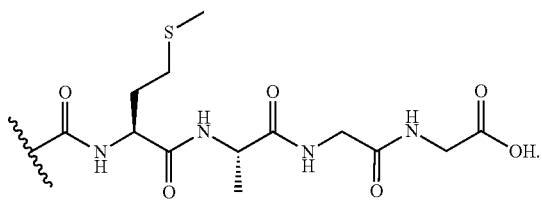 [SMILES: *C(=O)N[C@@H](CCSC)C(=O)N[C@@H](C)C(=O)NCC(=O)NCC(=O)O]
In some embodiments, LBM is
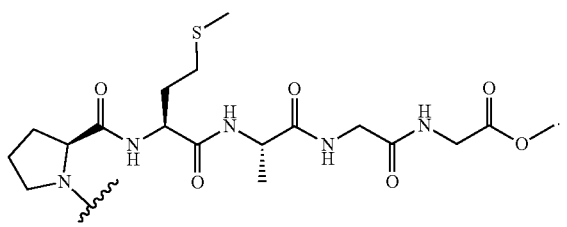 [SMILES: *N1CCC[C@H]1C(=O)N[C@@H](CCSC)C(=O)N[C@@H](C)C(=O)NCC(=O)NCC(=O)OC]
In some embodiments, LBM is
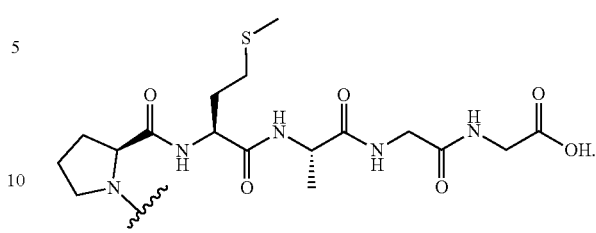
In some embodiments, LBM is
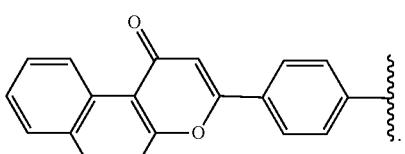
In some embodiments, LBM is
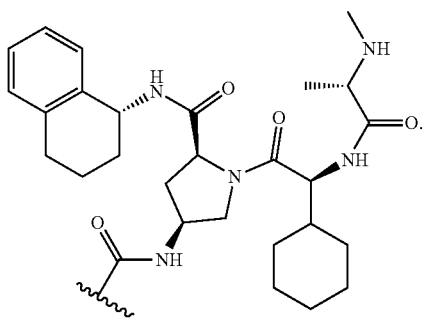 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]
In some embodiments, LBM is
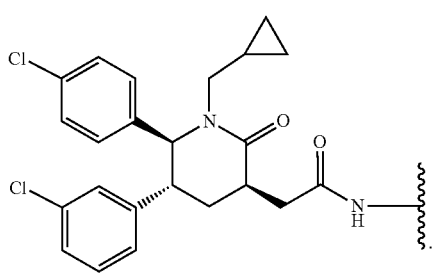 [SMILES: *NC(=O)C[C@H]1C[C@H](c2cccc(Cl)c2)[C@@H](c2ccc(Cl)cc2)N(CC2CC2)C1=O]

In some embodiments, LBM is

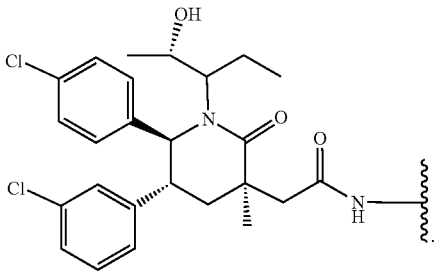 [SMILES: *NC(=O)C[C@@]1(C)C[C@H](c2cccc(Cl)c2)[C@@H](c2ccc(Cl)cc2)N(C(CC)[C@H](C)O)C1=O]

In some embodiments, LBM is

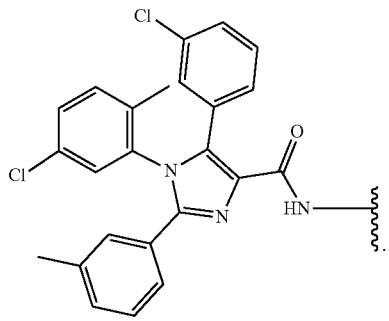 [SMILES: *NC(=O)c1nc(-c2cccc(C)c2)n(-c2cc(Cl)ccc2C)c1-c1cccc(Cl)c1]

In some embodiments, LBM is

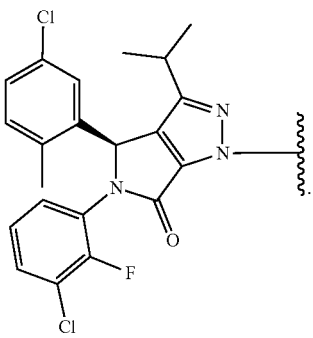 [SMILES: *n1nc(C(C)C)c2c1C(=O)N(c1cccc(Cl)c1F)[C@H]2c1cc(Cl)ccc1C]

In certain embodiments, the present invention provides a compound of formula I, wherein LBM is a CRBN E3 ubiquitin ligase binding moiety thereby forming a compound of formula I-qqq:

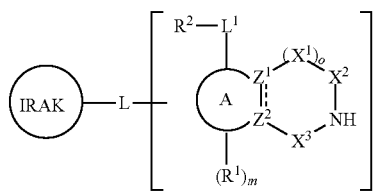

I-qqq or a pharmaceutically acceptable salt thereof, wherein L and IRAK are as defined above and described in embodiments herein, wherein:

each $X^1$ is independently —$CH_2$—, —O—, —NR—, —$CF_2$—,

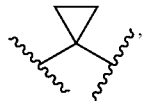

—C(O)—, —C(S)—, or

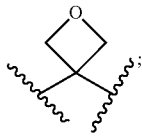

$X^2$ and $X^3$ are independently —$CH_2$—, —C(O)—, —C(S)—, or

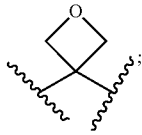 [SMILES: *C1(*)COC1]

$Z^1$ and $Z^2$ are independently a carbon atom or a nitrogen atom;

Ring A is a fused ring selected from benzo, a 4-6 membered saturated or partially unsaturated carbocyclic or heterocyclic ring having 1-3 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—;

each $R^1$ is independently selected from hydrogen, deuterium, $R^4$, halogen, —CN, —$NO_2$, —OR, —SR, —$NR_2$, —$S(O)_2R$, —$S(O)_2NR_2$, —S(O)R, —$CF_2R$, —$CR_2F$, —$CF_3$, —$CR_2(OR)$, —$CR_2(NR_2)$, —C(O)R, —C(O)OR, —$C(O)NR_2$, —C(O)N(R)OR, —OC(O)R, —$OC(O)NR_2$, —$C(S)NR_2$, —N(R)C(O)OR, —N(R)C(O)R, —$N(R)C(O)NR_2$, —$N(R)S(O)_2R$, —$OP(O)R_2$, —$OP(O)(OR)_2$, —$OP(O)(OR)NR_2$, —$OP(O)(NR_2)_2$, —$Si(OR)R_2$, and —$SiR_3$; or two $R^1$ groups are optionally taken together to form an optionally substituted 5-8 membered partially unsaturated or aryl fused ring having 0-2 heteroatoms independently selected from nitrogen, oxygen, or sulfur;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

$R^2$ is selected from

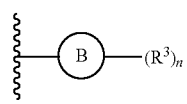

or hydrogen;

Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups;

each $R^3$ is independently selected from hydrogen, deuterium, $R^4$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, and —SiR$_3$;

each $R^4$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

==== is a single or double bond;

m is 0, 1, 2, 3 or 4;

n is 0, 1, 2, 3 or 4; and is 0, 1, or 2.

As defined above and described herein each $X^1$ is independently a covalent bond, —CH$_2$—, —O—, —NR—, —CF$_2$—,

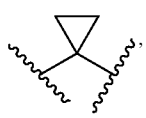

—C(O)—, —C(S)—, or

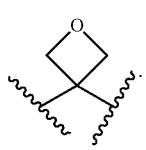 [SMILES: *C1(*)COC1]

In some embodiments, $X^1$ is a covalent bond. In some embodiments, $X^1$ is —CH$_2$—. In some embodiments, $X^1$ is —O—. In some embodiments, $X^1$ is —NR—. In some embodiments, $X^1$ is —CF$_2$—. In some embodiments, $X^1$ is

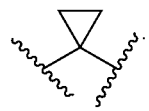 [SMILES: *C1(*)CC1]

In some embodiments, $X^1$ is —C(O)—. In some embodiments, $X^1$ is —C(S)—. In some embodiments, $X^1$ is

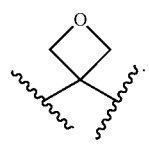

In certain embodiments, $X^1$ is selected from those shown in the compounds of Table 1.

As defined above and described herein, $X^2$ and $X^3$ are independently —CH$_2$—, —C(O)—, —C(S)—, or

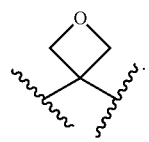

In some embodiments, $X^2$ and $X^3$ are independently —CH$_2$—. In some embodiments, $X^2$ and $X^3$ are independently —C(O)—. In some embodiments, $X^2$ and $X^3$ are independently —C(S)—. In some embodiments, $X^2$ and $X^3$ are independently

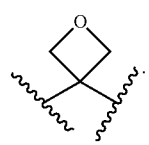

In certain embodiments, $X^2$ and $X^3$ are independently selected from those shown in the compounds of Table 1.

As defined above and described herein, $X^4$ is a covalent bond, —CH$_2$—, —CR$_2$—, —O—, —NR—, —CF$_2$—,

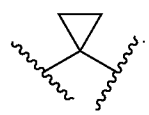

—C(O)—, —C(S)—, or

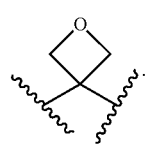

As define above and described herein, $Z^1$ and $Z^2$ are independently a carbon atom or a nitrogen atom.

In some embodiments, $Z^1$ and $Z^2$ are independently a carbon atom. In some embodiments, $Z^1$ and $Z^2$ are independently a carbon atom.

In certain embodiments, $Z^1$ and $Z^2$ are independently selected from those shown in the compounds of Table 1.

As defined above and described herein, Ring A is fused ring selected from benzo or a 5-6 membered heteroaryl ring having 1-4 heteroatoms independently selected from nitrogen, oxygen, and sulfur.

In some embodiments, Ring A is benzo. In some embodiments, Ring A is a 5-6 membered heteroaryl ring having 1-4 heteroatoms independently selected from nitrogen, oxygen, and sulfur.

In certain embodiments, Ring A is selected from those shown in the compounds of Table 1.

As defined above and described herein, $L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—.

In some embodiments, $L^1$ is a covalent bond. In some embodiments, $L^1$ is a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—.

In some embodiments, $L^1$ is —C(O)—.

In certain embodiments, $L^1$ is selected from those shown in the compounds of Table 1.

As defined above and described herein, each $R^1$ is independently selected from hydrogen, deuterium, $R^4$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —Si(OR)R$_2$, and —SiR$_3$, or two $R^1$ groups are optionally taken together to form an optionally substituted 5-8 membered partially unsaturated or aryl fused ring having 0-2 heteroatoms independently selected from nitrogen, oxygen, or sulfur.

In some embodiments, $R^1$ is hydrogen. In some embodiments, $R^1$ is deuterium. In some embodiments, $R^1$ is $R^4$. In some embodiments, $R^1$ is halogen. In some embodiments, $R^1$ is —CN. In some embodiments, $R^1$ is —NO$_2$. In some embodiments, $R^1$ is —OR. In some embodiments, $R^1$ is —SR. In some embodiments, $R^1$ is —NR$_2$. In some embodiments, $R^1$ is —S(O)$_2$R. In some embodiments, $R^1$ is —S(O)$_2$NR$_2$. In some embodiments, $R^1$ is —S(O)R. In some embodiments, $R^1$ is —CF$_2$R. In some embodiments, $R^1$ is —CF$_3$. In some embodiments, $R^1$ is —CR$_2$(OR). In some embodiments, $R^1$ is —CR$_2$(NR$_2$). In some embodiments, $R^1$ is —C(O)R. In some embodiments, $R^1$ is —C(O)OR. In some embodiments, $R^1$ is —C(O)NR$_2$. In some embodiments, $R^1$ is —C(O)N(R)OR. In some embodiments, $R^1$ is —OC(O)R. In some embodiments, $R^1$ is —OC(O)NR$_2$. In some embodiments, $R^1$ is —C(S)NR$_2$. In some embodiments, $R^1$ is —N(R)C(O)OR. In some embodiments, $R^1$ is —N(R)C(O)R. In some embodiments, $R^1$ is —N(R)C(O)NR$_2$. In some embodiments, $R^1$ is —N(R)S(O)$_2$R. In some embodiments, $R^1$ is —OP(O)R$_2$. In some embodiments, $R^1$ is —OP(O)(OR)$_2$. In some embodiments, $R^1$ is —OP(O)(OR)NR$_2$. In some embodiments, $R^1$ is —OP(O)(NR$_2$)$_2$. In some embodiments, $R^1$ is —Si(OR)R$_2$. In some embodiments, $R^1$ is —SiR$_3$. In some embodiments, two $R^1$ groups are optionally taken together to form an optionally substituted 5-8 membered partially unsaturated or aryl fused ring having 0-2 heteroatoms independently selected from nitrogen, oxygen, or sulfur.

In certain embodiments, each $R^1$ is independently selected from those shown in the compounds of Table 1.

As defined above and described here, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

As defined above and described herein, $R^2$ is selected from

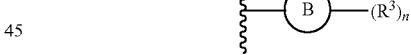

or hydrogen.

In some embodiment $R^2$ is

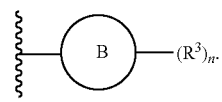

In some embodiments, $R^2$ is hydrogen.

In certain embodiments, $R^2$ is selected from those shown in the compounds of Table 1.

As defined above and described herein, Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups.

In some embodiments, Ring B is phenyl. In some embodiments, Ring B is a 4-10 membered saturated or partially unsaturated mono- or bicyclic carbocyclic or heterocyclic ring having 1-3 heteroatoms independently selected from nitrogen, oxygen, and sulfur In some embodiments, Ring B is a 5-6 membered heteroaryl ring having 1-4 heteroatoms independently selected from nitrogen, oxygen, and sulfur. In some embodiments, Ring B is further optionally substituted with 1-2 oxo groups.

In certain embodiments, Ring B is selected from those shown in the compounds of Table 1.

As defined above and described herein, each $R^3$ is independently selected from hydrogen, deuterium, $R^4$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, and —SiR$_3$.

In some embodiments, $R^3$ is hydrogen. In some embodiments, $R^3$ is deuterium. In some embodiments, $R^3$ is $R^4$. In some embodiments, $R^3$ is halogen. In some embodiments, $R^3$ is —CN. In some embodiments, $R^3$ is —NO$_2$. In some embodiments, $R^3$ is —OR. In some embodiments, $R^3$ is —SR. In some embodiments, $R^3$ is —NR$_2$. In some embodiments, $R^3$ is —S(O)$_2$R. In some embodiments, $R^3$ is —S(O)$_2$NR$_2$. In some embodiments, $R^3$ is —S(O)R. In some embodiments, $R^3$ is —CF$_2$R. In some embodiments, $R^3$ is —CF$_3$. In some embodiments, $R^3$ is —CR$_2$(OR). In some embodiments, $R^3$ is —CR$_2$(NR$_2$). In some embodiments, $R^3$ is —C(O)R. In some embodiments, $R^3$ is —C(O)OR. In some embodiments, $R^3$ is —C(O)NR$_2$. In some embodiments, $R^3$ is —C(O)N(R)OR. In some embodiments, $R^3$ is —OC(O)R. In some embodiments, $R^3$ is —OC(O)NR$_2$. In some embodiments, $R^3$ is —N(R)C(O)OR. In some embodiments, $R^3$ is —N(R)C(O)R. In some embodiments, $R^3$ is —N(R)C(O)NR$_2$. In some embodiments, $R^3$ is —N(R)S(O)$_2$R. In some embodiments, $R^3$ is —OP(O)R$_2$. In some embodiments, $R^3$ is —OP(O)(OR)$_2$. In some embodiments, $R^3$ is —OP(O)(OR)NR$_2$. In some embodiments, $R^3$ is —OP(O)(NR$_2$)$_2$. In some embodiments, $R^3$ is —SiR$_3$.

In certain embodiments, $R^3$ is selected from those shown in the compounds of Table 1.

As defined above and described herein, each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^4$ is an optionally substituted $C_{1-6}$ aliphatic. In some embodiments, $R^4$ is an optionally substituted phenyl. In some embodiments, $R^4$ is an optionally substituted 4-7 membered saturated or partially unsaturated heterocyclic ring having 1-2 heteroatoms independently selected from nitrogen, oxygen, and sulfur. In some embodiments, $R^4$ is an optionally substituted 5-6 membered heteroaryl ring having 1-4 heteroatoms independently selected from nitrogen, oxygen, and sulfur.

In certain embodiments, $R^4$ is selected from those shown in the compounds of Table 1.

As defined above and described herein, ==== is a single or double bond.

In some embodiments, ==== is a single bond. In some embodiments, ==== is a double bond.

In certain embodiments, ==== is selected from those shown in the compounds of Table 1.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In certain embodiments, m is selected from those shown in the compounds of Table 1.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In certain embodiments, n is selected from those shown in the compounds of Table 1.

As defined above and described herein, o is 0, 1, or 2.

In some embodiments, n is 0. In some embodiments, n is 1. In some embodiments, m is 2.

In certain embodiments, o is selected from those shown in the compounds of Table 1.

In some embodiments, the present invention provides a compound of formula I-qqq, wherein Ring A is benzo, o is 1, $X^1$ is —CH$_2$—, $X^2$ and $X^3$ are —C(O)—, and $Z^1$ and $Z^2$ are carbon atoms as shown, to provide a compound of formula I-qqq-1:

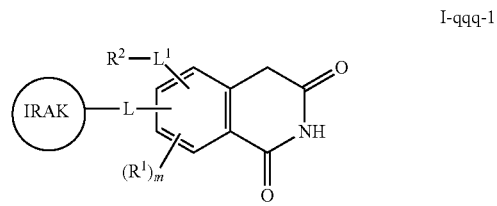

I-qqq-1 or a pharmaceutically acceptable salt thereof, wherein each of IRAK, L, $L^1$, $R^1$, $R^2$, and m is as defined above and described in embodiments herein, both singly and in combination.

In some embodiments, the present invention provides a compound of formula I-qqq, wherein Ring A is benzo, o is 1, $X^1$, $X^2$ and $X^3$ are —C(O)—, and $Z^1$ and $Z^2$ are carbon atoms as shown, to provide a compound of formula I-qqq-12:

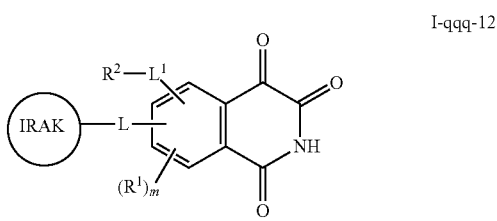

I-qqq-12 or a pharmaceutically acceptable salt thereof, wherein each of IRAK, L, $L^1$, $R^1$, $R^2$, and m is as defined above and described in embodiments herein, both singly and in combination.

In some embodiments, LBM is

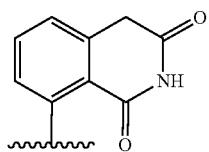 [SMILES: *c1cccc2c1C(=O)NC(=O)C2]

In some embodiments, LBM is

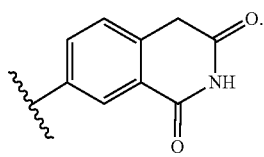 [SMILES: *c1ccc2c(c1)C(=O)NC(=O)C2]

In some embodiments, LBM is

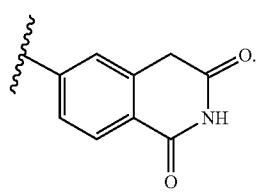 [SMILES: *c1ccc2c(c1)CC(=O)NC2=O]

In some embodiments, LBM is

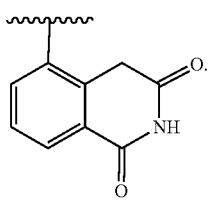 [SMILES: *c1cccc2c1CC(=O)NC2=O]

In some embodiments, LBM is

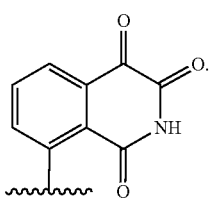 [SMILES: *c1cccc2c1C(=O)NC(=O)C2=O]

In some embodiments, LBM is

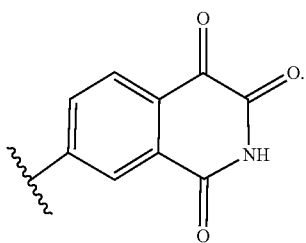 [SMILES: *c1ccc2c(c1)C(=O)NC(=O)C2=O]

In some embodiments, LBM is

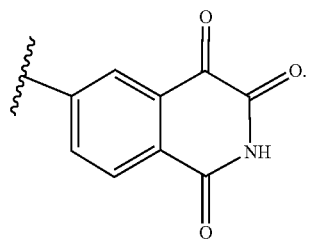 [SMILES: *c1ccc2c(c1)C(=O)C(=O)NC2=O]

In some embodiments, LBM is

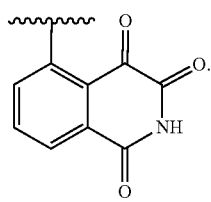 [SMILES: *c1cccc2c1C(=O)C(=O)NC2=O]

In some embodiments, LBM is selected from those in Table 1, below.

In certain embodiments, the present invention provides a compound of formula I, wherein LBM is a RPN13 binding moiety thereby forming a compound of formula I-rrr:

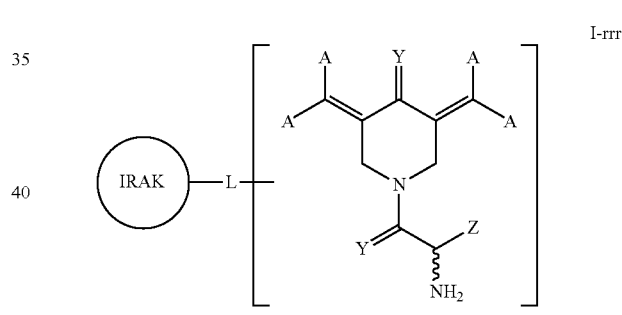

I-rrr or a pharmaceutically acceptable salt thereof, wherein L and IRAK are as defined above and described in embodiments herein, and wherein each of the variables A, Y, and Z is as described and defined in WO 2019/165229, the entirety of each of which is herein incorporated by reference.

In certain embodiments, the present invention provides a compound of formula I, wherein LBM is a Ubr1 binding moiety as described in Shanmugasundaram, K. et al, J. Bio. Chem. 2019, doi: 10.1074/jbc.AC119.010790, the entirety of each of which is herein incorporated by reference, thereby forming a compound of formula I-sss-1 or I-sss-2:

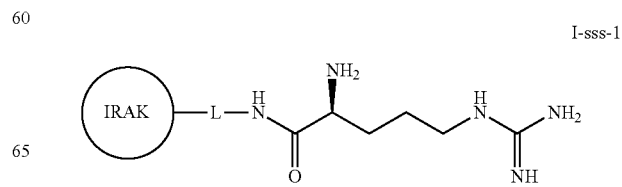

I-sss-1

I-sss-2

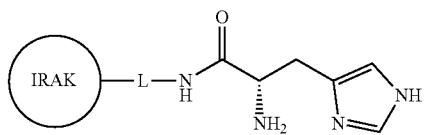

or a pharmaceutically acceptable salt thereof, wherein L and IRAK are as defined above and described in embodiments herein.

In certain embodiments, the present invention provides a compound of formula I, wherein LBM is a CRBN E3 ubiquitin ligase binding moiety thereby forming a compound of formula I-uuu-1, I-uuu-2, I-uuu-3 or I-uuu-4:

I-ttt-1

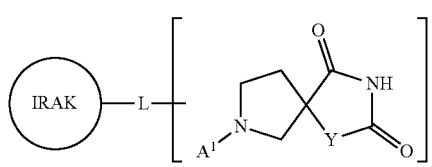

I-uuu-2

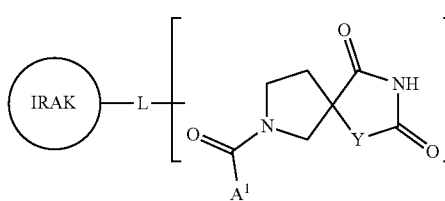

I-uuu-3

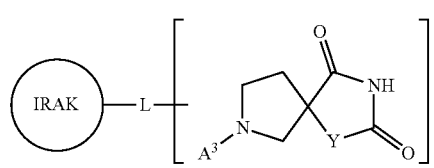

I-uuu-4

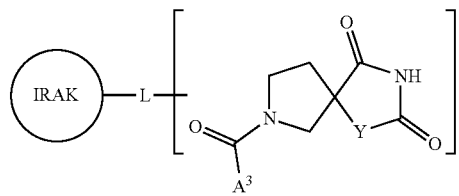

or a pharmaceutically acceptable salt thereof, wherein L and IRAK are as defined above and described in embodiments herein, and wherein each of the variables Y, $A^1$, and $A^3$ is as described and defined in WO 2019/236483, the entirety of each of which is herein incorporated by reference.

In certain embodiments, the present invention provides a compound of formula I, wherein LBM is human kelch-like ECH-associated protein 1 (KEAP1) thereby forming a compound of formula I-vvv:

I-vvv

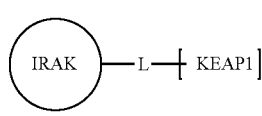

or a pharmaceutically acceptable salt thereof, wherein L and IRAK are as defined above and described in embodiments herein, both singly and in combination.

In certain embodiments, the present invention provides a compound of formula I, wherein LBM is KEAP1 binding moiety as recited in Lu et al., Euro. J. Med. Chem., 2018, 146:251-9, thereby forming a compound of formula I-www:

I-www

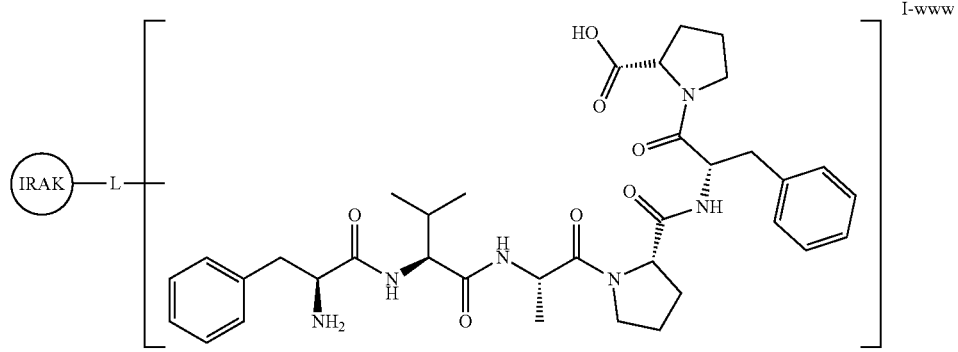

or a pharmaceutically acceptable salt thereof, wherein L and IRAK are as defined above and described in embodiments herein, both singly and in combination.

In certain embodiments, the present invention provides a compound of formula I, wherein LBM is KEAP1-NRF2 binding moiety thereby forming a compound of formula I-xxx or I-xxx-2:

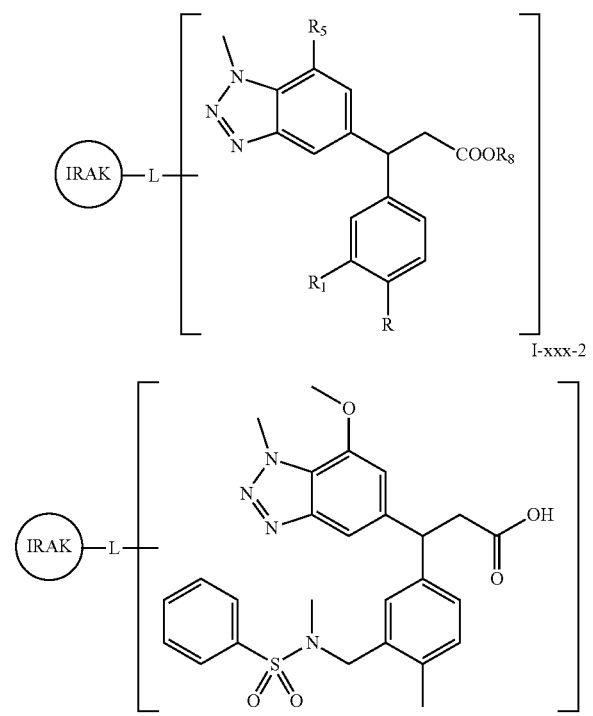

or a pharmaceutically acceptable salt thereof, wherein L and IRAK are as defined above and described in embodiments herein, and wherein each of the variables R, $R_1$, $R_5$, and $R_8$ is as described and defined in WO 2020/018788, the entirety of each of which is herein incorporated by reference.

In certain embodiments, the present invention provides a compound of formula I, wherein LBM is KEAP1-NRF2 binding moiety as recited in Tong et al., "Targeted Protein Degradation via a Covalent Reversible Degrader Based on Bardoxolone", ChemRxiv 2020, thereby forming a compound of formula I-yyy-1 or I-yyy-2:

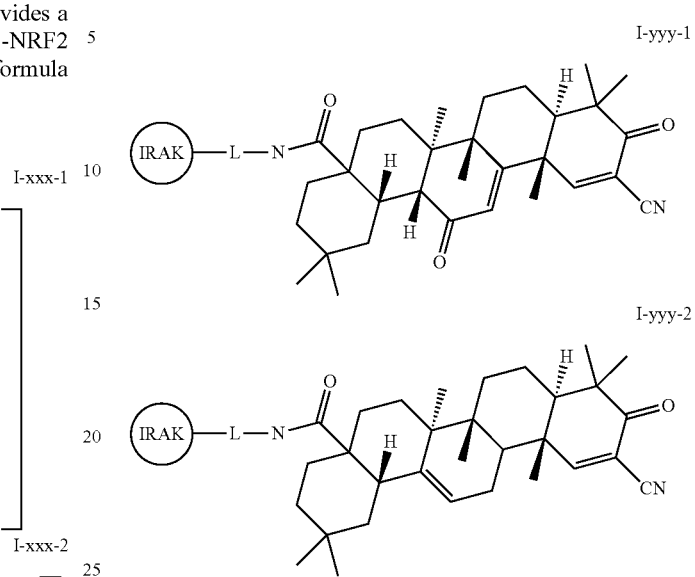

or a pharmaceutically acceptable salt thereof, wherein L and IRAK are as defined above and described in embodiments herein, both singly and in combination.

In some embodiments, the present invention provides a compound of formula I-a, wherein LBM is RNF114 E3 ubiquitin ligase

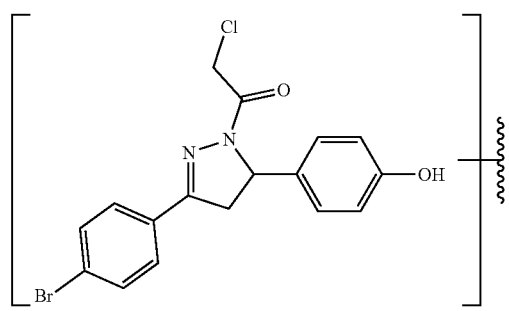

thereby forming a compound of formula I-zzz-1:

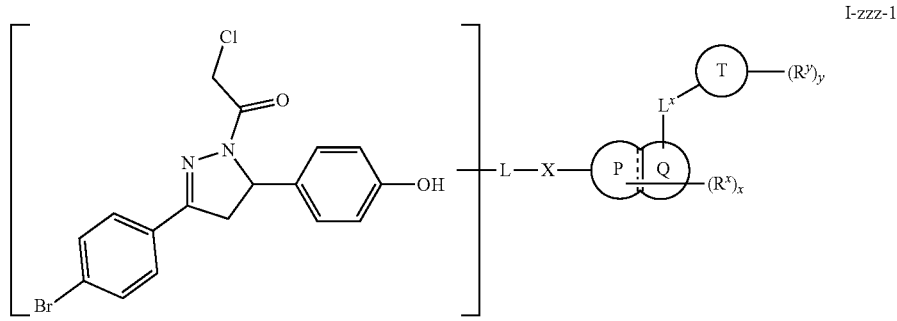

or a pharmaceutically acceptable salt thereof, wherein each of L, L$^x$, X, Ring P, Ring Q, Ring T, R$^x$, R$^y$, x, and y is as defined above and described in embodiments herein, both singly and in combination.

In some embodiments, the present invention provides a compound of formula I-a, wherein LBM is DCAF15 E3 ubiquitin ligase

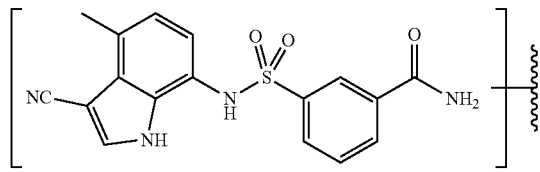

thereby forming a compound of formula I-zzz-2:

or -4) is achieved through the action of a lysine mimetic. In some embodiments, upon the binding of a compound of formula I to IRAK-1, the moiety that mimics a lysine undergoes ubiquitination thereby marking IRAK-1 for degradation via the Ubiquitin-Proteasome Pathway (UPP). In some embodiments, upon the binding of a compound of formula I to IRAK-2, the moiety that mimics a lysine undergoes ubiquitination thereby marking IRAK-2 for degradation via the Ubiquitin-Proteasome Pathway (UPP). In some embodiments, upon the binding of a compound of formula I to IRAK-3, the moiety that mimics a lysine undergoes ubiquitination thereby marking IRAK-3 for degradation via the Ubiquitin-Proteasome Pathway (UPP). In some embodiments, upon the binding of a compound of formula I to IRAK-4, the moiety that mimics a lysine undergoes ubiquitination thereby marking IRAK-4 for degradation via the Ubiquitin-Proteasome Pathway (UPP).

I-zzz-2

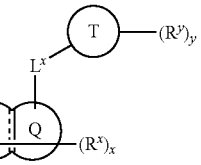

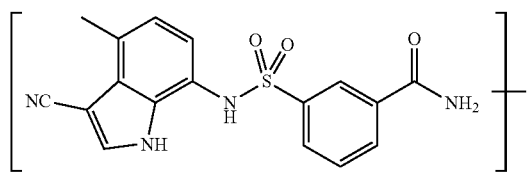

or a pharmaceutically acceptable salt thereof, wherein each of L, L$^x$, X, Ring P, Ring Q, Ring T, R$^x$, R$^y$, x, and y is as defined above and described in embodiments herein, both singly and in combination.

In some embodiments, LBM is

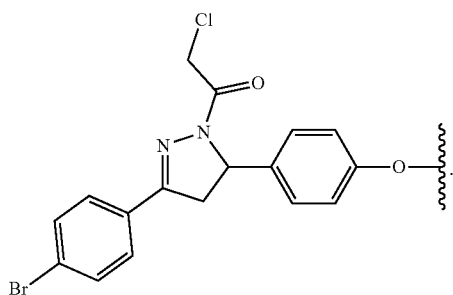 [SMILES: *Oc1ccc(C2CC(c3ccc(Br)cc3)=NN2C(=O)CCl)cc1]

In some embodiments, LBM is

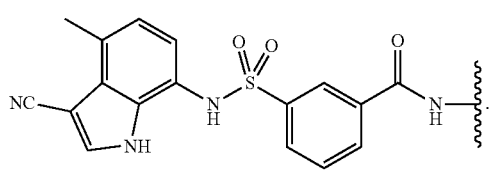 [SMILES: *NC(=O)c1cccc(S(=O)(=O)Nc2ccc(C)c3c(C#N)c[nH]c23)c1]

Lysine Mimetic

In some embodiments, DIM is LBM as described above and herein. In some embodiments, DIM is lysine mimetic. In some embodiments, the covalent attachment of ubiquitin to a member of the IRAK kinase family (i.e., IRAK-1, -2, -3, In some embodiments, DIM is

In some embodiments, DIM is

In some embodiments, DIM is

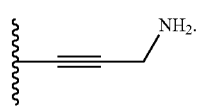

In some embodiments, DIM is selected from those depicted in Table 1, below.

In some embodiments, the present invention provides the compound of formula I wherein DIM is

thereby forming a compound of formula I-kkk-1:

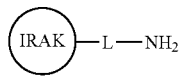

I-kkk-1 or a pharmaceutically acceptable salt thereof, wherein each of IRAK and L is as defined above and described in embodiments herein, both singly and in combination.

In some embodiments, the present invention provides the compound of formula I wherein DIM is

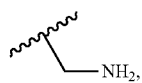

thereby forming a compound of formula I-kkk-2:

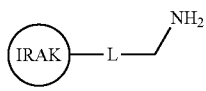

I-kkk-2 or a pharmaceutically acceptable salt thereof, wherein each of IRAK and L is as defined above and described in embodiments herein, both singly and in combination.

In some embodiments, the present invention provides the compound of formula I wherein DIM is

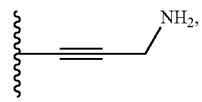

thereby forming a compound of formula I-kkk-3:

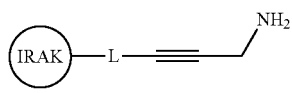

I-kkk-3 or a pharmaceutically acceptable salt thereof, wherein each of IRAK and L is as defined above and described in embodiments herein, both singly and in combination.

In certain embodiments, the present invention provides a compound of Formula I, wherein DIM is lysine mimetic

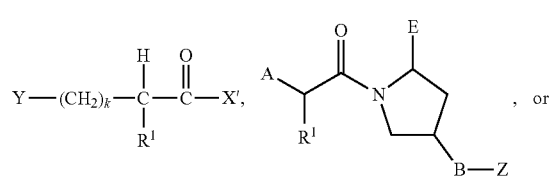

, or

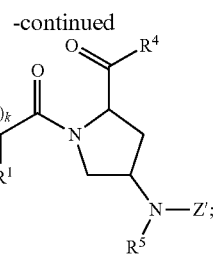

thereby forming a compound of formulae I-lll-1, I-lll-2, or I-lll-3, respectively:

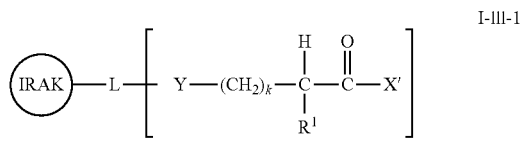

I-lll-1

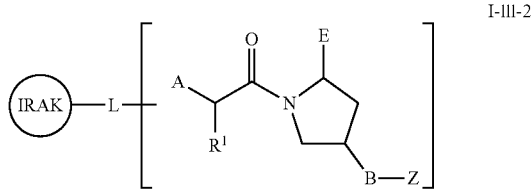

I-lll-2

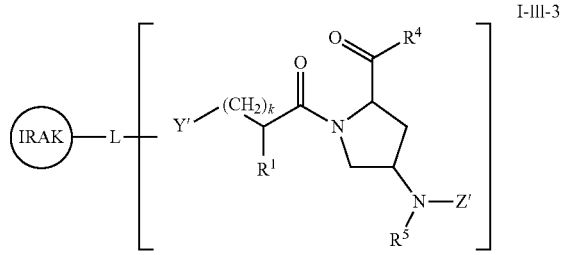

I-lll-3 or a pharmaceutically acceptable salt thereof, wherein L and IRAK are as defined above and described in embodiments herein, and wherein each of the variables $R^1$, $R^4$, $R^5$, A, B, E, Y, Y', Z, Z', and k are as defined and described in U.S. Pat. No. 7,622,496, the entirety of each of which is herein incorporated by reference.

Hydrogen Atom

In some embodiments, DIM is a hydrogen atom. In some embodiments, the covalent attachment of ubiquitin to one or more members of the IRAK kinase family (i.e., IRAK-1, -2, -3, or -4) is achieved through a provided compound wherein DIM is a hydrogen atom. In some embodiments, upon the binding of a compound of formula I to IRAK-1, the DIM moiety being hydrogen effectuates ubiquitination thereby marking IRAK-1 for degradation via the Ubiquitin-Proteasome Pathway (UPP). In some embodiments, upon the binding of a compound of formula I to IRAK-2, the DIM moiety being hydrogen effectuates ubiquitination thereby marking IRAK-2 for degradation via the Ubiquitin-Proteasome Pathway (UPP). In some embodiments, upon the binding of a compound of formula I to IRAK-3, the DIM moiety being hydrogen effectuates ubiquitination thereby marking IRAK-3 for degradation via the Ubiquitin-Proteasome Pathway (UPP). In some embodiments, upon the binding of a compound of formula I to IRAK-4, the DIM moiety being hydrogen effectuates ubiquitination thereby marking IRAK-4 for degradation via the Ubiquitin-Proteasome Pathway (UPP).

In some embodiments, DIM is selected from those depicted in Table 1, below.

In some embodiments, the present invention provides the compound of formula I wherein DIM is a hydrogen atom, thereby forming a compound of formula I-mmm:

I-mmm or a pharmaceutically acceptable salt thereof, wherein each of IRAK and L is as defined above and described in embodiments herein, both singly and in combination.

Linker (L)

As defined above and described herein, L is a bivalent moiety that connects IRAK to LBM or IRAK to DIM.

In some embodiments, L is a bivalent moiety that connects IRAK to LBM. In some embodiments, L is a bivalent moiety that connects IRAK to DIM. In some embodiments, L is a bivalent moiety that connects IRAK to a lysine mimetic.

In some embodiments, L is a covalent bond or a bivalent, saturated or unsaturated, straight or branched $C_{1-50}$ hydrocarbon chain, wherein 0-6 methylene units of L are independently replaced by —C(D)(H)—, —C(D)$_2$-, —CRF—, —CF$_2$—, -Cy-, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

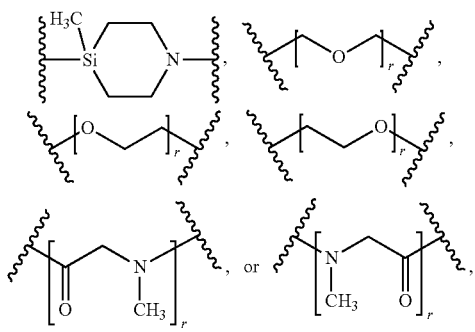

wherein: each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur, wherein r is 0, 1, 2, 3, 4, 5, 6, 7, 8, 9, or 10, and wherein R is as described above (e.g., in formula I-a).

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-11 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy- is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-11 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

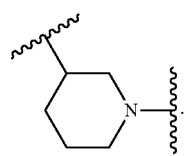 [SMILES: *C1CCCN(*)C1]

In some embodiments, -Cy- is

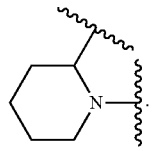 [SMILES: *C1CCCCN1*]

In some embodiments, -Cy- is

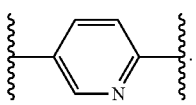

In some embodiments, -Cy- is
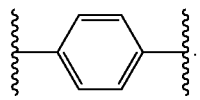
In some embodiments, -Cy- is
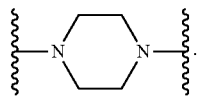
In some embodiments, -Cy- is
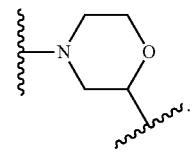 [SMILES: *C1CN(*)CCO1]
In some embodiments, -Cy- is
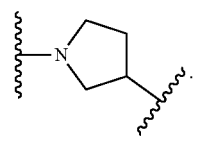 [SMILES: *C1CCN(*)C1]
In some embodiments, -Cy- is
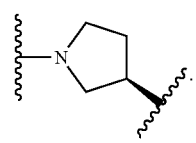 [SMILES: *[C@@H]1CCN(*)C1]
In some embodiments, -Cy- is
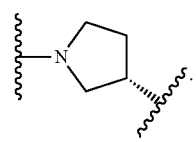 [SMILES: *[C@H]1CCN(*)C1]
In some embodiments, -Cy- is
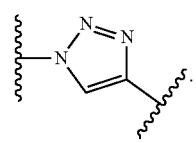 [SMILES: *c1cn(*)nn1]
In some embodiments, -Cy- is
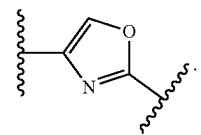 [SMILES: *c1coc(*)n1]
In some embodiments, -Cy- is
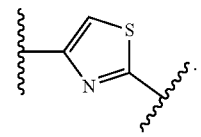 [SMILES: *c1csc(*)n1]
In some embodiments, -Cy- is
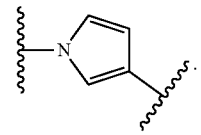 [SMILES: *c1ccn(*)c1]
In some embodiments, -Cy- is
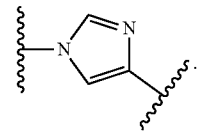 [SMILES: *c1cn(*)cn1]
In some embodiments, -Cy- is
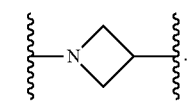
In some embodiments, -Cy- is
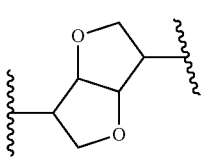

In some embodiments, -Cy- is

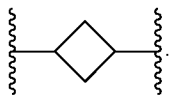

In some embodiments, -Cy- is

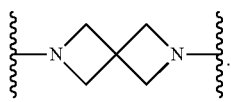 [SMILES: *N1CC2(C1)CN(*)C2]

In some embodiments, -Cy- is

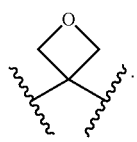 [SMILES: *C1(*)COC1]

In some embodiments, -Cy- is

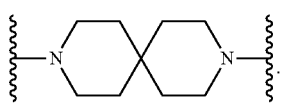 [SMILES: *N1CCC2(CC1)CCN(*)CC2]

In some embodiments, -Cy- is

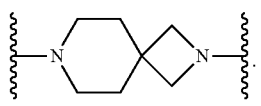 [SMILES: *N1CCC2(CC1)CN(*)C2]

In some embodiments, -Cy- is

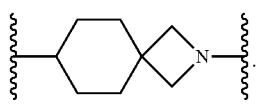

In some embodiments, -Cy- is

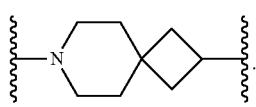

In some embodiments, -Cy- is

In some embodiments, -Cy- is

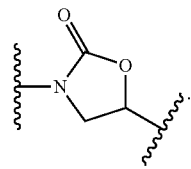 [SMILES: *C1CN(*)C(=O)O1]

In some embodiments, -Cy- is

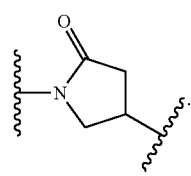 [SMILES: *C1CC(=O)N(*)C1]

In some embodiments, -Cy- is

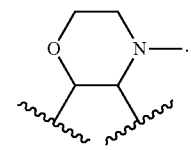 [SMILES: *C1OCCN(C)C1*]

In some embodiments, -Cy- is

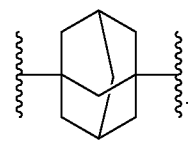 [SMILES: *C12CC3CC(C1)CC(*)(C3)C2]

In some embodiments, -Cy- is

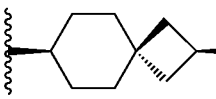

In some embodiments, -Cy- is

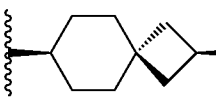

In some embodiments, -Cy- is

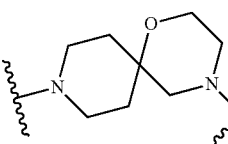

In some embodiments, -Cy- is

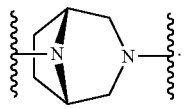 [SMILES: *N1C[C@H]2CC[C@@H](C1)N2*]

In some embodiments, -Cy- is

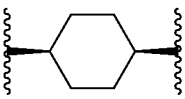

In some embodiments, -Cy- is

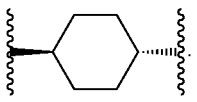

In some embodiments, -Cy- is

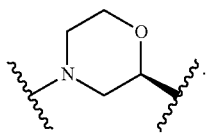 [SMILES: *[C@H]1CN(*)CCO1]

In some embodiments, -Cy- is

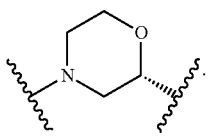 [SMILES: *[C@@H]1CN(*)CCO1]

In some embodiments, -Cy- is

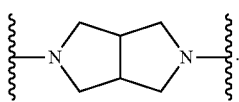

In some embodiments, -Cy- is

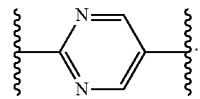

In some embodiments, -Cy- is

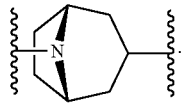 [SMILES: *C1C[C@H]2CC[C@@H](C1)N2*]

In some embodiments, -Cy- is

In some embodiments, -Cy- is

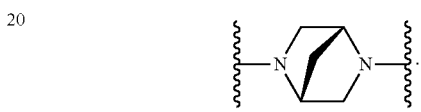

In some embodiments, -Cy- is

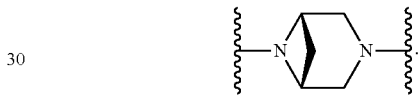

In some embodiments, an optionally substituted group on -Cy- is selected from —F, —$C_{1-6}$alkyl, —OH, —O$C_{1-6}$alkyl, —$CO_2H$, —$CO_2C_{1-6}$alkyl, —$(CH_2)_{1-6}CO_2H$, —$(CH_2)_{1-6}CO_2C_{1-6}$alkyl, —$P(O)(OH)_2$, —$P(O)(OC_{1-6}$alkyl$)_2$, —$(CH_2)_{1-6}P(O)(OH)_2$, and —$(CH_2)_{1-6}P(O)(OC_{1-6}$alkyl$)_2$.

In some embodiments, -Cy- is selected from those depicted in Table 1, below.

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is selected from those depicted in Table 1, below.

In some embodiments, L is substituted by a group selected from —F, —$C_{1-6}$alkyl, —OH, —O$C_{1-6}$alkyl, —$CO_2H$, —$CO_2C_{1-6}$alkyl, —$(CH_2)_{1-6}CO_2H$, —$(CH_2)_{1-6}CO_2C_{1-6}$alkyl, —$P(O)(OH)_2$, —$P(O)(OC_{1-6}$alkyl$)_2$, —$(CH_2)_{1-6}P(O)(OH)_2$, and —$(CH_2)_{1-6}P(O)(OC_{1-6}$ alkyl$)_2$.

In some embodiments, L is —NR—($C_{1-10}$ aliphatic)-. In some embodiments, L is —($C_{1-10}$ aliphatic)-NR—($C_{1-10}$ aliphatic)-. In some embodiments, L is —($C_{1-10}$ aliphatic)-NR—$(CH_2CH_2O)_{1-10}$ $CH_2CH_2$—. In some embodiments, L is -Cy-NR—($C_{1-10}$ aliphatic)-. In some embodiments, L is -Cy-($C_{1-10}$ aliphatic)-NR—. In some embodiments, L is -Cy-($C_{1-10}$ aliphatic)-NR—($C_{1-10}$ aliphatic)-. In some embodiments, L is —($C_{1-10}$ aliphatic)-Cy-NR—($C_{1-10}$ aliphatic)-. In some embodiments, L is —($C_{1-10}$ aliphatic)-Cy-($C_{1-10}$ aliphatic)-NR—. In some embodiments, L is —($C_{1-10}$ aliphatic)-Cy-($C_{1-10}$ aliphatic)-NR—($C_{1-10}$ aliphatic)-. In some embodiments, L is -Cy-($C_{1-10}$ aliphatic)-Cy-NR—. In some embodiments, L is -Cy-($C_{1-10}$ aliphatic)-NR-Cy-. In some embodiments, L is -Cy-($C_{1-10}$ aliphatic)-Cy-NR—($C_{1-10}$ aliphatic)-. In some embodiments, L is —Cy-($C_{1-10}$ aliphatic)-NR-Cy-($C_{1-10}$ aliphatic)-.

In some embodiments, L is —CONR—($C_{1-10}$ aliphatic)-. In some embodiments, L is —($C_{1-10}$ aliphatic)-CONR—($C_{1-10}$ aliphatic)-. In some embodiments, L is —($C_{1-10}$ aliphatic)-CONR—($CH_2CH_2O)_{1-10}CH_2CH_2$—. In some embodiments, L is -Cy-CONR—($C_{1-10}$ aliphatic)-. In some embodiments, L is -Cy-($C_{1-10}$ aliphatic)-CONR—. In some embodiments, L is -Cy-($C_{1-10}$ aliphatic)-CONR—($C_{1-10}$ aliphatic)-. In some embodiments, L is —($C_{1-10}$ aliphatic)-Cy-CONR—($C_{1-10}$ aliphatic)-. In some embodiments, L is —($C_{1-10}$ aliphatic)-Cy-($C_{1-10}$ aliphatic)-CONR—. In some embodiments, L is —($C_{1-10}$ aliphatic)-Cy-($C_{1-10}$ aliphatic)-CONR—($C_{1-10}$ aliphatic)-. In some embodiments, L is -Cy-($C_{1-10}$ aliphatic)-Cy-CONR—. In some embodiments, L is -Cy-($C_{1-10}$ aliphatic)-CONR-Cy-. In some embodiments, L is -Cy-($C_{1-10}$ aliphatic)-Cy-CONR—($C_{1-10}$ aliphatic)-. In some embodiments, L is -Cy-($C_{1-10}$ aliphatic)-CONR-Cy-($C_{1-10}$ aliphatic)-.

In some embodiments, L is —NRCO—($C_{1-10}$ aliphatic)-. In some embodiments, L is —($C_{1-10}$ aliphatic)-NRCO—($C_{1-10}$ aliphatic)-. In some embodiments, L is —($C_{1-10}$ aliphatic)-NRCO—($CH_2CH_2O)_{1-10}CH_2CH_2$—. In some embodiments, L is -Cy-NRCO—($C_{1-10}$ aliphatic)-. In some embodiments, L is -Cy-($C_{1-10}$ aliphatic)-NRCO—. In some embodiments, L is -Cy-($C_{1-10}$ aliphatic)-NRCO—($C_{1-10}$ aliphatic)-. In some embodiments, L is —($C_{1-10}$ aliphatic)-Cy-NRCO—($C_{1-10}$ aliphatic)-. In some embodiments, L is —($C_{1-10}$ aliphatic)-Cy-($C_{1-10}$ aliphatic)-NRCO—. In some embodiments, L is —($C_{1-10}$ aliphatic)-Cy-($C_{1-10}$ aliphatic)-NRCO—($C_{1-10}$ aliphatic)-. In some embodiments, L is -Cy-($C_{1-10}$ aliphatic)-Cy-NRCO—. In some embodiments, L is -Cy-($C_{1-10}$ aliphatic)-NRCO-Cy-. In some embodiments, L is -Cy-($C_{1-10}$ aliphatic)-Cy-NRCO—($C_{1-10}$ aliphatic)-. In some embodiments, L is -Cy-($C_{1-10}$ aliphatic)-NRCO-Cy-($C_{1-10}$ aliphatic)-.

In some embodiments, L is —O—($C_{1-10}$ aliphatic)-. In some embodiments, L is —($C_{1-10}$ aliphatic)-O—($C_{1-10}$ aliphatic)-. In some embodiments, L is —($C_{1-10}$ aliphatic)-O—($CH_2CH_2O)_{1-10}CH_2CH_2$—. In some embodiments, L is -Cy-O—($C_{1-10}$ aliphatic)-. In some embodiments, L is -Cy-($C_{1-10}$ aliphatic)-O—. In some embodiments, L is -Cy-($C_{1-10}$ aliphatic)-O—($C_{1-10}$ aliphatic)-. In some embodiments, L is —($C_{1-10}$ aliphatic)-Cy-O—($C_{1-10}$ aliphatic)-. In some embodiments, L is —($C_{1-10}$ aliphatic)-Cy-($C_{1-10}$ aliphatic)-O—. In some embodiments, L is —($C_{1-10}$ aliphatic)-Cy-($C_{1-10}$ aliphatic)-O—($C_{1-10}$ aliphatic)-. In some embodiments, L is —Cy-($C_{1-10}$ aliphatic)-Cy-O—. In some embodiments, L is -Cy-($C_{1-10}$ aliphatic)-O-Cy-. In some embodiments, L is -Cy-($C_{1-10}$ aliphatic)-Cy-O—($C_{1-10}$ aliphatic)-. In some embodiments, L is -Cy-($C_{1-10}$ aliphatic)-O-Cy-($C_{1-10}$ aliphatic)-.

In some embodiments, L is -Cy-($C_{1-10}$ aliphatic)-. In some embodiments, L is —($C_{1-10}$ aliphatic)-Cy-($C_{1-10}$ aliphatic)-. In some embodiments, L is —($C_{1-10}$ aliphatic)-Cy-($CH_2CH_2O)_{1-10}CH_2CH_2$—. In some embodiments, L is -Cy-($C_{1-10}$ aliphatic)-Cy-. In some embodiments, L is -Cy-($C_{1-10}$ aliphatic)-Cy-($C_{1-10}$ aliphatic)-. In some embodiments, L is -Cy-($C_{1-10}$ aliphatic)-Cy-($C_{1-10}$ aliphatic)-Cy-. In some embodiments, L is —($C_{1-10}$ aliphatic)-Cy-($C_{1-10}$ aliphatic)-Cy-($C_{1-10}$ aliphatic)-.

In some embodiments, L is —NR—($CH_2)_{1-10}$—. In some embodiments, L is —($CH_2)_{1-10}$—NR—($CH_2)_{1-10}$—. In some embodiments, L is —($CH_2)_{1-10}$—NR—($CH_2CH_2O)_{1-10}$ $CH_2CH_2$—. In some embodiments, L is -Cy-NR—($CH_2)_{1-10}$—. In some embodiments, L is -Cy-($CH_2)_{1-10}$—NR—. In some embodiments, L is -Cy-($CH_2)_{1-10}$—NR—($CH_2)_{1-10}$—. In some embodiments, L is —($CH_2)_{1-10}$-Cy-NR—($CH_2)_{1-10}$—. In some embodiments, L is —($CH_2)_{1-10}$-Cy-($CH_2)_{1-10}$—NR—. In some embodiments, L is —($CH_2)_{1-10}$-Cy-($CH_2)_{1-10}$—NR—($CH_2)_{1-10}$—. In some embodiments, L is -Cy-($CH_2)_{1-10}$-Cy-NR—. In some embodiments, L is -Cy-($CH_2)_{1-10}$—NR-Cy-. In some embodiments, L is -Cy-($CH_2)_{1-10}$-Cy-NR—($CH_2)_{1-10}$—. In some embodiments, L is -Cy-($CH_2)_{1-10}$—NR-Cy-($CH_2)_{1-10}$—.

In some embodiments, L is —CONR—($CH_2)_{1-10}$—. In some embodiments, L is —($CH_2)_{1-10}$—CONR—($CH_2)_{1-10}$—. In some embodiments, L is —($CH_2)_{1-10}$—CONR—($CH_2CH_2O)_{1-10}$ $CH_2CH_2$—. In some embodiments, L is -Cy-CONR—($CH_2)_{1-10}$—. In some embodiments, L is -Cy-($CH_2)_{1-10}$—CONR—. In some embodiments, L is -Cy-($CH_2)_{1-10}$—CONR—($CH_2)_{1-10}$—. In some embodiments, L is —($CH_2)_{1-10}$-Cy-CONR—($CH_2)_{1-10}$—. In some embodiments, L is —($CH_2)_{1-10}$-Cy-($CH_2)_{1-10}$—CONR—. In some embodiments, L is —($CH_2)_{1-10}$-Cy-($CH_2)_{1-10}$—CONR—($CH_2)_{1-10}$—. In some embodiments, L is -Cy-($CH_2)_{1-10}$-Cy-CONR—. In some embodiments, L is -Cy-($CH_2)_{1-10}$—CONR-Cy-. In some embodiments, L is -Cy-($CH_2)_{1-10}$-Cy-CONR—($CH_2)_{1-10}$—. In some embodiments, L is -Cy-($CH_2)_{1-10}$—CONR-Cy-($CH_2)_{1-10}$—.

In some embodiments, L is —NRCO—($CH_2)_{1-10}$—. In some embodiments, L is —($CH_2)_{1-10}$—NRCO—($CH_2)_{1-10}$—. In some embodiments, L is —($CH_2)_{1-10}$—NRCO—($CH_2CH_2O)_{1-10}$ $CH_2CH_2$—. In some embodiments, L is -Cy-NRCO—($CH_2)_{1-10}$—. In some embodiments, L is -Cy-($CH_2)_{1-10}$—NRCO—. In some embodiments, L is -Cy-($CH_2)_{1-10}$—NRCO—($CH_2)_{1-10}$—. In some embodiments, L is —($CH_2)_{1-10}$-Cy-NRCO—($CH_2)_{1-10}$—. In some embodiments, L is —($CH_2)_{1-10}$-Cy-($CH_2)_{1-10}$—NRCO—. In some embodiments, L is —($CH_2)_{1-10}$-Cy-($CH_2)_{1-10}$—NRCO—($CH_2)_{1-10}$—. In some embodiments, L is -Cy-($CH_2)_{1-10}$-Cy-NRCO—. In some embodiments, L is -Cy-($CH_2)_{1-10}$—NRCO-Cy-. In some embodiments, L is -Cy-($CH_2)_{1-10}$-Cy-NRCO—($CH_2)_{1-10}$—. In some embodiments, L is -Cy-($CH_2)_{1-10}$—NRCO-Cy-($CH_2)_{1-10}$—.

In some embodiments, L is —O—($CH_2)_{1-10}$—. In some embodiments, L is —($CH_2)_{1-10}$—O—($CH_2)_{1-10}$—. In some embodiments, L is —($CH_2)_{1-10}$—O—($CH_2CH_2O)_{1-10}$ $CH_2CH_2$—. In some embodiments, L is -Cy-O—($CH_2)_{1-10}$—. In some embodiments, L is -Cy-($CH_2)_{1-10}$—O—. In some embodiments, L is -Cy-($CH_2)_{1-10}$—O—($CH_2)_{1-10}$—. In some embodiments, L is —($CH_2)_{1-10}$-Cy-O—($CH_2)_{1-10}$—. In some embodiments, L is —($CH_2)_{1-10}$-Cy-($CH_2)_{1-10}$—O—. In some embodiments, L is —($CH_2)_{1-10}$-Cy-($CH_2)_{1-10}$—O—($CH_2)_{1-10}$—. In some embodiments, L is -Cy-($CH_2)_{1-10}$-Cy-O—. In some embodiments, L is -Cy-($CH_2)_{1-10}$—O-Cy-. In some embodiments, L is —Cy-($CH_2)_{1-10}$-Cy-O—($CH_2)_{1-10}$—. In some embodiments, L is -Cy-($CH_2)_{1-10}$—O-Cy-($CH_2)_{1-10}$—.

In some embodiments, L is -Cy-($CH_2)_{1-10}$—. In some embodiments, L is —($CH_2)_{1-10}$-Cy-($CH_2)_{1-10}$—. In some embodiments, L is —($CH_2)_{1-10}$-Cy-($CH_2CH_2O)_{1-10}$ $CH_2CH_2$—. In some embodiments, L is -Cy-($CH_2)_{1-10}$-Cy-. In some embodiments, L is -Cy-($CH_2)_{1-10}$-Cy-($CH_2)_{1-10}$—. In some embodiments, L is -Cy-($CH_2)_{1-10}$-Cy-($CH_2)_{1-10}$-Cy-. In some embodiments, L is —($CH_2)_{1-10}$-Cy-($CH_2)_{1-10}$-Cy-($CH_2)_{1-10}$—.

In some embodiments, L is
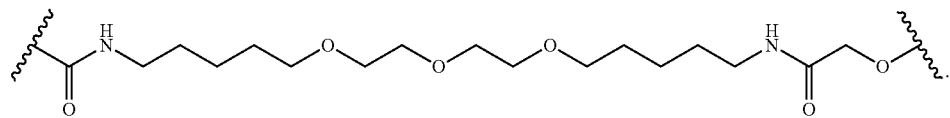 [SMILES: *OCC(=O)NCCCCCOCCOCCOCCCCCNC(*)=O]
In some embodiments, L is
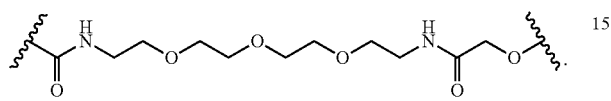
In some embodiments, L is
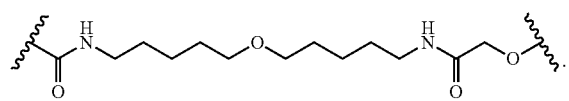 [SMILES: *OCC(=O)NCCCCCOCCCCCNC(*)=O]
In some embodiments, L is
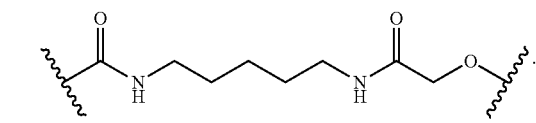
In some embodiments, L is
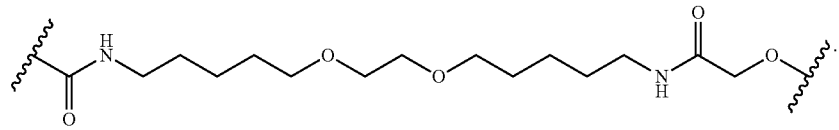 [SMILES: *OCC(=O)NCCCCCOCCOCCCCCNC(*)=O]
In some embodiments, L is
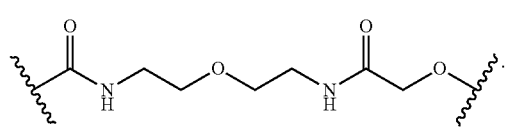 [SMILES: *OCC(=O)NCCOCCNC(*)=O]
In some embodiments, L is
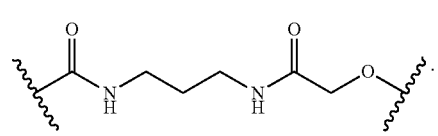 [SMILES: *OCC(=O)NCCCNC(*)=O]
In some embodiments, L is
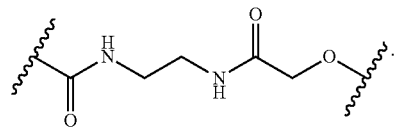 [SMILES: *OCC(=O)NCCNC(*)=O]
In some embodiments, L is
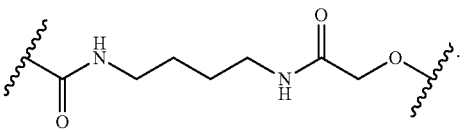 [SMILES: *OCC(=O)NCCCCNC(*)=O]
In some embodiments, L is
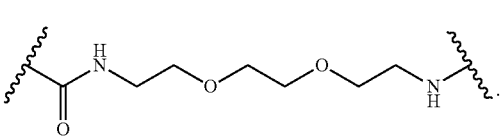 [SMILES: *NCCOCCOCCNC(*)=O]
In some embodiments, L is
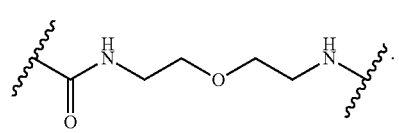 [SMILES: *NCCOCCNC(*)=O]
In some embodiments, L is
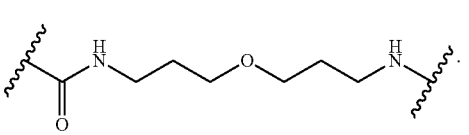 [SMILES: *NCCCOCCCNC(*)=O]

In some embodiments, L is
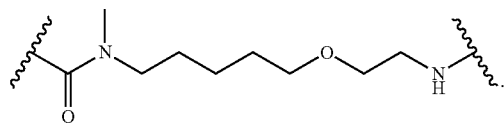 [SMILES: *NCCOCCCCCN(C)C(*)=O]
In some embodiments, L is
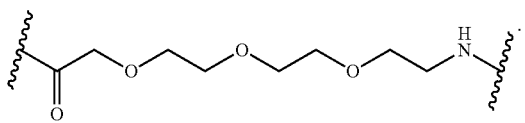
In some embodiments, L is
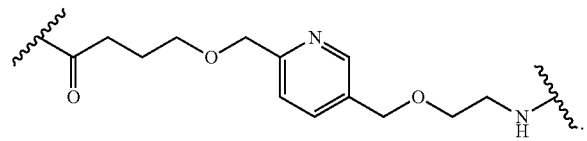 [SMILES: *NCCOCc1ccc(COCCCC(*)=O)nc1]
In some embodiments, L is
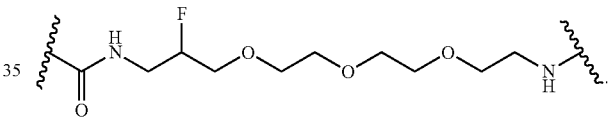
In some embodiments, L is
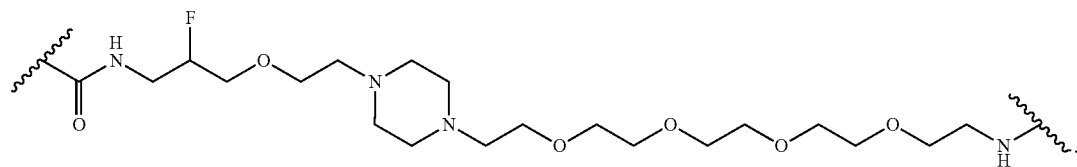
In some embodiments, L is
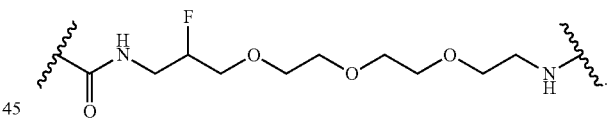
In some embodiments, L is
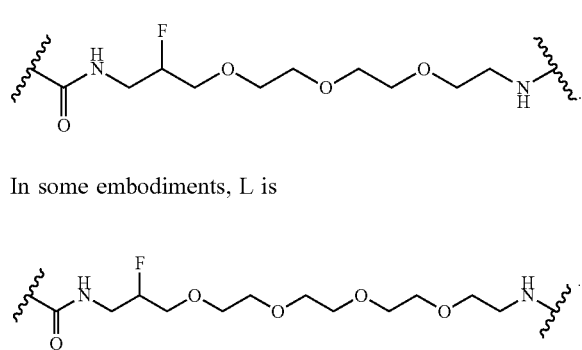
In some embodiments, L is
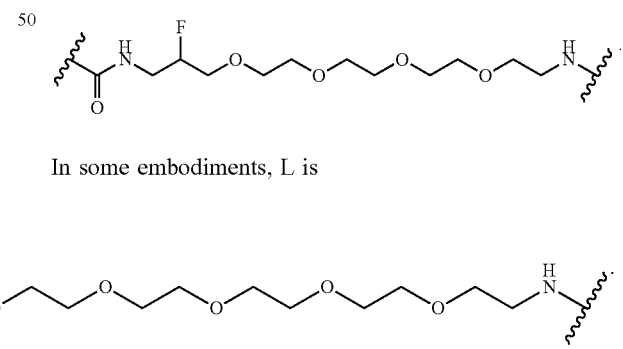

In some embodiments, L is
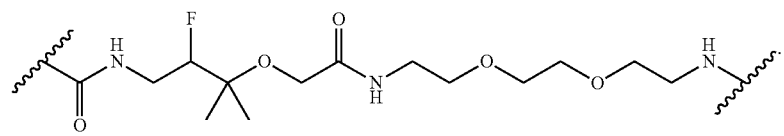
In some embodiments, L is
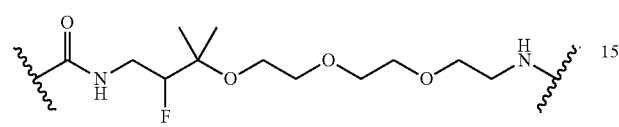
In some embodiments, L is
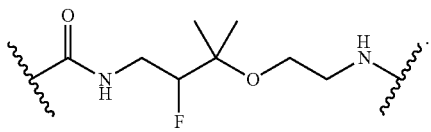
In some embodiments, L is
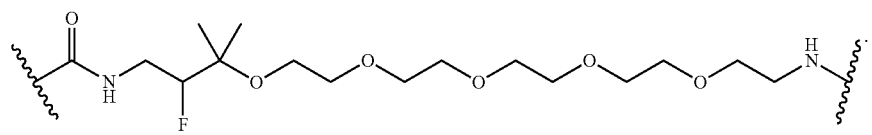
In some embodiments, L is
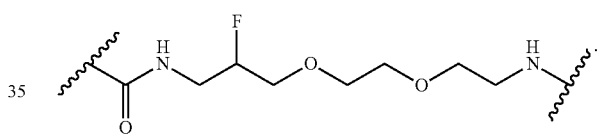
In some embodiments, L is
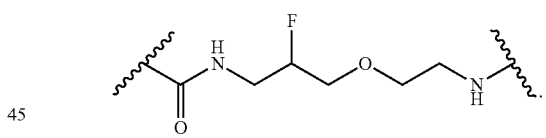
In some embodiments, L is
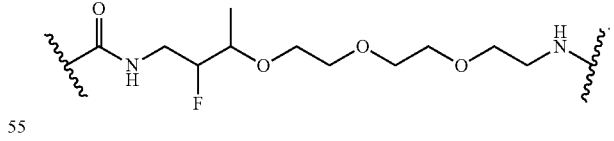
In some embodiments, L is
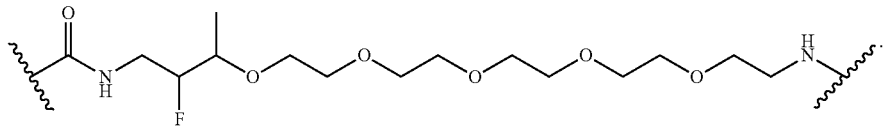 [SMILES: *NCCOCCOCCOCCOCCOC(C)C(F)CNC(*)=O]

In some embodiments, L is
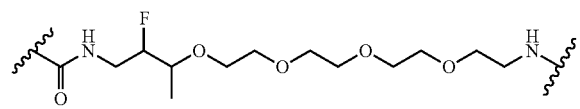
In some embodiments, L is
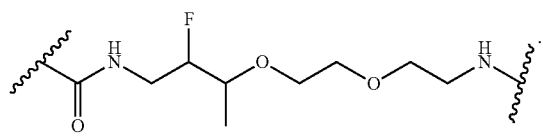 [SMILES: *NCCOCCOC(C)C(F)CNC(*)=O]
In some embodiments, L is
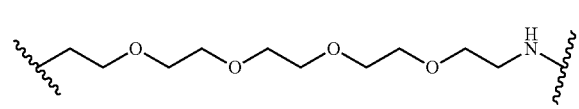
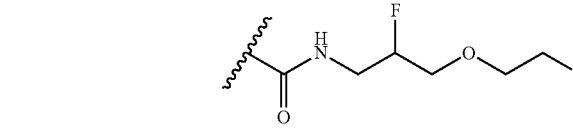
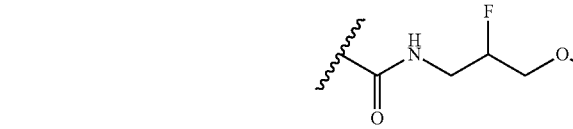
In some embodiments, L is
In some embodiments, L is
In some embodiments, L is
In some embodiments, L is In some embodiments, L is
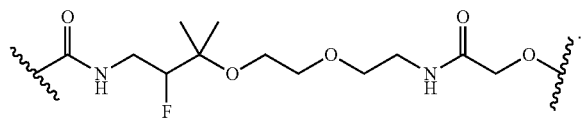 [SMILES: *OCC(=O)NCCOCCOC(C)(C)C(F)CNC(*)=O]
In some embodiments, L is
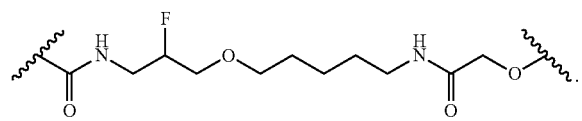 [SMILES: *OCC(=O)NCCCCCOCC(F)CNC(*)=O]
In some embodiments, L is
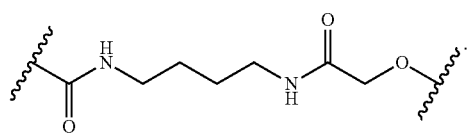 [SMILES: *OCC(=O)NCCCCNC(*)=O]
In some embodiments, L is
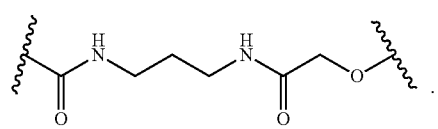 [SMILES: *OCC(=O)NCCCNC(*)=O]
In some embodiments, L is
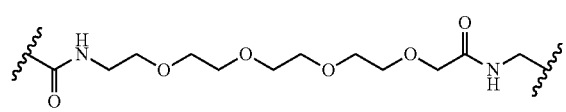
In some embodiments, L is
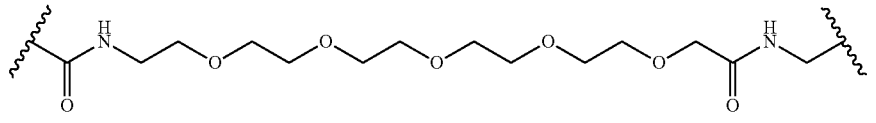
In some embodiments, L is
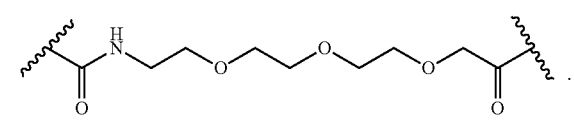 [SMILES: *C(=O)COCCOCCOCCNC(*)=O]
In some embodiments, L is
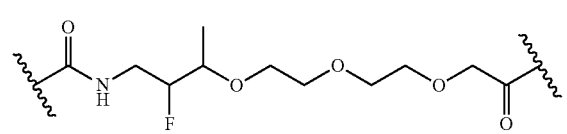
In some embodiments, L is
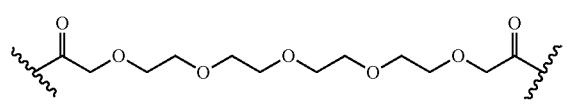
In some embodiments, L is
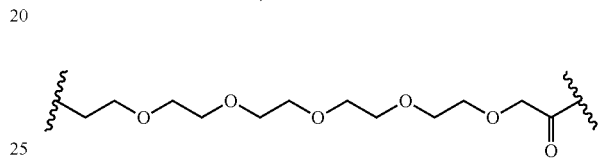
In some embodiments, L is
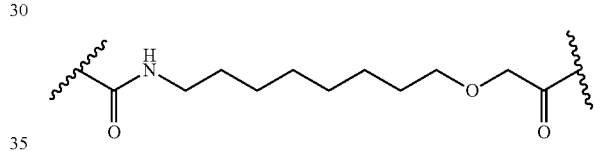
In some embodiments, L is
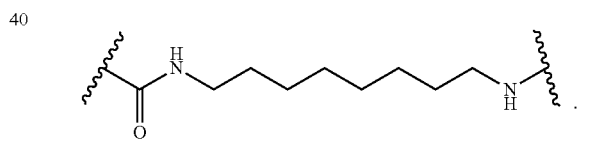
In some embodiments, L is
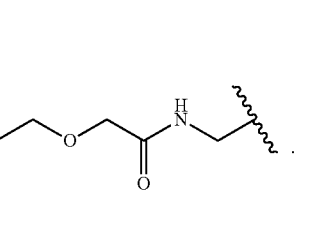
In some embodiments, L is
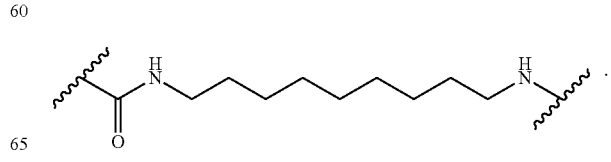

In some embodiments, L is

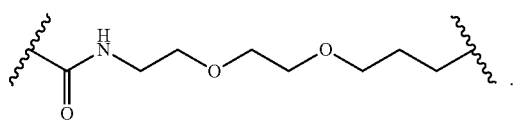 [SMILES: *CCCOCCOCCNC(*)=O]

In some embodiments, L is

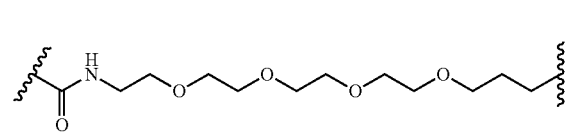

In some embodiments, L is

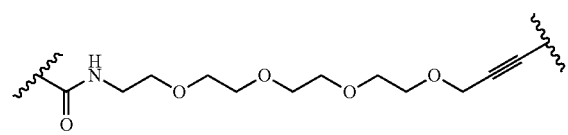

In some embodiments, L is

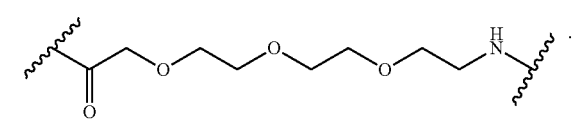 [SMILES: *NCCOCCOCCOCC(*)=O]

In some embodiments, L is

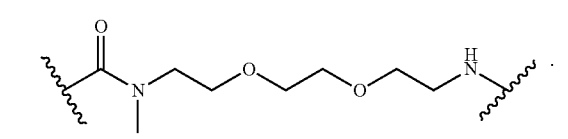 [SMILES: *NCCOCCOCCN(C)C(*)=O]

In some embodiments, L is

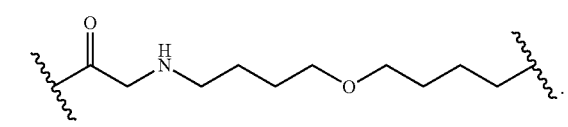 [SMILES: *CCCCOCCCCNCC(*)=O]

In some embodiments, L is

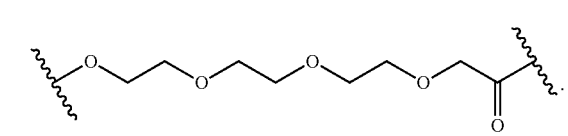 [SMILES: *OCCOCCOCCOCC(*)=O]

In some embodiments, L is

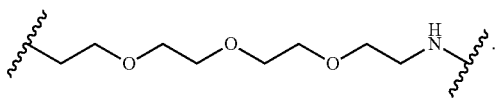 [SMILES: *CCOCCOCCOCCN*]

In some embodiments, L is

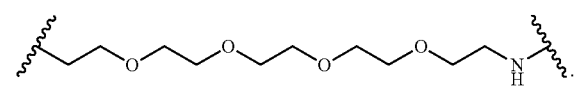 [SMILES: *CCOCCOCCOCCOCCN*]

In some embodiments, L is

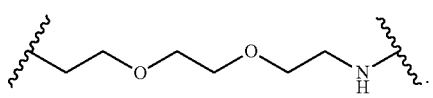 [SMILES: *CCOCCOCCN*]

In some embodiments, L is

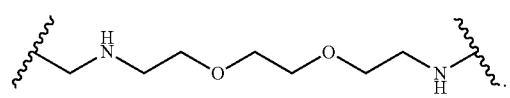 [SMILES: *CNCCOCCOCCN*]

In some embodiments, L is

In some embodiments, L is

In some embodiments, L is

In some embodiments, L is

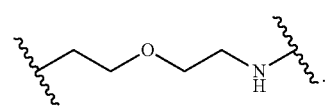 [SMILES: *CCOCCN*]

In some embodiments, L is
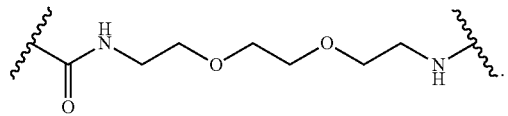 [SMILES: *NCCOCCOCCNC(*)=O]
In some embodiments, L is
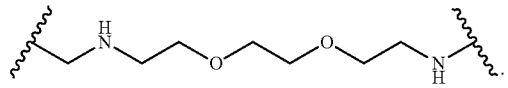 [SMILES: *CNCCOCCOCCN*]
In some embodiments, L is
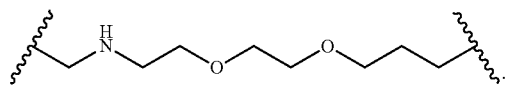 [SMILES: *CCCOCCOCCNC*]
In some embodiments, L is
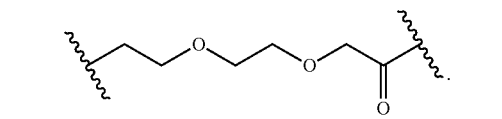 [SMILES: *CCOCCOCC(*)=O]
In some embodiments, L is
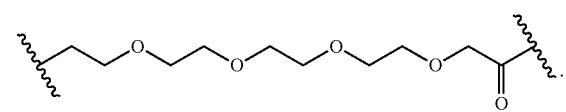 [SMILES: *CCOCCOCCOCCOCC(*)=O]
In some embodiments, L is
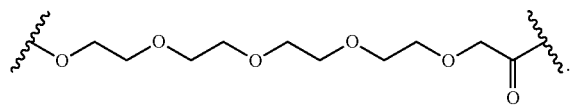 [SMILES: *OCCOCCOCCOCCOCC(*)=O]
In some embodiments, L is
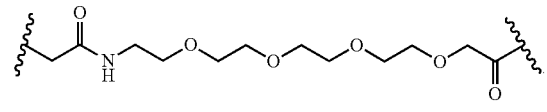 [SMILES: *CC(=O)NCCOCCOCCOCCOCC(*)=O]
In some embodiments, L is
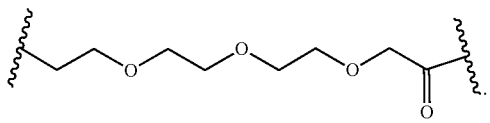 [SMILES: *CCOCCOCCOCC(*)=O]
In some embodiments, L is
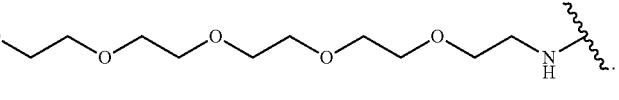
In some embodiments, L is
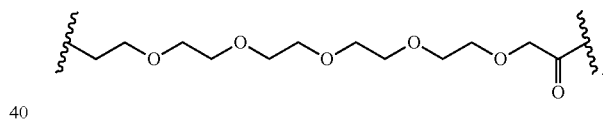
In some embodiments, L is
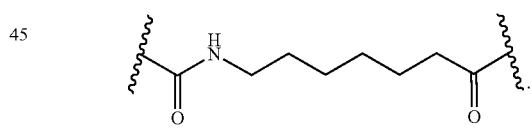
In some embodiments, L is
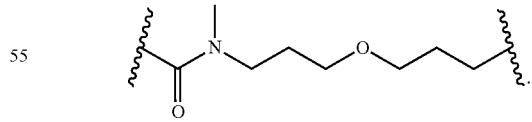
In some embodiments, L is
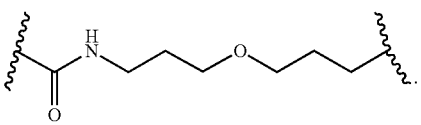 [SMILES: *CCCOCCCNC(*)=O]

In some embodiments, L is

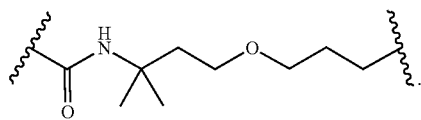 [SMILES: *CCCOCCC(C)(C)NC(*)=O]

In some embodiments, L is

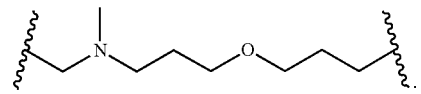 [SMILES: *CCCOCCCN(C)C*]

In some embodiments, L is

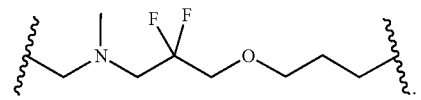 [SMILES: *CCCOCC(F)(F)CN(C)C*]

In some embodiments, L is

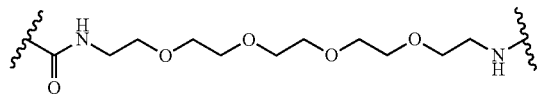 [SMILES: *NCCOCCOCCOCCOCCNC(*)=O]

In some embodiments, L is

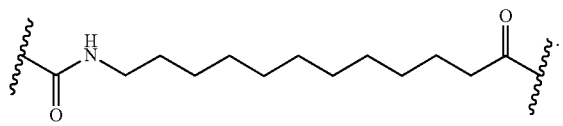 [SMILES: *C(=O)CCCCCCCCCCCNC(*)=O]

In some embodiments, L is

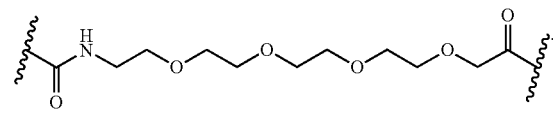 [SMILES: *C(=O)COCCOCCOCCOCCNC(*)=O]

In some embodiments, L is

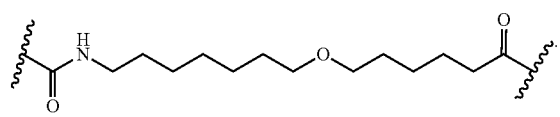 [SMILES: *C(=O)CCCCCOCCCCCCCNC(*)=O]

In some embodiments, L is

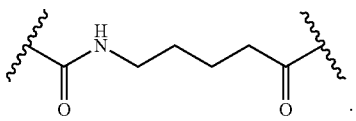 [SMILES: *C(=O)CCCCNC(*)=O]

In some embodiments, L is

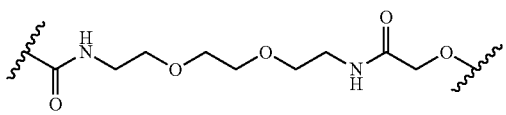

In some embodiments, L is

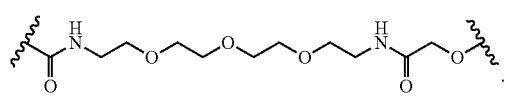 [SMILES: *OCC(=O)NCCOCCOCCOCCNC(*)=O]

In some embodiments, L is

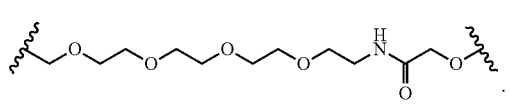 [SMILES: *COCCOCCOCCOCCNC(=O)CO*]

In some embodiments, L is

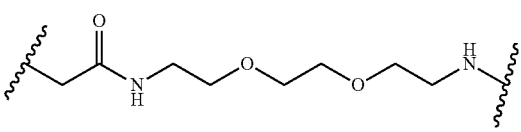

In some embodiments, L is

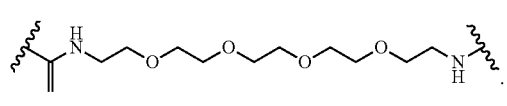 [SMILES: *NCCOCCOCCOCCOCCNC(*)=C]

In some embodiments, L is

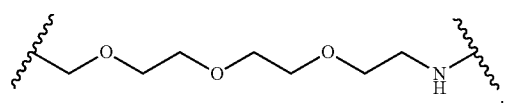 [SMILES: *COCCOCCOCCN*]

In some embodiments, L is

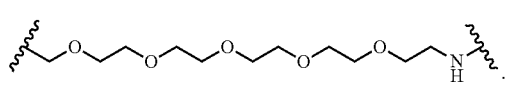 [SMILES: *COCCOCCOCCOCCOCCN*]

In some embodiments, L is
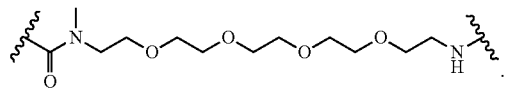 [SMILES: *NCCOCCOCCOCCOCCN(C)C(*)=O]
In some embodiments, L is
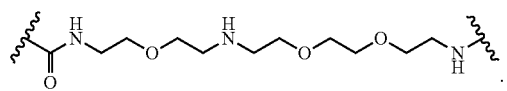 [SMILES: *NCCOCCOCCNCCOCCNC(*)=O]
In some embodiments, L is
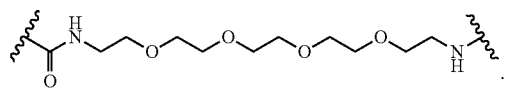 [SMILES: *NCCOCCOCCOCCOCCNC(*)=O]
In some embodiments, L is
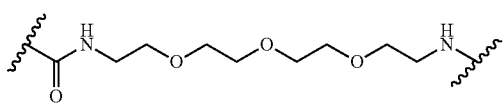
In some embodiments, L is
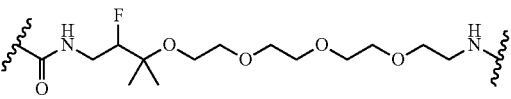
In some embodiments, L is
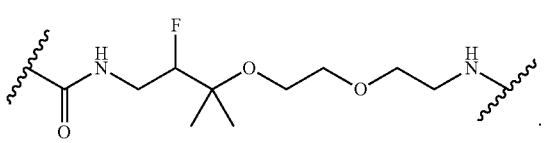 [SMILES: *NCCOCCOC(C)(C)C(F)CNC(*)=O]
In some embodiments, L is
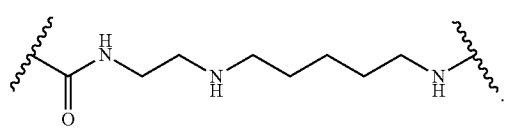 [SMILES: *NCCCCCNCCNC(*)=O]
In some embodiments, L is
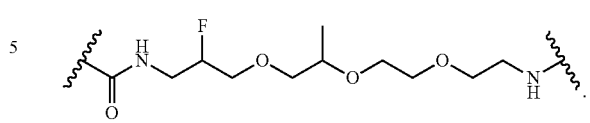
In some embodiments, L is
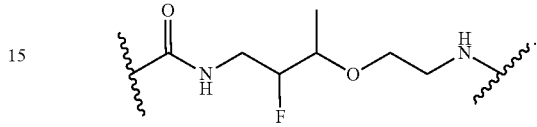
In some embodiments, L is
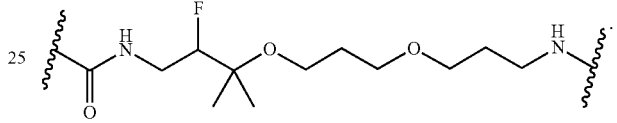
In some embodiments, L is
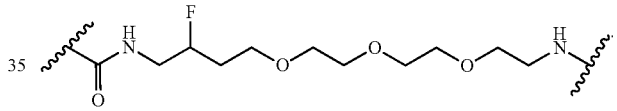
In some embodiments, L is
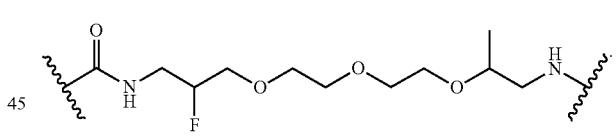
In some embodiments, L is
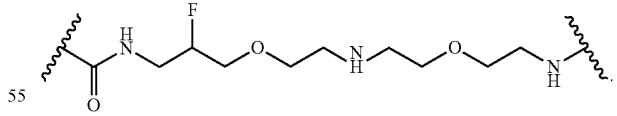
In some embodiments, L is
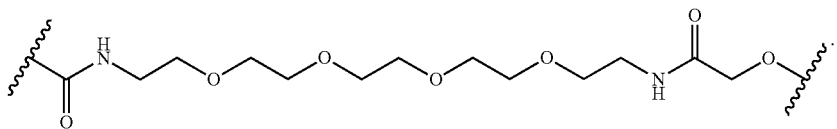 [SMILES: *OCC(=O)NCCOCCOCCOCCOCCNC(*)=O]

In some embodiments, L is
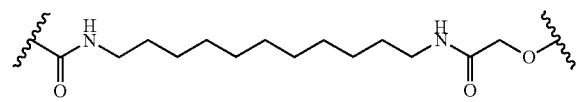
In some embodiments, L is
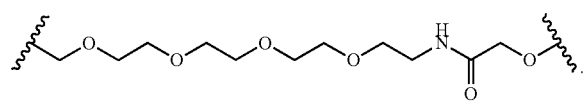
In some embodiments, L is
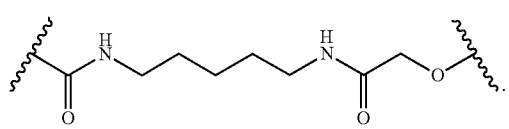
In some embodiments, L is
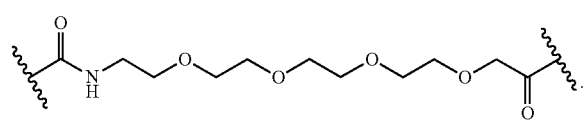 [SMILES: *C(=O)COCCOCCOCCOCCNC(*)=O]
In some embodiments, L is
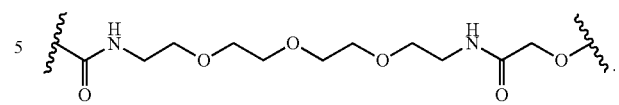
In some embodiments, L is
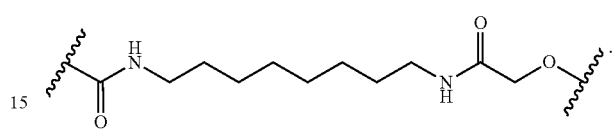
In some embodiments, L is
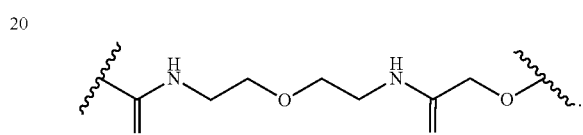
In some embodiments, L is
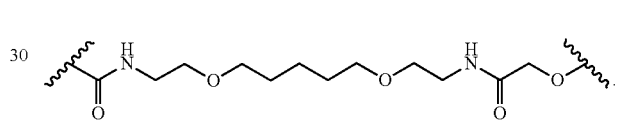
In some embodiments, L is
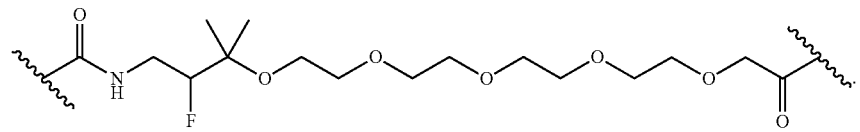 [SMILES: *C(=O)COCCOCCOCCOCCOC(C)(C)C(F)CNC(*)=O]
In some embodiments, L is
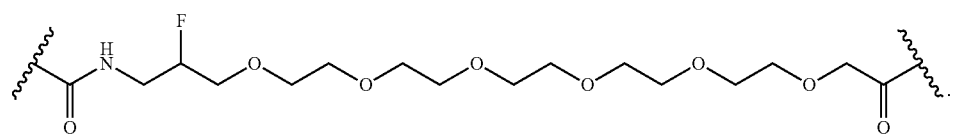 [SMILES: *C(=O)COCCOCCOCCOCCOCCOCC(F)CNC(*)=O]
In some embodiments, L is
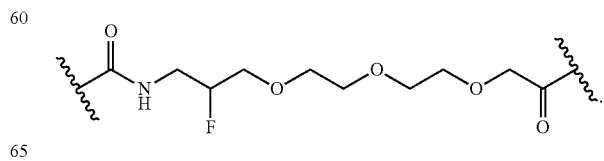

In some embodiments, L is
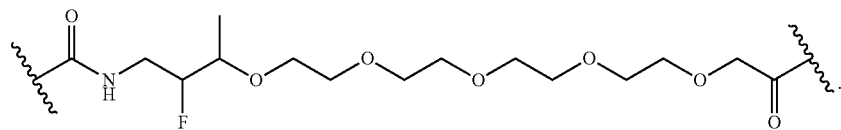 [SMILES: *C(=O)COCCOCCOCCOCCOC(C)C(F)CNC(*)=O]
In some embodiments, L is
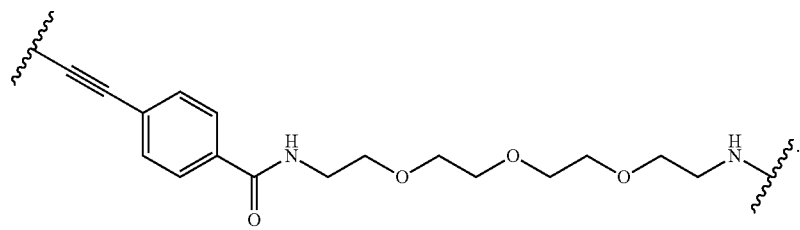 [SMILES: *C#Cc1ccc(C(=O)NCCOCCOCCOCCN*)cc1]
In some embodiments, L is
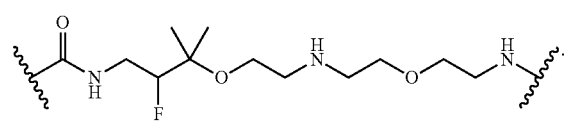 [SMILES: *NCCOCCNCCOC(C)(C)C(F)CNC(*)=O]
In some embodiments, L is
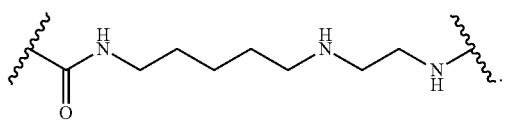
In some embodiments, L is
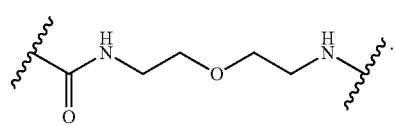 [SMILES: *NCCOCCNC(*)=O]
In some embodiments, L is
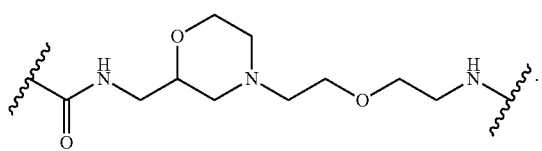 [SMILES: *NCCOCCN1CCOC(CNC(*)=O)C1]
In some embodiments, L is
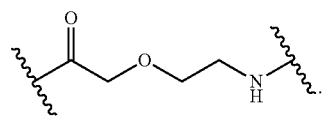 [SMILES: *NCCOCC(*)=O]
In some embodiments, L is
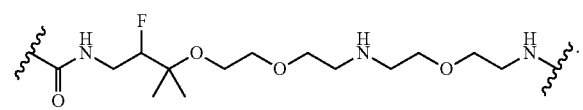
In some embodiments, L is
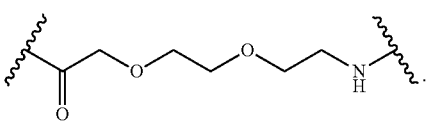 [SMILES: *NCCOCCOCC(*)=O]
In some embodiments, L is
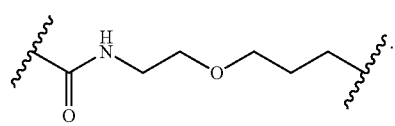
In some embodiments, L is
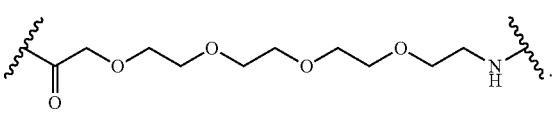 [SMILES: *NCCOCCOCCOCCOCC(*)=O]

In some embodiments, L is
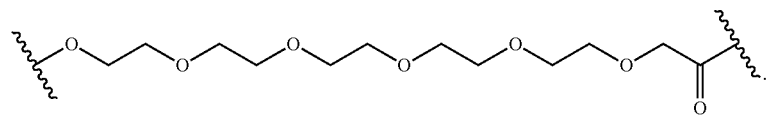 [SMILES: *OCCOCCOCCOCCOCCOCC(*)=O]
In some embodiments, L is
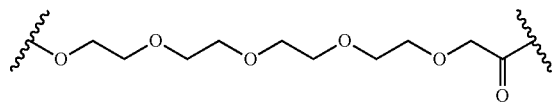
In some embodiments, L is
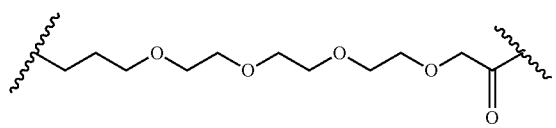
In some embodiments, L is
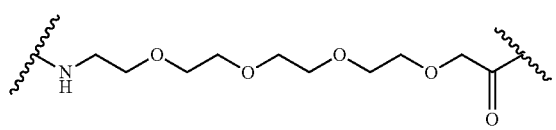
In some embodiments, L is
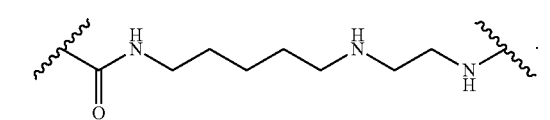 [SMILES: *NCCNCCCCCNC(*)=O]
In some embodiments, L is
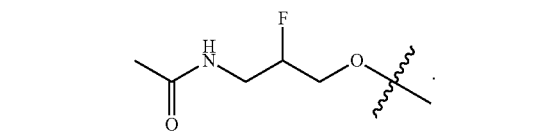 [SMILES: *OCC(F)CNC(C)=O]
In some embodiments, L is
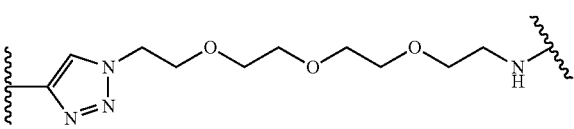 [SMILES: *NCCOCCOCCOCCn1cc(*)nn1]
In some embodiments, L is
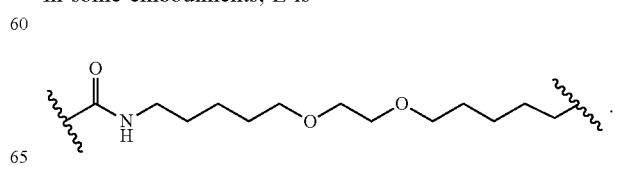
In some embodiments, L is
In some embodiments, L is
In some embodiments, L is
In some embodiments, L is
In some embodiments, L is
In some embodiments, L is In some embodiments, L is
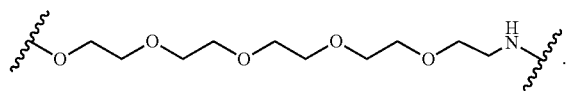 [SMILES: *NCCOCCOCCOCCOCCO*]
In some embodiments, L is
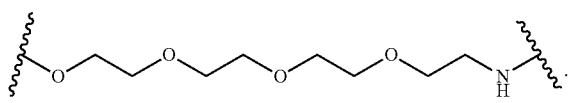 [SMILES: *NCCOCCOCCOCCO*]
In some embodiments, L is
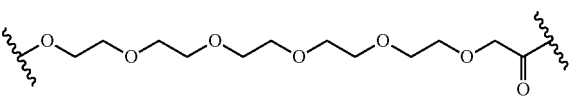 [SMILES: *OCCOCCOCCOCCOCCOCC(*)=O]
In some embodiments, L is
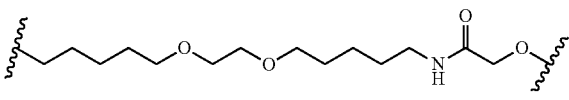 [SMILES: *CCCCCOCCOCCCCCNC(=O)CO*]
In some embodiments, L is
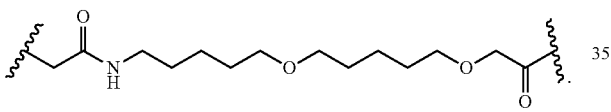
In some embodiments, L is
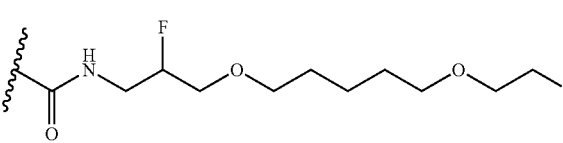
In some embodiments, L is
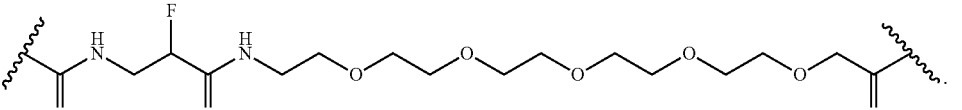
In some embodiments, L is
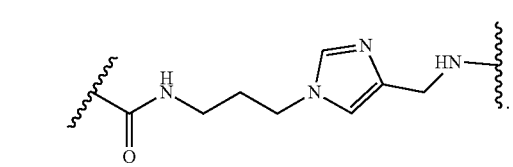 [SMILES: *NCc1cn(CCCNC(*)=O)cn1]
In some embodiments, L is
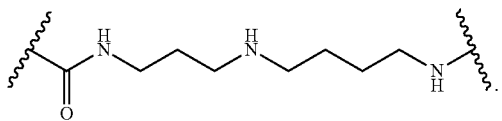 [SMILES: *NCCCCNCCCNC(*)=O]
In some embodiments, L is
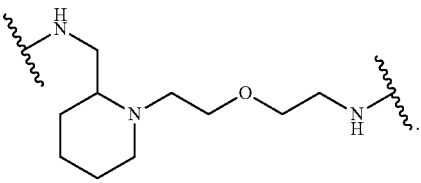 [SMILES: *NCCOCCN1CCCCC1CN*]
In some embodiments, L is
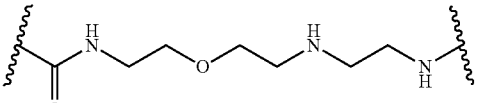
In some embodiments, L is
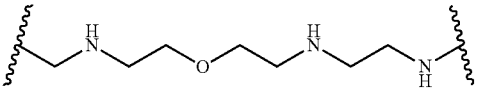
In some embodiment, L is
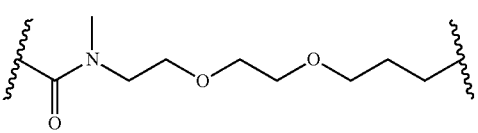

In some embodiment, L is

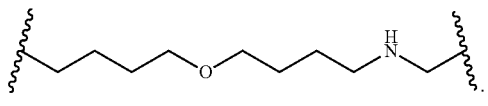 [SMILES: *CCCCOCCCCNC*]

In some embodiment, L is

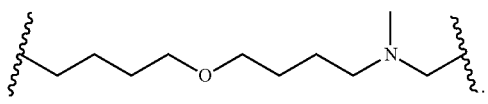 [SMILES: *CCCCOCCCCN(C)C*]

In some embodiments, L is

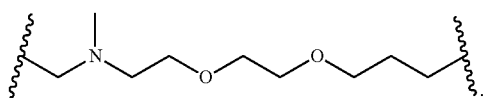 [SMILES: *CCCOCCOCCN(C)C*]

In some embodiments, L is

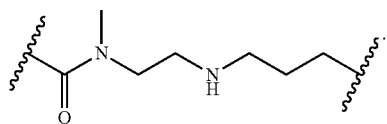 [SMILES: *CCCNCCN(C)C(*)=O]

In some embodiments, L is

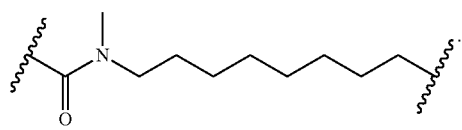 [SMILES: *CCCCCCCCN(C)C(*)=O]

In some embodiments, L is

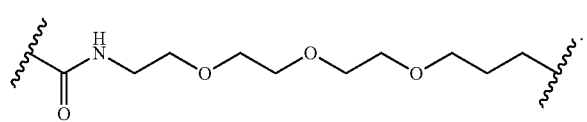 [SMILES: *CCCOCCOCCOCCNC(*)=O]

In some embodiments, L is

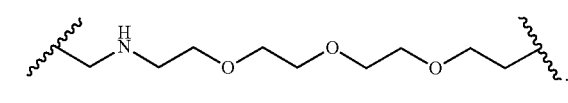 [SMILES: *CCOCCOCCOCCNC*]

In some embodiments, L is

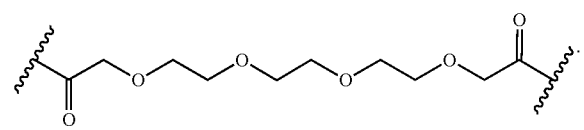 [SMILES: *C(=O)COCCOCCOCCOCC(*)=O]

In some embodiments, L is

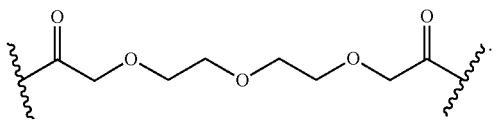 [SMILES: *C(=O)COCCOCCOCC(*)=O]

In some embodiments, L is

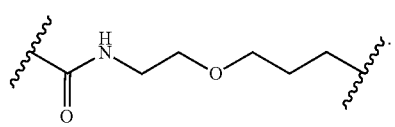 [SMILES: *CCCOCCNC(*)=O]

In some embodiments, L is

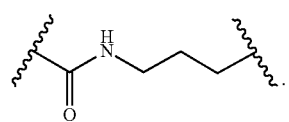

In some embodiments, L is

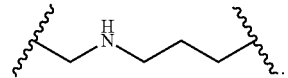 [SMILES: *CCCNC*]

In some embodiments, L is

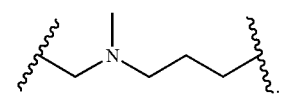 [SMILES: *CCCN(C)C*]

In some embodiments, L is

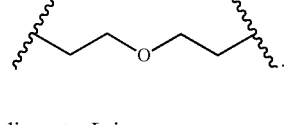

In some embodiments, L is

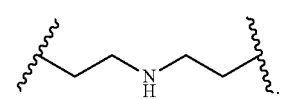 [SMILES: *CCNCC*]

In some embodiments, L is

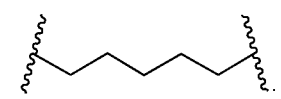 [SMILES: *CCCCC*]

In some embodiments, L is
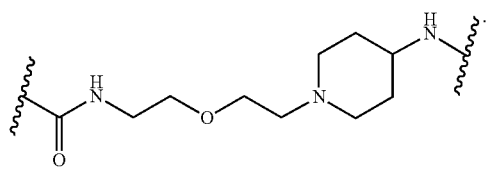 [SMILES: *NC1CCN(CCOCCNC(*)=O)CC1]
In some embodiments, L is
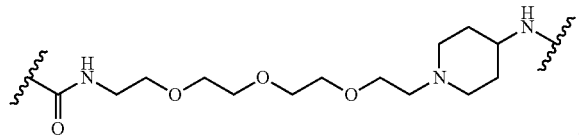
In some embodiments, L is
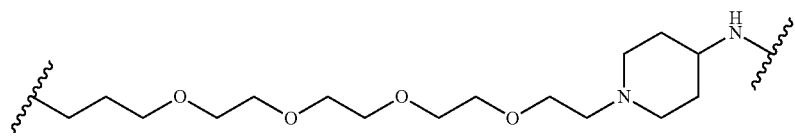
In some embodiments, L is
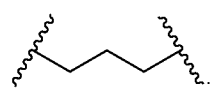 [SMILES: *CCC*]
In some embodiments, L is
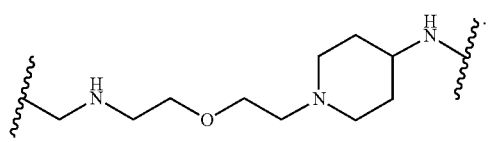 [SMILES: *CNCCOCCN1CCC(N*)CC1]
In some embodiments, L is
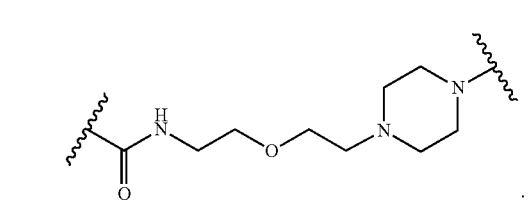
In some embodiments, L is
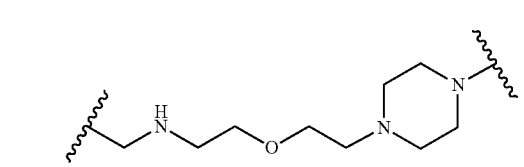
In some embodiments, L is
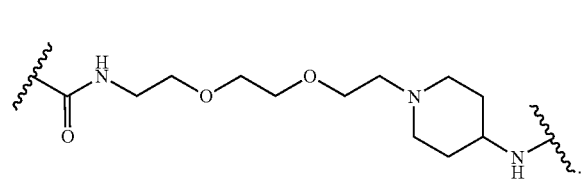 [SMILES: *NC1CCN(CCOCCOCCNC(*)=O)CC1]
In some embodiments, L is
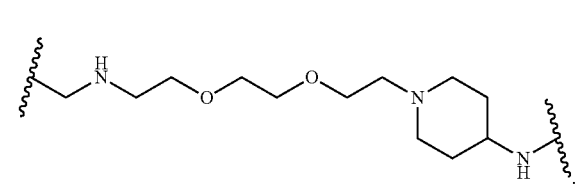 [SMILES: *CNCCOCCOCCN1CCC(N*)CC1]
In some embodiments, L is
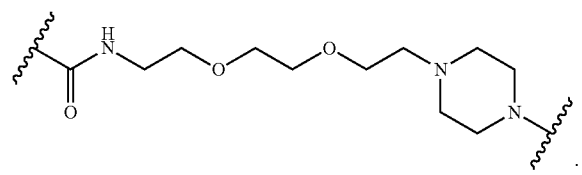

In some embodiments, L is

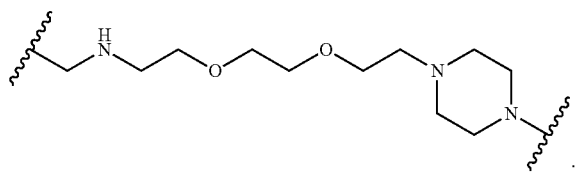

In some embodiments, L is

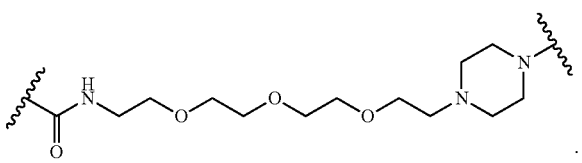 [SMILES: *C(=O)NCCOCCOCCOCCN1CCN(*)CC1]

In some embodiments, L is

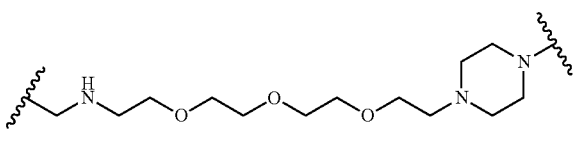

In some embodiments, L is

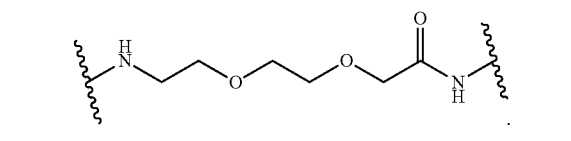 [SMILES: *NCCOCCOCC(=O)N*]

In some embodiments, L is

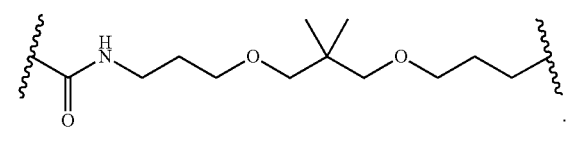 [SMILES: *CCCOCC(C)(C)COCCCNC(*)=O]

In some embodiments, L is

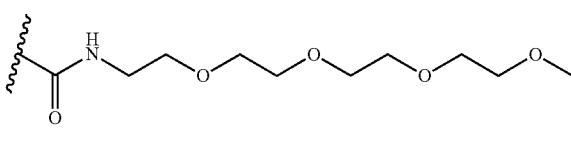

In some embodiments, L is

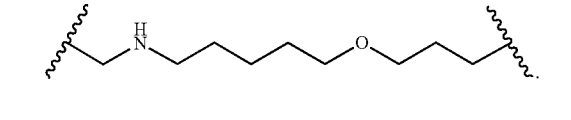 [SMILES: *CCCOCCCCCNC*]

In some embodiments, L is

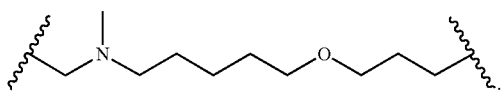 [SMILES: *CCCOCCCCCN(C)C*]

In some embodiments, L is

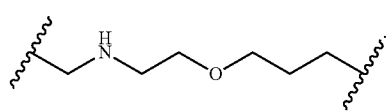

In some embodiments, L is

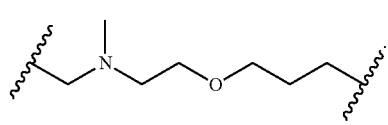

In some embodiments, L is

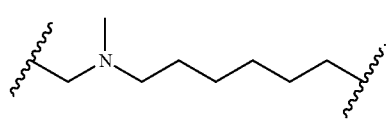

In some embodiments, L is

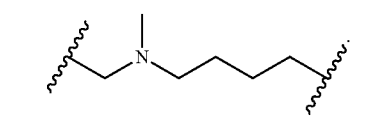

In some embodiments, L is

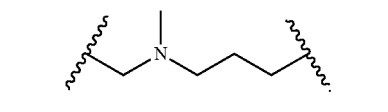

In some embodiments, L is

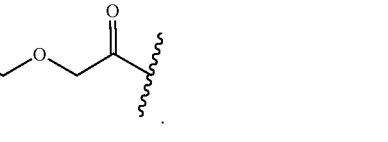

In some embodiments, L is

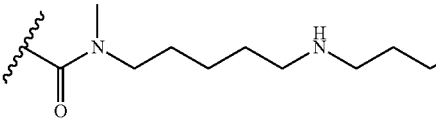

In some embodiments, L is

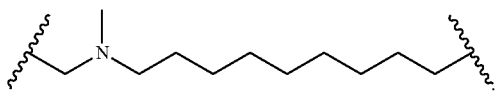

In some embodiments, L is

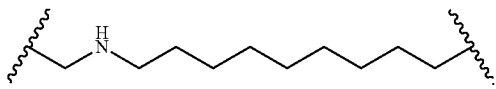

In some embodiments, L is

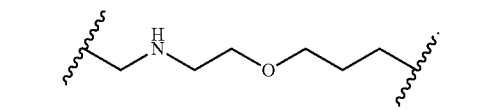

In some embodiments, L is

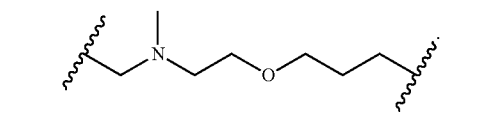

In some embodiments, L is

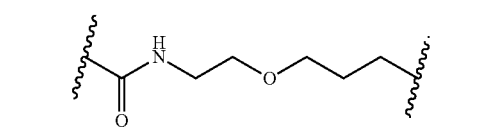

In some embodiments, L is

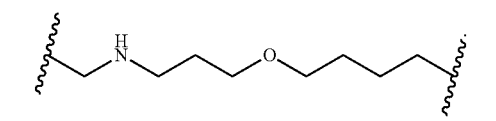

In some embodiments, L is

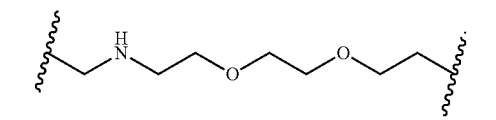

In some embodiments, L is

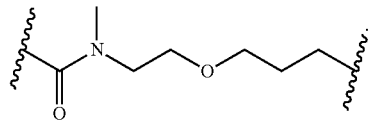

In some embodiments, L is

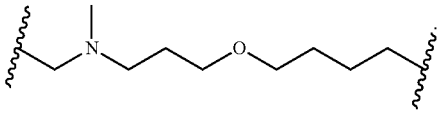

In some embodiments, L is

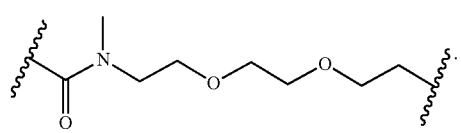 [SMILES: *CCOCCOCCN(C)C(*)=O]

In some embodiments, L is

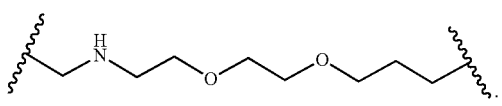 [SMILES: *CCCOCCOCCNC*]

In some embodiments, L is

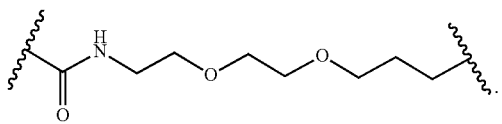 [SMILES: *CCCOCCOCCNC(*)=O]

In some embodiments, L is

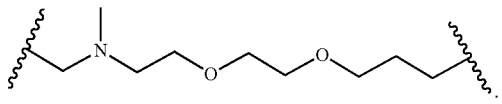 [SMILES: *CCCOCCOCCN(C)C*]

In some embodiments, L is

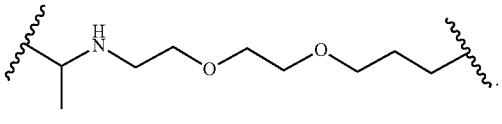 [SMILES: *CCCOCCOCCNC(*)C]

In some embodiments, L is

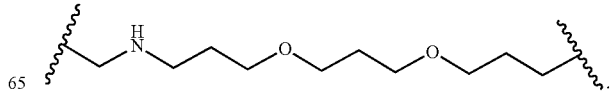

In some embodiment, L is
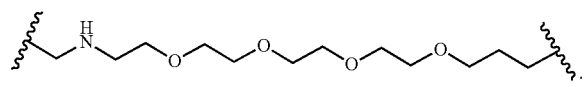 [SMILES: *CCCOCCOCCOCCOCCNC*]
In some embodiment, L is
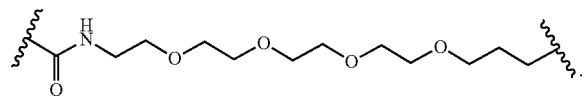 [SMILES: *CCCOCCOCCOCCOCCNC(*)=O]
In some embodiments, L is
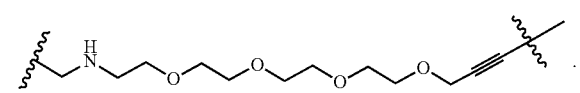 [SMILES: *C#CCOCCOCCOCCOCCNC*]
In some embodiments, L is
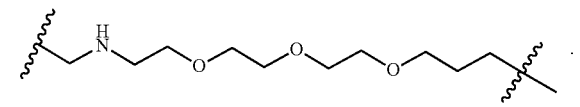 [SMILES: *CCCOCCOCCOCCNC*]
In some embodiments, L is
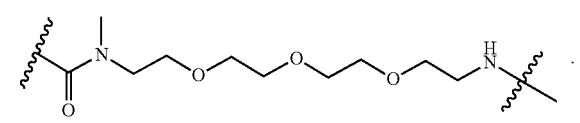 [SMILES: *NCCOCCOCCOCCN(C)C(*)=O]
In some embodiments, L is
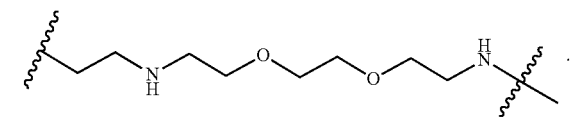 [SMILES: *CCNCCOCCOCCN*]
In some embodiments, L is
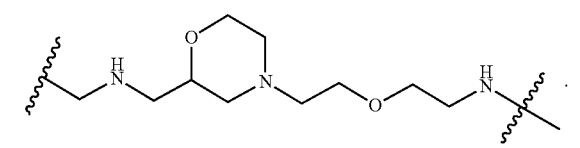 [SMILES: *CNCC1CN(CCOCCN*)CCO1]
In some embodiments, L is
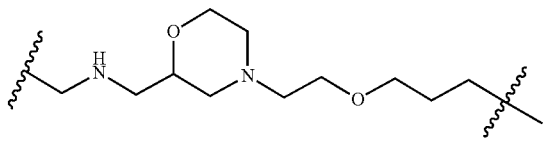
In some embodiments, L is
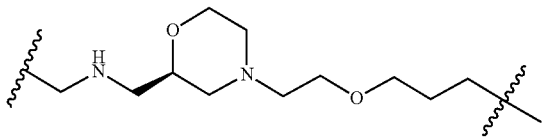
In some embodiments, L is
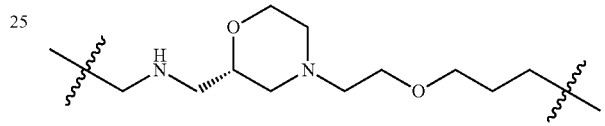
In some embodiments, L is
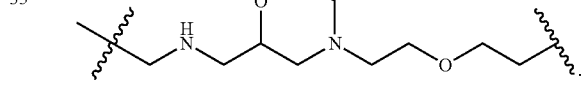
In some embodiments, L is
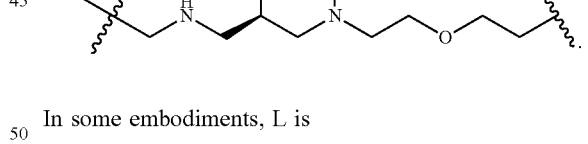
In some embodiments, L is
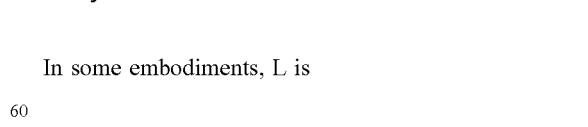
In some embodiments, L is
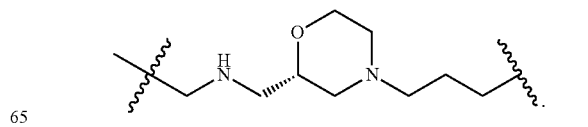

In some embodiments, L is
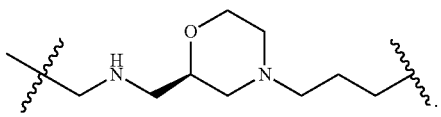 [SMILES: *CCCN1CCO[C@H](CNC*)C1]
In some embodiments, L is
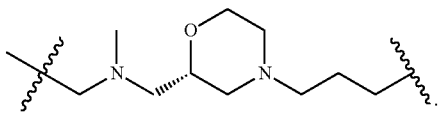 [SMILES: *CCCN1CCO[C@@H](CN(C)C*)C1]
In some embodiments, L is
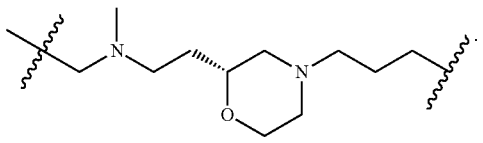 [SMILES: *CCCN1CCO[C@H](CCN(C)C*)C1]
In some embodiments, L is
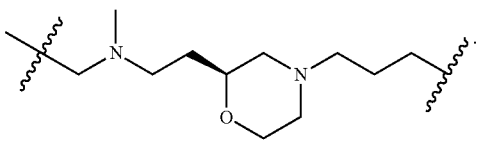 [SMILES: *CCCN1CCO[C@@H](CCN(C)C*)C1]
In some embodiments, L is
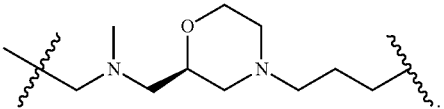 [SMILES: *CCCN1CCO[C@H](CN(C)C*)C1]
In some embodiments, L is
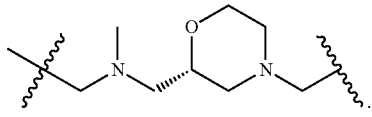 [SMILES: *CN(C)C[C@H]1CN(C*)CCO1]
In some embodiments, L is
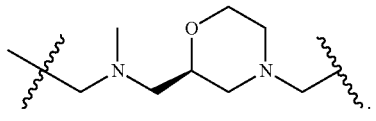 [SMILES: *CN(C)C[C@@H]1CN(C*)CCO1]
In some embodiments, L is
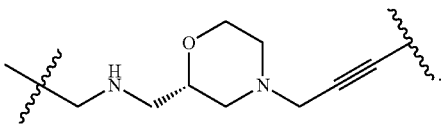 [SMILES: *C#CCN1CCO[C@@H](CNC*)C1]
In some embodiments, L is
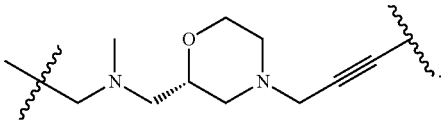 [SMILES: *C#CCN1CCO[C@@H](CN(C)C*)C1]
In some embodiments, L is
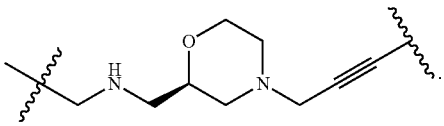 [SMILES: *C#CCN1CCO[C@H](CNC*)C1]
In some embodiments, L is
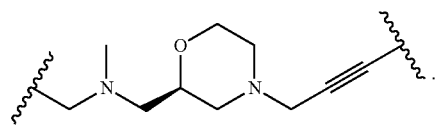 [SMILES: *C#CCN1CCO[C@H](CN(C)C*)C1]
In some embodiments, L is
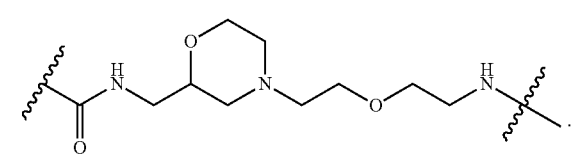 [SMILES: *NCCOCCN1CCOC(CNC(*)=O)C1]
In some embodiments, L is
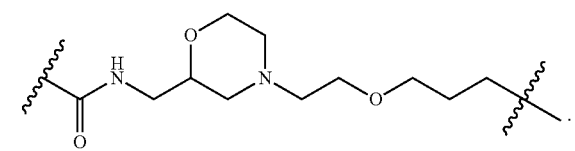 [SMILES: *CCCOCCN1CCOC(CNC(*)=O)C1]
In some embodiments, L is
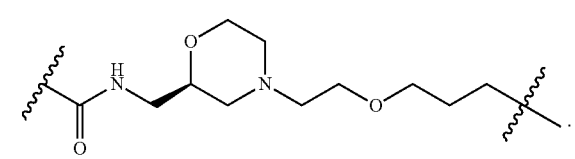 [SMILES: *CCCOCCN1CCO[C@H](CNC(*)=O)C1]

In some embodiments, L is
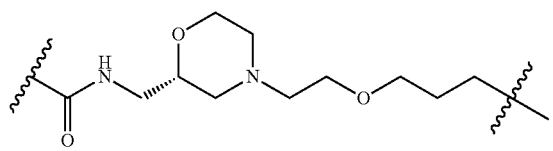
In some embodiments, L is
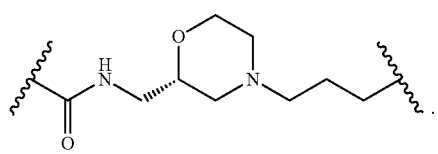 [SMILES: *CCCN1CCO[C@@H](CNC(*)=O)C1]
In some embodiments, L is
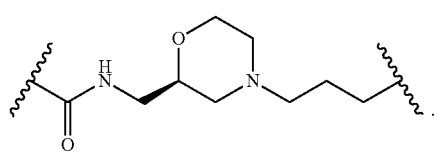 [SMILES: *CCCN1CCO[C@H](CNC(*)=O)C1]
In some embodiments, L is
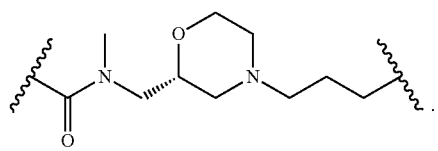 [SMILES: *CCCN1CCO[C@@H](CN(C)C(*)=O)C1]
In some embodiments, L is
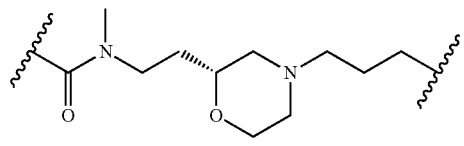
In some embodiments, L is
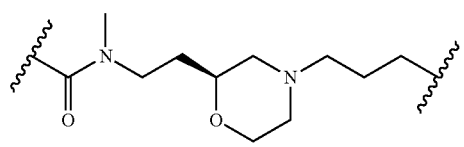
In some embodiments, L is
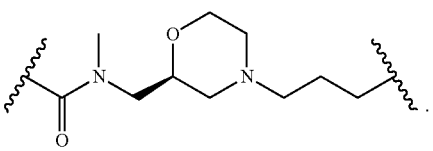 [SMILES: *CCCN1CCO[C@H](CN(C)C(*)=O)C1]
In some embodiments, L is
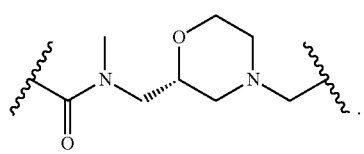 [SMILES: *CN1CCO[C@@H](CN(C)C(*)=O)C1]
In some embodiments, L is
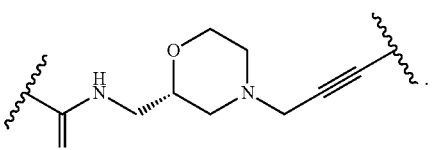
In some embodiments, L is
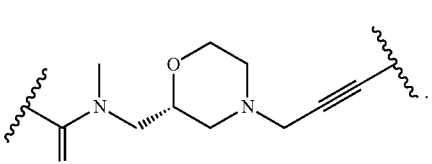
In some embodiments, L is
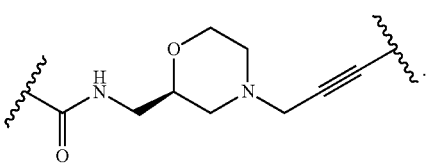 [SMILES: *C#CCN1CCO[C@H](CNC(*)=O)C1]
In some embodiments, L is
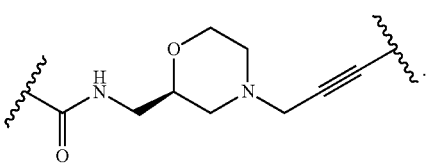 [SMILES: *C#CCN1CCO[C@H](CNC(*)=O)C1]

In some embodiments, L is
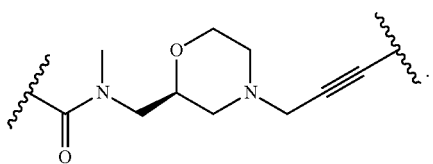 [SMILES: *C#CCN1CCO[C@H](CN(C)C(*)=O)C1]
In some embodiments, L is
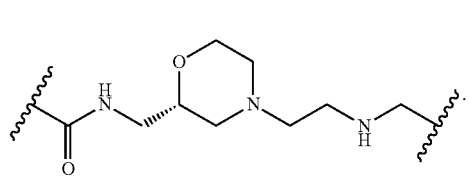 [SMILES: *CNCCN1CCO[C@@H](CNC(*)=O)C1]
In some embodiments, L is
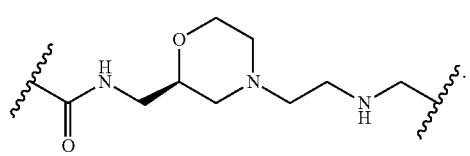
In some embodiments, L is
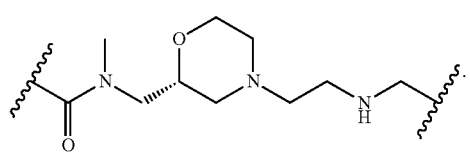 [SMILES: *CNCCN1CCO[C@@H](CN(C)C(*)=O)C1]
In some embodiments, L is
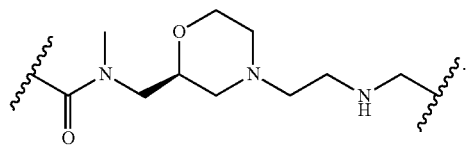 [SMILES: *CNCCN1CCO[C@H](CN(C)C(*)=O)C1]
In some embodiments, L is
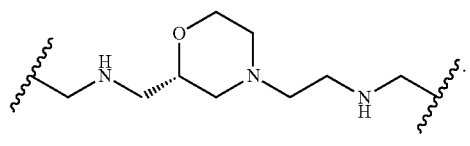
In some embodiments, L is
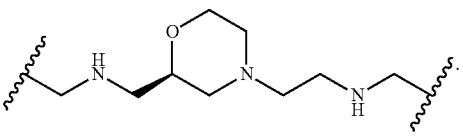 [SMILES: *CNCCN1CCO[C@H](CNC*)C1]
In some embodiments, L is
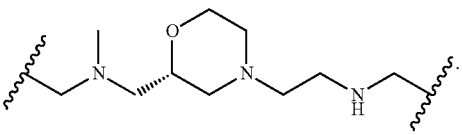 [SMILES: *CNCCN1CCO[C@@H](CN(C)C*)C1]
In some embodiments, L is
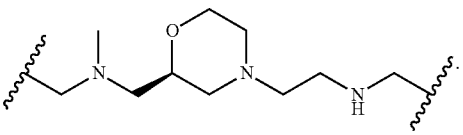 [SMILES: *CNCCN1CCO[C@H](CN(C)C*)C1]
In some embodiments, L is
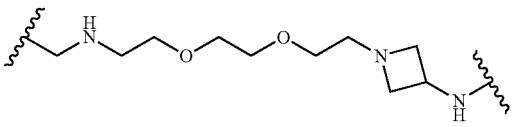
In some embodiments, L is
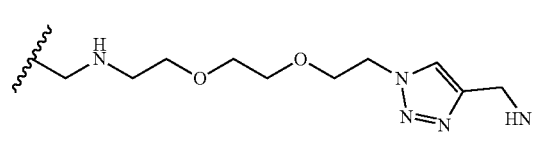
In some embodiments, L is
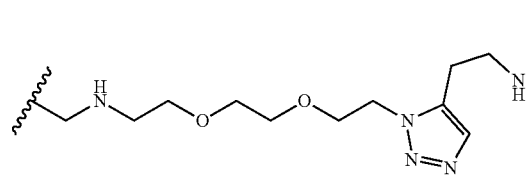
In some embodiments, L is
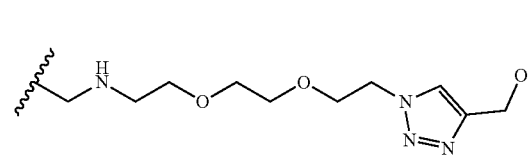

In some embodiments, L is
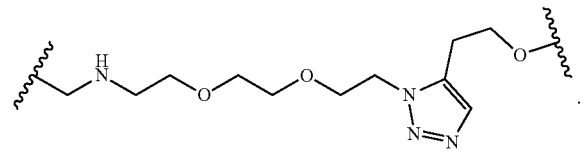 [SMILES: *CNCCOCCOCCn1nncc1CCO*]
In some embodiments, L is
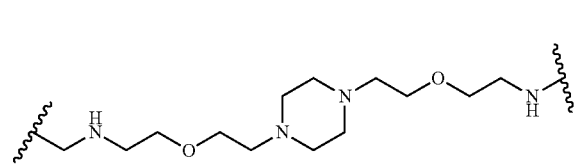
In some embodiments, L is
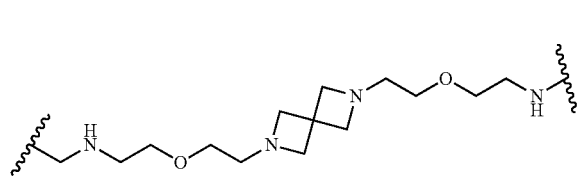
In some embodiments, L is
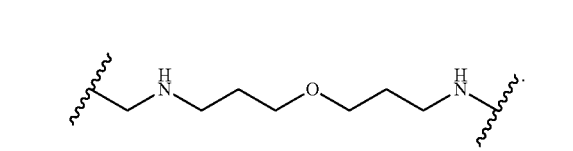 [SMILES: *CNCCCOCCCN*]
In some embodiments, L is
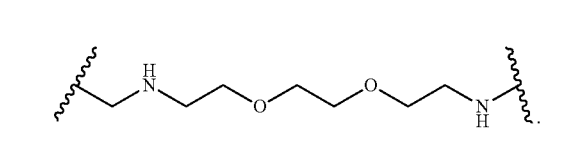 [SMILES: *CNCCOCCOCCN*]
In some embodiments, L is
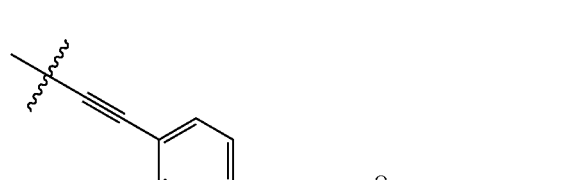
In some embodiments, L is
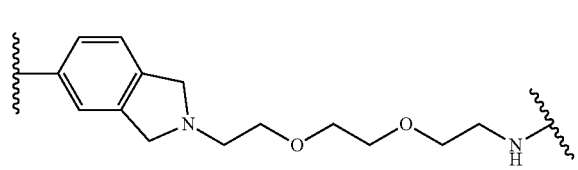
In some embodiments, L is
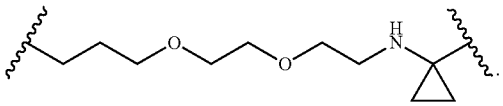 [SMILES: *CCCOCCOCCNC1(*)CC1]
In some embodiments, L is
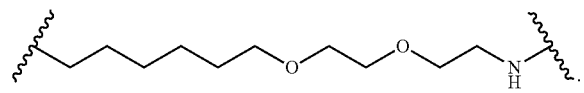 [SMILES: *CCCCCCOCCOCCN*]
In some embodiments, L is
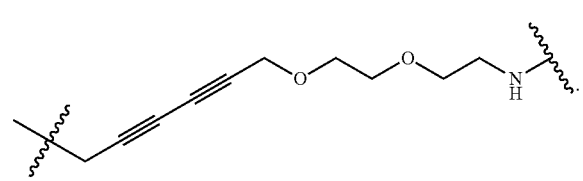 [SMILES: *CC#CC#CCOCCOCCN*]
In some embodiments, L is
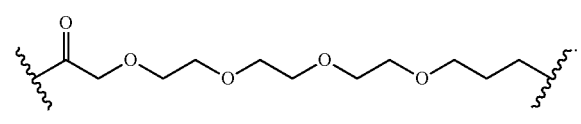 [SMILES: *CCCOCCOCCOCCOCC(*)=O]
In some embodiments, L is
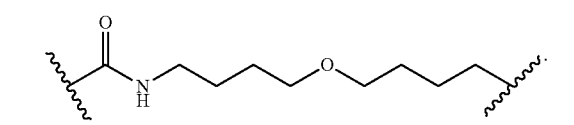 [SMILES: *CCCCOCCCCNC(*)=O]
In some embodiments, L is
In some embodiments, L is
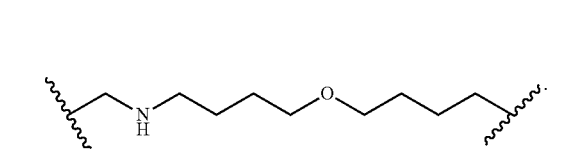 [SMILES: *CCCCOCCCCNC*]

In some embodiments, L is

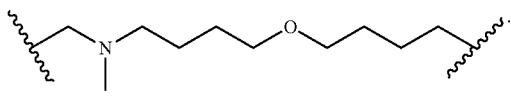 [SMILES: *CCCCOCCCCN(C)C*]

In some embodiments, L is

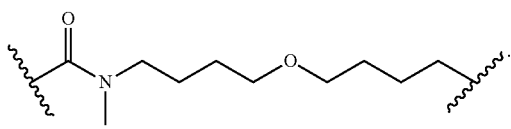 [SMILES: *CCCCOCCCCN(C)C(*)=O]

In some embodiments, L is

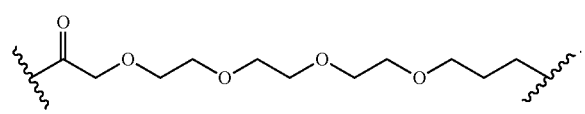 [SMILES: *CCCOCCOCCOCCOCC(*)=O]

In some embodiments, L is

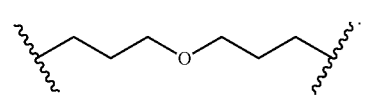 [SMILES: *CCCOCCC*]

In some embodiments, L is

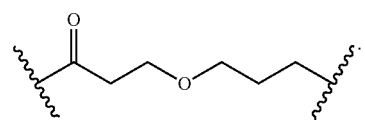 [SMILES: *CCCOCCC(*)=O]

In some embodiments, L is

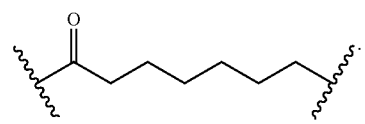 [SMILES: *CCCCCCC(*)=O]

In some embodiments, L is

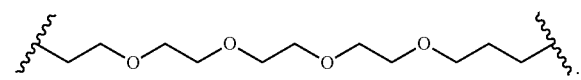 [SMILES: *CCCOCCOCCOCCOCC*]

In some embodiments, L is

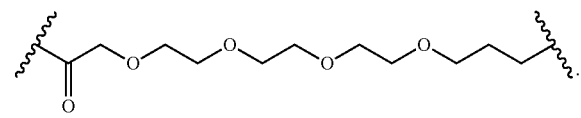 [SMILES: *CCCOCCOCCOCCOCC(*)=O]

In some embodiments, L is

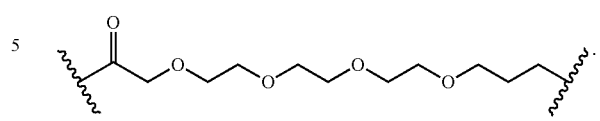

In some embodiments, L is

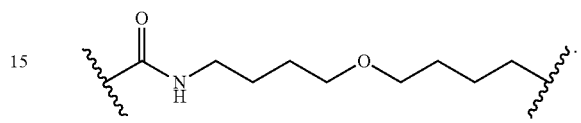

In some embodiments, L is

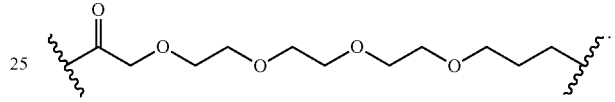

In some embodiments, L is

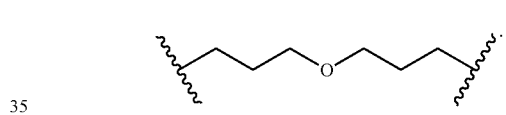

In some embodiments, L is

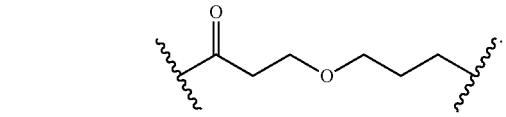 [SMILES: *CCCOCCC(*)=O]

In some embodiments, L is

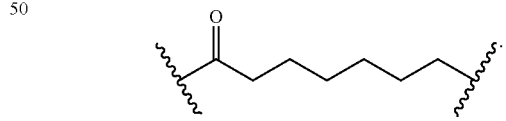

In some embodiments, L is

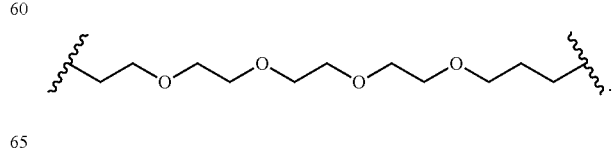

In some embodiments, L is
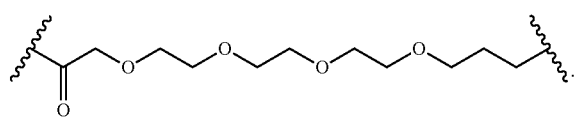 [SMILES: *CCCOCCOCCOCCOCC(*)=O]
In some embodiments, L is
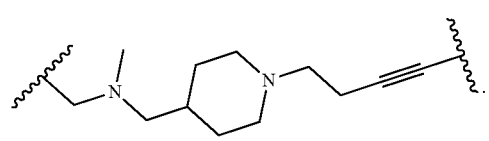 [SMILES: *C#CCCN1CCC(CN(C)C*)CC1]
In some embodiments, L is
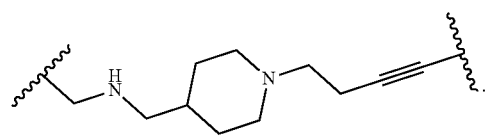 [SMILES: *C#CCCN1CCC(CNC*)CC1]
In some embodiments, L is
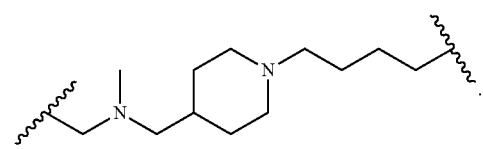 [SMILES: *CCCCN1CCC(CN(C)C*)CC1]
In some embodiments, L is
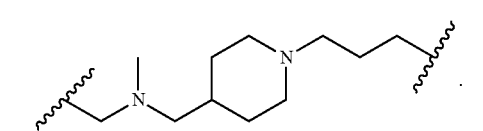 [SMILES: *CCCN1CCC(CN(C)C*)CC1]
In some embodiments, L is
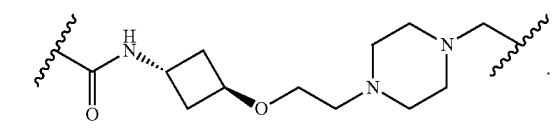 [SMILES: *CN1CCN(CCO[C@H]2C[C@H](NC(*)=O)C2)CC1]
In some embodiments, L is
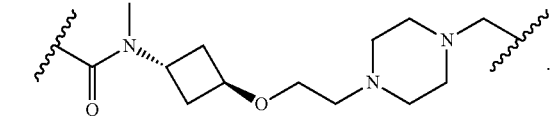 [SMILES: *CN1CCN(CCO[C@H]2C[C@H](N(C)C(*)=O)C2)CC1]
In some embodiments, L is
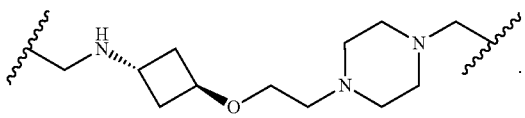 [SMILES: *CN[C@H]1C[C@H](OCCN2CCN(C*)CC2)C1]
In some embodiments, L is
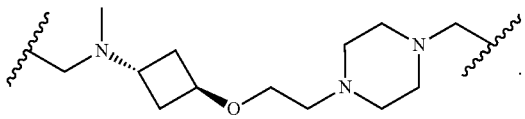 [SMILES: *CN1CCN(CCO[C@H]2C[C@H](N(C)C*)C2)CC1]
In some embodiments, L is
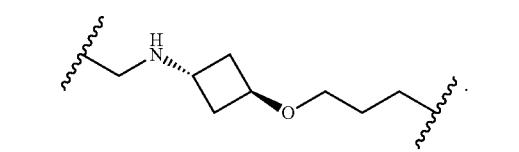 [SMILES: *CCCO[C@H]1C[C@H](NC*)C1]
In some embodiments, L is
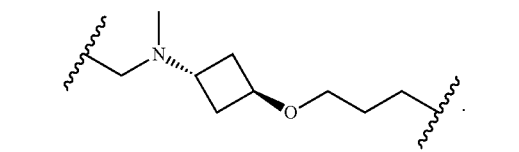 [SMILES: *CCCO[C@H]1C[C@H](N(C)C*)C1]
In some embodiments, L is
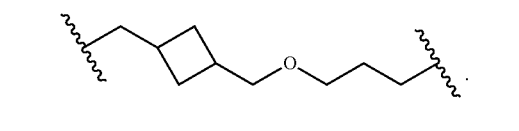 [SMILES: *CCCOCC1CC(C*)C1]
In some embodiments, L is
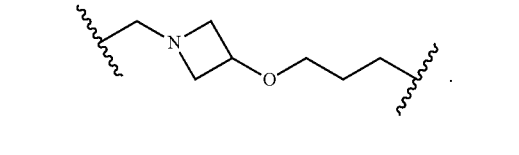 [SMILES: *CCCOC1CN(C*)C1]
In some embodiments, L is
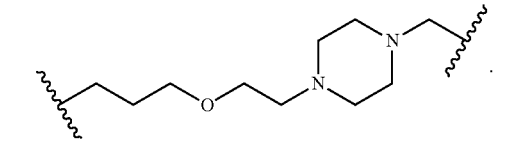 [SMILES: *CCCOCCN1CCN(C*)CC1]

In some embodiments, L is
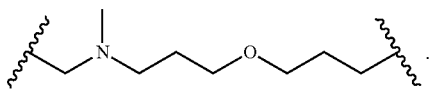
In some embodiments, L is
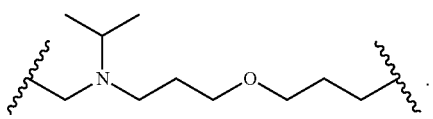 [SMILES: *CCCOCCCN(C*)C(C)C]
In some embodiments, L is
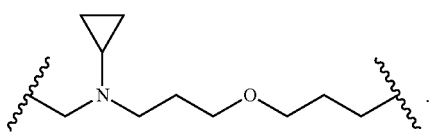 [SMILES: *CCCOCCCN(C*)C1CC1]
In some embodiments, L is
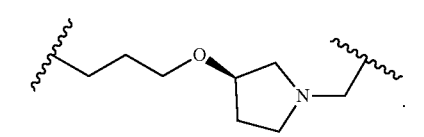 [SMILES: *CCCO[C@@H]1CCN(C*)C1]
In some embodiments, L is
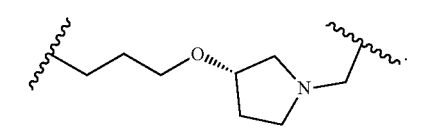 [SMILES: *CCCO[C@H]1CCN(C*)C1]
In some embodiments, L is
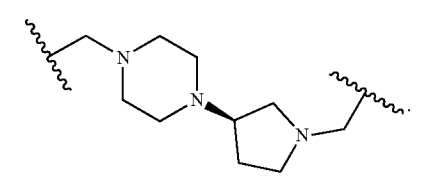 [SMILES: *CN1CCN([C@@H]2CCN(C*)C2)CC1]
In some embodiments, L is
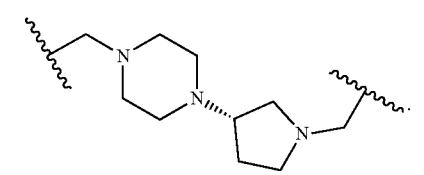 [SMILES: *CN1CCN([C@H]2CCN(C*)C2)CC1]
In some embodiments, L is
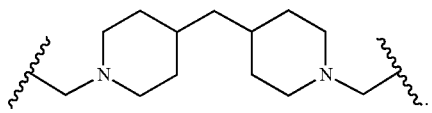 [SMILES: *CN1CCC(CC2CCN(C*)CC2)CC1]
In some embodiments, L is
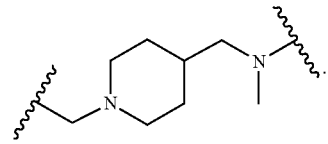
In some embodiments, L is
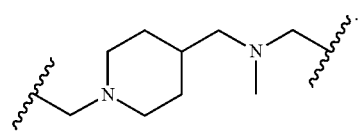 [SMILES: *CN(C)CC1CCN(C*)CC1]
In some embodiments, L is
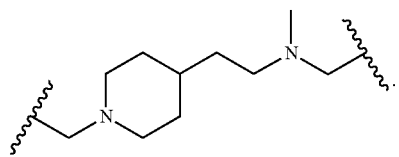 [SMILES: *CN(C)CCC1CCN(C*)CC1]
In some embodiments, L is
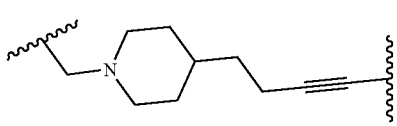
In some embodiments, L is
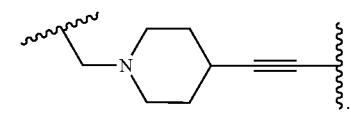
In some embodiments, L is
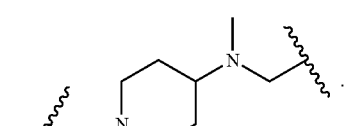

In some embodiments, L is
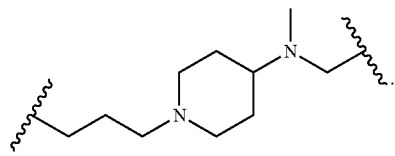 [SMILES: *CCCN1CCC(N(C)C*)CC1]
In some embodiments, L is
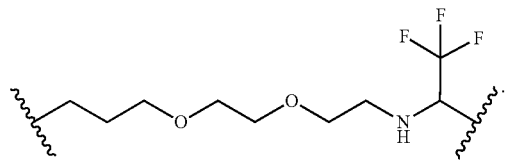 [SMILES: *CCCOCCOCCNC(*)C(F)(F)F]
In some embodiments, L is
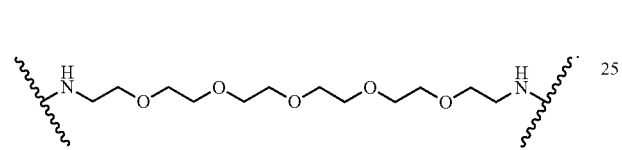
In some embodiments, L is
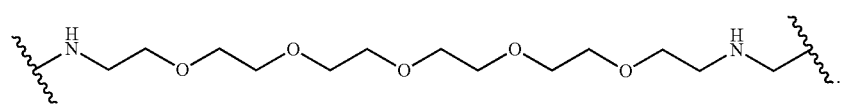 [SMILES: *CNCCOCCOCCOCCOCCOCCN*]
In some embodiments, L is
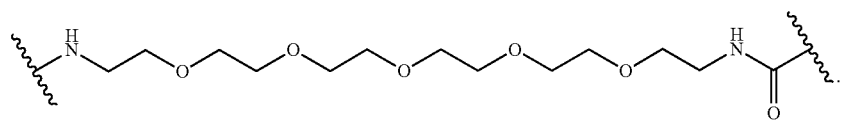 [SMILES: *NCCOCCOCCOCCOCCOCCNC(*)=O]
In some embodiments, L is
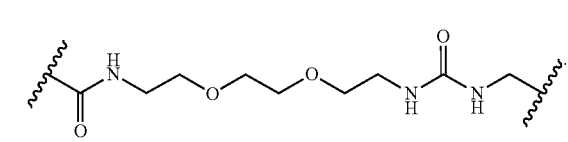 [SMILES: *CNC(=O)NCCOCCOCCNC(*)=O]
In some embodiments, L is
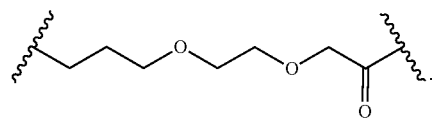 [SMILES: *CCCOCCOCC(*)=O]
In some embodiments, L is
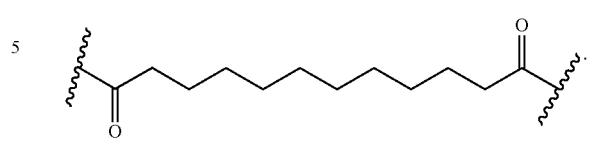
In some embodiments, L is
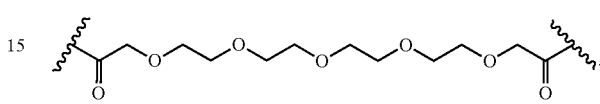
In some embodiments, L is
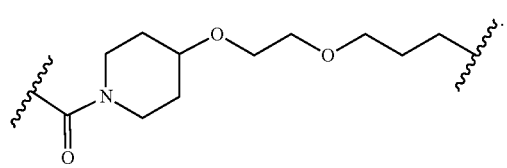 [SMILES: *CCCOCCOC1CCN(C(*)=O)CC1]
In some embodiments, L is
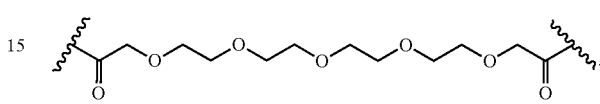
In some embodiments, L is
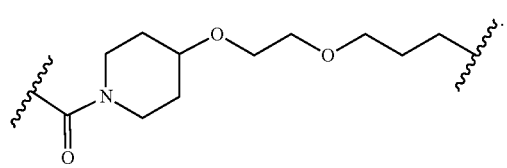 [SMILES: *CCCOCCOC1CCN(C(*)=O)CC1]

351
In some embodiments, L is
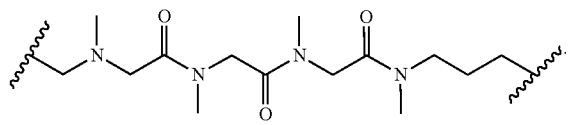 [SMILES: *CCCN(C)C(=O)CN(C)C(=O)CN(C)C(=O)CN(C)C*]
In some embodiments, L is
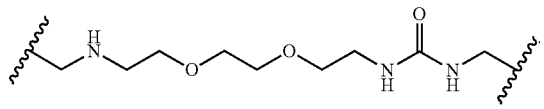 [SMILES: *CNCCOCCOCCNC(=O)NC*]
In some embodiment, L is
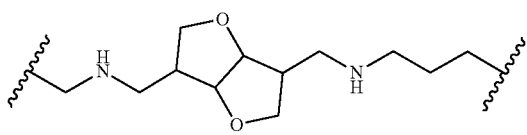
In some embodiments, L is
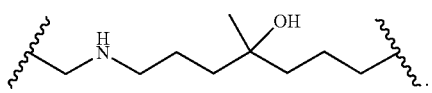 [SMILES: *CCCC(C)(O)CCCNC*]
In some embodiments, L is
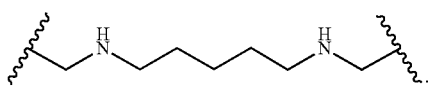 [SMILES: *CNCCCCCNC*]
In some embodiments, L is
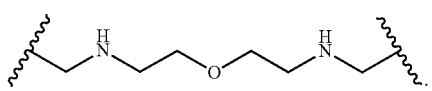 [SMILES: *CNCCOCCNC*]
In some embodiments, L is
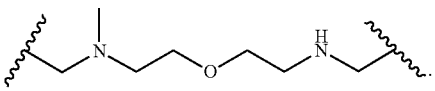 [SMILES: *CNCCOCCN(C)C*]
352
In some embodiments, L is
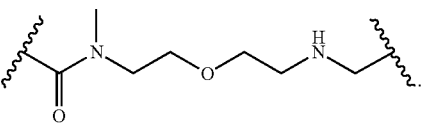 [SMILES: *CNCCOCCN(C)C(*)=O]
In some embodiments, L is
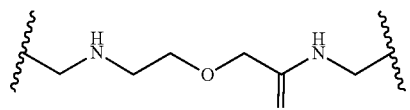
In some embodiments, L is
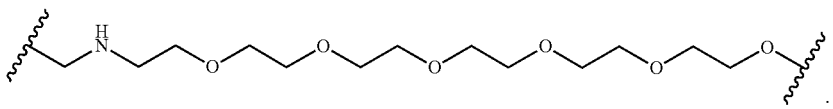 [SMILES: *CNCCOCCOCCOCCOCCOCCO*]
In some embodiments, L is
In some embodiments, L is
In some embodiments, L is
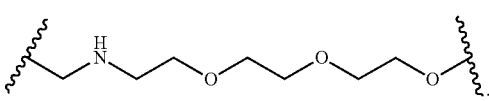 [SMILES: *CNCCOCCOCCO*]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is

[chemical structure]

In some embodiments, L is
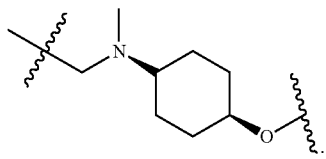
In some embodiments, L is
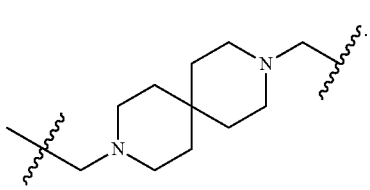 [SMILES: *CN1CCC2(CC1)CCN(C*)CC2]
In some embodiments, L is
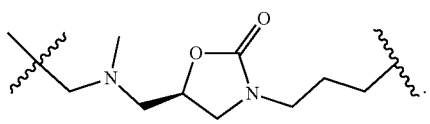 [SMILES: *CCCN1C[C@@H](CN(C)C*)OC1=O]
In some embodiments, L is
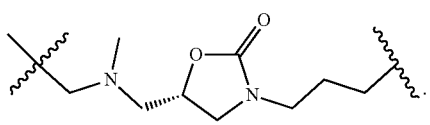 [SMILES: *CCCN1C[C@H](CN(C)C*)OC1=O]
In some embodiments, L is
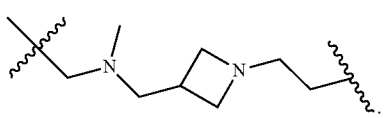 [SMILES: *CCN1CC(CN(C)C*)C1]
In some embodiments, L is
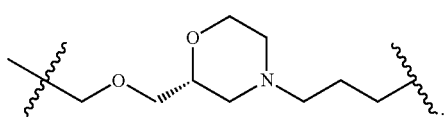 [SMILES: *CCCN1CCO[C@@H](COC*)C1]
In some embodiments, L is
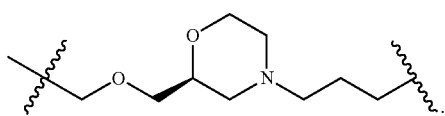 [SMILES: *CCCN1CCO[C@H](COC*)C1]
In some embodiments, L is
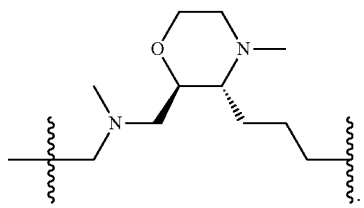 [SMILES: *CCC[C@@H]1[C@@H](CN(C)C*)OCCN1C]
In some embodiments, L is
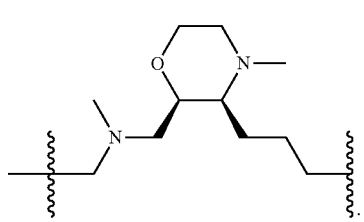 [SMILES: *CCC[C@H]1[C@@H](CN(C)C*)OCCN1C]
In some embodiments, L is
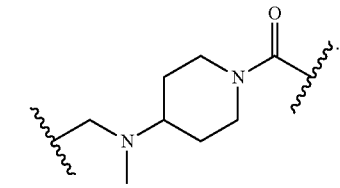 [SMILES: *CN(C)C1CCN(C(*)=O)CC1]
In some embodiments, L is
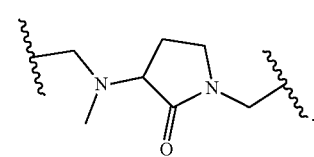 [SMILES: *CN1CCC(N(C)C*)C1=O]
In some embodiments, L is
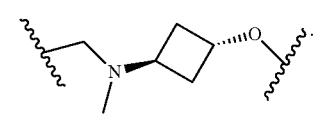 [SMILES: *CN(C)[C@H]1C[C@H](O*)C1]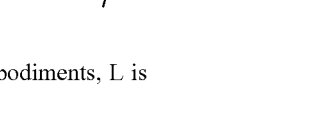
In some embodiments, L is
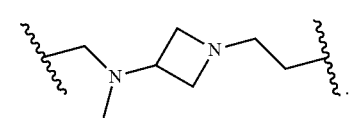 [SMILES: *CCN1CC(N(C)C*)C1]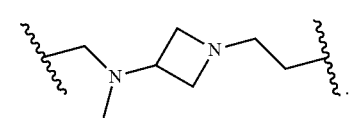 [SMILES: *CCN1CC(N(C)C*)C1]

In some embodiments, L is

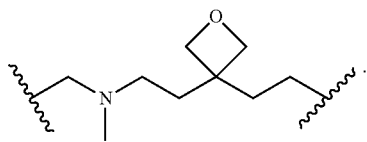 [SMILES: *CCC1(CCN(C)C*)COC1]

In some embodiments, L is

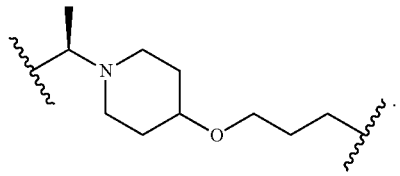 [SMILES: *CCCOC1CCN([C@@H](*)C)CC1]

In some embodiments, L is

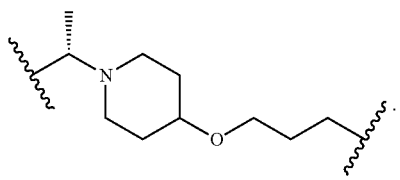 [SMILES: *CCCOC1CCN([C@H](*)C)CC1]

In some embodiments, L is

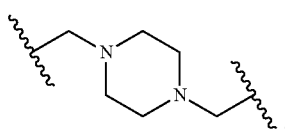

In some embodiments, L is

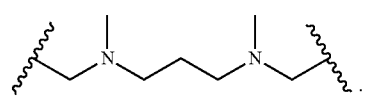 [SMILES: *CN(C)CCCN(C)C*]

In some embodiments, L is

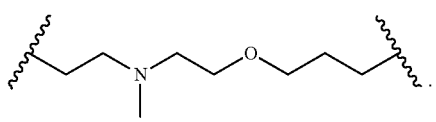 [SMILES: *CCCOCCN(C)CC*]

In some embodiments, L is

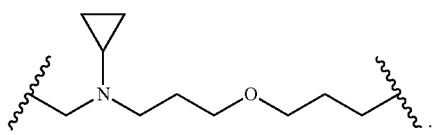 [SMILES: *CCCOCCCN(C*)C1CC1]

In some embodiments, L is

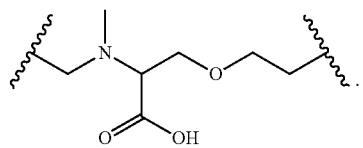 [SMILES: *CCOCC(C(=O)O)N(C)C*]

In some embodiments, L is

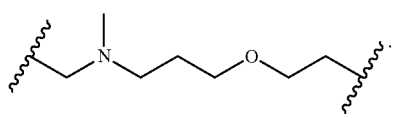 [SMILES: *CCOCCCN(C)C*]

In some embodiments, L is

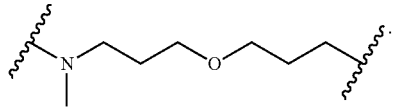 [SMILES: *CCCOCCCN(*)C]

In some embodiments, L is

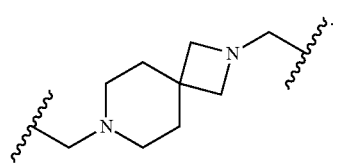 [SMILES: *CN1CCC2(CC1)CN(C*)C2]

In some embodiments, L is

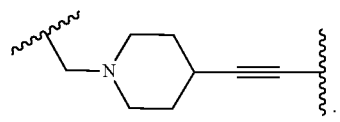 [SMILES: *C#CC1CCN(C*)CC1]

In some embodiments, L is

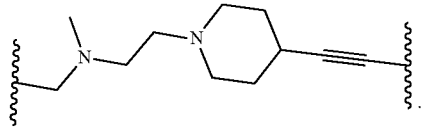 [SMILES: *C#CC1CCN(CCN(C)C*)CC1]

In some embodiments, L is

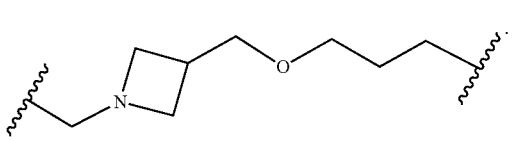 [SMILES: *CCCOCC1CN(C*)C1]

In some embodiments, L is a covalent bond. In some embodiments, L is

In some embodiments, L is

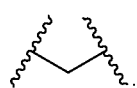 [SMILES: *C*]

In some embodiments, L is

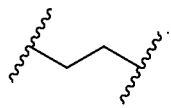

In some embodiments, L is

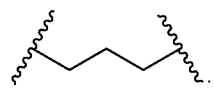 [SMILES: *CCC*]

In some embodiments, L is

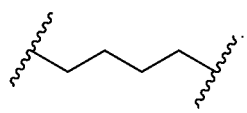

In some embodiments, L is

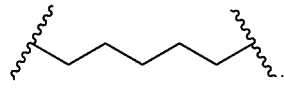 [SMILES: *CCCCC*]

In some embodiments, L is

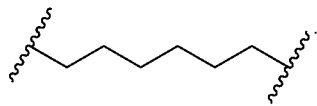 [SMILES: *CCCCCC*]

In some embodiments, L is

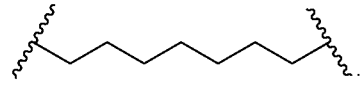 [SMILES: *CCCCCCC*]

In some embodiments, L is

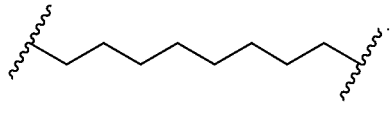 [SMILES: *CCCCCCCC*]

In some embodiments, L is

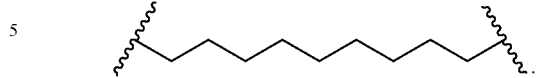

In some embodiments, L is a covalent bond. In some embodiments, L is

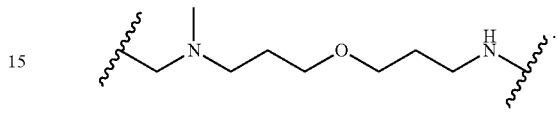

In some embodiments, L is

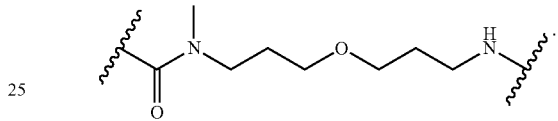

In some embodiments, L is

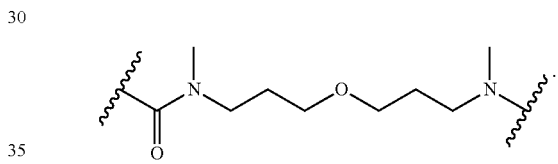

In some embodiments, L is

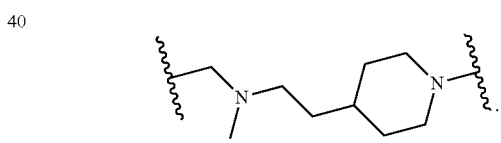

In some embodiments, L is

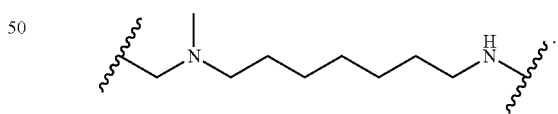

In some embodiments, L is

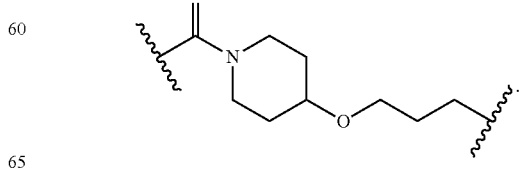

In some embodiments, L is
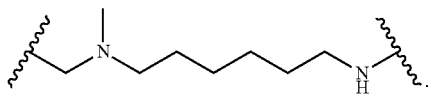 [SMILES: *CN(C)CCCCCCN*]
In some embodiments, L is
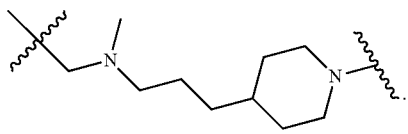 [SMILES: *CN(C)CCCC1CCN(*)CC1]
In some embodiments, L is
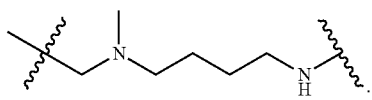 [SMILES: *CN(C)CCCCN*]
In some embodiments, L is
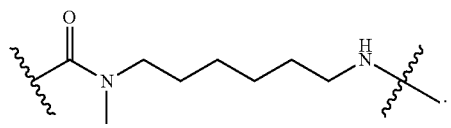 [SMILES: *NCCCCCCN(C)C(*)=O]
In some embodiments, L is
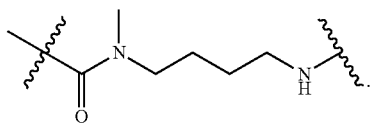 [SMILES: *NCCCCN(C)C(*)=O]
In some embodiments, L is
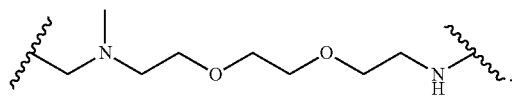 [SMILES: *CN(C)CCOCCOCCN*]
In some embodiments, L is
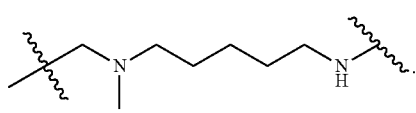 [SMILES: *CN(C)CCCCCN*]
In some embodiments, L is
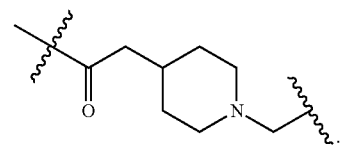 [SMILES: *CN1CCC(CC(*)=O)CC1]
In some embodiments, L is
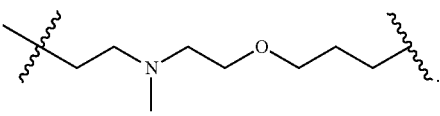 [SMILES: *CCCOCCN(C)CC*]
In some embodiments, L is
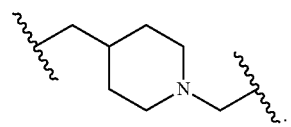 [SMILES: *CC1CCN(C*)CC1]
In some embodiments, L is
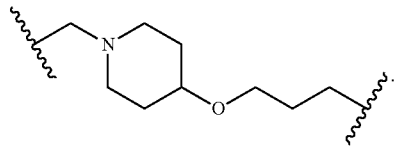 [SMILES: *CCCOC1CCN(C*)CC1]
In some embodiments, L is
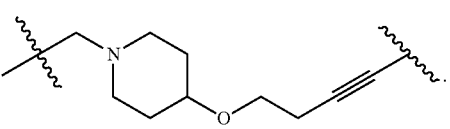 [SMILES: *C#CCCOC1CCN(C*)CC1]
In some embodiments, L is
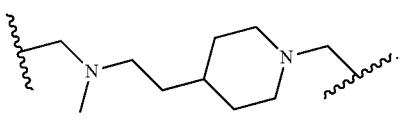 [SMILES: *CN(C)CCC1CCN(C*)CC1]
In some embodiments, L is
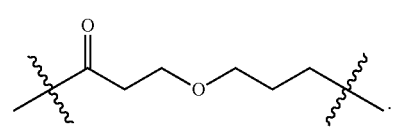 [SMILES: *CCCOCCC(*)=O]

In some embodiments, L is
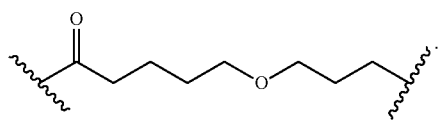 [SMILES: *CCCOCCCCC(*)=O]
In some embodiments, L is
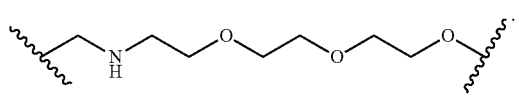 [SMILES: *CNCCOCCOCCO*]
In some embodiments, L is
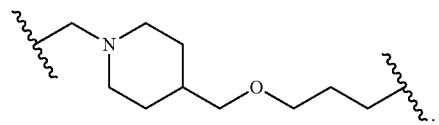 [SMILES: *CCCOCC1CCN(C*)CC1]
In some embodiments, L is
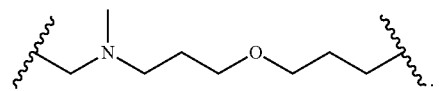 [SMILES: *CCCOCCCN(C)C*]
In some embodiments, L is
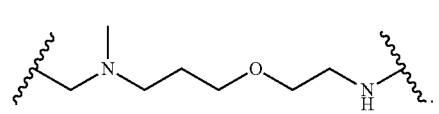 [SMILES: *CN(C)CCCOCCN*]
In some embodiments, L is
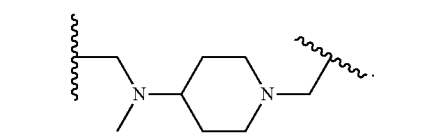 [SMILES: *CN1CCC(N(C)C*)CC1]
In some embodiments, L is
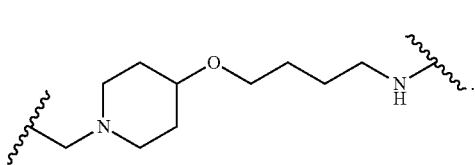 [SMILES: *CN1CCC(OCCCCN*)CC1]
In some embodiments, L is
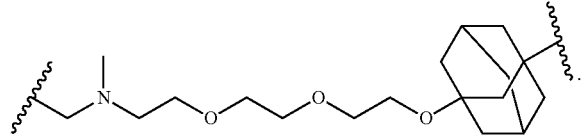 [SMILES: *CN(C)CCOCCOCCOC12CC3CC(CC(*)(C3)C1)C2]
In some embodiments, L is
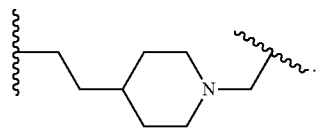 [SMILES: *CCC1CCN(C*)CC1]
In some embodiments, L is
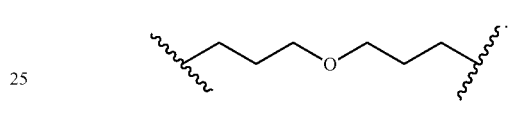
In some embodiments, L is
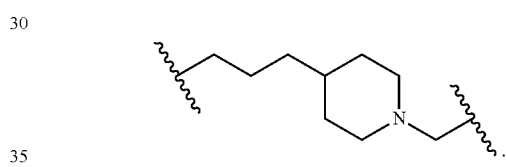
In some embodiments, L is
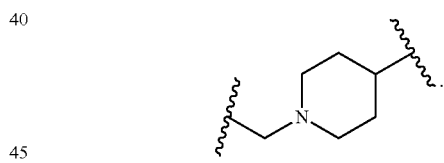
In some embodiments, L is
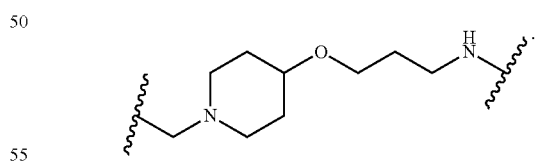
In some embodiments, L is
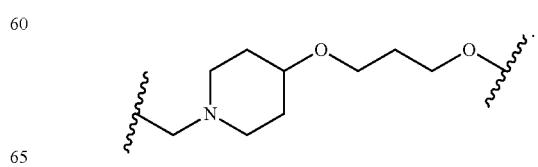

In some embodiments, L is
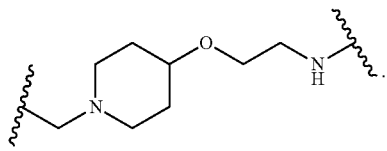 [SMILES: *CN1CCC(OCCN*)CC1]
In some embodiments, L is
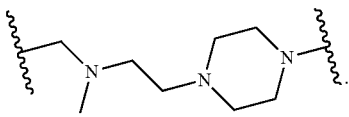
In some embodiments, L is
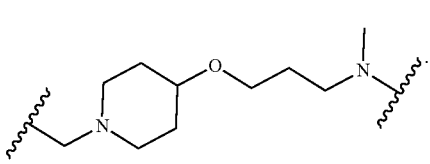 [SMILES: *CN1CCC(OCCCN(*)C)CC1]
In some embodiments, L is
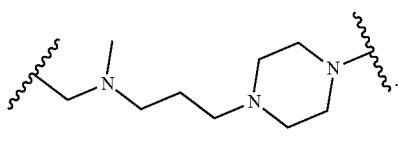
In some embodiments, L is
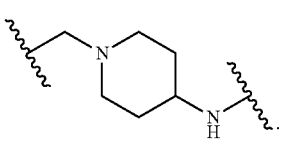 [SMILES: *CN1CCC(N*)CC1]
In some embodiments, L is
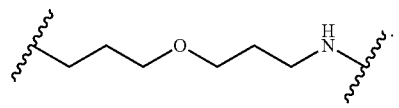
In some embodiments, L is
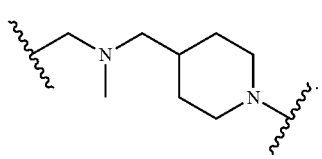 [SMILES: *CN(C)CC1CCN(*)CC1]
In some embodiments, L is
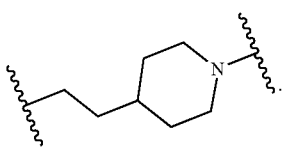 [SMILES: *CCC1CCN(*)CC1]
In some embodiments, L is
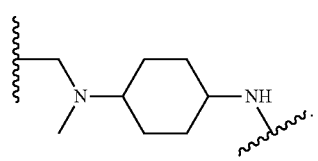
In some embodiments, L is
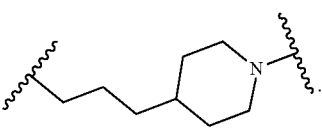 [SMILES: *CCCC1CCN(*)CC1]
In some embodiments, L is
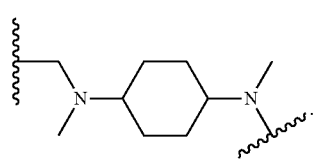
In some embodiments, L is
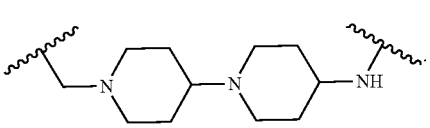

In some embodiments, L is
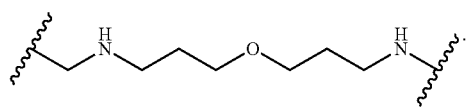 [SMILES: *CNCCCOCCCN*]
In some embodiments, L is
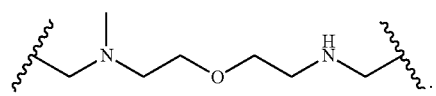 [SMILES: *CNCCOCCN(C)C*]
In some embodiments, L is
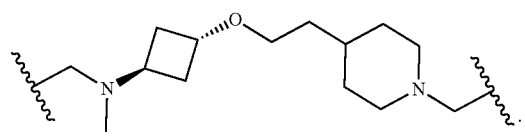 [SMILES: *CN1CCC(CCO[C@H]2C[C@H](N(C)C*)C2)CC1]
In some embodiments, L is
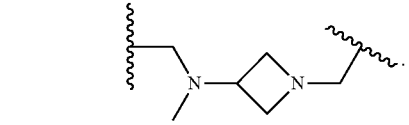 [SMILES: *CN1CC(N(C)C*)C1]
In some embodiments, L is
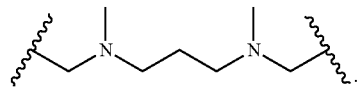 [SMILES: *CN(C)CCCN(C)C*]
In some embodiments, L is
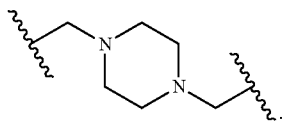 [SMILES: *CN1CCN(C*)CC1]
In some embodiments, L is
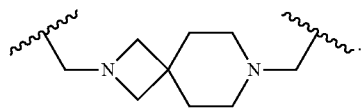
In some embodiments, L is
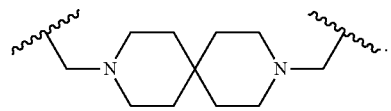 [SMILES: *CN1CCC2(CC1)CCN(C*)CC2]
In some embodiments, L is
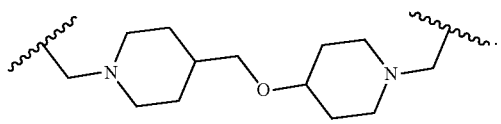 [SMILES: *CN1CCC(COC2CCN(C*)CC2)CC1]
In some embodiments, L is
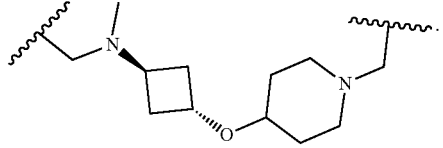 [SMILES: *CN1CCC(O[C@H]2C[C@H](N(C)C*)C2)CC1]
In some embodiments, L is
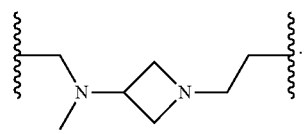 [SMILES: *CCN1CC(N(C)C*)C1]
In some embodiments, L is
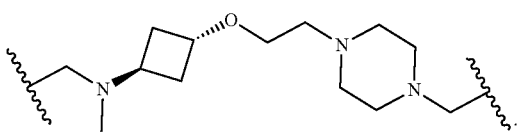 [SMILES: *CN1CCN(CCO[C@H]2C[C@H](N(C)C*)C2)CC1]
In some embodiments, L is
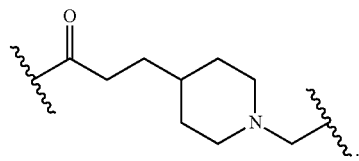 [SMILES: *CN1CCC(CCC(*)=O)CC1]
In some embodiments, L is
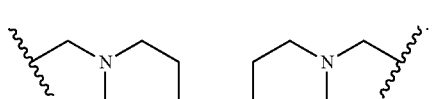

In some embodiments, L is
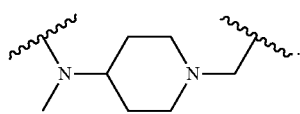
In some embodiments, L is
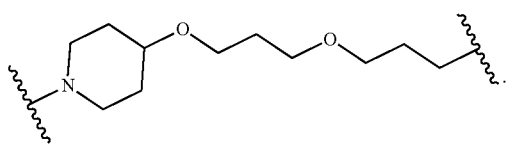 [SMILES: *CCCOCCCOC1CCN(*)CC1]
In some embodiments, L is
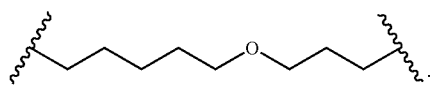 [SMILES: *CCCCCOCCC*]
In some embodiments, L is
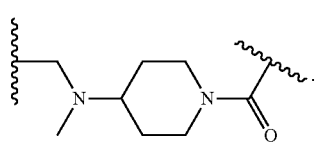 [SMILES: *CN(C)C1CCN(C(*)=O)CC1]
In some embodiments, L is
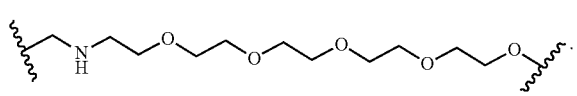 [SMILES: *CNCCOCCOCCOCCOCCO*]
In some embodiments, L is
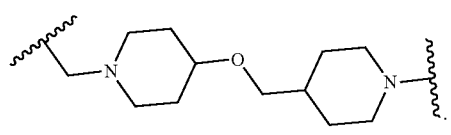 [SMILES: *CN1CCC(OCC2CCN(*)CC2)CC1]
In some embodiments, L is
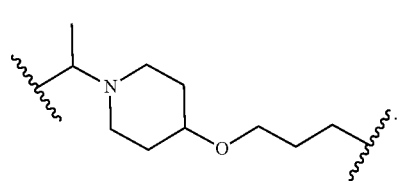 [SMILES: *CCCOC1CCN(C(*)C)CC1]
In some embodiments, L is
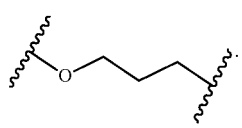 [SMILES: *CCCO*]
In some embodiments, L is
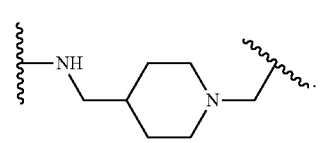 [SMILES: *CN1CCC(CN*)CC1]
In some embodiments, L is
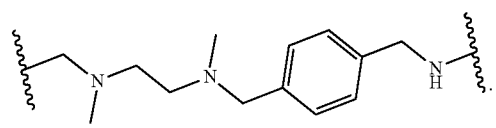 [SMILES: *CN(C)CCN(C)Cc1ccc(CN*)cc1]
In some embodiments, L is
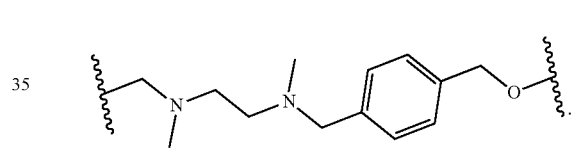
In some embodiments, L is
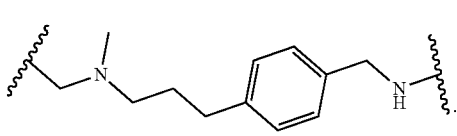 [SMILES: *CN(C)CCCc1ccc(CN*)cc1]
In some embodiments, L is
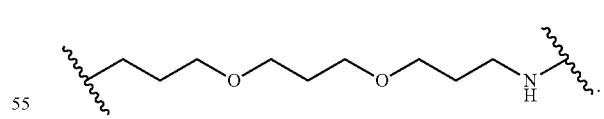
In some embodiments, L is

In some embodiments, L is
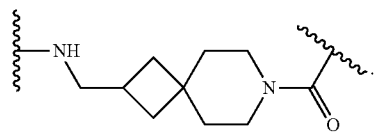 [SMILES: *NCC1CC2(CCN(C(*)=O)CC2)C1]
In some embodiments, L is
In some embodiments, L is
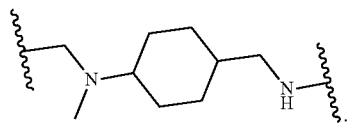 [SMILES: *CN(C)C1CCC(CN*)CC1]
In some embodiments, L is
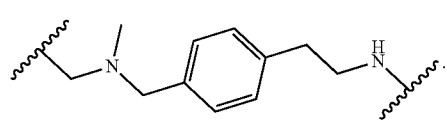 [SMILES: *CN(C)Cc1ccc(CCN*)cc1]
In some embodiments, L is
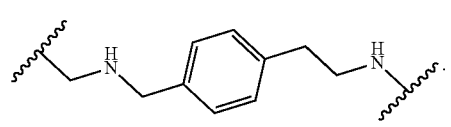 [SMILES: *CNCc1ccc(CCN*)cc1]
In some embodiments, L is
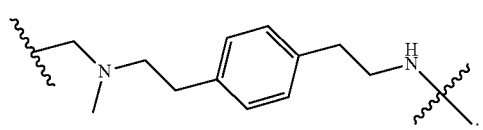 [SMILES: *CN(C)CCc1ccc(CCN*)cc1]
In some embodiments, L is
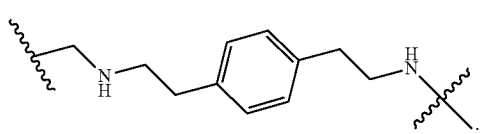 [SMILES: *CNCCc1ccc(CCN*)cc1]
In some embodiments, L is
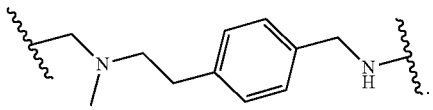 [SMILES: *CN(C)CCc1ccc(CN*)cc1]
In some embodiments, L is
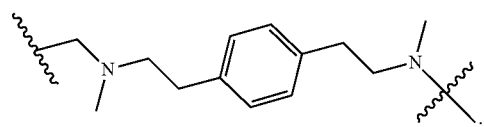 [SMILES: *CN(C)CCc1ccc(CCN(*)C)cc1]
In some embodiments, L is
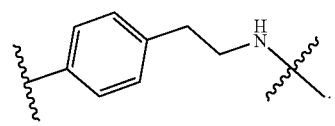 [SMILES: *NCCc1ccc(*)cc1]
In some embodiments, L is
In some embodiments, L is
In some embodiments, L is
In some embodiments, L is

In some embodiments, L is
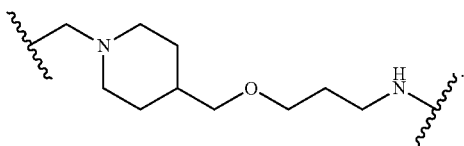 [SMILES: *CN1CCC(COCCCN*)CC1]
In some embodiments, L is
In some embodiments, L is
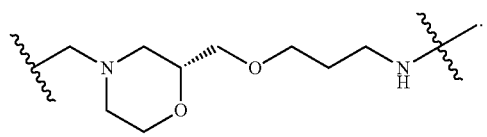 [SMILES: *CN1CCO[C@@H](COCCCN*)C1]
In some embodiments, L is
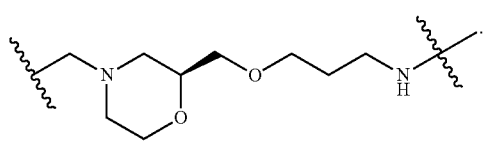 [SMILES: *CN1CCO[C@H](COCCCN*)C1]
In some embodiments, L is
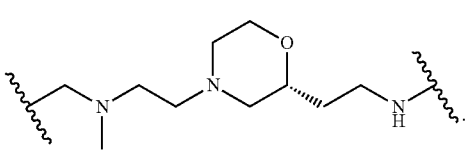 [SMILES: *CN(C)CCN1CCO[C@H](CCN*)C1]
In some embodiments, L is
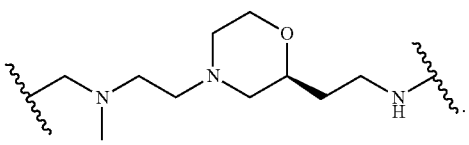 [SMILES: *CN(C)CCN1CCO[C@@H](CCN*)C1]
In some embodiments, L is
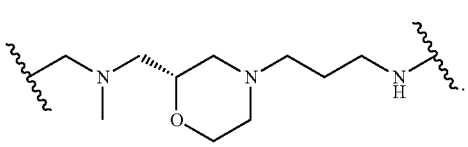 [SMILES: *CN(C)C[C@@H]1CN(CCCN*)CCO1]
In some embodiments, L is
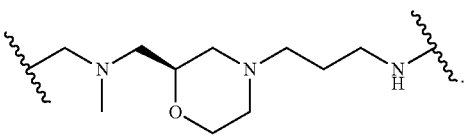 [SMILES: *CN(C)C[C@H]1CN(CCCN*)CCO1]
In some embodiments, L is
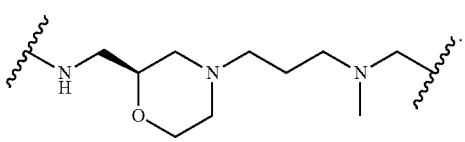 [SMILES: *CN(C)CCCN1CCO[C@@H](CN*)C1]
In some embodiments, L is
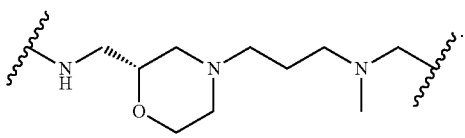 [SMILES: *CN(C)CCCN1CCO[C@H](CN*)C1]
In some embodiments, L is
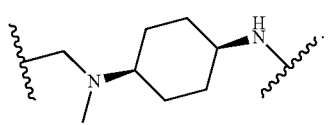 [SMILES: *CN(C)[C@H]1CC[C@@H](N*)CC1]
In some embodiments, L is
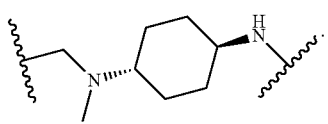 [SMILES: *CN(C)[C@H]1CC[C@H](N*)CC1]
In some embodiments, L is
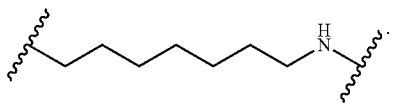 [SMILES: *CCCCCCCN*]
In some embodiments, L is
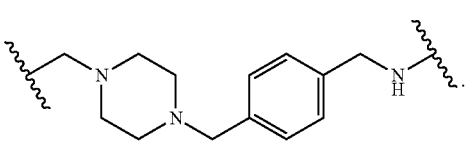 [SMILES: *CN1CCN(Cc2ccc(CN*)cc2)CC1]

In some embodiments, L is
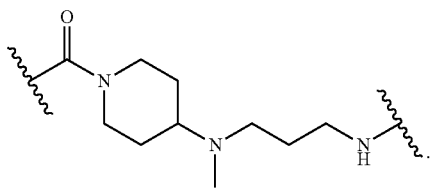 [SMILES: *NCCCN(C)C1CCN(C(*)=O)CC1]
In some embodiments, L is
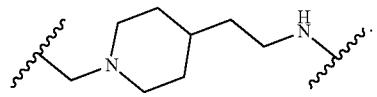 [SMILES: *CN1CCC(CCN*)CC1]
In some embodiments, L is
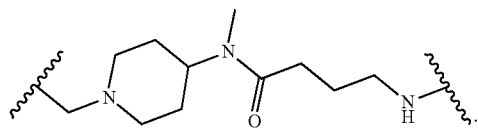 [SMILES: *CN1CCC(N(C)C(=O)CCCN*)CC1]
In some embodiments, L is
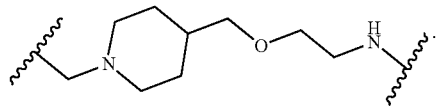 [SMILES: *CN1CCC(COCCN*)CC1]
In some embodiments, L is
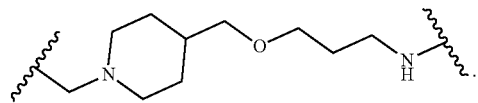 [SMILES: *CN1CCC(COCCCN*)CC1]
In some embodiments, L is
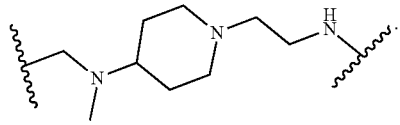 [SMILES: *CN(C)C1CCN(CCN*)CC1]
In some embodiments, L is
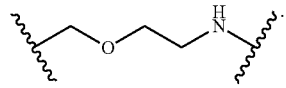 [SMILES: *COCCN*]
In some embodiments, L is
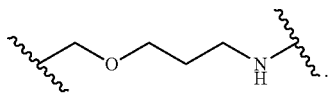 [SMILES: *COCCCN*]
In some embodiments, L is
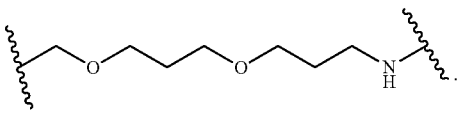 [SMILES: *COCCCOCCCN*]
In some embodiments, L is
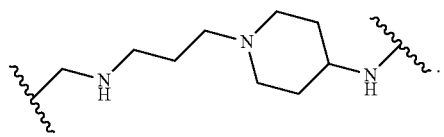 [SMILES: *CNCCCN1CCC(N*)CC1]
In some embodiments, L is
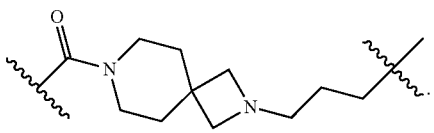 [SMILES: *CCCN1CC2(CCN(C(*)=O)CC2)C1]
In some embodiments, L is
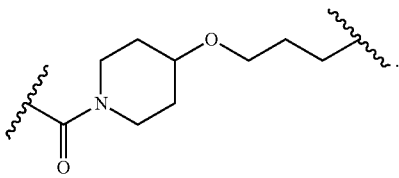 [SMILES: *CCCOC1CCN(C(*)=O)CC1]
In some embodiments, L is
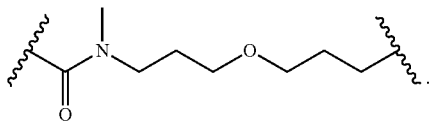 [SMILES: *CCCOCCCN(C)C(*)=O]
In some embodiments, L is
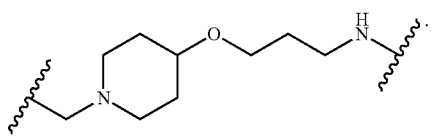 [SMILES: *CN1CCC(OCCCN*)CC1]

In some embodiments, L is
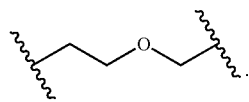 [SMILES: *CCOC*]
In some embodiments, L is
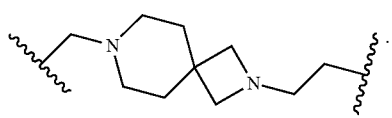 [SMILES: *CCN1CC2(CCN(C*)CC2)C1]
In some embodiments, L is
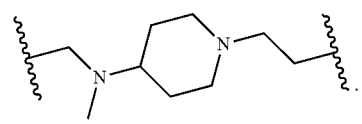 [SMILES: *CCN1CCC(N(C)C*)CC1]
In some embodiments, L is
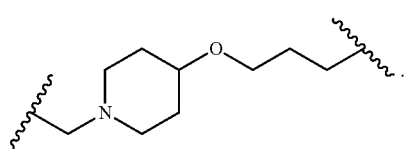 [SMILES: *CCCOC1CCN(C*)CC1]
In some embodiments, L is
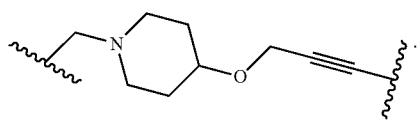 [SMILES: *C#CCOC1CCN(C*)CC1]
In some embodiments, L is
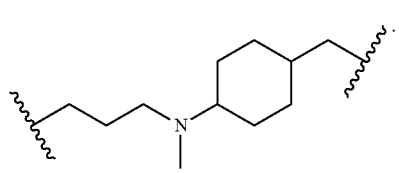 [SMILES: *CCCN(C)C1CCC(C*)CC1]
In some embodiments, L is
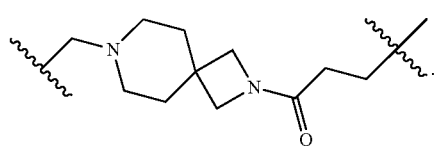 [SMILES: *CCC(=O)N1CC2(CCN(C*)CC2)C1]
In some embodiments, L is
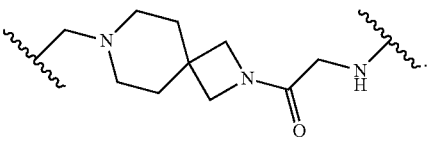 [SMILES: *CN1CCC2(CC1)CN(C(=O)CN*)C2]
In some embodiments, L is
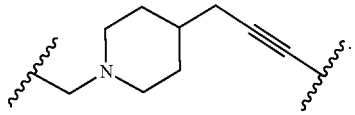 [SMILES: *C#CCC1CCN(C*)CC1]
In some embodiments, L is
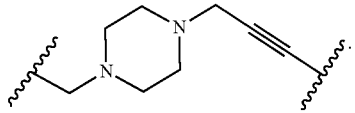 [SMILES: *C#CCN1CCN(C*)CC1]
In some embodiments, L is
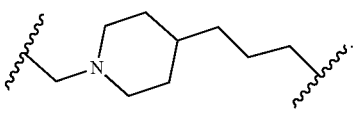 [SMILES: *CCCC1CCN(C*)CC1]
In some embodiments, L is
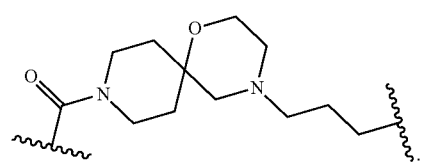 [SMILES: *CCCN1CCOC2(CCN(C(*)=O)CC2)C1]
In some embodiments, L is
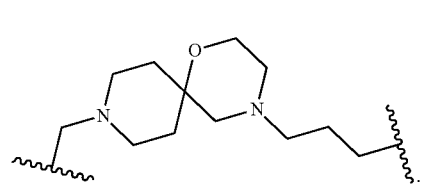 [SMILES: *CCCN1CCOC2(CCN(C*)CC2)C1]
In some embodiments, L is
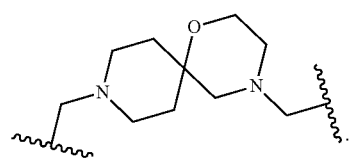 [SMILES: *CN1CCC2(CC1)CN(C*)CCO2]

In some embodiments, L is

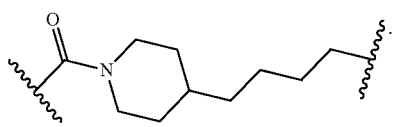 [SMILES: *CCCCC1CCN(C(*)=O)CC1]

In some embodiments, L is

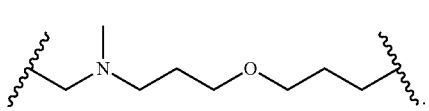 [SMILES: *CCCOCCCN(C)C*]

In some embodiments, L is

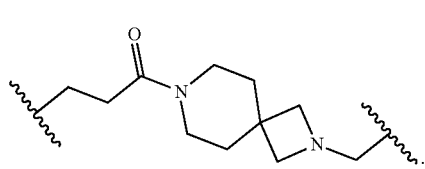 [SMILES: *CCC(=O)N1CCC2(CC1)CN(C*)C2]

In some embodiments, L is

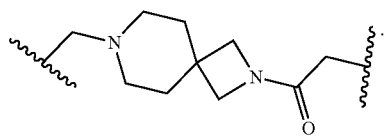 [SMILES: *CC(=O)N1CC2(CCN(C*)CC2)C1]

In some embodiments, L is

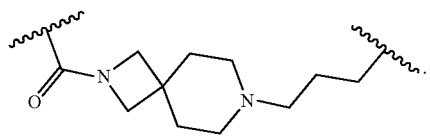 [SMILES: *CCCN1CCC2(CC1)CN(C(*)=O)C2]

In some embodiments, L is

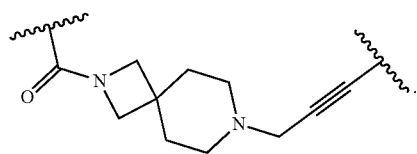 [SMILES: *C#CCN1CCC2(CC1)CN(C(*)=O)C2]

In some embodiments, L is

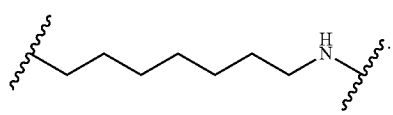 [SMILES: *CCCCCCCN*]

In some embodiments, L is

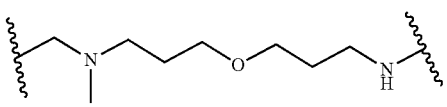

In some embodiments, L is

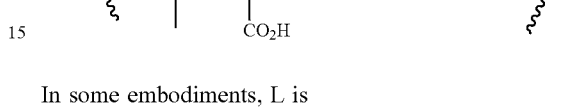

In some embodiments, L is

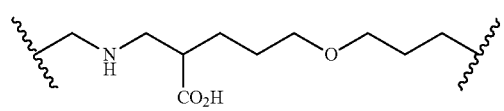

In some embodiments, L is

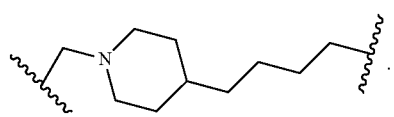 [SMILES: *CCCCC1CCN(C*)CC1]

In some embodiments, L is

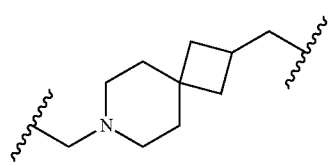

In some embodiments, L is

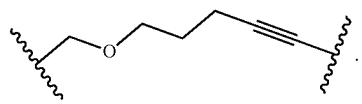 [SMILES: *C#CCCCOC*]

In some embodiments, L is

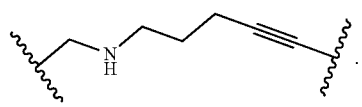 [SMILES: *C#CCCCNC*]

In some embodiments, L is

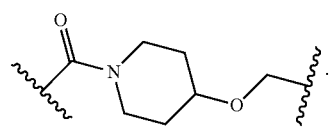 [SMILES: *COC1CCN(C(*)=O)CC1]

In some embodiments, L is
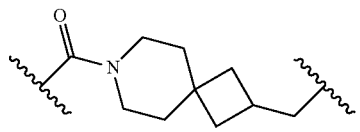
In some embodiments, L is
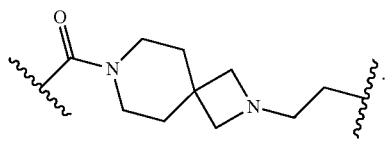 [SMILES: *CCN1CC2(CCN(C(*)=O)CC2)C1]
In some embodiments, L is
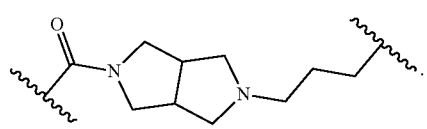 [SMILES: *CCCN1CC2CN(C(*)=O)CC2C1]
In some embodiments, L is
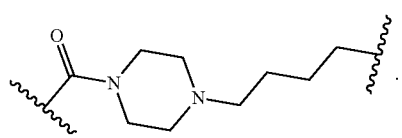 [SMILES: *CCCCN1CCN(C(*)=O)CC1]
In some embodiments, L is
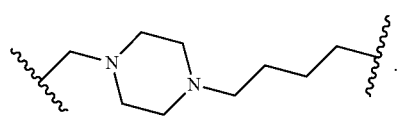 [SMILES: *CCCCN1CCN(C*)CC1]
In some embodiments, L is
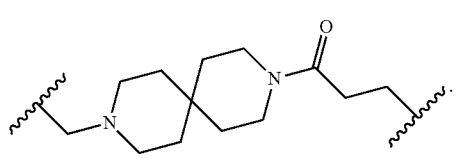 [SMILES: *CCC(=O)N1CCC2(CCN(C*)CC2)CC1]
In some embodiments, L is
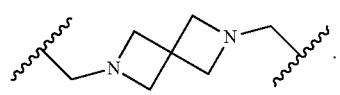 [SMILES: *CN1CC2(C1)CN(C*)C2]
In some embodiments, L is
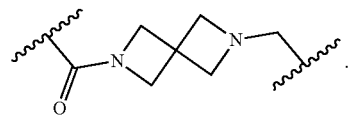 [SMILES: *CN1CC2(C1)CN(C(*)=O)C2]
In some embodiments, L is
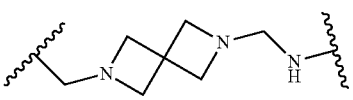
In some embodiments, L is
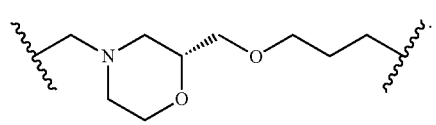 [SMILES: *CCCOC[C@H]1CN(C*)CCO1]
In some embodiments, L is
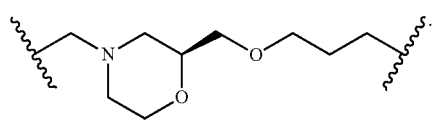 [SMILES: *CCCOC[C@@H]1CN(C*)CCO1]
In some embodiments, L is
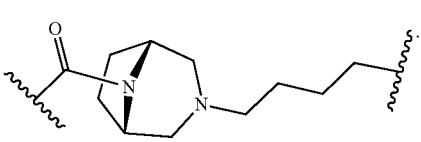 [SMILES: *CCCCN1C[C@H]2CC[C@@H](C1)N2C(*)=O]
In some embodiments, L is
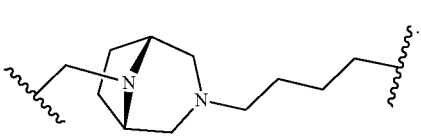
In some embodiments, L is
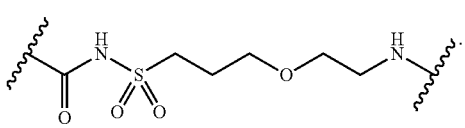 [SMILES: *NCCOCCCS(=O)(=O)NC(*)=O]

In some embodiments, L is
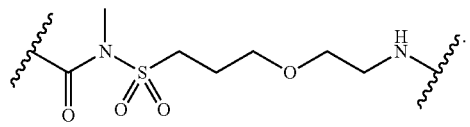 [SMILES: *NCCOCCCS(=O)(=O)N(C)C(*)=O]
In some embodiments, L is
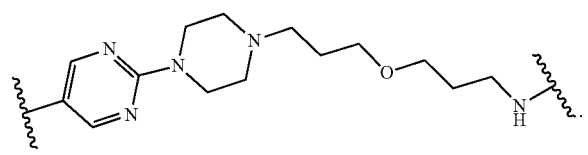 [SMILES: *NCCCOCCCN1CCN(c2ncc(*)cn2)CC1]
In some embodiments, L is
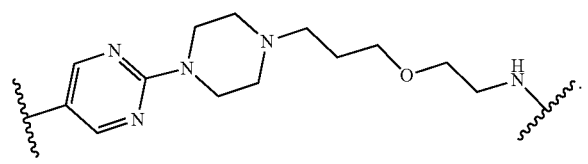 [SMILES: *NCCOCCCN1CCN(c2ncc(*)cn2)CC1]
In some embodiments, L is
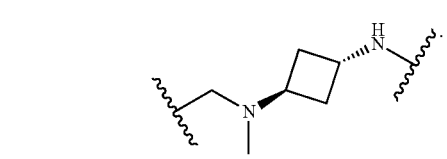 [SMILES: *CN(C)[C@H]1C[C@H](N*)C1]
In some embodiments, L is
In some embodiments, L is
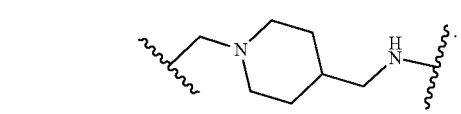 [SMILES: *CN1CCC(CN*)CC1]
In some embodiments, L is
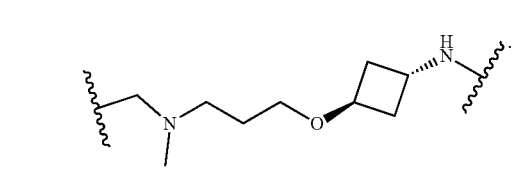 [SMILES: *CN(C)CCCO[C@H]1C[C@H](N*)C1]
In some embodiments, L is
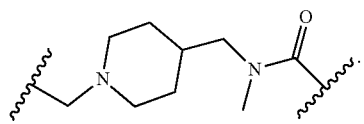 [SMILES: *CN1CCC(CN(C)C(*)=O)CC1]
In some embodiments, L is
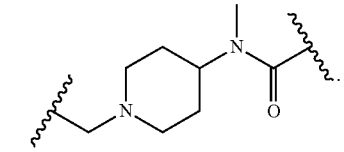 [SMILES: *CN1CCC(N(C)C(*)=O)CC1]
In some embodiments, L is
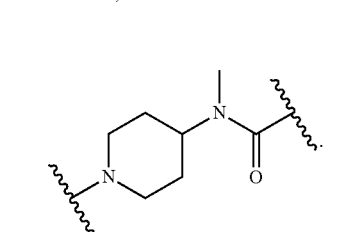
In some embodiments, L is
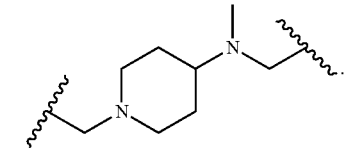 [SMILES: *CN1CCC(N(C)C*)CC1]
In some embodiments, L is
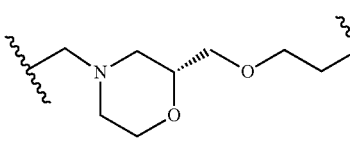
In some embodiments, L is
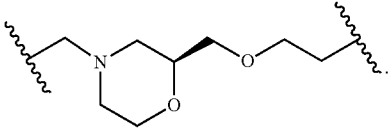 [SMILES: *CCOC[C@@H]1CN(C*)CCO1]

In some embodiments, L is
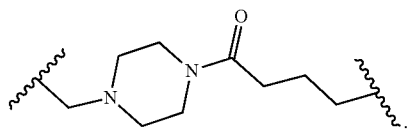 [SMILES: *CCCC(=O)N1CCN(C*)CC1]
In some embodiments, L is
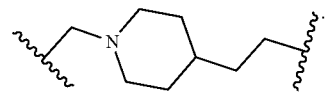 [SMILES: *CCC1CCN(C*)CC1]
In some embodiments, L is
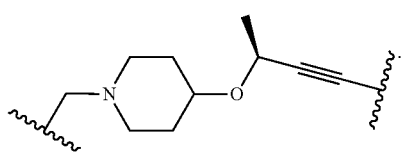
In some embodiments, L is
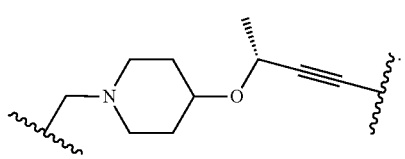 [SMILES: *C#C[C@@H](C)OC1CCN(C*)CC1]
In some embodiments, L is
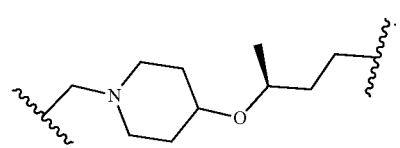 [SMILES: *CC[C@H](C)OC1CCN(C*)CC1]
In some embodiments, L is
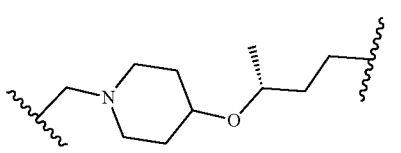
In some embodiments, L is
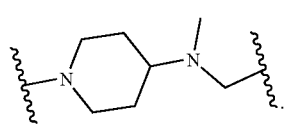 [SMILES: *CN(C)C1CCN(*)CC1]
In some embodiments, L is
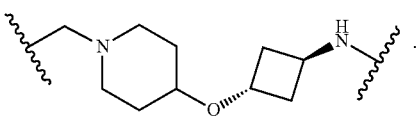 [SMILES: *CN1CCC(O[C@H]2C[C@H](N*)C2)CC1]
In some embodiments, L is
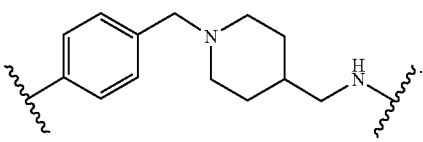 [SMILES: *NCC1CCN(Cc2ccc(*)cc2)CC1]
In some embodiments, L is
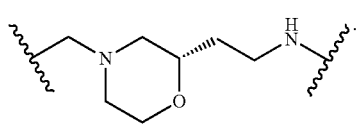 [SMILES: *CN1CCO[C@@H](CCN*)C1]
In some embodiments, L is
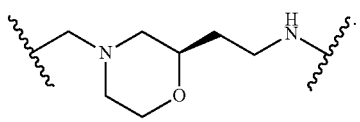 [SMILES: *CN1CCO[C@H](CCN*)C1]
In some embodiments, L is
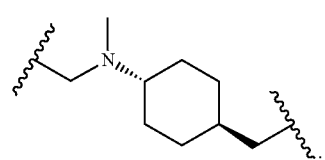 [SMILES: *CN(C)[C@H]1CC[C@H](C*)CC1]
In some embodiments, L is
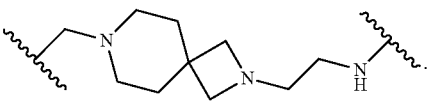 [SMILES: *CN1CCC2(CC1)CC(CCN*)C2]
In some embodiments, L is
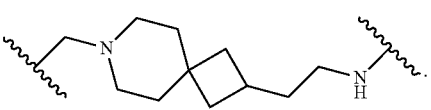

In some embodiments, L is

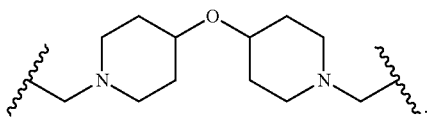 [SMILES: *CN1CCC(OC2CCN(C*)CC2)CC1]

In some embodiments, L is

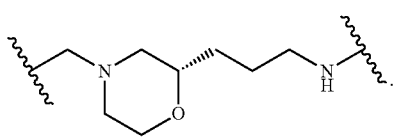 [SMILES: *CN1CCO[C@@H](CCCN*)C1]

In some embodiments, L is

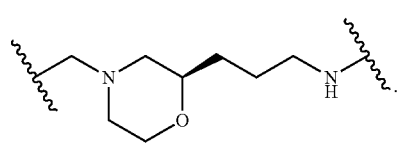 [SMILES: *CN1CCO[C@H](CCCN*)C1]

In some embodiments, L is

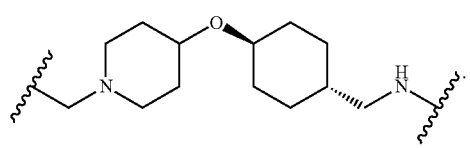 [SMILES: *CN1CCC(O[C@H]2CC[C@H](CN*)CC2)CC1]

In some embodiments, L is

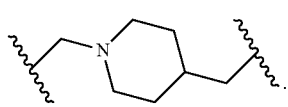 [SMILES: *CC1CCN(C*)CC1]

In some embodiments, L is

In some embodiments, L is

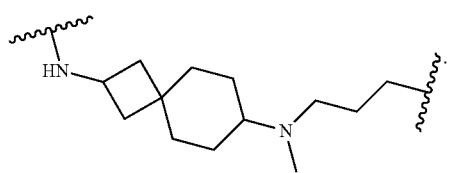 [SMILES: *CCCN(C)C1CCC2(CC1)CC(N*)C2]

In some embodiments, L is

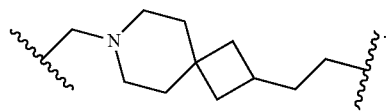 [SMILES: *CCC1CC2(CCN(C*)CC2)C1]

In some embodiments, L is

In some embodiments, L is

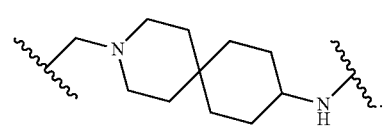 [SMILES: *CN1CCC2(CCC(N*)CC2)CC1]

In some embodiments, L is

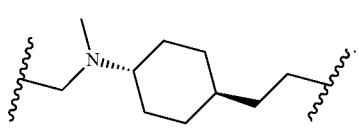 [SMILES: *CC[C@H]1CC[C@H](N(C)C*)CC1]

In some embodiments, L is

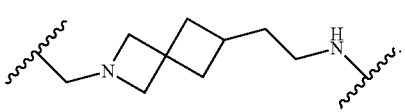 [SMILES: *CN1CC2(CC(CCN*)C2)C1]

In some embodiments, L is

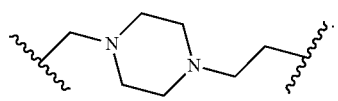 [SMILES: *CCN1CCN(C*)CC1]

In some embodiments, L is

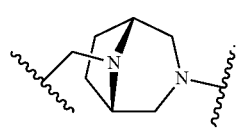

In some embodiments, L is

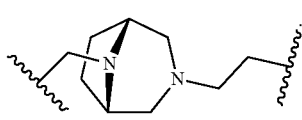

In some embodiments, L is
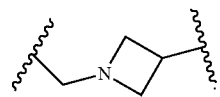
In some embodiments, L is
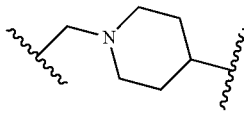
In some embodiments, L is
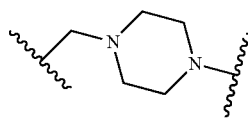
In some embodiments, L is
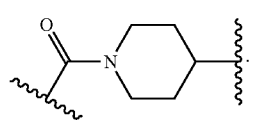
In some embodiments, L is
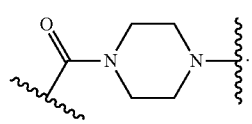
In some embodiments, L is
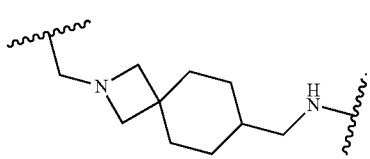
In some embodiments, L is
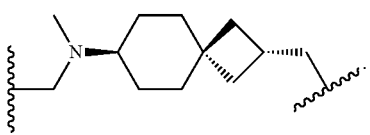
In some embodiments, L is
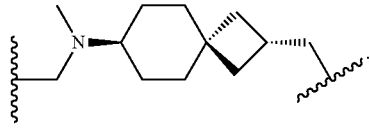
In some embodiments, L is
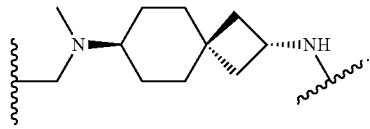
In some embodiments, L is
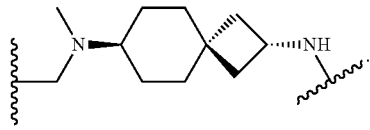
In some embodiments, L is
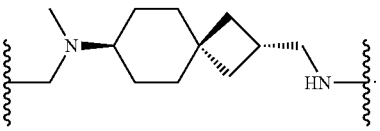
In some embodiments, L is
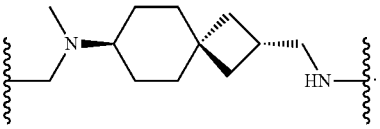
In some embodiments, L is
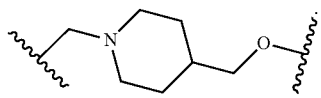
In some embodiments, L is
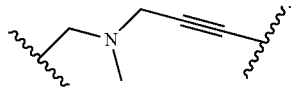 [SMILES: *C#CCN(C)C*]

In some embodiments, L is
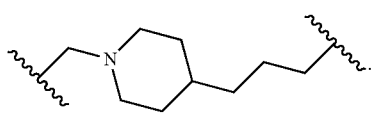 [SMILES: *CCCC1CCN(C*)CC1]
In some embodiments, L is
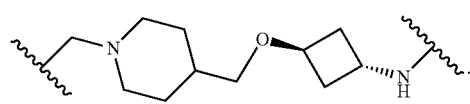 [SMILES: *CN1CCC(CO[C@H]2C[C@H](N*)C2)CC1]
In some embodiments, L is
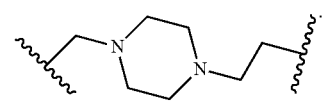 [SMILES: *CCN1CCN(C*)CC1]
In some embodiments, L is
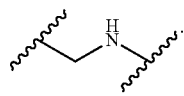 [SMILES: *CN*]
In some embodiments, L is
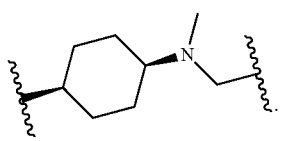 [SMILES: *CN(C)[C@H]1CC[C@@H](*)CC1]
In some embodiments, L is
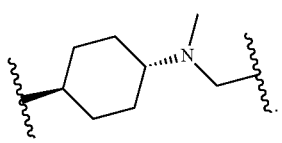 [SMILES: *CN(C)[C@H]1CC[C@H](*)CC1]
In some embodiments, L is
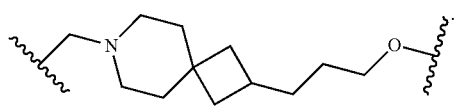 [SMILES: *CN1CCC2(CC1)CC(CCCO*)C2]
In some embodiments, L is
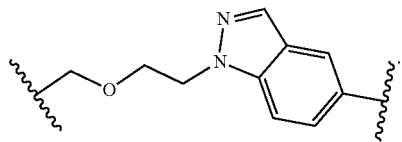 [SMILES: *COCCn1ncc2cc(*)ccc21]
In some embodiments, L is
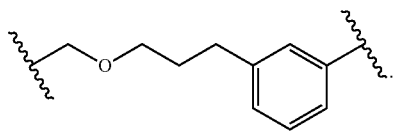 [SMILES: *COCCCc1cccc(*)c1]
In some embodiments, L is
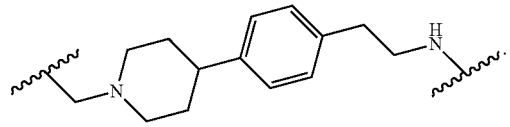 [SMILES: *CN1CCC(c2ccc(CCN*)cc2)CC1]
In some embodiments, L is
In some embodiments, L is
In some embodiments, L is
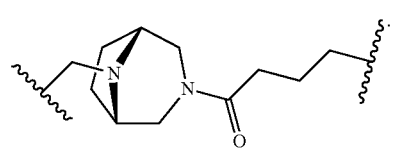 [SMILES: *CCCC(=O)N1C[C@H]2CC[C@@H](C1)N2C*]
In some embodiments, L is
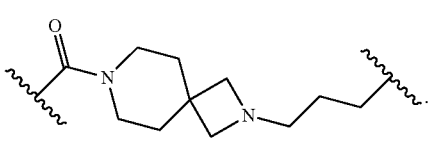 [SMILES: *CCCN1CC2(CCN(C(*)=O)CC2)C1]

In some embodiments, L is
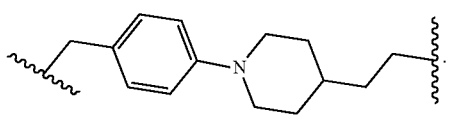 [SMILES: *CCC1CCN(c2ccc(C*)cc2)CC1]
In some embodiments, L is
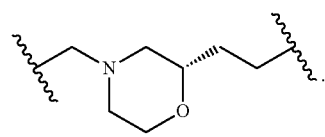 [SMILES: *CC[C@H]1CN(C*)CCO1]
In some embodiments, L is
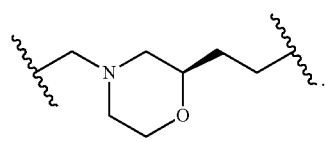 [SMILES: *CC[C@@H]1CN(C*)CCO1]
In some embodiments, L is
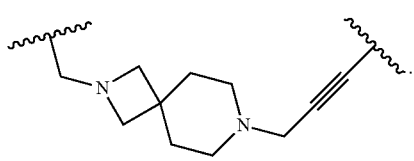 [SMILES: *C#CCN1CCC2(CC1)CN(C*)C2]
In some embodiments, L is
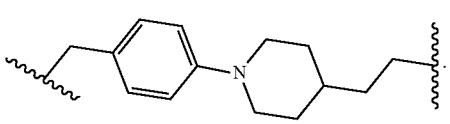 [SMILES: *CCC1CCN(c2ccc(C*)cc2)CC1]
In some embodiments, L is
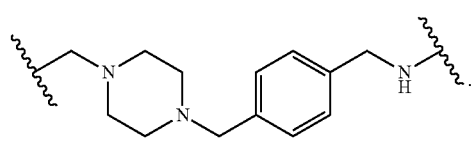 [SMILES: *CN1CCN(Cc2ccc(CN*)cc2)CC1]
In some embodiments, L is
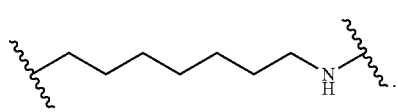 [SMILES: *CCCCCCCN*]
In some embodiments, L is
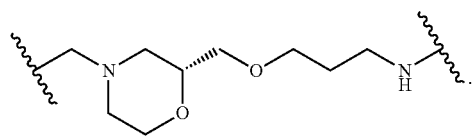 [SMILES: *CN1CCO[C@@H](COCCCN*)C1]
In some embodiments, L is
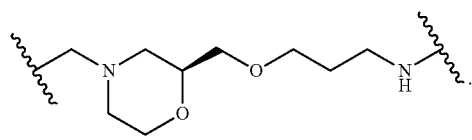 [SMILES: *CN1CCO[C@H](COCCCN*)C1]
In some embodiments, L is
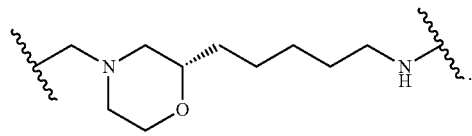 [SMILES: *CN1CCO[C@@H](CCCCCN*)C1]
In some embodiments, L is
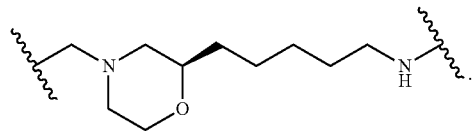 [SMILES: *CN1CCO[C@H](CCCCCN*)C1]
In some embodiments, L is
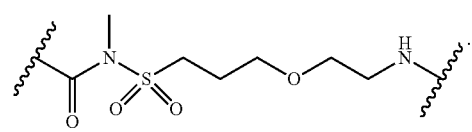 [SMILES: *NCCOCCCS(=O)(=O)N(C)C(*)=O]
In some embodiments, L is
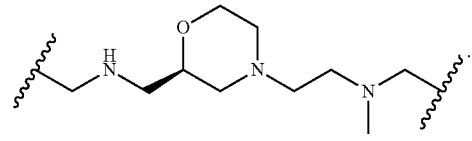 [SMILES: *CNC[C@@H]1CN(CCN(C)C*)CCO1]
In some embodiments, L is
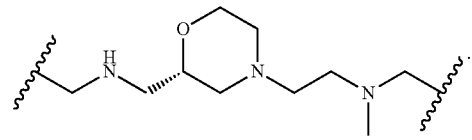 [SMILES: *CNC[C@H]1CN(CCN(C)C*)CCO1]

In some embodiments, L is
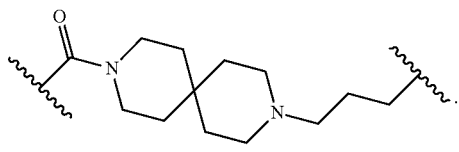 [SMILES: *CCCN1CCC2(CC1)CCN(C(*)=O)CC2]
In some embodiments, L is
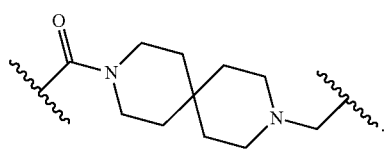 [SMILES: *CN1CCC2(CC1)CCN(C(*)=O)CC2]
In some embodiments, L is
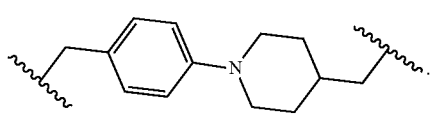 [SMILES: *Cc1ccc(N2CCC(C*)CC2)cc1]
In some embodiments, L is
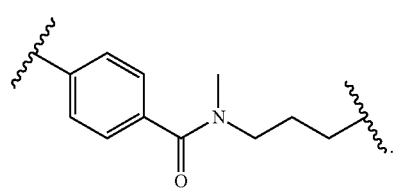 [SMILES: *CCCN(C)C(=O)c1ccc(*)cc1]
In some embodiments, L is
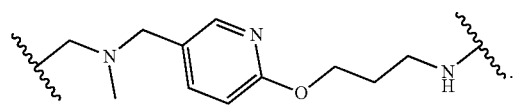 [SMILES: *CN(C)Cc1ccc(OCCCN*)nc1]
In some embodiments, L is
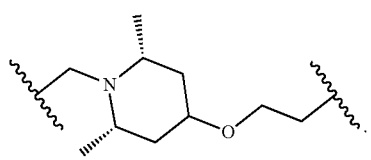 [SMILES: *CCOC1C[C@@H](C)N(C*)[C@@H](C)C1]
In some embodiments, L is
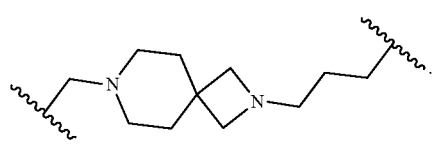 [SMILES: *CCCN1CC2(CCN(C*)CC2)C1]
In some embodiments, L is
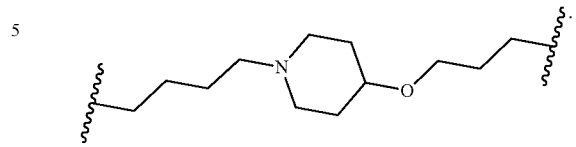
In some embodiments, L is
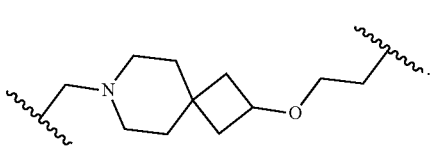 [SMILES: *CCOC1CC2(CCN(C*)CC2)C1]
In some embodiments, L is
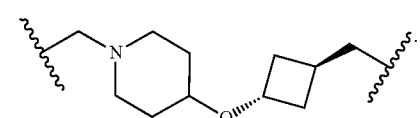
In some embodiments, L is
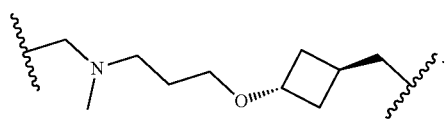 [SMILES: *CN(C)CCCO[C@H]1C[C@H](C*)C1]
In some embodiments, L is
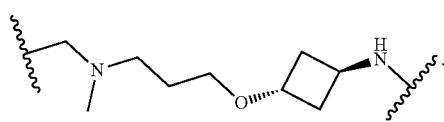 [SMILES: *CN(C)CCCO[C@H]1C[C@H](N*)C1]
In some embodiments, L is
In some embodiments, L is
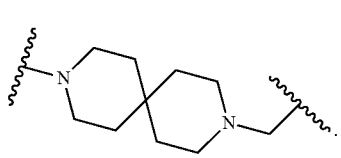 [SMILES: *CN1CCC2(CCN(*)CC2)CC1]

In some embodiments, L is
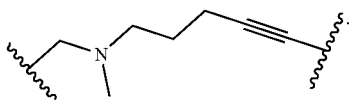 [SMILES: *C#CCCCN(C)C*]
In some embodiments, L is
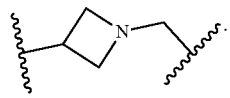 [SMILES: *CN1CC(*)C1]
In some embodiments, L is
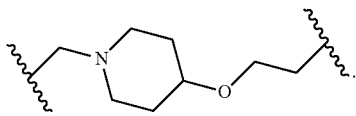 [SMILES: *CCOC1CCN(C*)CC1]
In some embodiments, L is
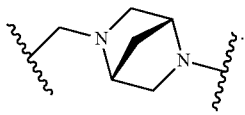 [SMILES: *CN1C[C@H]2C[C@@H]1CN2*]
In some embodiments, L is
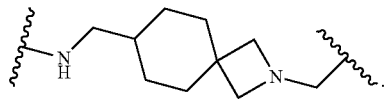 [SMILES: *CN1CC2(CCC(CN*)CC2)C1]
In some embodiments, L is
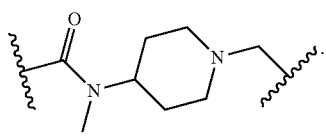 [SMILES: *CN1CCC(N(C)C(*)=O)CC1]
In some embodiments, L is
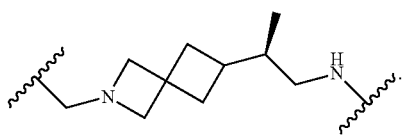 [SMILES: *CN1CC2(CC([C@@H](C)CN*)C2)C1]
In some embodiments, L is
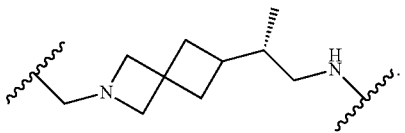 [SMILES: *CN1CC2(CC([C@H](C)CN*)C2)C1]
In some embodiments, L is
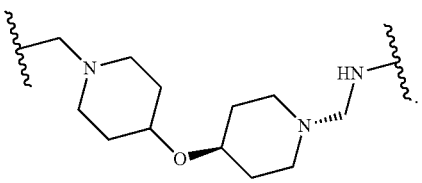
In some embodiments, L is
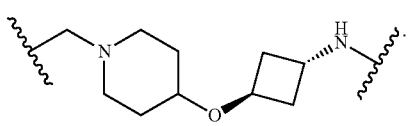 [SMILES: *CN1CCC(O[C@H]2C[C@H](N*)C2)CC1]
In some embodiments, L is
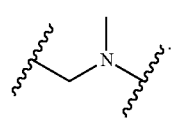
In some embodiments, L is
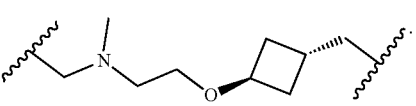 [SMILES: *CN(C)CCO[C@H]1C[C@H](C*)C1]
In some embodiments, L is
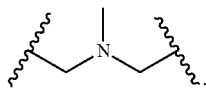 [SMILES: *CN(C)C*]
In some embodiments, L is
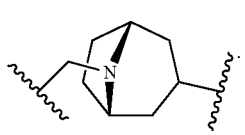 [SMILES: *CN1[C@@H]2CC[C@H]1CC(*)C2]

In some embodiments, L is
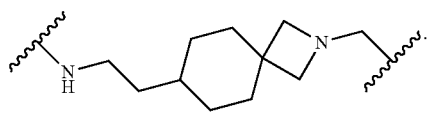 [SMILES: *CN1CC2(CCC(CCN*)CC2)C1]
In some embodiments, L is
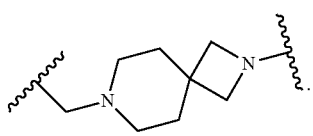 [SMILES: *CN1CCC2(CC1)CN(*)C2]
In some embodiments, L is
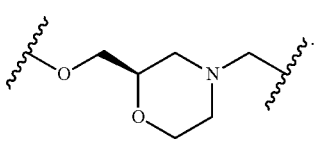 [SMILES: *CN1CCO[C@@H](CO*)C1]
In some embodiments, L is
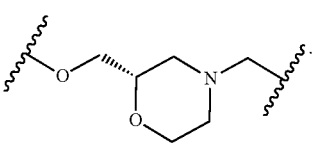 [SMILES: *CN1CCO[C@H](CO*)C1]
In some embodiments, L is
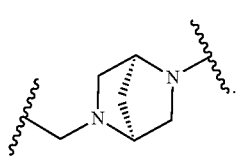 [SMILES: *CN1C[C@@H]2C[C@H]1CN2*]
In some embodiments, L is
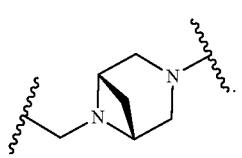 [SMILES: *CN1[C@@H]2C[C@H]1CN(*)C2]
In some embodiments, L is
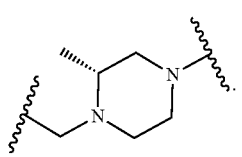 [SMILES: *CN1CCN(*)C[C@H]1C]
In some embodiments, L is
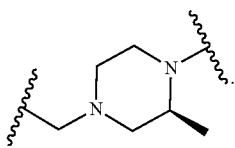 [SMILES: *CN1CCN(*)[C@@H](C)C1]
In some embodiments, L is
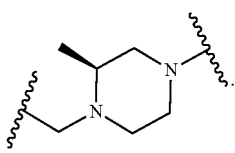 [SMILES: *CN1CCN(*)C[C@@H]1C]
In some embodiments, L is
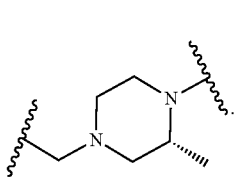 [SMILES: *CN1CCN(*)[C@H](C)C1]
In some embodiments, L is
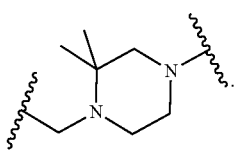 [SMILES: *CN1CCN(*)CC1(C)C]
In some embodiments, L is
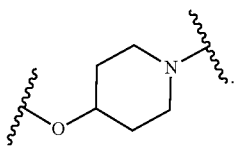 [SMILES: *OC1CCN(*)CC1]
In some embodiments, L is
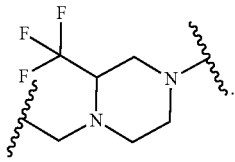 [SMILES: *CN1CCN(*)CC1C(F)(F)F]

In some embodiments, L is

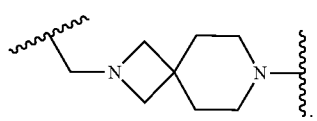 [SMILES: *CN1CC2(CCN(*)CC2)C1]

In some embodiments, L is

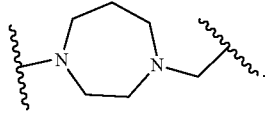 [SMILES: *CN1CCCN(*)CC1]

In some embodiments, L is

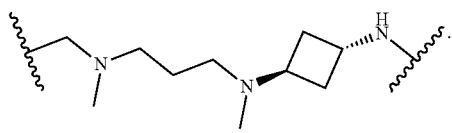 [SMILES: *CN(C)CCCN(C)[C@H]1C[C@H](N*)C1]

In some embodiments, L is

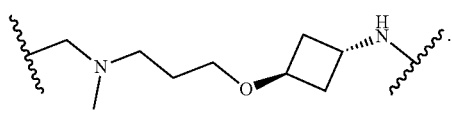 [SMILES: *CN(C)CCCO[C@H]1C[C@H](N*)C1]

In some embodiments, L is

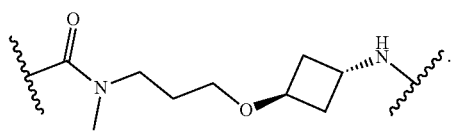 [SMILES: *N[C@H]1C[C@H](OCCCN(C)C(*)=O)C1]

In some embodiments, L is

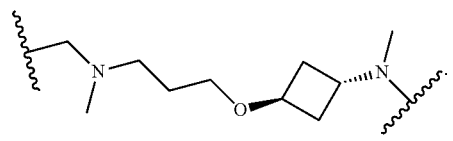 [SMILES: *CN(C)CCCO[C@H]1C[C@H](N(*)C)C1]

In some embodiments, L is

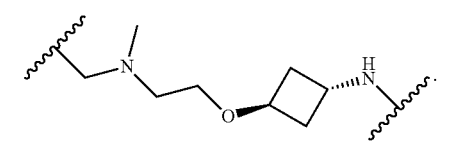 [SMILES: *CN(C)CCO[C@H]1C[C@H](N*)C1]

In some embodiments, L is

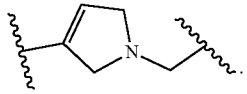 [SMILES: *CN1CC=C(*)C1]

In some embodiments, L is

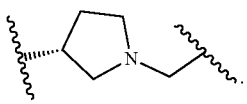 [SMILES: *CN1CC[C@@H](*)C1]

In some embodiments, L is

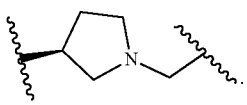 [SMILES: *CN1CC[C@H](*)C1]

In some embodiments, L is

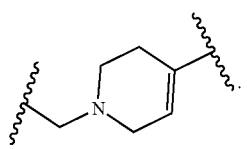 [SMILES: *CN1CC=C(*)CC1]

In some embodiments, L is

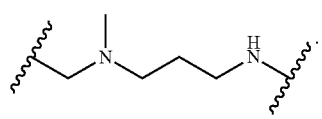 [SMILES: *CN(C)CCCN*]

In some embodiments, L is

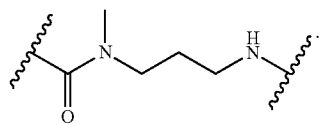 [SMILES: *NCCCN(C)C(*)=O]

In some embodiments, L is

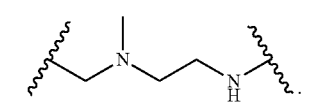 [SMILES: *CN(C)CCN*]

In some embodiments, L is

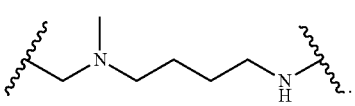 [SMILES: *CN(C)CCCCN*]

In some embodiments, L is

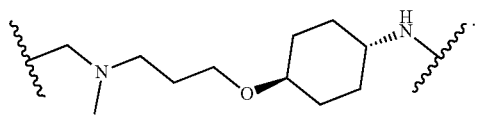 [SMILES: *CN(C)CCCO[C@H]1CC[C@H](N*)CC1]

In some embodiments, L is

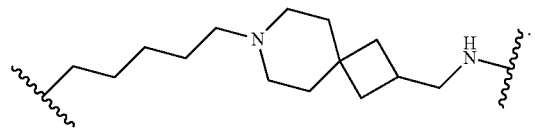 [SMILES: *CCCCCN1CCC2(CC1)CC(CN*)C2]

In some embodiments, L is

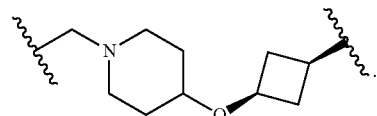

In some embodiments, L is

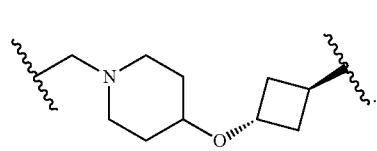 [SMILES: *CN1CCC(O[C@H]2C[C@H](*)C2)CC1]

In some embodiments, L is

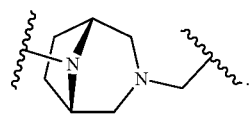 [SMILES: *CN1C[C@H]2CC[C@@H](C1)N2*]

In some embodiments, L is selected from those depicted in Table 1, below.

Without limitation, the point of attachment of L to IRAK and DIM can be, for example when L is

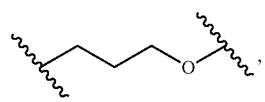 [SMILES: *CCCO*]

either

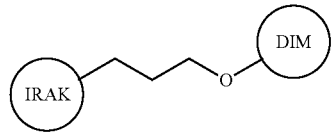

or

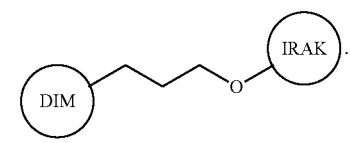

Exemplary compounds of the invention are set forth in Table 1, below.

TABLE 1

Exemplary Compounds

| I-# | Structure |
| --- | --- |
| I-1 | 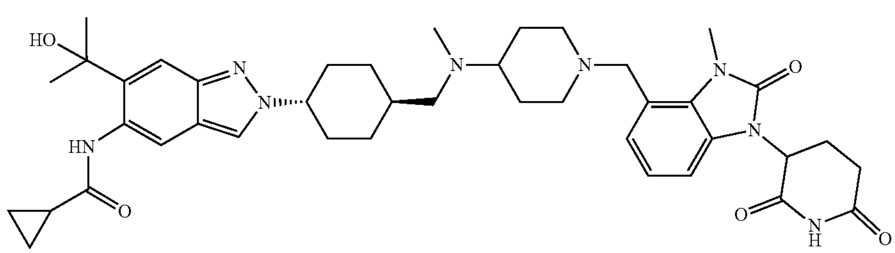 [SMILES: CN(C[C@H]1CC[C@H](n2cc3cc(NC(=O)C4CC4)c(C(C)(C)O)cc3n2)CC1)C1CCN(Cc2cccc3c2n(C)c(=O)n3C2CCC(=O)NC2=O)CC1] |

TABLE 1-continued
Exemplary Compounds
| I-# | Structure |
|---|---|
| I-2 | 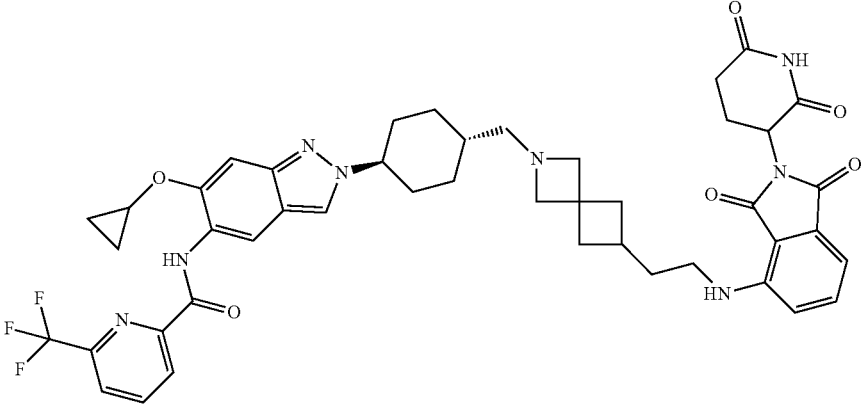 [SMILES: O=C1CCC(N2C(=O)c3cccc(NCCC4CC5(C4)CN(C[C@H]4CC[C@H](n6cc7cc(NC(=O)c8cccc(C(F)(F)F)n8)c(OC8CC8)cc7n6)CC4)C5)c3C2=O)C(=O)N1] |
| I-3 | 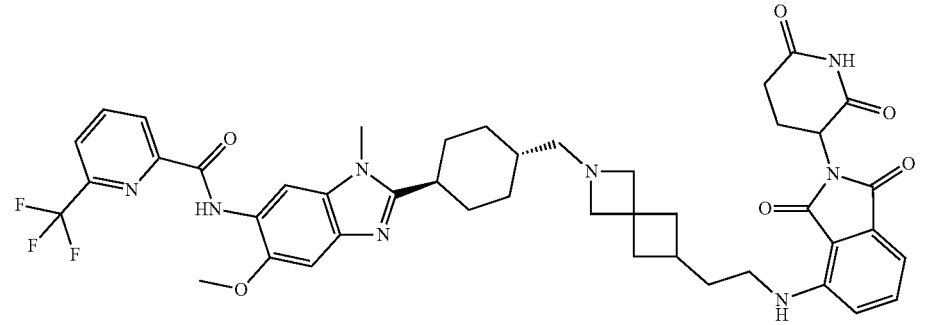 [SMILES: COc1cc2nc([C@H]3CC[C@H](CN4CC5(CC(CCNc6cccc7c6C(=O)N(C6CCC(=O)NC6=O)C7=O)C5)C4)CC3)n(C)c2cc1NC(=O)c1cccc(C(F)(F)F)n1] |
| I-4 | 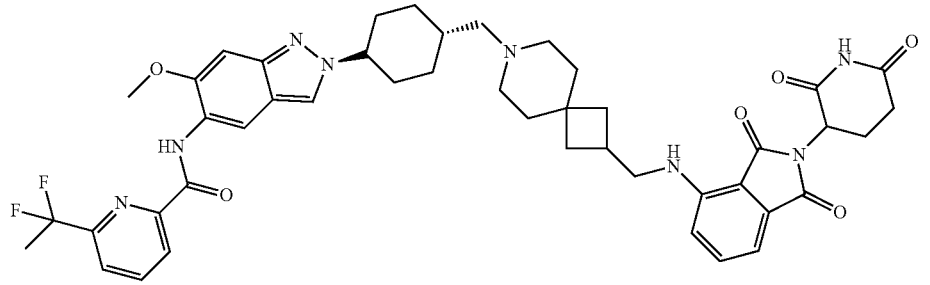 |
| I-5 | 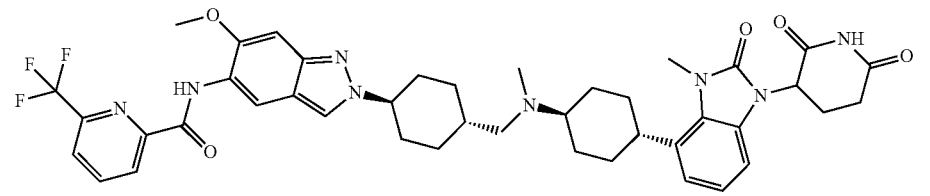 [SMILES: COc1cc2nn([C@H]3CC[C@H](CN(C)[C@H]4CC[C@H](c5cccc6c5n(C)c(=O)n6C5CCC(=O)NC5=O)CC4)CC3)cc2cc1NC(=O)c1cccc(C(F)(F)F)n1] |
| I-6 | 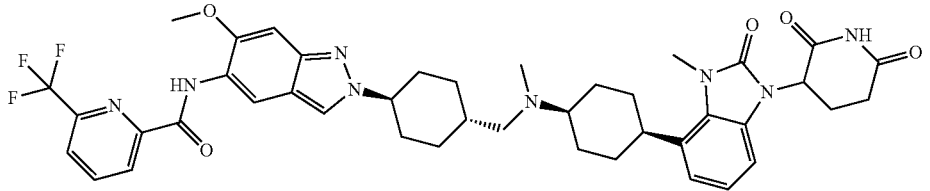 [SMILES: COc1cc2nn([C@H]3CC[C@H](CN(C)[C@H]4CC[C@@H](c5cccc6c5n(C)c(=O)n6C5CCC(=O)NC5=O)CC4)CC3)cc2cc1NC(=O)c1cccc(C(F)(F)F)n1] |

TABLE 1-continued
Exemplary Compounds
| I-# | Structure |
|---|---|
| I-7 | 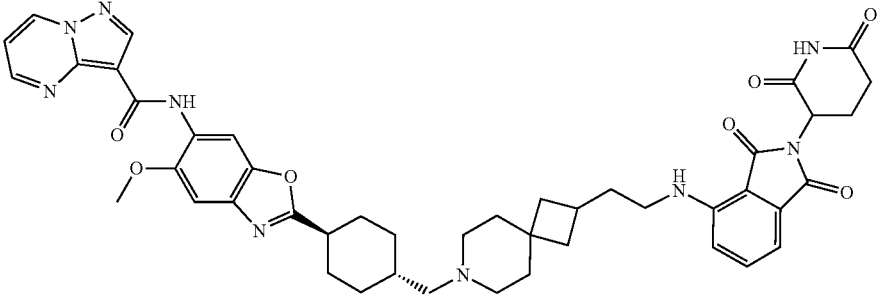 [SMILES: COc1cc2nc([C@H]3CC[C@H](CN4CCC5(CC4)CC(CCNc4cccc6c4C(=O)N(C4CCC(=O)NC4=O)C6=O)C5)CC3)oc2cc1NC(=O)c1cnn2cccnc12] |
| I-8 | 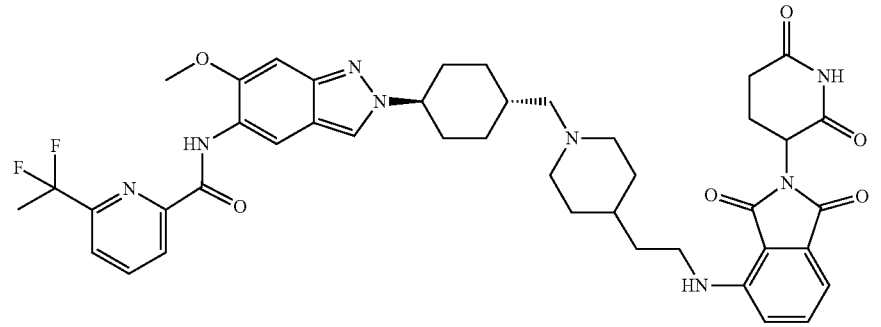 [SMILES: COc1cc2nn([C@H]3CC[C@H](CN4CCC(CCNc5cccc6c5C(=O)N(C5CCC(=O)NC5=O)C6=O)CC4)CC3)cc2cc1NC(=O)c1cccc(C(C)(F)F)n1] |
| I-9 | 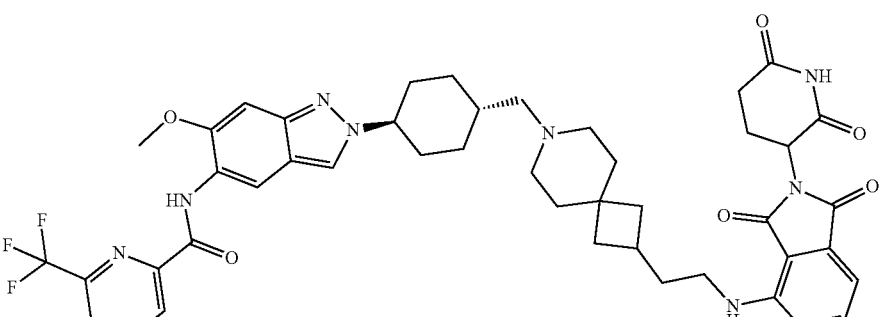 |
| I-10 | 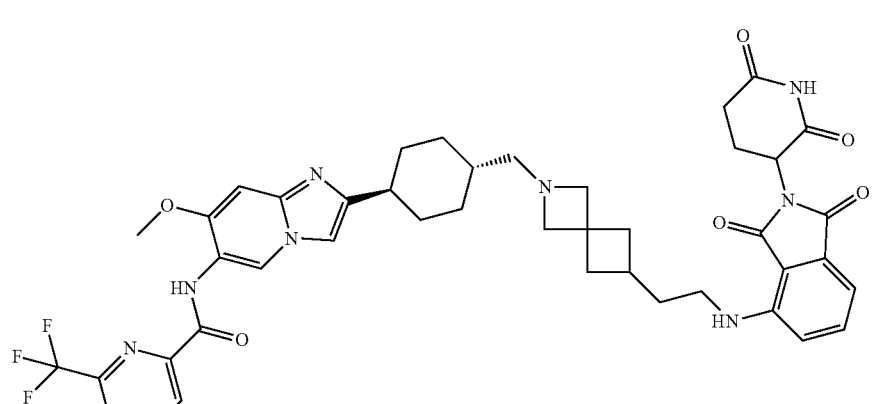 |

TABLE 1-continued

Exemplary Compounds

| I-# | Structure |
|---|---|
| I-11 | 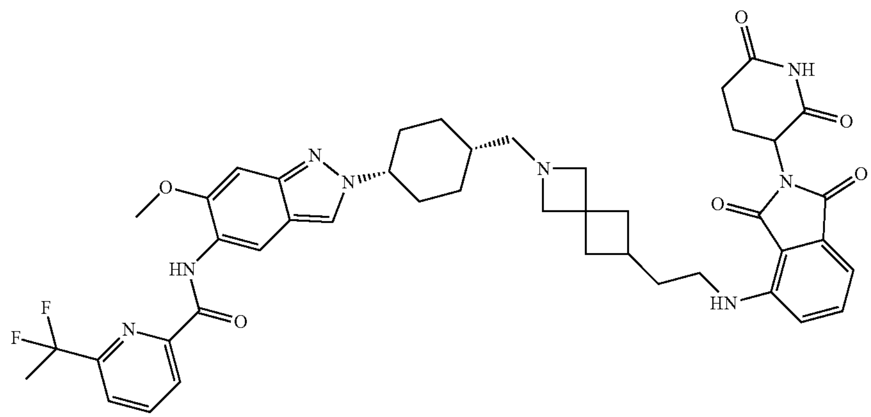 [SMILES: COc1cc2nn([C@H]3CC[C@@H](CN4CC5(CC(CCNc6cccc7c6C(=O)N(C6CCC(=O)NC6=O)C7=O)C5)C4)CC3)cc2cc1NC(=O)c1cccc(C(C)(F)F)n1] |
| I-12 | 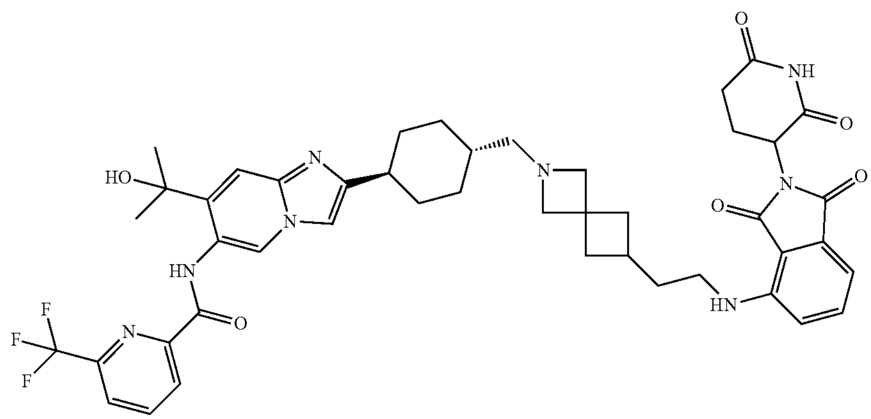 [SMILES: CC(C)(O)c1cc2nc([C@H]3CC[C@H](CN4CC5(CC(CCNc6cccc7c6C(=O)N(C6CCC(=O)NC6=O)C7=O)C5)C4)CC3)cn2cc1NC(=O)c1cccc(C(F)(F)F)n1] |
| I-13 | 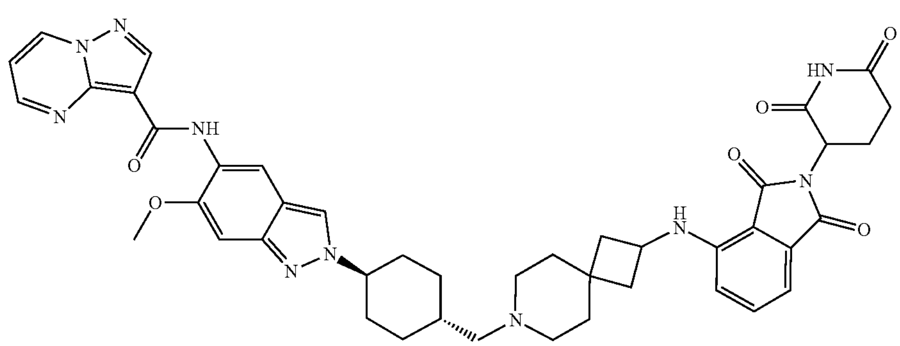 [SMILES: COc1cc2nn([C@H]3CC[C@H](CN4CCC5(CC4)CC(Nc4cccc6c4C(=O)N(C4CCC(=O)NC4=O)C6=O)C5)CC3)cc2cc1NC(=O)c1cnn2cccnc12] |
| I-14 | 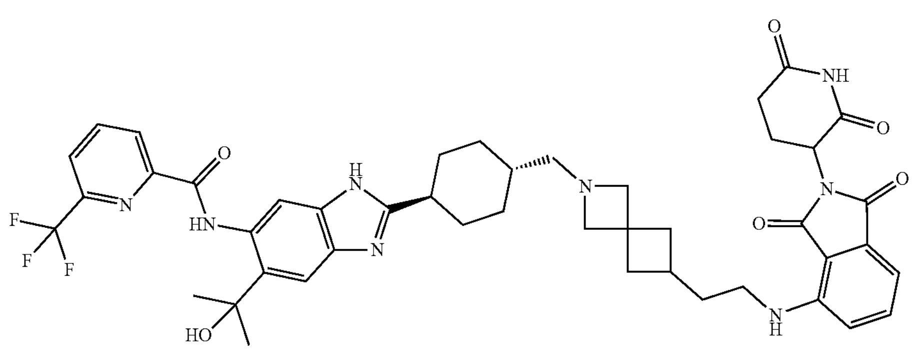 [SMILES: CC(C)(O)c1cc2nc([C@H]3CC[C@H](CN4CC5(CC(CCNc6cccc7c6C(=O)N(C6CCC(=O)NC6=O)C7=O)C5)C4)CC3)[nH]c2cc1NC(=O)c1cccc(C(F)(F)F)n1] |

TABLE 1-continued

Exemplary Compounds

| I-# | Structure |
|---|---|
| I-15 | 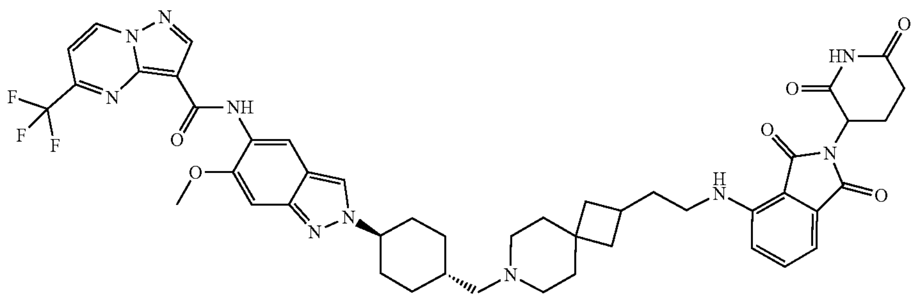 [SMILES: COc1cc2nn([C@H]3CC[C@H](CN4CCC5(CC4)CC(CCNc4cccc6c4C(=O)N(C4CCC(=O)NC4=O)C6=O)C5)CC3)cc2cc1NC(=O)c1cnn2ccc(C(F)(F)F)nc12] |
| I-16 | 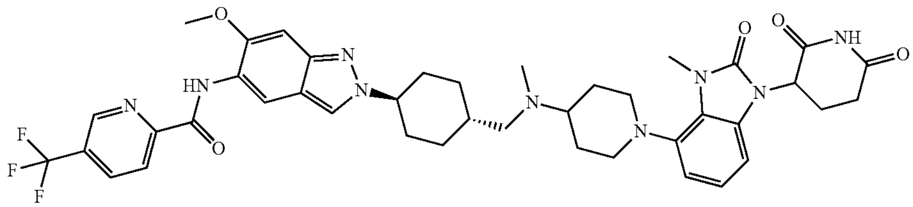 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1ccc(C(F)(F)F)cn1] |
| I-17 | 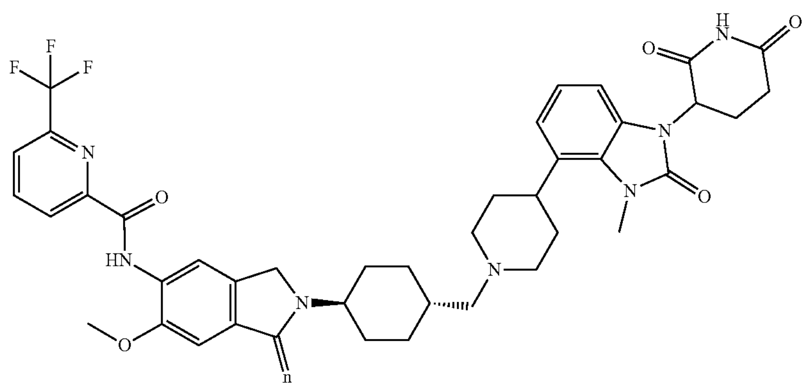 |
| I-18 | 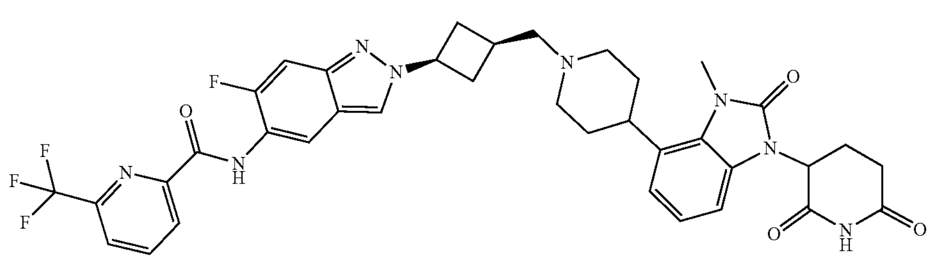 [SMILES: Cn1c(=O)n(C2CCC(=O)NC2=O)c2cccc(C3CCN(C[C@H]4C[C@@H](n5cc6cc(NC(=O)c7cccc(C(F)(F)F)n7)c(F)cc6n5)C4)CC3)c21] |
| I-19 | 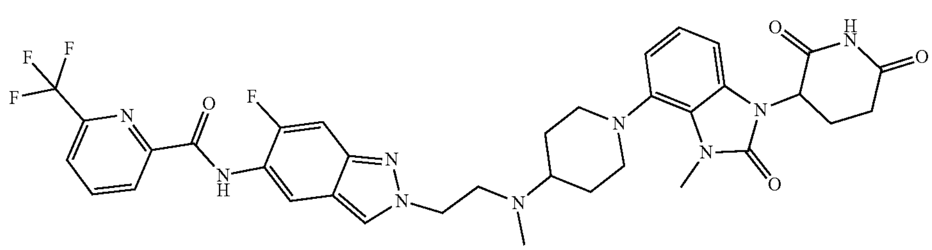 [SMILES: CN(CCn1cc2cc(NC(=O)c3cccc(C(F)(F)F)n3)c(F)cc2n1)C1CCN(c2cccc3c2n(C)c(=O)n3C2CCC(=O)NC2=O)CC1] |

TABLE 1-continued
Exemplary Compounds
| I-# | Structure |
|---|---|
| I-20 | 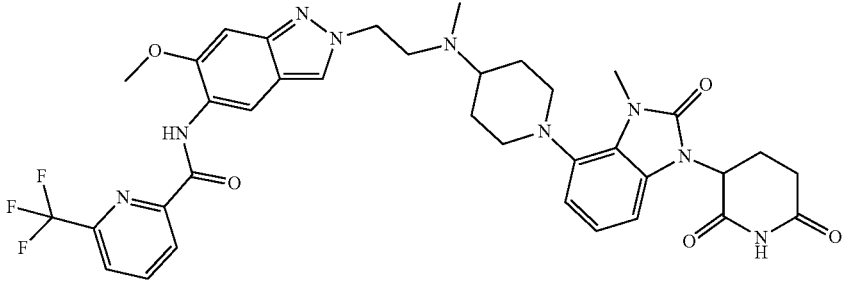 [SMILES: COc1cc2nn(CCN(C)C3CCN(c4cccc5c4n(C)c(=O)n5C4CCC(=O)NC4=O)CC3)cc2cc1NC(=O)c1cccc(C(F)(F)F)n1] |
| I-21 | 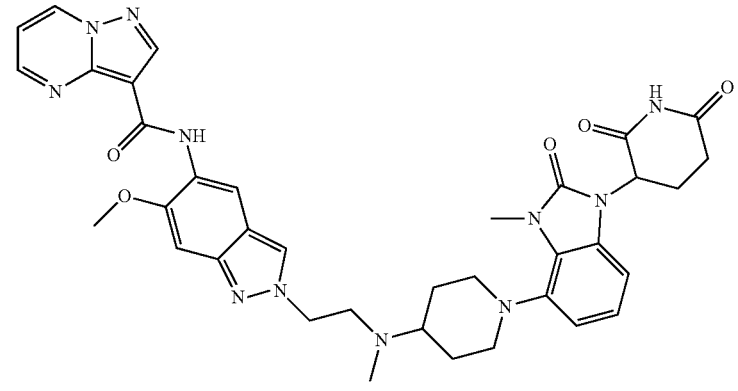 [SMILES: COc1cc2nn(CCN(C)C3CCN(c4cccc5c4n(C)c(=O)n5C4CCC(=O)NC4=O)CC3)cc2cc1NC(=O)c1cnn2cccnc12] |
| I-22 | 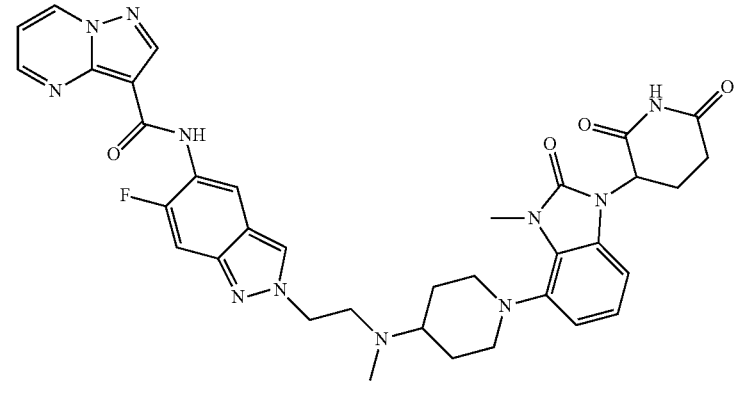 [SMILES: CN(CCn1cc2cc(NC(=O)c3cnn4cccnc34)c(F)cc2n1)C1CCN(c2cccc3c2n(C)c(=O)n3C2CCC(=O)NC2=O)CC1] |
| I-23 | 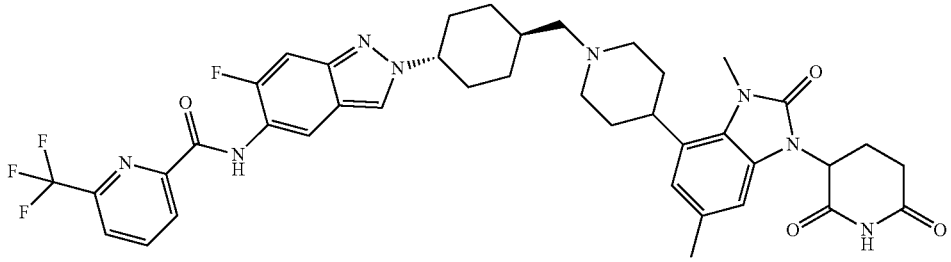 [SMILES: Cc1cc(C2CCN(C[C@H]3CC[C@H](n4cc5cc(NC(=O)c6cccc(C(F)(F)F)n6)c(F)cc5n4)CC3)CC2)c2c(c1)n(C1CCC(=O)NC1=O)c(=O)n2C] |

TABLE 1-continued

Exemplary Compounds

| I-# | Structure |
|---|---|
| I-24 | 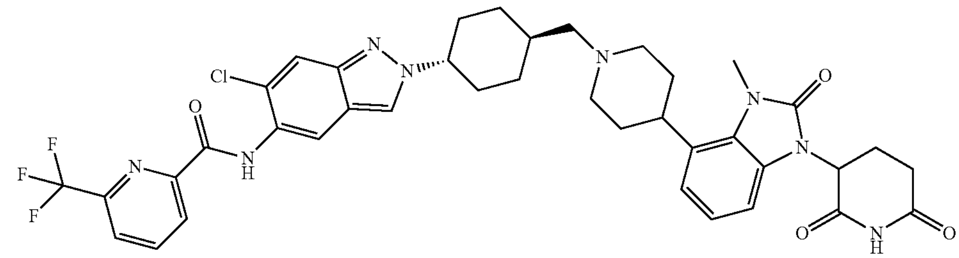 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(Cl)cc6n5)CC4)CC3)c21] |
| I-25 | 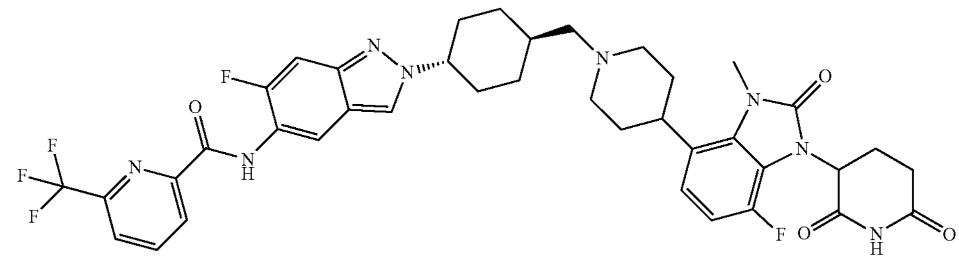 [SMILES: Cn1c(=O)n(C2CCC(=O)NC2=O)c2c(F)ccc(C3CCN(C[C@H]4CC[C@H](n5cc6cc(NC(=O)c7cccc(C(F)(F)F)n7)c(F)cc6n5)CC4)CC3)c21] |
| I-26 | 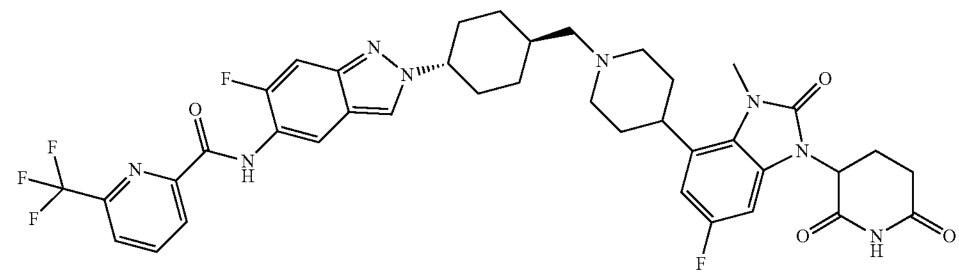 [SMILES: Cn1c(=O)n(C2CCC(=O)NC2=O)c2cc(F)cc(C3CCN(C[C@H]4CC[C@H](n5cc6cc(NC(=O)c7cccc(C(F)(F)F)n7)c(F)cc6n5)CC4)CC3)c21] |
| I-27 | 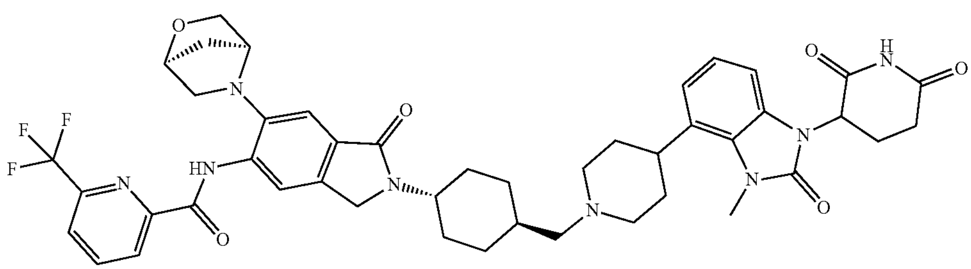 [SMILES: Cn1c(=O)n(C2CCC(=O)NC2=O)c2cccc(C3CCN(C[C@H]4CC[C@H](N5Cc6cc(NC(=O)c7cccc(C(F)(F)F)n7)c(N7C[C@@H]8C[C@H]7CO8)cc6C5=O)CC4)CC3)c21] |
| I-28 | 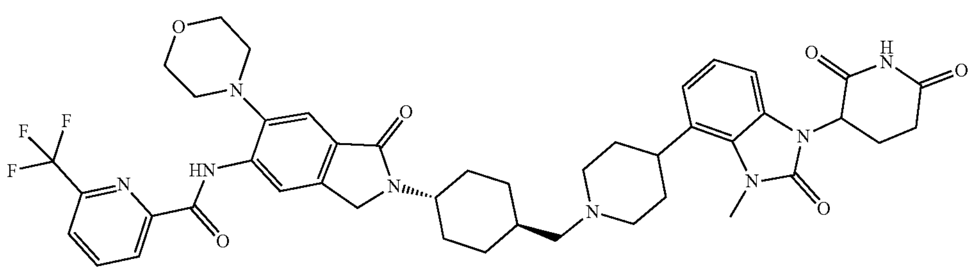 [SMILES: Cn1c(=O)n(C2CCC(=O)NC2=O)c2cccc(C3CCN(C[C@H]4CC[C@H](N5Cc6cc(NC(=O)c7cccc(C(F)(F)F)n7)c(N7CCOCC7)cc6C5=O)CC4)CC3)c21] |

TABLE 1-continued
Exemplary Compounds
| I-# | Structure |
|---|---|
| I-29 | 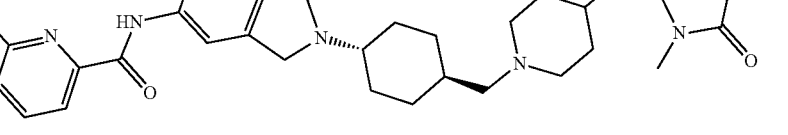 |
| I-30 | 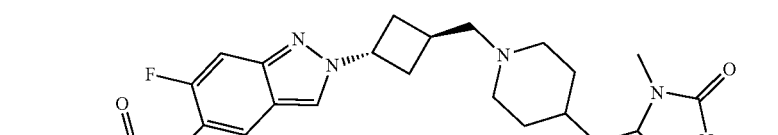 |
| I-31 | 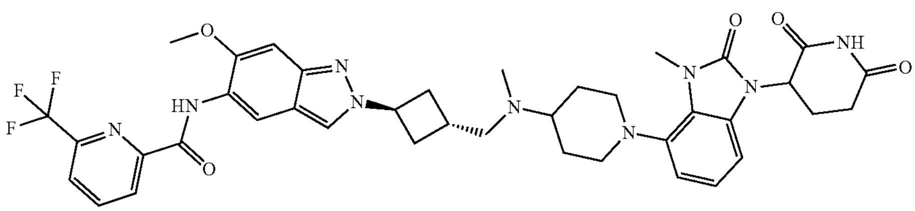 [SMILES: COc1cc2nn([C@H]3C[C@H](CN(C)C4CCN(c5cccc6c5n(C)c(=O)n6C5CCC(=O)NC5=O)CC4)C3)cc2cc1NC(=O)c1cccc(C(F)(F)F)n1] |
| I-32 | 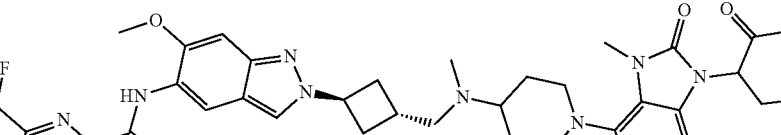 |
| I-33 | 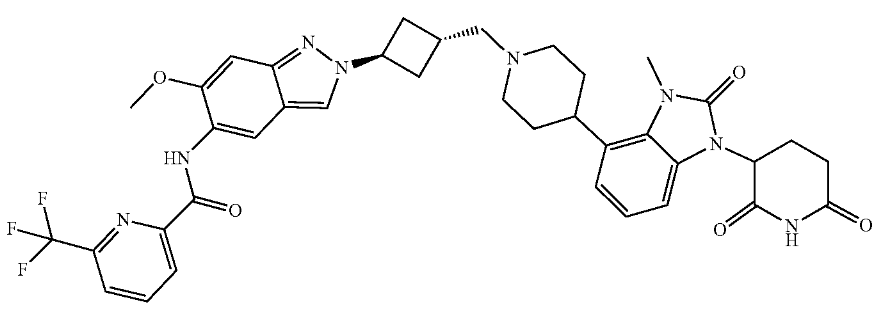 [SMILES: COc1cc2nn([C@H]3C[C@H](CN4CCC(c5cccc6c5n(C)c(=O)n6C5CCC(=O)NC5=O)CC4)C3)cc2cc1NC(=O)c1cccc(C(F)(F)F)n1] |
| I-34 | 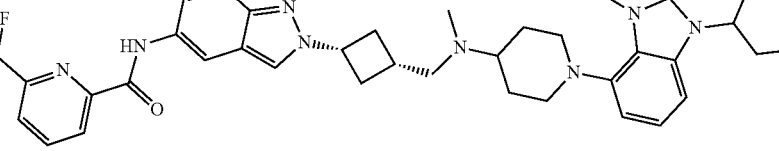 |

TABLE 1-continued

Exemplary Compounds

| I-# | Structure |
|---|---|
| I-35 | 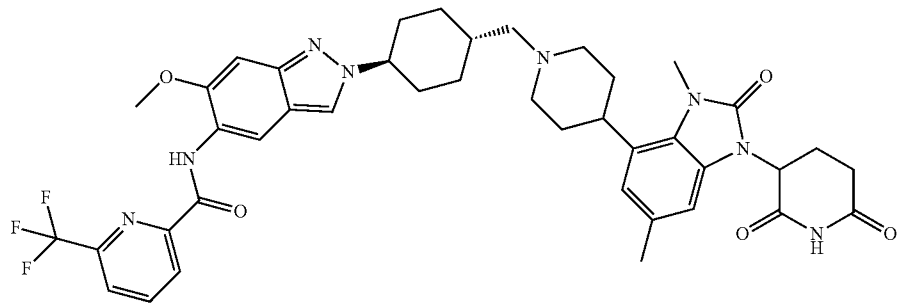 [SMILES: COc1cc2nn([C@H]3CC[C@H](CN4CCC(c5cc(C)cc6c5n(C)c(=O)n6C5CCC(=O)NC5=O)CC4)CC3)cc2cc1NC(=O)c1cccc(C(F)(F)F)n1] |
| I-36 | 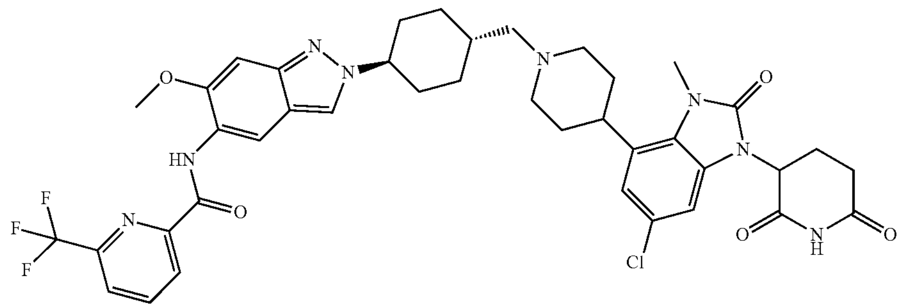 [SMILES: COc1cc2nn([C@H]3CC[C@H](CN4CCC(c5cc(Cl)cc6c5n(C)c(=O)n6C5CCC(=O)NC5=O)CC4)CC3)cc2cc1NC(=O)c1cccc(C(F)(F)F)n1] |
| I-37 | 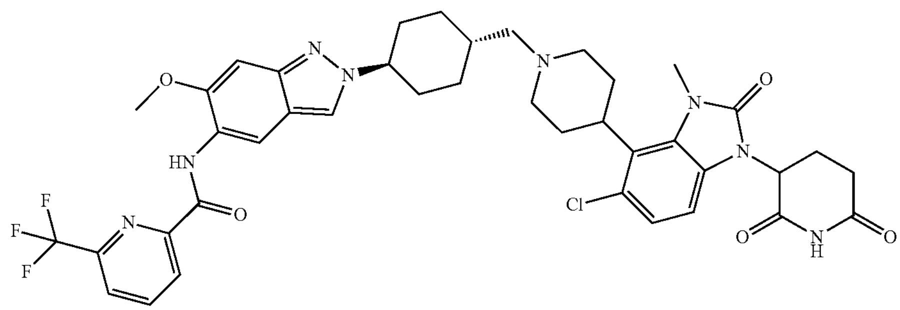 [SMILES: COc1cc2nn([C@H]3CC[C@H](CN4CCC(c5c(Cl)ccc6c5n(C)c(=O)n6C5CCC(=O)NC5=O)CC4)CC3)cc2cc1NC(=O)c1cccc(C(F)(F)F)n1] |
| I-38 | 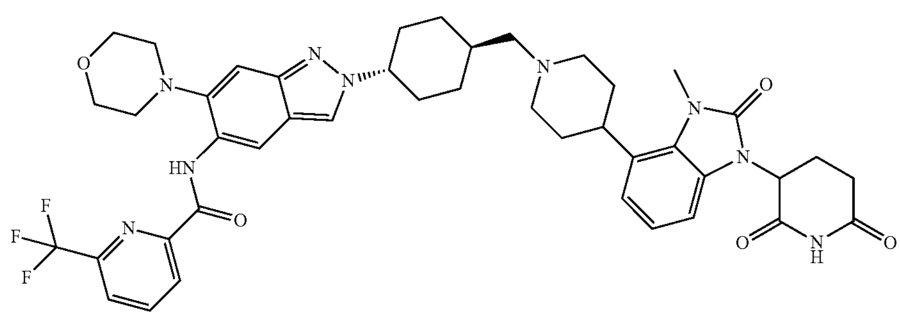 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(N7CCOCC7)cc6n5)CC4)CC3)c21] |
| I-39 | 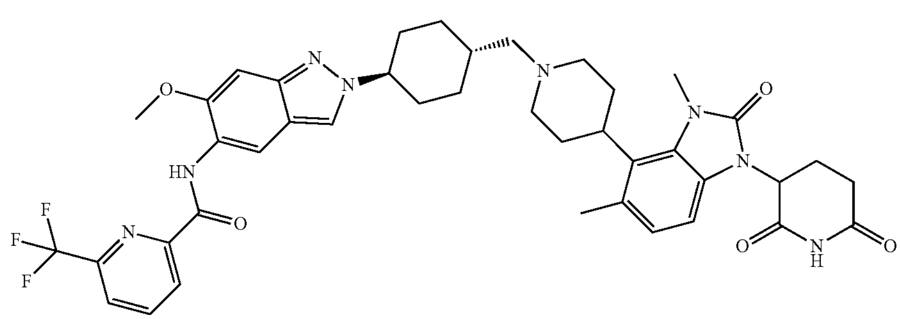 [SMILES: COc1cc2nn([C@H]3CC[C@H](CN4CCC(c5c(C)ccc6c5n(C)c(=O)n6C5CCC(=O)NC5=O)CC4)CC3)cc2cc1NC(=O)c1cccc(C(F)(F)F)n1] |

TABLE 1-continued

Exemplary Compounds

| I-# | Structure |
|---|---|
| I-40 | 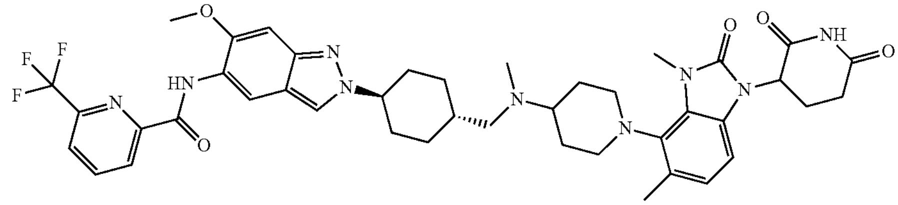 [SMILES: COc1cc2nn([C@H]3CC[C@H](CN(C)C4CCN(c5c(C)ccc6c5n(C)c(=O)n6C5CCC(=O)NC5=O)CC4)CC3)cc2cc1NC(=O)c1cccc(C(F)(F)F)n1] |
| I-41 | 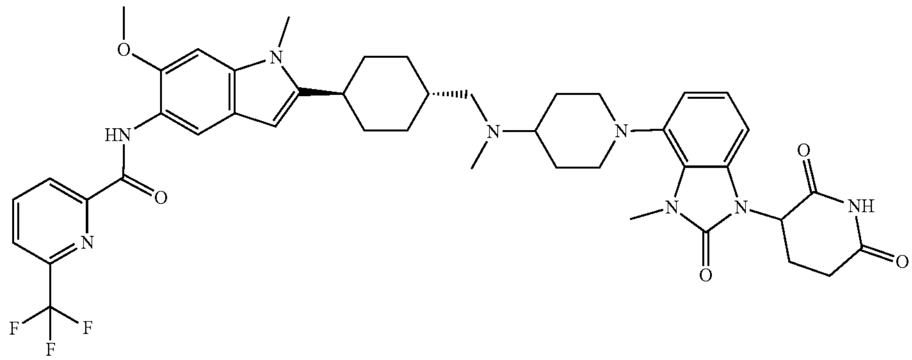 [SMILES: COc1cc2c(cc1NC(=O)c1cccc(C(F)(F)F)n1)cc([C@H]1CC[C@H](CN(C)C3CCN(c4cccc5c4n(C)c(=O)n5C4CCC(=O)NC4=O)CC3)CC1)n2C] |
| I-42 | 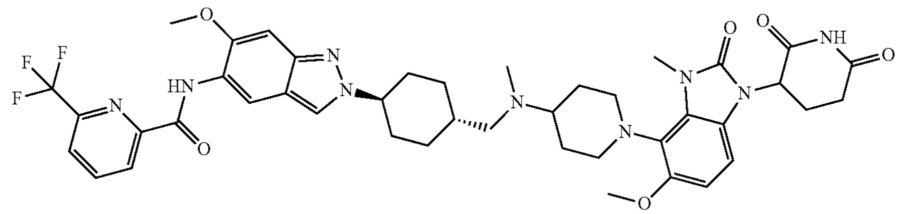 [SMILES: COc1cc2nn([C@H]3CC[C@H](CN(C)C4CCN(c5c(OC)ccc6c5n(C)c(=O)n6C5CCC(=O)NC5=O)CC4)CC3)cc2cc1NC(=O)c1cccc(C(F)(F)F)n1] |
| I-43 | 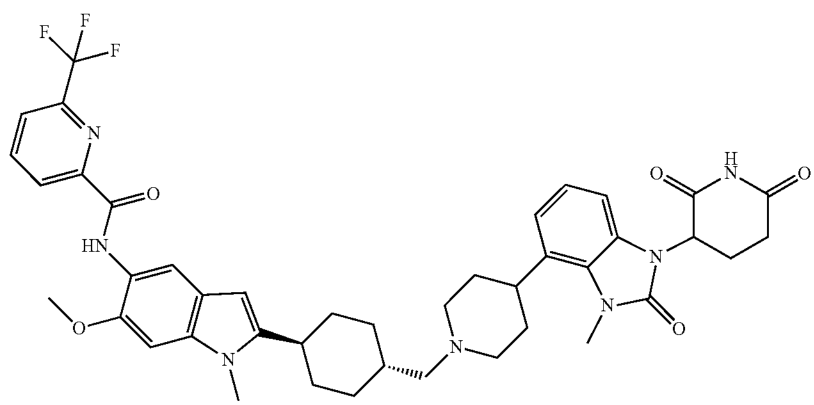 [SMILES: COc1cc2c(cc1NC(=O)c1cccc(C(F)(F)F)n1)cc([C@H]1CC[C@H](CN3CCC(c4cccc5c4n(C)c(=O)n5C4CCC(=O)NC4=O)CC3)CC1)n2C] |
| I-44 | 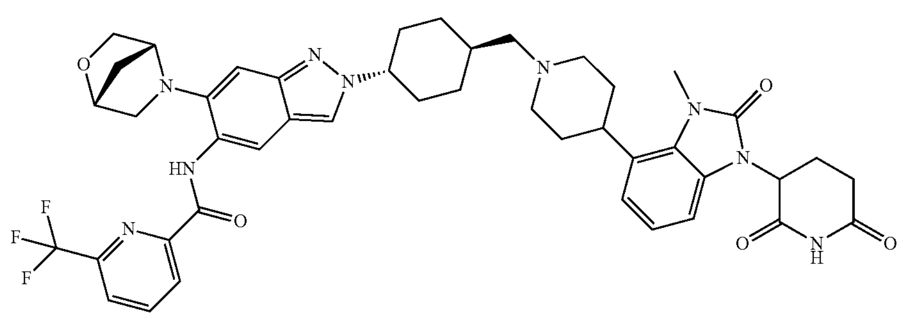 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(N7C[C@H]8C[C@@H]7CO8)cc6n5)CC4)CC3)c21] |

TABLE 1-continued

Exemplary Compounds

| I-# | Structure |
|---|---|
| I-45 | 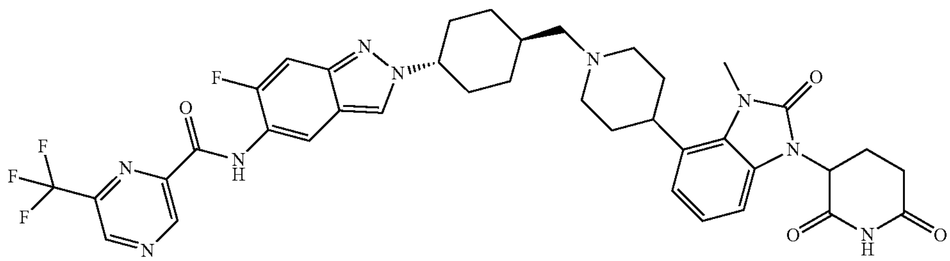 [SMILES: Cn1c(=O)n(C2CCC(=O)NC2=O)c2cccc(C3CCN(C[C@H]4CC[C@H](n5cc6cc(NC(=O)c7cncc(C(F)(F)F)n7)c(F)cc6n5)CC4)CC3)c21] |
| I-46 | 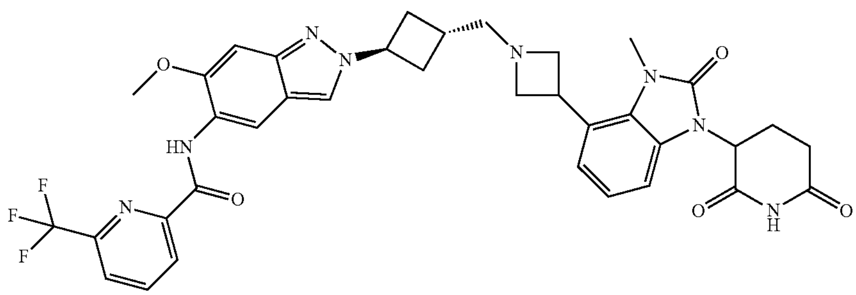 [SMILES: COc1cc2nn([C@H]3C[C@H](CN4CC(c5cccc6c5n(C)c(=O)n6C5CCC(=O)NC5=O)C4)C3)cc2cc1NC(=O)c1cccc(C(F)(F)F)n1] |
| I-47 | 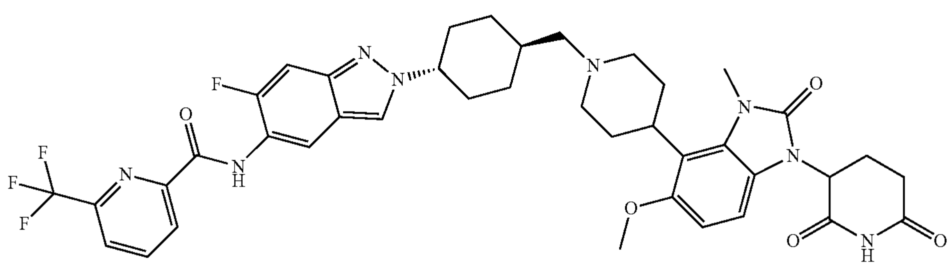 [SMILES: COc1ccc2c(c1C1CCN(C[C@H]3CC[C@H](n4cc5cc(NC(=O)c6cccc(C(F)(F)F)n6)c(F)cc5n4)CC3)CC1)n(C)c(=O)n2C1CCC(=O)NC1=O] |
| I-48 | 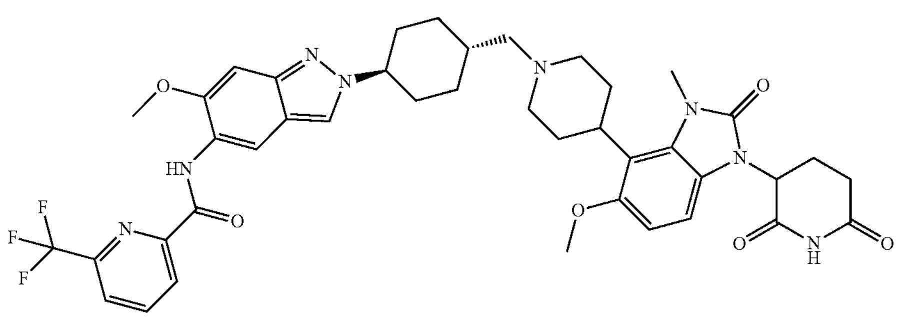 [SMILES: COc1cc2nn([C@H]3CC[C@H](CN4CCC(c5c(OC)ccc6c5n(C)c(=O)n6C5CCC(=O)NC5=O)CC4)CC3)cc2cc1NC(=O)c1cccc(C(F)(F)F)n1] |
| I-49 | 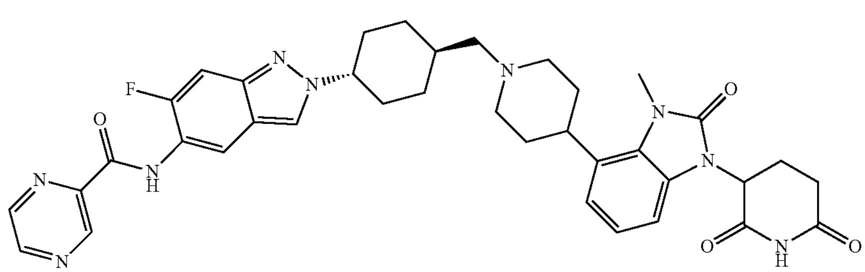 [SMILES: Cn1c(=O)n(C2CCC(=O)NC2=O)c2cccc(C3CCN(C[C@H]4CC[C@H](n5cc6cc(NC(=O)c7cnccn7)c(F)cc6n5)CC4)CC3)c21] |

TABLE 1-continued
Exemplary Compounds
| I-# | Structure |
|---|---|
| I-50 | 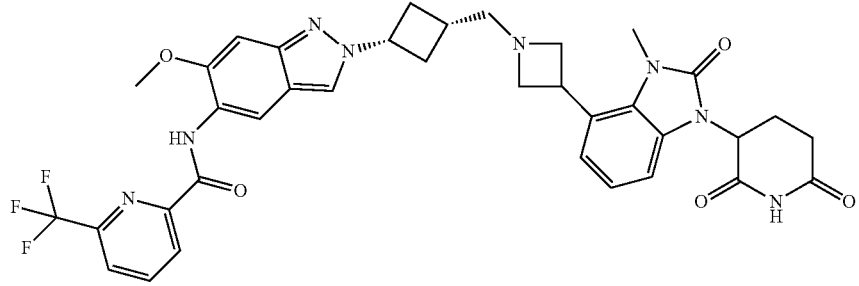 [SMILES: COc1cc2nn([C@H]3C[C@@H](CN4CC(c5cccc6c5n(C)c(=O)n6C5CCC(=O)NC5=O)C4)C3)cc2cc1NC(=O)c1cccc(C(F)(F)F)n1] |
| I-51 | 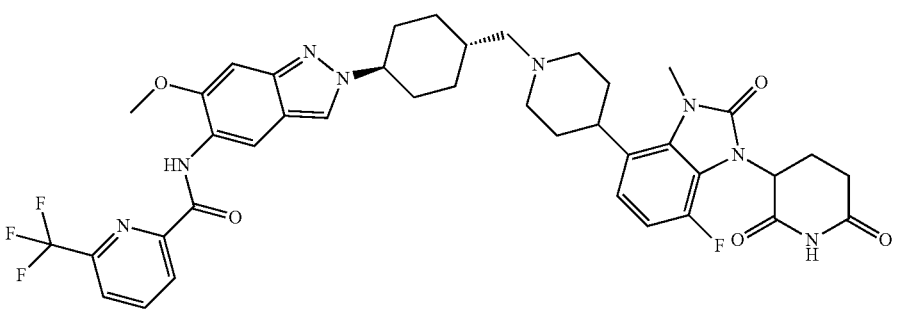 [SMILES: COc1cc2nn([C@H]3CC[C@H](CN4CCC(c5ccc(F)c6c5n(C)c(=O)n6C5CCC(=O)NC5=O)CC4)CC3)cc2cc1NC(=O)c1cccc(C(F)(F)F)n1] |
| I-52 | 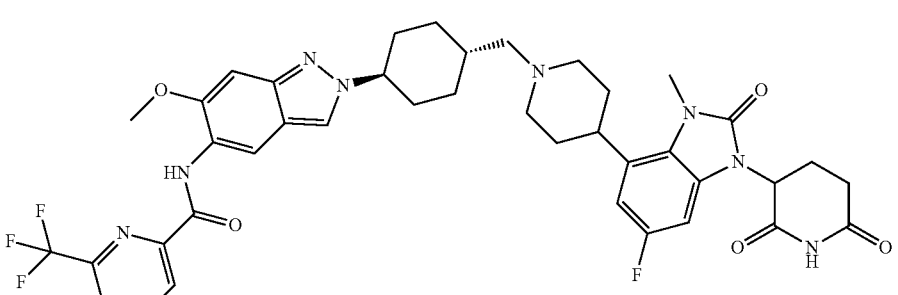 |
| I-53 | 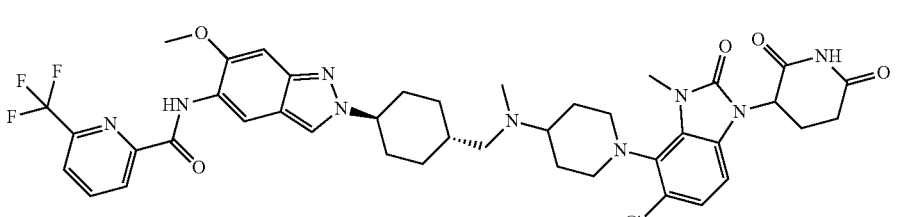 |
| I-54 | 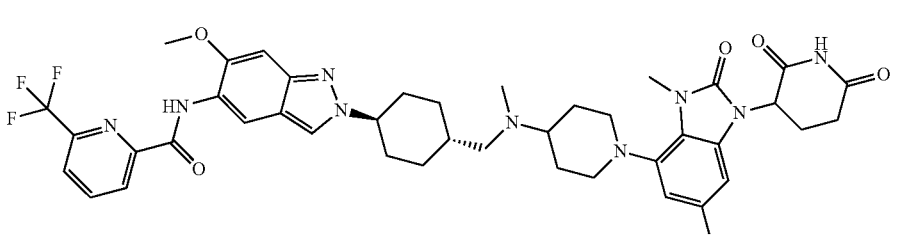 |

TABLE 1-continued

Exemplary Compounds

| I-# | Structure |
|---|---|
| I-55 | 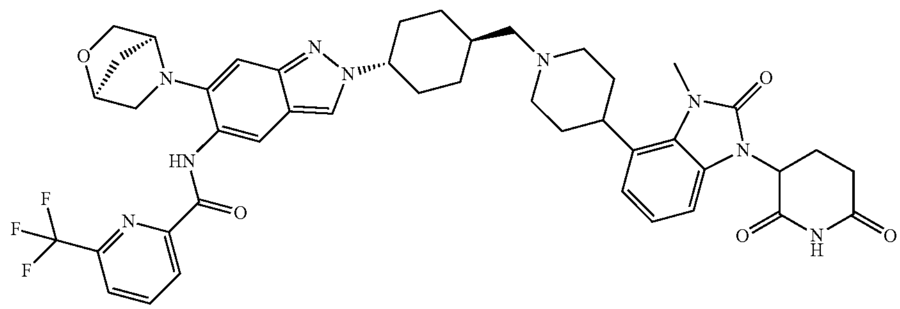 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(N7C[C@@H]8C[C@H]7CO8)cc6n5)CC4)CC3)c21] |
| I-56 | 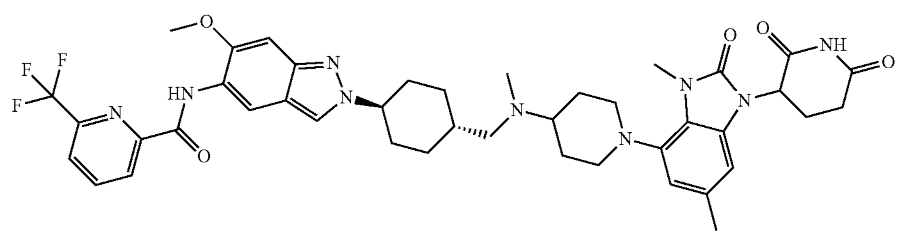 [SMILES: COc1cc2nn([C@H]3CC[C@H](CN(C)C4CCN(c5cc(C)cc6c5n(C)c(=O)n6C5CCC(=O)NC5=O)CC4)CC3)cc2cc1NC(=O)c1cccc(C(F)(F)F)n1] |
| I-57 | 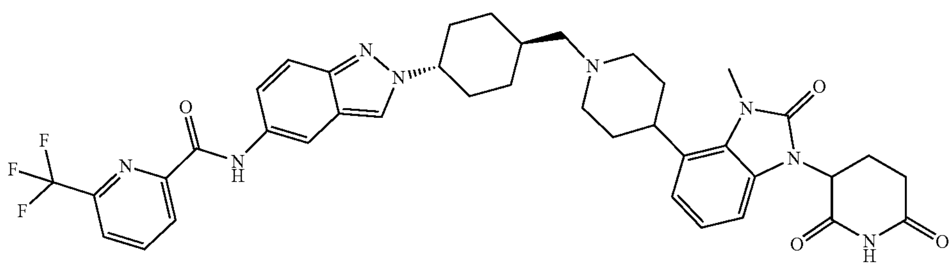 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ccc6n5)CC4)CC3)c21] |
| I-58 | 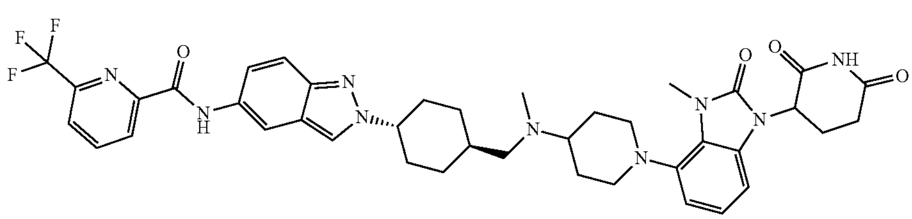 [SMILES: CN(C[C@H]1CC[C@H](n2cc3cc(NC(=O)c4cccc(C(F)(F)F)n4)ccc3n2)CC1)C1CCN(c2cccc3c2n(C)c(=O)n3C2CCC(=O)NC2=O)CC1] |
| I-59 | 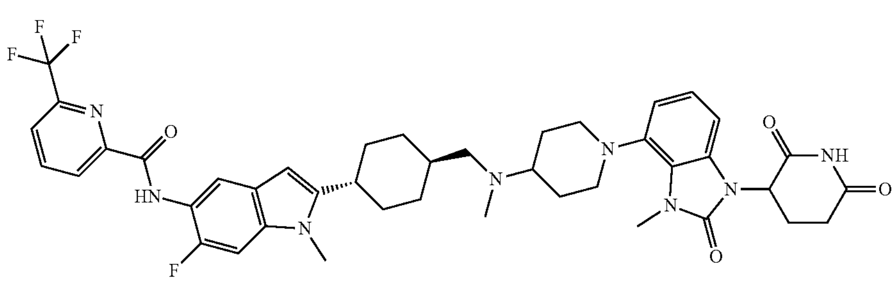 [SMILES: CN(C[C@H]1CC[C@H](c2cc3cc(NC(=O)c4cccc(C(F)(F)F)n4)c(F)cc3n2C)CC1)C1CCN(c2cccc3c2n(C)c(=O)n3C2CCC(=O)NC2=O)CC1] |

TABLE 1-continued

Exemplary Compounds

| I-# | Structure |
|---|---|
| I-60 | 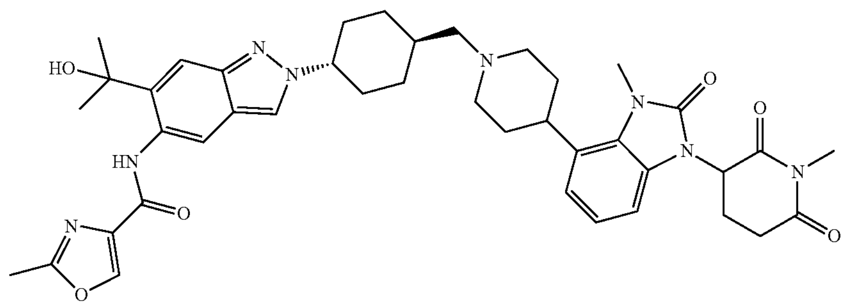 |
| I-61 | 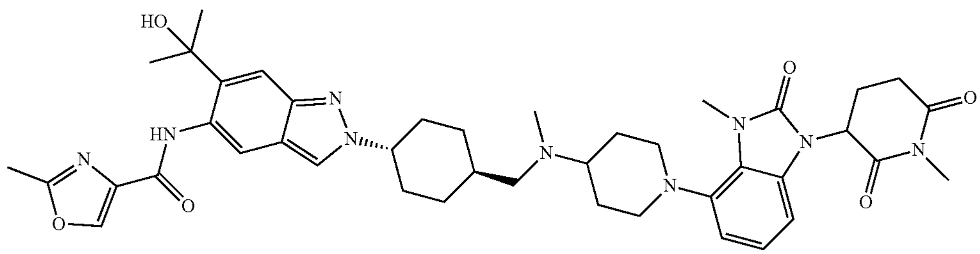 [SMILES: Cc1nc(C(=O)Nc2cc3cn([C@H]4CC[C@H](CN(C)C5CCN(c6cccc7c6n(C)c(=O)n7C6CCC(=O)N(C)C6=O)CC5)CC4)nc3cc2C(C)(C)O)co1] |
| I-62 | 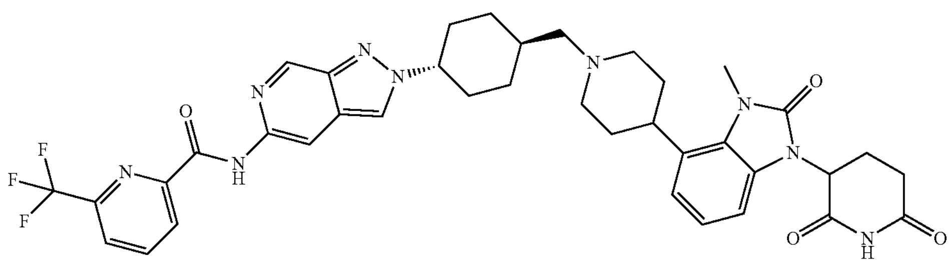 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ncc6n5)CC4)CC3)c21] |
| I-63 | 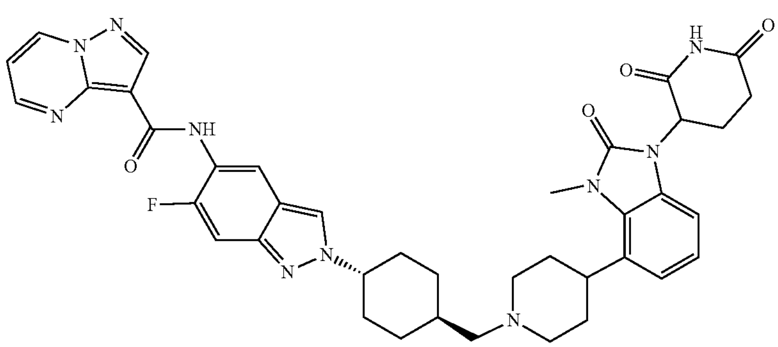 [SMILES: Cn1c(=O)n(C2CCC(=O)NC2=O)c2cccc(C3CCN(C[C@H]4CC[C@H](n5cc6cc(NC(=O)c7cnn8cccnc78)c(F)cc6n5)CC4)CC3)c21] |
| I-64 | 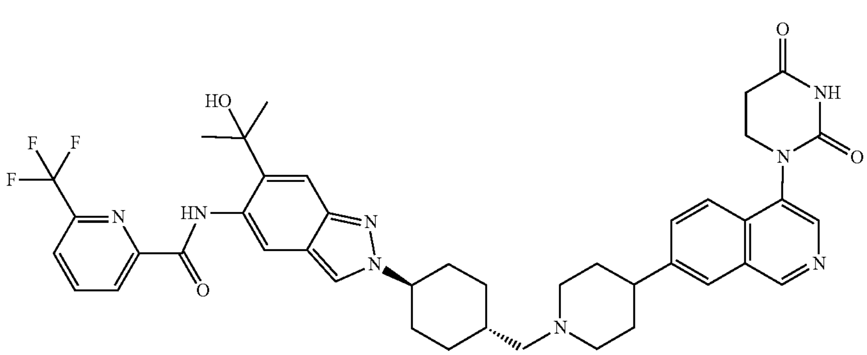 [SMILES: CC(C)(O)c1cc2nn([C@H]3CC[C@H](CN4CCC(c5ccc6c(N7CCC(=O)NC7=O)cncc6c5)CC4)CC3)cc2cc1NC(=O)c1cccc(C(F)(F)F)n1] |

TABLE 1-continued

Exemplary Compounds

| I-# | Structure |
| --- | --- |
| I-65 | 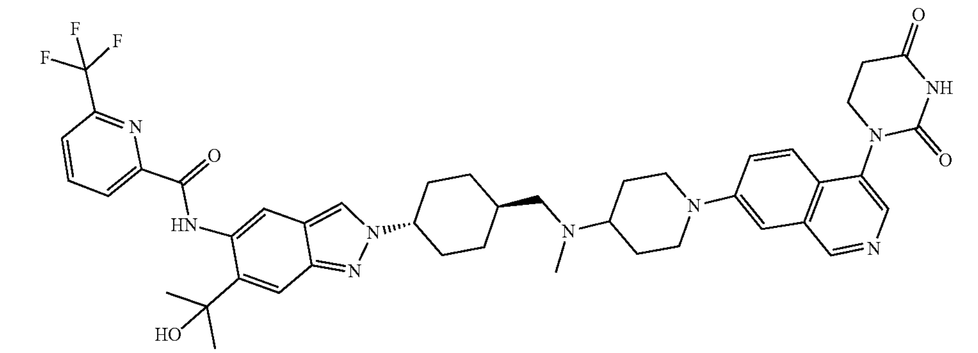 [SMILES: CN(C[C@H]1CC[C@H](n2cc3cc(NC(=O)c4cccc(C(F)(F)F)n4)c(C(C)(C)O)cc3n2)CC1)C1CCN(c2ccc3c(N4CCC(=O)NC4=O)cncc3c2)CC1] |
| I-66 | 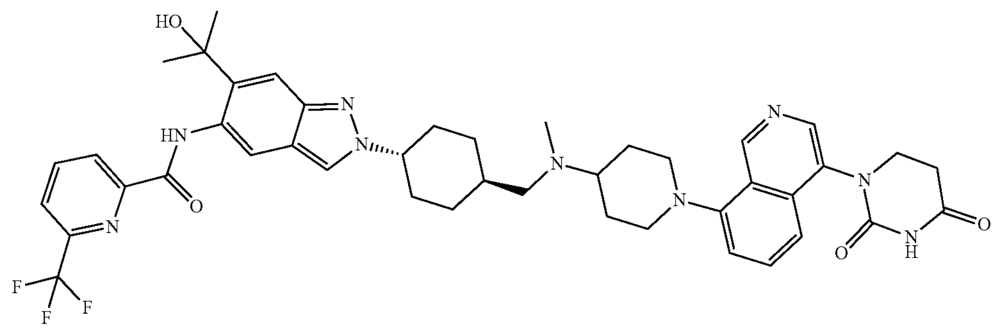 [SMILES: CN(C[C@H]1CC[C@H](n2cc3cc(NC(=O)c4cccc(C(F)(F)F)n4)c(C(C)(C)O)cc3n2)CC1)C1CCN(c2cccc3c(N4CCC(=O)NC4=O)cncc23)CC1] |
| I-67 | 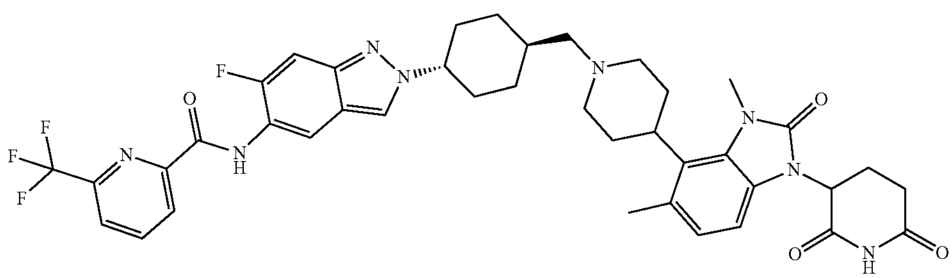 [SMILES: Cc1ccc2c(c1C1CCN(C[C@H]3CC[C@H](n4cc5cc(NC(=O)c6cccc(C(F)(F)F)n6)c(F)cc5n4)CC3)CC1)n(C)c(=O)n2C1CCC(=O)NC1=O] |
| I-68 | 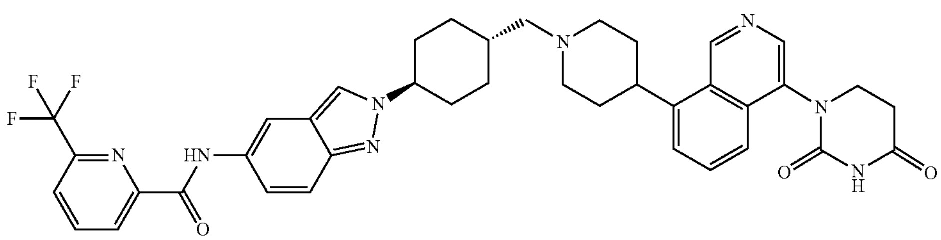 [SMILES: O=C1CCN(c2cncc3c(C4CCN(C[C@H]5CC[C@H](n6cc7cc(NC(=O)c8cccc(C(F)(F)F)n8)ccc7n6)CC5)CC4)cccc23)C(=O)N1] |
| I-69 | 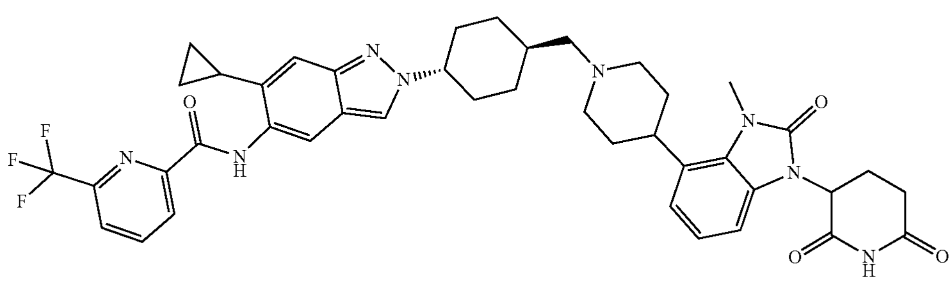 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C7CC7)cc6n5)CC4)CC3)c21] |

TABLE 1-continued

Exemplary Compounds

| I-# | Structure |
|-----|-----------|
| I-70 | 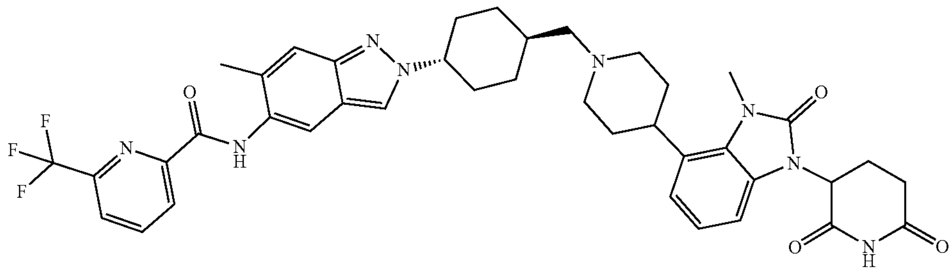 [SMILES: Cc1cc2nn([C@H]3CC[C@H](CN4CCC(c5cccc6c5n(C)c(=O)n6C5CCC(=O)NC5=O)CC4)CC3)cc2cc1NC(=O)c1cccc(C(F)(F)F)n1] |
| I-71 | 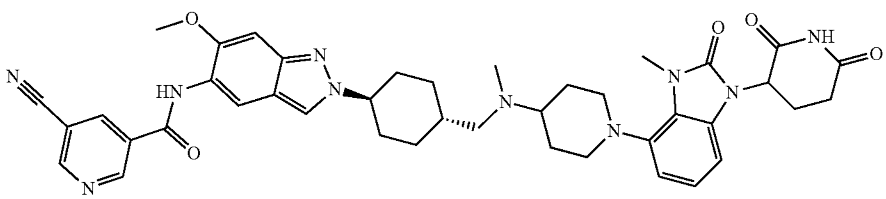 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncc(C#N)c1] |
| I-72 | 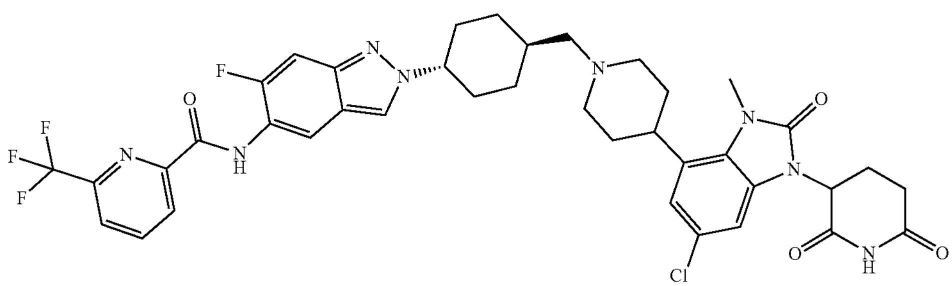 [SMILES: Cn1c(=O)n(C2CCC(=O)NC2=O)c2cc(Cl)cc(C3CCN(C[C@H]4CC[C@H](n5cc6cc(NC(=O)c7cccc(C(F)(F)F)n7)c(F)cc6n5)CC4)CC3)c21] |
| I-73 | 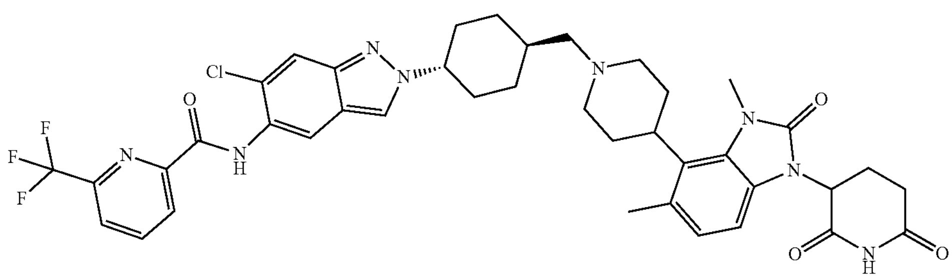 [SMILES: Cc1ccc2c(c1C1CCN(C[C@H]3CC[C@H](n4cc5cc(NC(=O)c6cccc(C(F)(F)F)n6)c(Cl)cc5n4)CC3)CC1)n(C)c(=O)n2C1CCC(=O)NC1=O] |
| I-74 | 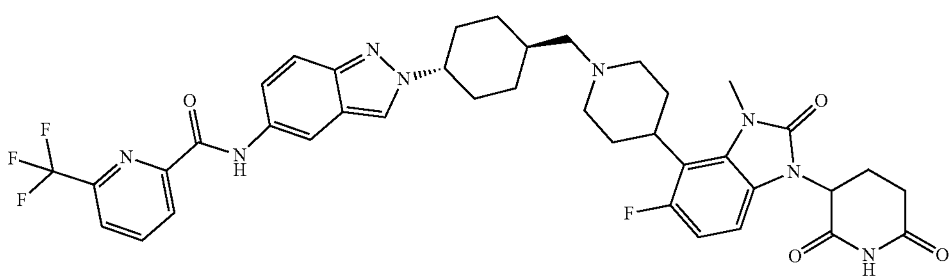 |

TABLE 1-continued

Exemplary Compounds

| I-# | Structure |
|---|---|
| I-75 | 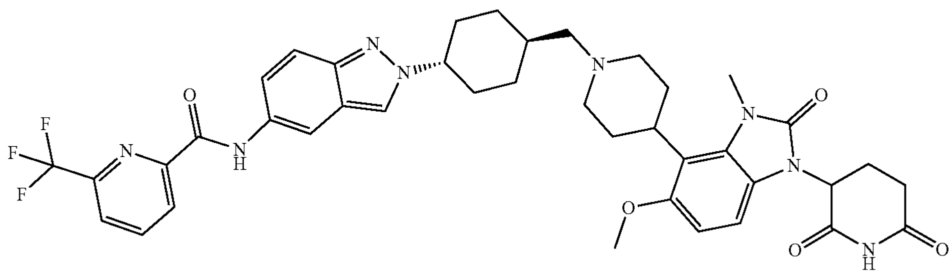 |
| I-76 | 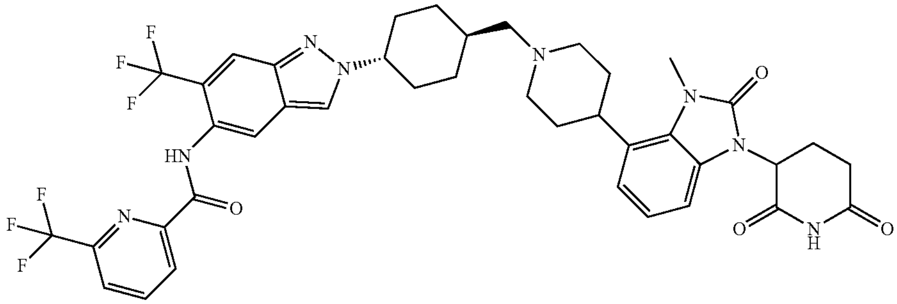 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C(F)(F)F)cc6n5)CC4)CC3)c21] |
| I-77 | 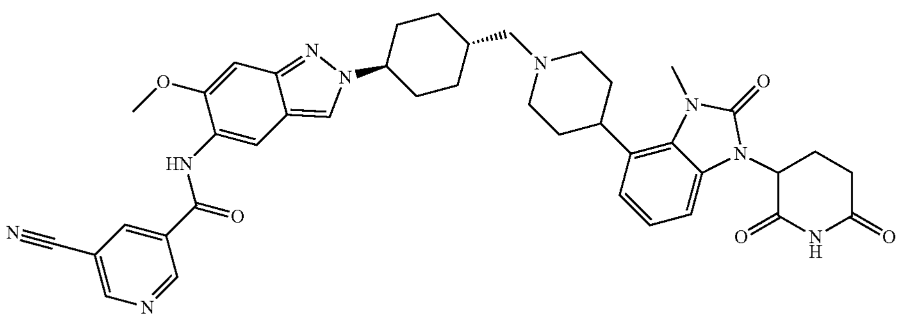 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cncc(C#N)c1] |
| I-78 | 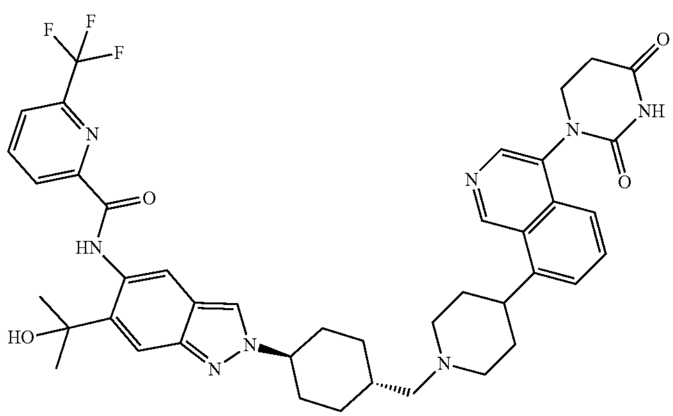 [SMILES: CC(C)(O)c1cc2nn([C@H]3CC[C@H](CN4CCC(c5cccc6c(N7CCC(=O)NC7=O)cncc56)CC4)CC3)cc2cc1NC(=O)c1cccc(C(F)(F)F)n1] |
| I-79 | 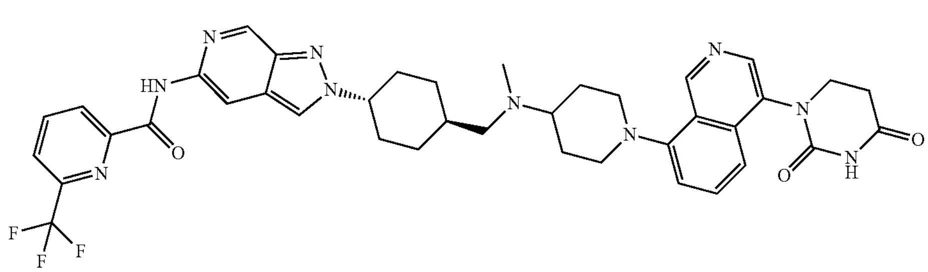 |

TABLE 1-continued

Exemplary Compounds

| I-# | Structure |
| --- | --- |
| I-80 | 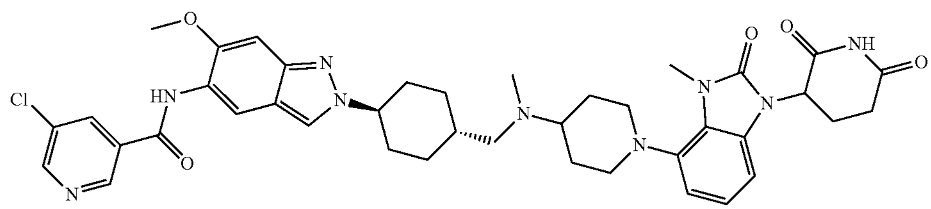 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncc(Cl)c1] |
| I-81 | 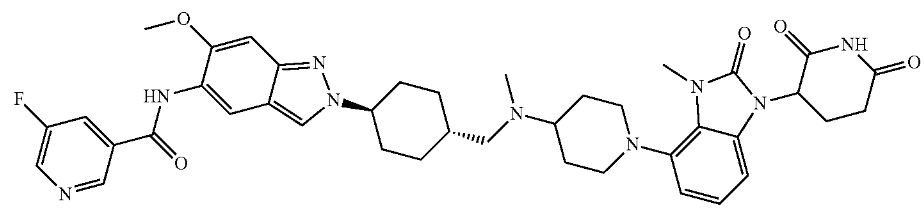 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncc(F)c1] |
| I-82 | 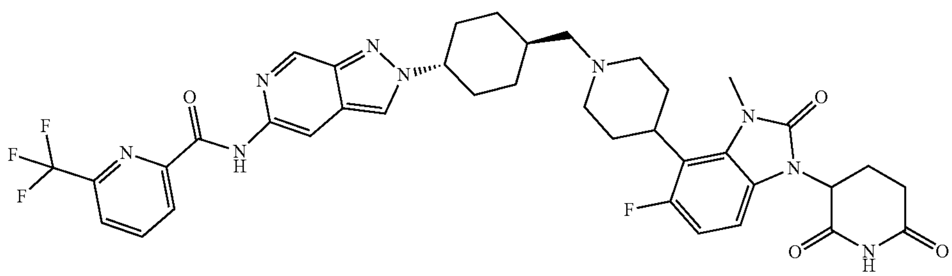 |
| I-83 | 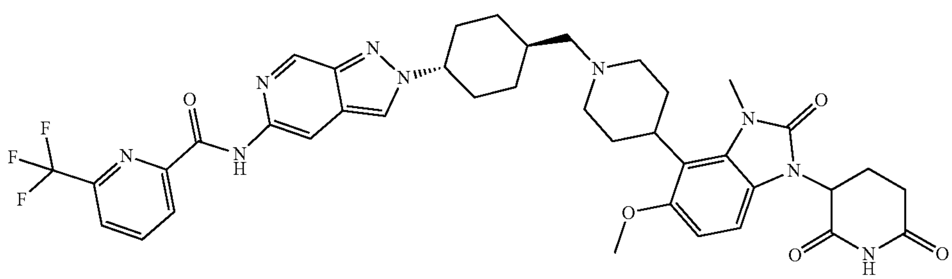 [SMILES: Cn1c(=O)n(C2CCC(=O)NC2=O)c2ccc(F)c(C3CCN(C[C@H]4CC[C@H](n5cc6cc(NC(=O)c7cccc(C(F)(F)F)n7)ncc6n5)CC4)CC3)c21] |
| I-84 | 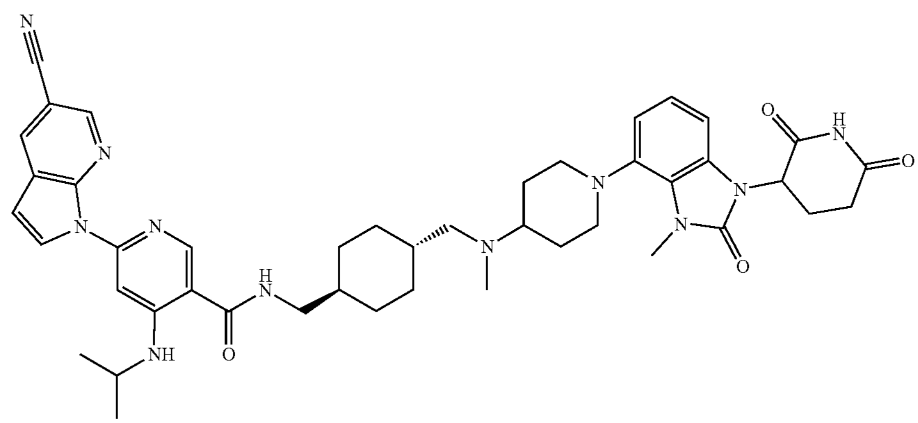 [SMILES: CC(C)Nc1cc(-n2ccc3cc(C#N)cnc32)ncc1C(=O)NC[C@H]1CC[C@H](CN(C)C2CCN(c3cccc4c3n(C)c(=O)n4C3CCC(=O)NC3=O)CC2)CC1] |

TABLE 1-continued

Exemplary Compounds

| I-# | Structure |
|---|---|
| I-85 | 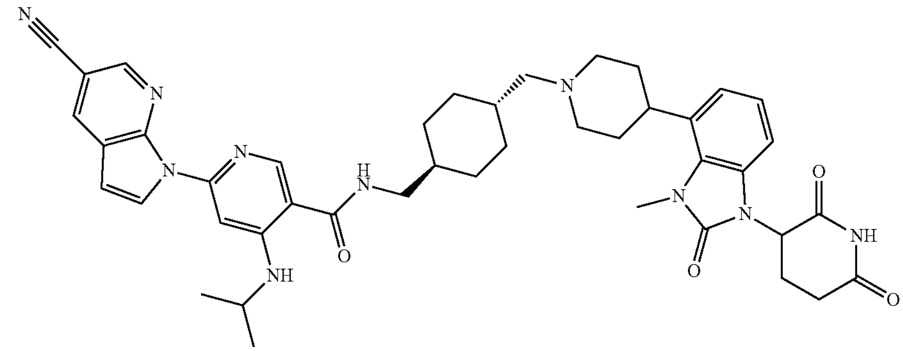 [SMILES: CC(C)Nc1cc(-n2ccc3cc(C#N)cnc32)ncc1C(=O)NC[C@H]1CC[C@H](CN2CCC(c3cccc4c3n(C)c(=O)n4C3CCC(=O)NC3=O)CC2)CC1] |
| I-86 | 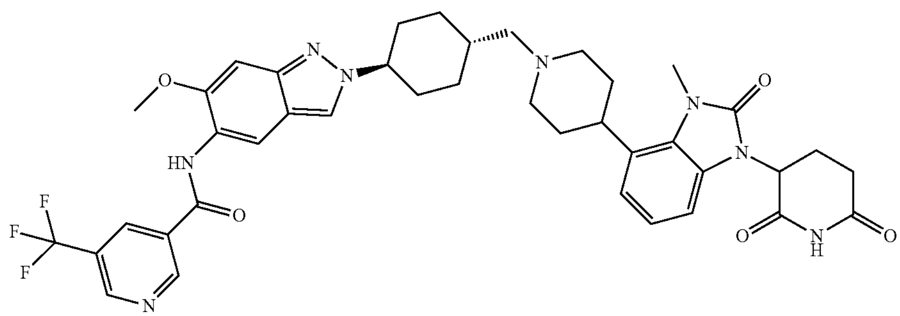 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cncc(C(F)(F)F)c1] |
| I-87 | 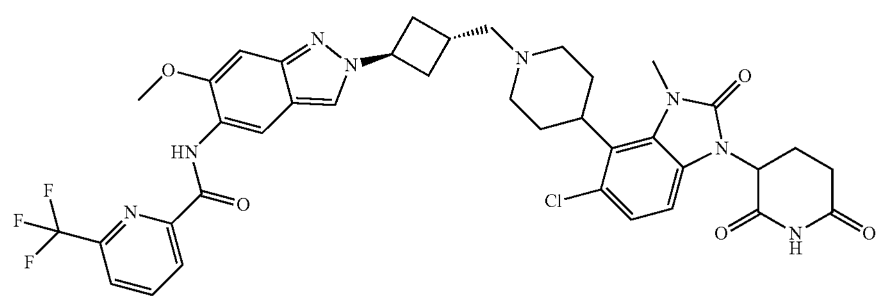 |
| I-88 | 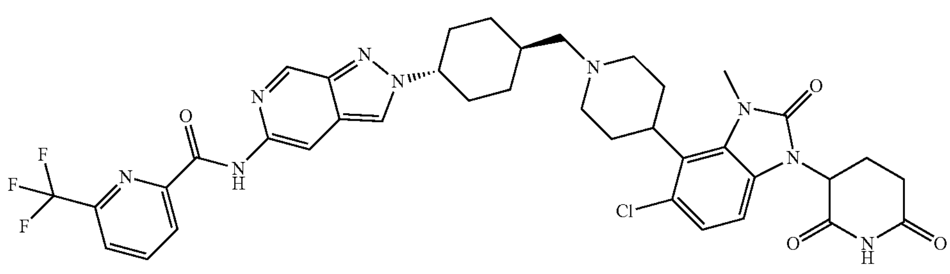 [SMILES: Cn1c(=O)n(C2CCC(=O)NC2=O)c2ccc(Cl)c(C3CCN(C[C@H]4CC[C@H](n5cc6cc(NC(=O)c7cccc(C(F)(F)F)n7)ncc6n5)CC4)CC3)c21] |
| I-89 | 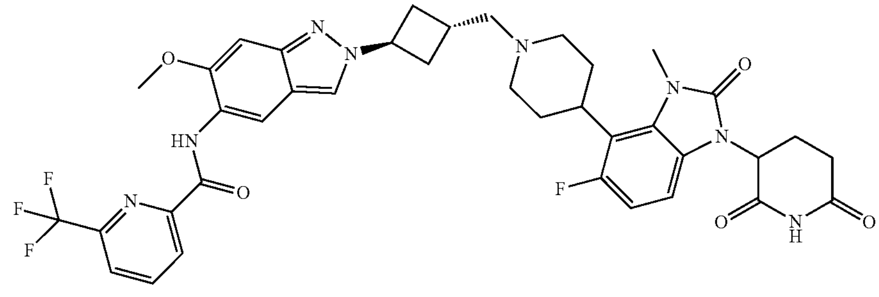 [SMILES: COc1cc2nn([C@H]3C[C@H](CN4CCC(c5c(F)ccc6c5n(C)c(=O)n6C5CCC(=O)NC5=O)CC4)C3)cc2cc1NC(=O)c1cccc(C(F)(F)F)n1] |

TABLE 1-continued
Exemplary Compounds
| I-# | Structure |
|---|---|
| I-90 | 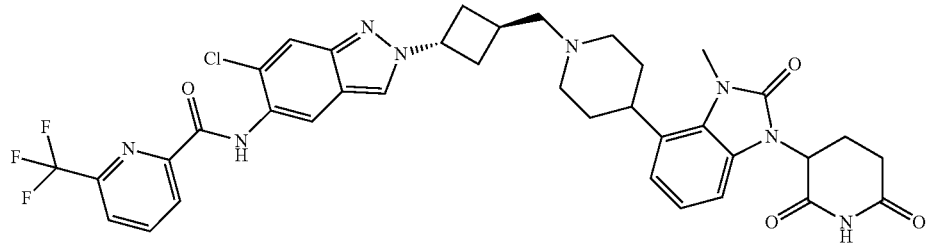 |
| I-91 | 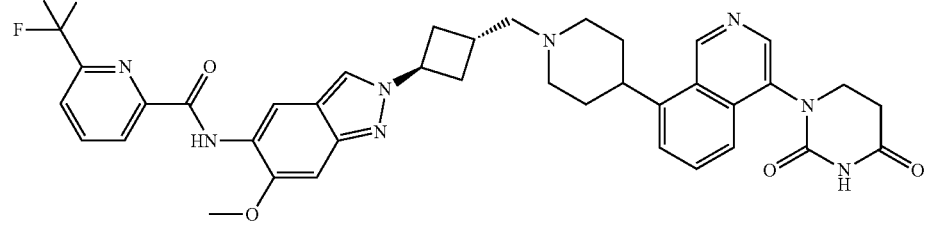 |
| I-92 | 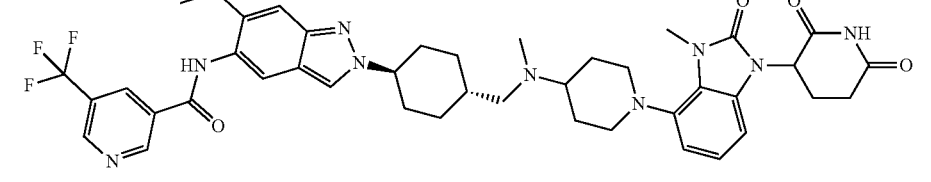 |
| I-93 | 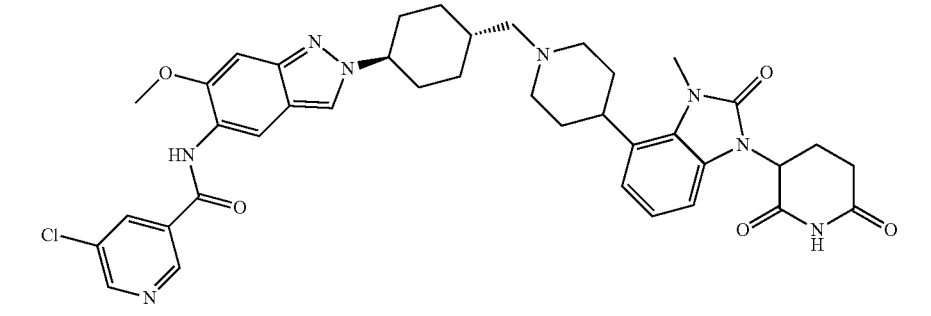 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cncc(Cl)c1] |
| I-94 | 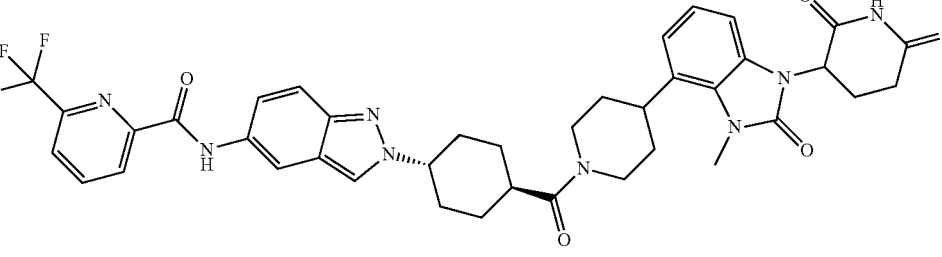 |
| I-95 | 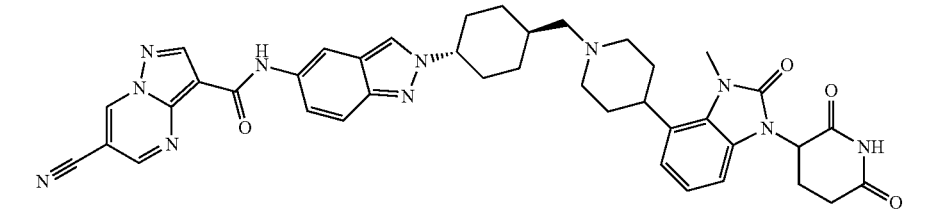 [SMILES: Cn1c(=O)n(C2CCC(=O)NC2=O)c2cccc(C3CCN(C[C@H]4CC[C@H](n5cc6cc(NC(=O)c7cnn8cc(C#N)cnc78)ccc6n5)CC4)CC3)c21] |

TABLE 1-continued
Exemplary Compounds
| I-# | Structure |
|---|---|
| I-96 | 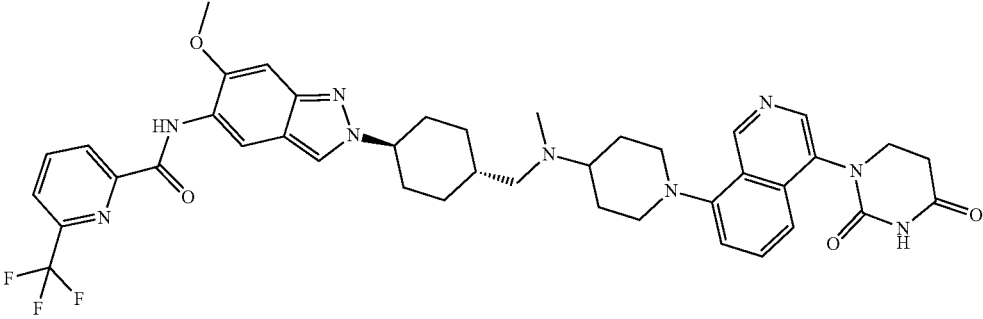 [SMILES: COc1cc2nn([C@H]3CC[C@H](CN(C)C4CCN(c5cccc6c(N7CCC(=O)NC7=O)cncc56)CC4)CC3)cc2cc1NC(=O)c1cccc(C(F)(F)F)n1] |
| I-97 | 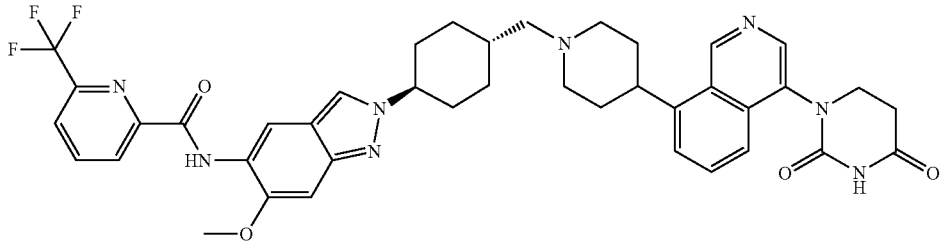 [SMILES: COc1cc2nn([C@H]3CC[C@H](CN4CCC(c5cccc6c(N7CCC(=O)NC7=O)cncc56)CC4)CC3)cc2cc1NC(=O)c1cccc(C(F)(F)F)n1] |
| I-98 | 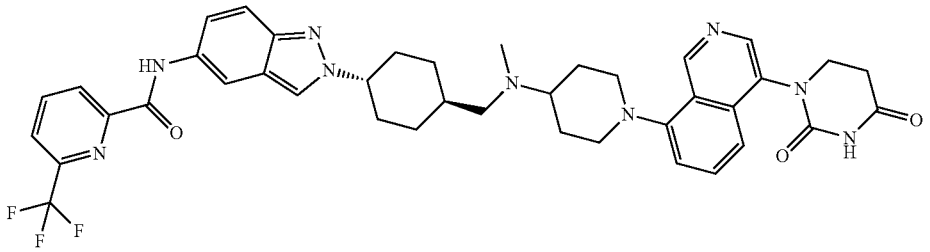 [SMILES: CN(C[C@H]1CC[C@H](n2cc3cc(NC(=O)c4cccc(C(F)(F)F)n4)ccc3n2)CC1)C1CCN(c2cccc3c(N4CCC(=O)NC4=O)cncc23)CC1] |
| I-99 | 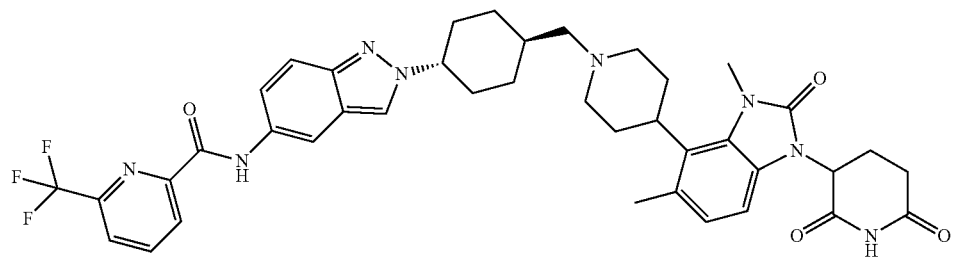 [SMILES: Cc1ccc2c(c1C1CCN(C[C@H]3CC[C@H](n4cc5cc(NC(=O)c6cccc(C(F)(F)F)n6)ccc5n4)CC3)CC1)n(C)c(=O)n2C1CCC(=O)NC1=O] |
| I-100 | 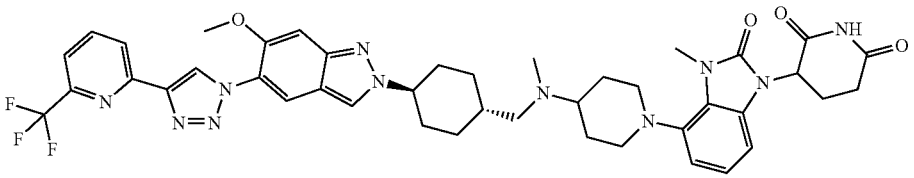 [SMILES: COc1cc2nn([C@H]3CC[C@H](CN(C)C4CCN(c5cccc6c5n(C)c(=O)n6C5CCC(=O)NC5=O)CC4)CC3)cc2cc1-n1cc(-c2cccc(C(F)(F)F)n2)nn1] |

TABLE 1-continued

Exemplary Compounds

| I-# | Structure |
|---|---|
| I-101 | 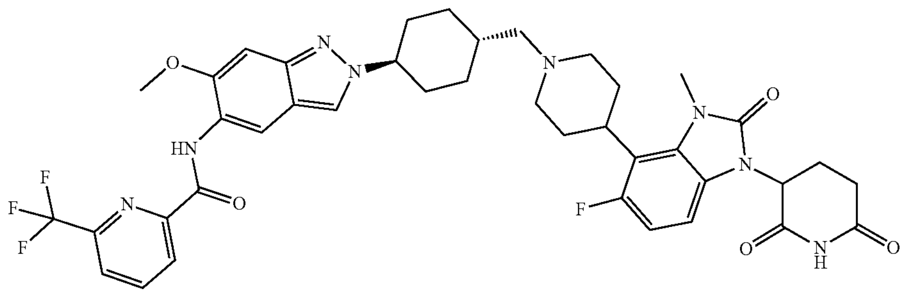 [SMILES: COc1cc2nn([C@H]3CC[C@H](CN4CCC(c5c(F)ccc6c5n(C)c(=O)n6C5CCC(=O)NC5=O)CC4)CC3)cc2cc1NC(=O)c1cccc(C(F)(F)F)n1] |
| I-102 | 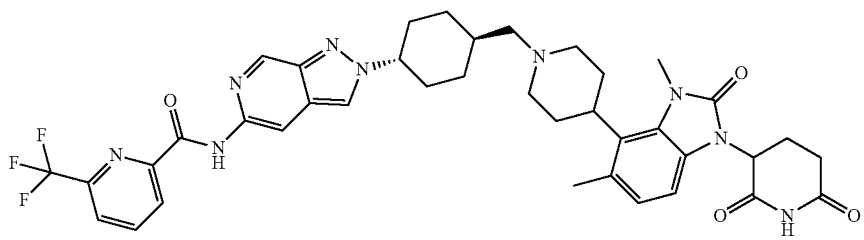 [SMILES: Cc1ccc2c(c1C1CCN(C[C@H]3CC[C@H](n4cc5cc(NC(=O)c6cccc(C(F)(F)F)n6)ncc5n4)CC3)CC1)n(C)c(=O)n2C1CCC(=O)NC1=O] |
| I-103 | 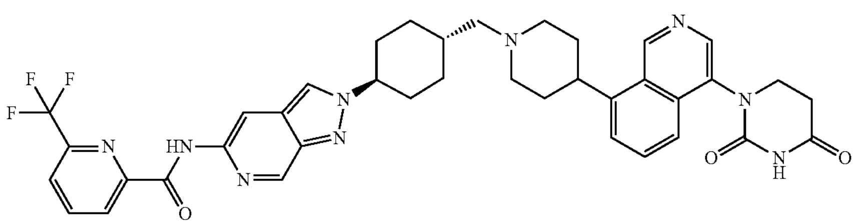 [SMILES: O=C1CCN(c2cncc3c(C4CCN(C[C@H]5CC[C@H](n6cc7cc(NC(=O)c8cccc(C(F)(F)F)n8)ncc7n6)CC5)CC4)cccc23)C(=O)N1] |
| I-104 | 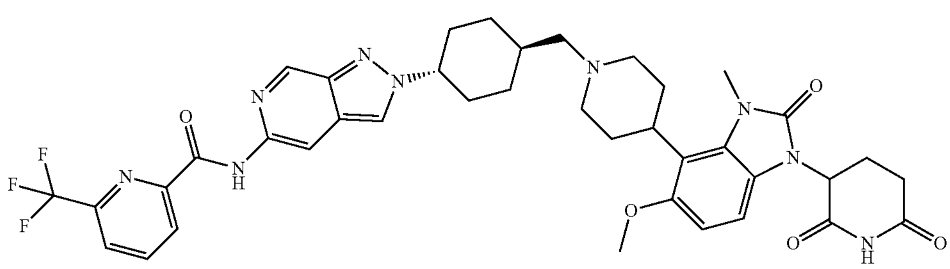 [SMILES: COc1ccc2c(c1C1CCN(C[C@H]3CC[C@H](n4cc5cc(NC(=O)c6cccc(C(F)(F)F)n6)ncc5n4)CC3)CC1)n(C)c(=O)n2C1CCC(=O)NC1=O] |
| I-105 | 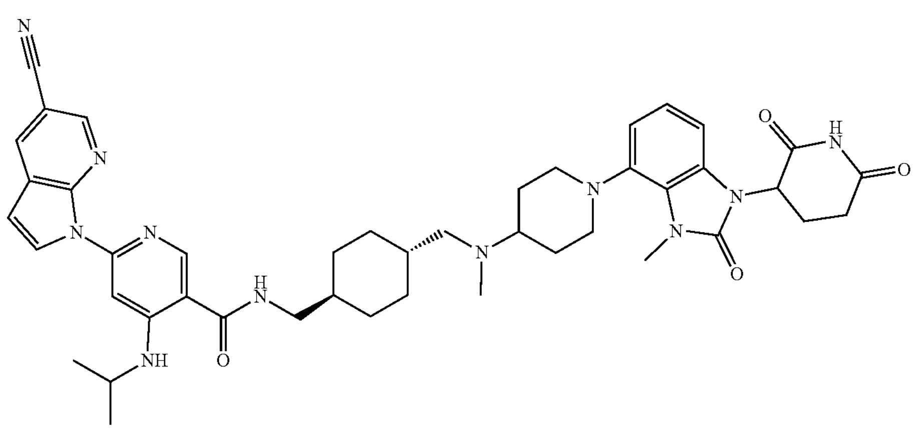 [SMILES: CC(C)Nc1cc(-n2ccc3cc(C#N)cnc32)ncc1C(=O)NC[C@H]1CC[C@H](CN(C)C2CCN(c3cccc4c3n(C)c(=O)n4C3CCC(=O)NC3=O)CC2)CC1] |

TABLE 1-continued
Exemplary Compounds
| I-# | Structure |
| --- | --- |
| I-106 | 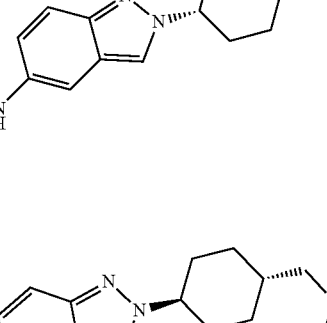 |
| I-107 | 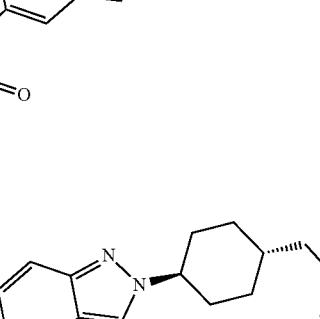 |
| I-108 | 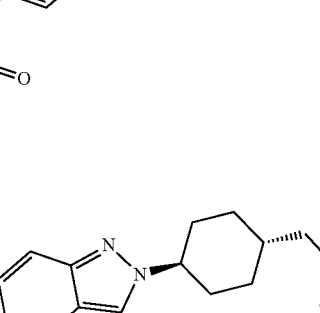 |
| I-109 | 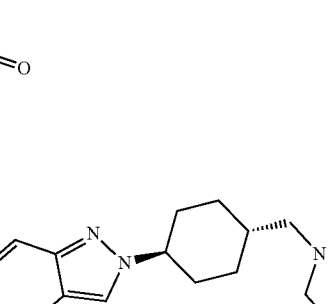 |
| I-110 | 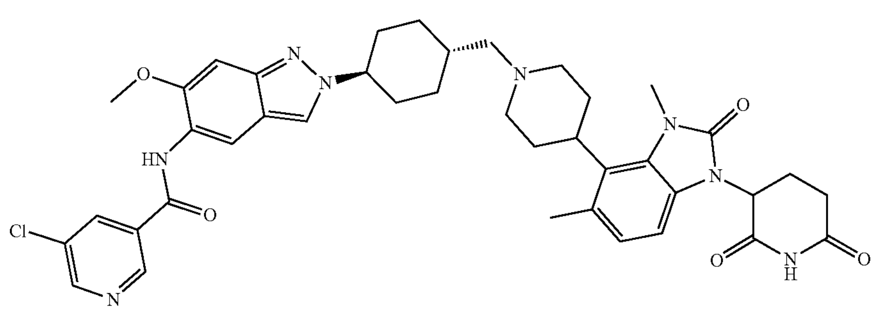 [SMILES: COc1cc2nn([C@H]3CC[C@H](CN4CCC(c5c(C)ccc6c5n(C)c(=O)n6C5CCC(=O)NC5=O)CC4)CC3)cc2cc1NC(=O)c1cncc(Cl)c1] |

TABLE 1-continued

Exemplary Compounds

| I-# | Structure |
|---|---|
| I-111 | 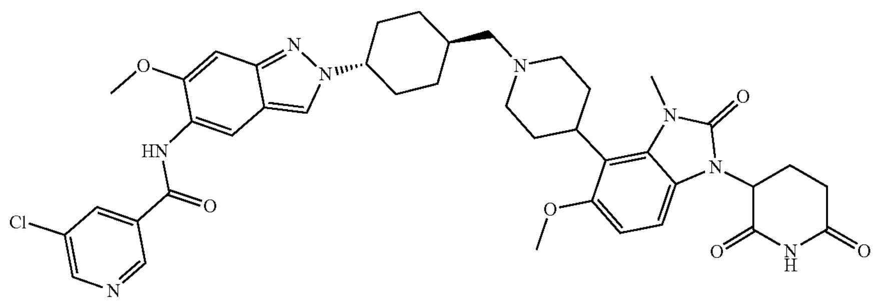 [SMILES: COc1cc2nn([C@H]3CC[C@H](CN4CCC(c5c(OC)ccc6c5n(C)c(=O)n6C5CCC(=O)NC5=O)CC4)CC3)cc2cc1NC(=O)c1cncc(Cl)c1] |
| I-112 | 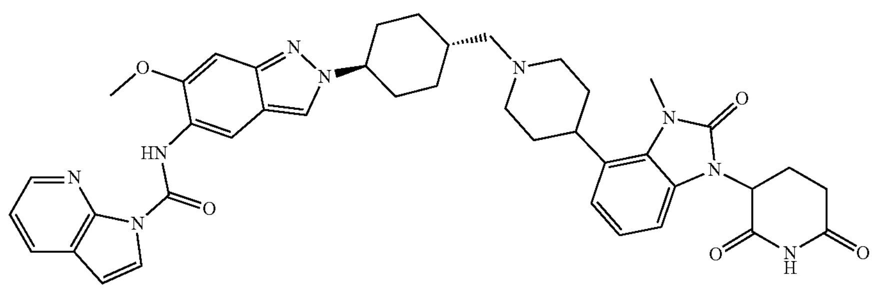 [SMILES: COc1cc2nn([C@H]3CC[C@H](CN4CCC(c5cccc6c5n(C)c(=O)n6C5CCC(=O)NC5=O)CC4)CC3)cc2cc1NC(=O)n1ccc2cccnc21] |
| I-113 | 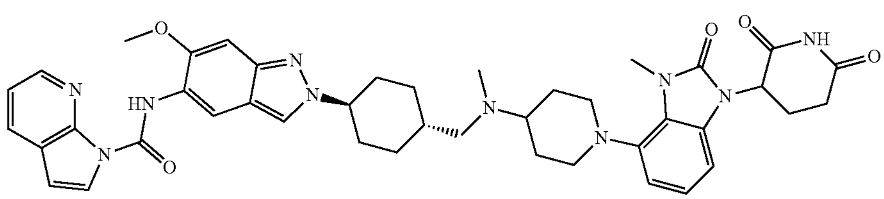 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)n1ccc2cccnc21] |
| I-114 | 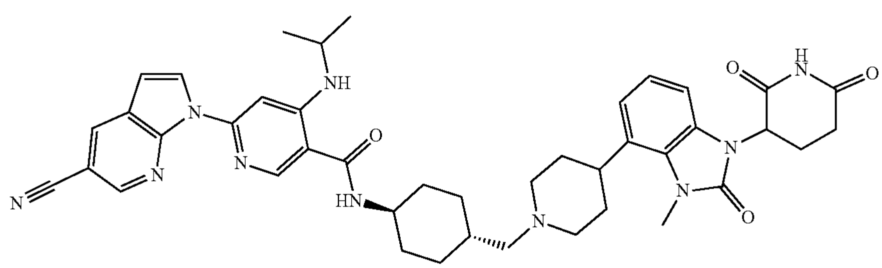 [SMILES: CC(C)Nc1cc(-n2ccc3cc(C#N)cnc32)ncc1C(=O)N[C@H]1CC[C@H](CN2CCC(c3cccc4c3n(C)c(=O)n4C3CCC(=O)NC3=O)CC2)CC1] |
| I-115 | 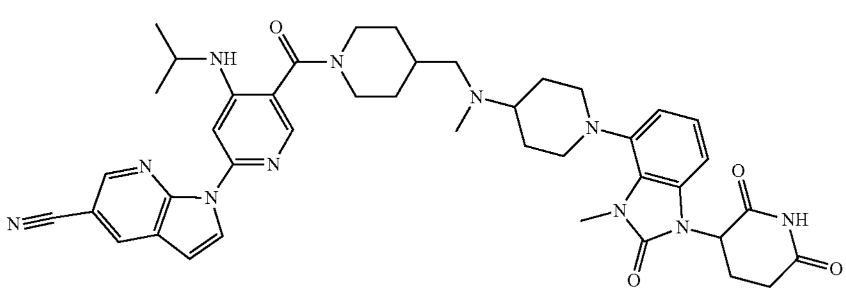 [SMILES: CC(C)Nc1cc(-n2ccc3cc(C#N)cnc32)ncc1C(=O)N1CCC(CN(C)C2CCN(c3cccc4c3n(C)c(=O)n4C3CCC(=O)NC3=O)CC2)CC1] |

TABLE 1-continued

Exemplary Compounds

| I-# | Structure |
|---|---|
| I-116 | 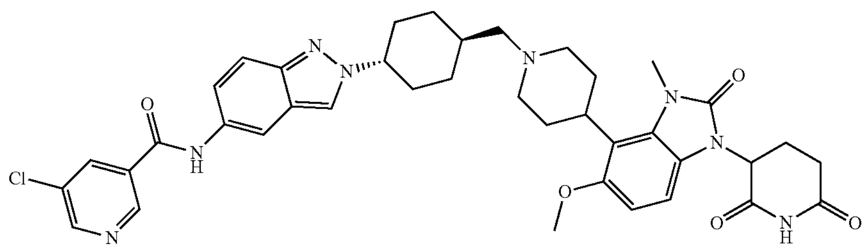 [SMILES: COc1ccc2c(c1C1CCN(C[C@H]3CC[C@H](n4cc5cc(NC(=O)c6cncc(Cl)c6)ccc5n4)CC3)CC1)n(C)c(=O)n2C1CCC(=O)NC1=O] |
| I-117 | 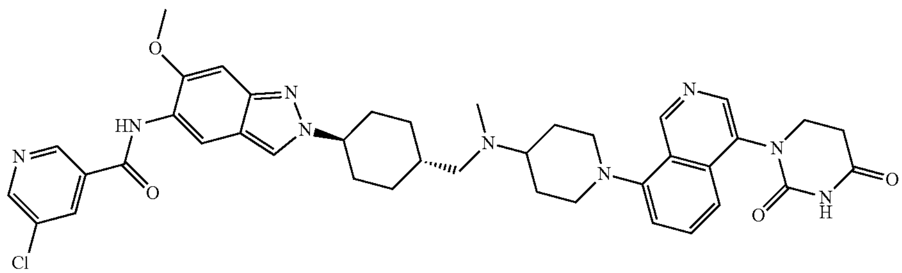 [SMILES: COc1cc2nn([C@H]3CC[C@H](CN(C)C4CCN(c5cccc6c(N7CCC(=O)NC7=O)cncc56)CC4)CC3)cc2cc1NC(=O)c1cncc(Cl)c1] |
| I-118 | 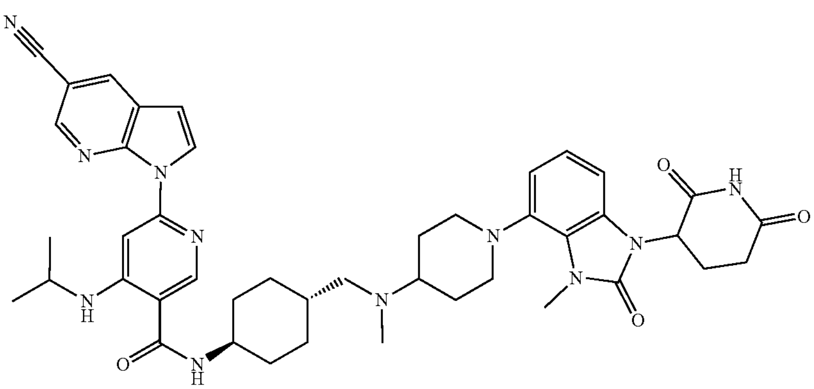 [SMILES: CC(C)Nc1cc(-n2ccc3cc(C#N)cnc32)ncc1C(=O)N[C@H]1CC[C@H](CN(C)C2CCN(c3cccc4c3n(C)c(=O)n4C3CCC(=O)NC3=O)CC2)CC1] |
| I-119 | 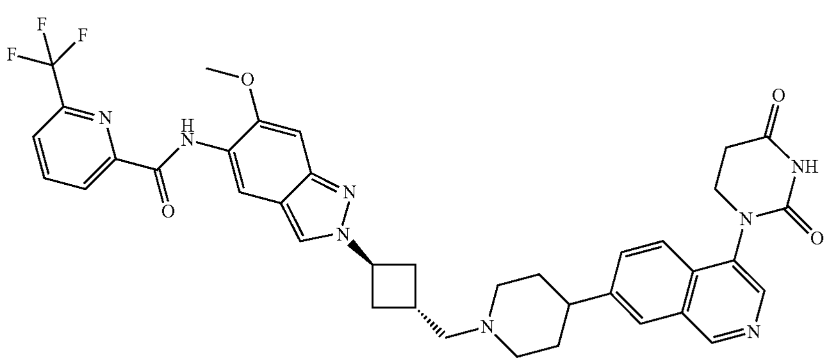 [SMILES: COc1cc2nn([C@H]3C[C@H](CN4CCC(c5ccc6c(N7CCC(=O)NC7=O)cncc6c5)CC4)C3)cc2cc1NC(=O)c1cccc(C(F)(F)F)n1] |

TABLE 1-continued
Exemplary Compounds
| I-# | Structure |
|---|---|
| I-120 | 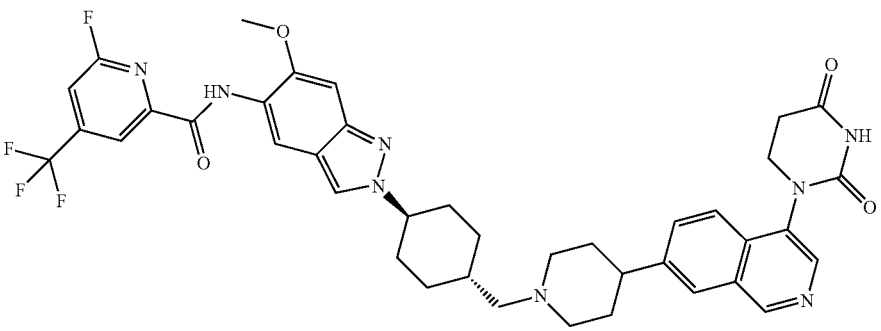 [SMILES: COc1cc2nn([C@H]3CC[C@H](CN4CCC(c5ccc6c(N7CCC(=O)NC7=O)cncc6c5)CC4)CC3)cc2cc1NC(=O)c1cc(C(F)(F)F)cc(F)n1] |
| I-121 | 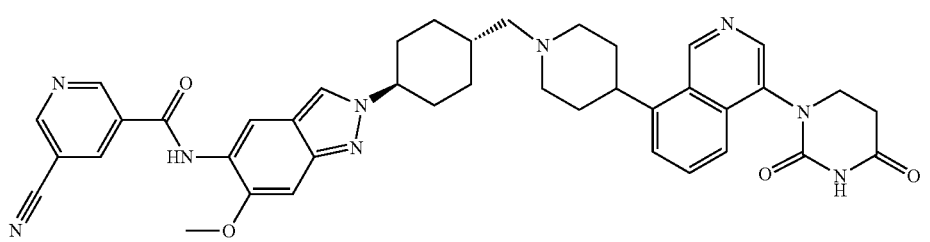 [SMILES: COc1cc2nn([C@H]3CC[C@H](CN4CCC(c5cccc6c(N7CCC(=O)NC7=O)cncc56)CC4)CC3)cc2cc1NC(=O)c1cncc(C#N)c1] |
| I-122 | 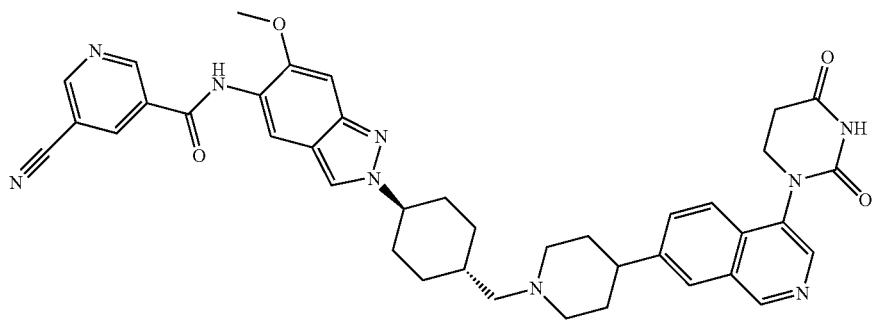 [SMILES: COc1cc2nn([C@H]3CC[C@H](CN4CCC(c5ccc6c(N7CCC(=O)NC7=O)cncc6c5)CC4)CC3)cc2cc1NC(=O)c1cncc(C#N)c1] |
| I-123 | 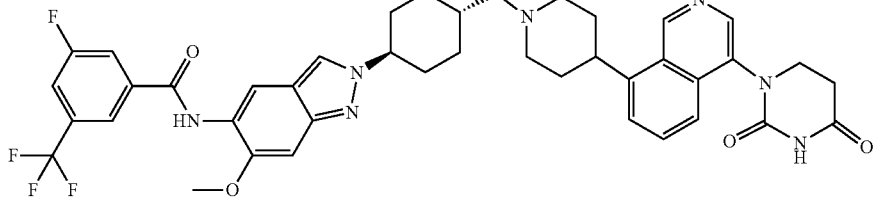 |
| I-124 | 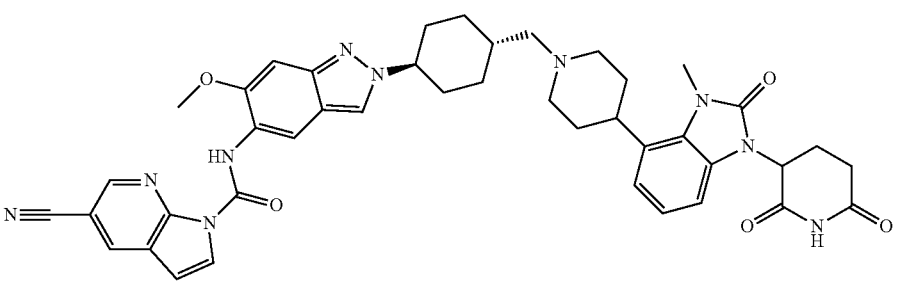 [SMILES: COc1cc2nn([C@H]3CC[C@H](CN4CCC(c5cccc6c5n(C)c(=O)n6C5CCC(=O)NC5=O)CC4)CC3)cc2cc1NC(=O)n1ccc2cc(C#N)cnc21] |

TABLE 1-continued
Exemplary Compounds
| I-# | Structure |
|---|---|
| I-125 | 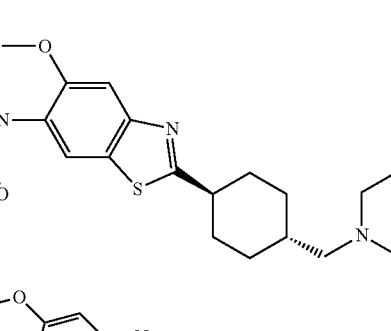 |
| I-126 | 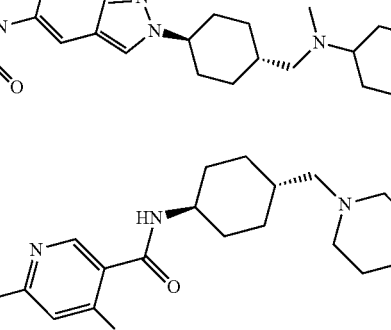 |
| I-127 | 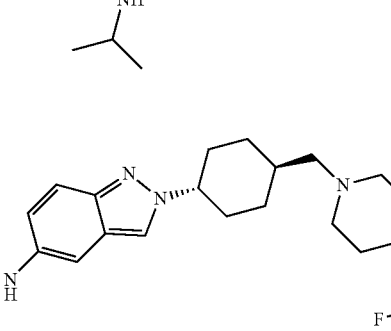 |
| I-128 | 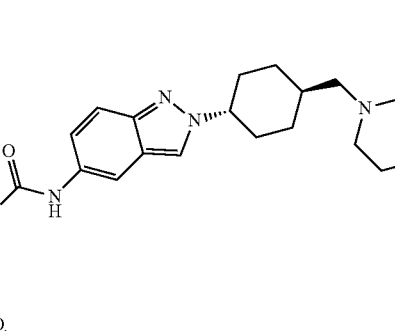 |
| I-129 | 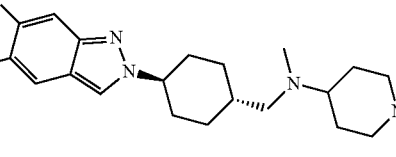 |
| I-130 | 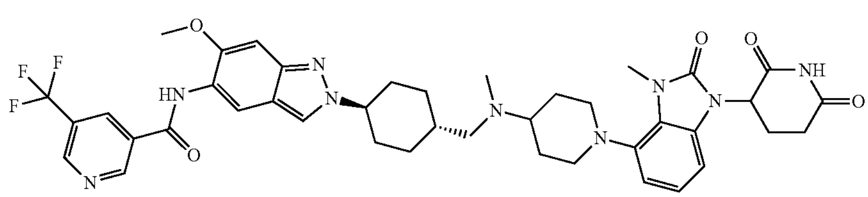 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cncc(C(F)(F)F)c1] |

TABLE 1-continued

Exemplary Compounds

| I-# | Structure |
|---|---|
| I-131 | 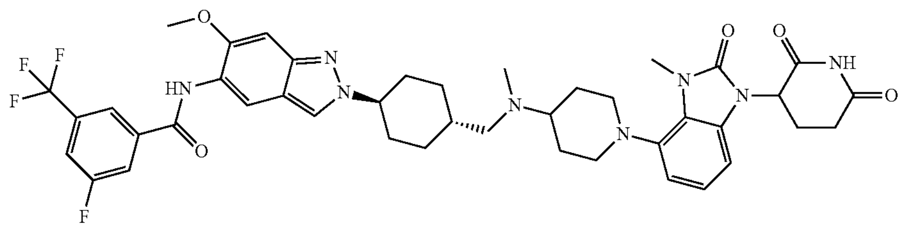 [SMILES: COc1cc2nn([C@H]3CC[C@H](CN(C)C4CCN(c5cccc6c5n(C)c(=O)n6C5CCC(=O)NC5=O)CC4)CC3)cc2cc1NC(=O)c1cc(F)cc(C(F)(F)F)c1] |
| I-132 | 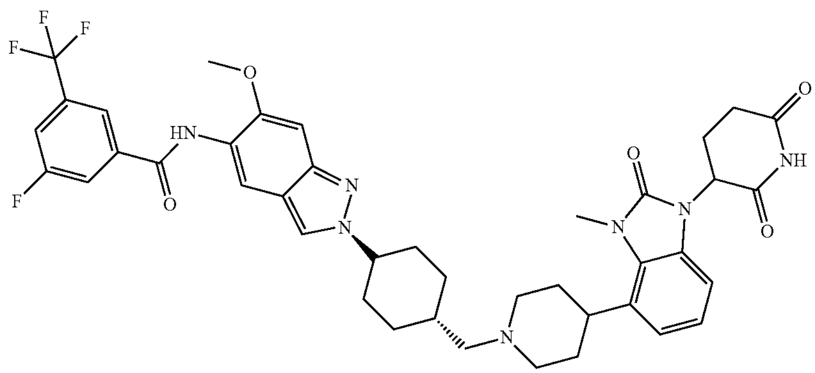 |
| I-133 | 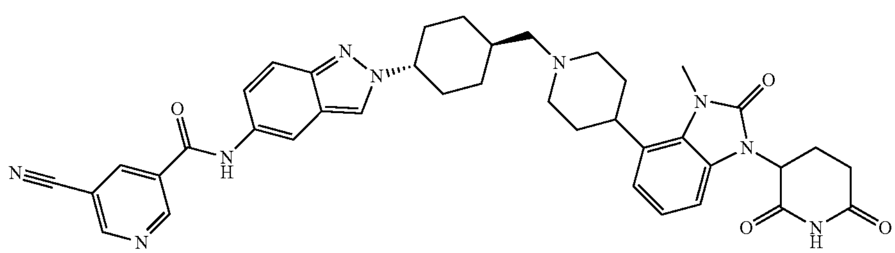 [SMILES: Cn1c(=O)n(C2CCC(=O)NC2=O)c2cccc(C3CCN(C[C@H]4CC[C@H](n5cc6cc(NC(=O)c7cncc(C#N)c7)ccc6n5)CC4)CC3)c21] |
| I-134 | 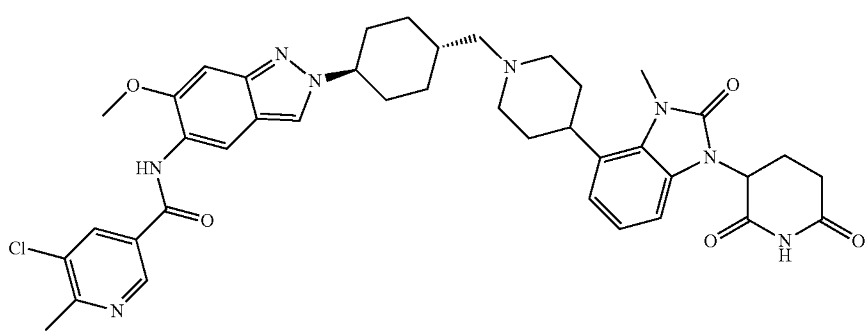 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cnc(C)c(Cl)c1] |
| I-135 | 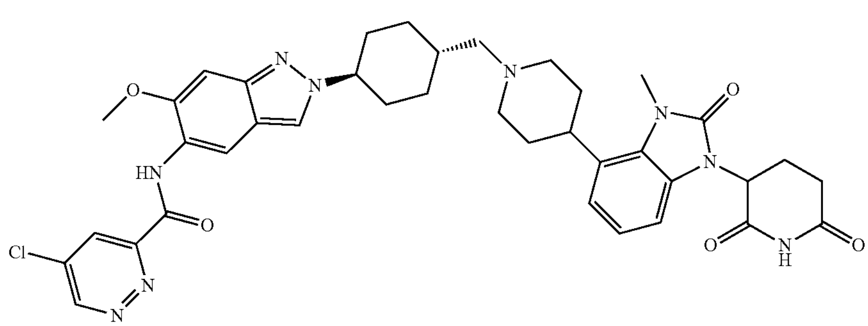 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cc(Cl)cnn1] |

TABLE 1-continued
Exemplary Compounds
| I-# | Structure |
|---|---|
| I-136 | 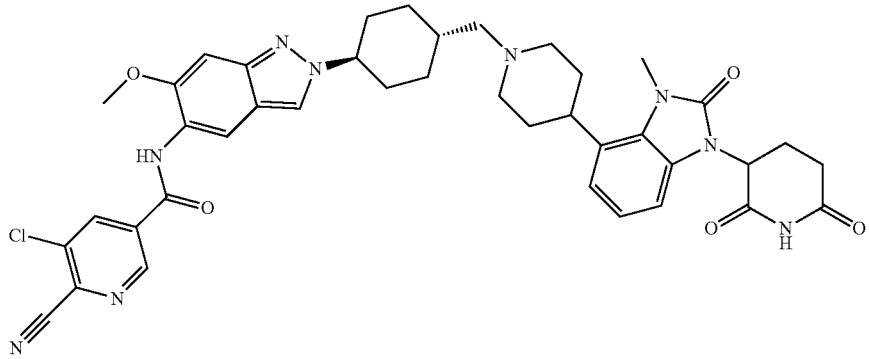 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cnc(C#N)c(Cl)c1] |
| I-137 | 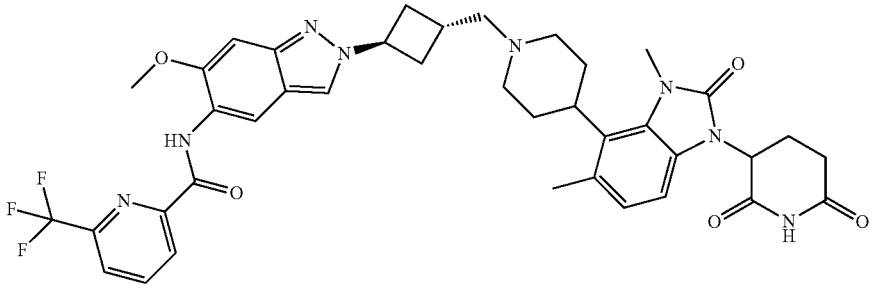 [SMILES: COc1cc2nn([C@H]3C[C@H](CN4CCC(c5c(C)ccc6c5n(C)c(=O)n6C5CCC(=O)NC5=O)CC4)C3)cc2cc1NC(=O)c1cccc(C(F)(F)F)n1] |
| I-138 | 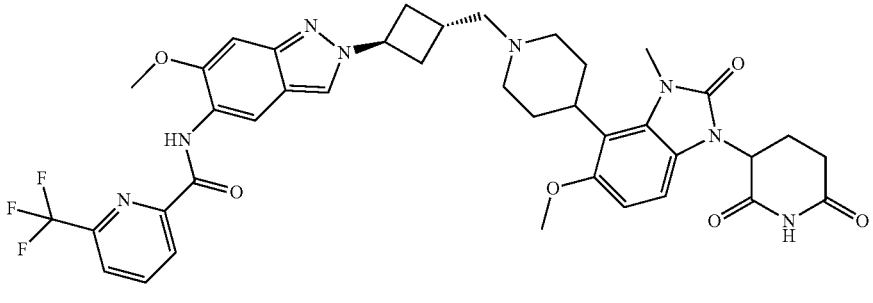 [SMILES: COc1cc2nn([C@H]3C[C@H](CN4CCC(c5c(OC)ccc6c5n(C)c(=O)n6C5CCC(=O)NC5=O)CC4)C3)cc2cc1NC(=O)c1cccc(C(F)(F)F)n1] |
| I-139 | 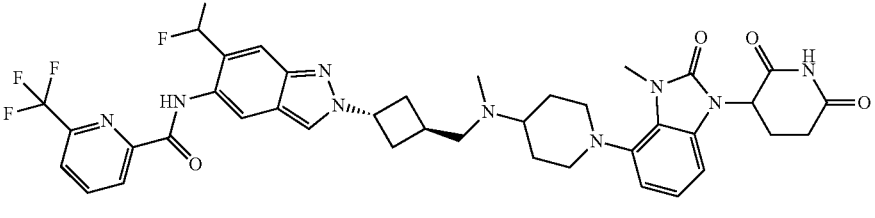 |
| I-140 | 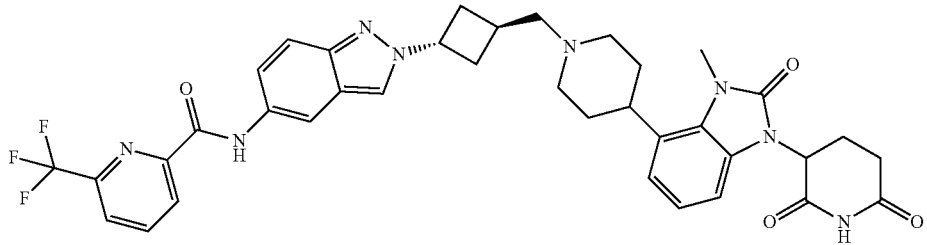 [SMILES: Cn1c(=O)n(C2CCC(=O)NC2=O)c2cccc(C3CCN(C[C@H]4C[C@H](n5cc6cc(NC(=O)c7cccc(C(F)(F)F)n7)ccc6n5)C4)CC3)c21] |

TABLE 1-continued

Exemplary Compounds

| I-# | Structure |
|---|---|
| I-141 | 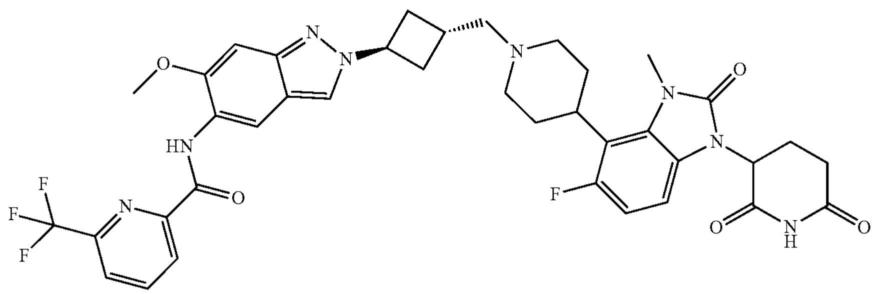 |
| I-142 | 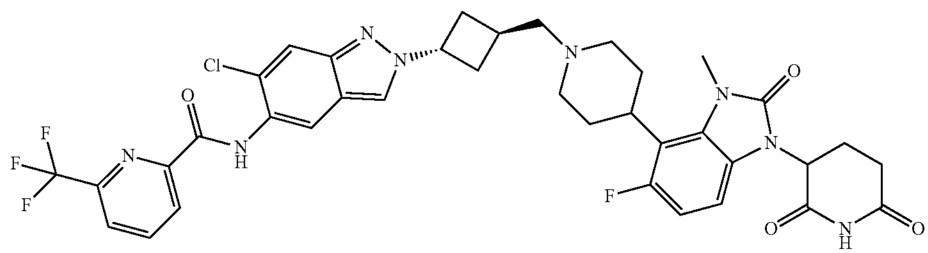 [SMILES: Cc1ccc2c(c1C1CCN(C[C@H]3C[C@H](n4cc5cc(NC(=O)c6cccc(C(F)(F)F)n6)c(Cl)cc5n4)C3)CC1)n(C)c(=O)n2C1CCC(=O)NC1=O] |
| I-143 | 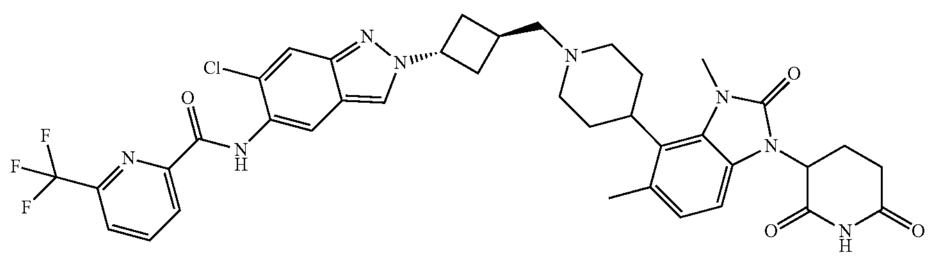 |
| I-144 | 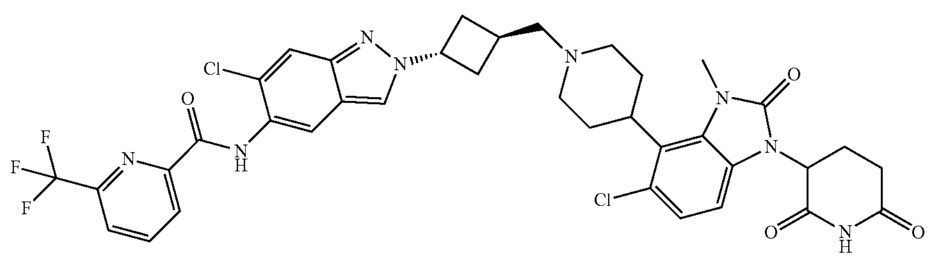 [SMILES: Cn1c(=O)n(C2CCC(=O)NC2=O)c2ccc(Cl)c(C3CCN(C[C@H]4C[C@H](n5cc6cc(NC(=O)c7cccc(C(F)(F)F)n7)c(Cl)cc6n5)C4)CC3)c21] |
| I-145 | 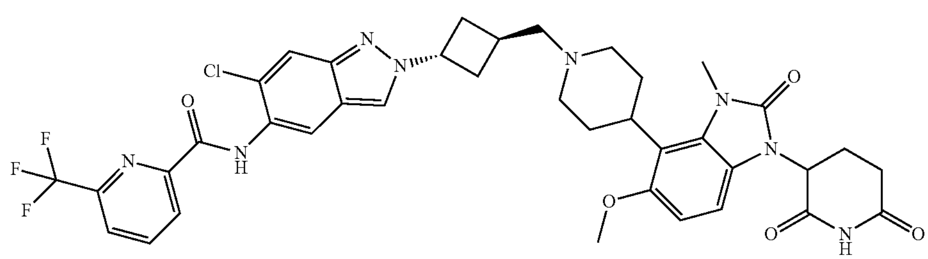 [SMILES: COc1ccc2c(c1C1CCN(C[C@H]3C[C@H](n4cc5cc(NC(=O)c6cccc(C(F)(F)F)n6)c(Cl)cc5n4)C3)CC1)n(C)c(=O)n2C1CCC(=O)NC1=O] |
| I-146 | 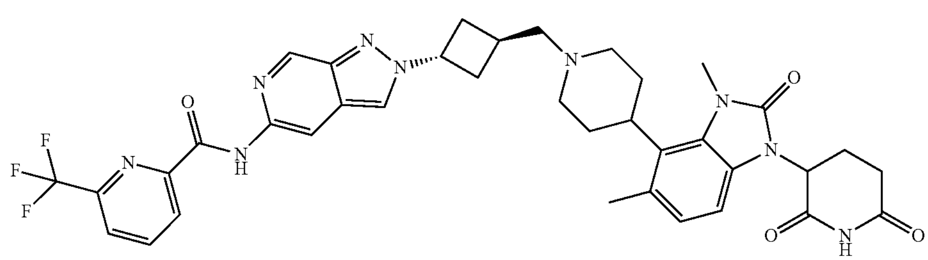 [SMILES: Cc1ccc2c(c1C1CCN(C[C@H]3C[C@H](n4cc5cc(NC(=O)c6cccc(C(F)(F)F)n6)ncc5n4)C3)CC1)n(C)c(=O)n2C1CCC(=O)NC1=O] |

TABLE 1-continued

Exemplary Compounds

| I-# | Structure |
|---|---|
| I-147 | 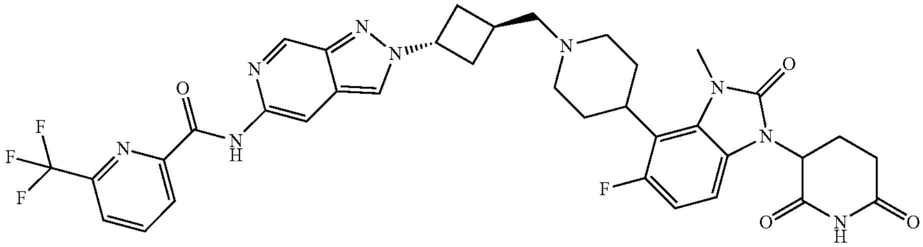 |
| I-148 | 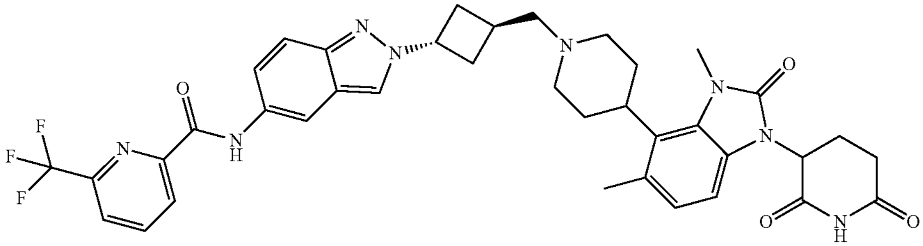 |
| I-149 | 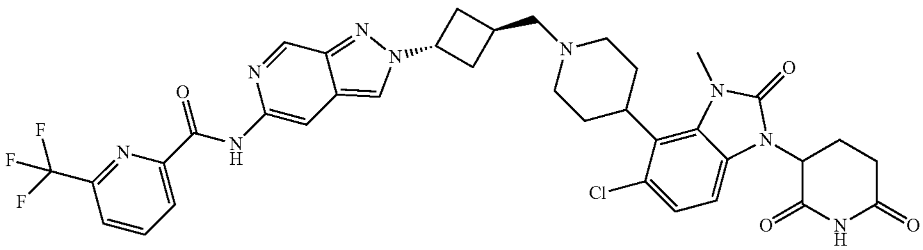 |
| I-150 | 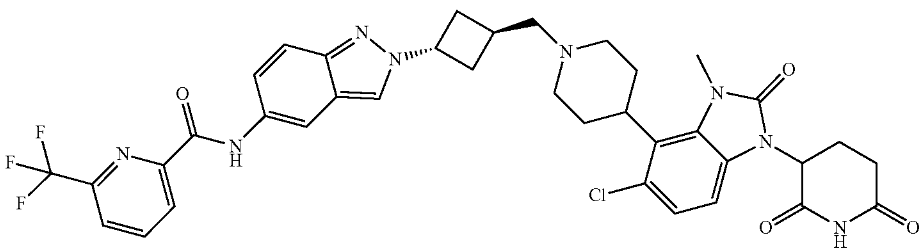 |
| I-151 | 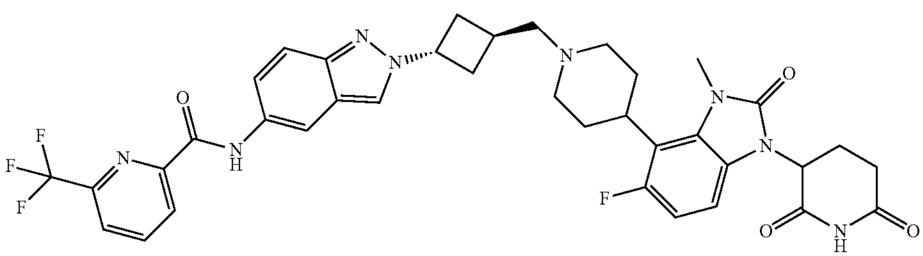 [SMILES: Cc1ccc2c(c1C1CCN(C[C@H]3C[C@H](n4cc5cc(NC(=O)c6cccc(C(F)(F)F)n6)ccc5n4)C3)CC1)n(C)c(=O)n2C1CCC(=O)NC1=O] |
| I-152 | 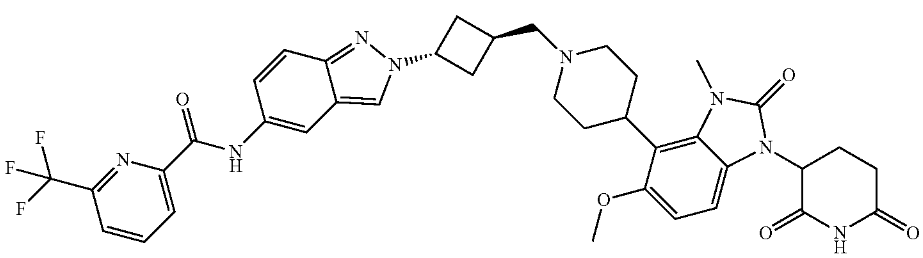 [SMILES: COc1ccc2c(c1C1CCN(C[C@H]3C[C@H](n4cc5cc(NC(=O)c6cccc(C(F)(F)F)n6)ccc5n4)C3)CC1)n(C)c(=O)n2C1CCC(=O)NC1=O] |

TABLE 1-continued

Exemplary Compounds

| I-# | Structure |
| --- | --- |
| I-153 | 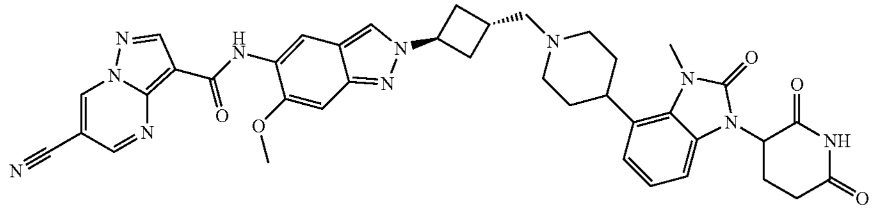 [SMILES: COc1cc2nn([C@H]3C[C@H](CN4CCC(c5cccc6c5n(C)c(=O)n6C5CCC(=O)NC5=O)CC4)C3)cc2cc1NC(=O)c1cnn2cc(C#N)cnc12] |
| I-154 | 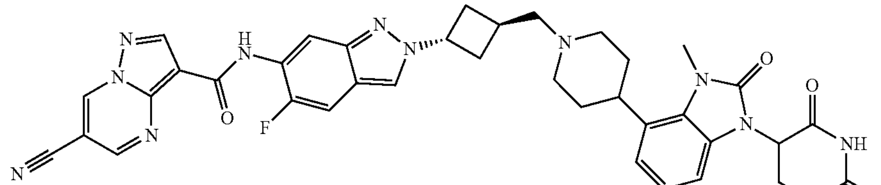 |
| I-155 | 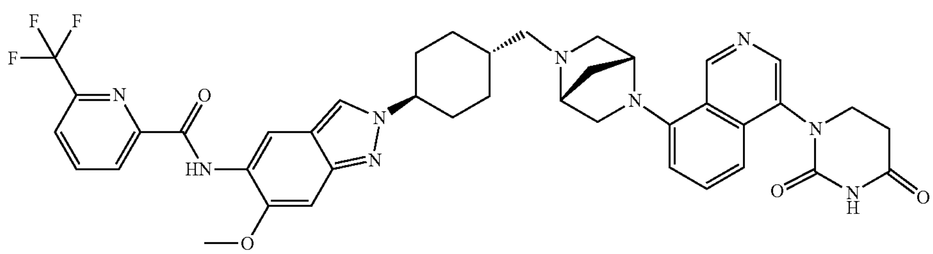 [SMILES: COc1cc2nn([C@H]3CC[C@H](CN4C[C@H]5C[C@@H]4CN5c4cccc5c(N6CCC(=O)NC6=O)cncc45)CC3)cc2cc1NC(=O)c1cccc(C(F)(F)F)n1] |
| I-156 | 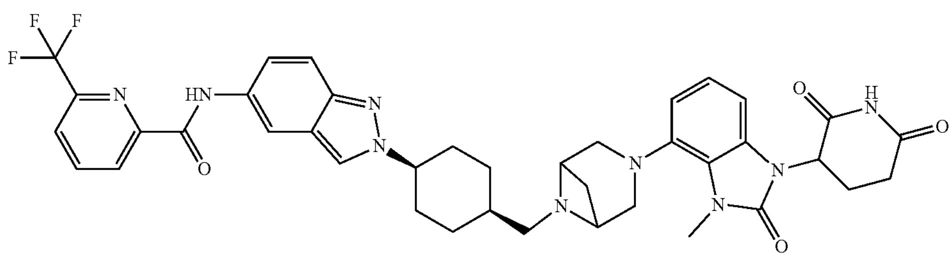 [SMILES: Cn1c(=O)n(C2CCC(=O)NC2=O)c2cccc(N3CC4CC(C3)N4C[C@H]3CC[C@@H](n4cc5cc(NC(=O)c6cccc(C(F)(F)F)n6)ccc5n4)CC3)c21] |
| I-157 | 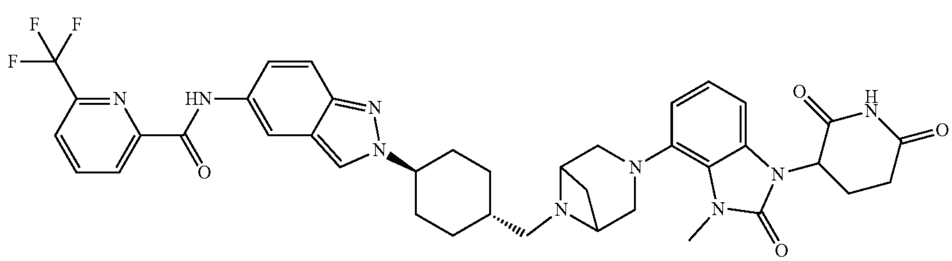 [SMILES: Cn1c(=O)n(C2CCC(=O)NC2=O)c2cccc(N3CC4CC(C3)N4C[C@H]3CC[C@H](n4cc5cc(NC(=O)c6cccc(C(F)(F)F)n6)ccc5n4)CC3)c21] |
| I-158 | 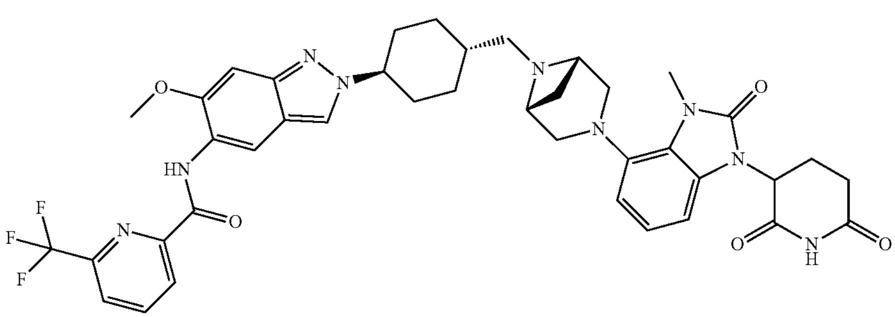 [SMILES: COc1cc2nn([C@H]3CC[C@H](CN4[C@@H]5C[C@H]4CN(c4cccc6c4n(C)c(=O)n6C4CCC(=O)NC4=O)C5)CC3)cc2cc1NC(=O)c1cccc(C(F)(F)F)n1] |

TABLE 1-continued

Exemplary Compounds

| I-# | Structure |
|---|---|
| I-159 | 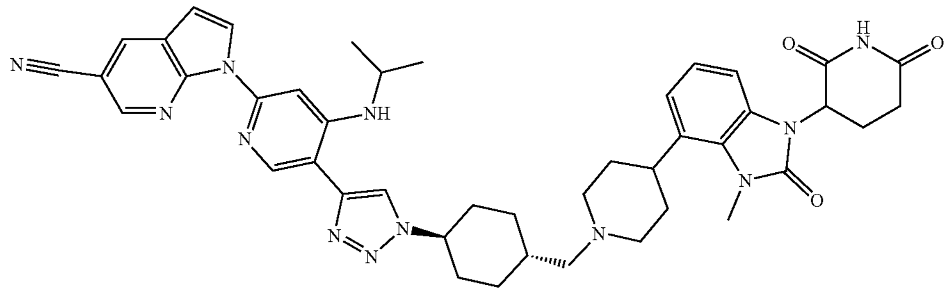 [SMILES: CC(C)Nc1cc(-n2ccc3cc(C#N)cnc32)ncc1-c1cn([C@H]2CC[C@H](CN3CCC(c4cccc5c4n(C)c(=O)n5C4CCC(=O)NC4=O)CC3)CC2)nn1] |
| I-160 | 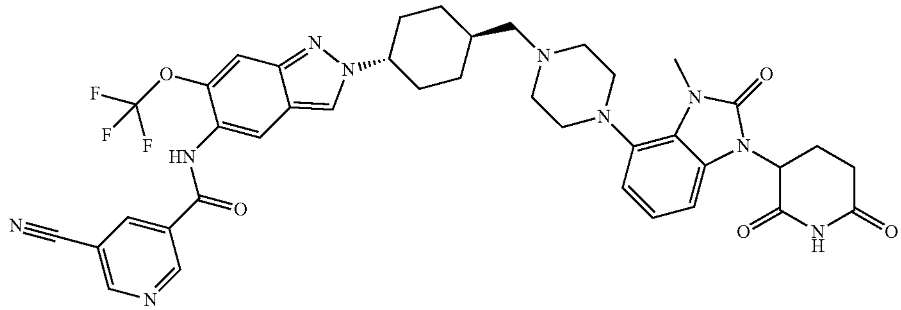 [SMILES: Cn1c(=O)n(C2CCC(=O)NC2=O)c2cccc(N3CCN(C[C@H]4CC[C@H](n5cc6cc(NC(=O)c7cncc(C#N)c7)c(OC(F)(F)F)cc6n5)CC4)CC3)c21] |
| I-161 | 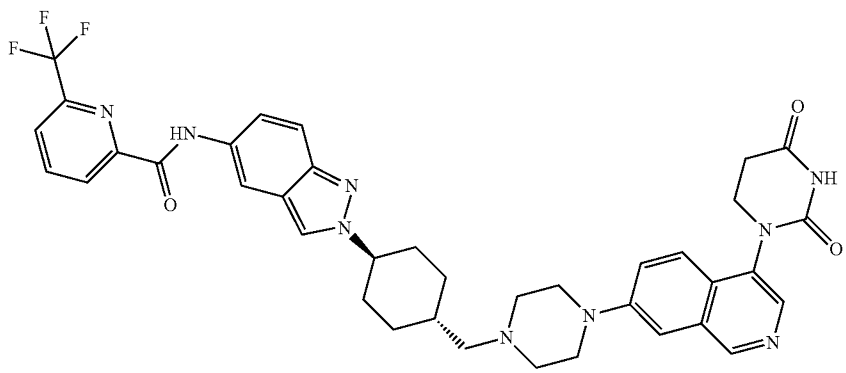 [SMILES: O=C1CCN(c2cncc3cc(N4CCN(C[C@H]5CC[C@H](n6cc7cc(NC(=O)c8cccc(C(F)(F)F)n8)ccc7n6)CC5)CC4)ccc23)C(=O)N1] |
| I-162 | 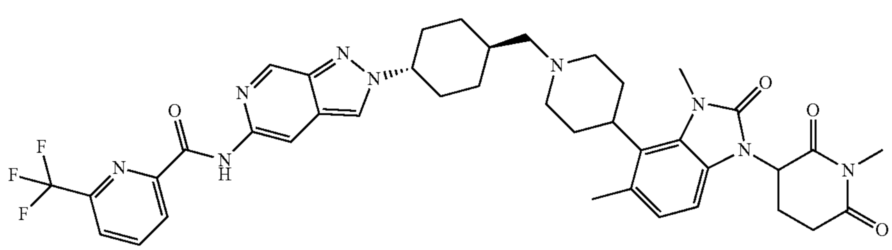 [SMILES: Cc1ccc2c(c1C1CCN(C[C@H]3CC[C@H](n4cc5cc(NC(=O)c6cccc(C(F)(F)F)n6)ncc5n4)CC3)CC1)n(C)c(=O)n2C1CCC(=O)N(C)C1=O] |
| I-163 | 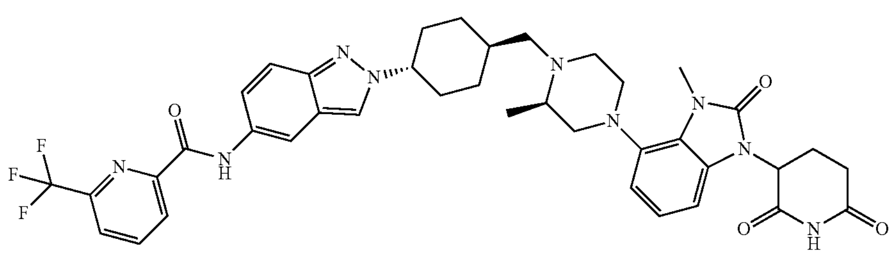 [SMILES: C[C@@H]1CN(c2cccc3c2n(C)c(=O)n3C2CCC(=O)NC2=O)CCN1C[C@H]1CC[C@H](n2cc3cc(NC(=O)c4cccc(C(F)(F)F)n4)ccc3n2)CC1] |

TABLE 1-continued

Exemplary Compounds

| I-# | Structure |
|---|---|
| I-164 | 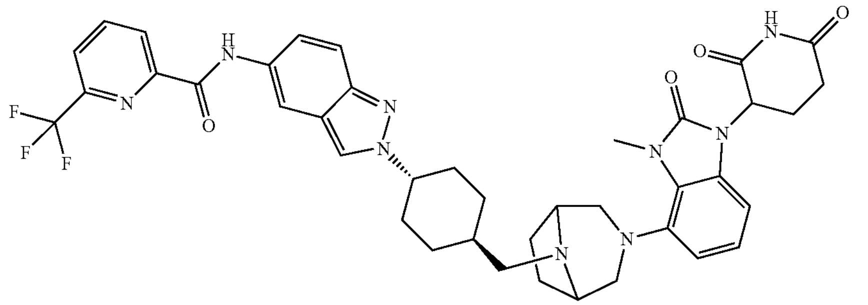 [SMILES: Cn1c(=O)n(C2CCC(=O)NC2=O)c2cccc(N3CC4CCC(C3)N4C[C@H]3CC[C@H](n4cc5cc(NC(=O)c6cccc(C(F)(F)F)n6)ccc5n4)CC3)c21] |
| I-165 | 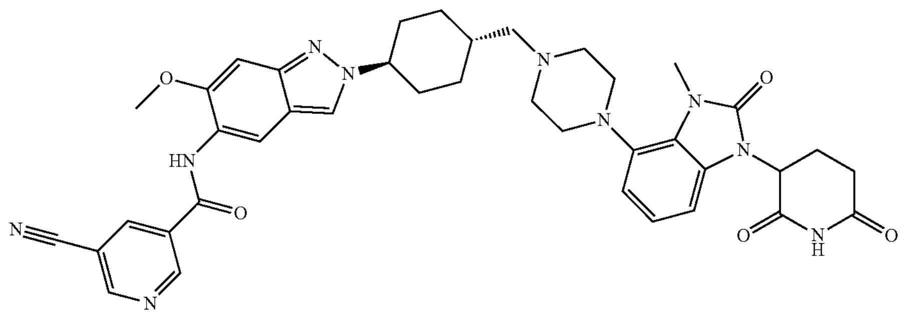 [SMILES: COc1cc2nn([C@H]3CC[C@H](CN4CCN(c5cccc6c5n(C)c(=O)n6C5CCC(=O)NC5=O)CC4)CC3)cc2cc1NC(=O)c1cncc(C#N)c1] |
| I-166 | 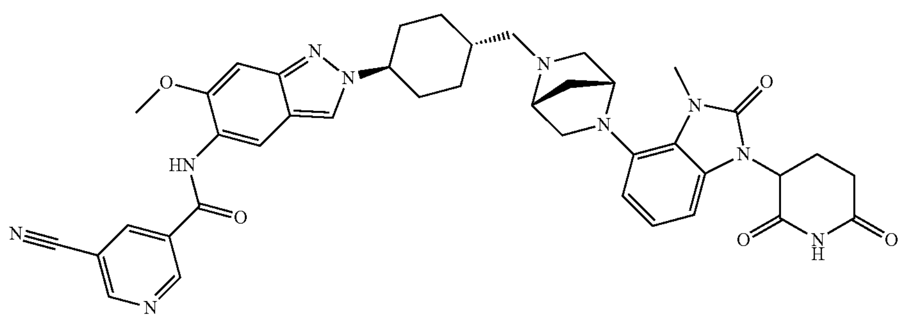 [SMILES: COc1cc2nn([C@H]3CC[C@H](CN4C[C@H]5C[C@@H]4CN5c4cccc5c4n(C)c(=O)n5C4CCC(=O)NC4=O)CC3)cc2cc1NC(=O)c1cncc(C#N)c1] |
| I-167 | 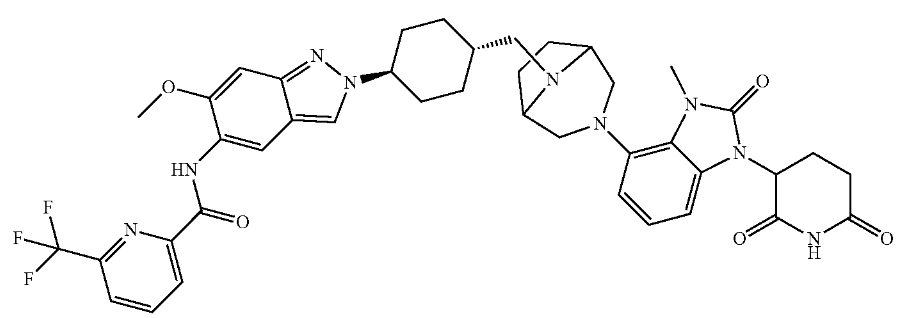 [SMILES: COc1cc2nn([C@H]3CC[C@H](CN4C5CCC4CN(c4cccc6c4n(C)c(=O)n6C4CCC(=O)NC4=O)C5)CC3)cc2cc1NC(=O)c1cccc(C(F)(F)F)n1] |
| I-168 | 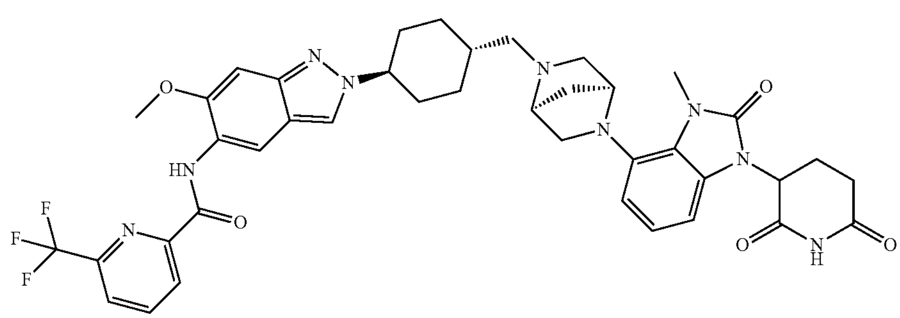 [SMILES: COc1cc2nn([C@H]3CC[C@H](CN4C[C@@H]5C[C@H]4CN5c4cccc5c4n(C)c(=O)n5C4CCC(=O)NC4=O)CC3)cc2cc1NC(=O)c1cccc(C(F)(F)F)n1] |

TABLE 1-continued

Exemplary Compounds

| I-# | Structure |
|---|---|
| I-169 | 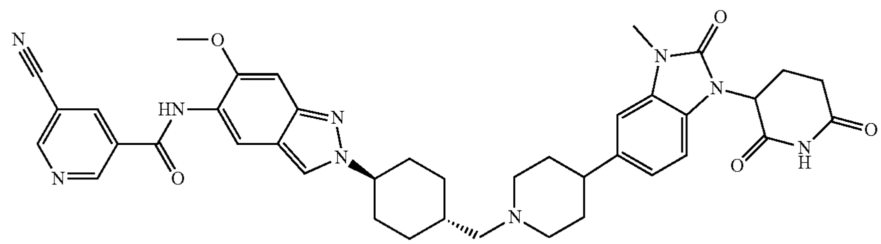 [SMILES: COc1cc2nn([C@H]3CC[C@H](CN4CCC(c5ccc6c(c5)n(C)c(=O)n6C5CCC(=O)NC5=O)CC4)CC3)cc2cc1NC(=O)c1cncc(C#N)c1] |
| I-170 | 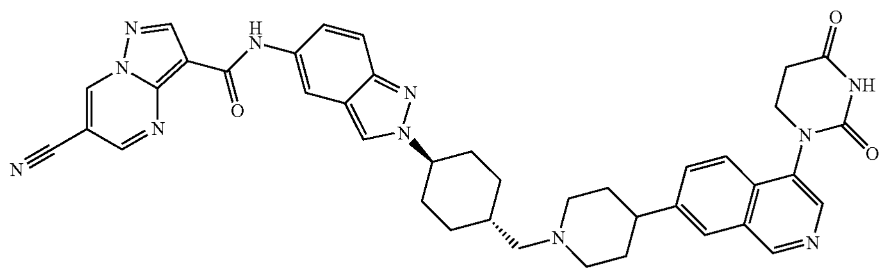 [SMILES: N#Cc1cnc2c(C(=O)Nc3ccc4nn([C@H]5CC[C@H](CN6CCC(c7ccc8c(N9CCC(=O)NC9=O)cncc8c7)CC6)CC5)cc4c3)cnn2c1] |
| I-171 | 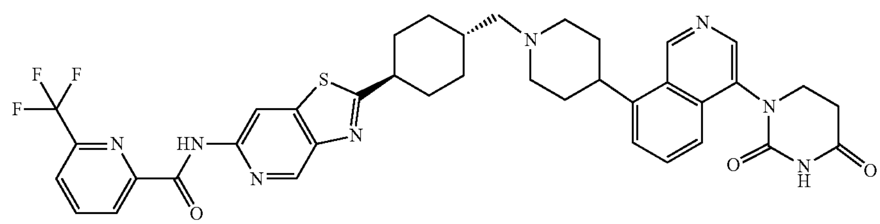 [SMILES: O=C1CCN(c2cncc3c(C4CCN(C[C@H]5CC[C@H](c6nc7cnc(NC(=O)c8cccc(C(F)(F)F)n8)cc7s6)CC5)CC4)cccc23)C(=O)N1] |
| I-172 | 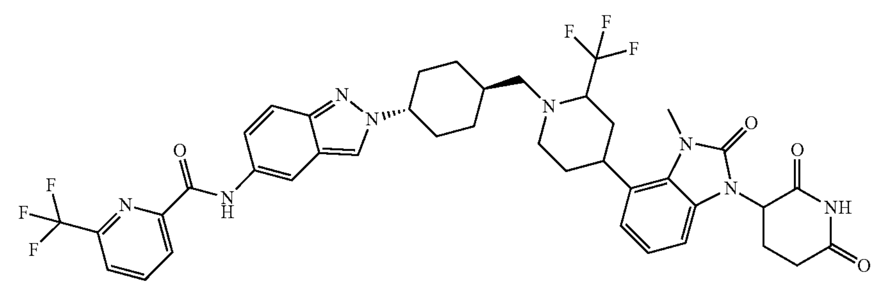 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)ccc6n5)CC4)C(C(F)(F)F)C3)c21] |
| I-173 | 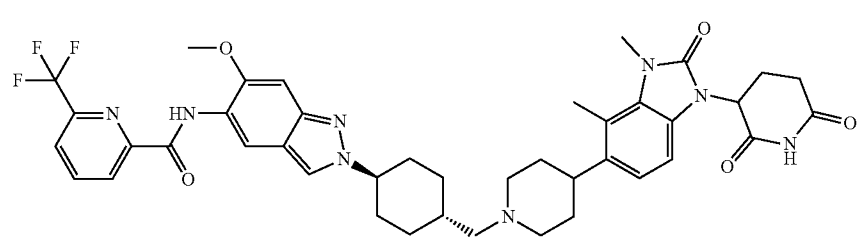 [SMILES: COc1cc2nn([C@H]3CC[C@H](CN4CCC(c5ccc6c(c5C)n(C)c(=O)n6C5CCC(=O)NC5=O)CC4)CC3)cc2cc1NC(=O)c1cccc(C(F)(F)F)n1] |

TABLE 1-continued

Exemplary Compounds

| I-# | Structure |
|---|---|
| I-174 | 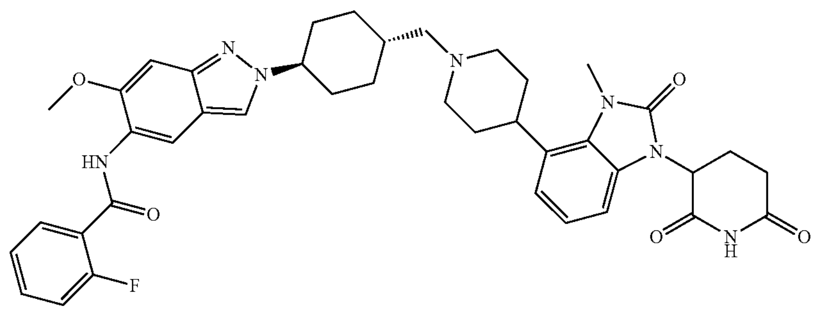 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1ccccc1F] |
| I-175 | 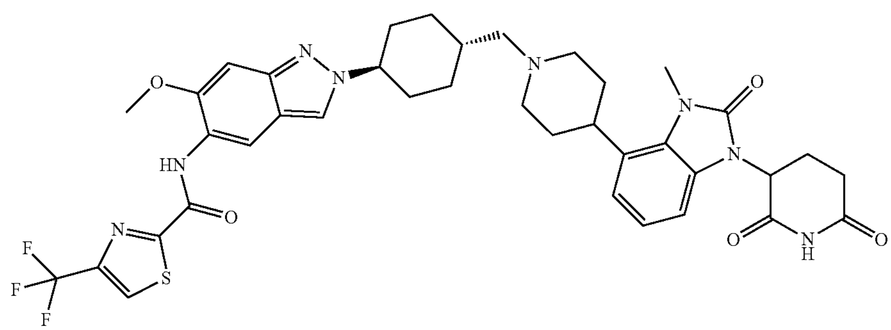 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1nc(C(F)(F)F)cs1] |
| I-176 | 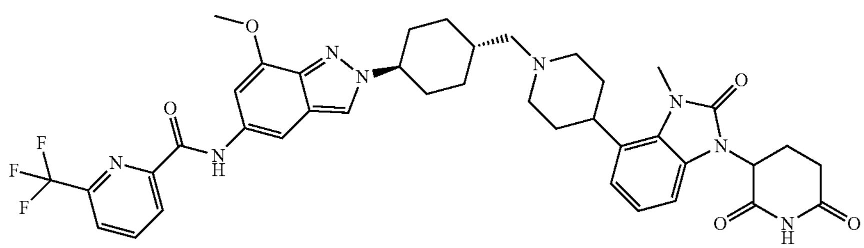 [SMILES: COc1cc(NC(=O)c2cccc(C(F)(F)F)n2)cc2cn([C@H]3CC[C@H](CN4CCC(c5cccc6c5n(C)c(=O)n6C5CCC(=O)NC5=O)CC4)CC3)nc12] |
| I-177 | 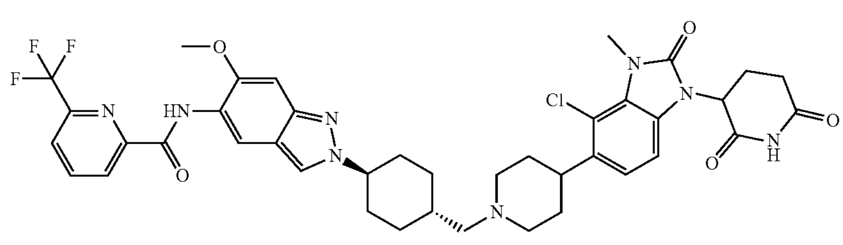 [SMILES: COc1cc2nn([C@H]3CC[C@H](CN4CCC(c5ccc6c(c5Cl)n(C)c(=O)n6C5CCC(=O)NC5=O)CC4)CC3)cc2cc1NC(=O)c1cccc(C(F)(F)F)n1] |
| I-178 | 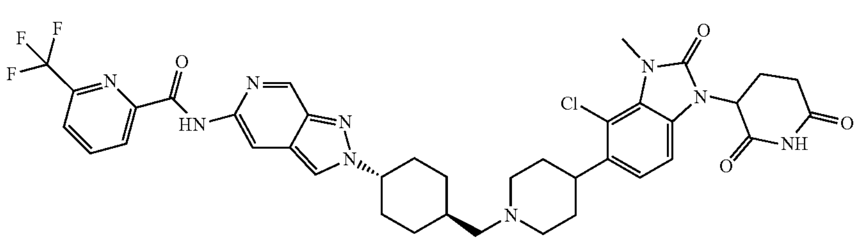 [SMILES: Cn1c(=O)n(C2CCC(=O)NC2=O)c2ccc(C3CCN(C[C@H]4CC[C@H](n5cc6cc(NC(=O)c7cccc(C(F)(F)F)n7)ncc6n5)CC4)CC3)c(Cl)c21] |

TABLE 1-continued

Exemplary Compounds

| I-# | Structure |
|---|---|
| I-179 | 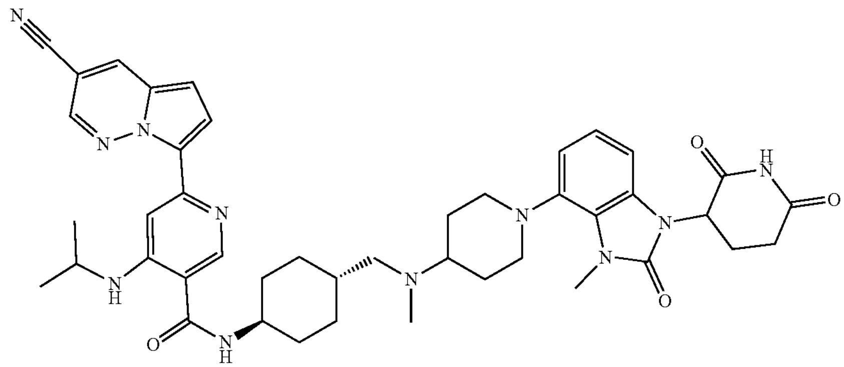 [SMILES: CC(C)Nc1cc(-c2ccc3cc(C#N)cnn23)ncc1C(=O)N[C@H]1CC[C@H](CN(C)C2CCN(c3cccc4c3n(C)c(=O)n4C3CCC(=O)NC3=O)CC2)CC1] |
| I-180 | 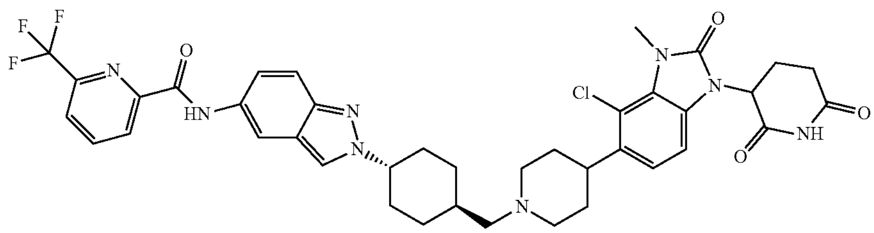 [SMILES: Cn1c(=O)n(C2CCC(=O)NC2=O)c2ccc(C3CCN(C[C@H]4CC[C@H](n5cc6cc(NC(=O)c7cccc(C(F)(F)F)n7)ccc6n5)CC4)CC3)c(Cl)c21] |
| I-181 | 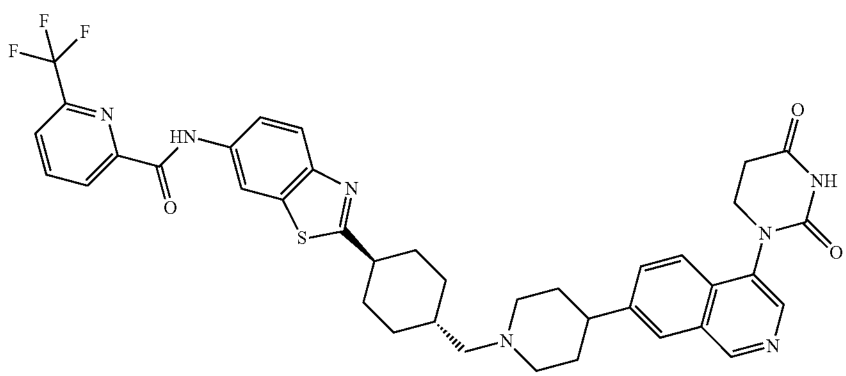 [SMILES: O=C1CCN(c2cncc3cc(C4CCN(C[C@H]5CC[C@H](c6nc7ccc(NC(=O)c8cccc(C(F)(F)F)n8)cc7s6)CC5)CC4)ccc23)C(=O)N1] |
| I-182 | 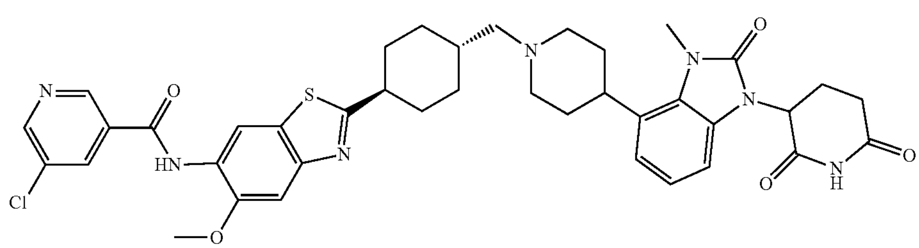 [SMILES: COc1cc2nc([C@H]3CC[C@H](CN4CCC(c5cccc6c5n(C)c(=O)n6C5CCC(=O)NC5=O)CC4)CC3)sc2cc1NC(=O)c1cncc(Cl)c1] |
| I-183 | 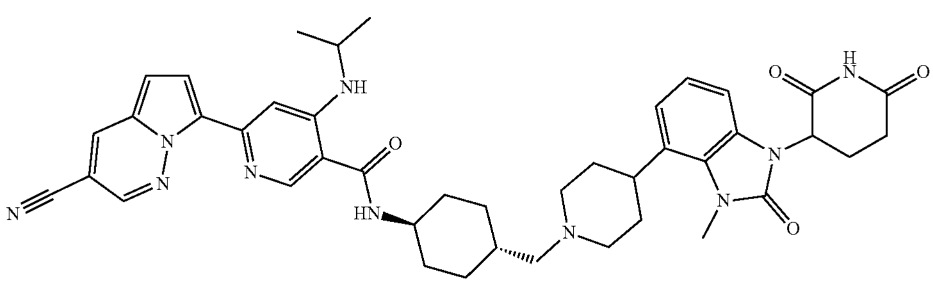 [SMILES: CC(C)Nc1cc(-c2ccc3cc(C#N)cnn23)ncc1C(=O)N[C@H]1CC[C@H](CN2CCC(c3cccc4c3n(C)c(=O)n4C3CCC(=O)NC3=O)CC2)CC1] |

TABLE 1-continued
Exemplary Compounds
| I-# | Structure |
|---|---|
| I-184 | 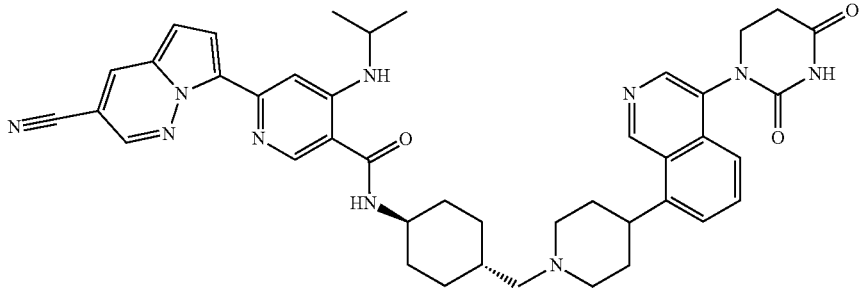 [SMILES: CC(C)Nc1cc(-c2ccc3cc(C#N)cnn23)ncc1C(=O)N[C@H]1CC[C@H](CN2CCC(c3cccc4c(N5CCC(=O)NC5=O)cncc34)CC2)CC1] |
| I-185 | 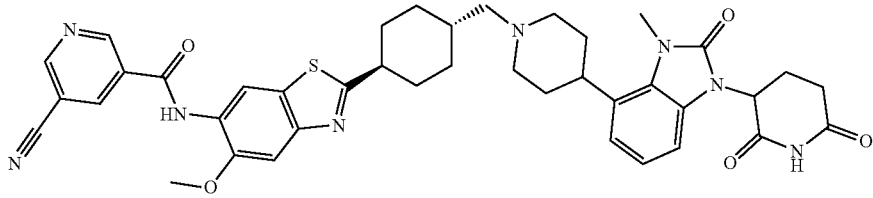 [SMILES: COc1cc2nc([C@H]3CC[C@H](CN4CCC(c5cccc6c5n(C)c(=O)n6C5CCC(=O)NC5=O)CC4)CC3)sc2cc1NC(=O)c1cncc(C#N)c1] |
| I-186 | 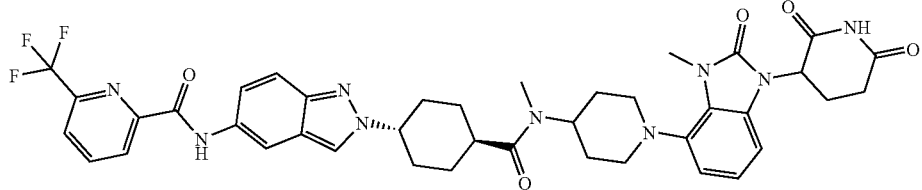 [SMILES: CN(C(=O)[C@H]1CC[C@H](n2cc3cc(NC(=O)c4cccc(C(F)(F)F)n4)ncc3n2)CC1)C1CCN(c2cccc3c2n(C)c(=O)n3C2CCC(=O)NC2=O)CC1] |
| I-187 | 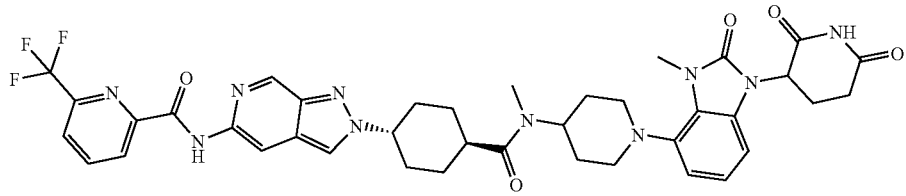 |
| I-188 | 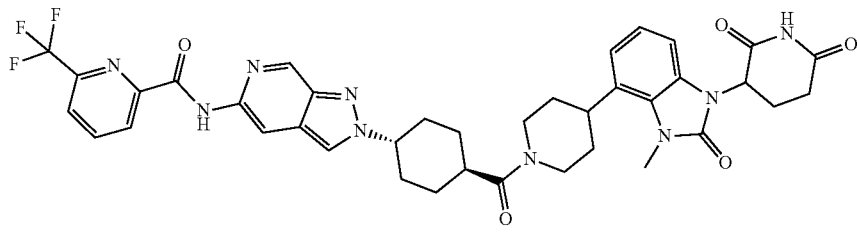 [SMILES: Cn1c(=O)n(C2CCC(=O)NC2=O)c2cccc(C3CCN(C(=O)[C@H]4CC[C@H](n5cc6cc(NC(=O)c7cccc(C(F)(F)F)n7)ncc6n5)CC4)CC3)c21] |
| I-189 | 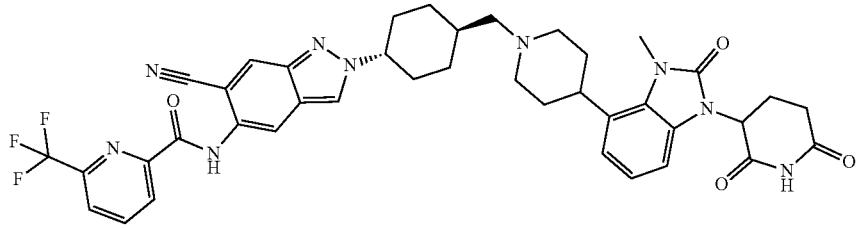 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)c(C#N)cc6n5)CC4)CC3)c21] |

TABLE 1-continued
Exemplary Compounds
| I-# | Structure |
|---|---|
| I-190 | 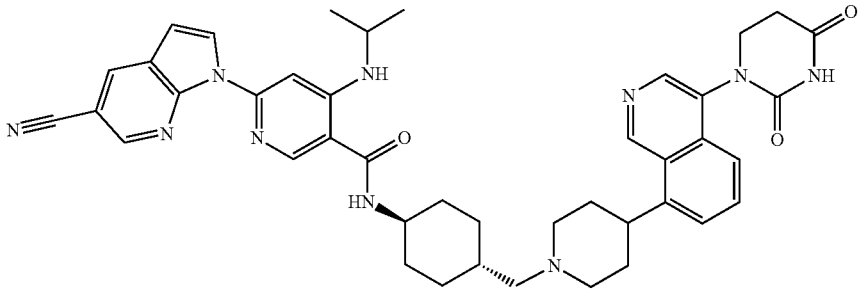 [SMILES: CC(C)Nc1cc(-n2ccc3cc(C#N)cnc32)ncc1C(=O)N[C@H]1CC[C@H](CN2CCC(c3cccc4c(N5CCC(=O)NC5=O)cncc34)CC2)CC1] |
| I-191 | 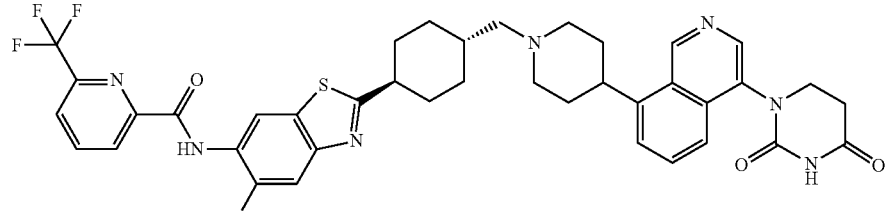 |
| I-193 | 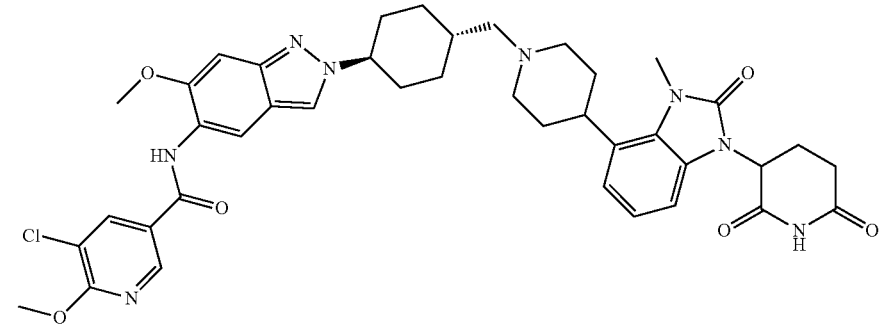 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cnc(OC)c(Cl)c1] |
| I-194 | 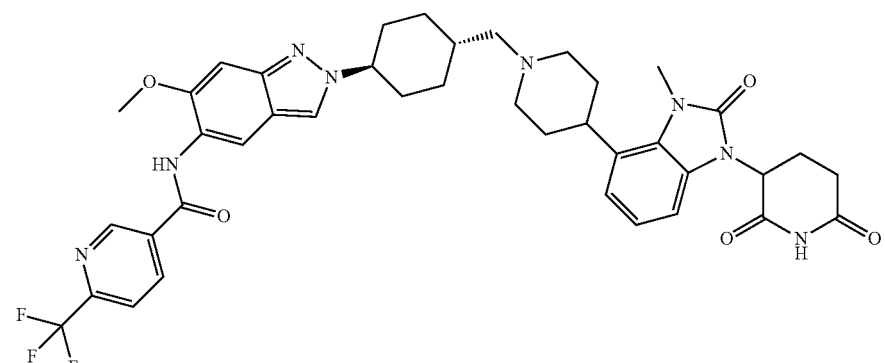 |
| I-195 | 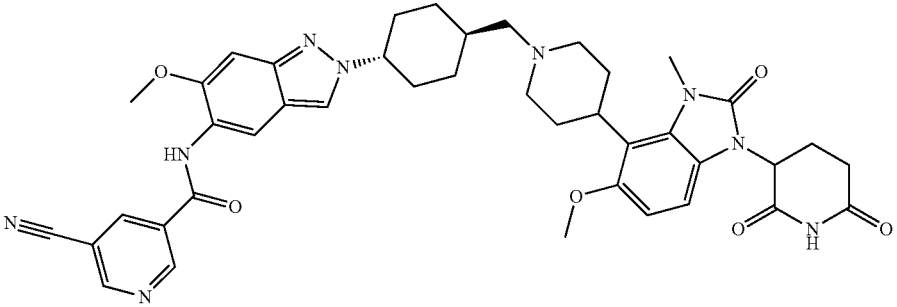 [SMILES: COc1cc2nn([C@H]3CC[C@H](CN4CCC(c5c(OC)ccc6c5n(C)c(=O)n6C5CCC(=O)NC5=O)CC4)CC3)cc2cc1NC(=O)c1cncc(C#N)c1] |

TABLE 1-continued
Exemplary Compounds
| I-# | Structure |
|---|---|
| I-196 | 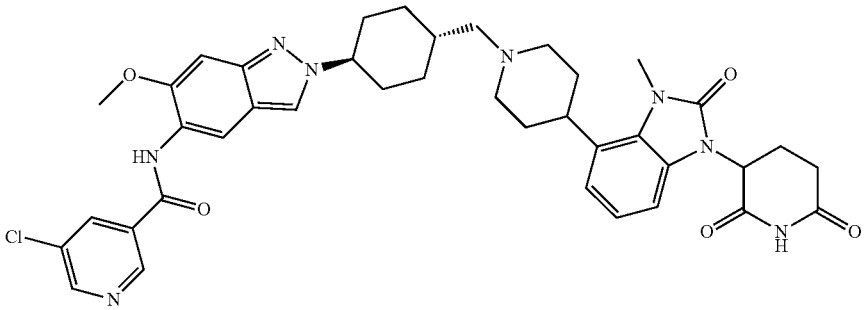 [SMILES: COc1cc2nn([C@H]3CC[C@H](CN4CCC(c5cccc6c5n(C)c(=O)n6C5CCC(=O)NC5=O)CC4)CC3)cc2cc1NC(=O)c1cncc(Cl)c1] |
| I-197 | 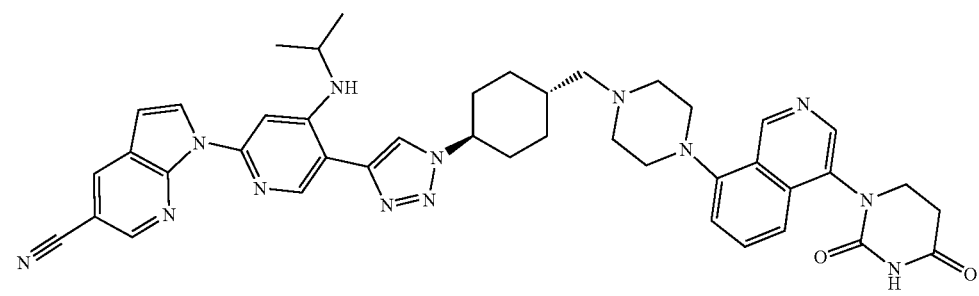 [SMILES: CC(C)Nc1cc(-n2ccc3cc(C#N)cnc32)ncc1-c1cn([C@H]2CC[C@H](CN3CCN(c4cccc5c(N6CCC(=O)NC6=O)cncc45)CC3)CC2)nn1] |
| I-198 | 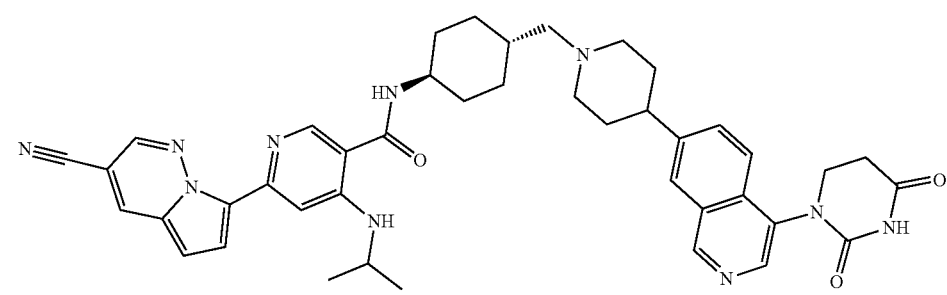 [SMILES: CC(C)Nc1cc(-c2ccc3cc(C#N)cnn23)ncc1C(=O)N[C@H]1CC[C@H](CN2CCC(c3ccc4c(N5CCC(=O)NC5=O)cncc4c3)CC2)CC1] |
| I-199 | 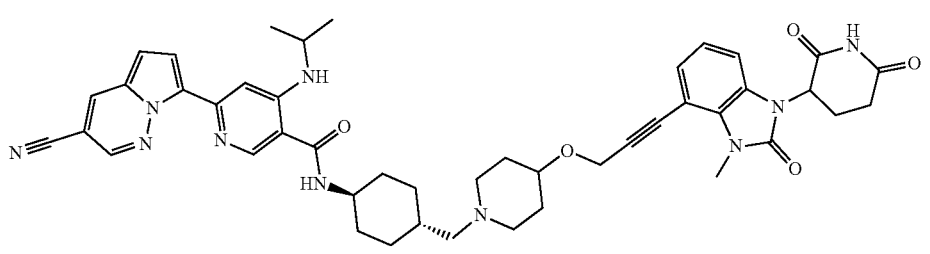 [SMILES: CC(C)Nc1cc(-c2ccc3cc(C#N)cnn23)ncc1C(=O)N[C@H]1CC[C@H](CN2CCC(OCC#Cc3cccc4c3n(C)c(=O)n4C3CCC(=O)NC3=O)CC2)CC1] |
| I-200 | 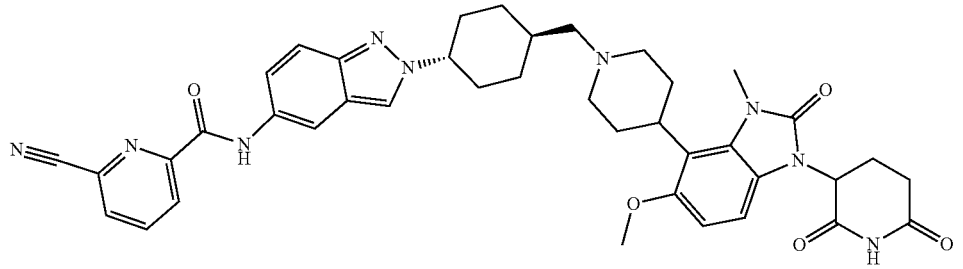 [SMILES: COc1ccc2c(c1C1CCN(C[C@H]3CC[C@H](n4cc5cc(NC(=O)c6cccc(C#N)n6)ccc5n4)CC3)CC1)n(C)c(=O)n2C1CCC(=O)NC1=O] |

TABLE 1-continued

Exemplary Compounds

| I-# | Structure |
|---|---|
| I-201 | 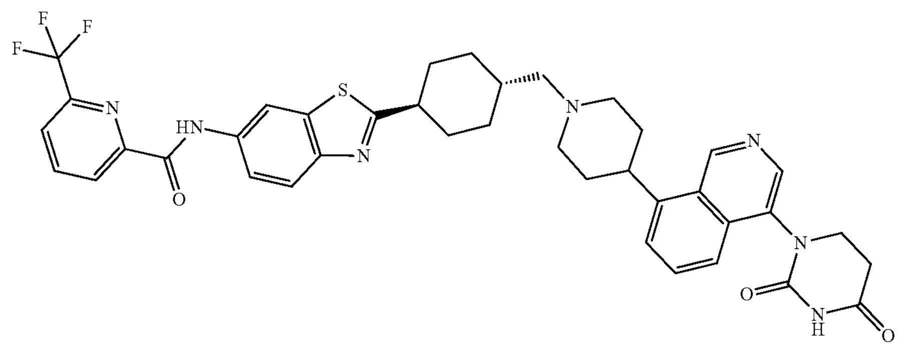 [SMILES: O=C1CCN(c2cncc3c(C4CCN(C[C@H]5CC[C@H](c6nc7ccc(NC(=O)c8cccc(C(F)(F)F)n8)cc7s6)CC5)CC4)cccc23)C(=O)N1] |
| I-202 | 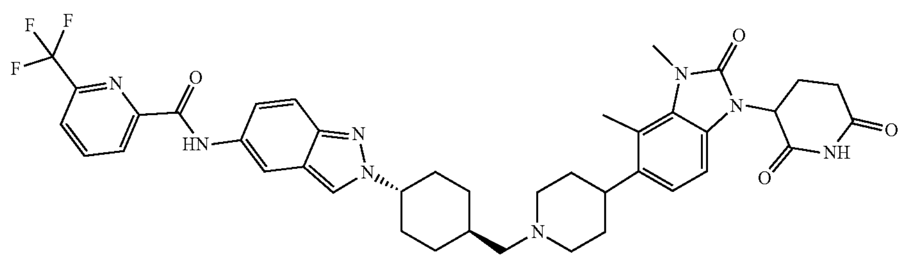 [SMILES: Cc1c(C2CCN(C[C@H]3CC[C@H](n4cc5cc(NC(=O)c6cccc(C(F)(F)F)n6)ccc5n4)CC3)CC2)ccc2c1n(C)c(=O)n2C1CCC(=O)NC1=O] |
| I-203 | 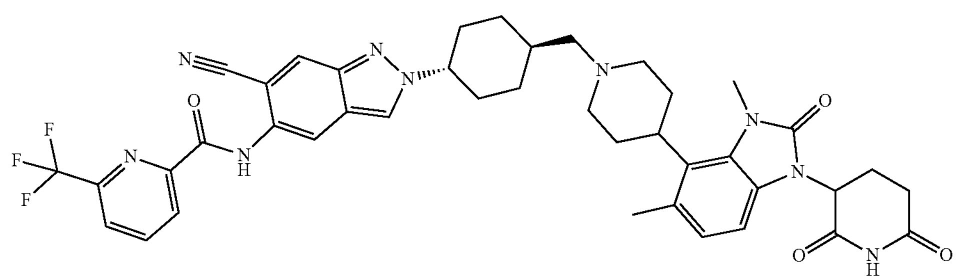 [SMILES: Cc1ccc2c(c1C1CCN(C[C@H]3CC[C@H](n4cc5cc(NC(=O)c6cccc(C(F)(F)F)n6)c(C#N)cc5n4)CC3)CC1)n(C)c(=O)n2C1CCC(=O)NC1=O] |
| I-204 | 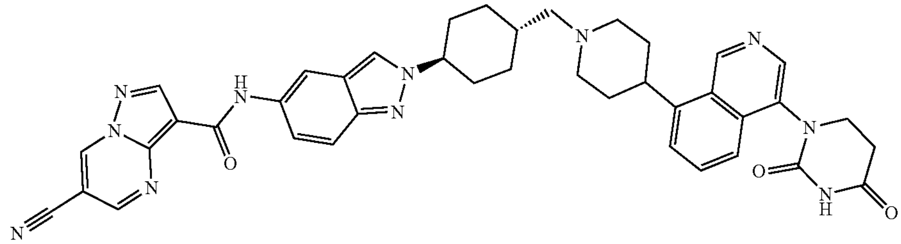 [SMILES: N#Cc1cnc2c(C(=O)Nc3ccc4nn([C@H]5CC[C@H](CN6CCC(c7cccc8c(N9CCC(=O)NC9=O)cncc78)CC6)CC5)cc4c3)cnn2c1] |
| I-205 | 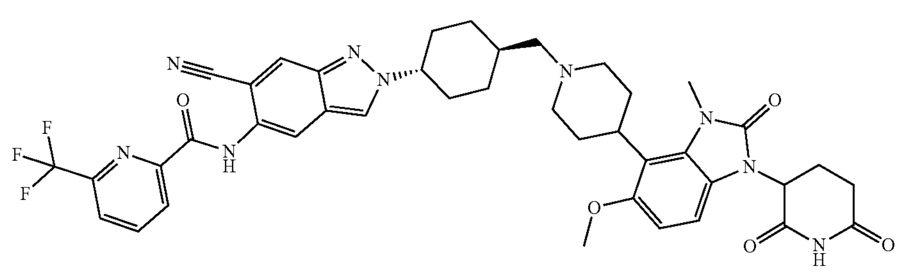 [SMILES: COc1ccc2c(c1C1CCN(C[C@H]3CC[C@H](n4cc5cc(NC(=O)c6cccc(C(F)(F)F)n6)c(C#N)cc5n4)CC3)CC1)n(C)c(=O)n2C1CCC(=O)NC1=O] |

TABLE 1-continued

Exemplary Compounds

| I-# | Structure |
|---|---|
| I-206 | 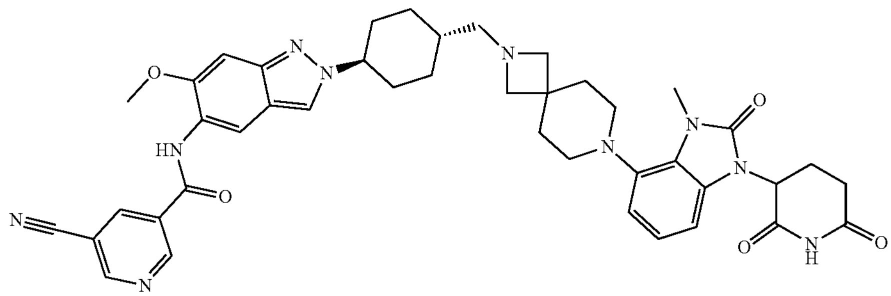 [SMILES: COc1cc2nn([C@H]3CC[C@H](CN4CC5(CCN(c6cccc7c6n(C)c(=O)n7C6CCC(=O)NC6=O)CC5)C4)CC3)cc2cc1NC(=O)c1cncc(C#N)c1] |
| I-207 | 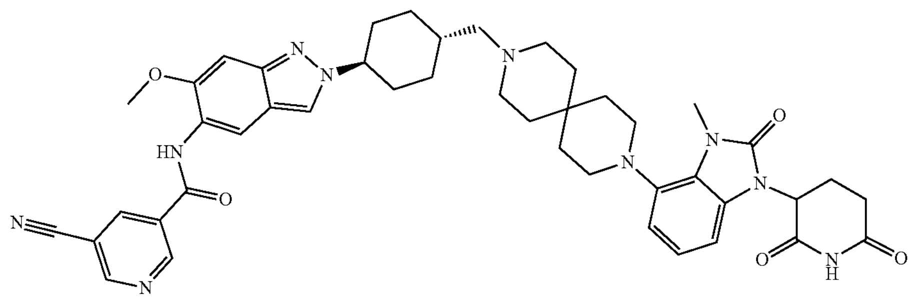 [SMILES: COc1cc2nn([C@H]3CC[C@H](CN4CCC5(CC4)CCN(c4cccc6c4n(C)c(=O)n6C4CCC(=O)NC4=O)CC5)CC3)cc2cc1NC(=O)c1cncc(C#N)c1] |
| I-208 | 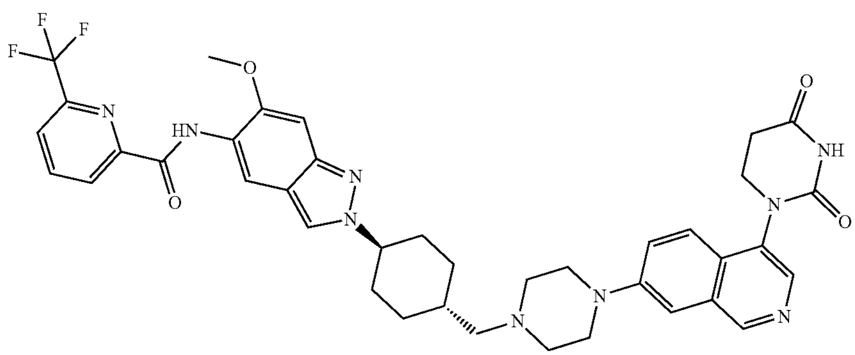 [SMILES: COc1cc2nn([C@H]3CC[C@H](CN4CCN(c5ccc6c(N7CCC(=O)NC7=O)cncc6c5)CC4)CC3)cc2cc1NC(=O)c1cccc(C(F)(F)F)n1] |
| I-209 | 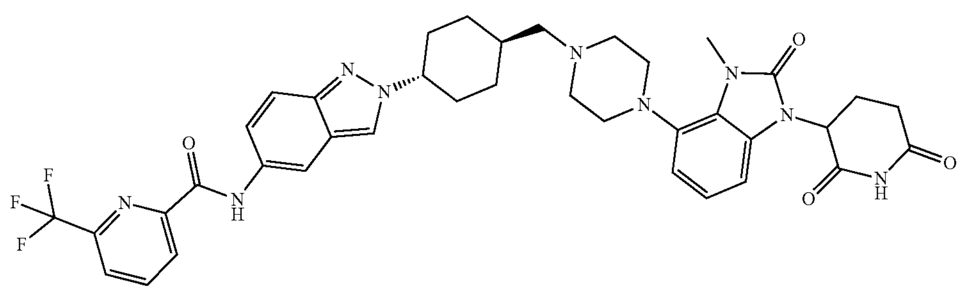 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)ccc6n5)CC4)CC3)c21] |
| I-210 | 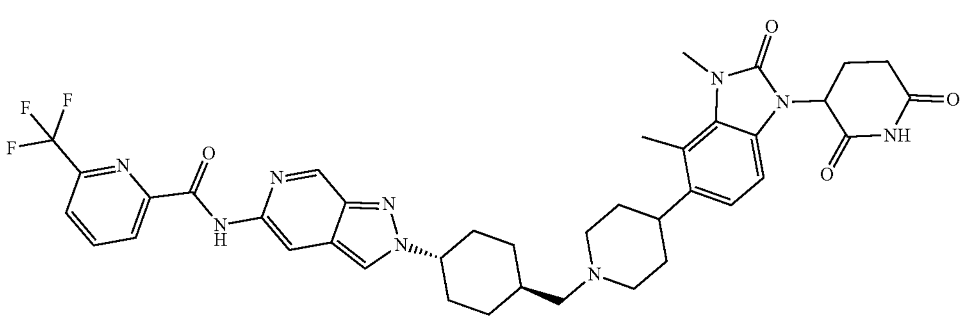 [SMILES: Cc1c(C2CCN(C[C@H]3CC[C@H](n4cc5cc(NC(=O)c6cccc(C(F)(F)F)n6)ncc5n4)CC3)CC2)ccc2c1n(C)c(=O)n2C1CCC(=O)NC1=O] |

TABLE 1-continued
Exemplary Compounds
| I-# | Structure |
|---|---|
| I-211 | 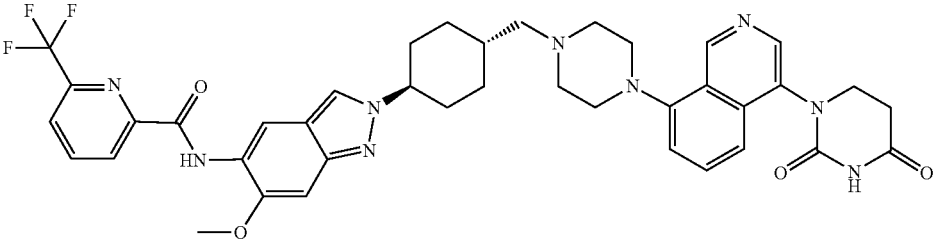 [SMILES: COc1cc2nn([C@H]3CC[C@H](CN4CCN(c5cccc6c(N7CCC(=O)NC7=O)cncc56)CC4)CC3)cc2cc1NC(=O)c1cccc(C(F)(F)F)n1] |
| I-212 | 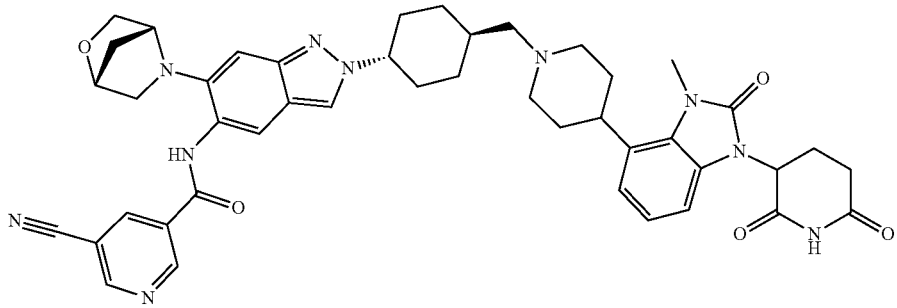 [SMILES: Cn1c(=O)n(C2CCC(=O)NC2=O)c2cccc(C3CCN(C[C@H]4CC[C@H](n5cc6cc(NC(=O)c7cncc(C#N)c7)c(N7C[C@H]8C[C@@H]7CO8)cc6n5)CC4)CC3)c21] |
| I-213 | 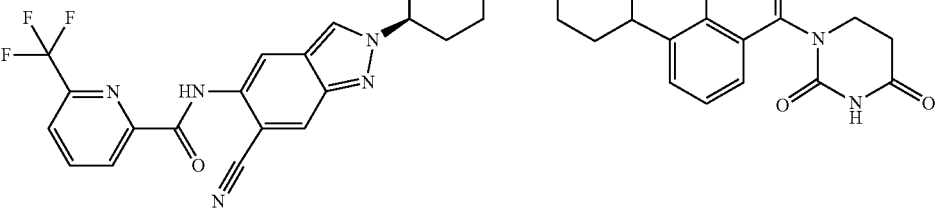 |
| I-214 | 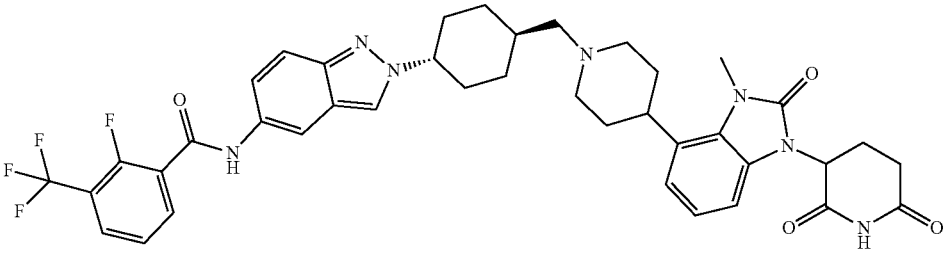 [SMILES: Cn1c(=O)n(C2CCC(=O)NC2=O)c2cccc(C3CCN(C[C@H]4CC[C@H](n5cc6cc(NC(=O)c7cccc(C(F)(F)F)c7F)ccc6n5)CC4)CC3)c21] |
| I-215 | 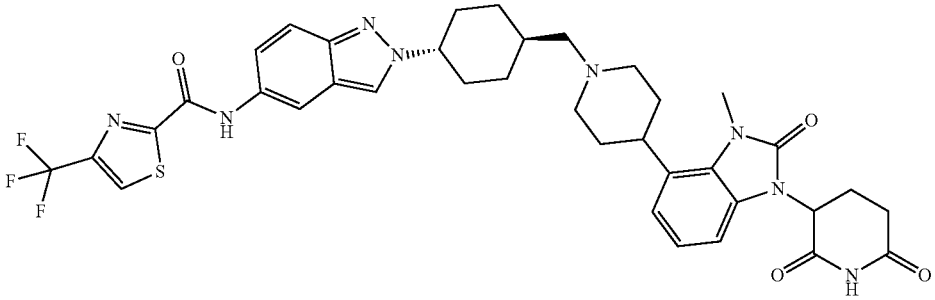 [SMILES: Cn1c(=O)n(C2CCC(=O)NC2=O)c2cccc(C3CCN(C[C@H]4CC[C@H](n5cc6cc(NC(=O)c7nc(C(F)(F)F)cs7)ccc6n5)CC4)CC3)c21] |

TABLE 1-continued
Exemplary Compounds
| I-# | Structure |
|---|---|
| I-216 | 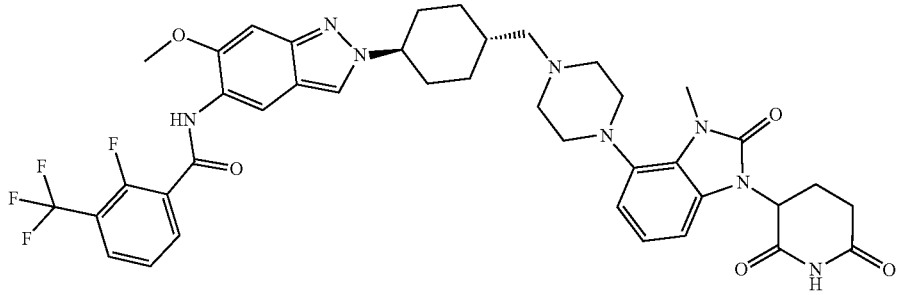 [SMILES: COc1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)c1F] |
| I-217 | 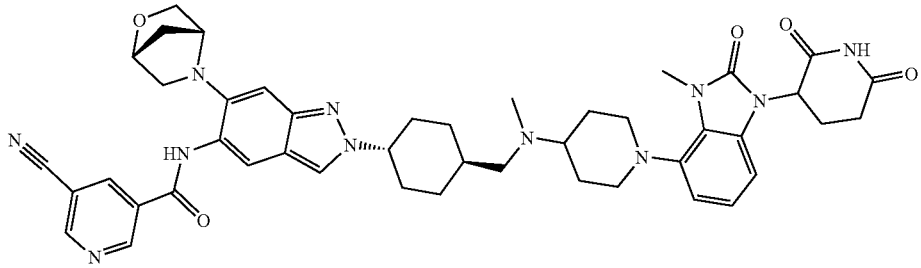 [SMILES: CN(C[C@H]1CC[C@H](n2cc3cc(NC(=O)c4cncc(C#N)c4)c(N4C[C@H]5C[C@@H]4CO5)cc3n2)CC1)C1CCN(c2cccc3c2n(C)c(=O)n3C2CCC(=O)NC2=O)CC1] |
| I-218 | 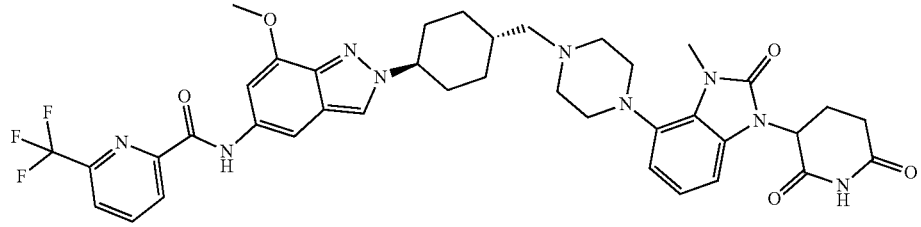 [SMILES: COc1cc(NC(=O)c2cccc(C(F)(F)F)n2)cc2cn([C@H]3CC[C@H](CN4CCN(c5cccc6c5n(C)c(=O)n6C5CCC(=O)NC5=O)CC4)CC3)nc12] |
| I-219 | 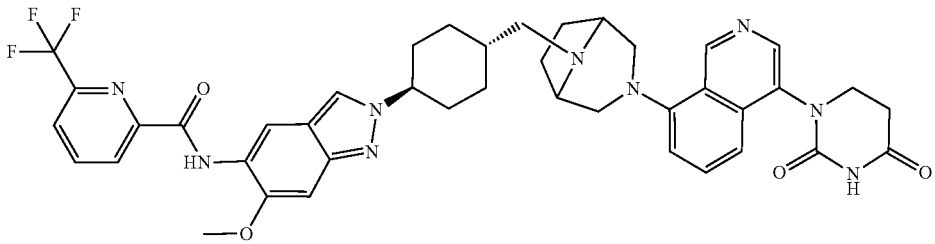 [SMILES: COc1cc2nn([C@H]3CC[C@H](CN4C5CCC4CN(c4cccc6c(N7CCC(=O)NC7=O)cncc46)C5)CC3)cc2cc1NC(=O)c1cccc(C(F)(F)F)n1] |
| I-220 | 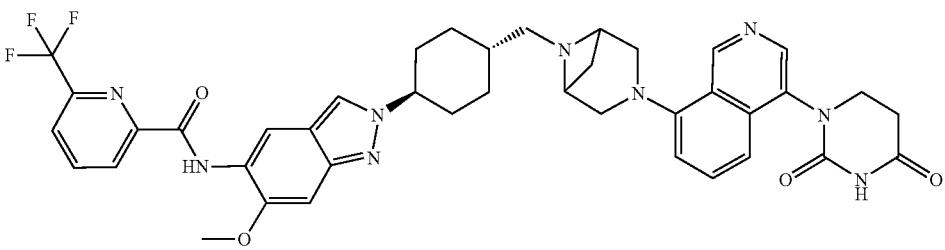 [SMILES: COc1cc2nn([C@H]3CC[C@H](CN4C5CC4CN(c4cccc6c(N7CCC(=O)NC7=O)cncc46)C5)CC3)cc2cc1NC(=O)c1cccc(C(F)(F)F)n1] |
| I-221 | 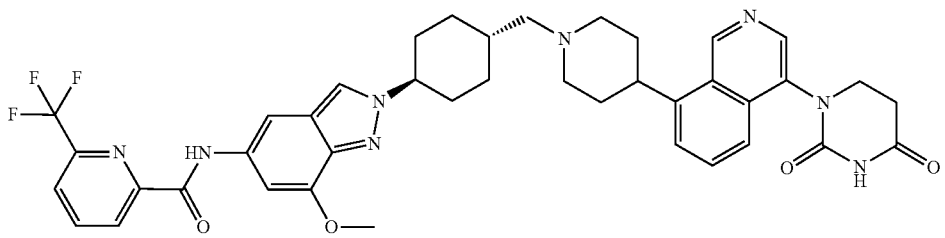 [SMILES: COc1cc(NC(=O)c2cccc(C(F)(F)F)n2)cc2cn([C@H]3CC[C@H](CN4CCC(c5cccc6c(N7CCC(=O)NC7=O)cncc56)CC4)CC3)nc12] |

TABLE 1-continued

Exemplary Compounds

| I-# | Structure |
|---|---|
| I-222 | 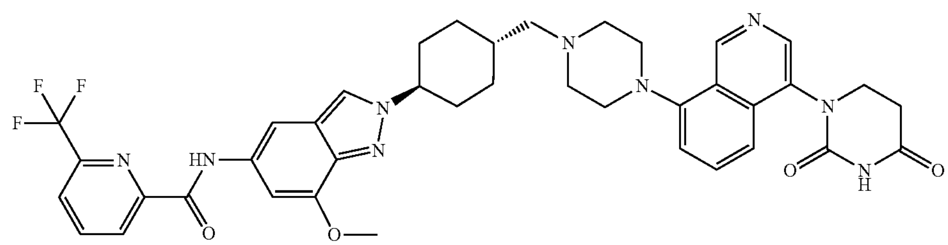 [SMILES: COc1cc(NC(=O)c2cccc(C(F)(F)F)n2)cc2cn([C@H]3CC[C@H](CN4CCN(c5cccc6c(N7CCC(=O)NC7=O)cncc56)CC4)CC3)nc12] |
| I-223 | 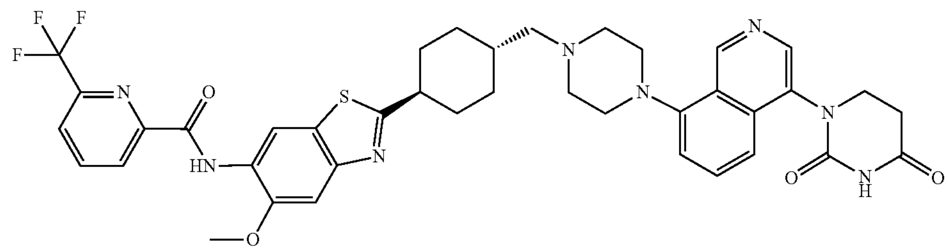 [SMILES: COc1cc2nc([C@H]3CC[C@H](CN4CCN(c5cccc6c(N7CCC(=O)NC7=O)cncc56)CC4)CC3)sc2cc1NC(=O)c1cccc(C(F)(F)F)n1] |
| I-224 | 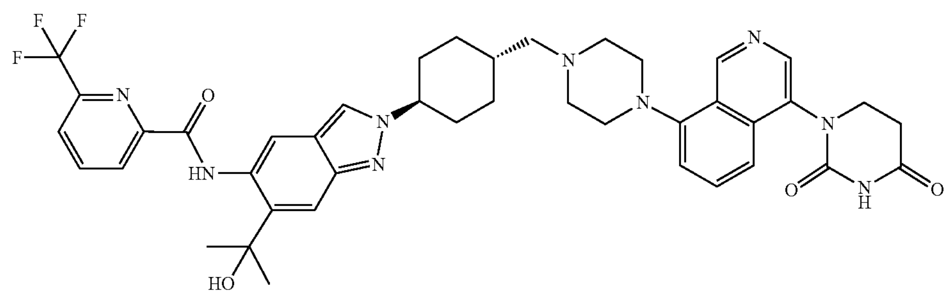 [SMILES: CC(C)(O)c1cc2nn([C@H]3CC[C@H](CN4CCN(c5cccc6c(N7CCC(=O)NC7=O)cncc56)CC4)CC3)cc2cc1NC(=O)c1cccc(C(F)(F)F)n1] |
| I-225 | 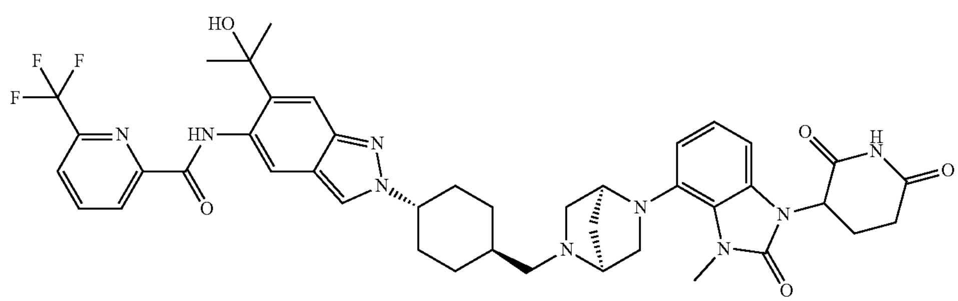 [SMILES: Cn1c(=O)n(C2CCC(=O)NC2=O)c2cccc(N3C[C@@H]4C[C@H]3CN4C[C@H]3CC[C@H](n4cc5cc(NC(=O)c6cccc(C(F)(F)F)n6)c(C(C)(C)O)cc5n4)CC3)c21] |
| I-226 | 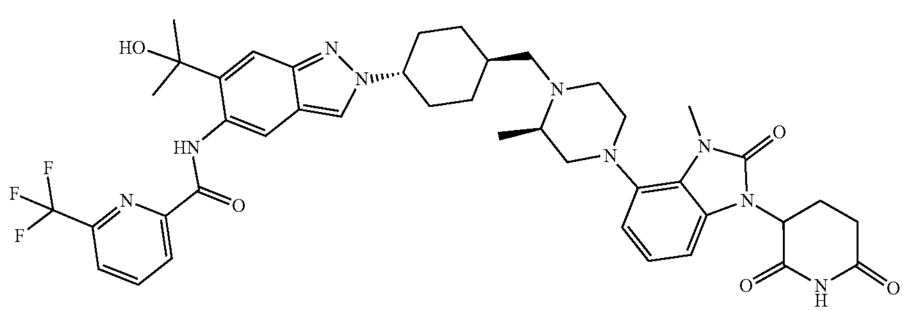 [SMILES: C[C@@H]1CN(c2cccc3c2n(C)c(=O)n3C2CCC(=O)NC2=O)CCN1C[C@H]1CC[C@H](n2cc3cc(NC(=O)c4cccc(C(F)(F)F)n4)c(C(C)(C)O)cc3n2)CC1] |

TABLE 1-continued

Exemplary Compounds

| I-# | Structure |
|---|---|
| I-227 | 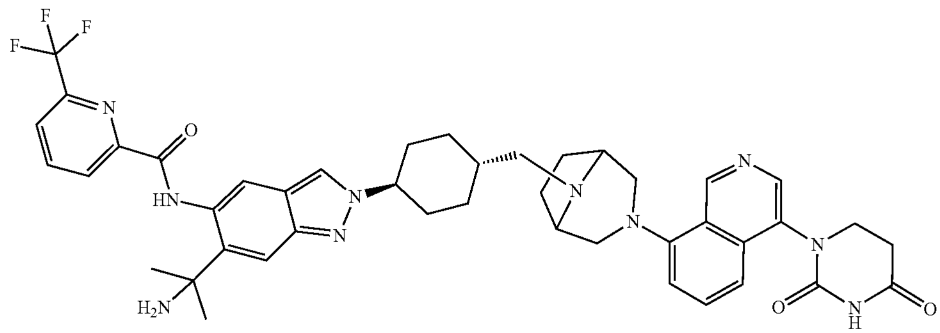 [SMILES: CC(C)(N)c1cc2nn([C@H]3CC[C@H](CN4C5CCC4CN(c4cccc6c(N7CCC(=O)NC7=O)cncc46)C5)CC3)cc2cc1NC(=O)c1cccc(C(F)(F)F)n1] |
| I-228 | 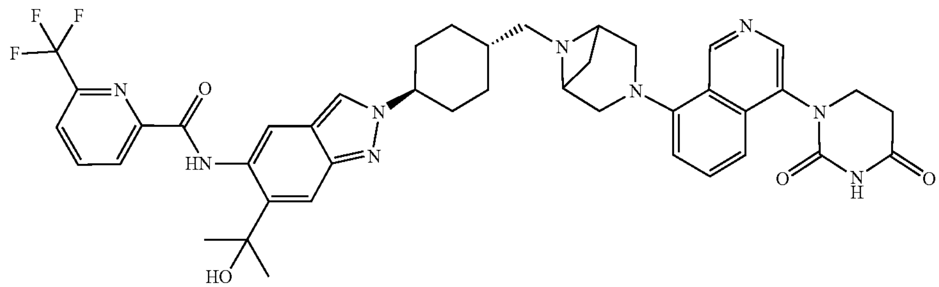 [SMILES: CC(C)(O)c1cc2nn([C@H]3CC[C@H](CN4C5CC4CN(c4cccc6c(N7CCC(=O)NC7=O)cncc46)C5)CC3)cc2cc1NC(=O)c1cccc(C(F)(F)F)n1] |
| I-229 | 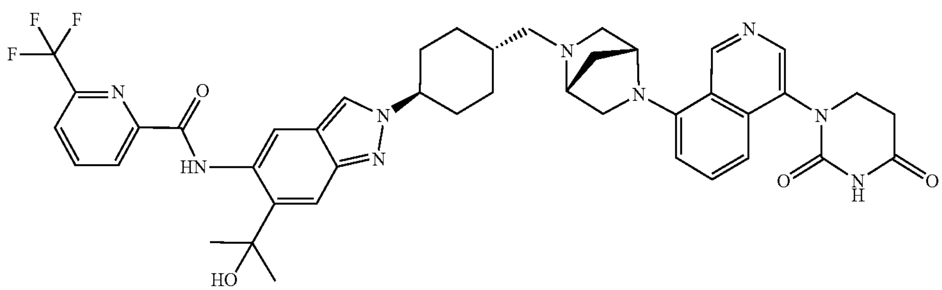 [SMILES: CC(C)(O)c1cc2nn([C@H]3CC[C@H](CN4C[C@H]5C[C@@H]4CN5c4cccc5c(N6CCC(=O)NC6=O)cncc45)CC3)cc2cc1NC(=O)c1cccc(C(F)(F)F)n1] |
| I-230 | 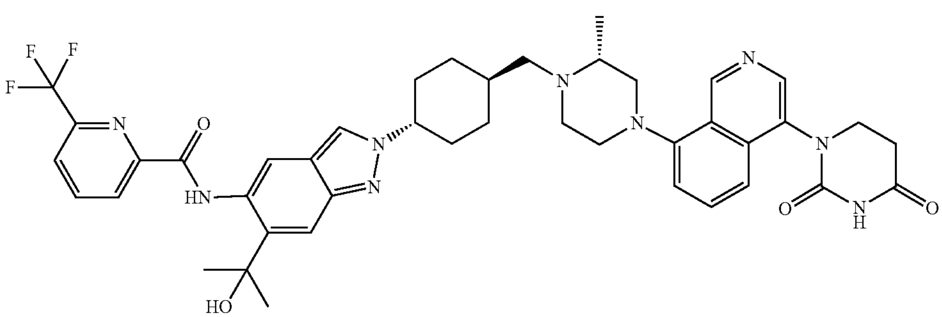 [SMILES: C[C@@H]1CN(c2cccc3c(N4CCC(=O)NC4=O)cncc23)CCN1C[C@H]1CC[C@H](n2cc3cc(NC(=O)c4cccc(C(F)(F)F)n4)c(C(C)(C)O)cc3n2)CC1] |
| I-231 | 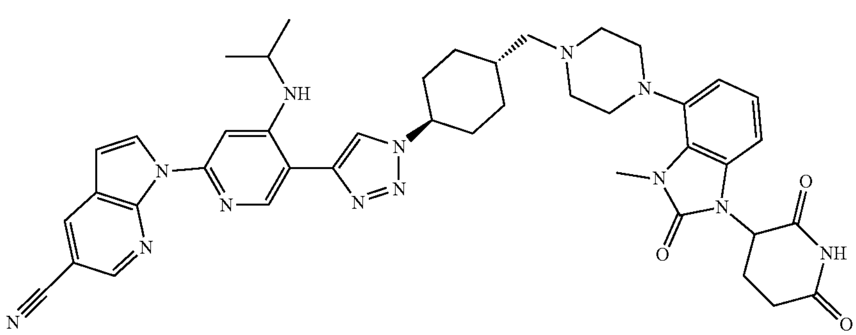 [SMILES: CC(C)Nc1cc(-n2ccc3cc(C#N)cnc32)ncc1-c1cn([C@H]2CC[C@H](CN3CCN(c4cccc5c4n(C)c(=O)n5C4CCC(=O)NC4=O)CC3)CC2)nn1] |

TABLE 1-continued
Exemplary Compounds
| I-# | Structure |
|---|---|
| I-232 | 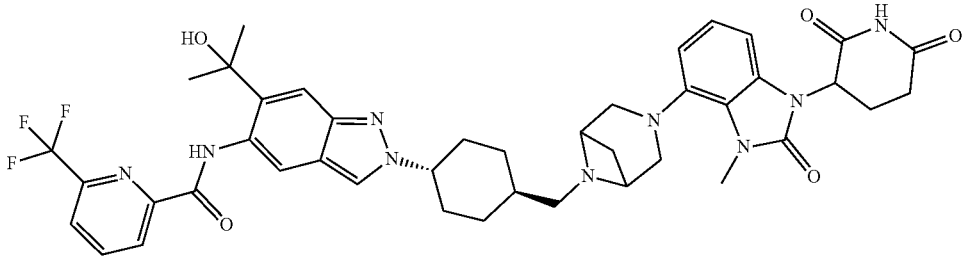 [SMILES: Cn1c(=O)n(C2CCC(=O)NC2=O)c2cccc(N3CC4CC(C3)N4C[C@H]3CC[C@H](n4cc5cc(NC(=O)c6cccc(C(F)(F)F)n6)c(C(C)(C)O)cc5n4)CC3)c21] |
| I-233 | 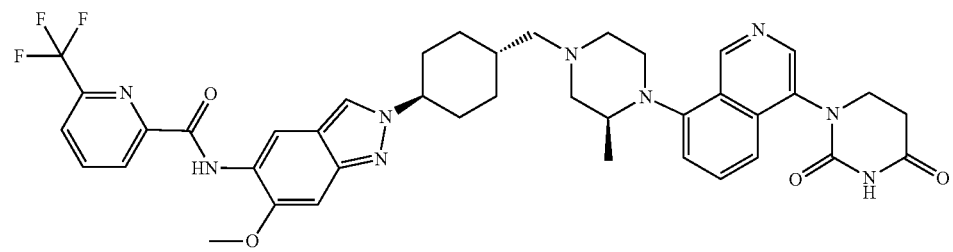 [SMILES: COc1cc2nn([C@H]3CC[C@H](CN4CCN(c5cccc6c(N7CCC(=O)NC7=O)cncc56)[C@@H](C)C4)CC3)cc2cc1NC(=O)c1cccc(C(F)(F)F)n1] |
| I-234 | 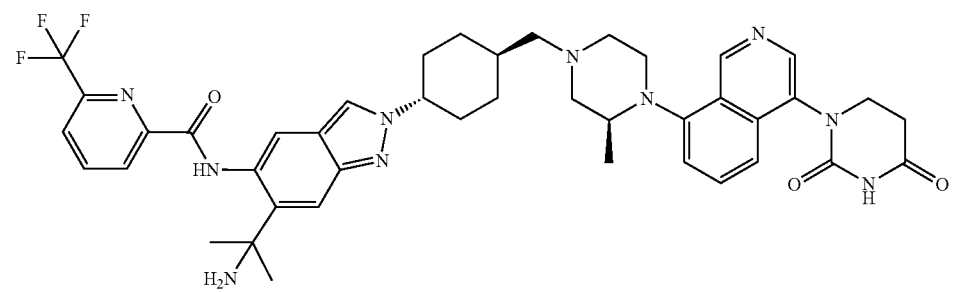 [SMILES: C[C@H]1CN(C[C@H]2CC[C@H](n3cc4cc(NC(=O)c5cccc(C(F)(F)F)n5)c(C(C)(C)N)cc4n3)CC2)CCN1c1cccc2c(N3CCC(=O)NC3=O)cncc12] |
| I-235 | 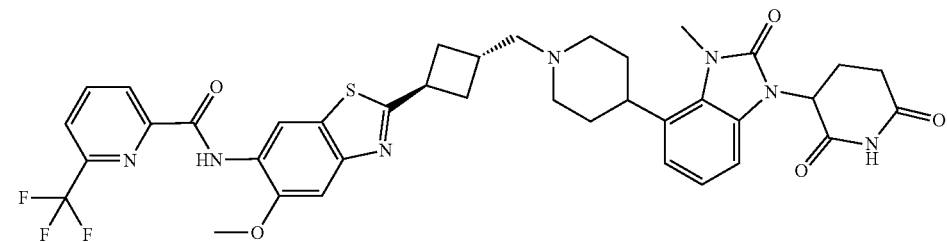 [SMILES: COc1cc2nc([C@H]3C[C@H](CN4CCC(c5cccc6c5n(C)c(=O)n6C5CCC(=O)NC5=O)CC4)C3)sc2cc1NC(=O)c1cccc(C(F)(F)F)n1] |
| I-236 | 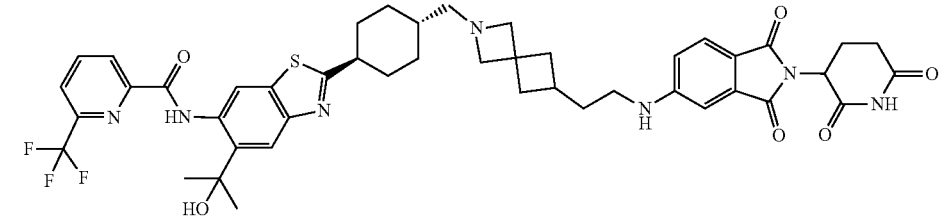 [SMILES: CC(C)(O)c1cc2nc([C@H]3CC[C@H](CN4CC5(CC(CCNc6ccc7c(c6)C(=O)N(C6CCC(=O)NC6=O)C7=O)C5)C4)CC3)sc2cc1NC(=O)c1cccc(C(F)(F)F)n1] |

TABLE 1-continued

Exemplary Compounds

| I-# | Structure |
| --- | --- |
| I-237 | 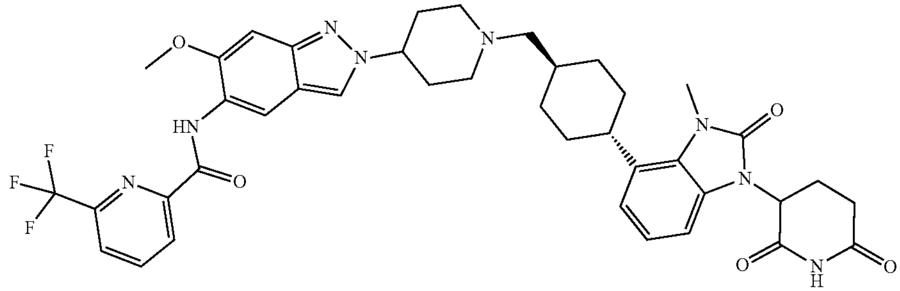 [SMILES: COc1cc2nn(C3CCN(C[C@H]4CC[C@H](c5cccc6c5n(C)c(=O)n6C5CCC(=O)NC5=O)CC4)CC3)cc2cc1NC(=O)c1cccc(C(F)(F)F)n1] |
| I-238 | 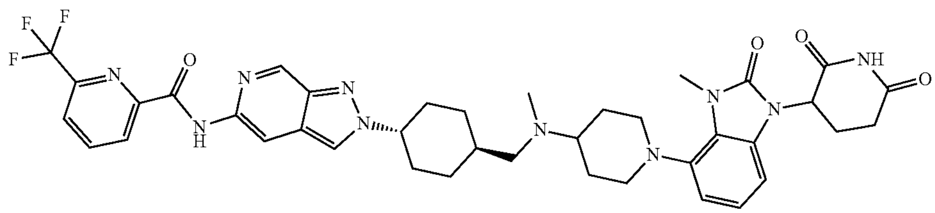 [SMILES: CN(C[C@H]1CC[C@H](n2cc3cc(NC(=O)c4cccc(C(F)(F)F)n4)ncc3n2)CC1)C1CCN(c2cccc3c2n(C)c(=O)n3C2CCC(=O)NC2=O)CC1] |
| I-239 | 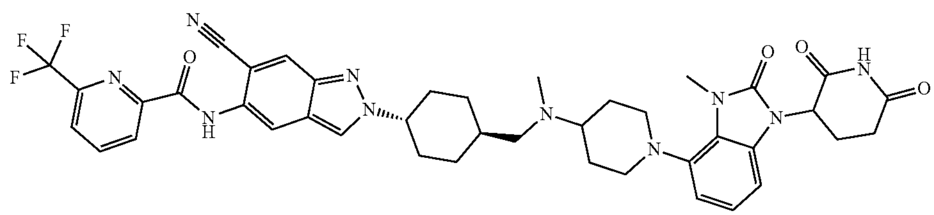 [SMILES: CN(C[C@H]1CC[C@H](n2cc3cc(NC(=O)c4cccc(C(F)(F)F)n4)c(C#N)cc3n2)CC1)C1CCN(c2cccc3c2n(C)c(=O)n3C2CCC(=O)NC2=O)CC1] |
| I-240 | 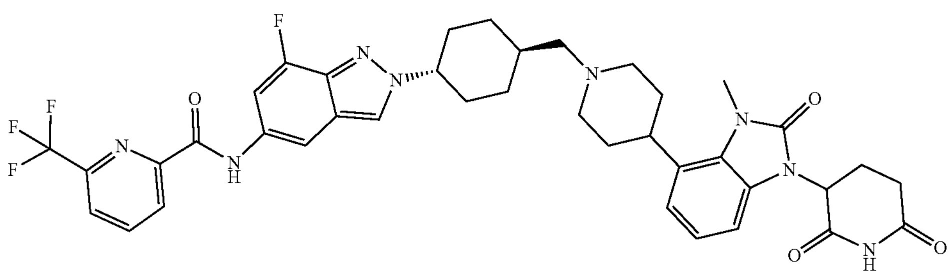 [SMILES: Cn1c(=O)n(C2CCC(=O)NC2=O)c2cccc(C3CCN(C[C@H]4CC[C@H](n5cc6cc(NC(=O)c7cccc(C(F)(F)F)n7)cc(F)c6n5)CC4)CC3)c21] |
| I-241 | 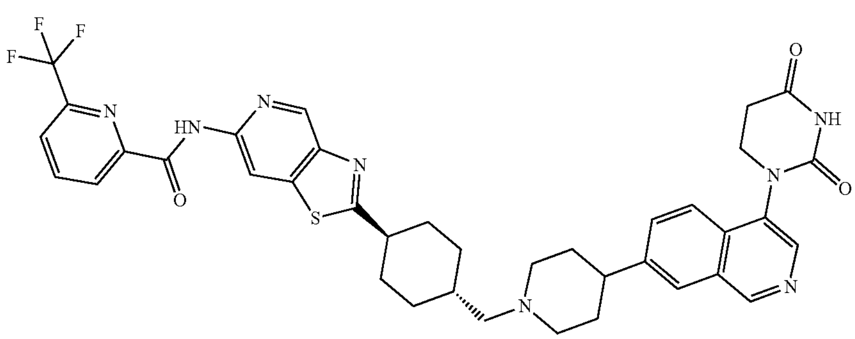 [SMILES: O=C1CCN(c2cncc3cc(C4CCN(C[C@H]5CC[C@H](c6nc7cnc(NC(=O)c8cccc(C(F)(F)F)n8)cc7s6)CC5)CC4)ccc23)C(=O)N1] |

TABLE 1-continued
Exemplary Compounds
| I-# | Structure |
|---|---|
| I-242 | 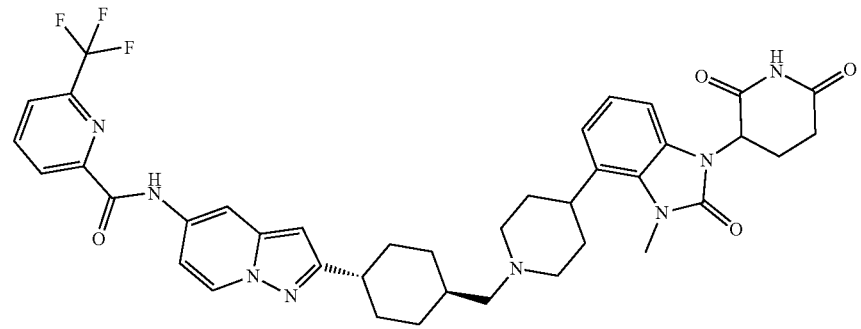 [SMILES: Cn1c(=O)n(C2CCC(=O)NC2=O)c2cccc(C3CCN(C[C@H]4CC[C@H](c5cc6cc(NC(=O)c7cccc(C(F)(F)F)n7)ccn6n5)CC4)CC3)c21] |
| I-243 | 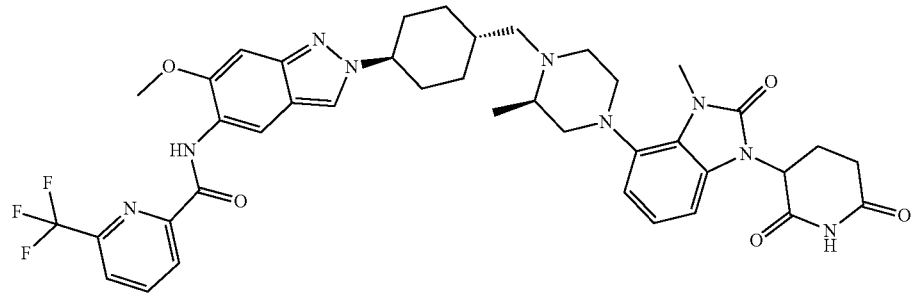 [SMILES: COc1cc2nn([C@H]3CC[C@H](CN4CCN(c5cccc6c5n(C)c(=O)n6C5CCC(=O)NC5=O)C[C@H]4C)CC3)cc2cc1NC(=O)c1cccc(C(F)(F)F)n1] |
| I-244 | 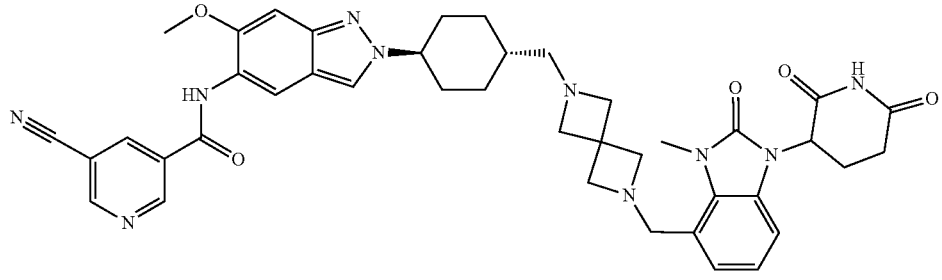 [SMILES: COc1cc2nn([C@H]3CC[C@H](CN4CC5(CN(Cc6cccc7c6n(C)c(=O)n7C6CCC(=O)NC6=O)C5)C4)CC3)cc2cc1NC(=O)c1cncc(C#N)c1] |
| I-245 | 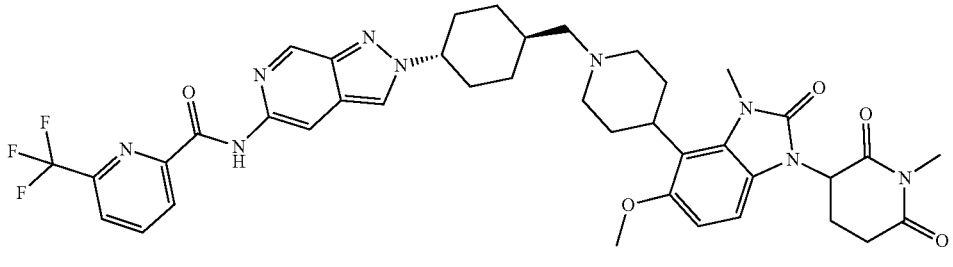 [SMILES: COc1ccc2c(c1C1CCN(C[C@H]3CC[C@H](n4cc5cc(NC(=O)c6cccc(C(F)(F)F)n6)ncc5n4)CC3)CC1)n(C)c(=O)n2C1CCC(=O)N(C)C1=O] |
| I-246 | 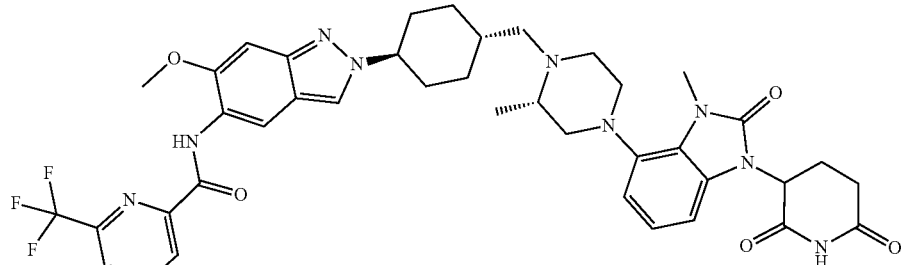 |

TABLE 1-continued

Exemplary Compounds

| I-# | Structure |
|---|---|
| I-247 | 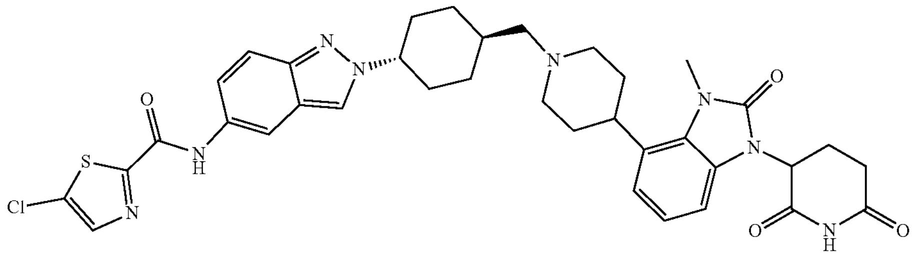 [SMILES: Cn1c(=O)n(C2CCC(=O)NC2=O)c2cccc(C3CCN(C[C@H]4CC[C@H](n5cc6cc(NC(=O)c7ncc(Cl)s7)ccc6n5)CC4)CC3)c21] |
| I-248 | 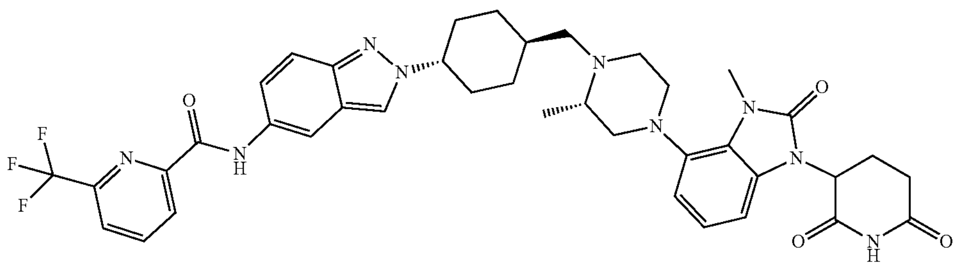 [SMILES: C[C@H]1CN(c2cccc3c2n(C)c(=O)n3C2CCC(=O)NC2=O)CCN1C[C@H]1CC[C@H](n2cc3cc(NC(=O)c4cccc(C(F)(F)F)n4)ccc3n2)CC1] |
| I-249 | 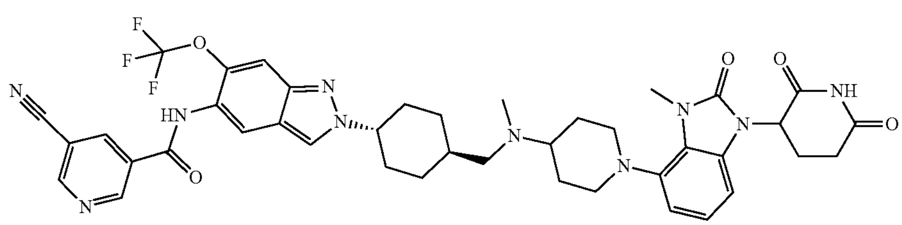 [SMILES: CN(C[C@H]1CC[C@H](n2cc3cc(NC(=O)c4cncc(C#N)c4)c(OC(F)(F)F)cc3n2)CC1)C1CCN(c2cccc3c2n(C)c(=O)n3C2CCC(=O)NC2=O)CC1] |
| I-250 | 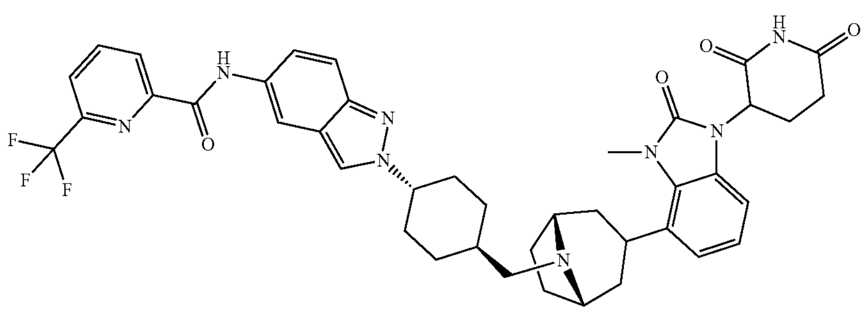 [SMILES: Cn1c(=O)n(C2CCC(=O)NC2=O)c2cccc(C3C[C@H]4CC[C@@H](C3)N4C[C@H]3CC[C@H](n4cc5cc(NC(=O)c6cccc(C(F)(F)F)n6)ccc5n4)CC3)c21] |
| I-251 | 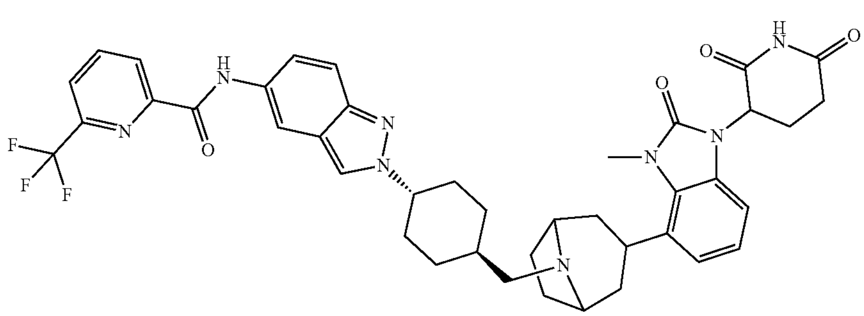 [SMILES: Cn1c(=O)n(C2CCC(=O)NC2=O)c2cccc(C3CC4CCC(C3)N4C[C@H]3CC[C@H](n4cc5cc(NC(=O)c6cccc(C(F)(F)F)n6)ccc5n4)CC3)c21] |

TABLE 1-continued

Exemplary Compounds

| I-# | Structure |
|---|---|
| I-252 | 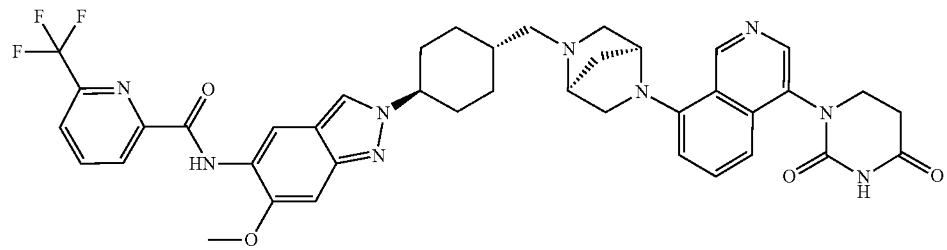 |
| I-253 | 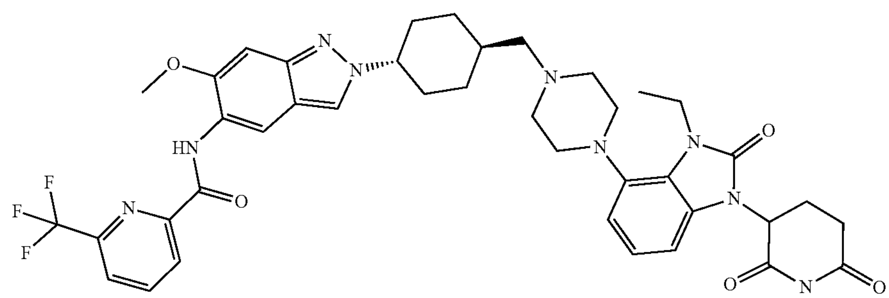 |
| I-254 | 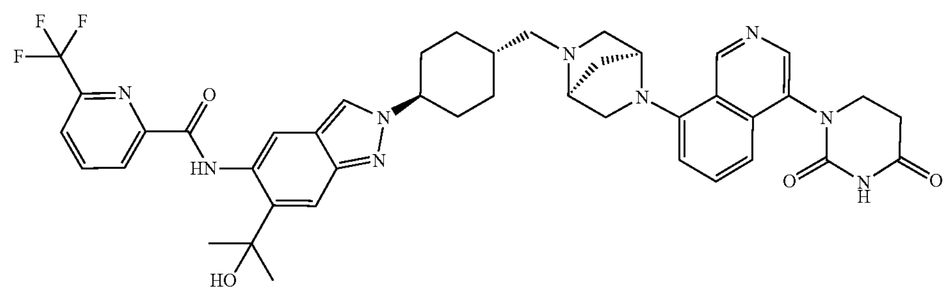 |
| I-255 | 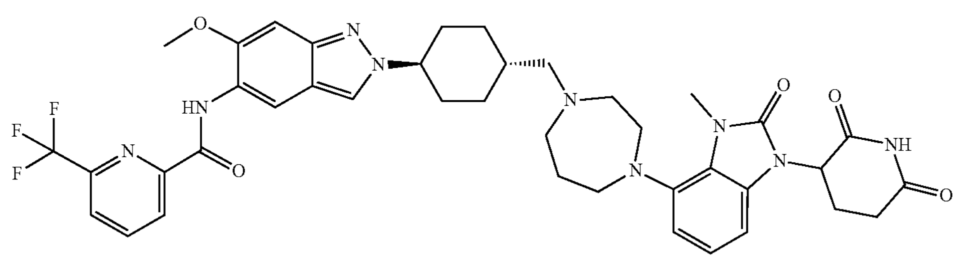 [SMILES: COc1cc2nn([C@H]3CC[C@H](CN4CCCN(c5cccc6c5n(C)c(=O)n6C5CCC(=O)NC5=O)CC4)CC3)cc2cc1NC(=O)c1cccc(C(F)(F)F)n1] |
| I-256 | 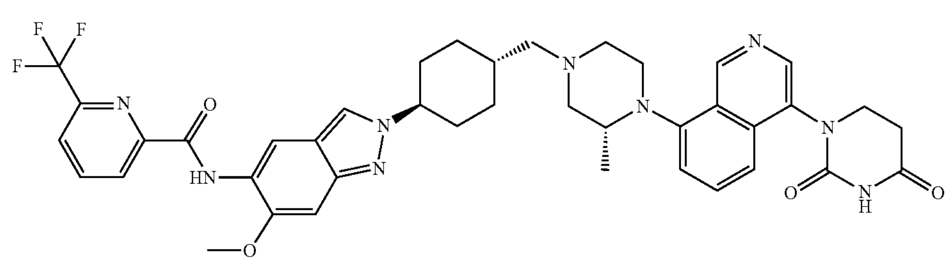 [SMILES: COc1cc2nn([C@H]3CC[C@H](CN4CCN(c5cccc6c(N7CCC(=O)NC7=O)cncc56)[C@H](C)C4)CC3)cc2cc1NC(=O)c1cccc(C(F)(F)F)n1] |

TABLE 1-continued
Exemplary Compounds
| I-# | Structure |
|---|---|
| I-257 | 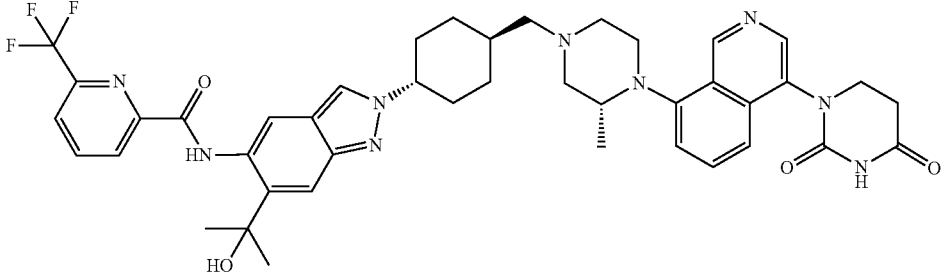 [SMILES: C[C@@H]1CN(C[C@H]2CC[C@H](n3cc4cc(NC(=O)c5cccc(C(F)(F)F)n5)c(C(C)(C)O)cc4n3)CC2)CCN1c1cccc2c(N3CCC(=O)NC3=O)cncc12] |
| I-258 | 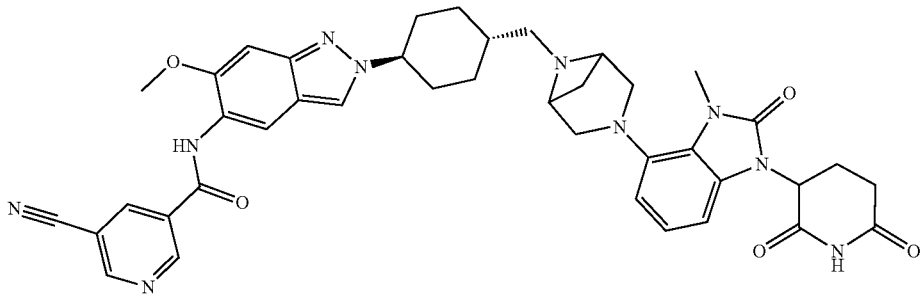 [SMILES: COc1cc2nn([C@H]3CC[C@H](CN4C5CC4CN(c4cccc6c4n(C)c(=O)n6C4CCC(=O)NC4=O)C5)CC3)cc2cc1NC(=O)c1cncc(C#N)c1] |
| I-259 | 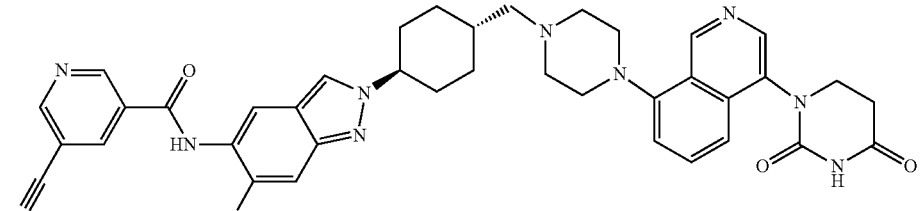 |
| I-260 | 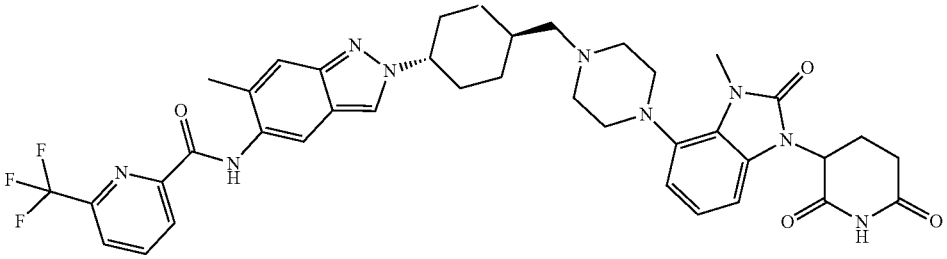 [SMILES: CC[C@H](CC[C@@H](C)CN1CCN(c2cccc3c2n(C)c(=O)n3C2CCC(=O)NC2=O)CC1)n1cc2cc(NC(=O)c3cccc(C(F)(F)F)n3)c(C)cc2n1] |
| I-261 | 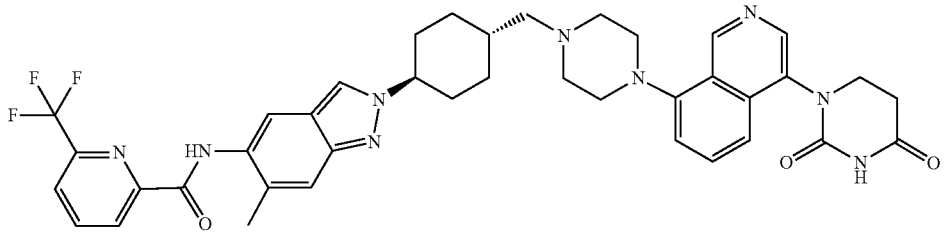 [SMILES: Cc1cc2nn([C@H]3CC[C@H](CN4CCN(c5cccc6c(N7CCC(=O)NC7=O)cncc56)CC4)CC3)cc2cc1NC(=O)c1cccc(C(F)(F)F)n1] |

TABLE 1-continued

Exemplary Compounds

| I-# | Structure |
|---|---|
| I-262 | 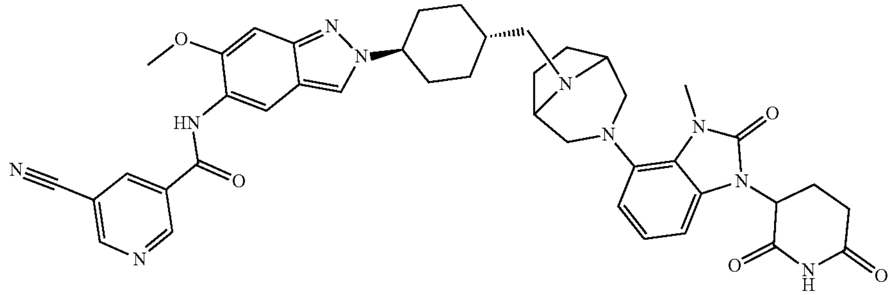 [SMILES: COc1cc2nn([C@H]3CC[C@H](CN4C5CCC4CN(c4cccc6c4n(C)c(=O)n6C4CCC(=O)NC4=O)C5)CC3)cc2cc1NC(=O)c1cncc(C#N)c1] |
| I-263 | 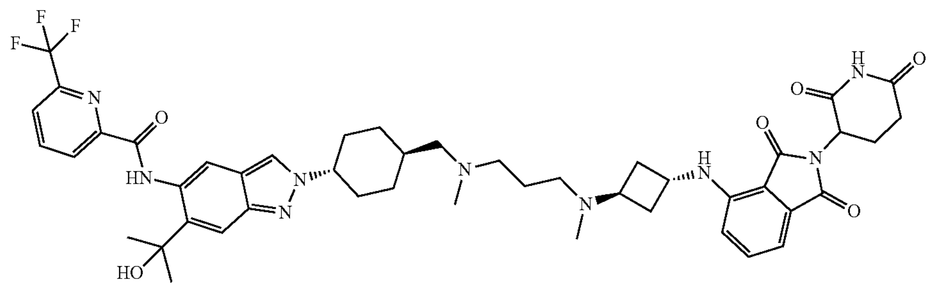 [SMILES: CN(CCCN(C)[C@H]1C[C@H](Nc2cccc3c2C(=O)N(C2CCC(=O)NC2=O)C3=O)C1)C[C@H]1CC[C@H](n2cc3cc(NC(=O)c4cccc(C(F)(F)F)n4)c(C(C)(C)O)cc3n2)CC1] |
| I-264 | 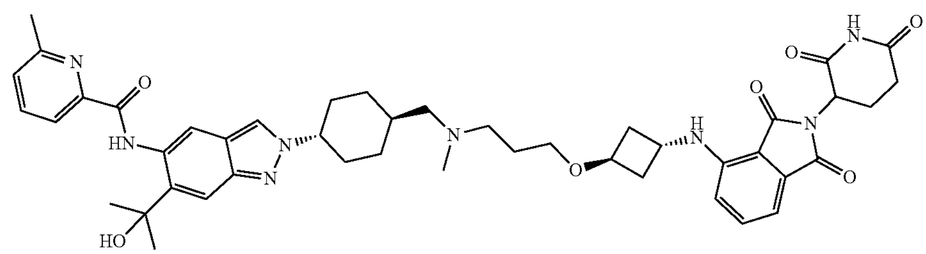 |
| I-265 | 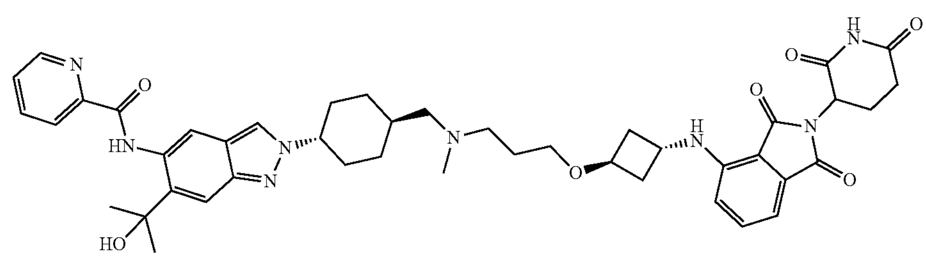 [SMILES: CN(CCCO[C@H]1C[C@H](Nc2cccc3c2C(=O)N(C2CCC(=O)NC2=O)C3=O)C1)C[C@H]1CC[C@H](n2cc3cc(NC(=O)c4ccccn4)c(C(C)(C)O)cc3n2)CC1] |
| I-266 | 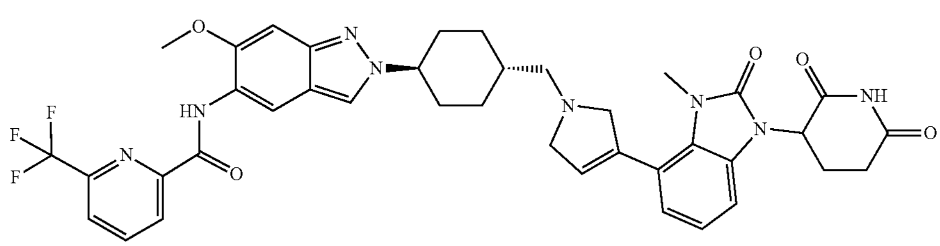 [SMILES: COc1cc2nn([C@H]3CC[C@H](CN4CC=C(c5cccc6c5n(C)c(=O)n6C5CCC(=O)NC5=O)C4)CC3)cc2cc1NC(=O)c1cccc(C(F)(F)F)n1] |

TABLE 1-continued

Exemplary Compounds

| I-# | Structure |
|-----|-----------|
| I-267 | 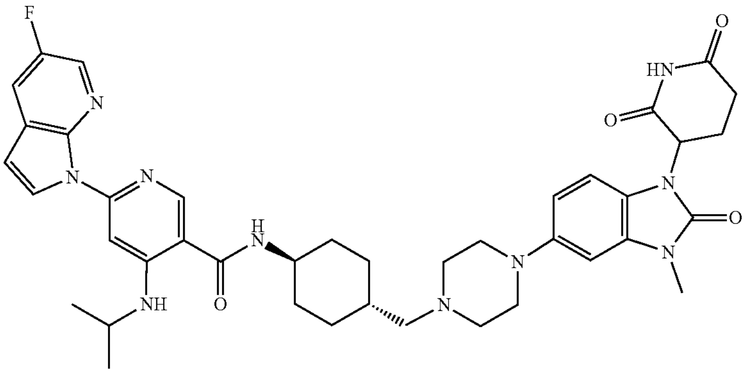 [SMILES: CC(C)Nc1cc(-n2ccc3cc(F)cnc32)ncc1C(=O)N[C@H]1CC[C@H](CN2CCN(c3ccc4c(c3)n(C)c(=O)n4C3CCC(=O)NC3=O)CC2)CC1] |
| I-268 | 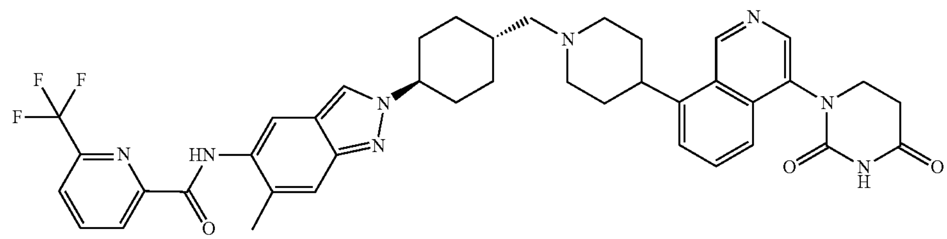 [SMILES: Cc1cc2nn([C@H]3CC[C@H](CN4CCC(c5cccc6c(N7CCC(=O)NC7=O)cncc56)CC4)CC3)cc2cc1NC(=O)c1cccc(C(F)(F)F)n1] |
| I-269 | 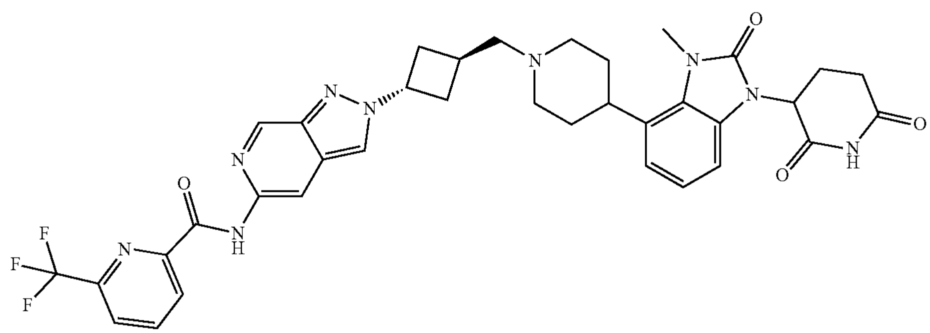 [SMILES: Cn1c(=O)n(C2CCC(=O)NC2=O)c2cccc(C3CCN(C[C@H]4C[C@H](n5cc6cc(NC(=O)c7cccc(C(F)(F)F)n7)ncc6n5)C4)CC3)c21] |
| I-270 | 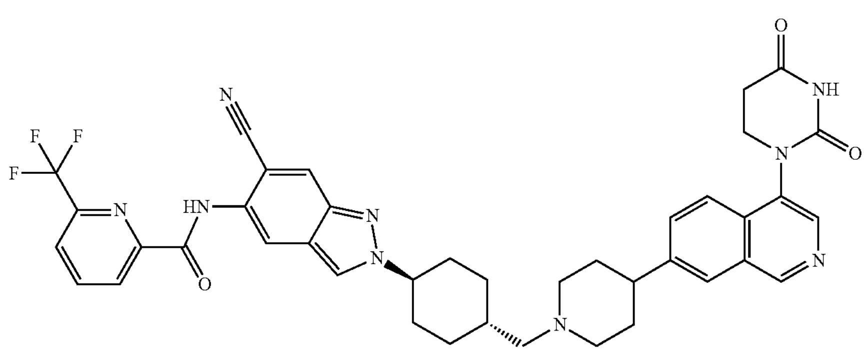 [SMILES: N#Cc1cc2nn([C@H]3CC[C@H](CN4CCC(c5ccc6c(N7CCC(=O)NC7=O)cncc6c5)CC4)CC3)cc2cc1NC(=O)c1cccc(C(F)(F)F)n1] |
| I-271 | 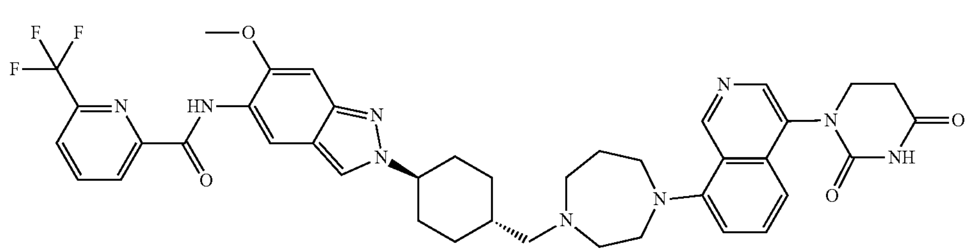 [SMILES: COc1cc2nn([C@H]3CC[C@H](CN4CCCN(c5cccc6c(N7CCC(=O)NC7=O)cncc56)CC4)CC3)cc2cc1NC(=O)c1cccc(C(F)(F)F)n1] |

TABLE 1-continued

Exemplary Compounds

| I-# | Structure |
|---|---|
| I-272 | 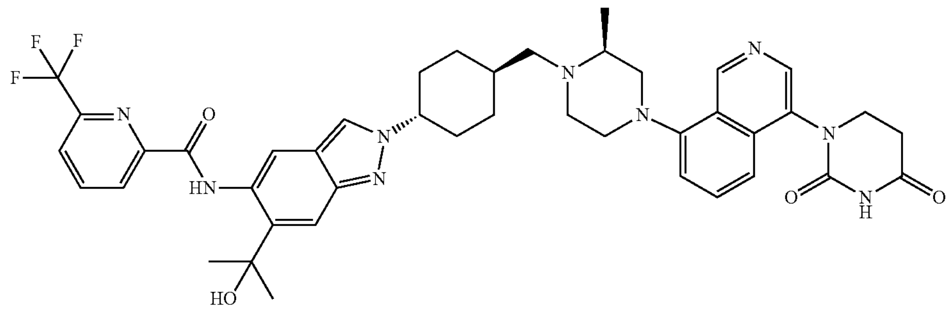 [SMILES: C[C@H]1CN(c2cccc3c(N4CCC(=O)NC4=O)cncc23)CCN1C[C@H]1CC[C@H](n2cc3cc(NC(=O)c4cccc(C(F)(F)F)n4)c(C(C)(C)O)cc3n2)CC1] |
| I-273 | 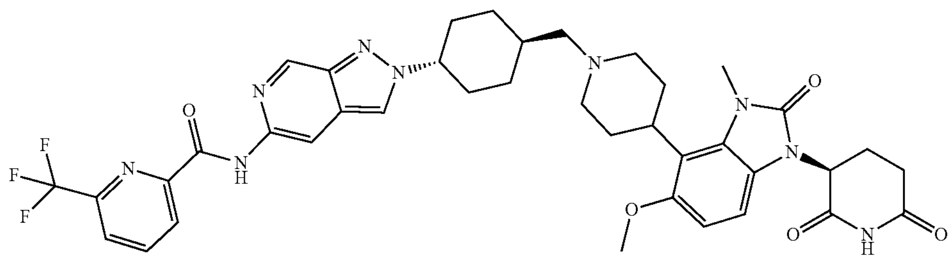 [SMILES: COc1ccc2c(c1C1CCN(C[C@H]3CC[C@H](n4cc5cc(NC(=O)c6cccc(C(F)(F)F)n6)ncc5n4)CC3)CC1)n(C)c(=O)n2[C@H]1CCC(=O)NC1=O] |
| I-274 | 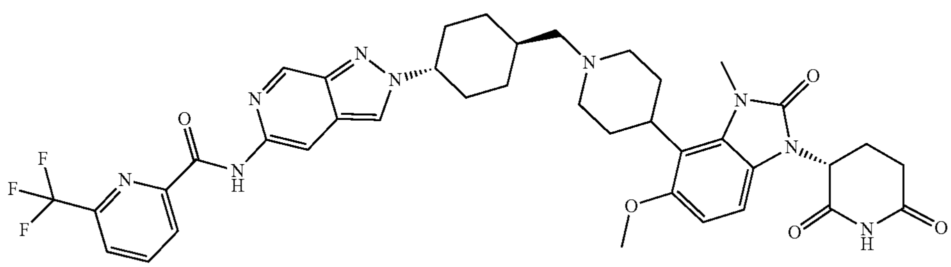 [SMILES: COc1ccc2c(c1C1CCN(C[C@H]3CC[C@H](n4cc5cc(NC(=O)c6cccc(C(F)(F)F)n6)ncc5n4)CC3)CC1)n(C)c(=O)n2[C@@H]1CCC(=O)NC1=O] |
| I-275 | 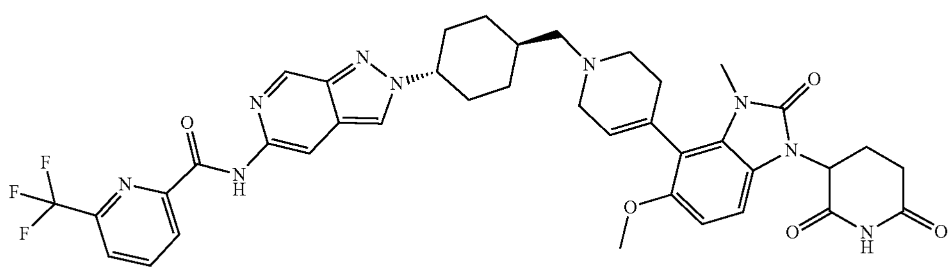 [SMILES: COc1ccc2c(c1C1=CCN(C[C@H]3CC[C@H](n4cc5cc(NC(=O)c6cccc(C(F)(F)F)n6)ncc5n4)CC3)CC1)n(C)c(=O)n2C1CCC(=O)NC1=O] |
| I-276 | 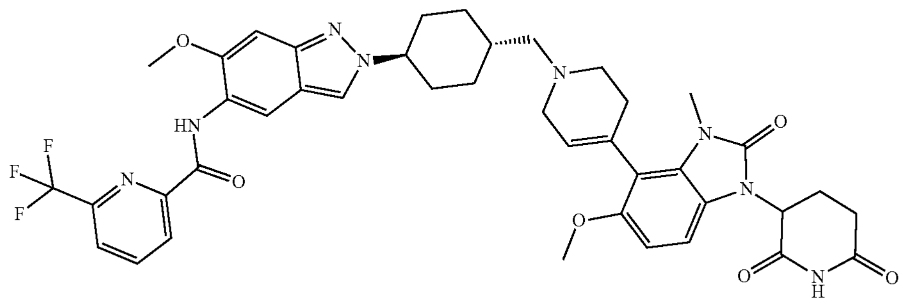 [SMILES: COc1cc2nn([C@H]3CC[C@H](CN4CC=C(c5c(OC)ccc6c5n(C)c(=O)n6C5CCC(=O)NC5=O)CC4)CC3)cc2cc1NC(=O)c1cccc(C(F)(F)F)n1] |

TABLE 1-continued

Exemplary Compounds

| I-# | Structure |
|---|---|
| I-277 | 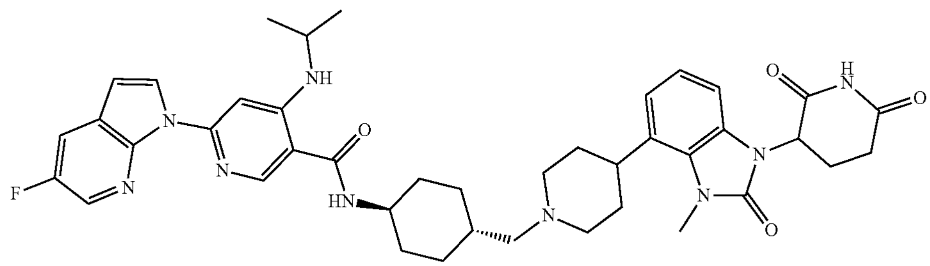 [SMILES: CC(C)Nc1cc(-n2ccc3cc(F)cnc32)ncc1C(=O)N[C@H]1CC[C@H](CN2CCC(c3cccc4c3n(C)c(=O)n4C3CCC(=O)NC3=O)CC2)CC1] |
| I-278 | 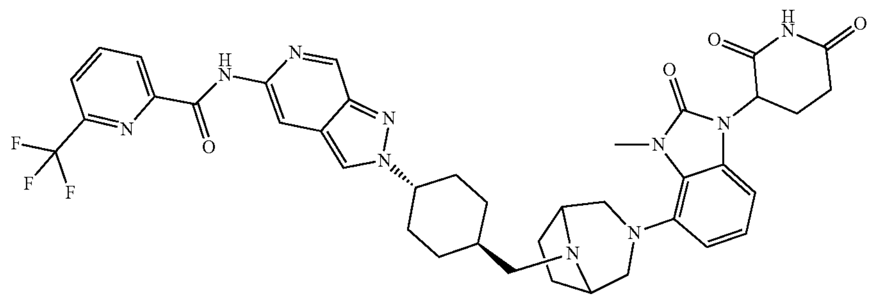 [SMILES: Cn1c(=O)n(C2CCC(=O)NC2=O)c2cccc(N3CC4CCC(C3)N4C[C@H]3CC[C@H](n4cc5cc(NC(=O)c6cccc(C(F)(F)F)n6)ncc5n4)CC3)c21] |
| I-279 | 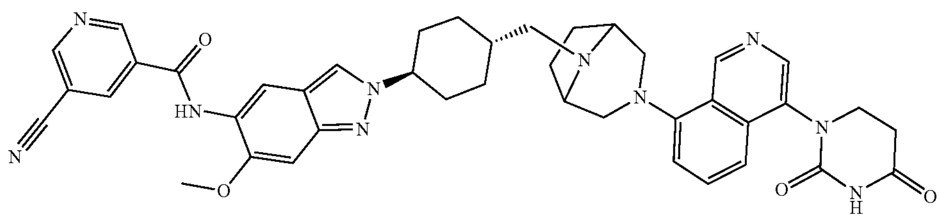 [SMILES: COc1cc2nn([C@H]3CC[C@H](CN4C5CCC4CN(c4cccc6c(N7CCC(=O)NC7=O)cncc46)C5)CC3)cc2cc1NC(=O)c1cncc(C#N)c1] |
| I-280 | 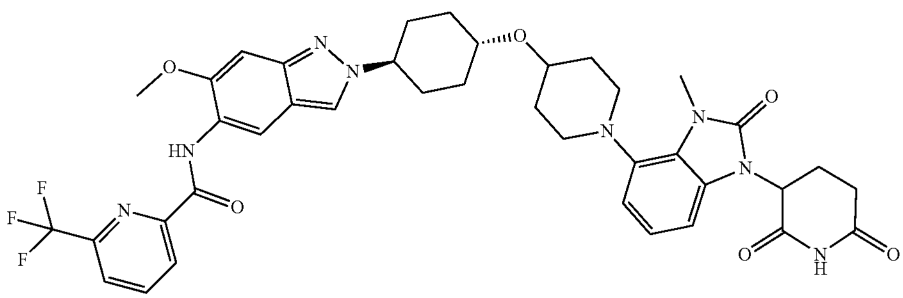 [SMILES: COc1cc2nn([C@H]3CC[C@H](OC4CCN(c5cccc6c5n(C)c(=O)n6C5CCC(=O)NC5=O)CC4)CC3)cc2cc1NC(=O)c1cccc(C(F)(F)F)n1] |
| I-281 | 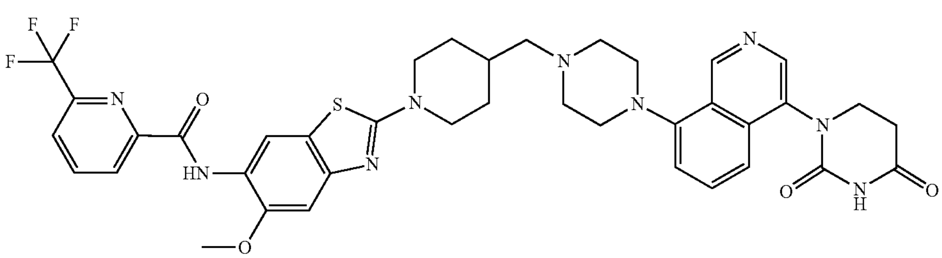 [SMILES: COc1cc2nc(N3CCC(CN4CCN(c5cccc6c(N7CCC(=O)NC7=O)cncc56)CC4)CC3)sc2cc1NC(=O)c1cccc(C(F)(F)F)n1] |

TABLE 1-continued

Exemplary Compounds

| I-# | Structure |
|---|---|
| I-282 | 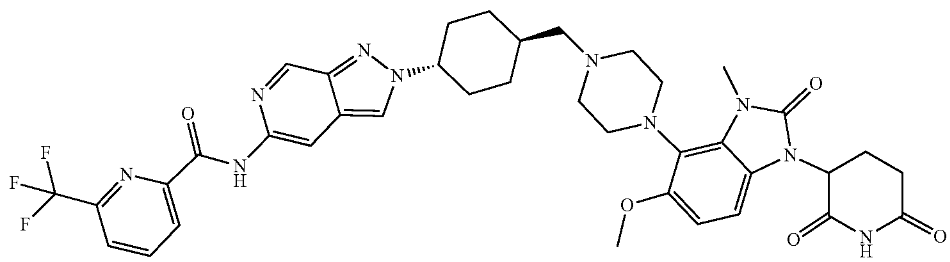 [SMILES: COc1ccc2c(c1N1CCN(C[C@H]3CC[C@H](n4cc5cc(NC(=O)c6cccc(C(F)(F)F)n6)ncc5n4)CC3)CC1)n(C)c(=O)n2C1CCC(=O)NC1=O] |
| I-283 | 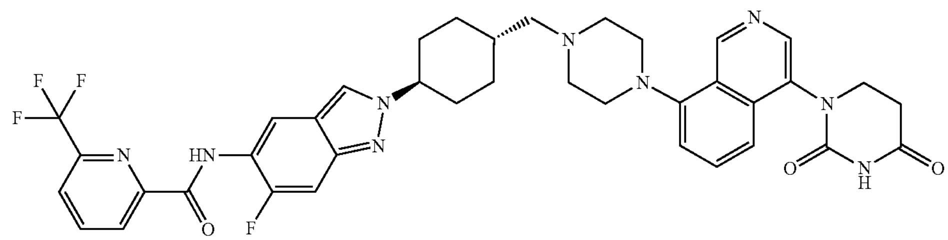 [SMILES: O=C1CCN(c2cncc3c(N4CCN(C[C@H]5CC[C@H](n6cc7cc(NC(=O)c8cccc(C(F)(F)F)n8)c(F)cc7n6)CC5)CC4)cccc23)C(=O)N1] |
| I-284 | 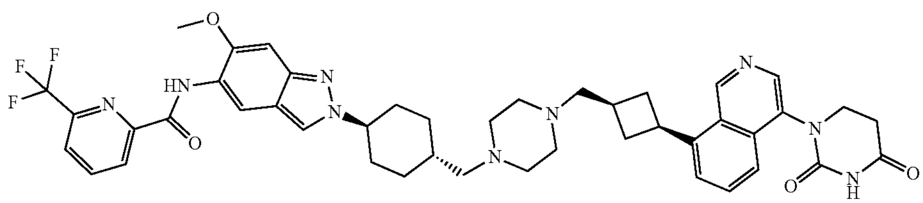 [SMILES: COc1cc2nn([C@H]3CC[C@H](CN4CCN(C[C@H]5C[C@@H](c6cccc7c(N8CCC(=O)NC8=O)cncc76)C5)CC4)CC3)cc2cc1NC(=O)c1cccc(C(F)(F)F)n1] |
| I-285 | 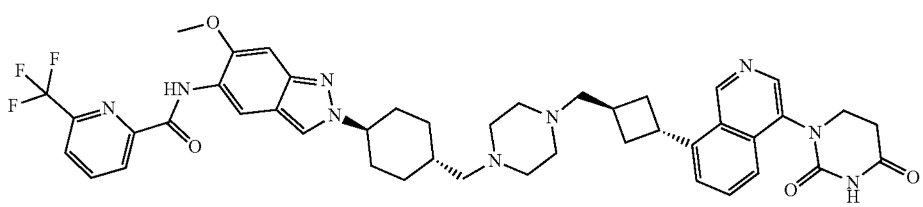 [SMILES: COc1cc2nn([C@H]3CC[C@H](CN4CCN(C[C@H]5C[C@H](c6cccc7c(N8CCC(=O)NC8=O)cncc76)C5)CC4)CC3)cc2cc1NC(=O)c1cccc(C(F)(F)F)n1] |
| I-286 | 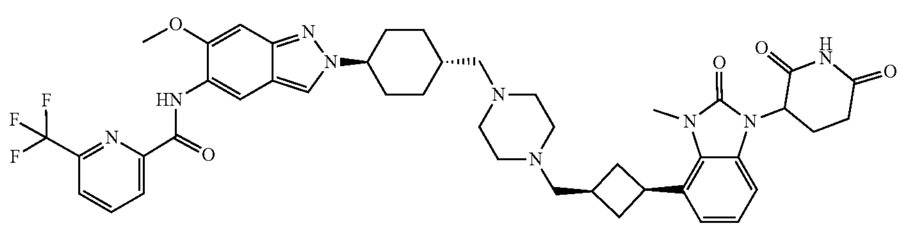 [SMILES: COc1cc2nn([C@H]3CC[C@H](CN4CCN(C[C@H]5C[C@@H](c6cccc7c6n(C)c(=O)n7C6CCC(=O)NC6=O)C5)CC4)CC3)cc2cc1NC(=O)c1cccc(C(F)(F)F)n1] |
| I-287 | 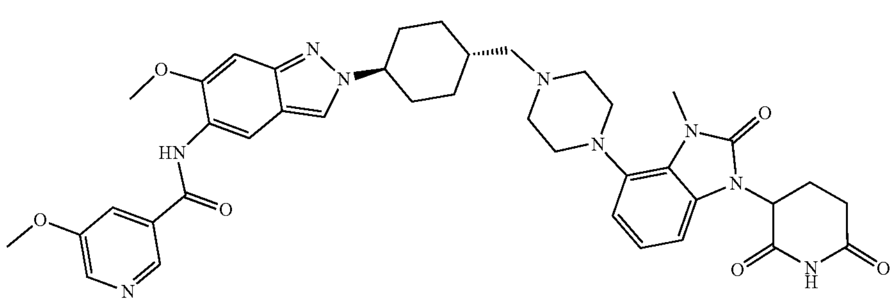 [SMILES: COc1cncc(C(=O)Nc2cc3cn([C@H]4CC[C@H](CN5CCN(c6cccc7c6n(C)c(=O)n7C6CCC(=O)NC6=O)CC5)CC4)nc3cc2OC)c1] |

TABLE 1-continued
Exemplary Compounds
| I-# | Structure |
|---|---|
| I-288 | 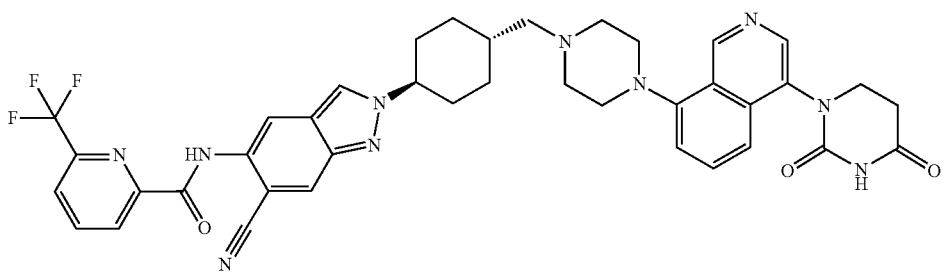 [SMILES: N#Cc1cc2nn([C@H]3CC[C@H](CN4CCN(c5cccc6c(N7CCC(=O)NC7=O)cncc56)CC4)CC3)cc2cc1NC(=O)c1cccc(C(F)(F)F)n1] |
| I-289 | 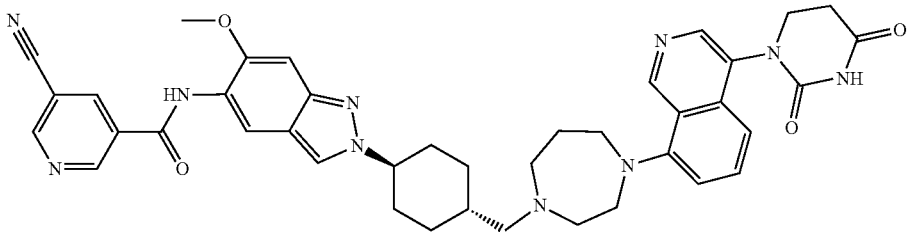 [SMILES: COc1cc2nn([C@H]3CC[C@H](CN4CCCN(c5cccc6c(N7CCC(=O)NC7=O)cncc56)CC4)CC3)cc2cc1NC(=O)c1cncc(C#N)c1] |
| I-290 | 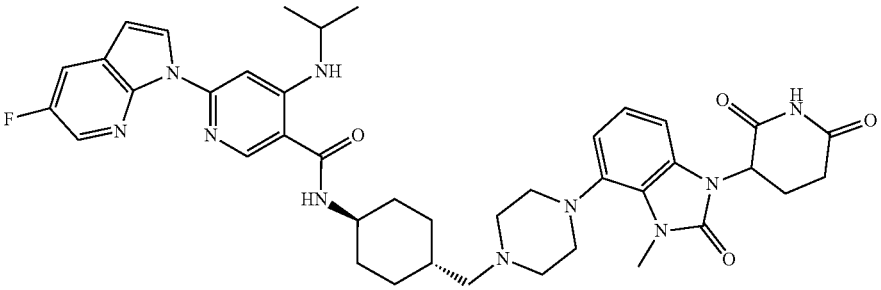 [SMILES: CC(C)Nc1cc(-n2ccc3cc(F)cnc32)ncc1C(=O)N[C@H]1CC[C@H](CN2CCN(c3cccc4c3n(C)c(=O)n4C3CCC(=O)NC3=O)CC2)CC1] |
| I-291 | 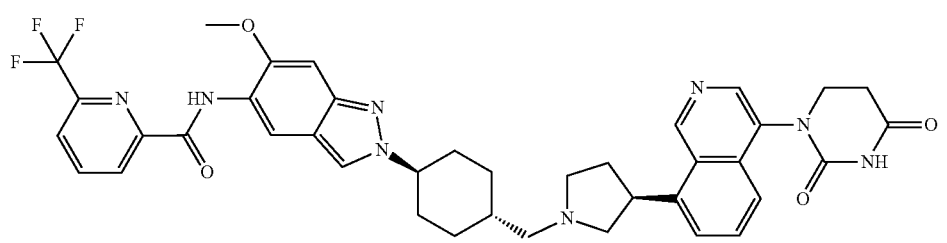 [SMILES: COc1cc2nn([C@H]3CC[C@H](CN4CC[C@@H](c5cccc6c(N7CCC(=O)NC7=O)cncc56)C4)CC3)cc2cc1NC(=O)c1cccc(C(F)(F)F)n1] |
| I-292 | 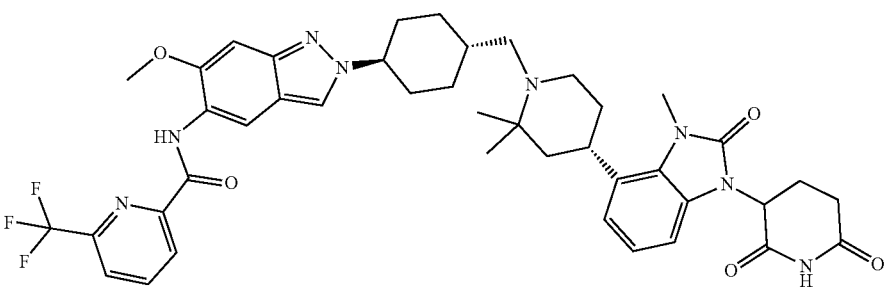 [SMILES: COc1cc2nn([C@H]3CC[C@H](CN4CC[C@H](c5cccc6c5n(C)c(=O)n6C5CCC(=O)NC5=O)CC4(C)C)CC3)cc2cc1NC(=O)c1cccc(C(F)(F)F)n1] |

TABLE 1-continued

Exemplary Compounds

| I-# | Structure |
|---|---|
| I-293 | 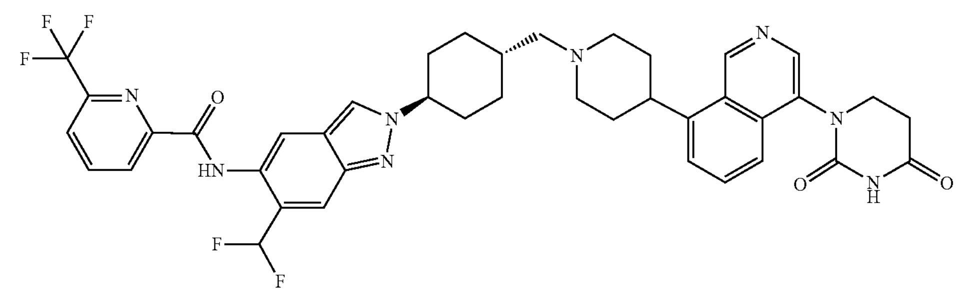 [SMILES: O=C1CCN(c2cncc3c(C4CCN(C[C@H]5CC[C@H](n6cc7cc(NC(=O)c8cccc(C(F)(F)F)n8)c(C(F)F)cc7n6)CC5)CC4)cccc23)C(=O)N1] |
| I-294 | 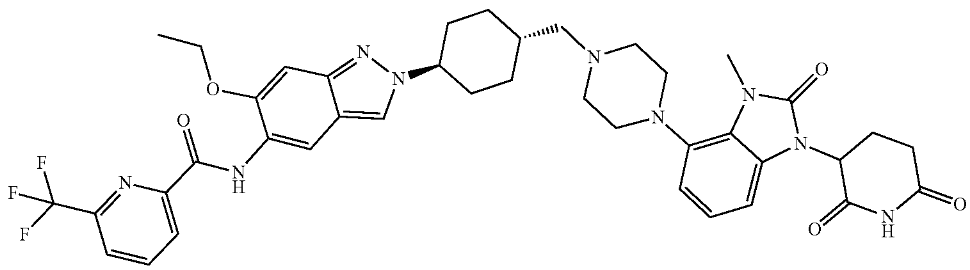 [SMILES: CCOc1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |
| I-295 | 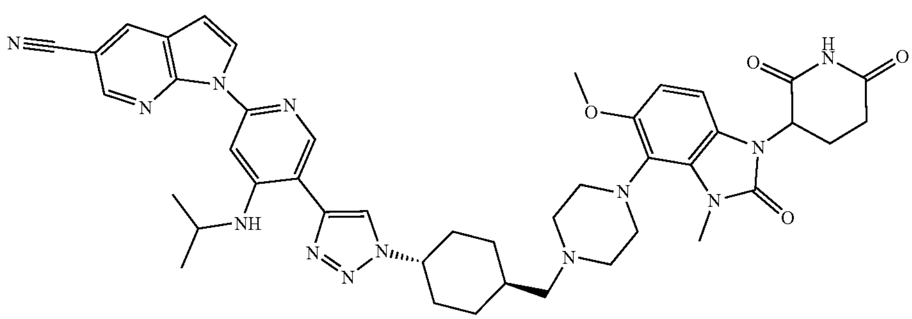 [SMILES: COc1ccc2c(c1N1CCN(C[C@H]3CC[C@H](n4cc(-c5cnc(-n6ccc7cc(C#N)cnc76)cc5NC(C)C)nn4)CC3)CC1)n(C)c(=O)n2C1CCC(=O)NC1=O] |
| I-296 | 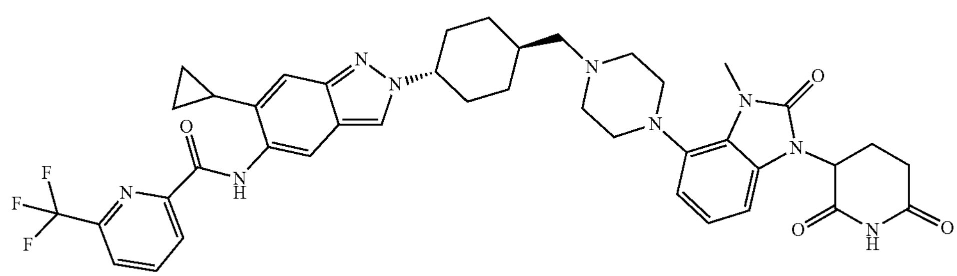 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(C7CC7)cc6n5)CC4)CC3)c21] |
| I-297 | 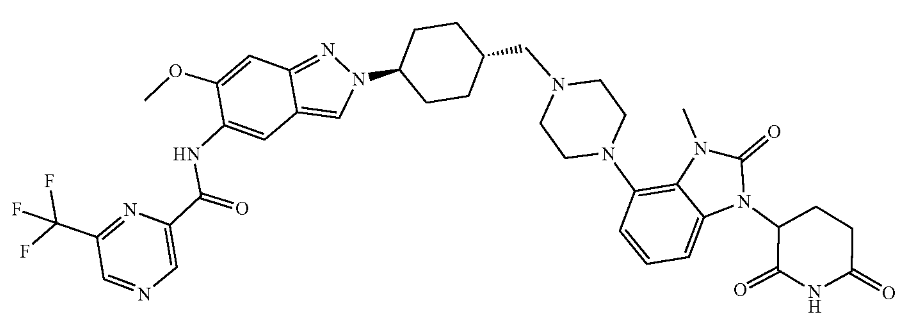 [SMILES: COc1cc2nn([C@H]3CC[C@H](CN4CCN(c5cccc6c5n(C)c(=O)n6C5CCC(=O)NC5=O)CC4)CC3)cc2cc1NC(=O)c1cncc(C(F)(F)F)n1] |

TABLE 1-continued

Exemplary Compounds

| I-# | Structure |
|---|---|
| I-298 | 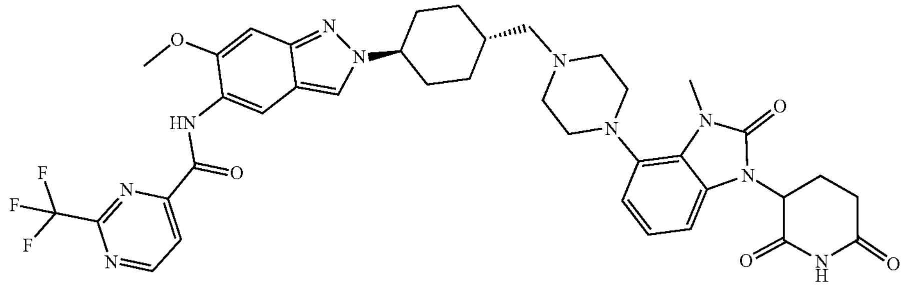 [SMILES: COc1cc2nn([C@H]3CC[C@H](CN4CCN(c5cccc6c5n(C)c(=O)n6C5CCC(=O)NC5=O)CC4)CC3)cc2cc1NC(=O)c1ccnc(C(F)(F)F)n1] |
| I-299 | 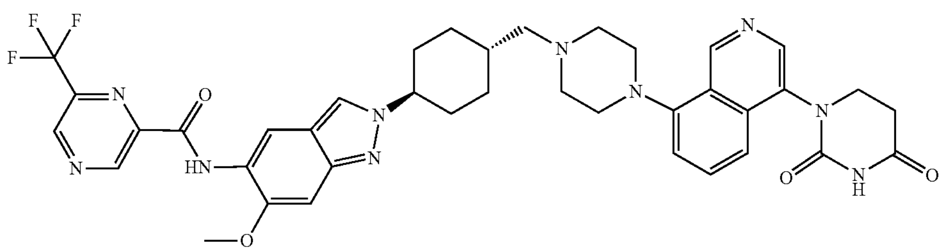 [SMILES: COc1cc2nn([C@H]3CC[C@H](CN4CCN(c5cccc6c(N7CCC(=O)NC7=O)cncc56)CC4)CC3)cc2cc1NC(=O)c1cncc(C(F)(F)F)n1] |
| I-300 | 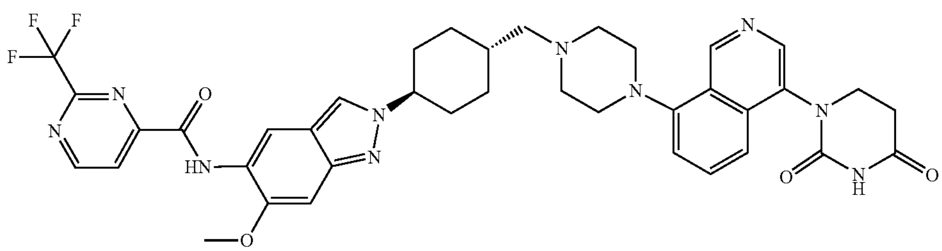 [SMILES: COc1cc2nn([C@H]3CC[C@H](CN4CCN(c5cccc6c(N7CCC(=O)NC7=O)cncc56)CC4)CC3)cc2cc1NC(=O)c1ccnc(C(F)(F)F)n1] |
| I-301 | 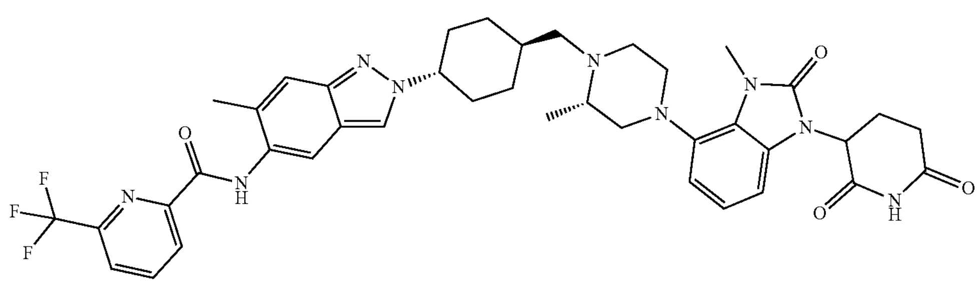 [SMILES: Cc1cc2nn([C@H]3CC[C@H](CN4CCN(c5cccc6c5n(C)c(=O)n6C5CCC(=O)NC5=O)C[C@@H]4C)CC3)cc2cc1NC(=O)c1cccc(C(F)(F)F)n1] |
| I-302 | 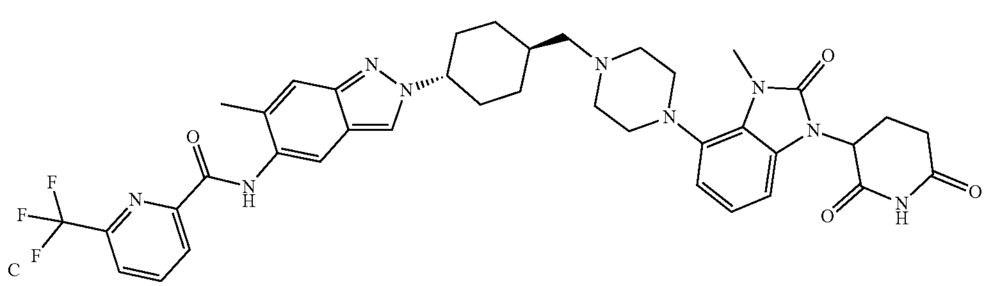 |

TABLE 1-continued

Exemplary Compounds

| I-# | Structure |
|---|---|
| I-303 | 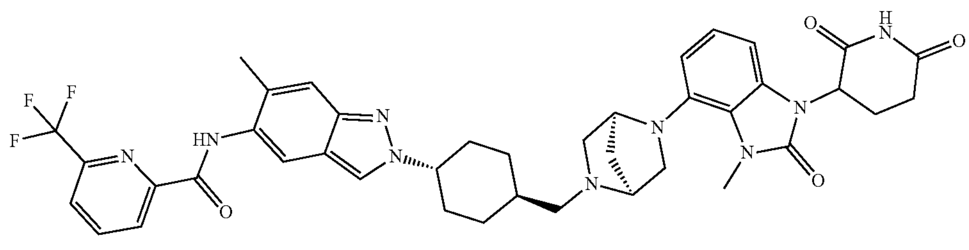 [SMILES: Cc1cc2nn([C@H]3CC[C@H](CN4C[C@@H]5C[C@H]4CN5c4cccc5c4n(C)c(=O)n5C4CCC(=O)NC4=O)CC3)cc2cc1NC(=O)c1cccc(C(F)(F)F)n1] |
| I-304 | 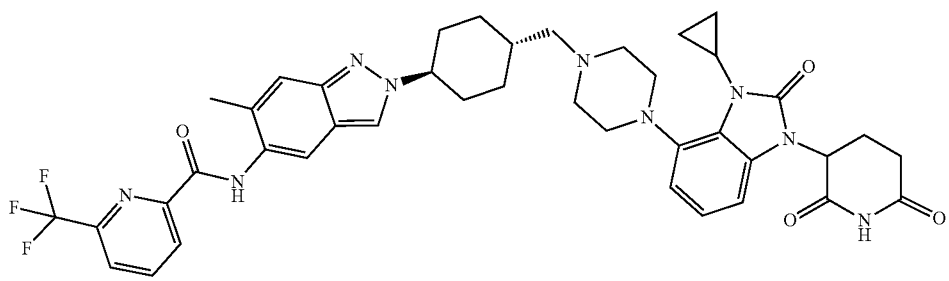 [SMILES: Cc1cc2nn([C@H]3CC[C@H](CN4CCN(c5cccc6c5n(C5CC5)c(=O)n6C5CCC(=O)NC5=O)CC4)CC3)cc2cc1NC(=O)c1cccc(C(F)(F)F)n1] |
| I-305 | 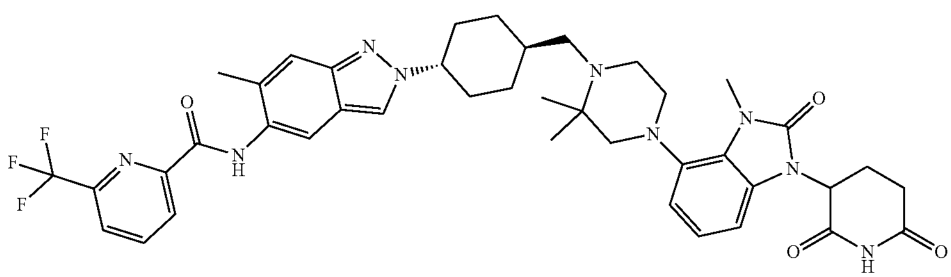 [SMILES: Cc1cc2nn([C@H]3CC[C@H](CN4CCN(c5cccc6c5n(C)c(=O)n6C5CCC(=O)NC5=O)CC4(C)C)CC3)cc2cc1NC(=O)c1cccc(C(F)(F)F)n1] |
| I-306 | 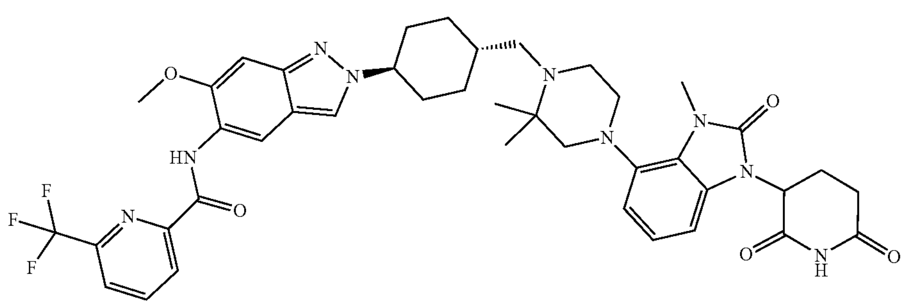 [SMILES: COc1cc2nn([C@H]3CC[C@H](CN4CCN(c5cccc6c5n(C)c(=O)n6C5CCC(=O)NC5=O)CC4(C)C)CC3)cc2cc1NC(=O)c1cccc(C(F)(F)F)n1] |
| I-307 | 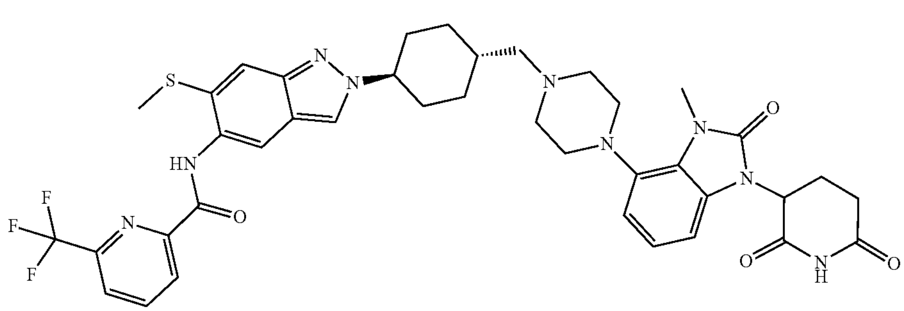 [SMILES: CSc1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |

TABLE 1-continued
Exemplary Compounds
| I-# | Structure |
|---|---|
| I-308 | 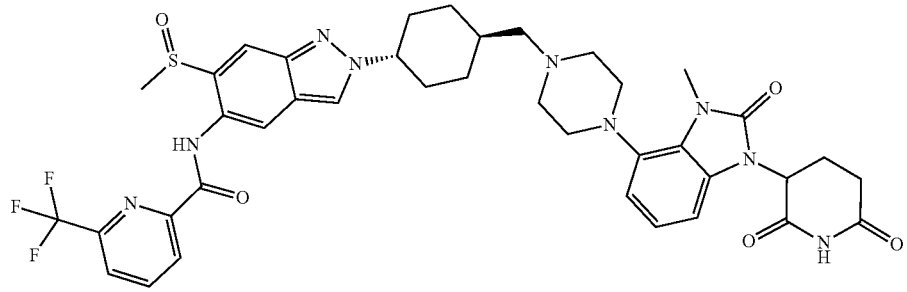 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(S(C)=O)cc6n5)CC4)CC3)c21] |
| I-309 | 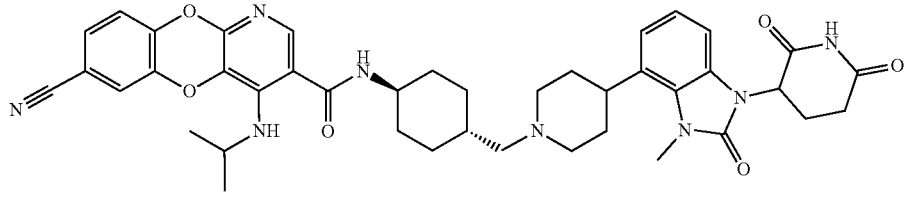 [SMILES: CC(C)Nc1c(C(=O)N[C@H]2CC[C@H](CN3CCC(c4cccc5c4n(C)c(=O)n5C4CCC(=O)NC4=O)CC3)CC2)cnc2c1Oc1cc(C#N)ccc1O2] |
| I-310 | 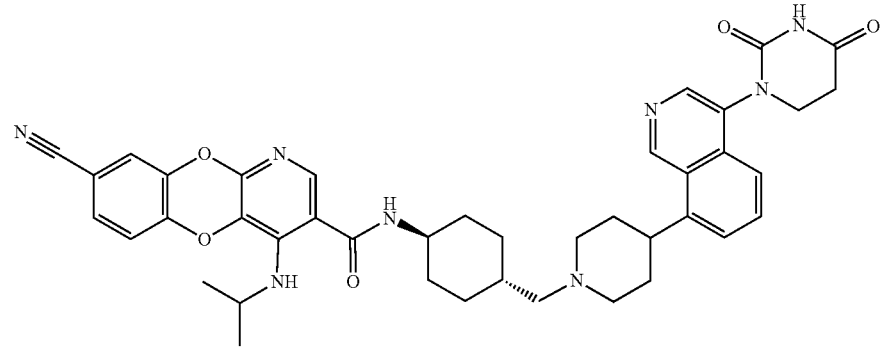 [SMILES: CC(C)Nc1c(C(=O)N[C@H]2CC[C@H](CN3CCC(c4cccc5c(N6CCC(=O)NC6=O)cncc45)CC3)CC2)cnc2c1Oc1ccc(C#N)cc1O2] |
| I-311 | 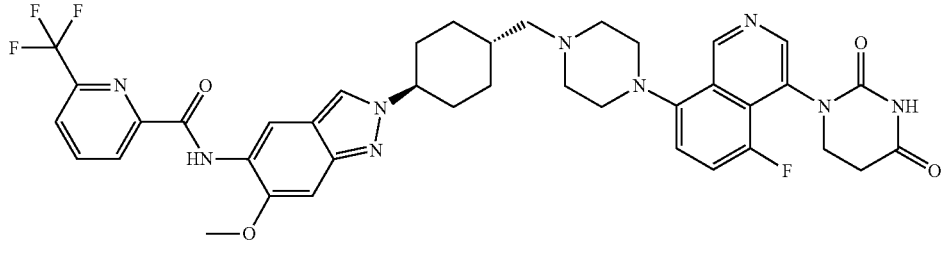 [SMILES: COc1cc2nn([C@H]3CC[C@H](CN4CCN(c5ccc(F)c6c(N7CCC(=O)NC7=O)cncc56)CC4)CC3)cc2cc1NC(=O)c1cccc(C(F)(F)F)n1] |
| I-312 | 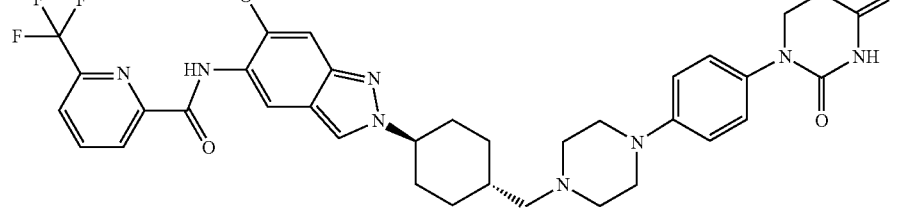 |

TABLE 1-continued

Exemplary Compounds

| I-# | Structure |
|---|---|
| I-313 | 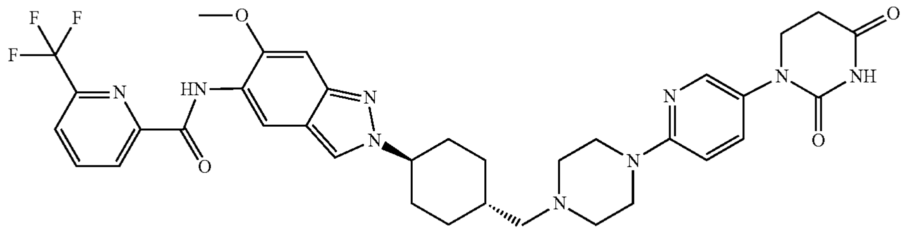 [SMILES: COc1cc2nn([C@H]3CC[C@H](CN4CCN(c5ccc(N6CCC(=O)NC6=O)cn5)CC4)CC3)cc2cc1NC(=O)c1cccc(C(F)(F)F)n1] |
| I-314 | 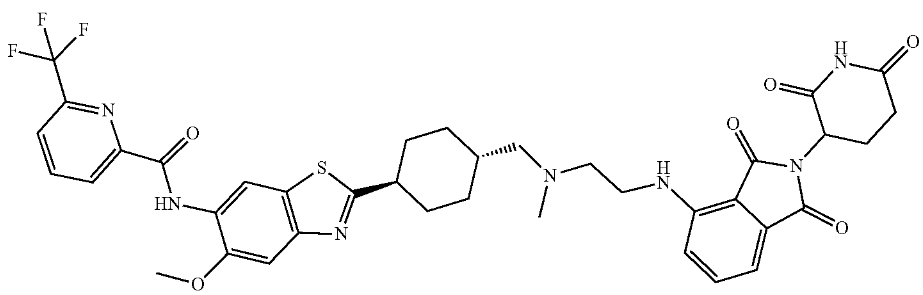 [SMILES: COc1cc2nc([C@H]3CC[C@H](CN(C)CCNc4cccc5c4C(=O)N(C4CCC(=O)NC4=O)C5=O)CC3)sc2cc1NC(=O)c1cccc(C(F)(F)F)n1] |
| I-315 | 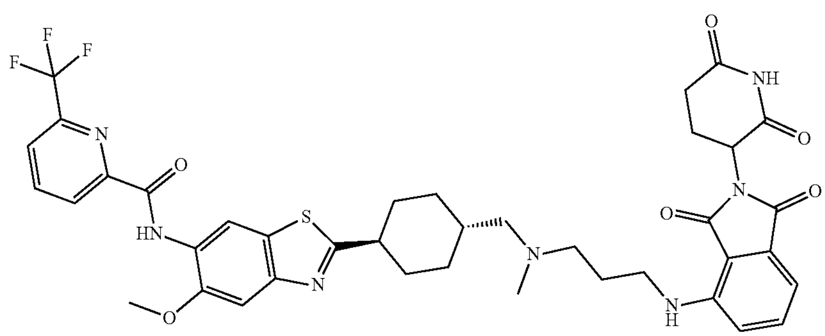 [SMILES: COc1cc2nc([C@H]3CC[C@H](CN(C)CCCNc4cccc5c4C(=O)N(C4CCC(=O)NC4=O)C5=O)CC3)sc2cc1NC(=O)c1cccc(C(F)(F)F)n1] |
| I-316 | 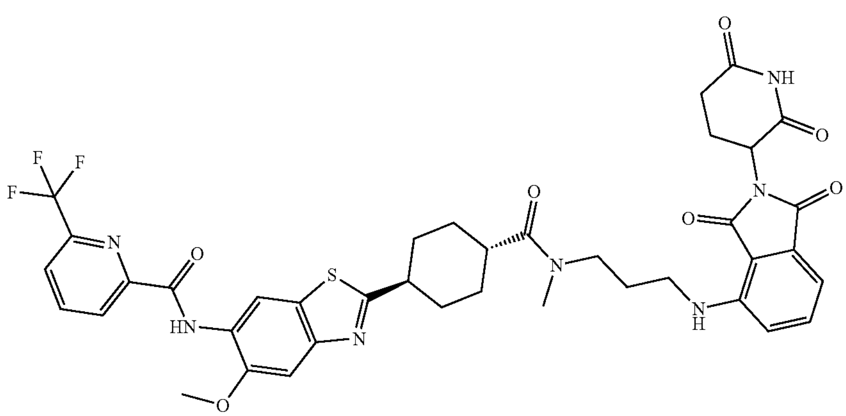 [SMILES: COc1cc2nc([C@H]3CC[C@H](C(=O)N(C)CCCNc4cccc5c4C(=O)N(C4CCC(=O)NC4=O)C5=O)CC3)sc2cc1NC(=O)c1cccc(C(F)(F)F)n1] |
| I-317 | 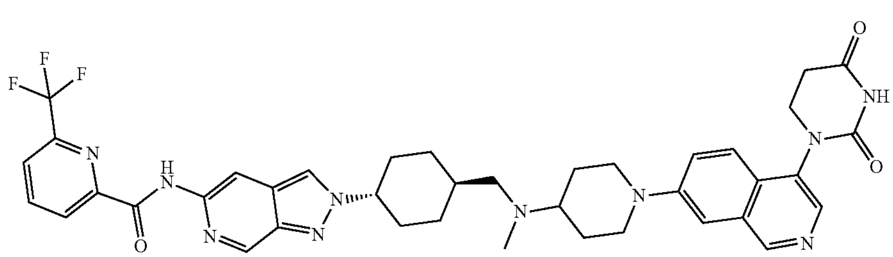 [SMILES: CN(C[C@H]1CC[C@H](n2cc3cc(NC(=O)c4cccc(C(F)(F)F)n4)ncc3n2)CC1)C1CCN(c2ccc3c(N4CCC(=O)NC4=O)cncc3c2)CC1] |

TABLE 1-continued

Exemplary Compounds

| I-# | Structure |
|---|---|
| I-318 | 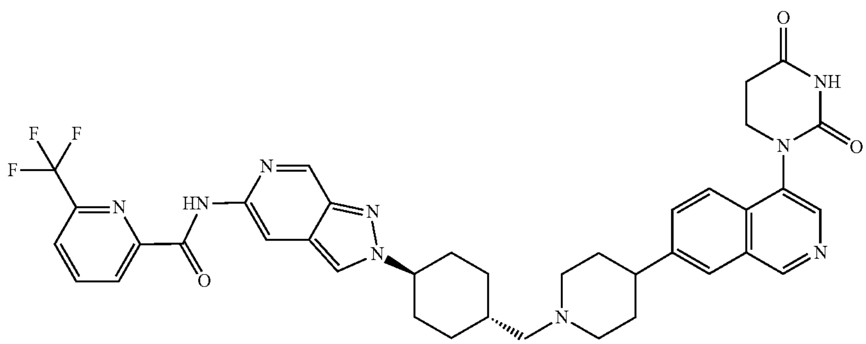 [SMILES: O=C1CCN(c2cncc3cc(C4CCN(C[C@H]5CC[C@H](n6cc7cc(NC(=O)c8cccc(C(F)(F)F)n8)ncc7n6)CC5)CC4)ccc23)C(=O)N1] |
| I-319 | 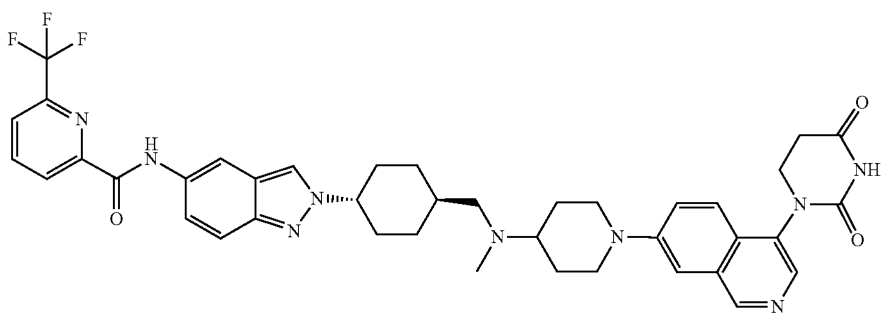 [SMILES: CN(C[C@H]1CC[C@H](n2cc3cc(NC(=O)c4cccc(C(F)(F)F)n4)ccc3n2)CC1)C1CCN(c2ccc3c(N4CCC(=O)NC4=O)cncc3c2)CC1] |
| I-320 | 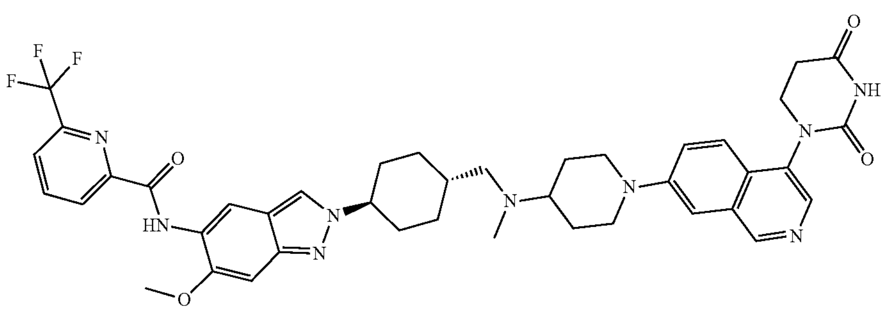 [SMILES: COc1cc2nn([C@H]3CC[C@H](CN(C)C4CCN(c5ccc6c(N7CCC(=O)NC7=O)cncc6c5)CC4)CC3)cc2cc1NC(=O)c1cccc(C(F)(F)F)n1] |
| I-321 | 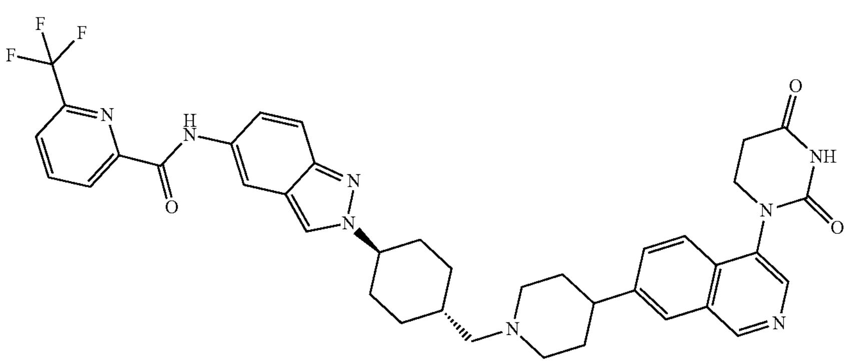 [SMILES: O=C1CCN(c2cncc3cc(C4CCN(C[C@H]5CC[C@H](n6cc7cc(NC(=O)c8cccc(C(F)(F)F)n8)ccc7n6)CC5)CC4)ccc23)C(=O)N1] |

531
532
TABLE 1-continued
Exemplary Compounds
| I-# | Structure |
|---|---|
| I-322 | 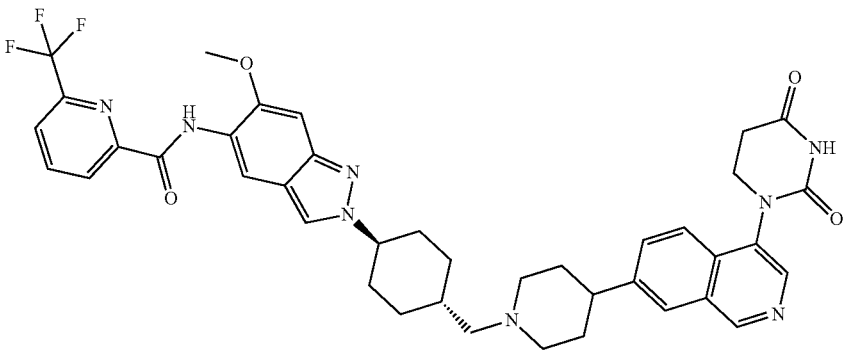 [SMILES: COc1cc2nn([C@H]3CC[C@H](CN4CCC(c5ccc6c(N7CCC(=O)NC7=O)cncc6c5)CC4)CC3)cc2cc1NC(=O)c1cccc(C(F)(F)F)n1] |
| I-323 | 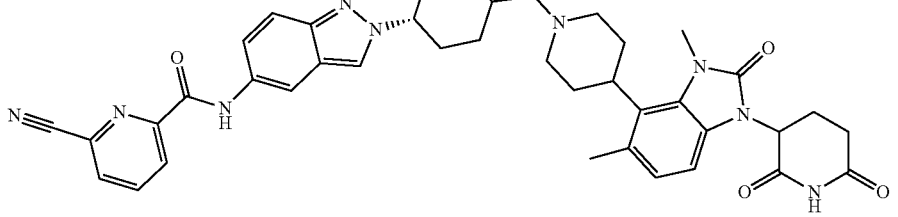 |
| I-324 | 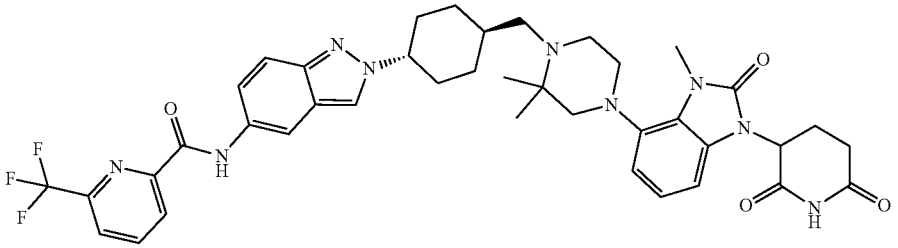 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)ccc6n5)CC4)C(C)(C)C3)c21] |
| I-325 | 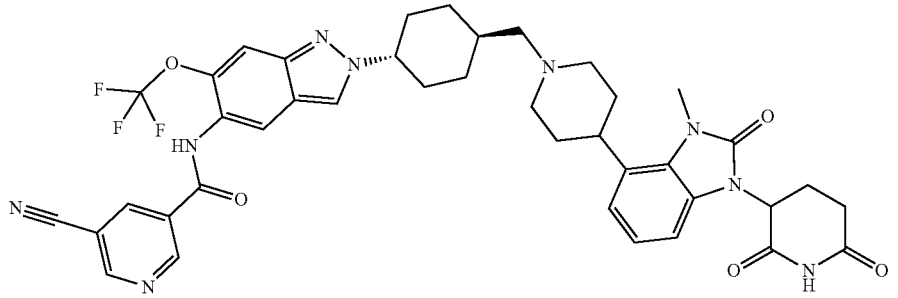 [SMILES: Cn1c(=O)n(C2CCC(=O)NC2=O)c2cccc(C3CCN(C[C@H]4CC[C@H](n5cc6cc(NC(=O)c7cncc(C#N)c7)c(OC(F)(F)F)cc6n5)CC4)CC3)c21] |
| I-326 | 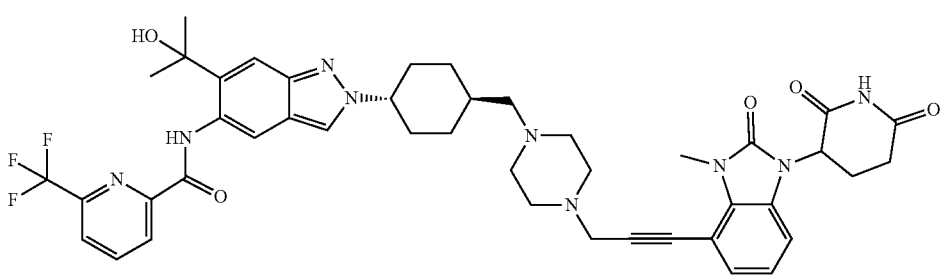 [SMILES: Cn1c(=O)n(C2CCC(=O)NC2=O)c2cccc(C#CCN3CCN(C[C@H]4CC[C@H](n5cc6cc(NC(=O)c7cccc(C(F)(F)F)n7)c(C(C)(C)O)cc6n5)CC4)CC3)c21] |

TABLE 1-continued

Exemplary Compounds

| I-# | Structure |
|---|---|
| I-327 | 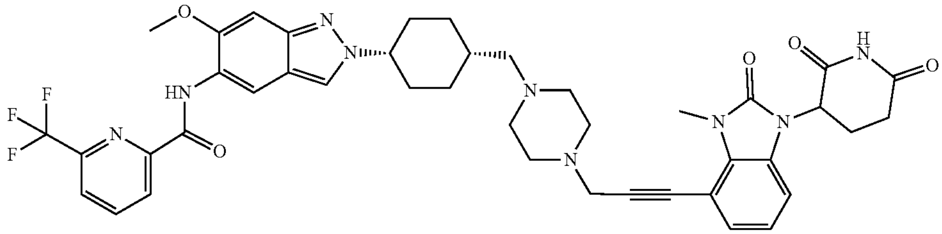 [SMILES: COc1cc2nn([C@H]3CC[C@@H](CN4CCN(CC#Cc5cccc6c5n(C)c(=O)n6C5CCC(=O)NC5=O)CC4)CC3)cc2cc1NC(=O)c1cccc(C(F)(F)F)n1] |
| I-328 | 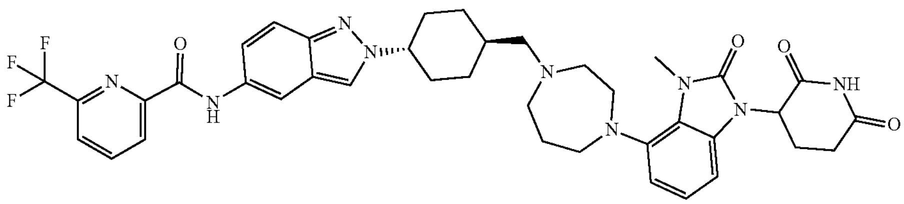 [SMILES: Cn1c(=O)n(C2CCC(=O)NC2=O)c2cccc(N3CCCN(C[C@H]4CC[C@H](n5cc6cc(NC(=O)c7cccc(C(F)(F)F)n7)ccc6n5)CC4)CC3)c21] |
| I-329 | 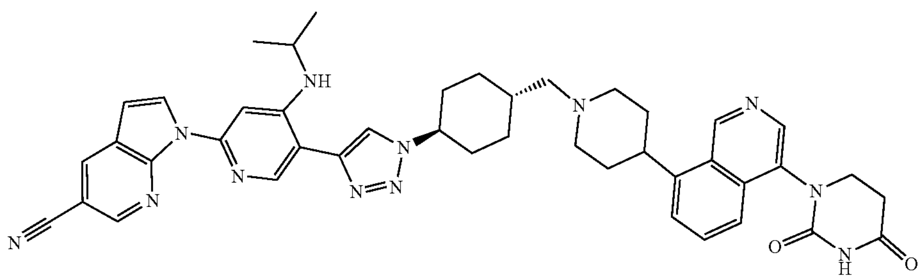 [SMILES: CC(C)Nc1cc(-n2ccc3cc(C#N)cnc32)ncc1-c1cn([C@H]2CC[C@H](CN3CCC(c4cccc5c(N6CCC(=O)NC6=O)cncc45)CC3)CC2)nn1] |
| I-330 | 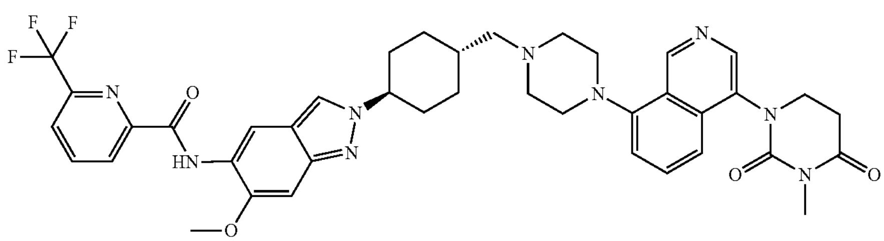 [SMILES: COc1cc2nn([C@H]3CC[C@H](CN4CCN(c5cccc6c(N7CCC(=O)N(C)C7=O)cncc56)CC4)CC3)cc2cc1NC(=O)c1cccc(C(F)(F)F)n1] |
| I-331 | 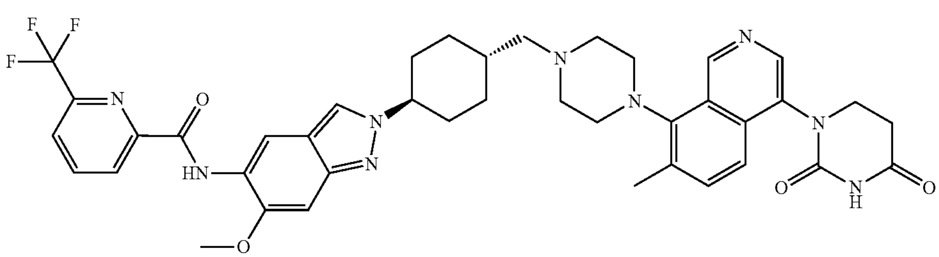 [SMILES: COc1cc2nn([C@H]3CC[C@H](CN4CCN(c5c(C)ccc6c(N7CCC(=O)NC7=O)cncc56)CC4)CC3)cc2cc1NC(=O)c1cccc(C(F)(F)F)n1] |
| I-332 | 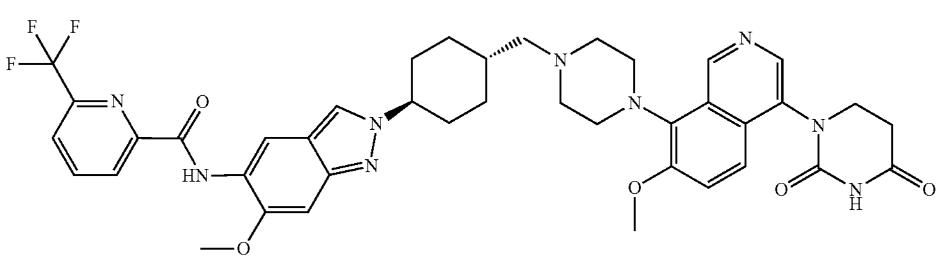 [SMILES: COc1cc2nn([C@H]3CC[C@H](CN4CCN(c5c(OC)ccc6c(N7CCC(=O)NC7=O)cncc56)CC4)CC3)cc2cc1NC(=O)c1cccc(C(F)(F)F)n1] |

TABLE 1-continued

Exemplary Compounds

| I-# | Structure |
| --- | --- |
| I-333 | 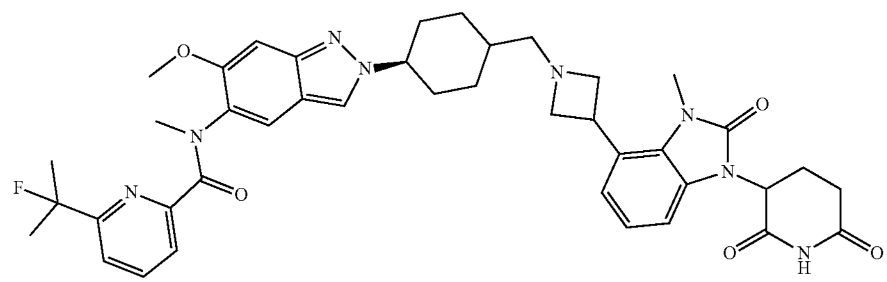 |
| I-334 | 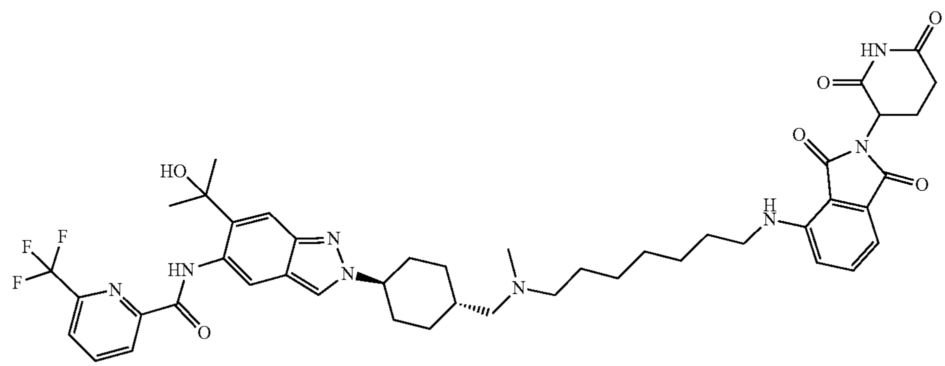 [SMILES: CN(CCCCCCCNc1cccc2c1C(=O)N(C1CCC(=O)NC1=O)C2=O)C[C@H]1CC[C@H](n2cc3cc(NC(=O)c4cccc(C(F)(F)F)n4)c(C(C)(C)O)cc3n2)CC1] |
| I-335 | 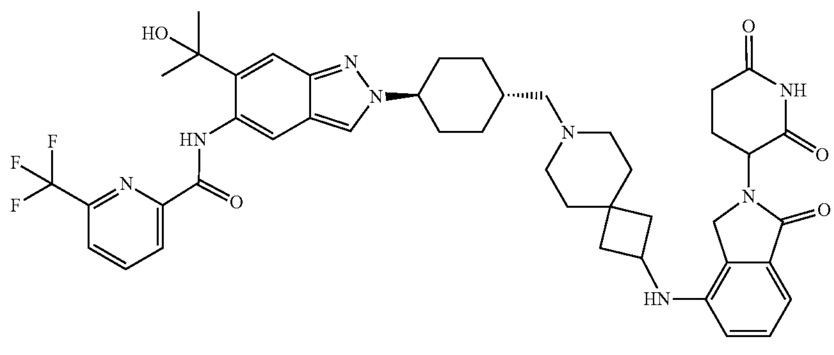 [SMILES: CC(C)(O)c1cc2nn([C@H]3CC[C@H](CN4CCC5(CC4)CC(Nc4cccc6c4CN(C4CCC(=O)NC4=O)C6=O)C5)CC3)cc2cc1NC(=O)c1cccc(C(F)(F)F)n1] |
| I-336 | 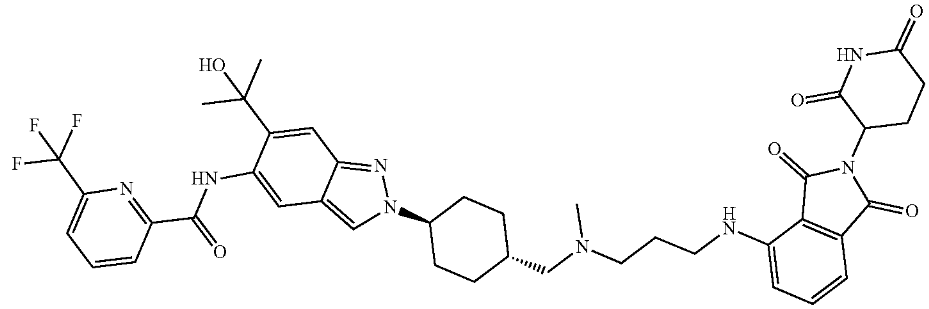 [SMILES: CN(CCCNc1cccc2c1C(=O)N(C1CCC(=O)NC1=O)C2=O)C[C@H]1CC[C@H](n2cc3cc(NC(=O)c4cccc(C(F)(F)F)n4)c(C(C)(C)O)cc3n2)CC1] |

TABLE 1-continued

Exemplary Compounds

| I-# | Structure |
|---|---|
| I-337 | 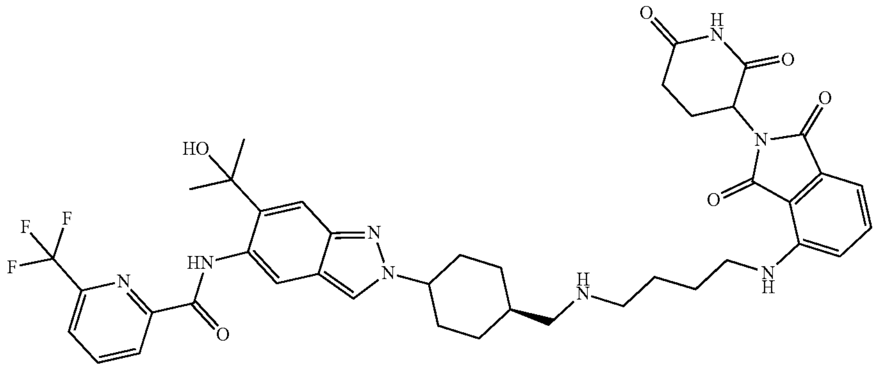 |
| I-338 | 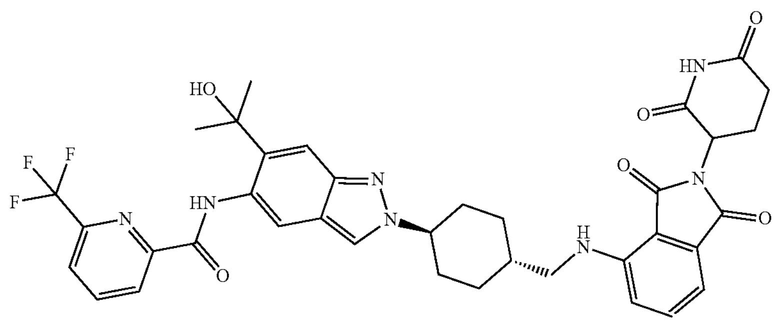 [SMILES: C=CC1=C(/C(=C\C)NC[C@H]2CC[C@H](n3cc4cc(NC(=O)c5cccc(C(F)(F)F)n5)c(C(C)(C)O)cc4n3)CC2)C(=O)N(C2CCC(=O)NC2=O)C1=O] |
| I-339 | 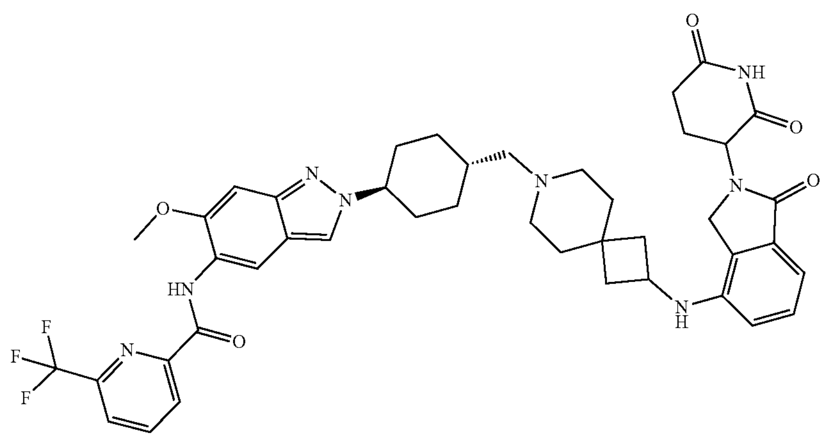 [SMILES: COc1cc2nn([C@H]3CC[C@H](CN4CCC5(CC4)CC(Nc4cccc6c4CN(C4CCC(=O)NC4=O)C6=O)C5)CC3)cc2cc1NC(=O)c1cccc(C(F)(F)F)n1] |
| I-340 | 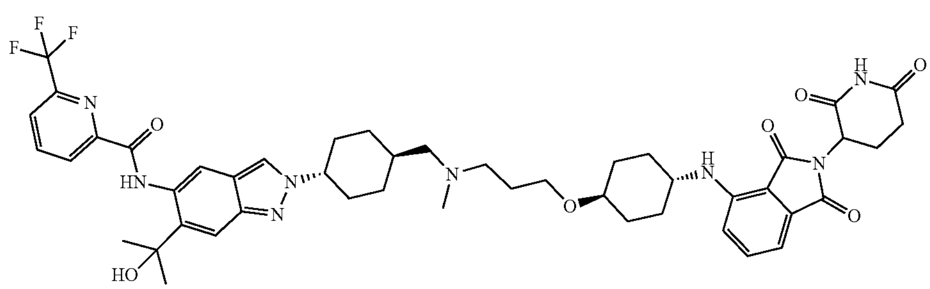 [SMILES: CN(CCCO[C@H]1CC[C@H](Nc2cccc3c2C(=O)N(C2CCC(=O)NC2=O)C3=O)CC1)C[C@H]1CC[C@H](n2cc3cc(NC(=O)c4cccc(C(F)(F)F)n4)c(C(C)(C)O)cc3n2)CC1] |

TABLE 1-continued

Exemplary Compounds

| I-# | Structure |
|---|---|
| I-341 | 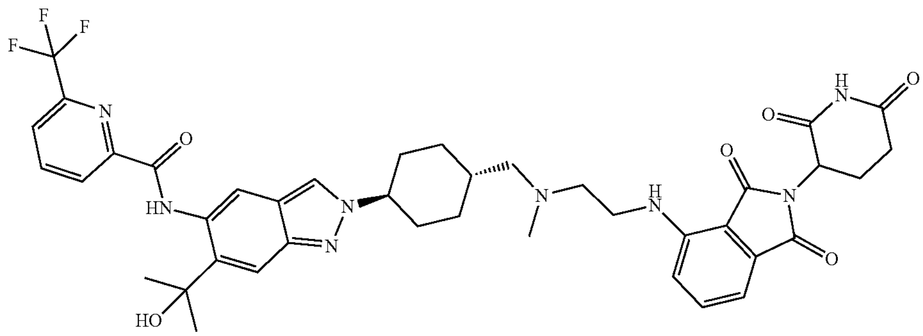 [SMILES: CN(CCNc1cccc2c1C(=O)N(C1CCC(=O)NC1=O)C2=O)C[C@H]1CC[C@H](n2cc3cc(NC(=O)c4cccc(C(F)(F)F)n4)c(C(C)(C)O)cc3n2)CC1] |
| I-342 | 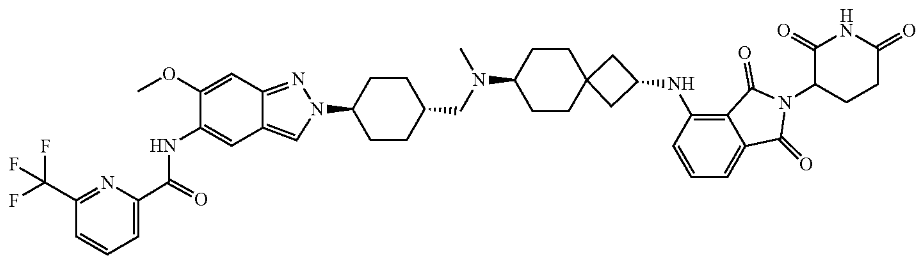 |
| I-343 | 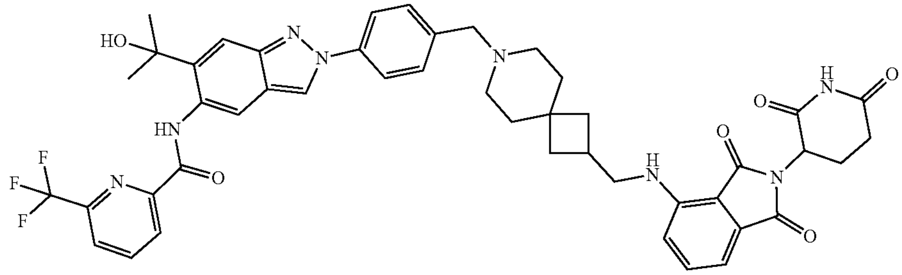 [SMILES: CC(C)(O)c1cc2nn(-c3ccc(CN4CCC5(CC4)CC(CNc4cccc6c4C(=O)N(C4CCC(=O)NC4=O)C6=O)C5)cc3)cc2cc1NC(=O)c1cccc(C(F)(F)F)n1] |
| I-344 | 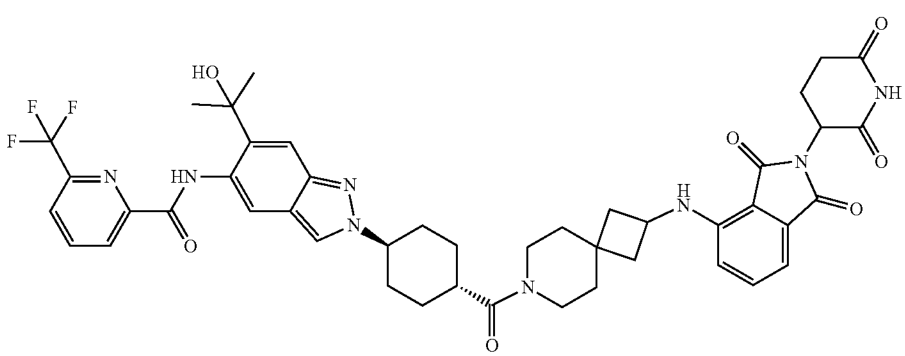 [SMILES: CC(C)(O)c1cc2nn([C@H]3CC[C@H](C(=O)N4CCC5(CC4)CC(Nc4cccc6c4C(=O)N(C4CCC(=O)NC4=O)C6=O)C5)CC3)cc2cc1NC(=O)c1cccc(C(F)(F)F)n1] |
| I-345 | 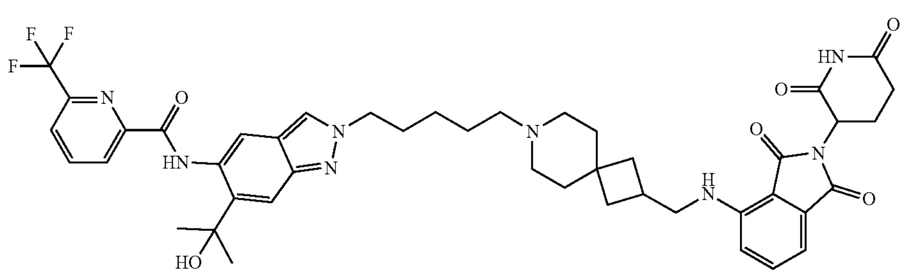 [SMILES: CC(C)(O)c1cc2nn(CCCCCN3CCC4(CC3)CC(CNc3cccc5c3C(=O)N(C3CCC(=O)NC3=O)C5=O)C4)cc2cc1NC(=O)c1cccc(C(F)(F)F)n1] |

TABLE 1-continued

Exemplary Compounds

| I-# | Structure |
|---|---|
| I-346 | 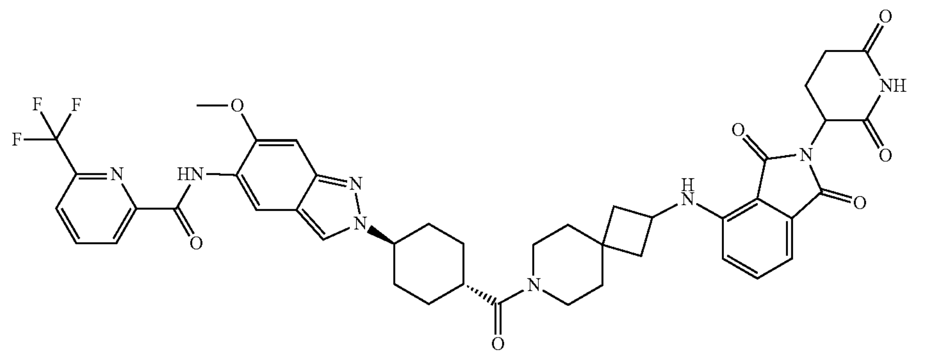 [SMILES: COc1cc2nn([C@H]3CC[C@H](C(=O)N4CCC5(CC4)CC(Nc4cccc6c4C(=O)N(C4CCC(=O)NC4=O)C6=O)C5)CC3)cc2cc1NC(=O)c1cccc(C(F)(F)F)n1] |
| I-347 | 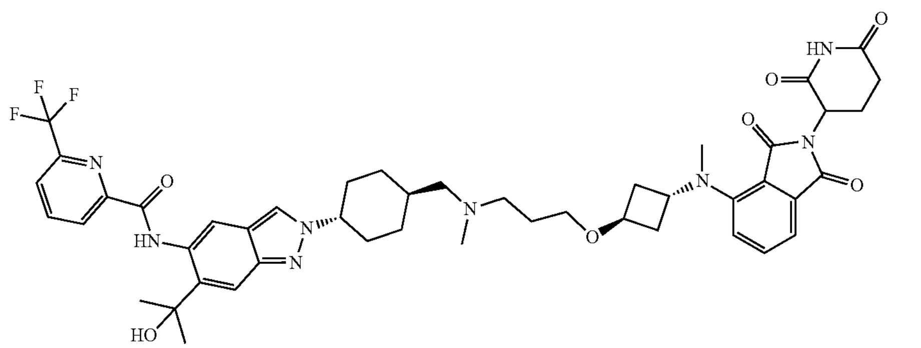 [SMILES: CN(CCCO[C@H]1C[C@H](N(C)c2cccc3c2C(=O)N(C2CCC(=O)NC2=O)C3=O)C1)C[C@H]1CC[C@H](n2cc3cc(NC(=O)c4cccc(C(F)(F)F)n4)c(C(C)(C)O)cc3n2)CC1] |
| I-348 | 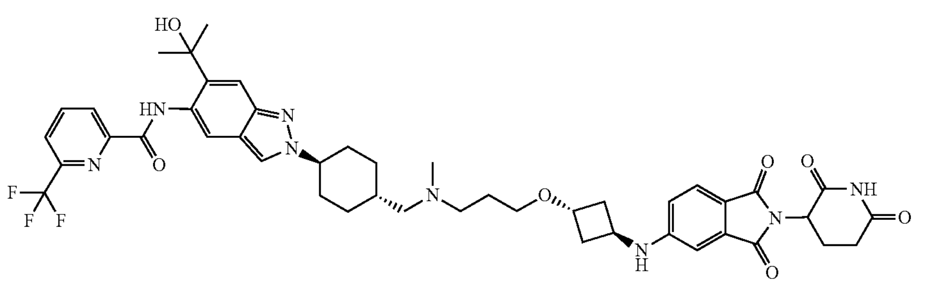 [SMILES: CN(CCCO[C@H]1C[C@H](Nc2ccc3c(c2)C(=O)N(C2CCC(=O)NC2=O)C3=O)C1)C[C@H]1CC[C@H](n2cc3cc(NC(=O)c4cccc(C(F)(F)F)n4)c(C(C)(C)O)cc3n2)CC1] |
| I-349 | 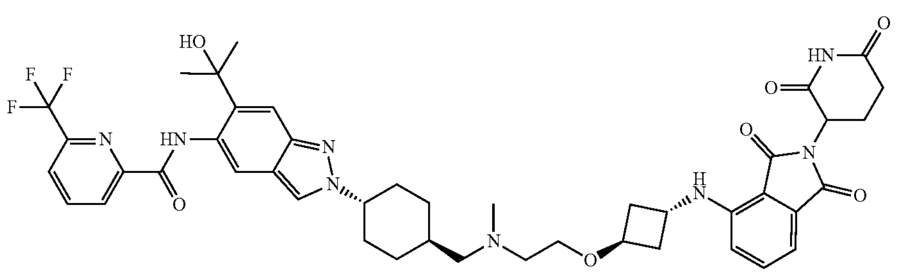 [SMILES: CN(CCO[C@H]1C[C@H](Nc2cccc3c2C(=O)N(C2CCC(=O)NC2=O)C3=O)C1)C[C@H]1CC[C@H](n2cc3cc(NC(=O)c4cccc(C(F)(F)F)n4)c(C(C)(C)O)cc3n2)CC1] |
| I-350 | 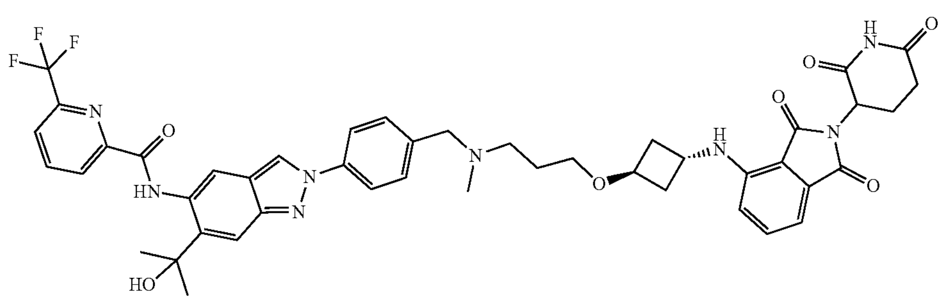 [SMILES: CN(CCCO[C@H]1C[C@H](Nc2cccc3c2C(=O)N(C2CCC(=O)NC2=O)C3=O)C1)Cc1ccc(-n2cc3cc(NC(=O)c4cccc(C(F)(F)F)n4)c(C(C)(C)O)cc3n2)cc1] |

TABLE 1-continued
Exemplary Compounds
| I-# | Structure |
|---|---|
| I-351 | 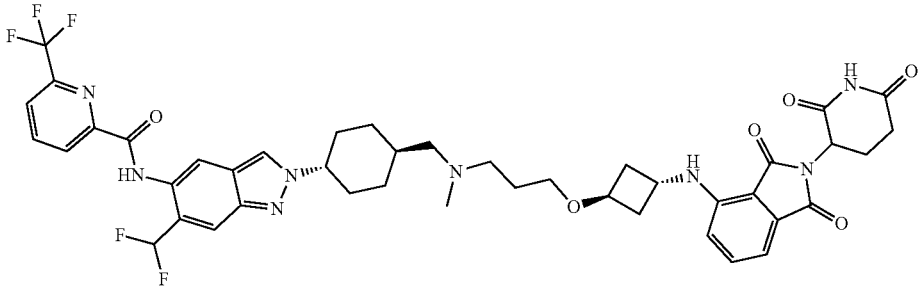 [SMILES: CN(CCCO[C@H]1C[C@H](Nc2cccc3c2C(=O)N(C2CCC(=O)NC2=O)C3=O)C1)C[C@H]1CC[C@H](n2cc3cc(NC(=O)c4cccc(C(F)(F)F)n4)c(C(F)F)cc3n2)CC1] |
| I-352 | 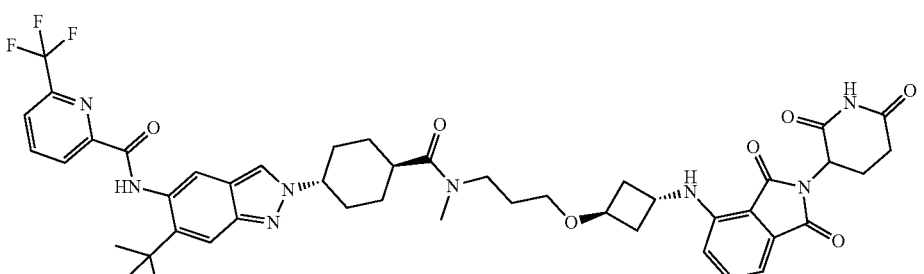 |
| I-353 | 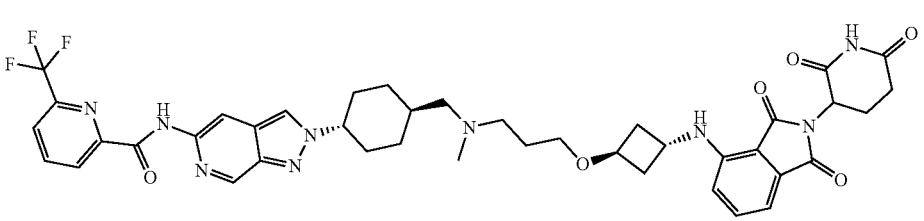 [SMILES: CN(CCCO[C@H]1C[C@H](Nc2cccc3c2C(=O)N(C2CCC(=O)NC2=O)C3=O)C1)C[C@H]1CC[C@H](n2cc3cc(NC(=O)c4cccc(C(F)(F)F)n4)ncc3n2)CC1] |
| I-354 | 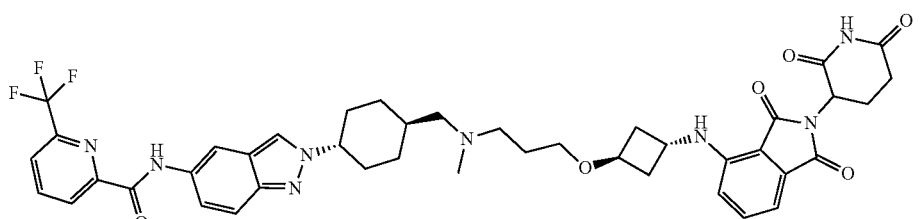 |
| I-355 | 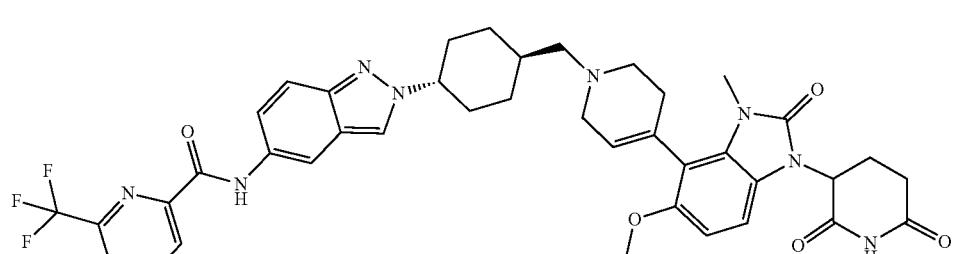 |

TABLE 1-continued
Exemplary Compounds
| I-# | Structure |
|---|---|
| I-356 | 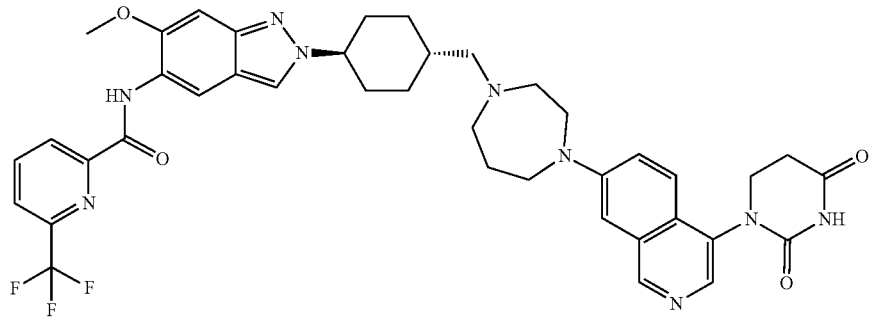 [SMILES: COc1cc2nn([C@H]3CC[C@H](CN4CCCN(c5ccc6c(N7CCC(=O)NC7=O)cncc6c5)CC4)CC3)cc2cc1NC(=O)c1cccc(C(F)(F)F)n1] |
| I-357 | 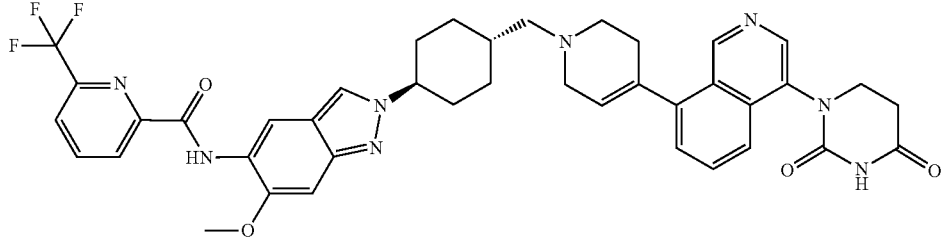 [SMILES: COc1cc2nn([C@H]3CC[C@H](CN4CC=C(c5cccc6c(N7CCC(=O)NC7=O)cncc56)CC4)CC3)cc2cc1NC(=O)c1cccc(C(F)(F)F)n1] |
| I-358 | 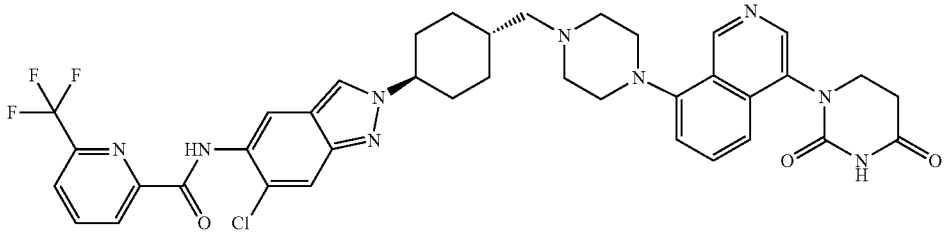 [SMILES: O=C1CCN(c2cncc3c(N4CCN(C[C@H]5CC[C@H](n6cc7cc(NC(=O)c8cccc(C(F)(F)F)n8)c(Cl)cc7n6)CC5)CC4)cccc23)C(=O)N1] |
| I-359 | 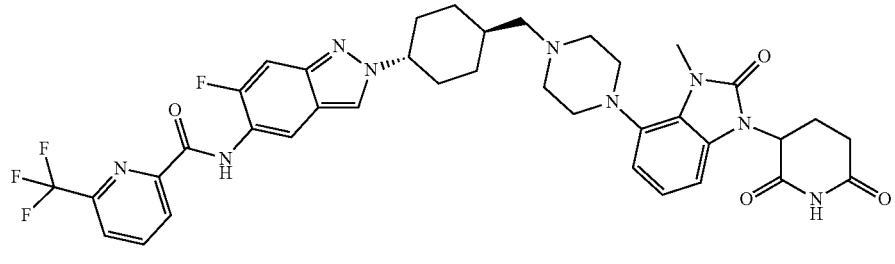 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(F)cc6n5)CC4)CC3)c21] |
| I-360 | 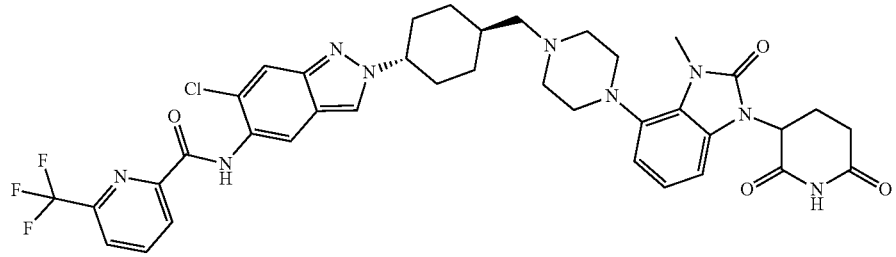 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(Cl)cc6n5)CC4)CC3)c21] |

TABLE 1-continued
Exemplary Compounds
| I-# | Structure |
|---|---|
| I-361 | 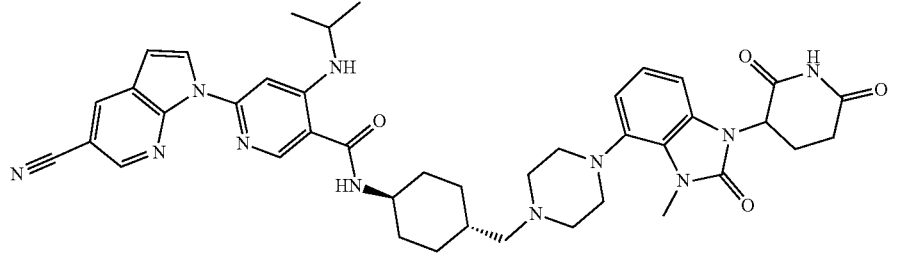 [SMILES: CC(C)Nc1cc(-n2ccc3cc(C#N)cnc32)ncc1C(=O)N[C@H]1CC[C@H](CN2CCN(c3cccc4c3n(C)c(=O)n4C3CCC(=O)NC3=O)CC2)CC1] |
| I-362 | 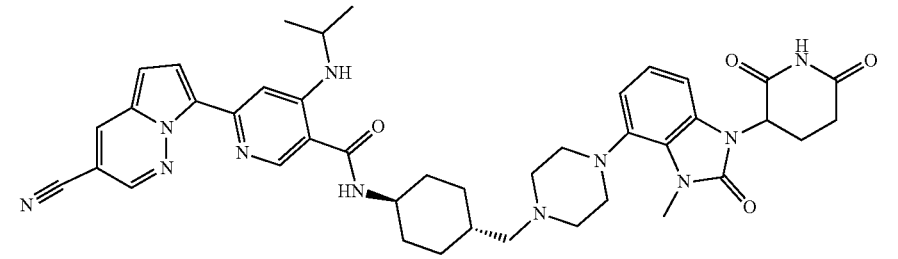 [SMILES: CC(C)Nc1cc(-c2ccc3cc(C#N)cnn23)ncc1C(=O)N[C@H]1CC[C@H](CN2CCN(c3cccc4c3n(C)c(=O)n4C3CCC(=O)NC3=O)CC2)CC1] |
| I-363 | 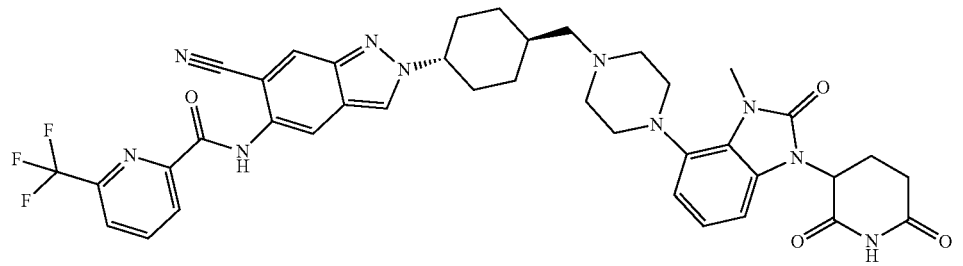 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(C#N)cc6n5)CC4)CC3)c21] |
| I-364 | 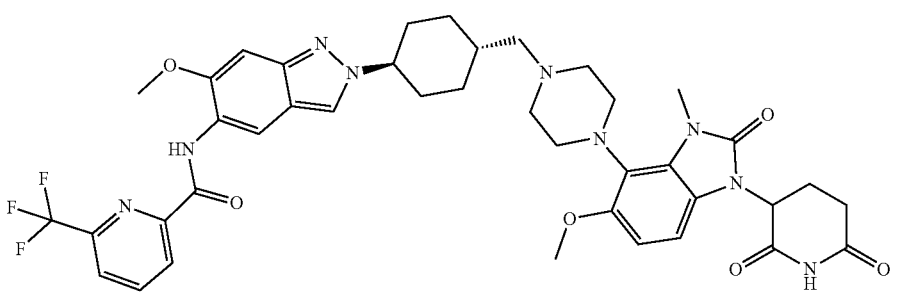 [SMILES: COc1cc2nn([C@H]3CC[C@H](CN4CCN(c5c(OC)ccc6c5n(C)c(=O)n6C5CCC(=O)NC5=O)CC4)CC3)cc2cc1NC(=O)c1cccc(C(F)(F)F)n1] |
| I-365 | 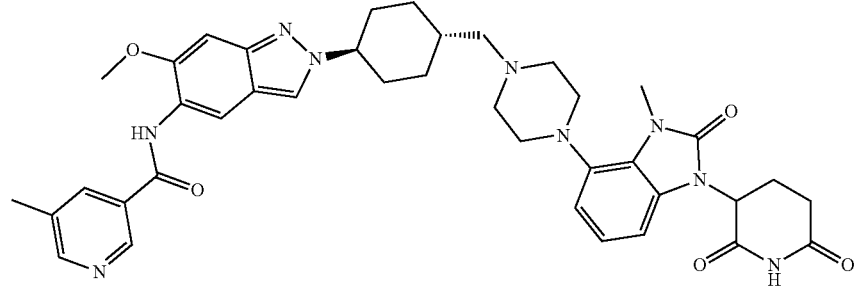 [SMILES: COc1cc2nn([C@H]3CC[C@H](CN4CCN(c5cccc6c5n(C)c(=O)n6C5CCC(=O)NC5=O)CC4)CC3)cc2cc1NC(=O)c1cncc(C)c1] |

TABLE 1-continued

Exemplary Compounds

| I-# | Structure |
|---|---|
| I-366 | 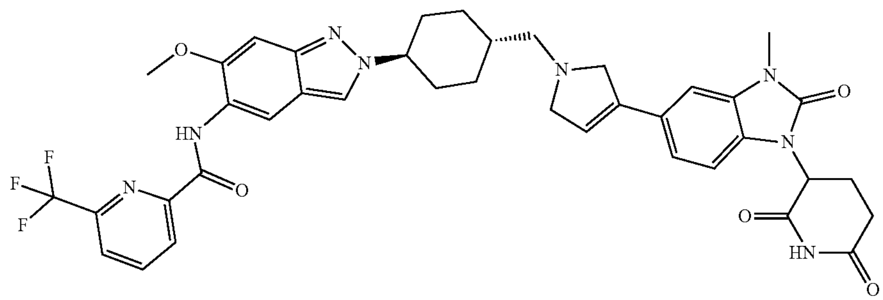 [SMILES: COc1cc2nn([C@H]3CC[C@H](CN4CC=C(c5ccc6c(c5)n(C)c(=O)n6C5CCC(=O)NC5=O)C4)CC3)cc2cc1NC(=O)c1cccc(C(F)(F)F)n1] |
| I-367 | 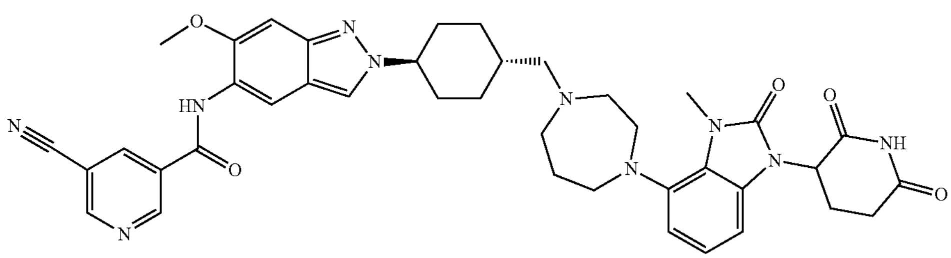 [SMILES: COc1cc2nn([C@H]3CC[C@H](CN4CCCN(c5cccc6c5n(C)c(=O)n6C5CCC(=O)NC5=O)CC4)CC3)cc2cc1NC(=O)c1cncc(C#N)c1] |
| I-368 | 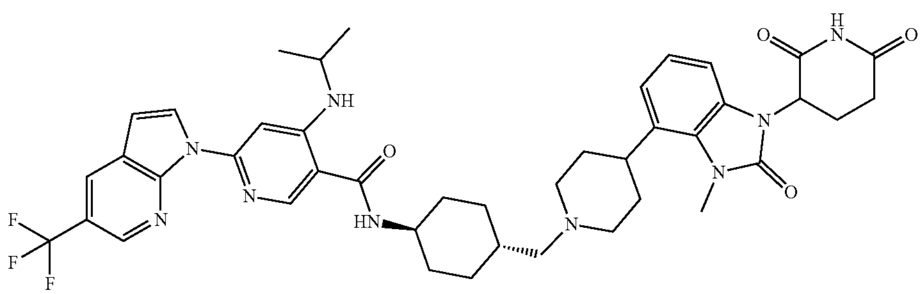 [SMILES: CC(C)Nc1cc(-n2ccc3cc(C(F)(F)F)cnc32)ncc1C(=O)N[C@H]1CC[C@H](CN2CCC(c3cccc4c3n(C)c(=O)n4C3CCC(=O)NC3=O)CC2)CC1] |
| I-369 | 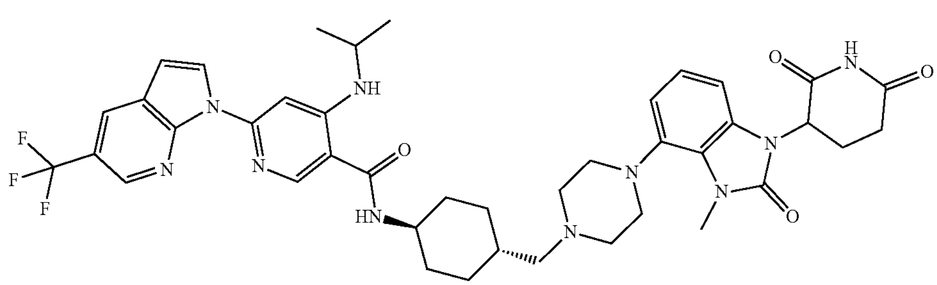 [SMILES: CC(C)Nc1cc(-n2ccc3cc(C(F)(F)F)cnc32)ncc1C(=O)N[C@H]1CC[C@H](CN2CCN(c3cccc4c3n(C)c(=O)n4C3CCC(=O)NC3=O)CC2)CC1] |
| I-370 | 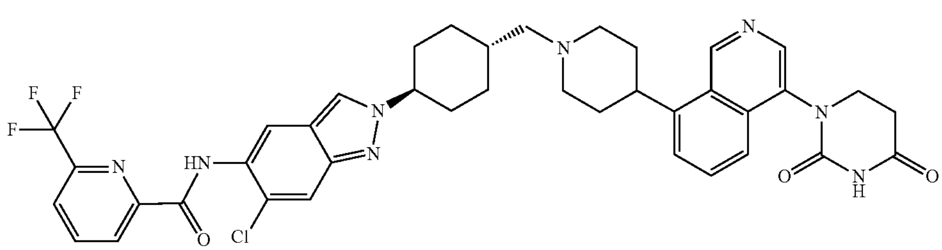 [SMILES: O=C1CCN(c2cncc3c(C4CCN(C[C@H]5CC[C@H](n6cc7cc(NC(=O)c8cccc(C(F)(F)F)n8)c(Cl)cc7n6)CC5)CC4)cccc23)C(=O)N1] |

TABLE 1-continued

Exemplary Compounds

| I-# | Structure |
|---|---|
| I-371 | 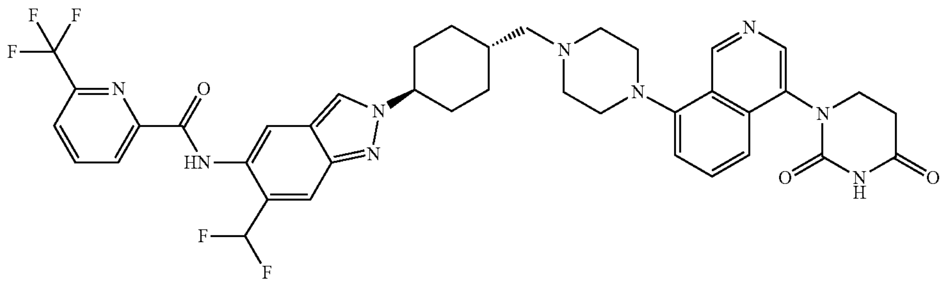 [SMILES: O=C1CCN(c2cncc3c(N4CCN(C[C@H]5CC[C@H](n6cc7cc(NC(=O)c8cccc(C(F)(F)F)n8)c(C(F)F)cc7n6)CC5)CC4)cccc23)C(=O)N1] |
| I-372 | 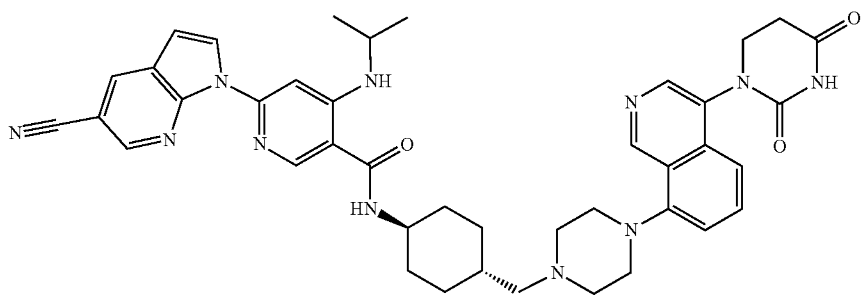 [SMILES: CC(C)Nc1cc(-n2ccc3cc(C#N)cnc32)ncc1C(=O)N[C@H]1CC[C@H](CN2CCN(c3cccc4c(N5CCC(=O)NC5=O)cncc34)CC2)CC1] |
| I-373 | 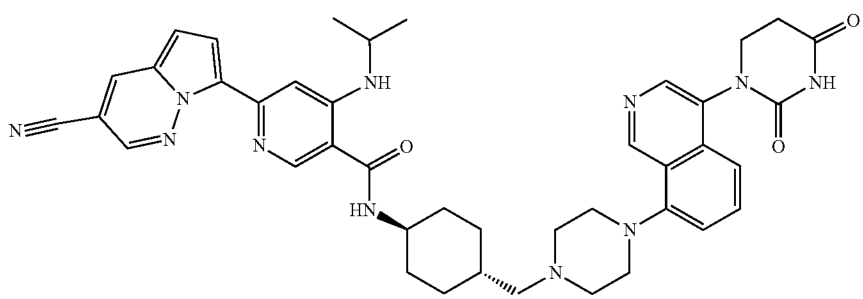 [SMILES: CC(C)Nc1cc(-c2ccc3cc(C#N)cnn23)ncc1C(=O)N[C@H]1CC[C@H](CN2CCN(c3cccc4c(N5CCC(=O)NC5=O)cncc34)CC2)CC1] |
| I-374 | 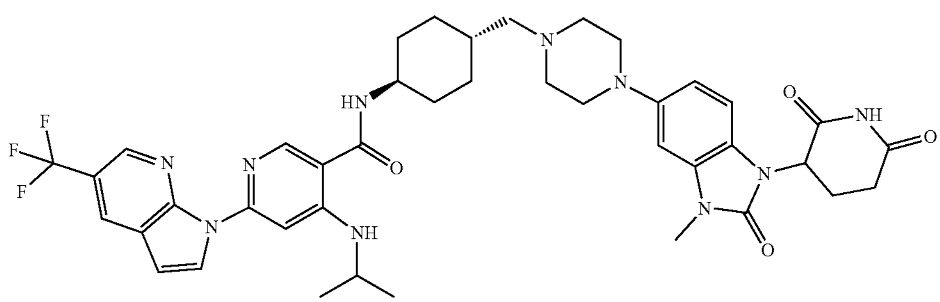 [SMILES: CC(C)Nc1cc(-n2ccc3cc(C(F)(F)F)cnc32)ncc1C(=O)N[C@H]1CC[C@H](CN2CCN(c3ccc4c(c3)n(C)c(=O)n4C3CCC(=O)NC3=O)CC2)CC1] |
| I-375 | 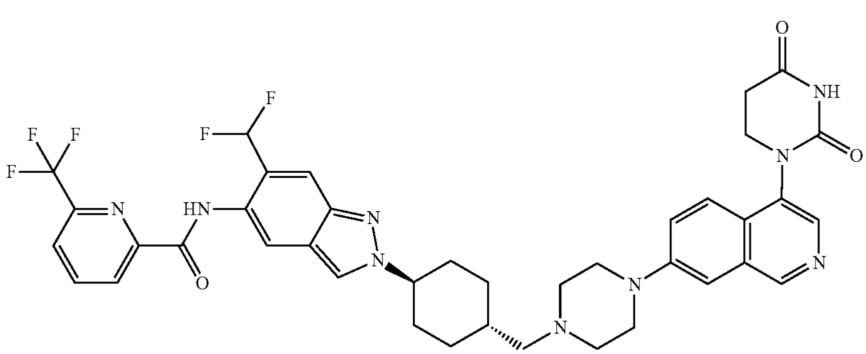 [SMILES: O=C1CCN(c2cncc3cc(N4CCN(C[C@H]5CC[C@H](n6cc7cc(NC(=O)c8cccc(C(F)(F)F)n8)c(C(F)F)cc7n6)CC5)CC4)ccc23)C(=O)N1] |

TABLE 1-continued

Exemplary Compounds

| I-# | Structure |
|---|---|
| I-376 | 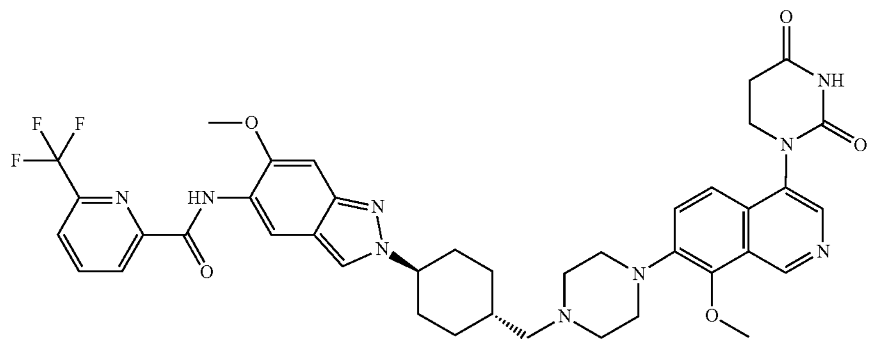 [SMILES: COc1cc2nn([C@H]3CC[C@H](CN4CCN(c5ccc6c(N7CCC(=O)NC7=O)cncc6c5OC)CC4)CC3)cc2cc1NC(=O)c1cccc(C(F)(F)F)n1] |
| I-377 | 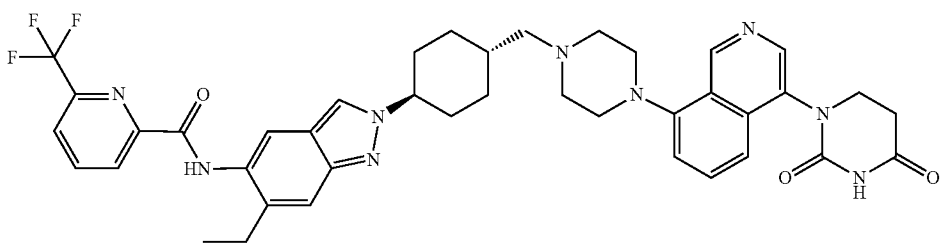 [SMILES: CCc1cc2nn([C@H]3CC[C@H](CN4CCN(c5cccc6c(N7CCC(=O)NC7=O)cncc56)CC4)CC3)cc2cc1NC(=O)c1cccc(C(F)(F)F)n1] |
| I-378 | 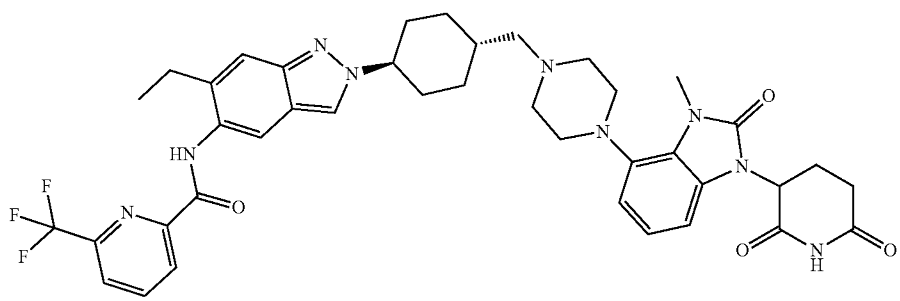 [SMILES: CCc1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |
| I-379 | 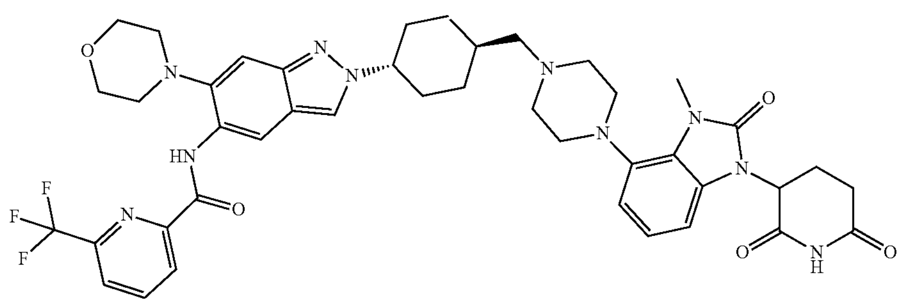 [SMILES: CC[C@H](CC[C@@H](C)CN1CCN(c2cccc3c2n(C)c(=O)n3C2CCC(=O)NC2=O)CC1)n1cc2cc(NC(=O)c3cccc(C(F)(F)F)n3)c(N3CCOCC3)cc2n1] |
| I-380 | 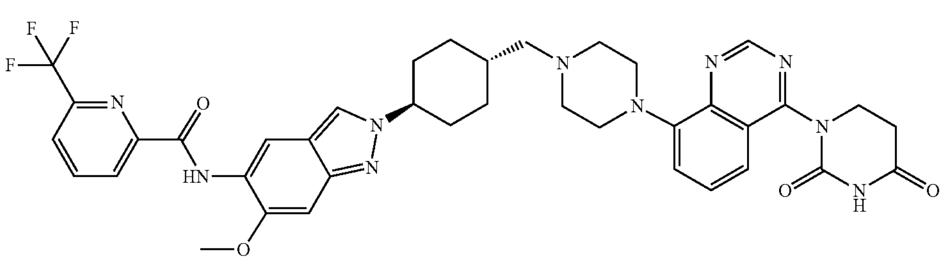 [SMILES: COc1cc2nn([C@H]3CC[C@H](CN4CCN(c5cccc6c(N7CCC(=O)NC7=O)ncnc56)CC4)CC3)cc2cc1NC(=O)c1cccc(C(F)(F)F)n1] |

TABLE 1-continued

Exemplary Compounds

| I-# | Structure |
|---|---|
| I-382 | 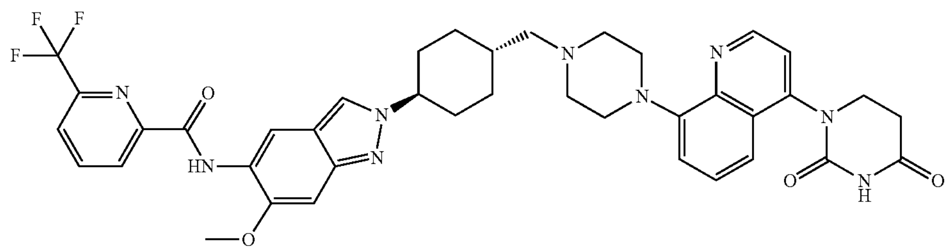 [SMILES: COc1cc2nn([C@H]3CC[C@H](CN4CCN(c5cccc6c(N7CCC(=O)NC7=O)ccnc56)CC4)CC3)cc2cc1NC(=O)c1cccc(C(F)(F)F)n1] |
| I-383 | 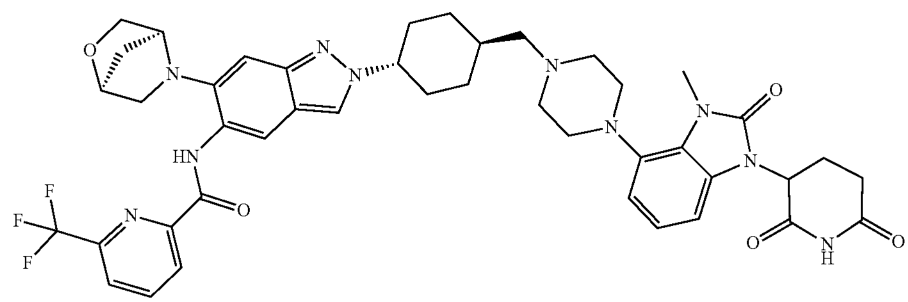 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(N7C[C@@H]8C[C@H]7CO8)cc6n5)CC4)CC3)c21] |
| I-384 | 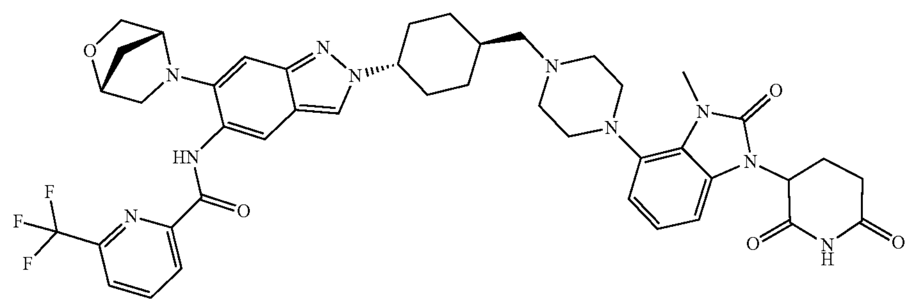 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(N7C[C@H]8C[C@@H]7CO8)cc6n5)CC4)CC3)c21] |
| I-385 | 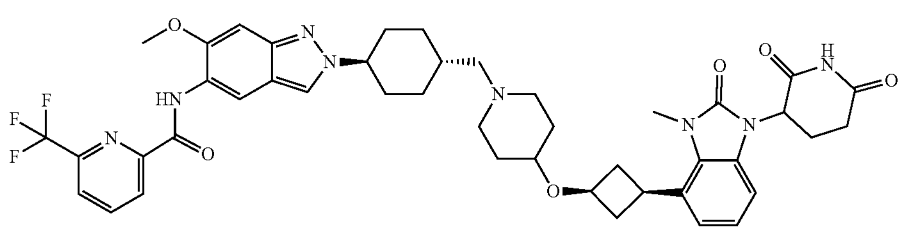 [SMILES: COc1cc2nn([C@H]3CC[C@H](CN4CCC(O[C@H]5C[C@@H](c6cccc7c6n(C)c(=O)n7C6CCC(=O)NC6=O)C5)CC4)CC3)cc2cc1NC(=O)c1cccc(C(F)(F)F)n1] |
| I-386 | 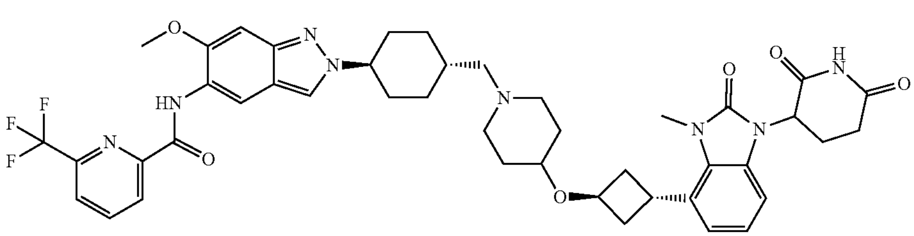 [SMILES: COc1cc2nn([C@H]3CC[C@H](CN4CCC(O[C@H]5C[C@H](c6cccc7c6n(C)c(=O)n7C6CCC(=O)NC6=O)C5)CC4)CC3)cc2cc1NC(=O)c1cccc(C(F)(F)F)n1] |

TABLE 1-continued

Exemplary Compounds

| I-# | Structure |
| --- | --- |
| I-387 | 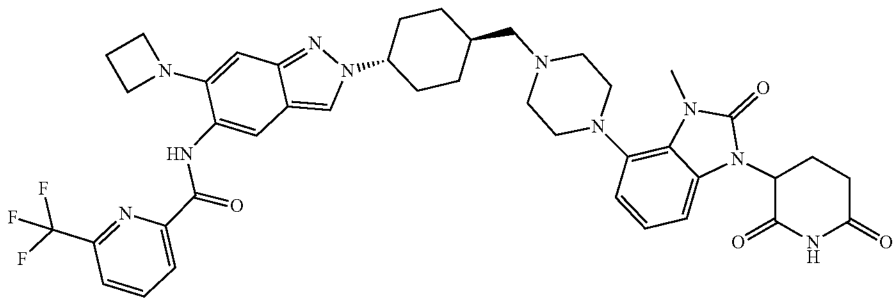 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(N7CCC7)cc6n5)CC4)CC3)c21] |
| I-388 | 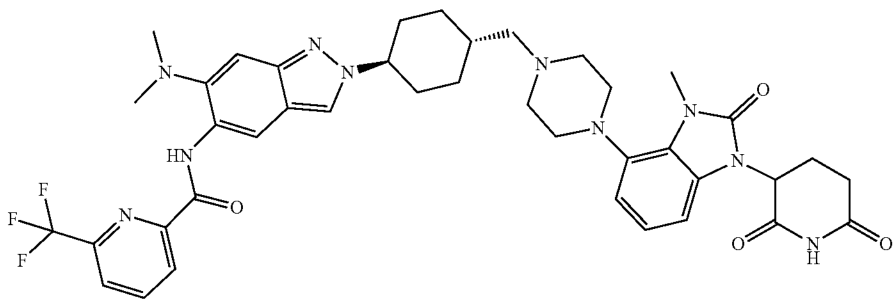 [SMILES: CN(C)c1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |
| I-389 | 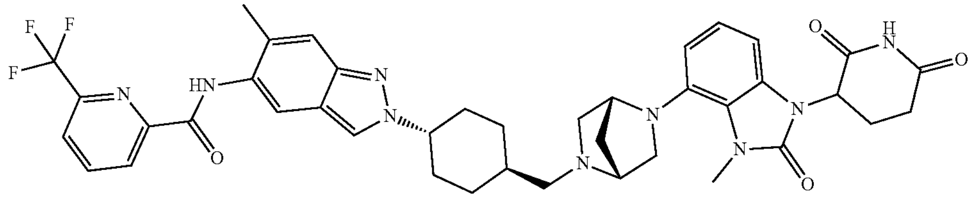 [SMILES: Cc1cc2nn([C@H]3CC[C@H](CN4C[C@H]5C[C@@H]4CN5c4cccc5c4n(C)c(=O)n5C4CCC(=O)NC4=O)CC3)cc2cc1NC(=O)c1cccc(C(F)(F)F)n1] |
| I-390 | 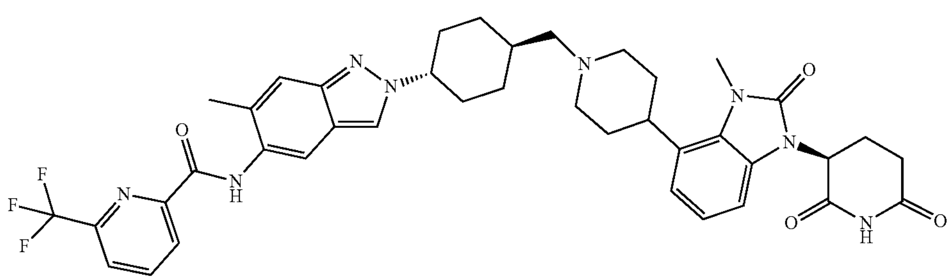 [SMILES: Cc1cc2nn([C@H]3CC[C@H](CN4CCC(c5cccc6c5n(C)c(=O)n6[C@H]5CCC(=O)NC5=O)CC4)CC3)cc2cc1NC(=O)c1cccc(C(F)(F)F)n1] |
| I-391 | 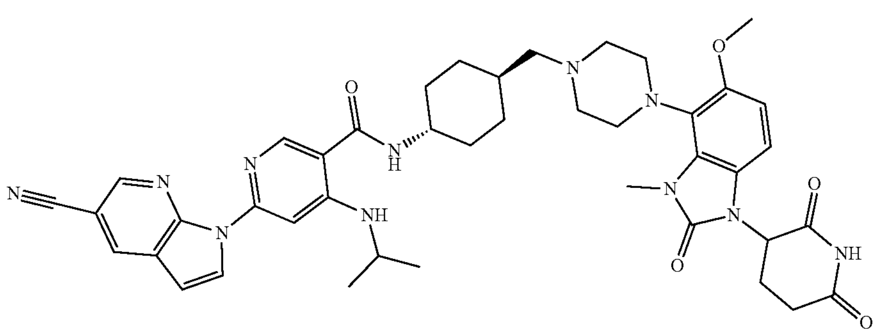 [SMILES: COc1ccc2c(c1N1CCN(C[C@H]3CC[C@H](NC(=O)c4cnc(-n5ccc6cc(C#N)cnc65)cc4NC(C)C)CC3)CC1)n(C)c(=O)n2C1CCC(=O)NC1=O] |

TABLE 1-continued
Exemplary Compounds
| I-# | Structure |
|---|---|
| I-392 | 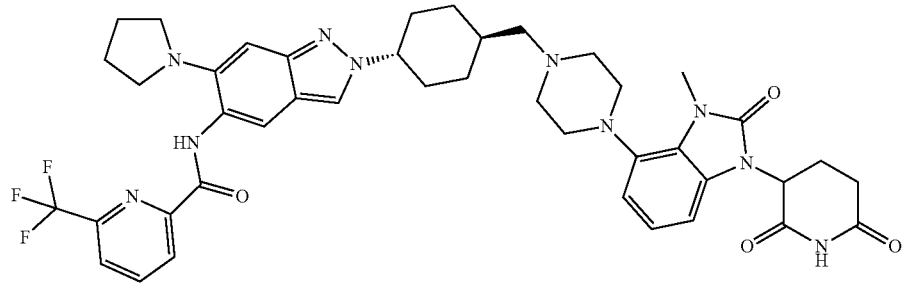 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(N7CCCC7)cc6n5)CC4)CC3)c21] |
| I-393 | 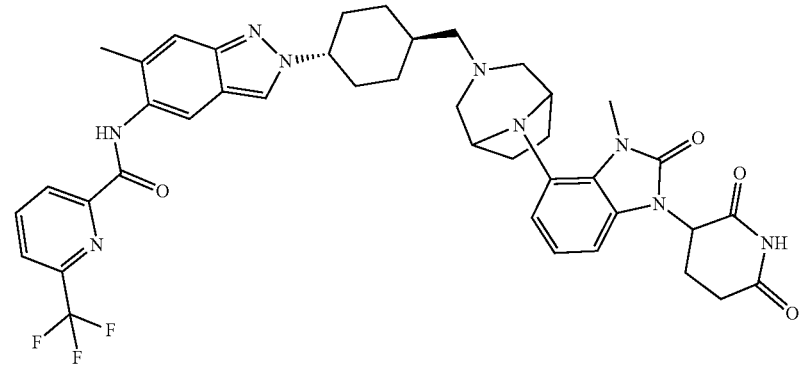 [SMILES: CCC1CN(C[C@H]2CC[C@H](n3cc4cc(NC(=O)c5cccc(C(F)(F)F)n5)c(C)cc4n3)CC2)CC(CC)N1c1cccc2c1n(C)c(=O)n2C1CCC(=O)NC1=O] |
| I-394 | 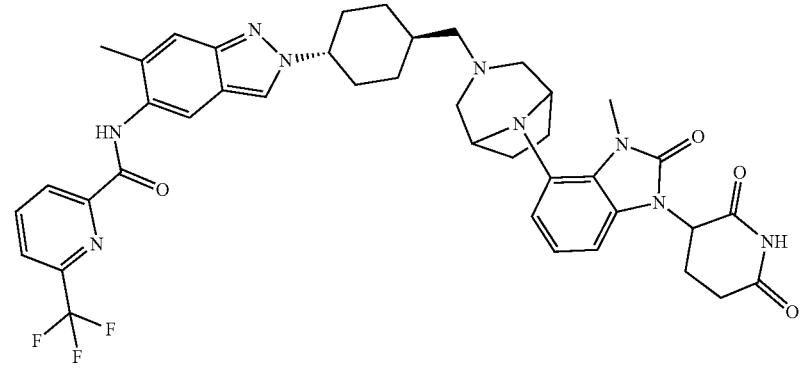 [SMILES: CCC1CN(C[C@H]2CC[C@H](n3cc4cc(NC(=O)c5cccc(C(F)(F)F)n5)c(C)cc4n3)CC2)CC(CC)N1c1cccc2c1n(C)c(=O)n2C1CCC(=O)NC1=O] |
| I-395 | 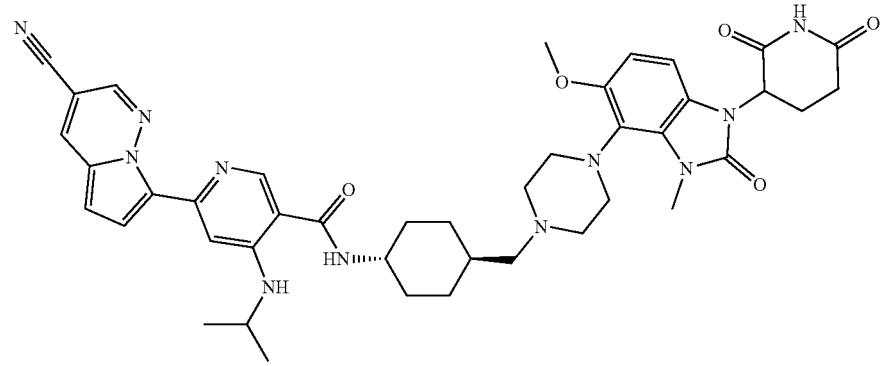 [SMILES: COc1ccc2c(c1N1CCN(C[C@H]3CC[C@H](NC(=O)c4cnc(-c5ccc6cc(C#N)cnn56)cc4NC(C)C)CC3)CC1)n(C)c(=O)n2C1CCC(=O)NC1=O] |

TABLE 1-continued

Exemplary Compounds

| I-# | Structure |
|---|---|
| I-396 | 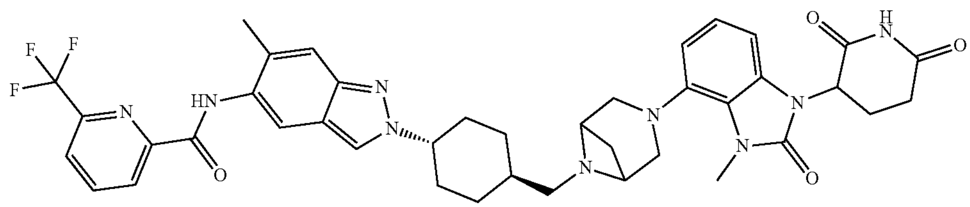 [SMILES: Cc1cc2nn([C@H]3CC[C@H](CN4C5CC4CN(c4cccc6c4n(C)c(=O)n6C4CCC(=O)NC4=O)C5)CC3)cc2cc1NC(=O)c1cccc(C(F)(F)F)n1] |
| I-397 | 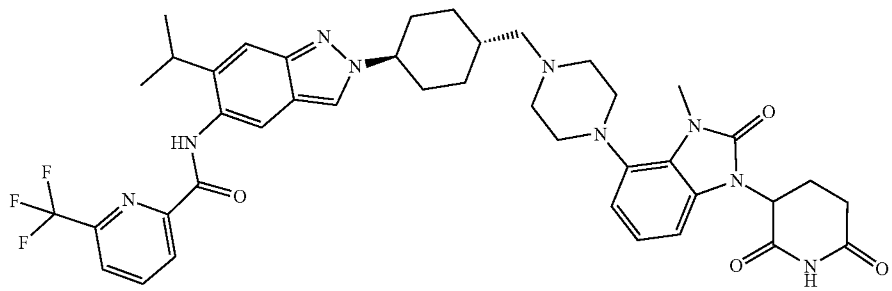 [SMILES: CC(C)c1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |
| I-398 | 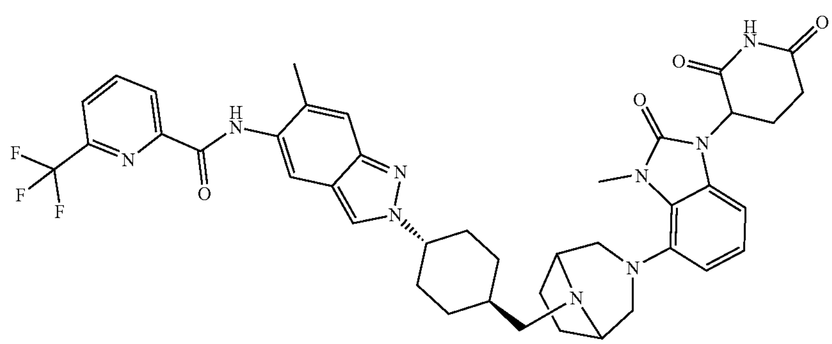 [SMILES: Cc1cc2nn([C@H]3CC[C@H](CN4C5CCC4CN(c4cccc6c4n(C)c(=O)n6C4CCC(=O)NC4=O)C5)CC3)cc2cc1NC(=O)c1cccc(C(F)(F)F)n1] |
| I-399 | 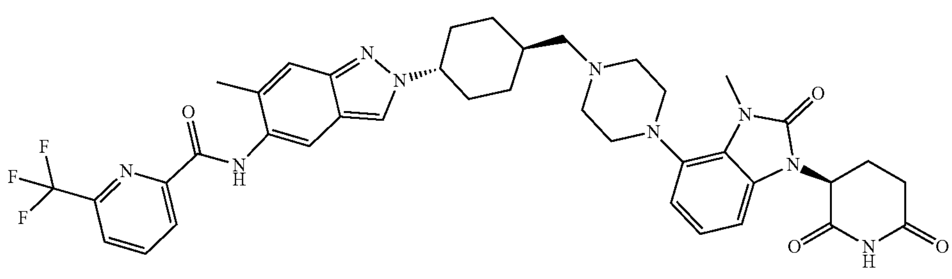 [SMILES: Cc1cc2nn([C@H]3CC[C@H](CN4CCN(c5cccc6c5n(C)c(=O)n6[C@H]5CCC(=O)NC5=O)CC4)CC3)cc2cc1NC(=O)c1cccc(C(F)(F)F)n1] |
| I-400 | 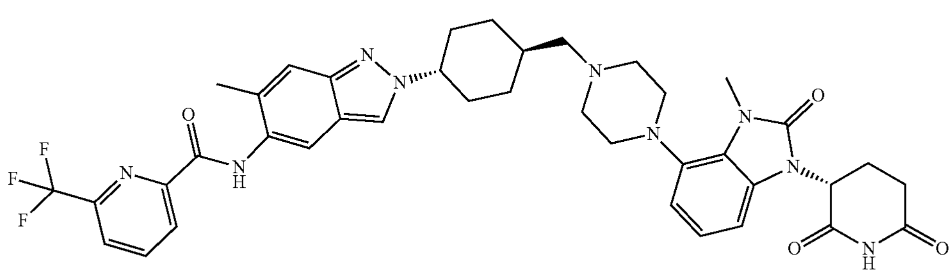 [SMILES: Cc1cc2nn([C@H]3CC[C@H](CN4CCN(c5cccc6c5n(C)c(=O)n6[C@@H]5CCC(=O)NC5=O)CC4)CC3)cc2cc1NC(=O)c1cccc(C(F)(F)F)n1] |

TABLE 1-continued

Exemplary Compounds

| I-# | Structure |
|---|---|
| I-401 | 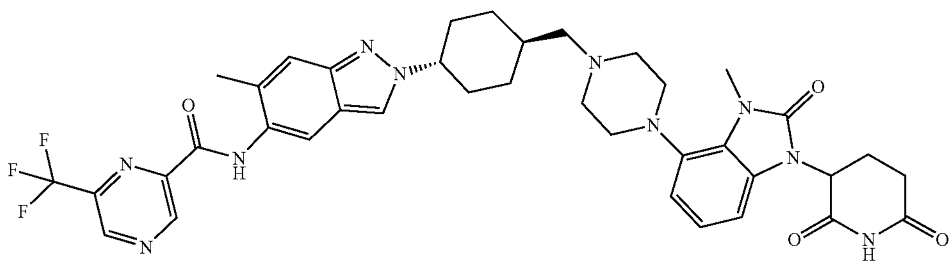 [SMILES: Cc1cc2nn([C@H]3CC[C@H](CN4CCN(c5cccc6c5n(C)c(=O)n6C5CCC(=O)NC5=O)CC4)CC3)cc2cc1NC(=O)c1cncc(C(F)(F)F)n1] |
| I-402 | 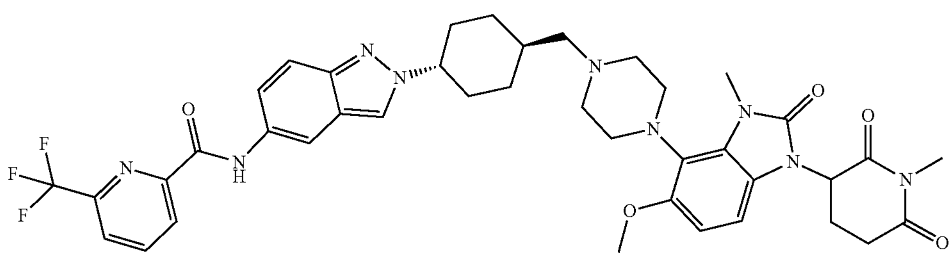 [SMILES: COc1ccc2c(c1N1CCN(C[C@H]3CC[C@H](n4cc5cc(NC(=O)c6cccc(C(F)(F)F)n6)ccc5n4)CC3)CC1)n(C)c(=O)n2C1CCC(=O)N(C)C1=O] |
| I-403 | 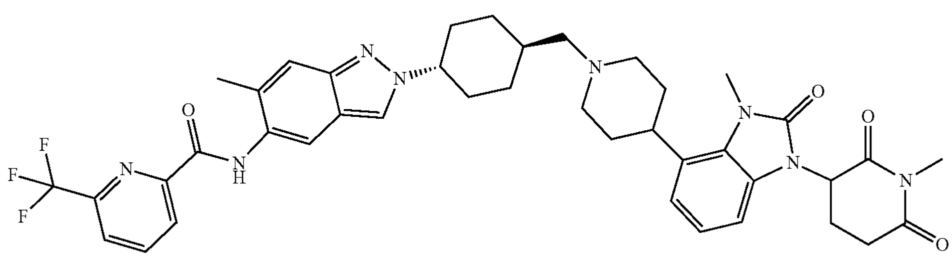 [SMILES: Cc1cc2nn([C@H]3CC[C@H](CN4CCC(c5cccc6c5n(C)c(=O)n6C5CCC(=O)N(C)C5=O)CC4)CC3)cc2cc1NC(=O)c1cccc(C(F)(F)F)n1] |
| I-404 | 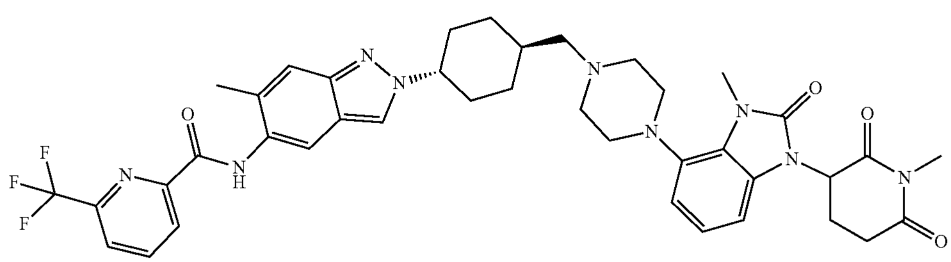 [SMILES: Cc1cc2nn([C@H]3CC[C@H](CN4CCN(c5cccc6c5n(C)c(=O)n6C5CCC(=O)N(C)C5=O)CC4)CC3)cc2cc1NC(=O)c1cccc(C(F)(F)F)n1] |
| I-405 | 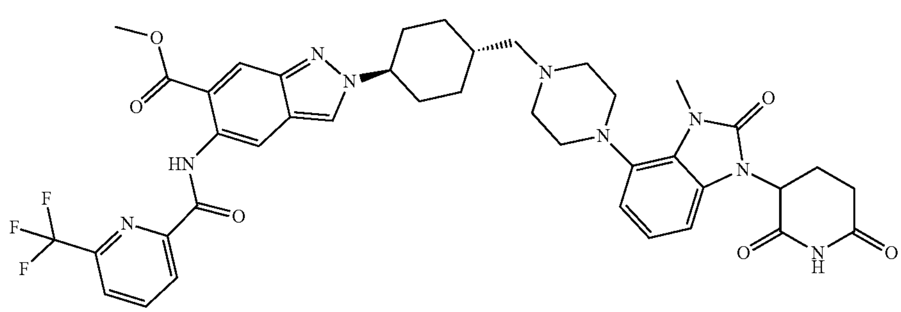 [SMILES: COC(=O)c1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |

TABLE 1-continued
Exemplary Compounds
| I-# | Structure |
|---|---|
| I-406 | 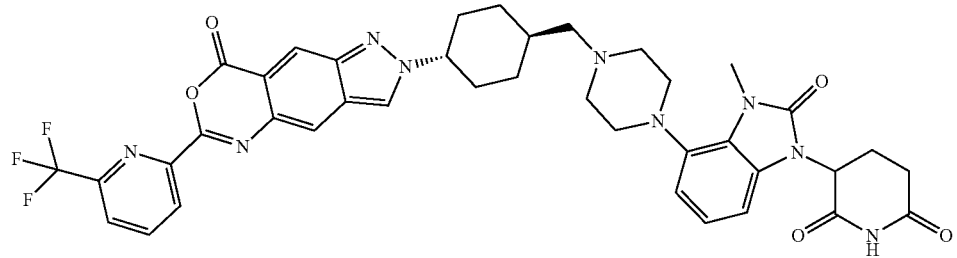 [SMILES: Cn1c(=O)n(C2CCC(=O)NC2=O)c2cccc(N3CCN(C[C@H]4CC[C@H](n5cc6cc7nc(-c8cccc(C(F)(F)F)n8)oc(=O)c7cc6n5)CC4)CC3)c21] |
| I-407 | 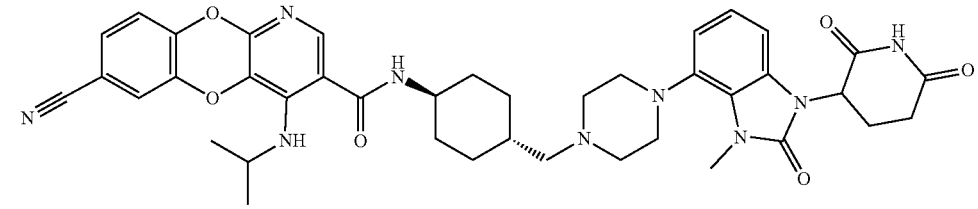 [SMILES: CC(C)Nc1c(C(=O)N[C@H]2CC[C@H](CN3CCN(c4cccc5c4n(C)c(=O)n5C4CCC(=O)NC4=O)CC3)CC2)cnc2c1Oc1cc(C#N)ccc1O2] |
| I-408 | 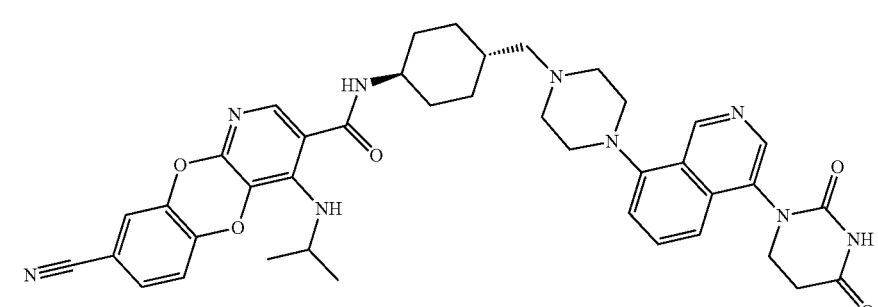 |
| I-409 | 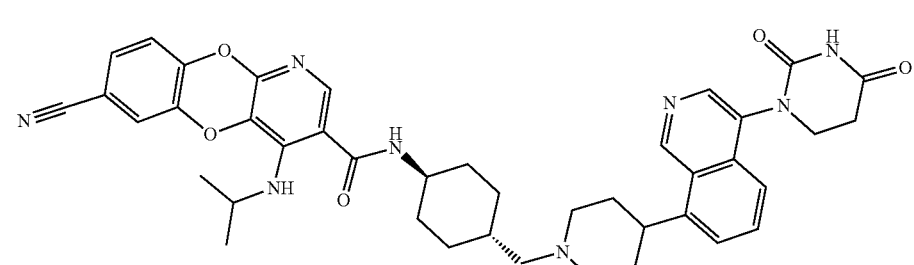 |
| I-410 | 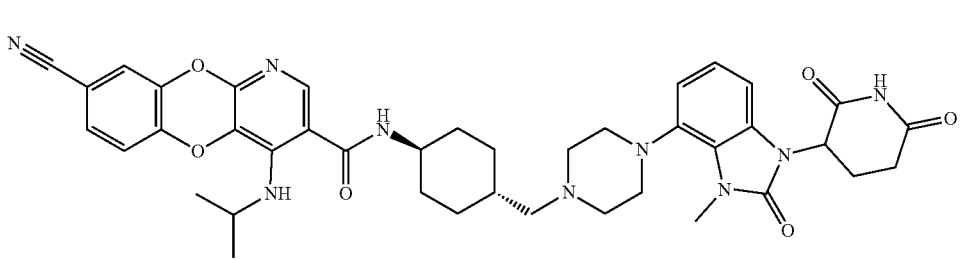 [SMILES: CC(C)Nc1c(C(=O)N[C@H]2CC[C@H](CN3CCN(c4cccc5c4n(C)c(=O)n5C4CCC(=O)NC4=O)CC3)CC2)cnc2c1Oc1ccc(C#N)cc1O2] |

TABLE 1-continued

Exemplary Compounds

| I-# | Structure |
| --- | --- |
| I-411 | 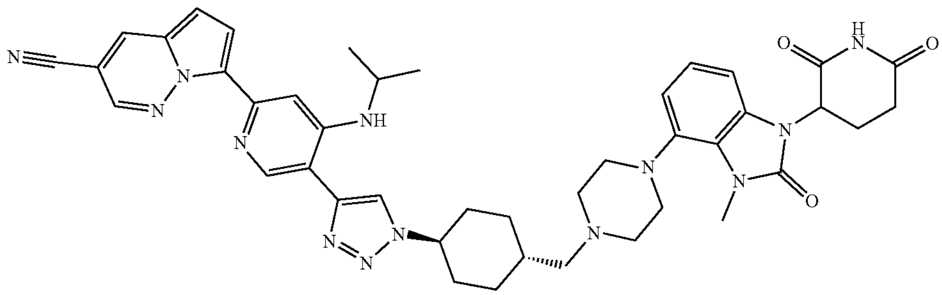 [SMILES: CC(C)Nc1cc(-c2ccc3cc(C#N)cnn23)ncc1-c1cn([C@H]2CC[C@H](CN3CCN(c4cccc5c4n(C)c(=O)n5C4CCC(=O)NC4=O)CC3)CC2)nn1] |
| I-412 | 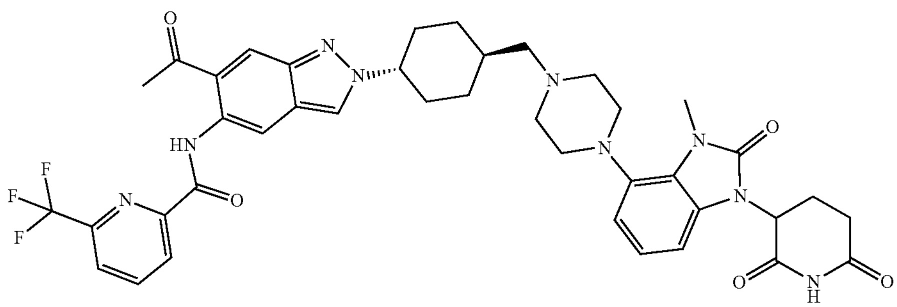 [SMILES: CC(=O)c1cc2nn([C@H]3CC[C@H](CN4CCN(c5cccc6c5n(C)c(=O)n6C5CCC(=O)NC5=O)CC4)CC3)cc2cc1NC(=O)c1cccc(C(F)(F)F)n1] |
| I-413 | 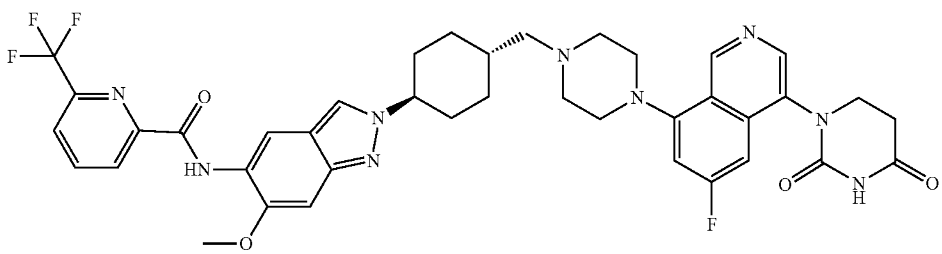 [SMILES: COc1cc2nn([C@H]3CC[C@H](CN4CCN(c5cc(F)cc6c(N7CCC(=O)NC7=O)cncc56)CC4)CC3)cc2cc1NC(=O)c1cccc(C(F)(F)F)n1] |
| I-414 | 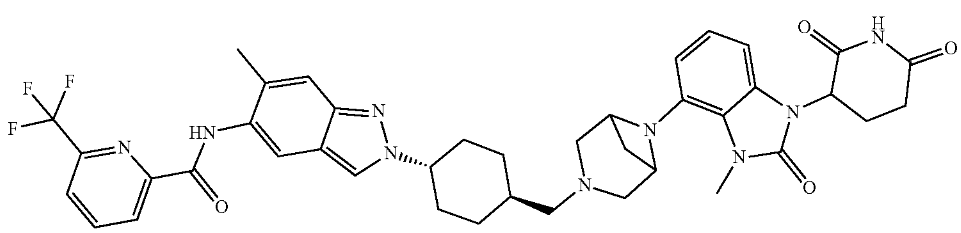 [SMILES: Cc1cc2nn([C@H]3CC[C@H](CN4CC5CC(C4)N5c4cccc5c4n(C)c(=O)n5C4CCC(=O)NC4=O)CC3)cc2cc1NC(=O)c1cccc(C(F)(F)F)n1] |
| I-415 | 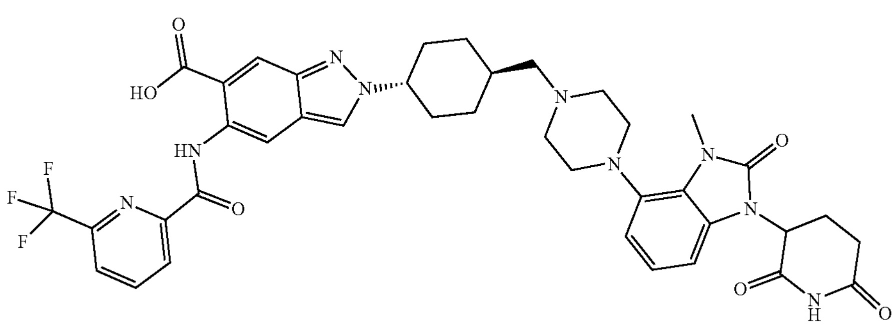 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(C(=O)O)cc6n5)CC4)CC3)c21] |

TABLE 1-continued

Exemplary Compounds

| I-# | Structure |
|---|---|
| I-416 | 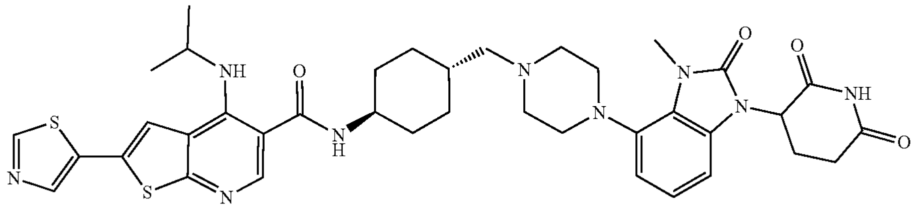 [SMILES: CC(C)Nc1c(C(=O)N[C@H]2CC[C@H](CN3CCN(c4cccc5c4n(C)c(=O)n5C4CCC(=O)NC4=O)CC3)CC2)cnc2sc(-c3cncs3)cc12] |
| I-417 | 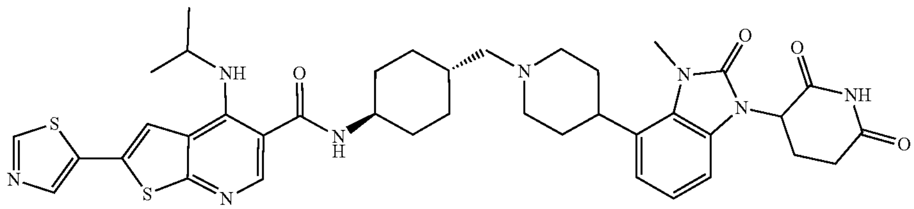 [SMILES: CC(C)Nc1c(C(=O)N[C@H]2CC[C@H](CN3CCC(c4cccc5c4n(C)c(=O)n5C4CCC(=O)NC4=O)CC3)CC2)cnc2sc(-c3cncs3)cc12] |
| I-418 | 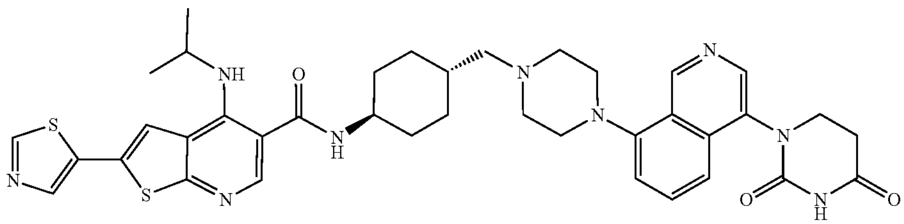 [SMILES: CC(C)Nc1c(C(=O)N[C@H]2CC[C@H](CN3CCN(c4cccc5c(N6CCC(=O)NC6=O)cncc45)CC3)CC2)cnc2sc(-c3cncs3)cc12] |
| I-419 | 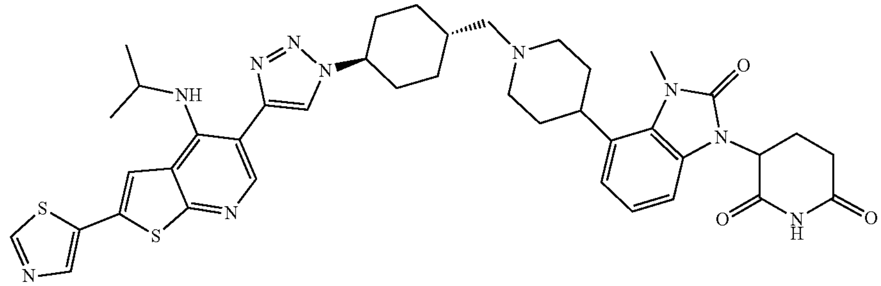 [SMILES: CC(C)Nc1c(-c2cn([C@H]3CC[C@H](CN4CCC(c5cccc6c5n(C)c(=O)n6C5CCC(=O)NC5=O)CC4)CC3)nn2)cnc2sc(-c3cncs3)cc12] |
| I-420 | 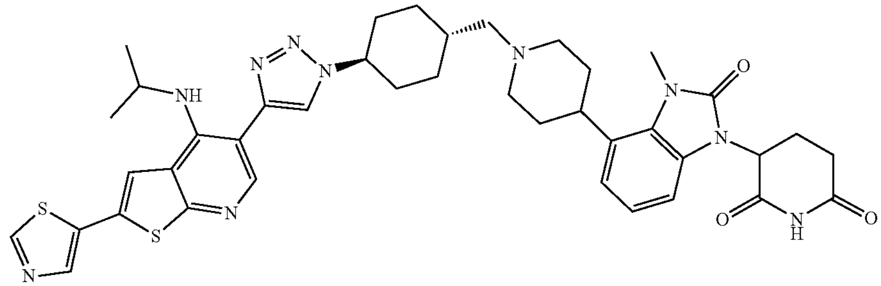 [SMILES: CC(C)Nc1c(-c2cn([C@H]3CC[C@H](CN4CCC(c5cccc6c5n(C)c(=O)n6C5CCC(=O)NC5=O)CC4)CC3)nn2)cnc2sc(-c3cncs3)cc12] |
| I-421 | 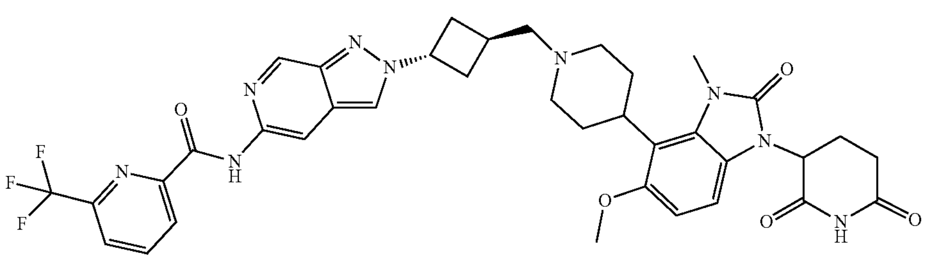 [SMILES: COc1ccc2c(c1C1CCN(C[C@H]3C[C@H](n4cc5cc(NC(=O)c6cccc(C(F)(F)F)n6)ncc5n4)C3)CC1)n(C)c(=O)n2C1CCC(=O)NC1=O] |

TABLE 1-continued

Exemplary Compounds

| I-# | Structure |
|---|---|
| I-422 | 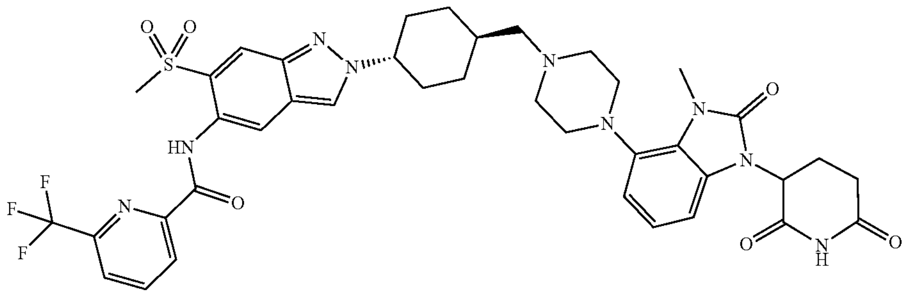 [SMILES: Cn1c(=O)n(C2CCC(=O)NC2=O)c2cccc(N3CCN(C[C@H]4CC[C@H](n5cc6cc(NC(=O)c7cccc(C(F)(F)F)n7)c(S(C)(=O)=O)cc6n5)CC4)CC3)c21] |
| I-423 | 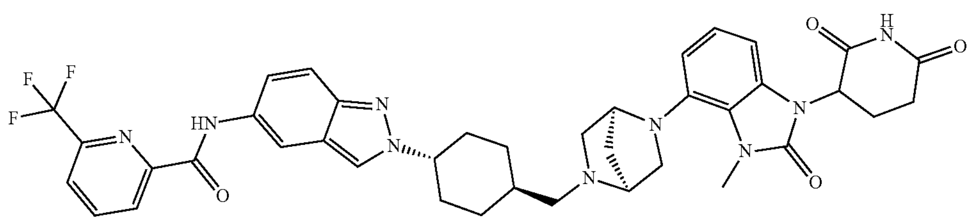 [SMILES: Cn1c(=O)n(C2CCC(=O)NC2=O)c2cccc(N3C[C@@H]4C[C@H]3CN4C[C@H]3CC[C@H](n4cc5cc(NC(=O)c6cccc(C(F)(F)F)n6)ccc5n4)CC3)c21] |
| I-424 | 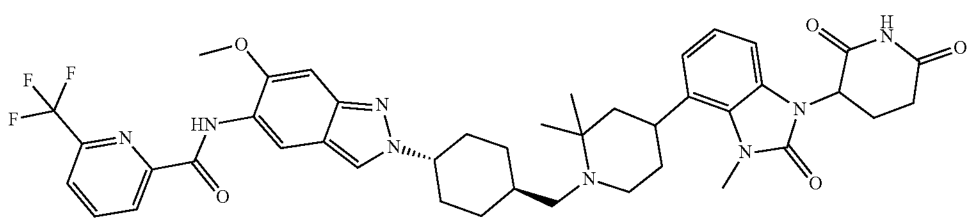 [SMILES: COc1cc2nn([C@H]3CC[C@H](CN4CCC(c5cccc6c5n(C)c(=O)n6C5CCC(=O)NC5=O)CC4(C)C)CC3)cc2cc1NC(=O)c1cccc(C(F)(F)F)n1] |
| I-425 | 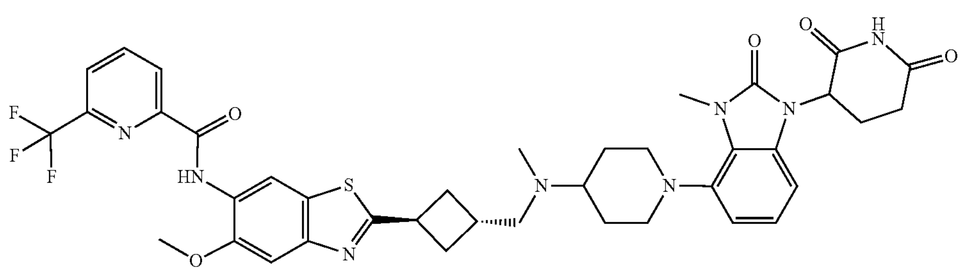 [SMILES: COc1cc2nc([C@H]3C[C@H](CN(C)C4CCN(c5cccc6c5n(C)c(=O)n6C5CCC(=O)NC5=O)CC4)C3)sc2cc1NC(=O)c1cccc(C(F)(F)F)n1] |
| I-426 | 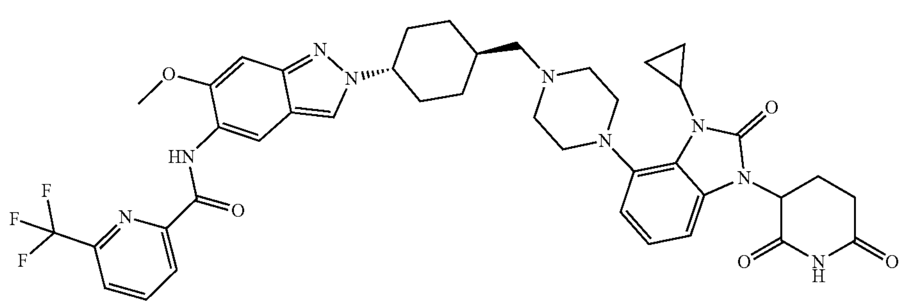 [SMILES: COc1cc2nn([C@H]3CC[C@H](CN4CCN(c5cccc6c5n(C5CC5)c(=O)n6C5CCC(=O)NC5=O)CC4)CC3)cc2cc1NC(=O)c1cccc(C(F)(F)F)n1] |

TABLE 1-continued

Exemplary Compounds

| I-# | Structure |
| --- | --- |
| I-427 | 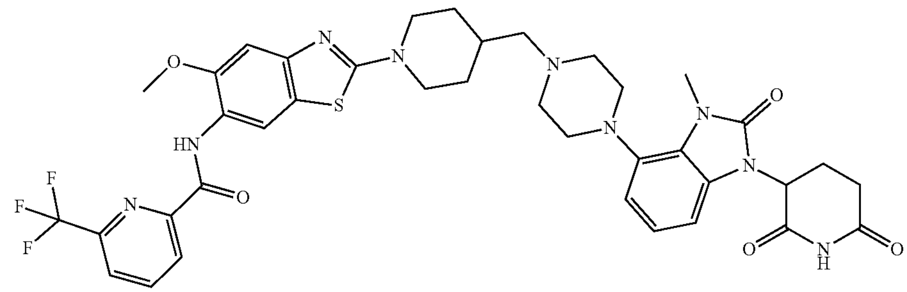 [SMILES: COc1cc2nc(N3CCC(CN4CCN(c5cccc6c5n(C)c(=O)n6C5CCC(=O)NC5=O)CC4)CC3)sc2cc1NC(=O)c1cccc(C(F)(F)F)n1] |
| I-428 | 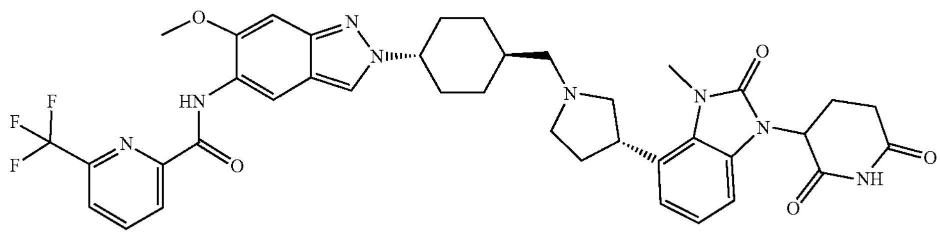 [SMILES: COc1cc2nn([C@H]3CC[C@H](CN4CC[C@@H](c5cccc6c5n(C)c(=O)n6C5CCC(=O)NC5=O)C4)CC3)cc2cc1NC(=O)c1cccc(C(F)(F)F)n1] |
| I-429 | 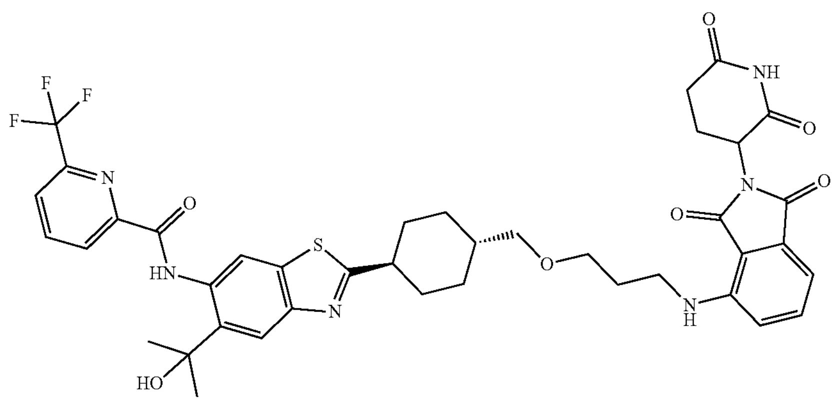 [SMILES: CC(C)(O)c1cc2nc([C@H]3CC[C@H](COCCCNc4cccc5c4C(=O)N(C4CCC(=O)NC4=O)C5=O)CC3)sc2cc1NC(=O)c1cccc(C(F)(F)F)n1] |
| I-430 | 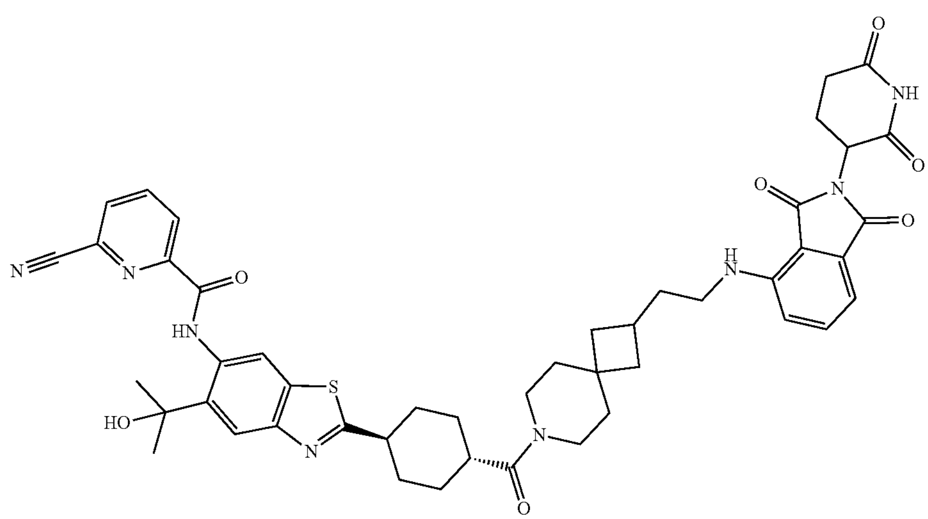 [SMILES: CC(C)(O)c1cc2nc([C@H]3CC[C@H](C(=O)N4CCC5(CC4)CC(CCNc4cccc6c4C(=O)N(C4CCC(=O)NC4=O)C6=O)C5)CC3)sc2cc1NC(=O)c1cccc(C#N)n1] |

TABLE 1-continued
Exemplary Compounds
| I-# | Structure |
|---|---|
| I-431 | 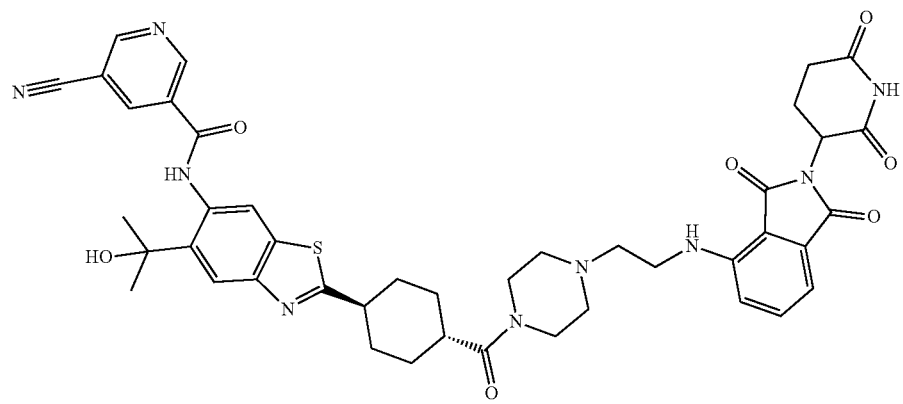 [SMILES: CC(C)(O)c1cc2nc([C@H]3CC[C@H](C(=O)N4CCN(CCNc5cccc6c5C(=O)N(C5CCC(=O)NC5=O)C6=O)CC4)CC3)sc2cc1NC(=O)c1cncc(C#N)c1] |
| I-432 | 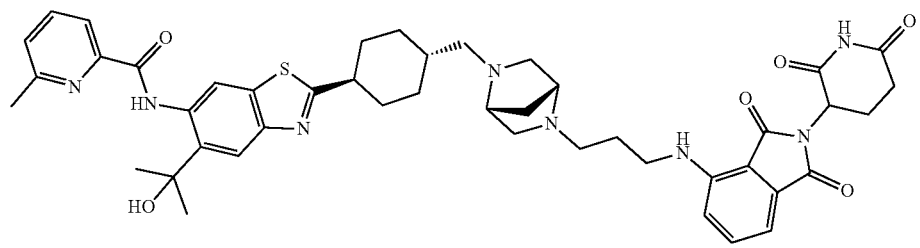 [SMILES: Cc1cccc(C(=O)Nc2cc3sc([C@H]4CC[C@H](CN5C[C@H]6C[C@@H]5CN6CCCNc5cccc6c5C(=O)N(C5CCC(=O)NC5=O)C6=O)CC4)nc3cc2C(C)(C)O)n1] |
| I-433 | 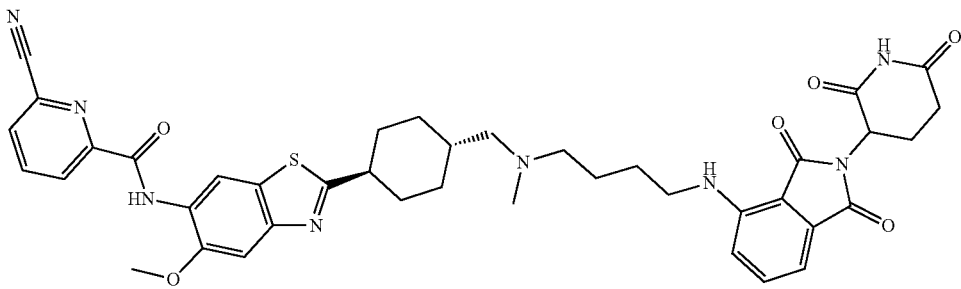 [SMILES: COc1cc2nc([C@H]3CC[C@H](CN(C)CCCCNc4cccc5c4C(=O)N(C4CCC(=O)NC4=O)C5=O)CC3)sc2cc1NC(=O)c1cccc(C#N)n1] |
| I-434 | 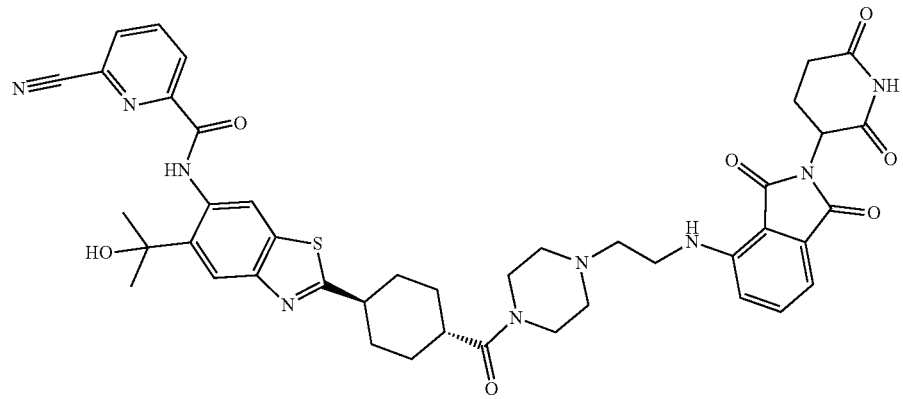 [SMILES: CC(C)(O)c1cc2nc([C@H]3CC[C@H](C(=O)N4CCN(CCNc5cccc6c5C(=O)N(C5CCC(=O)NC5=O)C6=O)CC4)CC3)sc2cc1NC(=O)c1cccc(C#N)n1] |

TABLE 1-continued

Exemplary Compounds

| I-# | Structure |
|---|---|
| I-435 | 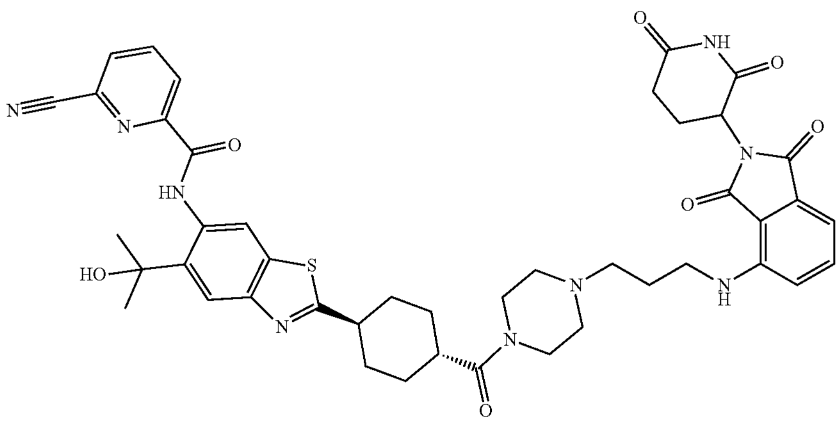 [SMILES: CC(C)(O)c1cc2nc([C@H]3CC[C@H](C(=O)N4CCN(CCCNc5cccc6c5C(=O)N(C5CCC(=O)NC5=O)C6=O)CC4)CC3)sc2cc1NC(=O)c1cccc(C#N)n1] |
| I-436 | 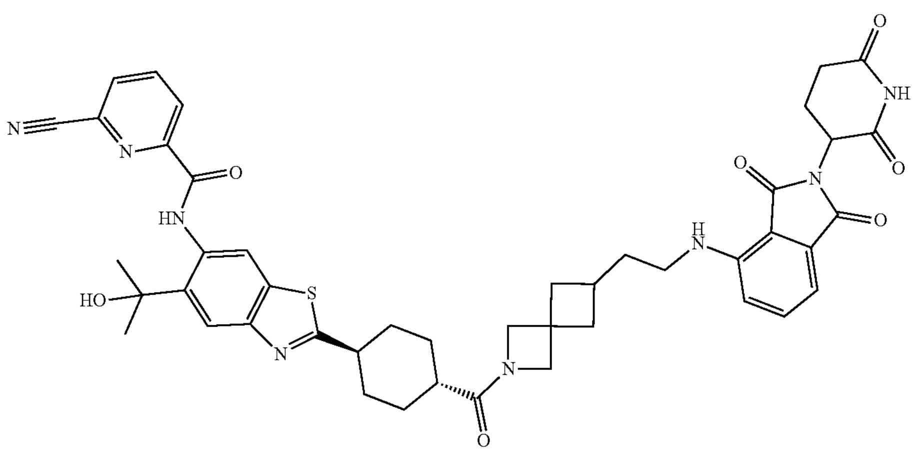 [SMILES: CC(C)(O)c1cc2nc([C@H]3CC[C@H](C(=O)N4CC5(CC(CCNc6cccc7c6C(=O)N(C6CCC(=O)NC6=O)C7=O)C5)C4)CC3)sc2cc1NC(=O)c1cccc(C#N)n1] |
| I-437 | 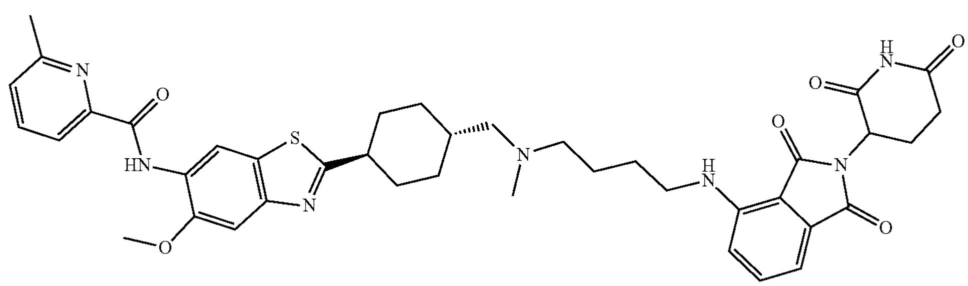 [SMILES: COc1cc2nc([C@H]3CC[C@H](CN(C)CCCCNc4cccc5c4C(=O)N(C4CCC(=O)NC4=O)C5=O)CC3)sc2cc1NC(=O)c1cccc(C)n1] |
| I-438 | 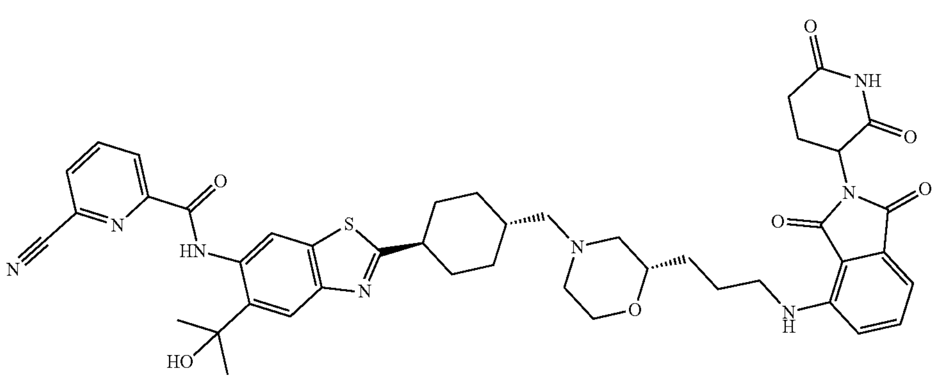 [SMILES: CC(C)(O)c1cc2nc([C@H]3CC[C@H](CN4CCO[C@@H](CCCNc5cccc6c5C(=O)N(C5CCC(=O)NC5=O)C6=O)C4)CC3)sc2cc1NC(=O)c1cccc(C#N)n1] |

TABLE 1-continued

Exemplary Compounds

| I-# | Structure |
| --- | --- |
| I-439 | 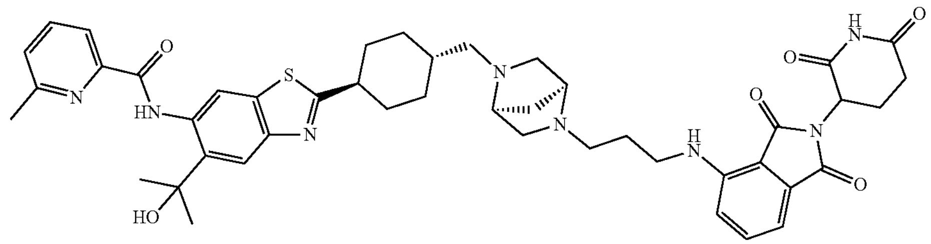 [SMILES: Cc1cccc(C(=O)Nc2cc3sc([C@H]4CC[C@H](CN5C[C@@H]6C[C@H]5CN6CCCNc5cccc6c5C(=O)N(C5CCC(=O)NC5=O)C6=O)CC4)nc3cc2C(C)(C)O)n1] |
| I-440 | 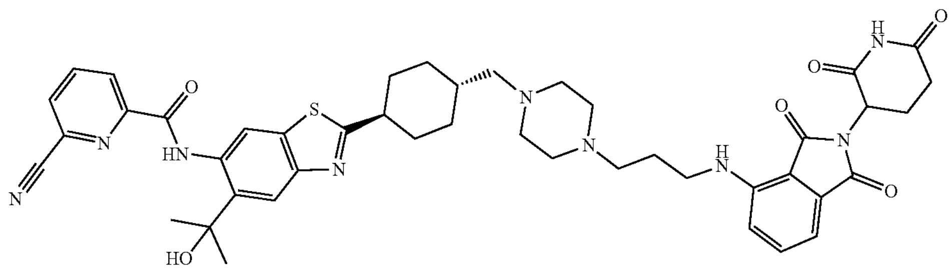 [SMILES: CC(C)(O)c1cc2nc([C@H]3CC[C@H](CN4CCN(CCCNc5cccc6c5C(=O)N(C5CCC(=O)NC5=O)C6=O)CC4)CC3)sc2cc1NC(=O)c1cccc(C#N)n1] |
| I-441 | 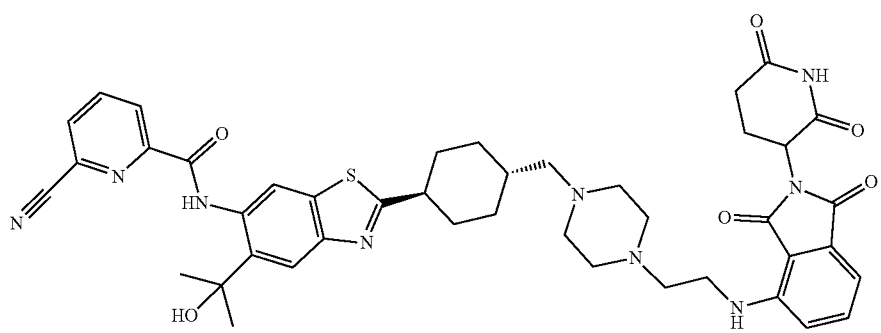 [SMILES: CC(C)(O)c1cc2nc([C@H]3CC[C@H](CN4CCN(CCNc5cccc6c5C(=O)N(C5CCC(=O)NC5=O)C6=O)CC4)CC3)sc2cc1NC(=O)c1cccc(C#N)n1] |
| I-442 | 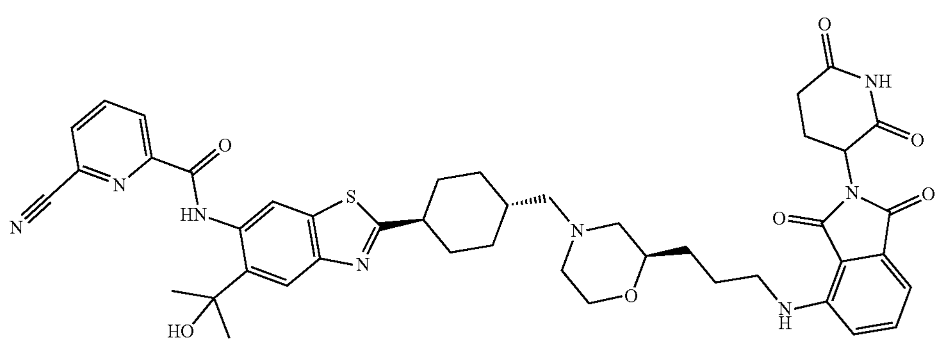 [SMILES: CC(C)(O)c1cc2nc([C@H]3CC[C@H](CN4CCO[C@H](CCCNc5cccc6c5C(=O)N(C5CCC(=O)NC5=O)C6=O)C4)CC3)sc2cc1NC(=O)c1cccc(C#N)n1] |
| I-443 | 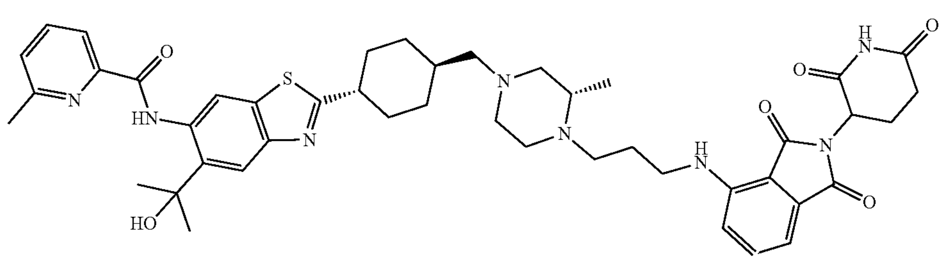 [SMILES: C=C/C(NCCCN1CCN(C[C@H]2CC[C@H](c3nc4cc(C(C)(C)O)c(NC(=O)c5cccc(C)n5)cc4s3)CC2)C[C@@H]1C)=C1/C(=O)N(C2CCC(=O)NC2=O)C(=O)/C1=C/C] |

TABLE 1-continued
Exemplary Compounds
| I-# | Structure |
|---|---|
| I-444 | 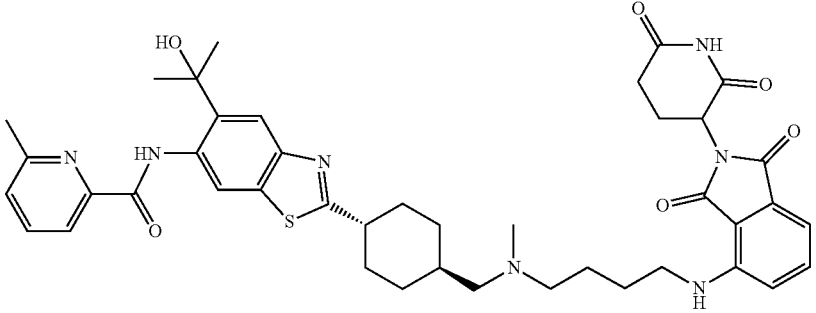 [SMILES: Cc1cccc(C(=O)Nc2cc3sc([C@H]4CC[C@H](CN(C)CCCCNc5cccc6c5C(=O)N(C5CCC(=O)NC5=O)C6=O)CC4)nc3cc2C(C)(C)O)n1] |
| I-445 | 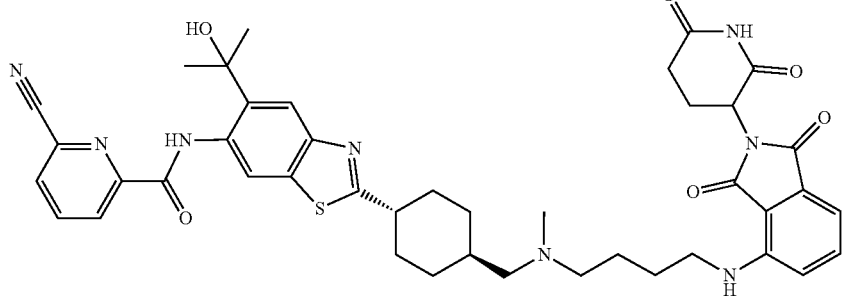 |
| I-446 | 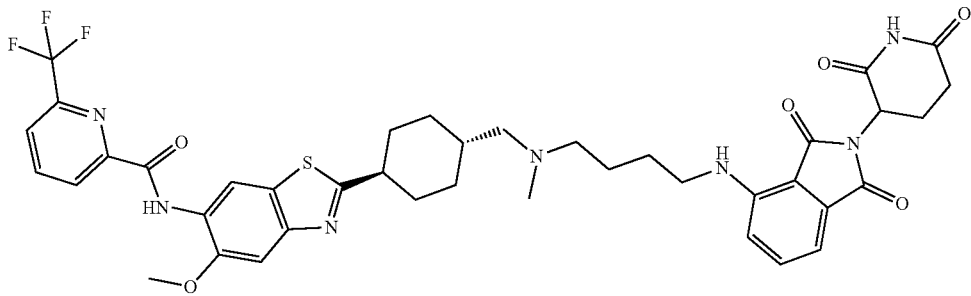 [SMILES: COc1cc2nc([C@H]3CC[C@H](CN(C)CCCCNc4cccc5c4C(=O)N(C4CCC(=O)NC4=O)C5=O)CC3)sc2cc1NC(=O)c1cccc(C(F)(F)F)n1] |
| I-447 | 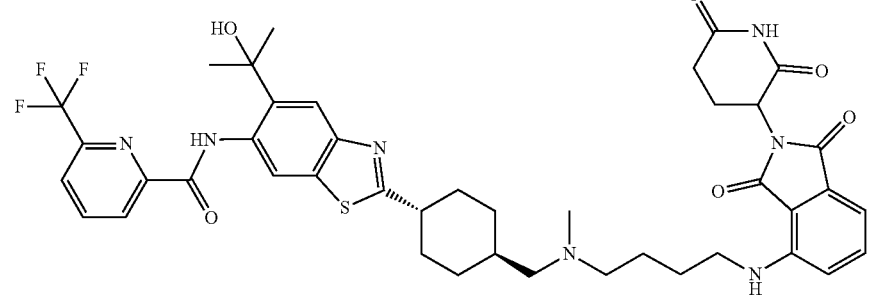 |

TABLE 1-continued

Exemplary Compounds

| I-# | Structure |
|---|---|
| I-448 | 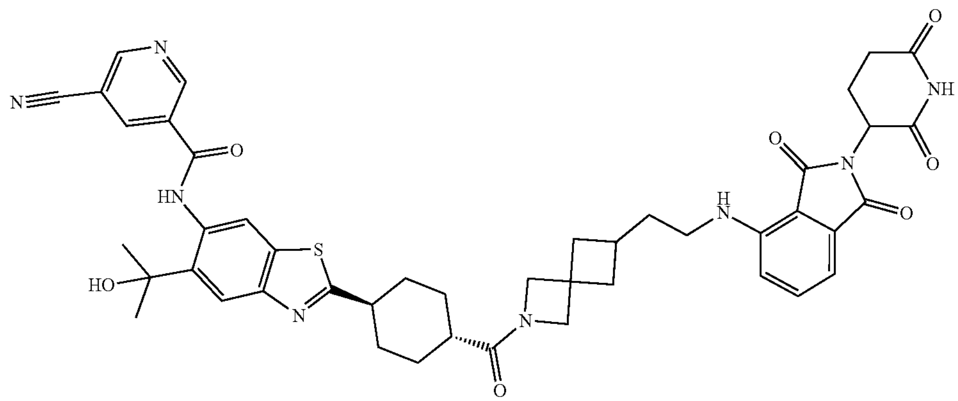 [SMILES: CC(C)(O)c1cc2nc([C@H]3CC[C@H](C(=O)N4CC5(CC(CCNc6cccc7c6C(=O)N(C6CCC(=O)NC6=O)C7=O)C5)C4)CC3)sc2cc1NC(=O)c1cncc(C#N)c1] |
| I-449 | 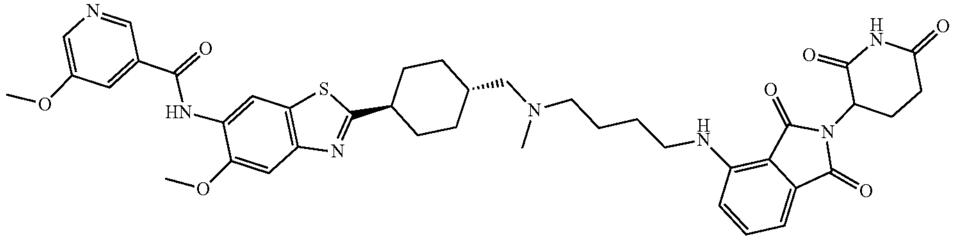 [SMILES: COc1cncc(C(=O)Nc2cc3sc([C@H]4CC[C@H](CN(C)CCCCNc5cccc6c5C(=O)N(C5CCC(=O)NC5=O)C6=O)CC4)nc3cc2OC)c1] |
| I-450 | 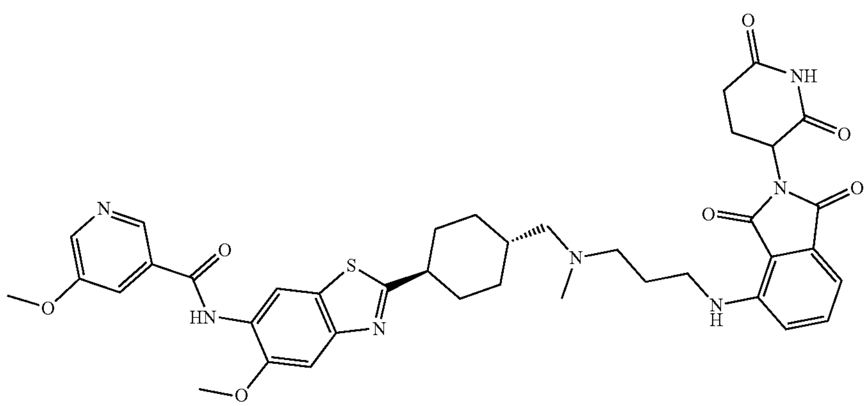 [SMILES: COc1cncc(C(=O)Nc2cc3sc([C@H]4CC[C@H](CN(C)CCCNc5cccc6c5C(=O)N(C5CCC(=O)NC5=O)C6=O)CC4)nc3cc2OC)c1] |
| I-451 | 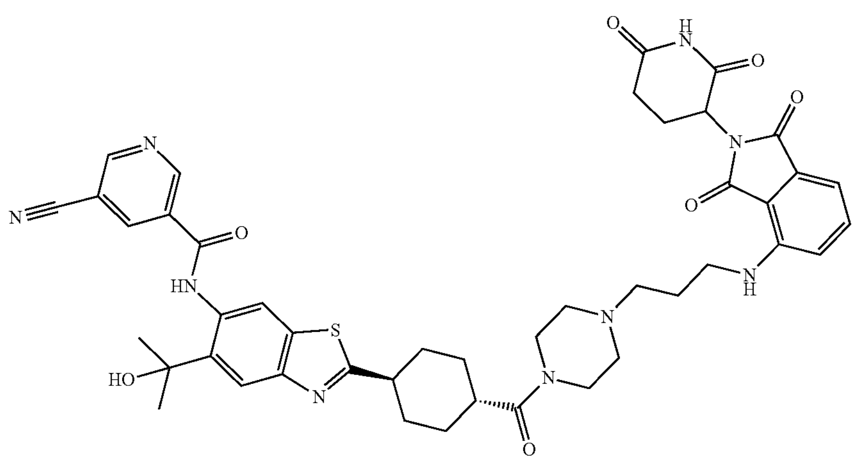 [SMILES: CC(C)(O)c1cc2nc([C@H]3CC[C@H](C(=O)N4CCN(CCCNc5cccc6c5C(=O)N(C5CCC(=O)NC5=O)C6=O)CC4)CC3)sc2cc1NC(=O)c1cncc(C#N)c1] |

TABLE 1-continued
Exemplary Compounds
| I-# | Structure |
|---|---|
| I-452 | 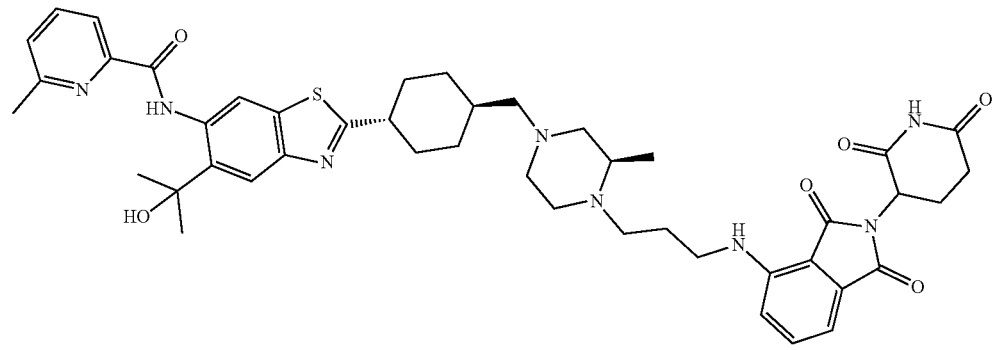 [SMILES: Cc1cccc(C(=O)Nc2cc3sc([C@H]4CC[C@H](CN5CCN(CCCNc6cccc7c6C(=O)N(C6CCC(=O)NC6=O)C7=O)[C@H](C)C5)CC4)nc3cc2C(C)(C)O)n1] |
| I-453 | 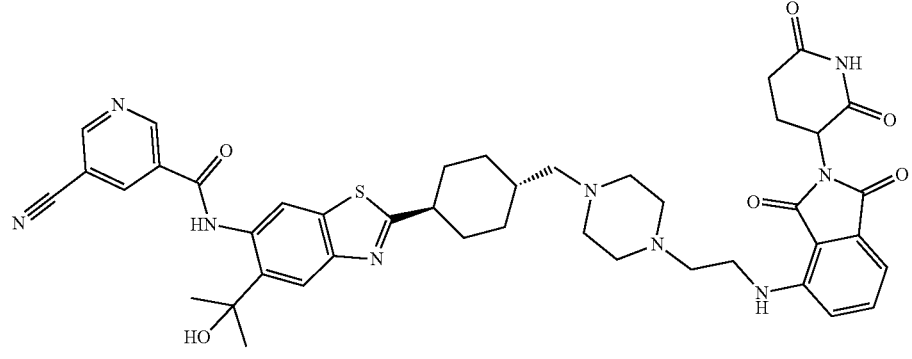 [SMILES: CC(C)(O)c1cc2nc([C@H]3CC[C@H](CN4CCN(CCNc5cccc6c5C(=O)N(C5CCC(=O)NC5=O)C6=O)CC4)CC3)sc2cc1NC(=O)c1cncc(C#N)c1] |
| I-454 | 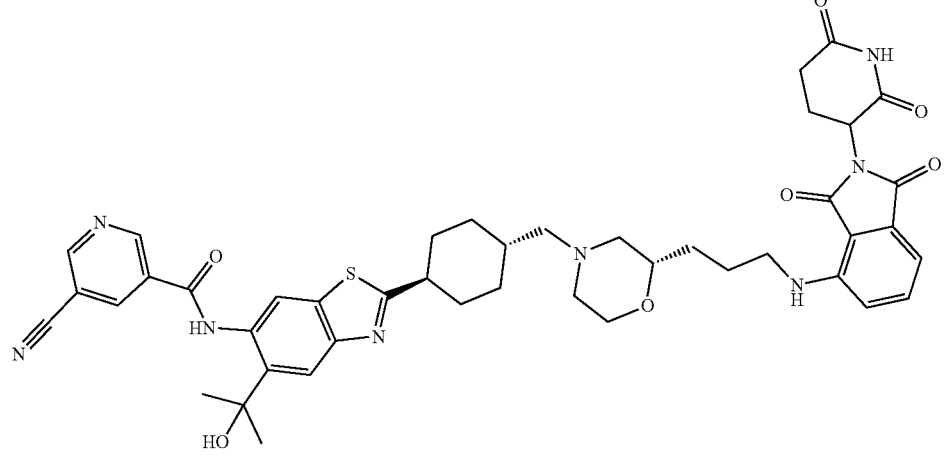 [SMILES: CC(C)(O)c1cc2nc([C@H]3CC[C@H](CN4CCO[C@@H](CCCNc5cccc6c5C(=O)N(C5CCC(=O)NC5=O)C6=O)C4)CC3)sc2cc1NC(=O)c1cncc(C#N)c1] |
| I-455 | 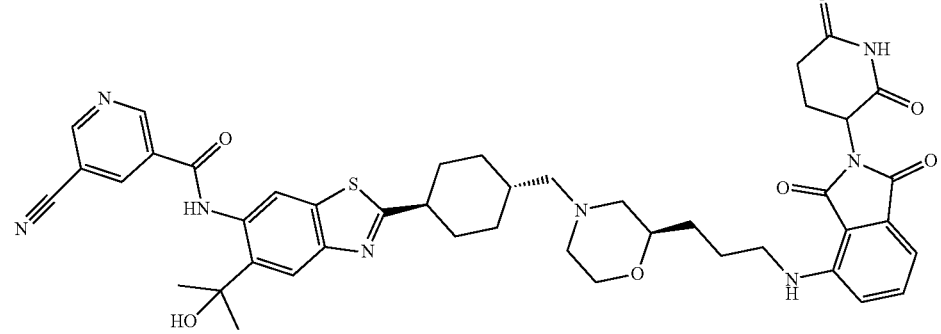 |

TABLE 1-continued

Exemplary Compounds

| I-# | Structure |
|---|---|
| I-456 | 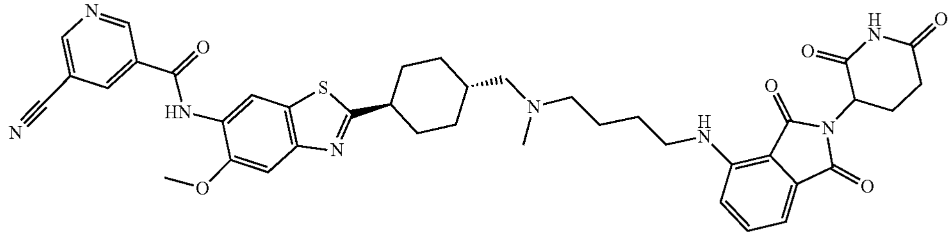 [SMILES: COc1cc2nc([C@H]3CC[C@H](CN(C)CCCCNc4cccc5c4C(=O)N(C4CCC(=O)NC4=O)C5=O)CC3)sc2cc1NC(=O)c1cncc(C#N)c1] |
| I-457 | 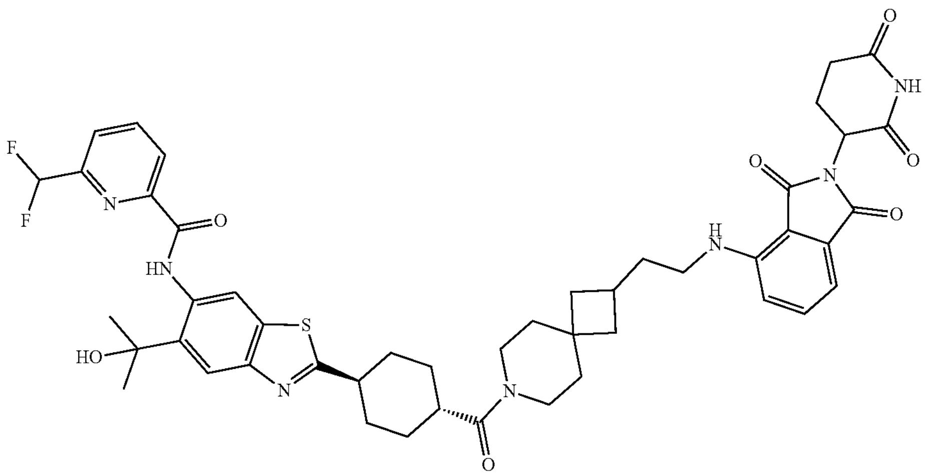 [SMILES: CC(C)(O)c1cc2nc([C@H]3CC[C@H](C(=O)N4CCC5(CC4)CC(CCNc4cccc6c4C(=O)N(C4CCC(=O)NC4=O)C6=O)C5)CC3)sc2cc1NC(=O)c1cccc(C(F)F)n1] |
| I-458 | 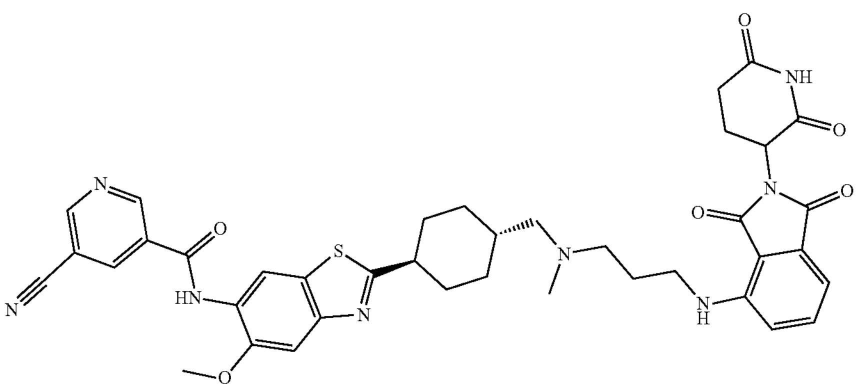 [SMILES: COc1cc2nc([C@H]3CC[C@H](CN(C)CCCNc4cccc5c4C(=O)N(C4CCC(=O)NC4=O)C5=O)CC3)sc2cc1NC(=O)c1cncc(C#N)c1] |
| I-459 | 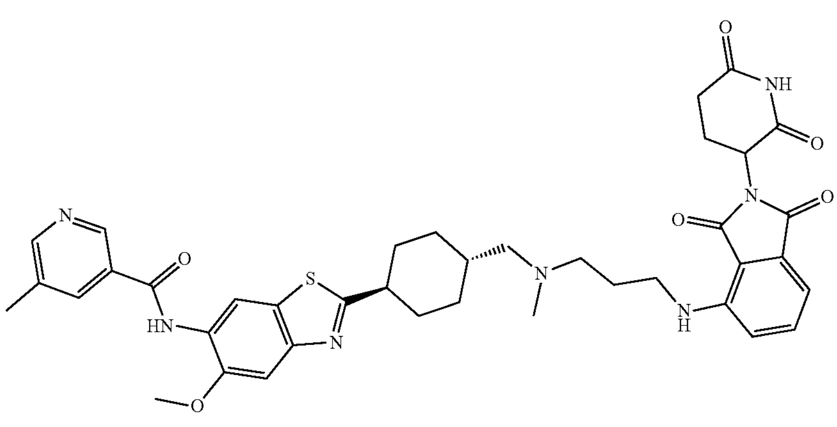 [SMILES: COc1cc2nc([C@H]3CC[C@H](CN(C)CCCNc4cccc5c4C(=O)N(C4CCC(=O)NC4=O)C5=O)CC3)sc2cc1NC(=O)c1cncc(C)c1] |

TABLE 1-continued

Exemplary Compounds

| I-# | Structure |
|---|---|
| I-460 | 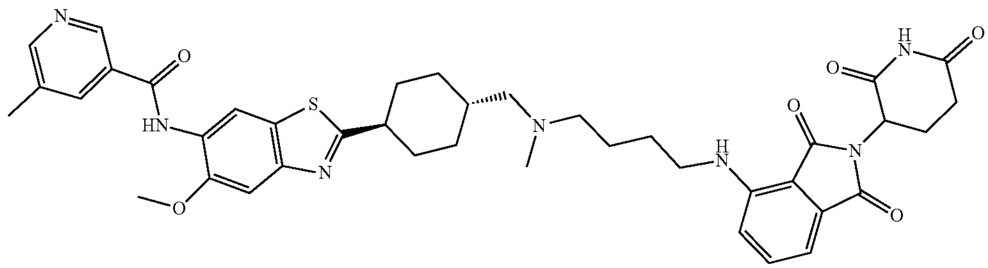 [SMILES: COc1cc2nc([C@H]3CC[C@H](CN(C)CCCCNc4cccc5c4C(=O)N(C4CCC(=O)NC4=O)C5=O)CC3)sc2cc1NC(=O)c1cncc(C)c1] |
| I-461 | 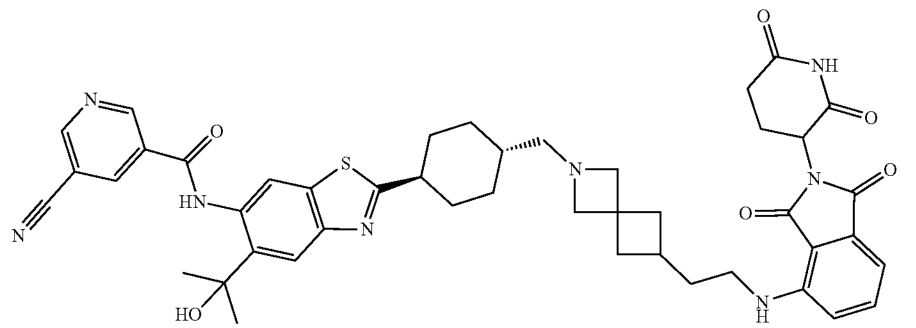 [SMILES: CC(C)(O)c1cc2nc([C@H]3CC[C@H](CN4CC5(CC(CCNc6cccc7c6C(=O)N(C6CCC(=O)NC6=O)C7=O)C5)C4)CC3)sc2cc1NC(=O)c1cncc(C#N)c1] |
| I-462 | 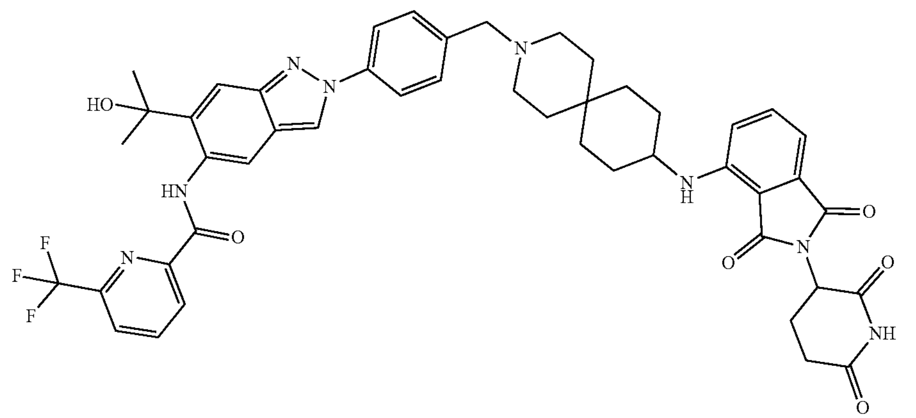 [SMILES: CC(C)(O)c1cc2nn(-c3ccc(CN4CCC5(CCC(Nc6cccc7c6C(=O)N(C6CCC(=O)NC6=O)C7=O)CC5)CC4)cc3)cc2cc1NC(=O)c1cccc(C(F)(F)F)n1] |
| I-463 | 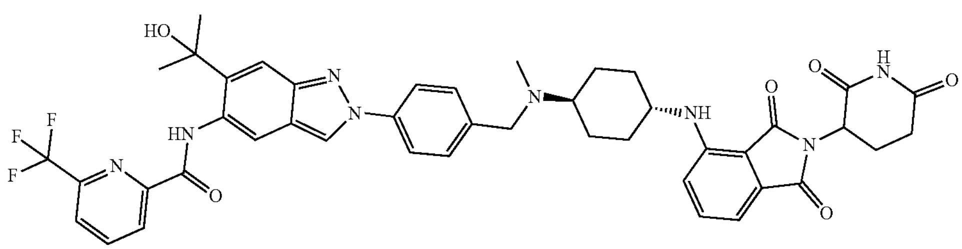 |
| I-464 | 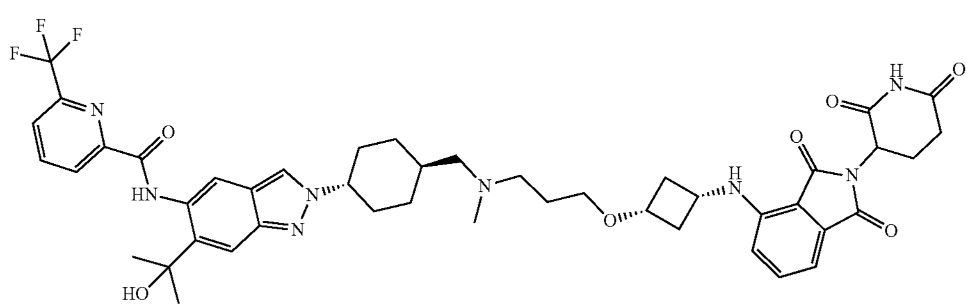 [SMILES: CN(CCCO[C@H]1C[C@@H](Nc2cccc3c2C(=O)N(C2CCC(=O)NC2=O)C3=O)C1)C[C@H]1CC[C@H](n2cc3cc(NC(=O)c4cccc(C(F)(F)F)n4)c(C(C)(C)O)cc3n2)CC1] |

TABLE 1-continued

Exemplary Compounds

| I-# | Structure |
|---|---|
| I-465 | 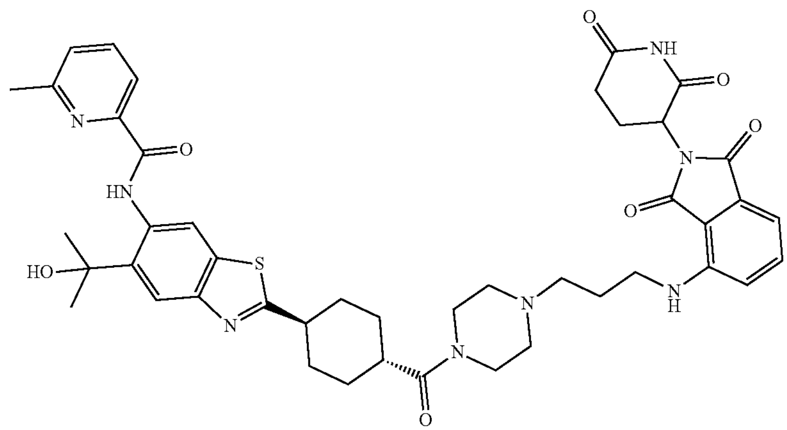 [SMILES: Cc1cccc(C(=O)Nc2cc3sc([C@H]4CC[C@H](C(=O)N5CCN(CCCNc6cccc7c6C(=O)N(C6CCC(=O)NC6=O)C7=O)CC5)CC4)nc3cc2C(C)(C)O)n1] |
| I-466 | 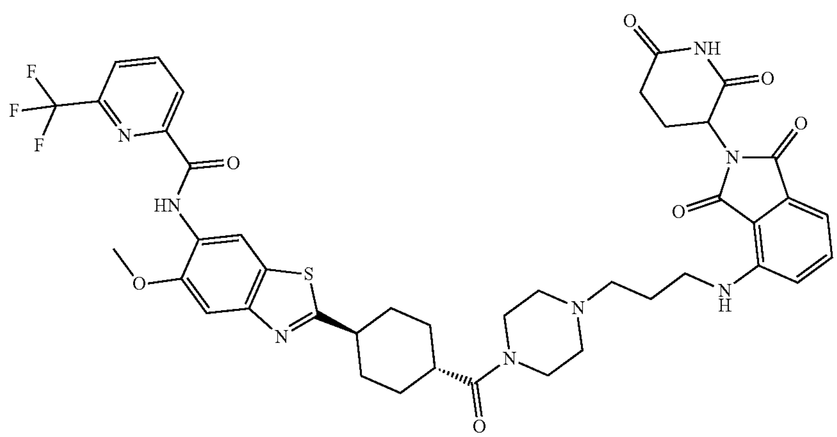 [SMILES: COc1cc2nc([C@H]3CC[C@H](C(=O)N4CCN(CCCNc5cccc6c5C(=O)N(C5CCC(=O)NC5=O)C6=O)CC4)CC3)sc2cc1NC(=O)c1cccc(C(F)(F)F)n1] |
| I-467 | 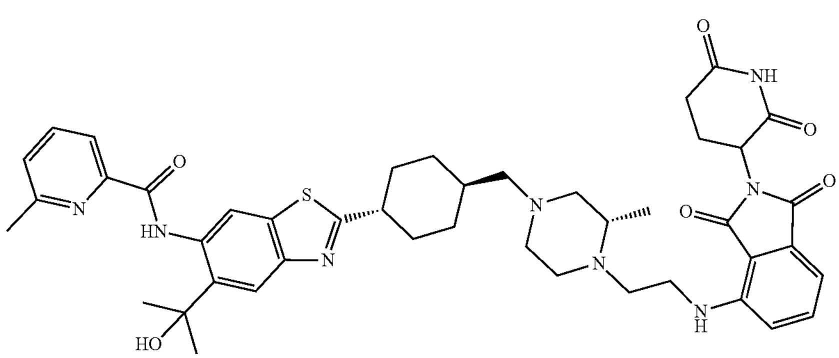 [SMILES: Cc1cccc(C(=O)Nc2cc3sc([C@H]4CC[C@H](CN5CCN(CCNc6cccc7c6C(=O)N(C6CCC(=O)NC6=O)C7=O)[C@@H](C)C5)CC4)nc3cc2C(C)(C)O)n1] |

TABLE 1-continued
Exemplary Compounds
| I-# | Structure |
|---|---|
| I-468 | 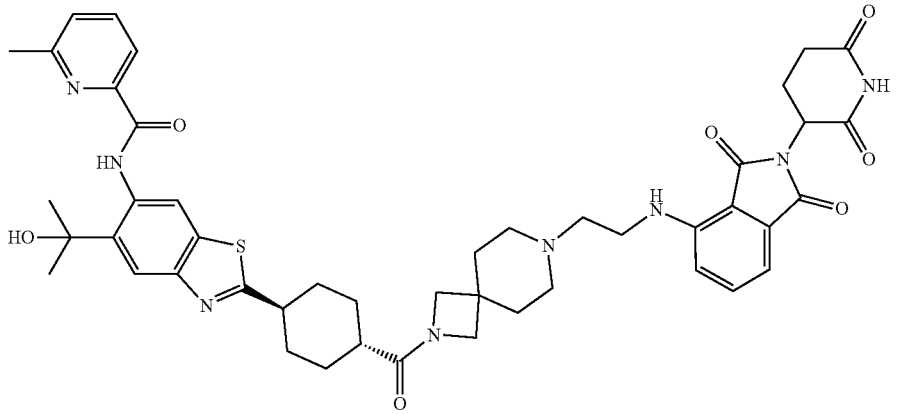 [SMILES: Cc1cccc(C(=O)Nc2cc3sc([C@H]4CC[C@H](C(=O)N5CC6(CCN(CCNc7cccc8c7C(=O)N(C7CCC(=O)NC7=O)C8=O)CC6)C5)CC4)nc3cc2C(C)(C)O)n1] |
| I-469 | 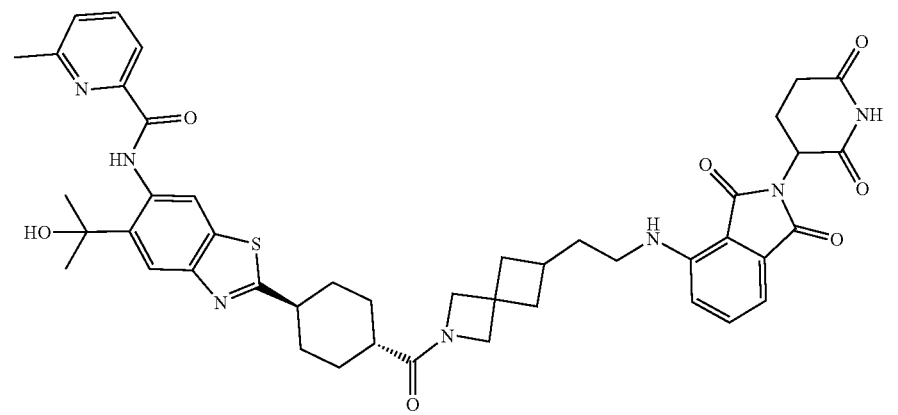 [SMILES: Cc1cccc(C(=O)Nc2cc3sc([C@H]4CC[C@H](C(=O)N5CC6(CC(CCNc7cccc8c7C(=O)N(C7CCC(=O)NC7=O)C8=O)C6)C5)CC4)nc3cc2C(C)(C)O)n1] |
| I-470 | 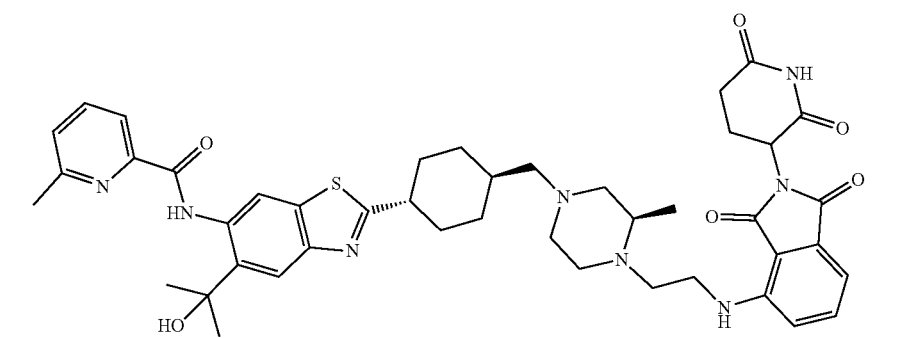 [SMILES: Cc1cccc(C(=O)Nc2cc3sc([C@H]4CC[C@H](CN5CCN(CCNc6cccc7c6C(=O)N(C6CCC(=O)NC6=O)C7=O)[C@H](C)C5)CC4)nc3cc2C(C)(C)O)n1] |

TABLE 1-continued

Exemplary Compounds

| I-# | Structure |
|---|---|
| I-471 | 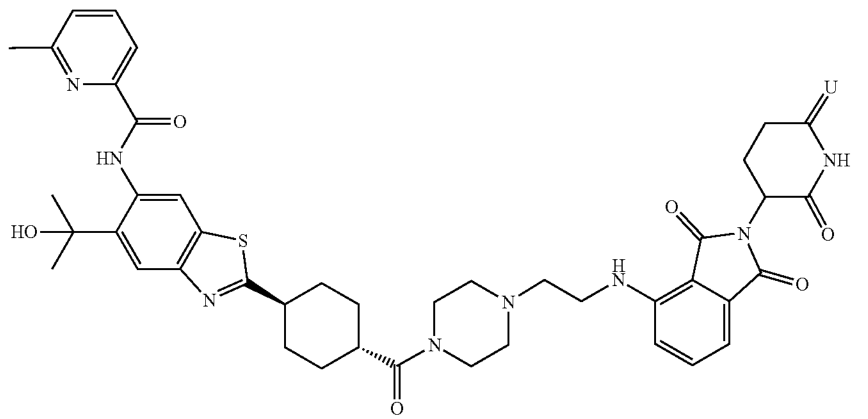 |
| I-472 | 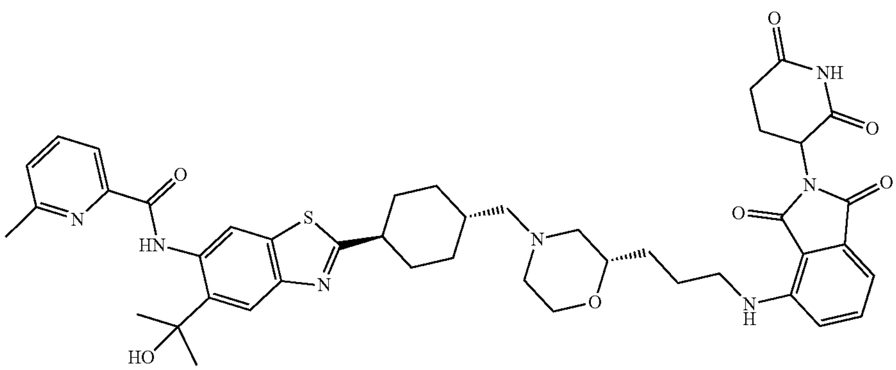 [SMILES: Cc1cccc(C(=O)Nc2cc3sc([C@H]4CC[C@H](CN5CCO[C@@H](CCCNc6cccc7c6C(=O)N(C6CCC(=O)NC6=O)C7=O)C5)CC4)nc3cc2C(C)(C)O)n1] |
| I-473 | 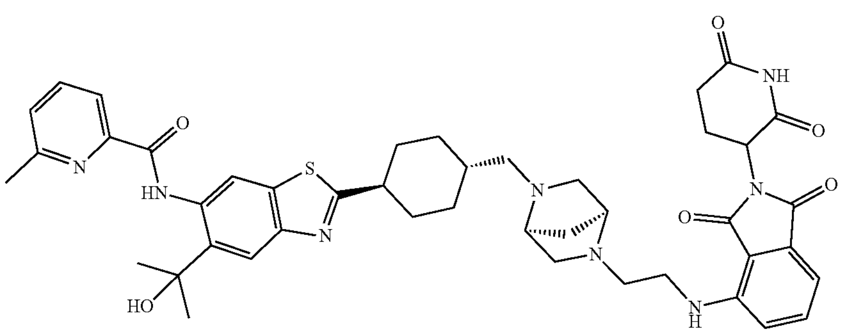 [SMILES: Cc1cccc(C(=O)Nc2cc3sc([C@H]4CC[C@H](CN5C[C@@H]6C[C@H]5CN6CCNc5cccc6c5C(=O)N(C5CCC(=O)NC5=O)C6=O)CC4)nc3cc2C(C)(C)O)n1] |
| I-474 | 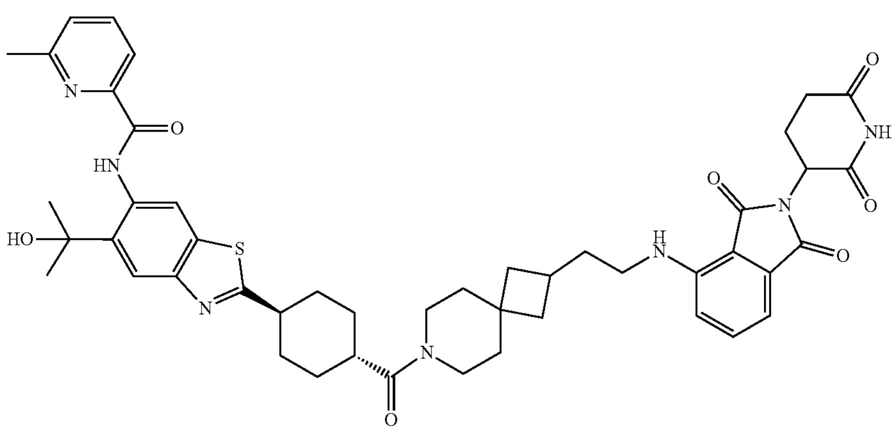 [SMILES: Cc1cccc(C(=O)Nc2cc3sc([C@H]4CC[C@H](C(=O)N5CCC6(CC5)CC(CCNc5cccc7c5C(=O)N(C5CCC(=O)NC5=O)C7=O)C6)CC4)nc3cc2C(C)(C)O)n1] |

TABLE 1-continued
Exemplary Compounds
| I-# | Structure |
|---|---|
| I-475 | 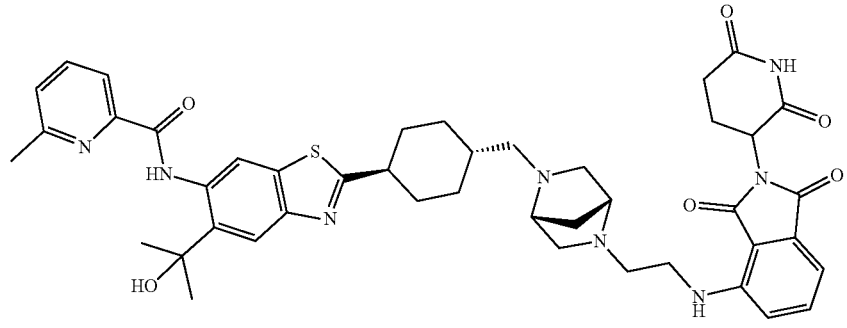 [SMILES: Cc1cccc(C(=O)Nc2cc3sc([C@H]4CC[C@H](CN5C[C@H]6C[C@@H]5CN6CCNc5cccc6c5C(=O)N(C5CCC(=O)NC5=O)C6=O)CC4)nc3cc2C(C)(C)O)n1] |
| I-476 | 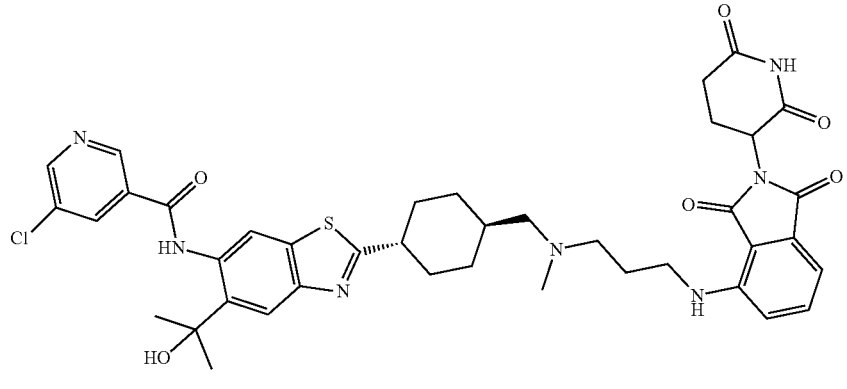 [SMILES: CN(CCCNc1cccc2c1C(=O)N(C1CCC(=O)NC1=O)C2=O)C[C@H]1CC[C@H](c2nc3cc(C(C)(C)O)c(NC(=O)c4cncc(Cl)c4)cc3s2)CC1] |
| I-477 | 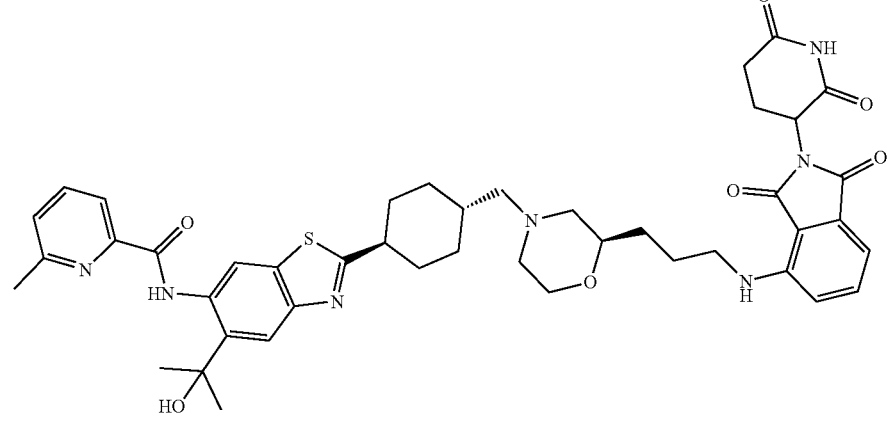 |
| I-478 | 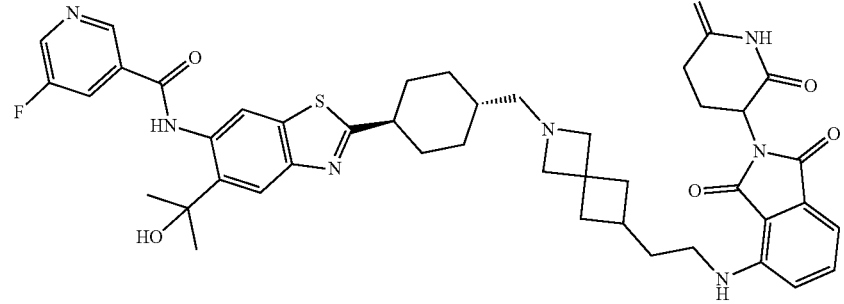 |

TABLE 1-continued
Exemplary Compounds
| I-# | Structure |
|---|---|
| I-479 | 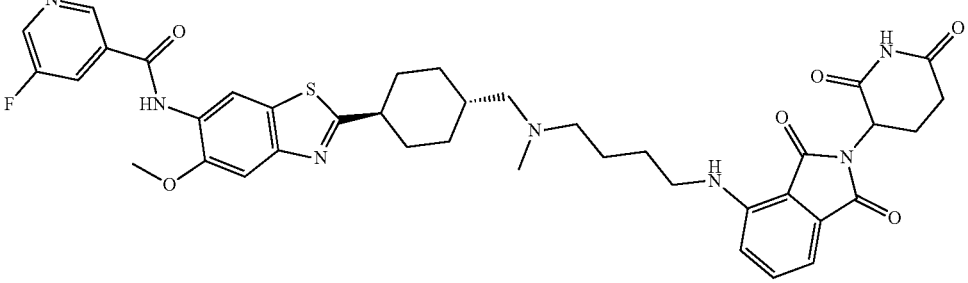 |
| I-480 | 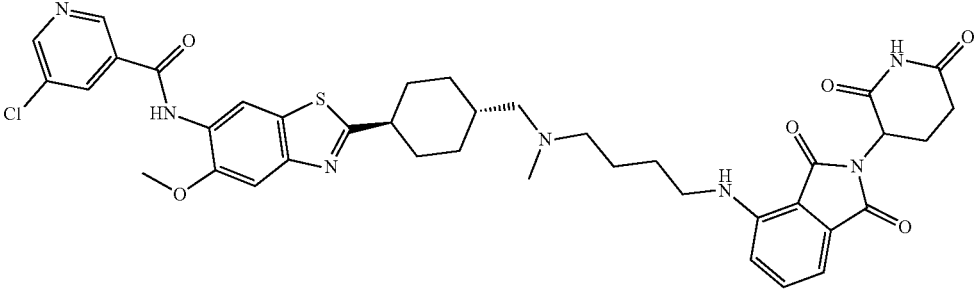 [SMILES: COc1cc2nc([C@H]3CC[C@H](CN(C)CCCCNc4cccc5c4C(=O)N(C4CCC(=O)NC4=O)C5=O)CC3)sc2cc1NC(=O)c1cncc(Cl)c1] |
| I-481 | 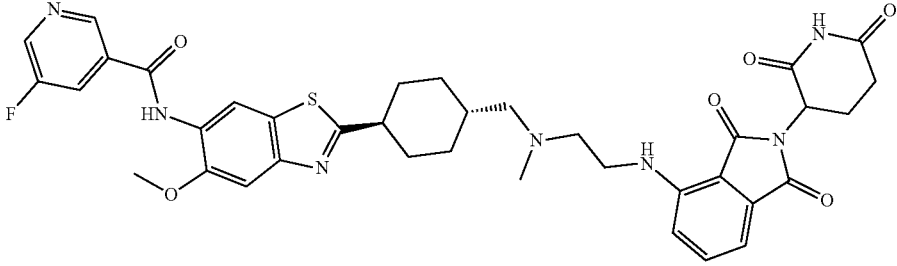 [SMILES: COc1cc2nc([C@H]3CC[C@H](CN(C)CCNc4cccc5c4C(=O)N(C4CCC(=O)NC4=O)C5=O)CC3)sc2cc1NC(=O)c1cncc(F)c1] |
| I-482 | 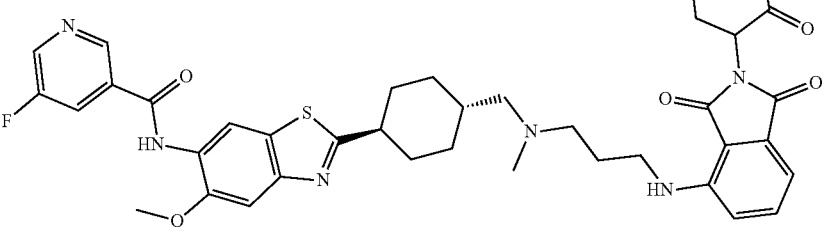 |
| I-483 | 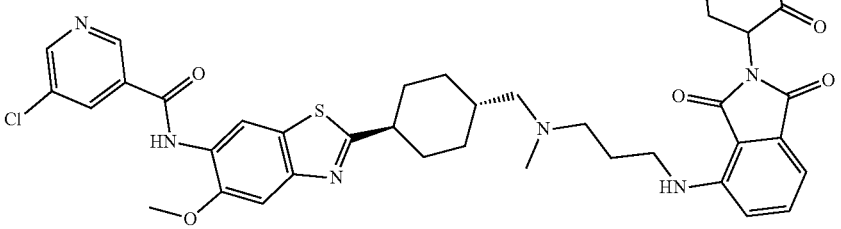 |

TABLE 1-continued

Exemplary Compounds

| I-# | Structure |
|---|---|
| I-484 | 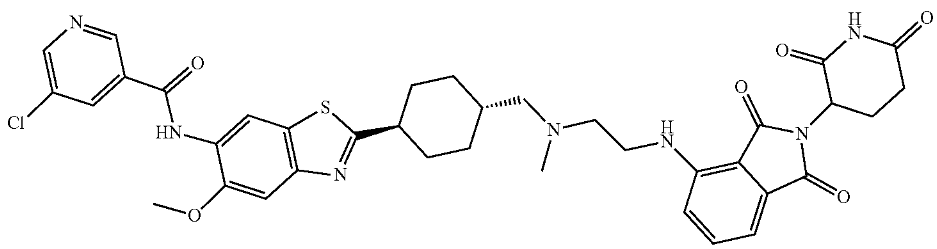 [SMILES: COc1cc2nc([C@H]3CC[C@H](CN(C)CCNc4cccc5c4C(=O)N(C4CCC(=O)NC4=O)C5=O)CC3)sc2cc1NC(=O)c1cncc(Cl)c1] |
| I-485 | 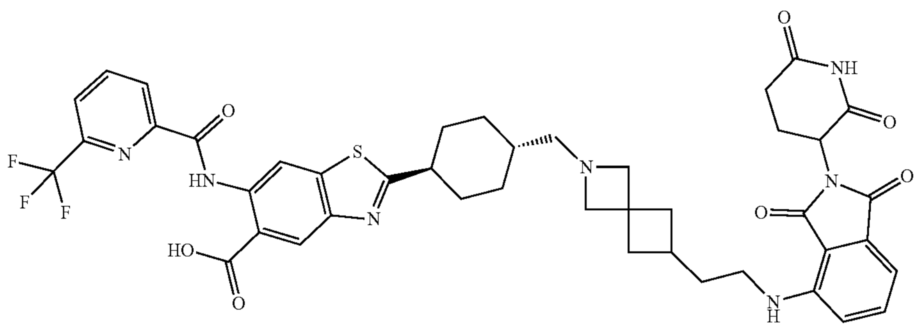 [SMILES: O=C1CCC(N2C(=O)c3cccc(NCCC4CC5(C4)CN(C[C@H]4CC[C@H](c6nc7cc(C(=O)O)c(NC(=O)c8cccc(C(F)(F)F)n8)cc7s6)CC4)C5)c3C2=O)C(=O)N1] |
| I-486 | 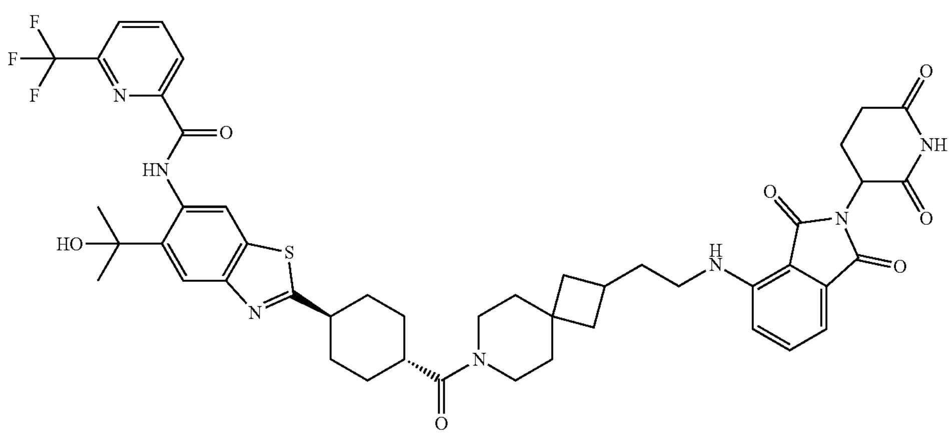 [SMILES: CC(C)(O)c1cc2nc([C@H]3CC[C@H](C(=O)N4CCC5(CC4)CC(CCNc4cccc6c4C(=O)N(C4CCC(=O)NC4=O)C6=O)C5)CC3)sc2cc1NC(=O)c1cccc(C(F)(F)F)n1] |
| I-487 | 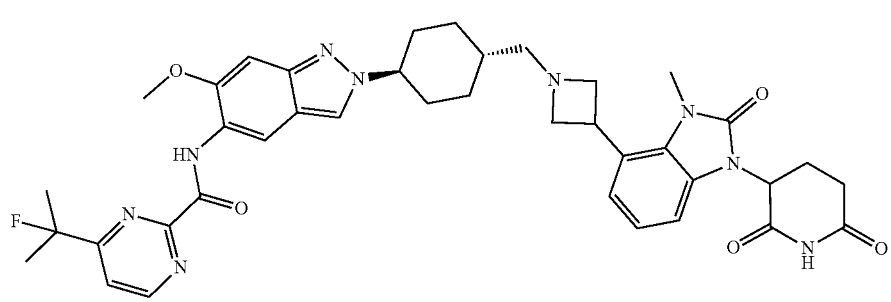 [SMILES: COc1cc2nn([C@H]3CC[C@H](CN4CC(c5cccc6c5n(C)c(=O)n6C5CCC(=O)NC5=O)C4)CC3)cc2cc1NC(=O)c1nccc(C(C)(C)F)n1] |

TABLE 1-continued

Exemplary Compounds

| I-# | Structure |
|---|---|
| I-488 | 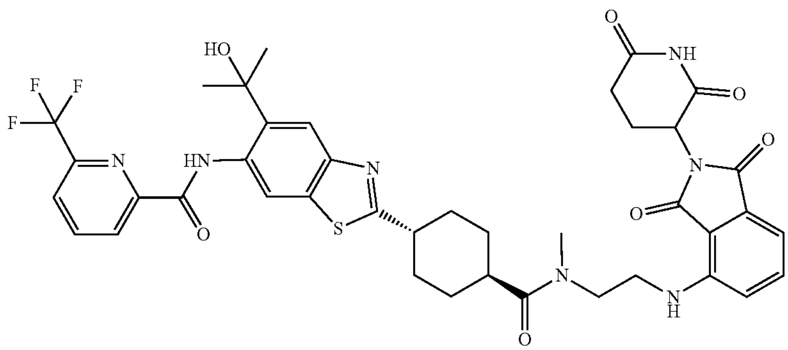 [SMILES: CN(CCNc1cccc2c1C(=O)N(C1CCC(=O)NC1=O)C2=O)C(=O)[C@H]1CC[C@H](c2nc3cc(C(C)(C)O)c(NC(=O)c4cccc(C(F)(F)F)n4)cc3s2)CC1] |
| I-489 | 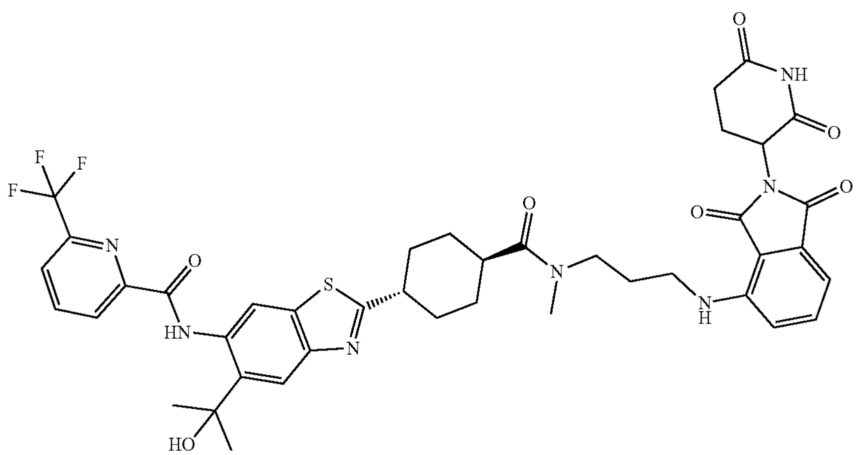 [SMILES: CN(CCCNc1cccc2c1C(=O)N(C1CCC(=O)NC1=O)C2=O)C(=O)[C@H]1CC[C@H](c2nc3cc(C(C)(C)O)c(NC(=O)c4cccc(C(F)(F)F)n4)cc3s2)CC1] |
| I-490 | 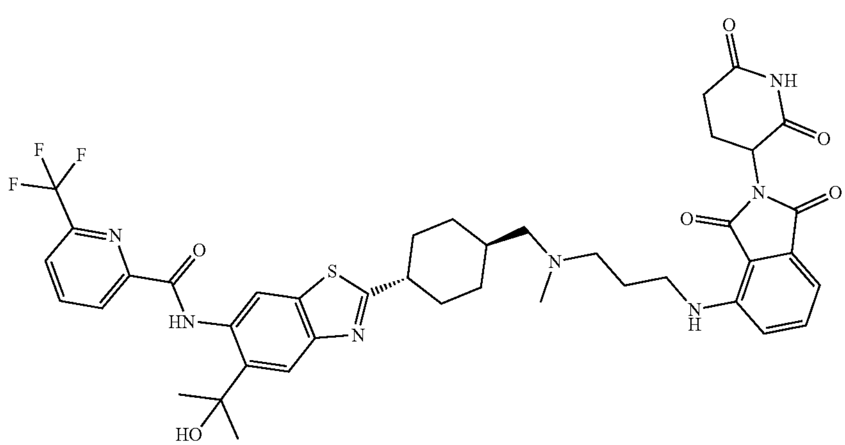 [SMILES: CN(CCCNc1cccc2c1C(=O)N(C1CCC(=O)NC1=O)C2=O)C[C@H]1CC[C@H](c2nc3cc(C(C)(C)O)c(NC(=O)c4cccc(C(F)(F)F)n4)cc3s2)CC1] |

TABLE 1-continued
Exemplary Compounds
| I-# | Structure |
|---|---|
| I-491 | 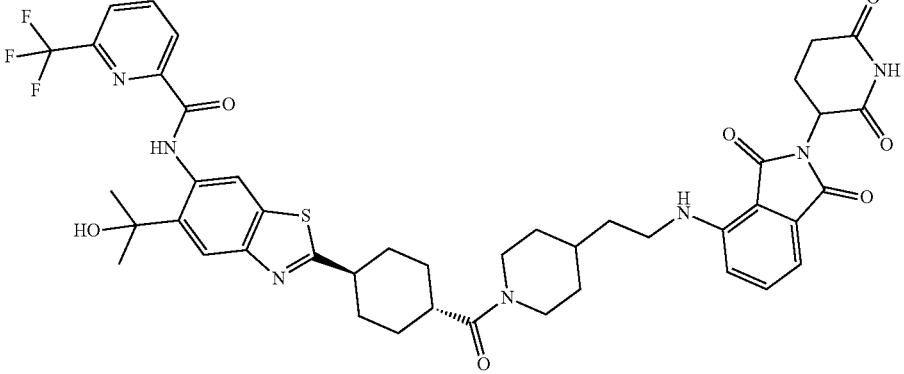 |
| I-492 | 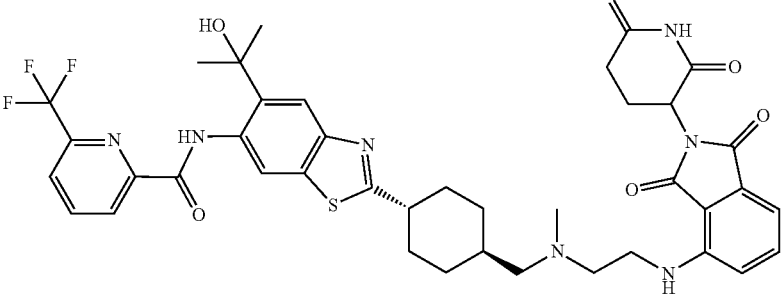 |
| I-493 | 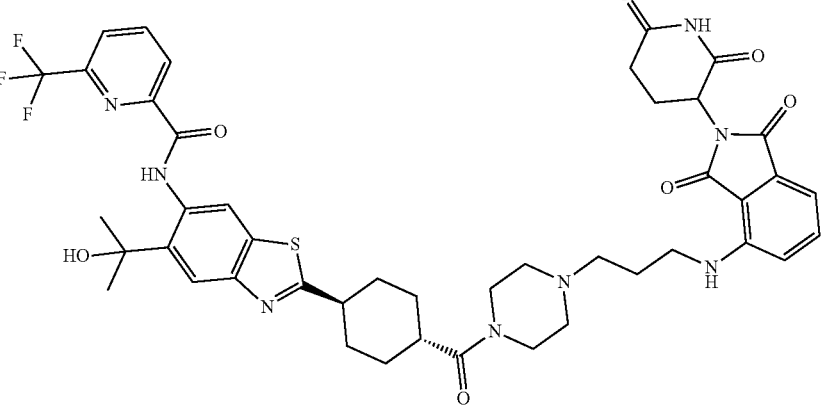 |
In some embodiments, the present invention provides a compound set forth in Table 1, above, or a pharmaceutically acceptable salt thereof.

In some embodiments, the present invention provides a compound that is not one or more of the following:
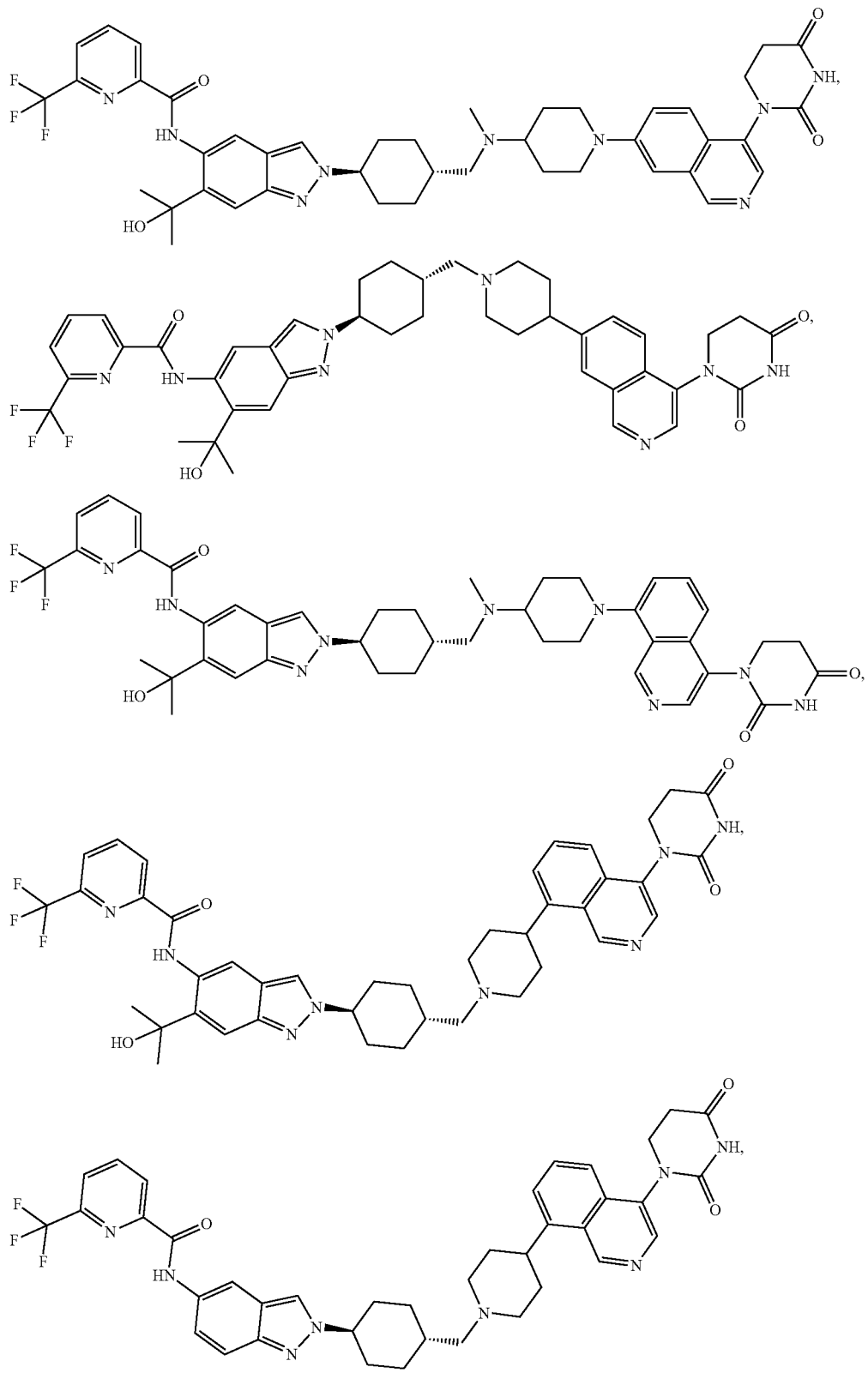

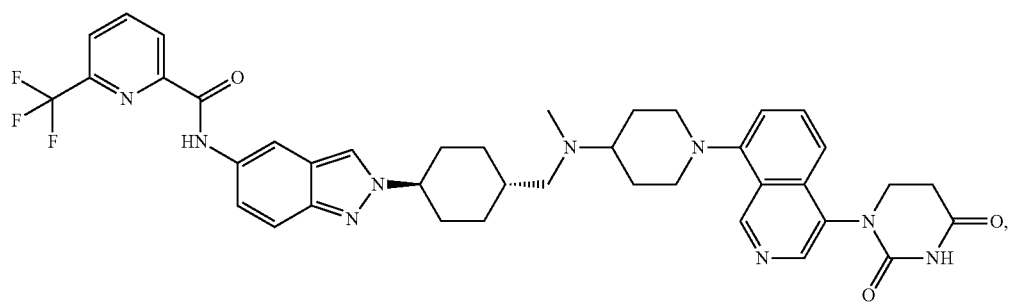
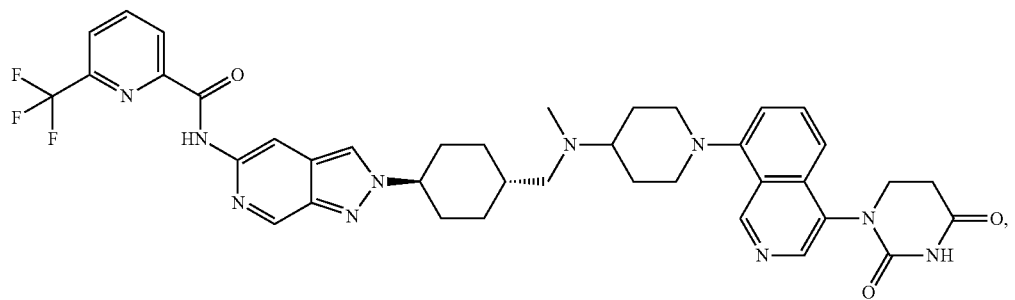
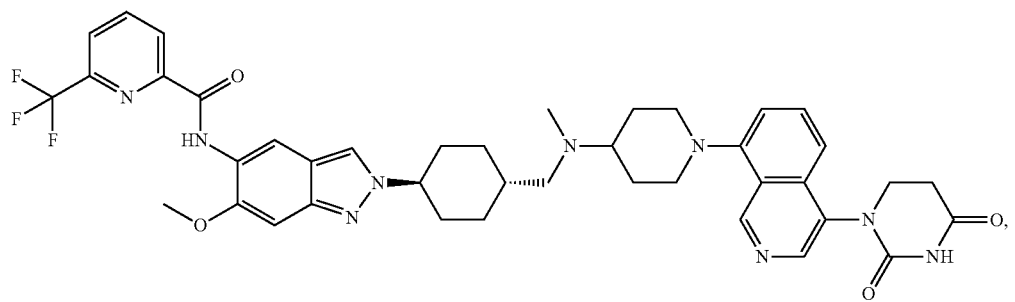
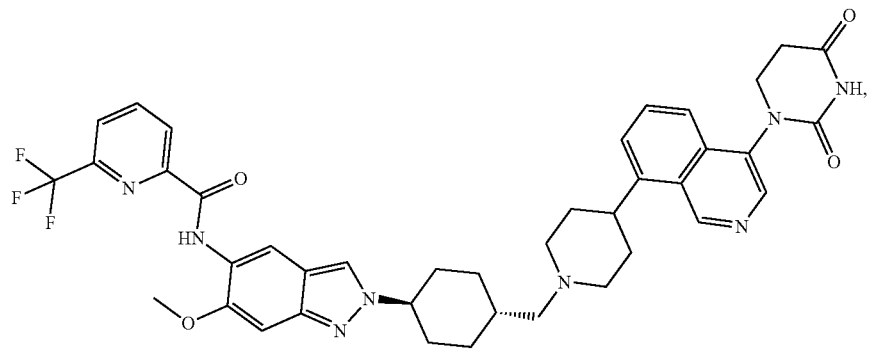
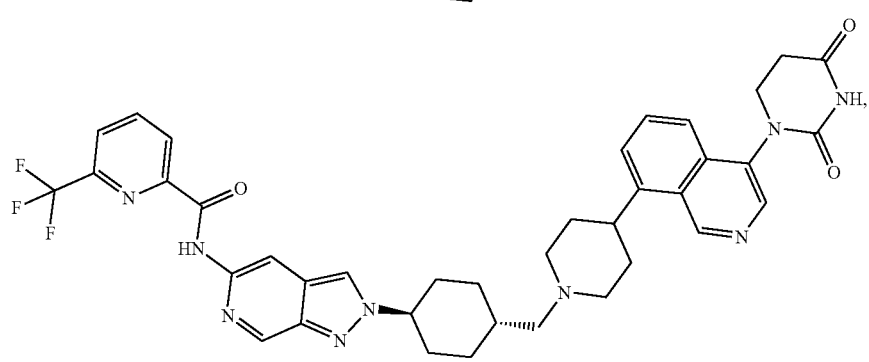

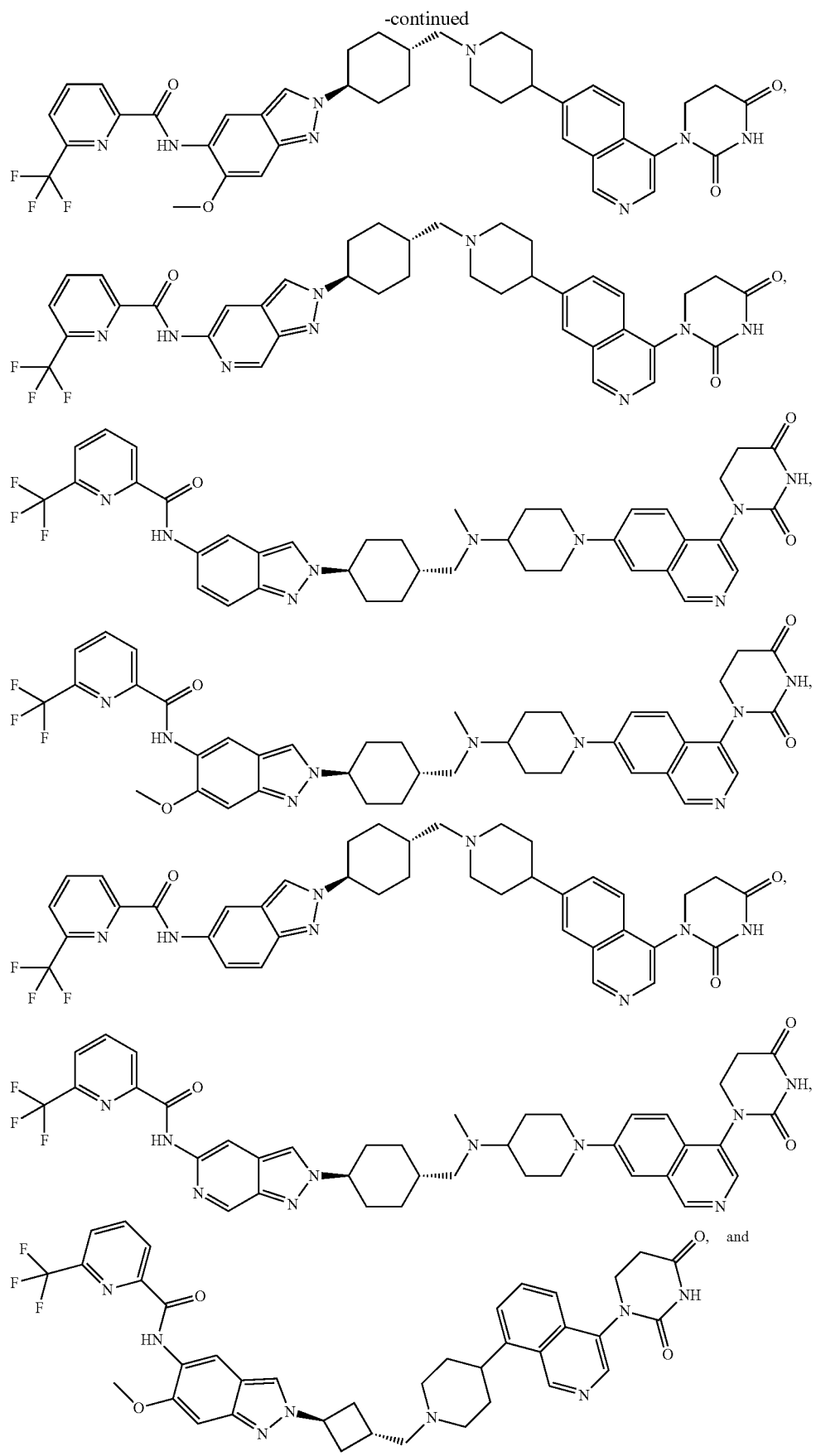

-continued

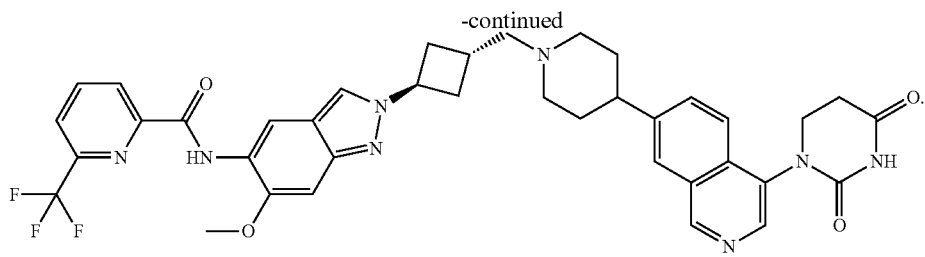

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In the schemes below, where a provided compound is formed having a reactive DIM moiety (e.g., amine, alcohol, etc.), it is not shown but it is generally appreciated and well known by those having ordinary skill in the art that the reactivity of said reactive DIM moiety may be masked by employing a suitable protecting group that can thereafter be removed in situ or during a separate synthetic step.

In certain embodiments, compounds of the present invention are generally prepared according to Scheme 1 set forth below:

Scheme 1: Synthesis of Compounds of the Invention

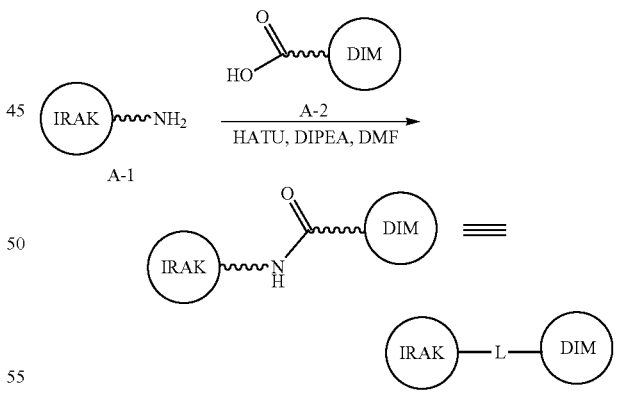

As depicted in Scheme 1, above, amine A-1 is coupled to acid A-2 using the coupling agent HATU in the presence of the base DIPEA in DMF to form a compound of the invention with a linker comprising an amide bond. The squiggly bond, ∿∿, represents the portion of the linker between IRAK and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of the Invention

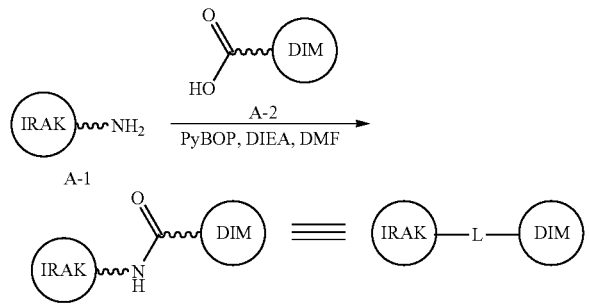

As depicted in Scheme 2, above, amine A-1 is coupled to acid A-2 using the coupling agent PyBOP in the presence of the base DIPEA in DMF to form a compound of the invention with a linker comprising an amide bond. The squiggly bond, ∿∿∿, represents the portion of the linker between IRAK and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of the Invention

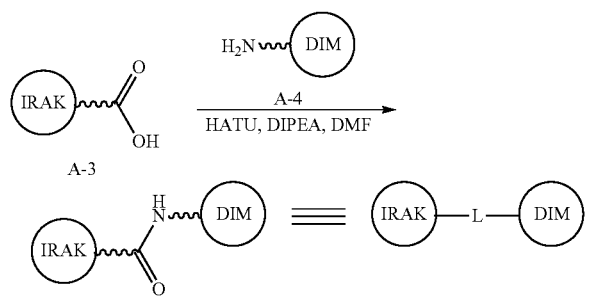

As depicted in Scheme 3, above, acid A-3 is coupled to amine A-4 using the coupling agent HATU in the presence of the base DIPEA in DMF to form a compound of the invention with a linker comprising an amide bond. The squiggly bond, ∿∿∿, represents the portion of the linker between IRAK and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of the Invention

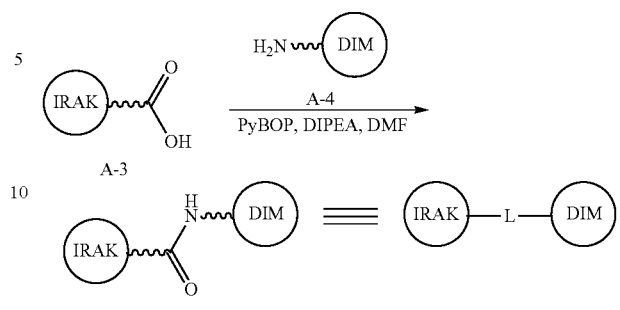

As depicted in Scheme 4, above, acid A-3 is coupled to amine A-4 using the coupling agent PyBOP in the presence of the base DIPEA in DMF to form a compound of the invention with a linker comprising an amide bond. The squiggly bond, ∿∿∿, represents the portion of the linker between IRAK and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of the Invention

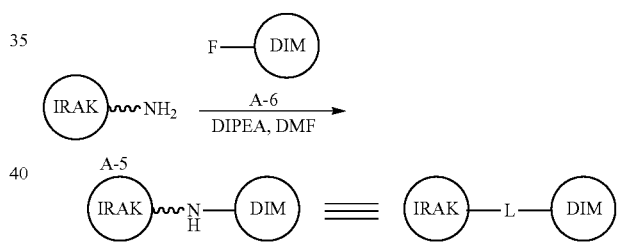

As depicted in Scheme 5, above, an $S_NAr$ displacement of fluoride A-6 by amine A-5 is effected in the presence of the base DIPEA in DMF to form a compound of the invention with a linker comprising a secondary amine. The squiggly bond, ∿∿∿, represents the portion of the linker between IRAK and the terminal amino group of A-5.

In certain embodiments, compounds of the present invention are generally prepared according to Scheme 6 set forth below:

Scheme 6: Synthesis of Compounds of the Invention

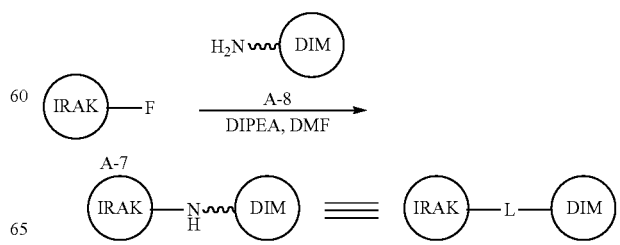

As depicted in Scheme 6, above, an $S_NAr$ displacement of fluoride A-7 by amine A-8 is effected in the presence of the base DIPEA in DMF to form a compound of the invention with a linker comprising a secondary amine. The squiggly bond, ∿, represents the portion of the linker between DIM and the terminal amino group of A-8.

In certain embodiments, compounds of the present invention are generally prepared according to Scheme 7 set forth below:

Scheme 7: Synthesis of Compounds of The Invention

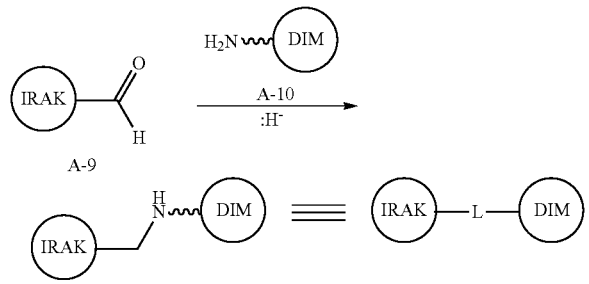

As depicted in Scheme 7, above, reductive alkylation of aldehyde A-9 by amine A-10 is effected in the presence of a mild hydride source (e.g., sodium cyanoborohydride or sodium triacetoxyborohydride) to form a provided compound with a linker comprising a secondary amine. The squiggly bond, ∿, represents the portion of the linker between DIM and the terminal amino group of A-10.

In certain embodiments, compounds of the present invention are generally prepared according to Scheme 8 set forth below:

Scheme 8: Synthesis of Compounds of The Invention

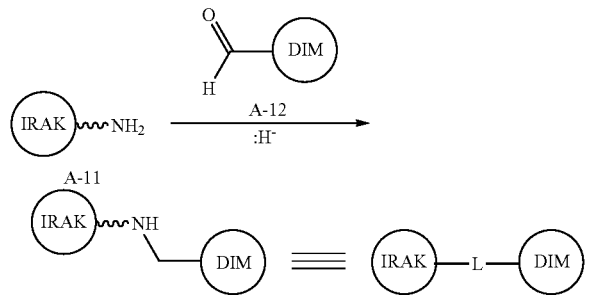

As depicted in Scheme 8, above, reductive alkylation of aldehyde A-12 by amine A-11 is effected in the presence of a mild hydride source (e.g., sodium cyanoborohydride or sodium triacetoxyborohydride) to form a provided compound with a linker comprising a secondary amine. The squiggly bond, ∿, represents the portion of the linker between IRAK and the terminal amino group of A-11.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See for example, "March's Advanced Organic Chemistry", $5^{th}$ Ed., Ed.: Smith, M. B. and March, J., John Wiley & Sons, New York: 2001, the entirety of each of which is herein incorporated by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that it is effective to measurably degrade and/or inhibit an IRAK protein kinase, or a mutant thereof, in a biological sample or in a patient. In certain embodiments, the amount of compound in compositions of this invention is such that it is effective to measurably degrade and/or inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of an IRAK protein kinase, or a mutant thereof.

As used herein, the term "degratorily active metabolite or residue thereof" means that a metabolite or residue thereof is also a degrader of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of kinase activity of one or more enzymes.

Examples of kinases that are degraded and/or inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase,"*PNAS* 2002, 99(8), 5567-5572, Flannery et al., "The interleukin-1 receptor-associated kinases: Critical regulators of innate immune signaling" Biochem Pharm 2010, 80(12), 1981-1991 incorporated by reference in its entirety.

The activity of a compound utilized in this invention as a degrader and/or inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204(5), 1025-1036; Lebakken et al., "A Fluorescence Lifetime Based Binding Assay to Characterize Kinase Inhibitors," *J. Biomol. Screen.* 2007, 12(6), 828-841; Maschera et al., "Overexpression of an enzymatically inactive interleukin-1-receptor-associated kinase activates nuclear factor-KB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, each of, the entirety of each of which is herein incorporated by reference. Detailed conditions for assaying a compound utilized in this invention as a degrader and/or inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medicine (Baltimore)*, 2010, 89(6), 043-25; Li, "IRAK4 in TLR/IL-1R signaling: Possible clinical applications," *Eur J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80(12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J. Exp. Med.* 2007 204(5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282(18), 13552-13560; Kubo-Murai et al., "IRAK-4-dependent Degradation of IRAK-1 is a Negative Feedback Signal for TLR-mediated NF-κB Activation," *J. Biochem.* 2008, 143, 295-302; Maschera et al., "Overexpression of an enzymatically inactive interleukin-1-receptor-associated kinase activates nuclear factor-KB," *Biochem. J.* 1999, 339, 227-231; Lin et al., "Helical assembly in the MyD88-IRAK4-IRAK2 complex in TLR/IL-1R signalling," *Nature* 2010, 465(17), 885-891; Suzuki et al., "IRAK-4 as the central TIR signaling mediator in innate immunity," *TRENDS in Immunol.* 2002, 23(10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), each of, the entirety of each of which is herein incorporated by reference. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204(10), 2407-

2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets,* 12(7), pp: 883-903 (2008); Gearing, A. "Targeting toll-like receptors for drug development: a summary of commercial approaches," *Immunology and Cell Biology,* 85, pp: 490-494 (2007); Dinarello, C. "IL-1: Discoveries, controversies and future directions," *European Journal of Immunology,* 40, pp: 595-653 (2010), each of, the entirety of each of which is herein incorporated by reference. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wang et al., "IRAK-4 Inhibitors for Inflammation," *Curr. Topics in Med. Chem.* 2009, 9, 724-737, each of, the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 1β-Induced Interleukin 6 Production and the Myeloma Proliferative Component," *Mayo Clinic Proceedings,* 84(2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of anti-inflammatory drugs," *Curr Opin. Cell Bio.* 2009, 21:317-324) and rheumatoid arthritis (see, e.g., Geyer, M. et al., "Actual status of antiinterleukin-1 therapies in rheumatic diseases," *Current Opinion in Rheumatology,* 22, pp: 246-251 (2010)), auto-inflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.,* 14, pp: 411-421 (2008)), inflammation (see, e.g., Dinarello, C. "Interleukin 1 and interleukin 18 as mediators of inflammation and the aging process," *The American Journal of Clinical Nutrition,* 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases,* 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomized, single-blind pilot study," *Annals of Rheumatic Diseases,* 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases,* 68, pp: 1602-1608 (2009)), neurological disorders, metabolic syndrome (see, e.g., Troseid, M. "The role of interleukin-18 in the metabolic syndrome," *Cardiovascular Diabetology,* 9:11, pp: 1-8 (2010)), immunodeficiency disorders such as AIDS and HIV (see, e.g., Iannello, A. et al., "Role of Interleukin-18 in the Development and Pathogenesis of AIDS," *AIDS Reviews*, 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" 53$^{rd}$ ASH Annual Meeting; Xu, et al., "A somatic variant in MYD88 (L256P) revealed by whole genome sequencing differentiates lymphoplasmacytic lymphoma from marginal zone lymphomas" 53$^{rd}$ ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53" ASH Annual Meeting; Iriyama et al., "Clinical significance of genetic mutations of CD79B, CARD11, MYD88, and EZH2 genes in diffuse large B-cell lymphoma patients" 53' ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit IRAK-1 only, IRAK-2-only, IRAK-4-only and/or IRAK1 and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma).

In some embodiments the proliferative disease which can be treated according to the methods of this invention is an MyD88 driven disorder. In some embodiments, the MyD88 driven disorder which can be treated according to the methods of this invention is selected from ABC DLBCL, Waldenström's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example anti-inflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, muscle wasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitis, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, systemic juvenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from systemic lupus erythematosus, multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the present invention provides a method of treating hidradenitis suppurativa in a patient in need thereof, comprising administering a compound of the present invention, or a pharmaceutically acceptable salt thereof.

In some embodiments, the present invention provides a method of treating atopic dermatitis in a patient in need thereof, comprising administering a compound of the present invention, or a pharmaceutically acceptable salt thereof.

In some embodiments, the present invention provides a method of treating rheumatoid arthritis in a patient in need thereof, comprising administering a compound of the present invention, or a pharmaceutically acceptable salt thereof.

In some embodiments, the present invention provides a method of treating solid and liquid tumors in a patient in need thereof, comprising administering a compound of the present invention, or a pharmaceutically acceptable salt thereof.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased Aβ levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32(43), 15112-15123.

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Multiple Degradation

In some embodiments, the invention provides compounds that modulate targeted ubiquitination and degradation of one or more IRAK kinase. In some embodiments, a provided compound modulates targeted ubiquitination and degradation of one or more IRAK kinase and one or more additional protein. In some instances, a provided compound modulates targeted ubiquitination and degradation of IRAK4 and one, two, three, four, or five additional proteins.

In certain embodiments, the invention provides compounds that are triple degraders. In certain embodiments, the invention provides compounds that combine IRAK kinase degradation with IKZF1 and IKZF3 degradation. Some of the most commonly employed E3 ligase ligands are thalidomide and its derivatives, lenalidomide and pomalidomide, commonly referred to as IMiDs (immunomodulatory imide drugs). These agents are small-molecule ligands of cereblon (CRBN) (Ito et al. "Identification of a primary target of thalidomide teratogenicity" Science 2010, 327(5971):1345-1350), a substrate adaptor for the ubiquitously expressed cullin ring ligase 4 (CUL4)-RBX1-DDB1-CRBN (CUL4CRBN) E3 ligase. It has been shown that thalidomide interacts with CRBN to form a novel surface, resulting in interactions with neosubstrates such as Ikaros (IKZF1) and Aiolos (IKZF3) and their ubiquitination and subsequent proteasomal degradation (Krönke et al. "Lenalidomide causes selective degradation of IKZF1 and IKZF3 in multiple myeloma cells" Science 2014, 343(6168):301-305; and Lu et al. "The myeloma drug lenalidomide promotes the cereblon-dependent destruction of Ikaros proteins" Science, 2014; 343(6168):305-309). This activity alone has potent antitumor effects in some liquid malignancies, and lenalidomide (Revlimid®) is US Food and Drug Administration approved for the treatment of MCL, multiple myeloma, and myelodysplastic syndromes with deletion of chromosome Sq. Lenalidomide is also undergoing late-stage clinical trials for a number of lymphomas, including MCL and the activated B-cell subtype of diffuse large B-cell lymphoma (ABC DLBCL).

In some instances, degradation of IRAK4 alone is not sufficient to kill the MYD88 L265P mutant DLBCL cell line OCI-LY10 either in vitro or as a flank xenograft in vivo. In some embodiments, a non-IMiD-based degraders effects IRAK degradation in MYD88 mutant ABC DLBCL cell line tumor xenografts but without causing regression. This is consistent with literature demonstrating no effect on growth of OCI-LY10 or other MYD88 mutant lines when the gene encoding IRAK4 is removed at the DNA level using CRISPR/Cas9 editing (Phelan et al. "A multiprotein supercomplex controlling oncogenic signaling in lymphoma" Nature, 2018, 7718:387-391).

It has been shown that activating MYD88 mutations increase production of beta-IFN, a pro-apoptotic cytokine, in ABC-DLBCL cells (Yang et al. "Exploiting synthetic lethality for the therapy of ABC diffuse large B cell lymphoma" Cancer Cell 2012, 21(6):723-737). The cells are rendered resistant to this effect by a concomitant MYD88-driven activation of NFkB signaling via IRF4 and SPIB transactivating CARD11 (Yang, Cancer Cell 2012). IMiDs are also known to increase the IFN response in MYD88 mutant ABC-DLBCL to levels sufficient to increase apoptosis (Yang, Cancer Cell 2012; and Hagner et al. "CC-122, a pleiotropic pathway modifier, mimics an interferon response and has antitumor activity in DLBCL" Blood 2015, 126: 779-789). This effect has been shown to synergize with inhibition of NFkB signaling to further drive DLBCL cell death (Yang, Cancer Cell 2012).

In some instances, the combination of an IMiD with a small molecule IRAK4 kinase inhibitor shows little to no additive effect on viability of the MYD88 mutant ABC DLBCL cell lines, such as OCI-LY10. In some embodiments, the combination of an IRAK4 inhibitor with IMiD is less active than an all-in-one IMiD-based IRAK4 degrader.

In certain embodiments, the combination of IRAK kinase degradation with IKZF1 and IKZF3 degradation in an all-in-one IMiD-based IRAK4 degrader shows potent, single agent activity versus MYD88 mutant ABC DLBCL cell lines in vitro and OCI-LY10 xenograft in vivo. In some embodiments, an all-in-one combination of an IMiD-based CRBN-binder and an IRAK4 binding moiety yields IRAK4 degraders that retain degradation of Ikaros (IKZF1) and other known IMiDs neosubstrates, while more strongly inducing an interferon response compared to pomalidomide alone. In some embodiments, IMiD-based IRAK4 degraders are potent at killing MYD88 mutant ABD-DLBCL cell lines in vitro, demonstrating increased activity versus that obtained from combining an IRAK4 inhibitor with IMiDs as single agents.

In certain embodiments, a provided compound comprising an IMiD-based E3 ligase degrades IRAK4, Ikaros, and Aiolos in MYD88 mutant ABC DLBCL cell line xenografts in vivo, and strongly induces a signature of interferon-driven proteins exemplified by IFIT1 (interferon-inducible transcript 1) and IFIT3 (interferon-inducible transcript 3). In some embodiments, a provided compound comprising an IMiD-based E3 ligase drives regression of tumor xenografts as a single agent.

In some embodiments, the provided compounds of present invention highlight a synergy obtained by combining IRAK4 degradation with IMiD induction of interferon response to drive single agent anti-tumor activity in MYD88 mutant DLBCL and possibly in other heme malignancies. In certain embodiments, a provided compound comprising an IMiD-based E3 ligase degrade IRAK4, Ikaros, and Aiolos acts synergistically. In some embodiments, a provided compound comprising an IRAK4 binder and an IMiD-based E3 ligase degrades IRAK4, Ikaros, and Aiolos with increased activity in comparison to a provided compound comprising the same IRAK4 binder and a non-IMiD-based E3 ligase and the same IMiD-based E3 ligase as a single agent.

In some embodiments, the present invention provides a method of treating MYD88-mutant Waldenstrom macroglobulinemia in a patient in need thereof, comprising administering a compound of the present invention, or a pharmaceutically acceptable salt thereof.

In some embodiments, the present invention provides a method of treating a AML, or a subset thereof, in a patient in need thereof, comprising administering a compound of the present invention, or a pharmaceutically acceptable salt thereof.

In some embodiments, the present invention provides a method of treating NSCLC in a patient in need thereof, comprising administering a compound of the present invention, or a pharmaceutically acceptable salt thereof.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound or a pharmaceutically acceptable salt thereof and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Araya®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Araya®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound or a pharmaceutically acceptable salt thereof and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound or a pharmaceutically acceptable salt thereof and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Uniphyl®, Theo-24®) and aminophylline, and IgE antibodies such as omalizumab (Xolair®).

In some embodiments, the present invention provides a method of treating COPD comprising administering to a patient in need thereof a provided compound or a pharmaceutically acceptable salt thereof and one or more additional therapeutic agents selected from beta-2 agonists such as albuterol (Ventolin® HFA, Proventil® levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a provided compound or a pharmaceutically acceptable salt thereof and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a provided compound or a pharmaceutically acceptable salt thereof and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In some embodiments, the present invention provides a method of treating DLBCL comprising administering to a patient in need thereof a provided compound or a pharmaceutically acceptable salt thereof and a CHOP (cyclophosphamide, Hydrodaunorubicin®, Oncovin®, and prednisone or prednisolone) or R-CHOP (rituximab, cyclophosphamide, Hydrodaunorubicin®, Oncovin®, and prednisone or prednisolone) chemotherapy regimen.

In some embodiments, the present invention provides a method of treating DLBCL comprising administering to a patient in need thereof a provided compound or a pharmaceutically acceptable salt thereof and a rituximab/bendamustine chemotherapy regimen.

In some embodiments, the present invention provides a method of treating DLBCL comprising administering to a patient in need thereof a provided compound or a pharmaceutically acceptable salt thereof and a BTK inhibitor (e.g., ibrutinib).

In some embodiments, the present invention provides a method of treating DLBCL comprising administering to a patient in need thereof a provided compound or a pharmaceutically acceptable salt thereof and an anti-CD20 antibody (e.g., rituximab).

In some embodiments, the present invention provides a method of treating DLBCL comprising administering to a patient in need thereof a provided compound or a pharmaceutically acceptable salt thereof and an anti-CD79B ADC (e.g., polatuzumab).

In some embodiments, the present invention provides a method of treating DLBCL comprising administering to a patient in need thereof a provided compound or a pharmaceutically acceptable salt thereof and a BCL2 inhibitor (e.g., venetoclax).

In some embodiments, the present invention provides a method of treating DLBCL comprising administering to a patient in need thereof a provided compound or a pharmaceutically acceptable salt thereof and lenalidomide In some embodiments, the present invention provides a method of treating DLBCL comprising administering to a patient in need thereof a provided compound or a pharmaceutically acceptable salt thereof and a PI3K inhibitor (e.g., umbralisib).

In some embodiments, the present invention provides a method of treating a T-cell disease or deficiency describing herein comprising administering to a patient in need thereof a provided compound or a pharmaceutically acceptable salt thereof and a PI3K inhibitor (e.g., umbralisib).

In some embodiments, the present invention provides a method of treating DLBCL comprising administering to a patient in need thereof a provided compound or a pharmaceutically acceptable salt thereof and a proteasome inhibitor (e.g., bortezomib)

In some embodiments, the present invention provides a method of treating a T-cell disease or deficiency describing herein comprising administering to a patient in need thereof a provided compound or a pharmaceutically acceptable salt thereof and a protesome inhibitor (e.g., bortezomib).

In another embodiment, the present invention provides a method of treating multiple myeloma comprising administering to a patient in need thereof a provided compound or a pharmaceutically acceptable salt thereof and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a provided compound or a pharmaceutically acceptable salt thereof and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap".

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

In some embodiments, the present invention provides a method of treating Alzheimer's disease comprising administering to a patient in need thereof a provided compound or a pharmaceutically acceptable salt thereof and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound or a pharmaceutically acceptable salt thereof and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound or a pharmaceutically acceptable salt thereof and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degrading a protein kinase in a biological sample comprising the step of contacting said biological sample with a compound of this invention, or a composition comprising said compound.

According to another embodiment, the invention relates to a method of inhibiting or degrading IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Inhibition and/or degradation of a protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™) The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bch 2/Bcl-xL inhibitors (Infinity Pharmaceuticals/Novartis Pharmaceuticals), Genasense (G3139), HA14-1 (and analogs thereof; see WO 2008/118802, US 2010/0197686), navitoclax (and analogs thereof, see U.S. Pat. No. 7,390, 799), NH-1 (Shenayng Pharmaceutical University), obatoclax (and analogs thereof, see WO 2004/106328, US 2005/0014802), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from Parke Davis; or dasatinib (BM S -354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, $C_{1-1033}$, EKB-569, GW-2016, E1.1, E2.4, E2.5, E6.2, E6.4, E2.11, E6.3 or E7.6.3, and 7H-pyrrolo[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO 2008/039218, US 2008/0108636 and WO 2011/090760, US 2010/0249092, the entirety of each of which is herein incorporated by reference.

Further examples of SYK inhibitory compounds, and conditions treatable by such compounds in combination with compounds of this invention can be found in WO 2003/063794, US 2004/0029902, WO 2005/007623, US 2005/0075306, and WO 2006/078846, US 2006/0211657, the entirety of each of which is herein incorporated by reference.

Further examples of PI3K inhibitory compounds, and conditions treatable by such compounds in combination with compounds of this invention can be found in WO 2004/019973, US 2004/0106569, WO 2004/089925, US 2004/0242631, U.S. Pat. No. 8,138,347, WO 2002/088112, US 2004/0116421, WO 2007/084786, US 2010/0249126, WO 2007/129161, US 2008/0076768, WO 2006/122806, US 2008/0194579, WO 2005/113554, US 2008/0275067, and WO 2007/044729, US 2010/0087440, the entirety of each of which is herein incorporated by reference.

Further examples of JAK inhibitory compounds, and conditions treatable by such compounds in combination with compounds of this invention can be found in WO 2009/114512, US 2009/0233903, WO 2008/109943, US 2010/0197671, WO 2007/053452, US 2007/0191405, WO 2001/0142246, US 2001/0053782, and WO 2007/070514, US 2007/0135461, the entirety of each of which is herein incorporated by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2′-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/070024, US 2011/0165156, WO 2011/107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MEDI4736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BM5-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BM5-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/053941, WO 2009/132238, US 2011/136796, WO 2011/056652, US 2012/277217, WO 2012/142237, US 2014/066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARS link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/cOresults?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+(\alpha\beta)$ T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLS-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, —Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF- 8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron -4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
"BuOH: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
Met iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-methylmorphohne N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations were performed under reduced pressure, preferably between about 15 mm Hg and 100 mm Hg (=20-133 mbar). The structure of final products, intermediates and starting materials was confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention were either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions were carried out under nitrogen or argon unless otherwise stated.

Proton NMR ($^1$H NMR) was conducted in deuterated solvent. In certain compounds disclosed herein, one or more $^1$H shifts overlap with residual proteo solvent signals; these signals have not been reported in the experimental provided hereinafter.

TABLE 2

Analytical instruments

| | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase are used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % NH$_3$·H$_2$O in water (solvent A) and acetonitrile (solvent B).

HPLC Analytical Method: HPLC was carried out on X Bridge C18 150*4.6 mm, 5 micron. Column flow is 1.0 ml/min and mobile phase are used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19)mm, 5µ. Column flow was 16.0 ml/min. Mobile phase used was (A) 0.1% Formic Acid in Water and (B) Acetonitrile. Basic method used was (A) 5 mM ammonium bicarbonate and 0.1% NH$_3$ in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates

N-[2-(4-formylcyclohexyl)-6-(1-hydroxy-1-methyl-ethyl)indazol-5-yl]cyclopropanecarboxamide (Intermediate BOX)

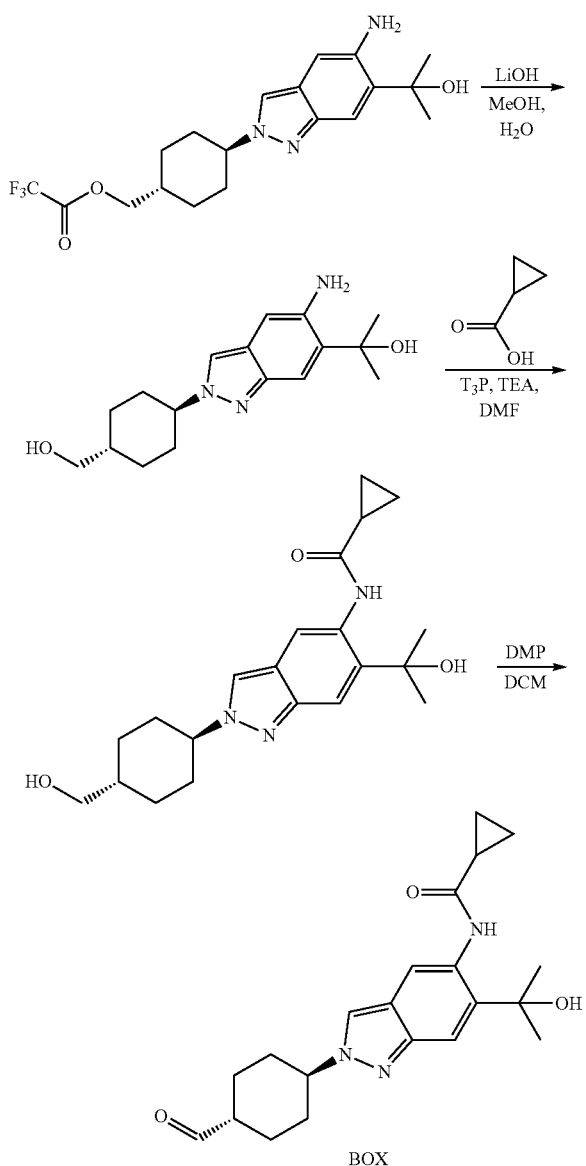

BOX

Step 1—2-[5-Amino-2-[4-(hydroxymethyl)cyclohexyl]indazol-6-yl]propan-2-ol

To a solution of [4-[5-amino-6-(1-hydroxy-1-methyl-ethyl)indazol-2-yl]cyclohexyl]methyl 2,2,2-trifluoroacetate (2.60 g, 6.51 mmol, synthesized via Steps 1-6 of Intermediate AOX) in a mixed solvent of THF (15 mL) and H$_2$O (5 mL) was added LiOH·H$_2$O (1.37 g, 32.5 mmol). The reaction mixture was stirred at 60° C. for 20 hrs. On completion, the residue was poured into water (5 mL) and stirred for 5 min. The aqueous phase was then extracted with ethyl acetate (50 mL×2), and the combined organic phase was washed with brine (50 mL×2), dried with anhydrous Na$_2$SO$_4$, filtered and concentrated in vacuo. The residue was purified by silica gel chromatography (DCM/MeOH=25/1) to give the title compound (840 mg, 35% yield) as yellow solid. $^1$H NMR (400 MHz, DMSO-d$_6$) δ 7.88 (s, 1H), 7.31 (s, 1H), 6.63 (s, 1H), 5.35-5.15 (m, 3H), 4.48 (t, J=5.2 Hz, 1H), 4.32-4.22 (m, 1H), 3.27 (t, J=5.6 Hz, 2H), 2.12-2.03 (m, 2H), 1.92-1.80 (m, 4H), 1.59 (s, 6H), 1.50-1.40 (m, 1H), 1.18-1.05 (m, 2H); LC-MS (ESI$^+$) m/z 304.1 (M+H)$^+$.

Step 2—N-[2-[4-(hydroxymethyl)cyclohexyl]-6-(1-hydroxy-1-methyl-ethyl)indazol-5-yl]cyclopropanecarboxamide To a solution 2-[5-amino-2-[4-(hydroxymethyl)cyclohexyl]indazol-6-yl]propan-2-ol (100 mg, 274 umol) and cyclopropanecarboxylic acid (23.6 mg, 275 umol, 21.7 uL, CAS #1029691-16-4) in DMF (2 mL) was added T$_3$P (349 mg, 549 umol, 326 uL, 50% solution), and DIEA (177 mg, 1.37 mmol, 239 uL). The reaction mixture was then stirred at 25° C. for 2 hrs. On completion, the reaction mixture was concentrated in vacuo and the crude product was purified by reversed phase flash (0.1% NH$_3$—H$_2$O) to give the title compound (80.0 mg, 73% yield) as white solid. $^1$H NMR (400 MHz, DMSO-d$_6$) δ 10.69 (s, 1H), 8.38-8.22 (m, 2H), 7.51 (s, 1H), 6.18 (s, 1H), 4.48 (t, J=5.2 Hz, 1H), 4.43-4.32 (m, 1H), 3.28-3.26 (m, 2H), 2.15-2.07 (m, 2H), 1.93-1.84 (m, 5H), 1.61 (s, 6H), 1.51-1.43 (m, 1H), 1.14 (dd, J=2.8, 12.4 Hz, 2H), 0.99 (s, 2H), 0.84-0.82 (m, 2H); LC-MS (ESI$^+$) m/z 372.2 (M+H)$^+$.

Step 3—N-[2-(4-formylcyclohexyl)-6-(1-hydroxy-1-methyl-ethyl)indazol-5-yl]cyclopropanecarboxamide To a solution of N-[2-[4-(hydroxymethyl)cyclohexyl]-(1-hydroxy-1-methyl-ethyl)indazol-5yl]cyclopropanecarboxamide (70.0 mg, 176 umol) in DCM (2 mL) was added DMP (372 mg, 878 umol, 272 uL) and the reaction mixture was stirred at 25° C. for 2 hrs. On completion, the mixture was quenched with sat. Na$_2$S$_2$O$_3$ (5 mL) and sat. NaHCO$_3$ (5 mL). The mixture was then extracted with DCM (2×20 mL). The organic layer was washed with brine (2×10 mL), dried with Na$_2$SO$_4$, filtered and the filtrate was concentrated in vacuo to give the title compound (40.0 mg, 29% yield) as white solid. LC-MS (ESI$^+$) m/z 370.2 (M+H)$^+$.

[4-(6-Bromo-5-methoxy-1-methyl-benzimidazol-2-yl)cyclohexyl]methanol (Intermediate BOY)

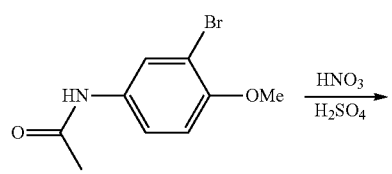

Step 1—N-(5-bromo-4-methoxy-2-nitro-phenyl)acetamide

HNO$_3$ (19.6 g, 311 mmol) was added to Ac$_2$O (38.2 g, 374 mmol), and the mixture was cooled to −10° C., then it was added to a solution of N-(3-bromo-4-methoxy-phenyl)acetamide (7.00 g, 28.7 mmol, CAS #6943-73-3) in Ac$_2$O (38.2 g, 374 mmol) dropwise at −5° C. The reaction mixture was then stirred at 25° C. for 1 h. On completion, the reaction was poured into cold water (200 mL) and a precipitate formed. The reaction was filtered and the filtered cake was washed with water (20 mL×3). Then the crude filter cake was triturated with EA (40 mL) to afford the title compound (5.50 g, 66% yield) as a yellow solid.

Step 2—5-Bromo-4-methoxy-2-nitro-aniline

To a solution of N-(5-bromo-4-methoxy-2-nitro-phenyl) acetamide (5.50 g, 19.0 mmol) in MeOH (200 mL) was added $H_2SO_4$ (18.7 g, 190 mmol) and the mixture was stirred at 70° C. for 2 hours. On completion, the organic solvent was removed under vacuum. Then the reaction was diluted with water (300 mL), extracted with EA (100 mL×3), washed with brine (100 mL), dried over $Na_2SO_4$, filtered and concentrated under vacuum to afford the title compound (4.00 g, 85% yield) as a yellow solid. LC-MS (ESI$^+$) m/z 247.0 (M+H)$^+$.

Step 3—5-Bromo-4-methoxy-N-methyl-2-nitro-aniline

To a solution of 5-bromo-4-methoxy-2-nitro-aniline (4.00 g, 16.2 mmol) in 1,1,1,3,3,3-hexafluoro-propan-2-ol (100 mL) was added methyl trifluoromethanesulfonate (3.99 g, 24.3 mmol) and the mixture was stirred at 25° C. for 3 hours. On completion, the reaction was diluted with EA (100 mL), washed with water (30 mL×3) and brine (4 mL), dried over $Na_2SO_4$, filtered and concentrated under vacuum to give the crude product. The residue was purified by silica gel column chromatography (PE:EA from 1:0 to 50:1) to afford the title compound (1.80 g, 34% yield) as a red solid. LC-MS (ESI$^+$) m/z 261.0 (M+H)$^+$.

Step 4—4-Bromo-5-methoxy-N2-methyl-benzene-1,2-diamine

To a solution of 5-bromo-4-methoxy-N-methyl-2-nitro-aniline (1.70 g, 6.51 mmol) in EtOH (100 mL) and $H_2O$ (30 mL) was added Fe (1.82 g, 32.6 mmol) and $NH_4Cl$ (3.48 g, 65.1 mmol) and the mixture was stirred at 60° C. for 2 hours. On completion, the reaction was filtered through a celite while it was still hot, the filtered cake was washed with EtOH (20 mL×3) and the combined solvent was concentrated in vacuo to afford a crude product. The residue was purified by reversed-phase HPLC (0.1% FA condition) to give the title compound (1.70 g, 90% yield) as an orange solid. LC-MS (ESI$^+$) m/z 231.5 (M+H)$^+$.

Step 5—Methyl 4-[[4-bromo-5-methoxy-2-(methylamino)phenyl]carbamoyl]cyclohexanecarboxylate To a solution of 4-bromo-5-methoxy-N2-methyl-benzene-1,2-diamine (1.70 g, 7.36 mmol) and 4-methoxycarbonylcyclohexanecarboxylic acid (1.51 g, 8.09 mmol, CAS #15177-67-0) in DMF (30 mL) was added DIEA (2.85 g, 22.1 mmol) and HATU (4.20 g, 11.0 mmol) and the mixture was stirred at 25° C. for 1 h. On completion, the reaction was diluted with water (200 mL), and extracted with EA (60 mL×3). The combined organic layer was washed with brine (50 mL), dried over $Na_2SO_4$, filtered and concentrated under vacuum to afford the title compound (2.20 g, 67% yield) as a yellow oil. LC-MS (ESI$^+$) m/z 399.1 (M+H)$^+$.

Step 6— Methyl 4-(6-bromo-5-methoxy-1-methyl-benzimidazol-2-yl)cyclohexanecarboxylate A solution of methyl 4-[[4-bromo-5-methoxy-2-(methylamino)phenyl]carbamoyl]cyclohexane carboxylate (2.10 g, 5.26 mmol) in HOAc (20 mL) was stirred at 80° C. for 1 hour. On completion, the reaction was concentrated in vacuo to give a crude which was purified by reversed phase HPLC (FA=0.1%) to afford the title compound (1.20 g, 2.83 mmol, 54% yield) as a yellow solid. LC-MS (ESI$^+$) m/z 381.1 (M+H)$^+$.

Step 7—[4-(6-Bromo-5-methoxy-1-methyl-benzimidazol-2-yl)cyclohexyl]methanol

To a solution of methyl 4-(6-bromo-5-methoxy-1-methyl-benzimidazol-2-yl)cyclohexanecarboxylate (1.00 g, 2.62 mmol) in THF (16 mL) and MeOH (2 mL) was added $LiBH_4$ (286 mg, 13.1 mmol) at 0° C. Then the mixture was stirred at 60° C. for 16 hours. Next, $LiBH_4$ (457 mg, 21.0 mmol) was added and the mixture was stirred at 60° C. for another 16 h. On completion, the reaction was poured into water (100 mL), extracted with EA (3×30 mL), washed with brine (30 mL), dried over $Na_2SO_4$, filtered and concentrated under vacuum to give the crude product. The residue was purified by silica gel column chromatography (PE:EA from 10:1 to 0:1) to give the title compound (140 mg, 357 umol, 14% yield) as a brown oil and remaining starting material (300 mg, 708 umol, 27% yield) as a yellow solid. LC-MS (ESI$^+$) m/z 353.1 (M+H)$^+$.

Next, to a solution of methyl 4-(6-bromo-5-methoxy-1-methyl-benzimidazol-2-yl)cyclohexanecarboxylate (250 mg, 656 umol) in THF (8 mL) was added LAH (40.0 mg, 1.05 mmol) at 0° C., and the mixture was stirred at 0° C. for 0.5 h. On completion, the reaction was quenched with water (2.4 mL), filtered and the filtered cake was washed with MeOH (5 mL×3), then the solvent was removed under vacuum. Then the crude was purified by prep-TLC to afford the title compound (140 mg, 357 umol, 54.4% yield) as brown oil. LC-MS (ESI$^+$) m/z 353.1 (M+H)$^+$.

N-[2-(4-formylcyclohexyl)-6-methoxy-3-methyl-benzimidazol-5-yl]-6-(trifluoromethyl) pyridine-2-carboxamide (Intermediate BOZ)

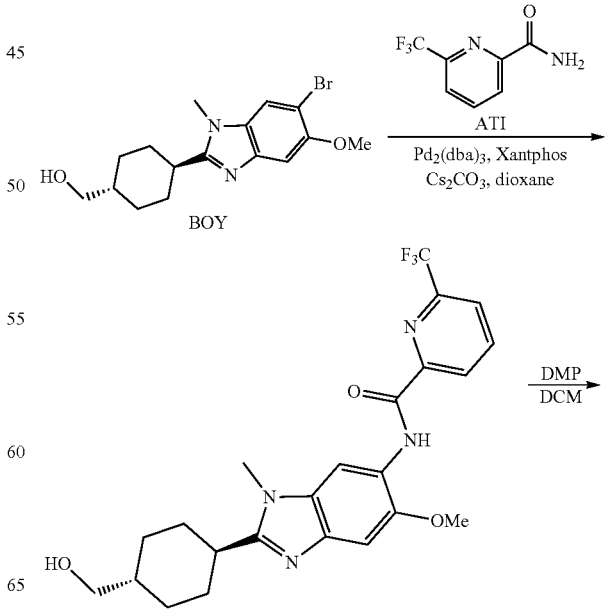

-continued

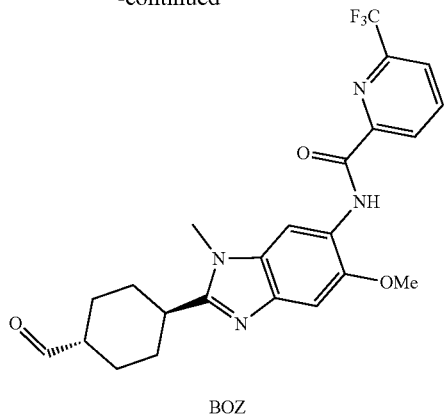

BOZ

Step 1—N-[2-[4-(hydroxymethyl)cyclohexyl]-6-methoxy-3-methyl-benzimidazol-5-yl]-6-(trifluoromethyl)pyridine-2-carboxamide To a solution of [4-(6-bromo-5-methoxy-1-methyl-benzimidazol-2-yl)cyclohexyl]methanol (250 mg, 708 umol, Intermediate BOY) and 6-(trifluoromethyl)pyridine-2-carboxamide (269 mg, 1.42 mmol, Intermediate ATI) in dioxane (4 mL) was added $Cs_2CO_3$ (461 mg, 1.42 mmol), Xantphos (81.9 mg, 141 umol) and $Pd_2(dba)_3$ (64.8 mg, 70.8 umol). The mixture was degassed and purged with $N_2$ three times and then it was stirred at 100° C. for 16 hours. On completion, the reaction was concentrated under vacuum to give a crude which was purified by reversed-phase HPLC (0.1% $NH_3·H_2O$ condition) to afford the title compound (90.0 mg, 175 umol, 25% yield) as a yellow solid. LC-MS (ESI$^+$) m/z 463.3 (M+H)$^+$.

Step 2—N-[2-(4-formylcyclohexyl)-6-methoxy-3-methyl-benzimidazol-5-yl]-6-(trifluoromethyl) pyridine-2-carboxamide To a solution of N-[2-[4-(hydroxymethyl)cyclohexyl]-6-methoxy-3-methyl-benzimidazol-5-yl]-6-(trifluoromethyl)pyridine-2-carboxamide (90.0 mg, 195 umol) in DCM (4 mL) was added DMP (165 mg, 389 umol) and the mixture was stirred at 25° C. for 1 hour. On completion, the reaction was quenched with sat. $Na_2S_2CO_3$ (10 mL), then diluted with EA (100 mL), washed with sat. $NaHCO_3$ (100 mL) and brine (40 mL). The mixture was then dried over $Na_2SO_4$, filtered and concentrated under vacuum to give the title compound (80.0 mg, 85% yield) as a yellow solid. LC-MS (ESI$^+$) m/z 461.2 (M+H)$^+$.

2-(2,6-Dioxo-3-piperidyl)-4-[2-(4-piperidyl)ethylamino]isoindoline-1,3-dione (Intermediate BPA)

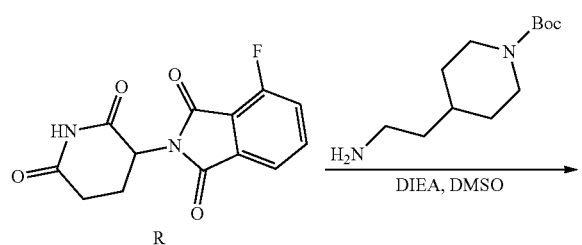

-continued

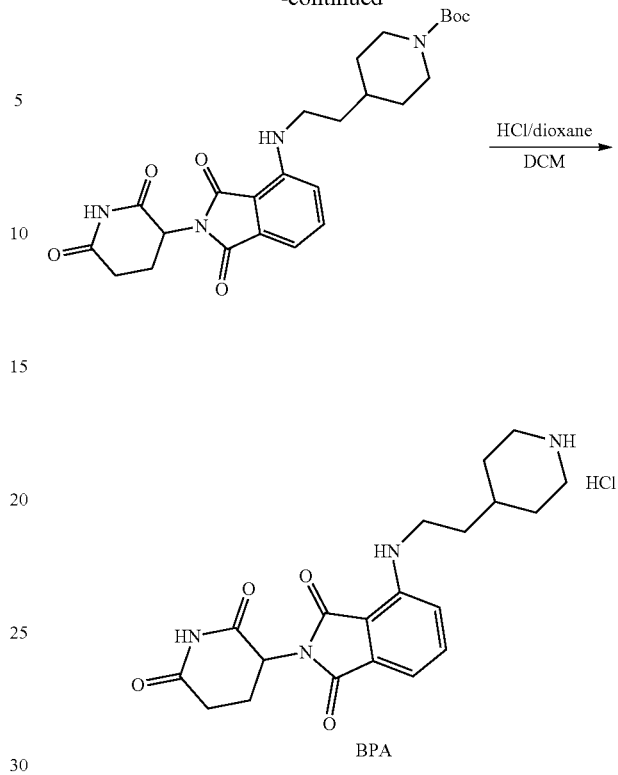

BPA

Step 1—Tert-butyl 4-[2-[[2-(2,6-dioxo -3-piperidyl)-1,3-dioxo-isoindolin-4-yl]amino]ethyl]piperidine -1-carboxylate To a mixture of 2-(2,6-dioxo-3-piperidyl)-4-fluoro-isoindoline-1,3-dione (2.10 g, 7.60 mmol, Intermediate R) and tert-butyl 4-(2-aminoethyl)piperidine-1-carboxylate (1.74 g, 7.60 mmol, CAS #146093-46-1) in DMSO (60 mL) was added DIEA (1.96 g, 15.2 mmol). The mixture was stirred at 130° C. for 4 hours. On completion, the mixture was purified by reverse phase flash (FA condition) to give the title compound (2.00 g, 51% yield). $^1$H NMR (400 MHz, DMSO-$d_6$) δ 11.09 (s, 1H), 7.58 (dd, J=7.2, 8.3 Hz, 1H), 7.09 (d, J=8.4 Hz, 1H), 7.02 (d, J=7.2 Hz, 1H), 6.51 (t, J=6.0 Hz, 1H), 5.05 (dd, J=5.6, 12.8 Hz, 1H), 3.96-3.85 (m, 2H), 2.94-2.81 (m, 1H), 2.75-2.65 (m, 2H), 2.60 (m, 1H), 2.56-2.54 (m, 1H), 2.08-1.98 (m, 1H), 1.69 (d, J=12.4 Hz, 2H), 1.52 (m, 3H), 1.38 (s, 11H), 1.04-1.01 (m, 2H); LC-MS (ESI$^+$) m/z 385.2 (M+H)$^+$.

Step 2—2-(2,6-Dioxo-3-piperidyl)-4-[2-(4-piperidyl)ethylamino]isoindoline-1,3-dione To a solution of tert-butyl 4-[2-[[2-(2,6-dioxo-3-piperidyl)-1,3-dioxo-isoindolin-4-yl]amino]ethyl]piperidine-1-carboxylate (100 mg, 206 umol) in DCM (3 mL) was added HCl/dioxane (4 M, 1.5 mL) at 25° C. and the mixture was stirred at 25° C. for 1 hour. On completion, the mixture was concentrated in vacuo to give the title compound (135 mg, 98% yield, HCl salt) as light yellow solid. LC-MS (ESI$^+$) m/z 385.2 (M+H)$^+$.

N-(2-((1R,4R)-4-formylcyclohexyl)-7-methoxyimidazo[1,2-a]pyridin-6-yl)-6-(trifluoromethyl)picolinamide (Intermediate BPB)

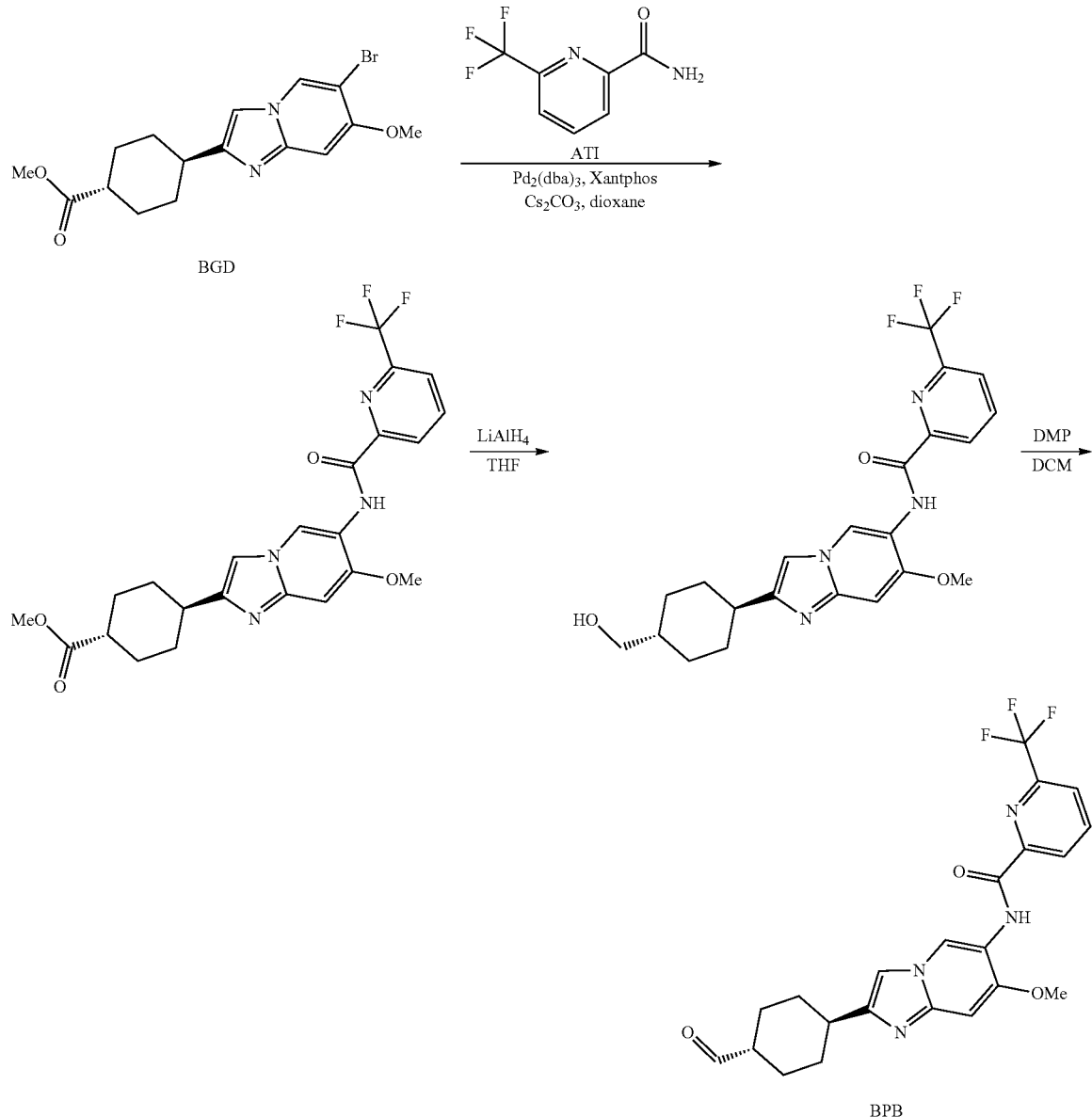

Step 1—(1R,4R)-methyl 4-(7-methoxy-6-(6-(trifluoromethyl)picolinamido)imidazo[1,2-a]pyridin-2-yl)cyclohexanecarboxylate To a solution of methyl 4-(6-bromo-7-methoxy-imidazo[1,2-a]pyridin-2-yl)cyclohexanecarboxylate (400 mg, 1.09 mmol, Intermediate BGD) and 6-(trifluoromethyl)pyridine-2-carboxamide (227 mg, 1.20 mmol, Intermediate ATI) in dioxane (5 mL) was added $Pd_2(dba)_3$ (99.7 mg, 108 umol), $Cs_2CO_3$ (709 mg, 2.18 mmol) and Xantphos (126 mg, 217 umol). The mixture was stirred at 80° C. for 12 hours under $N_2$ atmosphere. On completion, the reaction mixture was filtered and concentrated under reduced pressure to give a residue. The residue was purified by column chromatography ($SiO_2$, DCM/MeOH=100/1 to 20/1) to give the title compound (280 mg, 40% yield) as an off-white solid. LC-MS (ESI$^+$) m/z 477.4 (M+H)$^+$.

Step 2—N-(2-((1R,4R)-4-(hydroxymethyl)cyclohexyl)-7-methoxyimidazo[1,2-a]pyridine-6-yl)-6-(trifluoromethyl)picolinamide To a solution of methyl 4-[7-methoxy-6-[[6-(trifluoromethyl)pyridine-2-carbonyl]amino]imidazo[1,2-a]pyridin-2-yl]cyclohexanecarboxylate (180 mg, 377 umol) in THF (5 mL) was added $LiAlH_4$ (28.6 mg, 755 umol) at 0° C., and the mixture was stirred at 0° C. for 0.5 hour. On completion, the reaction mixture was quenched with $H_2O$ (0.1 mL), 15% NaOH aqueous (0.2 mL) and $H_2O$ (0.1 mL) at 0° C. Then the mixture was diluted with THF (50 mL) and dried over Na$_2$SO$_4$, filtered and concentrated under reduced pressure to give the title compound (160 mg, 94% yield) as a brown solid. LC-MS (ESI$^+$) m/z 449.4 (M+H)$^+$.

Step 3—N-(2-((1R,4R)-4-formylcyclohexyl)-7-methoxyimidazo[1,2-a]pyridin-6-yl)-6-(trifluoromethyl)picolinamide To a solution of N-[2-[4-(hydroxymethyl)cyclohexyl]-7-methoxy-imidazo[1,2-a]pyridin-6-yl]-6-(trifluoromethyl)pyridine-2-carboxamide (160 mg, 356 umol) in DCM (5 mL) was added DMP (227 mg, 535 umol) and the mixture was stirred at 25° C. for 0.5 hour. On completion, the reaction mixture was quenched with sat. Na$_2$SO$_3$ (20 mL) and sat. NaHCO$_3$ (20 mL) at 0° C., and then diluted with H$_2$O (20 mL) and extracted with DCM (3×50 mL). The combined organic layers were washed with brine (50 mL), dried over Na$_2$SO$_4$, filtered and concentrated under reduced pressure to give a residue. The residue was purified by prep-TLC (SiO$_2$, DCM:MeOH=20:1) to give the title compound (88.0 mg, 48% yield) as an off-white solid. LC-MS (ESI$^+$) m/z 447.1 (M+H)$^+$.

N-(2-((1r,4r)-4-formylcyclohexyl)-7-(2-hydroxypropan-2-yl)imidazo[1,2-a]pyridin-6-yl)-6-(trifluoromethyl)picolinamide (Intermediate BPC)

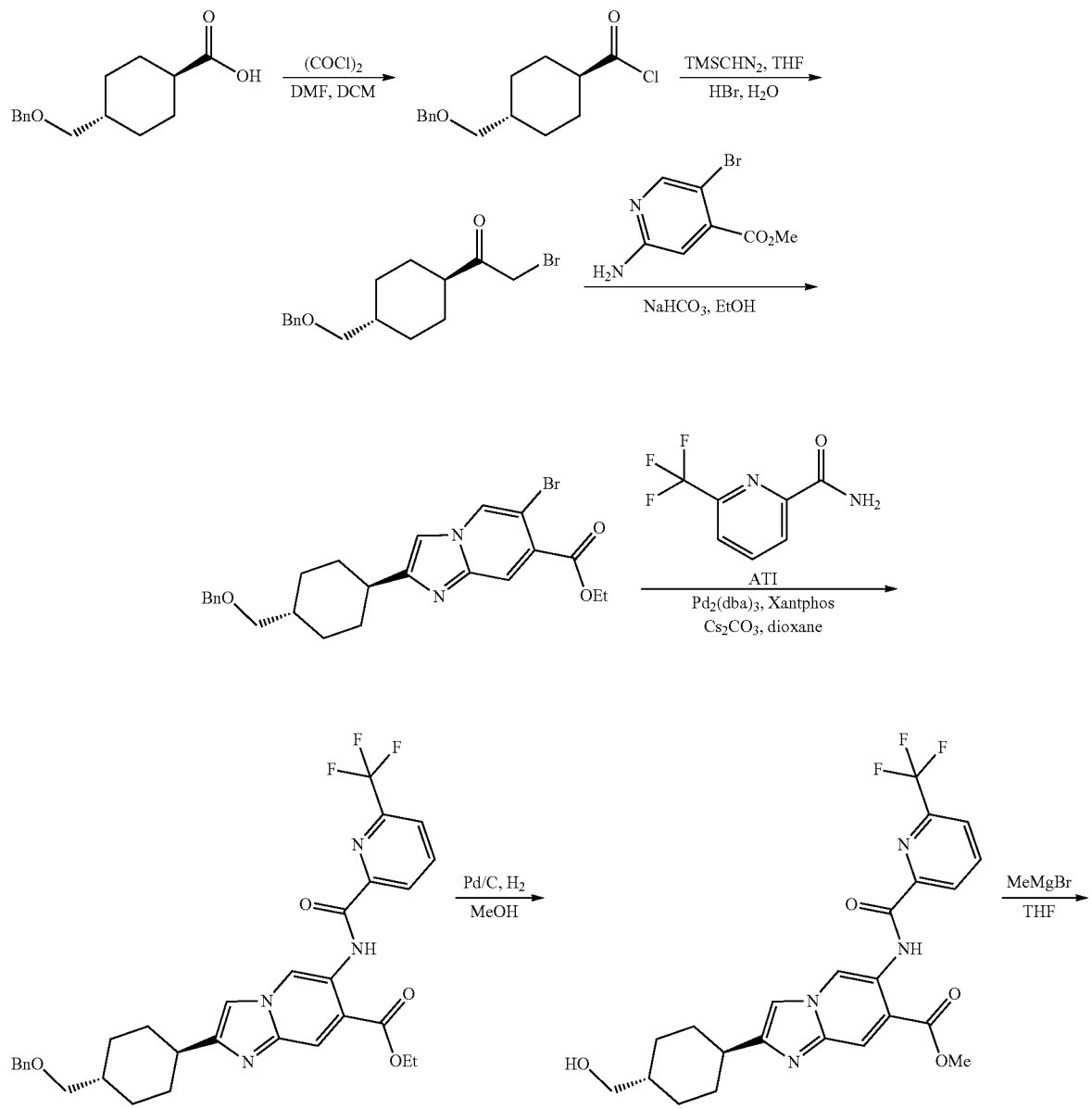

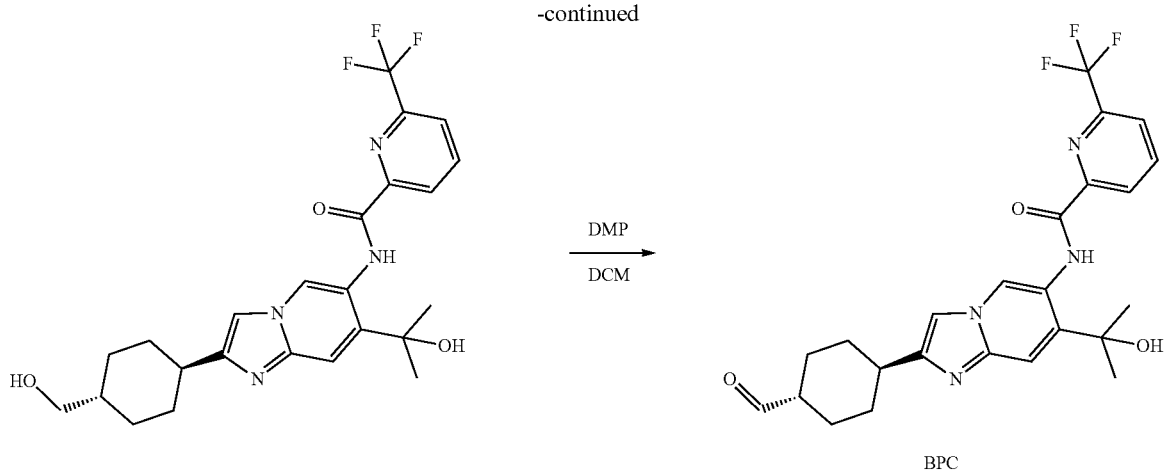

BPC

Step 1—(1R,4R)-4-((benzyloxy)methyl)cyclohexanecarbonyl Chloride

To a solution of 4-(benzyloxymethyl)cyclohexanecarboxylic acid (4.00 g, 16.1 mmol, synthesized via Steps 1-3 of Intermediate BAU) in DCM (20 mL) was added DMF (117 mg, 1.61 mmol) and dropwise (COCl)$_2$ (4.50 g, 35.4 mmol) at 0° C. Then the mixture was stirred at 25° C. for 1 hour. On completion, the reaction mixture was concentrated in vacuo to give the title compound (4.00 g, 93% yield) as brown oil.

Step 2—1-((1R,4R)-4-((benzyloxy)methyl)cyclohexyl)-2-bromoethanone

A solution of 4-(benzyloxymethyl)cyclohexanecarbonyl chloride (4.00 g, 14.9 mmol) in THF (20 mL) was added dropwise to TMSCHN$_2$ (2 M, 14.9 mL, 29.9 mmol) at 0° C. Then the reaction mixture was stirred at 0° C. for 1 hour and at 25° C. for 1 hour. Next, HBr (5.56 g, 32.9 mmol, 48% solution) was added dropwise and the mixture was stirred at 0° C. for 0.5 hour. On completion, the reaction mixture was quenched with sat. NaHCO$_3$ (100 mL) at 0° C., and then diluted with H$_2$O (50 mL) and extracted with EA (3×50 mL). The combined organic layers were washed with brine (50 mL), dried over Na$_2$SO$_4$, filtered and concentrated in vacuo to give a residue. The residue was purified by column chromatography (SiO$_2$, petroleum ether/ethyl acetate=100/1 to 3/1) to give the title compound (1.30 g, 24% yield) as an off-white solid. $^1$H NMR (400 MHz, chloroform-d) δ 7.39-7.28 (m, 5H), 4.50 (s, 2H), 4.17 (s, 1H), 3.97 (s, 1H), 3.67 (s, 1H), 3.31 (d, J=6.1 Hz, 2H), 2.77-2.57 (m, 1H), 2.04-1.84 (m, 4H), 1.73-1.55 (m, 1H), 1.50-1.33 (m, 2H), 1.17-0.95 (m, 2H); LC-MS (ESI$^+$) m/z 325.2 (M+H)$^+$.

Step 3— Ethyl 2-((1r,4r)-4-((benzyloxy)methyl)cyclohexyl)-6-bromoimidazo[1,2-a]pyridine-7-carboxylate To a solution of 1-[4-(benzyloxymethyl)cyclohexyl]-2-bromo-ethanone (1.30 g, 4.00 mmol) and methyl 2-amino-5-bromo-pyridine-4-carboxylate (923 mg, 4.00 mmol, CAS #882499-87-8) in EtOH (20 mL) was added NaHCO$_3$(671 mg, 7.99 mmol) and the mixture was stirred at 90° C. for 12 hours. On completion, the reaction mixture was concentrated under reduced pressure to remove the solvent. The residue was diluted with H$_2$O (100 mL) and extracted with DCM (3×50 mL). The combined organic layers were washed with brine (50 mL), dried over Na$_2$SO$_4$, filtered and concentrated under reduced pressure to give a residue. The residue was purified by column chromatography (SiO$_2$, DCM/MeOH=100/1 to 20/1) to give the title compound (0.45 g, 20% yield) as brown oil. $^1$H NMR (400 MHz, chloroform-d) δ 8.31 (s, 1H), 8.19 (s, 1H), 7.39 (s, 1H), 7.37-7.32 (m, 5H), 4.53 (s, 2H), 4.51-4.49 (m, 2H), 4.41 (m, 2H), 3.35 (m, 2H), 3.31-3.26 (m, 2H), 2.77 (s, 1H), 2.23-2.15 (m, 2H), 2.00 (m, 2H), 1.95-1.82 (m, 3H), 1.79-1.67 (m, 2H), 1.53 (m, 2H), 1.41 (m, 4H), 1.25 (m, 3H), 1.18 (m, 2H), 1.07-0.95 (m, 2H); LC-MS (ESI$^+$) m/z 471.3 (M+H)$^+$.

Step 4—Ethyl 2-((1r,4r)-4-((benzyloxy)methyl)cyclohexyl)-6-(6-(trifluoromethyl)picolinamido) imidazo[1,2-a]pyridine-7-carboxylate To a solution of ethyl 2-[4-(benzyloxymethyl)cyclohexyl]-6-bromo-imidazo[1,2-a]pyridine-7-carboxylate (400 mg, 848 umol) and 6-(trifluoromethyl)pyridine-2-carboxamide (177 mg, 933 umol, Intermediate ATI) in dioxane (4 mL) was added Pd$_2$(dba)$_3$ (77.7 mg, 84.8 umol), Cs$_2$CO$_3$ (552 mg, 1.70 mmol) and Xantphos (98.2 mg, 169 umol). The mixture was then stirred at 80° C. for 12 hours under nitrogen atmosphere. On completion, the reaction mixture was filtered and concentrated under reduced pressure to give a residue. The residue was purified by column chromatography (SiO$_2$, DCM/MeOH=100/1 to 20/1) to give the title compound (0.30 g, 29% yield) as brown oil. LC-MS (ESI$^+$) m/z 581.5 (M+H)$^+$.

Step 5—Ethyl 2-((1r,4r)-4-(hydroxymethyl)cyclohexyl)-6-(6-(trifluoromethyl)picolinamido)imidazo[1,2-a]pyridine-7-carboxylate To a solution of ethyl 2-[4-(benzyloxymethyl)cyclohexyl]-6-[[6-(trifluoromethyl)pyridine-2-carbonyl]amino] imidazo[1,2-a]pyridine-7-carboxylate (300 mg, 516 umol) in MeOH (3 mL) and THF (0.5 mL) was added Pd/C (10 wt %, 30.0 mg) under N$_2$ atmosphere. The suspension was degassed and purged with H$_2$ three times. The mixture was stirred under H$_2$ (50 Psi.) at 25° C. for 2 hours. On completion, the reaction mixture was filtered and concentrated under reduced pressure to give the title compound (90.0 mg, 36% yield) as brown oil. LC-MS (ESI$^+$) m/z 477.4 (M+H)$^+$.

Step 6—N-(2-((1r,4r)-4-(hydroxymethyl)cyclohexyl)-7-(2-hydroxypropan-2-yl)imidazo[1,2-a]pyridin-6-yl)-6-(trifluoromethyl)picolinamide To a solution of methyl 2-[4-(hydroxymethyl)cyclohexyl]-6-[[6-(trifluoromethyl)pyridine-2-carbonyl]amino]imidazo[1,2-a]pyridine-7-carboxylate (90.0 mg, 188 umol) in THF (1 mL) was added MeMgBr (3.0 M, 629 uL) dropwise at 0° C. The mixture was stirred at 0° C. for 1 hour. On completion, the reaction mixture was quenched with sat. NH$_4$Cl (20 mL) at 0° C., and then diluted with H$_2$O (20 mL) and extracted with DCM (3×50 mL). The combined organic layers were washed with brine (50 mL), dried over Na$_2$SO$_4$, filtered and concentrated under reduced pressure to give the title compound (90.0 mg, 100% yield) as brown oil. LC-MS (ESI$^+$) m/z 477.4 (M+H)$^+$.

Step 7—N-(2-((1r,4r)-4-formylcyclohexyl)-7-(2-hydroxypropan-2-yl)imidazo[1,2-a]pyridin-6-yl)-6-(trifluoromethyl)picolinamide To a solution of N-[2-[4-(hydroxymethyl)cyclohexyl]-7-(1-hydroxy-1-methyl-ethyl) imidazo[1,2-a] pyridin-6-yl]-6-(trifluoromethyl)pyridine-2-carboxamide (90.0 mg, 188 umol) in DCM (2 mL) was added DMP (104 mg, 245 umol) at 0° C. Then the mixture was stirred at 25° C. for 0.5 hour. On completion, the reaction mixture was quenched with sat. NaHCO$_3$ (20 mL) and sat. Na$_2$SO$_3$ (20 mL) at 0° C., and then diluted with H$_2$O (20 mL) and extracted with DCM (3×50 mL). The combined organic layers were washed with brine (50 mL), dried over Na$_2$SO$_4$, filtered and concentrated under reduced pressure to give a residue. The residue was purified by prep-TLC (SiO$_2$, DCM:MeOH=20:1) to give the title compound (58.0 mg, 58% yield) as an off-white solid. $^1$H NMR (400 MHz, chloroform-d) δ 12.16 (s, 1H), 9.69 (d, J=1.1 Hz, 1H), 9.57 (s, 1H), 8.47 (d, J=7.8 Hz, 1H), 8.14 (t, J=7.8 Hz, 1H), 7.87 (d, J=7.7 Hz, 1H), 7.53 (s, 1H), 7.34 (s, 1H), 2.74 (m, 1H), 2.48 (m, 1H), 2.42-2.33 (m, 1H), 2.38-2.31 (m, 2H), 2.26 (m, 2H), 1.77 (s, 6H), 1.61 (m, 2H), 1.44 (m, 2H); LC-MS (ESI$^+$) m/z 475.4 (M+H)$^+$.

N-[2-(4-formyl cyclohexyl)-6-(1-hydroxy-1-methyl-ethyl)-3H-benzimidazol-5-yl]-6-(trifluoromethyl)pyridine-2-carboxamide (Intermediate BPD)

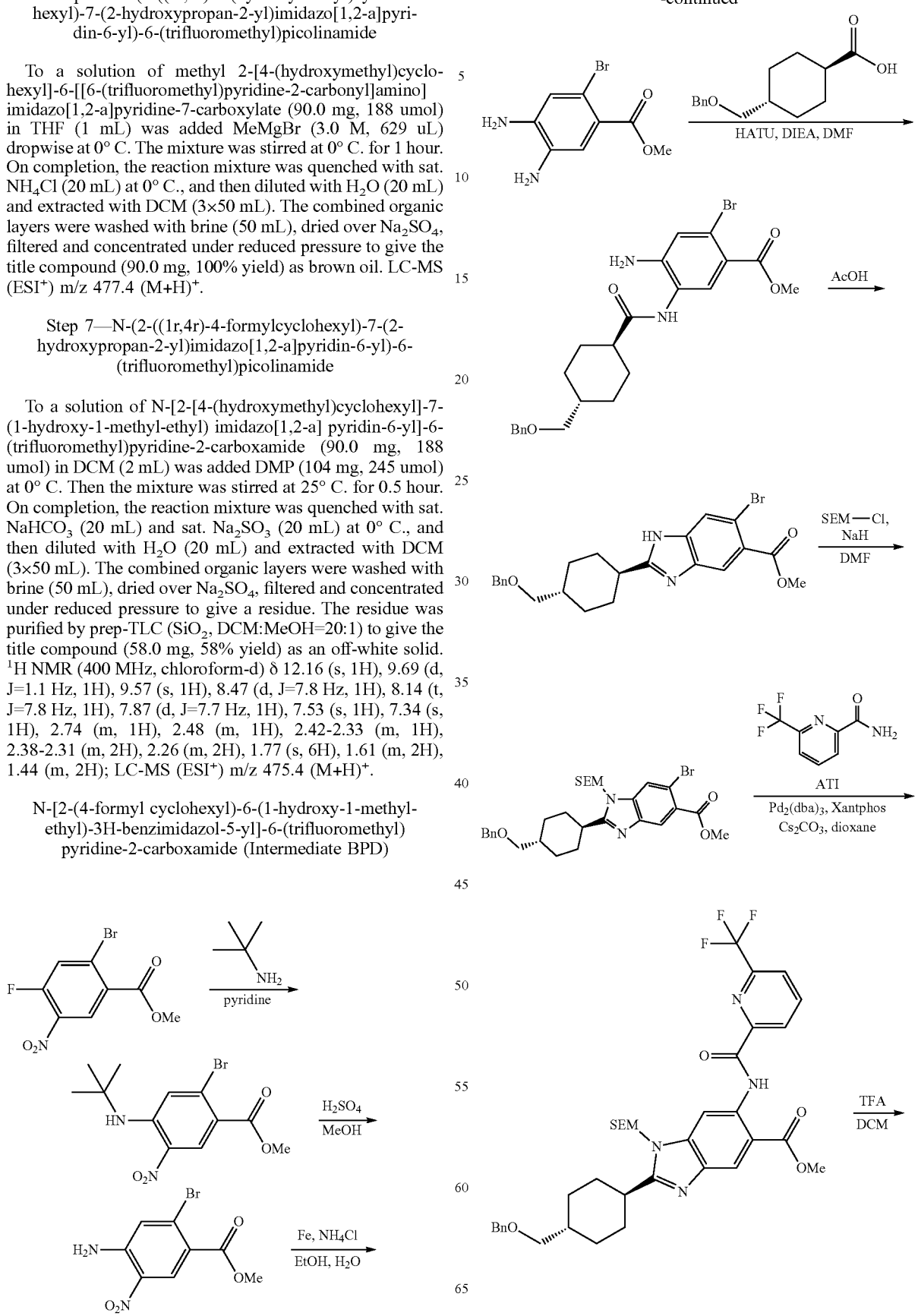

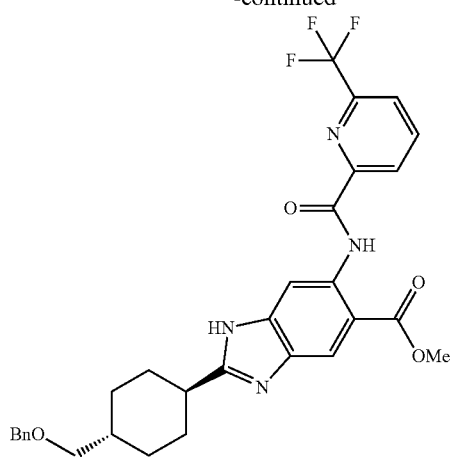

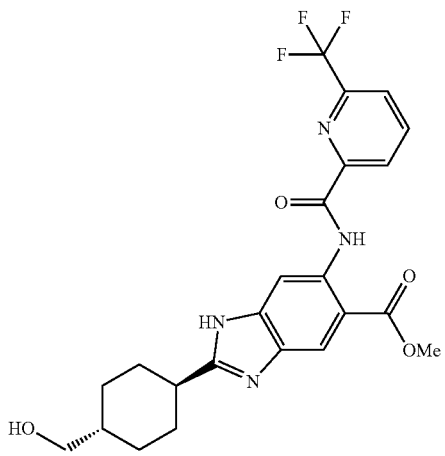

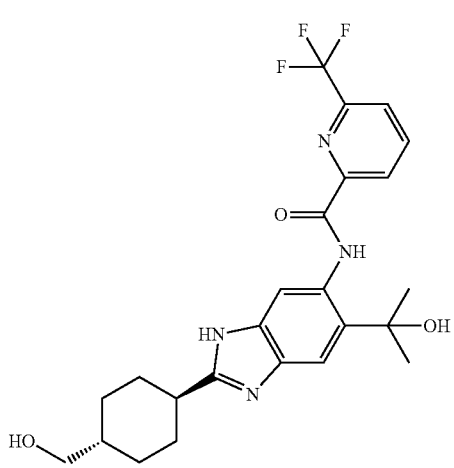

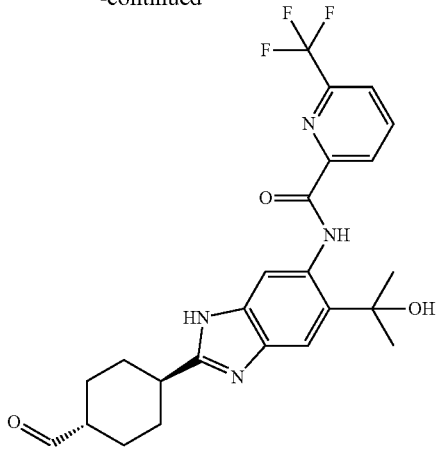

BPD

Step 1—Methyl 2-bromo-4-(tert-butylamino)-5-nitro-benzoate

To a solution of methyl 2-bromo-4-fluoro-5-nitro-benzoate (11.0 g, 39.5 mmol, synthesized via Steps 1-2 of Intermediate BEA) in pyridine (80 mL) was added 2-methylpropan-2-amine (5.79 g, 79.1 mmol, CAS #75-64-9) and the reaction mixture was stirred at 20° C. for 3 hrs. On completion, the reaction mixture was diluted with water (100 mL) and extracted with EA (3×90 mL). The combined organic layers were washed with water (3×80 mL), 1.0 M aq. HCl (2×60 mL), and brine (2×60 mL), then dried over $Na_2SO_4$, filtered and concentrated in vacuo. The residue was purified by silica gel chromatography (PE:EA=100:1) to give the title compound (9.60 g, 73% yield) as yellow solid. $^1$H NMR (400 MHz, $CDCl_3$) δ 8.85 (s, 1H), 8.53 (s, 1H), 7.40 (s, 1H), 3.90 (s, 3H), 1.54 (s, 9H).

Step 2—Methyl 4-amino-2-bromo-5-nitro-benzoate

To a solution of methyl 2-bromo-4-(tert-butylamino)-5-nitro-benzoate (3.50 g, 10.5 mmol) in MeOH (30 mL) was added $H_2SO_4$ (2.76 g, 28.1 mmol, 1.5 mL) at 20° C. The reaction mixture was then stirred at 80° C. for 16 hrs. On completion, the reaction mixture was concentrated in vacuo. The residue was diluted with water (30 mL), basified with saturated $NaHCO_3$ until the pH=8 and extracted with EA (3×120 mL). The combined organic layers were washed with brine (2×60 mL) dried over $Na_2SO_4$, filtered and concentrated in vacuo to give the title compound (2.70 g, 92% yield) as yellow solid. $^1$H NMR (400 MHz, DMSO-$d_6$) δ 8.53 (s, 1H), 7.96 (s, 2H), 7.38 (s, 1H), 3.80 (s, 3H).

Step 3—Methyl 4,5-diamino-2-bromo-benzoate

To a solution of methyl 4-amino-2-bromo-5-nitro-benzoate (2.50 g, 9.09 mmol) and $NH_4Cl$ (3.89 g, 72.7 mmol) in a mixed solvents of EtOH (20 mL) and water (20 mL) was added Fe (2.54 g, 45.4 mmol) at 80° C. and the reaction mixture was stirred at 80° C. for 2 hrs. On completion, the reaction mixture was filtered and the filter cake was washed with EtOH (50 mL). The filtrate was concentrated in vacuo to give a residue which was diluted with water (80 mL) and extracted with DCM (3×100 mL). The combined organic layers were washed with brine, dried over $Na_2SO_4$, filtered and concentrated in vacuo. The residue was purified by silica gel chromatography (PE:EA=3:1) to give the title compound (1.90 g, 85% yield) as brown solid. $^1$H NMR (400 MHz, CDCl$_3$) δ 7.33 (s, 1H), 6.94 (s, 1H), 3.87 (s, 3H), 3.80 (s, 2H), 3.33 (s, 2H).

Step 4—Methyl 4-amino-5-[[4-(benzyloxymethyl)cyclohexanecarbonyl]amino]-2-bromo-benzoate To a solution of methyl 4,5-diamino-2-bromo-benzoate (1.80 g, 7.34 mmol), 4-(benzyloxymethyl)cyclohexanecarboxylic acid (1.82 g, 7.34 mmol, synthesized via Steps 1-3 of Intermediate BAU) and DIEA (1.90 g, 14.6 mmol, 2.56 mL) in DMF (25 mL) was added HATU (3.35 g, 8.81 mmol) and the reaction mixture was stirred at 20° C. for 2 hrs. On completion, the reaction mixture was poured into water (150 mL) and extracted with EA (3×100 mL). The combined organic layers were washed with brine (2×50 mL), dried over Na$_2$SO$_4$, filtered and concentrated in vacuo. The residue was purified by silica gel chromatography (PE:EA=4:1) to give the title compound (2.70 g, 77% yield) as brown solid. $^1$H NMR (400 MHz, CDCl$_3$) δ 7.94 (s, 1H), 7.63 (s, 1H), 7.28-7.20 (m, 5H), 6.94 (s, 1H), 4.43 (s, 2H), 4.26 (s, 2H), 3.77 (s, 3H), 3.24 (d, J=6.0 Hz, 2H), 2.24-2.12 (m, 1H), 1.99-1.85 (m, 4H), 1.65-1.59 (m, 1H), 1.56-1.45 (m, 2H), 1.08-0.90 (m, 2H).

Step 5—Methyl 2-[4-(benzyloxymethyl)cyclohexyl]-6-bromo-1H-benzimidazole-5-carboxylate A solution of methyl 4-amino-5-[[4-(benzyloxymethyl)cyclohexanecarbonyl]amino]-2-bromo-benzoate (2.50 g, 5.26 mmol) in AcOH (25 mL) was stirred at 80° C. for 12 hrs. On completion, the reaction mixture was concentrated in vacuo to remove AcOH. The residue was diluted with DCM (150 mL), washed with saturated NaHCO$_3$ (2×40 mL), brine (2×40 mL), dried over Na$_2$SO$_4$, filtered and concentrated in vacuo. The residue was purified by silica gel chromatography (PE:EA=4:1) to give the title compound (2.00 g, 83% yield) as brown oil. $^1$H NMR (400 MHz, DMSO-d$_6$) δ 8.01-7.64 (m, 2H), 7.40-7.29 (m, 5H), 4.47 (s, 2H), 3.85 (s, 3H), 3.32-3.30 (m, 2H), 2.88-2.76 (m, 1H), 2.14-2.05 (m, 2H), 1.93-1.85 (m, 2H), 1.71-1.53 (m, 3H), 1.16-1.08 (m, 2H).

Step 6—Methyl 2-[4-(benzyloxymethyl)cyclohexyl]-6-bromo-1-(2-trimethylsilylethoxymethyl)benzimidazole-5-carboxylate To a solution of methyl 2-[4-(benzyloxymethyl)cyclohexyl]-6-bromo-1H-benzimidazole-5-carboxylate (1.80 g, 3.94 mmol) in DMF (20 mL) was added NaH (204 mg, 5.12 mmol, 60% dispersion in mineral oil) at 0° C. After 10 min, SEM-Cl (787 mg, 4.72 mmol) was added and the reaction mixture was stirred at 0° C. for 50 min. On completion, the reaction mixture was poured into saturated NH$_4$Cl (100 mL) and extracted with EA (3×80 mL). The combined organic layers were washed with brine (60 mL), dried over Na$_2$SO$_4$, filtered and concentrated in vacuo. The residue was purified by silica gel chromatography (PE:EA=10:1) to give the title compound (1.53 g, 66% yield) as yellow oil. $^1$H NMR (400 MHz, CDCl$_3$) δ 8.26-7.67 (m, 2H), 7.37-7.30 (m, 5H), 5.48 (d, J=16.0 Hz, 2H), 4.54 (s, 2H), 3.95 (d, J=5.2 Hz, 3H), 3.55 (t, J=8.0 Hz, 2H), 3.37 (d, J=6.0 Hz, 2H), 2.92-2.85 (m, 1H), 2.08-2.00 (m, 4H), 1.87-1.78 (m, 2H), 1.31-1.12 (m, 3H), 0.92 (t, J=8.0 Hz, 2H), −0.03 (d, J=3.6 Hz, 9H).

Step 7—Methyl 2-[4-(benzyloxymethyl)cyclohexyl]-6-[[6-(trifluoromethyl)pyridine-2-carbonyl]amino]-1-(2-trimethylsilylethoxymethyl)benzimidazole-5-carboxylate A mixture of methyl 2-[4-(benzyloxymethyl)cyclohexyl]-6-bromo-1-(2-trimethylsilylethoxymethyl) benzimidazole-5-carboxylate (1.60 g, 2.72 mmol), 6-(trifluoromethyl)pyridine-2-carboxamide (517 mg, 2.72 mmol, Intermediate ATI), Pd$_2$(dba)$_3$ (249 mg, 272 umol), Xantphos (315 mg, 544 umol) and Cs$_2$CO$_3$ (1.77 g, 5.45 mmol) in dioxane (20 mL) was stirred at 80° C. for 4 hrs. On completion, the reaction mixture was filtered and the filter cake was washed with DCM (50 mL). The filtrate was concentrated in vacuo and the residue was purified by silica gel chromatography (PE:EA=8:1 to 4:1) to give the title compound (1.50 g, 79% yield) as yellow oil. $^1$H NMR (400 MHz, CDCl3) δ 13.35-12.71 (m, 1H), 9.49-9.03 (m, 1H), 8.57-8.39 (m, 2H), 8.17-8.07 (m, 1H), 7.93-7.83 (m, 1H), 7.38-7.30 (m, 5H), 5.54 (d, J=9.6 Hz, 2H), 4.54 (s, 2H), 4.04 (d, J=8.8 Hz, 3H), 3.65-3.56 (m, 2H), 3.38 (dd, J=1.2, 6.4 Hz, 2H), 3.01-2.87 (m, 1H), 2.14-2.06 (m, 2H), 2.05-1.96 (m, 2H), 1.95-1.82 (m, 3H), 1.24-1.14 (m, 2H), 1.00-0.90 (m, 2H), −0.04 (d, J=5.6 Hz, 9H).

Step 8—Methyl 2-[4-(benzyloxymethyl)cyclohexyl]-6-[[6-(trifluoromethyl)pyridine-2-carbonyl]amino]-1H-benzimidazole-5-carboxylate To a solution of methyl 2-[4-(benzyloxymethyl)cyclohexyl]-6-[[6-(trifluoromethyl)pyridine-2-carbonyl]amino]-1-(2-trimethylsilylethoxymethyl)benzimidazole-5-carboxylate (1.00 g, 1.44 mmol) in DCM (10 mL) was added TFA (15.4 g, 135 mmol, 10.0 mL) and the reaction mixture was stirred at 20° C. for 12 hrs. On completion, the combined reaction mixture was concentrated in vacuo. The residue was diluted with DCM (200 mL), washed with sat. NaHCO$_3$(2× 40 mL), brine (2×40 mL), dried over Na$_2$SO$_4$, filtered and concentrated in vacuo. The residue was purified by silica gel chromatography (PE:EA=4:1) to give the title compound (620 mg, 76% yield) as yellow solid. $^1$H NMR (400 MHz, CDCl$_3$) δ 13.48-12.92 (m, 1H), 9.99-9.48 (m, 1H), 9.10 (s, 1H), 8.55-8.45 (m, 2H), 8.11 (t, J=7.6 Hz, 1H), 7.86 (dd, J=0.8, 7.6 Hz, 1H), 7.37-7.30 (m, 5H), 4.51 (s, 2H), 4.03 (s, 3H), 3.32 (d, J=6.4 Hz, 2H), 2.92-2.77 (m, 1H), 2.29-2.15 (m, 2H), 2.00-1.94 (m, 2H), 1.72-1.63 (m, 3H), 1.19-1.03 (m, 2H).

Step 9—Methyl 2-[4-(hydroxymethyl)cyclohexyl]-6-[[6-(trifluoromethyl)pyridine-2-carbonyl]amino]-1H-benzimidazole-5-carboxylate To a solution of methyl 2-[4-(benzyloxymethyl)cyclohexyl]-6-[[6-(trifluoromethyl)pyridine-2-carbonyl]amino]-1H-benzimidazole-5-carboxylate (750 mg, 1.32 mmol) in DCM (10 mL) was added a BCl$_3$-DCM solution (1 M, 13.2 mL) and the reaction mixture was stirred at 20° C. for 1 hr. On completion, the reaction mixture was quenched by saturated NaHCO$_3$ until the pH=8 and extracted with DCM/MeOH=10:1 (3×80 mL). The combined organic layers were washed with brine (2×50 mL), dried over Na$_2$SO$_4$, filtered and concentrated in vacuo. The residue was purified by reverse phase (0.1% FA) to give the title compound (430 mg, 68% yield) as yellow solid, $^1$H NMR (400 MHz, DMSO-d$_6$) δ 13.02-12.76 (m, 1H), 12.57-12.42 (m, 1H), 9.01-8.91 (m, 1H), 8.53-8.45 (m, 1H), 8.39 (t, J=8.0 Hz, 1H), 8.29-8.10 (m, 2H), 3.99-3.89 (m, 3H), 3.28-3.27 (m, 1H), 3.17 (d, J=5.2 Hz, 2H), 2.82 (d, J=12.4 Hz, 1H), 2.15-2.05 (m, 2H), 1.92-1.82 (m, 2H), 1.64-1.53 (m, 2H), 1.49-1.40 (m, 1H), 1.15-1.98 (m, 2H).

Step 10—N-[2-[4-(hydroxymethyl)cyclohexyl]-6-(1-hydroxy-1-methyl-ethyl)-3H-benzimidazol-5-yl]-6-(trifluoromethyl)pyridine-2-carboxamide To a solution of methyl 2-[4-(hydroxymethyl)cyclohexyl]-6-[[6-(trifluoromethyl)pyridine-2-carbonyl]amino]-1H-benzimidazole-5-carboxylate (400 mg, 839 umol) in THF (5 mL) was added MeMgBr (3 M, 2.80 mL) at 0° C. and the reaction mixture was stirred at 0° C. for 1 hr. On completion, the reaction mixture was quenched by saturated $NH_4Cl$ (5 mL) and extracted with DCM/MeOH=10:1 (3×40 mL). The combined organic layers were washed with brine (2×30 mL), dried over $Na_2SO_4$, filtered and concentrated in vacuo. The residue was purified by silica gel chromatography (DCM:MeOH=30:1) to give the title compound (250 mg, 62% yield) as yellow solid. $^1$H NMR (400 MHz, DMSO-$d_6$) δ 12.40 (s, 1H), 8.56 (s, 1H), 8.46 (d, J=7.6 Hz, 1H), 8.36 (t, J=7.6 Hz, 1H), 8.15 (d, J=7.2 Hz, 1H), 7.44 (s, 1H), 5.86 (s, 1H), 4.45 (s, 1H), 3.29-3.25 (m, 2H), 2.81-2.70 (m, 1H), 2.13-2.00 (m, 2H), 1.94-1.80 (m, 2H), 1.67-1.51 (m, 8H), 1.49-1.37 (m, 1H), 1.12-0.97 (m, 2H).

Step 11—N-[2-(4-formylcyclohexyl)-6-(1-hydroxy-1-methyl-ethyl)-3H-benzimidazol-5-yl]-6-(trifluoromethyl)pyridine-2-carboxamide To a solution of N-[2-[4-(hydroxymethyl)cyclohexyl]-6-(1-hydroxy-1-methyl-ethyl)-3H-benzimidazol-5-yl]-6-(trifluoromethyl)pyridine-2-carboxamide (230 mg, 482 umol) in DCM (3 mL) was added DMP (266 mg, 627 umol) and the reaction mixture was stirred at 20° C. for 1 hr. On completion, the reaction mixture was quenched by sat. aq. $Na_2S_2O_3$ (1 mL), basified with sat. aq. $NaHCO_3$ until the pH=8 and extracted with DCM/MeOH=10:1 (3×25 mL). The combined organic layers were washed with brine (2×20 mL), dried over $Na_2SO_4$, filtered and concentrated in vacuo to give the title compound (220 mg, 96% yield) as yellow solid. $^1$H NMR (400 MHz, DMSO-$d_6$) δ 12.52-12.23 (m, 1H), 12.15-11.94 (m, 1H), 8.61-8.53 (m, 1H), 8.51-8.42 (m, 1H), 8.40-8.32 (m, 1H), 8.15 (d, J=8.0 Hz, 1H), 7.55-7.30 (m, 1H), 5.86-5.83 (m, 1H), 2.82-2.68 (m, 1H), 2.15-1.90 (m, 4H), 1.60 (s, 6H), 1.56-1.34 (m, 3H), 1.25-1.10 (m, 2H).

5-(Trifluoromethyl)pyrazolo[1,5-a]pyrimidine-3-carboxamide (Intermediate BPE)

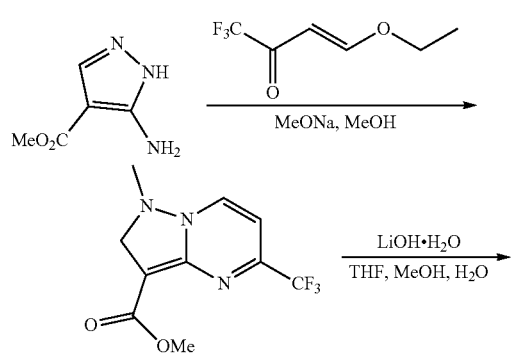

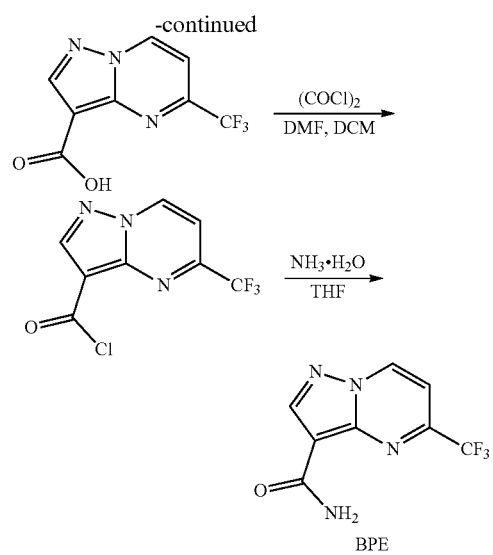

Step 1—5-(Trifluoromethyl)pyrazolo[1,5-a]pyrimidine-3-carboxylate

A mixture of methyl 5-amino-1H-pyrazole-4-carboxylate (1.00 g, 7.09 mmol), 4-ethoxy-1,1,1-trifluoro-but-3-en-2-one (1.20 g, 7.16 mmol, CAS #17129-06-5) and NaOMe (400 mg, 7.40 mmol) in MeOH (20 mL) as stirred at 25° C. for 1 hour. Then, the mixture was stirred at 60° C. for 15 hours. On completion, the mixture was concentrated in vacuo. The residue was diluted with DCM (30 mL), washed with brine (10 mL), dried over $Na_2SO_4$, filtered and concentrated in vacuo to give the title compound (1.10 g, 63% yield) as light yellow solid. $^1$H NMR (400 MHz, $CDCl_3$) δ 8.96 (d, J=7.2 Hz, 1H), 8.74 (s, 1H), 7.34 (d, J=7.2 Hz, 1H), 3.99 (s, 3H).

Step 2—5-(Trifluoromethyl)pyrazolo[1,5-a]pyrimidine-3-carboxylic Acid

To a solution of methyl 5-(trifluoromethyl)pyrazolo[1,5-a]pyrimidine-3-carboxylate (1.10 g, 4.49 mmol) in THF (9 mL) and MeOH (3 mL) was added a solution of LiOH·$H_2O$ (378 mg, 9.01 mmol) in $H_2O$ (3 mL) at 20° C. The mixture was stirred at 50° C. for 1 hour. On completion, after cooled to 25° C., the mixture was acidified to pH=4-5 with 1.0 M aq. HCl. The mixture was concentrated in vacuo and the residue was purified by reversed phase flash (FA condition) to give the title compound (800 mg, 77% yield) as light yellow solid. $^1$H NMR (400 MHz, DMSO-$d_6$) δ 9.60 (d, J=7.2 Hz, 1H), 8.80 (s, 1H), 7.71 (d, J=7.2 Hz, 1H).

Step 3—5-(Trifluoromethyl)pyrazolo[1,5-a]pyrimidine-3-carbonyl Chloride

To a solution of 5-(trifluoromethyl)pyrazolo[1,5-a]pyrimidine-3-carboxylic acid (800 mg, 3.46 mmol) and DMF (0.05 mL) in DCM (10 mL) was added (COCl)$_2$ (884 mg, 6.97 mmol) at 0° C. slowly. The mixture was stirred at 25° C. for 1 hour. On completion, the mixture was concentrated in vacuo to give the title compound (860 mg, 99% yield) as light yellow gum.

Step 4—5-(Trifluoromethyl)pyrazolo[1,5-a]pyrimidine-3-carboxamide

To $NH_3$·$H_2O$ (10 mL) was added a solution of 5-(trifluoromethyl)pyrazolo[1,5-a]pyrimidine-3-carbonyl chloride (860 mg, 3.45 mmol) in THF (10 mL) at 0° C. and the mixture was stirred at 0° C. for 0.5 hour. On completion, the mixture was extracted with EA (3×20 mL). The combine organic layer was washed with brine (10 mL), dried over Na$_2$SO$_4$, filtered and concentrated in vacuo. The residue was purified by column chromatography on silica gel (PE:EA=5: 1-1:1) to give the title compound (370 mg, 46% yield) as light yellow solid. $^1$H NMR (400 MHz, DMSO-d$_6$) δ 9.63 (d, J=7.2 Hz, 1H), 8.78 (s, 1H), 7.70 (d, J=7.2 Hz, 1H), 7.64 (s, 1H), 7.28 (s, 1H).

N-[2-(4-formylcyclohexyl)-6-methoxy-indazol-5-yl]-5-(trifluoromethyl)pyrazolo[1,5-a]pyrimidine-3-carboxamide (Intermediate BPF)

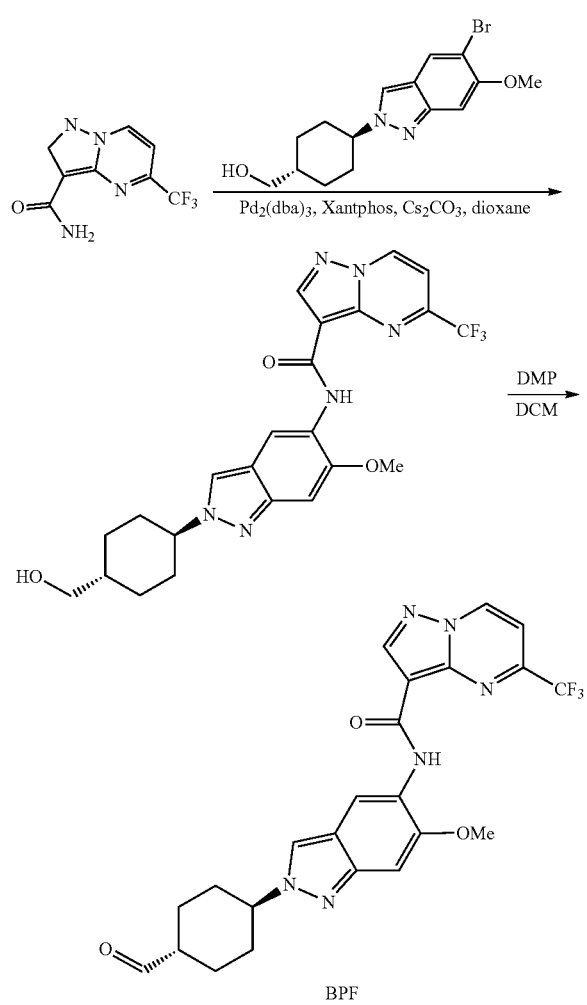

BPF

Step 1—N-[2-[4-(hydroxymethyl)cyclohexyl]-6-methoxy-indazol-5-yl]-5-(trifluoromethyl)pyrazolo[1,5-a]pyrimidine-3-carboxamide A mixture of 5-(trifluoromethyl)pyrazolo[1,5-a]pyrimidine-3-carboxamide (320 mg, 1.39 mmol, Intermediate BPE), [4-(5-bromo-6-methoxy-indazol-2-yl)cyclohexyl]methanol (400 mg, 1.18 mmol, synthesized via Steps 1-3 of Intermediate ATE), Pd$_2$(dba)$_3$ (109 mg, 119 umol), Xantphos (140 mg, 241 umol) and Cs$_2$CO$_3$ (768 mg, 2.36 mmol) in dioxane (10 mL) was stirred at 80° C. for 16 hours under N$_2$. On completion, after the reaction mixture was cooled to 25° C., the mixture was filtered and the filter cake was washed with THF (20 mL). The filtrate and washing were combined and concentrated in vacuo. The residue was purified by reversed phase flash (FA condition) and prep-HPLC (column: Phenomenex Synergi C18 150*25*10 um; mobile phase: [water (0.225% FA)-ACN]; B %: 32%-62%, 10 min) to give the title compound (80.0 mg, 13% yield) as light yellow solid. LC-MS (ESI$^+$) m/z 489.3 (M+H)$^+$.

Step 2—N-[2-(4-formylcyclohexyl)-6-methoxy-indazol-5-yl]-5-(trifluoromethyl)pyrazolo[1,5-a]pyrimidine-3-carboxamide To a solution of N-[2-[4-(hydroxymethyl)cyclohexyl]-6-methoxy-indazol-5-yl]-5-(trifluoromethyl) pyrazolo[1,5-a]pyrimidine-3-carboxamide (70.0 mg, 143 umol) in DCM (3 mL) was added Dess-Martin (70.0 mg, 165 umol) at 15° C. and the mixture was stirred at 15° C. for 2 hours. On completion, the reaction was quenched with sat. aq. Na$_2$S$_2$O$_3$ (5 mL) and the mixture was partitioned, and the aqueous phase was extracted with DCM (2×10 mL). The combined organic layer was washed with sat. aq. NaHCO$_3$ (5 mL) and brine (5 mL), dried over Na$_2$SO$_4$, filtered and concentrated in vacuo to give the title compound (68.0 mg, 98% yield) as light yellow solid. LC-MS (ESI$^+$) m/z 487.1 (M+H)$^+$.

N-(2-((1R,4R)-4-formylcyclohexyl)-6-methoxy-2H-indazol-5-yl)-5-(trifluoromethyl)picolinamide (Intermediate BPG)

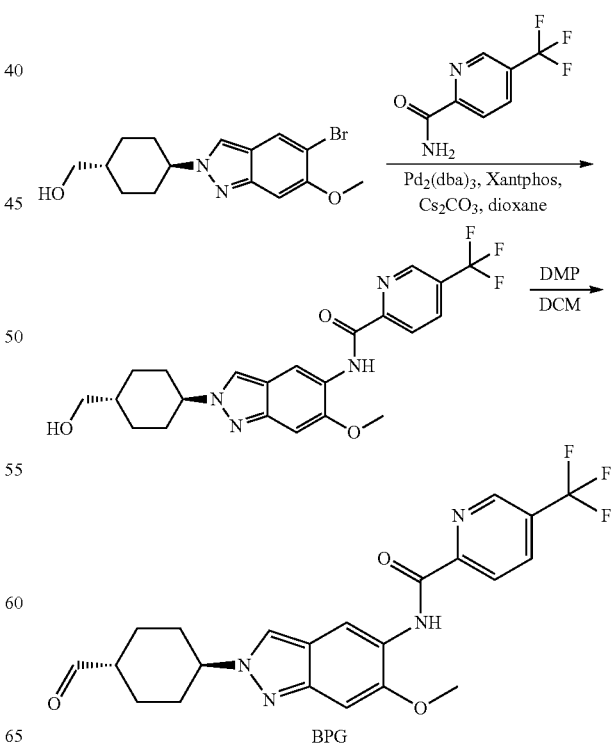

BPG

Step 1—N-(2-((1R,4R)-4-(hydroxymethyl)cyclohexyl)-6-methoxy-2H-indazol-5-yl)-5-(trifluoromethyl) picolinamide To solution of [4-(5-bromo-6-methoxy-indazol-2-yl)cyclohexyl]methanol (313 mg, 922 umol, synthesized via Steps 1-3 of Intermediate ATE) and 5-(trifluoromethyl)pyridine-2-carboxamide (175 mg, 922 umol, 22245-86-9) in the dioxane (10 mL) was added Pd2(dba)3 (84.5 mg, 92.2 umol), Xantphos (107 mg, 184 umol) and Cs$_2$CO$_3$ (601 mg, 1.85 mmol). The mixture was stirred at 100° C. for 24 hrs under N$_2$. On completion, the mixture was concentrated in vacuo and purified by column chromatography (SiO2, PE:EA=10:1 to 0:1) to give the title compound (360 mg, 87% yield) as yellow solid. $^1$H NMR (400 MHz, CHLOROFORM-d) δ=10.68 (s, 1H), 8.99-8.92 (m, 1H), 8.86 (s, 1H), 8.45 (d, J=8.1 Hz, 1H), 8.16 (dd, J=1.8, 8.2 Hz, 1H), 7.89 (s, 1H), 7.09 (s, 1H), 4.33 (tt, J=3.8, 11.9 Hz, 1H), 4.04 (s, 3H), 3.57 (t, J=5.5 Hz, 2H), 2.37-2.29 (m, 2H), 2.06-1.93 (m, 4H), 1.74-1.65 (m, 1H), 1.47 (t, J=5.2 Hz, 1H), 1.29-1.21 (m, 2H).

Step 2—N-(2-((1R,4R)-4-formylcyclohexyl)-6-methoxy-2H-indazol-5-yl)-5-(trifluoromethyl) picolinamide To a solution of N-[2-[4-(hydroxymethyl)cyclohexyl]-6-methoxy-indazol-5-yl]-5-(trifluoromethyl) pyridine-2-carboxamide (60.0 mg, 134 umol) in the DCM (2 mL) was added DMP (68.1 mg, 160 umol) and the mixture was stirred at 25° C. for 1 hour. On completion, the reaction mixture was quenched with saturated Na$_2$S$_2$O$_3$ (aq, 5 mL) and NaHCO$_3$(aq, 5 mL), then the mixture was extracted with DCM (2×20 mL). The organic layer was dried over Na$_2$SO$_4$, filtered and concentrated in vacuo to give the title compound (58.0 mg, 98% yield) as yellow solid. LC-MS (ESI$^+$) m/z 447.1 (M+H)$^+$.

[1-[(4-Methoxyphenyl) methyl]-2,6-dioxo-3-piperidyl] trifluoromethanesulfonate (Intermediate IQ)

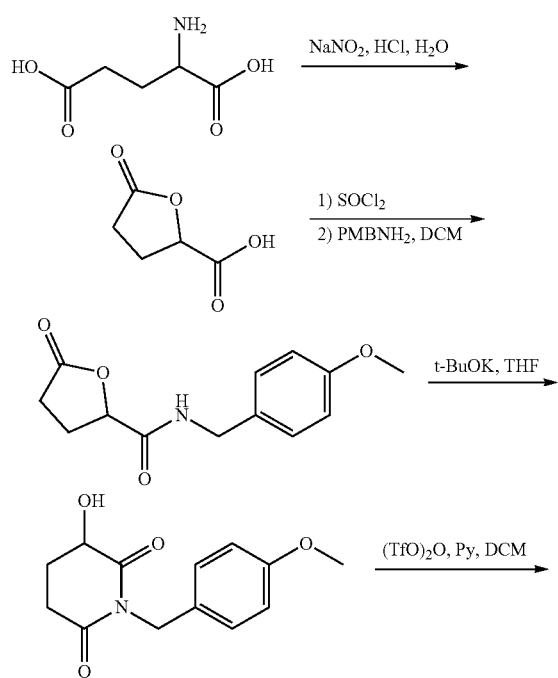

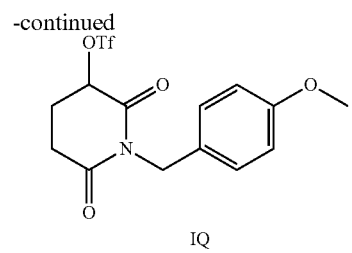

IQ

Step 1—5-Oxotetrahydrofuran-2-carboxylic Acid

To a solution of 2-aminopentanedioic acid (210 g, 1.43 mol, CAS #617-65-2) in H$_2$O (800 mL) and HCl (12 M, 210 mL) was added a solution of NaNO$_2$ (147 g, 2.13 mol) in H$_2$O (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over Na$_2$SO$_4$, filtered and concentrated in vacuo to give the title compound (200 g, crude) as yellow oil. $^1$H NMR (400 MHz, CDCl$_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added SOCl$_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under N$_2$. After that a solution of Et$_3$N (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1$H NMR (400 MHz, CDCl$_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS (ESI$^+$) m/z 272.0 (M+Na)$^+$.

Step 3—3-Hydroxy-1-[(4-methoxyphenyl)methyl]piperidine-2,6-dione

A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated NH$_4$Cl solution (100 mL). The mixture was extracted with ethyl acetate (3×1500 mL). The combined organic layer was washed with brine (300 mL), dried over anhydrous sodium sulfate and the filtrate was concentrated in vacuo. The residue was purified by silica gel chromatography (PE:EA=1:1) to give the title compound (128 g, 92% yield) as a white solid. $^1$H NMR (400 MHz, CDCl₃) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl] trifluoromethanesulfonate To a solution of 3-hydroxy-1-[(4-methoxyphenyl) methyl] piperidine-2,6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under N₂. On completion, the mixture was concentrated in vacuo. The residue was purified by column chromatography on silica gel (PE:EA=20:1/8:1) to give the title compound (45.0 g, 68% yield) as light yellow gum. ¹H NMR (400 MHz, CDCl₃) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

3-(4-Bromo-3-methyl-2-oxo-2,3-dihydro-1H-benzo[d]imidazol-1-yl)piperidine-2,6-dione (Intermediate HP)

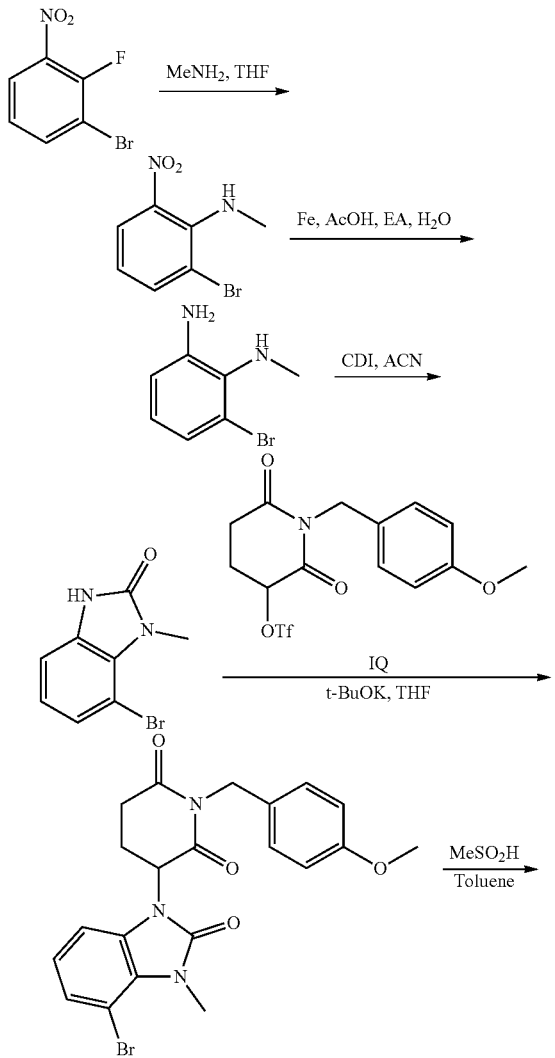

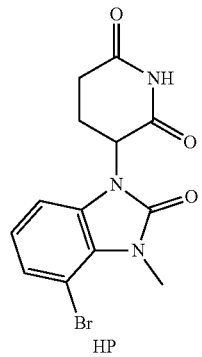

Step 1—2-Bromo-N-methyl-6-nitro-aniline

To a solution of 1-bromo-2-fluoro-3-nitro-benzene (40.0 g, 181 mmol, CAS #58534-94-4) in THF (40 mL) was added MeNH₂ (2 M, 400 mL). The reaction mixture was stirred at 60° C. for 12 hours. On completion, the reaction mixture was poured into sat.NaHCO₃(30 mL) and extracted with EA (3×200 mL). The combined organic layers were washed with brine (2×200 mL), dried with anhydrous Na₂SO₄, filtered and concentrated in vacuo to give the title compound (40.0 g, 95% yield) as red oil. LC-MS (ESI⁺) m/z 230.9 (M+H)⁺.

Step 2—3-Bromo-N2-methyl-benzene-1,2-diamine

To a mixture of 2-bromo-N-methyl-6-nitro-aniline (23.0 g, 99.5 mmol) in EA (300 mL) and H₂O (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over Na₂SO₄, filtered and concentrated in vacuo to give the title compound (20.0 g, 99% yield) as red oil. ¹H NMR (400 MHz, DMSO-d₆) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one

To a mixture of 3-bromo-N2-methyl-benzene-1,2-diamine (20.0 g, 99.4 mmol) in ACN (300 mL) was added CDI (32.2 g, 198 mmol). The reaction mixture was stirred at 85° C. for 12 hours under N₂ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. ¹H NMR (400 MHz, DMSO-d₆) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine-2,6-dione To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl] trifluoromethane-sulfonate (20.1 g, 52.8 mmol, Intermediate IQ) in a solution of THF (100 mL) was added dropwise. The resulting reaction mixture was stirred at 20° C. for 0.5 hr under N₂. On completion, the reaction mixture was quenched with saturated NH₄Cl (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. $^1$H NMR (400 MHz, CDCl₃) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione A mixture of 3-(4-bromo-3-methyl-2-oxo-benzimidazol-1-yl)-1-[(4-methoxyphenyl)methyl]piperidine-2,6-dione (13.3 g, 29.0 mmol) in a mixed solvent of Tol. (80 mL) and methane sulfonic acid (40 mL) was degassed and purged with N₂ for 3 times, and then the mixture was stirred at 120° C. for 2 hrs under N₂ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. $^1$H NMR (400 MHz, DMSO-d₆) δ 11.13 (s, 1H), 7.25 (d, J=8.0 Hz, 1H), 7.17 (d, J=8.0 Hz, 1H), 7.05-6.93 (m, 1H), 5.41 (dd, J=5.2, 12.8 Hz, 1H), 3.64 (s, 3H), 2.96-2.83 (m, 1H), 2.78-2.59 (m, 2H), 2.08-2.00 (m, 1H).

3-(3-Methyl-2-oxo-4-(piperidin-4-yl)-2,3-dihydro-1H-benzo[d]imidazol-1-yl)piperidine-2,6-dione (Intermediate AZK)

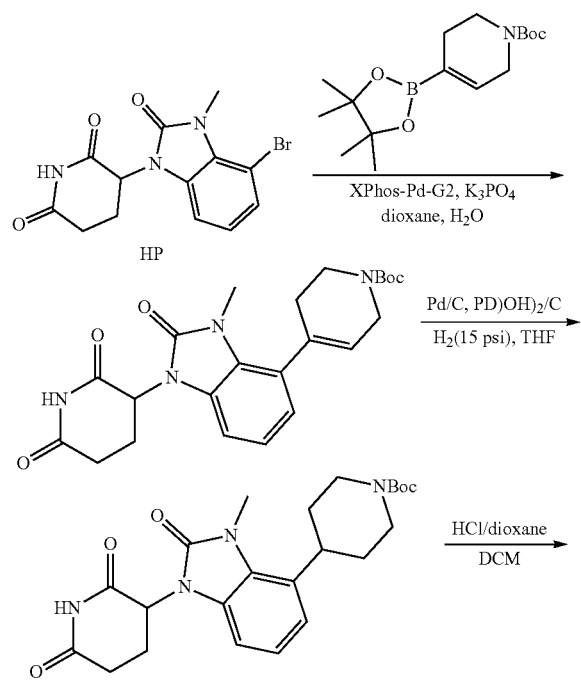

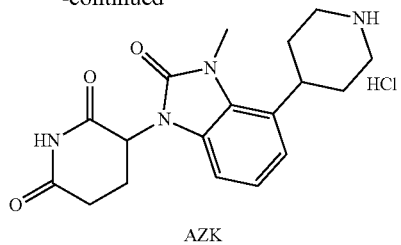

Step 1—Tert-butyl 4-(1-(2,6-dioxopiperidin-3-yl)-3-methyl-2-oxo-2,3-dihydro-1H-benzo[d]imidazol-4-yl)-5,6-dihydropyridine-1(2H)-carboxylate To a solution of 3-(4-bromo-3-methyl-2-oxo-benzimidazol-1-yl)piperidine-2,6-dione (9.00 g, 26.6 mmol, Intermediate HP), tert-butyl 4-(4,4,5,5-tetramethyl-1,3,2-dioxaborolan-2-yl)-3,6-dihydro-2H-pyridine-1-carboxylate (12.3 g, 39.9 mmol) and XPhos-Pd-G2 (2.09 g, 2.66 mmol) in dioxane (150 mL) and H₂O (15 mL) was added K₃PO₄ (11.3 g, 53.2 mmol). The reaction mixture was stirred at 80° C. for 4 hours under N₂. On completion, the reaction mixture was filtered. The filtrate was dried with anhydrous Na₂SO₄ and filtered. The filtrate was concentrated in vacuo. The residue was triturated with sat. NH₄Cl (2×50 mL), water (2×50 mL) and EA (2×50 mL) and filtered. The solid was dried in vacuo to give the title compound (8.00 g, 68% yield) as an off-white solid. LC-MS (ESI⁺) m/z 441.1 (M+H)⁺

Step 2—Tert-butyl 4-(1-(2,6-dioxopiperidin-3-yl)-3-methyl-2-oxo-2,3-dihydro-1H-benzo[d]imidazol-4-yl)piperidine-1-carboxylate To a solution of tert-butyl 4-[1-(2,6-dioxo-3-piperidyl)-3-methyl-2-oxo-benzimidazol-4-yl]-3,6-dihydro-2H-pyridine-1-carboxylate (8.00 g, 18.2 mmol) in DMF (20 mL) and THF (60 mL) was added H2, Pd/C (1.00 g, 10 wt %) and Pd(OH)₂ (1.00 g, 3.56 mmol, 50 wt %). The mixture was degassed and purged with nitrogen 3 times, then degassed and purged with hydrogen 3 times. The mixture was stirred at 25° C. for 16 hrs under hydrogen (15 psi) atmosphere. On completion, the reaction mixture was filtered and the combined filtrates were concentrated in vacuo to give the title compound (5.60 g, 70% yield) as a white solid. $^1$H NMR (400 MHz, DMSO-d₆) δ 11.10 (s, 1H), 7.06-6.92 (m, 3H), 5.38 (m, 1H), 4.18-3.96 (m, 2H), 3.60 (s, 3H), 3.48-3.39 (m, 1H), 2.97-2.81 (m, 3H), 2.76-2.61 (m, 2H), 2.05-1.94 (m, 1H), 1.81 (m, 2H), 1.65-1.50 (m, 2H), 1.47-1.40 (m, 9H). LC-MS (ESI⁺) m/z 287.4 (387.3)⁺.

Step 3—3-(3-Methyl-2-oxo-4-(piperidin-4-yl)-2,3-dihydro-1H-benzo[d]imidazol-1-yl)piperidine-2,6-dione To a solution of tert-butyl 4-[1-(2,6-dioxo-3-piperidyl)-3-methyl-2-oxo-benzimidazol-4-yl]piperidine -1-carboxylate (100 mg, 226 umol) in DCM (1 mL) was added HCl/dioxane (1 mL). The reaction mixture was stirred at 25° C. for 0.5 hr. On completion, the reaction mixture was concentrated in vacuo to give the title compound (85.0 mg, 99% yield) as a yellow solid. LC-MS (ESI⁺) m/z 343.3 (M+H)⁺.

1-(2,6-dioxo-3-piperidyl)-3-methyl-2-oxo-benzimidazole-4-carbaldehyde (Intermediate WW)

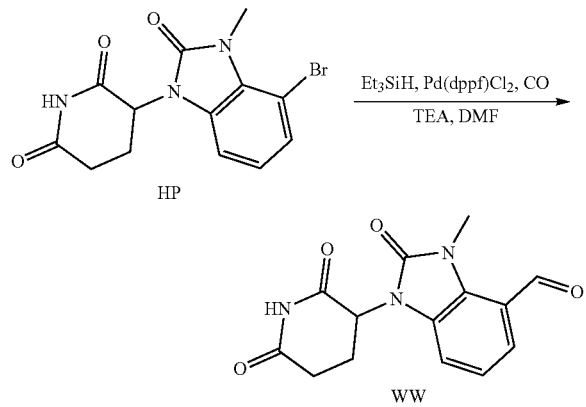

To a solution of 3-(4-bromo-3-methyl-2-oxo-2,3-dihydro-1H-benzo[d]imidazol-1-yl)piperidine-2,6-dione (500 mg, 1.48 mmol, Intermediate HP) in DMF (20 mL) was added TEA (448 mg, 4.44 mmol), Pd(dppf)Cl$_2$ (162 mg, 221 umol) and Et$_3$SiH (515 mg, 4.44 mmol). The reaction mixture was stirred at 80° C. for 16 hours under CO (50 Psi). On completion, the reaction mixture was concentrated in vacuo and purified by reverse phase (0.1% FA) to give the title compound (400 mg, 47% yield) as a white solid. LC-MS (ESI$^+$) m/z 288.0 (M+H)$^+$.

3-[3-Methyl-4-[[4-(methylamino)-1-piperidyl]methyl]-2-oxo-benzimidazol-1-yl]piperidine -2,6-dione (Intermediate WX)

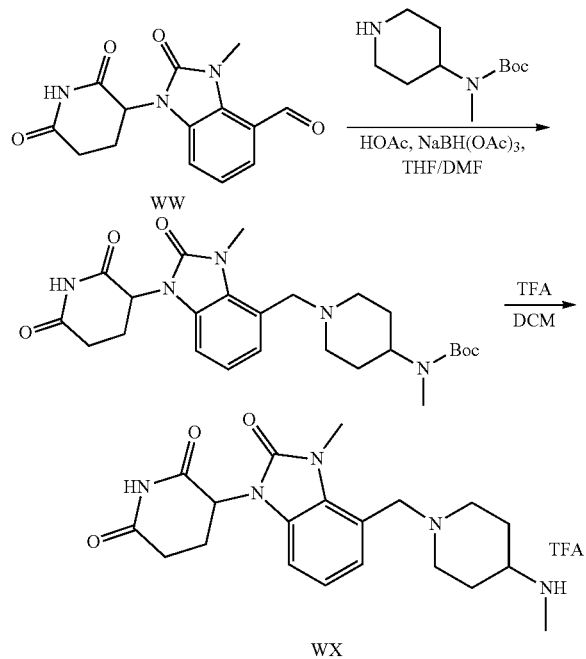

Step 1—Tert-butyl N-[1-[[1-(2,6-dioxo-3-piperidyl)-3-methyl-2-oxo-benzimidazol-4-yl]methyl]-4-piperidyl]-N-methyl-carbamate To a solution of 1-(2,6-dioxo-3-piperidyl)-3-methyl-2-oxo-benzimidazole-4-carbaldehyde (160 mg, 556 umol, Intermediate WW) and tert-butyl N-methyl-N-(4-piperidyl) carbamate (119 mg, 556 umol) in a mixed solvents of THF (3 mL) and DMF (1.5 mL) was added AcOH until pH=5-7. After the reaction mixture was stirred at 20° C. for 3 hours. NaBH(OAc)$_3$ (177 mg, 835 umol) was added to the reaction mixture. The mixture was stirred at 20° C. for 12 hours. On completion, the reaction mixture was quenched by water (3 drops) and filtered. The filtrate was concentrated in vacuo. The residue was purified by reverse phase (FA condition) to give the title compound (220 mg, 46% yield) as white solid. LC-MS (ESI$^+$) m/z 486.2 (M+H)$^+$.

Step 2—3-[3-Methyl-4-[[4-(methylamino)-1-piperidyl]methyl]-2-oxo-benzimidazol-1-yl]piperidine-2,6-dione To a solution of tert-butyl N-[1-[[1-(2,6-dioxo-3-piperidyl)-3-methyl-2-oxo-benzimidazol-4-yl]methyl]-4-piperidyl]-N-methyl-carbamate (200 mg, 235 umol) in DCM (3 mL) was added TFA (3 mL). The reaction mixture was stirred at 15° C. for 0.5 hour. On completion, the reaction mixture was concentrated in vacuo to give the title compound (220 mg, 100% yield, TFA salt) as yellow oil. LC-MS (ESI$^+$) m/z 386.2 (M+H)$^+$.

Tert-butyl 6-(2-aminoethyl)-2-azaspiro[3.3]heptane-2-carboxylate (Intermediate ATG)

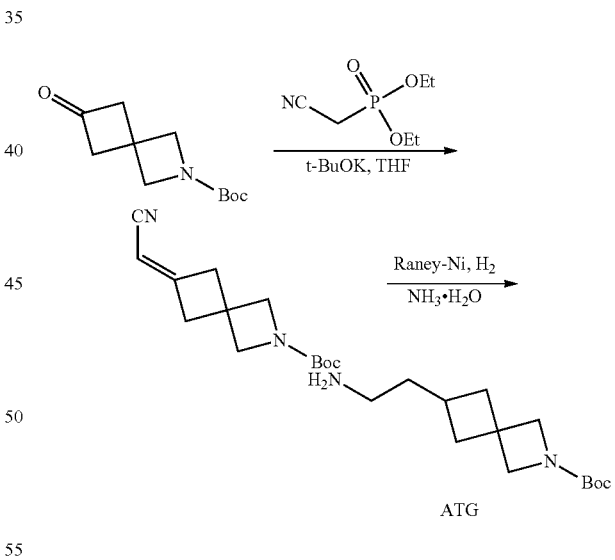

Step 1—Tert-butyl 6-(cyanomethylene)-2-azaspiro[3.3]heptane-2-carboxylate

To a solution of t-BuOK (3.98 g, 35.5 mmol) in THF (35 mL) was added a solution of 2-diethoxyphosphorylacetonitrile (6.29 g, 35.5 mmol) in THF (70 mL) at 0° C. dropwise, and the reaction was stirred at 25° C. for 0.5 h. After, the mixture was cooled to 0° C. and a solution of tert-butyl 6-oxo-2-azaspiro[3.3]heptane-2-carboxylate (5.00 g, 23.7 mmol, CAS #1147557-97-8) in THF (35 mL) was added and the reaction was stirred at 25° C. for 16 hours. On completion, the reaction was quenched with water (10 mL) and the solvent was removed in vacuo to give a residue. The residue was purified by silica gel column chromatography (PE:EA from 5:1 to 1:1) to give the title compound (4.10 g, 66% yield) as a yellow oil. $^1$H NMR (400 MHz, DMSO-d$_6$) δ 5.55 (t, J=2.4 Hz, 1H), 3.91 (d, J=2.0 Hz, 4H), 3.17-3.01 (m, 4H), 1.37 (s, 9H).

Step 2—Tert-butyl 6-(2-aminoethyl)-2-azaspiro[3.3]heptane-2-carboxylate

To a solution of tert-butyl 6-(cyanomethylene)-2-azaspiro[3.3]heptane-2-carboxylate (4.10 g, 17.5 mmol) in MeOH (80 mL) and NH$_3$·H$_2$O (8 mL) was added Raney-Ni (1.50 g, 17.5 mmol). The mixture was degassed and purged with H$_2$ gas 3 times and then was stirred at 25° C. under H$_2$ at 50 psi for 3 hours. On completion, the reaction was filtered through celite, the filtered cake was washed with MeOH (3×5 mL) and the filtrate was concentrated in vacuo to give the title compound (3.10 g, 66% yield) as yellow oil. $^1$H NMR (400 MHz, DMSO-d$_6$) δ 3.82 (d, J=7.6 Hz, 4H), 2.47-2.00 (m, 5H), 1.79-1.67 (m, 2H), 1.46-1.38 (m, 2H), 1.36 (s, 9H).

2-(2,6-Dioxopiperidin-3-yl)-4-fluoroisoindoline-1,3-dione (Intermediate R)

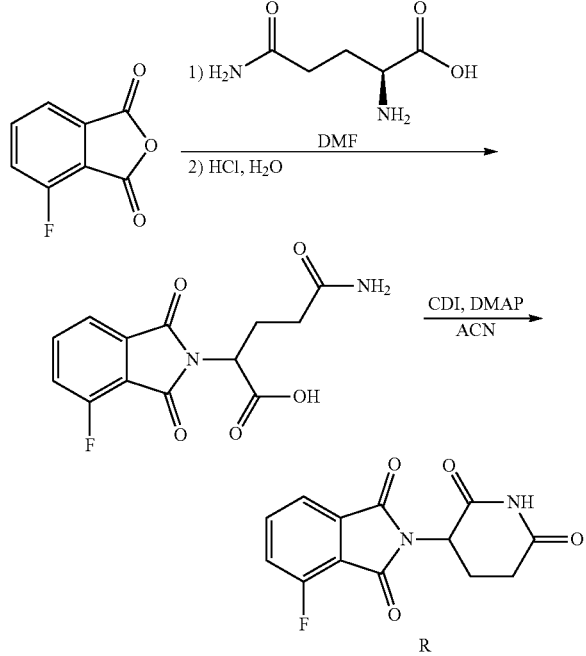

Step 1—5-amino-2-(4-fluoro-1,3-dioxoisoindolin-2-yl)-5-oxopentanoic Acid

To a stirred solution of 4-fluoroisobenzofuran-1,3-dione (25 g, 150 mmol, CAS #652-39-1) in DMF (100 mL) was added L-glutamine (22 g, 150 mmol) at rt. The resulting reaction mixture was heated to at 90° C. and stirred for 2 h. The reaction mixture was then evaporated under reduced pressure, transferred into 4N aqueous HCl solution and the resulting mixture was stirred for 36 h at rt. The solid precipitate was then filtered off, washed with cold water and dried under reduced pressure to give 5-amino-2-(4-fluoro-1,3-dioxoisoindolin-2-yl)-5-oxopentanoic acid as a white solid (28 g, 63%). LC-MS (ESI$^+$) m/z 295 (M+H)$^+$.

Step 2—2-(2,6-dioxopiperidin-3-yl)-4-fluoroisoindoline-1,3-dione

To a stirred solution of 5-amino-2-(4-fluoro-1,3-dioxoisoindolin-2-yl)-5-oxopentanoic acid (28 g, 95 mmol) in acetonitrile (200 mL) was added CDI (19 g, 110 mmol) and DMAP (0.14 g, 1.1 mmol) at rt. The resulting reaction mixture then heated to 90° C. and stirred for 5 h. The reaction mixture was then evaporated under reduced pressure. The crude product was purified using silica gel column chromatography (2% MeOH-DCM) to give 2-(2,6-dioxopiperidin-3-yl)-4-fluoroisoindoline-1,3-dione as a yellow solid (12 g, 46%). $^1$H NMR (400 MHz, DMSO) δ ppm 11.16 (s, 1H), 7.98-7.93 (m, 1H), 7.80-7.76 (m, 2H), 5.19-5.14 (m, 1H), 2.94-2.85 (m, 1H), 2.63-2.54 (m, 2H), 2.09-2.04 (m, 1H).

4-[2-(2-Azaspiro[3.3]heptan-6-yl)ethylamino]-2-(2,6-dioxo-3-piperidyl)isoindoline-1,3-dione (Intermediate ATH)

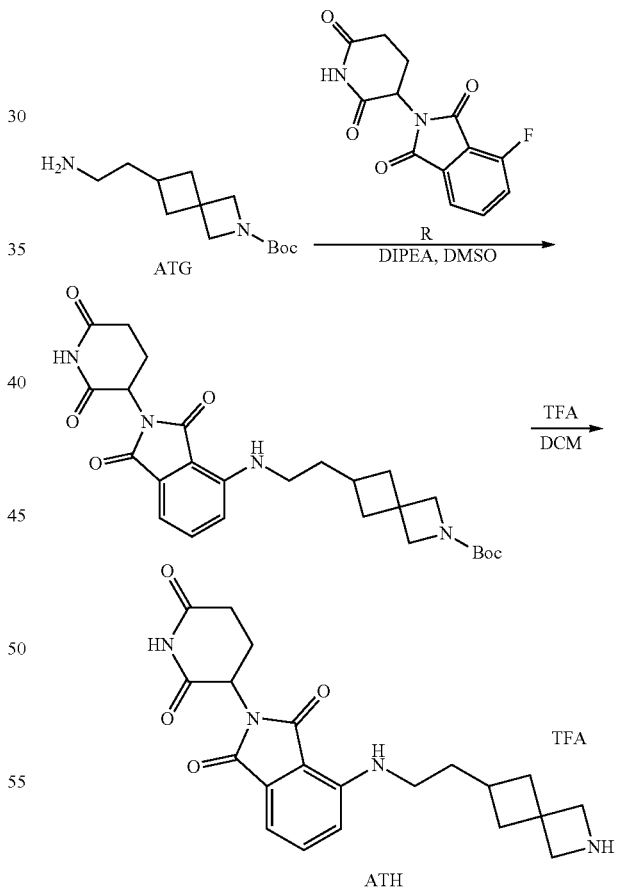

Step 1—Tert-butyl 6-[2-[[2-(2,6-dioxo-3-piperidyl)-1,3-dioxo-isoindolin-4-yl]amino]ethyl]-2-azaspiro[3.3]heptane-2-carboxylate To a solution of tert-butyl 6-(2-aminoethyl)-2-azaspiro[3.3]heptane-2-carboxylate (3.00 g, 12.5 mmol, Intermediate ATG) and 2-(2,6-dioxo-3-piperidyl)-4-fluoro-isoindoline-1,3-dione (3.79 g, 13.7 mmol, Intermediate R) in DMSO (30 mL) was added DIPEA (4.84 g, 37.5 mmol). The mixture was stirred at 130° C. for 1 hour. On completion, the reaction was diluted with EA (150 mL), washed with water (3×50 mL) and brine (100 mL), dried over $Na_2SO_4$, filtered and concentrated in vacuo to give a crude product which was purified by reversed phase (0.1% FA condition) to give the title compound (3.20 g, 46% yield) as a yellow solid. $^1$H NMR (400 MHz, DMSO-$d_6$) δ 11.10 (s, 1H), 7.59 (dd, J=7.2, 8.4 Hz, 1H), 7.11-6.97 (m, 2H), 6.49 (t, J=5.6 Hz, 1H), 5.06 (dd, J=5.6, 12.8 Hz, 1H), 3.84 (s, 2H), 3.73 (s, 2H), 3.22 (q, J=6.4 Hz, 2H), 2.91-2.83 (m, 1H), 2.65-2.54 (m, 2H), 2.32-2.22 (m, 2H), 2.16 (t, J=7.6 Hz, 1H), 2.04 (d, J=2.4 Hz, 1H), 1.86-1.78 (m, 2H), 1.65 (q, J=7.2 Hz, 2H), 1.36 (s, 9H); LC-MS (ESI$^+$) m/z 497.3 (M+H)$^+$.

Step 2—4-[2-(2-Azaspiro[3.3]heptan-6-yl)ethylamino]-2-(2,6-dioxo-3-piperidyl)isoindoline-1,3-dione To a solution of tert-butyl 6-[2-[[2-(2,6-dioxo-3-piperidyl)-1,3-dioxo-isoindolin-4-yl]amino]ethyl]-2-azaspiro[3.3]heptane-2-carboxylate (0.30 g, 604 umol) in DCM (3 mL) was added TFA (2.31 g, 20.3 mmol). The mixture was stirred at 25° C. for 1 hour. On completion, the reaction was concentrated in vacuo to give the title compound (0.18 g, TFA, 58% yield) as a yellow solid. LC-MS (ESI$^+$) m/z 397.2 (M+H)$^+$.

Tert-butyl 2-(aminomethyl)-7-azaspiro[3.5]nonane-7-carboxylate (Intermediate AJZ)

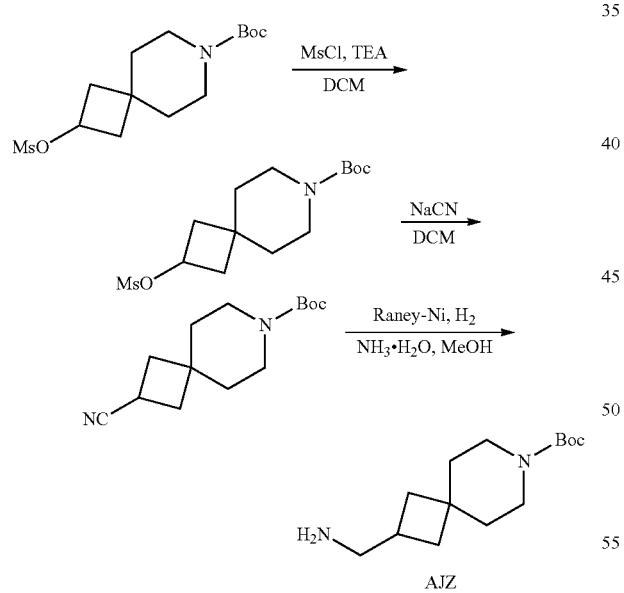

Step 1—Tert-butyl 2-methylsulfonyloxy-7-azaspiro[3.5]nonane-7-carboxylate

To a solution of tert-butyl 2-hydroxy-7-azaspiro[3.5]nonane-7-carboxylate (2.00 g, 8.29 mmol, CAS #240401-28-9) and TEA (2.10 g, 20.7 mmol) in DCM (30 mL) was added MsCl (1.14 g, 9.95 mmol) dropwise at 0° C. Then the reaction mixture was stirred at 20° C. for 2 hrs. On completion, the mixture was quenched with water (50 mL), then extracted with DCM (2×50 mL). The organic layer was washed with citric acid (100 ml), brine (2×100 mL), dried with $Na_2SO_4$, filtered and the filtrate was concentrated in vacuo to give the title compound (2.60 g, 98% yield) as a yellowish oil. $^1$H NMR (400 MHz, CDCl$_3$) δ 5.04 (t, J=7.2 Hz, 1H), 3.38-3.28 (m, 4H), 2.99 (s, 3H), 2.48-2.36 (m, 2H), 2.14-2.04 (m, 2H), 1.58-1.51 (m, 4H), 1.45 (s, 9H).

Step 2—Tert-butyl 2-cyano-7-azaspiro[3.5]nonane-7-carboxylate

To a solution of tert-butyl 2-methylsulfonyloxy-7-azaspiro[3.5]nonane-7-carboxylate (2.60 g, 8.14 mmol) in DMF (20 mL) was added NaCN (598 mg, 12.2 mmol). The reaction mixture was stirred at 120° C. for 3 days. On completion, the reaction mixture was cooled to 25° C., diluted with water (100 mL), then extracted with EA (2×100 mL). The organic layer was washed with brine (2×100 mL) and concentrated in vacuo. The residue was purified by silica gel chromatography to give the title compound (1.32 g, 65% yield) as a white solid. $^1$H NMR (400 MHz, CDCl$_3$) δ 3.36-3.29 (m, 4H), 3.13-3.02 (m, 1H), 2.30-2.14 (m, 4H), 1.66-1.62 (m, 2H), 1.58-1.53 (m, 2H), 1.45 (s, 9H).

Step 3—Tert-butyl 2-(aminomethyl)-7-azaspiro[3.5]nonane-7-carboxylate

To a solution of tert-butyl 2-cyano-7-azaspiro[3.5]nonane-7-carboxylate (200 mg, 799 umol) and $NH_3$—$H_2O$ (0.2 mL) in MeOH (5 mL) was added Raney-Ni (30 mg). The reaction mixture was stirred at 20° C. for 16 hrs under H$_2$ (15 Psi) atmosphere. On completion, the mixture was filtered and the filtrate was concentrated in vacuo to give the title compound (200 mg, 98% yield) as a white solid. $^1$H NMR (400 MHz, CDCl$_3$) δ 3.37-3.32 (m, 2H), 3.30-3.23 (m, 2H), 2.70 (d, J=7.2 Hz, 2H), 2.33-2.24 (m, 1H), 1.97-1.88 (m, 2H), 1.59-1.55 (m, 2H), 1.45 (s, 9H), 1.44-1.37 (m, 4H).

4-(7-azaspiro[3.5]nonan-2-ylmethylamino)-2-(2,6-dioxo-3-piperidyl)isoindoline-1,3-dione (Intermediate AJF)

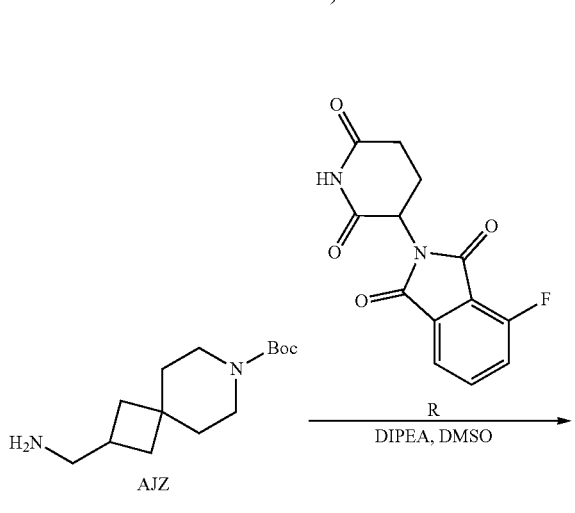

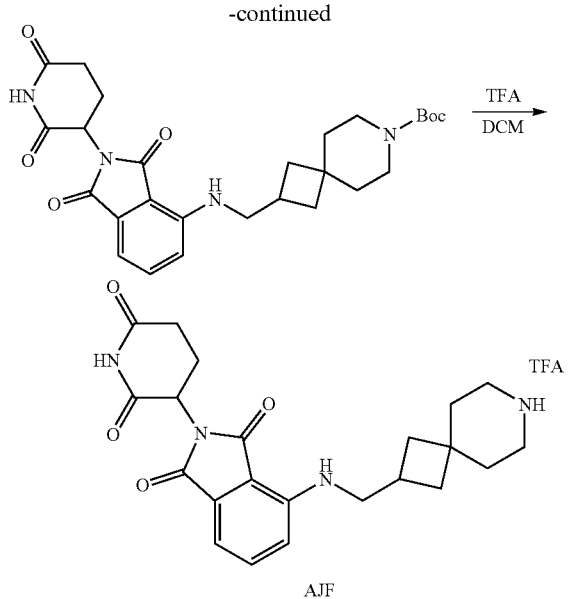

AJF

Step 1—Tert-butyl 2-[[[2-(2,6-dioxo-3-piperidyl)-1,3-dioxo-isoindolin-4-yl]amino]methyl]-7-azaspiro[3.5]nonane-7-carboxylate To a solution of tert-butyl 2-(aminomethyl)-7-azaspiro[3.5]nonane-7-carboxylate (200 mg, 786 umol, Intermediate AJZ) and 2-(2,6-dioxo-3-piperidyl)-4-fluoro-isoindoline-1,3-dione (228 mg, 825 umol, Intermediate R) in DMSO (3 mL) was added DIPEA (254 mg, 1.97 mmol). The reaction mixture was stirred at 125° C. for 3 hrs. On completion, the reaction mixture was diluted with water (50 mL), then extracted with EA (50 mL). The organic layer was concentrated in vacuo. The residue was purified by reverse phase (0.1% FA condition) to give the title compound (260 mg, 65% yield) as a yellow solid. LC-MS (ESI$^+$) m/z 511.3 (M+H)$^+$.

Step 2—4-(7-Azaspiro[3.5]nonan-2-ylmethyl-amino)-2-(2,6-dioxo-3-piperidyl)isoindoline-1,3-dione To a solution of tert-butyl 2-[[[2-(2,6-dioxo-3-piperidyl)-1,3-dioxo-isoindolin-4-yl]amino]methyl]-7-azaspiro[3.5]nonane-7-carboxylate (80.0 mg, 157 umol) in TFA (2 mL) was added DCM (2 mL). The reaction mixture was stirred at 20° C. for 2 hrs. On completion, the mixture was concentrated in vacuo to give the title compound (80 mg, 97% yield, TFA salt) as a yellow solid. LC-MS (ESI$^+$) m/z 411.2 (M+H)$^+$

Tert-butyl 2-(2-aminoethyl)-7-azaspiro[3.5]nonane-7-carboxylate (Intermediate ATB)

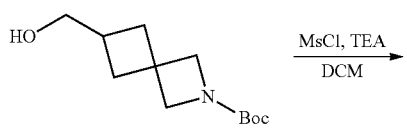

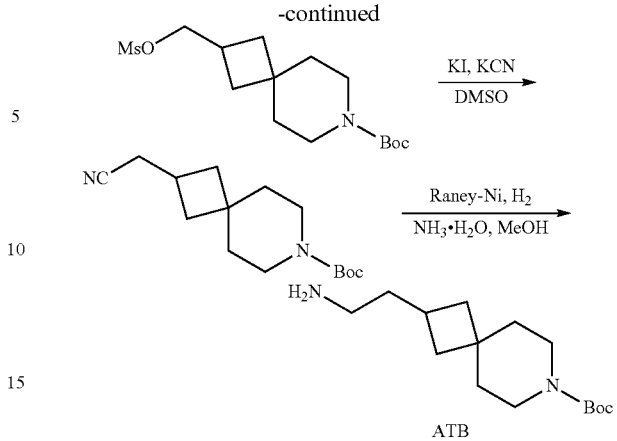

ATB

Step 1—Tert-butyl 2-(methylsulfonyloxymethyl)-7-azaspiro[3.5]nonane-7-carboxylate To a solution of tert-butyl 2-(hydroxymethyl)-7-azaspiro[3.5]nonane-7-carboxylate (1.00 g, 3.92 mmol, CAS #1356476-27-1) and TEA (594 mg, 5.87 mmol) in DCM (15 mL) was added MsCl (538 mg, 4.70 mmol) at 0° C. The reaction mixture was stirred at 0-20° C. for 1 hr. On completion, the reaction mixture was diluted with water (30 mL) and extracted with DCM (3×40 mL). The combined organic layers were washed with brine (2×30 mL), dried over Na$_2$SO$_4$, filtered and concentrated in vacuo to give the title compound (1.20 g, 91% yield) as yellow oil. $^1$H NMR (400 MHz, CDCl$_3$) δ 4.20 (d, J=6.4 Hz, 2H), 3.41-3.32 (m, 2H), 3.30-3.23 (m, 2H), 3.02 (s, 3H), 2.75-2.62 (m, 1H), 2.03-1.93 (m, 2H), 1.66-1.61 (m, 2H), 1.61-1.59 (m, 1H), 1.58-1.56 (m, 1H), 1.50-1.47 (m, 2H), 1.45 (s, 9H).

Step 2—Tert-butyl 2-(cyanomethyl)-7-azaspiro[3.5]nonane-7-carboxylate

To a solution of tert-butyl 2-(methylsulfonyloxymethyl)-7-azaspiro[3.5]nonane-7-carboxylate (1.20 g, 3.60 mmol) and KI (896 mg, 5.40 mmol) in DMSO (15 mL) was added KCN (257 mg, 3.96 mmol) at 25° C. The reaction mixture was stirred at 100° C. for 4 hrs. On completion, the reaction mixture was diluted with water (100 mL) and extracted with EA (3×60 mL). The combined organic layers were washed with brine (2×30 mL), dried over Na$_2$SO$_4$, filtered and concentrated in vacuo. The residue was purified by silica gel chromatography (PE:EA=10:1) to give the title compound (510 mg, 53% yield) as yellow solid. $^1$H NMR (400 MHz, CDCl$_3$) δ 3.43-3.33 (m, 2H), 3.31-3.22 (m, 2H), 2.70-2.52 (m, 1H), 2.45 (d, J=6.4 Hz, 2H), 2.14-1.99 (m, 2H), 1.68-1.58 (m, 4H), 1.54-1.48 (m, 2H), 1.46 (s, 9H).

Step 3—Tert-butyl 2-(2-aminoethyl)-7-azaspiro[3.5]nonane-7-carboxylate

To a solution of tert-butyl 2-(cyanomethyl)-7-azaspiro[3.5]nonane-7-carboxylate (0.50 g, 1.89 mmol) and NH$_3$—H$_2$O (910 mg, 7.27 mmol, 28% solution) in MeOH (10 mL) was added Raney-Ni (32.4 mg, 378 umol). The reaction mixture was stirred at 20° C. for 3 hrs under hydrogen (50 psi). On completion, the reaction mixture was filtered and the filter cake was washed with methanol (50 mL). The combined organic phase was concentrated in vacuo to give the title compound (400 mg, 78% yield) as colorless oil. $^1$H NMR (400 MHz, DMSO-d$_6$) δ 3.25-3.23 (m, 2H), 3.17-3.14 (m, 2H), 2.42 (t, J=7.2 Hz, 2H), 2.30-2.17 (m, 1H), 1.93-1.84 (m, 2H), 1.49-1.41 (m, 4H), 1.37 (s, 9H), 1.36-1.28 (m, 4H).

4-[2-(7-Azaspiro[3.5]nonan-2-yl)ethylamino]-2-(2,6-dioxo-3-piperidyl)isoindoline-1,3-dione (Intermediate ATC)

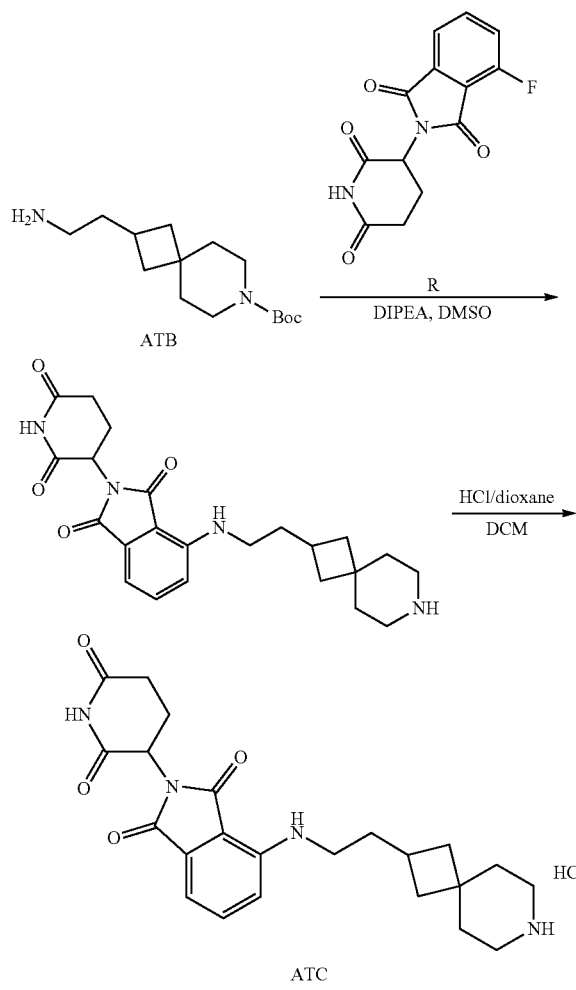

Step 1—Tert-butyl 2-[2-[[2-(2,6-dioxo-3-piperidyl)-1,3-dioxo-isoindolin-4-yl]amino]ethyl]-7-azaspiro[3.5]nonane-7-carboxylate To a solution of tert-butyl 2-(2-aminoethyl)-7-azaspiro[3.5]nonane-7-carboxylate (160 mg, 596 umol, Intermediate ATB) and 2-(2,6-dioxo-3-piperidyl)-4-fluoro-isoindoline-1,3-dione (181 mg, 655 umol, Intermediate R) in DMSO (3 mL) was added DIPEA (154 mg, 1.19 mmol). The reaction mixture was stirred at 130° C. for 2 hrs. On completion, the reaction mixture was diluted with water (10 mL) and extracted with EA (3×30 mL). The combined organic layers were washed with brine (20 mL), dried over Na$_2$SO$_4$, filtered and concentrated in vacuo. The residue was purified by reverse phase (0.1% FA) to give the title compound (200 mg, 63% yield) as yellow solid. $^1$H NMR (400 MHz, DMSO-d$_6$) δ 11.08 (s, 1H), 7.58 (dd, J=7.2, 8.4 Hz, 1H), 7.07 (d, J=8.4 Hz, 1H), 7.02 (d, J=6.8 Hz, 1H), 6.47 (t, J=5.6 Hz, 1H), 5.04 (dd, J=5.2, 12.8 Hz, 1H), 3.28-3.24 (m, 2H), 3.24-3.20 (m, 2H), 3.19-3.14 (m, 2H), 2.93-2.80 (m, 1H), 2.63-2.54 (m, 2H), 2.31-2.22 (m, 1H), 2.07-1.99 (m, 1H), 1.98-1.90 (m, 2H), 1.74-1.64 (m, 2H), 1.51-1.38 (m, 6H), 1.37 (s, 9H).

Step 2—4-[2-(7-Azaspiro[3.5]nonan-2-yl)ethylamino]-2-(2,6-dioxo-3-piperidyl)isoindoline-1,3-dione To a solution of tert-butyl 2-[2-[[2-(2,6-dioxo-3-piperidyl)-1,3-dioxo-isoindolin-4-yl]amino]ethyl]-7-azaspiro[3.5]nonane-7-carboxylate (50.0 mg, 95.3 umol) in DCM (1 mL) was added HCl/dioxane (4 M, 0.5 mL). The reaction mixture was stirred at 20° C. for 1 hr. On completion, the reaction mixture was concentrated in vacuo to give the title compound (43.0 mg, 97% yield, HCl salt) as yellow solid. LC-MS (ESI$^+$) m/z 425.3 (M+H)$^+$.

4-(7-Azaspiro[3.5]nonan-2-ylamino)-2-(2,6-dioxo-3-piperidyl)isoindoline-1,3-dione (Intermediate AML)

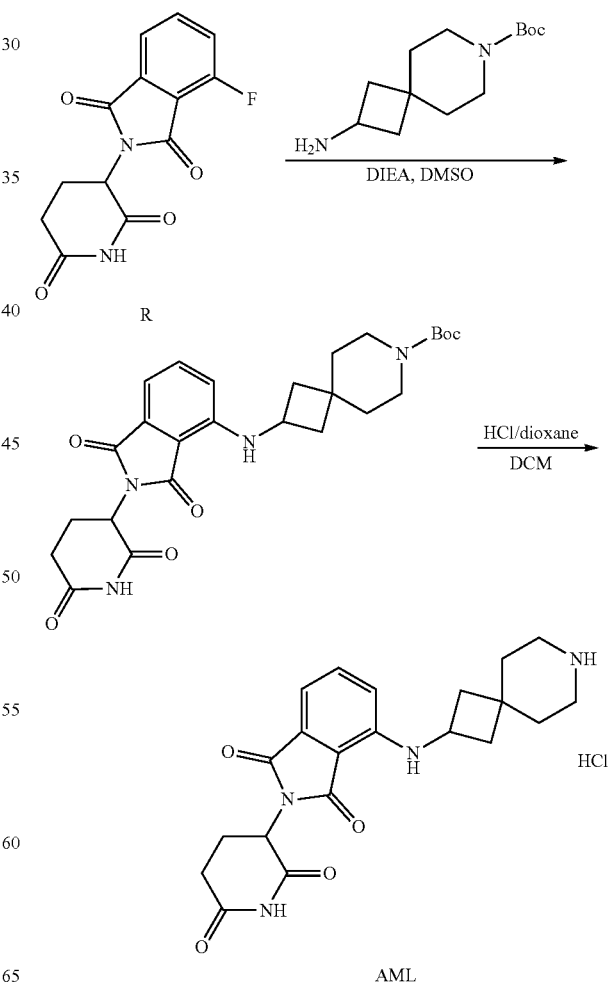

Step 1—Tert-butyl [[2-(2,6-dioxo-3-piperidyl)-1,3-dioxo-isoindolin-4-yl]amino]-7-azaspiro[3.5]nonane-7-carboxylate To a mixture of 2-(2,6-dioxo-3-piperidyl)-4-fluoro-isoindoline-1,3-dione (0.50 g, 1.81 mmol, Intermediate R) and tert-butyl 2-amino-7-azaspiro[3.5]nonane-7-carboxylate (478 mg, 1.99 mmol, CAS #1239319-82-4) in DMSO (10 mL) was added DIPEA (468 mg, 3.62 mmol). The mixture was stirred at 130° C. for 2 hours. On completion, the reaction mixture was poured into the water (30 mL), and extracted with EA (2×20 mL). The combined organic phase was washed with brine (2×30 mL), dried with anhydrous Na$_2$SO$_4$, filtered and concentrated in vacuo to give the title compound (0.80 g, 89% yield) as a yellow solid. $^1$H NMR (400 MHz, CDCl$_3$) δ 8.33 (s, 1H), 7.48 (d, J=7.8 Hz, 1H), 7.11 (d, J=7.2 Hz, 1H), 6.74 (d, J=8.4 Hz, 1H), 6.31 (d, J=5.6 Hz, 1H), 4.95-4.89 (m, 1H), 4.08-3.99 (m, 1H), 3.42-3.35 (m, 2H), 3.33-3.26 (m, 2H), 2.93-2.84 (m, 1H), 2.83-2.71 (m, 2H), 2.48-2.35 (m, 2H), 2.17-2.09 (m, 1H), 1.78-1.71 (m, 2H), 1.65-1.60 (m, 2H), 1.58-1.52 (m, 2H), 1.45 (s, 9H).

Step 2—4-(7-Azaspiro[3.5]nonan-2-ylamino)-2-(2,6-dioxo-3-piperidyl)isoindoline-1,3-dione To a mixture of tert-butyl 2-[[2-(2,6-dioxo-3-piperidyl)-1,3-dioxo-isoindolin-4-yl]amino]-7-azaspiro[3.5]nonane-7-carboxylate (0.80 g, 1.61 mmol) in DCM (20 mL) was added HCl/dioxane (4 M, 1.21 mL). The reaction mixture was stirred at 20° C. for 0.5 hour. On completion, the reaction mixture was concentrated in vacuo to give the title compound (690 mg, 98% yield) as a yellow solid. LC-MS (ESI$^+$) m/z 397.2 (M+H)$^+$.

3-[3-Methyl-4-[4-(methylamino)-1-piperidyl]-2-oxo-benzimidazol-1-yl]piperidine-2,6-dione (Intermediate AQK)

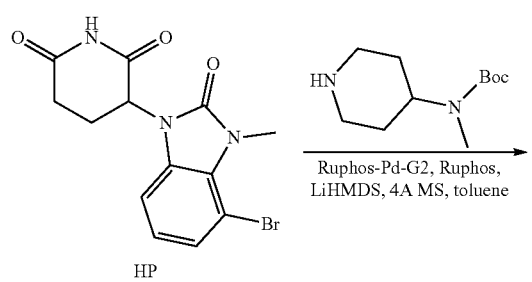

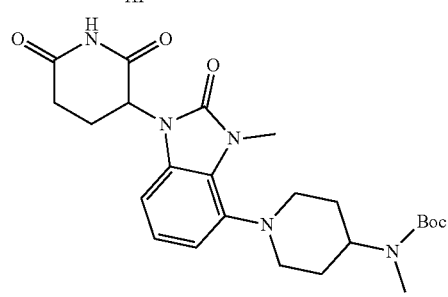

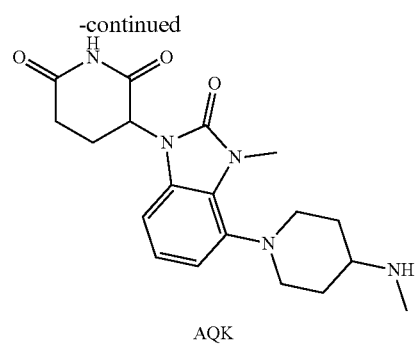

AQK

Step 1—Tert-butyl N-[1-[1-(2,6-dioxo-3-piperidyl)-3-methyl-2-oxo-benzimidazol-4-yl]-4-piperidyl]-N-methyl-carbamate To a solution of 3-(4-bromo-3-methyl-2-oxo-benzimidazol-1-yl)piperidine-2,6-dione (500 mg, 1.48 mmol, Intermediate HP), tert-butyl N methyl-N-(4-piperidyl)carbamate (633 mg, 2.96 mmol, CAS #108612-54-0) and 4 Å molecular sieves (500 mg) in toluene (10 mL) was added [2-(2-aminophenyl)phenyl]-chloro-palladium; dicyclohexyl-[2-(2,6-diisopropoxyphenyl)phenyl]phosphane (229 mg, 295 umol), RuPhos (138 mg, 295 umol) and LiHMDS (1.00 M, 8.87 mL) under N$_2$ atmosphere. The mixture was stirred at 80° C. for 1 hr under N$_2$ atmosphere. On completion, the mixture was concentrated in vacuo. The residue was diluted with DMF (6 mL), filtered and the filtrate was acidified with FA until the pH=5. The filtrate was concentrated in vacuo. The residue was purified by reverse phase (0.1% FA) and silica gel column (PE:EA=1:1) to give the title compound (70 mg, 10% yield) as a yellow solid. $^1$H NMR (400 MHz, DMSO-d$_6$) δ 11.08 (s, 1H), 7.01-6.84 (m, 3H), 5.42-5.27 (m, 1H), 3.64 (s, 3H), 3.36-3.33 (m, 1H), 3.22-3.09 (m, 2H), 2.94-2.77 (m, 3H), 2.75 (s, 3H), 2.70-2.57 (m, 2H), 2.04-1.98 (m, 1H), 1.95-1.84 (m, 2H), 1.72-1.59 (m, 2H), 1.42 (s, 9H), LC-MS (ESI$^+$) m/z 472.2 (M+H)$^+$.

Step 2—3-[3-Methyl-4-[4-(methylamino)-1-piperidyl]-2-oxo-benzimidazol-1-yl]piperidine-2,6-dione To a solution of tert-butyl N-[1-[1-(2,6-dioxo-3-piperidyl)-3-methyl-2-oxo-benzimidazol-4-yl]-4-piperidyl]-N-methylcarbamate (70.0 mg, 148 umol) in DCM (3.00 mL) was added HCl/dioxane (4.00 M, 2.00 mL). The mixture was stirred at 25° C. for 0.5 hr. On completion, the mixture was concentrated in vacuo to give the title compound (60 mg, 99% yield, HCl salt) as a yellow solid. LC-MS (ESI$^+$) m/z 372.3 (M+H)$^+$.

(4-Aminocyclohexyl)methanol (Intermediate ATD)

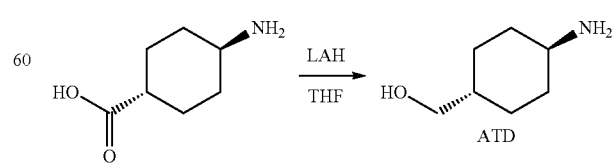

ATD

To a solution of LAH (26.5 g, 698 mmol) in THF (900 mL) was added 4-aminocyclohexanecarboxylic acid (50.0 g, 349 mmol, CAS #3685-25-4) dropwise at 0° C. The reaction mixture was stirred at 70° C. for 16 hrs. On completion, the reaction mixture was quenched by water (28 mL), then 10% NaOH aqueous (80 mL) and filtered. The filter cake was washed with DCM/THF=1/2 (5×800 mL). The combined organic layers were concentrated in vacuo to give the title compound (40.0 g, 88% yield) as light yellow solid. $^1$H NMR (400 MHz, DMSO-$d_6$) δ 4.33 (br s, 1H), 3.18 (d, J=6.4 Hz, 2H), 2.41 (tt, J=4.0, 10.4 Hz, 1H), 1.80-1.59 (m, 4H), 1.29-1.18 (m, 1H), 1.02-0.76 (m, 4H).

[4-(5-Amino-6-methoxy-indazol-2-yl)cyclohexyl]
methanol (Intermediate ATE)

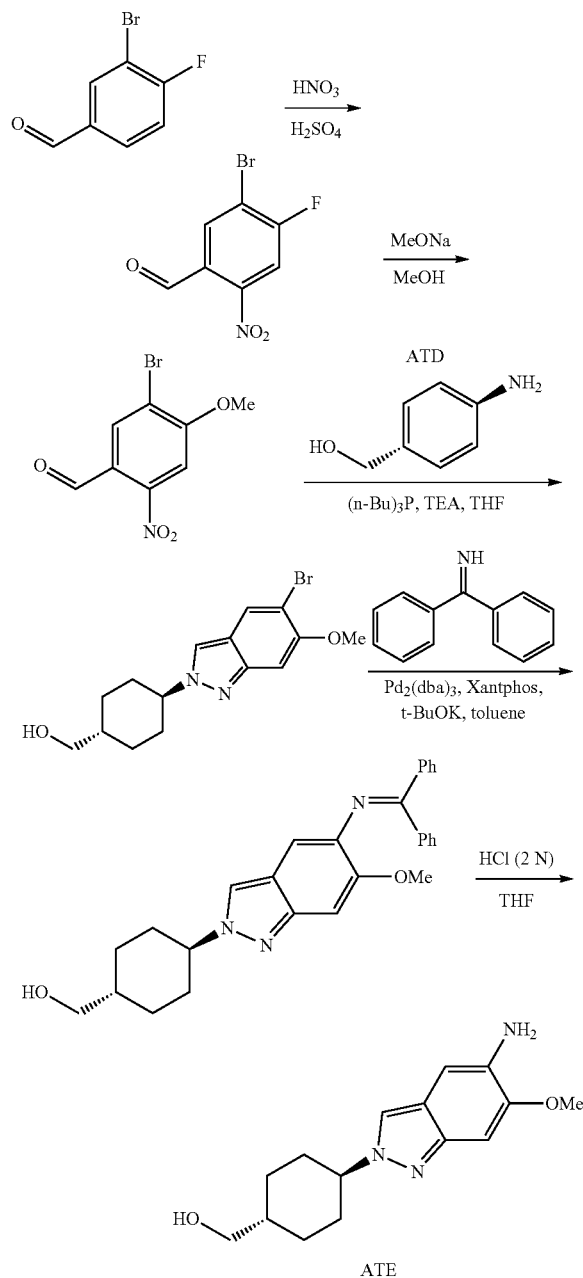

Step 1—5-Bromo-4-fluoro-2-nitro-benzaldehyde

To a solution of 3-bromo-4-fluoro-benzaldehyde (10.0 g, 49.2 mmol, CAS #77771-02-9) in $H_2SO_4$ (80 mL) was added $HNO_3$ (9.55 g, 98.5 mmol, 65% solution) dropwise at 0° C. The reaction mixture was stirred at 0-20° C. for 12 hrs. On completion, the reaction mixture was poured into cold water (600 mL) and extracted with EA (3×200 mL). The combined organic layers were washed with brine (200 mL), dried over $Na_2SO_4$, filtered and concentrated in vacuo. The residue was purified by silica gel chromatography (PE:EA=200:1) to give the title compound (9.60 g, 78% yield) as yellow solid. $^1$H NMR (400 MHz, DMSO-$d_6$) δ 10.14 (s, 1H), 8.31 (d, J=8.0 Hz, 1H), 8.26 (d, J=6.8 Hz, 1H).

Step 2—5-Bromo-4-methoxy-2-nitro-benzaldehyde

To a solution of 5-bromo-4-fluoro-2-nitro-benzaldehyde (4.00 g, 16.1 mmol) in MeOH (40 mL) was added NaOMe (1.31 g, 24.1 mmol) at 0° C. The reaction mixture was stirred at 0-20° C. for 16 hrs. On completion, the reaction mixture was quenched by water (10 mL), diluted with water (60 mL) and filtered. The filter cake was dried in vacuo to give the title compound (2.10 g, 40% yield) as yellow solid. $^1$H NMR (400 MHz, DMSO-$d_6$) δ 10.04 (s, 1H), 8.16 (s, 1H), 7.79 (s, 1H), 4.06 (s, 3H).

Step 3—[4-(5-Bromo-6-methoxy-indazol-2-yl)cyclohexyl]methanol

A mixture of 5-bromo-4-methoxy-2-nitro-benzaldehyde (1.90 g, 7.31 mmol) and (4-aminocyclohexyl) methanol (1.04 g, 8.04 mmol, Intermediate ATD) in IPA (20 mL) was stirred at 80° C. for 3 hrs. Then the solution was cooled to 25° C., and tributylphosphane (4.43 g, 21.9 mmol) was added and the reaction mixture was stirred at 80° C. for 16 hrs. On completion, the reaction mixture was concentrated in vacuo. The residue was purified by silica gel chromatography (PE:EA=1:1) to give the impure product. The impure product was triturated with PE (30 mL) to give the title compound (1.50 g, 60% yield) as white solid. $^1$H NMR (400 MHz, DMSO-$d_6$) δ 8.27 (s, 1H), 7.95 (s, 1H), 7.10 (s, 1H), 4.47 (t, J=5.6 Hz, 1H), 4.42-4.31 (m, 1H), 3.86 (s, 3H), 3.28 (t, J=6.0 Hz, 2H), 2.17-2.04 (m, 2H), 1.95-1.79 (m, 4H), 1.54-1.39 (m, 1H), 1.21-1.05 (m, 2H).

Step 4—[4-[5-(Benzhydrylideneamino)-6-methoxy-indazol-2-yl]cyclohexyl]methanol The reaction was performed in parallel two batches: A mixture of [4-(5-bromo-6-methoxy -indazol-2-yl)cyclohexyl]methanol (500 mg, 1.47 mmol), diphenylmethanimine (534 mg, 2.95 mmol), $Pd_2(dba)_3$ (134 mg, 147 umol), Xantphos (170 mg, 294 umol) and t-BuOK (496 mg, 4.42 mmol) in dioxane (10 mL) was stirred at 80° C. for 1 hr under nitrogen. On completion, the combined reaction mixture was quenched by methanol (1 mL), filtered and the filtrate was concentrated in vacuo. The residue was purified by silica gel chromatography (PE:EA=1:2) to give the title compound (600 mg, 11% yield) as yellow solid. LC-MS (ESI$^+$) m/z 440.2 (M+H)$^+$.

Step 5—[4-(5-Amino-6-methoxy-indazol-2-yl)cyclohexyl]methanol

To a solution of [4-[5-(benzhydrylideneamino)-6-methoxy-indazol-2-yl]cyclohexyl]methanol (650 mg, 1.48 mmol) in THF (3 mL) was added HCl/dioxane (2 M in water, 18.7 mL). The reaction mixture was stirred at 20° C. for 1 hr. On completion, the reaction mixture was concentrated in vacuo. The residue was purified by reverse phase (0.1% NH₃·H₂O) to give the title compound (180 mg, 33% yield) as yellow solid. LC-MS (ESI⁺) m/z 276.1 (M+H)⁺.

6-(1,1-Difluoroethyl)-N-[2-(4-formylcyclohexyl)-6-methoxy-indazol-5-yl]pyridine-2-carboxamide (Intermediate ATF)

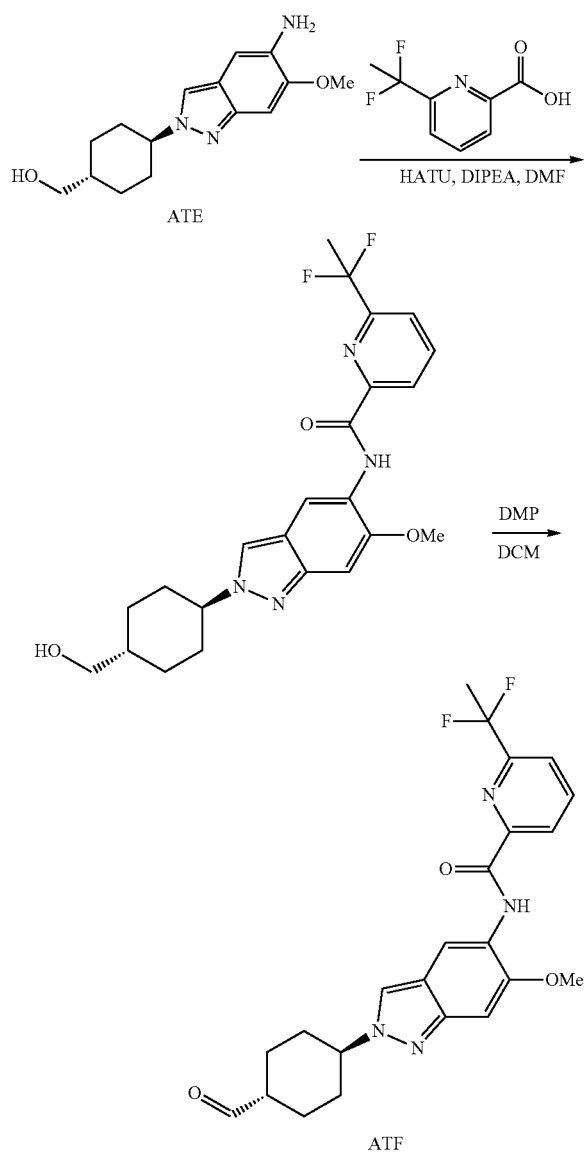

Step 1—6-(1,1-Difluoroethyl)-N-[2-[4-(hydroxymethyl)cyclohexyl]-6-methoxy-indazol-5-yl]pyridine-2-carboxamide To a solution of 6-(1,1-difluoroethyl)pyridine-2-carboxylic acid (80.8 mg, 432 umol, CAS #1211529-86-0), HATU (305 mg, 802 umol) and DIPEA (239 mg, 1.85 mmol) in DMF (3 mL) was added [4-(5-amino-6-methoxy-indazol-2-yl)cyclohexyl]methanol (170 mg, 617 umol, Intermediate ATE). The reaction mixture was stirred at 25° C. for 1 hr. On completion, the reaction mixture was quenched by water (0.1 mL) and concentrated in vacuo. The residue was purified by reverse phase (0.1% FA) to give the title compound (110 mg, 40% yield) as yellow solid. ¹H NMR (400 MHz, DMSO-d₆) δ 10.67 (s, 1H), 8.67 (s, 1H), 8.40-8.26 (m, 3H), 8.01 (dd, J=2.0, 6.8 Hz, 1H), 7.16 (s, 1H), 4.49 (t, J=5.2 Hz, 1H), 4.41-4.29 (m, 1H), 3.99 (s, 3H), 3.31-3.27 (m, 2H), 2.23-2.10 (m, 3H), 1.97-1.80 (m, 4H), 1.56-1.39 (m, 1H), 1.31-1.03 (m, 4H).

Step 2—6-(1,1-Difluoroethyl)-N-[2-(4-formylcyclohexyl)-6-methoxy-indazol-5-yl]pyridine-2-carboxamide To a solution of 6-(1,1-difluoroethyl)-N-[2-[4-(hydroxymethyl)cyclohexyl]-6-methoxy-indazol-5-yl]pyridine-2-carboxamide (100 mg, 224 umol) in DCM (1 mL) was added DMP (114 mg, 269 umol). The reaction mixture was stirred at 20° C. for 1 hr. On completion, the reaction mixture was quenched by saturated Na₂S₂SO₃ (1 mL), basified with saturated NaHCO₃ till pH=7-8 and extracted with DCM (3×20 mL). The combined organic layers were washed with brine (2×15 mL), dried over Na₂SO₄, filtered and concentrated in vacuo to give the title compound (90.0 mg, 90% yield) as yellow solid. ¹H NMR (400 MHz, DMSO-d₆) δ 10.67 (s, 1H), 9.64 (s, 1H), 8.67 (s, 1H), 8.35-8.25 (m, 3H), 8.01 (dd, J=2.4, 6.8 Hz, 1H), 7.16 (s, 1H), 4.47-4.32 (m, 1H), 3.99 (s, 3H), 2.46-2.37 (m, 1H), 2.23-2.13 (m, 3H), 2.12-2.06 (m, 2H), 2.02-1.89 (m, 2H), 1.51-1.37 (m, 2H), 1.29-1.21 (m, 2H).

6-(Trifluoromethyl)pyridine-2-carboxamide (Intermediate ATI)

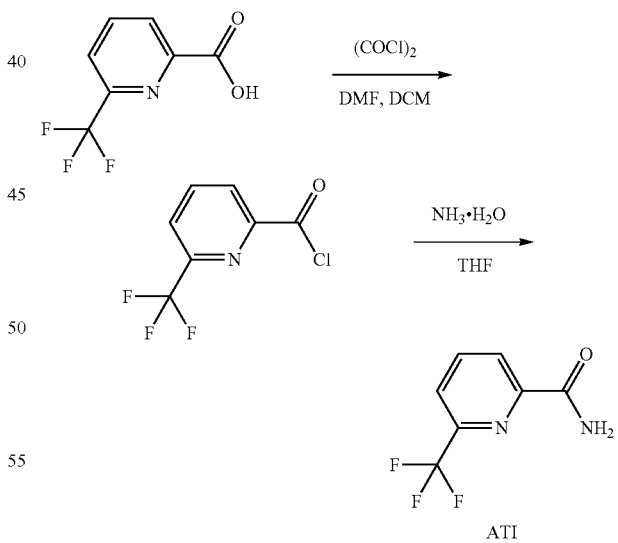

Step 1—6-(Trifluoromethyl)pyridine-2-carbonyl Chloride

To a mixture of 6-(trifluoromethyl)pyridine-2-carboxylic acid (21.0 g, 109 mmol, CAS #131747-42-7) and DMF (401 mg, 5.49 mmol) in DCM (300 mL) was added (COCl)₂ (27.9 g, 219 mmol) at 0° C. The mixture was stirred at 25° C. for 1 hour. On completion, the reaction mixture was concentrated in vacuo to give the title compound (22 g, 95% yield) as light yellow oil.

Step 2—6-(Trifluoromethyl)pyridine-2-carboxamide

A solution of 6-(trifluoromethyl)pyridine-2-carbonyl chloride (21.5 g, 102 mmol) in THF (100 mL) was added NH$_3$·H$_2$O (143 g, 1.03 mol, 158 mL, 25% solution) at 0° C. The mixture was stirred at 25° C. for 1 hour. On completion, the reaction mixture was concentrated in vacuo to remove THF and then filtered to give the filter cake as title product (19 g, 90% yield) as light yellow solid. $^1$H NMR (400 MHz, DMSO-d$_6$) δ 8.35-8.24 (m, 2H), 8.08 (dd, J=1.6, 6.8 Hz, 1H), 8.05-7.78 (m, 2H); LC-MS (ESI$^+$) m/z 191.0 (M+H)$^+$.

N-[2-(4-formylcyclohexyl)-6-methoxy-indazol-5-yl]-6-(trifluoromethyl)pyridine-2-carboxamide (Intermediate ATJ)

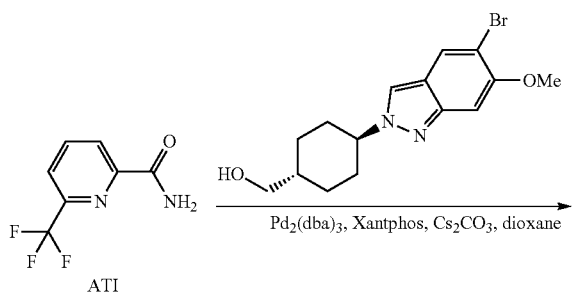

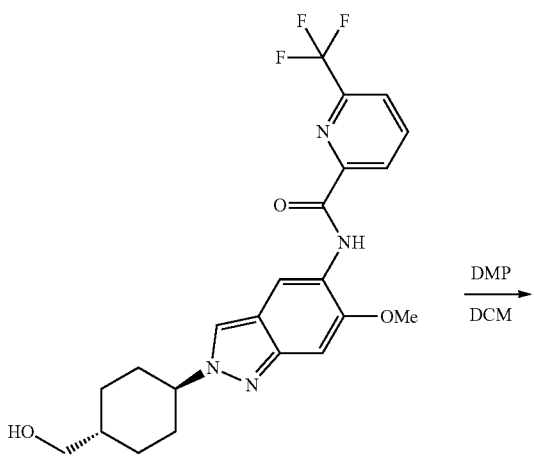

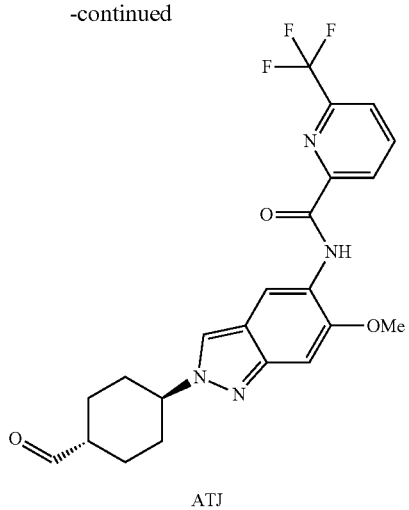

Step 1—N-[2-[4-(hydroxymethyl)cyclohexyl]-6-methoxy-indazol-5-yl]-6-(trifluoromethyl)pyridine-2-carboxamide To a solution of [4-(5-bromo-6-methoxy-indazol-2-yl)cyclohexyl]methanol (6.50 g, 19.1 mmol, synthesized via Steps 1-3 of Intermediate ATE) in dioxane (150 mL) was added Pd$_2$(dba)$_3$ (1.75 g, 1.92 mmol), Xantphos (2.22 g, 3.83 mmol), Cs$_2$CO$_3$ (12.4 g, 38.3 mmol) and 6-(trifluoromethyl)pyridine-2-carboxamide (4.01 g, 21.0 mmol, Intermediate ATI). The mixture was stirred at 80° C. for 16 hours. On completion, the reaction was filtered and concentrated in vacuo to give a residue. The residue was diluted with DCM (150 mL), and washed with water (2×30 mL). The combined organic layers was dried over Na$_2$SO$_4$, filtered and concentrated in vacuo to give a residue. The residue was purified by column chromatography (SiO$_2$, PE/EA=1/1) to give the title compound (6.50 g, 75% yield) as gray solid. $^1$H NMR (400 MHz, DMSO-d$_6$) δ 10.48 (s, 1H), 8.67 (s, 1H), 8.50-8.41 (m, 1H), 8.41-8.33 (m, 1H), 8.31 (s, 1H), 8.19 (dd, J=0.8, 7.6 Hz, 1H), 7.14 (s, 1H), 4.77-4.26 (m, 2H), 4.04-3.92 (m, 1H), 3.97 (s, 2H), 3.29 (d, J=6.0 Hz, 2H), 2.22-2.06 (m, 2H), 1.96-1.79 (m, 4H), 1.55-1.40 (m, 1H), 1.25-1.03 (m, 2H); LC-MS (ESI$^+$) m/z 449.4 (M+H)$^+$.

Step 2—N-[2-(4-formylcyclohexyl)-6-methoxy-indazol-5-yl]-6-(trifluoromethyl)pyridine-2-carboxamide To a solution of N-[2-[4-(hydroxymethyl)cyclohexyl]-6-methoxy-indazol-5-yl]-6-(trifluoromethyl) pyridine-2-carboxamide (6.70 g, 14.9 mmol) in DCM (200 mL) was added DMP (7.60 g, 17.9 mmol). The mixture was stirred at 25° C. for 2 hours. On completion, the reaction mixture was diluted with DCM (100 mL) and quenched by saturated Na$_2$S$_2$O$_3$ (100 mL) and saturated NaHCO$_3$ (100 mL) at 0° C. The mixture was then stirred at 25° C. for 30 minutes. After, the organic layers was separated, then washed with saturated NaHCO$_3$ (100 mL) and saturated NaCl (100 mL). The organic layers dried over Na$_2$SO$_4$, filtered and concentrated in vacuo to give a residue. The residue was triturated with (EA/DCM=10/1) to give the title compound (6.6 g, 95% yield) as light yellow solid. $^1$H NMR (400 MHz, DMSO-d$_6$) δ 10.49 (s, 1H), 9.64 (s, 1H), 8.68 (s, 1H), 8.45 (d, J=8.0 Hz, 1H), 8.38 (t, J=8.0 Hz, 1H), 8.31 (s, 1H), 8.19 (d, J=7.6 Hz, 1H), 7.14 (s, 1H), 4.42-4.34 (m, 1H), 3.97 (s, 3H), 2.46-2.36 (m, 1H), 2.20 (dd, J=2.8, 12.4 Hz, 2H), 2.10 (d, J=11.6 Hz, 2H), 1.99-1.89 (m, 2H), 1.48-1.38 (m, 2H); LC-MS (ESI$^+$) m/z 447.2 (M+H)$^+$.

((1R,4)-4-(5-bromo-6-fluoro-2H-indazol-2-yl)cyclohexyl)methanol (Intermediate BKP)

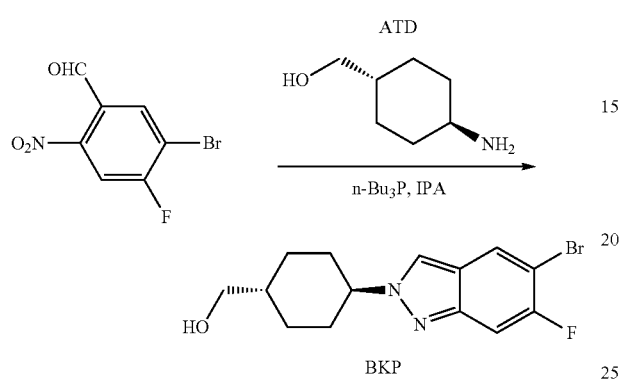

A mixture of 5-bromo-4-fluoro-2-nitro-benzaldehyde (500 mg, 2.02 mmol, synthesized via Step 1 of Intermediate ATE) and ((1r,4r)-4-aminocyclohexyl)methanol (286 mg, 2.22 mmol, Intermediate ATD) in IPA (6.00 mL) was stirred at 80° C. for 4 hrs under N$_2$. It was cooled to 25° C., then tributylphosphine (1.22 g, 6.05 mmol, 1.49 mL) was added. Then the reaction mixture was stirred at 80° C. for 16 hrs. On completion, the reaction mixture was concentrated in vacuo to give a residue. The residue was diluted with H$_2$O (10 mL) and extracted with EA (3×10 mL). The combined organic layers were washed with brine (2×20 mL), dried over anhydrous Na$_2$SO$_4$ then filtered. The filtrate was concentrated in vacuo to give a residue. The residue was purified by column chromatography (SiO$_2$, petroleum ether/ethyl acetate=1/1) to give the title compound (500 mg, 75% yield) as a yellow solid. $^1$H NMR (400 MHz, CDCl$_3$) δ 7.91 (s, 1H), 7.87 (d, J=6.8 Hz, 1H), 7.39 (d, J=9.6 Hz, 1H), 4.40-432 (m, 1H), 3.55 (d, J=6.4 Hz, 2H), 2.37-2.28 (m, 2H), 2.11-2.02 (m, 2H), 2.00-1.89 (m, 2H), 1.46-1.20 (m, 4H). LC-MS (ESI$^+$) m/z 327.0 (M+H)$^+$.

N-(6-fluoro-2-((1r,4r)-4-formylcyclohexyl)-2H-indazol-5-yl)-6-(trifluoromethyl) picolinamide (Intermediate BKQ)

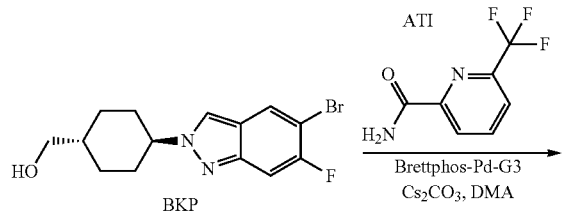

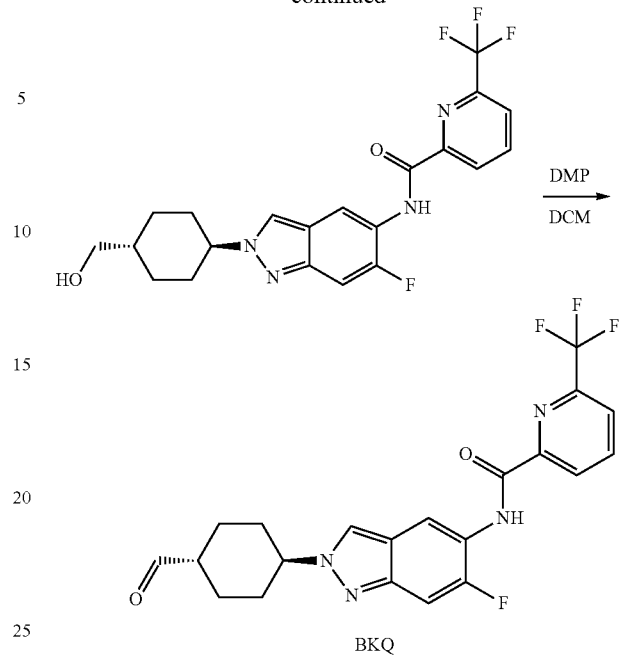

Step 1—N-(6-fluoro-2-((1r,4r)-4-(hydroxymethyl)cyclohexyl)-2H-indazol-5-yl)-6-(trifluoromethyl) picolinamide A mixture of ((1r,4r)-4-(5-bromo-6-fluoro-2H-indazol-2-yl)cyclohexyl)methanol (400 mg, 1.22 mmol, Intermediate BKP), 6-(trifluoromethyl)pyridine-2-carboxamide (255 mg, 1.34 mmol, Intermediate ATI), BrettPhos Pd G3 (55.4 mg, 61.1 umol) and Cs$_2$CO$_3$ (1.19 g, 3.67 mmol) in DMA (6 mL) was degassed and purged with N$_2$ for 3 times. The mixture was stirred at 100° C. for 2 hrs under N$_2$ atmosphere. On completion, the reaction mixture was filtered and the filtrate was concentrated in vacuo to give a residue. The residue was diluted with H$_2$O (50 mL) and extracted with EA (2×50 mL). The combined organic layers were washed with brine (2×60 mL), dried over anhydrous Na$_2$SO$_4$, filtered and concentrated in vacuo to give a residue. The residue was purified by reverse-phase (0.1% FA condition) to give the crude product. The crude product was triturated with PE (5 mL) at 25° C. for 0.5 hr to give the title compound (190 mg, 35% yield) as a yellow solid. $^1$H NMR (400 MHz, CDCl$_3$) δ 10.24 (d, J=2.8 Hz, 1H), 8.82 (d, J=7.6 Hz, 1H), 8.51 (d, J=7.6 Hz, 1H), 8.15 (t, J=8.0 Hz, 1H), 7.97 (s, 1H), 7.90 (d, J=7.6 Hz, 1H), 7.44 (d, J=11.6 Hz, 1H), 4.42-4.34 (m, 1H), 3.57 (d, J=6.0 Hz, 2H), 2.42-2.30 (m, 2H), 2.12-1.93 (m, 4H), 1.72-1.65 (m, 1H), 1.33-1.21 (m, 2H). LC-MS (ESI$^+$) m/z 437.2 (M+H)$^+$.

Step 2—N-(6-fluoro-2-((1r,4r)-4-formylcyclohexyl)-2H-indazol-5-yl)-6-(trifluoromethyl) picolinamide To a solution of N-(6-fluoro-2-((1r,4r)-4-(hydroxymethyl)cyclohexyl)-2H-indazol-5-yl)-6-(trifluoromethyl)picolinamide (160 mg, 366 umol) in DCM (3.00 mL) was added DMP (202 mg, 476 umol) at 0° C. The reaction mixture was stirred at 20° C. for 1 hr. On completion, the reaction mixture was quenched by addition saturated solution of Na$_2$S$_2$O$_3$ (5 mL), and saturated solution of NaHCO$_3$ (4 mL), then extracted with DCM (3×10 mL). The combined organic layers were washed with brine (2×20 mL). The organic was dried over anhydrous Na₂SO₄, filtered and concentrated in vacuo to give the title compound (140 mg, 88% yield) as a yellow solid. ¹H NMR (400 MHz, CDCl₃) δ 10.24 (d, J=3.2 Hz, 1H), 9.73 (s, 1H), 8.82 (d, J=7.8 Hz, 1H), 8.51 (d, J=7.6 Hz, 1H), 8.15 (t, J=8.0 Hz, 1H), 7.97 (s, 1H), 7.92-7.87 (m, 1H), 7.44 (d, J=11.6 Hz, 1H), 4.42-4.34 (m, 1H), 2.47-2.37 (m, 3H), 2.32-2.26 (m, 2H), 2.12-2.01 (m, 2H), 1.60-1.50 (m, 2H). LC-MS (ESI⁺) m/z 435.1 (M+H)⁺.

(1R,3R)-methyl 3-(6-fluoro-5-(6-(trifluoromethyl) picolinamido)-2H-indazol-2-yl) cyclobutanecarboxylate (Intermediate BQD) and (1 S,3 S)-methyl 3-(6-fluoro-5-(6-(trifluoromethyl)picolinamido)-2H-indazol-2-yl)cyclobutanecarboxylate (Intermediate BPH)

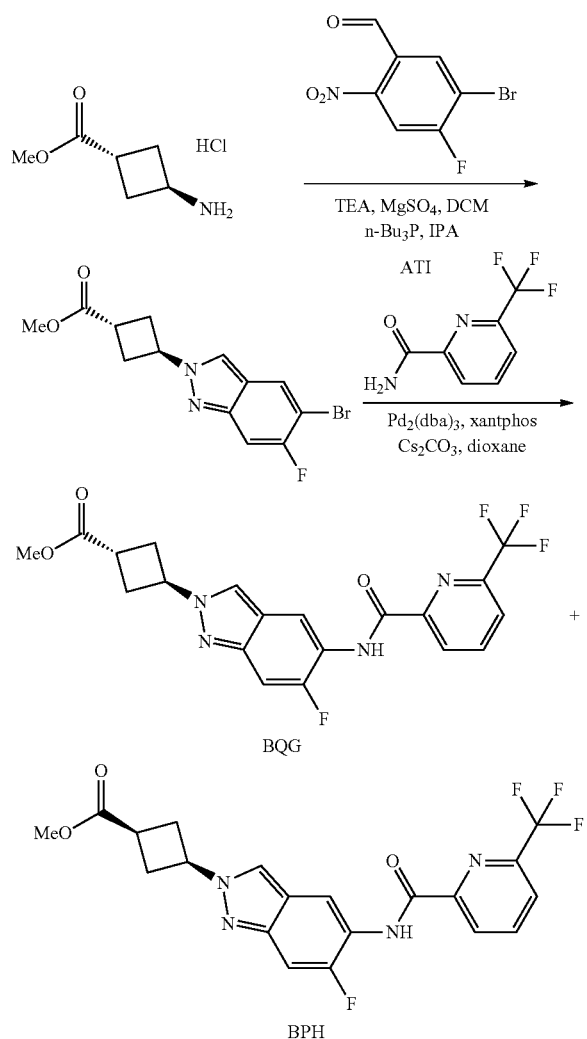

Step 1—(1R,3R)-methyl 3-(5-bromo-6-fluoro-2H-indazol-2-yl)cyclobutanecarboxylate To a solution of methyl 3-aminocyclobutanecarboxylate (1.00 g, 6.04 mmol, HCl salt, CAS #74316-29-3) and 5-bromo-4-fluoro-2-nitro-benzaldehyde (1.25 g, 5.03 mmol, synthesized via Step 1 of Intermediate ATE) in DCM (10 mL) was added TEA (610 mg, 6.04 mmol) and MgSO₄ (908 mg, 7.55 mmol) at 0° C. and the resulting mixture was stirred at rt for 2 hours. Then IPA (10 mL) and tributylphosphane (3.05 g, 15.1 mmol) were added and the mixture was stirred at 80° C. for 10 hours. The reaction mixture was concentrated under reduced pressure to give a residue. The residue was purified by column chromatography (SiO₂, Petroleum ether/Ethyl acetate=0/1 to 5/1) to give the title compound (1.30 g, 66% yield) as a white solid. LC-MS (ESI⁺) m/z 329.0 (M+H)⁺. ¹H NMR (400 MHz, CDCl₃) δ 7.91 (s, 1H), 7.88 (d, J=6.8 Hz, 1H), 7.43 (d, J=9.4 Hz, 1H), 5.36-5.20 (m, 1H), 3.78 (s, 3H), 3.41-3.25 (m, 1H), 3.15-3.03 (m, 2H), 2.92-2.80 (m, 2H).

Step 2—(1R,3R)-methyl 3-(6-fluoro-5-(6-(trifluoromethyl)picolinamido)-2H-indazol-2-yl) cyclobutanecarboxylate and (1S,3S)-methyl 3-(6-fluoro-5-(6-(trifluoromethyl)picolinamido)-2H-indazol-2-yl) cyclobutanecarboxylate To a solution of methyl 3-(5-bromo-6-fluoro-indazol-2-yl)cyclobutanecarboxylate (500 mg, 1.53 mmol) and 6-(trifluoromethyl)pyridine-2-carboxamide (319 mg, 1.68 mmol, Intermediate ATI) in DMA (5 mL) was added Cs₂CO₃ (995 mg, 3.06 mmol) and BrettPhos-Pd-G3 (138 mg, 152 umol) and the mixture was stirred at 90° C. for 12 hours. The reaction mixture was partitioned between H₂O (50 mL) and EA (100 mL). The organic phase was separated, washed with brine (50 mL), dried over Na₂SO₄, filtered and concentrated under reduced pressure to give a residue. The residue was purified by column chromatography (SiO₂, Petroleum ether/Ethyl acetate=10/1 to 3/1) to give compound (1R,3R)-methyl 3-(6-fluoro-5-(6-(trifluoromethyl)picolinamido)-2H-indazol-2-yl) cyclobutanecarboxylate (176 mg, 21% yield) as an off-white solid (¹H NMR (400 MHz, CDCl₃) δ 10.25 (d, J=3.2 Hz, 1H), 8.82 (d, J=7.6 Hz, 1H), 8.51 (d, J=7.8 Hz, 1H), 8.15 (t, J=7.8 Hz, 1H), 7.96 (d, J=0.8 Hz, 1H), 7.90 (dd, J=0.8, 7.8 Hz, 1H), 7.47 (d, J=11.6 Hz, 1H), 5.30 (t, J=8.2 Hz, 1H), 3.79 (s, 3H), 3.40-3.29 (m, 1H), 3.16-3.05 (m, 2H), 2.88 (m, 2H); LC-MS (ESI⁺) m/z 437.1 (M+H)⁺) and (1S,3S)-methyl 3-(6-fluoro-5-(6-(trifluoromethyl)picolinamido)-2H-indazol-2-yl)cyclobutanecarboxylate (240 mg, 35% yield) as an off-white solid (¹H NMR (400 MHz, CDCl₃) δ 10.26 (d, J=2.4 Hz, 1H), 8.84 (d, J=7.6 Hz, 1H), 8.51 (d, J=7.6 Hz, 1H), 8.15 (t, J=8.0 Hz, 1H), 8.06 (s, 1H), 7.90 (dd, J=0.9, 7.8 Hz, 1H), 7.46 (d, J=11.6 Hz, 1H), 5.02 (m, 1H), 3.76 (s, 3H), 3.15-3.03 (m, 1H), 3.02-2.84 (m, 4H); LC-MS (ESI⁺) m/z 437.1 (M+H)⁺.

N-(6-fluoro-2-((1S,3S)-3-formylcyclobutyl)-2H-indazol-5-yl)-6-(trifluoromethyl)picolinamide (Intermediate BPI)

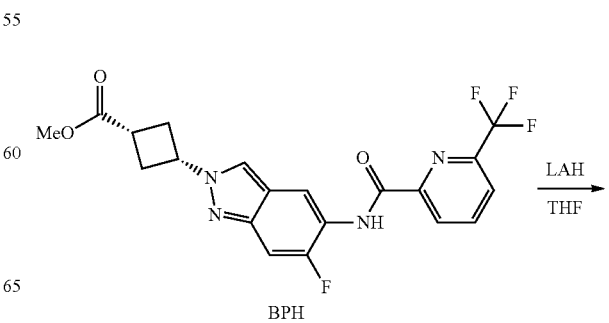

723

-continued

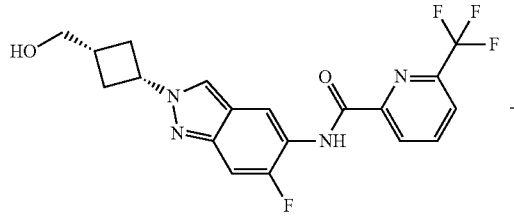

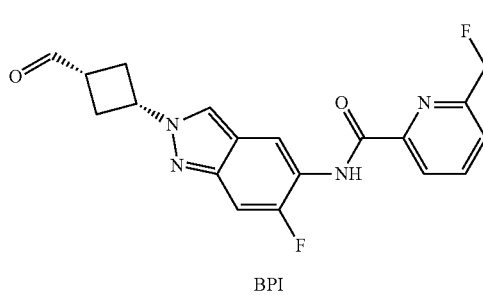

BPI

Step 1—N-(6-fluoro-2-((1s,3s)-3-(hydroxymethyl) cyclobutyl)-2H-indazol-5-yl)-6-(trifluoromethyl) picolinamide To a solution of methyl 3-[6-fluoro-5-[[6-(trifluoromethyl)pyridine-2-carbonyl]amino]indazol-2-yl]cyclobutanecarboxylate (100 mg, 229 umol, Intermediate BPH) in THF (2 mL) was added LiAlH$_4$ (17.3 mg, 458 umol) and the mixture was stirred at 0° C. for 1 hour. On completion, the reaction mixture was quenched by addition of 15% seignette salt (0.1 mL) at 0° C., and then diluted with THF (10 mL). The mixture was then filtered and concentrated under reduced pressure to give the title compound (90.0 mg, 88% yield) as an off-white solid. $^1$H NMR (400 MHz, CDCl$_3$) δ 10.25 (d, J=3.0 Hz, 1H), 8.81 (d, J=7.8 Hz, 1H), 8.51 (d, J=7.8 Hz, 1H), 8.15 (t, J=7.8 Hz, 1H), 7.99 (d, J=0.6 Hz, 1H), 7.90 (dd, J=0.8, 7.8 Hz, 1H), 7.45 (d, J=11.8 Hz, 1H), 4.99-4.85 (m, 1H), 3.86-3.69 (m, 3H), 2.84-2.69 (m, 2H), 2.64-2.42 (m, 3H); LC-MS (ESI$^+$) m/z 409.0 (M+H)$^+$.

Step 2—N-(6-fluoro-2-((1s,3 s)-3-formylcyclobutyl)-2H-indazol-5-yl)-6-(trifluoromethyl)picolin Amide To a solution of N-[6-fluoro-2-[3-(hydroxymethyl)cyclobutyl]indazol-5-yl]-6-(trifluoromethyl) pyridine-2-carboxamide (90.0 mg, 220 umol) in DCM (1 mL) was added DMP (140 mg, 330 umol) and the mixture was stirred at 20° C. for 1 hour. The reaction mixture was quenched by addition of sat. NaHCO$_3$ (10 mL) and sat. Na$_2$SO$_3$ (10 mL) at 0° C., and then diluted with H$_2$O (10 mL) and extracted with EA (3×30 mL). The combined organic layers were washed with brine (30 mL), dried over Na$_2$SO$_4$, filtered and concentrated under reduced pressure to give the title compound (89.0 mg, 92% yield) as a brown solid. LC-MS (ESI$^+$) m/z 407.0 (M+H)$^+$.

724

N-[6-fluoro-2-(2-iodoethyl)indazol-5-yl]-6-(trifluoromethyl)pyridine-2-carboxamide (Intermediate BPJ)

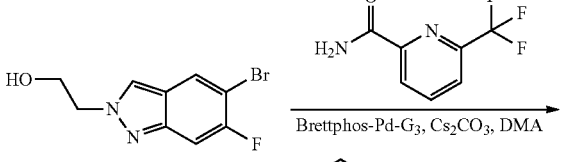

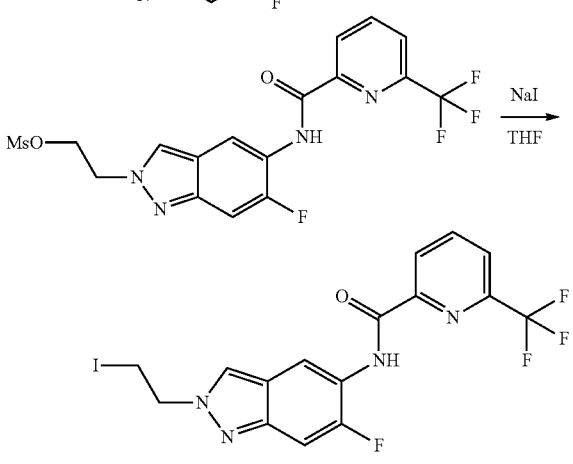

BPJ

Step 1—2-(5-Bromo-6-fluoro-indazol-2-yl)ethanol

A mixture of 5-bromo-4-fluoro-2-nitro-benzaldehyde (500 mg, 2.02 mmol) and 2-aminoethanol (135 mg, 2.22 mmol, 134 uL, CAS #141-43-5) in IPA (6.00 mL) was stirred at 80° C. for 4 hrs under N$_2$. The reaction was then cooled to 25° C. and tributylphosphane (1.23 g, 6.06 mmol, 1.50 mL) was added. The reaction mixture was stirred at 80° C. for 16 hrs. On completion, the reaction mixture was concentrated in vacuo to give a residue. The residue was diluted with H$_2$O (10 mL) and extracted with EA (3×10 mL). The combined organic layers were washed with brine (2×20 mL), dried over anhydrous Na$_2$SO$_4$, filtered and concentrated in vacuo to give a residue. The residue was purified by column chromatography (SiO$_2$, Petroleum ether/Ethyl acetate=3/1, Rf=0.12) to compound (250 mg, 48% yield) as a white solid. $^1$H NMR (400 MHz, DMSO-d$_6$) δ 8.40 (s, 1H), 8.16 (d, J=7.2 Hz, 1H), 7.57 (d, J=10.4 Hz, 1H), 4.99

(t, J=5.2 Hz, 1H), 4.44 (t, J=5.2 Hz, 2H), 3.85 (q, J=5.2 Hz, 2H). LC-MS (ESI⁺) m/z 258.9 (M+H)⁺.

Step 2—N-[6-fluoro-2-(2-hydroxyethyl)indazol-5-yl]-6-(trifluoromethyl)pyridine-2-carboxamide A mixture of 2-(5-bromo-6-fluoro-indazol-2-yl)ethanol (100 mg, 386 umol), 6-(trifluoromethyl) pyridine-2-carboxamide (88.1 mg, 463.19 umol, Intermediate ATI), BrettPhos Pd G3 (17.5 mg, 19.3 umol) and Cs$_2$CO$_3$ (251 mg, 772 umol) in DMA (2.00 mL) was degassed and purged with N$_2$ three times. The mixture was then stirred at 90° C. for 5 hrs under N$_2$ atmosphere. On completion, the reaction mixture was filtered and the filtrate was concentrated in vacuo to give a residue. The residue was diluted with H$_2$O (50 mL) and extracted with EA (2×50 mL). The combined organic layers were washed with brine (2×60 mL), dried over anhydrous Na$_2$SO$_4$, filtered and concentrated in vacuo to give a residue. The residue was purified by reverse phase (0.1% FA condition) to give the title compound (85.0 mg, 59% yield) as a yellow solid. $^1$H NMR (400 MHz, DMSO-d$_6$) δ 10.24 (s, 1H), 8.48-8.33 (m, 4H), 8.21 (d, J=7.6 Hz, 1H), 7.53 (d, J=12.0 Hz, 1H), 5.08-4.95 (m, 1H), 4.44 (t, J=5.6 Hz, 2H), 3.95-3.85 (m, 2H); LC-MS (ESI⁺) m/z 368.8 (M+H)⁺.

Step 3—2-[6-Fluoro-5-[[6-(trifluoromethyl)pyridine-2-carbonyl]amino]indazol-2-yl]ethyl methane sulfonate To a solution of N-[6-fluoro-2-(2-hydroxyethyl)indazol-5-yl]-6-(trifluoromethyl)pyridine-2-carboxamide (80.0 mg, 217 umol) and TEA (65.9 mg, 651 umol, 90.7 uL) in DCM (5.00 mL) and DMF (1.00 mL) was added MsCl (49.7 mg, 434 umol, 33.6 uL) at 0° C., then the mixture was stirred at 25° C. for 1 hr. On completion, the reaction mixture was quenched by the addition of ice water (0.5 mL), and then diluted with water (10 mL) and extracted with DCM (2×10 mL). The combined organic layers were washed with brine (3×20 mL), dried over anhydrous Na$_2$SO$_4$, filtered and concentrated in vacuo to give the title compound (90.0 mg, 92% yield) as yellow oil. LC-MS (ESI⁺) m/z 447.0 (M+H)⁺.

Step 4—N-[6-fluoro-2-(2-iodoethyl)indazol-5-yl]-6-(trifluoromethyl)pyridine -2-carboxamide To a solution of 2-[6-fluoro-5-[[6-(trifluoromethyl)pyridine-2-carbonyl]amino]indazol-2-yl]ethyl methanesulfonate (90.0 mg, 201 umol) in THF (5.00 mL) was added NaI (181 mg, 1.21 mmol), and the mixture was stirred at 50° C. for 16 hrs. On completion, the reaction mixture was quenched by the addition of water (10 mL), and extracted with EA (2×10 mL). The mixture was then washed with brine (2×20 mL), dried over anhydrous Na$_2$SO$_4$, filtered and concentrated in vacuo to give a residue. The crude product was triturated with PE/EA (20/1) (10 mL) for 30 min to give the title compound (75.0 mg, 77% yield) as a yellow solid. $^1$H NMR (400 MHz, DMSO-d$_6$) δ 10.25 (s, 1H), 8.85 (d, J=7.6 Hz, 1H), 8.52 (d, J=7.6 Hz, 1H), 8.16 (t, J=8.0 Hz, 1H), 8.00 (s, 1H), 7.90 (d, J=7.2 Hz, 1H), 7.43 (d, J=11.6 Hz, 1H), 4.74 (t, J=6.8 Hz, 2H), 3.69 (t, J=6.8 Hz, 2H). LC-MS (ESI⁺) m/z 478.9 (M+H)⁺.

N-[2-(2-iodoethyl)-6-methoxy-indazol-5-yl]-6-(trifluoromethyl)pyridine-2-carboxamide (Intermediate BPK)

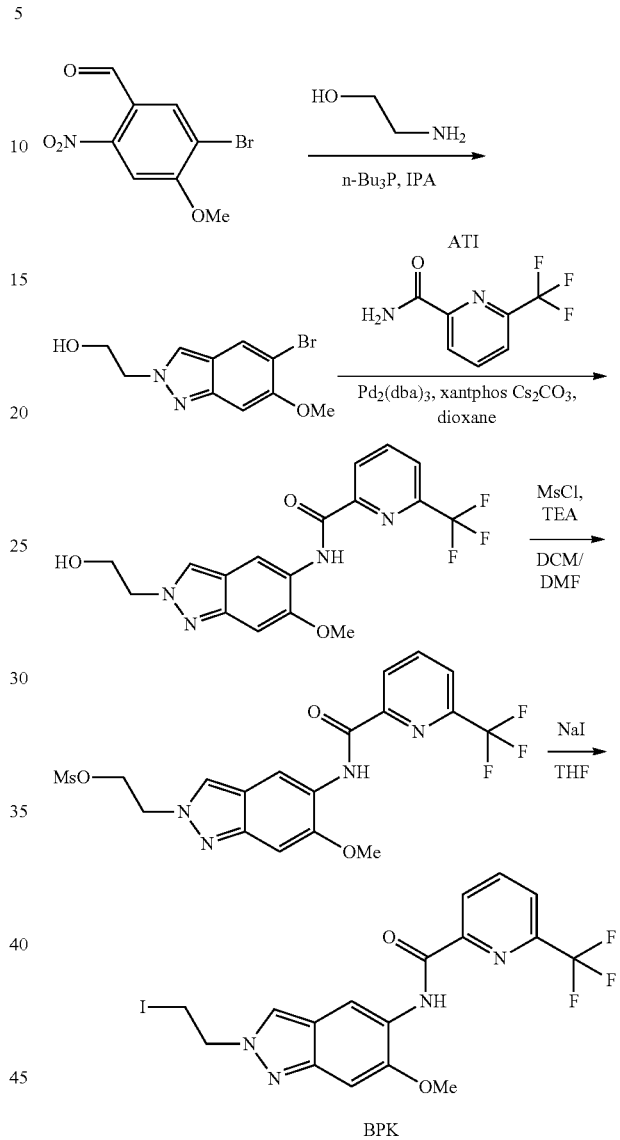

Step 1—2-(5-Bromo-6-methoxy-indazol-2-yl)ethanol

After a solution of 5-bromo-4-methoxy-2-nitro-benzaldehyde (1.00 g, 3.85 mmol, synthesized via Steps 1-2 of Intermediate ATE) and 2-aminoethanol (281 mg, 4.61 mmol) in IPA (20 mL) was stirred at 80° C. for 2 hrs. Then the reaction mixture was cooled to 25° C., and tributylphosphane (2.33 g, 11.5 mmol) was added and the reaction mixture was stirred at 80° C. for 16 hrs. On completion, the reaction mixture was concentrated in vacuo. The residue was purified by silica gel chromatography (PE:EA=2:1) to give the title compound (650 mg, 62% yield) as white solid. $^1$H NMR (400 MHz, CDCl$_3$) δ 7.89-7.83 (m, 2H), 7.01 (s, 1H), 4.50-4.45 (m, 2H), 4.14-4.06 (m, 2H), 3.95 (s, 3H), 3.36 (t, J=5.6 Hz, 1H).

Step 2—N-[2-(2-hydroxyethyl)-6-methoxy-indazol-5-yl]-6-(trifluoromethyl)pyridine-2-carboxamide A mixture of 2-(5-bromo-6-methoxy-indazol-2-yl)ethanol (300 mg, 1.11 mmol), 6-(trifluoromethyl) pyridine-2-carboxamide (231 mg, 1.22 mmol, Intermediate ATI), BrettPhos Pd G3 (100 mg, 110 umol) and Cs$_2$CO$_3$ (721 mg, 2.21 mmol) in DMA (7 mL) was stirred at 80° C. for 16 hrs. On completion, the reaction mixture was filtered, the filter cake was washed with MeOH (20 mL), and the filtrate was concentrated in vacuo. The residue was purified by reverse phase (0.1% FA) to give the title compound (300 mg, 71% yield) as yellow solid. $^1$H NMR (400 MHz, DMSO-d$_6$) δ 10.50 (s, 1H), 8.68 (s, 1H), 8.49-8.43 (m, 1H), 8.43-8.37 (m, 1H), 8.27 (s, 1H), 8.21 (dd, J=0.8, 7.6 Hz, 1H), 7.14 (s, 1H), 4.97 (t, J=5.2, 1H), 4.38 (t, J=5.6 Hz, 2H), 3.98 (s, 3H), 3.85 (d, J=5.6 Hz, 2H).

Step 3—2-[6-Methoxy-5-[[6-(trifluoromethyl)pyridine-2-carbonyl]amino]indazol-2-yl]ethyl Methane Sulfonate To a solution of N-[2-(2-hydroxyethyl)-6-methoxy-indazol-5-yl]-6-(trifluoromethyl)pyridine-2-carboxamide (200 mg, 525 umol) and TEA (106 mg, 1.05 mmol) in a mixed solvents of DMF (2 mL) and DCM (5 mL) was added MsCl (90.3 mg, 788 umol) at 0° C. The reaction mixture was stirred at 0-25° C. for 2 hrs. On completion, the reaction mixture was diluted with water (2 mL) and extracted with DCM (3×15 mL). The combined organic layers were washed with brine (2×10 mL), dried over Na$_2$SO$_4$, filtered and concentrated in vacuo to give the title compound (230 mg, 95% yield) as yellow solid. LC-MS (ESI$^+$) m/z 459.2 (M+H)$^+$.

Step 4—N-[2-(2-iodoethyl)-6-methoxy-indazol-5-yl]-6-(trifluoromethyl)pyridine-2-carboxamide A solution of 2-[6-methoxy-5-[[6-(trifluoromethyl)pyridine-2-carbonyl]amino]indazol-2-yl]ethyl methanesulfonate (230 mg, 501 umol) and NaI (376 mg, 2.51 mmol) in THF (6 mL) was stirred at 65° C. for 16 hrs. On completion, the reaction mixture was diluted with water (2 mL) and extracted with EA (3×15 mL). The combined organic layers were washed with brine (2×10 mL), dried over Na$_2$SO$_4$, filtered and concentrated in vacuo to give the title compound (230 mg, 95% yield) as yellow solid. LC-MS (ESI$^+$) m/z 491.1 (M+H)$^+$.

Pyrazolo[1,5-a]pyrimidine-3-carboxamide (Intermediate AWV)

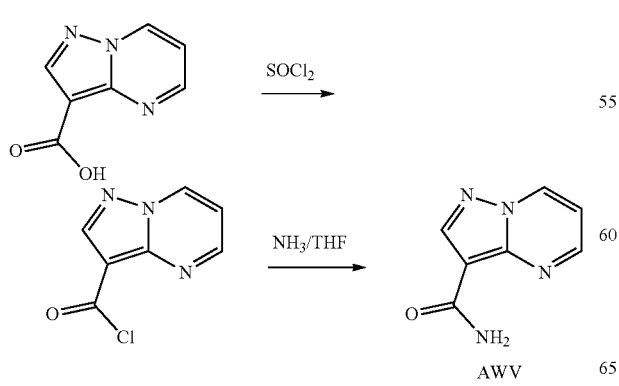

Step 1—Pyrazolo[1,5-a]pyrimidine-3-carbonyl Chloride

A mixture of pyrazolo[1,5-a]pyrimidine-3-carboxylic acid (1.00 g, 6.13 mmol, CAS #25940-35-6) in SOCl$_2$ (32.8 g, 276 mmol, 20 mL) was heated at 100° C. for 2 h. On completion, the reaction mixture was concentrated in vacuo to give the title compound (1.00 g, 90% yield) as a yellow solid. $^1$H NMR (400 MHz, DMSO-d$_6$) δ 9.30 (dd, J=1.6, 6.8 Hz, 1H), 8.85 (dd, J=1.6, 4.0 Hz, 1H), 8.66 (s, 1H), 7.31 (dd, J=4.0, 7.2 Hz, 1H), 3.83 (s, 3H).

Step 2—Pyrazolo[1,5-a]pyrimidine-3-carboxamide

A mixture of pyrazolo[1,5-a]pyrimidine-3-carbonyl chloride (500 mg, 2.75 mmol) in NH$_3$/THF (8.0 mL) was stirred at 25° C. for 5 hr. On completion, the reaction mixture was concentrated in vacuo to give the title compound (500 mg, 90% yield) as yellow solid. $^1$H NMR (400 MHz, DMSO-d$_6$) δ 9.31 (dd, J=1.6, 7.2 Hz, 1H), 8.81 (dd, J=1.6, 4.0 Hz, 1H), 8.57 (s, 1H), 7.57-7.28 (m, 2H), 7.27 (dd, J=4.4, 7.2 Hz, 1H).

N-[2-(2-iodoethyl)-6-methoxy-indazol-5-yl]pyrazolo[1,5-a]pyrimidine-3-carboxamide (Intermediate BPL)

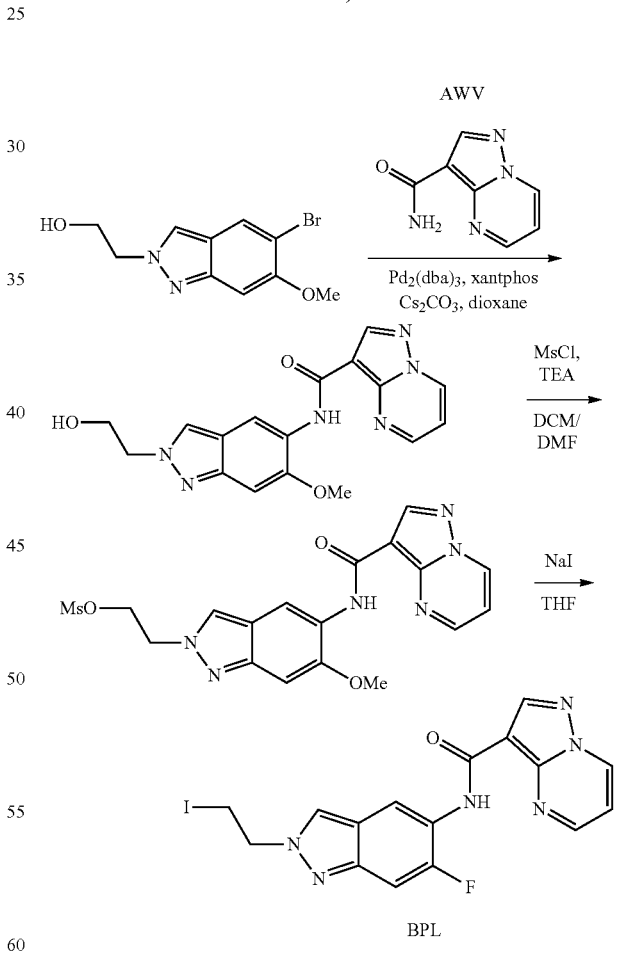

Step 1—N-[2-(2-hydroxyethyl)-6-methoxy-indazol-5-yl]pyrazolo[1,5-a]pyrimidine-3-carboxamide A mixture of 2-(5-bromo-6-methoxy-indazol-2-yl)ethanol (300 mg, 1.11 mmol, synthesized from Step 1 of Intermediate BPK), pyrazolo[1,5-a]pyrimidine-3-carboxamide (197 mg, 1.22 mmol, Intermediate AWV), BrettPhos Pd G3 (100 mg, 110 umol) and $Cs_2CO_3$ (721 mg, 2.21 mmol) in DMA (7 mL) was stirred at 80° C. for 16 hrs. On completion, the reaction mixture was filtered, the filter cake was washed with MeOH (20 mL) and filtrate was concentrated in vacuo. The residue was purified by reverse phase (0.1% FA) to give the title compound (180 mg, 45% yield) as brown solid. $^1$H NMR (400 MHz, DMSO-$d_6$) δ 10.53 (s, 1H), 9.36 (dd, J=1.6, 6.8 Hz, 1H), 8.95 (dd, J=1.6, 4.4 Hz, 1H), 8.69 (d, J=9.6 Hz, 2H), 8.22 (s, 1H), 7.34 (dd, J=4.4, 7.2 Hz, 1H), 7.09 (s, 1H), 5.07-4.83 (m, 1H), 4.36 (t, J=5.6 Hz, 2H), 4.02 (s, 3H), 3.87-3.82 (m, 2H).

Step 2—2-[6-Methoxy-5-(pyrazolo[1,5-a]pyrimidine-3-carbonyl amino)indazol-2-yl]ethyl methanesulfonate To a solution of N-[2-(2-hydroxyethyl)-6-methoxy-indazol-5-yl]pyrazolo[1,5-a]pyrimidine-3-carboxamide (140 mg, 397 umol) and TEA (100 mg, 993 umol) in a mixed solvents of DMF (2 mL) and DCM (6 mL) was added MsCl (91.0 mg, 794 umol) at 0° C. The reaction mixture was stirred at 0° C. for 1 hr. On completion, the reaction mixture was quenched with water (2 mL) and extracted with DCM (3×20 mL). The combined organic layers were washed with brine (2×10 mL), dried over $Na_2SO_4$, filtered and concentrated in vacuo to give the title compound (160 mg, 93% yield) as yellow solid. LC-MS (ESI$^+$) m/z 431.3 (M+H)$^+$.

Step 3—N-[2-(2-iodoethyl)-6-methoxy-indazol-5-yl]pyrazolo[1,5-a]pyrimidine-3-carboxamide To a solution of 2-[6-methoxy-5-(pyrazolo[1,5-a]pyrimidine-3-carbonylamino)indazol-2-yl]ethyl methanesulfonate (160 mg, 371 umol) in THF (6 mL) was added NaI (278 mg, 1.86 mmol). The reaction mixture was stirred at 65° C. for 16 hrs. On completion, the reaction mixture was diluted with water (10 mL) and extracted with EA (3×30 mL). The combined organic layers were washed with brine (2×15 mL), dried over $Na_2SO_4$, filtered and concentrated in vacuo to give the title compound (160 mg, 93% yield) as yellow solid. LC-MS (ESI$^+$) m/z 463.2 (M+H)$^+$.

Tert-butyl N-[6-fluoro-2-(2-iodoethyl)indazol-5-yl]carbamate (Intermediate BPM)

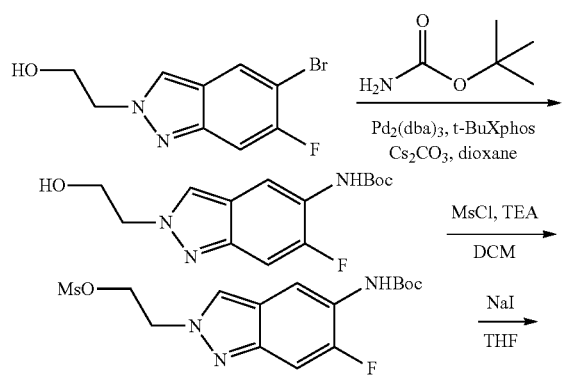

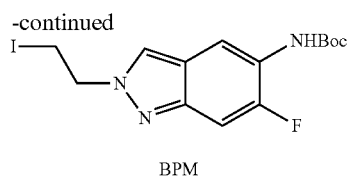

BPM

Step 1—Tert-butyl N-[6-fluoro-2-(2-hydroxyethyl)indazol-5-yl]carbamate

A mixture of 2-(5-bromo-6-fluoro-indazol-2-yl)ethanol (300 mg, 1.16 mmol, synthesized via Step 1 of Intermediate BPJ), tert-butyl carbamate (271 mg, 2.32 mmol, 73.8 uL), t-Bu Xphos (98.3 mg, 231 umol), $Pd_2(dba)_3$ (106 mg, 115 umol) and $Cs_2CO_3$ (755 mg, 2.32 mmol) in dioxane (6.00 mL) was degassed and purged with $N_2$ three times. Then the mixture was stirred at 80° C. for 16 hrs under $N_2$ atmosphere. On completion, the reaction mixture was filtered and the filtrate was concentrated in vacuo to give a residue. The residue was purified by reversed phase (0.1% FA condition) to give the title compound (260 mg, 76% yield) as a white solid. $^1$H NMR (400 MHz, DMSO-$d_6$) δ 8.74 (s, 1H), 8.30 (s, 1H), 7.79 (d, J=7.2 Hz, 1H), 7.35 (d, J=11.6 Hz, 1H), 4.98-4.94 (m, 1H), 4.40 (t, J=5.6 Hz, 2H), 3.86-3.81 (m, 2H), 1.45 (s, 9H). LC-MS (ESI$^+$) m/z 296.1 (M+H)$^+$.

Step 2—2-[5-(Tert-butoxycarbonylamino)-6-fluoro-indazol-2-yl]ethyl methanesulfonate To a solution of tert-butyl N-[6-fluoro-2-(2-hydroxyethyl)indazol-5-yl]carbamate (180 mg, 609 umol) and TEA (185 mg, 1.83 mmol, 254 uL) in DCM (10.0 mL) was added MsCl (139 mg, 1.22 mmol, 94.4 uL) at 0° C., then the mixture was stirred at 25° C. for 1 hr. On completion, the reaction mixture was quenched by addition ice water (0.5 mL), and then washed with brine (3×10 mL), dried over anhydrous $Na_2SO_4$, filtered and concentrated in vacuo to give the title compound (200 mg, 87% yield) as a yellow oil. LC-MS (ESI$^+$) m/z 374.1 (M+H)$^+$.

Step 3—Tert-butyl N-[6-fluoro-2-(2-iodoethyl)indazol-5-yl]carbamate

To a solution of 2-[5-(tert-butoxycarbonylamino)-6-fluoro-indazol-2-yl]ethyl methanesulfonate (200 mg, 535 umol) in THF (5.00 mL) was added NaI (481 mg, 3.21 mmol), and the reaction mixture was stirred at 50° C. for 16 hrs. On completion, the reaction mixture was quenched with water (10 mL), and then extracted with EA (2×10 mL). The combined organic layers were washed with brine (2×20 mL), dried over anhydrous $Na_2SO_4$, filtered and concentrated in vacuo to give a residue. The residue was purified by column chromatography ($SiO_2$, Petroleum ether/Ethyl acetate=8/1 to 6/1, PE:EA=5:1, Rf=4.0) to give the title compound (200 mg, 92% yield) as a white solid. $^1$H NMR (400 MHz, $CDCl_3$-d) δ 8.30 (d, J=7.2 Hz, 1H), 7.88 (s, 1H), 7.33 (d, J=12.0 Hz, 1H), 6.78 (s, 1H), 4.70 (t, J=6.8 Hz, 2H), 3.66 (t, J=6.8 Hz, 2H), 1.55 (s, 9H). LC-MS (ESI$^+$) m/z 406.3 (M+H)$^+$.

3-[4-[4-[2-(5-Amino-6-fluoro-indazol-2-yl)ethyl-methyl-amino]-1-piperidyl]-3-methyl-2-oxo-benzimidazol-1-yl]piperidine-2,6-dione (Intermediate BPN)

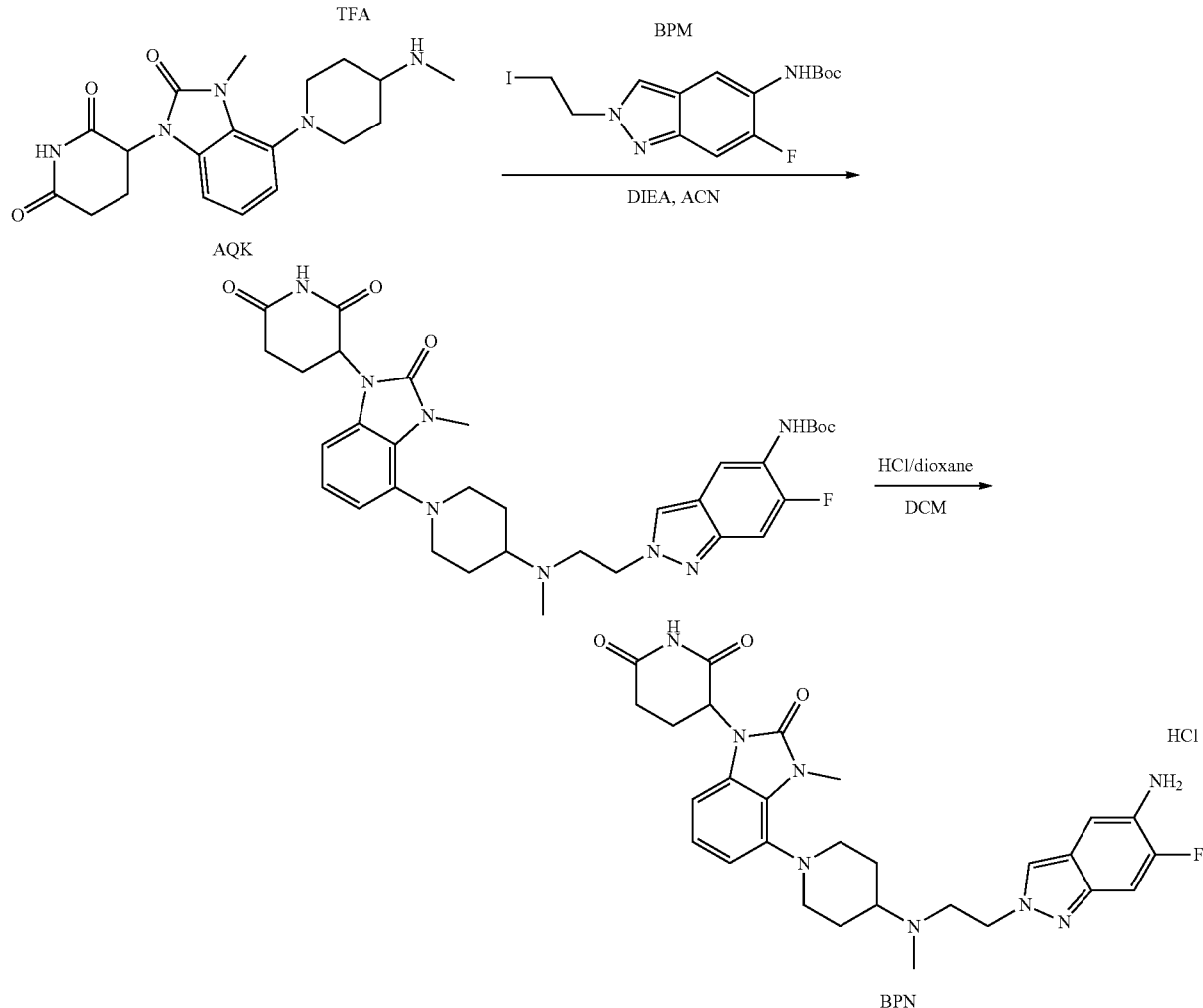

Step 1—Tert-butyl N-[2-[2-[[1-[1-(2,6-dioxo-3-piperidyl)-3-methyl-2-oxo-benzimidazol-4-yl]-4-piperidyl]-methylamino]ethyl]-6-fluoro-indazol-5-yl]carbamate To a solution of 3-[3-methyl-4-[4-(methylamino)-1-piperidyl]-2-oxo-benzimidazol-1-yl]piperidine-2,6-dione (227 mg, 468 umol, TFA, Intermediate AQK) and tert-butyl N-[6-fluoro-2-(2-iodoethyl)indazol-5-yl] carbamate (190 mg, 468 umol, Intermediate BPM) in ACN (6.00 mL) was added DIEA (181 mg, 1.41 mmol, 245 uL) at 25° C., and then the mixture was stirred at 80° C. for 16 hrs. On completion, the reaction mixture was quenched with ice water (0.5 mL), and then washed with brine (3×5 mL), dried over $Na_2SO_4$, filtered and concentrated in vacuo to give a residue. The residue was purified by reversed-phase (0.1% FA condition) to give the title compound (30.0 mg, 9.8% yield) as a white solid. $^1$H NMR (400 MHz, DMSO-$d_6$) δ 11.17-11.02 (m, 1H), 8.73 (s, 1H), 8.35 (s, 1H), 7.79 (d, J=7.2 Hz, 1H), 7.37 (d, J=11.2 Hz, 1H), 6.98-6.92 (m, 1H), 6.85 (d, J=7.2 Hz, 2H), 5.41-5.24 (m, 1H), 4.45 (t, J=6.4 Hz, 2H), 3.59 (s, 3H), 3.08 (d, J=9.2 Hz, 2H), 2.96 (t, J=6.4 Hz, 2H), 2.90-2.84 (m, 1H), 2.73-2.65 (m, 2H), 2.63-2.57 (m, 2H), 2.45-2.40 (m, 1H), 2.29 (s, 3H), 2.01-1.95 (m, 1H), 1.71-1.65 (m, 2H), 1.60-1.50 (m, 2H), 1.45 (s, 9H). LC-MS (ESI$^+$) m/z 649.3 (M+H)$^+$.

Step 2—3-[4-[4-[2-(5-Amino-6-fluoro-indazol-2-yl)ethyl-methyl-amino]-1-piperidyl]-3-methyl-2-oxo-benzimidazol-1-yl]piperidine-2,6-dione To a solution of tert-butyl N-[2-[2-[[1-[1-(2,6-dioxo-3-piperidyl)-3-methyl-2-oxo-benzimidazol-4-yl]-4-piperidyl]-methylamino]ethyl]-6-fluoro-indazol-5-yl]carbamate (25.0 mg, 38.5 umol) in DCM (1.00 mL) was added HCl/dioxane (4 M, 0.50 mL). The mixture was stirred at 25° C. for 1 hr. On completion, the reaction mixture was concentrated in vacuo to give a residue. The residue was purified by reverse phase (0.1% HCl condition) to give the title compound (10.0 mg, 44% yield, HCl) as a yellow solid. LC-MS (ESI$^+$) m/z 549.2 (M+H)$^+$.

3-(4-Bromo-3,6-dimethyl-2-oxo-benzimidazol-1-yl)piperidine-2,6-dione (Intermediate BPO)

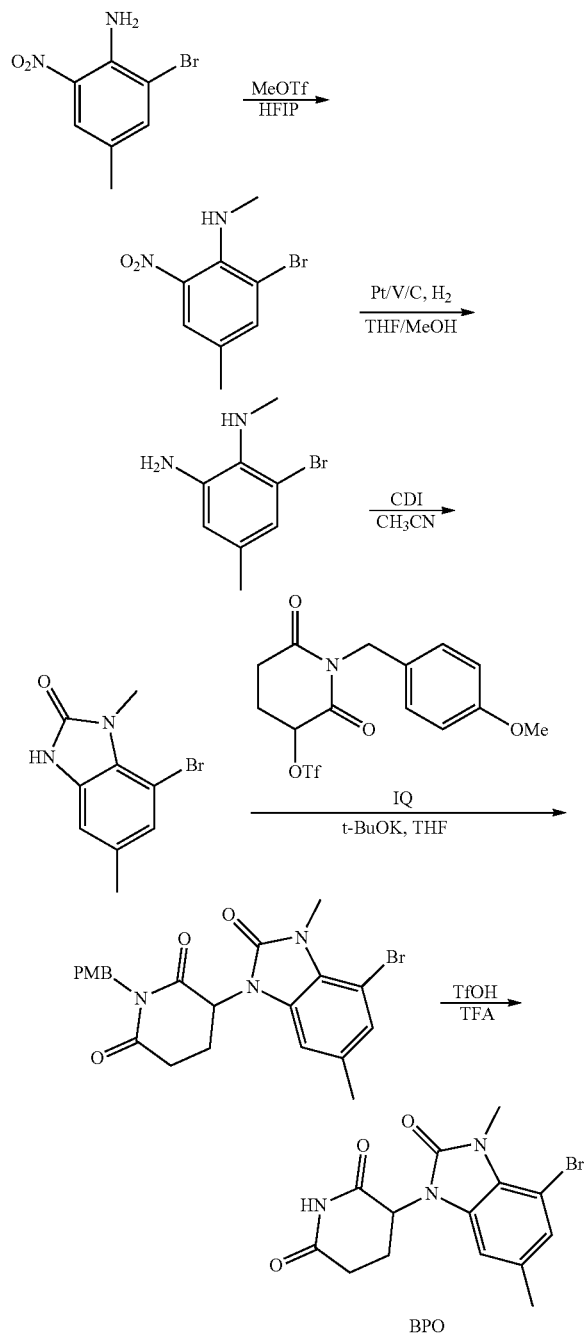

Step 1—2-Bromo-N,4-dimethyl-6-nitro-aniline

To a mixture of 2-bromo-4-methyl-6-nitro-aniline (1.00 g, 4.33 mmol, CAS #827-24-7) in HFIP (10 mL) was added methyl trifluoromethanesulfonate (781 mg, 4.76 mmol, 520 uL) at 0° C. dropwise. The reaction mixture was stirred at 25° C. for 12 h. On completion, the reaction mixture was concentrated in vacuo. The residue was diluted with water (30 mL) and extracted with EA (2×30 mL). The combined organic layer was dried over $Na_2SO_4$, filtered and concentrated in vacuo to give a residue. The residue was purified by column chromatography to give the title compound (0.99 g, 93% yield) as yellow oil. $^1$H NMR (400 MHz, CDCl$_3$) δ 7.70 (d, J=0.6 Hz, 1H), 7.54 (d, J=1.6 Hz, 1H), 2.99 (s, 3H), 2.28 (s, 3H).

Step 2—2,6-Dibromo-4-methoxy-aniline

To a mixture of 1,3-dibromo-5-methoxy-2-nitro-benzene (9.30 g, 29.9 mmol) in THF (40 mL) and MeOH (40 mL) was added Pt/V/C (5.00 g, 19.1 mmol). The reaction mixture was stirred at 25° C. for 12 hours under H$_2$ (15 PSI) atmosphere. On completion, the reaction mixture was filtered and concentrated in vacuo. The residue was purified by column chromatography to give the title compound (2.50 g, 29% yield) as white solid. $^1$H NMR (400 MHz, DMSO-d$_6$) δ 7.11 (s, 2H), 4.83 (s, 2H), 3.67 (s, 3H).

Step 3—4-Bromo-3,6-dimethyl-1H-benzimidazol-2-one

To a mixture of 3-bromo-N2,5-dimethyl-benzene-1,2-diamine (640 mg, 2.98 mmol) in ACN (10 mL) was added CDI (723 mg, 4.46 mmol). The reaction mixture was stirred at 90° C. for 12 h. On completion, the reaction mixture was concentrated in vacuo. Then residue was diluted with H$_2$O (50 mL) and filtered to give the title compound (660 mg, 92% yield) as white solid. $^1$H NMR (400 MHz, DMSO-d$_6$) δ 11.07 (s, 1H), 6.98 (s, 1H), 6.78 (s, 1H), 3.51 (s, 3H), 2.27 (s, 3H); LC-MS (ESI$^+$) m/z 241.1 (M+H)$^+$.

Step 4—3-(4-Bromo-3,6-dimethyl-2-oxo-benzimidazol-1-yl)-1-[(4-methoxyphenyl)methyl]piperidine-2,6-dione To a mixture of 4-bromo-3,6-dimethyl-1H-benzimidazol-2-one (0.66 g, 2.74 mmol) and t-BuOK (460 mg, 4.11 mmol) in THF (10 mL) was added a solution of [1-[(4-methoxyphenyl)methyl]-2,6-dioxo-3-piperidyl] trifluoromethanesulfonate (1.57 g, 4.11 mmol, Intermediate IQ) in THF (10 mL) dropwise at 0° C. The reaction mixture was stirred at 0° C. for 2 h. On completion, the reaction mixture was acidified with FA until the pH=5-6, then the residue was extracted with EA (2×30 mL). The combined organic layer was dried over Na$_2$SO$_4$, filtered and concentrated in vacuo to give a residue. The residue was purified by column chromatography to give the title compound (1.10 g, 85% yield) as white solid. $^1$H NMR (400 MHz, DMSO-d$_6$) δ 7.21 (d, J=8.4 Hz, 2H), 7.07 (s, 1H), 6.85 (d, J=8.4 Hz, 3H), 5.57-5.50 (m, 1H), 4.79 (d, J=3.2 Hz, 2H), 3.72 (s, 3H), 3.60 (s, 3H), 3.11-2.99 (m, 1H), 2.86-2.68 (m, 2H), 2.23 (s, 3H), 2.08-2.00 (m, 1H).

Step 5—3-(4-Bromo-3,6-dimethyl-2-oxo-benzimidazol-1-yl)piperidine-2,6-dione

A mixture of 3-(4-Bromo-3,6-dimethyl-2-oxo-benzimidazol-1-yl)-1-[(4-methoxyphenyl)methyl] piperidine-2,6-dione (0.20 g, 423 umol) in TfOH (2 mL) and TFA (0.4 mL) was stirred at 70° C. for 12 hour. On completion, the residue was basified with TEA until the pH=5-6 and then the mixture was concentrated in vacuo. The residue was purified by reverse phase (0.1% FA condition) to give the title compound (100 mg, 67% yield) as white solid. $^1$H NMR (400 MHz, DMSO-$d_6$) δ 11.21-10.96 (m, 1H), 7.08 (s, 1H), 7.02 (s, 1H), 5.41-5.35 (m, 1H), 3.60 (s, 3H), 2.95-2.83 (m, 1H), 2.75-2.58 (m, 2H), 2.29 (s, 3H), 2.05-1.96 (m, 1H); LC-MS (ESI$^+$) m/z 354.1 (M+H)$^+$.

3-[3,6-Dimethyl-2-oxo-4-(4-piperidyl)benzimidazol-1-yl]piperidine-2,6-dione (Intermediate BPP)

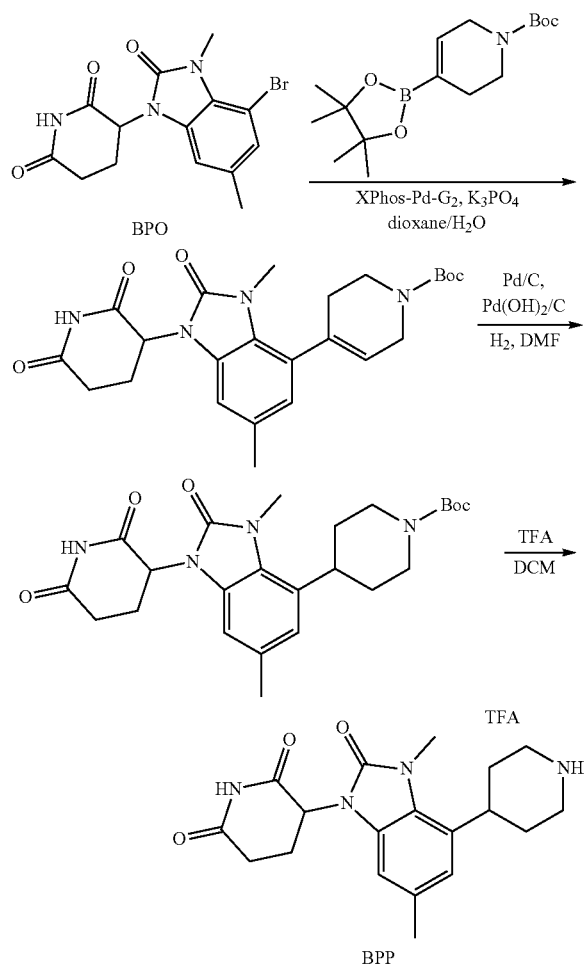

Step 1—Tert-butyl 4-[1-(2,6-dioxo-3-piperidyl)-3,6-dimethyl-2-oxo-benzimidazol-4-yl]-3,6-dihydro-2H-pyridine-1-carboxylate To a mixture of 3-(4-bromo-3,6-dimethyl-2-oxo-benzimidazol-1-yl)piperidine-2,6-dione (500 mg, 1.42 mmol, Intermediate BPO) tert-butyl 4-(4,4,5,5-tetramethyl-1,3,2-dioxaborolan-2-yl)-3,6-dihydro-2H-pyridine-1-carboxylate (877 mg, 2.84 mmol, CAS #286961-14-6) in dioxane (4 mL) and H$_2$O (0.2 mL) was added XPHOS-PD-G (111 mg, 141 umol) and K$_3$PO$_4$ (602 mg, 2.84 mmol). The reaction mixture was stirred at 80° C. for 3 h. On completion, the reaction mixture was filtered and concentrated in vacuo. The residue was purified by reverse phase (0.1% FA condition) to give the title compound (300 mg, 46% yield) as white solid. $^1$H NMR (400 MHz, DMSO-d$_6$) δ 11.07 (s, 1H), 6.90 (s, 1H), 6.64 (s, 1H), 5.68 (s, 1H), 5.39-5.32 (m, 1H), 3.99 (s, 2H), 3.61-3.52 (m, 2H), 3.28 (s, 3H), 2.96-2.83 (m, 1H), 2.79-2.68 (m, 1H), 2.68-2.57 (m, 1H), 2.37 (s, 2H), 2.29 (s, 3H), 2.02-1.93 (m, 1H), 1.44 (s, 9H).

Step 2—Tert-butyl 4-[1-(2,6-dioxo-3-piperidyl)-3,6-dimethyl-2-oxo-benzimidazol-4-yl]piperidine-1-carboxylate To a mixture of tert-butyl 4-[1-(2,6-dioxo-3-piperidyl)-3,6-dimethyl-2-oxo-benzimidazol-4-yl]-3,6-dihydro-2H-pyridine-1-carboxylate (100 mg, 220 umol) in DMF (3 mL) was added Pd/C (50 mg, 10 wt %) and Pd(OH)$_2$/C (50 mg, 10 wt %). The reaction mixture was stirred at 40° C. for 48 hours under H$_2$ (50 PSI) atmosphere. On completion, the reaction mixture was filtered and the mixture was diluted with water (10 mL) and extracted with EA (3×20 mL). The combined organic layer was dried over Na$_2$SO$_4$, filtered and concentrated in vacuo to give the title compound (100 mg, 99% yield) as light yellow solid. $^1$H NMR (400 MHz, DMSO-d$_6$) δ 11.07 (s, 1H), 6.82 (s, 1H), 6.80 (s, 1H), 5.38-5.30 (m, 1H), 4.15-4.02 (m, 2H), 3.56 (s, 3H), 3.42-3.35 (m, 1H), 2.95-2.89 (m, 1H), 2.85 (d, J=5.2 Hz, 1H), 2.72-2.67 (m, 1H), 2.65-2.56 (m, 1H), 2.52 (s, 1H), 2.28 (s, 3H), 2.01-1.92 (m, 1H), 1.79 (d, J=11.6 Hz, 2H), 1.63-1.51 (m, 2H), 1.42 (s, 9H).

Step 3—3-[3,6-Dimethyl-2-oxo-4-(4-piperidyl)benzimidazol-1-yl]piperidine-2,6-dione To a mixture of tert-butyl 4-[1-(2,6-dioxo-3-piperidyl)-3,6-dimethyl-2-oxo-benzimidazol-4-yl] piperidine-1-carboxylate (50.0 mg, 109 umol) in DCM (3 mL) was added TFA (1.54 g, 13.5 mmol) and the reaction mixture was stirred at 25° C. for 1 hour. On completion, the reaction mixture was concentrated in vacuo to give the title compound (50.0 mg, 97% yield, TFA) as red oil. LC-MS (ESI$^+$) m/z 357.2 (M+H)$^+$.

N-(6-chloro-2-((1r,4r)-4-formylcyclohexyl)-2H-indazol-5-yl)-6-(trifluoromethyl)picolinamide (Intermediate BPQ)

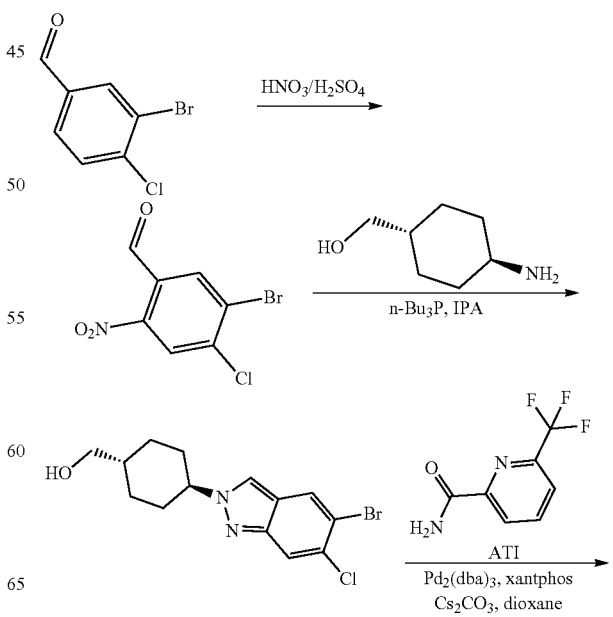

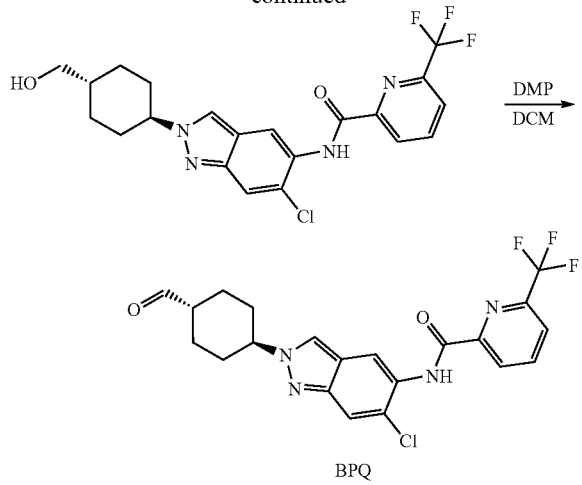

Step 1—5-Bromo-4-chloro-2-nitrobenzaldehyde

To a solution of NaNO$_3$ (426 mg, 5.01 mmol) in H2SO$_4$ (15 mL, 98% solution) was added 3-bromo-4-chloro-benzaldehyde (1.00 g, 4.56 mmol, CAS #86265-88-5) at 0° C. The mixture was stirred at 20° C. for 12 hours. On completion, the reaction mixture was poured into ice water (100 mL) at 0° C., and then diluted with H$_2$O (50 mL) and extracted with EA (3×50 mL). The combined organic layers were washed with brine (50 mL), dried over Na$_2$SO$_4$, filtered and concentrated in vacuo to give a residue. The residue was purified by column chromatography (SiO$_2$, Petroleum ether/Ethyl acetate=0/1 to 50/1) to give the title compound (650 mg, 50% yield) as a yellow solid. $^1$H NMR (400 MHz, CDCl$_3$) δ 10.40 (s, 1H), 8.24 (s, 1H), 8.23 (s, 1H); LC-MS (ESI$^+$) m/z 263.9 (M+H)$^+$.

Step 2—((1R,4r)-4-(5-bromo-6-chloro-2H-indazol-2-yl)cyclohexyl)methanol

A solution of 5-bromo-4-chloro-2-nitro-benzaldehyde (650 mg, 2.46 mmol) and (4-aminocyclohexyl) methanol (317 mg, 2.46 mmol, CAS #1467-84-1) in IPA (7 mL) was stirred at 80° C. for 3 hours. Then tributylphosphane (1.49 g, 7.37 mmol) was added and the mixture was stirred at 80° C. for 9 hours. On completion, the reaction mixture was concentrated under reduced pressure to give a residue. The residue was purified by column chromatography (SiO$_2$, Petroleum ether/Ethyl acetate=10/1 to 1/1) to give the title compound (600 mg, 70% yield) as a white solid. $^1$H NMR (400 MHz, CDCl$_3$) δ 7.98 (s, 1H), 7.91 (s, 1H), 7.86 (s, 1H), 4.38 (m, 1H), 3.57 (m, 2H), 2.42-2.28 (m, 2H), 2.10-2.03 (m, 2H), 2.02-1.90 (m, 2H), 1.68 (m, 1H), 1.26 (m, 2H); LC-MS (ESI$^+$) m/z 343.9 (M+H)$^+$.

Step 3—N-(6-chloro-2-((1r,4r)-4-(hydroxymethyl)cyclohexyl)-2H-indazol-5-yl)-6-(trifluoromethyl)picolinamide To a solution of [4-(5-bromo-6-chloro-indazol-2-yl)cyclohexyl]methanol (200 mg, 581 umol) and 6-(trifluoromethyl)pyridine-2-carboxamide (110 mg, 581 umol, Intermediate ATI) in dioxane (4 mL) was added Pd$_2$(dba)$_3$ (53.2 mg, 58.20 umol), Cs$_2$CO$_3$ (379 mg, 1.16 mmol) and Xantphos (67.3 mg, 116 umol). The mixture was stirred at 80° C. for 12 hours. On completion, the reaction mixture was filtered and concentrated under reduced pressure to give a residue. The residue was purified by column chromatography (SiO$_2$, Petroleum ether/Ethyl acetate=5/1 to 1/1) to give the title compound (240 mg, 91% yield) as an off-white solid. $^1$H NMR (400 MHz, CDCl$_3$) δ 10.71 (s, 1H), 8.91 (s, 1H), 8.51 (d, J=7.6 Hz, 1H), 8.15 (t, J=7.6 Hz, 1H), 7.98 (s, 1H), 7.90 (d, J=7.6 Hz, 1H), 7.85 (s, 1H), 4.40 (tt, J=4.4, 11.6 Hz, 1H), 3.57 (d, J=6.0 Hz, 2H), 2.41-2.31 (m, 2H), 2.12-1.93 (m, 4H), 1.78-1.65 (m, 1H), 1.33-1.21 (m, 2H); LC-MS (ESI$^+$) m/z 453.3 (M+H)$^+$.

Step 4—N-(6-chloro-2-((1r,4 r)-4-formylcyclohexyl)-2H-indazol-5-yl)-6-(trifluoromethyl)picolin Amide To a solution of N-[6-chloro-2-[4-(hydroxymethyl)cyclohexyl]indazol-5-yl]-6-(trifluoromethyl) pyridine-2-carboxamide (220 mg, 485 umol) in DCM (3 mL) was added DMP (309 mg, 728 umol). The mixture was stirred at 20° C. for 0.5 hour. On completion, the reaction mixture was quenched with sat. NaHCO$_3$ (20 mL) and sat. Na$_2$SO$_3$ (20 mL) at 0° C., and then diluted with H$_2$O (10 mL) and extracted with EA (3×50 mL). The combined organic layers were washed with brine (20 mL), dried over Na$_2$SO$_4$, filtered and concentrated under reduced pressure to give the title compound (200 mg, 89% yield) as a yellow solid. $^1$H NMR (400 MHz, CDCl$_3$) δ 10.72 (s, 1H), 9.74 (s, 1H), 8.92 (s, 1H), 8.51 (d, J=7.6 Hz, 1H), 8.15 (t, J=7.6 Hz, 1H), 7.97 (s, 1H), 7.90 (d, J=7.68 Hz, 1H), 7.85 (s, 1H), 4.40 (tt, J=4.0, 11.2 Hz, 1H), 2.48-2.37 (m, 3H), 2.29 (d, J=12.0 Hz, 2H), 2.14-1.99 (m, 2H), 1.56-1.48 (m, 2H).

3-(4-Bromo-7-fluoro-3-methyl-2-oxo-benzimidazol-1-yl)piperidine-2,6-dione (Intermediate BPR)

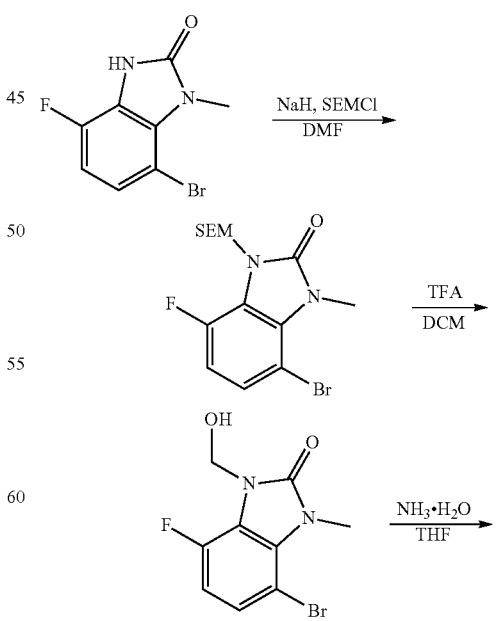

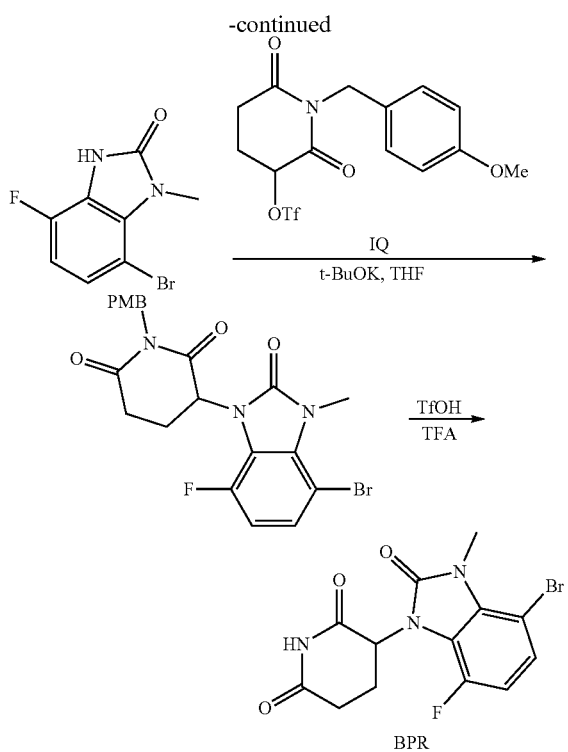

Step 1—7-bromo-4-fluoro-1-methyl-3-(2-trimethylsilylethoxymethyl)benzimidazol-2-one To a solution of 4-bromo-7-fluoro-3-methyl-1H-benzimidazol-2-one (8.7 g, 35.5 mmol, synthesized via Steps 1-4 of Intermediate BPT) in THF (20 mL) was added SEM-Cl (8.88 g, 53.2 mmol), and the mixture was stirred at 0° C. for 0.5 hour. Then to the mixture was added NaH (2.13 g, 53.2 mmol, 60% dispersion in mineral oil) in parts, then the mixture was stirred at 0° C. for 1 hour. On completion, the mixture was quenched by aq. NH$_4$Cl (40 mL) slowly. Then the mixture was extracted by EA (2×150 mL) and the combined organic layer was dried over by Na$_2$SO$_4$, and concentrated in vacuo to give the crude product. The crude product was purified by column chromatography on silica gel (PE:EA=50:1-8:1) to give as white solid (7.6 g, 57% yield). $^1$H NMR (400 MHz, DMSO-d$_6$) δ 7.24 (dd, J=4.4, 9.0 Hz, 1H), 6.95 (dd, J=9.2, 10.6 Hz, 1H), 5.27 (s, 2H), 3.62 (s, 3H), 3.55 (t, J=7.8 Hz, 2H), 0.83 (t, J=7.8 Hz, 2H), −0.01 (s, 1H), −0.08 (s, 8H); LC-MS (ESI+) m/z 347.1 (M+H)$^+$.

Step 2—4-Bromo-7-fluoro-1-(hydroxymethyl)-3-methyl-benzimidazol-2-one

To a solution of 7-bromo-4-fluoro-1-methyl-3-(2-trimethylsilylethoxymethyl)benzimidazol-2-one (2.00 g, 5.33 mmol) in DCM (20 mL) was added TFA (28.0 g, 245 mmol, 18 mL) and the reaction mixture was stirred at 25° C. for 1 hrs. On completion, the reaction mixture was concentrated in vacuo to give the title compound (1.47 g, 100% yield) as a white solid. LC-MS (ESI+) m/z 257.2 (M−17)$^+$.

Step 3—4-Bromo-7-fluoro-3-methyl-1H-benzimidazol-2-one

To a solution of 4-bromo-7-fluoro-1-(hydroxymethyl)-3-methyl-benzimidazol-2-one (1.47 g, 5.34 mmol) in THF (10 mL) was added NH$_3$·H$_2$O (64.9 mmol, 10 mL, 25% solution) and the reaction mixture was stirred at 25° C. for 1 hrs. On completion, the reaction mixture was triturated with H$_2$O at rt for 30 min, then filtered and dried under vacuum to give the title compound (1.25 g, 76% yield, 80% purity) as a white solid. LC-MS (ESI+) m/z 247.2 (M+3)$^+$.

Step 4—3-(4-Bromo-7-fluoro-3-methyl-2-oxo-benzimidazol-1-yl)-1-[(4-methoxyphenyl)methyl] piperidine-2,6-dione To a solution of 4-bromo-7-fluoro-3-methyl-1H-benzimidazol-2-one (1.25 g, 4.08 mmol) in THF (15 mL) was added t-BuOK (915 mg, 8.16 mmol) at 0° C. The mixture was then stirred at 0-25° C. for 0.5 hr. Then [1[(4-methoxyphenyl)methyl]-2,6-dioxo-3-piperidyl]trifluoromethanesulfonate (2.33 g, 6.12 mmol, Intermediate IQ) was added to above mixture at 0° C. Next, the reaction mixture was stirred at 0-25° C. for 2.5 hrs. On completion, the reaction mixture was concentrated in vacuo to give a residue. Then the mixture was diluted with H$_2$O 60 mL and extracted with EA 15 mL (3×20 mL). The combined organic layers were washed with brine 20 mL (2×10 mL), dried over by Na$_2$SO$_4$, filtered and the filtrate was concentrated in vacuo. The residue was purified by reverse phase (0.1% FA condition) to give the title compound (1.25 g, 64% yield) as a blue solid. $^1$H NMR (400 MHz, DMSO-d$_6$) δ 7.27 (dd, J=4.4, 8.8 Hz, 1H), 7.19 (d, J=8.4 Hz, 3H), 6.84 (d, J=8.8 Hz, 2H), 5.74 (dd, J=5.2, 12.8 Hz, 1H), 4.82 (s, 1H), 3.72 (s, 3H), 3.69 (s, 3H), 3.21-3.11 (m, 1H), 2.88-2.70 (m, 2H), 2.28-2.12 (m, 2H); LC-MS (ESI+) m/z 498.4 (M+23)$^+$.

Step 5—3-(4-Bromo-7-fluoro-3-methyl-2-oxo-benzimidazol-1-yl)piperidine-2,6-dione To a solution of 3-(4-bromo-7-fluoro-3-methyl-2-oxo-benzimidazol-1-yl)-1-[(4-methoxyphenyl) methyl]piperidine-2,6-dione (550 mg, 1.15 mmol) in TFA (5 mL) was added TfOH (11.3 mmol, 1 mL) at 25° C. Then the mixture was stirred at 65° C. for 2 hrs. On completion, the reaction mixture was concentrated in vacuo. The residue was purified by reverse phase (0.1% FA condition) to give the title compound (300 mg, 72% yield) as a green solid. LC-MS (ESI+) m/z 355.9 (M+H)$^+$.

3-[7-Fluoro-3-methyl-2-oxo-4-(4-piperidyl)benzimidazol-1-yl]piperidine-2,6-dione (Intermediate BPS)

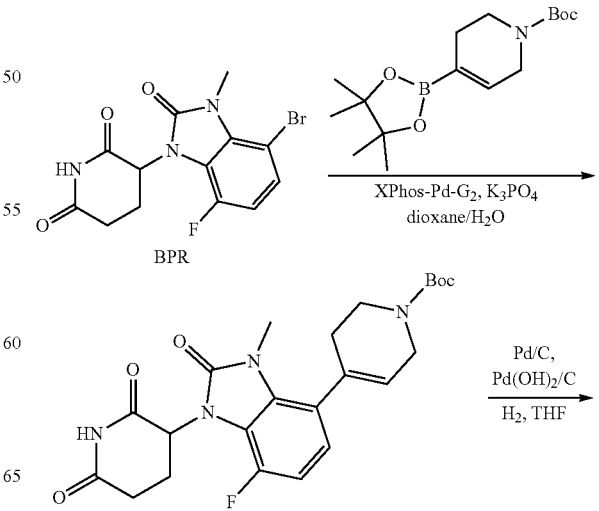

-continued

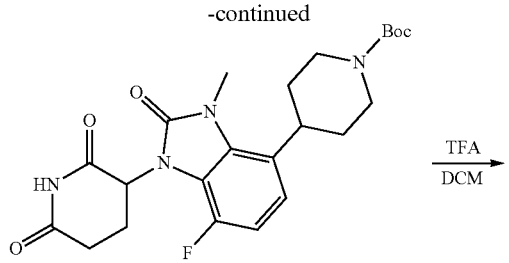

Step 1—Tert-butyl 4-[1-(2,6-dioxo-3-piperidyl)-7-fluoro-3-methyl-2-oxo-benzimidazol-4-yl]-3,6-dihydro-2H-pyridine -1-carboxylate To a solution of 3-(4-bromo-7-fluoro-3-methyl-2-oxo-benzimidazol-1-yl)piperidine-2,6-dione (270 mg, 758 umol, Intermediate BPR) and tert-butyl 4-(4,4,5,5-tetramethyl-1,3,2-dioxaborolan-2-yl)-3,6-dihydro-2H-pyridine -1-carboxylate (351 mg, 1.14 mmol, CAS #286961-14-6) in dioxane (5 mL) and H₂O (0.5 mL) was added XPHOS-PD-G2 (89.4 mg, 113 umol), K₃PO₄ (321 mg, 1.52 mmol) at 25° C. The reaction mixture was stirred at 80° C. for 6 hrs. On completion, the reaction mixture was filtered and the filtrate was concentrated in vacuo. The residue was purified by reverse phase (0.1% FA condition) to give the title compound (200 mg, 57% yield) as a white solid. ¹H NMR (400 MHz, DMSO-d₆) δ 11.18-11.01 (m, 1H), 6.97-6.87 (m, 1H), 6.86-6.81 (m, 1H), 5.76-5.67 (m, 1H), 5.58-5.48 (m, 1H), 3.99 (s, 2H), 3.57 (s, 2H), 3.35 (s, 3H), 3.08-2.92 (m, 1H), 2.65-2.58 (m, 1H), 2.37 (s, 2H), 2.30-2.16 (m, 1H), 2.14-2.03 (m, 1H), 1.43 (s, 9H); LC-MS (ESI+) m/z 459.4 (M+H)⁺.

Step 2—Tert-butyl 4-[1-(2,6-dioxo-3-piperidyl)-7-fluoro-3-methyl-2-oxo-benzimidazol-4-yl]piperidine-1-carboxylate To a solution of tert-butyl 4-[1-(2,6-dioxo-3-piperidyl)-7-fluoro-3-methyl-2-oxo-benzimidazol-4-yl]-3,6-dihydro-2H-pyridine-1-carboxylate (100 mg, 218 umol) in THF (2 mL) was added Pd/C (100 mg, 218 umol, 10 wt %) and Pd(OH)₂ (100 mg, 71.2 umol, 10 wt %) at 25° C. The reaction mixture was stirred at 25° C. for 3 hrs under H₂ (50 Psi). On completion, the reaction mixture was filtered with celite and the filtrate was concentrated in vacuo to give the title compound (70.0 mg, 69% yield) as a yellow solid. LC-MS (ESI+) m/z 405.1 (M−56)⁺.

Step 3—3-[7-Fluoro-3-methyl-2-oxo-4-(4-piperidyl)benzimidazol-1-yl]piperidine -2,6-dione To a solution of tert-butyl 4-[1-(2,6-dioxo-3-piperidyl)-7-fluoro-3-methyl-2-oxo-benzimidazol-4-yl]piperidine-1-carboxylate (70.0 mg, 152 umol) in DCM (1.5 mL) was added TFA (4.05 mmol, 0.3 mL) at 25° C. and the reaction mixture was stirred for 1 hr. On completion, the reaction mixture was concentrated in vacuo to give the title compound (70.0 mg, 97% yield) as yellow oil. LC-MS (ESI+) m/z 361.1 (M+H)⁺.

3-(4-bromo-7-fluoro-3-methyl-2-oxo-benzimidazol-1-yl)piperidine-2,6-dione (Intermediate BPT)

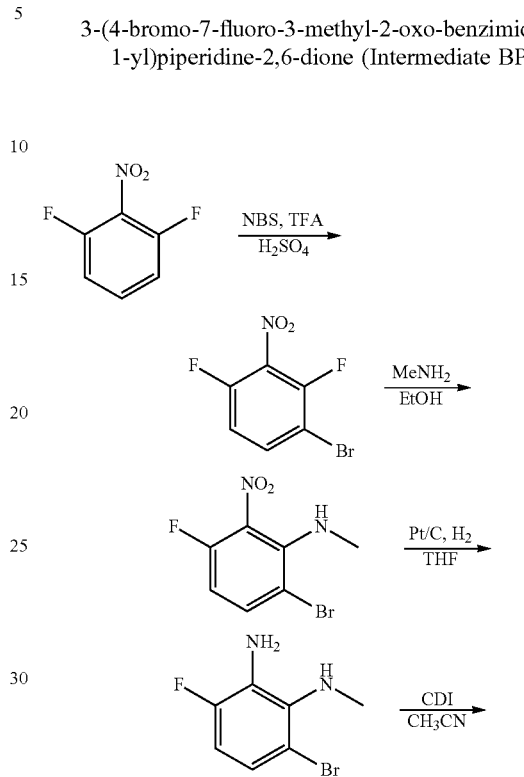

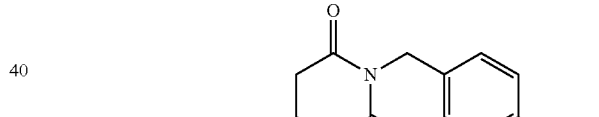

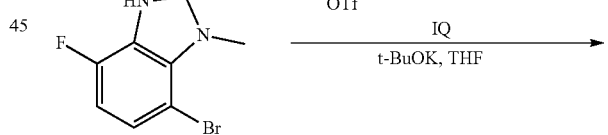

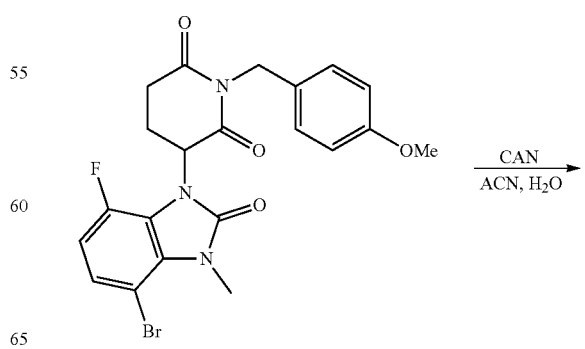

-continued

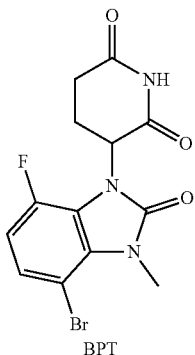

BPT

Step 1—1-bromo-2,4-difluoro-3-nitro-benzene

To a solution of $H_2SO_4$ (10 mL) was added TFA (50 mL) at 0° C. slowly. Then to the mixture was added 1,3-difluoro-2-nitro-benzene (5 g, 31.4 mmol), then added N-bromosuccinimide (5.59 g, 31.4 mmol) slowly in portions at 0° C., and the reaction was stirred at 70° C. for 18 hours. Next, after cooling the mixture to 25° C., more N-bromosuccinimide (1.68 g, 9.43 mmol) was added and the reaction was stirred at 70° C. for the other 1 hour. On completion, after the mixture was cooled to 25° C., the mixture was diluted with ice water (80 mL), acidified with sat. aq. $NaHCO_3$ to pH=8, then extracted with EA (3×100 mL). The combined organic layer was washed with brine (30 mL), dried over $Na_2SO_4$, filtered and concentrated in vacuo to give the title compound (7.1 g, 94% yield) as brown oil. $^1$H NMR (400 MHz, DMSO-$d_6$) δ 8.16 (m, 9.2 Hz, 1H), 7.54 (J=1.6, 9.6 Hz, 1H).

Step 2—6-bromo-3-fluoro-N-methyl-2-nitro-aniline

To a solution of 1-bromo-2,4-difluoro-3-nitro-benzene (2 g, 8.40 mmol) in EtOH (6 mL) was added $MeNH_2$ (1.19 g, 12.6 mmol, 2 mL, 33% solution) at 25° C. and the mixture was stirred for 2 hours. On completion, the mixture was concentrated in vacuo, diluted with water (30 mL), then extracted with EA (3×90 mL). The combined organic layer was washed with brine (20 mL), dried over $Na_2SO_4$, filtered and concentrated in vacuo to give the crude product. The crude product was purified by column chromatography on silica gel (PE:EA=1:0-10:1) to give the title compound (1.8 g, 86% yield) as brown solid. $^1$H NMR (400 MHz, DMSO-$d_6$) δ 7.71 (dd, J=6.0, 8.8 Hz, 1H), 6.67 (t, J=9.6 Hz, 1H), 6.27 (d, J=4.4 Hz, 1H), 2.70 (d, J=5.2 Hz, 3H).

Step 3—3-bromo-6-fluoro-N2-methyl-benzene-1,2-diamine

To a solution of 6-bromo-3-fluoro-N-methyl-2-nitro-aniline (500 mg, 2.01 mmol) in THF (4 mL) was added platinum (68 mg, 34.8 umol, 10 wt %, CAS #7440-06-4) at 25° C. under $H_2$ (15 psi). The mixture was stirred at 25° C. for 16 hours. The mixture was filtered and the filter cake was washed with EA (50 mL). The filtrate and washing were combined and concentrated in vacuo. The residue was diluted with water (15 mL), then extracted with EA (3×30 mL). The combined organic layer was washed with brine (10 mL), dried over $Na_2SO_4$, filtered and concentrated in vacuo to give the title compound (420 mg, 95% yield) as light brown solid. $^1$H NMR (400 MHz, DMSO-$d_6$) δ 6.79-6.62 (m, 2H), 4.96 (s, 2H), 3.90 (s, 1H), 2.61 (s, 3H); LC-MS (ESI$^+$) m/z 219.0 (M+H)$^+$.

Step 4—4-bromo-7-fluoro-3-methyl-1H-benzimidazol-2-one

To a solution of 3-bromo-6-fluoro-N2-methyl-benzene-1,2-diamine (420 mg, 1.92 mmol) in ACN (5 mL) was added CDI (466 mg, 2.88 mmol) at 25° C. Then the mixture was stirred at 85° C. for 16 hours. On completion, after the reaction was cooled to rt, the mixture was concentrated in vacuo, and diluted with water (15 mL) and $CH_3CN$ (3 mL). The mixture was filtered and the filter cake was washed with water (30 mL), then concentrated in vacuo to give the title compound (270 mg, 57% yield) as brown solid. $^1$H NMR (400 MHz, DMSO-$d_6$) δ 11.75 (s, 1H), 7.15 (dd, J=4.8, 9.2 Hz, 1H), 6.88 (t, J=9.6 Hz, 1H), 3.56 (s, 3H); LC-MS (ESI$^+$) m/z 247.0 (M+H)$^+$.

Step 5—3-(4-bromo-7-fluoro-3-methyl-2-oxo-benzimidazol-1-yl)-1-[(4-methoxyphenyl)methyl] piperidine-2,6-dione To a solution of 4-bromo-7-fluoro-3-methyl-1H-benzimidazol-2-one (130 mg, 530 umol) in THF (3 mL) was added t-BuOK (65.4 mg, 583 umol) at 0° C. The mixture was stirred at 0° C. for 0.5 h. Next, to the mixture was added [1-[(4-methoxyphenyl) methyl]-2,6-dioxo-3-piperidyl] trifluoromethanesulfonate (263 mg, 689 umol, Intermediate IQ) in THF (5 mL) at 0° C. The mixture was stirred at 0° C. for other 1.5 hours. On completion, the mixture was concentrated in vacuo. The residue was purified by column chromatography on silica gel (PE:EA=50:1-10:1) to give the title compound (195 mg, 77% yield) as light brown solid. $^1$H NMR (400 MHz, DMSO-$d_6$) δ 7.27 (dd, J=4.4, 9.2 Hz, 1H), 7.19 (d, J=8.4 Hz, 2H), 6.84 (d, J=8.8 Hz, 2H), 5.74 (dd, J=5.6, 12.8 Hz, 1H), 4.91-4.61 (m, 2H), 3.73-3.70 (m, 3H), 3.69 (s, 3H), 3.32 (s, 1H), 3.23-3.08 (m, 1H), 2.81 (d, J=18.0 Hz, 1H), 2.30-2.08 (m, 2H); LC-MS (ESI$^+$) m/z 478.2 (M+H)$^+$.

Step 6—3-(4-bromo-7-fluoro-3-methyl-2-oxo-benzimidazol-1-yl)piperidine-2,6-dione To a solution of 3-(4-bromo-7-fluoro-3-methyl-2-oxo-benzimidazol-1-yl)-1-[(4-methoxyphenyl) methyl] piperidine-2,6-dione (190 mg, 399 umol) in ACN (2 mL) was added CAN (1.09 g, 1.99 mmol) in $H_2O$ (1 mL) at 25° C. The mixture was stirred at 25° C. for 16 hours. On completion, the mixture was concentrated in vacuo to give the crude product. The crude product was purified by prep-HPLC (column: Phenomenex Synergi C18 150*25 mm*10 um; mobile phase:[water (0.225% FA)-ACN]; B %: 22%-52%, 10 min) to give the title compound (10.6 mg, 6.6% yield, FA salt) as white solid. $^1$H NMR (400 MHz, DMSO-$d_6$) δ 11.14 (s, 1H), 7.27 (dd, J=4.8, 9.2 Hz, 1H), 7.06-6.88 (m, 1H), 5.56 (dd, J=5.2, 12.4 Hz, 1H), 3.68 (s, 3H), 3.06-2.93 (m, 1H), 2.62 (d, J=17.6 Hz, 1H), 2.28-2.05 (m, 2H); LC-MS (ESI$^+$) m/z 356.1 (M+H)$^+$.

3-[6-Fluoro-3-methyl-2-oxo-4-(4-piperidyl)benzimidazol-1-yl]piperidine-2,6-dione (Intermediate BPU)

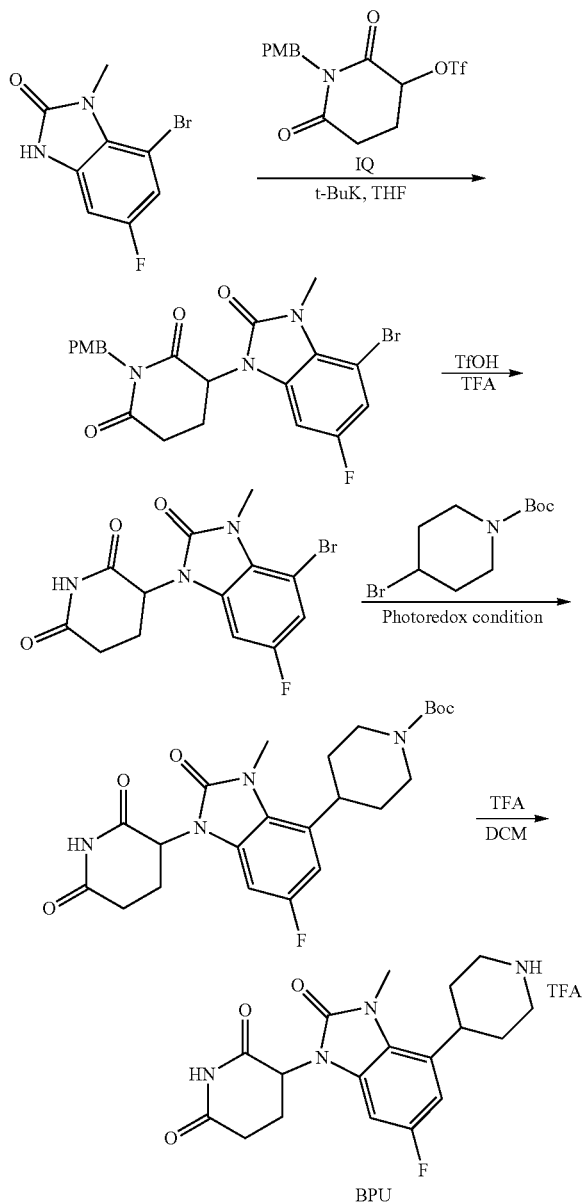

BPU

Step 1—3-(4-Bromo-6-fluoro-3-methyl-2-oxo-benzimidazol-1-yl)-1-[(4-methoxyphenyl)methyl] piperidine-2,6-dione To a solution of 4-bromo-6-fluoro-3-methyl-1H-benzimidazol-2-one (2 g, 8.16 mmol, synthesized via Steps 1-3 of Intermediate BQD) in THF (20 mL) was added t-BuOK (1.37 g, 12.2 mmol) at 0° C. The mixture was stirred at 0° C. for 0.5 hr, then a solution of [1-[(4-methoxyphenyl)methyl]-2,6-dioxo-3-piperidyl]trifluoromethanesulfonate (4.67 g, 12.2 mmol, Intermediate IQ) in THF (20 mL) was added dropwise to the mixture, and the reaction mixture was stirred at 0° C. for 3 hr. On completion, the mixture was acidified with FA to pH=3-5, diluted with water (100 mL), and extracted with EA (2×100 mL). The organic layer was washed with brine (100 mL), then concentrated in vacuo. The residue was purified by reverse phase (0.1% FA condition) to give the title compound (2.2 g, 56% yield) as a yellow solid. $^1$H NMR (400 MHz, DMSO-$d_6$) δ 7.28-7.07 (m, 4H), 6.84 (d, J=8.8 Hz, 2H), 5.56 (dd, J=5.2, 12.8 Hz, 1H), 4.89-4.68 (m, 2H), 3.71 (s, 3H), 3.61 (s, 3H), 3.08-2.94 (m, 1H), 2.88-2.68 (m, 2H), 2.14-2.01 (m, 1H); LC-MS (ESI+) m/z 478.3 (M+3)$^+$.

Step 2—3-(4-Bromo-6-fluoro-3-methyl-2-oxo-benzimidazol-1-yl)piperidine-2,6-dione To a solution of 3-(4-bromo-6-fluoro-3-methyl-2-oxo-benzimidazol-1-yl)-1-[(4-methoxyphenyl)methyl]piperidine-2,6-dione (1.60 g, 3.36 mmol) in TFA (10 mL) was added TfOH (4.25 g, 28.3 mmol), then the reaction mixture was stirred at 65° C. for 12 hrs. On completion, the reaction mixture was concentrated in vacuo to give a residue. The residue was purified by reverse phase (0.1% FA condition) to give the title compound (800 mg, 66% yield) as a yellow solid. 1H NMR (400 MHz, DMSO-$d_6$) δ 11.14 (s, 1H), 7.26 (dd, J=2.4, 8.8 Hz, 1H), 7.21 (dd, J=2.4, 9.6 Hz, 1H), 5.40 (dd, J=5.2, 12.4 Hz, 1H), 3.61 (s, 3H), 2.92-2.70 (m, 2H), 2.66-2.58 (m, 1H), 2.07-1.97 (m, 1H); LC-MS (ESI+) m/z 358.0 (M+3)$^+$.

Step 3—Tert-butyl 4-[1-(2,6-dioxo-3-piperidyl)-6-fluoro-3-methyl-2-oxo-benzimidazol-4-yl] piperidine-1-carboxyalate To an 8 mL vial equipped with a stir bar was added 3-(4-bromo-6-fluoro-3-methyl-2-oxo-benzimidazol-1-yl)piperidine-2,6-dione (600 mg, 1.68 mmol), tert-butyl 4-bromopiperidine-1-carboxylate (578 mg, 2.19 mmol, CAS #180695-79-8), Ir[dF (CF$_3$)ppy]$_2$(dtbpy)(PF$_6$) (18.9 mg, 16.8 umol), NiCl$_2$.dtbbpy (3.35 mg, 8.42 umol), TTMSS (418 mg, 1.68 mmol, 519 uL), and 2,6-lutidine (361 mg, 3.37 mmol, 392 uL) in DME (10 mL). The vial was sealed and placed under nitrogen was added. The reaction was stirred and irradiated with a 34 W blue LED lamp (7 cm away), with cooling fan to keep the reaction temperature at 25° C. for 14 hr. On completion, the reaction mixture was filtered and the filtrate was concentrated in vacuo to give a residue. The residue was purified by reverse phase (0.1% FA condition) to give the title compound (90 mg, 11% yield) as yellow oil. LC-MS (ESI$^+$) m/z 483.3 (M+Na)$^+$.

Step 4—3-[6-Fluoro-3-methyl-2-oxo-4-(4-piperidyl)benzimidazol-1-yl]piperidine -2,6-dione To a solution of tert-butyl 4-[1-(2,6-dioxo-3-piperidyl)-6-fluoro-3-methyl-2-oxo-benzimidazol-4-yl]piperidine-1-carboxylate (40.0 mg, 86.8 umol) in DCM (1 mL) was added TFA (462 mg, 4.05 mmol, 0.3 mL), then the reaction mixture was stirred at 25° C. for 0.5 hr. On completion, the reaction mixture was concentrated in vacuo to give the title compound (40.0 mg, 97% yield, TFA) as a yellow solid. LC-MS (ESI$^+$) m/z 361.3 (M+H)$^+$.

3-(4-Bromo-6-fluoro-3-methyl-2-oxo-2,3-dihydro-1H-benzo[d]imidazol-1-yl)piperidine-2,6-dione (Intermediate BQD)

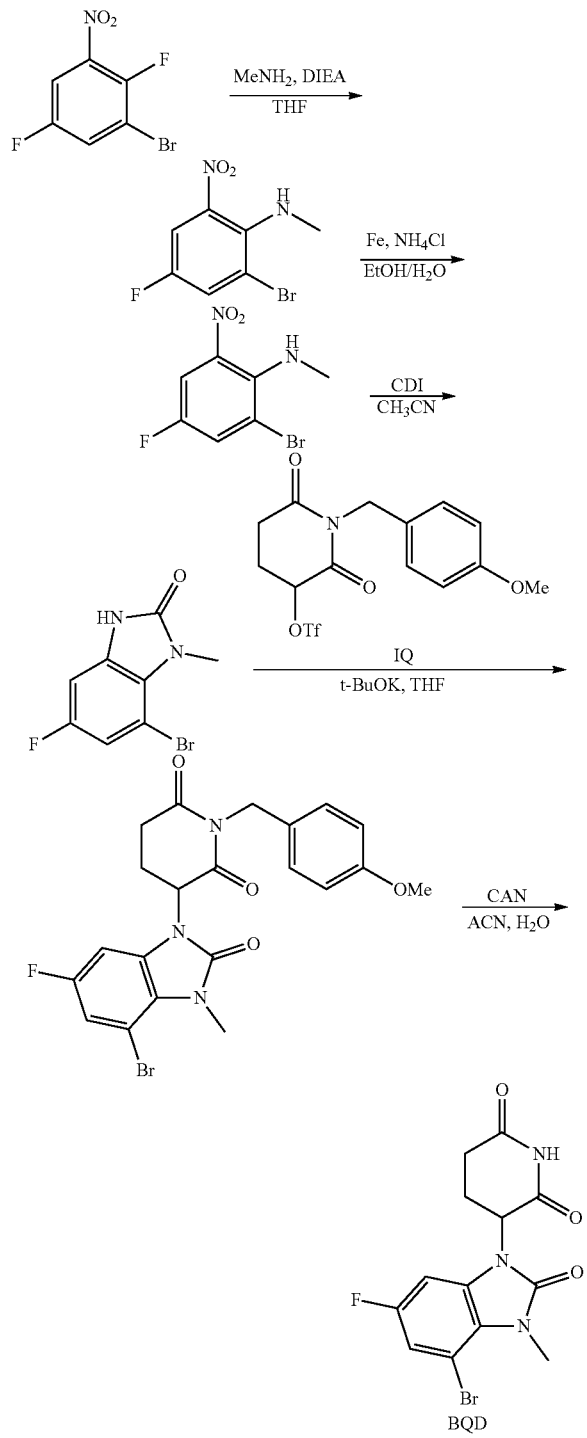

BQD

Step 1—2-Bromo-4-fluoro-N-methyl-6-nitroaniline

To a solution of 1-bromo-2,5-difluoro-3-nitro-benzene (3.00 g, 12.6 mmol, CAS #741721-51-7) and DIEA (3.26 g, 25.2 mmol) in DMF (20 mL) was added a solution of MeNH$_2$ (2 M, 31.5 mL) in THF (30 mL). The mixture was stirred at 80° C. for 6 hrs. On completion, the reaction mixture was concentrated in vacuo. The residue was diluted with EA (100 mL) and washed with water (3×100 mL). The organic layer was dried over Na$_2$SO$_4$, filtered and concentrated in vacuo to give the title compound (3.10 g, 99% yield) as yellow oil. $^1$H NMR (400 MHz, CDCl$_3$) δ 7.69 (dd, J=3.2, 8.2 Hz, 1H), 7.55 (dd, J=3.2, 7.1 Hz, 1H), 3.00 (s, 3H).

Step 2—6-Bromo-4-fluoro-N1-methylbenzene-1,2-diamine

To a solution of 2-bromo-4-fluoro-N-methyl-6-nitro-aniline (3.10 g, 12.4 mmol) in the EtOH (50 mL) and H$_2$O (10 mL) was added Fe (3.48 g, 62.2 mmol) and NH$_4$Cl (6.66 g, 124 mmol) and the mixture was stirred at 80° C. for 3 hrs. On completion, the reaction mixture was filtered and concentrated in vacuo. Then the residue was diluted with EA (100 mL) and washed with water (3×100 mL). The organic layer was dried over Na$_2$SO$_4$, filtered and concentrated in vacuo to give the title compound (2.70 g, 98% yield) as yellow oil. $^1$H NMR (400 MHz, CDCl$_3$) δ 6.77-6.58 (m, 1H), 6.46-6.32 (m, 1H), 4.17 (s, 2H), 2.68-2.00 (m, 3H).

Step 3—7-Bromo-5-fluoro-1-methyl-1H-benzo[d]imidazol-2(3H)-one

To a solution 3-bromo-5-fluoro-N2-methyl-benzene-1,2-diamine (1.35 g, 6.16 mmol) in the CH$_3$CN (20 mL) was added CDI (2.00 g, 12.3 mmol) and the mixture was stirred at 90° C. for 12 hrs under N$_2$. On completion, the reaction mixture was concentrated in vacuo and purified by column chromatography (PE:EA=10:1 to 1:1) to give the title compound (0.85 g, 56% yield) as white solid. $^1$H NMR (400 MHz, DMSO-d$_6$) δ 11.36 (s, 1H), 7.11 (dd, J=2.4, 9.8 Hz, 1H), 6.89 (dd, J=2.4, 8.4 Hz, 1H), 3.54 (s, 3H).

Step 4—3-(4-Bromo-6-fluoro-3-methyl-2-oxo-2,3-dihydro-1H-benzo[d]imidazol-1-yl)-1-(4-methoxybenzyl)piperidine-2,6-dione To a solution of 4-bromo-6-fluoro-3-methyl-1H-benzimidazol-2-one (800 mg, 3.26 mmol) in the THF (8 mL) was added tBuOK (549 mg, 4.90 mmol) at −5° C. and the mixture was stirred for 0.5 hr. Then a solution of [1[(4-methoxyphenyl)methyl]-2,6-dioxo-3-piperidyl]trifluoromethanesulfonate (1.49 g, 3.92 mmol, Intermediate IQ) in THF (4 mL) was added dropwise and the mixture was stirred at −5° C. for 3 hrs. On completion, the reaction mixture was concentrated in vacuo. The residue was diluted with EA (100 mL) and washed with saturated NH$_4$Cl (50 mL). The organic layer was dried over Na$_2$SO$_4$, filtered and concentrated in vacuo. The residue was purified by reversed phase (TFA, 0.1%) to give the title compound (400 mg, 26% yield) as gray solid. $^1$H NMR (400 MHz, CDCl$_3$) δ 7.36 (d, J=8.6 Hz, 2H), 7.00 (dd, J=2.3, 9.1 Hz, 1H), 6.84 (d, J=8.8 Hz, 2H), 6.20 (dd, J=2.3, 8.0 Hz, 1H), 5.21 (dd, J=5.5, 13.3 Hz, 1H), 4.97 (s, 2H), 3.80 (s, 3H), 3.77 (s, 3H), 3.06-2.99 (m, 1H), 2.89-2.84 (m, 1H), 2.56 (dq, J=4.6, 13.5 Hz, 1H), 2.22-2.12 (m, 1H).

Step 5—3-(4-Bromo-6-fluoro-3-methyl-2-oxo-2,3-dihydro-1H-benzo[d]imidazol-1-yl)piperidine-2,6-dione To a solution of 3-(4-bromo-6-fluoro-3-methyl-2-oxo-benzimidazol-1-yl)-1-[(4-methoxyphenyl) methyl]piperidine-2,6-dione (300 mg, 629 umol) in the MeCN (6 mL) was added a solution of CAN (1.73 g, 3.15 mmol) in the $H_2O$ (1.5 mL) at 0° C. The mixture was stirred at 20° C. for 12 hrs. On completion, the reaction mixture was concentrated in vacuo and the purified by prep-HPLC (column: Phenomenex Synergi C18 150*25 mm*10 um; mobile phase: [water (0.225% FA)-ACN]; B %: 24%-57%, 11 min) to give the title compound (20.0 mg, 9% yield) as pink solid. $^1$H NMR (400 MHz, DMSO-$d_6$) δ 11.14 (s, 1H), 7.26 (dd, J=2.2, 8.8 Hz, 1H), 7.22 (dd, J=2.2, 9.6 Hz, 1H), 5.40 (dd, J=5.4, 12.4 Hz, 1H), 3.62 (s, 3H), 2.90-2.77 (m, 1H), 2.76-2.70 (m, 1H), 2.68-2.62 (m, 1H), 2.07-1.98 (m, 1H); LC-MS (ESI$^+$) m/z 355.9 (M+H)$^+$.

Methyl 5-chloro-2-methyl-4-nitrobenzoate
(Intermediate BMM)

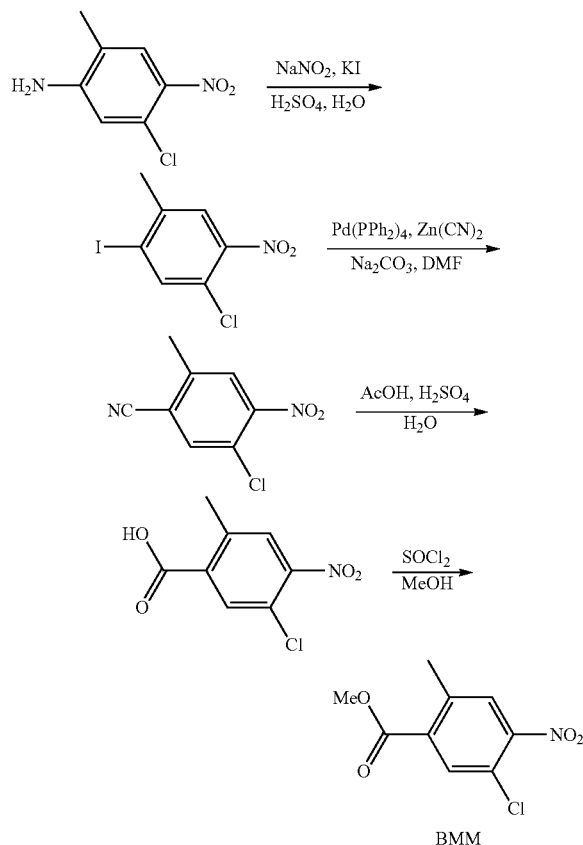

BMM

Step 1—1-Chloro-5-iodo-4-methyl-2-nitrobenzene

To a mixture of 5-chloro-2-methyl-4-nitro-aniline (10 g, 53.6 mmol, CAS #13852-51-2) in H2504 (3 M, 100 mL) was added dropwise a solution of NaNO$_2$ (3.70 g, 53.6 mmol) in H$_2$O (10 mL) over 1 hr at 0° C. Then a solution of KI (10.7 g, 64.3 mmol) in H$_2$O (10 mL) was added. The reaction mixture was stirred at 0° C. for 1 hr and allowed to warm to 25° C. for 1 hr. On completion, the reaction mixture was diluted with water (500 mL) and extracted with EA (3×200 mL). The organic layer was washed with saturated NaHCO$_3$ (aq., 2×500 mL) and brine (3×300 mL). The organic layer was dried over Na$_2$SO$_4$, filtered and concentrated in vacuo. The residue was purified by silica gel chromatography (PE:EA=1:0 to 100:1) to give the title compound (12.2 g, 76% yield) as yellow solid. $^1$H NMR (400 MHz, DMSO-$d_6$) δ 8.24 (s, 1H), 8.04 (s, 1H), 2.43 (s, 3H).

Step 2—5-Chloro-2-methyl-4-nitrobenzonitrile

To a mixture of 1-chloro-5-iodo-4-methyl-2-nitro-benzene (11.6 g, 39.2 mmol), Pd(PPh$_3$)$_4$ (4.53 g, 3.92 mmol) and Na$_2$CO$_3$ (8.31 g, 78.4 mmol) in DMF (80 mL) was added Zn(CN)$_2$ (2.76 g, 23.5 mmol, 1.49 mL). The reaction mixture was stirred at 50° C. for 24 hrs under N$_2$. On completion, the reaction mixture was diluted with water (500 mL) and extracted with EA (3×300 mL). The organic layer was washed with brine (3×300 mL), dried over Na$_2$SO$_4$, filtered and concentrated in vacuo. The residue was purified by silica gel chromatography (PE:EA=1:0 to 80:1) to give the title compound (6.30 g, 82% yield) as yellow solid. $^1$H NMR (400 MHz, CDCl$_3$) δ 7.82-7.79 (m, 2H), 2.64 (s, 3H).

Step 3—5-Chloro-2-methyl-4-nitrobenzoic Acid

A mixture of 5-chloro-2-methyl-4-nitro-benzonitrile (2.20 g, 11.2 mmol) in a mixed of AcOH (20 mL), H$_2$O (20 mL) and H$_2$SO$_4$ (20 mL) was stirred at 120° C. for 16 hrs. On completion, the reaction mixture was diluted with water (40 mL) and filtered. The filtrate cake was dried in vacuo to give the title compound (2.20 g, 91% yield) as off-white solid. $^1$H NMR (400 MHz, CDCl$_3$) δ 8.23 (s, 1H), 7.76 (s, 1H), 2.71 (s, 3H).

Step 4—Methyl 5-chloro-2-methyl-4-nitrobenzoate

To a mixture of 5-chloro-2-methyl-4-nitro-benzoic acid (2.20 g, 10.2 mmol) in MeOH (40 mL) was dropwise SOCl$_2$ (1.82 g, 15.3 mmol, 1.11 mL) at 0° C. The reaction mixture was stirred at 70° C. for 16 hrs under N$_2$. On completion, the reaction mixture was concentrated in vacuo and the residue was diluted with EA (100 mL) and washed with brine (3×100 mL). The organic layer was dried over Na$_2$SO$_4$, filtered and concentrated in vacuo to give the title compound (2.30 g, 98% yield) as off-white solid. $^1$H NMR (400 MHz, CDCl$_3$) δ 8.08 (s, 1H), 7.74 (s, 1H), 3.96 (s, 3H), 2.64 (s, 3H).

N-(2-((1r,4r)-4-formylcyclohexyl)-6-methoxy-1-oxoisoindolin-5-yl)-6-(trifluoromethyl)picolinamide
(Intermediate BMI)

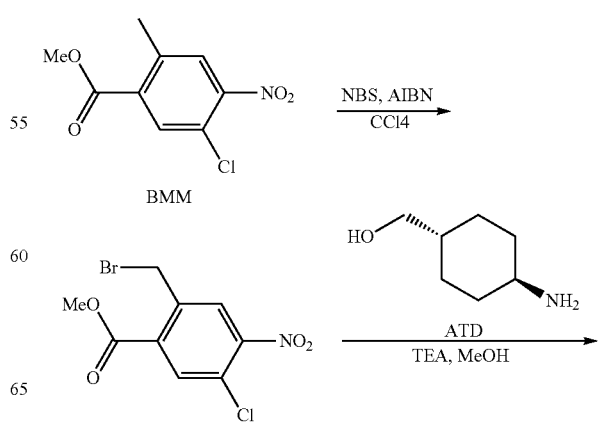

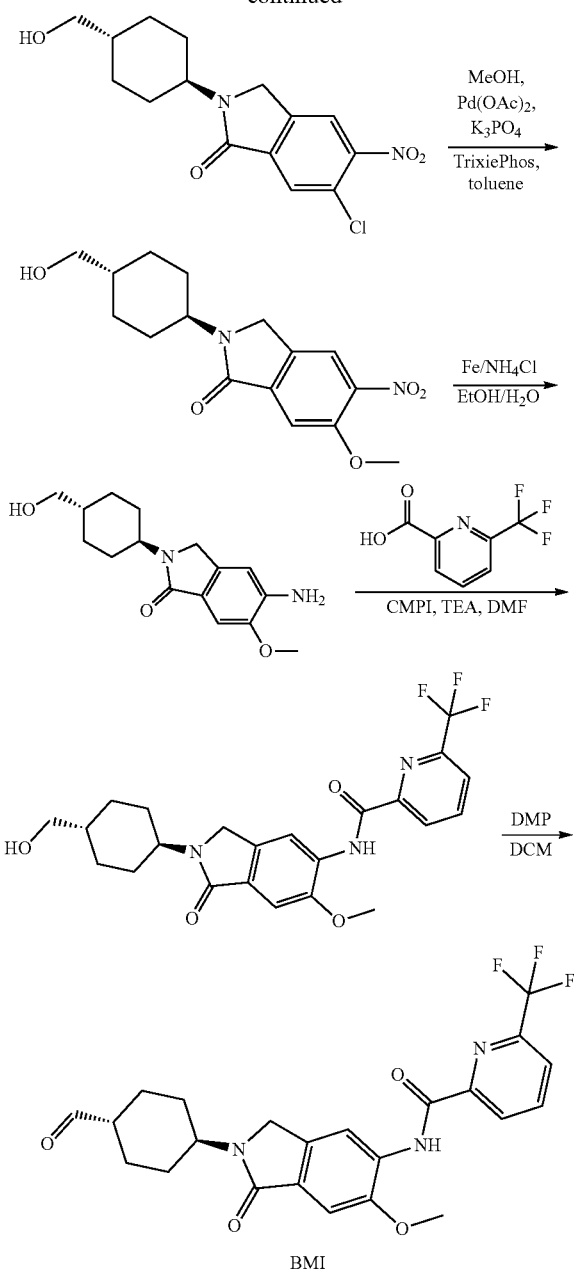

Step 1—Methyl 2-(bromomethyl)-5-chloro-4-nitrobenzoate

To a solution of methyl 5-chloro-2-methyl-4-nitro-benzoate (3.1 g, 13.5 mmol, Intermediate BMM) in ACN (60 mL) was added NBS (2.88 g, 16.2 mmol) and AIBN (111 mg, 675 umol). The mixture was stirred at 70° C. for 16 hours under $N_2$. On completion, the reaction mixture was concentrated in vacuo and the residue was diluted with EA (100 mL) and washed with brine (2×100 mL). The organic layer was dried over $Na_2SO_4$, filtered and concentrated in vacuo to give the title compound (4.0 g, 96% yield) as yellow solid. $^1$H NMR (400 MHz, $CDCl_3$) δ 8.15 (s, 1H), 7.99 (s, 1H), 4.92 (s, 2H), 4.01 (s, 3H).

Step 2—6-Chloro-2-((1r,4r)-4-(hydroxymethyl)cyclohexyl)-5-nitroisoindolin-1-one

To a solution of methyl 2-(bromomethyl)-5-chloro-4-nitro-benzoate (4.0 g, 13.0 mmol) and (4-aminocyclohexyl)methanol (2.01 g, 15.6 mmol, Intermediate ATD) in MeOH (40 mL) was added TEA (2.62 g, 25.9 mmol, 3.61 mL) and the mixture was stirred at 80° C. for 16 hours under $N_2$. On completion, the reaction mixture was concentrated in vacuo. The residue was purified by column chromatography ($SiO_2$, PE:EA=5:1 to 1:2) to give the title compound (2.86 g, 68% yield) as yellow solid. $^1$H NMR (400 MHz, $CDCl_3$) δ 8.01 (s, 1H), 7.91 (s, 1H), 4.44 (s, 2H), 4.25 (tt, J=3.6, 12.1 Hz, 1H), 3.53 (d, J=6.2 Hz, 2H), 2.01-1.93 (m, 4H), 1.62-1.55 (m, 2H), 1.55-1.49 (m, 1H), 1.46 (s, 1H), 1.28-1.17 (m, 2H).

Step 3—2-((1r,4r)-4-(Hydroxymethyl)cyclohexyl)-6-methoxy-5-nitroisoindolin-1-one To a solution of 6-chloro-2-[4-(hydroxymethyl)cyclohexyl]-5-nitro-isoindolin-1-one (1.0 g, 3.08 mmol) in MeOH (1.97 g, 61.6 mmol, 2.49 mL) and toluene (10 mL) was added $K_3PO_4$ (1.31 g, 6.16 mmol), $Pd(OAc)_2$ (69.1 mg, 308 umol) and ditert-butyl-[1-(1-naphthyl)-2-naphthyl]phosphane (245 mg, 616 umol), and the mixture was stirred at 80° C. for 16 hours under $N_2$. On completion, the reaction mixture was concentrated in vacuo and purified by column chromatography ($SiO_2$, PE/EA=10/1 to 1/10) to give the title compound (500 mg, 51% yield) as yellow solid. $^1$H NMR (400 MHz, $CDCl_3$) δ 7.86 (s, 1H), 7.55 (s, 1H), 4.37 (s, 2H), 4.31-4.21 (m, 1H), 4.02 (s, 3H), 3.53 (d, J=1.8 Hz, 2H), 1.97 (d, J=11.0 Hz, 4H), 1.61-1.49 (m, 3H), 1.44 (s, 1H), 1.29-1.17 (m, 2H).

Step 4—5-Amino-2-((1r,4r)-4-(hydroxymethyl)cyclohexyl)-6-methoxyisoindolin-1-one To a solution of 2-[4-(hydroxymethyl)cyclohexyl]-6-methoxy-5-nitro-isoindolin-1-one (500 mg, 1.56 mmol) in the EtOH (6.0 mL) and $H_2O$ (2.0 mL) was added Fe (436 mg, 7.80 mmol) and $NH_4Cl$ (417 mg, 7.80 mmol). The mixture was stirred at 80° C. for 4 hours. On completion, the reaction mixture was filtered and concentrated in vacuo. The residue was diluted with DCM (100 mL) and MeOH (1.0 mL), then the mixture was washed with water (100 mL). The organic layer was dried over $Na_2SO_4$, filtered and concentrated in vacuo to give the title compound (400 mg, 88% yield) as yellow solid. $^1$H NMR (400 MHz, DMSO-$d_6$) δ 6.98 (s, 1H), 6.72 (s, 1H), 5.36 (s, 2H), 4.43 (s, 1H), 4.19 (s, 2H), 3.90 (t, J=11.8 Hz, 1H), 3.81 (s, 3H), 3.24 (t, J=5.2 Hz, 2H), 1.82 (d, J=12.4 Hz, 2H), 1.71 (d, J=11.2 Hz, 2H), 1.50 (q, J=11.8 Hz, 2H), 1.38-1.29 (m, 1H), 1.03 (q, J=12.0 Hz, 2H).

Step 5—N-(2-((1r,4r)-4-(hydroxymethyl)cyclohexyl)-6-methoxy-1-oxoisoindolin-5-yl)-6-(trifluoromethyl)picolinamide To a solution of 5-amino-2-[4-(hydroxymethyl)cyclohexyl]-6-methoxy-isoindolin-1-one (100 mg, 344 umol) and 6-(trifluoromethyl)pyridine-2-carboxylic acid (65.8 mg, 344 umol) in the DMF (2 mL) was added CMPI (106 mg, 413 umol) and DIEA (133 mg, 1.03 mmol, 180 uL). The mixture was stirred at 25° C. for 1 hr. On completion, the reaction mixture was diluted with EA (20 mL) and washed with water (3×20 mL). The organic layer was dried over $Na_2SO_4$, filtered and concentrated in vacuo to give the title compound (155 mg, 97% yield) as yellow solid. ¹H NMR (400 MHz, CDCl₃) δ 10.76 (s, 1H), 8.74 (s, 1H), 8.50 (d, J=7.8 Hz, 1H), 8.15 (t, J=7.8 Hz, 1H), 7.90 (d, J=7.6 Hz, 1H), 7.41 (s, 1H), 4.34 (s, 2H), 4.25 (t, J=11.6 Hz, 1H), 4.05 (s, 3H), 3.53 (d, J=6.4 Hz, 2H), 1.97 (d, J=11.0 Hz, 4H), 1.62-1.54 (m, 3H), 1.29-1.24 (m, 2H).

Step 6—N-(2-((1r,4r)-4-formylcyclohexyl)-6-methoxy-1-oxoisoindolin-5-yl)-6-(trifluoromethyl)picolinamide To a solution of N-[2-[4-(hydroxymethyl)cyclohexyl]-6-methoxy-1-oxo-isoindolin-5-yl]-6-(trifluoromethyl)pyridine-2-carboxamide (155 mg, 334 umol) in the DCM (3 mL) was added DMP (170 mg, 401 umol) and the mixture was stirred at 25° C. for 1 hr. On completion, the reaction mixture was quenched by Na₂S₂O₃ (aq, 5 mL) and NaHCO₃ (aq, 5 mL), then the mixture was extracted with DCM (2×20 mL). The organic layer was dried over Na₂SO₄, filtered and concentrated in vacuo and purified by column chromatography (SiO2, PE/EA=10/1 to 1/1) to give the title compound (150 mg, 87% yield) as yellow solid. LC-MS (ESI⁺) m/z 462.2 (M+H)⁺.

N-[2-(4-formylcyclohexyl)-6-[(1S,4S)-2-oxa-5-azabicyclo[2.2.1]heptan-5-yl]-1-oxo-isoindolin-5-yl]-6-(trifluoromethyl)pyridine-2-carboxamide (Intermediate BQE)

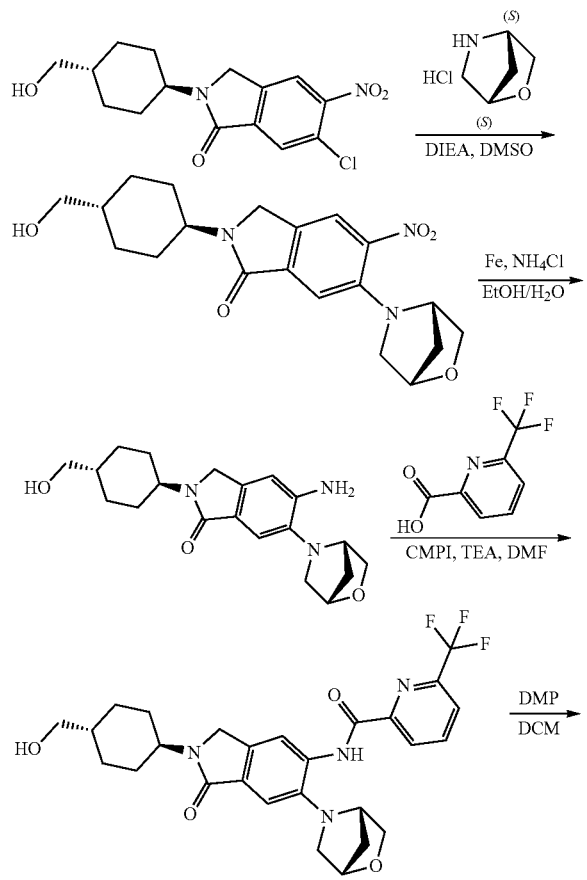

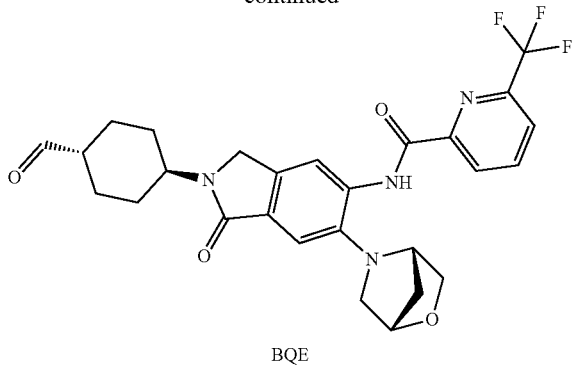

BQE

Step 1—2-[4-(Hydroxymethyl)cyclohexyl]-5-nitro-6-[(1S,4S)-2-oxa-5-azabicyclo[2.2.1]heptan-5-yl]isoindolin-1-one To a solution of 6-chloro-2-[4-(hydroxymethyl)cyclohexyl]-5-nitro-isoindolin-1-one (220 mg, 677 umol, synthesized via Steps 1-2 of Intermediate BMI) and (1S,4S)-2-oxa-5-azabicyclo[2.2.1]heptane (137.78 mg, 1.02 mmol, HCl salt, CAS #31560-06-2) in DMSO (3 mL) was added DIEA (175 mg, 1.35 mmol) at 25° C. Then the reaction mixture was stirred at 80° C. for 36 hrs. On completion, the reaction mixture was concentrated in vacuo. The residue was purified by prep-HPLC (column: Phenomenex luna C18 150*25 mm*10 um; mobile phase: [water (0.225% FA)-ACN]; B %: 22%-52%, 10 min) to give the title compound (45.0 mg, 17% yield) as a yellow solid. ¹H NMR (400 MHz, DMSO-d₆) δ 7.97 (s, 1H), 7.30 (s, 1H), 4.39 (s, 2H), 4.02-3.92 (m, 1H), 3.83-3.79 (m, 1H), 3.77-3.74 (m, 1H), 3.45 (d, J=10.0 Hz, 2H), 3.24 (d, J=5.6 Hz, 2H), 2.40 (d, J=10.0 Hz, 1H), 1.99-1.88 (m, 3H), 1.87-1.72 (m, 5H), 1.61-1.49 (m, 2H), 1.42-1.31 (m, 1H), 1.12-1.00 (m, 2H); LC-MS (ESI+) m/z 388.1 (M+H)⁺.

Step 2—5-Amino-2-[4-(hydroxymethyl)cyclohexyl]-6-[(1S,4S)-2-oxa-5-azabicyclo[2.2.1]heptan-5-yl]isoindolin-1-one To a solution of 2-[4-(hydroxymethyl)cyclohexyl]-5-nitro-6-[(1S,4S)-2-oxa-5-azabicyclo[2.2.1]heptan-5-yl]isoindolin-1-one (45.0 mg, 116 umol) in THF (0.1 mL), EtOH (0.5 mL) and H₂O (0.5 mL) was added NH₄Cl (62.1 mg, 1.16 mmol) and Fe (32.4 mg, 580 umol) at 70° C. The reaction mixture was then stirred at 80° C. for 2 hrs. On completion, the reaction mixture was filtered with celite and the filtrate was concentrated in vacuo to give a residue. The residue was diluted with H₂O (30 mL) and extracted with EA (3×10 mL). The combined organic layers were washed with brine 30 mL (2×15 mL), dried over by Na₂SO₄, filtered and concentrated in vacuo to give the title compound (35.0 mg, 84% yield) as a yellow solid. LC-MS (ESI+) m/z 358.1 (M+H)⁺.

Step 3—N-[2-[4-(hydroxymethyl)cyclohexyl]-6-[(1S,4S)-2-oxa-5-azabicyclo[2.2.1]heptan-5-yl]-1-oxo-isoindolin-5-yl]-6-(trifluoromethyl)pyridine-2-carboxamide To a solution of 5-amino-2-[4-(hydroxymethyl)cyclohexyl]-6-[(1S,4S)-2-oxa-5-azabicyclo[2.2.1]heptan-5-yl]isoindolin-1-one (35.0 mg, 97.9 umol) and 6-(trifluoromethyl)pyridine-2-carboxylic acid (18.71 mg, 97.9 umol, CAS #131747-42-7) in DMF (3 mL) was added DIEA (25.3 mg, 195 umol) and CMPI (40.0 mg, 156 umol) at 25° C. The reaction mixture was stirred at 25° C. for 1 hr. On completion, the reaction mixture was concentrated in vacuo. The residue was purified by reverse phase (0.1% FA condition) to give the title compound (17.0 mg, 32% yield) as a white solid. LC-MS (ESI+) m/z 531.4 (M+H)+.

Step 4—N-[2-(4-formylcyclohexyl)-6-[(1S,4S)-2-oxa-5-azabicyclo[2.2.1]heptan-5-yl]-1-oxo-isoindolin-5-yl]-6-(trifluoromethyl)pyridine-2-carboxamide To a solution of N-[2-[4-(hydroxymethyl)cyclohexyl]-6-[(1S,4S)-2-oxa-5-azabicyclo[2.2.1]heptan-5-yl]-1-oxo-isoindolin-5-yl]-6-(trifluoromethyl)pyridine-2-carboxamide (17.0 mg, 32.0 umol) in DCM (1 mL) was added DMP (21.7 mg, 51.2 umol) at 25° C. The reaction mixture was then stirred at 25° C. for 1 hr. On completion, the reaction mixture was quenched by addition 1 mL sat. aq. $Na_2S_2O_3$ and 1 mL $NaHCO_3$ and then diluted with 15 mL H2O. The mixture was extracted with DCM (3×5 mL) and the combined organic layers were washed with brine 10 mL (2×5 mL), dried over by $Na_2SO_4$, filtered and concentrated in vacuo to give the title compound (8.00 mg, 47% yield) as a white solid. LC-MS (ESI+) m/z 529.1 (M+H)+.

3-(3-Methyl-2-oxo-4-piperazin-1-yl-benzimidazol-1-yl)piperidine-2,6-dione (Intermediate BAI)

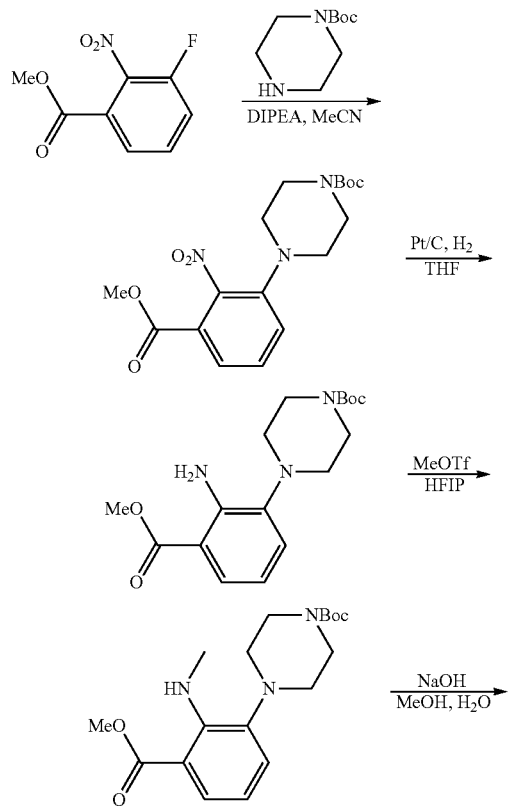

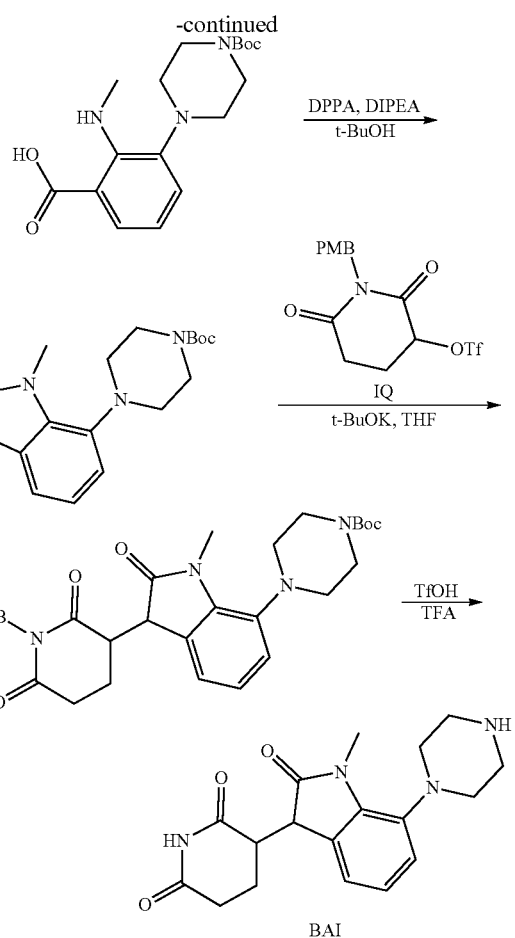

Step 1—Tert-butyl 4-(3-methoxycarbonyl-2-nitrophenyl)piperazine-1-carboxylate

To a solution of methyl 3-fluoro-2-nitro-benzoate (10.0 g, 50.2 mmol, CAS #1214353-57-7) and tert-butyl piperazine-1-carboxylate (11.2 g, 60.3 mmol, CAS #143238-38-4) in ACN (100 mL) was added DIPEA (19.5 g, 151 mmol). The reaction mixture was stirred at 50° C. for 12 hrs. On completion, the mixture was concentrated in vacuo. The residue was dissolved in water (200 mL), then extracted with EA (2×200 mL). The organic layer was washed with brine (2×100 mL), dried with $Na_2SO_4$, filtered and the filtrate was concentrated in vacuo to give the title compound (18.3 g, 100% yield) as yellow oil. $^1$H NMR (400 MHz, DMSO-$d_6$) δ 7.86 (dd, J=1.2, 8.0 Hz, 1H), 7.82-7.79 (m, 1H), 7.74-7.68 (m, 1H), 3.83 (s, 3H), 3.40-3.35 (m, 4H), 2.88-2.84 (m, 4H), 1.41 (s, 9H).

Step 2—Tert-butyl 4-(2-amino-3-methoxycarbonyl-phenyl)piperazine-1-carboxylate

To a solution of tert-butyl 4-(3-methoxycarbonyl-2-nitrophenyl)piperazine-1-carboxylate (17.0 g, 46.5 mmol) in THF (15 mL) was added Pd/C (2.00 g, 10 wt %). The reaction mixture was stirred at 20° C. for 12 hrs under $H_2$ (15 Psi) atmosphere. On completion, the mixture was filtered and the filtrate was concentrated in vacuo to give the title compound (15.2 g, 97% yield) as a yellow solid. $^1$H NMR (400 MHz, $CDCl_3$) δ 7.67 (dd, J=1.2, 8.0 Hz, 1H), 7.10 (dd, J=1.2, 7.6 Hz, 1H), 6.61 (t, J=7.6 Hz, 1H), 6.24 (br s, 2H), 4.28-3.95 (m, 2H), 3.87 (s, 3H), 3.16-2.84 (m, 4H), 2.80-2.55 (m, 2H), 1.49 (s, 9H).

Step 3—Tert-butyl 4-[3-methoxycarbonyl-2-(methylamino)phenyl]piperazine-1-carboxylate To a solution of tert-butyl 4-(2-amino-3-methoxycarbonyl-phenyl)piperazine-1-carboxylate (15.0 g, 44.7 mmol) in 1,1,1,3,3,3-hexafluoropropan-2-ol (40 mL) was added methyl trifluoromethanesulfonate (9.54 g, 58.1 mmol) at 0° C. The reaction mixture was stirred at 0° C. for 0.5 hr. On completion, the mixture was diluted with water (200 mL), then extracted with EA (2×200 mL). The organic layer was washed with brine (2×200 mL), dried with $Na_2SO_4$, filtered and the filtrate was concentrated in vacuo to give the title compound (15.0 g, 96% yield) as a yellow solid. $^1$H NMR (400 MHz, DMSO-$d_6$) δ 8.16-7.90 (m, 1H), 7.46 (dd, J=1.2, 8.0 Hz, 1H), 7.23 (d, J=7.6 Hz, 1H), 6.77 (t, J=7.6 Hz, 1H), 3.80 (s, 3H), 3.55-3.45 (m, 4H), 2.87 (s, 3H), 2.80-2.74 (m, 4H), 1.42 (s, 9H).

Step 4—3-(4-Tert-butoxycarbonylpiperazin-1-yl)-2-(methylamino)benzoic Acid

To a solution of tert-butyl 4-[3-methoxycarbonyl-2-(methylamino)phenyl]piperazine-1-carboxylate (14.0 g, 40.1 mmol) in a mixed solvent of $H_2O$ (20 mL) and MeOH (140 mL) was added NaOH (4.81 g, 120 mmol). The reaction mixture was stirred at 70° C. for 12 hrs. On completion, the mixture was concentrated in vacuo. The residue was diluted with water (200 mL), and extracted with EA (100 mL). The organic layer was discarded. The aqueous phase was acidified with HCl (1N) to pH=3-5, and extracted with EA (2×100 mL). The organic layer was washed with brine (200 mL), dried with $Na_2SO_4$, filtered and the filtrate was concentrated in vacuo. The residue was triturated with MeOH/$H_2O$ (1:10, 100 mL) and filtered. The filter cake was dried in vacuo to give the title compound (9.60 g, 71% yield) as a white solid. LC-MS (ESI$^+$) m/z 336.1 (M+H)$^+$.

Step 5—Tert-butyl 4-(3-methyl-2-oxo-1H-benzimidazol-4-yl)piperazine-1-carboxylate To a solution of 3-(4-tert-butoxycarbonylpiperazin-1-yl)-2-(methylamino)benzoic acid (9.60 g, 28.6 mmol) and DIPEA (11.1 g, 85.9 mmol) in t-BuOH (200 mL) was added DPPA (7.88 g, 28.6 mmol). The reaction mixture was stirred at 85° C. for 12 hrs. On completion, the mixture was concentrated in vacuo. The residue was diluted with water (200 mL), and extracted with EA (2×200 mL). The organic layer was washed with brine (200 mL) and concentrated in vacuo. The residue was purified by reverse phase (0.1% FA condition) to give the title compound (3.35 g, 35% yield) as a white solid. $^1$H NMR (400 MHz, DMSO-$d_6$) δ 10.84 (s, 1H), 6.94-6.87 (m, 1H), 6.85-6.79 (m, 1H), 6.75 (dd, J=1.2, 7.6 Hz, 1H), 4.06-3.80 (m, 2H), 3.55 (s, 3H), 3.20-2.87 (m, 4H), 2.76-2.56 (m, 2H), 1.42 (s, 9H).

Step 6—Tert-butyl 4-[1-[1-[(4-methoxyphenyl)methyl]-2,6-dioxo-3-piperidyl]-3-methyl-2-oxo-benzimidazol-4-yl]piperazine-1-carboxylate To a solution of tert-butyl 4-(3-methyl-2-oxo-1H-benzimidazol-4-yl)piperazine-1-carboxylate (3.30 g, 9.93 mmol) in THF (50 mL) was added t-BuOK (1.67 g, 14.9 mmol) at 0° C. 1 hr later, and a solution of [1[(4-methoxyphenyl) methyl]-2,6-dioxo-3-piperidyl]trifluoromethanesulfonate (4.54 g, 11.9 mmol, Intermediate IQ) in THF (20 mL) was added. The reaction mixture was stirred at 0° C. for 3 hrs. On completion, the mixture was acidified with FA to pH=3-5, diluted with water (300 mL), then extracted with EA (2×300 mL). The organic layer was washed with brine (200 mL) and concentrated in vacuo. The residue was purified by reverse phase flash (0.1% FA condition) to give the title compound (3.90 g, 70% yield) as a white solid. LC-MS (ESI$^+$) m/z 564.3 (M+H)$^+$.

Step 7—3-(3-Methyl-2-oxo-4-piperazin-1-yl-benzimidazol-1-yl)piperidine-2,6-dione To a solution of tert-butyl 4-[1-[1-[(4-methoxyphenyl)methyl]-2,6-dioxo-3-piperidyl]-3-methyl-2-oxo-benzimidazol-4-yl]piperazine-1-carboxylate (3.90 g, 6.92 mmol) in TFA (40 mL) was added TfOH (5 mL). The reaction mixture was stirred at 65° C. for 12 hrs. On completion, the mixture was concentrated in vacuo. The residue was purified by reverse phase flash (0.1% FA condition) to give the title compound (1.70 g, 63% yield, FA salt) as a blue solid. $^1$H NMR (400 MHz, DMSO-$d_6$) δ 11.09 (s, 1H), 7.06-6.99 (m, 1H), 6.96-6.92 (m, 2H), 5.36 (dd, J=5.2, 12.4 Hz, 1H), 3.63 (s, 3H), 3.35-3.25 (m, 4H), 3.16-2.97 (m, 4H), 2.91-2.82 (m, 1H), 2.76-2.57 (m, 2H), 2.05-1.93 (m, 1H).

N-[2-(4-formyl cyclohexyl)-6-morpholino-1-oxo-isoindolin-5-yl]-6-(trifluoromethyl)pyridine-2-carboxamide (Intermediate BOA)

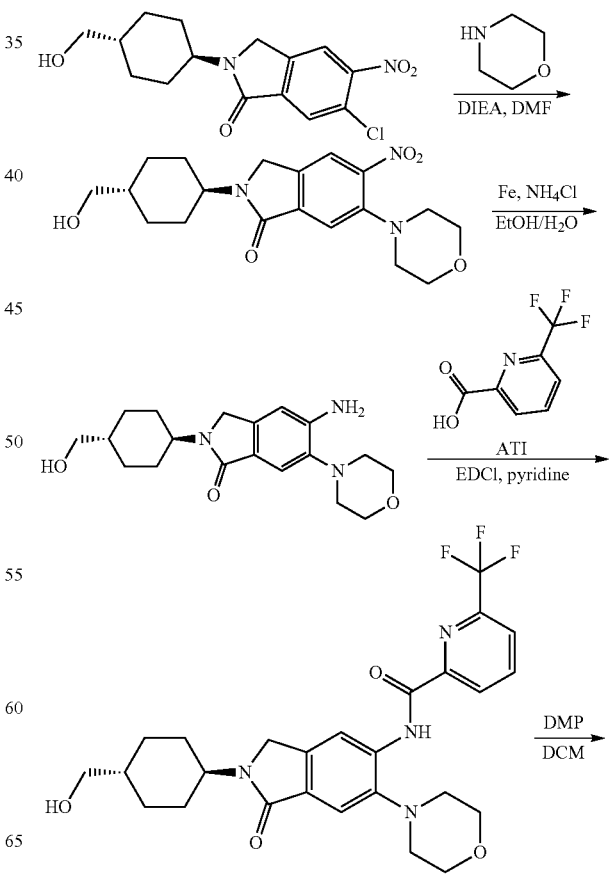

-continued

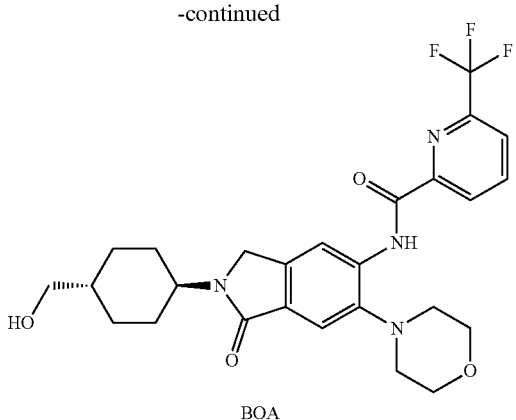

BOA

Step 1—2-[4-(Hydroxymethyl)cyclohexyl]-6-morpholino-5-nitro-isoindolin-1-one To a solution of 6-chloro-2-[4-(hydroxymethyl)cyclohexyl]-5-nitro-isoindolin-1-one (300 mg, 923 umol, synthesized via Steps 1-2 of Intermediate BMI) and morpholine (104 mg, 1.20 mmol) in DMSO (4 mL) was added DIEA (238 mg, 1.85 mmol) at 25° C. The reaction mixture was stirred at 80° C. for 12 hours. On completion, the reaction mixture was concentrated in vacuo. The residue was purified by reverse phase (0.1% FA condition) to give the title compound (240 mg, 69% yield) as a yellow solid. LC-MS (ESI$^+$) m/z 375.9 (M+H)$^+$.

Step 2—5-Amino-2-[4-(hydroxymethyl)cyclohexyl]-6-morpholino-isoindolin-1-one To a solution of 2-[4-(hydroxymethyl)cyclohexyl]-6-morpholino-5-nitro-isoindolin-1-one (140 mg, 372 umol) in H$_2$O (2.5 mL), EtOH (2.5 mL) and THF (0.5 mL) was added NH$_4$Cl (199 mg, 3.73 mmol) at 25° C. Then Fe (104 mg, 1.86 mmol) was added to the above mixture at 70° C., and the reaction mixture was stirred at 80° C. for 2 hours. On completion, the reaction mixture was filtered with celite and the filtrate was concentrated in vacuo. The residue was diluted with H$_2$O (30 mL) and extracted with EA (3×10 mL). The combined organic layers were washed with brine (2×15 mL), dried over Na$_2$SO$_4$, filtered and concentrated in vacuo. The residue was purified by reverse phase (0.1% FA condition) to give the title compound (30.0 mg, 23% yield) as a white solid. LC-MS (ESI$^+$) m/z 346.2 (M+H)$^+$.

Step 3—N-[2-[4-(hydroxymethyl)cyclohexyl]-6-morpholino-1-oxo-isoindolin-5-yl]-6-(trifluoromethy)pyridine-2-carboxamide To a solution of 5-amino-2-[4-(hydroxymethyl)cyclohexyl]-6-morpholino-isoindolin-1-one (30.0 mg, 86.8 umol) and 6-(trifluoromethyl)pyridine-2-carboxylic acid (19.9 mg, 104 umol, Intermediate ATI) in pyridine (0.6 mL) was added EDCI (24.9 mg, 130 umol) and the reaction mixture was stirred at 25° C. for 12 hours. On completion, the reaction mixture was concentrated in vacuo. The residue was purified by reverse phase (0.1% FA condition) to give the title compound (20.0 mg, 44% yield) as a white solid. LC-MS (ESI$^+$) m/z 519.2 (M+H)$^+$.

Step 4—N-[2-(4-formylcyclohexyl)-6-morpholino-1-oxo-isoindolin-5-yl]-6-(trifluoromethyl)pyridine-2-carboxamide To a solution of N-[2-[4-(hydroxymethyl)cyclohexyl]-6-morpholino-1-oxo-isoindolin-5-yl]-6-(trifluoromethyl)pyridine-2-carboxamide (15.0 mg, 28.9 umol) in DCM (1 mL) was added DMP (15.9 mg, 37.6 umol) and the reaction mixture was stirred at 25° C. for 1 hour. On completion, the reaction mixture was quenched with sat. aq. Na$_2$S$_2$O$_3$ (1 mL) and sat. aq. NaHCO$_3$(1 mL) and diluted with H$_2$O (15 mL) and were extracted with DCM (3×5 mL). The combined organic layers were washed with brine 10 mL (2×5 mL), dried over Na$_2$SO$_4$, filtered and concentrated in vacuo to give the title compound (14.0 mg, 93% yield) as a white solid. LC-MS (ESI$^+$) m/z 517.2 (M+H)$^+$.

N-[2-(4-formylcyclohexyl)-6-[(1R,4R)-2-oxa-5-azabicyclo[2.2.1]heptan-5-yl]-1-oxo-isoindolin-5-yl]-6-(trifluoromethyl)pyridine-2-carboxamide (Intermediate BQF)

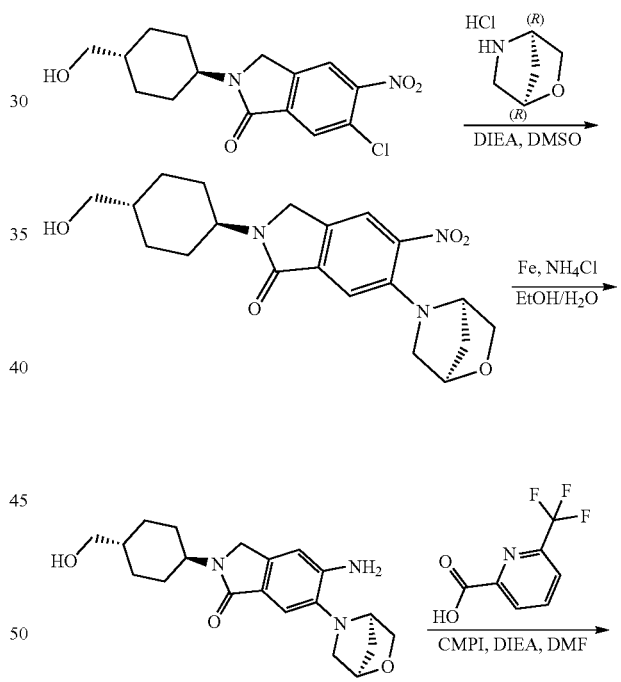

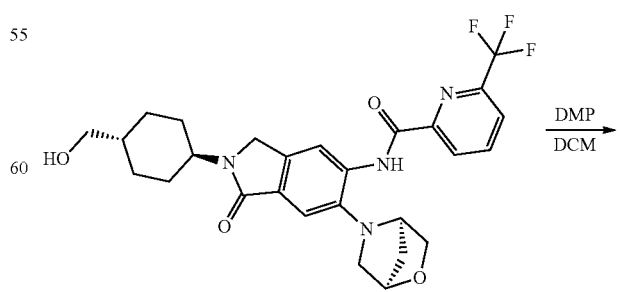

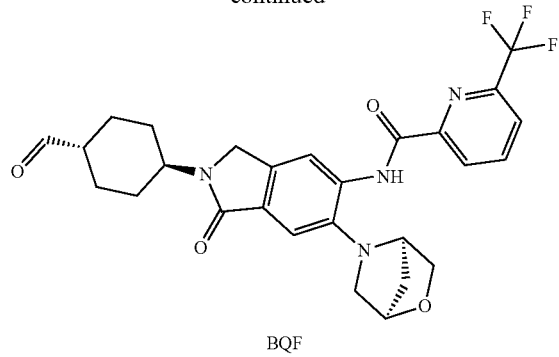

BQF

Step 1—2-[4-(Hydroxymethyl)cyclohexyl]-5-nitro-6-[(1R,4R)-2-oxa-5-azabicyclo[2.2.1]heptan-5-yl]isoindolin-1-one To a solution of 6-chloro-2-[4-(hydroxymethyl)cyclohexyl]-5-nitro-isoindolin-1-one (220 mg, 677 umol, synthesized via Steps 1-2 of Intermediate BMI) and (1R,4R)-2-oxa-5-azabicyclo[2.2.1]heptane (183 mg, 1.35 mmol, HCl salt, CAS #279-33-4) in DMSO (4 mL) was added DIEA (262 mg, 2.03 mmol) at 25° C. The reaction mixture was then stirred at 80° C. for 36 hrs. On completion, the reaction mixture was concentrated in vacuo. The residue was purified by reverse phase (0.1% FA condition) to give the title compound (55.0 mg, 20% yield) as a yellow solid. LC-MS (ESI+) m/z 388.4 (M+H)+.

Step 2—5-Amino-2-[4-(hydroxymethyl)cyclohexyl]-6-[(1R,4R)-2-oxa-5-azabicyclo[2.2.1]heptan-5-yl]isoindolin-1-one To a solution of 2-[4-(hydroxymethyl)cyclohexyl]-5-nitro-6-[(1R,4R)-2-oxa-5-azabicyclo[2.2.1]heptan-5-yl]isoindolin-1-one (55.0 mg, 141 umol) in EtOH (1 mL), THF (0.2 mL) and H2O (1 mL) was added NH4Cl (75.9 mg, 1.42 mmol) and Fe (39.6 mg, 709 umol) at 70° C. Then the reaction mixture was stirred at 80° C. for 1 hr. On completion, the reaction mixture was filtered with celite and the filtrate was concentrated in vacuo to give a residue. The residue was diluted with 30 mL H2O and extracted with EA (3×10 mL). The combined organic layers were washed with brine (2×15 mL), dried over by Na2SO4, filtered and concentrated in vacuo to give the title compound (35.0 mg, 68% yield) as a yellow solid. LC-MS (ESI+) m/z 357.9 (M+H)+.

Step 3—N-[2-[4-(hydroxymethyl)cyclohexyl]-6-[(1R,4R)-2-oxa-5-azabicyclo[2.2.1]heptan-5-yl]-1-oxo-isoindolin-5-yl]-6-(trifluoromethyl)pyridine-2-carboxamide To a solution of 5-amino-2-[4-(hydroxymethyl)cyclohexyl]-6-[(1R,4R)-2-oxa-5-azabicyclo[2.2.1]heptan-5-yl]isoindolin-1-one (35.0 mg, 97.9 umol) and 6-(trifluoromethyl)pyridine-2-carboxylic acid (18.7 mg, 97.9 umol, CAS #131747-42-7) in DMF (1 mL) was added DIEA (25.3 mg, 195 umol) and CMPI (40.0 mg, 156 umol). The mixture was stirred at 25° C. for 1 hr. On completion, the reaction mixture was concentrated in vacuo. The residue was purified by reverse phase (0.1% FA condition) to give the title compound (26.0 mg, 50% yield) as a white solid. LC-MS (ESI+) m/z 531.4 (M+H)+.

Step 4—N-[2-(4-formylcyclohexyl)-6-[(1R,4R)-2-oxa-5-azabicyclo[2.2.1]heptan-5-yl]-1-oxo-isoindolin-5-yl]-6-(trifluoromethyl)pyridine-2-carboxamide To a solution of N-[2-[4-(hydroxymethyl)cyclohexyl]-6-[(1R,4R)-2-oxa-5-azabicyclo[2.2.1]heptan-5-yl]-1-oxo-isoindolin-5-yl]-6-(trifluoromethyl)pyridine-2-carboxamide (26.0 mg, 49.0 umol) in DCM (1 mL) was added DMP (33.2 mg, 78.4 umol) at 25° C. and the reaction mixture was stirred at 25° C. for 1 hr. On completion, the reaction mixture was quenched by addition sat.aq. Na2S2O3 (1 mL) and NaHCO3 (1 mL) and then diluted with H2O 15 mL, then the mixture was extracted with DCM (3×5 mL). The combined organic layers were washed with brine 10 mL (2×5 mL), dried over by Na2SO4, filtered and concentrated in vacuo to give the title compound (20.0 mg, 77% yield) as a white solid. LC-MS (ESI+) m/z 529.2 (M+H)+.

N-(6-fluoro-2-((1R,3R)-3-formylcyclobutyl)-2H-indazol-5-yl)-6-(trifluoromethyl)picolinamide (Intermediate BQH)

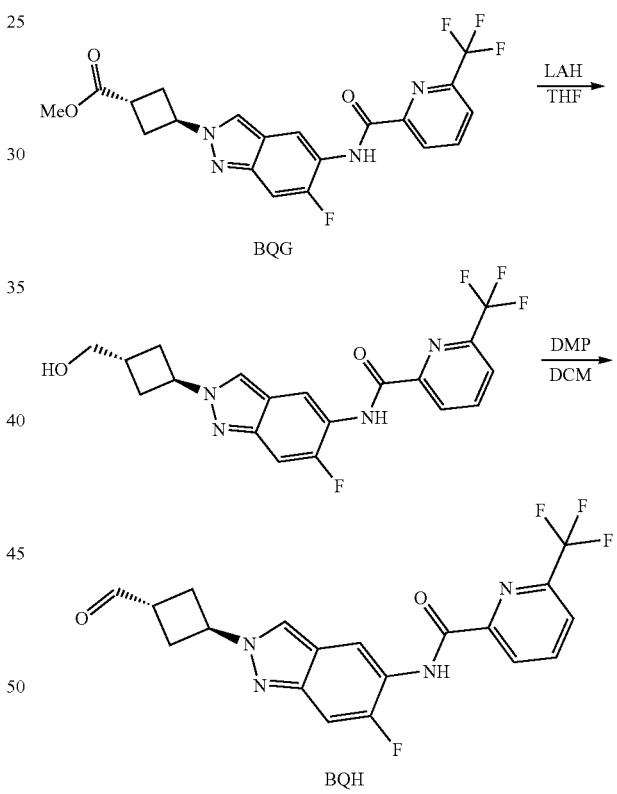

Step 1—N-(6-Fluoro-2-((1R,3R)-3-(hydroxymethyl)cyclobutyl)-2H-indazol-5-yl)-6-(trifluoromethyl)picolinamide To a solution of methyl 3-[6-fluoro-5-[[6-(trifluoromethyl)pyridine-2-carbonyl]amino]indazol-2-yl]cyclobutanecarboxylate (170 mg, 389 umol, Intermediate BQG) in THF (4 mL) was added LiAlH4 (29.5 mg, 779 umol). Then the reaction mixture was stirred at 0° C. for 1 hour. The reaction mixture was quenched by addition 15% seignette salt (0.1 mL) at 0° C., and then diluted with THF (10 mL), filtered and concentrated under reduced pressure to give the title compound (100 mg, 52% yield) as an off-white solid. LC-MS (ESI⁺) m/z 408.9 (M+H)⁺. $^1$H NMR (400 MHz, CDCl$_3$) δ 10.25 (d, J=3.2 Hz, 1H), 8.81 (d, J=7.8 Hz, 1H), 8.51 (d, J=7.8 Hz, 1H), 8.15 (t, J=7.8 Hz, 1H), 7.98 (s, 1H), 7.90 (dd, J=0.8, 7.8 Hz, 1H), 7.47 (d, J=11.6 Hz, 1H), 5.14 (t, J=7.8 Hz, 1H), 3.84 (d, J=6.2 Hz, 2H), 2.98-2.84 (m, 2H), 2.78-2.64 (m, 1H), 2.60-2.47 (m, 2H).

Step 2—N-(6-fluoro-2-((1R,3R)-3-formylcyclobutyl)-2H-indazol-5-yl)-6-(trifluoromethyl)picolinamide To a solution of N-[6-fluoro-2-[3-(hydroxymethyl)cyclobutyl]indazol-5-yl]-6-(trifluoromethyl) pyridine-2-carboxamide (159 mg, 389 umol) in DCM (2 mL) was added DMP (247 mg, 584 umol). The mixture was stirred at 20° C. for 1 hour. On completion, the reaction mixture was quenched by addition sat. NaHCO$_3$ (10 mL) and sat. Na$_2$SO$_3$ (10 mL) at 0° C., and then diluted with H$_2$O (10 mL) and extracted with EA (3×30 mL). The combined organic layers were washed with brine (20 mL), dried over Na$_2$SO$_4$, filtered and concentrated under reduced pressure to give the title compound (100 mg, 46% yield) as an off-white solid. LC-MS (ESI⁺) m/z 407.3 (M+H)⁺.

N-[2-[3-(hydroxymethyl)cyclobutyl]-6-methoxy-indazol-5-yl]-6-(trifluoromethyl)pyridine-2-carboxamide (Intermediate BQI)

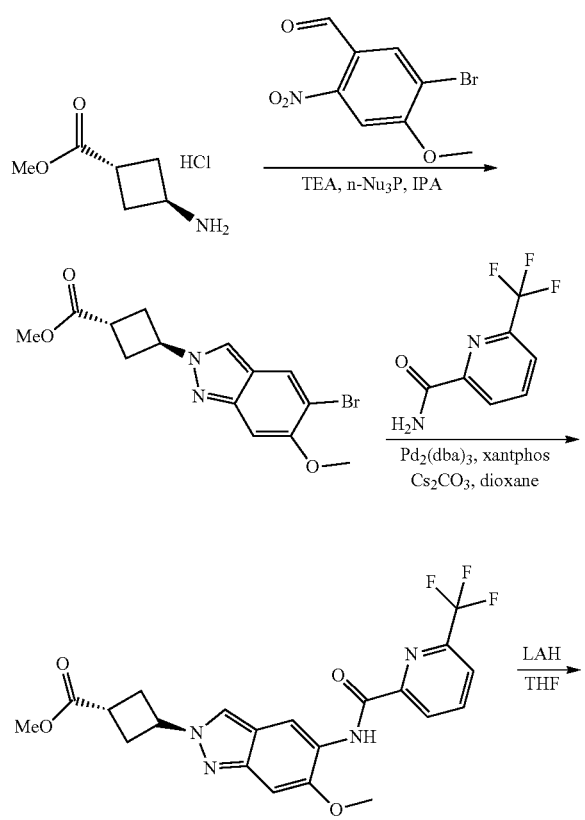

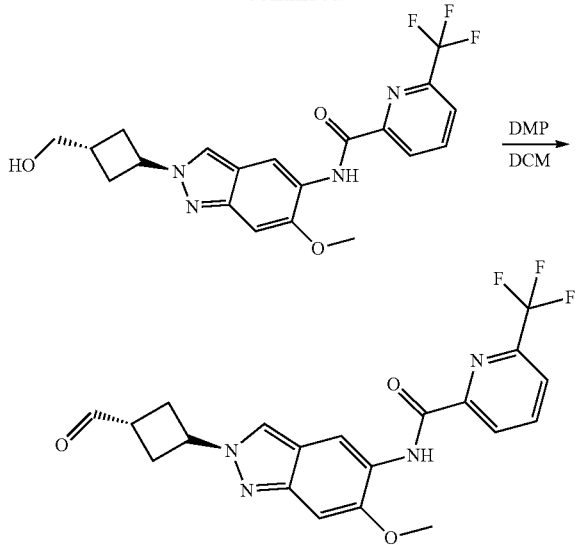

Step 1—Methyl 3-(5-bromo-6-methoxy-indazol-2-yl)cyclobutanecarboxylate

To a solution of methyl 3-aminocyclobutanecarboxylate (3 g, 18.11 mmol, HCl salt, CAS #74316-29-3) in IPA (60 mL) was added Et$_3$N (1.83 g, 18.1 mmol, 2.52 mL) and 5-bromo-4-methoxy-2-nitro-benzaldehyde (5.18 g, 19.9 mmol, synthesized via Steps 1-2 of Intermediate ATE) and the mixture was stirred at 80° C. for 4 hrs. After the reaction was cooled to rt, tributylphosphane (10.9 g, 54.3 mmol, 13.41 mL) was added to the mixture and the mixture was stirred at 80° C. for 4 hrs. On completion, the mixture was concentrated in vacuo. The residue was purified by column chromatography (SiO$_2$, PE:EA 5:1) to give the title compound (900 mg, 15% yield) as yellow solid. $^1$H NMR (400 MHz, DMSO-d$_6$) δ 8.34 (d, J=0.8 Hz, 1H), 7.97 (s, 1H), 7.14 (s, 1H), 5.32-5.22 (m, 1H), 3.87 (s, 3H), 3.69 (s, 3H), 3.33-3.27 (m, 1H), 2.94-2.84 (m, 2H), 2.77-2.69 (m, 2H).

Step 2—Methyl 3-[6-methoxy-5-[[6-(trifluoromethyl)pyridine-2-carbonyl]amino]indazol-2-yl]cyclobutanecarboxylate To a solution of methyl 3-(5-bromo-6-methoxy-indazol-2-yl)cyclobutanecarboxylate (600 mg, 1.77 mmol) and 6-(trifluoromethyl)pyridine-2-carboxamide (403 mg, 2.12 mmol, Intermediate ATI) in DMA (20 mL) was added BrettPhos Pd G3 (160 mg, 176 umol), Cs$_2$CO$_3$ (1.15 g, 3.54 mmol) and 4 Å molecular sieves (100 mg). The mixture was stirred at 90° C. for 6 hrs. On completion, the mixture was filtered with celite. The crude product was purified by reversed-phase HPLC (0.1% FA condition) to give the title compound (500 mg, 63% yield) as yellow solid. $^1$H NMR (400 MHz, DMSO-d$_6$) δ 10.51 (s, 1H), 8.68 (s, 1H), 8.48-8.36 (m, 3H), 8.22 (d, J=7.6 Hz, 1H), 7.20 (s, 1H), 5.25 (q, J=7.6 Hz, 1H), 3.99 (s, 3H), 3.70 (s, 3H), 3.31-3.27 (m, 1H), 2.97-2.85 (m, 2H), 2.81-2.69 (m, 2H); LC-MS (ESI⁺) m/z 449.3 (M+H)⁺.

Step 3—N-[2-[3-(hydroxymethyl)cyclobutyl]-6-methoxy-indazol-5-yl]-6-(trifluoromethyl)pyridine-2-carboxamide To a solution of methyl 3-[6-methoxy-5-[[6-(trifluoromethyl) pyridine-2-carbonyl]amino] indazol-2-yl]cyclobutanecarboxylate (150 mg, 334 umol) in THF (1 mL) was added LiAlH₄ (25.4 mg, 669 umol) and the mixture was stirred at 0° C. for 1 hr under N₂. On completion, water (0.5 mL) was added to the mixture at 0° C., then 15% NaOH.aq (0.5 mL) was added, and finally water (1.5 mL) was added. The mixture was dried over Na₂SO₄, filtered and concentrated under reduced pressure to give the title compound (130 mg, 92% yield) as yellow solid. ¹H NMR (400 MHz, DMSO-d₆) δ 10.50 (s, 1H), 8.67 (s, 1H), 8.49-8.32 (m, 3H), 8.21 (br d, J=7.6 Hz, 1H), 7.18 (s, 1H), 5.13 (br t, J=8.0 Hz, 1H), 4.98-4.62 (m, 2H), 3.98 (s, 3H), 3.58 (br s, 1H), 2.71-2.62 (m, 2H), 2.38-2.30 (m, 2H); LC-MS (ESI⁺) m/z 421.2 (M+H)⁺.

Step 4—N-[2-[3-(hydroxymethyl)cyclobutyl]-6-methoxy-indazol-5-yl]-6-(trifluoromethyl)pyridine-2-carboxamide To a solution of N-[2-[3-(hydroxymethyl)cyclobutyl]-6-methoxy-indazol-5-yl]-6-(trifluoromethyl)pyridine -2-carboxamide (65.0 mg, 154 umol) in DCM (10 mL) was added DMP (98.3 mg, 231 umol) and the mixture was stirred at 25° C. for 2 hrs. On completion, to the mixture was added sat. NaHCO₃. aq (10 ml) and sat. Na₂S₂O₃. aq (10 ml), and the mixture was extracted with DCM 150 mL (3×50 mL). The combined organic layers were washed with brine 100 mL, dried over Na₂SO₄, filtered and concentrated under reduced pressure to give the title compound (64.0 mg, 99% yield) as yellow solid. LC-MS (ESI⁺) m/z 421.2 (M+H)⁺.

Tert-butyl N-[2-(4-formylcyclohexyl)-6-methoxy-indazol-5-yl]carbamate (Intermediate BGT)

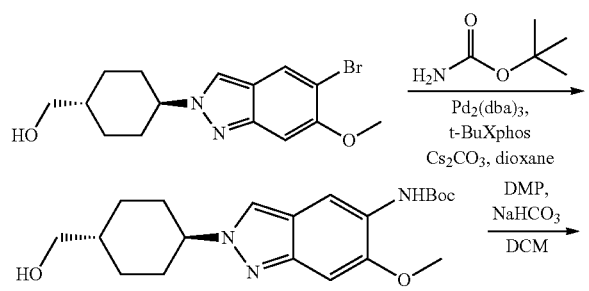

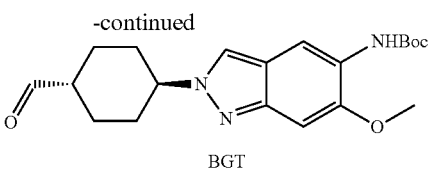

BGT

Step 1—Tert-butyl N-[2-[4-(hydroxymethyl)cyclohexyl]-6-methoxy-indazol-5-yl]carbamate A mixture of [4-(5-bromo-6-methoxy-indazol-2-yl)cyclohexyl]methanol (8.00 g, 23.6 mmol, synthesized via Steps 1-3 of Intermediate ATE), tert-butyl carbamate (4.14 g, 35.4 mmol), Pd₂(dba)₃ (2.16 g, 2.36 mmol), t-Bu Xphos (2.00 g, 4.72 mmol) and Cs₂CO₃ (15.4 g, 47.2 mmol) in dioxane (150 mL) was de-gassed and heated at 90° C. for 12 hrs. On completion, the mixture was concentrated in vacuo. The residue was purified by silica gel chromatography (SiO₂) and then re-purified by reverse phase (0.1% FA condition) to give the title compound (5.00 mg, 57% yield) as a white solid. LC-MS (ESI⁺) m/z 376.1 (M+H)⁺.

Step 2—Tert-butyl N-[2-(4-formylcyclohexyl)-6-methoxy-indazol-5-yl]carbamate To a mixture of tert-butyl N-[2-[4-(hydroxymethyl)cyclohexyl]-6-methoxy-indazol-5-yl]carbamate (800 mg, 2.13 mmol) and NaHCO₃ (716 mg, 8.52 mmol) in DCM (20 mL) was added DMP (1.36 g, 3.20 mmol). The reaction mixture was stirred at 20° C. for 2 hrs. On completion, the mixture was quenched with sat. Na₂S₂O₃ (50 mL) and NaHCO₃ (50 mL), stirred for 10 min, then extracted with DCM (2×50 mL). The organic layer was washed with brine (80 mL), dried in Na₂SO₄, filtered and the filtrate was concentrated in vacuo to give the title compound (700 mg, 88% yield) as a yellow solid. LC-MS (ESI⁺) m/z 374.2 (M+H)⁺.

3-[4-[4-[[4-(5-Amino-6-methoxy-indazol-2-yl)cyclohexyl]methyl-methyl-amino]-1-piperidyl]-3-methyl-2-oxo-benzimidazol-1-yl]piperidine -2,6-dione (Intermediate BGU)

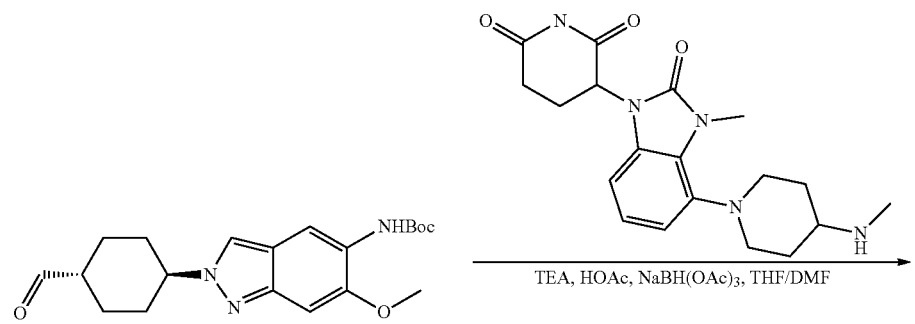

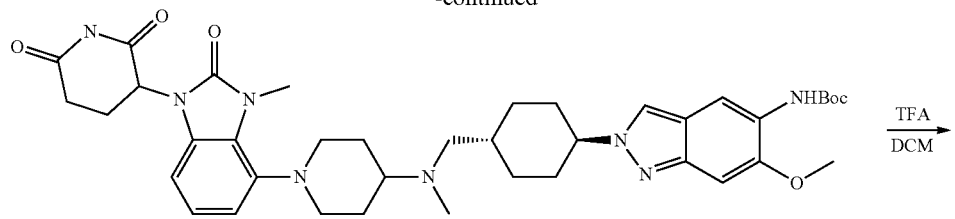

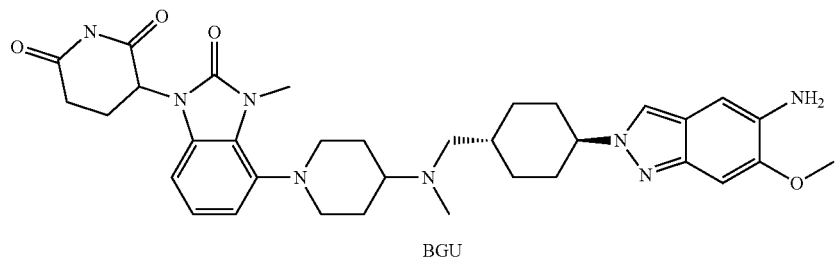

BGU

Step 1—Tert-butyl N-[2-[4-[[[1-[1-(2,6-dioxo-3-piperidyl)-3-methyl-2-oxo-benzimidazol-4-yl]-4-piperidyl]-methyl-amino]methyl]cyclohexyl]-6-methoxy-indazol-5-yl]carbamate To a solution of 3-[3-methyl-4-[4-(methylamino)-1-piperidyl]-2-oxo-benzimidazol-1-yl]piperidine-2,6-dione (873 mg, 2.14 mmol, HCl salt, Intermediate AQK) in a mixed solvent of DMF (10 mL) and THF (50 mL) was added KOAc (315 mg, 3.21 mmol). Then the mixture was cooled to 0° C. and tert-butyl N-[2-(4-formylcyclohexyl)-6-methoxy-indazol-5-yl]carbamate (800 mg, 2.14 mmol, Intermediate BGT) was added. Thirty minutes later, NaBH(OAc)$_3$ (907 mg, 4.28 mmol) was added into the above mixture and the reaction mixture was stirred at 0° C. for 3 hrs. On completion, the mixture was quenched with water (5 mL), concentrated in vacuo. The residue was purified by reverse phase (0.1% FA condition) to give the title compound (1.00 g, 64% yield) as a yellow solid. $^1$H NMR (400 MHz, DMSO-d$_6$) δ 11.08 (s, 1H), 8.17 (s, 1H), 7.89 (s, 1H), 7.75 (s, 1H), 7.08-6.77 (m, 4H), 5.34 (dd, J=5.2, 12.8 Hz, 1H), 4.40-4.24 (m, 1H), 3.84 (s, 3H), 3.63 (s, 3H), 3.16-3.12 (m, 2H), 2.96-2.81 (m, 1H), 2.76-2.57 (m, 4H), 2.47-2.39 (m, 1H), 2.28-2.26 (m, 2H), 2.24 (s, 3H), 2.15-2.06 (s, 2H), 1.99-1.74 (m, 7H), 1.72-1.51 (m, 3H), 1.45 (s, 9H), 1.14-1.01 (m, 2H).

Step 2—3-[4-[4-[[4-(5-Amino-6-methoxy-indazol-2-yl)cyclohexyl]methyl-methyl-amino]-1-piperidyl]-3-methyl-2-oxo-benzimidazol-1-yl]piperidine-2,6-dione To a solution of tert-butyl N-[2-[4-[[[1-[1-(2,6-dioxo-3-piperidyl)-3-methyl-2-oxo-benzimidazol-4-yl]-4-piperidyl]-methyl -amino]methyl]cyclohexyl]-6-methoxy-indazol-5-yl]carbamate (60.0 mg, 82.3 umol) in TFA (2 mL) was added DCM (2 mL). The reaction mixture was stirred at 20° C. for 0.5 hr. On completion, the mixture was concentrated in vacuo to give the title compound (60.0 mg, 98% yield, TFA salt) as a yellow solid. LC-MS (ESI$^+$) m/z 629.4 (M+H)$^+$.

6-(Trifluoromethyl)pyridazine-4-carboxylic acid (Intermediate BQJ)

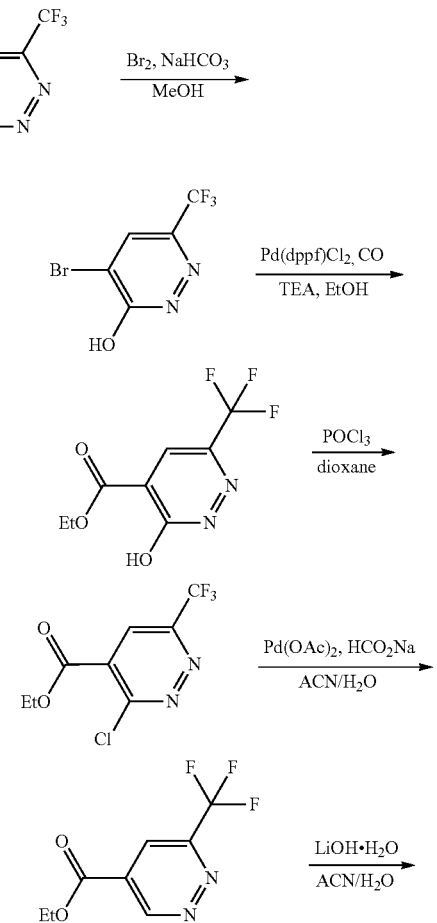

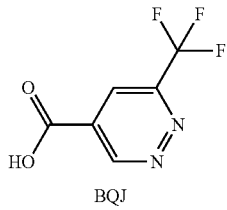

BQJ

Step 1—4-Bromo-6-(trifluoromethyl)pyridazin-3-ol

To a solution of 6-(trifluoromethyl)pyridazin-3-ol (3.00 g, 18.3 mmol) (CAS #174607-36-4), NaHCO$_3$ (4.61 g, 54.8 mmol, 2.13 mL) in MeOH (50 mL) was added Br$_2$ (4.38 g, 27.4 mmol) slowly. The reaction mixture was then stirred at 20° C. for 12 hrs. On completion, The reaction mixture was filtered and concentrated in vacuo. The crude was diluted with ethyl acetate (80 mL), washed with brine (20 mL), and dried over anhydrous sodium sulfate. The mixture was filtered and concentrated in vacuo to give the title compound (4.00 g, 90% yield) as a yellow solid. $^1$H NMR (400 MHz, CDCl$_3$) δ 11.61-11.26 (m, 1H), 7.92 (s, 1H) LC-MS (ESI$^+$) m/z 243.0 (M+H)$^+$.

Step 2—Ethyl 3-hydroxy-6-(trifluoromethyl)pyridazine-4-carboxylate

To a solution of 4-bromo-6-(trifluoromethyl)pyridazin-3-ol (4 g, 16.5 mmol) in EtOH (50 mL) was added Pd(dppf)Cl$_2$·CH$_2$Cl$_2$ (1.34 g, 1.65 mmol) and TEA (8.33 g, 82.3 mmol, 11.5 mL) under N$_2$ atmosphere. The suspension was degassed and purged with CO three times. The mixture was stirred under CO (50 psi) at 80° C. for 16 hrs. On completion, the reaction mixture was filtered and concentrated in vacuo. The residue was purified by silica gel chromatography (PE:EA=10:1 to 4:1) to give the title compound (3.10 g, 80% yield) as a white solid. $^1$H NMR (400 MHz, CDCl$_3$) δ 12.15-11.26 (m, 1H), 8.07 (s, 1H), 4.47 (q, J=7.2 Hz, 2H), 1.44 (t, J=7.2 Hz, 3H).

Step 3—Ethyl 3-chloro-6-(trifluoromethyl)pyridazine-4-carboxylate

To a solution of ethyl 3-hydroxy-6-(trifluoromethyl)pyridazine-4-carboxylate (1.4 g, 5.93 mmol) in dioxane (5 mL) was added POCl$_3$ (7.22 g, 47.0 mmol, 4.38 mL). The reaction mixture was then heated to 100° C. and stirred for 4 hrs. On completion, the reaction was quenched with water (30 mL) and basified with sodium bicarbonate solution (60 mL) and extracted with ethyl acetate (2×50 mL). The combined organic layers were washed with brine (30 mL) and dried over anhydrous sodium sulfate, filtered and the filtrate was concentrated in vacuo. The residue was purified by silica gel chromatography (PE:EA=10:1) to give the title compound (1.00 g, 66% yield) as a yellow liquid. $^1$H NMR (400 MHz, CDCl$_3$) δ 8.15 (s, 1H), 4.53 (q, J=7.2 Hz, 2H), 1.47 (t, J=7.2 Hz, 3H), LC-MS (ESI$^+$) m/z 255.0 (M+H)$^+$.

Step 4—Ethyl 6-(trifluoromethyl)pyridazine-4-carboxylate

To a solution of ethyl 3-chloro-6-(trifluoromethyl)pyridazine-4-carboxylate (1 g, 3.93 mmol) in a mixed solvent of ACN (5 mL) and H$_2$O (1 mL) was added HCOONa (400 mg, 5.88 mmol) and Pd(OAc)$_2$ (88.1 mg, 392 umol) under N$_2$. The suspension was then stirred at 105° C. for 4 hrs under N$_2$ atmosphere. On completion, the reaction mixture was filtered and the mixture solvent was purified by reversed-phase HPLC (0.1% HCl, condition) to give the title compound (200 mg, 23% yield) as a colorless oil. LC-MS (ESI$^+$) m/z 221.1 (M+H)$^+$.

Step 5—6-(Trifluoromethyl)pyridazine-4-carboxylic Acid

To a solution of ethyl 6-(trifluoromethyl)pyridazine-4-carboxylate (190 mg, 863 umol) in a mixed solvent of ACN (20 mL) and H$_2$O (50 mL) was added LiOH·H$_2$O (250 mg, 5.96 mmol) and the reaction mixture was stirred at 25° C. for 1 hr. On completion, the reaction mixture was acidified with HCl (1N) 6.0 mL, and extracted with ethyl acetate (3×50 mL). The combined organic layers were dried over anhydrous sodium sulfate, filtered and concentrated in vacuo to give the title compound (165 mg, 99% yield) as a white solid. $^1$H NMR (400 MHz, DMSO-d$_6$) δ 9.80 (d, J=2.0 Hz, 1H), 8.39 (d, J=2.0 Hz, 1H), LC-MS (ESI$^+$) m/z 193.1 (M+H)$^+$.

3-(4-bromo-6-chloro-3-methyl-2-oxo-2,3-dihydro-1H-benzo[d]imidazol-1-yl)piperidine-2,6-dione (Intermediate BQN)

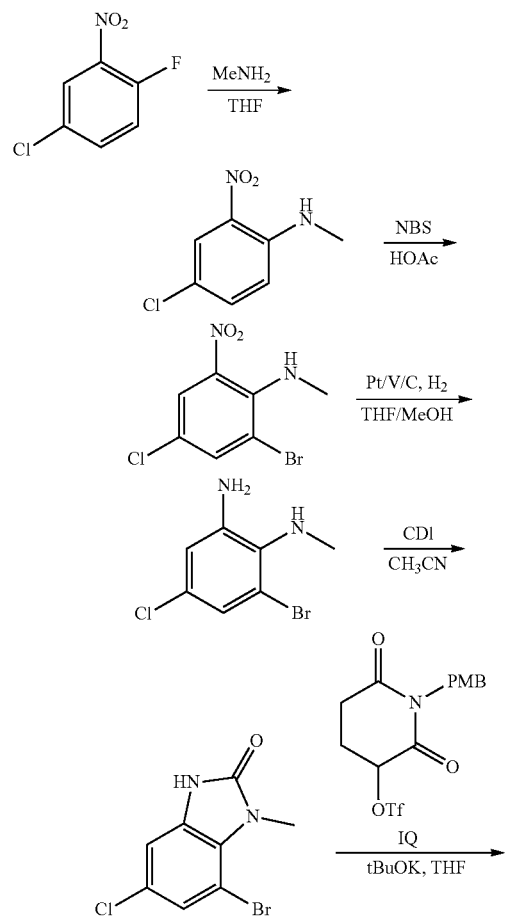

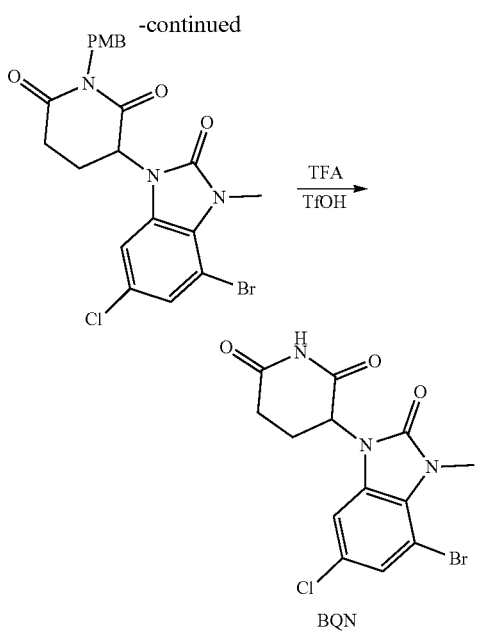

Step 1—4-Chloro-N-methyl-2-nitroaniline

To a solution of MeNH$_2$ (2 M, 22.8 mL) in the THF (25 mL) was added 4-chloro-1-fluoro-2-nitro-benzene (2 g, 11.4 mmol, CAS #345-18-6) and DIEA (2.94 g, 22.8 mmol). The mixture was stirred at 60° C. for 4 hrs. On completion, the reaction mixture was concentrated in vacuo. The residue was diluted with EA (100 mL) and washed with water (3×100 mL). The organic layer was dried over Na$_2$SO$_4$, filtered and concentrated in vacuo to give the title compound (2.1 g, 99% yield) as yellow solid. $^1$H NMR (400 MHz, CDCl$_3$) δ 8.18 (d, J=2.4 Hz, 1H), 8.02 (s, 1H), 7.42 (dd, J=2.4, 9.2 Hz, 1H), 6.82 (d, J=9.2 Hz, 1H), 3.04 (s, 3H).

Step 2—2-Bromo-4-chloro-N-methyl-6-nitroaniline

A solution of 4-chloro-N-methyl-2-nitro-aniline (2 g, 10.7 mmol) and NBS (2.86 g, 16.0 mmol) in the AcOH (20 mL) was stirred at 20° C. for 16 hrs. On completion, the reaction mixture was diluted with EA (200 mL) and washed with brine (100 mL), and NaHCO$_3$ (2×100 mL). The organic layer was dried over Na$_2$SO$_4$, filtered and concentrated in vacuo. The residue was purified by column chromatography (petroleum ether/ethyl acetate=1/0 to 50/1) to give the title compound (2.5 g, 88% yield) as yellow solid. $^1$H NMR (400 MHz, CDCl$_3$) δ 7.89 (d, J=2.4 Hz, 1H), 7.68 (d, J=2.4 Hz, 1H), 6.18 (s, 1H), 3.02 (s, 3H).

Step 3—6-Bromo-4-chloro-N1-methylbenzene-1,2-diamine

To a solution of 2-bromo-4-chloro-N-methyl-6-nitro-aniline (2.5 g, 9.42 mmol) in the THF (10 mL) and MeOH (10 mL) was added Pt/V/C (300 mg, 10 wt %). The mixture was stirred at 20° C. for 12 hrs under H$_2$ (15 psi). On completion, the reaction mixture was filtered and concentrated in vacuo and purified by column chromatography (PE:EA=1:0 to 50:1) to give the title compound (1.68 g, 76% yield) as yellow oil. $^1$H NMR (400 MHz, DMSO-d$_6$) δ 6.90 (d, J=2.4 Hz, 1H), 6.64 (d, J=2.4 Hz, 1H), 4.10 (s, 2H), 3.17 (s, 1H), 2.64 (s, 3H).

Step 4—7-Bromo-5-chloro-1-methyl-1H-benzo[d]imidazol-2(3H)-one

To a solution of 3-bromo-5-chloro-N2-methyl-benzene-1,2-diamine (1.56 g, 6.62 mmol) in the MeCN (20 mL) was added CDI (1.61 g, 9.94 mmol). The mixture was stirred at 90° C. for 16 hrs. On completion, the reaction mixture was concentrated in vacuo. The residue was diluted with water (50 mL) and filtered to give the cake as title compound (1.42 g, 82% yield) as off-white solid. $^1$H NMR (400 MHz, CDCl$_3$) δ 11.36 (s, 1H), 7.24 (d, J=2.0 Hz, 1H), 7.01 (d, J=2.0 Hz, 1H), 3.54 (s, 3H).

Step 5—3-(4-Bromo-6-chloro-3-methyl-2-oxo-2,3-dihydro-1H-benzo[d]imidazol-1-yl)-1-(4-methoxybenzyl)piperidine-2,6-dione To a solution of 4-bromo-6-chloro-3-methyl-1H-benzimidazol-2-one (1.42 g, 5.43 mmol) in the THF (20 mL) was added tBuOK (914 mg, 8.15 mmol) at -10-0° C. The mixture was stirred for 20 mins. Then a solution of [1-[(4-methoxyphenyl)methyl]-2,6-dioxo-3-piperidyl]trifluoromethanesulfonate (3.11 g, 8.15 mmol, Intermediate IQ) in the THF (5 mL) was added for 40 mins at -10-0° C. On completion, the reaction mixture was acidified with FA to pH=5-6. Then the mixture was diluted with EA (150 mL) and washed with water (100 mL) and brine (100 mL). The organic layer was dried over Na$_2$SO$_4$, filtered and concentrated in vacuo and purified by column chromatography (petroleum ether/ethyl acetate=10/1 to 3/1) to give the title compound (2.0 g, 75% yield) as white solid. $^1$H NMR (400 MHz, CDCl$_3$) δ 7.36 (d, J=8.4 Hz, 2H), 7.23 (d, J=1.6 Hz, 1H), 6.84 (d, J=8.4 Hz, 2H), 6.46 (s, 1H), 5.19 (dd, J=5.2, 13.6 Hz, 1H), 5.03-4.91 (m, 2H), 3.79 (s, 3H), 3.76 (s, 3H), 3.07-2.98 (m, 1H), 2.89-2.78 (m, 1H), 2.59 (dq, J=4.2, 13.2 Hz, 1H), 2.21-2.12 (m, 1H).

Step 6—3-(4-bromo-6-chloro-3-methyl-2-oxo-2,3-dihydro-1H-benzo[d]imidazol-1-yl)piperidine-2,6-dione To a solution of 3-(4-bromo-6-chloro-3-methyl-2-oxo-benzimidazol-1-yl)-1-[(4-methoxyphenyl) methyl]piperidine-2,6-dione (200 mg, 406 umol) in the TFA (2 mL) was added TfOH (0.4 mL). The mixture was stirred at 70° C. for 12 hrs. On completion, the reaction mixture was concentrated by N$_2$ and purified by reversed phase (0.1% HCl) to give the title compound (24.8 mg, 16% yield) as gray solid. $^1$H NMR (400 MHz, DMSO-d$_6$) δ 11.14 (s, 1H), 7.42 (d, J=1.6 Hz, 1H), 7.36 (d, J=1.6 Hz, 1H), 5.42 (dd, J=5.2, 12.4 Hz, 1H), 3.62 (s, 3H), 2.90-2.80 (m, 1H), 2.80-2.70 (m, 1H), 2.66-2.60 (m, 1H), 2.07-1.98 (m, 1H). LC-MS (ESI$^+$) m/z 374.0 (M+3)$^+$.

3-[6-chloro-3-methyl-2-oxo-4-(4-piperidyl)benzimidazol-1-yl]piperidine-2,6-dione (Intermediate BQK)

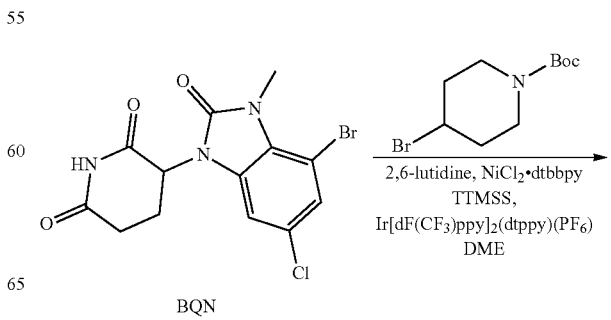

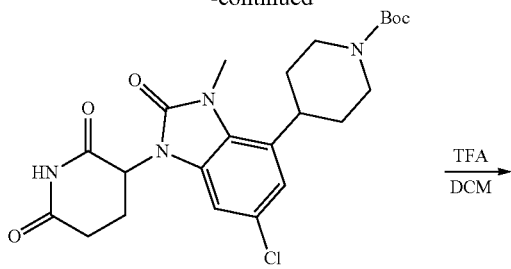

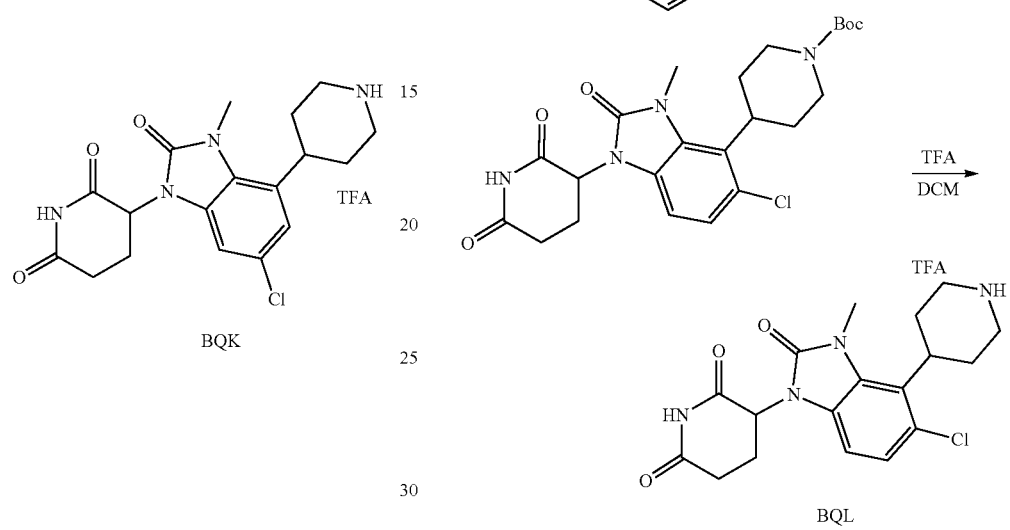

774

3-[5-chloro-3-methyl-2-oxo-4-(4-piperidyl)benzimidazol-1-yl]piperidine-2,6-dione (Intermediate BQL)

Step 1—Tert-butyl 4-[6-chloro-1-(2,6-dioxo-3-piperidyl)-3-methyl-2-oxo-benzimidazol-4-yl]piperidine-1-carboxylate To an 8 mL vial equipped with a stir bar was added 3-(4-bromo-6-chloro-3-methyl-2-oxo-benzimidazol-1-yl)piperidine-2,6-dione (600 mg, 1.61 mmol, Intermediate BQN), tert-butyl 4-bromopiperidine-1-carboxylate (425 mg, 1.61 mmol), Ir[dF(CF$_3$)ppy]$_2$(dtbpy)(PF$_6$) (18.0 mg, 16.10 umol), NiCl$_2$.dtbbpy (3.20 mg, 8.05 umol), TTMSS (400 mg, 1.61 mmol), and 2,6-lutidine (345 mg, 3.22 mmol) in DME (5 mL). The vial was sealed and placed under nitrogen. Then the reaction was stirred and irradiated with a 34 W blue LED lamp (7 cm away), with cooling fan to keep the reaction temperature at 25° C. for 14 hrs. On completion, the mixture was poured into the water (30 mL) and extracted with ethyl acetate (2×20 mL). The combined organic phase was washed with brine (2×30 mL), dried with anhydrous Na$_2$SO$_4$, filtered and concentrated in vacuo to give the residue. The residue was purified by reversed-phase HPLC (0.1% FA condition) to give the title compound (160 mg, 20% yield) as brown solid. LC-MS (ESI$^+$) m/z 421.2 (M–55)$^+$.

Step 2—3-[6-Chloro-3-methyl-2-oxo-4-(4-piperidyl)benzimidazol-1-yl]piperidine-2,6-dione To a solution of tert-butyl 4-[6-chloro-1-(2,6-dioxo-3-piperidyl)-3-methyl-2-oxo-benzimidazol-4-yl]piperidine-1-carboxylate (40.0 mg, 83.8 umol) in DCM (2 mL) was added TFA (19.1 mg, 167 umol). The reaction mixture was stirred at 25° C. for 0.5 hr. On completion, the mixture was concentrated in vacuo to give the title compound (40.0 mg, 97% yield) as brown oil. LC-MS (ESI$^+$) m/z 377.3 (M+H)$^+$.

Step 1—Tert-butyl 4-[5-chloro-1-(2,6-dioxo-3-piperidyl)-3-methyl-2-oxo-benzimidazol-4-yl] piperidine-1-carboxylate To a solution of tert-butyl 4-[1-(2,6-dioxo-3-piperidyl)-3-methyl-2-oxo-benzimidazol-4-yl] piperidine-1-carboxylate (1.00 g, 2.26 mmol, synthesized via Steps 1-2 of Intermediate AZK) in DCE (50.0 mL) was added PhI(OAc)$_2$ (727 mg, 2.26 mmol) and HCl (1 M, 11.30 mL). The mixture was stirred at 50° C. for 12 hrs. On completion, the reaction mixture was washed with saturated solution of NaHCO$_3$ (2× 50 mL) and saturated solution of Na$_2$S$_2$O$_3$ (2×50 mL). The organic layer was washed with brine (2×50 mL), then dried over anhydrous Na$_2$SO$_4$, filtered and concentrated in vacuo to give a residue. The residue was purified by reversed phase (0.1% FA condition) to give the crude product. The crude product was re-purified by prep-HPLC (column: Welch Ultimate XB-SiOH 250*50*10 um; mobile phase: [Hexane-EtOH]; B %: 1%-40%, 15 min) to give the title compound (250 mg, 23% yield) as a white solid. $^1$H NMR (400 MHz, CDCl$_3$-d) δ 8.20 (s, 1H), 7.07 (d, J=8.4 Hz, 1H), 6.61 (d, J=8.4 Hz, 1H), 5.18 (dd, J=4.4, 12.0 Hz, 1H), 4.42-4.16 (m, 2H), 3.71 (s, 3H), 3.67-3.57 (m, 1H), 3.02-2.91 (m, 1H), 2.90-2.65 (m, 6H), 2.27-2.18 (m, 1H), 1.50 (s, 9H).

Step 2—3-[5-Chloro-3-methyl-2-oxo-4-(4-piperidyl)benzimidazol-1-yl]piperidine-2,6-dione To a solution of tert-butyl 4-[5-chloro-1-(2,6-dioxo-3-piperidyl)-3-methyl-2-oxo-benzimidazol-4-yl] piperidine-1-carboxylate (30.0 mg, 62.9 umol) in DCM (2.00 mL) was added TFA (770 mg, 6.75 mmol, 0.50 mL). The mixture was stirred at 25° C. for 0.5 hr. On completion, the reaction 3-[3,5-Dimethyl-2-oxo-4-(4-piperidyl)benzimidazol-1-yl]piperidine-2,6-dione (Intermediate BQM)

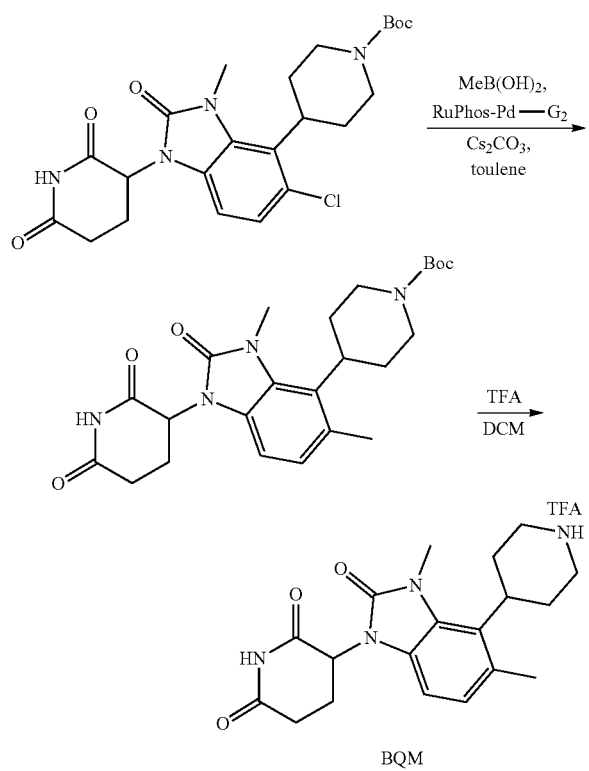

BQM

Step 1—Tert-butyl 4-[1-(2,6-dioxo-3-piperidyl)-3,5-dimethyl-2-oxo-benzimidazol-4-yl]piperidine-1-carboxylate To a mixture of tert-butyl 4-[5-chloro-1-(2,6-dioxo-3-piperidyl)-3-methyl-2-oxo-benzimidazol-4-yl] piperidine-1-carboxylate (95.0 mg, 199 umol, synthesized via Step 1 of Intermediate BQL) in toluene (4 mL) was added MeB(OH)$_2$ (238 mg, 3.98 mmol), Cs$_2$CO$_3$ (194 mg, 597 umol) and [2-(2-aminophenyl)phenyl]-chloro-palladium; dicyclohexyl-[2-(2,6-diisopropoxyphenyl)phenyl]phosphane (15.4 mg, 19.9 umol). Then the reaction mixture was stirred at 100° C. for 12 hours. On completion, the reaction mixture was filtered and concentrated in vacuo. The residue was purified by prep-HPLC (Column Phenomenex Luna C18 150*25 mm*10 um, Condition: water (0.225% FA)-ACN) to give the title compound (20.0 mg, 21% yield) as white solid. LC-MS (ESI$^+$) m/z 479.1 (M+Na)$^+$.

Step 2—3-[3,5-Dimethyl-2-oxo-4-(4-piperidyl)benzimidazol-1-yl]piperidine-2,6-dione To a mixture of tert-butyl 4-[1-(2,6-dioxo-3-piperidyl)-3,5-dimethyl-2-oxo-benzimidazol-4-yl] piperidine-1-carboxylate (20.0 mg, 43.8 umol) in DCM (3 mL) was added TFA (770 mg, 6.75 mmol, 0.5 mL) then the reaction mixture was stirred at 25° C. for 0.5 hour. On completion, the mixture was concentrated in vacuo to give the title compound (30.0 mg, 97% yield, TFA) as a white solid. LC-MS (ESI$^+$) m/z 377.3 (M+H)$^+$.

[4-(5-bromo-6-morpholino-indazol-2-yl)cyclohexyl]methanol (Intermediate AWW)

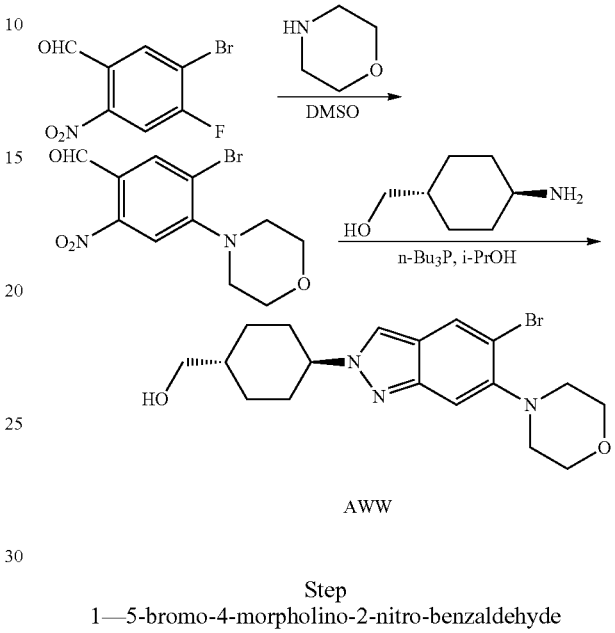

AWW

Step 1—5-bromo-4-morpholino-2-nitro-benzaldehyde

A solution of 5-bromo-4-fluoro-2-nitro-benzaldehyde (2.00 g, 8.06 mmol, synthesized via Step 1 of Intermediate ATE) in DMSO (25 mL) was added with morpholine (2.81 g, 32.3 mmol). The reaction mixture was stirred at 80° C. for 1 hours. On completion, the reaction mixture was then diluted in ethyl acetate (50 mL) and water (50 mL), then extracted with ethyl acetate (3×50 mL). The organic layer was dried over Na$_2$SO$_4$, filtered and concentrated in vacuo to afford the residue. The residue was purified by column chromatography (PE:EA=4:1) to give the title compound (1.50 g, 58% yield) as yellow solid. $^1$H NMR (400 MHz, CDCl$_3$) δ 10.33 (s, 1H), 8.21 (s, 1H), 7.63 (s, 1H), 4.07-3.82 (m, 4H), 3.32-3.24 (m, 4H). LC-MS (ESI$^+$) m/z 314.9, 316.9 (M+H)$^+$.

Step 2—[4-(5-bromo-6-morpholino-indazol-2-yl)cyclohexyl]methanol

To a solution of 5-bromo-4-morpholino-2-nitro-benzaldehyde (1.50 g, 4.76 mmol) in IPA (50 mL) was added (4-aminocyclohexyl) methanol (738 mg, 5.71 mmol, Intermediate ATD). The mixture was heated at 80° C. for 4 hr under N$_2$. Then the reaction was cooled to 25° C., and tributylphosphine (2.89 g, 14.3 mmol) was added. The reaction mixture was heated to 80° C. for 16 hr. On completion, the reaction mixture was concentrated in vacuo to remove some IPA, and a solid was precipitated. The mixture was filtered and the filter cake was washed by petroleum ether to give the title compound (1.00 g, 53% yield) as yellow solid. $^1$H NMR (400 MHz, CDCl$_3$) δ 7.93 (s, 1H), 7.86 (s, 1H), 7.32 (s, 1H), 4.39-4.32 (m, 1H), 4.02-3.86 (m, 4H), 3.58 (d, J=6.4 Hz, 2H), 3.10-3.09 (m, 4H), 2.51-2.22 (m, 2H), 2.15-1.89 (m, 4H), 1.78-1.64 (m, 2H), 1.34-1.25 (m, 2H). reaction mixture was concentrated in vacuo to give title compound (20.0 mg, 97% yield, TFA) as red oil. LC-MS (ESI$^+$) m/z 357.0 (M+H)$^+$.

N-[2-(4-formylcyclohexyl)-6-morpholino-indazol-5-yl]-6-(trifluoromethyl)pyridine-2-carboxamide (Intermediate AYL)

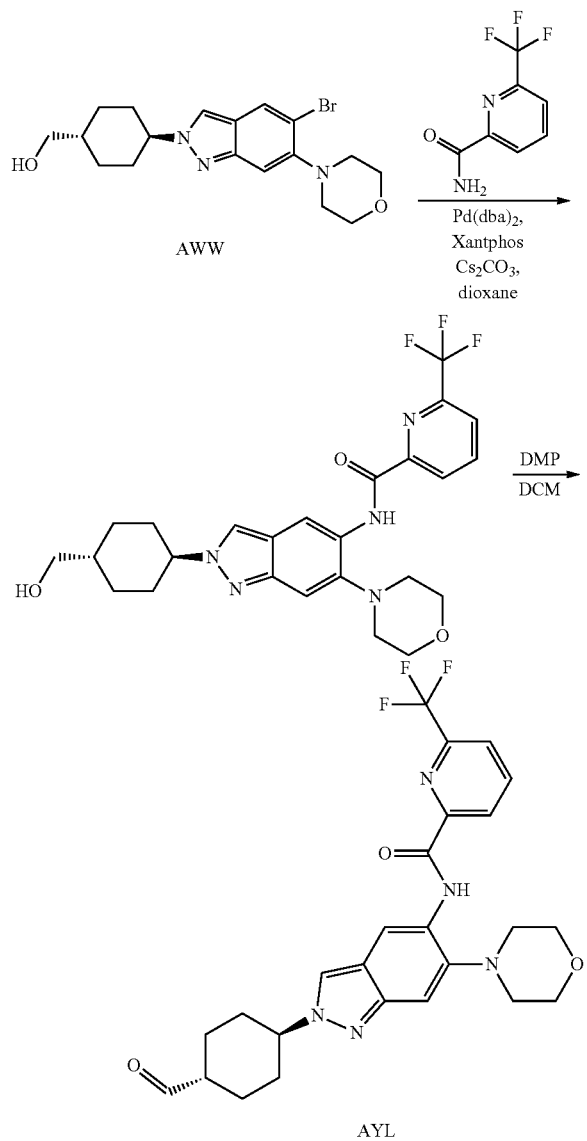

AYL

Step 1—N-[2-[4-(hydroxymethyl)cyclohexyl]-6-morpholino-indazol-5-yl]-6-(trifluoromethyl) pyridine-2-carboxamide To a solution of [4-(5-bromo-6-morpholino-indazol-2-yl)cyclohexyl]methanol (250 mg, 634 umol, Intermediate AWW) in dioxane (5.0 mL) was added Pd(dba)$_2$ (36.5 mg, 63.4 umol), Xantphos (73.4 mg, 127 umol), Cs$_2$CO$_3$ (413 mg, 1.27 mmol) and 6-(trifluoromethyl)pyridine-2-carboxamide (133 mg, 697 umol, Intermediate ATI). The mixture was stirred at 100° C. for 16 hours. On completion, the reaction mixture was filtered and concentrated in vacuo to give a residue. The residue was purified by reverse phase flash (0.1% FA condition) to give the title compound (100 mg, 31% yield) as a white solid. $^1$H NMR (400 MHz, CDCl$_3$) δ 11.25 (s, 1H), 8.93 (s, 1H), 8.57 (d, J=8.0 Hz, 1H), 8.16 (t, J=8.0 Hz, 1H), 8.00-7.85 (m, 2H), 7.54 (s, 1H), 4.38 (tt, J=3.6, 12.0 Hz, 1H), 4.10-3.95 (m, 4H), 3.59 (d, J=6.4 Hz, 2H), 3.18-2.97 (m, 4H), 2.44-2.27 (m, 2H), 2.14-1.90 (m, 5H), 1.53-1.39 (m, 1H), 1.35-1.19 (m, 2H). LC-MS (ESI$^+$) m/z 504.2 (M+H)$^+$.

Step 2—N-[2-(4-formylcyclohexyl)-6-morpholino-indazol-5-yl]-6-(trifluoromethyl)pyridine-2-carboxamide To a mixture of N-[2-[4-(hydroxymethyl)cyclohexyl]-6-morpholino-indazol-5-yl]-6-(trifluoromethyl) pyridine-2-carboxamide (100 mg, 200 umol) in DCM (3.0 mL) was added DMP (126 mg, 298 umol) at 25° C. under N$_2$. The mixture was stirred at 25° C. for 1 hr. On completion, the reaction mixture was quenched with Na$_2$S$_2$O$_3$ (6.0 mL) and extracted with DCM (2×5.0 mL). The combined organic layer was washed with NaHCO$_3$ aqueous and brine (2×5.0 mL), dried with anhydrous Na$_2$SO$_4$, filtered and concentrated in vacuo to give the title compound (100 mg, 96% yield) as white solid. LC-MS (ESI$^+$) m/z 502.2 (M+H)$^+$.

3-[3,5-Dimethyl-4-[4-(methylamino)-1-piperidyl]-2-oxo-benzimidazol-1-yl]piperidine-2,6-dione (Intermediate BQV)

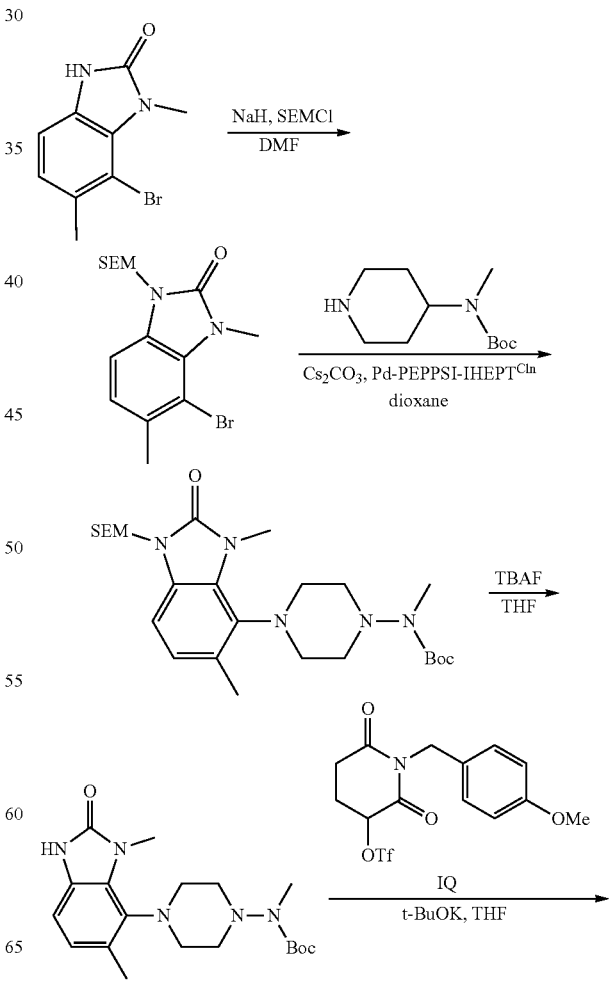

-continued

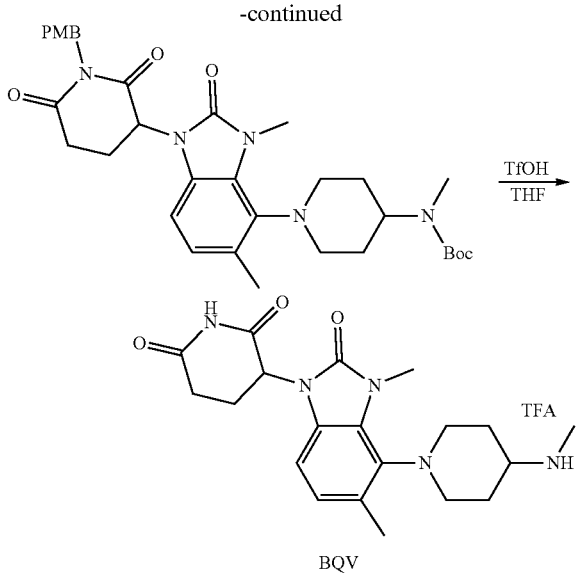

Step 1—4-Bromo-3,5-dimethyl-1-((2-(trimethylsilyl)ethoxy)methyl)-1H-benzo[d]imidazol-2(3H)-one To a solution of 4-bromo-3,5-dimethyl-1H-benzimidazol-2-one (1.00 g, 4.15 mmol, synthesized via Steps 1-5 of Intermediate BRG) in the DMF (10 mL) was added NaH (249 mg, 6.22 mmol, 60% dispersion in mineral oil) at 0° C. and the mixture was stirred for 30 mins. Then SEM-Cl (1.38 g, 8.30 mmol) was added and the mixture was stirred at 20° C. for 12 hrs. On completion, the reaction mixture was poured into ice water (50 mL) and extracted with EA (100 mL). The organic layer was dried over $Na_2SO_4$, filtered and concentrated in vacuo. The residue was purified by column chromatography (PE:EA=20:1) to give the title compound (900 mg, 58% yield) as white solid. $^1$H NMR (400 MHz, $CDCl_3$) δ 7.04-6.96 (m, 2H), 5.30 (s, 2H), 3.80 (s, 3H), 3.63-3.56 (m, 2H), 2.44 (s, 3H), 0.95-0.89 (m, 2H), −0.02 (s, 9H).

Step 2—Tert-butyl (1-(3,5-dimethyl-2-oxo-1-((2-(trimethylsilyl)ethoxy)methyl)-2,3-dihydro-1H-benzo[d]imidazol-4-yl)piperidin-4-yl)(methyl)carbamate To a solution of 4-bromo-3,5-dimethyl-1-(2-trimethylsilylethoxymethyl)benzimidazol-2-one (500 mg, 1.35 mmol) and tert-butyl N-methyl-N-(4-piperidyl)carbamate (432 mg, 2.02 mmol) in dioxane (5 mL) was added $Cs_2CO_3$ (1.32 g, 4.04 mmol) and catalyst Pd-PEPPSI-IHEPT$^{Cln}$ (40 mg, CAS #1612891-29-8). The mixture was stirred at 100° C. for 12 hours. On completion, the reaction mixture was concentrated under reduced pressure to remove the solvent. The residue was diluted with $H_2O$ (10 mL) and extracted with EA (3×30 mL). The combined organic layers were washed with brine (10 mL), dried over $Na_2SO_4$, filtered and concentrated under reduced pressure to give a residue. The crude product was purified by reverse phase (0.1% FA condition) to give the title compound (120 mg, 16% yield) as a brown solid. $^1$H NMR (400 MHz, $CDCl_3$) δ 6.91 (d, J=7.8 Hz, 1H), 6.80 (d, J=7.8 Hz, 1H), 5.28 (s, 2H), 3.77 (s, 3H), 3.64-3.57 (m, 2H), 3.46 (d, J=1.6 Hz, 2H), 3.09 (d, J=12.0 Hz, 2H), 2.81 (s, 3H), 2.41 (s, 3H), 1.87 (s, 2H), 1.68 (d, J=11.6 Hz, 2H), 1.50 (s, 9H), 0.96-0.89 (m, 2H), 0.88-0.73 (m, 1H), −0.03 (s, 9H). LC-MS (ESI$^+$) m/z 505.5 (M+H)$^+$.

Step 3—Tert-butyl (1-(3,5-dimethyl-2-oxo-2,3-dihydro-1H-benzo[d]imidazol-4-yl)piperidin-4-yl)(methyl)carbamate To a solution of tert-butyl N-[1-[3,5-dimethyl-2-oxo-1-(2-trimethylsilylethoxymethyl)benzimidazol-4-yl]-4-piperidyl]-N-methyl-carbamate (120 mg, 237 umol) in THF (2 mL) was added TBAF (621 mg, 2.38 mmol). The mixture was stirred at 80° C. for 12 hours. On completion, the reaction mixture was concentrated under reduced pressure to remove solvent and give a residue. The crude product was triturated with mixture of MeCN (0.5 mL) and $H_2O$ (1 mL) at 20° C. for 60 minutes to give the title compound (60.0 mg, 65% yield) as an off-white solid. $^1$H NMR (400 MHz, $CDCl_3$) δ 8.58 (s, 1H), 6.83-6.72 (m, 2H), 4.30-3.93 (m, 1H), 3.75 (s, 3H), 3.50-3.41 (m, 2H), 3.09 (m, 2H), 2.82 (s, 3H), 2.39 (s, 3H), 1.95-1.82 (m, 2H), 1.68 (m, 2H), 1.50 (s, 9H). LC-MS (ESI$^+$) m/z 375.0 (M+H)$^+$.

Step 4—Tert-butyl N-[1-[1-[1-[(4-methoxyphenyl)methyl]-2,6-dioxo-3-piperidyl]-3,5-dimethyl-2-oxo-benzimidazol-4-yl]-4-piperidyl]-N-methyl-carbamate To a solution of tert-butyl N-[1-(3,5-dimethyl-2-oxo-1H-benzimidazol-4-yl)-4-piperidyl]-N-methyl-carbamate (60.0 mg, 160 umol) in THF (2.00 mL) was added t-BuOK (26.9 mg, 240 umol) at -10° C. and the mixture was stirred at −10° C. for 1 hr. Then a solution of [1-[(4-methoxyphenyl)methyl]-2,6-dioxo-3-piperidyl]trifluoromethanesulfonate (91.6 mg, 240 umol, Intermediate IQ) in THF (1.00 mL) was added to the above solution and the mixture was stirred at −10° C. for 1 hr. On completion, the mixture was quenched with sat. $NH_4Cl$ (15 mL) and extracted with EA (3×10 mL). The organic layers were washed with brine (2×10 mL), dried over anhydrous $Na_2SO_4$, filtered and concentrated in vacuo. The mixture was purified by reverse phase: (0.1% FA) to give the title compound (60.0 mg, 61% yield) as yellow solid. 1H NMR (400 MHz, DMSO-$d_6$) δ 7.20 (d, J=8.8 Hz, 2H), 6.91-6.78 (m, 2H), 6.75-6.65 (m, 2H), 5.52-5.38 (m, 1H), 4.89-4.69 (m, 2H), 4.13-3.79 (m, 1H), 3.72 (s, 3H), 3.65 (s, 3H), 3.05-2.99 (m, 3H), 2.83-2.77 (m, 1H), 2.74 (s, 3H), 2.72-2.68 (m, 1H), 2.53-2.51 (m, 2H), 2.39-2.33 (m, 3H), 2.05-1.97 (m, 1H), 1.95-1.83 (m, 2H), 1.63-1.48 (m, 2H), 1.42 (s, 9H). LC-MS (ESI+) m/z 606.5 (M+H)$^+$.

Step 5—3-[3,5-Dimethyl-4-[4-(methylamino)-1-piperidyl]-2-oxo-benzimidazol-1-yl]piperidine-2,6-dione A solution of tert-butyl N-[1-[1-[1-[(4-methoxyphenyl)methyl]-2,6-dioxo-3-piperidyl]-3,5-dimethyl-2-oxo-benzimidazol-4-yl]-4-piperidyl]-N-methyl-carbamate (60.0 mg, 99.0 umol) in a mix solvent of TfOH (170 mg, 1.13 mmol) and TFA (1.23 g, 10.8 mmol). The mixture was stirred at 70° C. for 16 hrs. On completion, the mixture was concentrated in vacuo. The mixture was purified by prep-HPLC (GX-U, Phenomenex Luna C18 150*25 mm*10 um, water (0.1% TFA)-ACN, 5%-35%, 10 min) to give the title compound (35 mg, 91% yield) as white solid. $^1$H NMR (400 MHz, DMSO-$d_6$) δ 11.07 (s, 1H), 8.61 (s, 1H), 6.92-6.83 (m, 1H), 6.81-6.73 (m, 1H), 5.37-5.25 (m, 1H), 3.62 (s, 3H), 3.30-3.25 (m, 2H), 3.15-3.03 (m, 3H), 2.94-2.81 (m, 1H), 2.73-

2.62 (m, 2H), 2.62-2.58 (m, 3H), 2.33 (s, 3H), 2.05-1.91 (m, 3H), 1.83-1.65 (m, 2H). LC-MS (ESI⁺) m/z 386.1 (M+H)⁺.

N-[2-(4-formylcyclohexyl)-6-methoxy-1-methyl-indol-5-yl]-6-(trifluoromethyl)pyridine-2-carboxamide (Intermediate BQW)

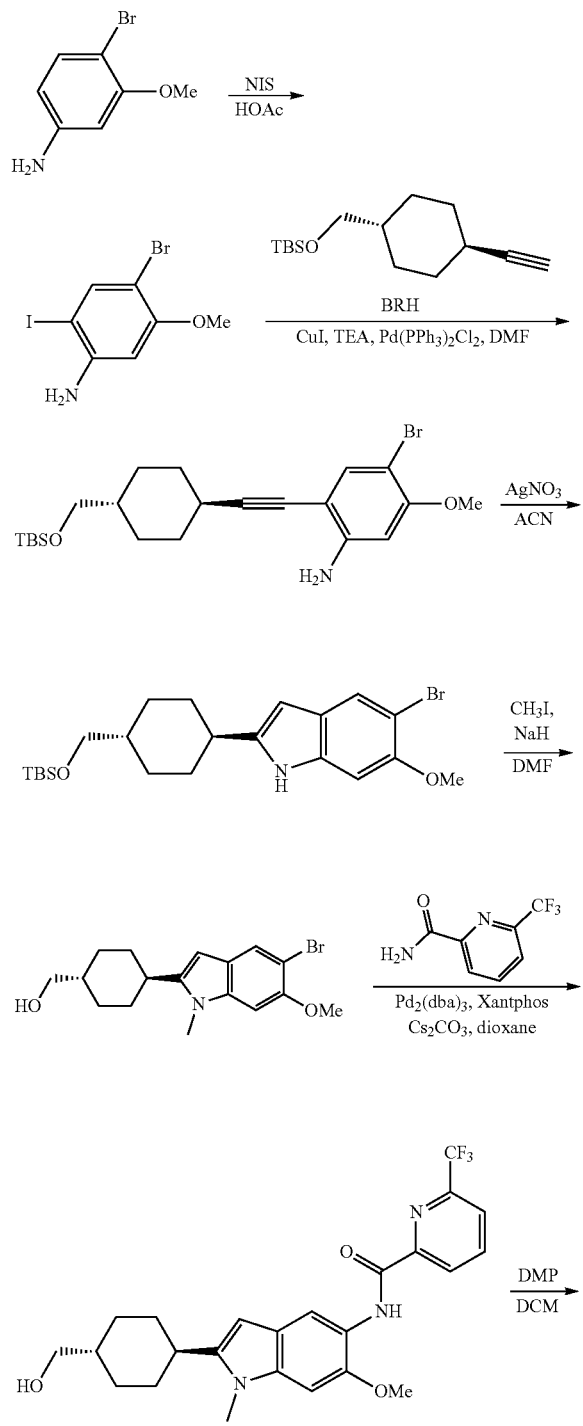

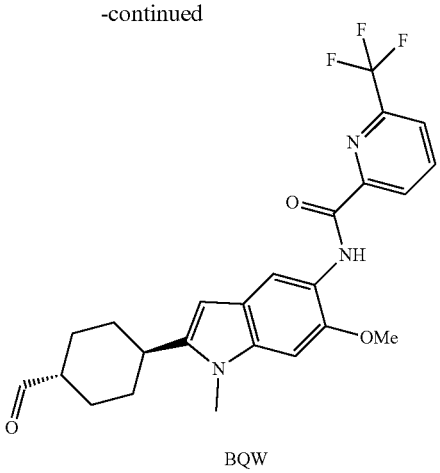

BQW

Step 1—4-Bromo-2-iodo-5-methoxy-aniline

To a solution of 4-bromo-3-methoxy-aniline (3 g, 14.8 mmol, CAS #19056-40-7) in HOAc (40 mL) was added NIS (3.34 g, 14.8 mmol) and the mixture was stirred at 25° C. for 1.5 hrs. On completion, the mixture was poured into H₂O (300 mL) and stirred for 5 min. The mixture was then filtered and the solid was dried in vacuo to give the title compound (4.4 g, 90% yield) as gray solid. ¹H NMR (400 MHz, CDCl₃) δ 7.70 (s, 1H), 6.33 (s, 1H), 4.13 (s, 2H), 3.83 (s, 3H), LC-MS (ESI⁺) m/z 328.1 (M+H)⁺.

Step 2—4-Bromo-2-[2-[4-[[tert-butyl(dimethyl)silyl]oxymethyl]cyclohexyl]ethynyl]-5-methoxy-aniline To a solution of 4-bromo-2-iodo-5-methoxy-aniline (800 mg, 2.44 mmol), tert-butyl-[(4-ethynylcyclohexyl)methoxy]-dimethyl-silane (800 mg, 3.17 mmol, Intermediate BRH) in DMF (8.00 mL) was added CuI (9.29 mg, 48.7 umol), Pd(PPh3)₂Cl₂ (34.2 mg, 48.7 umol) and TEA (987 mg, 9.76 mmol). The mixture was stirred at 25° C. for 3 hrs. On completion, the mixture was diluted with H₂O (50 mL) and extracted with EA (3×30 mL). The organic layers were washed with brine (2×30 mL), dried over anhydrous Na₂SO₄, filtered and concentrated in vacuo. The mixture was purified by reverse phase: (0.1% FA) to give the title compound (668 mg, 60% yield) as white solid. ¹H NMR (400 MHz, CDCl₃) δ 7.38 (s, 1H), 6.24 (s, 1H), 3.84 (s, 3H), 3.42 (d, J=6.0 Hz, 2H), 2.48-2.36 (m, 1H), 2.12-2.05 (m, 2H), 1.86-1.80 (m, 2H), 1.47-1.42 (m, 2H), 1.05-0.91 (m, 3H), 0.90 (s, 9H), 0.04 (s, 6H), LC-MS (ESI⁺) m/z 453.9 (M+H)⁺.

Step 3—[4-(5-Bromo-6-methoxy-1H-indol-2-yl)cyclohexyl]methoxy-tert-butyl-dimethyl-silane To a solution of 4-bromo-2-[2-[4-[[tert-butyl(dimethyl)silyl]oxymethyl]cyclohexyl]ethynyl]-5-methoxy-aniline (668 mg, 1.48 mmol) in ACN (5 mL) was added AgNO₃ (25.0 mg, 147 umol) and the mixture was stirred at 80° C. for 16 hrs. On completion, the mixture was filtered and concentrated in vacuo. The mixture was purified by silica gel column (PE:EA=5:1) to give the title compound (540 mg, 80% yield) as yellow solid. ¹H NMR (400 MHz, CDCl₃) δ 7.85 (s, 1H), 7.67 (s, 1H), 6.87 (s, 1H), 6.10 (s, 1H), 3.90 (s, 3H), 3.47 (d, J=6.0 Hz, 2H), 2.69-2.57 (m, 1H), 2.17-2.06 (m, 2H), 1.98-1.87 (m, 2H), 1.54-1.45 (m, 3H), 1.19-1.05 (m, 2H), 0.91 (s, 9H), 0.06 (s, 6H), LC-MS (ESI⁺) m/z 454.0 (M+H)⁺.

Step 4—[4-(5-Bromo-6-methoxy-1-methyl-indol-2-yl)cyclohexyl]methanol

To a solution of [4-(5-bromo-6-methoxy-1H-indol-2-yl)cyclohexyl]methoxy-tert-butyl-dimethyl-silane (490 mg, 1.08 mmol) in DMF (5.00 mL) was added NaH (51.9 mg, 1.30 mmol, 60% dispersion in mineral oil) at 0° C. The mixture was stirred at 0° C. for 0.5 hr, then CH₃I (307 mg, 2.17 mmol) was added and the mixture was stirred at 25° C. for 16 hrs. On completion, the mixture was diluted with H₂O (40 mL), and extracted with EA (3×20 mL). The organic layers were washed with brine (2×20 mL), dried over anhydrous Na₂SO₄, filtered and concentrated in vacuo. The mixture was purified by reverse phase: (0.1% FA) to give the title compound (300 mg, 78% yield) as yellow solid. ¹H NMR (400 MHz, DMSO-d₆) δ 7.59 (s, 1H), 7.11 (s, 1H), 6.07 (s, 1H), 4.42 (t, J=5.2 Hz, 1H), 3.85 (s, 3H), 3.65 (s, 3H), 3.28-3.23 (m, 2H), 2.72-2.60 (m, 1H), 2.04-1.92 (m, 2H), 1.90-1.76 (m, 2H), 1.48-1.28 (m, 3H), 1.17-1.02 (m, 2H), LC-MS (ESI⁺) m/z 353.9 (M+H)⁺.

Step 5—N-[2-[4-(hydroxymethyl)cyclohexyl]-6-methoxy-1-methyl-indol-5-yl]-6-(trifluoromethyl)pyridine-2-carboxamide To a solution of [4-(5-bromo-6-methoxy-1-methyl-indol-2-yl)cyclohexyl]methanol (280 mg, 794 umol), 6-(trifluoromethyl)pyridine-2-carboxamide (181 mg, 953 umol, Intermediate ATI) in dioxane (5 mL) was added Pd₂(dba)₃ (72.7 mg, 79.4 umol), Xantphos (91.9 mg, 158 umol) and Cs₂CO₃ (776 mg, 2.38 mmol) under N₂. The mixture was then stirred at 80° C. for 40 hr under N₂. On completion, the mixture was filtered and concentrated in vacuo. The mixture was purified by reverse phase: (0.1% FA) to give the title compound (150 mg, 40% yield) as yellow solid. ¹H NMR (400 MHz, DMSO-d₆) δ 10.36 (s, 1H), 8.49 (s, 1H), 8.47-8.42 (m, 1H), 8.42-8.36 (m, 1H), 8.19 (dd, J=1.2, 7.6 Hz, 1H), 7.17 (s, 1H), 6.16 (s, 1H), 4.43 (t, J=5.2 Hz, 1H), 3.98 (s, 3H), 3.69 (s, 3H), 3.30-3.25 (m, 2H), 2.74-2.65 (m, 1H), 2.05-1.96 (m, 2H), 1.92-1.80 (m, 2H), 1.49-1.34 (m, 3H), 1.18-1.05 (m, 2H), LC-MS (ESI⁺) m/z 462.1 (M+H)⁺.

Step 6—N-[2-(4-formylcyclohexyl)-6-methoxy-1-methyl-indol-5-yl]-6-(trifluoromethyl)pyridine-2-carboxamide To a solution of N-[2-[4-(hydroxymethyl)cyclohexyl]-6-methoxy-1-methyl-indol-5-yl]-6-(trifluoromethyl)pyridine-2-carboxamide (50.0 mg, 108 umol) in DCM (3.00 mL) was added DMP (68.9 mg, 162 umol) and the mixture was stirred at 25° C. for 1 hr. On completion, the mixture was diluted with DCM (20 mL), quenched with saturated Na₂S₂O₃ (15 mL), and washed with saturated NaHCO₃(2×20 mL). The organic layer was dried over anhydrous Na₂SO₄, filtered and concentrated in vacuo. The mixture was purified by prep-HPLC (Phenomenex luna C18 150*25 mm*10 um, water (0.225% FA)-ACN, B %: 60%-90%, 11 min) to give the title compound (25 mg, 50% yield) as yellow solid. ¹H NMR (400 MHz, DMSO-d₆) δ 10.36 (s, 1H), 9.64 (s, 1H), 8.50 (s, 1H), 8.47-8.43 (m, 1H), 8.42-8.36 (m, 1H), 8.19 (d, J=7.6 Hz, 1H), 7.18 (s, 1H), 6.18 (s, 1H), 3.98 (s, 3H), 3.70 (s, 3H), 2.77-2.72 (m, 1H), 2.40-2.35 (m, 1H), 2.11-2.01 (m, 4H), 1.54-1.39 (m, 4H), LC-MS (ESL) m/z 460.1 (M+H)⁺.

3-(5-methoxy-3-methyl-4-(4-(methylamino)piperidin-1-yl)-2-oxo-2,3-dihydro-1H-benzo[d]imidazol-1-yl)piperidine-2,6-dione (Intermediate BQX)

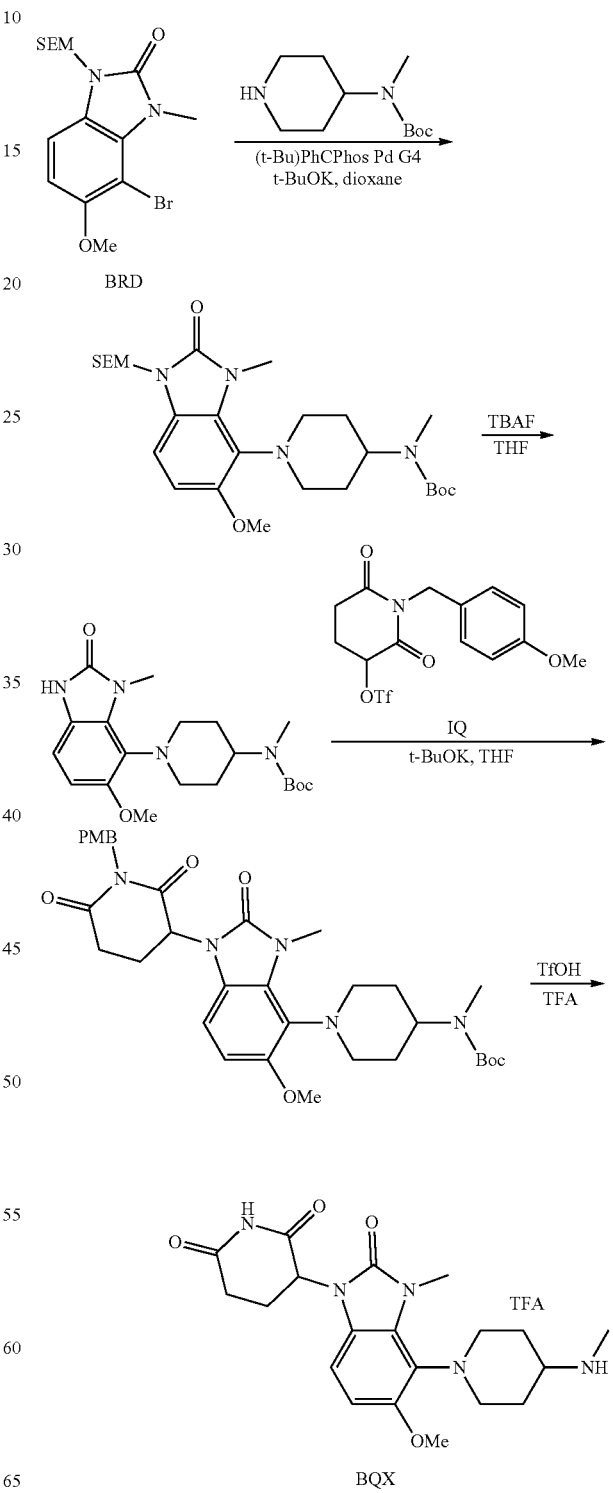

Step 1—Tert-butyl N-[1-[5-methoxy-3-methyl-2-oxo-1-(2-trimethylsilylethoxymethyl)benzimidazol-4-yl]-4-piperidyl]-N-methyl-carbamate A solution of 4-bromo-5-methoxy-3-methyl-1-(2-trimethylsilylethoxymethyl)benzimidazol-2-one (250 mg, 645 umol, Intermediate BRD) tert-butyl N-methyl-N-(4-piperidyl)carbamate (276 mg, 1.29 mmol, CAS 108612-54-0), (t-Bu)PhCPhos Pd G4 (35 mg, 64.5 umol) and t-BuOK (217 mg, 1.94 mmol) in dioxane (8 mL) was stirred at 85° C. under $N_2$ for 16 hrs. On completion, the reaction mixture was diluted with EtOAC (40 mL), and washed with brine (2×20 mL). The organic layer was separated and dried over $Na_2SO_4$ and concentrated in vacuo. The residue was purified by reverse phase (FA condition) to give the title compound (35.0 mg, 10% yield). $^1$H NMR (400 MHz, MeOD) δ 7.04 (d, J=8.8 Hz, 1H), 6.79 (d, J=8.8 Hz, 1H), 5.31 (s, 2H), 3.89 (s, 3H), 3.81 (s, 3H), 3.67-3.53 (m, 4H), 3.39 (s, 1H), 3.06-2.99 (m, 2H), 2.87 (s, 3H), 2.09-1.92 (m, 2H), 1.68 (d, J=12 Hz, 2H), 1.53 (s, 9H), 1.39-1.31 (m, 2H), 0.98-0.89 (m, 2H), 0.00 (s, 9H).

Step 2—Tert-butyl (1-(5-methoxy-3-methyl-2-oxo-2,3-dihydro-1H-benzo[d]imidazol-4-yl)piperidin-4-yl)(methyl)carbamate To a solution of tert-butyl N-[1-[5-methoxy-3-methyl-2-oxo-1-(2-trimethylsilylethoxymethyl) benzimidazol-4-yl]-4-piperidyl]-N-methyl-carbamate (40.0 mg, 76.8 umol) in THF (5 mL) was added TBAF (200 mg, 768 umol) at 25° C. The reaction was warmed to 70° C. and stirred for 16 hrs. On completion, the reaction mixture was diluted with EtOAc (60 mL), and washed with brine (4×30 mL). The organic layer was separated, dried over $Na_2SO_4$ and concentrated in vacuo to give the title compound (29.0 mg, 96% yield) as brown solid. $^1$H NMR (400 MHz, DMSO-$d_6$) δ 6.78 (d, J=8.4 Hz, 1H), 6.67 (d, J=8.4 Hz, 1H), 3.82 (s, 3H), 3.61 (s, 3H), 3.38-3.20 (m, 2H), 3.01-2.90 (m, 2H), 2.79 (s, 3H), 1.97-1.82 (m, 2H), 1.64-1.51 (m, 2H), 1.48 (s, 9H).

Step 3—Tert-butyl (1-(5-methoxy-1-(1-(4-methoxybenzyl)-2,6-dioxopiperidin-3-yl)-3-methyl-2-oxo-2,3-dihydro-1H-benzo[d]imidazol-4-yl)piperidin-4-yl)(methyl)carbamate To a solution of tert-butyl N-[1-(5-methoxy-3-methyl-2-oxo-1H-benzimidazol-4-yl)-4-piperidyl]-N-methyl-carbamate (24.0 mg, 61.4 umol) in THF (3 mL) was added tBuOK (13.8 mg, 122 umol) at 0° C. and the mixture was stirred at 0° C. for 30 min. Then, a solution of [1[(4-methoxyphenyl)methyl]-2,6-dioxo-3-piperidyl] trifluoromethanesulfonate (37.5 mg, 98.3 umol, Intermediate IQ) in THF (0.5 mL) was added into the mixture slowly and the reaction was stirred at 0° C. for 2 hrs. On completion, the reaction mixture was quenched with saturated $NH_4Cl$ solution (1 mL), and diluted with water (10 mL). The mixture was then extracted with EtOAc (2×40 mL). The organic layer was separated, dried over $Na_2SO_4$ and concentrated in vacuo. The residue was purified by prep-TLC (DCM:EtOAc=3:1, Rf=0.5) to give the title compound (36 mg, 94% yield) as yellow solid. LC-MS (ESI$^+$) m/z 622.2 (M+H)$^+$.

Step 4—3-(5-methoxy-3-methyl-4-(4-(methylamino)piperidin-1-yl)-2-oxo-2,3-dihydro-1H-benzo[d]imidazol-1-yl)piperidine-2,6-dione To a solution of tert-butyl N-[1-[5-methoxy-1-[1-[(4-methoxyphenyl)methyl]-2,6-dioxo-3-piperidyl]-3-methyl-2-oxo-benzimidazol-4-yl]-4-piperidyl]-N-methyl-carbamate (30.0 mg, 48.2 umol) in TFA (0.4 mL) was added TfOH (0.08 mL) at 25° C. The reaction mixture was warmed to 70° C. and stirred for 3 hrs. On completion, the reaction mixture was concentrated in vacuo. The residue was purified by prep-HPLC (column: Phenomenex Luna C18 150*25 mm*10 um; mobile phase: [water (0.225% FA)-ACN]; B %: 3%-33%, 11 min) to give the title compound (11.0 mg, 56% yield) as white solid. LC-MS (ESI$^+$) m/z 402.1 (M+H)$^+$.

N-[2-(4-formylcyclohexyl)-6-[(1R,4R)-2-oxa-5-azabicyclo[2.2.1]heptan-5-yl]indazol-5-yl]-6-(trifluoromethyl)pyridine-2-carboxamide (Intermediate BQY)

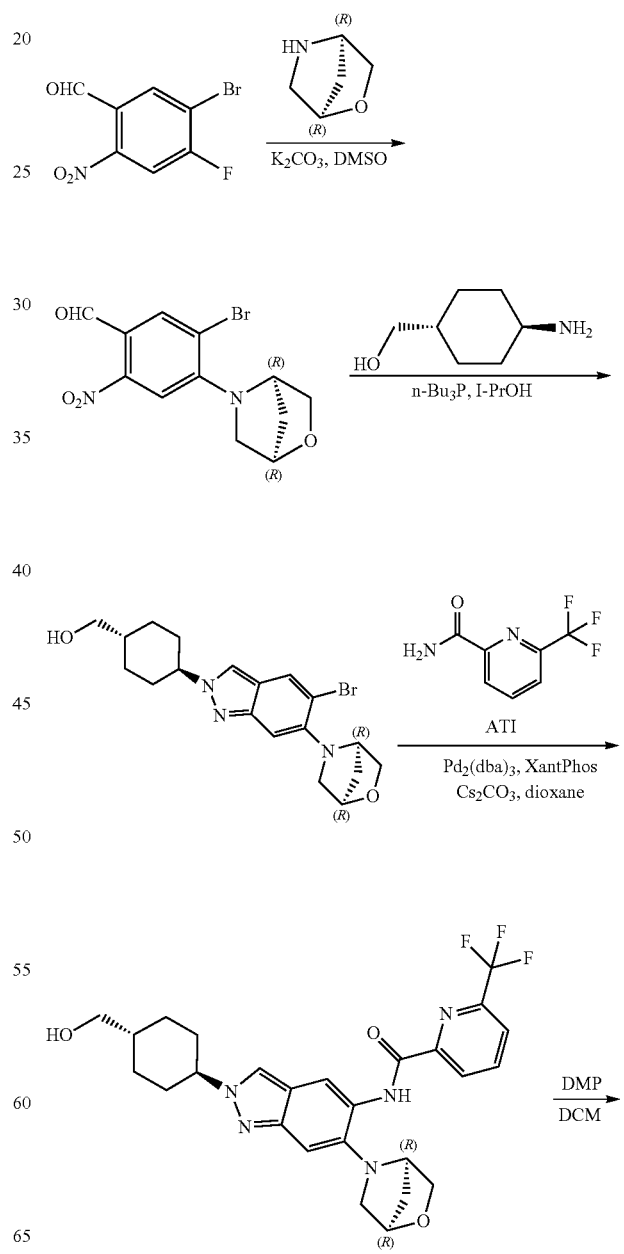

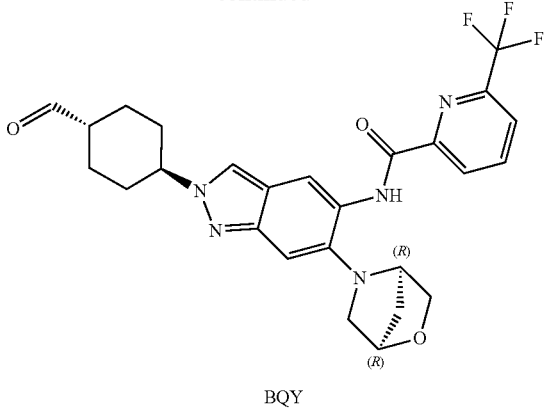

BQY

Step 1—5-Bromo-2-nitro-4-[(1R,4R)-2-oxa-5-azabicyclo[2.2.1]heptan-5-yl]benzaldehyde A solution of (1R,4R)-2-oxa-5-azabicyclo[2.2.1]heptane (1.20 g, 12.1 mmol, CAS #661470-56-0), $K_2CO_3$ (2.09 g, 15.1 mmol) and 5-bromo-4-fluoro-2-nitro-benzaldehyde (1.50 g, 6.05 mmol, CAS #213382-45-7) in DMSO (10 mL) was stirred at 80° C. for 2 hrs. On completion, the reaction was diluted with EtOAc (100 mL) and washed with brine (4×40 mL). The organic layer was separated, dried over $Na_2SO_4$, filtered and the filtrate was concentrated in vacuo to give the title compound (1.9 g, 90% yield) as yellow solid. $^1$H NMR (400 MHz, $CDCl_3$) δ 10.14 (s, 1H), 8.09 (s, 1H), 7.14 (s, 1H), 4.75 (d, J=1.6 Hz, 1H), 4.64 (s, 1H), 4.03-3.99 (m, 2H), 3.91 (dd, J=1.6, 8.0 Hz, 1H), 3.40 (dd, J=0.8, 10.4 Hz, 1H), 2.01-1.98 (m, 2H).

Step 2—[4-[5-Bromo-6-[(1R,4R)-2-oxa-5-azabicyclo[2.2.1]heptan-5-yl]indazol-2-yl]cyclohexyl]methanol To a solution of 5-bromo-2-nitro-4-[(1R,4R)-2-oxa-5-azabicyclo[2.2.1]heptan-5-yl]benzaldehyde (1.70 g, 5.20 mmol) in i-PrOH (30 mL) was added (4-aminocyclohexyl)methanol (805 mg, 6.24 mmol CAS #1467-84-1). The mixture was heated to 80° C. and stirred for 15 hrs. Then, the mixture was cooled to 25° C. and tri-n-butylphosphane (3.15 g, 15.5 mmol) was added. The reaction mixture was heated to 80° C. and stirred for 16 hrs. On completion, the reaction was concentrated in vacuo. The residue was purified by prep-HPLC (column: Phenomenex luna C18 (250*70 mm, 15 um); mobile phase: [water (0.225% FA)-ACN]; B %: 35%-65%, 20 min) to give the title compound (4.00 g, 81% yield) as a yellow solid. $^1$H NMR (400 MHz, $CDCl_3$) δ 7.88 (s, 1H), 7.79 (d, J=0.8 Hz, 1H), 7.15 (s, 1H), 4.61 (s, 1H), 4.36-4.26 (m, 2H), 4.22 (d, J=7.6 Hz, 1H), 3.83 (dd, J=2.0, 7.6 Hz, 1H), 3.63 (dd, J=1.8, 10.8 Hz, 1H), 3.55 (d, J=6.4 Hz, 2H), 3.45 (d, J=10.4 Hz, 1H), 2.33-2.27 (m, 2H), 2.08-1.98 (m, 4H), 1.98-1.89 (m, 3H), 1.75-1.59 (m, 1H), 1.30-1.17 (m, 2H).

Step 3—N-[2-[4-(hydroxymethyl)cyclohexyl]-6-[(1R,4R)-2-oxa-5-azabicyclo[2.2.1]heptan-5-yl]indazol-5-yl]-6-(trifluoromethyl)pyridine-2-carboxamide To a solution of [4-[5-bromo-6-[(1R,4R)-2-oxa-5-azabicyclo[2.2.1]heptan-5-yl]indazol-2-yl] cyclohexyl]methanol (150 mg, 369 umol) in dioxane (4.5 mL) was added $Pd_2$(dba)$_3$ (33.8 mg, 36.9 umol), Xantphos (42.7 mg, 73.8 umol), $Cs_2CO_3$ (240 mg, 738 umol) and 6-(trifluoromethyl)pyridine-2-carboxamide (105 mg, 553 umol, Intermediate ATI). The mixture was stirred at 110° C. for 16 hrs under $N_2$. On completion, the reaction mixture was filtered and concentrated in vacuo. The residue was purified by reverse phase flash (0.1% FA condition) to give the title compound (160 mg, 84% yield) as white solid. $^1$H NMR (400 MHz, DMSO-d6) δ 10.69 (s, 1H), 8.67 (s, 1H), 8.50-8.46 (m, 1H), 8.41 (t, J=7.6 Hz, 1H), 8.34 (s, 1H), 8.21 (dd, J=0.8, 7.6 Hz, 1H), 7.39 (s, 1H), 4.61 (s, 1H), 4.49 (t, J=5.2 Hz, 1H), 4.42-4.33 (m, 1H), 4.07-3.97 (m, 2H), 3.66 (dd, J=1.6, 7.6 Hz, 1H), 3.42 (d, J=9.6 Hz, 1H), 3.28-3.22 (m, 2H), 2.20-2.05 (m, 3H), 1.95-1.81 (m, 5H), 1.51-1.48 (m, 1H), 1.21-1.08 (m, 2H).

Step 4—N-[2-(4-formylcyclohexyl)-6-[(1R,4R)-2-oxa-5-azabicyclo[2.2.1]heptan-5-yl]indazol-5-yl]-6-(trifluoromethyl)pyridine-2-carboxamide To a solution of N-[2-[4-(hydroxymethyl)cyclohexyl]-6-[(1R,4R)-2-oxa-5-azabicyclo[2.2.1]heptan-5-yl]indazol-5-yl]-6-(trifluoromethyl)pyridine-2-carboxamide (50.0 mg, 96.9 umol) in DCM (2 mL) was added DMP (61.7 mg, 145 umol) at 0° C. The mixture was then stirred at 20° C. for 3 hrs. On completion, the mixture was quenched with saturated $Na_2S_2O_3$ (5 mL), and diluted with DCM (40 mL). The organic layer was washed with saturated $NaHCO_3$ (2×20 mL), dried over anhydrous $Na_2SO_4$, filtered and concentrated in vacuo to give the title compound (35.0 mg, 70% yield) as yellow solid. LC-MS (ESI$^+$) m/z 514.1 (M+H)$^+$.

6-(Trifluoromethyl)pyrazine-2-carboxamide (Intermediate BQZ)

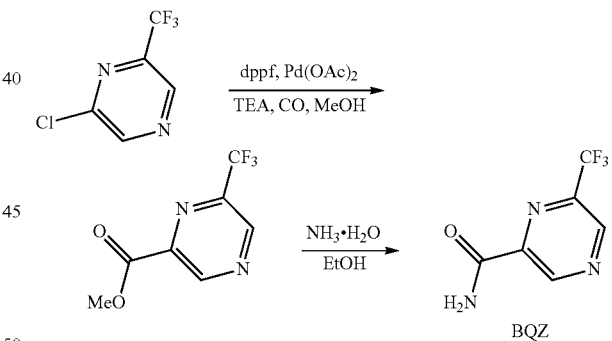

BQZ

Step 1—Methyl 6-(trifluoromethyl)pyrazine-2-carboxylate

To a solution of 2-chloro-6-(trifluoromethyl)pyrazine (1.80 g, 9.86 mmol, CAS #61655-69-4) in MeOH (20 mL) was added DPPF (273 mg, 493 umol), Pd(OAc)$_2$ (221 mg, 986 umol) and TEA (2.00 g, 19.7 mmol). The suspension was degassed under vacuum and purged with CO three times. The mixture was stirred under CO (50 psi) at 70° C. for 16 hours. On completion, the reaction mixture was concentrated in vacuo to give a residue. The residue was diluted with EA (30 mL) and washed with $H_2O$ (15 mL×2). The organic layer was dried over $Na_2SO_4$, filtered and concentrated in vacuo to give a residue. The residue was purified by reverse phase (FA condition) to give the title compound (1.30 g, 63% yield) as light yellow solid. $^1$H NMR (400 MHz, CDCl$_3$) δ 9.49 (s, 1H), 9.13 (s, 1H), 4.06 (s, 3H).

Step 2—6-(Trifluoromethyl)pyrazine-2-carboxamide

To a solution of methyl 6-(trifluoromethyl)pyrazine-2-carboxylate (300 mg, 1.46 mmol) in EtOH (1 mL) was added NH$_3$·H$_2$O (3.36 mL, 21.8 mmol, 25% solution) at 25° C. and the mixture was stirred at 25° C. for 1 hr. On completion, the mixture was concentrated in vacuo to give the title compound (250 mg, 80% yield) as white solid. $^1$H NMR (400 MHz, CDCl$_3$) δ 9.65 (s, 1H), 9.17 (s, 1H), 7.57 (s, 1H), 5.83 (s, 1H).

((1R,4R)-4-(5-amino-6-fluoro-2H-indazol-2-yl)cyclohexylmethanol (Intermediate BRA)

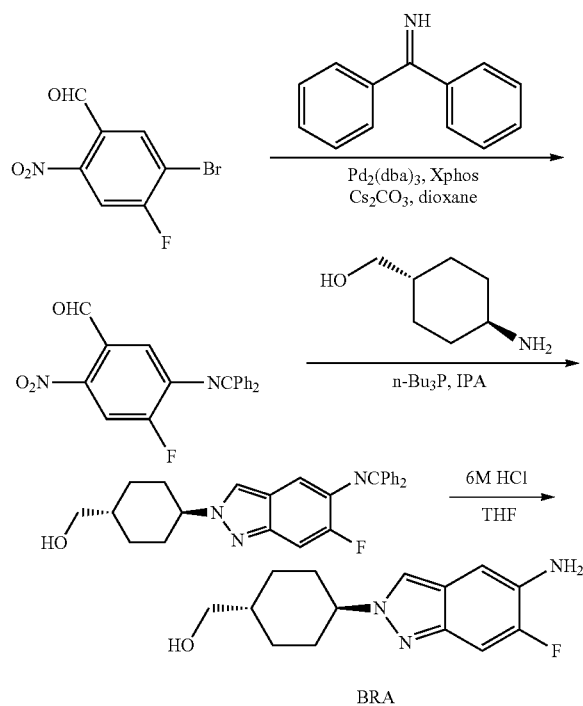

BRA

Step 1—5-(benzhydrylideneamino)-4-fluoro-2-nitrobenzaldehyde

To a solution of 5-bromo-4-fluoro-2-nitro-benzaldehyde (1 g, 4.03 mmol, CAS #213382-45-7) and diphenylmethanimine (1.02 g, 5.65 mmol, CAS #1013-88-3) in dioxane (15 mL) was added Pd$_2$(dba)$_3$ (369 mg, 403 umol), Xantphos (233 mg, 403 umol) and Cs$_2$CO$_3$ (2.63 g, 8.06 mmol). The mixture was stirred at 100° C. under N$_2$ for 16 hrs. On completion, the mixture was poured into water (40 mL) and the aqueous phase was extracted with ethyl acetate (2×40 mL). The combined organic phase was dried with anhydrous Na$_2$SO$_4$, filtered and concentrated in vacuo. The crude product was purified by silica gel chromatography (column height: 250 mm, diameter: 100 mm, 100-200 mesh silica gel, petroleum ether/ethyl acetate=20/1) to give the title compound (900 mg, 64% yield) as yellow solid. LC-MS (ESI+) m/z 348.9 (M+H)$^+$.

Step 2—((1r,4r)-4-(5-((diphenylmethylene)amino)-6-fluoro-2H-indazol-2-yl)cyclohexyl) methanol A solution of 5-(benzhydrylideneamino)-4-fluoro-2-nitro-benzaldehyde (700 mg, 2.01 mmol) and (4-aminocyclohexyl)methanol (285 mg, 2.21 mmol, CAS #1467-84-1) in IPA (15 mL) was stirred at 80° C. for 4 hrs. The mixture was cooled to 25° C., then n-Bu$_3$P (1.22 g, 6.03 mmol) was added into the mixture. The reaction was stirred at 80° C. for 16 hrs under N$_2$. On completion, the reaction mixture was concentrated in vacuo. The residue was purified by silica gel chromatography (column height: 250 mm, diameter: 100 mm, 100-200 mesh silica gel, petroleum ether/ethyl acetate=1/1) to give the title compound (735 mg, 85% yield) as yellow solid. $^1$H NMR (400 MHz, CDCl$_3$) δ 7.84-7.77 (m, 3H), 7.56-7.50 (m, 1H), 7.48-7.42 (m, 2H), 7.31-7.28 (m, 4H), 7.25-7.19 (m, 3H), 4.37-4.27 (m, 1H), 3.57 (d, J=6.4 Hz, 2H), 2.37-2.29 (m, 2H), 1.99-1.89 (m, 2H), 1.72-1.68 (m, 2H), 1.48-1.41 (m, 4H), 1.30-1.26 (m, 2H).

Step 3—((1r,4r)-4-(5-amino-6-fluoro-2H-indazol-2-yl)cyclohexylmethanol

To a solution of [4-[5-(benzhydrylideneamino)-6-fluoro-indazol-2-yl]cyclohexyl]methanol (50.0 mg, 116 umol) in THF (2.5 mL) was added HCl (6 M, 3 mL) and the mixture was stirred at 20° C. for 16 hrs. On completion, the reaction mixture was concentrated in vacuo. The residue was diluted with water (10 mL) and the aqueous phase was extracted with ethyl acetate (20 mL). The aqueous phase was separated and concentrated in vacuo to give the title compound (24 mg, 77% yield). $^1$H NMR (400 MHz, DMSO-d$_6$) δ 8.51 (s, 1H), 7.79 (d, J=8.0 Hz, 1H), 7.58 (d, J=12 Hz, 1H), 4.46-4.40 (m, J=3.9, 7.6, 11.4 Hz, 1H), 3.29 (d, J=6.1 Hz, 2H), 2.40-2.31 (m, 1H), 2.17-2.10 (m, 2H), 1.95-1.82 (m, 4H), 1.53-1.42 (m, 1H), 1.23-1.08 (m, 2H).

N-[6-fluoro-2-(4-formylcyclohexyl)indazol-5-yl]-6-(trifluoromethyl)pyrazine-2-carboxamide (Intermediate BRB)

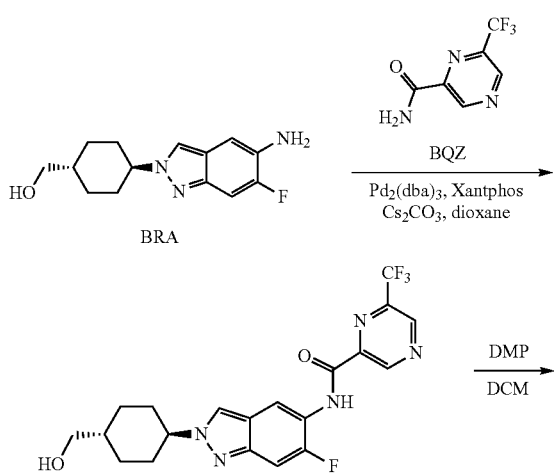

791

-continued

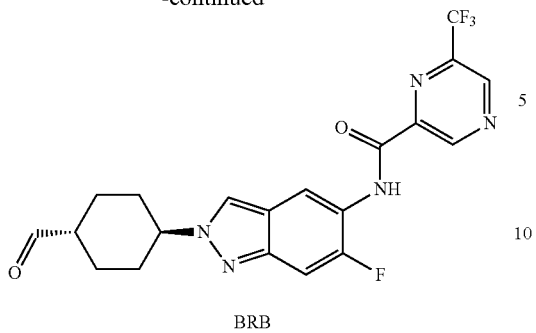

BRB

Step 1—N-[6-fluoro-2-[4-(hydroxymethyl)cyclohexyl]indazol-5-yl]-6-(trifluoromethyl)pyrazine-2-carboxamide A mixture of 6-(trifluoromethyl)pyrazine-2-carboxamide (180 mg, 942 umol, Intermediate BQZ), [4-(5-bromo-6-fluoro-indazol-2-yl)cyclohexyl]methanol (308 mg, 942 umol, Intermediate BRA), $Pd_2(dba)_3$ (86.2 mg, 94.2 umol), Xantphos (109 mg, 188 umol) and $Cs_2CO_3$ (614 mg, 1.88 mmol) in dioxane (10 mL) was degassed and purged with $N_2$ for three times, and then the mixture was stirred at 100° C. for 16 hrs under $N_2$ atmosphere. On completion, the reaction mixture was filtered and filtrate was concentrated in vacuo to give a residue. The residue was purified by column chromatography ($SiO_2$, petroleum ether/ethyl acetate=2/1) to give the title compound (210 mg, 51% yield) as yellow solid. $^1$H NMR (400 MHz, $CDCl_3$) δ 9.89 (d, J=3.2 Hz, 1H), 9.74 (s, 1H), 9.20 (s, 1H), 8.81 (d, J=7.6 Hz, 1H), 8.03 (s, 1H), 7.45 (d, J=11.6 Hz, 1H), 4.43-4.33 (m, 1H), 3.60-3.56 (m, 2H), 2.39-2.33 (m, 2H), 2.10-2.03 (m, 3H), 1.33-1.23 (m, 4H); LC-MS (ESI$^+$) m/z 438.1 (M+H)$^+$.

Step 2—N-[6-fluoro-2-(4-formylcyclohexyl)indazol-5-yl]-6-(trifluoromethyl)pyrazine-2-carboxamide To a solution of N-[6-fluoro-2-[4-(hydroxymethyl)cyclohexyl]indazol-5-yl]-6-(trifluoromethyl) pyrazine -2-carboxamide (140 mg, 320 umol) in DCM (3 mL) was added DMP (176 mg, 416 umol) at 0° C. Then the mixture was stirred at 25° C. for 1 hr. On completion, the reaction mixture was quenched with saturated $NaHCO_3$ (1 mL) and $Na_2S_2O_3$ (1 mL), then extracted with DCM (5 mL). The combined organic layer was washed with NaCl (1 mL×3), dried over $Na_2SO_4$, filtered and concentrated in vacuo to give the title compound (134 mg, 99% yield) as yellow solid. $^1$H NMR (400 MHz, $CDCl_3$) δ 9.90 (d, J=3.2 Hz, 1H), 9.74-9.73 (m, 1H), 8.82 (d, J=7.6 Hz, 1H), 8.00-7.95 (m, 1H), 7.45 (d, J=12.0 Hz, 1H), 7.31-7.28 (m, 1H), 4.43-4.31 (m, 1H), 2.45-2.40 (m, 3H), 2.30-2.26 (m, 2H), 2.12-2.00 (m, 2H), 1.60-1.50 (m, 2H), 1.30-1.23 (m, 1H); LC-MS (ESI$^+$) m/z 436.0 (M+H)$^+$.

N-[6-fluoro-2-(4-formylcyclohexyl)indazol-5-yl]pyrazine-2-carboxamide (Intermediate BRC)

792

-continued

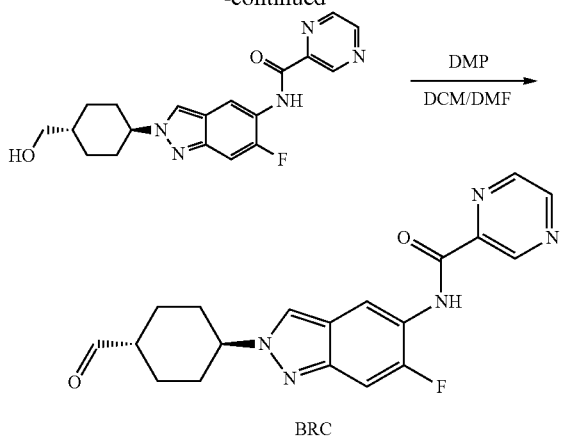

BRC

Step 1—N-[6-fluoro-2-[4-(hydroxymethyl)cyclohexyl]indazol-5-yl]pyrazine -2-carboxamide To a solution of [4-(5-amino-6-fluoro-indazol-2-yl)cyclohexyl]methanol (34.0 mg, 129 umol, Intermediate BRA) in DMF (2 mL) was added pyrazine-2-carboxylic acid (24.0 mg, 193 umol, CAS #98-97-5), DIEA (83.4 mg, 645 umol) and HATU (73.6 mg, 193 umol) at 0° C. Then the reaction was stirred at 0-25° C. for 1 h. On completion, the reaction mixture was diluted with EtOAc (100 mL), then washed with brine (4×40 mL). The organic layer was separated, dried over $Na_2SO_4$ and concentrated in vacuo. The residue was purified by reversed-phase HPLC (0.1% FA condition) to give the title compound (160 mg, 28% yield) as yellow solid. $^1$H NMR (400 MHz, DMSO-$d_6$) δ 10.31 (d, J=1.6 Hz, 1H), 9.32 (d, J=1.6 Hz, 1H), 8.97 (d, J=2.4 Hz, 1H), 8.84 (dd, J=1.6, 2.4 Hz, 1H), 8.49 (s, 1H), 8.32 (d, J=8.0 Hz, 1H), 7.53 (d, J=12.0 Hz, 1H), 4.54-4.36 (m, 2H), 2.19-2.10 (m, 2H), 1.96-1.82 (m, 5H), 1.51-1.48 (m, 1H), 1.22-1.11 (m, 2H).

Step 2—N-[6-fluoro-2-(4-formylcyclohexyl)indazol-5-yl]pyrazine-2-carboxamide

To a solution of N-[6-fluoro-2-[4-(hydroxymethyl)cyclohexyl]indazol-5-yl]pyrazine-2-carboxamide (20.0 mg, 54.1 umol) in DCM (1.50 mL) and DMF (0.2 mL) was added DMP (45.9 mg, 108 umol) at 0° C. Then the mixture was stirred at 0-25° C. for 3 hrs. On completion, the reaction mixture was diluted with DCM (30 mL), then quenched with $Na_2S_2O_3$ (aq.) (2 ml). The organic layer was washed with $NaHCO_3$ solution (2×20 mL), dried over $Na_2SO_4$ and concentrated in vacuo to give the title compound (17 mg, 85%) as a yellow solid. LC-MS (ESI+) m/z 368.0 (M+H)$^+$.

4-Bromo-5-methoxy-3-methyl-1H-benzimidazol-2-one (Intermediate BRD)

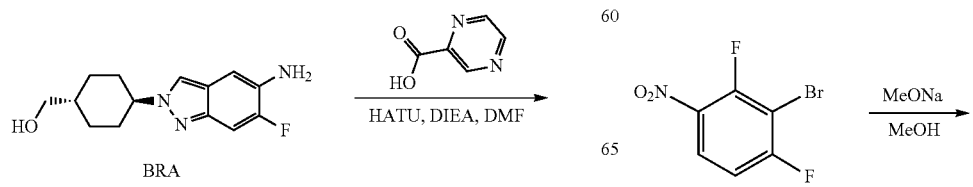

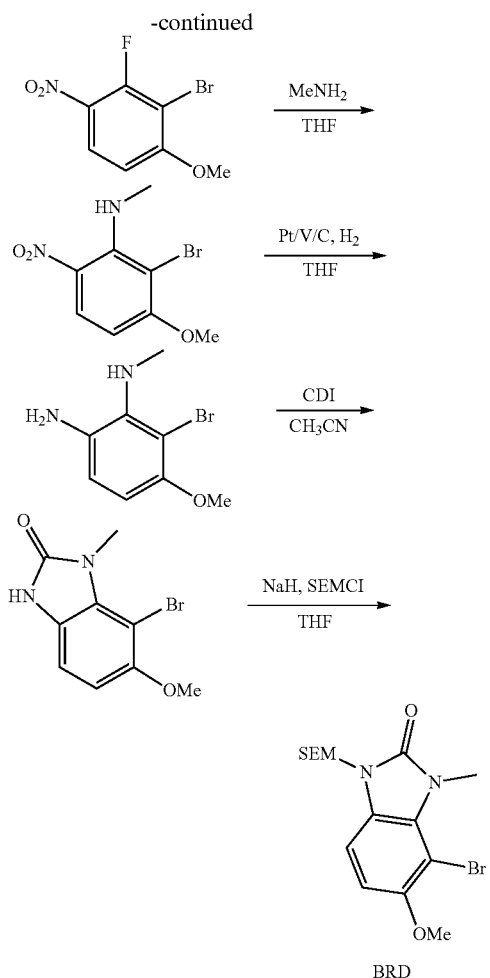

BRD

Step 1—2-Bromo-3-fluoro-1-methoxy-4-nitro-benzene

To a mixture of 2-bromo-1,3-difluoro-4-nitro-benzene (5.00 g, 21.01 mmol, from CAS #103977-78-2) in MeOH (50 mL) was added NaOMe (1.14 g, 21.0 mmol) at 0° C. The mixture was warmed to 20° C. and stirred for 2 hours. On completion, the mixture was poured into the water (60 mL) and the aqueous phase was extracted with ethyl acetate (2×40 mL). The combined organic phase was washed with brine (2×40 mL), dried with anhydrous $Na_2SO_4$, filtered and concentrated in vacuo to give the crude product. The crude product was triturated with PE:EA=20:1 (10 mL) to give the title compound (1.80 g, 34% yield) as white solid. $^1$H NMR (400 MHz, $CDCl_3$) δ 8.14 (dd, J=8.4, 9.2 Hz, 1H), 6.81 (dd, J=1.6, 9.2 Hz, 1H), 4.04 (s, 3H).

Step 2—2-Bromo-3-methoxy-N-methyl-6-nitro-aniline

To a mixture of 2-bromo-3-fluoro-1-methoxy-4-nitro-benzene (1.60 g, 6.40 mmol) in THF (20 mL) was added $MeNH_2$ (2 M, 4.80 mL) and the mixture was stirred at 20° C. for 2 hours. On completion, the mixture was concentrated in vacuo to give the residue. The residue was purified by column chromatography ($SiO_2$, petroleum ether/ethyl acetate=50:1 to 10:1) to give the title compound (1.40 g, 83% yield) as brown solid. $^1$H NMR (400 MHz, $CDCl_3$) δ 8.06 (d, J=9.6 Hz, 1H), 6.73 (s, 1H), 6.44 (d, J=9.2 Hz, 1H), 3.97 (s, 3H), 3.09 (d, J=5.2 Hz, 3H).

Step 3—3-Bromo-4-methoxy-N2-methyl-benzene-1,2-diamine

To a mixture of 2-bromo-3-methoxy-N-methyl-6-nitro-aniline (1.40 g, 5.36 mmol) in THF (10 mL) and MeOH (10 mL) was added platinum (104 mg, 53.6 umol, 10 wt %) under $H_2$ (15 psi) and stirred at 20° C. for 2 hours. On completion, the mixture was filtered and concentrated to give the title compound (1.20 g, 96% yield) as a yellow solid.

Step 4—4-Bromo-5-methoxy-3-methyl-1H-benzimidazol-2-one

To a mixture 3-bromo-4-methoxy-N2-methyl-benzene-1,2-diamine (1.1 g, 4.76 mmol) in $CH_3CN$ (20 mL) was added CDI (1.16 g, 7.14 mmol) and the mixture was stirred at 90° C. for 3 hours. On completion, the mixture was concentrated to remove the $CH_3CN$, then $H_2O$ (10 mL) was added into the mixture. The mixture was filtered to give the filter cake which was dried to give the title compound (1.00 g, 81% yield) as brown solid. $^1$H NMR (400 MHz, $CDCl_3$) δ 6.89 (d, J=8.4 Hz, 1H), 6.59 (d, J=8.8 Hz, 1H), 3.81 (s, 3H), 3.71 (s, 3H), 2.72 (d, J=2.4 Hz, 1H).

Step 5—4-Bromo-5-methoxy-3-methyl-1-((2-(trimethylsilyl)ethoxy)methyl)-1H-benzo[d]imidazol-2(3H)-one To a solution of 7-bromo-6-methoxy-1-methyl-1H-benzo[d]imidazol-2(3H)-one (1.00 g, 3.90 mmol) in THF (30 mL) was added NaH (234 mg, 5.85 mmol, 60% dispersion in mineral oil) at 0° C. and the mixture was stirred at 0° C. for 0.5 hr. Then SEM-Cl (0.98 g, 5.85 mmol) was added to above solution and the mixture was stirred at 65° C. for 10 hrs. On completion, the mixture was quenched with $H_2O$ (30 mL), and extracted with EA (2×30 mL). The organic layers were washed with brine (2×30 mL), dried over anhydrous $Na_2SO_4$, filtered and concentrated in vacuo. The mixture was purified by silica gel column (PE:EA=20:1) to give the title compound (1.30 g, 86% yield) as yellow oil. LC-MS ($ESI^+$) m/z 387.0 $(M+H)^+$.

3-(5-methoxy-3-methyl-2-oxo-4-(piperidin-4-yl)-2,3-dihydro-1H-benzo[d]imidazol-1-yl) piperidine-2,6-dione (Intermediate BRE)

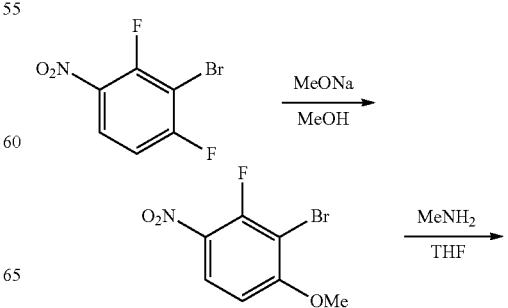

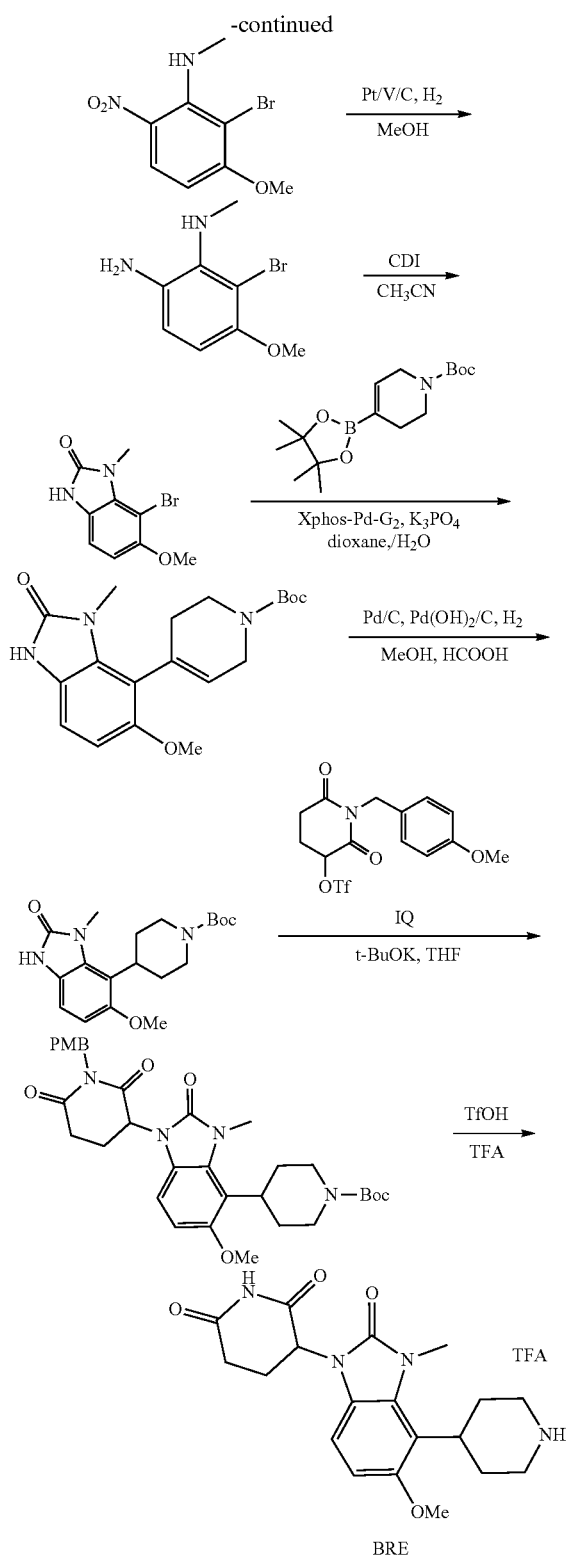

Step 1—2-bromo-3-fluoro-1-methoxy-4-nitrobenzene

To a solution of 2-bromo-1,3-difluoro-4-nitro-benzene (1 g, 4.20 mmol, from CAS #103977-78-2) in MeOH (10 mL) was added MeONa (226 mg, 4.20 mmol) at 0° C. The mixture was warmed to 20° C. and stirred for 2 hrs. On completion, the mixture was poured into the water (10 mL) and the aqueous phase was extracted with ethyl acetate (2×50 mL). The combined organic phase was separated, dried with anhydrous $Na_2SO_4$, filtered and the filtrate was concentrated in vacuo to give the crude product. The crude product was triturated with PE:EA=20:1 (20 mL) to give the title compound (130 mg, 12% yield) as white solid. $^1$H NMR (400 MHz, $CDCl_3$) δ 8.13 (t, J=8.8 Hz, 1H), 6.80 (dd, J=1.6, 9.2 Hz, 1H), 4.03 (s, 3H).

Step 2—2-bromo-3-methoxy-N-methyl-6-nitroaniline

To a solution of 2-bromo-3-fluoro-1-methoxy-4-nitro-benzene (3 g, 12.00 mmol) in THF (10 mL) was added 30% $MeNH_2$ (1.86 g, 18.00 mmol) in EtOH and the reaction was stirred at 25° C. for 2 hrs. On completion, the reaction was concentrated in vacuo. The residue was purified by column chromatography ($SiO_2$, petroleum ether/ethyl acetate=50/1 to 10/1) to give the title compound (3 g, 95% yield) as yellow solid. $^1$H NMR (400 MHz, $CDCl_3$) δ 8.08 (d, J=9.2 Hz, 1H), 6.45 (d, J=9.6 Hz, 1H), 3.99 (s, 3H), 3.13-3.09 (m, 3H).

Step 3—6-bromo-5-methoxy-N1-methylbenzene-1, 2-diamine

To a solution of 2-bromo-3-methoxy-N-methyl-6-nitro-aniline (100 mg, 383 umol) in MeOH (5 mL) was added Pt/V/C (30.0 mg, 10 wt %). The reaction mixture was stirred at 25° C. under $H_2$ (15 psi) for 2 hrs. On completion, the reaction mixture was filtered and the filtrate was concentrated in vacuo to give the title compound (80 mg, 90% yield) as brown oil. $^1$H NMR (400 MHz, $CDCl_3$) δ 6.58 (d, J=8.6 Hz, 1H), 6.46 (d, J=8.6 Hz, 1H), 3.74 (s, 3H), 2.65 (s, 3H).

Step 4—7-bromo-6-methoxy-1-methyl-1H-benzo[d] imidazol-2 (3H)-one

To a solution of 3-bromo-4-methoxy-N2-methyl-benzene-1,2-diamine (1.7 g, 7.36 mmol) in $CH_3CN$ (30 mL) was added CDI (1.79 g, 11.03 mmol) and the mixture was stirred at 90° C. for 3 hrs. On completion, the mixture was concentrated in vacuo to remove MeCN, then $H_2O$ (20 mL) was added. The mixture was filtered to give the filter cake. The filter cake was triturated with PE:EA=3:1 (40 mL) to give the title compound (1.7 g, 90% yield) as yellow solid. $^1$H NMR (400 MHz, DMSO-$d_6$) δ 10.94 (s, 1H), 6.91 (d, J=8.4 Hz, 1H), 6.75 (d, J=8.4 Hz, 1H), 3.79 (s, 3H), 3.57 (s, 3H).

Step 5—Tert-butyl 4-(5-methoxy-3-methyl-2-oxo-2, 3-dihydro-1H-benzo[d]imidazol-4-yl)-5,6-dihydro-pyridine-1(2H)-carboxylate A solution of 4-bromo-5-methoxy-3-methyl-1H-benzimi-dazol-2-one (300 mg, 1.17 mmol), tert-butyl 4-(4,4,5,5-tetramethyl-1,3,2-dioxaborolan-2-yl)-3,6-dihydro-2H-pyridine-1-carboxylate (541 mg, 1.75 mmol, CAS #286961-14-6), Xphos-PD-G2 (91.8 mg, 116 umol) and $K_3PO_4$ (495 mg, 2.33 mmol) in dioxane (10 mL) and $H_2O$ (1 mL) was stirred at 80° C. for 16 hrs under $N_2$. On completion, the reaction mixture was extracted with EtOAc (2×40 mL). The combined organic layers were washed with water (2×30 mL), dried over $Na_2SO_4$ and concentrated in vacuo. The residue was purified by reversed-phase HPLC (0.1% FA condition) to give the title compound (130 mg, 31% yield) as yellow solid. $^1$H NMR (400 MHz, MeOD) δ 6.94 (d, J=8.4 Hz, 1H), 6.73 (d, J=8.4 Hz, 1H), 5.64 (s, 1H), 4.22-4.12 (m, 1H), 4.09-3.97 (m, 1H), 3.80-3.73 (m, 4H), 3.65-3.53 (m, 1H), 3.36 (s, 3H), 3.34-3.31 (m, 2H), 2.60 (d, J=16.8 Hz, 1H), 2.29-2.19 (m, 1H), 1.52 (s, 10H).

Step 6—Tert-butyl 4-(5-methoxy-3-methyl-2-oxo-2,3-dihydro-1H-benzo[d]imidazol-4-yl)piperidine-1-carboxylate To a solution of tert-butyl 4-(5-methoxy-3-methyl-2-oxo-1H-benzimidazol-4-yl)-3,6-dihydro-2H-pyridine-1-carboxylate (100 mg, 278 umol) in HCOOH (0.05 mL) and MeOH (50 mL) was added Pd/C (50 mg, 10 wt %) and Pd(OH)$_2$/C (50 mg, 10 wt %). The reaction mixture was stirred at 60° C. for 48 hrs under H$_2$ (50 psi). On completion, the reaction mixture was filtered and the filtrate was concentrated in vacuo to give the title compound (80 mg, 79% yield) as white solid. $^1$H NMR (400 MHz, CDCl$_3$) δ 6.89 (d, J=8.4 Hz, 1H), 6.74 (d, J=8.4 Hz, 1H), 4.19 (d, J=13.2 Hz, 2H), 3.80 (s, 3H), 3.65 (s, 3H), 3.62-3.51 (m, 2H), 2.90 (s, 1H), 2.48-2.41 (m, 2H), 1.97-1.84 (m, 2H), 1.52 (s, 9H).

Step 7—Tert-butyl 4-(5-methoxy-1-(1-(4-methoxybenzyl)-2,6-dioxopiperidin-3-yl)-3-methyl-2-oxo-2,3-dihydro-1H-benzo[d]imidazol-4-yl)piperidine-1-carboxylate To a solution of tert-butyl 4-(5-methoxy-3-methyl-2-oxo-1H-benzimidazol-4-yl)piperidine-1-carboxylate (70.0 mg, 193 umol) and t-BuOK (43.4 mg, 387 umol) in THF (5 mL) was added a solution of [1[(4-methoxyphenyl)methyl]-2,6-dioxo-3-piperidyl]trifluoromethanesulfonate (147 mg, 387 umol, Intermediate IQ) in THF (0.5 mL) at 0° C. The reaction mixture was stirred at 0° C. for 2 h. On completion, the reaction was quenched with saturated NH$_4$Cl solution (0.5 mL), then diluted with EtOAc (50 mL). The organic layer was washed with brine (2×20 mL), dried over Na$_2$SO$_4$ and concentrated in vacuo. The residue was purified by prep-TLC (PE:EA=3:2, Rf=0.3) to give the title compound (70.0 mg, 60% yield). $^1$H NMR (400 MHz, CDCl$_3$) δ 7.30 (d, J=8.8 Hz, 2H), 6.75 (d, J=7.6 Hz, 2H), 6.40 (d, J=8.8 Hz, 1H), 6.19 (d, J=8.8 Hz, 1H), 5.15-5.05 (m, 1H), 4.89 (s, 2H), 4.20-4.14 (m, 1H), 3.72 (s, 3H), 3.69 (s, 3H), 3.59 (s, 3H), 3.39-3.30 (m, 1H), 2.97-2.89 (m, 1H), 2.86-2.66 (m, 4H), 2.62-2.47 (m, 2H), 2.41-2.22 (m, 3H), 2.11-2.03 (m, 1H), 1.43 (s, 9H).

Step 8—3-(5-methoxy-3-methyl-2-oxo-4-(piperidin-4-yl)-2,3-dihydro-1H-benzo[d]imidazol-1-yl) piperidine-2,6-dione A solution of tert-butyl 4-[5-methoxy-1-[1-[(4-methoxyphenyl) methyl]-2,6-dioxo-3-piperidyl]-3-methyl-2-oxo-benzimidazol-4-yl]piperidine-1-carboxylate (60 mg, 101 umol) in TFA (1 mL) and TfOH (0.2 mL) was stirred at 70° C. for 1 h. On completion, the reaction mixture was concentrated in vacuo. The residue was purified by prep-HPLC (column: Phenomenex Luna C18 150*25 mm*10 um; mobile phase: [water (0.1% TFA) ACN]; B %: 2%-32%, 10 min) to give the title compound (25 mg, 66% yield) as yellow solid. LC-MS (ESI$^+$) m/z 373.0 (M+H)$^+$.

3-(4-(Azetidin-3-yl)-3-methyl-2-oxo-2,3-dihydro-1H-benzo[d]imidazol-1-yl)piperidine-2,6-dione (Intermediate BRF)

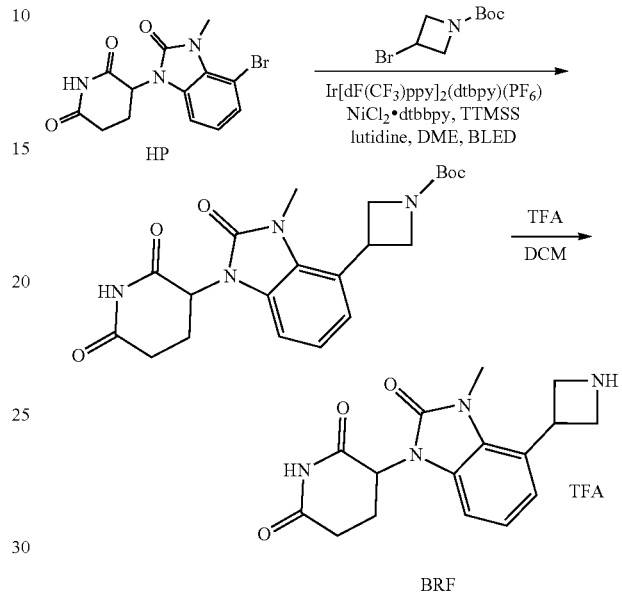

BRF

Step 1—Tert-butyl 3-(1-(2,6-dioxopiperidin-3-yl)-3-methyl-2-oxo-2,3-dihydro-1H-benzo[d]imidazol-4-yl)azetidine-1-carboxylate To a 40 mL vial equipped with a stir bar was added 3-(4-bromo-3-methyl-2-oxo-benzimidazol-1-yl)piperidine-2,6-dione (1.0 g, 2.96 mmol, Intermediate HP), tert-butyl 3-iodoazetidine-1-carboxylate (1.09 g, 3.84 mmol, CAS #254454-54-1), Ir[dF(CF3)ppy]2(dtbpy)(PF6) (33.1 mg, 29.5 umol), TTMSS (735 mg, 2.96 mmol), 2,6-dimethylpyridine (633 mg, 5.91 mmol) and NiCl$_2$.dtbbpy (5.88 mg, 14.7 umol) in DME (24 mL). The reaction was stirred and irradiated with a 34 W blue LED lamp at 25° C. for 14 hr. On completion, the mixture was filtered and the filtrate was concentrated in vacuo. The crude product was purified by reverse phase flash (0.1% FA condition) to give the title compound (900 mg, 71% yield) as white solid. 1H NMR (400 MHz, DMSO-d6) δ 11.10 (s, 1H), 7.24 (d, J=4.4 Hz, 1H), 7.14-7.00 (m, 2H), 5.42-5.34 (m, 1H), 4.56-4.46 (m, 1H), 4.29 (t, J=8.4 Hz, 2H), 3.97 (t, J=6.0 Hz, 2H), 3.51 (s, 3H), 2.96-2.81 (m, 1H), 2.78-2.59 (m, 2H), 2.06-1.95 (m, 1H), 1.42 (s, 9H).

Step 2—3-(4-(Azetidin-3-yl)-3-methyl-2-oxo-2,3-dihydro-1H-benzo[d]imidazol-1-yl)piperidine-2,6-dione To a solution of tert-butyl 3-[1-(2,6-dioxo-3-piperidyl)-3-methyl-2-oxo-benzimidazol-4-yl]azetidine-1-carboxylate (150 mg, 361 umol) in DCM (3.0 mL) was added TFA (1.54 g, 13.5 mmol). The mixture was stirred at 25° C. for 30 min. On completion, the reaction mixture was concentrated in vacuo to give the title compound (120 mg, 80% yield, TFA) as brown solid. LC-MS (ESI+) m/z 315.2 (M+H)$^+$.

3-(4-Bromo-3,5-dimethyl-2-oxo-2,3-dihydro-1H-benzo[d]imidazol-1-yl)piperidine-2,6-dione (Intermediate BRG)

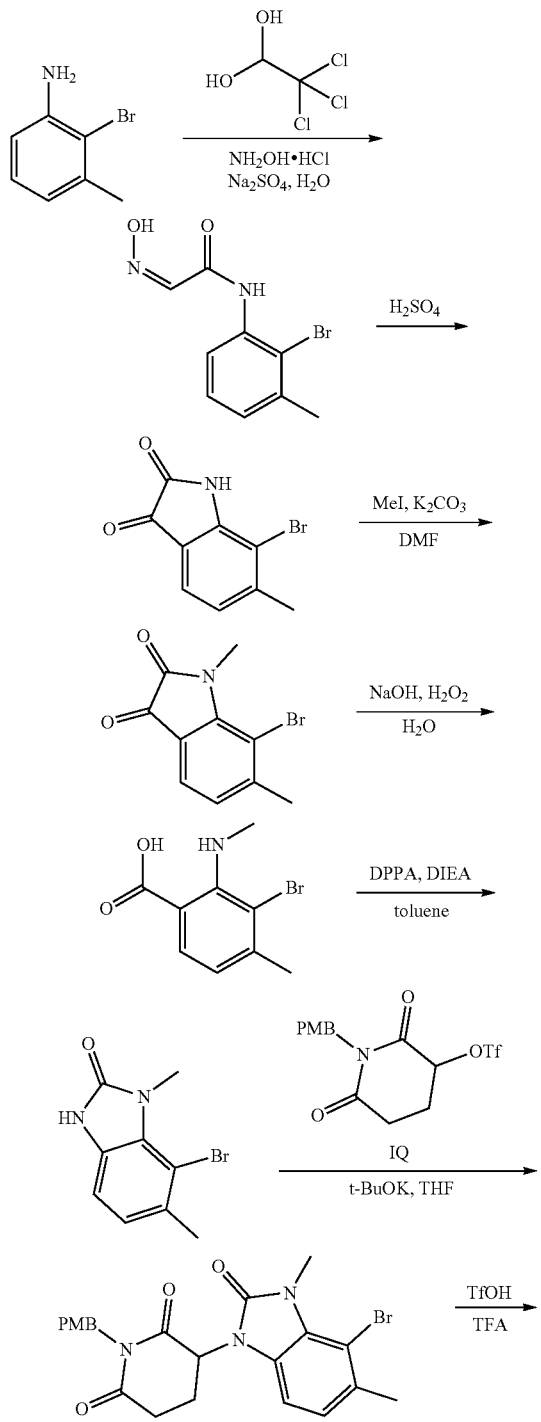

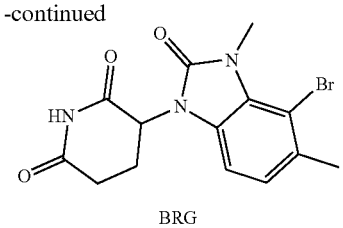

BRG

Step 1—(Z)—N-(2-bromo-3-methylphenyl)-2-(hydroxyimino)acetamide

To a mixture of 2-bromo-3-methyl-aniline (12.0 g, 64.5 mmol, CAS #54879-20-8) and 2,2,2-trichloroethane-1,1-diol (16.0 g, 96.7 mmol, CAS #302-17-0) in H$_2$O (250 mL) was added Na$_2$SO$_4$ (100 g, 709 mmol) and NH$_2$OH. HCl (6.27 g, 90.3 mmol) at 25° C. under N$_2$. The mixture was stirred at 25° C. for 16 hours. Then, HCl (12 M, 18.8 mL) was added, and the mixture was stirred at 100° C. for 16 hours. On completion, the reaction mixture was cooled to 0° C. and filtered. The filter cake was dried in vacuo to give the title compound (14.0 g, 84% yield) as a yellow solid. LC-MS (ESI$^+$) m/z 256.9 (M+H)$^+$.

Step 2—7-Bromo-6-methylindoline-2,3-dione

A mixture of (1E)-2-(2-amino-3-bromo-4-methyl-phenyl)-2-oxo-acetaldehyde oxime (14.0 g, 54.4 mmol) in H2SO4 (200 mL) was stirred at 80° C. for 3 hours. On completion, the reaction mixture was poured into ice water (1000 mL), and filtered. The filtered cake was collected and dried in vacuo to give the title compound (12 g, 92% yield) as a yellow solid. LC-MS (ESI$^+$) m/z 239.9 (M+H)$^+$.

Step 3—7-Bromo-1,4-dimethyl-indoline-2,3-dione

To a solution of 7-bromo-6-methyl-indoline-2,3-dione (2.00 g, 8.33 mmol) in the DMF (30 mL) was added K$_2$CO$_3$ (3.45 g, 25.0 mmol) and MeI (3.55 g, 25.0 mmol, 1.56 mL) and the mixture was stirred at 60° C. for 1 hr. On completion, the reaction was quenched with water (20 mL) and extracted with EA (100 mL). The organic layer was dried over Na$_2$SO$_4$, filtered and concentrated in vacuo. The residue was purified by column chromatography (petroleum ether/ethyl acetate=20/1 to 5/1) to give the title compound (800 mg, 38% yield) as a red solid. $^1$H NMR (400 MHz, CDCl$_3$) δ 7.47 (d, J=7.6 Hz, 1H), 7.03 (d, J=7.6 Hz, 1H), 3.69 (s, 3H), 2.50 (s, 3H).

Step 4—3-Bromo-4-methyl-2-(methylamino)benzoic Acid

To a solution of 7-bromo-1,6-dimethyl-indoline-2,3-dione (800 mg, 3.15 mmol) in the 2 M aqueous NaOH (1.26 g, 31.4 mmol) in H$_2$O (15 mL) was added H$_2$O$_2$ (1.43 g, 12.6 mmol, 1.21 mL, 30% solution) at 0° C. in dropwise. The mixture was stirred at 20° C. for 2 hrs. On completion, the reaction mixture was acidified with HCl (6 M) to pH=5-6 and the mixture was extracted with EA (100 mL). The organic layer was dried over Na$_2$SO$_4$, filtered and concentrated in vacuo to give the title compound (630 mg, 82% yield) as a yellow solid. ¹H NMR (400 MHz, DMSO-d₆) δ 7.64 (d, J=8.0 Hz, 1H), 6.84 (d, J=8.0 Hz, 1H), 2.87 (s, 3H), 2.36 (s, 3H).

Step 5—7-Bromo-1,6-dimethyl-1H-benzo[d]imidazol-2 (3H)-one

To a solution of 3-bromo-4-methyl-2-(methylamino)benzoic acid (400 mg, 1.64 mmol) in the t-BuOH (3 mL) was added DIEA (635 mg, 4.92 mmol) and DPPA (676 mg, 2.46 mmol). The mixture was stirred at 95° C. for 12 hrs under N₂. On completion, the mixture was concentrated in vacuo. The residue was diluted with toluene (3 mL), filtered and the filtered cake was collected and dried in vacuo to give the title compound (360 mg, 91% yield) as a gray solid. ¹H NMR (400 MHz, DMSO-d₆) δ 11.06 (s, 1H), 6.97 (d, J=8.0 Hz, 1H), 6.88 (d, J=8.0 Hz, 1H), 3.59 (s, 3H), 2.34 (s, 3H).

Step 6—3-(4-Bromo-3,5-dimethyl-2-oxo-2,3-dihydro-1H-benzo[d]imidazol-1-yl)-1-(4-methoxybenzyl) piperidine-2,6-dione To a solution of 4-bromo-3,5-dimethyl-1H-benzimidazol-2-one (360 mg, 1.49 mmol) in the THF (4 mL) was added tBuOK (251 mg, 2.24 mmol) at −10° C. Then [1-[(4-methoxyphenyl)methyl]-2,6-dioxo-3-piperidyl] trifluoromethanesulfonate (854 mg, 2.24 mmol, Intermediate IQ) in the THF (4 mL) was added at −10° C. and the mixture was stirred for 1 hr. On completion, the reaction mixture was acidified with FA to pH=5-6. Then the mixture was diluted with EA (30 mL) and washed with water (2×30 mL). The organic layer was dried over Na₂SO₄, filtered and concentrated in vacuo. The residue was purified by column chromatography (petroleum ether/ethyl acetate=10/1 to 2/1) to give the title compound (650 mg, 92% yield) as a white solid. LC-MS (ESI⁺) m/z 472.1 (M+H)⁺.

Step 7—3-(4-Bromo-3,5-dimethyl-2-oxo-2,3-dihydro-1H-benzo[d]imidazol-1-yl)piperidine-2,6-dione A solution of 3-(4-bromo-3,5-dimethyl-2-oxo-benzimidazol-1-yl)-1-[(4-methoxyphenyl)methyl] piperidine-2,6-dione (100 mg, 211 umol) in the TFA (1 mL) and TfOH (0.2 mL) was stirred at 70° C. for 3 hrs. On completion, the reaction mixture was concentrated by blowing with a steam N₂. The residue was purified by reversed-phase (0.1% FA condition) to give the title compound (55 mg, 74% yield) as a white solid. ¹H NMR (400 MHz, DMSO-d₆) δ 11.12 (s, 1H), 7.11-7.03 (m, 2H), 5.39 (dd, J=5.6, 12.6 Hz, 1H), 3.67 (s, 3H), 2.94-2.83 (m, 1H), 2.76-2.68 (m, 1H), 2.66-2.59 (m, 1H), 2.38 (s, 3H), 2.07-1.97 (m, 1H), LC-MS (ESI⁺) m/z 352.2 (M+H)⁺.

Tert-butyl-[(4-ethynylcyclohexyl)methoxy]-dimethyl-silane (Intermediate BRH)

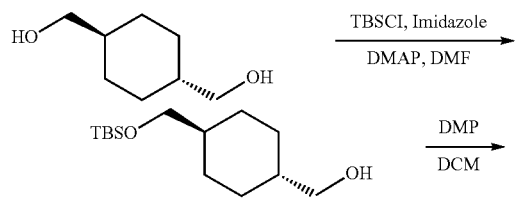

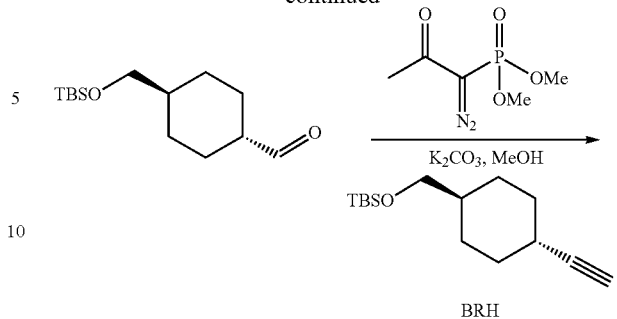

Step 1—[4-[[Tert-butyl(dimethyl)silyl]oxymethyl]cyclohexyl]methanol

To a mixture of [4-(hydroxymethyl)cyclohexyl]methanol (6.00 g, 41.6 mmol, CAS #3236-48-4), imidazole (5.67 g, 83.2 mmol) and DMAP (508 mg, 4.16 mmol) in DMF (70 mL) was added TBSCl (6.27 g, 41.6 mmol, 5.10 mL) slowly at 0° C. The reaction mixture was stirred at 25° C. for 12 hours. On completion, the reaction mixture was quenched with water (50 mL) and extracted with EA (3×60 mL). The combined organic layer was dried over Na₂SO₄, filtered and concentrated in vacuo to give a residue. The residue was purified by column chromatography to give the title compound (4.50 g, 41% yield) as colorless oil. ¹H NMR (400 MHz, CDCl₃) δ 3.46 (d, J=6.4 Hz, 2H), 3.41 (d, J=6.4 Hz, 2H), 1.88-1.75 (m, 4H), 1.51-1.40 (m, 2H), 1.37 (s, 1H), 1.02-0.91 (m, 4H), 0.90 (s, 9H), 0.07-0.01 (m, 6H).

Step 2—4-[[Tert-butyl(dimethyl)silyl]oxymethyl]cyclohexanecarbaldehyde

To a mixture of [4-[[tert-butyl(dimethyl)silyl]oxymethyl]cyclohexyl]methanol (4.50 g, 17.4 mmol) in DCM (50 mL) was added DMP (8.86 g, 20.8 mmol, 6.47 mL) at 0° C. dropwise. The reaction mixture was then stirred at 25° C. for 3 hr. On completion, the reaction mixture was quenched with saturated Na₂S₂O₃ (20 mL) and saturated NaHCO₃ (20 mL) at 25° C., and then stirred for 30 minutes. The mixture was then extracted with DCM (3×50 mL). Then the organic layers were separated and concentrated in vacuo to give the crude product. The residue was purified by column chromatography to give the title compound (3.00 g, 67% yield) as a light yellow oil. ¹H NMR (400 MHz, CDCl₃) δ 9.62 (d, J=1.6 Hz, 1H), 3.43 (d, J=6.0 Hz, 2H), 2.23-2.12 (m, 1H), 2.06-1.96 (m, 2H), 1.93-1.85 (m, 2H), 1.51-1.37 (m, 1H), 1.35-1.22 (m, 2H), 1.06-0.94 (m, 2H), 0.92-0.89 (m, 9H), 0.06-0.03 (m, 6H).

Step 3—Tert-butyl[(4-ethynylcyclohexyl)methoxy]-dimethyl-silane

To a mixture of 4-[[tert-butyl(dimethyl)silyl]oxymethyl]cyclohexanecarbaldehyde (3.00 g, 11.7 mmol) and K₂CO₃ (3.23 g, 23.4 mmol) in MeOH (30 mL) was added 1-diazo-1-dimethoxyphosphoryl-propan-2-one (3.37 g, 17.5 mmol, CAS #90965-06-3) at 0° C. dropwise. The reaction mixture was then stirred at 25° C. for 12 hours. On completion, the reaction mixture was diluted with water (50 mL) and extracted with EA (3×30 mL). The combined organic layer was dried over Na₂SO₄, filtered and concentrated in vacuo to give a residue. The residue was purified by column chromatography to give the title compound (2.60 g, 88% yield) as colorless oil. ¹H NMR (400 MHz, CDCl₃) δ 3.39 (d, J=6.4 Hz, 2H), 2.25-2.13 (m, 1H), 2.04 (d, J=2.4 Hz, 1H), 2.04-1.98 (m, 2H), 1.84-1.75 (m, 2H), 1.51-1.44 (m, 1H), 1.43-1.32 (m, 2H), 0.93 (d, J=3.2 Hz, 2H), 0.89 (s, 9H), 0.04 (s, 6H).

3-[5-Chloro-3-methyl-4-[4-(methylamino)-1-piperidyl]-2-oxo-benzimidazol-1-yl]piperidine -2,6-dione (Intermediate BOK)

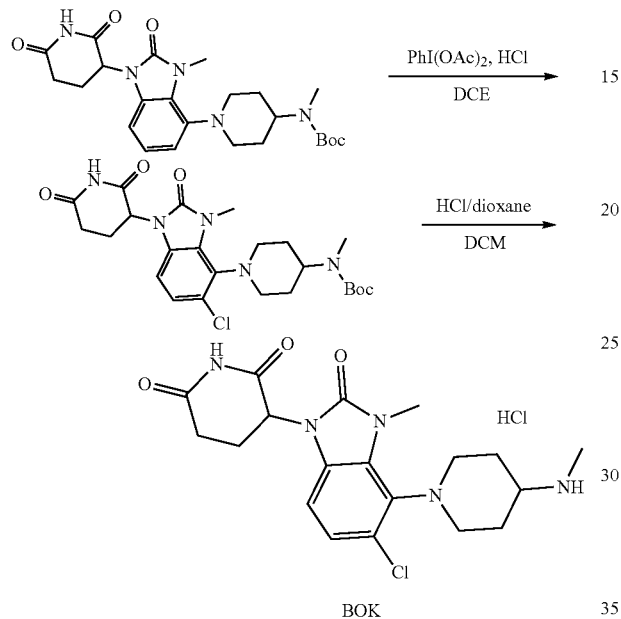

Step 1—Tert-butyl N-[1-[5-chloro-1-(2,6-dioxo-3-piperidyl)-3-methyl-2-oxo -benzimidazol-4-yl]-4-piperidyl]-N-methylcarbamate To a solution of tert-butyl N-[1-[1-(2,6-dioxo-3-piperidyl)-3-methyl-2-oxo-benzimidazol-4-yl]-4-piperidyl]-N-methyl-carbamate (50.0 mg, 106 umol, synthesized via Step 1 of Intermediate AQK) in DCE (5.00 mL) was added PhI(OAc)₂ (34.2 mg, 106 umol) and HCl (1 M, 530.17 uL). Then the mixture was stirred at 50° C. for 16 hrs. On completion, the reaction mixture was washed with saturated solution of NaHCO₃ (1×10 mL), and then washed with saturated solution of Na₂S₂O₃ (1×10 mL). The organic layer was washed with brine (2×10 mL), then dried over anhydrous Na₂SO₄, filtered and concentrated in vacuo to give a residue. The residue was purified by prep-TLC (SiO₂, EA:PE=2:1, Rf=0.35) to give the title compound (10.0 mg, 18% yield) as a white solid. ¹H NMR (400 MHz, CDCl₃) δ 8.46 (s, 1H), 6.97 (d, J=8.4 Hz, 1H), 6.57 (d, J=8.4 Hz, 1H), 5.20 (dd, J=5.6, 12.6 Hz, 1H), 3.77 (s, 3H), 3.76-3.72 (m, 1H), 3.05-2.97 (m, 2H), 2.96-2.89 (m, 1H), 2.87-2.77 (m, 4H), 2.75-2.63 (m, 1H), 2.24-2.17 (m, 1H), 1.93-1.81 (m, 2H), 1.74-1.67 (m, 4H), 1.49 (s, 9H); LC-MS (ESI⁺) m/z 506.1 (M+H)⁺.

Step 2—3-[5-Chloro-3-methyl-4-[4-(methylamino)-1-piperidyl]-2-oxo-benzimidazol-1-yl]piperidine-2, 6-dione To a solution of tert-butyl N-[1-[5-chloro-1-(2,6-dioxo-3-piperidyl)-3-methyl-2-oxo-benzimidazol-4-yl]-4-piperidyl]-N-methylcarbamate (10.0 mg, 19.7 umol) in DCM (0.50 mL) was added HCl/dioxane (4 M, 0.20 mL) and the mixture was stirred at 25° C. for 1 hr. On completion, the reaction mixture was concentrated in vacuo to give the title compound (8.00 mg, 91% yield, HCl) as a white solid. LC-MS (ESI⁺) m/z 406.1 (M+H)⁺.

3-(6-Chloro-3-methyl-4-(4-(methylamino)piperidin-1-yl)-2-oxo-2,3-dihydro-1H-benzo[d]imidazol-1-yl)piperidine-2,6-dione (Intermediate BQQ)

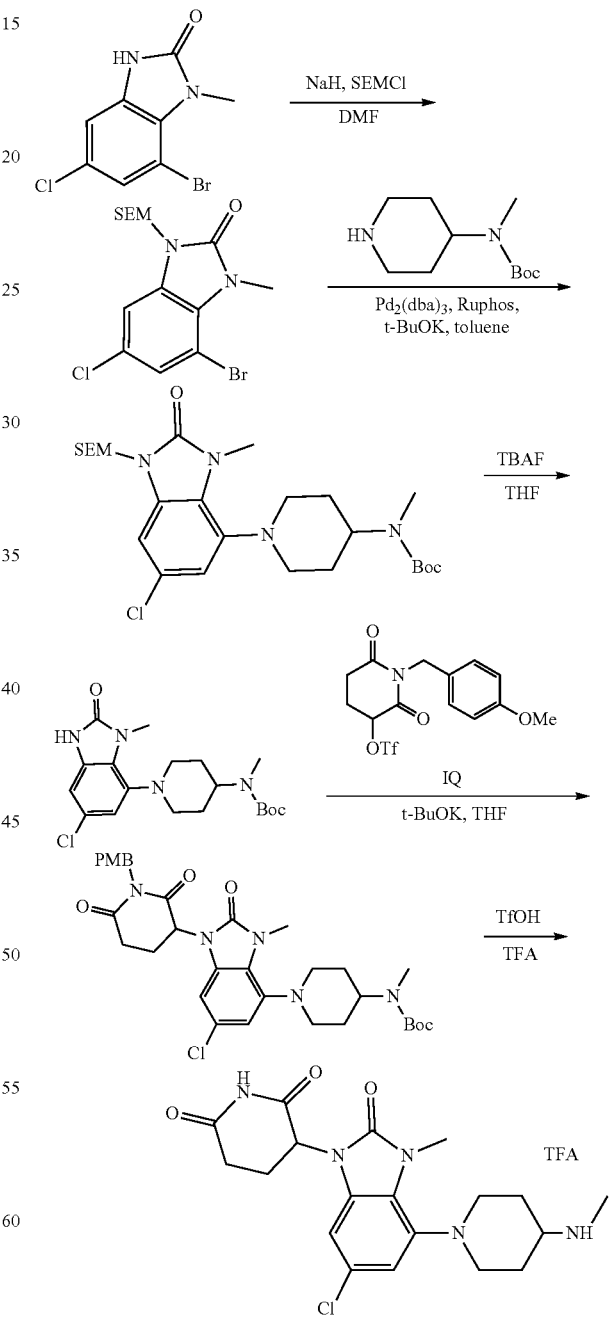

Step 1—4-Bromo-6-chloro-3-methyl-1-((2-(trimethyl silyl)ethoxy)methyl)-1H-benzo[d]imidazol-2(3H)-one To a solution of 4-bromo-6-chloro-3-methyl-1H-benzimidazol-2-one (3 g, 11.5 mmol, synthesized via Steps 1-4 of Intermediate BQN) in the DMF (40 mL) was added NaH (688 mg, 17.2 mmol, 60% dispersion in mineral oil) at 0° C. and the mixture was stirred for 30 mins. Then SEM-Cl (2.87 g, 17.2 mmol) was added at 0° C. and the mixture was stirred at 20° C. for 12 hrs. On completion, the reaction mixture was quenched by water (100 mL) and extracted with EA (200 mL). The organic layer was dried over $Na_2SO_4$, filtered and concentrated in vacuo. The residue was purified by column chromatography (PE:EA=50:1 to 20:1) to give the title compound (3.6 g, 80% yield) as white solid. $^1$H NMR (400 MHz, $CDCl_3$) δ 7.25 (d, J=2.0 Hz, 1H), 7.12 (d, J=2.0 Hz, 1H), 5.28 (s, 2H), 3.74 (s, 3H), 3.62-3.56 (m, 2H), 0.97-0.89 (m, 2H), 0.00 (s, 9H).

Step 2—Tert-butyl (1-(6-chloro-3-methyl-2-oxo-1-((2-(trimethylsilyl)ethoxy)methyl)-2,3-dihydro-1H-benzo[d]imidazol-4-yl)piperidin-4-yl)(methyl)carbamate A mixture of 4-bromo-6-chloro-3-methyl-1-(2-trimethylsilylethoxymethyl)benzimidazol-2-one (1 g, 2.55 mmol), tert-butyl N-methyl-N-(4-piperidyl)carbamate (656 mg, 3.06 mmol, CAS #108612-54-0), $Pd_2(dba)_3$ (234 mg, 255.26 umol), RuPhos (238 mg, 510 umol) and tBuONa (613 mg, 6.38 mmol) in the toluene (20 mL) was stirred at 60° C. for 1 hr under $N_2$. On completion, the reaction mixture was diluted with EA (200 mL) and washed with water (2×100 mL). The organic layer was dried over $Na_2SO_4$, filtered and concentrated in vacuo. Then the residue was purified by column chromatography (petroleum ether/ethyl acetate=20/1 to 3/1) to give the title compound (1.2 g, 90% yield) as yellow oil. $^1$H NMR (400 MHz, $CDCl_3$) δ 6.96 (d, J=2.0 Hz, 1H), 6.88 (d, J=1.6 Hz, 1H), 5.26 (s, 2H), 3.72 (s, 3H), 3.63-3.58 (m, 2H), 3.20 (d, J=11.8 Hz, 2H), 2.88-2.75 (m, 5H), 1.96-1.83 (m, 2H), 1.81-1.74 (m, 2H), 1.49 (s, 9H), 0.96-0.91 (m, 2H), 0.00 (s, 9H).

Step 3—Tert-butyl (1-(6-chloro-3-methyl-2-oxo-2,3-dihydro-1H-benzo[d]imidazol-4-yl)piperidin-4-yl)(methyl)carbamate To a solution of tert-butyl N-[1-[6-chloro-3-methyl-2-oxo-1-(2-trimethylsilylethoxymethyl) benzimidazol-4-yl]-4-piperidyl]-N-methyl-carbamate (1.2 g, 2.29 mmol) in the THF (6 mL) was added TBAF (5.97 g, 22.8 mmol). The mixture was then stirred at 80° C. for 12 hrs. On completion, the reaction mixture was filtered and concentrated in vacuo. The residue was purified by column chromatography (petroleum ether/ethyl acetate=10/1 to 1/1) to give the title compound (800 mg, 89% yield) as white solid. $^1$H NMR (400 MHz, $CDCl_3$) δ 10.23 (s, 1H), 6.89 (d, J=1.6 Hz, 1H), 6.82 (s, 1H), 3.72 (s, 3H), 3.19 (d, J=11.6 Hz, 2H), 2.85-2.76 (m, 5H), 1.95-1.85 (m, 2H), 1.80-1.74 (m, 2H), 0.89-0.84 (m, 1H).

Step 4—Tert-butyl (1-(6-chloro-1-(1-(4-methoxybenzyl)-2,6-dioxopiperidin-3-yl)-3-methyl-2-oxo-2,3-dihydro-1H-benzo[d]imidazol-4-yl)piperidin-4-yl)(methyl)carbamate To a solution of tert-butyl N-[1-(6-chloro-3-methyl-2-oxo-1H-benzimidazol-4-yl)-4-piperidyl]-N-methyl-carbamate (400 mg, 1.01 mmol) in the THF (5 mL) was added tBuOK (170.49 mg, 1.52 mmol) at −10° C. and the mixture was stirred for 30 mins. Then a solution of [1-[(4-methoxyphenyl)methyl]-2,6-dioxo-3-piperidyl]trifluoromethanesulfonate (463 mg, 1.22 mmol, Intermediate IQ) in the THF (3 mL) was added dropwise in the mixture at −10° C. The mixture was stirred for 1 hr at −10° C. On completion, the reaction mixture was acidified with FA to pH=5-6. Then the mixture was diluted with EA (100 mL), washed with $NH_4Cl$ (100 mL) and brine (100 mL). The organic layer was dried over $Na_2SO_4$, filtered and concentrated in vacuo. The residue was purified by column chromatography (petroleum ether/ethyl acetate=10/1 to 1/1) to give the title compound (600 mg, 95% yield) as yellow solid. $^1$H NMR (400 MHz, $CDCl_3$) δ 7.36 (d, J=8.8 Hz, 2H), 6.85 (d, J=8.8 Hz, 3H), 6.31 (s, 1H), 5.18 (dd, J=5.6, 13.2 Hz, 1H), 5.04-4.90 (m, 2H), 3.79 (s, 3H), 3.74 (s, 3H), 3.25-3.15 (m, 2H), 3.06-2.97 (m, 1H), 2.88-2.77 (m, 6H), 2.58 (dq, J=4.2, 13.4 Hz, 1H), 2.20-2.10 (m, 1H), 1.97-1.83 (m, 2H), 1.82-1.74 (m, 2H), 1.49 (s, 9H).

Step 5—3-(6-Chloro-3-methyl-4-(4-(methylamino)piperidin-1-yl)-2-oxo-2,3-dihydro-1H-benzo[d]imidazol-1-yl)piperidine-2,6-dione A mixture of tert-butyl N-[1-[6-chloro-1-[1-[(4-methoxyphenyl)methyl]-2,6-dioxo-3-piperidyl]-3-methyl-2-oxo-benzimidazol-4-yl]-4-piperidyl]-N-methyl-carbamate (200 mg, 319 umol) in the TFA (2 mL) and TfOH (0.4 mL) was stirred at 70° C. for 12 hrs. On completion, the reaction mixture was concentrated by $N_2$ and based with TEA to pH~7. The residue was purified by reversed phase (0.1%, FA) to give the title compound (100 mg, 76% yield) as yellow solid. LC-MS (ESI$^+$) m/z 406.2 (M+H)$^+$.

[4-[5-Bromo-6-[(1S,4S)-2-oxa-5-azabicyclo[2.2.1]heptan-5-yl]indazol-2-yl]cyclohexyl]methanol (Intermediate BAR)

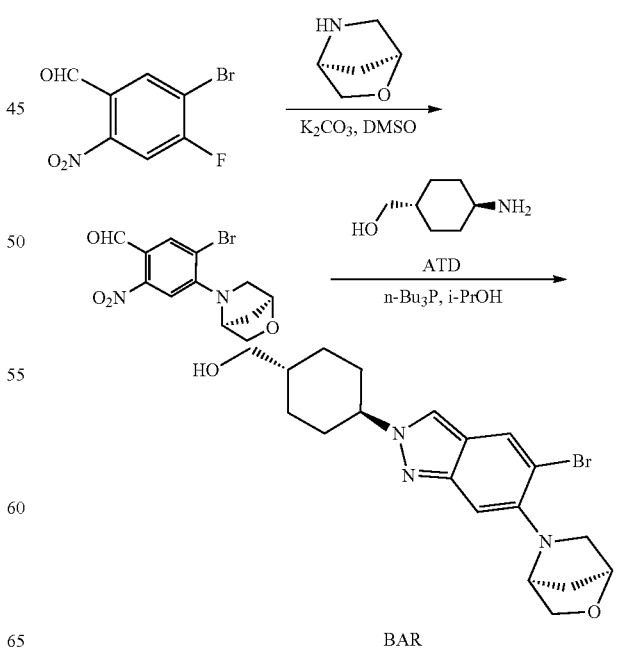

BAR

Step 1—[4-[5-Bromo-6-[(1S,4S)-2-oxa-5-azabicyclo[2.2.1]heptan-5-yl]indazol-2-yl]cyclohexyl]methanol To a solution of (1S,4S)-2-oxa-5-azabicyclo[2.2.1]heptane (4.00 g, 40.3 mmol, CAS #279-33-4), $K_2CO_3$ (5.57 g, 40.3 mmol) in DMSO (60 mL) was added with 5-bromo-4-fluoro-2-nitro-benzaldehyde (5.00 g, 20.2 mmol, synthesized via Step 1 of Intermediate ATE). The reaction mixture was stirred at 80° C. for 1 hours. On completion, the reaction mixture was diluted with EtOAc (50 mL) and extracted with EtOAc (3×50 mL). The combined organic layers were washed with saturated NaCl solution (3×50 mL), dried over $Na_2SO_4$, filtered and concentrated in vacuo to give the title compound (6.60 g, 91% yield) as a yellow solid. $^1$H NMR (400 MHz, CDCl$_3$) δ 10.23 (s, 1H), 8.18 (s, 1H), 7.22 (s, 1H), 4.87-4.70 (m, 2H), 4.11-4.09 (m, 1H), 4.00 (dd, J=1.6, 8.0 Hz, 1H), 3.49 (d, J=10.0 Hz, 1H), 2.08 (s, 2H), 1.65 (s, 1H).

Step 2—[4-[5-Bromo-6-[(1S,4S)-2-oxa-5-azabicyclo[2.2.1]heptan-5-yl]indazol-2-yl]cyclohexyl]methanol To a solution of 5-bromo-2-nitro-4-[(1S,4S)-2-oxa-5-azabicyclo[2.2.1]heptan-5-yl]benzaldehyde (2.00 g, 6.11 mmol) in IPA (50 mL) was added (4-aminocyclohexyl)methanol (948 mg, 7.34 mmol, Intermediate ATD). The mixture was heated at 80° C. for 4 hr under $N_2$. Then the mixture was cooled to 25° C. and tributylphosphane (3.71 g, 18.3 mmol) was added. The reaction mixture was heated to 80° C. for 16 hr. On completion, the reaction mixture was concentrated in vacuo to give a residue. The residue was purified by reverse phase flash (0.1% FA condition) to give the title compound (4.00 g, 81% yield) as a yellow solid. $^1$H NMR (400 MHz, DMSO-d$_6$) δ 8.24 (s, 1H), 7.95 (s, 1H), 7.14 (s, 1H), 4.57 (s, 1H), 4.41-4.29 (m, 2H), 3.97 (d, J=7.6 Hz, 1H), 3.74 (dd, J=1.6, 7.6 Hz, 1H), 3.53 (dd, J=1.6, 9.6 Hz, 2H), 3.30-3.23 (m, 4H), 2.18-2.05 (m, 2H), 1.96-1.76 (m, 6H), 1.20-1.09 (m, 2H).

N-[2-(4-formylcyclohexyl)-6-[(1S,4S)-2-oxa-5-azabicyclo[2.2.1]heptan-5-yl]indazol-5-yl]-6-(trifluoromethyl)pyridine-2-carboxamide (Intermediate BAS)

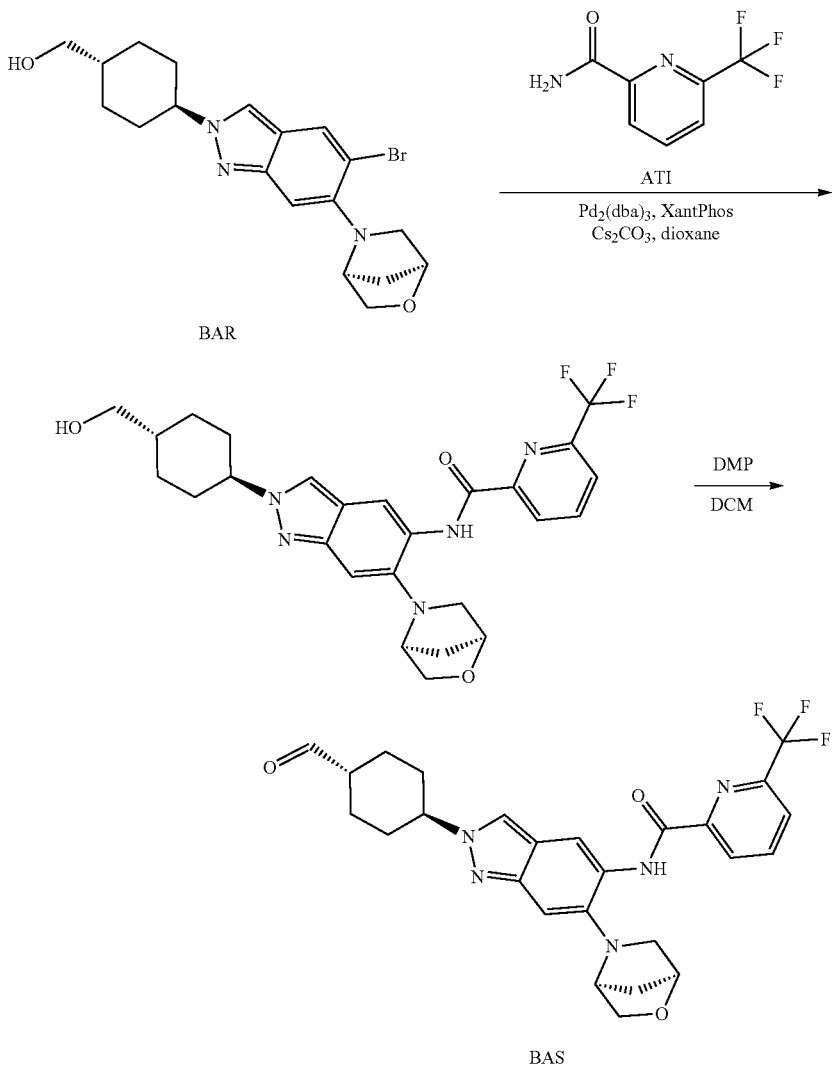

Step 1—N-[2-[4-(hydroxymethyl)cyclohexyl]-6-[(1S,4S)-2-oxa-5-azabicyclo[2.2.1]heptan-5-yl]indazol-5-yl]-6-(trifluoromethyl)pyridine-2-carboxamide To a solution of [4-[5-bromo-6-[(1S,4S)-2-oxa-5-azabicyclo[2.2.1]heptan-5-yl]indazol-2-yl]cyclohexyl]methanol (2.00 g, 4.92 mmol, Intermediate BAR) in dioxane (50 mL) was added Pd$_2$(dba)$_3$ (283 mg, 492 umol), Xantphos (570 mg, 984 umol), Cs$_2$CO$_3$ (3.21 g, 9.84 mmol) and 6-(trifluoromethyl)pyridine-2-carboxamide (1.40 g, 7.38 mmol, Intermediate ATI). The mixture was stirred at 110° C. for 16 hrs. On completion, the reaction mixture was filtered and the filtrate was concentrated in vacuo to give a residue. The residue was purified by reverse phase flash (0.1% FA condition) to give a residue. The residue was dissolved in solvent EtOAc, and the resulting suspension was stirred 30 min at 25° C., then the suspension was filtered and the filter cake was dried in vacuo to give the title compound (1.40 g, 55% yield). $^1$H NMR (400 MHz, DMSO-d$_6$) δ 10.69 (s, 1H), 8.68 (s, 1H), 8.54-8.38 (m, 2H), 8.34 (s, 1H), 8.22 (d, J=7.6 Hz, 1H), 7.40 (s, 1H), 4.62 (s, 1H), 4.54-4.27 (m, 2H), 4.12-3.94 (m, 2H), 3.67 (dd, J=1.6, 7.6 Hz, 1H), 3.43 (d, J=10.0 Hz, 1H), 3.32-3.23 (m, 4H), 2.17-2.07 (m, 3H), 1.92-1.80 (m, 4H), 1.47 (m, 1H), 1.26-1.06 (m, 2H).

Step 2—N-[2-(4-formylcyclohexyl)-6-[(1S,4S)-2-oxa-5-azabicyclo[2.2.1]heptan-5-yl]indazol-5-yl]-6-(trifluoromethyl)pyridine-2-carboxamide To a mixture of N-[2-[4-(hydroxymethyl)cyclohexyl]-6-[(1S,4S)-2-oxa-5-azabicyclo[2.2.1]heptan-5-yl]indazol-5-yl]-6-(trifluoromethyl)pyridine-2-carboxamide (201 mg, 390 umol) in DCM (5.0 mL) was added DMP (198 mg, 467 umol) at 0° C. under N$_2$. The mixture was stirred at 0° C. for 30 min. On completion, the mixture was quenched with saturated Na$_2$S$_2$O$_3$ (10 mL) and washed with saturated NaHCO$_3$ (2×10 mL). The organic layer was dried over anhydrous Na$_2$SO$_4$, filtered and concentrated in vacuo to give the title compound (200 mg, 94% yield) as yellow solid. LC-MS (ESI$^+$) m/z 514.2 (M+H)$^+$.

N-[2-(4-formylcyclohexyl)indazol-5-yl]-6-(trifluoromethyl)pyridine-2-carboxamide (Intermediate BRP)

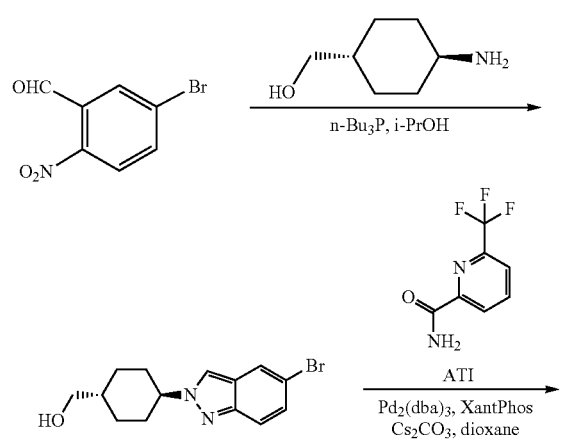

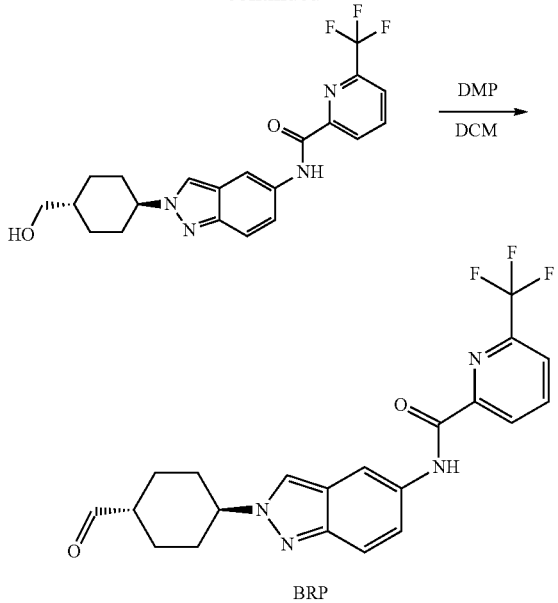

Step 1—[4-(5-Bromoindazol-2-yl)cyclohexyl]methanol

To a solution of 5-bromo-2-nitro-benzaldehyde (2.00 g, 8.70 mmol, CAS #20357-20-4) in i-PrOH (30 mL) was added and (4-aminocyclohexyl)methanol (1.24 g, 9.56 mmol, CAS #1467-84-1). The mixture was stirred at 80° C. for 5 hours, then the tributylphosphane (5.28 g, 26.0 mmol, 6.44 mL) was added at 25° C. Next, the reaction mixture was stirred at 80° C. for 5 hours. On completion, the reaction mixture was concentrated in vacuo. The residue was purified by column chromatography then the residue was triturated with PE (2 mL) and filtered to give the title compound (1.00 g, 37% yield) as yellow solid. $^1$H NMR (400 MHz, DMSO-d$_6$) δ 8.39 (d, J=0.8 Hz, 1H), 7.93 (dd, J=0.4, 2.0 Hz, 1H), 7.61-7.56 (m, 1H), 7.29 (dd, J=2.0, 9.2 Hz, 1H), 4.49 (t, J=5.2 Hz, 1H), 4.47-4.40 (m, 1H), 2.13-2.10 (m, 2H), 1.94-1.83 (m, 4H), 1.63-1.32 (m, 3H), 1.21-1.08 (m, 2H). LC-MS (ESI$^+$) m/z 309.1 (M+H)$^+$.

Step 2—N-[2-[4-(hydroxymethyl)cyclohexyl]indazol-5-yl]-6-(trifluoromethyl)pyridine-2-carboxamide A mixture of [4-(5-bromoindazol-2-yl)cyclohexyl]methanol (300 mg, 970 umol), 6-(trifluoromethyl) pyridine-2-carboxamide (276. mg, 1.46 mmol, Intermediate ATI), Cs$_2$CO$_3$ (632 mg, 1.94 mmol), Pd$_2$(dba)$_3$ (88.8 mg, 97.0 umol) and Xantphos (112 mg, 194 umol) in dioxane (8 mL) was purged with N$_2$ three times. Then the mixture was stirred at 100° C. for 6 hours under N$_2$ atmosphere. On completion, the filtrate was concentrated in vacuo. The residue was purified by column chromatography to give the title compound (328 mg, 80% yield) as yellow solid. $^1$H NMR (400 MHz, DMSO-d$_6$) δ 10.35 (s, 1H), 8.42-8.38 (m, 2H), 8.38-8.32 (m, 1H), 8.29 (d, J=1.2 Hz, 1H), 8.17 (dd, J=1.2, 7.6 Hz, 1H), 7.63-7.59 (m, 1H), 7.57-7.52 (m, 1H), 4.53-4.37 (m, 2H), 2.16-2.14 (m, 2H), 1.94-1.86 (m, 4H), 1.56-1.47 (m, 1H), 1.24-1.08 (m, 4H). LC-MS (ESI$^+$) m/z 419.5 (M+H)$^+$.

Step 3—N-[2-(4-formylcyclohexyl)indazol-5-yl]-6-(trifluoromethyl)pyridine-2-carboxamide To a solution of N-[2-[4-(hydroxymethyl)cyclohexyl]indazol-5-yl]-6-(trifluoromethyl)pyridine-2-carboxamide (100 mg, 239 umol) in DCM (1 mL) was added DMP (121 mg, 286 umol) at 25° C. and the mixture was stirred for 10 minutes. On completion, the reaction mixture was quenched with Na$_2$S$_2$O$_3$ (2 mL) and NaHCO$_3$(2 mL) at 25° C., and extracted with DCM (4×3 mL). The combined organic layers were dried over anhydrous Na$_2$SO$_4$, filtered and concentrated in vacuo to give the title compound (85.0 mg, 85% yield) as yellow solid. $^1$H NMR (400 MHz, DMSO-d$_6$) δ 10.36 (s, 1H), 9.65 (s, 1H), 8.43-8.33 (m, 3H), 8.30 (d, J=1.2 Hz, 1H), 8.17 (dd, J=1.2, 7.6 Hz, 1H), 7.64-7.53 (m, 2H), 4.47 (m, 1H), 2.26-2.07 (m, 4H), 1.99-1.94 (m, 2H), 1.50-1.44 (m, 2H), 1.23 (s, 1H). LC-MS (ESI$^+$) m/z 417.1 (M+H)$^+$.

N-[6-fluoro-2-(4-formylcyclohexyl)-1-methyl-indol-5-yl]-6-(trifluoromethyl)pyridine-2-carboxamide (Intermediate BRQ)

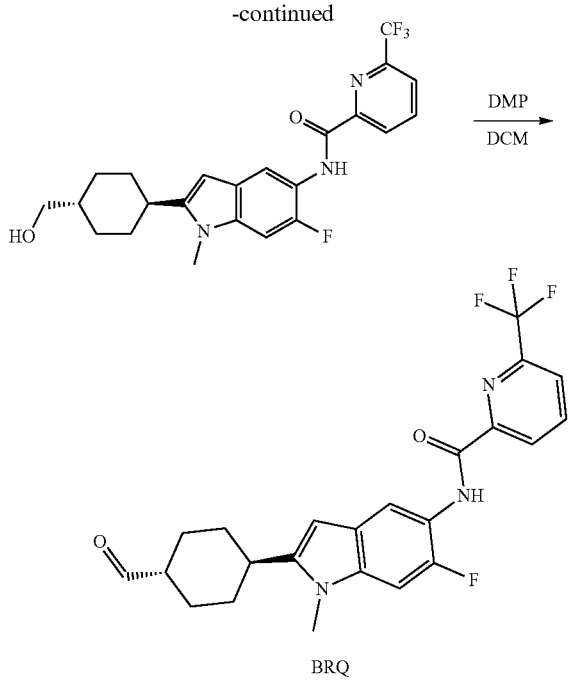

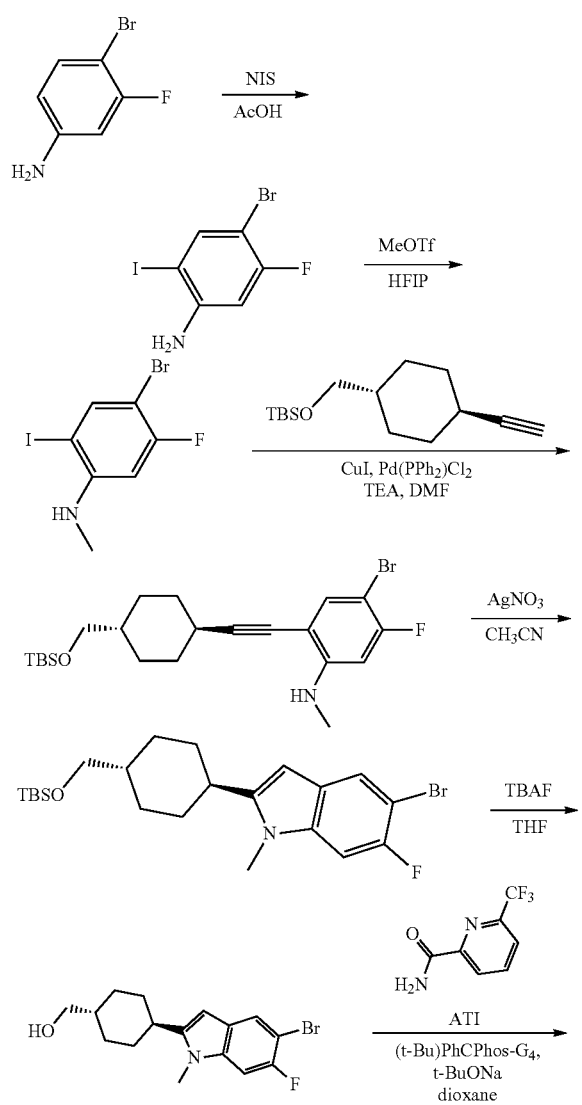

Step 1—4-Bromo-5-fluoro-2-iodo-aniline

To a solution of 4-bromo-3-fluoro-aniline (2.00 g, 10.5 mmol, CAS #656-65-5) in HOAc (40 mL) was added NIS (2.84 g, 12.63 mmol) and the mixture was stirred at 25° C. for 2 hrs. On completion, the reaction mixture was concentrated in vacuo to give a residue. The residue was diluted with EA (50 mL) and quenched with saturated NaHCO$_3$ until the pH=7. The organic layer separated and dried over Na$_2$SO$_4$, filtered and concentrated in vacuo to give a residue. The residue was purified by column chromatography (SiO$_2$, PE/EA=40:1) to give the title compound (1.70 g, 51% yield) as brown solid. $^1$H NMR (400 MHz, DMSO-d$_6$) δ 7.75 (d, J=7.6 Hz, 1H), 6.67 (d, J=11.2 Hz, 1H), 5.67 (s, 2H).

Step 2—4-Bromo-5-fluoro-2-iodo-N-methyl-aniline

To a solution of 4-bromo-5-fluoro-2-iodo-aniline (1.60 g, 5.06 mmol) in HFIP (20 mL) was added methyl trifluoromethanesulfonate (831 mg, 5.06 mmol) dropwise at 0° C., then the mixture was stirred at 25° C. for 48 hrs. On completion, the reaction was quenched with NaHCO$_3$(30 mL) and extracted with EA (30 mL×3). The combined organic layer was dried over Na$_2$SO$_4$, filtered and concentrated in vacuo to give a residue. The residue was purified by column chromatography (SiO$_2$, PE/EA=1:0) to give the title compound (1.00 g, 59% yield) was obtained as light yellow solid. $^1$H NMR (400 MHz, DMSO-d$_6$) δ 7.80 (d, J=7.6 Hz, 1H), 6.48 (d, J=12.4 Hz, 1H), 5.46 (d, J=3.2 Hz, 1H), 2.73 (d, J=4.8 Hz, 3H).

Step 3—4-Bromo-2-[2-[4-[[tert-butyl(dimethyl)silyl]oxymethyl]cyclohexyl]ethynyl]-5-fluoro-N-methyl-aniline To a solution of 4-bromo-5-fluoro-2-iodo-N-methyl-aniline (0.80 g, 2.42 mmol) and tert-butyl-[(4-ethynylcyclohexyl)methoxy]-dimethyl-silane (734 mg, 2.91 mmol, Intermediate BRH) in DMF (10 mL) was added TEA (1.23 g, 12.1 mmol), CuI (46.1 mg, 242 umol) and Pd(PPh$_3$)$_2$Cl$_2$ (340 mg, 484 umol). The mixture was stirred at 25° C. for 3 hrs. On completion, the reaction mixture was diluted with H$_2$O (40 mL) and extracted EA (20 mL×3). The combined organic layer was dried over Na$_2$SO$_4$, filtered and concentrated in vacuo to give a residue. The residue was purified by reverse phase (FA condition) to give the title compound (0.8 g, 72% yield) as light yellow oil. $^1$H NMR (400 MHz, CDCl$_3$) δ 7.32 (d, J=7.6 Hz, 1H), 6.28 (d, J=11.2 Hz, 1H), 3.37 (d, J=6.4 Hz, 2H), 2.82 (s, 3H), 3.41-2.34 (m, 2H), 2.08-2.01 (m, 2H), 1.94 (dd, J=3.2, 13.2 Hz, 1H), 1.82-1.75 (m, 2H), 1.66-1.57 (m, 1H), 1.45-1.37 (m, 3H), 1.00-0.89 (m, 2H), 0.86 (s, 9H), 0.01 (s, 6H).

Step 4—[4-(5-Bromo-6-fluoro-1-methyl-indol-2-yl)cyclohexyl]methoxy-tert-butyl-dimethyl-silane To a solution of 4-bromo-2-[2-[4-[[tert-butyl(dimethyl)silyl]oxymethyl]cyclohexyl]ethynyl]-5-fluoro-N-methyl-aniline (700 mg, 1.54 mmol) in CH$_3$CN (7 mL) was added AgNO$_3$ (26.1 mg, 154 umol) and the mixture was stirred at 80° C. for 16 hrs. On completion, the reaction was filtered and concentrated in vacuo to give a residue, then the residue was diluted with EA (30 mL) and washed with saturated NaCl (20 mL). The organic lay was dried over Na$_2$SO$_4$, filtered and concentrated in vacuo to give the title compound (0.7 g, 85% yield) as light yellow solid. $^1$H NMR (400 MHz, CDCl$_3$) δ 7.65 (d, J=6.8 Hz, 1H), 7.03 (d, J=9.2 Hz, 1H), 6.16 (s, 1H), 3.64 (s, 3H), 3.48 (d, J=6.4 Hz, 2H), 2.68-2.55 (m, 1H), 2.12-2.03 (m, 2H), 1.97-1.92 (m, 2H), 1.55-1.40 (m, 3H), 1.19-1.06 (m, 2H), 0.92 (s, 9H), 0.07 (s, 6H).

Step 5—[4-(5-Bromo-6-fluoro-1-methyl-indol-2-yl)cyclohexyl]methanol

To a solution of [4-(5-bromo-6-fluoro-1-methyl-indol-2-yl)cyclohexyl]methoxy-tert-butyl-dimethyl-silane (500 mg, 1.10 mmol) in THF (10 mL) was added TBAF (1 M, 2.20 mmol, 2.20 mL) and the mixture was stirred at 25° C. for 1 hr. On completion, the reaction mixture was diluted with EA (50 mL) and washed with saturated NaCl (20 mL×2). The organic layer was dried over Na$_2$SO$_4$, filtered and concentrated in vacuo to give the title compound (0.36 g, 80% yield) as light yellow solid. $^1$H NMR (400 MHz, CDCl$_3$) δ 7.65 (d, J=6.8 Hz, 1H), 7.04 (d, J=9.6 Hz, 1H), 6.17 (s, 1H), 3.64 (s, 3H), 3.55 (s, 2H), 2.71-2.58 (m, 1H), 2.10 (d, J=12.4 Hz, 2H), 1.98 (d, J=12.0 Hz, 2H), 1.68-1.60 (m, 1H), 1.55-1.44 (m, 2H), 1.36-1.28 (m, 1H), 1.26-1.10 (m, 2H).

Step 6—N-[6-fluoro-2-[4-(hydroxymethyl)cyclohexyl]-1-methyl-indol-5-yl]-6-(trifluoromethyl) pyridine-2-carboxamide To a solution of [4-(5-bromo-6-fluoro-1-methyl-indol-2-yl)cyclohexyl]methanol (200 mg, 587 umol) and 6-(trifluoromethyl)pyridine-2-carboxamide (122 mg, 646 umol, Intermediate ATI) in dioxane (4 mL) was added (t-Bu)PhCPhos Pd G4 (20 mg) and t-BuONa (112 mg, 1.18 mmol). The mixture was stirred at 80° C. for 16 hrs. On completion, the reaction was diluted with water (10 mL) and extracted with EA (10 mL×3). The combined organic layers were dried over Na$_2$SO$_4$, filtered and concentrated in vacuo to give a residue. The residue was purified by column chromatography (SiO$_2$, petroleum ether/ethyl acetate=1/1) and then re-purified by prep-TLC (PE/EA=1/1) to give the title compound (15.0 mg, 5% yield) as light yellow solid. $^1$H NMR (400 MHz, CDCl$_3$) δ 10.08 (s, 1H), 8.63-8.45 (m, 2H), 8.17-8.08 (m, 1H), 7.87 (d, J=8.0 Hz, 1H), 7.08 (d, J=11.6 Hz, 1H), 6.26 (s, 1H), 3.67 (s, 3H), 3.50-3.44 (m, 3H), 2.35-2.25 (m, 2H), 2.02-1.98 (m, 2H), 1.82-1.78 (m, 1H), 1.04-0.92 (m, 4H); LC-MS (ESI$^+$) m/z 450.1 (M+H)$^+$.

Step 7—N-[6-fluoro-2-(4-formylcyclohexyl)-1-methyl-indol-5-yl]-6-(trifluoromethyl)pyridine-2-carboxamide To a solution of N-[6-fluoro-2-[4-(hydroxymethyl)cyclohexyl]-1-methyl-indol-5-yl]-6-(trifluoro methyl)pyridine-2-carboxamide (13.0 mg, 28.9 umol) in DCM (1 mL) was added DMP (14.7 mg, 34.7 umol) and the mixture was stirred at 25° C. for 16 hrs. On completion, the reaction was diluted with DCM (10 mL) and quenched with saturated Na$_2$S$_2$O$_3$ (3 mL) and NaHCO$_3$ (10 mL). The organic layer was separated and dried over Na$_2$SO$_4$, filtered and concentrated in vacuo to give the title compound (12.0 mg, 90% yield) as light yellow solid. LC-MS (ESI$^+$) m/z 448.3 (M+H)$^+$.

1-Methyl-3-[3-methyl-2-oxo-4-(4-piperidyl)benzimidazol-1-yl]piperidine-2,6-dione (Intermediate BCD)

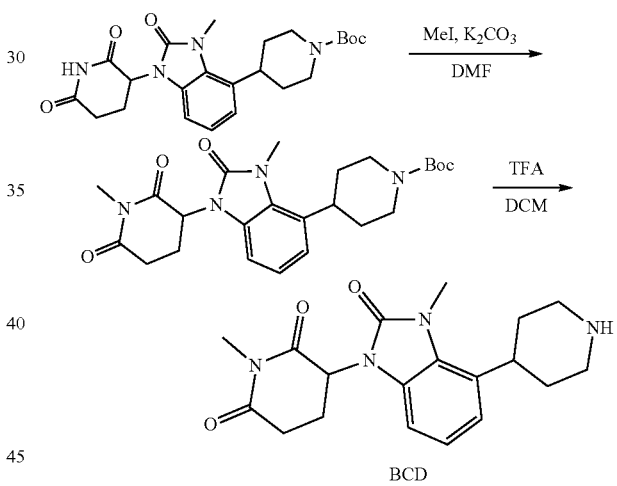

Step 1—Tert-butyl 4-[3-methyl-1-(1-methyl-2,6-dioxo-3-piperidyl)-2-oxo-benzimidazol-4-yl]piperidine-1-carboxylate To a solution of tert-butyl 4-[1-(2,6-dioxo-3-piperidyl)-3-methyl-2-oxo-benzimidazol-4-yl]piperidine-1-carboxylate (300 mg, 677 umol, synthesized via Steps 1-2 of Intermediate AZK) in DMF (4 mL) was added K$_2$CO$_3$ (93.7 mg, 677 umol). The reaction mixture was stirred at 0° C. for 15 min. Then MeI (192 mg, 1.36 mmol) was added and the reaction mixture was stirred at 25° C. for 4 hrs. On completion, the mixture was quenched with water (1 mL) and extracted with ethyl acetate (3×25 mL). The combined organic phase was dried over anhydrous sodium sulfate, filtered and concentrated to give a residue. The residue was triturated with NH$_4$Cl (20 mL) at 25° C. for 15 min to give the title compound (250 mg, 80% yield) as an off-white solid. $^1$H NMR (400 MHz, DMSO-d$_6$) δ 7.22 (s, 2H), 6.99 (s, 1H), 4.22-3.96 (m, 2H), 3.63-3.59 (m, 3H), 3.48-3.38 (m, 1H), 3.03 (s, 3H), 2.99-2.91 (m, 2H), 2.89 (s, 1H), 2.83-2.64 (m, 3H), 2.06-1.94 (m, 1H), 1.82 (d, J=12.4 Hz, 2H), 1.66-1.50 (m, 2H), 1.43 (s, 9H), LC-MS (ESI+) m/z 401.3 (M+1)+.

Step 2—1-Methyl-3-[3-methyl-2-oxo-4-(4-piperidyl)benzimidazol-1-yl]piperidine-2,6-dione To a solution of tert-butyl 4-[3-methyl-1-(1-methyl-2,6-dioxo-3-piperidyl)-2-oxo-benzimidazol-4-yl]piperidine-1-carboxylate (250 mg, 547 umol) in DCM (3 mL) was added TFA (1 mL). The reaction mixture was stirred at 25° C. for 1 hr. On completion, the mixture was concentrated to give the title compound (100 mg, 38% yield, TFA) as brown oil. LC-MS (ESI+) m/z 357.1 (M+1)+.

N-[2-[4-(hydroxymethyl)cyclohexyl]-6-(1-hydroxy-1-methyl-ethyl)indazol-5-yl]-6-methyl-pyridine-2-carboxamide (Intermediate AOX)

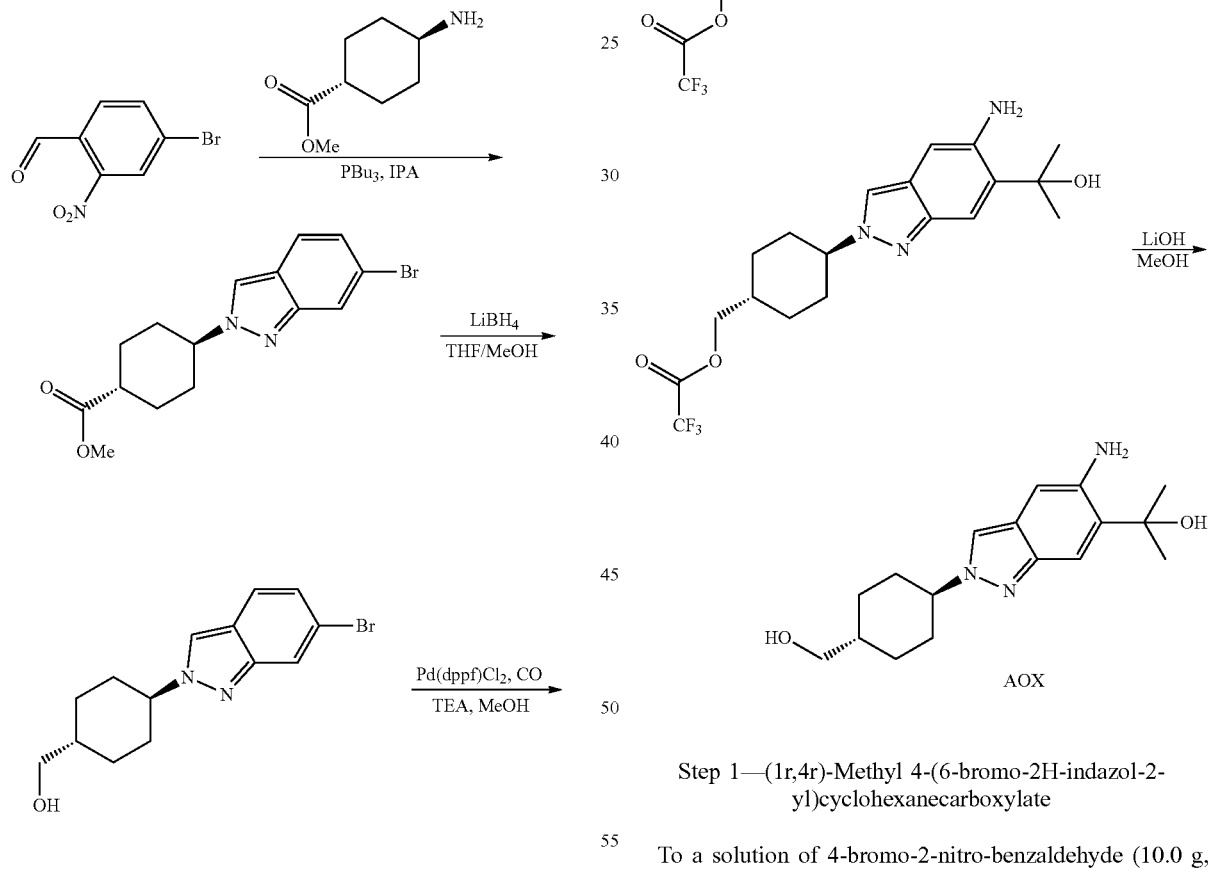

Step 1—(1r,4r)-Methyl 4-(6-bromo-2H-indazol-2-yl)cyclohexanecarboxylate

To a solution of 4-bromo-2-nitro-benzaldehyde (10.0 g, 43.5 mmol, CAS #62456-15-9) in IPA (100 mL) was added methyl 4-aminocyclohexanecarboxylate (6.83 g, 43.5 mmol, CAS #5551-12-2). The mixture was heated at 80° C. for 4 hrs under N₂. It was cooled to 25° C. Tributylphosphane (26.4 g, 130 mmol) was added and the reaction mixture was heated to 80° C. for 16 hrs. On completion, the reaction mixture was concentrated in vacuo to give a residue. The residue was purified by silica gel chromatography (PE: EA=10:1) to give the title compound (13.0 g, 87% yield) as a white solid. ¹H NMR (400 MHz, CDCl₃) δ 7.94 (d, J=0.8 Hz, 1H), 7.92-7.85 (m, 1H), 7.53 (d, J=8.8 Hz, 1H), 7.16

(dd, J=1.6, 8.8 Hz, 1H), 4.41 (tt, J=4.0, 12.0 Hz, 1H), 3.73 (s, 3H), 2.47 (tt, J=3.6, 12.4 Hz, 1H), 2.41-2.32 (m, 2H), 2.30-2.21 (m, 2H), 2.01 (dq, J=3.2, 12.8 Hz, 2H), 1.60-1.56 (m, 2H); LC-MS (ESI$^+$) m/z 339.0 (M+H)$^+$.

Step 2—((1r,4r)-4-(6-Bromo-2H-indazol-2-yl)cyclohexyl)methanol

To a solution of methyl 4-(6-bromoindazol-2-yl)cyclohexanecarboxylate (9.00 g, 26.7 mmol) in a mixed solvent of tetrahydrofuran (90.0 mL) and methanol (11.0 mL) was added LiBH4 (1.74 g, 80.0 mmol) at 25° C. The reaction mixture was stirred at 60° C. for 3 hr. On completion, the reaction mixture was quenched with saturated NH$_4$Cl (100 mL), then removed to tetrahydrofuran and methanol. The residue was extracted with dichloromethane (3×100 mL). The combined organic layers were washed with brine (50 mL), dried over anhydrous sodium sulfate, filtered and the filtrate was concentrated in vacuo to give the title compound (7.80 g, 95% yield) as a white solid. $^1$H NMR (400 MHz, CDCl$_3$) δ 7.95 (s, 1H), 7.92-7.89 (m, 1H), 7.54 (d, J=8.8 Hz, 1H), 7.16 (dd, J=1.6, 8.8 Hz, 1H), 4.75 (s, 1H), 4.39 (tt, J=3.6, 12.0 Hz, 1H), 3.58 (d, J=6.4 Hz, 2H), 2.47-2.26 (m, 2H), 2.14-1.91 (m, 4H), 1.68-1.63 (m, 1H), 1.27 (dq, J=3.2, 12.8 Hz, 2H), LC-MS (ESI$^+$) m/z 311.2 (M+H)$^+$.

Step 3—Ethyl 2-((1r,4r)-4-(hydroxymethyl)cyclohexyl)-2H-indazole-6-carboxylate

To a stirring solution of [4-(6-bromoindazol-2-yl)cyclohexyl]methanol (7.30 g, 23.6 mmol) in EtOH (70.0 mL) in a steel bomb under inert atmosphere were added Pd(dppf)Cl$_2$ (1.73 g, 2.36 mmol), TEA (11.9 g, 118 mmol, 16.4 mL) and the mixture was heated to 80° C. under CO gas atmosphere (50 psi) and stirred for 12 hrs. On completion, the reaction mixture was filtered and concentrated in vacuo to give a residue. The residue was purified by silica gel chromatography (PE:EA=2:1) to give the title compound (6.70 g, 93% yield) as a white solid. LC-MS (ESI$^+$) m/z 301.1 (M+H)$^+$.

Step 4—Ethyl 5-nitro-2-((1r,4r)-4-((2,2,2-trifluoroacetoxy)methyl)cyclohexyl)-2H-indazole-6-carboxylate To a solution of ethyl 2-[4-(hydroxymethyl)cyclohexyl]indazole-6-carboxylate (6.5 g, 21.5 mmol) in TFAA (22.6 g, 107 mmol, 15 mL). The reaction mixture was stirred at 20° C. for 2 hrs. After, KNO$_3$ (4.35 g, 43.0 mmol) in H$_2$SO$_4$ (60 mL) was added dropwise at –5° C. The reaction mixture was stirred at 20° C. for 1 hr. On completion, the reaction mixture was poured into cold water (10 mL) and extracted with EA (3×100 mL). The combined organic layers were washed with brine (2×100 mL), saturated NaHCO$_3$(5×200 mL) until the pH=7, dried over Na$_2$SO$_4$, filtered and concentrated in vacuo to give the title compound (9.30 g, 97% yield) as a yellow solid. $^1$H NMR (400 MHz, CDCl$_3$) δ 8.41 (s, 1H), 8.22 (d, J=0.6 Hz, 1H), 8.04 (s, 1H), 4.56-4.45 (m, 1H), 4.41 (q, J=7.2 Hz, 2H), 4.29 (d, J=6.4 Hz, 2H), 2.45-2.35 (m, 2H), 2.11-2.03 (m, 4H), 2.00-1.91 (m, 1H), 1.44-1.31 (m, 5H). LC-MS (ESI$^+$) m/z 444.1 (M+H)$^+$.

Step 5—Ethyl 5-amino-2-[4-[(2,2,2-trifluoroacetyl)oxymethyl]cyclohexyl]indazole-6-carboxylate To a solution of ethyl 5-nitro-2-[4-[(2,2,2-trifluoroacetyl)oxymethyl]cyclohexyl]indazole-6-carboxylate (9.20 g, 20.7 mmol) in THF (150.0 mL) was added Pd/C (1.00 g, 10 wt %). The reaction mixture was stirred at 25° C. for 12 hrs under H$_2$ (15 Psi) atmosphere. On completion, the reaction mixture was filtered and the filtrate was concentrated in vacuo to give the title compound (8.30 g, 96% yield) as a yellow solid. LC-MS (ESI$^+$) m/z 414.2 (M+H)$^+$.

Step 6—[4-[5-Amino-6-(1-hydroxy-1-methyl-ethyl)indazol-2-yl]cyclohexyl]methyl 2,2,2-trifluoroacetate To a solution of ethyl 5-amino-2-[4-[(2,2,2-trifluoroacetyl)oxymethyl]cyclohexyl]indazole-6-carboxylate (8.30 g, 20.1 mmol) in THF (80.0 mL) was added MeMgBr (3 M, 53.5 mL) dropwise at 0° C. Then the reaction mixture was stirred at 20° C. for 12 hrs. On completion, the reaction mixture was quenched with water (400 mL), and extracted with EA (2×300 mL). The organic layer was washed with brine (100 mL), and concentrated in vacuo. The residue was purified by silica gel chromatography (SiO$_2$, PE:EA=3:1) to give the title compound (5.00 g, 62% yield) as a yellow solid. LC-MS (ESI$^+$) m/z 400.1 (M+H)$^+$.

Step 7—N-[2-[4-(hydroxymethyl)cyclohexyl]-6-(1-hydroxy-1-methyl-ethyl)indazol-5-yl]-6-methyl-pyridine-2-carboxamide To a solution of [4-[5-amino-6-(1-hydroxy-1-methyl-ethyl)indazol-2-yl]cyclohexyl]methyl 2,2,2-trifluoroacetate (2.60 g, 6.51 mmol) in a mixed solvent of THF (15.0 mL) and H$_2$O (5.00 mL) was added LiOH·H$_2$O (1.37 g, 32.5 mmol). The reaction mixture was stirred at 60° C. for 20 hrs. On completion, the residue was poured into water (5 mL) and stirred for 5 minutes, then the aqueous phase was extracted with ethyl acetate (50 mL×2). The combined organic phase was washed with brine (2×50 mL), dried with anhydrous Na$_2$SO$_4$, filtered and concentrated in vacuo. The residue was purified by silica gel chromatography (column height: 250 mm, diameter: 100 mm, 100-200 mesh silica gel, DCM/MeOH=25/1, Rf=0.41) to afford the compound (840 mg, 35% yield) as yellow solid. $^1$H NMR (400 MHz, DMSO-d$_6$) δ 7.88 (s, 1H), 7.31 (s, 1H), 6.63 (s, 1H), 5.35-5.15 (m, 3H), 4.48 (t, J=5.2 Hz, 1H), 4.32-4.22 (m, 1H), 3.27 (t, J=5.6 Hz, 2H), 2.12-2.03 (m, 2H), 1.92-1.80 (m, 4H), 1.59 (s, 6H), 1.50-1.40 (m, 1H), 1.18-1.05 (m, 2H). LC-MS (ESI$^+$) m/z 304.1 (M+H)$^+$.

N-(2-((1r,4r)-4-formylcyclohexyl)-6-(2-hydroxypropan-2-yl)-2H-indazol-5-yl)-2-methyloxazole-4-carboxamide (Intermediate BGF)

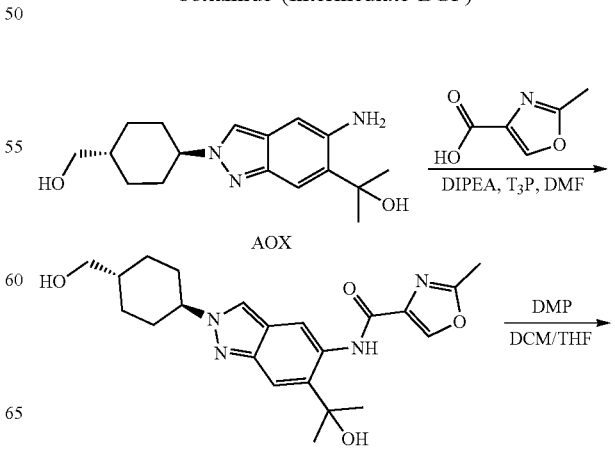

-continued

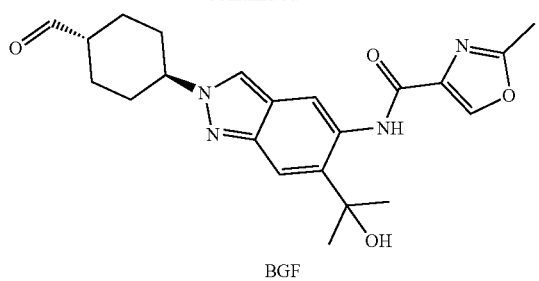

BGF

Step 1—N-(2-((1r,4r)-4-(hydroxymethyl)cyclo-hexyl)-6-(2-hydroxypropan-2-yl)-2H-indazol-5-yl)-2-methyloxazole-4-carboxamide To a solution of 2-[5-amino-2-[4-(hydroxymethyl)cyclohexyl]indazol-6-yl]propan-2-ol (200 mg, 659 umol, Intermediate AOX), 2-methyloxazole-4-carboxylic acid (CAS #23062-17-1, 83.7 mg, 659 umol) in DMF (2 mL) was added DIPEA (1.28 g, 9.89 mmol) and $T_3P$ (838 mg, 1.32 mmol, 50% solution) and the mixture was stirred at 20° C. for 12 hours. On completion, the reaction mixture was quenched with $H_2O$ (0.5 mL). The mixture was purified by reverse phase flash (0.1% FA) to give the title compound (200 mg, 63% yield) as a yellow solid. LC-MS (ESI$^+$) m/z 413.2 (M+H)$^+$.

Step 2—N-(2-((1r,4r)-4-formylcyclohexyl)-6-(2-hydroxypropan-2-yl)-2H-indazol-5-yl)-2-methyloxazole-4-carboxamide To a solution of N-[2-[4-(hydroxymethyl) cyclohexyl]-6-(1-hydroxy-1-methyl-ethyl)indazol-5-yl]-2-methyl-oxazole-4-carboxamide (180 mg, 436 umol) in DCM (9 mL) and THF (9 mL) was added DMP (222 mg, 523 umol) at 0° C. The mixture was stirred at 0-25° C. for 1 hour. On completion, the reaction mixture was quenched with $H_2O$ (10 mL) at 25° C. and extracted with EA (3×10 mL). The combined organic layers were washed with brine (2×10 mL), dried over $Na_2SO_4$ and filtered. The filtrate was concentrated in vacuo to give the title compound (175 mg, 95% yield) as a brown solid. LC-MS (ESI$^+$) m/z 411.4 (M+H)$^+$.

1-Methyl-3-[3-methyl-4-[4-(methylamino)-1-piperidyl]-2-oxo-benzimidazol-1-yl]piperidine-2,6-dione (Intermediate BFL)

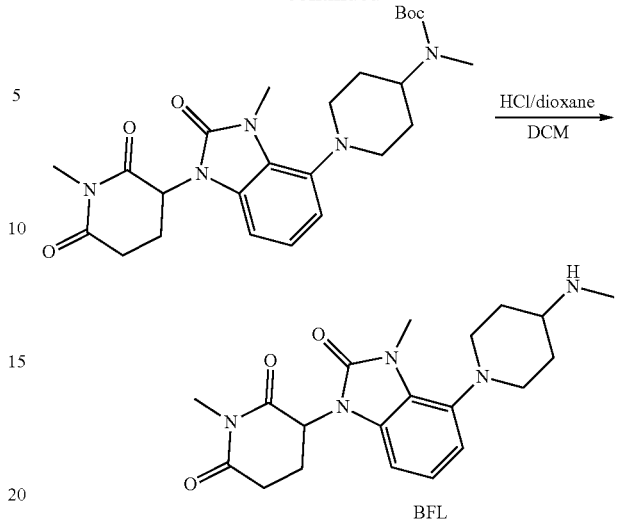

BFL

Step 1—Tert-butyl N-methyl-N-[1-[3-methyl-1-(1-methyl-2,6-dioxo-3-piperidyl)-2-oxo-benzimidazol-4-yl]-4-piperidyl]carbamate To a solution of tert-butyl N-[1-[1-(2,6-dioxo-3-piperidyl)-3-methyl-2-oxo-benzimidazol-4-yl]-4-piperidyl]-N-methyl-carbamate (353 mg, 742 umol, synthesized via Step 1 of Intermediate AQK) in DMF (5 mL) was added 4 Å molecular sieves (30.0 mg), $K_2CO_3$ (113 mg, 816 umol) at 25° C. The reaction mixture was stirred for 10 minutes. Then MeI (158 mg, 1.11 mmol, 69.3 uL) was added at 0° C. and the mixture was stirred at 25° C. for 16 hours. On completion, the reaction mixture was filtered and the filtrate was adjusted to pH 4-5 with FA. The residue was poured into ice-water (10 mL) and stirred for 2 min. The aqueous phase was then extracted with ethyl acetate (2×10 mL). The combined organic layer was washed with brine (2×20 mL), dried with anhydrous $Na_2SO_4$, filtered and concentrated in vacuo. The residue was purified by silica gel chromatography (ethyl acetate) to give the title compound (240 mg, 66% yield) as yellow solid. LC-MS (ESI$^+$) m/z 486.2 (M+H)$^+$.

Step 2—1-Methyl-3-[3-methyl-4-[4-(methylamino)-1-piperidyl]-2-oxo-benzimidazol-1-yl]piperidine-2,6-dione To a solution of tert-butyl N-methyl-N-[1-[3-methyl-1-(1-methyl-2,6-dioxo-3-piperidyl)-2-oxo-benzimidazol-4-yl]-4-piperidyl]carbamate (100 mg, 206 umol) in DCM (3 mL) was added HCl/dioxane (4 M, 3 mL) and the mixture was stirred at 25° C. for 2 hours. On completion, the reaction mixture was concentrated in vacuo to give the title compound (86.0 mg, 99% yield, HCl salt) as brown solid. LC-MS (ESI$^+$) m/z 386.1 (M+H)$^+$.

N-[2-(4-formylcyclohexyl)pyrazolo[3,4-c]pyridin-5-yl]-6-(trifluoromethyl)pyridine-2-carboxamide (Intermediate BRR)

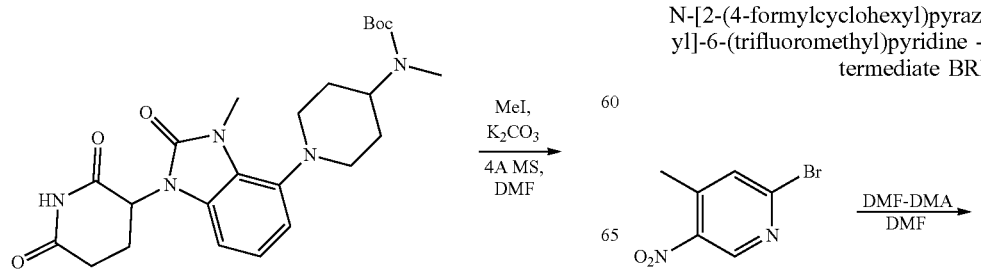

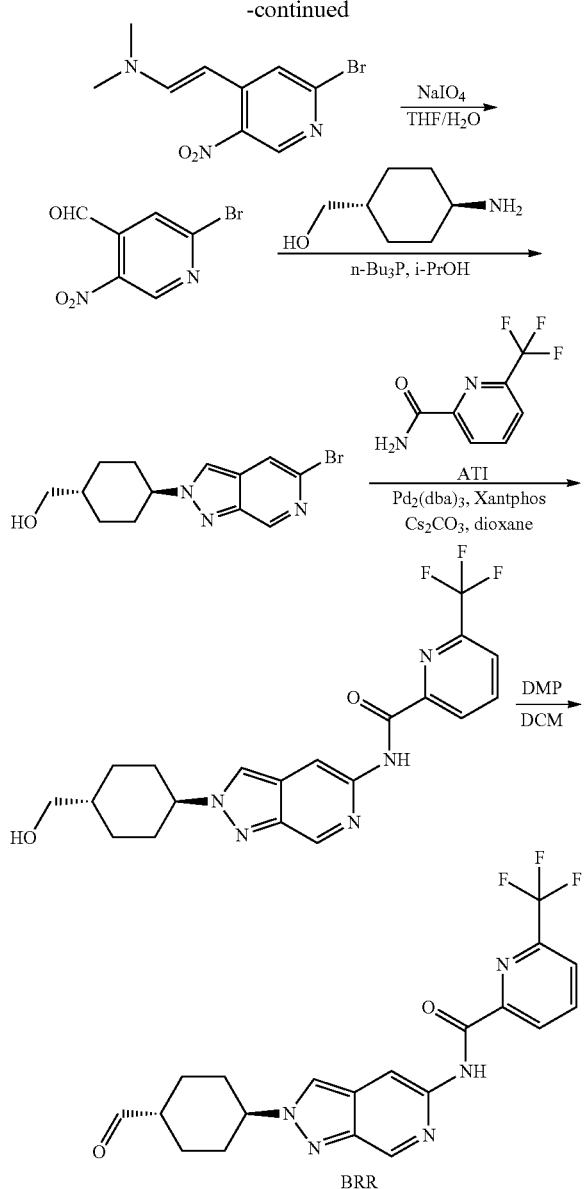

Step 1—(E)-2-(2-Bromo-5-nitro-4-pyridyl)-N,N-dimethyl-ethenamine

To a solution of 2-bromo-4-methyl-5-nitro-pyridine (10.0 g, 46.0 mmol, CAS #23056-47-5) in DMF (160 mL) was added DMF-DMA (10.9 g, 92.1 mmol) and the mixture was stirred at 60° C. for 2 hours. The reaction was then diluted with water (340 mL) and extracted with EA (60 mL×3). The combined organic layer was washed with an aqueous solution of NaCl (50 mL). The organic layer was dried over $Na_2SO_4$, filtered and concentrated in vacuo to give a residue. The residue was triturated with EA/PE (10/1, 100 mL), filtered to give the title compound (7.70 g, 80% yield) as brown solid. $^1$H NMR (400 MHz, $CDCl_3$) δ 8.72 (s, 1H), 7.41 (s, 1H), 7.32 (d, J=13.2 Hz, 1H), 5.91 (d, J=13.2 Hz, 1H), 3.05 (s, 6H).

Step 2—2-Bromo-5-nitro-pyridine-4-carbaldehyde

To a solution of (E)-2-(2-bromo-5-nitro-4-pyridyl)-N,N-dimethyl-ethenamine (6.70 g, 24.6 mmol) in THF (134 mL) and $H_2O$ (134 mL) was added $NaIO_4$ (15.8 g, 73.8 mmol) at 20° C. for 16 hours. On completion, an aqueous solution of $Na_2S_2O_3$ (50 mL) was added into the reaction mixture. Then the reaction mixture was stirred at 25° C. for 10 mins. After filtration via filter paper, the filtrates were diluted with water (300 mL) and extracted with ethyl acetate (100 mL×3). The combined organic layers were washed with an aqueous solution of NaCl (50 mL). The organic layer was dried over $Na_2SO_4$, filtered and concentrated in vacuo to give a residue. The residue was purified by silica gel chromatography (PE/EA=100/1, 50/1, 30/1, 0/1) to give the title compound (3.00 g, 52% yield) as yellow oil. $^1$H NMR (400 MHz, $CDCl_3$) δ 10.51 (s, 1H), 9.21 (s, 1H), 7.92 (s, 1H).

Step 3—[4-(5-Bromopyrazolo[3,4-c]pyridin-2-yl)cyclohexyl]methanol

To a solution of 2-bromo-5-nitro-pyridine-4-carbaldehyde (3.00 g, 12.99 mmol) and (4-aminocyclohexyl) methanol (1.85 g, 14.2 mmol) in i-PrOH (80 mL) was added tributylphosphane (7.88 g, 38.9 mmol, CAS #1467-84-1). The mixture was stirred at 80° C. for 16 hours. On completion, the reaction mixture was diluted with water (200 mL) and extracted with EA (50 mL×2). The combined organic layers were dried over $Na_2SO_4$, filtered and concentrated in vacuo to give a residue. The residue was purified by silica gel chromatography (PE/EA=5/1, 1/1, 0/1), then the residue was triturated with PE (2 mL) for 30 mins. The title compound (0.870 g, 21% yield) was obtained as yellow solid. $^1$H NMR (400 MHz, $CDCl_3$) δ 9.04 (s, 1H), 7.97 (s, 1H), 7.74 (d, J=1.2 Hz, 1H), 4.50-4.42 (m, 1H), 3.58 (d, J=6.0 Hz, 2H), 2.37-2.33 (m, 2H), 2.09-2.05 (m, 2H), 2.05-1.95 (m, 2H), 1.73-1.53 (m, 2H), 1.33-1.23 (m, 2H); LC-MS (ESI$^+$) m/z 309.9 (M+H)$^+$.

Step 4—N-[2-[4-(hydroxymethyl)cyclohexyl]pyrazolo[3,4-c]pyridin-5-yl]-6-(trifluoromethyl)pyridine-2-carboxamide To a solution of [4-(5-bromopyrazolo[3,4-c]pyridin-2-yl)cyclohexyl]methanol (500 mg, 1.61 mmol) and 6-(trifluoromethyl)pyridine-2-carboxamide (306 mg, 1.61 mmol, Intermediate ATI) in dioxane (20 mL) was added $Pd_2(dba)_3$ (147 mg, 161 umol), Xantphos (186 mg, 322 umol) and $Cs_2CO_3$ (1.58 g, 4.84 mmol) under $N_2$. The mixture was then stirred at 80° C. for 16 hours. On completion, the reaction mixture was filtered and the filtrate was diluted with water (50 mL) and extracted with EA (20 ml×2). Then the combined organic layer was washed with an aqueous of NaCl (10 mL). The organic layer was dried over $Na_2SO_4$, filtered and concentrated in vacuo to give the residue. The residue was purified by silica gel chromatography (PE/EA=10/1, 5/1, 1/1, 0/1) to give the title compound (180 mg, 26.63% yield) as white solid. $^1$H NMR (400 MHz, $CDCl_3$) δ 10.45 (s, 1H), 9.11 (s, 1H), 8.66-8.51 (m, 2H), 8.15-7.88 (m, 3H), 4.52-4.45 (m, 1H), 3.59 (d, J=6.4 Hz, 2H), 2.39-2.36 (m, 2H), 2.10-1.98 (m, 5H), 1.81-1.71 (m, 1H), 1.44-1.42 (m, 1H), 0.96-0.85 (m, 1H); LC-MS (ESI$^+$) m/z 420.3 (M+H)$^+$.

Step 5—N-[2-(4-formylcyclohexyl)pyrazolo[3,4-c]pyridin-5-yl]-6-(trifluoromethyl)pyridine-2-carboxamide To a solution of N-[2-[4-(hydroxymethyl)cyclohexyl]pyrazolo[3,4-c]pyridin-5-yl]-6-(trifluoromethyl) pyridine-2-carboxamide (80.0 mg, 190 umol) in DCM (4 mL) was added DMP (121 mg, 286 umol, 88.58 uL). The mixture was stirred at 0° C. for 6 hours. On completion, the reaction mixture was filtered and the filtrate was washed with an aqueous of NaHCO₃ (5 mL) and Na₂S₂O₃ (5 mL) and extracted with DCM (10 mL). The combined organic layer was dried over Na₂SO₄, filtered and concentrated in vacuo to give a residue. The residue was purified by reverse phase (0.1% FA) to give the title compound (70.0 mg, 87% yield) as white solid. $^1$H NMR (400 MHz, CDCl₃) δ 10.40 (s, 1H), 9.74 (s, 1H), 9.10 (s, 1H), 8.65-8.51 (m, 2H), 8.16-7.88 (m, 3H), 4.52-4.45 (m, 1H), 2.47-2.29 (m, 5H), 2.17-2.05 (m, 2H), 1.81-1.74 (m, 1H), 1.43 (s, 1H); LC-MS (ESI$^+$) m/z 418.2 (M+H)$^+$.

3-(3,6-Dimethyl-4-(4-(methylamino)piperidin-1-yl)-2-oxo-2,3-dihydro-1H-benzo[d]imidazol-1-yl)piperidine-2,6-dione (Intermediate BRS)

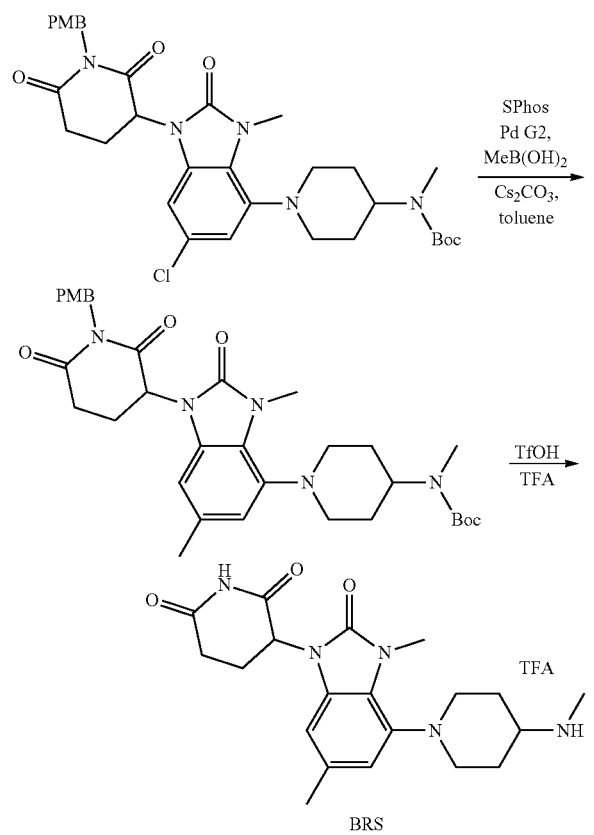

Step 1—Tert-butyl (1-(1-(1-(4-methoxybenzyl)-2,6-dioxopiperidin-3-yl)-3,6-dimethyl-2-oxo-2,3-dihydro-1H-benzo[d]imidazol-4-yl)piperidin-4-yl)(methyl)carbamate A mixture of tert-butyl N-[1-[6-chloro-1-[1-[(4-methoxyphenyl)methyl]-2,6-dioxo-3-piperidyl]-3-methyl-2-oxo-benzimidazol-4-yl]-4-piperidyl]-N-methyl-carbamate (100 mg, 159 umol, synthesized via Steps 1-4 of Intermediate BQQ), MeB(OH)₂ (191 mg, 3.19 mmol), Cs₂CO₃ (156 mg, 479 umol) and [2-(2-aminophenyl)phenyl]-chloro-palladium; dicyclohexyl-[2-(2,6-diisopropoxyphenyl)phenyl]phosphane (12.4 mg, 15.9 umol) in the toluene (2 mL) was stirred at 110° C. for 4 hrs under N₂. On completion, the reaction mixture was concentrated in vacuo and the residue was purified by prep-TLC (PE:EA=2:1) to give the title compound (90.0 mg, 93% yield) as a white solid. $^1$H NMR (400 MHz, CDCl₃) δ 7.39 (d, J=8.6 Hz, 2H), 6.83 (d, J=8.7 Hz, 2H), 6.68 (s, 1H), 6.07 (s, 1H), 5.21 (dd, J=5.4, 13.6 Hz, 1H), 4.98 (s, 2H), 3.79 (s, 3H), 3.75 (s, 3H), 3.27-3.13 (m, 2H), 3.05-2.97 (m, 1H), 2.90-2.77 (m, 6H), 2.66-2.53 (m, 1H), 2.22 (s, 3H), 2.18-2.09 (m, 1H), 1.99-1.85 (m, 2H), 1.81-1.73 (m, 2H), 1.50 (s, 9H).

Step 2—3-(3,6-Dimethyl-4-(4-(methylamino)piperidin-1-yl)-2-oxo-2,3-dihydro-1H-benzo[d]imidazol-1-yl)piperidine-2,6-dione A mixture of tert-butyl N-[1-[1-[1-[(4-methoxyphenyl)methyl]-2,6-dioxo-3-piperidyl]-3,6-dimethyl-2-oxo-benzimidazol-4-yl]-4-piperidyl]-N-methyl-carbamate (90.0 mg, 148 umol) in the TFA (1 mL) and TfOH (0.2 mL) was stirred at 70° C. for 12 hrs. On completion, the reaction mixture was concentrated with a stream of N₂ and the residue was basified with TEA to pH=5-6. The residue was then purified by reversed phase (FA, 0.1%) to give the title compound (55.0 mg, 96% yield) as a white solid. LC-MS (ESI$^+$) m/z 386.1 (M+H)$^+$.

[4-(5-Bromo-6-fluoro-indazol-2-yl)cyclohexyl]methanol (Intermediate BRT)

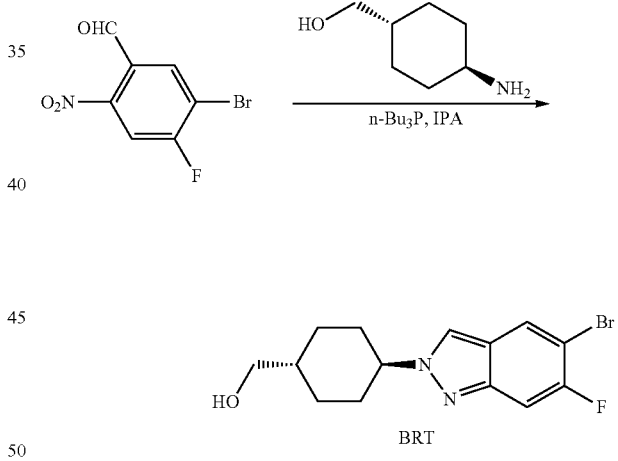

To a solution of 5-bromo-4-fluoro-2-nitro-benzaldehyde (2.00 g, 8.06 mmol, CAS #213382-45-7) in IPA (30 mL) was added (4-aminocyclohexyl)methanol (1.25 g, 9.68 mmol, CAS #1467-84-1), then the mixture was heated at 80° C. for 16 hours. The mixture was cooled to 25° C. then n-Bu₃P (4.89 g, 24.19 mmol) was added into the mixture, and the reaction was stirred at 80° C. for 16 hours. On completion, the reaction mixture was concentrated in vacuo to give the residue, then the residue was purified by flash silica gel chromatography to give the title compound (1.70 g, 64.43% yield) as yellow solid. $^1$H NMR (400 MHz, DMSO-d₆) δ 7.84 (d, J=0.8 Hz, 1H), 7.80 (d, J=6.4 Hz, 1H), 7.32 (d, J=9.6 Hz, 1H), 4.29 (tt, J=4.0, 12.0 Hz, 1H), 3.48 (d, J=6.4 Hz, 2H), 2.31-2.20 (m, 2H), 2.00-1.82 (m, 4H), 1.61-1.55 (m, 2H), 1.26-1.12 (m, 2H).

825

Pyrazolo[1,5-a]pyrimidine-3-carboxamide (Intermediate BRU)

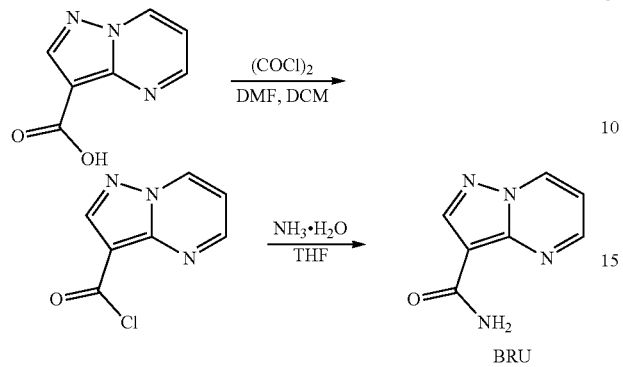

Step 1—Pyrazolo[1,5-a]pyrimidine-3-carbonyl Chloride

To a solution of pyrazolo[1,5-a]pyrimidine-3-carboxylic acid (2.00 g, 12.2 mmol, CAS #25940-35-6) in mixed solvent of DMF (1 mL) and DCM (100 mL) was added (COCl)$_2$ (6.99 g, 55.1 mmol, 4.83 mL) dropwise at 0° C. Then the mixture was stirred at 35° C. for 20 hours. On completion, the mixture was concentrated in vacuo to give the title compound (2.10 g, 94.33% yield).

Step 2—Pyrazolo[1,5-a]pyrimidine-3-carboxamide

To a solution of NH$_3$·H$_2$O (35.6 mL, 231 mmol, 25% solution), and then pyrazolo[1,5-a]pyrimidine-3-carbonyl chloride (2.10 g, 11.5 mmol) in THF (20 mL) was added dropwise at 0° C. The resulting mixture was stirred at 0° C. for 3 hours. On completion, the mixture was concentrated in vacuo to remove solvent and filtered to give the title compound (1.80 g, 95.70% yield) as yellow solid. LC-MS (ESI$^+$) m/z 146.1 (M-NH$_2$)$^+$.

N-[6-fluoro-2-(4-formylcyclohexyl)indazol-5-yl]pyrazolo[1,5-a]pyrimidine-3-carboxamide (Intermediate BRV)

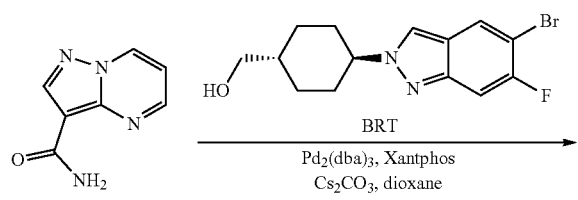

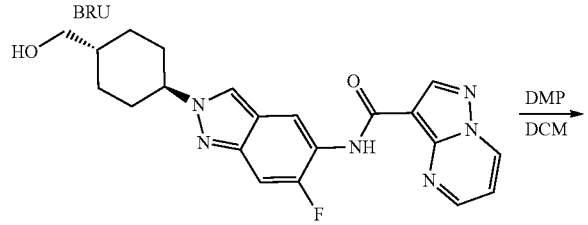

826

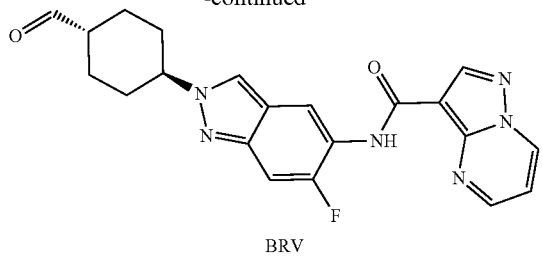

BRV

Step 1—N-[6-fluoro-2-[4-(hydroxymethyl)cyclohexyl]indazol-5-yl]pyrazolo[1,5-a]pyrimidine-3-carboxamide A mixture of pyrazolo[1,5-a]pyrimidine-3-carboxamide (371 mg, 2.29 mmol, Intermediate BRU), [4-(5-bromo-6-fluoro-indazol-2-yl)cyclohexyl]methanol (500 mg, 1.53 mmol, Intermediate BRT), Pd$_2$(dba)$_3$ (139 mg, 152 umol), Xantphos (176 mg, 305 umol) and Cs$_2$CO$_3$ (995 mg, 3.06 mmol) in dioxane (5 mL) was purged with N$_2$ three times. Then the mixture was stirred at 100° C. for 8 hours under N$_2$ atmosphere. On completion, the reaction mixture was filtered and concentrated in vacuo to give the residue, then the residue was diluted with water (50 mL) and extracted with EA (5×30 mL). The combined organic layer was dried over Na$_2$SO$_4$, filtered and concentrated in vacuo to give a residue. The residue was purified by reverse-phase to give the title compound (40 mg, 4.74% yield, 74% purity) as yellow solid. $^1$H NMR (400 MHz, DMSO-d$_6$) δ 10.18 (d, J=3.2 Hz, 1H), 9.40 (dd, J=1.6, 7.2 Hz, 1H), 8.93 (dd, J=1.6, 4.4 Hz, 1H), 8.74 (s, 1H), 8.65 (d, J=8.0 Hz, 1H), 8.48-8.43 (m, 1H), 7.55 (s, 1H), 7.37-7.34 (m, 1H), 4.54-4.34 (m, 3H), 2.15-2.12 (m, 2H), 1.90-1.88 (m, 3H), 1.49-1.44 (m, 1H), 1.23 (s, 2H), 1.17-1.13 (m, 2H). LC-MS (ESI$^+$) m/z 409.1 (M+H)$^+$.

Step 2—N-[6-fluoro-2-(4-formylcyclohexyl)indazol-5-yl]pyrazolo[1,5-a]pyrimidine-3-carboxamide To a solution of N-[6-fluoro-2-[4-(hydroxymethyl)cyclohexyl]indazol-5-yl]pyrazolo[1,5-a]pyrimidine-3-carboxamide (35.0 mg, 85.7 umol) in DCM (1 mL) was added DMP (54.5 mg, 128 umol), then the mixture was stirred at 25° C. for 30 min. On completion, the mixture was quenched with sat. Na$_2$S$_2$O$_3$ (3 mL) and sat.NaHCO$_3$(3 mL) under stirring. The mixture was extracted with DCM (5×5 mL), dried over Na$_2$SO$_4$, filtered and concentrated in vacuo to give the title compound (20.0 mg, 57.43%) as yellow solid. LC-MS (ESI$^+$) m/z 407.1 (M+H)$^+$.

Ethyl 4-(p-tolylsulfonyloxy)cyclohexanecarboxylate (Intermediate AGK)

-continued

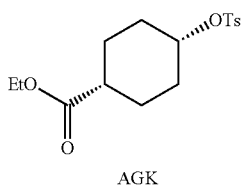

AGK

To a solution of ethyl 4-hydroxycyclohexanecarboxylate (10.0 g, 58.06 mmol, CAS #75877-66-6), DMAP (710 mg, 5.81 mmol) and TEA (17.6 g, 174 mmol) in DCM (150 mL) was added p-TsCl (22.1 g, 116 mmol) at 15° C. The mixture was stirred at 15° C. for 16 hours. On completion, the reaction was quenched with water (20 mL) and the mixture was partitioned. The organic layer was concentrated in vacuo. The residue was purified by column chromatography on silica gel to give the title compound (16.0 g, 84% yield) as white solid. $^1$H NMR (400 MHz, CDCl$_3$) δ 7.79 (d, J=8.2 Hz, 2H), 7.33 (d, J=7.9 Hz, 2H), 4.79-4.64 (m, 1H), 4.10 (q, J=7.2 Hz, 2H), 2.45 (s, 3H), 2.35-2.27 (m, 1H), 1.93-1.82 (m, 4H), 1.76-1.66 (m, 2H), 1.60-1.50 (m, 2H), 1.24 (t, J=7.2 Hz, 3H).

N-[6-(1-hydroxy-1-methyl-ethyl)-2H-indazol-5-yl]-6-(trifluoromethyl)pyridine -2-carboxamide (Intermediate TJ)

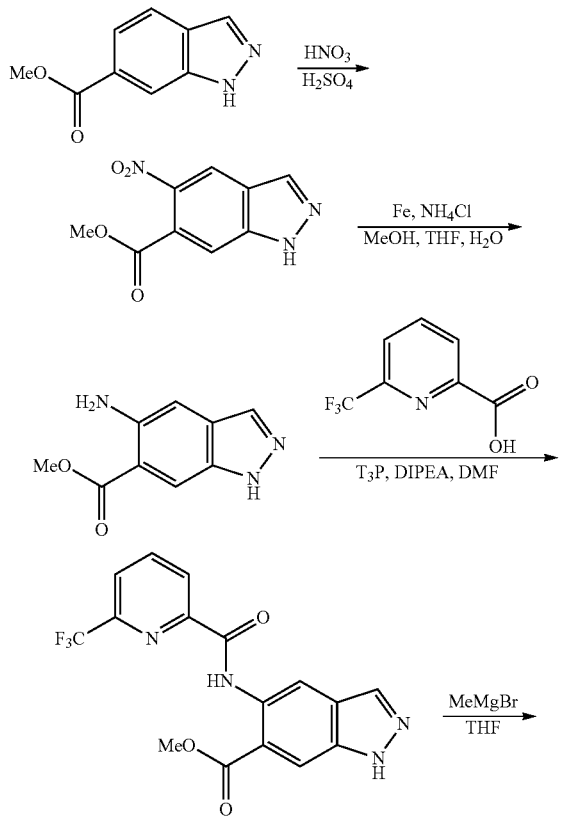

-continued

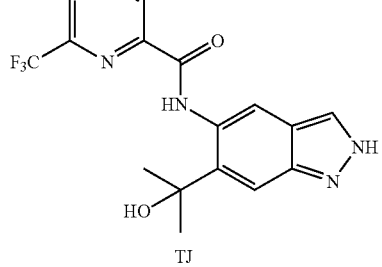

TJ

Step 1—Methyl 5-nitro-1H-indazole-6-carboxylate

To a solution of methyl 1H-indazole-6-carboxylate (10.0 g, 56.7 mmol) in H$_2$SO$_4$ (100 mL) was added a solution of HNO$_3$ (12.1 g, 125 mmol, 65% solution) in H2504 (20 mL) at -10-0° C. during 30 minutes. The mixture was stirred at -10-0° C. for 1 hour. On completion, the mixture was poured into ice/water (1.0 L) slowly. The mixture was filtered and the filter cake was washed with water (2×200 mL). Then the cake was collected and dried in vacuo to give the title compound (11.9 g, 94% yield) as yellow solid. $^1$H NMR (400 MHz, DMSO-d$_6$) δ 8.69 (s, 1H), 8.44 (s, 1H), 7.97 (s, 1H), 3.86 (s, 3H).

Step 2—Methyl 5-amino-1H-indazole-6-carboxylate

To a solution of methyl 5-nitro-1H-indazole-6-carboxylate (10.9 g, 49.2 mmol) in MeOH (100 mL) and THF (60 mL) was added a solution of NH$_4$Cl (26.3 g, 492 mmol) in H$_2$O (100 mL) at 25° C. Then Fe (13.7 g, 245 mmol) was added to the mixture in portions at 70° C., and the mixture was stirred at 70° C. for 1 hour. On completion, the mixture was filtered and the filter cake was washed with EA (200 mL). The filtrate was concentrated in vacuo. The residue was washed with water (100 mL), and extracted with EA (3×100 mL). The combined organic layer was washed with brine (100 mL), dried over Na$_2$SO$_4$, filtered and concentrated in vacuo to the title compound (7.30 g, 77% yield) as yellow solid. $^1$H NMR (400 MHz, DMSO-d$_6$) δ 12.82 (s, 1H), 7.99 (s, 1H), 7.85 (s, 1H), 6.99 (s, 1H), 6.00 (s, 2H), 3.85 (s, 3H).

Step 3—Methyl 5-[[6-(trifluoromethyl)pyridine-2-carbonyl]amino]-1H-indazole-6-carboxylate To a solution of methyl 5-amino-1H-indazole-6-carboxylate (7.20 g, 37.6 mmol), 6-(trifluoromethyl)pyridine-2-carboxylic acid (6.48 g, 33.9 mmol, CAS #131747-42-7) and DIPEA (7.35 g, 56.8 mmol) in THF (70 mL) was added T$_3$P (47.9 g, 44.8 mL, 50 wt %) slowly at 0° C. Then the mixture was stirred at 0-5° C. for 2 hours. On completion, the reaction was quenched with cold water (0.1 mL). The mixture was diluted with water (280 mL), and stirred at 25° C. for 0.5 hour. The mixture was filtered and the filter cake was washed with water (30 mL). The filter cake was collected and dried in vacuo to give the title compound (12.3 g, 99% yield) as yellow solid. $^1$H NMR (400 MHz, DMSO-d$_6$) δ 12.58 (s, 1H), 9.15 (s, 1H), 8.47 (d, J=7.6 Hz, 1H), 8.39 (t, J=7.6 Hz, 1H), 8.30 (s, 1H), 8.25 (s, 1H), 8.20 (d, J=8.0 Hz, 1H), 3.97 (s, 3H).

Step 4—N-[6-(1-hydroxy-1-methyl-ethyl)-2H-indazol-5-yl]-6-(trifluoromethyl)pyridine-2-carboxamide To a solution of methyl 5-[[6-(trifluoromethyl)pyridine-2-carbonyl]amino]-1H-indazole-6-carboxylate (4.00 g, 10.9 mmol) in THF (40 mL) was added MeMgBr-Et₂O solution (3.0 M, 29.3 mL) slowly at 0° C. The mixture was stirred at 0-25° C. for 16 hours. On completion, the reaction was quenched with sat.NH₄Cl (40 mL) slowly at 0-10° C. The mixture was extracted with EA (3×40 mL). The combined organic layer was concentrated in vacuo. The residue was purified by reverse phase chromatography (FA condition) to give the title compound (1.50 g, 37% yield) as light yellow solid. ¹H NMR (400 MHz, CDCl₃) δ 12.23 (s, 1H), 8.96 (s, 1H), 8.52 (d, J=7.6 Hz, 1H), 8.12 (t, J=7.6 Hz, 1H), 8.07 (s, 1H), 7.85 (d, J=7.6 Hz, 1H), 7.50 (s, 1H), 1.80 (s, 6H).

N-[2-(4-formylcyclohexyl)-6-(1-hydroxy-1-methyl-ethyl)indazol-5-yl]-6-(trifluoromethyl) pyridine-2-carboxamide (Intermediate AGL)

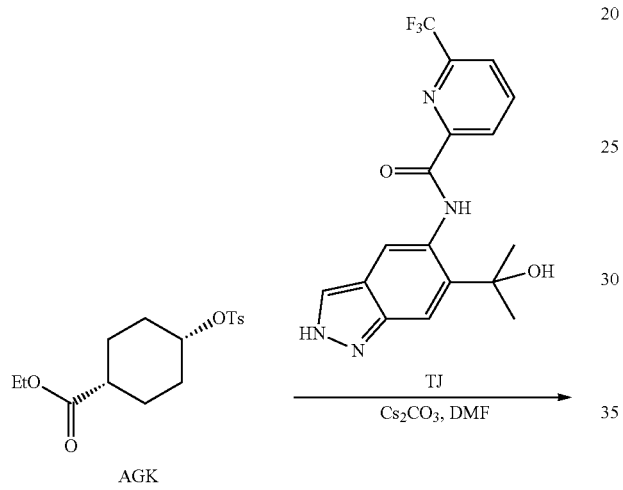

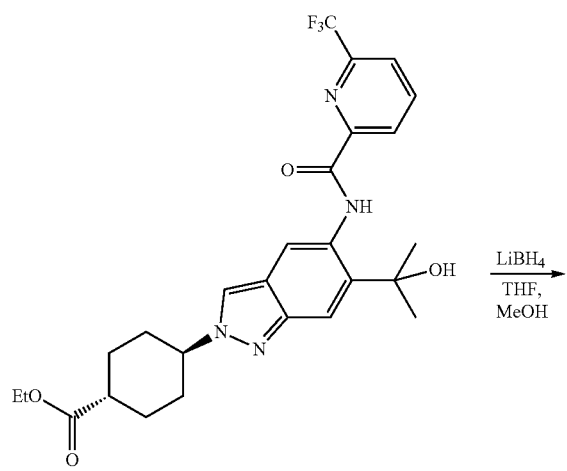

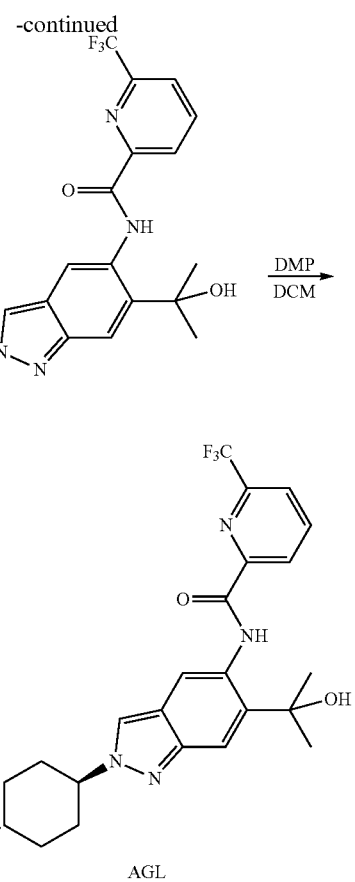

Step 1—Ethyl 4-[6-(1-hydroxy-1-methyl-ethyl)-5-[[6-(trifluoromethyl)pyridine-2-carbonyl]amino]indazol-2-yl]cyclohexanecarboxylate To a mixture of N-[6-(1-hydroxy-1-methyl-ethyl)-2H-indazol-5-yl]-6-(trifluoromethyl)pyridine-2-carboxamide (1.30 g, 3.57 mmol, Intermediate TJ), ethyl 4-(p-tolylsulfonyloxy)cyclohexane carboxylate (2.33 g, 7.14 mmol, Intermediate AGK) and Cs₂CO₃ (2.33 g, 7.14 mmol) in DMF (20 mL) was stirred at 80° C. for 16 hours. To the mixture was added ethyl 4-(p-tolylsulfonyloxy)cyclohexanecarboxylate (2.33 g, 7.14 mmol) and Cs₂CO₃ (2.33 g, 7.14 mmol) at 15° C. The mixture was stirred at 80° C. for 16 hours. On completion, after cooled to 15° C., the mixtures of two batches were combined, diluted with water (100 mL), and extracted with EA (3×60 mL). The organic layer was washed with brine (20 mL), dried over Na₂SO₄, filtered and concentrated in vacuo. The residue was purified by reverse phase flash and prep-HPLC (column: Phenomenex Synergi Max-RP 150*50 mm*10 um; mobile phase: [water (0.225% FA)-ACN]; B %: 52%-82%, 11 min) to give the title compound (530 mg, 14% yield) as white solid. ¹H NMR (400 MHz, CDCl₃) δ 12.28 (s, 1H), 8.87 (s, 1H), 8.50 (d, J=7.6 Hz, 1H), 8.10 (t, J=8.0 Hz, 1H), 7.92 (s, 1H), 7.84 (d, J=7.6 Hz, 1H), 7.74 (s, 1H), 4.43-4.35 (m, 1H), 4.17 (q, J=7.2 Hz, 2H), 2.48-2.40 (m, 1H), 2.36-2.34 (m, 2H), 2.28-2.19 (m, 3H), 2.10-1.97 (m, 2H), 1.81 (s, 6H), 1.76-1.64 (m, 2H), 1.29 (t, J=7.2 Hz, 3H).

Step 2—N-[2-[4-(hydroxymethyl)cyclohexyl]-6-(1-hydroxy-1-methyl-ethyl)indazol-5-yl]-6-(trifluoromethyl)pyridine-2-carboxamide To a solution of ethyl 4-[6-(1-hydroxy-1-methyl-ethyl)-5-[[6-(trifluoromethyl)pyridine-2-carbonyl]amino]indazol-2-yl]cyclohexanecarboxylate (200 mg, 385 umol) in THF (3 mL) and MeOH (0.4 mL) was added LiBH$_4$ (21.0 mg, 964 umol) at 0° C. The mixture was stirred at 50° C. for 1 hour. On completion, the reaction was quenched with sat. aq. NH$_4$Cl (5 mL). The mixture was diluted with water (40 mL), then extracted with EA (3×20 mL). The combined organic layer was washed with brine (10 mL), dried over Na$_2$SO$_4$, filtered and concentrated in vacuo to give the title compound (180 mg, 98% yield) as light yellow solid. $^1$H NMR (400 MHz, DMSO-d$_6$) δ 12.35 (s, 1H), 8.71 (s, 1H), 8.48-8.42 (m, 1H), 8.39-8.34 (m, 2H), 8.16 (d, J=7.6 Hz, 1H), 7.58 (s, 1H), 6.51 (s, 1H), 5.93 (s, 1H), 4.46-4.35 (m, 1H), 3.29 (s, 2H), 2.19-2.10 (m, 2H), 1.92-1.89 (m, 4H), 1.62 (s, 6H), 1.25-1.11 (m, 3H).

Step 3—N-[2-(4-formylcyclohexyl)-6-(1-hydroxy-1-methyl-ethyl)indazol-5-yl]-6-(trifluoromethyl) pyridine-2-carboxamide To a solution of N-[2-[4-(hydroxymethyl)cyclohexyl]-6-(1-hydroxy-1-methyl-ethyl)indazol-5-yl]-6-(trifluoromethyl)pyridine-2-carboxamide (50.0 mg, 104 umol) in DCM (5 mL) was added DMP (89.0 mg, 209 umol) at 0° C. The mixture was stirred at 0-10° C. for 6 hours. On completion, the reaction was quenched with sat. aq. Na$_2$S$_2$O$_3$ (5 mL), and extracted with DCM (2×10 mL). The combined organic layer was washed with sat. aq. NaHCO$_3$ (5 mL), dried over Na$_2$SO$_4$, filtered and concentrated in vacuo to give the title compound (49.0 mg, 98% yield) as light yellow solid. LC-MS (ESI$^+$) m/z 475.2 (M+H)$^+$.

3-(4-Methoxybenzyl)dihydropyrimidine-2,4(1H,3H)-dione (Intermediate BRW)

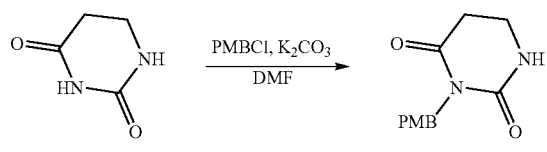

To a mixture of dihydropyrimidine-2,4(1H,3H)-dione (10.0 g, 87.6 mmol, CAS #504-07-4) in DMF (100 mL) was added PMB-Cl (13.7 g, 87.6 mmol, 11.9 mL), Cs$_2$CO$_3$ (28.5 g, 87.6 mmol) at 25° C. Then the mixture was stirred at 50° C. for 3 hours. On completion, the reaction mixture was quenched with of water (100 mL), and extracted with EtOAc (3×50 mL). The organic layer was dried over anhydrous Na$_2$SO$_4$, filtered and concentrated in vacuo. The crude product was purified by re-crystallization from EA/PE (20 mL, v/v=1/1) at 25° C. to give the title compound (9.40 g, 45% yield) as a white solid. $^1$H NMR (400 MHz, CDCl$_3$) δ 7.81 (s, 1H), 7.18 (d, J=8.4 Hz, 2H), 6.83 (d, J=8.4 Hz, 2H), 4.72 (s, 2H), 3.72 (s, 3H), 3.23-3.20 (m, 2H), 2.63 (t, J=6.8 Hz, 2H).

1-(7-Chloroisoquinolin-4-yl)dihydropyrimidine-2,4(1H,3H)-dione (Intermediate BRX)

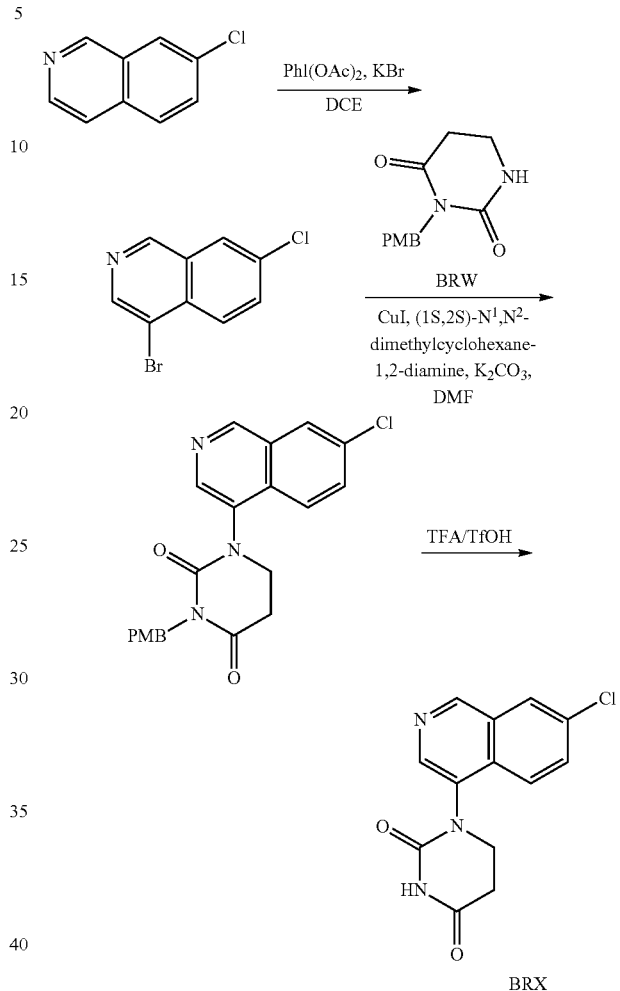

Step 1—4-Bromo-7-chloroisoquinoline

To a solution of 7-chloroisoquinoline (5.00 g, 30.5 mmol, CAS #34784-06-0) in DCE (50 mL) was added PhI(OAc)$_2$ (14.7 g, 45.8 mmol) and KBr (18.1 g, 152 mmol) and the mixture was stirred at 50° C. for 16 hours. On completion, the mixture was poured into water (100 mL), and extracted with EA (300 mL). The organic layer was washed with brine (2×100 mL), dried over anhydrous Na$_2$SO$_4$, filtered and concentrated in vacuo. The mixture was purified by silica gel column to give the title compound (5.50 g, 65% yield) as a white solid. $^1$H NMR (400 MHz, CDCl$_3$) δ 9.13 (s, 1H), 8.74 (s, 1H), 8.13 (d, J=9.2 Hz, 1H), 7.99 (d, J=2.0 Hz, 1H), 7.77 (dd, J=2.0, 9.2 Hz, 1H).

Step 2—1-(7-Chloro-4-isoquinolyl)-3-[(4-methoxyphenyl)methyl]hexahydropyrimidine-2,4-dione To a solution of 4-bromo-7-chloroisoquinoline (2.00 g, 8.25 mmol) and 3-(4-methoxybenzyl) dihydropyrimidine-2,4(1H,3H)-dione (1.93 g, 8.25 mmol, Intermediate BRW) in DMF (20 mL) was added (1S,2S)—N1,N2-dimethylcyclohexane-1,2-diamine (234 mg, 1.65 mmol), CuI (314 mg, 1.65 mmol) and K$_2$CO$_3$ (3.42 g, 24.7 mmol). Then the mixture was stirred at 100° C. for 16 hours under N$_2$. On completion, the reaction solution was diluted with water (100 mL) and then extracted with ethyl acetate (3×100 mL). The combined organic layers were washed with brine (2×100 mL), dried over anhydrous sodium sulfate, filtered and concentrated under vacuum. The mixture was purified by reversed phase flash: (C18, 10% to 40% MeCN in H2O, contained 0.1% FA in H2O 2O) to give the title compound (200 mg, 5% yield) as a light yellow solid. $^1$H NMR (400 MHz, DMSO-d$_6$) δ 9.31 (s, 1H), 8.60 (s, 1H), 8.39 (d, J=2.0 Hz, 1H), 8.00 (d, J=9.2 Hz, 1H), 7.83 (dd, J=2.0, 8.8 Hz, 1H), 7.25 (d, J=8.8 Hz, 2H), 6.90-6.86 (m, 2H), 4.83 (s, 2H), 4.00-3.94 (m, 1H), 3.79-3.76 (m, 1H), 3.73 (s, 3H), 3.19-3.11 (m, 1H), 2.99-2.92 (m, 1H).

Step 3—1-(7-Chloroisoquinolin-4-yl)dihydropyrimidine-2,4(1H,3H)-dione 1-(7-Chloroisoquinolin-4-yl)-3-(4-methoxybenzyl)dihydropyrimidine-2,4(1H,3H)-dione (50.0 mg, 126 umol) was added into TFA (0.5 mL) and TfOH (0.01 mL) and the mixture was stirred at 60° C. for 2 hours. On completion, the reaction solution was diluted with water (5 mL) and then extracted with ethyl acetate (3×5 mL). The combined organic layers were washed with brine (2×5 mL), dried over anhydrous sodium sulfate, filtered and concentrated in vacuo. The residue was further purified by prep-HPLC (Column: [Phenomenex luna C18, 150 mm*25 mm*10 um]; mobile phase: (water (0.225% FA)-MeCN, MeCN %: 8%-38%); 11 min) to give the title compound (5.18 mg, 14% yield) as a yellow solid. $^1$H NMR (400 MHz, DMSO-d$_6$) δ 10.56 (s, 1H), 9.31 (s, 1H), 8.59 (s, 1H), 8.38 (d, J=2.0 Hz, 1H), 8.06 (d, J=9.2 Hz, 1H), 7.84 (dd, J=2.4, 8.8 Hz, 1H), 4.00-3.93 (m, 1H), 3.75-3.69 (m, 1H), 3.02-2.94 (m, 1H), 2.78-2.71 (m, 1H). LC-MS (ESI$^+$) m/z 275.9 (M+H)$^+$.

1-(7-(Piperidin-4-yl)isoquinolin-4-yl)dihydropyrimidine-2,4(1H,3H)-dione (Intermediate BRY)

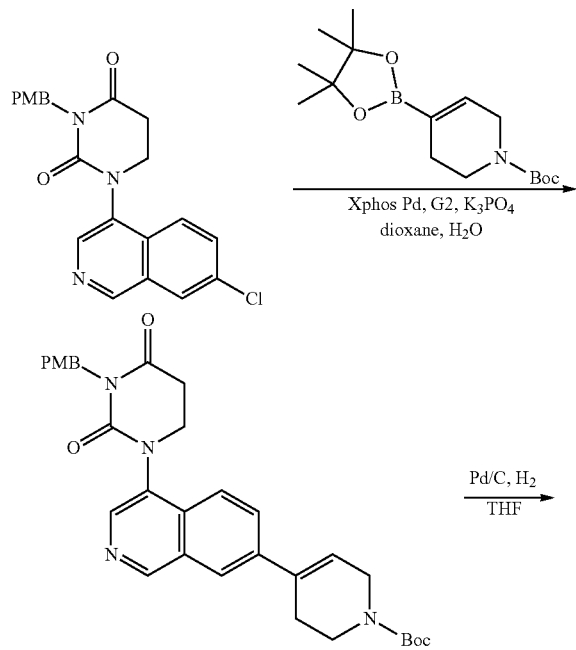

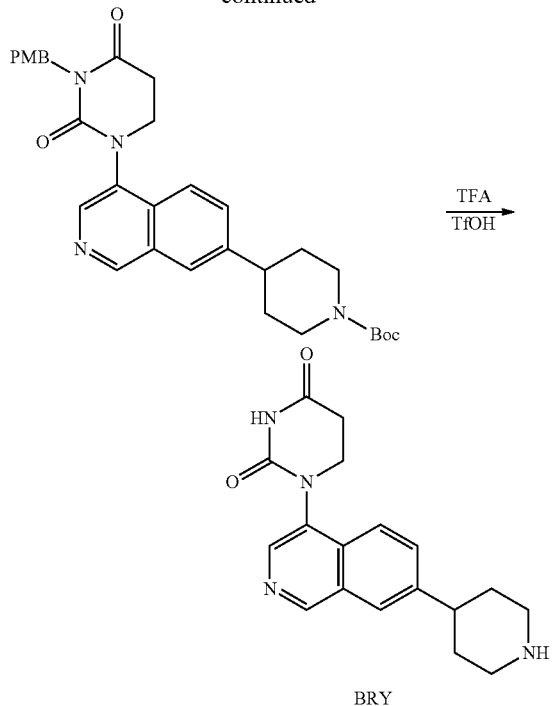

Step 1—Tert-butyl 4-(4-(3-(4-methoxybenzyl)-2,4-dioxotetrahydropyrimidin-1(2H)-yl)isoquinolin-7-yl)-5,6-dihydropyridine-1(2H)-carboxylate To a solution of 1-(7-chloroisoquinolin-4-yl)-3-(4-methoxybenzyl)dihydropyrimidine-2,4(1H,3H)-dione (150 mg, 378 umol, synthesized via Steps 1-2 of Intermediate BRX) and tert-butyl 4-(4,4,5,5-tetramethyl -1,3,2-dioxaborolan-2-yl)-5,6-dihydropyridine-1(2H)-carboxylate (140 mg, 454 umol, CAS #286961-14-6) in dioxane (2.0 mL) and water (0.2 mL) was added Xphos Pd G2 (29.8 mg, 37.8 umol) and K$_3$PO$_4$ (160 mg, 757 umol). Then the mixture was stirred at 80° C. for 6 hours. On completion, the reaction solution was diluted with water (20 mL) and then extracted with ethyl acetate (3×10 mL). The combined organic layers were washed with brine (2×10 mL), dried over anhydrous sodium sulfate, filtered and concentrated under vacuum. The residue was purified by prep-TLC to afford the title compound (170 mg, 67% yield) as a brown oil. LC-MS (ESI$^+$) m/z 543.4 (M+H)$^+$.

Step 2—Tert-butyl 4-(4-(3-(4-methoxybenzyl)-2,4-dioxotetrahydropyrimidin-1(2H)-yl)isoquinolin-7-yl)piperidine-1-carboxylate To a solution of tert-butyl 4-(4-(3-(4-methoxybenzyl)-2,4-dioxotetrahydropyrimidin-1(2H)-yl) isoquinolin-7-yl)-5,6-dihydropyridine-1(2H)-carboxylate (160 mg, 294 umol) in THF (20 mL) was added Pd/C (30 mg, 294 umol, 10 wt %) under N$_2$. The mixture was stirred at 20° C. for 1 hour under H2 balloon (15 psi). On completion, the mixture was filtered through celite, then washed with THF (50 mL). The filtrate was concentrated in vacuo to afford the title compound (130 mg, 72% yield) as brown oil. $^1$H NMR (400 MHz, DMSO-d$_6$) δ 9.26 (s, 1H), 8.49 (s, 1H), 8.06 (s, 1H), 7.85 (d, J=8.4 Hz, 1H), 7.75 (dd, J=1.6, 8.8 Hz, 1H), 7.25 (d, J=8.8 Hz, 2H), 6.90-6.86 (m, 2H), 4.83 (s, 2H), 4.13 (d, J=11.0 Hz, 2H), 3.94-3.91 (m, 1H), 3.73 (s, 3H), 3.66-3.54 (m, 4H), 3.15-3.08 (m, 1H), 3.02-2.97 (m, 1H), 1.88-1.85 (m, 2H), 1.68-1.57 (m, 2H), 1.35 (s, 9H); LC-MS (ESI$^+$) m/z 545.2 (M+H)$^+$.

Step 3—1-(7-(Piperidin-4-yl)isoquinolin-4-yl)dihydropyrimidine-2,4(1H,3H)-dione

A solution of tert-butyl 4-(4-(3-(4-methoxybenzyl)-2,4-dioxotetrahydropyrimidin-1(2H)-yl) isoquinolin-7-yl)piperidine-1-carboxylate (40.0 mg, 73.4 umol) in TFA (1.0 mL) and TfOH (0.05 mL) was stirred at 70° C. for 3 hours. On completion, the residue was concentrated in vacuo. The residue was purified by prep-HPLC (column: Phenomenex luna C18, 150 mm*25 mm*10 um; mobile phase: [water (0.225% FA)-MeCN]; B %: 1%-15%, 11.5 min), and then further purified by Prep-HPLC (column: Waters xbridge, 150 mm*25 mm*10 um; mobile phase: [water (10 mM NH$_4$HCO$_3$)-MeCN]; B %: 0%-26%, 11 min) to give the title compound (1.03 mg, 4% yield) as a white solid. $^1$H NMR (DMSO-d$_6$, 400 Hz) δ 10.53 (s, 1H), 9.26 (s, 1H), 8.48 (s, 1H), 8.01 (s, 1H), 7.92 (d, J=8.8 Hz, 1H), 7.77-7.74 (m, 1H), 3.96-3.89 (m, 1H), 3.75-3.69 (m, 1H), 3.09 (d, J=12.0 Hz, 2H), 3.00-2.72 (m, 4H), 2.65-2.62 (m, 2H), 1.80 (d, J=12 Hz, 2H), 1.68-1.58 (m, 2H); LC-MS (ESI$^+$) m/z 325.0 (M+H)$^+$.

1-(7-(4-(Methylamino)piperidin-1-yl)isoquinolin-4-yl)dihydropyrimidine-2,4(1H,3H)-dione (Intermediate BRZ)

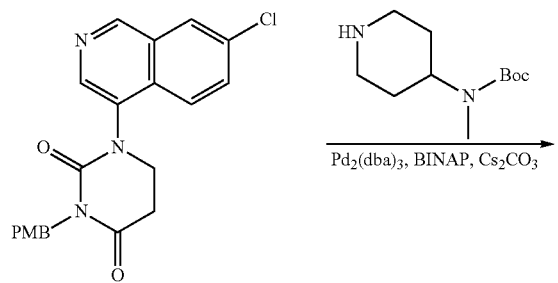

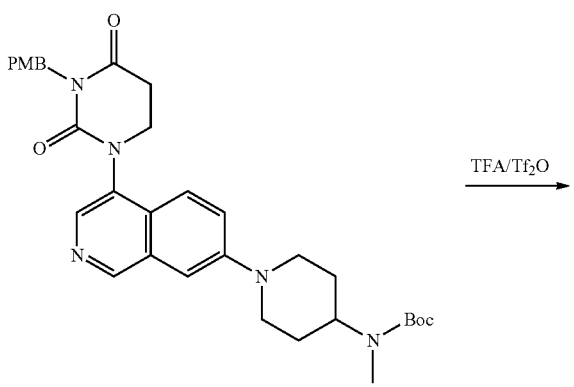

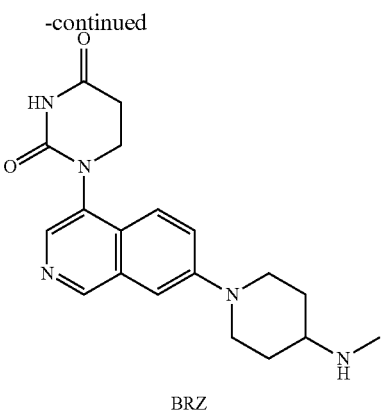

Step 1—Tert-butyl (1-(4-(3-(4-methoxybenzyl)-2,4-dioxotetrahydropyrimidin-1(2H)-yl)isoquinolin-7-yl)piperidin-4-yl)(methyl)carbamate To a solution of 1-(7-chloroisoquinolin-4-yl)-3-(4-methoxybenzyl)dihydropyrimidine-2,4(1H,3H)-dione (200 mg, 505 umol, synthesized via Steps 1-2 of Intermediate BRX) and tert-butyl methyl (piperidin-4-yl)carbamate (108 mg, 505 umol, CAS #108612-54-0) in dioxane (2 mL) was added Pd$_2$(dba)$_3$ (92.5 mg, 101 umol), BINAP (125 mg, 202 umol) and Cs$_2$CO$_3$ (329 mg, 1.01 mmol). Then the mixture was stirred at 100° C. for 12 hours under N$_2$. On completion, the mixture was poured into water (20 mL), then the mixture was extracted with EA (30 mL). The organic layer was washed with brine (2×10 mL), dried over anhydrous Na$_2$SO$_4$, filtered and concentrated in vacuo. The residue was purified by prep-HPLC (column: Phenomenex luna C18, 150 mm*25 mm*10 um; mobile phase: [water (0.225% FA)-MeCN]; B %: 33%-63%, 11.5 min) to give the title compound (50.0 mg, 15% yield) as a light yellow solid. $^1$H NMR (400 MHz, DMSO-d$_6$) δ 9.07 (s, 1H), 8.27 (s, 1H), 7.75-7.69 (m, 1H), 7.66-7.61 (m, 1H), 7.45 (d, J=2.0 Hz, 1H), 7.25 (d, J=8.8 Hz, 2H), 6.91-6.84 (m, 2H), 4.83 (s, 2H), 4.01 (d, J=12.8 Hz, 2H), 3.92-3.86 (m, 1H), 3.73 (s, 3H), 3.15-3.06 (m, 2H), 2.99-2.82 (m, 4H), 2.68 (s, 3H), 1.86-1.74 (m, 2H), 1.71-1.61 (m, 2H), 1.41 (s, 9H).

Step 2—1-(7-(4-(Methylamino)piperidin-1-yl)isoquinolin-4-yl)dihydropyrimidine-2,4(1H,3H)-dione To a solution of tert-butyl (1-(4-(3-(4-methoxybenzyl)-2,4-dioxotetrahydropyrimidin-1(2H)-yl)isoquinolin-7-yl)piperidin-4-yl)(methyl)carbamate (20.0 mg, 122 umol) was added into TFA (0.5 mL) and TfOH (0.01 mL). The solution was stirred at 60° C. for 2 hours. On completion, the mixture was concentrated in vacuo. The residue was adjusted with triethylamine to pH=7. The mixture was purified by reversed phase flash (column: Phenomenex luna C18, 150 mm*25 mm*10 um; mobile phase: [water (0.225% FA)-MeCN]; B %: 1%-20%, 11.5 min) and further purified by Prep-HPLC (column: Waters xbridge, 150 mm*25 mm*10 um; mobile phase: [water (10 mM NH$_4$HCO$_3$)-MeCN]; B %: 0%-15%, 11 min) to give the title compound (1.17 mg, 94% yield) as a white solid. $^1$H NMR (400 MHz, DMSO-d$_6$) δ ppm 10.49 (s, 1H), 9.05 (s, 1H), 8.25 (s, 1H), 7.81-7.74 (m, 1H), 7.65-7.63 (m, 1H), 7.41 (d, J=2.4 Hz, 1H), 3.93-3.79 (m, 3H), 3.71-3.69 (m, 1H), 2.95-2.89 (m, 4H), 2.88-2.71 (m, 2H), 2.32 (s, 3H), 1.94-1.91 (m, 2H), 1.41-1.36 (m, 2H). LC-MS (ESI⁺) m/z 354.2 (M+H)⁺.

1-[8-[4-(Methylamino)-1-piperidyl]-4-isoquinolyl] hexahydropyrimidine -2,4-dione (Intermediate BSA)

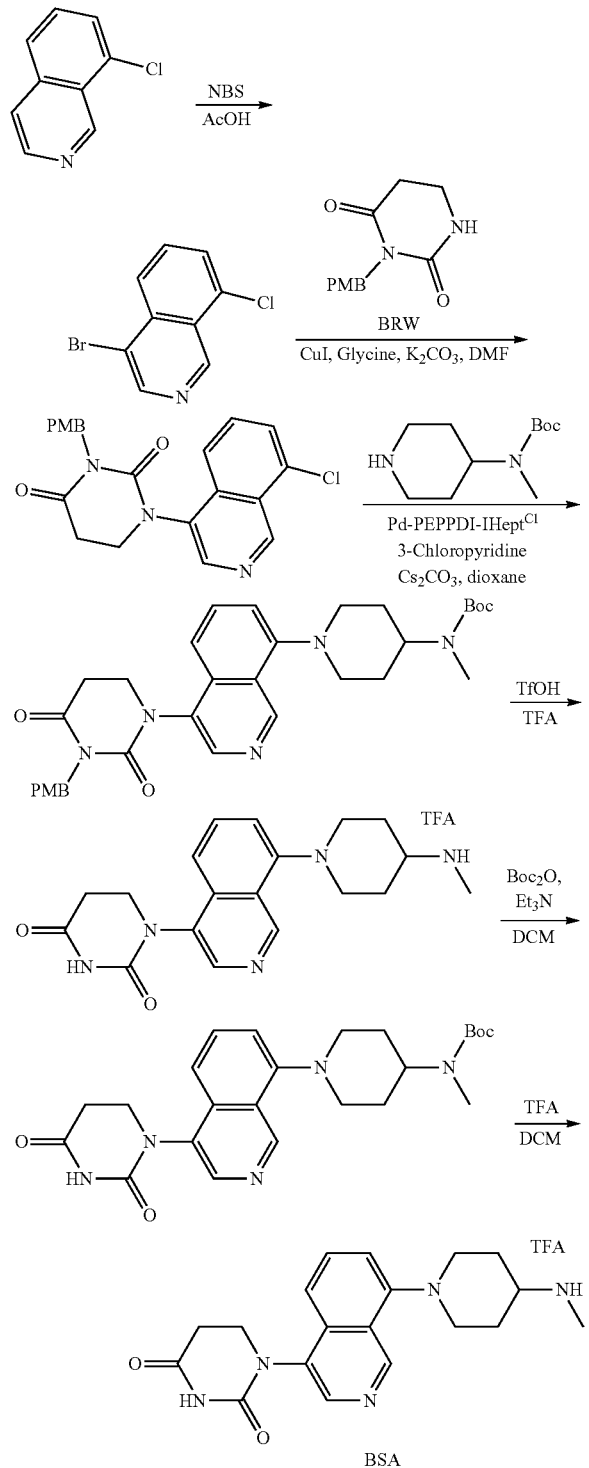

Step 1—4-Bromo-8-chloro-isoquinoline

A mixture of 8-chloroisoquinoline (5.00 g, 30.5 mmol, CAS #34784-07-1), NBS (7.07 g, 39.7 mmol) in HOAc (50 mL) was degassed and purged with N₂ three times, and then the mixture was stirred at 50° C. for 40 minutes under N₂ atmosphere. On completion, the reaction mixture was neutralized with 15% NaOH (20 mL) and the mixture was extracted with EA (3×20 mL). The combined organic layers were washed with water (50 mL), dried over anhydrous Na₂SO₄, filtered and concentrated in vacuo to give a residue. Then the residue was purified by column chromatography to give the title compound (400 mg, 73.90% yield) as yellow solid. ¹H NMR (400 MHz, CDCl₃-d) δ 9.58 (s, 1H), 8.79 (s, 1H), 8.12-8.05 (m, 1H), 7.73-7.66 (m, 2H).

Step 2—1-(8-Chloro-4-isoquinolyl)-3-[(4-methoxyphenyl)methyl]hexahydropyrimidine-2,4-dione To a solution of 4-bromo-8-chloro-isoquinoline (200 mg, 824 umol) and 3-[(4-methoxyphenyl)methyl]hexahydropyrimidine-2,4-dione (231 mg, 989 umol, Intermediate BRW) in DMF (3 mL) was added CuI (47.1 mg, 247 umol), K₂CO₃ (227 mg, 1.65 mmol) and 2-aminoacetic acid (18.5 mg, 247 umol). Then the mixture was purged with N₂ three times and stirred at 140° C. for 8 hours. On completion, the mixture was filtrated, diluted with water (100 mL) and extracted with EA (5×80 mL). The combined organic phase was dried with anhydrous Na₂SO₄, filtered and concentrated in vacuo to give the residue. Then the residue was purified by reversed-phase HPLC (0.1% FA) to give the title compound (99.2 mg, 30.41% yield) as yellow solid. ¹H NMR (400 MHz, DMSO-d₆) δ 9.56 (s, 1H), 8.72 (s, 1H), 7.98 (d, J=8.4 Hz, 1H), 7.91-7.87 (m, 1H), 7.83-7.77 (m, 1H), 7.29-7.23 (m, 2H), 6.91-6.84 (m, 2H), 4.84 (s, 2H), 4.01-3.94 (m, 1H), 3.80-3.75 (m, 1H), 3.73-3.71 (m, 3H), 3.20-3.12 (m, 1H), 3.01-2.93 (m, 1H). LC-MS (ESI⁺) m/z 396.0 (M+H)⁺.

Step 3—Tert-butyl N-[1-[4-[3-[(4-methoxyphenyl)methyl]oxo-hexahydropyrimidin-1-yl]-8-isoquinolyl]-4-pyridyl]-N-methyl-carbamate To a solution of 1-(8-chloro-4-isoquinolyl)-3-[(4-methoxyphenyl)methyl]hexahydropyrimidine-2,4-dione (200 mg, 505 umol) and tert-butyl N-methyl-N-(4-piperidyl) carbamate (119 mg, 555 umol, CAS #108612-54-0) in dioxane (4 mL) was added Cs₂CO₃ (329 mg, 1.01 mmol) and Pd-PEPPSI-IHept$^{Cl}$3-Chloropyridine (49.1 mg, 50.5 umol), then the mixture was stirred at 80° C. for 8 hours. On completion, the mixture was filtered, diluted with water (20 mL) and extracted with EA (4×10 mL). The extract was dried over anhydrous Na₂SO₄, filtered and concentrated in vacuo to give the title compound (216 mg, 74.52% yield) as yellow solid. ¹H NMR (400 MHz, DMSO-d₆) δ 9.45 (s, 1H), 8.53 (s, 1H), 7.72-7.66 (m, 1H), 7.54 (d, J=8.4 Hz, 1H), 7.31-7.24 (m, 3H), 6.88 (d, J=8.8 Hz, 2H), 4.83 (s, 2H), 3.93-3.87 (m, 1H), 3.78-3.71 (m, 4H), 3.50-3.42 (m, 2H), 3.17-3.08 (m, 1H), 2.99-2.96 (m, 1H), 2.81 (s, 3H), 2.18-2.03 (m, 2H), 1.75-1.68 (m, 2H), 1.43 (s, 9H), 0.88-0.70 (m, 3H); LC-MS (ESI⁺) m/z 574.3 (M+H)⁺.

Step 4—1-[8-[4-(Methylamino)-1-piperidyl]-4-isoquinolyl]hexahydropyrimidine-2,4-dione To a solution of tert-butyl N-[1-[4-[3-[(4-methoxyphenyl)methyl]-2,4-dioxo-hexahydropyrimidin-1-yl]-8-isoquinolyl]-4-piperidyl]-N-methyl-carbamate (206 mg, 359 umol) in TFA (0.5 mL) and TfOH (0.05 mL) was stirred at 70° C. for 1 hour. On completion, the mixture was concentrated in vacuo to give the title compound (100 mg, 78.80% yield, TFA) as yellow solid. LC-MS (ESI$^+$) m/z 354.0 (M+H)$^+$.

Step 5—Tert-butyl N-[1-[4-(2,4-dioxohexahydropyrimidin-1-yl)-8-isoquinolyl]-4-piperidyl]-N-methyl-carbamate To a solution of 1-[8-[4-(methylamino)-1-piperidyl]-4-isoquinolyl]hexahydropyrimidine-2,4-dione (100 mg, 282 umol) in DCM (1 mL) was added Et$_3$N (787 uL, 5.66 mmol) and Boc$_2$O (92.6 mg, 424 umol) at 0° C., then the mixture was stirred at 25° C. for 13 hours. On completion, the mixture was concentrated in vacuo to give the residue, then the residue was purified by reverse-phase (0.1% FA condition) to give the title compound (70.0 mg, 54.55% yield) as yellow solid. $^1$H NMR (400 MHz, DMSO-d$_6$) δ 10.53 (s, 1H), 9.45 (s, 1H), 8.53 (s, 1H), 7.75-7.68 (m, 1H), 7.61 (d, J=8.4 Hz, 1H), 7.28 (d, J=7.2 Hz, 1H), 4.15-3.96 (m, 1H), 3.92-3.86 (m, 1H), 3.72-3.66 (m, 1H), 3.48-3.41 (m, 2H), 3.01-2.84 (m, 3H), 2.81 (s, 3H), 2.78-2.71 (m, 1H), 2.19-2.02 (m, 2H), 1.72-1.70 (m, 2H), 1.43 (s, 9H). LC-MS (ESI$^+$) m/z 454.1 (M+H)$^+$.

Step 6—1-[8-[4-(Methylamino)-1-piperidyl]-4-isoquinolyl]hexahydropyrimidine-2,4-dione To a solution of tert-butyl N-[1-[4-(2,4-dioxohexahydropyrimidin-1-yl)-8-isoquinolyl]-4-piperidyl]-N-methyl-carbamate (60 mg, 132 umol) in DCM (1 mL) was added TFA (0.5 mL, 6.75 mmol), then the mixture was stirred at 25° C. for 1 hour. On completion, the mixture was concentrated in vacuo to give the title compound (58.0 mg, 93.79% yield, TFA) as yellow solid. LC-MS (ESI$^+$) m/z 354.0 (M+H)$^+$.

N-[6-cyclopropyl-2-(4-formylcyclohexyl)indazol-5-yl]-6-(trifluoromethyl)pyridine-2-carboxamide (Intermediate BSB)

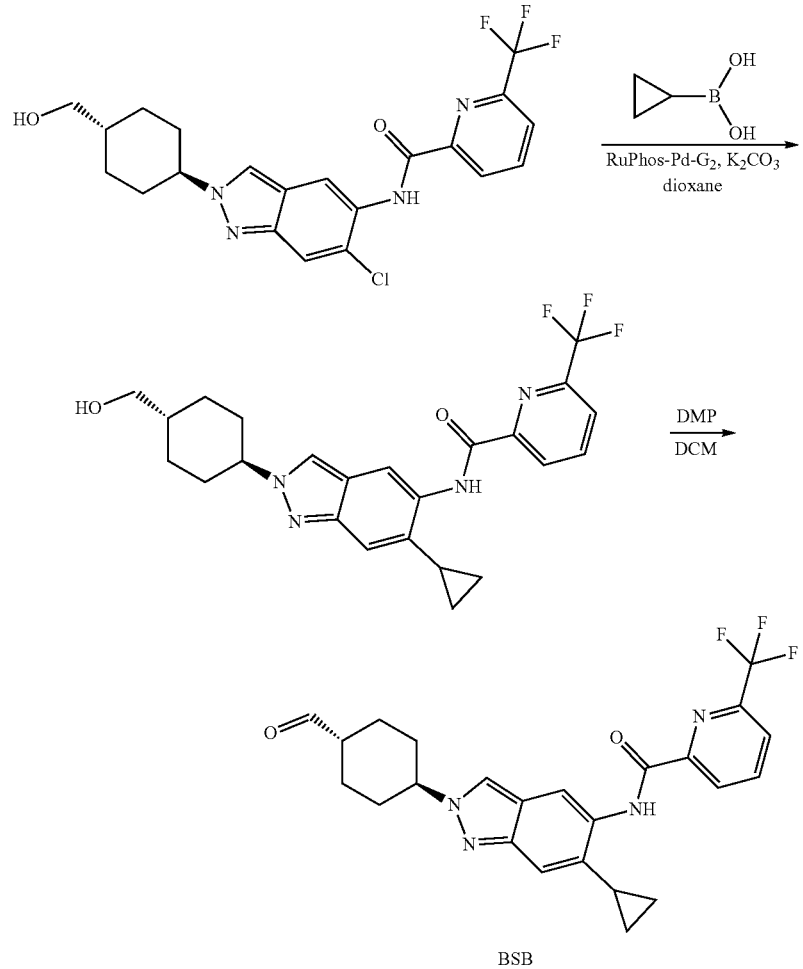

Step 1—N-[6-cyclopropyl-2-[4-(hydroxymethyl)cyclohexyl]indazol-5-yl]-6-(trifluoromethyl)pyridine-2-carboxamide To a solution of N-[6-chloro-2-[4-(hydroxymethyl)cyclohexyl]indazol-5-yl]-6-(trifluoromethyl) pyridine-2-carboxamide (100 mg, 220 umol, synthesized via Steps 1-3 of Intermediate BPQ) in dioxane (2.5 mL) was added cyclopropylboronic acid (37.9 mg, 441 umol, CAS #411235-57-9), K$_2$CO$_3$ (91.5 mg, 662 umol) and XPHOS-PD-G$_2$ (17.3 mg, 22.1 umol). The reaction mixture was stirred at 90° C.

for 12 hrs under N$_2$ atmosphere. On completion, the reaction mixture was filtered and concentrated in vacuo to give a residue. The residue was purified by prep-HPLC (column: Phenomenex Luna C18 150*25 mm*10 um; mobile phase: [water (0.225% FA)-ACN]; B %: 46%-76%, 10 min) to give the title compound (40 mg, 39% yield) as a white solid. $^1$H NMR (400 MHz, DMSO-d$_6$) δ 10.74 (s, 1H), 8.63 (s, 1H), 8.52-8.45 (m, 1H), 8.45-8.34 (m, 2H), 8.22 (d, J=7.6 Hz, 1H), 7.50-7.45 (m, 1H), 4.48 (t, J=5.2 Hz, 1H), 4.45-4.33 (m, 1H), 3.30-3.25 (m, 2H), 2.20-2.08 (m, 2H), 2.08-1.98 (m, 1H), 1.96-1.80 (m, 4H), 1.53-1.42 (m, 1H), 1.16-1.06 (m, 3H), 0.88 (q, J=7.2 Hz, 1H), 0.82-0.72 (m, 2H); LC-MS (ESI$^+$) m/z 459.0 (M+H)$^+$.

Step 2—N-[6-cyclopropyl-2-(4-formylcyclohexyl)indazol-5-yl]-6-(trifluoromethyl)pyridine-2-carboxamide To a solution of N-[6-cyclopropyl-2-[4-(hydroxymethyl)cyclohexyl]indazol-5-yl]-6-(trifluoromethyl) pyridine-2-carboxamide (40 mg, 87.2 umol) in DCM (0.5 mL) was added DMP (48.1 mg, 113 umol). The reaction mixture was stirred at 25° C. for 2 hrs. On completion, the reaction mixture was quenched by saturated Na$_2$S$_2$O$_3$ (2 mL) and saturated NaHCO$_3$(2 mL) at 25° C., and then the mixture was stirred for 15 minutes. The mixture was extracted with DCM (2×5 mL), then the combined organic layers was washed with saturated NaCl (2×10 mL). Then the combined organic layers was dried over Na$_2$SO$_4$, filtered and concentrated in vacuo to give title compound (30 mg, 75% yield) as yellow oil. $^1$H NMR (400 MHz, DMSO-d$_6$) δ 10.83-10.66 (m, 1H), 9.64 (s, 1H), 8.64 (s, 1H), 8.52-8.45 (m, 1H), 8.44-8.34 (m, 2H), 8.22 (d, J=7.6 Hz, 1H), 7.52-7.45 (m, 1H), 4.55-4.34 (m, 1H), 3.31-3.22 (m, 1H), 2.23-2.08 (m, 3H), 2.05-1.90 (m, 3H), 1.44 (dd, J=3.2, 12.4 Hz, 1H), 1.23 (s, 1H), 1.15-1.07 (m, 2H), 0.87 (q, J=7.2 Hz, 1H), 0.81-0.72 (m, 2H); LC-MS (ESI$^+$) m/z 457.3 (M+H)$^+$.

N-[2-(4-formylcyclohexyl)-6-methyl-indazol-5-yl]-6-(trifluoromethyl)pyridine-2-carboxamide (Intermediate BSC)

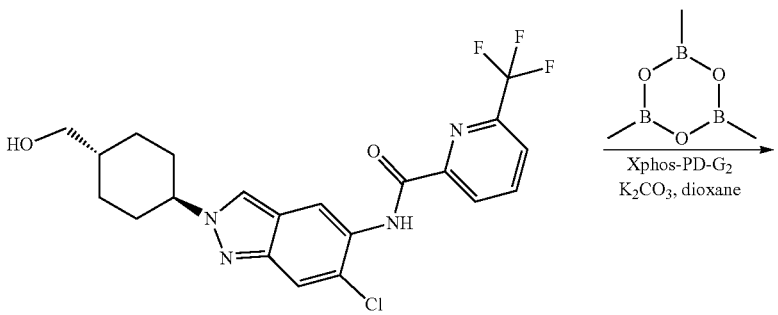

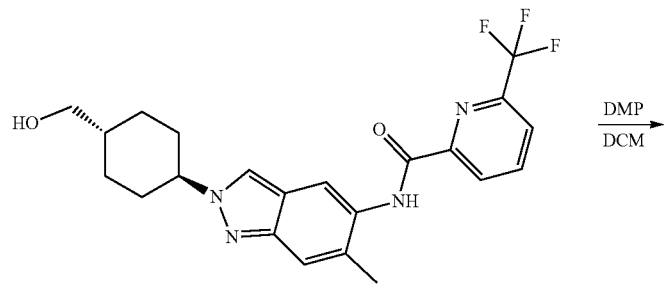

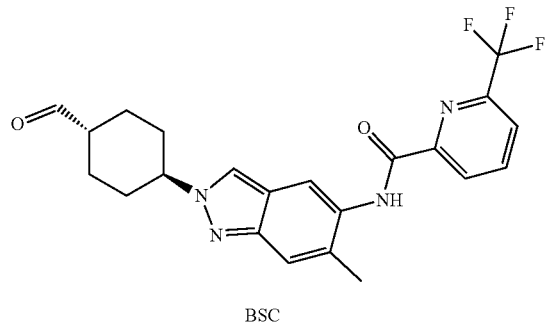

BSC

Step 1—N-[2-[4-(hydroxymethyl)cyclohexyl]-6-methyl-indazol-5-yl]-6-(trifluoromethyl)pyridine-2-carboxamide To a solution of N-[6-chloro-2-[4-(hydroxymethyl)cyclohexyl]indazol-5-yl]-6-(trifluoromethyl) pyridine-2-carboxamide (50.0 mg, 110 umol, via Steps 1-3 of Intermediate BPQ) in dioxane (1 mL) was added 2,4,6-trimethyl-1,3,5,2,4,6-trioxatriborinane (27.7 mg, 220 umol, CAS #823-96-1), $K_2CO_3$ (45.7 mg, 331 umol) and XPHOS-PD-G2 (8.69 mg, 11.0 umol). The reaction mixture was stirred at 90° C. for 16 hrs under $N_2$ atmosphere. On completion, the reaction mixture was diluted with water (5 mL) and extracted with DCM (2×10 mL). The combined organic layer was dried over $Na_2SO_4$, filtered and concentrated in vacuo to the title compound (38.0 mg, 79% yield) as a white solid. $^1H$ NMR (400 MHz, DMSO-$d_6$) δ 10.12 (s, 1H), 8.46-8.34 (m, 3H), 8.23-8.17 (m, 2H), 7.53-7.46 (m, 1H), 4.53-4.34 (m, 2H), 3.29 (s, 2H), 2.40 (s, 3H), 2.17-2.12 (m, 2H), 1.94-1.86 (m, 4H), 1.52-1.45 (m, 1H), 1.17-1.13 (m, 2H); LC-MS (ESI$^+$) m/z 433.3 (M+H)$^+$.

Step 2—N-[2-(4-formylcyclohexyl)-6-methyl-indazol-5-yl]-6-(trifluoromethyl)pyridine-2-carboxamide To a solution of N-[2-[4-(hydroxymethyl)cyclohexyl]-6-methyl-indazol-5-yl]-6-(trifluoromethyl) pyridine-2-carboxamide (38.0 mg, 87.8 umol) in DCM (0.5 mL) was added DMP (48.4 mg, 114 umol) and the mixture was stirred at 25° C. for 2 hrs. On completion, the reaction mixture was quenched with saturated $Na_2S_2O_3$ (2 mL) and saturated $NaHCO_3$ (2 mL) at 25° C., and then stirred for 15 minutes. The mixture was extracted with DCM (2×5 mL), then the combined organic layers was washed with saturated NaCl (2×10 mL). Then the combined organic layers was dried over $Na_2SO_4$, filtered and concentrated in vacuo to give the title compound (30.0 mg, 79% yield) as a yellow solid. $^1H$ NMR (400 MHz, DMSO-$d_6$) δ 10.13 (s, 1H), 9.65 (s, 1H), 8.49-8.32 (m, 3H), 8.27-8.14 (m, 2H), 7.51 (s, 1H), 4.55-4.33 (m, 1H), 2.40 (s, 3H), 2.21 (dd, J=2.4, 12.0 Hz, 2H), 2.14-2.08 (m, 2H), 1.98 (dd, J=3.2, 12.4 Hz, 2H), 1.45 (dd, J=3.2, 12.8 Hz, 2H), 1.25 (s, 1H); LC-MS (ESI$^+$) m/z 431.2 (M+H)$^+$.

1-(8-Chloro-4-isoquinolyl)hexahydropyrimidine-2,4-dione (Intermediate BSL)

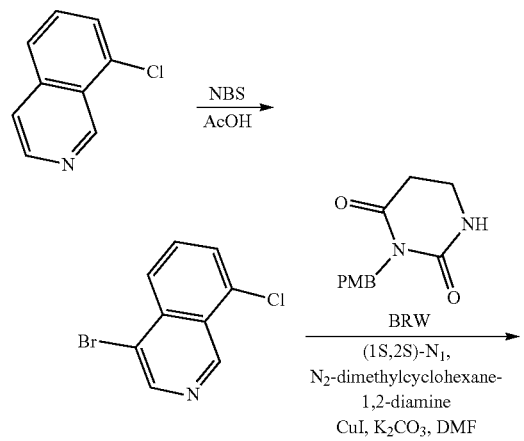

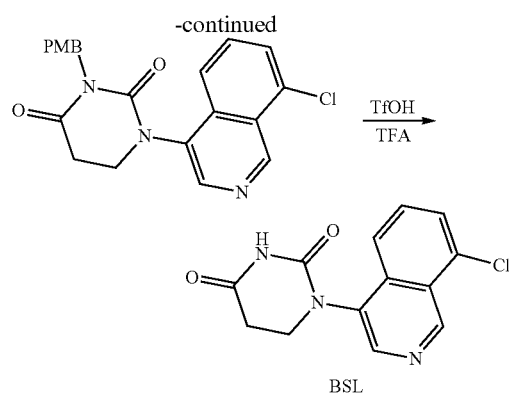

Step 1—4-Bromo-8-chloro-isoquinoline

To a solution of 8-chloroisoquinoline (5.00 g, 30.5 mmol, CAS #34784-07-1) in AcOH (50 mL) was added NBS (7.07 g, 39.7 mmol), then the reaction mixture was stirred at 50° C. for 40 min. On completion, the reaction mixture was diluted with water (100 mL), then extracted with EA (3×80 mL). The combined organic layer was basified with $NaHCO_3$ until the pH=6-7, then the mixture was extracted with EA (2×60 mL). The combined organic layers was dried over $Na_2SO_4$, filtered and concentrated in vacuo to give a residue. The residue was purified by column chromatography (SiO$_2$, PE:EA=100:1 to PE:EA=50:1, PE:EA=10:1, P1: R$_f$=0.74) to give the title compound (1.00 g, 37% yield) as yellow solid. $^1H$ NMR (400 MHz, CDCl$_3$) δ 9.56 (s, 1H), 8.78 (s, 1H), 8.10-8.03 (m, 1H), 7.73-7.64 (m, 2H). LC-MS (ESI$^+$) m/z 241.9 (M+H)$^+$.

Step 2—1-(8-Chloro-4-isoquinolyl)-3-[(4-methoxyphenyl)methyl]hexahydropyrimidine-2,4-dione To a solution of 4-bromo-8-chloro-isoquinoline (100 mg, 412 umol) and 3-[(4-methoxyphenyl)methyl]hexahydropyrimidine-2,4-dione (96.6 mg, 412.37 umol, Intermediate BRW) in DMF (1 mL) was added CuI (7.85 mg, 41.2 umol), (1S,2S)—N$_1$,N$_2$-dimethylcyclohexane-1,2-diamine (5.87 mg, 41.2 umol) and $K_3PO_4$ (175 mg, 824 umol), then the mixture was stirred at 110° C. for 8 hr. On completion, the reaction mixture was filtered and concentrated in vacuo to give the residue. The residue was diluted with water (50 mL) and extracted with EA (5×30 mL). Then the combined organic layers was dried over anhydrous $Na_2SO_4$, filtered and concentrated in vacuo to give a residue. The residue was purified by reverse-phase (0.1% FA) to give the title compound (15 mg, 3.06% yield) as yellow solid. $^1H$ NMR (400 MHz, DMSO-$d_6$) δ 9.89-9.56 (br s, 1H), 8.59 (br s, 1H), 7.73-7.68 (m, 1H), 7.64 (t, J=8.0 Hz, 1H), 7.60-7.55 (m, 1H), 7.43 (d, J=8.4 Hz, 2H), 6.85 (d, J=8.4 Hz, 2H), 5.00 (s, 2H), 3.95-3.86 (m, 1H), 3.80 (s, 3H), 3.78-3.69 (m, 1H), 3.07-2.99 (m, 2H); LC-MS (ESI$^+$) m/z 396.1 (M+H)$^+$.

Step 3—1-(8-Chloro-4-isoquinolyl)hexahydropyrimidine-2,4-dione

To a solution of 1-(8-chloro-4-isoquinolyl)-3-[(4-methoxyphenyl)methyl]hexahydropyrimidine-2,4-dione (40.0 mg, 101 umol) in TFA (0.49 mL) and TfOH (0.01 mL), then the mixture was stirred at 60° C. for 2 hours. On completion, the mixture was concentrated to give the residue and purified by prep-HPLC (0.1% FA) to give the title compound (3 mg, 10.77% yield) as yellow solid. ¹H NMR (400 MHz, DMSO-d₆) δ=10.59 (s, 1H), 9.56 (s, 1H), 8.71 (s, 1H), 8.03 (d, J=8.4 Hz, 1H), 7.92-7.87 (m, 1H), 7.85-7.78 (m, 1H), 4.00-3.93 (m, 1H), 3.75-3.69 (m 1H), 3.03-2.95 (m, 1H), 2.79-2.72 (m, 1H). LC-MS (ESI⁺) m/z 276.0 (M+H)⁺.

1-[8-(4-Piperidyl)-4-isoquinolyl]hexahydropyrimidine-2,4-dione (Intermediate BSN)

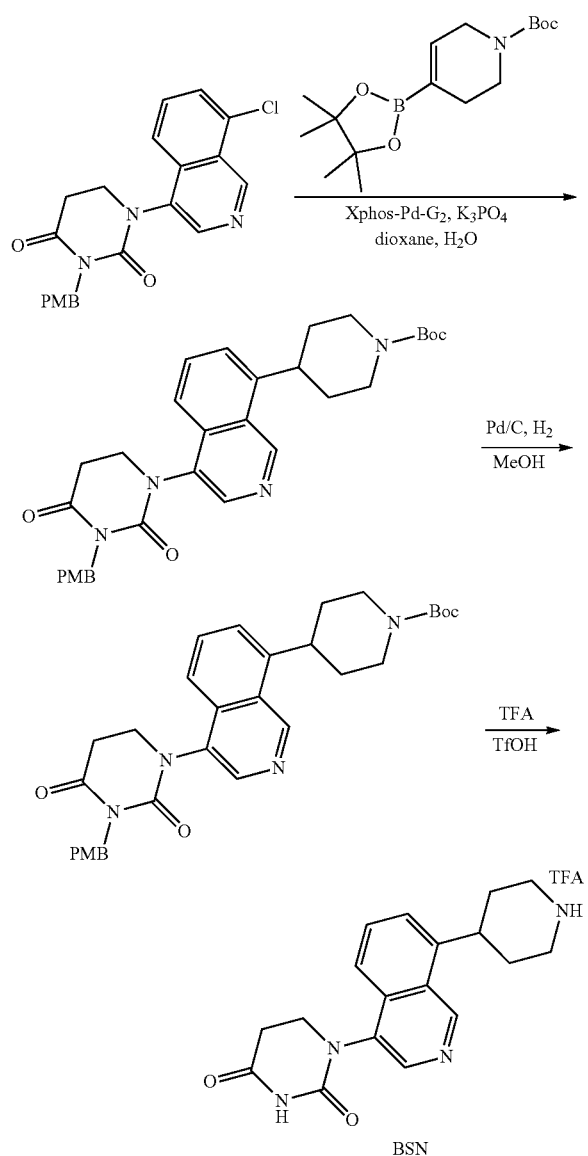

Step 1—Tert-butyl 4-[4-[3-[(4-methoxyphenyl)methyl]-2,4-dioxo-hexahydropyrimidin-1-yl]-8-isoquinolyl]-3,6-dihydro-2H-pyridine-1-carboxylate To a mixture of 1-(8-chloro-4-isoquinolyl)-3-[(4-methoxyphenyl)methyl]hexahydropyrimidine-2,4-dione (220 mg, 555 umol, synthesized via Steps 1-2 of Intermediate BSL), tert-butyl 4-(4,4,5,5-tetramethyl-1,3,2-dioxaborolan-2-yl)-3,6-dihydro-2H-pyridine-1-carboxylate (223 mg, 722 umol, CAS #286961-14-6) and K₃PO₄ (353 mg, 1.67 mmol) in dioxane (1 mL) and H₂O (0.05 mL) was added XPHOS-PD-G2 (43.7 mg, 55.5 umol). The reaction mixture was stirred at 80° C. for 2.5 hours. On completion, the reaction mixture was filtered and concentrated in vacuo. The residue was purified by reverse phase (0.1% FA condition) to give the title compound (240 mg, 79% yield) as light yellow solid. ¹H NMR (400 MHz, DMSO-d₆) δ 9.35 (s, 1H), 8.59 (s, 1H), 7.91-7.83 (m, 1H), 7.79 (dd, J=7.2, 8.4 Hz, 1H), 7.55 (d, J=7.2 Hz, 1H), 7.26 (d, J=8.4 Hz, 2H), 6.91-6.85 (m, 2H), 5.87 (s, 1H), 4.84 (s, 2H), 4.09 (s, 2H), 3.94 (ddd, J=5.2, 9.6, 12.0 Hz, 1H), 3.81-3.74 (m, 1H), 3.73 (s, 3H), 3.68 (t, J=5.4 Hz, 2H), 3.21-3.10 (m, 1H), 3.02-2.92 (m, 1H), 2.49-2.44 (m, 2H), 1.47 (s, 9H).

Step 2—Tert-butyl 4-[4-[3-[(4-methoxyphenyl)methyl]-2,4-dioxo-hexahydropyrimidin-1-yl]-8-isoquinolyl]piperidine-1-carboxylate To a mixture of tert-butyl 4-[4-[3-[(4-methoxyphenyl)methyl]-2,4-dioxo-hexahydropyrimidin-1-yl]-8-isoquinolyl]-3,6-dihydro-2H-pyridine-1-carboxylate (230 mg, 423 umol) in MeOH (10 mL) was added Pd/C (100 mg, 10 wt %). The reaction mixture was stirred at 40° C. for 3 hours under H₂ (15 Psi) atmosphere. On completion, the reaction mixture was filtered and concentrated in vacuo to give the title compound (220 mg, 95% yield) as white solid. ¹H NMR (400 MHz, DMSO-d₆) δ 9.68 (s, 1H), 8.58 (s, 1H), 7.82-7.72 (m, 2H), 7.62 (d, J=6.8 Hz, 1H), 7.28-7.23 (m, 2H), 6.90-6.86 (m, 2H), 4.83 (s, 2H), 4.14 (d, J=9.6 Hz, 2H), 3.92 (ddd, J=5.2, 9.6, 12.4 Hz, 1H), 3.83 (t, J=11.6 Hz, 1H), 3.78-3.74 (m, 1H), 3.73 (s, 3H), 3.15-2.92 (m, 4H), 1.95-1.85 (m, 2H), 1.74-1.60 (m, 2H), 1.44 (s, 9H).

Step 3—1-[8-(4-Piperidyl)-4-isoquinolyl]hexahydropyrimidine-2,4-dione

To a mixture of tert-butyl 4-[4-[3-[(4-methoxyphenyl)methyl]-2,4-dioxo-hexahydropyrimidin-1-yl]-8-isoquinolyl]piperidine-1-carboxylate (210 mg, 385 umol) in TFA (3 mL) was added TfOH (0.2 mL). The reaction mixture was stirred at 70° C. for 2 hr. On completion, the reaction mixture was concentrated in vacuo. The residue was purified by reverse phase (0.1% FA condition) to give the title compound (200 mg, 98% yield, TFA) as red oil. LC-MS (ESI⁺) m/z 325.0 (M+H)⁺.

3-(4-Bromo-5-fluoro-3-methyl-2-oxo-benzimidazol-1-yl)piperidine-2,6-dione (Intermediate BPW)

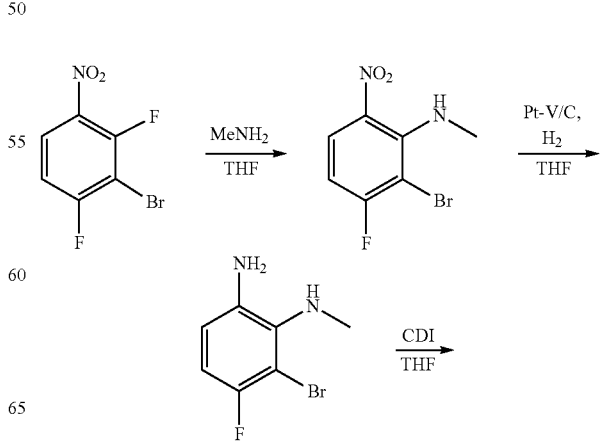

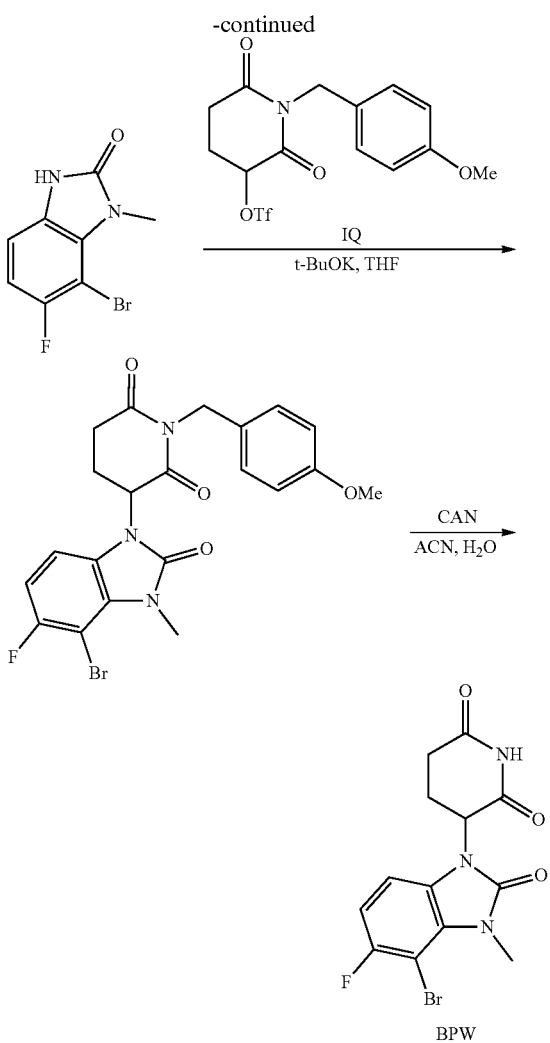

Step 1—2-Bromo-3-fluoro-N-methyl-6-nitro-aniline

A solution of 2-bromo-1,3-difluoro-4-nitro-benzene (10.0 g, 42.0 mmol, CAS #103977-78-2) in THF (100 mL) saturated with MeNH$_2$ (2.00 M, 31.5 mL) was stirred at 60° C. for 5 hrs in a sealed tube. Additional MeNH$_2$ (2.00 M, 10.5 mL) was added, and the mixture was stirred at 60° C. for 2 hrs in a sealed tube. On completion, the mixture was concentrated in vacuo. The mixture was purified by silica gel column (PE) to give the title compound (10.3 g, 98% yield) as yellow solid. $^1$H NMR (400 MHz, DMSO-d$_6$) δ 7.90 (dd, J=6.4, 9.6 Hz, 1H), 6.78 (dd, J=7.6, 9.6 Hz, 2H), 2.76 (d, J=5.2 Hz, 3H), LC-MS (ESI$^+$) m/z 248.9 (M+H)$^+$.

Step 2—3-Bromo-4-fluoro-N2-methyl-benzene-1,2-diamine

To a solution of 2-bromo-3-fluoro-N-methyl-6-nitro-aniline (10.0 g, 40.1 mmol) in THF (100 mL) was added Pt-V/C (524 mg, 2.01 mmol) and the mixture was stirred at 25° C. for 16 hrs under H$_2$ (15 psi). On completion, the mixture was filtered and concentrated in vacuo to give the title compound (8.7 g, 98% yield) as yellow solid. $^1$H NMR (400 MHz, DMSO-d$_6$) δ 6.75-6.65 (m, 1H), 6.60 (dd, J=6.0, 8.8 Hz, 1H), 4.82 (s, 2H), 3.91 (s, 1H), 2.62 (d, J=4.0 Hz, 3H), LC-MS (ESI$^+$) m/z 221.1 (M+H)$^+$.

Step 3—4-Bromo-5-fluoro-3-methyl-1H-benzimidazol-2-one

To a solution of 3-bromo-4-fluoro-N2-methyl-benzene-1,2-diamine (8.70 g, 39.7 mmol) in ACN (120 mL) was added CDI (19.3 g, 119 mmol) and the mixture was stirred at 85° C. for 16 hrs. On completion, the mixture was concentrated in vacuo. The mixture was diluted with H$_2$O (300 mL), filtered and the filtrate was dried in vacuo to give the title compound (8.9 g, 91% yield) as gray solid, $^1$H NMR (400 MHz, DMSO-d$_6$) δ 11.18 (s, 1H), 7.05-6.87 (m, 2H), 3.57 (s, 3H), LC-MS (ESI$^+$) m/z 245.0 (M+H)$^+$.

Step 4—3-(4-Bromo-5-fluoro-3-methyl-2-oxo-benzimidazol-1-yl)-1-[(4-methoxyphenyl)methyl]piperidine-2,6-dione To a solution of 4-bromo-5-fluoro-3-methyl-1H-benzimidazol-2-one (2.50 g, 10.2 mmol) in THF (30.0 mL) was added t-BuOK (2.06 g, 18.3 mmol) at −10° C. The mixture was stirred at −10° C. for 1 hr. Then a solution of [1[(4-methoxyphenyl) methyl]-2,6-dioxo-3-piperidyl] trifluoromethanesulfonate (7.00 g, 18.3 mmol, Intermediate IQ) in THF (30.0 mL) was added to above solution and the mixture was stirred at 25° C. for 16 hrs. On completion, the mixture was quenched with saturated NH$_4$Cl solution (50 mL) and concentrated in vacuo to remove THF. The solution was then extracted with EA (3×40 mL), the organic layers were washed with brine (2×40 mL) dried over anhydrous Na$_2$SO$_4$, filtered and concentrated in vacuo. The mixture was purified by reverse phase: (0.1% FA) to give the title compound (3.5 g, 72% yield) as blue solid. $^1$H NMR (400 MHz, DMSO-d$_6$) δ 7.23-7.18 (m, 2H), 7.12-7.00 (m, 2H), 6.87-6.83 (m, 2H), 5.61-5.56 (m, 1H), 4.86-4.71 (m, 2H), 3.72 (s, 3H), 3.65 (s, 3H), 3.12-2.91 (m, 1H), 2.87-2.69 (m, 2H), 2.09-2.00 (m, 1H), LC-MS (ESI$^+$) m/z 478.2 (M+H)$^+$.

Step 5—3-(4-Bromo-5-fluoro-3-methyl-2-oxo-benzimidazol-1-yl)piperidine-2,6-dione To a solution of 3-(4-bromo-5-fluoro-3-methyl-2-oxo-benzimidazol-1-yl)-1-[(4-methoxyphenyl) methyl] piperidine-2,6-dione (500 mg, 1.05 mmol) in ACN (20.0 mL) was added a solution of CAN (2.88 g, 5.25 mmol) in H$_2$O (5 mL) and the mixture was stirred at 25° C. for 16 hrs. On completion, the mixture was diluted with H$_2$O (20 mL) and extracted with EA (2×30 mL). The organic layers were washed with brine (2×20 mL), dried over anhydrous Na$_2$SO$_4$, filtered and concentrated in vacuo. The mixture was purified by prep-HPLC (column: 3 Phenomenex Luna C18 75*30 mm*3 um; mobile phase: [water (0.05% HCl)-ACN]; B %: 25%-45%, 7 min) to give the title compound (80 mg, 21% yield) as off-white solid. $^1$H NMR (400 MHz, DMSO-d$_6$) δ 11.13 (s, 1H), 7.20-7.13 (m, 1H), 7.12-7.03 (m, 1H), 5.45-5.35 (m, 1H), 3.64 (s, 3H), 2.94-2.79 (m, 1H), 2.77-2.67 (m, 1H), 2.66-2.58 (m, 1H), 2.10-1.95 (m, 1H), LC-MS (ESI$^+$) m/z 358.0 (M+H)$^+$.

3-[5-Fluoro-3-methyl-2-oxo-4-(4-piperidyl)benzimidazol-1-yl]piperidine-2,6-dione (Intermediate BSP)

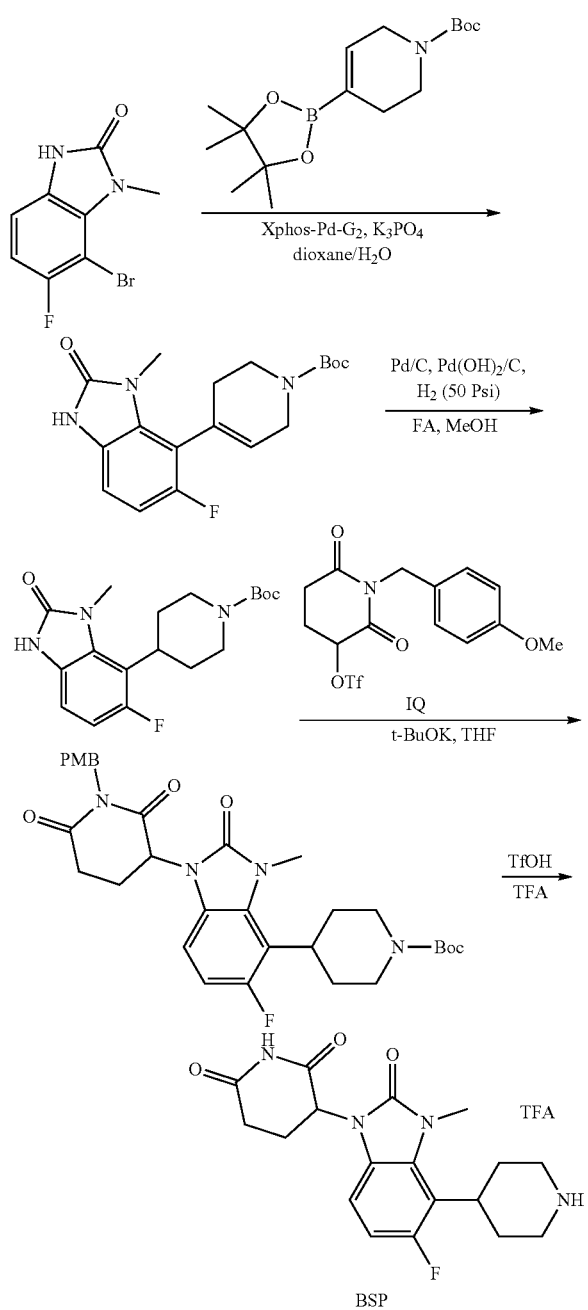

Step 1—Tert-butyl 4-(5-fluoro-3-methyl-2-oxo-1H-benzimidazol-4-yl)-3,6-dihydro-2H-pyridine-1-carboxylate To a mixture of 4-bromo-5-fluoro-3-methyl-1H-benzimidazol-2-one (0.50 g, 2.04 mmol, synthesized via Steps 1-3 of Intermediate BPW) and tert-butyl 4-(4,4,5,5-tetramethyl-1,3,2-dioxaborolan-2-yl)-3,6-dihydro-2H-pyridine-1-carboxylate (1.89 g, 6.12 mmol, CAS #286961-14-6) in dioxane (15 mL) and H$_2$O (0.5 mL) was added XPHOS-PD-G2 (160 mg, 204 umol) and K$_3$PO$_4$ (1.30 g, 6.12 mmol). The reaction mixture was stirred at 80° C. for 12 hr. On completion, the reaction mixture was filtered and concentrated in vacuo. The residue was purified by reverse phase (0.1% FA condition) to give the title compound (0.50 g, 35% yield) as white solid. $^1$H NMR (400 MHz, DMSO-d$_6$) δ 10.95 (s, 1H), 6.90-6.84 (m, 1H), 6.84-6.77 (m, 1H), 5.78 (s, 1H), 4.01 (s, 2H), 3.63-3.48 (m, 2H), 3.23 (s, 3H), 2.41-2.22 (m, 2H), 1.43 (s, 9H); LC-MS (ESI$^+$) m/z 348.0 (M+H)$^+$.

Step 2—Tert-butyl 4-(5-fluoro-3-methyl-2-oxo-1H-benzimidazol-4-yl)piperidine-1-carboxylate To a mixture of tert-butyl 4-(5-fluoro-3-methyl-2-oxo-1H-benzimidazol-4-yl)-3,6-dihydro-2H-pyridine-1-carboxylate (500 mg, 1.44 mmol) in MeOH (200 mL) was added formic acid (1.22 g, 26.5 mmol), Pd/C (400 mg, 10 wt %) and Pd(OH)$_2$/C (400 mg, 10 wt %). The reaction mixture was stirred at 60° C. for 48 hours under H$_2$ (50 Psi) atmosphere. On completion, the reaction mixture was filtered and concentrated in vacuo to give the title compound (350 mg, 69.% yield) as light yellow solid. LC-MS (ESI$^+$) m/z 293.9 (M−56+H)$^+$.

Step 3—Tert-butyl 4-[5-fluoro-1-[1-[(4-methoxyphenyl)methyl]-2,6-dioxo-3-piperidyl]-3-methyl-2-oxo-benzimidazol-4-yl]piperidine-1-carboxylate To a mixture of tert-butyl 4-(5-fluoro-3-methyl-2-oxo-1H-benzimidazol-4-yl)piperidine-1-carboxylate (350 mg, 1.00 mmol) and t-BuOK (168 mg, 1.50 mmol) in THF (8 mL) was added a solution of [1[(4-methoxyphenyl)methyl]-2,6-dioxo-3-piperidyl]trifluoromethanesulfonate (572 mg, 1.50 mmol, Intermediate IQ) in THF (8 mL) dropwise. The reaction mixture was stirred at 0° C. for 3 hr. On completion, the reaction mixture was quenched with NH$_3$Cl (2 mL) and concentrated in vacuo. The residue was purified by reverse phase (0.1% FA condition) to give the title compound (350 mg, 60% yield) as Brown solid. LC-MS (ESI$^+$) m/z 525.1 (M−56+H)$^+$.

Step 4—3-[5-Fluoro-3-methyl-2-oxo-4-(4-piperidyl)benzimidazol-1-yl]piperidine -2,6-dione To a mixture of tert-butyl 4-[5-fluoro-1-[1-[(4-methoxyphenyl)methyl]-2,6-dioxo-3-piperidyl]-3-methyl-2-oxo-benzimidazol-4-yl]piperidine-1-carboxylate (260 mg, 447 umol) in TFA (4 mL) was added TfOH (0.1 mL). The reaction mixture was stirred at 70° C. for 1 hour. On completion, the reaction mixture was concentrated in vacuo to give the title compound (210 mg, 98% yield, TFA) as red oil. LC-MS (ESI$^+$) m/z 361.1 (M+H)$^+$.

N-[2-(4-formylcyclohexyl)-6-(trifluoromethyl)indazol-5-yl]-6-(trifluoromethyl) pyridine -2-carboxamide (Intermediate BSQ)

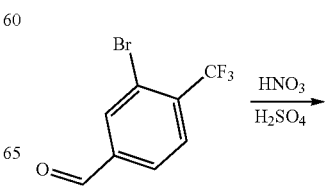

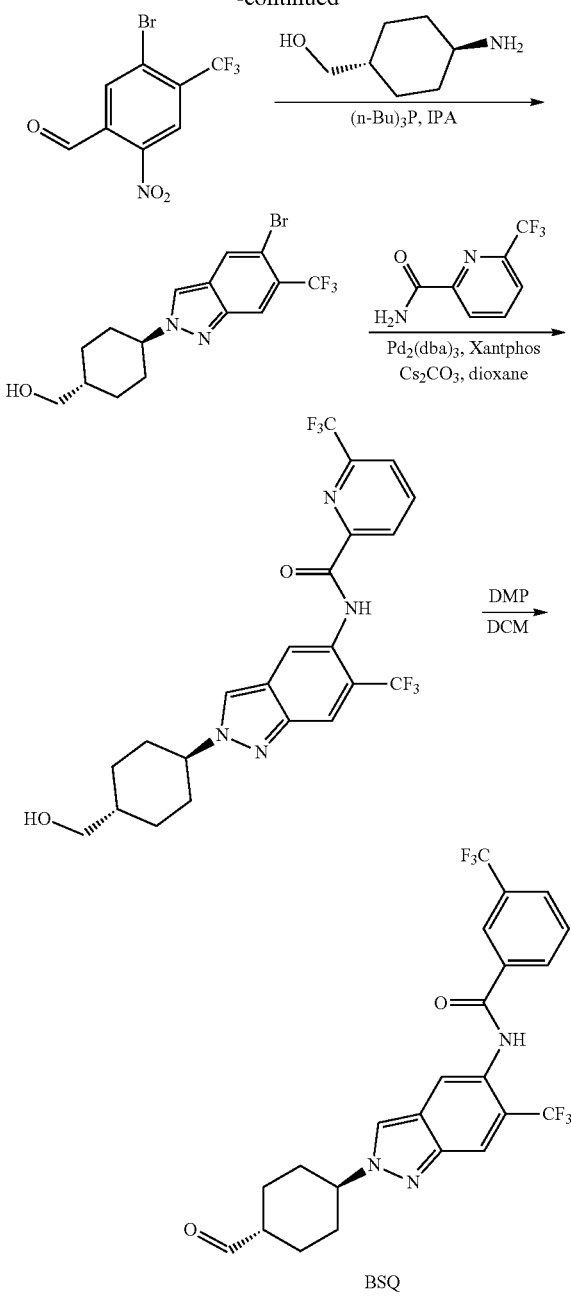

Step 1—5-Bromo-2-nitro-4-(trifluoromethyl)benzaldehyde

To a mixture of 3-bromo-4-(trifluoromethyl) benzaldehyde (4.50 g, 17.7 mmol, CAS #891180-59-9) in H2SO4 (50 mL) was added HNO₃ (1.46 g, 23.1 mmol) at 0° C. Then the reaction mixture was stirred at 25° C. for 2 hours. On completion, the reaction mixture was diluted with water (100 mL), light yellow solid was formed and filtered to give the title compound (5.30 g, 99% yield) as light yellow solid. ¹H NMR (400 MHz, DMSO-d₆) δ 10.26 (s, 1H), 8.49 (s, 1H), 8.31 (s, 1H).

Step 2—[4-[5-Bromo-6-(trifluoromethyl)indazol-2-yl]cyclohexyl]methanol

To a mixture of 5-bromo-2-nitro-4-(trifluoromethyl) benzaldehyde (4.80 g, 16.1 mmol) and (4-aminocyclohexyl)methanol (2.29 g, 17.7 mmol, CAS #1467-84-1) in IPA (55 mL) and the reaction mixture was stirred at 80° C. for 12 hours. Then to the reaction mixture was added tributylphosphane (9.78 g, 48.3 mmol) at 25° C., and the reaction mixture was stirred at 80° C. for 4 hours. On completion, the reaction mixture was concentrated in vacuo. The residue was purified by column chromatography to give the title compound (3.40 g, 56% yield) as white solid. ¹H NMR (400 MHz, DMSO-d₆) δ 8.56 (s, 1H), 8.26 (s, 1H), 8.21 (s, 1H), 4.58-4.52 (m, 1H), 4.50 (t, J=5.6 Hz, 1H), 3.28 (t, J=5.6 Hz, 2H), 2.17-2.11 (m, 2H), 1.93-1.86 (m, 4H), 1.53-1.43 (m, 1H), 1.20-1.10 (m, 2H).

Step 3—N-[2-[4-(hydroxymethyl)cyclohexyl]-6-(trifluoromethyl)indazol-5-yl]-6-(trifluoromethyl)pyridine-2-carboxamide To a mixture of [4-[5-bromo-6-(trifluoromethyl)indazol-2-yl]cyclohexyl]methanol (200 mg, 530 umol) and 6-(trifluoromethyl)pyridine-2-carboxamide (110 mg, 583 umol, Intermediate ATI) in dioxane (5 mL) was added Pd₂(dba)₃ (48.5 mg, 53.0 umol), Xantphos (30.6 mg, 53.0 umol) and Cs₂CO₃ (345 mg, 1.06 mmol) and the reaction mixture was stirred at 80° C. for 12 hours. On completion, the residue was diluted with water (10 mL), then the residue was extracted with EA (3×50 mL). The combined organic layer was dried over Na₂SO₄, filtered and concentrated in vacuo to give a residue. The residue was purified by reverse phase (0.1% FA condition) to give the title compound (130 mg, 50% yield) as white solid. LC-MS (ESI⁺) m/z 487.1 (M+H)⁺.

Step 4—N-[2-(4-formylcyclohexyl)-6-(trifluoromethyl)indazol-5-yl]-6-(trifluoromethyl) pyridine-2-carboxamide To a mixture of N-[2-[4-(hydroxymethyl)cyclohexyl]-6-(trifluoromethyl)indazol-5-yl]-6-(trifluoromethyl)pyridine-2-carboxamide (120 mg, 246 umol) in DCM (2 mL) was added DMP (156 mg, 370 umol) and the reaction mixture was stirred at 25° C. for 3 hours. On completion, the residue was diluted with water (50 mL), then the residue was extracted with DCM (3×70 mL). The combined organic layer was dried over Na₂SO₄, filtered and concentrated in vacuo to give the title compound (120 mg, 95% yield) as light yellow solid. LC-MS (ESI⁺) m/z 485.1 (M+H)⁺.

3-[4-[1-[[4-(5-Amino-6-methoxy-indazol-2-yl)cyclohexyl]methyl]-4-piperidyl]-3-methyl-2-oxo-benzimidazol-1-yl]piperidine-2,6-dione (Intermediate BSS)

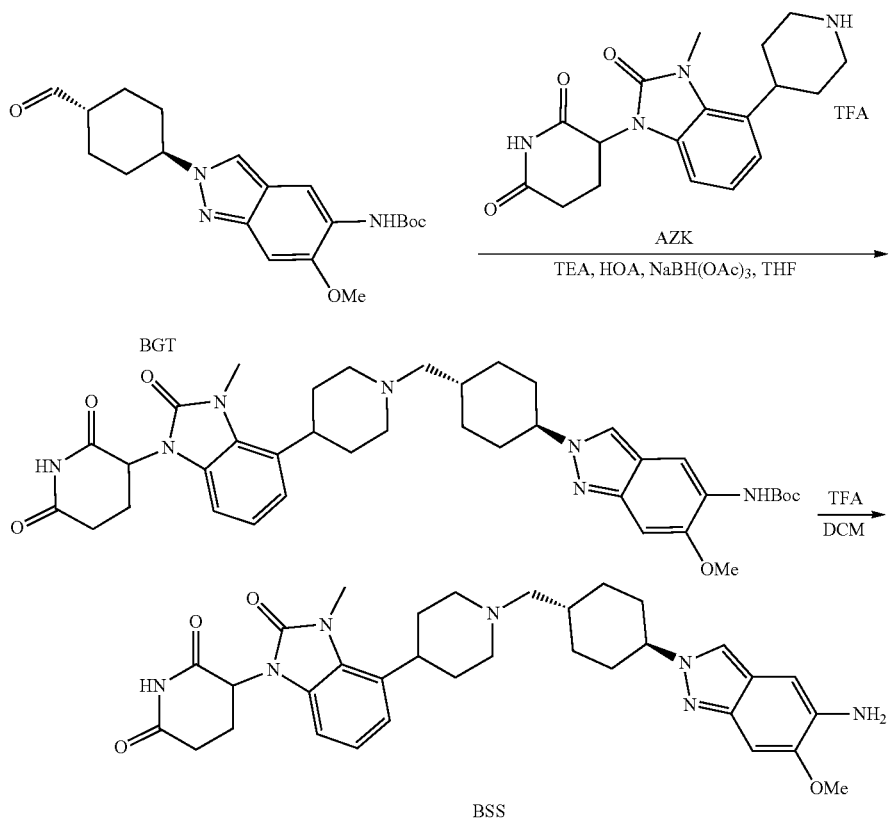

Step 1—Tert-butyl N-[2-[4-[[4-[1-(2,6-dioxo-3-piperidyl)-3-methyl-2-oxo-benzimidazol-4-yl]-1-piperidyl]methyl]cyclohexyl]-6-methoxy-indazol-5-yl]carbamate To a solution of 3-[3-methyl-2-oxo-4-(4-piperidyl)benzimidazol-1-yl]piperidine-2,6-dione (513 mg, 1.12 mmol, TFA, Intermediate AZK) in THF (8 mL) was added TEA (313.08 uL, 2.25 mmol) at −10° C. Then HOAc (128 uL, 2.25 mmol) and tert-butyl N-[2-(4-formylcyclohexyl)-6-methoxy-indazol-5-yl]carbamate (420 mg, 1.12 mmol, Intermediate BGT) was added to the mixture at −10° C. The mixture was stirred at −10° C. for 0.5 hr, then NaBH(OAc)$_3$ (357 mg, 1.69 mmol) was added at −10° C. and the mixture was stirred at −10° C. for 1 hr. On completion, the mixture was quenched by water (0.2 mL), and then concentrated in vacuo to give a residue. The residue was purified by reverse-phase (FA condition) to give the title compound (230 mg, 29% yield) as a white solid. $^1$H NMR (400 MHz, DMSO-d$_6$) δ 11.09 (s, 1H), 8.17 (d, J=7.2 Hz, 1H), 7.89 (s, 1H), 7.77 (s, 1H), 7.04-6.95 (m, 4H), 5.37 (dd, J=5.2, 12.4 Hz, 1H), 4.40-4.27 (m, 1H), 3.85 (s, 3H), 3.59 (s, 3H), 3.01 (d, J=10.4 Hz, 2H), 2.97-2.80 (m, 2H), 2.77-2.69 (m, 1H), 2.62 (d, J=17.6 Hz, 1H), 2.23 (d, J=6.8 Hz, 2H), 2.17-2.07 (m, 4H), 1.98-1.95 (m, 3H), 1.92-1.85 (m, 2H), 1.80 (s, 4H), 1.72-1.60 (m, 1H), 1.46 (s, 9H), 1.12 (q, J=12.4 Hz, 2H); LC-MS (ESI$^+$) m/z 700.2 (M+H)$^+$.

Step 2—3-[4-[1-[[4-(5-Amino-6-methoxy-indazol-2-yl)cyclohexyl]methyl]-4-piperidyl]-3-methyl-2-oxo-benzimidazol-1-yl]piperidine-2,6-dione To a solution of tert-butyl N-[2-[4-[[4-[1-(2,6-dioxo-3-piperidyl)-3-methyl-2-oxo-benzimidazol-4-yl]-1-piperidyl]methyl]cyclohexyl]-6-methoxy-indazol-5-yl]carbamate (70.0 mg, 100 umol) in DCM (1 mL) was added TFA (74.0 uL, 1.00 mmol). The mixture was stirred at 25° C. for 1 hr. On completion, the mixture was concentrated in vacuo to give the title compound (70.0 mg, 90% yield, TFA) as an off-white oil. LC-MS (ESI$^+$) m/z 600.2 (M+H)$^+$.

6-(5-cyanopyrrolo[2,3-b]pyridin-1-yl)-N-[(4-formyl-cyclohexyl)methyl]-4-(isopropylamino) pyridine-3-carboxamide (Intermediate BSU)

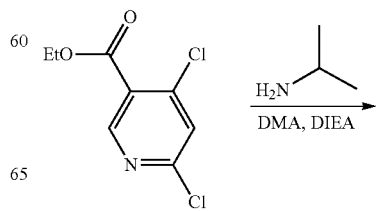

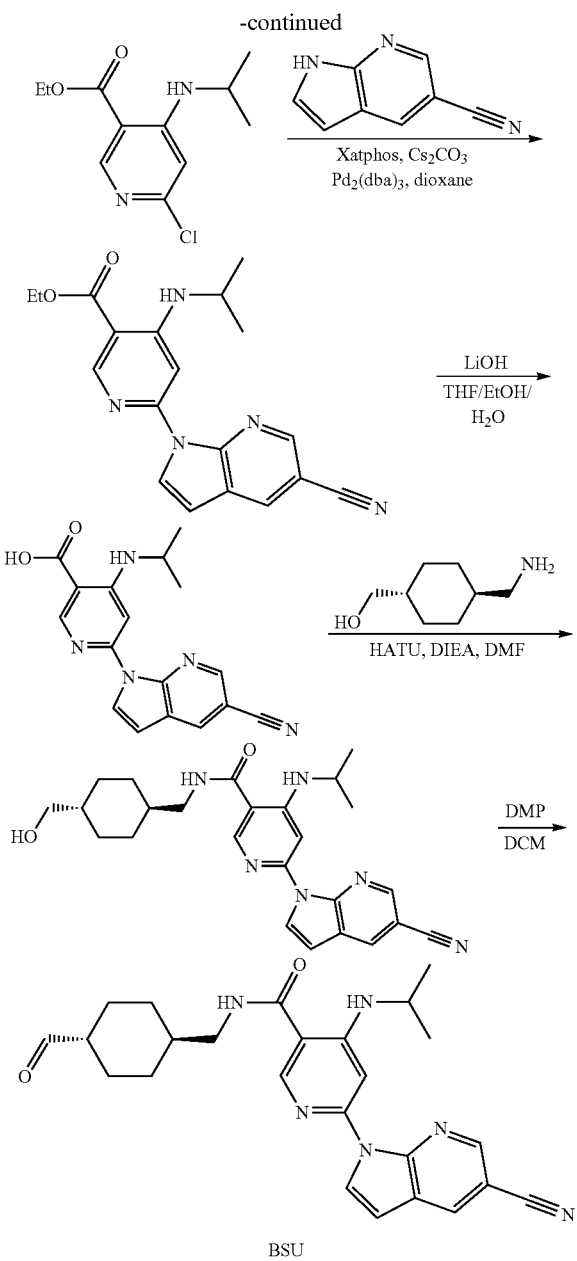

Step 1—Ethyl 6-chloro-4-(isopropylamino)pyridine-3-carboxylate

To a solution of ethyl 4,6-dichloropyridine-3-carboxylate (1 g, 4.54 mmol, CAS #40296-46-6) in DMA (10 mL) was added DIEA (2.94 g, 22.7 mmol, 3.96 mL) and propan-2-amine (537 mg, 9.09 mmol, CAS #4432-77-3). The reaction mixture was stirred at 50° C. for 3 hrs. On completion, the reaction mixture was diluted with EtOAc (50 mL) and washed with water (50 mL×3). The organic layer was dried over Na$_2$SO$_4$, filtered and concentrated in vacuo. The residue was purified by column chromatography (SiO$_2$, petroleum ether/ethyl acetate=10/1, P1: R$_f$=0.5) to give title compound (0.968 g, 87% yield) as yellow solid. $^1$H NMR (400 MHz, DMSO-d$_6$) δ 8.53 (s, 1H), 7.99 (d, J=6.8 Hz, 1H), 6.83 (s, 1H), 4.29 (q, J=7.2 Hz, 2H), 3.92-3.79 (m, 1H), 1.31 (t, J=7.2 Hz, 3H), 1.20 (d, J=6.4 Hz, 6H).

Step 2—Ethyl 6-(5-cyanopyrrolo[2,3-b]pyridin-1-yl)-4-(isopropylamino)pyridine-3-carboxylate To a solution of ethyl 6-chloro-4-(isopropylamino)pyridine-3-carboxylate (868 mg, 3.58 mmol) and 1H-pyrrolo[2,3-b]pyridine-5-carbonitrile (511 mg, 3.58 mmol, CAS #517918-95-5) in dioxane (9 mL) was added Xantphos (206 mg, 357 umol) and Cs$_2$CO$_3$ (2.33 g, 7.15 mmol). The reaction mixture was purged with N$_2$ several times, then Pd$_2$(dba)$_3$ (327 mg, 357 umol) was added and the mixture was purged with N$_2$ again. The mixture was then stirred at 110° C. for 16 hrs under N$_2$. On completion, the reaction mixture was filtered and concentrated in vacuo. The residue was purified by column chromatography (SiO$_2$, petroleum ether/ethyl acetate=10/1 to 5/1, P1: R$_f$=0.5) to give title compound (500 mg, 40% yield) as yellow solid. $^1$H NMR (400 MHz, CDCl$_3$) δ 8.83 (s, 1H), 8.67 (s, 1H), 8.57 (d, J=4.0 Hz, 1H), 8.25 (d, J=12.0 Hz, 2H), 8.19 (s, 1H), 6.71 (d, J=3.6 Hz, 1H), 4.37 (q, J=7.2 Hz, 2H), 3.98-3.88 (m, 1H), 1.44 (s, 9H).

Step 3—6-(5-cyanopyrrolo[2,3-b]pyridin-1-yl)-4-(isopropylamino)pyridine-3-carboxylic Acid To a solution of ethyl 6-(5-cyanopyrrolo[2,3-b]pyridin-1-yl)-4-(isopropylamino)pyridine-3-carboxylate (400 mg, 1.14 mmol) in EtOH (1 mL), THF (4 mL) and H$_2$O (0.6 mL) was added LiOH·H$_2$O (480 mg, 11.4 mmol). The mixture was then stirred at 50° C. for 9 hrs. On completion, the reaction mixture was filtered and the filtrate was diluted with water (4 mL). The aqueous layer was acidified to pH 5-6 using 2 M HCl and freeze-drying. The product was dissolved in DCM:MeOH=10:1 (11 mL) and filtered. The filtrate was concentrated in vacuo to give title compound (220 mg, 59% yield) as yellow solid. $^1$H NMR (400 MHz, DMSO-d$_6$) δ 10.02 (s, 1H), 8.77 (d, J=2.0 Hz, 1H), 8.66-8.61 (m, 2H), 8.51 (d, J=4.0 Hz, 1H), 7.83 (s, 1H), 6.82 (d, J=4.0 Hz, 1H), 3.75-3.65 (m, 1H), 1.33 (d, J=6.6 Hz, 1H), 1.27 (d, J=6.4 Hz, 6H).

Step 4—6-(5-cyanopyrrolo[2,3-b]pyridin-1-yl)-N-[[4-(hydroxymethyl)cyclohexyl]methyl]-4-(isopropylamino)pyridine-3-carboxamide To a solution of 6-(5-cyanopyrrolo[2,3-b]pyridin-1-yl)-4-(isopropylamino)pyridine-3-carboxylic acid (200 mg, 622 umol) and [4-(aminomethyl)cyclohexyl]methanol (115 mg, 809 umol, CAS #17879-23-1) in DMF (4 mL) were added DIEA (160 mg, 1.24 mmol) and HATU (473 mg, 1.24 mmol) at 25° C. The reaction mixture was stirred at 25° C. for 1 hr. On completion, the reaction mixture was diluted with EtOAc (20 ml). The organic layer was washed with water (20 mL×3) and concentrated in vacuo. The residue was purified by column chromatography (SiO$_2$, petroleum ether/ethyl acetate=1/1, P1: R$_f$=0.3) to give title compound (260 mg, 93% yield) as pink solid. $^1$H NMR (400 MHz, DMSO-d$_6$) δ 8.80 (d, J=2.0 Hz, 1H), 8.66 (d, J=2.0 Hz, 1H), 8.62 (d, J=7.2 Hz, 1H), 8.57 (s, 1H), 8.56-8.53 (m, 1H), 8.52 (d, J=4.0 Hz, 1H), 8.07 (s, 1H), 6.88 (d, J=4.0 Hz, 1H), 4.34 (t, J=5.2 Hz, 1H), 3.83-3.70 (m, 1H), 3.20 (t, J=5.6 Hz, 2H), 3.09 (t, J=6.4 Hz, 2H), 2.69 (s, 3H), 1.81-1.71 (m, 4H), 1.55-1.44 (m, 1H), 1.29 (d, J=6.4 Hz, 6H).

Step 5—6-(5-cyanopyrrolo[2,3-b]pyridin-1-yl)-N-[(4-formylcyclohexyl)methyl]-4-(isopropylamino)pyridine-3-carboxamide To a solution of 6-(5-cyanopyrrolo[2,3-b]pyridin-1-yl)-N-[[4-(hydroxymethyl)cyclohexyl]methyl]-4-(isopropylamino)pyridine-3-carboxamide (210 mg, 470 umol) in DCM (4 mL) and DMF (0.1 mL) was added DMP (398 mg, 940 umol). The reaction was stirred at 25° C. for 1 hr. On completion, the reaction mixture was quenched with $Na_2S_2O_3$ (6 mL) and $NaHCO_3$ (6 mL) aqueous and the mixture was extracted with DCM (30 mL×2). The combined organic layers were concentrated in vacuo to give title compound (155 mg, 348 umol, 74% yield) as yellow solid. LC-MS (ESI⁺) m/z 445.2 (M+H)⁺.

3-[5-Chloro-3-methyl-2-oxo-4-(4-piperidyl)benzimidazol-1-yl]piperidine -2,6-dione (Intermediate BSV)

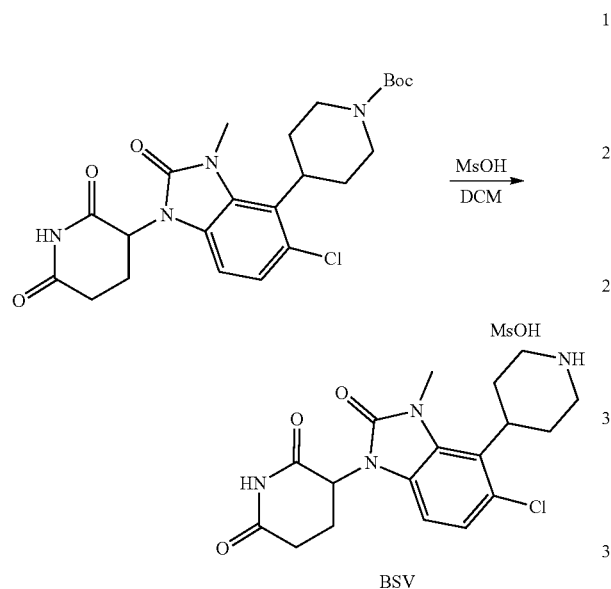

To a mixture of tert-butyl 4-[5-chloro-1-(2,6-dioxo-3-piperidyl)-3-methyl-2-oxo-benzimidazol-4-yl] piperidine-1-carboxylate (50.0 mg, 104 umol, synthesized via Step 1 of Intermediate BQL) in DCM (2 mL) was added MsOH (30.2 mg, 314 umol). The reaction mixture was stirred at 60° C. for 1 hour. On completion, the reaction mixture was filtered and the residue was concentrated in vacuo to give the title compound (45.0 mg) as white solid. LC-MS (ESI⁺) m/z 377.1 (M+H)⁺.

N-[2-[3-(iodomethyl)cyclobutyl]-6-methoxy-indazol-5-yl]-6-(trifluoromethyl)pyridine-2-carboxamide (Intermediate BSW)

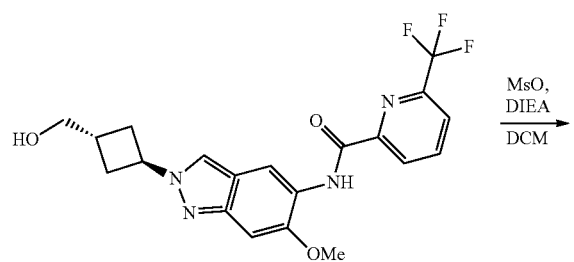

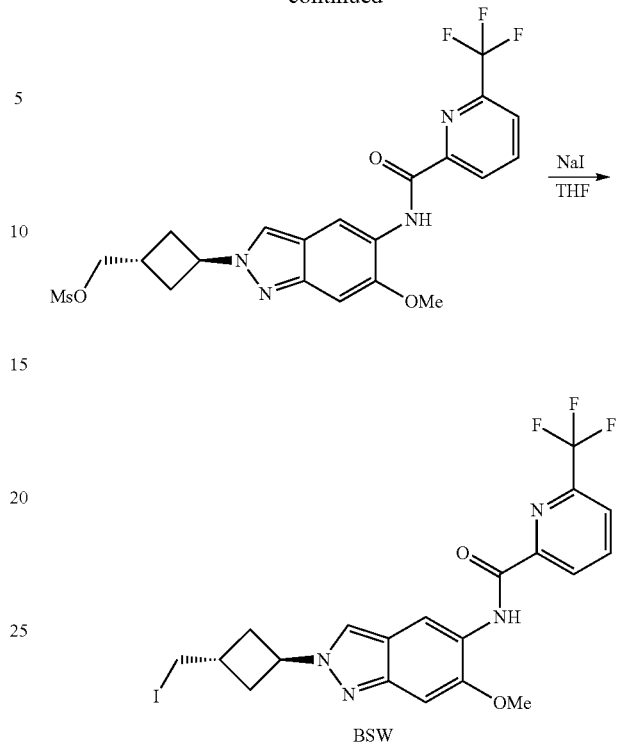

Step 1—3-[6-Methoxy-5-[[6-(trifluoromethyl)pyridine-2-carbonyl]amino]indazol-2-yl]cyclobutyl] methyl methanesulfonate To a mixture of N-[2-[3-(hydroxymethyl)cyclobutyl]-6-methoxy-indazol-5-yl]-6-(trifluoromethyl) pyridine-2-carboxamide (230 mg, 547 umol, synthesized via Steps 1-3 of Intermediate BQI) and DIEA (212 mg, 1.64 mmol, 285 uL) in THF (5 mL) was added methylsulfonyl methanesulfonate (142 mg, 820 umol). The reaction mixture was stirred at 25° C. for 12 hr. On completion, the reaction mixture was diluted with water (10 mL) and extracted with EA (2×20 mL). The combined organic layer was dried over $Na_2SO_4$, filtered and concentrated in vacuo to give a residue. The residue was purified by column chromatography to give the title compound (210 mg, 77% yield) as yellow solid. LC-MS (ESI⁺) m/z 499.1 (M+H)⁺.

Step 2—N-[2-[3-(iodomethyl)cyclobutyl]-6-methoxy-indazol-5-yl]-6-(trifluoromethyl)pyridine-2-carboxamide To a mixture of [3-[6-methoxy-5-[[6-(trifluoromethyl)pyridine-2-carbonyl]amino]indazol-2-yl]cyclobutyl]methyl methanesulfonate (210 mg, 421 umol) in THF (8 mL) was added NaI (284 mg, 1.90 mmol). The reaction mixture was stirred at 65° C. for 12 hr. On completion, the reaction mixture was filtered and concentrated in vacuo. The residue was diluted with water (10 mL) and extracted with EA (2×30 mL). The combined organic layers was dried over $Na_2SO_4$, filtered and concentrated in vacuo to give the title compound (210 mg, 396.02 umol, 94.00% yield) as yellow solid. LC-MS (ESI⁺) m/z 531.0 (M+H)⁺.

N-[6-chloro-2-[3-(iodomethyl)cyclobutyl]indazol-5-yl]-6-(trifluoromethyl)pyridine-2-carboxamide (Intermediate BSX)

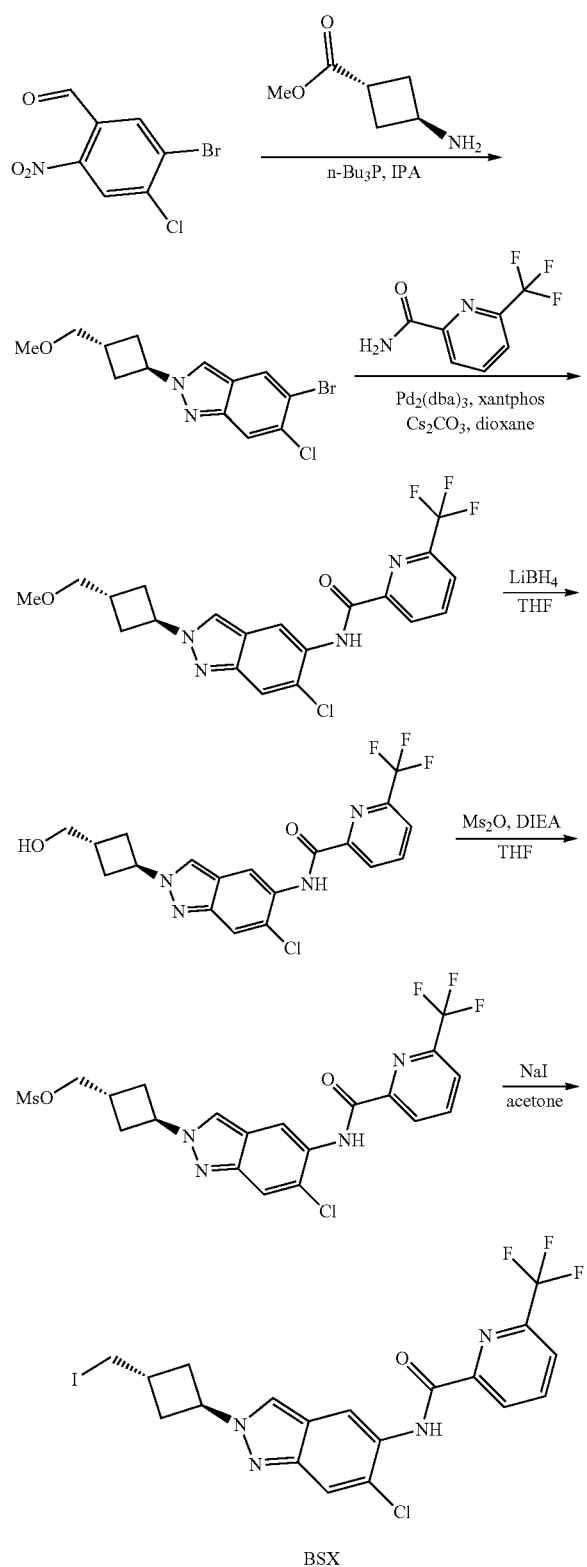

BSX

Step 1—methyl 3-(5-bromo-6-chloro-indazol-2-yl)cyclobutanecarboxylate

To a solution of methyl 3-aminocyclobutanecarboxylate (293 mg, 2.27 mmol, CAS #74316-29-3) and 5-bromo-4-chloro-2-nitro-benzaldehyde (500 mg, 1.89 mmol, synthesized via Step 1 of Intermediate BPQ) in IPA (10 mL) was stirred under $N_2$ at 20° C. for 3 hrs. Then, tributylphosphane (1.15 g, 5.67 mmol) was added into the mixture and stirred at 80° C. for 4 hr under $N_2$. On completion, the reaction mixture was concentrated in vacuo. The residue was purified by column chromatography ($SiO_2$, PE:EA=10:1 to PE:EA=5:1, PE:EA=3:1, PI:Rf=0.4) to give the title compound (220 mg, 33% yield) as yellow solid. $^1$H NMR (400 MHz, $CDCl_3$) δ 7.96 (s, 1H), 7.89 (d, J=6.4 Hz, 2H), 5.35-5.25 (m, 1H), 3.78 (s, 3H), 3.38-3.28 (m, 1H), 3.13-3.03 (m, 2H), 2.91-2.83 (m, 2H).

Step 2—methyl 3-[6-chloro-5-[[6-(trifluoromethyl)pyridine-2-carbonyl]amino]indazol-2-yl]cyclobutanecarboxylate A mixture of methyl 3-(5-bromo-6-chloro-indazol-2-yl)cyclobutanecarboxylate (200 mg, 582 umol), 6-(trifluoromethyl)pyridine-2-carboxamide (166 mg, 873 umol, Intermediate ATI), $Pd_2(dba)_3$ (53.3 mg, 58.2 umol), Xantphos (33.6 mg, 58.2 umol) and $Cs_2CO_3$ (379 mg, 1.16 mmol) in dioxane (3 mL) was degassed and purged with $N_2$ 3 times. Then the mixture was stirred at 100° C. for 16 hrs under $N_2$ atmosphere. On completion, the reaction mixture was diluted with EtOAc (40 mL), filtered and the filter cake was washed with 50% petroleum ether in EtOAc two times and water to give the title compound (190 mg, 72.% yield) as yellow solid. $^1$H NMR (400 MHz, DMSO-$d_6$) δ 10.53 (s, 1H), 8.61 (d, J=13.2 Hz, 2H), 8.48-8.44 (m, 1H), 8.44-8.39 (m, 1H), 8.24 (dd, J=0.8, 7.6 Hz, 1H), 7.98 (s, 1H), 5.40-5.30 (m, 1H), 3.70 (s, 3H), 3.37-3.33 (m, 1H), 2.99-2.87 (m, 2H), 2.82-2.73 (m, 2H).

Step 3—N-(6-chloro-2-((1r,3 r)-3-(hydroxymethyl)cyclobutyl)-2H-indazol-5-yl)-6-(trifluoromethyl)picolinamide To a solution of methyl 3-[6-chloro-5-[[6-(trifluoromethyl) pyridine-2-carbonyl]amino]indazol-2-yl]cyclobutanecarboxylate (150 mg, 331 umol) in THF (2 mL) was added $LiBH_4$ (37.5 mg, 1.72 mmol) at 0° C. under $N_2$. The reaction mixture was then stirred at 20° C. for 3 hrs. On completion, the reaction mixture was quenched with water (0.1 mL) and the reaction residue was diluted with water (20 mL), then extracted with EA (3×50 mL). The combined organic layers ware dried over $Na_2SO_4$, filtered and the filtrate was concentrated in vacuo. The residue was purified by prep-TLC ($SiO_2$, DCM:MeOH=20:1, P1:Rf=0.3) to give the title compound (40.0 mg, 28% yield) as white solid. LC-MS ($ESI^+$) m/z 425.0 $(M+H)^+$.

Step 4—[3-[6-chloro-5-[[6-(trifluoromethyl)pyridine-2-carbonyl]amino]indazol-2-yl]cyclobutyl]methyl methanesulfonate To a solution of N-[6-chloro-2-[3-(hydroxymethyl)cyclobutyl]indazol-5-yl]-6-(trifluoromethyl) pyridine-2-carboxamide (40.0 mg, 94.1 umol) in THF (1 mL) was added DIEA (36.5 mg, 282 umol), and the mixture was stirred at 0° C. for 5 mins. Next to the reaction mixture was added methylsulfonyl methanesulfonate (24.6 mg, 141 umol) at 0°

C., then the reaction mixture was stirred at 25° C. for 16 hrs. On completion, the reaction mixture was diluted with H₂O (10 mL), and the mixture was extracted with EtOAc (2×20 mL). The combined organic layers ware washed with H₂O (2×10 mL) and dried over Na₂SO₄, filtered and the filtrate was concentrated in vacuo to give the title compound (47.0 mg, 99% yield) as yellow solid. LC-MS (ESI⁺) m/z 503.0 (M+H)⁺.

Step 5—N-[6-chloro-2-[3-(iodomethyl)cyclobutyl] indazol-5-yl]-6-(trifluoromethyl)pyridine-2-carboxamide To a solution of [3-[6-chloro-5-[[6-(trifluoromethyl) pyridine-2-carbonyl]amino]indazol-2-yl]cyclobutyl]methyl methanesulfonate (47.0 mg, 93.4 umol) in acetone (2 mL) was added NaI (70.0 mg, 467.30 umol). The reaction mixture was stirred at 60° C. for 16 hrs. On completion, the reaction mixture was diluted with EtOAc (20 mL) and the layers were separated. The organic layer was washed with H₂O (2×10 mL) and dried over Na₂SO₄. The residue was filtered and the filtrate was concentrated in vacuo to give the title compound (49 mg, 98% yield) as yellow solid. ¹H NMR (400 MHz, DMSO-d₆) δ 10.53 (s, 1H), 8.63 (s, 1H), 8.57 (d, J=0.8 Hz, 1H), 8.49-8.44 (m, 1H), 8.44-8.38 (m, 1H), 8.24 (dd, J=1.2, 7.6 Hz, 1H), 7.98 (s, 1H), 5.36-5.27 (m, 1H), 3.60 (d, J=8.0 Hz, 2H), 3.30 (s, 1H), 2.95-2.83 (m, 1H), 2.77-2.68 (m, 2H), 2.39-2.35 (m, 1H).

3-[3-methyl-2-oxo-4-(4-piperidyl)benzimidazol-1-yl]piperidine -2,6-dione (Intermediate BSY)

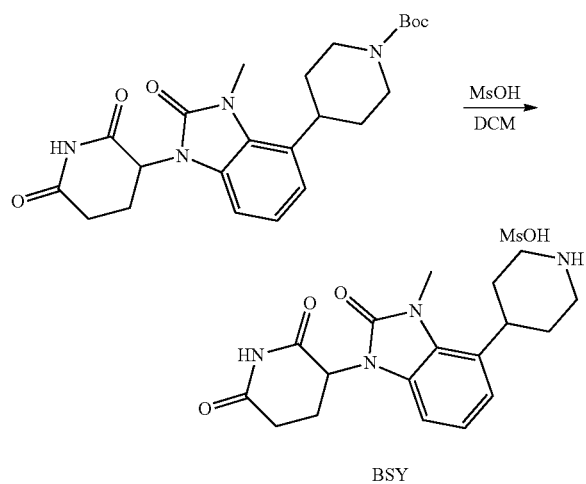

BSY

To a solution of tert-butyl 4-[1-(2,6-dioxo-3-piperidyl)-3-methyl-2-oxo-benzimidazol-4-yl]piperidine-1-carboxylate (150 mg, 338 umol, synthesized via Steps 1-2 of Intermediate AZK) in DCM (1 mL) was added methanesulfonic acid (97.7 mg, 1.02 mmol), then the reaction mixture was stirred at 20° C. for 3 hrs. On completion, the reaction mixture was diluted with MTBE (10 mL), and the mixture was stirred at 20° C. for 10 mins. The mixture was filtered and the filter cake was dried in vacuo to give the title compound (100 mg, 86% yield) as brown solid. LC-MS (ESI⁺) m/z 343.1 (M+H)⁺.

1-[8-(4-Piperidyl)-4-isoquinolyl]hexahydropyrimidine-2,4-dione (Intermediate BSZ)

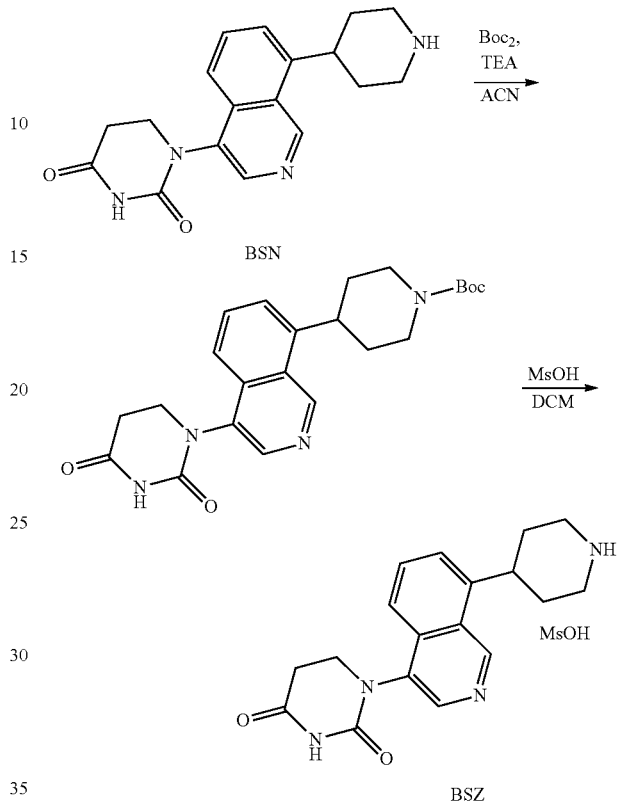

BSZ

Step 1—Tert-butyl 4-[4-(2,4-dioxohexahydropyrimidin-1-yl)-8-isoquinolyl]piperidine-1-carboxylate To a mixture of 1-[8-(4-piperidyl)-4-isoquinolyl]hexahydropyrimidine-2,4-dione (480 mg, 1.09 mmol, TFA, Intermediate BSN) in ACN (10 mL) was added Boc₂O (358 mg, 1.64 mmol) and TEA (332 mg, 3.28 mmol). The reaction mixture was stirred at 25° C. for 12 hours. On completion, the reaction mixture was filtered and concentrated in vacuo to give the title compound (350 mg, 75% yield) as brown oil. ¹H NMR (400 MHz, DMSO-d6) δ 10.54 (s, 1H), 9.67 (s, 1H), 8.57 (s, 1H), 7.88-7.85 (m, 1H), 7.76 (t, J=7.6 Hz, 1H), 7.61 (d, J=7.6 Hz, 1H), 4.14 (d, J=9.6 Hz, 2H), 3.96-3.88 (m, 1H), 3.83 (t, J=11.6 Hz, 1H), 3.74-3.68 (m, 1H), 3.02-2.93 (m, 2H), 2.79-2.72 (m, 1H), 1.94-1.87 (m, 2H), 1.73-1.59 (m, 3H), 1.44 (s, 9H).

Step 2—1-[8-(4-Piperidyl)-4-isoquinolyl]hexahydropyrimidine-2,4-dione

To a mixture of tert-butyl 4-[4-(2,4-dioxohexahydropyrimidin-1-yl)-8-isoquinolyl]piperidine-1-carboxylate (60.0 mg, 141 umol) in DCM (2 mL) was added MsOH (40.7 mg, 424 umol) and the reaction mixture was stirred at 25° C. for 1 hour. On completion, the reaction mixture was triturated with MTBE (3 mL) and filtered to afford a white solid which was collected and dried in vacuo to give the title compound (45.0 mg, 98% yield) as white solid. LC-MS (ESI+) m/z 325.1 (M+H)⁺

4-[6-Methoxy-5-[[6-(trifluoromethyl)pyridine-2-carbonyl]amino]indazol-2-yl]cyclohexane carboxylic acid (Intermediate AXQ)

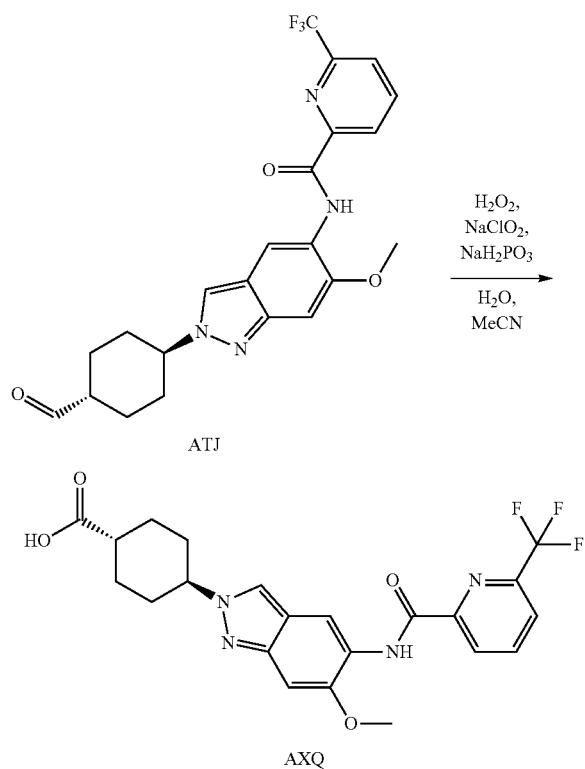

To a solution of N-[2-(4-formylcyclohexyl)-6-methoxyindazol-5-yl]-6-(trifluoromethyl)pyridine-2-carboxamide (1.00 g, 2.24 mmol, Intermediate ATJ) and NaH$_2$PO$_4$ (1.34 g, 11.2 mmol) in ACN (20 mL) was added H$_2$O$_2$ (507 mg, 4.48 mmol, 30% solution) dropwise at 0° C. Then a solution of sodium chlorite (1.42 g, 15.6 mmol) in H$_2$O (10 mL) was added and the reaction mixture was stirred at 0-25° C. for 1 hour. On completion, the reaction mixture was diluted with ACN (20 mL), quenched with Na$_2$SO$_3$ (10 mL) aqueous solution and filtered. The solid was dried in vacuo to give the title compound (800 mg, 80% yield) as brown solid. LC-MS (ESI$^+$) m/z 463.1 (M+H)$^+$.

N-[2-(4-formylcyclohexyl)indazol-5-yl]-6-(trifluoromethyl)pyridine-2-carboxamide (Intermediate BTW)

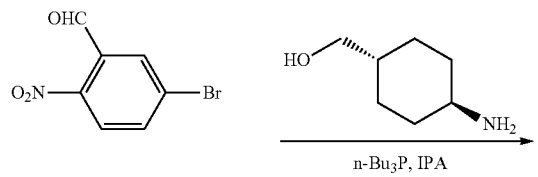

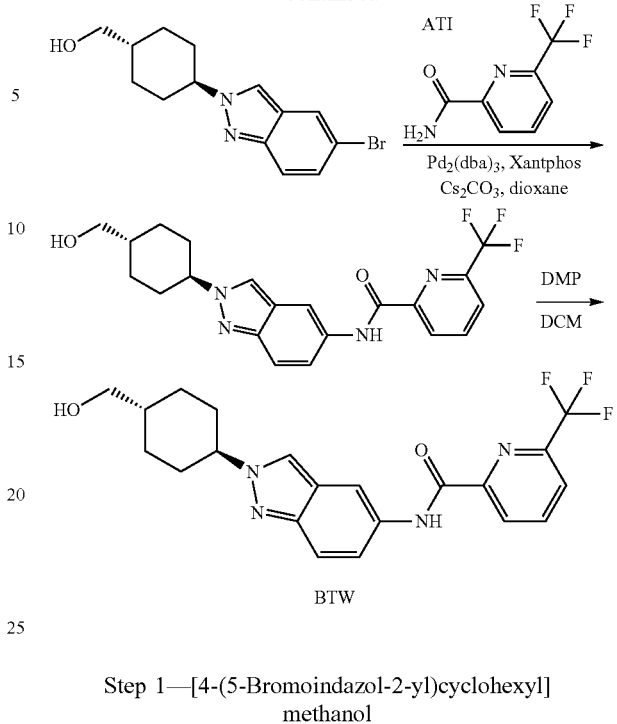

Step 1—[4-(5-Bromoindazol-2-yl)cyclohexyl]methanol

To a solution of 5-bromo-2-nitro-benzaldehyde (4.00 g, 17.3 mmol, CAS #20357-20-4) and (4-aminocyclohexyl)methanol (2.47 g, 19.1 mmol, CAS #1467-84-1) in IPA (60 mL), then the reaction mixture was stirred at 80° C. for 4 hrs under N$_2$. Next, the mixture was cooled to 25° C. and tributylphosphane (3.52 g, 17.3 mmol, 4.29 mL) was added. Then the mixture was stirred at 80° C. for 16 hrs under N$_2$. On completion, the reaction mixture was diluted with EA (50 mL) and extracted with EA (3×100 mL). The combined organic layers were washed with brine (2×100 mL), dried over anhydrous Na$_2$SO$_4$, filtered and concentrated to give the title compound (1.8 g, 33% yield) as a white solid. $^1$H NMR (400 MHz, DMSO-d$_6$) δ 8.39 (d, J=0.8 Hz, 1H), 7.93 (d, J=1.6 Hz, 1H), 7.58 (d, J=9.2 Hz, 1H), 7.29 (dd, J=2.0, 8.8 Hz, 1H), 4.54-4.48 (m, 1H), 4.48-4.36 (m, 1H), 3.28 (t, J=5.6 Hz, 2H), 2.18-2.06 (m, 2H), 1.95-1.81 (m, 3H), 1.96-1.79 (m, 1H), 1.47 (m, 1H), 1.22-1.06 (m, 2H); LC-MS (ESI$^+$) m/z 308.9 (M+H)$^+$.

Step 2—N-[2-[4-(hydroxymethyl)cyclohexyl]indazol-5-yl]-6-(trifluoromethyl)pyridine-2-carboxamide To a solution of [4-(5-bromoindazol-2-yl)cyclohexyl]methanol (800 mg, 2.59 mmol) and 6-(trifluoromethyl)pyridine-2-carboxamide (688 mg, 3.62 mmol, Intermediate ATI) in dioxane (15 mL) was added Pd$_2$(dba)$_3$ (236 mg, 258 umol), Xantphos (299 mg, 517 umol) and Cs$_2$CO$_3$ (1.69 g, 5.17 mmol), then the reaction mixture was stirred at 100° C. for 6 hrs under N$_2$. On completion, the reaction mixture was filtered and the filtrate was concentrated in vacuo to give a residue. The residue was purified by column chromatography (SiO$_2$, PE:EA=1:1 to PE:EA=0:1) to give the title compound (800 mg, 73% yield) as a white solid. $^1$H NMR (400 MHz, DMSO-d$_6$) δ 10.35 (s, 1H), 8.44-8.31 (m, 3H), 8.29 (d, 1H), 8.17 (d, J=7.2 Hz, 1H), 7.65-7.58 (m, 1H), 7.58-7.51 (m, 1H), 4.49 (t, J=5.2 Hz, 1H), 4.42 (m, 1H), 3.29

(t, J=5.6 Hz, 2H), 2.15 (d, J=9.6 Hz, 2H), 1.97-1.84 (m, 4H), 1.49 (m, 1H), 1.24-1.08 (m, 2H); LC-MS (ESI⁺) m/z 419.3 (M+H)⁺.

Step 3—N-[2-(4-formylcyclohexyl)indazol-5-yl]-6-(trifluoromethyl)pyridine-2-carboxamide To a solution of N-[2-[4-(hydroxymethyl)cyclohexyl]indazol-5-yl]-6-(trifluoromethyl)pyridine-2-carboxamide (400 mg, 956 umol) in DCM (3 mL) was added DMP (608 mg, 1.43 mmol, 443 uL), then the reaction mixture was stirred at 25° C. for 2 hrs. On completion, the reaction mixture was quenched with Na₂S₂O₃ (10 mL) and NaHCO₃ (10 mL) and extracted with DCM (2×40 mL). The combined organic phase was washed with NaHCO₃ (20 mL) and brine (2×20 mL), dried with anhydrous Na₂SO₄, filtered and concentrated in vacuo to give the title compound (390 mg, 97% yield) as a brown solid. LC-MS (ESI⁺) m/z 417.3 (M+H)⁺.

3-fluoro-5-(trifluoromethyl)benzoic acid (16.8 mg, 80.7 umol, CAS #161622-05-5) (Intermediate BTX)

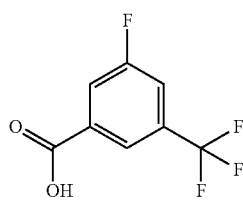

BTX 2-ethynyl-6-(trifluoromethyl)pyridine (Intermediate BTY)

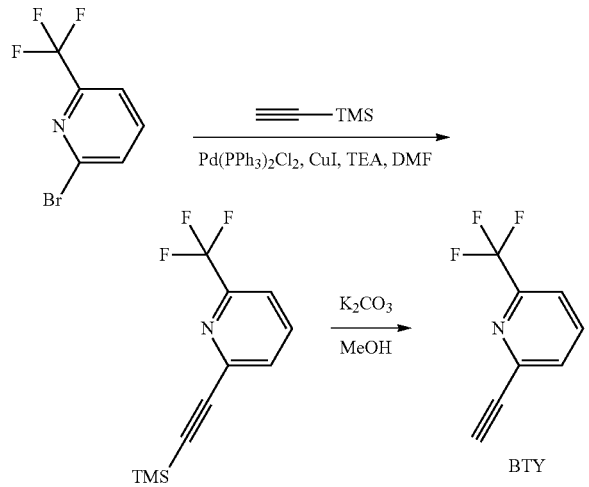

Step 1—Trimethyl-[2-[6-(trifluoromethyl)-2-pyridyl]ethynyl]silane

To a solution of 2-bromo-6-(trifluoromethyl)pyridine (2 g, 8.85 mmol, CAS #189278-27-1), TEA (2.69 g, 26.5 mmol) and ethynyl(trimethyl)silane (2.17 g, 22.1 mmol, CAS #1066-54-2) in DMF (20 mL) was added Pd(PPh₃)₂Cl₂ (621 mg, 884 umol) and CuI (337 mg, 1.77 mmol) under N₂. The reaction was stirred at 110° C. for 16 hrs. On completion, the reaction mixture was diluted with EtOAc (100 mL), which was then washed with brine (4×50 mL). The organic layer was separated and concentrated in vacuo. The residue was purified by column chromatography (SiO₂, petroleum ether/ethyl acetate=1/0 to 10/1) to give the title compound (1.1 g, 51% yield) as brown solid. ¹H NMR (400 MHz, CDCl₃) δ 7.80-7.71 (m, 1H), 7.54 (t, J=7.6 Hz, 2H), 0.24-0.15 (m, 9H).

Step 2—2-ethynyl-6-(trifluoromethyl)pyridine

To a solution of trimethyl[2-[6-(trifluoromethyl)-2-pyridyl]ethynyl]silane (400 mg, 1.64 mmol) in MeOH (4 mL) was added K₂CO₃ (249 mg, 1.81 mmol), and the reaction mixture was stirred at 25° C. for 1 hr. On completion, the reaction mixture was diluted with EtOAc (10 mL) and filtered. Then, the filtrate was concentrated in vacuo and the residue was purified by prep-TLC (PE:EA=10:1, Rf=0.47) to give the title compound (260 mg, 92% yield) as yellow oil. ¹H NMR (400 MHz, CDCl₃) δ=7.91-7.84 (m, 1H), 7.67 (d, J=8.0 Hz, 2H), 3.26 (s, 1H).

((1R,4R)-4-(6-methoxy-5-(4,4,5,5-tetramethyl-1,3,2-dioxaborolan-2-yl)-2H-indazol-2-yl) cyclohexyl)methanol (Intermediate BTZ)

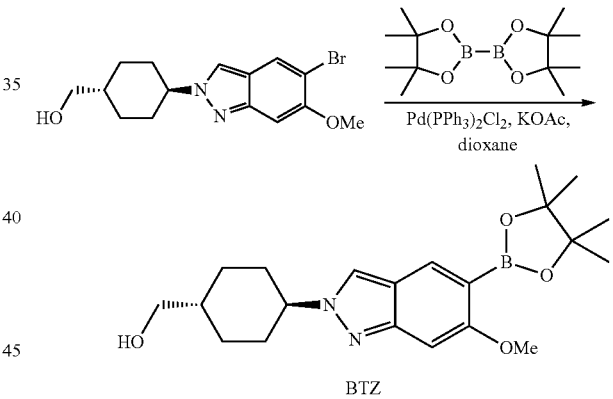

BTZ

A mixture of [4-(5-bromo-6-methoxy-indazol-2-yl)cyclohexyl]methanol (1.00 g, 2.95 mmol, synthesized via Steps 1-3 of Intermediate ATE), 4,4,5,5-tetramethyl-2-(4,4,5,5-tetramethyl-1,3,2-dioxaborolan-2-yl)-1,3,2-dioxaborolane (973 mg, 3.83 mmol, CAS #73183-34-3), Pd(PPh₃)₂Cl₂ (206 mg, 294 umol) and KOAc (578 mg, 5.90 mmol) in dioxane (15 mL) was degassed and purged with N₂ three times, and the mixture was stirred at 90° C. for 16 hrs under N₂ atmosphere for 16 hrs. On completion, the reaction mixture was diluted with EtOAc (30 mL) and filtered. The filtrate was concentrated in vacuo and the residue was purified by flash silica gel chromatography (Silica Flash Column, Eluent of 2050% Ethyl acetate/Petroleum ether gradient) to give the title compound (400 mg, 35% yield) as yellow solid. ¹H NMR (400 MHz, CDCl₃) δ 8.06 (s, 1H), 7.85 (s, 1H), 7.28 (s, 1H), 6.95 (s, 1H), 4.36-4.27 (m, 1H), 3.92-3.84 (m, 3H), 3.57 (d, J=5.6 Hz, 2H), 2.33 (d, J=14.4 Hz, 2H), 2.05-1.90 (m, 3H), 1.72-1.63 (m, 2H), 1.39 (s, 9H), 1.28-1.19 (m, 2H).

(1R,4R)-4-(6-methoxy-5-(4-(6-(trifluoromethyl)pyridin-2-yl)-1H-1,2,3-triazol-1-yl)-2H-indazol-2-yl)cyclohexanecarbaldehyde (Intermediate BUA)

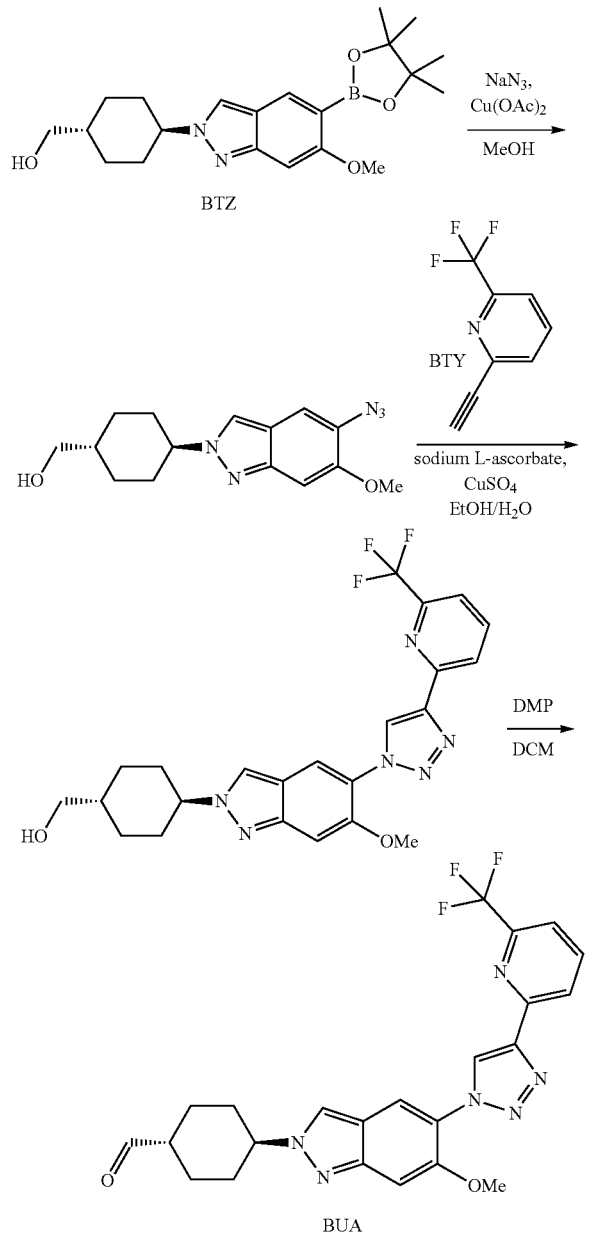

Step 1—((1R,4R)-4-(5-azido-6-methoxy-2H-indazol-2-yl)cyclohexyl)methanol

To a solution of ((1r,4r)-4-(6-methoxy-5-(4,4,5,5-tetramethyl-1,3,2-dioxaborolan-2-yl)-2H-indazol-2-yl) cyclohexyl)methanol (370 mg, 957 umol) in MeOH (6 mL) was added NaN$_3$ (80.9 mg, 1.25 mmol) and Cu(OAc)$_2$ (173 mg, 957 umol). The reaction mixture was stirred at 50° C. for 3 hrs. On completion, the reaction mixture was diluted with EtOAc (50 mL) and filtered. The filtrate was washed with brine (2×30 mL). The organic layer was separated, dried over Na$_2$SO$_4$ and concentrated in vacuo. The residue was purified by prep-TLC (SiO$_2$, 100% EA, Rf=0.4) to give the title compound (150 mg, 52% yield) as yellow solid. LC-MS (ESI$^+$) m/z 302.0 (M+H)$^+$.

Step 2—((1R,4R)-4-(6-methoxy-5-(4-(6-(trifluoromethyl)pyridin-2-yl)-1H-1,2,3-triazol-1-yl)-2H-indazol-2-yl)cyclohexyl)methanol To a solution of ((1r,4r)-4-(5-azido-6-methoxy-2H-indazol-2-yl)cyclohexyl)methanol (140 mg, 464 umol) and 2-ethynyl-6-(trifluoromethyl)pyridine (79.5 mg, 464 umol) in EtOH (3 mL) and H$_2$O (0.5 mL) was added sodium L-ascorbate (27.6 mg, 139 umol) and CuSO$_4$ (22.2 mg, 139 umol) at 25° C. The reaction was stirred at 25° C. for 16 hrs. On completion, the reaction mixture was diluted with EtOAc (50 mL), which was then washed with brine (30 mL×3). The organic layer was separated, dried over Na$_2$SO$_4$ and concentrated in vacuo. The residue was purified by prep-HPLC (column: Phenomenex luna C18 150*25 mm*10 um; mobile phase: [water (0.225% FA)-ACN]; B %: 40%-70%, 11.5 min) to give the title compound (40 mg, 18% yield) as yellow solid. $^1$H NMR (400 MHz, CD$_3$OD) δ 8.83 (s, 1H), 8.43-8.38 (m, 2H), 8.17 (t, J=7.9 Hz, 1H), 8.05 (s, 1H), 7.79 (d, J=7.6 Hz, 1H), 4.51-4.44 (m, 1H), 3.98 (s, 3H), 3.48 (d, J=6.4 Hz, 2H), 2.35-2.26 (m, 2H), 2.11-1.97 (m, 5H), 1.74-1.59 (m, 1H), 1.39-1.21 (m, 2H).

Step 3—(1R,4R)-4-(6-methoxy-5-(4-(6-(trifluoromethyl)pyridin-2-yl)-1H-1,2,3-triazol-1-yl)-2H-indazol-2-yl)cyclohexanecarbaldehyde To a solution of ((1r,4r)-4-(6-methoxy-5-(4-(6-(trifluoromethyl)pyridin-2-yl)-1H-1,2,3-triazol-1-yl)-2H-indazol-2-yl)cyclohexyl)methanol (35.0 mg, 74.1 umol) in DCM (0.5 mL) was added DMP (62.8 mg, 148 umol) at 25° C., then the reaction was stirred at 25° C. for 2 hrs. On completion, the reaction was diluted with DCM (30 mL), then quenched with saturated Na$_2$S$_2$O$_3$ solution (5 mL), followed by addition of saturated NaHCO$_3$ solution (5 mL). The combined mixture was stirred at 25° C. for 30 min. The organic layer was washed with saturated NaHCO$_3$ solution (20 mL×3), dried over Na$_2$SO$_4$ and concentrated in vacuo to give the title compound (34 mg, 97% yield) as yellow solid. LC-MS (ESI$^+$) m/z 471.1 (M+H)$^+$.

4-bromo-5-methoxy-3-methyl-1H-benzimidazol-2-one (Intermediate BUB)

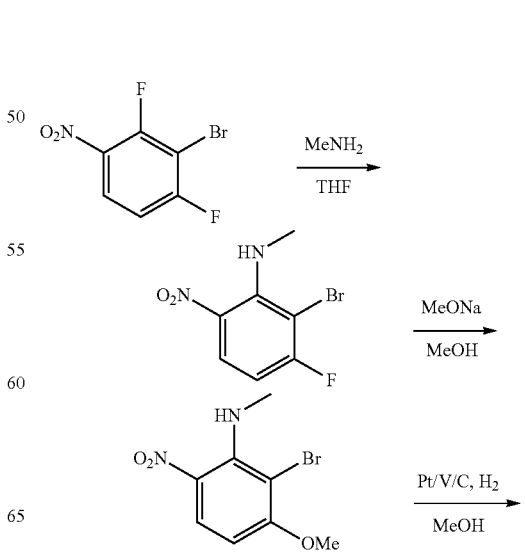

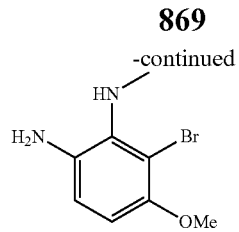

Step 1—2-bromo-3-fluoro-N-methyl-6-nitro-aniline

To a solution of 2-bromo-1,3-difluoro-4-nitro-benzene (10.0 g, 42.0 mmol, CAS #103977-78-2) in THF (120 mL) was added MeNH₂ (2 M, 42.0 mL) at 0° C. under N₂. The reaction was stirred at 0° C. for 1 hr. On completion, the reaction was diluted with EtOAc (200 mL). The organic layer was washed with water (200 mL×3) and concentrated in vacuo to give title compound (10.0 g, 95% yield) as yellow solid. $^1$H NMR (400 MHz, DMSO-$d_6$) δ 7.88 (dd, J=6.0, 9.2 Hz, 1H), 6.76 (dd, J=7.6, 9.2 Hz, 2H), 2.77 (d, J=5.2 Hz, 3H).

Step 2—2-bromo-3-methoxy-N-methyl-6-nitro-aniline

To a solution of 2-bromo-3-fluoro-N-methyl-6-nitro-aniline (10.0 g, 40.1 mmol) in MeOH (100 mL) was added NaOMe (2.82 g, 52.2 mmol) at 0° C. Then the reaction was stirred at 25° C. for 16 hrs. On completion, the reaction was concentrated in vacuo. The residue was purified by column chromatography (SiO₂, petroleum ether/ethyl acetate=20/1) to give title compound (10 g, 95% yield) as yellow solid. $^1$H NMR (400 MHz, DMSO-$d_6$) δ 7.90 (d, J=9.6 Hz, 1H), 6.64 (d, J=9.6 Hz, 1H), 6.53 (q, J=4.8 Hz, 1H), 3.92 (s, 3H), 2.77 (d, J=5.6 Hz, 3H).

Step 3—3-bromo-4-methoxy-N2-methyl-benzene-1,2-diamine

To a solution of 2-bromo-3-methoxy-N-methyl-6-nitro-aniline (5 g, 19.1 mmol) in MeOH (50 mL) was added Pt/V/C (499 mg, 1.92 mmol) under N₂. The suspension was degassed under in vacuo and purged with H₂ several times. The mixture was stirred under H₂ (15 psi) at 25° C. for 16 hours. On completion, the reaction was concentrated in vacuo to give title compound (4.40 g, 99% yield) as red solid. $^1$H NMR (400 MHz, CDCl₃) δ 6.64 (d, J=8.4 Hz, 1H), 6.53 (d, J=8.4 Hz, 1H), 3.82 (s, 3H), 3.66 (s, 2H), 2.71 (s, 3H).

Step 4—4-bromo-5-methoxy-3-methyl-1H-benzimidazol-2-one

A solution of 3-bromo-4-methoxy-N2-methyl-benzene-1,2-diamine (4.4 g, 19.0 mmol) and CDI (3.70 g, 22.8 mmol) in CH₃CN (70 mL) was stirred at 80° C. for 16 hrs under N₂. On completion, the reaction was added into water (200 mL) and filtered. The filter cake was triturated with PE:EA=3:1 at 25° C. for 30 mins and filtered. The solid was collected and dried in vacuo to give title compound (4 g, 81% yield) as gray solid. $^1$H NMR (400 MHz, DMSO-$d_6$) δ=10.93 (s, 1H), 6.90 (d, J=8.4 Hz, 1H), 6.74 (d, J=8.4 Hz, 1H), 3.79 (s, 3H), 3.56 (s, 3H).

3-[5-methoxy-3-methyl-2-oxo-4-(4-piperidyl)benzimidazol-1-yl]piperidine-2,6-dione (Intermediate BUC)

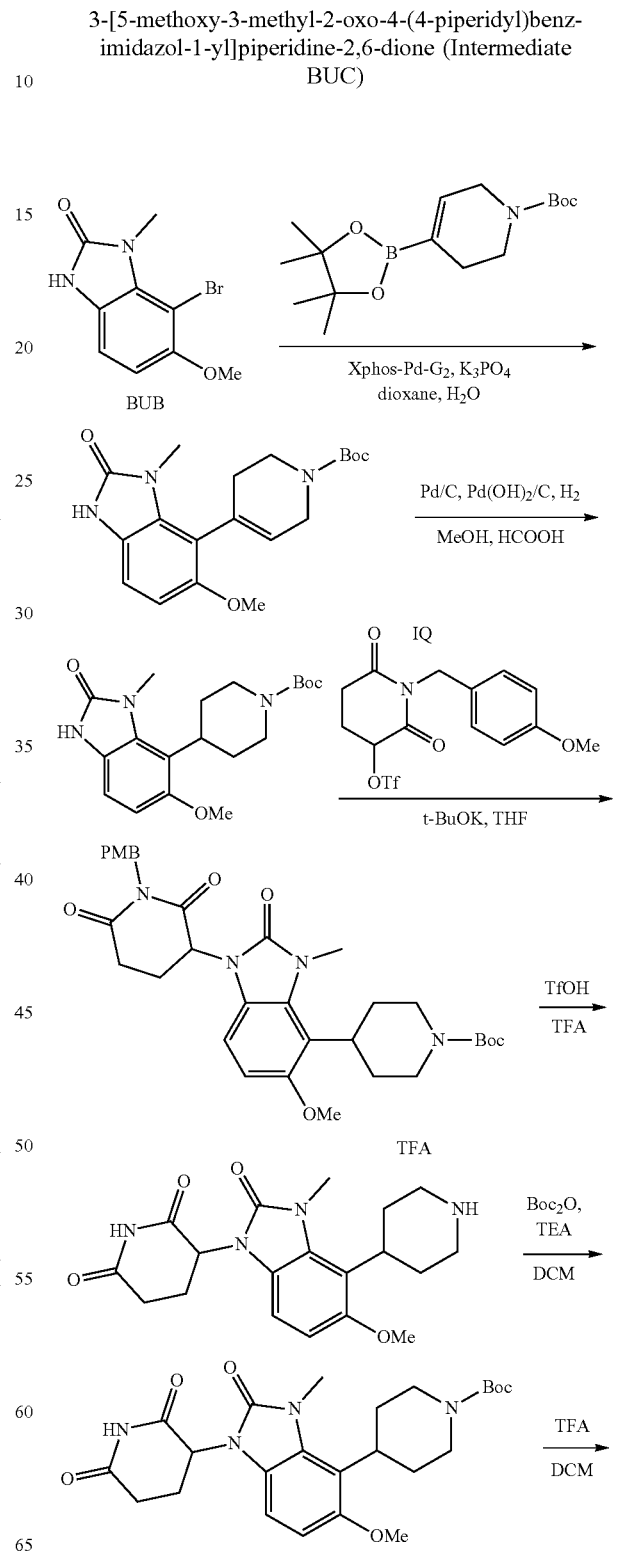

-continued

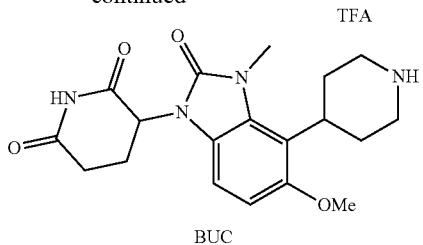

BUC

Step 1—Tert-butyl 4-(5-methoxy-3-methyl-2-oxo-1H-benzimidazol-4-yl)-3,6-dihydro-2H-pyridine-1-carboxylate A solution of 4-bromo-5-methoxy-3-methyl-1H-benzimidazol-2-one (2.00 g, 7.78 mmol, Intermediate BUB), tert-butyl 4-(4,4,5,5-tetramethyl-1,3,2-dioxaborolan-2-yl)-3,6-dihydro-2H-pyridine-1-carboxylate (3.13 g, 10.1 mmol, CAS #286961-14-6), $K_3PO_4$ (3.30 g, 15.5 mmol) and XPHOS-PD-$G_2$ (306 mg, 388 umol) in dioxane (50 mL) and $H_2O$ (10 mL) was stirred at 80° C. for 16 hrs under $N_2$. On completion, the reaction was filtered and filtrate was concentrated in vacuo. The residue was purified by column chromatography (SiO$_2$, petroleum ether/ethyl acetate=3/1 to 1/1) to give title compound as gray solid. $^1$H NMR (400 MHz, DMSO-d$_6$) δ 10.67 (s, 1H), 6.81 (d, J=8.4 Hz, 1H), 6.62 (d, J=8.4 Hz, 1H), 5.58 (s, 1H), 3.69 (s, 3H), 3.59-3.47 (m, 2H), 3.18 (s, 3H), 2.42 (s, 1H), 2.14 (d, J=16.8 Hz, 1H), 1.43 (s, 9H), 1.06 (s, 2H).

Step 2—Tert-butyl 4-(5-methoxy-3-methyl-2-oxo-1H-benzimidazol-4-yl)piperidine-1-carboxylate To a solution of tert-butyl 4-(5-methoxy-3-methyl-2-oxo-1H-benzimidazol-4-yl)-3,6-dihydro-2H-pyridine-1-carboxylate (600 mg, 1.67 mmol) in MeOH (20 mL) was added HCOOH (80.2 mg, 1.67 mmol), Pd/C (600 mg, 563 umol, 10 wt %) and Pd(OH)$_2$/C (600 mg, 427 umol, 10 wt %) under $N_2$ atmosphere. The suspension was degassed under vacuum and purged with $H_2$ several times. The mixture was stirred under $H_2$ (50 Psi) at 60° C. for 48 hrs. On completion, the reaction mixture was filtered and filtrate was concentrated in vacuo to give title compound (570 mg, 87% yield) as black solid. $^1$H NMR (400 MHz, CDCl$_3$) δ 6.83 (d, J=8.4 Hz, 1H), 6.55 (d, J=8.4 Hz, 1H), 4.16 (s, 2H), 3.71 (s, 3H), 3.58 (s, 3H), 3.35-3.30 (m, 1H), 2.76-2.62 (m, 2H), 2.43-2.29 (m, 2H), 1.53 (d, J=12.4 Hz, 2H), 1.43 (s, 9H), 1.38-1.36 (m, 1H).

Step 3—Tert-butyl 4-[5-methoxy-1-[1-[(4-methoxyphenyl)methyl]-2,6-dioxo-3-piperidyl]-3-methyl-2-oxo-benzimidazol-4-yl]piperidine-1-carboxylate To a solution of tert-butyl 4-(5-methoxy-3-methyl-2-oxo-1H-benzimidazol-4-yl)piperidine-1-carboxylate (1.49 g, 4.12 mmol) in THF (30 mL) was added t-BuOK (693 mg, 6.18 mmol) at 0° C. and the reaction was stirred for 0.5 hr. Then, a solution of [1-[(4-methoxyphenyl) methyl]-2,6-dioxo-3-piperidyl] trifluoromethanesulfonate (2.36 g, 6.18 mmol, Intermediate IQ) in THF (20 mL) solution was added dropwise into the mixture slowly. The reaction was stirred at 0° C. for 1.5 hrs. On completion, the reaction was quenched with NH$_4$Cl solution (10 mL). The mixture was diluted with water (150 mL) and extracted with EA (200 mL). The combined layers were washed with water (150 mL×2), dried over Na$_2$SO$_4$ and filtered. The filtrate was concentrated in vacuo. The residue was purified by reverse-phase HPLC (0.1% FA condition) and column chromatography (SiO$_2$, petroleum ether/ethyl acetate=2/1 to 1/2) to give title compound (1.53 g, 62% yield) as yellow solid. $^1$H NMR (400 MHz, CDCl$_3$) δ 7.39-7.35 (m, 2H), 6.83 (d, J=8.4 Hz, 2H), 6.48 (d, J=8.4 Hz, 1H), 6.27 (d, J=8.4 Hz, 1H), 5.22-5.13 (m, 1H), 4.97 (s, 2H), 4.24 (s, 2H), 3.78 (d, J=13.6 Hz, 6H), 3.66 (s, 3H), 3.47-3.37 (m, 1H), 3.04-2.96 (m, 1H), 2.87-2.71 (m, 3H), 2.67-2.53 (m, 1H), 2.42 (q, J=11.6 Hz, 2H), 2.19-2.10 (m, 1H), 1.63-1.55 (m, 2H), 1.51 (s, 9H).

Step 4—3-[5-methoxy-3-methyl-2-oxo-4-(4-piperidyl)benzimidazol-1-yl]piperidine-2,6-dione To a solution of tert-butyl 4-[5-methoxy-1-[1-[(4-methoxyphenyl)methyl]-2,6-dioxo-3-piperidyl]-3-methyl-2-oxo-benzimidazol-4-yl]piperidine-1-carboxylate (1.53 g, 2.58 mmol) in TFA (8 mL) was added TfOH (3.40 g, 22.6 mmol). The reaction was stirred at 70° C. for 4 hrs. On completion, the reaction was concentrated in vacuo to give title compound (1.26 g, 100% yield, TFA) as brown oil. LC-MS (ESI$^+$) m/z 373.3 (M+H)$^+$.

Step 5—Tert-butyl 4-[1-(2,6-dioxo-3-piperidyl)-5-methoxy-3-methyl-2-oxo-benzimidazol-4-yl] piperidine-1-carboxylate To a solution of 3-[5-methoxy-3-methyl-2-oxo-4-(4-piperidyl)benzimidazol-1-yl]piperidine-2,6-dione (1.26 g, 2.59 mmol) and TEA (2.62 g, 25.9 mmol) in DCM (15 mL) was added Boc$_2$O (847 mg, 3.89 mmol) at 0° C. Then the reaction was stirred at 25° C. for 1 hr. On completion, the reaction was diluted with DCM (30 mL). The organic layer was washed with water (20 mL×3), dried over Na$_2$SO$_4$ and filtered. The filtrate was concentrated in vacuo. The residue was purified by reverse phase (0.1% FA condition) to give title compound (0.9 g, 73% yield) as white solid. $^1$H NMR (400 MHz, DMSO-d$_6$) δ 11.08 (s, 1H), 6.92 (d, J=8.8 Hz, 1H), 6.72 (d, J=8.8 Hz, 1H), 5.37-5.29 (m, 1H), 4.08-3.95 (m, 2H), 3.73 (s, 3H), 3.59 (s, 3H), 3.52-3.43 (m, 1H), 2.94-2.76 (m, 3H), 2.71-2.61 (m, 2H), 2.28-2.17 (m, 2H), 2.02-1.93 (m, 1H), 1.59 (d, J=11.2 Hz, 2H), 1.44 (s, 9H).

Step 6—3-[5-methoxy-3-methyl-2-oxo-4-(4-piperidyl)benzimidazol-1-yl]piperidine-2,6-dione To a solution of tert-butyl 4-[1-(2,6-dioxo-3-piperidyl)-5-methoxy-3-methyl-2-oxo-benzimidazol-4-yl] piperidine-1-carboxylate (500 mg, 1.06 mmol) in DCM (5 mL) was added TFA (1.5 mL). The reaction was stirred at 25° C. for 1 hr. On completion, the reaction was concentrated in vacuo to give title compound (390 mg, 75% yield, TFA) as brown oil. LC-MS (ESI$^+$) m/z 373.2 (M+H)$^+$.

5-Bromo-4-(dimethylamino)-2-nitro-benzaldehyde (Intermediate BUD)

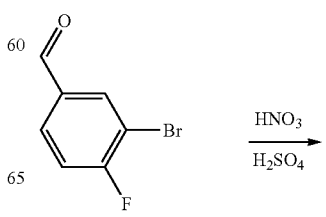

873
-continued

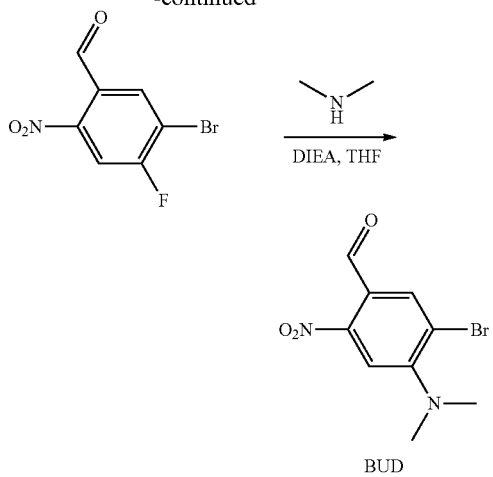

Step 1—5-Bromo-4-fluoro-2-nitro-benzaldehyde

To a solution of 3-bromo-4-fluoro-benzaldehyde (3.00 g, 14.7 mmol, CAS #77771-02-9) in $H_2SO_4$ (18 mL) was added $HNO_3$ (2.78 g, 29.5 mmol, 1.99 mL, 67% solution) at 0° C., the reaction was stirred at 25° C. for 3 hrs. On completion, the reaction mixture was poured into ice water (50 mL), then extracted with EA (2×30 mL). The organic phase was washed with brine, dried over $Na_2SO_4$, filtered and the filtrate was concentrated in vacuo to give the title compound (2.20 g, 60% yield) as a white solid. $^1H$ NMR (400 MHz, DMSO-$d_6$) δ 10.14 (s, 1H), 8.31 (d, J=8.4 Hz, 1H), 8.25 (d, J=7.2 Hz, 1H).

Step 2—5-Bromo-4-(dimethylamino)-2-nitro-benzaldehyde

To a solution of 5-bromo-4-fluoro-2-nitro-benzaldehyde (2.00 g, 8.06 mmol) and N-methylmethanamine (1.97 g, 24.1 mmol, 2.22 mL, HCl, CAS #124-40-3) in THF (20 mL) was added DIEA (5.21 g, 40.3 mmol, 7.02 mL). Then the reaction mixture was stirred at 100° C. for 12 hrs. On completion, the reaction mixture was concentrated in vacuo to give a residue. The residue was purified by reverse phase (0.1% FA condition) to give title compound (1.70 g, 77% yield) as a yellow solid. $^1H$ NMR (400 MHz, DMSO-$d_6$) δ 9.97 (s, 1H), 8.08 (s, 1H), 7.58 (s, 1H), 2.98 (s, 6H).

N-[6-(dimethylamino)-2-(4-formylcyclohexyl)indazol-5-yl]-6-(trifluoromethyl)pyridine-2-carboxamide (Intermediate BUE)

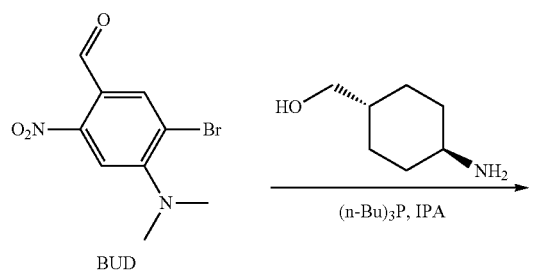

874
-continued

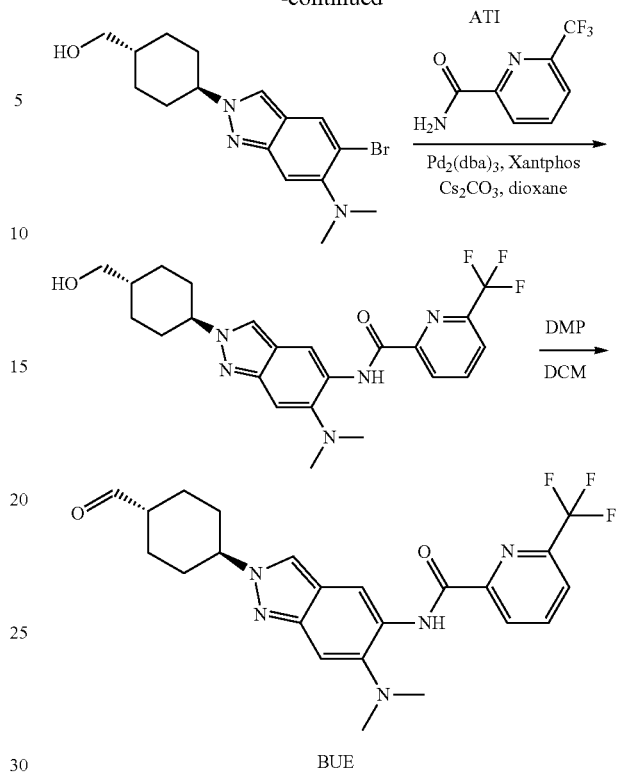

Step 1—[4-[5-Bromo-6-(dimethylamino)indazol-2-yl]cyclohexyl]methanol

A solution of 5-bromo-4-(dimethylamino)-2-nitro-benzaldehyde (1.60 g, 5.86 mmol, Intermediate BUD) and (4-aminocyclohexyl)methanol (756 mg, 5.86 mmol, CAS #1467-84-1) in IPA (30 mL) was stirred at 80° C. for 12 hrs. Then the mixture was cooled to 25° C., tributylphosphane (3.56 g, 17.5 mmol, 4.34 mL) was added to the mixture which was then stirred at 80° C. for 6 hrs. On completion, the reaction mixture was concentrated in vacuo to give a residue. The residue was purified by reverse phase (0.1% FA condition), then purified by column chromatography ($SiO_2$, Petroleum ether/Ethyl acetate=10/1 to 1/2) to give the title compound (1.70 g, 82% yield) as yellow oil. LC-MS (ESI$^+$) m/z 351.9 (M+H)$^+$.

Step 2—N-[6-(dimethylamino)-2-[4-(hydroxymethyl)cyclohexyl]indazol-5-yl]-6-(trifluoromethyl)pyridine-2-carboxamide To a solution of [4-[5-bromo-6-(dimethylamino)indazol-2-yl]cyclohexyl]methanol (300 mg, 851 umol), 6-(trifluoromethyl)pyridine-2-carboxamide (178 mg, 936 umol, Intermediate ATI) in dioxane (5 mL) was added $Cs_2CO_3$ (554 mg, 1.70 mmol), $Pd_2(dba)_3$ (77.9 mg, 85.1 umol) and Xantphos (49.2 mg, 85.1 umol). Then the reaction mixture was stirred at 100° C. for 12 hrs under $N_2$. On completion, the reaction mixture was filtered and the filtrate was concentrated in vacuo to give a residue. The residue was purified by reverse phase (0.1% FA condition) to give the title compound (230 mg, 58% yield) as a yellow solid. $^1H$ NMR (400 MHz, DMSO-$d_6$) δ 11.04 (s, 1H), 8.71 (s, 1H), 8.50-8.43 (m, 1H), 8.43-8.37 (m, 1H), 8.35 (s, 1H), 8.20 (dd, J=0.8, 7.6 Hz, 1H), 7.44 (s, 1H), 4.49 (t, J=5.2 Hz, 1H), 4.43-4.31 (m, 1H), 3.29 (t, J=5.6 Hz, 2H), 2.74 (s, 6H), 2.20-2.08 (m, 2H), 1.97-1.80 (m, 4H), 1.55-1.40 (m, 1H), 1.23-1.05 (m, 2H); LC-MS (ESI+) m/z 462.0 (M+H)+.

Step 3—N-[6-(dimethylamino)-2-(4-formylcyclohexyl)indazol-5-yl]-6-(trifluoromethyl)pyridine-2-carboxamide To a solution of N-[6-(dimethylamino)-2-[4-(hydroxymethyl)cyclohexyl]indazol-5-yl]-6-(trifluoromethyl) pyridine-2-carboxamide (220 mg, 476 umol) in DCM (2 mL) was added DMP (242 mg, 572 umol, 177 uL), then the reaction mixture was stirred at 25° C. for 2 hrs. On completion, the reaction mixture was quenched with Na$_2$S$_2$O$_3$ (15 mL) and extracted with DCM (2×30 mL). The combined organic phase was washed with NaHCO$_3$ and brine (2×15 mL), dried with anhydrous Na$_2$SO$_4$, filtered and concentrated in vacuo to the title compound (210 mg, 95% yield) as a yellow solid. $^1$H NMR (400 MHz, DMSO-d$_6$) δ 11.04 (s, 1H), 9.64 (s, 1H), 8.71 (s, 1H), 8.52-8.44 (m, 1H), 8.43-8.37 (m, 1H), 8.35 (s, 1H), 8.20 (d, J=7.8 Hz, 1H), 7.44 (s, 1H), 4.48-4.36 (m, 1H), 2.74 (s, 6H), 2.47-2.37 (m, 1H), 2.23-2.15 (m, 2H), 2.15-2.06 (m, 2H), 2.02-1.89 (m, 2H), 1.51-1.38 (m, 2H); LC-MS (ESI+) m/z 460.2 (M+H)+.

N-[6-(difluoromethyl)-2-[3-(iodomethyl)cyclobutyl]indazol-5-yl]-6-(trifluoromethyl) pyridine-2-carboxamide (Intermediate BUF)

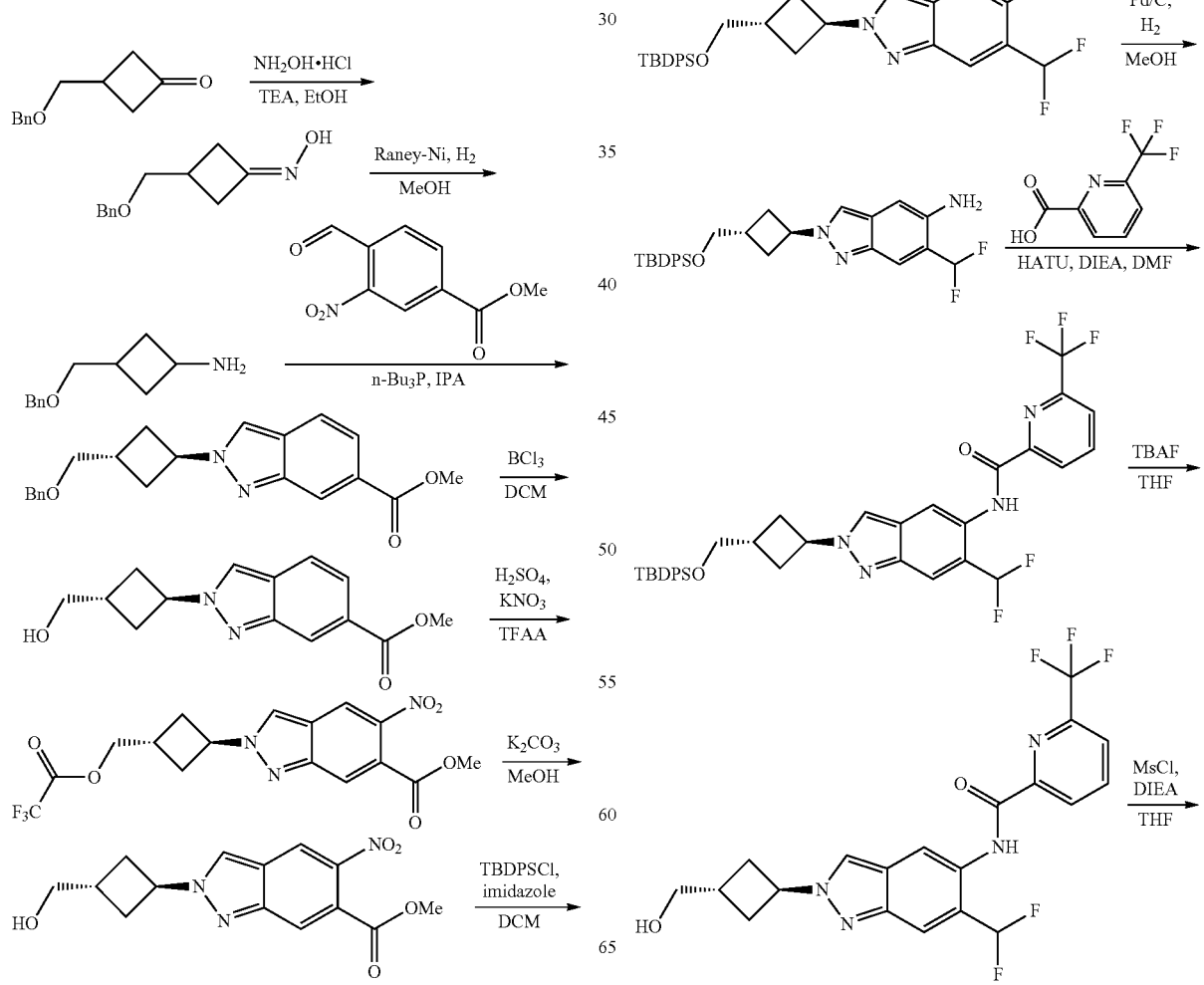

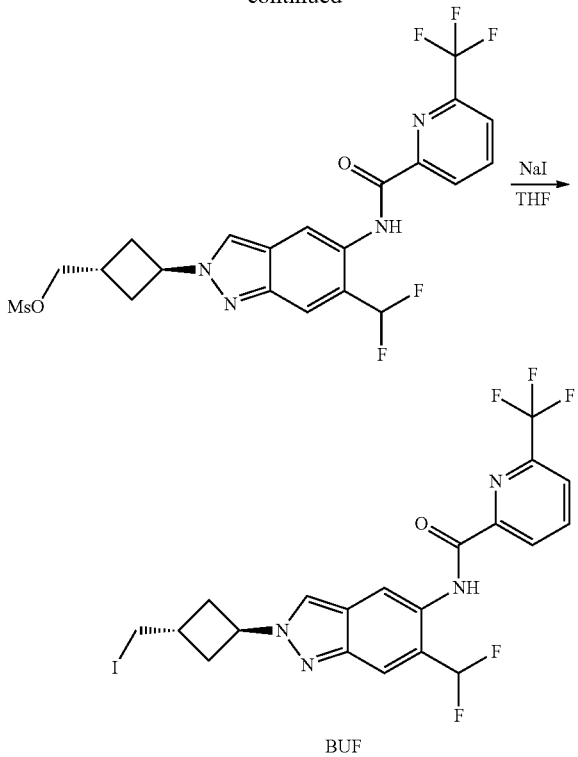

Step 1—3-(Benzyloxymethyl)cyclobutanone oxime

To a solution of 3-(benzyloxymethyl)cyclobutanone (10 g, 52.5 mmol, CAS #172324-67-3) in EtOH (100 mL) was added TEA (5.32 g, 52.5 mmol) and $NH_2OH \cdot HCl$ (3.65 g, 52.5 mmol). The mixture was then stirred at 40° C. for 16 hrs. On completion, the reaction mixture was quenched with water (100 mL) and extracted with ethyl acetate (2×200 mL). The combined organic layers were dried over $Na_2SO_4$, filtered and the filtrate was concentrated under reduced pressure to give the title compound (10.0 g, 92% yield) as colorless oil. $^1H$ NMR (400 MHz, CHLOROFORM-d) δ 7.44-7.27 (m, 5H), 4.55 (s, 2H), 3.53 (d, J=6.0 Hz, 2H), 3.11-2.95 (m, 2H), 2.75-2.64 (m, 3H). LC-MS (ESI$^+$) m/z 206.1 (M+H)$^+$.

Step 2—3-(Benzyloxymethyl)cyclobutanamine

To a solution of 3-(benzyloxymethyl)cyclobutanone oxime (10 g, 48.7 mmol) in MeOH (100 mL) was added Raney-Ni (417 mg, 4.87 mmol) at 25° C. under nitrogen atmosphere. After addition, the mixture was stirred at 50° C. for 4 hrs under $H_2$ atmosphere (50 psi). On completion, the mixture was filtrated and the filtrate was concentrated under reduced pressure. The filtrate was concentrated under reduced pressure to give the title compound (9.00 g, 96% yield) as colorless oil. LC-MS (ESI$^+$) m/z 192.2 (M+H)$^+$.

Step 3—Methyl 2-[3-(benzyloxymethyl)cyclobutyl]indazole-6-carboxylate

To a solution of methyl 4-formyl-3-nitro-benzoate (9.84 g, 47.0 mmol, CAS #153813-69-5) in IPA (180 mL) was added 3-(benzyloxymethyl)cyclobutanamine (9 g, 47.0 mmol) at 25° C. After addition, the mixture was stirred at 80° C. for 4 hrs. Next, tributylphosphane (28.5 g, 141 mmol, CAS #998-40-3) was added dropwise at 0° C. The resulting mixture was stirred at 80° C. for 16 hrs. On completion, the mixture was concentrated under reduced pressure to afford a residue and the residue was purified by column chromatography ($SiO_2$, petroleum ether/ethyl acetate=10/1 to 2/1) to give the title compound (4.20 g, 24% yield) as yellow oil. LC-MS (ESI$^+$) m/z 351.3 (M+H)$^+$.

Step 4—Methyl 2-[3-(hydroxymethyl)cyclobutyl]indazole-6-carboxylate

To a solution of methyl 2-[3-(benzyloxymethyl)cyclobutyl]indazole-6-carboxylate (4.2 g, 11.9 mmol) in DCM (30 mL) was added $BCL_3$ (1 M in CDM, 23.97 mL) at 0° C. Then the mixture was stirred at 25° C. for 4 hrs. On completion, the mixture was quenched with water (50 mL) and extracted with DCM (3×80 mL). The organic layer was dried over $Na_2SO_4$ and concentrated under reduced pressure to give the title compound (3.00 g, 96% yield) as a yellow solid. $^1H$ NMR (400 MHz, MeOD) δ 8.42-8.33 (m, 2H), 7.77-7.73 (m, 1H), 7.68-7.63 (m, 1H), 5.30-5.21 (m, 1H), 3.93 (s, 3H), 3.74 (d, J=6.4 Hz, 2H), 2.88-2.77 (m, 2H), 2.70-2.59 (m, 1H), 2.56-2.48 (m, 2H).

Step 5—Methyl 5-nitro-2-((1r,3r)-3-((2,2,2-trifluoroacetoxy)methyl)cyclobutyl)-2H-indazole-6-carboxylate A mixture of methyl 2-[3-(hydroxymethyl)cyclobutyl]indazole-6-carboxylate (3.00 g, 11.5 mmol) in TFAA (75.5 g, 359 mmol) was stirred at 25° C. for 1 hr. Then the reaction mixture was cool to 0° C. and $H_2SO_4$ (6.78 g, 69.1 mmol) was added at 0° C. Then $KNO_3$ (2.07 g, 20.4 mmol) was added to the reaction mixture at 0° C. and the reaction mixture was stirred at 0° C. for 2 hrs. On completion, the reaction mixture was poured into water (150 mL, 0° C.). The mixture was extracted with EA (3×200 mL) and the organic layer was washed with $NaHCO_3$ aqueous until the pH=8. The combined organic layer was concentrated under reduced pressure to afford a residue. The residue was purified by column chromatography ($SiO_2$, petroleum ether/ethyl acetate=5/1 to 1/1) to give the title compound (3.50 g, 84% yield) as a yellow solid. $^1H$ NMR (400 MHz, $CDCl_3$) δ 8.41 (s, 1H), 8.24-8.22 (m, 1H), 8.08 (s, 1H), 5.27-5.18 (m, 1H), 4.56 (d, J=5.6 Hz, 2H), 3.95 (s, 3H), 3.15-2.97 (m, 3H), 2.65-2.59 (m, 2H).

Step 6—Methyl 2-[3-(hydroxymethyl)cyclobutyl]-5-nitro-indazole-6-carboxylate To a solution of methyl 5-nitro-2-((1r,3r)-3-((2,2,2-trifluoroacetoxy)methyl)cyclobutyl)-2H-indazole-6-carboxylate (3.3 g, 10.8 mmol) in MeOH (50 mL) was added $K_2CO_3$ (2.69 g, 19.4 mmol). The mixture was stirred at 25° C. for 2 hrs. On completion, water (30 mL) was added to the reaction mixture and the mixture was extracted with EA (3×80 mL). The organic layer was dried over $Na_2SO_4$ and filtered. The filtrate was concentrated under reduced pressure to give the title compound (2.51 g, 100% yield) as yellow oil. LC-MS (ESI$^+$) m/z 306.1 (M+H)$^+$.

Step 7—Methyl 2-[3-[[tert-butyl(diphenyl)silyl]oxymethyl]cyclobutyl]-5-nitro-indazole-6-carboxylate To a mixture of methyl 2-[3-(hydroxymethyl)cyclobutyl]-5-nitro-indazole-6-carboxylate (3.00 g, 9.83 mmol), and tert-butyl-chloro-diphenyl-silane (3.24 g, 11.7 mmol) in DMF (30 mL) was added imidazole (2.01 g, 29.4 mmol) and tert-butyl-chloro-diphenyl-silane (3.24 g, 11.7 mmol) at 0° C. The mixture was then stirred at 25° C. for 3 hrs under $N_2$ atmosphere. On completion, the mixture was quenched with $H_2O$ (20 mL) and extracted with EA (3×100 mL). The organic layer was concentrated under reduced pressure to afford a residue. The residue was purified by column chromatography ($SiO_2$, petroleum ether/ethyl acetate=10/1 to 2/1) to give the title compound (2.50 g, 37% yield) as a yellow solid. LC-MS ($ESI^+$) m/z 544.4 $(M+H)^+$.

Step 8—2-[3-[[Tert-butyl(diphenyl)silyl]oxymethyl] cyclobutyl]-5-nitro-indazole-6-carboxylic Acid To a solution of methyl 2-[3-[[tert-butyl(diphenyl)silyl] oxymethyl]cyclobutyl]-5-nitro-indazole-6-carboxylate (2.6 g, 4.78 mmol) in THF (40 mL) and $H_2O$ (10 mL) was added LiOH $H_2O$ (1.00 g, 23.9 mmol). The mixture was then stirred at 50° C. for 16 hrs. On completion, the mixture was concentrated under reduced pressure to remove the THF and the mixture was adjusted pH=3 with HCl (1 M). Then the mixture was extracted with EA (3×100 mL) and dried over $Na_2SO_4$. The organic layer was filtered and the filtrate was concentrated under reduced pressure to give the title compound (2.50 g, 77% yield) as a yellow solid. LC-MS ($ESI^+$) m/z 530.1 $(M+H)^+$.

Step 9—Isopropoxycarbonyl 2-[3-[[tert-butyl(diphenyl)silyl]oxymethyl]cyclobutyl]-5-nitro-indazole-6-carboxylate To a solution of 2-[3-[[tert-butyl(diphenyl)silyl]oxymethyl]cyclobutyl]-5-nitro-indazole-6-carboxylic acid (2.50 g, 4.72 mmol) in THF (50 mL) was added TEA (1.43 g, 14.1 mmol) and isopropyl carbonochloridate (578 mg, 4.72 mmol, CAS #108-23-6). Then the mixture was stirred at 25° C. for 1 hr. On completion, the reaction mixture was concentrated under reduced pressure to give the title compound (2.50 g, 86% yield) as yellow liquid. LC-MS ($ESI^+$) m/z 616.2 $(M+H)^+$.

Step 10—[2-[3-[[Tert-butyl (diphenyl)silyl]oxymethyl]cyclobutyl]-5-nitro-indazol-6-yl]methanol A mixture of isopropoxycarbonyl 2-[3-[[tert-butyl(diphenyl)silyl]oxymethyl]cyclobutyl]-5-nitro-indazole-6-carboxylate (2.50 g, 4.06 mmol) in THF (50 mL) was added $LiBH_4$ (770 mg, 35.3 mmol) at 0° C. under nitrogen atmosphere. The mixture was degassed and purged with $N_2$ three times, and then the mixture was stirred at 0° C. for 2 hrs under $N_2$ atmosphere. On completion, the reaction was quenched with $H_2O$ (15 mL) at 0° C. and the mixture was extracted with EA (2×150 mL). The organic layers were combined and dried over $Na_2SO_4$. The organic layer was concentrated under reduced pressure to afford a residue. The residue was purified by column chromatography ($SiO_2$, petroleum ether/ethyl acetate=5/1 to 1/1) to give the title compound (2.00 g, 88% yield) as a yellow solid. $^1H$ NMR (400 MHz, $CDCl_3$-d) δ 8.63 (s, 1H), 8.20 (s, 1H), 7.94 (s, 1H), 7.73-7.70 (m, 4H), 7.47-7.40 (m, 6H), 5.26-5.17 (m, 1H), 5.01 (s, 2H), 3.83 (d, J=4.8 Hz, 2H), 2.90-2.83 (m, 2H), 2.76-2.70 (m, 1H), 2.68-2.61 (m, 2H), 2.38 (s, 1H), 1.13 (s, 9H). LC-MS ($ESI^+$) m/z 516.3 $(M+H)^+$.

Step 11—2-[3-[[Tert-butyl(diphenyl)silyl]oxymethyl]cyclobutyl]-5-nitro-indazole-6-carbaldehyde To a solution of [2-[3-[[tert-butyl(diphenyl)silyl]oxymethyl]cyclobutyl]-5-nitro-indazol-6-yl]methanol (1.90 g, 3.68 mmol) in DCM (20 mL) was added $MnO_2$ (6.41 g, 73.6 mmol). Then the reaction mixture was stirred at 25° C. for 2 hrs. On completion, the reaction mixture was filtered through celatom and the filtrate was concentrated under reduced pressure to give the title compound (1.80 g, 95% yield) as a yellow solid. LC-MS ($ESI^+$) m/z 514.2 $(M+H)^+$.

Step 12-Tert-butyl-[[3-[6-(difluoromethyl)-5-nitroindazol-2-yl]cyclobutyl]methoxy]-diphenyl-silane To a stirred solution of 2-[3-[[tert-butyl(diphenyl)silyl]oxymethyl]cyclobutyl]-5-nitro-indazole-6-carbaldehyde (900 mg, 1.75 mmol) in DCM (15 mL) under nitrogen atmosphere was added DAST (1.13 g, 7.01 mmol) at 0° C. Then the reaction mixture was stirred at 25° C. for 16 hrs under nitrogen atmosphere. On completion, the reaction was quenched with cold water (1 mL) and extracted with DCM (3×50 mL). The organic layer was washed with saturated sodium chloride (50 mL), dried over sodium sulfate, filtered and concentrated under reduced pressure to give the title compound (900 mg, 95% yield) as a yellow solid. LC-MS ($ESI^+$) m/z 536.2 $(M+H)^+$.

Step 13—2-[3-[[Tert-butyl(diphenyl)silyl]oxymethyl]cyclobutyl]-6-(difluoromethyl)indazol-5-amine A mixture of tert-butyl-[[3-[6-(difluoromethyl)-5-nitroindazol-2-yl]cyclobutyl]methoxy]-diphenyl-silane (800 mg, 1.49 mmol) and Pd/C (880 mg, 746 umol, 10 wt %) in MeOH (15 mL) was degassed and purged with $H_2$ three 3 times, and then the mixture was stirred at 25° C. for 3 hrs under $H_2$ atmosphere (15 psi). On completion, the reaction mixture was filtered through celatom and the filter cake was washed with MeOH (3×20 mL). The filtrate was concentrated under reduced pressure to give the title compound (700 mg, 78% yield) as a yellow solid. LC-MS ($ESI^+$) m/z 506.3 $(M+H)^+$.

Step 14—N-[2-[3-[[tert-butyl(diphenyl)silyl]oxymethyl]cyclobutyl]-6-(difluoromethyl)indazol-5-yl]-6-(trifluoromethyl)pyridine-2-carboxamide To a solution of 6-(trifluoromethyl)pyridine-2-carboxylic acid (661 mg, 3.46 mmol, CAS #131747-42-7) in DMF (10 mL) was added DIEA (536 mg, 4.15 mmol) and HATU (1.58 g, 4.15 mmol) and the mixture was stirred at 25° C. for 1 hr. Then the mixture was added to a solution of 2-[3-[[tert-butyl (diphenyl) silyl]oxymethyl]cyclobutyl]-6-(difluoromethyl) indazol-5-amine (700 mg, 1.38 mmol) in DMF (10 mL) at 25° C. and the mixture was stirred at 25° C. for 1 hr. On completion, the reaction mixture was quenched with $H_2O$ (0.5 mL) and concentrated under reduced pressure to afford a residue. The residue was purified by column chromatography ($SiO_2$, petroleum ether/ethyl acetate=10/1 to 1/1) to give the title compound (750 mg, 74% yield) as a yellow solid. $^1H$ NMR (400 MHz, CHLOROFORM-d) δ 10.53 (s, 1H), 8.73 (s, 1H), 8.51 (d, J=7.6 Hz, 1H), 8.18-8.12 (m, 1H), 8.03 (s, 1H), 7.94 (s, 1H), 7.91-7.88 (m, 1H), 7.73-7.70 (m, 4H), 7.47-7.40 (m, 6H), 6.97-6.68 (m, 1H), 5.27-5.16 (m, 1H), 3.83 (d, J=5.2 Hz, 2H), 2.93-2.83 (m, 2H), 2.77-2.69 (m, 1H), 2.67-2.60 (m, 2H), 1.13 (s, 8H). LC-MS ($ESI^+$) m/z 679.3 $(M+H)^+$.

Step 15—N-[6-(difluoromethyl)-2-[3-(hydroxymethyl)cyclobutyl]indazol-5-yl]-6-(trifluoromethyl) pyridine-2-carboxamide To a solution of N-[2-[3-[[tert-butyl(diphenyl)silyl]oxymethyl]cyclobutyl]-6-(difluoromethyl)indazol-5-yl]-6-(trifluoromethyl)pyridine-2-carboxamide (750 mg, 1.10 mmol) in THF (10 mL) was added TBAF (1 M in THF, 1.33 mL) at 0° C. Then the mixture was stirred at 25° C. for 2 hrs. On completion, the reaction mixture was concentrated under reduced pressure to afford a residue. The residue was purified by column chromatography (SiO$_2$, petroleum ether/ethyl acetate=10/1 to 1/1) to give the title compound (450 mg, 92% yield) as yellow oil. $^1$H NMR (400 MHz, MeOD-d$_4$) δ 8.54 (s, 1H), 8.48 (d, J=7.6 Hz, 1H), 8.41 (s, 1H), 8.31 (t, J=7.6 Hz, 1H), 8.07 (d, J=7.6 Hz, 1H), 7.93 (s, 1H), 7.17-6.88 (m, 1H), 5.49 (s, 1H), 5.32-5.22 (m, 1H), 3.75 (d, J=6.4 Hz, 2H), 2.88-2.80 (m, 2H), 2.72-2.60 (m, 1H), 2.57-2.50 (m, 2H).

Step 16—[3-[6-(Difluoromethyl)-5-[[6-(trifluoromethyl)pyridine -2-carbonyl]amino]indazol-2-yl]cyclobutyl]methyl methanesulfonate To a solution of N-[6-(difluoromethyl)-2-[3-(hydroxymethyl)cyclobutyl]indazol-5-yl]-6-(trifluoromethyl)pyridine-2-carboxamide (200 mg, 454 umol) in DCM (4 mL) was added TEA (68.9 mg, 681 umol) and methanesulfonyl chloride (410 mg, 3.58 mmol) at 0° C. The mixture was then stirred at 25° C. for 16 hrs. On completion, the reaction mixture was quenched by H$_2$O (2 mL) and extracted with DCM (3×50 mL). The combined organic layer was washed with brine (60 mL), dried over Na$_2$SO$_4$ and filtered. The filtrate was concentrated under reduced pressure to give the title compound (250 mg, 88% yield) as a yellow solid. LC-MS (ESI$^+$) m/z 519.2 (M+H)$^+$.

Step 17—N-[6-(difluoromethyl)-2-[3-(iodomethyl) cyclobutyl]indazol-5-yl]-6-(trifluoromethyl) pyridine-2-carboxamide A mixture of [3-[6-(difluoromethyl)-5-[[6-(trifluoromethyl)pyridine-2-carbonyl]amino]indazol-2-yl]cyclobutyl] methyl methanesulfonate (200 mg, 385 umol) and iodosodium (578 mg, 3.86 mmol) in acetone (10 mL) was degassed and purged with N$_2$ three times, and then the mixture was stirred at 60° C. for 4 hrs under N$_2$ atmosphere. On completion, to the mixture was added water (00 mL) and the solution was extracted with EA (3×50 mL). The organic layer was washed with brine (2×30 mL), dried over Na$_2$SO$_4$ and filtered. The filtrate was concentrated under reduced pressure to give the title compound (200 mg, 94% yield) as a yellow solid. LC-MS (ESI$^+$) m/z 551.2 (M+H)$^+$.

3-fluoro-N-[2-(4-formylcyclohexyl)-6-methoxy-indazol-5-yl]-5-(trifluoromethyl) benzamide (Intermediate BTO)

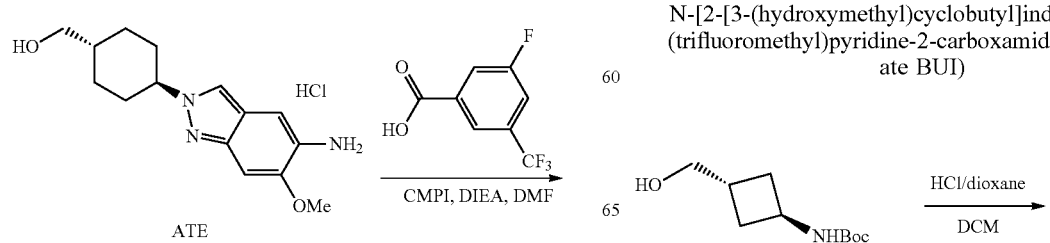

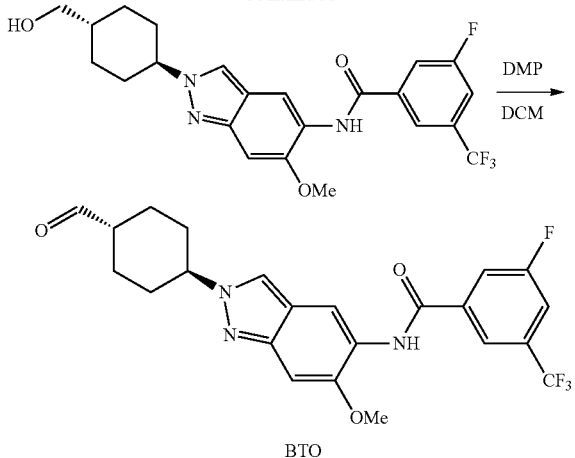

Step 1—3-Fluoro-N-[2-[4-(hydroxymethyl) cyclohexyl]-6-methoxy-indazol-5-yl]-5-(trifluoromethyl) benzamide To a solution of 3-fluoro-5-(trifluoromethyl) benzoic acid (146 mg, 705 umol, CAS #161622-05-5) in DMF (3 mL) was added CMPI (180 mg, 705 umol) and DIEA (248 mg, 1.92 mmol), then the mixture was stirred at 25° C. for 5 mins. Next, a solution of [4-(5-amino-6-methoxy-indazol-2-yl)cyclohexyl]methanol (200 mg, 641 umol, HCl, Intermediate ATE) in DMF (2 mL) was added to above mixture, and the reaction was stirred at 25° C. for 1 hrs. On completion, the reaction mixture was quenched by water (0.05 mL), and diluted with EtOAc (30 mL). The organic layer was washed with brine (2×10 mL). The organic layer was separated, dried over Na$_2$SO$_4$ and concentrated in vacuo to give the title compound (210 mg, 70.34% yield) as a brown solid. LC-MS (ESI$^+$) m/z 466.4 (M+H)$^+$.

Step 2—3-Fluoro-N-[2-(4-formylcyclohexyl)-6-methoxy-indazol-5-yl]-5-(trifluoromethyl)benzamide To a solution of 3-fluoro-N-[2-[4-(hydroxymethyl)cyclohexyl]-6-methoxy-indazol-5-yl]-5-(trifluoromethyl)benzamide (150 mg, 322 umol) in DCM (5 mL) was added DMP (177 mg, 418 umol) at 25° C., then the mixture was stirred at 25° C. for 2 hrs. On completion, the reaction mixture was quenched with Na$_2$S$_2$O$_3$ solution (3 mL), diluted with DCM (20 mL), and then washed with NaHCO$_3$ (2×15 mL). The organic layer was separated, dried over Na$_2$SO$_4$ and concentrated in vacuo to give the title compound (0.149 g, 79% yield) as a brown solid. LC-MS (ESI$^+$) m/z 464.1 (M+H)$^+$.

N-[2-[3-(hydroxymethyl)cyclobutyl]indazol-5-yl]-6-(trifluoromethyl)pyridine-2-carboxamide (Intermediate BUI)

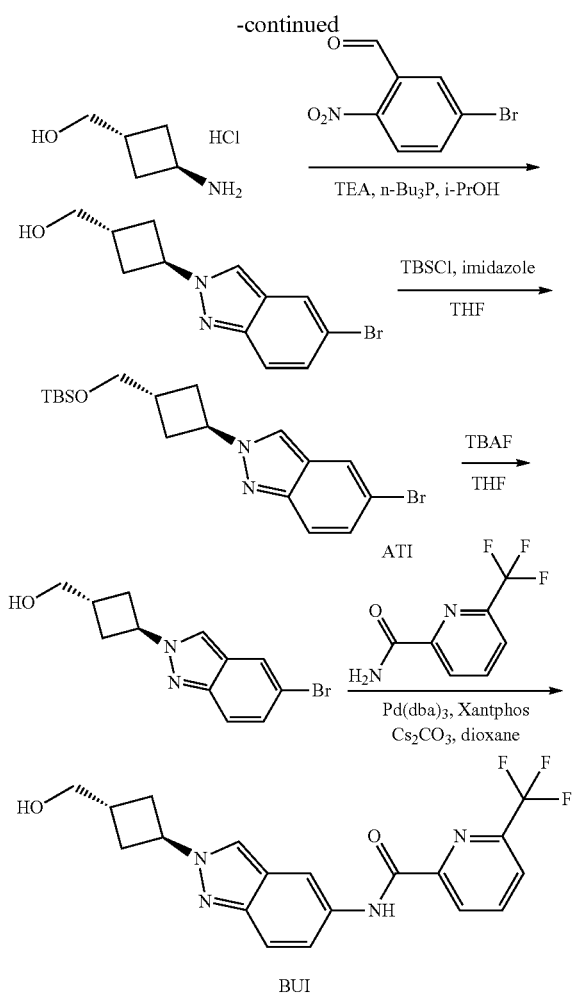

Step 1—(3-Aminocyclobutyl)methanol

To a solution of tert-butyl N-[3-(hydroxymethyl)cyclobutyl]carbamate (5.30 g, 26.3 mmol; CAS #167081-37-0) in DCM (30 mL) was added HCl/dioxane (4 M, 100 mL) at 25° C., and the mixture was stirred 25° C. for 16 hr. On completion, the reaction mixture was concentrated in vacuo to give the title compound (3.50 g, 96%) as colorless oil. $^1$H NMR (400 MHz, DMSO-$d_6$) δ8.23 (s, 2H), 3.74-3.59 (m, 2H), 3.44-3.36 (m, 2H), 2.38 (d, J=4.4, 8.9 Hz, 1H), 2.21-1.87 (m, 4H).

Step 2—[3-(5-Bromoindazol-2-yl)cyclobutyl]methanol

To a solution of (3-aminocyclobutyl)methanol (3.14 g, 22.8 mmol) in i-PrOH (50 mL) was added Et$_3$N (7.70 g, 76.0 mmol) at 0° C. The mixture was stirred at 0° C. for 0.5 hrs, then 5-bromo-2-nitro-benzaldehyde (3.5 g, 15.2 mmol, CAS #20357-20-4) was added to the mixture and stirred at 25° C. for 2 hrs. Next, tributylphosphane (9.24 g, 45.6 mmol) was added to the mixture and warmed up to 80° C. and stirred for 2 hrs. On completion, the reaction mixture was poured into 50 mL of water and extracted with EtOAc (100 mL×2). The combined organic layers were washed by saturated brine (100 mL), dried over Na$_2$SO$_4$, filtered and concentrated in vacuo to give a crude product. The crude product was purified by column chromatography (SiO$_2$, PE/EA=50:1 to EA) to give the title compound (3.60 g, 84% yield) as yellow oil. LC-MS (ESI$^+$) m/z 280.9 (M+H)$^+$.

Step 3—[3-(5-Bromoindazol-2-yl)cyclobutyl] methoxy-tert-butyl-dimethyl-silane To a solution of [3-(5-bromoindazol-2-yl)cyclobutyl] methanol (3.00 g, 10.6 mmol) in THF (20 mL) was added TBSCl (1.93 g, 12.8 mmol), imidazole (1.09 g, 16.0 mmol) at 25° C., then the mixture was stirred at 25° C. for 16 hrs. On completion, the reaction mixture was poured into 50 mL of water and extracted with EtOAc (100 mL×2). The combined organic layers were washed with saturated brine (100 mL), dried over Na$_2$SO$_4$, filtered and concentrated to give a crude product. The crude product was purified by column chromatography (SiO$_2$, Petroleum ether/Ethyl acetate=100/1 to 50/1) to give the title compound (1.00 g, 23% yield) as yellow solid. $^1$H NMR (400 MHz, CDCl$_3$) δ 7.91 (s, 1H), 7.80 (d, J=0.8 Hz, 1H), 7.63 (d, J=9.2 Hz, 1H), 7.33 (dd, J=1.2, 9.4 Hz, 1H), 5.08-5.16 (m, 1H), 3.77 (d, J=4.8 Hz, 2H), 2.89-2.74 (m, 2H), 2.64 (td, J=4.4, 9.2 Hz, 1H), 2.60-2.48 (m, 2H), 0.96 (s, 9H), 0.12 (s, 6H).

Step 4—[3-(5-Bromoindazol-2-yl)cyclobutyl]methanol

To a solution of [3-(5-bromoindazol-2-yl)cyclobutyl] methoxy-tert-butyl-dimethyl-silane (1.00 g, 2.53 mmol) in THF (15 mL) was added TBAF (1 M, 2.78 mL) and stirred at 25° C. for 1 hr. On completion, the mixture was poured into water (40 mL) and extracted with EA (20 mL×2). The combined organic layers were dried over Na$_2$SO$_4$, filtered and concentrated in vacuo to give a residue. The residue was purified by silica gel column chromatography (petroleum ether/ethyl acetate=100:1, 5:1) to give the title compound (650 mg, 91% yield) as white solid. $^1$H NMR (400 MHz, CDCl$_3$) δ 7.92 (s, 1H), 7.80 (d, J=1.2 Hz, 1H), 7.62 (d, J=9.2 Hz, 1H), 7.34 (d, J=9.2 Hz, 1H), 5.10-5.18 (m, 1H), 3.84 (d, J=6.4 Hz, 2H), 2.93-2.83 (m, 2H), 2.71 (d, J=2.8, Hz, 1H), 2.62-2.47 (m, 2H).

Step 5—N-[2-[3-(hydroxymethyl)cyclobutyl]indazol-5-yl]-6-(trifluoromethyl)pyridine-2-carboxamide To a solution of [3-(5-bromoindazol-2-yl)cyclobutyl] methanol (0.45 g, 1.60 mmol) in dioxane (8 mL) was added 6-(trifluoromethyl)pyridine-2-carboxamide (365 mg, 1.92 mmol, Intermediate ATI), Cs$_2$CO$_3$ (1.04 g, 3.20 mmol)Pd$_2$(dba)$_3$ (146 mg, 160 umol), and ditert-butyl -[2-(2,4,6-triisopropylphenyl) phenyl]phosphane (67.9 mg, 160 umol) at 25° C. under N$_2$. Then the mixture was stirred at 100° C. for 16 hrs. On completion, the mixture was diluted with water (20 mL) and extracted with EA (20 mL×2). The combined organic layers were dried over Na$_2$SO$_4$, filtered and concentrated in vacuo to give a residue. The residue was purified by silica gel chromatography (petroleum ether/ethyl acetate=100:1 to 1/3) to give the title compound (350 mg, 56% yield) as yellow solid. $^1$H NMR (400 MHz, DMSO-$d_6$) δ 10.37 (s, 1H), 8.44 (s, 1H), 8.42-8.33 (m, 2H), 8.29 (s, 1H), 8.17 (d, J=7.2 Hz, 1H), 7.66-7.53 (m, 2H), 5.16-5.24 (m, 1H), 4.76 (t, J=5.2 Hz, 1H), 3.58 (t, J=6.0 Hz, 2H), 2.81-2.61 (m, 2H), 2.48-2.44 (m, 1H), 2.41-2.34 (m, 2H).

N-[6-(1-hydroxy-1-methyl-ethyl)-2-[4-(iodomethyl)cyclohexyl]indazol-5-yl]-6-(trifluoro methyl)pyridine-2-carboxamide (Intermediate BUJ)

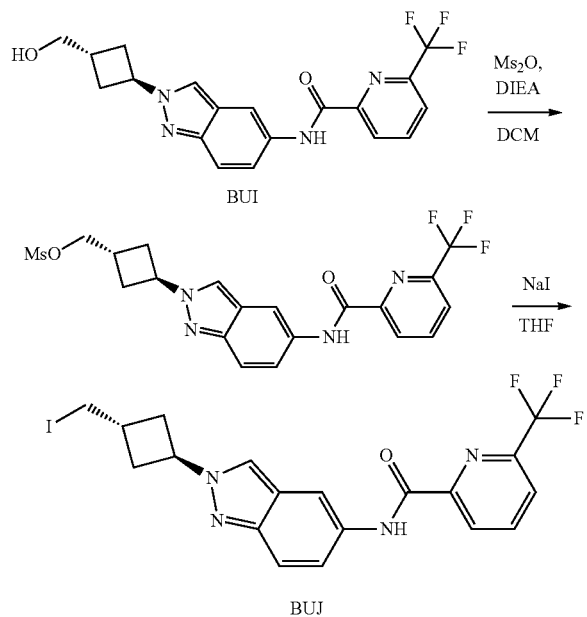

Step 1—[3-[5-[[6-(Trifluoromethyl)pyridine-2-carbonyl]amino]indazol-2-yl]cyclobutyl]methyl methanesulfonate To a solution of N-[2-[3-(hydroxymethyl)cyclobutyl]indazol-5-yl]-6-(trifluoromethyl)pyridine-2-arboxamide (0.06 g, 153 umol, Intermediate BUI) in THF (2 mL) was added methylsulfonyl methanesulfonate (80.3 mg, 461 umol) and DIEA (79.4 mg, 614 umol). Then the mixture was stirred at 25° C. for 2 hrs. On completion, the reaction mixture was poured into 10 mL of water and extracted with EtOAc (10 mL×2). The combined organic layers were washed with saturated brine (10 mL), dried over $Na_2SO_4$, filtered and concentrated in vacuo to give the title compound (68.0 mg, 94% yield) as yellow solid. $^1$H NMR (400 MHz, $CDCl_3$) δ 9.92 (s, 1H), 8.64-8.48 (m, 2H), 8.26-8.11 (m, 2H), 8.05-7.87 (m, 2H), 7.59 (d, J=9.2 Hz, 1H), 5.48 (s, 1H), 4.43 (d, J=3.2 Hz, 2H), 3.14 (s, 3H), 2.96 (s, 2H), 2.80-2.62 (m, 2H), 1.46-1.39 (m, 1H).

Step 2—N-[6-(1-hydroxy-1-methyl-ethyl)-2-[4-(iodomethyl)cyclohexyl]indazol-5-yl]-6-(trifluoro methyl)pyridine-2-carboxamide To a solution of [3-[5-[[6-(trifluoromethyl)pyridine-2-carbonyl]amino]indazol-2-yl]cyclobutyl]methyl methanesulfonate (66.0 mg, 140 umol) in THF (2 mL) was added NaI (95.0 mg, 634 umol). Then the mixture was stirred at 65° C. for 16 hrs. On completion, the reaction mixture was poured into 10 mL of water and extracted with EtOAc (10 mL×2). The combined organic layers were washed by saturated brine (10 mL), dried over $Na_2SO_4$, filtered and concentrated to give the title compound (65 mg, 92% yield) as yellow solid. $^1$H NMR (400 MHz, DMSO-$d_6$) δ 10.37 (s, 1H), 8.44 (s, 1H), 8.41-8.33 (m, 2H), 8.29 (d, J=1.2 Hz, 1H), 8.17 (dd, J=1.2, 7.6 Hz, 1H), 7.69-7.54 (m, 2H), 5.28 (q, J=7.2 Hz, 1H), 3.62-3.57 (m, 2H), 2.96-2.83 (m, 1H), 2.76-2.66 (m, 2H), 2.38-2.26 (m, 2H).

5-Chloro-N-[2-(4-formylcyclohexyl)-6-methoxy-indazol-5-yl]pyridine-3-carboxamide (Intermediate BUK)

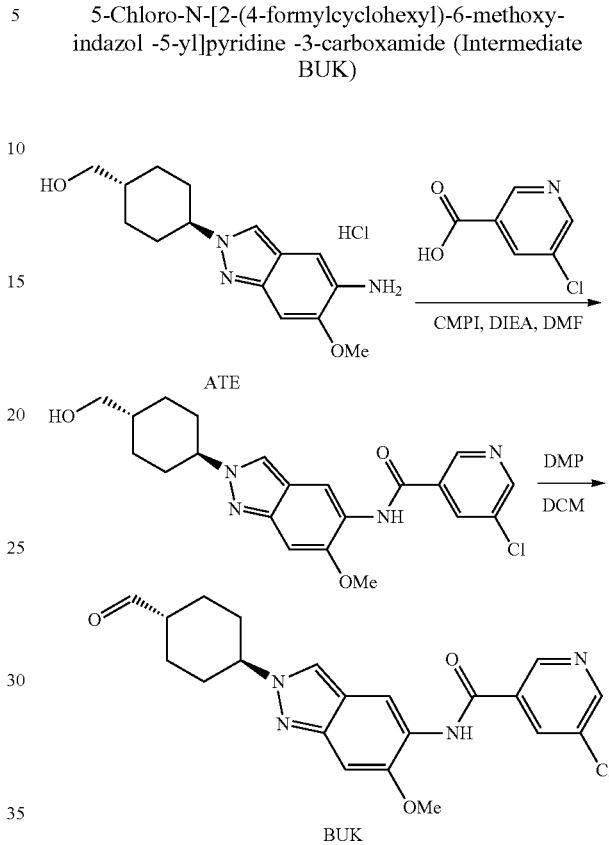

Step 1—5-Chloro-N-[2-[4-(hydroxymethyl)cyclohexyl]-6-methoxy-indazol-5-yl]pyridine-3-carboxamide To a solution of [4-(5-amino-6-methoxy-indazol-2-yl)cyclohexyl]methanol (200 mg, 726 umol, Intermediate ATE) in DMF (6 mL) was added CMPI (167 mg, 653 umol), 5-chloropyridine-3-carboxylic acid (103 mg, 653 umol, CAS #22620-27-5) and DIEA (375 mg, 2.91 mmol) in DMF (6 mL). The mixture was stirred at 25° C. for 1 hr. On completion, the mixture concentrated under reduced pressure to give a residue. The residue was purified by prep-HPLC (0.1% FA condition) to give the title compound (220 mg, 73% yield) as off-white solid. LC-MS (ESI+) m/z 415.3 (M+H)$^+$.

Step 2—5-Chloro-N-[2-(4-formylcyclohexyl)-6-methoxy-indazol-5-yl]pyridine-3-carboxamide To a solution of 5-chloro-N-[2-[4-(hydroxymethyl)cyclohexyl]-6-methoxy-indazol-5-yl]pyridine-3-carboxamide (50.0 mg, 120 umol) in DCM (1 mL) was added DMP (61.3 mg, 144 umol). The mixture was stirred at 25° C. for 2 hrs. On completion, the reaction mixture was quenched with $Na_2S_2O_3$ (10 mL) aqueous and $NaHCO_3$ aqueous (10 mL) at 25° C. Then the solution was diluted with $NaHCO_3$ aqueous (15 mL) and extracted with DCM (10 mL×2). The combined organic layers were dried over anhydrous $Na_2SO_4$, filtered and concentrated under reduced pressure to give the crude product (49.0 mg, 98% yield) as a yellow solid. LC-MS (ESI+) m/z 413.3 (M+H)+.

5-Chloro-N-[2-(4-formylcyclohexyl)-6-methoxy-indazol-5-yl]pyridine-3-carboxamide (Intermediate BUL)

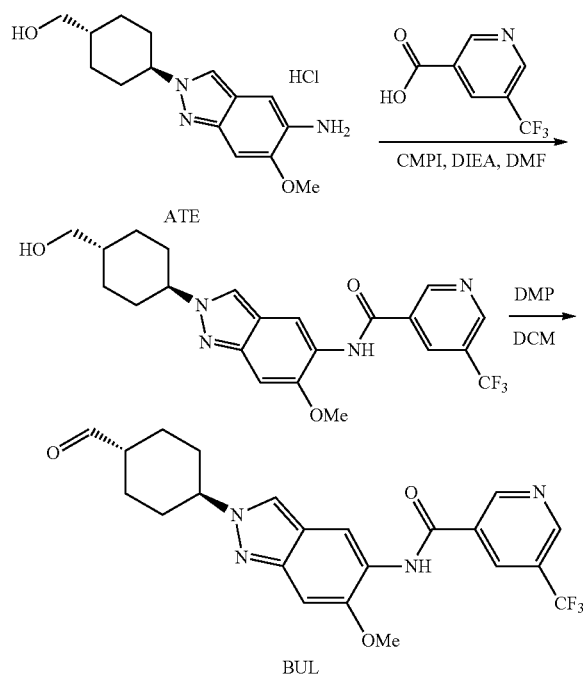

Step 1—N-[2-[4-(hydroxymethyl)cyclohexyl]-6-methoxy-indazol-5-yl]-5-(trifluoromethyl)pyridine-3-carboxamide To a solution of [4-(5-amino-6-methoxy-indazol-2-yl)cyclohexyl]methanol (150 mg, 544 umol, Intermediate ATE) in DMF (1 mL) was added CMPI (125 mg, 490 umol), 5-(trifluoromethyl)pyridine-3-carboxylic acid (93.7 mg, 490 umol, CAS #131747-40-5) and DIEA (281 mg, 2.18 mmol) in DMF (1 mL). The mixture was stirred at 25° C. for 1 hr. On completion, the mixture was concentrated in vacuo. The residue was purified by prep-HPLC (0.1% FA condition) to give the title compound (60.0 mg, 24% yield) as off-white solid. LC-MS (ESI+) m/z 449.3 (M+H)+.

Step 2—5-Chloro-N-[2-(4-formylcyclohexyl)-6-methoxy-indazol-5-yl]pyridine-3-carboxamide To a solution of N-[2-[4-(hydroxymethyl)cyclohexyl]-6-methoxy-indazol-5-yl]-5-(trifluoromethyl) pyridine-3-carboxamide (48.0 mg, 107 umol) in DCM (1 mL) was added DMP (54.4 mg, 128 umol). The mixture was stirred at 25° C. for 2 hrs. On completion, the mixture was quenched with Na2S2O3 aqueous (10 mL) and NaHCO3 aqueous (10 mL) at 25° C., and then the mixture was extracted with DCM (10 mL×2). The combined organic layers were dried over anhydrous Na2SO4, filtered and concentrated in vacuo to give the crude product (35.0 mg, 73% yield) as a yellow solid. LC-MS (ESI+) m/z 447.3 (M+H)+.

N-[2-(4-formylcyclohexyl)-6-methoxy-indazol-5-yl]pyrrolo[2,3-b]pyridine-1-carboxamide (Intermediate BUM)

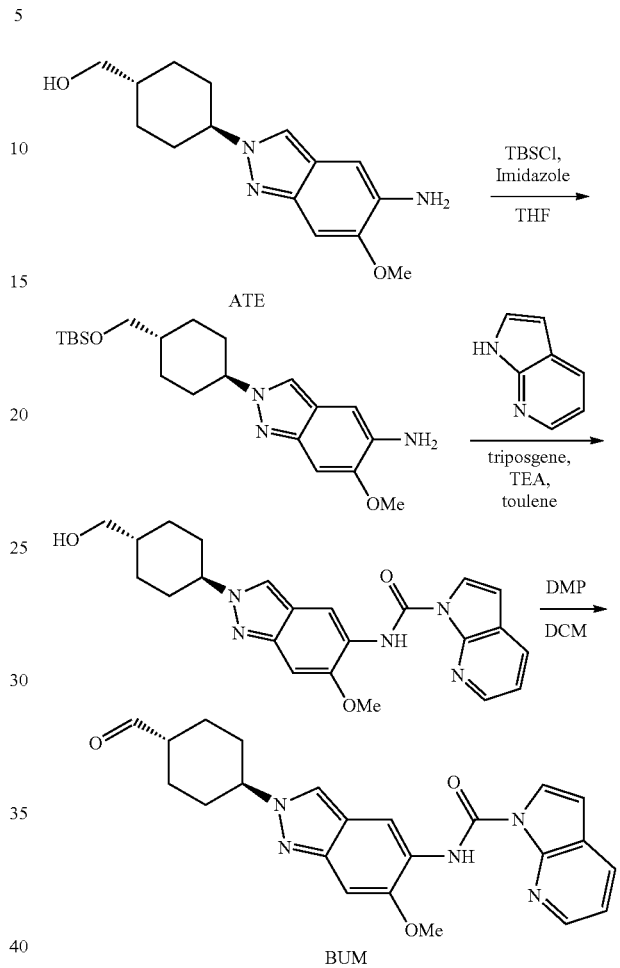

Step 1—2-[4-[[Tert-butyl(dimethyl)silyl]oxymethyl]cyclohexyl]-6-methoxy-indazol-5-amine To a solution of [4-(5-amino-6-methoxy-indazol-2-yl)cyclohexyl]methanol (400 mg, 1.28 mmol, HCl, Intermediate ATE) in THF (10 mL) was added Imidazole (174 mg, 2.57 mmol) and TBSCl (232 mg, 1.54 mmol), then the reaction mixture was stirred at 25° C. for 2 hrs. On completion, the reaction mixture was quenched with H2O (15 mL) and extracted with DCM (2×30 mL). The combined organic phase was brine (2×15 mL), dried with anhydrous Na2SO4, filtered and concentrated in vacuo to give title compound (495 mg, 99% yield) as a yellow solid. LC-MS (ESI+) m/z 390.7 (M+H)+.

Step 2—N-[2-[4-(hydroxymethyl)cyclohexyl]-6-methoxy-indazol-5-yl]pyrrolo[2,3-b]pyridine-1-carboxamide To a solution of 1H-pyrrolo[2,3-b]pyridine (150 mg, 1.27 mmol, CAS #517918-95-5) and TEA (642 mg, 6.35 mmol) in ACN (5 mL) was added triphosgene (226 mg, 761 umol). The mixture was stirred at 0° C. for 0.5 hr. Next, 2-[4-[[tert-butyl(dimethyl)silyl]oxymethyl]cyclohexyl]-6-methoxy-indazol-5-amine (494 mg, 1.27 mmol) was added to the mixture, and the reaction mixture was stirred at 25° C. for 12 hrs. On completion, the reaction mixture was quenched with NaHCO₃ (20 mL), then extracted with DCM (2×30 mL). The organic phase was dried over Na₂SO₄, filtered and the filtrate was concentrated in vacuo to give a residue. The residue was purified by reverse phase (0.1% FA condition) to give title compound (100 mg, 18% yield) as a brown solid. ¹H NMR (400 MHz, DMSO-d₆) δ 12.34 (s, 1H), 8.55 (dd, J=1.2, 4.8 Hz, 1H), 8.50 (s, 1H), 8.31 (s, 1H), 8.22 (dd, J=1.2, 7.6 Hz, 1H), 8.09 (d, J=4.0 Hz, 1H), 7.41 (dd, J=4.8, 8.0 Hz, 1H), 7.14 (s, 1H), 6.81 (d, J=4.0 Hz, 1H), 4.49 (t, J=4.8 Hz, 1H), 4.41-4.29 (m, 1H), 4.05 (s, 3H), 3.30-3.26 (m, 2H), 2.14 (dd, J=3.2, 12.4 Hz, 2H), 1.96-1.85 (m, 4H), 1.53-1.41 (m, 1H), 1.20-1.08 (m, 2H); LC-MS (ESI⁺) m/z 420.0 (M+H)⁺.

Step 3—N-[2-(4-formylcyclohexyl)-6-methoxy-indazol-5-yl]pyrrolo[2,3-b]pyridine-1-carboxamide To a solution of N-[2-[4-(hydroxymethyl)cyclohexyl]-6-methoxy-indazol-5-yl]pyrrolo[2,3-b]pyridine-1-carboxamide (95 mg, 226 umol) in DCM (0.5 mL) was added DMP (115 mg, 271 umol), then the reaction mixture was stirred at 25° C. for 2 hrs. On completion, the reaction mixture was quenched with Na₂S₂O₃ (15 mL) and extracted with DCM (2×30 mL). The combined organic phase was washed with NaHCO₃ and brine (2×15 mL), dried with anhydrous Na₂SO₄, filtered and concentrated in vacuo to give the title compound (90 mg, 95% yield) as a yellow solid. ¹H NMR (400 MHz, DMSO-d₆) δ 12.34 (s, 1H), 9.64 (s, 1H), 8.55 (dd, J=1.2, 4.8 Hz, 1H), 8.51 (s, 1H), 8.31 (s, 1H), 8.22 (dd, J=1.2, 8.0 Hz, 1H), 8.09 (d, J=4.0 Hz, 1H), 7.41 (dd, J=4.8, 8.0 Hz, 1H), 7.14 (s, 1H), 6.81 (d, J=4.0 Hz, 1H), 4.43-4.35 (m, 1H), 4.05 (s, 3H), 2.45-2.38 (m, 1H), 2.21 (dd, J=3.2, 12.8 Hz, 2H), 2.14-2.07 (m, 2H), 2.02-1.91 (m, 2H), 1.46-1.43 (m, 2H); LC-MS (ESI⁺) m/z 418.1 (M+H)⁺.

5-cyanopyridine-3-carboxylic acid (CAS #887579-62-6) (Intermediate BUN)

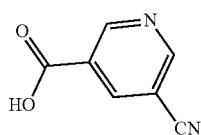

BUN

Tert-butyl N-[2-(4-formylcyclohexyl)indazol-5-yl]carbamate (Intermediate BUO)

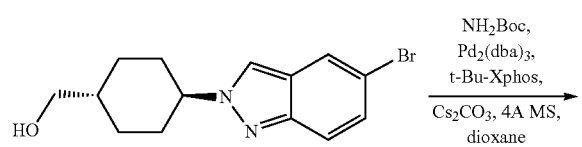

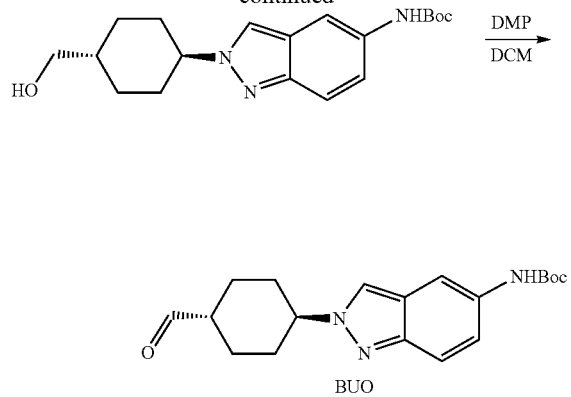

Step 1—Tert-butyl N-[2-[4-(hydroxymethyl)cyclohexyl]indazol-5-yl]carbamate

To a solution of [4-(5-bromoindazol-2-yl)cyclohexyl]methanol (1.00 g, 3.23 mmol, synthesized via Step 1 of Intermediate BTW) and tert-butyl carbamate (378 mg, 3.23 mmol) in dioxane (15 mL), was added Cs₂CO₃ (2.11 g, 6.47 mmol), Pd₂(dba)₃ (296 mg, 323 umol), 4 Å molecular sieves (250 mg, 323 umol), and t-Bu Xphos (274 mg, 646 umol) to the mixture. The mixture was then stirred at 90° C. for 16 hrs. On completion, the reaction mixture was filtered and the filtrate was concentrated in vacuo to give a residue. The residue was purified by reverse phase (0.1% FA condition) to give the title compound (500 mg, 44% yield) as a white solid. ¹H NMR (400 MHz, DMSO-d₆) δ 9.19 (s, 1H), 8.23 (s, 1H), 7.82 (s, 1H), 7.47 (d, J=9.2 Hz, 1H), 7.19 (dd, J=2.0, 9.2 Hz, 1H), 4.48 (t, J=5.2 Hz, 1H), 4.42-4.29 (m, 1H), 3.28 (t, J=6.0 Hz, 2H), 2.17-2.07 (m, 2H), 1.95-1.83 (m, 4H), 1.48 (m, 10H), 1.21-1.06 (m, 2H), LC-MS (ESI⁺) m/z 346.6 (M+H)⁺.

Step 2—Tert-butyl N-[2-(4-formylcyclohexyl)indazol-5-yl]carbamate

To a solution of tert-butyl N-[2-[4-(hydroxymethyl)cyclohexyl]indazol-5-yl]carbamate (190 mg, 550 umol) in DCM (1.5 mL) was added DMP (279 mg, 660 umol, 204 uL), then the reaction mixture was stirred at 25° C. for 2 hrs. On completion, the reaction mixture was quenched with Na₂S₂O₃ (10 mL) and NaHCO₃ (10 mL) and extracted with DCM (2×20 mL). The combined organic phase was washed with NaHCO₃ (15 mL) and brine (2×15 mL), dried with anhydrous Na₂SO₄, filtered and the filtrate was concentrated in vacuo to give the title compound (188 mg, 99% yield) as a purple solid. LC-MS (ESI⁺) m/z 344.2 (M+H)⁺.

3-[4-[1-[[4-(5-Aminoindazol-2-yl)cyclohexyl]
methyl]-4-piperidyl]-3-methyl-2-oxo-benzimidazol-
1-yl]piperidine-2,6-dione (Intermediate BUP)

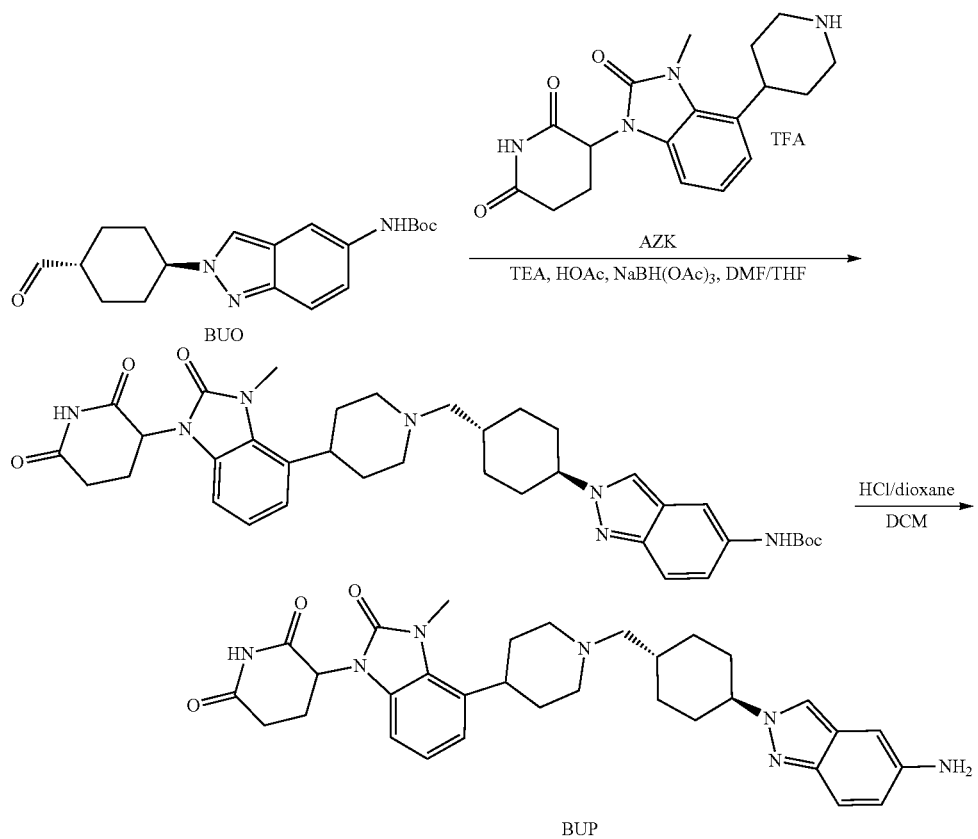

Step 1—Tert-butyl N-[2-[4-[[4-[1-(2,6-dioxo-3-piperidyl)-3-methyl-2-oxo-benzimidazol-4-yl]-1-piperidyl]methyl]cyclohexyl]indazol-5-yl]carbamate To a solution of 3-[3-methyl-2-oxo-4-(4-piperidyl)benzimidazol-1-yl]piperidine-2,6-dione (179 mg, 393 umol, TFA, Intermediate AZK) in THF (1.5 mL) and DMF (1.5 mL) was added TEA (39.7 mg, 393 umol, 54.7 uL), and the mixture was stirred at −10° C. for 10 mins. Then tert-butyl N-[2-(4-formylcyclohexyl)indazol-5-yl]carbamate (135 mg, 393 umol, Intermediate BUO) and AcOH (23.6 mg, 393 umol, 22.4 uL) was added to the mixture, and the mixture was stirred at −10° C. for 20 mins. Finally, NaBH(OAc)$_3$ (99.9 mg, 471 umol) was added to the mixture, and the mixture was stirred at −10° C. for 1 hr. On completion, the reaction mixture was quenched with water (0.5 mL) and concentrated in vacuo to give a residue. The residue was purified by reverse phase (0.1% FA condition) to give the title compound (80 mg, 30.0% yield) as a brown solid. $^1$H NMR (400 MHz, DMSO-d$_6$)) δ 11.10 (s, 1H), 9.20 (s, 1H), 8.24 (s, 1H), 7.84 (s, 1H), 7.48 (d, J=9.2 Hz, 1H), 7.20 (dd, J=2.0, 9.2 Hz, 1H), 7.07-6.96 (m, 3H), 5.38 (dd, J=5.2, 12.4 Hz 1H), 4.49-4.35 (m, 1H), 3.61 (s, 3H), 3.49-3.38 (m, 3H), 2.88-2.82 (m, 1H), 2.72-2.58 (m, 5H), 2.20-2.10 (m, 2H), 2.06-1.88 (m, 10H), 1.87-1.80 (m, 1H), 1.48 (s, 9H), 1.29-1.20 (m, 2H), LC-MS (ESI$^+$) m/z 670.4 (M+H)$^+$.

Step 2—3-[4-[1-[[4-(5-Aminoindazol-2-yl)cyclohexyl]methyl]-4-piperidyl]-3-methyl-2-oxo-benzimidazol-1-yl]piperidine-2,6-dione To a solution of tert-butyl N-[2-[4-[[4-[1-(2,6-dioxo-3-piperidyl)-3-methyl-2-oxo-benzimidazol-4-yl]-1-piperidyl]methyl]cyclohexyl]indazol-5-yl]carbamate (50.0 mg, 74.6 umol) in DCM (1 mL) was added HCl/dioxane (4 M, 1 mL), then the reaction mixture was stirred at 25° C. for 2 hrs. On completion, the reaction mixture was concentrated in vacuo to give the title compound (45 mg, 99% yield, HCl) as white solid. LC-MS (ESI$^+$) m/z 570.5 (M+H)$^+$.

6-(5-cyanopyrrolo[2,3-b]pyridin-1-yl)-4-(isopropylamino)pyridine-3-carboxylic acid (Intermediate BUQ)

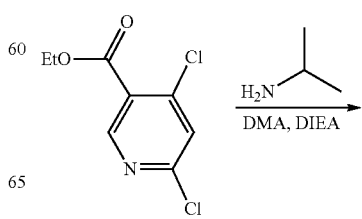

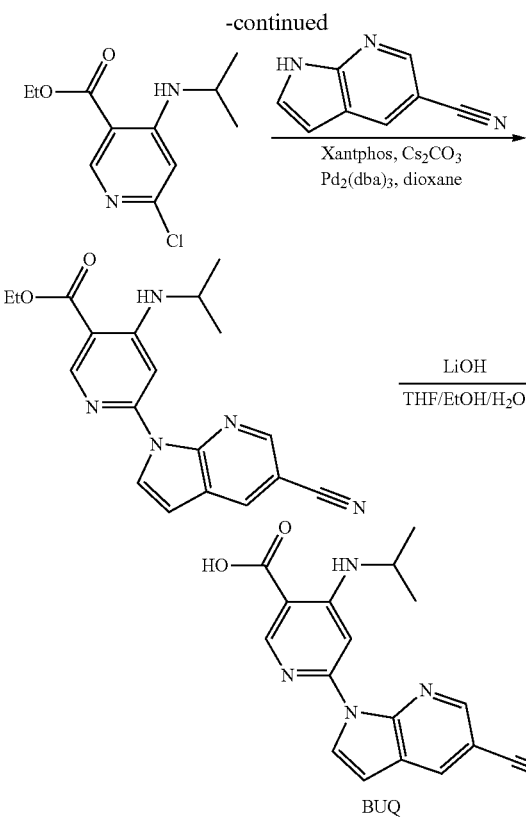

NMR (400 MHz, CDCl$_3$) δ 8.83 (s, 1H), 8.67 (s, 1H), 8.57 (d, J=4.0 Hz, 1H), 8.25 (d, J=12.0 Hz, 2H), 8.19 (s, 1H), 6.71 (d, J=3.6 Hz, 1H), 4.37 (q, J=7.2 Hz, 2H), 3.98-3.88 (m, 1H), 1.44 (s, 9H).

Step 3—6-(5-cyanopyrrolo[2,3-b]pyridin-1-yl)-4-(isopropylamino)pyridine-3-carboxylic Acid To a solution of ethyl 6-(5-cyanopyrrolo[2,3-b]pyridin-1-yl)-4-(isopropylamino)pyridine-3-carboxylate (1 g, 2.86 mmol) in EtOH (2 mL), THF (8 mL) and H$_2$O (1.2 mL) was added LiOH·H$_2$O (1.20 g, 28.6 mmol). The mixture was stirred at 50° C. for 9 hrs. On completion, the reaction mixture was filtered and diluted with water (10 mL). The aqueous layer was acidified to pH 5-6 with 6N HCl and lyophilized. The product was dissolved in DCM:MeOH=10:1 (22 mL) and filtered. The filtrate was concentrated in vacuo to give title compound (800 mg, 86% yield) as yellow solid. $^1$H NMR (400 MHz, DMSO-d$_6$) δ 13.20-13.11 (m, 1H), 9.53-9.52 (m, 1H), 8.82 (d, J=2.0 Hz, 1H), 8.71 (s, 1H), 8.67 (d, J=2.0 Hz, 1H), 8.54 (d, J=4.0 Hz, 1H), 8.28 (d, J=7.2 Hz, 1H), 6.89 (d, J=4.0 Hz, 1H), 3.89-3.79 (m, 1H), 1.33 (d, J=6.4 Hz, 6H).

6-(5-cyanopyrrolo[2,3-b]pyridin-1-yl)-N-(4-formylcyclohexyl)-4-(isopropylamino)pyridine-3-carboxamide (Intermediate BUR)

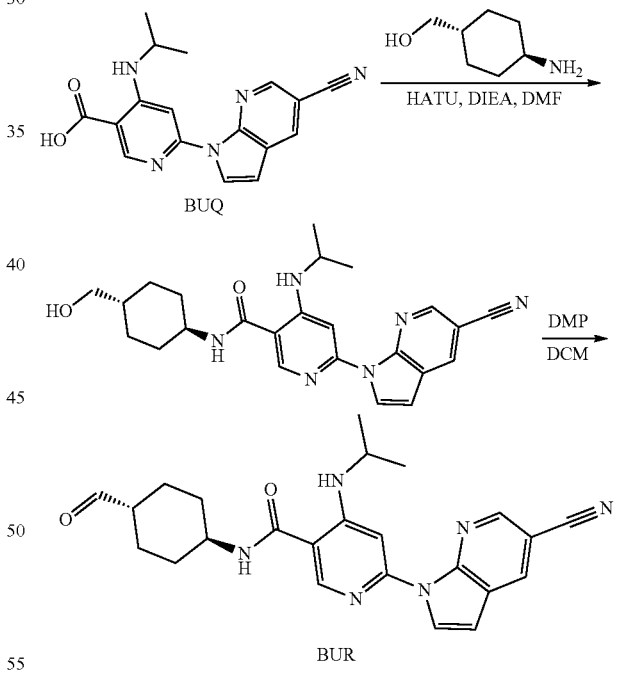

Step 1—6-(5-cyanopyrrolo[2,3-b]pyridin-1-yl)-N-[4-(hydroxymethyl)cyclohexyl]-4-(isopropylamino)pyridine-3-carboxamide To a solution of 6-(5-cyanopyrrolo[2,3-b]pyridin-1-yl)-4-(isopropylamino)pyridine-3-carboxylic acid (100 mg, 311 umol, Intermediate BUQ), (4-aminocyclohexyl)methanol (44.2 mg, 342 umol, CAS #1467-84-1) and DIEA (80.4 mg, 622 umol) in DMF (2 mL) was added HATU (236 mg, 622 umol). The reaction was then stirred at 25° C. for 1 hr. On Step 1—Ethyl 6-chloro-4-(isopropylamino)pyridine-3-carboxylate To a solution of ethyl 4,6-dichloropyridine-3-carboxylate (1 g, 4.54 mmol, CAS #40296-46-6) in DMA (10 mL) was added DIEA (2.94 g, 22.7 mmol, 3.96 mL) and propan-2-amine (537 mg, 9.09 mmol, CAS #4432-77-3). The reaction mixture was stirred at 50° C. for 3 hrs. On completion, the reaction mixture was diluted with EtOAc (50 mL) and washed with water (50 mL×3). The organic layer was dried over Na$_2$SO$_4$, filtered and concentrated in vacuo. The residue was purified by column chromatography (SiO$_2$, petroleum ether/ethyl acetate=10/1, P1: R$_f$=0.5) to give title compound (0.968 g, 87% yield) as yellow solid. $^1$H NMR (400 MHz, DMSO-d$_6$) δ 8.53 (s, 1H), 7.99 (d, J=6.8 Hz, 1H), 6.83 (s, 1H), 4.29 (q, J=7.2 Hz, 2H), 3.92-3.79 (m, 1H), 1.31 (t, J=7.2 Hz, 3H), 1.20 (d, J=6.4 Hz, 6H).

Step 2—Ethyl 6-(5-cyanopyrrolo[2,3-b]pyridin-1-yl)-4-(isopropylamino)pyridine-3-carboxylate To a solution of ethyl 6-chloro-4-(isopropylamino)pyridine-3-carboxylate (868 mg, 3.58 mmol) and 1H-pyrrolo[2,3-b]pyridine-5-carbonitrile (511 mg, 3.58 mmol, CAS #517918-95-5) in dioxane (9 mL) was added Xantphos (206 mg, 357 umol) and Cs$_2$CO$_3$ (2.33 g, 7.15 mmol). The reaction mixture was purged with N$_2$ gas several times, followed by addition of Pd$_2$(dba)$_3$ (327 mg, 357 umol), then the mixture was purged with N$_2$ again. The mixture was stirred at 110° C. for 16 hrs under N$_2$. On completion, the reaction mixture was filtered and concentrated in vacuo. The residue was purified by column chromatography (SiO$_2$, petroleum ether/ethyl acetate=10/1 to 5/1, P1: R$_f$=0.5) to give title compound (500 mg, 40% yield) as yellow solid. $^1$H completion, the reaction mixture was diluted with EtOAc (20 mL). The organic layer was washed with water (20 mL×3), dried over Na$_2$SO$_4$ and concentrated in vacuo. The residue was purified by column chromatography (SiO$_2$, petroleum ether/ethyl acetate=2/1 to 0/1) to give title compound (130 mg, 96% yield) as yellow solid. $^1$H NMR (400 MHz, DMSO-d$_6$) δ 8.81 (d, J=2.0 Hz, 1H), 8.67 (d, J=2.0 Hz, 1H), 8.60 (d, J=7.2 Hz, 1H), 8.57 (s, 1H), 8.52 (d, J=4.0 Hz, 1H), 8.31 (d, J=7.6 Hz, 1H), 8.08 (s, 1H), 6.89 (d, J=4.0 Hz, 1H), 4.40 (s, 1H), 3.81-3.66 (m, 2H), 3.24 (d, J=6.0 Hz, 2H), 1.88 (d, J=9.6 Hz, 2H), 1.79 (d, J=11.6 Hz, 2H), 1.36-1.31 (m, 2H), 1.29 (d, J=6.4 Hz, 6H), 1.04-0.91 (m, 2H).

Step 2—6-(5-cyanopyrrolo[2,3-b]pyridin-1-yl)-N-(4-formylcyclohexyl)-4-(isopropylamino)pyridine-3-carboxamide To a solution of 6-(5-cyanopyrrolo[2,3-b]pyridin-1-yl)-N-[4-(hydroxymethyl)cyclohexyl]-4-(isopropylamino)pyridine-3-carboxamide (75 mg, 173 umol) in DCM (2 mL) was added DMP (95.6 mg, 225 umol). Then the reaction was stirred at 25° C. for 1 hr. On completion, the reaction was quenched with Na$_2$S$_2$O$_3$ (4 mL) and NaHCO$_3$ (5 mL) and the mixture was diluted with DCM (20 mL). The combined organic layers were washed with water (20 mL×3), dried over Na$_2$SO$_4$, filtered and concentrated in vacuo to give title compound (60 mg, 80 yield) as yellow solid. LC-MS (ESI$^+$) m/z 431.1 (M+H)$^+$.

1-[5-(4-formylpiperidine-1-carbonyl)-4-(isopropylamino)-2-pyridyl]pyrrolo[2,3-b]pyridine-5-carbonitrile (Intermediate BUS)

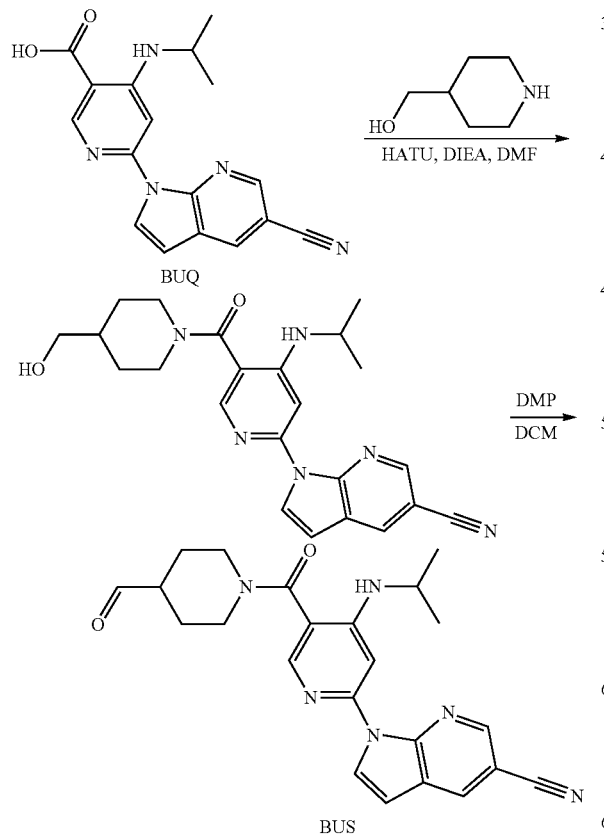

Step 1—1-[5-[4-(hydroxymethyl)piperidine-1-carbonyl]-4-(isopropylamino)-2-pyridyl]pyrrolo[2,3-b]pyridine-5-carbonitrile To a solution of 6-(5-cyanopyrrolo[2,3-b]pyridin-1-yl)-4-(isopropylamino)pyridine-3-carboxylic acid (100 mg, 311 umol, Intermediate BUQ), 4-piperidylmethanol (35.8 mg, 311 umol, CAS #6457-49-4) and DIEA (80.4 mg, 622 umol) in DMF (2 mL) was added HATU (130 mg, 342 umol). The reaction was stirred at 25° C. for 16 hrs. On completion, the reaction was quenched with water (10 mL) and extracted with EtOAc (20 mL×2). The organic layer was separated and concentrated in vacuo. The residue was purified by reversed-phase HPLC (0.1% FA condition) to give title compound (89 mg, 68% yield) as white solid. $^1$H NMR (400 MHz, DMSO-d$_6$) δ 8.80 (d, J=2.0 Hz, 1H), 8.66 (d, J=2.0 Hz, 1H), 8.49 (d, J=4.0 Hz, 1H), 8.01 (d, J=10.4 Hz, 2H), 6.87 (d, J=4.0 Hz, 1H), 6.19 (d, J=7.6 Hz, 1H), 4.54-4.47 (m, 1H), 4.20-3.91 (m, 2H), 3.84-3.72 (m, 1H), 3.28 (s, 2H), 3.00-2.86 (m, 2H), 1.75-1.59 (m, 3H), 1.27 (d, J=6.4 Hz, 6H), 1.20-1.08 (m, 2H).

Step 2—1-[5-(4-formylpiperidine-1-carbonyl)-4-(isopropylamino)-2-pyridyl]pyrrolo[2,3-b]pyridine-5-carbonitrile To a solution of 1-[5-[4-(hydroxymethyl)piperidine-1-carbonyl]-4-(isopropylamino)-2-pyridyl]pyrrolo[2,3-b]pyridine-5-carbonitrile (85 mg, 203 umol) in DCM (2 mL) was added DMP (111 mg, 264 umol). The reaction was stirred at 25° C. for 1 hr. On completion, the reaction was quenched with Na$_2$S$_2$O$_3$ (5 mL) and NaHCO$_3$ (6 mL) solution. The mixture was diluted with DCM (20 mL) and washed with water (20 mL×3). The organic layer was separated, dried over Na$_2$SO$_4$ and filtered. The filtrate was concentrated in vacuo to give title compound (83 mg, 98% yield) as yellow solid. LC-MS (ESI$^+$) m/z 417.4 (M+H)$^+$.

5-Chloro-N-[2-(4-formylcyclohexyl)indazol-5-yl]pyridine-3-carboxamide (Intermediate BUT)

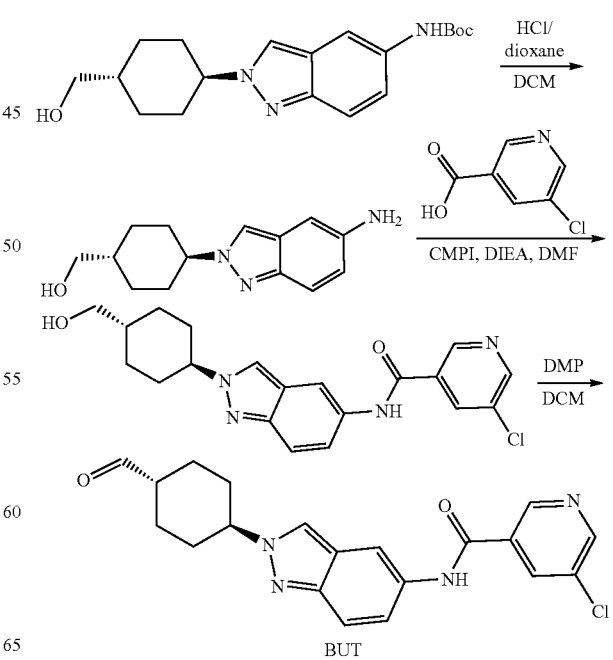

Step 1—[4-(5-Aminoindazol-2-yl)cyclohexyl] methanol

To a solution of tert-butyl N-[2-[4-(hydroxymethyl)cyclohexyl]indazol-5-yl]carbamate (100 mg, 289 umol, synthesized via Step 1 of Intermediate BUO) in DCM (1 mL) was added in HCl/dioxane (4 M, 1 mL). The mixture was stirred for 0.5 hour at 25° C. On completion, the reaction mixture was concentrated in vacuo to give the title compound (80 mg, 98% yield, HCl) as a yellow solid. LC-MS (ESI$^+$) m/z 246.0 (M+H)$^+$.

Step 2—5-Chloro-N-[2-[4-(hydroxymethyl)cyclohexyl]indazol-5-yl]pyridine-3-carboxamide To a solution of 5-chloropyridine-3-carboxylic acid (44.7 mg, 283 umol) in DMF (1 mL) was added CMPI (87.0 mg, 340 umol) and DIEA (183 mg, 1.42 mmol, 247 uL). After addition, the mixture was stirred at 25° C. for 10 minutes, and then [4-(5-aminoindazol-2-yl)cyclohexyl]methanol (80 mg, 283 umol, HCl) in DMF (1 mL) was added dropwise at 25° C. The resulting mixture was stirred 25° C. for 2 hours. On completion, the reaction mixture was diluted with H$_2$O (5 mL), filtered and the filter cake was concentrated in vacuo to give the title compound (92 mg, 84% yield) as a brown solid. LC-MS (ESI$^+$) m/z 385.1 (M+H)$^+$.

Step 3—5-Chloro-N-[2-(4-formylcyclohexyl)indazol-5-yl]pyridine-3-carboxamide To a solution of 5-chloro-N-[2-[4-(hydroxymethyl)cyclohexyl]indazol-5-yl]pyridine-3-carboxamide (92 mg, 239 umol) in DCM (1 mL) was added DMP (121 mg, 286 umol). The mixture was then stirred at 25° C. for 2 hours. On completion, the reaction mixture was quenched with saturated Na$_2$S$_2$O$_3$ (5 mL) and saturated NaHCO$_3$ (5 mL), then stirred for 10 minutes. The reaction mixture was then extracted with DCM (10 mL×2). The combined organic layers were separated and washed with saturated NaCl (5 mL×2), and concentrated in vacuo to give the title compound (50 mg, 54.6% yield) as purple solid. $^1$H NMR (400 MHz, DMSO-d$_6$) δ 10.45 (s, 1H), 9.63 (s, 1H), 9.09-9.02 (m, 1H), 8.83 (d, J=2.0 Hz, 1H), 8.50-8.40 (m, 2H), 7.66-7.58 (m, 1H), 7.45 (d, J=10.4 Hz, 1H), 4.53-4.39 (m, 1H), 3.29 (s, 2H), 2.26-2.18 (m, 2H), 2.16-2.08 (m, 2H), 2.01-1.95 (m, 2H), 1.51-1.39 (m, 2H), 1.26-1.21 (m, 1H). LC-MS (ESI$^+$) m/z 382.9 (M+H)$^+$.

N-[2-[3-(iodomethyl)cyclobutyl]pyrazolo[3,4-c]pyridin-5-yl]-6-(trifluoromethyl)pyridine-2-carboxamide (Intermediate BUU)

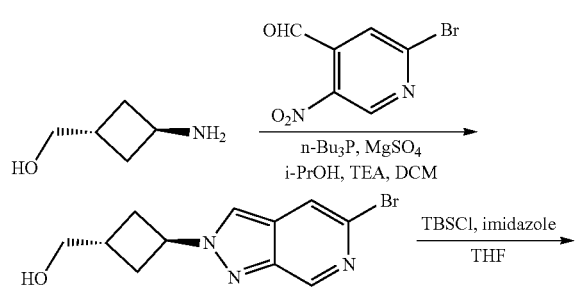

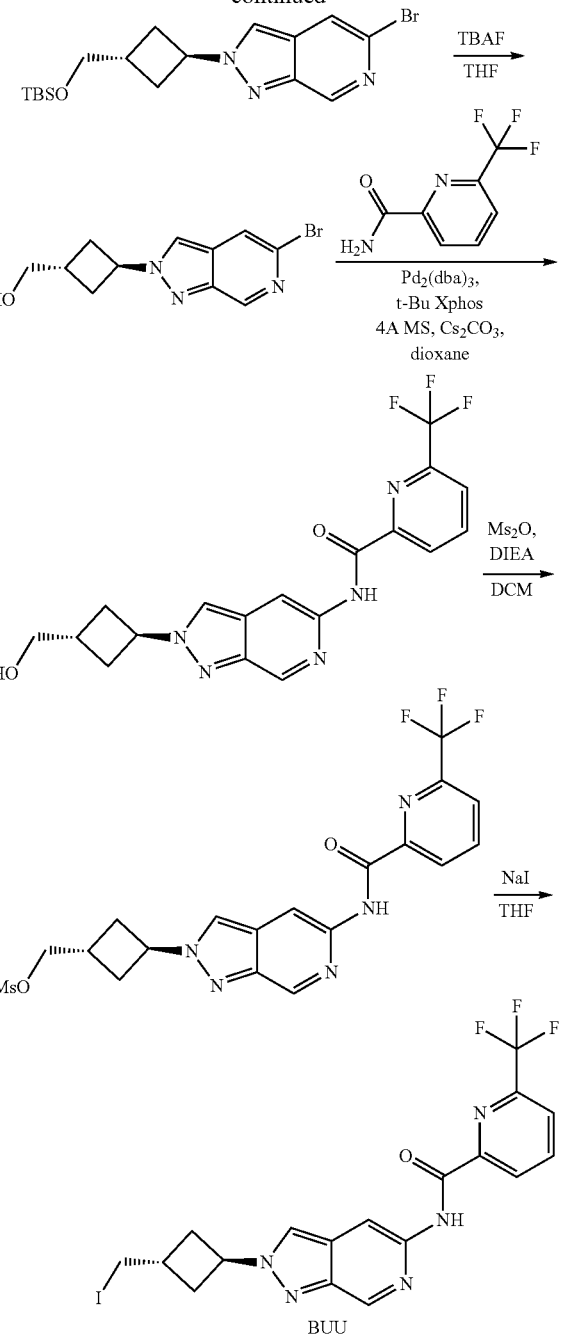

Step 1—4-[3-(5-Bromopyrazolo[3,4-c]pyridin-2-yl)cyclobutyl]methanol

To a solution of (3-aminocyclobutyl)methanol (2.68 g, 19.4 mmol, HCl, synthesized via Step 1 of Intermediate BUI) and 2-bromo-5-nitro-pyridine-4-carbaldehyde (3.00 g, 12.9 mmol, synthesized via Steps 1-2 of Intermediate BRR) in DCM (25 mL) was added tributylphosphane (7.88 g, 38.9 mmol, 9.61 mL) and TEA (3.94 g, 38.9 mmol, 5.42 mL) at 0° C. The mixture was stirred at 25° C. for 2 hrs. Next, MgSO$_4$ (2.34 g, 19.4 mmol) and IPA (25 mL) were added to the solution at 25° C. Then the mixture was stirred at 80° C. for 16 hrs. On completion, the reaction was filtered and concentrated in vacuo to give the title compound (2.50 g, 68% yield) as brown oil. LC-MS (ESI+) m/z 282.2 (M+H)+.

Step 2—[3-(5-Bromopyrazolo[3,4-c]pyridin-2-yl)cyclobutyl]methoxy-tert-butyl-dimethyl-silane To a solution of [3-(5-bromopyrazolo[3,4-c]pyridin-2-yl)cyclobutyl]methanol (2.50 g, 8.86 mmol) in THF (20 mL) was added imidazole (1.21 g, 17.7 mmol) and TBSCl (1.74 g, 11.5 mmol, 1.41 mL). The reaction mixture was stirred at 25° C. for 16 hrs. On completion, the reaction mixture was concentrated in vacuo to give a residue. The residue was purified by column chromatography to give the title compound (1.60 g, 45% yield) as a brown solid. $^1$H NMR (400 MHz, DMSO-$d_6$) δ 9.03 (s, 1H), 8.59 (s, 1H), 7.94 (d, J=0.8 Hz, 1H), 5.39-5.28 (m, 1H), 3.74 (d, J=6.0 Hz, 2H), 2.76-2.66 (m, 2H), 2.63-2.53 (m, 1H), 2.45-2.36 (m, 2H), 0.91 (s, 9H), 0.09 (s, 6H), LC-MS (ESI+) m/z 396.9 (M+H)+.

Step 3—[3-(5-Bromopyrazolo[3,4-c]pyridin-2-yl)cyclobutyl]methanol

To a solution of [3-(5-bromopyrazolo[3,4-c]pyridin-2-yl)cyclobutyl]methoxy-tert-butyl-dimethyl-silane (1.50 g, 3.78 mmol) in THF (10 mL) was added TBAF (1 M, 30.2 mL). The reaction mixture was stirred at 70° C. for 16 hrs. On completion, the mixture was diluted with water (30 mL) and extracted with EA (2×80 mL). The combined organic phase was washed with brine (50 mL), dried with anhydrous Na$_2$SO$_4$, filtered and concentrated in vacuo to give a residue. The residue was triturated with PE (3 mL) and filtered to give the title compound (850 mg, 79% yield) as a brown solid. LC-MS (ESI+) m/z 282.2 (M+H)+.

Step 4—N-[2-[3-(hydroxymethyl)cyclobutyl]pyrazolo[3,4-c]pyridin-5-yl]-6-(trifluoromethyl)pyridine-2-carboxamide To a solution of [3-(5-bromopyrazolo[3,4-c]pyridin-2-yl)cyclobutyl]methanol (750 mg, 2.66 mmol) and 6-(trifluoromethyl)pyridine-2-carboxamide (505 mg, 2.66 mmol, Intermediate ATI) in dioxane (10 mL) was added t-Bu Xphos (225 mg, 531 umol), Pd$_2$(dba)$_3$ (243 mg, 265 umol), Cs$_2$CO$_3$ (1.73 g, 5.32 mmol) and 4 Å molecular sieves (50.0 mg). The reaction mixture was stirred at 100° C. for 16 hrs. On completion, the reaction mixture was filtered and concentrated in vacuo to give a residue. The residue was purified by column chromatography to give the title compound (400 mg, 38% yield) as a brown solid. $^1$H NMR (400 MHz, DMSO-$d_6$) δ 10.19 (s, 1H), 9.09 (s, 1H), 8.63 (s, 1H), 8.52-8.45 (m, 2H), 8.45-8.37 (m, 1H), 8.23 (d, J=7.6 Hz, 1H), 5.37-5.26 (m, 1H), 4.78 (t, J=5.2 Hz, 1H), 3.58 (t, J=6.0 Hz, 2H), 2.76-2.66 (m, 2H), 2.58-2.52 (m, 1H), 2.46-2.38 (m, 2H); LC-MS (ESI+) m/z 392.2 (M+H)+.

Step 5—[3-[5-[[6-(Trifluoromethyl)pyridine-2-carbonyl]amino]pyrazolo[3,4-c]pyridin-2-yl]cyclobutyl]methyl methanesulfonate To a solution of N-[2-[3-(hydroxymethyl)cyclobutyl]pyrazolo[3,4-c]pyridin-5-yl]-6-(trifluoromethyl) pyridine-2-carboxamide (350 mg, 894 umol) in DCM (3.5 mL) was added DIEA (346 mg, 2.68 mmol, 467 uL). The methylsulfonyl methanesulfonate (311 mg, 1.79 mmol) was added at 0° C., then the reaction mixture was stirred at 25° C. for 2 hrs. On completion, the reaction was diluted with water (8 mL) and extracted with DCM (2×10 mL). The combined organic layers were washed with brine (10 mL), dried over Na$_2$SO$_4$, filtered and concentrated in vacuo to give the title compound (415 mg, 98% yield) as brown oil. LC-MS (ESI+) m/z 470.2 (M+H)+.

Step 6—N-[2-[3-(iodomethyl)cyclobutyl]pyrazolo[3,4-c]pyridin-5-yl]-6-(trifluoromethyl)pyridine-2-carboxamide To a solution of [3-[5-[[6-(trifluoromethyl)pyridine-2-carbonyl]amino]pyrazolo[3,4-c]pyridin-2-yl]cyclobutyl]methyl methanesulfonate (415 mg, 884 umol) in THF (3 mL) was added NaI (596 mg, 3.98 mmol), then the reaction mixture was stirred at 70° C. for 16 hrs. On completion, the reaction was diluted with water (10 mL) and extracted with DCM (2×10 mL). The combined organic layers were washed with brine (10 mL), dried over Na$_2$SO$_4$, filtered and concentrated in vacuo to give the title compound (440 mg, 99% yield) as a brown solid. $^1$H NMR (400 MHz, DMSO-$d_6$) δ 10.19 (s, 1H), 9.09 (s, 1H), 8.63 (s, 1H), 8.50-8.43 (m, 2H), 8.43-8.37 (m, 1H), 8.24-8.19 (m, 1H), 5.46-5.31 (m, 1H), 3.64-3.55 (m, 2H), 2.98-2.84 (m, 1H), 2.81-2.69 (m, 2H), 2.42-2.33 (m, 2H); LC-MS (ESI+) m/z 502.1 (M+H)+.

[(E)-2-cyano-3,3-diethoxy-prop-1-enoxy] potassium (Intermediate BUV

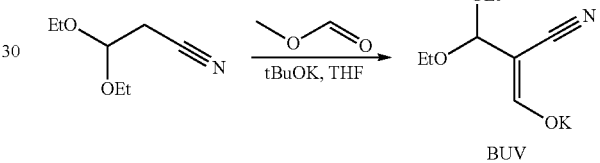

To a solution of 3,3-diethoxypropanenitrile (5.00 g, 34.9 mmol, CAS #2032-34-0) and methyl formate (2.73 g, 45.40 mmol, CAS #107-31-3) in THF (40 mL) was added potassium 2-methylpropan-2-olate (3.92 g, 34.9 mmol) slowly. The mixture was stirred at 10° C. for 2 hrs. On completion, hexane (200 mL) was added to the reaction mixture and stirred for 20 mins. Then the slurry was filtered and the cake washed with hexanes/THF (1:1) and dried at 60° C. in vacuo to give title product (4.60 g, 21.9 mmol, 62% yield) as a yellow solid. $^1$H NMR (400 MHz, CD$_3$OD) δ=5.22 (s, 1H), 4.68 (s, 1H), 3.57 (q, J=7.2 Hz, 4H), 1.14 (t, J=7.2 Hz, 6H).

6-Cyanopyrazolo[1,5-a]pyrimidine-3-carboxylic acid (Intermediate BUW)

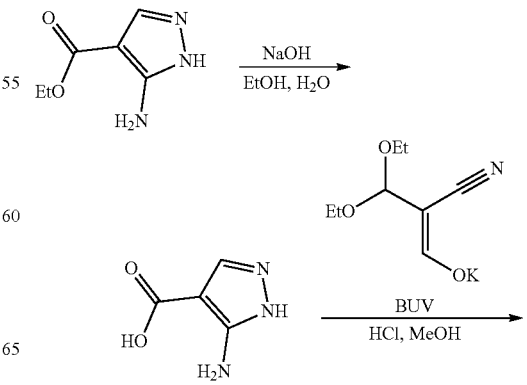

Step 1—5-Amino-1H-pyrazole-4-carboxylic Acid

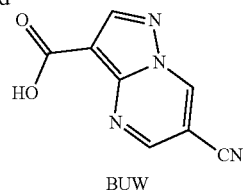
BUW

To a solution of ethyl 5-amino-1H-pyrazole-4-carboxylate (5.00 g, 32.2 mmol, CAS #6994-25-8) in EtOH (25 mL) and H$_2$O (25 mL) was added NaOH (2.58 g, 64.4 mmol), then the mixture was stirred at 80° C. for 12 hrs. On completion, the reaction mixture was concentrated in vacuo and the residue was purified by column chromatography (SiO$_2$, Petroleum ether/Ethyl acetate=10:1 to 1:1) to get the title compound (4.00 g, 28.3 mmol) as a white solid. $^1$H NMR (400 MHz, DMSO-d$_6$) δ 11.68 (s, 1H), 7.53 (s, 1H), 5.70 (s, 2H).

Step 2—6-Cyanopyrazolo[1,5-a]pyrimidine-3-carboxylic Acid

AcOH (472 mg, 7.87 mmol) was added to 5-amino-1H-pyrazole-4-carboxylic acid (50.0 mg, 393 umol) slowly and the mixture was stirred at 25° C. for 10 mins. Then a solution of [(E)-2-cyano-3,3-diethoxy-prop-1-enoxy]potassium (82.3 mg, 393 umol, Intermediate BUV) in EtOH (0.5 mL) was added. After addition, the reaction mixture was stirred at 80° C. for 2 hrs. Lots of solid was precipitated. The solid was filtered to give the title compound (50.0 mg, 265 umol) as white solid. $^1$H NMR (400 MHz, DMSO-d$_6$) δ 10.01 (d, J=2.0 Hz, 1H), 8.89 (d, J=2.0 Hz, 1H), 8.62 (s, 1H).

5-chloro-6-methyl-pyridine-3-carboxylic acid (CAS #1256835-19-4) (Intermediate BUX)

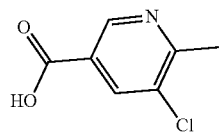

N-[2-(3-formylcyclobutyl)-6-methoxy-indazol-5-yl]-6-(trifluoromethyl)pyridine-2-carboxamide (Intermediate BUY)

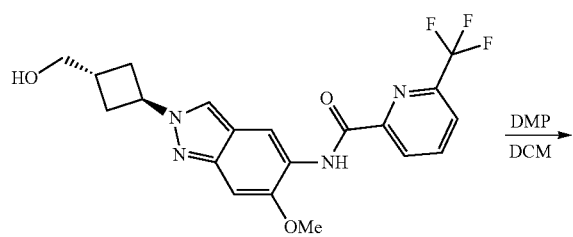

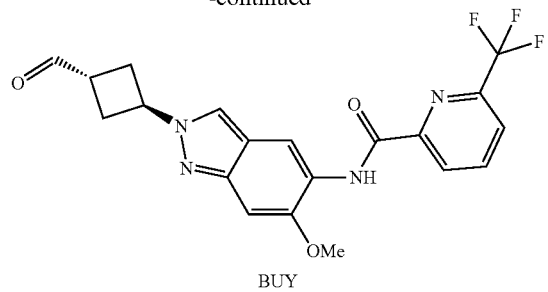
BUY

To a mixture of N-[2-[3-(hydroxymethyl) cyclobutyl]-6-methoxy-indazol-5-yl]-6-(trifluoromethyl) pyridine-2-carboxamide (50.0 mg, 118 umol, synthesized via Steps 1-3 of Intermediate BQI) in DCM (3 mL) was added DMP (75.6 mg, 178 umol). The reaction mixture was stirred at 25° C. for 12 hrs. On completion, the reaction mixture was quenched with saturated Na$_2$S$_2$O$_3$ (8 mL) and saturated NaHCO$_3$ (8 mL) at 25° C., and then stirred for 30 minutes. The mixture was extracted with DCM (2×30 mL). Then the organic layer was separated and concentrated in vacuo to give the title compound (49.0 mg, 98% yield) as yellow solid. LC-MS (ESI$^+$) m/s 419.1 (M+H)$^+$.

5-chloropyridazine-3-carboxylic acid (CAS #1211587-01-7) (Intermediate BUZ)

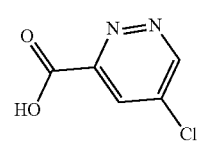
BUZ

3-[5-Methoxy-3-methyl-2-oxo-4-(4-piperidyl)benzimidazol-1-yl]piperidine-2,6-dione (Intermediate BVA)

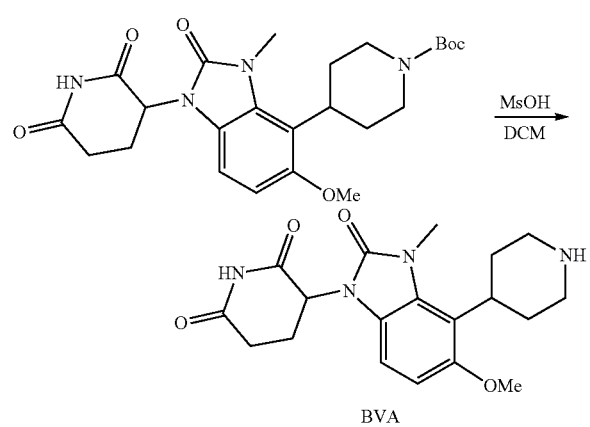
BVA

To a solution of tert-butyl 4-[1-(2,6-dioxo-3-piperidyl)-5-methoxy-3-methyl-2-oxo-benzimidazol-4-yl] piperidine-1-carboxylate (80.0 mg, 169 umol, synthesized via Steps 1-5 of Intermediate BUC) in DCM (0.5 mL) was added MsOH (48.8 mg, 507 umol). The reaction mixture was stirred at 25° C. for 30 mins. On completion, the reaction mixture was concentrated in vacuo to give the title compound (60.0 mg, 757% yield) as a gray solid. LC-MS (ESI+) m/z 373.3 (M+H)+.

5-Cyano-N-[2-(4-formylcyclohexyl)-6-methoxy-indazol-5-yl]pyridine-3-carboxamide (Intermediate BVB)

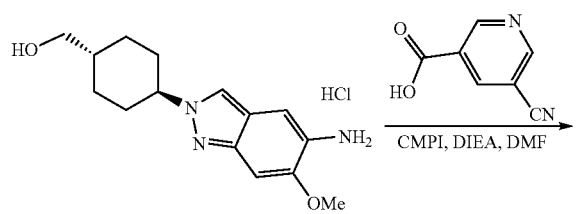

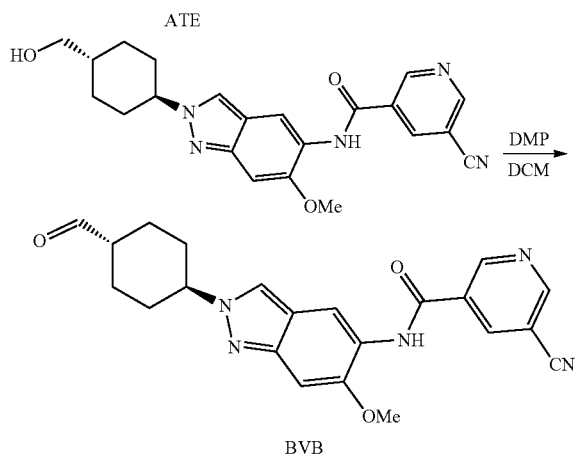

Step 1—5-Cyano-N-[2-[4-(hydroxymethyl)cyclo-hexyl]-6-methoxy-indazol-5-yl]pyridine-3-carbox-amide A mixture of [4-(5-amino-6-methoxy-indazol-2-yl)cyclohexyl]methanol (260 mg, 833 umol, HCl, Intermediate ATE) and DIEA (431 mg, 3.34 mmol) in DMF (3 mL) was stirred at 25° C. for 0.2 hour. Then, 5-cyanopyridine-3-carboxylic acid (111 mg, 750 umol, CAS #887579-62-6), DIEA (431 mg, 3.34 mmol) and CMPI (276 mg, 1.08 mmol) in DMF (3 mL) was stirred at 25° C. for 0.2 hour and it was then added to the reaction mixture dropwise. The reaction mixture was stirred at 25° C. for 1.5 hours. On completion, the mixture was diluted with water (30 mL) and extracted with EA (2×30 mL). The combined organic layer was dried over Na2SO4, filtered and concentrated in vacuo to give a residue. The residue was purified by reverse phase (0.1% FA condition) to give the title compound (335 mg, 99% yield) as light yellow solid. 1H NMR (400 MHz, CDCl3) δ 9.31 (d, J 1.6 Hz, 1H), 9.05 (d, J=1.6 Hz, 1H), 8.80-8.69 (m, 2H), 8.51 (s, 1H), 7.91 (s, 1H), 7.11 (s, 1H), 4.43-4.29 (m, 1H), 4.03 (s, 3H), 3.57 (d, J=6.4 Hz, 2H), 2.39-2.32 (m, 2H), 2.10-1.96 (m, 4H), 1.73-1.64 (m, 1H), 1.26 (s, 2H). LC-MS (ESI+) m/z 406.2 (M+H)+.

Step 2—5-Cyano-N-[2-(4-formylcyclohexyl)-6-methoxy-indazol-5-yl]pyridine-3-carboxamide To a mixture of 5-cyano-N-[2-[4-(hydroxymethyl)cyclohexyl]-6-methoxy-indazol-5-yl]pyridine-3-carboxamide (360 mg, 887 umol) in DCM (5 mL) was added DMP (489 mg, 1.15 mmol). The reaction mixture was stirred at 25° C. for 1 hour. On completion, the reaction mixture was quenched with saturated Na2S2O3 (10 mL) and saturated NaHCO3 (10 mL) at 25° C., and then the mixture was stirred for 30 minutes. The residue was diluted with water (50 mL) and extracted with DCM (2×50 mL). The combined organic layer was dried over Na2SO4, filtered and concentrated in vacuo to give a residue. The residue was purified by reverse phase (0.1% FA condition) to give the title compound (250 mg, 69% yield) as yellow solid. LC-MS (ESI+) m/z 404.2 (M+H)+.

5-Cyano-N-[2-(4-formylcyclohexyl)-6-methoxy-indazol-5-yl]pyrrolo[2,3-b]pyridine-1-carboxamide (Intermediate BVC)

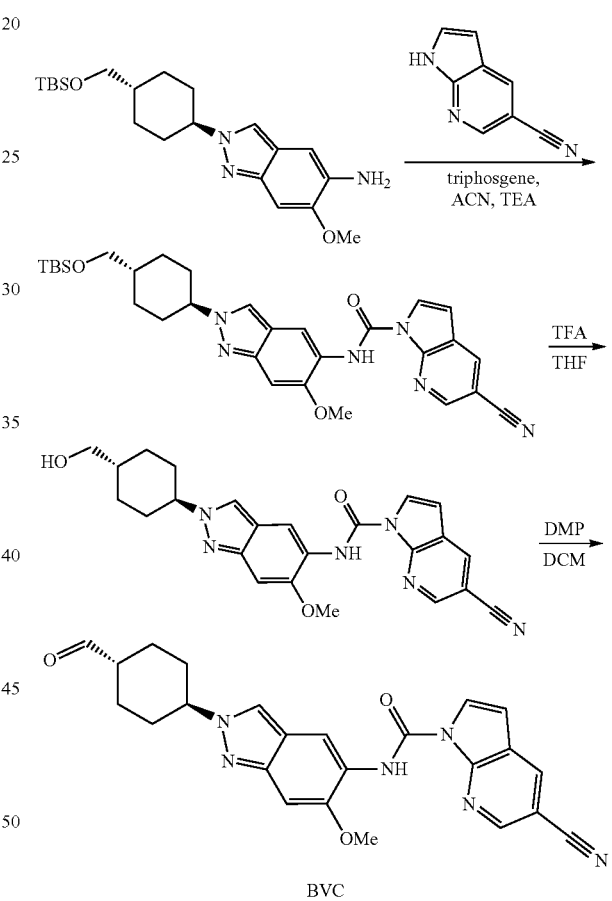

Step 1—N-[2-[4-[[tert-butyl(dimethyl)silyl]oxym-ethyl]cyclohexyl]-6-methoxy-indazol-5-yl]-5-cyano-pyrrolo[2,3-b]pyridine-1-carboxamide To a solution of 1H-pyrrolo[2,3-b]pyridine-5-carbonitrile (128 mg, 898 umol, CAS #517918-95-5) in ACN (3 mL) was added TEA (454 mg, 4.49 mmol, 625 uL), and the reaction mixture was stirred at 0° C., then triphosgene (360 mg, 1.21 mmol) was added. Next, 2-[4-[[tert-butyl (dimethyl)silyl]oxymethyl]cyclohexyl]-6-methoxy-indazol-5-amine (350 mg, 898 umol, synthesized via Step 1 of Intermediate BUM) was added, then the reaction mixture was stirred at 80° C. for 16 hrs. On completion, the mixture was quenched with water (8 mL), diluted with more water (10 mL), then extracted with DCM (2×15 mL). The combined organic layers were washed with brine (10 mL), dried over Na$_2$SO$_4$, filtered and concentrated in vacuo to give a residue. The residue was purified by reverse phase (0.1% FA condition) to give the title compound (200 mg, 39% yield) as a white solid. $^1$H NMR (400 MHz, DMSO-d$_6$) δ 12.05 (s, 1H), 9.06 (s, 1H), 8.76 (d, J=0.8 Hz, 1H), 8.49 (s, 1H), 8.32 (s, 1H), 8.26 (d, J=4.0 Hz, 1H), 7.15 (s, 1H), 6.91 (d, J=3.6 Hz, 1H), 4.42-4.29 (m, 1H), 4.07 (s, 3H), 3.47 (d, J=6.0 Hz, 2H), 2.19-2.10 (m, 2H), 1.96-1.80 (m, 4H), 1.62-1.48 (m, 1H), 1.24-1.12 (m, 2H), 0.89 (s, 9H), 0.06 (s, 6H), LC-MS (ESI$^+$) m/z 559.3 (M+H)$^+$.

Step 2—5-Cyano-N-[2-[4-(hydroxymethyl)cyclohexyl]-6-methoxy-indazol-5-yl]pyrrolo[2,3-b] pyridine-1-carboxamide To a solution of N-[2-[4-[[tert-butyl(dimethyl)silyl]oxymethyl]cyclohexyl]-6-methoxy-indazol-5-yl]-5-cyano-pyrrolo[2,3-b]pyridine-1-carboxamide (80.0 mg, 143 umol) in THF (1 mL) was added TFA (97.9 mg, 859 umol, 63.6 uL), then the reaction mixture was stirred at 50° C. for 16 hrs. On completion, the reaction mixture was diluted with THF (3 mL), then basified with TEA until the pH=7-8. Then the mixture was extracted with DCM (2×5 mL) and the combined organic layers was dried over Na$_2$SO$_4$, filtered and concentrated in vacuo to give the title compound (60 mg, 94% yield) as a white solid. $^1$H NMR (400 MHz, DMSO-d$_6$) δ 12.05 (s, 1H), 9.06 (d, J=2.0 Hz, 1H), 8.76 (d, J=1.6 Hz, 1H), 8.51-8.46 (m, 1H), 8.32 (s, 1H), 8.26 (d, J=4.0 Hz, 1H), 7.15 (s, 1H), 6.91 (d, J=4.0 Hz, 1H), 4.49 (t, J=5.2 Hz, 1H), 4.07 (s, 3H), 3.30-3.26 (m, 2H), 3.13-3.05 (m, 1H), 2.18-2.09 (m, 2H), 1.96-1.84 (m, 4H), 1.54-1.45 (m, 1H), 1.17-1.12 (m, 2H), LC-MS (ESI$^+$) m/z 445.2 (M+H)$^+$.

Step 3—5-Cyano-N-[2-(4-formylcyclohexyl)-6-methoxy-indazol-5-yl]pyrrolo[2,3-b]pyridine-1-carboxamide To a solution of 5-cyano-N-[2-[4-(hydroxymethyl)cyclohexyl]-6-methoxy-indazol-5-yl]pyrrolo[2,3-b]pyridine-1-carboxamide (60.0 mg, 134 umol) in DCM (1 mL) was added DMP (68.7 mg, 161 umol, 50.1 uL), then the reaction mixture was stirred at 25° C. for 2 hrs. On completion, the reaction mixture was quenched with Na$_2$S$_2$O$_3$ (2 mL) and NaHCO$_3$(2 mL) and extracted with DCM (2×5 mL). The combined organic phase was washed with NaHCO$_3$(3 mL) and brine (2×5 mL), dried with anhydrous Na$_2$SO$_4$, filtered and the filtrate was concentrated in vacuo to give the title compound (59 mg, 98% yield) as a white solid. LC-MS (ESI$^+$) m/z 443.2 (M+H)$^+$.

(1R,4R)-Methyl 4-(chlorocarbonyl)cyclohexanecarboxylate (Intermediate BCU)

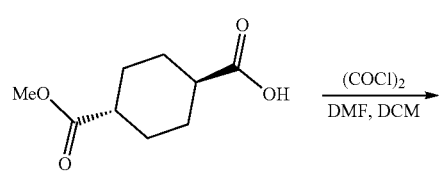

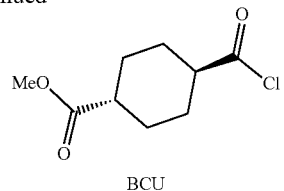

BCU

To a solution of 4-methoxycarbonylcyclohexanecarboxylic acid (500 mg, 2.69 mmol) in the DCM (10 mL) was added DMF (19.6 mg, 268 umol, 20.6 uL) and (COCl)$_2$ (511 mg, 4.03 mmol). The mixture was stirred at 25° C. for 1 hr. On completion, the reaction mixture was concentrated in vacuo to give the title compound (549 mg, 99% yield) as yellow oil.

Methyl 4-(6-bromo-5-methoxy-1,3-benzothiazol-2-yl)cyclohexanecarboxylate (Intermediate BFN)

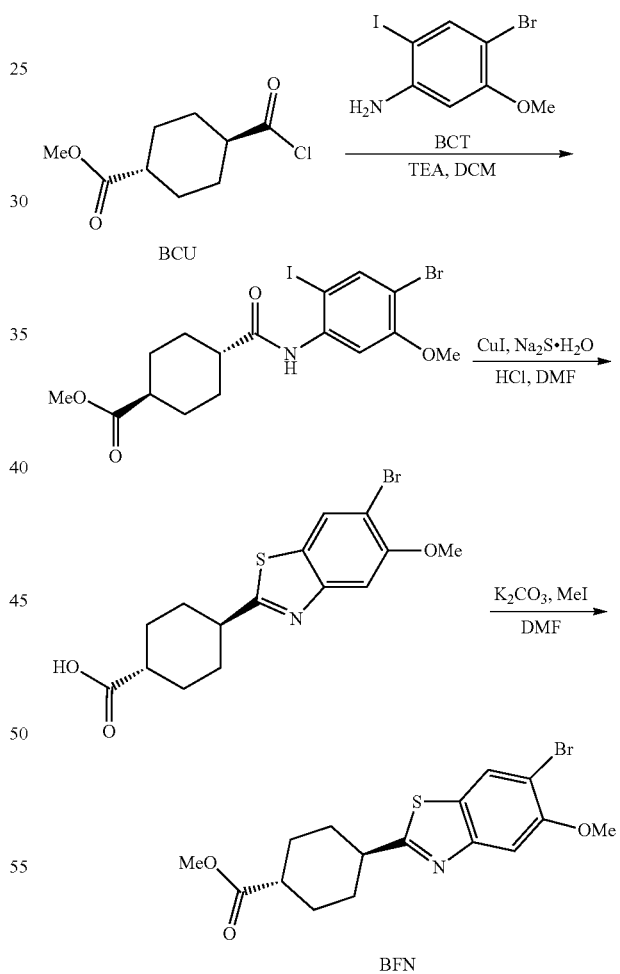

Step 1—(1r,4r)-Methyl 4-((4-bromo-2-iodo-5-methoxyphenyl)carbamoyl)cyclohexanecarboxylate To a solution of 4-bromo-2-iodo-5-methoxy-aniline (880 mg, 2.68 mmol, Intermediate BCT) and Et3N (814 mg, 8.05 mmol) in the DCM (10 mL) was added methyl 4-chlorocarbonylcyclohexanecarboxylate (549 mg, 2.68 mmol, Intermediate BCU). The mixture was stirred at 25° C. for 12 hrs. On completion, the reaction mixture was washed with water (50 mL). The organic layer was dried over $Na_2SO_4$, filtered and concentrated in vacuo and the residue was triturated with (PE:EA=3:1) to give the title compound (800 mg, 60% yield) as white solid. 1H NMR (400 MHz, $CDCl_3$) δ 8.15 (s, 1H), 7.86 (s, 1H), 7.52 (s, 1H), 3.91 (s, 3H), 3.70 (s, 3H), 2.41-2.27 (m, 2H), 2.15 (d, J=12.6 Hz, 4H), 1.69-1.49 (m, 4H).

Step 2—(1R,4r)-4-(6-Bromo-5-hydroxybenzo[d]thiazol-2-yl)cyclohexanecarboxylic Acid To a solution of methyl 4-[(4-bromo-2-iodo-5-methoxyphenyl)carbamoyl]cyclohexanecarboxylate (0.8 g, 1.61 mmol) in the DMF (10 mL) was added $Na_2S·9H_2O$ (774 mg, 3.22 mmol) and CuI (61.4 mg, 322 umol). The mixture was stirred at 80° C. for 12 hrs under $N_2$. Then the mixture was cooled down to room temperature and HCl (12 M, 1.34 mL, 36% solution) was added. The mixture was stirred at 25° C. for 5 hrs. On completion, the reaction mixture was diluted with EA (100 mL) and washed with water (3×100 mL). The organic layer was dried over $Na_2SO_4$, filtered and concentrated in vacuo to give the title compound (570 mg, 99% yield) as yellow solid. LC-MS ($ESI^+$) m/z 370.2 $(M+H)^+$.

Step 3—(1R,4r)-Methyl 4-(6-bromo-5-methoxybenzo[d]thiazol-2-yl)cyclohexanecarboxylate To a solution of 4-(6-bromo-5-hydroxy-1,3-benzothiazol-2-yl)cyclohexanecarboxylic acid (567 mg, 1.59 mmol) in the DMF (10 mL) was added $K_2CO_3$ (440 mg, 3.19 mmol) and MeI (678 mg, 4.78 mmol). The mixture was stirred at 25° C. for 3 hrs. On completion, the reaction mixture was diluted with EA (100 mL) and washed with water (3×100 mL). The organic layer was dried over $Na_2SO_4$, filtered and concentrated in vacuo and purified by column chromatography ($SiO_2$, Petroleum ether/Ethyl acetate=10/1 to 5/1) to give the title compound (320 mg, 47% yield) as white solid. $^1$H NMR (400 MHz, $CDCl_3$) δ 8.00 (s, 1H), 7.49 (s, 1H), 3.97 (s, 3H), 3.71 (s, 3H), 3.10-3.01 (m, 1H), 2.34-2.30 (m, 2H), 2.21-2.16 (m, 2H), 2.15-2.10 (m, 1H), 1.75-1.61 (m, 4H).

N-[2-(4-formylcyclohexyl)-5-methoxy-1,3-benzothiazol-6-yl]-6-(trifluoromethyl)pyridine-2-carboxamide (Intermediate BCN)

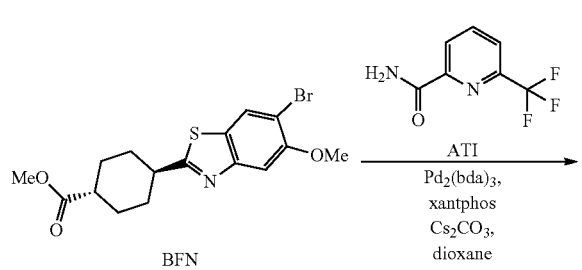

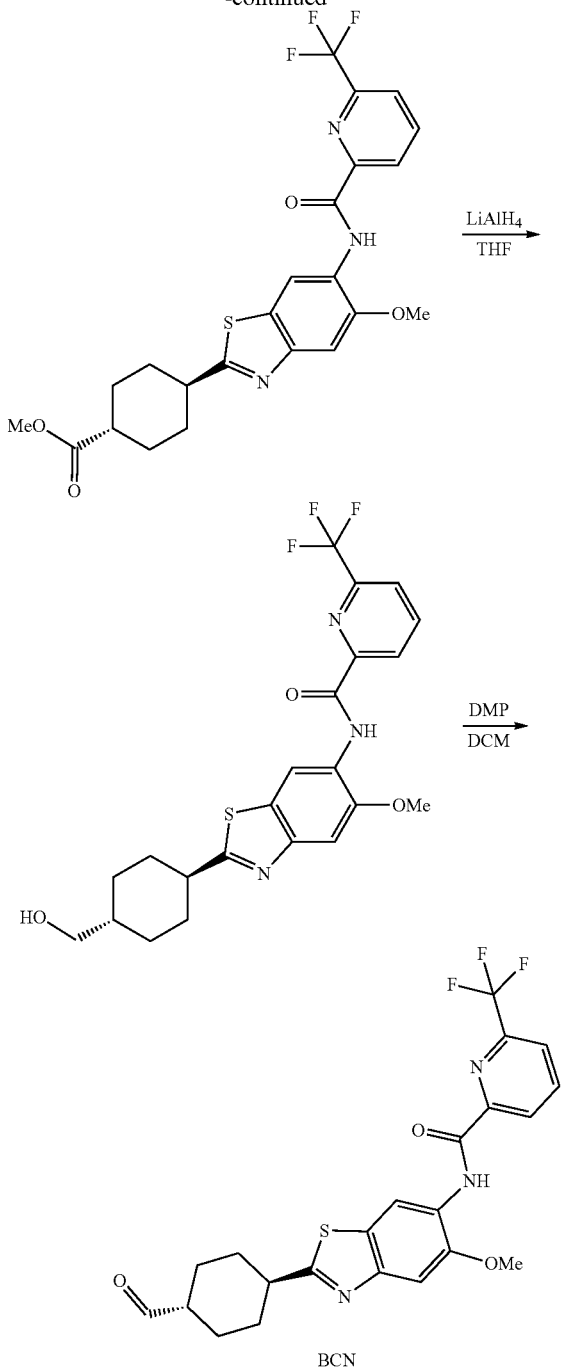

Step 1—(1R,4r)-Methyl 4-(5-methoxy-6-(6-(trifluoromethyl)picolinamido)benzo[d]thiazol-2-yl)cyclohexanecarboxylate To a solution of methyl 4-(6-bromo-5-methoxy-1,3-benzothiazol-2-yl)cyclohexanecarboxylate (300 mg, 780 umol, Intermediate BFN) and 6-(trifluoromethyl)pyridine-2-carboxamide (163 mg, 858 umol, Intermediate ATI) in the dioxane (3 mL) was added $Pd_2(dba)_3$ (71.4 mg, 78.0 umol), Xantphos (90.3 mg, 156 umol) and $Cs_2CO_3$ (508 mg, 1.56 mmol). The mixture was stirred at 100° C. for 6 hrs under $N_2$. On completion, the mixture was concentrated in vacuo.

The residue was purified by column chromatography (SiO₂, Petroleum ether/Ethyl acetate=10/1 to 3/1) to give the title compound (300 mg, 74% yield) as white solid. ¹H NMR (400 MHz, CDCl₃) δ 10.70 (s, 1H), 9.12 (s, 1H), 8.51 (d, J=8.0 Hz, 1H), 8.14 (t, J=8.0 Hz, 1H), 7.89 (d, J=7.6 Hz, 1H), 7.54 (s, 1H), 4.06 (s, 3H), 3.72 (s, 3H), 3.10-3.06 (m, 1H), 2.47-2.39 (m, 1H), 2.34 (d, J=11.2 Hz, 2H), 2.19 (d, J=11.2 Hz, 2H), 1.78-1.59 (m, 4H).

Step 2—N-(2-((1r,4 r)-4-(hydroxymethyl)cyclohexyl)-5-methoxybenzo[d]thiazol-6-yl)-6-(trifluoro methyl)picolinamide To a solution of methyl 4-[5-methoxy-6-[[6-(trifluoromethyl)pyridine-2-carbonyl]amino]-1,3-benzothiazol-2-yl]cyclohexanecarboxylate (50.0 mg, 101 umol) in the THF (1 mL) was added LiAlH₄ (3.85 mg, 101 umol) under 0° C. The mixture was stirred at 0° C. for 1 hr. On completion, the reaction mixture was quenched by water (0.05 mL) and NaOH (15% aq, 0.05 mL) at 0° C. Then the mixture was dried over Na₂SO₄, filtered and concentrated in vacuo to give the title compound (47.0 mg, 99% yield) as yellow solid. ¹H NMR (400 MHz, CDCl₃) δ 10.70 (s, 1H), 9.11 (s, 1H), 8.51 (d, J=7.6 Hz, 1H), 8.14 (t, J=7.6 Hz, 1H), 7.89 (d, J=7.6 Hz, 1H), 7.54 (s, 1H), 4.06 (s, 3H), 3.55 (t, J=6.0 Hz, 2H), 3.08-3.02 (m, 1H), 2.36-2.29 (m, 2H), 2.01 (dd, J=3.2, 13.2 Hz, 2H), 1.77-1.66 (m, 2H), 1.65-1.58 (m, 1H), 1.33 (t, J=5.6 Hz, 1H), 1.25-1.14 (m, 2H).

Step 3—N-(2-((1r,4 r)-4-formylcyclohexyl)-5-methoxybenzo[d]thiazol-6-yl)-6-(trifluoromethyl)picolinamide To a solution of N-[2-[4-(hydroxymethyl)cyclohexyl]-5-methoxy-1,3-benzothiazol-6-yl]-6-(trifluoro methyl)pyridine-2-carboxamide (47.0 mg, 100 umol) in the DCM (1 mL) was added DMP (51.4 mg, 121 umol). The mixture was stirred at 25° C. for 1 hour. On completion, the reaction mixture was quenched by the addition of Na₂S₂O₃ (aq. 3 mL) and NaHCO₃(aq. 3 mL). Then the mixture was extracted with DCM (2×20 mL). The organic layer was dried over Na₂SO₄, filtered and concentrated in vacuo to give the title compound (46.0 mg, 98% yield) as yellow solid. LC-MS (ESI⁺) m/z 464.1 (M+H)⁺.

Tert-butyl N-[6-fluoro-2-(4-formylcyclohexyl)indazol-5-yl]carbamate (Intermediate BVD)

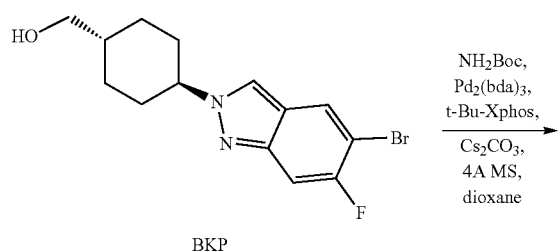

BKP

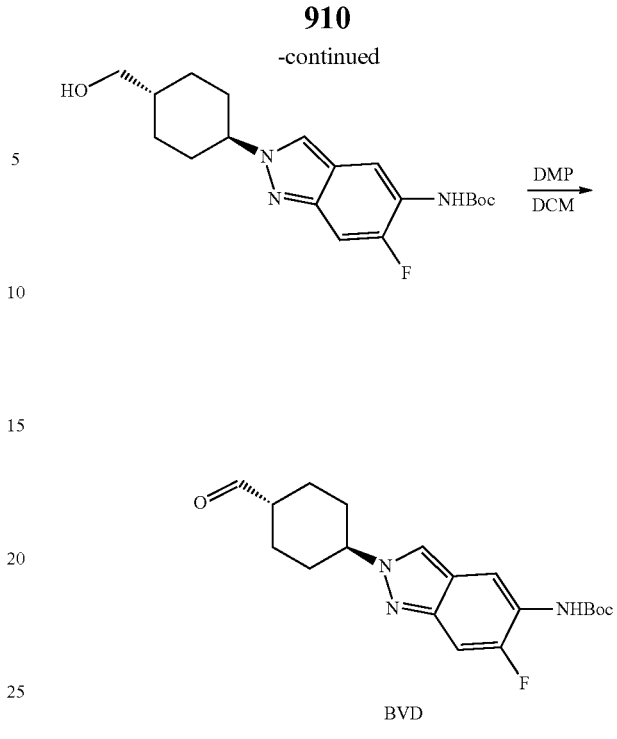

Step 1—Tert-butyl N-[6-fluoro-2-[4-(hydroxymethyl)cyclohexyl]indazol-5-yl]carbamate To a solution of [4-(5-bromo-6-fluoro-indazol-2-yl)cyclohexyl]methanol (1.00 g, 3.06 mmol, Intermediate BKP) and tert-butyl carbamate (358 mg, 3.06 mmol) in dioxane (10 mL), was added Pd₂(dba)₃ (279 mg, 305 umol), Cs₂CO₃ (1.99 g, 6.11 mmol), 4 Å molecular sieves (250 mg), and t-Bu Xphos (259 mg, 611 umol), then the mixture was stirred at 90° C. for 16 hrs. On completion, the mixture was concentrated in vacuo to give the residue. The residue was purified by reverse phase (0.1% FA condition) to give the title compound (600 mg, 54% yield) as a white solid. ¹H NMR (400 MHz, DMSO-d₆) δ 8.73 (s, 1H), 8.35 (s, 1H), 7.86-7.65 (m, 1H), 7.41-7.28 (m, 1H), 4.49 (t, J=5.6 Hz, 1H), 4.45-4.33 (m, 1H), 3.30-3.26 (m, 3H), 2.15-2.10 (m, 2H), 1.92-1.84 (m, 4H), 1.45 (s, 9H), 1.18-1.09 (m, 2H); LC-MS (ESI⁺) m/z 364.2 (M+H)⁺.

Step 2—Tert-butyl N-[6-fluoro-2-(4-formylcyclohexyl)indazol-5-yl]carbamate

To a solution of tert-butyl N-[6-fluoro-2-[4-(hydroxymethyl)cyclohexyl]indazol-5-yl]carbamate (100 mg, 275 umol) in DCM (1 mL) was added DMP (140 mg, 330 umol), then the reaction mixture was stirred at 25° C. for 2 hrs. On completion, the reaction mixture was quenched with Na₂S₂O₃ (5 mL) and NaHCO₃ (5 mL) and extracted with DCM (2×20 mL). The combined organic phase was washed with NaHCO₃ (10 mL) and brine (10 mL), dried with anhydrous Na₂SO₄, filtered and the filtrate was concentrated in vacuo to give the title compound (99 mg, 99% yield) as a purple solid. LC-MS (ESI⁺) m/z 362.4 (M+H)⁺.

3-[4-[1-[[4-(5-Amino-6-fluoro-indazol-2-yl)cyclo-hexyl]methyl]-4-piperidyl]-3-methyl-2-oxo-benzimi-dazol-1-yl]piperidine-2,6-dione (Intermediate BVE)

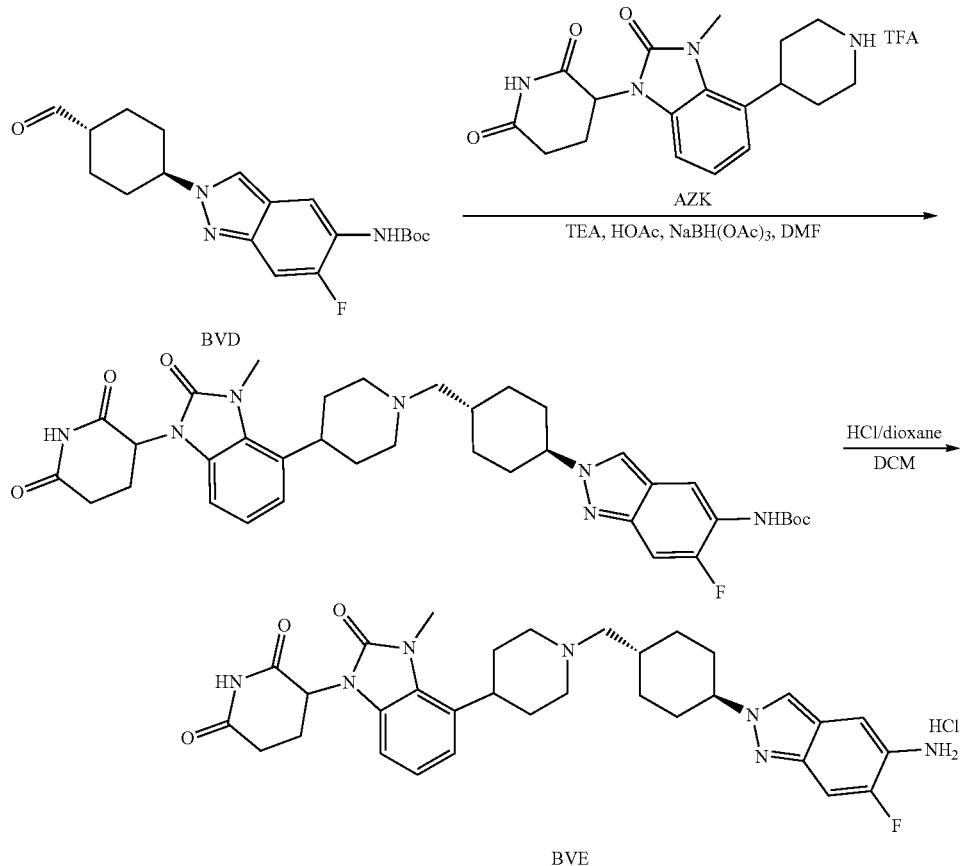

Step 1—4-Tert-butyl N-[2-[4-[[4-[1-(2,6-dioxo-3-piperidyl)-3-methyl-2-oxo-benzimidazol-4-yl]-1-piperidyl]methyl]cyclohexyl]-6-fluoro-indazol-5-yl]carbamate To a solution of 3-[3-methyl-2-oxo-4-(4-piperidyl)benz-imidazol-1-yl]piperidine-2,6-dione (183 mg, 401 umol, TFA, Intermediate AZK) in DMF (2 mL) and THF (2 mL) was added TEA (40.6 mg, 401 umol, 55.8 uL), then the mixture was stirred at −10° C. for 10 mins. Next, tert-butyl N-[6-fluoro-2-(4-formylcyclohexyl)indazol-5-yl]carbamate (145 mg, 401 umol, Intermediate BVD) and NaBH(OAc)$_3$ (102 mg, 481 umol) was added to the mixture, and the mixture was stirred at −10° C. for 20 mins. Finally, AcOH (24.0 mg, 401 umol, 22.9 uL) was added to the mixture, and the mixture was stirred at −10° C. for 1 hr. On completion, the reaction mixture was quenched with water (0.5 mL) and concentrated in vacuo to give a residue. The residue was purified by reverse phase (0.1% FA condition) to give the title compound (200 mg, 72% yield) as a white solid. $^1$H NMR (400 MHz, DMSO-d$_6$) δ 11.10 (s, 1H), 8.80-8.65 (m, 1H), 8.36 (s, 1H), 8.13 (s, 1H), 7.40-7.30 (m, 1H), 7.07-6.98 (m, 3H), 5.38 (dd, J=4.4, 12.0 Hz, 1H), 4.51-4.38 (m, 1H), 3.61 (s, 3H), 3.46-3.40 (m, 1H), 2.94-2.85 (m, 1H), 2.76-2.62 (m, 4H), 2.53-2.51 (m, 2H), 2.19-2.13 (m, 2H), 2.03-1.86 (m, 11H), 1.84-1.77 (m, 1H), 1.46 (s, 9H), 1.27-1.20 (m, 2H), LC-MS (ESI$^+$) m/z 688.3 (M+H)$^+$.

Step 2—3-[4-[1-[[4-(5-Amino-6-fluoro-indazol-2-yl)cyclohexyl]methyl]-4-piperidyl]-3-methyl-2-oxo-benzimidazol-1-yl]piperidine-2,6-dione To a solution of tert-butyl N-[2-[4-[[4-[1-(2,6-dioxo-3-piperidyl)-3-methyl-2-oxo-benzimidazol-4-yl]-1-piperidyl]methyl]cyclohexyl]-6-fluoro-indazol-5-yl]carbamate (85.0 mg, 123 umol) in DCM (1 mL) was added HCl/dioxane (4 M, 1 mL), then the reaction mixture was stirred at 25° C. for 0.5 hr. On completion, the reaction mixture was concentrated in vacuo to give the title compound (75 mg, 97% yield) as a white solid. LC-MS (ESI$^+$) m/z 588.5 (M+H)$^+$.

5-chloro-6-cyano-pyridine-3-carboxylic acid (Intermediate BVF)

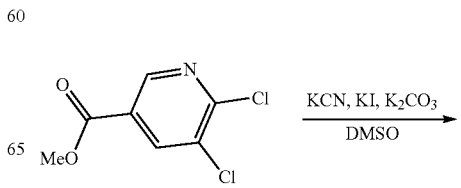

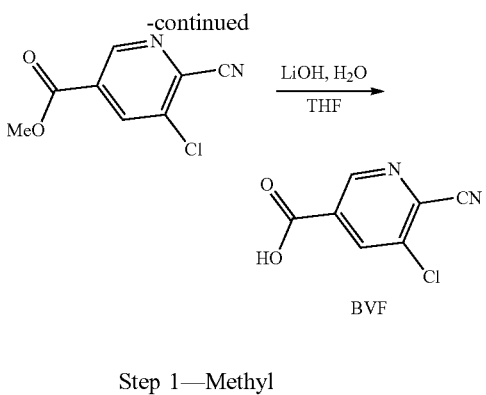

Step 1—Methyl 5-chloro-6-cyano-pyridine-3-carboxylate

To a solution of methyl 5,6-dichloropyridine-3-carboxylate (1.00 g, 4.85 mmol, CAS #56055-54-0) in DMSO (10 mL) was added KCN (370 mg, 5.68 mmol) and KI (403 mg, 2.43 mmol) and $K_2CO_3$ (1.34 g, 9.71 mmol). The mixture was stirred at 50° C. for 3 hrs. On completion, the mixture was diluted with EA (50 mL) and water (30 mL). The organic phase was washed with brine (20 mL×3), dried with anhydrous $Na_2SO_4$, filtered and the filtrate was concentrated in vacuo. The residue was purified by silica gel chromatography (petroleum ether/ethyl acetate=8/1) to give the title compound (240 mg, 25% yield) as a white solid. $^1H$ NMR (400 MHz, DMSO-$d_6$) δ 9.12 (d, J=1.6 Hz, 1H), 8.68-8.64 (m, 1H), 3.94 (s, 3H).

Step 2—5-chloro-6-cyano-pyridine-3-carboxylic Acid

To a solution of methyl 5-chloro-6-cyano-pyridine-3-carboxylate (50.0 mg, 254 umol) in $H_2O$ (0.5 mL) and THF (0.5 mL) was added LiOH·$H_2O$ (25.0 mg, 595 umol). The mixture was stirred at 20° C. for 2 hrs. On completion, the mixture was acidified with $KHSO_4$ (aq) until the pH=5, then the mixture was extracted with ethyl acetate (20 mL×2). The combined organic layers were dried with anhydrous $Na_2SO_4$, filtered and the filtrate was concentrated in vacuo to give the title compound (20 mg, 43% yield) as a white solid. $^1H$ NMR (400 MHz, DMSO-$d_6$) δ 9.10 (d, J=1.6 Hz, 1H), 8.61 (d, J=1.8 Hz, 1H).

4-[5-[[6-(Trifluoromethyl)pyridine-2-carbonyl]amino]indazol-2-yl]cyclohexanecarboxylic acid (Intermediate BVG)

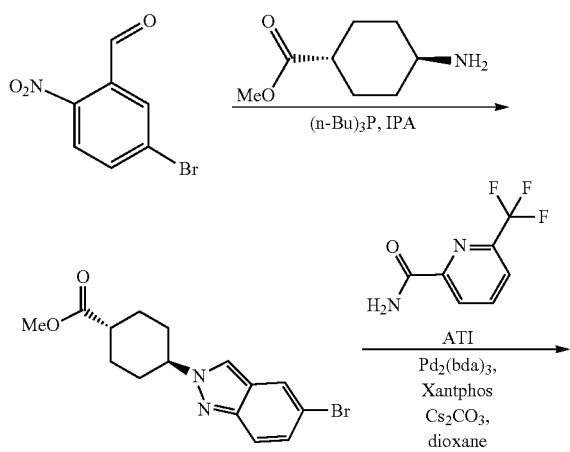

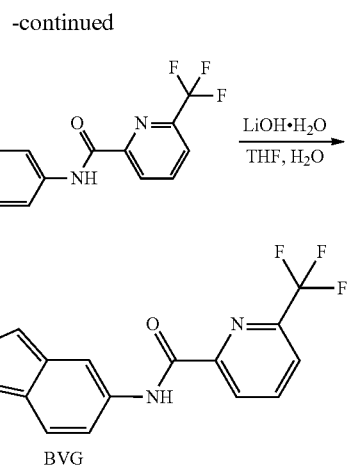

Step 1—Methyl 4-(5-bromoindazol-2-yl)cyclohexanecarboxylate

To a mixture of methyl 4-aminocyclohexanecarboxylate (4.51 g, 28.6 mmol CAS #62456-15-9) in IPA (100 mL) was added 5-bromo-2-nitro-benzaldehyde (6.00 g, 26.0 mmol CAS #20357-20-4). The mixture was stirred at 25° C. for 3 hours. Next, tributylphosphane (15.8 g, 78.2 mmol, 19.3 mL) was added and the reaction mixture was stirred at 80° C. for 4 hours. On completion, the reaction mixture was concentrated in vacuo. The residue was purified by column chromatography to give the title compound (3.80 g, 43% yield) as white solid. $^1H$ NMR (400 MHz, DMSO-$d_6$) δ 8.38 (s, 1H), 7.95 (s, 1H), 7.58 (d, J=9.2 Hz, 1H), 7.30 (dd, J=1.6, 9.2 Hz, 1H), 4.53 (tt, J=3.6, 11.6 Hz, 1H), 3.63 (s, 3H), 2.49-2.41 (m, 1H), 2.15 (d J=9.6 Hz, 2H), 2.07 (d, J=13.2 Hz, 2H), 2.02-1.88 (m, 2H), 1.68-1.52 (m, 2H).

Step 2—Methyl 4-[5-[[6-(trifluoromethyl)pyridine-2-carbonyl]amino]indazol-2-yl]cyclohexanecarboxylate To a mixture of methyl 4-(5-bromoindazol-2-yl)cyclohexanecarboxylate (2.00 g, 5.93 mmol) and 6-(trifluoromethyl)pyridine-2-carboxamide (1.35 g, 7.12 mmol, Intermediate ATI) in dioxane (20 mL) was added in $Cs_2CO_3$ (3.86 g, 11.8 mmol), Xantphos (686 mg, 1.19 mmol) and $Pd_2(dba)_3$ (543 mg, 593 umol), then the reaction mixture was stirred at 80° C. for 12 hours. On completion, the residue was diluted with water (30 mL) and extracted with EA (3×100 mL). The combined organic layer was dried over $Na_2SO_4$, filtered and concentrated in vacuo to give a residue. The residue was purified by reverse phase (0.1% FA condition) and then the residue was purified by column chromatography to give the title compound (770 mg, 29% yield) as yellow solid. $^1H$ NMR (400 MHz, DMSO-$d_6$) δ 10.36 (s, 1H), 8.42-8.33 (m, 3H), 8.29 (s, 1H), 8.17 (d, J=7.6 Hz, 1H), 7.63-7.53 (m, 2H), 4.54-4.46 (m, 1H), 3.63 (s, 3H), 2.48-2.43 (m, 1H), 2.18 (d, J=9.6 Hz, 2H), 2.08 (d, J=11.6 Hz, 2H), 2.03-1.93 (m, 2H), 1.67-1.53 (m, 2H).

Step 3—4-[5-[[6-(Trifluoromethyl)pyridine-2-carbonyl]amino]indazol-2-yl]cyclohexanecarboxylic Acid To a mixture of methyl 4-[5-[[6-(trifluoromethyl) pyridine-2-carbonyl]amino]indazol-2-yl]cyclohexanecarboxylate (300 mg, 672 umol) in MeOH (0.5 mL), $H_2O$ (2 mL)

915 and THF (6 mL) was added LiOH·H₂O (84.5 mg, 2.02 mmol). The reaction mixture was stirred at 25° C. for 1.5 hours. On completion, the residue was acidified with HCl (1N) until the pH=4-5. Then the residue mixture was filtered, the filter cake was dried to give the title compound (280 mg, 96% yield) as yellow solid. LC-MS (ESI+) m/z 433.2 (M+H)⁺.

6-Cyano-N-[2-(4-formylcyclohexyl)indazol-5-yl]pyridine-2-carboxamide (Intermediate BVH)

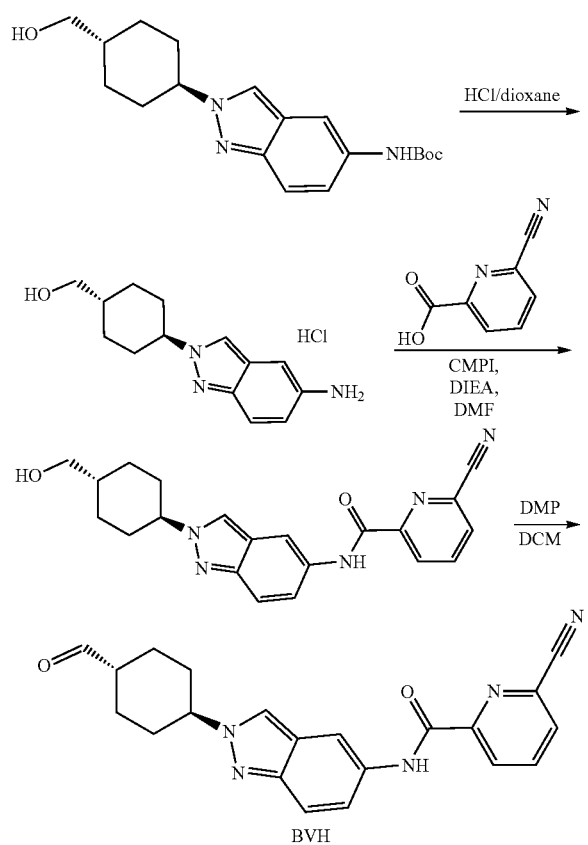

Step 1—6-Cyano-N-[2-[4-(hydroxymethyl)cyclohexyl]indazol-5-yl]pyridine-2-carboxamide To a solution of 6-cyanopyridine-2-carboxylic acid (126 mg, 851 umol, CAS #872602-74-9) in DMF (3 mL) was added DIEA (330 mg, 2.56 mmol, 445 uL) and CMPI (326 mg, 1.28 mmol). Then [4-(5-aminoindazol-2-yl)cyclohexyl]methanol (240 mg, 851 umol, HCl, synthesized via Step 1 of Intermediate BUT) was added and the mixture was stirred at 25° C. for 2 hrs. On completion, the reaction mixture was concentrated in vacuo to give a residue. The residue was purified by column chromatography to give the title compound (130 mg, 40% yield) as a white solid. ¹H NMR (400 MHz, DMSO-d₆) δ 10.59 (s, 1H), 8.44-8.37 (m, 2H), 8.34-8.27 (m, 3H), 7.60 (d, J=0.8 Hz, 2H), 4.48-4.36 (m, 1H), 3.31-3.28 (m, 3H), 2.20-2.10 (m, 2H), 1.98-1.83 (m, 4H), 1.56-1.42 (m, 1H), 1.22-1.09 (m, 2H); LC-MS (ESI⁺) m/z 376.1 (M+H)⁺.

916

Step 2—6-Cyano-N-[2-(4-formylcyclohexyl)indazol-5-yl]pyridine-2-carboxamide

To a solution of 6-cyano-N-[2-[4-(hydroxymethyl)cyclohexyl]indazol-5-yl]pyridine-2-carboxamide (65.0 mg, 173 umol) in DCM (2 mL) was added DMP (88.1 mg, 207 umol, 64.3 uL). The reaction mixture was stirred at 25° C. for 2 hrs. On completion, the reaction mixture was quenched with Na₂S₂O₃ (5 mL) and NaHCO₃ (5 mL) and extracted with DCM (2×10 mL). The combined organic phase was washed with NaHCO₃ (10 mL) and brine (2×10 mL), dried with anhydrous Na₂SO₄, filtered and the filtrate was concentrated in vacuo to give the title compound (64.0 mg, 98% yield) as a white solid. LC-MS (ESI⁺) m/z 374.1 (M+H)⁺.

2-[4-[[Tert-butyl (dimethyl)silyl]oxymethyl]cyclohexyl]indazol-5-amine (Intermediate BVI)

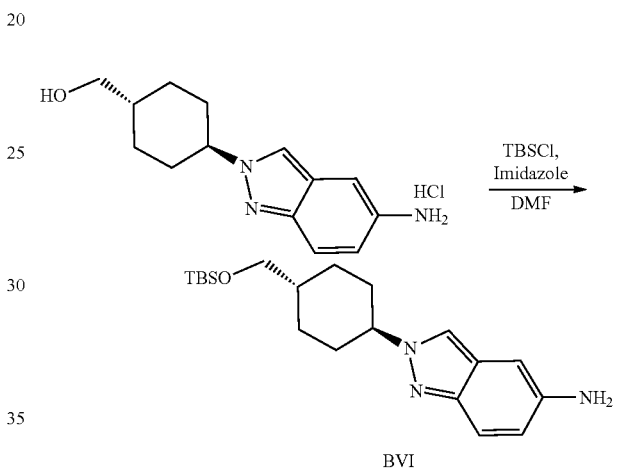

To a solution of [4-(5-aminoindazol-2-yl)cyclohexyl]methanol (240 mg, 851 umol, HCl, synthesized via Step 1 of Intermediate BUT) in THF (5 mL) was added imidazole (115 mg, 1.70 mmol) and TBSCl (166 mg, 1.11 mmol, 135 uL), then the reaction mixture was stirred at 25° C. for 2 hrs. On completion, the residue was diluted with water (10 mL) and extracted with DCM (2×15 mL). The combined organic layer was washed with brine (2×10 mL) and dried over Na₂SO₄, filtered and the filtrate was concentrated in vacuo to give the title compound (300 mg, 97% yield) as a brown solid. LC-MS (ESI⁺) m/z 360.2 (M+H)⁺.

5-Cyano-N-[2-(4-formylcyclohexyl)indazol-5-yl]pyrrolo[2,3-b]pyridine-1-carboxamide amine (Intermediate BVJ)

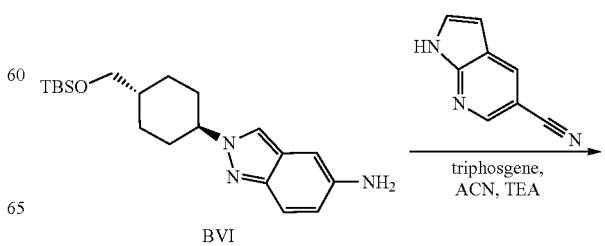

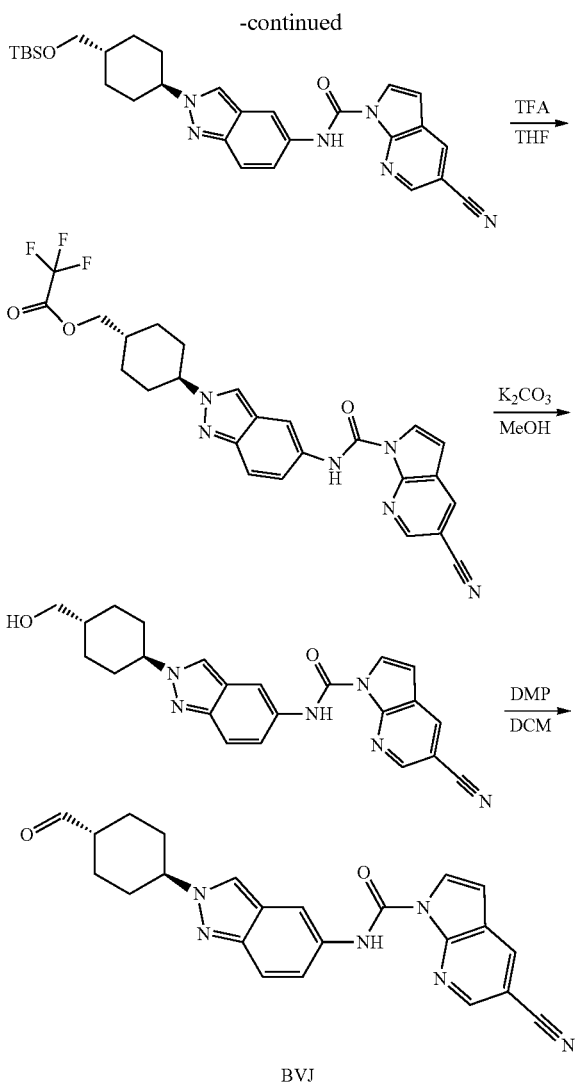

BVJ

Step 1—N-[2-[4-[[tert-butyl(dimethyl)silyl]oxymethyl]cyclohexyl]indazol-5-yl]-5-cyano-pyrrolo[2,3-b]pyridine-1-carboxamide To a solution of 1H-pyrrolo[2,3-b]pyridine-5-carbonitrile (119 mg, 834 umol, CAS #517918-95-5) in ACN (3 mL) was added TEA (422 mg, 4.17 mmol, 580 uL) and the reaction mixture was stirred at 0° C., then triphosgene (148 mg, 500 umol) was added and the reaction mixture was stirred at 0° C. for 0.5 hr. Next, 2-[4-[[tert-butyl(dimethyl) silyl]oxymethyl]cyclohexyl]indazol-5-amine (300 mg, 834 umol, Intermediate BVI) was added, and the reaction mixture was stirred at 80° C. for 0.5 hr. On completion, the mixture was quenched with NaHCO$_3$ (5 mL) and diluted with water (10 mL) and extracted with DCM (2×15 mL). The combined organic layers were washed with brine (10 mL), dried over Na$_2$SO$_4$, filtered and the filtrate was concentrated in vacuo to give a residue. The residue was purified by reverse phase (0.1% FA condition) to give the title compound (250 mg, 56% yield) as a white solid. $^1$H NMR (400 MHz, DMSO-d$_6$) δ 11.39 (s, 1H), 8.95 (d, J=2.0 Hz, 1H), 8.77 (d, J=2.0 Hz, 1H), 8.43 (s, 1H), 8.25 (d, J=4.0 Hz, 1H), 8.11 (d, J=2.0 Hz, 1H), 7.68 (d, J=9.2 Hz, 1H), 7.38 (dd, J=2.0, 9.2 Hz, 1H), 6.92 (d, J=4.0 Hz, 1H), 4.49-4.38 (m, 1H), 3.48 (d, J=6.0 Hz, 2H), 2.20-2.15 (m, 2H), 1.95-1.85 (m, 4H), 1.60-1.53 (m, 1H), 1.20-1.14 (m, 2H), 0.89 (s, 9H), 0.06 (s, 6H), LC-MS (ESI$^+$) m/z 529.4 (M+H)$^+$.

Step 2—[4-[5-[(5-Cyanopyrrolo[2,3-b]pyridine-1-carbonyl)amino]indazol-2-yl]cyclohexyl]methyl 2,2,2-trifluoroacetate To a solution of N-[2-[4-[[tert-butyl(dimethyl)silyl]oxymethyl]cyclohexyl]indazol-5-yl]-5-cyano-pyrrolo[2,3-b]pyridine-1-carboxamide (90.0 mg, 170 umol) in DCM (2 mL) was added TFA (116 mg, 1.02 mmol, 75.6 uL). The reaction mixture was stirred at 25° C. for 0.5 hr. On completion, the reaction mixture was diluted with THF (3 mL), then the mixture was extracted with DCM (2×5 mL) and washed with (2×5 mL). The combined organic layers was dried over Na$_2$SO$_4$, filtered and the filtrate was concentrated in vacuo to give the title compound (86.0 mg, 98% yield) as a white solid. LCMS (ESI$^+$) m/z 511.1 (M+H)$^+$.

Step 3—5-Cyano-N-[2-[4-(hydroxymethyl)cyclohexyl]indazol-5-yl]pyrrolo[2,3-b]pyridine-1-carboxamide To a solution of [4-[5-[(5-cyanopyrrolo[2,3-b]pyridine-1-carbonyl)amino]indazol-2-yl]cyclohexyl]methyl 2,2,2-trifluoroacetate (50.0 mg, 97.9 umol) in MeOH (1 mL) was added K$_2$CO$_3$ (27.0 mg, 195 umol), then the reaction mixture was stirred at 25° C. for 2 hrs. On completion, the reaction mixture was filtered and the filtrate was diluted with water (3 mL) and extracted with DCM (2×10 mL). The combined organic layers was washed with brine (2×15 mL) and dried over Na$_2$SO$_4$, filtered and the filtrate was concentrated in vacuo to give the title compound (40.0 mg, 98% yield) as a brown solid. LCMS (ESI$^+$) m/z 415.2 (M+H)$^+$.

Step 4—5-Cyano-N-[2-(4-formylcyclohexyl)indazol-5-yl]pyrrolo[2,3-b]pyridine-1-carboxamide To a solution of 5-cyano-N-[2-[4-(hydroxymethyl)cyclohexyl]indazol-5-yl]pyrrolo[2,3-b]pyridine-1-carboxamide (40.0 mg, 96.5 umol) in DCM (2 mL) was added DMP (49.1 mg, 115 umol, 35.8 uL), then the reaction mixture was stirred at 25° C. for 2 hrs. On completion, the reaction mixture was quenched with Na$_2$S$_2$O$_3$ (3 mL) and NaHCO$_3$ (3 mL), then extracted with DCM (2×8 mL). The combined organic phase was washed with NaHCO$_3$ (5 mL) and brine (2×8 mL), dried with anhydrous Na$_2$SO$_4$, filtered and the filtrate was concentrated in vacuo to give the title compound (39.0 mg, 97% yield) as a brown solid. LCMS (ESI$^+$) m/z 413.2 (M+H)$^+$.

3-[5-Fluoro-3-methyl-2-oxo-4-(4-piperidyl)benzimidazol-1-yl]piperidine-2,6-dione (Intermediate BVK)

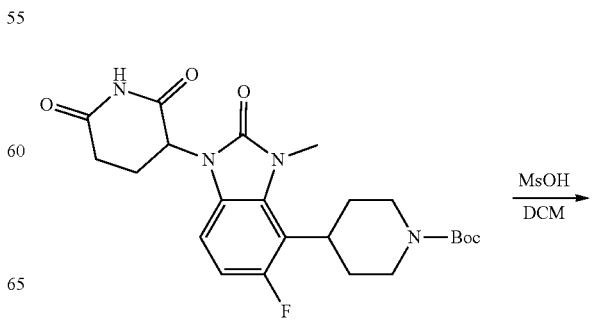

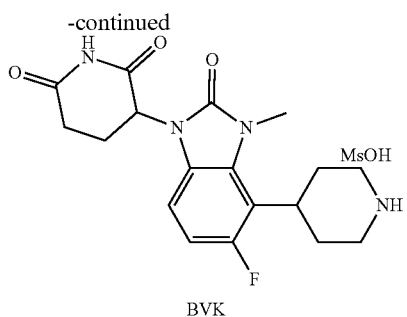

BVK

To a mixture of tert-butyl 4-[1-(2,6-dioxo-3-piperidyl)-5-fluoro-3-methyl-2-oxo-benzimidazol-4-yl]piperidine-1-carboxylate (60.0 mg, 130 umol, synthesized via Steps 1-3 of Intermediate BSP) in THF (1 mL) was added MsOH (37.5 mg, 390 umol, 27.8 uL). The reaction mixture was stirred at 65° C. for 1 hour. On completion, the reaction mixture was triturated with MTBE (5 mL). White solid formed which was filtered to give the title compound (46.0 mg, 97% yield) as white solid. LC-MS (ESI+) m/z 361.1 (M+H)+.

6-(5-cyanopyrrolo[2,3-b]pyridin-1-yl)-N-[(4-formyl-cyclohexyl)methyl]-4-(isopropylamino) pyridine-3-carboxamide (Intermediate BVL)

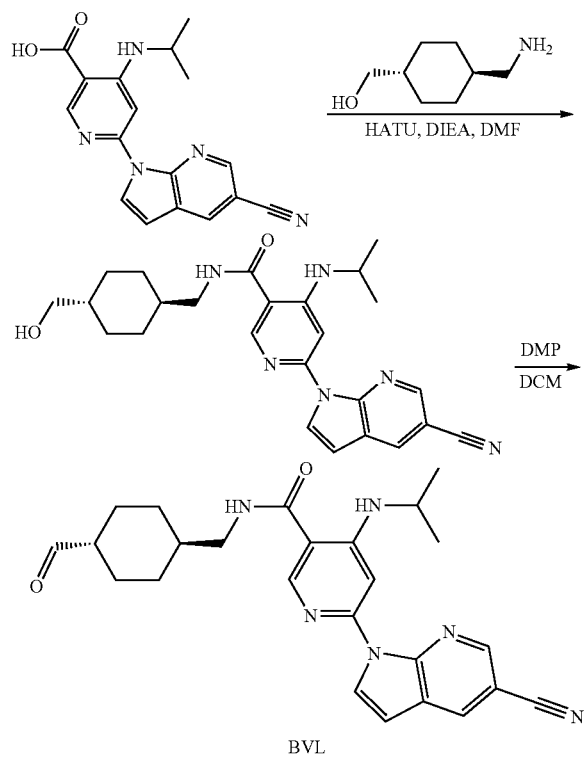

Step 1—6-(5-cyanopyrrolo[2,3-b]pyridin-1-yl)-N-[[4-(hydroxymethyl)cyclohexyl]methyl]-4-(isopropylamino)pyridine-3-carboxamide To a solution of 6-(5-cyanopyrrolo[2,3-b]pyridin-1-yl)-4-(isopropylamino)pyridine-3-carboxylic acid (200 mg, 622 umol, Intermediate BUQ) and [4-(aminomethyl)cyclohexyl]methanol (115 mg, 809 umol, CAS #17879-23-1) in DMF (4 mL) were added DIEA (160 mg, 1.24 mmol) and HATU (473 mg, 1.24 mmol) at 25° C. The reaction mixture was stirred at 25° C. for 1 hr. On completion, the reaction mixture was diluted with EtOAc (20 ml). The organic layer was washed with water (20 mL×3) and concentrated in vacuo. The residue was purified by column chromatography (SiO2, petroleum ether/ethyl acetate=1/1, P1: $R_f$=0.3) to give title compound (260 mg, 93% yield) as pink solid. 1H NMR (400 MHz, DMSO-$d_6$) δ 8.80 (d, J=2.0 Hz, 1H), 8.66 (d, J=2.0 Hz, 1H), 8.62 (d, J=7.2 Hz, 1H), 8.57 (s, 1H), 8.56-8.53 (m, 1H), 8.52 (d, J=4.0 Hz, 1H), 8.07 (s, 1H), 6.88 (d, J=4.0 Hz, 1H), 4.34 (t, J=5.2 Hz, 1H), 3.83-3.70 (m, 1H), 3.20 (t, J=5.6 Hz, 2H), 3.09 (t, J=6.4 Hz, 2H), 2.69 (s, 3H), 1.81-1.71 (m, 4H), 1.55-1.44 (m, 1H), 1.29 (d, J=6.4 Hz, 6H).

Step 2—6-(5-cyanopyrrolo[2,3-b]pyridin-1-yl)-N-[(4-formylcyclohexyl)methyl]-4-(isopropylamino) pyridine-3-carboxamide To a solution of 6-(5-cyanopyrrolo[2,3-b]pyridin-1-yl)-N-[[4-(hydroxymethyl)cyclohexyl]methyl]-4-(isopropylamino)pyridine-3-carboxamide (210 mg, 470 umol) in DCM (4 mL) and DMF (0.1 mL) was added DMP (398 mg, 940 umol). The reaction was stirred at 25° C. for 1 hr. On completion, the reaction mixture was quenched with $Na_2S_2O_3$ (6 mL) and $NaHCO_3$ (6 mL) aqueous. The combined layers were extracted with DCM (30 mL×2). The combined organic layers were concentrated in vacuo to give title compound (155 mg, 348 umol, 74% yield) as yellow solid. LC-MS (ESI+) m/z 445.2 (M+H)+.

3-[(4-methoxyphenyl)methyl]hexahydropyrimidine-2,4-dione (Intermediate BTJ)

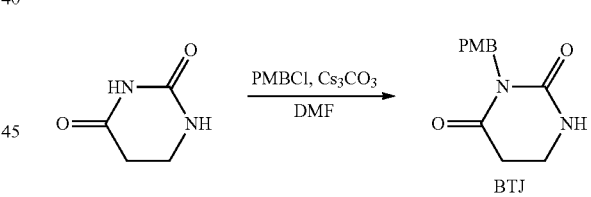

To the solution of hexahydropyrimidine-2,4-dione (3.0 g, 26.3 mmol, CAS #504-07-4) in DMF (60 mL) was added $Cs_2CO_3$ (17.1 g, 52.6 mmol) at 25° C., then 1-(chloromethyl)-4-methoxybenzene (3.71 g, 23.6 mmol) was dropwise added to the mixture slowly at 25° C. The mixture was stirred at 25° C. for 2 hours. On completion, the reaction was filtered and the filter cake was washed by EA (30 mL×2). The filtrate was poured into water (150 mL) and extracted with EA (100 mL×2). The combined organic layer was washed with water (100 mL) and saturated brine (100 mL). The organic layer was dried over $Na_2SO_4$, filtered and concentrated to give the crude product. The crude product was suspended in EA/PE (1/1, 80 mL) and stirred for 0.5 hour. The suspension was filtered, the filter cake was dried to give compound (2.80 g, 45% yield) as a white solid. 1H NMR (400 MHz, CHLOROFORM-d) δ 7.42-7.30 (m, 2H), 6.90-6.62 (m, 2H), 6.15 (s, 1H), 4.88 (s, 2H), 3.78 (s, 3H), 3.37 (dt, J=2.4, 6.8 Hz, 2H), 2.71 (t, J=6.8 Hz, 2H).

1-(7-Bromoimidazo[1,2-a]pyridin-3-yl)hexahydropyrimidine-2,4-dione (Intermediate BTK)

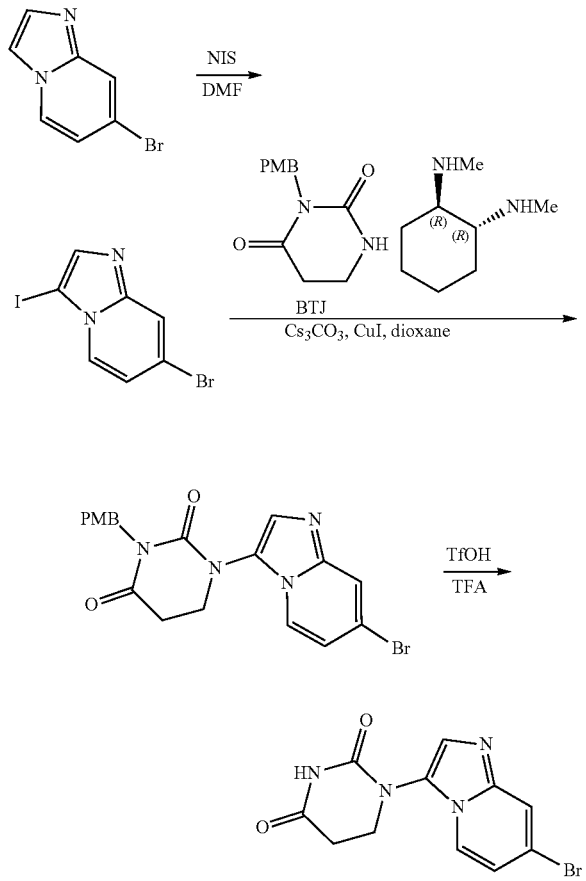

Step 1—7-bromo-3-iodo-imidazo[1,2-a]pyridine

To a solution of 7-bromoimidazo[1,2-a]pyridine (9.50 g, 48.2 mmol, CAS #808744-34-5) in DMF (150 mL) was added NIS (13.0 g, 57.8 mmol) at 25° C. The mixture was stirred at 100° C. for 1 hour. On completion, the reaction mixture was poured into 400 mL of water and extracted with EtOAc (200 mL×2). The organic layer was washed with water (200 mL) and saturated brine (200 mL), then dried over $Na_2SO_4$, filtered and concentrated to give the crude product. The crude product was purified by flash silica gel chromatography (120 g Column, Eluent of 0-5% ethyl acetate/petroleum ether gradient @ 150 mL/min) to give the compound (11.6 g, 74% yield) as a black brown solid. $^1$H NMR (400 MHz, CHLOROFORM-d) δ 8.00 (d, J=7.2 Hz, 1H), 7.82 (d, J=1.2 Hz, 1H), 7.67 (s, 1H), 7.04 (dd, J=2.0, 7.3 Hz, 1H).

Step 2—1-(7-bromoimidazo[1,2-a]pyridin-3-yl)-3-[(4-methoxyphenyl)methyl]hexahydropyrimidine-2,4-dione To a solution of 3-[(4-methoxyphenyl)methyl]hexahydropyrimidine-2,4-dione (4 g, 17.08 mmol, Intermediate BTJ), 7-bromo-3-iodo-imidazo[1,2-a]pyridine (6.62 g, 20.49 mmol) in 1,4-dioxane (100 mL) was added $Cs_2CO_3$ (11.1 g, 34.1 mmol), CuI (650 mg, 3.42 mmol) and (1R,2R)—N1,N2-Dimethylcyclohexane-1,2-diamine (485 mg, 3.42 mmol, CAS #68737-65-5) at 25° C. under $N_2$. Then the mixture was stirred at 80° C. for 16 hours. On completion, the reaction mixture was poured into 200 mL of water and extracted with EtOAc (100 mL×2). The combined organic layers were washed with water (200 mL) and saturated brine (200 mL), then dried over $Na_2SO_4$, filtered and concentrated to give a crude product. The crude product was purified by silica gel chromatography (eluted with petroleum ether/ethyl acetate=10/1 to 0/1 to give the title compound (2.00 g, 27% yield) as a yellow solid.

Step 3—1-(7-Bromoimidazo[1,2-a]pyridin-3-yl)hexahydropyrimidine-2,4-dione

A solution of 1-(7-bromoimidazo[1,2-a]pyridin-3-yl)-3-[(4-methoxyphenyl)methyl] hexahydropyrimidine-2,4-dione (2.30 g, 5.36 mmol) in TfOH (1.5 mL) was stirred at 65° C. for 4 hours. On completion, the mixture was concentrated to give residue, then the residue was adjusted pH to 6-7 with TEA at 0° C. Then the mixture was concentrated to give a residue. The residue was suspended in EtOAc (30 mL) and stirred for 0.5 hour. Next, the suspension was filtered and the filter cake was concentrated to give the title compound (1.55 g, 84% yield) as a white solid. $^1$H NMR (400 MHz, DMSO-$d_6$) δ 10.69 (s, 1H), 8.32 (d, J=7.2 Hz, 1H), 7.93 (d, J=1.2 Hz, 1H), 7.59 (s, 1H), 7.15 (dd, J=2.0, 7.2 Hz, 1H), 3.81 (t, J=6.8 Hz, 2H), 2.83 (t, J=6.4 Hz, 2H).

4-Bromo-3-methyl-1-(2-trimethylsilylethoxymethyl)benzimidazol-2-one (Intermediate BED)

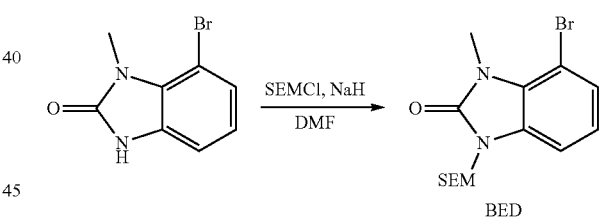

To a mixture of 4-bromo-3-methyl-1H-benzimidazol-2-one (50.0 g, 220 mmol, synthesized via Steps 1-3 of Intermediate HP) in DMF (500 mL) was added NaH (13.2 g, 330 mmol, 60% dispersion in mineral oil) at 0° C. The reaction mixture was stirred for 30 minutes. Then SEMCl (44.0 g, 264 mmol) was added dropwise at 0° C. and the reaction mixture was stirred for 16 hours. On completion, the mixture was poured into water (500 mL). The mixture was extracted with DCM (3×200 mL) and the combined organic layer was dried over by $Na_2SO_4$. The mixture was filtrated and the filtrate was concentrated in vacuo. The residue was purified by column chromatography (petroleum ether/ethyl acetate=20/1) to give the title compound (60.0 g, 76% yield) as yellow oil. $^1$H NMR (400 MHz, DMSO-$d_6$) δ 7.34-7.21 (m, 2H), 7.01-6.97 (m, 1H), 5.24 (s, 2H), 3.61 (s, 3H), 3.55-3.51 (m, 2H), 0.85-0.81 (m, 2H), 0.07 (s, 9H).

3-(4-((1R,4R)-2,5-diazabicyclo[2.2.1]heptan-2-yl)-3-methyl-2-oxo-2,3-dihydro-1H-benzo[d]imidazol-1-yl)piperidine-2,6-dione (Intermediate BDY)

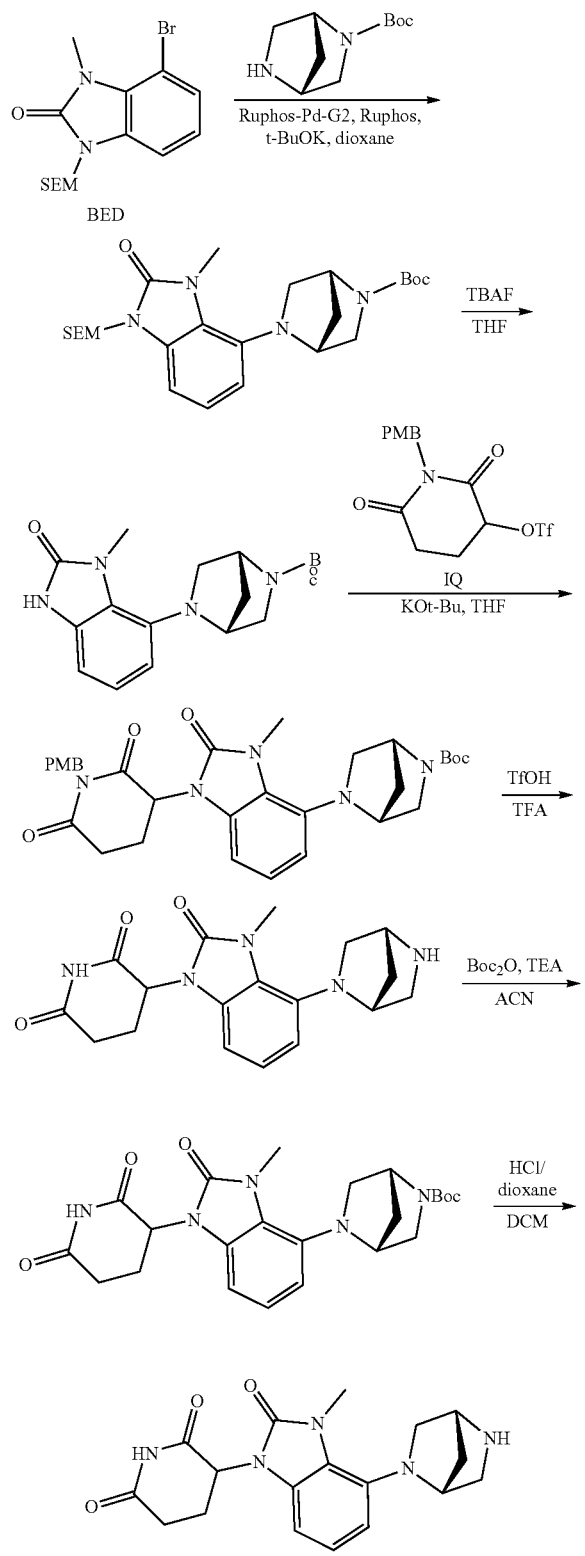

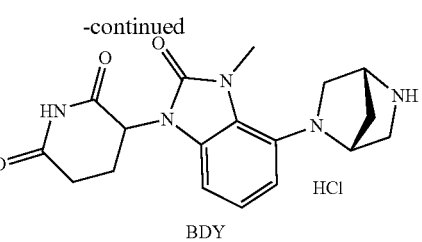

Step 1—(1R,4R)-tert-butyl 5-(3-methyl-2-oxo-1-((2-(trimethylsilyl)ethoxy)methyl)-2,3-dihydro-1H-benzo[d]imidazol-4-yl)-2,5-diazabicyclo[2.2.1]heptane-2-carboxylate To a solution of 4-bromo-3-methyl-1-(2-trimethylsilylethoxymethyl)benzimidazol-2-one (3.00 g, 8.40 mmol, Intermediate BED), tert-butyl (1R,4R)-2,5-diazabicyclo[2.2.1]heptane-2-carboxylate (1.66 g, 8.40 mmol, CAS #134003-84-2) and t-BuOK (1.88 g, 16.8 mmol) in dioxane (40 mL) was added RuPhos (196 mg, 420 umol) and [2-(2-aminophenyl)phenyl]-chloro-palladium; dicyclohexyl-[2-(2,6-diisopropoxyphenyl)phenyl]phosphane (326 mg, 420 umol). The reaction mixture was degassed and purged with nitrogen for 3 times, and then the mixture was stirred at 80° C. for 2 hrs under nitrogen atmosphere. On completion, the reaction mixture was filtered and the combined filtrate was concentrated in vacuo to give a residue. The residue was purified by silica gel chromatography (petroleum ether:ethyl acetate=3:1) to give the title compound (2.86 g, 71% yield) as yellow oil. $^1$H NMR (400 MHz, DMSO-$d_6$) δ 7.05-6.90 (m, 2H), 6.81 (d, J=8.0 Hz, 1H), 5.21 (s, 2H), 4.37 (m, 1H), 3.90 (m, 1H), 3.58 (s, 3H), 3.53 (t, J=8.0 Hz, 2H), 3.44-3.35 (m, 1H), 3.31-3.16 (m, 2H), 3.15-3.06 (m, 1H), 2.04 (m, 1H), 1.88 (m, 1H), 1.43 (m, 9H), 0.88-0.76 (m, 2H), −0.03--0.13 (m, 9H). LC-MS (ESI$^+$) m/z 475.3 (M+H)$^+$.

Step 2—(1R,4R)-tert-butyl 5-(3-methyl-2-oxo-2,3-dihydro-1H-benzo[d]imidazol-4-yl)-2,5-diazabicyclo[2.2.1]heptanes-2-carboxylate A solution of tert-butyl (1R,4R)-5-[3-methyl-2-oxo-1-(2-trimethylsilylethoxymethyl)benzimidazol-4-yl]-2,5-diazabicyclo[2.2.1]heptane-2-carboxylate (2.76 g, 5.81 mmol) in TBAF (40 mL, 1 M) was stirred at 80° C. for 16 hrs. On completion, the reaction mixture was diluted with water (80 mL) and extracted with ethyl acetate (3×25 mL). The combined organic layers were washed with sodium chloride solution (50 mL), dried over anhydrous sodium sulfate, filtered and concentrated in vacuo to give a residue. The residue was purified by silica gel chromatography (petroleum ether:ethyl acetate=1:2) to give the title compound (1.60 g, 79% yield) as a yellow solid. 1H NMR (400 MHz, CDCl$_3$) δ 10.34 (m, 1H), 7.03-6.94 (m, 1H), 6.88 (m, 1H), 6.81 (d, J=8.0 Hz, 1H), 4.66-4.41 (m, 1H), 3.85 (m, 1H), 3.73 (s, 3H), 3.66-3.53 (m, 1H), 3.48 (m, 1H), 3.30-3.12 (m, 2H), 2.17-2.07 (m, 1H), 1.95 (m, 1H), 1.51 (m, 9H). LC-MS (ESI$^+$) m/z 345.4 (M+H)$^+$.

Step 3—(1R,4R)-tert-butyl 5-(1-(1-(4-methoxybenzyl)-2,6-dioxopiperidin-3-yl)-3-methyl-2-oxo-2,3-dihydro-1H-benzo[d]imidazol-4-yl)-2,5-diazabicyclo[2.2.1]heptane-2-carboxylate To a solution of tert-butyl (1R,4R)-5-(3-methyl-2-oxo-1H-benzimidazol-4-yl)-2,5-diazabicyclo[2.2.1]heptanes-2- carboxylate (1.30 g, 3.77 mmol) in THF (30 mL) was added tBuOK (635 mg, 5.66 mmol) at 0° C. and stirred for 0.5 hr. Then the mixture was added [1-[(4-methoxyphenyl)methyl]-2,6-dioxo-3-piperidyl]trifluoromethanesulfonate (2.16 g, 5.66 mmol, Intermediate IQ) in batch at 0° C. and stirred at 25° C. for 2 hrs. On completion, the reaction mixture was poured into saturated ammonium chloride aqueous solution (50 mL) at 0° C. and extracted with ethyl acetate (3×25 mL). The combined organic layers were washed with sodium chloride solution (25 mL), dried over anhydrous sodium sulfate, filtered and concentrated in vacuo to give a residue. The residue was purified by silica gel chromatography (petroleum ether:ethyl acetate=1:1) and reversed-phase HPLC (FA condition) to give the title compound (1.50 g, 69% yield) as a blue solid. $^1$H NMR (400 MHz, CDCl$_3$) δ 7.37 (dd, J=8.8, 2.0 Hz, 2H), 6.90-6.77 (m, 4H), 6.27 (m, 1H), 5.34-5.08 (m, 1H), 5.03-4.87 (m, 2H), 4.61-4.43 (m, 1H), 3.86-3.76 (m, 4H), 3.72 (s, 3H), 3.63-3.40 (m, 2H), 3.29-3.13 (m, 2H), 3.05-2.95 (m, 1H), 2.89-2.76 (m, 1H), 2.68-2.51 (m, 1H), 2.21-2.07 (m, 3H), 1.96 (m, 1H), 1.51 (m, 9H). LC-MS (ESI$^+$) m/z 576.2 (M+H)$^+$.

Step 4—3-(4-((1R,4R)-2,5-diazabicyclo[2.2.1]heptan-2-yl)-3-methyl-2-oxo-2,3-dihydro-1H-benzo[d]imidazol-1-yl)piperidine-2,6-dione A solution of tert-butyl (1R,4R)-5-[1-[1-[(4-methoxyphenyl)methyl]-2,6-dioxo-3-piperidyl]-3-methyl-2-oxo-benzimidazol-4-yl]-2,5-diazabicyclo[2.2.1]heptane-2-carboxylate (800 mg, 1.39 mmol) in TfOH (1 mL) and TFA (10 mL) was stirred at 60° C. for 16 hrs. On completion, the reaction mixture was concentrated in vacuo to give the title compound (652 mg, 70% yield) as green oil. LC-MS (ESI$^+$) m/z 356.1 (M+H)$^+$.

Step 5—(1R,4R)-tert-butyl 5-(1-(2,6-dioxopiperidin-3-yl)-3-methyl-2-oxo-2,3-dihydro-1H-benzo[d]imidazol-4-yl)-2,5-diazabicyclo[2.2.1]heptane-2-carboxylate To a solution of 3-[4-[(1R,4R)-2,5-diazabicyclo[2.2.1]heptan-2-yl]-3-methyl-2-oxo-benzimidazol-1-yl]piperidine-2,6-dione (610 mg, 1.30 mmol, TFA) in ACN (5 mL) was added TEA (394 mg, 3.90 mmol) and (Boc)$_2$O (340 mg, 1.56 mmol). The mixture was stirred at 25° C. for 2 hrs. On completion, the reaction mixture was concentrated in vacuo to give a residue. The residue was diluted with saturated ammonium chloride aqueous solution (25 mL) and extracted with ethyl acetate (3×15 mL). The combined organic layers were washed with sodium chloride solution (25 mL), dried over anhydrous sodium sulfate, filtered and concentrated in vacuo to give a residue. The residue was purified by silica gel chromatography (petroleum ether:ethyl acetate=1:5) to give the title compound (580 mg, 90% yield) as a green solid. $^1$H NMR (400 MHz, CDCl$_3$) δ 8.25 (m, 1H), 7.05-6.94 (m, 1H), 6.85 (d, J=8.0 Hz, 1H), 6.57 (d, J=7.6 Hz, 1H), 5.29-5.15 (m, 1H), 4.63-4.43 (m, 1H), 3.90-3.79 (m, 1H), 3.73 (s, 3H), 3.58 (m, 1H), 3.47 (m, 1H), 3.31-3.13 (m, 2H), 2.98-2.65 (m, 3H), 2.29-2.16 (m, 1H), 2.11 (m, 1H), 1.97 (m, 1H), 1.51 (m, 9H). LC-MS (ESI$^+$) m/z 456.3 (M+H)$^+$.

Step 6—3-(4-((1R,4R)-2,5-diazabicyclo[2.2.1]heptan-2-yl)-3-methyl-2-oxo-2,3-dihydro-1H-benzo[d]imidazol-1-yl)piperidine-2,6-dione A solution of tert-butyl (1R,4R)-5-[1-(2,6-dioxo-3-piperidyl)-3-methyl-2-oxo-benzimidazol-4-yl]-2,5-diazabicyclo[2.2.1]heptane-2-carboxylate (100 mg, 220 umol) in HCl/dioxane (1 mL) and DCM was stirred at 25° C. for 0.5 hr. On completion, the reaction mixture was concentrated in vacuo to give the title compound (86 mg, 99% yield) as a yellow solid. LC-MS (ESI$^+$) m/z 356.4 (M+H)$^+$.

3-(5-bromo-3-methyl-2-oxo-benzimidazol-1-yl)piperidine-2,6-dione (Intermediate HN)

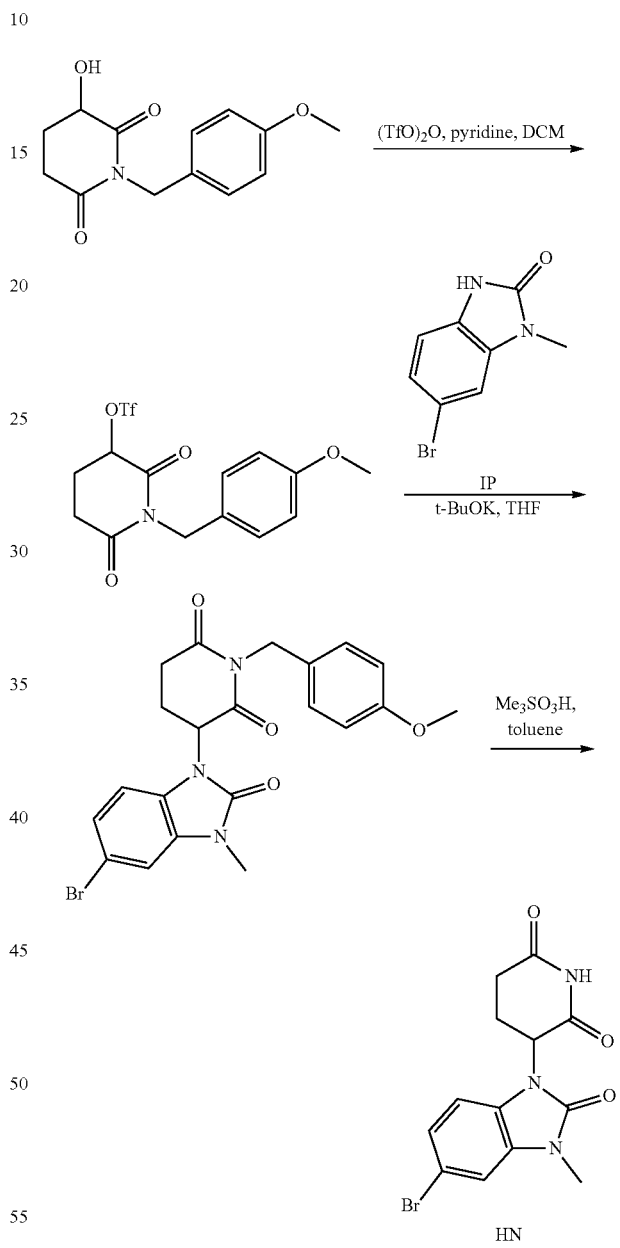

Step 1—[1-[(4-Methoxyphenyl) methyl]-2,6-dioxo-3-piperidyl] trifluoromethanesulfonate To a solution of 3-hydroxy-1-[(4-methoxyphenyl) methyl] piperidine-2,6-dione (43.0 g, 173 mmol, CAS #2357109-89-6) and pyridine (27.3 g, 345 mmol) in DCM (500 mL) was added trifluoromethylsulfonyl trifluoromethanesulfonate (73.0 g, 258.74 mmol) dropwise at 0° C. The mixture was stirred at 0-10° C. for 1.5 hours under N$_2$. On completion, the mixture was concentrated in vacuo. The residue was purified by column chromatography on silica gel to give the title compound (45.0 g, 68% yield) as light yellow gum. ¹H NMR (400 MHz, CDCl₃) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

Step 2—3-(5-Bromo-3-methyl-2-oxo-benzimidazol-1-yl)-1-[(4-methoxyphenyl)methyl]piperidine-2,6-dione To a solution of 5-bromo-3-methyl-1H-benzimidazol-2-one (4.90 g, 21.6 mmol, Intermediate IP) in THF (300 mL) was added t-BuOK (3.63 g, 32.3 mmol) at 0° C. The mixture was stirred at 0-10° C. for 1 hour under N₂. Then a solution of [1[(4-methoxyphenyl) methyl]-2,6-dioxo-3-piperidyl] trifluoromethanesulfonate (9.87 g, 25.9 mmol) in THF (100 mL) was added to the reaction mixture at 0-10° C. during 30 minutes. The mixture was stirred at 0-10° C. for 30 minutes under N₂. An additional solution of [1-[(4-methoxyphenyl) methyl]-2,6-dioxo-3-piperidyl] trifluoromethanesulfonate (2.47 g, 6.47 mmol) in THF (20 mL) was added to the reaction mixture at 0-10° C. dropwise. The mixture was then stirred at 0-10° C. for another 30 minutes under N₂. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield) as light yellow solid. The filtrate was also concentrated in vacuo and the residue was purified by column chromatography to give another batch title compound (1.80 g, 18% yield) as light yellow solid. ¹H NMR (400 MHz, DMSO-d₆) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 3—3-(5-Bromo-3-methyl-2-oxo-benzimidazol-1-yl)piperidine-2,6-dione

To a mixture of 3-(5-bromo-3-methyl-2-oxo-benzimidazol-1-yl)-1-[(4-methoxyphenyl)methyl]piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over Na₂SO₄, filtered and concentrated in vacuo. The residue was triturated with EA (80 mL) and filtered. The filtrate cake was collected and dried in vacuo to give the title compound (4.20 g, 67% yield) as off-white solid. ¹H NMR (400 MHz, DMSO-d₆) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

3-[3-Methyl-2-oxo-5-(4-piperidyl)benzimidazol-1-yl]piperidine-2,6-dione (Intermediate AZL)

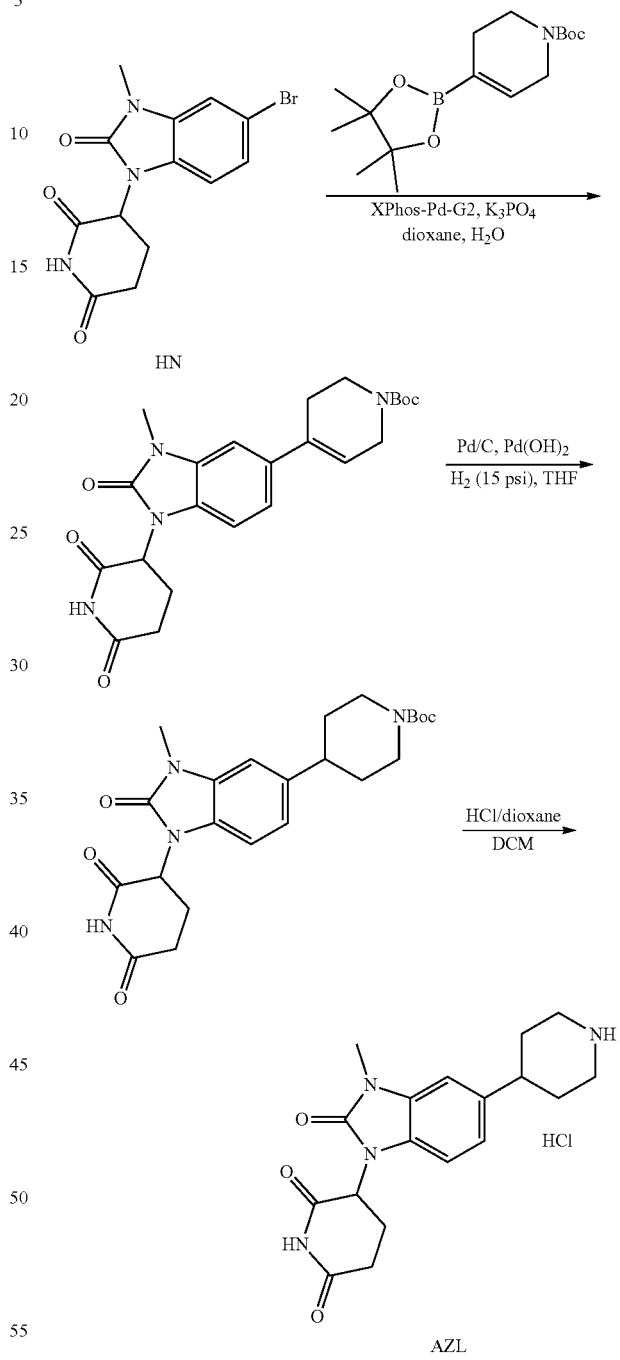

Step 1—Tert-butyl 4-[1-(2,6-dioxo-3-piperidyl)-3-methyl-2-oxo-benzimidazol-4-yl]-3,6-dihydro-2H-pyridine-1-carboxylate To a solution of 3-(5-bromo-3-methyl-2-oxo-benzimidazol-1-yl)piperidine-2,6-dione (5.00 g, 14.8 mmol, Intermediate FIN), tert-butyl 4-(4,4,5,5-tetramethyl-1,3,2-dioxaborolan-2-yl)-3,6-dihydro-2H-pyridine-1-carboxylate (5.49 g, 17.7 mmol, CAS #286961-14-6), K₃PO₄ (6.28 g, 29.6 mmol) and [2-(2-aminophenyl)phenyl]-chloro-palladium; dicyclohexyl-[3-(2,4,6-triisopropylphenyl)phenyl]phosphane (1.16 g, 1.48 mmol) in dioxane (100 mL) and H₂O (5.0 mL) was stirred at 80° C. for 4 hrs. On completion, the mixture filtered and the filtrate was concentrated in vacuo. The residue was purified by reversed phase flash (0.1% FA condition) to give the title compound (2.30 g, 53% yield) as white solid. ¹H NMR (400 MHz, DMSO-d₆) δ 11.09 (s, 1H), 7.27 (s, 1H), 7.14-7.04 (m, 2H), 6.11 (s, 1H), 5.36 (dd, J=12.8, 5.2 Hz, 1H), 4.01 (d, J=7.2 Hz, 2H), 3.55 (t, J=5.6 Hz, 2H), 3.35 (s, 3H), 2.95-2.83 (m, 1H), 2.73-2.59 (m, 2H), 2.06-1.95 (m, 2H), 1.46-1.39 (m, 9H), 1.17 (t, J=7.2 Hz, 1H). LC-MS (ESI⁺) m/z 441.2 (M+H)⁺.

Step 2—Tert-butyl 4-[1-(2,6-dioxo-3-piperidyl)-3-methyl-2-oxo-benzimidazol-5-yl]piperidine-1-carboxylate To a solution of tert-butyl 4-[1-(2,6-dioxo-3-piperidyl)-3-methyl-2-oxo-benzimidazol-5-yl]-3,6-dihydro-2H-pyridine-1-carboxylate (2.30 g, 5.22 mmol) in THF (150 mL) was added Pd/C (800 mg, 10 wt %) and Pd(OH)₂ (800 mg, 5.70 mmol) at 25° C. The reaction mixture was stirred at 60° C. for 16 hr under H₂ (15 psi). On completion, the reaction mixture was filtered with celite and the filtrate was concentrated in vacuo to give the title compound (2.30 g, 87% yield) as white solid. ¹H NMR (400 MHz, CDCl₃) δ 8.10 (s, 1H), 7.02-6.87 (m, 2H), 6.76 (d, J=8.0 Hz, 1H), 5.23 (dd, J=5.6, 12.6 Hz, 1H), 4.30-4.25 (m, 2H), 3.45 (s, 3H), 2.99-2.68 (m, 6H), 2.30-2.21 (m, 1H), 1.88-1.81 (m, 2H), 1.51 (s, 9H), 1.48-1.44 (m, 2H). LC-MS (ESI⁺) m/z 465.2 (M+23)⁺.

Step 3—3-[3-Methyl-2-oxo-5-(4-piperidyl)benzimidazol-1-yl]piperidine-2,6-dione

To a mixture of tert-butyl 4-[1-(2,6-dioxo-3-piperidyl)-3-methyl-2-oxo-benzimidazol-5-yl]piperidine-1-carboxylate (300 mg, 678 umol) in DCM (3.0 mL) was added HCl/dioxane (4 M, 170 uL) in one portion at 25° C. under N₂. The mixture was stirred at 25° C. for 30 min. On completion, the reaction mixture was concentrated in vacuo to give the title compound (250 mg, 91% yield, HCl salt) as white solid. LC-MS (ESI⁺) m/z 343.1 (M+H)⁺.

6-Cyanopyrazolo[1,5-a]pyrimidine-3-carbonyl Chloride (Intermediate BVQ)

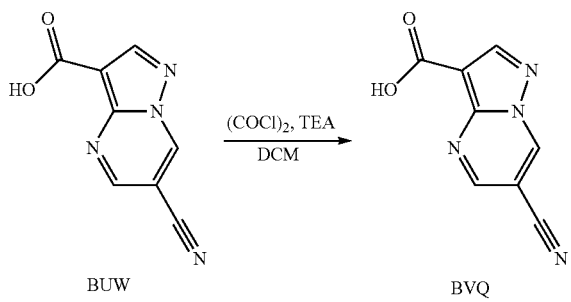 [SMILES: N#Cc1cnc2c(C(=O)O)cnn2c1 ; N#Cc1cnc2c(C(=O)O)cnn2c1 ; "BUW"]

To a solution of 6-cyanopyrazolo[1,5-a]pyrimidine-3-carboxylic acid (60.0 mg, 318 umol, Intermediate BUW) in DCM (2 mL) was added TEA (32.2 mg, 318 umol), then (COCl)₂ (40.4 mg, 318 umol) was added dropwise at 0° C. The mixture was then stirred at 20° C. for 0.5 hr. On completion, the mixture was concentrated in vacuo to give the title compound (65.0 mg, 98% yield) as brown solid.

(1R,4r)-4-((Benzyloxy)methyl)cyclohexanecarbonyl chloride (Intermediate BAU)

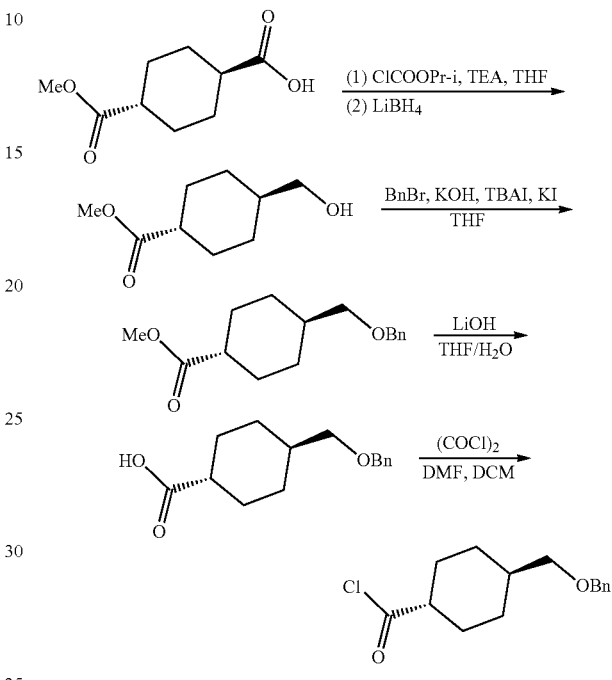

Step 1—(1R,4r)-Methyl 4-(hydroxymethyl)cyclohexanecarboxylate

To a solution of 4-methoxycarbonylcyclohexanecarboxylic acid (20.0 g, 107 mmol, CAS #15177-67-0) in the THF (200 mL) was added Et₃N (21.7 g, 215 mmol, 29.9 mL) and isopropyl carbonochloridate (19.7 g, 161 mmol, 22.4 mL) at 0° C. The mixture was stirred at 25° C. for 1 hour. Then the mixture was filtered and the LiBH₄ (11.7 g, 537 mmol) was added in portion at 0° C. The mixture was stirred at 25° C. for 4 hours. On completion, the mixture was quenched by water (500 mL) and extracted with EA (3×1000 mL). The organic layers were dried over Na₂SO₄, filtered and concentrated in vacuo. The residue was purified by column chromatography to give the title compound (9.70 g, 52% yield) as colorless oil. ¹H NMR (400 MHz, CDCl₃) δ 3.67 (s, 3H), 3.47 (d, J=6.0 Hz, 2H), 2.26 (tt, J=3.6, 12.4 Hz, 1H), 2.06-1.99 (m, 2H), 1.88 (dd, J=3.2, 13.6 Hz, 2H), 1.56-1.39 (m, 3H), 1.07-0.93 (m, 2H).

Step 2—(1R,4r)-Methyl 4-((benzyloxy)methyl)cyclohexanecarboxylate

To a solution of methyl 4-(hydroxymethyl)cyclohexanecarboxylate (9.70 g, 56.3 mmol) in the THF (100 mL) was added KOH (4.74 g, 84.5 mmol), TBAI (4.16 g, 11.3 mmol), KI (1.87 g, 11.3 mmol) and BnBr (14.5 g, 84.5 mmol, 10.0 mL). The mixture was stirred at 25° C. for 12 hours. On completion, the reaction mixture was filtered and concentrated in vacuo. The residue was purified by column chromatography to give the title compound (11.0 g, 74% yield) as colorless oil. $^1$H NMR (400 MHz, CDCl$_3$) δ 7.39-7.27 (m, 5H), 4.50 (s, 2H), 3.67 (s, 3H), 3.29 (d, J=6.4 Hz, 2H), 2.25 (tt, J=3.6, 12.4 Hz, 1H), 2.04-1.98 (m, 2H), 1.91 (br dd, J=3.6, 13.6 Hz, 2H), 1.71-1.61 (m, 1H), 1.45-1.42 (m, 2H), 1.08-0.94 (m, 2H).

Step 3—(1R,4r)-4-((benzyloxy)methyl)cyclohexanecarboxylic Acid

To a solution of methyl 4-(benzyloxymethyl)cyclohexanecarboxylate (11.0 g, 41.9 mmol) in the THF (100 mL), MeOH (20 mL) and H$_2$O (20 mL) was added LiOH (5.02 g, 210 mmol). The mixture was stirred at 25° C. for 12 hours. On completion, the reaction mixture was concentrated in vacuo. The residue was diluted with water (100 mL) and washed with PE (200 mL). The water phase was acidified by HCl (aq, 1M) to pH=4. Then the mixture was extracted with DCM (3×200 mL). The organic layer was dried over Na$_2$SO$_4$, filtered and concentrated in vacuo to give the title compound (10.1 g, 97% yield) as colorless oil. $^1$H NMR (400 MHz, CDCl$_3$) δ 7.41-7.26 (m, 5H), 4.50 (s, 2H), 3.30 (d, J=6.4 Hz, 2H), 2.28 (tt, J=3.6, 12.4 Hz, 1H), 2.05 (dd, J=2.8, 13.6 Hz, 2H), 1.92 (dd, J=2.8, 13.6 Hz, 2H), 1.65-1.62 (m, 1H), 1.46 (dq, J=3.6, 12.8 Hz, 2H), 1.11-0.95 (m, 2H).

Step 4—(1R,4r)-4-((Benzyloxy)methyl)cyclohexanecarbonyl Chloride

To a solution of 4-(benzyloxymethyl)cyclohexanecarboxylic acid (10.0 g, 40.3 mmol) in the DCM (100 mL) was added DMF (294 mg, 4.03 mmol) and (COCl)$_2$ (7.67 g, 60.4 mmol, 5.29 mL) in portion at 0° C. The mixture was stirred at 0° C. for 2 hrs. On completion, the reaction mixture was concentrated in vacuo to give the title compound (10.7 g, 99% yield) as yellow oil.

N-[2-(4-formylcyclohexyl)-1,3-benzothiazol-6-yl]-6-(trifluoromethyl)pyridine-2-carboxamide (Intermediate BTI)

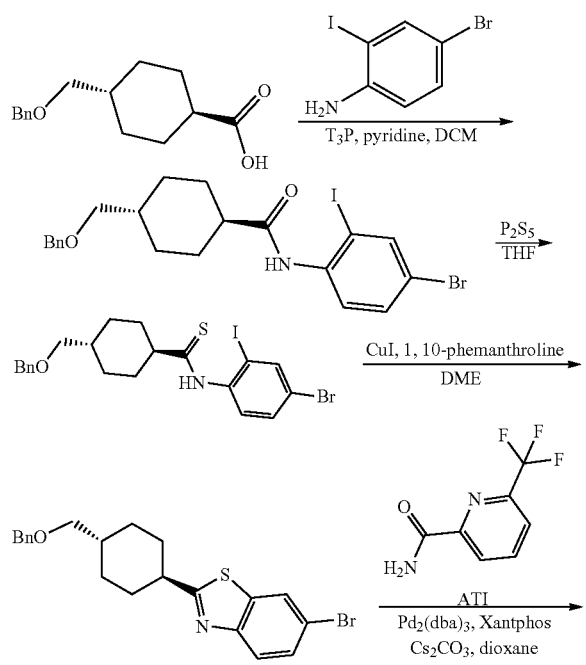

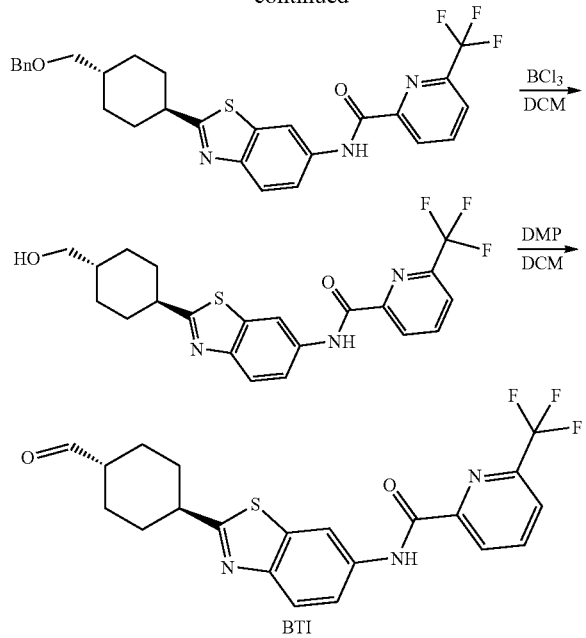

Step 1—4-(benzyloxymethyl)-N-(4-bromo-2-iodophenyl)cyclohexanecarboxamide

To a mixture of 4-(benzyloxymethyl)cyclohexanecarboxylic acid (10.0 g, 40.2 mmol, synthesized via Steps 1-3 of Intermediate BAU) and 4-bromo-2-iodo-aniline (6.00 g, 20.1 mmol, CAS #66416-72-6) in DCM (100 mL) was added pyridine (3.19 g, 40.2 mmol) and T$_3$P (76.8 g, 120 mmol). The reaction mixture was stirred at 50° C. for 24 hr. On completion, the reaction mixture was filtered and concentrated in vacuo. The residue was purified by reverse phase (0.1% FA condition) to give the title compound (4.27 g, 20% yield) as white solid. $^1$H NMR (400 MHz, DMSO-d$_6$) δ 9.36-9.29 (m, 1H), 8.04 (d, J=2.0 Hz, 1H), 7.55 (dd, J=2.0, 8.4 Hz, 1H), 7.46-7.24 (m, 6H), 4.45 (s, 2H), 3.39-3.28 (m, 2H), 3.27 (d, J=6.4 Hz, 2H), 2.42-2.29 (m, 1H), 1.96-1.89 (m, 2H), 1.87-1.78 (m, 2H), 1.47-1.42 (m, 1H), 1.08-0.95 (m, 2H).

Step 2—4-(Benzyloxymethyl)-N-(4-bromo-2-iodophenyl)cyclohexanecarbothioamide

To a mixture of 4-(benzyloxymethyl)-N-(4-bromo-2-iodo-phenyl)cyclohexanecarboxamide (4.27 g, 8.08 mmol) in THF (30 mL) was added P$_2$S$_5$ (2.70 g, 12.1 mmol). The reaction mixture was stirred at 25° C. for 12 hours. On completion, the reaction mixture was quenched with water (0.05 mL), then the reaction mixture was filtered and concentrated in vacuo. The residue was diluted with water (30 mL) and extracted with EA (2×200 mL). The combined organic layer was dried over Na$_2$SO$_4$, filtered and concentrated in vacuo to give the title compound (946 mg, 21% yield) as white solid. LC-MS (ESI$^+$) m/z 545.3 (M+H)$^+$.

Step 3—2-[4-(Benzyloxymethyl)cyclohexyl]-6-bromo-1,3-benzothiazole

To a mixture of 4-(benzyloxymethyl)-N-(4-bromo-2-iodo-phenyl)cyclohexanecarbothioamide (845 mg, 1.55 mmol) in DME (2 mL) was added CuI (29.5 mg, 155 umol)

and 1,10-phenanthroline (27.9 mg, 155 umol) in N₂. The reaction mixture was stirred at 40° C. for 12 hours. On completion, the reaction mixture was concentrated in vacuo. The residue was purified by column chromatography to give the title compound (429 mg, 66% yield) as yellow solid. ¹H NMR (400 MHz, DMSO-d₆) δ 8.34 (d, J=2.0 Hz, 1H), 7.86 (d, J=8.8 Hz, 1H), 7.62 (dd, J=2.0, 8.4 Hz, 1H), 7.38-7.25 (m, 5H), 4.46 (s, 2H), 3.29 (d, J=6.4 Hz, 2H), 3.10-3.00 (m, 1H), 2.22-2.10 (m, 2H), 1.93-1.84 (m, 2H), 1.71-1.50 (m, 3H), 1.25-1.08 (m, 2H).

Step 4—N-[2-[4-(benzyloxymethyl)cyclohexyl]-1,3-benzothiazol-6-yl]-6-(trifluoromethyl)pyridine-2-carboxamide To a mixture 2-[4-(benzyloxymethyl)cyclohexyl]-6-bromo-1,3-benzothiazole (389 mg, 934.26 umol) and 6-(trifluoromethyl)pyridine-2-carboxamide (195 mg, 1.03 mmol, Intermediate ATI) in dioxane (5 mL) was added Cs₂CO₃ (913 mg, 2.80 mmol), Pd₂(dba)₃ (85.5 mg, 93.4 umol) and Xantphos (54.0 mg, 93.4 umol). Then the reaction mixture was stirred at 80° C. for 2 hours. On completion, the residue was diluted with water (30 mL) and extracted with EA (2×50 mL). The combined organic layer was dried over Na₂SO₄, filtered and concentrated in vacuo. The residue was purified by reverse phase (0.1% FA condition) to give the title compound (188 mg, 38% yield) as yellow solid. LC-MS (ESI⁺) m/z 526.1 (M+H)⁺.

Step 5—N-[2-[4-(hydroxymethyl)cyclohexyl]-1,3-benzothiazol-6-yl]-6-(trifluoromethyl)pyridine-2-carboxamide To a mixture of N-[2-[4-(benzyloxymethyl)cyclohexyl]-1,3-benzothiazol-6-yl]-6-(trifluoromethyl) pyridine-2-carboxamide (178 mg, 338 umol) in DCM (3 mL) was added BCl₃ (1 M, 677 uL). Then the reaction mixture was stirred at 0° C. for 1 hour. On completion, the reaction mixture was quenched with water (0.05 mL) and concentrated in vacuo to give the title compound (112 mg, 75% yield) as yellow solid. ¹H NMR (400 MHz, DMSO-d₆) δ 10.62 (s, 1H), 8.60 (d, J=1.6 Hz, 1H), 8.43-8.34 (m, 2H), 8.19 (dd, J=1.2, 7.6 Hz, 1H), 7.95-7.87 (m, 2H), 3.29-3.24 (m, 3H), 3.09-3.00 (m, 1H), 2.22-2.15 (m, 2H), 1.92-1.84 (m, 2H), 1.64-1.52 (m, 2H), 1.50-1.39 (m, 1H), 1.16-1.04 (m, 2H).

Step 6—2—N-[2-(4-formylcyclohexyl)-1,3-benzothiazol-6-yl]-6-(trifluoromethyl)pyridine-2-carboxamide To a mixture of N-[2-[4-(hydroxymethyl)cyclohexyl]-1,3-benzothiazol-6-yl]-6-(trifluoromethyl) pyridine-2-carboxamide (102 mg, 234 umol) in DCM (2 mL) was added DMP (129 mg, 304 umol). Then the reaction mixture was stirred at 25° C. for 1 hours. On completion, the reaction mixture was quenched with saturated Na₂S₂O₃ (8 mL) and saturated NaHCO₃ (8 mL) at 25° C., and then the mixture was stirred for 30 minutes. The mixture was then extracted with DCM (2×20 mL). The combined organic layer was dried over Na₂SO₄, filtered and concentrated in vacuo to give the title compound (100 mg, 98% yield) as black brown solid. ¹H NMR (400 MHz, DMSO-d₆) δ 10.62 (s, 1H), 9.68-9.59 (m, 1H), 8.63-8.57 (m, 1H), 8.46-8.34 (m, 2H), 8.19 (d, J=7.6 Hz, 1H), 7.98-7.86 (m, 1H), 3.15-3.04 (m, 1H), 2.45-2.36 (m, 1H), 2.27-2.22 (m, 1H), 2.11-1.97 (m, 3H), 1.74-1.61 (m, 2H), 1.47-1.34 (m, 2H). LC-MS (ESI⁺) m/z 434.0 (M+H)⁺.

2-(2,6-dioxo-3-piperidyl)-5-fluoro-isoindoline-1,3-dione (Intermediate HX)

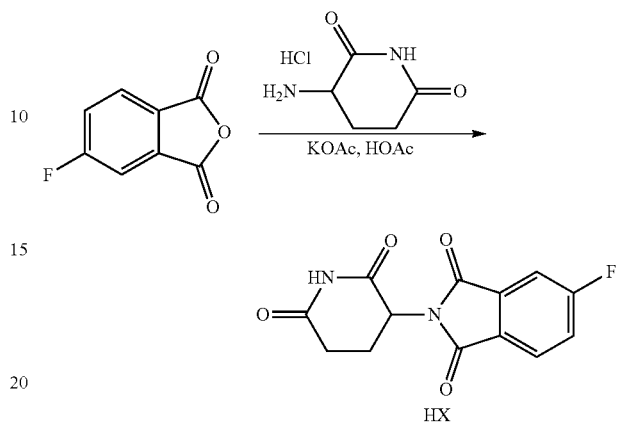

To a mixture of 3-aminopiperidine-2,6-dione (10.8 g, 65.8 mmol, HCl) and KOAc (18.2 g, 185 mmol) in HOAc (160 mL) was added 5-fluoroisobenzofuran-1,3-dione (9.95 g, 59.9 mmol, CAS #319-03-9). Then the mixture was stirred at 90° C. for 16 hours. On completion, the reaction mixture was cooled to 25° C. and diluted with water (600 mL), and then stirred at 0° C. for 0.5 hour then filtered. The filter cake was dried in vacuo to give the title compound (14.0 g, 84% yield) as black brown solid. ¹H NMR (400 MHz, DMSO-d₆) δ 11.15 (s, 1H), 8.01 (dd, J=4.4, 8.0 Hz, 1H), 7.84 (dd, J=2.4, 7.6 Hz, 1H), 7.76-7.67 (m, 1H), 5.17 (dd, J=5.6, 12.8 Hz, 1H), 2.97-2.83 (m, 1H), 2.65-2.51 (m, 2H), 2.13-2.03 (m, 1H).

5-[2-(2-Azaspiro[3.3]heptan-6-yl)ethylamino]-2-(2,6-dioxo-3-piperidyl)isoindoline-1,3-dione (Intermediate BTH)

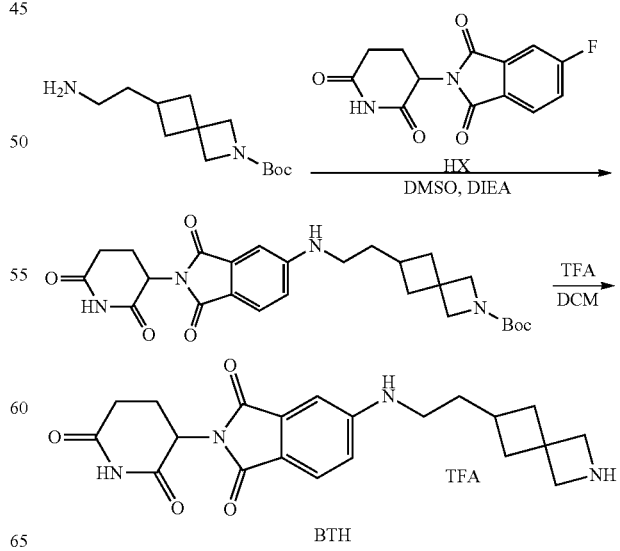

Step 1—Tert-butyl 6-[2-[[2-(2,6-dioxo-3-piperidyl)-1,3-dioxo-isoindolin-5-yl]amino]ethyl]-2-azaspiro[3.3]heptane-2-carboxylate To a solution of tert-butyl 6-(2-aminoethyl)-2-azaspiro[3.3]heptane-2-carboxylate (140 mg, 582 umol, Intermediate ATG) in DMSO (3 mL) was added 2-(2,6-dioxo-3-piperidyl)-5-fluoro-isoindoline-1,3-dione (193 mg, 699 umol, Intermediate HX) and DIEA (225 mg, 1.75 mmol). The mixture was degassed and purged with $N_2$ 3 times, and then the mixture was stirred at 130° C. for 3 hrs under $N_2$ atmosphere. On completion, the mixture was filtered and the filtrate was concentrated under reduced pressure to afford a residue. The residue was purified by reversed-phase HPLC (0.1% FA condition) to give the title compound (40.0 mg, 14% yield) as a green solid. $^1$H NMR (400 MHz, CHLOROFORM-d) δ 7.97 (s, 1H), 7.63 (d, J=8.4 Hz, 1H), 6.97 (s, 1H), 6.75 (d, J=8.4 Hz, 1H), 4.94 (dd, J=5.6, 12.4 Hz, 1H), 3.95 (s, 2H), 3.82 (s, 2H), 3.16 (t, J=7.2 Hz, 2H), 2.93-2.87 (m, 1H), 2.85-2.72 (m, 2H), 2.37-2.31 (m, 2H), 2.28-2.19 (m, 1H), 2.16-2.10 (m, 1H), 1.87-1.82 (m, 2H), 1.77-1.70 (m, 2H), 1.44 (s, 9H).

Step 2—5-[2-(2-Azaspiro[3.3]heptan-6-yl)ethylamino]-2-(2,6-dioxo-3-piperidyl)isoindoline-1,3-dione To a solution of tert-butyl 6-[2-[[2-(2,6-dioxo-3-piperidyl)-1,3-dioxo-isoindolin-5-yl]amino]ethyl]-2-azaspiro[3.3]heptane-2-carboxylate (40.0 mg, 80.5 umol) in DCM (2 mL) was added TFA (770 mg, 6.75 mmol) at 25° C. The mixture was stirred at 25° C. for 1 hr. On completion, the reaction mixture was concentrated under reduced pressure to give the title compound (40.0 mg, 97% yield, TFA salt) as yellow oil. LC-MS (ESI$^+$) m/z 397.2 (M+H)$^+$.

(1R,4r)-4-((Benzyloxy)methyl)cyclohexanecarbonyl chloride (Intermediate BAU)

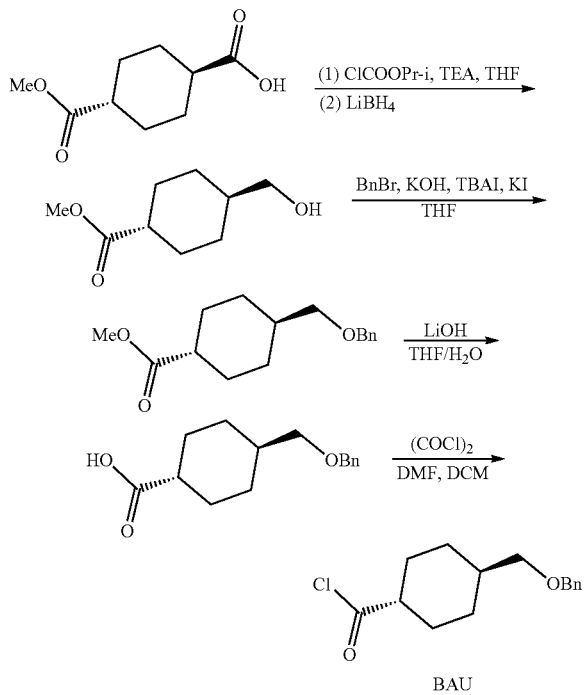

BAU

Step 1—(1R,4r)-Methyl 4-(hydroxymethyl)cyclohexanecarboxylate

To a solution of 4-methoxycarbonylcyclohexanecarboxylic acid (20.0 g, 107 mmol, CAS #15177-67-0) in the THF (200 mL) was added Et$_3$N (21.7 g, 215 mmol, 29.9 mL) and isopropyl carbonochloridate (19.7 g, 161 mmol, 22.4 mL) at 0° C. The mixture was stirred at 25° C. for 1 hour. Then the mixture was filtered and the LiBH$_4$ (11.7 g, 537 mmol) was added in portion at 0° C. The mixture was stirred at 25° C. for 4 hours. On completion, the mixture was quenched by water (500 mL) and extracted with EA (3×1000 mL). The organic layers were dried over Na$_2$SO$_4$, filtered and concentrated in vacuo. The residue was purified by column chromatography to give the title compound (9.70 g, 52% yield) as colorless oil. $^1$H NMR (400 MHz, CDCl$_3$) δ 3.67 (s, 3H), 3.47 (d, J=6.0 Hz, 2H), 2.26 (tt, J=3.6, 12.4 Hz, 1H), 2.06-1.99 (m, 2H), 1.88 (dd, J=3.2, 13.6 Hz, 2H), 1.56-1.39 (m, 3H), 1.07-0.93 (m, 2H).

Step 2—(1R,4r)-Methyl 4-((benzyloxy)methyl)cyclohexanecarboxylate

To a solution of methyl 4-(hydroxymethyl)cyclohexanecarboxylate (9.70 g, 56.3 mmol) in the THF (100 mL) was added KOH (4.74 g, 84.5 mmol), TBAI (4.16 g, 11.3 mmol), KI (1.87 g, 11.3 mmol) and BnBr (14.5 g, 84.5 mmol, 10.0 mL). The mixture was stirred at 25° C. for 12 hours. On completion, the reaction mixture was filtered and concentrated in vacuo. The residue was purified by column chromatography to give the title compound (11.0 g, 74% yield) as colorless oil. $^1$H NMR (400 MHz, CDCl$_3$) δ 7.39-7.27 (m, 5H), 4.50 (s, 2H), 3.67 (s, 3H), 3.29 (d, J=6.4 Hz, 2H), 2.25 (tt, J=3.6, 12.4 Hz, 1H), 2.04-1.98 (m, 2H), 1.91 (br dd, J=3.6, 13.6 Hz, 2H), 1.71-1.61 (m, 1H), 1.45-1.42 (m, 2H), 1.08-0.94 (m, 2H).

Step 3—(1R,4r)-4-((benzyloxy)methyl)cyclohexanecarboxylic Acid

To a solution of methyl 4-(benzyloxymethyl)cyclohexanecarboxylate (11.0 g, 41.9 mmol) in the THF (100 mL), MeOH (20 mL) and H$_2$O (20 mL) was added LiOH (5.02 g, 210 mmol). The mixture was stirred at 25° C. for 12 hours. On completion, the reaction mixture was concentrated in vacuo. The residue was diluted with water (100 mL) and washed with PE (200 mL). The water phase was acidified by HCl (aq, 1M) to pH=4. Then the mixture was extracted with DCM (3×200 mL). The organic layer was dried over Na$_2$SO$_4$, filtered and concentrated in vacuo to give the title compound (10.1 g, 97% yield) as colorless oil. $^1$H NMR (400 MHz, CDCl$_3$) δ 7.41-7.26 (m, 5H), 4.50 (s, 2H), 3.30 (d, J=6.4 Hz, 2H), 2.28 (tt, J=3.6, 12.4 Hz, 1H), 2.05 (dd, J=2.8, 13.6 Hz, 2H), 1.92 (dd, J=2.8, 13.6 Hz, 2H), 1.65-1.62 (m, 1H), 1.46 (dq, J=3.6, 12.8 Hz, 2H), 1.11-0.95 (m, 2H).

Step 4—(1R,4r)-4-((Benzyloxy)methyl)cyclohexanecarbonyl Chloride

To a solution of 4-(benzyloxymethyl)cyclohexanecarboxylic acid (10.0 g, 40.3 mmol) in the DCM (100 mL) was added DMF (294 mg, 4.03 mmol) and (COCl)$_2$ (7.67 g, 60.4 mmol, 5.29 mL) in portion at 0° C. The mixture was stirred at 0° C. for 2 hrs. On completion, the reaction mixture was concentrated in vacuo to give the title compound (10.7 g, 99% yield) as yellow oil.

937

Methyl 5-amino-2-bromo-4-iodo-benzoate (Intermediate BAV)

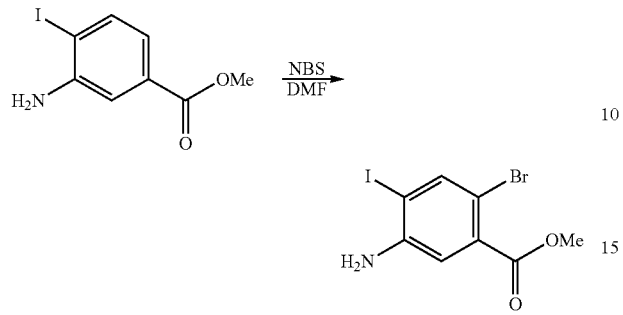

To a solution of methyl 3-amino-4-iodo-benzoate (5.00 g, 18.1 mmol, CAS #412947-54-7) in DMF (25 mL) was added NBS (3.28 g, 18.4 mmol). The mixture was stirred at 0° C. for 2 hours. On completion, the mixture was poured into 500 mL water and a solid was obtained. The mixture was filtered then the filtered cake was washed with water (3×50 mL) and dried in vacuo to give the title compound (6.00 g, 93% yield) as yellow solid. $^1$H NMR (400 MHz, DMSO-$d_6$) δ 7.84 (s, 1H), 7.13 (s, 1H), 5.66 (br s, 2H), 3.81 (s, 3H).

Methyl 6-bromo-2-[4-(hydroxymethyl)cyclohexyl]-1,3-benzothiazole-5-carboxylate (Intermediate BAW)

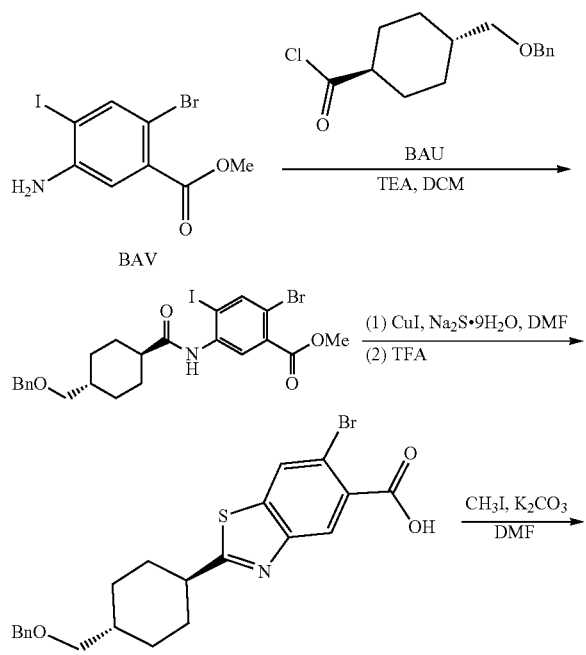

938

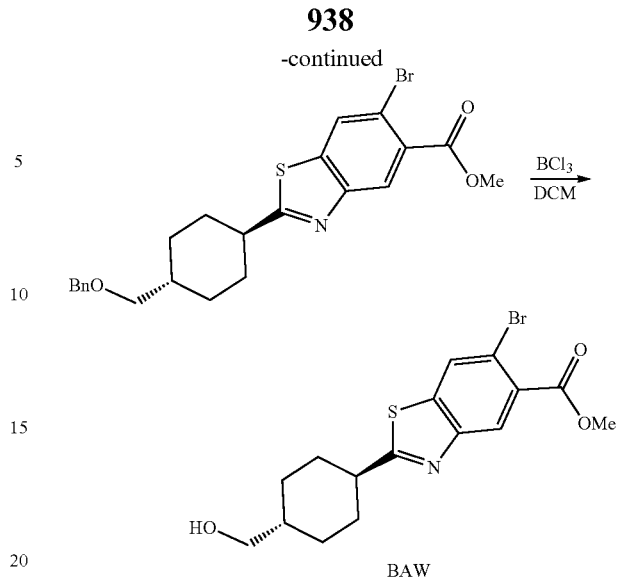

Step 1—Methyl 5-[[4-(benzyloxymethyl)cyclohexanecarbonyl]amino]-2-bromo-4-iodo-benzoate To a solution of methyl 5-amino-2-bromo-4-iodo-benzoate (707 mg, 1.9 mmol, Intermediate BAV) in DCM (10 mL) was added Et$_3$N (603 mg, 5.96 mmol). Then a mixture of 4-(benzyloxymethyl)cyclohexane carbonyl chloride (530 mg, 1.99 mmol, Intermediate BAU) in DCM (20 mL) was added to the reaction mixture. The mixture was stirred at 0° C. for 2 hours. On completion, the mixture was concentrated in vacuo. The residue was diluted with water (50 mL) and extracted with EA (3×100 mL). The combined organic layers were washed with brine (50 mL), dried over Na$_2$SO$_4$, filtered and concentrated of most solvent. Then the solid was precipitated out, then filtered, the cake was dried in vacuo to give the title compound (660 mg, 56% yield) as white solid. $^1$H NMR (400 MHz, CDCl$_3$) δ 8.76 (d, J=1.6 Hz, 1H), 8.09 (d, J=1.6 Hz, 1H), 7.52 (s, 1H), 7.41-7.27 (m, 5H), 4.52 (d, J=1.6 Hz, 2H), 3.92 (d, J=1.6 Hz, 3H), 3.34 (dd, J=1.6, 6.0 Hz, 2H), 2.35-2.24 (m, 1H), 2.12 (d, J=13.2 Hz, 2H), 2.00 (d, J=13.2 Hz, 2H), 1.77-1.58 (m, 3H), 1.19-1.05 (m, 2H).

Step 2—2-[4-(Benzyloxymethyl)cyclohexyl]-6-bromo-1,3-benzothiazole-5-carboxylic Acid To a solution of methyl 5-[[4-(benzyloxymethyl)cyclohexanecarbonyl]amino]-2-bromo-4-iodo-benzoate (5.60 g, 9.55 mmol) in DMF (50 mL) was added CuI (363 mg, 1.91 mmol) and Na$_2$S·9H$_2$O (13.7 g, 57.3 mmol). The mixture was stirred at 80° C. for 6 hours, and then cooled to rt. Then TFA (15.4 g, 135 mmol) was added to the mixture and the mixture was stirred at 25° C. for 6 hours. On completion, the residue was diluted with water (100 mL) and extracted with EA (3×100 mL). The combined organic layers were washed with brine (100 mL), dried over Na$_2$SO$_4$, filtered and concentrated in vacuo to give the title compound (4.00 g, 56% yield) as yellow oil. LC-MS (ESI+) m/z 462.1 (M+3)$^+$.

Step 3—Methyl 2-[4-(benzyloxymethyl)cyclohexyl]-6-bromo-1,3-benzothiazole-5-carboxylate To a solution of 2-[4-(benzyloxymethyl)cyclohexyl]-6-bromo-1,3-benzothiazole-5-carboxylic acid (4.00 g, 8.69 mmol) in DMF (20 mL) was added CH$_3$I (2.47 g, 17.3 mmol) and K₂CO₃ (2.40 g, 17.3 mmol). The mixture was stirred at 15° C. for 2 hours. On completion, the mixture was filtered and concentrated in vacuo. The residue was purified by flash silica gel chromatography (PE:EA 3:1) to give title compound (3.00 g, 72% yield) as white solid. ¹H NMR (400 MHz, CDCl₃) δ 8.31 (s, 1H), 8.05 (s, 1H), 7.31-7.21 (m, 5H), 4.44 (s, 2H), 3.88 (s, 3H), 3.27 (d, J=6.0 Hz, 2H), 2.97 (t, J=12.0 Hz, 1H), 2.87 (s, 5H), 2.80 (s, 5H), 2.19 (d, J=12.4 Hz, 2H), 1.95 (d, J=13.6 Hz, 2H), 1.73-1.65 (m, 1H), 1.58 (q, J=12.8 Hz, 2H), 1.20-1.07 (m, 2H).

Step 4—Methyl 6-bromo-2-[4-(hydroxymethyl)cyclohexyl]-1,3-benzothiazole-5-carboxylate To a solution of methyl 2-[4-(benzyloxymethyl)cyclohexyl]-6-bromo-1,3-benzothiazole-5-carboxylate (2.00 g, 4.22 mmol) in DCM (40 mL) was added BCl₃ (9.88 g, 84.3 mmol). The mixture was stirred at 25° C. for 2 hours. On completion, to the mixture was added sat.NaHCO₃. aq (50 mL) then extracted with DCM (3×50 mL). The combined organic layers were washed with brine (100 mL), dried over Na₂SO₄, filtered and concentrated in vacuo to give the title compound (1.60 g, 90% yield) as white solid. ¹H NMR (400 MHz, CDCl₃) δ 8.48 (s, 1H), 8.21-8.13 (m, 1H), 3.98 (s, 3H), 3.55 (d, J=6.0 Hz, 2H), 3.25-3.12 (m, 1H), 2.42-2.26 (m, 2H), 2.09-1.98 (m, 2H), 1.78-1.62 (m, 3H), 1.29-1.16 (m, 2H).

N-[2-(4-formylcyclohexyl)-5-(1-hydroxy-1-methyl-ethyl)-1,3-benzothiazol-6-yl]-6-(trifluoromethyl)pyridine-2-carboxamide (Intermediate BAX)

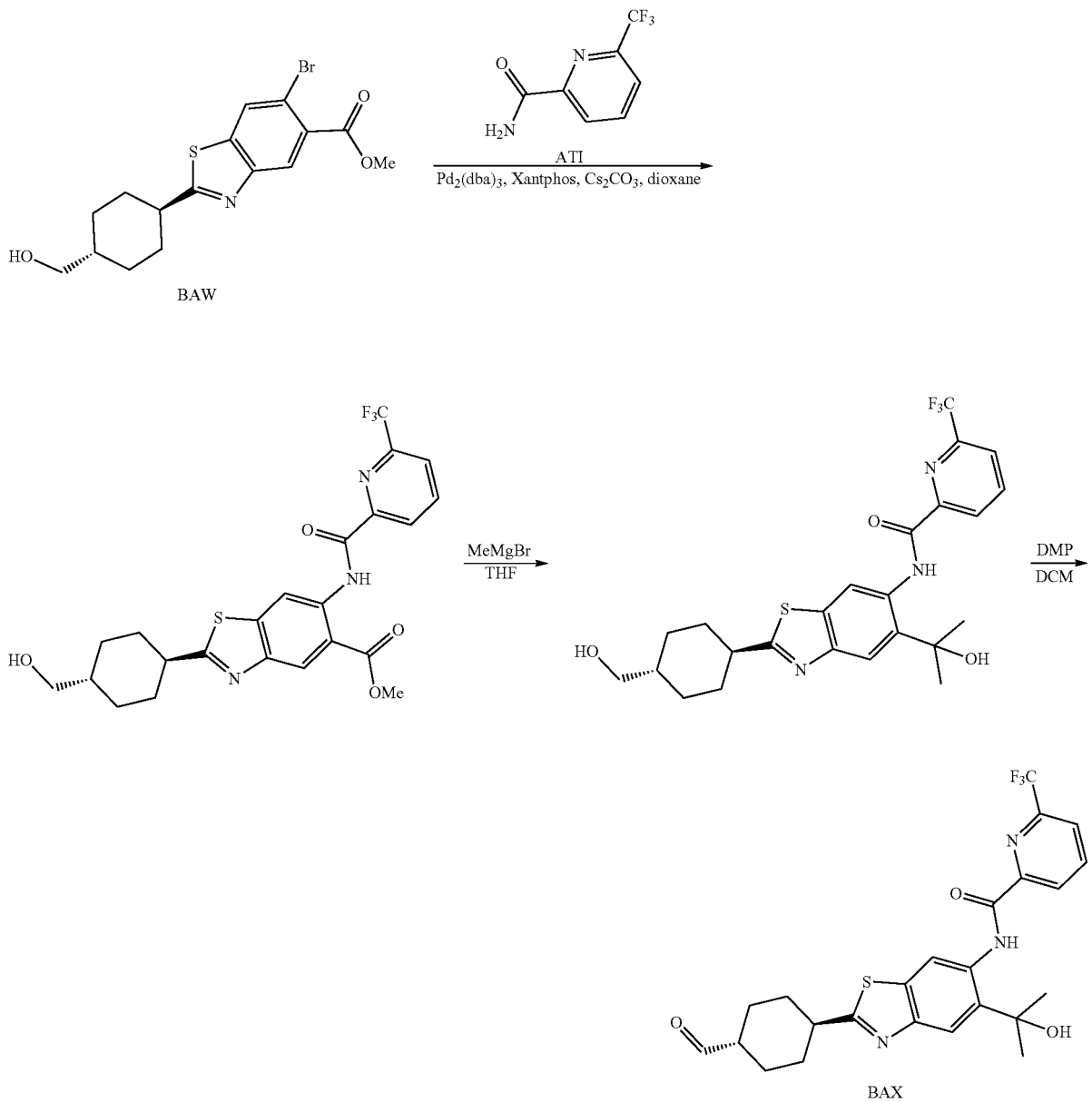

Step 1—Methyl 2-[4-(hydroxymethyl)cyclohexyl]-6-[[6-(trifluoromethyl)pyridine-2-carbonyl]amino]-1,3-benzothiazole-5-carboxylate To a solution of methyl 6-bromo-2-[4-(hydroxymethyl) cyclohexyl]-1,3-benzothiazole-5-carboxylate (300 mg, 780 umol, Intermediate BAW) and 6-(trifluoromethyl)pyridine-2-carboxamide (163 mg, 858 umol, Intermediate ATI) in dioxane (30 mL) was added Xantphos (90.3 mg, 156 umol), $Cs_2CO_3$ (763 mg, 2.34 mmol) and $Pd_2(dba)_3$ (71.4 mg, 78.1 umol) at 25° C. The mixture was stirred at 80° C. for 12 hrs under $N_2$. On completion, the mixture was filtered with celite and concentrated in vacuo. The residue was purified by column chromatography to give title compound (120 mg, 31% yield) as yellow solid. $^1$H NMR (400 MHz, DMSO-$d_6$) δ 12.82 (s, 1H), 9.44 (s, 1H), 8.54 (s, 1H), 8.50-8.46 (m, 1H), 8.45-8.38 (m, 1H), 8.23 (d, J=7.8 Hz, 1H), 4.53-4.40 (m, 1H), 3.98 (s, 3H), 3.27 (t, J=5.6 Hz, 2H), 3.08 (s, 1H), 2.19 (d, J=13.0 Hz, 2H), 1.93-1.83 (m, 2H), 1.66-1.51 (m, 2H), 1.48-1.38 (m, 1H), 1.18-1.05 (m, 2H).

Step 2—N-[2-[4-(hydroxymethyl)cyclohexyl]-5-(1-hydroxy-1-methyl-ethyl)-1,3-benzothiazol-6-yl]-6-(trifluoromethyl)pyridine-2-carboxamide To a solution of methyl 2-[4-(hydroxymethyl)cyclohexyl]-6-[[6-(trifluoromethyl)pyridine-2-carbonyl]amino]-1,3-benzothiazole-5-carboxylate (120 mg, 243 umol) in THF (10 mL) was added MeMgBr (3 M, 405 uL). The mixture was stirred at 0° C. for 2 hours. The reaction mixture was quenched by addition sat. $NH_4Cl$ (10 mL) at 0° C., and then diluted with water (50 mL) and extracted with EA (3×50 mL). The combined organic layers were washed with brine (100 mL), dried over $Na_2SO_4$, filtered and concentrated in vacuo to give a residue. The residue was purified by prep-HPLC (column: Phenomenex Synergi C18 150*25*10 um; mobile phase: [water (0.225% FA)-ACN]; B %: 44%-74%, 10 min) to give the title compound (80.0 mg, 60% yield) as white solid. $^1$H NMR (400 MHz, DMSO-$d_6$) δ 12.56 (s, 1H), 9.07 (s, 1H), 8.51-8.45 (m, 1H), 8.39 (t, J=8.0 Hz, 1H), 8.20 (d, J=7.6 Hz, 1H), 7.94-7.88 (m, 1H), 6.08 (s, 1H), 4.46 (t, J=5.2 Hz, 1H), 3.28 (t, J=5.6 Hz, 2H), 3.10-3.00 (m, 1H), 2.19 (d, J=11.2 Hz, 2H), 1.94-1.84 (m, 2H), 1.64 (s, 6H), 1.61-1.53 (m, 2H), 1.50-1.40 (m, 1H), 1.19-1.06 (m, 2H).

Step 3—N-[2-(4-formylcyclohexyl)-5-(1-hydroxy-1-methyl-ethyl)-1,3-benzothiazol-6-yl]-6-(trifluoromethyl)pyridine-2-carboxamide To a solution of N-[2-[4-(hydroxymethyl)cyclohexyl]-5-(1-hydroxy-1-methyl-ethyl)-1,3-benzothiazol-6-yl]-6-(trifluoromethyl)pyridine-2-carboxamide (50.0 mg, 101 umol) in DCM (10 mL) was added DMP (51.5 mg, 121 umol). The mixture was stirred at 25° C. for 2 hours. On completion, the mixture was added 10 mL sat. $NaHCO_3$ and 10 mL sat. $Na_2S_2O_3$, then extracted with DCM (3×50 mL). The combined organic layers were washed with brine (100 mL), dried over $Na_2SO_4$, filtered and concentrated in vacuo to give the title compound (60.0 mg, 90% yield) as yellow solid. LC-MS (ESI$^+$) m/z 492.2 (M+1)$^+$.

2-(2,6-Dioxo-3-piperidyl)-4-[[3-(methylamino)cyclobutyl]amino]isoindoline-1,3-dione (Intermediate AOW)

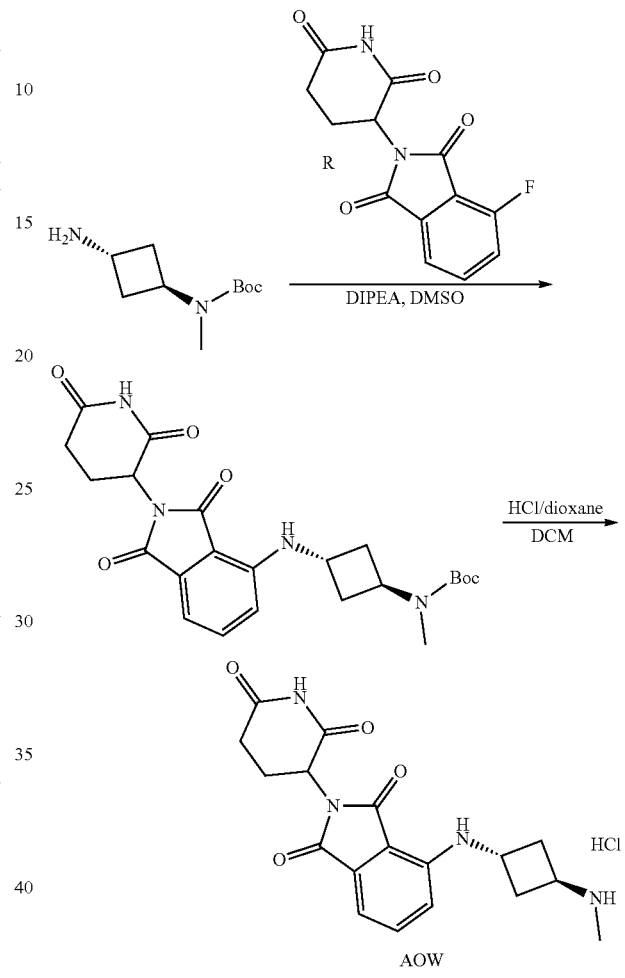

Step 1—Tert-butyl N-[3-[[2-(2,6-dioxo-3-piperidyl)-1,3-dioxo-isoindolin-4-yl]amino]cyclobutyl]-N-methyl-carbamate To a solution of tert-butyl N-(3-aminocyclobutyl)-N-methyl-carbamate (250 mg, 1.25 mmol, CAS #1392803-14-3) and 2-(2,6-dioxo-3-piperidyl)-4-fluoro-isoindoline-1,3-dione (362 mg, 1.31 mmol, Intermediate R) in DMSO (12 mL) was added DIPEA (322 mg, 2.50 mmol) at 25° C. The reaction mixture was stirred at 130° C. for 3 hrs. On completion, the reaction mixture was concentrated in vacuo. The residue was purified by reverse phase (0.1% FA condition) to give the title compound (500 mg, 87% yield) as a yellow solid. $^1$H NMR (400 MHz, DMSO-$d_6$) δ 11.09 (s, 1H), 7.60 (dd, J=7.2, 8.4 Hz, 1H), 7.09 (d, J=6.8 Hz, 1H), 6.89 (d, J=8.4 Hz, 1H), 6.55 (d, J=5.6 Hz, 1H), 5.07 (dd, J=5.2, 12.8 Hz, 1H), 4.77-4.52 (m, 1H), 4.15-3.95 (m, 1H), 2.96-2.84 (m, 1H), 2.82 (s, 3H), 2.66-2.52 (m, 4H), 2.20 (t, J=8.8 Hz, 2H), 2.10-1.97 (m, 1H), 1.39 (s, 9H); LC-MS (ESI+) m/z 457.0 (M+H)$^+$.

Step 2—2-(2,6-Dioxo-3-piperidyl)-4-[[3-(methyl-amino)cyclobutyl]amino]isoindoline-1,3-dione To a solution of tert-butyl N-[3-[[2-(2,6-dioxo-3-piperidyl)-1,3-dioxo-isoindolin-4-yl]amino] cyclobutyl]-N-methyl-carbamate (80.0 mg, 175 umol) in DCM (5 mL) was added HCl/dioxane (4 M, 2 mL) at 25° C. The mixture was stirred at 25° C. for 2 hrs. The mixture was stirred at 25° C. for 2 hrs. On completion, the reaction mixture was concentrated in vacuo to give the title compound (68 mg, 98% yield, HCl salt) as a yellow solid. LC-MS (ESI+) m/z 357.2 (M+H)$^+$.

Benzyl N-[3-(3-aminocyclobutoxy)propyl]-N-methyl-carbamate (Intermediate AOY)

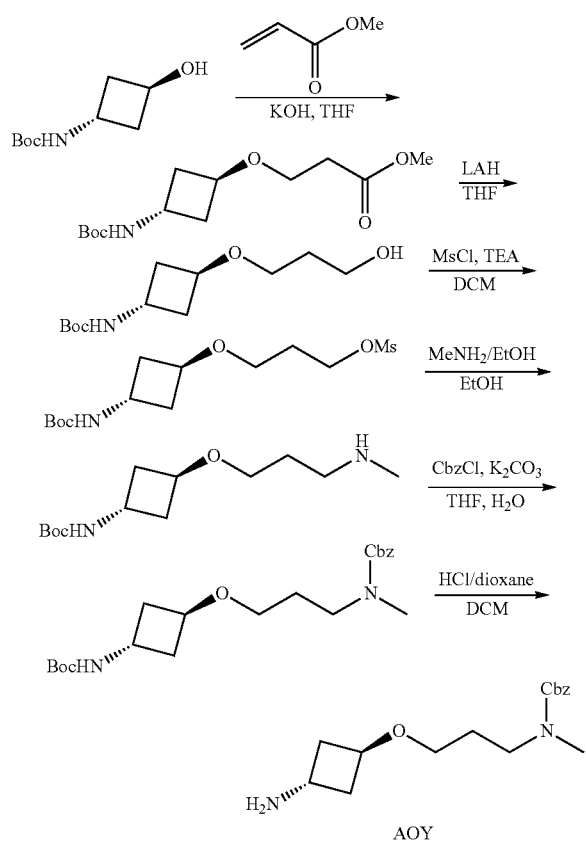

Step 1—Methyl 3-[3-(tert-butoxycarbonylamino)cyclobutoxy]propanoate

To a solution of tert-butyl N-(3-hydroxycyclobutyl)carbamate (2.50 g, 13.3 mmol, CAS #389890-42-0) and methyl prop-2-enoate (2.30 g, 26.7 mmol, CAS #96-33-3) in THF (25 mL) was added KOH (74.9 mg, 1.34 mmol). The reaction mixture was stirred at 20° C. for 16 hrs. On completion, the reaction mixture was diluted with water (80 mL) and extracted with EA (3×80 mL). The combined organic layers were washed with brine (2×50 mL), dried over Na$_2$SO$_4$, filtered and concentrated in vacuo. The residue was purified by silica gel chromatography (PE:EA=8:1) to give the title compound (1.80 g, 49% yield) as colorless oil. $^1$H NMR (400 MHz, CDCl$_3$) δ 4.81-4.59 (m, 1H), 4.26-4.03 (m, 2H), 3.70 (s, 3H), 3.59 (t, J=6.4 Hz, 2H), 2.57 (t, J=6.4 Hz, 2H), 2.42-2.30 (m, 2H), 2.19-2.06 (m, 2H), 1.44 (s, 9H).

Step 2—Tert-butyl N-[3-(3-hydroxypropoxy)cyclobutyl]carbamate

To a solution of methyl 3-[3-(tert-butoxycarbonylamino)cyclobutoxy]propanoate (1.80 g, 6.59 mmol) in THF (20 mL) was added LAH (274 mg, 7.24 mmol). The reaction mixture was stirred at 0° C. for 1 hr. On completion, the reaction mixture was quenched by water (0.25 mL), added 15% NaOH (0.3 mL), water (0.8 mL), diluted with EA (50 mL), dried over Na$_2$SO$_4$, filtered and concentrated in vacuo to give the title compound (1.50 g, 92.% yield) as yellow oil. $^1$H NMR (400 MHz, CDCl$_3$) δ 4.70 (s, 1H), 4.54-4.41 (m, 1H), 4.27-4.14 (m, 1H), 4.12-4.04 (m, 1H), 3.81-3.74 (m, 2H), 3.50 (t, J=6.0 Hz, 2H), 2.37-2.30 (m, 2H), 2.24-2.14 (m, 2H), 1.86-1.80 (m, 2H), 1.44 (s, 9H).

Step 3—3-[3-(Tert-butoxycarbonylamino)cyclobutoxy]propyl methanesulfonate

To a solution of tert-butyl N-[3-(3-hydroxypropoxy)cyclobutyl]carbamate (1.50 g, 6.11 mmol) and TEA (928 mg, 9.17 mmol) in DCM (20 mL) was added MsCl (840 mg, 7.34 mmol) at 0° C. The reaction mixture was stirred at 0° C. for 1 hr. On completion, the reaction mixture was diluted with water (20 mL) and extracted with DCM (3×40 mL). The combined organic layers were washed with brine (2×30 mL), dried over Na$_2$SO$_4$, filtered and concentrated in vacuo to give the title compound (1.90 g, crude) as yellow oil. $^1$H NMR (400 MHz, CDCl$_3$) δ 5.23-5.11 (m, 1H), 4.79-4.66 (m, 1H), 4.34 (t, J=6.0 Hz, 2H), 4.09-4.04 (m, 1H), 3.42 (t, J=6.0 Hz, 2H), 3.02 (s, 3H), 2.51-2.26 (m, 4H), 2.00 (q, J=6.0 Hz, 2H), 1.44 (s, 9H).

Step 4—Tert-butyl N-[3-[3-(methylamino)propoxy]cyclobutyl]carbamate

A mixture of 3-[3-(tert-butoxycarbonylamino)cyclobutoxy]propyl methanesulfonate (1.90 g, 5.87 mmol) and MeNH$_2$/EtOH (5.87 mmol, 10 mL, 30% solution) was stirred at 70° C. for 12 hrs in a sealed tube (15 psi). On completion, the reaction mixture was concentrated in vacuo to give the title compound (1.80 g, crude) as yellow oil and used for next step directly. LC-MS (ESI$^+$) m/z 259.0 (M+H)$^+$.

Step 5—Benzyl N-[3-[3-(tert-butoxycarbonylamino)cyclobutoxy]propyl]-N-methyl-carbamate To a solution of tert-butyl N-[3-[3-(methylamino)propoxy]cyclobutyl]carbamate (1.80 g, 6.97 mmol) and K$_2$CO$_3$ (1.93 g, 13.9 mmol) in a mixed solvents of THF (15 mL) and water (5 mL) was added CbzCl (1.78 g, 10.4 mmol). The reaction mixture was stirred at 20° C. for 2 hrs. On completion, the reaction mixture was diluted with water (30 mL) and extracted with EA (3×50 mL). The combined organic layers were washed with brine (2×30 mL), dried over Na$_2$SO$_4$, filtered and concentrated in vacuo. The residue was purified by silica gel chromatography (PE:EA=5:1) to give the title compound (1.30 g, 41% yield) as yellow oil. $^1$H NMR (400 MHz, CDCl$_3$) δ 7.39-7.29 (m, 5H), 5.13 (s, 2H), 4.79-4.58 (m, 1H), 4.32-4.14 (m, 1H), 4.07-3.92 (m, 1H), 3.42-3.21 (m, 4H), 2.94 (s, 3H), 2.39-2.23 (m, 2H), 2.14-2.05 (m, 2H), 1.87-1.72 (m, 2H), 1.45 (s, 9H).

Step 6—Benzyl N-[3-(3-aminocyclobutoxy)propyl]-N-methyl-carbamate

To a solution of benzyl N-[3-[3-(tert-butoxycarbonylamino)cyclobutoxy]propyl]-N-methyl-carbamate (1.60 g, 4.08 mmol) in DCM (20 mL) was added HCl/dioxane (4 M, 15 mL). The reaction mixture was stirred at 20° C. for 1 hour. On completion, the reaction mixture was concentrated in vacuo to give the title compound (1.30 g, 96% yield, HCl salt) as yellow semisolid. LC-MS (ESI⁺) m/z 293.2 (M+H)⁺.

N-[6-(difluoromethyl)-2-(4-formylcyclohexyl)indazol-5-yl]-6-(trifluoromethyl) pyridine-2-carboxamide (Intermediate ALU)

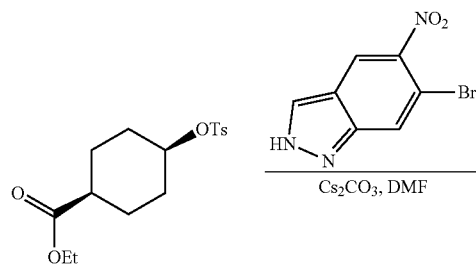

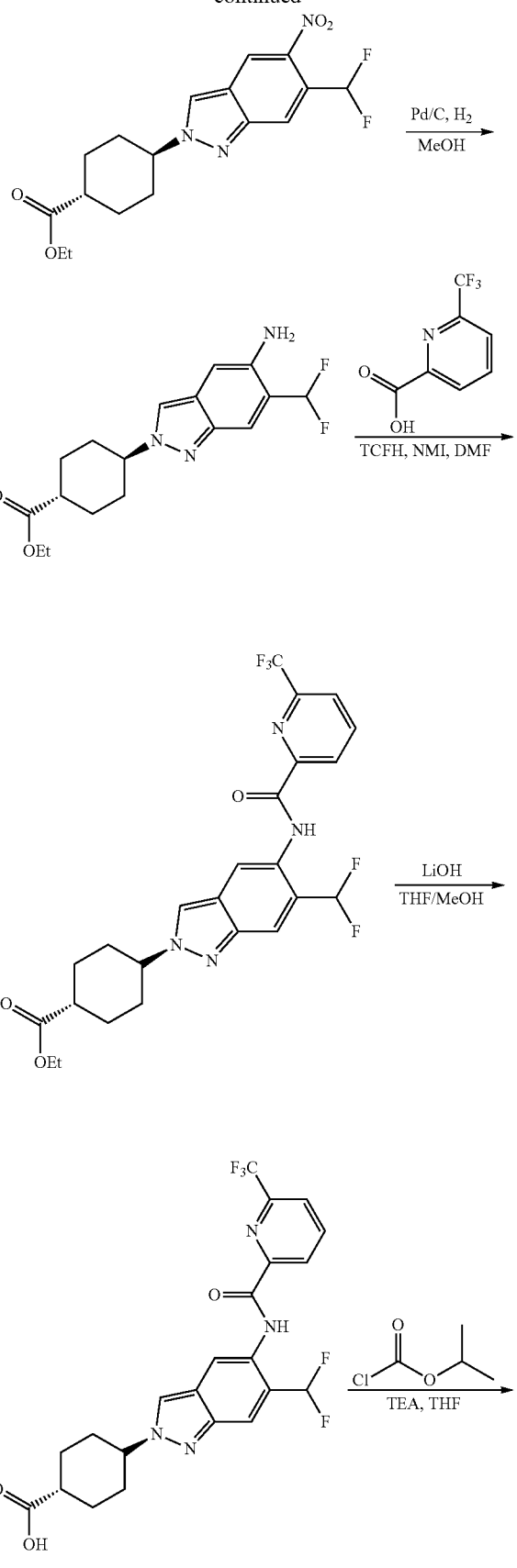

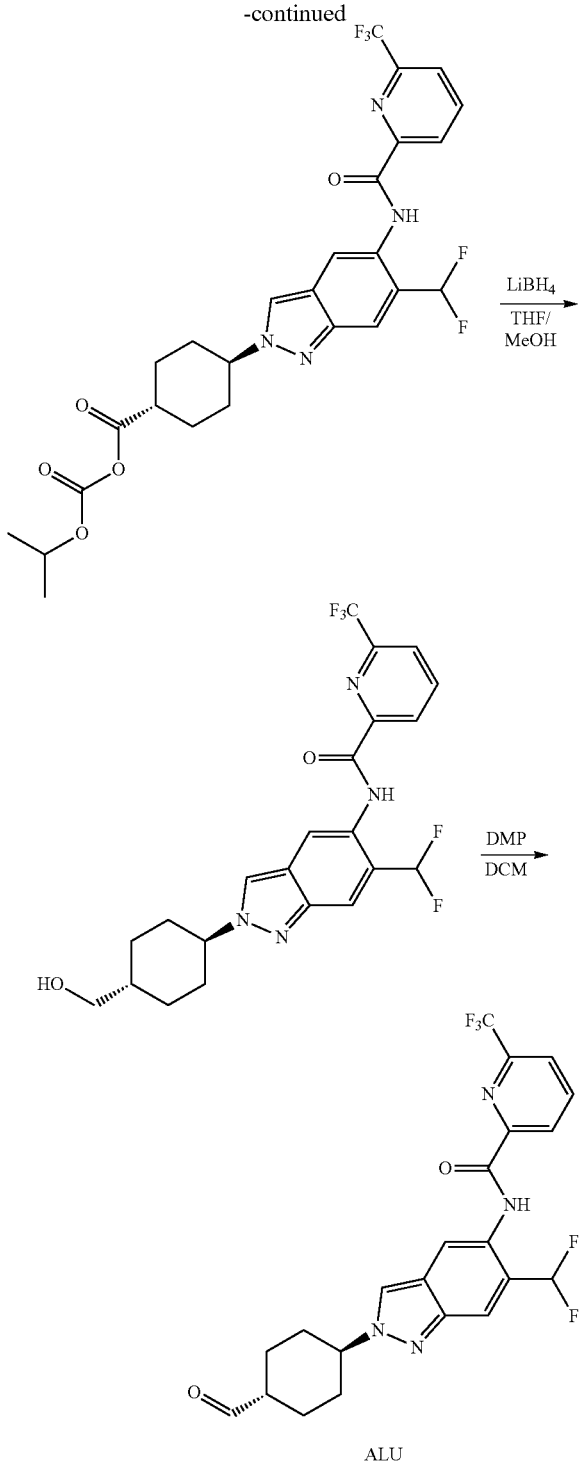

Step 1—Ethyl 4-(6-bromo-5-nitro-indazol-2-yl)cyclohexanecarboxylate

To a solution of 6-bromo-5-nitro-2H-indazole (8.30 g, 34.3 mmol, CAS #1351813-02-9) and ethyl 4-(p-tolylsulfonyloxy)cyclohexanecarboxylate (22.4 g, 68.6 mmol, Intermediate AGK) in DMF (100 mL) was added $Cs_2CO_3$ (22.4 g, 68.6 mmol). The mixture was stirred at 80° C. for 24 hrs. On completion, the reaction mixture was concentrated in vacuo to remove solvent. Then to the mixture was added 100 mL water and extracted with EA 150 mL (3×50 mL). The combined organic layers were washed with 100 mL brine, dried over $Na_2SO_4$, filtered and concentrated in vacuo to give a residue. The residue was purified by flash silica gel chromatography (PE:EA 2:1) and then the residue was purified by pre-HPLC (column: Phenomenex Synergi Max-RP 250*50 mm*10 um; mobile phase: [water (0.1% TFA)-ACN]; B %: 45ACN %-75ACN %, 29 min) to give the title compound (1.60 g, 40% yield) as yellow solid. $^1$H NMR (400 MHz, DMSO-$d_6$) δ 8.60 (s, 1H), 8.45 (s, 1H), 8.34 (s, 1H), 4.91-4.71 (m, 1H), 4.08 (q, J=7.2 Hz, 2H), 2.47-2.40 (m, 1H), 2.10-1.89 (m, 6H), 1.74-1.55 (m, 2H), 1.20 (t, J=7.2 Hz, 3H).

Step 2—2-(2,6-Dioxo-3-piperidyl)-4-[[(2R)-morpholin-2-yl]methylamino]isoindoline-1,3-dione To a solution of ethyl 4-(6-bromo-5-nitro-indazol-2-yl) cyclohexanecarboxylate (1.60 g, 4.04 mmol) and potassium; trifluoro(vinyl)boranuide (1.62 g, 12.1 mmol) and potassium; trifluoro(vinyl)boranuide (1.62 g, 12.1 mmol) in dioxane (100 mL) was added $Pd(dppf)Cl_2$ (329 mg, 403 umol) and $NaHCO_3$ (2 M, 4.04 mL). The mixture was stirred at 90° C. for 6 hrs. On completion, the mixture was filtered with celite and concentrated in vacuo. The crude product was purified by flash silica gel chromatography (PE:EA 1:1) to give the title compound (1.39 g, 50% yield) as yellow solid. LC-MS (ESI+) m/z 344.1 (M+1)$^+$.

Step 3—Ethyl 4-(6-formyl-5-nitro-indazol-2-yl) cyclohexanecarboxylate

A mixture of ethyl 4-(5-nitro-6-vinyl-indazol-2-yl)cyclohexanecarboxylate (1.39 g, 4.20 mmol), $NaIO_4$ (3.74 g, 17.4 mmol), $OsO_4$ (33.3 mg, 131 umol) and 2,6-dimethylpyridine (936 mg, 8.74 mmol, 1.02 mL) in a mixed solvents of dioxane (20 mL) and $H_2O$ (20 mL) was stirred at 0° C. for 1 hour. On completion, the mixture was added 10 mL $Na_2S_2O_4$ and extracted with DCM 150 mL (3×50 mL). The combined organic layers were washed with 100 mL brine, dried over $Na_2SO_4$, filtered and concentrated in vacuo to give the title compound (1.50 g, 80% yield) as yellow solid. LC-MS (ESI$^+$) m/z 346.0 (M+1)$^+$.

Step 4—Ethyl 4-[6-(difluoromethyl)-5-nitro-indazol-2-yl]cyclohexanecarboxylate

To a solution of ethyl 4-(6-formyl-5-nitro-indazol-2-yl) cyclohexanecarboxylate (1.50 g, 4.34 mmol) in DCM (80 mL) was added DAST (1.75 g, 10.8 mmol). The mixture was stirred at 0° C. for 2 hrs. On completion, to the mixture was added 2 mL $H_2O$ slowly at 0° C., then the solution was concentrated in vacuo. The crude product was purified by reverse phase HPLC (0.1% TFA condition) to give the title compound (900 mg, 56% yield) as yellow solid. $^1$H NMR (400 MHz, DMSO-$d_6$) δ 8.87 (d, J=5.2 Hz, 2H), 8.07 (s, 1H), 7.73-7.37 (m, 1H), 4.71-4.66 (m, 1H), 4.09 (q, J=7.2 Hz, 2H), 2.24-2.15 (m, 2H), 2.13-1.92 (m, 4H), 1.61 (dq, J=3.1, 12.8 Hz, 2H), 1.20 (t, J=7.2 Hz, 3H); LC-MS (ESI$^+$) m/z 368.1 (M+1)$^+$.

Step 5—Ethyl 4-[5-amino-6-(difluoromethyl)indazol-2-yl]cyclohexanecarboxylate

To a solution of ethyl 4-[6-(difluoromethyl)-5-nitro-indazol-2-yl]cyclohexanecarboxylate (900 mg, 2.45 mmol) in THF (20 mL) was added Pd/C (500 mg, 10 wt %). The mixture was stirred at 15° C. for 2 hrs under H$_2$ (15 psi). On completion, the mixture was filtered through celite and concentrated in vacuo to give the title compound (800 mg, 96% yield) as yellow oil. $^1$H NMR (400 MHz, DMSO-d$_6$) δ 8.07 (s, 1H), 7.65 (s, 1H), 7.23-6.91 (m, 1H), 6.84 (s, 1H), 4.78 (s, 2H), 4.48-4.32 (m, 1H), 3.62 (s, 3H), 2.48-2.40 (m, 1H), 2.17-2.02 (m, 4H), 1.99-1.86 (m, 2H), 1.64-1.50 (m, 2H).

Step 6—Ethyl 4-[6-(difluoromethyl)-5-[[6-(trifluoromethyl)pyridine-2-carbonyl]amino]indazol-2-yl]cyclohexanecarboxylate To a solution of 6-(trifluoromethyl)pyridine-2-carboxylic acid (679 mg, 3.56 mmol) and ethyl 4-[5-amino-6-(difluoromethyl)indazol-2-yl]cyclohexanecarboxylate (800 mg, 2.37 mmol) in DMF (20 mL) was added HATU (1.35 g, 3.56 mmol) and DIPEA (919 mg, 7.11 mmol). The mixture was stirred at 70° C. for 2 hrs. On completion, the mixture was added 0.5 mL water, the residue was purified by prep-HPLC (column: Phenomenex luna C18 250*50 mm*10 um; mobile phase: [water (0.1% TFA)-ACN]; B %: 68%-98%, 9 min) to give the title compound (750 mg, 59% yield) as light yellow solid. $^1$H NMR (400 MHz, DMSO-d$_6$) δ 10.50 (s, 1H), 8.56 (s, 1H), 8.49 (s, 1H), 8.48-8.38 (m, 2H), 8.23 (dd, J=1.2, 7.6 Hz, 1H), 8.00 (s, 1H), 7.43-7.09 (m, 1H), 4.65-4.52 (m, 1H), 4.10 (q, J=7.2 Hz, 2H), 2.26-2.16 (m, 2H), 2.12-1.95 (m, 4H), 1.69-1.56 (m, 2H), 1.21 (t, J=7.2 Hz, 3H); LC-MS (ESI+) m/z 511.1 (M+1)$^+$.

Step 7—Ethyl 4-[6-(difluoromethyl)-5-[[6-(trifluoromethyl)pyridine-2-carbonyl]amino]indazol -2-yl]cyclohexane carboxylic Acid To a solution of ethyl 4-[6-(difluoromethyl)-5-[[6-(trifluoromethyl)pyridine-2-carbonyl]amino]indazol-2-yl]cyclohexanecarboxylate (300 mg, 587 umol) in THF (1 mL) and MeOH (0.1 mL) and H$_2$O (1 mL) was added LiOH·H$_2$O (123 mg, 2.94 mmol). The mixture was stirred at 15° C. for 2 hrs. On completion, the mixture was concentrated in vacuo and M HCl was added to the mixture until the pH=5-6 then the mixture was filtered. The filtered cake was dried in vacuo to give the title compound (250 mg, 88% yield) as yellow solid. LC-MS (ESI+) m/z 483.2 (M+1)$^+$.

Step 8—Isopropoxycarbonyl 4-[6-(difluoromethyl)-5-[[6-(trifluoromethyl)pyridine-2-carbonyl]amino]indazol-2-yl]cyclohexanecarboxylate To a solution of 4-[6-(difluoromethyl)-5-[[6-(trifluoromethyl)pyridine-2-carbonyl]amino]indazol-2-yl]cyclohexanecarboxylic acid (100 mg, 207 umol) in THF (1 mL) was added Et$_3$N (83.9 mg, 829 umol) and isopropyl carbonochloridate (63.5 mg, 518 umol). The mixture was stirred at 0° C. for 2 hrs. On completion, the mixture was filtered and the cake was washed with THF (3×5 mL). The organic phase was concentrated in vacuo to give the title compound (100 mg, 85% yield) as yellow oil. LC-MS (ESI+) m/z 569.0 (M+1)$^+$.

Step 9—N-[6-(difluoromethyl)-2-[4-(hydroxymethyl)cyclohexyl]indazol-5-yl]-6-(trifluoromethyl)pyridine-2-carboxamide To a solution of isopropoxycarbonyl 4-[6-(difluoromethyl)-5-[[6-(trifluoromethyl)pyridine-2-carbonyl]amino]indazol-2-yl]cyclohexanecarboxylate (100 mg, 175 umol) in THF (10 mL) and H$_2$O (1 mL) was added LiBH$_4$ (23.0 mg, 1.06 mmol). The mixture was stirred at 0° C. for 2 hrs. The mixture was added 10 mL NH$_4$Cl and extracted with EA (3×50 mL). The combined organic layers were washed with 50 mL brine, dried over Na$_2$SO$_4$, filtered and concentrated in vacuo to give the title compound (80.0 mg, 97% yield) as yellow solid. LC-MS (ESI+) m/z 469.0 (M+1)$^+$.

Step 10—N-[6-(difluoromethyl)-2-(4-formylcyclohexyl)indazol-5-yl]-6-(trifluoromethyl) pyridine-2-carboxamide To a solution of N-[6-(difluoromethyl)-2-[4-(hydroxymethyl)cyclohexyl]indazol-5-yl]-6-(trifluoro methyl)pyridine-2-carboxamide (80.0 mg, 170 umol) in DCM (10 mL) was added DMP (108 mg, 256 umol). The mixture was stirred at 15° C. for 2 hrs. On completion, the mixture was added 10 mL sat. Na$_2$S$_2$O$_3$ and 10 mL sat. NaHCO$_3$ and extracted with DCM 150 mL (3×50 mL). The combined organic layers were washed with 100 mL brine, dried over Na$_2$SO$_4$, filtered and the organic phase was concentrated in vacuo to give the title compound (80.0 mg, 95% yield) as yellow solid. LC-MS (ESI+) m/z 467.1 (M+1)$^+$.

4-[6-(1-hydroxy-1-methyl-ethyl)-5-[[6-(trifluoromethyl)pyridine-2-carbonyl]amino]indazol-2-yl]cyclohexanecarboxylic Acid (Intermediate AMY)

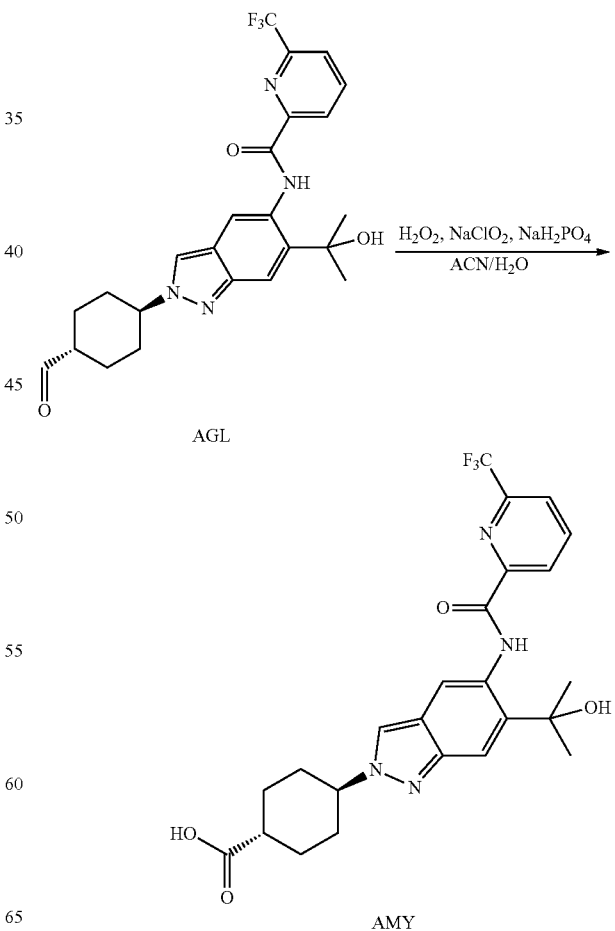

951

To a solution of N-[2-(4-formylcyclohexyl)-6-(1-hydroxy-1-methyl-ethyl)indazol-5-yl]-6-(trifluoro methyl)pyridine-2-carboxamide (200 mg, 421 umol, Intermediate AGL) and NaH$_2$PO$_4$ (252 mg, 2.11 mmol) in ACN (6 mL) was added H$_2$O$_2$ (95.5 mg, 843 umol, 81 uL, 30% solution) dropwise at 0° C. Then sodium chlorite (266 mg, 2.95 mmol) in H$_2$O (3 mL) was added to the mixture at 0° C. The reaction mixture was stirred at 25° C. for 1 hour. On completion, the reaction mixture was diluted with ACN (20 mL) and the reaction was quenched with sat.Na$_2$SO$_3$ (20 mL) at 0° C. The reaction mixture was extracted with ACN (3×10 mL). The combined organic layers were concentrated in vacuo to give the title compound (200 mg, 96% yield) as a yellow solid. LC-MS (ESI+) m/z 491.1 (M+1)$^+$.

3H-[1,2,3]triazolo[4,5-b]pyridin-3-yl pyrazolo[1,5-a]pyrimidine -3-carboxylate (Intermediate BIJ)

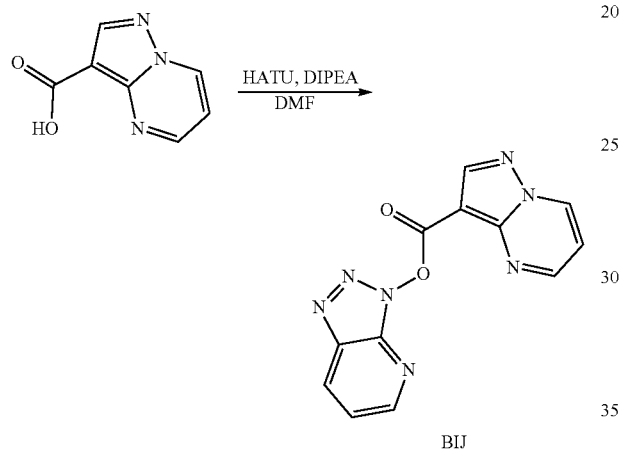

BIJ

To a solution of pyrazolo[1,5-a]pyrimidine-3-carboxylic acid (1 g, 6.13 mmol, CAS #25940-35-6) in DMF (20 mL) was added HATU (2.33 g, 6.13 mmol) and DIPEA (1.58 g, 12.2 mmol). Then the reaction mixture was stirred at 40° C. for 2 hours. On completion, the reaction mixture was filtered. The filter cake was washed with DCM (2×4 mL) and dried in vacuo to give the title compound (1.10 g, 68% yield) as an off-white solid. LC-MS (ESI$^+$) m/z 282.0 (M+H)$^+$.

N-[3-(difluoromethyl)-1-[4-(hydroxymethyl)cyclohexyl]pyrazol-4-yl]pyrazolo[1,5-a] pyrimidine-3-carboxamide (Intermediate BIK)

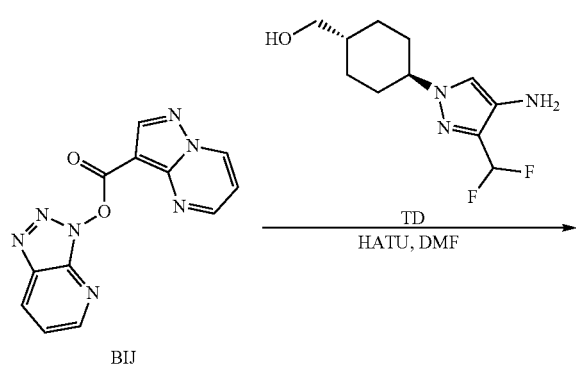

BIJ

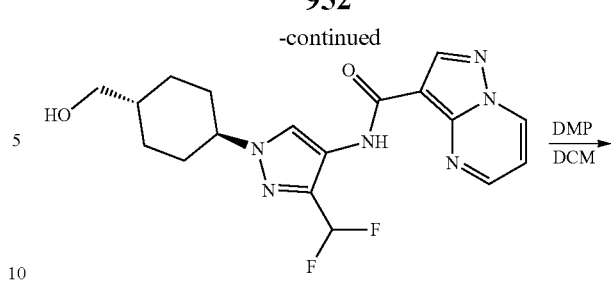

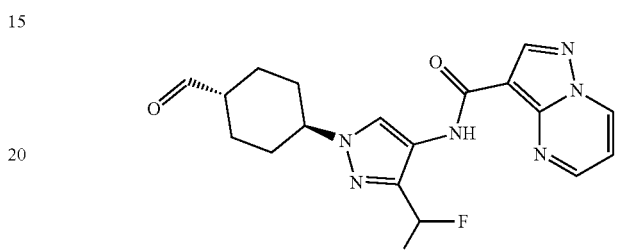

BIK

Step 1—N-[3-(difluoromethyl)-1-[4-(hydroxymethyl)cyclohexyl]pyrazol-4-yl]pyrazolo[1,5-a]pyrimidine-3-carboxamide To a solution of [4-[4-amino-3-(difluoromethyl)pyrazol-1-yl]cyclohexyl]methanol (468 mg, 1.91 mmol, Intermediate TD) in DMF (15 mL) was added triazolo[4,5-b]pyridin-3-yl pyrazolo[1,5-a]pyrimidine-3-carboxylate (536 mg, 1.91 mmol, Intermediate BIJ). The reaction mixture was stirred at 40° C. for 5 hours. On completion, the reaction was quenched with sat. NH$_4$Cl (30 mL) and extracted with DCM (3×100 mL). The combined organic layers were washed with brine (50 mL), dried with anhydrous Na$_2$SO$_4$ and filtered. The filtrate was concentrated in vacuo. The residue was purified by reverse phase (0.1% FA) to give the title compound (400 mg, 53% yield) as a white solid. LC-MS (ESI$^+$) m/z 391.2 (M+H)$^+$.

Step 2—N-[3-(difluoromethyl)-1-[4-(hydroxymethyl)cyclohexyl]pyrazol-4-yl]pyrazolo[1,5-a]pyrimidine-3-carboxamide To a solution of N-[3-(difluoromethyl)-1-[4-(hydroxymethyl)cyclohexyl]pyrazol-4-yl]pyrazolo[1,5-a]pyrimidine-3-carboxamide (200 mg, 512 umol) in DCM (10 mL) was added DMP (325 mg, 768 umol). The reaction mixture was stirred at 25° C. for 1 hour. On completion, the reaction was quenched with sat. NaS$_2$O$_3$ (30 mL) and extracted with DCM (2×30 mL). The combined organic layers were washed with brine (20 mL), dried with anhydrous Na$_2$SO$_4$ and filtered. The filtrate was concentrated in vacuo to give the title compound (198 mg, 509 umol, 99% yield) as a white solid. LC-MS (ESI$^+$) m/z 389.2 (M+H)$^+$.

N-[3-(difluoromethyl)-1-(4-formylcyclohexyl) pyrazol-4-yl] pyrazolo[1,5-a]pyrimidine-3-carboxamide (Intermediate BHI)

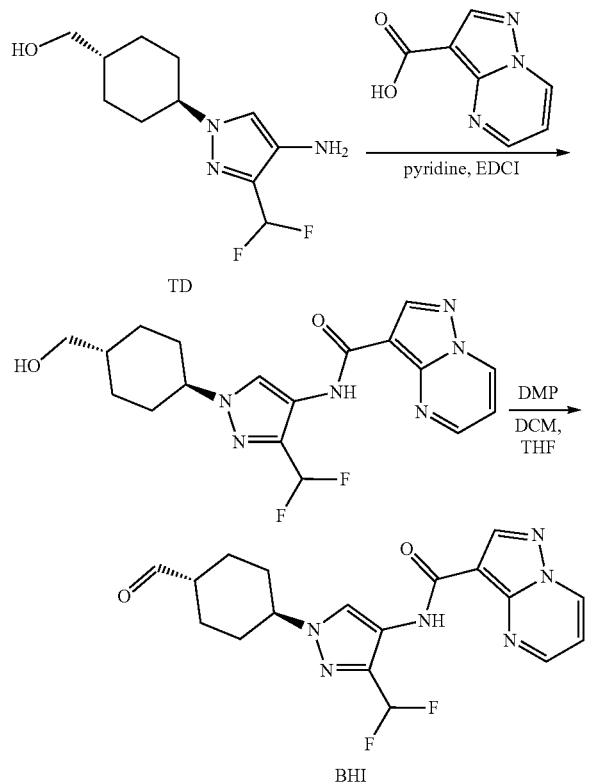

Step 1—N-[3-(difluoromethyl)-1-[4-(hydroxymethyl) cyclohexyl] pyrazol-4-yl]pyrazolo[1,5-a]pyrimidine-3-carboxamide To a mixture of pyrazolo[1,5-a]pyrimidine-3-carboxylic acid (0.13 g, 796 umol, CAS #25940-35-6) and [4-[4-amino-3-(difluoromethyl) pyrazol-1-yl]cyclohexyl]methanol (195 mg, 796 umol, Intermediate TD) in pyridine (2 mL) was added EDCI (183.32 mg, 956.27 umol) in one portion at 25° C. under $N_2$ and the mixture was stirred at 25° C. for 3 hrs. On completion, the mixture was concentrated in vacuo to give the residue. The residue was purified by column chromatography (petroleum ether/ethyl acetate=1/0 to DCM/MeOH=3/1) to give title compound (200 mg, 64% yield) as a yellow solid. $^1$H NMR (400 MHz, CDCl$_3$) δ=10.21 (s, 1H), 8.82 (dd, J=6.8, 1.6 Hz, 1H), 8.77-8.71 (m, 2H), 8.37 (s, 1H), 7.06 (dd, J=6.8, 4.0 Hz, 1H), 6.70-6.99 (m, 1H), 4.12-4.08 (m, 1H), 3.55 (t, J=5.6 Hz, 2H), 2.29-2.22 (m, 2H), 2.06-1.98 (m, 2H), 1.85-1.80 (m, 2H), 1.41-1.38 (m, 1H), 1.27-1.14 (m, 3H).

Step 2—N-[3-(difluoromethyl)-1-(4-formylcyclohexyl) pyrazol-4-yl] pyrazolo[1,5-a]pyrimidine-3-carboxamide To a mixture of N-[3-(difluoromethyl)-1-[4-(hydroxymethyl)cyclohexyl]pyrazol-4-yl]pyrazolo[1,5-a]pyrimidine-3-carboxamide (0.14 g, 358 umol) in DCM (2 mL) and THF (0.5 mL) was added DMP (182 mg, 430 umol) in one portion at 25° C. and the mixture was stirred at 25° C. for 1 h. The reaction mixture was then quenched by addition saturated solution of $Na_2S_2O_3$ (2 mL), and saturated solution of $NaHCO_3$ (10 mL), then extracted with DCM (10 mL×2). The combined organic layer was washed with brine (10 mL×2), dried over $Na_2SO_4$, filtered and concentrated in vacuo to give crude title compound (139 mg, 99% yield) as yellow solid. $^1$H NMR (400 MHz, CDCl$_3$) δ=10.22 (s, 1H), 9.71 (d, J=0.8 Hz, 1H), 8.83 (dd, J=7.2, 1.6 Hz, 1H), 8.76-8.73 (m, 2H), 8.39 (s, 1H), 7.07 (dd, J=6.8, 4.0 Hz, 1H), 6.98-6.69 (m, 1H), 4.15-4.05 (m, 1H), 2.34 (dd, J=12.4, 2.8 Hz, 2H), 2.27-2.20 (m, 2H), 1.96-1.82 (m, 3H), 1.57-1.50 (m, 2H).

N-[3-(difluoromethyl)-1-(3-formylcyclobutyl)pyrazol-4-yl]-5-[(1R,4R)-2-oxa-5-azabicyclo[2.2.1]heptan-5-yl]pyrazolo[1,5-a]pyrimidine-3-carboxamide (Intermediate BWA)

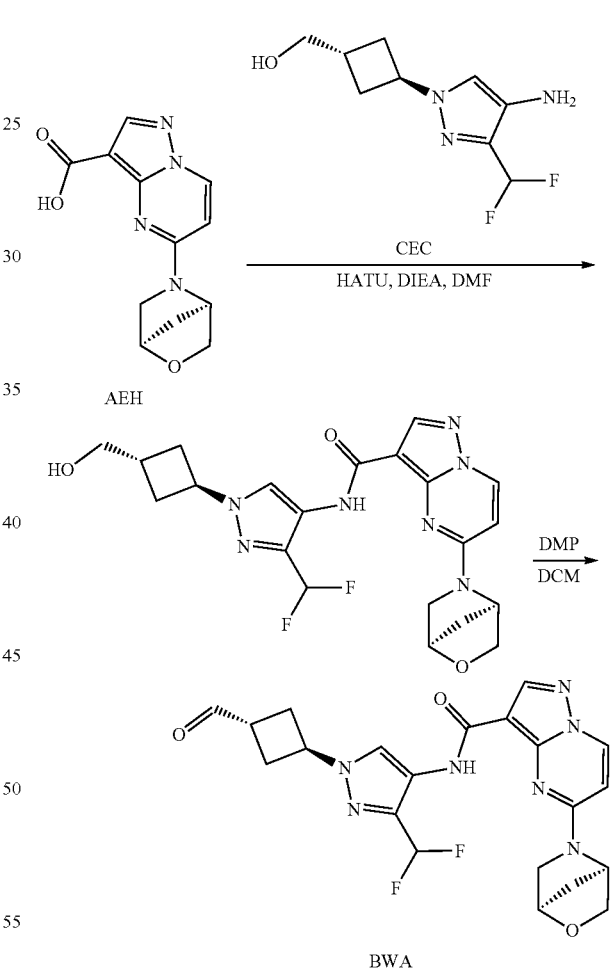

Step 1—Methyl 5-[[4-(benzyloxymethyl)cyclohexanecarbonyl]amino]-2-bromo-4-iodo-benzoate To a solution of 5-[(1R,4R)-2-oxa-5-azabicyclo[2.2.1]heptan-5-yl]pyrazolo[1,5-a]pyrimidine-3-carboxylic acid (335 mg, 1.29 mmol, Intermediate AEH) and DIEA (357 mg, 2.76 mmol) in DMF (4 mL) was added HATU (420 mg, 1.10 mmol). The reaction mixture was stirred at 25° C. for 1 hour. Then [3-[4-amino-3-(difluoromethyl) pyrazol-1-yl] cyclobutyl]methanol (200 mg, 920 umol, Intermediate CEC) was added and the reaction mixture was stirred at 25° C. for 14 hours. On completion, the reaction mixture was poured into saturated aqueous sodium bicarbonate (40 mL). The mixture was extracted with ethyl acetate (30 mL×4). The combined organic layers were dried over sodium sulfate and then concentrated under vacuum to get the residue. The residue was purified by prep-TLC (10% methanol in dichloromethane) to give the title compound (211 mg, 50% yield) as white solid. $^1$H NMR (400 MHz, DMSO-$d_6$) δ 9.50 (d, J=5.2 Hz, 1H), 8.78 (d, J=7.6 Hz, 1H), 8.40 (d, J=4.8 Hz, 1H), 8.26 (d, J=5.6 Hz, 1H), 7.32-6.98 (m, 1H), 6.90-6.37 (m, 1H), 5.35-5.03 (m, 1H), 5.01-4.90 (m, 1H), 4.77-4.78 (m, 1H), 4.72-4.70 (m, 1H), 3.84-3.71 (m, 2H), 3.67-3.57 (m, 2H), 3.56-3.49 (m, 2H), 3.43-3.45 (m, 1H), 2.43-2.34 (m, 1H), 2.30-2.19 (m, 2H), 2.06-1.87 (m, 2H), 1.32-1.20 (m, 1H). LC-MS (ESI$^+$) m/z 460.3 (M+H)$^+$.

Step 2—N-[3-(difluoromethyl)-1-(3-formylcyclobutyl)pyrazol-4-yl]-5-[(1R,4R)-2-oxa-5-azabicyclo[2.2.1]heptan-5-yl]pyrazolo[1,5-a]pyrimidine-3-carboxamide To a solution of N-[3-(difluoromethyl)-1-[3-(hydroxymethyl)cyclobutyl]pyrazol-4-yl]-5-[(1R,4R)-2-oxa-5-azabicyclo[2.2.1]heptan-5-yl]pyrazolo[1,5-a]pyrimidine -3-carboxamide (80.0 mg, 174 umol) in DCM (3 mL) at 0° C. was added DMP (81.2 mg, 191 umol). The reaction mixture was stirred at 20° C. for 1 hour. On completion, the reaction mixture was partitioned between dichloromethane (30 mL) and NaHCO$_3$ (10 mL), then diluted with water (10 mL). The organic phase was separated, washed with H$_2$O (10 mL), dried over anhydrous sodium sulfate, concentrated under reduced pressure to give a residue. The residue was purified by column chromatography (SiO$_2$, Dichloromethane/Methanol=20/1) to give the title compound (79.0 mg, 72% yield) as white solid. $^1$H NMR (400 MHz, CDCl$_3$) δ 9.92 (s, 1H), 9.62 (s, 1H), 8.51-8.41 (m, 2H), 8.37-8.30 (m, 1H), 6.68-6.93 (m, 1H), 6.13 (d, J=7.6 Hz, 1H), 5.46 (s, 1H), 4.87-4.76 (m, 2H), 4.01-3.94 (m, 2H), 3.39-3.27 (m, 1H), 3.17-2.90 (m, 1H), 2.86-2.80 (m, 3H), 2.15-2.07 (m, 3H), 1.98-1.99 (m, 2H). LC-MS (ESI$^+$) m/z 458.3 (M+H)$^+$.

1-[8-[(1R,4R)-2,5-diazabicyclo[2.2.1]heptan-2-yl]-4-isoquinolyl]hexahydropyrimidine -2,4-dione (Intermediate BWB)

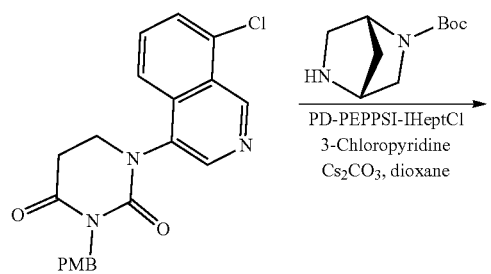

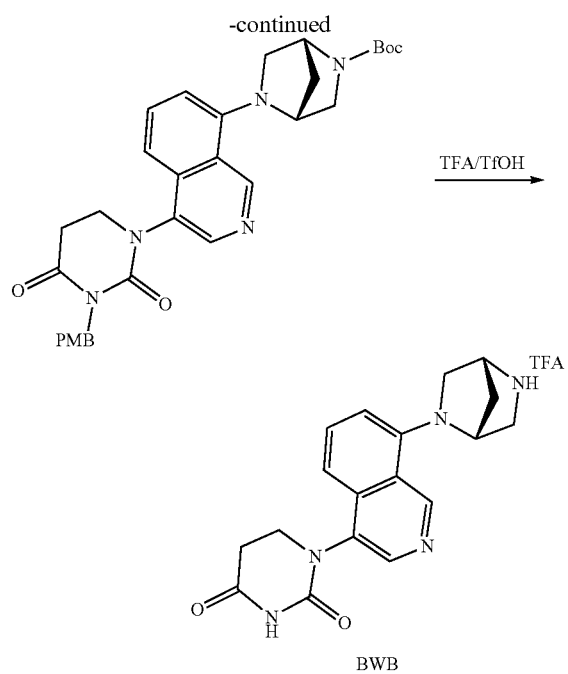

Step 1—Tert-butyl (1R,4R)-5-[4-[3-[(4-methoxyphenyl)methyl]-2,4-dioxo-hexahydropyrimidin-1-yl]-8-isoquinolyl]-2,5-diazabicyclo[2.2.1]heptane-2-carboxylate To a mixture of 1-(8-chloro-4-isoquinolyl)-3-[(4-methoxyphenyl) methyl]hexahydropyrimidine-2,4-dione (500 mg, 1.26 mmol, synthesized via Steps 1-2 of Intermediate BSA) and tert-butyl (1R,4R)-2,5-diazabicyclo[2.2.1] heptane-2-carboxylate (275 mg, 1.39 mmol, CAS #134003-84-2) in dioxane (10 mL) was added PD-PEPPSI-IHeptCl 3-Chloropyridine (122 mg, 126 umol) and Cs$_2$CO$_3$ (1.23 g, 3.79 mmol). The reaction mixture was then stirred at 80° C. for 12 hours. On completion, the residue was diluted with water (30 mL), then the residue was extracted with EA (3×30 mL). The combined organic layer was dried over Na$_2$SO$_4$, filtered and concentrated in vacuo to give a residue. The residue was purified by reverse phase (0.1% FA condition) to give the title compound (236 mg, 33% yield) as yellow solid. $^1$H NMR (400 MHz, DMSO-$d_6$) δ 9.38 (d, J=8.0 Hz, 1H), 8.45 (d, J=6.8 Hz, 1H), 7.62-7.54 (m, 1H), 7.31-7.18 (m, 3H), 7.03 (t, J=8.4 Hz, 1H), 6.90-6.85 (m, 2H), 4.87-4.77 (m, 2H), 4.55 (d, J=6.0 Hz, 1H), 4.50-4.41 (m, 1H), 4.17-4.01 (m, 1H), 3.92 (ddd, J=5.2, 9.6, 12.0 Hz, 1H), 3.87-3.79 (m, 1H), 3.73 (s, 3H), 3.73-3.68 (m, 1H), 3.63-3.53 (m, 1H), 3.45-3.35 (m, 2H), 3.10 (tdd, J=6.0, 9.6, 16.4 Hz, 1H), 3.00-2.91 (m, 1H), 2.05 (s, 1H), 2.00-1.89 (m, 1H), 1.37 (d, J=5.2 Hz, 9H).

Step 2—1-[8-[(1R,4R)-2,5-diazabicyclo[2.2.1]heptan-2-yl]-4-isoquinolyl]hexahydropyrimidine -2,4-dione To a mixture of tert-butyl (1R,4R)-5-[4-[3-[(4-methoxyphenyl)methyl]-2,4-dioxo-hexahydropyrimidin-1-yl]-8-isoquinolyl]-2,5-diazabicyclo[2.2.1]heptane-2-carboxylate (150 mg, 268 umol) in TFA (1 mL) was added TfOH (0.3 mL). The reaction mixture was stirred at 70° C. for 1 hour. On completion, the reaction mixture was concentrated in vacuo to give the title compound (120 mg, 98% yield, TFA). LC-MS (ESI⁺) m/z 338.2 (M+H)⁺.

3-[4-(3,6-Diazabicyclo[3.1.1]heptan-3-yl)-3-methyl-2-oxo-benzimidazol-1-yl]piperidine-2,6-dione (Intermediate BWC)

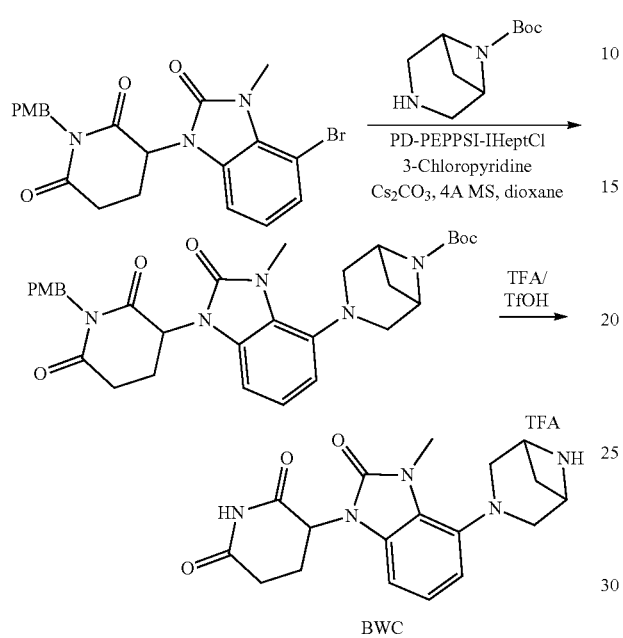

BWC

Step 1—Tert-butyl 3-[1-[1-[(4-methoxyphenyl)methyl]-2,6-dioxo-3-piperidyl]-3-methyl-2-oxo-benzimidazol-4-yl]-3,6-diazabicyclo[3.1.1]heptane-6-carboxylate To a mixture of 3-(4-bromo-3-methyl-2-oxo-benzimidazol-1-yl)-1-[(4-methoxyphenyl)methyl]piperidine-2,6-dione (1.00 g, 2.18 mmol, synthesized via Steps 1-4 of Intermediate HP) and tert-butyl 3,6-diazabicyclo[3.1.1]heptane-6-carboxylate (432 mg, 2.18 mmol, CAS #869494-16-6) in dioxane (15 mL) was added PD-PEPPSI-IHeptCl3-Chloropyridine (200 mg, 2.18 mmol) and Cs₂CO₃ (2.13 g, 6.55 mmol) and 4 Å molecular sieves (200 mg, 2.18 mmol). The reaction mixture was stirred at 100° C. for 12 hrs. On completion, the residue was diluted with water (30 mL), then the residue was extracted with EA (3×100 mL). The combined organic layer was dried over Na₂SO₄, filtered and concentrated in vacuo to give a residue. The residue was purified by column chromatography and the residue was purified by reverse phase (0.1% FA condition) to give the title compound (470 mg, 37% yield) as white solid. ¹H NMR (400 MHz, DMSO-d₆) δ 7.21 (d, J=8.4 Hz, 2H), 7.04-6.99 (m, 1H), 6.96-6.93 (m, 1H), 6.86 (d, J=8.4 Hz, 3H), 5.55-5.49 (m, 1H), 4.85-4.73 (m, 2H), 4.14 (d, J=5.6 Hz, 2H), 3.72 (s, 3H), 3.69-3.62 (m, 1H), 3.56 (s, 3H), 3.52-3.42 (m, 1H), 3.23-2.99 (m, 3H), 2.85-2.65 (m, 2H), 2.46-2.35 (m, 1H), 2.08-2.02 (m, 1H), 1.89 (d, J=8.0 Hz, 1H), 1.45 (s, 9H). LC-MS (ESI⁺) m/z 576.3 (M+H)⁺.

Step 2—3-[4-(3,6-Diazabicyclo[3.1.1]heptan-3-yl)-3-methyl-2-oxo-benzimidazol-1-yl]piperidine-2,6-dione To a solution of tert-butyl 3-[1-[1-[(4-methoxyphenyl)methyl]-2,6-dioxo-3-piperidyl]-3-methyl-2-oxo-benzimidazol-4-yl]-3,6-diazabicyclo[3.1.1]heptane-6-carboxylate (100 mg, 173 umol) in TFA (2 mL) was added TfOH (0.4 mL). The reaction mixture was then stirred at 70° C. for 2 hrs. On completion the reaction mixture was concentrated in vacuo to give the title compound (80.0 mg, 98% yield, TFA) as brown liquid. LC-MS (ESI⁺) m/z 356.2 (M+H)⁺.

Methyl 4-azidocyclohexanecarboxylate (Intermediate BWD)

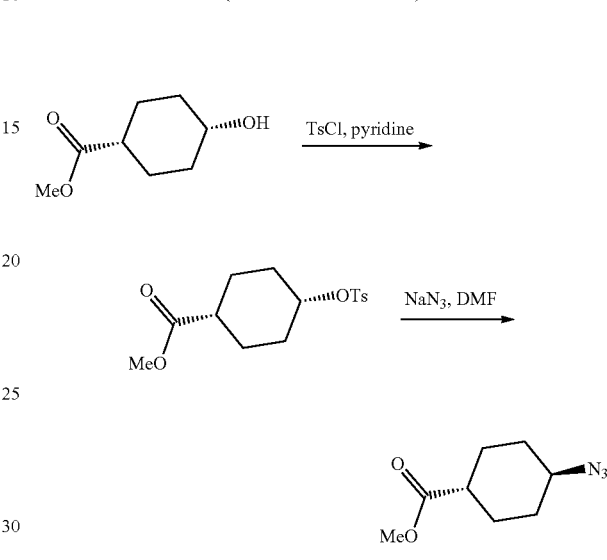

BWD

Step 1—Methyl 4-(p-tolylsulfonyloxy)cyclohexanecarboxylate

To a solution of methyl 4-hydroxycyclohexanecarboxylate (500 mg, 3.16 mmol) in pyridine (2 mL) was added TOSCl (903 mg, 4.74 mmol, CAS #3618-03-9), then the reaction mixture was stirred at 50° C. for 2 hrs. On completion, the reaction mixture was quenched with NaHCO₃ (10 mL), and extracted with EA (2×20 mL). The combined organic phase was washed with brine (2×15 mL), dried with anhydrous Na₂SO₄, filtered and the filtrate was concentrated in vacuo to give the title compound (800 mg, 81% yield) as a colorless oil. ¹H NMR (400 MHz, DMSO-d₆) δ 7.80 (d, J=8.4 Hz, 2H), 7.47 (d, J=8.0 Hz, 2H), 4.70-4.60 (m, 1H), 3.59 (s, 3H), 2.42 (s, 3H), 2.40-2.30 (m, 1H), 1.69-1.51 (m, 8H).

Step 2—Methyl 4-azidocyclohexanecarboxylate

To a solution of methyl 4-(p-tolylsulfonyloxy)cyclohexanecarboxylate (800 mg, 2.56 mmol) in DMF (10 mL) was added NaN₃ (460 mg, 7.08 mmol), then the reaction mixture was stirred at 80° C. for 16 hrs. On completion, the reaction mixture was diluted with water (50 mL) and extracted with EA (2×20 mL). The combined organic layer was washed with brine (2×20 mL), dried over Na₂SO₄, filtered and the filtrate was concentrated to give the title compound (460 mg, 98% yield) as colorless oil. ¹H NMR (400 MHz, DMSO-d₆) δ 3.59 (s, 3H), 3.48-3.36 (m, 1H), 2.37-2.27 (m, 1H), 1.98-1.86 (m, 4H), 1.49-1.25 (m, 4H).

959

2-Chloro-5-ethynyl-N-isopropyl-pyridin-4-amine (Intermediate BWE)

960

1-[5-[1-(4-Formylcyclohexyl)triazol-4-yl]-4-(isopropylamino)-2-pyridyl]pyrrolo[2,3-b]pyridine-5-carbonitrile (Intermediate BWF)

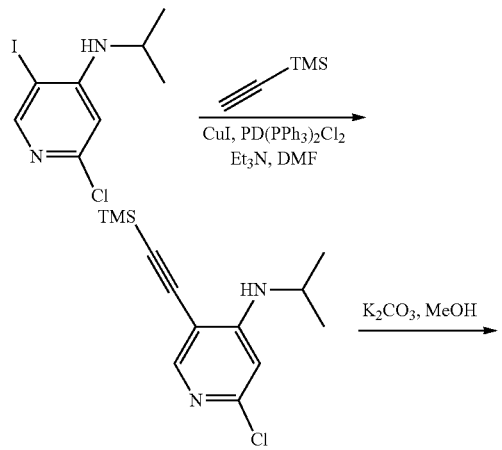

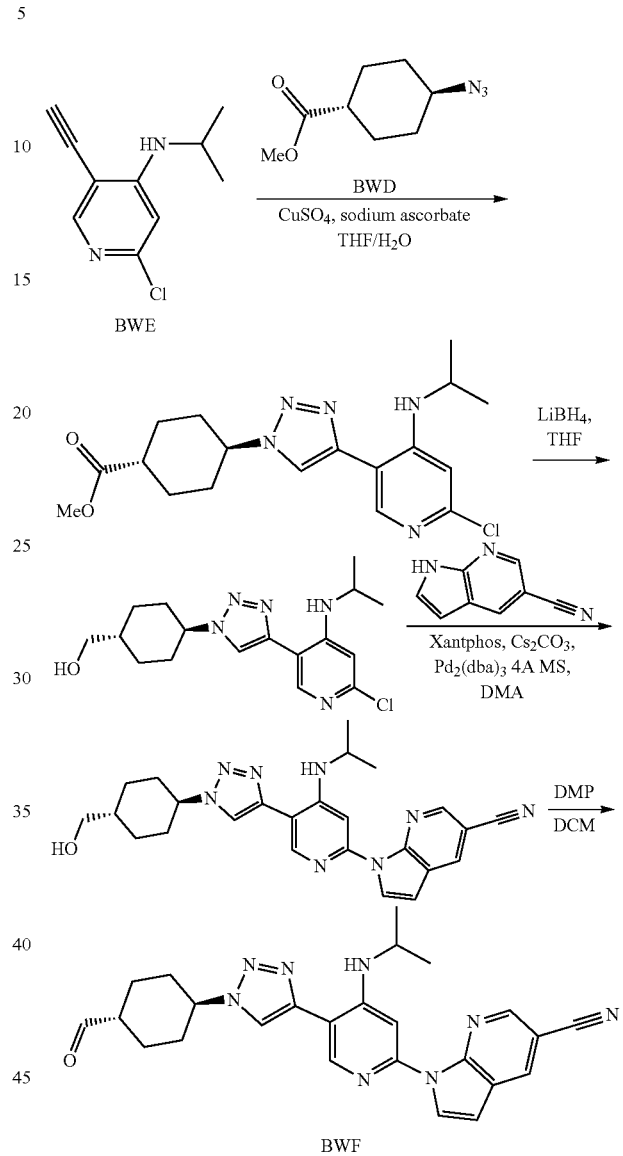

Step 1—2-Chloro-N-isopropyl-5-(2-trimethylsilyl-ethynyl)pyridin-4-amine

To a solution of 2-chloro-5-iodo-N-isopropyl-pyridin-4-amine (2.00 g, 6.74 mmol, CAS #1447227-69-1) and ethynyl(trimethyl)silane (2.65 g, 26.9 mmol, 3.74 mL, CAS #1066-54-2) in DMF (15 mL) was added CuI (128 mg, 674 umol), TEA (3.41 g, 33.7 mmol, 4.69 mL) and Pd(PPh$_3$)$_2$Cl$_2$ (473 mg, 674 umol). Then the reaction mixture was stirred at 80° C. for 16 hrs under N$_2$. On completion, the reaction mixture was diluted with water (50 mL) and extracted with EA (2×30 mL). The combined organic layer was washed with brine (2×20 mL) and dried over Na$_2$SO$_4$, filtered and the filtrate was concentrated in vacuo to give a residue. The residue was purified by reverse phase (0.1% FA condition) and then column chromatography (SiO$_2$, PE:EA=50:1 to PE:EA=5:1, PE:EA=3:1, Rf=0.54) to give the title compound (800 mg, 44% yield) as colorless oil. $^1$H NMR (400 MHz, DMSO-d$_6$) δ 8.00 (s, 1H), 6.70 (s, 1H), 5.44 (d, J=8.0 Hz, 1H), 3.90-3.75 (m, 1H), 1.19 (d, J=6.0 Hz, 6H), 0.26 (s, 9H), LC-MS (ESI$^+$) m/z 267.4 (M+H)$^+$.

Step 2—2-Chloro-5-ethynyl-N-isopropyl-pyridin-4-amine

To a solution of 2-chloro-N-isopropyl-5-(2-trimethylsilylethynyl)pyridin-4-amine (680 mg, 2.55 mmol) in MeOH (5 mL) was added K$_2$CO$_3$ (704 mg, 5.10 mmol), then the reaction mixture was stirred at 25° C. for 2 hrs. On completion, the reaction mixture was filtered and the filtrate was concentrated in vacuo to give the title compound (480 mg, 96% yield) as colorless oil. LC-MS (ESI$^+$) m/z 195.1 (M+H)$^+$.

Step 1—Methyl 4-[4-[6-chloro-4-(isopropylamino)-3-pyridyl]triazol-1-yl]cyclohexanecarboxylate To a solution of 2-chloro-5-ethynyl-N-isopropyl-pyridin-4-amine (430 mg, 2.21 mmol, Intermediate BWE) and methyl 4-azidocyclohexanecarboxylate (367 mg, 2.01 mmol, Intermediate BWD) in H$_2$O (3 mL) and THF (3 mL) was added sodium ascorbate (159 mg, 803 umol) and CuSO$_4$.5H$_2$O (200 mg, 803 umol). Then the reaction mixture was stirred at 25° C. for 5 hrs. On completion, the reaction mixture was filtered and the filtrate was concentrated in vacuo to give a residue. The residue was diluted with water (30 mL) and extracted with EA (2×30 mL). The combined organic layer was washed with brine (2×20 mL) and dried over Na$_2$SO$_4$, filtered and the filtrate was concentrated in vacuo to give a residue. The residue was purified by prep-HPLC (column: YMC Triart C18 250*50 mm*7 um;

mobile phase: [water (0.225% FA)-ACN]; B %: 45%-75%, 10 min) to give the title compound (500 mg, 65% yield) as a white solid. $^1$H NMR (400 MHz, DMSO-$d_6$) δ 8.82 (s, 1H), 8.35 (s, 1H), 8.26 (d, J=7.2 Hz, 1H), 6.71 (s, 1H), 4.64-4.52 (m, 1H), 3.84 (dd, J=6.4, 13.2 Hz, 1H), 3.63 (s, 3H), 2.47-2.39 (m, 1H), 2.26-2.18 (m, 2H), 2.13-2.03 (m, 2H), 1.95-1.80 (m, 2H), 1.68-1.55 (m, 2H), 1.23 (d, J=6.4 Hz, 6H), LC-MS (ESI$^+$) m/z 378.2 (M+H)$^+$.

Step 2—[4-[4-[6-Chloro-4-(isopropylamino)-3-pyridyl]triazol-1-yl]cyclohexyl]methanol To a solution of methyl 4-[4-[6-chloro-4-(isopropylamino)-3-pyridyl]triazol-1-yl] cyclohexanecarboxylate (200 mg, 529 umol) in THF (3 mL) was added LiBH$_4$ (30.0 mg, 1.38 mmol) at 0° C., then the reaction mixture was stirred at 70° C. for 2 hrs. On completion, the reaction mixture was quenched with water (15 mL) and extracted with DCM (2×15 mL). The combined organic layer was washed with brine (2×10 mL) and dried over Na$_2$SO$_4$, filtered and the filtrate was concentrated in vacuo to give the title compound (180 mg, 97% yield) as a white solid. LC-MS (ESI$^+$) m/z 350.2 (M+H)$^+$.

Step 3—1-[5-[1-[4-(Hydroxymethyl)cyclohexyl]triazol-4-yl]-4-(isopropylamino)-2-pyridyl]pyrrolo[2,3-b]pyridine-5-carbonitrile To a solution of [4-[4-[6-chloro-4-(isopropylamino)-3-pyridyl]triazol-1-yl]cyclohexyl]methanol (168 mg, 480 umol) and 1H-pyrrolo[2,3-b]pyridine-5-carbonitrile (103 mg, 720 umol, CAS #517918-95-5) in DMA (4 mL) was added Pd$_2$(dba)$_3$ (43.9 mg, 48.0 umol), 4 Å molecular sieves (50.0 mg), Xantphos (27.7 mg, 48.0 umol) and Cs$_2$CO$_3$ (312 mg, 960 umol) in DMA (4 mL). Then the reaction mixture was stirred at 130° C. for 16 hrs. On completion, the reaction mixture was filtered and the filtrate was concentrated in vacuo to give a residue. The residue was purified by prep-HPLC (column: Phenomenex Luna C18 150*25 mm*10 um; mobile phase: [water (0.225% FA)-ACN]; B %: 35%-%, 10 min) to give the title compound (40 mg, 18% yield) as a yellow solid. LC-MS (ESI$^+$) m/z 457.2 (M+H)$^+$.

Step 4—1-[5-[1-(4-Formylcyclohexyl)triazol-4-yl]-4-(isopropylamino)-2-pyridyl]pyrrolo[2,3-b]pyridine-5-carbonitrile To a solution of 1-[5-[1-[4-(hydroxymethyl)cyclohexyl]triazol-4-yl]-4-(isopropylamino)-2-pyridyl]pyrrolo[2,3-b]pyridine-5-carbonitrile (25.0 mg, 54.7 umol) in DCM (2 mL) was added DMP (30.1 mg, 71.1 umol, 22.0 uL) at 0° C., then the reaction mixture was stirred at 25° C. for 5 hrs. On completion, the reaction mixture was quenched with Na$_2$S$_2$O$_3$ (5 mL) and NaHCO$_3$ (5 mL), then extracted with DCM (2×10 mL). The combined organic phase was washed with NaHCO$_3$ (8 mL) and brine (2×8 mL), dried with anhydrous Na$_2$SO$_4$, filtered and the filtrate was concentrated in vacuo to give the title compound (24 mg, 96% yield) as a yellow solid. LC-MS (ESI$^+$) m/z 455.2 (M+H)$^+$.

[4-[5-amino-6-(trifluoromethoxy)indazol-2-yl]cyclohexyl]methanol (Intermediate BWG)

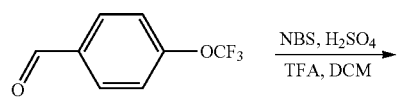

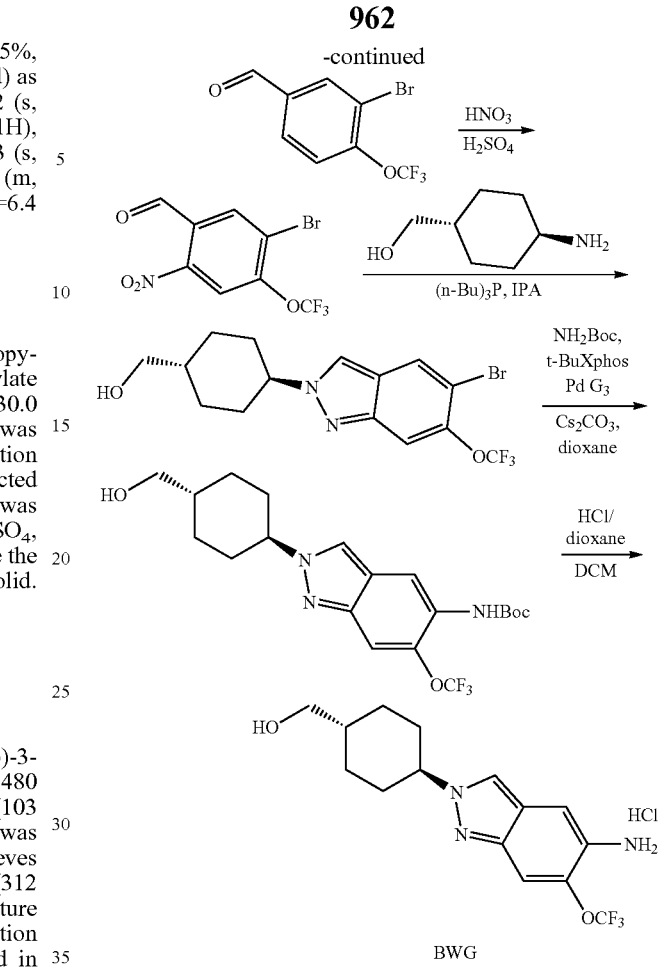

Step 1—3-bromo-4-(trifluoromethoxy)benzaldehyde

To a solution of 4-(trifluoromethoxy) benzaldehyde (30 g, 157 mmol, CAS #659-68-9) in a mixture of TFA (20 mL), H$_2$SO$_4$ (10 mL) and DCM (20 mL) was added NBS (56.1 g, 315 mmol) in portions. The mixture was stirred at 25° C. for 16 hrs. On completion, the residue was diluted with water (150 mL) and extracted with DCM (2×50 mL). The combined organic phase was washed with NaHCO$_3$ (60 mL) and brine (2×50 mL), dried with anhydrous Na$_2$SO$_4$, filtered and the filtrate was concentrated in vacuo to give the title compound (20.7 mg, 49% yield) as yellow solid. $^1$H NMR (400 MHz, CDCl$_3$) δ 10.02 (s, 1H), 7.95 (d, J=8.4 Hz, 2H), 7.39 (s, 1H).

Step 2—5-bromo-2-nitro-4-(trifluoromethoxy)benzaldehyde

To a solution of 3-bromo-4-(trifluoromethoxy)benzaldehyde (20 g, 74.3 mmol) in H2504 (150 mL) was added HNO$_3$ (14.4 g, 153 mmol) at 0° C. The mixture was then stirred at 0° C. for 12 hrs. On completion, the reaction mixture was quenched with water (0.05 mL) and concentrated in vacuo. The residue was purified by column chromatography (SiO$_2$, PE:EA=50:1 to PE:EA=5:1, PE:EA=3:1, P1: Rf=0.3) to give the title compound (5 g, 21% yield) as yellow oil. $^1$H NMR (400 MHz, CDCl$_3$) δ 10.43 (s, 1H), 8.28 (s, 1H), 8.08 (d, J=1.2 Hz, 1H).

Step 3—[4-[5-bromo-6-(trifluoromethoxy)indazol-2-yl]cyclohexyl]methanol

A mixture of 5-bromo-2-nitro-4-(trifluoromethoxy)benzaldehyde (4.5 g, 14.33 mmol) and (4-aminocyclohexyl)methanol (1.85 g, 14.3 mmol, CAS #1467-84-1) in IPA (30 mL) was stirred at 80° C. for 2 hrs under nitrogen atmosphere. Then the reaction mixture was cool to 20° C., followed by addition of tributylphosphane (8.70 g, 42.9 mmol). The mixture was then stirred at 80° C. for 12 hrs under $N_2$ atmosphere. On completion, the residue was concentrated in vacuo and the residue was purified by reverse phase (0.1% FA condition) to give the title compound (3 g, 53% yield) as yellow solid. $^1$H NMR (400 MHz, DMSO-$d_6$) δ 8.51 (s, 1H), 8.21 (s, 1H), 7.80 (s, 1H), 4.48 (ddd, J=4.0, 7.8, 11.2 Hz, 1H), 3.28 (d, J=6.4 Hz, 2H), 2.12 (d, J=9.2 Hz, 2H), 1.99-1.79 (m, 4H), 1.67-1.28 (m, 2H), 1.21-1.05 (m, 2H).

Step 4—Tert-butyl N-[2-[4-(hydroxymethyl)cyclohexyl]-6-(trifluoromethoxy)indazol-5-yl]carbamate A mixture of [4-[5-bromo-6-(trifluoromethoxy)indazol-2-yl]cyclohexyl]methanol (500 mg, 1.27 mmol), $NH_2Boc$ (163 mg, 1.40 mmol), $Cs_2CO_3$ (1.24 g, 3.81 mmol) and [2-(2-aminophenyl) phenyl]-methylsulfonyloxy-palladium; ditertbutyl-[2-(2,4,6-triisopropylphenyl)phenyl]phosphane (101 mg, 127 umol) in dioxane (8 mL) was degassed and purged with $N_2$ for 3 times. Then the mixture was stirred at 80° C. for 24 hrs under $N_2$ atmosphere. On completion, the residue was purified by reverse phase (0.1% FA condition) to give the title compound (350 mg, 58% yield) as yellow solid. $^1$H NMR (400 MHz, $CDCl_3$) δ 8.33 (s, 1H), 7.88 (s, 1H), 7.60 (s, 1H), 6.75 (d, J=1.2 Hz, 1H), 4.36 (t, J=11.6 Hz, 1H), 3.57 (d, J=6.0 Hz, 2H), 2.32 (d, J=10.4 Hz, 2H), 2.10-1.89 (m, 8H), 1.55 (s, 9H); LC-MS (ESI+) m/z 430.3 (M+H)$^+$.

Step 5—[4-[5-amino-6-(trifluoromethoxy)indazol-2-yl]cyclohexyl]methanol

Tert-butyl N-[2-[4-(hydroxymethyl)cyclohexyl]-6-(trifluoromethoxy)indazol-5-yl]carbamate (300 mg, 698 umol) was added into in HCl/dioxane (6 mL). The mixture was then stirred at 25° C. for 16 hrs. On completion, the mixture was concentrated in vacuo to give the title compound (200 mg, 78% yield) as a brown oil. LC-MS (ESI+) m/z 330.3 (M+H)$^+$.

5-cyano-N-(2-((1r,4r)-4-formylcyclohexyl)-6-(trifluoromethoxy)-2H-indazol-5-yl) nicotinamide (Intermediate BWH)

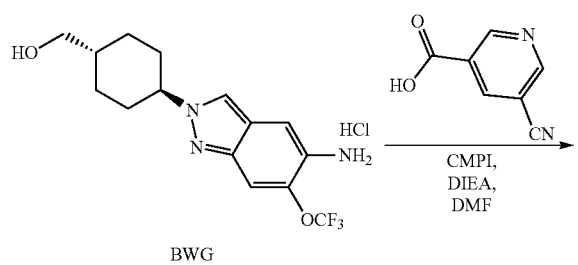

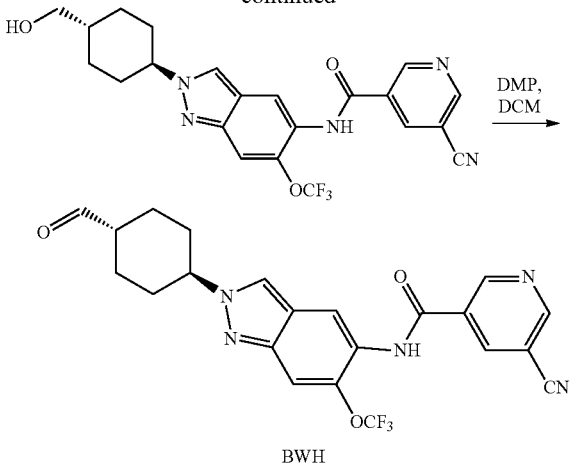

Step 1—5-cyano-N-[2-[4-(hydroxymethyl)cyclohexyl]-6-(trifluoromethoxy)indazol-5-yl]pyridine-3-carboxamide To a solution of 5-cyanopyridine-3-carboxylic acid (32.8 mg, 221 umol, CAS #887579-62-6), CMPI (56.5 mg, 221 umol) and DIEA (31.8 mg, 246 umol) in DMF (2 mL) was added [4-[5-amino-6-(trifluoromethoxy)indazol-2-yl]cyclohexyl]methanol (90 mg, 246 umol, Intermediate BWG) and DIEA (31.8 mg, 246 umol) in DMF (2 mL). The mixture was then stirred at 25° C. for 1 hr. On completion, the reaction was diluted with EA (35 mL) and $H_2O$ (20 mL), then extracted with EA (15 mL×2). The combined organic layers were washed with $H_2O$ (15 mL×2), dried over $Na_2SO_4$, filtered and concentrated under reduced pressure. The residue was purified by column chromatography ($SiO_2$, PE:EA=5:1 to PE:EA=1:1, PE:EA=1:1, Pl:Rf=0.3) to give the title compound (100 mg, 88% yield) as a white solid. LC-MS (ESI+) m/z 460.2 (M+H)$^+$.

Step 2—5-cyano-N-(2-((1r,4r)-4-formylcyclohexyl)-6-(trifluoromethoxy)-2H-indazol-5-yl) nicotinamide To a solution of 5-cyano-N-[2-[4-(hydroxymethyl)cyclohexyl]-6-(trifluoromethoxy)indazol-5-yl]pyridine-3-carboxamide (100 mg, 217 umol) in DCM (3 mL) was added DMP (110 mg, 261 umol). The mixture was then stirred at 25° C. for 1 hr. On completion, the reaction mixture was quenched by addition of aqueous $Na_2S_2SO_3$ (8 mL) and $NaHCO_3$ (8 mL) at 25° C., and then extracted with DCM 30 mL (15 mL×2). The combined organic layers were dried over anhydrous $Na_2SO_4$ and concentrated in vacuo to give the title compound (80 mg, 80% yield) as a brown solid. LC-MS (ESI+) m/z 457.9 (M+H)$^+$.

1-(7-Piperazin-1-yl-4-isoquinolyl)hexahydropyrimidine-2,4-dione (Intermediate BWL)

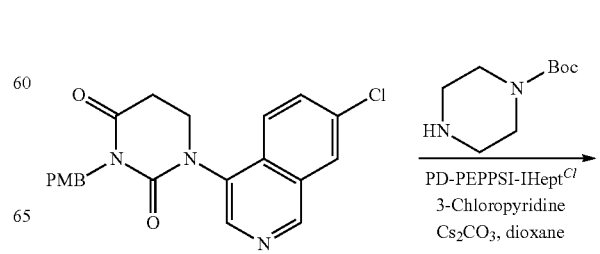

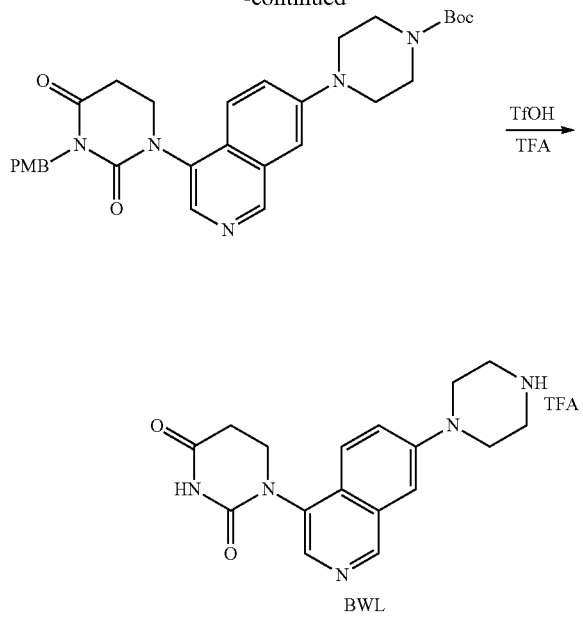

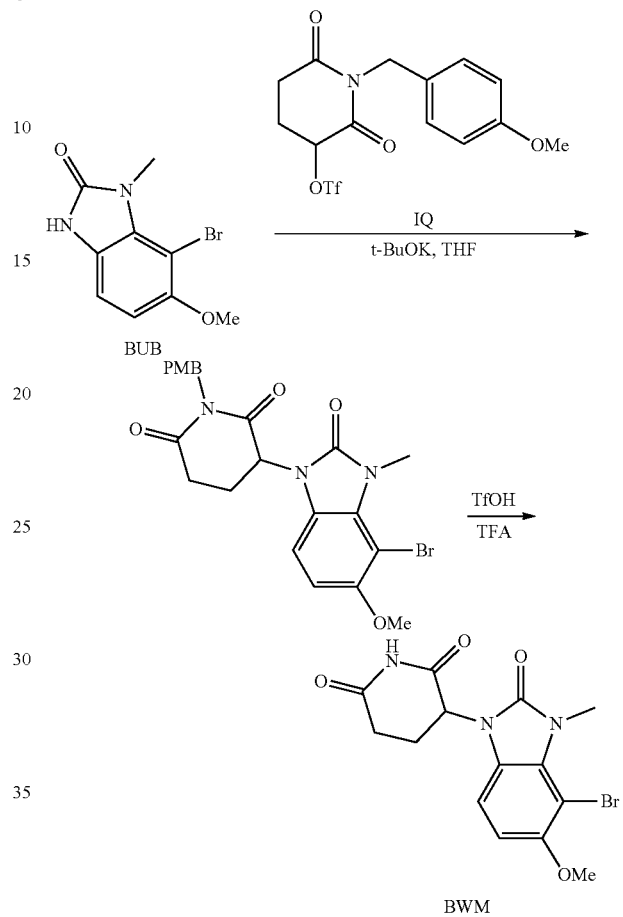

966
3-(4-Bromo-5-methoxy-3-methyl-2-oxo-benzimidazol-1-yl)piperidine-2,6-dione (Intermediate BWM)

Step 1—Tert-butyl 4-[4-[3-[(4-methoxyphenyl)methyl]-2,4-dioxo-hexahydropyrimidin-1-yl]-7-isoquinolyl]piperazine-1-carboxylate To a solution of 1-(7-chloro-4-isoquinolyl)-3-[(4-methoxyphenyl)methyl]hexahydropyrimidine-2,4-dione (500 mg, 1.26 mmol, synthesized via Steps 1-2 of Intermediate BRX), and tert-butyl piperazine-1-carboxylate (258 mg, 1.39 mmol, CAS #143238-38-4) in dioxane (8 mL) was added Cs$_2$CO$_3$ (823 mg, 2.53 mmol) and Pd-PEPPSI-IHeptCl 3-Chloropyridine (122 mg, 126 umol). Then the reaction mixture was stirred at 80° C. for 12 hrs under N$_2$. On completion, the reaction mixture was filtered and the filtrate was concentrated in vacuo to give a residue. The residue was purified by reverse phase (0.1% FA condition) to give the title compound (450 mg, 65% yield) as yellow solid. $^1$H NMR (400 MHz, DMSO-d$_6$) δ 9.09 (s, 1H), 8.30 (s, 1H), 7.77 (d, J=9.2 Hz, 1H), 7.65 (dd, J=2.4, 9.2 Hz, 1H), 7.45 (d, J=2.4 Hz, 1H), 7.25 (d, J=8.8 Hz, 2H), 6.88 (d, J=8.4 Hz, 2H), 4.83 (s, 2H), 3.95-3.84 (m, 1H), 3.81-3.68 (m, 4H), 3.64-3.46 (m, 4H), 3.31-3.26 (m, 2H), 3.18-3.05 (m, 1H), 3.02-2.89 (m, 1H), 2.65-2.52 (m, 2H), 1.44 (s, 9H); LC-MS (ESI$^+$) m/z 546.2 (M+H)$^+$.

Step 2—1-(7-Piperazin-1-yl-4-isoquinolyl)hexahydropyrimidine-2,4-dione

To a solution of tert-butyl 4-[4-[3-[(4-methoxyphenyl)methyl]-2,4-dioxo-hexahydropyrimidin-1-yl]-7-isoquinolyl]piperazine-1-carboxylate (80.0 mg, 146 umol) in TfOH (170 mg, 1.13 mmol) was added TFA (770 mg, 6.75 mmol). Then the reaction was stirred at 70° C. for 2 hrs. On completion, the reaction mixture was concentrated in vacuo to give the title compound (60.0 mg, 93% yield, TFA) as yellow oil. LC-MS (ESI$^+$) m/z 326.1 (M+H)$^+$.

Step 1—3-(4-Bromo-5-methoxy-3-methyl-2-oxo-benzimidazol-1-yl)-1-[(4-methoxyphenyl) methyl] piperidine-2,6-dione A solution of 4-bromo-5-methoxy-3-methyl-1H-benzimidazol-2-one (518 mg, 2.02 mmol, Intermediate BUB) in THF (5 mL) was stirred at −10° C., then the t-BuOK (407 mg, 3.63 mmol) was added and the mixture was stirred at −10° C. for 1 hr. Then the solution of [1-[(4-methoxyphenyl)methyl]-2,6-dioxo-3-piperidyl] trifluoromethanesulfonate (1.00 g, 2.62 mmol, Intermediate IQ) in THF (4 mL) was added dropwise into the above solution. The mixture was stirred at −10° C. for 5 hrs. On completion, the mixture was quenched by NH$_4$Cl (10 mL), diluted with H$_2$O (40 mL), then extracted with EA (2×50 mL). Then the mixture was washed with brine (2×50 mL), dried with anhydrous Na$_2$SO$_4$ and concentrated in vacuo. The crude product was purified by reversed phase (0.1% FA) to give the title compound (740 mg, 75% yield) as green solid. $^1$H NMR (400 MHz, DMSO-d$_6$) δ 7.20 (d, J=8.8 Hz, 2H), 7.00 (d, J=8.4 Hz, 1H), 6.87-6.84 (m, 2H), 6.77 (d, J=8.8 Hz, 1H), 5.52 (dd, J=5.6, 13.2 Hz, 1H), 4.85-4.72 (m, 2H), 3.82 (s, 3H), 3.72 (s, 3H), 3.64 (s, 3H), 3.10-2.98 (m, 1H), 2.85-2.77 (m, 1H), 2.77-2.69 (m, 1H), 2.10-2.01 (m, 1H). LC-MS (ESI$^+$) m/z 489.9 (M+H)$^+$.

Step 2—3-(4-Bromo-5-methoxy-3-methyl-2-oxo-benzimidazol-1-yl) piperidine-2,6-dione To a solution of 3-(4-bromo-5-methoxy-3-methyl-2-oxo-benzimidazol-1-yl)-1-[(4-methoxyphenyl) methyl] piperidine-2,6-dione (800 mg, 1.64 mmol) in mixture solvent of TfOH (200 uL) and TFA (1.6 mL). The mixture was then stirred at 70° C. for 2 hrs. On completion, the mixture was concentrated in vacuo, then dissolved in ACN (3 mL) and adjusted mixture pH=5-6 with TEA. The residue was purified by reversed phase (0.1% FA condition) to give the title compound (218 mg, 36% yield) as white solid. $^1$H NMR (400 MHz, DMSO-$d_6$) δ 11.11 (s, 1H), 7.10 (d, J=2.8 Hz, 1H), 6.82 (d, J=8.4 Hz, 1H), 5.37 (dd, J=5.2, 12.4 Hz, 1H), 3.82 (s, 3H), 3.64 (s, 3H), 2.90-2.83 (m, 1H), 2.73-2.62 (m, 2H), 2.05-1.99 (m, 1H). LC-MS (ESI$^+$) m/z 370.2 (M+H)$^+$.

Tert-butyl 4-prop-2-ynoxypiperidine-1-carboxylate (Intermediate BWO)

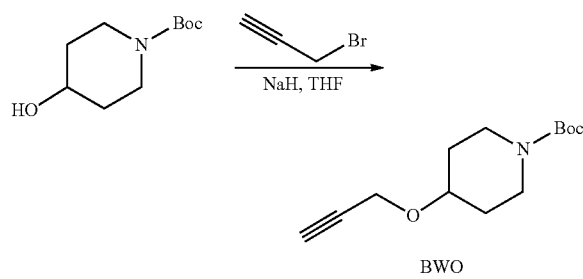

To a solution of tert-butyl 4-hydroxypiperidine-1-carboxylate (2.00 g, 9.94 mmol, CAS #109384-19-2) in anhydrous THF (10 mL) was cooled to 0° C., and subsequently NaH (477 mg, 11.9 mmol, 60% dispersion in mineral oil) was added. The reaction mixture was stirred at 0° C. for 0.5 hr. Then, 3-bromoprop-1-yne (1.18 g, 9.94 mmol, 856 uL) was added. The resulting reaction mixture was stirred at 25° C. for 12 hrs. On completed, the reaction mixture was quenched with water (1 mL), then diluted with ethyl acetate (100 mL). The organic layers were washed with brine (20 mL), dried over anhydrous sodium sulfate, filtered and the filtrate was concentrated in vacuo. The residue was purified by column chromatography to give the title compound (2.38 g, 100% yield) as yellow oil. $^1$H NMR (400 MHz, CDCl$_3$) δ 4.22 (d, J=2.4 Hz, 2H), 3.84-3.75 (m, 2H), 3.73-3.70 (m, 1H), 3.15-3.09 (m, 2H), 2.43 (t, J=2.4 Hz, 1H), 1.93-1.82 (m, 2H), 1.61-1.50 (m, 2H), 1.47 (s, 9H).

3-[3,5-Dimethyl-2-oxo-4-(4-piperidyl)benzimidazol-1-yl]-1-methyl-piperidine-2,6-dione (Intermediate BWQ)

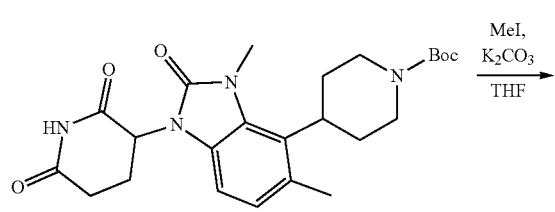

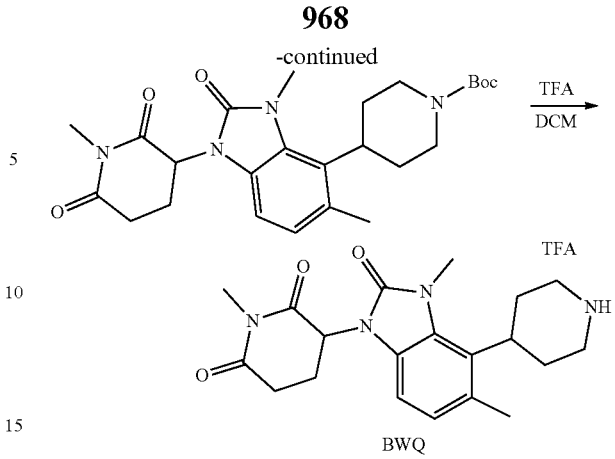

Step 1—Tert-butyl 4-[3,5-dimethyl-1-(1-methyl-2,6-dioxo-3-piperidyl)-2-oxo-benzimidazol-4-yl] piperidine-1-carboxylate To a mixture of tert-butyl 4-[1-(2,6-dioxo-3-piperidyl)-3,5-dimethyl-2-oxo-benzimidazol-4-yl] piperidine-1-carboxylate (100 mg, 219 umol, synthesized via Step 1 of Intermediate BQM) in THF (1 mL) was added K$_2$CO$_3$ (60.5 mg, 438 umol) and MeI (46.6 mg, 328 umol). The reaction mixture was then stirred at 25° C. for 1 hour. On completion, the residue was diluted with water (20 mL) and extracted with EA (2×20 mL). The combined organic layer was dried over Na$_2$SO$_4$, filtered and concentrated in vacuo to give a residue. The residue was purified by reverse phase (0.1% FA condition) to give the title compound (68.0 mg, 65% yield) as white solid. $^1$H NMR (400 MHz, DMSO-$d_6$) δ 6.91-6.86 (m, 1H), 6.84-6.78 (m, 1H), 5.44-5.36 (m, 1H), 4.15-4.00 (m, 2H), 3.62 (s, 3H), 3.57 (s, 1H), 3.05-3.01 (m, 3H), 2.95-2.86 (m, 2H), 2.79-2.67 (m, 2H), 2.39 (s, 2H), 2.28 (s, 1H), 2.13-1.92 (m, 3H), 1.83-1.52 (m, 3H), 1.43 (s, 9H). LC-MS (ESI$^+$) m/z 493.2 (M+Na)$^+$.

Step 2—3-[3,5-Dimethyl-2-oxo-4-(4-piperidyl)benzimidazol-1-yl]-1-methyl-piperidine-2,6-dione To a mixture of tert-butyl 4-[3,5-dimethyl-1-(1-methyl-2,6-dioxo-3-piperidyl)-2-oxo-benzimidazol-4-yl]piperidine-1-carboxylate (68.0 mg, 144 umol) in DCM (2 mL) was added TFA (16.4 mg, 144 umol). The reaction mixture was then stirred at 25° C. for 1 hour. On completion, the reaction mixture was concentrated in vacuo to give the title compound (70.0 mg, 99% yield, TFA) as brown oil. LC-MS (ESI$^+$) m/z 371.1 (M+H)$^+$.

3-[3-Methyl-4-[(3R)-3-methylpiperazin-1-yl]-2-oxo-benzimidazol-1-yl]piperidine-2,6-dione (Intermediate BWR)

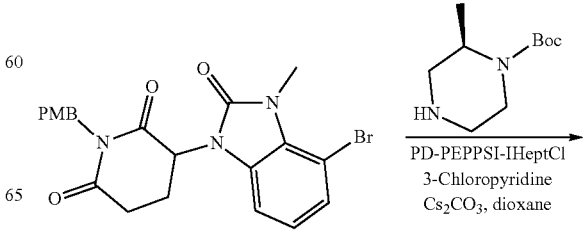

-continued

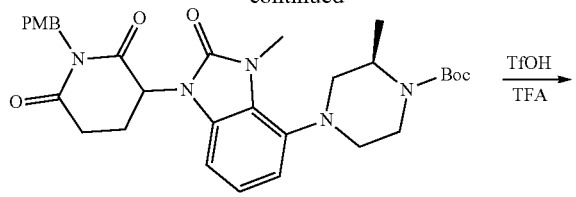

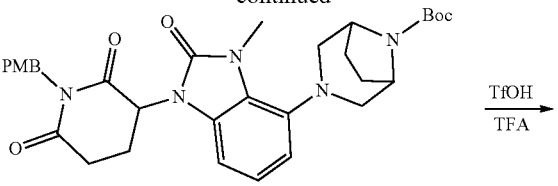

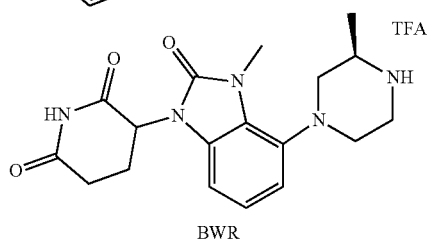

BWR

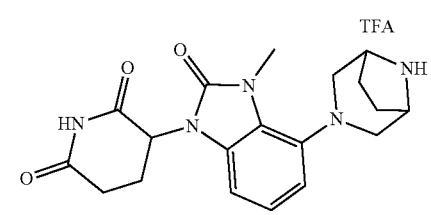

BWS

Step 1—Tert-butyl (2R)-4-[1-[1-[(4-methoxyphenyl)methyl]-2,6-dioxo-3-piperidyl]-3-methyl-2-oxo-benzimidazol-4-yl]-2-methyl-piperazine-1-carboxylate A mixture of 3-(4-bromo-3-methyl-2-oxo-benzimidazol-1-yl)-1-[(4-methoxyphenyl)methyl]piperidine-2,6-dione (1.00 g, 2.18 mmol, synthesized via Steps 1-4 of Intermediate HP), tert-butyl (2R)-2-methylpiperazine-1-carboxylate (524 mg, 2.62 mmol, CAS #170033-47-3), Pd-PEPPSI-IHeptCl 3-Chloropyridine (212 mg, 218 umol), and Cs$_2$CO$_3$ (1.42 g, 4.36 mmol) in dioxane (15 mL) was degassed and purged with N$_2$ three times. Then the mixture was stirred at 100° C. for 16 hrs under N$_2$ atmosphere. The residue was purified by column chromatography (SiO$_2$, PE/EA=10:1 to 2:1) to give the title compound (785 mg, 65% yield) as yellow solid. $^1$H NMR (400 MHz, CDCl$_3$) δ 7.39-7.33 (m, 2H), 6.90-6.85 (m, 2H), 6.84-6.79 (m, 2H), 6.31 (s, 1H), 5.22 (dd, J=5.2, 12.8 Hz, 1H), 5.00-4.91 (m, 2H), 4.55-4.27 (m, 1H), 4.04-3.84 (m, 1H), 3.79 (d, J=5.2 Hz, 6H), 3.41-3.23 (m, 1H), 3.17-2.95 (m, 3H), 2.95-2.75 (m, 2H), 2.74-2.54 (m, 2H), 2.22-2.10 (m, 1H), 1.50 (s, 9H), 1.34 (d, J=6.8 Hz, 3H).

Step 2—3-[3-Methyl-4-[(3R)-3-methylpiperazin-1-yl]-2-oxo-benzimidazol-1-yl]piperidine-2,6-dione To a solution of tert-butyl (2R)-4-[1-[1-[(4-methoxyphenyl)methyl]-2,6-dioxo-3-piperidyl]-3-methyl-2-oxo-benzimidazol-4-yl]-2-methyl-piperazine-1-carboxylate (150 mg, 259 umol) in TFA (3 mL) was added TfOH (0.6 mL). The mixture was then stirred at 70° C. for 3 hrs. On completion, the mixture was concentrated in vacuo to give the title compound (110 mg, 90% yield) as black brown oil. LC-MS (ESI+) m/z 358.3 (M+H)$^+$.

3-[4-(3,8-Diazabicyclo[3.2.1]octan-3-yl)-3-methyl-2-oxo-benzimidazol-1-yl]piperidine -2,6-dione (Intermediate BWS)

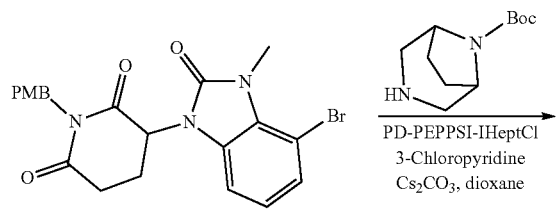

Step 1—Tert-butyl 3-[1-[1-[(4-methoxyphenyl)methyl]-2,6-dioxo-3-piperidyl]-3-methyl-2-oxo-benzimidazol-4-yl]-3,8-diazabicyclo[3.2.1]octane-8-carboxylate To a solution of 3-(4-bromo-3-methyl-2-oxo-benzimidazol-1-yl)-1-[(4-methoxyphenyl)methyl]piperidine-2,6-dione (1.00 g, 2.18 mmol, synthesized via Steps 1-4 of Intermediate HP) and tert-butyl 3,8-diazabicyclo[3.2.1]octane-8-carboxylate (462 mg, 2.18 mmol, CAS #149771-44-8) in dioxane (10 mL) was added PD-PEPPSI-IHeptCl 3-Chloropyridine (200 mg, 10.9 umol) and Cs$_2$CO$_3$ (1.42 g, 4.36 mmol). Then the reaction mixture was stirred at 100° C. for 16 hrs under N$_2$. On completion, the reaction mixture was filtered and the filtrate was concentrated in vacuo to give a residue. The residue was purified by reverse phase (0.1% FA condition) to give the title compound (700 mg, 54% yield) as a white solid. $^1$H NMR (400 MHz, DMSO-d$_6$) δ 7.21 (d, J=8.4 Hz, 2H), 7.03-6.92 (m, 2H), 6.90-6.80 (m, 3H), 5.51 (dd, J=5.6, 13.2 Hz, 1H), 4.90-4.70 (m, 2H), 4.19 (s, 2H), 3.72 (s, 3H), 3.71 (s, 3H), 3.11-3.01 (m, 1H), 3.00-2.86 (m, 4H), 2.85-2.77 (m, 1H), 2.76-2.65 (m, 1H), 2.06-1.96 (m, 3H), 1.93-1.83 (m, 2H), 1.45 (s, 9H); LCMS (ESI$^+$) m/z 590.4 (M+H)$^+$.

Step 2—3-[4-(3,8-Diazabicyclo[3.2.1]octan-3-yl)-3-methyl-2-oxo-benzimidazol-1-yl]piperidine -2,6-dione To a mixture of tert-butyl 3-[1-[1-[(4-methoxyphenyl)methyl]-2,6-dioxo-3-piperidyl]-3-methyl-2-oxo-benzimidazol-4-yl]-3,8-diazabicyclo[3.2.1]octane-8-carboxylate (153 mg, 260 umol) in TFA (1.5 mL) was added TfOH (510 mg, 3.40 mmol, 300 uL). Then the reaction mixture was stirred at 70° C. for 3 hrs. On completion, the reaction mixture was concentrated in vacuo to give title compound (120 mg, 95% yield, TFA) as brown oil. LCMS (ESI$^+$) m/z 370.2 (M+H)$^+$.

3-[4-[(1S,4S)-2,5-Diazabicyclo[2.2.1]heptan-2-yl]-3-methyl-2-oxo-benzimidazol-1-yl]piperidine-2,6-dione (Intermediate BWT)

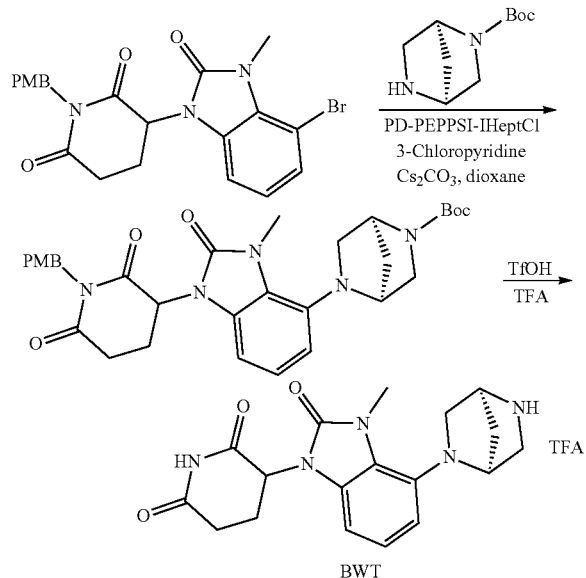

BWT

Step 1—Tert-butyl (1S,4S)-5-[1-[1-[(4-methoxyphenyl)methyl]-2,6-dioxo-3-piperidyl]-3-methyl-2-oxo-benzimidazol-4-yl]-2,5-diazabicyclo[2.2.1]heptane-2-carboxylate To a solution of 3-(4-bromo-3-methyl-2-oxo-benzimidazol-1-yl)-1-[(4-methoxyphenyl)methyl] piperidine-2,6-dione (1.00 g, 2.18 mmol, synthesized via Steps 1-4 of Intermediate HP) in dioxane (15 mL) was added PD-PEPPSI-IHeptCl 3-Chloropyridine (212 mg, 218 umol), Cs$_2$CO$_3$ (1.42 g, 4.36 mmol) and tert-butyl (1S,4S)-2,5-diazabicyclo[2.2.1]heptane-2-carboxylate (519 mg, 2.62 mmol, CAS #113451-59-5). The mixture was degassed and purged with N$_2$ three times, and then the mixture was stirred at 100° C. for 8 hrs under N$_2$ atmosphere. On completion, the mixture was filtered and the cake was washed with ethyl acetate. Then the mixture was concentrated to give a residue, and the residue was purified by column chromatography (SiO$_2$, Petroleum ether/Ethyl acetate=2:1 to 1:2). The combined organic layers were concentrated under reduced pressure to give the title compound (581 mg, 46% yield) as light pink solid. $^1$H NMR (400 MHz, CDCl$_3$) δ 7.30 (dd, J=1.6, 8.4 Hz, 2H), 6.83-6.72 (m, 4H), 6.20 (d, J=6.8 Hz, 1H), 5.19-5.08 (m, 1H), 4.95-4.84 (m, 2H), 4.56-4.37 (m, 1H), 3.76 (s, 1H), 3.73 (d, J=2.0 Hz, 3H), 3.66 (s, 3H), 3.56-3.46 (m, 1H), 3.45-3.35 (m, 1H), 3.23-3.07 (m, 2H), 2.97-2.89 (m, 1H), 2.82-2.69 (m, 1H), 2.62-2.47 (m, 1H), 2.13-2.00 (m, 2H), 1.92-1.84 (m, 1H), 1.45 (d, J=9.6 Hz, 9H); LC-MS (ESI$^+$) m/z 576.3 (M+H)$^+$.

Step 2—3-[4-[(1S,4S)-2,5-Diazabicyclo[2.2.1]heptan-2-yl]-3-methyl-2-oxo-benzimidazol-1-yl]piperidine-2,6-dione To a solution of tert-butyl (1S,4S)-5-[1-[1-[(4-methoxyphenyl)methyl]-2,6-dioxo-3-piperidyl]-3-methyl-2-oxo-benzimidazol-4-yl]-2,5-diazabicyclo[2.2.1]heptane-2-carboxylate (280 mg, 486 umol) in TFA (4 mL) was added TfOH (109 mg, 729 umol). Then the mixture was stirred at 70° C. for 8 hrs. On completion, the mixture was concentrated to give the title compound (164 mg, 94% yield, TFA salt) as black oil. LC-MS (ESI$^+$) m/z 356.4 (M+H)$^+$.

Step 3—Tert-butyl (1S,4S)-5-[1-(2,6-dioxo-3-piperidyl)-3-methyl-2-oxo-benzimidazol-4-yl]-2,5-diazabicyclo[2.2.1]heptane-2-carboxylate To a solution of 3-[4-[(1S,4S)-2,5-diazabicyclo[2.2.1]heptan-2-yl]-3-methyl-2-oxo-benzimidazol-1-yl]piperidine-2,6-dione (160 mg, 450 umol) in ACN (5 mL) was added Boc$_2$O (147 mg, 675 umol) and TEA (45.5 mg, 450 umol). Then the mixture was stirred at 25° C. for 3 hrs. On completion, the mixture was diluted with H$_2$O (8 mL) and extracted with ethyl acetate (8 mL×2). The combined organic layers were filtered and concentrated under reduced pressure to give a residue to give the title compound (190 mg, 92% yield) as brown solid. LC-MS (ESI$^+$) m/z 456.0 (M+H)$^+$.

Step 4—3-[4-[(1S,4S)-2,5-Diazabicyclo[2.2.1]heptan-2-yl]-3-methyl-2-oxo-benzimidazol-1-yl]piperidine-2,6-dione To a solution of tert-butyl (1S,4S)-5-[1-(2,6-dioxo-3-piperidyl)-3-methyl-2-oxo-benzimidazol-4-yl]-2,5-diazabicyclo[2.2.1]heptane-2-carboxylate (190 mg, 417 umol) in DCM (3 mL) was added TFA (770 mg, 6.75 mmol). The mixture was stirred at 25° C. for 0.5 hr. On completion, the mixture was concentrated to give the title compound (140 mg, 94% yield, TFA) as black oil. LC-MS (ESI$^+$) m/z 356.2 (M+H)$^+$.

N-[2-(4-formylcyclohexyl)thiazolo[4,5-c]pyridin-6-yl]-6-(trifluoromethyl)pyridine-2-carboxamide (Intermediate BWU)

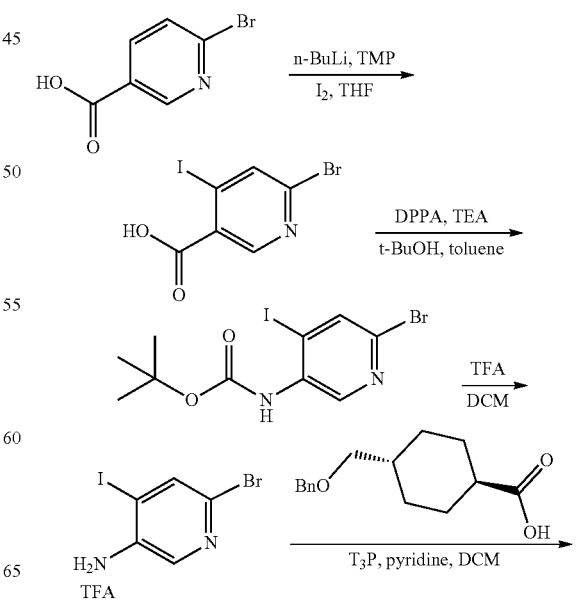

973

-continued

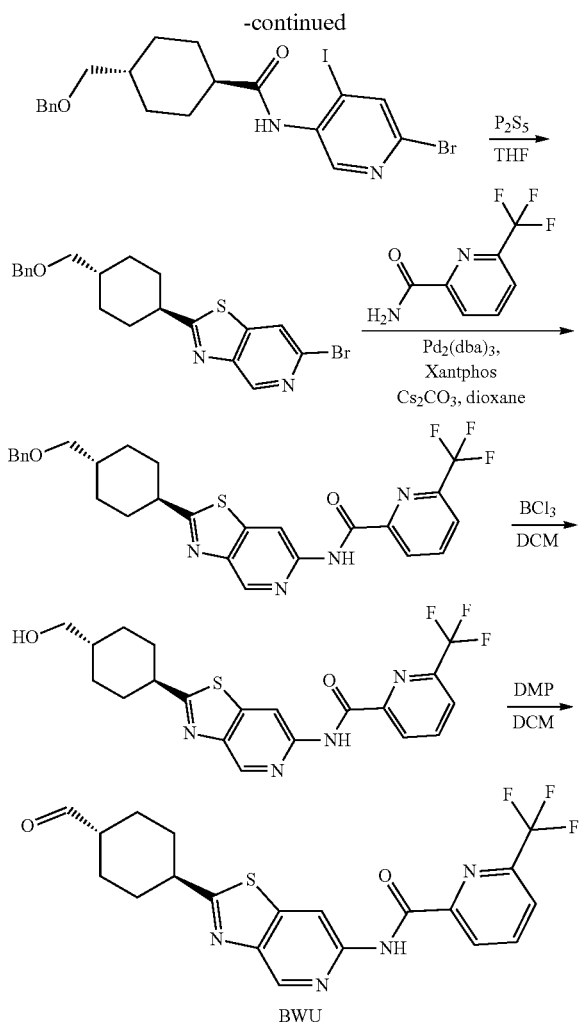

BWU

Step 1—6-Bromo-4-iodo-pyridine-3-carboxylic Acid

A dry three neck-round bottom flask (250 mL) containing TMP (10.4 g, 74.2 mmol) and THF (50 mL) under $N_2$ was cooled to below −55° C. Then, n-BuLi (2.5 M, 29.7 mL) was added dropwise to the cooled solution. The suspension was stirred for 30 mins at below −40° C. Then 6-bromopyridine-3-carboxylic acid (5 g, 24.7 mmol, CAS #6311-35-9) was added quickly in four portions and the suspension was stirred at −20° C. for 2 hrs, over which time the reaction turned from orange to brown. The reaction mixture was then cooled to below −50° C. and quickly transferred into a pre-cooled solution of 12 (18.8 g, 74.2 mmol) in THF (50 mL) under $N_2$. The resulting mixture was allowed to warm to 25° C. and stirred for 12 hrs. On completion, the reaction mixture was quenched with $NH_4Cl$ (100 mL), then extracted with DCM (2×100 mL). The aqueous phase was separated and the pH adjust to 2 by the addition of 1N HCl, then extracted with EA (2×100 mL). The organic phase was dried over $Na_2SO_4$, filtered and the filtrate was concentrated in vacuo to give the title compound (3.2 g, 39% yield) as yellow solid. $^1$H NMR (400 MHz, DMSO-$d_6$) δ 14.13-13.56 (m, 1H), 8.61 (s, 1H), 8.35 (s, 1H).

974

Step 2—Tert-butyl N-(6-bromo-4-iodo-3-pyridyl)carbamate

To a solution of 6-bromo-4-iodo-pyridine-3-carboxylic acid (3 g, 9.15 mmol) and TEA (2.78 g, 27.4 mmol, 3.82 mL) in t-BuOH (15 mL) and toluene (15 mL) was added DPPA (3.78 g, 13.7 mmol, 2.97 mL). Then the reaction mixture was stirred at 110° C. for 3 hrs. On completion, the reaction mixture was diluted with $H_2O$ (30 mL), then extracted with EA (2×50 mL). The organic phase was combined dried with $Na_2SO_4$, and then filtered and the filtrate was concentrated in vacuo to give a residue. The residue was purified by reverse phase (0.1% FA condition) to give the title compound (2.75 g, 75% yield) as yellow solid. $^1$H NMR (400 MHz, CDCl$_3$) δ 8.95 (s, 1H), 7.87 (s, 1H), 6.65 (s, 1H), 1.55 (s, 9H); LC-MS (ESI$^+$) m/z 398.8 (M+H)$^+$.

Step 3—6-Bromo-4-iodo-pyridin-3-amine

To a solution of tert-butyl N-(6-bromo-4-iodo-3-pyridyl)carbamate (2.75 g, 6.89 mmol) in DCM (30 mL) was added TFA (9.63 g, 84.4 mmol, 6.25 mL). Then the reaction mixture was stirred at 25° C. for 30 mins. On completion, the reaction mixture was concentrated in vacuo to give a residue. The residue was diluted with a saturated solution of $NaHCO_3$ to adjust pH=9, then extracted with EA (2×50 mL). The combined organic layer was dried over $Na_2SO_4$, filtered and the filtrate was concentrated in vacuo to give the title compound (2 g, 97% yield) as yellow solid. $^1$H NMR (400 MHz, CDCl$_3$) δ 7.80 (s, 1H), 7.73 (s, 1H), 4.50-3.68 (s, 2H); LC-MS (ESI$^+$) m/z 298.8 (M+H)$^+$.

Step 4—4-(Benzyloxymethyl)-N-(6-bromo-4-iodo-3-pyridyl)cyclohexanecarboxamide To a solution of 4-(benzyloxymethyl)cyclohexanecarboxylic acid (1.20 g, 4.83 mmol, synthesized via Steps 1-3 of Intermediate BAU) and 6-bromo-4-iodo-pyridin-3-amine (1.37 g, 4.58 mmol) in DCM (20 mL) was added pyridine (1.11 mL, 13.7 mmol) and $T_3P$ (5.82 g, 9.15 mmol). Then the reaction mixture was stirred at 25° C. for 12 hrs. On completion, the reaction mixture was diluted with $H_2O$ (30 mL) and extracted with DCM mL (2×40 mL). The combined organic layers were washed with brine (20 mL), dried over $Na_2SO_4$, filtered and concentrated in vacuo to give the title compound (2.3 g, 94% yield) as white solid. LC-MS (ESI$^+$) m/z 530.8 (M+H)$^+$.

Step 5—2-[4-(Benzyloxymethyl)cyclohexyl]-6-bromo-thiazolo[4,5-c]pyridine

To a solution of 4-(benzyloxymethyl)-N-(6-bromo-4-iodo-3-pyridyl)cyclohexanecarboxamide (1.7 g, 3.21 mmol) in THF (20 mL) was added $P_2S_5$ (785 mg, 3.53 mmol, 375 uL), then the reaction mixture was stirred at 25° C. for 16 hrs. On completion, the reaction mixture was diluted with $H_2O$ (50 mL), then extracted with DCM (2×80 mL). The organic phase was washed with brine (50 mL), then dried over $Na_2SO_4$, filtered and the filtrate was concentrated in vacuo to give a residue. The residue was purified by reverse phase (0.1% FA condition) to give the title compound (800 mg, 59% yield) as light yellow solid. $^1$H NMR (400 MHz, DMSO-$d_6$) δ 9.00 (s, 1H), 8.45 (s, 1H), 7.41-7.21 (m, 5H), 4.46 (s, 2H), 3.30 (d, J=6.4 Hz, 2H), 3.19-3.06 (m, 1H), 2.18

(d, J=11.6 Hz, 2H), 1.89 (d, J=10.8 Hz, 2H), 1.72-1.65 (m, 1H), 1.64-1.53 (m, 2H), 1.22-1.10 (m, 2H); LC-MS (ESI+) m/z 417.4 (M+H)+.

Step 6—N-[2-[4-(benzyloxymethyl)cyclohexyl]thiazolo[4,5-c]pyridin-6-yl]-6-(trifluoromethyl) pyridine-2-carboxamide To a solution of 2-[4-(benzyloxymethyl)cyclohexyl]-6-bromo-thiazolo[4,5-c]pyridine (750 mg, 1.80 mmol), 6-(trifluoromethyl)pyridine-2-carboxamide (375 mg, 1.98 mmol, CAS #22245-84-7) in dioxane (10 mL) was added $Cs_2CO_3$ (1.17 g, 3.59 mmol), $Pd_2(dba)_3$ (164 mg, 179 umol) and Xantphos (103 mg, 179 umol). Then the reaction mixture was stirred at 80° C. for 12 hrs under $N_2$. On completion, the mixture was filtered and the filtrate was concentrated in vacuo to give a residue. The residue was purified by reverse phase (0.1% FA condition) to give the title compound (460 mg, 48% yield) as yellow solid. $^1$H NMR (400 MHz, DMSO-$d_6$) δ 10.39 (s, 1H), 9.01 (s, 1H), 8.92 (s, 1H), 8.51-8.44 (m, 1H), 8.44-8.37 (m, 1H), 8.24 (d, J=7.6 Hz, 1H), 7.40-7.27 (m, 5H), 4.51-4.41 (m, 2H), 3.30 (d, J=6.4 Hz, 2H), 3.16-3.04 (m, 1H), 2.19 (d, J=10.8 Hz, 2H), 1.90 (d, J=10.8 Hz, 2H), 1.73-1.54 (m, 3H), 1.23-1.11 (m, 2H).

Step 7—N-[2-[4-(hydroxymethyl)cyclohexyl]thiazolo[4,5-c]pyridin-6-yl]-6-(trifluoromethyl)pyridine-2-carboxamide To a solution of N-[2-[4-(benzyloxymethyl)cyclohexyl]thiazolo[4,5-c]pyridin-6-yl]-6-(trifluoromethyl) pyridine-2-carboxamide (400 mg, 759 umol) in DCM (10 mL) was added $BCl_3$ (1 M, 2.28 mL) dropwise at 0° C., then the reaction mixture was stirred at 0° C. for 1 hr. On completion, the reaction mixture was diluted with $H_2O$ (20 mL) and extracted with DCM mL (2×30 mL). The combined organic layers were washed with brine (20 mL), dried over $Na_2SO_4$, filtered and concentrated in vacuo to give a residue. The residue was purified by reverse phase (0.1% FA condition) to give the title compound (280 mg, 84% yield) as a white solid. $^1$H NMR (400 MHz, DMSO-$d_6$) δ 10.39 (s, 1H), 9.01 (d, J=0.4 Hz, 1H), 8.92 (d, J=0.8 Hz, 1H), 8.51-8.45 (m, 1H), 8.45-8.38 (m, 1H), 8.24 (dd, J=0.8, 7.6 Hz, 1H), 4.46 (t, J=5.2 Hz, 1H), 3.27 (t, J=5.6 Hz, 2H), 3.15-3.03 (m, 1H), 2.26-2.13 (m, 2H), 1.94-1.82 (m, 2H), 1.65-1.52 (m, 2H), 1.50-1.36 (m, 1H), 1.16-1.04 (m, 2H).

Step 8—N-[2-(4-formylcyclohexyl)thiazolo[4,5-c]pyridin-6-yl]-6-(trifluoromethyl)pyridine-2-carboxamide To a solution of N-[2-[4-(hydroxymethyl)cyclohexyl]thiazolo[4,5-c]pyridin-6-yl]-6-(trifluoromethyl) pyridine-2-carboxamide (55.0 mg, 126 umol) in DCM (1 mL) was added DMP (64.1 mg, 151 umol), then the reaction mixture was stirred at 25° C. for 1 hr. On completion, the reaction mixture was quenched with $Na_2S_2O_3$ (15 mL) and extracted with DCM (2×30 mL). The combined organic phase was washed with $NaHCO_3$ and brine (2×15 mL), dried with anhydrous $Na_2SO_4$, filtered and concentrated in vacuo to give the title compound (50.0 mg, 91% yield) as yellow solid. LC-MS (ESI+) m/z 435.0 (M+H)+.

Tert-butyl 4-(4,4,5,5-tetramethyl-1,3,2-dioxaborolan-2-yl)-2-(trifluoromethyl)-3,6-dihydro -2H-pyridine-1-carboxylate (Intermediate BWV)

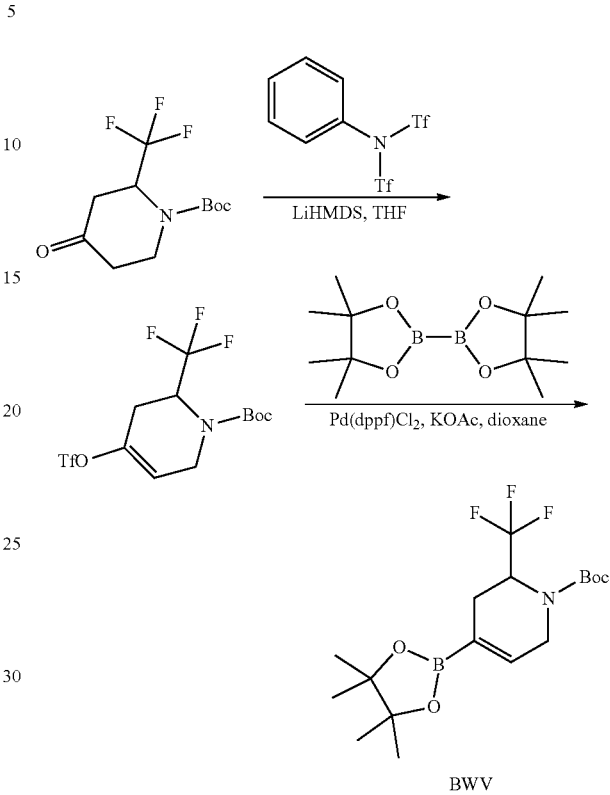

BWV

Step 1—Tert-butyl 2-(trifluoromethyl)-4-(trifluoromethylsulfonyloxy)-3,6-dihydro-2H-pyridine-1-carboxylate To a solution of tert-butyl 4-oxo-2-(trifluoromethyl)piperidine-1-carboxylate (3.50 g, 13.1 mmol, CAS #1245648-32-1) in THF (30 mL), LiHMDS (1 M, 19.6 mL) was dropwise added into the above solution at −70° C. and stirred for 2 hrs. Then the solution of 1,1,1-trifluoro-N-phenyl-N-(trifluoromethylsulfonyl) methanesulfonamide (5.61 g, 15.7 mmol, CAS #37595-74-7) in THF (50 mL) was dropwise added into above solution at −70° C., then the mixture was stirred at -70-25° C. for 16 hrs. On completion, the mixture was quenched with saturation solution of $NH_4Cl$ (100 mL), then extracted with EA (3×100 mL), washed with brine (3×100 mL), dried with anhydrous $Na_2SO_4$, filtered and concentrated in vacuo. The residue was purified by column chromatography to give the title compound (3.10 g, 59% yield) as colorless oil. $^1$H NMR (400 MHz, $CDCl_3$) δ 5.83 (s, 1H), 5.43-5.07 (m, 1H), 4.56-4.21 (m, 1H), 3.35-3.07 (m, 1H), 2.60 (s, 1H), 2.38-2.23 (m, 1H), 1.50 (s, 9H).

Step 2—Tert-butyl 4-(4,4,5,5-tetramethyl-1,3,2-dioxaborolan-2-yl)-2-(trifluoromethyl)-3,6-dihydro -2H-pyridine-1-carboxylate To a solution of tert-butyl 2-(trifluoromethyl)-4-(trifluoromethylsulfonyloxy)-3,6-dihydro-2H-pyridine -1-carboxylate (1.25 g, 3.13 mmol) and 4,4,5,5-tetramethyl-2-(4,4,5,5-tetramethyl-1,3,2-dioxaborolan-2-yl)-1,3,2-dioxaborolane (794 mg, 3.13 mmol, CAS #73183-34-3) in dioxane (15 mL) was added Pd(dppf)Cl₂ (229 mg, 313 umol) and KOAc (921 mg, 9.39 mmol). The mixture was degassed and purged with N₂ three times and stirred at N₂ atmosphere at 65° C. for 40 hrs. On completion, the mixture was filtered and concentrated in vacuo. The residue was purified by column chromatography to give the title compound (0.90 g, 76% yield) as colorless oil. ¹H NMR (400 MHz, DMSO-d₆) δ 6.31 (s, 1H), 5.25-5.00 (m, 1H), 4.20-3.96 (m, 1H), 2.96-2.64 (m, 1H), 2.19-2.03 (m, 2H), 1.41 (s, 9H), 1.22 (s, 12H).

3-[3-Methyl-2-oxo-4-[2-(trifluoromethyl)-4-piperidyl]benzimidazol-1-yl]piperidine -2,6-dione (Intermediate BWW)

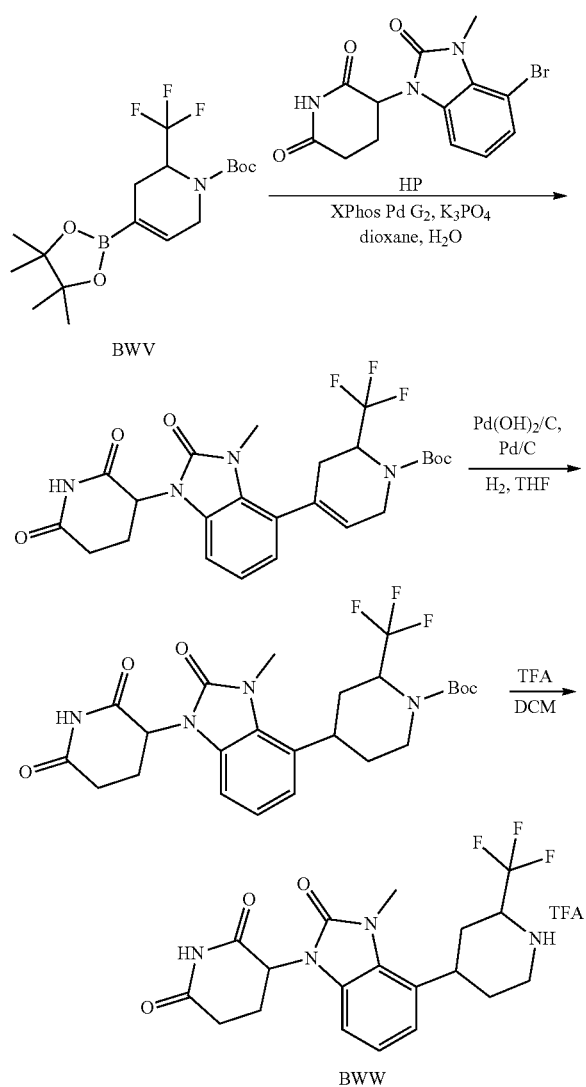

Step 1—Tert-butyl 4-[1-(2,6-dioxo-3-piperidyl)-3-methyl-2-oxo-benzimidazol-4-yl]-2-(trifluoromethyl)-3,6-dihydro-2H-pyridine-1-carboxylate To a solution of 3-(4-bromo-3-methyl-2-oxo-benzimidazol-1-yl)piperidine-2,6-dione (1.11 g, 3.28 mmol, Intermediate HP) and tert-butyl 4-(4,4,5,5-tetramethyl-1,3,2-dioxaborolan-2-yl)-2-(trifluoromethyl)-3,6-dihydro-2H-pyridine-1-carboxylate (1.61 g, 4.27 mmol, Intermediate BWV) in the mixture solvent of dioxane (20 mL) and H₂O (200 uL) was added XPHOS-PD-G2 (258 mg, 328 umol), and K₃PO₄ (2.09 g, 9.85 mmol). The mixture was degassed and purged with N₂ three times, and then stirred at for under N₂ atmosphere at 80° C. for 24 hr. On completion, the mixture was filtered and concentrated in vacuo. The crude product was purified by prep-HPLC (reverse phase: 0.1% FA) to give the title compound (670 mg, 40% yield) as brown solid. ¹H NMR (400 MHz, DMSO-d₆) δ 11.11 (s, 1H), 7.13-7.08 (m, 1H), 7.04 (t, J=7.6 Hz, 1H), 6.87 (d, J=7.6 Hz, 1H), 5.78 (s, 1H), 5.40 (dd, J=5.2, 12.8 Hz, 1H), 4.37-4.12 (m, 1H), 3.28 (s, 3H), 3.22 (s, 1H), 3.16-3.02 (m, 1H), 2.95-2.84 (m, 1H), 2.78-2.68 (m, 1H), 2.68-2.61 (m, 1H), 2.44-2.37 (m, 1H), 2.37-2.31 (m, 1H), 2.05-1.97 (m, 1H), 1.46 (s, 9H).

Step 2—Tert-butyl 4-[1-(2,6-dioxo-3-piperidyl)-3-methyl-2-oxo-benzimidazol-4-yl]-2-(trifluoromethyl) piperidine-1-carboxylate To a solution of tert-butyl 4-[1-(2,6-dioxo-3-piperidyl)-3-methyl-2-oxo-benzimidazol-4-yl]-2-(trifluoromethyl)-3,6-dihydro-2H-pyridine-1-carboxylate (470 mg, 924 umol) in THF (8 mL) was added Pd/C (250 mg, 924 umol, 10 wt %) and Pd(OH)₂/C (250 mg, 356 umol, 20 wt %) under Ar atmosphere. The mixture was then place under H₂ atmosphere (50 psi) and stirred at 50° C. for 48 hrs. On completion, the mixture was filtered and concentrated in vacuo to give the title compound (230 mg, 48% yield) as white solid. ¹H NMR (400 MHz, DMSO-d₆) δ 11.09 (s, 1H), 7.13-7.09 (m, 1H), 7.08-7.04 (m, 1H), 7.02-6.98 (m, 1H), 5.41-5.36 (m, 1H), 4.95-4.83 (m, 1H), 3.95-3.85 (m, 1H), 3.57-3.53 (m, 3H), 3.26-3.18 (m, 1H), 2.87-2.82 (m, 1H), 2.72-2.62 (m, 2H), 2.24-2.17 (m, 1H), 2.16-2.09 (m, 1H), 2.08-1.94 (m, 3H), 1.65-1.55 (m, 1H), 1.45 (s, 9H). LC-MS (ESI⁺) m/z 511.2 (M+H)⁺.

Step 3—3-[3-Methyl-2-oxo-4-[2-(trifluoromethyl)-4-piperidyl]benzimidazol-1-yl]piperidine-2,6-dione To a solution of tert-butyl 4-[1-(2,6-dioxo-3-piperidyl)-3-methyl-2-oxo-benzimidazol-4-yl]-2-(trifluoromethyl) piperidine-1-carboxylate (200 mg, 391 umol) in DCM (4 mL) was added TFA (616 mg, 5.40 mmol). The mixture was then stirred at 25° C. for 2 hrs. On completion, the mixture was concentrated in vacuo, then dissolved with DMF (1 mL), and the solution adjusted pH=6-7 with TEA. The crude product was purified by prep-HPLC (column: 3 Phenomenex Luna C 18 75*30 mm*3 um; mobile phase: [water (10 mM NH₄HCO₃)-ACN]; B %: 15%-45%, 10 min) to give the title compound (75.0 mg, 46% yield) as white solid. ¹H NMR (400 MHz, DMSO-d₆) δ 11.09 (s, 1H), 7.06-7.01 (m, 2H), 7.01-6.97 (m, 1H), 5.37 (dd, J=5.2, 12.4 Hz, 1H), 3.59 (s, 3H), 3.52-3.48 (m, 1H), 3.10 (d, J=12.4 Hz, 1H), 2.97-2.82 (m, 2H), 2.80-2.62 (m, 3H), 2.59-2.52 (m, 1H), 2.03-1.96 (m, 1H), 1.91 (d, J=11.6 Hz, 1H), 1.79-1.73 (m, 1H), 1.67-1.54 (m, 2H). LC-MS (ESI⁺) m/z 411.2 (M+H)⁺.

979

3-[4-chloro-3-methyl-2-oxo-5-(4-piperidyl)benzimidazol-1-yl]piperidine-2,6-dione (Intermediate BWX)

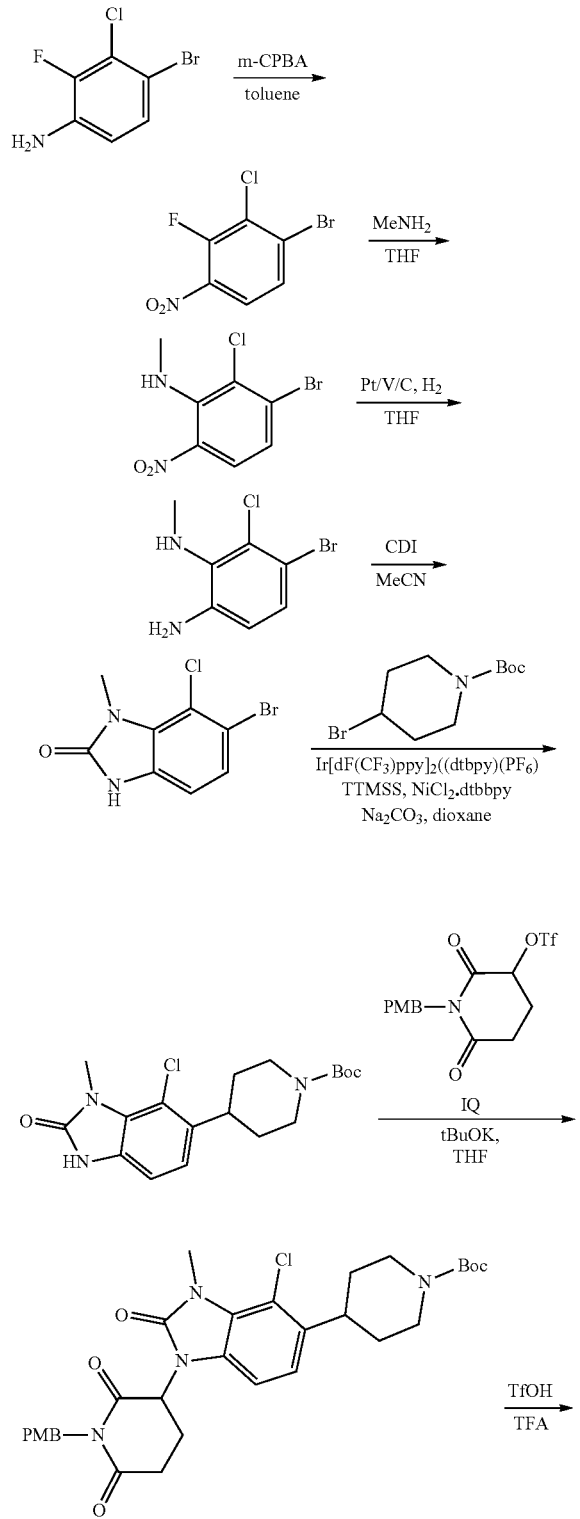

980

-continued

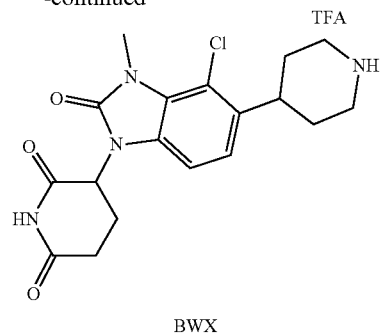

BWX

Step 1—1-bromo-2-chloro-3-fluoro-4-nitro-benzene

To a solution of 4-bromo-3-chloro-2-fluoro-aniline (2 g, 8.91 mmol, CAS #115843-99-7) in toluene (15 mL) was added m-CPBA (7.69 g, 35.6 mmol, 80% solution). The reaction was stirred at 50° C. for 24 hrs. On completion, the reaction was quenched with Na$_2$SO$_3$ solution (8 g Na$_2$SO$_3$) and stirred at 0° C. for 0.5 hr. The mixture was diluted with EA (250 mL). The organic layer was washed with water (250 mL×3), dried over Na$_2$SO$_4$ and filtered. The filtrate was concentrated in vacuo. The residue was purified by column chromatography (SiO$_2$, Petroleum ether/Ethyl acetate=10/1) to give title compound (0.66 g, 29% yield) as yellow solid. $^1$H NMR (400 MHz, CDCl$_3$) δ=7.81 (dd, J=7.2, 9.2 Hz, 1H), 7.55 (dd, J=2.0, 9.2 Hz, 1H).

Step 2—3-bromo-2-chloro-N-methyl-6-nitro-aniline

To a solution of 1-bromo-2-chloro-3-fluoro-4-nitro-benzene (1.65 g, 6.48 mmol) in THF (20 mL) was added MeNH$_2$ (6.48 mL, 2M) in THF at 0° C. The reaction was stirred at 25° C. for 1 hr. On completion, the reaction was diluted with EA (150 mL). The organic layer was washed with water (100 mL×3), dried over Na$_2$SO$_4$ and filtered. The filtrate was concentrated in vacuo to give title compound (1.71 g, 99% yield) as red solid. $^1$H NMR (400 MHz, CDCl$_3$) δ 7.69 (d, J=9.2 Hz, 1H), 6.99 (d, J=9.2 Hz, 1H), 6.67 (s, 1H), 3.01 (d, J=2.0 Hz, 3H).

Step 3—4-bromo-3-chloro-N2-methyl-benzene-1,2-diamine

To a solution of 3-bromo-2-chloro-N-methyl-6-nitro-aniline (1.71 g, 6.44 mmol) in MeOH (20 mL) was added Pt/V/C (1 g, 114 umol, 3 wt %) under N$_2$. The suspension was degassed under vacuum and purged with H$_2$ several times. The mixture was stirred under H$_2$ (15 psi) at 25° C. for 4 hrs. On completion, the reaction was filtered. The filtrate was concentrated in vacuo to give title compound (1.3 g, 85% yield) as yellow oil. $^1$H NMR (400 MHz, CDCl$_3$) δ 7.04 (d, J=8.4 Hz, 1H), 6.44 (d, J=8.4 Hz, 1H), 4.01-3.36 (m, 3H), 2.61 (s, 3H).

Step 4—5-bromo-4-chloro-3-methyl-1H-benzimidazol-2-one

A mixture of 4-bromo-3-chloro-N2-methyl-benzene-1,2-diamine (1.3 g, 5.52 mmol) and CDI (1.52 g, 9.38 mmol) in MeCN (20 mL) was stirred at 80° C. for 4 hrs. On completion, the mixture was diluted with water (100 mL) and filtered. The filter cake was concentrated in vacuo to give title compound (1.3 g, 90% yield) as yellow solid. $^1$H NMR (400 MHz, DMSO-d$_6$) δ 11.33 (s, 1H), 7.34 (d, J=8.4 Hz, 1H), 6.90 (d, J=8.4 Hz, 1H), 3.56 (s, 3H).

Step 5—Tert-butyl 4-(4-chloro-3-methyl-2-oxo-1H-benzimidazol-5-yl)piperidine-1-carboxylate To a 15 mL vial equipped with a stir bar was added 5-bromo-4-chloro-3-methyl-1H-benzimidazol-2-one (1.3 g, 4.97 mmol), tert-butyl 4-bromopiperidine-1-carboxylate (1.71 g, 6.46 mmol, CAS #180695-79-8), Ir[dF(CF$_3$)ppy]$_2$(dtbpy)(PF$_6$) (55.7 mg, 49.7 umol), NiCl$_2$.dtbbpy (9.89 mg, 24.8 umol), TTMSS (1.24 g, 4.97 mmol) and Na$_2$CO$_3$ (1.05 g, 9.94 mmol) in DME (30 mL). The vial was sealed and placed under nitrogen was added. The reaction was stirred and irradiated with a 10 W [455 nm] blue LED lamp (3 cm away), with cooling water to keep the reaction temperature at 25° C. for 14 hrs. On completion, the reaction was diluted with EA (150 mL). The organic layer was washed with water (150 mL×3), dried over Na$_2$SO$_4$ and filtered. The filtrate was concentrated in vacuo. The residue was purified by reverse phase. (0.1% FA condition) to give title compound (500 mg, 27% yield) as white solid. $^1$H NMR (400 MHz, DMSO-d$_6$) δ 11.22-10.94 (m, 1H), 7.04-6.82 (m, 2H), 4.14-4.01 (m, 2H), 3.59-3.55 (m, 3H), 3.19-3.11 (m, 1H), 2.92-2.77 (m, 2H), 1.72 (d, J=12.0 Hz, 2H), 1.52-1.44 (m, 2H), 1.41 (s, 9H).

Step 6—Tert-butyl 4-[4-chloro-1-[1-[(4-methoxyphenyl)methyl]-2,6-dioxo-3-piperidyl]-3-methyl-2-oxo-benzimidazol-5-yl]piperidine-1-carboxylate To a solution of tert-butyl 4-(4-chloro-3-methyl-2-oxo-1H-benzimidazol-5-yl)piperidine-1-carboxylate (50.0 mg, 136 umol) in THF (0.5 mL) was added t-BuOK (23.0 mg, 205 umol) at 0° C. The reaction was stirred at 0° C. for 0.5 hr. Then, a solution of [1-[(4-methoxyphenyl)methyl]-2,6-dioxo-3-piperidyl]trifluoromethanesulfonate (78.1 mg, 205 umol, Intermediate IQ) in THF (1 mL) was added into the mixture at 0° C. The reaction was stirred at 0° C. for 3.5 hrs. On completion, the reaction was diluted with EA (30 mL). The organic layer was washed with water (30 mL×3), dried over Na$_2$SO$_4$ and concentrated in vacuo. The residue was purified by prep-TLC (SiO$_2$, PE:EA=1:2, P1: R$_f$=0.5) to give title compound (46 mg, 56% yield) as white solid. $^1$H NMR (400 MHz, DMSO-d$_6$) δ 7.20 (d, J=8.8 Hz, 2H), 6.98 (s, 2H), 6.89-6.80 (m, 2H), 5.55 (dd, J=5.6, 13.2 Hz, 1H), 4.85-4.71 (m, 2H), 4.17-4.04 (m, 2H), 3.73 (s, 3H), 3.66 (s, 3H), 3.20-3.14 (m, 1H), 3.12-2.98 (m, 1H), 2.94-2.64 (m, 4H), 2.10-2.00 (m, 1H), 1.73 (d, J=12.4 Hz, 2H), 1.59-1.46 (m, 2H), 1.42 (s, 9H).

Step 7—3-[4-chloro-3-methyl-2-oxo-5-(4-piperidyl)benzimidazol-1-yl]piperidine-2,6-dione A mixture of tert-butyl 4-[4-chloro-1-[1-[(4-methoxyphenyl)methyl]-2,6-dioxo-3-piperidyl]-3-methyl-2-oxo-benzimidazol-5-yl]piperidine-1-carboxylate (46 mg, 77.0 umol) and TfOH (340.00 mg, 2.27 mmol) in TFA (1 mL) was stirred at 70° C. for 4 hrs. On completion, the reaction was concentrated in vacuo to give title compound (37.8 mg, 99% yield, TFA) as brown oil. LC-MS (ESI$^+$) m/z 377.3 (M+H)$^+$.

3-[3,4-dimethyl-2-oxo-5-(4-piperidyl)benzimidazol-1-yl]piperidine-2,6-dione (Intermediate BWY)

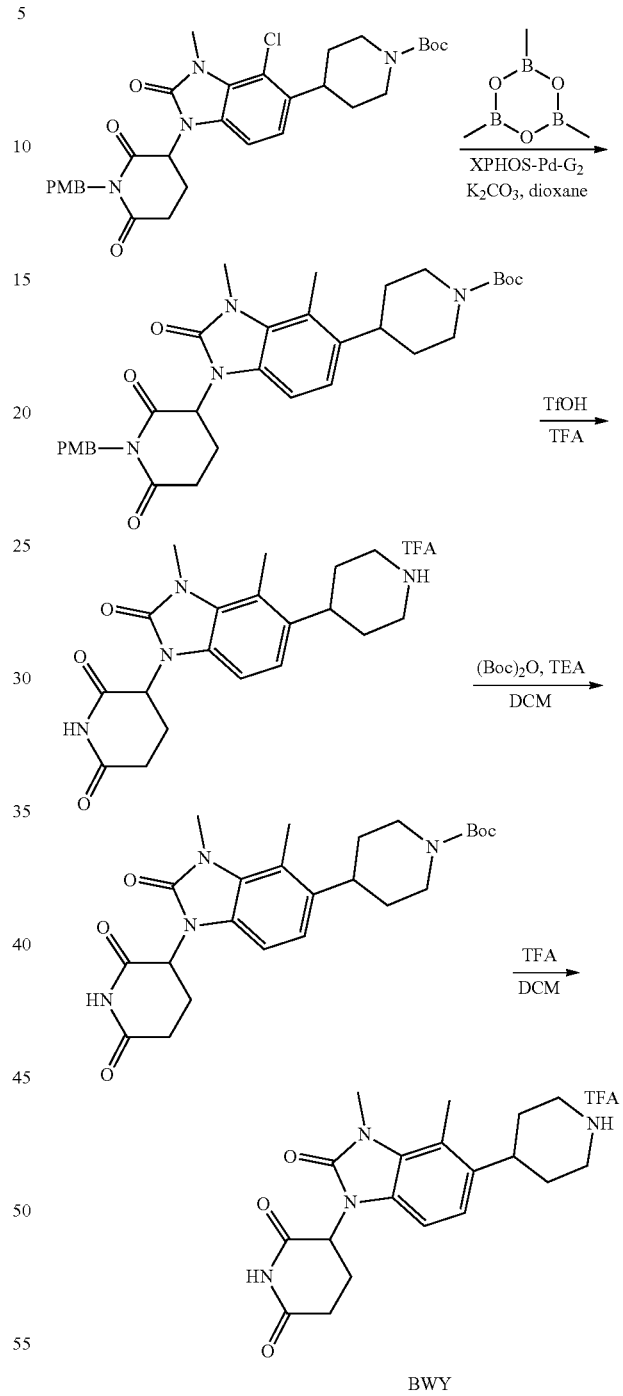

BWY

Step 1—Tert-butyl 4-[1-[1-[(4-methoxyphenyl)methyl]-2,6-dioxo-3-piperidyl]-3,4-dimethyl-2-oxo-benzimidazol-5-yl]piperidine-1-carboxylate A solution of tert-butyl 4-[4-chloro-1-[1-[(4-methoxyphenyl)methyl]-2,6-dioxo-3-piperidyl]-3-methyl-2-oxo-benzimidazol-5-yl]piperidine-1-carboxylate (200 mg, 334 umol, synthesized via Steps 1-6 of Intermediate BWX), 2,4,6- trimethyl-1,3,5,2,4,6-trioxatriborinane (84.1 mg, 669 umol, CAS #823-96-1), K₂CO₃ (138 mg, 1.00 mmol) and XPHOS-PD-G2 (26.3 mg, 33.5 umol) in dioxane (3 mL) was stirred at 90° C. for 16 hrs under N₂. On completion, the reaction was filtered and the filtrate was concentrated in vacuo. The residue was purified by reverse phase (0.1% FA condition) to give title compound (190 mg, 98% yield) as pink solid. ¹H NMR (400 MHz, DMSO-d₆) δ 7.20 (d, J=8.4 Hz, 2H), 6.88-6.79 (m, 3H), 6.76 (s, 1H), 5.75 (s, 1H), 5.48 (dd, J=5.2, 12.8 Hz, 1H), 4.85-4.73 (m, 2H), 4.08 (d, J=10.0 Hz, 2H), 3.72 (s, 3H), 3.61 (s, 3H), 3.10-2.93 (m, 3H), 2.75-2.67 (m, 2H), 2.56 (s, 3H), 2.05-1.95 (m, 1H), 1.65 (d, J=12.4 Hz, 2H), 1.51-1.45 (m, 2H), 1.42 (s, 9H).

Step 2—3-[3,4-dimethyl-2-oxo-5-(4-piperidyl)benz-imidazol-1-yl]piperidine-2,6-dione To a mixture of tert-butyl 4-[1-[1-[(4-methoxyphenyl)methyl]-2,6-dioxo-3-piperidyl]-3,4-dimethyl-2-oxo-benzimidazol-5-yl]piperidine-1-carboxylate (160 mg, 277 umol) in TFA (2 mL) was added TfOH (0.5 mL), then the reaction was stirred at 70° C. for 4 hrs. On completion, the reaction was concentrated in vacuo to give title compound (130 mg, 99% yield, TFA) as brown oil. LC-MS (ESI⁺) m/z 357.4 (M+H)⁺.

Step 3—Tert-butyl 4-[1-(2,6-dioxo-3-piperidyl)-3,4-dimethyl-2-oxo-benzimidazol-5-yl]piperidine-1-carboxylate A mixture of 3-[3,4-dimethyl-2-oxo-5-(4-piperidyl)benzimidazol-1-yl]piperidine-2,6-dione (130 mg, 276.34 umol, TFA), (Boc)₂O (90.4 mg, 414 umol) and TEA (279 mg, 2.76 mmol) in DCM (2 mL) was stirred at 25° C. for 2 hrs. On completion, the reaction was concentrated in vacuo. The residue was purified by prep-HPLC (column: Phenomenex luna C18 150*25 mm*10 um; mobile phase: [water (0.225% FA)-ACN]; B %: 36%-66%, 10 min) to give title compound (75 mg, 59% yield) as white solid. ¹H NMR (400 MHz, DMSO-d₆) δ 11.07 (s, 1H), 6.89 (s, 2H), 5.32 (dd, J=5.2, 12.4 Hz, 1H), 4.07 (d, J=10.0 Hz, 2H), 3.61 (s, 3H), 3.30 (s, 1H), 3.02-2.78 (m, 4H), 2.74-2.65 (m, 1H), 2.56 (s, 3H), 2.01-1.92 (m, 1H), 1.66 (d, J=12.0 Hz, 2H), 1.52-1.44 (m, 2H), 1.42 (s, 9H).

Step 4—3-[3,4-dimethyl-2-oxo-5-(4-piperidyl)benz-imidazol-1-yl]piperidine-2,6-dione To a solution of tert-butyl 4-[1-(2,6-dioxo-3-piperidyl)-3,4-dimethyl-2-oxo-benzimidazol-5-yl]piperidine-1-carboxylate (40 mg, 87.6 umol) in DCM (1 mL) was added TFA (0.3 mL), then the reaction was stirred at 25° C. for 1 hr. On completion, the reaction was concentrated in vacuo to give title compound (41 mg, 99% yield, TFA) as brown oil. LC-MS (ESI⁺) m/z 357.2 (M+H)⁺.

2-[4-(Benzyloxymethyl)cyclohexyl]-6-bromo-5-methoxy-1,3-benzothiazole (Intermediate BWZ)

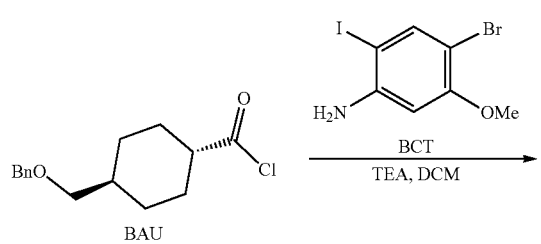

Step 1—4-(Benzyloxymethyl)-N-(4-bromo-2-iodo-5-methoxy-phenyl)cyclohexanecarboxamide To a mixture of 4-bromo-2-iodo-5-methoxy-aniline (7.00 g, 21.3 mmol, Intermediate BCT) and TEA (6.48 g, 64.0 mmol) in DCM (70 mL) was added a solution of 4-(benzyloxymethyl)cyclohexanecarbonyl chloride (5.69 g, 21.3 mmol, Intermediate BAU) in DCM (70 mL). The reaction mixture was stirred at 25° C. for 12 hr. On completion, the reaction mixture was diluted with water (30 mL) and extracted with EA (2×80 mL). The combined organic layer was dried over Na₂SO₄, filtered and concentrated in vacuo to give a residue. The residue was purified by column chromatography to give the title compound (11.9 g, 99% yield) as light yellow solid. ¹H NMR (400 MHz, DMSO-d₆) δ 9.26 (s, 1H), 7.99-7.95 (m, 1H), 7.38-7.22 (m, 6H), 4.45 (s, 2H), 3.82-3.79 (m, 3H), 3.27 (d, J=6.0 Hz, 2H), 2.43-2.31 (m, 1H), 1.95 (d, J=12.0 Hz, 2H), 1.88-1.80 (m, 2H), 1.64-1.53 (m, 1H), 1.44 (dq, J=3.6, 12.8 Hz, 2H), 1.09-0.95 (m, 2H). LC-MS (ESI⁺) m/z 558.1 (M+H)⁺.

Step 2—4-(Benzyloxymethyl)-N-(4-bromo-2-iodo-5-methoxy-phenyl)cyclohexanecarbothioamide To a mixture of 4-(benzyloxymethyl)-N-(4-bromo-2-iodo-5-methoxy-phenyl)cyclohexanecarboxamide (14.0 g, 25.0 mmol) in THF (140 mL) was added P₂S₅ (5.57 g, 25.0 mmol). The reaction mixture was stirred at 25° C. for 2 hrs. On completion, the reaction mixture was filtered and the filtrate was diluted with water (30 mL), then the filtrate was extracted with EA (3×200 mL). The combined organic layer was dried over Na₂SO₄, filtered and concentrated in vacuo to give the title compound (14.4 g, 99% yield) as brown oil. ¹H NMR (400 MHz, DMSO-d₆) δ 11.34-11.28 (m, 1H), 8.03 (s, 1H), 7.38-7.30 (m, 5H), 7.02 (s, 1H), 4.46 (s, 2H), 3.81 (s, 3H), 3.29 (d, J=6.4 Hz, 2H), 2.80-2.74 (m, 1H), 1.93 (s, 2H), 1.86 (d, J=10.8 Hz, 2H), 1.70 (dd, J=2.0, 12.4 Hz, 2H), 1.62-1.58 (m, 1H), 1.13-1.03 (m, 2H).

Step 6—2-[4-(Benzyloxymethyl)cyclohexyl]-6-bromo-5-methoxy-1,3-benzothiazole To a mixture of 4-(benzyloxymethyl)-N-(4-bromo-2-iodo-5-methoxy-phenyl)cyclohexanecarbothioamide (14.4 g, 25.0 mmol) in DME (150 mL) was added CuI (477 mg, 2.51 mmol), 1,10-phenanthroline (451 mg, 2.51 mmol). The reaction mixture was then stirred at 40° C. for 12 hrs. On completion, the residue was diluted with water (100 mL), then the residue was extracted with EA (3×200 mL). The combined organic layer was dried over $Na_2SO_4$, filtered and concentrated in vacuo to give a residue. The residue was purified by column chromatography to give the title compound (11.0 g, 98% yield) as white solid. $^1$H NMR (400 MHz, DMSO-$d_6$) δ 8.30 (s, 1H), 7.64 (s, 1H), 7.38-7.35 (m, 1H), 7.33 (d, J=2.8 Hz, 3H), 7.30-7.27 (m, 1H), 4.46 (s, 2H), 3.91 (s, 3H), 3.29 (d, J=6.0 Hz, 2H), 3.02 (tt, J=3.6, 12.0 Hz, 1H), 2.17-2.12 (m, 2H), 1.88 (dd, J=2.8, 13.6 Hz, 2H), 1.56 (dq, J=3.2, 12.8 Hz, 3H), 1.15 (dd, J=3.6, 12.4 Hz, 2H).

3-[4-[1-[[4-(5-amino-6-methoxy-indazol-2-yl)cyclohexyl] methyl]-4-piperidyl]-3-methyl-2-oxo-benzimidazol-1-yl]piperidine-2,6-dione (Intermediate BXA)

mediate AZK) in THF (8 mL) and DMF (1 mL) was added TEA (222 mg, 2.20 mmol) and HOAc (132 mg, 2.20 mmol) until the pH=6. Then tert-butyl (2-((1r,4r)-4-formylcyclohexyl)-6-methoxy-2H-indazol-5-yl)carbamate (820 mg, 2.20 mmol, Intermediate BGT) was added into the mixture. The reaction was stirred at −10° C. for 30 min, followed by addition of NaBH(OAc)$_3$ (931 mg, 4.39 mmol). The reaction was then stirred at −10° C. for 2 hrs. On completion, the mixture was quenched with water (0.05 mL) and concentrated in vacuo to give the title compound (820 mg, 53% yield) as a brown solid. $^1$H NMR (400 MHz, DMSO-$d_6$) δ 11.10 (s, 1H), 8.24-8.14 (m, 1H), 7.79 (s, 1H), 7.12-7.00 (m, 2H), 6.99-6.89 (m, 2H), 5.39 (dd, J=5.2, 12.4 Hz, 1H), 4.45-4.33 (m, 1H), 4.03 (m, J=7.1 Hz, 1H), 3.85 (s, 3H), 3.63 (s, 3H), 3.12-2.99 (m, 2H), 2.94-2.84 (m, 1H), 2.77-2.63 (m, 2H), 2.16 (d, J=11.6 Hz, 2H), 2.05-1.94 (m, 8H), 1.94-1.89 (m, 2H), 1.46 (s, 9H), 1.40 (s, 1H), 1.27 (d, J=4.6, 7.3 Hz, 2H), 1.17 (t, J=7.0 Hz, 2H), 0.86-0.81 (m, 2H); LC-MS (ESI$^+$) m/z 700.6 (M+H)$^+$.

Step 2—3-[4-[1-[[4-(5-amino-6-methoxy-indazol-2-yl) cyclohexyl] methyl]-4-piperidyl]-3-methyl-2-oxo-benzimidazol-1-yl] piperidine-2,6-dione To a solution of tert-butyl (2-((1r,4r)-4-((4-(1-(2,6-dioxopiperidin-3-yl)-3-methyl-2-oxo-2,3-dihydro-1H-benzo

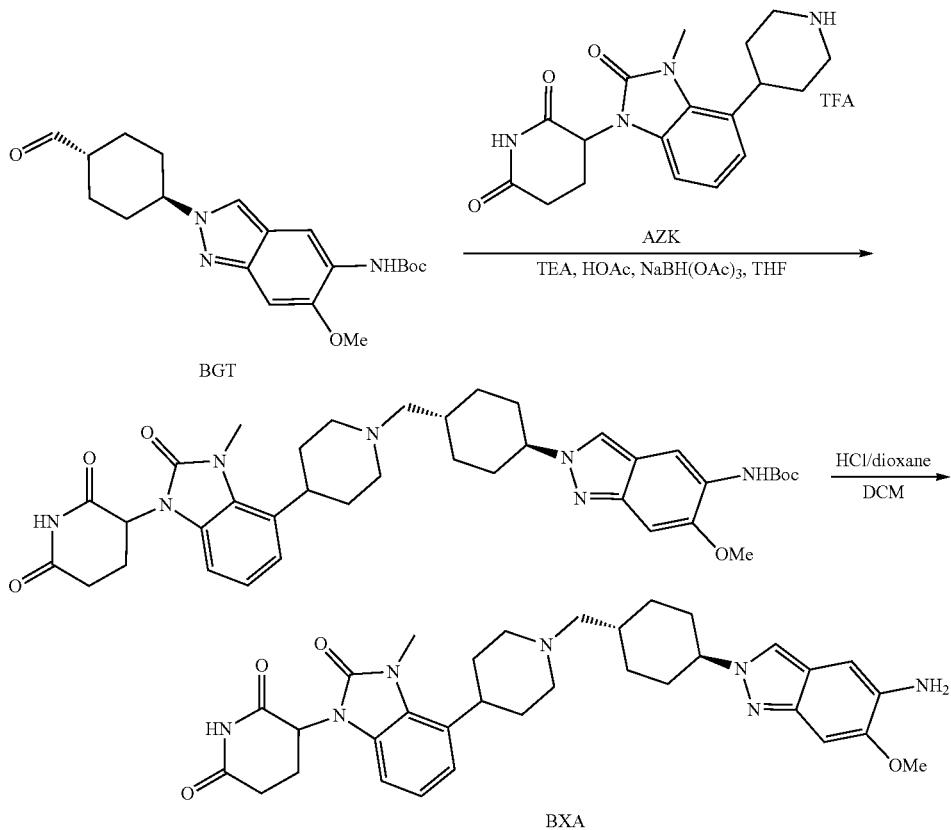

Step 1—Tert-butyl N-[2-[4-[[4-[1-(2,6-dioxo-3-piperidyl)-3-methyl-2-oxo-benzimidazol-4-yl]-1-piperidyl]methyl]cyclohexyl]-6-methoxy-indazol-5-yl]carbamate To a solution of 3-[3-methyl-2-oxo-4-(4-piperidyl)benzimidazol-1-yl]piperidine-2,6-dione (1 g, 2.20 mmol, Inter-

[d]imidazol-4-yl)piperidin-1-yl)methyl)cyclohexyl)-6-methoxy-2H-indazol-5-yl)carbamate (100 mg, 143 umol) in DCM (1.5 mL) was added HCl/dioxane (4 M, 3 mL). The mixture was stirred at 10° C. for 2 hrs. On completion, the mixture was concentrated in vacuo to give the title compound (66 mg, 77% yield) as a brown solid. LC-MS (ESI$^+$) m/z 600.6 (M+H)$^+$.

987

6-(Trifluoromethyl)nicotinic acid (CAS #231291-22-8) (Intermediate BXB)

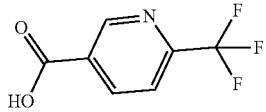

BXB

2-Fluorobenzoic acid (CAS #445-29-4) (Intermediate BXC)

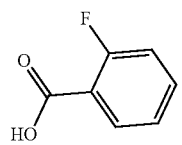

BXC 4-(trifluoromethyl)thiazole-2-carboxylic acid (CAS #944900-55-4) (Intermediate BXD)

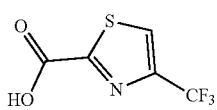

BXD

N-[2-(4-formylcyclohexyl)-7-methoxy-indazol-5-yl]-6-(trifluoromethyl)pyridine-2-carboxamide (Intermediate BXE)

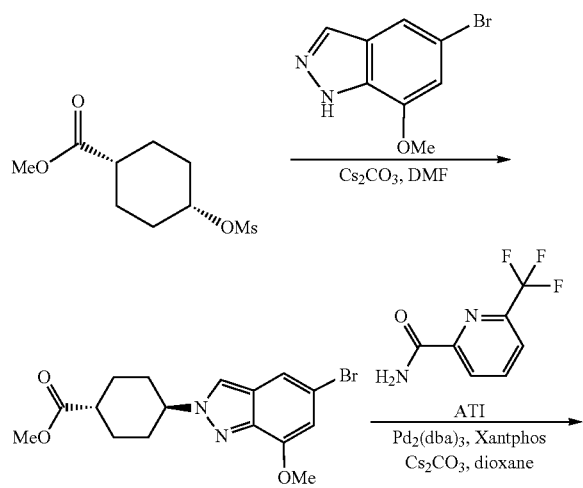

988

-continued

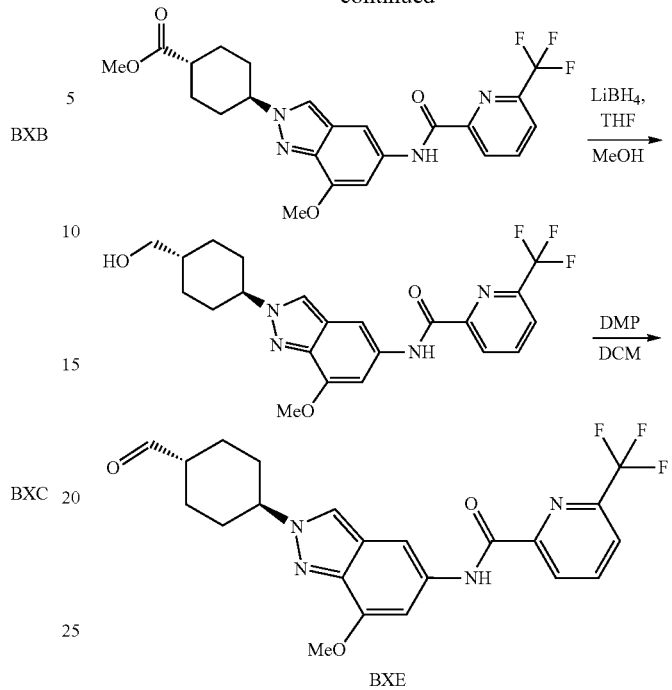

BXE

Step 1—Methyl 4-(5-bromo-7-methoxy-indazol-2-yl)cyclohexanecarboxylate

To a solution of methyl 4-methylsulfonyloxycyclohexanecarboxylate (2.08 g, 1.76 mmol, synthesized via Step 1 of Intermediate QS) and 5-bromo-7-methoxy-2H-indazole (1.00 g, 881 umol, CAS #1374652-62-6) in DMF (2 mL) was added $Cs_2CO_3$ (574 mg, 1.76 mmol). The mixture was then stirred at 80° C. for 16 hrs. On completion, the reaction mixture was filtered and concentrated under reduced pressure to give a residue. The reaction mixture was purified by reversed phase flash (0.1% FA condition) to give the title compound (198 mg, 12% yield) as a brown solid. $^1H$ NMR (400 MHz, CHLOROFORM-d) δ=7.85 (s, 1H), 7.38 (d, J=1.2 Hz, 1H), 6.63 (d, J=1.6 Hz, 1H), 4.42 (tt, J=4.0, 12.0 Hz, 1H), 4.01 (s, 3H), 3.71 (s, 3H), 2.44 (tt, J=3.6, 12.4 Hz, 1H), 2.39-2.32 (m, 2H), 2.26-2.18 (m, 2H), 2.07-1.96 (m, 2H), 1.68 (dq, J=3.3, 13.2 Hz, 2H). LC-MS (ESI+) m/z 369.0 (M+H)$^+$.

Step 2—Methyl 4-[7-methoxy-5-[[6-(trifluoromethyl)pyridine-2-carbonyl]amino]indazol-2-yl]cyclohexanecarboxylate To a solution of methyl 4-(5-bromo-7-methoxy-indazol-2-yl)cyclohexanecarboxylate (332 mg, 880 umol) and 6-(trifluoromethyl)pyridine-2-carboxamide (167 mg, 879.54 umol, Intermediate ATI) in dioxane (10 mL) was added Xantphos (102 mg, 175.91 umol), $Cs_2CO_3$ (860 mg, 2.64 mmol) and $Pd_2(dba)_3$ (80.5 mg, 88.0 umol). The mixture was then stirred under $N_2$ at 110° C. for 16 hrs. On completion, the reaction mixture was filtered and concentrated under reduced pressure to give a residue. The residue was purified by prep-HPLC (column: Phenomenex Luna C18 150*25 mm*10 um; mobile phase: [water (0.05% HCl)-ACN]; B %: 42%-72%, 10 min) to give the title compound (95.0 mg, 17% yield) as an off-white solid. LC-MS (ESI+) m/z 447.3 (M+H)$^+$.

Step 3—N-[2-[4-(hydroxymethyl)cyclohexyl]-7-methoxy-indazol-5-yl]-6-(trifluoromethyl)pyridine-2-carboxamide A mixture of methyl methyl 4-[7-methoxy-5-[[6-(trifluoromethyl)pyridine-2-carbonyl]amino]indazol -2-yl]cyclohexanecarboxylate (90.0 mg, 145 umol) in THF (0.8 mL) and MeOH (0.2 mL) was degassed and purged with $N_2$ for three times. Then to the mixture was added LiBH$_4$ (100 mg, 4.59 mmol), and then the mixture was stirred at 60° C. for 16 hrs under $N_2$ atmosphere. On completion, the reaction mixture was quenched by addition H$_2$O (2 mL) at 25° C., and then extracted with EA 15 mL (3×5 mL). The combined organic layers were washed with brine (2×5 mL), dried over Na$_2$SO$_4$, filtered and concentrated under reduced pressure to give a residue. The residue was purified by prep-TLC (SiO$_2$, DCM:MeOH=15:1) to give the title compound (44.0 mg, 56% yield) as a yellow solid. LC-MS (ESI+) m/z 449.4 (M+H)$^+$.

Step 4—N-[2-(4-formylcyclohexyl)-7-methoxy-indazol-5-yl]-6-(trifluoromethyl)pyridine-2-carboxamide To a solution of N-[2-[4-(hydroxymethyl)cyclohexyl]-7-methoxy-indazol-5-yl]-6-(trifluoromethyl) pyridine-2-carboxamide (44.0 mg, 98.1 umol) in DCM (1 mL) was added DMP (49.9 mg, 118 umol). The reaction mixture was stirred at 0° C. for 1 hr. On completion, the reaction mixture was quenched with saturated sodium thiosulfate (5 mL), then the organic layer was washed with saturated sodium hydrogen carbonate (5 mL×2) and brine (10 mL). Then the organics were dried over anhydrous sodium sulfate, filtered and concentrated in vacuo. The residue was purified by prep-HPLC (column: Phenomenex Luna C18 150*25 mm*10 um; mobile phase: [water (0.225% FA)-ACN]; B %: 43%-73%, 11.5 min) to give the title compound (20.0 mg, 44% yield) as a pink solid. $^1$H NMR (400 MHz, DMSO-d$_6$) δ 10.24 (s, 1H), 9.65 (s, 1H), 8.45-8.31 (m, 3H), 8.17 (d, J=8.0 Hz, 1H), 7.93 (d, J=1.6 Hz, 1H), 7.03 (d, J=1.6 Hz, 1H), 3.93 (s, 3H), 3.30 (br s, 2H), 2.22-2.15 (m, 2H), 2.11 (br d, J=12.0 Hz, 2H), 1.98 (dq, J=2.8, 12.8 Hz, 2H), 1.44 (br dd, J=3.2, 13.2 Hz, 2H). LC-MS (ESI+) m/z 477.3 (M+H)$^+$.

7-bromopyrrolo[1,2-b]pyridazine-3-carbonitrile (Intermediate BVT)

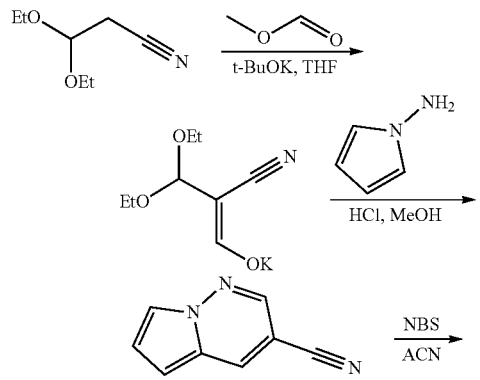

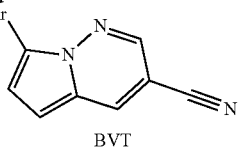

Step 1—[(E)-2-cyano-3,3-diethoxy-prop-1-enoxy] potassium

To a solution of 3,3-diethoxypropanenitrile (10.0 g, 69.8 mmol, CAS #2032-34-0) and methyl formate (5.45 g, 90.8, CAS #107-31-3) in THF (80 mL) was added 1M t-BuOK in THF (69.84 mL) slowly. The mixture was stirred at 20° C. for 2 hr. On completion, the mixture was added hexane (400 mL) and stirred for 20 min. Then the slurry was filtered and the filter cake washed with hexanes/THF (1:1) and dried at 60° C. in a vacuo to give the title compound (7 g, 48% yield) as a yellow solid. $^1$H NMR (400 MHz, CD$_3$OD) δ 8.12 (s, 1H), 7.95 (s, 1H), 5.22 (s, 1H), 4.68 (s, 1H), 3.60-3.50 (m, J=7.0 Hz, 4H), 1.14 (t, J=7.0 Hz, 6H).

Step 2—Pyrrolo[1,2-b]pyridazine-3-carbonitrile

To a solution of [(E)-2-cyano-3,3-diethoxy-prop-1-enoxy]potassium (4 g, 19.1 mmol) was added HCl (12 M, 5.57 mL) slowly and stirred at 25° C. for 0.2 hr. Then the mixture was added pyrrol-1-amine (1.57 g, 19.1 mmol, CAS #765-39-9) in MeOH (20 mL). After the addition, the reaction mixture was stirred at 90° C. for 2 hrs. On completion, to the mixture was added NaHCO$_3$(aq.) carefully until the resulting residue until bubbling stopped. Then the mixture was extracted with ethyl acetate (30 mL), the organic phase was washed with brine (20 mL×2), dried over anhydrous Na$_2$SO$_4$, filtered and concentrated in vacuo. The residue was purified by silica gel chromatography gel, Petroleum ether/Ethyl acetate=20/1) to give the title compound (2 g, 73% yield) as a yellow solid. $^1$H NMR (400 MHz, CDCl$_3$) δ 8.14-8.11 (m, 2H), 7.94 (dd, J=1.6, 2.0 Hz, 1H), 7.05 (dd, J=2.8, 4.6 Hz, 1H), 6.85 (dd, J=1.2, 4.4 Hz, 1H).

Step 3—7-bromopyrrolo[1,2-b]pyridazine-3-carbonitrile

To a solution of pyrrolo[1,2-b]pyridazine-3-carbonitrile (1.00 g, 6.99 mmol) in ACN (20 mL) was added NBS (1.24 g, 6.99 mmol), the mixture was stirred at 20° C. for 1 hr. On completion, the mixture was filtered and filter concentrated in vacuo to give a residue. The residue was triturated with Petroleum ether at 20° C. for 20 mins, the solid was collected by filtration. The residue was purified by reverse phase (0.1% FA condition) to give the title compound (1.40 g, 90% yield) as yellow solid. $^1$H NMR (400 MHz, CDCl$_3$) δ 8.28 (d, J=1.6 Hz, 1H), 8.10 (d, J=2.0 Hz, 1H), 7.12 (d, J=4.8 Hz, 1H), 6.93 (d, J=4.6 Hz, 1H).

6-(3-cyanopyrrolo[1,2-b]pyridazin-7-yl)-N-(4-formylcyclohexyl)-4-(isopropylamino)pyridine-3-carboxamide (Intermediate BVU)

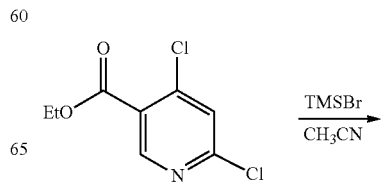

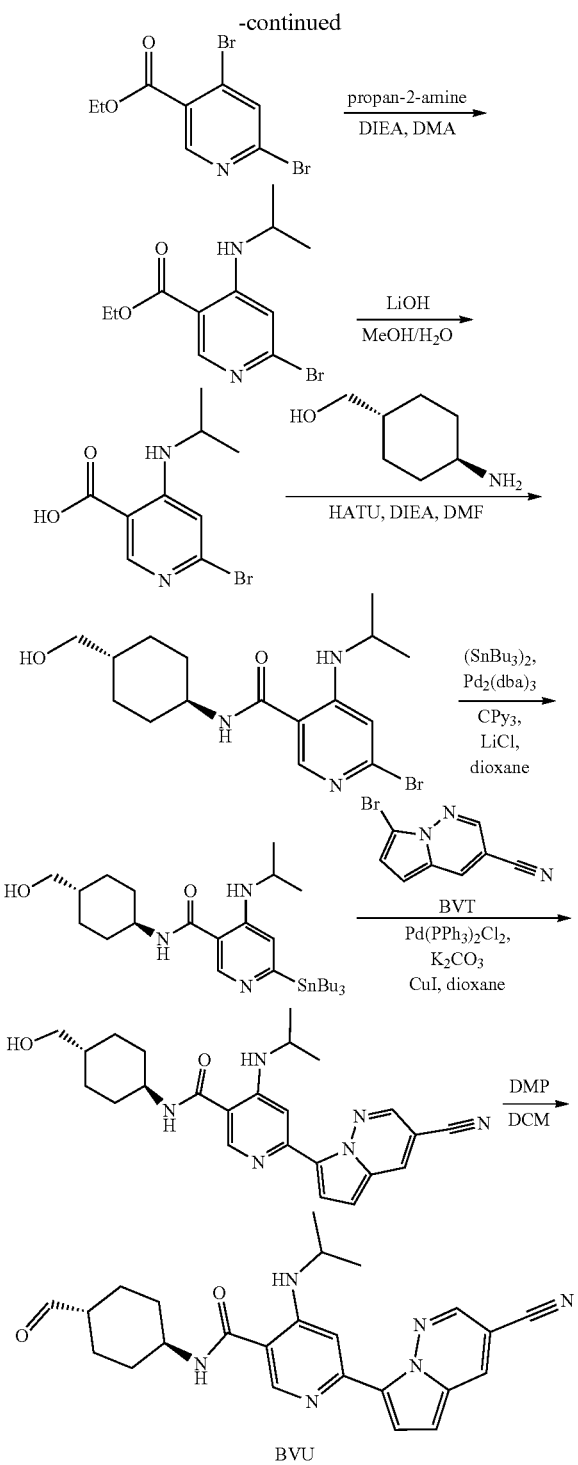

Step 1—Ethyl 4,6-dibromopyridine-3-carboxylate

To a solution of ethyl 4,6-dichloropyridine-3-carboxylate (10.0 g, 45.4 mmol) in ACN (200 mL) was added TMSBr (34.8 g, 227 mmol). The mixture was stirred at 80° C. for 16 hrs. On completion, the reaction mixture was extracted with ethyl acetate (500 mL). The organic phase was washed with brine (100 mL×3), dried with anhydrous $Na_2SO_4$, filtered and concentrated in vacuo to give the title compound (13 g, 93% yield) as gray oil. $^1$H NMR (400 MHz, $CDCl_3$) δ 8.77 (s, 1H), 7.86 (s, 1H), 4.44 (M, J=7.0 Hz, 2H), 1.43 (t, J=7.1 Hz, 3H); LC-MS (ESI$^+$) m/z 309.8 (M+H)$^+$.

Step 2—Ethyl 6-bromo-4-(isopropylamino)pyridine-3-carboxylate

To a solution of ethyl 4,6-dibromopyridine-3-carboxylate (13.0 g, 42.1 mmol) in DMA (50 mL) was added DIEA (27.2 g, 210 mmol) and propan-2-amine (2.49 g, 42.1 mmol). The mixture was stirred at 50° C. for 3 hrs. On completion, the reaction mixture was extracted with ethyl acetate (80 mL). The organic phase was washed with brine (40 mL), dried over anhydrous $Na_2SO_4$, filtered and the filtrated was concentrated in vacuo. The residue was purified by silica gel chromatography (silica gel, Petroleum ether/Ethyl acetate=10/1) to give the title compound (9.00 g, 74% yield) as yellow oil. $^1$H NMR (400 MHz, $CDCl_3$) δ 8.53 (s, 1H), 8.01 (d, J=6.0 Hz, 1H), 6.64 (s, 1H), 4.26-4.23 (M, J=7.0 Hz, 2H), 3.61 (d, J=6.4, 13.2 Hz, 1H), 1.31 (t, J=7.2 Hz, 3H), 1.21 (d, J=6.4 Hz, 6H).

Step 3—6-bromo-4-(isopropylamino)pyridine-3-carboxylic Acid

To a solution of ethyl 6-bromo-4-(isopropylamino)pyridine-3-carboxylate (5.00 g, 17.4 mmol) in MeOH (25 mL) and $H_2O$ (25 mL) was added LiOH·$H_2O$ (3.65 g, 87.1 mmol). The mixture was then stirred at 50° C. for 16 hrs. On completion, the reaction mixture was added $KHSO_4$ (aq.) until the pH=5. Then the mixture was extracted with ethyl acetate (80 mL×2), and the organic phase was washed with brine (40 mL), dried with anhydrous $Na_2SO_4$, filtered and concentrated in vacuo to give the title compound (3.2 g, 71% yield) as a white solid. $^1$H NMR (400 MHz, DMSO-$d_6$) δ 13.34 (s, 1H), 8.45 (s, 1H), 6.92 (s, 1H), 3.91-3.74 (m, 1H), 3.32 (s, 1H), 1.18 (d, J=6.3 Hz, 6H); LC-MS (ESI$^+$) m/z 259.0 (M+H)$^+$.

Step 4—6-bromo-N-[4-(hydroxymethyl)cyclohexyl]-4-(isopropylamino)pyridine-3-carboxamide To a solution of 6-bromo-4-(isopropylamino)pyridine-3-carboxylic acid (3.20 g, 12.4 mmol) in DMF (30 mL) was added HATU (5.64 g, 14.8 mmol), DIEA (4.79 g, 37.1 mmol) and (4-aminocyclohexyl)methanol (1.76 g, 13.6 mmol, CAS #1467-84-1). The mixture was then stirred at 25° C. for 1 hr. On completion, the reaction mixture was added into water (200 mL), the precipitate was collected by filtration to give the title compound (3.8 g, 83% yield) as white solid. $^1$H NMR (400 MHz, DMSO-$d_6$) δ 8.40 (d, J=7.6 Hz, 1H), 8.31 (d, J=7.6 Hz, 1H), 6.80 (s, 1H), 4.39 (t, J=5.3 Hz, 1H), 3.78-3.62 (m, 2H), 3.22 (t, J=5.8 Hz, 2H), 2.07 (s, 2H), 1.87-1.74 (m, 4H), 1.29 (dd, J=2.4, 12.0 Hz, 2H), 1.15 (d, J=6.4 Hz, 6H), 1.01-0.88 (m, 2H); LC-MS (ESI$^+$) m/z 372.1 (M+H)$^+$.

Step 5—N-[4-(hydroxymethyl)cyclohexyl]-4-(isopropylamino)-6-tributylstannyl-pyridine-3-carboxamide To a solution of 6-bromo-N-((1r,4r)-4-(hydroxymethyl)cyclohexyl)-4-(isopropylamino)nicotinamide (500 mg, 1.35 mmol) in dioxane (3 mL) was added LiCl (172 mg, 4.05 mmol), $Pd_2(dba)_3$ (123 mg, 135 umol), $(SnBu_3)_2$ (2.35 g, 4.05 mmol) and $CPy_3$ (37.9 mg, 135 umol). Then the mixture was stirred at 100° C. for 8 hr under nitrogen atmosphere. On completion, the reaction mixture was concentrated in vacuo to give the title compound (700 mg, 89% yield) as a yellow solid. LC-MS (ESI⁺) m/z 582.4 (M+H)⁺.

Step 6—6-(3-cyanopyrrolo[1,2-b]pyridazin-7-yl)-N-[4-(hydroxymethyl)cyclohexyl]-4-(isopropylamino)pyridine-3-carboxamide To a solution of N-((1r,4r)-4-(hydroxymethyl)cyclohexyl)-4-(isopropylamino)-6-(tributylstannyl) nicotinamide (700 mg, 1.21 mmol) and 7-bromopyrrolo[1,2-b]pyridazine-3-carbonitrile (250 mg, 1.13 mmol, Intermediate BVT) in dioxane (15 mL) was added Pd(PPh$_3$)$_2$Cl$_2$ (84.7 mg, 121), CuI (23.0 mg, 121 umol) and K$_2$CO$_3$ (166 mg, 1.21 mmol). The mixture was then stirred at 110° C. under N$_2$ for 1 hr. On completion, the reaction mixture was filtered and the filtrate was concentrated in vacuo. The residue was purified by silica gel chromatography (100-200 mesh silica gel, Petroleum ether/Ethyl acetate=0/1) to give the title compound (300 mg, 58% yield) as yellow solid. ¹H NMR (400 MHz, DMSO-d$_6$) δ 8.83 (d, J=2.0 Hz, 1H), 8.70 (d, J=2.0 Hz, 1H), 8.67 (s, 1H), 8.46 (d, J=7.0 Hz, 1H), 8.26 (d, J=7.6 Hz, 1H), 8.05 (s, 1H), 7.82 (d, J=4.8 Hz, 1H), 7.10 (d, J=4.8 Hz, 1H), 4.40 (t, J=5.3 Hz, 1H), 3.81-3.68 (m, 2H), 3.23 (t, J=5.8 Hz, 2H), 1.90-1.84 (m, 2H), 1.79 (d, J=12.4 Hz, 2H), 1.39-1.29 (m, 3H), 1.27 (d, J=6.4 Hz, 6H), 1.03-0.92 (m, 2H).

Step 7—6-(3-cyanopyrrolo[1,2-b]pyridazin-7-yl)-N-(4-formylcyclohexyl)-4-(isopropylamino)pyridine-3-carboxamide To a solution of 6-(3-cyanopyrrolo[1,2-b]pyridazin-7-yl)-N-[4-(hydroxymethyl) cyclohexyl]-4-(isopropylamino) pyridine-3-carboxamide (210 mg, 486 umol) in DCM (5 mL) was added DMP (309 mg, 728 umol). The mixture was stirred at 20° C. for 4 hrs. On completion, the reaction mixture was diluted with DCM (40 mL), quenched with Na$_2$S$_2$O$_3$ (aq. 20 mL) and NaHCO$_3$ (aq. 20 mL). The mixture was stirred at 20° C. for 30 min, then the organic layer was washed with brine (3×10 mL). The organic phase was separated and dried with anhydrous Na$_2$SO$_4$, filtered and the filtrate was concentrated in vacuo. The residue was purified by silica gel chromatography (Petroleum ether/Ethyl acetate=3/1) to give the title compound (80 mg, 38% yield) as a yellow solid. LC-MS (ESI⁺) m/z 431.3 (M+H)⁺.

5-Chloro-N-[2-(4-formylcyclohexyl)-5-methoxy-1,3-benzothiazol-6-yl]pyridine-3-carboxamide (Intermediate BXF)

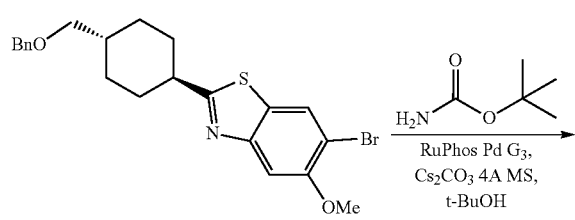

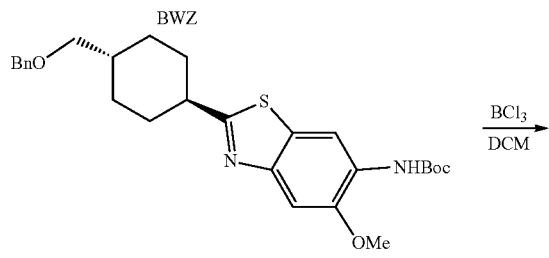

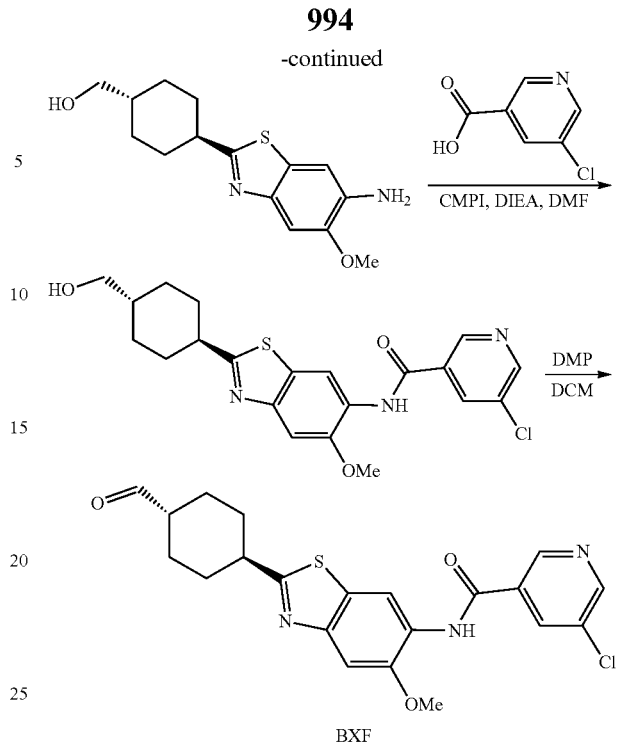

Step 1—tert-butyl N-[2-[4-(benzyloxymethyl)cyclohexyl]-5-methoxy-1,3-benzothiazol-6-yl]carbamate A mixture of 2-[4-(benzyloxymethyl)cyclohexyl]-6-bromo-5-methoxy-1,3-benzothiazole (2.00 g, 4.48 mmol, Intermediate BWZ), tert-butyl carbamate (524 mg, 4.48 mmol, CAS #4248-19-5), RuPhos Pd G3 (374 mg, 448 umol), Cs$_2$CO$_3$ (4.38 g, 13.4 mmol) and 4 Å molecular sieves (200 mg, 4.48 mmol) in t-BuOH (25 mL) was stirred at 80° C. for 12 hrs. On completion, the reaction mixture was filtered then the filtrate was diluted with water (30 mL), and extracted with EA (3×70 mL). The combined organic layer was dried over Na$_2$SO$_4$, filtered and concentrated in vacuo to give a residue. The residue was purified by reverse phase (0.1% FA condition) to give the title compound (1.06 g, 49% yield) as brown solid. ¹H NMR (400 MHz, DMSO-d$_6$) δ 8.27 (s, 1H), 8.07 (s, 1H), 7.54 (s, 1H), 7.38-7.35 (m, 1H), 7.34 (d, J=2.8 Hz, 2H), 7.32-7.26 (m, 2H), 4.46 (s, 2H), 3.88 (s, 3H), 3.33-3.28 (m, 4H), 3.05-2.96 (m, 1H), 2.15 (d, J=10.8 Hz, 2H), 1.89 (dd, J=2.8, 13.6 Hz, 2H), 1.70-1.63 (m, 1H), 1.46 (s, 9H), 1.20-1.13 (m, 2H). LC-MS (ESI⁺) m/z 483.3 (M+H)⁺.

Step 2—[4-(6-Amino-5-methoxy-1,3-benzothiazol-2-yl)cyclohexyl]methanol

To a mixture of tert-butyl N-[2-[4-(benzyloxymethyl)cyclohexyl]-5-methoxy-1,3-benzothiazol-6-yl]carbamate (1.00 g, 2.07 mmol) in DCM (10 mL) was added BCl$_3$ (1 M, 6.22 mL). The reaction mixture was stirred at 0° C. for 1.5 hr. On completion, the reaction mixture was quenched with water (10 mL) and extracted with DCM (3×200 mL). The aqueous phase layer was filtered and concentrated in vacuo to give the title compound (1.00 g, 60% yield) as yellow solid. LC-MS (ESI⁺) m/z 293.1 (M+H)⁺.

Step 3—5-Chloro-N-[2-[4-(hydroxymethyl)cyclohexyl]-5-methoxy-1,3-benzothiazol-6-yl]pyridine-3-carboxamide To a mixture of 5-chloropyridine-3-carboxylic acid (86.2 mg, 547 umol, CAS #22620-27-5) in DMF (4 mL) was added CMPI (209 mg, 820 umol) and DIEA (265 mg, 2.05 mmol). Then a mixture of [4-(6-amino-5-methoxy-1,3-benzothiazol-2-yl)cyclohexyl]methanol (200 mg, 684 umol) in DMF (4 mL) was added into the reaction mixture. The reaction mixture was then stirred at 25° C. for 2 hrs. On completion, the reaction mixture was quenched with water (0.05 mL) and concentrated in vacuo. The residue was purified by reverse phase (0.1% FA condition) to give the title compound (37.0 mg, 12% yield) as white solid. LC-MS (ESI$^+$) m/z 432.1 (M+H)$^+$.

Step 4—5-Chloro-N-[2-(4-formylcyclohexyl)-5-methoxy-1,3-benzothiazol-6-yl]pyridine-3-carboxamide To a mixture of 5-chloro-N-[2-[4-(hydroxymethyl) cyclohexyl]-5-methoxy-1,3-benzothiazol-6-yl]pyridine-3-carboxamide (37.0 mg, 85.6 umol) in DCM (1 mL) was added DMP (54.5 mg, 128 umol). The reaction mixture was stirred at 25° C. for 1 hr. On completion, the reaction mixture was quenched with saturated Na$_2$S$_2$O$_3$ (3 mL) and saturated NaHCO$_3$(3 mL) at 25° C., and then stirred for 30 minutes. The mixture was extracted with DCM (2×70 mL) then the combined organic layers was dried over Na$_2$SO$_4$, filtered and concentrated in vacuo to give the title compound (70.0 mg, 90% yield)) as white solid. LC-MS (ESI$^+$) m/z 430.2 (M+H)$^+$.

5-Cyano-N-[2-(4-formylcyclohexyl)-5-methoxy-1,3-benzothiazol-6-yl]pyridine-3-carboxamide (Intermediate BXG)

Step 1—5-Cyano-N-[2-[4-(hydroxymethyl)cyclohexyl]-5-methoxy-1,3-benzothiazol-6-yl]pyridine-3-carboxamide To a mixture of [4-(6-amino-5-methoxy-1,3-benzothiazol-2-yl)cyclohexyl]methanol (140 mg, 478 umol, synthesized via Steps 1-2 of Intermediate BXF) in DMF (1 mL) was added DIEA (61.8 mg, 478 umol. To a solution of 5-cyanopyridine-3-carboxylic acid (70.9 mg, 478 umol, CAS #887579-62-6) in DMF (1 mL) was added CMPI (122 mg, 478 umol) and DIEA (61.8 mg, 478 umol) and the mixture was stirred at 25° C. for 0.2 hour. Then the mixture was added to the reaction mixture solution dropwise. The reaction mixture was then stirred at 25° C. for 2 hours. On completion, the residue was diluted with water (30 mL) and extracted with EA (2×50 mL). The combined organic layer was dried over Na$_2$SO$_4$, filtered and concentrated in vacuo to give a residue. The residue was purified by reverse phase (0.1% FA condition) to give the title compound (50.0 mg, 24% yield) as white solid. LC-MS (ESI$^+$) m/z 423.2 (M+H)$^+$.

Step 2—5-Cyano-N-[2-(4-formylcyclohexyl)-5-methoxy-1,3-benzothiazol-6-yl]pyridine-3-carboxamide To a mixture of 5-cyano-N-[2-[4-(hydroxymethyl)cyclohexyl]-5-methoxy-1,3-benzothiazol-6-yl]pyridine-3-carboxamide (40.0 mg, 94.6 umol) in DCM (1 mL) was added DMP (52.2 mg, 123 umol). The reaction mixture was then stirred at 25° C. for 1 hour. On completion, the reaction mixture was quenched by saturated Na$_2$S$_2$O$_3$ (1 mL) and saturated NaHCO$_3$(1 mL) at 25° C., and then stirred for 30 minutes. The residue was diluted with water (15 mL) and extracted with DCM (2×20 mL). The combined organic layer was dried over Na$_2$SO$_4$, filtered and concentrated in vacuo to give the title compound (28.0 mg, 70% yield) as yellow solid. LC-MS (ESI$^+$) m/z 421.2 (M+H)$^+$.

4-[5-[[6-(Trifluoromethyl)pyridine-2-carbonyl]amino]pyrazolo[3,4-c]pyridin-2-yl]cyclohexanecarboxylic acid (Intermediate BXH)

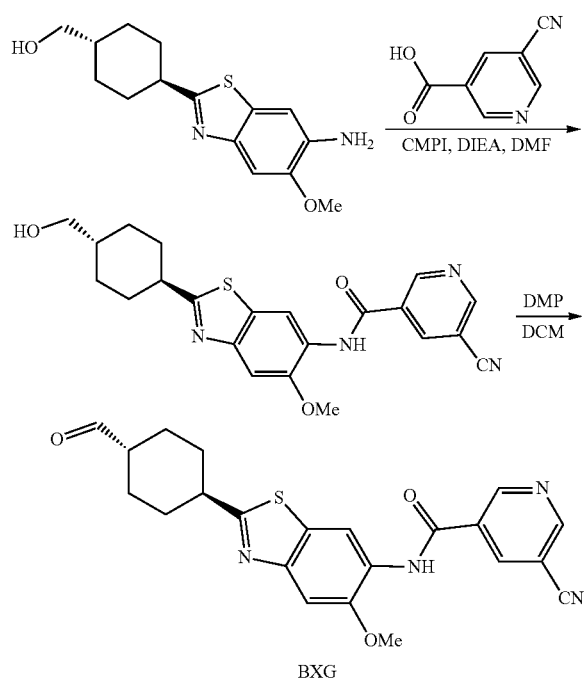

BXG

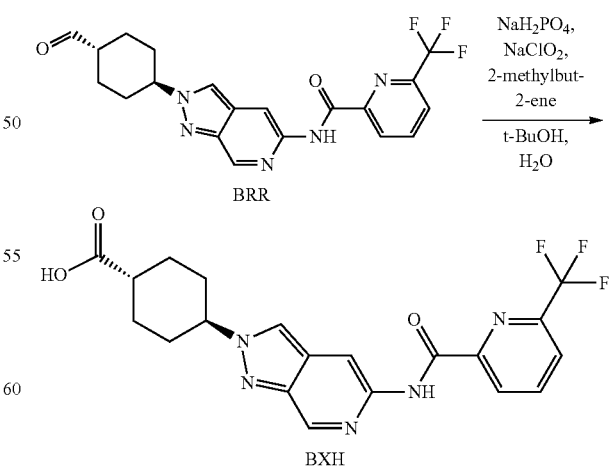

BXH

To a mixture of N-[2-(4-formylcyclohexyl)pyrazolo[3,4-c]pyridin-5-yl]-6-(trifluoromethyl)pyridine -2-carboxamide (100 mg, 239 umol, Intermediate BRR), NaH$_2$PO$_4$ (28.7 mg, 239 umol) and 2-methylbut-2-ene (67.1 mg, 958 umol) in t-BuOH (3 mL) and H₂O (1 mL) was added sodium chlorite (65.0 mg, 718 umol) at 0° C. The mixture was then stirred at 25° C. for 4 hrs. On completion, the mixture was adjusted pH to 2-3 with HCl (0.5 M), then concentrated under reduced pressure to give a residue. The residue was diluted with DCM (4 mL) and extracted with DCM 30 mL (15 mL×2). The combined organic layers were washed with H₂O 30 mL (15 mL×2), dried over Na₂SO₄, then concentrated under reduced pressure to give the title compound (100 mg, 96% yield) as white solid. LC-MS (ESI⁺) m/z 434.4 (M+H)⁺.

N-[6-cyano-2-(4-formylcyclohexyl)indazol-5-yl]-6-(trifluoromethyl)pyridine-2-carboxamide (Intermediate BXI)

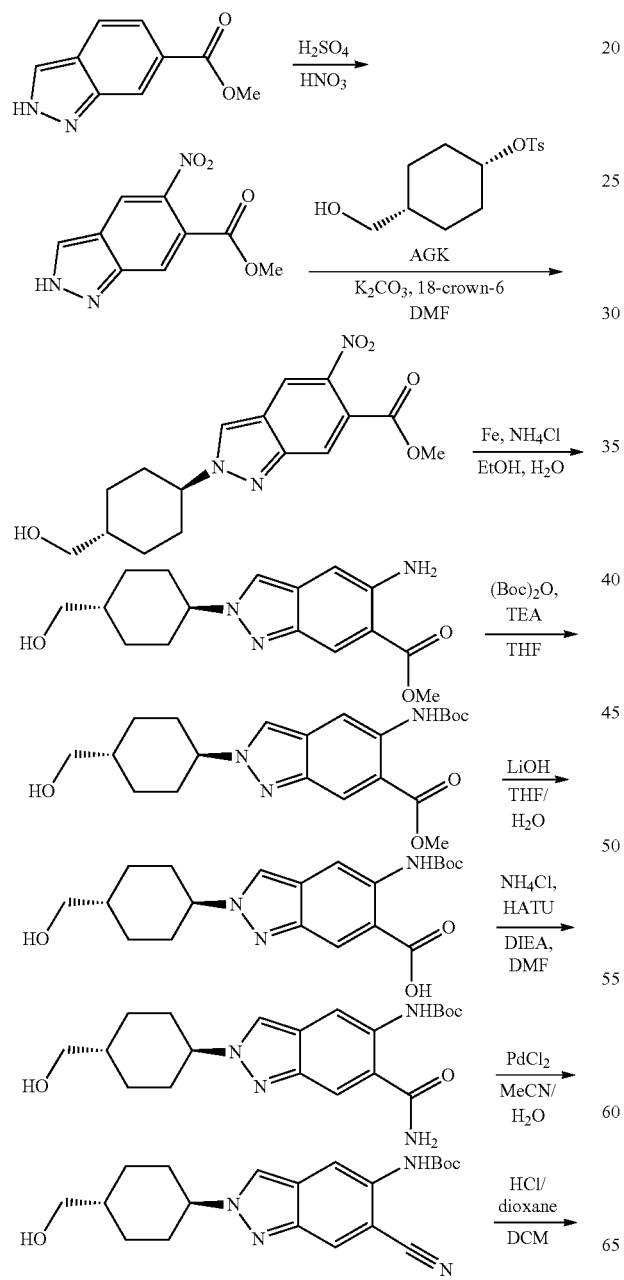

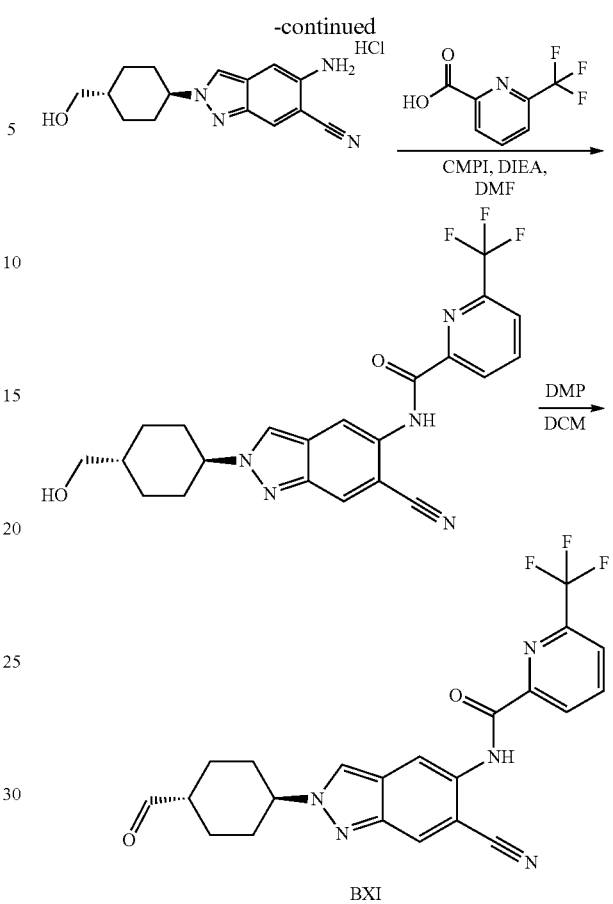

BXI

Step 1—Methyl 5-nitro-2H-indazole-6-carboxylate

To a solution of methyl 2H-indazole-6-carboxylate (30.0 g, 170 mmol, CAS #170487-40-8) in H₂SO₄ (200 mL) was added a solution of HNO₃ (45.9 g, 511 mmol, 70% solution) in H2504 (40 mL) dropwise at 0-10° C. The reaction mixture was stirred at 0° C. for 30 minutes. On completion, the mixture was poured into ice water (1.5 L), stirred and filtered. The filter cake was washed with water (4×100 mL), then dried in vacuo to give the title compound (34.0 g, 90% yield) as a yellow solid. ¹H NMR (400 MHz, DMSO-d₆) δ 8.69 (s, 1H), 8.45 (s, 1H), 7.96 (s, 1H), 3.87 (s, 3H)

Step 2—Methyl 2-[4-(hydroxymethyl)cyclohexyl]-5-nitro-indazole-6-carboxylate

To a solution of methyl 5-nitro-2H-indazole-6-carboxylate (15.0 g, 67.8 mmol) and [4-(hydroxymethyl)cyclohexyl] 4-methylbenzenesulfonate (48.2 g, 169 mmol, Intermediate AGK) in DMF (300 mL) was added K₂CO₃ (23.4 g, 169 mmol), 18-CROWN-6 (1.79 g, 6.78 mmol) and 4 Å molecular sieves (2 g). The reaction mixture was stirred at 80° C. for 2 days. On completion, the mixture was concentrated in vacuo, then diluted with water (1 L), and extracted with EA (2×300 mL). The organic layer was washed with brine (200 mL), then concentrated in vacuo. The residue was purified by silica gel chromatography (SiO₂) to give the title compound (5.00 g, 22% yield) as a yellow solid. ¹H NMR (400 MHz, CDCl₃) δ 8.42 (s, 1H), 8.23 (d, J=0.6 Hz, 1H), 8.03 (s, 1H), 4.55-4.40 (m, H), 3.93 (s, 3H), 3.57 (t, J=5.2 Hz, 2H), 2.44-2.31 (m, 2H), 2.14-1.95 (m, 4H), 1.68-1.62 (m, 1H), 1.55 (t, J=4.8 Hz, 1H), 1.35-1.24 (m, 2H).

Step 3—Methyl 5-amino-2-[4-(hydroxymethyl)cyclohexyl]indazole-6-carboxylate

To a solution of methyl 2-[4-(hydroxymethyl)cyclohexyl]-5-nitro-indazole-6-carboxylate (4.94 g, 14.8 mmol) in a mixed solvent of EtOH (70 mL) and $H_2O$ (20 mL) was added Fe (8.28 g, 148 mmol) and $NH_4Cl$ (7.93 g, 148 mmol). The reaction mixture was stirred at 70° C. for 1 hr. On completion, the mixture was diluted with water (200 mL), then extracted with EA (2×200 mL). The organic layer was washed with brine (200 mL), dried with $Na_2SO_4$, filtered and the filtrate was concentrated in vacuo to give the title compound (3.60 g, 80% yield) as a yellow solid. LC-MS (ESI$^+$) m/z 304.1 (M+H)$^+$.

Step 4—Methyl 5-(tert-butoxycarbonylamino)-2-[4-(hydroxymethyl)cyclohexyl]indazole-6-carboxylate To a solution of methyl 5-amino-2-[4-(hydroxymethyl)cyclohexyl]indazole-6-carboxylate (520 mg, 1.71 mmol) in THF (5 mL) was added TEA (260 mg, 2.57 mmol) and (Boc)$_2$O (411 mg, 1.89 mmol) dropwise. Then the mixture was stirred at 60° C. for 4 hrs. On completion, the mixture was quenched with $H_2O$ (5 mL), then extracted with EA (5 mL×3). The combined organic phase was dried over anhydrous sodium sulfate, filtered and concentrated to give a residue. The residue was purified by column chromatography (SiO$_2$, PE/EA=100:1 to 50:1) to give the title compound (450 mg, 65% yield) as yellow solid. $^1$H NMR (400 MHz, CDCl$_3$) δ 10.05 (s, 1H), 8.61-8.49 (m, 2H), 7.87 (s, 1H), 4.46-4.37 (m, 1H), 3.97 (s, 3H), 3.58 (d, J=6.0 Hz, 2H), 2.39-2.32 (m, 2H), 2.12-1.94 (m, 5H), 1.75-1.63 (m, 1H), 1.56 (s, 9H), 1.30-1.24 (m, 2H).

Step 5—5-(Tert-butoxycarbonylamino)-2-[4-(hydroxymethyl)cyclohexyl]indazole-6-carboxylic Acid To a solution of methyl 5-(tert-butoxycarbonylamino)-2-[4-(hydroxymethyl)cyclohexyl]indazole-6-carboxylate (400 mg, 991 umol) in THF (2 mL) and $H_2O$ (0.5 mL) was added LiOH·$H_2O$ (124 mg, 2.97 mmol). The mixture was then stirred at 50° C. for 4 hrs. On completion, the mixture was concentrated in vacuo, then diluted with $H_2O$ (8 mL), and adjusted to pH of 4 using 0.5 M HCl aqueous to precipitate a solid. The solid was filtered, and the filter cake was dried in vacuo to give the title compound (377 mg, 97% yield) as yellow solid. LC-MS (ESI$^+$) m/z 390.2 (M+H)$^+$.

Step 6—Tert-butyl N-[6-carbamoyl-2-[4-(hydroxymethyl)cyclohexyl]indazol-5-yl]carbamate To a solution of 5-(tert-butoxycarbonylamino)-2-[4-(hydroxymethyl)cyclohexyl]indazole-6-carboxylic acid (370 mg, 950 umol) in DMF (5 mL) was added $NH_4Cl$ (203 mg, 3.80 mmol), HATU (433 mg, 1.14 mmol) and DIEA (245 mg, 1.90 mmol). The mixture was then stirred at 20° C. for 2 hrs. On completion, the mixture was quenched with $H_2O$ (10 mL), and extracted with EA (20 mL×3). The combined organic phase was dried over anhydrous sodium sulfate, filtered and concentrated to give the title compound (320 mg, 86% yield) as yellow solid. $^1$H NMR (400 MHz, DMSO-d$_6$) δ 10.32 (s, 1H), 8.38-8.27 (m, 3H), 8.10 (s, 1H), 7.70 (s, 1H), 4.54-4.38 (m, 2H), 3.68-3.57 (m, 1H), 3.29 (t, J=5.6 Hz, 2H), 3.20-3.11 (m, 1H), 2.39-2.20 (m, 2H), 1.89 (s, 2H), 1.48 (s, 9H), 1.22-1.09 (m, 3H).

Step 7—Tert-butyl N-[6-cyano-2-[4-(hydroxymethyl)cyclohexyl]indazol-5-yl]carbamate To a solution of tert-butyl N-[6-carbamoyl-2-[4-(hydroxymethyl)cyclohexyl]indazol-5-yl]carbamate (300 mg, 772 umol) in MeCN (1 mL) and $H_2O$ (1 mL) was added PdCl$_2$ (13.6 mg, 77.2 umol). Then the mixture was then stirred at 55° C. for 2 hrs. On completion, the residue was filtered and the filtrate was purified by reverse phase (0.1% FA condition) to give the title compound (210 mg, 73% yield) as brown solid. $^1$H NMR (400 MHz, DMSO-d6) δ 9.14-9.06 (m, 1H), 8.53 (s, 1H), 8.29 (s, 1H), 7.65 (s, 1H), 4.57-4.46 (m, 2H), 2.39-2.18 (m, 2H), 1.97-1.83 (m, 6H), 1.46 (s, 9H), 1.23-1.12 (m, 3H).

Step 8—5-Amino-2-[4-(hydroxymethyl)cyclohexyl]indazole-6-carbonitrile

Tert-butyl N-[6-cyano-2-[4-(hydroxymethyl)cyclohexyl]indazol-5-yl]carbamate (150 mg, 404 umol) was dissolved in HCl/dioxane (4 M, 3 mL). The mixture was then stirred at 20° C. for 1 hrs. On completion, the mixture was concentrated in vacuo to give the title compound (124 mg, 99% yield, HCl) as yellow solid. LC-MS (ESI$^+$) m/z 271.2 (M+H)$^+$.

Step 9—N-[6-cyano-2-[4-(hydroxymethyl)cyclohexyl]indazol-5-yl]-6-(trifluoromethyl)pyridine-2-carboxamide To a solution of 6-(trifluoromethyl)pyridine-2-carboxylic acid (36.4 mg, 190 umol, CAS #131747-42-7) in DMF (0.5 mL) was added CMPI (48.7 mg, 190 umol) and DIEA (54.7 mg, 423 umol). Then 5-amino-2-[4-(hydroxymethyl)cyclohexyl]indazole-6-carbonitrile (65.0 mg, 211 umol, HCl) in DMF (0.5 mL) was added dropwise. The mixture was then stirred at 20° C. for 16 hrs. On completion, the mixture was quenched with $H_2O$ (0.5 mL) and purified by pre-HPLC (column: Phenomenex Luna C18 150*25 mm*10 um; mobile phase: [water (0.225% FA)-ACN]; B %: 38%-68%, 11.5 min.) to give the title compound (48.0 mg, 51% yield) as white solid. $^1$H NMR (400 MHz, DMSO-d$_6$) δ 10.64 (s, 1H), 8.64 (s, 1H), 8.47-8.36 (m, 3H), 8.27-8.20 (m, 2H), 4.62-4.47 (m, 2H), 3.31-3.28 (m, 2H), 2.25-2.12 (m, 2H), 2.01-1.89 (m, 4H), 1.62-1.41 (m, 1H), 1.25-1.13 (m, 2H).

Step 10—N-[6-cyano-2-(4-formylcyclohexyl)indazol-5-yl]-6-(trifluoromethyl)pyridine-2-carboxamide To a solution of N-[6-cyano-2-[4-(hydroxymethyl)cyclohexyl]indazol-5-yl]-6-(trifluoromethyl) pyridine-2-carboxamide (40.0 mg, 90.2 umol) in DCM (2 mL) was added DMP (45.9 mg, 108 umol). The mixture was then stirred at 20° C. for 1 hr. On completion, the mixture was quenched with Na$_2$S$_2$O$_3$ aqueous, and extracted with DCM (5 mL×3). The combined organic phase was washed with NaHCO$_3$ aqueous, water, brine, dried over anhydrous Na$_2$SO$_4$, filtered and concentrated in vacuo to give the title compound (39.0 mg, 97% yield) as off-white solid. LC-MS (ESI$^+$) m/z 464.1 (M+H)$^+$.

1001

5-chloro-6-methoxy-pyridine-3-carboxylic acid (CAS #884494-85-3) (Intermediate BXJ)

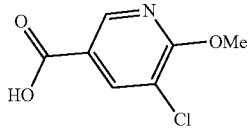
BXJ 5-chloropyridine-3-carboxylic acid (CAS #22620-27-5) (Intermediate BXK)

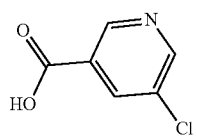
BXK 1-(8-Piperazin-1-yl-4-isoquinoly)hexahydropyrimidine-2,4-dione (Intermediate BXL)

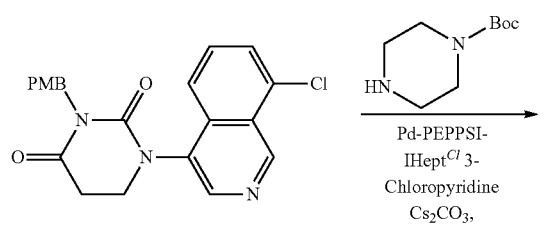

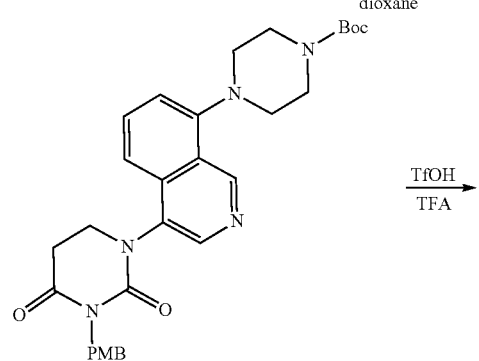

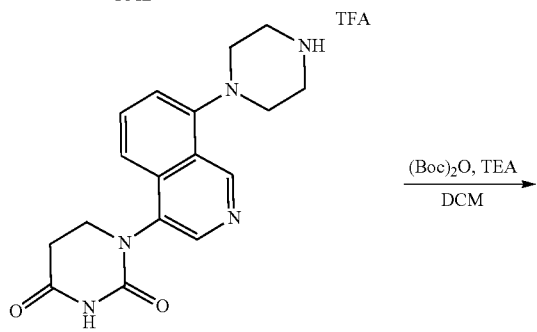

1002

-continued

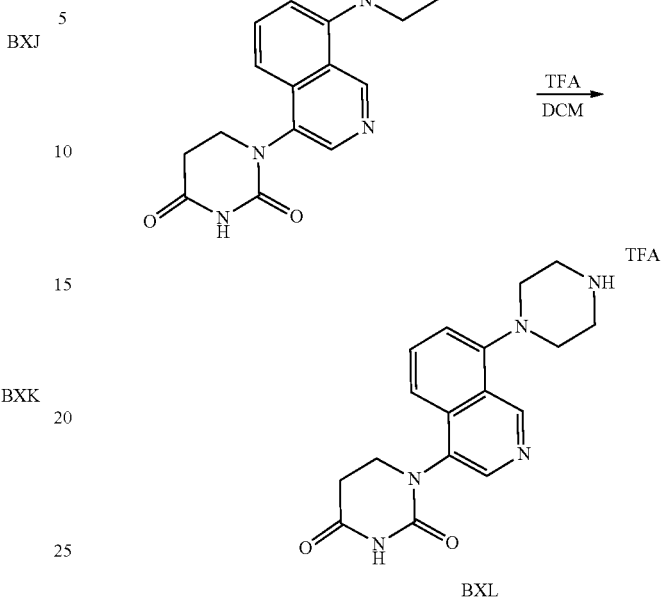
BXL

Step 1—Tert-butyl 4-[4-[3-[(4-methoxyphenyl)methyl]-2,4-dioxo-hexahydropyrimidin-1-yl]-8-isoquinolyl]piperazine-1-carboxylate To a solution of 1-(8-chloro-4-isoquinolyl)-3-[(4-methoxyphenyl)methyl]hexahydropyrimidine-2,4-dione (900 mg, 2.27 mmol, synthesized via Steps 1-2 of Intermediate BSL) and tert-butyl piperazine-1-carboxylate (508 mg, 2.73 mmol, CAS #143238-38-4) in dioxane (15 mL) was added Pd-PEPPSI-IHeptCl 3-Chloropyridine (221 mg, 227 umol) and $Cs_2CO_3$ (1.48 g, 4.55 mmol), then the mixture was stirred at 80° C. for 8 hours. On completion, the mixture was filtered and concentrated in vacuo to give the title compound (1.20 g, 96% yield) as a brown solid. $^1$H NMR (400 MHz, $CDCl_3$-d) δ 9.52 (s, 1H), 8.40 (s, 1H), 7.56 (t, J=8.0 Hz, 1H), 7.37 (d, J=8.8 Hz, 2H), 7.23-7.19 (m, 1H), 7.09 (d, J=7.6 Hz, 1H), 6.78 (d, J=8.4 Hz, 2H), 4.94 (s, 2H), 3.85-3.75 (m, 2H), 3.74 (s, 3H), 3.70-3.64 (m, J=6.4, 12.4 Hz, 4H), 3.34-3.31 (m, 1H), 3.13-3.07 (m, 2H), 2.97-2.93 (m, 2H), 2.76-2.73 (m, 1H), 1.45 (s, 9H). LC-MS (ESI$^+$) m/z 546.6 (M+H)$^+$.

Step 2—1-(8-Piperazin-1-yl-4-isoquinolyl)hexahydropyrimidine-2,4-dione

To a solution of tert-butyl 4-[4-[3-[(4-methoxyphenyl)methyl]-2,4-dioxo-hexahydropyrimidin-1-yl]-8-isoquinolyl]piperazine-1-carboxylate (600 mg, 1.10 mmol) in TFA (6 mL) was added TfOH (1 mL), then the mixture was stirred at 70° C. for 2 hours. On completion, the mixture was concentrated in vacuo to give the title compound (480 mg, 99% yield, TFA) as a black brown solid. LC-MS (ESI$^+$) m/z 326.1 (M+H)$^+$.

Step 3—Tert-butyl 4-[4-(2,4-dioxohexahydropyrimidin-1-yl)-8-isoquinolyl]piperazine-1-carboxylate To a solution of 1-(8-piperazin-1-yl-4-isoquinoly)hexahydropyrimidine-2,4-dione (480 mg, 1.09 mmol, TFA) in DCM (5 mL) was added TEA (304 uL, 2.18 mmol) and Boc₂O (357 mg, 1.64 mmol), then the mixture was stirred at 25° C. for 10 hours. On completion, the mixture was diluted with DCM (300 mL) and extracted with water (200 mL×3). The combined organic layer was dried over anhydrous Na₂SO₄, filtered and concentrated in vacuo to give the residue. The residue was purified by reverse-phase (0.1% FA condition) to give the title compound (150 mg, 32% yield) as a yellow solid. ¹H NMR (400 MHz, CDCl₃-d) δ 9.61 (s, 1H), 8.52 (s, 1H), 8.26 (s, 1H), 7.69 (t, J=8.0 Hz, 1H), 7.47 (d, J=8.4 Hz, 1H), 7.18 (d, J=7.6 Hz, 1H), 4.03-3.91 (m, 1H), 3.90-3.77 (m, 2H), 3.73 (s, 3H), 3.23-3.02 (m, 4H), 3.01-2.88 (m, 2H), 1.51 (s, 9H). LC-MS (ESI⁺) m/z 426.1 (M+H)⁺.

Step 4—1-(8-Piperazin-1-yl-4-isoquinolyl)hexahydropyrimidine-2,4-dione

To a solution of tert-butyl 4-[4-(2,4-dioxohexahydropyrimidin-1-yl)-8-isoquinolyl]piperazine-1-carboxylate (80.0 mg, 188 umol) in DCM (2 mL) was added TFA (0.5 mL, 6.75 mmol), then the mixture was stirred at 25° C. for 1 hour. On completion, the mixture was concentrated in vacuo to give the title compound (80.0 mg, 96% yield, TFA) as a brown solid. LC-MS (ESI⁺) m/z 326.1 (M+H)⁺.

3-(3-methyl-2-oxo-4-(3-(piperidin-4-yloxy)prop-1-yn-1-yl)-2,3-dihydro-1H-benzo[d]imidazol-1-yl) piperidine-2,6-dione (Intermediate BXN)

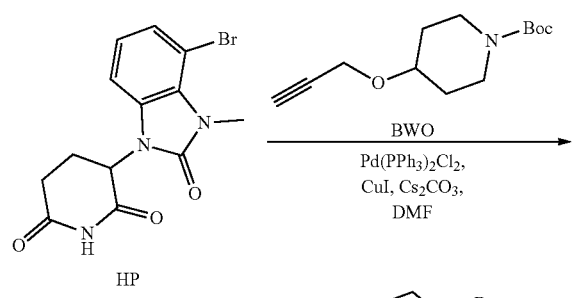

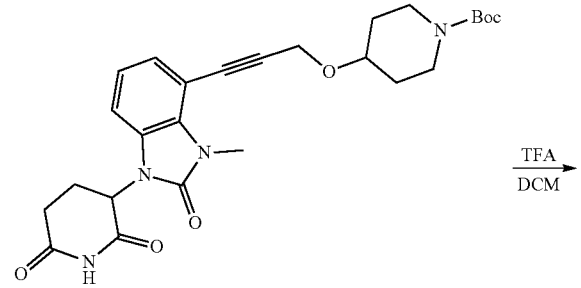

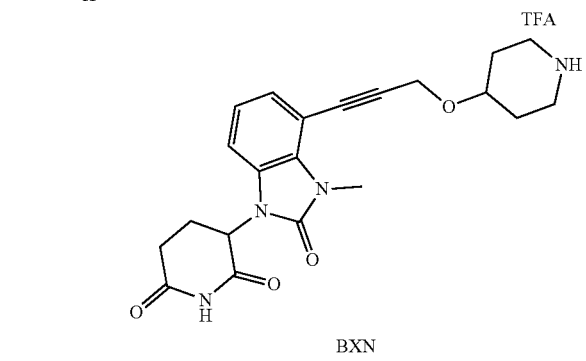

Step 1—Tert-butyl 4-((3-(1-(2,6-dioxopiperidin-3-yl)-3-methyl-2-oxo-2,3-dihydro-1H-benzo[d]imidazol-4-yl)prop-2-yn-1-yl)oxy)piperidine-1-carboxylate A mixture of 3-(4-bromo-3-methyl-2-oxo-benzimidazol-1-yl)piperidine-2,6-dione (1.70 g, 5.01 mmol, Intermediate HP), tert-butyl 4-prop-2-ynoxypiperidine-1-carboxylate (1 g, 4.18 mmol, Intermediate BWO), Pd(PPh₃)₂Cl₂ (293 mg, 417 umol), Cs₂CO₃ (2.72 g, 8.36 mmol) and CuI (79.5 mg, 417 umol) in DMF (25 mL) was degassed and purged with N₂ for 3 times. Then the mixture was stirred at 80° C. for 16 hrs under N₂ atmosphere. On completion, the reaction mixture was diluted by EtOAc (50 mL), filtered and the filtrate was concentrated in vacuo. The residue was purified by reverse phase (0.1% FA condition) to give the title compound (900 mg, 43% yield) as yellow solid. ¹H NMR (400 MHz, DMSO-d₆) δ 11.12 (s, 1H), 7.17 (d, J=7.9 Hz, 1H), 7.14-7.09 (m, 1H), 7.06-7.00 (m, 1H), 5.40 (dd, J=5.6, 12.8 Hz, 1H), 4.50 (s, 2H), 3.75-3.71 (m, 1H), 3.68-3.60 (m, 5H), 3.04 (t, J=9.6 Hz, 2H), 2.95-2.83 (m, 1H), 2.75-2.60 (m, 2H), 2.06-1.99 (m, 1H), 1.89-1.79 (m, 2H), 1.41 (d, J=4.0 Hz, 1H), 1.39 (s, 9H), 1.37-1.33 (m, 1H).

Step 2—3-(3-methyl-2-oxo-4-(3-(piperidin-4-yloxy) prop-1-yn-1-yl)-2,3-dihydro-1H-benzo[d]imidazol-1-yl)piperidine-2,6-dione To a solution of tert-butyl 4-[3-[1-(2,6-dioxo-3-piperidyl)-3-methyl-2-oxo-benzimidazol-4-yl]prop-2-ynoxy]piperidine-1-carboxylate (50 mg, 100 umol) in DCM (1 mL) was added TFA (0.3 mL). The reaction mixture was then stirred at 25° C. for 1 hr. On completion, the reaction mixture was concentrated in vacuo to give the title compound (39 mg, 97% yield) as brown oil. LC-MS (ESI⁺) m/z 397.1 (M+H)⁺.

Intermediate BXO

1-[8-[[4-4-(5-Aminoindazol-2-yl)cyclohexyl] methyl]-4-piperidyl]-4-isoquinolylihexahydro pyrimidine-2,4-dione (Intermediate BXP)

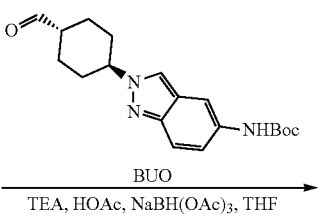

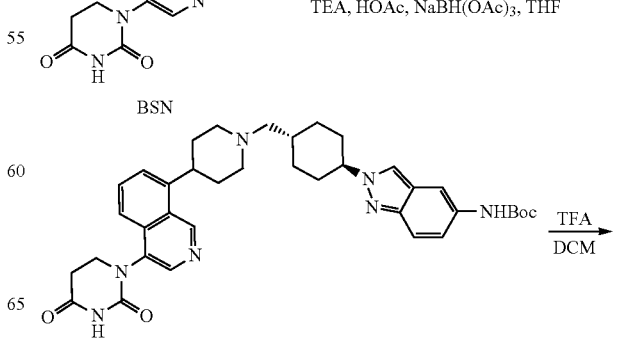

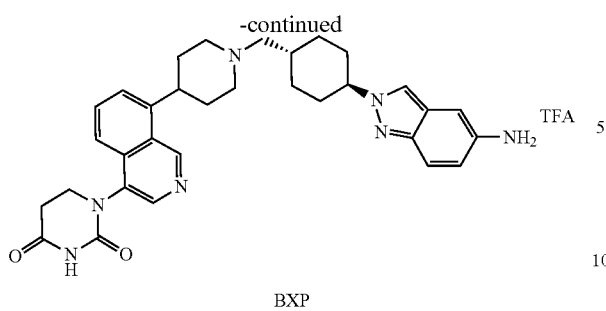

BXP

Step 1—Tert-butyl N-[2-[4-[[4-[4-(2,4-dioxohexahydropyrimidin-1-yl)-8-isoquinolyl]-1-piperidyl]methyl]cyclohexyl]indazol-5-yl]carbamate To a mixture of 1-[8-(4-piperidyl)-4-isoquinolyl]hexahydropyrimidine-2,4-dione (180 mg, 554 umol, Intermediate BSN) in DMF (5 mL) was added TEA (56.1 mg, 554 umol) until pH stabilized at 8. The mixture was stirred at 25° C. for 0.25 hr, then AcOH (33.3 mg, 554 umol) was added at −15° C. until the pH stabilized at 5~6. Subsequently, tert-butyl N-[2-(4-formylcyclohexyl)indazol-5-yl]carbamate (190 mg, 554 umol, Intermediate BUO) was added and stirred for 0.5 hr. After that, NaBH(OAc)$_3$ (152 mg, 721 umol) was added in one portion. The resulting reaction mixture was stirred at −15° C. for 1 hr. On completion, the mixture was quenched with H$_2$O (0.5 mL) and purified by reversed-phase (0.1% FA condition) to give the title compound (140 mg, 39% yield) as pink solid. $^1$H NMR (400 MHz, DMSO-d$_6$) δ 10.55 (s, 1H), 9.63 (s, 1H), 9.21 (s, 1H), 8.58 (s, 1H), 8.16 (s, 1H), 7.95-7.77 (m, 3H), 7.69-7.64 (m, 1H), 7.50-7.41 (m, 1H), 7.24-7.16 (m, 1H), 4.50-4.33 (m, 1H), 3.98-3.89 (m, 1H), 3.69-3.60 (m, 1H), 3.17 (d, J=10.4 Hz, 2H), 2.92-2.88 (m, 1H), 2.47-2.41 (m, 3H), 2.21-2.11 (m, 2H), 2.06-1.88 (m, 8H), 1.81-1.70 (m, 1H), 1.49 (s, 9H), 1.17 (t, J=7.2 Hz, 5H); LC-MS (ESI$^+$) m/z 652.4 (M+H)$^+$.

Step 2—1-[8-[1-[[4-(5-Aminoindazol-2-yl)cyclohexyl]methyl]-4-piperidyl]-4-isoquinolyl]hexahydropyrimidine-2,4-dione To a solution of tert-butyl N-[2-[4-[[4-[4-(2,4-dioxohexahydropyrimidin-1-yl)-8-isoquinolyl]-1-piperidyl]methyl]cyclohexyl]indazol-5-yl]carbamate (48.0 mg, 73.6 umol) in CH$_2$Cl$_2$ (2 mL) was added TFA (770 mg, 6.75 mmol). The mixture was then stirred at 20° C. for 1 hr. On completion, the mixture was concentrated to give the title compound (46.0 mg, 93% yield, TFA) as pink solid. LC-MS (ESI$^+$) m/z 552.40 (M+H)$^+$.

3-[4-(2,7-Diazaspiro[3.5]nonan-7-yl)-3-methyl-2-oxo-benzimidazol-1-yl]piperidine-2,6-dione (Intermediate BXQ)

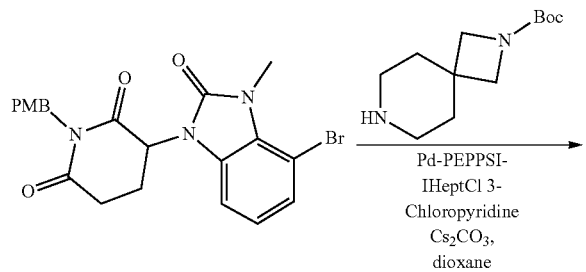

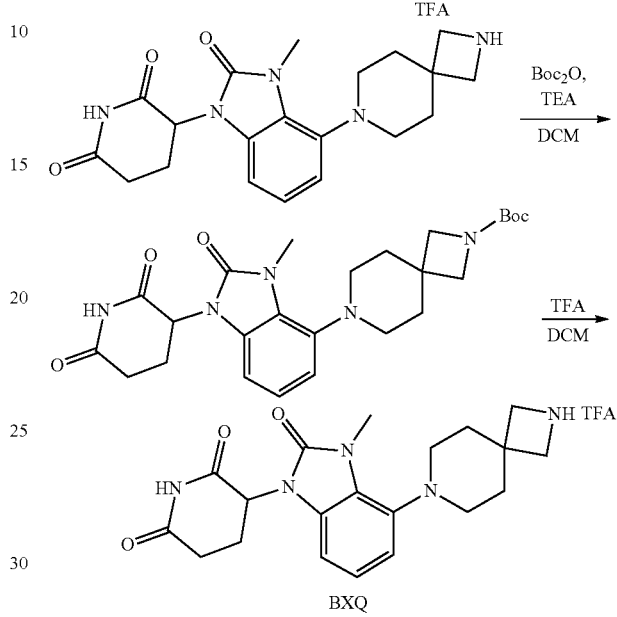

BXQ

Step 1—Tert-butyl 7-[1-[1-[(4-methoxyphenyl)methyl]-2,6-dioxo-3-piperidyl]-3-methyl-2-oxo-benzimidazol-4-yl]-2,7-diazaspiro[3.5]nonane-2-carboxylate To a solution of 3-(4-bromo-3-methyl-2-oxo-benzimidazol-1-yl)-1-[(4-methoxyphenyl)methyl]piperidine-2,6-dione (1.00 g, 2.18 mmol, synthesized via Steps 1-4 of Intermediate HP) and tert-butyl2,7-diazaspiro[3.5]nonane-2-carboxylate (592 mg, 2.62 mmol, CAS #236406-55-6) in dioxane (20 mL) was added Cs$_2$CO$_3$ (1.42 g, 4.36 mmol) and Pd-PEPPSI-IHeptCl 3-Chloropyridine (212 mg, 218 umol). Then the mixture was stirred at 100° C. for 12 hours. On completion, the mixture was filtered and concentrated in vacuo to give the residue. The residue was purified by reverse-phase (0.1% FA condition) to give the title compound (380 mg, 28% yield) as a yellow solid. $^1$H NMR (400 MHz, CDCl$_3$-d) δ 7.37 (d, J=8.4 Hz, 2H), 6.88-6.81 (m, 4H), 6.29 (dd, J=1.6, 6.8 Hz, 1H), 5.20 (dd, J=5.6, 13.2 Hz, 1H), 5.02-4.91 (m, 2H), 3.79 (s, 3H), 3.75 (s, 5H), 3.67 (s, 2H), 3.15-2.94 (m, 3H), 2.88-2.77 (m, 1H), 2.74-2.55 (m, 3H), 2.17-2.16 (m, 1H), 1.95 (s, 4H), 1.47 (s, 9H); LC-MS (ESI$^+$) m/z 604.5 (M+H)$^+$.

Step 2—3-[4-(2,7-Diazaspiro[3.5]nonan-7-yl)-3-methyl-2-oxo-benzimidazol-1-yl]piperidine-2,6-dione To a solution of tert-butyl 7-[1-[1-[(4-methoxyphenyl)methyl]-2,6-dioxo-3-piperidyl]-3-methyl-2-oxo -benzimidazol-4-yl]-2,7-diazaspiro[3.5]nonane-2-carboxylate (200 mg, 331 umol) in TFA (2 mL) was added TfOH (0.2 mL), then the mixture was stirred at 60° C. for 2 hours. On completion, the mixture was concentrated in vacuo to give the title compound (150 mg, 91% yield, TFA) as a brown solid. LC-MS (ESI+) m/z 384.2 (M+H)+.

Step 3—Tert-butyl 7-[1-(2,6-dioxo-3-piperidyl)-3-methyl-2-oxo-benzimidazol-4-yl]-2,7-diazaspiro[3.5]nonane-2-carboxylate To a solution of 3-[4-(2,7-diazaspiro[3.5]nonan-7-yl)-3-methyl-2-oxo-benzimidazol-1-yl]piperidine-2,6-dione (150 mg, 301 umol, TFA) in DCM (4 mL) was added TEA (83.9 uL, 603 umol) and Boc₂O (98.7 mg, 452 umol), then the mixture was stirred at 25° C. for 10 hours. On completion, the mixture was diluted with DCM (100 mL) and extracted with water (50 mL×3). The combined organic layer was dried over anhydrous Na₂SO₄, filtered and concentrated in vacuo to give the title compound (140 mg, 96% yield) as a brown solid. ¹H NMR (400 MHz, CDCl₃-d) δ 8.45 (s, 1H), 7.01-6.96 (m, 1H), 6.87 (d, J=8.0 Hz, 1H), 6.62-6.57 (m, 1H), 5.21 (dd, J=5.2, 12.4 Hz, 1H), 3.75 (s, 3H), 3.67 (s, 2H), 3.14-3.07 (m, J=7.6, 14.8 Hz, 3H), 2.94-2.88 (m, 1H), 2.85-2.80 (m, J=4.8, 13.2 Hz, 1H), 2.75-2.65 (m, 3H), 2.25-2.15 (m, 2H), 1.94 (s, 4H), 1.46 (s, 9H). LC-MS (ESI+) m/z 484.3 (M+H)+.

Step 4—3-[4-(2,7-Diazaspiro[3.5]nonan-7-yl)-3-methyl-2-oxo-benzimidazol-1-yl]piperidine-2,6-dione To a solution of tert-butyl 7-[1-(2,6-dioxo-3-piperidyl)-3-methyl-2-oxo-benzimidazol-4-yl]-2,7-diazaspiro[3.5]nonane-2-carboxylate (80.0 mg, 165 umol) in DCM (2 mL) was added TFA (1 mL, 13.5 mmol), then the mixture was stirred at 25° C. for 1 hour. On completion, the mixture was concentrated in vacuo to give the title compound (80.0 mg, 97% yield, TFA) as a black-brown solid. LC-MS (ESI+) m/z 384.2 (M+H)+.

3-[4-(3,9-Diazaspiro[5.5]undecan-3-yl)-3-methyl-2-oxo-benzimidazol-1-yl]piperidine-2,6-dione (Intermediate BXR)

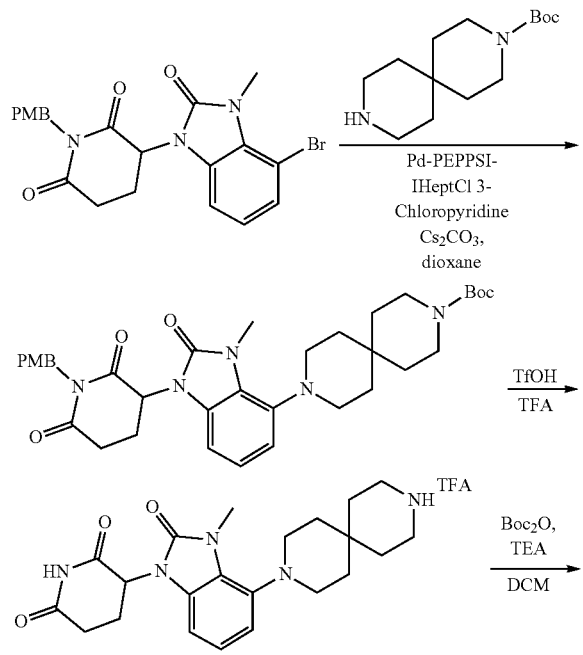

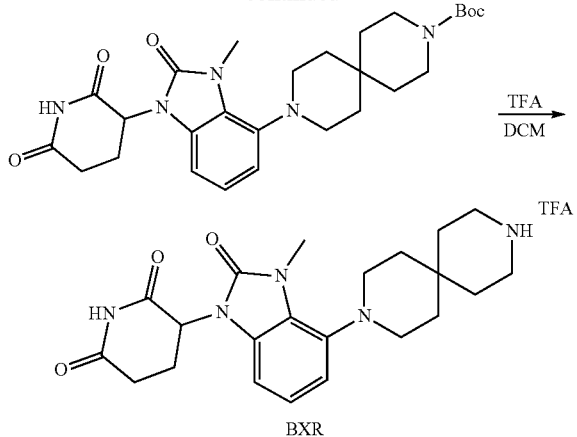

Step 1—3-[4-(3,9-Diazaspiro[5.5]undecan-3-yl)-3-methyl-2-oxo-benzimidazol-1-yl]piperidine-2,6-dione To a solution of 3-(4-bromo-3-methyl-2-oxo-benzimidazol-1-yl)-1-[(4-methoxyphenyl)methyl]piperidine-2,6-dione (1.00 g, 2.18 mmol, synthesized via Steps 1-4 of Intermediate HP) and tert-butyl-3,9-diazaspiro[5.5]undecane-3-carboxylate (666 mg, 2.62 mmol, CAS #173405-78-2) in dioxane (15 mL) was added Pd-PEPPSI-IHEPTCl 3-Chloropyridine (212 mg, 218 umol) and Cs₂CO₃ (1.42 g, 4.36 mmol). Then the mixture was stirred at 100° C. for 10 hours. On completion, the mixture was filtered and concentrated in vacuo to give the residue. The residue was purified by reverse-phase (0.1% FA) to give the title compound (400 mg, 29% yield) as yellow solid. ¹H NMR (400 MHz, CDCl₃-d) δ 7.40-7.35 (m, 2H), 6.93-6.86 (m, 2H), 6.86-6.80 (m, 2H), 6.28 (d, J=7.2 Hz, 1H), 5.21 (dd, J=5.4, 13.0 Hz, 1H), 5.02-4.92 (m, 2H), 3.80 (s, 3H), 3.76 (s, 3H), 3.47-3.39 (m, 4H), 3.04-2.90 (m, 5H), 2.87-2.77 (m, 1H), 2.68-2.55 (m, 1H), 2.18-2.11 (m, 1H), 1.74 (s, 2H), 1.65-1.63 (m, 4H), 1.48 (s, 9H), 1.43 (s, 2H). LC-MS (ESI+) m/z 632.4 (M+H)+.

Step 2—3-[4-(3,9-Diazaspiro[5.5]undecan-3-yl)-3-methyl-2-oxo-benzimidazol-1-yl]piperidine-2,6-dione To a solution of tert-butyl 9-[1-[1-[(4-methoxyphenyl)methyl]-2,6-dioxo-3-piperidyl]-3-methyl-2-oxo-benzimidazol-4-yl]-3,9-diazaspiro[5.5]undecane-3-carboxylate (200 mg, 316 umol) in TFA (2 mL) was added TfOH (0.2 mL). Then the mixture was stirred at 60° C. for 2 hours. On completion, the mixture was concentrated in vacuo to give the title compound (150 mg, 90% yield, TFA) as a brown solid. LC-MS (ESI+) m/z 412.2 (M+H)+.

Step 3—Tert-butyl 9-[1-(2,6-dioxo-3-piperidyl)-3-methyl-2-oxo-benzimidazol-4-yl]-3,9-diazaspiro[5.5]undecane-3-carboxylate To a solution of 3-[4-(3,9-diazaspiro[5.5]undecan-3-yl)-3-methyl-2-oxo-benzimidazol-1-yl]piperidine-2,6-dione (150 mg, 285 umol, TFA) in DCM (4 mL) was added TEA (79.4 uL, 570 umol) and Boc₂O (93.4 mg, 428 umol), then the mixture was stirred at 25° C. for 10 hours. On completion, the mixture was diluted with DCM (100 mL) and extracted with water (50 mL×3). The combined organic layer was dried over anhydrous Na₂SO₄, filtered and concentrated in vacuo to give the title compound (140 mg, 96% yield) as a brown solid. ¹H NMR (400 MHz, CDCl₃-d) δ 8.46-8.34 (m, 1H), 7.02-6.92 (m, 2H), 6.57 (d, J=7.2 Hz, 1H), 5.22 (dd, J=5.2, 12.4 Hz, 1H), 3.99-3.90 (m, 1H), 3.77 (s, 3H), 3.46-3.40 (m, 4H), 2.97-2.88 (m, 5H), 2.83 (dd, J=4.8, 13.2 Hz, 1H), 2.77-2.73 (m, J=4.0, 15.2 Hz, 1H), 2.22-2.16 (m, J=2.8, 5.2, 10.8 Hz, 1H), 1.74 (s, 3H), 1.65-1.63 (m, J=8.0 Hz, 4H), 1.48 (s, 9H). LC-MS (ESI⁺) m/z 512.4 (M+H)⁺.

Step 4—3-[4-(3,9-Diazaspiro[5.5]undecan-3-yl)-3-methyl-2-oxo-benzimidazol-1-yl]piperidine-2,6-dione To a solution of tert-butyl 9-[1-(2,6-dioxo-3-piperidyl)-3-methyl-2-oxo-benzimidazol-4-yl]-3,9-diazaspiro[5.5]undecane-3-carboxylate (80.0 mg, 156 umol) in DCM (2 mL) was added TFA (1 mL, 13.5 mmol), then the mixture was stirred at 25° C. for 1 hour. On completion, the mixture was concentrated in vacuo to give the title compound (80.0 mg, 97% yield, TFA) as a blackibrown solid. LC-MS (ESI⁺) m/z 412.2 (M+H)⁺.

5-cyano-N-[2-(4-formylcyclohexyl)-6-[(1R,4R)-2-oxa-5-azabicyclo[2.2.1]heptan-5-yl]indazol-5-yl]pyridine-3-carboxamide (Intermediate BXS)

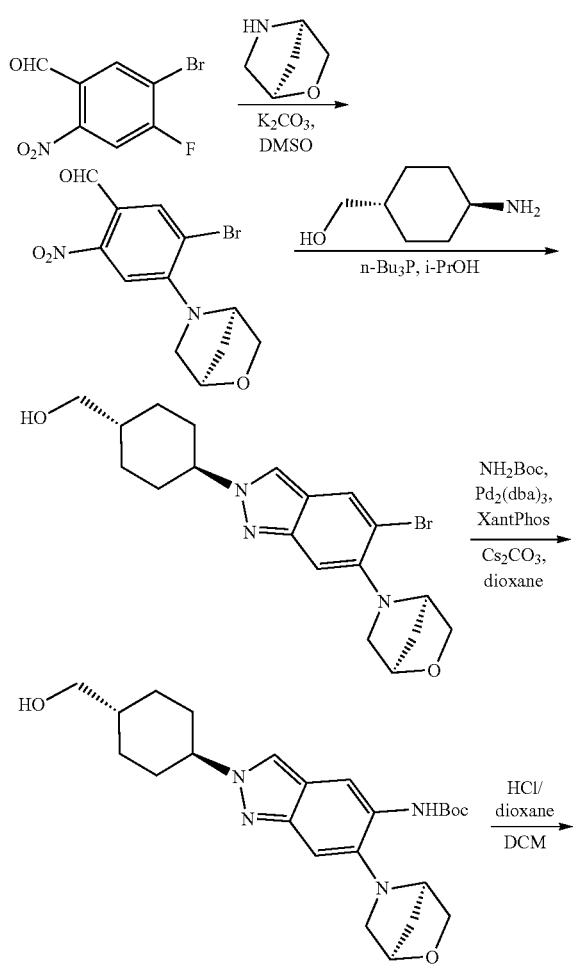

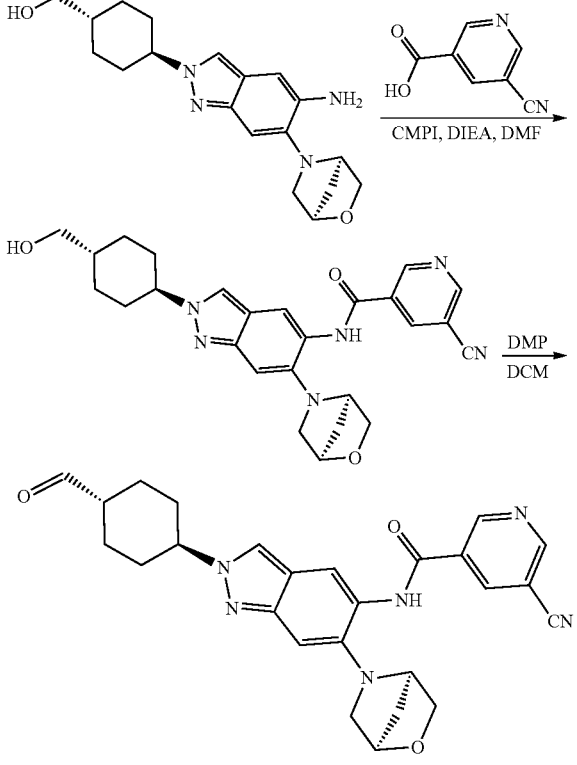

BXS

Step 1—5-bromo-2-nitro-4-[(1R,4R)-2-oxa-5-azabicyclo[2.2.1]heptan-5-yl]benzaldehyde To a solution of (1R,4R)-2-oxa-5-azabicyclo[2.2.1]heptane (1.23 g, 9.07 mmol, HCl salt, CAS #66147-56-0) and K₂CO₃ (1.67 g, 12.10 mmol) in DMSO (15 mL) was added 5-bromo-4-fluoro-2-nitro-benzaldehyde (1.5 g, 6.05 mmol, CAS #213382-45-7). Then the reaction mixture was stirred at 80° C. for 2 hours. On completion, the reaction was diluted with EtOAc (100 mL) and washed with brine (40 mL×4). The organic layer was dried over Na₂SO₄ and filtered. The filtrate was concentrated in vacuo to give the title compound (1.50 g, 76% yield) as yellow solid. ¹H NMR (400 MHz, CDCl₃) δ 10.22 (s, 1H), 8.17 (s, 1H), 7.21 (s, 1H), 4.83 (d, J=1.2 Hz, 1H), 4.72 (s, 1H), 4.12-4.07 (m, 2H), 3.99 (dd, J=1.6, 8.0 Hz, 1H), 3.48 (d, J=10.0 Hz, 1H), 2.10-2.05 (m, 2H).

Step 2—[4-[5-bromo-6-[(1R,4R)-2-oxa-5-azabicyclo[2.2.1]heptan-5-yl]indazol-2-yl]cyclohexyl]methanol To a solution of 5-bromo-2-nitro-4-[(1R,4R)-2-oxa-5-azabicyclo[2.2.1]heptan-5-yl]benzaldehyde (1.50 g, 4.59 mmol) in i-PrOH (15 mL) was added (4-aminocyclohexyl)methanol (710 mg, 5.50 mmol, CAS #1467-84-1). The mixture was heated at 80° C. for 8 hours under N₂. Then, the mixture was cooled to 25° C. and tritert-butylphosphane (2.78 g, 13.7 mmol) was added. The reaction mixture was then heated to 80° C. for 10 hours. On completion, the reaction mixture was concentrated in vacuo. The residue was purified by column chromatography (SiO₂, PE:EA=3:1 to 0:1, PE:EA=0:1, Pl:R=0.3) to give the title compound (1 g, 54% yield) as yellow solid. $^1$H NMR (400 MHz, DMSO-d$_6$) δ 8.23 (s, 1H), 7.94 (s, 1H), 7.13 (s, 1H), 4.56 (s, 1H), 4.48 (t, J=5.2 Hz, 1H), 4.41-4.33 (m, 1H), 4.33-4.29 (m, 1H), 3.96 (d, J=7.6 Hz, 1H), 3.73 (dd, J=1.6, 7.5 Hz, 1H), 3.52 (dd, J=1.2, 9.8 Hz, 1H), 3.28 (t, J=5.6 Hz, 2H), 3.24 (d, J=10.1 Hz, 1H), 2.14-2.05 (m, 2H), 1.91-1.76 (m, 6H), 1.63-1.52 (m, 1H), 1.19-1.10 (m, 2H).

Step 3—Tert-butyl N-[2-[4-(hydroxymethyl)cyclohexyl]-6-[(1R,4R)-2-oxa-5-azabicyclo[2.2.1]heptan-5-yl]indazol-5-yl]carbamate To a solution of [4-[5-bromo-6-[(1R,4R)-2-oxa-5-azabicyclo[2.2.1]heptan-5-yl]indazol-2-yl]cyclohexyl]methanol (500 mg, 1.23 mmol), NH$_2$Boc (288 mg, 2.46 mmol), Xantphos (142 mg, 246 umol) and Cs$_2$CO$_3$ (1.20 g, 3.69 mmol) in dioxane (5 mL) was added Pd$_2$(dba)$_3$ (112 mg, 123 umol). Then the mixture was stirred at 110° C. for 16 hours under N$_2$. On completion, the reaction mixture was filtered and the filtrate was concentrated in vacuo. The residue was purified by prep-HPLC (column: YMC Triart C18 250*50 mm*7 um; mobile phase: [water (0.225% FA)-ACN]; B %: 35%-65%, min) to give the title compound (140 mg, 26% yield) as yellow solid. $^1$H NMR (400 MHz, DMSO-d$_6$) δ 8.20-8.13 (m, 1H), 8.08 (s, 1H), 7.48 (s, 1H), 6.86 (s, 1H), 4.54 (s, 1H), 4.39-4.27 (m, 1H), 4.21 (s, 1H), 3.97 (d, J=7.6 Hz, 1H), 3.72 (d, J=7.2 Hz, 1H), 3.46 (d, J=9.6 Hz, 1H), 3.28 (d, J=6.0 Hz, 2H), 3.04 (d, J=9.6 Hz, 1H), 2.12-2.07 (m, 3H), 1.95-1.75 (m, 6H), 1.61-1.47 (m, 1H), 1.43 (s, 9H), 1.28-1.05 (m, 2H).

Step 4—[4-[5-amino-6-[(1R,4R)-2-oxa-5-azabicyclo[2.2.1]heptan-5-yl]indazol-2-yl]cyclohexyl]methanol To a solution of tert-butyl N-[2-[4-(hydroxymethyl)cyclohexyl]-6-[(1R,4R)-2-oxa-5-azabicyclo[2.2.1]heptan-5-yl]indazol-5-yl]carbamate (140 mg, 316 umol) in DCM (1 mL) was added HCl/dioxane (4 M, 12.6 mL), then the reaction mixture was stirred at 25° C. for 2 hours. On completion, the reaction mixture was concentrated in vacuo to give the title compound (119 mg, 99% yield, HCl) as brown solid. LC-MS (ESI$^+$) m/z 343.1 (M+H)$^+$.

Step 5—5-cyano-N-[2-[4-(hydroxymethyl)cyclohexyl]-6-[(1R,4R)-2-oxa-5-azabicyclo[2.2.1]heptan-5-yl]indazol-5-yl]pyridine-3-carboxamide To a mixture of 5-cyanopyridine-3-carboxylic acid (46.5 mg, 314 umol, CAS #887575-62-6) and DIEA (60.8 mg, 471 umol) in DMF (1 mL) was added CMPI (80.2 mg, 314 umol), then the mixture was stirred at 20° C. for 10 mins. Then the mixture was add into a solution of [4-[5-amino-6-[(1R,4R)-2-oxa-5-azabicyclo[2.2.1]heptan-5-yl]indazol-2-yl]cyclohexyl]methanol (119 mg, 314 umol, HCl salt) and DIEA (60.8 mg, 471 umol) in DMF (0.5 mL) at 20° C. The reaction mixture was stirred at 20° C. for 2 hours. On completion, the reaction mixture was added dropwise into H$_2$O (100 mL), filtered and the filtrate was concentrated in vacuo. The residue was purified by prep-HPLC (column: Phenomenex Synergi C18 100*21.2 mm*4 um; mobile phase: [water (0.225% FA)-ACN]; B %: 17%-47%, 11.5 min) to give the title compound (90 mg, 61% yield) as brown solid. $^1$H NMR (400 MHz, DMSO-d$_6$) δ 10.10 (s, 1H), 9.36 (d, J=2.0 Hz, 1H), 9.21 (d, J=1.6 Hz, 1H), 8.80 (s, 1H), 8.25 (s, 1H), 7.64 (s, 1H), 6.94 (s, 1H), 4.47 (s, 2H), 4.40-4.29 (m, 2H), 4.01 (d, J=7.6 Hz, 1H), 3.72 (d, J=6.4 Hz, 1H), 3.43 (d, J=8.4 Hz, 1H), 3.29 (s, 2H), 2.99 (d, J=9.6 Hz, 1H), 2.13 (d, J=9.2 Hz, 2H), 1.93-1.81 (m, 5H), 1.76 (d, J=9.6 Hz, 1H), 1.53-1.41 (m, 1H), 1.20-1.07 (m, 2H).

Step 6—5-cyano-N-[2-(4-formylcyclohexyl)-6-[(1R,4R)-2-oxa-5-azabicyclo[2.2.1]heptan-5-yl]indazol-5-yl]pyridine-3-carboxamide To a solution of 5-cyano-N-[2-[4-(hydroxymethyl)cyclohexyl]-6-[(1R,4R)-2-oxa-5-azabicyclo[2.2.1]heptan-5-yl]indazol-5-yl]pyridine-3-carboxamide (80.0 mg, 169 umol) in DCM (1 mL) was added DMP (93.3 mg, 220 umol), then the reaction mixture was stirred at 25° C. for 2 hours. On completion, the reaction mixture was quenched with saturated Na$_2$S$_2$O$_3$ (15 mL) and saturated NaHCO$_3$ (10 mL) at 25° C., and then stirred for 15 minutes. The mixture was extracted with DCM (30 mL×2), then the combined organic layers were washed with saturated NaCl (20 mL×2) and dried over Na$_2$SO$_4$, and filtered. The filtrate was concentrated in vacuo to give the title compound (80 mg, 40% yield) as white solid. LC-MS (ESI$^+$) m/z 471.2 (M+H)$^+$.

2-fluoro-3-(trifluoromethyl)benzoic acid (CAS #115029-22-6) (Intermediate BXV)

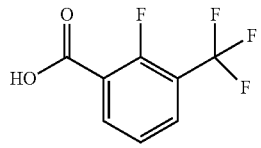

4-(trifluoromethyl)thiazole-2-carboxylic acid (CAS #944900-55-4) (Intermediate BXW)

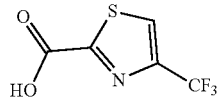

2-Fluoro-N-[2-(4-formylcyclohexyl)-6-methoxyindazol-5-yl]-3-(trifluoromethyl)benzamide (Intermediate BXX)

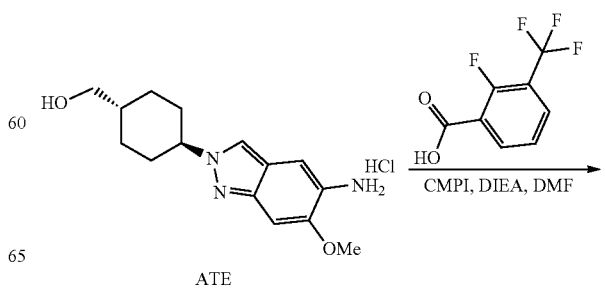

1013
-continued

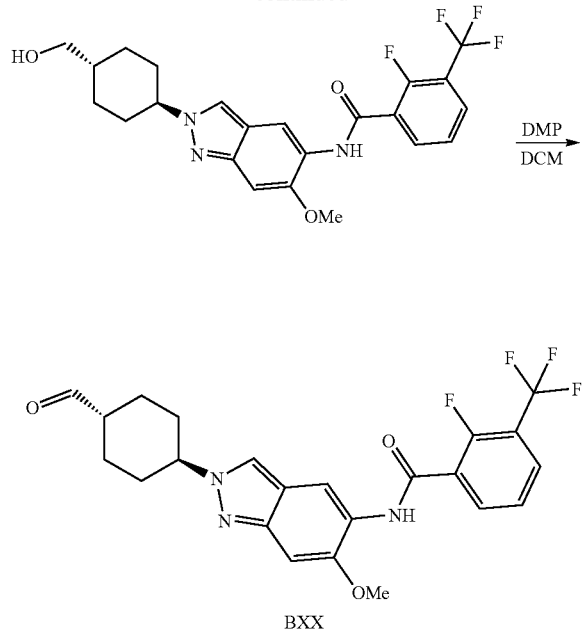

BXX

Step 1—2-Fluoro-N-[2-[4-(hydroxymethyl)cyclohexyl]-6-methoxy-indazol-5-yl]-3-(trifluoromethyl)benzamide To a solution of [4-(5-amino-6-methoxy-indazol-2-yl)cyclohexyl]methanol (300 mg, 962 umol, HCl, Intermediate ATE) and 2-fluoro-3-(trifluoromethyl)benzoic acid (200 mg, 962 umol, CAS #115029-22-6) in DMF (5 mL) was added DIEA (335 uL, 1.92 mmol) and CMPI (295 mg, 1.15 mmol), then the mixture was stirred at 25° C. for 1 hour. On completion, the mixture was poured into water (15 mL), then filtered and the filter cake was dried in vacuo to give the title compound (311 mg, 69% yield) as a brown solid. LC-MS (ESI$^+$) m/z 466.2 (M+H)$^+$.

Step 2—2-Fluoro-N-[2-(4-formylcyclohexyl)-6-methoxy-indazol-5-yl]-3-(trifluoromethyl)benzamide To a solution of 2-fluoro-N-[2-[4-(hydroxymethyl)cyclohexyl]-6-methoxy-indazol-5-yl]-3-(trifluoromethyl)benzamide (150 mg, 322 umol) in DCM (3 mL) was added DMP (150 uL, 483 umol), then the mixture was stirred at 25° C. for 1 hour. On completion, the mixture was quenched with sodium thiosulfate pentahydrate (3 mL) and NaHCO$_3$ (3 mL), then extracted with DCM (20 mL×3). The combined organic layer was concentrated in vacuo to give the title compound (140 mg, 93% yield) as a brown solid. $^1$H NMR (400 MHz, DMSO-d$_6$) δ 9.74 (d, J=4.0 Hz, 1H), 9.64 (s, 1H), 8.36 (s, 1H), 8.31 (s, 1H), 8.08 (t, J=6.8 Hz, 1H), 7.55 (t, J=7.6 Hz, 1H), 7.09 (s, 1H), 4.40 (tt, J=3.6, 11.6 Hz, 1H), 3.90 (s, 3H), 2.45-2.37 (m, 1H), 2.20 (dd, J=2.8, 12.4 Hz, 2H), 2.14-2.07 (m, 2H), 1.96 (dt, J=9.2, 12.4 Hz, 2H), 1.44 (dq, J=3.2, 12.8 Hz, 2H), 1.23 (s, 1H). LC-MS (ESI$^+$) m/z 464.2 (M+H)$^+$.

1014

1-[8-(3,8-Diazabicyclo[3.2.1]octan-3-yl)-4-isoquinolyl]hexahydropyrimidine-2,4-dione (Intermediate BXY)

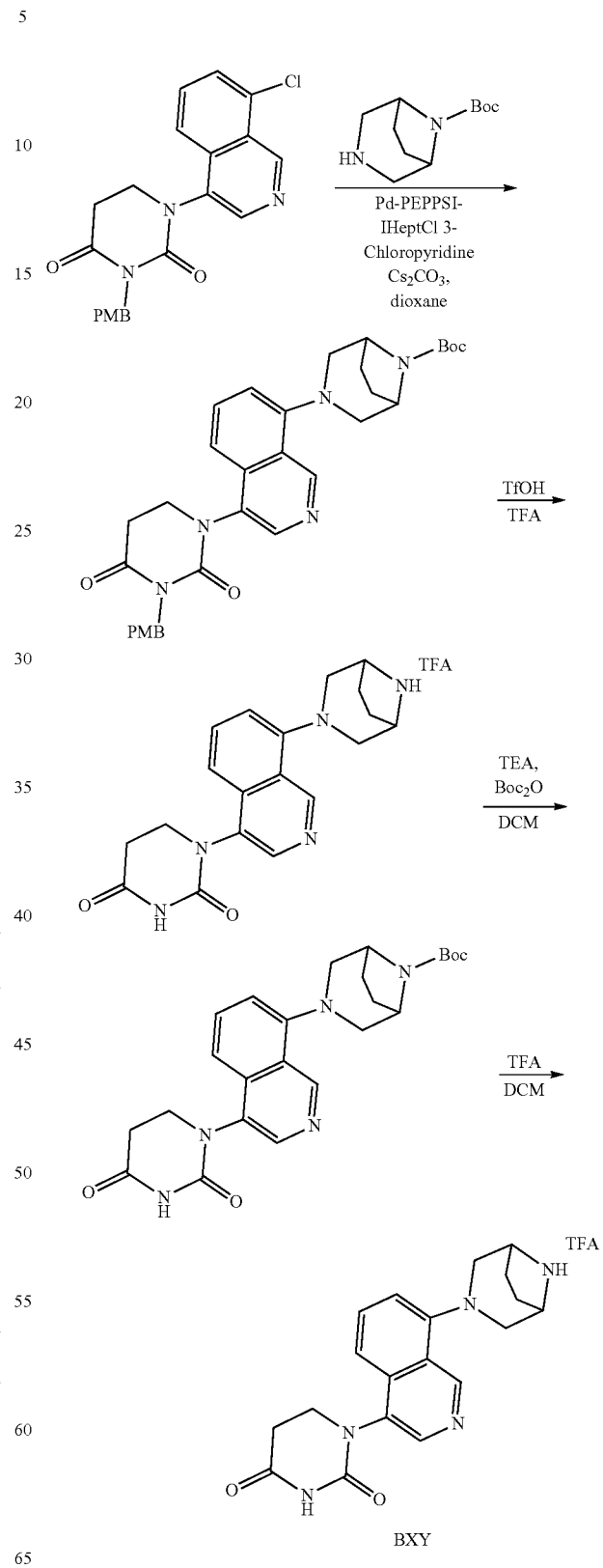

BXY

Step 1—Tert-butyl 3-[4-[3-[(4-methoxyphenyl)methyl]-2,4-dioxo-hexahydropyrimidin-1-yl]-8-isoquinolyl]-3,8-diazabicyclo[3.2.1]octane-8-carboxylate To a solution of 1-(8-chloro-4-isoquinolyl)-3-[(4-methoxyphenyl)methyl]hexahydropyrimidine-2,4-dione (500 mg, 1.26 mmol, synthesized via Steps 1-2 of Intermediate BSL) and tert-butyl3,8-diazabicyclo[3.2.1]octane-8-carboxylate (321 mg, 1.52 mmol, CAS #149771-44-8) in dioxane (8 mL) was added Pd-PEPPSI-IHEPTCl 3-Chloropyridine (123 mg, 126 umol) and Cs$_2$CO$_3$ (823 mg, 2.53 mmol). Then the mixture was stirred at 80° C. for 8 hours. On completion, the mixture was filtered and the filtrate was extracted with water (50 mL) and EA (30 mL×3). The combined organic layer was concentrated in vacuo to give the title compound (660 mg, 91% yield) as a yellow solid. $^1$H NMR (400 MHz, CDCl$_3$-d) δ 9.66 (s, 1H), 8.45 (s, 1H), 7.61 (t, J=8.0 Hz, 1H), 7.41 (d, J=8.4 Hz, 2H), 7.32 (d, J=8.4 Hz, 1H), 7.20 (d, J=7.6 Hz, 1H), 6.83 (d, J=8.8 Hz, 2H), 4.98 (s, 2H), 4.46-4.30 (m, 2H), 3.89-3.80 (m, 1H), 3.78 (s, 3H), 3.73-3.67 (m, 1H), 3.27-3.07 (m, 4H), 3.02-2.96 (m, 2H), 2.30-2.17 (m, 2H), 1.50 (s, 9H), 1.47 (d, J=2.0 Hz, 2H). LC-MS (ESI$^+$) m/z 572.2 (M+H)$^+$.

Step 2—1-[8-(3,8-Diazabicyclo[3.2.1]octan-3-yl)-4-isoquinolyl]hexahydropyrimidine-2,4-dione To a solution of tert-butyl 3-[4-[3-[(4-methoxyphenyl)methyl]-2,4-dioxo-hexahydropyrimidin-1-yl]-8-isoquinolyl]-3,8-diazabicyclo[3.2.1]octane-8-carboxylate (660 mg, 1.15 mmol) in TFA (6 mL) was added TfOH (1 mL), then the mixture was stirred at 70° C. for 2 hours. On completion, the mixture was concentrated in vacuo to give the title compound (500 mg, 93% yield, TFA) as a brown solid.

Step 3—Tert-butyl 3-[4-(2,4-dioxohexahydropyrimidin-1-yl)-8-isoquinolyl]-3,8-diazabicyclo[3.2.1]octane-8-carboxylate To a solution of 1-[8-(3,8-diazabicyclo[3.2.1] octan-3-yl)-4-isoquinolyl]hexahydropyrimidine-2,4-dione (500 mg, 1.07 mmol, TFA) in DCM (5 mL) was added TEA (299 uL, 2.15 mmol) and Boc$_2$O (370 uL, 1.61 mmol), then the mixture was stirred at 25° C. for 10 hours. On completion, the mixture was filtered and filtrate was extracted with DCM (50 mL) and water (30 mL×3). The combined organic layer was dried over anhydrous Na$_2$SO$_4$, then concentrated in vacuo to give the residue. The residue was purified by reverse-phase (0.1% FA condition) to give the title compound (212 mg, 44% yield) as a yellow solid. $^1$H NMR (400 MHz, CDCl$_3$-d) δ 9.73 (s, 1H), 8.56 (s, 1H), 7.85 (s, 1H), 7.77-7.71 (m, 1H), 7.50 (d, J=8.4 Hz, 1H), 7.29 (s, 1H), 4.06-3.95 (m, 1H), 3.86 (td, J=6.0, 12.4 Hz, 1H), 3.79-3.70 (m, 1H), 3.33-3.10 (m, 4H), 3.06-2.95 (m, 2H), 2.28 (d, J=8.4 Hz, 2H), 2.17-2.03 (m, 3H), 1.53 (s, 9H). LC-MS (ESI$^+$) m/z 452.2 (M+H)$^+$.

Step 4—1-[8-(3,8-Diazabicyclo[3.2.1]octan-3-yl)-4-isoquinolyl]hexahydropyrimidine-2,4-dione To a solution of tert-butyl 3-[4-(2,4-dioxohexahydropyrimidin-1-yl)-8-isoquinolyl]-3,8-diazabicyclo[3.2.1]octane-8-carboxylate (70.0 mg, 155 umol) in DCM (1.5 mL) was added TFA (0.5 mL, 6.75 mmol), then the mixture was stirred at 25° C. for 1 hour. On completion, the mixture was concentrated in vacuo to give the title compound (60.0 mg, 83% yield, TFA) as a brown solid. LC-MS (ESI$^+$) m/z 352.2 (M+H)$^+$.

1-[8-(3,6-Diazabicyclo[3.1.1]heptan-3-yl)-4-isoquinolyl]hexahydropyrimidine-2,4-dione (Intermediate BXZ)

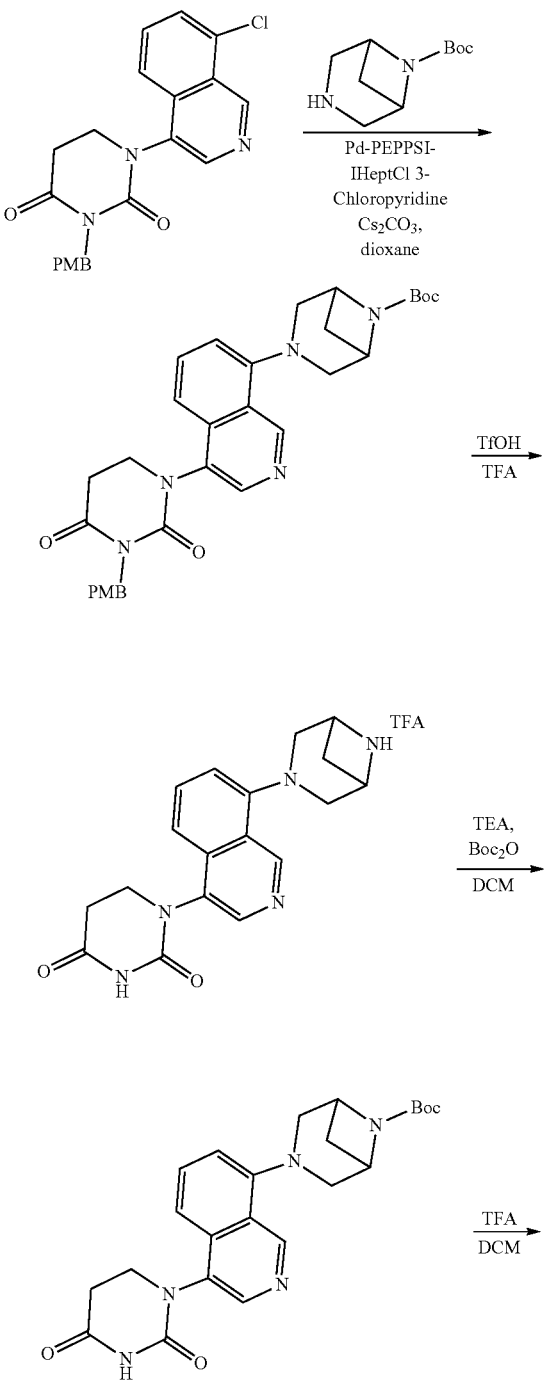

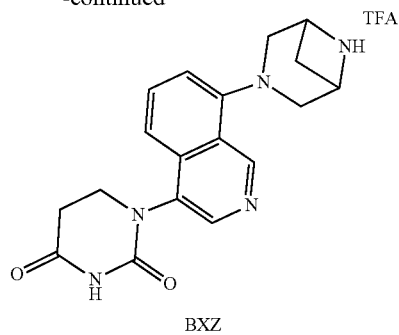

BXZ

Step 1—Tert-butyl 3-[4-[3-[(4-methoxyphenyl)methyl]-2,4-dioxo-hexahydropyrimidin-1-yl]-8-isoquinolyl]-3,6-diazabicyclo[3.1.1]heptane-6-carboxylate To a solution of 1-(8-chloro-4-isoquinolyl)-3-[(4-methoxyphenyl)methyl]hexahydropyrimidine-2,4-dione (500 mg, 1.26 mmol, synthesized via Steps 1-2 of Intermediate BSL) and tert-butyl3,6-diazabicyclo[3.1.1]heptane-6-carboxylate (275 mg, 1.39 mmol, CAS #869494-16-6) in dioxane (10 mL) was added Pd-PEPPSI-IHEPTCl 3-Chloropyridine (122 mg, 126 umol) and $Cs_2CO_3$ (823 mg, 2.53 mmol), then the mixture was stirred at 80° C. for 10 hours. On completion, the mixture was filtered and diluted with water (40 mL), then extracted with EA (4×50 mL), dried over anhydrous $Na_2SO_4$, filtered and concentrated in vacuo to give the title compound (650 mg, 92% yield) as a yellow solid. $^1$H NMR (400 MHz, DMSO-$d_6$) δ 9.58 (s, 1H), 8.51 (s, 1H), 7.75-7.68 (m, 1H), 7.56 (d, J=8.4 Hz, 1H), 7.47 (d, J=7.6 Hz, 1H), 7.26 (d, J=8.4 Hz, 2H), 6.88 (d, J=8.4 Hz, 2H), 4.83 (s, 2H), 4.20 (s, 2H), 3.73 (s, 3H), 3.33 (s, 4H), 3.17-3.06 (m, 1H), 3.00-2.91 (m, 1H), 2.61-2.53 (m, 1H), 1.66 (d, J=7.6 Hz, 1H), 1.37 (s, 9H), 0.88-0.72 (m, 2H). LC-MS (ESI$^+$) m/z 558.3 (M+H)$^+$.

Step 2—1-[8-(3,6-Diazabicyclo[3.1.1]heptan-3-yl)-4-isoquinolyl]hexahydropyrimidine-2,4-dione To a solution of tert-butyl 3-[4-[3-[(4-methoxyphenyl)methyl]-2,4-dioxo-hexahydropyrimidin-1-yl]-8-isoquinolyl]-3,6-diazabicyclo[3.1.1]heptane-6-carboxylate (600 mg, 1.08 mmol) in TFA (6 mL) was added TfOH (1.70 g, 11.3 mmol), then the mixture was stirred at 70° C. for 2 hours. On completion, the mixture was concentrated in vacuo to give the title compound (330 mg, 90% yield) as a yellow oil.

Step 3—Tert-butyl 3-[4-(2,4-dioxohexahydropyrimidin-1-yl)-84 isoquinolyl]-3,6-diazabicyclo[3.1.1]heptane-6-carboxylate To a solution of 1-[8-(3,6-diazabicyclo[3.1.1]heptan-3-yl)-4-isoquinolyl]hexahydropyrimidine-2,4-dione (330 mg, 978 umol) in DCM (5 mL) was added TEA (198 mg, 1.96 mmol) and $Boc_2O$ (320 mg, 1.47 mmol), then the mixture was stirred at 25° C. for 8 hours. On completion, the mixture was diluted with DCM (30 mL) and water (50 mL), then extracted with DCM (4×70 mL), dried over anhydrous $Na_2SO_4$, filtered and concentrated in vacuo to give the residue. The residue was purified by reverse-phase (0.1% FA) to give the title compound (200 mg, 46% yield) as a yellow solid. LC-MS (ESI$^+$) m/z 438.2 (M+H)$^+$.

Step 4—1-[8-(3,6-Diazabicyclo[3.1.1]heptan-3-yl)-4-isoquinolyl]hexahydropyrimidine-2,4-dione To a solution of tert-butyl 3-[4-(2,4-dioxohexahydropyrimidin-1-yl)-8-isoquinolyl]-3,6-diazabicyclo[3.1.1]heptane-6-carboxylate (70.0 mg, 160 umol) in DCM (1.5 mL) was added TFA (770 mg, 6.75 mmol), then the mixture was stirred at 25° C. for 1 hour. On completion, the mixture was concentrated in vacuo to give the title compound (70.0 mg, 96% yield, TFA) as a yellow oil. LC-MS (ESI$^+$) m/z 338.1 (M+H)$^+$.

(1R,3R)-methyl 3-(5-methoxy-6-(6-(trifluoromethyl)picolinamido)benzo[d]thiazol-2-yl) cyclobutanecarboxylate (Intermediate CAA)

-continued

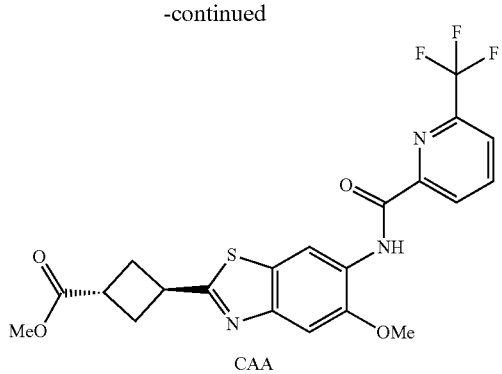

CAA

Step 1—(1r,3r)-Methyl 3-((4-bromo-2-iodo-5-methoxyphenyl)carbamoyl)cyclobutanecarboxylate To a solution of 3-methoxycarbonylcyclobutanecarboxylic acid (2.00 g, 12.6 mmol, CAS 1401103-71-6), 4-bromo-2-iodo-5-methoxy-aniline (4.15 g, 12.6 mmol, Intermediate BCT) in DCM (50 mL) was added $T_3P$ (12.0 g, 18.9 mmol) and pyridine (5.00 g, 63.2 mmol). The mixture was stirred at 25° C. for 3 hours. On completion, the reaction mixture was diluted with water (50 mL), then extracted with EA (3×50 ml). The combined organic layers were concentrated in vacuo to give the title compound (5.9 g, 99% yield) as a white solid. LC-MS (ESI$^+$) m/z 467.8 (M+H)$^+$.

Step 2—(1R,3R)-methyl 3-((4-bromo-2-iodo-5-methoxyphenyl)carbamothioyl)cyclobutane carboxylate To a solution of methyl 3-[(4-bromo-2-iodo-5-methoxyphenyl)carbamoyl]-cyclobutanecarboxylate (5.90 g, 12.6 mmol) in THF (60 mL) was added $P_2S_5$ (3.36 g, 15.1 mmol). The reaction mixture was stirred at 25° C. for 5 hours. On completion, the reaction was filtered, and the filtrate was concentrated in vacuo to give the title compound (6.1 g, 99% yield) as a white solid.

Step 3—(1R,3R)-methyl 3-(6-bromo-5-methoxybenzo[d]thiazol-2-yl)cyclobutanecarboxylate A mixture of methyl 3-[(4-bromo-2-iodo-5-methoxy-phenyl)carbamothioyl]cyclobutanecarboxylate (6.10 g, 12.6 mmol), CuI (239 mg, 1.26 mmol), 1,10-phenanthroline (227 mg, 1.26 mmol) and $Cs_2CO_3$ (8.21 g, 25.2 mmol) in DME (100 mL) was degassed and purged with $N_2$ three times. Then the mixture was stirred at 40° C. for 3 hours under $N_2$ atmosphere. On completion, the reaction was filtered, and the filtrate was concentrated in vacuo. The residue was purified by column chromatography (SiO$_2$, Petroleum ether/Ethyl acetate=10/1 to 5/1) to give the title compound (2.4 g, 53% yield) as a white solid. LC-MS (ESI$^+$) m/z 358.0 (M+H)$^+$.

Step 4—(1R,3R)-methyl 3-(5-methoxy-6-(6-(trifluoromethyl)picolinamido)benzo[d]thiazol-2-yl)cyclobutanecarboxylate A mixture of methyl 3-(6-bromo-5-methoxy-1,3-benzothiazol-2-yl)cyclobutanecarboxylate (1.20 g, 3.37 mmol), 6-(trifluoromethyl)pyridine-2-carboxamide (768 mg, 4.04 mmol, CAS #22245-84-7), Pd$_2$(dba)$_3$ (308 mg, 336 umol), Xantphos (389 mg, 673 umol) and $Cs_2CO_3$ (3.29 g, 10.1 mmol) in dioxane (10.0 mL) was degassed and purged with $N_2$ three times. Then the mixture was stirred at 80° C. for 16 hours under $N_2$ atmosphere. On completion, the reaction was filtered, and the filtrate was concentrated in vacuo. The residue was purified by column chromatography (SiO$_2$, Petroleum ether/Ethyl acetate=10/1 to 3/1) to give the title compound (1.2 g, 71% yield) as a white solid. $^1$H NMR (400 MHz, CDCl$_3$) δ 10.63 (s, 1H), 9.04 (s, 1H), 8.43 (d, J=8.0 Hz, 1H), 8.07 (t, J=8.0 Hz, 1H), 7.81 (dd, J=0.8, 8.0 Hz, 1H), 7.48 (s, 1H), 7.46 (s, 1H), 4.01-3.95 (m, 4H), 3.69 (s, 3H), 3.65 (s, 1H), 3.34-3.23 (m, 1H), 2.81-2.65 (m, 5H); LC-MS (ESI$^+$) m/z 466.0 (M+H)$^+$.

1-[8-[(3R)-3-methylpiperazin-1-yl]-4-isoquinolyl] hexahydropyrimidine -2,4-dione (Intermediate CAB)

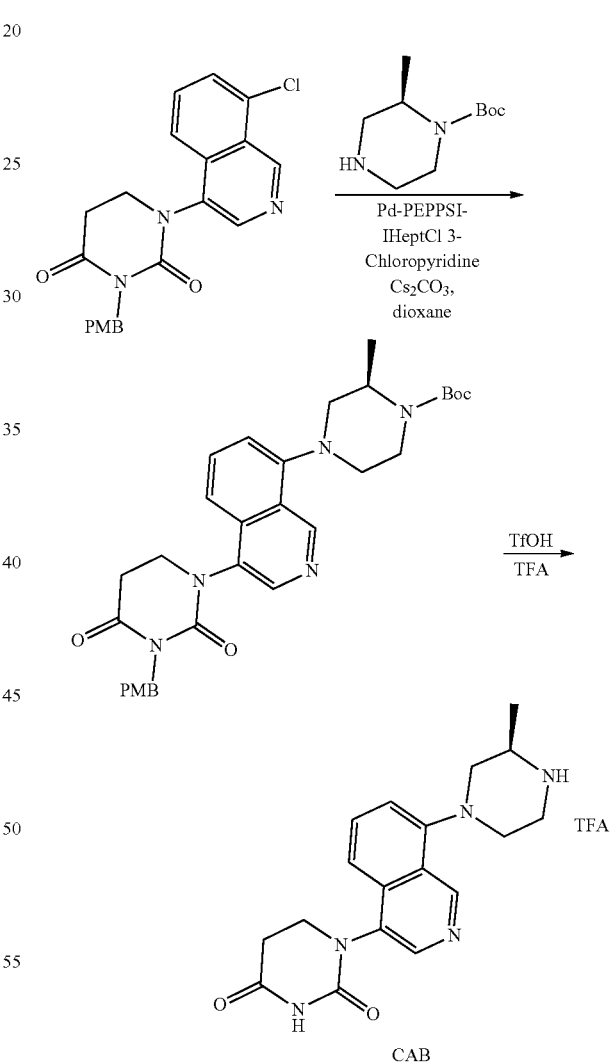

CAB

Step 1—Tert-butyl (2R)-4-[4-[3-[(4-methoxyphenyl)methyl]-2,4-dioxo-hexahydropyrimidin-1-yl]-8-isoquinolyl]-2-methyl-piperazine-1-carboxylate A mixture of 1-(8-chloro-4-isoquinolyl)-3-[(4-methoxyphenyl)methyl]hexahydropyrimidine-2,4-dione (200 mg, 505 umol, synthesized via Steps 1-2 of Intermediate BSL), tert-butyl (2R)-2-methylpiperazine-1-carboxylate (111 mg, 555 umol, CAS #170033-47-3), Cs$_2$CO$_3$ (493 mg, 1.52 mmol), 4 Å molecular sieves (100 mg, 505 umol) and PD-PEPPSI-IHeptCl 3-Chloropyridine (100 mg, 252 umol) was dissolved in dioxane (6 mL). The reaction mixture was then stirred at 100° C. for 12 hrs. On completion, the residue was diluted with water (30 mL), then the residue was extracted with EA (3×70 mL). The combined organic layer was dried over Na$_2$SO$_4$, filtered and concentrated in vacuo to give a residue. The residue was purified by reverse phase (0.1% FA condition) to give title compound (250 mg, 88% yield) as white solid. $^1$H NMR (400 MHz, DMSO-d$_6$) δ 9.54 (s, 1H), 8.56 (m, 1H), 7.74-7.69 (m, 1H), 7.59 (d, J=8.4 Hz, 1H), 7.30-7.24 (m, 3H), 6.90-6.86 (m, 2H), 4.83 (s, 2H), 4.33-4.29 (m, 1H), 3.96-3.87 (m, 2H), 3.76-3.74 (m, 1H), 3.73 (s, 3H), 3.46-3.43 (m, 1H), 3.20-3.08 (m, 2H), 3.00-2.92 (m, 2H), 2.82-2.73 (m, 3H), 1.44 (s, 9H). LC-MS (ESI$^+$) m/z 560.3 (M+H)$^+$.

Step 2—1-[8-[(3R)-3-methylpiperazin-1-yl]-4-isoquinolyl]hexahydropyrimidine -2,4-dione To a solution of tert-butyl (2R)-4-[4-[3-[(4-methoxyphenyl)methyl]-2,4-dioxo-hexahydropyrimidin-1-yl]-8-isoquinolyl]-2-methyl-piperazine-1-carboxylate (100 mg, 178 umol) in TFA (1 mL) was added TfOH (0.2 mL). The reaction mixture was stirred at 70° C. for 0.2 hr. On completion, the reaction mixture was concentrated in vacuo to give title compound (80.0 mg, 98% yield, TFA) as brown oil. LC-MS (ESI$^+$) m/z 339.1 (M+H)$^+$.

1-[8-[(2 S)-2-methylpiperazin-1-yl]-4-isoquinolyl]hexahydropyrimidine -2,4-dione (Intermediate CAC)

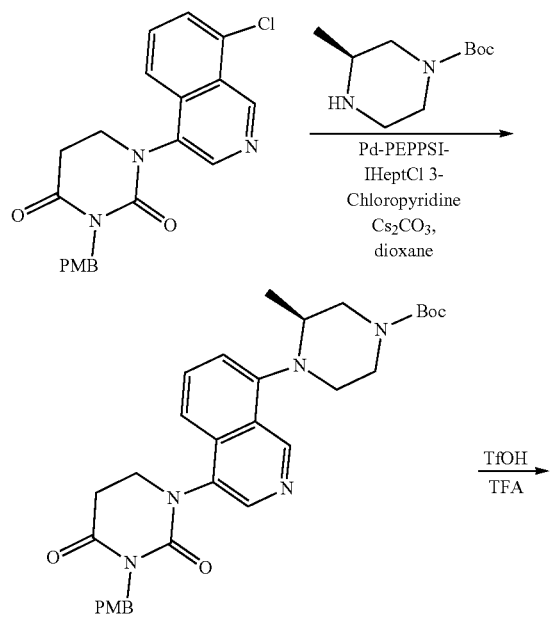

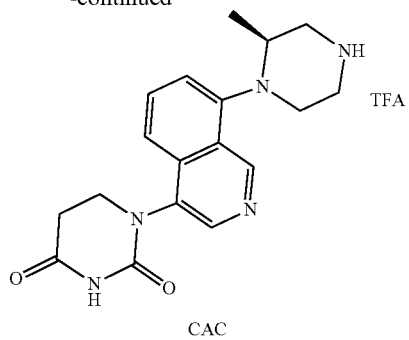

CAC

Step 1—Tert-butyl (3S)-4-[4-[3-[(4-methoxyphenyl)methyl]-2,4-dioxo-hexahydropyrimidin-1-yl]-8-isoquinolyl]-3-methyl-piperazine-1-carboxylate A mixture of 1-(8-chloro-4-isoquinolyl)-3-[(4-methoxyphenyl)methyl]hexahydropyrimidine-2,4-dione (170 mg, 429 umol, synthesized via Steps 1-2 of Intermediate BSL), tert-butyl (3S)-3-methylpiperazine-1-carboxylate (103 mg, 515 umol, from CAS #147081-29-6), Cs$_2$CO$_3$ (279 mg, 858 umol), 4 Å molecular sieves (429 umol) and Pd-PEPPSI-IHeptCl 3-Chloropyridine (41.7 mg, 42.9 umol) in dioxane (5 mL) was stirred at 100° C. for 12 hrs under N$_2$ atmosphere. On completion, the mixture was filtered and concentrated to give a residue. The residue was purified by reversed phase flash (0.1% FA condition) to give the title compound (200 mg, 82% yield) as white solid. $^1$H NMR (400 MHz, DMSO-d$_6$) δ 9.62 (d, J=5.6 Hz, 1H), 8.55 (d, J=2.8 Hz, 1H), 7.79-7.71 (m, 1H), 7.65 (d, J=8.4 Hz, 1H), 7.49-7.40 (m, 1H), 7.26 (d, J=1.6 Hz, 2H), 6.88 (d, J=8.0 Hz, 2H), 4.83 (s, 2H), 4.01-3.82 (m, 2H), 3.80-3.74 (m, 1H), 3.73 (s, 3H), 3.67-3.37 (m, 3H), 3.24-3.06 (m, 3H), 2.96 (d, J=5.6 Hz, 1H), 2.76 (d, J=8.0 Hz, 1H), 1.45 (s, 9H), 0.82 (d, J=6.0 Hz, 3H); LC-MS (ESI+) m/z 560.3 (M+H)$^+$.

Step 2—1-[8-[(2S)-2-methylpiperazin-1-yl]isoquinolyl]hexahydropyrimidine -2,4-dione To a mixture of tert-butyl (3S)-4-[4-[3-[(4-methoxyphenyl)methyl]-2,4-dioxo-hexahydropyrimidin-1-yl]-8-isoquinolyl]-3-methyl-piperazine-1-carboxylate (100 mg, 178 umol) in TFA (2 mL) was added TfOH (0.4 mL). The mixture was then stirred at 70° C. for 1 hr. On completion, the mixture was concentrated to give the title compound (80.0 mg, 176 umol, TFA) as a brown oil. LC-MS (ESI$^+$) m/z 340.1 (M+H)$^+$.

N-(2-((1r,3r)-3-(iodomethyl)cyclobutyl)-5-methoxybenzo[d]thiazol-6-yl)-6-(trifluoromethyl)picolinamide (Intermediate CAD)

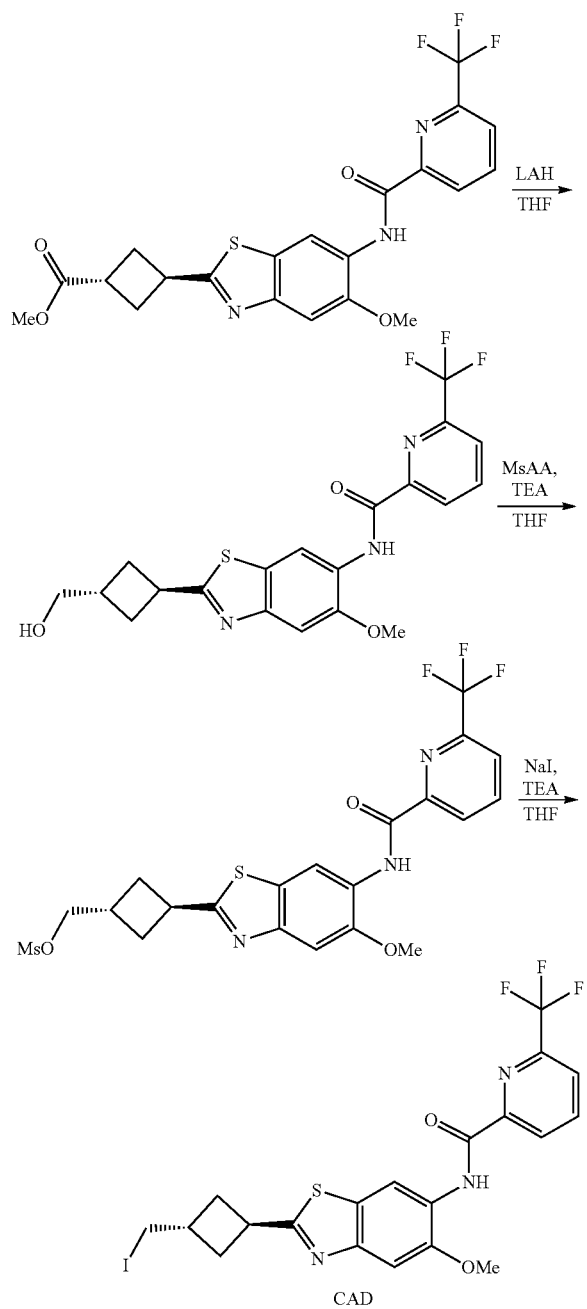

Step 1—N-(2-((1r,3r)-3-(hydroxymethyl)cyclobutyl)-5-methoxybenzo[d]thiazol-6-yl)-6-(trifluoromethyl)picolinamide To a solution of methyl 3-[5-methoxy-6-[[6-(trifluoromethyl)pyridine-2-carbonyl]amino]-1,3-benzothiazol-2-yl]cyclobutanecarboxylate (330 mg, 709 umol, Intermediate CAA) in THF (4 mL) was added LiAlH₄ (40.3 mg, 1.06 mmol). The mixture was then stirred at 0° C. for 2 h. On completion, water (0.05 ml) was added into reaction, then 15% NaOH(aq) (0.05 ml) was added to quench the reaction mixture. The mixture was then filtered and the filtrate was concentrated under vacuum. The residue was purified by column chromatography (SiO₂, Petroleum ether/Ethyl acetate=4/1 to 1.5/1) to give the title compound (120 mg, 39% yield). $^1$H NMR (400 MHz, CDCl₃) δ 10.73 (s, 1H), 9.13 (s, 1H), 8.52 (d, J=8.0 Hz, 1H), 8.16 (t, J=7.6 Hz, 1H), 7.90 (dd, J=0.8, 7.6 Hz, 1H), 7.59 (s, 1H), 4.08 (s, 3H), 4.04-3.94 (m, 1H), 3.83 (d, J=6.4 Hz, 2H), 2.78-2.69 (m, 1H), 2.70-2.59 (m, 2H), 2.49-2.38 (m, 2H).

Step 2—((1r,3r)-3-(5-methoxy-6-(6-(trifluoromethyl)picolinamido)benzo[d]thiazol-2-yl)cyclobutyl)methyl methanesulfonate To a solution of N-[2-[3-(hydroxymethyl)cyclobutyl]-5-methoxy-1,3-benzothiazol-6-yl]-6-(trifluoromethyl) pyridine-2-carboxamide (120 mg, 274 umol) in THF (2 mL) was added methane sulfonic anhydride (477 mg, 2.74 mmol) and TEA (83.2 mg, 822 umol). The mixture was then stirred at 25° C. for 16 h. On completion, the reaction mixture was diluted with water (5 ml), then extracted with EA (3×5 ml). The combined organic layers were concentrated in vacuo to give the title compound as a yellow solid (140 mg, 99% yield). $^1$H NMR (400 MHz, CDCl₃) δ 10.64 (s, 1H), 9.04 (s, 1H), 8.43 (d, J=8.0 Hz, 1H), 8.07 (t, J=7.6 Hz, 1H), 7.81 (d, J=8.0 Hz, 1H), 7.50 (s, 1H), 4.30 (d, J=6.4 Hz, 2H), 3.99 (s, 3H), 3.91 (s, 1H), 3.00 (s, 3H), 2.92-2.81 (m, 1H), 2.68-2.57 (m, 2H), 2.41 (m, 2H).

Step 3—N-(2-((1r,3 r)-3-(iodomethyl)cyclobutyl)-5-methoxybenzo[d]thiazol-6-yl)-6-(trifluoromethyl)picolinamide To a solution of [3-[5-methoxy-6-[[6-(trifluoromethyl)pyridine-2-carbonyl]amino]-1,3-benzothiazol-2-yl]cyclobutyl]methyl methane sulfonate (140 mg, 271 umol) in THF (3 mL) was added NaI (203 mg, 1.36 mmol) and TEA (54.9 mg, 543 umol). The reaction mixture was then stirred at 75° C. for 16 h. On completion, the reaction mixture was diluted with water (5 ml), then extracted with EA (3×5 ml). The combined organic layers were concentrated in vacuo to give the title compound as a yellow solid (140 mg, 94% yield). $^1$H NMR (400 MHz, CDCl₃) δ 10.63 (s, 1H), 9.03 (s, 1H), 8.43 (d, J=8.0 Hz, 1H), 8.07 (t, J=8.0 Hz, 1H), 7.81 (d, J=7.6 Hz, 1H), 7.47 (s, 1H), 3.99 (s, 3H), 3.86-3.72 (m, 1H), 3.34 (d, J=7.6 Hz, 2H), 2.93-2.79 (m, 1H), 2.62-2.48 (m, 2H), 2.24 (m, 2H).

N-[6-methoxy-2-(4-piperidyl)indazol-5-yl]-6-(trifluoromethyl) pyridine-2-carboxamide (Intermediate CAE)

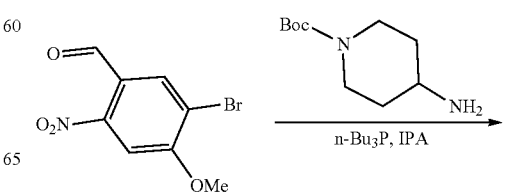

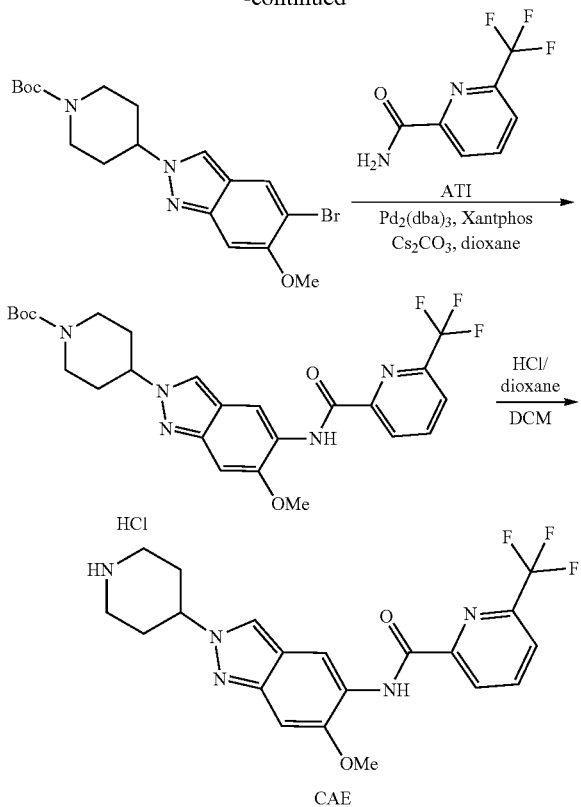

CAE

Step 1—Tert-butyl 4-(5-bromo-6-methoxy-indazol-2-yl) piperidine-1-carboxylate A solution of tert-butyl 4-aminopiperidine-1-carboxylate (462 mg, 2.31 mmol, CAS #502482-34-0) and 5-bromo-4-methoxy-2-nitro-benzaldehyde (500 mg, 1.92 mmol, synthesized via Steps 1-2 of Intermediate ATE) in IPA (10 mL) was stirred at 80° C. for 16 hrs. Then the reaction mixture was cooled to 25° C., and tributylphosphane (1.17 g, 5.77 mmol) was added to the solution which was then stirred at 80° C. for 6 hrs. On completion, the mixture was concentrated in vacuo. The crude product was purified by reversed phase (0.1% FA condition) to give the title compound (610 mg, 77% yield) as a white solid. $^1$H NMR (400 MHz, DMSO-$d_6$) δ 8.32 (s, 1H), 7.96 (s, 1H), 7.11 (s, 1H), 4.69-4.58 (m, 1H), 4.07 (d, J=11.6 Hz, 2H), 3.86 (s, 3H), 2.94 (s, 2H), 2.11-2.04 (m, 2H), 1.97-1.85 (m, 2H), 1.42 (s, 9H). LC-MS (ESI$^+$) m/z 412.0 (M+H)$^+$.

Step 2—Tert-butyl 4-[6-methoxy-5-[[6-(trifluoromethyl) pyridine-2-carbonyl]amino] indazol-2-yl] piperidine-1-carboxylate To a solution of tert-butyl 4-(5-bromo-6-methoxy-indazol-2-yl)piperidine-1-carboxylate (550 mg, 1.34 mmol) and 6-(trifluoromethyl)pyridine-2-carboxamide (305 mg, 1.61 mmol, CAS #22245-84-7, Intermediate ATI) in dioxane (1 mL) was added Pd$_2$(dba)$_3$ (122 mg, 134 umol), Xantphos (155 mg, 268 umol) and Cs$_2$CO$_3$ (873 mg, 2.68 mmol). Then the mixture was degassed and purged with N$_2$ three times, and the mixture was stirred at 100° C. for 4 hrs under N$_2$ atmosphere. On completion, the mixture was filtered through a pad of Celite and the pad of filter cake was washed with EA, then the filter liquor was concentrated in vacuo. The crude product was purified by reversed phase (0.1% FA condition) to give the title compound (686 mg, 98% yield) as an orange solid. $^1$H NMR (400 MHz, DMSO-$d_6$) δ 10.50 (s, 1H), 8.69 (s, 1H), 8.49-8.43 (m, 1H), 8.43-8.36 (m, 2H), 8.21 (dd, J=1.2, 7.6 Hz, 1H), 7.16 (s, 1H), 4.70-4.50 (m, 1H), 4.08 (d, J=11.6 Hz, 2H), 3.98 (s, 3H), 3.06-2.86 (m, 2H), 2.17-2.05 (m, 2H), 2.00-1.86 (m, 2H), 1.43 (s, 9H). LC-MS (ESI$^+$) m/z 520.1 (M+H)$^+$.

Step 3—N-[6-methoxy-2-(4-piperidyl)indazol-5-yl]-6-(trifluoromethyl) pyridine-2-carboxamide To a solution of tert-butyl 4-[6-methoxy-5-[[6-(trifluoromethyl) pyridine-2-carbonyl]amino] indazol-2-yl]piperidine-1-carboxylate (60 mg, 115 umol) in DCM (1 mL) was added HCl/dioxane (4 M, 1 mL). The mixture was then stirred at 25° C. for 4 hrs. On completion, the mixture was concentrated in vacuo to give the title compound (52 mg, 98% yield, HCl) as a pink solid. $^1$H NMR (400 MHz, DMSO-$d_6$) δ 10.51 (s, 1H), 9.15-9.01 (m, 1H), 8.71 (s, 1H), 8.49-8.44 (m, 1H), 8.42 (d, J=7.6 Hz, 1H), 8.40-8.36 (m, 1H), 8.22 (dd, J=1.2, 7.6 Hz, 1H), 7.19 (s, 1H), 4.83-4.71 (m, 1H), 3.99 (s, 3H), 3.44 (d, J=12.0 Hz, 2H), 3.20-3.05 (m, 2H), 2.34-2.25 (m, 4H). LC-MS (ESI$^+$) m/z 420.6 (M+H)$^+$.

Tert-butyl-dimethyl-[[4-(4,4,5,5-tetramethyl-1,3,2-dioxaborolan-2-yl) cyclonex-3-en-1-yl]methoxy] silane (Intermediate CAF)

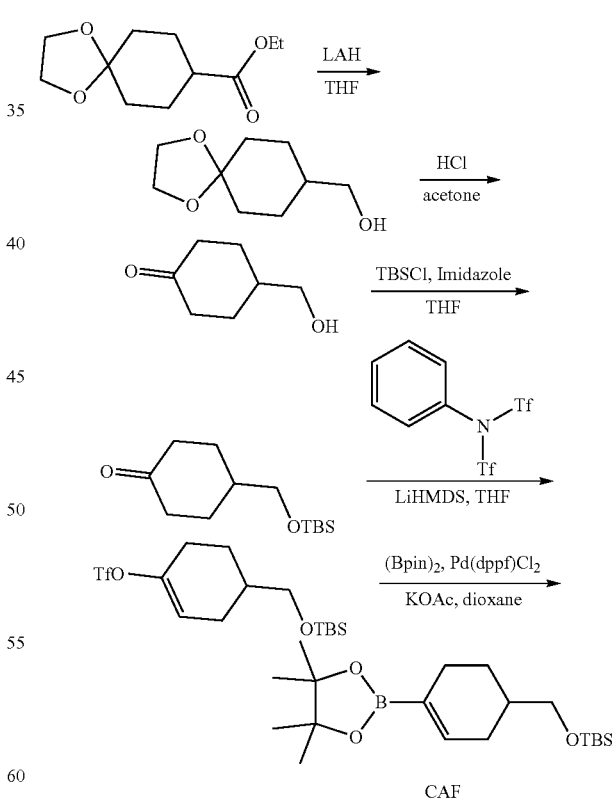

CAF

Step 1—1,4-Dioxaspiro[4.5]decan-8-ylmethanol

To a solution of LiAlH$_4$ (3.19 g, 84.0 mmol) in THF (50 mL) was added a solution of ethyl 1,4-dioxaspiro[4.5]

decane-8-carboxylate (15 g, 70.0 mmol, CAS #1489-97-0) in THF (90 mL) dropwise at 0° C. The mixture was stirred at 0° C. for 1 hr. On completion, the mixture was quenched with H$_2$O (3.2 mL), followed by 15% NaOH (3.2 mL), and H$_2$O (9.6 mL). Then the mixture was dried over anhydrous Na$_2$SO$_4$, filtered and concentrated in vacuo to give the title compound (11 g, 91% yield) as colorless oil. $^1$H NMR (400 MHz, CDCl$_3$) δ 4.01-3.89 (m, 4H), 3.50 (d, J=6.4 Hz, 2H), 1.79 (d, J=10.0 Hz, 4H), 1.61-1.51 (m, 3H), 1.35-1.19 (m, 2H).

Step 2—4-(Hydroxymethyl) cyclohexanone

To a solution of 1,4-dioxaspiro[4.5]decan-8-ylmethanol (11 g, 63.8 mmol) in acetone (70 mL) was added HCl (2 M, 24.5 mL). The mixture was then stirred at 25° C. for 13 hrs. On completion, the mixture was adjusted to pH=8 with saturated NaHCO$_3$, then extracted with DCM (5×80 mL). The organic layers were dried over anhydrous Na$_2$SO$_4$, filtered and concentrated in vacuo to give the title compound (8.0 g, 97% yield) as yellow oil. $^1$H NMR (400 MHz, CDCl$_3$) δ 3.58 (d, J=6.4 Hz, 2H), 2.52-2.28 (m, 4H), 2.19-2.08 (m, 2H), 2.03-1.89 (m, 1H), 1.52-1.38 (m, 2H).

Step 3—4-[[Tert-butyl (dimethyl)silyl]oxymethyl] cyclohexanone

To a solution of 4-(hydroxymethyl) cyclohexanone (7.7 g, 60.0 mmol) and imidazole (8.18 g, 120 mmol) in THF (80 mL) was added TBSCl (10.8 g, 72.0 mmol) and DMF (439 mg, 6.01 mmol). The mixture was then stirred at 25° C. for 2 hrs. On completion, the mixture was quenched with H$_2$O (40 mL) and the organic layer was concentrated in vacuo. The residue was purified by silica gel column (PE:EA=10:1) to give the title compound (13.5 g, 92% yield) as colorless oil. $^1$H NMR (400 MHz, CDCl$_3$) δ 3.52 (d, J=6.4 Hz, 2H), 2.48-2.27 (m, 4H), 2.16-2.03 (m, 2H), 1.99-1.82 (m, 1H), 1.47-1.40 (m, 2H), 0.90 (s, 9H), 0.06 (s, 6H).

Step 4—[4-[[Tert-butyl (dimethyl)silyl]oxymethyl] cyclohexen-1-yl] trifluoromethanesulfonate To a solution of 4-[[tert-butyl (dimethyl)silyl]oxymethyl] cyclohexanone (5 g, 20.6 mmol) in THF (50 mL) was added LiHMDS (1 M, 30.9 mL) at −70° C. The mixture was then stirred at −70° C. for 2 hrs. Then a solution of 1,1,1-trifluoro-Nphenyl-N-(trifluoromethylsulfonyl) methanesulfonamide (8.84 g, 24.7 mmol, CAS #37595-74-7) in THF (20 mL) was added to above solution dropwise. Then the mixture was warm to 20° C. and stirred for 2 hrs. On completion, the mixture was quenched with saturated NH$_4$Cl (10 mL) and extracted with EA (2×5 mL). The organic layer was washed with brine (2×10 mL), dried over anhydrous Na$_2$SO$_4$, filtered and concentrated in vacuo. The residue was purified by silica gel column (PE/EA=100/1) to give the title compound (6.75 g, 87% yield) as colorless oil. $^1$H NMR (400 MHz, CDCl$_3$) δ 5.8-5.7 (m, 1H), 3.51 (d, J=6.0 Hz, 2H), 2.44-2.15 (m, 3H), 2.01-1.85 (m, 2H), 1.84-1.75 (m, 1H), 1.52-1.41 (m, 1H), 0.90 (s, 9H), 0.04 (s, 6H).

Step 5—Tert-butyl-dimethyl-[[4-(4,4,5,5-tetramethyl-1,3,2-dioxaborolan-2-yl) cyclohex-3-en-1-yl] methoxy] silane To a solution of [4-[[tert-butyl (dimethyl)silyl]oxymethyl] cyclohexen-1-yl] trifluoromethanesulfonate (6.75 g, 18.0 mmol), 4,4,5,5-tetramethyl-2-(4,4,5,5-tetramethyl-1,3,2-dioxaborolan-2-yl)-1,3,2-dioxaborolane (4.58 g, 18.0 mmol) and KOAc (5.31 g, 54.0 mmol) in dioxane (80 mL) was added Pd(dppf)Cl$_2$ (1.32 g, 1.80 mmol) under N$_2$. The mixture was then stirred at 65° C. for 16 hrs. On completion, the mixture was concentrated in vacuo. The residue was purified by silica gel column (PE/EA=100/1) to give the title compound (3.7 g, 58% yield) as a white solid. $^1$H NMR (400 MHz, CDCl$_3$) δ 6.61-6.53 (m, 1H), 3.48 (d, J=6.0 Hz, 2H), 2.29-2.14 (m, 2H), 2.13-1.80 (m, 2H), 1.80-1.70 (m, 2H), 1.27 (s, 12H), 1.25-1.22 (m, 1H), 0.89 (s, 9H), 0.04 (s, 6H).

4-[1-(2,6-Dioxo-3-piperidyl)-3-methyl-2-oxo-benzimidazol-4-yl]cyclohexanecarbaldehyde (Intermediate CAG)

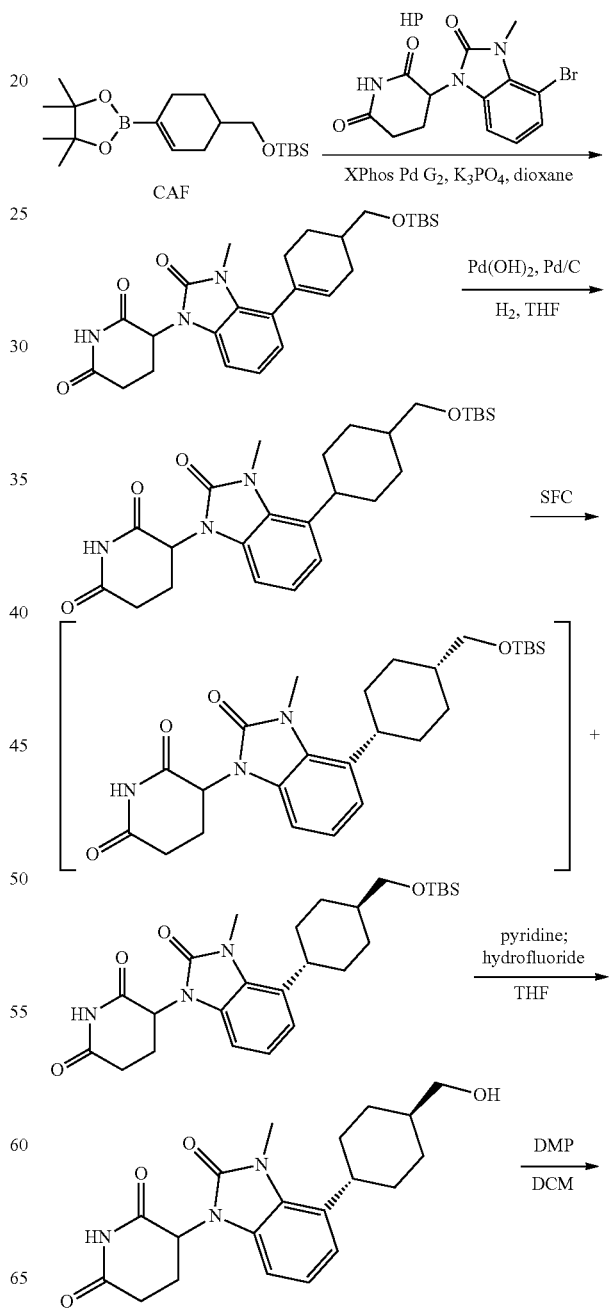

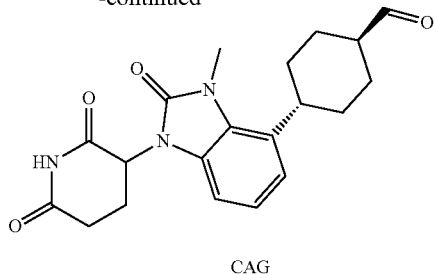

CAG

Step 1—3-[4-[4-[[Tert-butyl (dimethyl)silyl]oxymethyl] cyclohexen-1-yl]-3-methyl-2-oxo-benzimidazol-1-yl] piperidine-2,6-dione To a solution of tert-butyl-dimethyl-[[4-(4,4,5,5-tetramethyl-1,3,2-dioxaborolan-2-yl) cyclohex -3-en-1-yl] methoxy] silane (1.35 g, 3.84 mmol, Intermediate CAF), 3-(4-bromo-3-methyl-2-oxo-benzimidazol-1-yl)piperidine-2,6-dione (1 g, 2.96 mmol, Intermediate HP) and $K_3PO_4$ (1.88 g, 8.87 mmol) in dioxane (13 mL) was added XPHOS-PD-G2 (232 mg, 295 umol) under $N_2$. The mixture was stirred at 80° C. for 16 hrs under $N_2$. On completion, the mixture was filtered and concentrated in vacuo. The residue was purified by prep-HPLC (reverse phase: 0.1% FA) to give the title compound (600 g, 41% yield) as a yellow solid. $^1H$ NMR (400 MHz, DMSO-$d_6$) δ 11.09 (s, 1H), 7.09-6.91 (m, 2H), 6.77 (dd, J=1.2, 7.2 Hz, 1H), 5.70-5.60 (m, 1H), 5.37 (dd, J=5.2, 12.4 Hz, 1H), 3.61-3.48 (m, 2H), 3.32 (s, 3H), 2.96-2.80 (m, 1H), 2.75-2.66 (m, 1H), 2.65-2.56 (m, 1H), 2.41-2.32 (m, 1H), 2.30-2.17 (m, 2H), 2.04-1.97 (m, 1H), 1.92-1.74 (m, 3H), 1.44-1.37 (m, 1H), 0.88 (s, 9H), 0.11 (s, 6H). LC-MS (ESI$^+$) m/z 484.5 (M+H)$^+$.

Step 2—3-[4-[4-[[Tert-butyl (dimethyl)silyl]oxymethyl] cyclohexyl]-3-methyl-2-oxo-benzimidazol-1-yl] piperidine-2,6-dione To a solution of 3-[4-[4-[[tert-butyl(dimethyl)silyl]oxymethyl]cyclohexen-1-yl]-3-methyl-2-oxo-benzimidazol-1-yl] piperidine-2,6-dione (500 mg, 1.03 mmol) in THF (10 mL) was added Pd/C (300 mg, 10 wt %) and Pd(OH)$_2$ (300 mg, 213 umol, 10 wt %). The mixture was stirred at 60° C. for 16 hrs under H2 (15 psi). On completion, the mixture was filtered and concentrated in vacuo to give the title compound (500 mg, 99% yield) as a white solid. $^1H$ NMR (400 MHz, DMSO-$d_6$) δ 11.08 (s, 1H), 7.05-6.98 (m, 2H), 6.97-6.92 (m, 1H), 5.36 (dd, J=5.2, 12.4 Hz, 1H), 3.71 (d, J=7.6 Hz, 1H), 3.60-3.54 (m, 3H), 3.45 (d, J=6.4 Hz, 1H), 3.27-3.15 (m, 1H), 2.96-2.82 (m, 1H), 2.76-2.67 (m, 1H), 2.65-2.57 (m, 1H), 2.03-1.94 (m, 1H), 1.92-1.71 (m, 4H), 1.70-1.59 (m, 4H), 1.58-1.47 (m, 1H), 0.89 (s, 9H), 0.01 (s, 6H). LC-MS (ESI$^+$) m/z 486.2 (M+H)$^+$.

Step 3—3-(4-((1r,4r)-4-(((tert-butyldimethyl silyl)oxy)methyl)cyclohexyl)-3-methyl-2-oxo-2,3-dihydro-1H-benzo[d]imidazol-1-yl)piperidine-2,6-dione & 3-(4-((1s,4s)-4-(((tert-butyl dimethylsilyl)oxy)methyl)cyclohexyl)-3-methyl-2-oxo-2,3-dihydro-1H-benzo[d]imidazol-1-yl) piperidine-2,6-dione 3-[4-[4-[[tert-butyl (dimethyl)silyl]oxymethyl] cyclohexyl]-3-methyl-2-oxo-benzimidazol-1-yl]piperidine-2,6-dione (590 mg, 1.21 mmol) was separated by SFC (column: DAICEL CHIRALPAK AD (250 mm*30 mm, 10 um); mobile phase: [0.1% NH$_3$H$_2$O IPA]; B %: 25%-25%, 4; 90 min), then purified by prep-HPLC (reverse phase: 0.1% FA) to give 3-[4-[4-[[Tert-butyl (dimethyl)silyl]oxymethyl] cyclohexyl]-3-methyl-2-oxo-benzimidazol -1-yl] piperidine-2,6-dione (50 mg, 8% yield) as a white solid $^1H$ NMR (400 MHz, CDCl$_3$) δ 7.98 (s, 1H), 7.02-6.93 (m, 2H), 6.64-6.52 (m, 1H), 5.23-5.06 (m, 1H), 3.62 (s, 3H), 3.41 (d, J=6.0 Hz, 2H), 3.16-3.02 (m, 1H), 2.93-2.60 (m, 3H), 2.18-2.10 (m, 1H), 1.89 (d, J=11.2 Hz, 4H), 1.53-1.46 (m, 3H), 1.12-0.98 (m, 2H), 0.85 (s, 9H), 0.00 (s, 6H). LC-MS (ESI$^+$) m/z 486.3 (M+H)$^+$) and 3-[4-[4-[[tert-butyl (dimethyl)silyl]oxymethyl cyclohexyl]-3-methyl-2-oxobenzimidazol-piperidine-2,6-dione (200 mg, 34% yield) as a white solid ($^1H$ NMR (400 MHz, CDCl$_3$) δ 8.20 (s, 1H), 7.11-6.97 (m, 2H), 6.71-6.59 (m, 1H), 5.30-5.13 (m, 1H), 3.78-3.66 (m, 5H), 3.32-3.18 (m, 1H), 2.99-2.68 (m, 3H), 2.26-2.18 (m, 1H), 2.01-1.84 (m, 3H), 1.78-1.58 (m, 6H), 0.93 (s, 9H), 0.09 (s, 6H). LC-MS (ESI$^+$) m/z 486.3 (M+H)$^+$). The cis/trans isomers were confirmed by 2D NMR.

Step 4—3-(4-((1r,4r)-4-(hydroxymethyl)cyclohexyl)-3-methyl-2-oxo-2,3-dihydro-1H-benzo[d] imidazol-1-yl)piperidine-2,6-dione To a solution of 3-[4-[4-[[tert-butyl (dimethyl)silyl]oxymethyl] cyclohexyl]-3-methyl-2-oxo-benzimidazol-1-yl]piperidine-2,6-dione (50 mg, 102 umol) in THF (2 mL) was added pyridine; hydrofluoride (550 mg, 5.55 mmol). The mixture was stirred at 25° C. for 0.5 hr. On completion, the mixture was concentrated in vacuo. The crude product was purified by reversed phase (0.1% FA condition) to give the title compound (30 mg, 78% yield) as a white solid. LC-MS (ESI$^+$) m/z 372.1 (M+H)$^+$.

Step 5—(1r,4r)-4-(1-(2,6-dioxopiperidin-3-yl)-3-methyl-2-oxo-2,3-dihydro-1H-benzo[d]imidazol-4-yl)cyclohexane-1-carbaldehyde To a solution of 3-[4-[4-(hydroxymethyl) cyclohexyl]-3-methyl-2-oxo-benzimidazol-1-yl] piperidine-2,6-dione (15 mg, 40.3 umol) in DCM (2 mL) was added DMP (25.6 mg, 60.5 umol). The mixture was stirred at 25° C. for 1 hr. On completion, the mixture was diluted with DCM (100 mL), quenched with saturated Na$_2$S$_2$O$_3$ (10 mL) and washed with saturated NaHCO$_3$(2×15 mL). The organic layer was dried over anhydrous Na$_2$SO$_4$, filter and concentrated in vacuo to give the title compound (20 mg, 100% yield) as a white solid. LC-MS (ESI$^+$) m/z 370.3 (M+H)$^+$.

N-[7-fluoro-2-(4-formylcyclohexyl)indazol-5-yl]-6-(trifluoromethyl)pyridine-2-carboxamide (Intermediate CAH)

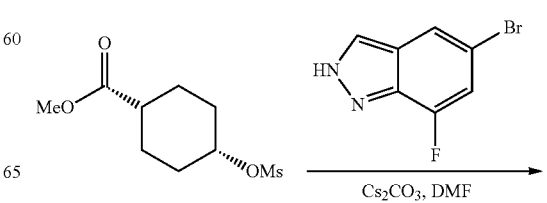

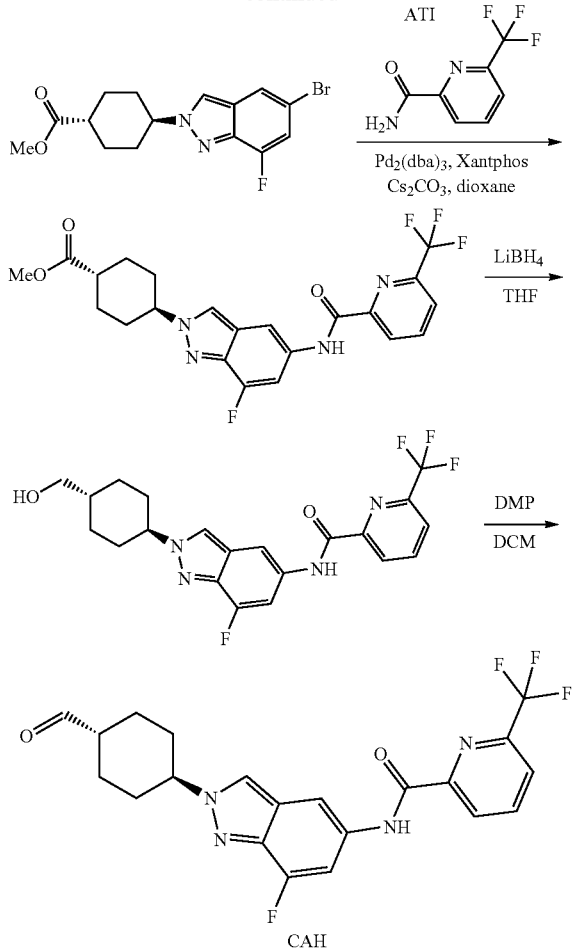

Step 1—Methyl-4-(5-bromo-7-fluoro-indazol-2-yl)cyclohexanecarboxylate

To a solution of 5-bromo-7-fluoro-2H-indazole (404 mg, 1.88 mmol, CAS #1260381-83-6) and methyl 4-methylsulfonyloxycyclohexanecarboxylate (890 mg, 3.77 mmol, synthesized via Step 1 of Intermediate QS) in DMF (10 mL) was added $Cs_2CO_3$ (1.23 g, 3.77 mmol). The mixture was then stirred at 80° C. for 16 hrs. On completion, the reaction mixture was filtered and concentrated under reduced pressure to give a residue, and the residue was purified by reversed-phase HPLC (0.1% FA condition) to give the title compound (120 mg, 17% yield) as yellow solid. LC-MS (ESI$^+$) m/z 355.0 (M+1)$^+$. $^1$H NMR (400 MHz, CDCl$_3$) δ 7.95 (d, J=2.8 Hz, 1H), 7.60 (d, J=1.6 Hz, 1H), 7.06 (dd, J=1.6, 10.4 Hz, 1H), 4.48-4.40 (m, 1H), 3.72 (s, 3H), 2.50-2.42 (m, 1H), 2.39-2.34 (m, 2H), 2.28-2.22 (m, 2H), 2.07-1.97 (m, 2H), 1.76-1.65 (m, 2H).

Step 2—Methyl-4-[7-fluoro-5-[[6-(trifluoromethyl)pyridine-2-carbonyl]amino]indazol-2-yl]cyclohexanecarboxylate A mixture of methyl 4-(5-bromo-7-fluoro-indazol-2-yl)cyclohexanecarboxylate (100 mg, 281 umol), 6-(trifluoromethyl)pyridine-2-carboxamide (64.2 mg, 337 umol, CAS #22245-84-7, Intermediate ATI), Pd$_2$(dba)$_3$ (25.7 mg, 28.1 umol), Xantphos (16.2 mg, 28.1 umol) and Cs$_2$CO$_3$ (183 mg, 563 umol) in dioxane (5 mL) was degassed and purged with N$_2$ three times. Then the mixture was stirred at 80° C. for 16 hours under N$_2$ atmosphere. On completion, the reaction mixture was filtered and concentrated under reduced pressure to give a residue. The residue was purified by prep-HPLC (column: Phenomenex luna C18 150*25 mm*10 um; mobile phase: [water (0.225% FA)-ACN]; B %: 50%-80%, 11.5 min) to give the title compound (129 mg, 95% yield) as a white solid. LC-MS (ESI$^+$) m/z 465.1 (M+H)$^+$. $^1$H NMR (400 MHz, DMSO-d$_6$) δ 10.47 (s, 1H), 8.55 (d, J=2.8 Hz, 1H), 8.42-8.34 (m, 2H), 8.21-8.13 (m, 2H), 7.56 (dd, J=1.2, 13.2 Hz, 1H), 4.59-4.51 (m, 1H), 3.64 (s, 3H), 3.30 (s, 1H), 2.21-2.17 (m, 2H), 2.13-2.06 (m, 2H), 2.05-1.94 (m, 2H), 1.66-1.56 (m, 2H).

Step 3—N-[7-fluoro-2-[4-(hydroxymethyl)cyclohexyl]indazol-5-yl]-6-(trifluoromethyl)pyridine-2-carboxamide A mixture of methyl 4-[7-fluoro-5-[[6-(trifluoromethyl)pyridine-2-carbonyl]amino]indazol-2-yl]cyclohexanecarboxylate (100 mg, 215 umol) in THF (2 mL) and MeOH (0.25 mL) was degassed and purged with N$_2$ three times. To the mixture was added LiBH4 (75.0 mg, 3.45 mmol), and then the mixture was stirred at 60° C. for 36 hours under N$_2$ atmosphere. On completion, the reaction mixture was quenched with H$_2$O (4 mL) at 25° C., and then extracted with EA (3×3 mL). The combined organic layers were washed with brine (2×3 mL), dried over Na$_2$SO$_4$, filtered and concentrated under reduced pressure to give the title compound (81 mg, 83% yield) as white solid. LC-MS (ESI$^+$) m/z 437.1 (M+H)$^+$. $^1$H NMR (400 MHz, DMSO-d$_6$) δ 10.46 (s, 1H), 8.56 (d, J=2.8 Hz, 1H), 8.45-8.32 (m, 2H), 8.22-8.12 (m, 2H), 7.54 (d, J=13.6 Hz, 1H), 4.51-4.39 (m, 2H), 3.31-3.26 (m, 3H), 2.18-2.15 (m, 2H), 1.94-1.86 (m, 4H), 1.19-1.15 (m, 2H).

Step 4—N-[7-fluoro-2-(4-formylcyclohexyl)indazol-5-yl]-6-(trifluoromethyl)pyridine-2-carboxamide To a solution of N-[7-fluoro-2-[4-(hydroxymethyl)cyclohexyl]indazol-5-yl]-6-(trifluoromethyl) pyridine-2-carboxamide (60.0 mg, 137 umol) in DCM (2 mL) was added DMP (139 mg, 329 umol) at 0° C. The mixture was then stirred at 25° C. for 4 hours. On completion, the reaction mixture was quenched with Na$_2$S$_2$O$_3$ (1 mL) at 25° C., and then diluted with NaHCO$_3$ (5 mL) and extracted with DCM (3×10 mL). The combined organic layers were washed with brine (2×10 mL), dried over Na$_2$SO$_4$, filtered and concentrated under reduced pressure to give the title compound (59 mg, 90% yield) as a white solid LC-MS (ESI$^+$) m/z 435.1 (M+H)$^+$.

N-[2-(4-formylcyclohexyl)pyrazolo[1,5-a]pyridin-5-yl]-6-(trifluoromethyl)pyridine-2-carboxamide (Intermediate CAI)

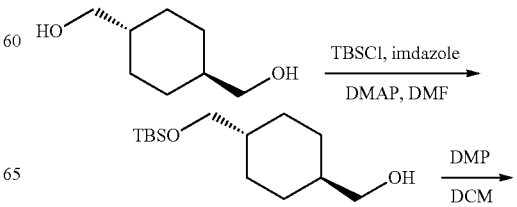

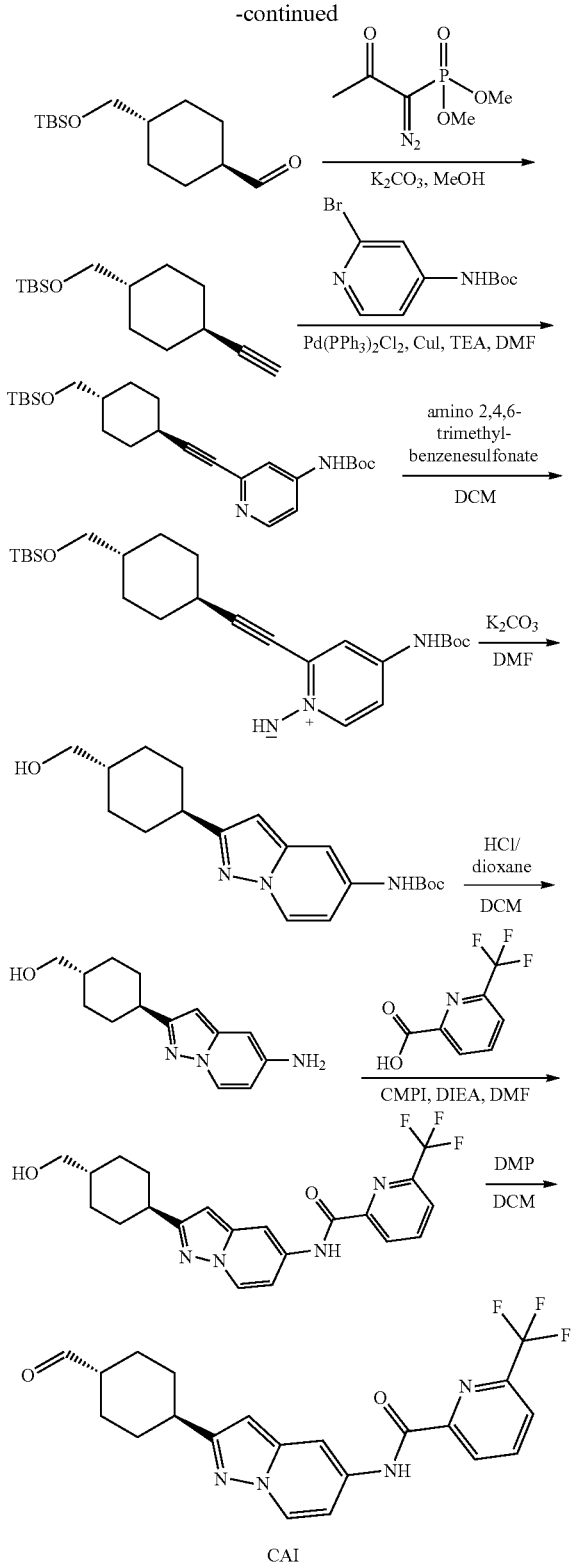

Step 1—[4-[[Tert-butyl(dimethyl)silyl]oxymethyl]cyclohexyl]methanol

To a solution of [4-(hydroxymethyl)cyclohexyl]methanol (20 g, 138 mmol, CAS #3236-48-4) in DMF (150 mL) was added TBSCl (16.7 g, 110 mmol), imidazole (18.8 g, 277 mmol) and DMAP (1.69 g, 13.8 mmol). The mixture was stirred at 25° C. for 16 hrs. On completion, the reaction mixture was quenched with H$_2$O (150 mL) and extracted with EA (2×300 mL). The combined organic phase was brine (2×150 mL), dried with anhydrous Na$_2$SO$_4$, filtered and concentrated in vacuo to give a residue. The residue was purified by silica gel chromatography (PE:EA=20:1 to 5:1, Rf=0.5) to give the title compound (10.9 g, 30% yield) as yellow oil. $^1$H NMR (400 MHz, CDCl$_3$) δ 3.47 (d, J=6.4 Hz, 2H), 3.42 (d, J=6.4 Hz, 2H), 1.88-1.76 (m, 4H), 1.44-1.41 (m, 2H), 1.03-0.93 (m, 4H), 0.91-0.88 (m, 9H), 0.09-0.02 (m, 6H).

Step 2—4-[[Tert-butyl(dimethyl)silyl]oxymethyl]cyclohexanecarbaldehyde

To a solution of [4-[[tert-butyl(dimethyl)silyl]oxymethyl]cyclohexyl]methanol (2.4 g, 9.29 mmol) in DCM (20 mL) was added DMP (5.12 g, 12 mmol). The reaction mixture was stirred at 25° C. for 2 hrs. On completion, the reaction mixture was quenched with Na$_2$S$_2$O$_3$ (20 mL) and saturated NaHCO$_3$ (20 mL) at 25° C., and then stirred for 15 minutes. On completion, the reaction mixture was extracted with DCM (2×30 mL), then the combined organic layers was washed with saturated NaCl (2×15 mL). Then the combined organic layers was dried over Na$_2$SO$_4$, filtered and concentrated in vacuo to give title compound (2.3 g, 96% yield) was obtained as yellow oil. $^1$H NMR (400 MHz, CDCl$_3$) δ 9.63 (s, 1H), 3.45-3.40 (m, 2H), 2.23-2.10 (m, 1H), 2.07-1.99 (m, 2H), 1.90 (dd, J=2.8, 13.2 Hz, 2H), 1.48-1.42 (m, 1H), 1.33-1.22 (m, 2H), 1.05-0.93 (m, 2H), 0.90 (s, 9H), 0.05 (s, 6H).

Step 3—Tert-butyl[(4-ethynylcyclohexyl)methoxy]-dimethyl-silane

To a solution of 4-[[tert-butyl(dimethyl)silyl]oxymethyl]cyclohexanecarbaldehyde (2.3 g, 8.97 mmol) and K$_2$CO$_3$ (2.48 g, 17.9 mmol) in MeOH (15 mL) was added 1-diazo-1-dimethoxyphosphoryl-propan-2-one (2.58 g, 13.4 mmol, CAS #90965-06-3) at 0° C. The reaction mixture was stirred at 25° C. for 12 hrs. On completion, the reaction mixture was quenched with water (15 mL) at 25° C., and then stirred for 30 minutes. The reaction mixture was extracted with EA (2×20 mL) then the organic layers were dried and concentrated in vacuo to give the residue. The residue was purified by column chromatography (SiO$_2$, PE:EA=1:0 to PE:EA=100:1, PE:EA=50:1, Pl:Rf=0.4) to give the title compound (1.3 g, 57% yield) as yellow oil. $^1$H NMR (400 MHz, CDCl$_3$) δ 3.39 (d, J=6.4 Hz, 2H), 2.18 (m, 1H), 2.05 (d, J=2.4 Hz, 1H), 2.04-1.97 (m, 2H), 1.84-1.75 (m, 2H), 1.49-1.43 (m, 1H), 1.43-1.32 (m, 2H), 0.99-0.92 (m, 2H), 0.90 (s, 9H), 0.10-0.00 (m, 6H).

Step 4—Tert-butyl N-[2-[2-[4-[[tert-butyl(dimethyl)silyl]oxymethyl]cyclohexyl]ethynyl]-4-pyridyl]carbamate To a solution of tert-butyl-[(4-ethynylcyclohexyl)methoxy]-dimethyl-silane (1 g, 3.96 mmol), tert-butyl N-(2-bromo-4-pyridyl)carbamate (721 mg, 2.64 mmol, CAS #433711-95-6), Pd(PPh$_3$)$_2$Cl$_2$ (185 mg, 264 umol) and CuI (100 mg, 528 umol) in DMF (10 mL) was added DIEA (1.71 g, 13.2 mmol). The mixture was stirred at 80° C. for 12 hrs. On completion, the reaction mixture was filtered and concentrated in vacuo to give a residue. The residue was purified by reverse phase (0.1% FA condition) and purified by column chromatography (SiO$_2$, PE:EA=15:1 to PE:EA=5:1, PE:EA=2:1, Pl:Rf=0.27) to give the title compound (434 mg, 37% yield) as a yellow solid. $^1$H NMR (400 MHz, DMSO-d$_6$) δ 9.88 (s, 1H), 8.26 (s, 1H), 7.51 (s, 1H), 7.31 (dd, J=1.6, 5.6 Hz, 1H), 3.38 (d, J=6.4 Hz, 2H), 2.46-2.39 (m, 1H), 2.02-1.97 (m, 2H), 1.74 (dd, J=2.8, 13.2 Hz, 2H), 1.48 (s, 9H), 1.44-1.31 (m, 3H), 1.02-0.90 (m, 2H), 0.86 (s, 9H), 0.09-0.03 (m, 6H); LC-MS (ESI$^+$) m/z 445.4 (M+H)$^+$.

Step 5—[4-(Tert-butoxycarbonylamino)-2-[2-[4-[[tert-butyl(dimethyl)silyl]oxymethyl]cyclohexyl]ethynyl]pyridin-1-ium-1-yl]azanide To a solution of tert-butyl N-[2-[2-[4-[[tert-butyl(dimethyl)silyl]oxymethyl]cyclohexyl]ethynyl]-4-pyridyl]carbamate (228 mg, 512 umol) in DCM (4 mL) was added amino 2,4,6-trimethylbenzenesulfonate (165 mg, 769 umol). The reaction mixture was stirred at 25° C. for 48 hrs. On completion, the mixture was concentrated in vacuo to give the title compound (235 mg, 100% yield) as a gray solid. LC-MS (ESI$^+$) m/z 460.3 (M+H)$^+$.

Step 6—Tert-butyl N-[2-[4-(hydroxymethyl)cyclohexyl]pyrazolo[1,5-a]pyridin-5-yl]carbamate To a solution of [4-(tert-butoxycarbonylamino)-2-[2-[4-[[tert-butyl(dimethyl)silyl]oxymethyl]cyclohexyl]ethynyl]pyridin-1-ium-1-yl]azanide (200 mg, 435 umol) in DMF (2 mL) was added K$_2$CO$_3$ (120 mg, 870 umol). The mixture was stirred at 25° C. for 24 hrs. On completion, the reaction mixture was filtered and concentrated in vacuo to give a residue. The residue was purified by prep-HPLC (column: Phenomenex luna C18 150*25 mm*10 um; mobile phase: [water (0.225% FA)-ACN]; B %: 35%-65%, 10 min) to give the title compound (23 mg, 14% yield) as a white solid. $^1$H NMR (400 MHz, DMSO-d$_6$) δ 9.59 (s, 1H), 8.40 (d, J=7.6 Hz, 1H), 7.69 (s, 1H), 6.76 (dd, J=2.4, 7.6 Hz, 1H), 6.20 (s, 1H), 4.40 (t, J=5.2 Hz, 1H), 3.25 (t, J=5.6 Hz, 2H), 2.66-2.57 (m, 1H), 2.05-1.97 (m, 2H), 1.87-1.80 (m, 2H), 1.49 (s, 9H), 1.46-1.38 (m, 3H), 1.08-0.97 (m, 2H); LC-MS (ESI$^+$) m/z 346.2 (M+H)$^+$.

Step 7—[4-(5-Aminopyrazolo[1,5-a]pyridin-2-yl)cyclohexyl]methanol

To a solution of tert-butyl N-[2-[4-(hydroxymethyl)cyclohexyl]pyrazolo[1,5-a]pyridin-5-yl]carbamate (23 mg, 66.5 umol) in DCM (1 mL) was added HCl/dioxane (4 M, 16.6 uL). The reaction mixture was stirred at 25° C. for 2 hrs. On completion, the reaction mixture was concentrated in vacuo to give the title compound (18 mg, 95% yield, HCl) as a yellow solid. LC-MS (ESI$^+$) m/z 246.1 (M+H)$^+$.

Step 8—N-[2-[4-(hydroxymethyl)cyclohexyl]pyrazolo[1,5-a]pyridin-5-yl]-6-(trifluoromethyl)pyridine-2-carboxamide To a solution of 6-(trifluoromethyl)pyridine-2-carboxylic acid (9.77 mg, 51.1 umol, CAS #131747-42-7) in DMF (1 mL) was added dropwise DIEA (41.2 mg, 319 umol) and CMPI (19.5 mg, 76.6 umol) at 25° C. After addition, the mixture was stirred at this temperature for 30 min, and then [4-(5-aminopyrazolo[1,5-a]pyridin-2-yl)cyclohexyl]methanol (18 mg, 63.8 umol, HCl) in DMF (1 mL) was added dropwise at 25° C. The resulting mixture was stirred at 25° C. for 2 hrs. On completion, the reaction mixture was quenched with water (0.05 mL) and concentrated in vacuo to give a residue. The residue was diluted with water (4 mL) and extracted with EA (2×5 mL). The combined organic layer was dried over Na$_2$SO$_4$, filtered and concentrated in vacuo to give the title compound (26 mg, 77% yield) as a yellow solid. $^1$H NMR (400 MHz, DMSO-d$_6$) δ 10.61 (s, 1H), 8.55 (d, J=7.6 Hz, 1H), 8.43-8.34 (m, 2H), 8.25-8.15 (m, 2H), 7.25 (dd, J=2.4, 7.6 Hz, 1H), 6.37 (s, 1H), 4.40 (s, 1H), 3.26 (d, J=5.6 Hz, 2H), 2.71-2.63 (m, 1H), 2.04 (dd, J=2.0, 13.2 Hz, 2H), 1.85 (d, J=10.8 Hz, 2H), 1.53-1.41 (m, 3H), 1.11-1.01 (m, 2H); LC-MS (ESI$^+$) m/z 419.1 (M+H)$^+$.

Step 9—N-[2-(4-formylcyclohexyl)pyrazolo[1,5-a]pyridin-5-yl]-6-(trifluoromethyl)pyridine-2-carboxamide To a solution of N-[2-[4-(hydroxymethyl)cyclohexyl]pyrazolo[1,5-a]pyridin-5-yl]-6-(trifluoromethyl) pyridine-2-carboxamide (26 mg, 62.1 umol) in DCM (1 mL) was added DMP (31.6 mg, 74.5 umol). The reaction mixture was stirred at 25° C. for 2 hrs. On completion, the reaction mixture was quenched by saturated Na$_2$S$_2$O$_3$ (2 mL) and saturated NaHCO$_3$ (2 mL) at 25° C., and then stirred for 15 minutes. The mixture was extracted with DCM (2×5 mL), then the combined organic layers was washed with saturated NaCl (2×10 mL). Then the combined organic layers was dried over Na$_2$SO$_4$, filtered and concentrated in vacuo to give the title compound (24 mg, 63% yield) as a brown solid. LC-MS (ESI$^+$) m/z 417.1 (M+H)$^+$.

3-[4-(2,6-Diazaspiro[3.3]heptan-2-ylmethyl)-3-methyl-2-oxo-benzimidazol-1-yl] piperidine-2,6-dione (Intermediate CAJ)

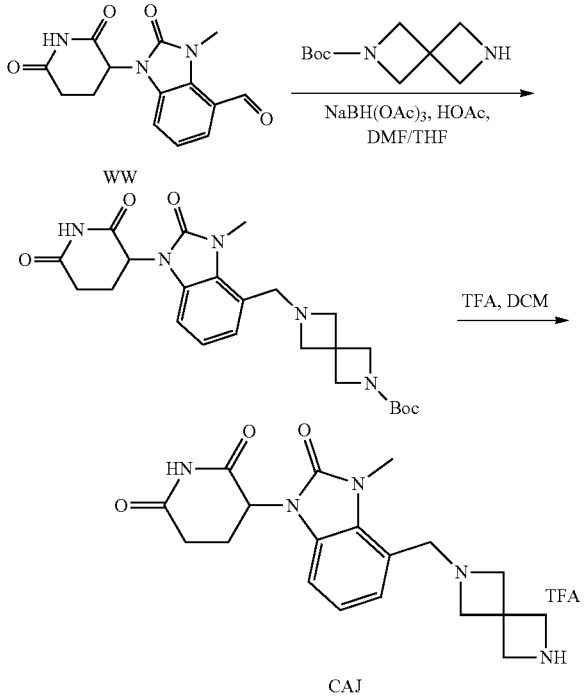

CAJ

Step 1—Tert-butyl 6-[[1-(2,6-dioxo-3-piperidyl)-3-methyl-2-oxo-benzimidazol-4-yl]methyl]-2,6-diazaspiro[3.3]heptane-2-carboxylate To a solution of tert-butyl 2,6-diazaspiro[3.3]heptane-2-carboxylate; oxalic acid (100 mg, 348 umol, CAS #1041026-70-3) in DMF (0.5 mL) was added TEA (70.4 mg, 696 umol). The reaction mixture was stirred at 25° C. for 10 min. Then HOAc (41.8 mg, 696 umol) and 1-(2,6-dioxo-3-piperidyl)-3-methyl-2-oxo-benzimidazole-4-carbaldehyde (100 mg, 348 umol, Intermediate WW) was added at 25° C. The mixture was stirred at 25° C. for 20 min. Then NaBH(OAc)$_3$ (88.5 mg, 417 umol) was added to the mixture and the mixture was stirred at 25° C. for 2 hrs. On completion, the reaction mixture was quenched with water (0.05 mL) and concentrated in vacuo to give a residue. The residue was purified by reverse phase (0.1% FA condition) to give the title compound (100 mg, 56% yield) as a yellow solid. $^1$H NMR (400 MHz, DMSO-d$_6$) δ 11.09 (s, 1H), 7.05 (d, J=7.6 Hz, 1H), 6.99-6.85 (m, 2H), 5.36 (dd, J=5.6, 12.4 Hz, 1H), 4.23 (s, 1H), 3.98 (s, 3H), 3.89 (s, 4H), 3.76 (s, 2H), 3.62 (s, 3H), 2.95-2.82 (m, 1H), 2.77-2.61 (m, 2H), 2.04-1.96 (m, 1H), 1.36 (d, J=6.0 Hz, 9H); LC-MS (ESI$^+$) m/z 470.0 (M+H)$^+$.

Step 2—3-[4-(2,6-Diazaspiro[3.3]heptan-2-ylmethyl)-3-methyl-2-oxo-benzimidazol-1-yl]piperidine-2,6-dione To a solution of tert-butyl 6-[[1-(2,6-dioxo-3-piperidyl)-3-methyl-2-oxo-benzimidazol-4-yl] methyl]-2,6-diazaspiro [3.3]heptane-2-carboxylate (50 mg, 106 umol) in DCM (1 mL) was added TFA (308 mg, 2.70 mmol). The mixture was then stirred at 25° C. for 0.5 hr. On completion, the reaction mixture was concentrated in vacuo to give title compound (50 mg, 97% yield, TFA salt) as yellow oil. LC-MS (ESI$^+$) m/z 370.1 (M+H)$^+$.

3-[5-methoxy-3-methyl-2-oxo-4-(4-piperidyl)benzimidazol-1-yl]-1-methyl-piperidine-2,6-dione (Intermediate CAK)

Step 1—Tert-butyl 4-[5-methoxy-3-methyl-1-(1-methyl-2,6-dioxo-3-piperidyl)-2-oxo-benzimidazol-4-yl]piperidine-1-carboxylate A mixture of tert-butyl 4-[1-(2,6-dioxo-3-piperidyl)-5-methoxy-3-methyl-2-oxo-benzimidazol-4-yl] piperidine-1-carboxylate (100 mg, 211 umol, synthesized via Steps 1-5 of Intermediate BUC), MeI (45.0 mg, 317 umol) and K$_2$CO$_3$ (87.7 mg, 634 umol) in THF (1 mL) was stirred at 50° C. for 1 hr. On completion, the reaction was diluted with EA (100 mL). The organic layer was washed with water (100 mL×3), dried over Na$_2$SO$_4$ and filtered. The filtrate was concentrated in vacuo to give title compound (100 mg, 97% yield) as yellow solid. $^1$H NMR (400 MHz, DMSO-d$_6$) δ 7.43 (d, J=8.8 Hz, 1H), 7.21 (d, J=8.8 Hz, 1H), 5.90 (dd, J=5.6, 12.8 Hz, 1H), 4.54 (q, J=7.2 Hz, 2H), 4.24 (s, 3H), 4.11-4.07 (m, 3H), 4.04-3.92 (m, 1H), 3.54 (s, 3H), 3.50-3.41 (m, 1H), 3.38-3.24 (m, 3H), 3.22-3.14 (m, 1H), 2.79-2.67 (m, 2H), 2.09 (d, J=11.2 Hz, 2H), 1.95 (s, 9H), 1.69 (t, J=7.2 Hz, 1H).

Step 2—3-[5-methoxy-3-methyl-2-oxo-4-(4-piperidyl)benzimidazol-1-yl]-1-methyl-piperidine-2,6-dione A mixture of tert-butyl 4-[5-methoxy-3-methyl-1-(1-methyl-2,6-dioxo-3-piperidyl)-2-oxo-benzimidazol-4-yl]piperidine-1-carboxylate (40.0 mg, 82.2 umol) and TFA (385 mg, 3.38 mmol) in DCM (1 mL) was stirred at 25° C. for 1 hr. On completion, the reaction was concentrated in vacuo to give title compound (41 mg, 99% yield, TFA) as brown oil. LC-MS (ESI$^+$) m/z 387.4 (M+H)$^+$.

[3-Methyl-4-[(3S)-3-methylpiperazin-1-yl]-2-oxobenzimidazol-1-yl]piperidine-2,6-dione (Intermediate CAL)

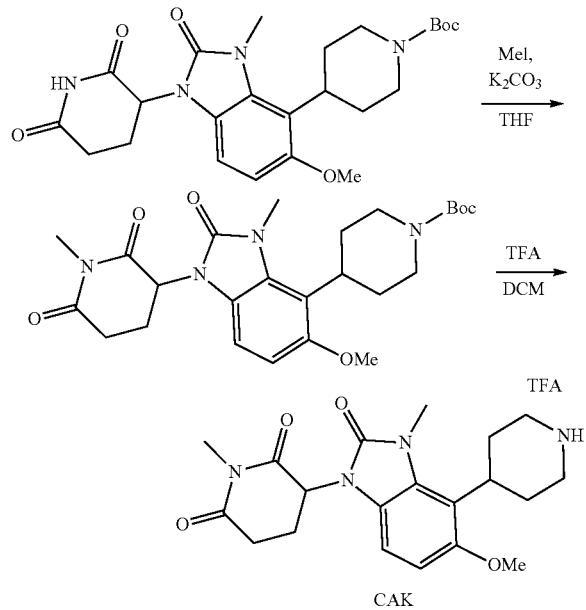

CAK

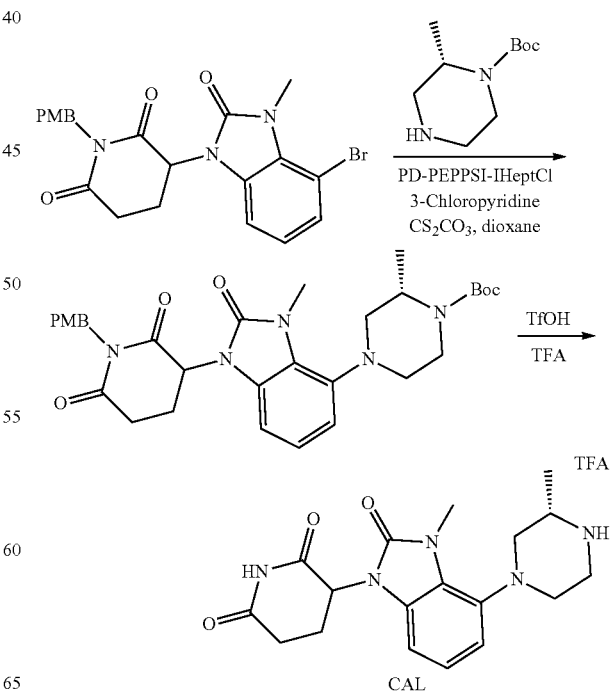

CAL

Step 1—Tert-butyl (2S)-4-[1-[1-[(4-methoxyphenyl)methyl]-2,6-dioxo-3-piperidyl]-3-methyl-2-oxo-benzimidazol-4-yl]-2-methyl-piperazine-1-carboxylate To a solution of 3-(4-bromo-3-methyl-2-oxo-benzimidazol-1-yl)-1-[(4-methoxyphenyl)methyl] piperidine-2,6-dione (800 mg, 1.75 mmol, synthesized via Steps 1-4 of Intermediate HP) and tert-butyl (2S)-2-methylpiperazine-1-carboxylate (419 mg, 2.09 mmol, CAS #169447-70-5) in dioxane (15 mL) was added PD-PEPPSI-IHeptCl 3-Chloropyridine (100 mg, 103 umol) and $Cs_2CO_3$ (1.14 g, 3.49 mmol). Then the mixture was stirred at 100° C. for 16 hrs. On completion, the mixture was diluted with $H_2O$ (30 mL) and extracted with EA (30 mL×3). The combined organic layers were washed with saturated NaCl (20 mL), dried over $Na_2SO_4$, filtered and concentrated in vacuo to give a residue. The residue was triturated with EA:PE=1:20 and filtered to give the title compound (450 mg, 45% yield) as yellow solid. $^1H$ NMR (400 MHz, DMSO-$d_6$) δ 7.22 (d, J=8.4 Hz, 2H), 7.12-6.98 (m, 1H), 6.94 (s, 1H), 6.90-6.80 (m, 3H), 5.57-5.47 (m, 1H), 4.85-4.74 (m, 2H), 4.27-4.25 (m, 1H), 3.73 (s, 2H), 3.82-3.72 (m, 1H), 3.68 (s, 3H), 3.15-3.00 (m, 3H), 2.92-2.69 (m, 3H), 2.09-2.01 (m, 1H), 1.44 (s, 9H), 1.28-1.27 (m, 3H), 1.18-1.05 (m, 1H), 0.87-0.81 (m, 2H).

Step 2—[3-Methyl-4-[(3S)-3-methylpiperazin-1-yl]-2-oxo-benzimidazol-1-yl]piperidine-2,6-dione A solution of tert-butyl (2S)-4-[1-[1-[(4-methoxyphenyl)methyl]-2,6-dioxo-3-piperidyl]-3-methyl-2-oxo-benzimidazol-4-yl]-2-methyl-piperazine-1-carboxylate (200 mg, 346 umol) in TFA (1.5 mL) was added TfOH (0.3 mL), then the mixture was stirred at 70° C. for 1 hr. On completion, the mixture was concentrated in vacuo to give the title compound (150 mg, 92% yield, TFA) as brown oil. LC-MS (ESI$^+$) m/z 358.2 (M+H)$^+$.

5-chlorothiazole-2-carboxylic acid (CAS #101012-16-2) (Intermediate CAM)

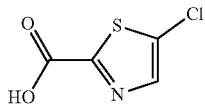

3-[4-(8-azabicyclo[3.2.1]octan-3-yl)-3-methyl-2-oxo-benzimidazol-1-yl]piperidine-2,6-dione (Intermediate CAN)

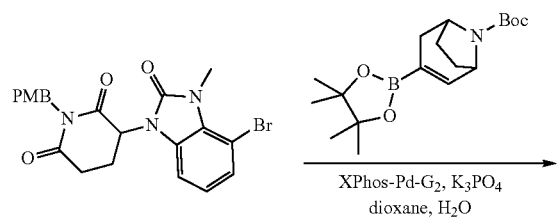

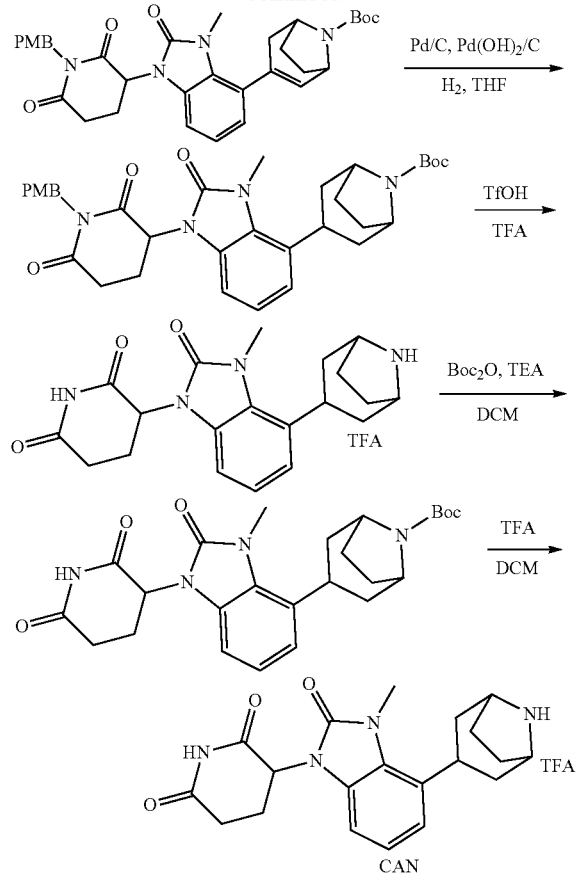

Step 1—3-[1-[1-[(4-methoxyphenyl)methyl]-2,6-dioxo-3-piperidyl]-3-methyl-2-oxo-benzimidazol-4-yl]-8-azabicyclo[3.2.1]oct-2-ene-8-carboxylate To a solution of 3-(4-bromo-3-methyl-2-oxo-benzimidazol-1-yl)-1-[(4-methoxyphenyl)methyl]piperidine-2,6-dione (500 mg, 1.09 mmol, synthesized via Steps 1-4 of Intermediate HP), tert-butyl 3-(4,4,5,5-tetramethyl-1,3,2-dioxaborolan-2-yl)-8-azabicyclo[3.2.1]oct-2-ene-8-carboxylate (365 mg, 1.09 mmol, CAS #900503-08-4) and $K_3PO_4$ (694 mg, 3.27 mmol) in dioxane (10 mL) and $H_2O$ (2 mL) was added XPHOS-PD-G2 (85.8 mg, 109 umol). The reaction mixture was stirred at 80° C. under $N_2$ for 2 hrs. On completion, the reaction mixture was filtered and the filtrate was concentrated in vacuo. The residue was purified by column chromatography (SiO$_2$, PE/EA=3/1 to 1/1; PE/EA=1/1, P1: $R_f$=0.3) to give title compound (589 mg, 92% yield) as white solid. $^1H$ NMR (400 MHz, DMSO-$d_6$) δ 7.21 (d, J=8.4 Hz, 2H), 6.99-6.89 (m, 2H), 6.85 (d, J=8.8 Hz, 2H), 6.80-6.72 (m, 1H), 6.06-5.99 (m, 1H), 5.57-5.49 (m, 1H), 4.79 (q, J=14.4 Hz, 2H), 4.37 (s, 1H), 4.32-4.21 (m, 1H), 3.72 (s, 3H), 3.30 (s, 3H), 3.10-2.99 (m, 1H), 2.96-2.69 (m, 3H), 2.25-2.12 (m, 2H), 2.08-2.01 (m, 1H), 1.96 (s, 2H), 1.89-1.78 (m, 1H), 1.42 (s, 9H); LC-MS (ESI$^+$) m/z 587.3 (M+H)$^+$.

Step 2—Tert-butyl3-[1-[1-[(4-methoxyphenyl)methyl]-2,6-dioxo-3-piperidyl]-3-methyl-2-oxo-benzimidazol-4-yl]-8-azabicyclo[3.2.1]octane-8-carboxylate To a solution of tert-butyl 3-[1-[1-[(4-methoxyphenyl)methyl]-2,6-dioxo-3-piperidyl]-3-methyl-2-oxo-benzimidazol-4-yl]-8-azabicyclo[3.2.1]oct-2-ene-8-carboxylate (500 mg, 852 umol) in THF (5 mL) was added Pd/C (200 mg, 852 umol, 10 wt %) and Pd/(OH)$_2$/C (200 mg, 852 umol, 10 wt %) under N$_2$. The suspension was degassed under vacuo and purged with H$_2$ several times. The mixture was stirred under H$_2$ (15 psi) at 25° C. for 4 hrs. On completion, the reaction was filtered and concentrated in vacuo to give title compound (500 mg, 99% yield) as yellow solid. $^1$H NMR (400 MHz, DMSO-d$_6$) δ 7.20 (d, J=8.8 Hz, 2H), 7.06 (d, J=7.6 Hz, 1H), 7.01-6.92 (m, 1H), 6.90-6.77 (m, 3H), 5.57-5.46 (m, 1H), 4.79 (q, J=14.4 Hz, 2H), 4.17 (s, 2H), 3.72 (s, 3H), 3.66 (s, 1H), 3.62-3.58 (m, 1H), 3.51 (s, 2H), 3.23-3.11 (m, 1H), 3.10-2.96 (m, 1H), 2.85-2.64 (m, 2H), 2.44-2.31 (m, 2H), 2.07-1.90 (m, 3H), 1.78-1.73 (m, 2H), 1.47-1.41 (m, 9H), 1.35 (s, 1H).

Step 3—3-[4-(8-azabicyclo[3.2.1]octan-3-yl)-3-methyl-2-oxo-benzimidazol-1-yl]piperidine-2,6-dione To a solution of tert-butyl 3-[1-[1-[(4-methoxyphenyl)methyl]-2,6-dioxo-3-piperidyl]-3-methyl-2-oxo-benzimidazol-4-yl]-8-azabicyclo[3.2.1]octane-8-carboxylate (250 mg, 424 umol) in TFA (7.70 g, 67.5 mmol, 5 mL) was added TfOH (2.13 g, 14.1 mmol, 1.25 mL). The reaction mixture was stirred at 70° C. for 2 hrs. On completion, the reaction mixture was concentrated in vacuo to give title compound (156 mg, 76% yield, TFA) as brown oil. LC-MS (ESI$^+$) m/z 369.2 (M+H)$^+$.

Step 4—Tert-butyl 3-[1-(2,6-dioxo-3-piperidyl)-3-methyl-2-oxo-benzimidazol-4-yl]-8-azabicyclo [3.2.1] octane-8-carboxylate To a solution of 3-[4-(8-azabicyclo[3.2.1]octan-3-yl)-3-methyl-2-oxo-benzimidazol-1-yl]piperidine-2,6-dione (156 mg, 323 umol, TFA) and TEA (327 mg, 3.23 mmol, 450 uL) in DCM (2 mL) was added Boc$_2$O (106 mg, 485 umol, 111 uL). The reaction mixture was stirred at 25° C. for 2 hrs. On completion, the reaction mixture was concentrated in vacuo. The residue was purified by prep-HPLC (column: Phenomenex luna C18 150*25 mm*10 um; mobile phase: [water (0.225% FA)-ACN]; B %: 38%-68%, 10 min) to give title compound (25 mg, 16% yield) as white solid. $^1$H NMR (400 MHz, DMSO-d$_6$) δ 11.09 (s, 1H), 7.11-6.99 (m, 2H), 6.98-6.94 (m, 1H), 5.40-5.33 (m, 1H), 4.17 (s, 2H), 3.66 (s, 1H), 3.51 (s, 3H), 2.90-2.83 (m, 1H), 2.76-2.68 (m, 1H), 2.65-2.58 (m, 1H), 2.05-1.93 (m, 3H), 1.88-1.82 (m, 1H), 1.78-1.67 (m, 2H), 1.60-1.50 (m, 1H), 1.47-1.41 (m, 11H).

Step 5—3-[4-(8-azabicyclo[3.2.1]octan-3-yl)-3-methyl-2-oxo-benzimidazol-1-yl]piperidine-2,6-dione To a solution of tert-butyl 3-[1-(2,6-dioxo-3-piperidyl)-3-methyl-2-oxo-benzimidazol-4-yl]-8-azabicyclo[3.2.1]octane-8-carboxylate (42.8 mg, 91.3 umol) in DCM (1 mL) was added TFA (459 mg, 4.03 mmol, 298 uL). The reaction was stirred at 25° C. for 2 hrs. On completion, the reaction mixture was concentrated in vacuo to give title compound (44 mg, 99% yield, TFA) as brown oil. LC-MS (ESI$^+$) m/z 369.2 (M+H)$^+$.

1-[8-[(1S,4S)-2,5-diazabicyclo[2.2.1]heptan-2-yl]-4-isoquinolyl]hexahydropyrimidine -2,4-dione (Intermediate CAO)

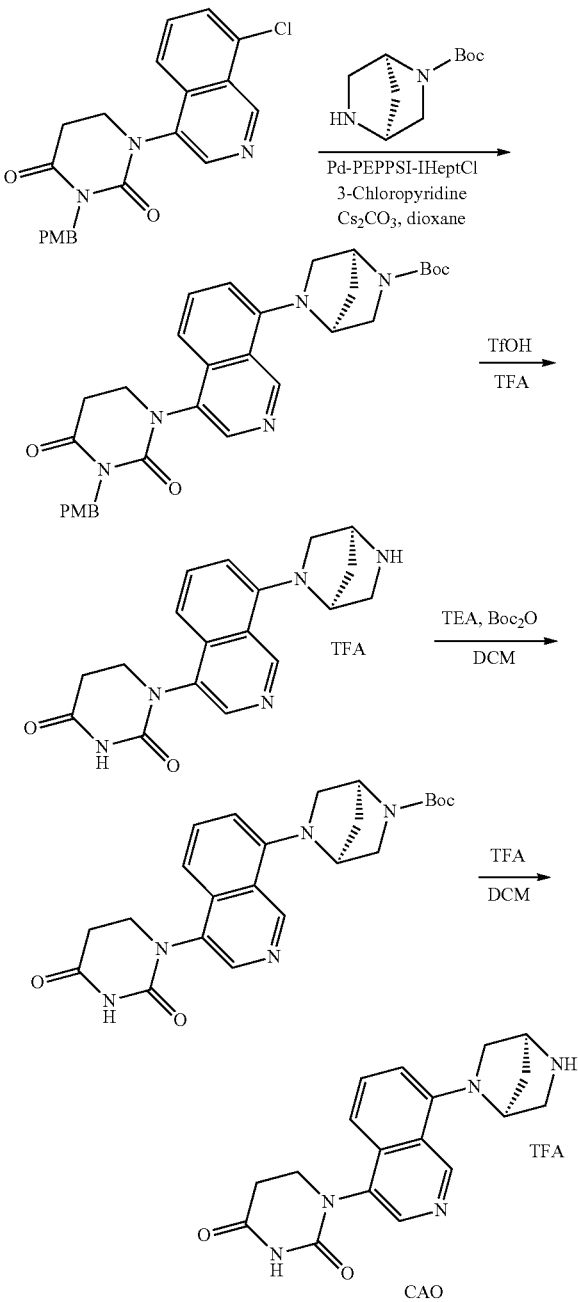

Step 1—Tert-butyl (1S,4S)-5-[4-[3-[(4-methoxyphenyl)methyl]-2,4-dioxo-hexahydropyrimidin-1-yl]-8-isoquinolyl]-2,5-diazabicyclo[2.2.1]heptane-2-carboxylate A solution of 1-(8-chloro-4-isoquinolyl)-3-[(4-methoxyphenyl)methyl]hexahydropyrimidine-2,4-dione (250 mg, 631 umol, synthesized via Steps 1-2 of Intermediate BSL), tert-butyl (1S,4S)-2,5-diazabicyclo[2.2.1]heptane-2-carboxylate (137 mg, 694 umol, CAS #113451-59-5), Cs₂CO₃ (411 mg, 1.26 mmol) and PD-PEPPSI-IHeptCl₃-Chloropyridine (30.7 mg, 31.5 umol) in dioxane (4.5 mL) was stirred at 80° C. under N₂ for 16 hrs. On completion, the reaction mixture was filtered and the filtrate was concentrated in vacuo. The residue was purified by reversed phase HPLC (0.1% FA condition) to give the title compound (330 mg, 93% yield) as yellow solid. ¹H NMR (400 MHz, DMSO-d₆) δ 9.38 (d, J=8.0 Hz, 1H), 8.45 (d, J=6.8 Hz, 1H), 7.62-7.54 (m, 1H), 7.31-7.23 (m, 3H), 7.03 (t, J=8.4 Hz, 1H), 6.91-6.85 (m, 2H), 4.86-4.81 (m, 2H), 4.59-4.52 (m, 1H), 4.50-4.42 (m, 1H), 4.14-4.01 (m, 1H), 3.94-3.79 (m, 1H), 3.73 (s, 3H), 3.63-3.54 (m, 1H), 3.16-3.05 (m, 1H), 2.99-2.91 (m, 1H), 2.58-2.53 (m, 1H), 2.08-1.89 (m, 2H), 1.48-1.25 (m, 11H); LC-MS (ESI⁺) m/z 558.3 (M+H)⁺.

Step 2—1-[8-[(1S,4S)-2,5-diazabicyclo[2.2.1]heptan-2-yl]-4-isoquinolyl]hexahydropyrimidine-2,4-dione To a solution of tert-butyl (1S,4S)-5-[4-[3-[(4-methoxyphenyl)methyl]-2,4-dioxo-hexahydropyrimidin-1-yl]-8-isoquinolyl]-2,5-diazabicyclo[2.2.1]heptane-2-carboxylate (150 mg, 268 umol) in TFA (3.08 g, 27.0 mmol) was added TfOH (680 mg, 4.53 mmol). The reaction mixture was then stirred at 70° C. for 2 hrs. On completion, the reaction mixture was concentrated in vacuo to give the title compound (121 mg, 99% yield, TFA) as red oil. LC-MS (ESI⁺) m/z 338.2 (M+H)⁺.

Step 3—Tert-butyl (1S,4S)-5-[4-(2,4-dioxohexahydropyrimidin-1-yl)-8-isoquinolyl]-2,5-diazabicyclo[2.2.1]heptane-2-carboxylate To a solution of 1-[8-[(1S,4S)-2,5-diazabicyclo[2.2.1]heptan-2-yl]-4-isoquinolyl]hexahydropyrimidine-2,4-dione (120 mg, 265 umol, TFA) and TEA (269 mg, 2.66 mmol) in DCM (1.5 mL) was added Boc₂O (87.0 mg, 398 umol) at 25° C. The reaction mixture was then stirred at 25° C. for 2 hrs. On completion, the reaction mixture was diluted with DCM (30 mL) and washed with water (30 mL×3). The organic layer was dried over Na₂SO₄, filtered and concentrated in vacuo to give the title compound (114 mg, 98% yield) as yellow solid. LC-MS (ESI⁺) m/z 438.2 (M+H)⁺.

Step 4—1-[8-[(1S,4S)-2,5-diazabicyclo[2.2.1]heptan-2-yl]-4-isoquinolyl]hexahydropyrimidine-2,4-dione To a solution of tert-butyl (1S,4S)-5-[4-(2,4-dioxohexahydropyrimidin-1-yl)-8-isoquinolyl]-2,5-diazabicyclo[2.2.1]heptane-2-carboxylate (95.0 mg, 217 umol) in DCM (1 mL) was added TFA (462 mg, 4.05 mmol). The reaction mixture was then stirred at 25° C. for 1 hr. On completion, the reaction mixture was concentrated in vacuo to give the title compound (98.0 mg, 99% yield, TFA) as red oil. LC-MS (ESI⁺) m/z 338.2 (M+H)⁺.

3-(4-bromo-3-ethyl-2-oxo-benzimidazol-1-yl)-1-[(4-methoxyphenyl)methyl]piperidine-2,6-dione (Intermediate CAP)

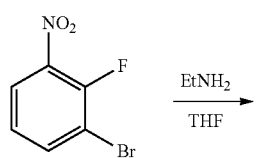

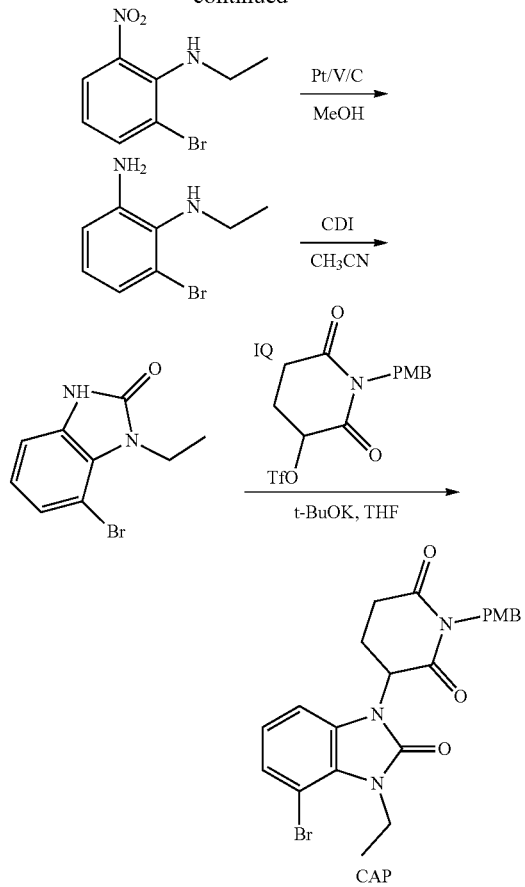

Step 1—2-Bromo-N-ethyl-6-nitro-aniline

To a solution of 1-bromo-2-fluoro-3-nitro-benzene (5 g, 22.7 mmol, CAS #58534-94-4) in THF (50 mL) was added ethanamine (2.05 g, 45.4 mmol) at 0° C. under N₂. The reaction was stirred at 25° C. for 16 hrs. On completion, the mixture was quenched with H₂O (50 mL), diluted with EA (50 mL), and extracted with EA (3×50 mL). The combined organic layer was washed with brine (3×50 mL), filtered and concentrated in vacuo to give the title compound (5.5 g, 100% yield) as yellow solid. ¹H NMR (400 MHz, DMSO-d₆) δ 7.86-7.78 (m, 2H), 6.80 (t, J=8.0 Hz, 1H), 5.99-5.89 (m, 1H), 3.11 (q, J=7.2 Hz, 2H), 1.11 (t, J=7.2 Hz, 3H). LC-MS (ESI⁺) m/z 244.8. (M+H)⁺.

Step 2—3-Bromo-N2-ethyl-benzene-1,2-diamine

To a solution of 2-bromo-N-ethyl-6-nitro-aniline (500 mg, 2.04 mmol) in THF (8 mL) was added Pt/V/C (250 mg, 957 umol) under N₂. The suspension was degassed under vacuum and purged with H2 three times. The mixture was stirred under H₂ (15 psi) at 25° C. for 16 hours. On completion, the mixture was filtered and concentrated in vacuo to give the title compound (400 mg, 91% yield) as brown oil. ¹H NMR (400 MHz, DMSO-d₆) δ 6.74-6.69 (m, 1H), 6.68-6.59 (m, 2H), 5.36-4.63 (m, 2H), 2.90 (q, J=7.2 Hz, 2H), 1.09 (t, J=7.2 Hz, 3H). LC-MS (ESI⁺) m/z 217.0 (M+H)⁺.

Step 3—4-Bromo-3-ethyl-1H-benzimidazol-2-one

To a solution of 3-bromo-N2-ethyl-benzene-1,2-diamine (400 mg, 1.86 mmol) in ACN (10 mL) was added CDI (361 mg, 2.23 mmol). The mixture was stirred at 80° C. for 16 hrs. On completion, the mixture was dropwise into H$_2$O (20 mL), then filtered and concentrated in vacuo to give the title compound (270 mg, 60% yield) as yellow solid. $^1$H NMR (400 MHz, DMSO-d$_6$) δ 11.19 (s, 1H), 7.17 (dd, J=1.2, 8.0 Hz, 1H), 7.01-6.97 (m, 1H), 6.95-6.89 (m, 1H), 4.11 (q, J=7.2 Hz, 2H), 1.22 (t, J=7.2 Hz, 3H). LC-MS (ESI$^+$) m/z 240.8 (M+H)$^+$.

Step 4—3-(4-Bromo-3-ethyl-2-oxo-benzimidazol-1-yl)-1-[(4-methoxyphenyl)methyl]piperidine-2,6-dione To a solution of 4-bromo-3-ethyl-1H-benzimidazol-2-one (240 mg, 995 umol) in THF (4 mL) was stirred at −10° C., then the t-BuOK (201 mg, 1.79 mmol) was added in above solution was stirred at −° C. for 1.5 hrs. Then a solution of [1-[(4-methoxyphenyl)methyl]-2,6-dioxo-3-piperidyl]trifluoromethanesulfonate (379 mg, 995 umol, Intermediate IQ) in THF (4 mL) was dropwise added into above solution. The mixture was stirred at −10° C. for 2.5 hrs. On completion, the reaction mixture was quenched by NH$_4$Cl (10 mL), diluted with H$_2$O (20 mL), and extracted with EA (2×20 mL). Then the combined organic layer was washed with brine (2×20 mL), dried with anhydrous Na$_2$SO$_4$ and concentrated in vacuo. The mixture was purified by reversed phase (0.1% FA) to give the title compound (340 mg, 72% yield) as green solid. $^1$H NMR (400 MHz, DMSO-d$_6$) δ 7.28-7.16 (m, 3H), 7.08 (d, J=6.8 Hz, 1H), 6.99-6.91 (m, 1H), 6.89-6.81 (m, 2H), 5.57 (dd, J=5.6, 13.2 Hz, 1H), 4.79 (q, J=14.4 Hz, 2H), 4.25-4.14 (m, 2H), 3.72 (s, 3H), 3.12-2.98 (m, 1H), 2.89-2.73 (m, 2H), 2.12-2.04 (m, 1H), 1.26 (t, J=7.2 Hz, 3H). LC-MS (ESI$^+$) m/z 474.1 (M+H)$^+$.

3-(3-ethyl-2-oxo-4-piperazin-1-yl-benzimidazol-1-yl)piperidine-2,6-dione (Intermediate CAQ)

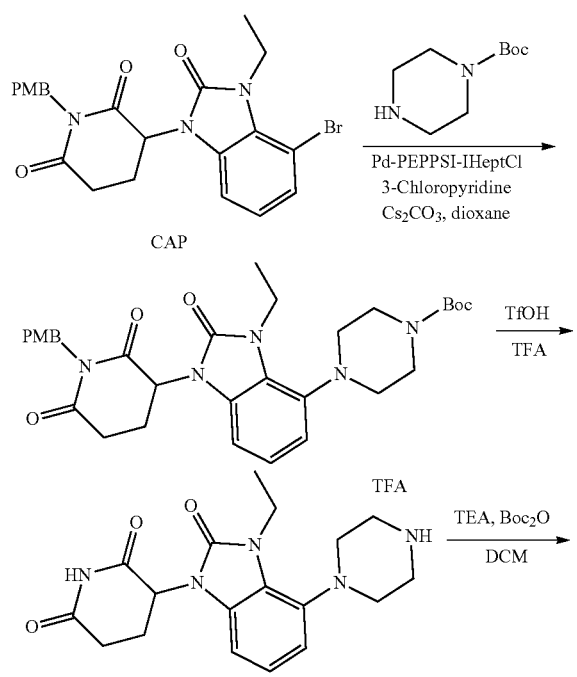

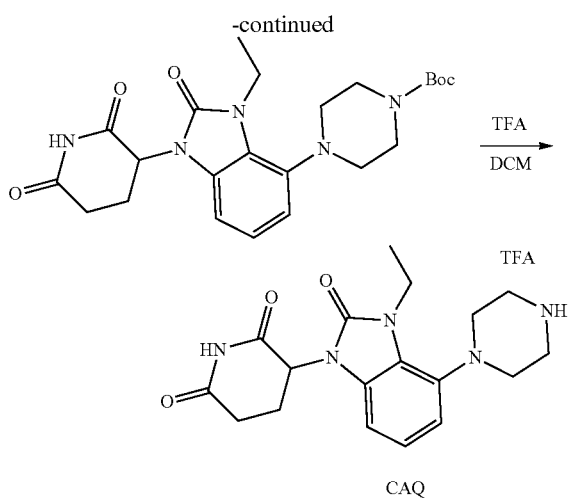

Step 1—Tert-butyl 4-[3-ethyl-1-[1-[(4-methoxyphenyl)methyl]-2,6-dioxo-3-piperidyl]-2-oxo-benzimidazol-4-yl]piperazine-1-carboxylate A mixture of 3-(4-bromo-3-ethyl-2-oxo-benzimidazol-1-yl)-1-[(4-methoxyphenyl)methyl]piperidine-2,6-dione (200 mg, 423 umol, Intermediate CAP), tert-butyl piperazine-1-carboxylate (157 mg, 846 umol, CAS #143238-38-4), Cs$_2$CO$_3$ (413 mg, 1.27 mmol) and Pd-PEPPSI-IHeptCl$_3$-Chloropyridine (41.1 mg, 42.3 umol) in dioxane (3.5 mL) was stirred at 100° C. for 5 hrs under N$_2$. On completion, the reaction mixture was diluted with EtOAc (30 mL), filtered and concentrated in vacuo. The residue was purified by prep-HPLC (column: Phenomenex Luna C18 150*25 mm*10 um; mobile phase: [water (0.225% FA)-ACN]; B %: 50%-80%, 10 min) to give the title compound (149 mg, 60% yield) as yellow solid. $^1$H NMR (400 MHz, DMSO-d$_6$) δ 7.21 (d, J=8.4 Hz, 2H), 7.02-6.91 (m, 2H), 6.88-6.78 (m, 3H), 5.54-5.48 (m, 1H), 4.79 (q, J=14.4 Hz, 2H), 4.11 (q, J=6.8 Hz, 2H), 4.02-3.92 (m, 2H), 3.72 (s, 3H), 3.11-2.92 (m, 5H), 2.84-2.68 (m, 4H), 2.08-2.01 (m, 1H), 1.43 (s, 9H), 1.22-1.17 (m, 3H); LC-MS (ESI$^+$) m/z 578.3 (M+H)$^+$.

Step 2—3-(3-ethyl-2-oxo-4-piperazin-1-yl-benzimidazol-1-yl)piperidine-2,6-dione

To a solution of tert-butyl 4-[3-ethyl-1-[1-[(4-methoxyphenyl)methyl]-2,6-dioxo-3-piperidyl]-2-oxo-benzimidazol-4-yl]piperazine-1-carboxylate (140 mg, 242 umol) in TFA (1.5 mL) was added TfOH (510 mg, 3.40 mmol). The reaction mixture was then stirred at 70° C. for 2 hrs. On completion, the reaction mixture was concentrated in vacuo to give title compound (114 mg, 99% yield, TFA) as red oil. LC-MS (ESI$^+$) m/z 358.2 (M+H)$^+$.

Step 3—Tert-butyl 4-[1-(2,6-dioxo-3-piperidyl)-3-ethyl-2-oxo-benzimidazol-4-yl]piperazine-1-carboxylate To a solution of 3-(3-ethyl-2-oxo-4-piperazin-1-yl-benzimidazol-1-yl)piperidine-2,6-dione (110 mg, 233 umol, TFA) and TEA (47.2 mg, 466 umol) in DCM (1 mL) was added Boc$_2$O (76.3 mg, 350 umol) at 25° C. The reaction mixture was then stirred at 25° C. for 16 hrs. On completion, the reaction mixture was diluted with DCM (30 mL) and washed with water (20 mL×3). The organic layer was dried over Na$_2$SO$_4$, filtered and concentrated in vacuo. The residue was purified by column chromatography (SiO$_2$, PE/EA=0/1) to give the title compound (100 mg, 93% yield) as yellow solid. 1H NMR (400 MHz, DMSO-d$_6$) δ 11.08 (s, 1H), 7.01 (d, J=4.4 Hz, 2H), 6.94 (q, J=4.4 Hz, 1H), 5.38-5.31 (m, 1H), 4.11 (q, J=6.8 Hz, 2H), 4.01-3.93 (m, 2H), 2.98 (d, J=10.4 Hz, 3H), 2.95-2.82 (m, 2H), 2.80-2.73 (m, 2H), 2.70-2.58 (m, 2H), 2.07-1.99 (m, 1H), 1.43 (s, 9H), 1.22-1.19 (m, 3H); LC-MS (ESI+) m/z 458.2 (M+H)$^+$.

Step 4—3-(3-ethyl-2-oxo-4-piperazin-1-yl-benzimidazol-1-yl)piperidine-2,6-dione

To a solution of tert-butyl 4-[1-(2,6-dioxo-3-piperidyl)-3-ethyl-2-oxo-benzimidazol-4-yl]piperazine-1-carboxylate (45.0 mg, 98.3 umol) in DCM (0.5 mL) was added TFA (770 mg, 6.75 mmol) at 25° C. The reaction mixture was then stirred at 25° C. for 2 hrs. On completion, the reaction mixture was concentrated in vacuo to give the title compound (46.3 mg, 100% yield, TFA) was obtained as brown solid. LC-MS (ESI$^+$) m/z 358.2 (M+H)$^+$.

3-[4-(1,4-Diazepan-1-yl)-3-methyl-2-oxo -benzimidazol-1-yl]piperidine-2,6-dione (Intermediate CAR)

Intermediate HP) and tert-butyl 1,4-diazepane-1-carboxylate (131 mg, 654 umol, CAS #112275-50-0) in dioxane (5 mL) was added Cs$_2$CO$_3$ (426 mg, 1.31 mmol) and Pd-PEPPSI-IHept$^{cl}$ 3-Chloropyridine (51.9 mg, 65.4 umol). The mixture was stirred at 80° C. for 16 hrs. On completion, the reaction mixture was filtered and the filtrate was concentrated in vacuo to give a residue. The residue was purified by column chromatography (SiO$_2$, PE:EA=5:1 to PE:EA=1:1, PE:EA=3:1, P1:Rf=0.3) to give the title compound (217 mg, 57% yield) as an off-white solid. 1H NMR (400 MHz, DMSO-d$_6$) δ 7.21 (d, J=8.8 Hz, 2H), 6.93 (d, J=4.0 Hz, 2H), 6.85 (d, J=8.8 Hz, 2H), 6.78 (s, 1H), 5.58-5.43 (m, 1H), 4.84-4.73 (m, 2H), 3.72 (s, 3H), 3.60 (d, J=4.4 Hz, 3H), 3.56-3.41 (m, 4H), 3.08 (d, J=6.0 Hz, 4H), 2.87-2.63 (m, 3H), 2.10-2.00 (m, 1H), 1.86 (s, 2H), 1.43 (d, J=4.4 Hz, 9H); LC-MS (ESI+) m/z 578.4 (M+H)$^+$.

Step 2—3-[4-(1,4-Diazepan-1-yl)-3-methyl-2-oxo-benzimidazol-1-yl]piperidine -2,6-dione To a solution of tert-butyl 4-[1-[1-[(4-methoxyphenyl) methyl]-2,6-dioxo-3-piperidyl]-3-methyl-2-oxo-benzimidazol-4-yl]-1,4-diazepane-1-carboxylate (100 mg, 173 umol) in TFA (2 mL) was added TfOH (510 mg, 3.40 mmol, 0.3 mL). Then the reaction mixture was stirred at 70° C. for 2 hrs. On completion, the reaction mixture was concentrated in vacuo to give the title compound (65 mg, 90% yield, TFA salt) as brown oil. LC-MS (ESI+) m/z 358.2 (M+H)$^+$.

1-[8-[(2R)-2-methylpiperazin-1-yl]-4-isoquinolyl] hexahydropyrimidine -2,4-dione (Intermediate CAS)

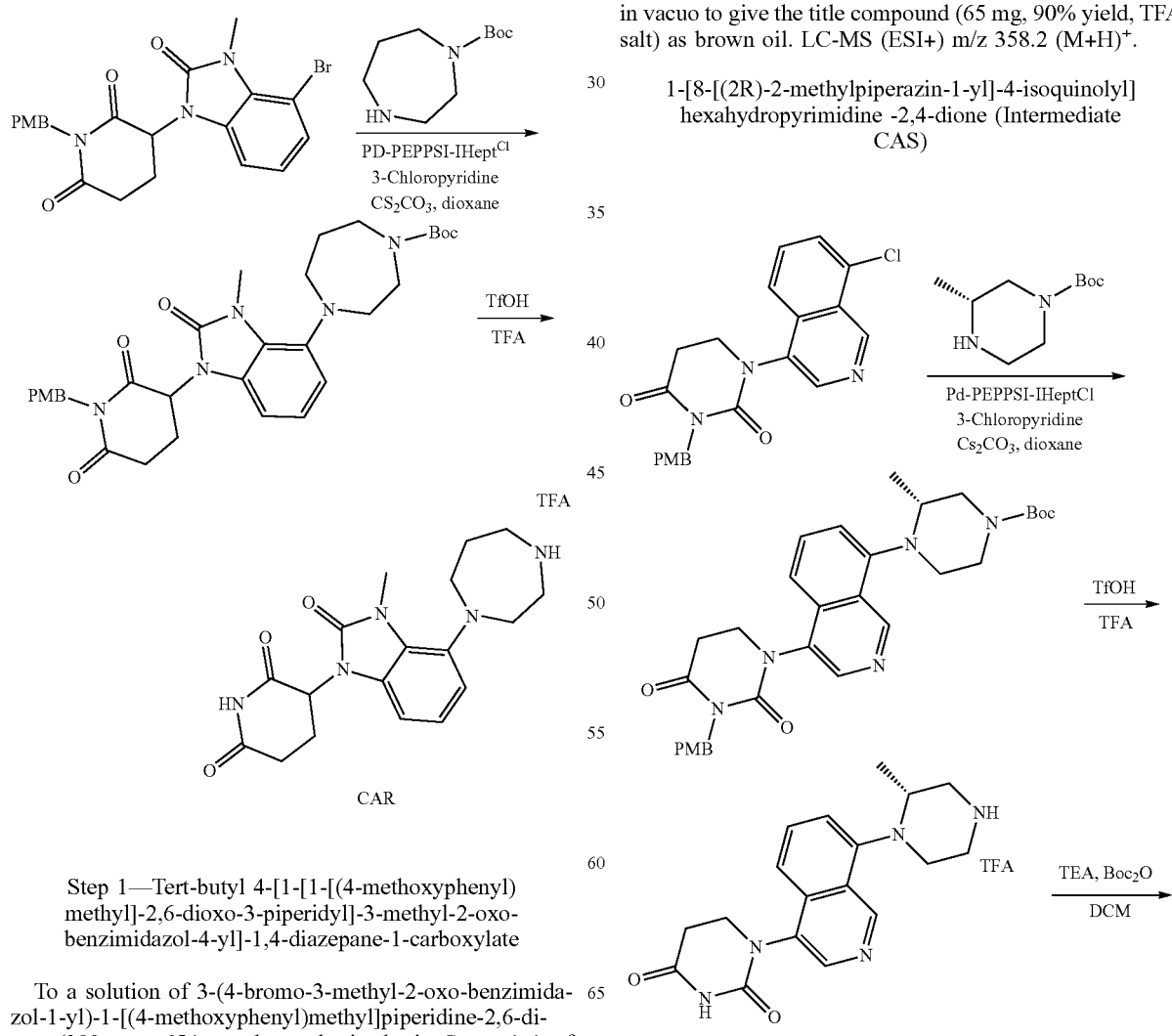

Step 1—Tert-butyl 4-[1-[1-[(4-methoxyphenyl) methyl]-2,6-dioxo-3-piperidyl]-3-methyl-2-oxo-benzimidazol-4-yl]-1,4-diazepane-1-carboxylate To a solution of 3-(4-bromo-3-methyl-2-oxo-benzimidazol-1-yl)-1-[(4-methoxyphenyl)methyl]piperidine-2,6-dione (300 mg, 654 umol, synthesized via Steps 1-4 of

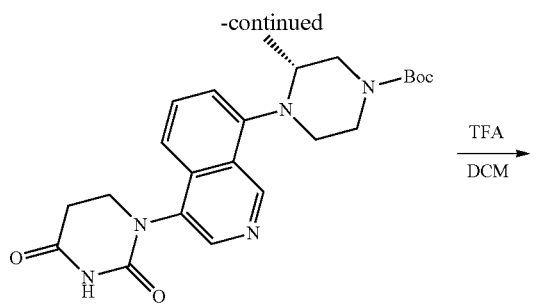

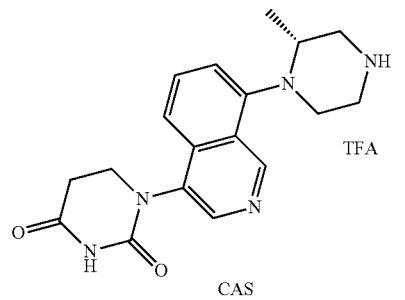

Step 1—Tert-butyl(3R)-4-[4-[3-[(4-methoxyphenyl)methyl]-2,4-dioxo-hexahydropyrimidin-1-yl]-8-isoquinolyl]-3-methyl-piperazine-1-carboxylate A mixture of 1-(8-chloro-4-isoquinolyl)-3-[(4-methoxyphenyl)methyl]hexahydropyrimidine-2,4-dione (250 mg, 631 umol, synthesized via Steps 1-2 of Intermediate BSL), tert-butyl (3R)-3-methylpiperazine-1-carboxylate (189 mg, 947 umol, CAS #163765-44-4), Cs$_2$CO$_3$ (617 mg, 1.89 mmol) and PD-PEPPSI-IHeptCl$_3$-Chloropyridine (36.8 mg, 37.8 umol) in dioxane (6 mL) was stirred at 110° C. for 16 hrs under N$_2$ atmosphere. On completion, the reaction mixture was diluted with EA (50 mL), filtered and concentrated in vacuo. The residue was purified by prep-HPLC (column: Phenomenex luna C18 150*25 mm*10 um; mobile phase: [water (0.225% FA)-ACN]; B %: 40%-70%, 10 min) to give the title compound (153 mg, 43% yield) as yellow solid. $^1$H NMR (400 MHz, DMSO-d$_6$) δ 9.62 (d, J=6.0 Hz, 1H), 8.55 (d, J=2.8 Hz, 1H), 7.78-7.72 (m, 1H), 7.67-7.63 (m, 1H), 7.45 (t, J=8.4 Hz, 1H), 7.28-7.23 (m, 2H), 6.88 (d, J=8.0 Hz, 2H), 4.83 (s, 2H), 3.99-3.84 (m, 2H), 3.80-3.74 (m, 1H), 3.73 (s, 3H), 3.69-3.52 (m, 2H), 3.46-3.39 (m, 1H), 3.21 (m, 1H), 3.19-3.07 (m, 2H), 3.00-0.92 (m, 1H), 2.80-2.72 (m, 1H), 1.45 (s, 9H), 0.84-0.80 (m, 3H).

Step 2—1-[8-[(2R)-2-methylpiperazin-1-yl]-4-isoquinolyl]hexahydropyrimidine-2,4-dione To a solution of tert-butyl (3R)-4-[4-[3-[(4-methoxyphenyl)methyl]-2,4-dioxo-hexahydropyrimidin-1-yl]-8-isoquinolyl]-3-methyl-piperazine-1-carboxylate (75.0 mg, 134 umol) in TFA (770 mg, 6.75 mmol) was added TfOH (170 mg, 1.13 mmol). The reaction mixture was then stirred at 70° C. for 2 hrs. On completion, the reaction mixture was concentrated in vacuo to give the title compound (60.0 mg, 99% yield, TFA) as red oil. LC-MS (ESI$^+$) m/z 340.3 (M+H)$^+$.

Step 3—Tert-butyl (3R)-4-[4-(2,4-dioxohexahydropyrimidin-1-yl)-8-isoquinolyl]-3-methyl-piperazine-1-carboxylate A mixture of 1-[8-[(2R)-2-methylpiperazin-1-yl]-4-isoquinolyl]hexahydropyrimidine-2,4-dione (60.0 mg, 132 umol, TFA), TEA (26.7 mg, 264 umol) and Boc$_2$O (43.3 mg, 198 umol) in DCM (1 mL) was stirred at 25° C. for 1 hr. On completion, the reaction mixture was diluted with DCM (20 mL) and washed with water (15 mL×3). The organic layer was dried over Na$_2$SO$_4$ and filtered. The filtrate was concentrated in vacuo to give the title compound (58.0 mg, 99% yield) as yellow solid. $^1$H NMR (400 MHz, DMSO-d$_6$) δ 10.36-10.29 (m, 1H), 7.41-7.33 (m, 1H), 7.30-7.23 (m, 1H), 7.16-6.99 (m, 3H), 3.94-3.78 (m, 2H), 3.66-3.55 (m, 2H), 3.26-3.07 (m, 3H), 2.78-2.69 (m, 2H), 2.68-2.57 (m, 2H), 1.52 (s, 9H), 1.45 (s, 3H).

Step 4—1-[8-[(2R)-2-methylpiperazin-1-yl]-4-isoquinolyl]hexahydropyrimidine-2,4-dione To a solution of tert-butyl (3R)-4-[4-(2,4-dioxohexahydropyrimidin-1-yl)-8-isoquinolyl]-3-methyl-piperazine-1-carboxylate (38 mg, 86.4 umol) in DCM (1 mL) was added TFA (585 mg, 5.13 mmol) at 25° C. The reaction mixture was stirred at 25° C. for 1 hr. On completion, the reaction mixture was concentrated in vacuo to give title compound (39.1 mg, 99% yield, TFA) as brown oil. LC-MS (ESI$^+$) m/z 340.2 (M+H)$^+$.

2-(2,6-Dioxo-3-piperidyl)-4-[[3-[methyl-[3-(methylamino)propyl]amino]cyclobutyl]amino]isoindoline-1,3-dione (Intermediate CAT)

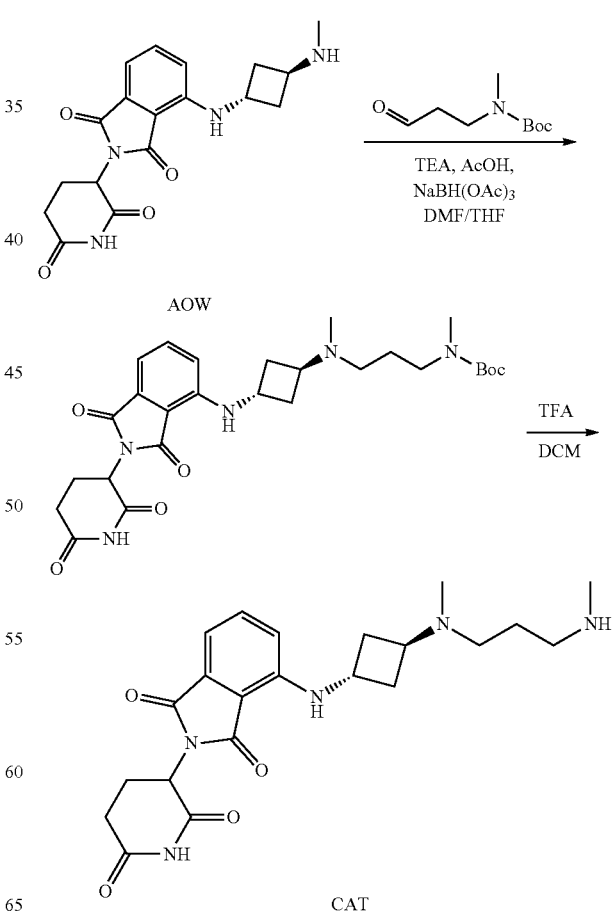

Step 1—Tert-butyl N-[3-[[3-[[2-(2,6-dioxo-3-piperidyl)-1,3-dioxo-isoindolin-4-yl]amino]cyclobutyl]-methyl-amino]propyl]-N-methyl-carbamate To a solution of 2-(2,6-dioxo-3-piperidyl)-4-[[3-(methylamino)cyclobutyl]amino]isoindoline-1,3-dione (100 mg, 212 umol, Intermediate AOW) and tert-butyl N-methyl-N-(3-oxopropyl)carbamate (39.8 mg, 212 umol, CAS #273757-11-2) in mixture solvent THF (4 mL) and DMF (1 mL) was added TEA (43.0 mg, 425 umol), then the mixture was stirred at 25° C. for 5 mins. Next, AcOH (38.3 mg, 637 umol) was added to the solution, and the mixture was stirred at 25° C. for 25 mins. Then NaBH(OAc)₃ (90.1 mg, 425 umol) was added to the solution, and the mixture and stirred at 25° C. for 1.5 hours. On completion, the mixture was quenched with H₂O (0.5 mL) and concentrated in vacuo. The crude product was purified by prep-HPLC (column: Phenomenex Luna C18 150*25 mm*10 um; mobile phase: [water (FA)-ACN]; B %: 12%-42%, 10.5 min) to give the title compound (112 mg, 99% yield) as a yellow solid. $^1$H NMR (400 MHz, DMSO-$d_6$) δ 11.11 (s, 1H), 7.66-7.58 (m, 1H), 7.12 (d, J=7.2 Hz, 1H), 6.90 (d, J=8.8 Hz, 1H), 6.65-6.57 (m, 1H), 5.06 (dd, J=5.6, 12.8 Hz, 1H), 4.15-4.10 (m, 1H), 3.20 (t, J=7.2 Hz, 3H), 3.00-2.82 (m, 2H), 2.78 (s, 3H), 2.64-2.60 (m, 1H), 2.59-2.51 (m, 5H), 2.47-2.37 (m, 2H), 2.31-2.21 (m, 2H), 2.07-2.00 (m, 1H), 1.83-1.69 (m, 2H), 1.39 (s, 9H). LC-MS (ESI⁺) m/z 528.2 (M+H)⁺.

Step 2—2-(2,6-Dioxo-3-piperidyl)-4-[[3[methyl-[3-(methylamino) propyl]amino] cyclobutyl]amino] isoindoline-1,3-dione To a solution of tert-butyl N-[3-[[3-[[2-(2,6-dioxo-3-piperidyl)-1,3-dioxo-isoindolin-4-yl] amino] cyclobutyl]-methyl-amino] propyl]-N-methyl-carbamate (50 mg, 94.7 umol) in DCM (2 mL) was added TFA (154 mg, 1.35 mmol). The mixture was then stirred at 25° C. for 2 hrs. On completion, the mixture was concentrated in vacuo to give the title compound (51 mg, 99% yield, TFA) as yellow oil. LC-MS (ESI⁺) m/z 428.3 (M+H)⁺.

N-[2-(4-formylcyclohexyl)-6-(1-hydroxy-1-methyl-ethyl)indazol-5-yl]-6-methyl-pyridine-2-carboxamide (Intermediate CAU)

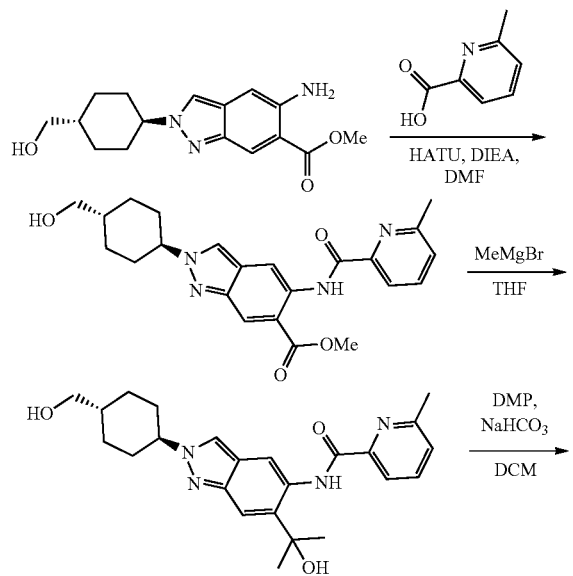

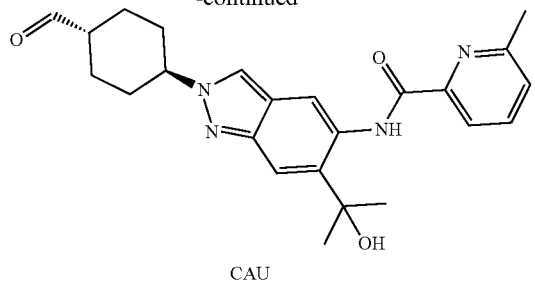

CAU

Step 1—Methyl 2-[4-(hydroxymethyl)cyclohexyl]-5-[(6-methylpyridine-2-carbonyl)amino]indazole-6-carboxylate A mixture of 6-methylpyridine-2-carboxylic acid (162 mg, 1.19 mmol, CAS #934-60-1) in DMF (2 mL) was added DIEA (383 mg, 2.97 mmol) and HATU (752 mg, 1.98 mmol) at 0° C. The mixture was stirred at 0° C. for 0.5 hr. Then methyl 5-amino-2-[4-(hydroxymethyl)cyclohexyl]indazole-6-carboxylate (300 mg, 988 umol, synthesized via Steps 1-3 of Intermediate BXI) in DMF (2 mL) was added the mixture at 0° C. The mixture was then stirred at 25° C. for 2 hrs. On completion, the reaction mixture was concentrated under reduced pressure to give a residue. The residue was purified by prep-HPLC (column: YMC Triart C18 250*50 mm*7 um; mobile phase: [water (NH₄HCO₃)-ACN]; B %: 48%-78%, 10 min) to give the title compound (230 mg, 54% yield, FA salt) as white liquid. LC-MS (ESI⁺) m/z 423.0 (M+H)⁺. $^1$H NMR (400 MHz, DMSO-$d_6$) δ 12.59 (s, 1H), 9.07 (s, 1H), 8.55 (s, 1H), 8.45 (s, 1H), 8.00-7.93 (m, 2H), 7.55-7.53 (m, 1H), 4.53-4.74 (m, 2H), 3.98 (s, 3H), 3.30-3.27 (m, 2H), 2.65 (s, 3H), 2.52 (d, J=1.6 Hz, 2H), 2.18 (d, J=9.2 Hz, 2H), 1.92 (d, J=10.8 Hz, 2H), 1.50 (s, 1H), 1.25-1.09 (m, 2H).

Step 2—N-[2-[4-(hydroxymethyl)cyclohexyl]-6-(1-hydroxy-1-methyl-ethyl)indazol-5-yl]-6-methyl-pyridine-2-carboxamide A mixture of methyl 2-[4-(hydroxymethyl)cyclohexyl]-5-[(6-methylpyridine-2-carbonyl)amino] indazole-6-carboxylate (230 mg, 544 umol) in THF (20 mL) was degassed and purged with N₂ three times and the mixture was added MeMgBr (3 M, 3.63 mL). Then the mixture was stirred at 25° C. for 4 hrs under N₂ atmosphere. On completion, the reaction mixture was quenched by addition NH₄Cl aq. (10 mL) at 25° C., and then extracted with EA (3×50 mL). The combined organic layers were washed with NaHCO₃ aq. (2×25 mL) and brine (2×25 mL), dried over Na₂SO₄, filtered and concentrated under reduced pressure to give a residue. The residue was purified by prep-HPLC (column: Phenomenex luna C18 150*25 mm*10 um; mobile phase: [water (FA)-ACN]; B %: 27%-57%, 10.5 min) to give the title compound (150 mg, 65% yield) as a white solid. LC-MS (ESI⁺) m/z 445.0 (M+Na)⁺, $^1$H NMR (400 MHz, DMSO-$d_6$) δ 12.38 (s, 1H), 8.69 (s, 1H), 8.33 (s, 1H), 7.99-7.88 (m, 2H), 7.56 (s, 1H), 7.49 (d, J=0.8, 7.2 Hz, 1H), 5.90 (s, 1H), 4.58-4.31 (m, 2H), 3.30 (s, 2H), 2.60 (s, 3H), 2.19-2.08 (m, 2H), 1.90 (d, J=10.4 Hz, 4H), 1.63 (s, 6H), 1.48 (s, 1H), 1.22-1.07 (m, 2H).

Step 3—N-[2-(4-formylcyclohexyl)-6-(1-hydroxy-1-methyl-ethyl)indazol-5-yl]-6-methyl-pyridine-2-carboxamide To a mixture of N-[2-[4-(hydroxymethyl)cyclohexyl]-6-(1-hydroxy-1-methyl-ethyl)indazol-5-yl]-6-methyl-pyridine-2-carboxamide (50.0 mg, 118 umol) and NaHCO$_3$ (49.7 mg, 591 umol) in THF (3 mL) was added DMP (75.2 mg, 177 umol) at 0° C. The reaction mixture was then stirred at 25° C. for 5 hrs. On completion, the reaction mixture was diluted with saturated Na$_2$S$_2$O$_3$ aq. (15 mL) and saturated NaHCO$_3$ aqueous (15 mL). The mixture was diluted with water (20 mL) and extracted with DCM (3×20 mL). The organic layer was washed with saturated NaHCO$_3$ aqueous (2×10 mL) and brine (2×10 mL). The organic layer was dried over anhydrous sodium sulfate and filtered to give the title compound (90 mg, 90% yield) as a white solid. $^1$H NMR (400 MHz, DMSO-d$_6$) δ 12.39 (s, 1H), 9.65 (s, 1H), 8.70 (s, 1H), 8.34 (s, 1H), 8.00-7.89 (m, 2H), 7.57 (s, 1H), 7.49 (d, J=7.2 Hz, 1H), 5.90 (s, 1H), 4.48-4.40 (m, 1H), 2.60 (s, 3H), 2.46-2.39 (m, 1H), 2.22-2.18 (m, 2H), 2.11 (d, J=11.6 Hz, 2H), 2.03-1.92 (m, 2H), 1.63 (s, 6H), 1.50-1.39 (m, 2H).

3-[1-(2,6-Dioxo-3-piperidyl)-3-methyl-2-oxo-benzimidazol-4-yl]cyclobutane carbaldehyde (Intermediate CAV)

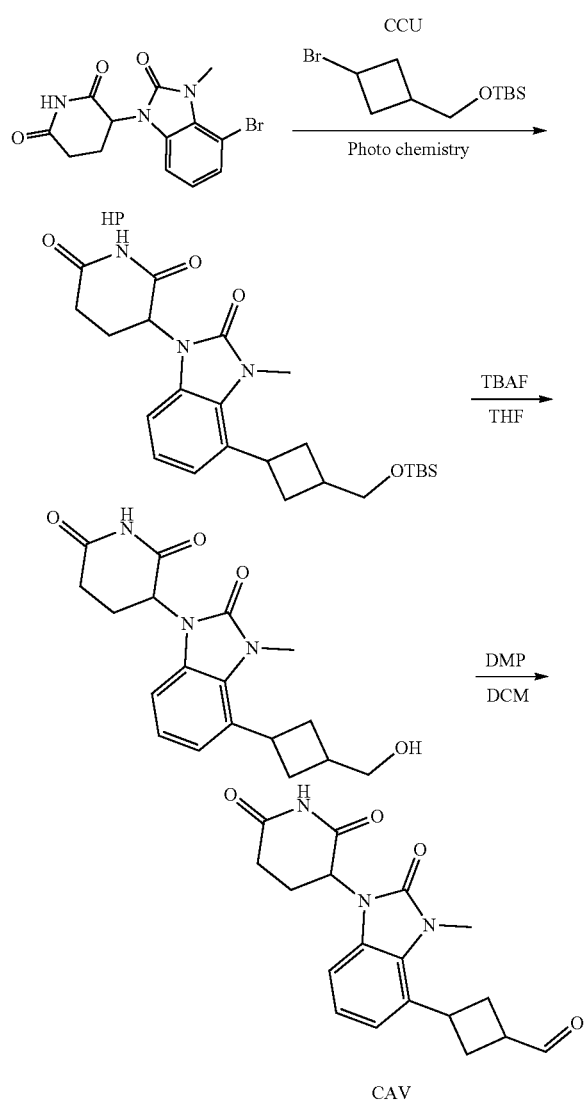

Step 1—3-[4-[3-[[Tert-butyl(dimethyl)silyl]oxymethyl]cyclobutyl]-3-methyl-2-oxo-benzimidazol-1-yl]piperidine-2,6-dione To an 15 mL vial equipped with a stir bar was added 3-(4-bromo-3-methyl-2-oxo-benzimidazol-1-yl)piperidine-2,6-dione (745 mg, 2.20 mmol, Intermediate HP), (3-bromocyclobutyl)methoxy-tert-butyl-dimethyl-silane (800 mg, 2.86 mmol, Intermediate CCU), Ir[dF(CF$_3$)ppy]$_2$(dtbpy)(PF6) (24.7 mg, 22.0 umol), NiCl$_2$.dtbbpy (4.38 mg, 11.0 umol), TTMSS (680 uL, 2.20 mmol), and 2,6-lutidine (513 uL, 4.41 mmol) in DME (2 mL). The vial was sealed and placed under nitrogen and the reaction was stirred and irradiated with a 10 W blue LED lamp (3 cm away), with cooling water to keep the reaction temperature at 25° C. for 14 hr. On completion, the mixture was filtered and the filtrate was washed with water (50 mL) and extracted with EA (30 mL×3). The combined organic layer was dried over anhydrous Na$_2$SO$_4$, then concentrated in vacuo to give a residue. The residue was purified by reverse-phase (0.1% FA condition) to give the title compound (335 mg, 33% yield) as a yellow solid. $^1$H NMR (400 MHz, CDCl$_3$-d) δ 8.75 (s, 1H), 7.24-7.12 (m, 1H), 7.08-7.00 (m, 1H), 6.68 (dd, J=5.6, 7.2 Hz, 1H), 5.23 (dd, J=5.2, 12.2 Hz, 1H), 4.11 (quin, J=8.0 Hz, 1H), 3.75 (d, J=6.0 Hz, 1H), 3.69 (s, 1H), 3.63 (s, 2H), 3.60 (d, J=5.2 Hz, 1H), 2.92-2.79 (m, 1H), 2.84-2.79 (m, 1H), 2.76-2.67 (m, 1H), 2.58-2.46 (m, 1H), 2.41-2.31 (m, 2H), 2.31-2.23 (m, 1H), 2.21-2.09 (m, 2H), 0.93-0.93 (m, 1H), 0.93 (d, J=8.0 Hz, 8H), 0.09 (d, J=11.2 Hz, 5H). LC-MS (ESI$^+$) m/z 458.4 (M+H)$^+$.

Step 2—3-[4-[3-(Hydroxymethyl)cyclobutyl]-3-methyl-2-oxo-benzimidazol-1-yl]piperidine-2,6-dione To a solution of 3-[4-[3-[[tert-butyl(dimethyl)silyl]oxymethyl]cyclobutyl]-3-methyl-2-oxo-benzimidazol-1-yl]piperidine-2,6-dione (100 mg, 218 umol) in THF (1 mL) was added TBAF (1 M, 218 uL), then the mixture was stirred at 25° C. for 1 hour. On completion, the mixture was washed with water (30 mL) and extracted with EA (20 mL×3). The combined organic layer was dried over anhydrous Na$_2$SO$_4$, then concentrated in vacuo to give a residue. The residue was purified by column chromatography to give the title compound (70.0 mg, 93% yield) as a white solid. $^1$H NMR (400 MHz, CDCl$_3$-d) δ 8.06 (s, 1H), 7.15-7.05 (m, 2H), 6.71-6.66 (m, 1H), 5.25-5.15 (m, 1H), 4.02-3.89 (m, 1H), 3.70 (s, 3H), 3.68-3.63 (m, 3H), 2.99-2.90 (m, 1H), 2.88-2.82 (m, 1H), 2.81-2.70 (m, 2H), 2.56 (d, J=7.2 Hz, 1H), 2.48-2.41 (m, 2H), 2.31-2.18 (m, 2H). LC-MS (ESI$^+$) m/z 344.1 (M+H)$^+$.

Step 3—3-[1-(2,6-Dioxo-3-piperidyl)-3-methyl-2-oxo-benzimidazol-4-yl]cyclobutanecarbaldehyde To a solution of 3-[4-[3-(hydroxymethyl)cyclobutyl]-3-methyl-2-oxo-benzimidazol-1-yl]piperidine-2,6-dione (100 mg, 291 umol) in DCM (2 mL) was added DMP (135 uL, 436 umol), then the mixture was stirred at 25° C. for 1 hour. On completion, the mixture was quenched with sodium thiosulfate pentahydrate (5 mL) and NaHCO$_3$ (5 mL), then extracted with DCM (30 mL×3). The combined organic layer was dried over anhydrous Na$_2$SO$_4$, then concentrated in vacuo to give the title compound (95.0 mg, 95% yield) as a white solid. LC-MS (ESI$^+$) m/z 342.1 (M+H)$^+$.

2-(2,6-dioxo-3-piperidyl)-4-[[3-[3-(methylamino) propoxy] cyclobutyl]amino]isoindoline-1,3-dione (Intermediate AOQ)

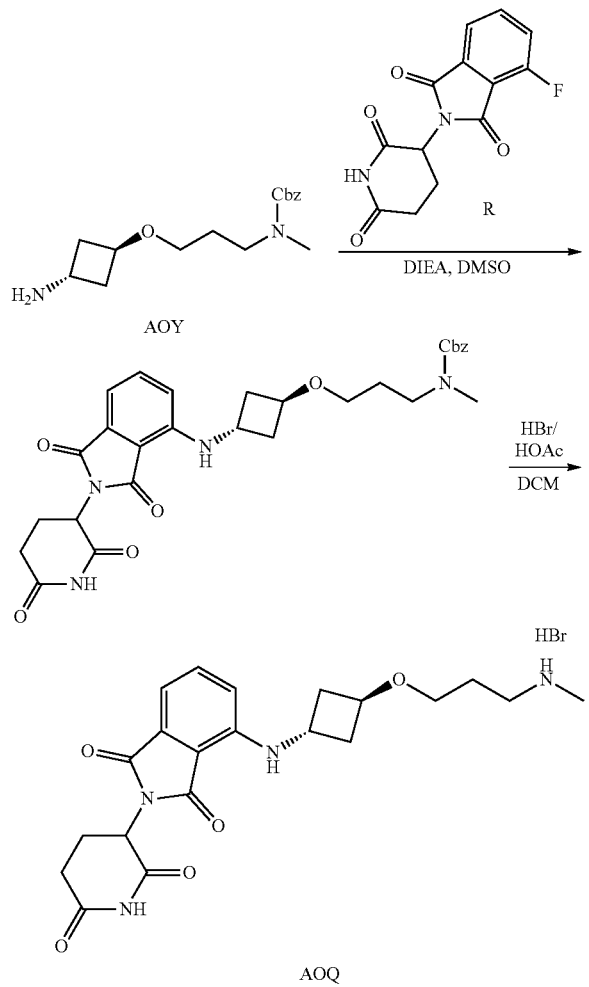

Step 1—Benzyl N-[3-[3-[[2-(2,6-dioxo-3-piperidyl)-1,3-dioxo-isoindolin-4-yl]amino]cyclobutoxy] propyl]-N-methyl-carbamate To a solution of benzyl N-[3-(3-aminocyclobutoxy)propyl]-N-methyl-carbamate (1.30 g, 3.95 mmol, HCl salt, Intermediate AOY) and 2-(2,6-dioxo-3-piperidyl)-4-fluoro-isoindoline-1,3-dione (928 mg, 3.36 mmol, Intermediate R) in DMSO (15 mL) was added DIPEA (2.55 g, 19.7 mmol). The reaction mixture was stirred at 130° C. for 3 hrs. On completion, the reaction mixture was diluted with water (50 mL) and extracted with EA (3×70 mL). The combined organic layers were washed with brine (50 mL), dried over $Na_2SO_4$, filtered and concentrated in vacuo. The residue was purified by reverse phase (0.1% FA) to give the title compound (810 mg, 37% yield) as yellow solid. $^1$H NMR (400 MHz, $CDCl_3$) δ 8.02 (s, 1H), 7.54-7.47 (m, 1H), 7.42-7.28 (m, 5H), 7.14 (d, J=7.2 Hz, 1H), 6.80-6.64 (m, 1H), 6.36-6.22 (m, 1H), 5.14 (s, 2H), 4.99-4.87 (m, 1H), 4.24-4.05 (m, 2H), 3.47-3.28 (m, 4H), 2.95 (s, 3H), 2.93-2.84 (m, 1H), 2.84-2.70 (m, 2H), 2.57-2.35 (m, 2H), 2.28-2.09 (m, 3H), 1.90-1.74 (m, 2H).

Step 2—2-(2,6-Dioxo-3-piperidyl)-4-[[3-[3-(methylamino)propoxy]cyclobutyl]amino]isoindoline-1,3-dione To a solution of benzyl N-[3-[3-[[2-(2,6-dioxo-3-piperidyl)-1,3-dioxo-isoindolin-4-yl]amino] cyclobutoxy]propyl]-N-methyl-carbamate (0.80 g, 1.46 mmol) in DCM (10 mL) was added HBr/AcOH (1.46 mmol, 10 mL, 30% solution). The reaction mixture was stirred at 20° C. for 1 hour. On completion, the reaction mixture was dried by nitrogen. The residue was diluted with $ACN/H_2O$=1/1 (100 mL) and lyophilizated to give the title compound (722 mg, 99% yield, HBr salt) as yellow solid. $^1$H NMR (400 MHz, DMSO-$d_6$) δ 11.09 (s, 1H), 8.32 (s, 2H), 7.60 (dd, J=7.2, 8.4 Hz, 1H), 7.09 (d, J=7.0 Hz, 1H), 6.91 (d, J=8.4 Hz, 1H), 6.68-6.25 (m, 1H), 5.06 (dd, J=5.6, 12.8 Hz, 1H), 4.22-4.11 (m, 2H), 3.38 (t, J=6.0 Hz, 2H), 3.04-2.80 (m, 3H), 2.63-2.55 (m, 4H), 2.54-2.52 (m, 1H), 2.44-2.33 (m, 2H), 2.29-2.18 (m, 2H), 2.12-1.97 (m, 1H), 1.90-1.76 (m, 2H).

N-[2-(4-formylcyclohexyl)-6-(1-hydroxy-1-methylethyl)indazol-5-yl]pyridine-2-carboxamide (Intermediate CAW)

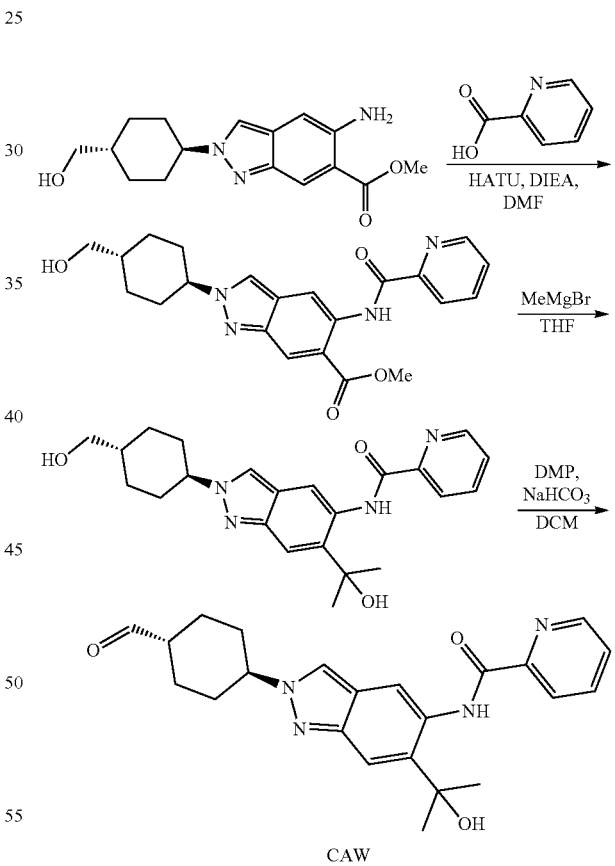

Step 1—Methyl 2-[4-(hydroxymethyl)cyclohexyl]-5-(pyridine-2-carbonylamino)indazole-6-carboxylate To a mixture of pyridine-2-carboxylic acid (146 mg, 1.19 mmol, CAS #636-80-6) in DMF (2 mL) was added DIEA (383 mg, 2.97 mmol) and HATU (752 mg, 1.98 mmol) at 0° C. The mixture was stirred at 0° C. for 0.5 hr. Then methyl 5-amino-2-[4-(hydroxymethyl)cyclohexyl]indazole-6-carboxylate (300 mg, 988 umol, synthesized via Steps 1-3 of Intermediate BXI) in DMF (2 mL) was added the mixture at 0° C. The mixture was stirred at 25° C. for 2 hrs. On completion, the reaction mixture was concentrated under reduced pressure to give a residue. The residue was purified by prep-HPLC (column: YMC-Triart Prep C18 150*40 mm*7 um; mobile phase: [water(NH4HCO3)-ACN]; B %: 39%-69%, 8 min) to give the title compound (220 mg, 53% yield) as yellow solid. LC-MS (ESI$^+$) m/z 409.0 (M+H)$^+$. $^1$H NMR (400 MHz, DMSO-d$_6$) δ 12.63 (s, 1H), 9.09 (s, 1H), 8.79 (d, J=4.8 Hz, 1H), 8.56 (s, 1H), 8.47 (s, 1H), 8.20 (d, J=7.6 Hz, 1H), 8.10-8.06 (m, 1H), 7.69-7.66 (m, 1H), 4.56-4.45 (m, 2H), 3.97 (s, 3H), 3.31-3.25 (m, 3H), 2.19-2.16 (m, 2H), 1.93-1.90 (m, 3H), 1.50-1.49 (m, 1H), 1.26-1.09 (m, 2H).

Step 2—N-[2-[4-(hydroxymethyl)cyclohexyl]-6-(1-hydroxy-1-methyl-ethyl)indazol-5-yl]pyridine-2-carboxamide A mixture of methyl 2-[4-(hydroxymethyl)cyclohexyl]-S-(pyridine-2-carbonylamino)indazole-6-carboxylate (220 mg, 538 umol) in THF (50 mL) was degassed and purged with N$_2$ three times Next, MeMgBr (3 M, 3.59 mL) was added to the reaction mixture and then the mixture was stirred at 25° C. for 4 hrs under N$_2$ atmosphere. On completion, the reaction mixture was quenched by addition NH$_4$Cl aq. 10 mL at 25° C., and then extracted with EA (3×50 mL). The combined organic layers were washed with NaHCO$_3$ aq. (2×25 mL) and brine (2×25 mL), dried over Na$_2$SO$_4$, filtered and concentrated under reduced pressure to give a residue. The residue was purified by prep-HPLC (column: Phenomenex luna C18 150*25 mm*10 um; mobile phase: [water (FA)-ACN]; B %: 23%-53%, 10.5 min) to give the title compound (131 mg, 59% yield) as a white solid. LC-MS (ESI$^+$) m/z 408.9 (M+H)$^+$, $^1$H NMR (400 MHz, DMSO-d$_6$) δ 12.32 (s, 1H), 8.69-8.67 (m, 2H), 8.34 (s, 1H), 8.26-7.97 (m, 2H), 7.73-7.47 (m, 2H), 6.02 (s, 1H), 4.61-4.27 (m, 2H), 3.30-3.23 (m, 2H), 2.13 (s, 2H), 1.90 (d, J=10.4 Hz, 4H), 1.61 (s, 6H), 1.48-1.47 (m, 1H), 1.25-1.08 (m, 2H).

Step 3—N-[2-(4-formylcyclohexyl)-6-(1-hydroxy-1-methyl-ethyl)indazol-5-yl]pyridine-2-carboxamide To a mixture of N-[2-[4-(hydroxymethyl)cyclohexyl]-6-(1-hydroxy-1-methyl-ethyl)indazol-5-yl]pyridine-2-carboxamide (50.0 mg, 122 umol) and NaHCO$_3$ (51.4 mg, 612 umol) in THF (3 mL) was added DMP (129 mg, 306 umol) at 0° C. The reaction mixture was stirred at 25° C. for 8 hrs. On completion, the reaction mixture was diluted with saturated Na$_2$S$_2$O$_3$ aq. (15 mL) and saturated NaHCO$_3$ aqueous (15 mL). Then the mixture was diluted with water (20 mL) and extracted with DCM (3×20 mL). The organic layer was washed with saturated NaHCO$_3$ aqueous (2×10 mL) and brine (2×10 mL). The organic layer was dried over anhydrous sodium sulfate and filtered to give the title compound (99 mg, 95% yield) as a white solid. LC-MS (ESI$^+$) m/z 407.1 (M+H)$^+$, NMR (400 MHz, DMSO-d$_6$) δ 12.33 (s, 1H), 9.65 (s, 1H), 8.74-8.65 (m, 2H), 8.35 (s, 1H), 8.19 (d, J=7.6 Hz, 1H), 8.08-8.04 (m, 1H), 7.67-7.60 (m, 1H), 7.56 (s, 1H), 6.02 (s, 1H), 4.49-4.41 (m, 1H), 2.46-2.40 (m, 1H), 2.22-2.18 (m, 2H), 2.11 (br d, J=11.2 Hz, 2H), 2.04-1.99 (m, 1H), 1.98-1.92 (m, 1H), 1.62 (s, 6H), 1.45 (q, J=4.0, 13.2 Hz, 2H).

3-[4-(2,5-Dihydro-1H-pyrrol-3-yl)-3-methyl-2-oxo-benzimidazol-1-yl]piperidine-2,6-dione (Intermediate CAX)

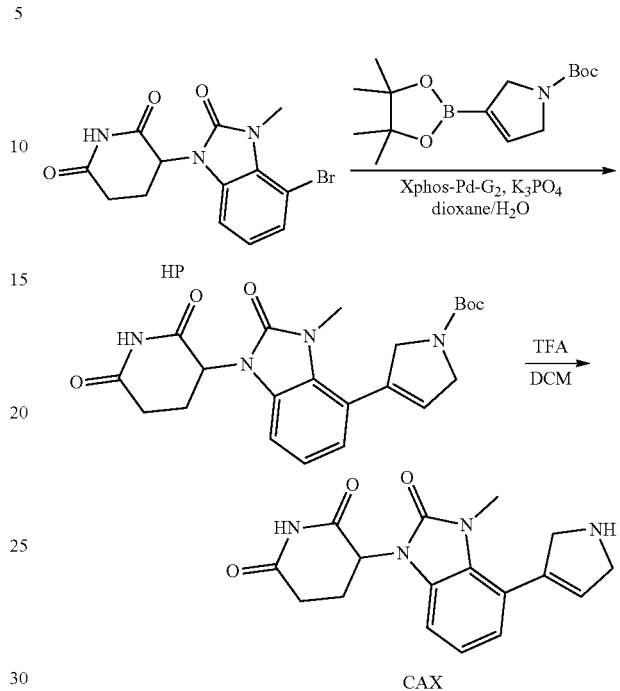

Step 1—Tert-butyl 3-[1-(2,6-dioxo-3-piperidyl)-3-methyl-2-oxo-benzimidazol-4-yl]-2,5-dihydropyrrole-1-carboxylate A mixture of 3-(4-bromo-3-methyl-2-oxo-benzimidazol-1-yl)piperidine-2,6-dione (2 g, 5.91 mmol, Intermediate HP), tert-butyl 3-(4,4,5,5-tetramethyl-1,3,2-dioxaborolan-2-yl)-2,5-dihydropyrrole-1-carboxylate (2.09 g, 7.10 mmol, CAS #212127-83-8), XPHOS-PD-G2 (465 mg, 591 umol), K$_3$PO$_4$ (3.77 g, 17.7 mmol) in dioxane (20 mL) and H$_2$O (4 mL) was degassed and purged with N$_2$ three times. Then the mixture was stirred at 80° C. for 2 hrs under N$_2$ atmosphere. On completion, the reaction mixture was filtered to give the filtrate. The filtrate was diluted with EA (100 mL) and washed with H$_2$O (2×30 mL). The combined organic layer was dried over Na$_2$SO$_4$, filtered and concentrated in vacuo. The residue was purified by prep-HPLC (1% FA condition) to give the title compound (2.5 g, 99% yield) as a yellow solid. $^1$H NMR (400 MHz, CDCl$_3$) δ 8.73 (s, 1H), 7.09-6.97 (m, 1H), 6.90 (d, J=7.6 Hz, 1H), 6.77 (d, J=7.6 Hz, 1H), 5.91-5.63 (m, 1H), 5.25 (d, J=5.2, 12.4 Hz, 1H), 4.52-4.10 (m, 4H), 3.42 (d, J=3.2 Hz, 3H), 2.96-2.67 (m, 4H), 1.49 (d, J=8.1 Hz, 9H). LC-MS (ESI$^+$) m/z 427.2 (M+H)$^+$.

Step 2—3-[4-(2,5-Dihydro-1H-pyrrol-3-yl)-3-methyl-2-oxo-benzimidazol-1-yl]piperidine-2,6-dione To a solution of tert-butyl 3-[1-(2,6-dioxo-3-piperidyl)-3-methyl-2-oxo-benzimidazol-4-yl]-2,5-dihydropyrrole-1-carboxylate (100 mg, 234 umol) in DCM (1 mL) was added TFA (0.3 mL). The mixture was stirred at 25° C. for 2 hrs. On completion, the reaction was concentrated in vacuo to give the title compound (103 mg, 99% yield, TFA) as yellow oil. LC-MS (ESI+) m/z 327.1 (M+H)+.

3-(3-methyl-2-oxo-5-piperazin-1-yl-benzimidazol-1-yl)piperidine-2,6-dione (Intermediate CAY)

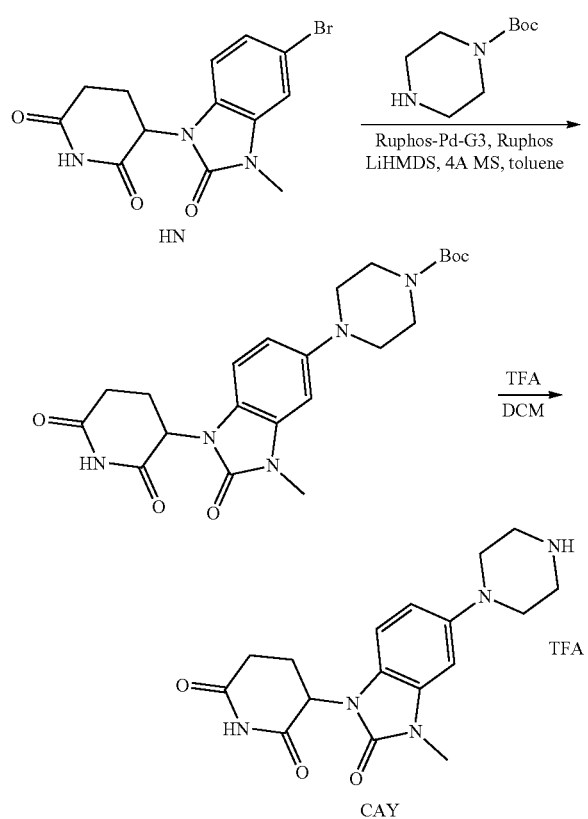

Step 1—Tert-butyl 4-[1-(2,6-dioxo-3-piperidyl)-3-methyl-2-oxo-benzimidazol-5-yl]piperazine-1-carboxylate To a solution of 3-(5-bromo-3-methyl-2-oxo-benzimidazol-1-yl)piperidine-2,6-dione (500 mg, 1.48 mmol, Intermediate FIN) and tert-butyl piperazine-1-carboxylate (413 mg, 2.22 mmol, CAS #143238-38-4) in toluene (4 mL) was added RuPhos Pd G3 (247 mg, 295umol), RuPhos (138 mg, 295 umol) and LiHMDS (1 M, 6 mL). Then the mixture was stirred at 100° C. for 16 hr under $N_2$ atmosphere. On completion, the reaction mixture was quenched with FA (12 mL) and concentrated in vacuo. The mixture was purified by column chromatography ($SiO_2$, DCM:EtOH=10:1) and concentrated in vacuo. The residue was purified by prep-HPLC (column: Phenomenex Luna C18 150*25 mm*10 um; mobile phase: [water(FA)-ACN]; B %: 24%-54%, 10.5 mins) concentrated in vacuo to give the title compound (150 mg, 23% yield) as brown solid. $^1$H NMR (400 MHz, DMSO-$d_6$) δ 11.06 (s, 1H), 6.96 (d, J=8.4 Hz, 1H), 6.87 (d, J=2.0 Hz, 1H), 6.66 (dd, J=2.4, 8.4 Hz, 1H), 5.29 (dd, J=5.6, 12.8 Hz, 1H), 3.51-3.44 (m, 4H), 3.30 (s, 3H), 3.06-3.00 (m, 4H), 2.93-2.84 (m, 1H), 2.73-2.65 (m, 1H), 2.59 (d, J=2.4 Hz, 1H), 2.02-1.94 (m, 1H), 1.42 (s, 9H); LC-MS (ESI+) m/z 444.2 (M+H)+.

Step 2—3-(3-methyl-2-oxo-5-piperazin-1-yl-benzimidazol-1-yl)piperidine -2,6-dione To a solution of tert-butyl 4-[1-(2,6-dioxo-3-piperidyl)-3-methyl-2-oxo-benzimidazol -5-yl] piperazine -1-carboxylate (40 mg, 90.1 umol) in DCM (0.5 mL) was added TFA (154 mg, 1.35 mmol), then the mixture was stirred at 25° C. for 0.5 hr. On completion, the reaction mixture was concentrated in vacuo to give the title compound (40 mg, 96% yield, TFA) as red solid. LC-MS (ESI+) m/z 344.2 (M+H)+.

6-(5-fluoropyrrolo[2,3-b]pyridin-1-yl)-N-(4-formyl-cyclohexyl)-4-(isopropylamino)pyridine-3-carboxamide (Intermediate CAZ)

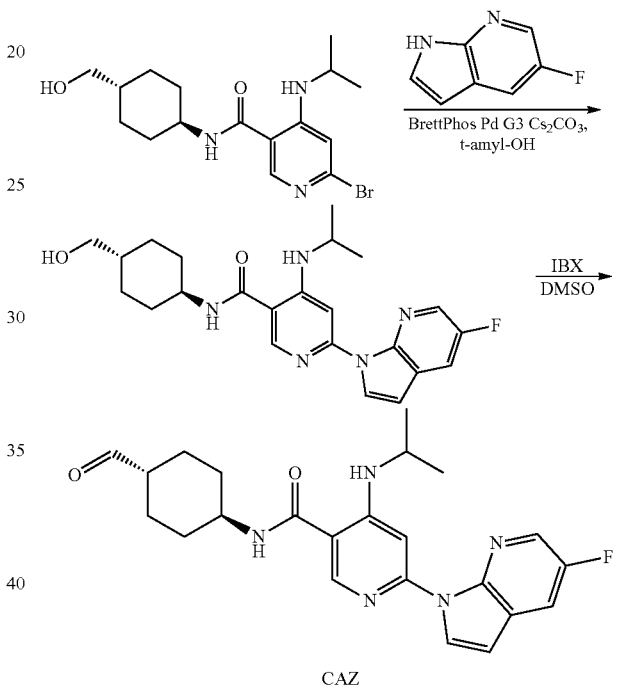

Step 1—6-(5-Fluoropyrrolo[2,3-b]pyridin-1-yl)-N-[4-(hydroxymethyl)cyclohexyl]-4-(isopropylamino) pyridine-3-carboxamide To a solution of 6-bromo-N-[4-(hydroxymethyl)cyclohexyl]-4-(isopropylamino) pyridine-3-carboxamide (250 mg, 675 umol, synthesized via Steps 1-4 of Intermediate BVU) and 5-fluoro-1H-pyrrolo[2,3-b]pyridine (110 mg, 810 umol, CAS #866319-00-8) in t-amyl-OH (1 mL) was added $Cs_2CO_3$ (439 mg, 1.35 mmol) and BrettPhos Pd G3 (61.2 mg, 67.5 umol). Then the mixture was stirred at 100° C. for 16 hrs under $N_2$ atmosphere. On completion, the reaction mixture was filtered to give the filtrate. The residue was purified by reverse phase (0.1% FA condition) to give the title compound (135 mg, 23% yield) as white solid. $^1$H NMR (400 MHz, DMSO-$d_6$) δ 8.57 (d, J=7.2 Hz, 1H), 8.54 (s, 1H), 8.47 (d, J=4.0 Hz, 1H), 8.40 (dd, J=1.2, 2.8 Hz, 1H), 8.26 (d, J=8.0 Hz, 1H), 8.19 (s, 1H), 8.03 (dd, J=2.8, 9.2 Hz, 1H), 6.74 (d, J=4.0 Hz, 1H), 4.40 (s, 1H), 3.81-3.73 (m, 1H), 3.73-3.64 (m, 1H), 3.23 (d, J=6.0 Hz, 2H), 2.52 (d, J=1.6 Hz, 1H), 1.93-1.83 (m, 2H), 1.79 (d, J=11.6 Hz, 2H), 1.39-1.31 (m, 2H), 1.29 (d, J=6.4 Hz, 6H), 1.05-0.90 (m, 2H); LC-MS (ESI⁺) m/z 426.3 (M+H)⁺.

Step 2—6-(5-Fluoropyrrolo[2,3-b]pyridin-1-yl)-N-(4-formylcyclohexyl)-4-(isopropylamino) pyridine-3-carboxamide To a solution of 6-(5-fluoropyrrolo[2,3-b]pyridin-1-yl)-N-[4-(hydroxymethyl) cyclohexyl]-4-(isopropylamino)pyridine-3-carboxamide (35 mg, 82.3 umol) in DMSO (0.5 mL) was added IBX (69.1 mg, 246 umol), then the mixture was stirred at 50° C. for 1 hr. On completion, the mixture was quenched with saturated NaHCO₃ (5 mL) and saturated Na₂S₂O₃ (5 mL), and the mixture was stirred at 25° C. for 0.5 hr. Next, the mixture was diluted with DCM (20 mL) and the organic layer was washed with saturated NaHCO₃ (10 mL×3). The organic layer was separated and washed with saturated NaCl (10 mL), the organic layer was dried over Na₂SO₄, filtered and concentrated in vacuo to give the title compound (32 mg, 91% yield) as yellow solid. ¹H NMR (400 MHz, DMSO-d₆) δ 9.59 (d, J=0.8 Hz, 1H), 8.58-8.51 (m, 2H), 8.47 (d, J=4.0 Hz, 1H), 8.40 (dd, J=1.2, 2.4 Hz, 1H), 8.32 (d, J=7.6 Hz, 1H), 8.19 (s, 1H), 8.03-7.76 (m, 1H), 6.75 (d, J=3.6 Hz, 1H), 3.82-3.75 (m, 1H), 3.75-3.66 (m, 1H), 2.55-2.52 (m, 2H), 2.26-2.12 (m, 1H), 2.05-1.88 (m, 4H), 1.42-1.32 (m, 2H), 1.29 (d, J=6.4 Hz, 6H); LC-MS (ESI⁺) m/z 424.3 (M+H)⁺.

3-[3-methyl-2-oxo-4-[3-(piperazin-1-ylmethyl)cyclobutyl]benzimidazol-1-yl]piperidine-2,6-dione (Intermediate CBA)

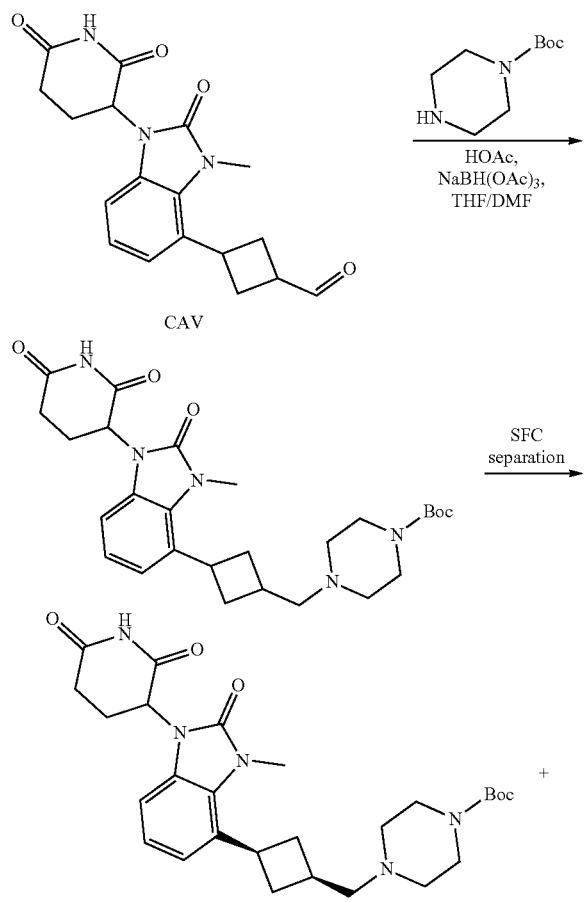

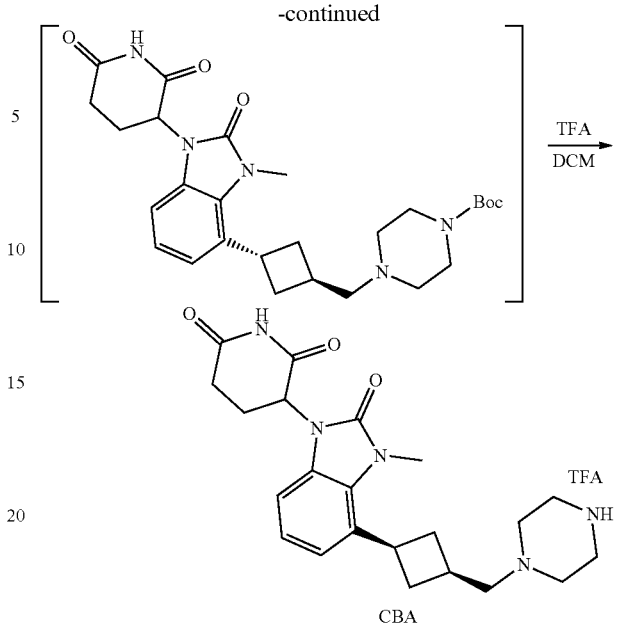

Step 1—Tert-butyl 4-[[3-[1-(2,6-dioxo-3-piperidyl)-3-methyl-2-oxo-benzimidazol-4-yl]cyclobutyl]methyl]piperazine-1-carboxylate To a solution of 3-[1-(2,6-dioxo-3-piperidyl)-3-methyl-2-oxo-benzimidazol-4-yl]cyclobutanecarbaldehyde (160 mg, 468 umol, Intermediate CAV) in THF (3 mL) was added tert-butylpiperazine-1-carboxylate (104 mg, 562 umol, CAS #143238-38-4), then HOAc (26.8 uL, 468 umol) was added, then the mixture was stirred at 25° C. for 0.5 hour. Then NaBH(OAc)₃ (149 mg, 703 umol) was added, and the mixture was stirred at 25° C. for 1.5 hours. On completion, the mixture was concentrated in vacuo to give the residue. The residue was purified by prep-HPLC (column: Phenomenex luna C18 150*25 mm*10 um; mobile phase: [water (0.225% FA)-ACN]; B %: 8%-38%, 10 min) to give the title compound (74.0 mg, 30% yield) as a white solid. ¹H NMR (400 MHz, CDCl₃-d) δ 8.14 (s, 1H), 7.13-7.01 (m, 2H), 6.73-6.65 (m, 1H), 5.21 (dd, J=5.2, 12.4 Hz, 1H), 3.68 (s, 3H), 3.64-3.49 (m, 4H), 2.99-2.85 (m, 2H), 2.84-2.47 (m, 10H), 2.35-2.17 (m, 2H), 2.03 (d, J=9.6 Hz, 2H), 1.47 (s, 9H). LC-MS (ESI⁺) m/z 512.4 (M+H)⁺.

Step 2—Tert-butyl 4-[[3-[1-(2,6-dioxo-3-piperidyl)-3-methyl-2-oxo-benzimidazol-4-yl]cyclobutyl]methyl]piperazine-1-carboxylate and tert-butyl 4-[[3-[1-(2,6-dioxo-3-piperidyl)-3-methyl-2-oxo-benzimidazol-4-yl]cyclobutyl]methyl]piperazine-1-carboxylate Tert-butyl 4-[[3-[1-(2,6-dioxo-3-piperidyl)-3-methyl-2-oxo-benzimidazol-4-yl]cyclobutyl]methyl]piperazine-1-carboxylate (610 mg) was separated by SFC (column: DAICEL CHIRALPAK IC (250 mm*30 mm, 10 um); mobile phase: [IPA-ACN]; B %: 80%-80%, 6; 40 min) to give the title compound tert-butyl 4-[[3-[1-(2,6-dioxo-3-piperidyl)-3-methyl-2-oxo-benzimidazol-4-yl]cyclobutyl]methyl]piperazine-1-carboxylate (150 mg, 50% yield) as a white solid and the title compound tert-butyl 4-[[3-[1-(2,6-dioxo-3-piperidyl)-3-methyl-2-oxo-benzimidazol-4-yl]cyclobutyl]methyl]piperazine-1-carboxylate (70.0 mg, 23% yield) as a white solid. $^1$H NMR (400 MHz, DMSO-$d_6$) δ 11.09 (s, 1H), 7.09-6.95 (m, 3H), 5.37-5.32 (m, 1H), 4.34-4.04 (m, 3H), 3.99-3.89 (m, 2H), 3.56 (s, 3H), 2.96-2.81 (m, 1H), 2.75-2.58 (m, 2H), 2.46-2.37 (m, 4H), 2.34-2.28 (m, 4H), 2.02-1.94 (m, 1H), 1.91-1.81 (m, 2H), 1.39 (s, 9H).

Step 3—3-[3-Methyl-2-oxo-4-[3-(piperazin-1-ylmethyl)cyclobutyl]benzimidazol-1-yl]piperidine-2,6-dione To a solution of tert-butyl 4-[[3-[1-(2,6-dioxo-3-piperidyl)-3-methyl-2-oxo-benzimidazol-4-yl]cyclobutyl]methyl]piperazine-1-carboxylate (50.0 mg, 97.7 umol) in DCM (2 mL) was added TFA (300 uL, 4.05 mmol), then the mixture was stirred at 25° C. for 1 hour. On completion, the residue was concentrated in vacuo to give the title compound (50.0 mg, 97% yield, TFA) as a white solid. LC-MS (ESI$^+$) m/z 412.2 (M+H)$^+$.

N-[2-[4-(iodomethyl)cyclohexyl]indazol-5-yl]-6-(trifluoromethyl)pyridine-2-carboxamide (Intermediate CBB)

Step 1—[4-[5-[[6-(Trifluoromethyl)pyridine-2-carbonyl]amino]indazol-2-yl]cyclohexyl]methyl methanesulfonate To a solution of N-[2-[4-(hydroxymethyl)cyclohexyl]indazol-5-yl]-6-(trifluoromethyl)pyridine-2-carboxamide (100 mg, 239 umol, synthesized via Steps 1-2 of Intermediate BRP) in DCM (5 mL) was added methylsulfonyl methanesulfonate (124 mg, 717 umol) and DIEA (123 mg, 956 umol), then the mixture was stirred at 25° C. for 2 hrs. On completion, the reaction mixture was poured into water (10 mL) and extracted with DCM (10 mL×2). The combined organic layers were dried over Na$_2$SO$_4$, filtered and concentrated in vacuo give the title compound (110 mg, 93% yield) as yellow solid. LC-MS (ESI$^+$) m/z 497.3 (M+H)$^+$.

Step 2—N-[2-[4-(iodomethyl)cyclohexyl]indazol-5-yl]-6-(trifluoromethyl)pyridine-2-carboxamide To a solution of [4-[5-[[6-(trifluoromethyl)pyridine-2-carbonyl]amino]indazol-2-yl]cyclohexyl]methyl methanesulfonate (110 mg, 221 umol) in THF (4 mL) was added NaI (99.6 mg, 664 umol), then the mixture was stirred at 60° C. for 16 hrs. On completion, the reaction mixture was poured into 10 mL of water and extracted with EtOAc (10 mL×2). The combined organic layers were washed by saturated brine (10 mL), dried over Na$_2$SO$_4$, filtered and concentrated in vacuo give the title compound (110 mg, 94% yield) as yellow solid. LC-MS (ESI$^+$) m/z 529.1 (M+H)$^+$.

3-[4-(3,3-dimethylpiperazin-1-yl)-3-methyl-2-oxo-benzimidazol-1-yl]piperidine-2,6-dione (Intermediate CBC)

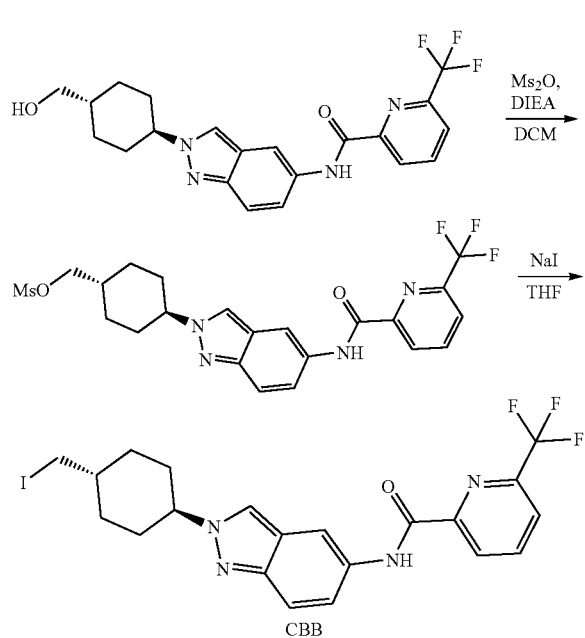

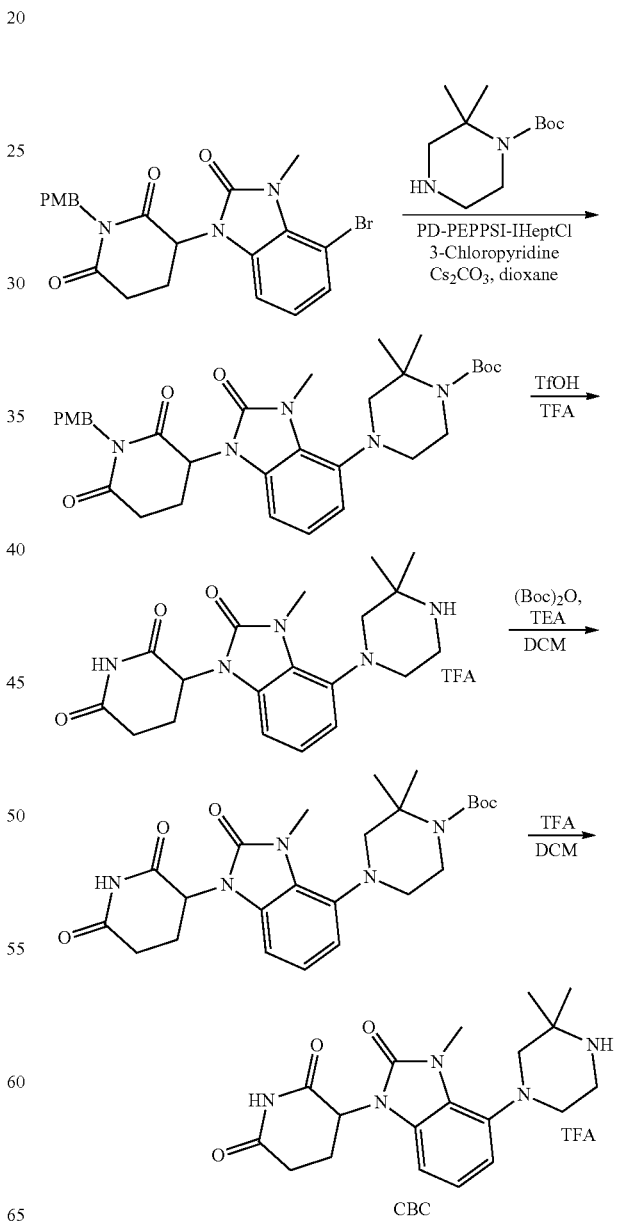

Step 1—Tert-butyl 4-[1-[1-[(4-methoxyphenyl)methyl]-2,6-dioxo-3-piperidyl]-3-methyl-2-oxo-benzimidazol-4-yl]-2,2-dimethyl-piperazine-1-carboxylate To a solution of 3-(4-bromo-3-methyl-2-oxo-benzimidazol-1-yl)-1-[(4-methoxyphenyl)methyl]piperidine-2,6-dione (1 g, 2.18 mmol, synthesized via Steps 1-4 of Intermediate HP) and tert-butyl 2,2-dimethylpiperazine-1-carboxylate (701 mg, 3.27 mmol, CAS #674792-07-5) in dioxane (3 mL) was added Cs$_2$CO$_3$ (1.42 g, 4.36 mmol) and PD-PEPPSI-IHeptCl 3-Chloropyridine (40 mg, 0.218 mmol), then the solution was stirred at 100° C. for 16 hrs. On completion, the reaction mixture was filtered. The filtrate was diluted with water (10 mL) and extracted with EA (30 mL×2). The combined organic layer was washed with saturated brine (10 mL). The organic layer was dried over Na$_2$SO$_4$, filtered and concentrated in vacuo to give a residue. The residue was purified by reverse phase (0.1% FA condition) to give the title compound (590 mg, 46% yield) as brown solid. $^1$H NMR (400 MHz, DMSO-d$_6$) δ 7.21 (d, J=8.8 Hz, 2H), 6.94 (d, J=4.0 Hz, 2H), 6.90-6.74 (m, 3H), 5.51 (dd, J=5.6, 12.8 Hz, 1H), 4.86-4.72 (m, 2H), 3.72 (s, 3H), 3.67 (s, 3H), 3.12-2.96 (m, 2H), 2.90-2.60 (m, 6H), 2.52-2.51 (m, 1H), 2.07-1.97 (m, 1H), 1.56-1.37 (m, 15H).

Step 2—3-[4-(3,3-Dimethylpiperazin-1-yl)-3-methyl-2-oxo-benzimidazol-1-yl]piperidine-2,6-dione A solution of tert-butyl 4-[1-[1-[(4-methoxyphenyl)methyl]-2,6-dioxo-3-piperidyl]-3-methyl-2-oxo-benzimidazol-4-yl]-2,2-dimethyl-piperazine-1-carboxylate (500 mg, 845 umol) in TfOH (1 mL) and TFA (5 mL) was stirred at 70° C. for 2 hrs. On completion, the reaction mixture was adjusted to pH=7-8 with TEA and then concentrated in vacuo to give the title compound (300 mg, 96% yield). LC-MS (ESI-0 m/z 372.2 (M+H)$^+$.

Step 3—Tert-butyl 4-[1-(2,6-dioxo-3-piperidyl)-3-methyl-2-oxo-benzimidazol-4-yl]-2,2-dimethyl-piperazine-1-carboxylate To a solution of 3-[4-(3,3-dimethylpiperazin-1-yl)-3-methyl-2-oxo-benzimidazol-1-yl]piperidine-2,6-dione (300 mg, 807 umol) in DCM (5 mL) was added TEA (163 mg, 1.62 mmol) and (Boc)$_2$O (264 mg, 1.21 mmol), the reaction was stirred at 25° C. for 16 hrs. On completion, the reaction mixture was diluted with water (10 mL) and extracted with DCM (10 mL×2). The organic layer was dried over Na$_2$SO$_4$, filtered and concentrated in vacuo to give a residue. The residue was purified by reverse phase (0.1% FA condition) to give the title compound (340 mg, 89% yield) as yellow oil. LC-MS (ESI+) m/z 472.3 (M+H)$^+$.

Step 4—3-[4-(3,3-Dimethylpiperazin-1-yl)-3-methyl-2-oxo-benzimidazol-1-yl]piperidine-2,6-dione A solution of tert-butyl 4-[1-(2,6-dioxo-3-piperidyl)-3-methyl-2-oxo-benzimidazol-4-yl]-2,2-dimethyl-piperazine-1-carboxylate (240 mg, 508 umol) in TFA (1 mL) and DCM (6 mL) was stirred at 25° C. for 1 hr. On completion, the reaction mixture was concentrated in vacuo to give the title compound (180 mg, 95% yield, TFA) as yellow oil. LC-MS (ESI+) m/z 372.3 (M+H)$^+$.

3-[3-Methyl-2-oxo-4-(3-piperazin-1-ylprop-1-ynyl)benzimidazol-1-yl]piperidine-2,6-dione (Intermediate CBD)

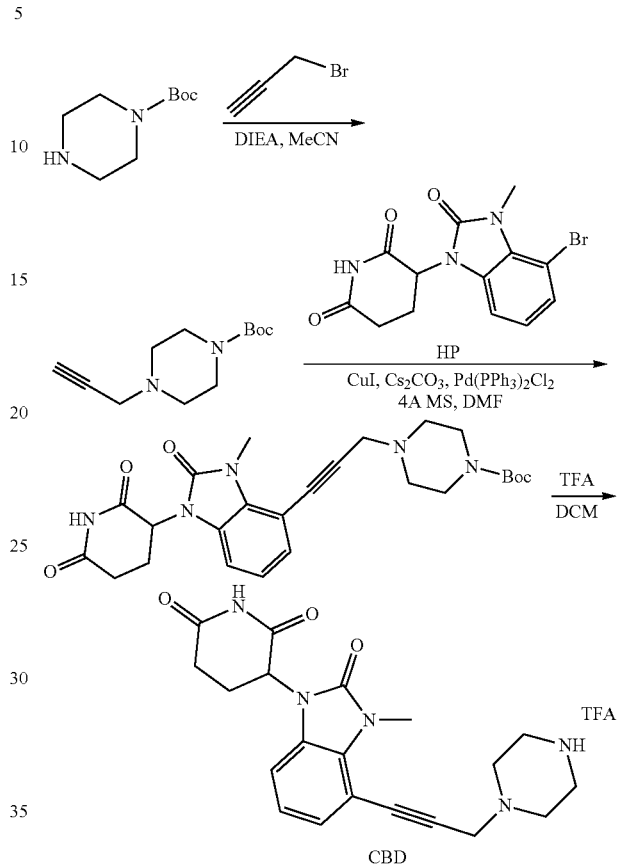

Step 1—Tert-butyl 4-prop-2-ynylpiperazine-1-carboxylate

To a solution of tert-butyl piperazine-1-carboxylate (1.00 g, 5.37 mmol) in ACN (150 mL) was added DIEA (1.39 g, 10.7 mmol). Next, 3-bromoprop-1-yne (574 mg, 4.83 mmol) was dissolved in ACN (150 mL) and was added dropwise to the reaction mixture. The mixture was stirred at 25° C. for 2 hrs. On completion, the reaction mixture was diluted with H$_2$O (20 mL) and extracted with EA (20 mL×2). The combined organic layers were concentrated under reduced pressure to give a residue. The residue was purified by column chromatography (SiO$_2$, Petroleum ether/Ethyl acetate=8/1 to 3/1) to give the title compound (1.00 g, 83% yield) as yellow oil. $^1$H NMR (400 MHz, DMSO-d$_6$) δ 3.32 (s, 4H), 3.28 (d, J=2.4 Hz, 2H), 3.16 (t, J=2.4 Hz, 1H), 2.40-2.34 (m, 4H), 1.39 (s, 9H)

Step 2—Tert-butyl 4-[3-[1-(2,6-dioxo-3-piperidyl)-3-methyl-2-oxo-benzimidazol-4-yl]prop-2-ynyl]piperazine-1-carboxylate A mixture of tert-butyl 4-prop-2-ynylpiperazine-1-carboxylate (2 g, 8.92 mmol), 3-(4-bromo-3-methyl-2-oxobenzimidazol-1-yl)piperidine-2,6-dione (2.01 g, 5.94 mmol, Intermediate HP), CuI (56.6 mg, 297 umol), Cs$_2$CO$_3$ (5.81 g, 17.8 mmol) and Pd(PPh$_3$)$_2$Cl$_2$ (208 mg, 297 umol) in DMF (15 mL) was stirred at 80° C. for 3 hrs under N$_2$ atmosphere. On completion, the reaction mixture was filtered and the filtrate was diluted with H$_2$O (50 mL). Then the mixture was extracted with EA (2×50 mL). The combined organic layer was concentrated in vacuo to give a residue. The residue was purified by reverse phase (0.1% FA condition) to give the title compound (1.6 g, 55.8% yield) as an off-white solid. $^1$H NMR (400 MHz, DMSO-d$_6$) δ 11.12 (s, 1H), 7.19-7.06 (m, 2H), 7.03-6.98 (m, 1H), 5.39 (dd, J=5.2, 12.8 Hz, 1H), 3.63 (s, 3H), 3.60 (s, 2H), 3.39-3.33 (m, 6H), 2.95-2.82 (m, 1H), 2.75 (d, J=4.0 Hz, 1H), 2.66-2.59 (m, 1H), 2.48 (s, 2H), 2.07-1.99 (m, 1H), 1.39 (s, 9H); LC-MS (ESI+) m/z 482.3 (M+H)$^+$.

Step 3—3-[3-Methyl-2-oxo-4-(3-piperazin-1-ylprop-1-ynyl)benzimidazol-1-yl]piperidine-2,6-dione To a solution of tert-butyl 4-[3-[1-(2,6-dioxo-3-piperidyl)-3-methyl-2-oxo-benzimidazol-4-yl]prop-2-ynyl]piperazine-1-carboxylate (70 mg, 145.37 umol) in DCM (1 mL) was added TFA (770 mg, 6.75 mmol). The mixture was then stirred at 25° C. for 1 hr. On completion, the reaction mixture was concentrated in vacuo to give the title compound (65 mg, 90% yield) as a brown solid. LC-MS (ESI+) m/z 382.0 (M+H)$^+$.

3-Methyl-1-(8-piperazin-1-yl-4-isoquinoly)hexahydropyrimidine-2,4-dione (Intermediate CBE)

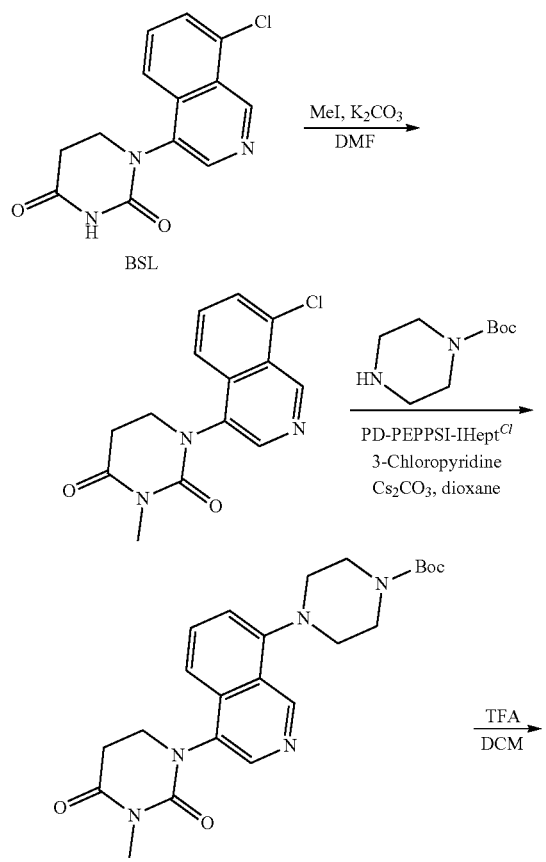

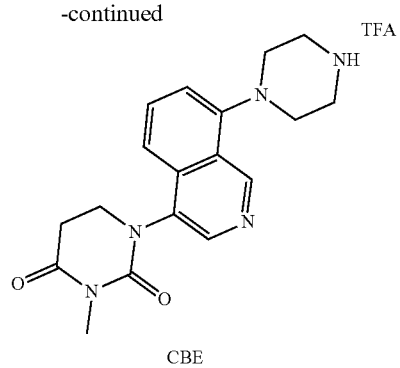

CBE

Step 1—1-(8-Chloro-4-isoquinolyl)-3-methyl-hexahydropyrimidine-2,4-dione

To a solution of 1-(8-chloro-4-isoquinolyl)hexahydropyrimidine-2,4-dione (500 mg, 1.81 mmol, Intermediate BSL) in DMF (5 mL) was added K$_2$CO$_3$ (501 mg, 3.63 mmol) and MeI (169 uL, 2.72 mmol), then the mixture was stirred at 60° C. for 6 hours. On completion, the mixture was filtered and the filtrate was extracted with water (50 mL) and EA (50 mL×3). The combined organic layer was dried over anhydrous Na$_2$SO$_4$, then concentrated in vacuo to give the residue. The residue was purified by reverse-phase (0.1% FA condition) to give the title compound (170 mg, 32% yield) as a yellow solid. $^1$H NMR (400 MHz, DMSO-d$_6$) δ 9.56 (d, J=0.4 Hz, 1H), 8.71 (s, 1H), 8.06 (d, J=8.4 Hz, 1H), 7.91-7.87 (m, 1H), 7.83-7.77 (m, 1H), 3.91-3.89 (m, 1H), 3.69-3.66 (m, 1H), 3.09 (s, 3H), 3.05-3.02 (m, 1H), 2.95-2.91 (m, 1H). LC-MS (ESI$^+$) m/z 290.1 (M+H)$^+$.

Step 2—Tert-butyl 4-[4-(3-methyl-2,4-dioxo-hexahydropyrimidin-1-yl)-8-isoquinolyl]piperazine-1-carboxylate To a solution of 1-(8-chloro-4-isoquinolyl)-3-methyl-hexahydropyrimidine-2,4-dione (140 mg, 483 umol) and tert-butyl piperazine-1-carboxylate (108 mg, 580 umol, CAS #57260-71-6) in dioxane (5 mL) was added Pd-PEPPSI-IHeptCl$_3$-Chloropyridine (47.0 mg, 48.3 umol) and Cs$_2$CO$_3$ (314 mg, 966 umol), then the mixture was stirred at 80° C. for 8 hours. On completion, the mixture was filtered and the filtrate was concentrated in vacuo to give the residue. The residue was purified by reverse-phase (0.1% FA condition) to give the title compound (106 mg, 50% yield) as a yellow solid. $^1$H NMR (400 MHz, DMSO-d$_6$) δ 9.49 (s, 1H), 8.55 (s, 1H), 7.75-7.66 (m, 2H), 7.32-7.27 (m, 1H), 3.93-3.83 (m, 1H), 3.74-3.58 (m, 5H), 3.46-3.41 (m, 2H), 3.10-3.04 (m, 6H), 2.93-2.86 (m, 1H), 1.45 (s, 8H). LC-MS (ESI$^+$) m/z 440.2 (M+H)$^+$.

Step 3—3-Methyl-1-(8-piperazin-1-yl-4-isoquinoly)hexahydropyrimidine-2,4-dione

To a solution of tert-butyl 4-[4-(3-methyl-2,4-dioxo-hexahydropyrimidin-1-yl)-8-isoquinolyl]piperazine-1-carboxylate (106 mg, 241 umol) in DCM (2 mL) was added TFA (1 mL, 13.5 mmol), then the mixture was stirred at 25° C. for 1 hour. On completion, the mixture was concentrated in vacuo to give the title compound (100 mg, 91% yield, TFA) as a yellow oil. LC-MS (ESI$^+$) m/z 340.1 (M+H)$^+$.

1-(8-bromo-7-methyl-4-isoquinolyl)-3-[(4-methoxy-phenyl)methyl]hexahydro pyrimidine -2,4-dione (Intermediate CBF)

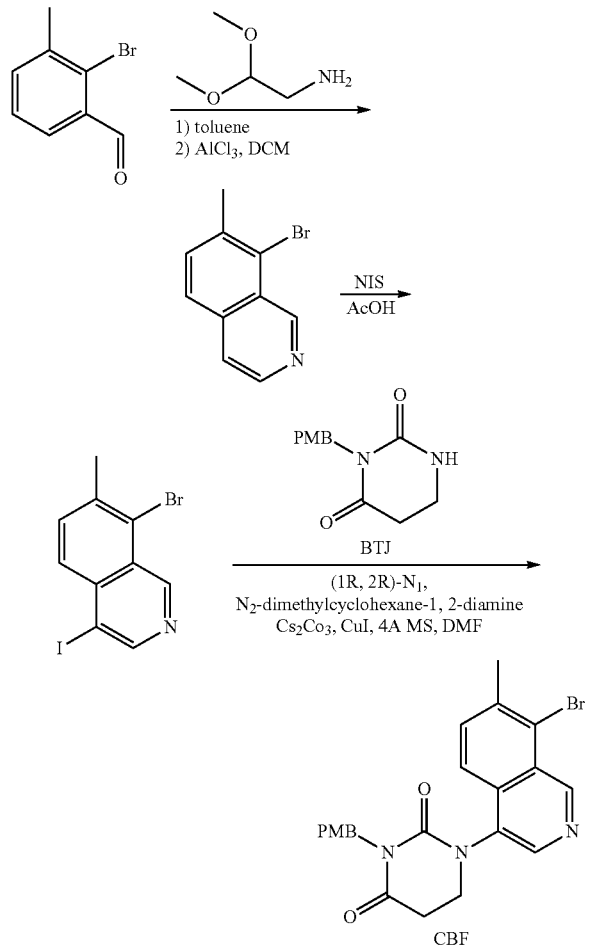

Step 1—8-Bromo-7-methyl-isoquinoline

To a solution of 2-bromo-3-methyl-benzaldehyde (500 mg, 2.51 mmol, CAS #109179-31-9) in toluene (8 mL) was added 2,2-dimethoxyethanamine (277 mg, 2.64 mmol, CAS #22483-09-6). The mixture was stirred at 100° C. for 4 hrs. Then the reaction mixture was concentrated in vacuo to give a residue. The residue was dissolved in DCM (15 mL) and cooled to 0° C. Then, AlCl$_3$ (1.11 g, 8.29 mmol) was added to the mixture and the reaction mixture was stirred at 25° C. for 18 hrs. On completion, the reaction mixture was added into ice water dropwise (80 mL). The reaction mixture was carefully basified with 2 M aqueous NaOH solution (120 mL). The resulting solution was diluted with water (80 mL) and extracted with DCM (2×60 mL). The combined organic layer was dried over Na$_2$SO$_4$, filtered and concentrated in vacuo to give a residue. The residue was purified by column chromatography (SiO$_2$, PE:EA=10:1 to PE:EA=3:1, Pl:Rf=0.42) to give the title compound (420 mg, 75% yield) as a yellow solid. $^1$H NMR (400 MHz, CDCl$_3$) δ 9.67 (s, 1H), 8.56 (d, J=6.0 Hz, 1H), 7.69 (d, J=8.4 Hz, 1H), 7.59-7.54 (m, 2H), 2.64 (s, 3H); LC-MS (ESI$^+$) m/z 222.0 (M+H)$^+$.

Step 2—8-Bromo-4-iodo-7-methyl-isoquinoline

To a solution of 8-bromo-7-methyl-isoquinoline (270 mg, 1.22 mmol) in AcOH (4 mL) was added NIS (601 mg, 2.67 mmol). The reaction mixture was stirred at 100° C. for 12 hrs. On completion, the mixture was concentrated in vacuo to give a residue. The residue was purified by column chromatography (SiO$_2$, PE:EA=1:0 to PE:EA=50:1, Pl:Rf=0.58) to give the title compound (173 mg, 40% yield) as a yellow solid. $^1$H NMR (400 MHz, DMSO-d$_6$) δ 9.44 (s, 1H), 8.98 (s, 1H), 8.01-7.79 (m, 2H), 2.61 (s, 3H); LC-MS (ESI$^+$) m/z 349.8 (M+H)$^+$.

Step 3—1-(8-Bromo-7-methyl-4-isoquinolyl)-3-[(4-methoxyphenyl)methyl]hexahydropyrimidine -2,4-dione To a solution of 8-bromo-4-iodo-7-methyl-isoquinoline (110 mg, 316 umol) and 3-(4-methoxybenzyl)dihydropyrimidine-2,4(1H,3H)-dione (74 mg, 316 umol, Intermediate BTJ) in DMF (3 mL) was added 4 Å molecular sieves (50 mg), Cs$_2$CO$_3$ (205 mg, 632 umol), CuI (24.1 mg, 126 umol) and (1R,2R)—N1,N2-dimethylcyclohexane-1,2-diamine (17.9 mg, 126 umol). The reaction mixture was degassed and purged with N$_2$ three times and the mixture was stirred at 100° C. for 16 hrs under N$_2$ atmosphere. On completion, the reaction mixture was filtered and concentrated in vacuo to give a residue. The residue was purified by prep-HPLC (column: Phenomenex luna C18 150*25 mm*10 um; mobile phase: [water (0.225% FA)-ACN]; B %: 38%-68%, 10 min) to give the title compound (80 mg, 55% yield) as a white solid. LC-MS (ESI$^+$) m/z 456.0 (M+H)$^+$.

1-(7-Methyl-8-piperazin-1-yl-4-isoquinoly)hexahydropyrimidine-2,4-dione (Intermediate CBG)

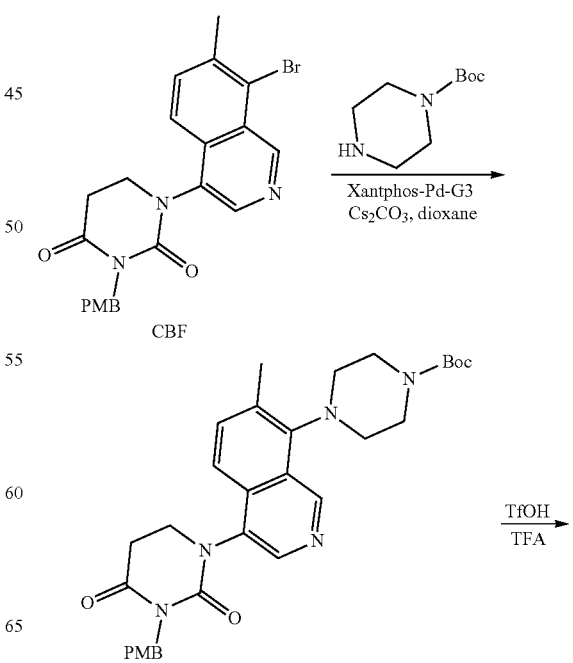

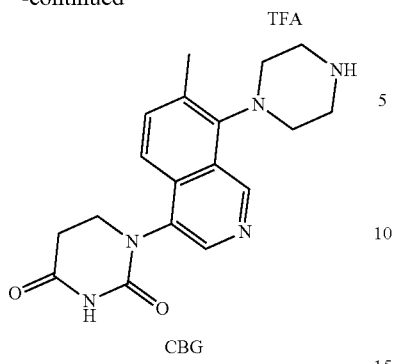

CBG

Step 1—Tert-butyl 4-[4-[3-[(4-methoxyphenyl)methyl]-2,4-dioxo-hexahydropyrimidin-1-yl]-7-methyl-8-isoquinolyl]piperazine-1-carboxylate To a solution of 1-(8-bromo-7-methyl-4-isoquinolyl)-3-[(4-methoxyphenyl)methyl]hexahydro pyrimidine-2,4-dione (135 mg, 299 umol, Intermediate CBF), and tert-butyl piperazine-1-carboxylate (111 mg, 598 umol, CAS #143238-8-4) in dioxane (5 mL) was added $Cs_2CO_3$ (292 mg, 897 umol) and XantPhos Pd G3 (28.3 mg, 29.9 umol). Then the reaction mixture was stirred at 110° C. for 16 hrs under $N_2$. On completion, the reaction mixture was filtered and the filtrate was concentrated in vacuo to give a residue. The residue was purified by prep-HPLC (column: Phenomenex Luna C18 100*30 mm*5 um; mobile phase: [water (FA)-ACN]; B %: 39%-69%, 8 min) to give the title compound (50.0 mg, 30% yield) as an yellow solid. $^1$H NMR (400 MHz, DMSO-$d_6$) δ 9.66 (s, 1H), 8.53 (s, 1H), 7.71-7.58 (m, 2H), 7.25 (d, J=8.8 Hz, 2H), 6.91-6.82 (m, 2H), 4.83 (s, 2H), 3.95-3.87 (m, 1H), 3.85-3.76 (m, 2H), 3.73 (s, 3H), 3.61-3.45 (m, 4H), 3.31-3.21 (m, 2H), 3.18-3.07 (m, 3H), 3.00-2.92 (m, 1H), 2.54-2.50 (m, 2H), 1.46 (s, 9H); LC-MS (ESI$^+$) m/z 560.2 (M+H)$^+$.

Step 2—1-(7-Methyl-8-piperazin-1-yl-4-isoquinoly) hexahydropyrimidine-2,4-dione

To a solution of tert-butyl 4-[4-[3-[(4-methoxyphenyl)methyl]-2,4-dioxo-hexahydropyrimidin-1-yl]-7-methyl-8-isoquinolyl]piperazine-1-carboxylate (50.0 mg, 89.3 umol) in TFA (770 mg, 6.75 mmol, 0.5 mL) was added TfOH (170 mg, 1.13 mmol, 0.1 mL). Then the reaction was stirred at 70° C. for 2 hrs. On completion, the reaction mixture was concentrated in vacuo to give the title compound (40.0 mg, 98% yield, TFA) as yellow oil. LC-MS (ESI$^+$) m/z 340.1 (M+H)$^+$.

1-(8-bromo-7-methoxy-4-isoquinolyl)-3-[(4-methoxyphenyl)methyl] hexahydropyrimidine-2,4-dione (Intermediate CBH)

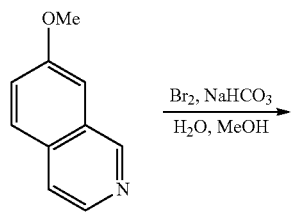

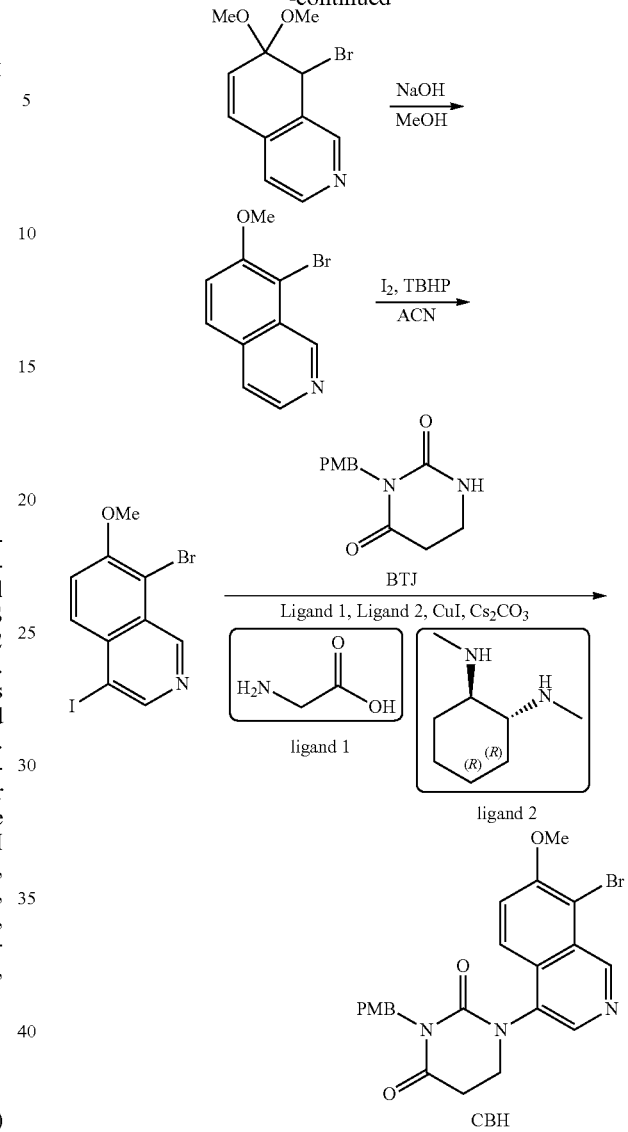

Step 1—8-bromo-7,7-dimethoxy-8H-isoquinoline

To a solution of 7-methoxyisoquinoline (3.6 g, 23 mmol) in MeOH (70 mL) was added NaHCO$_3$ (3.32 g, 40 mmol, 1.54 mL) and Br$_2$ (5.42 g, 34 mmol, 1.75 mL). The mixture was stirred at 25° C. for 5 mins. Then H$_2$O (30 mL) was added into above solution, and the mixture was stirred at 25° C. for 5 mins. On completion, the mixture was quenched by Na$_2$SO$_3$ and H$_2$O (50 mL), then extracted with DCM (3×30 mL). The combined organic layer was washed with brine (3×30 mL), dried with anhydrous Na$_2$SO$_4$, then filtered and the liquor was concentrated in vacuo to give the title compound (4.4 g, 17 mmol, 72% yield) as a brown solid. LC-MS (ESI$^+$) m/z 270.0 (M+H)$^+$.

Step 2—8-bromo-7-methoxy-isoquinoline

To a solution of 8-bromo-7,7-dimethoxy-8H-isoquinoline (4.4 g, 17 mmol) in MeOH (80 mL) was added NaOH (3.26 g, 82 mmol). The mixture was stirred at 25° C. for 10 mins. On completion, the mixture was diluted with H$_2$O (50 mL), then extracted with DCM (3×100 mL). The combined organic layer was washed with brine (3×100 mL), dried with anhydrous Na$_2$SO$_4$, then filtered and the liquor was concentrated in vacuo and the residue was purified by column chromatography (SiO$_2$, Petroleum ether/Ethyl acetate=100/1 to 5/1, PE:EA=1:1, Rf=0.50) to give the title compound (2.8 g, 72% yield) as a white solid. $^1$H NMR (400 MHz, CDCl$_3$-d) 69.64 (s, 1H), 8.50 (d, J=5.6 Hz, 1H), 7.84 (d, J=9.0 Hz, 1H), 7.60 (d, J=5.6 Hz, 1H), 7.50 (d, J=9.0 Hz, 1H), 4.07 (s, 3H). LC-MS (ESI$^+$) m/z 238.0 (M+H)$^+$.

Step 3—8-bromo-4-iodo-7-methoxy-isoquinoline

To a solution of 8-bromo-7-methoxy-isoquinoline (1.84 g, 7.73 mmol) in ACN (120 mL) was added I$_2$ (2.35 g, 9.27 mmol, 1.87 mL) and TBHP (7.96 g, 61.8 mmol, 8.47 mL, 70% solution) at 25° C. The mixture was then stirred at 80° C. for 16 hrs. On completion, the mixture was quenched by Na$_2$S$_2$O$_3$—H$_2$O (100 mL), diluted with H$_2$O (50 mL), then extracted with EA (3×100 mL). The combined organic layer was washed with brine (3×100 mL), dried with anhydrous Na$_2$SO$_4$. The mixture was filtered and the liquor was concentrated in vacuo, the residue was purified by column chromatography (SiO$_2$, Petroleum ether/Ethyl acetate=50/1 to 3/1)(PE:EA=1:1, Rf=0.7) to give the title compound (1.12 g, 40% yield) as a yellow solid. 1H NMR (400 MHz, CDCl$_3$-d) δ9.56 (s, 1H), 8.88 (s, 1H), 8.07 (d, J=9.4 Hz, 1H), 7.58 (d, J=9.4 Hz, 1H), 4.10 (s, 3H). LC-MS (ESI$^+$) m/z 363.8 (M+H)$^+$.

Step 4—1-(8-bromo-7-methoxy-4-isoquinolyl)-3-[(4-methoxyphenyl)methyl]hexahydropyrimidine-2,4-dione To a solution of 8-bromo-4-iodo-7-methoxy-isoquinoline (300 mg, 824 umol) and 3-[(4-methoxyphenyl)methyl]hexahydropyrimidine-2,4-dione (193.08 mg, 824 umol, Intermediate BTJ) in DMF (15 mL) was added 4 Å molecular sieves (375 mg), Cs$_2$CO$_3$ (537.10 mg, 1.65 mmol), CuI (62.79 mg, 329.7 umol), 2-aminoacetic acid (24.75 mg, 329.7 umol) and (1R,2R)—N1,N2-dimethylcyclohexane-1,2-diamine (46.90 mg, 329.7 umol). The mixture was then stirred at 100° C. for 16 hrs. On completion, the mixture was filtered and the liquor was concentrated in vacuo. The crude product was purified by reversed-phase HPLC (0.1% FA condition) to give the title compound (95 mg, 25% yield) as a yellow solid. $^1$H NMR (400 MHz, CHLOROFORM-d) δ7.58 (br s, 1H), 7.56 (br s, 1H), 7.44 (d, J=8.6 Hz, 4H), 6.88 (s, 2H), 5.00 (d, J=3.6 Hz, 2H), 3.82 (s, 3H), 3.76-3.68 (m, 2H), 3.04 (br s, 2H), 2.06 (s, 1H). LC-MS (ESI$^+$) m/z 471.9 (M+H)$^+$.

1-(7-Methoxy-8-piperazin-1-yl-4-isoquinoly)hexahydropyrimidine-2,4-dione (Intermediate CBI)

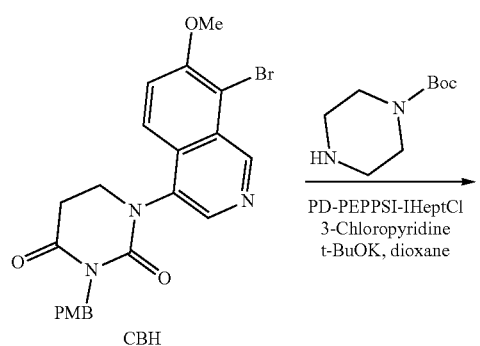

CBH

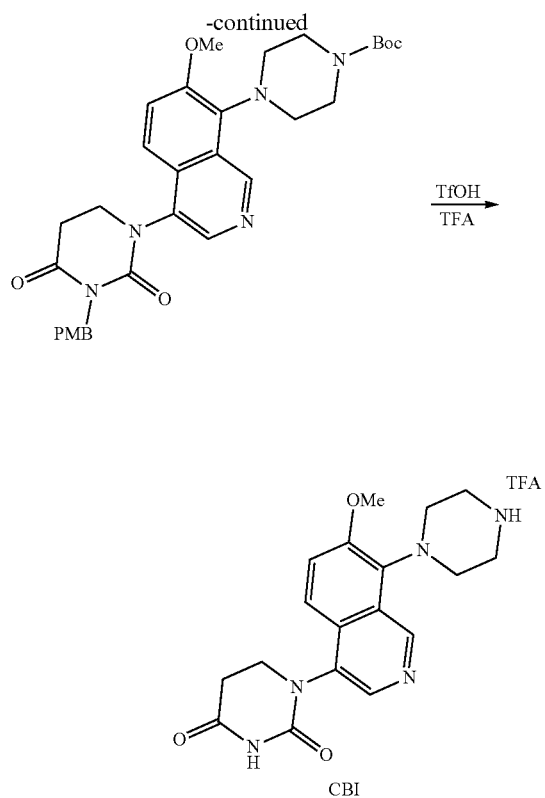

CBI

Step 1—Tert-butyl 4-[7-methoxy-4-[3-[(4-methoxyphenyl)methyl]-2,4-dioxo-hexahydropyrimidin-1-yl]-8-isoquinolyl]piperazine-1-carboxylate To a solution of 1-(8-bromo-7-methoxy-4-isoquinolyl)-3-[(4-methoxyphenyl)methyl] hexahydropyrimidine-2,4-dione (100 mg, 212 umol, Intermediate CBH) and tert-butyl piperazine-1-carboxylate (47.5 mg, 255 umol, CAS #143238-38-4) in DMA (2 mL) was added RuPhos Pd G3 (17.7 mg, 21.2 umol) and Cs$_2$CO$_3$ (138 mg, 425 umol). Then the mixture was stirred at 110° C. for 10 hours. On completion, the mixture was filtered and concentrated in vacuo to give the residue. The residue was purified by reverse-phase (0.1% FA condition) to give the title compound (50.0 mg, 20% yield) as yellow solid. $^1$H NMR (400 MHz, DMSO-d$_6$) δ 9.69 (s, 1H), 8.42 (s, 1H), 8.10 (d, J=7.6 Hz, 2H), 7.81-7.76 (m, 1H), 7.72-7.67 (m, 1H), 7.47 (d, J=8.0 Hz, 2H), 7.25 (d, J=8.4 Hz, 2H), 6.88 (d, J=8.4 Hz, 2H), 4.83 (s, 2H), 3.96 (s, 3H), 3.73 (s, 3H), 3.30 (br s, 2H), 3.18-3.06 (m, 3H), 3.00-2.81 (m, 4H), 2.52 (br s, 3H), 1.45 (s, 9H); LC-MS (ESI$^+$) m/z 576.2 (M+H)$^+$.

Step 2—1-(7-Methoxy-8-piperazin-1-yl-4-isoquinoly)hexahydropyrimidine-2,4-dione

To a solution of tert-butyl 4-[7-methoxy-4-[3-[(4-methoxyphenyl)methyl]-2,4-dioxo-hexahydropyrimidin-1-yl]-8-isoquinolyl]piperazine-1-carboxylate (30.0 mg, 52.1 umol) in TFA (1 mL) was added TfOH (0.2 mL, 2.27 mmol), then the mixture was stirred at 70° C. for 30 minutes. On completion, the mixture was concentrated in vacuo to give the title compound (24.0 mg, 98% yield, TFA) as yellow oil. LC-MS (ESI$^+$) m/z 356.1 (M+H)$^+$.

6-(1-Fluoro-1-methyl-ethyl)pyridine -2-carboxylic acid (Intermediate CBJ)

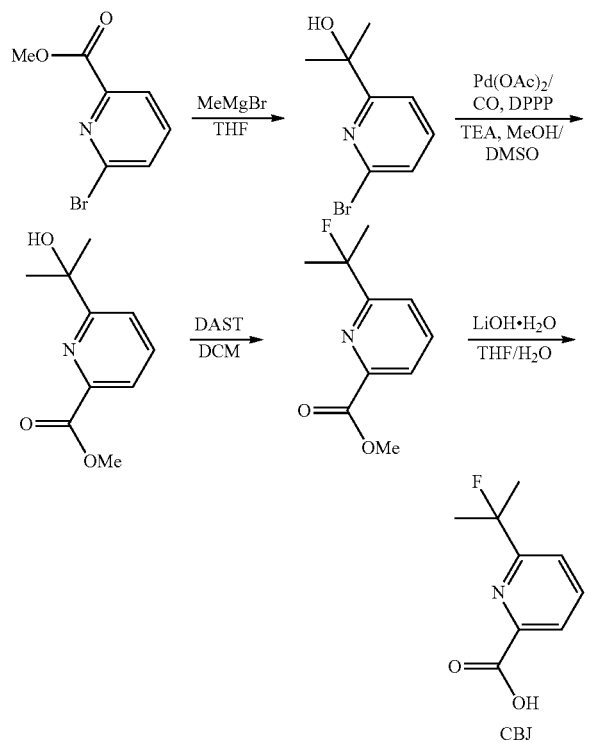

Step 1—2-(6-Bromo-2-pyridyl)propan-2-ol

To a solution of methyl 6-bromopyridine-2-carboxylate (10 g, 46.2 mmol, CAS #26218-75-7) in THF (100 mL) was added MeMgBr (3 M, 77.1 mL, CAS #75-16-1) at 0° C. under $N_2$. The mixture was stirred at 25° C. for 1 hour. On completion, the reaction was quenched with $NH_4Cl$ (200 mL, aq.), then extracted with EA (150 mL×3). The combined organic layer was washed with $NaHCO_3$ (100 mL X 3, aq.) and brine (100 mL), dried over $Na_2SO_4$, filtered and concentrated in vacuo to afford the title compound (5 g, 50% yield) as a white solid. LC-MS (ESI$^+$) m/z 215.8 (M+H)$^+$.

Step 2—Methyl 6-(1-hydroxy-1-methyl-ethyl)pyridine-2-carboxylate

To a solution of 2-(6-bromo-2-pyridyl)propan-2-ol (3.5 g, 16.2 mmol) in MeOH (35 mL) and DMSO (35 mL) were added DPPP (668 mg, 1.62 mmol), Pd(OAc)$_2$ (363 mg, 1.62 mmol) and TEA (4.10 g, 40.5 mmol, 5.64 mL). The mixture was degassed and purged with CO (16.2 mmol) three times, then the mixture was stirred at 25° C. for 30 minutes. Next, the solution was warmed up to 80° C. and stirred under CO at 40 psi for 16 hours. On completion, the reaction was filtered and the filtrate was diluted with water (150 mL), and extracted with EA (50 mL×3). The organics phase was then washed with brine (30 mL×2), dried over $Na_2SO_4$, filtered and concentrated under reduced pressure to give the desired product. Then the crude was purified by column chromatography (SiO$_2$, Petroleum ether/Ethyl acetate=100/1 to 10/1) to afford the title compound (3 g, 95% yield) as a white solid. $^1$H NMR (400 MHz, CDCl$_3$) δ 8.02 (d, J=7.6 Hz, 1H), 7.86 (t, J=8.0 Hz, 1H), 7.57 (d, J=8.0 Hz, 1H), 5.37-4.52 (m, 1H), 3.99 (s, 3H), 1.58 (s, 6H). LC-MS (ESI$^+$) m/z 196.3 (M+H)$^+$.

Step 3—Methyl 6-(1-fluoro-1-methyl-ethyl)pyridine-2-carboxylate

To a solution of methyl-6-(1-hydroxy-1-methyl-ethyl) pyridine-2-carboxylate (1 g, 5.12 mmol) in DCM (20 mL) was added DAST (1.01 g, 5.63 mmol, 90% solution) at 0° C. Then the mixture was stirred at 25° C. for 16 hours. On completion, the reaction was diluted with water (100 mL), and extracted with EA (30 mL×3). The combined organic layers were washed with brine (20 mL×2), dried over $Na_2SO_4$, filtered and concentrated under reduced pressure to give a residue. Then the residue was purified by column chromatography (SiO$_2$, Petroleum ether/Ethyl acetate=100/1 to 20/1) to afford the title compound (2 g, 48% yield) as a white solid. LC-MS (ESI$^+$) m/z 198.3 (M+H)$^+$.

Step 4—6-(1-Fluoro-1-methyl-ethyl)pyridine -2-carboxylic Acid

To a solution of methyl 6-(1-fluoro-1-methyl-ethyl)pyridine-2-carboxylate (1.9 g, 9.63 mmol) in THF (12 mL) and $H_2O$ (4 mL) was added LiOH·H$_2$O (808 mg, 19.3 mmol) at 0° C. The mixture was then stirred at 25° C. for 3 hours. On completion, the organic solvent was removed in vacuo and the crude product was purified by reversed-phase HPLC (0.1% FA) to give the title compound (1.7 g, 90% yield) as a yellow solid. LC-MS (ESI$^+$) m/z 184.1 (M+H)$^+$.

6-(1-fluoro-1-methyl-ethyl)-N-[2-(4-formylcyclohexyl)-6-methoxy-indazol-5-yl]-N-methyl-pyridine-2-carboxamide (Intermediate CBK)

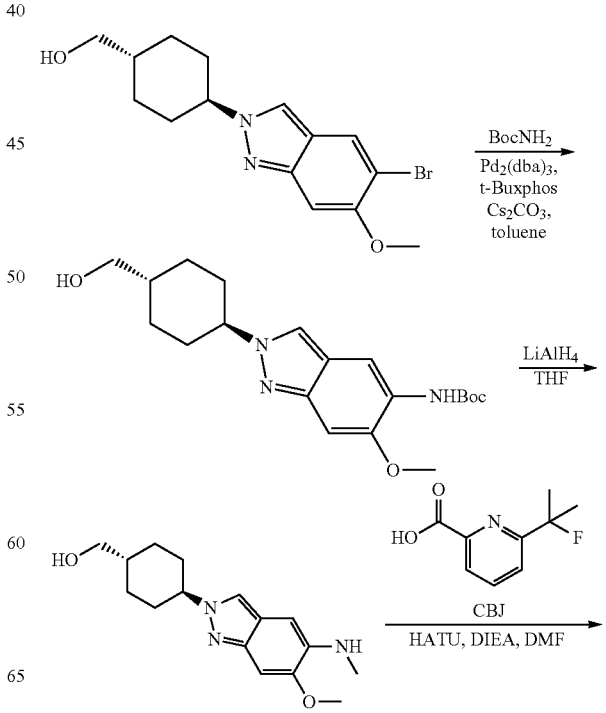

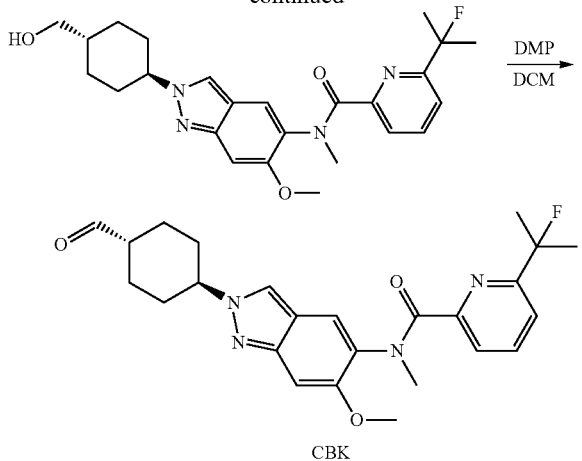

Step 1—[4-[6-methoxy-5-(methylamino)indazol-2-yl]cyclohexyl]methanol

To a solution of tert-butyl N-[2-[4-(hydroxymethyl)cyclohexyl]-6-methoxy-indazol-5-yl]carbamate (1 g, 2.66 mmol, synthesized via Step 1 of Intermediate BGT) in THF (30 mL) was added LiAlH₄ (505 mg, 13.3 mmol) at 0° C. After 10 minutes, the cooling bath was removed and after stirring at 25° C. for 20 minutes, the mixture was stirred at 60° C. for 16 hours under N₂ atmosphere. On completion, the reaction mixture was quenched with H₂O (1 mL) at 0° C., and then diluted with NaOH (1 M, 1 mL, aq.) and dried over Na₂SO₄, filtered and concentrated under reduced pressure to give a residue. The residue was purified by prep-HPLC (column: YMC Triart C18 250*50 mm*7 um; mobile phase: [water (HCl)-ACN]; B %: 5%-35%, 23 minutes) to afford the title compound (400 mg, 44% yield) as a yellow solid. ¹H NMR (400 MHz, DMSO-d₆) δ 8.47 (s, 1H), 7.83 (d, J=7.2 Hz, 1H), 7.23 (s, 1H), 4.48-4.34 (m, 2H), 3.94 (s, 3H), 3.28 (d, J=6.4 Hz, 2H), 2.87 (s, 4H), 2.12 (d, J=8.0 Hz, 2H), 1.92-1.86 (m, 4H), 1.53-1.41 (m, 1H), 1.19-1.09 (m, 2H). LC-MS (ESI⁺) m/z 290.3 (M+H)⁺.

Step 2—6-(1-fluoro-1-methyl-ethyl)-N-[2-[4-(hydroxymethyl)cyclohexyl]-6-methoxy-indazol-5-yl]-N-methyl-pyridine-2-carboxamide To a solution of [4-[6-methoxy-5-(methylamino)indazol-2-yl]cyclohexyl]methanol (400 mg, 1.38 mmol) in DMF (4 mL) and HATU (788 mg, 2.07 mmol) was added dropwise DIEA (535 mg, 4.15 mmol, 722 uL) until the pH=8 at 0° C. After addition, the mixture was stirred at this temperature for 30 minutes, and then 6-(1-fluoro-1-methyl-ethyl) pyridine-2-carboxylic acid (278 mg, 1.52 mmol, Intermediate CBJ) in DMF (4 mL) was added dropwise at 0° C. The resulting mixture was then stirred at 25° C. for 2 hours. On completion, the reaction mixture was quenched with H₂O (1 mL), the residue was diluted with H₂O (10 mL) and extracted with EA (8 mL×3). The combined organic layers were washed with brine (5 mL×2), dried over Na₂SO₄, filtered and concentrated under reduced pressure to give a residue. The residue was purified by reversed-phase (0.1% FA condition) to give the title compound (320 mg, 47% yield) as yellow oil. ¹H NMR (400 MHz, DMSO-d₆) δ 8.15 (s, 1H), 7.78 (s, 1H), 7.52 (d, J=8.0 Hz, 1H), 7.33 (s, 1H), 7.28 (d, J=7.6 Hz, 1H), 6.89 (s, 1H), 4.46 (s, 1H), 4.34-4.23 (m, 1H), 3.71 (s, 3H), 3.27 (s, 4H), 2.03 (d, J=6.4 Hz, 2H), 1.89-1.77 (m, 4H), 1.43 (d, J=8.2 Hz, 1H), 1.24-0.96 (m, 9H). LC-MS (ESI⁺) m/z 455.3 (M+H)⁺.

Step 3—6-(1-fluoro-1-methyl-ethyl)-N-[2-(4-formylcyclohexyl)-6-methoxy-indazol-5-yl]-N-methyl-pyridine-2-carboxamide To a solution of 6-(1-fluoro-1-methyl-ethyl)-N-[2-[4-(hydroxymethyl)cyclohexyl]-6-methoxy-indazol-5-yl]-N-methyl-pyridine-2-carboxamide (200 mg, 440 umol) in DCM (2 mL) was added DMP (279 mg, 660 umol). Then the mixture was stirred at 25° C. for 3 hours. On completion, the reaction mixture was quenched with Na₂S₂O₃ (2 mL, aq.) at 25° C., and then diluted with NaHCO₃ (60 mL, aq.) and extracted with DCM (30 mL×3). The combined organic layers were washed with brine (50 mL), dried over Na₂SO₄, filtered and concentrated under reduced pressure to give the title compound (200 mg, 90% yield) as a yellow oil. LC-MS (ESI⁺) m/z 453.2 (M+H)⁺.

3-[4-(azetidin-3-yl)-3-methyl-2-oxo-benzimidazol-1-yl]piperidine-2,6-dione (Intermediate CBL)

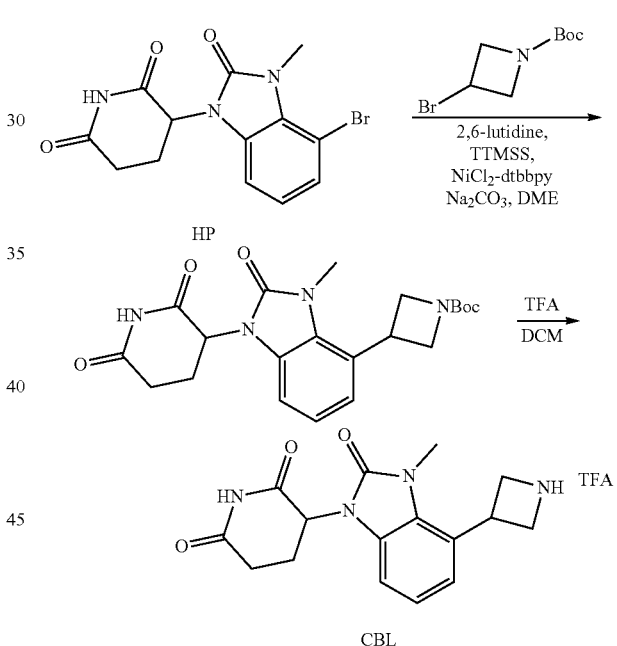

Step 1—Tert-butyl 3-[1-(2,6-dioxo-3-piperidyl)-3-methyl-2-oxo-benzimidazol-4-yl]azetidine-1-carboxylate To a solution of 3-(4-bromo-3-methyl-2-oxo-benzimidazol-1-yl)piperidine-2,6-dione (3.5 g, 10.3 mmol, Intermediate HP) in DME (5 mL) was added tert-butyl 3-bromoazetidine-1-carboxylate (3.18 g, 13.4 mmol, CAS #106419-10-0), Ir[dF(CF₃)ppy]2(dtbpy)(PF6) (232 mg, 207 umol), NiCl2-dtbbpy (123 mg, 310 umol) 2,6-lutidine (2.22 g, 20.7 mmol, 2.41 mL) and TTMSS (2.57 g, 10.3 mmol, 3.19 mL). The mixture was then stirred at 25° C. for 14 hours. On completion, the reaction mixture was filtered and concentrated under reduced pressure to give a residue. The residue was purified by column chromatography (SiO₂, DCM/Ethyl acetate=100/1 to 20/1) to give the title compound (2.2 g, 50% yield) as a white solid. $^1$H NMR (400 MHz, DMSO-$d_6$) δ 11.09 (s, 1H), 7.24 (d, J=8.0 Hz, 1H), 7.14-7.01 (m, 2H), 5.41-5.34 (m, 1H), 4.49 (t, J=6.4 Hz, 1H), 4.28 (t, J=8.0 Hz, 2H), 3.96 (s, 2H), 3.50 (s, 3H), 2.93-2.83 (m, 1H), 2.06-1.92 (m, 1H), 1.41 (s, 9H), 1.04 (d, J=6.4 Hz, 2H). LC-MS (ESI$^+$) m/z 359.0 (M+H)$^+$.

Step 2—3-[4-(azetidin-3-yl)-3-methyl-2-oxo-benzimidazol-1-yl]piperidine-2,6-dione To a solution of tert-butyl 3-[1-(2,6-dioxo-3-piperidyl)-3-methyl-2-oxo-benzimidazol-4-yl]azetidine-1-carboxylate (500 mg, 1.21 mmol) in DCM (3 mL) was added TFA (1.54 g, 13.5 mmol, 1 mL). The mixture was then stirred at 25° C. for 3 hours. On completion, the reaction was concentrated under reduced pressure to give the title compound (300 mg, 76% yield, TFA salt) as a colorless oil. LC-MS (ESI$^+$) m/z 315.1 (M+H)$^+$.

2-(2,6-dioxo-3-piperidyl)-4-[7-(methylamino)heptylamino]isoindoline-1,3-dione (Intermediate CBM)

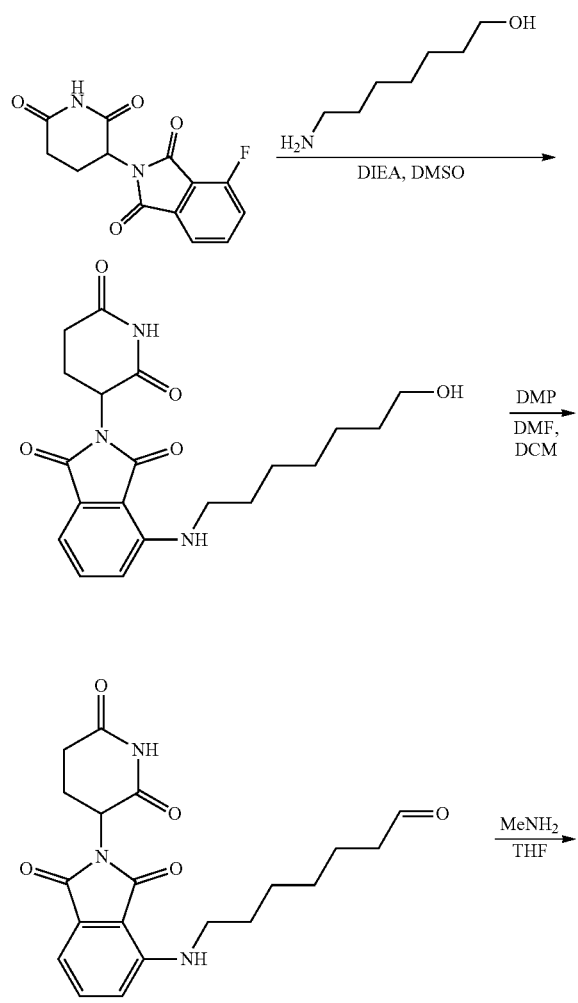

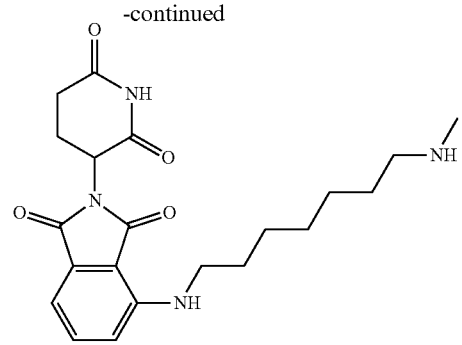

CBM

Step 1—2-(2,6-dioxo-3-piperidyl)-4-(7-hydroxyheptylamino)isoindoline-1,3-dione

A mixture of 2-(2,6-dioxo-3-piperidyl)-4-fluoro-isoindoline-1,3-dione (200 mg, 724 umol, CAS #835616-60-9), 7-aminoheptan-1-ol (114 mg, 868 umol, CAS #19243-04-0), DIEA (280 mg, 2.17 mmol) in DMSO (2 mL) was stirred at 130° C. for 1 hour. On completion, the reaction mixture was partitioned between ethyl acetate (1 mL×3) and water (2 mL). The combined organic phase was dried over anhydrous sodium sulfate, filtered and concentrated to give the title compound (230 mg, 70% yield) LC-MS (ESI+) m/z 388.2 (M+H)$^+$.

Step 2—7-[[2-(2,6-dioxo-3-piperidyl)-1,3-dioxo-isoindolin-4-yl]amino]heptanal

To a solution of 2-(2,6-dioxo-3-piperidyl)-4-(7-hydroxyheptylamino)isoindoline-1,3-dione (200 mg, 516 umol) in DMF (1 mL), DCM (1 mL) was added DMP (284 mg, 671 umol). The mixture was stirred at 25° C. for 1 hour. On completion, the reaction mixture was quenched with water (10 mL) at 20° C., and then diluted with sodium thiosulfate (4 mL) and extracted with DCM (2 mL×3). The combined organic layers were washed with NaHCO$_3$ 1 mL (1 mL×3), dried over anhydrous sodium sulfate, filtered and concentrated under reduced pressure to give the title compound (240 mg, 80% yield). LC-MS (ESI+) m/z 386.1 (M+H)$^+$.

Step 3—2-(2,6-dioxo-3-piperidyl)-4-[7-(methyl amino)heptylamino]isoindoline-1,3-dione To a solution of 7-[[2-(2,6-dioxo-3-piperidyl)-1,3-dioxo-isoindolin-4-yl]amino]heptanal (240 mg, 622 umol) in THF (1 mL) was added methanamine; hydrochloride (50.4 mg, 747 umol) and NaBH(OAc)$_3$ (329 mg, 1.56 mmol). The mixture was stirred at 25° C. for 0.5 hour. On completion, the residue was purified by reverse phase to give the title compound (40.0 mg, 70% yield). LC-MS (ESI+) m/z 401.2 (M+H)$^+$.

1081

N-1-[2-(4-formylcyclohexyl)-6-(1-hydroxy-1-methyl-ethyl)indazol-5-yl]-6-(trifluoromethyl)pyridine-2-carboxamide (Intermediate CBN)

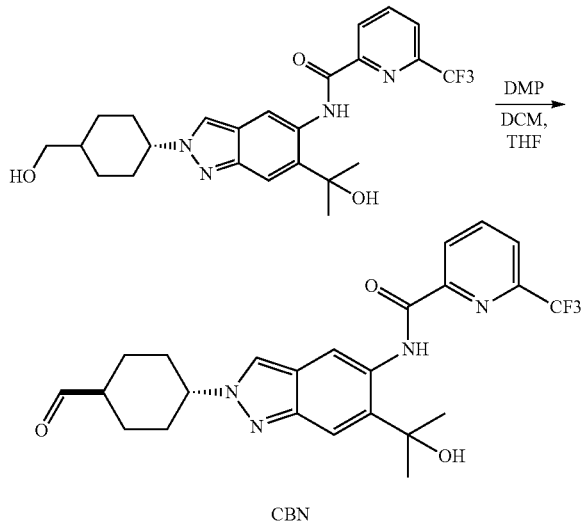

To a solution of N-[2-[4-(hydroxymethyl)cyclohexyl]-6-(1-hydroxy-1-methyl-ethyl)indazol-5-yl]-6-(trifluoromethyl)pyridine-2-carboxamide (100 mg, 209 umol, synthesized via Steps 1-2 of Intermediate AGL) in DCM (0.5 mL) THF (0.5 mL) was added DMP (115 mg, 272 umol). The mixture was then stirred at 25° C. for 20 min. On completion, the reaction mixture was partitioned between ethyl acetate (3 mL×3) and water (5 mL). The combined organic phase was dried over anhydrous sodium sulfate, filtered and concentrated to give the title compound (105 mg, 90% yield). LC-MS (ESI+) m/z 474.9 (M+H)+.

3-[4-(7-azaspiro[3.5]nonan-2-ylamino)-1-oxo-isoindolin-2-yl]piperidine-2,6-dione (Intermediate CBO)

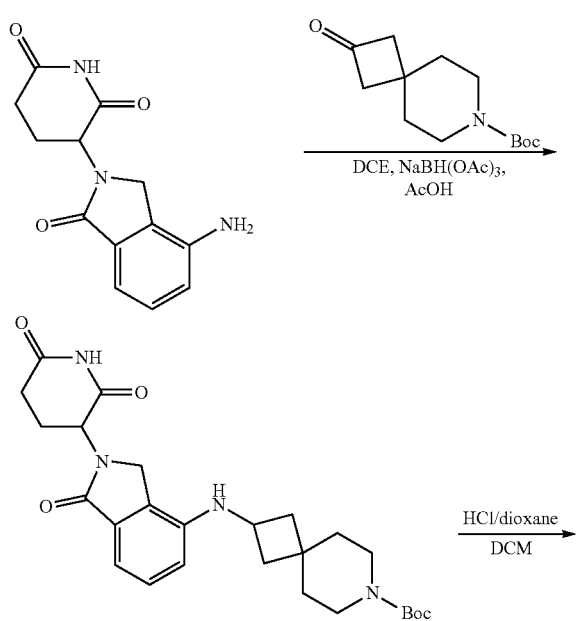

1082

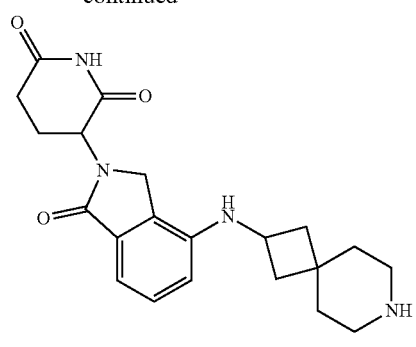

Step 1—Tert-butyl 2-[[2-(2,6-dioxo-3-piperidyl)-1-oxo-isoindolin-4-yl]amino]-7-azaspiro[3.5]nonane-7-carboxylate To a solution of 3-(4-amino-1-oxo-isoindolin-2-yl) piperidine-2,6-dione (500 mg, 1.93 mmol, CAS #191732-72-6) and tert-butyl 2-oxo-7-azaspiro[3.5]nonane-7-carboxylate (507 mg, 2.12 mmol, CAS #203661-69-2) in DCE (10.0 mL) was added NaBH(OAc)$_3$ (531 mg, 2.51 mmol) and AcOH (1.97 g, 32.7 mmol, 1.8 mL). The mixture was then stirred at 25° C. for 2 hours. On completion, the mixture was filtered and concentrated under reduced pressure to give a residue. The crude product was triturated with dichloromethane: acetonitrile (1:10, 80.0 mL) at 25° C. for 30 minutes to give the title compound (670 mg, 71% yield). LC-MS (ESI+) m/z 483.2 (M+H)+

Step 2—3-[4-(7-Azaspiro[3.5] nonan-2-ylamino)-1-oxo-isoindolin-2-yl]piperidine-2,6-dione To a solution of tert-butyl 2-[[2-(2,6-dioxo-3-piperidyl)-1-oxo-isoindolin-4-yl]amino]-7-azaspiro[3.5]nonane-7-carboxylate (120 mg, 248 umol) in DCM (3 mL) was added HCl/dioxane (4 M, 1.2 mL). The mixture was then stirred at 25° C. for 30 min. On completion, the reaction mixture was concentrated under reduced pressure to remove solvent to give the title compound (100 mg, 95% yield) as a white solid. LC-MS (ESI+) m/z 383.1 (M+H)+.

2-(2,6-dioxo-3-piperidyl)-4-[3-(methylamino)propylamino]isoindoline-1,3-dione (Intermediate CBP)

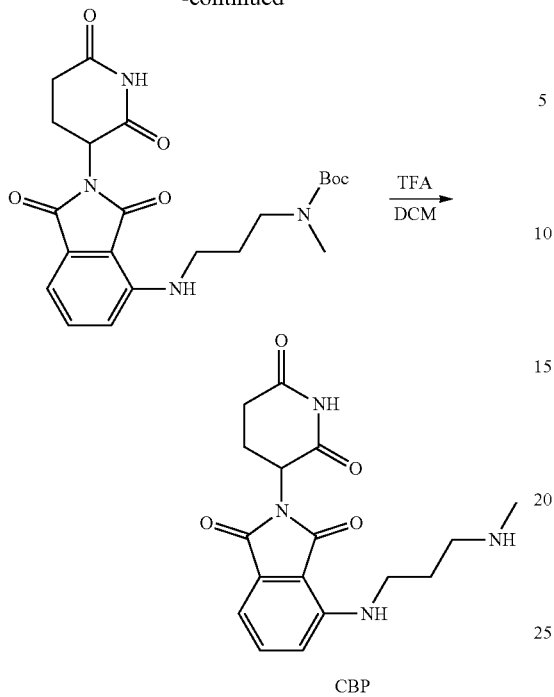

CBP

Step 1—Tert-butyl N-[3-[[2-(2,6-dioxo-3-piperidyl)-1,3-dioxo-isoindolin-4-yl]amino]propyl]-N-methyl-carbamate To a solution of 2-(2,6-dioxo-3-piperidyl)-4-fluoro-isoindoline-1,3-dione (150 mg, 543 umol, CAS #835616-60-9), and tert-butyl N-(3-aminopropyl)-N-methyl-carbamate (122 mg, 651 umol, CAS #150349-30-3) in DMSO (2 mL) was added DIEA (210 mg, 1.63 mmol). The mixture was then stirred at 130° C. for 1 hours. On completion, the mixture was filtered by H$_2$O and concentrated in vacuo to give the title compound (200 mg, 80% yield) as green solid. LC-MS (ESI$^+$) m/z 345.1 (M+H)$^{-1\circ\,\circ}$.

Step 2—2-(2,6-Dioxo-3-piperidyl)-4-[3-(methylamino)propylamino]isoindoline-1,3-dione To a solution of tert-butyl N-[3-[[2-(2,6-dioxo-3-piperidyl)-1,3-dioxo-isoindolin-4-yl]amino]propyl]-N-methyl-carbamate (200 mg, 449 umol) in DCM (1 mL) was added TFA (1.54 g, 13.5 mmol, 1 mL). The mixture was then stirred at 25° C. for 5 min. On completion, the reaction mixture was concentrated in vacuo to give the title compound (160 mg, 95% yield) as green solid. LC-MS (ESI$^+$) m/z 345.0 (M+H)$^+$.

4-(4-Aminobutylamino)-2-(2,6-dioxo-3-piperidyl)isoindoline-1,3-dione (Intermediate CBQ)

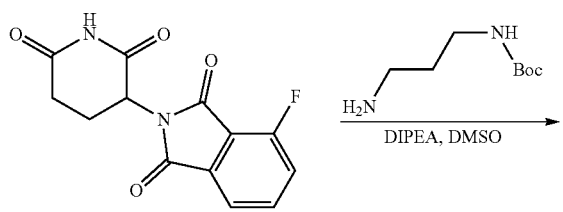

Step 1—Tert-butyl N-[4-[[2-(2,6-dioxo-3-piperidyl)-1,3-dioxo-isoindolin-4-yl]amino]butyl]carbamate To a solution of 2-(2,6-dioxo-3-piperidyl)-4-fluoro-isoindoline-1,3-dione (200 mg, 724 umol CAS #835616-60-9) tert-butyl N-(4-aminobutyl)carbamate (163 mg, 868 umol, CAS #68076-36-8) in DMSO (3.0 mL) was added DIEA (280 mg, 2.17 mmol). The mixture was stirred at 130° C. for 2 hours. On completion, the mixture was filtered and concentrated to give the title compound (250 mg, 77% yield) as a yellow solid. $^1$H NMR (400 MHz, DMSO-d$_6$) δ 11.34-10.33 (m, 1H), 7.58 (t, J=7.6 Hz, 1H), 7.11 (d, J=8.4 Hz, 1H), 7.02 (d, J=7.2 Hz, 1H), 5.05 (dd, J=5.6, 12.8 Hz, 1H), 3.31-3.27 (m, 2H), 3.00-2.89 (m, 4H), 2.02 (dd, J=5.2, 10.4 Hz, 1H), 1.59-1.42 (m, 6H), 1.37 (s, 9H), 1.36 (s, 2H).

Step 2—4-(4-aminobutylamino)-2-(2,6-dioxo-3-piperidyl)isoindoline-1,3-dione

To a solution of tert-butyl N-[4-[[2-(2,6-dioxo-3-piperidyl)-1,3-dioxo-isoindolin-4-yl]amino] butyl]carbamate (150 mg, 337 umol) in DCM (1 mL) was added TFA (1.54 g, 13.5 mmol). The mixture was stirred at 20° C. for 0.5 hours. On completion, the mixture was filtered and concentrated to give the title compound (116 mg, 95% yield) as a yellow solid. LC-MS (ESI+) m/z 345.1 (M+H)$^+$.

1085

N-[2-[4-(aminomethyl)cyclohexyl]-6-(1-hydroxy-1-methyl-ethyl)indazol-5-yl]-6-(trifluoromethyl)pyridine-2-carboxamide (Intermediate CBR)

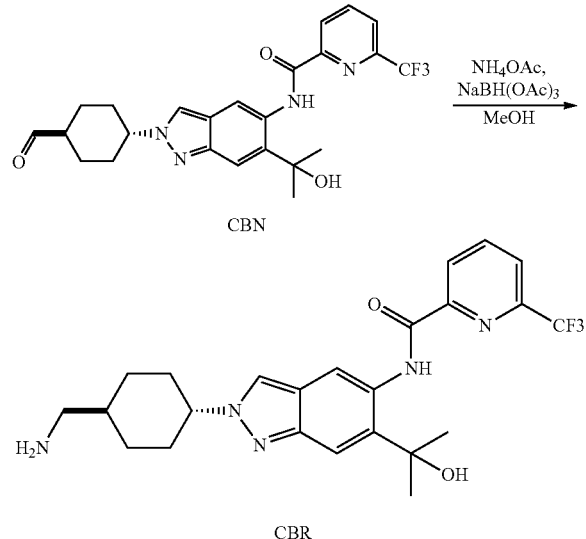

A mixture of N-[2-(4-formylcyclohexyl)-6-(1-hydroxy-1-methyl-ethyl)indazol-5-yl]-6-(trifluoromethyl)pyridine-2-carboxamide (100 mg, 210 umol, Intermediate CBN), NH₄OAc (324 mg, 4.22 mmol), NaBH₃CN (19.8 mg, 316 umol) in MeOH (1 mL) was degassed and purged with $N_2$ three times. Then the mixture was stirred at 25° C. for 12 hours. On completion, the crude product was purified by reversed-phase HPLC (0.1% FA condition) to give the title compound (80 mg, 70% yield) as brown liquid. ¹H NMR (400 MHz, DMSO-d6) δ 12.37 (s, 1H), 8.72 (s, 1H), 8.50-8.42 (m, 1H), 8.41-8.31 (m, 3H), 8.17 (dd, J=0.9, 7.6 Hz, 1H), 7.58 (s, 1H), 4.50-4.37 (m, 1H), 3.51-3.49 (m, 2H), 2.16 (d, J=10.8 Hz, 3H), 2.01-1.84 (m, 5H), 1.63 (s, 6H), 1.29-1.12 (m, 3H). LC-MS (ESI⁺) m/z 476.1 (M+H)⁺.

Tert-butyl N-[3-(4-aminocyclohexoxy)propyl]-N-methyl-carbamate (Intermediate CBS)

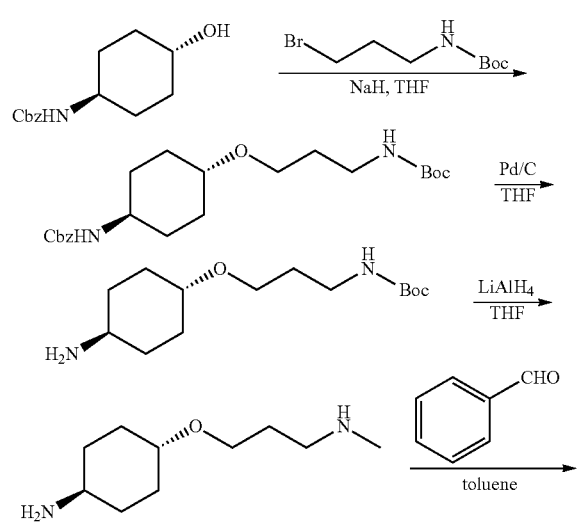

1086

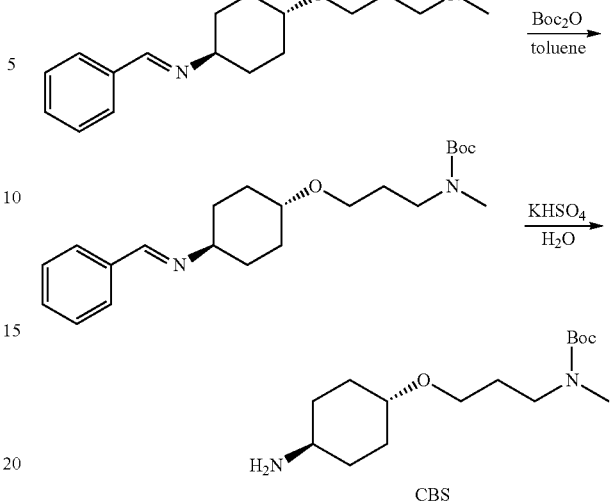

Step 1—Tert-butyl N-[3-[4-(benzyloxycarbonylamino)cyclohexoxy]propyl]carbamate To a solution of benzyl N-(4-hydroxycyclohexyl) carbamate (6 g, 24.1 mmol) in DMF (160 mL) was added NaH (1.06 g, 26.4 mmol, 60% dispersion in mineral oil), then the mixture was stirred at 25° C. for 0.5 hour. Next, tert-butyl N-(3-bromopropyl) carbamate (8.60 g, 36.1 mmol, CAS #83948-53-2) was added to the solution stirred at 25° C. for 15.5 hours. On completion, the mixture was quenched with H₂O (150 mL), diluted with H₂O (500 mL), then extracted with DCM (3×200 mL), washed with brine (3×200 mL), dried with anhydrous Na₂SO₄, filtered and the filtrate was concentrated in vacuo. The residue was purified by column chromatography (SiO₂, Petroleum ether/Ethyl acetate=100/1 to 2/1, Rf=0.65, PE:EA=1:1) to give the title compound (1.2 g, 2.95 mmol, 12% yield) as a white solid. LC-MS (ESI⁺) m/z 307.1 (M+H)⁺

Step 2—Tert-butyl N-[3-(4-aminocyclohexoxy)propyl]carbamate

To a solution of Pd/C (10 mg, 49.2 umol, 10 wt %) in THF (2 mL) was added tert-butyl N-[3-[4-(benzyloxycarbonylamino)cyclohexoxy]propyl]carbamate (100 mg, 245 umol). The mixture was stirred at 25° C. for 1 hour under H₂. On completion, the mixture was filtered and the filtrate was concentrated in vacuo to give the title compound (49 mg, 73% yield) as a colorless oily liquid. ¹H NMR (400 MHz, DMSO-d₆). ¹H NMR (400 MHz, CDCl₃) δ 4.89 (s, 1H), 3.52 (t, J=6.0 Hz, 2H), 3.28-3.17 (m, 3H), 2.80-2.69 (m, 1H), 2.09-1.98 (m, 3H), 1.78-1.64 (m, 3H), 1.45 (s, 9H), 1.37-1.11 (m, 6H).

Step 3—4-[3-(Methylamino)propoxy]cyclohexanamine

A mixture of tert-butyl N-[3-(4-aminocyclohexoxy)propyl]carbamate (760 mg, 2.79 mmol) in THF (13 mL) was degassed and purged with N₂ three times, and then LiAlH₄ (529 mg, 13.9 mmol) was added at 0° C. Then the mixture was stirred at 70° C. for 3 hours under N₂ atmosphere. On completion, the mixture was quenched with H₂O (530 uL)

and NaOH (530 uL, 1 mol/L) at 0° C., dried with anhydrous Na$_2$SO$_4$ then filtered and washed with EA (50 mL). The filtrate was concentrated in vacuo to give the title compound (500 mg, 96% yield) as a colorless oily liquid. $^1$H NMR (400 MHz, DMSO-d6) δ 3.45-3.34 (m, 3H), 3.16-3.08 (m, 1H), 2.48-2.43 (m, 2H), 2.27-2.20 (m, 3H), 1.94-1.83 (m, 1H), 1.84-1.82 (m, 1H), 1.79-1.65 (m, 3H), 1.60-1.52 (m, 2H), 1.36 (d, J=4.0 Hz, 1H), 1.15-0.92 (m, 5H).

Step 4—3-[4-[(E)-benzylideneamino]cyclohexoxy]-N-methyl-propan-1-amine

A mixture of 4-[3-(methylamino)propoxy]cyclohexanamine (250 mg, 1.34 mmol), benzaldehyde (149 mg, 1.41 mmol, 142 uL, CAS #100-52-7) in toluene (4 mL) was stirred at 120° C. for 16 hours. The mixture was concentrated in vacuo to give the title compound (320 mg, 86% yield) as a brown oily liquid. $^1$H NMR (400 MHz, DMSO-d$_6$) δ 8.38 (s, 1H), 7.89-7.78 (m, 1H), 7.75-7.64 (m, 1H), 7.48-7.37 (m, 2H), 7.32-7.30 (m, 1H), 4.49 (s, 1H), 3.70-3.49 (m, 3H), 2.88-2.59 (m, 3H), 2.10-1.93 (m, 2H), 1.71-1.50 (m, 4H), 1.41-1.18 (m, 4H), 0.92-0.64 (m, 1H), 0.02-0.01 (m, 2H); LC-MS (ESI$^+$) m/z 375.0 (M+H)$^+$.

Step 5—Tert-butyl N-[3-[4-[(E)-benzylideneamino]cyclohexoxy]propyl]-N-methyl-carbamate To a solution of 3-[4-[(E)-benzylideneamino]cyclohexoxy]-N-methyl-propan-1-amine (320 mg, 1.17 mmol) in toluene (8 mL) was added tert-butoxycarbonyl tert-butyl carbonate (254 mg, 1.17 mmol, 267 uL, CAS #24424-99-5). The mixture was then stirred at 25° C. for 3 hours. On completion, the mixture was concentrated in vacuo to give the title compound (400 mg, 91% yield) as a brown oily liquid. LC-MS (ESI$^+$) m/z 375.1 (M+H)$^+$.

Step 6—Tert-butyl N-[3-(4-aminocyclohexoxy)propyl]-N-methyl-carbamate

A mixture of tert-butyl N-[3-[4-[(E)-benzylideneamino]cyclohexoxy]propyl]-N-methyl-carbamate (400 mg, 1.07 mmol) and KHSO$_4$ (290 mg, 2.14 mmol) in H$_2$O (10 mL) was stirred at 0° C. for 3 hours. On completion, the mixture was diluted with H$_2$O (10 mL), extracted with MTBE (3×20 mL), and water phase was extracted with DCM (3×20 mL). The combined organic layer was washed with brine (3×20 mL), dried with anhydrous Na$_2$SO$_4$, filtered and the filtrate was concentrated in vacuo to give the title compound (220 mg, 71% yield) as a colorless oily liquid. $^1$H NMR (400 MHz, DMSO-d$_6$) δ 3.38-3.35 (m, 2H), 3.22-3.14 (m, 2H), 2.78-2.71 (m, 3H), 2.67 (s, 1H), 2.34 (d, J=12.4 Hz, 1H), 2.07 (s, 1H), 1.89 (d, J=10.0 Hz, 2H), 1.76-1.56 (m, 6H), 1.43-1.35 (m, 9H), 1.16-0.95 (m, 4H) LC-MS (ESI$^+$) m/z 287.1 (M+H)$^+$ 2-(2,6-Dioxo-3-piperidyl)-4-[[4-[3-(methylamino)propoxy] cyclohexyl]amino]isoindoline-1,3-dione (Intermediate CBT)

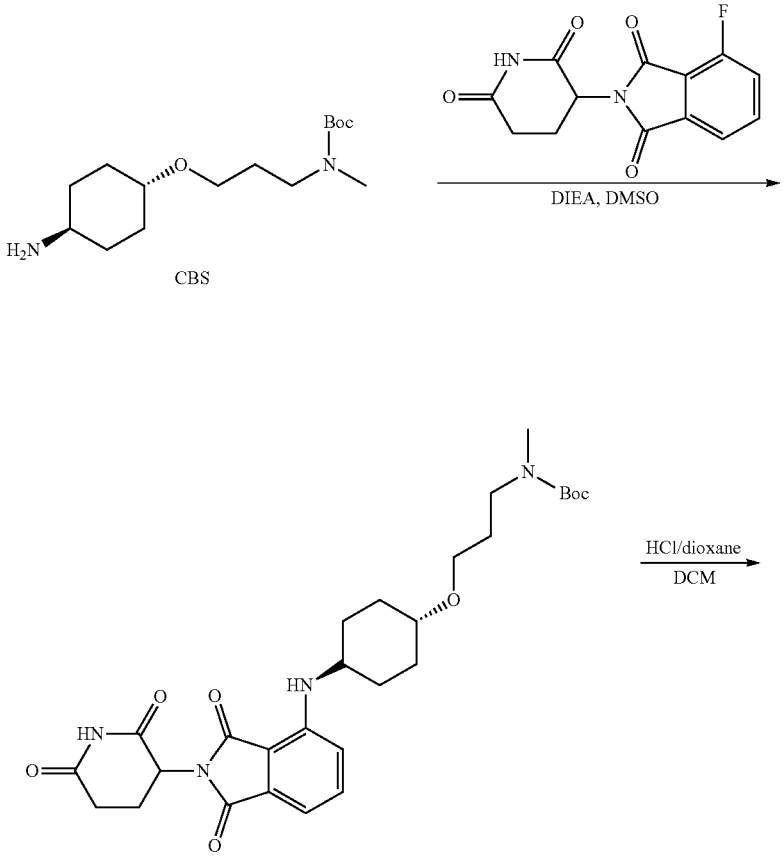

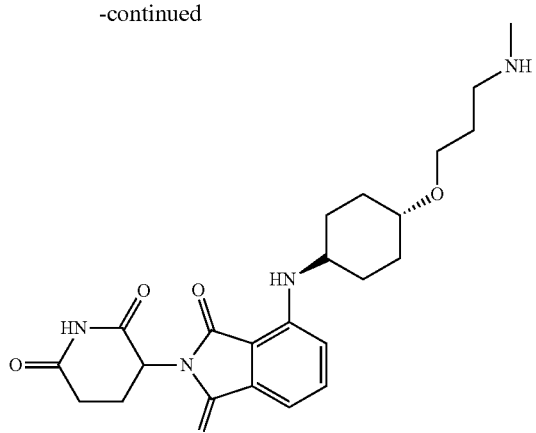

CBT

Step 1—Tert-butyl-N-[3-[4-[[2-(2,6-dioxo-3-piperidyl)-1,3-dioxo-isoindolin-4-yl]amino]cyclohexoxy]propyl]-N-methyl-carbamate A mixture of tert-butyl N-[3-(4-aminocyclohexoxy)propyl]-N-methyl-carbamate (220 mg, 768 umol, Intermediate CBS), 2-(2,6-dioxo-3-piperidyl)-4-fluoro-isoindoline-1,3-dione (212 mg, 768 umol, CAS #835616-60-9), and DIEA (198 mg, 1.54 mmol, 267 uL) in DMSO (7 mL) was stirred at 130° C. for 2 hours. The mixture was diluted with H₂O (10 mL), and extracted with EA (3×30 mL). The combined organic layer was washed with brine (3×30 mL), dried with anhydrous Na₂SO₄, then filtered and the filtrate was concentrated in vacuo. The mixture was purified by pre-HPLC (column: Phenomenex Luna C18 200*40 mm*10 um; mobile phase: [water(FA)-ACN]; B %: 48%-78%, 8 min) to give the title compound (60 mg, 14% yield) as a yellow solid. $^1$H NMR (400 MHz, DMSO-$d_6$) δ 11.09 (s, 1H), 7.71-7.53 (m, 1H), 7.17 (d, J=8.8 Hz, 1H), 7.04 (d, J=6.8 Hz, 1H), 6.19 (d, J=8.4 Hz, 1H), 5.04 (dd, J=5.2, 12.8 Hz, 1H), 3.21 (t, J=7.2 Hz, 4H), 2.77 (s, 4H), 2.67 (d, J=2.0 Hz, 3H), 2.35-2.31 (m, 1H), 2.09-1.92 (m, 6H), 1.70-1.61 (m, 2H), 1.39 (s, 9H), 1.37-1.29 (m, 4H), LC-MS (ESI$^+$) m/z 287.1 (M+H)$^+$.

Step 2—2-(2,6-Dioxo-3-piperidyl)-4-[[4-[3-(methylamino)propoxy] cyclohexyl]amino]isoindoline-1,3-dione To a solution of tert-butyl N-[3-[4-[[2-(2,6-dioxo-3-piperidyl)-1,3-dioxo-isoindolin-4-yl]amino] cyclohexoxy]propyl]-N-methyl-carbamate (60 mg, 111 umol) in DCM (2 mL) was added HCl/dioxane (4 M, 1 mL). The mixture was then stirred at 25° C. for 1 hour. The mixture was concentrated in vacuo to give the title compound (48 mg, 98% yield) as a yellow solid. LC-MS (ESI$^+$) m/z 443.3 (M+H)$^+$.

4-(2-aminoethylamino)-2-(2,6-dioxo-3-piperidyl) isoindoline-1,3-dione (Intermediate CBU)

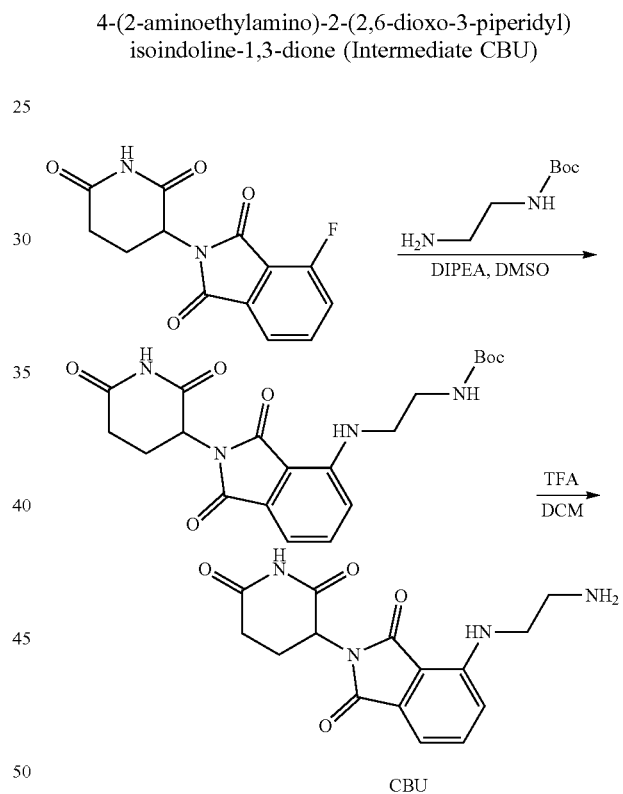

CBU

Step 1—Tert-butyl N-[2-[[2-(2,6-dioxo-3-piperidyl)-1,3-dioxo-isoindolin-4-yl]amino]ethyl]carbamate To a solution of 2-(2,6-dioxo-3-piperidyl)-4-fluoro-isoindoline-1,3-dione (300 mg, 1.09 mmol) and tert-butyl N-(2-aminoethyl)carbamate (208 mg, 1.30 mmol, 204 uL) in DMSO (3.0 mL) was added DIEA (421 mg, 3.26 mmol, 567 uL). The mixture was then stirred at 130° C. for 1 hour. On completion, the mixture was added H₂O and filtered. The solid was dried to give the title compound (470 mg, 85% yield) as a green solid. $^1$H NMR (400 MHz, DMSO-$d_6$) δ 11.08 (s, 1H), 7.61-7.54 (m, 1H), 7.14 (d, J=8.4 Hz, 1H), 7.03 (d, J=7.2 Hz, 1H), 6.71 (t, J=6.0 Hz, 1H), 5.05 (dd, J=5.6, 12.8 Hz, 1H), 3.36 (d, J=6.4 Hz, 2H), 3.16-3.07 (m, 3H), 2.95-2.83 (m, 1H), 2.60 (d, J=2.4 Hz, 2H), 2.05-1.96 (m, 1H), 1.36 (s, 9H). LC-MS (ESI+) m/z 417.0 (M+H)+.

Step 2—4-(2-Aminoethylamino)-2-(2,6-dioxo-3-piperidyl)isoindoline-1,3-dione

To a solution of tert-butyl N-[2-[[2-[(2,6-dioxo-3-piperidyl)-1,3-dioxo-isoindolin-4-yl]amino]ethyl]carbamate (150 mg, 360 umol) in DCM (1.00 mL) was added TFA (1.54 g, 13.5 mmol, 1 mL). The mixture was then stirred at 25° C. for 0.5 hours. On completion, the mixture was concentrated to give the title compound (113 mg, 99% yield) as a brown oil. LC-MS (ESI+) m/z 317.0 (M+H)+.

Benzyl N-(2-aminospiro[3.5]nonan-7-yl)-N-methyl-carbamate (Intermediate AXA)

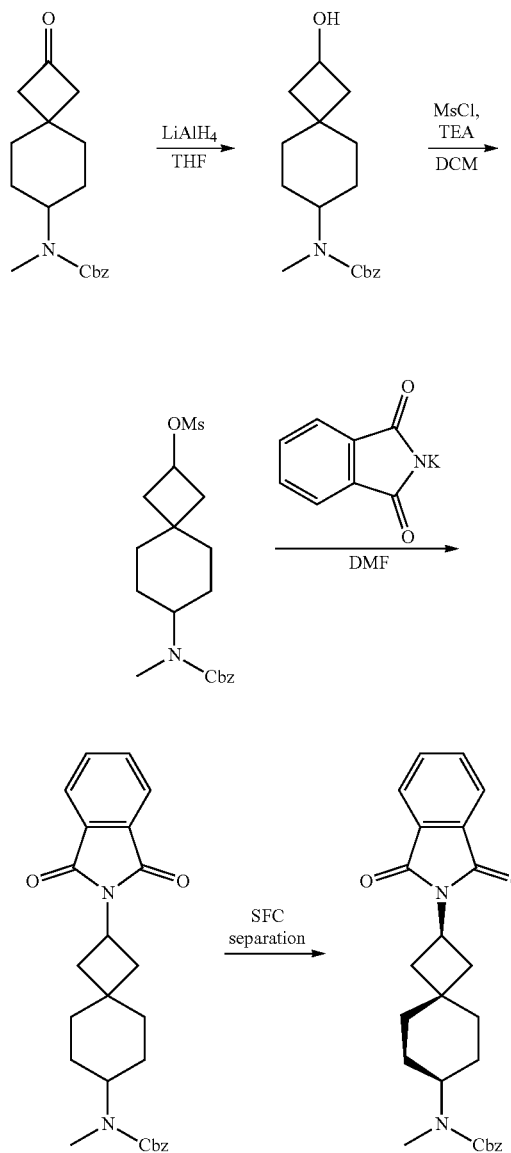

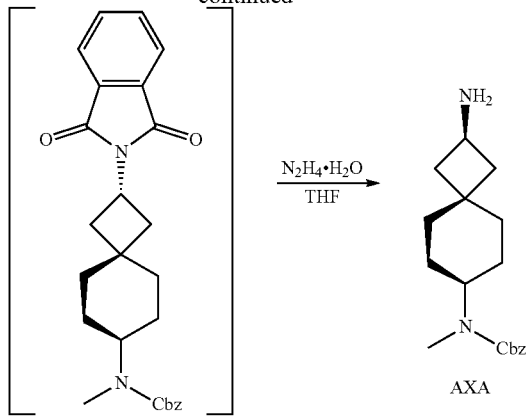

Step 1—Benzyl N-(2-hydroxyspiro[3.5]nonan-7-yl)-N-methyl-carbamate

To a solution of benzyl N-methyl-N-(2-oxospiro[3.5]nonan-7-yl)carbamate (1.00 g, 3.32 mmol, synthesized via Steps 1-5 of Intermediate ANJ) in THF (15 mL) was added LiAlH4 (151 mg, 3.98 mmol) at 0° C. The mixture was stirred at 0° C. for 0.1 hr. On completion, the reaction mixture was quenched with water (0.5 mL) and NaOH (0.5 mL, 15%) at 0° C., then the mixture was stirred at 0° C. for 0.5 hr. Then the mixture was filtered and the filtrate was dried over Na2SO4, filtered and concentrated in vacuo to give the title compound (1.00 g, 95% yield) as colorless oil. 1H NMR (400 MHz, CDCl3) δ 7.44-7.29 (m, 5H), 5.13 (s, 2H), 4.34-4.23 (m, 1H), 3.95 (s, 1H), 3.75 (t, J=6.4 Hz, 1H), 2.79 (s, 3H), 2.38-2.27 (m, 1H), 2.17-2.11 (m, 1H), 1.87-1.84 (m, 1H), 1.77-1.69 (m, 2H), 1.61-1.42 (m, 7H).

Step 2—[7-[Benzyloxycarbonyl(methyl)amino]spiro [3.5]nonan-2-yl]methanesulfonate To a solution of benzyl N-(2-hydroxyspiro[3.5]nonan-7-yl)-N-methyl-carbamate (1.00 g, 3.30 mmol) and TEA (1.00 g, 9.89 mmol) in DCM (20 mL) was added MsCl (566 mg, 4.94 mmol) at 0° C. The mixture was stirred at 30° C. for 0.5 hr. On completion, the mixture was quenched with water (20 mL), then washed with water (3×20 mL). The organic layer were dried over Na2SO4, filtered and concentrated in vacuo to give the title compound (1.20 g, 95% yield) as colorless oil. 1H NMR (400 MHz, CDCl3) δ 7.48-7.28 (m, 5H), 5.13 (s, 2H), 5.04-4.92 (m, 1H), 4.04-3.75 (m, 1H), 3.01-2.96 (s, 3H), 2.78 (s, 3H), 2.50-2.40 (m, 1H), 2.30-2.24 (m, 1H), 2.13-2.05 (m, 1H), 2.00 (dd, J=7.2, 12.0 Hz, 1H), 1.77-1.68 (m, 2H), 1.61-1.52 (m, 3H), 1.52-1.41 (m, 3H).

Step 3—Benzyl N-[2-(1,3-dioxoisoindolin-2-yl) spiro[3.5]nonan-7-yl]-N-methyl-carbamate To a solution of [7-[benzyloxycarbonyl(methyl)amino] spiro[3.5]nonan-2-yl]methanesulfonate (1.10 g, 2.88 mmol) in DMF (15 mL) was added (1,3-dioxoisoindolin-2-yl) potassium (801 mg, 4.33 mmol). The mixture was stirred at 100° C. for 16 hrs. On completion, the reaction mixture diluted with water (50 mL) and extracted with EA (3×20 mL). The combined organic layers were dried over Na2SO4, filtered and concentrated in vacuo to give a residue. On completion, the reaction mixture was purified by prep-HPLC (column: Phenomenex luna C18 150*40 mm*15 um;

mobile phase: [water (0.225% FA)-ACN]) to give the title compound (0.35 g, 28% yield) as light yellow solid. $^1$H NMR (400 MHz, CDCl$_3$) δ 7.88-7.76 (m, 2H), 7.75-7.66 (m, 2H), 7.44-7.28 (m, 5H), 5.15 (s, 2H), 4.78-4.69 (m, 1H), 4.11-3.72 (m, 1H), 2.79 (s, 3H), 2.73-2.65 (m, 1H), 2.59 (t, J=10.0 Hz, 1H), 2.31-2.17 (m, 1H), 2.12-1.99 (m, 2H), 1.98-1.87 (m, 1H), 1.64-1.35 (m, 6H); LC-MS (ESI$^+$) m/z 433.4 (M+H)$^+$.

Step 4—Benzyl ((2S,4s,7S)-2-(1,3-dioxoisoindolin-2-yl)spiro[3.5] nonan-7-yl)(methyl)carbamate and benzyl 42R,4r,7R)-2-(1,3-dioxoisoindolin-2-yl)spiro [3.5]nonan-7-yl)(methyl)carbamate Benzyl N-[2-(1,3-dioxoisoindolin-2-yl)spiro[3.5]nonan-7-yl]-N-methyl-carbamate (0.30 g, 693 umol) was purified by SFC (column: DAICEL CHIRALPAK AD (250 mm*30 mm, 10 um); mobile phase: [0.1% NH$_3$·H$_2$O EtOH]; B %: 60%-60%, 4.4 min) to give to give two isomers. The first fraction was benzyl ((2S,4s,7S)-2-(1,3-dioxoisoindolin-2-yl)spiro[3.5]nonan-7-yl)(methyl)carbamate (120 mg, 38% yield, tR=1.50) isolated as yellow solid. $^1$H NMR (400 MHz, CDCl$_3$) δ 7.75-7.73 (m, 2H), 7.67-7.58 (m, 2H), 7.35-7.19 (m, 5H), 5.07 (s, 2H), 4.70-4.61 (m, 1H), 4.04-3.71 (m, 1H), 2.72 (s, 3H), 2.62 (dd, J=9.6, 10.8 Hz, 1H), 2.51 (t, J=10.0 Hz, 1H), 2.24-2.11 (m, 1H), 2.03-1.92 (m, 2H), 1.88-1.84 (m, 1H), 1.72-1.31 (m, 6H); LC-MS (ESI$^+$) m/z 433.0 (M+H)$^+$. The second fraction was benzyl ((2R, 4r,7R)-2-(1,3-dioxoisoindolin-2-yl) spiro[3.5]nonan-7-yl) (methyl)carbamate (120 mg, 38% yield, tR=1.89) isolated as yellow solid. $^1$H NMR (400 MHz, CDCl$_3$) δ 7.79-7.70 (m, 2H), 7.68-7.59 (m, 2H), 7.36-7.20 (m, 5H), 5.07 (s, 2H), 4.70-4.61 (m, 1H), 4.02-3.73 (m, 1H), 2.72 (s, 3H), 2.62 (dd, J=9.6, 10.8 Hz, 1H), 2.51 (t, J=10.0 Hz, 1H), 2.22-2.11 (m, 1H), 2.05-1.92 (m, 2H), 1.88-1.84 (m, 1H), 1.67-1.32 (m, 6H); LC-MS (ESI$^+$) m/z 433.0 (M+H)$^+$.

Step 5—Benzyl N-(2-aminospiro[3.5]nonan-7-yl)-N-methyl-carbamate

To a solution of benzyl N-[2-(1,3-dioxoisoindolin-2-yl) spiro[3.5]nonan-7-yl]-N-methyl-carbamate (0.11 g, 254 umol) in EtOH (3 mL) was added N$_2$H$_4$·H$_2$O (129 mg, 2.54 mmol, 98% purity). The mixture was stirred at 80° C. for 6 hrs. On completion, the reaction mixture was filtered to give the filtrate and concentrated in vacuo to give a residue. The residue was diluted with DCM (10 mL), filtered to give the filtrate and concentrated in vacuo to give the title compound (75.0 mg, 92% yield) as light yellow solid. $^1$H NMR (400 MHz, CDCl$_3$) δ 7.45-7.28 (m, 5H), 5.13 (s, 2H), 4.06-3.74 (m, 1H), 3.44-3.36 (m, 1H), 2.78 (s, 3H), 2.34-2.23 (m, 1H), 2.11-2.05 (m, 1H), 1.76-1.68 (m, 1H), 1.63-1.36 (m, 9H); LC-MS (ESI$^+$) m/z 303.1 (M+H)$^+$.

2-(2,6-Dioxo-3-piperidyl)-4-[[7-(methylamino)spiro [3.5]nonan-2-yl]amino]isoindoline-1,3-dione (Intermediate AXB)

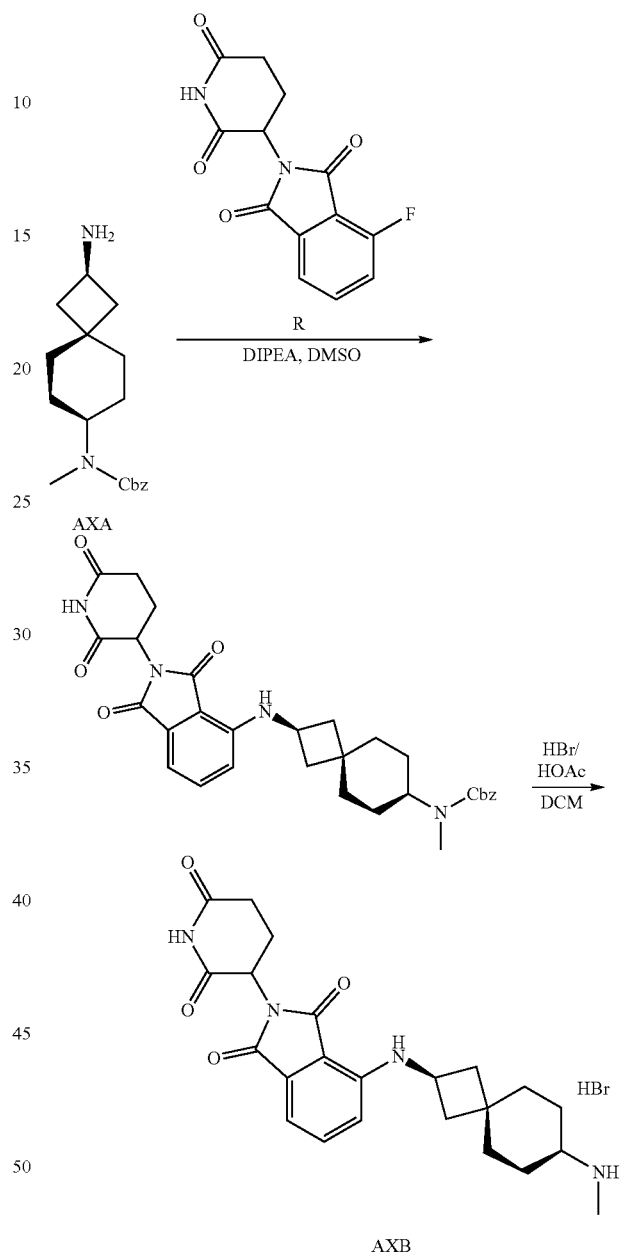

Step 1—Benzyl N-[2-[[2-(2,6-di oxo-3-piperidyl)-1, 3-dioxo-isoindolin-4-yl]amino] spiro[3.5]nonan-7-yl]-N-methyl-carbamate To a solution of benzyl N-(2-aminospiro[3.5]nonan-7-yl)-N-methyl-carbamate (70.0 mg, 231 umol, Intermediate AXA) and 2-(2,6-dioxo-3-piperidyl)-4-fluoro-isoindoline-1, 3-dione (83.1 mg, 300 umol, Intermediate R) in DMSO (2 mL) was added DIPEA (89.7 mg, 694 umol). The mixture was stirred at 130° C. for 3 hrs. On completion, the reaction mixture was diluted with water (8 mL) and extracted with EA (3×10 mL). The combined organic layers were dried over Na₂SO₄, filtered and concentrated in vacuo to give a residue. The residue was purified by reverse phase (FA condition) to give the title compound (65.0 mg, 50% yield) as yellow solid. ¹H NMR (400 MHz, CDCl₃) δ 8.14 (s, 1H), 7.48 (dd, J=7.2, 8.4 Hz, 1H), 7.43-7.28 (m, 5H), 7.11 (d, J=7.2 Hz, 1H), 6.74 (d, J=8.4 Hz, 1H), 6.30 (d, J=5.6 Hz, 1H), 5.14 (s, 2H), 4.98-4.88 (m, 1H), 4.11-3.78 (m, 2H), 2.95-2.68 (m, 6H), 2.46 (t, J=7.6 Hz, 1H), 2.32-2.27 (m, 1H), 2.19-2.10 (m, 1H), 1.90-1.82 (m, 1H), 1.79-1.65 (m, 4H), 1.59-1.39 (m, 5H); LC-MS (ESI⁺) m/z 559.2 (M+H)⁺.

Step 2—2-(2,6-Dioxo-3-piperidyl)-4-[[7-(methylamino)spiro[3.5]nonan-2-yl]amino]isoindoline-1,3-dione To a solution of benzyl N-[2-[[2-(2,6-dioxo-3-piperidyl)-1,3-dioxo-isoindolin-4-yl]amino]spiro[3.5] nonan-7-yl]-N-methyl-carbamate (60.0 mg, 107 umol) in DCM (2 mL) was added HBr/HOAc (107 umol, 1 mL, 33% solution). The mixture was stirred at 25° C. for 2 hrs. On completion, the mixture was concentrated under N₂ flow to give the title compound (50.0 mg, 90% yield, HBr salt) as yellow solid. LC-MS (ESI⁺) m/z 425.2 (M+H)⁺.

N-[2-(4-formylphenyl)-6-(1-hydroxy-1-methylethyl)indazol-5-yl]-6-(trifluoromethyl)pyridine-2-carboxamide (Intermediate CBW)

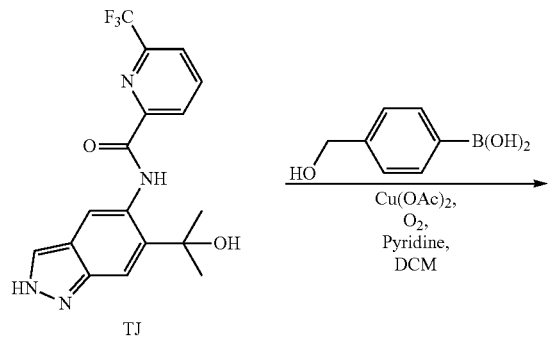

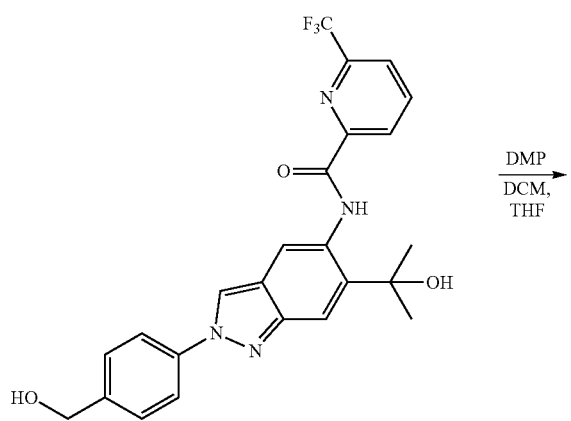

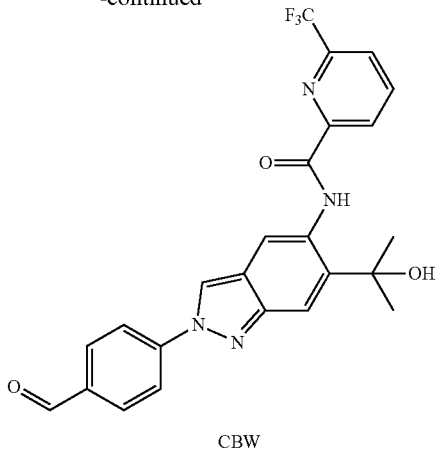

Step 1—N-[6-(1-hydroxy-1-methyl-ethyl)-2-[4-(hydroxymethyl)phenyl]indazol-5-yl]-6-(trifluoromethyl)pyridine-2-carboxamide To a solution of N-[6-(1-hydroxy-1-methyl-ethyl)-2H-indazol-5-yl]-6-(rifluoromethyl)pyridine-2-carboxamide (300 mg, 824 umol, Intermediate TJ) and [4-(hydroxymethyl)phenyl]boronic acid (150 mg, 988 umol CAS #59016-93-2) in DCM (10 mL) was added Cu(OAc)₂ (179 mg, 988 umol) and pyridine (390 mg, 4.94 mmol). The mixture was stirred at 25° C. for 72 hours under 02 atmosphere. On completion, the mixture was filtered and washed with DCM (3×10 mL). The filtrate was adjust pH=5 with HCl (2 mL, 1 mol/L), washed with H₂O (3×10 mL) then washed with brine (3×10 mL), dried with anhydrous Na₂SO₄, filtered and the filtrate was concentrated in vacuo. The residue was purified by column chromatography (SiO₂, Petroleum ether/Ethyl acetate=100/1 to 1/1) to give the title compound (47.0 mg, 99.9 umol, 12% yield) as a yellow solid. ¹H NMR (400 MHz, DMSO-d₆) δ 12.46 (s, 1H), 9.06 (s, 1H), 8.83 (s, 1H), 8.47 (d, J=7.6 Hz, 1H), 8.38 (t, J=7.6 Hz, 1H), 8.17 (d, J=7.2 Hz, 1H), 8.03 (d, J=8.4 Hz, 2H), 7.70 (s, 1H), 7.52 (d, J=8.4 Hz, 2H), 6.05 (s, 1H), 5.32 (t, J=5.6 Hz, 1H), 4.58 (d, J=5.6 Hz, 2H), 1.66 (s, 6H). LC-MS (ESI⁺) m/z 471.3 (M+H)⁺.

Step 2—N-[2-(4-formylphenyl)-6-(1-hydroxy-1-methyl-ethyl)indazol-5-yl]-6-(trifluoromethyl)pyridine-2-carboxamide To a solution of N-[6-(1-hydroxy-1-methyl-ethyl)-2-[4-(hydroxymethyl)phenyl]indazol-5-yl]-6-(trifluoromethyl)pyridine-2-carboxamide (57.0 mg, 121 umol) in DCM (1 mL) and THF (1 mL) was added DMP (77.1 mg, 181 umol, 56.2 uL). The mixture was then stirred at 25° C. for 1 hour. On completion, the mixture was diluted with DCM (5 mL), and quenched with Na₂S₂O₃ (10 mL) and NaHCO₃ (10 mL). The combined organic layer was washed with brine (3×10 mL), then dried with anhydrous Na₂SO₄, filtered and the filtrate was concentrated in vacuo. The crude product was purified by pre-HPLC (column: Phenomenex luna C18 150*25 mm*10 um; mobile phase: [water(FA)-ACN]; B %: 47%-77%, 9 min) to give the title compound (10 mg, 18% yield) as a yellow solid. ¹H NMR (400 MHz, DMSO-d₆) δ 12.49 (s, 1H), 10.08 (s, 1H), 9.24 (s, 1H), 8.85 (s, 1H), 8.47 (d, J=7.6 Hz, 1H), 8.38 (s, 1H), 8.35 (s, 1H), 8.33 (s, 1H), 8.18 (d, J=7.6 Hz, 1H), 8.13 (d, J=8.6 Hz, 2H), 6.09 (s, 1H), 2.35-2.31 (m, 1H), 1.66 (s, 6H), LC-MS(ESI$^+$) m/z 469.0 (M+H)$^+$.

3-[5-methoxy-3-methyl-2-oxo-4-(1,2,3,6-tetrahydropyridin-4-yl)benzimidazol-1-yl]piperidine-2,6-dione (Intermediate CBX)

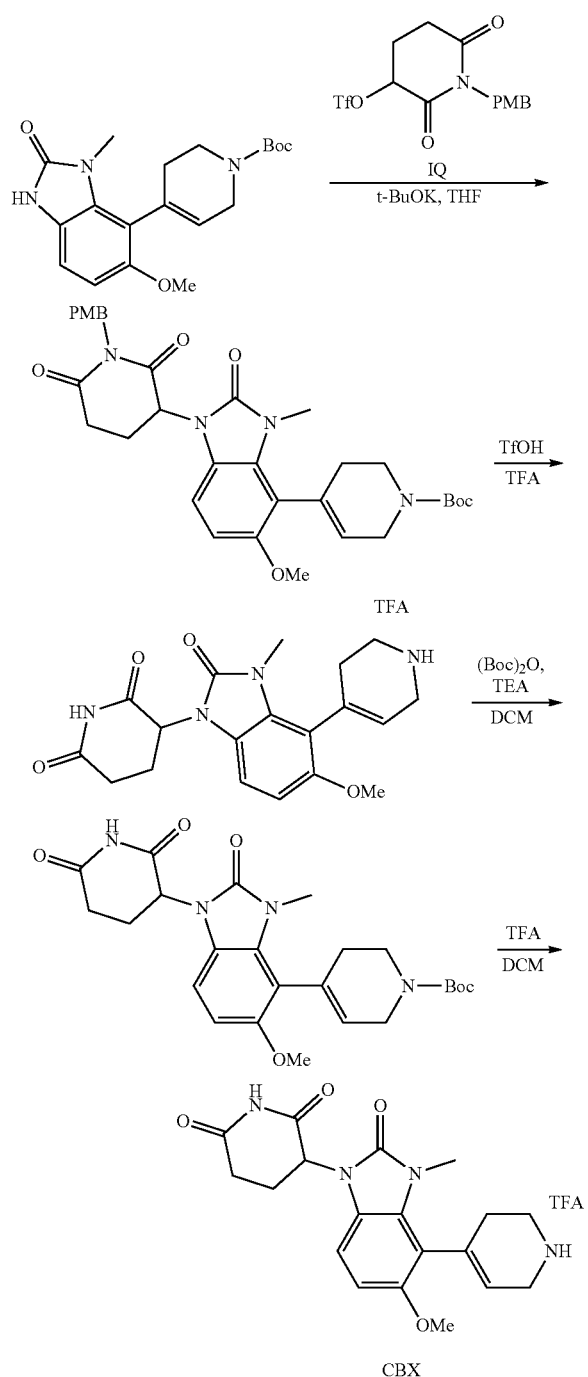

Step 1—Tert-butyl 4-[5-methoxy-1-[1-[(4-methoxyphenyl)methyl]-2,6-dioxo-3-piperidyl]-3-methyl-2-oxo-benzimidazol-4-yl]-3,6-dihydro-2H-pyridine-1-carboxylate To a solution of tert-butyl 4-(5-methoxy-3-methyl-2-oxo-1H-benzimidazol-4-yl)-3,6-dihydro-2H-pyridine-1-carboxylate (500 mg, 1.39 mmol, synthesized via Step 1 of Intermediate BUC) in THF (10 mL) was added t-BuOK (234 mg, 2.09 mmol) at 0° C. The mixture was stirred at 0° C. for 0.5 hr. Then, to the above mixture was added [1[(4-methoxyphenyl)methyl]-2,6-dioxo-3-piperidyl]trifluoromethanesulfonate (795 mg, 2.09 mmol, Intermediate IQ) in THF (4 mL). The mixture was stirred at 0° C. for 3.5 hrs. On completion, the reaction was quenched with NH$_4$Cl solution (5 mL), and extracted with EA (100×2 mL). The organic layer was washed with water (100 mL×3), dried over Na$_2$SO$_4$ and filtered. The filtrate was concentrated in vacuo. The residue was purified by column chromatography (SiO$_2$, Petroleum ether/Ethyl acetate=3/2 to 1/2) to give the title compound (750 mg, 91% yield) as blue solid. $^1$H NMR (400 MHz, DMSO-d$_6$) δ=7.21 (d, J=8.4 Hz, 2H), 6.86 (d, J=8.4 Hz, 3H), 6.64 (dd, J=3.6, 8.4 Hz, 1H), 5.62 (s, 1H), 5.49 (dd, J=5.2, 13.2 Hz, 1H), 4.91-4.70 (m, 2H), 4.02-3.89 (m, 2H), 3.72 (s, 3H), 3.71 (s, 3H), 3.62-3.46 (m, 2H), 3.26 (s, 3H), 3.10-2.99 (m, 1H), 2.86-2.64 (m, 2H), 2.43 (s, 1H), 2.24-2.13 (m, 1H), 2.08-2.00 (m, 1H), 1.44 (s, 9H).

Step 2—3-[5-methoxy-3-methyl-2-oxo-4-(1,2,3,6-tetrahydropyridin-4-yl)benzimidazol-1-yl]piperidine-2,6-dione A mixture of tert-butyl 4-[5-methoxy-1-[1-[(4-methoxyphenyl)methyl]-2,6-dioxo-3-piperidyl]-3-methyl-2-oxo-benzimidazol-4-yl]-3,6-dihydro-2H-pyridine-1-carboxylate (100 mg, 169 umol) and TfOH (340 mg, 2.27 mmol) in TFA (1 mL) was stirred at 70° C. for 1 hr. On completion, the reaction was concentrated in vacuo to give the title compound (82.0 mg, 99% yield, TFA) as brown oil. LC-MS (ESI$^+$) m/z 371.1 (M+H)$^+$.

Step 3—Tert-butyl 4-[1-(2,6-dioxo-3-piperidyl)-5-methoxy-3-methyl-2-oxo-benzimidazol-4-yl]-3,6-dihydro-2H-pyridine-1-carboxylate To a mixture of 3-[5-methoxy-3-methyl-2-oxo-4-(1,2,3,6-tetrahydropyridin-4-yl)benzimidazol-1-yl]piperidine-2,6-dione (82.0 mg, 169 umol, TFA) and TEA (51.3 mg, 507 umol) in DCM (2 mL) was added Boc$_2$O (55.4 mg, 253 umol). The mixture was then stirred at 25° C. for 16 hrs. On completion, the reaction was diluted with DCM (50 mL). The organic layer was washed with water (50 mL×3), dried over Na$_2$SO$_4$ and filtered. The filtrate was concentrated in vacuo. The residue was purified by prep-HPLC (column: Phenomenex luna C18 150*25 mm*10 um; mobile phase: [water (FA)-ACN]; B %: 33%-63%, 10 min) to give the title compound (40.0 mg, 50% yield) as white solid. $^1$H NMR (400 MHz, DMSO-d$_6$) δ 11.09 (s, 1H), 6.98 (dd, J=1.6, 8.4 Hz, 1H), 6.70 (d, J=8.4 Hz, 1H), 5.64 (s, 1H), 5.34 (dd, J=5.2, 12.4 Hz, 1H), 4.08-3.91 (m, 2H), 3.72 (s, 3H), 3.65-3.47 (m, 2H), 3.27 (s, 3H), 2.96-2.83 (m, 1H), 2.76-2.62 (m, 2H), 2.45 (d, J=8.0 Hz, 1H), 2.26-2.13 (m, 1H), 2.05-1.94 (m, 1H), 1.44 (s, 9H).

Step 4—3-[5-methoxy-3-methyl-2-oxo-4-(1,2,3,6-tetrahydropyridin-4-yl)benzimidazol-1-yl]piperidine-2,6-dione A mixture of tert-butyl 4-[1-(2,6-dioxo-3-piperidyl)-5-methoxy-3-methyl-2-oxo-benzimidazol-4-yl]-3,6-dihydro- 2H-pyridine-1-carboxylate (40.0 mg, 85.0 umol) and TFA (308 mg, 2.70 mmol) in DCM (1 mL) was stirred at 25° C. for 1 hr. On completion, the reaction was concentrated in vacuo to give the title compound (41.0 mg, 99% yield, TFA) as yellow oil. LC-MS (ESI$^+$) m/z 371.2 (M+H)$^+$.

5-[tert-butyl(diphenyl)silyl]oxypentylmethane-sulfonate (Intermediate CBY)

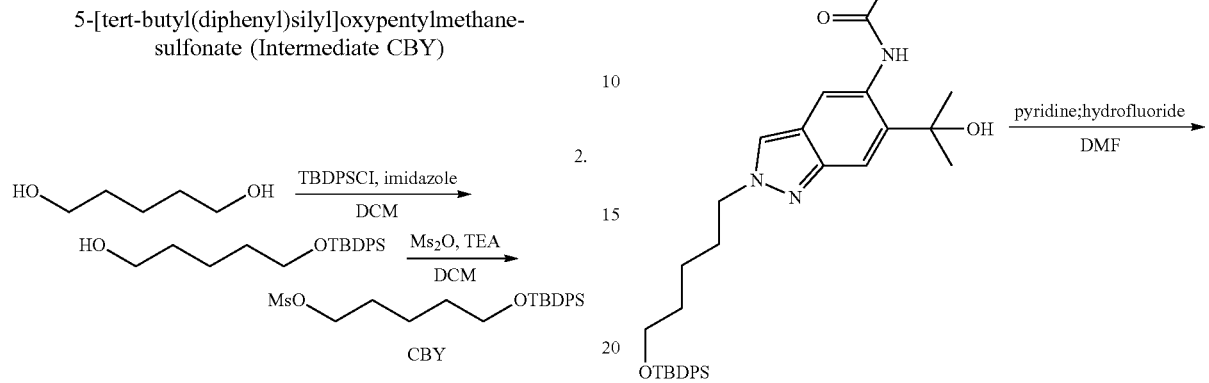

Step 1—5-[tert-butyl(diphenyl)silyl]oxypentan-1-ol

To a solution of pentane-1,5-diol (2 g, 19.2 mmol, 2.02 mL, from CAS #111-29-5) in DCM (20 mL) was added imidazole (522 mg, 7.68 mmol) and TBDPSCl (1.06 g, 3.84 mmol, 986 uL) at 0° C. The mixture was then stirred at 25° C. for 3 hours. On completion, the reaction mixture was concentrated under reduced pressure to give the title compound (1.20 g, 91% yield) as colorless oil.

Step 2—5-[tert-butyl(diphenyl)silyl]oxypentyl methanesulfonate

To a solution of 5-[tert-butyl(diphenyl)silyl]oxypentan-1-ol (300 mg, 875 umol) in DCM (3 mL) was added TEA (177 mg, 1.75 mmol, 243 uL) and methylsulfonyl methane-sulfonate (228 mg, 1.31 mmol). The mixture was then stirred at 25° C. for 2 hours. On completion, the reaction mixture was concentrated under reduced pressure to give the title compound (210 mg, 57% yield) as colorless oil. LC-MS (ESI$^+$) m/z 421.2 (M+H)$^+$.

N-[6-(1-hydroxy-1-methyl-ethyl)-2-(5-oxopentyl) indazol-5-yl]-6-(trifluoromethyl)pyridine-2-carbox-amide (Intermediate CBZ)

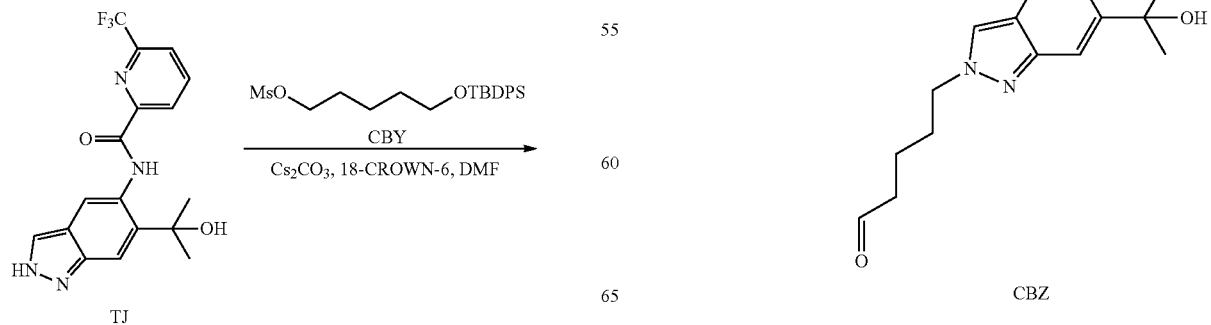

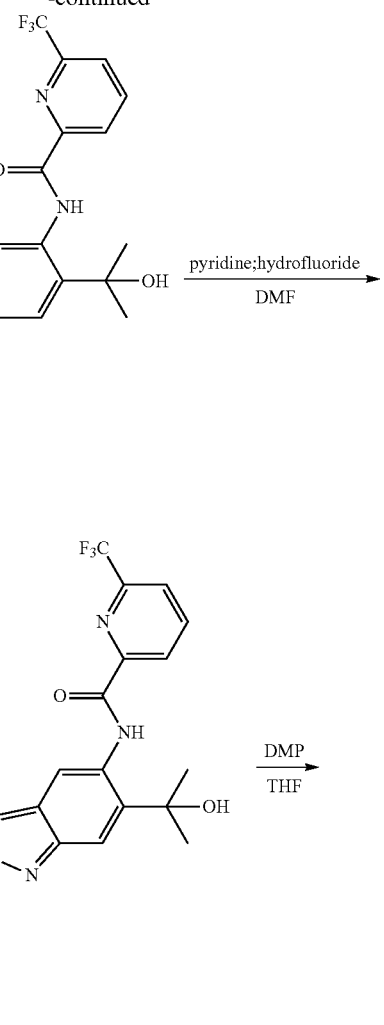

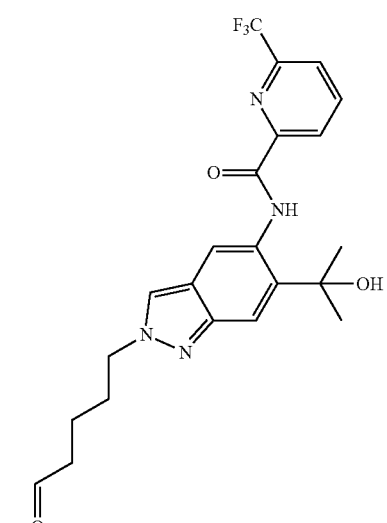

Step 1—N-[2-[5-[tert-butyl (diphenyl)silyl]oxypentyl]-6-(1-hydroxy-1-methyl-ethyl)indazol-yl]-6-(trifluoromethyl)pyridine-2-carboxamide To a solution of 5-[tert-butyl(diphenyl)silyl]oxypentyl methanesulfonate (200 mg, 475 umol, Intermediate CBY) in DMF (3 mL) was added N-[6-(1-hydroxy-1-methyl-ethyl)-2H-indazol-5-yl]-6-(trifluoromethyl)pyridine-2-carboxamide (86.6 mg, 237 umol, Intermediate TJ), $Cs_2CO_3$ (232 mg, 713 umol) and 18-CROWN-6 (12.5 mg, 47.5 umol). The mixture was stirred at 80° C. for 17 hours. On completion, the reaction mixture concentrated under reduced pressure to give the title compound (115 mg, 70% yield) as white solid. LC-MS (ESI$^+$) m/z 689.3 (M+H)$^+$.

Step 2—N-[6-(1-hydroxy-1-methyl-ethyl)-2-(5-hydroxypentyl)indazol-5-yl]-6-(trifluoromethyl) pyridine-2-carboxamide To a solution of N-[2-[5-[tert-butyl(diphenyl)silyl]oxypentyl]-6-(1-hydroxy-1-methyl-ethyl)indazol-5-yl]-6-(trifluoromethyl)pyridine-2-carboxamide (300 mg, 435 umol) in DMF (3 mL) was added pyridine; hydrofluoride (43.1 mg, 435 umol, 39.2 uL). The mixture was stirred at 25° C. for 2 hours. On completion, the reaction mixture was concentrated under reduced pressure to give a residue. The residue was purified by prep-HPLC (column: Phenomenex Luna C18 150*25 mm*10 um; mobile phase: [water(FA)-ACN]; B %: 33%-63%, 9 min) to give the title compound (37 mg, 19% yield) as colorless oil. LC-MS (ESI$^+$) m/z 451.4 (M+H)$^+$. $^1$H NMR (400 MHz, CDCl$_3$) δ 12.28 (s, 1H), 8.87 (s, 1H), 8.51 (d, J=8.0 Hz, 1H), 8.11 (t, J=8.0 Hz, 1H), 7.89 (s, 1H), 7.85 (d, J=7.6 Hz, 1H), 7.74 (s, 1H), 4.43 (t, J=7.2 Hz, 2H), 3.65 (t, J=6.4 Hz, 2H), 2.37-2.16 (m, 1H), 2.10-2.02 (m, 2H), 1.81 (s, 7H), 1.64 (d, J=7.2 Hz, 2H), 1.47-1.39 (m, 2H).

Step 3—N-[6-(1-hydroxy-1-methyl-ethyl)-2-(5-oxopentyl)indazol-5-yl]-6-(trifluoromethyl)pyridine-2-carboxamide To a solution of N-[6-(1-hydroxy-1-methyl-ethyl)-2-(5-hydroxypentyl)indazol-5-yl]-6-(trifluoromethyl)pyridine-2-carboxamide (30 mg, 66.6 umol) in THF (2 mL) was added DMP (48.0 mg, 113 umol, 35.0 uL) at 0° C. The mixture was then stirred at 25° C. for 32 hours. On completion, the reaction mixture concentrated under reduced pressure to give the title compound (29.0 mg, 97% yield) as white oil. LC-MS (ESI$^+$) m/z 449.0 (M+H)$^+$.

2-Benzyl N-methyl-N-[3-[3-(methylamino)cyclobutoxy]propyl]carbamate (Intermediate CCA)

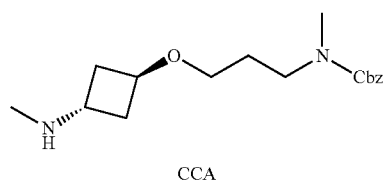

CCA

Step 1—Tert-butyl N-[3-[3-[benzyloxycarbonyl(methyl)amino]propoxy]cyclobutyl]-N-methyl-carbamate To a solution of benzyl N-[3-[3-(tert-butoxycarbonylamino)cyclobutoxy]propyl]-N-methyl-carbamate (1 g, 2.55 mmol, synthesized via Steps 1-5 of Intermediate AOY) in THF (10 mL) was added NaH (305 mg, 7.65 mmol, 60% dispersion in mineral oil) at 0° C. for 30 minutes. Then CH$_3$I (1.08 g, 7.65 mmol) was added into the solution and the mixture was stirred at 25° C. for 5.5 hours. On completion, the mixture was quenched with H$_2$O (10 mL), diluted with H$_2$O (20 mL), and extracted with EA (30 mL×3). The combined organic layer was washed with brine (30 mL×3), dried with anhydrous Na$_2$SO$_4$, filtered and concentrated in vacuo to give the title compound (1.00 g, 96% yield) as a yellow oil. $^1$H NMR (400 MHz, CDCl$_3$) δ 7.40-7.28 (m, 5H), 5.14 (s, 2H), 4.83-4.60 (m, 1H), 4.00-3.86 (m, 1H), 3.42-3.35 (m, 2H), 2.95 (s, 3H), 2.81 (s, 3H), 2.66-2.56 (m, 2H), 2.33-2.19 (m, 4H), 1.88-1.75 (m, 2H), 1.46 (s, 9H).

Step 2—2-Benzyl N-methyl-N-[3-[3-(methylamino)cyclobutoxy]propyl]carbamate

To a solution of tert-butyl N-[3-[3-[benzyloxycarbonyl(methyl)amino]propoxy]cyclobutyl]-N-methyl-carbamate (400 mg, 983 umol) in DCM (8 mL) was added HCl/dioxane (4 M, 4 mL). The mixture was then stirred at 25° C. for 2 hours. On completion, the mixture was concentrated in vacuo to give the title compound (337 mg, 99% yield, HCl) as a yellow oil. LC-MS (ESI$^+$) m/z 307.0 (M+H)$^+$.

2-(2,6-Dioxo-3-piperidyl)-4-[methyl-[3-[3-(methylamino)propoxy]cyclobutyl]amino]isoindoline-1,3-dione (Intermediate CCB)

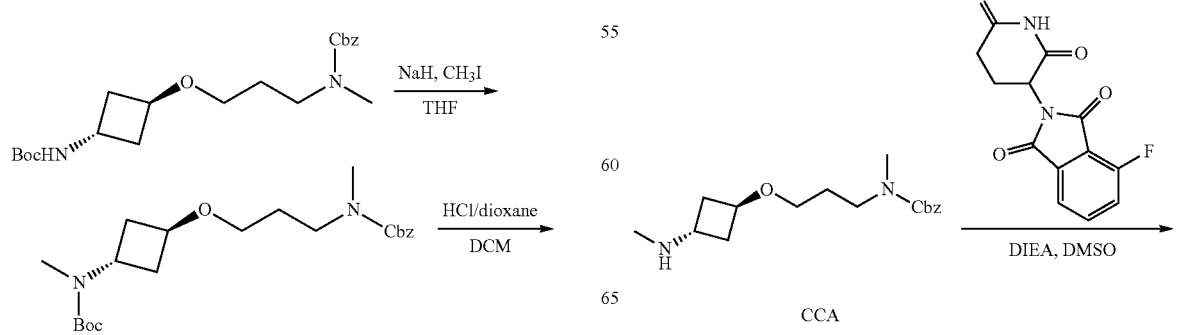

-continued

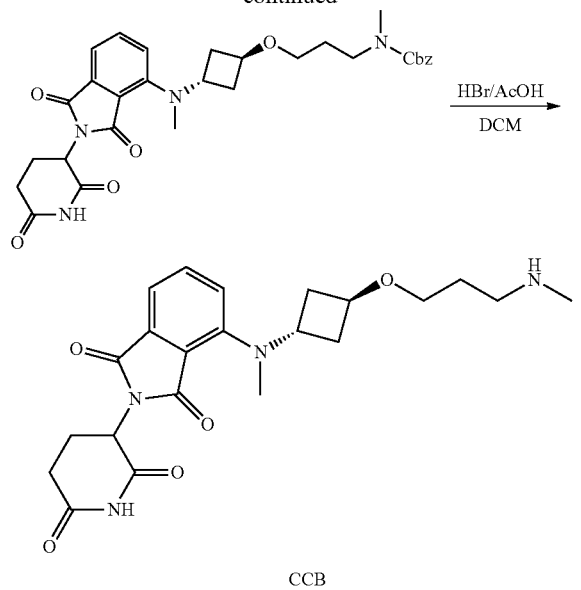

CCB

Step 1—3-Benzyl N-[3-[3-[[2-(2,6-dioxo-3-piperidyl)-1,3-dioxo-isoindolin-4-yl]-methyl-amino]cyclobutoxy]propyl]-N-methyl-carbamate To a solution of benzyl N-methyl-N-[3-[3-(methylamino)cyclobutoxy]propyl]carbamate (337 mg, 982 umol, HCl, Intermediate CCA) and 2-(2,6-dioxo-3-piperidyl)-4-fluoro-isoindoline-1,3-dione (226 mg, 819 umol, CAS #835616-60-9) in DMSO (5 mL) was added DIEA (529 mg, 4.10 mmol). The mixture was then stirred at 130° C. for 5 hours. On completion, the mixture was diluted with H$_2$O (20 mL), and extracted with EA (20 mL×3). The combined organic layer was washed with brine (50 mL×3), dried with anhydrous Na$_2$SO$_4$, filtered and concentrated in vacuo. The residue was purified by prep-HPLC (column: Phenomenex Luna C 18 200*40 mm*10 um; mobile phase: [water (FA)-ACN]; B %: 43%-73%, 10 minutes) to give the title compound (206 mg, 44% yield) as a yellow solid. $^1$H NMR (400 MHz, DMSO-d$_6$) δ 11.07 (s, 1H), 7.62 (t, J=7.2 Hz, 1H), 7.40-7.26 (m, 6H), 7.16-7.05 (m, 1H), 5.13-5.07 (m, 1H), 5.05 (s, 2H), 4.32-4.15 (m, 1H), 3.98-3.85 (m, 1H), 3.29-3.22 (m, 3H), 2.93 (s, 3H), 2.89-2.82 (m, 4H), 2.71-2.58 (m, 4H), 2.30-2.20 (m, 4H), 1.76-1.68 (m, 2H). LC-MS (ESI$^+$) m/z 563.4 (M+H)$^+$.

Step 2—2-(2,6-Dioxo-3-piperidyl)-4-[methyl-[3-[3-(methylamino)propoxy]cyclobutyl]amino]isoindoline-1,3-dione To a solution of benzyl N-[3-[3-[[2-(2,6-dioxo-3-piperidyl)-1,3-dioxo-isoindolin-4-yl]-methyl-amino] cyclobutoxy]propyl]-N-methyl-carbamate (100 mg, 177 umol) in DCM (5 mL) was added hydrogen bromide (2.88 g, 10.6 mmol, 30% solution). The mixture was then stirred at 25° C. for 1 hour. On completion, the mixture was dried with N$_2$, then washed with DCM (4 mL×3) and concentrated in vacuo to give the title compound (90.0 mg, 99% yield, HBr) as a yellow solid. LC-MS (ESI$^+$) m/z 429.0 (M+H)$^+$.

2-(2,6-Dioxo-3-piperidyl)-5-[[3-[3-(methylamino)propoxy]cyclobutyl]amino]isoindoline -1,3-dione (Intermediate CCC)

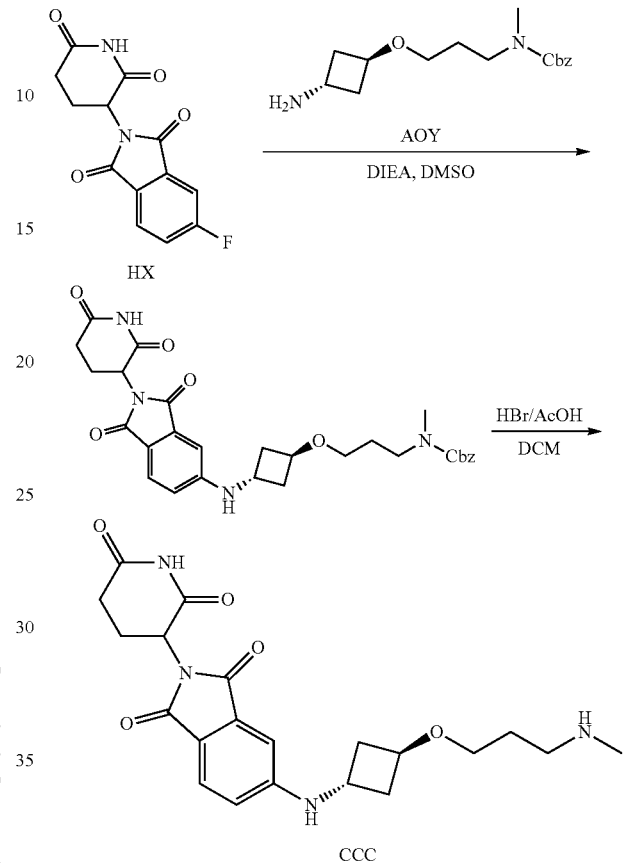

CCC

Step 1—Benzyl N-[3-[3-[[2-(2,6-dioxo-3-piperidyl)-1,3-dioxo-isoindolin-5-yl]amino]cyclobutoxy]propyl]-N-methyl-carbamate To a solution of benzyl N-[3-(3-aminocyclobutoxy)propyl]-N-methyl-carbamate (190 mg, 577 umol, HCl, Intermediate AOY) and 2-(2,6-dioxo-3-piperidyl)-5-fluoro-isoindoline-1,3-dione (133 mg, 481 umol, Intermediate HX) in DMSO (2 mL) was added DIEA (311 mg, 2.41 mmol, 419 uL). The mixture was then stirred at 130° C. for 3 hours. On completion, the mixture was diluted with H$_2$O (3 mL) and extracted with EA (3×5 mL). The combined organic layer was washed with brine (3×5 mL), dried with anhydrous Na$_2$SO$_4$, then filtered and the filtrate was concentrated in vacuo. The mixture was purified by pre-HPLC (column: Phenomenex Luna C18 200*40 mm*10 um; mobile phase: [water(FA)-ACN]; B %: 38%-68%, 10 min) to give the title compound (35 mg, 13% yield) as a brown solid. LC-MS (ESI$^+$) m/z 549.3 (M+H)$^+$.

Step 2—2-(2,6-Dioxo-3-piperidyl)-5-[[3-[3-(methylamino)propoxy] cyclobutyl]amino]isoindoline-1,3-dione To a solution of benzyl N-[3-[3-[[2-(2,6-dioxo-3-piperidyl)-1,3-dioxo-isoindolin-5-yl]amino] cyclobutoxy]propyl]-N-methyl-carbamate (75.0 mg, 136 umol) in DCM (3 mL) was added HBr/AcOH (2.21 g, 8.20 mmol, 1.48 mL, 30% solution). The mixture was then stirred at 25° C. for 1 hour. On completion the mixture was dried with N₂, then washed with DCM (3×4 mL) and concentrated in vacuo. The mixture was without purification to give the title compound (35 mg, 63.8umol, 13% yield) as a brown solid. LC-MS (ESI⁺) m/z 415.2 (M+H)⁺.

Benzyl N-[2-(3-aminocyclobutoxy)ethyl]-N-methyl-carbamate (Intermediate CCD)

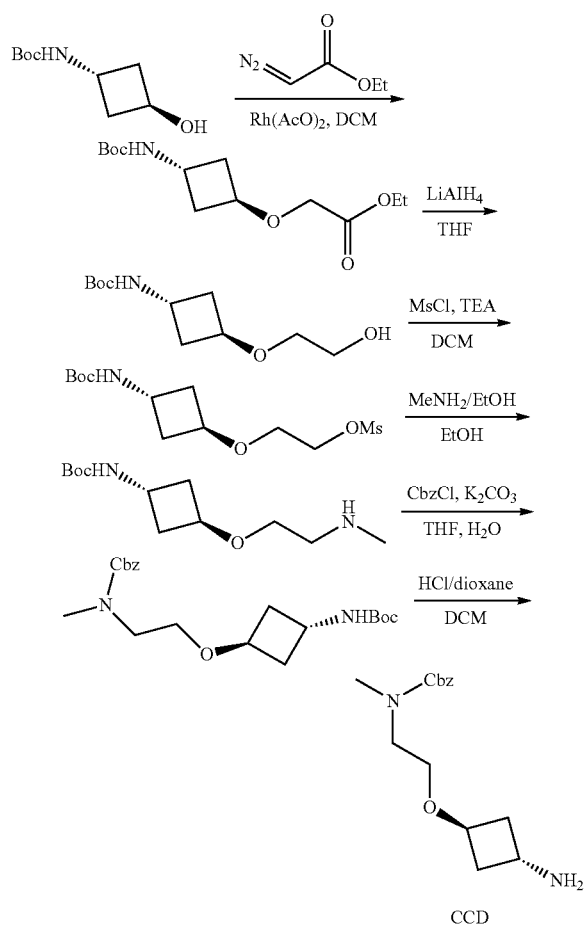

Step 1—Ethyl 2-[3-(tert-butoxycarbonylamino)cyclobutoxy]acetate

To a solution of tert-butyl N-(3-hydroxycyclobutyl)carbamate (2.5 g, 13.3 mmol) in DCM (80 mL) was added Rh(AcO)₂ (295 mg, 667 umol, CAS #15956-28-2) and ethyl 2-diazoacetate (4.57 g, 40 mmol, CAS #623-73-4). The mixture was then stirred at 25° C. for 16 hours. On completion, the mixture was washed with H₂O (3×100 mL), then washed with brine, and the organic layer was dried with anhydrous Na₂SO₄, filtered and the filtrate was concentrated in vacuo. The residue was purified by column chouromatography (SiO₂, Petroleum ether/Ethyl acetate=100/1 to 5/1) (Rf=0.51, PE:EA=2:1) to give the title compound (0.93 g, 3.40 mmol, 25% yield) as a white solid. ¹H NMR (400 MHz, DMSO-d₆) δ 7.15 (d, J=6.8 Hz, 1H), 4.10 (q, J=7.2 Hz, 3H), 4.01-3.91 (m, 3H), 2.24-2.13 (m, 2H), 2.11-2.01 (m, 2H), 1.36 (s, 9H), 1.19 (t, J=7.2 Hz, 3H).

Step 2—Tert-butyl N-[3-(2-hydroxyethoxy)cyclobutyl]carbamate

To a solution of ethyl 2-[3-(tert-butoxycarbonylamino)cyclobutoxy]acetate (1.86 g, 6.81 mmol) in THF (20 mL) was added LiAlH₄ (387 mg, 10.2 mmol). The mixture was stirred at 0° C. for 2 hours under N₂, The mixture was quenched with H₂O (0.4 mL) and NaOH (0.4 mL, 10% solution), dried with anhydrous Na₂SO₄ then filtered and the filtrate was concentrated in vacuo to give the title compound (1.28 g, 81% yield) as a white solid. ¹H NMR (400 MHz, DMSO-d₆) δ 7.15 (d, J=6.8 Hz, 1H), 4.57 (t, J=5.2 Hz, 1H), 4.04-3.90 (m, 2H), 3.46 (q, J=5.2 Hz, 2H), 3.29-3.24 (m, 2H), 2.14-2.02 (m, 4H), 1.37 (s, 9H).

Step 3—2-[3-(Tert-butoxycarbonylamino)cyclobutoxy] ethyl methanesulfonate

To a solution of tert-butyl N-[3-(2-hydroxyethoxy)cyclobutyl]carbamate (200 mg, 864 umol) in DCM (8 mL) was added TEA (262 mg, 2.59 mmol, 361 uL) and methylsulfonyl methanesulfonate (301.26 mg, 1.73 mmol, CAS #7143-01-3). The mixture was stirred at 25° C. for 2 hours. On completion, the mixture was washed with H₂O (3×10 mL), then washed with brine (3×10 mL), dried with anhydrous Na₂SO₄, filtered and the filtrate was concentrated in vacuo to give the title compound (236 mg, 88% yield) as a white solid. ¹H NMR (400 MHz, DMSO-d₆) δ 7.17 (d, J=6.8 Hz, 1H), 4.30-4.27 (m, 2H), 4.10-4.02 (m, 1H), 4.00-3.93 (m, 1H), 3.54-3.49 (m, 2H), 3.18 (s, 3H), 2.18 (d, J=3.6 Hz, 1H), 2.13 (td, J=8.0, 4.0 Hz, 2H), 2.09 (d, J=6.0 Hz, 1H), 1.37 (s, 9H).

Step 4—Tert-butyl N-[3-[2-(methylamino)ethoxy] cyclobutyl]carbamate

To a solution of 2-[3-(tert-butoxycarbonylamino)cyclobutoxy]ethyl methanesulfonate (236 mg, 762 umol) in EtOH (5 mL) was added MeNH₂ (1.61 g, 15.5 mmol, 2 mL, 30% solution). The mixture was stirred at 80° C. for 16 hrs. On completion, the mixture was concentrated in vacuo to give the title compound (186 mg, 99% yield) as a brown liquid. ¹H NMR (400 MHz, CDCl₃) δ 4.70 (s, 1H), 4.43-4.32 (m, 2H), 4.14 (dt, J=7.2, 3.2 Hz, 2H), 3.63-3.54 (m, 2H), 3.07 (s, 3H), 2.42-2.33 (m, 2H), 2.15 (td, J=12.4, 6.4 Hz, 2H), 1.65-1.57 (m, 1H), 1.44 (s, 9H).

Step 5—Benzyl N-[2-[3-(tert-butoxycarbonylamino) cyclobutoxy]ethyl]-N-methyl-carbamate To a solution of tert-butyl N-[3-[2-(methylamino)ethoxy] cyclobutyl]carbamate (186 mg, 761 umol) in THF (10 mL) and H₂O (3 mL) was added K₂CO₃ (210 mg, 1.52 mmol) and CbzCl (194 mg, 1.14 mmol, 162 uL, CAS #501-53-1). The mixture was stirred at 25° C. for 16 hours. On completion, the mixture was diluted with H₂O (5 mL), and extracted with EA (3×20 mL). The combined organic layer was washed with brine (3×20 mL), dried with anhydrous Na₂SO₄, then filtered and the filtrate was concentrated in vacuo. The residue was purified by column chromatography (SiO₂, Petroleum ether/Ethyl acetate=100/1 to 5/1) (Rf=0.35, PE:EA=2:1) to give the title compound (1.50 g, 396% yield) as a colorless oily liquid ¹H NMR (400 MHz, CDCl₃) δ 7.27 (d, J=3.6 Hz, 5H), 7.18 (d, J=1.2 Hz, 1H), 5.05 (s, 2H), 4.65-4.50 (m, 1H), 3.99-3.91 (m, 1H), 3.37 (s, 4H), 2.91 (s, 3H), 2.22 (td, J=4.0, 1.6 Hz, 2H), 1.99 (s, 2H), 1.36 (s, 9H). LC-MS (ESI+) m/z 379.1 (M+H)+.

Step 6—Benzyl N-[2-(3-aminocyclobutoxy)ethyl]-N-methyl-carbamate

To a solution of benzyl N-[2-[3-(tert-butoxycarbonylamino)cyclobutoxy]ethyl]-N-methyl-carbamate (500 mg, 1.32 mmol) in DCM (10 mL) was added HCl/dioxane (4 M, 5 mL). The mixture was stirred at 25° C. for 1 hour. On completion, the mixture was concentrated in vacuo to give the title compound (367 mg, 88% yield, HCl) as a colorless oily liquid. $^1$H NMR (400 MHz, DMSO-d$_6$) δ 7.15 (d, J=6.8 Hz, 1H), 4.57 (t, J=5.4 Hz, 1H), 4.07-3.84 (m, 2H), 3.65-3.56 (m, 1H), 3.46 (q, J=5.2 Hz, 2H), 3.30-3.21 (m, 2H), 2.20-1.95 (m, 4H), 1.37 (s, 9H). LC-MS (ESI+) m/z 279.1 (M+H)+.

2-(2,6-Dioxo-3-piperidyl)-4-[[3-[2-(methylamino)ethoxy] cyclobutyl]amino]isoindoline-1,3-dione (Intermediate CCE)

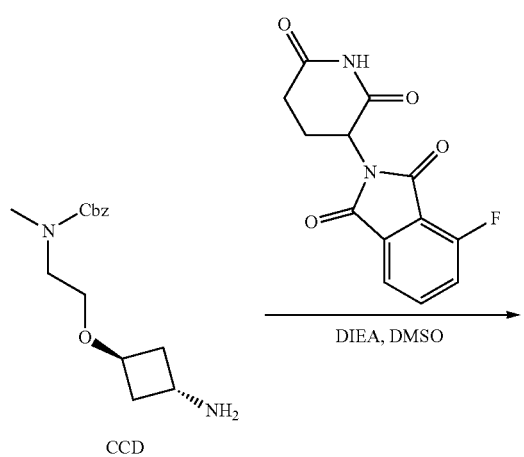

CCD

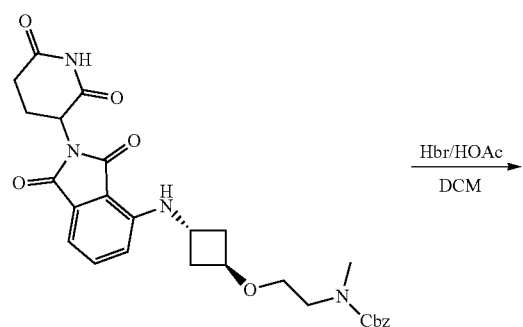

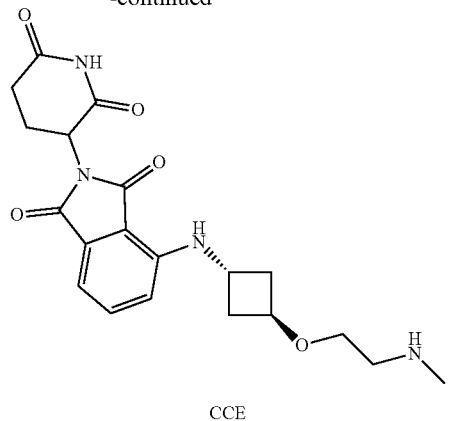

CCE

Step 1—Benzyl N-[2-[3-[[2-(2,6-dioxo-3-piperidyl)-1,3-dioxo-isoindolin-4-yl]amino]cyclobutoxy]ethyl]-N-methyl-carbamate To a solution of benzyl N-[2-(3-aminocyclobutoxy) ethyl]-N-methyl-carbamate (230 mg, 732 umol, HCl, Intermediate CCD) and 2-(2,6-dioxo-3-piperidyl)-4-fluoro-isoindoline-1,3-dione (168 mg, 610 umol) in DMSO (2 mL) was added DIEA (394 mg, 3.05 mmol, 531 uL). The mixture was then stirred at 130° C. for 3 hours. On completion, the mixture was diluted with H$_2$O (0.5 mL), and extracted with EA (3×5 mL). The combined organic layer was washed with brine (3×5 mL), dried with anhydrous Na$_2$SO$_4$, then filtered and the filtrate was concentrated in vacuo. The mixture was purified with pre-HPLC (column: Welch Xtimate C18 150*25 mm*5 um; mobile phase: [water(FA)-ACN]; B %: 42%-72%, 10 min) to give the title compound (170 mg, 52% yield) as a brown solid. $^1$H NMR (400 MHz, DMSO-d$_6$) δ 11.10 (s, 1H), 7.59 (t, J=7.8 Hz, 1H), 7.38-7.26 (m, 5H), 7.09 (d, J=7.2 Hz, 1H), 6.94-6.84 (m, 1H), 6.49 (s, 1H), 5.07 (s, 2H), 4.13 (s, 2H), 3.42 (s, 5H), 2.91 (d, J=17.6 Hz, 4H), 2.36-2.30 (m, 2H), 2.21 (d, J=3.2 Hz, 2H), 2.09-1.98 (m, 1H). LC-MS (ESI+) m/z 535.3 (M+H)+.

Step 2—2-(2,6-Dioxo-3-piperidyl)-4-[[3-[2-(methylamino)ethoxy] cyclobutyl]amino]isoindoline-1,3-dione To a solution of benzyl N-[2[3-[[2-(2,6-dioxo-3-piperidyl)-1,3-dioxo-isoindolin-4-yl]amino] cyclobutoxy] ethyl]-N-methyl-carbamate (60 mg, 112 umol) in DCM (1 mL) was added HBr/HOAc (1.83 g, 6.80 mmol, 1.23 mL, 30% solution). The mixture was stirred at 25° C. for 1 hour. On completion, the mixture was concentrated in vacuo to give the title compound (44 mg, 81% yield, HBr) as a brown solid. LC-MS (ESI+) m/z 401.1 (M+H)+.

1109

1-[7-(1,4-Diazepan-1-yl)-4-isoquinolyl]hexahydro-pyrimidine-2,4-dione (Intermediate CCF)

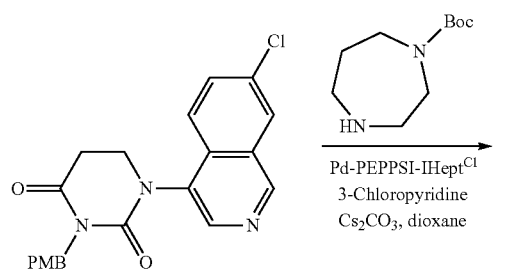

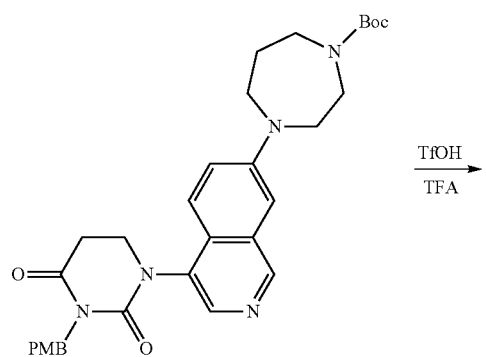

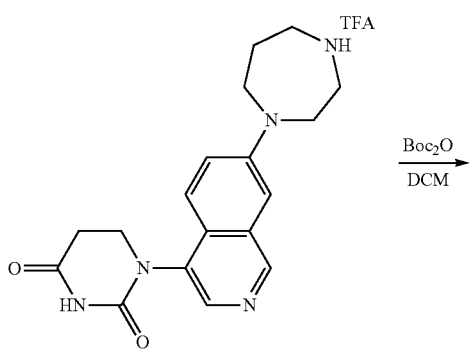

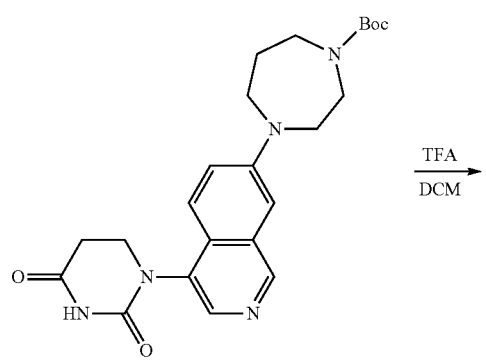

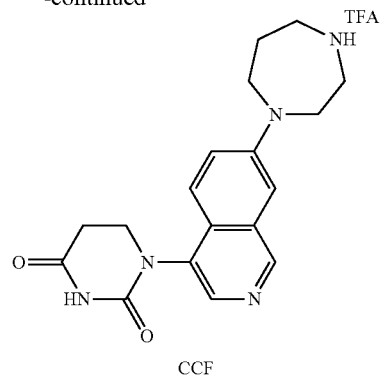

CCF

Step 1—Tert-butyl 4-[4-[3-[(4-methoxyphenyl)methyl]-2,4-dioxo-hexahydropyrimidin-1-yl]-7-isoquinolyl]-1,4-diazepane-1-carboxylate A mixture of 1-(7-chloro-4-isoquinolyl)-3-[(4-methoxyphenyl)methyl]hexahydropyrimidine-2,4-dione (300 mg, 757 umol, synthesized via Steps 1-2 of Intermediate BRX), tert-butyl 1,4-diazepane-1-carboxylate (166 mg, 833 umol, CAS #112275-50-0), $Cs_2CO_3$ (493 mg, 1.52 mmol), Pd-PEPPSI-IHeptCl$_3$—Chloropyridine (73.6 mg, 75.7 umol) in dioxane (5 mL) was degassed and purged with $N_2$ three times, and then the mixture was stirred at 80° C. for 48 hrs under $N_2$ atmosphere. On completion, filtered and concentrated under reduced pressure to give a residue. The residue was purified by column chromatography ($SiO_2$, PE:EA=1:1) to give the title compound (388 mg, 78% yield) as yellow solid. $^1H$ NMR (400 MHz, DMSO-$d_6$) δ 9.01 (s, 1H), 8.16 (s, 1H), 7.69 (d, J=9.2 Hz, 1H), 7.45 (d, J=9.2 Hz, 1H), 7.31-7.19 (m, 3H), 6.88 (d, J=8.4 Hz, 2H), 4.83 (s, 2H), 4.03 (q, J=7.1 Hz, 1H), 3.91-3.80 (m, 1H), 3.73 (s, 3H), 3.69-3.52 (m, 4H), 3.33 (s, 2H), 3.26-2.90 (m, 4H), 2.01-1.89 (m, 2H), 1.30-1.05 (m, 9H).

Step 2—1-[7-(1,4-Diazepan-1-yl)-44 isoquinolyl]hexahydropyrimidine-2,4-dione To a solution of tert-butyl 4-[4-[3-[(4-methoxyphenyl)methyl]-2,4-dioxo-hexahydropyrimidin-1-yl]-7-isoquinolyl]-1,4-diazepane-1-carboxylate (380 mg, 678 umol) in TFA (2 mL) was added TfOH (1.02 g, 6.79 mmol). The mixture was stirred at 60° C. for 3 hrs. On completion, the mixture was concentrated in vacuo to give the title compound (220 mg, 95% yield) as a black oil. LC-MS (ESI+) m/z 340.2 (M+H)$^+$.

Step 3—Tert-butyl 4-[4-(2,4-dioxohexahydropyrimidin-1-yl)-7-isoquinolyl]-1,4-diazepane-1-carboxylate To a solution of 1-[7-(1,4-diazepan-1-yl)-4-isoquinolyl]hexahydropyrimidine-2,4-dione (220 mg, 648 umol) in DCM (4 mL) was added (Boc)$_2$O (282 mg, 1.30 mmol) and TEA (196 mg, 1.94 mmol). The mixture was then stirred at 25° C. for 16 hrs. On completion, filtered and concentrated under reduced pressure to give a residue. The residue was purified by reverse phase (0.1% FA condition) to give the title compound (230 mg, 80% yield) as brown solid. LC-MS (ESI+) m/z 440.4 (M+H)$^+$.

Step 4—1-[7-(1,4-Diazepan-1-yl)-4-isoquinolyl]hexahydropyrimidine-2,4-dione

To a solution of tert-butyl 4-[4-(2,4-dioxohexahydropyrimidin-1-yl)-7-isoquinolyl]-1,4-diazepane-1-carboxylate (88.0 mg, 200 umol) in DCM (2 mL) was added TFA (228 mg, 2.00 mmol). The mixture was then stirred at 25° C. for 0.5 hr. On completion, the mixture was concentrated in vacuo to give the title compound (85.0 mg, 93% yield) as a black brown oil. LC-MS (ESI+) m/z 340.2 (M+H)⁺.

1-[8-(1,2,3,6-Tetrahydropyridin-4-yl)-4-isoquinolyl]hexahydropyrimidine-2,4-dione (Intermediate CCG)

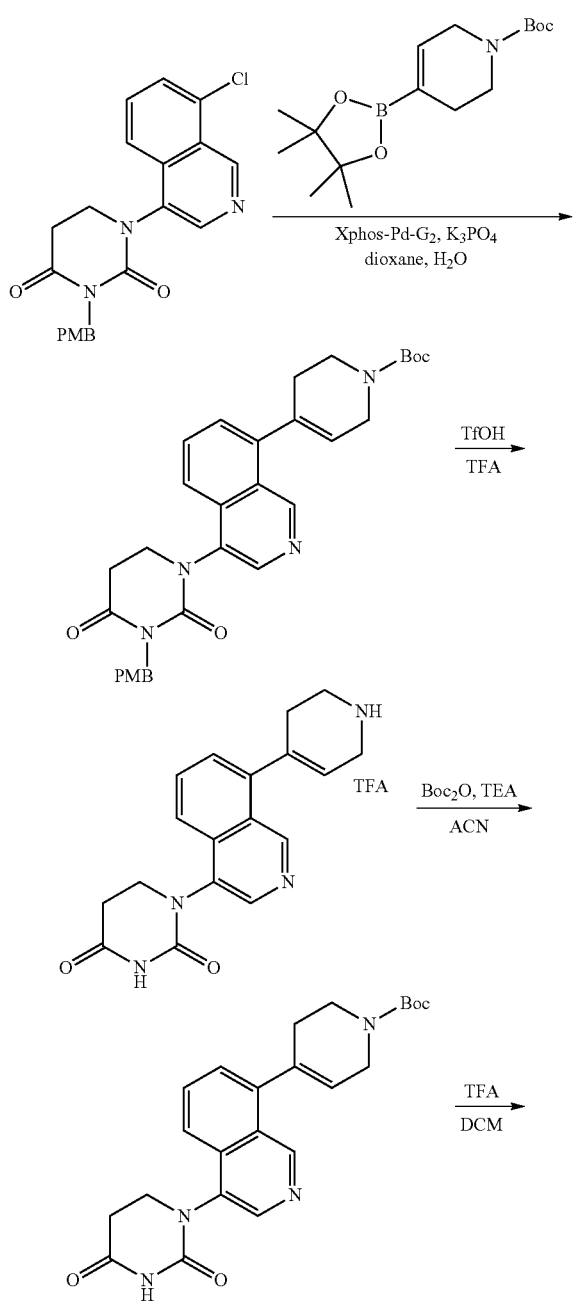

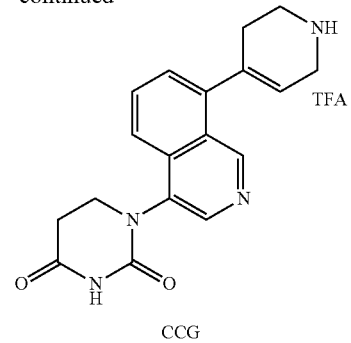

CCG

Step 1—Tert-butyl 4-[4-[3-[(4-methoxyphenyl)methyl]-2,4-dioxo-hexahydropyrimidin-1-yl]-8-isoquinolyl]-3,6-dihydro-2H-pyridine-1-carboxylate A mixture of 1-(8-chloro-4-isoquinolyl)-3-[(4-methoxyphenyl)methyl]hexahydropyrimidine-2,4-dione (250 mg, 631 umol, synthesized via Steps 1-2 of Intermediate BSL), tert-butyl 4-(4,4,5,5-tetramethyl-1,3,2-dioxaborolan-2-yl)-3,6-dihydro-2H-pyridine-1-carboxylate (253 mg, 821 umol, CAS #286961-14-6), Xphos-Pd-G2 (49.6 mg, 63.1 umol) and K₃PO₄ (402 mg, 1.89 mmol) in dioxane (3 mL) and H₂O (0.06 mL) was stirred at 80° C. for 12 hrs under N₂. On completion, the mixture was filtered and concentrated to give a residue. The residue was purified by reversed phase flash (0.1% FA condition) to give the title compound (340 mg, 88% yield) as a yellow solid. ¹H NMR (400 MHz, DMSO-d₆) δ 9.33 (s, 1H), 8.57 (s, 1H), 7.92-7.82 (m, 1H), 7.82-7.72 (m, 1H), 7.54 (d, J=6.8 Hz, 1H), 7.26 (d, J=8.4 Hz, 2H), 6.88 (d, J=8.4 Hz, 2H), 5.87 (s, 1H), 4.84 (s, 2H), 4.09 (s, 2H), 4.06-3.89 (m, 2H), 3.81-3.74 (m, 2H), 3.73 (s, 3H), 3.68 (t, J=5.2 Hz, 2H), 3.15 (d, J=9.6 Hz, 1H), 3.02-2.92 (m, 1H), 1.46 (s, 9H); LC-MS (ESI+) m/z 543.3 (M+H)⁺.

Step 2—1-[8-(1,2,3,6-Tetrahydropyridin-4-yl)-4-isoquinolyl]hexahydropyrimidine-2,4-dione To mixture of tert-butyl 4-[4-[3-[(4-methoxyphenyl)methyl]-2,4-dioxo-hexahydropyrimidin-1-yl]-8-isoquinolyl]-3,6-dihydro-2H-pyridine-1-carboxylate (240 mg, 442 umol) in TFA (5 mL) was added TfOH (1 mL). The mixture was stirred at 70° C. for 1 hr. On completion, the mixture was filtered and concentrated to give the title compound (193 mg, 99% yield, TFA salt) as a brown oil.

Step 3—Tert-butyl 4-[4-(2,4-dioxohexahydropyrimidin-1-yl)-8-isoquinolyl]-3,6-dihydro-2H-pyridine-1-carboxylate To a mixture of 1-[8-(1,2,3,6-tetrahydropyridin-4-yl)-4-isoquinolyl]hexahydropyrimidine-2,4-dione (193 mg, 442 umol, TFA salt) in ACN (3 mL) was added TEA (44.7 mg, 442 umol) until the pH~7-8 at 0° C., then Boc₂O (144 mg, 663 umol) in ACN (1 mL) was added. The mixture was stirred at 25° C. for 12 hrs. On completion, the mixture was filtered and concentrated to give a residue. The residue was diluted with water (30 mL) and extracted with EA (3×20 mL). The combined organic layer was dried over Na₂SO₄, filtered and concentrated in vacuo to give the title compound (186 mg, 76% yield) as a brown oil. LC-MS (ESI+) m/z 423.2 (M+H)⁺.

Step 4—1-[8-(1,2,3,6-Tetrahydropyridin-4-yl)-44 isoquinolyl]hexahydropyrimidine-2,4-dione To a mixture of tert-butyl 4-[4-(2,4-dioxohexahydropyrimidin-1-yl)-8-isoquinolyl]-3,6-dihydro-2H-pyridine-1-carboxylate (90.0 mg, 213 umol) in DCM (2 mL) was added TFA (1 mL). The mixture was stirred at 25° C. for 0.5 hr. On completion, the mixture was filtered and concentrated to give the title compound (92.9 mg, 100% yield, TFA salt) as a brown oil. LC-MS (ESI+) m/z 323.1 (M+H)⁺.

N-[6-chloro-2-(4-formylcyclohexyl)indazol-5-yl]-6-(trifluoromethyl)pyridine-2-carboxamide (Intermediate CCH)

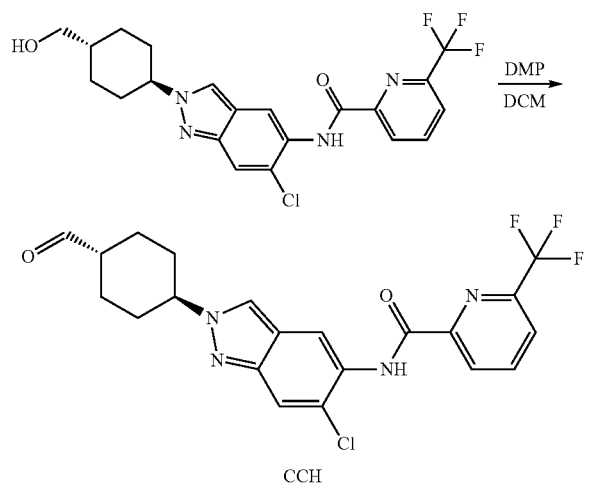

To a solution of N-[6-chloro-2-[4-(hydroxymethyl)cyclohexyl]indazol-5-yl]-6-(trifluoromethyl) pyridine-2-carboxamide (100 mg, 220 umol, synthesized via Steps 1-3 of Intermediate BPQ) in DCM (2 mL) was added DMP (121 mg, 287 umol). The reaction mixture was then stirred at 25° C. for 2 hours. On completion, the reaction mixture was quenched with saturated Na₂S₂O₃ (10 mL) and saturated NaHCO₃ (10 mL) at 25° C. Then, the mixture was stirred for 15 minutes then extracted with DCM (30 mL×2). The combined organic layers were washed with saturated NaCl solution (15 mL×2), dried over Na₂SO₄, filtered and concentrated in vacuo to give the title compound (98 mg, 98.4% yield) as yellow solid. LC-MS (ESI+) m/z 451.1 (M+H)⁺.

1-[7-[4-(Methylamino)-1-piperidyl]-4-isoquinolyl]hexahydropyrimidine-2,4-dione (Intermediate CCI)

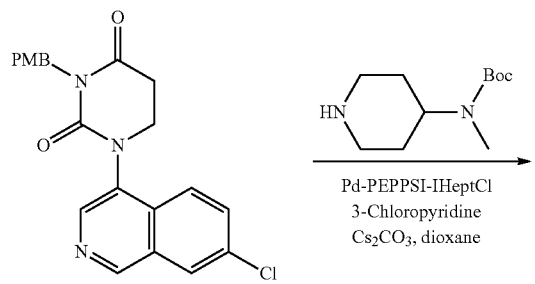

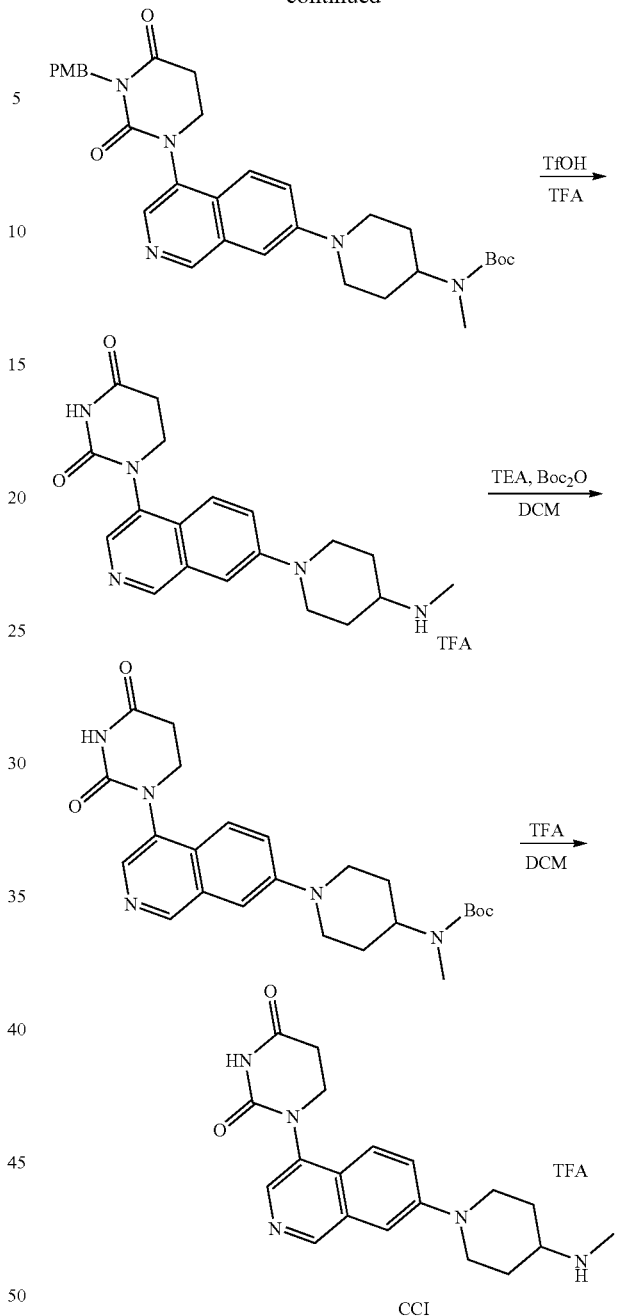

Step 1—Tert-butyl N-[1-[4-[3-[(4-methoxyphenyl)methyl]-2,4-dioxo-hexahydropyrimidin-1-yl]-7-isoquinolyl]-4-piperidyl]-N-methyl-carbamate To a solution of 1-(7-chloro-44 isoquinolyl)-3-[(4-methoxyphenyl)methyl]hexahydropyrimidine-2,4-dione (500 mg, 1.26 mmol, synthesized via Steps 1-2 of Intermediate BRX), tert-butyl N-methyl-N-(4-piperidyl)carbamate (270 mg, 1.26 mmol, CAS #108612-54-0), Pd-PEPPSI-IHEPTCl 3-Chloropyridine (122 mg, 126 umol) and Cs₂CO₃ (82.0 mg, 2.53 mmol) in dioxane (5 mL). The reaction mixture was then stirred at 80° C. for 16 hrs under N₂. On completion, the reaction mixture was filtered and the filtrate was concentrated in vacuo to give a residue. The residue was purified by reverse phase (0.1% FA condition) to give the title compound (200 mg, 27% yield) as a white solid. LC-MS (ESI+) m/z 574.2 (M+H)+.

Step 2—1-[7-[4-(Methylamino)-1-piperidyl]-4-isoquinolyl]hexahydropyrimidine-2,4-dione To a solution of tert-butyl N-[1-[4-[3-[(4-methoxyphenyl)methyl]-2,4-dioxo-hexahydropyrimidin-1-yl]-7-isoquinolyl]-4-piperidyl]-N-methyl-carbamate (198 mg, 345 umol) and in TFA (2 mL) was added TfOH (609 mg, 4.06 mmol). Then the reaction mixture was stirred at 70° C. for 2 hrs. On completion, the reaction mixture was concentrated in vacuo to give the title compound (150 mg, 92% yield, TFA salt) as a brown oil. LC-MS (ESI+) m/z 354.1 (M+H)+.

Step 3—Tert-butyl N-[1-[4-(2,4-dioxohexahydropyrimidin-1-yl)-74 isoquinolyl]-4-piperidyl]-N-methyl-carbamate To a solution of 1-[7-[4-(methylamino)-1-piperidyl]-4-isoquinolyl]hexahydropyrimidine-2,4-dione (150 mg, 424 umol) in DCM (2 mL) was added TEA (42.9 mg, 424 umol), then Boc$_2$O (92.6 mg, 424 umol) was added. The reaction was then stirred at 25° C. for 3 hrs. On completion, the reaction mixture was filtered. Then the mixture was diluted with H$_2$O (30 mL) and extracted with DCM (2×50 mL). The combined organic layers were dried over Na$_2$SO$_4$, filtered and concentrated in vacuo to give the title compound (170 mg, 88% yield) as a yellow solid. LC-MS (ESI+) m/z 454.2 (M+H)+.

Step 4—1-[7-[4-(Methylamino)-1-piperidyl]-4-isoquinolyl]hexahydropyrimidine-2,4-dione To a solution of tert-butyl N-[1-[4-(2,4-dioxohexahydropyrimidin-1-yl)-7-isoquinolyl]-4-piperidyl]-N-methyl-carbamate (80.3 mg, 177 umol) in DCM (1 mL) was added TFA (616 mg, 5.4 mmol). The mixture was then stirred at 25° C. for 2 hrs. On completion, the reaction mixture was concentrated in vacuo to give the title compound (80.0 mg, 96% yield, TFA salt) as a brown solid. LC-MS (ESI+) m/z 354.2 (M+H)+.

3-[4-[4-[(4-Aminocyclohexyl)methyl]piperazin-1-yl]-3-methyl-2-oxo-benzimidazol-1-yl]piperidine-2,6-dione (Intermediate CCJ)

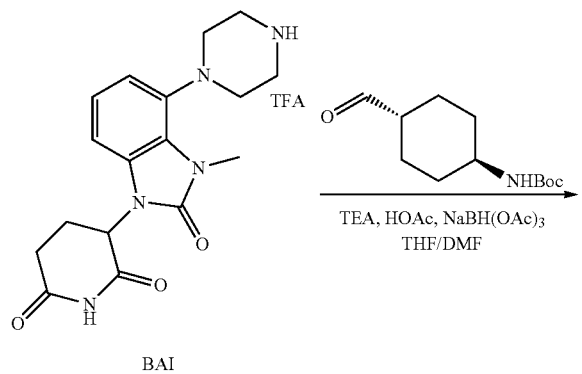

BAI

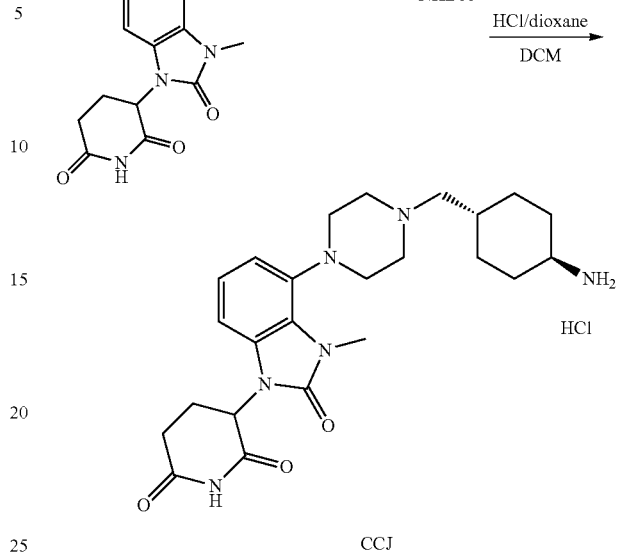

CCJ

Step 1—Tert-butyl N-[4-[[4-[1-(2,6-dioxo-3-piperidyl)-3-methyl-2-oxo-benzimidazol-4-yl] piperazin-1-yl]methyl]cyclohexyl]carbamate To a solution of 3-(3-methyl-2-oxo-4-piperazin-1-yl-benzimidazol-1-yl)piperidine-2,6-dione (300 mg, 655 umol, TFA, Intermediate BAI) in THF (5 mL) and DMF (5 mL) was added TEA (66.3 mg, 655 umol), then the reaction mixture was stirred at −10° C. for 5 mins. Next, HOAc (78.7 mg, 1.31 mmol) and tert-butyl N-(4-formylcyclohexyl)carbamate (178 mg, 787 umol, CAS #181308-57-6) were added then the mixture was stirred at −10° C. for 25 mins. Finally, NaBH(OAc)$_3$ (208 mg, 983 umol) was added to the mixture, and the reaction mixture was stirred at −10° C. for 1 hr. On completion, the reaction mixture was quenched with H$_2$O (0.5 mL) and then concentrated in vacuo to give a residue. The residue was purified by reverse phase (0.1% FA condition) to give the title compound (270 mg, 74% yield) as a white solid. $^1$H NMR (400 MHz, DMSO-d$_6$) δ 11.10 (s, 1H), 7.05-6.98 (m, 1H), 6.97-6.86 (m, 2H), 6.74 (d, J=7.6 Hz, 1H), 5.36 (dd, J=5.2, 12.4 Hz, 1H), 3.63 (s, 3H), 3.23-2.98 (m, 6H), 2.96-2.81 (m, 2H), 2.76-2.57 (m, 3H), 2.56-2.52 (m, 3H), 2.06-1.93 (m, 1H), 1.86-1.73 (m, 4H), 1.65-1.46 (m, 1H), 1.38 (s, 9H), 1.24-1.09 (m, 2H), 1.07-0.87 (m, J=9.6 Hz, 2H); LC-MS (ESI+) m/z 555.3 (M+H)+.

Step 2—3-[4-[4-[(4-Aminocyclohexyl)methyl]piperazin-1-yl]-3-methyl-2-oxo-benzimidazol-1-yl]piperidine-2,6-dione To a solution of tert-butyl N-[4-[[4-[1-(2,6-dioxo-3-piperidyl)-3-methyl-2-oxo-benzimidazol-4-yl]piperazin-1-yl]methyl]cyclohexyl]carbamate (50.0 mg, 90.1 umol) in DCM (1 mL) was added HCl/dioxane (4 M, 500 uL), then the reaction mixture was stirred at 25° C. for 30 mins. On completion, the reaction mixture was concentrated in vacuo to give the title compound (40.0 mg, 90% yield, HCl salt) as a white solid. LC-MS (ESI+) m/z 455.2 (M+H)+.

1-[8-(1,4-Diazepan-1-yl)-4-isoquinolyl]hexahydropyrimidine-2,4-dione (Intermediate CCK)

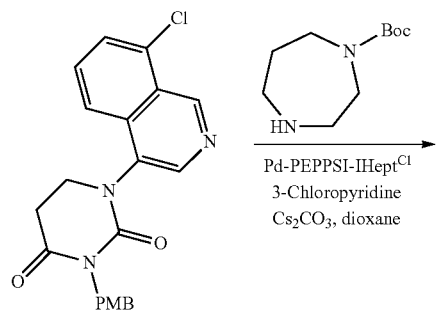

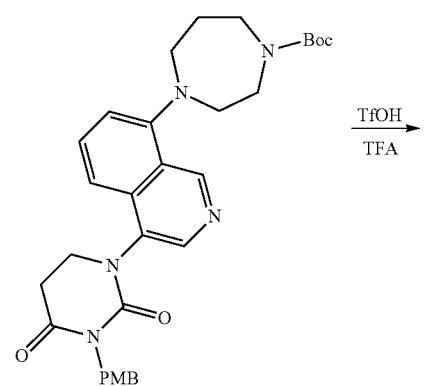

Step 1—Tert-butyl 4-[4-[3-[(4-methoxyphenyl)methyl]-2,4-dioxo-hexahydropyrimidin-1-yl]-8-isoquinolyl]-1,4-diazepane-1-carboxylate A mixture of 1-(8-chloro-4-isoquinolyl)-3-[(4-methoxyphenyl)methyl]hexahydropyrimidine-2,4-dione, (600 mg, 1.52 mmol, Steps 1-2 of Intermediate BSL) tert-butyl 1,4-diazepane-1-carboxylate (303 mg, 1.52 mmol, CAS #112275-50-0), PD-PEPPSI -IHeptCl[3]-Chloropyridine (29.4 mg, 30.3 umol), and Cs$_2$CO$_3$ (987 mg, 3.03 mmol) in dioxane (2 mL) was degassed and purged with N$_2$ three times. Then the mixture was stirred at 80° C. for 5 hrs under N$_2$ atmosphere. On completion, the reaction mixture was diluted with water (20 mL) and extracted with EA (40 mL×2). The combined organic layers were washed with NaCl (10 mL), dried over Na$_2$SO$_4$, filtered and concentrated in vacuo to give a residue. The residue was purified by reverse phase (FA condition) to give the title compound (600 mg, 70% yield) as a white solid. $^1$H NMR (400 MHz, DMSO-d$_6$) δ 9.49 (s, 1H), 8.53 (s, 1H), 7.72-7.63 (m, 1H), 7.53 (d, J=8.4 Hz, 1H), 7.35 (d, J=8.0 Hz, 1H), 7.25 (d, J=8.4 Hz, 2H), 6.92-6.83 (m, 2H), 4.83 (s, 2H), 3.90 (m, 1H), 3.77-3.69 (m, 4H), 3.68-3.61 (m, 2H), 3.60-3.52 (m, 2H), 3.31 (s, 2H), 3.26 (s, 2H), 3.18-3.06 (m, 1H), 2.96 (m, 1H), 2.00 (d, J=3.6 Hz, 2H), 1.45 (d, J=4.0 Hz, 9H). LC-MS (ESI$^+$) m/z 560.3 (M+H)$^+$.

Step 2—1-[8-(1,4-Diazepan-1-yl)-4-isoquinolyl]hexahydropyrimidine-2,4-dione

A mixture of tert-butyl 4-[4-[3-[(4-methoxyphenyl)methyl]-2,4-dioxo-hexahydropyrimidin-1-yl]-8-isoquinolyl]-1,4-diazepane-1-carboxylate (200 mg, 357 umol) in TFA (1 mL) and TfOH (0.2 mL) was degassed and purged with N$_2$ three times. Then the mixture was stirred at 25° C. for 2 hrs under N$_2$ atmosphere. On completion, the reaction mixture was concentrated in vacuo to give the title compound (162 mg, 99% yield, TFA) as a black oil. LC-MS (ESI$^+$) m/z 340.2 (M+H)$^+$.

1-[8-[(3S)-3-methylpiperazin-1-yl]-4-isoquinolyl]hexahydropyrimidine -2,4-dione (Intermediate CCL)

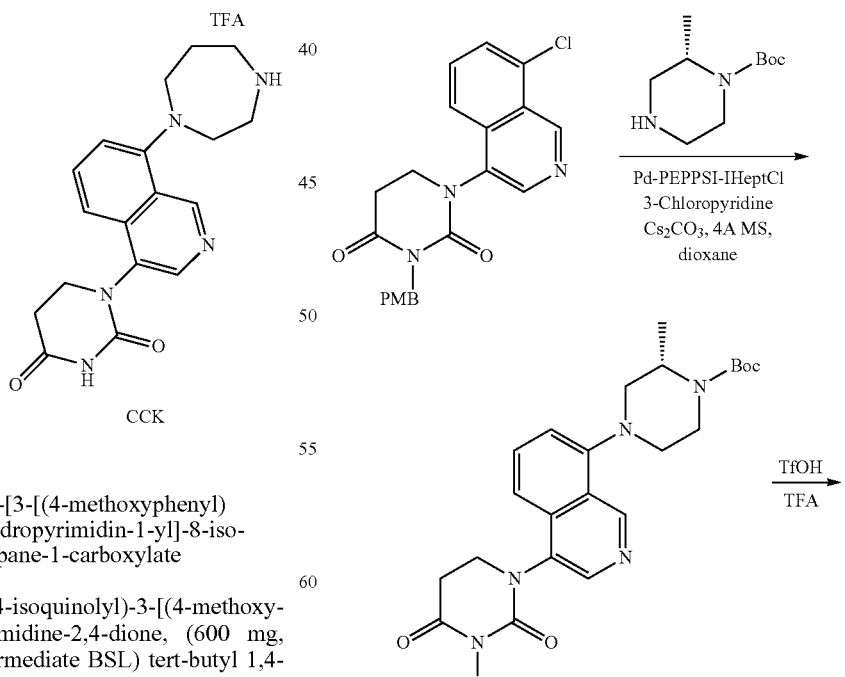

-continued

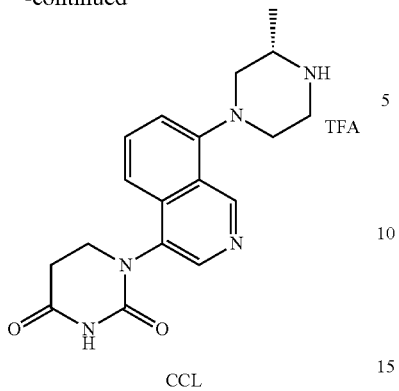

CCL

Step 1—Tert-butyl (2S)-4-[4-[3-[(4-methoxyphenyl)methyl]-2,4-dioxo-hexahydropyrimidin-1-yl]-8-isoquinolyl]-2-methyl-piperazine-1-carboxylate A mixture of 1-(8-chloro-4-isoquinolyl)-3-[(4-methoxyphenyl)methyl]hexahydropyrimidine-2,4-dione (600 mg, 1.52 mmol, Steps 1-2 of Intermediate BSL), tert-butyl (2S)-2-methylpiperazine-1-carboxylate (333 mg, 1.67 mmol, CAS #169447-70-5), PD-PEPPSI-IHeptCl 3-Chloropyridine (147 mg, 151 umol), $Cs_2CO_3$ (987 mg, 3.03 mmol) and 4 Å molecular sieves (20 mg) in dioxane (6 mL) was stirred at 100° C. for 12 hrs. On completion, the reaction mixture was filtered and filtrate was concentrated in vacuo to give a residue. The residue was diluted with water (20 mL) and extracted with EA (10 mL×3). The combined organic layer was dried over $Na_2SO_4$, filtered and concentrated in vacuo to give a residue. The residue was purified by reverse phase (0.1% FA condition) to give the title compound (480 mg, 57% yield) as a white solid. $^1$H NMR (400 MHz, DMSO-$d_6$) δ 9.55 (s, 1H), 8.56 (s, 1H), 7.77-7.67 (m, 1H), 7.59 (d, J=8.4 Hz, 1H), 7.33-7.21 (m, 3H), 6.94-6.81 (m, 2H), 4.83 (s, 2H), 4.31 (d, J=2.4 Hz, 1H), 3.96-3.85 (m, 2H), 3.73 (s, 4H), 3.52-3.32 (m, 2H), 3.26-3.09 (m, 2H), 3.01-2.92 (m, 2H), 2.78 (q, J=3.2, 11.4 Hz, 1H), 1.45 (s, 9H), 1.42 (s, 3H); LC-MS (ESI$^+$) m/z 560.3 (M+H)$^+$.

Step 2—1-[8-[(3S)-3-methylpiperazin-1-yl]-4-isoquinolyl]hexahydropyrimidine-2,4-dione To a solution of tert-butyl (2S)-4-[4-[3-[(4-methoxyphenyl)methyl]-2,4-dioxo-hexahydropyrimidin-1-yl]-8-isoquinolyl]-2-methyl-piperazine-1-carboxylate (200 mg, 357 umol) in TFA (2 mL) was added TfOH (340 mg, 2.27 mmol), then the mixture was stirred at 60° C. for 2 hrs. On completion, the reaction mixture was concentrated in vacuo to give the title compound (650 mg, TFA, 95% yield) as a yellow oil. LC-MS (ESI$^+$) m/z 340.3 (M+H)$^+$.

6-(trifluoromethyl)pyridine-2-carboxylic acid (CAS #131747-42-7) (Intermediate CCM)

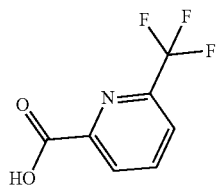

CCM

Tert-butyl N-(5-formyl-2-methoxy-4-nitro-phenyl)carbamate (Intermediate CCN)

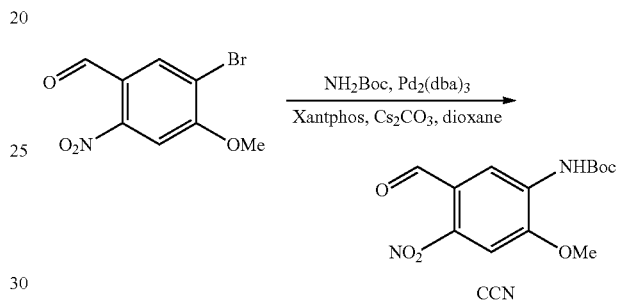

CCN

To a mixture of 5-bromo-4-methoxy-2-nitro-benzaldehyde (4.7 g, 18.0 mmol, synthesized via Steps 1-2 of Intermediate ATE) and tert-butyl carbamate (2.54 g, 21.6 mmol, CAS #4248-19-5) in dioxane (100 mL) was added Pd$_2$(dba)$_3$ (1.66 g, 1.81 mmol), Xantphos (2.09 g, 3.61 mmol) and Cs$_2$CO$_3$ (17.6 g, 54.2 mmol). The reaction mixture was then stirred at 90° C. for 12 hrs. On completion, the residue was diluted with water (30 mL) and extracted with EA (2×50 mL). The combined organic layers were washed with saturated NaCl (40 mL). The combined organic layer was dried over Na$_2$SO$_4$, filtered and concentrated in vacuo to give a residue. The residue was purified by column chromatography (SiO$_2$, PE:EA=20:1 to PE:EA=1:1,PE:EA=5:1, P1:Rf=0.3) then triturated with EA/PE=5/1 (50 mL) to give the title compound (4.57 g, 85% yield) as an yellow solid. $^1$H NMR (400 MHz, DMSO-$d_6$) δ 10.17 (s, 1H), 8.75 (s, 1H), 8.40 (s, 1H), 7.72 (s, 1H), 4.00 (s, 3H), 1.49 (s, 9H); LC-MS (ESI$^+$) m/z 296.9 (M+H)$^+$.

Benzyl 4-(4-aminocyclohexoxy)piperidine-1-carboxylate (Intermediate CCO)

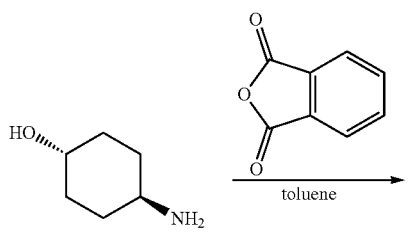

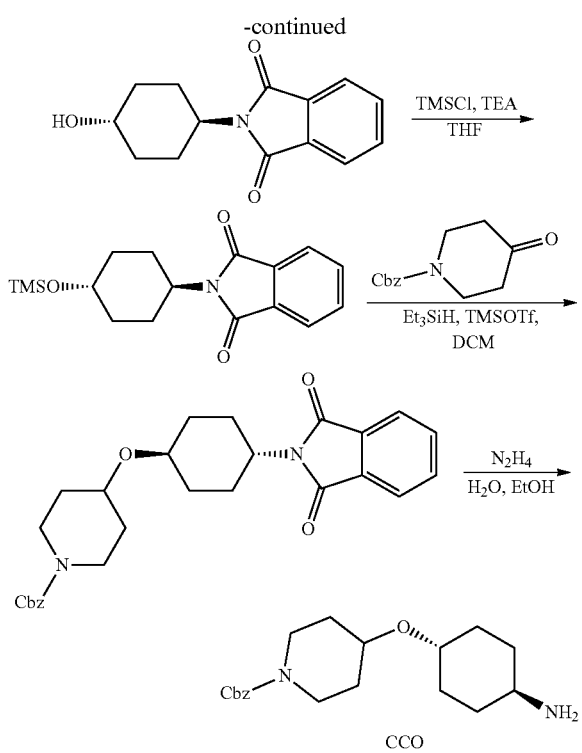

Step 1—2-(4-Hydroxycyclohexyl)isoindoline-1,3-dione

A solution of 4-aminocyclohexanol (5.00 g, 43.41 mmol, CAS #27489-62-9) and isobenzofuran-1,3-dione (6.43 g, 43.4 mmol, CAS #85-44-9) in DMF (50 mL) and toluene (50 mL) was stirred at 120° C. for 16 hrs. On completion, the reaction mixture was concentrated in vacuo to remove toluene, then the residue was diluted with H$_2$O (200 mL) and filtered. The filter cake was dried in vacuo to give the title compound (10.0 g, 93% yield) as a white solid. LC-MS (ESI$^+$) m/z 246.1 (M+H)$^+$.

Step 2—2-(4-Trimethylsilyloxycyclohexyl)isoindoline-1,3-dione

To a solution of 2-(4-hydroxycyclohexyl)isoindoline-1,3-dione (4 g, 16.3 mmol) in THF (50 mL) was added TEA (1.98 g, 19.5 mmol, 2.72 mL), then TMSCl (1.86 g, 17.12 mmol, 2.17 mL) was added at 0° C. dropwise. Then the reaction mixture was stirred at 25° C. for 3 hrs. On completion, the reaction mixture was diluted with H$_2$O (80 mL) and extracted with EA (2×40 mL). The combined organic layers were dried over Na$_2$SO$_4$, filtered and the filtrate was concentrated in vacuo to give the title compound (4.70 g, 90% yield) as a white solid. $^1$H NMR (400 MHz, CDCl$_3$) δ 7.73-7.62 (m, 2H), 7.60-7.51 (m, 2H), 3.98 (tt, J=4.0, 12.4 Hz, 1H), 3.56 (tt, J=4.4, 10.8 Hz, 1H), 2.19 (dq, J=3.6, 13.2 Hz, 2H), 1.88-1.77 (m, 2H), 1.65-1.54 (m, 2H), 1.41-1.26 (m, 2H), 0.00 (s, 9H).

Step 3—Benzyl 4-[4-(1,3-dioxoisoindolin-2-yl)cyclohexoxy]piperidine-1-carboxylate To a solution of 2-(4-trimethylsilyloxycyclohexyl)isoindoline-1,3-dione (4.70 g, 14.8 mmol) and benzyl 4-oxopiperidine-1-carboxylate (3.45 g, 14.8 mmol, 2.95 mL, CAS #19099-93-5) in DCM (100 mL) was added Et$_3$SiH (1.89 g, 16.2 mmol, 2.60 mL) and TMSOTf (1.65 g, 7.40 mmol, 1.34 mL) at −60° C. Then the reaction mixture was stirred at 25° C. for 1 hr. On completion, the reaction mixture was diluted with H$_2$O (60 mL) and extracted with DCM (2×40 mL). The combined organic layers were dried over Na$_2$SO$_4$, filtered and the filtrate was concentrated under reduced pressure to give a residue. The residue was purified by reverse phase (0.1% FA condition) to give the title compound (4.30 g, 62% yield) as white solid. $^1$H NMR (400 MHz, DMSO-d$_6$) δ 7.88-7.78 (m, 4H), 7.43-7.25 (m, 5H), 5.06 (s, 2H), 3.98 (tt, J=4.0, 12.4 Hz, 1H), 3.78-3.59 (m, 3H), 3.49-3.38 (m, 1H), 3.22-3.02 (m, 2H), 2.16 (dq, J=3.2, 12.8 Hz, 2H), 2.06-1.96 (m, 2H), 1.84-1.65 (m, 4H), 1.41-1.20 (m, 4H); LC-MS (ESI$^+$) m/z 463.2 (M+H)$^+$.

Step 4—Benzyl 4-(4-aminocyclohexoxy)piperidine-1-carboxylate

To a solution of benzyl 4-[4-(1,3-dioxoisoindolin-2-yl)cyclohexoxy]piperidine-1-carboxylate (4.30 g, 9.30 mmol) in EtOH (40 mL) was added N$_2$H$_4$.H$_2$O (2.27 g, 44.3 mmol, 2.2 mL, 98% solution), then the reaction mixture was stirred at 80° C. for 2 hrs. On completion, the reaction mixture was filtered and the filtrate was concentrated in vacuo to give a residue. The residue was then diluted with DCM (30 mL), filtered and the filtrate was concentrated in vacuo to give the title compound (2.90 g, 94% yield) as colorless oil. $^1$H NMR (400 MHz, CDCl$_3$) δ 7.62-7.28 (m, 5H), 5.13 (s, 2H), 3.91-3.75 (m, 2H), 3.64-3.53 (m, 1H), 3.39-3.28 (m, 1H), 3.22-3.13 (m, 2H), 2.78-2.67 (m, 1H), 1.99-1.89 (m, 3H), 1.88-1.84 (m, 3H), 1.83-1.72 (m, 2H), 1.61-1.45 (m, 2H), 1.39-1.25 (m, 2H), 1.23-1.08 (m, 2H).

Tert-butyl N-[6-methoxy-2-[4-(4-piperidyloxy)cyclohexyl]indazol-5-yl]carbamate (Intermediate CCP)

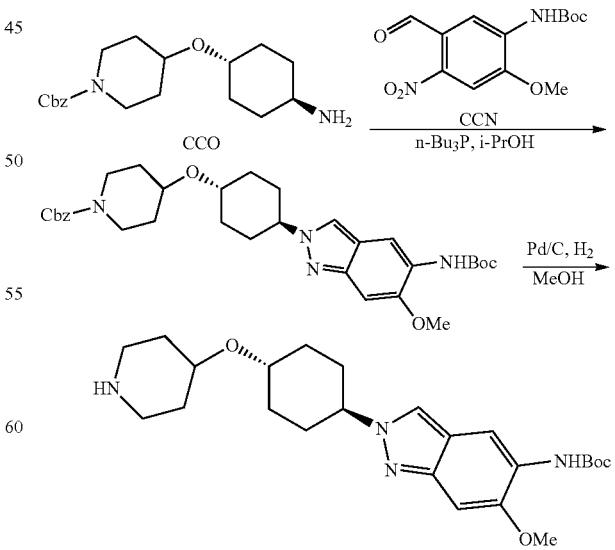

Step 1—Benzyl 4-[4-[5-(tert-butoxycarbonylamino)-6-methoxy-indazol-2-yl]cyclohexoxy]piperidine-1-carboxylate A solution of benzyl 4-(4-aminocyclohexoxy)piperidine-1-carboxylate (2.70 g, 8.12 mmol, Intermediate CCO) and tert-butyl N-(5-formyl-2-methoxy-4-nitro-phenyl)carbamate (2.41 g, 8.12 mmol, Intermediate CCN) in IPA (50 mL) was stirred at 80° C. for 4 hrs. Next, the mixture was cooled to 25° C., and tributylphosphane (4.93 g, 24.3 mmol, 6.01 mL) was added. Then the reaction mixture was stirred at 80° C. for 12 hrs. On completion, the reaction mixture was concentrated in vacuo to give a residue. The residue was purified by reverse phase (0.1% FA condition) to give the title compound (2.30 g, 49% yield) as a yellow solid. $^1$H NMR (400 MHz, DMSO-$d_6$) δ 8.16 (s, 1H), 7.90 (s, 1H), 7.77 (s, 1H), 7.46-7.25 (m, 5H), 6.98 (s, 1H), 5.07 (s, 2H), 4.43-4.30 (m, 1H), 3.84 (s, 3H), 3.77-3.68 (m, 2H), 3.67-3.58 (m, 1H), 3.53-3.45 (m, 1H), 3.21-3.06 (m, 2H), 2.11-2.00 (m, 4H), 1.98-1.85 (m, 2H), 1.84-1.74 (m, 2H), 1.46 (s, 9H), 1.42-1.27 (m, 4H); LC-MS (ESI$^+$) m/z 579.6 (M+H)$^+$.

Step 2—Tert-butyl N-[6-methoxy-2-[4-(4-piperidyloxy)cyclohexyl]indazol-5-yl]carbamate To a solution of benzyl 4-[4-[5-(tert-butoxycarbonylamino)-6-methoxy-indazol-2-yl]cyclohexoxy]piperidine-1-carboxylate (2.30 g, 3.97 mmol) in MeOH (30 mL) was added Pd/C (500 mg, 10 wt %), then the reaction mixture was stirred at 25° C. for 16 hrs under $H_2$ (15 psi). On completion, the mixture was filtered and the filtrate was concentrated in vacuo to give the title compound (1.75 g, 99% yield) as a yellow solid. LC-MS (ESI$^+$) m/z 445.3 (M+H)$^+$.

3-[4-[4-[4-(5-Amino-6-methoxy-indazol-2-yl)cyclohexoxy]-1-piperidyl]-3-methyl-2-oxo-benzimidazol-1-yl]piperidine-2,6-dione (Intermediate CCQ)

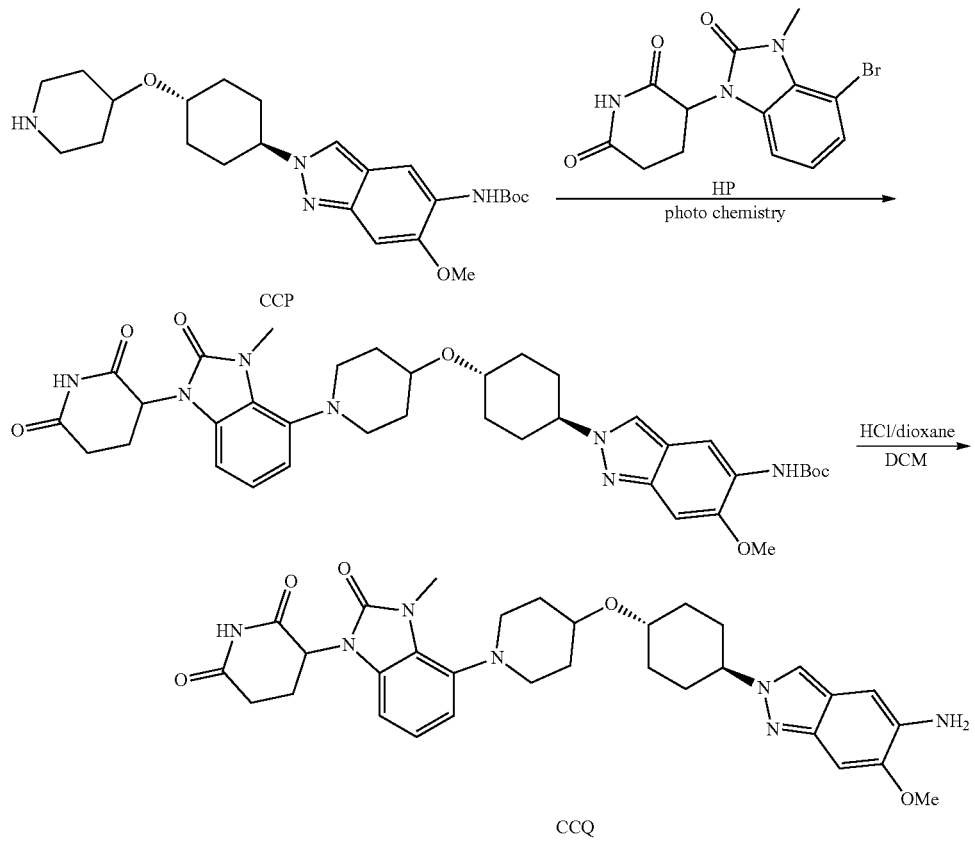

Step 1—Tert-butyl N-[2-[4-[[1-[1-(2,6-dioxo-3-piperidyl)-3-methyl-2-oxo-benzimidazol-4-yl]-4-piperidyl]oxy]cyclohexyl]-6-methoxy-indazol-5-yl]carbamate A mixture of 3-(4-bromo-3-methyl-2-oxo-benzimidazol-1-yl)piperidine-2,6-dione (304 mg, 899 umol, Intermediate HP), tert butyl N-[6-methoxy-2-[4-(4-piperidyloxy)cyclohexyl]indazol-5-yl]carbamate (400 mg, 8 umol, Intermediate CCP), DABCO (181 mg, 1.62 mmol), IR(PPY)$_2$(DTBBPY)PF$_6$ (16.4 mg, 18.0 umol), and NiBr$_2$·glyme (13.9 mg, 45.0 umol) in DMA (8 mL) was degassed three times with $N_2$. The reaction vial was then sealed with parafilm, placed 2 cm away from one blue LED, and irradiated at 25° C. for 14 hrs. On completion, the mixture was diluted with EA (15 mL×3) and washed with H2O (30 mL). The combined organic phase was dried over anhydrous sodium sulfate, filtered and concentrated to give a residue. The residue was purified by reverse phase (0.1% FA condition) to give the title compound (25 mg, 4% yield) as a white solid. $^1$H NMR (400 MHz, DMSO-$d_6$) δ 11.09 (s, 1H), 8.19 (s, 1H), 7.90 (s, 1H), 7.78 (s, 1H), 7.01-6.95 (m, 2H), 6.93-6.85 (m, 2H), 5.35 (dd, J=5.2, 12.4 Hz, 1H), 4.46-4.34

(m, 1H), 3.85 (s, 3H), 3.64 (s, 3H), 3.62-3.47 (m, 2H), 3.16-2.99 (m, 2H), 2.95-2.79 (m, 2H), 2.78-2.62 (m, 3H), 2.18-2.05 (m, 5H), 2.04-1.89 (m, 5H), 1.67-1.54 (m, 2H), 1.47 (s, 12H); LC-MS (ESI+) m/z 702.3 (M+H)+.

Step 2—3-[4-[4-[4-(5-Amino-6-methoxy-indazol-2-yl)cyclohexoxy]-1-piperidyl]-3-methyl-2-oxo-benzimidazol-1-yl]piperidine-2,6-dione To a solution of tert-butyl N-[2-[4-[[1-[1-(2,6-dioxo-3-piperidyl)-3-methyl-2-oxo-benzimidazol-4-yl]-4-piperidyl]oxy]cyclohexyl]-6-methoxy-indazol-5-yl]carbamate (18.0 mg, 25.6 umol) in DCM (1 mL) was added HCl/dioxane (4 M, 0.5 mL). Then the reaction mixture was stirred at 25° C. for 30 mins. On completion, the reaction mixture was concentrated in vacuo to give residue to give the title compound (16 mg, 97% yield, HCl salt) as a white solid. LC-MS (ESI+) m/z 602.4 (M+H)+.

6-Bromo-5-methoxy-2-methylsulfonyl-1,3-benzothiazole (Intermediate BJM)

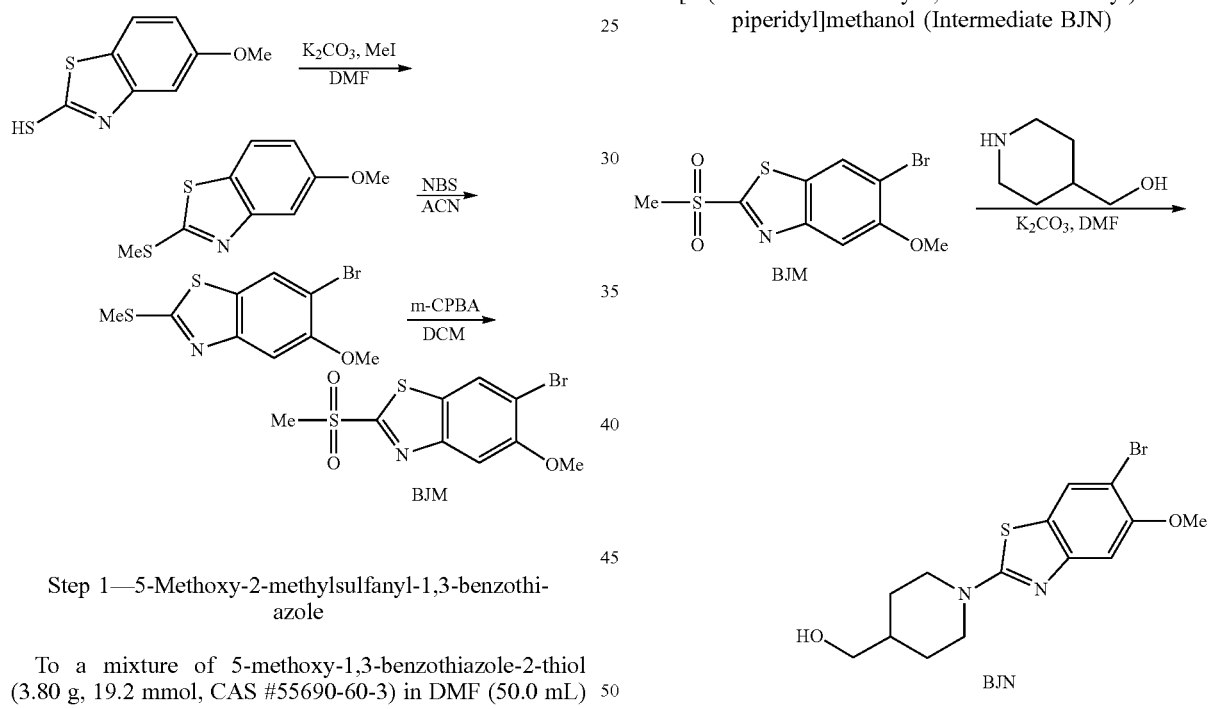

Step 1—5-Methoxy-2-methylsulfanyl-1,3-benzothiazole

To a mixture of 5-methoxy-1,3-benzothiazole-2-thiol (3.80 g, 19.2 mmol, CAS #55690-60-3) in DMF (50.0 mL) was added K2CO3 (5.32 g, 38.5 mmol) and CH3I (4.10 g, 28.8 mmol) at 0° C. The mixture was stirred at 20° C. for 0.5 hour. On completion, the mixture was poured into the water (120 mL) and the aqueous phase was extracted with ethyl acetate (2×50 mL). The combined organic phase was washed with brine (2×50 mL), dried with anhydrous Na2SO4, filtered and concentrated in vacuo to give the title compound (4.00 g, 98% yield) as brown oil. 1H NMR (400 MHz, CDCl3) δ 7.60 (d, J=8.8 Hz, 1H), 7.40 (d, J=2.4 Hz, 1H), 6.94 (dd, J=2.4, 8.8 Hz, 1H), 3.87 (s, 3H), 2.78 (s, 3H).

Step 2—6-Bromo-5-methoxy-2-methylsulfanyl-1,3-benzothiazole

To a mixture of 5-methoxy-2-methylsulfanyl-1,3-benzothiazole (3.8 g, 17.9 mmol) in CH3CN (40 mL) was added NBS (3.20 g, 17.9 mmol) at 0° C. The mixture was stirred at 0° C. for 0.5 hour. On completion, the mixture was concentrated at 45° C. The residue was purified by recrystallization from EA (5 mL) and MTBA (15 mL) at 60° C. to give the title compound (2.00 g, 38% yield) as white solid. 1H NMR (400 MHz, CDCl3) δ 7.81 (s, 1H), 7.32 (s, 1H), 3.88 (s, 3H), 2.70 (s, 3H).

Step 3—6-Bromo-5-methoxy-2-methyl sulfonyl-1,3-benzothiazole

To a mixture of 6-bromo-5-methoxy-2-methylsulfanyl-1,3-benzothiazole (2.00 g, 6.89 mmol) in DCM (20 mL) was added m-CPBA (2.80 g, 13.7 mmol, 85% solution). The reaction mixture was stirred at 25° C. for 0.5 hour. On completion, the mixture was poured into the water (200 mL), and extracted with DCM (2×150 mL). The combined organic phase was washed with brine (2×200 mL), dried with anhydrous Na2SO4, filtered and concentrated in vacuo at 45° C. to give the title compound (2.70 g, 80% yield) as white solid, 1H NMR (400 MHz, CDCl3) δ 8.10 (s, 1H), 7.55 (s, 1H), 3.93 (s, 3H), 3.32 (s, 3H).

[1-(6-Bromo-5-methoxy-1,3-benzothiazol-2-yl)-4-piperidyl]methanol (Intermediate BJN)

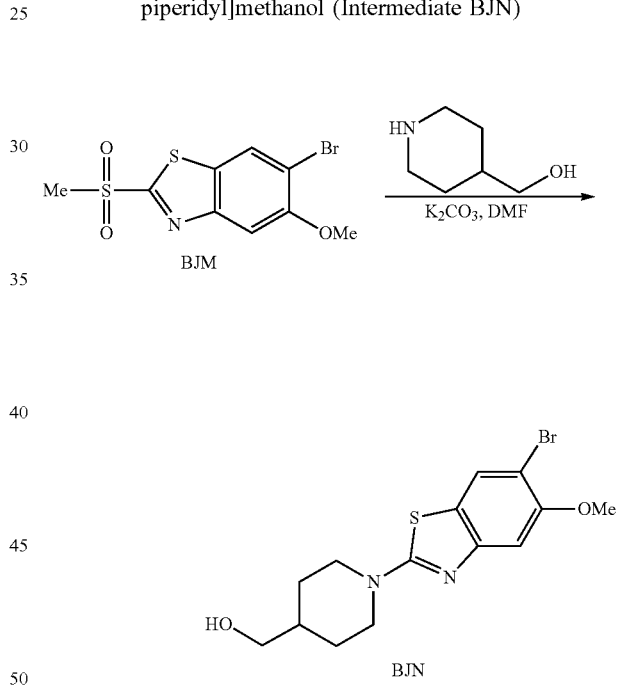

To a solution of 6-bromo-5-methoxy-2-methylsulfonyl-1,3-benzothiazole (2.7 g, 8.38 mmol, Intermediate BJM) and 4-piperidylmethanol (1.06 g, 9.22 mmol, CAS #6457-49-4) in DMF (30 mL) was added K2CO3 (2.32 g, 16.7 mmol), the mixture was stirred at 60° C. for 16 hrs. On completion, the mixture was diluted with H2O (180 mL), then extracted with EA (3×50 mL). The organic layers were washed with brine (3×50 mL) and dried over anhydrous Na2SO4, filtered and concentrated in vacuo. The mixture was purified by silica gel column (PE:EA=2:3) to give the title compound (1.70 g, 56% yield) as white solid. 1H NMR (400 MHz, DMSO-d6) δ 7.94 (s, 1H), 7.17 (s, 1H), 4.54 (t, J=5.2 Hz, 1H), 4.05-3.95 (m, 2H), 3.84 (s, 3H), 3.31-3.27 (m, 2H), 3.18-3.08 (m, 2H), 1.83-1.73 (m, 2H), 1.72-1.60 (m, 1H), 1.28-1.11 (m, 2H), LC-MS (ESI+) m/z 359.0 (M+H)+.

N-[2-(4-formyl-1-piperidyl)-5-methoxy-1,3-benzo-thiazol-6-yl]-6-(trifluoromethyl)pyridine-2-carbox-amide (Intermediate CCR)

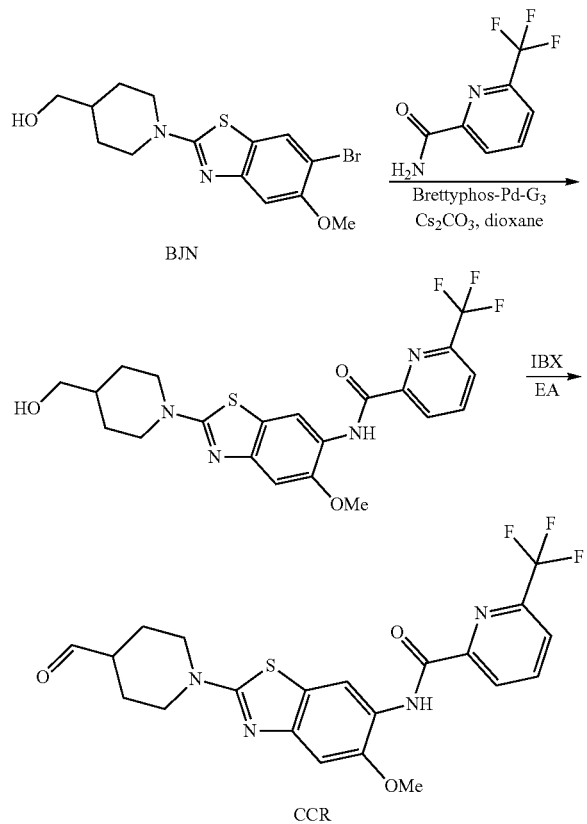

Step 1—N-[2-[4-(hydroxymethyl)-1-piperidyl]-5-methoxy-1,3-benzothiazol-6-yl]-6-(trifluoromethyl)pyridine-2-carboxamide To a solution of [1-(6-bromo-5-methoxy-1,3-benzothiazol-2-yl)-4-piperidyl]methanol (1.40 g, 3.92 mmol, Intermediate BJN) in dioxane (20 mL) was added 6-(trifluoromethyl)pyridine-2-carboxamide (894 mg, 4.70 mmol), 4 Å MS (3.92 mmol), Cs$_2$CO$_3$ (2.55 g, 7.84 mmol) and [2-(2-aminophenyl)phenyl]-methyl sulfonyloxy-palladium; dicyclohexyl-[3,6-dimethoxy-2-(2,4,6-triisopropylphenyl)phenyl]phosphane (355 mg, 391 umol, CAS #22245-84-7). The mixture was then stirred at 90° C. for 12 hrs under N$_2$. On completion, the mixture was filtered and concentrated in vacuo. The residue was purified by column chromatography (SiO$_2$, Petroleum ether/Ethyl acetate=5:1 to 1:1) to give the title compound (250 mg, 12% yield) as a yellow solid. $^1$H NMR (400 MHz, DMSO-d$_6$) δ 10.33 (s, 1H), 8.70 (s, 1H), 8.53-8.42 (m, 1H), 8.42-8.32 (m, 1H), 8.21 (dd, J=1.2, 7.6 Hz, 1H), 7.27 (s, 1H), 4.54 (t, J=5.2 Hz, 1H), 4.07-3.98 (m, 2H), 3.95 (s, 3H), 3.30-3.27 (m, 2H), 3.14 (dt, J=2.4, 12.4 Hz, 2H), 1.83-1.60 (m, 3H), 1.28-1.15 (m, 2H); LC-MS (ESI$^+$) m/z 466.9 (M+H)$^+$.

Step 2—N-[2-(4-formyl-1-piperidyl)-5-methoxy-1,3-benzothiazol-6-yl]-6-(trifluoromethyl)pyridine-2-carboxamide To a solution of N-[2-[4-(hydroxymethyl)-1-piperidyl]-5-methoxy-1,3-benzothiazol-6-yl]-6-(trifluoromethyl)pyridine-2-carboxamide (100 mg, 214 umol) in EA (1 mL) were added IBX (180 mg, 643 umol) and 4 Å molecular sieves (50.0 mg, 214 umol). The mixture was then stirred at 50° C. for 12 hrs. On completion, the mixture was filtered and concentrated to give a residue. The residue was purified by prep-TLC (SiO$_2$, PE:EA=1:1) to give the title compound (100 mg, 85% yield) as a yellow solid. $^1$H NMR (400 MHz, DMSO-d$_6$) δ 10.33 (s, 1H), 9.63 (s, 1H), 8.71 (s, 1H), 8.49-8.34 (m, 2H), 8.20 (dd, J=0.8, 7.6 Hz, 1H), 7.28 (s, 1H), 3.95 (s, 3H), 3.92 (t, J=3.6 Hz, 2H), 3.31-3.26 (m, 2H), 2.72-2.61 (m, 1H), 2.03-1.94 (m, 2H), 1.66-1.53 (m, 2H); LC-MS (ESI$^+$) m/z 465.0 (M+H)$^+$.

3-(5-methoxy-3-methyl-2-oxo-4-piperazin-1-yl-benzimidazol-1-yl)piperidine-2,6-dione (Intermediate CCS)

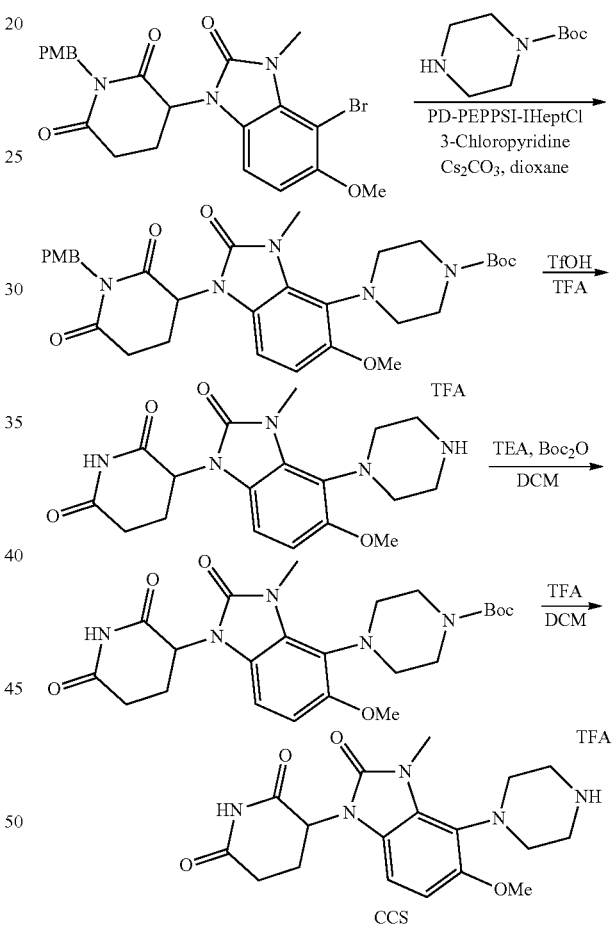

Step 1—Tert-butyl 4-[5-methoxy-1-[1-[(4-methoxyphenyl)methyl]-2,6-dioxo-3-piperidyl]-3-methyl-2-oxo-benzimidazol-4-yl]piperazine-1-carboxylate To a solution of 3-(4-bromo-5-methoxy-3-methyl-2-oxo-benzimidazol-1-yl)-1-[(4-methoxyphenyl)methyl]piperidine-2,6-dione (200 mg, 409 umol, synthesized via Step 1 of Intermediate BWM) and tert-butyl piperazine-1-carboxylate (114 mg, 614 umol, CAS #143238-38-4) in dioxane (5 mL) was added Cs$_2$CO$_3$ (400 mg, 1.23 mmol) and PD-PEPPSI-IHeptCl$_3$-Chloropyridine (39.8 mg, 40.9 umol) at 25° C.

Then the reaction mixture was stirred at 100° C. for 10 hours under N$_2$. On completion, the reaction mixture was filtered and concentrated in vacuo. The residue was purified by prep-HPLC (column: YMC Triart C18 250*50 mm*7 um; mobile phase: [water (FA)-ACN]; B %: 60%-90%, 10 min) to give the title compound (110 mg, 15% yield) as yellow solid. $^1$H NMR (400 MHz, DMSO-d$_6$) δ 7.20 (d, J=8.8 Hz, 2H), 6.86 (d, J=8.8 Hz, 2H), 6.78 (d, J=8.4 Hz, 1H), 6.63 (d, J=8.4 Hz, 1H), 5.46 (dd, J=5.2, 12.8 Hz, 1H), 4.85-4.71 (m, 2H), 3.92-3.79 (m, 2H), 3.76 (s, 3H), 3.72 (s, 3H), 3.61 (s, 3H), 3.31-3.25 (m, 3H), 3.10-2.97 (m, 2H), 2.86-2.77 (m, 3H), 2.75-2.64 (m, 1H), 2.06-1.97 (m, 1H), 1.43 (s, 9H).

Step 2—3-(5-methoxy-3-methyl-2-oxo-4-piperazin-1-yl-benzimidazol-1-yl)piperidine -2,6-dione To a solution of tert-butyl 4-[5-methoxy-1-[1-[(4-methoxyphenyl) methyl]-2,6-dioxo-3-piperidyl]-3-methyl-2-oxo-benzimidazol-4-yl]piperazine-1-carboxylate (80.0 mg, 134 umol) in TFA (1 mL) was added TfOH (340 mg, 2.27 mmol). Then the reaction mixture was stirred at 70° C. for 3 hours. On completion, the reaction mixture was concentrated in vacuo to give the title compound (65.0 mg, 98% yield, TFA) as brown oil. LC-MS (ESI$^+$) m/z 374.1 (M+H)$^+$.

Step 3—Tert-butyl 4-[1-(2,6-dioxo-3-piperidyl)-5-methoxy-3-methyl-2-oxo-benzimidazol-4-yl]piperazine-1-carboxylate To a solution of 3-(5-methoxy-3-methyl-2-oxo-4-piperazin-1-yl-benzimidazol-1-yl)piperidine-2,6-dione (80.0 mg, 164 umol, TFA) in DCM (2 mL) was added TEA (49.8 mg, 492 umol) and Boc$_2$O (42.9 mg, 196 umol). Then the reaction mixture was stirred at 25° C. for 5 hours. On completion, the reaction mixture was diluted with DCM (80 mL), washed with water (50 mL×4), filtered and concentrated in vacuo to give the title compound (77 mg, 99.0% yield) as brown solid. LC-MS (ESI$^+$) m/z 474.3 (M+H)$^+$.

Step 4—3-(5-methoxy-3-methyl-2-oxo-4-piperazin-1-yl-benzimidazol-1-yl)piperidine -2,6-dione To a solution of tert-butyl 4-[1-(2,6-dioxo-3-piperidyl)-5-methoxy-3-methyl-2-oxo-benzimidazol-4-yl]piperazine-1-carboxylate (50.0 mg, 105 umol) in DCM (0.7 mL) was added TFA (462 mg, 4.05 mmol), then the reaction mixture was stirred at 25° C. for 0.5 hours. On completion, the reaction mixture was concentrated in vacuo to give the title compound (50.0 mg, 97% yield, TFA) as brown soil. LC-MS (ESI$^+$) m/z 374.1 (M+H)$^+$.

1-(8-Bromo-4-isoquinolyl)hexahydropyrimidine-2,4-dione (Intermediate CCT)

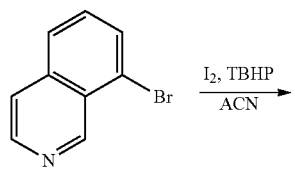

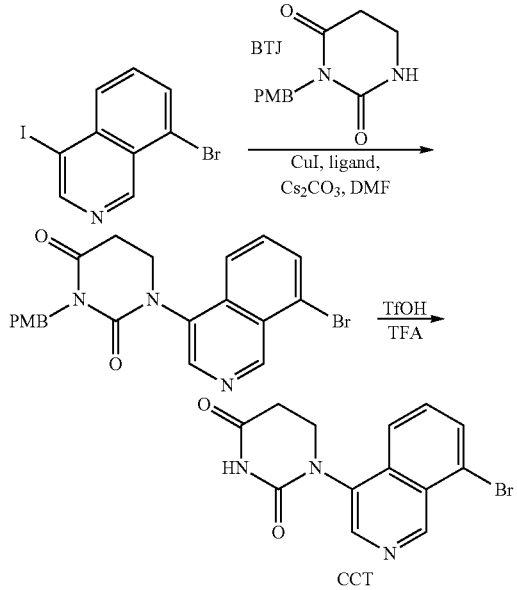

Step 1—8-Bromo-4-iodo-isoquinoline

To a solution of 8-bromoisoquinoline (2.20 g, 10.5 mmol, CAS #63927-22-0) in DCE (50 mL) was added I$_2$ (5.37 g, 21.1 mmol) and TBHP (2.86 g, 31.7 mmol). The mixture was then stirred at 85° C. for 16 hrs. On completion, the mixture was quenched with Na$_2$S$_2$O$_3$ aqueous (25 mL) and extracted with ethyl acetate (25 mL×3). The combined organic phase was dried over anhydrous sodium sulfate, filtered and concentrated to give a residue. The residue was triturated with EA to give the crude compound (1.9 g, 53% yield) as yellow solid. $^1$H NMR (400 MHz, CDCl$_3$) δ9.54 (s, 1H), 9.03 (s, 1H), 8.02 (d, J=8.4 Hz, 1H), 7.92 (d, J=7.6 Hz, 1H), 7.63 (dd, J=7.6, 8.4 Hz, 1H).

Step 2—1-(8-Bromo-4-isoquinolyl)-3-[(4-methoxyphenyl)methyl]hexahydropyrimidine-2,4-dione To a solution of 3[(4-methoxyphenyl)methyl]hexahydropyrimidine-2,4-dione (1.77 g, 7.55 mmol, Intermediate BTJ) in DMF (20 mL) was added 8-bromo-4-iodo-isoquinoline (1.68 g, 5.03 mmol), CuI (383 mg, 2.01 mmol), Cs$_2$CO$_3$ (3.28 g, 10.0 mmol), (1R,2R)—N1,N2-dimethylcyclohexane-1,2-diamine (286 mg, 2.01 mmol) and 4 Å molecular sieves (300 mg, 2.01 mmol) under N2. The mixture was stirred at 65° C. for 12 hrs. On completion, the mixture was filtered, and the filtrate was concentrated in vacuo. The residue was purified by column chromatography (SiO$_2$, Petroleum ether/Ethyl acetate=5:1 to 0:1) to give the title compound (1.2 g, 54% yield) as yellow solid. $^1$H NMR (400 MHz, CDCl$_3$) δ 9.57 (s, 1H), 8.49 (s, 1H), 7.83 (dd, J=0.8, 7.2 Hz, 1H), 7.60-7.50 (m, 1H), 7.50-7.44 (m, 1H), 7.35 (d, J=8.4 Hz, 2H), 6.79-6.76 (m, 2H), 4.92 (s, 2H), 3.83 (ddd, J=6.4, 8.0, 12.4 Hz, 1H), 3.73 (s, 3H), 3.30-3.27 (m, 1H), 2.99-2.91 (m, 2H).

Step 3—1-(8-Bromo-4-isoquinolyl)hexahydropyrimidine-2,4-dione

To a mixture of 1-(8-bromo-4-isoquinolyl)-3-[(4-methoxyphenyl)methyl]hexahydropyrimidine-2,4-dione (1 g, 2.27 mmol) in TFA (10 mL) was added TfOH (2 mL). The mixture was stirred at 70° C. for 12 hr. On completion, the reaction mixture was concentrated in vacuo, then diluted with EA (10 mL) and basified with TEA until the pH=8-9. The mixture was filtered and concentrated in vacuo to give the title compound (500 mg, 58% yield) as a brown solid. LC-MS (ESI+) m/z 319.7 (M+H)$^+$.

(3-bromocyclobutyl)methoxy-tert-butyl-dimethyl-silane (Intermediate CCU)

1-[8-[3-[[Tert-butyl (dimethyl)silyl]oxymethyl]cyclobutyl]-4-isoquinolyl]hexahydropyrimidine-2,4-dione (Intermediate CCV) and 1-[8-[3-[[tert-butyl (dimethyl)silyl]oxymethyl]cyclobutyl]-4-isoquinolyl]hexahydropyrimidine-2,4-dione (Intermediate CCW)

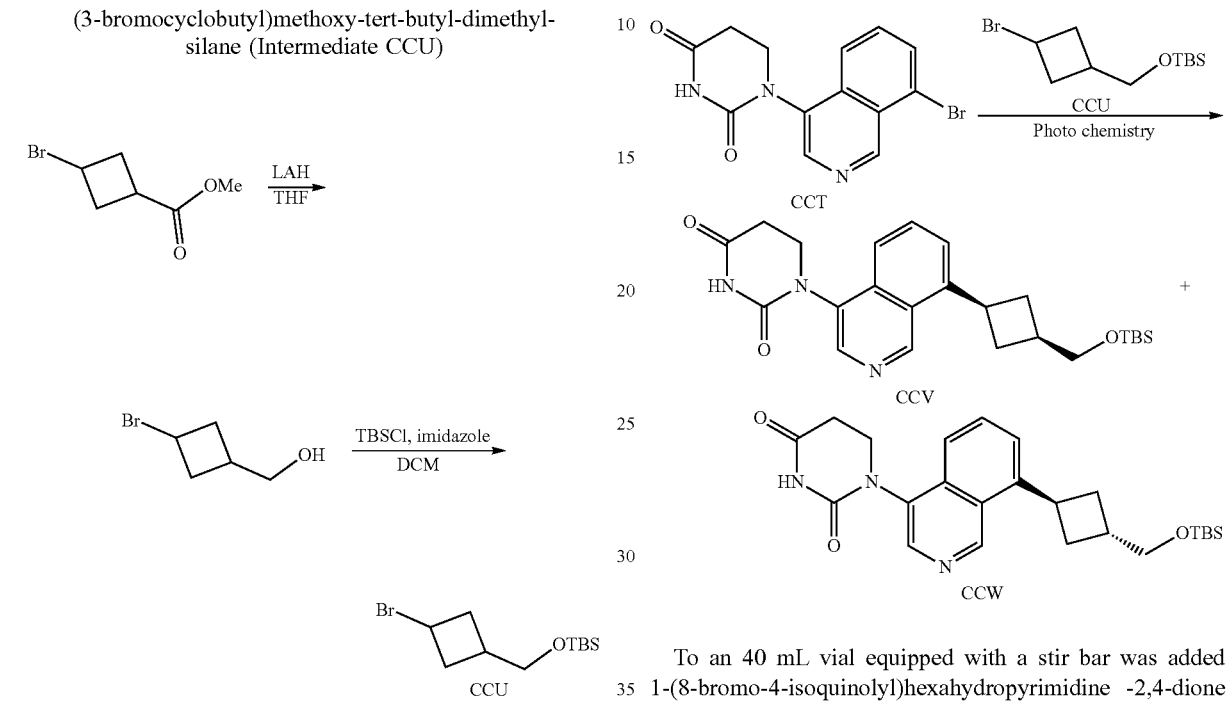

Step 1—3-Bromocyclobutyl)methanol

To a solution of methyl 3-bromocyclobutanecarboxylate (2.00 g, 10.3 mmol, CAS #4935-00-6) in THF (30 mL) was added LAH (393 mg, 10.3 mmol) at 0° C., then the mixture was stirred at 25° C. for 1 hr. On completion, the mixture was quenched with water (0.4 mL), 15% NaOH (0.4 mL) and water (1.2 mL), and filtered to give the title compound (1.60 g, 93% yield) as yellow oil. $^1$H NMR (400 MHz, CDCl$_3$-d) δ 4.60-4.53 (m, 1H), 3.66-3.64 (m, 2H), 2.81-2.72 (m, 1H), 2.63-2.52 (m, 4H), 1.61 (s, 1H).

Step 2—(3-Bromocyclobutyl)methoxy-tert-butyl-dimethyl-silane

To a solution of (3-bromocyclobutyl)methanol (500 mg, 3.03 mmol) in DCM (8 mL) was added TBSCl (557 uL, 4.54 mmol) and imidazole (412 mg, 6.06 mmol), then the mixture was stirred at 25° C. for 3 hours. On completion, the mixture was quenched with NH$_4$Cl (10 mL) and DCM (5 mL). Then the mixture was extracted with DCM (20 mL×3), the combined organic layers was concentrated in vacuo to give the residue. The residue was purified by column chromatography to give the title compound (800 mg, 94% yield) as a colorless oil. $^1$H NMR (400 MHz, CDCl$_3$-d) δ 4.60-4.53 (m, 1H), 3.66-3.64 (m, 2H), 2.81-2.72 (m, 1H), 2.63-2.52 (m, 4H), 1.61 (s, 1H).

To an 40 mL vial equipped with a stir bar was added 1-(8-bromo-4-isoquinolyl)hexahydropyrimidine -2,4-dione (500 mg, 1.56 mmol, Intermediate CCT), (3-bromocyclobutyl)methoxy-tert-butyl-dimethyl-silane (436 mg, 1.56 mmol, Intermediate CCU), Ir[dF(CF$_3$)ppy]$_2$(dtbpy)(PF6) (17.5 mg, 15.6 umol), NiCl2.dtbbpy (3.11 mg, 7.81 umol), TTMSS (388 mg, 1.56 mmol), and 2,6-Lutidine (334 mg, 3.12 mmol) in DME (5 mL). The vial was sealed and placed under nitrogen. The reaction was stirred and irradiated with a 50 W [455 nm] blue LED lamp (3 cm away), with cooling water to keep the reaction temperature at 25° C. for 14 hrs. On completion, the reaction mixture was diluted with MeOH (10 mL) and concentrated to give a residue. The residue was purified by column chromatography (SiO$^2$, DCM/EA=30:1 to 1:1) to give 1-[8-[3-[[Tert-butyl(dimethyl)silyl]oxymethyl]cyclobutyl]-4-isoquinolyl]hexahydropyrimidine-2,4-dione (150 mg, 19% yield) as a white solid ($^1$H NMR (400 MHz, DMSO-d$_6$) δ 10.53 (s, 1H), 9.31 (s, 1H), 8.56 (s, 1H), 7.89-7.81 (m, 1H), 7.81-7.73 (m, 1H), 7.64 (d, J=7.2 Hz, 1H), 4.44 (m, 1H), 3.97-3.83 (m, 3H), 3.71 (d, J=12.0 Hz, 1H), 2.97 (d, J=6.0 Hz, 1H), 2.76 (d, J=5.6 Hz, 1H), 2.42-2.31 (m, 5H), 0.93 (s, 9H), 0.12 (s, 6H); LC-MS (ESI+) m/z 440.1 (M+H)$^+$), and 1-[8-[3-[[tert-butyl (dimethyl)silyl]oxymethyl]cyclobutyl]-4-isoquinolyl]hexahydropyrimidine-2,4-dione (120 mg, 13% yield) as a white solid ($^1$H NMR (400 MHz, DMSO-d$_6$) δ10.51 (s, 1H), 9.90 (s, 1H), 9.40 (s, 1H), 8.55 (s, 1H), 7.83-7.77 (m, 1H), 7.53-7.45 (m, 1H), 4.26-4.07 (m, 1H), 3.99-3.65 (m, 3H), 3.57 (s, 1H), 3.02-2.93 (m, 1H), 2.81-2.71 (m, 1H), 2.45-2.28 (m, 5H), 0.85 (d, J=1.6 Hz, 9H), 0.03 (d, J=1.6 Hz, 6H); LC-MS (ESI+) m/z 440.1 (M+H)$^+$).

1133

3-[4-(2,4-Dioxohexahydropyrimidin-1-yl)-8-isoquinolyl]cyclobutanecarbaldehyde (Intermediate CCX)

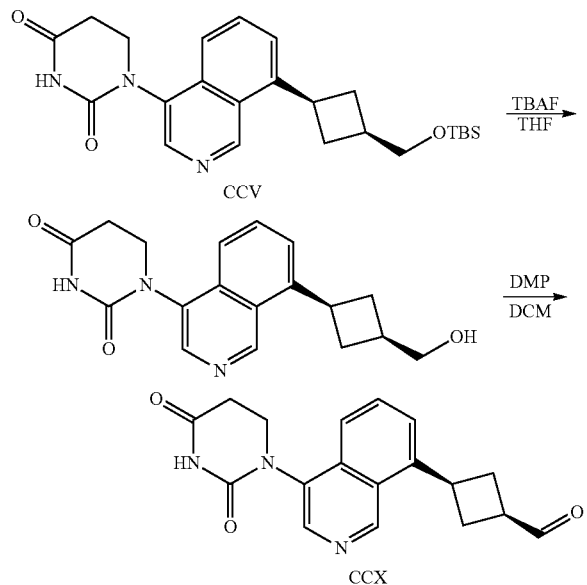

1134

Step 1—1-[8-[3-(Hydroxymethyl)cyclobutyl]-4-isoquinolyl]hexahydropyrimidine -2,4-dione To a mixture of 1-[8-[3-[[tert-butyl(dimethyl)silyl]oxymethyl]cyclobutyl]-4-isoquinolyl]hexahydropyrimidine-2,4-dione (140 mg, 318 umol, Intermediate CCV) in THF (2 mL) was added TBAF (1 M, 318 uL). The mixture was stirred at 25° C. for 1 hr. On completion, the mixture was filtered and concentrated to give the title compound (100 mg, 79% yield) as a yellow oil. LC-MS (ESI+) m/z 326.0 (M+H)$^+$.

Step 2—3-[4-(2,4-Dioxohexahydropyrimidin-1-yl)-8-isoquinolyl]cyclobutanecarbaldehyde To a mixture of 1-[8-[3-(hydroxymethyl)cyclobutyl]-4-isoquinolyl]hexahydropyrimidine-2,4-dione (90.0 mg, 276 umol) in DCM (2 mL) was added DMP (586 mg, 1.38 mmol). The mixture was then stirred at 25° C. for 1 hr. On completion, the reaction mixture was quenched with sat. Na$_2$S$_2$O$_3$ solution (2 mL) and sat. NaHCO$_3$ solution (2 mL) under stirring. Then the mixture was extracted with DCM (2×5 mL). The combined organic layer was dried over Na$_2$SO$_4$, filtered and concentrated in vacuo to give the title compound (50.0 mg, 45% yield) as a white solid. LC-MS (ESI+) m/z 324.0 (M+H)$^+$.

N-[6-methoxy-2-[4-(piperazin-1-ylmethyl)cyclohexyl]indazol-5-yl]-6-(trifluoromethyl) pyridine-2-carboxamide (Intermediate CCY)

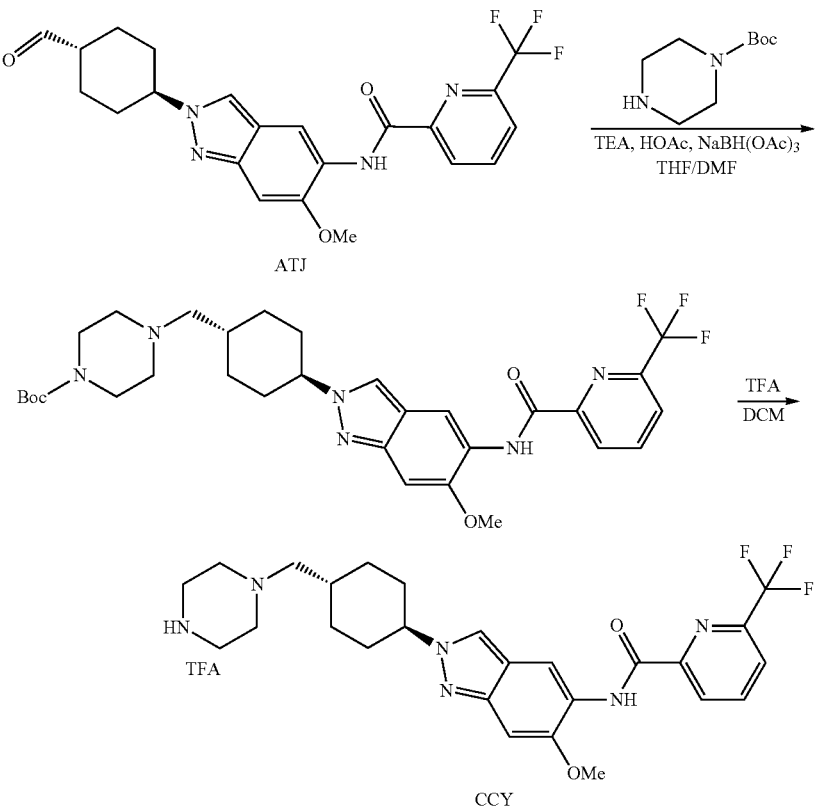

Step 1—Tert-butyl 4-[[4-[6-methoxy-5-[[6-(trifluoromethyl)pyridine-2-carbonyl]amino] indazol-2-yl] cyclohexyl]methyl]piperazine-1-carboxylate To a mixture of tert-butyl piperazine-1-carboxylate (450 mg, 2.02 mmol, HCl salt, CAS #143238-38-4) in DMF (3 mL) was added TEA (68.1 mg, 673 umol) at 20° C. until the pH stabilized at 8. The mixture was stirred at 20° C. for 0.25 hr, then AcOH (40.4 mg, 673 umol) was added at 20° C. until the pH stabilized at 5~6. The mixture was then cooled to −15° C. Subsequently, N-[2-(4-formylcyclohexyl)-6-methoxy-indazol-5-yl]-6-(trifluoromethyl)pyridine-2-carboxamide (300 mg, 673 umol, Intermediate ATJ) was added and the mixture was stirred for 0.5 hr. Next, NaBH(OAc)$_3$ (285 mg, 1.35 mmol) was added in one portion. The resulting reaction mixture was stirred at −15° C. for 1 hr. On completion, the mixture was filtered and the cake was concentrated in vacuo to give the title compound (240 mg, 52% yield) as a brown solid. $^1$H NMR (400 MHz, DMSO-d$_6$) δ 10.50 (s, 1H), 8.68 (s, 1H), 8.51-8.43 (m, 1H), 8.43-8.36 (m, 1H), 8.32 (s, 1H), 8.21 (dd, J=0.8, 7.6 Hz, 1H), 7.15 (s, 1H), 4.42-4.27 (m, 1H), 3.98 (s, 3H), 3.29-3.16 (m, 4H), 2.64-2.53 (m, 1H), 2.29 (t, J=4.8 Hz, 3H), 2.19-2.09 (m, 4H), 1.98-1.81 (m, 4H), 1.69-1.52 (m, 1H), 1.45-1.34 (m, 9H), 1.20-1.01 (m, 2H); LC-MS (ESI+) m/z 617.2 (M+H)$^+$.

Step 2—N-[6-methoxy-2-[4-(piperazin-1-ylmethyl)cyclohexyl]indazol-5-yl]-6-(trifluoromethyl) pyridine-2-carboxamide To a mixture of tert-butyl 4-[[4-[6-methoxy-5-[[6-(trifluoromethyl)pyridine-2-carbonyl]amino]indazol-2-yl]cyclohexyl]methyl]piperazine-1-carboxylate (40.0 mg, 64.8 umol) in DCM (1 mL) was added TFA (0.5 mL). The mixture was stirred at 25° C. for 1 hr. On completion, the mixture was filtered and concentrated to give a residue to give the title compound (40.9 mg, 99% yield, TFA salt) as a brown solid. LC-MS (ESI+) m/z 517.2 (M+H)$^+$.

3-[4-(2,4-Dioxohexahydropyrimidin-1-yl)-8-isoquinolyl]cyclobutanecarbaldehyde (Intermediate CCZ)

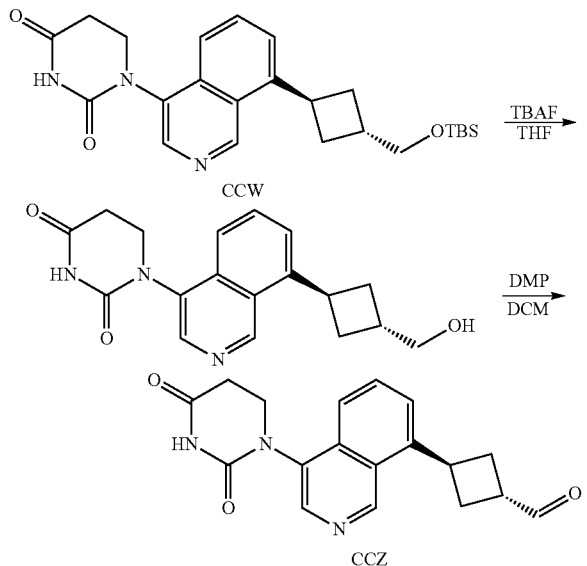

Step 1—1-[8-[3-(hydroxymethyl)cyclobutyl]-4-isoquinolyl]hexahydropyrimidine -2,4-dione To a solution of 1-[8-[3-[[tert-butyl(dimethyl)silyl]oxymethyl]cyclobutyl]-4-isoquinolyl]hexahydro-pyrimidine-2,4-dione (80 mg, 181.9 umol, Intermediate CCW) in DCM (1 mL) was added HCl/dioxane (4 M, 1.60 mL). The mixture was stirred at 25° C. for 0.5 hr. On completion, the mixture was concentrated to give the title compound (59.2 mg, 164 umol, 90% yield) as a white solid. LC-MS (ESI+) m/z 326.0 (M+H)$^+$.

Step 2—3-[4-(2,4-Dioxohexahydropyrimidin-1-yl)-8-isoquinolyl]cyclobutanecarbaldehyde To a solution of 1-[8-[3-(hydroxymethyl)cyclobutyl]-4-isoquinolyl]hexahydropyrimidine-2,4-dione (59.2 mg, 182 umol) in DCM (5 mL) and DMSO (0.1 mL) was added DMP (154.3 mg, 364 umol). The mixture was stirred at 25° C. for 1 hr. On completion, the reaction mixture was quenched by addition of Na$_2$S$_2$O$_4$ (5 mL) and NaHCO$_3$ (5 mL). The reaction mixture was filtered and concentrated in vacuo. The residue was diluted with DCM (20 mL). The mixture was filtered and concentrated to give the title compound (56 mg, 67% yield) as a white solid. LC-MS (ESI+) m/z 324 (M+H)$^+$.

N-[2-(4-Formylcyclohexyl)-6-methoxy-indazol-5-yl]-5-methoxy-pyridine-3-carboxamide (Intermediate CEE)

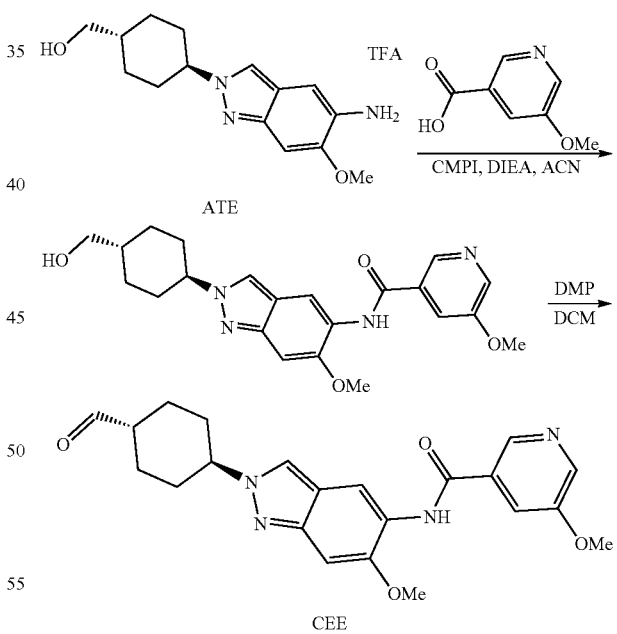

Step 1—N-[2-[4-(hydroxymethyl)cyclohexyl]-6-methoxy-indazol-5-yl]-5-methoxy-pyridine -3-carboxamide A mixture of [4-(5-amino-6-methoxy-indazol-2-yl)cyclohexyl]methanol (518 mg, 1.33 mmol, TFA, Intermediate ATE) and DIEA (515 mg, 3.99 mmol) in ACN (5 mL) was stirred for 2 min. Then a mixture of 5-methoxypyridine-3- carboxylic acid (203 mg, 1.33 mmol, CAS #1044919-31-4), DIEA (515 mg, 3.99 mmol) and CMPI (407 mg, 1.60 mmol) in ACN (2 mL) was added. The reaction mixture was stirred at 25° C. for 1 hr. On completion, the residue was diluted with water (20 mL), then the residue was extracted with EA (3×30 mL). The combined organic layer was dried over Na₂SO₄, filtered and concentrated in vacuo to give a residue. Then the residue was diluted with EA (10 ml) and the NaHCO₃ (100 mg, solid) was added at 25° C. for 10 min. Then the residue was extracted with EA (3×30 mL), dried over Na₂SO₄, filtered and concentrated to give title compound (310 mg, 56% yield) as yellow solid. ¹H NMR (400 MHz, DMSO-d₆) δ 9.65 (s, 1H), 8.72 (s, 1H), 8.47 (d, J=2.8 Hz, 1H), 8.29 (s, 1H), 8.01 (s, 1H), 7.85 (s, 1H), 7.07 (s, 1H), 4.48 (t, J=5.2 Hz, 1H), 4.39-4.32 (m, 1H), 3.91 (s, 3H), 3.86 (s, 3H), 3.29 (t, J=5.6 Hz, 2H), 2.17-2.11 (m, 2H), 1.93-1.86 (m, 4H), 1.53-1.42 (m, 1H), 1.20-1.09 (m, 2H); LC-MS (ESI⁺) m/z 411.2 (M+H)⁺.

Step 2—N-[2-(4-Formylcyclohexyl)-6-methoxy-indazol-5-yl]-5-methoxy-pyridine-3-carboxamide To a mixture of N-[2-[4-(hydroxymethyl)cyclohexyl]-6-methoxy-indazol-5-yl]-5-methoxy-pyridine-3-carboxamide (310 mg, 755 umol) in DCM (5 mL) was added DMP (480 mg, 1.13 mmol). The reaction mixture was stirred at 25° C. for 1 hr. On completion, the reaction mixture was quenched by saturated Na₂S₂O₃ (8 mL) and saturated NaHCO₃ (8 mL) at 25° C., and then stirred for 30 minutes. The mixture was extracted with DCM (2×20 mL), then the combined organic layer was dried over Na₂SO₄, filtered and concentrated in vacuo to give title compound (300 mg, 97% yield) as red solid. ¹H NMR (400 MHz, DMSO-d₆) δ 9.65 (d, J=7.6 Hz, 2H), 8.72 (s, 1H), 8.47 (d, J=2.8 Hz, 1H), 8.30 (s, 1H), 7.85 (s, 1H), 7.80-7.74 (m, 1H), 7.07 (s, 1H), 4.44-4.36 (m, 1H), 3.91 (s, 3H), 3.86 (s, 3H), 2.45-2.38 (m, 1H), 2.22-22.18 (m, 2H), 2.13-2.09 (m, 2H), 2.01-1.93 (m, 2H), 1.49-1.39 (m, 2H). LC-MS (ESI⁺) m/z 409.2 (M+H)⁺.

Tert-butyl (S)-3-(4-(3-(4-methoxybenzyl)-2,4-dioxo-tetrahydropyrimidin-1(2H)-yl)isoquinolin-8-yl)pyrrolidine-1-carboxylate (Intermediate CEF) and tert-butyl (R)-3-(4-(3-(4-methoxybenzyl)-2,4-dioxotetrahydropyrimidin-1(2H)-yl)isoquinolin-8-yl)pyrrolidine-1-carboxylate (Intermediate CEG)

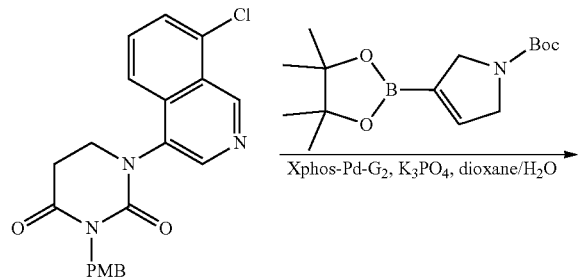

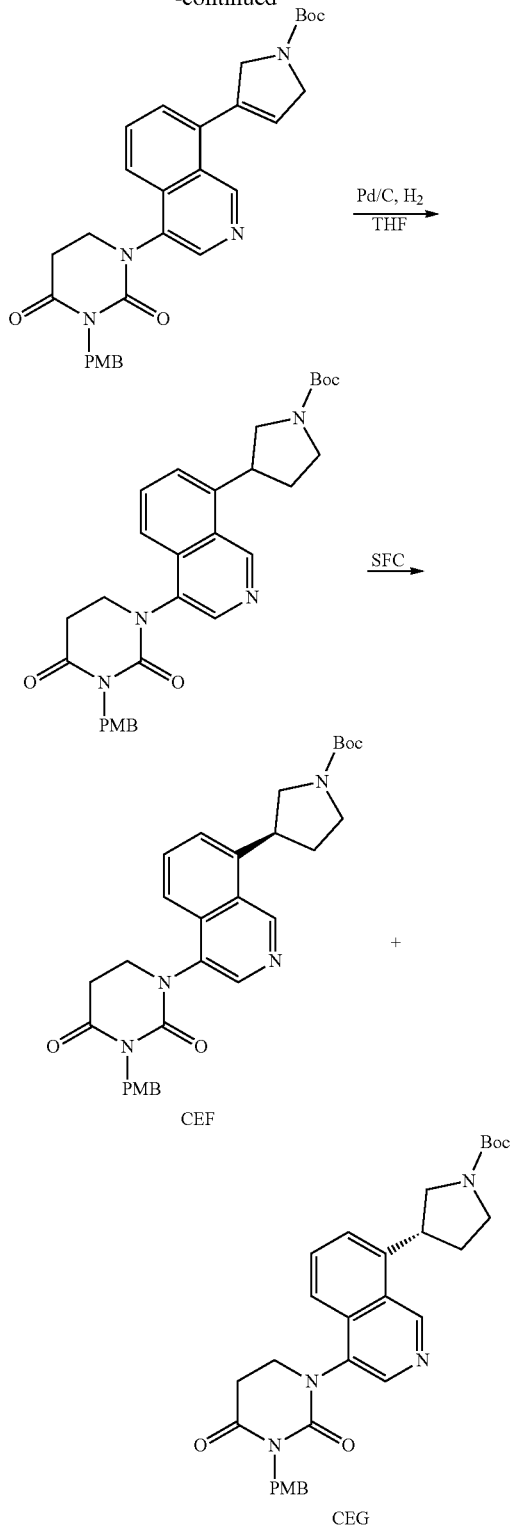

Step 1—Tert-butyl3-[4-[3-[(4-methoxyphenyl)methyl]-2,4-dioxo-hexahydropyrimidin-1-yl]-8-isoquinolyl]-2,5-dihydropyrrole-1-carboxylate To a solution of tert-butyl 3-(4,4,5,5-tetramethyl-1,3,2-dioxaborolan-2-yl)-2,5-dihydropyrrole-1-carboxylate (2.91 g, 9.85 mmol, CAS #212127-83-8) and 1-(8-chloro-4-isoquinolyl)-3-[(4-methoxyphenyl)methyl] hexahydropyrimidine-2,4-dione (3 g, 7.58 mmol, synthesized via Steps 1-2 of Intermediate BSL) in dioxane (30 mL) and H$_2$O (10 mL) was added K$_3$PO$_4$ (4.83 g, 22.7 mmol) and XPHOS-PD-G2 (596 mg, 757 umol). Then the mixture was stirred at 80° C. for 5 hrs. On completion, the reaction mixture was filtered and concentrated in vacuo to give a residue. The residue was purified by reverse phase (0.1% FA condition) to give the title compound (2 g, 49% yield) as a white solid. $^1$H NMR (400 MHz, DMSO-d$_6$) δ 9.54 (s, 1H), 8.60 (s, 1H), 7.91 (d, J=8.4 Hz, 1H), 7.79 (t, J=7.6 Hz, 1H), 7.71 (d, J=6.8 Hz, 1H), 7.26 (d, J=8.4 Hz, 2H), 6.88 (d, J=8.4 Hz, 2H), 6.21 (d, J=11.6 Hz, 1H), 5.75 (s, 1H), 4.84 (s, 2H), 4.55 (s, 2H), 4.38 (d, J=3.6 Hz, 2H), 4.05-3.87 (m, 1H), 3.73 (s, 3H), 3.21-3.11 (m, 1H), 2.97 (d, J=5.6, 16.4 Hz, 1H), 1.46 (d, J=7.9 Hz, 9H). LC-MS (ESI$^+$) m/z 529.3 (M+H)$^+$.

Step 2—Tert-butyl 3-[4-[3-[(4-methoxyphenyl)methyl]-2,4-dioxo-hexahydropyrimidin-1-yl]-8-isoquinolyl]pyrrolidine-1-carboxylate To a solution of tert-butyl 3-[4-[3-[(4-methoxyphenyl)methyl]-2,4-dioxo-hexahydropyrimidin-1-yl]-8-isoquinolyl]-2,5-dihydropyrrole-1-carboxylate (1 g, 1.89 mmol) in THF (10 mL) was added Pd/C (1 g, 10 wt %), then the mixture was stirred at 25° C. for 2 hrs under H$_2$ (15 psi). On completion, the reaction mixture was filtered and concentrated in vacuo to give a residue. The residue was purified by column chromatography (SiO$_2$, PE:EA=50:1 to PE:EA=3:1) to give the title compound (800 mg, 79% yield) as a yellow solid. $^1$H NMR (400 MHz, DMSO-d$_6$) δ 9.68 (s, 1H), 8.61 (s, 1H), 7.88-7.73 (m, 2H), 7.66 (d, J=6.4 Hz, 1H), 7.27 (d, J=8.8 Hz, 2H), 6.93-6.86 (m, 2H), 4.84 (s, 2H), 4.43-4.30 (m, 1H), 3.99-3.77 (m, 3H), 3.74 (s, 3H), 3.55-3.41 (m, 3H), 3.20-3.11 (m, 1H), 2.98 (d, J=5.6, 16.4 Hz, 1H), 2.42-2.32 (m, 1H), 2.19-2.07 (m, 1H), 1.43 (d, J=9.6 Hz, 9H). LC-MS (ESI$^+$) m/z 531.4 (M+H)$^+$.

Step 3—Tert-butyl (S)-3-(4-(3-(4-methoxybenzyl)-2,4-dioxotetrahydropyrimidin-1(2H)-yl)isoquinolin-8-yl)pyrrolidine-1-carboxylate and tert-butyl (R)-3-(4-(3-(4-methoxybenzyl)-2,4-dioxotetrahydropyrimidin-1(2H)-yl)isoquinolin-8-yl)pyrrolidine-1-carboxylate Tert-butyl 3-[4-(2,4-dioxohexahydropyrimidin-1-yl)-8-isoquinolyl]pyrrolidine-1-carboxylate (380 mg, 925 umol) separated by SFC to give tert-butyl (S)-3-(4-(3-(4-methoxybenzyl)-2,4-dioxotetrahydropyrimidin-1(2H)-yl)isoquinolin-8-yl)pyrrolidine-1-carboxylate (190 mg, 50% yield, tR=1.48) as a white solid ($^1$H NMR (400 MHz, DMSO-d$_6$) δ 10.54 (s, 1H), 9.66 (s, 1H), 8.59 (s, 1H), 7.90 (d, J=8.4 Hz, 1H), 7.79 (t, J=7.6 Hz, 1H), 7.65 (d, J=6.8 Hz, 1H), 4.49-4.36 (m, 1H), 3.97-3.80 (m, 2H), 3.76-3.66 (m, 1H), 3.53-3.36 (m, 3H), 2.98 (d, J=6.4, 16.4 Hz, 1H), 2.76-2.74 (m, 1H), 2.42-2.35 (m, 1H), 2.19-2.07 (m, 1H), 1.43 (d, J=9.6 Hz, 9H). LC-MS (ESI$^+$) m/z 411.3 (M−120+H)$^+$) and tert-butyl (R)-3-(4-(3-(4-methoxybenzyl)-2,4-dioxotetrahydropyrimidin-1(2H)-yl)isoquinolin-8-yl)pyrrolidine-1-carboxylate (80 mg, 42% yield, t$_R$=1.61). $^1$H NMR (400 MHz, DMSO-d$_6$) δ 9.66 (s, 1H), 8.59 (s, 1H), 7.90 (d, J=8.4 Hz, 2H), 4.50-4.33 (m, 1H), 4.02-3.80 (m, 2H), 3.76-3.64 (m, 1H), 3.54-3.35 (m, 3H), 2.98 (d, J=6.0, 10.0, 16.4 Hz, 1H), 2.82-2.65 (m, 2H), 2.21-2.07 (m, 2H), 1.42 (d, J=9.6 Hz, 9H); LC-MS (ESI$^+$) m/z 411.3 (M−120+H)$^+$. Absolute stereochemistry was arbitrarily assigned.

1-[8-[(3S)-pyrrolidin-3-yl]-4-isoquinolyl]hexahydropyrimidine-2,4-dione (Intermediate CEH)

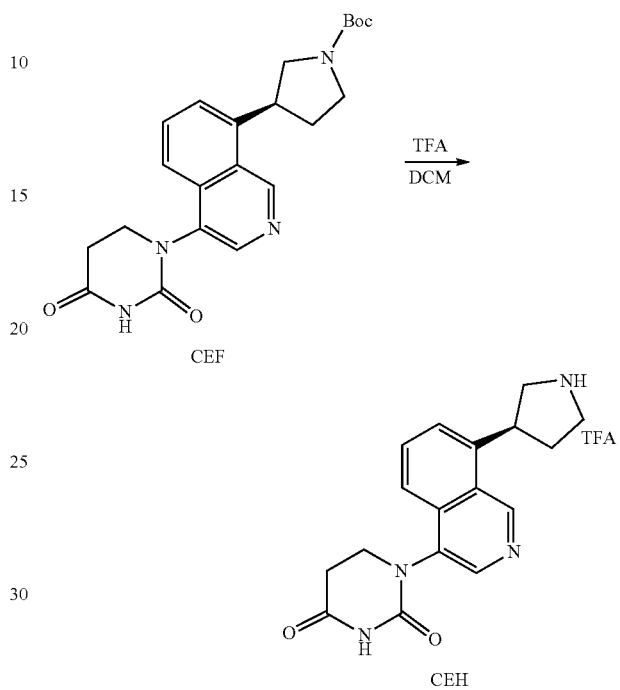

To a solution of tert-butyl (3S)-3-[4-(2,4-dioxohexahydropyrimidin-1-yl)-8-isoquinolyl]pyrrolidine-1-carboxylate (30 mg, 73.0 umol) in DCM (0.5 mL) was added TFA (462 mg, 4.05 mmol), then the mixture was stirred at 25° C. for 1 hr. On completion, the reaction mixture was concentrated in vacuo to give the title compound (30 mg, 96% yield) as a yellow oil. LC-MS (ESI$^+$) m/z 311.3 (M+H)$^+$.

N-[2-[4-(iodomethyl)cyclohexyl]-6-methoxy-indazol-5-yl]-6-(trifluoromethyl)pyridine-2-carboxamide (Intermediate CEI)

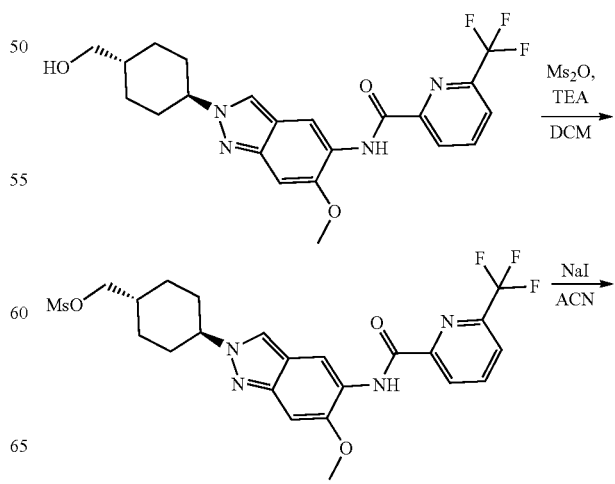

-continued

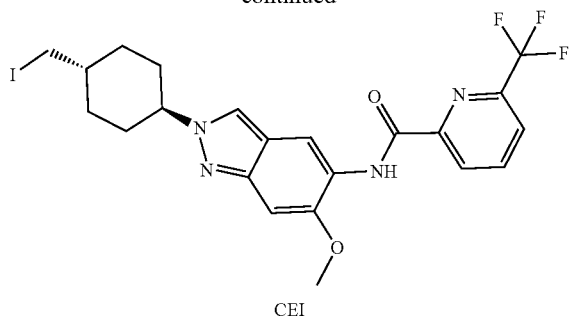

CEI

Step 1—[4-[6-Methoxy-5-[[6-(trifluoromethyl)pyridine-2-carbonyl]amino]indazol-2-yl]cyclohexyl] methyl methanesulfonate To a solution of N-[2-[4-(hydroxymethyl)cyclohexyl]-6-methoxy-indazol-5-yl]-6-(trifluoromethyl) pyridine-2-carboxamide (300 mg, 668 umol, synthesized via Step 1 of Intermediate ATJ) in DCM (3 mL) was added TEA (203 mg, 2.01 mmol) and methylsulfonyl methanesulfonate (174 mg, 1.00 mmol). The reaction mixture was stirred at 25° C. for 3 hrs. On completion, the reaction mixture was diluted with H$_2$O (10 mL), and extracted with DCM (2×15 mL). The combined organic layer was washed with brine (2×15 mL), dried over Na$_2$SO$_4$ and filtered. The filtrate was concentrated in vacuo to give the title compound (320 mg, 90% yield) as a white solid. LC-MS (ESI+) m/z 527.1 (M+H)$^+$.

Step 2—N-[2-[4-(iodomethyl)cyclohexyl]-6-methoxy-indazol-5-yl]-6-(trifluoromethyl)pyridine-2-carboxamide To a solution of [4-[6-methoxy-5-[[6-(trifluoromethyl) pyridine-2-carbonyl]amino]indazol-2-yl]cyclohexyl]methyl methanesulfonate (320 mg, 607 umol) in ACN (4 mL) was added NaI (455 mg, 3.04 mmol). The reaction was stirred at 80° C. for 16 hrs. On completion, the reaction mixture was diluted with H$_2$O (15 mL), and extracted with EA (2×20 mL). The combined organic layer was washed with brine (2×20 mL), dried over Na$_2$SO$_4$ and filtered. The filtrate was concentrated in vacuo to give a residue. The residue was purified by reverse phase (0.1% FA condition) to give the title compound (240 mg, 70% yield) as a yellow solid. $^1$H NMR (400 MHz, DMSO-d$_6$) δ 10.48 (s, 1H), 8.67 (s, 1H), 8.47-8.42 (m, 1H), 8.41-8.36 (m, 1H), 8.30 (s, 1H), 8.19 (d, J=7.6 Hz, 1H), 7.14 (s, 1H), 4.43-4.27 (m, 1H), 3.97 (s, 3H), 3.28 (d, J=6.0 Hz, 2H), 2.13 (d, J=11.6 Hz, 2H), 2.04-1.85 (m, 4H), 1.58-1.45 (m, 1H), 1.31-1.16 (m, 2H); LC-MS (ESI+) m/z 559.0 (M+H)$^+$.

Tert-butyl (4R)-2,2-dimethyl-4-[3-methyl-2-oxo-1-(2-trimethylsilylethoxymethyl) benzimidazol-4-yl] piperidine-1-carboxylate (Intermediate CEJ) and tert-butyl (4S)-2,2-dimethyl-4-[3-methyl-2-oxo-1-(2-trimethylsilylethoxymethyl)benzimidazol-4-yl] piperidine-1-carboxylate (Intermediate CEK)

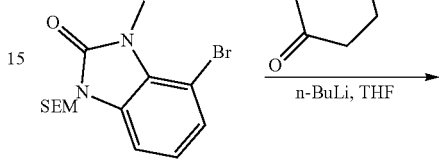

BED

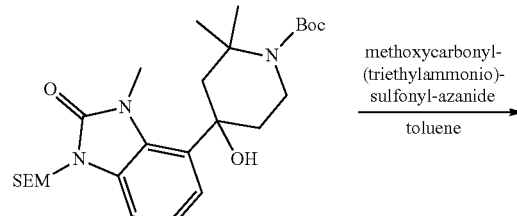

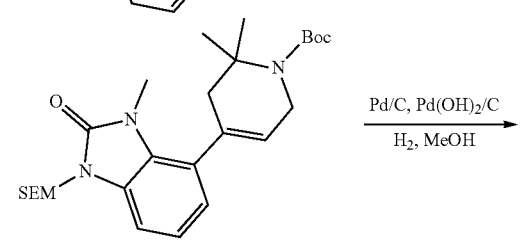

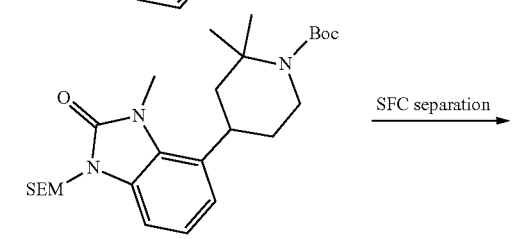

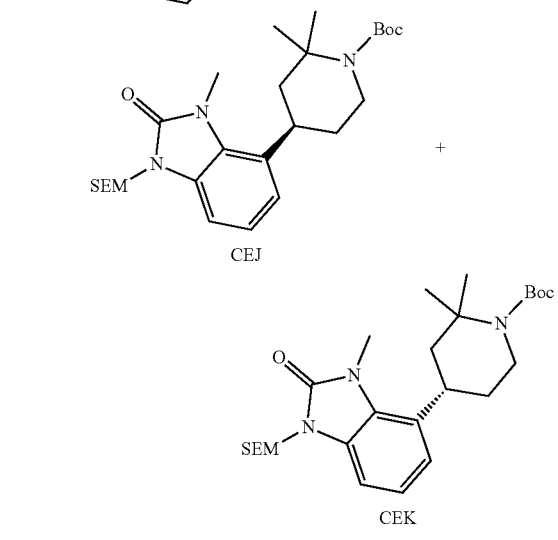

CEJ

CEK

Step 1—Tert-butyl 4-hydroxy-2,2-dimethyl-4-[3-methyl-2-oxo-1-(2-trimethylsilylethoxymethyl) benzimidazol-4-yl]piperidine-1-carboxylate To a solution of 4-bromo-3-methyl-1-(2-trimethylsilylethoxymethyl)benzimidazol-2-one (714 mg, 2.00 mmol, Intermediate BED) in THF (10 mL) was added n-BuLi (2.5 M, 879 uL) at −78° C., the reaction mixture was stirred at −78° C. for 30 mins, then tert-butyl 2,2-dimethyl-4-oxo-piperidine-1-carboxylate (500 mg, 2.20 mmol, CAS #346893-03-1) was added to the mixture. Then the reaction mixture was stirred at −78° C. for 1 hr. On completion, the reaction mixture was quenched with NH$_4$Cl (10 mL), then extracted with EA (2×20 mL). The organic phase was combined and dried with Na$_2$SO$_4$, then filtered and the filtrate was concentrated in vacuo to give a residue. The residue was purified by reverse phase (0.1% FA condition) to give the title compound (1.50 g, 37% yield) as a white solid. LC-MS (ESI$^+$) m/z 506.1 (M+H)$^+$.

Step 2—Tert-butyl 6,6-dimethyl-4-[3-methyl-2-oxo-1-(2-trimethylsilylethoxymethyl)benzimidazol-4-yl]-2,5-dihydropyridine-1-carboxylate To a solution of tert-butyl 4-hydroxy-2,2-dimethyl-4-[3-methyl-2-oxo-1-(2-trimethylsilylethoxymethyl)benzimidazol-4-yl]piperidine-1-carboxylate (1.50 g, 2.97 mmol) in toluene (5 mL) was added methoxycarbonyl-(triethylammonio)sulfonylazanide (1.06 g, 4.45 mmol). Then the reaction mixture was stirred at 90° C. for 12 hrs. On completion, the reaction mixture was concentrated in vacuo to give a residue. The residue was purified by reverse phase (0.1% FA condition) to give the title compound (1.00 g, 69% yield) as colorless oil. $^1$H NMR (400 MHz, DMSO-d$_6$) δ 7.17-7.12 (m, 1H), 7.08-7.04 (m, 1H), 6.86-6.84 (m, 1H), 5.86 (t, J=4.0 Hz, 1H), 5.25 (s, 2H), 4.03-3.94 (m, 2H), 3.55 (t, J=8.0 Hz, 2H), 3.30 (s, 3H), 2.46 (s, 2H), 1.45 (s, 6H), 1.43 (s, 9H), 0.87-0.83 (m, 2H), 0.06 (s, 9H).

Step 3—Tert-butyl 2,2-dimethyl-4-[3-methyl-2-oxo-1-(2-trimethylsilylethoxymethyl)benzimidazol-4-yl]piperidine-1-carboxylate To a solution of tert-butyl 6,6-dimethyl-4-[3-methyl-2-oxo-1-(2-trimethylsilylethoxymethyl) benzimidazol-4-yl]-2,5-dihydropyridine-1-carboxylate (1.00 g, 2.05 mmol) in MeOH (20 mL) was added Pd/C (0.50 g, 10 wt %). The reaction mixture was then stirred at 40° C. for 16 hrs under H$_2$ (50 psi). On completion, the reaction mixture was filtered and the filtrate was concentrated in vacuo to give the title compound (980 mg, 98% yield) as a white solid. $^1$H NMR (400 MHz, DMSO-d$_6$) δ 7.11-6.99 (m, 3H), 5.46 (s, 1H), 5.23 (s, 2H), 3.91-3.85 (m, 1H), 3.61 (s, 3H), 3.55-3.50 (m, 2H), 3.17 (d, J=5.2 Hz, 2H), 1.89-1.86 (m, 1H), 1.77-1.70 (m, 2H), 1.50-1.35 (m, 15H), 0.88-0.79 (m, 2H), 0.06 (m, 9H).

Step 4—Tert-butyl (4R)-2,2-dimethyl-4-[3-methyl-2-oxo-1-(2-trimethylsilylethoxymethyl) benzimidazol-4-yl]piperidine-1-Carboxylate and tert-butyl (4S)-2,2-dimethyl-4-[3-methyl-2-oxo-1-(2-trimethylsilylethoxymethyl)benzimidazol-4-yl]piperidine-1-carboxylate Tert-butyl 2,2-dimethyl-4-[3-methyl-2-oxo-1-(2-trimethylsilylethoxymethyl)benzimidazol-4-yl]piperidine-1-carboxylate (1.00 g, 2.04 mmol) separated by SFC (column: DAICEL CHIRALPAK IC (250 mm*30 mm, 10 um); mobile phase: [0.1% NH$_3$—H$_2$O MEOH]; B %: 40%-40%, 7; 150 min) and SFC(column: Phenomenex-Cellulose-2 (250 mm*30 mm, 10 um); mobile phase: [0.1% NH$_3$—H$_2$O MEOH]; B %: 20%-20%, 2.1; 30 min) to give tert-butyl (4R)-2,2-dimethyl-4-[3-methyl-2-oxo-1-(2-trimethylsilylethoxymethyl) benzimidazol-4-yl]piperidine-1-carboxylate (240 mg, 24% yield) as a white solid ($^1$H NMR (400 MHz, DMSO-d$_6$) δ 7.13-7.09 (m, 3H), 5.29 (s, 2H), 3.96-3.93 (m, 1H), 3.68 (s, 3H), 3.65-3.56 (m, 3H), 3.32-3.22 (m, 1H), 2.00-1.90 (m, 1H), 1.85-1.72 (m, 3H), 1.56 (s, 3H), 1.48 (s, 9H), 1.43 (s, 3H), 0.94-0.85 (m, 2H), 0.008 (s, 9H), LC-MS (ESI$^+$) m/z 490.2 (M+H)$^+$) and tert-butyl (4S)-2,2-dimethyl-4-[3-methyl-2-oxo-1-(2-trimethylsilylethoxymethyl)benzimidazol-4-yl]piperidine-1-carboxylate (322 mg, 32% yield) as a white solid ($^1$H NMR (400 MHz, DMSO-d$_6$) δ 7.10-7.00 (m, 3H), 5.23 (s, 2H), 3.90-3.60 (m, 1H), 3.61 (s, 3H), 3.60-3.50 (m, 3H), 3.22-3.20 (m, 1H), 1.95-1.84 (m, 1H), 1.78-1.65 (m, 3H), 1.49 (s, 3H), 1.42 (s, 9H), 1.37 (s, 3H), 0.89-0.80 (m, 2H), 0.07 (s, 9H), LC-MS (ESI$^+$) m/z 490.2 (M+H)$^+$). Absolute stereochemistry was assigned arbitrarily.

3-[4-[(4 S)-2,2-dimethyl-4-piperidyl]-3-methyl-2-oxo-benzimidazol-1-yl]piperidine-2,6-dione (Intermediate CEL)

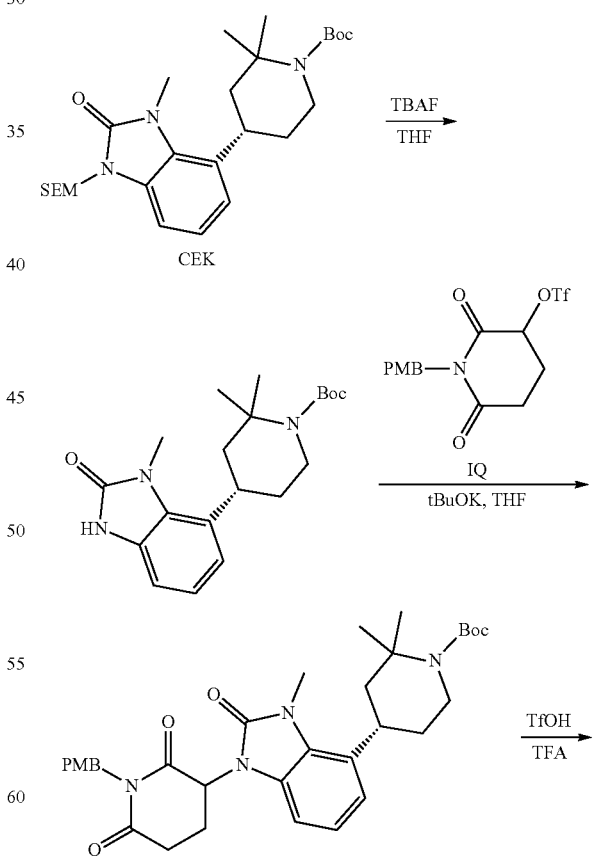

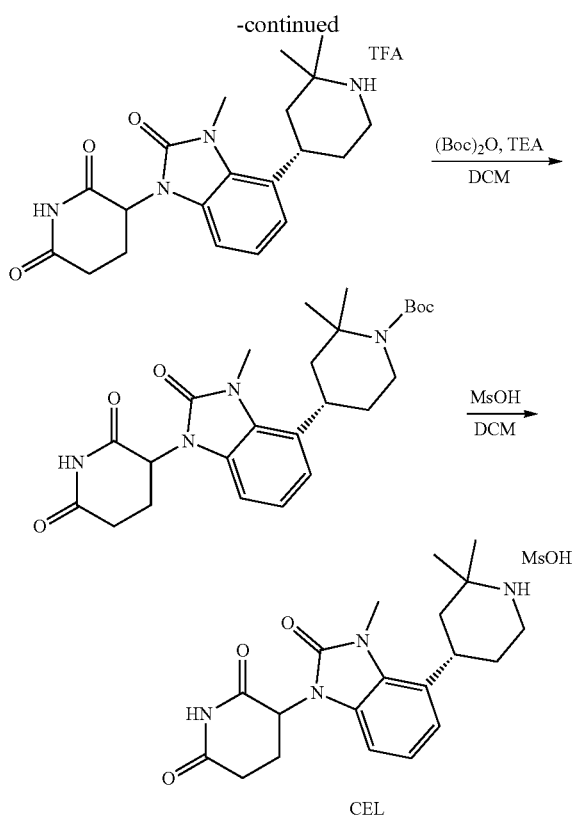

CEL

Step 1—Tert-butyl (4S)-2,2-dimethyl-4-(3-methyl-2-oxo-1H-benzimidazol-4-yl)piperidine-1-carboxylate To a solution of tert-butyl (4S)-2,2-dimethyl-4-[3-methyl-2-oxo-1-(2-trimethylsilylethoxymethyl) benzimidazol-4-yl] piperidine-1-carboxylate (300 mg, 612 umol, Intermediate CEK) in THF (3 mL) was added TBAF (1 M, 3.06 mL). The reaction mixture was stirred at 70° C. for 16 hrs. On completion, the reaction mixture was diluted with $H_2O$ (15 mL), and extracted with EA (2×20 mL). The combined organic layer was washed with brine (2×20 mL), dried over $Na_2SO_4$ and filtered. The filtrate was concentrated in vacuo to give the title compound (210 mg, 95% yield) as a white solid. LC-MS (ESI+) m/z 304.2 (M+H−56)+.

Step 2—Tert-butyl (4S)-4-[1-[1-[(4-methoxyphenyl) methyl]-2,6-dioxo-3-piperidyl]-3-methyl-2-oxo-benzimidazol-4-yl]-2,2-dimethyl-piperidine-1-carboxylate To a solution of tert-butyl (4S)-2,2-dimethyl-4-(3-methyl-2-oxo-1H-benzimidazol-4-yl) piperidine-1-carboxylate (135 mg, 375 umol) in THF (2 mL) was added t-BuOK (63.2 mg, 563 umol). The mixture was stirred at −10° C. for 30 mins. Then a solution of [1-[(4-methoxyphenyl) methyl]-2,6-dioxo-3-piperidyl]trifluoromethanesulfonate (214 mg, 563 umol, Intermediate IQ) in THF (2 mL) was added dropwise to the mixture, and the reaction mixture was stirred at −10° C. for 30 mins. On completion, the reaction mixture was diluted with $H_2O$ (15 mL), and extracted with EA (2×20 mL). The combined organic layer was washed with brine (2×20 mL), dried over $Na_2SO_4$ and filtered. The filtrate was concentrated in vacuo to give a residue. The residue was purified by reverse phase (0.1% FA condition) to give the title compound (125 mg, 56% yield) as a white solid. $^1$H NMR (400 MHz, DMSO-$d_6$) δ 7.21 (d, J=8.4 Hz, 2H), 7.06-6.93 (m, 2H), 6.85 (d, J=8.4 Hz, 3H), 5.52 (dd, J=5.2, 12.8 Hz, 1H), 4.90-4.68 (m, 2H), 3.89 (td, J=4.4, 13.2 Hz, 1H), 3.75-3.67 (m, 3H), 3.62 (s, 3H), 3.59-3.53 (m, 1H), 3.23-3.17 (m, 1H), 3.10-2.99 (m, 1H), 2.86-2.69 (m, 2H), 2.06-2.01 (m, 1H), 1.90 (td, J=4.4, 8.8 Hz, 1H), 1.80-1.65 (m, 3H), 1.49 (s, 3H), 1.42 (s, 9H), 1.37 (s, 3H); LC-MS (ESI+) m/z 591.5 (M+H)+.

Step 3—3-[4-[(4S)-2,2-Dimethyl-4-piperidyl]-3-methyl-2-oxo-benzimidazol-1-yl]piperidine-2,6-dione To a solution of tert-butyl (4S)-4-[1-[1-[(4-methoxyphenyl)methyl]-2,6-dioxo-3-piperidyl]-3-methyl-2-oxo-benzimidazol-4-yl]-2,2-dimethyl-piperidine-1-carboxylate (120 mg, 203.15 umol) and in TFA (1.5 mL) was added TfOH (510 mg, 3.40 mmol). Then the reaction mixture was stirred at 70° C. for 2 hrs. On completion, the reaction mixture was concentrated in vacuo to give the title compound (90.0 mg, 91% yield, TFA) as a yellow solid. LC-MS (ESI+) m/z 371.1 (M+H)+.

Step 4—Tert-butyl (4S)-4-[1-(2,6-dioxo-3-piperidyl)-3-methyl-2-oxo-benzimidazol-4-yl]-2,2-dimethyl-piperidine-1-carboxylate To a solution of 3-[4-[(4S)-2,2-dimethyl-4-piperidyl]-3-methyl-2-oxo-benzimidazol-1-yl]piperidine-2,6-dione (90.0 mg, 185 umol, TFA) in DCM (1 mL) was added TEA (93.9 mg, 928 umol). Then $Boc_2O$ (48.6 mg, 222 umol) was added. The reaction was stirred at 25° C. for 16 hrs. On completion, the reaction mixture was diluted with $H_2O$ (5 mL) and extracted with DCM (2×5 mL). The combined organic layer was washed with brine (2×5 mL), dried over $Na_2SO_4$ and filtered. The filtrate was concentrated in vacuo to give a residue. The residue was purified by reverse phase (neutral condition) to give the title compound (70.0 mg, 80% yield) as a white solid. $^1$H NMR (400 MHz, DMSO-$d_6$) δ 11.08 (s, 1H), 7.07-6.93 (m, 3H), 5.37 (dd, J=5.2, 12.4 Hz, 1H), 3.89 (td, J=4.4, 13.6 Hz, 1H), 3.62 (s, 3H), 3.27-3.17 (m, 1H), 2.95-2.82 (m, 1H), 2.78-2.55 (m, 3H), 2.05-1.95 (m, 1H), 1.90 (dd, J=3.2, 12.4 Hz, 1H), 1.83-1.64 (m, 3H), 1.49 (s, 3H), 1.42 (s, 9H), 1.37 (s, 3H); LC-MS (ESI+) m/z 471.2 (M+H)+.

Step 5—3-[4-[(4S)-2,2-dimethyl-4-piperidyl]-3-methyl-2-oxo-benzimidazol-1-yl]piperidine-2,6-dione To a solution of tert-butyl (4S)-4-[1-(2,6-dioxo-3-piperidyl)-3-methyl-2-oxo-benzimidazol-4-yl]-2,2-dimethyl-piperidine-1-carboxylate (70.0 mg, 148 umol) in DCM (0.5 mL) was added MsOH (42.8 mg, 446 umol). The reaction was stirred at 25° C. for 1 hr. On completion, the reaction mixture was concentrated in vacuo to give the title compound (69.0 mg, 99% yield, MsOH) as a colorless oil. LC-MS (ESI+) m/z 371.1 (M+H)+.

N-[6-ethoxy-2-(4-formylcyclohexyl)indazol-5-yl]-6-(trifluoromethyl)pyridine-2-carboxamide (Intermediate CEM)

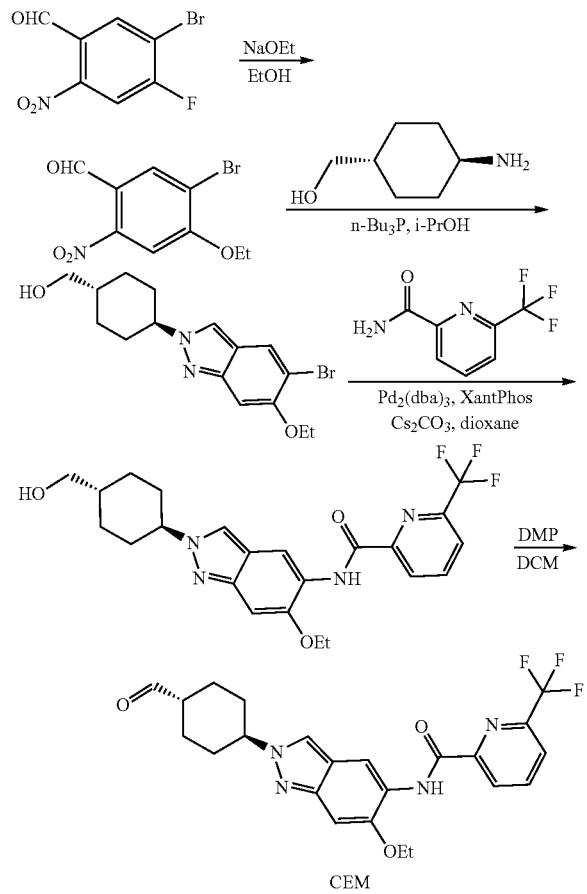

Step 1—5-Bromo-4-ethoxy-2-nitro-benzaldehyde

The solution of 5-bromo-4-fluoro-2-nitro-benzaldehyde (3.0 g, 12.1 mmol, synthesized via Step 1 of Intermediate ATE) in EtOH (60 mL) was cooled to 0° C., then NaOEt (988 mg, 14.5 mmol) was added. The reaction mixture was then stirred at 25° C. for 12 hrs. On completion, the reaction mixture was quenched with water (50 mL), then extracted by EtOAc (100 ml×3). The organic layers were combined, washed with brine (50 mL), dried over anhydrous $Na_2SO_4$, and concentrated in vacuo to give the residue. The residue was purified by column chromatography ($SiO_2$, Petroleum ether/Ethyl acetate=50/1 to 30/1) to give the title compound (770 mg, 23% yield) as yellow solid. $^1$H NMR (400 MHz, DMSO-$d_6$) δ 10.03 (s, 1H), 8.16 (s, 1H), 7.77 (s, 1H), 4.34-4.32 (m, 2H), 1.41 (t, J=6.8 Hz, 3H).

Step 2—[4-(5-Bromo-6-ethoxy-indazol-2-yl)cyclohexyl]methanol

A solution of 5-bromo-4-ethoxy-2-nitro-benzaldehyde (1.19 g, 4.34 mmol) and (4-aminocyclohexyl) methanol (617 mg, 4.78 mmol, CAS #1467-84-1) in IPA (30 mL) was stirred at 80° C. for 12 hrs under $N_2$ atmosphere. Then the mixture was cooled to 25° C., and tributylphosphane (2.64 g, 13.0 mmol) was added. The reaction mixture was stirred at 80° C. for 6 hrs under $N_2$ atmosphere. On completion, the reaction mixture was concentrated in vacuo to give the residue. The residue was purified by column chromatography ($SiO_2$, Petroleum ether/Ethyl acetate=30/1 to 1/1) to give the title compound (740 mg, 46% yield) as orange solid. $^1$H NMR (400 MHz, DMSO-$d_6$) δ 8.26 (s, 1H), 7.95 (s, 1H), 7.08 (s, 1H), 4.54-4.52 (m, 1H), 4.49 (t, J=5.2 Hz, 1H), 4.36-4.34 (m, 1H), 4.09-4.06 (m, 2H), 3.28 (t, J=6.0 Hz, 2H), 2.17-2.05 (m, 2H), 1.94-1.82 (m, 3H), 1.39 (t, J=6.8 Hz, 3H), 1.15 (s, 2H), 0.91-0.83 (m, 1H). LC-MS (ESI+) m/z 353.1 (M+H)$^+$.

Step 3—N-[6-ethoxy-2-[4-(hydroxymethyl)cyclohexyl]indazol-5-yl]-6-(trifluoromethyl)pyridine-2-carboxamide A mixture of [4-(5-bromo-6-ethoxy-indazol-2-yl)cyclohexyl]methanol (500 mg, 1.42 mmol), 6-(trifluoromethyl)pyridine-2-carboxamide (323 mg, 1.70 mmol, CAS #22245-84-7), [2-(2-aminophenyl) phenyl]-methyl sulfonyloxypalladium; ditert-butyl-[2-(2,4,6-triisopropylphenyl)phenyl] phosphane (112 mg, 141 umol), and t-BuOK (317 mg, 2.83 mmol) in dioxane (10 mL) was degassed and purged with $N_2$ three times. Then the mixture was stirred at 80° C. for 16 hrs under $N_2$ atmosphere. On completion, the reaction mixture was filtered to give a filtrate, then concentrated in vacuo to give a residue. The residue was purified by reverse phase (0.1% FA condition) to give the title compound (100 mg, 15% yield) as yellow solid. $^1$H NMR (400 MHz, DMSO-$d_6$) δ 10.74 (s, 1H), 8.70 (s, 1H), 8.54-8.38 (m, 2H), 8.34 (s, 1H), 8.23 (d, J=7.2 Hz, 1H), 7.14 (s, 1H), 4.49 (t, J=5.6 Hz, 1H), 4.42-4.30 (m, 1H), 4.20 (q, J=6.4 Hz, 2H), 3.30-3.28 (m, 3H), 2.14 (d, J=10.8 Hz, 2H), 1.96-1.82 (m, 4H), 1.51 (t, J=6.8 Hz, 3H), 1.22-1.07 (m, 2H). LC-MS (ESI+) m/z 463.1 (M+H)$^+$.

Step 4—N-[6-ethoxy-2-(4-formylcyclohexyl)indazol-5-yl]-6-(trifluoromethyl)pyridine-2-carboxamide To a solution of N-[6-ethoxy-2-[4-(hydroxy methyl)cyclohexyl]indazol-5-yl]-6-(trifluoromethyl) pyridine-2-carboxamide (100 mg, 216 umol) in DCM (2 mL) was added DMP (110 mg, 259 umol). The mixture was then stirred at 20° C. for 1 hr. On completion, the reaction mixture was quenched by saturated aqueous $Na_2S_2O_3$ (1 ml) and saturated aqueous $NaHCO_3$ (1 ml). The organic layer was washed by brine (1 ml), dried over anhydrous sodium sulfate and concentrated in vacuo to give the title compound (99 mg, 94% yield) as off-white solid. $^1$H NMR (400 MHz, DMSO-$d_6$) δ 10.73 (s, 1H), 9.64 (s, 1H), 8.70 (s, 1H), 8.50-8.35 (m, 2H), 8.33 (s, 1H), 8.21 (dd, J=1.2, 8.0 Hz, 1H), 7.12 (s, 1H), 4.39-4.37 (m, 1H), 4.19-4.17 (m, 2H), 2.42-2.40 (m, 1H).

N-[6-cyclopropyl-2-(4-formylcyclohexyl)indazol-5-yl]-6-(trifluoromethyl)pyridine-2-carboxamide (Intermediate CEN)

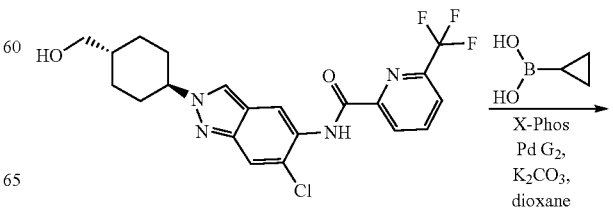

1149

-continued

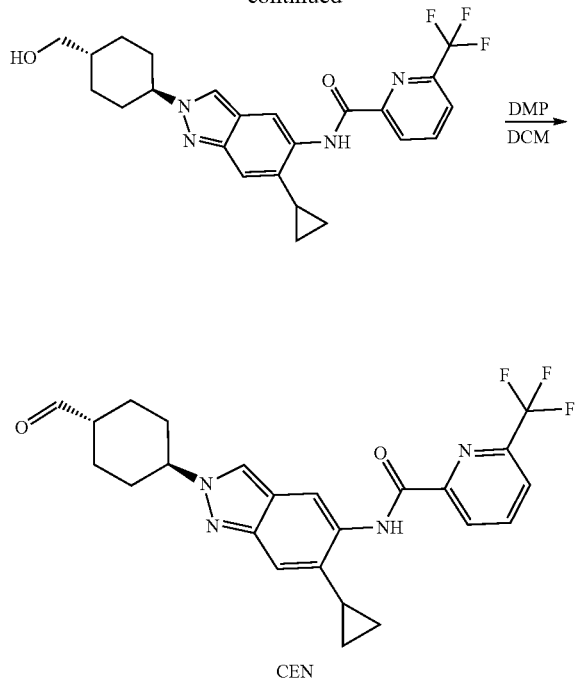

Step 1—N-[6-cyclopropyl-2-[4-(hydroxymethyl)cyclohexyl]indazol-5-yl]-6-(trifluoromethyl)pyridine-2-carboxamide A mixture of N-[6-chloro-2-[4-(hydroxymethyl)cyclohexyl]indazol-5-yl]-6-(trifluoromethyl)pyridine-2-carboxamide (300 mg, 662 umol, via Steps 1-3 of Intermediate BPQ), cyclopropylboronic acid (227 mg, 2.65 mmol, CAS #411235-57-9), XPHOS-PD-G$_2$ (52.1 mg, 66.2 umol) and K$_2$CO$_3$ (274 mg, 1.99 mmol) in dioxane (3 mL) was stirred at 90° C. for 16 hrs under N$_2$. On completion, the reaction mixture was filtered and the filtrate was concentrated in vacuo to give a residue. The residue was purified by prep-HPLC (column: Phenomenex luna C18 250*50 mm*15 um; mobile phase: [water(FA)-ACN]; B %: 48%-78%, 8 min) to give the title compound (140 mg, 46% yield) as white solid. LC-MS (ESI+) m/z 459.1 (M+H)$^+$.

Step 2—N-[6-cyclopropyl-2-(4-formylcyclohexyl)indazol-5-yl]-6-(trifluoromethyl)pyridine-2-carboxamide To a solution of N-[6-cyclopropyl-2-[4-(hydroxymethyl)cyclohexyl]indazol-5-yl]-6-(trifluoromethyl) pyridine-2-carboxamide (140 mg, 305 umol) in DCM (2 mL) was added DMP (194 mg, 458 umol). The reaction was stirred at 25° C. for 1 hr. On completion, the reaction mixture was quenched with saturated Na$_2$S$_2$O$_3$ (5 mL) and saturated NaHCO$_3$ (5 mL) at 25° C., and then the reaction mixture was stirred for 30 minutes. On completion, the mixture was extracted with DCM (2×15 mL). Then the combined organic layer was washed with NaHCO$_3$(2×15 mL) and washed with saturated salt solution (2×15 mL). The combined organic layer was dried over Na$_2$SO$_4$, filtered and the filtrate was concentrated in vacuo to give the title compound (90.0 mg, 64% yield) as brown solid. LC-MS (ESI+) m/z 457.1 (M+H)$^+$.

1150

N-[2-(4-formylcyclohexyl)-6-methoxy-indazol-5-yl]-6-(trifluoromethyl)pyrazine-2-carboxamide (Intermediate CEO)

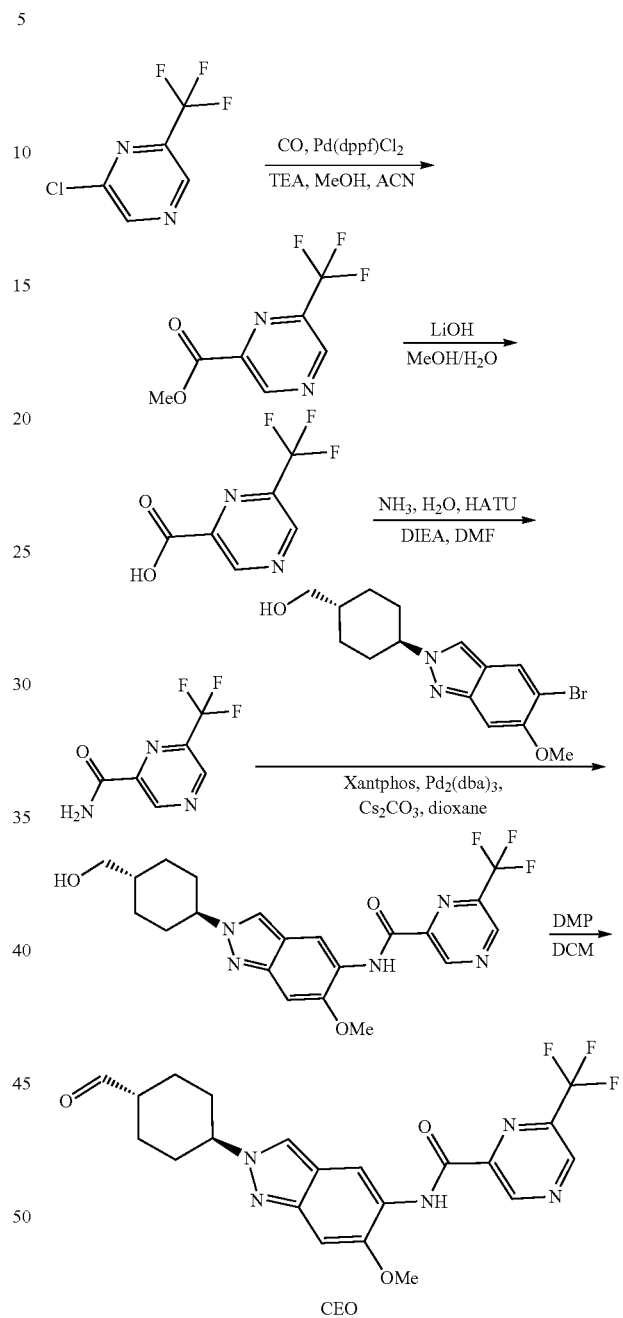

Step 1—Methyl 6-(trifluoromethyl)pyrazine-2-carboxylate

To a mixture of 2-chloro-6-(trifluoromethyl)pyrazine (2 g, 10.9 mmol, CAS #61655-69-4) in MeOH (20 mL) were added Pd(dppf)Cl$_2$ (801 mg, 1.10 mmol), and TEA (3.33 g, 32.8 mmol). Then the mixture was stirred at 70° C. for 16 hrs under CO atmosphere (50 psi). On completion, the mixture was filtered and concentrated to give a residue. The residue was purified by column chromatography (SiO$_2$, Petroleum ether/Ethyl acetate=1:0 to 5:1) to give the title compound (1 g, 44% yield) as a yellow oil. ¹H NMR (400 MHz, CDCl₃) δ 9.51 (s, 1H), 9.15 (s, 1H), 4.08 (s, 3H); LC-MS (ESI+) m/z 206.9 (M+H)⁺.

Step 2—6-(Trifluoromethyl)pyrazine-2-carboxylic Acid

To a solution of methyl 6-(trifluoromethyl)pyrazine-2-carboxylate (500 mg, 2.43 mmol) in H₂O (1 mL) and MeOH (2 mL) was added LiOH·H₂O (203 mg, 4.85 mmol) at 25° C. The reaction mixture was stirred at 25° C. for 0.5 hr. On completion, the mixture was concentrated to give a residue, then 1N HCl was added until the pH=3. The mixture was filtered and the filter cake was dried to give the title compound (465 mg, 99% yield) as a yellow solid.

Step 3—6-(Trifluoromethyl)pyrazine-2-carboxamide

To a solution of 6-(trifluoromethyl)pyrazine-2-carboxylic acid (465 mg, 2.43 mmol), HATU (1.20 g, 3.15 mmol) and DIEA (940 mg, 7.28 mmol) in DMF (3 mL) was added NH₃·H₂O (10.2 g, 72.7 mmol, 25% solution) in THF (2 mL). The mixture was then stirred at 25° C. for 1 hr. On completion, the residue was diluted with water (20 mL) and extracted with EA (2×20 mL). The combined organic layer was dried over Na₂SO₄, filtered and concentrated in vacuo to give the title compound (237 mg, 48% yield) as a white solid. ¹H NMR (400 MHz, CDCl₃) δ 9.65 (s, 1H), 9.17 (s, 1H), 7.77-7.43 (m, 1H), 5.95 (s, 1H); LC-MS (ESI+) m/z 192.0 (M+H)⁺.

Step 4—N-[2-[4-(hydroxymethyl)cyclohexyl]-6-methoxy-indazol-5-yl]-6-(trifluoromethyl) pyrazine-2-carboxamide A mixture of 6-(trifluoromethyl)pyrazine-2-carboxamide (167 mg, 873 umol), [4-(5-bromo-6-methoxy-indazol-2-yl)cyclohexyl]methanol (296 mg, 873 umol, synthesized via Steps 1-3 of Intermediate ATE), 4 Å molecular sieves (873 umol), Cs₂CO₃ (569 mg, 1.75 mmol), Xantphos (101 mg, 174 umol) and Pd₂(dba)₃ (80.0 mg, 87.3 umol) in dioxane (10 mL) was degassed and purged with N₂ three times. Then the mixture was stirred at 100° C. for 16 hrs under N₂ atmosphere. On completion, the mixture was filtered and concentrated to give a residue. The residue was purified by column chromatography (SiO₂, Petroleum ether/Ethyl acetate=0/1) to give the title compound (260 mg, 65% yield) as a yellow solid. ¹H NMR (400 MHz, CDCl₃) δ 10.40 (s, 1H), 9.73 (s, 1H), 9.17 (s, 1H), 8.83 (s, 1H), 7.91 (s, 1H), 7.09 (s, 1H), 4.43-4.24 (m, 1H), 4.03 (s, 3H), 3.57 (d, J=6.0 Hz, 2H), 2.34 (d, J=12.0 Hz, 2H), 2.14-1.90 (m, 4H), 1.72-1.66 (m, 1H), 1.49-1.36 (m, 1H), 1.33-1.20 (m, 2H); LC-MS (ESI+) m/z 450.0 (M+H)⁺.

Step 5—N-[2-(4-formylcyclohexyl)-6-methoxy-indazol-5-yl]-6-(trifluoromethyl)pyrazine-2-carboxamide To a mixture of N-[2-[4-(hydroxymethyl)cyclohexyl]-6-methoxy-indazol-5-yl]-6-(trifluoromethyl) pyrazine-2-carboxamide (100 mg, 222 umol) in DCM (5 mL) was added DMP (141 mg, 333 umol). The mixture was then stirred at 25° C. for 1 hr. On completion, the reaction mixture was quenched with saturated NaHCO₃ (2.5 mL) and Na₂S₂O₃ (2.5 mL). Then the mixture was extracted with DCM (3×5 mL). The combined organic layer was washed with NaCl (5 mL×2), dried over Na₂SO₄, filtered and concentrated in vacuo to give the title compound (99.5 mg, 96% yield) as a yellow solid. ¹H NMR (400 MHz, CDCl₃) δ 10.39 (s, 1H), 9.72 (s, 2H), 9.16 (s, 1H), 8.82 (s, 1H), 7.89 (s, 1H), 7.08 (s, 1H), 4.43-4.26 (m, 1H), 4.02 (s, 3H), 2.48-2.34 (m, 3H), 2.32-2.21 (m, 2H), 2.13-2.02 (m, 2H), 1.56-1.48 (m, 2H); LC-MS (ESI+) m/z 448.1 (M+H)⁺.

N-[2-(4-formylcyclohexyl)-6-methoxy-indazol-5-yl]-2-(trifluoromethyl)pyrimidine-4-carboxamide (Intermediate CEP)

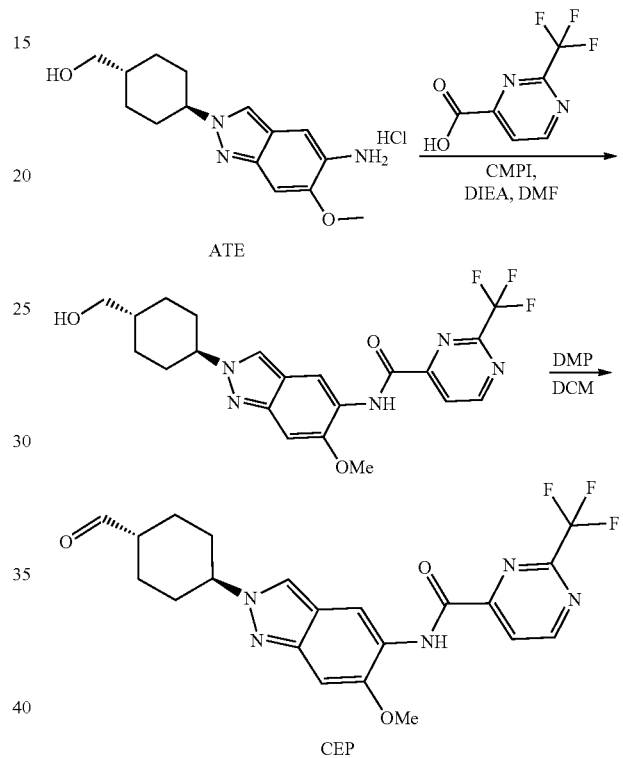

Step 1—N-[2-[4-(hydroxymethyl)cyclohexyl]-6-methoxy-indazol-5-yl]-2-(trifluoromethyl) pyrimidine A mixture of 2-(trifluoromethyl)pyrimidine-4-carboxylic acid (50.9 mg, 265 umol, HCl, CAS #878742-59-7), CMPI (88 mg, 344 umol) and DIPEA (102 mg, 795 umol) in DMF (0.5 mL) was stirred at 25° C. for 15 min. Then a solution of [4-(5-amino-6-methoxy-indazol-2-yl)cyclohexyl]methanol (73 mg, 265 umol, Intermediate ATE) in DMF (0.5 mL) was added. The reaction mixture was stirred at 25° C. for 0.5 hour. On completion, the reaction mixture was quenched with H₂O (0.1 mL). The residue was purified by reversed phase flash (0.1% FA condition) to give the title compound (93 mg, 71% yield) as a white solid. LC-MS (ESI+) m/z 450.1 (M+H)⁺.

Step 2—N-[2-(4-formylcyclohexyl)-6-methoxy-indazol-5-yl]-2-(trifluoromethyl)pyrimidine-4-carboxamide To a mixture of N-[2-[4-(hydroxymethyl)cyclohexyl]-6-methoxy-indazol-5-yl]-2-(trifluoromethyl) pyrimidine-4- carboxamide (80 mg, 178 umol) in DCM (2 mL) was added DMP (90.6 mg, 213 umol). The mixture was then stirred at 25° C. for 2 hrs. On completion, the reaction mixture was quenched with sat. Na₂S₂O₃ solution (2 mL) and sat. NaHCO₃ solution (2 mL) under stirring. Then the mixture was extracted with DCM (2×5 mL). The combined organic layer was dried over Na₂SO₄, filtered and concentrated in vacuo to give the title compound (100 mg, 98% yield) as a yellow solid. LC-MS (ESI+) m/z 447.9 (M+H)⁺.

3-(3-cyclopropyl-2-oxo-4-piperazin-1-yl-benzimidazol-1-yl)piperidine -2,6-dione (Intermediate CEQ)

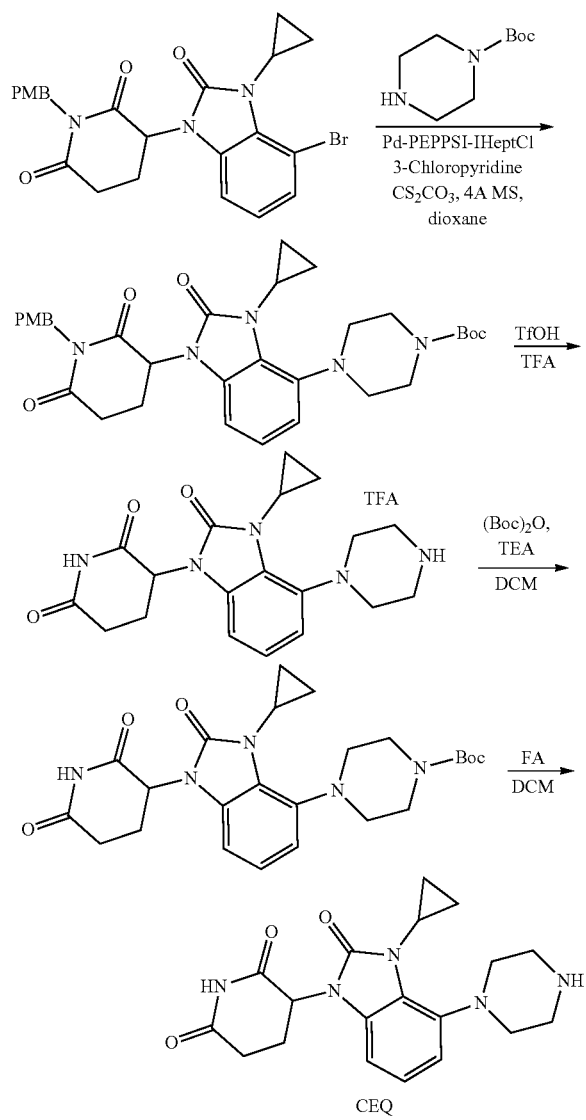

CEQ

Step 1—Tert-butyl 4-[3-cyclopropyl-1-[1-[(4-methoxyphenyl)methyl]-2,6-dioxo-3-piperidyl]-2-oxo-benzimidazol-4-yl]piperazine-1-carboxylate A mixture of 3-(4-bromo-3-cyclopropyl-2-oxo-benzimidazol-1-yl)-1-[(4-methoxyphenyl)methyl]piperidine-2,6-dione (300 mg, 619 umol, synthesized via Steps 1-4 of Intermediate CGN), tert-butyl piperazine-1-carboxylate (173 mg, 929 umol), Pd-PEPPSI-IHeptCl 3—Chloropyridine (40.0 mg, 61.9 umol), Cs₂CO₃ (403 mg, 1.24 mmol) and 4 Å molecular sieves (50 mg) in dioxane (6 mL) was stirred at 100° C. for 16 hrs. On completion, the reaction was filtered and concentrated to give a residue. The residue was purified by reverse phase (FA condition) to give the title compound (500 mg, 68.4% yield) as yellow solid. ¹H NMR (400 MHz, DMSO-d₆) δ 7.20 (d, J=8.4 Hz, 2H), 7.02-6.94 (m, 2H), 6.85 (d, J=8.4 Hz, 3H), 6.03-5.92 (m, 1H), 5.53 (dd, J=5.2, 12.8 Hz, 1H), 5.05 (dd, J=1.2, 10.4 Hz, 1H), 4.88-4.79 (m, 2H), 4.79-4.69 (m, 3H), 4.01-3.86 (m, 2H), 3.72 (s, 3H), 3.12-2.93 (m, 3H), 2.90 (d, J=10.4 Hz, 2H), 2.83 (d, J=2.4 Hz, 1H), 2.81-2.69 (m, 3H), 2.11-2.02 (m, 1H), 1.42 (s, 9H); LC-MS (ESI+) m/z 590.4 (M+H)⁺.

Step 2—3-(3-Cyclopropyl-2-oxo-4-piperazin-1-yl-benzimidazol-1-yl)piperidine-2,6-dione To a solution of tert-butyl 4-[3-cyclopropyl-1-[1-[(4-methoxyphenyl)methyl]-2,6-dioxo-3-piperidyl]-2-oxo-benzimidazol-4-yl]piperazine-1-carboxylate (120 mg, 203 umol) in TFA (1.5 mL) was added TfOH (127 mg, 849 umol), then the mixture was stirred at 70° C. for 1 hr. On completion, the reaction mixture was concentrated in vacuo to give title compound (65 mg, 66% yield, TFA) as black brown liquid. LC-MS (ESI+) m/z 370.2 (M+H)⁺.

Step 3—Tert-butyl 4-[3-cyclopropyl-1-(2,6-dioxo-3-piperidyl)-2-oxo-benzimidazol-4-yl]piperazine-1-carboxylate To a solution of 3-(3-cyclopropyl-2-oxo-4-piperazin-1-yl-benzimidazol-1-yl)piperidine -2,6-dione (40.0 mg, 82.7 umol, TFA) in DCM (1 mL) was added TEA (25.1 mg, 248 umol) and (Boc)₂O (27.0 mg, 124 umol), then the mixture was stirred at 25° C. for 2 hrs. On completion, the reaction mixture was concentrated in vacuo to give the residue. The residue was purified by reversed-phase (0.1% FA condition) to give the title compound (35 mg, 90.0% yield) as a white solid. LC-MS (ESI+) m/z 470.3 (M+H)⁺.

Step 4—3-(3-Cyclopropyl-2-oxo-4-piperazin-1-yl-benzimidazol-1-yl)piperidine-2,6-dione To a solution of tert-butyl 4-[3-cyclopropyl-1-(2,6-dioxo-3-piperidyl)-2-oxo-benzimidazol-4-yl] piperazine-1-carboxylate (35 mg, 74.5 umol) in DCM (0.20 mL) was added HCOOH (3.58 mg, 74.5 umol), then the mixture was stirred at 25° C. for 1 hr. On completion, the reaction mixture was concentrated in vacuo to give the title compound (25 mg, 80% yield, FA) as black brown liquid. LC-MS (ESI+) m/z 370.3 (M+H)⁺.

3-[4-(3,3-Dimethylpiperazin-1-yl)-3-methyl-2-oxo-benzimidazol-1-yl]-1-[(4-methoxyphenyl) methyl] piperidine-2,6-dione (Intermediate CER)

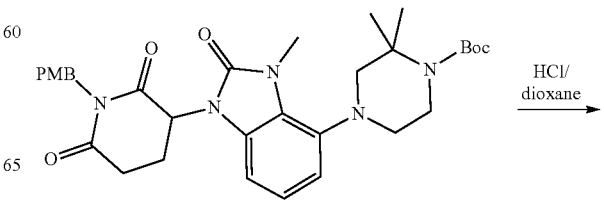

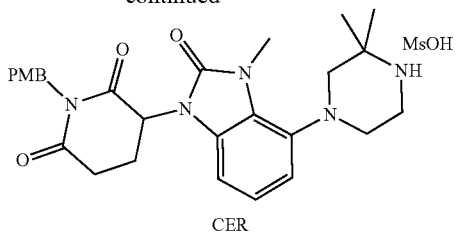

CER

To a solution of tert-butyl-4-[1-[1-[(4-methoxyphenyl)methyl]-2,6-dioxo-3-piperidyl]-3-methyl-2-oxo-benzimidazol-4-yl]-2,2-dimethyl-piperazine-1-carboxylate (230 mg, 388 umol, synthesized via Step 1 of Intermediate CBC) in DCM (2 mL) was added HCl/dioxane (4 M, 97.1 uL). Then the reaction mixture was stirred at 25° C. for 0.5 hr. On completion, the reaction mixture was concentrated in vacuo to give the title compound (205 mg, 100% yield, HCl salt) as a yellow solid. LC-MS (ESI$^+$) m/z 492.2 (M+H)$^+$.

N-[2-[4-(iodomethyl)cyclohexyl]-6-methyl-indazol-5-yl]-6-(trifluoromethyl)pyridine-2-carboxamide
(Intermediate CES)

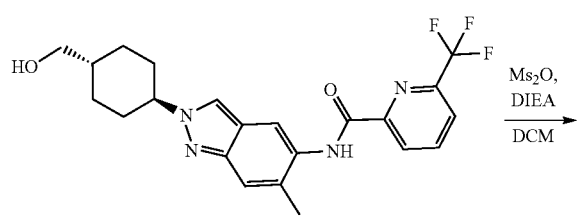

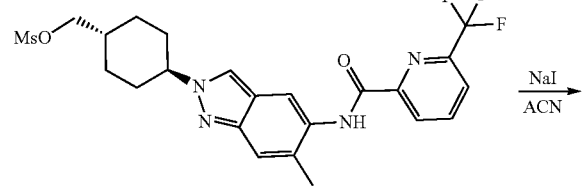

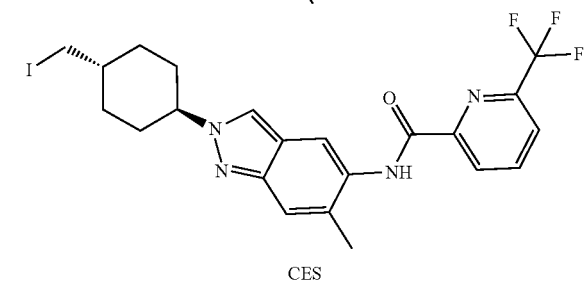

CES

Step 1—[4-[6-Methyl-5-[[6-(trifluoromethyl)pyridine-2-carbonyl]amino]indazol-2-yl]cyclohexyl]methyl methanesulfonate To a solution of N-[2-[4-(hydroxymethyl)cyclohexyl]-6-methyl-indazol-5-yl]-6-(trifluoromethyl) pyridine-2-carboxamide (500 mg, 1.16 mmol, synthesized via Step 1 of Intermediate BSC) in DCM (8 mL) was added DIEA (448 mg, 3.47 mmol, 604 uL), then methylsulfonyl methanesulfonate (402 mg, 2.31 mmol) was added at 0° C. Then the reaction mixture was stirred at 25° C. for 2 hrs. On completion, the mixture was diluted with water (15 mL) and extracted with DCM (2×20 mL). The combined organic layers were washed with brine (15 mL), dried over Na$_2$SO$_4$, filtered and concentrated in vacuo to give the title compound (580 mg, 98% yield) as a yellow solid. LC-MS (ESI$^+$) m/z 511.1 (M+H)$^+$.

Step 2—N-[2-[4-(iodomethyl)cyclohexyl]-6-methyl-indazol-5-yl]-6-(trifluoromethyl)pyridine-2-carboxamide To a solution of [4-[6-methyl-5-[[6-(trifluoromethyl)pyridine-2-carbonyl]amino]indazol-2-yl]cyclohexyl]methyl methanesulfonate (484 mg, 949 umol) in ACN (5 mL) was added NaI (640 mg, 4.27 mmol), then the reaction mixture was stirred at 70° C. for 16 hrs. On completion, the mixture was diluted with water (10 mL) and extracted with DCM (2×20 mL). The combined organic layers were washed with brine (10 mL), dried over Na$_2$SO$_4$, filtered and concentrated in vacuo to give a residue. The residue was purified by reverse phase (0.1% FA condition) to give the title compound (500 mg, 97% yield) as brown solid. $^1$H NMR (400 MHz, DMSO-d$_6$) δ 10.12 (s, 1H), 8.45-8.41 (m, 1H), 8.39 (d, J=7.6 Hz, 1H), 8.36 (s, 1H), 8.23-8.17 (m, 2H), 7.51 (s, 1H), 4.51-4.32 (m, 1H), 3.30 (d, J=6.0 Hz, 2H), 2.40 (s, 3H), 2.21-2.10 (m, 2H), 2.05-1.87 (m, 4H), 1.62-1.47 (m, 1H), 1.33-1.16 (m, 2H), LC-MS (ESI$^+$) m/z 543.0 (M+H)$^+$.

5-Bromo-4-hydroxy-2-nitro-benzaldehyde (Intermediate AWN)

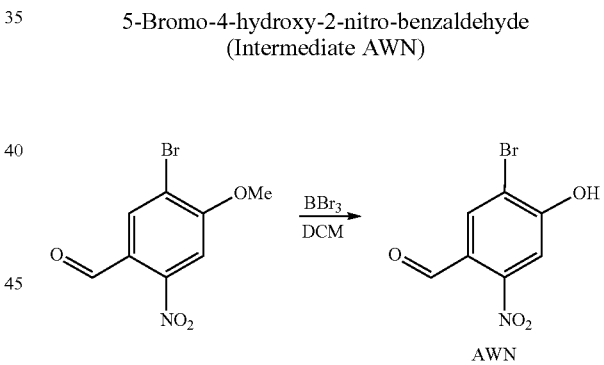

AWN

To a mixture of 5-bromo-4-methoxy-2-nitro-benzaldehyde (7.20 g, 27.6 mmol, synthesized via Steps 1-2 of Intermediate ATE) in DCM (100 mL) was added BBr$_3$ (20.8 g, 83.0 mmol). The reaction mixture was stirred at −70° C. to 25° C. for 12 hours. On completion, the reaction mixture was quenched with MeOH (10 mL) and concentrated in vacuo. The residue was triturated with DCM/PE=1/2, filtered and concentrated in vacuo to give to the title compound (4.70 g, 69% yield) as yellow solid. $^1$H NMR (400 MHz, DMSO-d$_6$) δ 12.63-12.10 (m, 1H), 10.02 (s, 1H), 8.08 (s, 1H), 7.52 (s, 1H).

1157

N-[2-(4-formylcyclohexyl)-6-methylsulfanyl-indazol-5-yl]-6-(trifluoromethyl)pyridine-2-carboxamide (Intermediate BIZ)

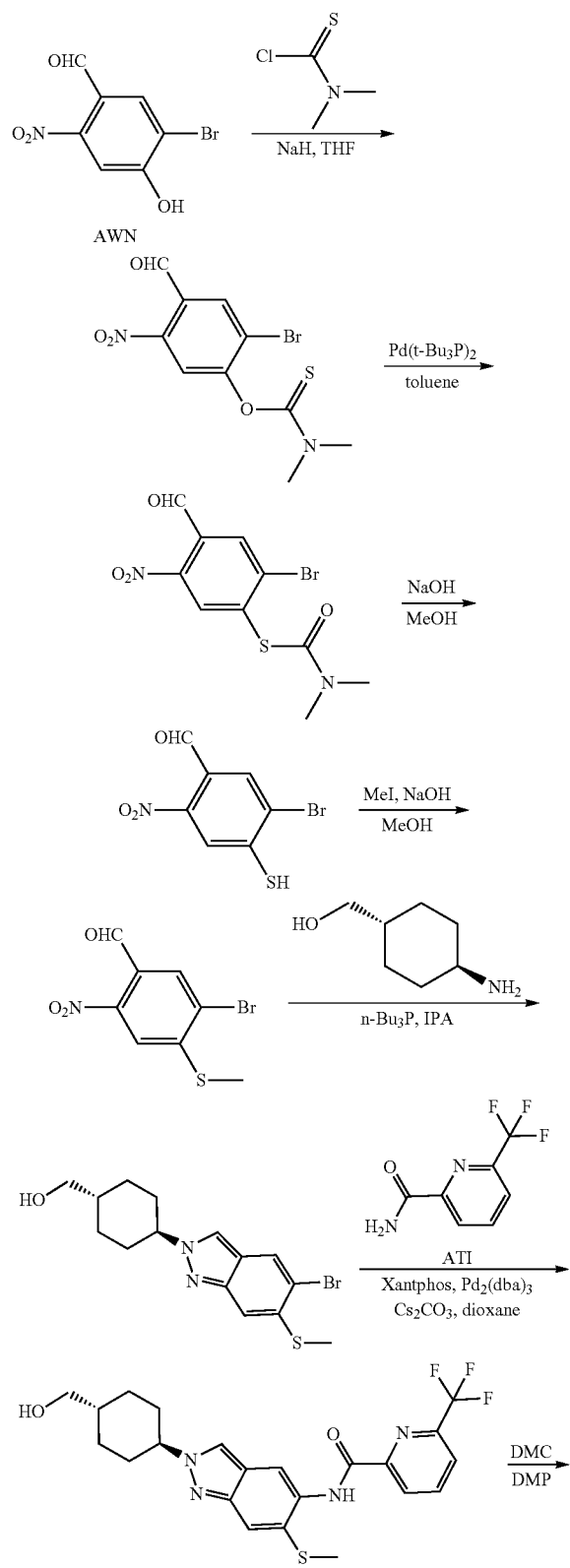

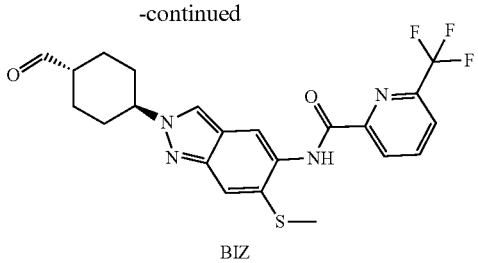

BIZ

Step 1—O-(2-bromo-4-formyl-5-nitro-phenyl) N,N-dimethylcarbamothioate

To a solution of 5-bromo-4-hydroxy-2-nitro-benzaldehyde (5.00 g, 20.3 mmol, Intermediate AWN) in THF (250 mL) was added NaH (894 mg, 22.3 mmol, 60% dispersion in mineral oil) at 0° C. for 0.5 hour. Then the mixture was stirred at 25° C. for 1 hour. Then N,N dimethylcarbamothioylchloride (3.01 g, 24.4 mmol, CAS #16420-13-6) in THF (100 mL) was added at 0° C. Then the mixture was stirred 25° C. for 12 hours. On completion, the reaction mixture was diluted in H$_2$O (100 mL) and EA (300 mL). The organic phase was separated, washed with brine (100 mL), dried over Na$_2$SO$_4$, filtered and concentrated. The residue was purified by column chromatography (petroleum ether/ethyl acetate=10/1 to 0/1) to give the title compound (13.0 g, 64% yield) as a yellow solid. $^1$H NMR (400 MHz, CDCl$_3$) δ 10.43 (s, 1H), 8.21 (s, 1H), 7.98 (s, 1H), 3.50 (s, 3H), 3.46 (s, 3H).

Step 2—5-(2-bromo-4-formyl-5-nitro-phenyl) N,N-dimethylcarbamothioate

A mixture of O-(2-bromo-4-formyl-5-nitro-phenyl) N,N-dimethylcarbamothioate (13 g, 39.0 mmol), Pd(t-Bu$_3$P)$_2$ (399 mg, 780 umol) in toluene (200 mL) was degassed and purged with N$_2$ for 3 times, and then the mixture was stirred at 120° C. for 24 hours under N$_2$ atmosphere. On completion, the reaction mixture was concentrated under reduced pressure to remove toluene. The residue was diluted with H$_2$O (200 mL) and extracted with DCM (400 mL×2). The combined organic layers were washed with brine (200 mL), dried over Na$_2$SO$_4$, filtered and concentrated under reduced pressure to give a residue. The residue was triturated with EA (20 mL) to give the title compound (7.00 g, 53% yield) as a yellow solid. $^1$H NMR (400 MHz, CDCl$_3$) δ 10.42 (s, 1H), 8.47 (s, 1H), 8.18 (s, 1H), 3.17 (s, 3H), 3.09 (s, 3H).

Step 3—5-Bromo-2-nitro-4-sulfanyl-benzaldehyde

A mixture of S-(2-bromo-4-formyl-5-nitro-phenyl) N,N-dimethylcarbamothioate (2.00 g, 6.00 mmol), NaOH (480 mg, 12.0 mmol) in MeOH (80 mL) was degassed and purged with N$_2$ for 3 times, and then the mixture was stirred at 25° C. for 12 hours under N$_2$ atmosphere. On completion, the reaction mixture was quenched by addition HCl (1M) and adjusted to pH=5-6 at 25° C., and then filtered. The filter cake was dried in vacuo to give the title compound (1.50 g, 90% yield) as a brown solid.

Step 4—5-Bromo-4-methylsulfanyl-2-nitro-benzaldehyde

To a solution of 5-bromo-2-nitro-4-sulfanyl-benzaldehyde (1.5 g, 5.72 mmol), NaOH (458 mg, 11.5 mmol) in MeOH (80 mL) was stirred for 0.5 hr. Then iodomethane (4.06 g, 28.6 mmol) was added at 25° C. and the mixture was stirred at 25° C. for 3 hours. On completion, the reaction mixture was quenched by addition HCl (1 M) to adjust the pH=7-8 at 0° C., and then the reaction mixture was concentrated under reduced pressure to remove MeOH. The residue was diluted with H$_2$O (20 mL) and extracted with EA (2×200 mL). The combined organic layers were washed with brine (100 mL), dried over Na$_2$SO$_4$, filtered and concentrated in vacuo to give a residue. The residue was purified by column chromatography (petroleum ether/ethyl acetate=10/1 to 1/1) to give the title compound (1.50 g, 94% yield) as a yellow solid. $^1$H NMR (400 MHz, CDCl$_3$) δ 10.34 (s, 1H), 8.12 (s, 1H), 7.74 (s, 1H), 2.62 (s, 3H).

Step 5—[4-(5-Bromo-6-methylsulfanyl-indazol-2-yl)cyclohexyl]methanol

A mixture of 5-bromo-4-methylsulfanyl-2-nitro-benzaldehyde (1.30 g, 4.71 mmol) and (4-aminocyclohexyl)methanol (608 mg, 4.71 mmol, CAS #1467-84-1) in IPA (45 mL) was stirred at 80° C. for 16 hours under N$_2$. The mixture was cooled to 25° C. and tributylphosphane (2.86 g, 14.1 mmol) was added. The reaction mixture was stirred at 80° C. for 6 hours. On completion, the reaction mixture was partitioned between H$_2$O (100 mL) and EA (400 mL). The organic phase was separated, washed with brine (100 mL), dried over Na$_2$SO$_4$, filtered and concentrated in vacuo. The residue was purified by column chromatography (petroleum ether/ethyl acetate=10/1 to 1/1) to give the title compound (1.10 g, 65% yield) as a yellow solid. $^1$H NMR (400 MHz, CDCl$_3$) δ 7.85 (d, J=6.8 Hz, 2H), 7.39 (s, 1H), 4.36-430 (m, 1H), 3.54 (s, 2H), 2.50 (s, 3H), 2.30 (d, J=10.8 Hz, 2H), 2.05-1.94 (m, 4H), 1.67-1.65 (m, 1H), 1.44-1.43 (m, 1H), 1.28-1.19 (m, 2H); LC-MS (ESI+) m/z 357.0 (M+H)$^+$.

Step 6—N-[2-[4-(hydroxymethyl)cyclohexyl]-6-methyl sulfanyl-indazol-5-yl]-6-(trifluoromethyl)pyridine-2-carboxamide A mixture of [4-(5-bromo-6-methylsulfanyl-indazol-2-yl)cyclohexyl]methanol (1.00 g, 2.81 mmol), 6-(trifluoromethyl)pyridine-2-carboxamide (535 mg, 2.81 mmol, Intermediate ATI), Cs$_2$CO$_3$ (1.83 g, 5.63 mmol), Xantphos (326 mg, 563 umol) and Pd$_2$(dba)$_3$ (258 mg, 281 umol) in dioxane (15 mL) was degassed and purged with N$_2$ for 3 times, and then the mixture was stirred at 95° C. for 24 hours under N$_2$ atmosphere. The reaction mixture was filtered and concentrated under reduced pressure to give a residue. The residue was purified by column chromatography (petroleum ether/ethyl acetate=20/1 to 1/1) to give the title compound (700 mg, 46% yield) as a brown solid. $^1$H NMR (400 MHz, CDCl$_3$) δ 11.04 (s, 1H), 8.76 (s, 1H), 8.43 (d, J=8.0 Hz, 1H), 8.06 (t, J=8.0 Hz, 1H), 7.88 (d, J=7.2 Hz, 2H), 7.81 (d, J=7.2 Hz, 1H), 4.35-4.27 (m, 1H), 3.49 (d, J=6.0 Hz, 2H), 2.42 (s, 3H), 2.29-2.25 (m, 2H), 2.00-1.90 (m, 4H), 1.65-1.56 (m, 2H), 1.24-1.14 (m, 2H).

Step 7—N-[2-(4-formylcyclohexyl)-6-methylsulfanyl-indazol-5-yl]-6-(trifluoromethyl)pyridine-2-carboxamide To a solution of N-[2-[4-(hydroxymethyl)cyclohexyl]-6-methylsulfanyl-indazol-5-yl]-6-(trifluoromethyl) pyridine-2-carboxamide (120 mg, 258 umol) in DCM (2 mL) was added DMP (142 mg, 336 umol) at 0° C. The mixture was stirred at 0-25° C. for 1 hour. On completion, the reaction mixture was quenched by addition of Na$_2$S$_2$O$_3$ (1 mL). Then NaHCO$_3$ (1 mL) was added until the pH=8 at 25° C. The mixture was next diluted with H$_2$O (5 mL) and extracted with DCM (2×10 mL). The combined organic layers were dried over Na$_2$SO$_4$, filtered and concentrated in vacuo to give the title compound (100 mg, 84% yield) as a yellow solid. LC-MS (ESI+) m/z 463.2 (M+H)$^+$.

N-[2-(4-formylcyclohexyl)-6-methylsulfonyl-indazol-5-yl]-6-(trifluoromethyl)pyridine-2-carboxamide (Intermediate BJB)

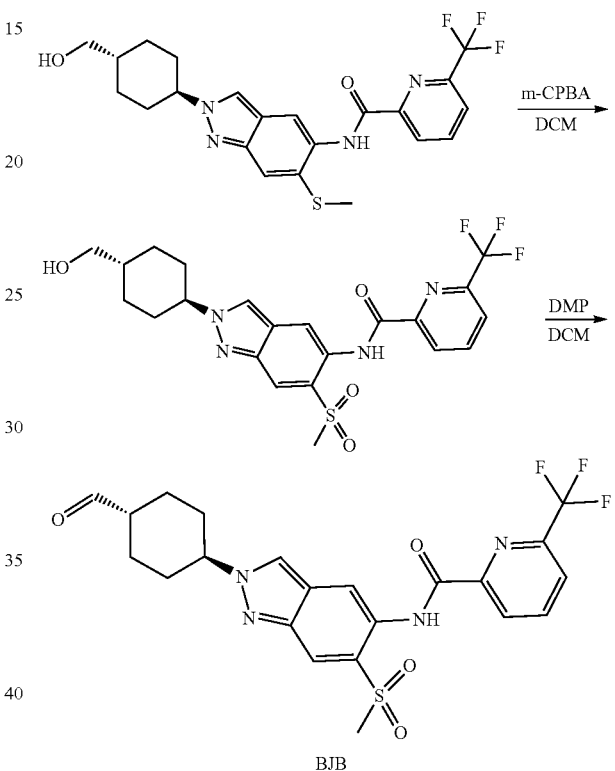

Step 1—N-[2-[4-(hydroxymethyl)cyclohexyl]-6-methylsulfonyl-indazol-5-yl]-6-(trifluoromethyl) pyridine-2-carboxamide To a solution of N-[2-[4-(hydroxymethyl)cyclohexyl]-6-methylsulfanyl-indazol-5-yl]-6-(trifluoromethyl)pyridine-2-carboxamide (400 mg, 861 umol, synthesized via Steps 1-6 of Intermediate BIZ) in DCM (15 mL) was added m-CPBA (928 mg, 4.31 mmol, 80% solution) at 0° C. The mixture was then stirred at 25° C. for 12 hours. On completion, the reaction mixture was concentrated in vacuo to give a residue. The residue was purified by column chromatography (petroleum ether/ethyl acetate=10/1 to 3/1) to give the title compound (300 mg, 56% yield) as a yellow solid. LC-MS (ESI+) m/z 497.1 (M+H)$^+$.

Step 2—N-[2-(4-formylcyclohexyl)-6-methylsulfonyl-indazol-5-yl]-6-(trifluoromethyl)pyridine-2-carboxamide To a solution of N-[2-[4-(hydroxymethyl)cyclohexyl]-6-methylsulfonyl-indazol-5-yl]-6-(trifluoromethyl)pyridine- 2-carboxamide (70.0 mg, 140 umol) in DCM (2 mL) was added DMP (77.7 mg, 183 umol). The mixture was stirred at 0-25° C. for 1 hour. The reaction mixture was quenched by addition saturated NaHCO$_3$ (1 mL) and Na$_2$S$_2$O$_3$ (1 mL), and then diluted with H$_2$O (5 mL) and extracted with DCM (2×25 mL). The combined organic layers were washed with brine (10 mL), dried over Na$_2$SO$_4$, filtered and concentrated in vacuo to give the title compound (60.0 mg, 86% yield) as a yellow solid. LC-MS (ESI+) m/z 495.1 (M+H)$^+$.

N-[2-(4-formylcyclohexyl)-6-methylsulfinyl-indazol-5-yl]-6-(trifluoromethyl)pyridine-2-carboxamide (Intermediate CEU)

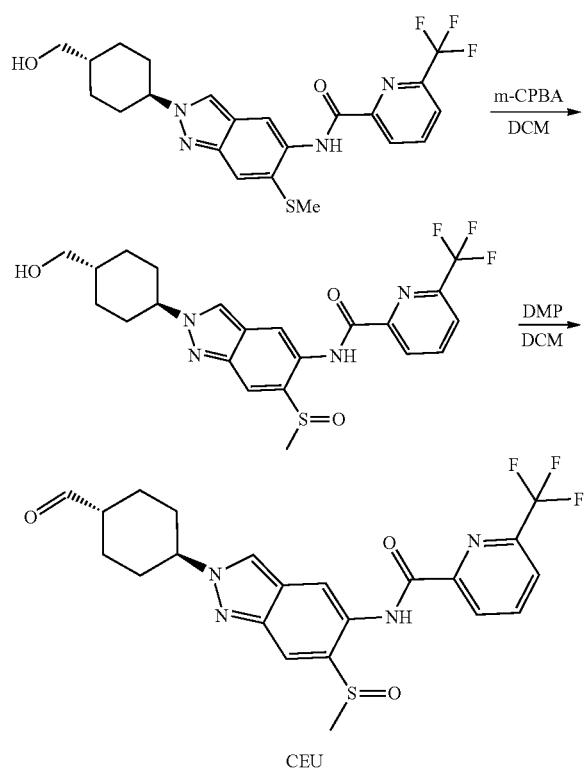

CEU

Step 1—N-[2-[4-(hydroxymethyl)cyclohexyl]-6-methylsulfinyl -indazol-5-yl]-6-(trifluoromethyl) pyridine-2-carboxamide To a solution of N-[2-[4-(hydroxymethyl)cyclohexyl]-6-methylsulfanyl-indazol-5-yl]-6-(trifluoromethyl)pyridine-2-carboxamide (200 mg, 430 umol, synthesized via Steps 1-6 of Intermediate BIZ) in DCM (2 mL) was added a mixture of m-CPBA (111 mg, 517 umol, 80% solution) in DCM (2 mL) dropwise at −10° C., then the mixture was stirred at −10° C. for 0.5 hr. On completion, the mixture was diluted with DCM (10 mL), then quenched with saturated NaHCO$_3$ (10 mL) and saturated Na$_2$S$_2$O$_3$ (10 mL), and the mixture was stirred at 25° C. for 0.5 hr. After that, the organic layer was washed with saturated NaHCO$_3$ (10 mL×3), the organic layer was separated and washed with saturated NaCl (20 mL). The organic layer was dried over Na$_2$SO$_4$, filtered and concentrated in vacuo to give the title compound (160 mg, 77% yield) as yellow solid. $^1$H NMR (400 MHz, DMSO-d$_6$) δ 11.4 (s, 1H), 8.59 (s, 1H), 8.44 (s, 1H), 8.43-8.34 (m, 2H), 8.19 (d, J=7.6 Hz, 1H), 8.02 (s, 1H), 4.55-4.47 (m, 2H), 3.31-3.27 (m, 2H), 2.86 (s, 3H), 2.17 (d, J=9.2 Hz, 2H), 1.93 (d, J=10.4 Hz, 4H), 1.55-1.45 (m, 1H), 1.23 (s, 2H); LC-MS (ESI$^+$) m/z 481.1 (M+H)$^+$.

Step 2—N-[2-(4-formylcyclohexyl)-6-methylsulfinyl -indazol-5-yl]-6-(trifluoromethyl)pyridine -2-carboxamide To a solution of N-[2-[4-(hydroxymethyl)cyclohexyl]-6-methylsulfinyl-indazol-5-yl]-6-(trifluoromethyl)pyridine-2-carboxamide (160 mg, 333 umol) in DCM (2 mL) was added DMP (169 mg, 399 umol), then the mixture was stirred at 25° C. for 0.5 hr. On completion, the mixture was diluted with DCM (20 mL), then quenched with saturated NaHCO$_3$ (10 mL) and saturated Na$_2$S$_2$O$_3$ (10 mL). The mixture was stirred at 25° C. for 0.5 hr. Next, the organic layer was washed with saturated NaHCO$_3$ (20 mL×3), the organic layer was separated and washed with saturated NaCl (10 mL). The organic layer was dried over Na$_2$SO$_4$, filtered and concentrated in vacuo to give the title compound (140 mg, 88% yield) as yellow solid. $^1$H NMR (400 MHz, DMSO-d$_6$) δ 11.46 (s, 1H), 9.65 (s, 1H), 8.59 (s, 1H), 8.45 (s, 1H), 8.44-8.35 (m, 2H), 8.19 (d, J=7.6 Hz, 1H), 8.03 (s, 1H), 4.61-4.50 (m, 1H), 2.86 (s, 3H), 2.47-2.40 (m, 1H), 2.26-2.19 (m, 2H), 2.17-2.09 (m, 2H), 2.07-1.97 (m, 2H), 1.47-1.42 (m, 2H); LC-MS (ESI$^+$) m/z 479.0 (M+H)$^+$.

Methyl 7-cyano -4-(isopropylamino)-[1,4] benzodioxino[2,3-b]pyridine -3-carboxylate (Intermediate CEV) and methyl 8-cyano-4-(isopropylamino)-[1,4] benzodioxino[2,3-b]pyridine-3-carboxylate (Intermediate CEW)

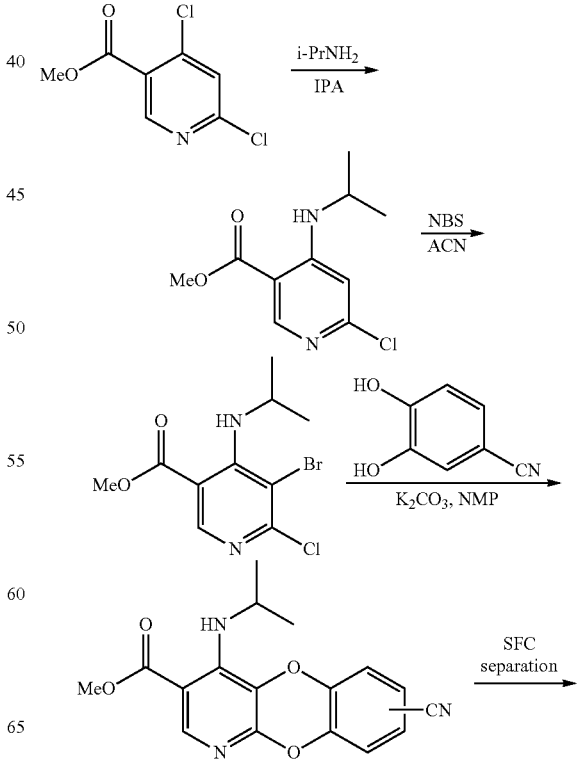

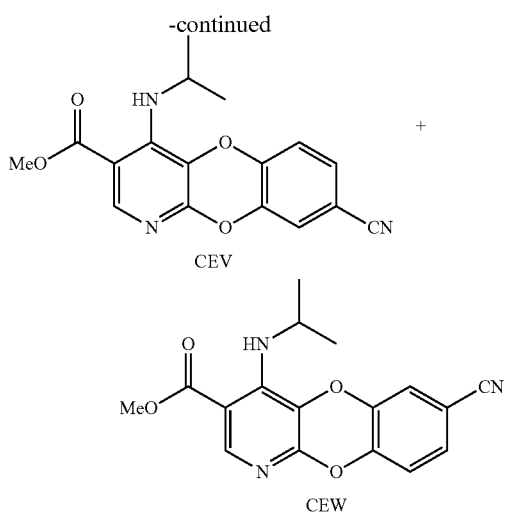

Step 1—Methyl 6-chloro-4-(isopropylamino)pyridine-3-carboxylate

To a solution of methyl 4,6-dichloropyridine-3-carboxylate (6.50 g, 31.5 mmol) and propan-2-amine (1.86 g, 31.5 mmol, 2.71 mL, CAS #65973-52-6) in IPA (80 mL) was added DIEA (20.3 g, 157 mmol, 27.4 mL), then the reaction mixture was stirred at 50° C. for 16 hrs. On completion, the reaction mixture was concentrated in vacuo to give a residue. The residue was purified by column chromatography (SiO$_2$, PE:EA=100:1 to PE:EA=15:1, Pl:Rf=0.22) to give the title compound (4.40 g, 61% yield) as a white solid. $^1$H NMR (400 MHz, DMSO-d$_6$) δ 8.51 (s, 1H), 7.96 (d, J=8.0 Hz, 1H), 6.83 (s, 1H), 3.90-3.84 (m, 1H), 3.82 (s, 3H), 1.20 (s, 3H), 1.19 (s, 3H). LC-MS (ESI$^+$) m/z 228.9 (M+H)$^+$.

Step 2—Methyl 5-bromo-6-chloro-4-(isopropylamino)pyridine-3-carboxylate

To a solution of methyl 6-chloro-4-(isopropylamino)pyridine-3-carboxylate (4.10 g, 17.9 mmol) in ACN (10 mL) was added NBS (3.19 g, 17.9 mmol), then the reaction mixture was stirred at 25° C. for 4 hrs. On completion, the reaction mixture was filtered and concentrated in vacuo to give a residue. The residue was diluted with water (40 mL) and extracted with EA (2×80 mL). The combined organic layers were washed with brine (30 mL), dried over Na$_2$SO$_4$, filtered and the filtrate was concentrated in vacuo to give the title compound (5.50 g, 100% crude yield) as white solid. $^1$H NMR (400 MHz, DMSO-d$_6$) δ 11.05 (s, 1H), 7.50 (d, J=8.4 Hz, 1H), 4.39-4.21 (m, 1H), 3.86 (s, 3H), 1.20 (s, 3H), 1.19 (s, 3H), LC-MS (ESI$^+$) m/z 309.1 (M+H)$^+$.

Step 3—Methyl 8-cyano-4-(isopropylamino)-[1,4]benzodioxino[2,3-b]pyridine-3-carboxylate To a solution of methyl 5-bromo-6-chloro-4-(isopropylamino)pyridine-3-carboxylate (4.80 g, 15.6 mmol) and 3,4-dihydroxybenzonitrile (2.32 g, 17.1 mmol, CAS #17345-61-8) in NMP (50 mL) was added K$_2$CO$_3$ (6.47 g, 46.8 mmol). Then the reaction mixture was stirred at 130° C. for 2 hrs. On completion, the reaction mixture was filtered and concentrated in vacuo to give a residue. The residue was diluted with water (250 mL) and extracted with EA (2×50 mL). The combined organic layers were washed with brine (2×50 mL) and dried over Na$_2$SO$_4$, filtered and the filtrate was concentrated in vacuo to give a residue. The water (20 mL) was added slowly to the residue while stirring. The precipitated white solid was isolated by filtration and the residue was washed with water. The crude product was triturated with PE:EA=(10:1) to give the title compound (1.00 g, 20% yield) as a white solid. LC-MS (ESI$^+$) m/z 326.2 (M+H)$^+$.

Step 4—Methyl 7-cyano-4-(isopropylamino)-[1,4]benzodioxino[2,3-b]pyridine-3-carboxylate and methyl 8-cyano-4-(isopropylamino)-[1,4]benzodioxino[2,3-b]pyridine-3-carboxylate Methyl 8-cyano-4-(isopropylamino)-[1,4]benzodioxino[2,3-b]pyridine-3-carboxylate (1.00 g, 3.07 mmol) was separated by SFC (column: DAICEL CHIRALPAK AD (250 mm*30 mm, 10 um); mobile phase: [0.1% NH3H2O MEOH]; B %: 25%-25%, 3; 45 min) to give methyl 7-cyano-4-(isopropylamino)-[1,4]benzodioxino[2,3-b]pyridine-3-carboxylate (250 mg, 25% yield) as a white solid ($^1$H NMR (400 MHz, DMSO-d$_6$) δ 8.38 (s, 1H), 8.23 (d, J=7.2 Hz, 1H), 7.30-7.27 (m, 1H), 7.23 (d, J=1.6 Hz, 1H), 6.91 (d, J=8.0 Hz, 1H), 4.48-4.32 (m, 1H), 3.88 (s, 3H), 1.32 (s, 3H), 1.31 (s, 3H) and methyl 8-cyano-4-(isopropylamino)-[1,4]benzodioxino[2,3-b]pyridine-3-carboxylate (500 mg, 50% yield) as a white solid ($^1$H NMR (400 MHz, DMSO-d$_6$) δ 8.37 (s, 1H), 8.23 (d, J=7.6 Hz, 1H), 7.30-7.27 (m, 1H), 7.13 (d, J=1.6 Hz, 1H), 7.04 (d, J=8.4 Hz, 1H), 4.51-4.30 (m, 1H), 3.88 (s, 3H), 1.33 (s, 3H), 1.31 (s, 3H). LC-MS (ESI$^+$) m/z 195.1 (M+H)$^+$).

7-Cyano-4-(isopropylamino)-[1,4]benzodioxino[2,3-b]pyridine-3-carboxylic acid (Intermediate CEX)

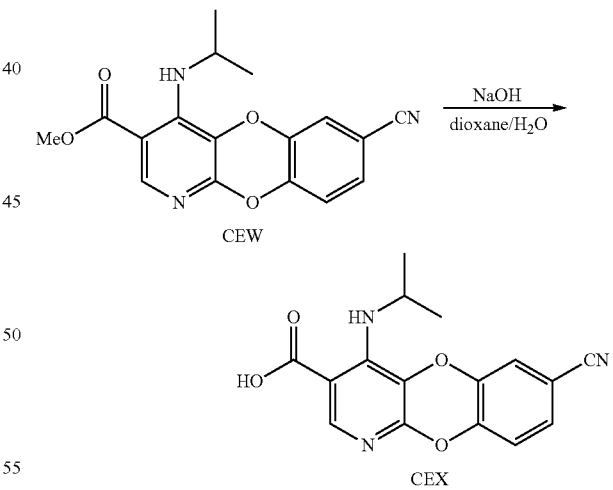

To a solution of methyl 7-cyano-4-(isopropylamino)-[1,4]benzodioxino[2,3-b]pyridine-3-carboxylate (15.0 mg, 46.1 umol, Intermediate CEW) in dioxane (0.5 mL) and H$_2$O (0.15 mL) was added NaOH (7.38 mg, 184 umol), then the reaction mixture was stirred at 25° C. for 8 hrs. On completion, the reaction mixture was filtered and the filtrate was concentrated in vacuo to give a residue. The residue was diluted with water (5 mL) and acidified with citric acid until the pH=5-6, then the residue was extracted with EA (2×5 mL). The combined organic layers were washed with brine 3-[4-[1-[(4-Aminocyclohexyl)methyl]-4-piperidyl]-3-methyl-2-oxo-benzimidazol-1-yl]piperidine-2,6-dione (Intermediate CEY)

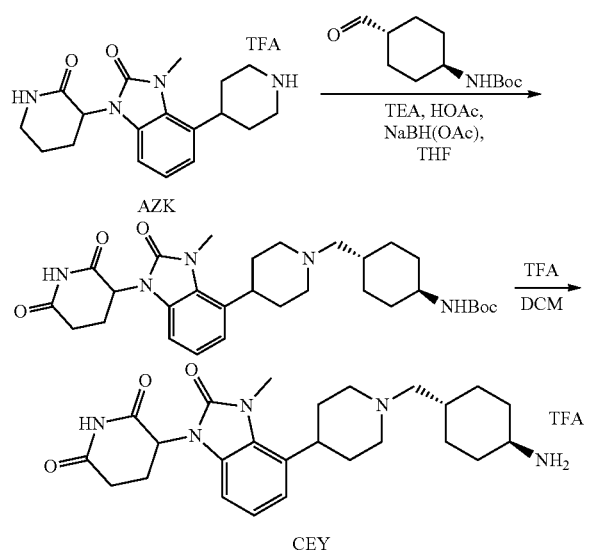

Step 1—Tert-butyl N-[4-[[4-[1-(2,6-dioxo-3-piperidyl)-3-methyl-2-oxo-benzimidazol-4-yl]-1-piperidyl]methyl]cyclohexyl]carbamate To a solution of 3-[3-methyl-2-oxo-4-(4-piperidyl)benzimidazol-1-yl]piperidine-2,6-dione (820 mg, 1.80 mmol, TFA, Intermediate AZK) in THF (5 mL) was added TEA (181 mg, 1.80 mmol, 250 uL), and the mixture was stirred at −10° C. for 10 mins. Then tert-butyl N-(4-formylcyclohexyl)carbamate (408 mg, 1.80 mmol, CAS #181308-57-6) and AcOH (107 mg, 1.80 mmol, 102 uL) was added to the mixture, and the mixture was stirred at −10° C. for 20 mins. Next, NaBH(OAc)$_3$ (495 mg, 2.34 mmol) was added to the mixture, and the mixture was stirred at −10° C. for 1 hr. On completion, the reaction mixture was quenched with H$_2$O (0.5 mL) and concentrated in vacuo to give a residue. The residue was purified by prep-HPLC (column: Phenomenex luna C18 250*50 mm*15 um; mobile phase: [water(FA)-ACN]; B %: 15%-45%, 20 min) to give the title compound (500 mg, 50% yield) as an-off white solid. $^1$H NMR (400 MHz, DMSO-d$_6$) δ 11.09 (s, 1H), 7.03-6.99 (m, 2H), 6.99-6.93 (m, 1H), 6.69 (d, J=8.0 Hz, 1H), 5.36 (dd, J=5.2, 12.4 Hz, 1H), 2.96 (d, J=10.8 Hz, 3H), 2.92-2.83 (m, 1H), 2.76-2.62 (m, 2H), 2.24-2.04 (m, 5H), 2.03-1.93 (m, 1H), 1.85-1.70 (m, 9H), 1.45-1.35 (m, 11H), 1.20-0.79 (m, 5H). LC-MS (ESI$^+$) m/z 554.5 (M+H)$^+$.

Step 2—3-[4-[1-[(4-Aminocyclohexyl)methyl]-4-piperidyl]-3-methyl-2-oxo-benzimidazol-1-yl] piperidine-2,6-dione To a solution of tert-butyl N-[4-[[4-[1-(2,6-dioxo-3-piperidyl)-3-methyl-2-oxo-benzimidazol-4-yl]-1-piperidyl]methyl]cyclohexyl]carbamate (25.0 mg, 45.1 umol) in DCM (1 mL) was added TFA (308 mg, 2.70 mmol, 0.20 mL). Then, the reaction mixture was stirred at 25° C. for 2 hrs. On completion, the reaction mixture was concentrated in vacuo to give the title compound (25.0 mg, 98% yield, TFA salt) as colorless oil. LC-MS (ESI$^+$) m/z 454.3 (M+H)$^+$.

8-cyano-4-(isopropylamino)-[1,4]benzodioxino[2,3-b]pyridine-3-carboxylic acid (Intermediate CEZ)

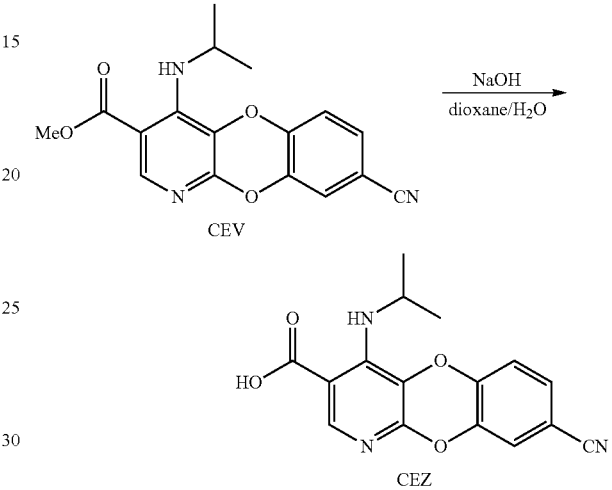

To a solution of methyl 8-cyano-4-(isopropylamino)-[1,4]benzodioxino[2,3-b]pyridine-3-carboxylate (50 mg, 153 umol, Intermediate CEV) in dioxane (1 mL) and H$_2$O (0.5 mL) was added NaOH (24.5 mg, 614 umol), then the mixture was stirred at 25° C. for 2 hrs. On completion, the reaction mixture was adjusted to pH=4, then extracted with DCM/MeOH=10/1 (5 mL×5). The organic layers were dried with Na$_2$SO$_4$, filtered and concentrated in vacuo to give the title compound (42 mg, 87% yield) as white solid. $^1$H NMR (400 MHz, DMSO-d$_6$) δ 8.30 (d, J=8.0 Hz, 1H), 8.22 (s, 1H), 7.63 (d, J=2.0 Hz, 1H), 7.53 (dd, J=2.0, 8.4 Hz, 1H), 7.22 (d, J=8.4 Hz, 1H), 3.57 (s, 2H), 1.23 (d, J=6.4 Hz, 6H); LC-MS (ESI+) m/z 312.0 (M+H)$^+$.

1-[8-[1-[(4-Aminocyclohexyl)methyl]-4-piperidyl]-4-isoquinolyl]hexahydropyrimidine-2,4-dione (Intermediate CFA)

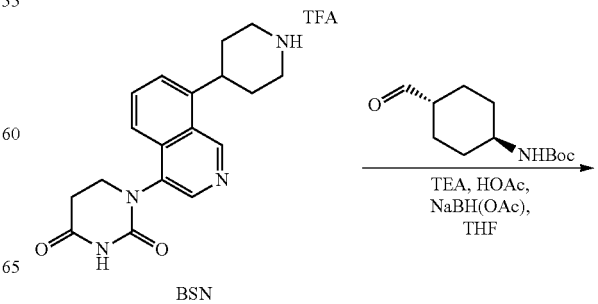

1167

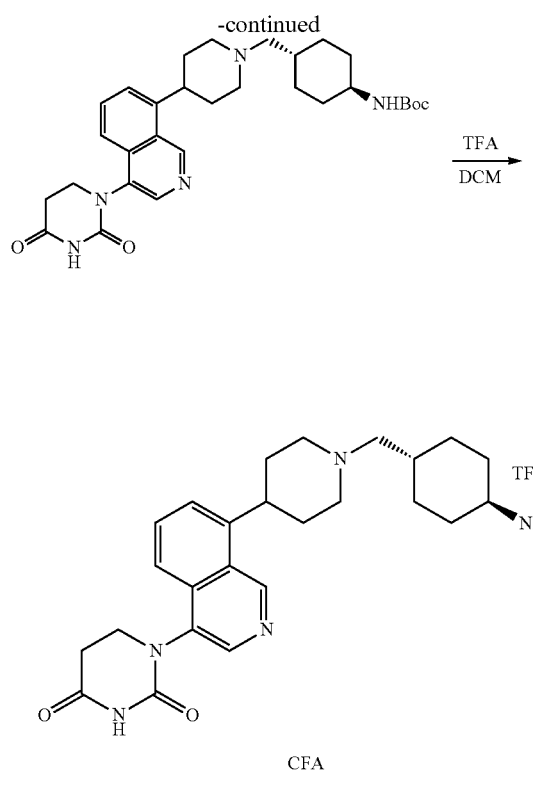

CFA

Step 1—Tert-butyl N-[4-[[4-[4-(2,4-dioxohexahydropyrimidin-1-yl)-8-isoquinolyl]-1-piperidyl]methyl]cyclohexyl]carbamate To a mixture of 1-[8-(4-piperidyl)-4-isoquinolyl]hexahydropyrimidine-2,4-dione (60.0 mg, 184 umol, Intermediate BSN) in THF (1 mL) was added TEA (18.7 mg, 184 umol) at −15° C. until the pH stabilized at 8. The mixture was stirred at −15° C. for 0.25 hr, then AcOH (11.1 mg, 184 umol) was added at −15° C. until the pH stabilized at 5~6. Subsequently, tert-butyl N-(4-formylcyclohexyl)carbamate (33.6 mg, 147 umol) in DMF (1 mL) was added at −15° C. and the mixture was stirred for 0.25 hr. Next, NaBH(OAc)$_3$ (78.4 mg, 369 umol) was added in one portion. The resulting reaction mixture was stirred at −15° C. for 1 hr. On completion, the reaction mixture was concentrated in vacuo. The residue was purified by reversed phase flash (Phenomenex luna C18 150*25 mm*10 um; mobile phase: [water(FA)-ACN]; B %: 5%-35%, 10.5 min), to give the title compound (70.0 mg, 69% yield) as a white solid. LC-MS (ESI+) m/z 536.3 (M+H)$^+$.

Step 2—1-[8-[1-[(4-Aminocyclohexyl)methyl]-4-piperidyl]-4-isoquinolyl]hexahydropyrimidine-2,4-dione To a solution of tert-butyl N-[4-[[4-[4-(2,4-dioxohexahydropyrimidin-1-yl)-8-isoquinolyl]-1-piperidyl]methyl]cyclohexyl]carbamate (70.0 mg, 130 umol) in DCM (2 mL) was added TFA (308 mg, 2.70 mmol). The mixture was then stirred at 25° C. for 1 hr. On completion, the reaction mixture was concentrated in vacuo to give the title compound (70.0 mg, 97% yield, TFA) as a yellow oil. LC-MS (ESI+) m/z 436.3 (M+H)$^+$.

1168

1-(5-Fluoro-8-piperazin-1-yl-4-isoquinolyl)hexahydropyrimidine-2,4-dione (Intermediate CFB)

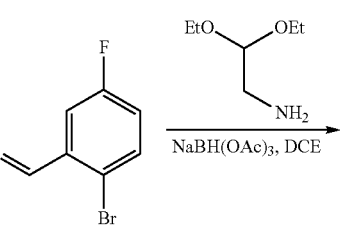

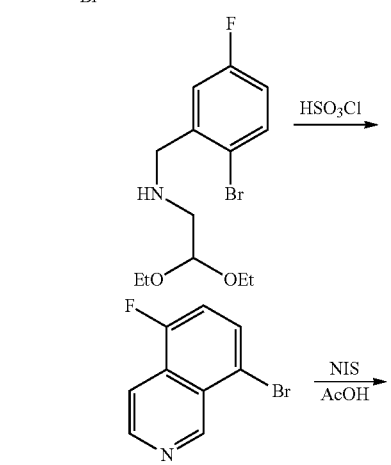

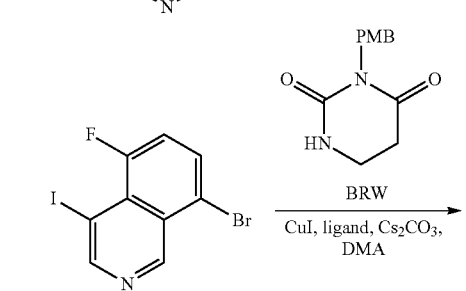

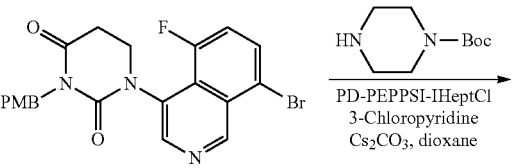

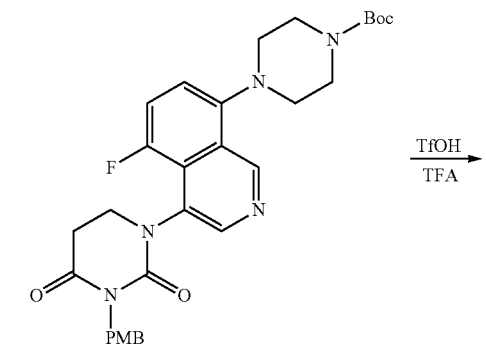

-continued

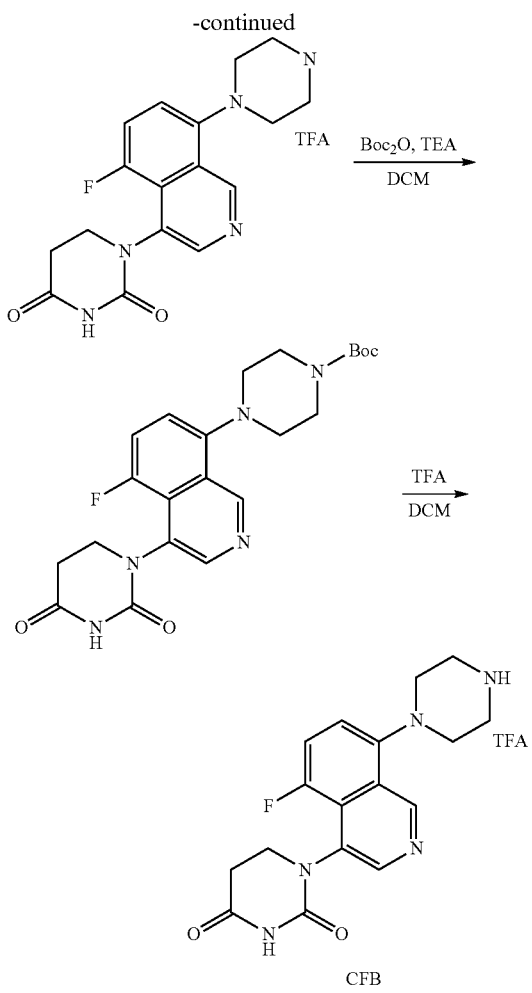

Step 1—N-[(2-bromo-5-fluoro-phenyl)methyl]-2,2-diethoxy-ethanamine

To a solution of 2-bromo-5-fluoro-benzaldehyde (5.00 g, 24.6 mmol, CAS #59142-68-6) and 2,2-diethoxyethanamine (3.28 g, 24.6 mmol, CAS #645-36-3) in DCE (120 mL) was added NaBH(OAc)$_3$ (7.31 g, 34.4 mmol). The mixture was then stirred at 25° C. for 16 hrs. On completion, the mixture was diluted with DCM (100 mL) and quenched with NaOH aqueous (1M) until the pH=14. The organic layer was separated, washed with NaCl (100 mL), dried over Na$_2$SO$_4$, filtered and concentrated under reduced pressure to give the title compound (9.00 g, 79% yield) as yellow oil. LC-MS (ESI+) m/z 319.9 (M+H)$^+$.

Step 2—8-Bromo-5-fluoro-isoquinoline

To a solution of N-[(2-bromo-5-fluoro-phenyl)methyl]-2,2-diethoxy-ethanamine (4.91 g, 15.3 mmol) in sulfurochloridic acid (17.8 g, 153 mmol) was stirred at 100° C. for 0.5 hr. On completion, the reaction was quenched with ice and extracted with DCM (50 mL). The organic layer was discarded and the aqueous layer was basified with 50% NaOH solution until the pH=14, and then extracted with CH$_2$Cl$_2$ (50 mL×2). The combined organic layers were washed with brine, dried over Na$_2$SO$_4$, filtered and concentrated in vacuo. The residue was purified by column chromatography (SiO$_2$, Petroleum ether/Ethyl acetate=20:1 to 10:1) to give the title compound (1.50 g, 37% yield) as yellow solid. LC-MS (ESI+) m/z 227.9 (M+H)$^+$.

Step 3—8-Bromo-5-fluoro-4-iodo-isoquinoline

To a solution of 8-bromo-5-fluoro-isoquinoline (0.9 g, 3.98 mmol) in CH$_3$COOH (10 mL) was added NIS (1.34 g, 5.97 mmol). The mixture was stirred at 80° C. for 16 hrs. On completion, the reaction mixture was quenched with Na$_2$S$_2$O$_4$ (0.1 mL). The mixture was quenched with ice and extracted with DCM (10 mL), and the mixture was concentrated to give a residue. The residue was purified by column chromatography (SiO$_2$, Petroleum ether/Ethyl acetate=30/1 to 20/1) to give the title compound (876 mg, 60% yield) as yellow solid. LC-MS (ESI+) m/z 353.7 (M+H)$^+$.

Step 4—1-(8-Bromo-5-fluoro-4-isoquinolyl)-3-[(4-methoxyphenyl)methyl]hexahydropyrimidine-2,4-dione A mixture of 8-bromo-5-fluoro-4-iodo-isoquinoline (500 mg, 1.42 mmol), 3-[(4-methoxyphenyl) methyl]hexahydropyrimidine-2,4-dione (624 mg, 2.66 mmol, Intermediate BRW), CuI (33.8 mg, 177 umol), Cs$_2$CO$_3$ (1.74 g, 5.33 mmol), 4 Å molecular sieves (50.0 mg, 1.78 mmol) and 3,4,7,8-tetramethyl-1,10-phenanthroline (41.9 mg, 177 umol) in DMA (5 mL) was degassed and purged with N$_2$ three times. Then the mixture was stirred at 95° C. for 5 hrs under N$_2$ atmosphere. On completion, the mixture was filtered and concentrated to give a residue. The crude product was purified by reversed-phase HPLC (0.1% FA condition) to give the title compound (130 mg, 14% yield) as yellow solid. LC-MS (ESI+) m/z 458 (M+H)$^+$.

Step 5—Tert-butyl 4-[5-fluoro-4-[3-[(4-methoxyphenyl)methyl]-2,4-dioxo-hexahydropyrimidin-1-yl]-8-isoquinolyl]piperazine-1-carboxylate A mixture of 1-(8-bromo-5-fluoro-4-isoquinolyl)-3-[(4-methoxyphenyl)methyl]hexahydropyrimidine-2,4-dione (73.0 mg, 159 umol), tert-butyl piperazine-1-carboxylate (98.0 mg, 398 umol, HOAc, CAS #143238-38-4), 4 Å molecular sieves (25.0 mg, 199 umol), Cs$_2$CO$_3$ (194 mg, 597 umol) and 1,3-bis[2,6-bis(1-propylbutyl)phenyl]-4,5-dichloro-2H-imidazol-1-ium-2-ide; 3-chloropyridine; dichloropalladium (19.3 mg, 19.9 umol) in DMSO (2.5 mL) was degassed and purged with N$_2$ for 3 times, and then the mixture was stirred at 90° C. for 16 hrs under N$_2$ atmosphere. On completion, the reaction mixture was filtered and concentrated in vacuo to give a residue. The residue was then diluted with H$_2$O (8 mL) and extracted with EA (10 mL×3). The mixture was filtered and organic layers were dried over Na$_2$SO$_4$, filtered and concentrated in vacuo to give a residue. The residue was purified by column chromatography (Petroleum ether: Ethyl acetate=5:1 to 1:1) to give the title compound (120 mg, 86% yield) as black oil. LC-MS (ESI+) m/z 564.2 (M+H)$^+$.

Step 6—1-(5-Fluoro-8-piperazin-1-yl-44 isoquinolyl)hexahydropyrimidine-2,4-dione To a solution of tert-butyl 4-[5-fluoro-4-[3-[(4-methoxyphenyl)methyl]-2,4-dioxo-hexahydropyrimidin-1-yl]-8-isoquinolyl]piperazine-1-carboxylate (100 mg, 177 umol) was added TfOH (0.1 mL) and TFA (1 mL). The mixture was stirred at 70° C. for 16 hrs. On completion, the mixture was concentrated to give the title compound (60.0 mg, 68% yield) as black oil. LC-MS (ESI+) m/z 344.0 (M+H)⁺.

Step 7—Tert-butyl 4-[4-(2,4-dioxohexahydropy-rimidin-1-yl)-5-fluoro-8-isoquinolyl]piperazine-1-carboxylate To a solution of 1-(5-fluoro-8-piperazin-1-yl-4-isoqui-nolyl)hexahydropyrimidine-2,4-dione (50.0 mg, 145 umol) in DCM (0.5 mL) was added TEA (14.7 mg, 145 umol) at 0° C. until the pH stabilized at 9-10. Then to the mixture was added Boc₂O (34.9 mg, 160 umol) in DCM (0.5 mL) at 0° C. The mixture was stirred at 25° C. for 3 hrs. On completion, the mixture was concentrated in vacuo to give the title compound (60 mg, 92% yield) as red oil. LC-MS (ESI+) m/z 444.0 (M+H)⁺.

Step 8—1-(5-Fluoro-8-piperazin-1-yl-4-isoquinolyl)hexahydropyrimidine-2,4-dione

To a solution of 1-(5-fluoro-8-piperazin-1-yl-4-isoqui-nolyl)hexahydropyrimidine-2,4-dione (50.0 mg, 145 umol) in DCM (0.5 mL) was added TEA (14.7 mg, 145 umol) at 0° C. until the pH stabilized at 9-10. Then the mixture was added Boc₂O (34.9 mg, 160 umol) in DCM (0.5 mL) at 0° C. The mixture was stirred at 25° C. for 3 hrs. On completion, the mixture was concentrated to give the title compound (25.0 mg, 53% yield) as red oil. LC-MS (ESI+) m/z 344.1 (M+H)⁺.

1-(4-Piperazin-1-ylphenyl)hexahydropyrimidine-2,4-dione (Intermediate CFC)

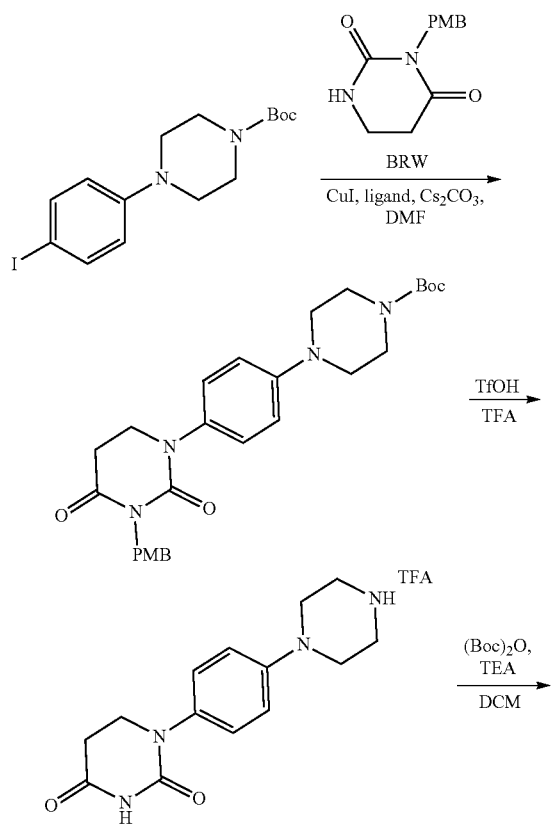

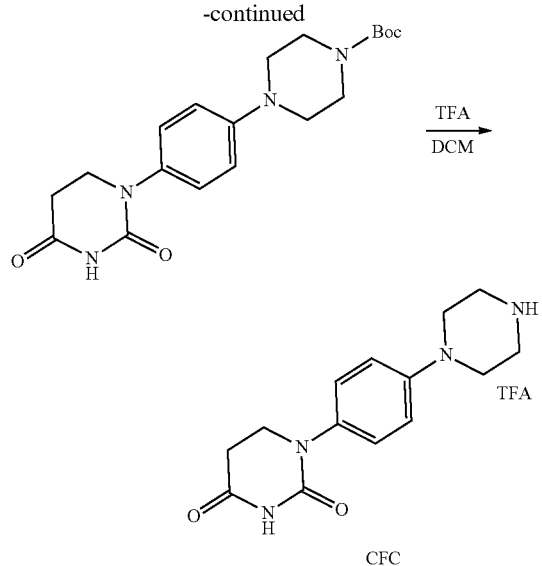

Step 1—Tert-butyl 4-[4-[3-[(4-methoxyphenyl)methyl]-2,4-dioxo-hexahydropyrimidin-1-yl]phenyl]piperazine-1-carboxylate A mixture of tert-butyl 4-(4-iodophenyl)piperazine-1-carboxylate (500 mg, 1.29 mmol, CAS #151978-66-4), 3-[(4-methoxyphenyl)methyl]hexahydropyrimidine-2,4-dione (331 mg, 1.42 mmol, Intermediate BRW), Cs₂CO₃ (839 mg, 2.58 mmol), CuI (49.0 mg, 257 umol) and (1R,2R)—N1, N2-dimethylcyclohexane-1,2-diamine (36.6 mg, 257 umol) in DMF (8 mL) was degassed and purged with N₂ three times. Then the mixture was stirred at 70° C. for 12 hr under N₂ atmosphere. On completion, the reaction mixture was filtered and concentrated in vacuo. The residue was purified by column chromatography (SiO₂, Petroleum ether/Ethyl acetate=50/1 to 10/1) to give the title compound (630 mg, 98% yield) as brown solid. LC-MS (ESI⁺) m/z 495.1 (M+H)⁺.

Step 2—1-(4-Piperazin-1-ylphenyl)hexahydropy-rimidine-2,4-dione

Tert-butyl 4-[4-[3-[(4-methoxyphenyl)methyl]-2,4-di-oxo-hexahydropyrimidin-1-yl]phenyl]piperazine-1-car-boxylate (320 mg, 647 umol) was dissolved in TFA (2 mL) and TfOH (0.4 mL). The mixture was stirred at 70° C. for 12 hr. On completion, the reaction mixture was concentrated in vacuo to give the title compound (250 mg, 99% yield, TFA) as black brown oil. LC-MS (ESI⁺) m/z 274.9 (M+H)⁺.

Step 3—Tert-butyl 4-[4-(2,4-dioxohexahydropy-rimidin-1-yl)phenyl]piperazine-1-carboxylate To a solution of 1-(4-piperazin-1-ylphenyl)hexahydropy-rimidine-2,4-dione (250 mg, 643 umol, TFA) in DCM (5 mL) was added TEA (130 mg, 1.29 mmol) at 25° C. until the pH stabilized at 8. Then Boc₂O (281 mg, 1.29 mmol) was added and the mixture was stirred at 25° C. for 4 hrs. On completion, the reaction mixture was quenched with H₂O (10 mL) at 25° C., and then extracted with EA 40 mL (20 mL×2). The combined organic layers were filtered and concentrated under reduced pressure to give a residue. The residue was purified by reversed phase (0.1% FA condition)

to give the title compound (160 mg, 66% yield) as pink solid. $^1$H NMR (400 MHz, DMSO-$d_6$) δ 10.28 (s, 1H), 7.17 (d, J=8.8 Hz, 2H), 6.95 (d, J=8.8 Hz, 2H), 3.70 (t, J=6.4 Hz, 2H), 3.45 (d, J=4.8 Hz, 4H), 3.13-3.03 (m, 4H), 2.68 (t, J=6.8 Hz, 2H), 1.42 (s, 9H); LC-MS (ESI$^+$) m/z 375.1 (M+H)$^+$.

Step 4—1-(4-Piperazin-1-ylphenyl)hexahydropyrimidine-2,4-dione

To a solution of tert-butyl 4-[4-(2,4-dioxohexahydropyrimidin-1-yl)phenyl]piperazine-1-carboxylate (60.0 mg, 160 umol) in DCM (1 mL) was added TFA (182 mg, 1.60 mmol). The mixture was stirred at 25° C. for 1 hr. On completion, the reaction mixture was concentrated in vacuo to give the title compound (60.0 mg, 96% yield, TFA) as brown solid. LC-MS (ESI$^+$) m/z 274.8 (M+H)$^+$.

1-(6-Piperazin-1-yl-3-pyridyl)hexahydropyrimidine-2,4-dione (Intermediate CFD)

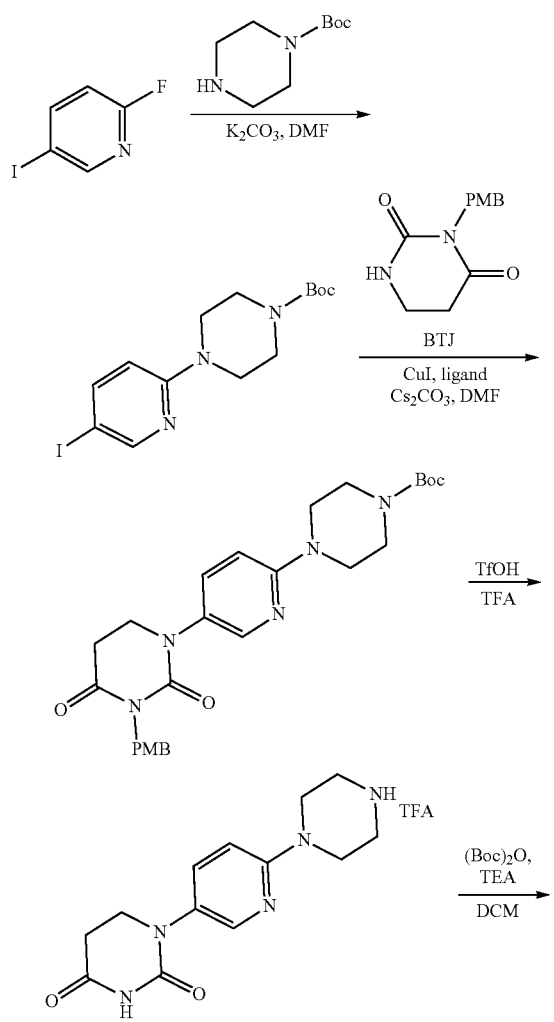

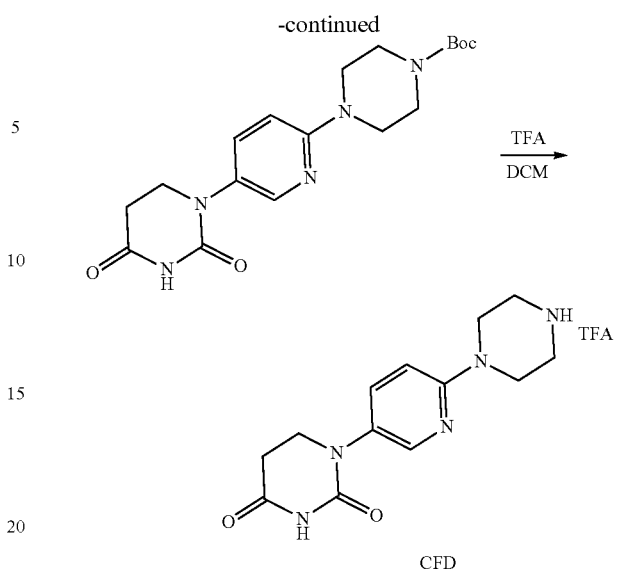

Step 1—Tert-butyl 4-(5-iodo-2-pyridyl)piperazine-1-carboxylate

To a solution of 2-fluoro-5-iodo-pyridine (3.00 g, 13.4 mmol, CAS #171193-80-1) and tert-butyl piperazine-1-carboxylate (3.98 g, 16.1 mmol, HOAc, CAS #143238-38-4) in DMF (30 mL) was added K$_2$CO$_3$ (3.72 g, 26.9 mmol). The mixture was then stirred at 110° C. for 12 hrs. On completion, the mixture was quenched with water (120 mL) and extracted with EA (50 mL×3). The combined organic phase was dried over anhydrous sodium sulfate, filtered and concentrated to give a residue. The residue was purified by column chromatography (SiO$_2$, PE:EA=10:1 to 7:1), to give the title compound (4.22 g, 79% yield) as a white solid. LC-MS (ESI+) m/z 389.9 (M+H)$^+$.

Step 2—Tert-butyl 4-[5-[3-[(4-methoxyphenyl)methyl]-2,4-dioxo-hexahydropyrimidin-1-yl]-2-pyridyl]piperazine-1-carboxylate To a solution of 3-[(4-methoxyphenyl)methyl]hexahydropyrimidine-2,4-dione (406 mg, 1.73 mmol, Intermediate BTJ) in DMF (7 mL) was added tert-butyl 4-(5-iodo-2-pyridyl)piperazine-1-carboxylate (450 mg, 1.16 mmol), CuI (88.0 mg, 462 umol), Cs$_2$CO$_3$ (753 mg, 2.31 mmol), (1R,2R)—N1,N2-dimethylcyclohexane-1,2-diamine (65.7 mg, 462 umol) and 4 Å molecular sieves (100 mg, 1.16 mmol) under N$_2$. On completion, the mixture was stirred at 70° C. for 12 hrs. On completion, the mixture was filtered and concentrated in vacuo to give a residue. The residue was purified by column chromatography (SiO$_2$, Petroleum ether/Ethyl acetate=3:1 to 1:1) to give the title compound (600 mg, 74% yield) as a white solid. LC-MS (ESI+) m/z 496.2 (M+H)$^+$.

Step 3—1-(6-Piperazin-1-yl-3-pyridyl)hexahydropyrimidine-2,4-dione

To a solution of tert-butyl 4-[5-[3-[(4-methoxyphenyl)methyl]-2,4-dioxo-hexahydropyrimidin-1-yl]-2-pyridyl]piperazine-1-carboxylate (400 mg, 807 umol) in TFA (2 mL) was added TfOH (0.2 mL). The mixture was stirred at 70° C. for 2 hrs. On completion, the reaction mixture was concentrated in vacuo to give the title compound (310 mg, 98% yield, TFA) as a yellow oil. LC-MS (ESI+) m/z 276.0 (M+H)⁺.

Step 4—Tert-butyl 4-[5-(2,4-dioxohexahydropyrimidin-1-yl)-2-pyridyl]piperazine-1-carboxylate To a solution of 1-(6-piperazin-1-yl-3-pyridyl)hexahydropyrimidine-2,4-dione (340 mg, 873 umol, TFA) in DCM (1 mL) was added TEA (88.3 mg, 873 umol) at 0° C. until pH stabilized at 9-10. Then the mixture was added (Boc)₂O (209 mg, 960 umol) in DCM (0.5 mL) at 0° C. The mixture was stirred at 25° C. for 3 hrs. On completion, the mixture was quenched with water (5 mL) and extracted with ethyl acetate (10 mL×3). The combined organic phase was dried over anhydrous sodium sulfate, filtered and concentrated to give a residue. The crude product was triturated with PE:DCM=7:1 (10 mL) at 25° C. for 10 mins to give the title compound (320 mg, 96% yield) as a yellow solid. LC-MS (ESI+) m/z 376.1 (M+H)⁺.

Step 5—1-(6-Piperazin-1-yl-3-pyridyl)hexahydropyrimidine-2,4-dione

To a solution of tert-butyl 4-[5-(2,4-dioxohexahydropyrimidin-1-yl)-2-pyridyl]piperazine-1-carboxylate (80.0 mg, 213 umol) in DCM (1 mL) was added TFA (154 mg, 1.35 mmol). The mixture was stirred at 25° C. for 1 hr. On completion, the reaction mixture was concentrated in vacuo to give the title compound (80.0 mg, 96% yield, TFA) as a yellow oil. LC-MS (ESI+) m/z 276.1 (M+H)⁺.

2-(2,6-dioxo-3-piperidyl)-4-[2-(methylamino)ethylamino]isoindoline-1,3-dione (Intermediate CFE)

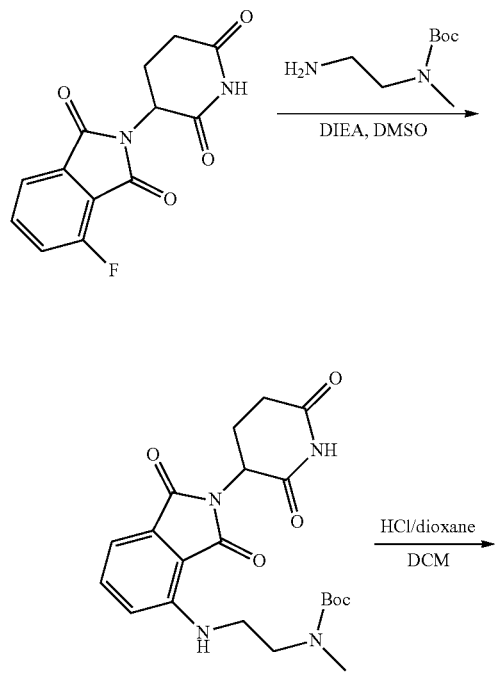

Step 1—Tert-butyl N-[2-[[2-(2,6-dioxo-3-piperidyl)-1,3-dioxo-isoindolin-4-yl]amino]ethyl]-N-methyl-carbamate To a solution of 2-(2,6-dioxo-3-piperidyl)-4-fluoro-isoindoline-1,3-dione (1.00 g, 3.62 mmol, CAS #835616-60-9) and tert-butyl N-(2-aminoethyl)-N-methyl-carbamate (756 mg, 4.34 mmol, CAS #121492-06-6) in DMSO (8 mL) was added DIEA (1.40 g, 10.8 mmol, 1.89 mL). Then the reaction mixture was stirred at 130° C. for 4 hrs. On completion, the reaction mixture was added to water (40 ml) dropwise, then filtered and the filter cake was concentrated in vacuo to give the title compound (1.5 g, 96% yield) as a green solid. LC-MS (ESI⁺) m/z 330.9 (M–100+H)⁺.

Step 2—2-(2,6-Dioxo-3-piperidyl)-4-[2-(methylamino)ethylamino]isoindoline -1,3-dione To a solution of tert-butyl N-[2-[[2-(2,6-dioxo-3-piperidyl)-1,3-dioxo-isoindolin-4-yl]amino]ethyl]-N-methyl-carbamate (100 mg, 232 umol) in DCM (1 mL) was added HCl/dioxane (4 M, 1 mL), then the reaction mixture was stirred at 25° C. for 1 hr. On completion, the reaction mixture was concentrated in vacuo to give the title compound (85 mg, 99% yield, HCl) as blue oil. LC-MS (ESI⁺) m/z 330.8 (M+H)⁺.

4-[5-Methoxy-6-[[6-(trifluoromethyl) pyridine-2-carbonyl]amino]-1,3-benzothiazol-2-yl] cyclohexanecarboxylic acid (Intermediate CFF)

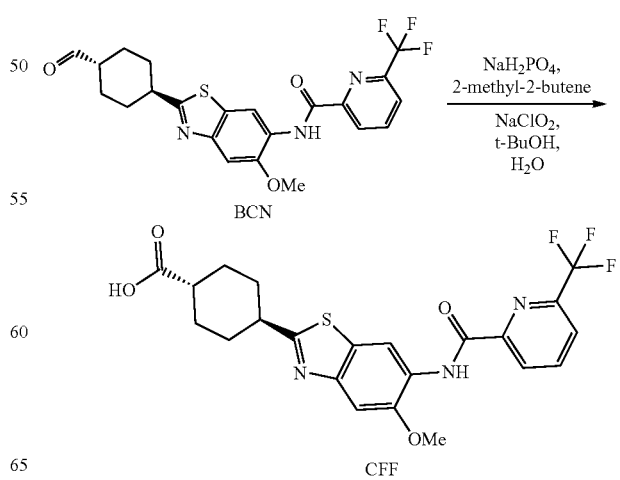

To a mixture of N-[2-(4-formylcyclohexyl)-5-methoxy-1,3-benzothiazol-6-yl]-6-(trifluoromethyl)pyridine-2-carboxamide (100 mg, 215 umol, Intermediate BCN) in t-BuOH (3 mL) and H$_2$O (1 mL) was added 2-methylbut-2-ene (60.5 mg, 863 umol, 91.4 uL), NaH$_2$PO$_4$ (25.8 mg, 215 umol) and sodium chlorite (58.5 mg, 647 umol) at 0° C. Then the reaction mixture was stirred at 25° C. for 2 hours. On completion, the residue was diluted with water (10 mL), then the residue was extracted with DCM (3×30 mL). The combined organic layer was dried over Na$_2$SO$_4$, filtered and concentrated in vacuo to give the title compound (100 mg, 97% yield) as yellow solid. LC-MS (ESI$^+$) m/z 480.0 (M+H)$^+$.

N-[2-(4-formylcyclohexyl)-6-methoxy-indazol-5-yl]-5-methyl-pyridine-3-carboxamide (Intermediate CFG)

(100 mg, 253 umol) in DCM (5 mL) was added DMP (139 mg, 329 umol). The reaction mixture was stirred at 25° C. for 2 hours. On completion, the reaction mixture was quenched with saturated Na$_2$S$_2$O$_3$ (10 mL) and saturated NaHCO$_3$ (10 mL) at 25° C., then the mixture was stirred for 30 minutes. The residue was diluted with water (20 mL) and extracted with DCM (2×20 mL). The combined organic layer was dried over Na$_2$SO$_4$, filtered and concentrated in vacuo to give a residue to give the title compound (91 mg, 91% yield) as yellow solid. LC-MS (ESI$^+$) m/z 393.2 (M+H)$^+$.

3-[5-(2,5-Dihydro-1H-pyrrol-3-yl)-3-methyl-2-oxo-benzimidazol-1-yl]piperidine-2,6-dione (Intermediate CFH)

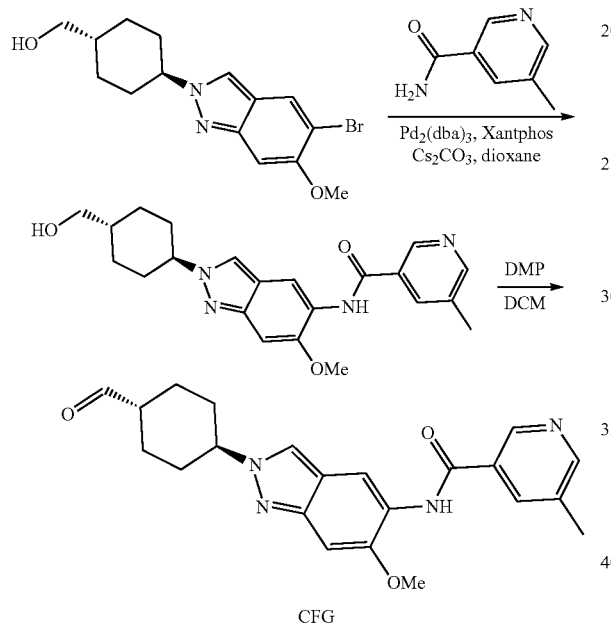

CFG

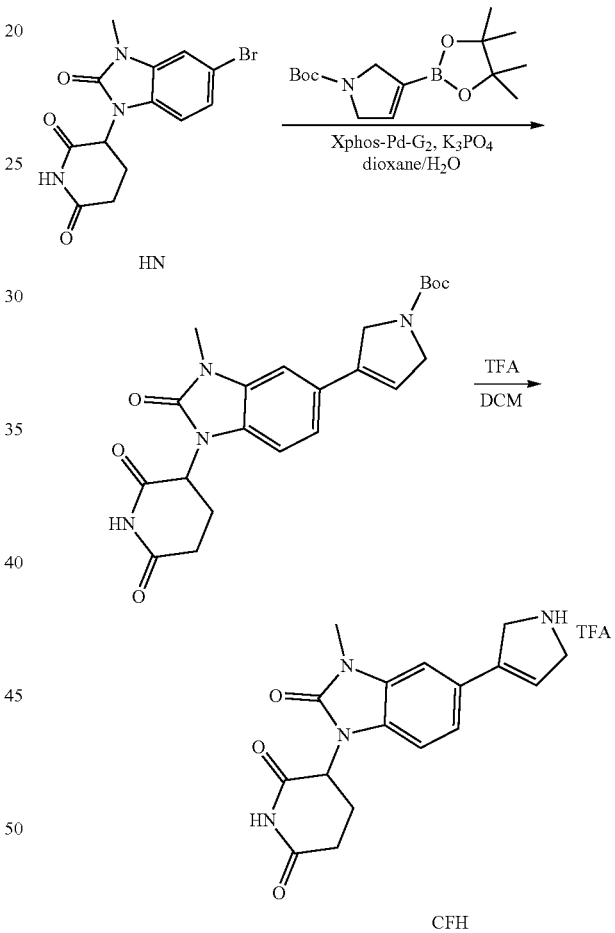

CFH

Step 1—N-[2-[4-(hydroxymethyl)cyclohexyl]-6-methoxy-indazol-5-yl]-5-methyl-pyridine-3-carboxamide To a mixture of [4-(5-bromo-6-methoxy-indazol-2-yl)cyclohexyl]methanol (500 mg, 1.47 mmol, synthesized via Steps 1-3 of Intermediate ATE) and 5-methylpyridine-3-carboxamide (240 mg, 1.77 mmol, CAS #70-57-5) in dioxane (10 mL) was added Pd$_2$(dba)$_3$ (134 mg, 147 umol), Xantphos (85.2 mg, 147 umol) and Cs$_2$CO$_3$ (1.44 g, 4.42 mmol). The reaction mixture was then stirred at 100° C. for 12 hours. On completion, the residue was diluted with water (30 mL) and extracted with DCM (2×30 mL). The combined organic layer was dried over Na$_2$SO$_4$, filtered and concentrated in vacuo to give a residue. The residue was purified by reverse phase (0.1% FA condition) to give the title compound (100 mg, 17% yield) as white solid. LC-MS (ESI$^+$) m/z 395.1 (M+H)$^+$.

Step 2—N-[2-(4-formylcyclohexyl)-6-methoxy-indazol-5-yl]-5-methyl-pyridine-3-carboxamide To a mixture of N-[2-[4-(hydroxymethyl)cyclohexyl]-6-methoxy-indazol-5-yl]-5-methyl-pyridine-3-carboxamide Step 1—Tert-butyl3-(1-(2,6-dioxopiperidin-3-yl)-3-methyl-2-oxo-2,3-dihydro-1H-benzo[d]imidazol-5-yl)-2,5-dihydro-1H-pyrrole-1-carboxylate A mixture of 3-(5-bromo-3-methyl-2-oxo-benzimidazol-1-yl)piperidine-2,6-dione (300 mg, 887 umol, Intermediate FIN) tert-butyl 3-(4,4,5,5-tetramethyl-1,3,2-dioxaborolan-2-yl)-2,5-dihydropyrrole-1-carboxylate (340 mg, 1.15 mmol, CAS #212127-83-8), XPHOS-PDG2 (69.8 mg, 88.7 umol) and K$_3$PO$_4$ (564 mg, 2.66 mmol) in dioxane (5 mL) and H$_2$O (1 mL) was degassed and purged with N$_2$ three times. Then the mixture was stirred at 80° C. for 16 h under N₂ atmosphere. On completion, the reaction mixture was cooled to room temperature and filtered, the filtrate was concentrated in vacuo. The residue was purified by reverse phase (0.1% FA condition) to give the title compound (200 mg, 52% yield) as a white solid. LC-MS (ESI+) m/z 427.2 (M+H)⁺.

3-[5-(2,5-Dihydro-1H-pyrrol-3-yl)-3-methyl-2-oxo-benzimidazol-1-yl]piperidine-2,6-dione To a solution of tert-butyl 3-[1-(2,6-dioxo-3-piperidyl)-3-methyl-2-oxo-benzimidazol-5-yl]-2,5-dihydropyrrole-1-carboxylate(60.0 mg, 140 umol) in DCM (2 mL) was added TFA (160 mg, 1.41 mmol). The mixture was stirred at 25° C. for 1 hr. On completion, the mixture was concentrated in vacuo to give the title compound (60.0 mg, 96% yield, TFA salt) as a yellow oil. LC-MS (ESI+) m/z 327.0 (M+H)⁺.

N-(4-formylcyclohexyl)-4-(isopropylamino)-6-[5-(trifluoromethyl)pyrrolo[2,3-b]pyridin-1-yl] pyridine-3-carboxamide (Intermediate CFI)

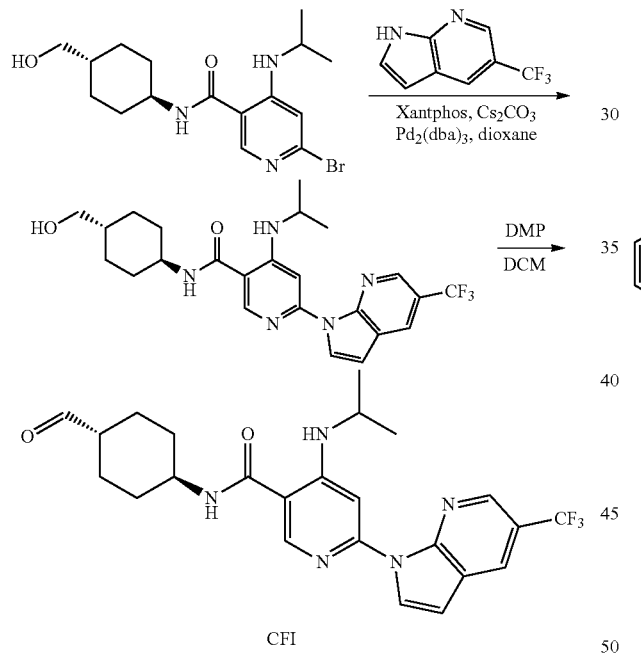

CFI

Step 1—N-[4-(hydroxymethyl)cyclohexyl]-4-(isopropylamino)-6-[5-(trifluoromethyl)pyrrolo[2,3-b] pyridin-1-yl]pyridine-3-carboxamide To a solution of 6-bromo-N-[4-(hydroxymethyl)cyclohexyl]-4-(isopropylamino)pyridine-3-carboxamide (50.0 mg, 135 umol, synthesized via Steps 1-4 of Intermediate BVU) and 5-(trifluoromethyl)-1H-pyrrolo[2,3-b]pyridine (27.7 mg, 148 umol, CAS #1036027-54-9) in dioxane (2 mL) was added TBUBRETTPHOS PD G3 (11.5 mg, 13.5 umol) and tBuONa (2 M, 203 uL)/Then the mixture was stirred at 90° C. for 16 hours. On completion, the mixture was filtered and the filtrate was concentrated in vacuo to give the residue. The residue was purified by prep-HPLC (column: Phenomenex luna C18 150*25 mm*10 um; mobile phase: [water(FA)-ACN]; B %: 42%-72%, 10.5 min) to give the title compound (15.5 mg, 24% yield) as a yellow solid. ¹H NMR (400 MHz, DMSO-d₆) δ 8.77 (d, J=1.6 Hz, 1H), 8.62-8.51 (m, 4H), 8.30 (d, J=7.6 Hz, 1H), 8.18 (s, 1H), 6.90 (d, J=4.0 Hz, 1H), 4.41 (s, 1H), 3.83-3.66 (m, 2H), 3.24-3.22 (m, 2H), 2.52-2.51 (m, 1H), 1.91-1.84 (m, 2H), 1.80-1.77 (m, 2H), 1.34 (s, 2H), 1.30 (s, 3H), 1.29 (s, 3H), 1.03-0.92 (m, 2H). LC-MS (ESI⁺) m/z 476.5 (M+H)⁺.

Step 2—N-(4-formylcyclohexyl)-4-(isopropylamino)-6-[5-(trifluoromethyl)pyrrolo[2,3-b]pyridin-1-yl] pyridine-3-carboxamide To a solution of N-[4-(hydroxymethyl)cyclohexyl]-4-(isopropylamino)-6-[5-(trifluoromethyl)pyrrolo[2,3-b]pyridine-1-yl]pyridine-3-carboxamide (80.0 mg, 168 umol) in DCM (3 mL) was added DMP (78.1 u, 252 umol) at 0° C. Then the mixture was stirred at 25° C. for 1 hour. On completion, the mixture was quenched with sodium thiosulfate pentahydrate (10 mL) and NaHCO₃ (10 mL), then extracted with DCM (20 mL×3). The combined organic layer was dried over anhydrous Na₂SO₄, then concentrated in vacuo to give the title compound (74.0 mg, 93% yield) as a yellow solid. LC-MS (ESI+) m/z 474.3 (M+H)⁺.

1-(7-Bromo-8-methoxy-4-isoquinolyl)-3-[(4-methoxyphenyl) methyl] hexahydropyrimidine-2,4-dione (Intermediate CFJ)

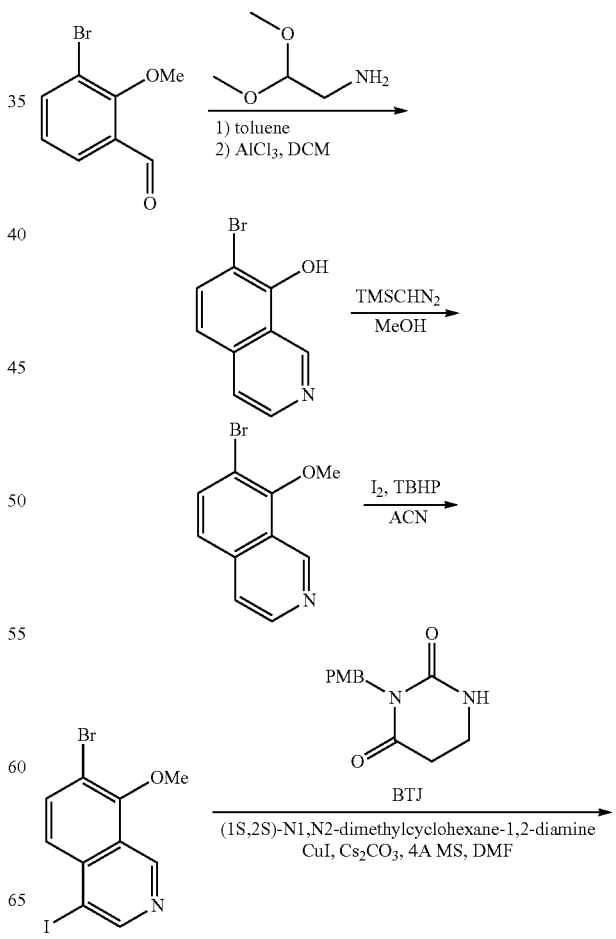

-continued

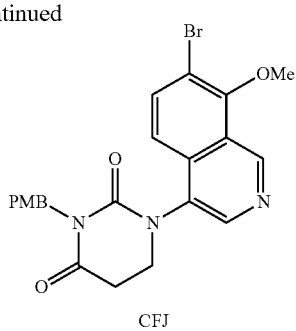

CFJ

Step 1—7-Bromoisoquinolin-8-ol

To a solution of 3-bromo-2-methoxy-benzaldehyde (3 g, 13.9 mmol, CAS #88275-87-0) in toluene (40 mL) was added 2,2-dimethoxyethanamine (1.54 g, 14.6 mmol, CAS #22483-09-6). The mixture was stirred at 100° C. for 4 hrs. Then the mixture was concentrated in vacuo and dissolved in DCM (20 mL) and cooled to 0° C. Next, AlCl$_3$ (6.14 g, 46.0 mmol) was added to above solution portion-wise and the resulting dark red suspension was left to stir at 0° C. for 30 minutes and was then allowed to slowly warm to 25° C. and stirred for 16 hours. On completion, the mixture was quenched with MeOH (20 mL) and concentrated in vacuo. The crude product was purified by prep-HPLC (reverse phase: 0.1% FA) to give the title compound (1.2 g, 38% yield) as a yellow solid. $^1$H NMR (400 MHz, DMSO-d$_6$) δ 10.61 (s, 1H), 9.56 (s, 1H), 8.50 (d, J=5.6 Hz, 1H), 7.83 (d, J=8.8 Hz, 1H), 7.77 (d, J=5.6 Hz, 1H), 7.39 (d, J=8.0 Hz, 1H). LC-MS (ESI$^+$) m/z 224.0 (M+H)$^+$.

Step 2—7-Bromo-8-methoxy-isoquinoline

To a solution of 7-bromoisoquinolin-8-ol (1 g, 4.46 mmol) in MeOH (15 mL) was added TMSCHN$_2$ (2 M, 11.16 mL). The mixture was then stirred at 25° C. for 16 hrs. On completion, the mixture was quenched with HOAc (5 mL) and concentrated in vacuo. The crude product was purified by silica gel column to give the title compound (305 mg, 28% yield) as yellow solid. $^1$H NMR (400 MHz, DMSO-d$_6$) δ 9.47 (s, 1H), 8.61 (d, J=6.0 Hz, 1H), 7.95 (d, J=8.8 Hz, 1H), 7.91-7.86 (m, 1H), 7.74 (d, J=8.8 Hz, 1H), 4.02 (s, 3H). LC-MS (ESI$^+$) m/z 238.0 (M+H)$^+$.

Step 3—7-Bromo-4-iodo-8-methoxy-isoquinoline

To a solution of 7-bromo-8-methoxy-isoquinoline (305 mg, 1.28 mmol) in ACN (8 mL) was added I2 (390 mg, 1.54 mmol) and TBHP (1.32 g, 10.2 mmol 70% solution). The mixture was stirred at 80° C. for 16 hrs. On completion, the mixture was quenched with sat. Na$_2$S$_2$O$_3$ (20 mL), then diluted with H$_2$O (50 mL), and extracted with EA (3×50 mL). The organic layers were washed with brine (3×50 mL), dried over anhydrous Na$_2$SO$_4$, filtered and concentrated in vacuo. The residue was purified by column chromatography (SiO$_2$, PE:EA=50:1) to give the title compound (429 mg, 90% yield) as yellow solid. $^1$H NMR (400 MHz, DMSO-d$_6$) δ 9.40 (s, 1H), 9.02 (s, 1H), 8.11 (d, J=8.8 Hz, 1H), 7.71 (d, J=9.2 Hz, 1H), 4.03 (s, 3H). LC-MS (ESI$^+$) m/z 365.8 (M+H)$^+$.

Step 4—1-(7-Bromo-8-methoxy-4-isoquinolyl)-3-[(4-methoxyphenyl) methyl]hexahydropyrimidine-2,4-dione To a solution of 7-bromo-4-iodo-8-methoxy-isoquinoline (300 mg, 824 umol) and 3-[(4-methoxyphenyl)methyl]hexahydropyrimidine-2,4-dione (212 mg, 906 umol, Intermediate BTJ) in DMF (20 mL) was added (1S,2S)—N1,N2-dimethylcyclohexane-1,2-diamine (46.9 mg, 329 umol), Cs$_2$CO$_3$ (537 mg, 1.65 mmol), 4 Å molecular sieves (50 mg) and CuI (62.7 mg, 329 umol). The mixture was degassed and purged with N$_2$ three times and the mixture was stirred at 70° C. for 16 hrs under N$_2$ atmosphere. On completion, the mixture was filtered and concentrated in vacuo. The mixture was purified by reversed phase (0.1% FA) to give the title compound (130 mg, 33% yield) as brown oil. $^1$H NMR (400 MHz, DMSO-d$_6$) δ 9.46 (s, 1H), 8.67 (s, 1H), 7.97 (d, J=8.8 Hz, 1H), 7.70 (d, J=9.6 Hz, 1H), 7.25 (d, J=8.8 Hz, 2H), 6.90-6.86 (m, 2H), 4.83 (s, 2H), 4.04 (s, 3H), 3.73 (s, 3H), 3.20-3.06 (m, 2H), 3.04-2.71 (m, 2H). LC-MS (ESI$^+$) m/z 472.1 (M+H)$^+$.

1-(8-Methoxy-7-piperazin-1-yl-4-isoquinoly)hexahydropyrimidine-2,4-dione (Intermediate CFK)

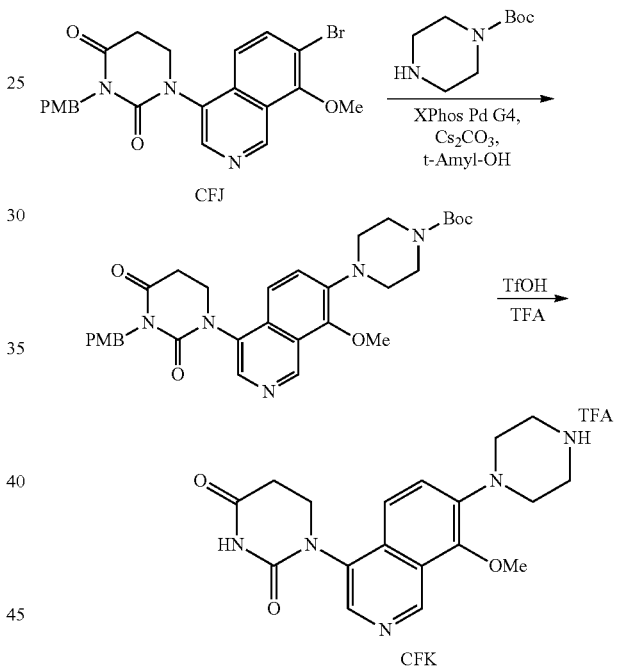

Step 1—Tert-butyl 4-[8-methoxy-4-[3-[(4-methoxyphenyl)methyl]-2,4-dioxo-hexahydropyrimidin-1-yl]-7-isoquinolyl]piperazine-1-carboxylate To a mixture of 1-(7-bromo-8-methoxy-4-isoquinolyl)-3-[(4-methoxyphenyl)methyl]hexahydropyrimidine-2,4-dione (250 mg, 531 umol, Intermediate CFJ) and tert-butyl piperazine-1-carboxylate (297 mg, 1.59 mmol, CAS #143238-38-4) in t-Amyl-OH (3 mL) was added Xphos Pd G4 (45.7 mg, 53.1 umol) and Cs$_2$CO$_3$ (519 mg, 1.59 mmol). The reaction mixture was stirred at 100° C. for 1 hour. On completion, the reaction mixture was filtered and diluted with water (10 mL) and extracted with EA (2×30 mL). The combined organic layer was dried over Na$_2$SO$_4$, filtered and concentrated in vacuo to give a residue. The residue was purified by reverse phase (0.1% FA condition) to give the title compound (80.0 mg, 26% yield) as white solid. $^1$H NMR (400 MHz, DMSO-d$_6$) δ 9.37 (s, 1H), 8.42 (s, 1H), 7.65-7.56 (m, 2H), 7.25 (d, J=8.4 Hz, 2H), 6.88 (d, J=8.4 Hz, 2H), 4.82 (s, 2H), 3.99 (s, 3H), 3.94-3.86 (m, 1H), 3.76-3.69 (m, 4H), 3.56 (s, 4H), 3.19-3.13 (m, 4H), 3.13-3.05 (m, 1H), 3.00-2.92 (m, 1H), 1.43 (s, 9H).

Step 2—1-(8-Methoxy-7-piperazin-1-yl-4-isoquinolyl)hexahydropyrimidine-2,4-dione To a mixture of tert-butyl 4-[8-methoxy-4-[3-[(4-methoxyphenyl)methyl]-2,4-dioxo-hexahydropyrimidin-1-yl]-7-isoquinolyl]piperazine-1-carboxylate (80.0 mg, 138 umol) in TFA (3 mL) was added TfOH (850 mg, 5.66 mmol, 0.5 mL). The reaction mixture was then stirred at 80° C. for 1 hour. On completion, the reaction mixture was concentrated in vacuo to give the title compound (60.0 mg, 91% yield, TFA) as red oil. LC-MS (ESI+) m/z 356.1 (M+H)$^+$.

N-[6-ethyl-2-(4-formylcyclohexyl)indazol-5-yl]-6-(trifluoromethyl)pyridine-2-carboxamide (Intermediate CFL)

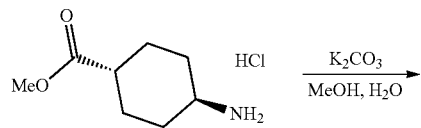

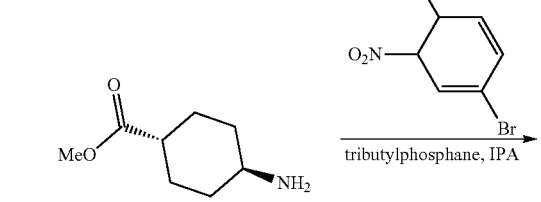

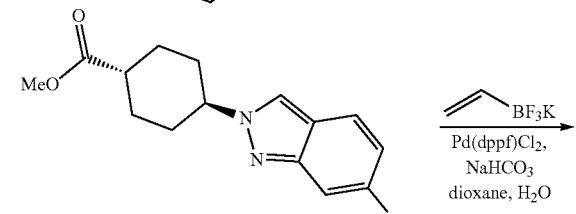

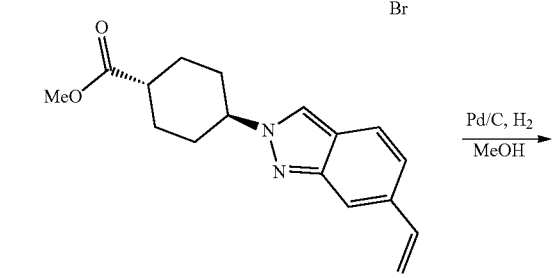

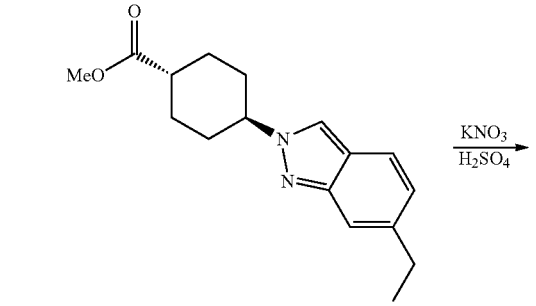

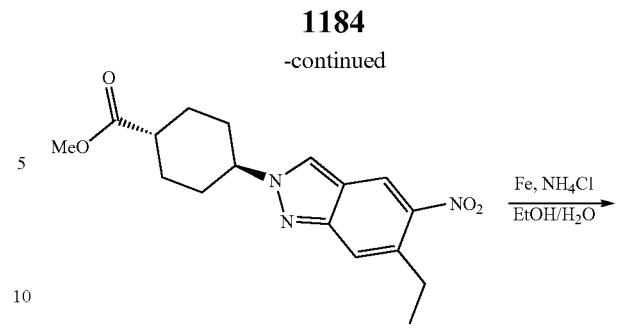

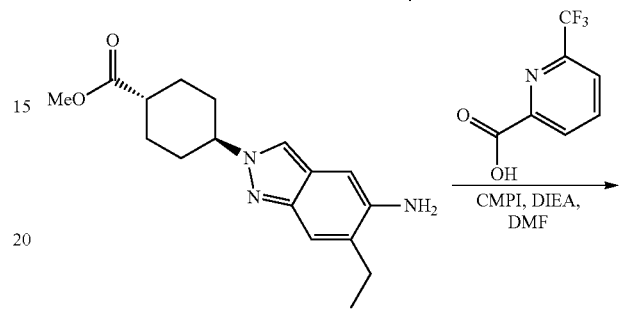

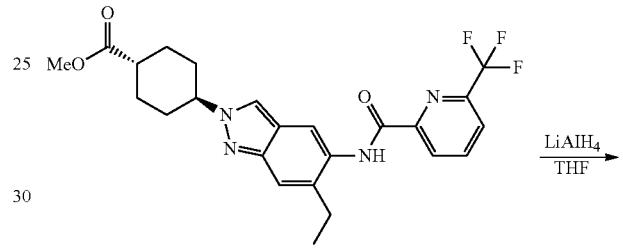

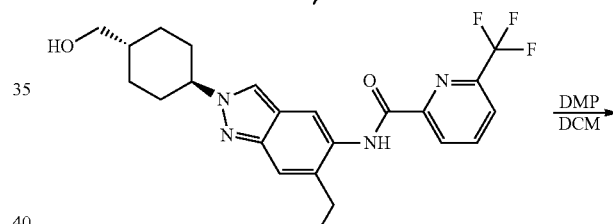

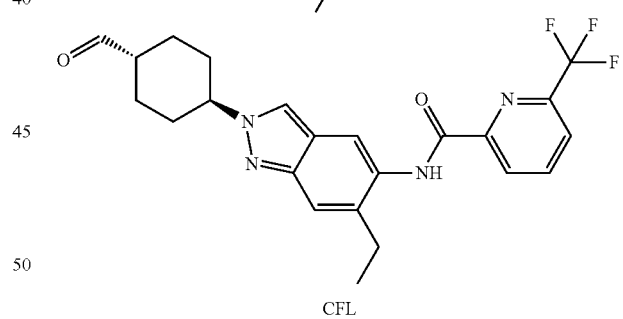

CFL

Step 1—Methyl 4-aminocyclohexanecarboxylate

To a mixture of methyl 4-aminocyclohexanecarboxylate (5.00 g, 25.8 mmol, HCl, CAS #61367-07-5) in MeOH (50 mL) and H$_2$O (0.5 mL) was added K$_2$CO$_3$ (3.57 g, 25.8 mmol) at 25° C. The mixture was then stirred at 25° C. for 4 hrs. On completion, the reaction mixture was filtered and the filtrate concentrated in vacuo to give the title compound (4.00 g, 98% yield) as a white solid.

Step 2—Methyl 4-(6-bromoindazol-2-yl)cyclohexanecarboxylate

To a solution of methyl 4-aminocyclohexanecarboxylate (4.00 g, 25.4 mmol) in IPA (50 mL) was added 4-bromo-2-nitro-benzaldehyde (5.85 g, 25.4 mmol, CAS #5551-12-2). The mixture was then stirred at 80° C. for 3 hours under $N_2$ atmosphere. Next, tributylphosphane (15.4 g, 76.3 mmol) was added at 25° C. then the reaction mixture was stirred at 80° C. for 12 hours under $N_2$ atmosphere. On completion, the mixture was concentrated in vacuo, then triturated with petroleum ether (100 mL) at 25° C. for 10 mins and filtered. The filter cake was dried in vacuo to give the title compound (6.00 g, 69% yield) as a yellow solid. LC-MS (ESI$^+$) m/z 338.9 (M+3)$^+$.

Step 3—Methyl 4-(6-vinylindazol-2-yl)cyclohexanecarboxylate

A mixture of methyl 4-(6-bromoindazol-2-yl)cyclohexanecarboxylate (6.00 g, 17.7 mmol), potassium hydride; trifluoro(vinyl)boron (7.15 g, 53.3 mmol, CAS #233664-53-4), Pd(dppf)Cl$_2$ (650 mg, 889 umol) and NaHCO$_3$ (2.99 g, 35.5 mmol) in a mixed solvent of dioxane (100 mL) and H$_2$O (10 mL) was stirred at 90° C. for 4 hours under nitrogen atmosphere. On completion, the reaction mixture was filtered and the filtrate was concentrated in vacuo. The residue was purified by silica gel chromatography (petroleum ether:ethyl acetate=5:1) to give the title compound (4.00 g, 79% yield) as a brown solid. LC-MS (ESI$^+$) m/z 285.1 (M+H)$^+$.

Step 4—Methyl 4-(6-ethylindazol-2-yl)cyclohexanecarboxylate

To a mixture of methyl 4-(6-vinylindazol-2-yl)cyclohexanecarboxylate (2.00 g, 7.0 mmol) in MeOH (15 mL) was added Pd/C (50.0 mg, 7.0 mmol, 10 wt %). The mixture was added at 25° C. for 0.5 hr under H$_2$ (15 Psi). On completion, the mixture was filtered and concentrated to give the title compound (1.90 g, 91% yield) as yellow solid. $^1$H NMR (400 MHz, DMSO-d$_6$) δ 8.28 (s, 1H), 7.58 (d, J=8.4 Hz, 1H), 7.34 (s, 1H), 6.90 (d, J=8.4 Hz, 1H), 4.45 (m, 1H), 3.80-3.43 (m, 3H), 2.66 (q, J=7.6 Hz, 2H), 2.47-2.38 (m, 1H), 2.17-1.89 (m, 6H), 1.59 (m, 2H), 1.24-1.18 (m, 3H); LC-MS (ESI+) m/z 287.0 (M+H)$^+$.

Step 5—Methyl 4-(6-ethyl-5-nitro-indazol-2-yl)cyclohexanecarboxylate

To a solution of methyl 4-(6-ethylindazol-2-yl)cyclohexanecarboxylate (600 mg, 2.10 mmol) in H$_2$SO$_4$ (5 mL) was added KNO$_3$ (211 mg, 2.10 mmol) at −10° C. The reaction mixture was stirred at −10° C. for 3 hrs. On completion, the mixture was quenched with ice water and extracted with ethyl acetate (50 mL×3). The combined organic phase was washed with NaHCO$_3$ (80 mL) and H$_2$O (80 mL), dried over anhydrous sodium sulfate, filtered and concentrated to the title compound (680 mg, 94% yield) as yellow oil. $^1$H NMR (400 MHz, DMSO-d$_6$) δ 8.68 (s, 1H), 8.52 (s, 1H), 7.62 (s, 1H), 4.61-4.53 (m, 1H), 3.63 (d, J=1.6 Hz, 3H), 2.90 (q, J=7.6 Hz, 2H), 2.46-2.39 (m, 1H), 2.16 (d, J=12.4 Hz, 2H), 2.07 (d, J=13.6 Hz, 2H), 1.97-1.90 (m, 2H), 1.59 (d, J=12.4 Hz, 2H), 1.21-1.17 (m, 3H); LC-MS (ESI+) m/z 331.9 (M+H)$^+$.

Step 6—Methyl 4-(5-amino-6-ethyl-indazol-2-yl)cyclohexanecarboxylate

A mixture of methyl 4-(6-ethyl-5-nitro-indazol-2-yl)cyclohexanecarboxylate (680 mg, 2.0 mmol), Fe (802 mg, 14.3 mmol) and NH$_4$Cl (1.10 g, 20.5 mmol) in a mixed solvent of EtOH (10 mL) and H$_2$O (2 mL) was stirred at 80° C. for 12 hrs under $N_2$. On completion, the reaction mixture was filtered through celite and the filtrate was concentrated in vacuo. The residue was purified by prep-HPLC purification (column: YMC Triart C18 250*50 mm*7 um; mobile phase: [water (FA)-ACN]; B %: 17%-47%, 10 min) to give the title compound (110 mg, 17% yield) as brown solid. $^1$H NMR (400 MHz, DMSO-d$_6$) δ 7.88 (s, 1H), 7.18 (s, 1H), 6.65 (s, 1H), 4.75-4.42 (m, 2H), 4.41-4.24 (m, 1H), 3.62 (s, 3H), 2.59-2.54 (m, 2H), 2.46-2.38 (m, 1H), 2.13-2.01 (m, 4H), 1.97-1.83 (m, 2H), 1.63-1.50 (m, 2H), 1.19 (t, J=7.2 Hz, 3H); LC-MS (ESI+) m/z 301.9 (M+H)$^+$.

Step 7—Methyl 4-[6-ethyl-5-[[6-(trifluoromethyl)pyridine-2-carbonyl]amino]indazol-2-yl]cyclohexanecarboxylate A mixture of 6-(trifluoromethyl)pyridine-2-carboxylic acid (57.0 mg, 298.6 umol, CAS #131747-42-7), CMPI (99.1 mg, 388 umol) and DIPEA (115 mg, 895 umol) in DMF (0.5 mL) was stirred at 25° C. for 15 min. Then a solution of methyl 4-(5-amino-6-ethyl-indazol-2-yl)cyclohexanecarboxylate (90.0 mg, 298 umol) in DMF (0.5 mL) was added. The reaction mixture was stirred at 25° C. for 0.5 hr. On completion, the mixture was quenched with ice water (5 mL) and filtered to give the title compound (105 mg, 73% yield) as a brown solid. LC-MS (ESI+) m/z 475.0 (M+H)$^+$.

Step 8—N-[6-ethyl-2-[4-(hydroxymethyl)cyclohexyl]indazol-5-yl]-6-(trifluoromethyl)pyridine-2-carboxamide To a mixture of methyl 4-[6-ethyl-5-[[6-(trifluoromethyl)pyridine-2-carbonyl]amino]indazol-2-yl]cyclohexanecarboxylate (105.0 mg, 221.3 umol) in THF (5 mL) was added LiAlH4 (16.8 mg, 442.5 umol) at 0° C. The mixture was then stirred at 25° C. for 1 hr. On completion, the reaction mixture was quenched with H$_2$O (1 mL) and 15% NaOH (6 mL) at 20° C. Then the mixture was dried over anhydrous sodium sulfate, filtered and concentrated under reduced pressure to give a residue to give the title compound (89.0 mg, 79% yield) as a brown solid. LC-MS (ESI+) m/z 447.0 (M+H)$^+$.

Step 9—N-[6-ethyl-2-(4-formylcyclohexyl)indazol-5-yl]-6-(trifluoromethyl)pyridine-2-carboxamide To a solution of N-[6-ethyl-2-[4-(hydroxymethyl)cyclohexyl]indazol-5-yl]-6-(trifluoromethyl) pyridine-2-carboxamide (89.0 mg, 199.3 umol) in DCM (3 mL) was added DMP (126.8 mg, 299.0 umol) at 0° C. The mixture was then stirred at 25° C. for 2 hrs. On completion, the mixture was quenched with saturated solution of Na$_2$S$_2$O$_3$ (40 mL) and saturated solution of NaHCO$_3$ (30 mL), then extracted with DCM (40 mL×3). The combined organic phase was dried over anhydrous sodium sulfate, filtered and concentrated to give a residue. The crude product was triturated with PE (1 mL) at 25° C. for 10 mins to give the title compound (80.0 mg, 77% yield) as brown solid. $^1$H NMR (400 MHz, DMSO-d$_6$) δ 10.18 (s, 1H), 9.65 (s, 1H), 8.48-8.42 (m, 1H), 8.40 (d, J=7.6 Hz, 1H), 8.38 (s, 1H), 8.24 (s, 1H), 8.21 (d, J=7.2 Hz, 1H), 7.50 (s, 1H), 4.55-4.37 (m, 1H), 2.78 (q, J=7.6 Hz, 2H), 2.44-2.39 (m, 1H), 2.21 (d, J=12.4 Hz, 2H), 2.11 (d, J=11.6 Hz, 2H), 2.04-1.93 (m, 2H), 1.51-1.39 (m, 2H), 1.26 (t, J=7.6 Hz, 3H); LC-MS (ESI+) m/z 445.1 (M+H)$^+$.

N-[2-(4-formylcyclohexyl)-6-morpholino-indazol-5-yl]-6-(trifluoromethyl)pyridine -2-carboxamide (Intermediate CFM)

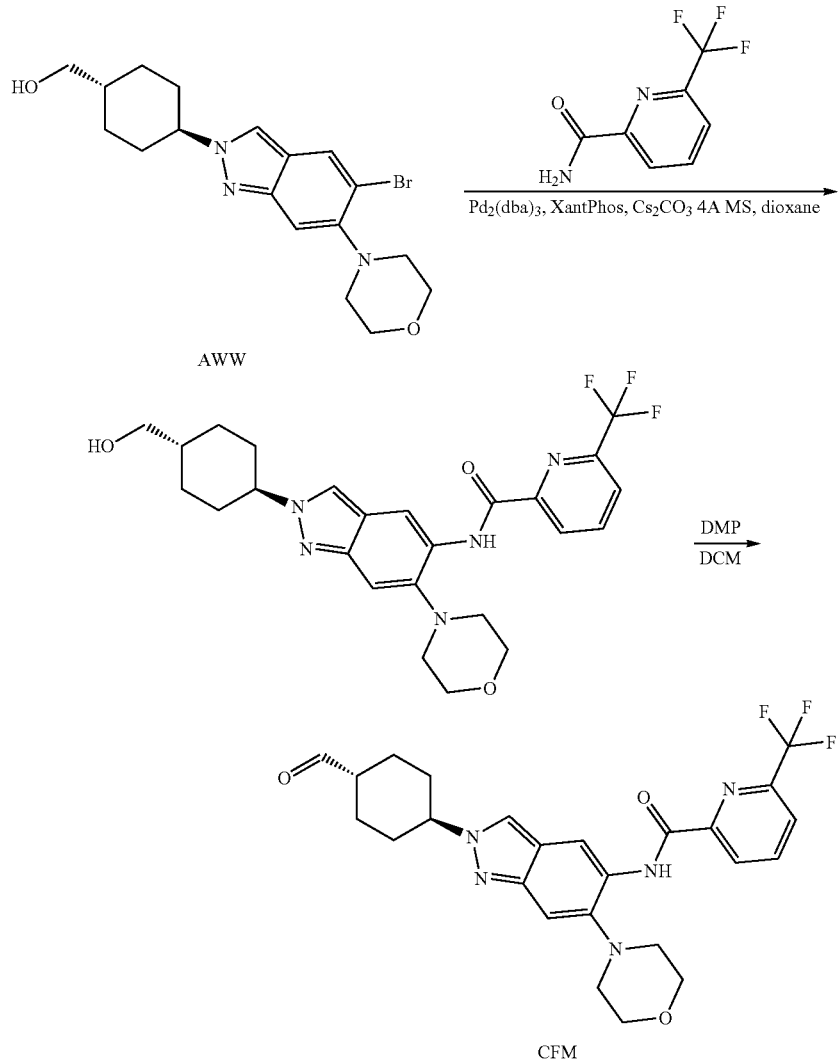

Step 1—N-[2-[4-(hydroxymethyl)cyclohexyl]-6-morpholino-indazol-5-yl]-6-(trifluoromethyl)pyridine-2-carboxamide To a mixture of [4-(5-bromo-6-morpholino-indazol-2-yl)cyclohexyl]methanol (1.20 g, 3.04 mmol, Intermediate AWW) and 6-(trifluoromethyl)pyridine-2-carboxamide (694 mg, 3.65 mmol, CAS #22245-84-7) in dioxane (20 mL) was added 4 Å molecular sieves (1.00 g, 3.04 mmol), $Pd_2(dba)_3$ (278 mg, 304 umol), Xantphos (352 mg, 608 umol) and $Cs_2CO_3$ (2.97 g, 9.13 mmol). The reaction mixture was then stirred at 100° C. for 12 hours. On completion, the reaction mixture was filtered and concentrated in vacuo. The residue was diluted with water (30 mL) and extracted with EA (2×30 mL). The combined organic layer was dried over $Na_2SO_4$, filtered and concentrated in vacuo to give a residue. The residue was purified by reverse phase (0.1% FA condition) to give the title compound (940 mg, 61% yield) as white solid. LC-MS (ESI$^+$) m/z 504.3 (M+H)$^+$.

Step 2—N-[2-(4-formylcyclohexyl)-6-morpholino-indazol-5-yl]-6-(trifluoromethyl)pyridine-2-carboxamide To a mixture of N-[2-[4-(hydroxymethyl)cyclohexyl]-6-morpholino-indazol-5-yl]-6-(trifluoromethyl) pyridine-2-carboxamide (100 mg, 198 umol) in DCM (3 mL) was added DMP (109 mg, 258 umol, 79.9 uL). The reaction mixture was then stirred at 25° C. for 1 hr. On completion, the reaction mixture was quenched with saturated $Na_2S_2O_3$ (3 mL) and saturated $NaHCO_3$(3 mL) at 25° C., and then stirred for 30 minutes. The residue was diluted with water (10 mL) and extracted with DCM (2×20 mL). The combined organic layer was dried over $Na_2SO_4$, filtered and concentrated in vacuo to give the title compound (80.0 mg, 80% yield) as white solid. LC-MS (ESI$^+$) m/z 502.2 (M+H)$^+$.

1-(8-Bromoquinazolin-4-yl)-3-[(4-methoxyphenyl)methyl]hexahydropyrimidine-2,4-dione (Intermediate CFN)

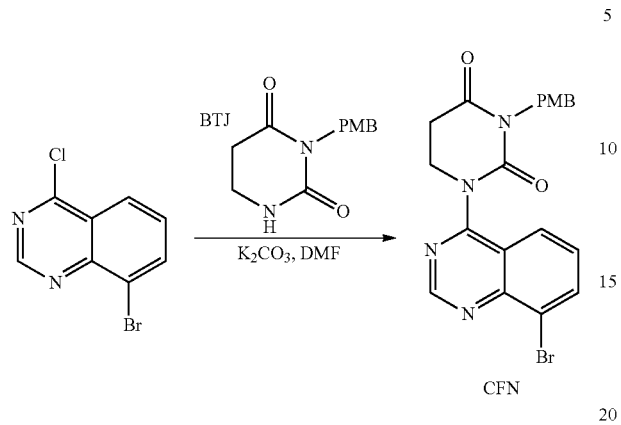

To a solution of 8-bromo-4-chloro-quinazoline (2.00 g, 8.21 mmol, CAS #125096-72-2) and 3[(4-methoxyphenyl)methyl]hexahydropyrimidine-2,4-dione (2.89 g, 12.3 mmol, Intermediate BTJ) in DMF (25 mL) was added $K_2CO_3$ (3.41 g, 24.6 mmol), then the mixture was stirred at 60° C. for 10 hours. On completion, the mixture was filtered and the filtrate was extracted with water (200 mL) and EA (150 mL×3). The combined organic layers was dried over anhydrous $Na_2SO_4$, then concentrated in vacuo to give the residue. The residue was purified by reverse-phase (0.1% FA condition) to give the title compound (1.10 g, 30% yield) as a yellow solid. $^1$H NMR (400 MHz, DMSO-$d_6$) δ 9.29 (s, 1H), 8.37-8.35 (m, 1H), 8.11-8.09 (m, 1H), 7.65-7.54 (m, 1H), 7.22 (d, J=8.8 Hz, 2H), 6.89-6.85 (m, 2H), 4.84 (s, 2H), 4.06 (s, 2H), 3.72 (s, 3H), 3.09-3.01 (m, 2H). LC-MS (ESI$^+$) m/z 442.9 (M+H)$^+$.

1-(8-Piperazin-1-ylquinazolin-4-yl)hexahydropyrimidine-2,4-dione (Intermediate CFO)

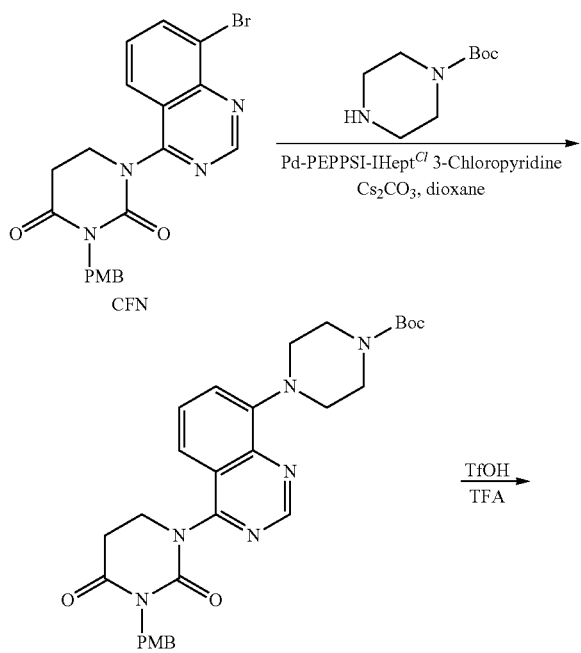

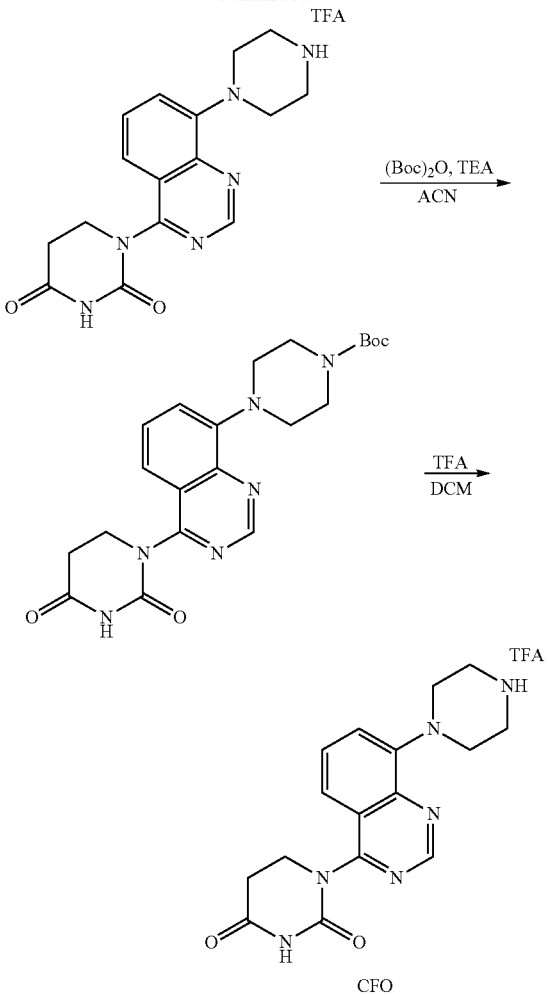

Step 1—Tert-butyl 4-[4-[3-[(4-methoxyphenyl)methyl]-2,4-dioxo-hexahydropyrimidin-1-yl] quinazolin-8-yl]piperazine-1-carboxylate To a solution of 1-(8-bromoquinazolin-4-yl)-3-[(4-methoxyphenyl)methyl]hexahydropyrimidine -2,4-dione (500 mg, 1.13 mmol, Intermediate CFN) and tert-butyl piperazine-1-carboxylate (316 mg, 1.70 mmol, CAS #143238-38-4) in dioxane (6 mL) was added Pd-PEPPSI-IHeptCl 3-Chloropyridine (110 mg, 113 umol) and $Cs_2CO_3$ (738 mg, 2.27 mmol). Then the mixture was stirred at 80° C. for 10 hours. On completion, the mixture was filtered and the filtrate was concentrated in vacuo to give the residue. The residue was purified by reverse-phase (0.1% FA condition) to give the title compound (230 mg, 37% yield) as a yellow solid. $^1$H NMR (400 MHz, DMSO-$d_6$) δ 9.15 (s, 1H), 7.61-7.51 (m, 2H), 7.36-7.34 (m, 1H), 7.22 (d, J=8.4 Hz, 2H), 6.89-6.85 (m, 2H), 4.83 (s, 2H), 4.01 (s, 2H), 3.72 (s, 3H), 3.59 (s, 4H), 3.28 (s, 2H), 3.12-2.96 (m, 2H), 2.52-2.50 (m, 2H), 1.44 (s, 9H). LC-MS (ESI$^+$) m/z 547.5 (M+H)$^+$.

Step 2—1-(8-Piperazin-1-ylquinazolin-4-yl)hexahydropyrimidine-2,4-dione

To a solution of tert-butyl 4-[4-[3-[(4-methoxyphenyl)methyl]-2,4-dioxo-hexahydropyrimidin-1-yl]quinazolin-8- yl]piperazine-1-carboxylate (200 mg, 365 umol) in TFA (5 mL) was added TfOH (2 mL, 22.6 mmol), then the mixture was stirred at 70° C. for 1 hour. On completion, the mixture was concentrated in vacuo to give the title compound (150 mg, 93% yield, TFA) as a brown solid.

Step 3—Tert-butyl 4-[4-(2,4-dioxohexahydropyrimidin-1-yl)quinazolin-8-yl]piperazine-1-carboxylate To a solution of 1-(8-piperazin-1-ylquinazolin-4-yl)hexahydropyrimidine-2,4-dione (150 mg, 340 umol, TFA) in DCM (4 mL) was added TEA (94.8 uL, 681 umol) and $Boc_2O$ (117 uL, 510 umol), then the mixture was stirred at 25° C. for 10 hours. On completion, the mixture was concentrated in vacuo to give the residue. The residue was purified by prep-HPLC (column: Phenomenex luna C18 150*25 mm*10 um; mobile phase: [water(FA)-ACN]; B %: 26%-56%, 9 min) to give the title compound (90.0 mg, 62% yield) as a yellow solid. $^1$H NMR (400 MHz, DMSO-$d_6$) δ 10.75 (s, 1H), 9.15 (s, 1H), 7.65-7.60 (m, 1H), 7.58-7.52 (m, 1H), 7.35 (d, J=6.8 Hz, 1H), 4.02 (s, 2H), 3.59 (s, 4H), 2.84 (s, 2H), 2.52-2.50 (m, 4H), 1.44 (s, 9H). LC-MS (ESI$^+$) m/z 427.3 (M+H)$^+$.

Step 4—1-(8-Piperazin-1-ylquinazolin-4-yl)hexahydropyrimidine-2,4-dione

To a solution of tert-butyl 4-[4-(2,4-dioxohexahydropyrimidin-1-yl)quinazolin-8-yl]piperazine-1-carboxylate (90.0 mg, 211 umol) in DCM (2 mL) was added TFA (0.8 mL, 10.8 mmol), then the mixture was stirred at 25° C. for 1 hour. On completion, the mixture was concentrated in vacuo to give the title compound (90.0 mg, 96% yield, TFA) as a green solid. LC-MS (ESI$^+$) m/z 327.1 (M+H)$^+$.

1-(8-bromo-4-quinolyl)-3-[(4-methoxyphenyl) methyl]hexahydropyrimidine-2,4-dione (Intermediate CFP)

Step 1—(8-Bromo-4-quinolyl) trifluoromethanesulfonate

To a mixture of 8-bromoquinolin-4-ol (0.500 g, 2.23 mmol, CAS #57798-00-2), pyridine (529 mg, 6.69 mmol) and DMAP (13.6 mg, 111 umol) in DCM (10 mL) was added $Tf_2O$ (944 mg, 3.35 mmol) at 0° C. Then the reaction mixture was stirred at 25° C. for 2 hour. On completion, the reaction mixture was diluted with water (10 mL) and extracted with EA (2×20 mL). The combined organic layer was dried over $Na_2SO_4$, filtered and concentrated in vacuo to give the title compound (720 mg, 90% yield) as light yellow solid. $^1$H NMR (400 MHz, DMSO-$d_6$) δ 9.19 (d, J=5.2 Hz, 1H), 8.60-8.55 (m, 1H), 8.38-8.32 (m, 1H), 8.06 (d, J=8.4 Hz, 1H), 7.91 (d, J=5.2 Hz, 1H).

Step 2—1-(8-Bromo-4-quinolyl)-3-[(4-methoxyphenyl)methyl]hexahydropyrimidine-2,4-dione To a mixture of (8-bromo-4-quinolyl) trifluoromethanesulfonate (500 mg, 1.40 mmol) and 3-[(4-methoxyphenyl) methyl]hexahydropyrimidine-2,4-dione (328 mg, 1.40 mmol, Intermediate BTJ) in dioxane (10 mL) was added $Pd_2(dba)_3$ (128 mg, 140 umol), Xantphos (162 mg, 280 umol) and $Cs_2CO_3$ (1.37 g, 4.21 mmol). The reaction mixture was then stirred at 80° C. for 4 hour. On completion, the residue was diluted with water (10 mL) and extracted with EA (2×10 mL). The combined organic layer was dried over $Na_2SO_4$, filtered and concentrated in vacuo to give a residue. The residue was purified by prep-HPLC (column: Waters xbridge 150*25 mm 10 um; mobile phase: [water ($NH_4HCO3$)-ACN]; B %: 32%-62%, 8 min) to give the title compound (97.0 mg, 15% yield) as white solid. $^1$H NMR (400 MHz, DMSO-$d_6$) δ 9.09 (d, J=4.4 Hz, 1H), 8.23-8.18 (m, 1H), 8.05-8.00 (m, 1H), 7.70 (d, J=4.4 Hz, 1H), 7.57-7.48 (m, 1H), 7.28-7.24 (m, 2H), 6.93-6.84 (m, 2H), 4.83 (s, 2H), 4.12-4.00 (m, 1H), 3.73 (s, 4H), 3.27-3.14 (m, 1H), 2.97-2.86 (m, 1H).

1-(8-piperazin-1-yl-4-quinolyl)hexahydropyrimidine-2,4-dione (Intermediate CFQ)

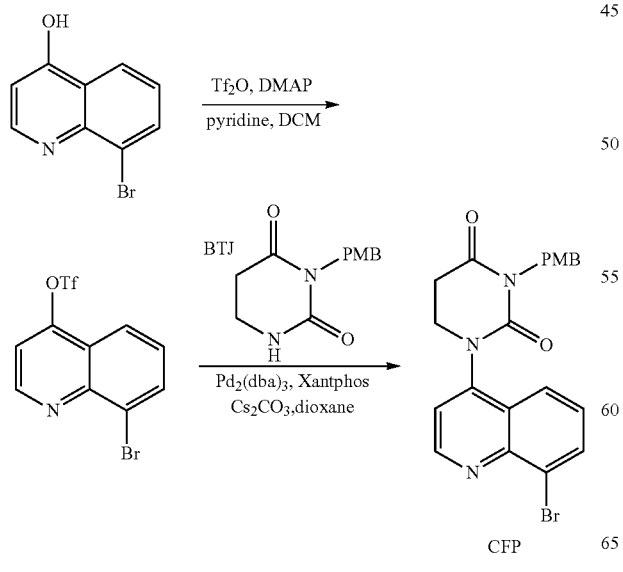

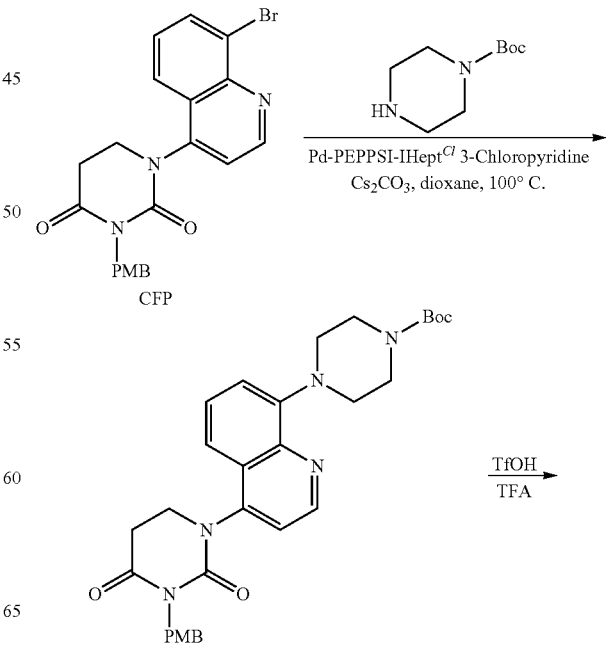

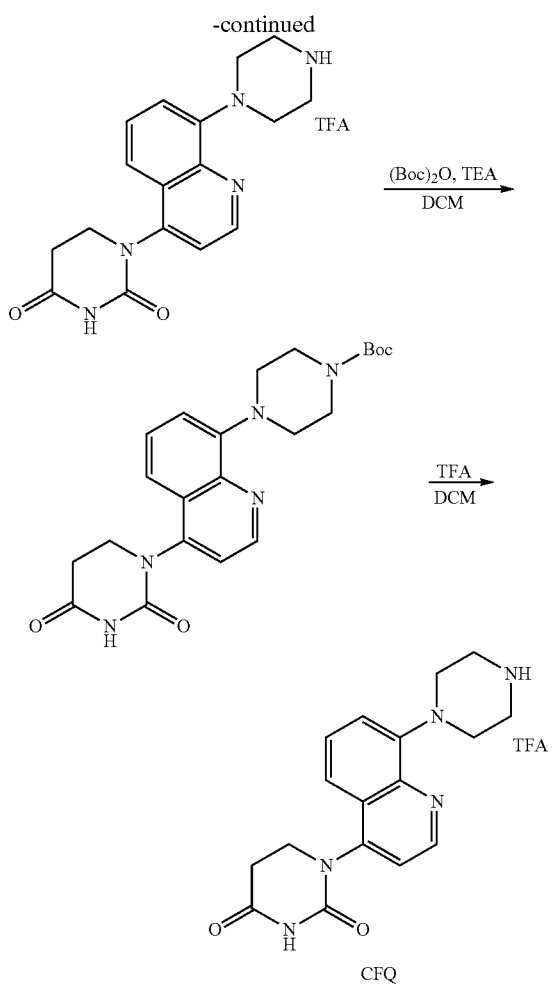

CFQ

Step 1—Tert-butyl 4-[4-[3-[(4-methoxyphenyl)methyl]-2,4-dioxo-hexahydropyrimidin-1-yl]-8-quinolyl]piperazine -1-carboxylate A solution of 1-(8-bromo-4-quinolyl)-3-[(4-methoxyphenyl)methyl]hexahydropyrimidine-2,4-dione (468 mg, 1.06 mmol, Intermediate CFP), tert-butyl piperazine-1-carboxylate (237 mg, 1.28 mmol, CAS #57260-71-6), $Cs_2CO_3$ (1.04 g, 3.19 mmol) and Pd-PEPPSI-IHept$^{Cl}$ 3-Chloropyridine (103 mg, 106 umol) in dioxane (7 mL) was stirred at 100° C. under $N_2$ for 2 hrs. On completion, the reaction mixture was diluted with EtOAc (80 mL), filtered and concentrated in vacuo. The residue was purified by column chromatography ($SiO_2$, PE:EA=3:1 to 2:3) to give the title compound (490 mg, 84% yield) as yellow solid. LC-MS (ESI$^+$) m/z 546.3 (M+H)$^+$.

Step 2—1-(8-piperazin-1-yl-4-quinolyl)hexahydropyrimidine-2,4-dione

To a solution of tert-butyl 4-[4-[3-[(4-methoxyphenyl)methyl]-2,4-dioxo-hexahydropyrimidin-1-yl]-8-quinolyl]piperazine-1-carboxylate (470 mg, 861 umol) in TFA (3 mL) was added TfOH (1.02 g, 6.80 mmol). The reaction was stirred at 70° C. for 1 hr. On completion, the reaction mixture was concentrated in vacuo to give the title compound (378 mg, 99% yield, TFA) as brown oil. LC-MS (ESI$^+$) m/z 326.2 (M+H)$^+$.

Step 3—Tert-butyl 4-[4-(2,4-dioxohexahydropyrimidin-1-yl)-8-quinolyl]piperazine -1-carboxylate To a solution of 1-(8-piperazin-1-yl-4-quinolyl)hexahydropyrimidine-2,4-dione (378 mg, 860 umol, TFA) and TEA (174 mg, 1.72 mmol) in DCM (4 mL) was added $Boc_2O$ (281 mg, 1.29 mmol) at 25° C. The reaction was then stirred at 25° C. for 1 hr. On completion, the reaction was diluted with DCM (100 mL) washed with water (50 mL×3). The organic layer was dried over $Na_2SO_4$, filtered and concentrated in vacuo. The residue was triturated with solvent (EA:PE=1:10, 20 mL) at 25° C. for 20 mins to give the title compound (312 mg, 85% yield) as brown solid. $^1$H NMR (400 MHz, DMSO-d$_6$) δ 10.57 (s, 1H), 8.92 (d, J=4.4 Hz, 1H), 7.64-7.46 (m, 3H), 7.19 (d, J=7.2 Hz, 1H), 4.02-3.93 (m, 1H), 3.69-3.63 (m, 1H), 3.59 (s, 4H), 3.47-3.33 (m, 2H), 3.29-3.20 (m, 2H), 3.05-2.94 (m, 1H), 2.74-2.66 (m, 1H), 1.47-1.42 (m, 9H).

Step 4—1-(8-piperazin-1-yl-4-quinolyl)hexahydropyrimidine-2,4-dione

To a solution of tert-butyl 4-[4-(2,4-dioxohexahydropyrimidin-1-yl)-8-quinolyl]piperazine-1-carboxylate (50 mg, 117 umol) in DCM (1 mL) was added TFA (308 mg, 2.70 mmol) at 25° C. The reaction was then stirred at 25° C. for 1 hr. On completion, the reaction mixture was concentrated in vacuo to give the title compound (51 mg, 98% yield, TFA) as brown oil. LC-MS (ESI$^+$) m/z 326.2 (M+H)$^+$.

3-(3-Methyl-2-oxo-4-((1s,3s)-3-(piperidin-4-yloxy)cyclobutyl)-2,3-dihydro-1H-benzo[d] imidazol-1-yl) piperidine-2,6-dione (Intermediate CFR)

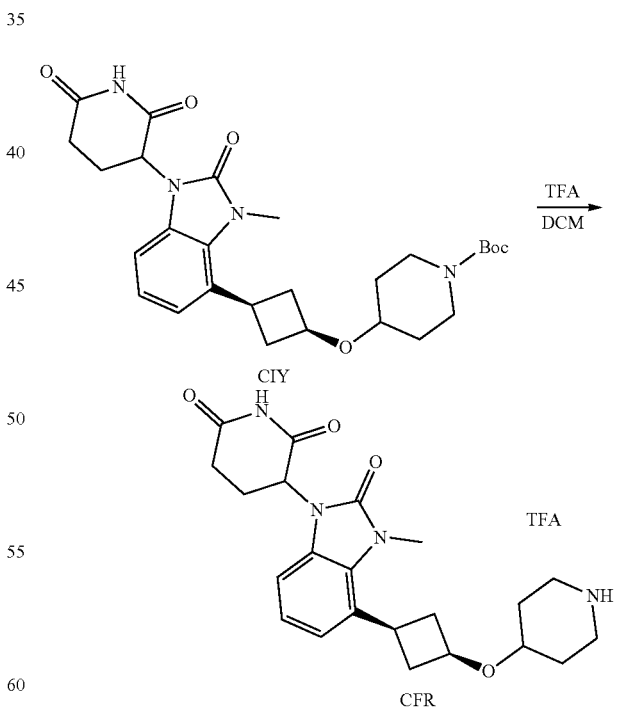

A mixture of tert-butyl 4-[3-[1-(2,6-dioxo-3-piperidyl)-3-methyl-2-oxo-benzimidazol-4-yl]cyclobutoxy]piperidine-1-carboxylate (25.0 mg, 48.7 umol, Intermediate CIV) and TFA (513 mg, 4.50 mmol) in DCM (1 mL) was stirred at 25° C. for 1 hour. On completion, the reaction was concentrated in vacuo to give the title compound (25.0 mg, 97% yield) as yellow oil. LC-MS (ESI⁺) m/z 413.3 (M+H)⁺.

Tert-butyl 4-((1r,3r)-3-(1-(2,6-dioxopiperidin-3-yl)-3-methyl-2-oxo-2,3-dihydro-1H-benzo[d]imidazol-4-yl)cyclobutoxy)piperidine-1-carboxylate (Intermediate CFS)

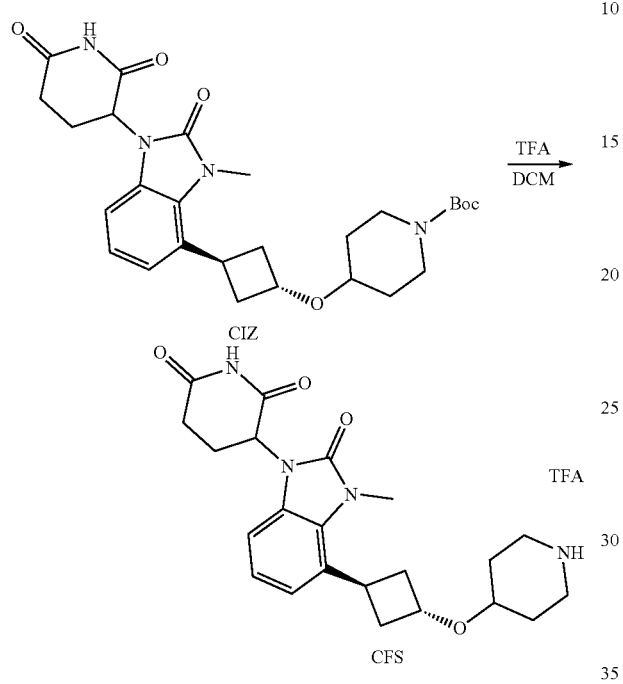

To a solution of tert-butyl 4-[3-[1-(2,6-dioxo-3-piperidyl)-3-methyl-2-oxo-benzimidazol-4-yl]cyclobutoxy]piperidine-1-carboxylate (15.0 mg, 29.2 umol, Intermediate CIZ) in DCM (1 mL) was added TFA (0.3 mL), then the reaction mixture was stirred at 25° C. for 2 hours. On completion, the reaction was concentrated in vacuo to give the title compound (15.0 mg, 97.3% yield) as yellow oil. LC-MS (ESI⁺) m/z 413.2 (M+H)⁺.

N-[6-(azetidin-1-yl)-2-(4-formylcyclohexyl)indazol-5-yl]-6-(trifluoromethyl)pyridine-2-carboxamide (Intermediate CFT)

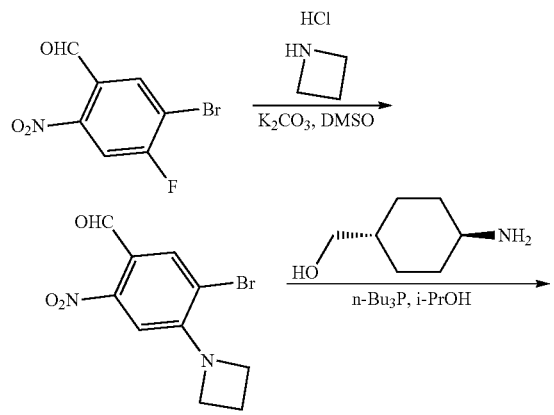

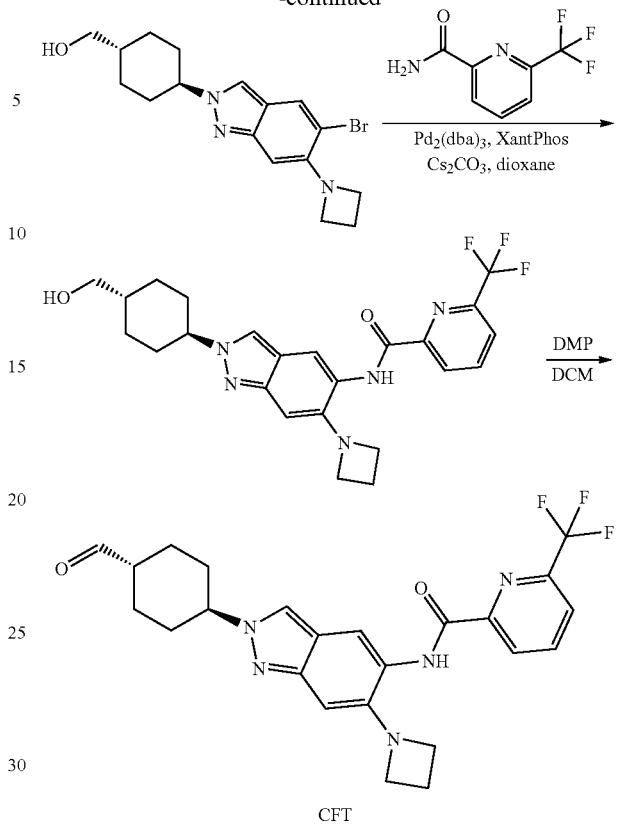

Step 1—4-(Azetidin-1-yl)-5-bromo-2-nitro-benzaldehyde

To a solution of azetidine (2.30 g, 40.3 mmol, CAS #503-29-7) and 5-bromo-4-fluoro-2-nitro-benzaldehyde (2 g, 8.06 mmol, CAS #213382-45-7) in DMSO (10 mL) was added TEA (4.08 g, 40.3 mmol). The mixture was stirred at 80° C. for 1 hr. On completion, the residue was diluted with water (30 mL) and extracted with EA (30 mL×2). The combined organic layer was dried over Na₂SO₄, filtered and concentrated in vacuo to give the title compound (2.0 g, 78% yield) as a brown oil. ¹H NMR (400 MHz, CDCl₃) δ 8.50 (s, 1H), 8.10 (s, 1H), 3.65-3.58 (m, 2H), 2.45 (t, J=7.3 Hz, 2H), 1.70 (q, J=7.2 Hz, 2H).

Step 2—[4-[6-(Azetidin-1-yl)-5-bromo-indazol-2-yl]cyclohexyl]methanol

To a solution of 4-(azetidin-1-yl)-5-bromo-2-nitro-benzaldehyde (1.8 g, 6.31 mmol) and (4-aminocyclohexyl)methanol (815 mg, 6.31 mmol) in i-PrOH (20 mL), then the reaction mixture was stirred at 80° C. for 2 hrs under N₂. Then the mixture was cooled to 25° C. and tributylphosphane (3.19 g, 15.7 mmol) was added. Then the mixture was stirred at 80° C. for 2 hrs under N₂. On completion, the residue was purified by column chromatography (SiO₂, PE:EA=6:1 to PE:EA=2:1, PE:EA=2:1, Pl:Rf=0.3) to give the title compound (850 mg, 36% yield) as yellow solid. ¹H NMR (400 MHz, DMSO-d₆) δ 8.17 (s, 1H), 7.83 (s, 1H), 6.67 (s, 1H), 4.48 (t, J=5.2 Hz, 1H), 4.38-4.25 (m, 1H), 3.92 (t, J=7.2 Hz, 4H), 3.27 (t, J=5.6 Hz, 2H), 2.17 (quin, J=7.2

Hz, 2H), 2.08 (d, J=10.4 Hz, 2H), 1.92-1.76 (m, 4H), 1.52-1.38 (m, 1H), 1.19-1.03 (m, 2H); LC-MS (ESI⁺) m/z 364.0 (M+H)⁺.

Step 3—N-[6-(azetidin-1-yl)-2-[4-(hydroxymethyl)cyclohexyl]indazol-5-yl]-6-(trifluoromethyl)pyridine-2-carboxamide A mixture of [4-[6-(azetidin-1-yl)-5-bromo-indazol-2-yl]cyclohexyl]methanol (200 mg, 549 umol), 6-(trifluoromethyl)pyridine-2-carboxamide (135 mg, 713 umol, CAS #22245-84-7), Pd$_2$(dba)$_3$ (50.2 mg, 54.9 umol), Xantphos (63.5 mg, 109 umol) and Cs$_2$CO$_3$ (357 mg, 1.10 mmol) in dioxane (4 mL) was degassed and purged with N$_2$ three times. Then the mixture was stirred at 100° C. for 8 hrs under N$_2$ atmosphere. On completion, the reaction mixture was filtered and concentrated in vacuo. The residue was diluted with DCM (15 mL) and extracted with DCM (15 mL×2). The combined organic layers were washed with H$_2$O (10 mL×3), filtered and concentrated in vacuo. The residue was purified by column chromatography (SiO$_2$, PE:EA=5:1 to PE:EA=0:1, PE:EA=1:1, Pl:Rf=0.2). Then, the residue was purified by prep-HPLC (column: Phenomenex Luna C18 150*25 mm*10 um; mobile phase: [water (FA)-ACN]; B %: 37%-67%, 10.5 min) to give the title compound (60 mg, 23% yield) as a yellow solid. $^1$H NMR (400 MHz, DMSO-d$_6$) δ 10.18 (s, 1H), 8.48-8.37 (m, 3H), 8.28 (s, 1H), 8.22 (dd, J=0.8, 7.6 Hz, 1H), 6.92 (s, 1H), 4.48 (t, J=5.2 Hz, 1H), 4.40-4.29 (m, 1H), 3.87 (t, J=7.2 Hz, 4H), 3.30-3.25 (m, 2H), 2.25 (quin, J=7.2 Hz, 2H), 2.12 (dd, J=3.6, 9.2 Hz, 2H), 1.94-1.82 (m, 4H), 1.54-1.42 (m, 1H), 1.21-1.08 (m, 2H).

Step 4—N-[6-(azetidin-1-yl)-2-(4-formylcyclohexyl)indazol-5-yl]-6-(trifluoromethyl)pyridine-2-carboxamide To a solution of N-[6-(azetidin-1-yl)-2-[4-(hydroxymethyl)cyclohexyl]indazol-5-yl]-6-(trifluoromethyl)pyridine-2-carboxamide (45.0 mg, 95.0 umol) in DMSO (1 mL) was added IBX (79.8 mg, 285 umol). The mixture was then stirred at 50° C. for 3 hrs. On completion, the reaction mixture was quenched with saturated Na$_2$S$_2$O$_3$ (5 mL) and saturated NaHCO$_3$ (5 mL) at 25° C. and stirred for 5 minutes. The mixture was then extracted with DCM (20 mL×2) and washed with H$_2$O (10 mL×2). The reaction mixture was concentrated under reduced pressure to give the title compound (40 mg, 80% yield) as a yellow solid. LC-MS (ESI⁺) m/z 472.0 (M+H)⁺.

N-[2-(4-formylcyclohexyl)-6-pyrrolidin-1-yl-indazol-5-yl]-6-(trifluoromethyl)pyridine -2-carboxamide (Intermediate CFU)

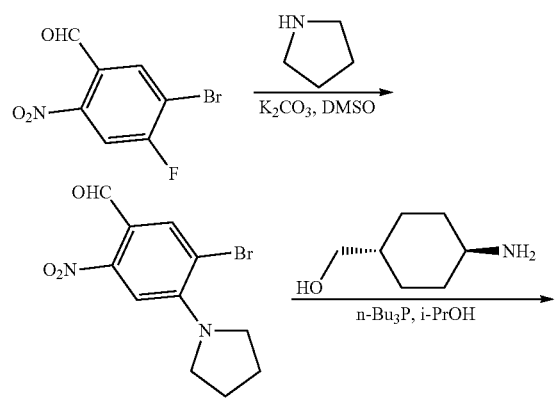

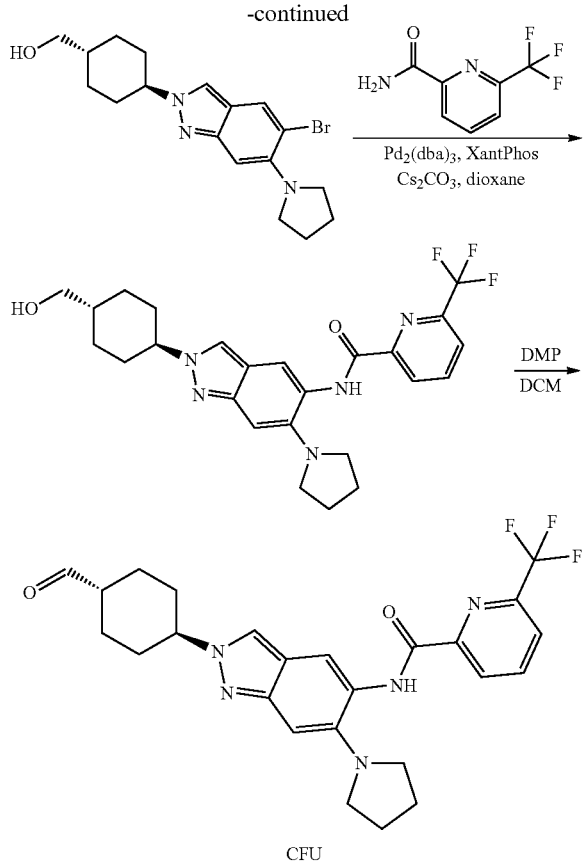

CFU

Step 1—5-Bromo-2-nitro-4-pyrrolidin-1-yl-benzaldehyde

To a solution of 5-bromo-4-fluoro-2-nitro-benzaldehyde (5.00 g, 20.1 mmol, CAS #213382-45-7) and pyrrolidine (2.87 g, 40.3 mmol, CAS #123-75-1) in DMF (80 mL) was added K$_2$CO$_3$ (5.57 g, 40.3 mmol), then the mixture was stirred at 50° C. for 1 hour. On completion, the mixture was filtered and washed with water (150 mL) and extracted with EA (200 mL×3). The combined organic layer was dried over anhydrous Na$_2$SO$_4$, then concentrated in vacuo to give the residue. The residue was purified by column chromatography (SiO$_2$, PE:EA=20:1 to 12:1) to give the title compound (5.90 g, 97% yield) as a red solid. $^1$H NMR (400 MHz, DMSO-d$_6$) δ 8.91 (d, J=2.8 Hz, 2H), 8.51 (d, J=2.8 Hz, 1H), 8.49 (d, J=2.8 Hz, 1H), 8.08 (d, J=8.8 Hz, 2H). LC-MS (ESI⁺) m/z 299.0 (M+H)⁺.

Step 2—[4-(5-Bromo-6-pyrrolidin-1-yl-indazol-2-yl)cyclohexyl]methanol

To a solution of 5-bromo-2-nitro-4-pyrrolidin-1-yl-benzaldehyde (1.50 g, 5.01 mmol) in IPA (15 mL) was added (4-aminocyclohexyl)methanol (1.94 g, 15.0 mmol, CAS #1467-84-1), and the mixture stirred at 80° C. for 4 hours. Next, tributylphosphane (1.52 g, 7.52 mmol) was added at 25° C. and the mixture was stirred at 80° C. for 5 hours. On completion, the mixture was concentrated in vacuo to give the residue. The residue was purified by reverse-phase (0.1% FA condition) to give the title compound (2.20 g, 38% yield) as a white solid. $^1$H NMR (400 MHz, DMSO-d$_6$) δ 8.23 (s, 1H), 7.90-7.88 (m, 1H), 7.13 (s, 1H), 4.48-4.46 (m, 1H), 4.38-4.31 (m, 1H), 3.29-3.26 (m, 2H), 3.19-3.16 (m, 4H), 2.11-2.08 (m, 2H), 1.91-1.82 (m, 7H), 1.48-1.43 (m, 2H), 1.20-1.05 (m, 2H) LC-MS (ESI$^+$) m/z 380.0 (M+H)$^+$.

Step 3—N-[2-[4-(hydroxymethyl)cyclohexyl]-6-pyrrolidin-1-yl-indazol-5-yl]-6-(trifluoromethyl)-pyridine-2-carboxamide To a solution of [4-(5-bromo-6-pyrrolidin-1-yl-indazol-2-yl)cyclohexyl]methanol (500 mg, 1.32 mmol) and 6-(trifluoromethyl)pyridine-2-carboxamide (376 mg, 1.98 mmol, CAS #22245-84-7) in dioxane (6 mL) was added Pd$_2$(dba)$_3$ (121 mg, 132 umol), Cs$_2$CO$_3$ (861 mg, 2.64 mmol) and Xantphos (76.4 mg, 132 umol), then the mixture was stirred at 110° C. for 16 hours. On completion, the mixture was filtered and extracted with EA (10 mL×3), then the combined organic phase was dried over anhydrous Na$_2$SO$_4$ and concentrated in vacuo to give the residue. The residue was purified by reverse phase (0.1% FA condition) to give the title compound (560 mg, 86% yield) as a yellow solid. $^1$H NMR (400 MHz, DMSO-d$_6$) δ 10.89 (s, 1H), 8.70 (s, 1H), 8.50-8.45 (m, 1H), 8.43-8.37 (m, 1H), 8.34 (s, 1H), 8.21 (d, J=7.6 Hz, 1H), 7.43 (s, 1H), 4.50-4.48 (m, 1H), 4.40-4.34 (m, 1H), 3.30-3.27 (m, 2H), 3.07 (s, 4H), 2.14-2.10 (m, 2H), 1.98-1.97 (m, 4H), 1.89-1.87 (m, 4H), 1.49-1.44 (m, 1H), 1.19-1.12 (m, 2H). LC-MS (ESI$^+$) m/z 488.2 (M+H)$^+$.

Step 4—N-[2-(4-formylcyclohexyl)-6-pyrrolidin-1-yl-indazol-5-yl]-6-(trifluoromethyl)pyridine-2-carboxamide To a solution of N-[2-[4-(hydroxymethyl)cyclohexyl]-6-pyrrolidin-1-yl-indazol-5-yl]-6-(trifluoro-methyl)pyridine-2-carboxamide (60.0 mg, 123 umol) in DCM (2 mL) was added DMP (78.3 mg, 184 umol) at 0° C., then the mixture was stirred at 25° C. for 1 hour. On completion, the mixture was quenched with sat. Na$_2$S$_2$O$_3$ (3 mL) and sat. NaHCO$_3$(3 mL), then the mixture was extracted with DCM (10 mL×3). The combined organic layer was dried over anhydrous Na$_2$SO$_4$, filtered and concentrated in vacuo to give the title compound (40.0 mg, 66% yield) as a black oil. LC-MS (ESI$^+$) m/z 486.1 (M+H)$^+$.

3-[4-(3,8-diazabicyclo[3.2.1]octan-8-yl)-3-methyl-2-oxo-benzimidazol-1-yl] piperidine-2,6-dione (Intermediate CET)

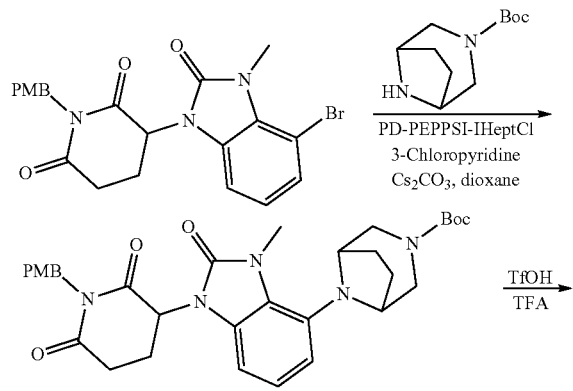

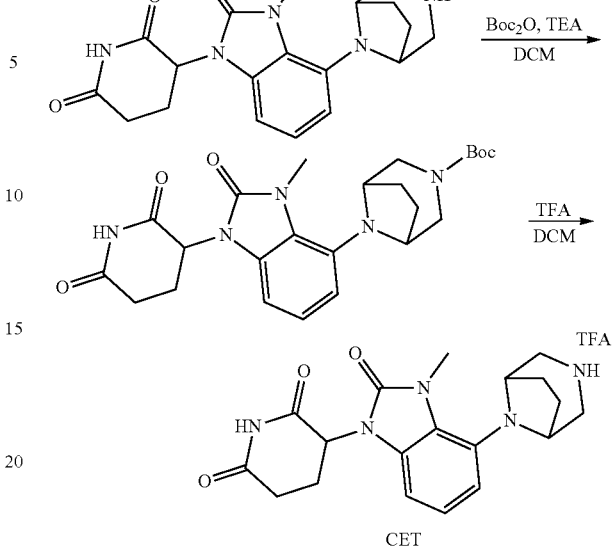

CET

Step 1—Tert-butyl 8-(1-(1-(4-methoxybenzyl)-2,6-dioxopiperidin-3-yl)-3-methyl-2-oxo-2,3-dihydro-1H-benzo[d]imidazol-4-yl)-3,8-diazabicyclo[3.2.1]octane-3-carboxylate 4

To a solution of 3-(4-bromo-3-methyl-2-oxo-benzimidazol-1-yl)-1-[(4-methoxyphenyl)methyl] piperidine-2,6-dione (500 mg, 1.09 mmol, synthesized via Steps 1-4 of Intermediate HP), tert-butyl 3,8-diazabicyclo[3.2.1]octane-3-carboxylate (301 mg, 1.42 mmol), PD-PEPPSIIHeptCl 3-Chloropyridine (105 mg, 109 umol) and Cs$_2$CO$_3$ (710.92 mg, 2.18 mmol) in dioxane (3 mL) was de-gassed and then heated to 100° C. for 16 hours under N$_2$. On completion, the reaction mixture was diluted with EA (60 mL), and extracted with H$_2$O (10 mL×3). The organic layer was separated, dried over Na$_2$SO$_4$, filtered and concentrated in vacuo. The residue was purified by column chromatography (SiO$_2$, Petroleum ether/Ethyl acetate=2/1 to 1/1) to give the title compound (270 mg, 41% yield) as yellow solid. LC-MS (ESI$^+$) m/z 590.2 (M+H)$^+$.

Step 2—3-(4-(3,8-Diazabicyclo[3.2.1]octan-8-yl)-3-methyl-2-oxo-2,3-dihydro-1H-benzo[d]imidazol-1-yl)piperidine-2,6-dione To a solution of tert-butyl 8-[1-[1-[(4-methoxyphenyl)methyl]-2,6-dioxo-3-piperidyl]-3-methyl-2-oxo-benzimidazol-4-yl]-3,8-diazabicyclo[3.2.1]octane-3-carboxylate (70 mg, 118 umol) in TFA (0.6 mL) was added TfOH (0.2 mL) 25° C. Then the reaction was stirred at 70° C. for 1 h. On completion, the reaction mixture was concentrated in vacuo to give the title compound (57 mg, 99% yield) as brown oil. LC-MS (ESI$^+$) m/z 370.2 (M+H)$^+$.

Step 3—Tert-butyl 8-(1-(2,6-dioxopiperidin-3-yl)-3-methyl-2-oxo-2,3-dihydro-1H-benzo[d]imidazol-4-yl)-3,8-diazabicyclo[3.2.1]octane -3-carboxylate To a solution of 3-[4-(3,8-diazabicyclo[3.2.1] octan-8-yl)-3-methyl-2-oxo-benzimidazol-1-yl] piperidine-2,6-dione (57 mg, 117 umol) in DCM (2 mL) was added TEA (0.3 mL)

until the pH=8. Then, Boc2O (30.88 mg, 141 umol) was added into above mixture at 0° C. The reaction was then stirred at 25° C. for 1 h. On completion, the reaction mixture was diluted with DCM (30 mL), and extracted with water (20 mL×2). The organic layer was separated, dried over Na$_2$SO$_4$ and concentrated in vacuo. The residue was purified by reverse phase (FA) to give the title compound (50.0 mg, 90% yield) as yellow solid. LC-MS (ESI$^+$) m/z 470.2 (M+H)$^+$.

Step 4—3-(4-(3,8-Diazabicyclo[3.2.1]octan-8-yl)-3-methyl-2-oxo-2,3-dihydro-1H-benzo[d]imidazol-1-yl)piperidine-2,6-dione To a solution of tert-butyl 8-[1-(2,6-dioxo-3-piperidyl)-3-methyl-2-oxo-benzimidazol-4-yl]-3,8-diazabicyclo[3.2.1]octane-3-carboxylate (50 mg, 106 umol) in DCM (2 mL) was added TFA (12.14 mg, 106.49 umol) at 25° C. The reaction was then stirred at 25° C. for 1 h. On completion, the reaction mixture was concentrated in vacuo to give the title compound (50 mg, TFA salt, 95% yield) as yellow solid. LC-MS (ESI$^+$) m/z 370.2 (M+H)$^+$.

N-[2-(4-formylcyclohexyl)-6-isopropyl-indazol-5-yl]-6-(trifluoromethyl)pyridine-2-carboxamide (Intermediate CFV)

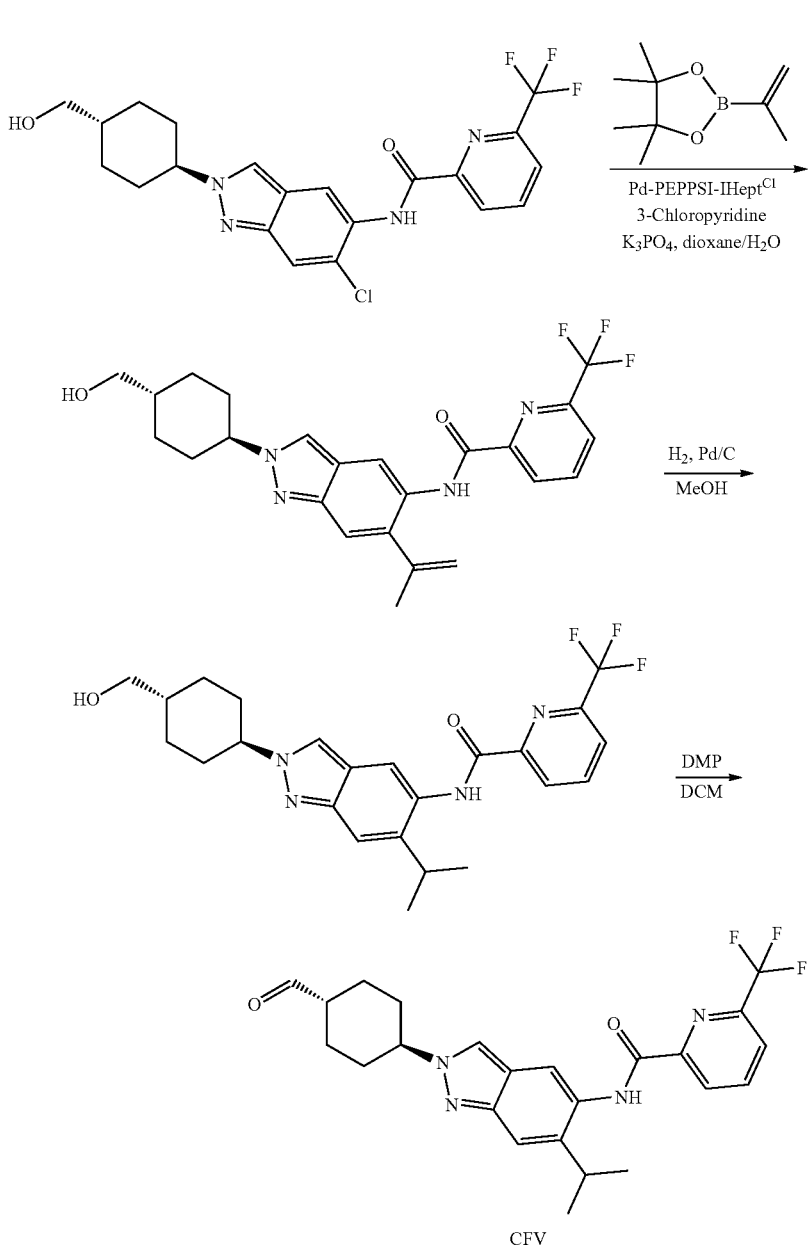

Step 1—N-[2-[4-(hydroxymethyl)cyclohexyl]-6-isopropenyl-indazol-5-yl]-6-(trifluoromethyl)pyridine-2-carboxamide To a solution of N-[6-chloro-2-[4-(hydroxymethyl)cyclohexyl]indazol-5-yl]-6-(trifluoromethyl) pyridine-2-carboxamide (1.00 g, 2.21 mmol, via Steps 1-3 of Intermediate BPQ) and 2-isopropenyl-4,4,5,5-tetramethyl-1,3,2-dioxaborolane (742 mg, 4.42 mmol, CAS #126726-62-3) in dioxane (15 mL) and $H_2O$ (1.5 mL) was added $K_3PO_4$ (1.41 g, 6.62 mmol) and [2-(2-aminophenyl)phenyl]-chloro-palladium; dicyclohexyl-[3-(2,4,6-triisopropylphenyl)phenyl]phosphane (173 mg, 220 umol). Then the mixture was purged with $N_2$ for three times and stirred at 90° C. for 12 hours. On completion, the mixture was concentrated in vacuo to give the residue. The residue was purified by prep-HPLC (column: Phenomenex Luna C18 200*40 mm*10 um; mobile phase: [water(FA)-ACN]; B %: 50%-80%, 10 min) to give the title compound (440 mg, 43% yield) as a brown solid. $^1$H NMR (400 MHz, DMSO-$d_6$) δ 10.41 (s, 1H), 8.70 (s, 1H), 8.46 (d, 2H), 8.40 (t, 1H), 8.20 (d, J=7.6 Hz, 1H), 7.51 (s, 1H), 5.51 (s, 1H), 5.14 (s, 1H), 4.52-4.48 (m, 1H), 4.43-4.40 (m, 1H), 3.30-3.27 (m, 2H), 2.52-2.48 (m, 3H), 2.15 (s, 2H), 1.96-1.85 (m, 4H), 1.54-1.43 (m, 1H), 1.22-1.10 (m, 2H). LC-MS (ESI$^+$) m/z 459.1 (M+H)$^+$.

Step 2—N-[2-[4-(hydroxymethyl)cyclohexyl]-6-isopropyl-indazol-5-yl]-6-(trifluoromethyl)pyridine-2-carboxamide To a solution of N-[2-[4-(hydroxymethyl)cyclohexyl]-6-isopropenyl-indazol-5-yl]-6-(trifluoromethyl) pyridine-2-carboxamide (100 mg, 218 umol) in MeOH (3 mL) was added Pd/C (30 mg, 10 wt %), then purged with $H_2$ (30.0 mg, 14.9 mmol) for three times, then the mixture was stirred at 25° C. for 2 hr under $H_2$ (15 psi). On completion, the mixture was filtered and concentrated in vacuo to give the title compound (90 mg, 89.61% yield) as a yellow solid. $^1$H NMR (400 MHz, DMSO-$d_6$) δ 10.22 (s, 1H), 8.45-8.35 (m, 3H), 8.21-8.19 (m, 1H), 8.13 (s, 1H), 7.54 (s, 1H), 4.49 (t, J=5.2 Hz, 1H), 4.46-4.37 (m, 1H), 3.30-3.26 (m, 2H), 2.14-2.12 (m, 2H), 1.97-1.84 (m, 4H), 1.55-1.43 (m, 1H), 1.29 (d, J=6.8 Hz, 6H), 1.24-1.10 (m, 3H). LC-MS (ESI$^+$) m/z 461.1 (M+H)$^+$.

Step 3—N-[2-(4-formylcyclohexyl)-6-isopropyl-indazol-5-yl]-6-(trifluoromethyl)pyridine-2-carboxamide To a solution of N-[2-[4-(hydroxymethyl)cyclohexyl]-6-isopropyl-indazol-5-yl]-6-(trifluoromethyl) pyridine-2-carboxamide (50.0 mg, 108 umol) in DCM (2 mL) was added DMP (69.0 mg, 162 umol) at 0° C., then the mixture was stirred at 25° C. for 1 hour. On completion, the mixture was diluted with DCM (2 mL), then quenched with sat.$Na_2S_2O_3$ (2 mL) and sat.$NaHCO_3$(2 mL), and the mixture was stirred at 25° C. for 10 minutes. Then the mixture was extracted with DCM (2 mL×3). Then the combined organic layers were dried over anhydrous $Na_2SO_4$, filtered and concentrated in vacuo to give the title compound (49.0 mg, 98% yield) as a yellow solid. LC-MS (ESI$^+$) m/z 459.1 (M+H)$^+$.

N-[2-(4-formylcyclohexyl)-6-methyl-indazol-5-yl]-6-(trifluoromethyl)pyrazine-2-carboxamide (Intermediate CFW)

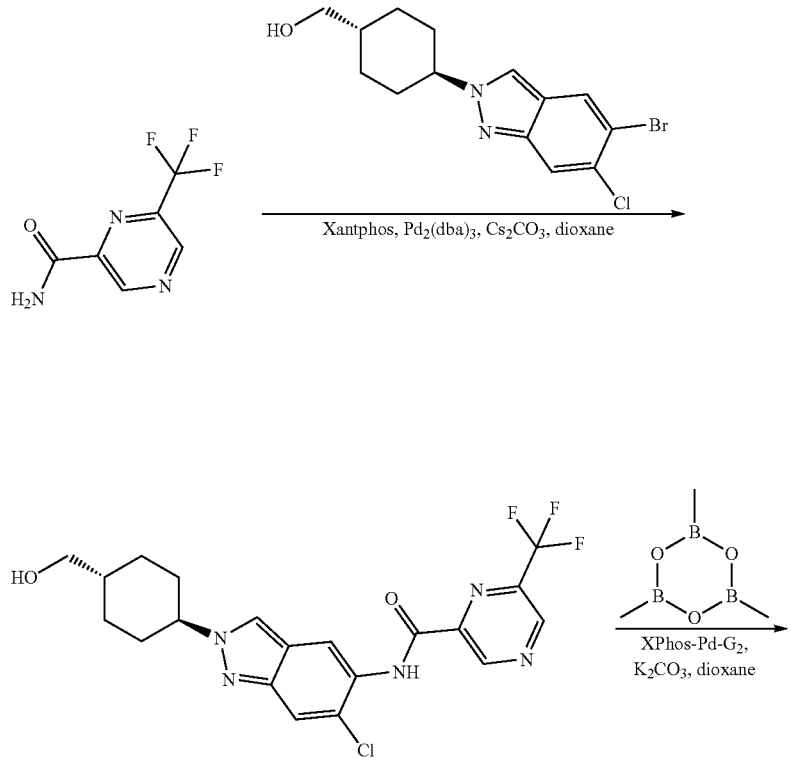

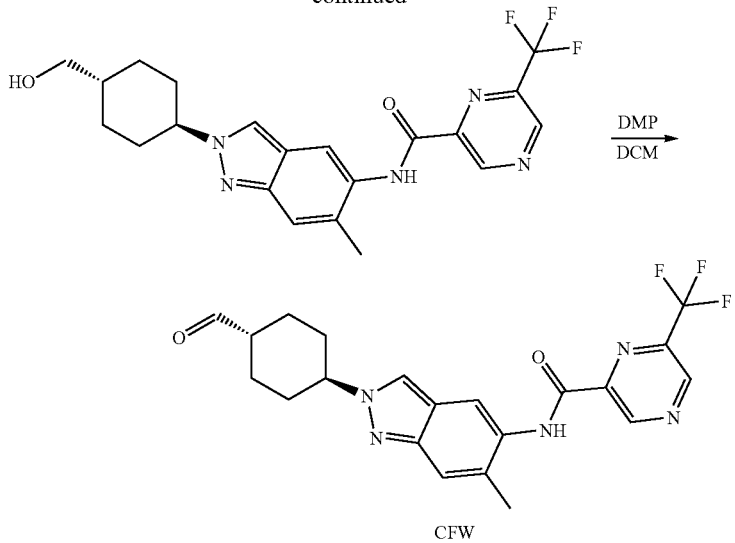

Step 1—N-[6-chloro-2-[4-(hydroxymethyl)cyclohexyl]indazol-5-yl]-6-(trifluoromethyl)pyrazine-2-carboxamide To a solution of [4-(5-bromo-6-chloro-indazol-2-yl)cyclohexyl]methanol (500 mg, 1.45 mmol, synthesized via Steps 1-2 of Intermediate BPQ) and 6-(trifluoromethyl)pyrazine-2-carboxamide (417 mg, 2.18 mmol, synthesized via Steps 1-2 of Intermediate CEO) in dioxane (5 mL) was added Pd$_2$(dba)$_3$ (133 mg, 145 umol), Xantphos (84.1 mg, 145 umol) and Cs$_2$CO$_3$ (948 mg, 2.91 mmol), then the mixture was stirred at 100° C. for 8 hours. On completion, the mixture was filtered and extracted with H$_2$O (10 mL) and EA (10 mL×3), dried over anhydrous Na$_2$SO$_4$, then concentrated in vacuo to give the residue. The residue was purified by column chromatography (SiO$_2$, PE:EA=15:1 to 1:5) give the title compound (413 mg, 62% yield) as a yellow solid. 1H NMR (400 MHz, DMSO-d$_6$) δ 10.41 (s, 1H), 9.61 (s, 1H), 9.51 (s, 1H), 8.54 (s, 1H), 8.43 (s, 1H), 7.92 (s, 1H), 4.51-4.42 (m, 2H), 3.30-3.27 (m, 2H), 2.17-2.14 (m, 2H), 1.95-1.85 (m, 4H), 1.55-1.43 (m, 1H), 1.23-1.12 (m, 2H). LC-MS (ESI$^+$) m/z 454.1 (M+H)$^+$.

Step 2—N-[2-[4-(hydroxymethyl)cyclohexyl]-6-methyl-indazol-5-yl]-6-(trifluoromethyl)pyrazine-2-carboxamide To a solution of 2,4,6-trimethyl-1,3,5,2,4,6-trioxatriborinane (110 mg, 881 umol) and N-[6-chloro-2-[4-(hydroxymethyl)cyclohexyl]indazol-5-yl]-6-(trifluoromethyl)pyrazine-2-carboxamide (200 mg, 440 umol) in dioxane (2 mL) was added K$_2$CO$_3$ (182 mg, 1.32 mmol) and XPhos-Pd-G2 (34.6 mg, 44.0 umol), then the mixture was stirred at 90° C. for 8 hours under N$_2$ atmosphere. On completion, the mixture was filtered, then washed with H$_2$O (3 mL) and extracted with EA (5 mL×3). The combined organic layer was dried over anhydrous Na$_2$SO$_4$, and concentrated in vacuo to give the residue. The residue was purified by column chromatography (SiO$_2$, PE:EA=10:1 to 1:5) to give the title compound (180 mg, 94% yield) as a yellow solid. 1H NMR (400 MHz, DMSO-d$_6$) δ 10.19 (s, 1H), 9.58 (s, 1H), 9.48 (s, 1H), 8.37 (s, 1H), 7.96 (s, 1H), 7.51 (s, 1H), 4.50-4.47 (m, 1H), 4.40-4.38 (m, 1H), 3.30-3.27 (m, 2H), 2.36 (s, 3H), 2.16-2.13 (m, 2H), 1.91-1.88 (m, 4H), 1.51-1.46 (m, 1H), 1.20-1.19 (m, 1H), 1.15-1.13 (m, 1H). LC-MS (ESI$^+$) m/z 434.1 (M+H)$^+$.

Step 3—N-[2-(4-formylcyclohexyl)-6-methyl-indazol-5-yl]-6-(trifluoromethyl)pyrazine-2-carboxamide To a solution of N-[2-[4-(hydroxymethyl)cyclohexyl]-6-methyl-indazol-5-yl]-6-(trifluoromethyl) pyrazine-2-carboxamide (70.0 mg, 161 umol) in DCM (2 mL) was added DMP (102 mg, 242 umol) at 0° C., then the mixture was stirred at 25° C. for 1 hour. On completion, the mixture was quenched with sat. Na$_2$S$_2$O$_3$ (1 mL) and sat. NaHCO$_3$(1 mL), then the mixture was stirred at 25° C. for 0.5 hour. On completion, the mixture was extracted with DCM (2 mL×3), dried over anhydrous Na$_2$SO$_4$, then concentrated in vacuo to give the title compound (60.0 mg, 86% yield) as a yellow solid. LC-MS (ESI$^+$) m/z 432.1 (M+H)$^+$.

1-Methyl-3-(3-methyl-2-oxo-4-piperazin-1-yl-benzimidazol-1-yl)piperidine-2,6-dione (Intermediate CFX)

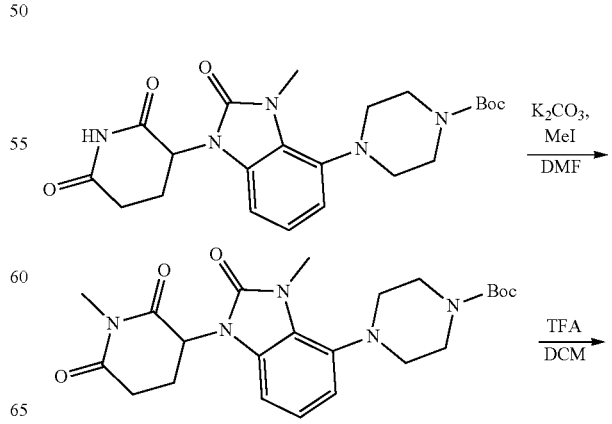

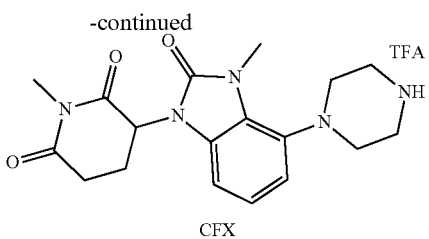

CFX

Step 1—Tert-butyl 4-[3-methyl-1-(1-methyl-2,6-dioxo-3-piperidyl)-2-oxo-benzimidazol-4-yl]piperazine-1-carboxylate To a solution of tert-butyl 4-[1-(2,6-dioxo-3-piperidyl)-3-methyl-2-oxo-benzimidazol-4-yl]piperazine-1-carboxylate (200 mg, 450 umol, synthesized via Steps 1-6 of Intermediate BAI) in DMF (4 mL) was added $K_2CO_3$ (124 mg, 901 umol) and $CH_3I$ (96.0 mg, 676 umol), then the mixture was stirred at 60° C. for 4 hours. On completion, the mixture was diluted with sat. $NH_4CL$ (50 mL) and extracted with EA (25 mL×3). Then the combined organic layers were dried over anhydrous $Na_2SO_4$, filtered and concentrated in vacuo to give the title compound (160 mg, 77% yield) as a brown solid. $^1$H NMR (400 MHz, DMSO-$d_6$) δ 7.00-6.88 (m, 3H), 5.42 (d, J=12.8 Hz, 1H), 3.63 (s, 3H), 3.12-3.01 (m, 6H), 2.98-2.94 (m, 2H), 2.81-2.74 (m, 2H), 2.72-2.65 (m, 2H), 2.60-2.52 (m, 2H), 2.05-1.96 (m, 1H), 1.43 (s, 9H). LC-MS (ESI$^+$) m/z 458.1 (M+H)$^+$.

Step 2—1-Methyl-3-(3-methyl-2-oxo-4-piperazin-1-yl-benzimidazol-1-yl)piperidine-2,6-dione To a solution of tert-butyl 4-[3-methyl-1-(1-methyl-2,6-dioxo-3-piperidyl)-2-oxo-benzimidazol-4-yl]piperazine-1-carboxylate (80.0 mg, 174 umol) in DCM (2 mL) was added TFA (0.5 mL, 6.75 mmol), then the mixture was stirred at 25° C. for 1 hour. On completion, the mixture was concentrated in vacuo to give the title compound (80.0 mg, 97% yield, TFA) as a black brown oil. LC-MS (ESI$^+$) m/z 358.1 (M+H)$^+$.

N-[6-acetyl-2-(4-formylcyclohexyl)indazol-5-yl]-6-(trifluoromethyl)pyridine-2-carboxamide (Intermediate CFY)

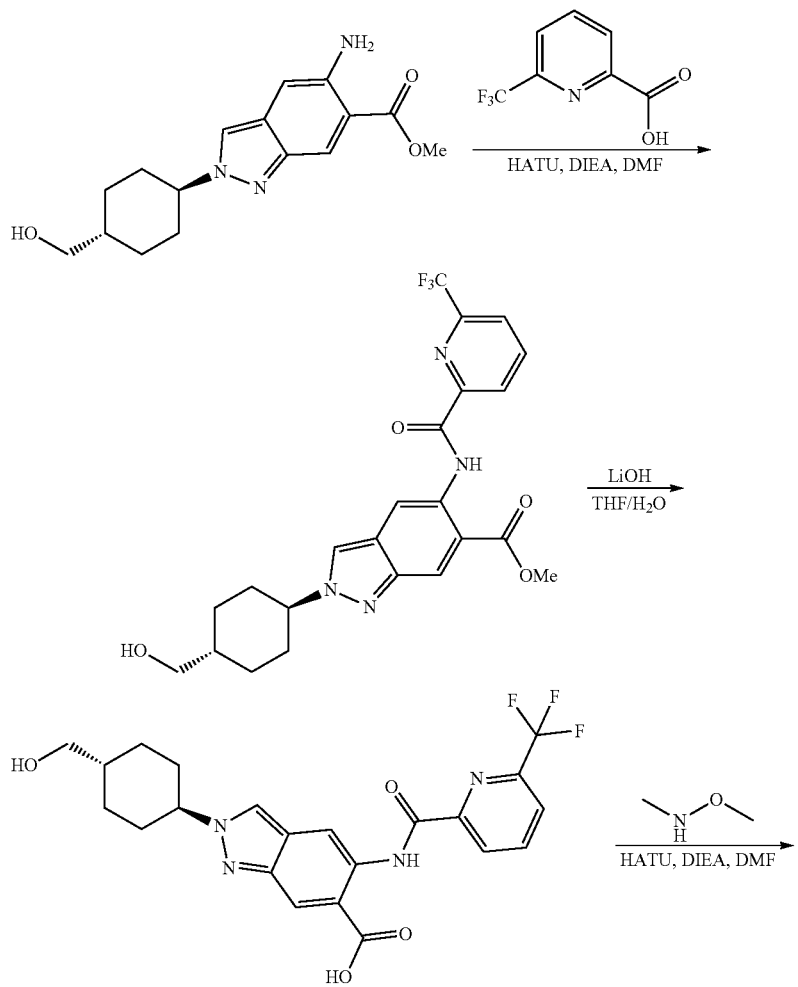

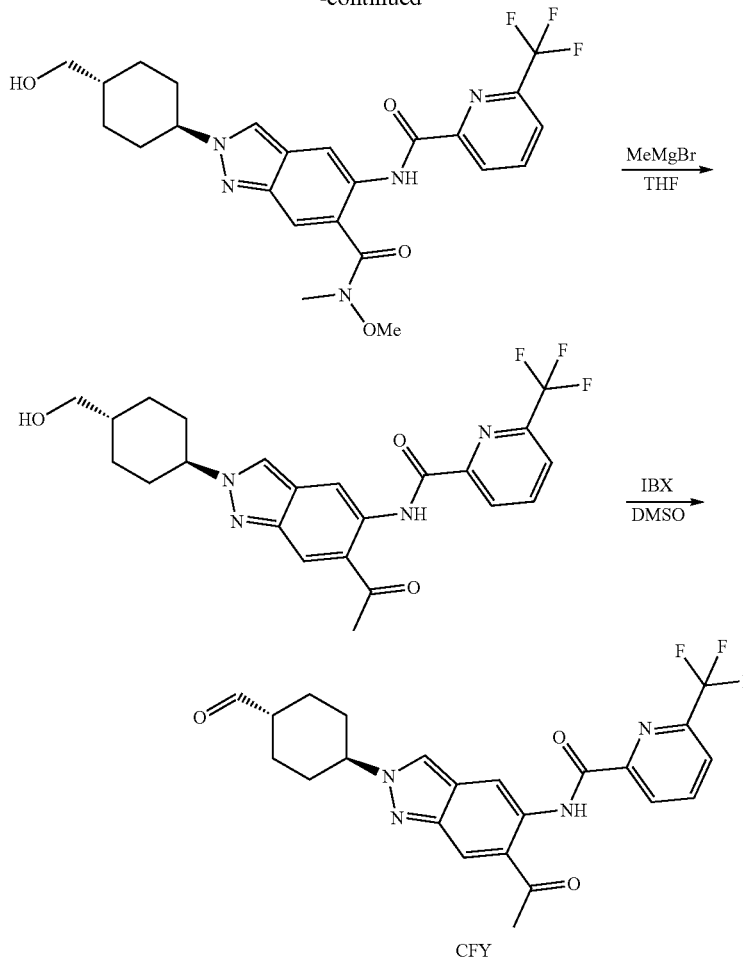

CFY

Step 1—Methyl 2-[4-(hydroxymethyl)cyclohexyl]-5-[[6-(trifluoromethyl)pyridine-2-carbonyl]amino]indazole-6-carboxylate To a solution of methyl 5-amino-2-[4-(hydroxymethyl)cyclohexyl]indazole-6-carboxylate (3.50 g, 11.54 mmol, synthesized via Steps 1-3 of Intermediate BXI), 6-(trifluoromethyl)pyridine-2-carboxylic acid (2.09 g, 11.0 mmol, CAS #131747-42-7) and DIEA (4.47 g, 34.6 mmol) in DMF (40 mL) was added HATU (4.83 g, 12.7 mmol). The reaction mixture was stirred at 20° C. for 0.5 hr. On completion, the mixture was quenched with water (200 mL), stirred and filtered. The filter cake was dried in vacuo to give the title compound (5.10 g, 93% yield) as a yellow solid. LC-MS (ESI$^+$) m/z 477.2 (M+H)$^+$

Step 2—2-[4-(Hydroxymethyl)cyclohexyl]-5-[[6-(trifluoromethyl)pyridine-2-carbonyl]amino]indazole-6-carboxylic Acid To a solution of methyl 2-[4-(hydroxymethyl)cyclohexyl]-5-[[6-(trifluoromethyl)pyridine-2-carbonyl]amino]indazole-6-carboxylate (1.00 g, 2.10 mmol) in THF (8 mL) and H$_2$O (2 mL) was added LiOH·H$_2$O (264 mg, 6.30 mmol). The mixture was then stirred at 25° C. for 2 hrs. On completion, the residue was acidified with HCl (4 M) until the pH=4-5, concentrated in vacuo to give the title compound (970 mg, 99% yield) as white solid. $^1$H NMR (400 MHz, DMSO-d$_6$) δ 13.18 (s, 1H), 9.14 (s, 1H), 8.54 (s, 1H), 8.50-8.41 (m, 2H), 8.37 (t, J=7.6 Hz, 1H), 8.17 (d, J=7.6 Hz, 1H), 4.68-4.39 (m, 2H), 3.28 (d, J=6.0 Hz, 2H), 2.16 (d, J=9.2 Hz, 2H), 1.99-1.83 (m, 4H), 1.49 (d, J=2.8 Hz, 1H), 1.23-1.08 (m, 2H).

Step 3—2-[4-(Hydroxymethyl)cyclohexyl]-N-methoxy-N-methyl-5-[[6-(trifluoromethyl)pyridine-2-carbonyl]amino]indazole-6-carboxamide To a solution of 2-[4-(hydroxymethyl)cyclohexyl]-5-[[6-(trifluoromethyl)pyridine-2-carbonyl]amino]indazole-6-carboxylic acid (400 mg, 865 umol) and N-methoxymethanamine (590 mg, 6.06 mmol) in DMF (2 mL) was added DIEA (670 mg, 5.19 mmol). Then, to the reaction was added HATU (361 mg, 951 umol). The mixture was stirred at 25° C. for 16 hrs. On completion, the residue was purified by prep-HPLC(column: Phenomenex Luna C18 200*40 mm*10 um; mobile phase: [water (FA)-ACN]; B %: 31%-61%, 10 min) to give the title compound (220 mg, 50% yield) as white solid. LC-MS (ESI$^+$) m/z 506.2 (M+H)$^+$.

Step 4—N-[6-acetyl-2-[4-(hydroxymethyl)cyclohexyl]indazol-5-yl]-6-(trifluoromethyl)pyridine-2-carboxamide To a solution of 2-[4-(hydroxymethyl)cyclohexyl]-N-methoxy-N-methyl-5-[[6-(trifluoromethyl)pyridine-2-carbonyl]amino]indazole-6-carboxamide (150 mg, 296 umol) in THF (4 mL) was added MeMgBr (3 M, 989 uL) at 0° C. The mixture was stirred at 25° C. for 2 hrs. On completion, the reaction mixture was quenched with NH₄Cl (15 mL). The residue was diluted with water (20 mL) and extracted with EA (25 mL×2). The combined organic layer was washed with brine (25 mL×2), dried over Na₂SO₄ and filtered. The filtrate was concentrated in vacuo. Then, the residue was purified by prep-HPLC (column: Phenomenex luna C18 150*25 mm*10 um; mobile phase: [water (FA)-ACN]; B %: 37%-67%, 10.5 min) to give the title compound (60 mg, 44% yield) as yellow solid. LC-MS (ESI⁺) m/z 461.1 (M+H)⁺.

Step 5—N-[6-acetyl-2-(4-formylcyclohexyl)indazol-5-yl]-6-(trifluoromethyl)pyridine-2-carboxamide To a solution of N-[6-acetyl-2-[4-(hydroxymethyl)cyclohexyl]indazol-5-yl]-6-(trifluoromethyl)pyridine-2-carboxamide (50 mg, 108 umol) in DMSO (2 mL) was added IBX (91.2 mg, 325 umol). The mixture was stirred at 50° C. for 1 hr. On completion, the reaction mixture was quenched with saturated Na₂S₂O₃ (5 mL) and saturated NaHCO₃ (5 mL) at 25° C. Then the mixture was stirred for 5 minutes. The mixture was then extracted with EA (20 mL×2) and washed with H₂O (10 mL×2). The reaction mixture was concentrated under reduced pressure to give the title compound (48 mg, 96% yield) as a yellow solid. LC-MS (ESI⁺) m/z 459.1 (M+H)⁺.

Methyl 2-(4-formylcyclohexyl)-5-[[6-(trifluoromethyl)pyridine-2-carbonyl]amino]indazole-6-carboxylate (Intermediate CFZ)

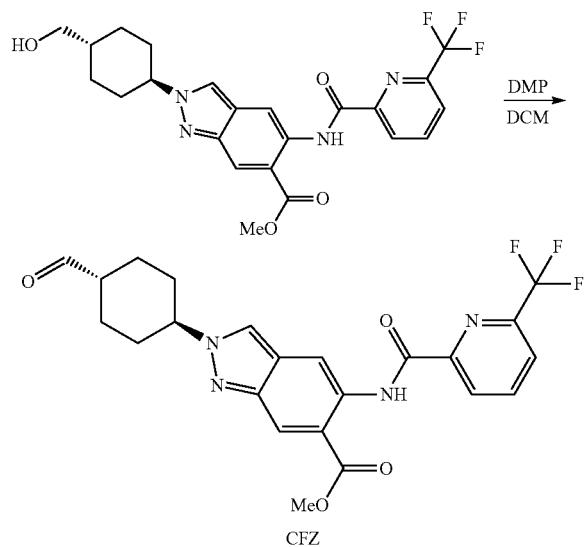

CFZ

To a solution of methyl 2-[4-(hydroxymethyl)cyclohexyl]-5-[[6-(trifluoromethyl)pyridine-2-carbonyl]amino]indazole-6-carboxylate (100 mg, 209 umol, synthesized via Step 1 of Intermediate CFY) in DCM (2 mL) and DMF (0.25 mL) was added DMP (133 mg, 314 umol). The reaction was stirred at 25° C. for 16 hrs. On completion, the reaction mixture was quenched with saturated Na₂S₂O₃ solution (10 mL) and saturated NaHCO₃ (10 mL) and stirred for 10 min. The mixture was extracted with DCM (10 mL×2). The combined organic layers were dried over Na₂SO₄, filtered and concentrated in vacuo to give the title compound (90.0 mg, 90% yield) as brown solid. ¹H NMR (400 MHz, DMSO-d₆) δ 12.53 (s, 1H), 9.65 (s, 1H), 9.06 (s, 1H), 8.58 (s, 1H), 8.49-8.44 (m, 2H), 8.39 (t, J=7.6 Hz, 1H), 8.20 (d, J=7.6 Hz, 1H), 4.56 (tt, J=3.6, 11.6 Hz, 1H), 3.96 (s, 3H), 2.45-2.40 (m, 1H), 2.25 (dd, J=2.8, 12.4 Hz, 2H), 2.13 (d, J=11.6 Hz, 2H), 2.06-1.96 (m, 2H), 1.46 (dq, J=3.2, 12.8 Hz, 2H), LC-MS (ESI⁺) m/z 475.0 (M+H)⁺.

4-[8-Oxo-6-[6-(trifluoromethyl)-2-pyridyl]pyrazolo[3,4-g][3,1]benzoxazin-2-yl]cyclohexanecarbaldehyde (Intermediate CGA)

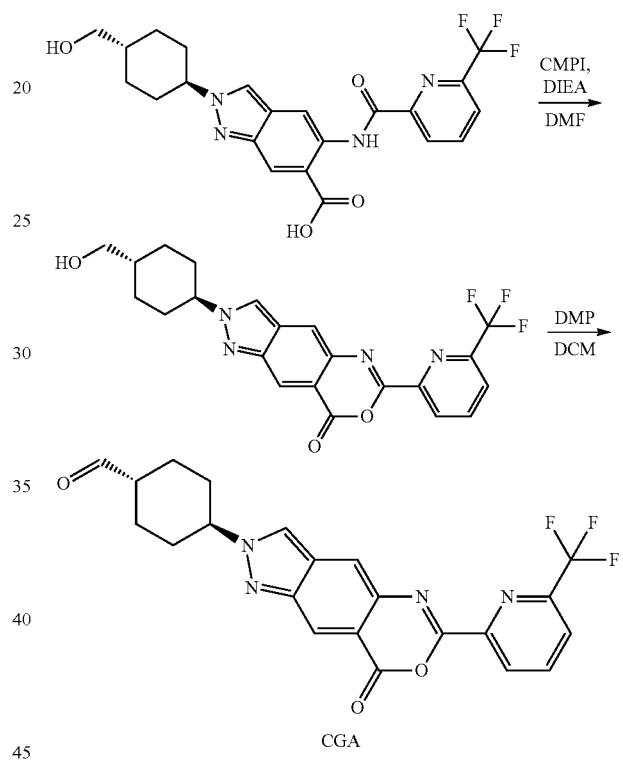

CGA

Step 1—2-[4-(Hydroxymethyl)cyclohexyl]-6-[6-(trifluoromethyl)-2-pyridyl]pyrazolo[3,4-g][3,1]benzoxazin-8-one To a solution of 2-[4-(hydroxymethyl)cyclohexyl]-5-[[6-(trifluoromethyl)pyridine-2-carbonyl]amino]indazole-6-carboxylic acid (200 mg, 432 umol, synthesized via Steps 1-2 of CFY) in DMF (2 mL) was added CMPI (165 mg, 648 umol) and DIEA (167 mg, 1.30 mmol). The mixture was stirred at 25° C. for 1 hr. On completion, the residue was diluted with water (30 mL) and extracted with EA (20 mL×2). The combined organic layer was dried over Na₂SO₄, filtered and concentrated in vacuo to give the title compound (170 mg, 88% yield) as a white solid. ¹H NMR (400 MHz, DMSO-d₆) δ 8.79 (s, 1H), 8.61-8.55 (m, 2H), 8.33 (t, J=8.0 Hz, 1H), 8.19 (s, 1H), 8.13 (d, J=7.6 Hz, 1H), 4.70-4.55 (m, 1H), 4.50 (t, J=5.2 Hz, 1H), 3.31-3.27 (m, 2H), 2.21 (d, J=10.0 Hz, 2H), 2.03-1.90 (m, 4H), 1.60-1.45 (m, 1H), 1.25-1.15 (m, 2H).

Step 2—4-[8-Oxo-6-[6-(trifluoromethyl)-2-pyridyl]pyrazolo[3,4-g][3,1]benzoxazin-2-yl]cyclohexanecarbaldehyde To a solution of 2-[4-(hydroxymethyl)cyclohexyl]-6-[6-(trifluoromethyl)-2-pyridyl]pyrazolo[3,4-g][3,1]benzoxazin-8-one (120 mg, 270 umol) in DCM (2 mL) was added DMP (171 mg, 405 umol). The mixture was stirred at 25° C. for 16 hrs. On completion, the reaction mixture was quenched with saturated Na$_2$S$_2$O$_3$ (5 mL) and saturated NaHCO$_3$ (5 mL) at 25° C., and stirred for 5 minutes. The mixture was extracted with DCM (20 mL×2) and washed with H$_2$O (10 mL×2). Then the reaction mixture was concentrated under reduced pressure to give the title compound (110 mg, 92% yield) as yellow solid. LC-MS (ESI$^+$) m/z 443.0 (M+H)$^+$.

1-[8-[4-[(4-aminocyclohexyl)methyl]piperazin-1-yl]-4-isoquinolyl]hexahydropyrimidine-2,4-dione (Intermediate CGB)

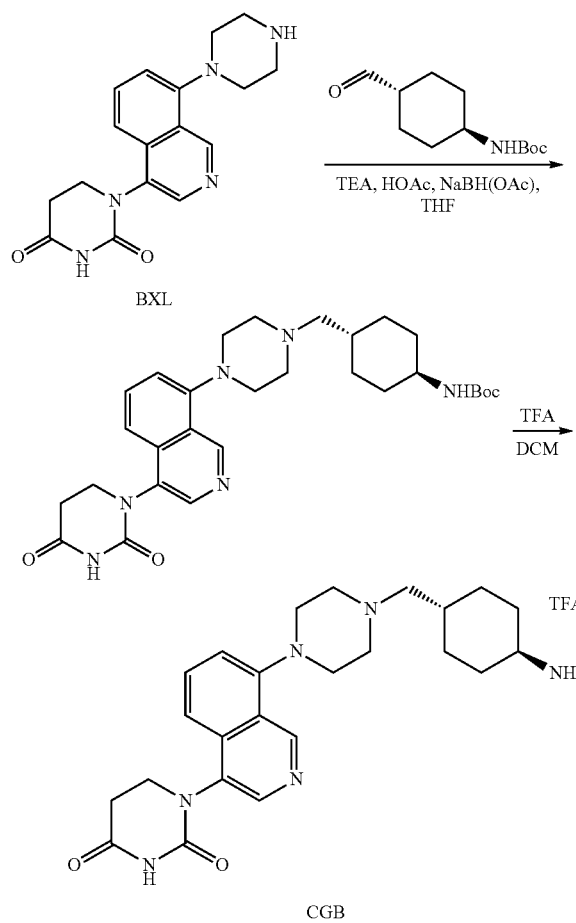

Step 1—Tert-butyl N-[4-[[4-[4-(2,4-dioxohexahydropyrimidin-1-yl)-8-isoquinolyl]piperazin-1-yl]methyl]cyclohexyl]carbamate A solution of 1-(8-piperazin-1-yl-4-isoquinoly)hexahydropyrimidine-2,4-dione (414 mg, 942 umol, TFA, Intermediate BXL), TEA (190 mg, 1.88 mmol), HOAc (169 mg, 2.83 mmol) and tert-butyl N-(4-formylcyclohexyl)carbamate (257 mg, 1.13 mmol, CAS #181308-57-6) in THF (4 mL) was stirred at -10° C. for 0.5 hr. Then, to the above mixture was added NaBH(OAc)$_3$ (399 mg, 1.88 mmol) and stirred at -10° C. for 2 hrs. On completion, the reaction mixture was quenched by addition water (0.2 mL). The reaction mixture was diluted with EA (100 mL) and washed with water (50 mL). The water phase was extracted with EA (50 mL×3). The combined organic layers were concentrated in vacuo. The residue was purified by prep-HPLC (column: Welch Xtimate C18 250*50 mm*10 um; mobile phase: [water (FA)-ACN]; B %: 2%-30%, 12 min) to give title compound (500 mg, 98% yield) as yellow solid. $^1$H NMR (400 MHz, DMSO-d$_6$) δ 10.52 (s, 1H), 9.43 (s, 1H), 8.54 (s, 1H), 7.77-7.69 (m, 1H), 7.64 (d, J=8.0 Hz, 1H), 7.29 (d, J=7.2 Hz, 1H), 6.79-6.64 (m, 1H), 3.94-3.86 (m, 1H), 3.73-3.66 (m, 1H), 3.27-3.02 (m, 7H), 3.02-2.90 (m, 2H), 2.80-2.70 (m, 2H), 2.67-2.58 (m, 1H), 2.30-2.11 (m, 1H), 1.84-1.76 (m, 4H), 1.60-1.44 (m, 1H), 1.38 (s, 9H), 1.21-1.10 (m, 2H), 0.95 (d, J=6.4 Hz, 2H).

Step 2—1-[8-[4-[(4-aminocyclohexyl)methyl]piperazin-1-yl]-4-isoquinolyl]hexahydropyrimidine-2,4-dione To a solution of tert-butyl N-[4-[[4-[4-(2,4-dioxohexahydropyrimidin-1-yl)-8-isoquinolyl]piperazin-1-yl]methyl]cyclohexyl]carbamate (114 mg, 212 umol) in DCM (2 mL) was added TFA (616 mg, 5.40 mmol) at 25° C. The mixture was stirred at 25° C. for 1 hr. On completion, the reaction mixture was concentrated in vacuo to give title compound (116 mg, 100% yield, TFA) as yellow oil. LC-MS (ESI$^+$) m/z 437.1 (M+H)$^+$.

[4-[4-[4-(Isopropylamino)-6-(4,4,5,5-tetramethyl-1,3,2-dioxaborolan-2-yl)-3-pyridyl] triazol-1-yl]cyclohexyl]methanol (Intermediate CGC)

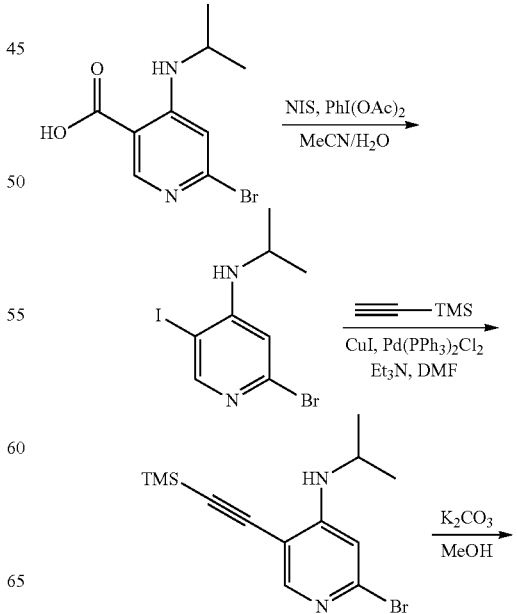

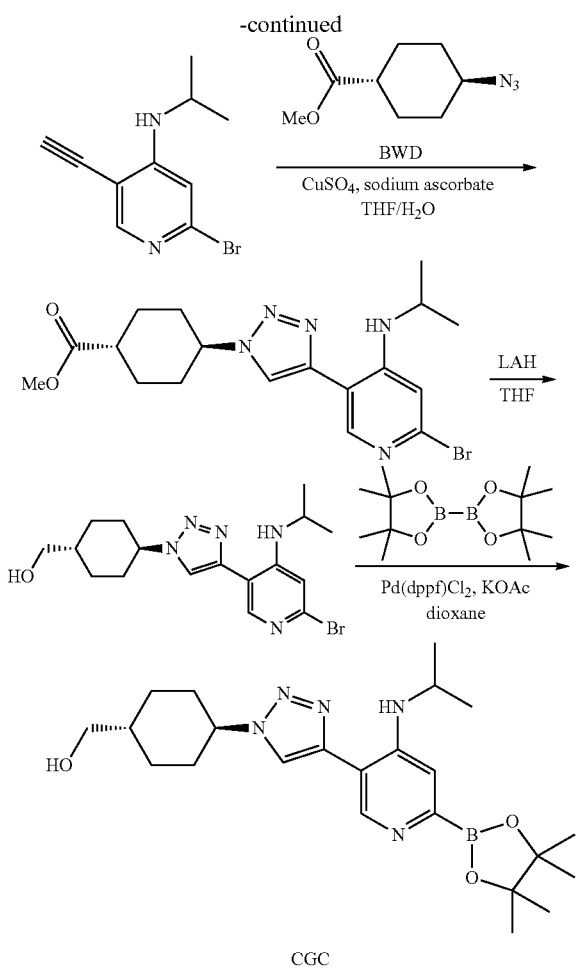

Step 1—2-Bromo-5-iodo-N-isopropyl-pyridin-4-amine

To a mixture of 6-bromo-4-(isopropylamino)pyridine-3-carboxylic acid (9.40 g, 36.2 mmol, synthesized via Steps 1-3 of Intermediate BVU) in ACN (90 mL) and H₂O (30 mL) was added PhI(OAc)₂ (5.84 g, 18.1 mmol), then the reaction mixture was stirred at 60° C. for 0.5 hr. Next, NIS (8.98 g, 39.9 mmol) was added to the mixture, and the reaction mixture was stirred at 60° C. for 12 hr. On completion, the residue was diluted with water (100 mL) and extracted with EA (2×80 mL). The combined organic layers were dried over Na₂SO₄, filtered and concentrated in vacuo to give a residue. The residue was purified by reversed phase flash (0.1% FA condition) to give the title compound (15.0 g, 60% yield) as a yellow solid. ¹H NMR (400 MHz, DMSO-d₆) δ 8.21 (s, 1H), 6.73 (s, 1H), 5.38 (d, J=8.0 Hz, 1H), 3.91-3.72 (m, 1H), 1.19 (d, J=6.4 Hz, 6H); LC-MS (ESI+) m/z 342.5 (M+H)⁺.

Step 2—2-Bromo-N-isopropyl-5-(2-trimethylsilylethynyl)pyridin-4-amine

To a solution of 2-bromo-5-iodo-N-isopropyl-pyridin-4-amine (9.00 g, 26.3 mmol) and ethynyl(trimethyl)silane (3.89 g, 39.5 mmol, CAS #1066-54-2) in DMF (50 mL) were added CuI (502 mg, 2.64 mmol), Pd(PPh₃)₂Cl₂ (1.85 g, 2.64 mmol) and TEA (8.01 g, 79.1 mmol). Then the reaction mixture was stirred at 80° C. for 0.5 hr under N₂. On completion, the residue was diluted with water (50 mL) and extracted with EA (2×20 mL). The combined organic layers were washed with brine (2×15 mL) and dried over Na₂SO₄, filtered and the filtrate was concentrated in vacuo to give a residue. The residue was purified by column chromatography (SiO₂, PE:EA=5:1, Rf=0.7) to give the title compound (7.00 g, 77% yield) as a yellow oil. ¹H NMR (400 MHz, DMSO-d₆) δ 7.96 (s, 1H), 6.83 (s, 1H), 5.42 (d, J=7.6 Hz, 1H), 3.83 (qd, J=6.0, 12.8 Hz, 1H), 1.18 (d, J=6.0 Hz, 6H), 0.28-0.16 (m, 9H); LC-MS (ESI+) m/z 312.9 (M+H)⁺.

Step 3—2-Bromo-5-ethynyl-N-isopropyl-pyridin-4-amine

To a solution of 2-bromo-N-isopropyl-5-(2-trimethylsilylethynyl)pyridine-4-amine (6.00 g, 19.2 mmol) in MeOH (30 mL) was added K₂CO₃ (5.33 g, 38.5 mmol), then the reaction mixture was stirred at 25° C. for 1 hr. On completion, the reaction mixture was filtered and the filtrate was concentrated in vacuo to give a residue. The residue was diluted with water (30 mL) and extracted with EA (2×20 mL). The combined organic layer was washed with brine (15 mL) and dried over Na₂SO₄, filtered and the filtrate was concentrated in vacuo to give the title compound (5.00 g, 98% yield) as a brown oil. ¹H NMR (400 MHz, DMSO-d₆) δ 7.97 (s, 1H), 6.80 (s, 1H), 5.83 (d, J=8.4 Hz, 1H), 4.66 (s, 1H), 3.80 (qd, J=6.4, 14.8 Hz, 1H), 1.17 (d, J=6.4 Hz, 6H); LC-MS (ESI+) m/z 240.7 (M+H)⁺.

Step 4—Methyl 4-[4-[6-bromo-4-(isopropylamino)-3-pyridyl]triazol-1-yl]cyclohexanecarboxylate To a solution of 2-bromo-5-ethynyl-N-isopropyl-pyridin-4-amine (2.9 g, 12.1 mmol) and methyl 4-azidocyclohexanecarboxylate (2.44 g, 13.3 mmol, Intermediate BWD) in H₂O (20 mL) and THF (20 mL) was added sodium ascorbate (961 mg, 4.85 mmol) and CuSO₄·5H₂O (1.21 g, 4.85 mmol), then the reaction mixture was stirred at 25° C. for 12 hrs. On completion, the reaction mixture was filtered and concentrated in vacuo. The residue was diluted with water (30 mL) and extracted with EA (2×30 mL). The combined organic layer was washed with brine (30 mL) and dried over Na₂SO₄, filtered and the filtrate was concentrated in vacuo to give a residue. The residue was purified by reversed phase flash (0.1% FA condition) to give the title compound (3 g, 58% yield) as a white solid. ¹H NMR (400 MHz, DMSO-d6) δ 8.82 (s, 1H), 8.32 (s, 1H), 8.24 (d, J=7.6 Hz, 1H), 6.84 (s, 1H), 4.65-4.50 (m, 1H), 3.91-3.76 (m, 1H), 3.63 (s, 3H), 2.48-2.39 (m, 1H), 2.28-2.17 (m, 2H), 2.08 (dd, J=2.8, 11.2 Hz, 2H), 1.88 (dq, J=3.2, 12.4 Hz, 2H), 1.70-1.53 (m, 2H), 1.23 (d, J=6.4 Hz, 6H); LC-MS (ESI+) m/z 422.3 (M+H)⁺.

Step 5—[4-[4-[6-Bromo-4-(isopropylamino)-3-pyridyl]triazol-1-yl]cyclohexyl]methanol To a mixture of methyl 4-[4-[6-bromo-4-(isopropylamino)-3-pyridyl]triazol-1-yl] cyclohexanecarboxylate (1.90 g, 4.50 mmol) in THF (30 mL) was added LAH (221 mg, 5.85 mmol) at 0° C. The mixture was then stirred at 0° C. for 0.5 hr. On completion, the reaction mixture was quenched with H₂O (0.1 mL) and 15% NaOH (0.6 mL) at 20° C., then dried over anhydrous sodium sulfate, filtered and concentrated under reduced pressure to give a residue. The residue was purified by reversed phase flash (0.1% FA condition) to give the title compound (2.40 g, 98% yield) as a white solid. ¹H NMR (400 MHz, DMSO-d₆) δ 8.84 (s, 1H), 8.32 (s, 1H), 8.27 (d, J=7.6 Hz, 1H), 6.84 (s, 1H), 4.56-4.44 (m, 2H), 3.83 (qd, J=6.4, 13.2 Hz, 1H), 3.28 (t, J=5.6 Hz, 2H), 2.18 (d, J=9.6 Hz, 2H), 1.90 (d, J=11.6 Hz, 2H), 1.86-1.72 (m, 2H), 1.55-1.38 (m, 1H), 1.23 (d, J=6.4 Hz, 6H), 1.21-1.07 (m, 2H); LC-MS (ESI+) m/z 396.1 (M+H)⁺.

Step 6—[4-[4-[4-(Isopropylamino)-6-(4,4,5,5-tetramethyl-1,3,2-dioxaborolan-2-yl)-3-pyridyl]triazol-1-yl]cyclohexyl]methanol To a solution of [4-[4-[6-bromo-4-(isopropylamino)-3-pyridyl]triazol-1-yl]cyclohexyl]methanol (100 mg, 253 umol) and 4,4,5,5-tetramethyl-2-(4,4,5,5-tetramethyl-1,3,2-dioxaborolan-2-yl)-1,3,2-dioxaborolane (128 mg, 507 umol, CAS #73183-34-3) in dioxane (4 mL) were added KOAc (74.6 mg, 760 umol) and Pd(dppf)Cl₂·CH₂Cl₂ (20.7 mg, 25.3 umol). The mixture was stirred at 100° C. for 3 hrs under N₂. On completion, the crude compound was used without work-up and further purification to give the title compound (447 mg, 99% yield) as a frey solid. LC-MS (ESI+) m/z 442.2 (M+H)⁺.

7-[5-[1-(4-Formylcyclohexyl)triazol-4-yl]-4-(isopropylamino)-2-pyridyl]pyrrolo[1,2-b]pyridazine-3-carbonitrile (Intermediate CGD)

Step 1—7-[5-[1-[4-(Hydroxymethyl)cyclohexyl]triazol-4-yl]-4-(isopropylamino)-2-pyridyl]pyrrolo[1,2-b]pyridazine-3-carbonitrile To a solution of [4-[4-[4-(isopropylamino)-6-(4,4,5,5-tetramethyl-1,3,2-dioxaborolan-2-yl)-3-pyridyl]triazol-1-yl]cyclohexyl]methanol (111 mg, 251 umol, Intermediate CGC) and 7-bromopyrrolo[1,2-b]pyridazine-3-carbonitrile (44.6 mg, 201 umol, Intermediate BVT) in dioxane (4 mL) and H₂O (0.4 mL) were added KOAc (24.6 mg, 251 umol) and Pd(dppf)Cl₂·CH₂Cl₂ (20.5 mg, 25.1 umol). The mixture was then stirred at 100° C. for 2 hrs under N₂. On completion, the reaction mixture was diluted with EA (60 mL), filtered and concentrated in vacuo. The residue was purified by reversed phase flash (0.1% FA condition), then purified by prep-TLC (SiO₂, DCM:MeOH=10:1) to give the title compound (59.0 mg, 12% yield) as a yellow solid. ¹H NMR (400 MHz, DMSO-d₆) δ 8.85 (s, 1H), 8.81 (d, J=2.0 Hz, 1H), 8.72-8.65 (m, 2H), 8.18 (d, J=7.2 Hz, 1H), 8.13 (s, 1H), 7.81 (d, J=4.8 Hz, 1H), 7.10 (d, J=4.8 Hz, 1H), 4.60-4.47 (m, 2H), 3.89 (qd, J=6.4, 12.8 Hz, 1H), 3.30-3.27 (m, 2H), 2.21 (d, J=11.6 Hz, 2H), 1.98-1.77 (m, 4H), 1.56-1.41 (m, 1H), 1.34 (d, J=6.4 Hz, 6H), 1.25-1.10 (m, 2H); LC-MS (ESI+) m/z 457.6 (M+H)⁺.

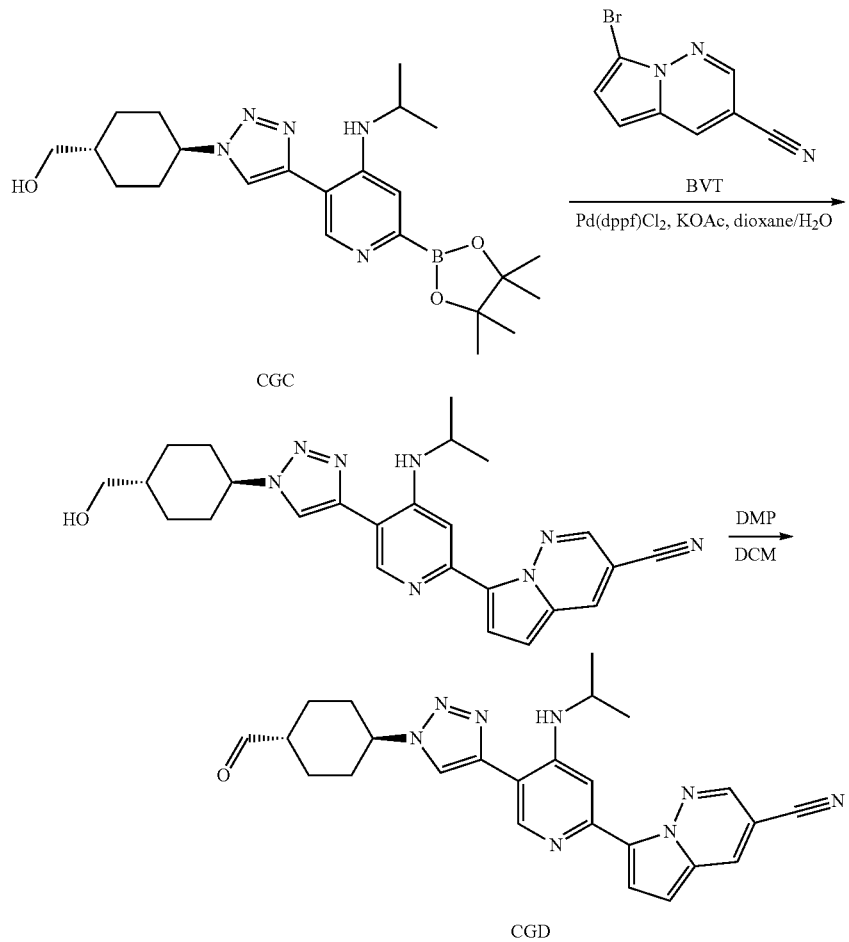

Step 2—7-[5-[1-(4-Formylcyclohexyl)triazol-4-yl]-4-(isopropylamino)-2-pyridyl]pyrrolo[1,2-b]pyridazine-3-carbonitrile To a mixture of 7-[5-[1-[4-(hydroxymethyl)cyclohexyl]triazol-4-yl]-4-(isopropylamino)-2-pyridyl]pyrrolo[1,2-b]pyridazine-3-carbonitrile (49.0 mg, 107 umol) in DCM (1.5 mL) was added DMP (68.2 mg, 160 umol). The mixture then was stirred at 25° C. for 1 hr. On completion, the reaction mixture was quenched by saturated NaHCO$_3$ (2.5 mL) and Na$_2$S$_2$O$_3$ (2.5 mL), then the mixture was extracted with DCM (3×5 mL). The combined organic layers were washed with NaCl (5 mL×2), dried over Na$_2$SO$_4$, filtered and concentrated in vacuo to give the title compound (57.0 mg, 99% yield) as a yellow solid. LC-MS (ESI+) m/z 455.1 (M+H)$^+$.

1-(8-bromo-6-fluoro-4-isoquinolyl)-3-[(4-methoxyphenyl)methyl]hexahydropyrimidine-2,4-dione (Intermediate CGE)

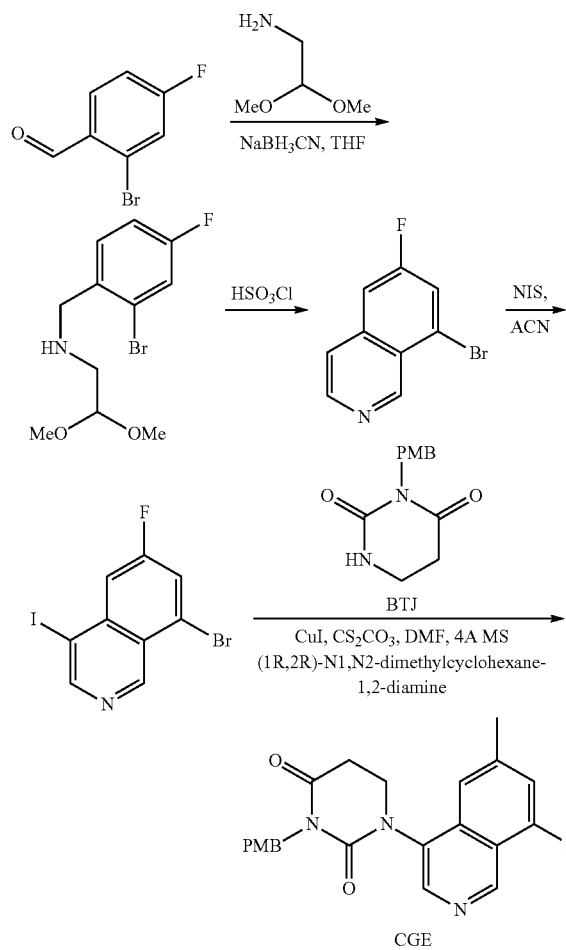

CGE

Step 1—N-[(2-bromo-4-fluoro-phenyl)methyl]-2,2-dimethoxy-ethanamine

To a solution of 2-bromo-4-fluoro-benzaldehyde (5 g, 24.6 mmol, CAS #59142-68-6) and 2,2-dimethoxy-ethanamine (2.85 g, 27.0 mmol, CAS #645-36-3) in MeOH (60 mL) was added NaBH$_3$CN (3.10 g, 49.2 mmol), then the reaction was stirred at 25° C. for 2 hrs. On completion, the reaction was quenched with water (5 mL) and the reaction was diluted with EA (80 mL), and washed water (30 mL×4). The organic layer was separated and dried over Na$_2$SO$_4$, filtered and concentrated in vacuo. The residue was purified by column chromatography (SiO$_2$, PE:EA=5:1 to 3:1) to give the title compound (3.2 g, 44% yield) as yellow oil. $^1$H NMR (400 MHz, DMSO-d$_6$) δ 7.59-7.46 (m, 2H), 7.25-7.20 (m, 1H), 4.40 (t, J=5.6 Hz, 1H), 3.74 (s, 2H), 3.25 (s, 6H), 2.59 (d, J=5.6 Hz, 2H), 2.01 (s, 1H).

Step 2—8-Bromo-6-fluoro-isoquinoline

To a solution of HSO$_3$Cl (3.99 g, 34.2 mmol, 2.28 mL) was added N-[(2-bromo-4-fluoro-phenyl)methyl]-2,2-dimethoxy-ethanamine (1.00 g, 3.42 mmol) slowly at −10° C., then the reaction mixture was stirred at 90° C. for 1 hr. On completion, the reaction mixture was added into ice water (40 mL), and extracted with DCM (80 mL). To the aqueous phase was add NaOH (1N) until the pH=8, then extracted with DCM (100 mL). The organic layer was washed with water (30 mL×4), dried over Na$_2$SO$_4$, filtered and concentrated in vacuo to give the title compound (449 mg, 58% yield) as brown oil. $^1$H NMR (400 MHz, DMSO-d$_6$) δ 9.45 (s, 1H), 8.64 (d, J=5.6 Hz, 1H), 8.09 (dd, J=2.4, 8.8 Hz, 1H), 7.94-7.87 (m, 2H).

Step 3—8-bromo-6-fluoro-4-iodo-isoquinoline

To a solution of 8-bromo-6-fluoro-isoquinoline (349 mg, 1.54 mmol) in AcOH (4 mL) was added NIS (416 mg, 1.85 mmol), then the reaction mixture was stirred at 50° C. for 10 hrs. On completion, the residue was diluted with EA (20 mL), and concentrated in vacuo. The residue was purified by column chromatography (SiO$_2$, PE:PA=10:1) to give the title compound (158 mg, 29% yield) as a white solid. LC-MS (ESI$^+$) m/z 351.8 (M+H)$^+$.

Step 4—1-(8-bromo-6-fluoro-4-isoquinolyl)-3-[(4-methoxyphenyl)methyl]hexahydropyrimidine-2,4-dione To a solution of 8-bromo-6-fluoro-4-iodo-isoquinoline (20 mg, 56.8 umol) and 3-[(4-methoxyphenyl)methyl]hexahydropyrimidine-2,4-dione (14.6 mg, 62.5 umol, Intermediate BTJ) in DMF (2 mL) was added Cs$_2$CO$_3$ (37.0 mg, 113 umol), CuI (4.33 mg, 22.7 umol), (1R,2R)—N1,N2-dimethylcyclohexane-1,2-diamine (3.23 mg, 22.73 umol) and 4 Å molecular sieves. Then the reaction mixture was stirred at 70° C. for 16 hrs under N$_2$. On completion, the mixture was concentrated in vacuo. The crude product was purified by reversed-phase HPLC (column: Phenomenex luna C18 150*25 mm*10 um; mobile phase: [water (FA)-ACN]; B %: 39%-69%, 8 min) to give the title compound (4 mg, 15% yield) as a white solid. LC-MS (ESI$^+$) m/z 459.7 (M+H)$^+$.

1-(6-fluoro-8-piperazin-1-yl-4-isoquinolyl)hexahydropyrimidine-2,4-dione (Intermediate CGF)

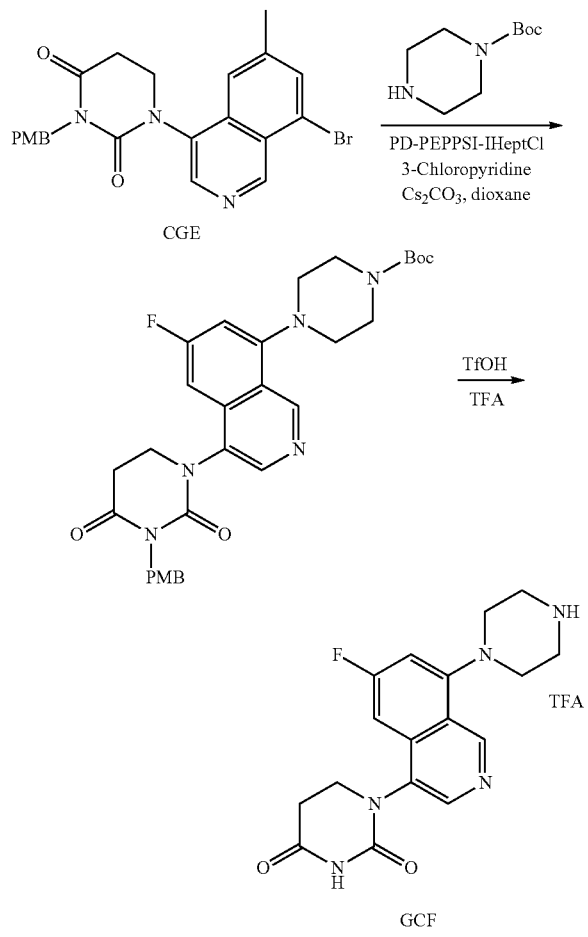

3-[4-(3,6-Diazabicyclo[3.1.1]heptan-6-yl)-3-methyl-2-oxo-benzimidazol-1-yl]piperidine-2,6-dione (Intermediate CGG)

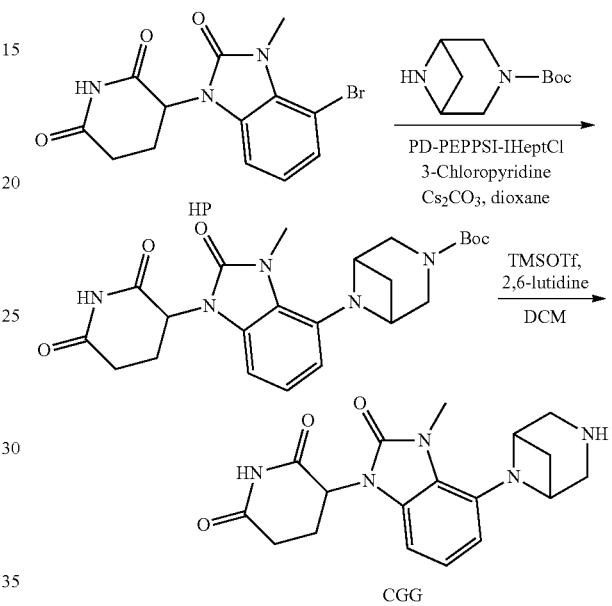

Step 1—Tert-butyl 4-[6-fluoro-4-[3-[(4-methoxyphenyl)methyl]-2,4-dioxo-hexahydropyrimidin-1-yl]-8-isoquinolyl]piperazine -1-carboxylate To a solution of 1-(8-bromo-6-fluoro-4-isoquinolyl)-3[(4-methoxyphenyl)methyl]hexahydropyrimidine-2,4-dione (100 mg, 218 umol, Intermediate CGE) and tert-butyl piperazine-1-carboxylate (64.5 mg, 261 umol, HOAc, CAS #143238-38-4) in dioxane (3 mL) was added Cs$_2$CO$_3$ (213 mg, 654 umol) and PD-PEPPSI-IHeptCl 3-Chloropyridine (20.2 mg, 21.8 umol). The reaction was stirred at 100° C. for 16 hours under N$_2$. On completion, the reaction mixture was filtered and concentrated in vacuo. The residue was purified by prep-TLC (SiO$_2$, PE:EA=1:2, P1:Rf=0.5) to give the title compound (120 mg, 97% yield) as yellow solid. $^1$H NMR (400 MHz, DMSO-d$_6$) δ 9.40 (s, 1H), 8.56 (s, 1H), 7.35 (dd, J=1.6, 9.6 Hz, 1H), 7.26 (d, J=8.4 Hz, 2H), 7.17 (dd, J=2.0, 11.2 Hz, 1H), 6.87 (d, J=8.4 Hz, 2H), 4.90-4.76 (m, 2H), 3.95-3.86 (m, 1H), 3.78-3.69 (m, 4H), 3.64 (s, 3H), 3.26-3.03 (m, 6H), 2.93 (m, 1H), 1.44 (s, 9H).

Step 2—1-(6-fluoro-8-piperazin-1-yl-4-isoquinoly) hexahydropyrimidine-2,4-dione To a solution of tert-butyl 4-[6-fluoro-4-[3-[(4-methoxyphenyl)methyl]-2,4-dioxo-hexahydropyrimidin-1-yl]-8-isoquinolyl]piperazine-1-carboxylate (50.0 mg, 88.7 umol) in TFA (0.3 mL) was added TfOH (340 mg, 2.27 mmol), then the reaction was stirred at 70° C. for 0.5 hour. On completion, the reaction mixture was concentrated in vacuo to give the title compound (40 mg, 98% yield, TFA) as brown oil. LC-MS (ESI$^+$) m/z 344.0 (M+H)$^+$.

Step 1—Tert-butyl 6-[1-(2,6-dioxo-3-piperidyl)-3-methyl-2-oxo-benzimidazol-4-yl]-3,6-diazabicyclo[3.1.1]heptane-3-carboxylate To a mixture of 3-(4-bromo-3-methyl-2-oxo-benzimidazol-1-yl)piperidine-2,6-dione (100 mg, 295 umol, Intermediate HP) in dioxane (5 mL) was tert-butyl 3,6-diazabicyclo[3.1.1]heptane-3-carboxylate (70.3 mg, 354 umol, CAS #1251017-66-9), Cs$_2$CO$_3$ (289 mg, 887 umol) and PD-PEPPSI-IHeptCl 3-Chloropyridine (14.3 mg, 14.7 umol). Then the reaction mixture was stirred at 100° C. for 48 hrs. On completion, the reaction mixture was filtered and concentrated in vacuo. The residue was purified by reverse phase (0.1% FA condition) to give the title compound (200 mg, 29% yield) as white solid. LC-MS (ESI$^+$) m/z 456.1 (M+H)$^+$.

Step 2—3-[4-(3,6-Diazabicyclo[3.1.1]heptan-6-yl)-3-methyl-2-oxo-benzimidazol-1-yl]piperidine -2,6-dione To a solution of tert-butyl 6-[1-(2,6-dioxo-3-piperidyl)-3-methyl-2-oxo-benzimidazol-4-yl]-3,6-diaza bicyclo[3.1.1] heptane-3-carboxylate (40 mg, 87.8 umol) in DCM (2 mL) were added 2,6-lutidine (18.8 mg, 175 umol, 20.4 uL) and TMSOTf (29.2 mg, 131 umol, 23.8 uL) at 0° C. Then the reaction mixture was stirred for 5 hr at 25° C. On completion, the reaction mixture was concentrated in vacuo. The residue was purified by prep-HPLC (column: Phenomenex Luna C18 150*25 mm*10 um; mobile phase: [water(FA)-ACN]; B %: 1%-22%, 10.5 min) to give the title compound (12.0 mg, 38% yield) as white solid. LC-MS (ESI⁺) m/z 356.3 (M+H)⁺.

4-(Isopropylamino)-2-thiazol-5-yl-thieno[2,3-b]pyridine-5-carboxylic acid (Intermediate CGH)

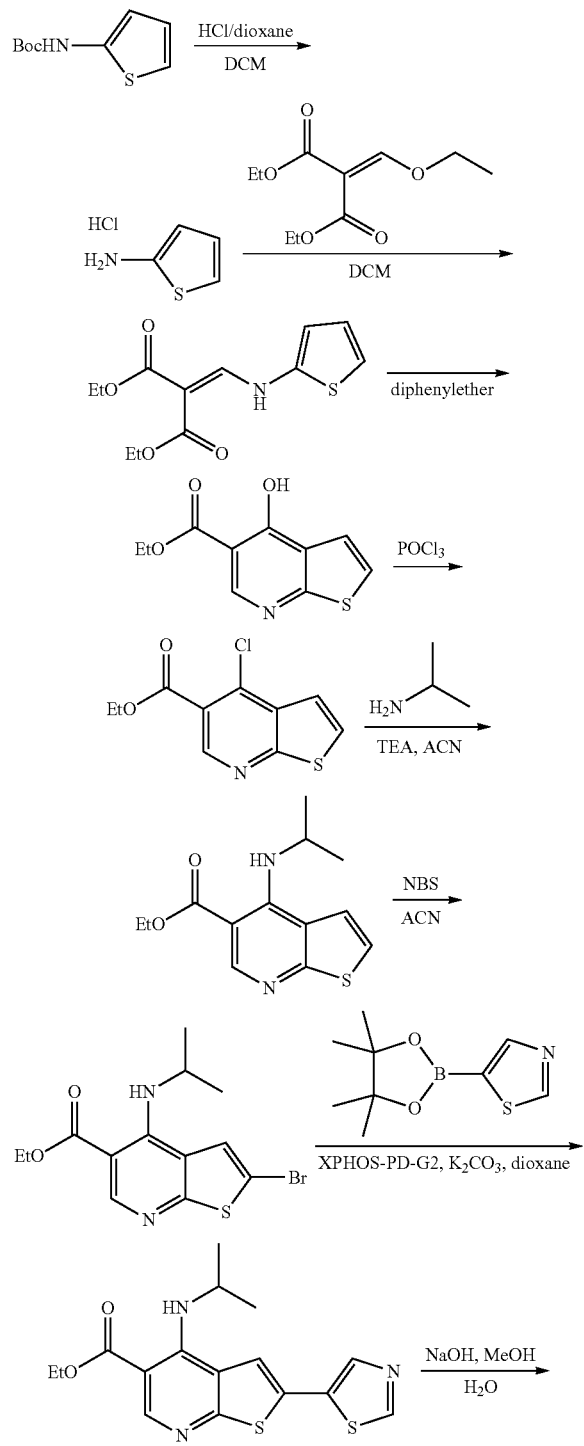

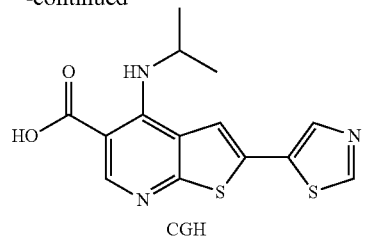

Step 1—Thiophen-2-amine

To a mixture of tert-butyl N-(2-thienyl)carbamate (20.0 g, 100 mmol, CAS #56267-50-6) in DCM (80 mL) was added HCl/dioxane (4 M, 70 mL). The reaction mixture was stirred at 25° C. for 6 hr. On completion, the reaction mixture was concentrated in vacuo. The residue was diluted with NH₃·H₂O (30 mL) and H₂O (200 ml) and extracted with DCM (2×300 mL). The combined organic layer was dried over Na₂SO₄, filtered and concentrated in vacuo to give the compound (7.00 g, 70% yield) as brown solid.

Step 2—Diethyl 2[(2-thienylamino)methylene]propanedioate

A mixture of thiophen-2-amine (7.00 g, 70.6 mmol) and diethyl 2-(ethoxymethylene)propanedioate (15.2 g, 70.6 mmol) in DCM (50 mL) was stirred at 25° C. for 12 hour. On completion, the reaction mixture was concentrated in vacuo. The residue was purified by column chromatography to give the title compound (6.10 g, 32% yield) as yellow oil. ¹H NMR (400 MHz, CDCl₃) δ 11.12 (d, J=12.8 Hz, 1H), 8.24 (d, J=13.2 Hz, 1H), 6.92-6.83 (m, 2H), 6.70-6.63 (m, 1H), 4.34-4.27 (m, 2H), 4.26-4.20 (m, 2H), 1.38 (t, J=7.2 Hz, 3H), 1.32 (t, J=7.2 Hz, 3H). LC-MS (ESI⁺) m/z 270.0 (M+H)⁺.

Step 3—Ethyl 4-hydroxythieno[2,3-b]pyridine-5-carboxylate

A mixture of diethyl 2[(2-thienylamino)methylene]propanedioate (5.60 g, 20.7 mmol) in diphenylether (30 mL) was stirred at 230° C. for 5 hour. On completion, the reaction mixture was concentrated in vacuo. The residue was purified by column chromatography to give the title compound (2.90 g, 62% yield) as yellow solid. ¹H NMR (400 MHz, CDCl₃) δ 11.12 (d, J=13.2 Hz, 1H), 8.25 (d, J=13.2 Hz, 1H), 6.90-6.87 (m, 1H), 6.74-6.64 (dd, 1H), 4.35-4.27 (m, 2H), 1.38 (t, J=7.2 Hz, 3H).

Step 4—Ethyl 4-chlorothieno[2,3-b]pyridine-5-carboxylate

To a mixture of ethyl 4-hydroxythieno[2,3-b]pyridine-5-carboxylate (2.60 g, 11.6 mmol) in dioxane (20 mL) was added POCl₃ (10.7 g, 69.8 mmol). The reaction mixture was stirred at 105° C. for 2 hour. On completion, the residue was purified by column chromatography to give the title compound (2.80 g, 99% yield) as brown. ¹H NMR (400 MHz, DMSO-d₆) δ 8.91 (s, 1H), 8.13 (d, J=6.0 Hz, 1H), 7.59 (d, J=6.0 Hz, 1H), 4.43-4.32 (m, 2H), 1.35 (t, J=7.2 Hz, 3H), LC-MS (ESI⁺) m/z 242.0 (M+H)⁺.

Step 5—Ethyl 4-(isopropylamino)thieno[2,3-b]pyridine-5-carboxylate

To a mixture of ethyl 4-chlorothieno[2,3-b]pyridine-5-carboxylate (2.80 g, 11.5 mmol) and propan-2-amine (3.42 g, 57.9 mmol) in ACN (30 mL) was added TEA (5.86 g, 57.9 mmol). The reaction mixture was stirred at 90° C. for 6 hr. On completion, the residue was diluted with water (60 mL) and extracted with EA (2×60 mL). The combined organic layer was dried over $Na_2SO_4$, filtered and concentrated in vacuo to give the title compound (2.80 g, 91% yield) as brown solid. LC-MS (ESI$^+$) m/z 265.2 (M+H)$^+$.

Step 6—Ethyl 2-bromo-4-(isopropylamino)thieno[2,3-b]pyridine-5-carboxylate

To a mixture of ethyl 4-(isopropylamino)thieno[2,3-b]pyridine-5-carboxylate (2.80 g, 10.5 mmol) in ACN (30 mL) was added NBS (2.83 g, 15.8 mmol). The reaction mixture was stirred at 25° C. for 6 hr. On completion, the residue was diluted with water (50 mL) and extracted with EA (2×60 mL). The combined organic layer was dried over $Na_2SO_4$, filtered and concentrated in vacuo to give a residue. The residue was purified by reverse phase (0.1% FA condition) to give the title compound (2.02 g, 55% yield) as brown solid. $^1$H NMR (400 MHz, DMSO-d$_6$) δ 9.15-8.61 (m, 1H), 7.78 (s, 1H), 4.40-4.22 (m, 2H), 3.35 (s, 5H), 1.37-1.23 (m, 6H). LC-MS (ESI$^+$) m/z 344.9 (M+H)$^+$.

Step 7—Ethyl 4-(isopropylamino)-2-thiazol-5-yl-thieno[2,3-b]pyridine-5-carboxylate To a mixture of ethyl 2-bromo-4-(isopropylamino)thieno[2,3-b]pyridine-5-carboxylate (1.97 g, 5.74 mmol) and 5-(4,4,5,5-tetramethyl-1,3,2-dioxaborolan-2-yl)thiazole (4.85 g, 22.9 mmol) in dioxane (20 mL) was added XPHOS-PD-G2 (451 mg, 573 umol) and $K_2CO_3$ (2.38 g, 17.2 mmol). The reaction mixture was then stirred at 90° C. for 12 hour. On completion, the residue was diluted with water (50 mL) and extracted with EA (2×50 mL). The combined organic layer was dried over $Na_2SO_4$, filtered and concentrated in vacuo to give a residue. The residue was purified by reverse phase (0.1% FA condition) to give the title compound (1.80 g, 90% yield) as brown solid. LC-MS (ESI$^+$) m/z 348.5 (M+H)$^+$.

Step 8—4-(Isopropylamino)-2-thiazol-5-yl-thieno[2,3-b]pyridine-5-carboxylic Acid To a mixture of ethyl 4-(isopropylamino)-2-thiazol-5-yl-thieno[2,3-b]pyridine-5-carboxylate (1.30 g, 3.74 mmol) in MeOH (12 mL) and $H_2O$ (3 mL) was added NaOH (299 mg, 7.48 mmol). Then the reaction mixture was stirred at 60° C. for 2 hour. On completion, the residue was diluted with water (30 mL) and extracted with EA (2×30 mL). The combined organic layer was dried over $Na_2SO_4$, filtered and concentrated in vacuo to give a residue. The reaction mixture was diluted with water (20 mL) and acidified with citric acid until the pH=3-4. A solid precipitation formed which was then filtered and dried in vacuo to give the title compound (950 mg, 79% yield) as brown solid. $^1$H NMR (400 MHz, DMSO-d$_6$) δ 9.43-9.34 (d, 1H), 9.14 (s, 1H), 8.70 (s, 1H), 8.32 (s, 1H), 7.81 (s, 1H), 4.52-4.36 (m, 1H), 1.32 (d, J=6.0 Hz, 6H). LC-MS (ESI$^+$) m/z 319.9 (M+H)$^+$.

4-[4-[4-(Isopropylamino)-2-thiazol-5-yl-thieno[2,3-b]pyridin-5-yl]triazol-1-yl]cyclohexanecarbaldehyde (Intermediate CGI)

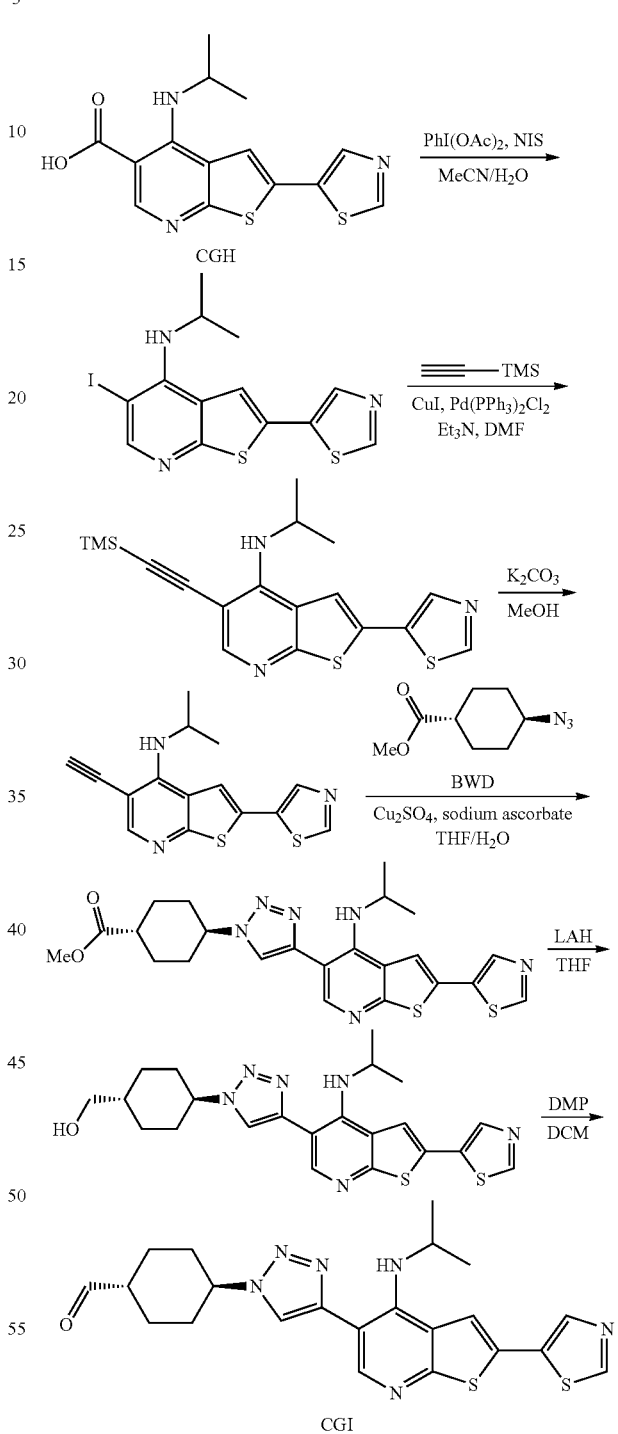

Step 1—5-Iodo-N-isopropyl-2-thiazol-5-yl-thieno[2,3-b]pyridin-4-amine

To a mixture of 4-(isopropylamino)-2-thiazol-5-yl-thieno[2,3-b]pyridine-5-carboxylic acid (900 mg, 2.82 mmol, Intermediate CGH) in MeCN (12 mL) and $H_2O$ (4 mL) was added PhI(OAc)$_2$ (453 mg, 1.41 mmol). The reaction mixture was stirred at 60° C. for 0.5 hour, then NIS (697 mg, 3.10 mmol) was added to the mixture and the reaction mixture was stirred at 60° C. for 12 hr. On completion, the residue was diluted with water (30 mL) and extracted with EA (2×30 mL). The combined organic layer was dried over Na$_2$SO$_4$, filtered and concentrated in vacuo to give a residue. The residue was purified by reverse phase (0.1% FA condition) to give title compound (1.00 g, 88% yield) as brown solid. LC-MS (ESI$^+$) m/z 401.8 (M+H)$^+$.

Step 2—N-isopropyl-2-thiazol-5-yl-5-(2-trimethylsilylethynyl)thieno[2,3-b]pyridin-4-amine To a mixture of 5-iodo-N-isopropyl-2-thiazol-5-yl-thieno[2,3-b]pyridin-4-amine (1.00 g, 2.49 mmol) and ethynyl(trimethyl)silane (1.22 g, 12.4 mmol) in DMF (20 mL) was added Pd(PPh$_3$)$_2$Cl$_2$ (174 mg, 249 umol), CuI (47.4 mg, 249 umol) and Et$_3$N (1.26 g, 12.4 mmol). The reaction mixture was then stirred at 80° C. for 16 hours. On completion, the residue was diluted with water (30 mL) and extracted with EA (2×30 mL). The combined organic layer was dried over Na$_2$SO$_4$, filtered and concentrated in vacuo to give a residue. The residue was purified by column chromatography to give the title compound (400 mg, 43% yield) as brown oil. $^1$H NMR (400 MHz, CDCl$_3$) δ 8.78 (s, 1H), 8.26 (s, 1H), 8.05 (s, 1H), 7.45 (s, 1H), 2.97-2.88 (m, 2H), 1.40 (d, J=6.4 Hz, 6H), 0.34-0.28 (m, 9H).

Step 3—5-Ethynyl-N-isopropyl-2-thiazol-5-yl-thieno[2,3-b]pyridin-4-amine

To a mixture of N-isopropyl-2-thiazol-5-yl-5-(2-trimethylsilylethynyl)thieno[2,3-b]pyridin-4-amine (200 mg, 538 umol) in MeOH (2 mL) was added K$_2$CO$_3$ (148 mg, 1.08 mmol). The reaction mixture was then stirred at 25° C. for 1 hr. On completion, the residue was diluted with water (30 mL) and extracted with EA (2×20 mL). The combined organic layer was dried over Na$_2$SO$_4$, filtered and concentrated in vacuo to give the title compound (160 mg, 99% yield) as brown solid. LC-MS (ESI$^+$) m/z 300.0 (M+H)$^+$.

Step 4—Methyl 4-[4-[4-(isopropylamino)-2-thiazol-5-yl-thieno[2,3-b]pyridin-5-yl]triazol-1-yl]cyclohexanecarboxylate To a mixture of methyl 4-azidocyclohexanecarboxylate (85.6 mg, 467 umol, Intermediate BWD) and 5-ethynyl-N-isopropyl-2-thiazol-5-yl-thieno[2,3-b]pyridin-4-amine (140 mg, 467 umol) in THF (1 mL) and H$_2$O (1 mL) was added CuSO$_4$ (29.8 mg, 187 umol) and sodium ascorbate (37.0 mg, 187 umol). The reaction mixture was then stirred at 25° C. for 1 hour. On completion, the residue was diluted with water (30 mL) and extracted with EA (2×20 mL). The combined organic layer was dried over Na$_2$SO$_4$, filtered and concentrated in vacuo to give a residue. The residue was purified by reverse phase (0.1% FA condition) to give the title compound (170 mg, 75% yield) as brown solid. $^1$H NMR (400 MHz, DMSO-d$_6$) δ 9.14 (s, 1H), 8.86-8.76 (m, 2H), 8.51 (s, 1H), 8.30 (s, 1H), 7.85 (s, 1H), 4.66-4.54 (m, 1H), 4.45-4.32 (m, 1H), 3.64 (s, 3H), 2.27-2.21 (m, 2H), 2.13-2.04 (m, 3H), 1.96-1.87 (m, 2H), 1.67-1.55 (m, 2H), 1.31 (d, J=6.0 Hz, 6H). LC-MS (ESI$^+$) m/z 483.2 (M+H)$^+$.

Step 5—[4-[4-[4-(Isopropylamino)-2-thiazol-5-yl-thieno[2,3-b]pyridin-5-yl]triazol-1-yl]cyclohexyl]methanol To a mixture of methyl 4-[4-[4-(isopropylamino)-2-thiazol-5-yl-thieno[2,3-b]pyridin-5-yl]triazol-1-yl]cyclohexanecarboxylate (60.0 mg, 124 umol) in THF (1 mL) was added LiAlH$_4$ (5.19 mg, 136 umol) at 0° C. The reaction mixture was then stirred at 0° C. for 0.5 hour. On completion, the reaction mixture was quenched with water (0.1 mL), then to the mixture was added NaOH (15%) 0.2 ml. Next, DCM (3 mL) was added, then the mixture was filtered and concentrated in vacuo to give the title compound (50.0 mg, 88% yield) as yellow solid. LC-MS (ESI$^+$) m/z 455.2 (M+H)$^+$.

Step 6—4-[4-[4-(Isopropylamino)-2-thiazol-5-yl-thieno[2,3-b]pyridin-5-yl]triazol-1-yl]cyclohexanecarbaldehyde To a mixture of [4-[4-[4-(isopropylamino)-2-thiazol-5-yl-thieno[2,3-b]pyridin-5-yl]triazol-1-yl]cyclohexyl]methanol (50.0 mg, 109 umol) in DCM (1 mL) was added DMP (60.6 mg, 142 umol). The reaction mixture was then stirred at 25° C. for 1 hour. On completion, the reaction mixture was quenched with Na$_2$S$_2$O$_3$ (8 mL) and saturated NaHCO$_3$(8 mL) at 25° C., then stirred for 20 minutes. The mixture was then extracted with DCM (2×20 mL) and the organic layers were separated and concentrated in vacuo to give the title compound (45.0 mg, 90% yield) as yellow solid. LC-MS (ESI$^+$) m/z 453.1 (M+H)$^+$.

Benzyl 4-[(3-bromo-1-bicyclo[1.1.1]pentanyl)methoxy] piperidine-1-carboxylate (Intermediate CGJ)

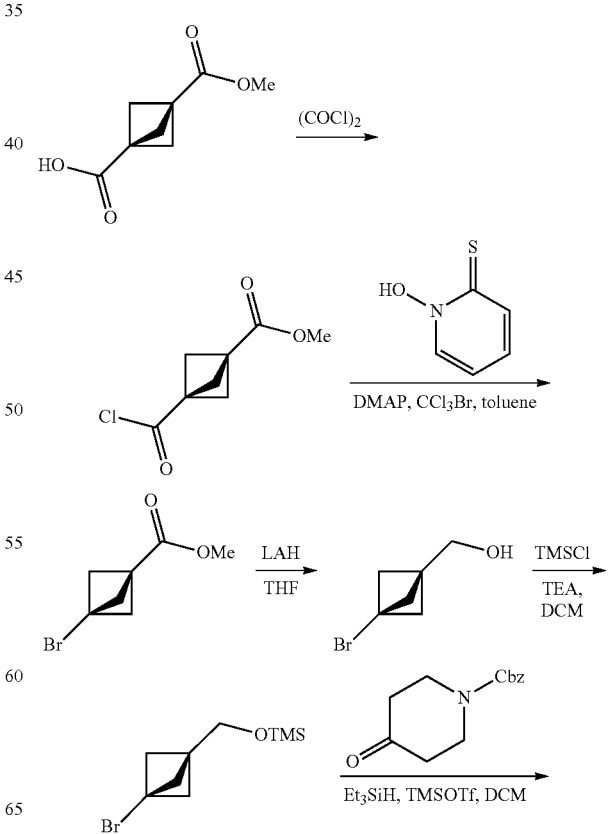

-continued

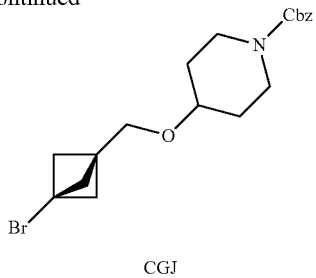

CGJ

Step 1—Methyl 3-chlorocarbonylbicyclo[1.1.1]pentane-1-carboxylate

To a solution of 3-methoxycarbonylbicyclo[1.1.1]pentane-1-carboxylic acid (14.0 g, 82.2 mmol, CAS #83249-10-9) was dissolved in (COCl)$_2$ (40 mL). The mixture was then stirred at 70° C. for 2 hrs. On completion, the reaction mixture was concentrated under reduced pressure to give the title compound (15.5 g, 99% yield) as white solid.

Step 2—Methyl 3-bromobicyclo[1.1.1]pentane-1-carboxylate

A mixture of sodium; 1-oxidopyridin-1-ium-2-thiolate (13.4 g, 90.4 mmol, CAS #3811-73-2), methyl 3-chlorocarbonylbicyclo[1.1.1]pentane-1-carboxylate (15.5 g, 82.1 mmol), DMAP (502 mg, 4.11 mmol) and bromo(trichloro)methane (81.4 g, 410 mmol) in toluene (150 mL) was degassed and purged with N$_2$ three times. Then the mixture was stirred at 110° C. for 2 hrs under N$_2$ atmosphere and 200 W mercury lamp. On completion, the mixture was filtered, the organic phase was diluted with H$_2$O (300 mL) and extracted with EA (200 mL×3). The combined organic layers were, dried over Na$_2$SO$_4$, filtered and concentrated under reduced pressure to give a residue. The residue was purified by column chromatography (SiO$_2$, Petroleum ether/Ethyl acetate=50/1 to 20/1) to give the title compound (6.80 g, 40% yield) as colorless oil.

Step 3—(3-Bromo-1-bicyclo[1.1.1]pentanyl)methanol

To a solution of methyl 3-bromobicyclo[1.1.1]pentane-1-carboxylate (5.80 g, 28.2 mmol) in THF (40 mL) was added LiAlH$_4$ (1.07 g, 28.2 mmol). The mixture was then stirred at 0° C. for 1 hr. On completion, the reaction mixture was quenched with H$_2$O (6 mL) at 0° C., and then 10% NaOH (10 mL) was added at 0° C. Then the organic layer was dried over Na$_2$SO$_4$, filtered and concentrated under reduced pressure to give the title compound (4.00 g, 79% yield) as yellow oil.

Step 4—(3-Bromo-1-bicyclo[1.1.1]pentanyl)methoxy-trimethyl-silane

To a solution of (3-bromo-1-bicyclo[1.1.1]pentanyl) methanol (2.30 g, 12.9 mmol) in THF (20 mL) was added TEA (3.16 g, 31.1 mmol, 4.34 mL), then TMSCl (2.82 g, 25.9 mmol, 3.30 mL) was added at 0° C. dropwise. The reaction mixture was then stirred at 25° C. for 12 hrs. On completion, the reaction mixture was diluted with H$_2$O (30 mL) and extracted with EA 60 mL (2×30 mL). The combined organic layers were dried over Na$_2$SO$_4$, filtered and the filtrate was concentrated under reduced pressure to give the title compound (2.6 g, 80% yield) as yellow oil. $^1$H NMR (400 MHz, CDCl$_3$) δ 3.64 (s, 2H), 2.16 (s, 6H), 0.10 (s, 9H).

Step 5—Benzyl 4-[(3-bromo-1-bicyclo[1.1.1]pentanyl)methoxy]piperidine-1-carboxylate To a solution of (3-bromo-1-bicyclo[1.1.1]pentanyl) methoxy-trimethyl-silane (2.60 g, 10.4 mmol) and benzyl 4-oxopiperidine-1-carboxylate (2.43 g, 10.4 mmol, 2.08 mL, CAS #19099-93-5) in DCM (20 mL) was added Et$_3$SiH (1.33 g, 11.4 mmol, 1.83 mL) and TMSOTf (1.16 g, 5.22 mmol, 942 uL) at −60° C. Then the reaction mixture was stirred at 0° C. for 1 hr. On completion, the reaction mixture was diluted with H$_2$O (30 mL) and extracted with DCM (2×30 mL). The combined organic layers were dried over Na$_2$SO$_4$, filtered and the filtrate was concentrated under reduced pressure to give a residue. The residue was purified by reverse phase (0.1% FA condition) to give the title compound (1.75 g, 42% yield) as a white solid. $^1$H NMR (400 MHz, CDCl$_3$) δ 7.40-7.29 (m, 5H), 5.13 (s, 2H), 3.80-3.72 (m, 2H), 3.51 (s, 2H), 3.48-3.40 (m, 1H), 3.29-3.19 (m, 2H), 2.19 (s, 6H), 1.83-1.72 (m, 2H), 1.60-1.46 (m, 2H); LC-MS (ESI+) m/z 396.0 (M+H)$^+$.

3-[1-(2,6-Dioxo-3-piperidyl)-3-methyl-2-oxo-benzimidazol-4-yl]bicyclo[1.1.1]pentane-1-carbaldehyde (Intermediate CGL)

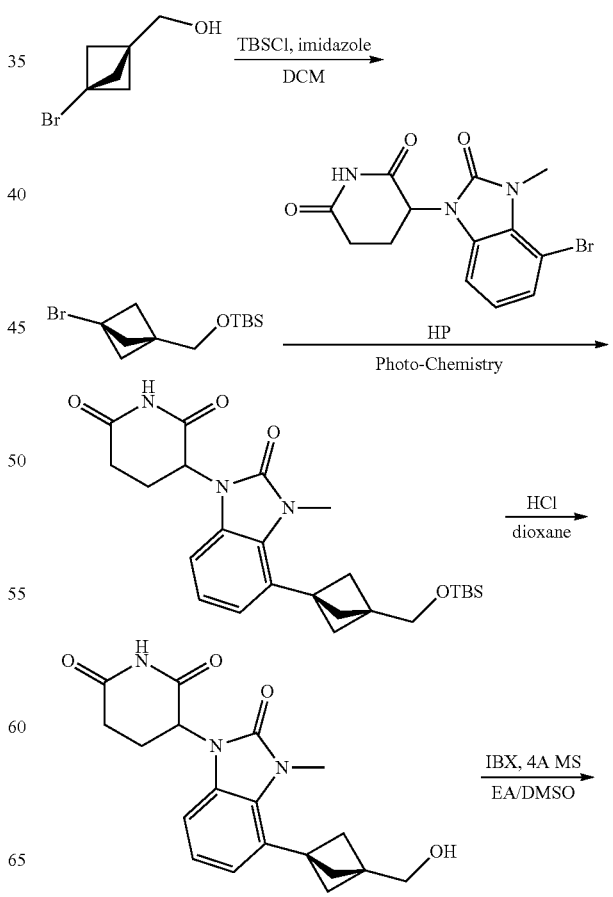

-continued

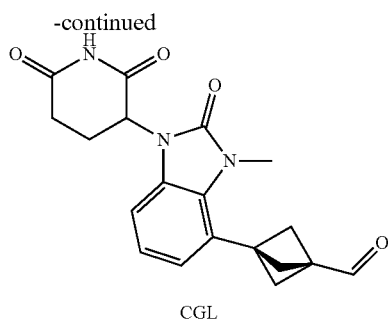

CGL

Step 1—(3-Bromo-1-bicyclo[1.1.1]pentanyl) methoxy-tert-butyl-dimethyl-silane To a solution of (3-bromo-1-bicyclo[1.1.1]pentanyl) methanol (2.50 g, 14.1 mmol, synthesized via Steps 1-2 of Intermediate CGJ) in DCM (30 mL) was added tert-butyl-chloro-dimethyl-silane (3.19 g, 21.1 mmol) and imidazole (1.92 g, 28.2 mmol). The mixture was stirred at 25° C. for 3 hrs. On completion, the reaction mixture was quenched with NH$_4$Cl saturated solution (60 mL) at 25° C., and then extracted with DCM 150 mL (50 mL×3). The combined organic layers were dried over Na$_2$SO$_4$, filtered and concentrated under reduced pressure to give a residue. The residue was purified by column chromatography (SiO$_2$, Petroleum ether) to give the title compound (1.60 g, 38% yield) as colorless oil. $^1$H NMR (400 MHz, CDCl$_3$) δ 3.66 (s, 2H), 2.15 (s, 6H), 0.90-0.88 (m, 9H), 0.05-0.02 (m, 6H).

Step 2—3-[4-[3-[[tert-butyl(dimethyl)silyl]oxymethyl]-1-bicyclo[1.1.1]pentanyl]-3-methyl-2-oxo-benzimidazol-1-yl]piperidine-2,6-dione To a 40 mL vial equipped with a stir bar was added (3-bromo-1-bicyclo[1.1.1]pentanyl) methoxy-tert-butyl-dimethyl-silane (1.23 g, 4.23 mmol), 3-(4-bromo-3-methyl-2-oxo-benzimidazol-1-yl)piperidine-2,6-dione (1.10 g, 3.25 mmol, Intermediate HP), Ir[dF(CF$_3$)ppy]$_2$(dtbpy)(PF$_6$) (36.4 mg, 32.5 umol), NiCl$_2$.dtbbpy (19.4 mg, 48.7 umol), TTMSS (808 mg, 3.25 mmol), and 2,6-lutine (697 mg, 6.51 mmol) in DME (35 mL). The vial was sealed and placed under nitrogen was added. The reaction was stirred and irradiated with a 10 W blue LED lamp (3 cm away), with cooling water to keep the reaction temperature at 25° C. for 14 hrs. On completion, the mixture was filtered and concentrated under reduced pressure to give a residue. The residue was purified by prep-HPLC purification (column: Phenomenex Luna C18 200*40 mm*10 um; mobile phase: [water(FA)-ACN]; B %: 63%-93%, 10 min) to give the title compound (150 mg, 9% yield) as light yellow solid. LC-MS (ESI$^+$) m/z 470.1 (M+H)$^+$.

Step 3—3-[4-[3-(Hydroxymethyl)-1-bicyclo[1.1.1] pentanyl]-3-methyl-2-oxo-benzimidazol-1-yl]piperidine-2,6-dione 3-[4-[3-[[tert-butyl(dimethyl)silyl]oxymethyl]-1-bicyclo [1.1.1]pentanyl]-3-methyl-2-oxo-benzimidazol-1-yl]piperidine-2,6-dione (95.0 mg, 202 umol) was dissolved in HCl/dioxane (3 mL). The mixture was then stirred at 25° C. for 1 hr. On completion, the reaction mixture was concentrated under reduced pressure to give the title compound (70.0 mg, 97% yield) as brown solid. LC-MS (ESI) m/z 355.9 (M+H)$^+$.

Step 4—3-[1-(2,6-Dioxo-3-piperidyl)-3-methyl-2-oxo-benzimidazol-4-yl]bicyclo[1.1.1]pentane-1-carbaldehyde To a solution of 3-[4-[3-(hydroxymethyl)-1-bicyclo [1.1.1] pentanyl]-3-methyl-2-oxo-benzimidazol-1-yl]piperidine-2,6-dione (70.0 mg, 196 umol) in EA (2 mL) and DMSO (0.3 mL) was added IBX (359 mg, 590 umol, 46% solution) and 4 Å molecular sieves (70.0 mg, 196 umol). The mixture was then stirred at 50° C. for 3 hrs. On completion, the reaction mixture was quenched with Na$_2$S$_2$O$_3$ (20 mL) and NaHCO$_3$ (20 mL) at 25° C., and then extracted with EA (20 mL×3). The combined organic layers were concentrated under reduced pressure to give a residue to give the title compound (60.0 mg, 86% yield) as light yellow solid. LC-MS (ESI$^+$) m/z 372.1 (M+H$_2$O)$^+$.

3-[3-Methyl-2-oxo-4-[3-(piperazin-1-ylmethyl)-1-bicyclo[1.1.1] pentanyl]benzimidazol-1-yl] piperidine-2,6-dione (Intermediate CGM)

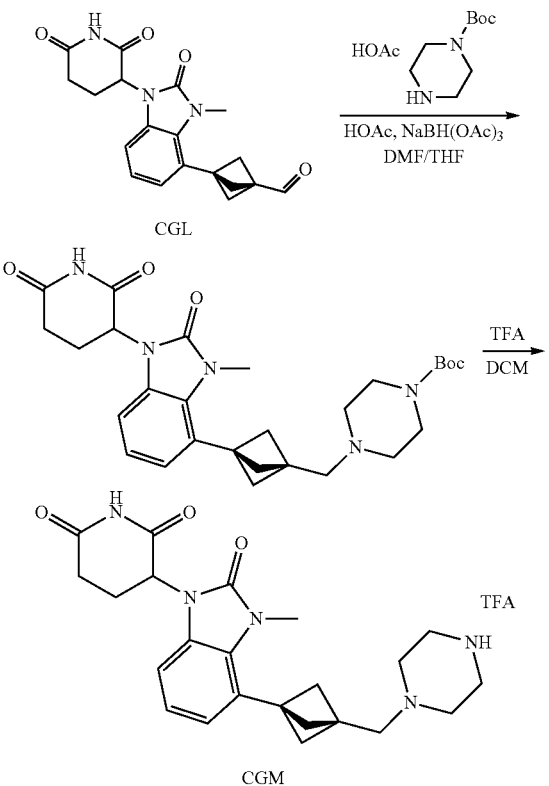

Step 1—Tert-butyl 4-[[3-[1-(2,6-dioxo-3-piperidyl)-3-methyl-2-oxo-benzimidazol-4-yl]-1-bicyclo[1.1.1] pentanyl]methyl]piperazine-1-carboxylate To a solution of tert-butyl piperazine-1-carboxylate (209 mg, 848 umol, HOAc salt, CAS #143238-38-4) in DMF (1.5 mL) was added TEA (34.3 mg, 339 umol) at 25° C. until the pH stabilized at 8. The mixture was stirred at 25° C. for 0.5 hr, then AcOH (20.3 mg, 339 umol) was added at 25° C. to solution until pH stabilized at 5~6. The mixture was then cooled to −15° C. and 3-[1-(2,6-dioxo-3-piperidyl)-3-methyl-2-oxo-benzimidazol-4-yl]bicyclo[1.1.1]pentane-1-carbaldehyde (60.0 mg, 169 umol, Intermediate CGL) was added to the mixture which was then stirred for 0.5 hr. Next, NaBH(OAc)₃ (71.9 mg, 339 umol) was added one portion and the resulting reaction mixture was stirred at −15° C. for 1 hr. On completion, the reaction was quenched with H₂O (0.1 mL) at −15° C., and then filtered and concentrated under reduced pressure to give a residue. The residue was purified by prep-HPLC purification (column: Phenomenex Luna C18 150*25 mm*10 um; mobile phase: [water(HCl)-ACN]; B %: 13%-43%, 10 min) to give the title compound (10.0 mg, 11% yield) as yellow solid. LC-MS (ESI⁺) m/z 524.4 (M+H)⁺.

Step 2—3-[3-Methyl-2-oxo-4-[3-(piperazin-1-ylmethyl)-1-bicyclo[1.1.1]pentanyl]benzimidazol-1-yl]piperidine-2,6-dione To a solution of tert-butyl 4-[[3-[1-(2,6-dioxo-3-piperidyl)-3-methyl-2-oxo-benzimidazol-4-yl]-1-bicyclo[1.1.1]pentanyl]methyl]piperazine-1-carboxylate (10.0 mg, 19.1 umol) in DCM (1 mL) was added TFA (10.8 mg, 95.4 umol). The mixture was stirred at 25° C. for 1 hr. On completion, the mixture was concentrated under reduced pressure to give the title compound (10.0 mg, 97% yield, TFA) as yellow solid. LC-MS (ESI⁺) m/z 424.4 (M+H)⁺.

3-(4-bromo-3-cyclopropyl-2-oxo-benzimidazol-1-yl)piperidine-2,6-dione (Intermediate CGN)

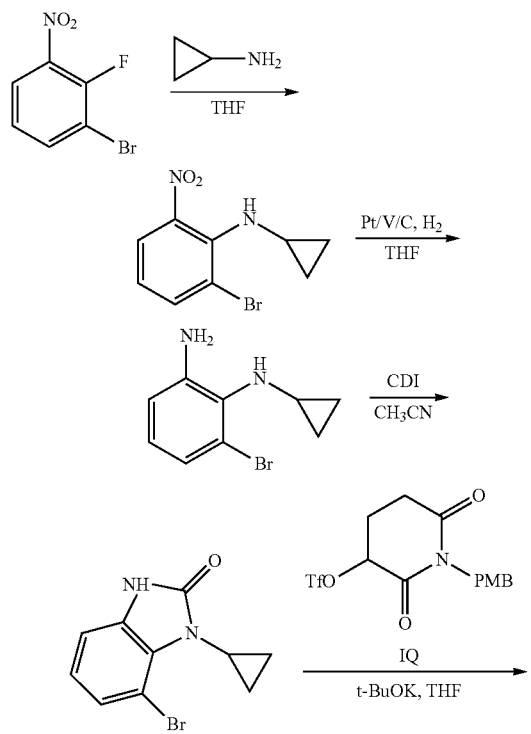

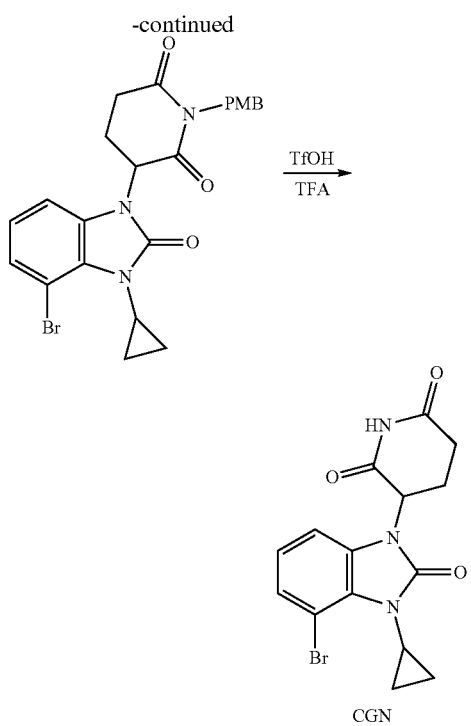

Step 1—2-Bromo-N-cyclopropyl-6-nitro-aniline

To a solution of 1-bromo-2-fluoro-3-nitro-benzene (5 g, 22.7 mmol, CAS #58534-94-4) in THF (50 mL) was added cyclopropanamine (3.89 g, 68.1 mmol) at 0° C. under N₂. The reaction was then stirred at 25° C. for 16 hrs. On completion, the mixture was quenched with H₂O (100 mL), diluted with EA (100 mL), and extracted with EA (3×100 mL). The combined organic layer was washed with brine (3×100 mL), filtered and concentrated in vacuo to give the title compound (5.8 g, 99% yield) as orange oil. ¹H NMR (400 MHz, DMSO-d₆) δ 7.77-7.70 (m, 2H), 6.72 (t, J=8.0 Hz, 1H), 6.42 (s, 1H), 2.61-2.54 (m, 1H), 0.65-0.56 (m, 2H), 0.41-0.35 (m, 2H).

Step 2—3-Bromo-N2-cyclopropyl-benzene-1,2-diamine

To a solution of 2-bromo-N-cyclopropyl-6-nitro-aniline (6.4 g, 24.8 mmol) in THF (90 mL) was added Pt/V/C (4.5 g, 17.2 mmol) under N₂. The suspension was degassed in vacuo and purged with H₂ three times. The mixture was then stirred under H₂ (15 psi) at 25° C. for 16 hours. On completion, the mixture was filtered and concentrated in vacuo to give the title compound (5.5 g, 97% yield) as brown oil. ¹H NMR (400 MHz, DMSO-d₆) δ 6.74-6.70 (m, 1H), 6.68-6.60 (m, 2H), 5.60-5.00 (m, 2H), 3.52-3.19 (m, 1H), 2.72-2.62 (m, 1H), 0.53-0.49 (m, 2H), 0.48-0.43 (m, 2H). LC-MS (ESI⁺) m/z 227.1 (M+H)⁺.

Step 3—4-Bromo-3-cyclopropyl-1H-benzimidazol-2-one

To a solution of 3-bromo-N2-cyclopropyl-benzene-1,2-diamine (5.5 g, 24.2 mmol) in ACN (130 mL) was added CDI (7.85 g, 48.4 mmol). The mixture was then stirred at 80° C. for 3 hrs. On completion, the mixture was concentrated in vacuo. The crude product was triturated with H₂O (50 mL) for 30 min, filtered and the cake was dried in vacuo to give the title compound (5.4 g, 88% yield) as yellow solid. ¹H NMR (400 MHz, DMSO-d₆) δ 11.00 (s, 1H), 7.16 (dd, J=1.2, 8.0 Hz, 1H), 6.94-6.88 (m, 2H), 3.06-2.97 (m, 1H), 1.08-1.04 (m, 4H).

Step 4—3-(4-Bromo-3-cyclopropyl-2-oxo-benzimidazol-1-yl)-1-[(4-methoxyphenyl)methyl]piperidine-2,6-dione To a solution of 4-bromo-3-cyclopropyl-1H-benzimidazol-2-one (800 mg, 3.16 mmol) in THF (10 mL) was stirred at −10° C., then the t-BuOK (638 mg, 5.69 mmol) was added in above solution was stirred at −10° C. for 1.5 hrs. Then the solution of [1[(4-methoxyphenyl)methyl]-2,6-dioxo-3-piperidyl]trifluoromethanesulfonate (1.45 g, 3.79 mmol, Intermediate IQ) in THF (15 mL) was dropwise into the above solution. The mixture was stirred at −10° C. for 2.5 hrs. On completion, the mixture was quenched with NH₄Cl (10 mL), diluted with H₂O (30 mL), and extracted with EA (2×50 mL). The combined organic layer was then washed with brine (2×50 mL), dried with anhydrous Na₂SO₄, filtered and concentrated in vacuo. The mixture was purified by reversed phase (0.1% FA) to give the title compound (1 g, 65% yield) as green solid. ¹H NMR (400 MHz, DMSO-d₆) δ 7.25 (d, J=8.4 Hz, 1H), 7.20 (d, J=8.4 Hz, 2H), 7.01 (s, 1H), 6.96-6.90 (m, 1H), 6.88-6.83 (m, 2H), 5.51 (dd, J=5.6, 13.0 Hz, 1H), 4.78 (q, J=14.4 Hz, 2H), 3.72 (s, 3H), 3.14-3.08 (m, 1H), 3.06-2.97 (m, 1H), 2.86-2.77 (m, 1H), 2.76-2.66 (m, 1H), 2.10-1.99 (m, 1H), 1.15-1.06 (m, 4H). LC-MS (ESI⁺) m/z 484.1 (M+H)⁺.

Step 5—3-(4-Bromo-3-cyclopropyl-2-oxo-benzimidazol-1-yl)piperidine-2,6-dione

To a solution of 3-(4-bromo-3-cyclopropyl-2-oxo-benzimidazol-1-yl)-1-[(4-methoxyphenyl)methyl]piperidine-2,6-dione (400 mg, 825 umol) in TFA (5 mL) was added TfOH (100 uL). The mixture was then stirred at 70° C. for 5.5 hrs. On completion, the mixture was diluted with ACN (5 mL) and adjusted to pH=6-7 with TEA, then the mixture was concentrated in vacuo. The crude product was purified by reversed phase (0.1% FA) to give the title compound (106 mg, 35% yield) as white solid. ¹H NMR (400 MHz, DMSO-d₆) δ 11.10 (s, 1H), 7.26 (dd, J=1.2, 8.4 Hz, 1H), 7.12 (d, J=7.6 Hz, 1H), 7.01-6.95 (m, 1H), 5.35 (dd, J=5.6, 12.8 Hz, 1H), 3.14-3.07 (m, 1H), 2.92-2.81 (m, 1H), 2.74-2.60 (m, 2H), 2.05-1.96 (m, 1H), 1.15-1.05 (m, 4H). LC-MS (ESI⁺) m/z 366.0 (M+H)⁺.

Tert-butyl 4-(3-bromocyclobutoxy)piperidine-1-carboxylate (Intermediate CGS)

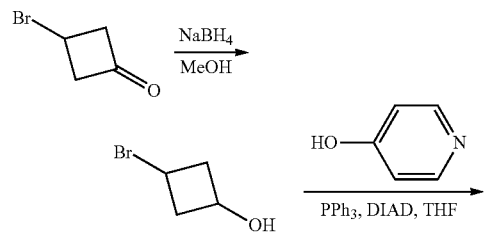

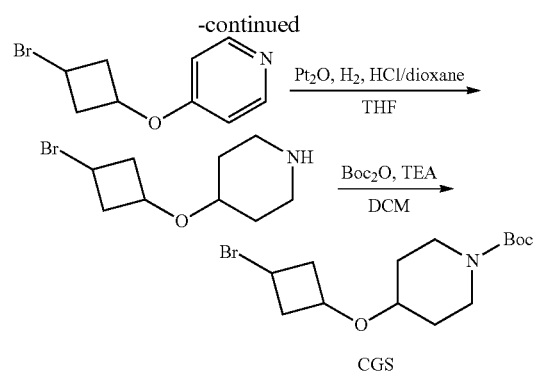

Step 1—3-bromocyclobutanol

To a solution of 3-bromocyclobutanone (3.00 g, 20.1 mmol, CAS #23761-24-2) in MeOH (10 mL) was added NaBH₄ (1.95 g, 51.5 mmol) at 0° C. The reaction was then stirred at 25° C. for 2 hrs. On completion, the reaction was quenched with NH₄Cl saturated solution (7 mL). The mixture was diluted with EA (200 mL). The organic layer was washed with water (200 mL×3) and concentrated in vacuo to give title compound (3 g, 98% yield) as brown oil. ¹H NMR (400 MHz, CHCl₃) δ 4.11-4.02 (m, J=7.2 Hz, 1H), 3.92-3.83 (m, 1H), 3.08 (d, J=8.4 Hz, 1H), 3.04-2.94 (m, 2H), 2.44-2.34 (m, 2H).

Step 2—4-(3-bromocyclobutoxy)pyridine

To a solution of 3-bromocyclobutanol (2.9 g, 19.2 mmol) and pyridin-4-ol (1.83 g, 19.1 mmol) in THF (10 mL) was added PPh₃ (7.56 g, 28.8 mmol) at 0° C. Then, DIAD (5.83 g, 28.8 mmol) was added into the above mixture at 0° C. Then the mixture was stirred at 50° C. for 16 hrs. On completion, the reaction was filtered and the filtrate was concentrated in vacuo. The residue was purified by column chromatography (SiO₂, Petroleum ether/Ethyl acetate=2/1 to 1/1) to give title compound (2 g, 45% yield) as colorless oil. ¹H NMR (400 MHz, CHCl₃) δ 8.47 (d, J=6.0 Hz, 2H), 6.80 (d, J=6.4 Hz, 2H), 5.22-5.12 (m, 1H), 5.05-4.90 (m, J=6.3, 12.5 Hz, 1H), 2.97-2.94 (m, 2H), 2.91-2.88 (m, 2H).

Step 3—4-(3-bromocyclobutoxy)piperidine

To a solution of 4-(3-bromocyclobutoxy)pyridine (500 mg, 2.19 mmol) and HCl/dioxane (4 M, 500 uL) in THF (120 mL) was added PtO₂ (300 mg, 1.32 mmol) under N₂. The suspension was degassed under vacuo and purged with H₂ several times. The mixture was stirred under H₂ (50 psi) at 25° C. for 16 hours. On completion, the reaction was filtered and the filtrate was concentrated in vacuo to give title compound (350 mg, 68% yield) as colorless oil. ¹H NMR (400 MHz, DMSO-d₆) δ 5.30-5.13 (m, 1H), 4.87-4.69 (m, 2H), 3.19-3.09 (m, 1H), 3.05-2.98 (m, 1H), 2.97-2.82 (m, 6H), 2.69-2.56 (m, 3H), 2.00-1.84 (m, 1H), 1.65-1.53 (m, 1H).

Step 4—Tert-butyl 4-(3-bromocyclobutoxy)piperidine-1-carboxylate

A mixture of 4-(3-bromocyclobutoxy)piperidine (300 mg, 1.28 mmol), TEA (259 mg, 2.56 mmol) and Boc₂O (559 mg, 2.56 mmol) in DCM (2 mL) was stirred at 25° C. for 2 hrs.

On completion, the reaction was diluted with DCM (50 mL). The organic layer was washed with water (50 mL×3) and concentrated in vacuo. The residue was purified by column chromatography (SiO₂, Petroleum ether/Ethyl acetate=20/1 to 10/1, Pl:Rf=0.2) to give title compound (250 mg, 58% yield) as yellow oil. LC-MS (ESI⁺) m/z 278.1 (M−56+H)⁺.

1-[8-[3-(4-Piperidyloxy)cyclobutyl]-4-isoquinolyl] hexahydropyrimidine-2,4-dione (Intermediate CGT)

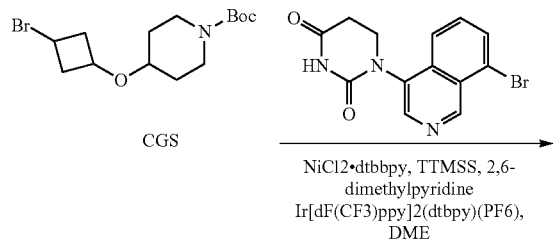

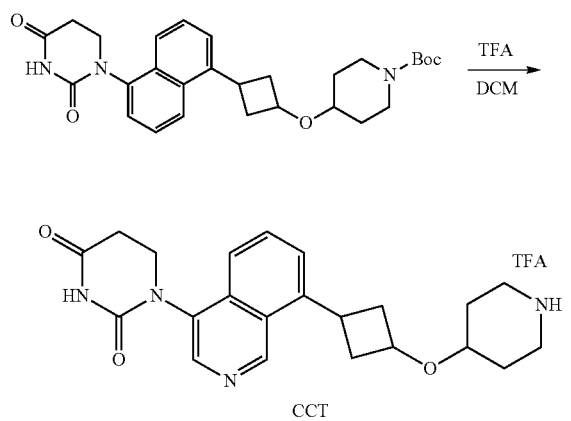

Step 1—Tert-butyl 4-[3-[4-(2,4-dioxohexahydropyrimidin-1-yl)-8-isoquinolyl] cyclobutoxy]piperidine-1-carboxylate To a solution of 1-(8-bromo-4-isoquinolyl)hexahydropyrimidine-2,4-dione (368 mg, 1.15 mmol, Intermediate CCT) and tert-butyl 4-(3-bromocyclobutoxy)piperidine-1-carboxylate (500 mg, 1.50 mmol, Intermediate CGS) in DME (3 mL) were added Ir[dF(CF₃)ppy]2(dtbpy)(PF6) (25.8 mg, 23.0 umol), NiCl2.dtbbpy (9.16 mg, 23.0 umol), TTMSS (286 mg, 1.15 mmol) and 2,6-dimethylpyridine (246 mg, 2.30 mmol). The vial was sealed and placed under nitrogen, then the reaction was stirred and irradiated with a 10 W blue LED lamp (3 cm away), with cooling water to keep the reaction temperature at 25° C. for 1 hr. On completion, the reaction mixture was filtered and concentrated in vacuo to give a residue. The residue was purified by reverse phase (FA condition) to give the title compound (200 mg, 35% yield) as white solid. ¹H NMR (400 MHz, DMSO-d₆) δ 10.6 (s, 1H), 9.45-9.30 (m, 1H), 8.58 (s, 1H), 7.90-7.84 (m, 1H), 7.82-7.76 (m, 1H), 7.75-7.55 (m, 1H), 4.35-4.18 (m, 1H), 3.98-3.88 (m, 1H), 3.86-3.75 (m, 1H), 3.74-3.62 (m, 3H), 3.58-3.52 (m, 1H), 3.51-3.48 (m, 1H), 3.05-2.87 (m, 4H), 2.80-2.70 (m, 1H), 2.66 (s, 1H), 2.54 (s, 2H), 2.18-2.03 (m, 1H), 1.85-1.71 (m, 2H), 1.39 (s, 9H); LC-MS (ESI⁺) m/z 495.1 (M+H)⁺.

Step 2—1-[8-[3-(4-Piperidyloxy)cyclobutyl]-4-isoquinolyl]hexahydropyrimidine-2,4-dione To a solution of tert-butyl 4-[3[4-(2,4-dioxohexahydropyrimidin-1-yl)-8-isoquinolyl]cyclobutoxy]piperidine-1-carboxylate (50 mg, 101 umol) in DCM (1 mL) was added TFA (308 mg, 2.70 mmol). The mixture was then stirred at 25° C. for 1 hr. On completion, the reaction mixture was concentrated in vacuo to give the title compound (50 mg, 97% yield, TFA) as a red oil. LC-MS (ESI⁺) m/z 395.0 (M+H)⁺.

N-(2-((1r,3r)-3-formylcyclobutyl)-5-methoxybenzo [d]thiazol-6-yl)-6-(trifluoromethyl)picolinamide (Intermediate CGY)

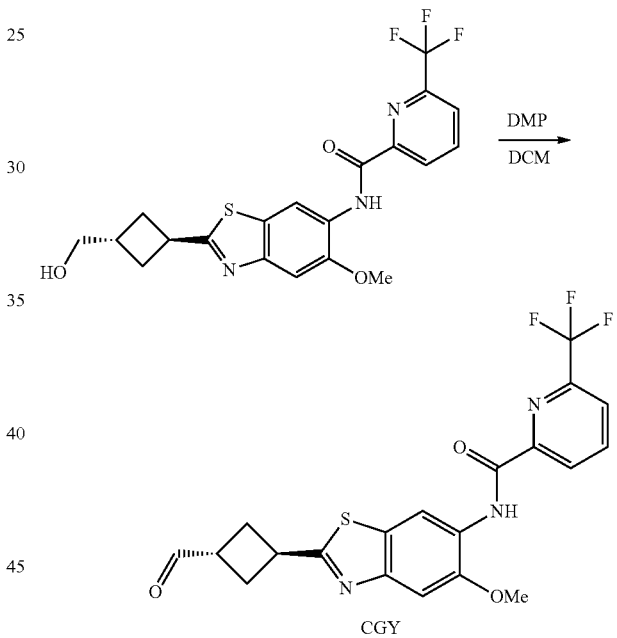

To a solution of N-[2-[3-(hydroxymethyl)cyclobutyl]-5-methoxy-1,3-benzothiazol-6-yl]-6-(trifluoromethyl)pyridine-2-carboxamide (280 mg, 640 umol, synthesized via Step 1 of Intermediate CAD) in DMF (2 mL) and THF (2 mL) was added DMP (407 mg, 960 umol). The mixture was then stirred at 25° C. for 16 hours. On completion, the reaction mixture was diluted with water (5 mL), then extracted with EA (3×5 ml). The combined organic layers were concentrated in vacuo to give the title compound (250 mg, 89% yield) as a yellow solid. ¹H NMR (400 MHz, CDCl₃) δ 10.64 (s, 1H), 9.87 (d, J=1.2 Hz, 1H), 9.11-8.94 (m, 1H), 8.43 (d, J=8.0 Hz, 1H), 8.07 (t, J=8.0 Hz, 1H), 7.95 (s, 1H), 7.81 (d, J=8.0 Hz, 1H), 7.51-7.45 (m, 1H), 4.05-3.97 (m, 3H), 3.86-3.24 (m, 1H), 2.82 (s, 2H), 2.79-2.72 (m, 1H), 2.71-2.60 (m, 2H).

1239

3-[3-methyl-2-oxo-4-[3-(4-piperidyloxy)cyclobutyl]benzimidazol-1-yl]piperidine-2,6-dione (Intermediate CGZ)

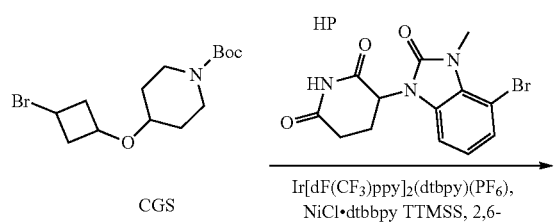

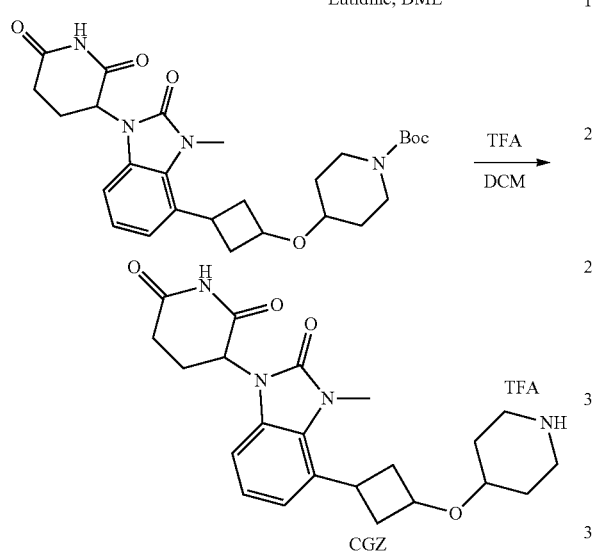

Step 1—Tert-butyl 4-[3-[1-(2,6-dioxo-3-piperidyl)-3-methyl-2-oxo-benzimidazol-4-yl]cyclobutoxy]piperidine-1-carboxylate To an 15 mL vial equipped with a stir bar was added 3-(4-bromo-3-methyl-2-oxo-benzimidazol-1-yl)piperidine-2,6-dione (67.6 mg, 0.2 mmol, Intermediate HP), tert-butyl 4-(3-bromocyclobutoxy)piperidine-1-carboxylate (86.9 mg, 260 umol, Intermediate CGS), Ir[dF(CF$_3$)ppy]$_2$(dtbpy)(PF6) (2.24 mg, 2.00 umol), NiCl2.dtbbpy (1.19 mg, 3.00 umol), TTMSS (49.7 mg, 200 umol) and 2,6-lutidine (42.8 mg, 400 umol) in DME (2 mL). The vial was sealed and placed under nitrogen then the reaction was stirred and irradiated with a 10 W blue LED lamp (3 cm away), with cooling water to keep the reaction temperature at 25° C. for 14 hrs. On completion, the reaction was diluted with EA (100 mL). The organic layer was washed with water (100 mL×3) and concentrated in vacuo. The residue was purified by prep-HPLC (column: Phenomenex luna C18 150*25 mm*10 um; mobile phase: [water (0.225% FA)-ACN]; B %: 36%-66%, 10 min) to give title compound (35.0 mg, 34% yield) as white solid. $^1$H NMR (400 MHz, DMSO-d$_6$) δ 11.08 (s, 1H), 7.16-6.96 (m, 3H), 5.35 (dd, J=5.6, 12.4 Hz, 1H), 4.28-4.05 (m, 1H), 3.71-3.61 (m, 2H), 3.59-3.44 (m, 4H), 3.05-2.83 (m, 3H), 2.75-2.56 (m, 4H), 2.45-2.36 (m, 1H), 2.08-1.93 (m, 2H), 1.82-1.72 (m, 2H), 1.38 (s, 9H), 1.35-1.25 (m, 2H), 0.08-0.02 (m, 1H).

1240

Step 2—3-[3-methyl-2-oxo-4-[3-(4-piperidyloxy)cyclobutyl]benzimidazol-1-yl]piperidine -2,6-dione A mixture of tert-butyl 4-[3-[1-(2,6-dioxo-3-piperidyl)-3-methyl-2-oxo-benzimidazol-4-yl]cyclobutoxy]piperidine-1-carboxylate (20.0 mg, 39.0 umol) and TFA (154 mg, 1.35 mmol) in DCM (0.5 mL) was stirred at 25° C. for 1 hr. On completion, the reaction was concentrated in vacuo to give title compound (20 mg, 97% yield, TFA) as yellow oil. LC-MS (ESI$^+$) m/z 413.2 (M+H)$^+$.

Tert-butyl (4R)-4-[1-(2,6-dioxo-3-piperidyl)-3-methyl-2-oxo-benzimidazol-4-yl]-2,2-dimethyl-piperidine-1-carboxylate (Intermediate CHA)

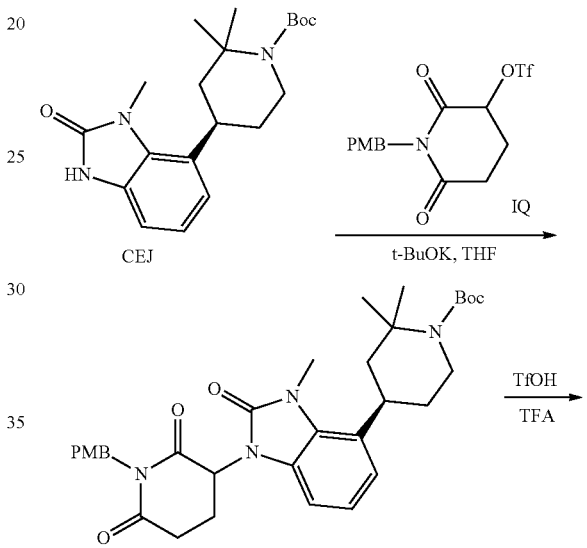

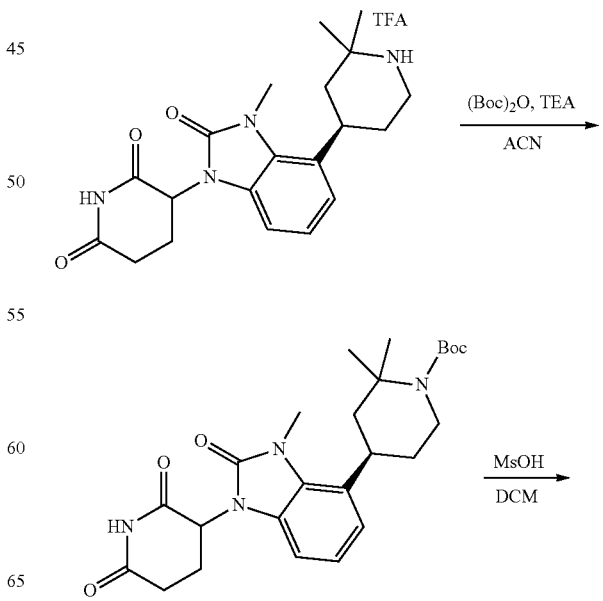

-continued

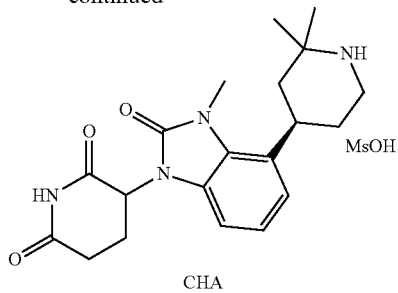

CHA

Step 1—Tert-butyl (4R)-2,2-dimethyl-4-(3-methyl-2-oxo-1H-benzimidazol-4-yl)piperidine-1-carboxylate To a solution of tert-butyl (4R)-2,2-dimethyl-4-[3-methyl-2-oxo-1-(2-trimethylsilylethoxymethyl) benzimidazol-4-yl]piperidine-1-carboxylate (240 mg, 490 umol, Intermediate CEJ) in THF (1 mL) was added TBAF (1 M, 2.45 mL), the reaction mixture was then stirred at 70° C. for 12 hrs. On completion, the reaction mixture was diluted with H$_2$O (50 mL), then extracted with EA (2×20 mL). The combined organic layers were washed with brine (30 mL), dried over Na$_2$SO$_4$, filtered and concentrated in vacuo to give the title compound (170 mg, 96.5% yield) as a white solid. $^1$H NMR (400 MHz, DMSO-d$_6$) δ 10.86 (s, 1H), 6.97-6.89 (m, 2H), 6.83-6.81 (m, 1H), 3.89-3.86 (m, 1H), 3.62-3.48 (m, 4H), 3.21-3.15 (m, 1H), 1.93-1.82 (m, 1H), 1.77-1.63 (m, 3H), 1.49 (s, 3H), 1.41 (s, 9H), 1.36 (s, 3H). LC-MS (ESI$^+$) m/z 303.9 (M−56+H)$^+$

Step 2—Tert-butyl (4R)-4-[1-[1-[(4-methoxyphenyl)methyl]-2,6-dioxo-3-piperidyl]-3-methyl-2-oxo-benzimidazol-4-yl]-2,2-dimethyl-piperidine-1-carboxylate To a solution of tert-butyl (4R)-2,2-dimethyl-4-(3-methyl-2-oxo-1H-benzimidazol-4-yl)piperidine-1-carboxylate (170 mg, 472.93 umol) in THF (2 mL) was added tBuOK (79.6 mg, 709 umol) at −10° C. The mixture was stirred for 30 mins, then a solution of [1-[(4-methoxyphenyl)methyl]-2,6-dioxo-3-piperidyl]trifluoromethanesulfonate (234 mg, 614 umol, Intermediate IQ) in THF (2 mL) was added dropwise to the mixture, then the reaction mixture was stirred at −10° C. for 2 hrs. On completion, the reaction mixture was acidified with FA to pH=5-6. Then the mixture was diluted with EA (100 mL), washed with NH$_4$Cl (100 mL) and brine (100 mL). The organic layer was dried over Na$_2$SO$_4$, filtered and concentrated in vacuo to give a residue. The residue was purified by reverse phase (0.1% FA condition) to give the title compound (200 mg, 71% yield) as a white solid. $^1$H NMR (400 MHz, DMSO-d$_6$) δ 7.21 (d, J=8.4 Hz, 2H), 7.03-7.00 (m, 1H), 6.96-6.94 (m, 1H), 6.89-6.82 (m, 3H), 5.53 (dd, J=5.2, 12.8 Hz, 1H), 4.84-4.73 (m, 2H), 3.90-3.86 (m, 1H), 3.72 (s, 3H), 3.62 (s, 3H), 3.26-3.16 (m, 1H), 3.11-2.99 (m, 1H), 2.84-2.68 (m, 2H), 2.08-2.00 (m, 1H), 1.94-1.84 (m, 1H), 1.78-1.65 (m, 4H), 1.49 (s, 3H), 1.42 (s, 9H), 1.37 (s, 3H); LC-MS (ESI$^+$) m/z 591.2 (M+H)$^+$.

Step 3—3-[4-[(4R)-2,2-dimethyl-4-piperidyl]-3-methyl-2-oxo-benzimidazol-1-yl]piperidine-2,6-dione To a solution of tert-butyl (4R)-4-[1-[1-[(4-methoxyphenyl)methyl]-2,6-dioxo-3-piperidyl]-3-methyl-2-oxo-benzimidazol-4-yl]-2,2-dimethyl-piperidine-1-carboxylate (200 mg, 338 umol) in TFA (1.54 g, 13.5 mmol) was added TfOH (340 mg, 2.27 mmol), then the reaction was stirred at 70° C. for 2 hrs. On completion, the reaction mixture was concentrated in vacuo to give the title compound (160 mg, 97% yield) as yellow oil. LC-MS (ESI$^+$) m/z 371.1 (M+H)$^+$.

Step 4—Tert-butyl (4R)-4-[1-(2,6-dioxo-3-piperidyl)-3-methyl-2-oxo-benzimidazol-4-yl]-2,2-dimethyl-piperidine-1-carboxylate To a mixture of 3-[4-[(4R)-2,2-dimethyl-4-piperidyl]-3-methyl-2-oxo-benzimidazol-1-yl]piperidine -2,6-dione (160 mg, 330 umol, TFA) in TEA (100 mg, 990 umol, 137 uL) in ACN (3 mL) was added (Boc)$_2$O (79.2 mg, 363 umol, 83.4 uL), then the reaction was stirred at 25° C. for 16 hrs. On completion the reaction mixture was concentrated in vacuo to give a residue. The residue was purified by reverse phase (0.1% TFA condition) to give the title compound (120 mg, 77% yield) as a white solid. $^1$H NMR (400 MHz, DMSO-d$_6$) δ 11.08 (s, 1H), 7.17-6.85 (m, 3H), 5.37 (dd, J=4.8, 12.0 Hz, 1H), 3.94-3.84 (m, 1H), 3.75-3.47 (m, 4H), 3.25-3.17 (m, 1H), 2.94-2.83 (m, 1H), 2.77-2.59 (m, 3H), 2.04-1.95 (m, 1H), 1.95-1.85 (m, 1H), 1.82-1.65 (m, 3H), 1.49 (s, 3H), 1.42 (s, 8H), 1.37 (s, 3H). LC-MS (ESI$^+$) m/z 471.1 (M+H)$^+$.

Tert-butyl 4-((1s,3s)-3-(1-(2,6-dioxopiperidin-3-yl)-3-methyl-2-oxo-2,3-dihydro-1H-benzo[d]imidazol-4-yl)cyclobutoxy)piperidine-1-carboxylate (Intermediate CIY) and tert-butyl 4-((1r,3r)-3-(1-(2,6-dioxopiperidin-3-yl)-3-methyl-2-oxo-2,3-dihydro-1H-benzo[d]imidazol-4-yl)cyclobutoxy)piperidine-1-carboxylate (Intermediate CIZ)

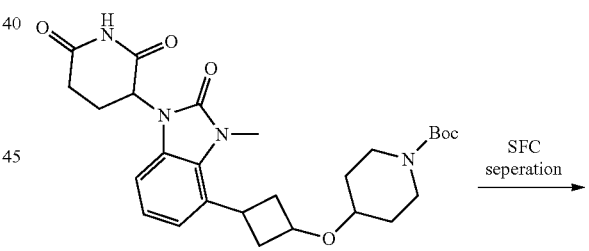

SFC seperation

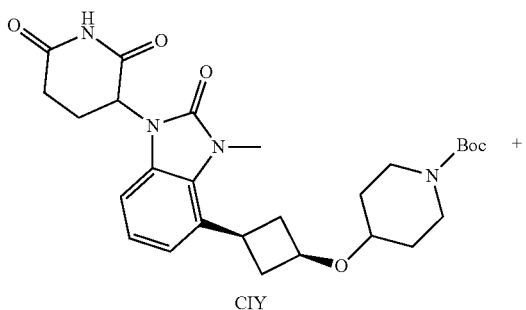

CIY

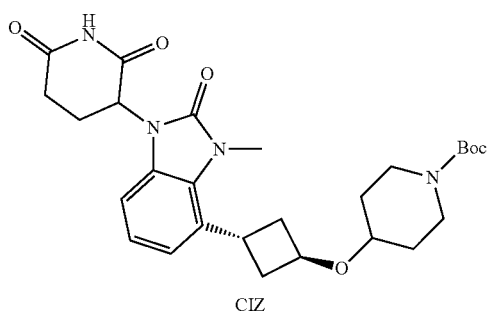

CIZ

The tert-butyl 4-[3-[1-(2,6-dioxo-3-piperidyl)-3-methyl-2-oxo-benzimidazol-4-yl]cyclobutoxy] piperidine-1-carboxylate (50.0 mg, synthesized via Step 1 of Intermediate CGZ) was purified by SFC (column: DAICEL CHIRAL-PAK IC (250 mm*30 mm, 10 um); mobile phase: [Neu-MeOH]; B %: 70%-70%, 5.5; 40 min) (column: DAICEL CHIRALPAK AD (250 mm*30 mm, 10 um); mobile phase: [0.1% NH₃H₂O ETOH]; B %: 50%-50%, 3.4; 40 min) and concentrated in vacuo to give tert-butyl 4-((1 s,3 s)-3-(1-(2,6-dioxopiperidin-3-yl)-3-methyl-2-oxo-2,3-dihydro-1H-benzo[d]imidazol-4-yl)cyclobutoxy)piperidine-1-carboxylate (26.0 mg, 96.5% yield) and tert-butyl 4-((1r,3r)-3-(1-(2,6-dioxopiperidin-3-yl)-3-methyl-2-oxo-2,3-dihydro-1H-benzo[d]imidazol-4-yl)cyclobutoxy)piperidine-1-carboxylate (15.0 mg, 96.5% yield) as yellow solid. LC-MS (ESI⁺) m/z 535.3 (M+Na)⁺. Absolute stereochemistry isomers was assigned arbitrarily.

5-(trifluoromethyl)pyridine-3-carboxylic acid (CAS #131747-40-5) (Intermediate CBV)

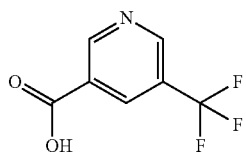

CBV

3-[3-methyl-2-oxo-5-[(3S)-pyrrolidin-3-yl]benzimidazol-1-yl]piperidine-2,6-dione (Intermediate CJA)

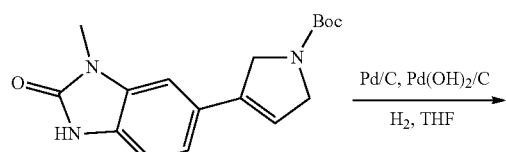

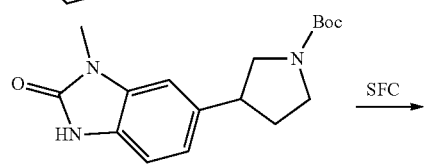

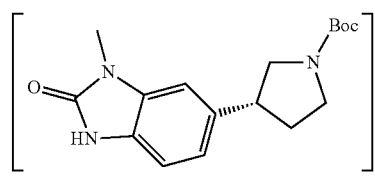

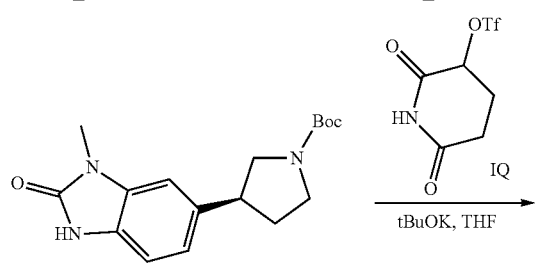

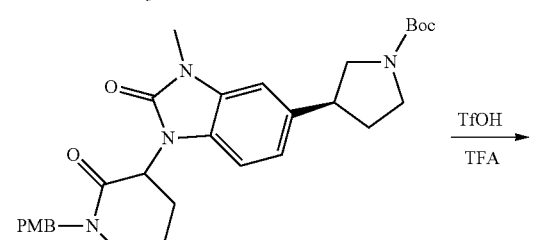

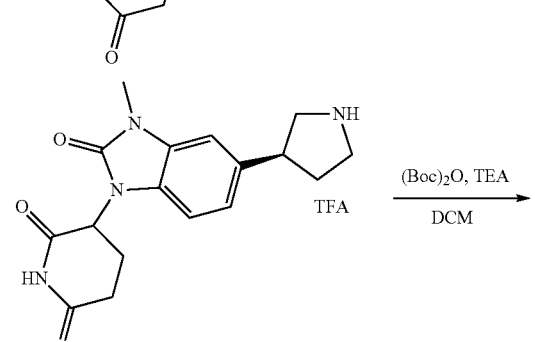

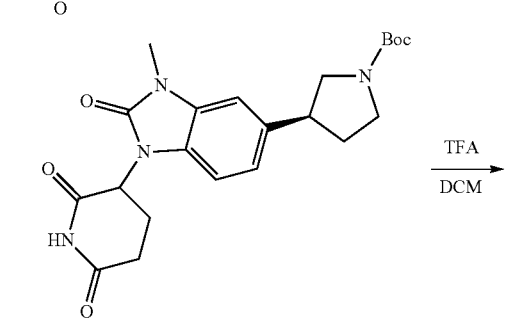

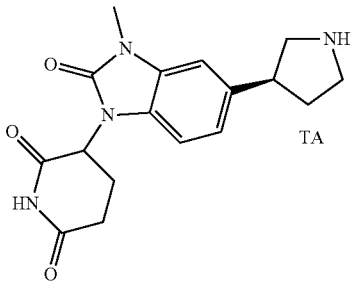

CJA

Step 1—Tert-butyl 3-(3-methyl-2-oxo-1H-benzimidazol-5-yl)pyrrolidine-1-carboxylate A mixture of tert-butyl 3-(3-methyl-2-oxo-1H-benzimidazol-5-yl)-2,5-dihydropyrrole-1-carboxylate (1 g, 3.17 mmol, synthesized via Step 1 of Intermediate CFH), Pd/C (500 mg, 10 wt %) and Pd(OH)$_2$/C (6.00 g, 4.27 mmol) in MeOH (5 mL) was degassed and purged with H$_2$ three times. Then the mixture was stirred at 25° C. for 2 hrs under H$_2$ atmosphere. On completion, the reaction mixture was filtered and concentrated in vacuo to give the title compound (1.0 g, 99% yield) as white solid. $^1$H NMR (400 MHz, DMSO-d$_6$) δ 7.04 (s, 1H), 6.89 (s, 2H), 6.82-6.82 (m, 1H), 3.68 (s, 1H), 3.48 (s, 1H), 3.31 (d, J=4.0 Hz, 1H), 3.26 (s, 3H), 3.20-3.11 (m, 1H), 2.24-1.84 (m, 2H), 1.40 (s, 9H).

Step 2—Tert-butyl (3S)-3-(3-methyl-2-oxo-1H-benzimidazol-5-yl)pyrrolidine-1-carboxylate and tert-butyl (3R)-3-(3-methyl-2-oxo-1H-benzimidazol-5-yl)pyrrolidine-1-carboxylate Tert-butyl 3-(3-methyl-2-oxo-1H-benzimidazol-5-yl)pyrrolidine-1-carboxylate (2 g, 6.30 mmol) was purified by SFC (column: DAICEL CHIRALCEL OJ (250 mm*50 mm, 10 um); mobile phase: [0.1% NH3H2OMEOH]; B %: 30%-30%, 2; 160 min). After SFC purification, the eluent was concentrated or evaporated to remove organic solvents. The residual aqueous solution was lyophilized to tert-butyl (3S)-3-(3-methyl-2-oxo-1H-benzimidazol-5-yl)pyrrolidine-1-carboxylate (1 g, 3.15 mmol, 50% yield) ($^1$H NMR (400 MHz, DMSO-d$_6$) δ 10.73 (s, 1H), 7.05 (s, 1H), 6.89 (s, 2H), 3.68 (t, J=8.8 Hz, 1H), 3.56-3.35 (m, 2H), 3.26 (s, 3H), 3.20-3.12 (m, 1H), 2.16 (dd, J=4.8, 10.0 Hz, 1H), 2.09-1.84 (m, 2H), 1.41 (d, J=6.0 Hz, 9H)) and tert-butyl (3R)-3-(3-methyl-2-oxo-1H-benzimidazol-5-yl)pyrrolidine-1-carboxylate (800 mg, 40% yield).

Step 3—Tert-butyl (3S)-3-[1-[1-[(4-methoxyphenyl)methyl]-2,6-dioxo-3-piperidyl]-3-methyl-2-oxo-benzimidazol-5-yl]pyrrolidine-1-carboxylate To a solution of tert-butyl (3S)-3-(3-methyl-2-oxo-1H-benzimidazol-5-yl)pyrrolidine -1-carboxylate (450 mg, 1.42 mmol) in THF (6 mL) was added t-BuOK (238 mg, 2.13 mmol). Then, to the above mixture was added [1[(4-methoxyphenyl)methyl]-2,6-dioxo-3-piperidyl]trifluoromethanesulfonate (810 mg, 2.13 mmol, Intermediate IQ), then the mixture was stirred at 0° C. for 2 hrs. On completion, the reaction mixture was concentrated in vacuo. The residue was diluted with water (100 mL) and extracted with EA (40 mL×2). The combined organic layer was dried over Na$_2$SO$_4$, filtered and concentrated in vacuo. The residue was purified by prep-HPLC (column: Phenomenex Luna C18 200*40 mm*10 um; mobile phase: [water (FA)-ACN]; B %:47%-77%, 10 min) to give the title compound (600 mg, 77% yield) as a white solid. $^1$H NMR (400 MHz, DMSO-d$_6$) δ 7.23-7.14 (m, 3H), 6.92 (s, 2H), 6.85 (d, J=8.4 Hz, 2H), 5.50 (dd, J=5.6, 12.8 Hz, 1H), 4.87-4.71 (m, 2H), 3.72 (s, 3H), 3.70-3.65 (m, 1H), 3.49 (t, J=8.4 Hz, 1H), 3.42-3.36 (m, 1H), 3.34 (s, 3H), 3.27 (d, J=1.6 Hz, 1H), 3.23-3.15 (m, 1H), 3.12-3.00 (m, 1H), 2.86-2.69 (m, 2H), 2.21-1.93 (m, 3H), 1.41 (d, J=6.0 Hz, 9H).

Step 4—3-[3-methyl-2-oxo-5-[(3S)-pyrrolidin-3-yl]benzimidazol-1-yl]piperidine-2,6-dione To a solution of tert-butyl (3S)-3-[1-[1-[(4-methoxyphenyl)methyl]-2,6-dioxo-3-piperidyl]-3-methyl-2-oxo-benzimidazol-5-yl]pyrrolidine-1-carboxylate (200 mg, 364 umol) in TFA (2 mL) was added TfOH (711 mg, 4.74 mmol). The mixture was then stirred at 25° C. for 3 hrs. On completion, the reaction mixture was concentrated under reduced pressure to give the title compound (118 mg, 99% yield) as black brown oil. LC-MS (ESI$^+$) m/z 329.2 (M+H)$^+$.

Step 5—Tert-butyl (3S)-3-[1-(2,6-dioxo-3-piperidyl)-3-methyl-2-oxo-benzimidazol-5-yl]pyrrolidine -1-carboxylate To a solution of 3-[3-methyl-2-oxo-5-[(3S)-pyrrolidin-3-yl]benzimidazol-1-yl]piperidine-2,6-dione (110 mg, 334 umol) in DCM (5 mL) was added TEA (101 mg, 1.00 mmol) at 0° C. Then, to the above mixture was added (Boc)$_2$O (73.1 mg, 334 umol). The mixture was stirred at 25° C. for 3 hrs. On completion, the residue was diluted with water (30 mL) and extracted with DCM (20 mL×2). The combined organic layer was dried over Na$_2$SO$_4$, filtered and concentrated in vacuo. The residue was purified by prep-HPLC(column: Phenomenex luna C18 150*25 mm*10 um; mobile phase: [water(FA)-ACN]; B %: 28%-58%, 10.5 min) to give the title compound (135 mg, 92% yield) as white solid. $^1$H NMR (400 MHz, DMSO-d$_6$) δ 11.08 (s, 1H), 7.17 (s, 1H), 7.10-7.00 (m, 1H), 7.00-6.92 (m, 1H), 5.34 (dd, J=5.6, 12.8 Hz, 1H), 3.69 (t, J=8.4 Hz, 1H), 3.54-3.45 (m, 1H), 3.36 (s, 3H), 3.31-3.24 (m, 2H), 3.24-3.13 (m, 1H), 2.96-2.84 (m, 1H), 2.77-2.58 (m, 2H), 2.18 (dd, J=5.6, 11.2 Hz, 1H), 2.07-1.93 (m, 2H), 1.41 (d, J=6.4 Hz, 9H); LC-MS (ESI+) m/z 373.1 (M−56).

Step 6—3-[3-methyl-2-oxo-5-[(3S)-pyrrolidin-3-yl]benzimidazol-1-yl]piperidine-2,6-dione To a solution of tert-butyl (3S)-3-[1-(2,6-dioxo-3-piperidyl)-3-methyl-2-oxo-benzimidazol-5-yl]pyrrolidine-1-carboxylate (65 mg, 151 umol) in DCM (2 mL) was added TFA (17.3 mg, 151 umol). The mixture was then stirred at 25° C. for 1 hr. On completion, the reaction mixture was concentrated under reduced pressure to give the title compound (65.0 mg, 96% yield) as a brown oil. LC-MS (ESI+) m/z 329.3 (M+H)$^+$.

Example 1 (Method 1): Synthesis of N-[2-[4-[4-[1-(2,6-dioxo-3-piperidyl)-3-methyl-2-oxo-benzimidazol-4-yl]piperidine-1-carbonyl]cyclohexyl]indazol-5-yl]-6-(trifluoromethyl)pyridine-2-carboxamide (I-94)

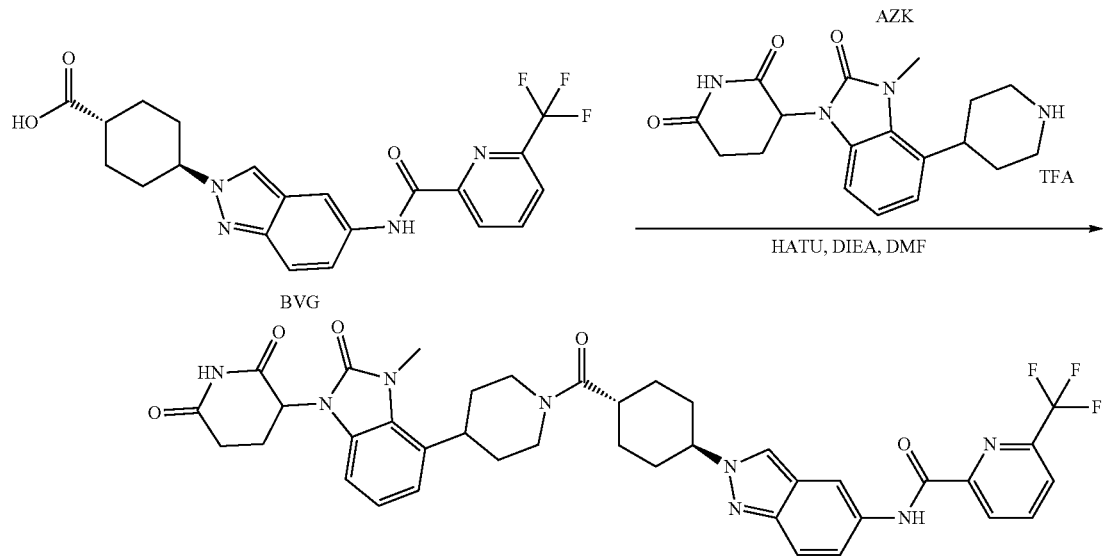

To a mixture of 3-[3-methyl-2-oxo-4-(4-piperidyl)benzimidazol-1-yl]piperidine-2,6-dione (130 mg, 284 umol, TFA, Intermediate AZK) and DIEA (110 mg, 854 umol, 148 uL) in DMF (2 mL) was added in 4-[5-[[6-(trifluoromethyl)pyridine-2-carbonyl]amino]indazol-2-yl]cyclohexanecarboxylic acid (123 mg, 284 umol, Intermediate BVG) and HATU (129 mg, 341 umol). The reaction mixture was then stirred at 25° C. for 1.5 hours. On completion, the reaction mixture was quenched with water (0.05 mL). The residue was purified by prep-HPLC(column: Phenomenex luna C18 150*25 mm*10 um; mobile phase: [water (0.225% FA)-ACN]; B %: 42%-72%, 10 min) to give the title compound (56.8 mg, 25% yield) as light yellow solid. $^1$H NMR (400 MHz, DMSO-$d_6$) δ 11.10 (s, 1H), 10.36 (s, 1H), 8.42-8.29 (m, 4H), 8.17 (d, J=7.6 Hz, 1H), 7.64-7.53 (m, 2H), 7.03-6.99 (m, 2H), 5.38 (dd, J=5.2, 12.4 Hz, 1H), 4.62 (d, J=13.2 Hz, 1H), 4.57-4.47 (m, 1H), 4.18 (d, J=12.0 Hz, 1H), 3.64 (s, 3H), 3.55 (t, J=11.6 Hz, 1H), 3.29-3.19 (m, 1H), 2.95-2.80 (m, 2H), 2.77-2.63 (m, 3H), 2.19 (d, J=10.4 Hz, 2H), 2.13-1.81 (m, 8H), 1.77-1.62 (m, 3H), 1.61-1.51 (m, 1H); LC-MS (ESI$^+$) m/z 757.6 (M+H)$^+$.

The following compounds in Table 3 where prepared according to the same procedure of Method 2 above.

TABLE 3

Compounds synthesized via Method 1.

| I-#[a] | Intermediate Amine | Intermediate Acid | LCMS (ES+) m/z (M + H)$^+$ | $^1$HNMR (400 MHz, DMSO-d6) δ |
|---|---|---|---|---|
| I-95[b] | BUP | BUW | 740.6 | 11.09 (s, 1H), 10.22 (d, J = 2.0 Hz, 1H), 9.82 (s, 1H), 9.16 (d, J = 2.0 Hz, 1H), 8.93 (s, 1H), 8.39 (s, 1H), 8.23 (s, 1H), 7.63 (d, J = 8.4 Hz, 1H), 7.35 (d, J = 10.8 Hz, 1H), 7.05-6.95 (m, 3H), 5.37 (dd, J = 6.0, 12.8 Hz, 1H), 4.48-4.40 (m, 1H), 3.59 (s, 3H), 3.04-2.97 (m, 2H), 2.94-2.83 (m, 1H), 2.76-2.68 (m, 1H), 2.65-2.58 (m, 1H), 2.26-2.21 (m, 2H), 2.19-2.15 (m, 2H), 2.12-2.05 (m, 2H), 2.03-1.93 (m, 5H), 1.86-1.75 (m, 5H), 1.71-1.64 (m, 1H), 1.17-1.11 (m, 2H) |
| I-186 | AQK | BVG | 786.7 | 11.09 (s, 1H), 10.36 (s, 1H), 8.42-8.39 (m, 2H), 8.38-8.34 (m, 1H), 8.30 (s, 1H), 8.19-8.16 (m, 1H), 7.63-7.54 (m, 2H), 7.01-6.94 (m, 2H), 6.91-6.87 (m, 1H), 5.39-5.33 (m, 1H), 4.55-4.42 (m, 1H), 3.66 (s, 3H), 3.29 (s, 1H), 3.19-3.15 (m, 2H), 2.99 (s, 3H), 2.90-2.82 (m, 2H), 2.79 (s, 2H), 2.76-2.70 (m, 1H), 2.65-2.59 (m, 1H), 2.22-2.12 (m, 3H), 2.08-1.98 (m, 3H), 1.92-1.83 (m, 3H), 1.74-1.62 (m, 3H), 1.60-1.55 (m, 1H) |
| I-187 | AQK | BXH | 787.6 | 11.09 (s, 1H), 10.20 (s, 1H), 9.06 (s, 1H), 8.60 (s, 1H), 8.51-8.47 (m, 2H), 8.42 (t, J = 7.6 Hz, 1H), 8.26-8.22 (m, 1H), 7.02-6.95 (m, 2H), 6.92-6.86 (m, 1H), 5.39-5.32 (m, 1H), 4.71-4.62 (m, 1H), 4.52-4.37 (m, 1H), 3.67 (s, 3H), 3.20- |

TABLE 3-continued

Compounds synthesized via Method 1.

| I-#[a] | Intermediate Amine | Intermediate Acid | LCMS (ES+) m/z (M + H)+ | ¹HNMR (400 MHz, DMSO-d6) δ |
|---|---|---|---|---|
| | | | | 3.14 (m, 2H), 3.00 (s, 3H), 2.91-2.75 (m, 5H), 2.64 (s, 1H), 2.21-2.17 (m, 3H), 2.08-2.02 (m, 2H), 1.94-1.85 (m, 3H), 1.75-1.63 (m, 3H), 1.62-1.53 (m, 2H) |
| I-188 | AZK | BXH | 758.6 | 11.17-11.00 (m, 1H), 10.20 (s, 1H), 9.06 (s, 1H), 8.60 (s, 1H), 8.53-8.46 (m, 2H), 8.45-8.38 (m, 1H), 8.26-8.20 (m, 1H), 7.00 (s, 3H), 5.41-5.35 (m, 1H), 4.73-4.54 (m, 2H), 4.25-4.11 (m, 1H), 3.64 (s, 3H), 3.59-3.51 (m, 1H), 2.95-2.82 (m, 2H), 2.76-2.63 (m, 3H), 2.20 (s, 3H), 2.15-2.07 (m, 3H), 1.97-1.88 (m, 4H), 1.74-1.64 (m, 3H), 1.58-1.51 (m, 1H) |
| I-309 | CEY | CEX | 747.3 | 11.10 (s, 1H), 8.36 (d, J = 8.0 Hz, 1H), 8.16 (d, J = 8.4 Hz, 1H), 7.98 (s, 1H), 7.65 (d, J = 2.0 Hz, 1H), 7.52 (dd, J = 2.0, 8.4 Hz, 1H), 7.23 (d, J = 8.4 Hz, 1H), 7.12-6.95 (m, 3H), 5.38 (dd, J = 4.8, 12.4 Hz, 1H), 4.36-4.25 (m, 1H), 3.78-3.65 (m, 1H), 3.61 (s, 3H), 3.56-3.42 (m, 2H), 2.95-2.85 (m, 2H), 2.77-2.70 (m, 1H), 2.65-2.61 (m, 1H), 2.55-2.52 (m, 2H), 2.05-1.81 (m, 10H), 1.77-1.65 (m, 1H), 1.42-1.30 (m, 2H), 1.19 (s, 3H), 1.18 (s, 3H), 1.12-1.01 (m, 2H) |
| I-310 | CFA | CEZ | 729.3 | 10.55 (s, 1H), 9.66 (br s, 1H), 8.59 (s, 1H), 8.40 (br d, J = 7.6 Hz, 1H), 8.21-8.11 (m, 1H), 7.98 (s, 1H), 7.90 (br d, J = 8.4 Hz, 1H), 7.85-7.78 (m, 1H), 7.60 (br d, J = 1.2 Hz, 2H), 7.56 (br d, J = 8.4 Hz, 1H), 7.22 (d, J = 8.4 Hz, 1H), 4.27 (br dd, J = 6.4, 13.6 Hz, 1H), 4.02-3.98 (m, 1H), 3.87-3.49 (m, 4H), 3.18-2.92 (m, 3H), 2.78 (td, J = 5.6, 16.8 Hz, 3H), 2.04 (br s, 4H), 1.92 (br d, J = 10.4 Hz, 4H), 1.79-1.63 (m, 1H), 1.36 (br d, J = 12.4 Hz, 2H), 1.20 (d, J = 6.4 Hz, 7H), 1.12-1.01 (m, 2H) |
| I-316 | CBP | CFF | 806.3 | 11.11-11.03 (m, 1H), 10.51 (d, J = 2.4 Hz, 1H), 9.00 (d, J = 4.0 Hz, 1H), 8.51-8.45 (m, 1H), 8.44-8.39 (m, 1H), 8.24 (d, J = 7.6 Hz, 1H), 7.69 (d, J = 9.2 Hz, 1H), 7.60 (q, J = 7.6 Hz, 1H), 7.11-7.01 (m, 1H), 6.79-6.64 (m, 1H), 5.11-4.93 (m, 1H), 4.04 (d, J = 6.0 Hz, 3H), 3.48-3.41 (m, 1H), 3.40-3.35 (m, 2H), 3.28-3.22 (m, 1H), 3.16-2.97 (m, 2H), 2.96-2.78 (m, 2H), 2.76-2.68 (m, 1H), 2.61 (d, J = 1.6 Hz, 1H), 2.47-2.35 (m, 2H), 2.19 (d, J = 11.2 Hz, 1H), 2.13-1.98 (m, 2H), 1.93-1.80 (m, 2H), 1.78-1.63 (m, 4H), 1.62-1.50 (m, 2H), 1.45-1.32 (m, 1H) |
| I-352 | CCC | AMY | 887.8 | 12.35 (d, J = 4.0 Hz, 1 H) 11.10 (d, J = 3.6 Hz, 1 H) 8.71 (d, J = 5.2 Hz, 1 H) 8.42-8.47 (m, 1 H) 8.32-8.39 (m, 2 H) 8.16 (d, J = 8.0 Hz, 1H) 7.50-7.63 (m, 2H) 7.07 (dd, J = 12.0, 7.2 Hz, 1 H) 6.94 (dd, J = 15.6, 8.4 Hz, 1 H) 6.47-6.56 (m, 1 H) 5.93 (d, J = 6.0 Hz, 1 H) 5.05 (dt, J = 12.4, 4.8 Hz, 1 H) 4.49 (d, J = 4.4 Hz, 1 H) 4.08-4.25 (m, 2 H) 3.45 (s, 1 H) 3.36 (s, 1 H) 3.28 (s, 1 H) 2.81-3.07 (m, 4 H) 2.73 (s, 1 H) 2.55 (s, 3 H) 2.36-2.41 (m, 2 H) 2.21-2.31 (m, 2 H) 2.13-2.20 (m, 2 H) 1.97-2.06 (m, 3 H) 1.77-1.90 (m, 3 H) 1.69 (d, J = 6.8 Hz, 2 H) 1.60 (d, J = 12.4 Hz, 8 H) |
| I-407 | CCJ | CEX | 748.3 | 11.10 (s, 1H), 8.37 (d, J = 7.2 Hz, 1H), 8.19-8.10 (m, 1H), 7.98 (s, 1H), 7.65 (d, J = 2.0 Hz, 1H), 7.56-7.50 (m, 1H), 7.23 (d, J = 8.4 Hz, 1H), 7.07-7.00 (m, 1H), 6.96 (d, J = 6.4 Hz, 2H), 5.42-5.32 (m, 1H), 4.31 (d, J = 6.3, 8.0 Hz, 1H), 3.75-3.69 (m, 1H), 3.63 (s, 3H), 3.60-3.54 (m, 1H), 3.20-3.00 (m, 5H), 2.96-2.84 (m, 2H), 2.76-2.70 (m, 1H), 2.69-2.63 (m, 2H), 2.03-1.96 (m, 1H), 1.86 (d, J = 8.8 Hz, 4H), 1.78-1.65 (m, 1H), 1.40-1.30 (m, 2H), 1.27-1.22 (m, 1H), 1.19 (d, J = 6.4 Hz, 6H), 1.16-1.07 (m, 3H) |
| I-408 | CGB | CEZ | 730.4 | 0.52 (s, 1H), 9.44 (s, 1H), 8.54 (s, 1H), 8.35 (d, J = 7.6 Hz, 1H), 8.19-8.11 (m, 1H), 7.98 (s, 1H), 7.77-7.70 (m, 1H), 7.68-7.63 (m, 1H), 7.62 (d, J = 1.6 Hz, 1H), 7.55-7.49 (m, 1H), 7.33-7.27 (m, 1H), 7.21 (d, J = 8.4 Hz, 1H), 4.32-4.21 (m, 1H), 3.95-3.86 (m, 1H), 3.75-3.65 (m, 2H), 3.27-3.09 (m, 6H), 3.03-2.90 (m, 2H), 2.81-2.70 (m, 2H), 1.88 (d, J = 10.0 Hz, 4H), 1.71-1.50 (m, 1H), 1.41-1.29 (m, 2H), 1.27-1.23 (m, 2H), 1.19 (d, J = 6.4 Hz, 6H), 1.11-0.91 (m, 2H) |
| I-409 | CFA | CEX | 729.2 | 10.54 (s, 1H), 9.62 (s, 1H), 8.58 (s, 1H), 8.35 (d, J = 7.2 Hz, 1H), 8.17 (d, J = 8.4 Hz, 1H), 7.98 (s, 1H), 7.88 (d, 1H), 7.80 (t, 1H), 7.62 (t, J = 8.4 Hz, 2H), 7.52 (d, J = 8.4 Hz, 1H), 7.23 (d, J = 8.4 Hz, 1H), 4.36-4.26 (m, 1H), 3.96-3.88 (m, 1H), 3.74-3.68 (m, 2H), 3.30 (s, 2H), 3.04-2.92 (m, 2H), 2.81-2.70 (m, 2H), 2.03-1.82 (m, 9H), 1.67-1.54 (m, 1H), 1.39-1.21 (m, 4H), 1.19 (d, J = 6.4 Hz, 6H), 1.08-0.95 (m, 2H) |
| I-410 | CCJ | CEZ | 748.2 | 0.90-1.02 (m, 2 H) 1.18 (d, J = 6.4 Hz,6 H) 1.25-1.37 (m, 2 H) 1.43-1.56 (m, 1 H) 1.84 (d, J = 10.8 Hz, 4 H) 1.95-2.04 (m, 1 H) 2.20 (s, 3 H) 2.61-2.75 (m, 3 H) 2.77-3.08 (m, 7 H) 3.62 (s, 3 H) 3.65-3.74 (m, 1 H) 4.19-4.32 (m, 1 H) 5.35 (dd, J = 12.4, 5.2 Hz, 1 H) 6.86-7.02 (m, 3 H) 7.21 (d, J = 8.4 Hz, 1 H) 7.52 |

TABLE 3-continued

Compounds synthesized via Method 1.

| I-#[a] | Inter-<br>mediate<br>Amine | Inter-<br>mediate<br>Acid | LCMS<br>(ES+) m/z<br>(M + H)+ | $^1$HNMR (400 MHz, DMSO-d6) δ |
|---|---|---|---|---|
| | | | | (dd, J = 8.4, 1.6 Hz, 1 H) 7.62 (d, J = 1.6 Hz, 1 H) 7.97 (s, 1 H) 8.18 (d, J = 8.4 Hz, 1 H) 8.34 (d, J = 1.6 Hz, 1 H) 11.09 (s, 1 H) |

[a]Coupling ran from 1-4 hrs from 0° C.-rt.
[b](COCl)$_2$ was used in place of HATU for the coupling, which was run at rt for 2.5 hrs with TEA in DCM.

Example 2 (Method 2): Synthesis of N-[2-[4-[[4-[4-(2,4-dioxohexahydropyrimidin-1-yl)-8-isoquinolyl]-1-piperidyl]methyl] cyclohexyl]-6-(1-hydroxy-1-methyl-ethyl)indazol-5-yl]-6-(trifluoromethyl)pyridine-2-carboxamide (I-78)

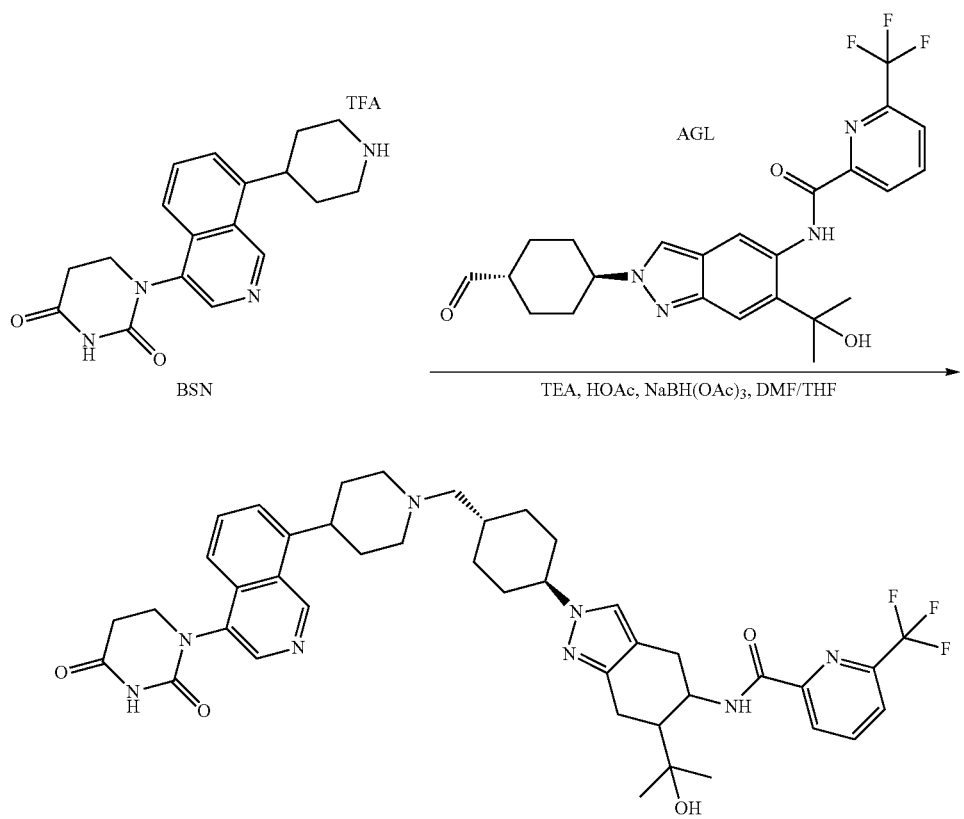

To a mixture of 1-[8-(4-piperidyl)-4-isoquinolyl]hexahydropyrimidine-2,4-dione (50.0 mg, 114 umol, TFA, Intermediate BSN) in DMF (0.5 mL) and THF (3 mL) was added TEA (11.5 mg, 114 umol, 15.8 uL) and the reaction mixture was stirred at −10° C. for 12 min. Then N-[2-(4-formylcyclohexyl)-6-(1-hydroxy-1-methyl-ethyl)indazol-5-yl]-6-(trifluoromethyl)pyridine-2-carboxamide (54.1 mg, 114 umol, Intermediate AGL) and HOAc (6.85 mg, 114 umol, 6.52 uL) was added to the mixture and the mixture was stirred at −10° C. for 0.5 hour. Next, NaBH(OAc)$_3$ (36.2 mg, 171 umol) was added to the mixture at -10° C. and the reaction mixture was stirred at −10° C. for 1 hour. On completion, the reaction mixture was quenched with water (0.05 mL) and concentrated in vacuo. The residue was purified by prep-HPLC (column: Welch Xtimate C18 150*25 mm*5 um; mobile phase: [water (0.225% FA)-ACN]; B %: 17%-47% 11 min) to give the title compound (84.2 mg, 87% yield, FA) as white solid. $^1$H NMR (400 MHz, DMSO-d$_6$) δ 12.37 (s, 1H), 10.56 (s, 1H), 9.68 (s, 1H), 8.73 (s, 1H), 8.61 (s, 1H), 8.48-8.44 (m, 1H), 8.41-8.35 (m, 2H), 8.17 (dd, J=0.8, 7.6 Hz, 1H), 7.94-7.89 (m, 1H), 7.83 (t, J=7.8 Hz, 1H), 7.64 (d, J=6.8 Hz, 1H), 7.58 (s, 1H), 5.96 (s, 1H), 4.54-4.44 (m, 1H), 3.94 (ddd, J=5.2, 9.6, 12.0 Hz, 1H), 3.90-3.79 (m, 1H), 3.72 (td, J=6.0, 12.0 Hz, 1H), 3.57-3.44 (m, 2H), 2.99 (ddd, J=6.0, 10.0, 16.4 Hz, 2H), 2.92-2.83 (m, 1H), 2.80 (t, J=5.6 Hz, 1H), 2.76 (t, J=5.6 Hz, 1H), 2.21 (d, J=11.2 Hz, 2H), 2.15-1.84 (m, 9H), 1.63 (s, 6H), 1.34-1.20 (m, 2H); LC-MS (ESI+) m/z 783.3 (M+H)+.

The following compounds in Table 4 where prepared according to the same procedure of Method 2 above.

TABLE 4

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-1 | WX | BOX | 739.6 | 11.09 (s, 1H), 10.67 (s, 1H), 8.24-8.21 (m, 2H), 7.51 (s, 1H), 7.07 (d, J = 7.6 Hz, 1H), 6.99-6.93 (m, 1H), 6.87 (d, J = 7.6 Hz, 1H), 6.24-6.11 (m, 1H), 5.38 (dd, J = 5.6, 12.8 Hz, 1H), 4.42-4.30 (m, 1H), 3.68 (s, 4H), 3.62 (s, 3H), 2.92-2.84 (m, 4H), 2.71 (d, J = 13.2 Hz, 2H), 2.22 (d, J = 7.2 Hz, 2H), 2.17-2.17 (m, 1H), 2.18 (s, 3H), 2.13-2.06 (m, 3H), 1.98-1.85 (m, 6H), 1.61 (s, 7H), 1.43-1.35 (m, 2H), 1.11-1.01 (m, 2H), 0.86-0.78 (m, 4H) |
| I-2 | ATH | BBH | 853.5 | 11.10 (s, 1H), 10.51 (s, 1H), 8.68 (s, 1H), 8.47-8.37 (m, 2H), 8.33 (s, 1H), 8.22 (dd, J = 1.2, 7.6 Hz, 1H), 7.59 (dd, J = 7.2, 8.4 Hz, 1H), 7.40 (s, 1H), 7.05 (dd, J = 7.6, 17.6 Hz, 2H), 6.48 (t, J = 5.6 Hz, 1H), 5.06 (dd, J = 5.6, 12.8 Hz, 1H), 4.40-4.27 (m, 1H), 4.13 (td, J = 3.2, 6.0 Hz, 1H), 3.31 (s, 2H), 3.22 (q, J = 6.8 Hz, 2H), 3.12 (s, 2H), 3.02 (s, 2H), 2.95-2.83 (m, 1H), 2.65-2.54 (m, 2H), 2.24-2.18 (m, 4H), 2.14-2.02 (m, 3H), 1.93-1.79 (m, 4H), 1.79-1.71 (m, 2H), 1.65 (q, J = 6.8 Hz, 2H), 1.31 (dd, J = 3.6, 7.8 Hz, 1H), 1.16-1.01 (m, 2H), 0.97-0.90 (m, 2H), 0.80-0.74 (m, 2H) |
| I-3 | ATH | BOZ | 841.4 | 11.15-11.05 (m, 1H), 10.51 (s, 1H), 8.53 (s, 1H), 8.49-8.38 (m, 2H), 8.23 (d, J = 7.6 Hz, 1H), 7.59 (t, J = 7.6 Hz, 1H), 7.36-7.29 (m, 1H), 7.05 (dd, J = 7.6, 18.4 Hz, 2H), 6.48 (br t, J = 6.0 Hz, 1H), 5.06 (dd, J = 5.6, 12.8 Hz, 1H), 3.96 (s, 3H), 3.74 (s, 3H), 3.22 (br d, J = 6.4 Hz, 2H), 3.18 (br s, 2H), 3.08 (br s, 3H), 2.96-2.80 (m, 3H), 2.64-2.55 (m, 2H), 2.26-2.18 (m, 4H), 2.06-2.00 (m, 1H), 1.97-1.89 (m, 2H), 1.85-1.73 (m, 4H), 1.70-1.52 (m, 5H), 1.40-1.28 (m, 1H), 1.13-1.00 (m, 2H) |
| I-4 | AJF | ATF | 837.2 | 11.09 (s, 1H), 10.67 (s, 1H), 8.66 (s, 1H), 8.32-8.25 (m, 3H), 8.01 (dd, J = 2.4, 6.8 Hz, 1H), 7.58 (dd, J = 12, 8.4 Hz, 1H), 7.14 (s, 1H), 7.10 (d, J = 8.4 Hz, 1H), 7.02 (d, J = 7.2 Hz, 1H), 6.46 (t, J = 5.6 Hz, 1H), 5.05 (dd, J = 5.4, 12.8 Hz, 1H), 4.39-4.29 (m, 1H), 3.99 (s, 3H), 2.93-2.83 (m, 1H), 2.63-2.52 (m, 4H), 2.31-2.23 (m, 2H), 2.23-1.98 (m, 11H), 1.94-1.83 (m, 6H), 1.57 (m, 3H), 1.53-1.45 (m, 4H), 1.13-1.01 (m, 2H) |
| I-7 | ATC | BEO | 828.5 | 11.00 (s, 1H), 10.60 (s, 1H), 9.39 (dd, J = 1.2, 7.2 Hz, 1H), 8.96 (dd, J = 1.2, 4.0 Hz, 1H), 8.73 (s, 2H), 7.58 (t, J = 7.6 Hz, 1H), 7.42 (s, 1H), 7.36 (dd, J = 4.0, 6.8 Hz, 1H), 7.04 (dd, J = 8.8, 19.6 Hz, 2H), 6.47 (t, J = 5.2 Hz, 1H), 5.05 (dd, J = 5.2, 12.8 Hz, 1H), 4.03 (s, 3H), 3.21 (d, J = 5.6 Hz, 2H), 2.92-2.81 (m, 2H), 2.64-2.53 (m, 3H), 2.30-2.24 (m, 2H), 2.22-2.10 (m, 4H), 2.09-1.97 (m, 3H), 1.95-1.81 (m, 4H), 1.73-1.64 (m, 2H), 1.62-1.42 (m, 7H), 1.41-1.32 (m, 2H), 1.04-0.95 (m, 2H) |
| I-8 | BPA | ATF | 811.5 | 11.09 (s, 1H), 10.67 (s, 1H), 8.67 (s, 1H), 8.34-8.26 (m, 3H), 8.01 (dd, J = 1.8, 6.8 Hz, 1H), 7.59 (t, J = 7.6 Hz, 1H), 7.15 (s, 1H), 7.09 (d, J = 8.4 Hz, 1H), 7.02 (d, J = 7.2 Hz, 1H), 6.50 (t, J = 5.2 Hz, 1H), 5.05 (dd, J = 5.2, 12.8 Hz, 1H), 4.41-4.30 (m, 1H), 3.99 (s, 3H), 2.84 (d, J = 9.2 Hz, 3H), 2.63-2.51 (m, 4H), 2.23-2.10 (m, 7H), 2.07-1.99 (m, 1H), 1.96-1.82 (m, 6H), 1.69 (d, J = 12 Hz, 2H), 1.61 (m, 1H), 1.52 (q, J = 6.4 Hz, 2H), 1.41-1.28 (m, 1H), 1.26-1.16 (m, 2H), 1.15-1.02 (m, 2H) |
| I-9 | ATC | ATJ | 855.4 | 11.10 (s, 1H), 10.50 (s, 1H), 9.94 (s, 1H), 8.69 (s, 1H), 8.48-8.44 (m, 1H), 8.43-8.37 (m, 1H), 8.34 (s, 1H), 8.21 (d, J = 7.6 Hz, 1H), 7.59 (t, J = 7.6 Hz, 1H), 7.15 (s, 1H), 7.10-6.99 (m, 2H), 6.66-6.29 (m, 1H), 5.09-5.02 (m, 1H), 4.45-4.35 (m, 1H), 3.98 (s, 3H), 3.41-3.28 (m, 2H), 3.23 (t, J = 6.4 Hz, 2H), 2.93 (d, J = 5.2 Hz, 2H), 2.91-2.83 (m, 2H), 2.82-2.71 (m, 1H), 2.65-2.51 (m, 2H), 2.36-2.25 (m, 1H), 2.20-2.11 (m, 2H), 2.10-1.99 (m, 4H), 1.99-1.83 (m, 7H), 1.77-1.63 (m, 3H), 1.58-1.50 (m, 1H), 1.46 (t, J = 9.6 Hz, 1H), 1.31-1.17 (m, 2H) |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-10 | ATH | BPB | 827.6 | 11.17-11.00 (m, 1H), 10.18 (s, 1H), 9.39-9.27 (m, 1H), 8.47-8.38 (m, 2H), 8.34 (s, 1H), 8.23 (m, 1H), 7.65-7.52 (m, 2H), 7.11-6.97 (m, 3H), 6.47 (t, J = 5.9 Hz, 1H), 5.05 (m, 1H), 3.98 (s, 3H), 3.21 (m, 2H), 3.15-3.09 (m, 3H), 3.05-2.97 (m, 2H), 2.94-2.80 (m, 1H), 2.63-2.55 (m, 1H), 2.22-2.15 (m, 5H), 2.06-1.96 (m, 3H), 1.84-1.72 (m, 4H), 1.67-1.57 (m, 2H), 1.44-1.18 (m, 4H), 1.06-0.90 (m, 2H) |
| I-12 | ATH | BPC | 855.7 | 12.21 (s, 1H), 11.09 (s, 1H), 9.52 (s, 1H), 8.48-8.35 (m, 2H), 8.26-8.18 (m, 2H), 7.73 (s, 1H), 7.58 (t, J = 7.9 Hz, 1H), 7.39 (s, 1H), 7.04 (dd, J = 7.7, 18.7 Hz, 2H), 6.48 (m, 1H), 6.19-6.07 (m, 1H), 5.05 (m, 1H), 3.22 (m, 4H), 2.95-2.81 (m, 1H), 2.63-2.53 (m, 2H), 2.39-2.31 (m, 2H), 2.27-2.10 (m, 4H), 2.08-1.97 (m, 3H), 1.86-1.72 (m, 4H), 1.69-1.55 (m, 9H), 1.46-1.22 (m, 4H), 1.08-0.91 (m, 2H) |
| I-13 | AML | BAT | 799.5 | 11.26-10.90 (m, 1H), 10.53 (s, 1H), 9.37 (d, J = 7.2 Hz, 1H), 8.95 (d, J = 2.0 Hz, 1H), 8.69 (d, J = 10.0 Hz, 2H), 8.26 (s, 1H), 7.58 (t, J = 7.6 Hz, 1H), 7.35 (d, J = 4.4 Hz, 1H), 7.09 (s, 1H), 7.06 (d, J = 6.4 Hz, 1H), 6.99 (d, J = 8.8 Hz, 1H), 6.44 (d, J = 6.0 Hz, 1H), 5.05 (dd, J = 5.2, 12.4 Hz, 1H), 4.40-4.28 (m, 1H), 4.18-4.07 (m, 1H), 4.02 (s, 3H), 2.96-2.82 (m, 1H), 2.65-2.55 (m, 2H), 2.32 (d, J = 8.4 Hz, 4H), 2.26-2.07 (m, 6H), 2.06-1.98 (m, 1H), 1.96-1.81 (m, 4H), 1.72-1.52 (m, 7H), 1.13-1.02 (m, 2H) |
| I-14 | ATH | BPD | 855.4 | 12.52-12.21 (m, 1H), 12.12-11.93 (m, 1H), 11.24-10.81 (m, 1H), 8.60-8.52 (m, 1H), 8.50-8.41 (m, 1H), 8.36 (t, J = 7.6 Hz, 1H), 8.15 (d, J = 7.6 Hz, 1H), 7.58 (t, J = 7.6 Hz, 1H), 7.52-7.27 (m, 1H), 7.11-6.97 (m, 2H), 6.55-6.38 (m, 1H), 5.83 (s, 1H), 5.05 (dd, J = 5.2, 12.8 Hz, 1H), 3.25-3.17 (m, 2H), 3.10 (s, 2H), 3.00 (s, 2H), 2.95-2.81 (m, 1H), 2.79-2.68 (m, 1H), 2.64-2.53 (m, 2H), 2.24-2.17 (m, 4H), 2.17-2.11 (m, 1H), 2.08-1.97 (m, 3H), 1.89-1.79 (m, 2H), 1.79-1.71 (m, 2H), 1.68-1.62 (m, 2H), 1.59 (s, 6H), 1.57-1.47 (m, 2H), 1.34-1.19 (m, 1H), 1.09-0.91 (m, 2H) |
| I-15 | ATC | BPF | 895.3 | 10.20 (s, 1H), 9.73 (d, J = 7.2 Hz, 1H), 8.93 (s, 1H), 8.75 (s, 1H), 8.28 (s, 1H), 7.80 (d, J = 7.2 Hz, 1H), 7.58-7.56 (m, 1H), 7.11 (s, 1H), 7.07 (d, J = 8.4 Hz, 1H), 7.02 (d, J = 7.2 Hz, 1H), 6.51-6.45 (m, 1H), 5.07-5.03 (m, 1H), 4.39-4.27 (m, 1H), 3.98 (s, 3H), 3.24-3.21 (m, 2H), 2.94-2.82 (m, 1H), 2.63-2.55 (m, 1H), 2.31-1.99 (m, 11H), 1.95-1.82 (m, 6H), 1.73-1.65 (m, 2H), 1.61-1.51 (m, 3H), 1.47-1.45 (m, 2H), 1.41-1.36 (m, 2H), 1.13-1.00 (m, 2H) |
| I-16 | AQK | BPG | 802.5 | 11.09 (s, 1H), 10.54 (s, 1H), 9.22-9.16 (m, 1H), 8.73 (s, 1H), 8.53 (dd, J = 1.7, 8.4 Hz, 1H), 8.39 (d, J = 8.1 Hz, 1H), 8.35 (s, 1H), 7.17 (s, 1H), 7.01-6.95 (m, 1H), 6.94-6.85 (m, 2H), 5.36 (dd, J = 5.4, 12.7 Hz, 1H), 4.42-4.33 (m, 1H), 4.00 (s, 3H), 3.65 (s, 3H), 3.16 (d, J = 11.0 Hz, 2H), 2.94-2.85 (m, 1H), 2.81-2.68 (m, 3H), 2.58-2.50 (m, 1H), 2.36-2.25 (m 2H), 2.27 (s, 3H), 2.19-1.98 (m, 5H), 1.96-1.40 (m, 10H), 1.20-1.02 (m, 2H) |
| I-17 | AZK | BMI | 788.3 | 11.10 (s, 1H), 10.58 (s, 1H), 8.66 (s, 1H), 8.50-8.46 (m, 1H), 8.45-8.40 (m, 1H), 8.26 (dd, J = 0.9, 7.6 Hz, 1H), 7.38 (s, 1H), 7.05-6.97 (m, 3H), 5.38 (dd, J = 5.3, 12.5 Hz, 1H), 4.44 (s, 2H), 4.03 (s, 3H), 4.03-3.97 (m, 1H), 3.60 (s, 3H), 3.09 (d, J = 6.4 Hz, 2H), 2.95-2.85 (m, 1H), 2.77-2.69 (m, 1H), 2.66-2.60 (m, 1H), 2.55-2.51 (m, 1H), 2.40-2.32 (m, 2H), 2.30-2.16 (m, 2H), 2.03-1.98 (m, 1H), 1.93 (d, J = 11.9 Hz, 2H), 1.87-1.77 (m, 6H), 1.68-1.57 (m, 3H), 1.16-1.05 (m, 2H) |
| I-18 | AZK | BPI | 733.4 | 11.09 (s, 1H), 10.24 (d, J = 2.2 Hz, 1H), 8.54 (s, 1H), 8.41 (m, 3H), 8.22 (d, J = 7.0 Hz, 1H), 7.58 (d, J = 11.6 Hz, 1H), 7.06-6.92 (m, 3H), 5.36 (dd, J = 4.8, 12.4 Hz, 1H), 5.09-4.97 (m, 1H), 3.58 (s, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 3H), 3.07-2.94 (m, 3H), 2.94-2.82 (m, 1H), 2.74-2.63 (m, 4H), 2.61-2.54 (m, 2H), 2.36-2.26 (m, 3H), 2.22-2.11 (m, 2H), 2.04-1.94 (m, 1H), 1.84-1.72 (m, 4H) |
| I-23 | BPP | BKQ | 775.5 | 11.07 (s, 1H), 10.23 (d, J = 2.0 Hz, 1H), 8.50 (s, 1H), 8.47-8.30 (m, 4H), 8.22 (d, J = 7.6 Hz, 1H), 7.54 (d, J = 12.0 Hz, 1H), 6.83 (d, J = 14.6 Hz, 2H), 5.37-5.30 (m, 1H), 4.51-4.41 (m, 1H), 3.55 (s, 3H), 3.21-3.12 (m, 2H), 2.98 (d, J = 10.4 Hz, 2H), 2.94-2.84 (m, 1H), 2.74-2.59 (m, 2H), 2.29 (s, 3H), 2.21 (d, J = 7.2 Hz, 2H), 2.16 (s, 1H), 2.09-2.03 (m, 2H), 2.01-1.94 (m, 4H), 1.93-1.88 (m, 1H), 1.78 (s, 4H), 1.70-1.61 (m, 1H), 1.21-1.06 (m, 2H) |
| I-24 | AZK | BPQ | 777.5 | 11.11 (s, 1H), 10.53 (s, 1H), 8.63 (s, 1H), 8.54 (s, 1H), 8.49-8.45 (m, 1H), 8.44-8.37 (m, 1H), 8.24 (d, J = 7.8 Hz, 1H), 8.17 (s, 1H), 7.94 (s, 1H), 7.06-6.94 (m, 3H), 5.38 (dd, J = 5.4, 12.4 Hz, 1H), 4.53-4.43 (m, 1H), 3.63-3.55 (m, 3H), 3.05-2.98 (m, 2H), 2.94-2.82 (m, 1H), 2.77-2.57 (m, 3H), 2.28-2.06 (m, 6H), 2.03-1.87 (m, 5H), 1.86-1.62 (m, 5H), 1.22-1.08 (m, 2H) |
| I-25 | BPS | BKQ | 779.3 | 11.11 (s, 1H), 10.23 (d, J = 2.4 Hz, 1H), 8.50 (s, 1H), 8.46-8.38 (m, 3H), 8.23 (dd, J = 0.8, 7.6 Hz, 1H), 7.54 (d, J = 12.0 Hz, 1H), 7.06-6.99 (m, 1H), 6.95-6.86 (m, 1H), 5.53 (dd, J = 5.2, 12.8 Hz, 1H), 4.51-4.40 (m, 1H), 3.65 (s, 3H), 3.59-3.53 (m, 1H), 3.04 (d, J = 8.0 Hz, 2H), 2.64-2.57 (m, 1H), 2.31-2.25 (m, 2H), 2.22-2.08 (m, 6H), 2.00-1.91 (m, 4H), 1.86-1.66 (m, 6H), 1.19-1.08 (m, 2H) |
| I-26 | BPU | BKQ | 779.2 | 11.11 (s, 1H), 10.24 (d, J = 2.0 Hz, 1H), 8.50 (s, 1H), 8.47-8.37 (m, 3H), 8.23 (d, J = 7.6 Hz, 1H), 7.55 (d, J = 11.6 Hz, 1H), 7.04-6.96 (m, 1H), 6.85 (dd, J = 2.4, 11.6 Hz, 1H), 5.36 (dd, J = 5.2, 12.8 Hz, 1H), 4.50-4.41 (m, 1H), 3.57 (s, 3H), 3.23-3.23 (m, 1H), 2.98 (d, J = 10.8 Hz, 2H), 2.88-2.70 (m, 2H), 2.65-2.57 (m, 1H), 2.24-2.14 (m, 4H), 2.10-1.84 (m, 8H), 1.81-1.61 (m, 5H), 1.19-1.07 (m, 2H) |
| I-27 | AZK | BQE | 855.6 | 11.17-11.01 (m, 1H), 10.74 (s, 1H), 8.58 (s, 1H), 8.52-8.47 (m, 1H), 8.43 (d, J = 8.0 Hz, 1H), 8.24 (d, J = 6.8 Hz, 1H), 7.47 (s, 1H), 7.05-6.95 (m, 3H), 5.41-5.33 (m, 1H), 4.62 (s, 1H), 4.43 (s, 2H), 4.14-4.07 (m, 1H), 4.07-3.97 (m, 1H), 3.93 (d, J = 7.6 Hz, 1H), 3.68 (d, J = 6.4 Hz, 1H), 3.59 (s, 3H), 3.00-2.95 (m, 2H), 2.64-2.60 (m, 2H), 2.18 (d, J = 6.0 Hz, 2H), 2.09-1.96 (m, 5H), 1.95-1.85 (m, 4H), 1.83-1.72 (m, 7H), 1.66-1.49 (m, 4H), 1.13-1.00 (m, 2H) |
| I-28 | BAI | BOA | 844.4 | 11.23 (s, 1H), 11.09 (s, 1H), 8.73 (s, 1H), 8.54-8.49 (m, 1H), 8.46-8.40 (m, 1H), 8.29-8.25 (m, 1H), 7.62 (s, 1H), 7.01-6.92 (m, 2H), 6.88 (d, J = 7.2 Hz, 1H), 5.40-5.30 (m, 1H), 4.46 (s, 2H), 4.06-3.99 (m, 1H), 3.87-3.84 (m, 4H), 3.63 (s, 3H), 3.00-2.84 (m, 12H), 2.22 (d, J = 8.0 Hz, 2H), 2.04-1.89 (m, 4H), 1.83-1.72 (m, 3H), 1.68-1.53 (m, 4H), 1.11-1.03 (m, 2H) |
| I-29 | AZK | BQF | 855.4 | 10.75 (s, 1H), 8.58 (s, 1H), 8.52-8.47 (m, 1H), 8.44-8.42 (m, 1H), 8.25 (d, J = 6.8 Hz, 1H), 7.47 (s, 1H), 7.06-6.93 (m, 3H), 5.42-5.32 (m, 1H), 4.62 (s, 1H), 4.43 (s, 2H), 4.10 (s, 1H), 4.05-3.98 (m, 1H), 3.93 (d, J = 8.0 Hz, 1H), 3.68 (d, J = 6.0 Hz, 1H), 3.59 (s, 3H), 3.00-2.94 (m, 2H), 2.92-2.84 (m, 1H), 2.65-2.63 (m, 2H), 2.20-2.15 (m, 2H), 2.09-2.00 (m, 4H), 1.95-1.85 (m, 4H), 1.84-1.69 (m, 7H), 1.69-1.46 (m, 4H), 1.14-1.01 (m, 2H) |
| I-30 | AZK | BQH | 733.3 | 11.09 (s, 1H), 10.24 (s, 1H), 8.54 (s, 1H), 8.48-8.37 (m, 3H), 8.23 (d, J = 7.6 Hz, 1H), 7.59 (d, J = 12.4 Hz, 1H), 7.08-6.93 (m, 3H), 5.41-5.34 (m, 1H), 5.31-5.22 (m, 1H), 3.59 (s, 3H), 3.02 (d, J = 11.2 Hz, 2H), 2.95-2.80 (m, 1H), 2.76-2.64 (m, 4H), 2.61-2.56 (m, 3H), 2.40-2.29 (m, 3H), 2.21-2.09 (m, 2H), 2.06-1.92 (m, 1H), 1.84-1.71 (m, 4H) |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-33 | AZK | BQI | 744.5 | 11.10 (s, 1H), 10.52 (s, 1H), 8.69 (s, 1H), 8.49-8.45 (m, 1H), 8.43-8.37 (m, 2H), 8.22 (d, J = 7.6 Hz, 1H), 7.21 (s, 1H), 7.06-6.95 (m, 3H), 5.41-5.33 (m, 1H), 5.24-5.16 (m, 1H), 3.99 (s, 3H), 3.59 (s, 3H), 3.05-3.01 (m, 2H), 2.90-2.87 (m, 1H), 2.74-2.68 (m, 6H), 2.59 (br s, 2H), 2.39-2.34 (m, 2H), 2.17-2.10 (m, 2H), 2.01-1.97 (m, 1H), 1.84-1.77 (m, 4H) |
| I-35 | BPP | ATJ | 787.3 | METHANOL-d4) δ 8.76 (s, 1H), 8.47 (d, J = 8.0 Hz, 1H), 8.34 (s, 1H), 8.31 (t, J = 8.4 Hz, 1H), 8.20 (s, 1H), 7.80 (s, 1H), 7.08 (s, 1H), 6.92 (s, 1H), 6.88 (s, 1H), 5.48-5.45 (m, 1H), 4.52-4.42 (m, 1H), 4.06 (s, 3H), 3.78 (d, J = 10.4 Hz, 2H), 3.72-3.62 (m, 4H), 3.30-3.22 (m, 2H), 3.21-3.12 (m, 2H), 2.98-2.75 (m, 3H), 2.37 (s, 3H), 2.35-2.28 (m, 2H), 2.24-2.01 (m, 10H), 1.51-1.36 (m, 2H) |
| I-36 | BQK | ATJ | 807.3 | 11.10 (s, 1H), 10.50 (s, 1H), 8.69 (s, 1H), 8.49-8.44 (m, 1H), 8.43-8.38 (m, 1H), 8.34 (s, 1H), 8.22 (d, J = 7.6 Hz, 1H), 7.19 (s, 1H), 7.16 (s, 1H), 7.01 (d, J = 1.6 Hz, 1H), 5.38 (dd, J = 5.6, 12.4 Hz, 1H), 4.44-4.33 (m, 1H), 3.98 (s, 3H), 3.58 (s, 3H), 3.22-3.18 (m, 1H), 2.98 (d, J = 10.4 Hz, 2H), 2.91-2.79 (m, 1H), 2.78-2.70 (m, 1H), 2.68-2.59 (m, 1H), 2.21 (d, J = 6.4 Hz, 2H), 2.18-2.12 (m, 2H), 2.11-2.03 (m, 2H), 2.02-1.94 (m, 3H), 1.94-1.85 (m, 2H), 1.84-1.73 (m, 4H), 1.70-1.57 (m, 1H), 1.13 (q, J = 11.2 Hz, 2H) |
| I-37 | BQL | ATJ | 807.2 | 11.12 (s, 1H), 10.51 (s, 1H), 8.69 (s, 1H), 8.49-8.44 (m, 1H), 8.43-8.38 (m, 1H), 8.34 (s, 1H), 8.22 (dd, J = 1.2, 7.6 Hz, 1H), 7.15 (s, 1H), 7.13-7.04 (m, 2H), 5.40 (dd, J = 5.2, 12.8 Hz, 1H), 4.46-4.34 (m, 1H), 3.98 (s, 3H), 3.65 (s, 3H), 3.64-3.57 (m, 1H), 2.91-2.83 (m, 1H), 2.78-2.57 (m, 5H), 2.53-2.51 (m, 3H), 2.17 (d, J = 10.8 Hz, 2H), 2.05-1.87 (m, 6H), 1.87-1.69 (m, 3H), 1.27-1.12 (m, 2H) |
| I-38 | AZK | AYL | 828.3 | 11.09 (s, 2H), 8.79 (s, 1H), 8.52-8.48 (m, 1H), 8.44-8.40 (m, 1H), 8.38 (s, 1H), 8.23 (dd, J = 0.8, 7.8 Hz, 1H), 7.51 (s, 1H), 7.07-6.95 (m, 3H), 5.38 (dd, J = 5.2, 12.4 Hz, 1H), 4.49-4.37 (m, 1H), 3.93-3.81 (m, 4H), 3.60 (s, 3H), 3.23-3.02 (m, 2H), 2.95-2.90 (m, 4H), 2.90-2.84 (m, 1H), 2.78-2.67 (m, 1H), 2.66-2.57 (m, 1H), 2.53-2.51 (m, 1H), 2.42-2.23 (m, 2H), 2.22-2.10 (m, 3H), 2.06-1.93 (m, 5H), 1.92 (s, 1H), 1.90-1.80 (m, 4H), 1.78-1.64 (m, 1H), 1.27-1.09 (m, 2H) |
| I-39 | BQM | ATJ | 787.3 | 11.08 (s 1H), 10.50 (s, 1H), 8.69 (s, 1H), 8.48-8.45 (m, 1H), 8.43-8.38 (m, 1H), 8.34 (s, 1H), 8.31 (s, 1H), 8.22 (dd, J = 0.8, 7.7 Hz, 1H), 7.16 (s, 1H), 6.90-6.80 (m, 2H), 5.33 (dd, J = 5.6, 12.4 Hz, 1H), 4.43-4.33 (m, 1H), 3.98 (s, 3H), 3.61 (s, 3H), 3.00 (d, J = 10.8 Hz, 2H), 2.92-2.82 (m, 1H), 2.75-2.68 (m, 1H), 2.64-2.59 (m, 1H), 2.46 (s, 3H), 2.31-2.25 (m, 1H), 2.23-2.19 (m, 3H), 2.18-2.12 (m, 2H), 2.07-1.85 (m, 8H), 1.71-1.65 (m, 2H), 1.21-1.08 (m, 2H) |
| I-40 | BQV | ATJ | 816.4 | 11.06 (s, 1H), 10.49 (s, 1H), 8.68 (s, 1H), 8.50-8.36 (m, 2H), 8.33 (s, 1H), 8.23-8.18 (M, 1H), 7.15 (s, 1H), 6.89-6.80 (m, 1H), 6.78-6.69 (m, 1H), 5.35-5.25 (m, 1H), 4.46-4.28 (m, 1H), 4.03 (s, 3H), 3.64 (s, 3H), 3.27-3.24 (m, 2H), 3.10-2.98 (m, 2H), 2.90-2.79 (m, 1H), 2.72-2.63 (m, 1H), 2.63-2.55 (m, 1H), 2.52-2.50 (m, 2H), 2.35 (s, 3H), 2.31-2.23 (m, 4H), 2.19-2.08 (m, 2H), 2.04-1.83 (m, 5H), 1.76-1.50 (m, 5H), 1.18-1.00 (m, 2H) |
| I-41 | AQK | BQW | 815.4 | 11.08 (s, 1H), 10.37 (s, 1H), 8.50 (s, 1H), 8.47-8.35 (m, 2H), 8.28-8.11 (m, 1H), 7.18 (s, 1H), 7.04-6.84 (m, 3H), 6.17 (s, 1H), 5.40-5.28 (m, 1H), 3.98 (s, 3H), 3.70 (s, 3H), 3.65 (s, 3H), 3.29 (s, 3H), 3.23-3.15 (m, 2H), 2.93-2.85 (m, 1H), 2.81-2.69 (m, 4H), 2.67-2.58 (m, 2H), 2.11-1.84 (m, 8H), 1.82-1.53 (m, 4H), 1.52-1.34 (m, 2H), 1.21-1.05 (m, 2H) |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-42 | BQX | ATJ | 832.3 | 10.51 (s, 1H), 8.69 (s, 1H), 8.49-8.45 (m, 1H), 8.44-8.39 (m, 1H), 8.35 (s, 1H), 8.29 (s, 1H), 8.22 (dd, J = 1.0, 7.6 Hz, 1H), 7.16 (s, 1H), 6.86 (d, J = 8.8 Hz, 1H), 6.68 (d, J = 8.8 Hz, 1H), 5.34-5.27 (m, 1H), 4.45-4.32 (m, 1H), 3.99 (s, 3H), 3.78 (s, 3H), 3.63 (s, 3H), 2.99-2.82 (m, 6H), 2.69-2.65 (m, 2H), 2.33 (d, J = 3.6 Hz, 2H), 2.30 (d, J = 6.8 Hz, 2H), 2.26 (s, 3H), 2.19-2.12 (m, 3H), 2.02-1.92 (m, 4H), 1.75-1.69 (m, 2H), 1.62-1.55 (m, 2H), 1.18-1.11 (m, 2H) |
| I-43 | AZK | BQW | 786.3 | 11.09 (s, 1H), 10.37 (s, 1H), 8.50 (s, 1H), 8.47-8.43 (m, 1H), 8.42-8.36 (m, 1H), 8.22-8.17 (m, 1H), 7.18 (s, 1H), 7.08-6.92 (m, 3H), 6.17 (s, 1H), 5.48-5.28 (m, 1H), 3.98 (s, 3H), 3.70 (s, 3H), 3.60 (s, 3H), 3.30-3.28 (m, 2H), 3.17-3.01 (m, 2H), 2.94-2.82 (m, 1H), 2.78-2.68 (m, 2H), 2.66-2.56 (m, 2H), 2.07-1.91 (m, 6H), 1.90-1.76 (m, 4H), 1.75-1.56 (m, 2H), 1.52-1.39 (m, 2H), 1.20-1.08 (m, 2H) |
| I-44 | AZK | BQY | 840.4 | 11.10 (s, 1H), 10.70 (s, 1H), 8.68 (s, 1H), 8.51-8.47 (m, 1H), 8.41 (t, J = 8.0 Hz, 1H), 8.35 (s, 1H), 8.31-8.27 (m, 1H), 8.22 (dd, J = 0.8, 7.8 Hz, 1H), 7.40 (s, 1H), 7.06-6.95 (m, 3H), 5.37 (dd, J = 5.2, 12.8 Hz, 1H), 4.62 (s, 1H), 4.48-4.33 (m, 1H), 4.06 (s, 1H), 4.01 (d, J = 7.6 Hz, 1H), 3.69-3.65 (m, 1H), 3.60 (s, 3H), 3.00 (d, J = 11.2 Hz, 2H), 2.95-2.84 (m, 2H), 2.78-2.70 (m, 1H), 2.69-2.64 (m, 2H), 2.61 (s, 1H), 2.35-2.33 (m, 1H), 2.22 (d, J = 6.8 Hz, 2H), 2.17-2.13 (m, 2H), 2.12-2.04 (m, 3H), 2.03-1.87 (m, 6H), 1.86-1.76 (m, 5H), 1.70-1.63 (m, 1H), 1.20-1.11 (m, 2H) |
| I-45 | AZK | BRB | 762.3 | 11.09 (s, 1H), 10.32 (s, 1H), 9.59 (s, 1H), 9.49 (s, 1H), 8.51 (s, 1H), 8.24 (d, J = 7.6 Hz, 1H), 7.54 (d, J = 12.0 Hz, 1H), 7.03-6.99 (m, 3H), 5.37 (dd, J = 4.8, 11.6 Hz, 1H), 4.49-4.40 (m, 1H), 3.59 (s, 3H), 3.03 (d, J = 11.2 Hz, 2H), 2.93-2.85 (m, 1H), 2.72-2.64 (m, 2H), 2.27 (d, J = 7.2 Hz, 2H), 2.17 (d, J = 10.4 Hz, 4H), 2.05-1.92 (m, 6H), 1.86-1.78 (m, 4H), 1.71-1.67 (m, 1H), 1.20-1.11 (m, 2H) |
| I-47 | BRE | BKQ | 791.3 | 11.08 (s, 1H), 10.24 (d, J = 2.1 Hz, 1H), 8.51 (s, 1H), 8.47-8.38 (m, 3H), 8.24-8.21 (m, 1H), 7.55 (d, J = 11.9 Hz, 1H), 6.91 (d, J = 8.4 Hz, 1H), 6.72 (d, J = 8.8 Hz, 1H), 5.39-5.27 (m, 1H), 4.52-4.39 (m, 1H), 3.77 (s, 3H), 3.56 (s, 3H), 2.97 (d, J = 11.2 Hz, 2H), 2.71-2.62 (m, 3H), 2.22-2.13 (m, 6H), 2.02-1.94 (m, 7H), 1.71-1.54 (m, 4H), 1.20-1.10 (m, 2H) |
| I-48 | BRE | ATJ | 803.3 | 11.08 (s, 1H), 10.51 (s, 1H), 8.70 (s, 1H), 8.49-8.45 (m, 1H), 8.44-8.39 (m, 1H), 8.34 (s, 1H), 8.22 (d, J = 7.6 Hz, 1H), 7.17 (s, 1H), 6.91 (d, J = 8.4 Hz, 1H), 6.72 (d, J = 8.8 Hz, 1H), 5.33 (dd, J = 4.4, 12.4 Hz, 1H), 4.39 (t, J = 11.6 Hz, 1H), 3.99 (s, 3H), 3.77 (s, 3H), 3.57 (s, 3H), 2.97 (d, J = 10.0 Hz, 2H), 2.92-2.86 (m, 1H), 2.71-2.59 (m, 2H), 2.41-2.34 (m, 4H), 2.22-2.15 (m, 4H), 2.00-1.91 (m, 6H), 1.66 (d, J = 1.4 Hz, 1H), 1.61-1.55 (m, 2H), 1.19-1.10 (m, 2H) |
| I-49 | AZK | BRC | 694.2 | 11.13-11.05 (m, 1H), 10.40-10.24 (m, 1H), 9.40-9.29 (m, 1H), 9.00-8.81 (m, 2H), 8.55-8.43 (m, 1H), 8.39-8.28 (m, 1H), 7.61-7.47 (m, 1H), 7.10-6.92 (m, 3H), 5.43-5.34 (m, 1H), 4.55-4.39 (m, 1H), 3.59 (s, 3H), 3.04-3.00 (m, 2H), 2.95-2.85 (m, 2H), 2.71-2.64 (m, 2H), 2.26-2.23 (m, 2H), 2.12-2.07 (m, 2H), 2.13-2.09 (m, 2H), 2.03-1.93 (m, 6H), 1.84-1.75 (m, 4H), 1.21-1.11 (m, 2H) |
| I-51 | BPS | ATJ | 791.2 | 11.10 (s, 1H), 10.50 (s, 1H), 8.69 (s, 1H), 8.49-8.44 (m, 1H), 8.43-8.37 (m, 1H), 8.33 (s, 1H), 8.21 (d, J = 8.4 Hz, 1H), 7.16 (s, 1H), 7.07-6.99 (m, 1H), 6.94-6.78 (m, 1H), 5.59-5.23 (m, 1H), 4.43-4.30 (m, 1H), 3.98 (s, 3H), 3.64 (s, 2H), 3.58 (d, J = 7.2 Hz, 1H), 3.23-3.13 (m, 2H), 3.04-2.92 (m, 3H), 2.65-2.55 (m, 1H), 2.21 (d, J = 7.0 Hz, 2H), 2.18-2.12 (m, 2H), 2.11-1.94 (m, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 5H), 1.93-1.84 (m, 2H), 1.83-1.57 (m, 5H), 1.21-1.03 (m, 2H) |
| I-52 | BPU | ATJ | 791.3 | 11.10 (s, 1H), 10.50 (s, 1H), 8.69 (s, 1H), 8.49-8.44 (m, 1H), 8.43-8.37 (m, 1H), 8.34 (s, 1H), 8.22 (d, J = 7.2 Hz, 1H), 7.16 (s, 1H), 7.02 (d, J = 8.8 Hz, 1H), 6.89-6.74 (m, 1H), 5.36 (dd, J = 5.6, 12.4 Hz, 1H), 4.46-4.33 (m, 1H), 3.98 (s, 3H), 3.59 (s, 3H), 3.27-3.05 (m, 4H), 2.91-2.70 (m, 2H), 2.65-2.57 (m, 1H), 2.46-2.34 (m, 3H), 2.20-2.14 (m, 2H), 2.02-1.71 (m, 10H), 1.27-1.10 (m, 2H) |
| I-53 | BOK | ATJ | 836.3 | 11.11 (s, 1H), 10.50 (s, 1H), 8.69 (s, 1H), 8.49-8.44 (m, 1H), 8.43-8.37 (m, 1H), 8.34 (s, 1H), 8.23-8.20 (m, 1H), 7.16 (s, 1H), 7.06-6.97 (m, 2H), 5.37 (dd, J = 5.2, 12.8 Hz, 1H), 4.44-4.30 (m, 1H), 3.98 (s, 3H), 3.65 (s, 3H), 3.54 (t, J = 10.8 Hz, 2H), 3.02 (d, J = 10.8 Hz, 2H), 2.92-2.81 (m, 1H), 2.72-2.57 (m, 2H), 2.45-2.36 (m, 1H), 2.30 (d, J = 6.8 Hz, 2H), 2.25 (s, 3H), 2.15 (d, J = 11.6 Hz, 2H), 2.04-1.86 (m, 5H), 1.76-1.50 (m, 5H), 1.17-1.04 (m, 2H) |
| I-54 | BQQ | ATJ | 836.2 | 11.09 (s, 1H), 10.50 (s, 1H), 8.69 (s, 1H), 8.49-8.44 (m, 1H), 8.43-8.37 (m, 1H), 8.34 (s, 1H), 8.21 (dd, J = 0.8, 7.6 Hz, 1H), 7.15 (s, 1H), 7.09 (s, 1H), 6.91 (d, J = 2.0 Hz, 1H), 5.36 (dd, J = 5.2, 12.4 Hz, 1H), 4.44-4.32 (m, 1H), 3.98 (s, 3H), 3.62 (s, 3H), 3.17 (d, J = 10.2 Hz, 2H), 2.89-2.81 (m, 1H), 2.79-2.69 (m, 3H), 2.65-2.54 (m, 2H), 2.47-2.22 (m, 5H), 2.19-2.12 (m, 2H), 2.02-1.81 (m, 7H), 1.77-1.55 (m, 3H), 1.21-1.05 (m, 2H) |
| I-55 | AZK | BAS | 840.3 | 11.09 (s, 1H), 10.69 (s, 1H), 8.68 (s, 1H), 8.51-8.46 (m, 1H), 8.41 (t, J = 7.6 Hz, 1H), 8.34 (s, 1H), 8.21 (dd, J = 0.8, 7.6 Hz, 1H), 7.39 (s, 1H), 7.05-6.93 (m, 3H), 5.37 (dd, J = 5.2, 12.4 Hz, 1H), 4.61 (s, 1H), 4.46-4.32 (m, 1H), 4.05 (s, 1H), 4.00 (d, J = 7.6 Hz, 1H), 3.66 (dd, J = 1.6, 7.6 Hz, 1H), 3.59 (s, 3H), 3.44-3.41 (m, 1H), 3.26-3.22 (m, 2H), 3.04-2.96 (m, 2H), 2.93-2.84 (m, 1H), 2.77-2.61 (m, 2H), 2.21 (d, J = 6.8 Hz, 2H), 2.18-2.04 (m, 5H), 2.03-1.88 (m, 5H), 1.87-1.75 (m, 5H), 1.68-1.61 (m, 1H), 1.13 (q, J = 11.6 Hz, 2H) |
| I-56 | BRS | ATJ | 816.3 | 11.06 (s, 1H), 10.50 (s, 1H), 8.69 (s, 1H), 8.49-8.44 (m, 1H), 8.44-8.37 (m, 1H), 8.34 (s, 1H), 8.22 (dd, J = 1.2, 7.6 Hz, 1H), 7.16 (s, 1H), 6.71 (s, 2H), 5.32 (dd, J = 5.2, 12.8 Hz, 1H), 4.44-4.31 (m, 1H), 3.98 (s, 3H), 3.61 (s, 3H), 3.16-3.12 (m, 2H), 2.93-2.84 (m, 1H), 2.76-2.61 (m, 4H), 2.45-2.40 (m, 1H), 2.32-2.28 (m, 2H), 2.28 (s, 3H), 2.25 (s, 3H), 2.18-2.11 (m, 2H), 2.00-1.84 (m, 5H), 1.82-1.75 (m, 2H), 1.71-1.50 (m, 3H), 1.18-1.03 (m, 2H) |
| I-57 | AZK | BRP | 743.4 | 11.09 (s, 1H), 10.36 (s, 1H), 8.43-8.33 (m, 3H), 8.30 (d, J = 1.2 Hz, 1H), 8.20-8.13 (m, 1H), 7.64-7.59 (m, 1H), 7.58-7.52 (m, 1H), 7.05-6.95 (m, 3H), 5.37 (dd, J = 5.4, 12.4 Hz, 1H), 4.51-4.39 (m, 1H), 3.59 (s, 3H), 3.06-3.03 (m, 3H), 2.94-2.83 (m, 1H), 2.77-2.68 (m, 1H), 2.66-2.57 (m, 1H), 2.29-2.27 (m, 2H), 2.18-2.16 (m, 4H), 2.04-1.94 (m, 4H), 1.94-1.88 (m, 1H), 1.81-1.78 (m, 3H), 1.75-1.63 (m, 1H), 1.23-1.08 (m, 2H) |
| I-58 | AQK | BRP | 772.3 | 11.09 (s, 1H), 10.36 (s, 1H), 8.42-8.33 (m, 3H), 8.29 (d, J = 1.2 Hz, 1H), 8.20-8.14 (m, 1H), 7.64-7.59 (m, 1H), 7.58-7.52 (m, 1H), 7.01-6.95 (m, 1H), 6.94-6.84 (m, 2H), 5.35 (dd, J = 5.2, 12.4 Hz, 1H), 4.50-4.39 (m, 1H), 3.64 (s, 3H), 3.16 (d, J = 12.0 Hz, 3H), 2.95-2.83 (m, 1H), 2.78-2.60 (m, 4H), 2.34-2.29 (m, 2H), 2.27 (s, 3H), 2.16 (m, 2H), 2.04-1.89 (m, 5H), 1.80 (m 2H), 1.73-1.53 (m, 3H), 1.18-1.05 (m, 2H) |
| I-59 | AQK | BRQ | 803.6 | 11.09 (s, 1H), 10.14 (s, 1H), 8.47-8.34 (m, 2H), 8.21 (d, J = 8.4 Hz, 1H), 8.07 (d, J = 7.6 Hz, 1H), 7.46 (d, J = 12.0 Hz, 1H), 7.02-6.85 (m, 3H), 6.25 (s, 1H), 5.39-5.31 (m, 1H), 3.69 (s, 3H), 3.64 (s, |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| | | | | 3H), 3.17 (d, J = 10.0 Hz, 3H), 2.96-2.84 (m, 2H), 2.82-2.69 (m, 5H), 2.62-2.58 (s, 2H), 2.10-1.90 (m, 6H), 1.89-1.81 (m, 2H), 1.77-1.64 (m, 3H), 1.62-1.53 (m, 1H), 1.51-1.38 (m, 2H), 1.17-1.05 (m, 2H) |
| I-60 | BCD | BGF | 751.4 | 11.50 (s, 1H), 8.59 (s, 1H), 8.54 (s, 1H), 8.33 (s, 1H), 8.19 (s, 1H), 7.53 (s, 1H), 7.07-6.94 (m, 3H), 6.08 (s, 1H), 5.44 (dd, J = 5.2, 12.8 Hz, 1H), 4.47-4.35 (m, 1H), 3.59 (s, 3H), 3.03 (s, 3H), 3.02-2.91 (m, 4H), 2.82-2.64 (m, 3H), 2.22 (d, J = 6.8 Hz, 2H), 2.18-2.05 (m, 4H), 2.04-1.86 (m, 6H), 1.85-1.73 (m, 4H), 1.70-1.64 (m, 1H), 1.61 (s, 6H), 1.21-1.05 (m, 2H) |
| I-61 | BFL | BGF | 780.8 | 11.49 (s, 1H), 8.58 (s, 1H), 8.54 (s, 1H), 8.33 (s, 1H), 7.53 (s, 1H), 7.02-6.83 (m, 3H), 6.07 (s, 1H), 5.41 (dd, J = 5.2, 12.8 Hz, 1H), 4.46-4.37 (m, 1H), 3.65 (s, 3H), 3.19-3.13 (m, 2H), 3.03 (s, 3H), 2.98-2.95 (m, 1H), 2.81-2.71 (m, 6H), 2.30 (d, J = 6.8 Hz, 2H), 2.26 (s, 3H), 2.17-2.11 (m, 2H), 2.04-1.85 (m, 7H), 1.83-1.77 (m, 2H), 1.71-1.65 (m, 2H), 1.61 (s, 6H), 1.58-1.53 (m, 1H), 1.17-1.06 (m, 2H) |
| I-62 | AZK | BRR | 744.3 | 11.09 (s, 1H), 10.20 (s, 1H), 9.06 (s, 1H), 8.61 (s, 1H), 8.49-8.47 (m, 2H), 8.41 (t, J = 7.6 Hz, 1H), 8.23 (d, J = 7.6 Hz, 1H), 7.04-6.96 (m, 3H), 5.37 (dd, J = 5.2, 12.4 Hz, 1H), 4.60-4.55 (m, 1H), 3.59 (s, 3H), 3.22 (s, 1H), 3.01 (d, J = 10.4 Hz, 2H), 2.93-2.84 (m, 1H), 2.75-2.59 (m, 2H), 2.24-2.18 (m, 4H), 2.12-2.07 (m, 2H), 2.01-1.92 (m, 5H), 1.80-1.69 (m, 5H), 1.23-1.11 (m, 2H) |
| I-63 | AZK | BRV | 733.6 | 11.09 (s, 1H), 10.18 (d, J = 3.2 Hz, 1H), 9.39 (d, J = 7.2 Hz, 1H), 8.97-8.89 (m, 1H), 8.74 (s, 1H), 8.66 (d, J = 7.6 Hz, 1H), 8.46 (s, 1H), 8.31 (br s, 1H), 7.53 (d, J = 12.0 Hz, 1H), 7.36 (dd, J = 4.2, 6.8 Hz, 1H), 7.06-6.92 (m, 3H), 5.39-5.34 (m, 1H), 4.48-4.37 (m, 1H), 3.59 (s, 3H), 3.00-2.99 (m, 2H), 2.94-2.83 (m, 2H), 2.73-2.64 (m, 2H), 2.23-2.13 (m, 4H), 2.04-1.86 (m, 6H), 1.85-1.74 (m, 4H), 1.70-1.61 (m, 1H), 1.19-1.08 (m, 2H) |
| I-64 | BRY | AGL | 783.3 | 12.37 (s, 1H), 10.54 (s, 1H), 9.26 (s, 1H), 8.72 (s, 1H), 8.48 (s, 1H), 8.45 (d, J = 7.6 Hz, 1H), 8.37 (t, J = 7.6 Hz, 2H), 8.16 (d, J = 7.6 Hz, 1H), 8.06 (s, 1H), 7.92 (d, J = 8.8 Hz, 1H), 7.79 (dd, J = 1.4, 8.8 Hz, 1H), 7.58 (s, 1H), 5.94 (s, 1H), 4.47-4.41 (m, 1H), 3.97-3.90 (m, 1H), 3.76-3.70 (m, 1H), 3.08-3.04 (m, 2H), 3.01-2.92 (m, 1H), 2.79-2.71 (m, 2H), 2.29-2.25 (m, 2H), 2.21-2.07 (m, 4H), 2.03-1.76 (m, 8H), 1.71-1.67 (m, 1H), 1.62 (s, 6H), 1.24-1.08 (m, 2H) |
| I-65 | BRZ | AGL | 812.5 | 12.35 (s, 1H), 10.50 (d, J = 3.6 Hz, 1H), 9.07 (d, J = 3.6 Hz, 1H), 8.71 (d, J = 4.0 Hz, 1H), 8.45-8.43 (m, 1H), 8.41-8.32 (m, 2H), 8.26 (d, J = 4.4 Hz, 1H), 8.19-8.13 (m, 1H), 7.79-7.76 (m, 1H), 7.67-7.65 (m, 1H), 7.57 (d, J = 3.6 Hz, 1H), 7.42 (s, 1H), 5.94 (d, J = 4.4 Hz, 1H), 4.44-4.38 (m, 1H), 4.02-3.95 (m, 2H), 3.92-3.87 (m, 1H), 3.71-3.67 (m, 1H), 2.99-2.90 (m, 2H), 2.77-2.66 (m, 4H), 2.34-2.29 (m, 2H), 2.24 (s, 3H), 2.16-2.10 (m, 2H), 1.99-1.88 (m, 4H), 1.84-1.67 (m, 2H), 1.65-1.56 (m, 8H), 1.16-1.05 (m, 2H) |
| I-66 | BSA | AGL | 812.3 | 12.37 (s, 1H), 10.53 (s, 1H), 9.43 (s, 1H), 8.72 (s, 1H), 8.53 (s, 1H), 8.48-8.43 (m, 1H), 8.39-8.34 (m, 2H), 8.16 (d, J = 8.0 Hz, 1H), 7.74-7.68 (m, 1H), 7.62-7.56 (m, 2H), 7.26 (d, J = 7.6 Hz, 1H), 5.94 (s, 1H), 4.50-4.38 (m, 1H), 3.93-3.87 (m, 1H), 3.73-3.67 (m, 1H), 3.49-3.42 (m, 2H), 3.00-2.92 (m, 1H), 2.90-2.80 (m, 2H), 2.78-2.71 (m, 1H), 2.60-2.51 (m, 2H), 2.36 (d, J = 6.8 Hz, 2H), 2.31 (s, 3H), 2.16 (d, J = 12.0 Hz, 2H), 2.05-1.81 (m, 8H), 1.62 (s, 6H), 1.22-1.06 (m, 2H) |
| I-67 | BQM | BKQ | 775.5 | 11.08 (s, 1H), 10.23 (d, J = 2.4 Hz, 1H), 8.50 (s, 1H), 8.47-8.35 (m, 3H), 8.23 (dd, J = 1.2, 8.0 Hz, 1H), 7.55 (d, J = 12.0 Hz, 1H), 6.92-6.77 (m, 2H), 5.34 (dd, J = 5.2, 12.4 Hz, 1H), 4.53-4.39 |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | (m, 1H), 3.61 (s, 3H), 3.50-3.43 (m, 1H), 3.02 (d, J = 11.2 Hz, 2H), 2.93-2.82 (m, 1H), 2.74-2.58 (m, 2H), 2.46 (s, 3H), 2.30-2.14 (m, 6H), 2.10-1.89 (m, 7H), 1.69 (d, J = 10.0 Hz, 3H), 1.21-1.07 (m, 2H) |
| I-68 | BSN | BRP | 725.5 | 10.54 (s, 1H), 10.36 (s, 1H), 9.63 (s, 1H), 8.57 (s, 1H), 8.45-8.32 (m, 3H), 8.30 (s, 1H), 8.24-8.08 (m, 1H), 7.90-7.84 (m, 1H), 7.79 (t, J = 7.2 Hz, 1H), 7.69-7.58 (m, 2H), 7.58-7.50 (m, 1H), 4.53-4.42 (m, 1H), 3.92 (m, 1H), 3.76-3.65 (m, 2H), 3.21-3.11 (m, 3H), 2.98 (s, 1H), 2.76 (m, 1H), 2.47-2.34 (m, 3H), 2.25-2.13 (m, 2H), 2.09-1.84 (m, 8H), 1.82-1.71 (m, 1H), 1.27-1.11 (m, 2H) |
| I-69 | AZK | BSB | 783.4 | 11.09 (s, 1H), 10.74 (s, 1H), 8.68-8.61 (m, 1H), 8.53-8.46 (m, 1H), 8.45-8.36 (m, 2H), 8.24-8.22 (m, 1H), 7.49 (s, 1H), 7.06-6.94 (m, 3H), 5.37 (dd, J = 5.2, 12.4 Hz, 1H), 4.49-4.36 (m, 1H), 3.59 (s, 3H), 3.24-3.18 (m, 1H), 2.99 (d, J = 11.2 Hz, 2H), 2.95-2.81 (m, 1H), 2.77-2.68 (m, 1H), 2.62 (d, J = 17.6 Hz, 1H), 2.21 (d, J = 6.8 Hz, 2H), 2.18-2.12 (m, 2H), 2.10-2.04 (m, 2H), 2.03-1.86 (m, 6H), 1.85-1.73 (m, 4H), 1.70-1.60 (m, 1H), 1.20-1.05 (m, 4H), 0.81-0.74 (m, 2H) |
| I-70 | AZK | BSC | 757.4 | 11.10 (s, 1H), 10.13 (s, 1H), 8.47-8.35 (m, 3H), 8.24-8.13 (m, 2H), 7.51 (s, 1H), 7.11-6.93 (m, 3H), 5.38 (dd, J = 5.2, 12.8 Hz, 1H), 4.53-4.40 (m, 1H), 3.61 (s, 3H), 3.30 (s, 4H), 2.92-2.85 (m, 1H), 2.76-2.58 (m, 3H), 2.41 (s, 3H), 2.19 (d, J = 10.4 Hz, 3H), 2.10-1.67 (m, 11H), 1.31-1.16 (m, 2H) |
| I-72 | BQK | BKQ | 795.4 | 11.10 (s, 1H), 10.23 (d, J = 2.0 Hz, 1H), 8.50 (s, 1H), 8.47-8.36 (m, 3H), 8.22 (d, J = 7.6 Hz, 1H), 7.54 (d, J = 12.0 Hz, 1H), 7.19 (s, 1H), 7.01 (d, J = 1.6 Hz, 1H), 5.38 (dd, J = 5.2, 12.4 Hz, 1H), 4.52-4.39 (m, 1H), 3.58 (s, 3H), 2.98 (d, J = 10.8 Hz, 2H), 2.90-2.57 (m, 4H), 2.24-2.12 (m, 4H), 2.11-1.88 (m, 8H), 1.85-1.72 (m, 4H), 1.21-1.09 (m, 2H) |
| I-73 | BQM | BPQ | 791.3 | 11.08 (s, 1H), 10.52 (s, 1H), 8.64 (s, 1H), 8.54 (s, 1H), 8.49-8.39 (m, 2H), 8.24 (dd, J = 0.8, 7.6 Hz, 1H), 7.94 (s, 1H), 6.94-6.82 (m, 2H), 5.35 (dd, J = 5.2, 12.4 Hz, 1H), 4.58-4.45 (m, 1H), 3.64 (s, 3H), 3.59 (d, J = 14.4 Hz, 1H), 2.92-2.84 (m, 1H), 2.76-2.58 (m, 3H), 2.52 (s, 2H), 2.47 (s, 3H), 2.47-2.34 (m, 3H), 2.20 (d, J = 10.0 Hz, 3H), 2.05-1.91 (m, 6H), 1.90-1.72 (m, 3H), 1.35-1.12 (m, 2H) |
| I-74 | BSP | BRP | 761.3 | 11.12-11.08 (m, 1H), 10.36 (s, 1H), 8.42-8.33 (m, 3H), 8.30 (d, J = 1.2 Hz, 1H), 8.19-8.15 (m, 1H), 7.64-7.60 (m, 1H), 7.57-7.53 (m, 1H), 7.08-6.97 (m, 1H), 6.92-6.83 (m, 1H), 5.42-5.34 (m, 1H), 4.51-4.40 (m, 1H), 3.59 (s, 2H), 3.36 (s, 1H), 3.29 (s, 3H), 3.15-2.96 (m, 2H), 2.93-2.82 (m, 1H), 2.72-2.60 (m, 3H), 2.22-2.13 (m, 4H), 2.10 (d, J = 1.6 Hz, 1H), 2.04-1.93 (m, 6H), 1.80-1.74 (m, 1H), 1.73-1.62 (m, 1H), 1.21-1.11 (m, 2H) |
| I-75 | BRE | BRP | 772.8 | 11.09 (s, 1H), 10.37 (s, 1H), 8.42 (s, 1H), 8.41-8.33 (m, 2H), 8.31 (d, J = 1.3 Hz, 1H), 8.20-8.14 (m, 1H), 7.65-7.61 (m, 1H), 7.58-7.54 (m, 1H), 6.93 (d, J = 8.6 Hz, 1H), 6.74 (d, J = 8.8 Hz, 1H), 5.33 (dd, J = 5.2, 12.8 Hz, 1H), 4.53-4.42 (m, 1H), 3.79 (s, 3H), 3.58 (s, 3H), 3.19-3.09 (m, 2H), 2.94-2.83 (m, 1H), 2.76-2.57 (m, 3H), 2.49-2.42 (m, 4H), 2.25-2.15 (m, 3H), 2.05-1.89 (m, 6H), 1.82-1.71 (m, 1H), 1.66 (d, J = 10.4 Hz, 2H), 1.25-1.14 (m, 2H) |
| I-76 | AZK | BSQ | 811.3 | 11.09 (s, 1H), 10.29 (s, 1H), 8.65 (s, 1H), 8.47-8.39 (m, 3H), 8.24 (dd, J = 1.2, 7.6 Hz, 1H), 8.19 (s, 1H), 7.06-6.95 (m, 3H), 5.37 (dd, J = 5.6, 12.4 Hz, 1H), 4.61-4.53 (m, 1H), 3.59 (s, 3H), 3.00 (d, J = 11.6 Hz, 2H), 2.93-2.84 (m, 1H), 2.75-2.69 (m, 1H), 2.65-2.59 (m, 2H), 2.23-2.17 (m, 4H), 2.11-2.04 (dt, J = 2.8, 11.6 Hz, 2H), 2.02-1.95 (m, 5H), 1.85-1.75 (m, 4H), 1.71-1.65 (m, 1H), 1.23-1.10 (m, 2H) |
| I-79 | BSA | BRR | 755.2 | 10.52 (s, 1H), 10.20 (s, 1H), 9.43 (s, 1H), 9.07 (s, 1H), 8.62 (s, 1H), 8.53 (s, 1H), 8.50-8.47 (m, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 2H), 8.42 (t, J = 7.6 Hz, 1H), 8.23 (d, J = 7.6 Hz, 1H), 7.75-7.68 (m, 1H), 7.60 (d, J = 8.4 Hz, 1H), 7.26 (d, J = 7.6 Hz, 1H), 4.64-4.53 (m, 1H), 3.95-3.85 (m, 1H), 3.75-3.65 (m, 1H), 3.52-3.45 (m, 2H), 3.00-2.92 (m, 1H), 2.91-2.79 (m, 2H), 2.79-2.71 (m, 1H), 2.61-2.54 (m, 1H), 2.37 (d, J = 6.8 Hz, 2H), 2.32 (s, 3H), 2.22-2.19 (m, 2H), 2.06-1.94 (m, 4H), 1.88 (m, 4H), 1.68-1.55 (m, 1H), 1.23-1.09 (m, 2H) |
| I-82 | BSP | BRR | 762.4 | 11.11 (s, 1H), 10.20 (s, 1H), 9.06 (s, 1H), 8.61 (s, 1H), 8.50-8.47 (m, 2H), 8.42 (t, J = 7.6 Hz, 1H), 8.23 (d, J = 8.0 Hz, 1H), 7.08-6.98 (m, 1H), 6.92-6.85 (m, 1H), 5.40-5.35 (m, 1H), 4.63-4.55 (m, 1H), 3.60 (s, 2H), 3.37-3.35 (m, 1H), 3.30 (s, 3H), 3.19-3.02 (m, 2H), 2.92-2.83 (m, 1H), 2.75-2.69 (m, 1H), 2.65-2.52 (m, 3H), 2.23-2.20(m, 3H), 2.02-1.94 (m, 6H), 1.86-1.71 (m, 3H), 1.24-1.14 (m, 2H) |
| I-83 | BRE | BRR | 774.5 | 11.08 (s, 1H), 10.21 (s, 1H), 9.07 (s, 1H), 8.62 (s, 1H), 8.51-8.48 (m, 2H), 8.42 (t, J = 8.0 Hz, 1H), 8.24 (dd, J = 0.8, 7.6 Hz, 1H), 6.91 (d, J = 8.8 Hz, 1H), 6.73 (d, J = 8.8 Hz, 1H), 5.33 (dd, J = 5.6, 12.4 Hz, 1H), 4.64-4.54 (m, 1H), 3.77 (s, 3H), 3.57 (s, 3H), 2.99 (d, J = 10.4 Hz, 2H), 2.92-2.84 (m, 1H), 2.71-2.60 (m, 2H), 2.42 (d, J = 11.6 Hz, 2H), 2.22 (d, J = 6.8 Hz, 4H), 2.07-1.94 (m, 8H), 1.76-1.64 (m, 1H), 1.59 (d, J = 12.0 Hz, 2H), 1.22-1.12 (m, 2H) |
| I-84 | AQK | BSU | 800.5 | 11.08 (s, 1H), 8.81 (d, J = 2.0 Hz, 1H), 8.67 (d, J = 2.0 Hz, 1H), 8.62 (d, J = 7.2 Hz, 1H), 8.59-8.54 (m, 2H), 8.52 (d, J = 3.9 Hz, 1H), 8.08 (s, 1H), 6.99-6.93 (m, 1H), 6.92-6.84 (m, 3H), 5.34 (dd, J = 5.2, 12.8 Hz, 1H), 3.84-3.74 (m, 1H), 3.62 (s, 3H), 3.17-3.09 (m, 4H), 2.93-2.83 (m, 1H), 2.78-2.54 (m, 6H), 2.36-2.25 (m, 4H), 2.04-1.95 (m, 1H), 1.81 (t, J = 12.4 Hz, 6H), 1.72-1.61 (m, 2H), 1.56-1.41 (m, 2H), 1.29 (d, J = 6.4 Hz, 6H), 1.01-0.82 (m, 4H) |
| I-85 | AZK | BSU | 771.5 | 11.08 (s, 1H), 8.81 (d, J = 2.0 Hz, 1H), 8.67 (d, J = 2.0 Hz, 1H), 8.63 (d, J = 7.2 Hz, 1H), 8.59-8.55 (m, 2H), 8.52 (d, J = 4.0 Hz, 1H), 8.08 (s, 1H), 7.06-6.93 (m, 3H), 6.88 (d, J = 4.0 Hz, 1H), 5.40-5.32 (m, 1H), 3.83-3.72 (m, 1H), 3.57 (s, 3H), 3.23-3.18 (m, 1H), 3.14-3.06 (m, 2H), 3.01-2.92 (m, 2H), 2.90-2.82 (m, 1H), 2.74-2.58 (m, 2H), 2.16 (d, J = 5.6 Hz, 2H), 2.09-1.97 (m, 3H), 1.85-1.73 (m, 8H), 1.55-1.45 (m, 2H), 1.29 (d, J = 6.4 Hz, 6H), 0.99-0.80 (m, 4H) |
| I-88 | BQL | BRR | 778.4 | 11.12 (s, 1H), 10.20 (s, 1H), 9.07 (s, 1H), 8.61 (s, 1H), 8.51-8.47 (m, 2H), 8.44-8.39 (m, 1H), 8.24 (d, J = 8.4 Hz, 1H), 7.14-7.04 (m, 2H), 5.40 (dd, J = 5.2, 12.5 Hz, 1H), 4.65-4.57 (m, 1H), 3.66 (s, 3H), 3.10-2.97 (m, 2H), 2.93-2.83 (m, 2H), 2.75-2.70 (m, 1H), 2.68-2.63 (m, 2H), 2.62-2.57 (m, 1H), 2.26-2.17 (m, 3H), 2.07-1.91 (m, 8H), 1.78-1.58 (m, 2H), 1.34-1.13 (m, 3H) |
| I-96 | BSA | ATJ | 784.3 | 10.52 (d, J = 9.2 Hz, 2H), 9.43 (s, 1H), 8.69 (s, 1H), 8.53 (s, 1H), 8.49-8.44 (m, 1H), 8.44-8.38 (m, 1H), 8.35 (s, 1H), 8.22 (dd, J = 1.2, 7.6 Hz, 1H), 7.74-7.67 (m, 1H), 7.60 (d, J = 8.4 Hz, 1H), 7.26 (d, J = 7.6 Hz, 1H), 7.16 (s, 1H), 4.44-4.34 (m, 1H), 3.98 (s, 3H), 3.90 (ddd, J = 5.2, 10.0, 12.2 Hz, 1H), 3.70 (td, J = 6.0, 12.2 Hz, 1H), 3.50-3.42 (m, 2H), 2.96 (ddd, J = 6.0, 10.0, 16.4 Hz, 1H), 2.90-2.81 (m, 2H), 2.80-2.71 (m, 1H), 2.64-2.54 (m, 1H), 2.39 (d, J = 6.4 Hz, 2H), 2.33 (s, 3H), 2.21-2.10 (m, 2H), 2.00 (d, J = 11.6 Hz, 2H), 1.85 (m, 6H), 1.67-1.53 (m, 1H), 1.21-1.08 (m, 2H) |
| I-97 | BSN | ATJ | 754.2 | 10.54 (s, 1H), 10.51 (s, 1H), 9.66 (s, 1H), 8.70 (s, 1H), 8.59 (s, 1H), 8.46 (d, J = 8.0 Hz, 1H), 8.43-8.38 (m, 1H), 8.35 (s, 1H), 8.22 (d, J = 7.6 Hz, 1H), 7.91-7.87 (d, J = 8.4 Hz, 1H), 7.84-7.78 (m, 1H), 7.67-7.62 (m, 1H), 7.16 (s, 1H), 4.46- |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 4.36 (m, 1H), 3.99 (s, 3H), 3.96-3.88 (m, 1H), 3.85-3.65 (m, 2H), 3.04-2.93 (m, 1H), 2.91-2.56 (m, 4H), 2.54-2.51 (m, 3H), 2.23-2.14 (m, 2H), 2.11-1.89 (m, 8H), 1.87-1.75 (m, 1H), 1.30-1.13 (m, 2H) |
| I-98 | BSA | BTW | 754.2 | 10.52 (s, 1H), 10.36 (s, 1H), 9.43 (s, 1H), 8.53 (s, 1H), 8.44-8.37 (m, 2H), 8.37-8.21 (m, 2H), 8.17 (d, J = 7.5 Hz, 1H), 7.74-7.68 (m, 1H), 7.64-7.58 (m, 2H), 7.57-7.53 (m, 1H), 7.26 (d, J = 7.5 Hz, 1H), 4.52-4.40 (m, 1H), 3.90 (d, J = 5.1, 9.8, 12.2 Hz, 1H), 3.74-3.66 (m, 1H), 3.55-3.40 (m, 3H), 3.04-2.91 (m, 1H), 2.90-2.71 (m, 3H), 2.36 (br d, J = 6.5 Hz, 2H), 2.32 (s, 3H), 2.18 (br d, J = 10.8 Hz, 2H), 2.09-1.92 (m, 4H), 1.88 (s, 4H), 1.67-1.52 (m, 1H), 1.22-1.08 (m, 2H) |
| I-99 | BQM | BTW | 757.3 | 11.08 (s, 1H), 10.36 (s, 1H), 8.42-8.33 (m, 3H), 8.30 (s, 1H), 8.17 (d, J = 7.6 Hz, 1H), 7.63 (d, J = 9.2 Hz, 1H), 7.57-7.53 (m, 1H), 6.92-6.87 (m, 1H), 6.85-6.81 (m, 1H), 5.38-5.31 (m, 1H), 4.52-4.43 (m, 1H), 3.63 (s, 3H), 3.61-3.56 (m, 1H), 3.25-3.23 (m, 1H), 2.94-2.83 (m, 1H), 2.76-2.58 (m, 3H), 2.54-2.51 (m, 2H), 2.47 (s, 3H), 2.40-2.29 (m, 3H), 2.23-2.15 (m, 2H), 2.05-1.90 (m, 6H), 1.86-1.73 (m, 3H), 1.27-1.74 (m, 2H) |
| I-100 | AQK | BUA | 826.4 | 11.10 (s, 1H), 8.93 (s, 1H), 8.51 (s, 1H), 8.41 (d, J = 8.0 Hz, 1H), 8.28-8.22 (m, 1H), 8.02 (s, 1H), 7.90 (d, J = 8.0 Hz, 1H), 7.28 (s, 1H), 7.02-6.86 (m, 3H), 5.36 (dd, J = 5.6, 12.8 Hz, 1H), 4.53-4.43 (m, 1H), 3.87 (s, 3H), 3.65 (s, 3H), 3.16 (d, J = 10.8 Hz, 2H), 2.96-2.85 (m, 1H), 2.77-2.61 (m, 4H), 2.48-2.42 (m, 1H), 2.31 (d, J = 6.4 Hz, 2H), 2.27 (s, 3H), 2.18 (d, J = 10.8 Hz, 2H), 2.03-1.89 (m, 5H), 1.81 (d, J = 10.8 Hz, 2H), 1.73-1.53 (m, 3H), 1.20-1.07 (m, 2H) |
| I-101 | BSP | ATJ | 791.3 | 11.11 (s, 1H), 10.51 (s, 1H), 8.71-8.67 (m, 1H), 8.47 (d, J = 1.2, 7.2 Hz, 1H), 8.43-8.38 (m, 1H), 8.34 (s, 1H), 8.24-8.20 (m, 1H), 7.18-7.14 (m, 1H), 7.09-6.99 (m, 1H), 6.94-6.86 (m, 1H), 5.43-5.36 (m, 1H), 4.46-4.36 (m, 1H), 3.99 (s, 3H), 3.63 (s, 2H), 3.36 (s, 1H), 3.30 (s, 3H), 2.92-2.83 (m, 1H), 2.76-2.58 (m, 3H), 2.53-2.52 (m, 3H), 2.32-2.25 (m, 1H), 2.24-2.11 (m, 3H), 2.05-1.83 (m, 8H), 1.31-1.14 (m, 2H) |
| I-102 | BQM | BRR | 758.4 | 11.08 (s, 1H), 10.20 (s, 1H), 9.07 (s, 1H), 8.61 (s, 1H), 8.52-8.46 (m, 2H), 8.41 (t, J = 7.6 Hz, 1H), 8.23 (d, J = 7.6 Hz, 1H), 6.93-6.78 (m, 2H), 5.34 (dd, J = 5.2, 12.6 Hz, 1H), 4.66-4.54 (m, 1H), 3.63 (s, 3H), 3.61-3.53 (m, 1H), 3.24-3.16 (m, 2H), 2.95-2.83 (m, 1H), 2.75-2.55 (m, 3H), 2.47 (s, 3H), 2.39-2.27 (m, 3H), 2.22 (d, J = 9.6 Hz, 2H), 2.07-1.91 (m, 6H), 1.77 (d, J = 9.6 Hz, 4H), 1.30-1.13 (m, 2H) |
| I-103 | BSN | BRR | 726.6 | 10.54 (s, 1H), 10.20 (s, 1H), 9.64 (s, 1H), 9.07 (d, J = 1.0 Hz, 1H), 8.60 (d, J = 14.2 Hz, 2H), 8.52-8.45 (m, 2H), 8.41 (t, J = 7.8 Hz, 1H), 8.23 (dd, J = 1.0, 7.8 Hz, 1H), 7.91-7.84 (m, 1H), 7.80 (t, J = 7.8 Hz, 1H), 7.65 (d, J = 6.6 Hz, 1H), 4.66-4.54 (m, 1H), 3.93 (ddd, J = 5.2, 9.8, 12.2 Hz, 1H), 3.72 (d, J = 6.0, 12.2 Hz, 2H), 3.25-3.06 (m, 2H), 3.02-2.93 (m, 1H), 2.80-2.73 (m, 1H), 2.64-2.52 (m, 1H), 2.39 (dd, J = 3.0, 8.8 Hz, 2H), 2.22 (d, J = 10.4 Hz, 2H), 2.10-1.90 (m, 8H), 1.86-1.75 (m, 1H), 1.29-1.15 (m, 2H) |
| I-104 | BUC | BRR | 774.6 | 11.08 (s, 1H), 10.20 (s, 1H), 9.07 (s, 1H), 8.62 (s, 1H), 8.51-8.47 (m, 2H), 8.45-8.39 (m, 1H), 8.24 (d, J = 7.6 Hz, 1H), 6.93 (d, J = 8.4 Hz, 1H), 6.73 (d, J = 8.8 Hz, 1H), 5.39-5.27 (m, 1H), 4.60 (t, J = 11.6 Hz, 1H), 3.78 (s, 3H), 3.58 (s, 3H), 3.40 (s, 1H), 3.18 (s, 2H), 2.96-2.83 (m, 1H), 2.76-2.58 (m, 3H), 2.49-2.42 (m, 4H), 2.22 (d, J = 8.4 Hz, 2H), 2.10-1.89 (m, 6H), 1.86-1.74 (m, 1H), 1.67 (d, J = 10.4 Hz, 2H), 1.31-1.12 (m, 2H) |
| I-105[b] | AQK | BVL | 800.5 | 11.08 (s, 1H), 8.81 (d, J = 2.0 Hz, 1H), 8.67 (d, J = 2.0 Hz, 1H), 8.62 (d, J = 7.2 Hz, 1H), 8.59-8.54 (m, 2H), 8.52 (d, J = 3.9 Hz, 1H), 8.08 (s, 1H), |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 6.99-6.93 (m, 1H), 6.92-6.84 (m, 3H), 5.34 (dd, J = 5.2, 12.8 Hz, 1H), 3.84-3.74 (m, 1H), 3.62 (s, 3H), 3.17-3.09 (m, 4H), 2.93-2.83 (m, 1H), 2.78-2.54 (m, 6H), 2.36-2.25 (m, 4H), 2.04-1.95 (m, 1H), 1.81 (t, J = 12.4 Hz, 6H), 1.72-1.61 (m, 2H), 1.56-1.41 (m, 2H), 1.29 (d, J = 6.4 Hz, 6H), 1.01-0.82 (m, 4H) |
| I-106 | BQL | BTW | 777.4 | 11.16-11.06 (m, 1H), 10.36 (s, 1H), 8.42-8.33 (m, 3H), 8.30 (s, 1H), 8.21-8.15 (m, 1H), 7.66-7.52 (m, 2H), 7.14-7.00 (m, 2H), 5.39 (dd, J = 5.2, 12.8 Hz, 1H), 4.50-4.40 (m, 1H), 3.62 (s, 3H), 3.54-3.46 (m, 1H), 3.01 (d, J = 10.4 Hz, 2H), 2.92-2.82 (m, 1H), 2.75-2.67 (m, 1H), 2.67 (s, 3H), 2.24-2.14 (m, 4H), 2.07-1.95 (m, 6H), 1.93 (s, 1H), 1.65 (d, J = 11.2 Hz, 3H), 1.22-1.07 (m, 2H) |
| I-107 | AZK | BUE | 786.7 | 11.09 (s, 1H), 11.05 (s, 1H), 8.71 (s, 1H), 8.51-8.44 (m, 1H), 8.43-8.37 (m, 1H), 8.35 (s, 1H), 8.21 (d, J = 8.0 Hz, 1H), 7.44 (s, 1H), 7.06-6.93 (m, 3H), 5.37 (dd, J = 5.2, 12.4 Hz, 1H), 4.47-4.33 (m, 1H), 3.59 (s, 3H), 3.21-3.16 (m, 1H), 2.99 (d, J = 11.2 Hz, 2H), 2.94-2.83 (m, 1H), 2.74 (s, 6H), 2.72-2.60 (m, 2H), 2.21 (d, J = 7.2 Hz, 2H), 2.18-2.12 (m, 2H), 2.11-2.03 (m, 2H), 2.02-1.86 (m, 5H), 1.84-1.71 (m, 4H), 1.70-1.59 (m, 1H), 1.20-1.05 (m, 2H) |
| I-108 | BQM | BUL | 787.6 | 11.07 (s, 1H), 10.01 (s, 1H), 9.37 (s, 1H), 9.18 (s, 1H), 8.67 (s, 1H), 8.32 (s, 1H), 8.03 (s, 1H), 7.09 (s, 1H), 6.90-6.79 (m, 2H), 5.34 (dd, J = 5.2, 12.8 Hz, 1H), 4.47-4.31 (m, 1H), 3.87 (s, 3H), 3.61 (s, 3H), 3.50-3.42 (m, 1H), 3.01-2.99 (m, 2H), 2.93-2.82 (m, 1H), 2.70-2.56 (m, 2H), 2.46 (s, 3H), 2.30-2.13 (m, 6H), 2.08-1.85 (m, 7H), 1.96-1.69 (m, 3H), 1.21-1.07 (m, 2H) |
| I-109[b] | BQM | BVB | 744.6 | 11.07 (s, 1H), 9.90 (s, 1H), 9.31 (s, 1H), 9.21 (d, J = 1.6 Hz, 1H), 8.78 (s, 1H), 8.31 (s, 1H), 8.08 (s, 1H), 7.09 (s, 1H), 6.90-6.85 (m, 1H), 6.84-6.80 (m, 1H), 5.34 (dd, J = 5.2, 12.4 Hz, 1H), 4.43-4.34 (m, 1H), 3.88 (s, 3H), 3.61 (s, 3H), 3.49-3.42 (m, 1H), 3.02 (d, J = 10.4 Hz, 2H), 2.92-2.83 (m, 1H), 2.67 (d, J = 3.6 Hz, 1H), 2.64-2.58 (m, 1H), 2.46 (s, 2H), 2.31-2.12 (m, 7H), 2.08-1.86 (m, 8H), 1.69 (d, J = 12.0 Hz, 3H), 1.18-1.10 (m, 2H) |
| I-110 | BQM | BUK | 753.5 | 11.07 (s, 1H), 9.82 (s, 1H), 9.05 (s, 1H), 8.83 (d, J = 2.0 Hz, 1H), 8.41 (s, 1H), 8.31 (s, 1H), 8.03 (s, 1H), 7.08 (s, 1H), 6.94-6.75 (m, 2H), 5.40-5.23 (m, 1H), 4.46-4.29 (m, 1H), 3.87 (s, 3H), 3.61 (s, 3H), 3.51-3.39 (m, 1H), 3.05-2.96 (m, 2H), 2.91-2.81 (m, 1H), 2.71-2.61 (m, 2H), 2.46 (s, 3H), 2.29-2.13 (m, 6H), 2.06-1.83 (m, 7H), 1.74-1.60 (m, 3H), 1.20-1.08 (m, 2H) |
| I-111 | BUC | BUK | 769.6 | 11.07 (s, 1H), 9.83 (s, 1H), 9.05 (s, 1H), 8.83 (d, J = 2.3 Hz, 1H), 8.41 (s, 1H), 8.31 (s, 1H), 8.03 (s, 1H), 7.08 (s, 1H), 6.91 (d, J = 8.4 Hz, 1H), 6.72 (d, J = 8.4 Hz, 1H), 5.39-5.27 (m, 1H), 4.47-4.31 (m, 1H), 3.87 (s, 3H), 3.77 (s, 3H), 3.56 (s, 3H), 2.97 (d, J = 10.0 Hz, 2H), 2.89-2.82 (m, 1H), 2.71-2.62 (m, 2H), 2.42-2.32 (m, 3H), 2.21-2.11 (m, 4H), 2.04-1.88 (m, 7H), 1.58 (d, J = 11.2 Hz, 3H), 1.20-1.09 (m, 2H) |
| I-112 | AZK | BUM | 744.2 | 12.34 (s, 1H), 11.09 (s, 1H), 8.55 (dd, J = 1.6, 4.8 Hz, 1H), 8.51 (s, 1H), 8.31 (s, 1H), 8.22 (dd, J = 1.6, 8.0 Hz, 1H), 8.09 (d, J = 4.0 Hz, 1H), 7.44-7.38 (m, 1H), 7.15 (s, 1H), 7.05-6.92 (m, 3H), 6.81 (d, J = 4.0 Hz, 1H), 5.37 (dd, J = 5.6, 12.4 Hz, 1H), 4.41-4.32 (m, 1H), 4.05 (s, 3H), 3.59 (s, 3H), 3.22-3.17 (m, 1H), 2.99 (d, J = 11.2 Hz, 2H), 2.94-2.84 (m, 1H), 2.78-2.68 (m, 1H), 2.66-2.58 (m, 1H), 2.21 (d, J = 7.2 Hz, 2H), 2.15 (d, J = 12.0 Hz, 2H), 2.10-2.04 (m, 2H), 2.01-1.95 (m, 3H), 1.93-1.85 (m, 2H), 1.83-1.75 (m, 4H), 1.70-1.60 (m, 1H), 1.18-1.07 (m, 2H) |
| I-113 | AQK | BUM | 773.3 | 12.34 (s, 1H), 11.09 (s, 1H), 8.55 (dd, J = 1.6, 4.8 Hz, 1H), 8.51 (s, 1H), 8.31 (s, 1H), 8.22 (dd, J = |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 1.6, 7.6 Hz, 1H), 8.09 (d, J = 4.0 Hz, 1H), 7.44-7.38 (m, 1H), 7.14 (s, 1H), 7.00-6.94 (m, 1H), 6.93-6.84 (m, 2H), 6.81 (d, J = 4.0 Hz, 1H), 5.35 (dd, J = 5.2, 12.4 Hz, 1H), 4.44-4.30 (m, 1H), 4.05 (s, 3H), 3.64 (s, 3H), 3.15 (d, J = 10.8 Hz, 2H), 2.95-2.84 (m, 1H), 2.76-2.58 (m, 4H), 2.46-2.42 (m, 1H), 2.30 (d, J = 6.8 Hz, 2H), 2.26 (s, 3H), 2.21-2.10 (m, 2H), 2.03-1.84 (m, 5H), 1.84-1.75 (m, 2H), 1.73-1.60 (m, 2H), 1.59-1.48 (m, 1H), 1.19-1.03 (m, 2H) |
| I-114 | AZK | BUR | 757.6 | 11.10 (s, 1H), 8.82 (d, J = 2.0 Hz, 1H), 8.68 (d, J = 2.0 Hz, 1H), 8.63-8.56 (m, 2H), 8.53 (d, J = 4.0 Hz, 1H), 8.34 (d, J = 8.0 Hz, 1H), 8.09 (s, 1H), 7.05-6.95 (m, 3H), 6.90 (d, J = 4.0 Hz, 1H), 5.38 (dd, J = 5.2, 12.8 Hz, 1H), 3.82-3.71 (m, 2H), 3.59 (s, 3H), 3.25-3.18 (m, 1H), 3.02-2.85 (m, 3H), 2.78-2.59 (m, 2H), 2.18 (d, J = 6.4 Hz, 2H), 2.10-1.97 (m, 3H), 1.93-1.75 (m, 8H), 1.57-1.46 (m, 1H), 1.42-1.33 (m, 2H), 1.30 (d, J = 6.4 Hz, 6H), 1.04-0.91 (m, 2H) |
| I-115 | AQK | BUS | 772.6 | 11.08 (s, 1H), 8.80 (d, J = 2.0 Hz, 1H), 8.67 (d, J = 2.0 Hz, 1H), 8.49 (d, J = 4.0 Hz, 1H), 8.03 (d, J = 5.6 Hz, 2H), 7.00-6.94 (m, 1H), 6.92-6.84 (m, 3H), 6.22 (d, J = 7.6 Hz, 1H), 5.35 (dd, J = 5.2, 12.4 Hz, 1H), 4.33-3.87 (m, 2H), 3.84-3.74 (m, 1H), 3.63 (s, 3H), 3.15 (d, J = 10.8 Hz, 2H), 3.01-2.84 (m, 3H), 2.77-2.56 (m, 5H), 2.42-2.28 (m, 6H), 2.04-1.95 (m, 1H), 1.79 (d, J = 8.8 Hz, 4H), 1.66 (d, J = 9.6 Hz, 2H), 1.28 (d, J = 6.4 Hz, 6H), 1.19-1.09 (m, 2H) |
| I-116 | BUC | BUT | 739.2 | 11.07 (s, 1H), 10.45 (s, 1H), 9.06 (d, J = 1.6 Hz, 1H), 8.83 (d, J = 2.4 Hz, 1H), 8.44 (t, J = 2.0 Hz, 1H), 8.40 (s, 1H), 8.25 (s, 1H), 7.61 (d, J = 9.2 Hz, 1H), 7.45 (dd, J = 1.6, 9.2 Hz, 1H), 6.91 (d, J = 8.4 Hz, 1H), 6.72 (d, J = 8.8 Hz, 1H), 5.32 (dd, J = 5.2, 12.8 Hz, 1H), 4.52-4.36 (m, 1H), 3.77 (s, 3H), 3.56 (s, 3H), 2.97 (d, J = 10.0 Hz, 2H), 2.93-2.83 (m, 1H), 2.76-2.61 (m, 2H), 2.40 (s, 2H), 2.23-2.14 (m, 4H), 2.05-1.79 (m, 8H), 1.74-1.63 (m, 1H), 1.58 (d, J = 12.4 Hz, 2H), 1.21-1.07 (m, 2H) |
| I-117 | BSA | BUK | 750.5 | 10.53 (s, 1H), 9.83 (s, 1H), 9.43 (s, 1H), 9.05 (s, 1H), 8.83 (d, J = 2.0 Hz, 1H), 8.53 (s, 1H), 8.41 (s, 1H), 8.31 (s, 1H), 8.03 (s, 1H), 7.76-7.67 (m, 1H), 7.60 (d, J = 8.4 Hz, 1H), 7.26 (d, J = 7.6 Hz, 1H), 7.08 (s, 1H), 4.48-4.31 (m, 1H), 3.95-3.89 (m, 1H), 3.87 (s, 3H), 3.73-3.67 (m, 1H), 3.53-3.43 (m, 3H), 3.00-2.92 (m, 1H), 2.92-2.80 (m, 2H), 2.80-2.71 (m, 1H), 2.62-2.53 (m, 1H), 2.37 (d, J = 6.8 Hz, 2H), 2.32 (s, 3H), 2.16 (d, J = 10.8 Hz, 2H), 2.00 (d, J = 11.6 Hz, 2H), 1.94-1.82 (m, 5H), 1.65-1.53 (m, 1H), 1.18-1.09 (m, 2H) |
| I-118 | AQK | BUR | 786.4 | 11.09 (s, 1H), 8.81 (d, J = 2.0 Hz, 1H), 8.67 (d, J = 2.0 Hz, 1H), 8.62-8.55 (m, 2H), 8.52 (d, J = 4.0 Hz, 1H), 8.32 (d, J = 7.6 Hz, 1H), 8.08 (s, 1H), 7.01-6.93 (m, 1H), 6.93-6.84 (m, 3H), 5.35 (dd, J = 5.6, 12.4 Hz, 1H), 3.75 (d, J = 6.0, 12.8 Hz, 2H), 3.64 (s, 3H), 3.15 (d, J = 11.2 Hz, 2H), 2.95-2.84 (m, 1H), 2.77-2.58 (m, 4H), 2.45-2.39 (m, 1H), 2.28-2.21 (m, 5H), 2.04-1.96 (m, 1H), 1.92-1.75 (m, 6H), 1.71-1.57 (m, 2H), 1.44-1.31 (m, 3H), 1.29 (d, J = 6.4 Hz, 6H), 0.94 (q, J = 12.0 Hz, 2H) |
| I-119 | BRY | BUY | 727.2 | 10.52 (d, J = 6.4 Hz, 2H), 9.25 (s, 1H), 8.69 (s, 1H), 8.50-8.40 (m, 3H), 8.38 (s, 1H), 8.23-8.20 (m, 1H), 8.06 (s, 1H), 7.91 (d, J = 8.4 Hz, 1H), 7.79 (dd, J = 1.6, 8.8 Hz, 1H), 7.20 (s, 1H), 5.27-5.17 (m, 1H), 3.99 (s, 3H), 3.96-3.89 (m, 1H), 3.72 (td, J = 6.0, 12.0 Hz, 1H), 3.06 (d, J = 11.6 Hz, 2H), 3.00-2.92 (m, 1H), 2.79-2.70 (m, 5H), 2.62-2.59 (s, 2H), 2.37-2.32 (m, 2H), 2.18-2.12 (m, 2H), 1.89-1.76 (m, 4H) |
| I-120 | BRY | BTO | 772.6 | 10.53 (s, 1H), 9.88 (s, 1H), 9.26 (s, 1H), 8.48 (s, 1H), 8.31 (s, 1H), 8.17 (d, J = 3.2 Hz, 1H), 8.11 (d, J = 8.4 Hz, 1H), 8.07 (s, 1H), 7.99-7.94 (m, 2H), 7.92 (d, J = 8.8 Hz, 1H), 7.79 (dd, J = 1.4, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 8.8 Hz, 1H), 7.08 (s, 1H), 4.44-4.35 (m, 1H), 3.93 (m, 1H), 3.86 (s, 3H), 3.76-3.69 (m, 1H), 3.06-2.99 (m, 2H), 2.99-2.91 (m, 1H), 2.76 (td, J = 5.6, 16.8 Hz, 2H), 2.23 (d, J = 7.0 Hz, 2H), 2.17 (d, J = 11.2 Hz, 2H), 2.07 (t, J = 10.4 Hz, 2H), 1.99 (d, J = 15.0 Hz, 2H), 1.93 (d, J = 2.4 Hz, 1H), 1.91-1.84 (m, 3H), 1.80 (d, J = 10.0 Hz, 2H), 1.73-1.62 (m, 1H), 1.21-1.09 (m, 2H) |
| I-121 | BSN | BVB | 712.3 | 10.54 (s, 1H), 9.90 (s, 1H), 9.61 (s, 1H), 9.31 (s, 1H), 9.21 (d, J = 1.6 Hz, 1H), 8.78 (s, 1H), 8.57 (s, 1H), 8.32 (s, 1H), 8.08 (s, 1H), 7.89-7.83 (m, 1H), 7.78 (t, J = 7.6 Hz, 1H), 7.66 (d, J = 7.2 Hz, 1H), 7.09 (s, 1H), 4.45-4.34 (m, 1H), 3.96-3.91 (m, 1H), 3.88 (s, 3H), 3.75-3.68 (m, 1H), 3.64 3.56 (m, 1H), 3.08-3.01 (m, 2H), 3.01-2.93 (m, 1H), 2.80-2.72 (m, 1H), 2.60-2.55 (m, 2H), 2.28-2.26 (m, 2H), 2.25-2.21 (m, 1H), 2.20-2.13 (m, 2H), 2.05-1.97 (m, 2H), 1.94-1.84 (m, 5H), 1.75-1.65 (m, 1H), 1.22-1.08 (m, 2H) |
| I-122 | BRY | BVB | 712.6 | 10.54 (s, 1H), 9.90 (s, 1H), 9.32-9.20 (m, 2H), 8.78 (s, 1H), 8.48 (s, 1H), 8.31 (s, 1H), 8.14-8.06 (m, 2H), 7.92 (d, J = 8.4 Hz, 1H), 7.78 (dd, J = 1.6, 8.8 Hz, 1H), 7.63-7.45 (m, 1H), 7.08 (s, 1H), 4.45-4.37 (m, 1H), 3.97-3.90 (m, 1H), 3.87 (s, 3H), 3.72 (td, J = 6.0, 12.0 Hz, 1H), 3.17-3.07 (m, 2H), 3.01-2.92 (m, 1H), 2.84-2.72 (m, 2H), 2.53-2.51 (m, 2H), 2.38-2.34 (m, 1H), 2.19-2.15 (m, 2H), 2.03-1.96 (m, 2H), 1.94-1.82 (m, 6H), 1.77-1.69 (m, 1H), 1.47-1.31 (m, 1H), 1.19-1.13 (m, 1H) |
| I-123 | BSN | BTO | 772.6 | 10.51 (s, 1H), 9.86 (s, 1H), 9.59 (s, 1H), 8.55 (s, 1H), 8.29 (s, 1H), 8.22-8.14 (m, 1H), 8.12-8.05 (m, 1H), 7.99-7.90 (m, 2H), 7.87-7.81 (m, 1H), 7.76 (d, J = 7.6 Hz, 1H), 7.64 (d, J = 6.8 Hz, 1H), 7.06 (s, 1H), 4.43-4.33 (m, 1H), 3.96-3.87 (m, 1H), 3.84 (s, 3H), 3.74-3.65 (m, 1H), 3.62-3.53 (m, 1H), 3.08-2.99 (m, 2H), 2.98-2.91 (m, 1H), 2.81-2.69 (m, 1H), 2.31 (d, J = 1.6, 3.6 Hz, 1H), 2.28-2.19 (m, 4H), 2.18-2.10 (m, 2H), 1.99 (d, J = 1.6, 13.9 Hz, 2H), 1.93-1.83 (m, 5H), 1.72-1.60 (m, 1H), 1.19-1.06 (m, 2H) |
| I-124 | AZK | BVC | 769.3 | 12.42-12.25 (m, 1H), 11.09 (s, 1H), 8.59 (d, J = 2.0 Hz, 1H), 8.55-8.48 (m, 1H), 8.30-8.22 (m, 1H), 7.73-7.67 (m, 1H), 7.38 (s, 1H), 7.12 (s, 1H), 7.06-6.94 (m, 3H), 6.61 (dd, J = 1.6, 3.6 Hz, 1H), 5.37 (dd, J = 4.4, 12.4 Hz, 1H), 4.44-4.32 (m, 1H), 3.95 (s, 3H), 3.59 (s, 3H), 3.26-3.18 (m, 1H), 3.04-2.94 (m, 2H), 2.94-2.82 (m, 1H), 2.77-2.62 (m, 2H), 2.25-2.17 (m, 2H), 2.15-2.02 (m, 4H), 2.01-1.85 (m, 5H), 1.83-1.73 (m, 4H), 1.64 (m, 1H), 1.18-1.04 (m, 2H) |
| I-125 | BRY | BCN | 772.5 | 10.52 (d, J = 10.8 Hz, 2H), 9.25 (s, 1H), 9.01 (s, 1H), 8.49-8.46 (m, 2H), 8.44-8.39 (m, 1H), 8.24 (dd, J = 0.8, 7.6 Hz, 1H), 8.06 (s, 1H), 7.91 (d, J = 8.8 Hz, 1H), 7.78 (dd, J = 1.6, 8.8 Hz, 1H), 7.71 (s, 1H), 4.03 (s, 3H), 3.97-3.89 (m, 1H), 3.73 (td, J = 5.6, 12.0 Hz, 1H), 3.11-3.05 (m, 1H), 3.04-3.00 (m, 2H), 2.96-2.91 (m, 1H), 2.79-2.72 (m, 2H), 2.23-2.18 (m, 4H), 2.08-2.02 (m, 2H), 1.97 (d, J = 10.8 Hz, 2H), 1.88-1.78 (m, 4H), 1.66-1.56 (m, 3H), 1.15-1.05 (m, 2H) |
| I-126 | AQK | BVC | 798.3 | 12.07 (s, 1H), 11.09 (s, 1H), 9.07 (d, J = 1.6 Hz, 1H), 8.77 (d, J = 2.0 Hz, 1H), 8.50 (s, 1H), 8.33 (s, 1H), 8.26 (d, J = 4.0 Hz, 1H), 7.15 (s, 1H), 7.00-6.94 (m, 1H), 6.93-6.84 (m, 3H), 5.35 (dd, J = 5.2, 12.4 Hz, 1H), 4.46-4.31 (m, 1H), 4.08 (s, 3H), 3.64 (s, 3H), 3.19-3.13 (m, 2H), 2.94-2.84 (m, 1H), 2.78-2.69 (m, 2H), 2.66-2.57 (m, 1H), 2.31-2.28 (m, 2H), 2.26 (s, 3H), 2.21-2.09 (m, 3H), 2.04-1.85 (m, 6H), 1.84-1.77 (m, 2H), 1.73-1.61 (m, 2H), 1.60-1.50 (m, 1H), 1.17-1.05 (m, 2H) |
| I-127 | BRY | BUR | 739.7 | 10.54 (s, 1H), 9.27 (s, 1H), 8.82 (d, J = 2.0 Hz, 1H), 8.68 (d, J = 2.0 Hz, 1H), 8.62-8.56 (m, 2H), 8.53 (d, J = 4.0 Hz, 1H), 8.49 (s, 1H), 8.35 (d, J = |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| | | | | 7.6 Hz, 1H), 8.10-8.05 (m, 2H), 7.93 (d, J = 8.4 Hz, 1H), 7.78 (dd, J = 1.4, 8.8 Hz, 1H), 6.89 (d, J = 4.0 Hz, 1H), 3.94 (ddd, J = 5.1, 9.6, 12.2 Hz, 1H), 3.81-3.70 (m, 3H), 3.16-3.07 (m, 2H), 2.97 (ddd, J = 6.0, 9.2, 16.4 Hz, 1H), 2.84-2.72 (m, 2H), 2.52 (d, J = 1.9 Hz, 2H), 2.28-2.17 (m, 2H), 1.93-1.82 (m, 8H), 1.58 (dd, J = 6.0, 13.1 Hz, 1H), 1.44-1.34 (m, 2H), 1.30 (d, J = 6.4 Hz, 6H), 1.01 (q, J = 12.0 Hz, 2H) |
| I-128 | BVK | BVH | 718.6 | 11.10 (s, 1H), 10.59 (s, 1H), 8.43-8.38 (m, 2H), 8.35-8.27 (m, 3H), 7.61 (s, 2H), 6.99 (dd, J = 4.0, 8.8 Hz, 1H), 6.91-6.83 (m, 1H), 5.37 (dd, J = 5.2, 12.8 Hz, 1H), 4.50-4.38 (m, 1H), 3.59 (s, 3H), 3.05-2.95 (m, 2H), 2.94-2.80 (m, 1H), 2.76-2.67 (m, 1H), 2.65-2.58 (m, 1H), 2.25-2.20 (m, 2H), 2.19-2.10 (m, 4H), 2.09-2.02 (m, 2H), 2.02-1.87 (m, 6H), 1.83-1.73 (m, 2H), 1.72-1.62 (m, 1H), 1.21-1.08 (m, 2H) |
| I-129 | AZK | BVJ | 739.6 | 11.40 (s, 1H), 11.09 (s, 1H), 8.96 (d, J = 2.0 Hz, 1H), 8.78 (d, J = 2.0 Hz, 1H), 8.44 (s, 1H), 8.25 (d, J = 4.0 Hz, 1H), 8.13 (s, 1H), 7.69 (d, J = 9.2 Hz, 1H), 7.39 (dd, J = 1.2, 8.8 Hz, 1H), 7.07-6.94 (m, 3H), 6.93 (d, J = 4.0 Hz, 1H), 5.37 (dd, J = 6.0, 12.0 Hz, 1H), 4.53-4.40 (m, 1H), 3.59 (s, 3H), 3.05-2.96 (m, 2H), 2.94-2.84 (m, 1H), 2.77-2.68 (m, 1H), 2.65-2.59 (m, 1H), 2.24-2.16 (m, 4H), 2.11-2.04 (m, 2H), 2.03-1.88 (m, 6H), 1.84-1.75 (m, 4H), 1.71-1.63 (m, 1H), 1.19-1.11 (m, 2H) |
| I-155 | BWB | ATJ | 768.4 | 10.56-10.47 (m, 2H), 9.48-9.36 (m, 1H), 8.72-8.66 (m, 1H), 8.49 (s, 1H), 8.48-8.44 (m, 1H), 8.43-8.38 (m, 1H), 8.33 (d, J = 2.4 Hz, 1H), 8.22 (d, J = 7.6 Hz, 1H), 7.64 (q, J = 8.0 Hz, 1H), 7.42 (d, J = 1.2 Hz, 1H), 7.14 (s, 1H), 7.13-7.01 (m, 1H), 4.76-4.47 (m, 1H), 4.45-4.31 (m, 1H), 3.98 (s, 3H), 3.96-3.87 (m, 1H), 3.87-3.78 (m, 1H), 3.73-3.63 (m, 1H), 3.29-3.04 (m, 2H), 3.00-2.89 (m, 1H), 2.76 (td, J = 5.2, 16.8 Hz, 1H), 2.56-2.51 (m, 1H), 2.49-2.44 (m, 3H), 2.15 (d, J = 9.2 Hz, 3H), 2.09-1.80 (m, 5H), 1.79-1.57 (m, 1H), 1.32-1.12 (m, 2H) |
| I-158 | BWC | ATJ | 786.3 | 11.11 (s, 1H), 10.50 (s, 1H), 8.70 (s, 1H), 8.48-8.45 (m, 1H), 8.43-8.38 (m, 1H), 8.37-8.35 (m, 1H), 8.22 (d, J = 7.6 Hz, 1H), 7.53-7.39 (m, 1H), 7.17-7.12 (m, 2H), 7.06-7.02 (m, 1H), 5.42-5.37 (m, 1H), 4.59-4.37 (m, 3H), 3.98 (s, 3H), 3.86-3.76 (m, 2H), 3.60-3.55 (m, 5H), 3.13-3.02 (m, 1H), 2.94-2.90 (m, 1H), 2.76-2.70 (m, 2H), 2.62-2.60 (s, 2H), 2.39-2.35 (m, 1H), 2.24-2.17 (m, 2H), 2.03-1.91 (m, 6H), 1.46-1.29 (m, 2H) |
| I-159 | AZK | BWF | 781.2 | 11.10 (s, 1H), 8.84 (s, 1H), 8.81 (d, J = 2.0 Hz, 1H), 8.67 (d, J = 1.6 Hz, 1H), 8.56 (s, 1H), 8.52 (d, J = 4.0 Hz, 1H), 8.33 (d, J = 6.8 Hz, 1H), 8.09 (s, 1H), 7.09-6.96 (m, 3H), 6.88 (d, J = 3.6 Hz, 1H), 5.38 (dd, J = 5.2, 12.4 Hz, 1H), 4.64-4.52 (m, 1H), 3.94-3.83 (m, 1H), 3.61 (s, 3H), 3.30-3.29 (m, 2H), 2.94-2.84 (m, 1H), 2.77-2.69 (m, 1H), 2.66-2.56 (m, 2H), 2.53-2.51 (m, 2H), 2.30-2.20 (m, 3H), 2.07-1.95 (m, 4H), 1.95-1.72 (m, 7H), 1.36 (d, J = 6.4 Hz, 6H), 1.29-1.17 (m, 2H) |
| I-160 | BAI | BWH | 785.2 | 11.09 (s, 1H), 10.52 (s, 1H), 9.32 (d, J = 1.6 Hz, 1H), 9.24 (d, J = 1.6 Hz, 1H), 8.77 (s, 1H), 8.56 (s, 1H), 7.98 (s, 1H), 7.72 (s, 1H), 7.03-6.96 (m, 1H), 6.96-6.92 (m, 1H), 6.91-6.86 (m, 1H), 5.35 (dd, J = 4.8, 12.8 Hz, 1H), 4.58-4.46 (m, 1H), 3.64 (s, 3H), 3.05-2.80 (m, 7H), 2.77-2.68 (m, 1H), 2.65-2.56 (m, 2H), 2.28-2.24 (m, 2H), 2.23-2.13 (m, 3H), 2.03-1.95 (m, 4H), 1.95-1.90 (m, 1H), 1.75-1.63 (m, 1H), 1.22-1.08 (m, 2H) |
| I-161 | BWL | BTW | 726.4 | 10.52 (s, 1H), 10.37 (s, 1H), 9.18-9.04 (m, 1H), 8.46-8.22 (m, 5H), 8.21-8.16 (m, 1H), 7.93-7.79 (m, 1H), 7.78-7.68 (m, 1H), 7.65-7.59 (m, 1H), 7.59-7.39 (m, 2H), 4.57-4.42 (m, 1H), 4.15-4.00 (m, 1H), 3.96-3.86 (m, 1H), 3.78-3.63 (m, 2H), 3.27-3.05 (m, 4H), 3.00-2.90 (m, 1H), |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-162 | BWQ | BRR | 772.4 | 10.20 (s, 1H), 9.07 (s, 1H), 8.61 (s, 1H), 8.51-8.46 (m, 2H), 8.41 (t, J = 8.0 Hz, 1H), 8.26-8.21 (m, 1H), 6.90-6.78 (m, 2H), 5.46-5.36 (m, 1H), 4.64-4.52 (m, 1H), 3.63-3.54 (m, 3H), 3.04-3.02 (m, 3H), 3.02-2.90 (m, 3H), 2.81-2.68 (m, 2H), 2.52 (s, 1H), 2.46 (s, 3H), 2.29 (s, 1H), 2.27-2.15 (m, 6H), 2.09-1.91 (m, 8H), 1.81-1.76 (m, 1H), 1.72-1.66 (m, 2H), 1.22-1.10 (m, 2H) 2.79-2.72 (m, 1H), 2.64-2.52 (m, 3H), 2.29-2.12 (m, 3H), 2.10-1.87 (m, 5H), 1.39-1.16 (m, 2H) |
| I-163[c] | BWR | BTW | 758.4 | 11.10 (s, 1H), 10.36 (s, 1H), 8.41 (s, 1H), 8.39-8.30 (m, 3H), 8.18 (d, J = 7.2 Hz, 1H), 7.66-7.58 (m, 1H), 7.58-7.51 (m, 1H), 7.10-6.83 (m, 3H), 5.44-5.30 (m, 1H), 4.55-4.39 (m, 1H), 3.80-3.50 (m, 4H), 3.13-2.80 (m, 5H), 2.66-2.57 (m, 2H), 2.27-2.09 (m, 4H), 2.09-1.81 (m, 6H), 1.72-1.56 (m, 1H), 1.45-1.00 (m, 6H) |
| I-164 | BWS | BTW | 770.3 | 11.10 (s, 1H), 10.37 (s, 1H), 8.44-8.34 (m, 3H), 8.31 (s, 1H), 8.21-8.15 (m 1H), 7.67-7.59 (m, 1H), 7.58-7.51 (m, 1H), 7.20-7.15 (m, 1H), 7.07 (t, J = 6.8 Hz, 1H), 7.02-6.92 (m, 1H), 5.37 (dd, J = 4.8, 12.4 Hz, 1H), 4.55-4.46 (m, 1H), 3.71 (s, 3H), 3.05-2.98 (m, 2H), 2.94-2.85 (m, 3H), 2.75-2.70 (m, 2H), 2.68-2.58 (m, 5H), 2.28-2.13 (m, 5H), 2.12-2.05 (m, 3H), 2.03-1.94 (m, 3H), 1.40-1.22 (m, 2H) |
| I-165 | BAI | BVB | 731.3 | 11.09 (s, 1H), 9.90 (s, 1H), 9.31 (s, 1H), 9.21 (s, 1H), 8.78 (s, 1H), 8.31 (s, 1H), 8.08 (s, 1H), 7.08 (s, 1H), 7.03-6.97 (m, 1H), 6.96-6.89 (m, 2H), 5.40-5.32 (m, 1H), 4.47-4.35 (m, 1H), 3.87 (s, 3H), 3.64 (s, 3H), 3.29 (s, 3H), 3.02-2.83 (m, 6H), 2.73-2.69 (m, 1H), 2.64-2.59 (m, 1H), 2.28-2.23 (m, 1H), 2.21-2.11 (m, 3H), 2.01-1.97 (m, 3H), 1.95-1.87 (m, 2H), 1.76-1.58 (m, 1H), 1.24-1.11 (m, 2H) |
| I-166 | BDY | BVB | 743.3 | 11.09 (s, 1H), 9.91 (s, 1H), 9.31 (S, 1H), 9.20 (d, J = 1.6 Hz, 1H), 8.78 (s, 1H), 8.30 (d, J = 10.4 Hz, 2H), 7.08 (s, 1H), 7.00-6.91 (m, 2H), 6.81-6.79 (m, 1H), 5.38-5.30 (m, 1H), 4.46-4.32 (m, 1H), 3.87 (s, 3H), 3.76 (s, 1H), 3.63 (s, 3H), 3.48 (s, 2H), 3.48-3.46 (m, 1H), 2.89 (d, J = 4.0 Hz, 1H), 2.73-2.62 (m, 4H), 2.60-2.59 (m, 1H), 2.43-2.40 (m, 1H), 2.20-2.11 (m, 2H), 2.02-2.00 (m, 2H), 1.92-1.79 (m, 4H), 1.78-1.62 (m, 1H), 1.55-1.41 (m, 1H), 1.22-1.09 (m, 2H) |
| I-167 | BWS | ATJ | 800.4 | 11.10 (s, 1H), 10.51 (s, 1H), 8.70 (s, 1H), 8.49-8.44 (m, 1H), 8.44-8.38 (m, 1H), 8.35 (s, 1H), 8.25-8.20 (m, 1H), 7.16 (s, 2H), 7.10-6.93 (m, 2H), 5.45-5.30 (m, 1H), 4.49-4.35 (m, 1H), 3.99 (s, 3H), 3.71 (s, 3H), 3.10-2.80 (m, 4H), 2.76-2.68 (m, 1H), 2.65-2.59 (m, 1H), 2.53-2.52 (m, 3H), 2.31-2.04 (m, 8H), 2.03-1.46 (m, 6H), 1.39-1.18 (m, 2H) |
| I-168 | BWT | ATJ | 786.7 | 11.09 (s, 1H), 10.51 (s, 1H), 8.70 (s, 1H), 8.48-8.44 (m, 1H), 8.43-8.38 (m, 1H), 8.35 (s, 1H), 8.22 (d, J = 7.6 Hz, 1H), 7.15 (s, 1H), 7.05-6.96 (m, 2H), 6.87 (d, J = 3.6 Hz, 1H), 5.35 (dd, J = 5.2, 12.4 Hz, 1H), 4.46-4.37 (m, 1H), 3.98 (s, 3H), 3.63 (s, 3H), 3.26 (s, 2H), 2.97-2.82 (m, 2H), 2.77-2.56 (m, 7H), 2.25-2.13 (m, 3H), 2.09-1.86 (m, 7H), 1.30-1.20 (m, 2H) |
| I-169 | AZL | BVB | 730.7 | 11.08 (s, 1H), 9.91 (s, 1H), 9.31 (d, J = 1.8 Hz, 1H), 9.21 (d, J = 1.8 Hz, 1H), 8.78 (s, 1H), 8.31 (s, 1H), 8.08 (s, 1H), 7.10 (d, J = 9.2 Hz, 2H), 7.01 (d, J = 8.0 Hz, 1H), 6.95-6.91 (m, 1H), 5.34 (dd, J = 5.4, 12.8 Hz, 1H), 4.46-4.32 (m, 1H), 3.88 (s, 3H), 3.34 (s, 3H), 3.06 (d, J = 7.6 Hz, 2H), 2.96-2.83 (m, 2H), 2.73 (d, J = 8.4 Hz, 3H), 2.31 (s, 1H), 2.16 (d, J = 10.8 Hz, 4H), 2.04-1.87 (m, 6H), 1.78 (s, 4H), 1.21-1.05 (m, 2H) |
| I-171 | BSN | BWU | 743.3 | 10.54 (s, 1H), 10.43 (s, 1H), 9.64 (s, 1H), 9.04 (s, 1H), 8.96 (s, 1H), 8.58 (s, 1H), 8.52-8.47 (m, 1H), 8.46-8.40 (m, 1H), 8.29-8.23 (m, 1H), 7.91-7.86 (m, 1H), 7.80 (t, J = 7.2 Hz, 1H), 7.68-7.61 |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | (m, 1H), 3.98-3.88 (m, 1H), 3.85-3.50 (m, 2H), 3.31-3.26 (m, 2H), 3.21-3.13 (m, 1H), 3.10-2.85 (m, 2H), 2.81-2.72 (m, 1H), 2.53-2.51 (m, 3H), 2.29-2.20 (m, 2H), 2.19-1.74 (m, 7H), 1.74-1.59 (m, 2H), 1.30-1.05 (m, 2H) |
| I-172[d] | BWW | BTW | 811.3 | 11.10 (s, 1H), 10.36 (s, 1H), 8.43-8.33 (m, 3H), 8.30 (s, 1H), 8.17 (d, J = 7.2 Hz, 1H), 7.64-7.59 (m, 1H), 7.58-7.52 (m, 1H), 7.13-7.08 (m, 1H), 7.07-6.97 (m, 2H), 5.42-5.34 (m, 1H), 4.50-4.40 (m, 1H), 3.70-3.59 (m, 2H), 3.55 (s, 3H), 3.02-2.97 (m, 1H), 2.94-2.84 (m, 2H), 2.77-2.70 (m, 2H), 2.65-2.57 (m, 2H), 2.24-2.13 (m, 3H), 2.04-1.94 (m, 6H), 1.94-1.83 (m, 3H), 1.74-1.62 (m, 2H) |
| I-173 | BWY | ATJ | 787.2 | 11.07 (s, 1H), 10.50 (s, 1H), 8.69 (s, 1H), 8.49-8.37 (m, 2H), 8.34 (s, 1H), 8.22 (d, J = 8.4 Hz, 1H), 7.15 (s, 1H), 6.92 (s, 2H), 5.33 (dd, J = 5.2, 12.8 Hz, 1H), 4.45-4.33 (m, 1H), 3.98 (s, 3H), 3.61 (s, 3H), 3.23-3.07 (m, 3H), 2.98-2.81 (m, 2H), 2.74-2.62 (m, 2H), 2.56 (s, 3H), 2.40-2.36 (m, 1H), 2.19-2.13 (m, 2H), 2.06-1.86 (m, 6H), 1.85-1.55 (m, 6H), 1.24-1.11 (m, 2H) |
| I-176 | AZK | BXE | 773.3 | 11.09 (s, 1H), 10.24 (s, 1H), 8.43-8.35 (m, 2H), 8.34 (s, 1H), 8.18 (dd, J = 1.2, 7.6 Hz, 1H), 7.93 (d, J = 1.6 Hz, 1H), 7.05-7.00 (m, 3H), 7.00-6.96 (m, 1H), 5.37 (dd, J = 5.6, 12.8 Hz, 1H), 4.47-4.36 (m, 1H), 3.93 (s, 3H), 3.59 (s, 3H), 2.99 (br d, J = 11.2 Hz, 2H), 2.92-2.85 (m, 1H), 2.78-2.68 (m, 1H), 2.65-2.58 (m, 1H), 2.21 (br d, J = 7.2 Hz, 2H), 2.15 (br d, J = 12.4 Hz, 2H), 2.10-2.04 (m, 2H), 2.01-1.96 (m, 3H), 1.93 (br d, J = 12.4 Hz, 2H), 1.82-1.74 (m, 4H), 1.74-1.60 (m, 2H), 1.19-1.10 (m, 2H) |
| I-177 | BWX | ATJ | 807.3 | 11.13 (s, 1H), 10.51 (s, 1H), 8.70 (s, 1H), 8.49-8.45 (m, 1H), 8.44-8.39 (m, 1H), 8.34 (s, 1H), 8.23 (d, J = 8.0 Hz, 1H), 7.16 (s, 1H), 7.14-7.04 (m, 2H), 5.44-5.37 (m, 1H), 4.45-4.33 (m, 1H), 3.99 (s, 3H), 3.67 (s, 3H), 3.30 (s, 4H), 3.17-3.00 (m, 2H), 2.93-2.83 (m, 1H), 2.18-2.14 (m, 2H), 2.07-1.89 (m, 7H), 1.85-1.67 (m, 5H), 1.26-1.10 (m, 3H) |
| I-178 | BWX | BRR | 778.5 | 11.12 (s, 1H), 10.20 (s, 1H), 9.06 (s, 1H), 8.61 (s, 1H), 8.52-8.47 (m, 2H), 8.45-8.37 (m, 1H), 8.23 (d, J = 8.0 Hz, 1H), 7.16-7.02 (m, 2H), 5.40 (dd, J = 6.0, 12.8 Hz, 1H), 4.66-4.53 (m, 1H), 3.66 (s, 3H), 3.29 (s, 3H), 2.88 (d, J = 2.4 Hz, 1H), 2.77-2.69 (m, 1H), 2.61 (s, 1H), 2.22 (d, J = 10.4 Hz, 4H), 2.01 (d, J = 5.6 Hz, 7H), 1.86-1.77 (m, 5H), 1.26-1.16 (m, 2H) |
| I-179 | AQK | BVU | 786.7 | 11.09 (s, 1H), 8.83 (d, J = 2.0 Hz, 1H), 8.71 (d, J = 2.0 Hz, 1H), 8.68 (s, 1H), 8.45 (d, J = 7.6 Hz, 1H), 8.27 (d, J = 7.6 Hz, 1H), 8.05 (s, 1H), 7.82 (d, J = 4.8 Hz, 1H), 7.10 (d, J = 4.8 Hz, 1H), 6.99-6.95 (m, 1H), 6.89-6.85 (m, 1H), 5.35 (dd, J = 5.6, 12.4 Hz, 1H), 3.83-3.70 (m, 2H), 3.64 (s, 3H), 3.15 (d, J = 11.0 Hz, 2H), 2.94-2.82 (m, 1H), 2.75-2.63 (m, 4H), 2.42 (s, 2H), 2.27-2.22 (m, 5H), 1.99 (s, 1H), 1.91-1.75 (m, 7H), 1.66 (s, 2H), 1.39-1.32 (m, 2H), 1.27 (d, J = 6.4 Hz, 6H), 0.94 (m, J = 11.5 Hz, 2H) |
| I-180 | BWX | BTW | 777.6 | 11.11 (s, 1H), 10.36 (s, 1H), 8.42-8.32 (m, 3H), 8.29 (s, 1H), 8.17 (d, J = 8.0 Hz, 1H), 7.64-7.59 (m, 1H), 7.57-7.52 (m, 1H), 7.12-7.06 (m, 2H), 5.44.5.34 (m, 1H), 4.50-4.40 (m, 1H), 3.66 (s, 3H), 3.03-2.94 (m, 3H), 2.94-2.83 (m, 1H), 2.71 (d, J = 4.4 Hz, 1H), 2.66-2.58 (m, 1H), 2.24-2.14 (m, 4H), 2.02 (d, J = 10.4 Hz, 3H), 2.00-1.88 (m, 4H), 1.77-1.63 (m, 5H), 1.20-1.10 (m, 2H) |
| I-181 | BRY | BH | 742.5 | 10.62 (s, 1H), 10.54 (s, 1H), 9.27 (s, 1H), 8.62 (d, J = 1.6 Hz, 1H), 8.49 (s, 1H), 8.43-8.35 (m, 2H), 8.19 (dd, J = 1.2, 7.6 Hz, 1H), 8.06 (s, 1H), 7.96-7.88 (m, 3H), 7.78 (dd, J = 1.6, 8.8 Hz, 1H), 3.98-3.90 (m, 1H), 3.76-3.69 (m, 1H), 3.29-3.19 (m, 3H), 3.14-3.06 (m, 1H), 3.01-2.92 (m, 1H), 2.91-2.83 (m, 1H), 2.80-2.73 (m, 1H), 2.68- |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 2.54 (m, 2H), 2.39-2.31 (m, 1H), 2.25-2.18 (m, 2H), 2.00-1.89 (m, 6H), 1.80-1.73 (m, 1H), 1.69-1.59 (m, 2H), 1.21-1.10 (m, 2H) |
| I-182 | AZK | BXF | 756.6 | 11.09 (s, 1H), 10.05 (s, 1H), 9.05 (s, 1H), 8.84 (d, J = 2.4 Hz, 1H), 8.42 (s, 1H), 8.36 (s, 1H), 7.65 (s, 1H), 7.05-6.96 (m, 3H), 5.40-5.34 (m, 1H), 3.92 (s, 3H), 3.58 (s, 3H), 3.26-3.21 (m, 1H), 3.10-3.05 (m, 1H), 2.99 (d, J = 10.8 Hz, 2H), 2.93-2.85 (m, 1H), 2.75-2.69 (m, 1H), 2.64-2.58 (m, 1H), 2.22-2.16 (m, 4H), 2.10-2.05 (m, 2H), 2.00-1.93 (m, 3H), 1.82-1.72 (m, 4H), 1.66-1.56 (m, 3H), 1.19-1.03 (m, 2H) |
| I-183 | AZK | BVU | 757.7 | 11.09 (s, 1H), 8.84 (d, J = 2.0 Hz, 1H), 8.70 (d, J = 2.0 Hz, 1H), 8.68 (s, 1H), 8.46 (d, J = 6.9 Hz, 1H), 8.28 (d, J = 8.0 Hz, 1H), 8.16 (s, 1H), 8.05 (s, 1H), 7.84 (d, J = 4.8 Hz, 1H), 7.10 (d, J = 4.9 Hz, 1H), 7.04-7.00 (m, 2H), 7.00 (d, J = 4.1 Hz, 1H), 5.36 (dd, J = 5.5, 12.5 Hz, 1H), 3.82-3.75 (m, 1H), 3.58 (s, 3H), 3.00 (d, J = 9.6 Hz, 2H), 2.91-2.83 (m, 1H), 2.76-2.62 (m, 2H), 2.20 (d, J = 6.3 Hz, 2H), 2.13-2.05 (m, 2H), 2.02-1.96 (m, 1H), 1.92-1.74 (m, 10H), 1.36 (d, J = 10.0 Hz, 2H), 1.28 (d, J = 6.4 Hz, 6H), 1.02-0.92 (m, 2H) |
| I-184 | BSN | BVU | 739.7 | 10.53 (s, 1H), 9.62 (s, 1H), 8.83 (s, 1H), 8.68 (d, J = 7.6 Hz, 2H), 8.57 (s, 1H), 8.44 (d, J = 7.0 Hz, 1H), 8.30 (d, J = 7.9 Hz, 1H), 8.14 (s, 1H), 8.06 (s, 1H), 7.89-7.85 (m, 1H), 7.83-7.77 (m, 1H), 7.64 (d, J = 6.6 Hz, 1H), 7.10 (d, J = 4.9 Hz, 1H), 3.92 (d, J = 4.9, 10.9 Hz, 1H), 3.83-3.67 (m, 5H), 3.19-3.14 (m, 2H), 3.02-2.94 (m, 1H), 2.76 (d, J = 5.3, 17.0 Hz, 1H), 1.98-1.86 (m, 10H), 1.64-1.56 (m, 1H), 1.36 (d, J = 10.6 Hz, 2H), 1.28 (d, J = 6.1 Hz, 6H), 1.04 (d, J = 10.3 Hz, 2H) |
| I-185 | AZK | BXG | 747.6 | 11.09 (s, 1H), 10.13 (s, 1H), 9.32 (s, 1H), 9.22 (s, 1H), 8.79 (s, 1H), 8.41 (s, 1H), 7.66 (s, 1H), 7.05-6.95 (m, 3H), 5.39-5.35 (m, 1H), 3.93 (s, 3H), 3.59 (s, 3H), 3.24-3.22 (m, 1H), 3.10-3.03 (m, 1H), 2.99 (d, J = 10.4 Hz, 2H), 2.91-2.84 (m, 1H), 2.74-2.57 (m, 3H), 2.22-2.18 (m, 4H), 2.09-2.05 (m, 2H), 1.97-1.94 (m, 3H), 1.79 (s, 4H), 1.65-1.58 (m, 2H), 1.15-1.06 (m, 2H) |
| I-189 | AZK | BXI | 768.3 | 11.10 (s, 1H), 10.65 (s, 1H), 8.64 (s, 1H), 8.49-8.36 (m, 3H), 8.27-8.21 (m, 2H), 7.07-6.94 (m, 3H), 5.44-5.34 (m, 1H), 4.63-4.52 (m, 1H), 3.60 (s, 3H), 3.26-3.18 (m, 1H), 3.07-2.97 (m, 2H), 2.94-2.84 (m, 1H), 2.75-2.60 (m, 2H), 2.27-2.16 (m, 4H), 2.15-2.05 (m, 2H), 2.04-1.91 (m, 5H), 1.85-1.65 (m, 5H), 1.24-1.10 (m, 2H) |
| I-190 | BSN | BUR | 739.6 | 10.54 (s, 1H), 9.64 (s, 1H), 8.81 (d, J = 2.0 Hz, 1H), 8.68 (d, J = 2.0 Hz, 1H), 8.61-8.56 (m, 3H), 8.52 (d, J = 4.0 Hz, 1H), 8.36 (d, J = 7.6 Hz, 1H), 8.08 (s, 1H), 7.92-7.85 (m, 1H), 7.80 (t, J = 7.6 Hz, 1H), 7.64 (d, J = 6.4 Hz, 1H), 6.89 (d, J = 4.0 Hz, 1H), 3.97-3.87 (m, 1H), 3.83-3.63 (m, 5H), 3.86-2.87 (m, 2H), 2.83-2.71 (m, 2H), 2.52 (s, 2H), 2.06-1.82 (m, 9H), 1.71-1.60 (m, 1H), 1.39 (q, J = 11.7 Hz, 2H), 1.29 (d, J = 6.3 Hz, 6H), 1.13-1.00 (m, 2H) |
| I-191 | BSN | BCN | 772.5 | 10.55 (s, 1H), 10.51 (s, 1H), 9.70 (s, 1H), 9.02 (s, 1H), 8.61 (s, 1H), 8.49-8.39 (m, 2H), 8.26-8.21 (m, 1H), 7.95-7.90 (m, 1H), 7.86-7.81 (m, 1H), 7.70 (s, 1H), 7.63 (d, J = 7.2 Hz, 1H), 4.03 (s, 3H), 4.00-3.89 (m, 2H), 3.75-3.67 (m, 2H), 3.67-3.63 (m, 1H), 3.31-3.21 (m, 2H), 3.17-3.11 (m, 1H), 3.10-3.05 (m, 2H), 3.03-2.95 (m, 1H), 2.81-2.73 (m, 1H), 2.54-2.52 (m, 1H), 2.27-2.21 (m, 2H), 2.20-2.10 (m, 3H), 2.06-1.91 (m, 3H), 1.75-1.61 (m, 2H), 1.34-1.19 (m, 2H) |
| I-192 | BSN | BTO | 772.6 | 10.51 (s, 1H), 9.86 (s, 1H), 9.59 (s, 1H), 8.55 (s, 1H), 8.29 (s, 1H), 8.22-8.14 (m, 1H), 8.12-8.05 (m, 1H), 7.99-7.90 (m, 2H), 7.87-7.81 (m, 1H), 7.76 (d, J = 7.6 Hz, 1H), 7.64 (d, J = 6.8 Hz, 1H), 7.06 (s, 1H), 4.43-4.33 (m, 1H), 3.96-3.87 (m, 1H), 3.84 (s, 3H), 3.74-3.65 (m, 1H), 3.62-3.53 (m, 1H), 3.08-2.99 (m, 2H), 2.98-2.91 (m, 1H), |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| I-195 | BUC | BVB | 760.6 | 2.81-2.69 (m, 1H), 2.31 (d, J = 1.6, 3.6 Hz, 1H), 2.28-2.19 (m, 4H), 2.18-2.10 (m, 2H), 1.99 (d, J = 1.6, 13.9 Hz, 2H), 1.93-1.83 (m, 5H), 1.72-1.60 (m, 1H), 1.19-1.06 (m, 2H) 11.07 (s, 1H), 9.90 (s, 1H), 9.33-9.19 (m, 1H), 8.86-8.72 (m, 1H), 8.33-8.28 (m, 1H), 8.24-8.07 (m, 1H), 7.09 (s, 1H), 7.06-6.98 (m, 1H), 6.90 (d, J = 8.6 Hz, 1H), 6.72 (d, J = 8.8 Hz, 1H), 5.32 (dd, J = 5.4, 12.8 Hz, 1H), 4.46-4.31 (m, 1H), 3.90-3.85 (m, 3H), 3.77 (s, 3H), 3.56 (s, 3H), 3.00 (d, J = 9.2 Hz, 2H), 2.93-2.82 (m, 1H), 2.72 (d, J = 4.4 Hz, 1H), 2.65-2.56 (m, 1H), 2.44-2.36 (m, 2H), 2.24 (d, J = 6.0 Hz, 2H), 2.16 (d, J = 9.8 Hz, 2H), 2.07-1.86 (m, 8H), 1.73-1.63 (m, 1H), 1.6 (d, J = 11.9 Hz, 2H), 1.21-1.09 (m, 2H) |
| I-197 | BXL | BWF | 764.5 | 10.54 (s, 1H), 9.45 (s, 1H), 8.85 (s, 1H), 8.81 (d, J = 2.0 Hz, 1H), 8.67 (d, J = 2.0 Hz, 1H), 8.58-8.50 (m, 3H), 8.34 (d, J = 7.2 Hz, 1H), 8.09 (s, 1H), 7.78-7.70 (m, 1H), 7.65 (d, J = 7.6 Hz, 1H), 7.31 (d, J = 7.2 Hz, 1H), 6.88 (d, J = 3.6 Hz, 1H), 4.66-4.53 (m, 1H), 3.97-3.82 (m, 2H), 3.70 (td, J = 6.0, 12.0 Hz, 1H), 3.30-3.08 (m, 5H), 2.97 (ddd, J = 6.0, 10.0, 16.4 Hz, 2H), 2.76 (td, J = 5.6, 16.8 Hz, 2H), 2.52 (s, 3H), 2.25 (d, J = 10.8 Hz, 2H), 2.03 (d, J = 12.0 Hz, 2H), 1.97-1.84 (m, 2H), 1.83-1.68 (m, 1H), 1.36 (d, J = 6.4 Hz, 6H), 1.30-1.15 (m, 2H) |
| I-198 | BRY | BVU | 739.4 | 10.54 (s, 1H), 9.27 (s, 1H), 8.83 (d, J = 2.0 Hz, 1H), 8.73-8.66 (m, 2H), 8.50 (s, 1H), 8.45 (d, J = 6.8 Hz, 1H), 8.31 (d, J = 7.2 Hz, 1H), 8.13 (s, 1H), 8.06 (s, 2H), 7.94 (d, J = 8.4 Hz, 1H), 7.86-7.72 (m, 2H), 7.10 (d, J = 4.8 Hz, 1H), 3.90-3.97 (m, 1H), 3.85-3.63 (m, 4H), 2.92 (s, 1H), 2.90-2.81 (m, 1H), 2.73-2.79 (m, 1H), 2.04-1.78 (m, 10H), 1.75-1.49 (m, 2H), 1.42-1.32 (m, 2H), 1.28 (d, J = 6.4 Hz, 6H), 1.20-1.11 (m, 1H), 1.08-0.97 (m, 2H) |
| I-199 | BXN | BVU | 811.8 | 11.13 (s, 1H), 8.84 (d, J = 2.4 Hz, 1H), 8.71 (d, J = 2.0 Hz, 1H), 8.68 (s, 1H), 8.43 (d, J = 7.2 Hz, 1H), 8.31 (d, J = 7.6 Hz, 1H), 8.05 (s, 1H), 7.82 (d, J = 4.8 Hz, 1H), 7.19 (d, J = 8.0 Hz, 1H), 7.15-7.09 (m, 2H), 7.07-7.01 (m, 1H), 5.40 (dd, J = 5.2, 12.8 Hz, 1H), 4.53 (s, 2H), 3.85-3.67 (m, 3H), 3.65 (s, 3H), 2.95-2.84 (m, 2H), 2.77-2.62 (m, 3H), 2.52 (s, 2H), 2.45-2.36 (m, 2H), 2.02 (m, 3H), 1.94-1.79 (m, 5H), 1.75-1.60 (m, 2H), 1.43-1.30 (m, 2H), 1.27 (d, J = 6.4 Hz, 6H), 1.11-0.97 (m, 2H) |
| I-200[b] | BUC | BVH | 730.2 | 11.0 (s, 1H), 10.59 (s, 1H), 8.44-8.36 (m, 2H), 8.35-8.25 (m, 3H), 7.61 (d, J = 1.0 Hz, 1H), 6.91 (d, J = 8.4 Hz, 1H), 6.72 (d, J = 8.8 Hz, 1H), 5.32 (dd, J = 5.2, 12.4 Hz, 1H), 4.51-4.39 (m, 1H), 3.77 (s, 3H), 3.56 (s, 3H), 2.98 (d, J = 10.4 Hz, 2H), 2.92-2.84 (m, 1H), 2.71-2.59 (m, 2H), 2.42 (d, J = 11.2 Hz, 2H), 2.24-2.15 (m, 4H), 2.07-1.87 (m, 8H), 1.72-1.64 (m, 1H), 1.58 (d, J = 10.8 Hz, 2H), 1.20-1.10 (m, 2H) |
| I-201 | BSN | BH | 742.6 | 10.62 (s, 1H), 10.54 (s, 1H), 9.62 (s, 1H), 8.61 (s, 1H), 8.57 (s, 1H), 8.44-8.34 (m, 2H), 8.19 (d, J = 7.6 Hz, 1H), 8.15 (s, 1H), 7.96-7.86 (m, 2H), 7.79 (t, J = 7.6 Hz, 1H), 7.65 (d, J = 7.2 Hz, 1H), 3.97-3.88 (m, 1H), 3.71 (td, J = 6.0, 12.0 Hz, 1H), 3.64 (d, J = 4.0 Hz, 1H), 3.18-3.04 (m, 3H), 3.03-2.93 (m, 1H), 2.76 (td, J = 5.2, 16.4 Hz, 1H), 2.47-2.35 (m, 4H), 2.21 (d, J = 11.2 Hz, 2H), 2.05-1.82 (m, 6H), 1.72 (d, J = 0.8 Hz, 1H), 1.69-1.56 (m, 2H), 1.20-1.06 (m, 2H) |
| I-202 | BWY | BTW | 757.3 | 11.07 (s, 1H), 10.35 (s, 1H), 8.42-8.33 (m, 3H), 8.30 (s, 1H), 8.17 (dd, J = 1.2, 7.6 Hz, 1H), 7.65-7.58 (m, 1H), 7.58-7.51 (m, 1H), 6.97-6.86 (m, 2H), 5.33 (dd, J = 5.2, 12.4 Hz, 1H), 4.51-4.39 (m, 1H), 3.61 (s, 3H), 3.06-2.97 (m, 2H), 2.95-2.67 (m, 3H), 2.65-2.58 (m, 1H), 2.55 (s, 3H), 2.26 (d, J = 7.2 Hz, 2H), 2.20-2.08 (m, 4H), 2.03-1.89 (m, 5H), 1.74-1.60 (m, 5H), 1.21-1.07 (m, 2H) |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-203 | BQM | BXI | 782.4 | 11.11-11.04 (m, 1H), 10.64 (s, 1H), 8.63 (s, 1H), 8.47-8.37 (m, 3H), 8.26-8.21 (m, 2H), 6.90-6.78 (m, 2H), 5.33 (dd, J = 5.2, 12.4 Hz, 1H), 4.57 (t, J = 11.6 Hz, 1H), 3.62-3.53 (m, 3H), 3.23-3.15 (m, 1H), 3.05-2.96 (m, 2H), 2.93-2.81 (m, 1H), 2.75-2.59 (m, 2H), 2.46 (s, 3H), 2.29 (s, 1H), 2.27-2.17 (m, 5H), 2.06 (d, J = 10.8 Hz, 2H), 1.98 (t, J = 11.6 Hz, 5H), 1.78 (s, 1H), 1.69 (d, J = 10.4 Hz, 2H), 1.23-1.08 (m, 2H) |
| I-205 | BQM | BXI | 798.5 | 11.08 (s, 1H), 10.65 (s, 1H), 8.64 (s, 1H), 8.50-8.35 (m, 3H), 8.26-8.21 (m, 2H), 6.94 (d, J = 8.8 Hz, 1H), 6.75 (d, J = 8.8 Hz, 1H), 5.33 (dd, J = 5.2, 12.4 Hz, 1H), 4.67-4.54 (m, 1H), 3.79 (s, 3H), 3.60 (s, 3H), 3.51-3.42 (m, 1H), 3.14-3.05 (m, 1H), 2.94-2.81 (m, 2H), 2.78-2.52 (m, 6H), 2.22 (d, J = 9.2 Hz, 2H), 2.09-1.92 (m, 6H), 1.91-1.82 (m, 1H), 1.80-1.66 (m, 2H), 1.26 (dd, J = 1.6, 10.0 Hz, 2H), 1.17 (t, J = 7.2 Hz, 1H) |
| I-206[h] | BXQ | BVB | 771.2 | 9.31 (d, J = 1.6 Hz, 1H), 9.04 (d, J = 1.6 Hz, 1H), 8.74 (d, J = 11.6 Hz, 2H), 8.51 (s, 1H), 8.31-8.11 (m, 1H), 7.88 (s, 1H), 7.09 (s, 1H), 7.04-6.96 (m, 1H), 6.87 (d, J = 8.0 Hz, 1H), 6.59 (d, J = 7.6 Hz, 1H), 5.23-5.18 (m, J = 5.2, 12.4 Hz, 1H), 4.35-4.29 (m, J = 3.6, 8.0, 11.6 Hz, 1H), 4.02 (s, 3H), 3.74 (s, 3H), 3.64-3.62 (m, J = 4.4 Hz, 2H), 3.15-3.08 (m, 2H), 2.99-2.91 (m, 2H), 2.89-2.83 (m, 3H), 2.80-2.68 (m, 4H), 2.34-2.31 (m, J = 10.8 Hz, 2H), 2.25-2.14 (m, 3H), 2.09-2.06 (m, J = 11.6 Hz, 2H), 2.01-1.89 (m, 4H), 1.85-1.75 (m, 1H), 1.35-1.22 (m, 2H) |
| I-207[h] | BXR | BVB | 799.2 | 9.31 (d, J = 2.0 Hz, 1H), 9.04 (d, J = 2.0 Hz, 1H), 8.74 (d, J = 11.2 Hz, 2H), 8.51 (t, J = 2.0 Hz, 1H), 8.25-8.13 (m, 1H), 7.89 (s, 1H), 7.09 (s, 1H), 7.04-6.99 (m, 1H), 6.96-6.92 (m, 1H), 6.59 (d, J = 7.6 Hz, 1H), 5.23-5.18 (m, J = 5.2, 12.4 Hz, 1H), 4.39-4.28 (m, 1H), 4.02 (s, 3H), 3.76 (s, 3H), 3.06-2.87 (m, 10H), 2.80-2.70 (m, 4H), 2.35-2.32 (m, J = 11.2 Hz, 2H), 2.27-2.16 (m, 2H), 2.14-2.11 (m, J = 12.4 Hz, 2H), 2.06-1.96 (m, 4H), 1.79 (s, 3H), 1.72-1.65 (m, 2H), 1.37-1.26 (m, 2H). |
| I-208 | BWL | ATJ | 756.1 | 10.51 (d, J = 2.0 Hz, 2H), 9.34-9.17 (m, 1H), 9.13 (s, 1H), 8.70 (s, 1H), 8.50-8.38 (m, 2H), 8.35 (s, 1H), 8.22 (d, J = 7.6 Hz, 1H), 7.88 (d, J = 8.4 Hz, 1H), 7.73 (d, J = 8.4 Hz, 1H), 7.56 (s, 1H), 7.15 (s, 1H), 4.51-4.37 (m, 1H), 4.19-4.01 (m, 2H), 3.99 (s, 3H), 3.95-3.86 (m, 1H), 3.82-3.59 (m, 3H), 3.28-3.09 (m, 6H), 3.01-2.89 (m, 1H), 2.80-2.71 (m, 1H), 2.25-2.14 (m, 2H), 2.07-1.87 (m, 5H), 1.40-1.18 (m, 2H) |
| I-209 | BAI | BTW | 744.6 | 11.26-10.96 (m, 1H), 10.37 (s, 1H), 8.42-8.34 (m, 3H), 8.33-8.30 (m, 2H), 8.18 (d, J = 1.2 Hz, 7.6 Hz, 1H), 7.65-7.60 (m, 1H), 7.58-7.53 (m, 1H), 7.02-6.84 (m, 3H), 5.36 (s, 1H), 4.52-4.41 (m, 1H), 3.64 (s, 3H), 3.03-2.86 (m, 6H), 2.78-2.58 (m, 4H), 2.26 (d, J = 7.2 Hz, 2H), 2.18 (d, J = 10.4 Hz, 2H), 2.04-1.89 (m, 5H), 1.68 (d, J = 6.8 Hz, 1H), 1.27-1.03 (m, 4H) |
| I-210 | BWY | BRR | 758.3 | 11.07 (s, 1H), 10.20 (s, 1H), 9.06 (s, 1H), 8.61 (s, 1H), 8.51-8.45 (m, 2H), 8.45-8.38 (m, 1H), 8.23 (d, J = 8.0 Hz, 1H), 6.98-6.85 (m, 2H), 5.32 (dd, J = 52, 12.4 Hz, 1H), 4.65-4.51 (m, 1H), 3.61 (s, 3H), 3.00 (d, J = 10.8 Hz, 2H), 2.95-2.83 (m, 1H), 2.82-2.72 (m, 1H), 2.66-2.54 (m, 5H), 2.26-2.17 (m, 4H), 2.13-2.05 (m, 2H), 1.98 (t, J = 11.2 Hz, 5H), 1.67 (s, 5H), 1.22-1.09 (m, 2H) |
| I-211 | BXL | ATJ | 756.5 | 10.52 (d, J = 13.2 Hz, 2H), 9.46 (s, 1H), 8.70 (s, 1H), 8.55 (s, 1H), 8.49-8.44 (m, 1H), 8.43-8.37 (m, 1H), 8.34 (s, 1H), 8.22 (d, J = 7.6 Hz, 1H), 7.80-7.60 (m, 2H), 7.31 (s, 1H), 7.16 (s, 1H), 4.41 (s, 1H), 4.03-3.86 (m, 4H), 3.73-3.67 (m, J = 5.6, 12.0 Hz, 1H), 3.62-3.43 (m, 1H), 3.31-3.08 (m, 5H), 3.01-2.93 (m, 1H), 2.82-2.62 (m, 3H), 2.58-2.52 (m, 2H), 2.19-2.16 (m, J = 10.4 Hz, 2H), 2.06-1.69 (m, 5H), 1.33-1.08 (m, 2H) |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-212 | AZK | BXS | 797.4 | 11.09 (s, 1H), 10.11 (s, 1H), 9.36 (d, J = 1.6 Hz, 1H), 9.21 (d, J = 1.6 Hz, 1H), 8.80 (s, 1H), 8.30 (s, 1H), 8.25 (s, 1H), 7.65 (s, 1H), 7.08-6.88 (m, 4H), 5.37 (dd, J = 5.2, 12.4 Hz, 1H), 4.47 (s, 1H), 4.37 (s, 1H), 4.30 (s, 1H), 4.01 (d, J = 7.2 Hz, 1H), 3.72 (d, J = 7.6 Hz, 1H), 3.59 (s, 3H), 2.99 (d, J = 9.2 Hz, 3H), 2.93-2.85 (m, 1H), 2.76-2.68 (m, 1H), 2.62 (d, J = 17.6 Hz, 1H), 2.21 (d, J = 6.8 Hz, 2H), 2.18-2.12 (m, 2H), 2.11-2.03 (m, 3H), 2.02-1.95 (m, 3H), 1.93-1.85 (m, 3H), 1.84-1.72 (m, 6H), 1.70-1.63 (m, 1H), 1.19-1.06 (m, 2H) |
| I-213 | BSN | BXI | 750.4 | 10.64 (s, 1H), 10.53 (s, 1H), 9.61 (s, 1H), 8.64 (s, 1H), 8.57 (s, 1H), 8.47-8.36 (m, 3H), 8.27-8.20 (m, 2H), 7.89-7.83 (m, 1H), 7.78 (t, J = 7.6 Hz, 1H), 7.66 (d, J = 7.2 Hz, 1H), 4.64-4.54 (m, 1H), 3.92 (ddd, J = 5.2, 9.8, 12.0 Hz, 1H), 3.72 (td, J = 6.0, 12.1 Hz, 1H), 3.62 (t, J = 15.2 Hz, 1H), 3.07 (d, J = 10.0 Hz, 2H), 2.98 (ddd, J = 6.0, 10.0, 16.5 Hz, 1H), 2.76 (td, J = 5.4, 16.6 Hz, 1H), 2.52 (s, 1H), 2.31 (dd, J = 2.4, 8.0 Hz, 3H), 2.24-2.17 (m, 2H), 2.07-1.84 (m, 8H), 1.78-1.65 (m, 1H), 1.25-1.11 (m, 2H) |
| I-216[h] | BAI | BXX | 791.4 | 9.36 (d, J = 14.0 Hz, 1H), 8.83 (s, 1H), 8.42 (t, J = 6.4 Hz, 1H), 8.05 (s, 1H), 7.88 (s, 1H), 7.81 (t, J = 6.4 Hz, 1H), 7.44 (t, J = 7.6 Hz, 1H), 7.08 (s, 1H), 7.03 (d, J = 6.8 Hz, 1H), 6.68-6.58 (m, 1H), 5.21 (dd, J = 5.2, 12.8 Hz, 1H), 4.43-4.28 (m, 1H), 4.02 (s, 3H), 3.77 (s, 3H), 3.18-3.03 (m, 3H), 3.01-2.72 (m, 6H), 2.36 (d, J = 11.6 Hz, 3H), 2.27-2.20 (m, 2H), 2.18-2.10 (m, 1H), 2.07-1.96 (m, 2H), 1.67-1.59 (m, 4H), 1.19 (d, J = 5.2 Hz, 2H) |
| I-217 | AQK | BXS | 826.4 | 11.09 (s, 1H), 10.06 (s, 1H), 9.36 (d, J = 1.6 Hz, 1H), 9.21 (d, J = 1.6 Hz, 1H), 8.80 (s, 1H), 8.25 (s, 1H), 7.65 (s, 1H), 7.00-6.86 (m, 4H), 5.35 (dd, J = 5.2, 12.8 Hz, 1H), 4.47 (s, 1H), 4.42-4.33 (m, 1H), 4.31 (s, 1H), 4.01 (d, J = 7.2 Hz, 1H), 3.72 (d, J = 6.4 Hz, 1H), 3.64 (s, 3H), 3.43 (d, J = 8.0 Hz, 2H), 3.19-3.15 (m, 2H), 2.99 (d, J = 9.6 Hz, 1H), 2.95-2.83 (m, 2H), 2.77-2.70 (m, 3H), 2.63 (d, J = 3.6 Hz, 1H), 2.17-2.12 (m, 2H), 2.07 (s, 3H), 2.00-1.95 (m, 3H), 1.92 (d, J = 3.6 Hz, 1H), 1.89 (d, J = 8.0 Hz, 2H), 1.86-1.81 (m, 2H), 1.77 (d, J = 10.4 Hz, 2H), 1.71-1.66 (m, 2H), 1.63-1.58 (m, 1H), 1.18-1.09 (m, 2H) |
| I-218 | BAI | BXE | 774.4 | 11.09 (s, 1H), 10.24 (s, 1H), 8.42-8.38 (m, 1H), 8.37-8.33 (m, 2H), 8.16 (d, J = 7.6 Hz, 1H), 7.94 (s, 1H), 7.02 (s, 1H), 6.99-6.93 (m, 2H), 6.90 (dd, J = 2.4, 3.6 Hz, 1H), 5.36 (dd, J = 4.8, 12.4 Hz, 1H), 4.52-4.38 (m, 1H), 3.93 (s, 3H), 3.64 (s, 3H), 3.03-2.84 (m, 6H), 2.67-2.58 (m, 2H), 2.30-2.22 (m, 2H), 2.20-2.12 (m, 3H), 2.05-1.87 (m, 7H), 1.77-1.59 (m, 1H), 1.26-1.09 (m, 2H) |
| I-219 | BXY | ATJ | 782.2 | 10.51 (d, J = 8.4 Hz, 2H), 9.52 (s, 1H), 8.69 (s, 1H), 8.53 (s, 1H), 8.48-8.44 (m, 1H), 8.43-8.38 (m, 1H), 8.35 (s, 1H), 8.21 (d, J = 7.6 Hz, 1H), 7.74-7.68 (m, 1H), 7.64-7.59 (m, 1H), 7.32 (d, J = 7.6 Hz, 1H), 7.16 (s, 1H), 4.45-4.33 (m, 1H), 3.98 (s, 3H), 3.91 (ddd, J = 5.2, 9.6, 12.4 Hz, 1H), 3.70 (td, J = 6.0, 12.0 Hz, 1H), 3.23-3.05 (m, 5H), 3.01-2.92 (m, 1H), 2.75 (td, J = 5.6, 16.8 Hz, 1H), 2.34-2.27 (m, 2H), 2.20-2.03 (m, 9H), 2.00-1.84 (m, 3H), 1.24-1.13 (m, 2H) |
| I-220 | BXZ | ATJ | 768.2 | 10.51 (d, J = 12.0 Hz, 2H), 9.52 (s, 1H), 8.68 (s, 1H), 8.49 (s, 1H), 8.48-8.44 (m, 1H), 8.43-8.37 (m, 1H), 8.32 (s, 1H), 8.26-8.19 (m, 1H), 7.78-7.72 (m, 1H), 7.59 (dd, J = 2.4, 8.0 Hz, 2H), 7.15 (s, 1H), 4.37 (d, J = 3.2 Hz, 1H), 3.98 (s, 3H), 3.95-3.85 (m, 2H), 3.80 (d, J = 11.2 Hz, 1H), 3.75-3.71 (m, 1H), 3.70-3.66 (m, 2H), 3.49 (d, J = 11.2 Hz, 2H), 3.02-2.91 (m, 1H), 2.79-2.72 (m, 1H), 2.20-2.10 (m, 3H), 2.02-1.99 (m, 2H), 1.95-1.82 (m, 2H), 1.55-1.43 (m, 1H), 1.28-1.13 (m, 2H) |
| I-221 | BSN | BXE | 755.4 | 10.54 (s, 1H), 10.24 (s, 1H), 9.61 (s, 1H), 8.57 (s, 1H), 8.43-8.38 (m, 1H), 8.37-8.33 (m, 2H), 8.20-8.15 (m, 1H), 7.96 (d, J = 1.2 Hz, 1H), 7.88- |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 7.84 (m, 1H), 7.78 (t, J = 7.6 Hz, 1H), 7.68 (d, J = 7.2 Hz, 1H), 7.04 (d, J = 1.2 Hz, 1H), 4.47-4.38 (m, 1H), 3.93 (s, 3H), 3.92-3.88 (m, 1H), 3.72 (d, J = 6.0, 12.4 Hz, 1H), 3.66-3.57 (m, 1H), 3.07 (d, J = 11.1 Hz, 2H), 3.02-2.94 (m, 1H), 2.80-2.72 (m, 1H), 2.52 (s, 1H), 2.32 (d, J = 5.6 Hz, 3H), 2.20-2.13 (m, 2H), 2.04-1.98 (m, 2H), 1.97-1.85 (m, 6H), 1.76-1.66 (m, 1H), 1.24-1.11 (m, 2H) |
| I-222 | BXL | BXE | 756.4 | 10.53 (s, 1H), 10.24 (s, 1H), 9.43 (s, 1H), 8.53 (s, 1H), 8.43-8.38 (m, 1H), 8.37-8.33 (m, 2H), 8.16 (d, J = 7.2 Hz, 1H), 7.92 (d, J = 1.2 Hz, 1H), 7.77-7.69 (m, 1H), 7.64 (d, J = 8.4 Hz, 1H), 7.28 (d, J = 7.2 Hz, 1H), 7.04 (d, J = 1.2 Hz, 1H), 4.48-4.39 (m, 1H), 3.94-3.93 (m, 3H), 3.92-3.86 (m, 1H), 3.70 (d, J = 6.0, 12.0 Hz, 1H), 3.22-3.10 (m, 5H), 3.00-2.92 (m, 1H), 2.80-2.75 (m, 1H), 2.75-2.68 (m, 4H), 2.21-2.13 (m, 2H), 2.00 (d, J = 15.6 Hz, 2H), 1.97-1.88 (m, 2H), 1.78-1.64 (m, 2H), 1.24-1.10 (m, 2H) |
| I-223 | BXL | BCN | 773.3 | 10.56 (s, 1H), 10.52 (s, 1H), 9.52 (s, 1H), 9.02 (s, 1H), 8.60 (s, 1H), 8.50-8.39 (m, 2H), 8.25 (d, J = 8.4 Hz, 1H), 7.82-7.69 (m, 3H), 7.39 (d, J = 7.2 Hz, 1H), 4.04 (s, 3H), 3.93 (m, 3H), 3.78-3.65 (m, 4H), 3.35-3.08 (m, 8H), 2.98 (m, 1H), 2.82-2.73 (m, 1H), 2.25 (d, J = 11.6 Hz, 2H), 2.01 (d, J = 10.8 Hz, 3H), 1.75-1.62 (m, 2H), 1.34-1.22 (m, 2H) |
| I-224 | BXL | AGL | 784.4 | 1.11-1.34 (m, 2 H) 1.62 (s, 6 H) 2.01 (s, 5 H) 2.19 (d, J = 9.6 Hz, 2 H) 2.52 (s, 2 H) 2.76 (dt, J = 16.8, 5.2 Hz, 2H) 2.97 (s, 2 H) 3.05-3.29 (m, 5 H) 3.44-3.61 (m, 1 H) 3.70 (dt, J = 12.0, 6.0 Hz, 1 H) 3.85-3.97 (m, 1 H) 4.48 (s, 1 H) 5.95 (s, 1 H) 7.32 (dd, J = 4.0, 1.2 Hz, 1 H) 7.58 (s, 1 H) 7.60-7.70 (m, 1 H) 7.71-7.78 (m, 1 H) 8.17 (s, 1 H) 8.34-8.40 (m, 2 H) 8.44 (s, 1 H) 8.56 (s, 1 H) 8.72 (s, 1 H) 9.46 (s, 1 H) 10.54 (s, 1 H) 12.37 (s, 1 H) |
| I-225 | BWT | AGL | 814.4 | 12.36 (s, 1H), 11.09 (s, 1H), 8.72 (s, 1H), 8.49-8.41 (m, 1H), 8.41-8.33 (m, 2H), 8.19-8.14 (m, 1H), 7.57 (s, 1H), 6.98 (d, J = 4.4 Hz, 2H), 6.90-6.81 (m, 1H), 5.94 (s, 1H), 5.43-5.25 (m, 1H), 4.58-4.31 (m, 1H), 3.86 (s, 1H), 3.63 (d, J = 1.2 Hz, 3H), 3.57 (d, J = 10.0 Hz, 1H), 3.13 (d, J = 8.0 Hz, 1H), 3.03-2.75 (m, 4H), 2.71 (dd, J = 5.2, 7.2 Hz, 1H), 2.62 (d, J = 16.0 Hz, 2H), 2.17 (d, J = 12.0 Hz, 2H), 2.08-1.86 (m, 8H), 1.62 (s, 7H), 1.21 (J = 7.6, 12.0 Hz, 2H) |
| I-226 | BWR | AGL | 816.3 | 12.36 (s, 1H), 11.09 (s, 1H), 8.72 (s, 1H), 8.48-8.42 (m, 1H), 8.40-8.32 (m, 2H), 8.21-8.10 (m, 1H), 7.57 (s, 1H), 7.03-6.86 (m, 3H), 5.95 (s, 1H), 5.36 (dd, J = 5.4, 12.8 Hz, 1H), 4.54-4.35 (m, 1H), 3.64 (s, 3H), 3.21-2.98 (m, 4H), 2.97-2.78 (m, 3H), 2.71-2.58 (m, 3H), 2.16 (s, 3H), 2.03-1.84 (m, 5H), 1.62 (s, 7H), 1.40-0.97 (m, 6H) |
| I-227 | BXY | AGL | 810.2 | 12.36 (s, 1H), 10.53 (s, 1H), 9.53 (s, 1H), 8.72 (s, 1H), 8.54 (s, 1H), 8.47-8.43 (m, 1H), 8.40-8.32 (m, 2H), 8.18-8.12 (m, 1H), 7.75-7.69 (m, 1H), 7.64 (d, J = 8.4 Hz, 1H), 7.57 (s, 1H), 7.35 (d, J = 7.2 Hz, 1H), 5.94 (s, 1H), 4.52-4.39 (m, 1H), 3.91 (ddd, J = 5.2, 9.6, 12.4 Hz, 1H), 3.70 (td, J = 6.0, 12.0 Hz, 1H), 3.29-3.07 (m, 6H), 2.96 (ddd, J = 6.0, 10.0, 16.4 Hz, 1H), 2.76 (td, J = 5.6, 16.4 Hz, 1H), 2.55-2.51 (m, 4H), 2.22-2.04 (m, 7H), 1.95 (q, J = 12.0 Hz, 2H), 1.62 (s, 6H), 1.31-1.13 (m, 2H) |
| I-228 | BXZ | AGL | 796.2 | 12.36 (s, 1H), 10.54 (s, 1H), 9.54 (s, 1H), 8.71 (s, 1H), 8.51 (s, 1H), 8.47-8.42 (m, 1H), 8.41-8.32 (m, 2H), 8.16 (d, J = 7.6 Hz, 1H), 7.80-7.74 (m, 1H), 7.62 (d, J = 8.0 Hz, 2H), 7.57 (s, 1H), 5.95 (s, 1H), 4.50-4.36 (m, 1H), 3.96-3.81 (m, 4H), 3.71 (td, J = 6.0, 12.4 Hz, 1H), 3.65-3.45 (m, 6H), 2.97 (ddd, J = 6.0, 10.0, 16.4 Hz, 1H), 2.76 (td, J = 5.2, 16.8 Hz, 1H), 2.52 (d, J = 2.0 Hz, 2H), 2.15 (d, J = 10.8 Hz, 2H), 2.05-1.85 (m, 4H), 1.61 (s, 6H), 1.32-1.17 (m, 2H) |
| I-229 | BWB | AGL | 796.4 | 12.36 (s, 1H), 10.52 (d, J = 6.2 Hz, 1H), 9.42 (d, J = 12.4 Hz, 1H), 8.71 (s, 1H), 8.50-8.33 (m, 4H), |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| | | | | 8.16 (d, J = 7.6 Hz, 1H), 7.63 (q, J = 8.0 Hz, 1H), 7.56 (s, 1H), 7.47-7.32 (m, 1H), 7.14-6.98 (m, 1H), 5.94 (s, 1H), 4.66-4.50 (m, 1H), 4.49-4.37 (m, 1H), 3.98-3.89 (m, 1H), 3.86-3.78 (m, 1H), 3.69 (td, J = 6.0, 11.9 Hz, 2H), 3.46-3.37 (m, 2H), 2.99-2.91 (m, 1H), 2.76 (td, J = 5.2, 16.6 Hz, 2H), 2.59 (s, 1H), 2.21-2.09 (m, 3H), 2.04-1.86 (m, 5H), 1.75-1.65 (m, 1H), 1.61 (s, 6H), 1.33-1.09 (m, 3H) |
| I-230 | CAB | AGL | 798.4 | 12.36 (s, 1H), 10.54 (s, 1H), 9.57-9.43 (m, 1H), 8.72 (s, 1H), 8.60-8.52 (m, 1H), 8.46-8.43 (m, 1H), 8.39-8.34 (m, 2H), 8.18-8.15 (m, 1H), 7.77-7.61 (m, 2H), 7.57 (s, 1H), 7.40-7.24 (m, 1H), 5.94 (s, 1H), 4.53-4.42 (m, 1H), 3.95-3.88 (m, 1H), 3.73-3.67 (m, 1H), 3.63-3.52 (m, 1H), 3.24-3.17 (m, 2H), 3.16-3.03 (m, 2H), 3.00-2.93 (m, 1H), 2.80-2.72 (td, J = 5.6, 16.8 Hz, 2H), 2.26-2.07 (m, 5H), 2.03-1.87 (m, 4H), 1.62 (s, 6H), 1.49-1.35 (m, 2H), 1.26-1.06 (m, 4H) |
| I-231 | BAI | BWF | 782.4 | 11.09 (s, 1H), 8.84 (s, 1H), 8.81 (s, 1H), 8.67 (s, 1H), 8.55 (s, 1H), 8.52 (d, J = 3.6 Hz, 1H), 8.34 (d, J = 7.2 Hz, 1H), 8.09 (s, 1H), 7.04-6.89 (m, 3H), 6.88 (d, J = 3.6 Hz, 1H), 5.36 (dd, J = 5.6, 12.8 Hz, 1H), 4.57 (t, J = 10.8 Hz, 1H), 3.95-3.80 (m, 1H), 3.64 (s, 3H), 3.31-3.24 (m, 2H), 3.21-2.78 (m, 7H), 2.76-2.63 (m, 2H), 2.31-2.13 (m, 4H), 2.06-1.95 (m, 3H), 1.95-1.82 (m, 2H), 1.78-1.59 (m, 1H), 1.36 (d, J = 6.4 Hz, 6H), 1.28-1.09 (m, 2H) |
| I-232 | BWC | AGL | 814.4 | 12.36 (s, 1H), 11.11 (s, 1H), 8.71 (s, 1H), 8.49-8.41 (m, 1H), 8.40-8.32 (m, 2H), 8.16 (d, J = 7.2 Hz, 1H), 7.57 (s, 1H), 7.33 (d, J = 8.0 Hz, 1H), 7.10 (t, J = 8.0 Hz, 1H), 6.97 (d, J = 7.6 Hz, 1H), 5.94 (s, 1H), 5.45-5.30 (m, 1H), 4.49-4.41 (m, 1H), 3.77-3.65 (m, 2H), 3.62 (d, J = 11.2 Hz, 2H), 3.57 (s, 3H), 3.14-3.04 (m, 2H), 2.95-2.85 (m, 1H), 2.77-2.69 (m, 1H), 2.65 (m, 1H), 2.61 (s, 2H), 2.16 (d, J = 10.4 Hz, 2H), 2.03 (d, J = 8.0 Hz, 4H), 1.98-1.85 (m, 3H), 1.62 (s, 6H), 1.58-1.50 (m, 1H), 1.31-1.20 (m, 2H) |
| I-233 | CAC | ATJ | 770.3 | 10.55 (s, 1H), 10.51 (s, 1H), 9.83-9.25 (m, 1H), 8.70 (s, 1H), 8.58 (s, 1H), 8.50-8.44 (m, 1H), 8.44-8.37 (m, 1H), 8.35 (s, 1H), 8.25-8.20 (m, 1H), 7.92-7.69 (m, 2H), 7.69-7.46 (m, 1H), 7.15 (s, 1H), 4.50-4.36 (m, 1H), 3.99 (m, 3H), 3.95-3.86 (m, 1H), 3.81-3.60 (m, 3H), 3.60-3.47 (m, 1H), 3.26-3.06 (m, 3H), 2.98 (d, J = 6.0 Hz, 2H), 2.88-2.69 (m, 2H), 2.20 (d, J = 6.4 Hz, 2H), 2.14-1.86 (m, 5H), 1.43-0.94 (m, 3H), 0.89 (t, J = 7.2 Hz, 3H) |
| I-234 | CAC | AGL | 798.3 | 12.37 (s, 1H), 10.55 (s, 1H), 9.83-9.23 (m, 1H), 8.73 (s, 1H), 8.58 (s, 1H), 8.47-8.42 (m, 1H), 8.40-8.33 (m, 2H), 8.16 (d, J = 7.6 Hz, 1H), 7.93-7.70 (m, 2H), 7.57 (s, 2H), 5.95 (s, 1H), 4.49 (d, J = 1.6 Hz, 1H), 4.03-3.85 (m, 1H), 3.82-3.41 (m, 4H), 3.24-3.06 (m, 2H), 3.05-2.90 (m, 2H), 2.86-2.69 (m, 2H), 2.52 (d, J = 2.0 Hz, 1H), 2.19 (s, 3H), 2.02 (d, J = 10.4 Hz, 5H), 1.62 (s, 6H), 1.40-1.14 (m, 2H), 0.90 (t, J = 6.8 Hz, 3H) |
| I-236[h] | BTH | BAX | 872.4 | 10.88 (s, 1H), 7.60 (d, J = 8.4 Hz, 2H), 7.44 (s, 1H), 7.43-7.37 (m, 1H), 7.15 (d, J = 8.4 Hz, 2H), 5.18 (s, 1H), 4.31-4.16 (m, 2H), 3.70-3.66 (m, 4H), 2.85-2.76 (m, 2H), 2.70-2.63 (m, 2H), 1.83 (d, J = 12.4 Hz, 2H), 1.73-1.67 (m, 6H), 1.63-1.56 (m, 2H), 1.49 (s, 9H) |
| I-237 | CAE | CAG | 773.3 | 11.08 (s, 1H), 10.51 (s, 1H), 8.73-8.67 (m, 1H), 8.48-8.43 (m, 1H), 8.43-8.35 (m, 2H), 8.20 (d, J = 7.6 Hz, 1H), 7.16 (s, 1H), 7.04-6.93 (m, 3H), 5.35 (dd, J = 5.2, 12.4 Hz, 1H), 4.83-4.70 (m, 1H), 3.98 (s, 3H), 3.58 (s, 3H), 3.49-3.45 (m, 2H), 3.27-3.14 (m, 5H), 3.03 (s, 2H), 2.94-2.83 (m, 2H), 2.71-2.64 (m, 2H), 2.35 (s, 1H), 2.04-1.95 (m, 4H), 1.89 (d, J = 11.6 Hz, 2H), 1.67-1.55 (m, 2H), 1.29-1.22 (m, 2H) |
| I-238 | AQK | BRR | 773.4 | 11.09 (s, 1H), 10.20 (s, 1H), 9.06 (s, 1H), 8.61 (s, 1H), 8.52-8.45 (m, 2H), 8.45-8.38 (m, 1H), 8.32- |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| | | | | 8.22 (m, 1H), 7.02-6.94 (m, 1H), 6.94-6.84 (m, 2H), 5.35 (dd, J = 5.6, 12.8 Hz, 1H), 4.66-4.51 (m, 1H), 3.65 (s, 3H), 3.17 (d, J = 11.2 Hz, 2H), 2.95-2.83 (m, 1H), 2.80-2.56 (m, 5H), 2.48-2.25 (m, 5H), 2.20 (d, J = 9.2 Hz, 2H), 2.06-1.91 (m, 5H), 1.83 (s, 2H), 1.78-1.58 (m, 3H), 1.25-1.08 (m, 2H) |
| I-239 | AQK | BXI | 797.6 | 11.09 (s, 1H), 10.64 (s, 1H), 8.64 (s, 1H), 8.49-8.35 (m, 3H), 8.29-8.20 (m, 2H), 7.04-6.79 (m, 3H), 5.35 (dd, J = 5.4, 12.8 Hz, 1H), 4.62-4.51 (m, 1H), 3.64 (s, 3H), 3.16 (d, J = 11.2 Hz, 2H), 2.94-2.84 (m, 1H), 2.77-2.60 (m, 4H), 2.30 (d, J = 6.8 Hz, 2H), 2.26 (s, 3H), 2.19 (d, J = 9.6 Hz, 2H), 2.07-1.88 (m, 6H), 1.80 (d, J = 11.2 Hz, 2H), 1.73-1.55 (m, 3H), 1.20-1.05 (m, 2H) |
| I-240 | AZK | CAH | 761.4 | 11.11 (s, 1H), 10.46 (s, 1H), 8.56 (d, J = 2.8 Hz, 1H), 8.43-8.32 (m, 2H), 8.18-8.11 (m, 2H), 7.55 (dd, J = 0.8, 13.2 Hz, 1H), 7.05-6.94 (m, 3H), 5.42-5.31 (m, 1H), 4.56-4.45 (m, 1H), 3.60 (s, 3H), 3.09 (d, J = 8.8 Hz, 3H), 2.92-2.85 (m, 1H), 2.75-2.60 (m, 2H), 2.33-2.32 (m, 2H), 2.25-2.16 (m, 5H), 2.02-1.94 (m, 5H), 1.83 (s, 3H), 1.75-1.70 (m, 1H), 1.22-1.12 (m, 2H) |
| I-241 | BRY | BWU | 743.3 | 10.54 (s, 1H), 10.42 (s, 1H), 9.28 (s, 1H), 9.04 (s, 1H), 8.96 (s, 1H), 8.54-8.47 (m, 2H), 8.46-8.38 (m, 1H), 8.28-8.22 (m, 1H), 8.06 (s, 1H), 7.95 (d, J = 8.8 Hz, 1H), 7.78 (d, J = 8.4 Hz, 1H), 3.99-3.89 (m, 1H), 3.72 (td, J = 6.0, 12.0 Hz, 1H), 3.31-3.26 (m, 2H), 3.21-3.13 (m, 1H), 3.04-2.90 (m, 2H), 2.89-2.70 (m, 2H), 2.54-2.51 (m, 3H), 2.28-2.19 (m, 2H), 2.13-1.77 (m, 7H), 1.74-1.59 (m, 2H), 1.30-1.06 (m, 2H) |
| I-242 | AZK | CAI | 743.4 | 11.09 (s, 1H), 10.61 (s, 1H), 8.55 (d, J = 7.6 Hz, 1H), 8.42-8.33 (m, 2H), 8.22-8.18 (m, 2H), 7.35-7.18 (m, 1H), 7.08-6.90 (m, 3H), 6.38 (s, 1H), 5.37 (dd, J = 5.2, 12.4 Hz, 1H), 3.59 (s, 3H), 2.98 (d, J = 10.8 Hz, 2H), 2.93-2.85 (m, 1H), 2.77-2.68 (m, 2H), 2.65-2.58 (m, 1H), 2.19 (d, J = 6.8 Hz, 2H), 2.11-1.98 (m, 5H), 1.96-1.89 (m, 2H), 1.78 (s, 4H), 1.68-1.39 (m, 4H), 1.12-0.99 (m, 2H) |
| I-243 | BWR | ATJ | 788.3 | 11.11 (s, 1H), 10.51 (s, 1H), 8.92-8.78 (m, 1H), 8.70 (s, 1H), 8.48-8.45 (m, 1H), 8.43-8.39 (m, 1H), 8.22 (d, J = 8.4 Hz, 1H), 7.14 (s, 1H), 7.08-7.02 (m, 1H), 7.01-6.93 (m, 2H), 5.38 (dd, J = 5.4, 12.8 Hz, 1H), 4.51-4.34 (m, 1H), 3.99 (s, 3H), 3.76 (d, J = 11.6 Hz, 1H), 3.65 (s, 3H), 3.62-3.52 (m, 1H), 3.27 (s, 1H), 3.21-2.81 (m, 5H), 2.78-2.53 (m, 3H), 2.46-2.35 (m, 1H), 2.21 (d, J = 11.6 Hz, 2H), 2.13-1.82 (m, 6H), 1.55-1.23 (m, 5H) |
| I-244 | CAJ | BVB | 757.4 | 11.10 (s, 1H), 9.90 (s, 1H), 9.30 (s, 1H), 9.20 (d, J = 1.6 Hz, 1H), 8.77 (s, 1H), 8.29 (s, 1H), 8.07 (s, 1H), 7.12-7.01 (m, 2H), 7.00-6.87 (m, 2H), 5.36 (dd, J = 5.2, 12.4 Hz, 1H), 4.41-4.29 (m, 1H), 3.87 (s, 3H), 3.76 (d, J = 2.4 Hz, 2H), 3.63 (s, 3H), 3.54 (s, 4H), 3.27 (s, 4H), 2.99-2.81 (m, 2H), 2.76-2.68 (m, 1H), 2.66-2.53 (m, 2H), 2.11 (d, J = 9.6 Hz, 2H), 2.03-1.96 (m, 1H), 1.91-1.80 (m, 4H), 1.50-1.37 (m, 1H), 1.19-1.06 (m, 2H) |
| I-245 | CAK | BRR | 788.4 | 10.20 (s, 1H), 9.07 (s, 1H), 8.62 (s, 1H), 8.51-8.47 (m, 2H), 8.42 (t, J = 7.6 Hz, 1H), 8.24 (d, J = 7.6 Hz, 1H), 6.94-6.87 (m, 1H), 6.71 (d, J = 8.8 Hz, 1H), 5.39 (dd, J = 5.6, 12.8 Hz, 1H), 4.64-4.54 (m, 1H), 3.77 (s, 3H), 3.57 (s, 3H), 3.03 (s, 3H), 3.01-2.92 (m, 3H), 2.82-2.68 (m, 2H), 2.44-2.39 (m, 2H), 2.20 (d, J = 6.4 Hz, 4H), 2.07-1.87 (m, 8H), 1.75-1.64 (m, 1H), 1.58 (d, J = 10.8 Hz, 2H), 1.24-1.12 (m, 2H) |
| I-246[b] | CAL | ATJ | 788.4 | 11.1 (s, 1H), 10.5 (s, 1H), 8.70 (s, 1H), 8.48-8.44 (m, 1H), 8.43-8.38 (m, 1H), 8.35 (s, 1H), 8.22 (d, J = 8.0 Hz, 1H), 7.15 (s, 1H), 7.08-6.92 (m, 3H), 5.41-5.33 (m, 1H), 4.48-4.37 (m, 1H), 3.99 (s, 3H), 3.65 (s, 3H), 3.21-3.04 (m, 4H), 3.03-2.84 (m, 3H), 2.77-2.69 (m, 1H), 2.65-2.59 (m, 1H), 2.20-2.19 (m, 2H), 2.11 (d, J = 12.8 Hz, 1H), 2.08- |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-248[b] | CAL | BTW | 758.3 | 1.84 (m, 6H), 1.53-1.41 (m, 1H), 1.39-1.33 (m, 2H), 1.29-1.22 (m, 1H), 1.21-1.13 (m, 3H) 11.11 (s, 1H), 10.37 (s, 1H), 8.43 (s, 1H), 8.41-8.33 (m, 2H), 8.32 (d, J = 0.8 Hz, 1H), 8.18 (dd, J = 1.2, 7.6 Hz, 1H), 7.65-7.59 (m, 1H), 7.58-7.53 (m, 1H), 7.10-7.02 (m, 1H), 7.01-6.90 (m, 2H), 5.38 (dd, J = 5.6, 12.8 Hz, 1H), 4.56-4.44 (m, 1H), 3.76 (d, J = 11.2 Hz, 1H), 3.65 (s, 3H), 3.62-3.53 (m, 1H), 3.22-3.10 (m, 2H), 3.09-2.99 (m, 2H), 2.99-2.78 (m, 2H), 2.77-2.68 (m, 1H), 2.66 (s, 1H), 2.31-2.16 (m, 3H), 2.04 (m, 2H), 2.03-1.96 (m, 3H), 1.94-1.84 (m, 1H), 1.50 (s, 1H), 1.37 (d, J = 5.6 Hz, 3H), 1.31 (d, J = 12.8 Hz, 1H), 1.26-1.13 (m, 1H) |
| I-249 | AQK | BWH | 813.5 | 11.10 (s, 1H), 10.53 (s, 1H), 9.32 (d, J = 1.6 Hz, 1H), 9.25 (d, J = 1.6 Hz, 1H), 8.79-8.75 (m, 1H), 8.58 (s, 1H), 7.99 (s, 1H), 7.71 (s, 1H), 7.04-6.97 (m, 1H), 6.96-6.86 (m, 2H), 5.36 (dd, J = 5.2, 12.8 Hz, 1H), 4.63-4.47 (m, 1H), 3.65 (s, 3H), 3.27-3.18 (m, 3H), 2.99-2.73 (m, 6H), 2.70-2.56 (m, 3H), 2.24-2.16 (m, 2H), 2.12-1.94 (m, 7H), 1.94-1.61 (m, 4H), 1.40-1.17 (m, 2H) |
| I-252 | CAO | ATJ | 768.3 | 10.55-10.47 (m, 2H), 9.42 (d, J = 11.2 Hz, 1H), 8.68 (s, 1H), 8.50-8.43 (m, 2H), 8.42-8.36 (m, 1H), 8.32 (s, 1H), 8.21 (d, J = 7.6 Hz, 1H), 7.62 (q, J = 7.2 Hz, 1H), 7.39 (s, 1H), 7.14 (s, 1H), 7.09-6.97 (m, 1H), 4.70-4.46 (m, 1H), 4.41-4.33 (m, 1H), 3.98 (s, 3H), 3.95-3.77 (m, 2H), 3.76-3.62 (m, 2H), 3.38-3.34 (m, 5H), 2.99-2.91 (m, 1H), 2.80-2.72 (m, 1H), 2.25-2.08 (m, 3H), 2.04-1.81 (m, 5H), 1.76-1.50 (m, 1H), 1.28-1.09 (m, 2H) |
| I-253 | CAQ | ATJ | 788.3 | 11.09 (s, 1H), 10.50 (s, 1H), 8.69 (s, 1H), 8.48-8.44 (m, 1H), 8.43-8.38 (m, 1H), 8.34 (s, 1H), 8.24-8.20 (m, 1H), 7.16 (s, 1H), 7.05-6.98 (m, 2H), 6.97-6.89 (m, 1H), 5.40-5.30 (m, 1H), 4.45-4.34 (m, 1H), 4.16-4.08 (m, 2H), 3.98 (s, 3H), 3.01-2.84 (m, 6H), 2.76-2.68 (m, 1H), 2.67-2.56 (m, 2H), 2.28-2.13 (m, 5H), 2.06-1.84 (m, 6H), 1.75-1.60 (m, 1H), 1.25-1.10 (m, 5H) |
| I-254 | CAO | AGL | 796.4 | 12.36 (s, 1H), 10.51 (d, J = 6.0 Hz, 1H), 9.42 (d, J = 12.0 Hz, 1H), 8.71 (s, 1H), 8.49-8.42 (m, 2H), 8.39-8.33 (m, 2H), 8.17-8.13 (m, 1H), 7.63 (q, J = 7.6 Hz, 1H), 7.56 (s, 1H), 7.44-7.36 (m, 1H), 7.11-6.98 (m, 1H), 5.94 (s, 1H), 4.58-4.40 (m, 2H), 4.16-4.02 (m, 1H), 3.99-3.89 (m, 1H), 3.87-3.59 (m, 4H), 3.00-2.88 (m, 2H), 2.81-2.72 (m, 2H), 2.52-2.51 (m, 1H), 2.20-2.09 (m, 4H), 2.03-1.87 (m, 5H), 1.61 (s, 6H), 1.24-1.13 (m, 2H) |
| I-255 | CAR | ATJ | 788.3 | 11.08 (s, 1H), 10.40 (s, 1H), 8.68 (s, 1H), 8.50-8.37 (m, 2H), 8.32 (s, 1H), 8.28-822 (m, 1H), 7.16 (s, 1H), 7.02-6.92 (m, 2H), 6.88-6.84 (m, 1H), 5.36 (dd, J = 5.2 Hz, 12.8 1H), 4.45-4.31 (m, 1H), 3.98 (s, 3H), 3.66 (s, 3H), 3.16 (d, 4H), 2.94-2.84 (m, 1H), 2.76 (s, 4H), 2.66-2.55 (m, 2H), 2.32 (d, 2H), 2.16 (d, 2H), 2.05-1.82 (m, 8H), 1.68-1.51 (m, 1H), 1.21-1.05 (m, 2H) |
| I-256 | CAS | ATJ | 770.4 | 10.54 (s, 1H), 10.51 (s, 1H), 9.77-9.52 (m, 1H), 8.70 (s, 1H), 8.62-8.51 (m, 1H), 8.48-8.44 (m, 1H), 8.43-8.38 (m, 1H), 8.34 (s, 1H), 8.23-8.19 (m, 1H), 7.89-7.69 (m, 2H), 7.62-7.41 (m, 1H), 7.15 (s, 1H), 4.48-4.37 (m, 1H), 3.99 (s, 3H), 3.96-3.86 (m, 1H), 3.85-3.59 (m, 3H), 3.59-3.47 (m, 1H), 3.21-3.14 (m, 1H), 3.02-2.84 (m, 2H), 2.83-2.69 (m, 2H), 2.56-2.51 (m, 1H), 2.31-2.11 (m, 4H), 2.09-1.89 (m, 5H), 1.38-1.12 (m, 2H), 0.89 (t, J = 6.8 Hz, 3H) |
| I-257 | CAS | AGL | 798.4 | 12.37 (s, 1H), 10.55 (s, 1H), 9.59 (s, 1H), 8.73 (s, 1H), 8.55 (d, J = 2.4 Hz, 1H), 8.48-8.44 (m, 1H), 8.40-8.34 (m, 2H), 8.19-8.13 (m, 1H), 7.83-7.77 (m, 1H), 7.75-7.69 (m, 1H), 7.61-7.55 (m, 1H), 7.48 (s, 1H), 5.95 (s, 1H), 4.53-4.41 (m, 1H), 4.02-3.85 (m, 1H), 3.78-3.69 (m, 1H), 3.61-3.47 (m, 1H), 3.28-3.19 (m, 1H), 3.03-2.84 (m, 3H), 2.81-2.73 (m, 2H), 2.33-2.24 (m, 2H), |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 2.19 (d, J = 11.2 Hz, 2H), 2.09-1.89 (m, 5H), 1.83-1.66 (m, 2H), 1.63 (s, 6H), 1.27-1.15 (m, 2H), 0.90 (t, J = 5.2 Hz, 3H) |
| I-258 | BWC | BVB | 743.4 | 11.11 (s, 1H), 9.91 (s, 1H), 9.31 (s, 1H), 9.21 (d, J = 2.0 Hz, 1H), 8.78 (s, 1H), 8.31 (s, 1H), 8.08 (s, 1H), 7.45-7.25 (m, 1H), 7.19-7.05 (m, 2H), 7.03-6.94 (m, 1H), 5.38 (dd, J = 4.8, 12.0 Hz, 1H), 4.48-4.34 (m, 1H), 3.87 (s, 3H), 3.83-3.60 (m, 4H), 3.57 (s, 3H), 3.18-3.04 (m, 2H), 2.95-2.85 (m, 1H), 2.79-2.67 (m, 2H), 2.66-2.58 (m, 2H), 2.21-2.12 (m, 2H), 2.10-1.82 (m, 7H), 1.67-1.47 (m, 1H), 1.34-1.18 (m, 2H) |
| I-259 | BXL | BVB | 713.6 | 10.53 (s, 1H), 9.90 (s, 1H), 9.43 (s, 1H), 9.34-9.30 (m, 1H), 9.22-9.18 (m, 1H), 8.78 (s, 1H), 8.53 (s, 1H), 8.32 (s, 1H), 8.08 (s, 1H), 7.76-7.69 (m, 1H), 7.62 (d, J = 8.4 Hz, 1H), 7.29 (d, J = 7.2 Hz, 1H), 7.09 (s, 1H), 4.45-4.33 (m, 1H), 3.95-3.89 (m, 1H), 3.88 (s, 3H), 3.74-3.67 (m, 1H), 3.48-3.40 (m, 1H), 3.24-3.09 (m, 4H), 3.03-2.90 (m, 1H), 2.79-2.67 (m, 4H), 2.36-2.28 (m, 2H), 2.21-2.12 (m, 2H), 2.06-1.97 (m, 2H), 1.97-1.86 (m, 2H), 1.79-1.64 (m, 1H), 1.25-1.09 (m, 2H) |
| I-260 | BAI | BSC | 758.5 | 11.10 (s, 1H), 10.14 (s, 1H), 8.51-8.31 (m, 3H), 8.24-8.11 (m, 2H), 7.52 (s, 1H), 7.09-6.85 (m, 3H), 5.37 (d, J = 5.2 Hz, 1H), 4.53-4.39 (m, 1H), 3.65 (s, 3H), 3.15-2.82 (m, 6H), 2.77-2.58 (m, 4H), 2.41 (s, 3H), 2.30-2.12 (m, 4H), 2.08-1.86 (m, 6H), 1.84-1.57 (m, 1H), 1.30-1.08 (m, 2H) |
| I-261[b] | BXL | BSC | 740.3 | 10.5 (s, 1H), 10.13 (s, 1H), 9.54-9.38 (m, 1H), 8.56 (s, 1H), 8.46-8.35 (m, 3H), 8.23-8.12 (m, 2H), 7.79-7.71 (m, 1H), 7.70-7.62 (m, 1H), 7.52 (s, 1H), 7.37-7.23 (m, 1H), 4.53-4.40 (m, 1H), 3.96-3.87 (m, 1H), 3.73-3.74 (m, 1H), 3.29-3.11 (m, 5H), 2.97-2.93 (m, 2H), 2.79-2.72 (m, 2H), 2.52 (s, 1H), 2.41 (s, 3H), 2.20 (d, J = 10.0 Hz, 3H), 2.11-1.88 (m, 5H), 1.85-1.67 (m, 1H), 1.32-1.14 (m, 2H) |
| I-262[b] | BWS | BVB | 757.4 | 11.13-11.03 (m, 1H), 9.91 (s, 1H), 9.31 (s, 1H), 9.20 (d, J = 1.6 Hz, 1H), 8.78 (s, 1H), 8.32 (s, 1H), 8.08 (s, 1H), 7.13-7.07 (m, 2H), 7.00 (d, J = 7.8 Hz, 1H), 6.91 (d, J = 7.6 Hz, 1H), 5.35 (d, J = 12.6 Hz, 1H), 4.45-4.34 (m, 1H), 3.88 (s, 3H), 3.71 (s, 3H), 3.07 (d, J = 10.4 Hz, 2H), 2.80 (d, J = 7.8 Hz, 2H), 2.70 (d, J = 5.6 Hz, 1H), 2.65-2.62 (m, 1H), 2.60 (br d, J = 0.8 Hz, 1H), 2.26 (d, J = 6.8 Hz, 3H), 2.20-2.13 (m, 3H), 2.07 (d, J = 12 Hz, 2H), 1.90 (d, J = 5.2 Hz, 6H), 1.60-1.50 (m, 1H), 1.23-1.14 (m, 2H) |
| I-263 | CAT | AGL | 886.5 | 11.10 (s, 1H), 8.72 (s, 1H), 8.46-8.43 (m, 1H), 8.40-8.34 (m, 2H), 8.18-8.14 (m, 1H), 7.62 (t, J = 7.6 Hz, 1H), 7.55 (s, 1H), 7.12 (d, J = 6.0 Hz, 1H), 6.90 (d, J = 8.8 Hz, 1H), 6.69-6.54 (m, 2H), 5.94 (s, 1H), 5.07 (dd, J = 5.6, 12.8 Hz, 1H), 4.51-4.40 (m, 1H), 4.14-4.05 (m, 1H), 3.80-3.49 (m, 3H), 2.95-2.80 (m, 4H), 2.64-2.60 (m, 2H), 2.57 (s, 3H), 2.55-2.53 (m, 1H), 2.37 (s, 3H), 2.25-2.14 (m, 4H), 2.07-2.00 (m, 2H), 1.99-1.92 (m, 4H), 1.91-1.68 (m, 4H), 1.62 (s, 6H), 1.28-1.17 (m, 2H) |
| I-264 | AOQ | CAU | 801.8[e] | 12.38 (s, 1H), 11.09 (s, 1H), 8.69 (s, 1H), 8.32 (s, 1H), 8.01-7.87 (m, 2H), 7.64-7.53 (m, 2H), 7.52-7.45 (m, 1H), 7.07 (d, J = 7.2 Hz, 1H), 6.92 (d, J = 8.4 Hz, 1H), 6.51 (d, J = 6.0 Hz, 1H), 5.90 (s, 1H), 5.07-5.03 (m, 1H), 4.49-4.33 (m, 1H), 4.22-4.05 (m, 2H), 3.37-3.35 (m, 3H), 2.94-2.80 (m, 1H), 2.60 (s, 3H), 2.56 (s, 1H), 2.52-2.51 (m, 2H), 2.42-2.35 (m, 3H), 2.28-2.20 (m, 7H), 2.14-2.12 (m, 2H), 2.06-2.00 (m, 1H), 1.95-1.90 (m, 4H), 1.72-1.66 (m, 2H), 1.63 (s, 6H), 1.17-1.06 (m, 2H) |
| I-265 | AOQ | CAW | 805.8 | 12.32 (s, 1H), 11.09 (s, 1H), 8.74-8.69 (m, 1H), 8.67 (s, 1H), 8.33 (s, 1H), 8.19 (d, J = 6.4 Hz, 1H), 8.06 (t, J = 1., 7.6 Hz, 1H), 7.65-7.62 (m, 1H), 7.58 (d, J = 7.2, 8.4 Hz, 1H), 7.54 (s, 1H), 7.07 (d, J = 6.8 Hz, 1H), 6.92 (d, J = 8.4 Hz, 1H), 6.50 (d, J = 6.0 Hz, 1H), 6.02 (s, 1H), 5.07-5.02 (m, 1H), |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-266 | CAX | ATJ | 757.3 | 4.46-4.36 (m, 1H), 4.19-4.09 (m, 2H), 3.35 (s, 2H), 2.92-2.83 (m, 1H), 2.61-2.55 (m, 1H), 2.52-2.51 (m, 1H), 2.43-2.38 (m, 2H), 2.37-2.34 (m, 2H), 2.27-2.20 (m, 2H), 2.16 (s, 4H), 2.15-2.11 (m, 3H), 2.05-1.99 (m, 1H), 1.96-1.86 (m, 4H), 1.69-1.63 (m, 2H), 1.61 (s, 6H), 1.15-1.02 (m, 3H) |
| I-267 | CAY | CAZ | 751.1 | 11.14 (s, 1H), 10.51 (s, 2H), 8.70 (s, 1H), 8.54-8.31 (m, 3H), 8.22 (d, J = 7.6 Hz, 1H), 7.22-7.14 (m, 2H), 7.11 (t, J = 7.6 Hz, 1H), 7.00 (d, J = 7.6 Hz, 1H), 6.04 (s, 1H), 5.44 (d, J = 5.2, 12.7 Hz, 1H), 4.83-4.11 (m, 5H), 3.99 (s, 3H), 3.37 (s, 3H), 3.00-2.86 (m, 1H), 2.82-2.70 (m, 1H), 2.69-2.63 (m, 1H), 2.59-2.52 (m, 2H), 2.20 (d, J = 10.4 Hz, 2H), 2.10-1.89 (m, 6H), 1.30 (d, J = 11.6 Hz, 2H) |
| I-268 | CBA | ATJ | 842.4 | 11.1 (s, 1H), 8.58-8.54 (m, 2H), 8.47 (d, J = 4.0 Hz, 1H), 8.42-8.39 (m, 1H), 8.31 (d, J = 7.6 Hz, 1H), 8.20 (s, 1H), 8.03 (dd, J = 2.8, 9.2 Hz, 1H), 6.97 (d, J = 8.4 Hz, 1H), 6.88 (s, 1H), 6.75 (d, J = 4.0 Hz, 1H), 6.66 (d, J = 7.4 Hz, 1H), 5.30 (dd, J = 5.2, 12.8 Hz, 1H), 3.82-3.76 (m, 1H), 3.74 (d, J = 6.0 Hz, 1H), 3.32 (s, 3H), 3.16-3.04 (m, 3H), 2.97-2.83 (m, 2H), 2.76-2.65 (m, 2H), 2.61 (d, J = 16.4 Hz, 2H), 2.53 (d, J = 6.8 Hz, 3H), 2.02-1.96 (m, 1H), 1.93-1.83 (m, 4H), 1.70-1.51 (m, 1H), 1.49-1.31 (m, 3H), 1.29 (d, J = 6.4 Hz, 6H), 1.16-0.96 (m, 2H) |
| I-269 | BSN | BSC | 739.4 | 11.1 (s, 1H), 10.50 (s, 1H), 8.69 (s, 1H), 8.47-8.43 (m, 1H), 8.42-8.37 (m, 1H), 8.32 (s, 1H), 8.21 (d, J = 7.6 Hz, 1H), 7.15 (s, 1H), 7.10-7.06 (m, 1H), 7.06-7.02 (m, 1H), 7.01-6.97 (m, 1H), 5.36 (dd, J = 5.6, 12.4 Hz, 1H), 4.42-4.32 (m, 1H), 3.98 (s, 3H), 3.57 (s, 3H), 3.13-3.03 (m, 1H), 3.00-2.82 (m, 4H), 2.81-2.66 (m, 4H), 2.66-2.54 (m, 4H), 2.54 (s, 3H), 2.14 (d, J = 10.4 Hz, 4H), 2.03-1.82 (m, 8H), 1.65 (s, 1H), 1.20-1.08 (m, 2H) |
| I-269 | BSN | BSC | 739.4 | 10.55 (s, 1H), 10.14 (s, 1H), 9.67 (s, 1H), 8.64-8.56 (m, 1H), 8.49-8.32 (m, 3H), 8.22 (d, J = 3.2 Hz, 2H), 8.00-7.74 (m, 2H), 7.70-7.47 (m, 2H), 4.56-4.40 (m, 1H), 3.94 (d, J = 5.2, 9.9, 12.1 Hz, 1H), 3.88-3.66 (m, 2H), 3.52-3.37 (m, 1H), 2.99 (d, J = 16.4 Hz, 2H), 2.89-2.58 (m, 4H), 2.42 (s, 3H), 2.21 (d, J = 10.8 Hz, 2H), 2.13-1.80 (m, 9H), 1.30-1.19 (m, 2H) |
| I-271 | BRY | BXI | 750.6 | 10.64 (s, 1H), 10.56-10.50 (m, 1H), 9.28-9.23 (m, 1H), 8.66-8.61 (m, 1H), 8.48 (s, 1H), 8.47-8.36 (m, 3H), 8.26-8.19 (m, 2H), 8.07 (s, 1H), 7.92 (d, J = 8.8 Hz, 1H), 7.79 (dd, J = 1.2, 8.8 Hz, 1H), 4.63-4.52 (m, 1H), 3.99-3.87 (m, 1H), 3.76-3.66 (m, 1H), 3.07-2.92 (m, 3H), 2.76 (td, J = 5.6, 16.8 Hz, 2H), 2.26-2.16 (m, 4H), 2.11-1.94 (m, 6H), 1.89-1.63 (m, 5H), 1.23-1.11 (m, 2H) |
| I-272 | CCK | ATJ | 770.2 | 10.52 (d, J = 13.6 Hz, 2H), 9.52 (s, 1H), 8.70 (s, 1H), 8.55 (s, 1H), 8.48-8.37 (m, 2H), 8.35 (s, 1H), 8.22 (dd, J = 0.8, 7.6 Hz, 1H), 7.78-7.70 (m, 1H), 7.64 (d, J = 8.4 Hz, 1H), 7.37 (d, J = 7.2 Hz, 1H), 7.15 (s, 1H), 4.48-4.37 (m, 1H), 3.99 (s, 3H), 3.91 (m, 1H), 3.70 (m, 1H), 3.60 (s, 2H), 3.42 (m, 5H), 3.09 (s, 1H), 2.97 (m, 2H), 2.76 (m, 1H), 2.52 (d, J = 2.0 Hz, 1H), 2.20 (d, J = 9.6 Hz, 4H), 2.07-1.85 (m, 5H), 1.36-1.21 (m, 2H) |
| I-273 | CCL | AGL | 798.3 | 12.37 (s, 1H), 10.55 (s, 1H), 9.62-9.42 (m, 1H), 8.73 (s, 1H), 8.63-8.52 (m, 1H), 8.48-8.33 (m, 3H), 8.21-8.11 (m, 1H), 7.75 (d, J = 2.8 Hz, 2H), 7.57 (s, 1H), 7.44-7.25 (m, 1H), 5.95 (s, 1H), 4.55-4.40 (m, 1H), 3.99-3.81 (m, 2H), 3.74-3.51 (m, 3H), 3.17-3.04 (m, 2H), 3.03-2.87 (m, 2H), 2.84-2.73 (m, 2H), 2.28-2.09 (m, 4H), 2.07-1.88 (m, 4H), 1.62 (s, 7H), 1.50-1.29 (m, 3H), 1.25-1.07 (m, 2H) |
| I-276 | CBX | BRR | 772.3 | 11.1 (s, 1H), 10.20 (s, 1H), 9.07 (s, 1H), 8.61 (s, 1H), 8.51-8.49 (m, 1H), 8.47 (s, 1H), 8.41 (t, J = 7.6 Hz, 1H), 8.23 (dd, J = 0.8, 7.6 Hz, 1H), 7.03-6.93 (m, 1H), 6.75-6.63 (m, 1H), 5.66 (s, 1H), 5.35 (dd, J = 5.6, 12.4 Hz, 1H), 4.67-4.57 (m, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 1H), 3.75 (s, 3H), 3.34-3.34 (m, 3H), 2.96-2.81 (m, 2H), 2.76-2.57 (m, 4H), 2.55-2.51 (m, 1H), 2.48-2.42 (m, 3H), 2.24-2.22 (m, 3H), 2.06-1.96 (m, 6H), 1.35-1.21 (m, 2H) |
| I-277 | CBX | ATJ | 801.3 | 11.10 (s, 1H), 10.51 (s, 1H), 8.70 (s, 1H), 8.49-8.44 (m, 1H), 8.44-8.38 (m, 1H), 8.35 (s, 1H), 8.22 (dd, J = 0.8, 7.6 Hz, 1H), 7.16 (s, 1H), 6.99 (d, J = 7.6 Hz, 1H), 6.71 (d, J = 8.0 Hz, 1H), 5.64 (s, 1H), 5.35 (dd, J = 4.4, 12.4 Hz, 1H), 4.46-4.35 (m, 1H), 3.99 (s, 3H), 3.74 (s, 3H), 3.38-3.33 (m, 4H), 2.95-2.84 (m, 1H), 2.76-2.68 (m, 1H), 2.67-2.56 (m, 2H), 2.56-2.51 (m, 7H), 2.18 (d, J = 10.8 Hz, 2H), 2.05-1.89 (m, 5H), 1.35-1.12 (m, 2H) |
| I-278 | AZK | CAZ | 750.4 | 11.1 (s, 1H), 8.59-8.54 (m, 2H), 8.47 (d, J = 3.6 Hz, 1H), 8.42-8.39 (m, 1H), 8.29 (d, J = 7.6 Hz, 1H), 8.19 (s, 1H), 8.03 (dd, J = 2.8, 9.2 Hz, 1H), 7.02 (d, J = 4.8 Hz, 2H), 6.99-6.95 (m, 1H), 6.75 (d, J = 4.0 Hz, 1H), 5.37 (dd, J = 5.2, 12.4 Hz, 1H), 3.81-3.71 (m, 2H), 3.59 (s, 3H), 3.02 (d, J = 10.4 Hz, 2H), 2.93-2.85 (m, 1H), 2.77-2.68 (m, 1H), 2.67-2.55 (m, 2H), 2.24 (s, 2H), 2.15 (s, 2H), 1.99-1.93 (m, 1H), 1.88-1.83 (m, 4H), 1.80 (s, 4H), 1.57-1.48 (m, 1H), 1.42-1.32 (m, 2H), 1.29 (d, J = 6.4 Hz, 6H), 1.03-0.92 (m, 2H) |
| I-279 | BWS | BRR | 771.7 | 11.1 (s, 1H), 10.2 (s, 1H), 9.07 (s, 1H), 8.63 (s, 1H), 8.51 (d, J = 1.2 Hz, 1H), 8.50-8.47 (m, 1H), 8.44-8.39 (m, 1H), 8.24 (d, J = 7.6 Hz, 1H), 7.20-6.95 (m, 3H), 5.38 (dd, J = 5.2, 12.4 Hz, 1H), 4.69-4.57 (m, 1H), 4.26-4.06 (m, 1H), 3.71 (s, 3H), 3.63-3.37 (m, 2H), 3.17-2.96 (m, 3H), 2.96-2.82 (m, 2H), 2.76-2.67 (m, 1H), 2.66-2.59 (m, 1H), 2.52 (d, J = 2.0 Hz, 1H), 2.25 (d, J = 10.8 Hz, 5H), 2.09 (d, J = 13.6 Hz, 3H), 2.05-1.95 (m, 4H), 1.39-1.24 (m, 2H) |
| I-280 | BXY | BVB | 739.3 | 10.54 (s, 1H), 9.91 (s, 1H), 9.54 (s, 1H), 9.31 (d, J = 1.2 Hz, 1H), 9.21 (d, J = 1.6 Hz, 1H), 8.78 (s, 1H), 8.56 (s, 1H), 8.33 (s, 1H), 8.09 (s, 1H), 7.82-7.57 (m, 2H), 7.37 (d, J = 1.6 Hz, 1H), 7.08 (s, 1H), 4.43 (t, J = 11.6 Hz, 1H), 3.97-3.90 (m, 1H), 3.88 (s, 3H), 3.70 (td, J = 6.0, 12.0 Hz, 1H), 3.32-3.29 (m, 3H), 3.26-3.05 (m, 3H), 3.01-2.92 (m, 1H), 2.76 (td, J = 5.6, 16.4 Hz, 1H), 2.59 (s, 2H), 2.19 (d, J = 10.4 Hz, 4H), 2.08 (d, J = 12.0 Hz, 3H), 2.02-1.85 (m, 3H), 1.85-1.50 (m, 1H), 1.36-1.12 (m, 2H) |
| I-282 | BXL | CCR | 774.3 | 10.53 (s, 1H), 10.34 (s, 1H), 9.43 (s, 1H), 8.72 (s, 1H), 8.53 (s, 1H), 8.47-8.33 (m, 2H), 8.21 (d, J = 7.6 Hz, 1H), 7.76-7.70 (m, 1H), 7.62 (d, J = 8.4 Hz, 1H), 7.29 (t, J = 3.6 Hz, 2H), 4.03 (d, J = 12.0 Hz, 2H), 3.96 (s, 3H), 3.93-3.86 (m, 1H), 3.70 (td, J = 6.0, 12.4 Hz, 1H), 3.23-3.08 (m, 6H), 2.98-2.94 (m, 1H), 2.79-2.74 (m, 1H), 2.70 (s, 4H), 2.34-2.31 (m, 2H), 1.89 (d, J = 11.6 Hz, 3H), 1.31-1.18 (m, 2H) |
| I-283 | CCS | BRR | 775.3 | 11.07 (s, 1H), 10.20 (s, 1H), 9.07 (s, 1H), 8.61 (s, 1H), 8.52-8.45 (m, 2H), 8.41 (t, J = 7.6 Hz, 1H), 8.23 (d, J = 7.6 Hz, 1H), 6.88 (d, J = 8.4 Hz, 1H), 6.68 (d, J = 8.8 Hz, 1H), 5.36-5.26 (m, 1H), 4.65-4.53 (m, 1H), 3.79 (s, 3H), 3.62 (s, 3H), 3.51 (t, J = 10.0 Hz, 2H), 2.83-2.74 (m, 4H), 2.65-2.57 (m, 3H), 2.25-2.14 (m, 6H), 1.98 (t, J = 11.2 Hz, 5H), 1.70 (s, 1H), 1.25-1.07 (m, 2H) |
| I-284 | BXL | BKQ | 744.3 | 10.53 (s, 1H), 10.24 (d, J = 2.4 Hz, 1H), 9.44 (s, 1H), 8.54 (s, 1H), 8.51 (s, 1H), 8.48-8.37 (m, 3H), 8.24-8.20 (m, 1H), 7.76-7.69 (m, 1H), 7.62 (d, J = 8.4 Hz, 1H), 7.55 (d, J = 12.0 Hz, 1H), 7.29 (d, J = 7.6 Hz, 1H), 4.52-4.43 (m, 1H), 3.91 (m, J = 5.2, 9.6, 12.0 Hz, 1H), 3.71 (m, J = 6.0, 12.0 Hz, 1H), 3.16 (d, J = 5.2 Hz, 4H), 2.97 (m, J = 6.0, 10.0, 16.4 Hz, 1H), 2.80-2.67 (m, 5H), 2.32 (d, J = 7.2 Hz, 2H), 2.18 (d, J = 11.2 Hz, 2H), 2.05-1.89 (m, 4H), 1.78-1.67 (m, 1H), 1.24-1.11 (m, 2H) |
| I-285 | CCY | CCX | 824.4 | 10.56 (d, J = 2.4 Hz, 1H), 10.51 (s, 1H), 9.42 (d, J = 8.4 Hz, 1H), 8.70 (s, 1H), 8.61 (d, J = 3.2 Hz, 1H), 8.49-8.44 (m, 1H), 8.44-8.38 (m, 1H), 8.23 (d, J = 7.6 Hz, 1H), 7.93-7.88 (m, 1H), 7.87- |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 7.81 (m, 1H), 7.71 (d, J = 7.2 Hz, 1H), 7.28-6.98 (m, 2H), 4.60-4.19 (m, 2H), 3.98 (s, 3H), 3.95-3.89 (m, 1H), 3.72 (d, J = 2.8 Hz, 2H), 3.05-2.92 (m, 2H), 2.88-2.69 (m, 4H), 2.52 (d, J = 2.0 Hz, 10H), 2.23-1.86 (m, 8H), 1.41-1.06 (m, 3H) |
| I-286 | CCY | CCZ | 824.0 | 10.51 (d, J = 12 Hz, 2H), 9.39 (s, 1H), 8.68 (s, 1H), 8.56 (s, 1H), 8.49-8.44 (m, 1H), 8.43-8.36 (m, 1H), 8.33 (s, 1H), 8.22 (d, J = 7.6 Hz, 1H), 7.87-7.71 (m, 2H), 7.53 (d, J = 7.2 Hz, 1H), 7.16 (s, 1H), 4.42-4.30 (m, 1H), 4.22-4.10 (m, 1H), 3.98 (s, 3H), 3.95-3.86 (m, 1H), 3.78-3.64 (m, 1H), 3.04-2.91 (m, 1H), 2.84-2.68 (m, 3H), 2.64-2.56 (m, 2H), 2.36 (d, J = 6 Hz, 7H), 2.14 (d, J = 6 Hz, 5H), 1.98-1.85 (m, 6H), 1.69-1.52 (m, 1H), 1.31-0.99 (m, 3H) |
| I-287 | BAI | CEE | 736.6 | 11.08 (s, 1H), 9.65 (s, 1H), 8.72 (s, 1H), 8.47 (d, J = 2.8 Hz, 1H), 8.29 (s, 1H), 8.02 (s, 1H), 7.85 (s, 1H), 7.07 (s, 1H), 7.02-6.88 (m, 3H), 5.37-5.33 (m, 1H), 4.43-4.34 (m, 1H), 3.91 (s, 3H), 3.87 (s, 3H), 3.63 (s, 3H), 3.01-2.84 (m, 7H), 2.75-2.59 (m, 3H), 2.31-2.26 (m, 1H), 2.21-2.12 (m, 3H), 2.05-1.87 (m, 6H), 1.74-1.67 (m, 1H), 1.21-1.12 (m, 2H) |
| I-288 | BXL | BXI | 751.4 | 10.64 (s, 1H), 10.53 (s, 1H), 9.43 (s, 1H), 8.67-8.61 (m, 1H), 8.53 (s, 1H), 8.47-8.37 (m, 3H), 8.28-8.20 (m, 2H), 7.77-7.68 (m, 1H), 7.62 (d, J = 8.0 Hz, 1H), 7.29 (d, J = 7.2 Hz, 1H), 4.66-4.51 (m, 1H), 3.95-3.86 (m, 1H), 3.75-3.66 (m, 1H), 3.20-3.10 (m, 4H), 2.98-2.94 (m, 1H), 2.80-2.75 (m, 1H), 2.74-2.69 (m, 3H), 2.24-2.17 (m, 3H), 2.13 (s, 1H), 2.07-1.93 (m, 5H), 1.80-1.69 (m, 1H), 1.24-1.14 (m, 2H) |
| I-289 | CCK | BVB | 727.6 | 10.5 (s, 1H), 9.90 (s, 1H), 9.49 (s, 1H), 9.31 (d, J = 1.6 Hz, 1H), 9.20 (d, J = 2.0 Hz, 1H), 8.78 (s, 1H), 8.52 (s, 1H), 8.32 (s, 1H), 8.09 (s, 1H), 7.74-7.67 (m, 1H), 7.58 (d, J = 8.4 Hz, 1H), 7.33 (d, J = 7.6 Hz, 1H), 7.08 (s, 1H), 4.47-4.35 (m, 1H), 3.96-3.89 (m, 1H), 3.88 (s, 3H), 3.72-3.66 (m, 1H), 3.54 (s, 2H), 3.48-3.39 (m, 3H), 3.26-3.14 (m, 3H), 3.11-2.92 (m, 2H), 2.79-2.72 (m, 2H), 2.19-2.16 (m, 2H), 2.12 (s, 2H), 2.03-1.96 (m, 2H), 1.96-1.93 (m, 2H), 1.78-1.76 (m, 1H), 1.27-1.14 (m, 2H) |
| I-290 | BAI | CAZ | 751.4 | 11.1 (s, 1H), 8.58-8.54 (m, 2H), 8.47 (d, J = 4.0 Hz, 1H), 8.41 (dd, J = 1.2, 2.8 Hz, 1H), 8.31 (d, J = 7.4 Hz, 1H), 8.20 (s, 1H), 8.03 (dd, J = 2.8, 9.4 Hz, 1H), 7.00 (d, J = 7.4 Hz, 1H), 6.94 (d, J = 8.0 Hz, 2H), 6.75 (d, J = 4.0 Hz, 1H), 5.36 (dd, J = 5.6, 12.4 Hz, 1H), 3.83-3.76 (m, 1H), 3.76-3.70 (m, 1H), 3.63 (s, 3H), 3.17-3.04 (m, 2H), 3.00-2.81 (m, 4H), 2.76-2.70 (m, 1H), 2.70-2.66 (m, 1H), 2.64 (s, 1H), 2.60 (s, 1H), 2.54 (s, 1H), 2.24-2.22 (m, 2H), 1.99-1.96 (m, 1H), 1.93-1.84 (m, 4H), 1.62-1.44 (m, 1H), 1.37 (d, J = 11.6 Hz, 2H), 1.29 (d, J = 6.4 Hz, 6H), 1.11-0.91 (m, 2H) |
| I-291 | CEH | ATJ | 741.1 | 10.61-10.47 (m, 2H), 9.75-9.59 (m, 1H), 8.69 (s, 1H), 8.62 (s, 1H), 8.49-8.37 (m, 2H), 8.34 (s, 1H), 8.22 (d, J = 1.2, 7.6 Hz, 1H), 7.98-7.89 (m, 1H), 7.87-7.75 (m, 2H), 7.14 (s, 1H), 4.45-4.38 (m, 1H), 3.98 (s, 3H), 3.97-3.83 (m, 2H), 3.75-3.68 (m, 1H), 2.99 (d, J = 6.0, 16.4 Hz, 2H), 2.81-2.74 (m, 1H), 2.64-2.51 (m, 6H), 2.18 (d, J = 10.4 Hz, 2H), 2.08-1.87 (m, 5H), 1.79-1.62 (m, 1H), 1.35-1.17 (m, 2H) |
| I-293 | BSN | ALU | 775.2 | 10.55 (s, 1H), 10.50 (s, 1H), 9.68 (s, 1H), 8.59 (d, J = 7.2 Hz, 2H), 8.52-8.36 (m, 3H), 8.23 (d, J = 7.6 Hz, 1H), 8.00 (s, 1H), 7.97-7.88 (m, 1H), 7.82 (t, J = 7.6 Hz, 1H), 7.67-7.55 (m, 1H), 7.41-7.08 (m, 1H), 4.66-4.49 (m, 1H), 4.09-3.84 (m, 2H), 3.71 (td, J = 6.0, 12.0 Hz, 2H), 3.49-3.37 (m, 2H), 3.01-2.97 (m, 2H), 2.77 (td, J = 5.2, 16.8 Hz, 2H), 2.23 (d, J = 9.2 Hz, 3H), 2.15-1.65 (m, 9H), 1.38-1.19 (m, 2H) |
| I-294 | BAI | CEM | 788.3 | 11.09 (s, 1H), 10.73 (s, 1H), 8.70 (s, 1H), 8.49-8.36 (m, 2H), 8.33 (s, 1H), 8.21 (dd, J = 0.8, 7.6 Hz, 1H), 7.13 (s, 1H), 7.02-6.91 (m, 2H), 6.89 (d, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-295 | CCS | BWF | 812.3 | J = 7.2 Hz, 1H), 5.35 (dd, J = 5.2, 12.4 Hz, 1H), 4.43-4.32 (m, 1H), 4.20-4.18 (m, 2H), 3.63 (s, 3H), 3.13-2.77 (m, 7H), 2.69-2.57 (m, 2H), 2.54-2.52 (m, 1H), 2.24 (d, J = 7.2 Hz, 3H), 2.15 (d, J = 11.6 Hz, 2H), 2.04-1.86 (m, 5H), 1.71-1.61 (m, 1H), 1.50 (t, J = 6.8 Hz, 3H), 1.19-1.08 (m, 2H) 11.08 (s, 1H), 9.13 (s, 1H), 8.88-8.76 (m, 2H), 8.67 (d, J = 2.0 Hz, 1H), 8.57 (s, 1H), 8.52 (d, J = 3.6 Hz, 1H), 8.32 (d, J = 6.8 Hz, 1H), 6.95 (d, J = 8.4 Hz, 1H), 6.88 (d, J = 4.0 Hz, 1H), 6.74 (d, J = 8.8 Hz, 1H), 5.33 (dd, J = 5.6, 12.4 Hz, 1H), 4.69-4.51 (m, 1H), 3.94-3.86 (m, 1H), 3.83 (s, 3H), 3.75 (t, J = 12.4 Hz, 2H), 3.62 (s, 3H), 3.59-3.52 (m, 2H), 3.24-3.19 (m, 1H), 3.18-3.04 (m, 5H), 2.95-2.82 (m, 1H), 2.75-2.68 (m, 1H), 2.64-2.59 (m, 1H), 2.31-2.24 (m, 2H), 2.08-1.87 (m, 6H), 1.36 (d, J = 6.4 Hz, 6H), 1.21-1.13 (m, 2H) |
| I-296 | BAI | CEN | 784.3 | 11.10 (s, 1H), 10.75 (s, 1H), 8.65 (s, 1H), 8.51-8.46 (m, 1H), 8.45-8.37 (m, 2H), 8.23 (d, J = 7.6 Hz, 1H), 7.48 (s, 1H), 7.07-6.98 (m, 1H), 6.95 (d, J = 7.2 Hz, 2H), 5.37 (dd, J = 4.8, 12.8 Hz, 1H), 4.53-4.37 (m, 1H), 3.64 (s, 3H), 3.25-3.12 (m, 3H), 3.06-2.80 (m, 4H), 2.79-2.62 (m, 3H), 2.25-2.11 (m, 3H), 2.00 (dd, J = 7.2, 12.6 Hz, 8H), 1.36-1.19 (m, 2H), 1.11 (d, J = 8.4 Hz, 3H), 0.85-0.70 (m, 2H) |
| I-297 | BAI | CEO | 775.3 | 11.10 (s, 1H), 10.24 (s, 1H), 9.62 (s, 1H), 9.50 (s, 1H), 8.66 (s, 1H), 8.36 (s, 1H), 7.17 (s, 1H), 7.07-6.98 (m, 1H), 6.98-6.94 (m, 1H), 6.94-6.84 (m, 1H), 5.36 (dd, J = 5.6, 12.4 Hz, 1H), 4.51-4.33 (m, 1H), 3.98 (s, 3H), 3.64 (s, 3H), 3.53 (s, 1H), 3.13-2.83 (m, 6H), 2.77-2.60 (m, 5H), 2.25-2.07 (m, 3H), 2.05-1.72 (m, 6H), 1.28-1.10 (m, 2H) |
| I-298 | BAI | CEP | 775.4 | 11.09 (s, 1H), 10.47 (s, 1H), 9.39 (d, J = 52 Hz, 1H), 8.69 (s, 1H), 8.43 (d, J = 5.2 Hz, 1H), 8.36 (s, 1H), 7.18 (s, 1H), 7.12-6.97 (m, 1H), 6.96 (s, 1H), 6.94-6.81 (m, 1H), 5.44-5.23 (m, 1H), 4.56-4.29 (m, 1H), 3.99 (s, 3H), 3.64 (s, 3H), 3.50-3.38 (m, 4H), 3.12-2.81 (m, 6H), 2.30-2.11 (m, 4H), 2.05-1.83 (m, 6H), 1.30-1.11 (m, 3H) |
| I-299 | BXL | CEO | 757.3 | 9.70 (s, 1H), 9.41 (s, 1H), 8.79 (s, 1H), 8.68 (s, 1H), 8.61 (s, 1H), 8.59-8.59 (m, 1H), 7.83 (s, 1H), 7.71 (s, 1H), 7.54 (s, 1H), 6.96-6.86 (m, 1H), 6.81 (s, 1H), 6.46 (d, J = 7.2 Hz, 1H), 6.37-6.33 (m, 1H), 3.66-3.52 (m, 1H), 3.17-3.13 (m, 1H), 3.19-3.13 (m, 1H), 3.15 (s, 1H), 3.13-3.04 (m, 1H), 2.93-2.83 (m, 1H), 2.41-2.26 (m, 4H), 2.20-2.09 (m, 1H), 1.97-1.86 (m, 4H), 1.51-1.48 (m, 1H), 1.43-1.43 (m, 1H), 1.35 (d, J = 10.0 Hz, 2H), 1.25-1.04 (m, 4H), 0.97-0.81 (m, 1H), 0.35 (d, J = 12.4 Hz, 2H) |
| I-300 | BXL | CEP | 757.3 | 10.57-10.45 (m, 2H), 9.43 (s, 2H), 8.69 (s, 1H), 8.53 (s, 1H), 8.43 (d, J = 4.0 Hz, 1H), 8.37 (s, 1H), 7.77-7.69 (m, 1H), 7.62 (d, J = 9.6 Hz, 1H), 7.29 (d, J = 7.6 Hz, 1H), 7.2 (s, 1H), 4.46-4.36 (m, 1H), 3.99 (s, 3H), 3.95-3.87 (m, 1H), 3.73-3.66 (m, 1H), 3.20-3.10 (m, 5H), 2.98-2.93 (m, 1H), 2.81-2.72 (m, 4H), 2.20-2.14 (m, 2H), 2.03-1.90 (m, 4H), 1.77-1.65 (m, 1H), 1.26-1.13 (m, 4H) |
| I-301 | CAL | BSC | 772.4 | 11.1 (s, 1H), 10.14 (s, 1H), 8.47-8.35 (m, 3H), 8.25-8.15 (m, 2H), 7.51 (s, 1H), 7.10-6.86 (m, 3H), 5.44-5.31 (m, 1H), 4.47 (s, 1H), 3.75 (d, J = 10.0 Hz, 1H), 3.65 (s, 3H), 3.61-3.44 (m, 1H), 3.27 (s, 1H), 3.22-2.82 (m, 5H), 2.77-2.58 (m, 3H), 2.41 (s, 3H), 2.27-2.09 (m, 3H), 2.07-1.88 (m, 5H), 1.64-0.95 (m, 6H) |
| I-302 | BWR | BSC | 772.3 | 11.09 (s, 1H), 10.13 (s, 1H), 8.48-8.33 (m, 3H), 8.25-8.16 (m, 2H), 7.51 (s, 1H), 7.12-6.82 (m, 3H), 5.47-5.25 (m, 1H), 4.57-4.36 (m, 1H), 3.65 (s, 4H), 3.12-2.80 (m, 5H), 2.78-2.62 (m, 3H), 2.41 (s, 3H), 2.36-2.13 (m, 4H), 2.12-1.91 (m, 5H), 1.75-1.51 (m, 1H), 1.45-0.98 (m, 6H) |
| I-303 | BWT | BSC | 770.3 | 11.09 (s, 1H), 10.13 (s, 1H), 8.48-8.33 (m, 3H), 8.26-8.15 (m, 2H), 7.51 (s, 1H), 7.10-6.95 (m, 2H), 6.89 (d, J = 2.4 Hz, 1H), 5.36 (dd, J = 5.2, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 12.4 Hz, 1H), 4.52-4.41 (m, 1H), 4.15-3.89 (m, 1H), 3.85-3.68 (m, 1H), 3.63 (s, 3H), 3.21-2.99 (m, 2H), 2.99-2.79 (m, 2H), 2.76-2.59 (m, 3H), 2.52 (d, J = 1.6 Hz, 3H), 2.41 (s, 3H), 2.27-2.12 (m, 3H), 2.11-1.89 (m, 6H), 1.37-1.16 (m, 2H) |
| I-304 | CEQ | BSC | 784.4 | 11.13-10.98 (m, 1H), 10.13 (s, 1H), 8.46-8.35 (m, 3H), 8.24-8.16 (m, 2H), 7.51 (s, 1H), 7.02-6.95 (m, 1H), 6.92-6.86 (m, 1H), 6.82 (d, J = 8.0 Hz, 1H), 5.28 (dd, J = 5.2, 12.4 Hz, 1H), 4.48-4.38 (m, 1H), 3.06-2.91 (m, 4H), 2.88-2.81 (m, 1H), 2.65-2.54 (m, 7H), 2.40 (s, 3H), 2.24 (d, J = 6.4 Hz, 2H), 2.16 (d, J = 10.4 Hz, 2H), 2.02-1.89 (m, 5H), 1.73-1.61 (m, 1H), 1.20-1.09 (m, 2H), 1.07-0.99 (m, 2H), 0.97-0.89 (m, 2H) |
| I-307 | BAI | BIZ | 790.3 | 11.11 (s, 1H), 10.77 (s, 1H), 8.57 (s, 1H), 8.50-8.39 (m, 3H), 8.24 (d, J = 7.6 Hz, 1H), 7.81 (s, 1H), 7.03-6.87 (m, 3H), 5.36 (dd, J = 5.2, 12.8 Hz, 1H), 4.54-4.41 (m, 1H), 3.64 (s, 3H), 3.10-2.79 (m, 8H), 2.62 (d, J = 19.2 Hz, 3H), 2.26 (d, J = 6.0 Hz, 3H), 2.17 (d, J = 11.2 Hz, 3H), 2.04-1.90 (m, 5H), 1.68 (d, J = 7.2 Hz, 1H), 1.16 (d, J = 10.8 Hz, 3H) |
| I-308[h] | BAI | CEU | 806.3 | 11.8 (s, 1H), 8.89 (s, 1H), 8.48 (d, J = 7.6 Hz, 1H), 8.38 (s, 1H), 8.13 (t, J = 8.0 Hz, 1H), 8.02 (d, J = 9.2 Hz, 2H), 7.88 (d, J = 7.6 Hz, 1H), 7.05-6.94 (m, 2H), 6.60 (d, J = 7.6 Hz, 1H), 5.22 (dd, J = 5.2, 12.4 Hz, 1H), 4.45-4.42 (m, 1H), 3.77 (s, 3H), 3.05 (d, J = 4.4 Hz, 4H), 2.96 (s, 3H), 2.92 (d, J = 4.4 Hz, 1H), 2.88-2.82 (m, 1H), 2.79-2.71 (m, 1H), 2.44-2.31 (m, 6H), 2.24-2.22 (m, 1H), 2.13 (d, J = 12.8 Hz, 3H), 2.05-1.93 (m, 4H), 1.81-1.71 (m, 1H), 1.28-1.16 (m, 2H) |
| I-311 | CFB | CEP | 774.2 | 10.52 (d, J = 11.6 Hz, 2H), 9.50 (d, J = 2.4 Hz, 1H), 8.69 (s, 1H), 8.57 (s, 1H), 8.50-8.44 (m, 1H), 8.43-8.37 (m, 1H), 8.34 (s, 1H), 8.25-8.18 (m, 1H), 7.56 (dd, J = 8.4, 12.4 Hz, 1H), 7.31 (dd, J = 4.0, 8.4 Hz, 1H), 7.16 (s, 1H), 4.40 (br t, J = 11.6 Hz, 1H), 3.98 (s, 3H), 3.88-3.80 (m, 1H), 3.78-3.69 (m, 1H), 3.29 (s, 2H), 3.18-3.04 (m, 4H), 2.91-2.87 (m, 1H), 2.75-2.70 (m, 2H), 2.30 (s, 1H), 2.24-2.08 (m, 3H), 2.06-1.96 (m, 2H), 1.96-1.86 (m, 2H), 1.78-1.66 (m, 1H), 1.25-1.09 (m, 3H) |
| I-312 | CFC | ATJ | 705.2 | 10.50 (s, 1H), 10.26 (s, 1H), 8.69 (s, 1H), 8.51-8.38 (m, 2H), 8.36-8.30 (m, 1H), 8.22 (d, J = 7.6 Hz, 1H), 7.20-7.09 (m, 3H), 6.94 (d, J = 8.4 Hz, 2H), 4.44-4.31 (m, 1H), 3.98 (s, 3H), 3.70 (t, J = 6.4 Hz, 2H), 3.23-3.05 (m, 4H), 2.66 (s, 2H), 2.60 (s, 4H), 2.30-2.19 (m, 2H), 2.15 (d, J = 10.4 Hz, 2H), 2.04-1.85 (m, 4H), 1.76-1.60 (m, 1H), 1.21-1.06 (m, 2H) |
| I-313 | CFD | ATJ | 706.2 | 10.50 (s, 1H), 10.35 (s, 1H), 8.69 (s, 1H), 8.49-8.44 (m, 1H), 8.43-8.38 (m, 1H), 8.34 (s, 1H), 8.24-8.19 (m, 1H), 8.08 (d, J = 2.8 Hz, 1H), 7.52 (dd, J = 2.8, 9.2 Hz, 1H), 7.16 (s, 1H), 6.86 (d, J = 92 Hz, 1H), 4.46-4.30 (m, 1H), 3.98 (s, 3H), 3.72 (t, J = 6.8 Hz, 2H), 3.50 (s, 5H), 3.30-3.14 (m, 3H), 2.72 (t, J = 6.8 Hz, 2H), 2.24 (d, J = 6.0 Hz, 2H), 2.16 (d, J = 11.6 Hz, 2H), 2.05-1.82 (m, 4H), 1.69 (s, 1H), 1.22-1.05 (m, 2H) |
| I-314 | CFE | BCN | 778.2 | 0.97-1.12 (3H, m) 1.48-1.60 (3H, m) 1.92-2.04 (3H, m) 2.14 (2H, d, J = 11.6 Hz) 2.20 (1H, s) 2.22 (3H, s) 2.55-2.60 (4H, m) 2.80-2.92 (1H, m) 2.98-3.07 (1H, m) 3.38-3.48 (2H, m) 4.03 (3H, s) 5.05 (1H, dd, J = 12.8, 5.2 Hz) 6.75 (1H, t, J = 4.4 Hz) 7.04 (1H, d, J = 7.2 Hz) 7.08-7.13 (1H, m) 7.57-7.63 (1H, m) 7.70 (1H, s) 8.24 (1H, d, J = 7.6 Hz) 8.39-8.44 (1H, m) 8.46-8.50 (1H, m) 9.00 (1H, s) 10.50 (1H, s) 11.07 (1H, s) |
| I-315 | CBP | BCN | 792.4 | 11.08 (s, 1H), 10.50 (s, 1H), 9.00 (s, 1H), 8.52-8.45 (m, 1H), 8.45-8.39 (m, 1H), 8.27-8.20 (m, 1H), 7.69 (s, 1H), 7.63-7.55 (m, 1H), 7.11 (d, J = 8.4 Hz, 1H), 7.02 (d, J = 7.2 Hz, 1H), 6.72 (t, J = 5.2 Hz, 1H), 5.08-5.00 (m, 1H), 4.03 (s, 3H), 3.07-2.97 (m, 1H), 2.93-2.80 (m, 2H), 2.57-2.55 (m, 2H), 2.41 (d, J = 5.2 Hz, 2H), 2.23-2.07 (m, 7H), 2.03-1.95 (m, 1H), 1.94-1.85 (m, 2H), 1.74 |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | (quind, J = 6.0, 12.8 Hz, 2H), 1.62-1.45 (m, 3H), 1.28-1.11 (m, 1H), 1.10-0.93 (m, 2H) |
| I-317 | BRZ | BRR | 755.5 | 10.50 (s, 1H), 10.19 (s, 1H), 9.06(d, J = 7.6 Hz, 2H), 8.60 (s, 1H), 8.48 (d, J = 7.6 Hz, 2H), 8.41 (t, J = 8.0 Hz, 1H), 8.26 (s, 1H), 8.23 (d, J = 8.4 Hz, 1H), 8.14 (s, 1H), 7.79(d, J = 9.2 Hz, 1H), 7.69-7.65 (m, 1H), 7.43 (d, J = 2.4 Hz, 1H), 4.60-4.52 (m, 1H), 4.01 (d, J = 12.0 Hz, 2H), 3.93-3.86 (m, 1H), 3.73-3.67 (m, 1H), 2.99-2.81 (m, 4H), 2.80-2.70 (m, 2H), 2.38-2.30 (m, 3H), 2.19 (br d, J = 9.8 Hz, 2H), 1.97 (t, J = 10.4 Hz, 5H), 1.92-1.85 (m, 2H), 1.64 (s, 3H), 1.19-1.10 (m, 2H) |
| I-318 | BRY | BRR | 726.3 | 10.53 (s, 1H), 10.20 (s, 1H), 9.26 (s, 1H), 9.07 (s, 1H), 8.62 (s, 1H), 8.50-8.47 (m, 3H), 8.44-8.39 (m, 1H), 8.23 (d, J = 7.8 Hz, 1H), 8.07 (s, 1H), 7.92 (d, J = 8.4 Hz, 1H), 7.79 (dd, J = 1.2, 8.8 Hz, 1H), 4.64-4.53 (m, 1H), 3.96-3.89 (m, 1H), 3.77-3.68 (m, 1H), 3.03 (d, J = 11.2 Hz, 2H), 2.99-2.91 (m, 1H), 2.76 (td, J = 5.6, 16.4 Hz, 2H), 2.26-2.18 (m, 4H), 2.12-1.95 (m, 6H), 1.91-1.78 (m, 4H), 1.75-1.65 (m, 1H), 1.25-1.08 (m, 1H) |
| I-319 | BRZ | BTW | 754.2 | 10.50 (s, 1H), 10.35 (s, 1H), 9.07 (s, 1H), 8.41-8.34 (m, 3H), 8.29 (d, J = 0.8 Hz, 1H), 8.26 (s, 1H), 8.19-8.15 (m, 1H), 7.78 (d, J = 9.6 Hz, 1H), 7.68-7.65 (m, 1H), 7.62-7.58 (m, 1H), 7.56-7.53 (m, 1H), 7.42 (d, J = 2.4 Hz, 1H), 4.47-4.40 (m, 1H), 3.98 (d, J = 12.4 Hz, 2H), 3.93-3.86 (m, 1H), 3.73-3.67 (m, 1H), 2.97-2.93 (m, 1H), 2.85 (s, 2H), 2.76 (d, J = 5.6 Hz, 1H), 2.28 (d, J = 6.4 Hz, 2H), 2.23 (s, 3H), 2.18-2.14 (m, 2H), 2.00-1.93 (m, 4H), 1.87-1.76 (m, 3H), 1.62-1.54 (m, 3H), 1.15-1.08 (m, 2H) |
| I-320 | BRZ | ATJ | 784.2 | 10.50 (s, 2H), 9.07 (s, 1H), 8.68 (s, 1H), 8.48-8.37 (m, 2H), 8.33 (s, 1H), 8.26 (s, 1H), 8.23-8.19 (m, 1H), 7.78 (d, J = 9.6 Hz, 1H), 7.70-7.63 (m, 1H), 7.42 (d, J = 2.0 Hz, 1H), 7.15 (s, 1H), 4.40-4.32 (m, 1H), 4.05-3.98 (m, 2H), 3.98 (s, 3H), 3.93-3.86 (m, 1H), 3.73-3.67 (m, 1H), 2.98-2.90 (m, 1H), 2.84 (t, J = 12.0 Hz, 2H), 2.78-2.71 (m, 1H), 2.28 (d, J = 6.8 Hz, 2H), 2.23 (s, 3H), 2.16-2.12 (m, 2H), 2.01-1.89 (m, 4H), 1.88-1.80 (m, 3H), 1.62-1.53 (m, 3H), 1.15-1.07 (m, 2H) |
| I-321 | BRY | BTW | 725.1 | 10.54 (s, 1H), 10.34 (s, 1H), 9.26 (s, 1H), 8.48 (s, 1H), 8.40 (d, J = 92 Hz, 1H), 8.36 (s, 1H), 8.30 (s, 1H), 8.18 (s, 1H), 8.07 (s, 1H), 7.90 (s, 1H), 7.61 (s, 1H), 7.56 (s, 1H), 7.55 (s, 1H), 4.49-4.47 (m, 1H), 3.94-3.93 (m, 1H), 3.74-3.73 (m, 1H), 3.05-2.96 (m, 3H), 2.78-2.52 (m, 2H), 2.26-2.4 (m, 4H), 2.09-1.99 (m, 2H), 1.98-1.97 (m, 8H), 1.87-1.70 (m, 1H), 1.20-1.14 (m, 2H) |
| I-322 | BRY | ATJ | 755.2 | 10.53 (d, J = 12.4 Hz, 2H), 9.27 (s, 1H), 8.69 (s, 1H), 8.49 (s, 1H), 8.48-8.43 (m, 1H), 8.41-8.36 (m, 1H), 8.34 (s, 1H), 8.22 (d, J = 7.6 Hz, 1H), 8.06 (s, 1H), 7.95 (d, J = 8.8 Hz, 1H), 7.79-7.70 (m, 1H), 4.44-4.38 (m, 1H), 3.98 (s, 3H), 3.97-3.90 (m, 1H), 3.74-3.71 (m, 1H), 3.40-3.34 (m, 4H), 2.96-2.78 (m, 3H), 2.49-2.40 (m, 2H), 2.20-2.16 (m, 2H), 2.00-1.94 (m, 8H), 1.92-1.84 (m, 1H), 1.23-1.14 (m, 2H) |
| I-323 | BQM | BVH | 714.3 | 11.09 (s, 1H), 10.60 (s, 1H), 8.43-8.38 (m, 2H), 8.35-8.28 (m, 3H), 7.61 (s, 2H), 6.93-6.81 (m, 2H), 5.39-5.30 (m, 1H), 4.55-4.42 (m, 1H), 3.65 (s, 3H), 3.58 (s, 1H), 3.29 (s, 2H), 3.21-2.98 (m, 2H), 2.94-2.84 (m, 1H), 2.78-2.68 (m, 1H), 2.65-2.58 (m, 1H), 2.48-2.47 (m, 4H), 2.25-2.15 (m, 3H), 1.98 (d, J = 6.0 Hz, 9H), 1.34-0.93 (m, 3H) |
| I-325 | AZK | BWH | 784.3 | 11.09 (s, 1H), 10.52 (s, 1H), 9.32 (s, 1H), 9.24 (s, 1H), 8.77 (s, 1H), 8.56 (s, 1H), 7.98 (s, 1H), 7.72 (s, 1H), 7.08-6.92 (m, 3H), 5.37 (dd, J = 5.4, 12.4 Hz, 1H), 4.59-4.46 (m, 1H), 3.59 (s, 3H), 3.05-2.98 (m, 2H), 2.94-2.84 (m, 1H), 2.77-2.62 (m, 2H), 2.24 (d, J = 6.4 Hz, 2H), 2.18 (d, J = 10.4 Hz, 2H), 2.14-2.05 (m, 2H), 2.04-1.95 (m, 4H), 1.95-1.90 (m, 1H), 1.88-1.59 (m, 6H), 1.15 (q, J = 12.2 Hz, 2H) |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-326 | CBD | AGL | 840.4 | 12.36 (s, 1H), 11.12 (s, 1H), 8.71 (s, 1H), 8.50-8.41 (m, 1H), 8.40-8.28 (m, 2H), 8.17-8.13 (m, 1H), 7.57 (s, 1H), 7.23-7.06 (m, 2H), 7.05-6.97 (m, 1H), 5.94 (s, 1H), 5.39 (dd, J = 5.2, 12.8 Hz, 1H), 4.50-4.35 (m, 1H), 3.65 (s, 3H), 3.62 (s, 1H), 2.93-2.84 (m, 1H), 2.36-2.29 (m, 1H), 2.14 (d, J = 9.6 Hz, 2H), 2.05-1.99 (m, 1H), 1.97-1.86 (m, 4H), 1.61 (s, 6H), 1.20-1.07 (m, 2H) |
| I-327 | CBD | ATJ | 812.3 | 11.12 (s, 1H), 10.50 (s, 1H), 8.73 (s, 1H), 8.49 (s, 2H), 8.32 (s, 1H), 8.22 (d, J = 7.6 Hz, 1H), 7.19-7.09 (m, 3H), 7.06-6.99 (m, 1H), 5.39 (dd, J = 5.6, 12.4 Hz, 1H), 4.43-4.31 (m, 1H), 3.98 (s, 3H), 3.75-3.47 (m, 6H), 2.96-2.81 (m, 2H), 2.79-2.55 (m, 7H), 2.26-2.07 (m, 4H), 2.05-1.99 (m, 1H), 1.99-1.82 (m, 5H), 1.73-1.57 (m, 1H), 1.22-1.05 (m, 2H) |
| I-328 | CAR | BTW | 758.3 | 11.09 (s, 1H), 10.36 (s, 1H), 8.43-8.33 (m, 3H), 8.30 (s, 1H), 8.17 (dd, J = 1.2, 7.2 Hz, 1H), 7.64-7.59 (m, 1H), 7.57-7.52 (m, 1H), 7.03-6.96 (m, 2H), 6.89 (d, J = 5.6 Hz, 1H), 5.35 (dd, J = 5.2, 12.8 Hz, 1H), 4.51-4.41 (m, 1H), 3.66 (s, 3H), 3.29 (s, 2H), 3.26-3.12 (m, 4H), 3.04-2.82 (m, 4H), 2.76-2.68 (m, 1H), 2.65-2.56 (m, 2H), 2.19 (d, J = 10.4 Hz, 2H), 2.04-1.90 (m, 7H), 1.79-1.62 (m, 1H), 1.26-1.12 (m, 2H) |
| I-329 | BSN | BWF | 763.5 | 10.55 (s, 1H), 9.64 (s, 1H), 8.86 (s, 1H), 8.82 (d, J = 2.0 Hz, 1H), 8.68 (d, J = 2.0 Hz, 1H), 8.59 (s, 1H), 8.56 (s, 1H), 8.53 (d, J = 4.0 Hz, 1H), 8.34 (d, J = 7.2 Hz, 1H), 8.10 (s, 1H), 7.91-7.85 (d, 1H), 7.81 (t, J = 7.6 Hz, 1H), 7.66 (d, J = 7.2 Hz, 1H), 6.89 (d, J = 4.0 Hz, 1H), 4.65-4.51 (m, 1H), 4.01-3.83 (m, 2H), 3.72 (m, 2H), 3.14-2.93 (m, 3H), 2.81-2.74 (m, 1H), 2.53 (d, J = 2.0 Hz, 2H), 2.32-2.15 (m, 3H), 2.13-1.85 (m, 9H), 1.83-1.75 (m, 1H), 1.37 (d, J = 6.4 Hz, 6H), 1.30-1.20 (m, 2H) |
| I-330 | CBE | ATJ | 770.3 | 10.51 (s, 1H), 9.54-9.52 (m, 1H), 8.70 (s, 1H), 8.61-8.59 (m, 1H), 8.49-8.44 (m, 1H), 8.43-8.38 (m, 1H), 8.35 (s, 1H), 8.22 (d, J = 7.6 Hz, 1H), 7.76-7.73 (m, 2H), 7.38-7.37 (m, 1H), 7.16 (s, 1H), 4.50-4.37 (m, 1H), 3.99 (s, 3H), 3.95-3.84 (m, 1H), 3.81-3.65 (m, 3H), 3.63-3.46 (m, 3H), 3.24-3.21 (m, 3H), 3.12-3.03 (m, 4H), 2.92-2.87 (m, 1H), 2.78-2.64 (m, 1H), 2.52-2.50 (m, 1H), 2.19 (m, 2H), 2.08-1.87 (m, 5H), 1.42-1.10 (m, 2H) |
| I-331 | CBG | ATJ | 770.3 | 10.53 (s, 1H), 10.51 (s, 1H), 9.78-9.06 (m, 1H), 8.71 (s, 1H), 8.52 (s, 1H), 8.48-8.44 (m, 1H), 8.43-8.38 (m, 1H), 8.36 (s, 1H), 8.22 (d, J = 7.6 Hz, 1H), 7.87-7.69 (m, 1H), 7.68-7.58 (m, 1H), 7.16 (s, 1H), 4.53-4.38 (m, 1H), 3.99 (s, 3H), 3.95-3.86 (m, 1H), 3.85-3.74 (m, 1H), 3.73-3.41 (m, 4H) 3.27-3.08 (m, 3H), 3.02-2.92 (m, 1H), 2.90-2.69 (m, 2H), 2.55 (s, 3H), 2.54-2.50 (m, 2H), 2.26-2.14 (m, 2H), 2.13-1.83 (m, 5H), 1.43-1.15 (m, 2H) |
| I-332 | CBI | ATJ | 786.4 | 10.52 (br d, J = 9.2 Hz, 2H), 9.67 (br s, 1H), 8.70 (s, 1H), 8.49-8.38 (m, 3H), 8.35 (s, 1H), 8.22 (d, J = 7.6 Hz, 1H), 7.91-7.82 (m, 1H), 7.74 (br d, J = 9.2 Hz, 1H), 7.16 (s, 1H), 4.47-4.36 (m, 1H), 3.99 (s, 6H), 3.95-3.85 (m, 2H), 3.72-3.67 (m, 2H), 3.00-2.91 (m, 3H), 2.81-2.71 (m, 2H), 2.53-2.52 (m, 4H), 2.24-2.14 (m, 3H), 2.07-1.88 (m, 5H), 1.29-1.13 (m, 2H) |
| I-333 | CBL | CBK | 751.5 | 11.1 (s, 1H), 8.19-8.12 (m, 1H), 7.79 (t, J = 8.0 Hz, 1H), 7.52 (d, J = 8.0 Hz, 1H), 7.35 (s, 1H), 7.28 (d, J = 7.6 Hz, 2H), 7.14-7.06 (m, 2H), 6.87 (s, 1H), 5.44-5.34 (m, 1H), 4.67-4.47 (m, 1H), 4.36-4.29 (m, 1H), 4.25-4.13 (m, 1H), 3.72 (s, 3H), 3.54 (s, 3H), 3.27 (s, 3H), 2.89 (s, 2H), 2.78-2.57 (m, 4H), 2.22-1.94 (m, 4H), 1.92-1.77 (m, 4H), 1.70-1.52 (m, 1H), 1.30-0.98 (m, 9H) |
| I-334 | CBM | CBN | 859.2 | 12.36 (s, 1H), 11.16-11.02 (m, 1H), 8.71 (s, 1H), 8.49-8.42 (m, 1H), 8.39-8.34 (m, 2H), 8.16 (d, J = 7.8 Hz, 1H), 7.60-7.55 (m, 2H), 7.10 (d, J = 8.6 Hz, 1H), 7.01 (d, J = 7.0 Hz, 1H), 5.94 (s, 1H), 5.05 (dd, J = 5.4, 13.2 Hz, 1H), 4.46-4.35 (m, |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| | | | | 1H), 2.97-2.79 (m, 3H), 2.28-2.24 (m, 2H), 2.13 (s, 3H), 2.04-1.98 (m, 2H), 1.96-1.89 (m, 4H), 1.62 (s, 6H), 1.43-1.39 (m, 2H), 1.38-1.30 (m, 6H), 1.12-1.03 (m, 1H), 1.11-1.03 (m, 1H) |
| I-335 | CBO | AGL | 841.3 | 12.36 (s, 1H), 11.02 (s, 1H), 8.72 (s, 1H), 8.48-8.41 (m, 1H), 8.40-8.32 (m, 2H), 8.19-8.13 (m, 1H), 7.61-7.55 (m, 1H), 7.27 (t, J = 7.8 Hz, 1H), 6.95 (d, J = 7.4 Hz, 1H), 6.64 (d, J = 7.9 Hz, 1H), 5.94 (s, 1H), 5.78 (br d, J = 6.6 Hz, 1H), 5.16-5.09 (m, 1H), 4.47-4.37 (m, 1H), 4.30-4.11 (m, 2H), 3.99-3.88 (m, 1H), 2.99-2.88 (m, 1H), 2.63 (br d, J = 18.5 Hz, 3H), 2.31-2.20 (m, 5H), 2.13 (br d, J = 6.4 Hz, 4H), 2.08-2.00 (m, 1H), 1.98-1.86 (m, 4H), 1.70-1.59 (m, 12H), 1.56 (brs, 2H), 1.18-1.06 (m, 2H) |
| I-336 | CBP | CBN | 803.2 | 12.37 (s, 1H), 11.10 (s, 1H), 8.72 (s, 1H), 8.50-8.42 (m, 1H), 8.42-8.32 (m, 2H), 8.21-8.11 (m, 1H), 7.67-7.52 (m, 2H), 7.20-7.12 (m, 1H), 7.10-7.02 (m, 1H), 6.76 (d, J = 6.4 Hz, 1H), 5.97-5.89 (m, 1H), 5.06 (dd, J = 5.5, 12.6 Hz, 1H), 4.46-4.39 (m, 1H), 3.44-3.41 (m, 2H), 2.92-2.88 (m, 2H), 2.84 (d, J = 5.2 Hz, 5H), 2.53-2.52 (m, 3H), 2.15-2.10 (m, 3H), 1.96-1.88 (m, 5H), 1.63 (s, 6H), 1.27-1.09 (m, 3H) |
| I-337 | CBQ | CBN | 803.3 | 12.36 (s, 1H), 8.71 (s, 1H), 8.48-8.42 (m, 1H), 8.41-8.32 (m, 3H), 8.16 (d, J = 7.6 Hz, 1H), 7.63-7.53 (m, 2H), 7.12 (d, J = 8.4 Hz, 2H), 7.03 (d, J = I2 Hz, 1H), 6.59 (br t, J = 5.6 Hz, 1H), 6.03-5.85 (m, 1H), 5.13-4.98 (m, 1H), 4.49-4.34 (m, 1H), 2.88 (ddd, J = 4.4, 14.0, 17.2 Hz, 2H), 2.65-2.59 (m, 3H), 2.58-2.54 (m, 4H), 2.13 (d, J = 11.6 Hz, 2H), 2.08-1.98 (m, 2H), 1.97-1.83 (m, 4H), 1.64 (s, 2H), 1.62 (s, 6H), 1.59-1.51 (m, 3H), 1.16 (d, J = 10.0 Hz, 2H) |
| I-339 | CBO | ATJ | 813.1 | 1.06-1.17 (m, 2 H) 1.51-1.73 (m, 8 H) 1.78-I.99 (m, 5 H) 1.99-2.07 (m, 1 H) 2.09-2.19 (m, 4 H) 2.21-2.32 (m, 5 H) 2.59-2.65 (m, 1 H) 2.85-3.03 (m, 2 H) 3.93 (d, J = 12 Hz, 1 H) 3.98 (s, 3 H) 4.09-4.29 (m, 2 H) 4.31-4.42 (m, 1 H) 5.12 (dd, J = 13.38, 5.2 Hz, 1 H) 6.63 (d, J = 7.6 Hz, 1 H) 6.94 (d, J = 7.2 Hz, 1 H) 7.15 (s, 1 H) 7.27 (t, J = 7.6 Hz, 1 H) 8.15 (d, J = 3.6 Hz, 1 H) 8.22 (dd, J = 7.63, 0.88 Hz, 1 H) 8.32 (s, 1 H) 8.37-8.43 (m, 1 H) 8.44-8.49 (m, 1 H) 8.68 (s, 1 H) 10.50 (s, 1 H) 11.01 (s, 1 H) |
| I-340 | CBT | AGL | 901.3 | 12.35 (s, 1H), 11.08 (s, 1H), 8.71 (s, 1H), 8.51-8.41 (m, 1H), 8.39-8.32 (m, 2H), 8.16 (d, J = 7.6 Hz, 1H), 7.61-7.53 (m, 2H), 7.16 (d, J = 8.8 Hz, 1H), 7.03 (d, J = 7.2 Hz, 1H), 6.19 (d, J = 8.4 Hz, 1H), 5.93 (s, 1H), 5.03 (dd, J = 5.2, 12.4 Hz, 1H), 4.48-4.37 (m, 1H), 3.64-3.51 (m, 1H), 3.46 (t, J = 6.0 Hz, 2H), 2.97-2.80 (m, 1H), 2.72-2.65 (m, 1H), 2.58 (d, J = 2.8 Hz, 2H), 2.40-2.29 (m, 3H), 2.17-2.12 (m, 6H), 2.05-1.88 (m, 9H), 1.71-1.52 (m, 9H), 1.34 (t, J = 8.8 Hz, 4H), 1.17-1.02 (m, 2H) |
| I-342 | AXB | ATJ | 855.4 | 1.02-1.12 (m, 2 H) 1.24 (d, J = 4.4 Hz, 1 H) 1.29-1.37 (m, 3 H) 1.48-1.55 (m, 2 H) 1.59-1.64 (m, 2 H) 1.66-1.74 (m, 3 H) 1.85-1.96 (m, 6 H) 2.00-2.07 (m, 2 H) 2.10-2.15 (m, 2 H) 2.18 (s, 3 H) 2.22 (d, J = 5.6 Hz, 3 H) 2.59-2.61 (m, 2 H) 2.87 (d, J = 10.4 Hz, 1 H) 3.98 (s, 3 H) 4.06-4.12 (m, 1 H)4.31-4.40 (m, 1 H) 5.03-5.09 (m, 1 H) 6.43 (d, J = 6.4 Hz, 1 H) 7.00 (d, J = 8.4 Hz, 1 H) 7.04-7.08 (m, 1 H) 7.15 (s, 1 H) 7.56-7.63 (m, 1 H) 8.22 (d, J = 7, 6 Hz.1 H) 8.33 (s, 1 H) 8.40 (t, J = 7.6 Hz, 1 H) 8.45-8.48 (m, 1 H) 8.68 (s, 1 H) 10.50 (s, 1 H) 11.10 (s, 1 H) |
| I-343 | AJF | CBW | 863.3 | 12.55-12.33 (m, 1H), 11.20-10.96 (m, 1H), 9.03 (d, J = 8.4 Hz, 1H), 8.87-8.77 (m, 1H), 8.53-8.23 (m, 3H), 8.21-8.10 (m, 1H), 8.03-7.96 (m, 1H), 7.68 (dd, J = 9.6, 1.2 Hz, 1H), 7.60-7.41 (m, 3H), 7.17-6.96 (m, 2H), 6.53-6.38 (m, 1H), 6.13- |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-345 | AJF | CBZ | 843.7 | 12.34 (s, 1H), 11.11-11.03 (m, 1H), 8.75-8.65 (m, 1H), 8.47-8.42 (m, 1H), 8.38-8.30 (m, 2H), 8.18-8.11 (m, 1H), 7.59-7.52 (m, 2H), 7.11-6.99 (m, 2H), 6.44 (s, 1H), 5.93 (s, 1H), 5.04 (dd, J = 12.8, 4.0 Hz, 1H), 4.38 (t, J = 6.8 Hz, 2H), 2.93-2.82 (m, 2H), 2.69-2.64 (m, 1H), 2.22-2.17 (m, 4H), 2.06-1.98 (m, 2H), 1.91-1.80 (m, 5H), 1.62 (s, 6H), 1.53-1.40 (m, 10H), 1.25-1.14 (m, 3H) |
| | | | | 5.96 (m, 1H), 5.13-4.93 (m, 1H), 2.31 (d, J = 9.6 Hz, 6H), 2.10-1.76 (m, 7H), 1.64 (d, J = 8.0 Hz, 6H), 1.57-1.40 (m, 6H), 1.31-1.15 (m, 2H) |
| I-347 | CCB | AGL | 887.2 | 12.36 (s, 1H), 11.08 (s, 1H), 8.71 (s, 1H), 8.47-8.43 (m, 1H), 8.40-8.32 (m, 2H), 8.17-8.14 (m, 1H), 7.65-7.59 (m, 1H), 7.56 (s, 1H), 7.29 (d, J = 6.8 Hz, 1H), 7.13 (d, J = 8.4 Hz, 1H), 5.93 (s, 1H), 5.12-5.05 (m, 1H), 4.46-4.36 (m, 1H), 4.33-4.25 (m, 1H), 4.05-3.94 (m, 1H), 3.36-3.34 (m, 2H), 2.95 (s, 3H), 2.92-2.83 (m, 1H), 2.62-2.53 (m, 2H), 2.43-2.37 (m, 2H), 2.34-2.25 (m, 5H), 2.22-2.16 (m, 5H), 2.15-2.09 (m, 2H), 2.06-1.99 (m, 1H), 1.97-1.88 (m, 4H), 1.71-1.64 (m, 2H), 1.61 (s, 6H), 1.16-1.03 (m, 2H) |
| I-348 | CCC | AGL | 873.6 | 12.35 (s, 1H), 11.05 (s, 1H), 8.71 (s, 1H), 8.47-8.41 (m, 1H), 8.39-8.33 (m, 2H), 8.16 (d, J = 8.4 Hz, 1H), 7.61-7.53 (m, 2H), 7.44 (d, J = 5.2 Hz, 1H), 6.87-6.69 (m, 2H), 5.93 (s, 1H), 5.02 (dd, J = 12.8, 5.2 Hz, 1H), 4.51-4.35 (m, 1H), 4.13 (t, J = 5.6 Hz, 1H), 4.05-3.97 (m, 1H), 3.38 (s, 2H), 3.36 (s, 2H), 2.94-2.80 (m, 1H), 2.58 (s, 2H), 2.55-2.54 (m, 2H), 2.36 (d, J = 5.2 Hz, 2H), 2.27 (d, J = 2.0 Hz, 3H), 2.20 (s, 5H), 2.01-1.86 (m, 5H), 1.70 (d, J = 5.6 Hz, 2H), 1.61 (s, 6H), 1.19-1.07 (m, 2H) |
| I-349 | CCE | AGL | 859.4 | 12.36 (s, 1H), 11.10 (s, 1H), 8.71 (s, 1H), 8.49-8.41 (m, 1H), 8.41-8.32 (m, 2H), 8.16 (d, J = 7.6 Hz, 1H), 7.66-7.53 (m, 2H), 7.08 (d, J = 7.2 Hz, 1H), 6.92 (d, J = 8.4 Hz, 1H), 6.51 (d, J = 5.6 Hz, 1H), 5.94 (s, 1H), 5.05 (dd, J = 12.8, 5.6 Hz, 1H), 4.47-4.38 (m, 1H), 4.20-4.12 (m, 2H), 3.43-3.41 (m, 2H), 2.91-2.86 (m, 1H), 2.60 (d, J = 3.2 Hz, 2H), 2.38 (dd, J = 7.6, 4.4 Hz, 2H), 2.33 (s, 1H), 2.26 (d, J = 6.4 Hz, 3H), 2.22 (s, 3H), 2.17-2.11 (m, 2H), 2.06-1.84 (m, 1H), 1.62 (s, 8H), 1.16-1.03 (m, 2H) |
| I-350[f] | AOQ | CBW | 867.3 | 12.45 (s, 1H), 11.09 (s, 1H), 9.03 (s, 1H), 8.81 (s, 1H), 8.46 (d, J = 7.6 Hz, 1H), 8.38 (t, J = 7.6 Hz, 1H), 8.17 (d, J = 7.6 Hz, 1H), 8.02 (d, J = 8.4 Hz, 2H), 7.68 (s, 1H), 7.58-7.47 (m, 3H), 7.05 (d, J = 7.2 Hz, 1H), 6.86 (d, J = 8.4 Hz, 1H), 6.48 (d, J = 5.6 Hz, 1H), 6.04 (s, 1H), 5.05 (J = 5.2, 12.8 Hz, 1H), 4.16-4.04 (m, 2H), 3.53 (s, 3H), 2.95-2.81 (m, 2H), 2.60 (d, J = 2.0 Hz, 2H), 2.43 (t, J = 7.2 Hz, 3H), 2.33 (d, J = 4.8 Hz, 2H), 2.21 (d, J = 6.0 Hz, 2H), 2.16 (s, 2H), 2.09-1.94 (m, 2H), 1.75-1.69 (m, 2H), 1.65 (s, 6H) |
| I-351 | CCC | ALU | 865.4 | 11.09 (s, 1H), 10.49 (s, 1H), 8.55 (s, 1H), 8.50-8.36 (m, 3H), 8.22(dd, J = 8.0, 0.8 Hz, 1H), 7.97(s, 1H), 7.58(dd, J = 8.4, 7.2 Hz, 1H), 7.41-7.10(m, 1H), 7.07(d, J = 7.2 Hz, 1H), 6.92(d, J = 8, 4 Hz, 1H), 6.50 (d, J = 5.6 Hz, 1H), 5.05 (dd, J = 12.8, 5.2 Hz, 1H), 4.62-4.44(m, 1H), 4.25-4.06(m, 2H), 3.37(s, 2H), 2.94-2.80(m, 1H), 2.56(s, 2H), 2.41-2.36(m, 3H), 2.34-2.32(m, 1H), 2.29-2.10(m, 10H), 2.06-1.99(m, 1H), 1.98-1.86(m, 4H), 1.68-1.53(m, 3H), 1.20-1.03(m, 2H) |
| I-353 | CCC | BRR | 816.7 | 11.10 (s, 1H), 10.20 (s, 1H), 9.06 (s, 1H), 8.60 (s, 1H), 8.52-8.46 (m, 2H), 8.42 (t, J = 7.6 Hz, 1H), 8.24 (d, J = 8.0 Hz, 1H), 7.64-7.54 (m, 1H), 7.08 (d, J = 7.2 Hz, 1H), 6.92 (d, J = 8.4 Hz, 1H), 6.51 (d, J = 6.0 Hz, 1H), 5.06 (dd, J = 12.4, 5.6 Hz, 1H), 4.66-4.45 (m, 1H), 4.26-4.05 (m, 2H), 3.00-2.79 (m, 1H), 2.72-2.64 (m, 1H), 2.64-2.53 (m, 3H), 2.31-2.12 (m, 11H), 2.09-1.88 (m, 6H), 1.77-1.47 (m, 4H), 1.14 (q, J = 11.6 Hz, 2H) |
| I-354 | CCC | BRP | 815.5 | 11.18-11.02 (m, 1H), 10.36 (s, 1H), 8.40 (s, 3H), 8.29 (d, J = 1.2 Hz, 1H), 8.19-8.17 (m, 1H), 7.58 |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| | | | | (dd, J = 2.0, 13.6 Hz, 3H), 7.08 (d, J = 7.2 Hz, 1H), 6.93 (d, J = 8.4 Hz, 1H), 6.57-6.45 (m, 1H), 5.10-5.00 (m, 1H), 4.51-4.39 (m, 1H), 4.22-4.09 (m, 2H), 2.97-2.79 (m, 1H), 2.71-2.65 (m, 1H), 2.63-2.55 (m, 1H), 2.53 (s, 3H), 2.41-2.35 (m, 5H), 2.35-2.31 (m, 2H), 2.29-2.21 (m, 3H), 2.05-1.86 (m, 6H), 1.74-1.53 (m, 4H), 1.19-1.06 (m, 2H) |
| I-355 | CBX | BRP | 771.3 | 11.10 (s, 1H), 10.37 (s, 1H), 8.44-8.30 (m, 4H), 8.18 (dd, J = 1.2, 7.6 Hz, 1H), 7.65-7.60 (m, 1H), 7.59-7.53 (m, 1H), 7.05-6.95 (m, 1H), 6.72 (d, J = 7.6 Hz, 1H), 5.65 (t, J = 8.0 Hz, 1H), 5.36 (dd, J = 5.2, 12.4 Hz, 1H), 4.58-4.43 (m, 1H), 3.75 (s, 3H), 3.73 (s, 1H), 3.34-3.33 (m, 3H), 3.30 (s, 1H), 3.26 (s, 1H), 3.18-3.06 (m, 1H), 2.98-2.83 (m, 2H), 2.77-2.69 (m, 1H), 2.63 (d, J = 17.2 Hz, 2H), 2.53 (s, 1H), 2.21 (d, J = 10.3 Hz, 3H), 2.08-1.93 (m, 6H), 1.39-1.16 (m, 2H) |
| I-356 | CCF | ATJ | 770.3 | 10.49 (d, J = 6.4 Hz, 2H), 9.02 (s, 1H), 8.69 (s, 1H), 8.48-8.44 (m, 1H), 8.43-8.37 (m, 1H), 8.31 (s, 1H), 8.21 (d, J = 7.6 Hz, 1H), 8.17 (s, 1H), 7.77 (d, J = 9.2 Hz, 1H), 7.50 (dd, J = 2.0, 9.2 Hz, 1H), 7.22 (s, 1H), 7.14 (s, 1H), 4.36 (t, J = 11.6 Hz, 1H), 3.98 (s, 3H), 3.92-3.73 (m, 3H), 3.72-3.66 (m, 1H), 3.63 (t, J = 6.4 Hz, 2H), 3.13-2.80 (m, 4H), 2.78-2.70 (m, 2H), 2.52 (s, 1H), 2.11 (s, 4H), 1.99-1.39 (m, 6H), 1.26-1.00 (m, 2H) |
| I-357 | CCG | ATJ | 753.3 | 10.56 (s, 1H), 10.51 (s, 1H), 9.57-9.30 (m, 1H), 8.70 (s, 1H), 8.59 (s, 1H), 8.49-8.44 (m, 1H), 8.44-8.38 (m, 1H), 8.36 (s, 1H), 8.22 (d, J = 7.6 Hz, 1H), 8.06-7.88 (m, 1H), 7.88-7.74 (m, 1H), 7.58 (dd, J = 1.6, 4.8 Hz, 1H), 7.16 (s, 1H), 5.88 (s, 1H), 4.52-4.37 (m, 1H), 4.34 (t, J = 5.2 Hz, 1H), 3.99 (s, 3H), 3.98-3.85 (m, 2H), 3.73 (td, J = 6.0, 12.0 Hz, 1H), 3.44 (t, J = 2.0 Hz, 1H), 3.26-3.11 (m, 2H), 3.10-2.92 (m, 2H), 2.77 (d, J = 5.2 Hz, 2H), 2.21 (d, J = 2.0 Hz, 2H), 2.12-1.84 (m, 5H), 1.46-1.07 (m, 3H) |
| I-358 | BXL | CCH | 760.6 | 10.57-10.49 (m, 2H), 9.52-9.24 (m, 1H), 8.65 (s, 1H), 8.60-8.51 (m, 2H), 8.49-8.38 (m, 2H), 8.25-8.23 (m, 1H), 7.94 (s, 1H), 7.80-7.60 (m, 2H), 7.41-7.25 (m, 1H), 4.60-4.46 (m, 1H), 3.98-3.85 (m, 1H), 3.73-3.67 (m, 2H), 3.62-3.44 (m, 2H), 3.28-3.08 (m, 4H), 3.01-2.92 (m, 1H), 2.79-2.72 (m, 2H), 2.53-2.51 (m, 1H), 2.22-2.20 (m, 2H), 2.04-2.01 (m, 5H), 1.88-1.59 (m, 1H), 1.40-1.14 (m, 2H) |
| I-359 | BAI | BKQ | 762.6 | 11.10 (s, 1H), 10.23 (d, J = 2.0 Hz, 1H), 8.50 (s, 1H), 8.46-8.38 (m, 3H), 8.22 (d, J = 7.6 Hz, 1H), 7.55 (d, J = 11.6 Hz, 1H), 7.08-6.86 (m, 3H), 5.40-5.31 (m, 1H), 4.55-4.25 (m, 1H), 3.64 (s, 3H), 3.31-3.23 (m, 3H), 3.22-3.13 (m, 2H), 3.04-2.97 (m, 1H), 2.94-2.84 (m, 2H), 2.76-2.59 (m, 3H), 2.29-2.15 (m, 3H), 2.03-1.89 (m, 6H), 1.87-1.57 (m, 1H), 1.40-1.07 (m, 2H) |
| I-360 | BAI | CCH | 778.6 | 11.10 (s, 1H), 10.53 (s, 1H), 8.64 (s, 1H), 8.54 (s, 1H), 8.50-8.37 (m, 2H), 8.24 (d, J = 7.6 Hz, 1H), 7.94 (s, 1H), 7.09-6.86 (m, 3H), 5.37 (dd, J = 5.2, 12.4 Hz, 1H), 4.52 (s, 1H), 3.65 (s, 4H), 3.26-3.06 (m, 4H), 3.04-2.80 (m, 3H), 2.78-2.55 (m, 3H), 2.29-2.13 (m, 3H), 2.08-1.89 (m, 6H), 1.88-1.49 (m, 1H), 1.40-1.10 (m, 2H) |
| I-361 | BAI | BUR | 758.4 | 11.09 (s, 1H), 8.81 (s, 1H), 8.67 (s, 1H), 8.58 (s, 2H), 8.52 (d, J = 2.0 Hz, 1H), 8.42-8.27 (m, 1H), 8.08 (s, 1H), 7.14-6.80 (m, 4H), 5.43-5.27 (m, 1H), 3.83-3.70 (m, 2H), 3.63 (s, 3H), 3.61-3.52 (m, 1H), 3.22-3.07 (m, 3H), 3.05-2.77 (m, 4H), 2.76-2.68 (m, 1H), 2.65-2.58 (m, 1H), 2.29-2.09 (m, 2H), 2.05-1.71 (m, 6H), 1.53-1.34 (m, 2H), 1.29 (d, J = 5.6 Hz, 6H), 1.24-0.86 (m, 3H) |
| I-362 | BAI | BVU | 758.3 | 11.09 (s, 1H), 8.83 (d, J = 2.0 Hz, 1H), 8.71 (d, J = 2.0 Hz, 1H), 8.68 (s, 1H), 8.46 (d, J = 7.2 Hz, 1H), 8.30 (d, J = 7.6 Hz, 1H), 8.05 (s, 1H), 7.82 (d, J = 4.8 Hz, 1H), 7.10 (d, J = 4.8 Hz, 1H), 7.01- |

TABLE 4-continued

Compounds prepared by Method 2.

| I-# | Intermediate Amine | Intermediate Aldehyde | LCMS (ES+) m/z (M + H)⁺ | 1H NMR (400 MHz, DMSO-d6) δ |
|---|---|---|---|---|
| | | | | 6.92 (m, 2H), 6.88 (d, J = 7.6 Hz, 1H), 5.38-5.31 (m, 1H), 3.81-3.71 (m, 2H), 3.63 (s, 3H), 3.02-2.80 (m, 8H), 2.72-2.69 (m, 1H), 2.19 (d, J = 7.2 Hz, 3H), 2.03-1.96 (m, 1H), 1.91-1.82 (m, 4H), 1.55-1.46 (m, 1H), 1.43-1.30 (m, 3H), 1.27 (d, J = 6.4 Hz, 6H), 1.03-0.92 (m, 2H) |
| I-363 | BAI | BXI | 769.4 | 11.09 (s, 1H), 10.64 (s, 1H), 8.63 (s, 1H), 8.52-8.31 (m, 3H), 8.28-8.19 (m, 2H), 7.03-6.88 (m, 3H), 5.36 (dd, J = 5.2, 12.8 Hz, 1H), 4.67-4.50 (m, 1H), 3.64 (s, 3H), 3.12-2.97 (m, 3H), 2.95-2.81 (m, 3H), 2.64 (dd, J = 12.8, 17.2 Hz, 4H), 2.31-2.25 (m, 1H), 2.20 (d, J = 9.6 Hz, 3H), 2.10-1.86 (m, 6H), 1.81-1.63 (m, 1H), 1.32-1.12 (m, 2H) |
| I-364 | CCS | ATJ | 804.6 | 11.10 (s, 1H), 10.53 (s, 1H), 8.64 (s, 1H), 8.54 (s, 1H), 8.50-8.37 (m, 2H), 8.24 (d, J = 7.6 Hz, 1H), 7.94 (s, 1H), 7.09-6.86 (m, 3H), 5.37 (dd, J = 5.2, 12.4 Hz, 1H), 4.52 (s, 1H), 3.65 (s, 4H), 3.26-3.06 (m, 4H), 3.04-2.80 (m, 3H), 2.78-2.55 (m, 3H), 2.29-2.13 (m, 3H), 2.08-1.89 (m, 6H), 1.88-1.49 (m, 1H), 1.40-1.10 (m, 2H) |
| I-365 | BAI | CFG | 720.6 | 11.08 (s, 1H), 9.60 (s, 1H), 8.92 (s, 1H), 8.60 (s, 1H), 8.29 (s, 1H), 8.13 (s, 1H), 8.07 (s, 1H), 7.07 (s, 1H), 7.02-6.92 (m, 2H), 6.89 (d, J = 7.6 Hz, 1H), 5.40-5.31 (m, 1H), 4.44-4.33 (m, 1H), 3.87 (s, 3H), 3.64 (s, 3H), 3.30 (s, 1H), 3.10-2.79 (m, 7H), 2.76-2.62 (m, 2H), 2.52 (s, 1H), 2.39 (s, 3H), 2.27-2.23 (m, 2H), 2.20-2.13 (m, 2H), 2.02-1.86 (m, 5H), 1.74-1.60 (m, 1H), 1.22-1.07 (m, 2H) |
| I-366 | CFH | ATJ | 757.5 | 11.12 (s, 1H), 10.51 (s, 1H), 8.70 (s, 1H), 8.48-8.38 (m, 2H), 8.35 (s, 1H), 8.22 (d, J = 7.6 Hz, 1H), 7.39 (s, 1H), 7.22-7.11 (m, 3H), 6.37 (s, 1H), 5.39 (dd, J = 5.2, 12.4 Hz, 1H), 4.54-4.31 (m, 2H), 3.99 (s, 3H), 3.38 (s, 3H), 3.26-3.02 (m, 2H), 3.01-2.82 (m, 2H), 2.80-2.61 (m, 3H), 2.19 (d, J = 12.0 Hz, 2H), 2.12-1.88 (m, 6H), 1.88-1.70 (m, 1H), 1.37-1.16 (m, 2H) |
| I-367 | CAR | BVB | 745.4 | 11.10 (s, 1H), 9.92 (s, 1H), 9.32 (d, J = 1.6 Hz, 1H), 9.22 (d, J = 1.6 Hz, 1H), 8.79 (s, 1H), 8.33 (s, 1H), 8.12 (d, J = 19.6 Hz, 1H), 7.08 (s, 1H), 7.03-6.97 (m, 2H), 6.92 (d, J = 5.2 Hz, 1H), 5.37 (dd, J = 5.6, 12.4 Hz, 1H), 4.48-4.35 (m, 1H), 3.89 (s, 3H), 3.66 (s, 3H), 3.31-3.30 (m, 1H), 3.22-3.06 (m, 4H), 2.96-2.83 (m, 2H), 2.78-2.69 (m, 1H), 2.69-2.58 (m, 2H), 2.53 (d, J = 2.0 Hz, 2H), 2.19 (d, J = 12.0 Hz, 2H), 2.12-1.85 (m, 8H), 1.82-1.68 (m, 1H), 1.31-1.13 (m, 2H) |
| I-368 | AZK | CFI | 800.4 | 11.09 (s, 1H), 8.77 (s, 1H), 8.60-8.52 (m, 4H), 8.33 (d, J = 7.6 Hz, 1H), 8.19 (s, 1H), 7.04-6.94 (m, 3H), 6.91 (d, J = 4.0 Hz, 1H), 5.39-5.35 (m, 1H), 3.86-3.69 (m, 2H), 3.59 (s, 3H), 3.13-3.01 (m, 2H), 2.96-2.82 (m, 1H), 2.77-2.68 (m, 1H), 2.64-2.59 (m, 1H), 2.52-2.51 (m, 4H), 2.03-1.96 (m, 1H), 1.95-1.74 (m, 9H), 1.61-1.50 (m, 1H), 1.38-1.35 (m, 2H), 1.30-1.29 (m, 6H), 1.06-0.93 (m, 2H) |
| I-369 | BAI | CFI | 801.7 | 11.09 (s, 1H), 8.77 (d, J = 1.6 Hz, 1H), 8.61-8.49 (m, 4H), 8.39-8.30 (m, 1H), 8.19 (s, 1H), 7.05-6.85 (m, 4H), 5.38-5.34 (m, 1H), 3.85-3.71 (m, 2H), 3.64 (s, 3H), 3.21-3.03 (m, 3H), 2.94-2.83 (m, 2H), 2.76-2.68 (m, 1H), 2.66-2.58 (m, 1H), 2.52-2.51 (m, 7H), 2.04-1.96 (m, 1H), 1.95-1.84 (m, 4H), 1.47-1.34 (m, 2H), 1.30-0.29 (m, 6H), 1.17-0.95 (m, 2H) |
| I-370 | BSN | CCH | 759.2 | 9.74-9.69 (m, 2H), 8.84 (s, 1H), 7.82 (s, 1H), 7.78-7.74 (m, 1H), 7.72 (s, 1H), 7.67-7.63 (m, 1H), 7.62-7.57 (m, 1H), 7.42 (d, J = 7.6 Hz, 1H), 7.13-7.10 (m, 1H), 7.09-7.05 (m, 1H), 6.99 (t, J = 7.6 Hz, 1H), 6.82-6.80 (m, 1H), 3.76-3.65 (m, 1H), 3.17-3.06 (m, 1H), 2.94-2.85 (m, 1H), 2.56-2.51 (m, 3H), 2.20-2.12 (m, 1H), 1.98-1.91 (m, 2H), 1.70-1.69 (m, 4H), 1.40-1.37 (m, 2H), 1.28-1.11 (m, 7H), 0.49-0.34 (m, 2H) |
| I-371 | BXL | ALU | 776.1 | 10.55 (s, 1H), 10.50 (s, 1H), 9.54-9.26 (m, 1H), 8.58 (s, 2H), 8.50 (s, 1H), 8.48-8.44 (m, 1H), 8.43-8.37 (m, 1H), 8.23 (d, J = 7.6 Hz, 1H), 8.00 |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| | | | | (s, 1H), 7.85-7.59 (m, 2H), 7.42-7.07 (m, 2H), 4.69-4.47 (m, 1H), 4.01-3.84 (m, 1H), 3.79-3.65 (m, 2H), 3.65-3.42 (m, 3H), 3.31-3.07 (m, 6H), 2.98 (d, J = 6.0 Hz, 1H), 2.76 (d, J = 5.6 Hz, 2H), 2.29-2.18 (m, 2H), 2.04 (d, J = 7.6 Hz, 4H), 1.47-1.11 (m, 2H) |
| I-372 | BXL | BUR | 740.4 | 10.54 (s, 1H), 9.46 (s, 1H), 8.81 (d, J = 2.0 Hz, 1H), 8.68 (d, J = 2.0 Hz, 1H), 8.60-8.54 (m, 3H), 8.52 (d, J = 4.0 Hz, 1H), 8.37 (d, J = 7.6 Hz, 1H), 8.08 (s, 1H), 7.80-7.60 (m, 2H), 7.32 (s, 1H), 6.89 (d, J = 4.0 Hz, 1H), 3.91 (ddd, J = 5.2, 9.6, 12.0 Hz, 1H), 3.83-3.65 (m, 4H), 3.40 (s, 1H), 3.25-3.05 (m, 4H), 2.97 (ddd, J = 6.0, 10.0, 16.4 Hz, 2H), 2.76 (td, J = 5.6, 16.8 Hz, 2H), 2.52 (d, J = 2.0 Hz, 2H), 1.91 (d, J = 8.0 Hz, 4H), 1.48-1.36 (m, 2H), 1.29 (d, J = 6.4 Hz, 6H), 1.21-1.12 (m, 1H), 1.05 (t, J = 7.2 Hz, 2H) |
| I-373 | BXL | BVU | 740.4 | 10.54 (s, 1H), 9.51-9.43 (m, 1H), 8.84 (d, J = 2.0 Hz, 1H), 8.73-8.67 (m, 2H), 8.56 (s, 1H), 8.51-8.43 (m, 1H), 8.34 (d, J = 6.0 Hz, 1H), 8.05 (s, 1H), 7.83 (d, J = 4.8 Hz, 1H), 7.78-7.64 (m, 2H), 7.40-7.26 (m, 1H), 7.11 (d, J = 4.8 Hz, 1H), 3.96-3.87 (m, 1H), 3.83-3.75 (m, 2H), 3.73-3.65 (m, 2H), 3.58-3.44 (m, 2H), 3.21-3.08 (m, 3H), 3.03-2.91 (m, 2H), 2.81-2.70 (m, 2H), 2.52 (d, J = 2.0 Hz, 2H), 1.91 (d, J = 8.4 Hz, 5H), 1.47-1.34 (m, 2H), 1.28 (d, J = 6.4 Hz, 6H), 1.19-1.05 (m, 2H) |
| I-374 | CAY | CFI | 801.2 | 11.07 (s, 1H), 8.77 (d, J = 1.6 Hz, 1H), 8.61-8.55 (m, 3H), 8.54 (d, J = 4.0 Hz, 1H), 8.35 (d, J = 7.6 Hz, 1H), 8.19 (s, 1H), 7.02-6.93 (m, 1H), 6.91 (d, J = 4.0 Hz, 2H), 6.73-6.59 (m, 1H), 5.30 (dd, J = 4.8, 12.8 Hz, 1H), 3.86-3.67 (m, 3H), 3.67-3.48 (m, 1H), 3.33-3.33 (m, 3H), 3.24-2.98 (m, 5H), 2.96-2.84 (m, 1H), 2.75-2.57 (m, 3H), 2.52 (d, J = 2.0 Hz, 1H), 2.26-2.08 (m, 1H), 2.04-1.66 (m, 6H), 1.46-1.33 (m, 2H), 1.30 (d, J = 6.4 Hz, 6H), 1.17-0.89 (m, 2H) |
| I-375 | BWL | ALU | 776.3 | 10.54-10.46 (m, 2H), 9.08 (s, 1H), 8.57 (s, 1H), 8.49 (s, 1H), 8.48-8.44 (m, 1H), 8.43-8.36 (m, 1H), 8.28 (s, 1H), 8.23 (dd, J = 0.4, 7.2 Hz, 1H), 7.99 (s, 1H), 7.81 (d, J = 9.2 Hz, 1H), 7.68 (dd, J = 2.4, 9.6 Hz, 1H), 7.42 (d, J = 2.0 Hz, 1H), 7.39-7.09 (m, 1H), 4.61-4.48 (m, 1H), 3.97-3.84 (m, 1H), 3.76-3.62 (m, 1H), 3.40-3.34 (m, 4H), 3.00-2.88 (m, 1H), 2.80-2.70 (m, 1H), 2.63-2.56 (m, 4H), 2.31-2.22 (m, 2H), 2.23-2.12 (m, 2H), 2.06-1.91 (m, 4H), 1.80-1.65 (m, 1H), 1.27-1.10 (m, 2H) |
| I-376 | CFK | ATJ | 786.6 | 10.53 (d, J = 14.4 Hz, 2H), 9.40 (s, 1H), 9.28-9.16 (m, 1H), 8.71 (s, 1H), 8.47-8.45 (m, 1H), 8.44-8.38 (m, 1H), 8.35 (s, 1H), 8.22 (d, J = 7.6 Hz, 1H), 7.78-7.71 (m, 1H), 7.70-7.63 (m, 1H), 7.15 (s, 1H), 4.45 (t, J = 11.2 Hz, 1H), 4.02 (s, 3H), 3.99 (s, 3H), 3.92 (ddd, J = 5.2, 9.6, 12.0 Hz, 1H), 3.79 (d, J = 12.4 Hz, 2H), 3.75-3.66 (m, 3H), 3.27-3.17 (m, 5H), 3.15-3.06 (m, 1H), 2.99-2.88 (m, 1H), 2.85-2.73 (m, 1H), 2.21 (d, J = 10.4 Hz, 2H), 2.05-1.92 (m, 5H), 1.39-1.23 (m, 2H) |
| I-377 | BXL | CFL | 754.4 | 10.53 (s, 1H), 10.18 (s, 1H), 9.44 (s, 1H), 8.54 (s, 1H), 8.46-8.42 (m, 1H), 8.40 (d, J = 7.6 Hz, 1H), 8.39-8.36 (m, 1H), 8.25 (s, 1H), 8.21 (d, J = 1.2 Hz, 1H), 7.78-7.70 (m, 1H), 7.67-7.59 (m, 1H), 7.53-7.47 (m, 1H), 7.34-7.26 (m, 1H), 4.53-4.41 (m, 1H), 3.91 (d, J = 12.0 Hz, 1H), 3.75-3.65 (m, 1H), 3.26-3.08 (m, 4H), 2.97 (d, J = 6.0 Hz, 2H), 2.82-2.69 (m, 6H), 2.23-2.13 (m, 2H), 2.07-1.88 (m, 5H), 1.81-1.65 (m, 1H), 1.31-1.12 (m, 6H) |
| I-378 | BAI | CFL | 772.2 | 11.10 (s, 1H), 10.18 (s, 1H), 8.51-8.42 (m, 1H), 8.40 (d, J = 7.6 Hz, 1H), 8.38 (s, 1H), 8.25 (s, 1H), 8.22 (d, J = 1.2 Hz, 1H), 7.50 (s, 1H), 7.07-6.99 (m, 1H), 6.99-6.88 (m, 2H), 5.37 (d, J = 5.2 Hz, 1H), 4.55-4.41 (m, 1H), 3.65 (s, 4H), 3.29-3.02 (m, 5H), 2.97-2.84 (m, 2H), 2.83-2.70 (m, 3H), 2.70-2.60 (m, 2H), 2.27-2.12 (m, 3H), 2.06-1.86 (m, 6H), 1.26 (t, J = 7.6 Hz, 6H) |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| I-379 | BAI | CFM | 829.7 | 11.14-11.05 (m, 2H), 8.79 (s, 1H), 8.52-8.47 (m, 1H), 8.44-8.37 (m, 2H), 8.29-8.21 (m, 1H), 7.51 (s, 1H), 7.08-6.86 (m, 3H), 5.42-5.33 (m, 12.4 Hz, 1H), 4.51-4.38 (m, 1H), 3.87 (s, 4H), 3.65 (s, 3H), 3.25-3.05 (m, 4H), 2.92 (s, 5H), 2.77-2.59 (m, 5H), 2.54 (s, 2H), 2.21-2.14 (m, 2H), 2.06-1.88 (m, 6H), 1.44-1.03 (m, 3H) |
| I-380 | CFO | ATJ | 757.6 | 10.78 (s, 1H), 10.51 (s, 1H), 9.17 (s, 1H), 8.70 (s, 1H), 8.48-8.44 (m, 1H), 8.44-8.38 (m, 1H), 8.35 (s, 1H), 8.23-8.21 (m, 1H), 7.69 (d, J = 7.6 Hz, 1H), 7.61-7.57 (m, J = 7.6 Hz, 1H), 7.44 (d, J = 6.4 Hz, 1H), 7.16 (s, 1H), 4.49-4.39 (m, 1H), 4.15-4.01 (m, 3H), 3.99 (s, 3H), 3.80-3.66 (m, 2H), 3.47-3.37 (m, 2H), 3.27-3.14 (m, 3H), 2.85-2.84 (m, 2H), 2.52-2.50 (m, 2H), 2.21-2.18 (m, 2H), 2.08-1.89 (m, 5H), 1.32-1.29 (m, 2H) |
| I-381 | CGV | AJB | 865.5 | 11.12 (s, 1H), 9.50 (d, J = 6.4 Hz, 1H), 8.78 (d, J = 7.6 Hz, 1H), 8.39 (s, 1H), 8.25 (d, J = 5.6 Hz, 1H), 7.25-6.95 (m, 4H), 6.91-6.41 (m, 1H), 5.40 (dd, J = 5.2, 12.4 Hz, 1H), 5.30-5.03 (m, 1H), 4.82-4.70 (m, 1H), 4.30-4.12 (m, 1H), 3.86-3.71 (m, 3H), 3.66 (s, 3H), 3.63-3.42 (m, 3H), 3.04-2.96 (m, 1H), 2.93-2.83 (m, 2H), 2.78-2.68 (m, 2H), 2.68-2.59 (m, 2H), 2.52-2.51 (m, 2H), 2.24-1.86 (m, 9H), 1.85-1.47 (m, 4H), 1.31 (s, 2H), 1.20-0.92 (m, 3H) |
| I-382 | CFQ | ATJ | 756.2 | 10.59 (s, 1H), 10.51 (s, 1H), 8.93 (d, J = 4.4 Hz, 1H), 8.70 (s, 1H), 8.49-8.44 (m, 1H), 8.43-8.37 (m, 1H), 8.35 (s, 1H), 8.22 (d, J = 8.4 Hz, 1H), 7.70-7.50 (m, 3H), 7.27 (s, 1H), 7.16 (s, 1H), 4.48-4.38 (m, 1H), 4.29-4.09 (m, 1H), 4.07-3.91 (m, 5H), 3.87-3.59 (m, 3H), 3.54-3.34 (m, 3H), 3.29-3.15 (m, 3H), 3.06-2.96 (m, 1H), 2.75-2.68 (m, 1H), 2.19 (d, J = 8.0 Hz, 2H), 2.09-1.88 (m, 5H), 1.42-1.18 (m, 2H) |
| I-383 | BAI | BAS | 841.4 | 11.08 (s, 1H), 10.69 (s, 1H), 8.68 (s, 1H), 8.45-8.53 (m, 1H), 8.40 (t, J = 7.6 Hz, 1H), 8.34 (s, 1H), 8.26-8.16(m, 1H), 7.39 (s, 1H), 6.92-7.03 (m, 2H), 6.89 (d, J = 7.6 Hz, 1H), 5.35 (dd, J = 12.8, 5.2 Hz, 1H), 4.61 (s, 1H), 4.32-4.47 (m, 1H), 4.05 (s, 1H), 4.00 (d, J = 7.6 Hz, 1H), 3.66 (dd, J = 7.6, 1.6 Hz, 1H), 3.64 (s, 3H), 3.42 (d, J = 10.0 Hz, 1H), 3.24 (d, J = 9.2 Hz, 1H), 2.84-3.01 (m, 6H), 2.56-2.77 (m, 3H), 2.24-2.35 (m, 3H), 2.13 (dd, J = 17.6, 10.8 Hz, 3H), 1.82-2.05 (m, 7H), 1.61-1.74 (m, 1H), 1.10-1.24 (m, 2H) |
| I-384 | BAI | BQY | 841.4 | 11.10 (s, 1H), 10.69 (s, 1H), 8.69 (s, 1H), 8.53-8.45 (m, 1H), 8.41 (t, J = 7.6 Hz, 1H), 8.35 (s, 1H), 8.22 (d, J = 7.6 Hz, 1H), 7.38 (s, 1H), 7.12-6.81 (m, 3H), 5.47-5.29 (m, 1H), 4.62 (s, 1H), 4.54-4.35 (m, 1H), 4.05 (s, 1H), 4.00 (d, J = 7.6 Hz, 1H), 3.71-3.58 (m, 5H), 3.43 (d, J = 10.0 Hz, 1H), 3.29-3.22 (m, 3H), 3.21-3.10 (m, 3H), 2.95-2.84 (m, 2H), 2.77-2.69 (m, 1H), 2.69-2.62 (m, 2H), 2.62-2.57 (m, 1H), 2.29-2.14 (m, 3H), 2.11 (d, J = 9.2 Hz, 1H), 2.06-1.90 (m, 6H), 1.85 (d, J = 9.2 Hz, 1H), 1.41-1.06 (m, 2H) |
| I-385 | CFR | ATJ | 843.6 | 11.09 (s, 1H), 10.50 (s, 1H), 8.69 (d, J = 0.8 Hz, 1H), 8.52-8.36 (m, 2H), 8.33 (s, 1H), 8.22 (d, J = 7.6 Hz, 1H), 7.15 (s, 1H), 7.11-6.92 (m, 3H), 5.36 (dd, J = 4.8, 12.0 Hz, 1H), 4.37 (d, J = 14.8 Hz, 2H), 4.16-4.05 (m, 1H), 3.98 (s, 3H), 3.57 (s, 4H), 3.43 (d, J = 4.0 Hz, 1H), 3.14-3.07 (m, 1H), 2.96-2.83 (m, 2H), 2.74-2.59 (m, 5H), 2.22-2.05 (m, 4H), 2.03-1.88 (m, 7H), 1.83-1.55 (m, 3H), 1.26-1.13 (m, 2H), 1.06 (m, 2H) |
| I-386 | CFS | ATJ | 843.2 | 11.09 (s, 1H), 10.50 (s, 1H), 8.69 (s, 1H), 8.50-8.36 (m, 2H), 8.33 (s, 1H), 8.22 (d, J = 7.6 Hz, 1H), 7.22-7.09 (m, 2H), 7.08-6.94 (m, 2H), 5.37 (dd, J = 4.8, 12.0 Hz, 1H), 4.46-4.31 (m, 2H), 4.30-4.21 (m, 1H), 4.08 (s, 1H), 3.98 (s, 3H), |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 3.51 (s, 4H), 3.43 (d, J = 5.2 Hz, 1H), 3.11 (s, 1H), 2.96-2.83 (m, 2H), 2.81-2.58 (m, 5H), 2.16 (d, J = 8.4 Hz, 2H), 2.09-1.85 (m, 8H), 1.84-1.62 (m, 3H), 1.28-1.12 (m, 2H), 1.11-1.01 (m, 2H) |
| I-387 | BAI | CFT | 799.3 | 11.10 (s, 1H), 10.19 (s, 1H), 8.49-8.36 (m, 3H), 8.29 (s, 1H), 8.23 (d, J = 7.6 Hz, 1H), 7.10-6.92 (m, 3H), 6.91 (s, 1H), 5.47-5.28 (m, 1H), 4.54-4.29 (m, 1H), 3.88 (t, J = 7.2 Hz, 4H), 3.65 (s, 3H), 3.64-3.54 (m, 1H), 3.44-3.34 (m, 2H), 3.17 (s, 4H), 3.06-2.78 (m, 3H), 2.77-2.63 (m, 2H), 2.31-2.21 (m, 3H), 2.18 (d, J = 4.4 Hz, 2H), 2.09-1.80 (m, 6H), 1.40-1.06 (m, 2H) |
| I-388 | BAI | BUE | 787.5 | 11.10 (s, 1H), 11.05 (s, 1H), 8.73 (s, 1H), 8.49-8.45 (m, 1H), 8.44-8.38 (m, 1H), 8.36 (s, 1H), 8.21 (d, J = 7.6 Hz, 1H), 7.44 (s, 1H), 7.11-7.00 (m, 1H), 7.00-6.84 (m, 2H), 5.48-5.26 (m, 1H), 4.55-4.34 (m, 1H), 3.65 (s, 4H), 3.40-3.00 (m, 6H), 2.98-2.81 (m, 2H), 2.80-2.70 (m, 6H), 2.73-2.68 (m, 1H), 2.65-2.58 (m, 1H), 2.47-2.41 (m, 1H), 2.29-2.09 (m, 3H), 2.06-1.85 (m, 6H), 1.39-1.18 (m, 2H) |
| I-389 | BDY | BSC | 770.2 | 11.10 (s, 1H), 10.13 (s, 1H), 8.47-8.33 (m, 4H), 8.25-8.16 (m, 2H), 7.56-7.47 (m, 1H), 7.14-6.84 (m, 4H), 5.36 (d, J = 5.2 Hz, 1H), 4.52-4.41 (m, 2H), 4.15-3.96 (m, 1H), 3.85 (d, J = 3.2 Hz, 1H), 3.74-3.58 (m, 5H), 2.98-2.82 (m, 2H), 2.77-2.56 (m, 4H), 2.20 (d, J = 10.8 Hz, 3H), 2.10-1.88 (m, 7H), 1.78-1.67 (m, 1H), 1.36-1.19 (m, 2H) |
| I-391 | CCS | BUR | 788.3 | 11.08 (s, 1H), 8.81 (d, J = 2.0 Hz, 1H), 8.68 (d, J = 2.0 Hz, 1H), 8.58 (s, 2H), 8.52 (d, J = 3.6 Hz, 1H), 8.36 (d, J = 7.2 Hz, 1H), 8.08 (s, 1H), 6.92 (d, J = 8.4 Hz, 1H), 6.89 (d, J = 4.0 Hz, 1H), 6.72 (d, J = 8.8 Hz, 1H), 5.32 (dd, J = 5.2, 12.4 Hz, 1H), 3.81 (s, 3H), 3.79-3.73 (m, 2H), 3.61 (s, 5H), 3.14-3.06 (m, 1H), 3.04-2.93 (m, 2H), 2.92-2.81 (m, 2H), 2.73-2.57 (m, 4H), 2.01-1.81 (m, 6H), 1.80-1.54 (m, 1H), 1.39 (d, J = 11.2 Hz, 2H), 1.29 (d, J = 6.4 Hz, 6H), 1.24-1.14 (m, 1H), 1.13-1.00 (m, 2H) |
| I-392 | BAI | CFU | 813.3 | 11.10 (s, 1H), 10.89 (s, 1H), 8.71 (s, 1H), 8.50-8.46 (m, 1H), 8.40 (t, J = 7.6 Hz, 1H), 8.35 (s, 1H), 8.21 (d, J = 7.2 Hz, 1H), 7.42 (s, 1H), 7.09-6.86 (m, 3H), 5.41-5.31 (m, 1H), 4.51-4.34 (m, 1H), 3.64 (s, 3H), 3.23-3.14 (m, 2H), 3.07 (s, 4H), 2.96-2.83 (m, 3H), 2.72-2.58 (m, 6H), 2.29-2.12 (m, 4H), 2.03-1.94 (m, 9H), 1.29-1.22 (m, 2H), 1.18-1.11 (m, 1H) |
| I-393 | CET | BSC | 784.2 | 11.11 (s, 1H), 10.14 (s, 1H), 8.81-8.60 (m, 1H), 8.46-8.37 (m, 3H), 8.24-8.20 (m, 2H), 7.52 (s, 1H), 6.98-6.86 (m, 2H), 6.74 (d, J = 8.0 Hz, 1H), 5.41-5.33 (m, 1H), 4.56-4.44 (m, 1H), 4.03 (s, 2H), 3.71 (s, 3H), 3.62-3.54 (m, 2H), 3.46-3.40 (m, 2H), 3.15 (d, J = 4.4 Hz, 2H), 2.96-2.85 (m, 1H), 2.76-2.70 (m, 1H), 2.63 (d, J = 18.4 Hz, 2H), 2.42 (s, 3H), 2.24-2.18 (m, 2H), 2.13-2.07 (m, 3H), 2.04-1.94 (m, 6H), 1.42-1.27 (m, 2H) |
| I-395 | CCS | BVU | 788.4 | 11.08 (s, 1H), 9.10-9.00 (m, 1H), 8.88 (s, 1H), 8.75 (s, 1H), 8.67 (s, 1H), 8.55-8.34 (m, 1H), 8.01 (s, 1H), 7.93-7.82 (m, 1H), 7.19-7.07 (m, 1H), 6.99-6.89 (m, 1H), 6.74 (d, J = 8.8 Hz, 1H), 5.36-5.29 (m, 1H), 3.83 (s, 3H), 3.78-3.69 (m, 3H), 3.61 (s, 3H), 3.53 (d, J = 11.6 Hz, 2H), 3.21-3.17 (m, 1H), 3.12-3.04 (m, 4H), 2.95-2.83 (m, 1H), 2.75-2.67 (m, 1H), 2.65-2.57 (m, 1H), 2.01-1.85 (m, 6H), 1.84-1.76 (m, 1H), 1.45-1.36 (m, 2H), 1.29 (d, J = 6.4 Hz, 6H), 1.21-1.08 (m, 3H) |
| I-396 | BWC | BSC | 770.3 | 11.10 (s, 1H), 10.13 (s, 1H), 8.45-8.36 (m, 3H), 8.21 (dd, J = 1.6, 5.6 Hz, 2H), 7.53-7.47 (m, 2H), 7.17-7.10 (m, 1H), 7.07-7.00 (m, 1H), 5.39 (dd, J = 5.6, 12.0 Hz, 1H), 4.59 (s, 1H), 4.54-4.45 (m, 1H), 4.44-4.39 (m, 1H), 3.88-3.74 (m, 2H), 3.63-3.54 (m, 5H), 3.43 (d, J = 6.0 Hz, 2H), 3.08 (t, J = |

TABLE 4-continued

Compounds prepared by Method 2.

| I-# | Intermediate Amine | Intermediate Aldehyde | LCMS (ES+) m/z (M + H)⁺ | 1H NMR (400 MHz, DMSO-d6) δ |
|---|---|---|---|---|
| | | | | 5.6 Hz, 1H), 2.95-2.86 (m, 1H), 2.78-2.63 (m, 3H), 2.40 (s, 3H), 2.23 (d, J = 8.4 Hz, 2H), 2.05-1.90 (m, 6H), 1.46-1.29 (m, 2H) |
| I-397 | BAI | CFV | 786.3 | 11.08 (s, 1H), 10.23 (s, 1H), 8.42 (d, 1H), 8.36 (d, 1H), 8.37 (s, 1H), 8.20 (d, 1H), 8.14 (s, 1H), 7.54 (s, 1H), 7.00-6.93 (q, 2H), 6.90 (d, 1H), 5.38-5.32 (m, 1H), 4.48-4.42 (m, 1H), 3.64 (s, 3H), 3.21-3.15 (m, 2H), 3.01-2.84 (m, 6H), 2.76-2.68 (m, 2H), 2.66-2.62 (m, 1H), 2.61-2.58 (m, 1H), 2.29-2.22 (m, 3H), 2.21-2.12 (m, 3H), 2.03-1.93 (m, 6H), 1.30 (s, 3H), 1.29 (s, 3H) |
| I-398 | BWS | BSC | 784.4 | 11.10 (s, 1H), 10.14 (s, 1H), 8.43 (d, 1H), 8.41 (t, 2H), 8.20 (d, 2H), 7.52 (s, 1H), 7.14 (d, 1H), 7.03 (t, J = 7.6 Hz, 1H), 6.95 (d, J = 7.6 Hz, 1H), 5.36 (d, J = 12.4 Hz, 1H), 4.50-4.42 (m, 1H), 3.71 (s, 3H), 2.96-2.83 (m, 3H), 2.75-2.70 (m, 1H), 2.66-2.64 (m, 2H), 2.62-2.58 (m, 2H), 2.55-2.53 (m, 3H), 2.41 (s, 3H), 2.20 (d, J = 10.4 Hz, 3H), 2.11-1.91 (m, 9H), 1.28-1.18 (m, 2H) |
| I-401 | BAI | CFW | 759.2 | 11.09 (s, 1H), 10.20 (s, 1H), 9.58 (s, 1H), 9.48 (s, 1H), 8.38 (s, 1H), 7.97 (s, 1H), 7.51 (s, 1H), 7.11-6.83 (m, 3H), 5.43-5.27 (m, 1H), 4.53-4.37 (m, 1H), 3.64 (s, 3H), 3.22-3.10 (m, 2H), 3.04-2.82 (m, 5H), 2.64-2.58 (m, 2H), 2.37 (s, 3H), 2.25-2.14 (m, 4H), 2.00-1.94 (m, 6H), 1.76-1.62 (m, 1H), 1.29-1.12 (m, 3H) |
| I-402 | CAK | BTW | 787.2 | 10.37 (s, 1H), 9.04-8.85 (m, 1H), 8.44-8.29 (m, 4H), 8.19-8.17 (m, 1H), 7.66-7.52 (m, 2H), 7.01-6.95 (m, 1H), 6.75 (d, J = 8.8 Hz, 1H), 5.46-5.37 (m, 1H), 4.58-4.46 (m, 1H), 3.82 (s, 3H), 3.67-3.53 (m, 6H), 3.18-3.13 (m, 1H), 3.07-2.93 (m, 6H), 2.83-2.70 (m, 3H), 2.26-2.20 (m, 2H), 2.12-1.95 (m, 7H), 1.92-1.83 (m, 2H), 1.40-1.27 (m, 2H) |
| I-403 | BCD | BSC | 771.3 | 10.13 (s, 1H), 9.00-8.89 (m, 1H), 8.47-8.33 (m, 3H), 8.25-8.17 (m, 2H), 7.52 (s, 1H), 7.12-6.92 (m, 3H), 5.46 (dd, J = 5.6, 12.8 Hz, 1H), 4.56-4.41 (m, 1H), 3.67-3.58 (m, 5H), 3.24-3.17 (m, 2H), 3.10-3.02 (m, 5H), 2.99-2.92 (m, 1H), 2.84-2.70 (m, 2H), 2.41 (s, 3H), 2.24-2.17 (m, 2H), 2.12-1.96 (m, 10H), 1.35-1.22 (m, 2H) |
| I-404 | CFX | BSC | 772.3 | 10.13 (s, 1H), 8.45-8.36 (m, 3H), 8.20 (d, 2H), 7.51 (s, 1H), 7.03-6.88 (m, 3H), 5.43 (d, J = 12.8 Hz, 1H), 4.50-4.40 (m, 1H), 3.65 (s, 3H), 3.03 (s, 3H), 3.02-2.90 (m, 4H), 2.82-2.78 (m, 1H), 2.74-2.64 (m, 2H), 2.62-2.58 (m, 3H), 2.41 (s, 3H), 2.32-2.11 (m, 5H), 2.06-1.86 (m, 6H), 1.27-1.10 (m, 2H) |
| I-405 | BAI | CFZ | 802.2 | 12.54 (s, 1H), 11.10 (s, 1H), 9.08 (s, 1H), 8.59 (d, J = 0.8 Hz, 1H), 8.50-8.44 (m, 2H), 8.40 (t, J = 8.0 Hz, 1H), 8.21 (dd, J = 0.8, 7.6 Hz, 1H), 7.08-6.91 (m, 3H), 5.37 (dd, J = 4.8, 12.4 Hz, 1H), 4.66-4.51 (m, 1H), 3.96 (s, 3H), 3.65 (s, 3H), 3.30-3.27 (m, 2H), 3.24-3.08 (m, 4H), 2.97-2.83 (m, 2H), 2.78-2.68 (m, 1H), 2.66-2.57 (m, 1H), 2.52 (s, 1H), 2.27-2.20 (m, 2H), 2.09-1.93 (m, 7H), 1.43-1.19 (m, 3H) |
| I-406 | BAI | CGA | 770.3 | 11.10 (s, 1H), 8.81 (s, 1H), 8.67-8.54 (m, 2H), 8.34 (t, J = 8.0 Hz, 1H), 8.22 (s, 1H), 8.15 (d, J = 7.6 Hz, 1H), 7.06-6.79 (m, 3H), 5.36 (dd, J = 5.2, 12.8 Hz, 1H), 4.66 (t, J = 11.2 Hz, 1H), 3.64 (s, 3H), 3.10-2.78 (m, 7H), 2.77-2.58 (m, 3H), 2.30-2.19 (m, 5H), 2.08-1.97 (m, 5H), 1.79-1.63 (m, 1H), 1.25-1.11 (m, 2H) |
| I-411 | BAI | CGD | 782.3 | 11.10 (s, 1H), 9.43-9.16 (m, 1H), 9.02-8.83 (m, 2H), 8.77 (s, 1H), 8.70 (s, 1H), 8.05 (s, 1H), 7.96-7.86 (m, 1H), 7.17 (d, J = 4.8 Hz, 1H), 7.09-7.01 (m, 1H), 6.99-6.90 (m, 2H), 5.38 (dd, J = 5.2, 12.4 Hz, 1H), 4.74-4.53 (m, 1H), 4.14-3.91 (m, 1H), 3.65 (s, 5H), 3.27-3.07 (m, 6H), 2.97-2.84 (m, 1H), 2.77-2.68 (m, 1H), 2.61 (s, 1H), 2.31-2.25 (m, 2H), 2.12-1.83 (m, 7H), 1.37 (d, J = 6.4 Hz, 6H), 1.36-1.29 (m, 3H) |
| I-412 | BAI | CFY | 786.4 | 13.15 (s, 1H), 11.10 (s, 1H), 9.08 (s, 1H), 8.67 (s, 1H), 8.56 (s, 1H), 8.47-8.43 (m, 1H), 8.40-8.35 (m, 1H), 8.20 (d, J = 7.6 Hz, 1H), 7.04-6.84 (m, 3H), 5.36 (dd, J = 5.6, 12.4 Hz, 1H), 4.64-4.46 (m, 1H), 3.64 (s, 3H), 3.16 (s, 1H), 3.04-2.84 (m, |

TABLE 4-continued

Compounds prepared by Method 2.

| I-# | Intermediate Amine | Intermediate Aldehyde | LCMS (ES+) m/z (M + H)+ | 1H NMR (400 MHz, DMSO-d6) δ |
|---|---|---|---|---|
| | | | | 6H), 2.80 (s, 3H), 2.65 (d, J = 11.6 Hz, 2H), 2.30-2.13 (m, 6H), 2.04-1.93 (m, 5H), 1.77-1.59 (m, 1H), 1.24-1.12 (m, 2H) |
| I-413 | CGF | ATJ | 774.3 | 10.52 (d, J = 7.6 Hz, 2H), 9.42 (s, 1H), 8.71 (s, 1H), 8.60 (s, 1H), 8.49-8.37 (m, 2H), 8.35 (s, 1H), 8.22 (d, J = 7.6 Hz, 1H), 7.51 (d, J = 9.6 Hz, 1H), 7.29 (d, J = 9.2 Hz, 1H), 7.15 (s, 1H), 4.51-4.38 (m, 1H), 3.99 (s, 3H), 3.97-3.87 (m, 1H), 3.80-3.45 (m, 6H), 3.40-3.33 (m, 2H), 3.21 (s, 3H), 3.03 (m, 1H), 2.77-2.68 (m, 1H), 2.21 (d, J = 11.2 Hz, 2H), 2.10-1.89 (m, 5H), 1.39-1.22 (m, 2H) |
| I-414 | CGG | BSC | 770.4 | 11.07 (s, 1H), 10.13 (s, 1H), 8.45-8.34 (m, 3H), 8.26-8.18 (m, 2H), 7.51 (s, 1H), 6.97-6.90 (m, 1H), 6.79 (d, J = 8.0 Hz, 1H), 6.69 (d, J = 7.6 Hz, 1H), 5.31 (dd, J = 5.4, 12.4 Hz, 1H), 4.46-4.33 (m, 1H), 4.15 (d, J = 5.6 Hz, 2H), 3.51 (s, 3H), 3.08 (d, J = 9.6 Hz, 2H), 2.97 (dd, J = 3.6, 10.0 Hz, 2H), 2.93-2.83 (m, 1H), 2.82-2.74 (m, 1H), 2.64-2.56 (m, 2H), 2.40 (s, 3H), 2.38 (d, J = 7.2 Hz, 2H), 2.15-2.06 (m, 3H), 2.02-1.94 (m, 1H), 1.93-1.81 (m, 4H), 1.69-1.59 (m, 1H), 1.13-1.00 (m, 2H) |
| I-419 | AQK | BXS | 826.4 | 11.09 (s, 1H), 10.06 (s, 1H), 9.36 (d, J = 1.6 Hz, 1H), 9.21 (d, J = 1.6 Hz, 1H), 8.80 (s, 1H), 8.25 (s, 1H), 7.65 (s, 1H), 7.00-6.86 (m, 4H), 5.35 (dd, J = 5.2, 12.8 Hz, 1H), 4.47 (s, 1H), 4.42-4.33 (m, 1H), 4.31 (s, 1H), 4.01 (d, J = 7.2 Hz, 1H), 3.72 (d, J = 6.4 Hz, 1H), 3.64 (s, 3H), 3.43 (d, J = 8.0 Hz, 2H), 3.19-3.15 (m, 2H), 2.99 (d, J = 9.6 Hz, 1H), 2.95-2.83 (m, 2H), 2.77-2.70 (m, 3H), 2.63 (d, J = 3.6 Hz, 1H), 2.17-2.12 (m, 2H), 2.07 (s, 3H), 2.00-1.95 (m, 3H), 1.92 (d, J = 3.6 Hz, 1H), 1.89 (d, J = 8.0 Hz, 1H), 1.86-1.81 (m, 2H), 1.77 (d, J = 10.4 Hz, 2H), 1.71-1.66 (m, 2H), 1.63-1.58 (m, 1H), 1.18-1.09 (m, 2H) |
| I-420 | BAI | CGI | 780.4 | 11.09 (s, 1H), 9.14 (s, 1H), 8.86-8.78 (m, 2H), 8.52 (s, 1H), 7.85 (s, 1H), 7.06-6.87 (m, 3H), 5.40-5.31 (m, 1H), 4.63-4.52 (m, 1H), 4.46-4.35 (m, 1H), 3.64 (s, 3H), 3.12-2.83 (m, 6H), 2.77-2.60 (m, 3H), 2.52 (s, 2H), 2.30-2.22 (m, 3H), 2.10-1.96 (m, 4H), 1.95-1.86 (m, 2H), 1.86-1.61 (m, 2H), 1.32 (d, J = 6.4 Hz, 6H), 1.28-1.14 (m, 2H) |
| I-422[h] | BAI | BJB | 822.3 | 11.54 (s, 1H), 8.93 (s, 1H), 8.59 (s, 1H), 8.50 (d, J = 8.0 Hz, 1H), 8.16 (t, J = 8.0 Hz, 1H), 8.09-8.05 (m, 2H), 7.92 (d, J = 8.0 Hz, 1H), 7.08-6.99 (m, 2H), 6.64 (m, 1H), 5.21 (dd, J = 5.6, 12.0 Hz, 1H), 4.54-4.43 (m, 1H), 3.77 (s, 3H), 3.29-3.18 (m, 2H), 3.17 (s, 3H), 3.13 (m, 2H), 3.00-2.91 (m, 2H), 2.90-2.83 (m, 1H), 2.81-2.72 (m, 2H), 2.67-2.49 (m, 2H), 2.43-2.33 (m, 2H), 2.28-2.15 (m, 3H), 2.11-2.00 (m, 2H), 1.94-1.84 (m, 1H), 1.38 (m, 2H), 1.34-1.28 (m, 1H), 1.26-1.21 (m, 1H) |
| I-423 | BWT | BRP | 756.3 | 11.09 (s, 1H), 10.36 (s, 1H), 8.44-8.33 (m, 3H), 8.30 (d, J = 0.8 Hz, 1H), 8.18 (dd, J = 1.2, 7.6 Hz, 1H), 7.65-7.58 (m, 1H), 7.58-7.51 (m, 1H), 6.99 (d, J = 4.4 Hz, 2H), 6.85 (d, J = 4.0 Hz, 1H), 5.39-5.30 (m, 1H), 4.52-4.41 (m, 1H), 3.89 (s, 2H), 3.63 (d, J = 1.2 Hz, 3H), 3.59 (d, J = 10.8 Hz, 1H), 3.15 (d, J = 8.8 Hz, 1H), 3.01-2.81 (m, 3H), 2.79-2.57 (m, 4H), 2.19 (d, J = 12.0 Hz, 2H), 2.09-1.88 (m, 7H), 1.74-1.58 (m, 1H), 1.29-1.13 (m, 2H) |
| I-425 | AQK | CGY | 791.3 | 11.16-10.99 (m, 1H), 10.51 (s, 1H), 9.01 (s, 1H), 8.52-8.41 (m, 2H), 8.25 (d, J = 0.8 Hz, 1H), 7.74 (s, 1H), 7.04-6.82 (m, 3H), 5.39-5.29 (m, 1H), 4.03 (s, 3H), 3.84 (s, 1H), 3.63 (s, 3H), 2.72-2.62 (m, 7H), 2.37-2.30 (m, 4H), 2.24 (s, 3H), 2.06-1.97 (m, 3H), 1.86-1.75 (m, 3H), 1.71-1.57 (m, 3H) |
| I-426 | CEQ | ATJ | 800.4 | 11.07 (s, 1H), 10.50 (s, 1H), 8.69 (s, 1H), 8.49-8.44 (m, 1H), 8.43-8.37 (m, 1H), 8.34 (s, 1H), 8.22 (d, J = 7.6 Hz, 1H), 7.16 (s, 1H), 7.03-6.96 (m, 1H), 6.89 (d, J = 7.6 Hz, 1H), 6.82 (d, J = 7.6 Hz, 1H), 5.42-5.23 (m, 1H), 5.12-4.71 (m, 1H), 4.44-4.31 (m, 1H), 3.98 (s, 3H), 3.25-3.14 (m, |

TABLE 4-continued

Compounds prepared by Method 2.

| I-# | Inter-mediate Amine | Inter-mediate Aldehyde | LCMS (ES+) m/z (M + H)+ | 1H NMR (400 MHz, DMSO-d6) δ |
|---|---|---|---|---|
| I-427 | BAI | CCR | 792.0 | 2H), 3.06-2.80 (m, 6H), 2.65-2.56 (m, 2H), 2.27-2.10 (m, 5H), 2.03-1.87 (m, 5H), 1.73-1.59 (m, 1H), 1.21-0.89 (m, 6H) 11.09 (s, 1H), 10.34 (s, 1H), 8.72 (s, 1H), 8.53-8.43 (m, 1H), 8.43-8.32 (m, 1H), 8.22 (d, J = 7.6 Hz, 1H), 7.28 (s, 1H), 7.10-6.98 (m, 1H), 6.98-6.94 (m, 1H), 6.94-6.80 (m, 1H), 5.44-5.25 (m, 1H), 4.10-3.99 (m, 2H), 3.96 (s, 3H), 3.63 (s, 3H), 3.23-3.09 (m, 4H), 3.02-2.81 (m, 5H), 2.64 (s, 3H), 2.26 (d, J = 3.6 Hz, 2H), 2.04-1.95 (m, 1H), 1.95-1.80 (m, 3H), 1.44-1.30 (m, 1H), 1.28-1.15 (m, 2H) |
| I-428 | CJA | ATJ | 759.2 | 11.10 (s, 1H), 10.50 (s, 1H), 8.69 (s, 1H), 8.48-8.37 (m, 2H), 8.34 (s, 1H), 8.22 (d, J = 7.8 Hz, 1H), 7.21 (s, 1H), 7.14 (s, 1H), 7.11-7.00 (m, 2H), 5.37 (dd, J = 5.2, 12.8 Hz, 1H), 4.42 (t, J = 11.6 Hz, 1H), 3.98 (s, 3H), 3.79-3.41 (m, 3H), 3.36 (s, 3H), 3.21-3.01 (m, 2H), 2.99-2.79 (m, 2H), 2.78-2.59 (m, 3H), 2.44-2.35 (m, 1H), 2.18 (d, J = 11.6 Hz, 2H), 2.08-1.88 (m, 6H), 1.83 (s, 1H), 1.39-1.11 (m, 2H) |

[a]For Method 2, when the amine is the HCl salt, TEA was added to free base the salt, followed by HOAc to adjust the pH to 3-4. KOAc could also be used in place of the TEA/HOAc combination. Step 1 was run anywhere from 0.5-48 hrs and the reaction temperature was run anywhere from −15° C. to rt. The final products were isolated under standard purification techniques including reverse HPLC, silica gel chromatography, and prep-TLC with appropriate solvent conditions.
[b]No DMF used as a co-solvent.
[c]No DMF used as a co-solvent.
[d]For the reductive amination tetraisopropoxytitanium was used and the mixture was stirred at 80° C. for 16 hrs. Then the reaction mixture was cooled to 25° C., and NaBH$_3$CN was added and the mixture was stirred at 25° C. for 8 hrs.
[e]LCMS reported as (M-H20)+ ion.
[f]Reaction run for 96 hr at rt.
[g]DIEA used as the base.
[h]CDCl$_3$ used as the solvent for the NMR data.

Example 3 (Method 5): Synthesis of 5-cyano-N-[2-[4-[[[1-[1-(2,6-dioxo-3-piperidyl)-3-methyl-2-oxo-benzimidazol-4-yl]-4-piperidyl]-methyl-amino]methyl]cyclohexyl]-6-methoxy-indazol-5-yl]pyridine-3-carboxamide (I-71)

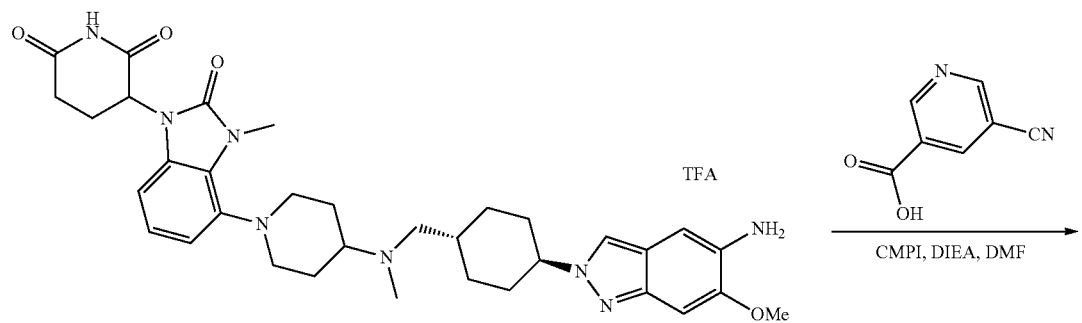

-continued

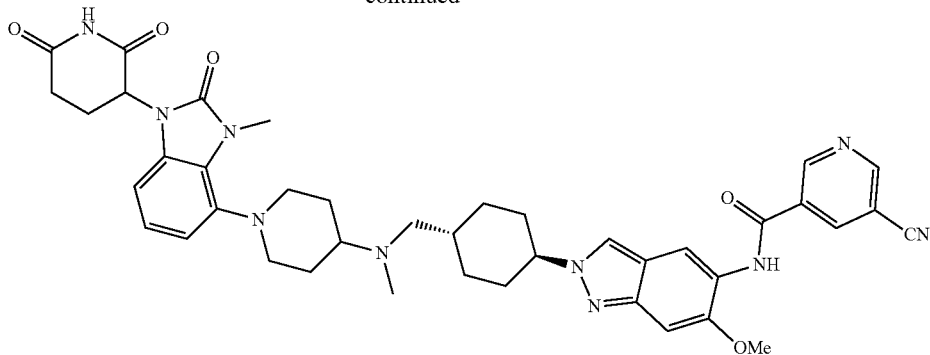

To a solution of 5-cyanopyridine-3-carboxylic acid (11.9 mg, 80.7 umol), CMPI (24.7 mg, 96.9 umol) and DIEA (52.2 mg, 403 umol) in DMF (1 mL) was added 3-[4-[4-[[4-(5-amino-6-methoxy-indazol-2-yl)cyclohexyl]methyl-methyl-amino]-1-piperidyl]-3-methyl-2-oxo-benzimidazol-1-yl]piperidine-2,6-dione (60.0 mg, 80.7 umol, TFA, Intermediate BGU). The reaction mixture was then stirred at 25° C. for 1.5 hrs. On completion, the reaction mixture was concentrated in vacuo to give a residue. The residue was purified by prep-HPLC (column: Phenomenex luna C18 150*25 mm*10 um; mobile phase: [water (0.225% FA)-ACN]; B %: 10%-40%, 11.5 min) to give the title compound (27.5 mg, 42% yield) as an off-white solid. $^1$H NMR (400 MHz, DMSO-$d_6$) δ 11.09 (s, 1H), 9.90 (s, 1H), 9.31 (s, 1H), 9.21 (d, J=1.6 Hz, 1H), 8.88-8.73 (m, 1H), 8.32 (s, 1H), 8.08 (s, 1H), 7.08 (s, 1H), 7.02-6.95 (m, 1H), 6.95-6.85 (m, 2H), 5.35 (dd, J=5.2, 12.4 Hz, 1H), 4.46-4.32 (m, 1H), 3.88 (s, 3H), 3.65 (s, 3H), 3.27 (s, 3H), 3.18 (d, J=10.0 Hz, 2H), 2.94-2.84 (m, 1H), 2.80-2.69 (m, 3H), 2.66-2.56 (m, 2H), 2.43-2.34 (m, 2H), 2.16 (d, J=11.2 Hz, 2H), 2.03-1.83 (m, 7H), 1.80-1.57 (m, 3H), 1.24-1.07 (m, 2H); LC-MS (ESI$^+$) m/z 759.2 (M+H)$^+$.

The following compounds in Table 5 where prepared according to the same procedure of Method 5 above.

TABLE 5

Compounds prepared by Method 5.

| I-# | Intermediate Amine | Intermediate Acid | LCMS (ES+) m/z (M + H)$^+$ | 1H NMR (400 MHz, DMSO-d6) δ |
|---|---|---|---|---|
| I-34 | BGU | BQJ | 803.3 | 11.10 (s, 1H), 10.29 (s, 1H), 9.89 (d, J = 1.6 Hz, 1H), 8.65 (d, J = 1.6 Hz, 1H), 8.34 (s, 1H), 8.11 (s, 1H), 7.11 (s, 1H), 7.01-6.86 (m, 3H), 5.35 (dd, J = 5.2, 12.4 Hz, 1H), 4.45-4.33 (m, 1H), 3.88 (s, 3H), 3.65 (s, 3H), 3.16 (d, J = 11.6 Hz, 2H), 2.93-2.85 (m, 1H), 2.77-2.71 (m, 2H), 2.68-2.58 (m, 2H), 2.46-2.42 (m, 1H), 2.31-2.29 (m, 2H), 2.26 (s, 3H), 2.18-2.14 (m, 2H), 2.05-1.92 (m, 4H), 1.90-1.88 (m, 1H), 1.85-1.77 (m, 2H), 1.73-1.62 (m, 2H), 1.60-1.53 (m, 1H), 1.17-1.06 (m, 2H) |
| I-77 | BSS | 5-cyanopyridine-3-carboxylic acid (CAS# 887579-62-6) | 730.5 | 11.1 (s, 1H), 9.90 (s, 1H), 9.31 (s, 1H), 9.21 (d, J = 1.6 Hz, 1H), 8.78 (s, 1H), 8.31 (s, 1H), 8.08 (s, 1H), 7.12-7.06 (m, 1H), 7.06-6.94 (m, 3H), 5.37 (dd, J = 5.2, 12.8 Hz, 1H), 4.45-4.31 (m, 1H), 3.88 (s, 3H), 3.59 (s, 3H), 3.05-2.83 (m, 4H), 2.75 (d, J = 3.2 Hz, 1H), 2.65-2.59 (m, 1H), 2.23 (d, J = 6.8 Hz, 2H), 2.18-2.06 (m, 4H), 2.01-1.86 (m, 5H), 1.84-1.62 (m, 5H), 1.20-1.11 (m, 2H) |
| I-80 | BGU | 5-chloropyridine-3-carboxylic acid (CAS# 22620-27-5) | 768.4 | 11.09 (s, 1H), 9.83 (s, 1H), 9.05 (s, 1H), 8.83 (d, J = 2.4 Hz, 1H), 8.41 (s, 1H), 8.31 (s, 1H), 8.03 (s, 1H), 7.07 (s, 1H), 7.01-6.94 (m, 1H), 6.94-6.84 (m, 2H), 5.35 (dd, J = 5.6, 12.8 Hz, 1H), 4.45-4.32 (m, 1H), 3.87 (s, 3H), 3.65 (s, 3H), 3.31-3.28 (m, 3H), 3.17 (d, J = 11.2 Hz, 2H), 2.96-2.83 (m, 1H), 2.80-2.67 (m, 3H), 2.66-2.53 (m, 2H), 2.41-2.34 (m, 2H), 2.16 (d, J = 10.8 Hz, 2H), 2.03-1.80 (m, 7H), 1.77-1.57 (m, 3H), 1.21-1.06 (m, 2H) |
| I-81 | BGU | 5-fluoropyridine-3-carboxylic acid (CAS# 402-66-4) | 752.4 | 11.10 (s, 1H), 9.81 (s, 1H), 9.00 (s, 1H), 8.96-8.83 (m, 1H), 8.80 (d, J = 2.8 Hz, 1H), 8.32 (s, 1H), 8.21 (d, J = 9.6 Hz, 1H), 7.06 (s, 1H), 7.04-6.97 (m, 1H), 6.96-6.89 (m, 2H), 5.36 (dd, J = 5.6, 12.8 Hz, 1H), 4.49-4.36 (m, 1H), 3.88 (s, 3H), 3.66 (s, 3H), 3.28-3.19 (m, 4H), 3.05- |

TABLE 5-continued

Compounds prepared by Method 5.

| I-# | Intermediate Amine | Intermediate Acid | LCMS (ES+) m/z (M + H)+ | 1H NMR (400 MHz, DMSO-d6) δ |
|---|---|---|---|---|
| I-86 | BSS | 5-(trifluoromethyl)pyridine-3-carboxylic acid (CAS# 131747-40-5) | 773.6 | 2.95 (m, 1H), 2.94-2.77 (m, 6H), 2.76-2.68 (m, 1H), 2.65-2.57 (m, 1H), 2.23-2.16 (m, 2H), 2.15-2.03 (m, 3H), 2.03-1.86 (m, 7H), 1.41-1.19 (m, 2H) 11.1 (s, 1H), 10.0 (s, 1H), 9.37 (s, 1H), 9.20-9.13 (m, 1H), 8.67 (s, 1H), 8.32 (s, 1H), 8.03 (s, 1H), 7.08 (s, 1H), 7.06-6.97 (m, 3H), 5.38 (dd, J = 5.6, 12.4 Hz, 1H), 4.46-4.35 (m, 1H), 3.87 (s, 3H), 3.61 (s, 3H), 3.31-3.29 (m, 4H), 2.93-2.85 (m, 1H), 2.74-2.68 (m, 1H), 2.67-2.58 (m, 2H), 2.17 (d, J = 11.6 Hz, 3H), 2.04-1.94 (m, 5H), 1.93-1.81 (m, 5H), 1.80-1.69 (m, 1H), 1.26-1.14 (m, 2H) |
| I-92 | BGU | 5-(trifluoromethyl)pyridine-3-carboxylic acid (CAS# 131747-40-5) | 802.5 | 11.10 (s, 1H), 10.03 (s, 1H), 9.38 (s, 1H), 9.19 (s, 1H), 8.68 (s, 1H), 8.34 (s, 1H), 8.04 (s, 1H), 7.08 (s, 1H), 7.04-6.97 (m, 1H), 6.96-6.87 (m, 2H), 5.37 (dd, J = 5.6, 12.8 Hz, 1H), 4.48-4.36 (m, 1H), 3.88 (s, 3H), 3.66 (s, 3H), 3.30 (s, 3H), 3.23 (d, J = 11.2 Hz, 2H), 2.97-2.71 (m, 6H), 2.67-2.59 (m, 2H), 2.19 (d, J = 11.2 Hz, 2H), 2.09-1.90 (m, 7H), 1.89-1.71 (m, 3H), 1.33-1.14 (m, 2H) |
| I-93 | BSS | 5-chloropyridine-3-carboxylic acid (CAS# 22620-27-5) | 739.1 | 11.10 (s, 1H), 9.84 (s, 1H), 9.04 (s, 1H), 8.83 (d, J = 2.4 Hz, 1H), 8.41 (s, 1H), 8.31 (s, 1H), 8.04 (s, 1H), 7.07 (s, 1H), 7.06-6.97 (m, 3H), 5.38 (dd, J = 5.2, 12.4 Hz, 1H), 4.48-4.35 (m, 1H), 3.87 (s, 3H), 3.61 (s, 3H), 2.97-2.67 (m, 4H), 2.65-2.57 (m, 2H), 2.52 (s, 2H), 2.18 (d, J = 10.8 Hz, 2H), 2.05-1.86 (m, 10H), 1.82 (s, 1H), 1.29-1.15 (m, 3H) |
| I-130 | BGU | CBV | 802.5 | 11.10 (s, 1H), 10.03 (s, 1H), 9.38 (s, 1H), 9.19 (s, 1H), 8.68 (s, 1H), 8.34 (s, 1H), 8.04 (s, 1H), 7.08 (s, 1H), 7.04-6.97 (m, 1H), 6.96-6.87 (m, 2H), 5.37 (dd, J = 5.6, 12.8 Hz, 1H), 4.48-4.36 (m, 1H), 3.88 (s, 3H), 3.66 (s, 3H), 3.30 (s, 3H), 3.23 (d, J = 11.2 Hz, 2H), 2.97-2.71 (m, 6H), 2.67-2.59 (m, 2H), 2.19 (m, 2H), 2.09-1.90 (m, 7H), 1.89-1.71 (m, 3H), 1.33-1.14 (m, 2H) |
| I-131 | BGU | BTX | 819.6 | 11.10 (s, 1H), 9.89 (s, 1H), 8.32 (s, 1H), 8.18 (s, 1H), 8.12 (d, J = 8.8 Hz, 1H), 8.02-7.92 (m, 2H), 7.08 (s, 1H), 7.03-6.96 (m, 1H), 6.96-6.85 (m, 2H), 5.36 (dd, J = 5.6, 12.8 Hz, 1H), 4.47-4.34 (m, 1H), 3.87 (s, 3H), 3.65 (s, 3H), 3.29 (s, 3H), 3.20 (d, J = 10.0 Hz, 2H), 2.96-2.69 (m, 5H), 2.69-2.57 (m, 3H), 2.17 (d, J = 10.4 Hz, 2H), 2.06-1.87 (m, 7H), 1.86-1.61 (m, 3H), 1.30-1.08 (m, 2H) |
| I-132 | BSS | BTX | 790.6 | 11.09 (s, 1H), 9.88 (s, 1H), 8.31 (s, 1H), 8.18 (s, 1H), 8.11 (d, J = 8.8 Hz, 1H), 8.02-7.91 (m, 2H), 7.08 (s, 1H), 7.05-6.94 (m, 3H), 5.37 (m, 1H), 4.46-4.33 (m, 1H), 3.86 (s, 3H), 3.59 (s, 3H), 3.23 (s, 1H), 3.00 (d, J = 10.8 Hz, 2H), 2.95-2.83 (m, 1H), 2.77-2.62 (m, 2H), 2.22 (d, J = 7.2 Hz, 2H), 2.16 (d, J = 11.2 Hz, 2H), 2.12-2.04 (m, 2H), 2.02-1.95 (m, 3H), 1.95-1.86 (m, 2H), 1.84-1.74 (m, 4H), 1.71-1.61 (m, 1H), 1.21-1.06 (m, 2H) |
| I-133 | BUP | BUN | 700.5 | 11.09 (s, 1H), 10.51 (s, 1H), 9.33 (d, J = 2.0 Hz, 1H), 9.21 (d, J = 2.0 Hz, 1H), 8.82 (t, J = 2.4 Hz, 1H), 8.40 (s, 1H), 8.26 (d, J = 1.2 Hz, 1H), 7.62 (d, J = 9.2 Hz, 1H), 7.44 (dd, J = 2.0, 9.2 Hz, 1H), 7.07-6.91 (m, 3H), 5.37 (dd, J = 5.2, 12.8 Hz, 1H), 4.50-4.39 (m, 1H), 3.52 (s, 3H), 3.24-3.19 (m, 1H), 3.05-2.96 (m, 2H), 2.94-2.83 (m, 1H), 2.77-2.58 (m, 2H), 2.27-2.20 (m, 2H), 2.10-2.14 (m, 2H), 2.13-2.06 (m, 2H), 2.02-1.88 (m, 5H), 1.86-1.75 (m, 4H), 1.72-1.61 (m, 1H), 1.21-1.07 (m, 2H) |
| I-134 | BSS | BUX | 753.5 | 11.09 (s, 1H), 9.75 (s, 1H), 8.94 (s, 1H), 8.36 (s, 1H), 8.30 (s, 1H), 8.01 (s, 1H), 7.07 (s, 1H), 7.05-7.00 (m, 2H), 6.99 (d, J = 3.6 Hz, 1H), 5.37 (dd, J = 5.6, 12.4 Hz, 1H), 4.44-4.33 (m, 1H), 3.87 (s, 3H), 3.59 (s, 3H), 3.25 (d, J = 4.4 Hz, 1H), 3.03 (d, J = 11.2 Hz, 2H), 2.94-2.83 (m, 1H), 2.77-2.67 (m, 1H), 2.63 (s, 3H), 2.61-2.57 (m, 1H), 2.26 (d, J = 6.8 Hz, 2H), 2.15 (d, J = 11.2 Hz, 4H), 1.98 (d, J = 12.4 Hz, 3H), |

TABLE 5-continued

Compounds prepared by Method 5.

| I-# | Intermediate Amine | Intermediate Acid | LCMS (ES+) m/z (M + H)+ | 1H NMR (400 MHz, DMSO-d6) δ |
|---|---|---|---|---|
| | | | | 1.94-1.86 (m, 2H), 1.85-1.76 (m, 4H), 1.68 (d, J = 1.2 Hz, 1H), 1.21-1.07 (m, 2H) |
| I-135 | BSS | BUZ | 740.3 | 11.09 (s, 1H), 10.59 (s, 1H), 9.66 (d, J = 2.4 Hz, 1H), 8.67 (s, 1H), 8.49 (d, J = 2.4 Hz, 1H), 8.35 (s, 1H), 7.17 (s, 1H), 7.06-6.93 (m, 3H), 5.37 (J = 5.6, 12.0 Hz, 1H), 4.44-4.35 (m, 1H), 4.01 (s, 3H), 3.59 (s, 3H), 3.26-3.19 (m, 2H), 3.02 (d, J = 12.0 Hz, 2H), 2.94-2.83 (m, 1H), 2.75-2.61 (m, 2H), 2.24 (d, J = 8.0 Hz, 2H), 2.19-2.08 (m, 4H), 1.98 (d, J = 12.0 Hz, 3H), 1.91 (d, J = 12.0 Hz, 1H), 1.77 (s, 4H), 1.67 (d, J = 3.6 Hz, 1H), 1.21-1.09 (m, 2H) |
| I-136 | BSS | BVF | 764.8 | 11.09 (s, 1H), 10.04 (s, 1H), 9.14 (d, J = 1.2 Hz, 1H), 8.71 (d, J = 1.6 Hz, 1H), 8.32 (s, 1H), 8.06 (s, 1H), 7.09 (s, 1H), 7.05-6.95 (m, 3H), 5.37 (dd, J = 5.2, 12.6 Hz, 1H), 4.45-4.33 (m, 1H), 3.87 (s, 3H), 3.59 (s, 3H), 3.25-3.19 (m, 1H), 3.04-2.97 (m, 2H), 2.94-2.84 (m, 1H), 2.77-2.69 (m, 1H), 2.62 (d, J = 17.0 Hz, 1H), 2.23 (d, J = 7.0 Hz, 2H), 2.19-2.06 (m, 4H), 2.02-1.95 (m, 3H), 1.94-1.85 (m, 2H), 1.84-1.75 (m, 4H), 1.67 (dd, J = 3.6, 10.4 Hz, 1H), 1.20-1.08 (m, 2H) |
| I-174 | BXA | BXC | 722.3 | 11.11 (s, 1H), 9.48 (d, J = 9.6 Hz, 1H), 8.51 (s, 1H), 8.31 (s, 1H), 7.92 (t, J = 7.6 Hz, 1H), 7.67-7.60 (m, 1H), 7.44-7.36 (m, 2H), 7.11-7.06 (m, 2H), 7.06-7.02 (m, 1H), 6.96 (d, J = 8.2 Hz, 1H), 5.40 (dd, J = 5.4, 12.4 Hz, 1H), 4.48-4.38 (m, 1H), 3.93 (s, 3H), 3.68-3.55 (m, 6H), 3.25-3.16 (m, 2H), 3.04 (d, J = 0.8 Hz, 2H), 2.94-2.84 (m, 1H), 2.77-2.68 (m, 1H), 2.68-2.64 (m, 1H), 2.24-2.13 (m, 4H), 2.08-1.91 (m, 8H), 1.30 (d, J = 11.2 Hz, 2H) |
| I-175 | BXA | BXD | 779.2 | 11.09 (s, 1H), 9.77 (s, 1H), 8.89 (s, 1H), 8.42 (s, 1H), 8.35 (s, 1H), 7.16 (s, 1H), 7.05-6.95 (m, 3H), 5.38 (dd, J = 6.0, 12.8 Hz, 1H), 4.44-4.34 (m, 1H), 3.96 (s, 3H), 3.60 (s, 3H), 3.30-3.28 (m, 4H), 3.11-3.02 (m, 1H), 2.95-2.83 (m, 1H), 2.77-2.68 (m, 1H), 2.65-2.57 (m, 1H), 2.18-2.14 (m, 2H), 2.04-1.94 (m, 4H), 1.94-1.88 (m, 2H), 1.88-1.79 (m, 4H), 1.76-1.66 (m, 1H), 1.26-1.07 (m, 3H) |
| I-193 | BXA | BXJ | 769.2 | 11.09 (s, 1H), 9.61 (s, 1H), 9.59-9.56 (m, 1H), 8.74 (d, J = 1.6 Hz, 1H), 8.40 (d, J = 2.0 Hz, 1H), 8.29 (s, 1H), 8.00 (s, 1H), 7.07 (s, 1H), 7.05-7.00 (m, 2H), 7.00-6.95 (m, 1H), 5.37 (d, J = 5.6, 12.4 Hz, 1H), 4.43-4.33 (m, 1H), 4.03 (s, 3H), 3.87 (s, 3H), 3.59 (s, 3H), 3.23-3.21 (m, 1H), 3.00 (d, J = 10.8 Hz, 2H), 2.94-2.84 (m, 1H), 2.75-2.60 (m, 2H), 2.23 (d, J = 6.8 Hz, 2H), 2.18-2.06 (m, 4H), 2.02-1.87 (m, 5H), 1.84-1.75 (m, 4H), 1.71-1.62 (m, 1H), 1.19-1.08 (m, 2H) |
| I-194 | BXA | BXB | 773.5 | 11.09 (s, 1H), 9.93 (s, 1H), 9.25 (s, 1H), 8.56 (d, J = 8.0 Hz, 1H), 8.31 (s, 1H), 8.12-8.05 (m, 2H), 7.09 (s, 1H), 7.04-6.96 (m, 3H), 5.37 (dd, J = 5.6, 12.8 Hz, 1H), 4.44-4.32 (m, 1H), 3.87 (s, 3H), 3.59 (s, 3H), 3.01 (d, J = 12.0 Hz, 2H), 2.95-2.83 (m, 1H), 2.76-2.60 (m, 2H), 2.26-2.20 (m, 2H), 2.18-2.07 (m, 4H), 2.05-1.95 (m, 4H), 1.93-1.86 (m, 2H), 1.84-1.76 (m, 4H), 1.70-1.62 (m, 1H), 1.20-1.06 (m, 2H) |
| I-196 | BSS | BXK | 739.1 | 11.10 (s, 1H), 9.84 (s, 1H), 9.04 (s, 1H), 8.83 (d, J = 2.4 Hz, 1H), 8.41 (s, 1H), 8.31 (s, 1H), 8.04 (s, 1H), 7.07 (s, 1H), 7.06-6.97 (m, 3H), 5.38 (dd, J = 5.2, 12.4 Hz, 1H), 4.48-4.35 (m, 1H), 3.87 (s, 3H), 3.61 (s, 3H), 2.97-2.67 (m, 4H), 2.65-2.57 (m, 2H), 2.52 (s, 2H), 2.18 (d, J = 10.8 Hz, 2H), 2.05-1.86 (m, 10H), 1.82 (s, 1H), 1.29-1.15 (m, 3H) |
| I-214 | BUP | BXV | 760.4 | 11.09 (s, 1H), 10.55 (s, 1H), 8.39 (s, 1H), 8.25 (d, J = 1.2 Hz, 1H), 8.04-7.92 (m, 2H), 7.62-7.52 (m, 2H), 7.35 (dd, J = 2.0, 9.2 Hz, 1H), 7.05-6.95 (m, 3H), 5.37 (dd, J = 5.2, 12.8 Hz, 1H), 4.50-4.39 (m, 1H), 3.59 (s, 3H), 3.08 (d, J = 8.4 Hz, 3H), 2.92-2.84 (m, 1H), 2.72 (d, J = |

TABLE 5-continued

Compounds prepared by Method 5.

| I-# | Intermediate Amine | Intermediate Acid | LCMS (ES+) m/z (M + H)+ | 1H NMR (400 MHz, DMSO-d6) δ |
|---|---|---|---|---|
| I-215 | BUP | BXW | 749.3 | 4.0 Hz, 1H), 2.64-2.58 (m, 1H), 2.19-2.14 (m, 4H), 2.03-1.89 (m, 6H), 1.85-1.81 (m, 4H), 1.73-1.65 (m, 1H), 1.23-1.10 (m, 3H) 11.1 (s, 1H), 10.8 (s, 1H), 8.85 (s, 1H), 8.41 (s, 1H), 8.24-8.21 (m, 1H), 7.60 (d, J = 1.2 Hz, 2H), 7.04-6.96 (m, 3H), 5.37 (dd, J = 5.6, 12.4 Hz, 1H), 4.49-4.39 (m, 1H), 3.59 (s, 3H), 3.00 (d, J = 11.2 Hz, 2H), 2.93-2.84 (m, 1H), 2.76-2.68 (m, 1H), 2.65-2.59 (m, 1H), 2.22 (d, J = 7.2 Hz, 2H), 2.16 (d, J = 10.4 Hz, 2H), 2.12-2.06 (m, 2H), 2.02-1.94 (m, 4H), 1.92-1.88 (m, 1H), 1.80 (s, 4H), 1.77-1.61 (m, 2H), 1.19-1.09 (m, 2H) |
| I-247 | BUP | CAM | 715.2 | 11.1 (s, 1H), 10.7 (s, 1H), 8.40 (s, 1H), 8.26 (s, 1H), 8.17-8.13 (m, 1H), 7.59 (d, J = 1.2 Hz, 2H), 7.04-6.97 (m, 3H), 5.37 (dd, J = 5.2, 12.4 Hz, 1H), 4.50-4.41 (m, 1H), 3.60 (s, 3H), 2.90-2.83 (m, 1H), 2.72 (d, J = 4.4 Hz, 1H), 2.64 (d, J = 4.0 Hz, 1H), 2.60 (d, J = 1.2 Hz, 1H), 2.44-2.36 (m, 4H), 2.20-2.15 (m, 2H), 2.02-1.91 (m, 6H), 1.90-1.82 (m, 4H), 1.26-1.12 (m, 4H) |
| I-281 | CCQ | CCM | 775.4 | 11.09 (s, 1H), 10.50 (s, 1H), 8.69 (s, 1H), 8.50-8.44 (m, 1H), 8.43-8.37 (m, 1H), 8.33 (s, 1H), 8.22 (dd, J = 0.8, 7.6 Hz, 1H), 7.16 (s, 1H), 7.02-6.95 (m, 1H), 6.89 (dd, J = 7.8, 13.2 Hz, 2H), 5.35 (dd, J = 5.6, 12.8 Hz, 1H), 4.50-4.37 (m, 1H), 3.98 (s, 3H), 3.64 (s, 3H), 3.62-3.48 (m, 2H), 3.19-2.97 (m, 2H), 2.91-2.73 (m, 3H), 2.72-2.57 (m, 2H), 2.19-2.08 (m, 4H), 2.06-1.95 (m, 4H), 1.94-1.53 (m, 3H), 1.52-1.36 (m, 2H) |
| I-416 | CCJ | CGH | 756.3 | 11.09 (s, 1H), 9.14 (s, 1H), 8.98-8.80 (m, 1H), 8.44-8.32 (m, 2H), 8.27 (s, 1H), 7.84 (s, 1H), 7.05-6.83 (m, 3H), 5.42-5.29 (m, 1H), 4.38-4.21 (m, 1H), 3.81-3.69 (m, 1H), 3.62 (s, 3H), 3.03-2.80 (m, 7H), 2.75-2.61 (m, 4H), 2.19 (d, J = 6.0 Hz, 2H), 2.04-1.95 (m, 1H), 1.94-1.80 (m, 4H), 1.58-1.45 (m, 1H), 1.34 (d, J = 12.8 Hz, 2H), 1.26 (d, J = 6.0 Hz, 6H), 1.07-0.89 (m, 2H) |
| I-417 | CEY | CGH | 755.3 | 11.09 (s, 1H), 9.14 (s, 1H), 8.95-8.83 (m, 1H), 8.42-8.33 (m, 2H), 8.27 (s, 1H), 7.84 (s, 1H), 7.05-6.93 (m, 3H), 5.37 (dd, J = 5.2, 12.4 Hz, 1H), 4.42-4.20 (m, 1H), 3.82-3.65 (m, 1H), 3.63-3.55 (m, 3H), 3.01-2.83 (m, 3H), 2.72-2.59 (m, 3H), 2.16 (d, J = 6.8 Hz, 2H), 2.09-1.97 (m, 3H), 1.87 (t, J = 12.4 Hz, 4H), 1.82-1.70 (m, 4H), 1.58-1.43 (m, 1H), 1.41-1.31 (m, 2H), 1.26 (d, J = 6.4 Hz, 6H), 1.07-0.89 (m, 2H) |
| I-418 | CGB | CGH | 738.5 | 10.53 (s, 1H), 9.42 (s, 1H), 9.14 (s, 1H), 8.94-8.84 (m, 1H), 8.53 (s, 1H), 8.42-8.34 (m, 2H), 8.27 (s, 1H), 7.84 (s, 1H), 7.76-7.68 (m, 1H), 7.62 (d, J = 8.4 Hz, 1H), 7.28 (d, J = 7.2 Hz, 1H), 4.37-4.25 (m, 1H), 3.96-3.85 (m, 1H), 3.80-3.65 (m, 2H), 3.22-3.05 (m, 4H), 3.02-2.91 (m, 1H), 2.81-2.66 (m, 5H), 2.31-2.23 (m, 2H), 1.96-1.84 (m, 4H), 1.62-1.47 (m, 1H), 1.44-1.30 (m, 2H), 1.27 (d, J = 6.0 Hz, 6H), 1.8-0.94 (m, 2H) |

[a]Coupling was run anywhere from 30 min-2 hrs at rt.

Example 4 (Method 6): Synthesis of N-[2-[3-[[4-[5-chloro-1-(2,6-dioxo-3-piperidyl)-3-methyl-2-oxo-benzimidazol-4-yl]-1-piperidyl]methyl]cyclobutyl]-6-methoxy-indazol-5-yl]-6-(trifluoromethyl)pyridine-2-carboxamide (I-87)

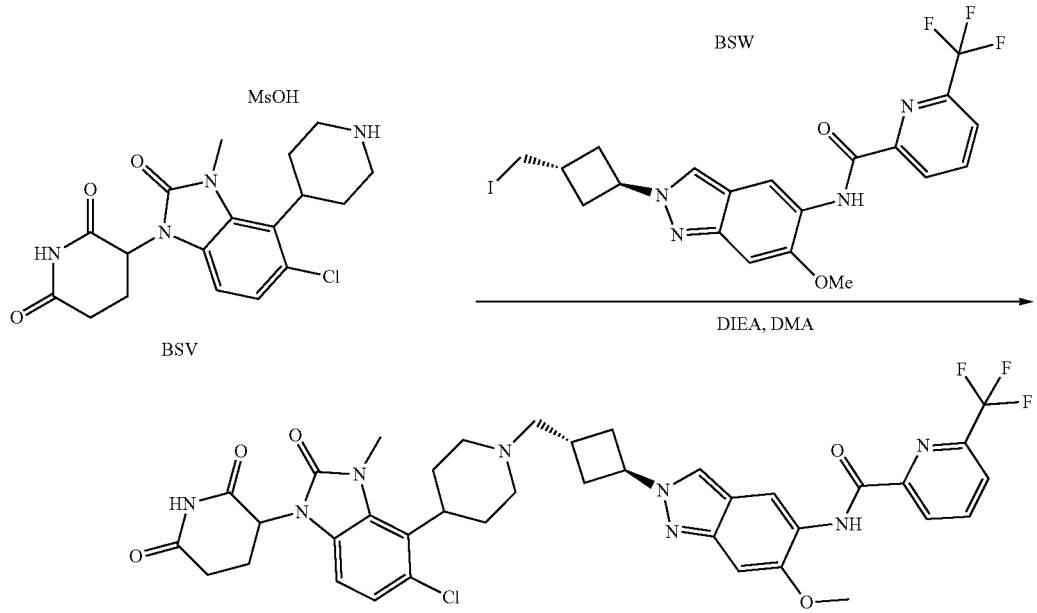

To a mixture of 3-[5-chloro-3-methyl-2-oxo-4-(4-piperidyl)benzimidazol-1-yl]piperidine-2,6-dione (40.0 mg, 106 umol, Intermediate BSV) and N-[2-[3-(iodomethyl)cyclobutyl]-6-methoxy-indazol-5-yl]-6-(trifluoromethyl)pyridine-2-carboxamide (56.2 mg, 106 umol, Intermediate BSW) in DMA (1 mL) was added DIEA (41.1 mg, 318 umol). The reaction mixture was stirred at 70° C. for 24 hours. On completion, the reaction mixture was concentrated in vacuo. The residue was purified by prep-HPLC (column: Welch Xtimate C18 150*25 mm*5 um; mobile phase: [water (0.225% FA)-ACN]; B %: 20%-50%, 11 min) to give the title compound (16.1 mg, 99% purity) as white solid. $^1$H NMR (400 MHz, DMSO-d$_6$) δ 11.12 (s, 1H), 10.52 (s, 1H), 8.70 (s, 1H), 8.48-8.45 (m, 1H), 8.41-8.38 (m, 2H), 8.22 (d, J=7.6 Hz, 1H), 7.20 (s, 1H), 7.12-7.09 (m, 1H), 7.07-7.04 (m, 1H), 5.40-(dd, J=5.2, 13.2 Hz, 1H), 5.22-5.17 (m, 1H), 4.00 (s, 3H), 3.65 (s, 3H), 3.38-3.35 (m, 3H), 2.92-2.83 (m, 2H), 2.77-2.73 (m, 3H), 2.70 (d, J=3.6 Hz, 1H), 2.64 (s, 1H), 2.60 (s, 1H), 2.54-2.52 (m, 3H), 2.44-2.37 (m, 2H), 2.04-1.95 (m, 2H), 1.79-1.67 (m, 2H). LC-MS (ESI$^+$) m/z 779.4 (M+H)$^+$.

The following compounds in Table 6 where prepared according to the same procedure of Method 6 above.

TABLE 6

Compounds prepared by Method 6.

| I-# | Intermediate Amine | Intermediate Iodide | LCMS (ES+) m/z (M + H)$^+$ | 1H NMR (400 MHz, DMSO-d6) δ |
|---|---|---|---|---|
| I-89 | BSP | BSW | 763.4 | 11.10 (s, 1H), 10.54-10.49 (m, 1H), 8.69 (s, 1H), 8.49-8.45 (m, 1H), 8.42 (d, J = 7.6 Hz, 1H), 8.28 (s, 1H), 8.22 (d, J = 8.0 Hz, 1H), 7.21 (s, 1H), 6.99 (dd, J = 4.4, 8.6 Hz, 1H), 6.91-6.82 (m, 1H), 5.41-5.34 (m, 1H), 5.24-5.15 (m, 1H), 3.99 (s, 3H), 3.59 (s, 3H), 3.00 (d, J = 6.4 Hz, 2H), 2.89-2.83 (m, 1H), 2.75-2.68 (m, 3H), 2.65-2.53 (m, 3H), 2.35-2.29 (m, 3H), 2.18-2.03 (m, 5H), 2.02-1.97 (m, 1H), 1.82-1.73 (m, 2H) |
| I-90 | BSY | BSX | 749.4 | 11.09 (s, 1H), 10.53 (s, 1H), 8.64 (s, 1H), 8.58 (s, 1H), 8.46 (s, 1H), 8.44-8.39 (m, 1H), 8.26-8.23 (m, 1H), 7.98 (s, 1H), 7.07-6.94 (m, 3H), 5.37 (dd, J = 5.6, 12.4 Hz, 1H), 5.32-5.26 (m, 1H), 3.59 (s, 3H), 3.02 (d, J = 9.6 Hz, 2H), 2.94-2.84 (m, 1H), 2.75-2.70 (m, 3H), 2.69-2.62 (m, 2H), 2.60 (s, 2H), 2.37 (t, J = 8.4 Hz, 3H), 2.19-2.11 (m, 2H), 2.04-1.96 (m, 1H), 1.85-1.74 (m, 4H) |

TABLE 6-continued

Compounds prepared by Method 6.

| I-# | Intermediate Amine | Intermediate Iodide | LCMS (ES+) m/z (M + H)+ | 1H NMR (400 MHz, DMSO-d6) δ |
|---|---|---|---|---|
| I-91 | BSZ | BSW | 727.5 | 10.55-10.50 (m, 2H), 9.61 (s, 1H), 8.70 (s, 1H), 8.57 (s, 1H), 8.49-8.40 (m, 2H), 8.39 (s, 1H), 8.22 (d, J = 7.6 Hz, 1H), 7.87-7.84 (m, 1H), 7.78 (t, J = 7.6 Hz, 1H), 7.66 (d, J = 7.6 Hz, 1H), 7.21 (s, 1H), 5.26-5.17 (m, 1H), 3.99 (s, 3H), 3.92 (ddd, J = 52, 9.8, 12.4 Hz, 1H), 3.75-3.68 (m, 1H), 3.65-3.55 (m, 1H), 3.06 (d, J = 11.6 Hz, 2H), 3.01-2.93 (m, 1H), 2.80-2.76 (m, 1H), 2.76-2.70 (m, 3H), 2.64 (s, 2H), 2.38-2.28 (m, 4H), 1.97 (s, 4H) |
| I-137 | BQM | BSW | 759.4 | 11.08 (s, 1H), 10.51 (s, 1H), 8.70-8.68 (m, 1H), 8.48-8.45 (m, 1H), 8.43-8.37 (m, 2H), 8.22 (dd, J = 1.2, 7.6 Hz, 1H), 7.20 (s, 1H), 6.90-6.86 (m, 1H), 6.84-6.80 (m, 1H), 5.38-5.29 (m, 1H), 5.25-5.15 (m, 1H), 3.99 (s, 3H), 3.62 (s, 3H), 3.53-3.46 (m, 1H), 3.10-3.04 (m, 2H), 2.91-2.83 (m, 1H), 2.76-2.68 (m, 4H), 2.65-2.59 (m, 2H), 2.46 (s, 3H), 2.39-2.34 (m, 2H), 2.30-2.13 (m, 5H), 2.00-1.94 (m, 1H), 1.74-1.67 (m, 2H) |
| I-138 | BUC | BSW | 775.5 | 11.08 (s, 1H), 10.52 (s, 1H), 8.70 (s, 1H), 8.50-8.45 (m, 1H), 8.44-8.38 (m, 2H), 8.23 (dd, J = 0.8, 8.0 Hz, 1H), 7.22 (s, 1H), 6.94-6.87 (m, 1H), 6.72 (d, J = 8.8 Hz, 1H), 5.33 (dd, J = 5.2, 12.8 Hz, 1H), 5.24-5.16 (m, 1H), 4.00 (s, 3H), 3.77 (s, 3H), 3.57 (s, 3H), 2.99 (d, J = 12.0 Hz, 2H), 2.93-2.83 (m, 1H), 2.74-2.66 (m, 4H), 2.62-2.54 (m, 3H), 2.44-2.31 (m, 5H), 2.10-2.02 (m, 2H), 2.01-1.95 (m, 1H), 1.58 (d, J = 10.8 Hz, 2H) |
| I-139 | AQK | BUF | 794.6 | 11.09 (s, 1H), 10.50 (s, 1H), 8.61 (s, 1H), 8.50 (s, 1H), 8.48-8.38 (m, 2H), 8.24-8.21 (m, 1H), 8.02 (s, 1H), 7.40-7.11 (m, 1H), 7.01-6.95 (m, 1H), 6.94-6.90 (m, 1H), 6.87 (d, J = 7.6 Hz, 1H), 5.40-5.30 (m, 2H), 3.66 (s, 3H), 3.18 (d, J = 11.2 Hz, 2H), 2.94-2.85 (m, 1H), 2.78-2.70 (m, 4H), 2.69-2.66 (m, 3H), 2.66-2.58 (m, 2H), 2.52 (d, J = 2.0 Hz, 1H), 2.40-2.34 (m, 2H), 2.27 (s, 3H), 2.03-1.96 (m, 1H), 1.86 (d, J = 10.4 Hz, 2H), 1.77-1.67 (m, 2H) |
| I-140 | AZK | BUJ | 715.1 | 11.09 (s, 1H), 10.37 (s, 1H), 8.45 (s, 1H), 8.43-8.33 (m, 2H), 8.30 (d, J = 1.2 Hz, 1H), 8.18 (dd, J = 1.2, 7.6 Hz, 1H), 7.69-7.62 (m, 1H), 7.60-7.54 (m, 1H), 7.06-6.94 (m, 3H), 5.42-5.33 (m, 1H), 5.31-5.22 (m, 1H), 3.59 (s, 3H), 3.26-3.19 (m, 2H), 3.02 (d, J = 10.8 Hz, 2H), 2.95-2.83 (m, 1H), 2.76-2.70 (m, 3H), 2.66-2.62 (m, 1H), 2.59 (d, J = 5.2 Hz, 2H), 2.36 (t, J = 8.4 Hz, 2H), 2.14 (dt, J = 3.2, 11.2 Hz, 2H), 2.03-1.95 (m, 1H), 1.85-1.72 (m, 4H) |
| I-141 | BVK | BSW | 763.4 | 11.10 (s, 1H), 10.54-10.49 (m, 1H), 8.69 (s, 1H), 8.49-8.45 (m, 1H), 8.42 (d, J = 7.6 Hz, 1H), 8.28 (s, 1H), 8.22 (d, J = 8.0 Hz, 1H), 7.21 (s, 1H), 6.99 (dd, J = 4.4, 8.6 Hz, 1H), 6.91-6.82 (m, 1H), 5.41-5.34 (m, 1H), 5.24-5.15 (m, 1H), 3.99 (s, 3H), 3.59 (s, 3H), 3.00 (d, J = 6.4 Hz, 2H), 2.89-2.83 (m, 1H), 2.75-2.68 (m, 3H), 2.65-2.53 (m, 3H), 2.35-2.29 (m, 3H), 2.18-2.03 (m, 5H), 2.02-1.97 (m, 1H), 1.82-1.73 (m, 2H) |
| I-142 | BSP | BSX | 767.4 | 11.09 (s, 1H), 10.53 (s, 1H), 8.66 (s, 1H), 8.59 (d, J = 0.4 Hz, 1H), 8.47-8.40 (m, 1H), 8.38 (s, 1H), 8.22 (dd, J = 1.2, 7.6 Hz, 1H), 7.97 (s, 1H), 7.85 (s, 1H), 7.04 (dd, J = 4.2, 8.7 Hz, 1H), 6.91 (dd, J = 8.8, 12.8 Hz, 1H), 5.37 (dd, J = 5.2, 12.6 Hz, 1H), 5.32-5.24 (m, 1H), 3.64 (s, 3H), 3.55 (d, J = 12.4 Hz, 2H), 3.40 (d, J = 7.2 Hz, 2H), 3.20 (t, J = 12.2 Hz, 2H), 3.12-3.01 (m, 1H), 2.94-2.79 (m, 3H), 2.74-2.63 (m, 2H), 2.62-2.54 (m, 2H), 2.41-2.28 (m, 2H), 2.06 (d, J = 13.6 Hz, 2H), 2.02-1.95 (m, 1H) |
| I-143 | BQM | BSX | 763.4 | 11.08 (s, 1H), 10.53 (s, 1H), 8.64 (s, 1H), 8.58 (s, 1H), 8.49 (d, J = 7.6 Hz, 1H), 8.44-8.39 (m, 1H), 8.24 (d, J = 7.6 Hz, 1H), 7.98 (s, 1H), 6.89-6.85 (m, 1H), 6.84-6.80 (m, 1H), 5.37-5.26 (m, 1H), 3.61 (s, 3H), 3.51-3.45 (m, 1H), 3.05-3.00 (m, 2H), 2.90-2.83 (m, 1H), 2.76-2.68 (m, 4H), 2.65-2.61 (m, 1H), 2.60-2.57 (m, 2H), 2.46 (s, 3H), 2.40-2.36 (m, 2H), 2.23 (m, 2H), 2.13-2.07 (m, 2H), 2.00-1.94 (m, 1H), 1.72-1.66 (m, 2H) |

TABLE 6-continued

Compounds prepared by Method 6.

| I-# | Intermediate Amine | Intermediate Iodide | LCMS (ES+) m/z (M + H)+ | 1H NMR (400 MHz, DMSO-d6) δ |
|---|---|---|---|---|
| I-144 | BQL | BSX | 783.4 | 11.12 (s, 1H), 10.53 (s, 1H), 8.64 (s, 1H), 8.58 (s, 1H), 8.51-8.45 (m, 1H), 8.45-8.38 (m, 1H), 8.24 (dd, J = 0.8, 7.6 Hz, 1H), 8.18 (s, 1H), 7.98 (s, 1H), 7.12-7.06 (m, 1H), 7.05-7.00 (m, 1H), 5.39 (dd, J = 5.2, 12.4 Hz, 1H), 5.29 (s, 1H), 3.63 (s, 3H), 3.49 (dd, J = 3.6, 12.0 Hz, 1H), 3.02 (d, J = 11.2 Hz, 2H), 2.92-2.83 (m, 1H), 2.75-2.69 (m, 3H), 2.68-2.62 (m, 2H), 2.59 (s, 3H), 2.37 (t, J = 8.0 Hz, 2H), 2.11 (t, J = 11.2 Hz, 2H), 2.05-1.96 (m, 1H), 1.65 (d, J = 10.0 Hz, 2H) |
| I-145 | BUC | BSX | 779.5 | 11.07 (s, 1H), 10.53 (s, 1H), 8.64 (s, 1H), 8.58 (s, 1H), 8.49-8.45 (m, 1H), 8.45-8.39 (m, 1H), 8.26-8.23 (m, 1H), 8.19 (s, 1H), 7.98 (s, 1H), 6.91 (d, J = 8.4 Hz, 1H), 6.72 (d, J = 8.8 Hz, 1H), 5.35-5.25 (m, 2H), 3.76 (s, 3H), 3.56 (s, 3H), 2.99 (d, J = 11.2 Hz, 2H), 2.92-2.83 (m, 1H), 2.76-2.61 (m, 5H), 2.59 (s, 2H), 2.45-2.35 (m, 5H), 2.07 (t, J = 11.2 Hz, 2H), 2.01-1.93 (m, 1H), 1.58 (d, J = 11.6 Hz, 2H) |
| I-146 | BQM | BUU | 730.2 | 11.07 (s, 1H), 10.21 (s, 1H), 9.10 (s, 1H), 8.65 (s, 1H), 8.54-8.45 (m, 2H), 8.42 (t, J = 8.0 Hz, 1H), 8.24 (d, J = 7.6 Hz, 1H), 6.91-6.79 (m, 2H), 5.43-5.29 (m, 2H), 3.62 (s, 3H), 3.53-3.41 (m, 2H), 3.07-3.01 (m, 2H), 2.92-2.82 (m, 1H), 2.80-2.70 (m, 3H), 2.68-2.57 (m, 4H), 2.46 (s, 3H), 2.29-2.21 (m, 2H), 2.21-2.07 (m, 3H), 2.02-1.93 (m, 1H), 1.74-1.64 (m, 2H) |
| I-147 | BSP | BUU | 734.2 | 11.10 (s, 1H), 10.21 (s, 1H), 9.10 (s, 1H), 8.65 (s, 1H), 8.51-8.46 (m, 2H), 8.45-8.39 (m, 1H), 8.23 (dd, J = 0.8, 7.6 Hz, 1H), 6.99 (dd, J = 4.4, 8.4 Hz, 1H), 6.86 (dd, J = 8.4, 12.9 Hz, 1H), 5.41-5.34 (m, 2H), 3.59 (s, 3H), 3.01 (d, J = 6.0 Hz, 2H), 2.92-2.83 (m, 1H), 2.79-2.73 (m, 3H), 2.71 (d, J = 4.4 Hz, 1H), 2.65-2.57 (m, 3H), 2.52 (d, J = 2.0 Hz, 1H), 2.41 (t, J = 8.4 Hz, 2H), 2.12 (s, 4H), 1.99 (td, J = 5.2, 10.4 Hz, 1H), 1.77 (d, J = 3.4 Hz, 2H) |
| I-148 | BQM | BUJ | 729.5 | 11.08 (s, 1H), 10.38 (s, 1H), 8.46 (s, 1H), 8.43-8.33 (m, 2H), 8.31 (d, J = 1.2 Hz, 1H), 8.18 (dd, J = 1.2, 7.5 Hz, 1H), 7.68-7.63 (m, 1H), 7.60-7.55 (m, 1H), 6.98-6.73 (m, 2H), 5.39-5.20 (m, 2H), 3.62 (s, 3H), 3.52-3.41 (m, 2H), 3.03 (d, J = 10.8 Hz, 2H), 2.90-2.82 (m, 1H), 2.76-2.69 (m, 3H), 2.67 (dd, J = 1.6, 3.6 Hz, 1H), 2.59 (d, J = 6.0 Hz, 2H), 2.46 (s, 3H), 2.42-2.32 (m, 3H), 2.27-2.17 (m, 2H), 2.17-2.04 (m, 2H), 2.01-1.94 (m, 1H), 1.69 (d, J = 11.2 Hz, 2H) |
| I-149 | BSV | BUU | 750.5 | 11.12 (s, 1H), 10.21 (s, 1H), 9.10 (s, 1H), 8.65 (s, 1H), 8.50-8.47 (m, 2H), 8.42 (t, J = 7.6 Hz, 1H), 8.25-8.22 (m, 1H), 7.11-7.07 (m, 1H), 7.05-7.02 (m, 1H), 5.42-5.36 (m, 2H), 3.63 (s, 3H), 3.53-3.47 (m, 1H), 3.02 (d, J = 10.4 Hz, 2H), 2.93-2.83 (m, 1H), 2.77-2.72 (m, 3H), 2.68-2.62 (m, 3H), 2.60 (s, 3H), 2.43-2.39 (m, 2H), 2.11 (t, J = 10.8 Hz, 2H), 2.03-1.98 (m, 1H), 1.65 (d, J = 11.6 Hz, 2H) |
| I-150 | BQL | BUJ | 749.1 | 11.12 (s, 1H), 10.37 (s, 1H), 8.45 (s, 1H), 8.42-8.34 (m, 2H), 8.30 (s, 1H), 8.23-8.15 (m, 1H), 7.68-7.62 (m, 1H), 7.60-7.54 (m, 1H), 7.16-6.99 (m, 2H), 5.44-5.18 (m, 2H), 3.63 (s, 3H), 3.54-3.49 (m, 1H), 3.02 (d, J = 10.4 Hz, 2H), 2.89-2.83 (m, 1H), 2.72 (d, J = 4.4 Hz, 3H), 2.65 (d, J = 11.6 Hz, 2H), 2.59 (s, 2H), 2.40-2.31 (m, 4H), 2.10 (t, J = 10.8 Hz, 2H), 2.02-1.97 (m, 1H), 1.65 (d, J = 12.0 Hz, 2H) |
| I-151 | BVK | BUJ | 733.5 | 11.10 (s, 1H), 10.37 (s, 1H), 8.45 (s, 1H), 8.42-8.38 (m, 1H), 8.38-8.33 (m, 1H), 8.30 (s, 1H), 8.17 (dd, J = 1.2, 7.6 Hz, 1H), 7.68-7.63 (m, 1H), 7.68 (dd, J = 1.6, 8.8 Hz, 1H), 7.03-6.96 (m, 1H), 6.90-6.82 (m, 1H), 5.41-5.33 (m, 1H), 5.3-5.21 (m, J = 6.8 Hz, 1H), 3.59 (s, 3H), 3.05-2.96 (m, 2H), 2.92-2.82 (m, 1H), 2.75-2.69 (m, 3H), 2.69-2.61 (m, 2H), 2.60-2.56 (m, 2H), 2.52 (s, 1H), 2.40-2.35 (m, 2H), 2.15-2.05 (m, 4H), 2.04-1.95 (m, 1H), 1.82-1.74 (m, 2H) |
| I-152 | BVA | BUJ | 745.2 | 11.08 (s, 1H), 10.38 (s, 1H), 8.47 (s, 1H), 8.44-8.35 (m, 2H), 8.31 (d, J = 1.2 Hz, 1H), 8.23-8.16 (m, 1H), 7.70-7.64 (m, 1H), 7.58 (dd, J = 2.0, 9.2 |

TABLE 6-continued

Compounds prepared by Method 6.

| I-# | Inter-mediate Amine | Inter-mediate Iodide | LCMS (ES+) m/z (M + H)+ | 1H NMR (400 MHz, DMSO-d6) δ |
|---|---|---|---|---|
| | | | | Hz, 1H), 6.91 (d, J = 8.4 Hz, 1H), 6.73 (d, J = 8.8 Hz, 1H), 5.39-5.22 (m, 2H), 3.77 (s, 3H), 3.57 (s, 3H), 2.99 (d, J = 10.4 Hz, 2H), 2.94-2.83 (m, 1H), 2.80-2.64 (m, 5H), 2.59 (d, J = 5.6 Hz, 2H), 2.44-2.33 (m, 5H), 2.12-1.95 (m, 3H), 1.59 (d, J = 11.6 Hz, 2H) |
| I-235 | AZK | CAD | 762.3 | 11.09 (s, 1H), 10.52 (s, 1H), 9.02 (s, 1H), 8.55-8.38 (m, 2H), 8.29-8.20 (m, 2H), 7.76 (s, 1H), 7.10-6.90 (m, 3H), 4.05 (s, 3H), 4.01-3.89 (m, 1H), 3.59 (s, 3H), 2.99 (d, J = 11.6 Hz, 4H), 2.76-2.62 (m, 4H), 2.36-2.23 (m, 4H), 2.13 (d, J = 2.4 Hz, 4H), 1.79 (d, J = 1.6 Hz, 4H) |
| I-270 | AZK | BUU | 716.5 | 11.09 (s, 1H), 10.21 (s, 1H), 9.10 (s, 1H), 8.65 (s, 1H), 8.52-8.46 (m, 2H), 8.42 (t, J = 7.6 Hz, 1H), 8.26-8.20 (m, 1H), 7.07-6.93 (m, 3H), 5.43-5.34 (m, 2H), 3.59 (s, 3H), 3.21 (s, 1H), 3.02 (d, J = 10.4 Hz, 2H), 2.91-2.84 (m, 1H), 2.80-2.68 (m, 4H), 2.65-2.57 (m, 3H), 2.42-2.37 (m, 2H), 2.19-2.10 (m, 2H), 2.03-1.96 (m, 1H) |
| I-292[b] | CEL | CEI | 801.4 | 11.09 (s, 1H), 10.51 (s, 1H), 8.69 (s, 1H), 8.50-8.44 (m, 1H), 8.44-8.37 (m, 1H), 8.34 (s, 1H), 8.22 (d, J = 7.6 Hz, 1H), 7.17 (s, 1H), 7.09-6.89 (m, 3H), 5.37 (dd, J = 5.2, 12.8 Hz, 1H), 4.44-4.31 (m, 1H), 3.98 (s, 3H), 3.62 (s, 3H), 3.57-3.46 (m, 1H), 2.96-2.79 (m, 2H), 2.78-2.69 (m, 1H), 2.62 (d, J = 17.2 Hz, 2H), 2.24-2.13 (m, 3H), 2.05-1.86 (m, 4H), 1.86-1.72 (m, 4H), 1.67 (dd, J = 1.2, 11.6 Hz, 1H), 1.60-1.44 (m, 2H), 1.26-1.13 (m, 2H), 1.08 (d, J = 18.0 Hz, 6H) |
| I-305[c] | CER | CES | 786.3 | 11.10 (s, 1H), 10.13 (s, 1H), 8.53 (s, 1H), 8.45-8.35 (m, 3H), 8.22-8.21 (m, 1H), 7.52 (s, 1H), 7.10-7.03 (m, 1H), 7.02-6.94 (m, 2H), 5.39 (dd, J = 4.4, 12.4 Hz, 1H), 4.54-4.42 (m, 1H), 3.66 (s, 3H), 3.64-3.55 (m, 2H), 3.33-3.26 (m, 3H), 3.14-3.09 (m, 1H), 3.06-2.96 (m, 1H), 2.96-2.79 (m, 2H), 2.78-2.63 (m, 2H), 2.41 (s, 3H), 2.30-2.15 (m, 3H), 2.09-1.84 (m, 5H), 1.51 (s, 3H), 1.45 (s, 3H), 1.41-1.23 (m, 2H) |
| I-306[c] | CER | CEI | 802.3 | 11.10 (s, 1H), 10.50 (s, 1H), 8.69 (s, 1H), 8.49-8.44 (m, 1H), 8.43-8.38 (m, 1H), 8.35 (s, 1H), 8.22 (d, J = 7.6 Hz, 1H), 7.15 (s, 1H), 7.08-6.88 (m, 3H), 5.43-5.31 (m, 1H), 4.54-4.27 (m, 1H), 3.98 (s, 3H), 3.67 (s, 3H), 3.62 (d, J = 4.0 Hz, 1H), 3.20-2.97 (m, 2H), 2.96-2.79 (m, 2H), 2.73-2.64 (m, 3H), 2.20 (s, 3H), 2.09-1.73 (m, 6H), 1.66-1.19 (m, 6H), 1.10 (s, 4H) |
| I-324[d] | CBC | CBB | 772.2 | 11.09 (s, 1H), 10.36 (s, 1H), 8.42-8.33 (m, 3H), 8.29 (d, J = 1.2 Hz, 1H), 8.17 (dd, J = 1.2, 7.6 Hz, 1H), 7.64-7.59 (m, 1H), 7.57-7.51 (m, 1H), 7.02-6.84 (m, 3H), 5.36 (dd, J = 5.2, 12.8 Hz, 1H), 4.45 (t, J = 11.6 Hz, 1H), 3.68 (s, 3H), 3.16-3.08 (m, 1H), 2.94-2.84 (m, 1H), 2.80-2.58 (m, 7H), 2.24-2.12 (m, 3H), 2.02-1.77 (m, 5H), 1.59-1.48 (m, 1H), 1.46-1.23 (m, 2H), 1.10 (s, 6H), 0.86 (t, J = 7.2 Hz, 1H) |
| I-421 | BVA | BUU | 746.3 | 11.08 (s, 1H), 10.21 (s, 1H), 9.11 (s, 1H), 8.65 (s, 1H), 8.52-8.46 (m, 2H), 8.42 (t, J = 8.0 Hz, 1H), 8.24 (d, J = 8.0 Hz, 1H), 6.90 (d, J = 8.8 Hz, 1H), 6.72 (d, J = 8.8 Hz, 1H), 5.43-5.27 (m, 2H), 3.76 (s, 3H), 3.56 (s, 3H), 3.03-2.94 (m, 2H), 2.93-2.82 (m, 1H), 2.79-2.72 (m, 3H), 2.71-2.57 (m, 4H), 2.44-2.35 (m, 4H), 2.13-2.02 (m, 2H), 2.01-1.92 (m, 1H), 1.61-1.54 (m, 2H), 1.46-1.31 (m, 1H) |

TABLE 6-continued

Compounds prepared by Method 6.

| I-# | Inter-mediate Amine | Inter-mediate Iodide | LCMS (ES+) m/z (M + H)+ | 1H NMR (400 MHz, DMSO-d6) δ |
|---|---|---|---|---|
| I-424[b] | CHA | CEI | 801.3 | 11.09 (s, 1H), 10.85 (s, 1H), 10.51 (s, 1H), 8.69 (s, 1H), 8.49-8.44 (m, 1H), 8.44-8.38 (m, 1H), 8.34 (s, 1H), 8.22 (d, J = 7.6 Hz, 1H), 7.17 (s, 1H), 7.06-6.79 (m, 3H), 5.37 (dd, J = 5.2, 12.4 Hz, 1H), 4.44-4.31 (m, 1H), 3.98 (s, 3H), 3.62 (s, 2H), 3.54-3.53 (s, 2H), 2.98-2.68 (m, 3H), 2.63-2.61 (m, 2H), 2.23-2.12 (m, 3H), 2.04-1.96 (m, 1H), 1.95-1.73 (m, 6H), 1.71-1.61 (m, 1H), 1.60-1.44 (m, 2H), 1.25-0.96 (m, 9H) |

[a]The coupling was run at 60-90° C. for 12-32 hrs.
[b]K₂CO₃ used as the base for the coupling with 4 Å molecular sieves in DMA at 90° C. for 16 hrs.
[c]TEA and KI in DMA was stirred at 90° C. for 16 hrs. The coupled product was deprotected with TfOH in TFA at 70° C. for 2 hrs, then purified via prep HPLC to give the final cmpd.
[d]Cs₂CO₃ in DMF was used for the coupling at 60° C. for 16 hrs.

Example 5 (Method 7): 6-cyano-N-[2-[4-[[4-[1-(2,6-dioxo-3-piperidyl)-3-methyl-2-oxo-benzimidazol-4-yl]-1-piperidyl]methyl]cyclohexyl]-6-methoxy-indazol-5-yl]pyrazolo[1,5-a] pyrimidine-3-carboxamide (I-153)

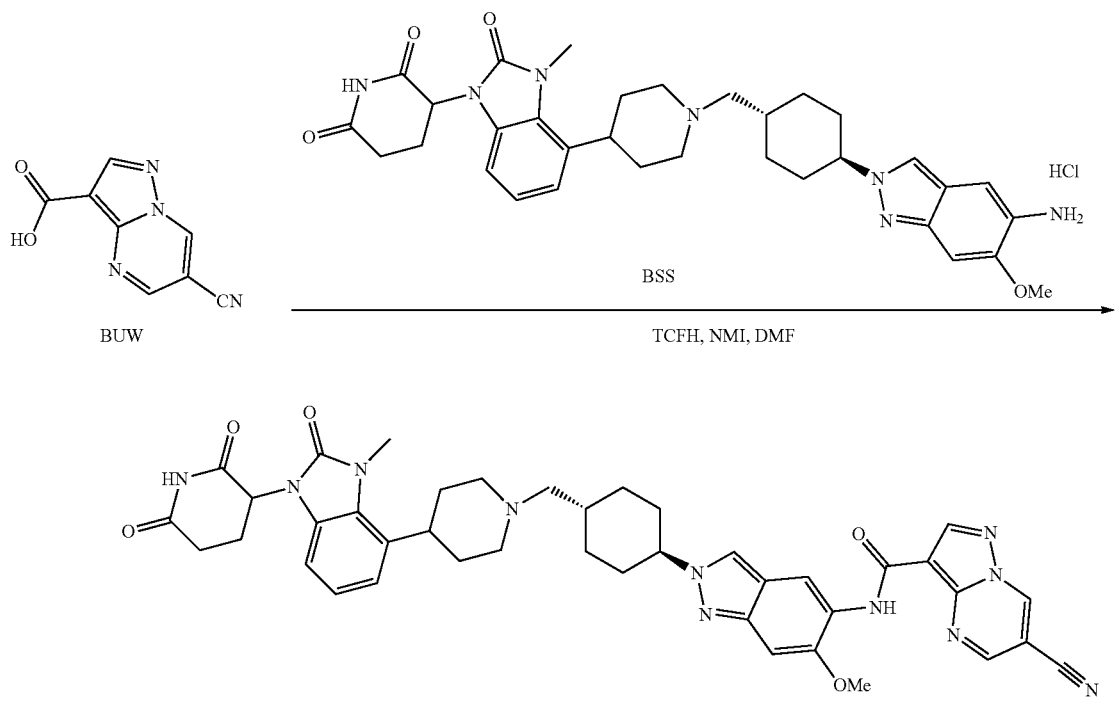

To a solution of 3-[4-[1-[[4-(5-amino-6-methoxy-indazol-2-yl)cyclohexyl]methyl]-4-piperidyl]-3-methyl-2-oxo-benzimidazol-1-yl]piperidine-2,6-dione (35.0 mg, 55.0 umol, HCl, Intermediate BSS) in DMF (2 mL) was added 6-cyanopyrazolo[1,5-a]pyrimidine-3-carboxylic acid (10.3 mg, 55.0 umol, Intermediate BUW) and 1-methylimidazole (13.5 mg, 165 umol). Then [chloro(dimethylamino)methylene]-dimethyl-ammonium; hexafluorophosphate (18.5 mg, 66.0 umol) in DMF (1 mL) was added at 0° C. Next, the mixture was stirred at 20° C. for 2 hrs. On completion, the mixture was quenched with H₂O 0.5 mL and purified by pre-HPLC (column: Phenomenex luna C18 150*25 mm*10 um; mobile phase: [water (0.225% FA)-ACN]; B %: 10%-40%, 11.5 min) to give the title compound (7.32 mg, 9.26 umol, 16% yield) as yellow solid. ¹H NMR (400 MHz, DMSO-d₆) δ 11.11 (s, 1H), 10.43 (s, 1H), 10.25 (d, J=2.0 Hz, 1H), 9.28 (d, J=2.0 Hz, 1H), 8.92 (s, 1H), 8.68 (s, 1H), 8.31 (s, 1H), 7.11 (s, 1H), 7.09-6.94 (m, 3H), 5.44-5.34 (m, 1H), 4.49-4.36 (m, 1H), 4.04 (s, 3H), 3.63 (s, 6H), 3.07-2.85 (m, 3H), 2.77-2.65 (m, 2H), 2.24-2.17 (m, 2H), 2.14-1.83 (m, 12H), 1.36-1.22 (m, 2H). LC-MS (ESI⁺) m/z 770.3 (M+H)⁺.

TABLE 5

Compounds synthesized via Method 7, with the corresponding amine and acid.

| I-# | Inter-mediate Amine | Inter-mediate Acid | LCMS (ES+) m/z (M + H)+ | 1HNMR (400 MHz, DMSO-d6) δ |
|---|---|---|---|---|
| I-154 | BYE | BUW | 758.3 | 11.09 (s, 1H), 10.25 (d, J = 2.0 Hz, 1H), 9.97 (d, J = 3.2 Hz, 1H), 9.23 (d, J = 2.0 Hz, 1H), 8.95 (s, 1H), 8.63-8.58 (m, 1H), 8.47 (s, 1H), 7.55 (d, J = 12.0 Hz, 1H), 7.07-6.93 (m, 3H), 5.37 (dd, J = 6.0, 13.2 Hz, 1H), 4.51-4.37 (m, 1H), 3.59 (s, 3H), 3.22-3.19 (m, 1H), 3.05-2.95 (m, 2H), 2.94-2.82 (m, 1H), 2.78-2.68 (m, 1H), 2.66-2.57 (m, 1H), 2.25-2.20 (m, 2H), 2.19-2.12 (m, 2H), 2.12-2.03 (m, 2H), 2.03-1.95 (m, 3H), 1.95-1.86 (m, 2H), 1.85-1.73 (m, 4H), 1.71-1.61 (m, 1H), 1.21-1.06 (m, 2H) |
| I-344[a] | AML | AMY | 869.3 | 1.48 (J = 3.20 Hz, 1 H) 1.55-1.71 (m, 12 H) 1.73-1.90 (m, 5 H) 1.97-2.09 (m, 4 H) 2.11-2.20 (m, 2 H) 2.57-2.63 (m, 3 H) 2.73-2.81 (m, 1 H) 2.83-2.95 (m, 1 H) 3.45-3.55 (m, 2 H) 4.12-4.25 (m, 1 H) 4.41-4.54 (m, 1 H) 5.06 (dd, J = 12..4, 5.6 Hz, 1 H) 5.93 (s, 1 H) 6.49 (d, J = 6.0 Hz, 1 H) 6.96-7.13 (m, 2 H) 7.51-7.66 (m, 2 H) 8.16 (d, J = 7, 2 Hz, 1 H) 8.31-8.39 (m, 2 H) 8.42-8.49 (m, 1 H) 8.71 (s, 1 H) 11.09 (s, 1 H) 12.35 (s, 1 H) |
| I-346[a] | AML | AXQ | 841.3 | 11.09 (s, 1H), 10.50 (s, 1H), 8.69 (s, 1H), 8.53-8.36 (m, 2H), 8.32 (d, J = 2.1 Hz, 1H), 8.22 (d, J = 7.6 Hz, 1H), 7.65-7.53 (m, 1H), 7.14 (s, 1H), 7.10-6.99 (m, 2H), 6.49 (d, J = 6.6 Hz, 1H), 5.10-5.03 (m, 1H), 4.52-4.33 (m, 1H), 4.25-4.12 (m, 1H), 3.98 (s, 3H), 3.57-3.34 (m, 4H), 2.97-2.83 (m, 1H), 2.80-2.70 (m, 1H), 2.64-2.54 (m, 2H), 2.20-2.11 (m, 3H), 2.06-1.99 (m, 3H), 1.90-1.73 (m, 5H), 1.70-1.63 (m, 2H), 1.62-1.55 (m, 3H), 1.53-1.45 (m, 1H) |

[a]ACN was used as the solvent for the coupling.

Examples 6: Synthesis of N-[2-[4-[[[4-[1-(2,6-di-oxo-3-piperidyl)-3-methyl-2-oxo-benzimidazol-4-yl]cyclohexyl]-methyl-amino] methyl]cyclohexyl]-6-methoxy-indazol-5-yl]-6-(trifluoromethyl)pyridine-2-carboxamide (I-5) and N-[2-[4-[[[4-[1-(2,6-dioxo-3-piperidyl)-3-methyl-2-oxo-benzimidazol-4-yl]cyclohexyl]-methyl-amino] methyl]cyclohexyl]-6-methoxy-indazol-5-yl]-6-(trifluoromethyl)pyridine-2-carboxamide (I-6)

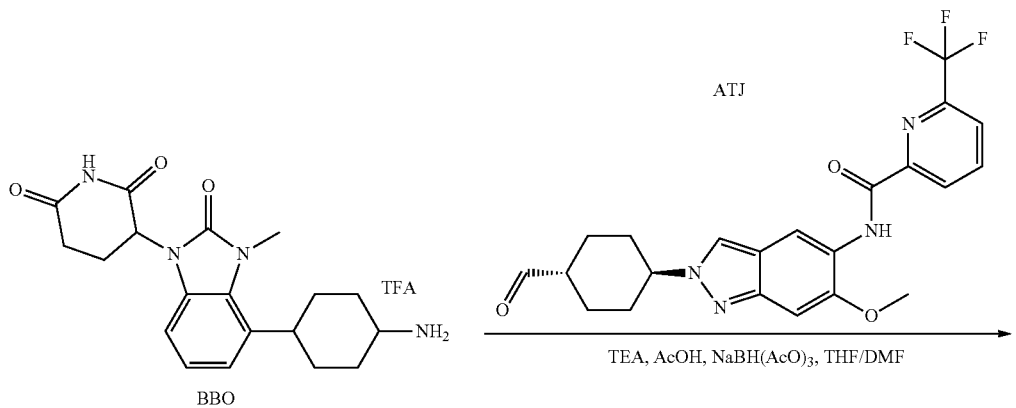

-continued

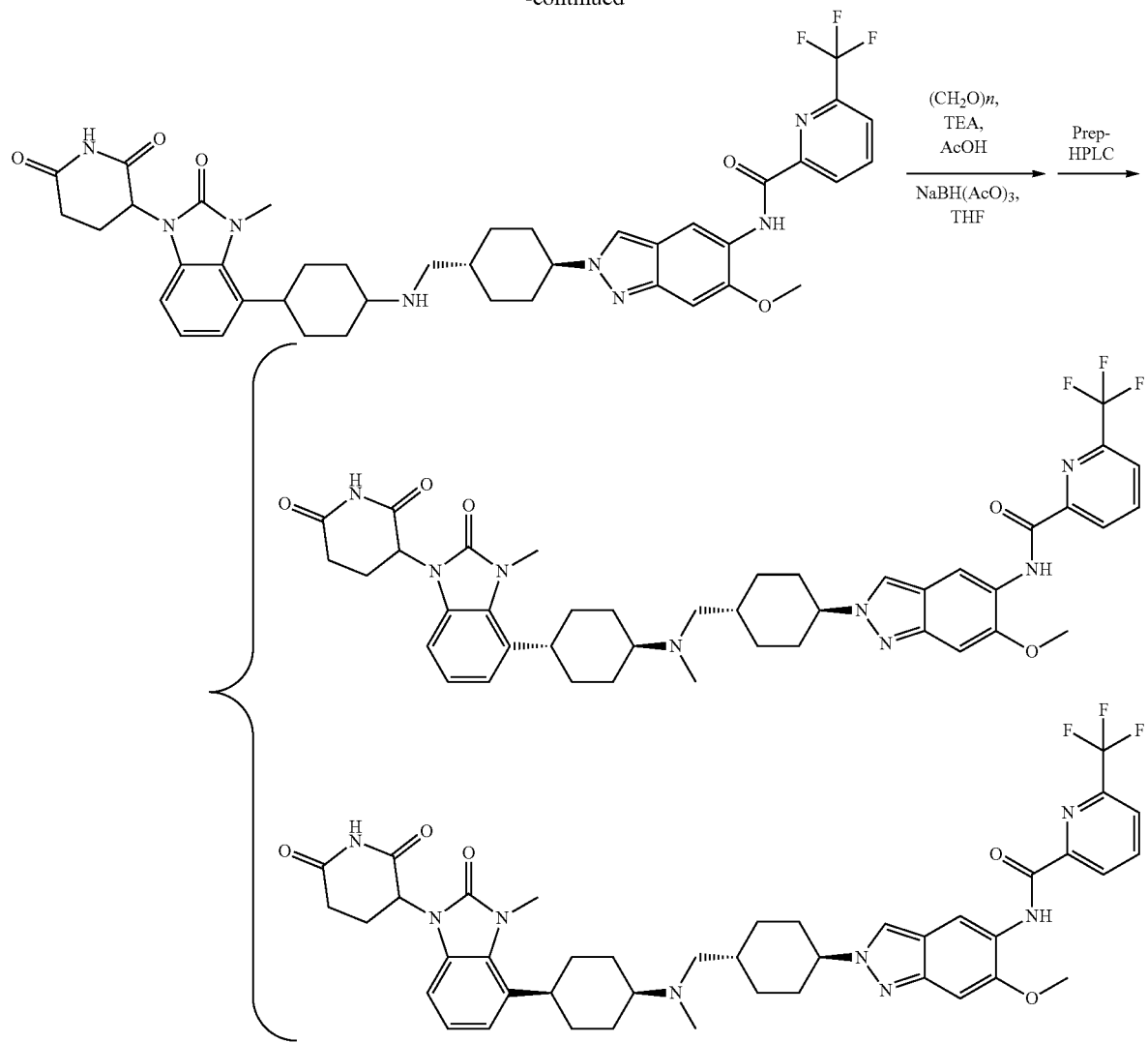

Step 1—N-[2-[4-[[[4-[1-(2,6-dioxo-3-piperidyl)-3-methyl-2-oxo-benzimidazol-4-yl]cyclohexyl]amino]methyl]cyclohexyl]-6-methoxy-indazol-5-yl]-6-(trifluoromethyl)pyridine-2-carboxamide To a solution of 3-[4-(4-aminocyclohexyl)-3-methyl-2-oxo-benzimidazol-1-yl]piperidine-2,6-dione (790 mg, 1.68 mmol, TFA, Intermediate BBO) in THF (5 mL) and DMF (1 mL) was added TEA (113 mg, 1.12 mmol). Then HOAc (134 mg, 2.24 mmol) and N-[2-(4-formylcyclohexyl)-6-methoxy-indazol-5-yl]-6-(trifluoromethyl)pyridine-2-carboxamide (0.5 g, 1.12 mmol, Intermediate ATJ) was added at 0° C., then the mixture was stirred at −10° C. for 0.5 hr. Next, NaBH(OAc)$_3$ (712 mg, 3.36 mmol) was added and the mixture was stirred at −10° C. for 1 hr. On completion, the reaction mixture was quenched by addition water (0.1 mL) and concentrated in vacuo. The crude product was purified by reversed phase flash (0.1% FA condition) to give the title compound (0.85 g, 86% yield) as white solid. LC-MS (ESI$^+$) m/z 787.4 (M+H)$^+$.

Step 2—N-[2-[4-[[[4-[1-(2,6-dioxo-3-piperidyl)-3-methyl-2-oxo-benzimidazol-4-yl]cyclohexyl]-methyl-amino]methyl]cyclohexyl]-6-methoxy-indazol-5-yl]-6-(trifluoromethyl)pyridine-2-carboxamide and N-[2-[4-[[[4-[1-(2,6-dioxo-3-piperidyl)-3-methyl-2-oxo-benzimidazol-4-yl]cyclohexyl]-methyl-amino]methyl]cyclohexyl]-6-methoxy-indazol-5-yl]-6-(trifluoromethyl)pyridine-2-carboxamide A solution of N-[2-[4-[[[4-[1-(2,6-dioxo-3-piperidyl)-3-methyl-2-oxo-benzimidazol-4-yl]cyclohexyl]amino]methyl]cyclohexyl]-6-methoxy-indazol-5-yl]-6-(trifluoromethyl)pyridine-2-carboxamide (0.8 g, 1.02 mmol), TEA (10.2 mg, 101 umol), HOAc (12.2 mg, 203 umol) and (HCHO)n (0.04 g, 10.1 mmol) in THF (5 mL) was stirred at 25° C. for 12 hr. Then NaBH(OAc)$_3$ (430 mg, 2.03 mmol) was added and the mixture was stirred at 25° C. for 12 hr. On completion, the reaction mixture was quenched by addition water (0.5 mL) and concentrated in vacuo. The residue was purified by prep-HPLC (column: Phenomenex luna C18 150*40 mm*15 um; mobile phase: [water (0.225% FA)-ACN]; B %: 22%-52%, 10 min) and prep-HPLC(column: Waters Vinridis Silica 2-EP OBD 50*150 mm*5 um; mobile phase: [n-Heptane-IPA (0.1% NH$_3$·H$_2$O)]; B %: 20%-60%, 10 min) to give two impure product. N-[2-[4-[[[4-[1-(2,6-dioxo-3-piperidyl)-3-methyl-2-oxo-benzimidazol-4-yl]cyclohexyl]-methyl-amino]methyl]cyclohexyl]-6-methoxy-indazol-5-yl]-6-(trifluoromethyl)pyridine-2-carboxamide (0.06 g, 6% yield) was isolated as a white solid. This product was re-purified by prep-HPLC (column: 3 Phenomenex Luna C18 75*30 mm*3 um; mobile phase: [water (0.225% FA)-ACN]; B %: 24%-44%, 8 min) to give the title compound (21.0 mg, 42% yield) as white solid. $^1$H NMR (400 MHz, DMSO-d$_6$) δ 11.09 (s, 1H), 10.50 (s, 1H), 8.68 (s, 1H), 8.45 (d, J=7.6 Hz, 1H), 8.40 (d, J=7.6 Hz, 1H), 8.33 (s, 1H), 8.23-8.20 (m, 1H), 7.15 (s, 1H), 7.03-6.97 (m, 3H), 5.37 (dd, J=5.2, 12.8 Hz, 1H), 4.38-4.35 (m, 1H), 3.98 (s, 3H), 3.59 (s, 3H), 3.24-3.20 (m, 2H), 2.95-2.83 (m, 1H), 2.77-2.60 (m, 2H), 2.33-2.30 (m, 2H), 2.27 (s, 3H), 2.15 (d, J=10.8 Hz, 2H), 2.04-1.87 (m, 9H), 1.70-1.40 (m, 5H), 1.18-1.03 (m, 2H); LC-MS (ESI$^+$) m/z 801.3 (M+H)$^+$. N-[2-[4-[[[4-[1-(2,6-dioxo-3-piperidyl)-3-methyl-2-oxo-benzimidazol-4-yl]cyclohexyl]amino]methyl]cyclohexyl]-6-methoxy-indazol-5-yl]-6-(trifluoromethyl)pyridine-2-carboxamide (0.06 g, 7% yield) was isolated as white solid. This product was re-purified by prep-HPLC (column: 3 Phenomenex Luna C18 75*30 mm*3 um; mobile phase: [water (0.225% FA)-ACN]; B %: 26%-46%, 8 min) to give the title compound (41.0 mg, 68% yield) as white solid. $^1$H NMR (400 MHz, DMSO-d$_6$) δ 11.08 (s, 1H), 10.50 (s, 1H), 8.68 (s, 1H), 8.45 (d, J=7.6 Hz, 1H), 8.40 (d, J=7.6 Hz, 1H), 8.32 (s, 1H), 8.23-8.20 (m, 1H), 7.16 (s, 1H), 7.03-6.93 (m, 3H), 5.35 (dd, J=5.2, 12.8 Hz, 1H), 4.41-4.35 (m, 1H), 3.97 (s, 3H), 3.59 (s, 3H), 3.24-3.20 (m, 2H), 2.89-2.86 (m, 1H), 2.72-2.67 (m, 1H), 2.65-2.62 (m, 1H) 2.26-2.23 (m, 2H), 2.20 (s, 3H), 2.16-2.13 (m, 2H), 2.04-1.94 (m, 5H), 1.92-1.89 (m, 4H), 1.60-1.55 (m, 5H), 1.16-1.10 (m, 2H); LC-MS (ESI$^+$) m/z 801.3 (M+H)$^+$. The absolute stereochemistry of the trans and cis-isomers was randomly assigned.

Example 7: Synthesis of 6-(1,1-Difluoroethyl)-N-[2-[4-[[6-[2-[[2-(2,6-dioxo-3-piperidyl)-1,3-dioxo-isoindolin-4-yl]amino]ethyl]-2-azaspiro[3.3]heptan-2-yl]methyl]cyclohexyl]-6-methoxy-indazol-5-yl]pyridine-2-carboxamide (I-11)

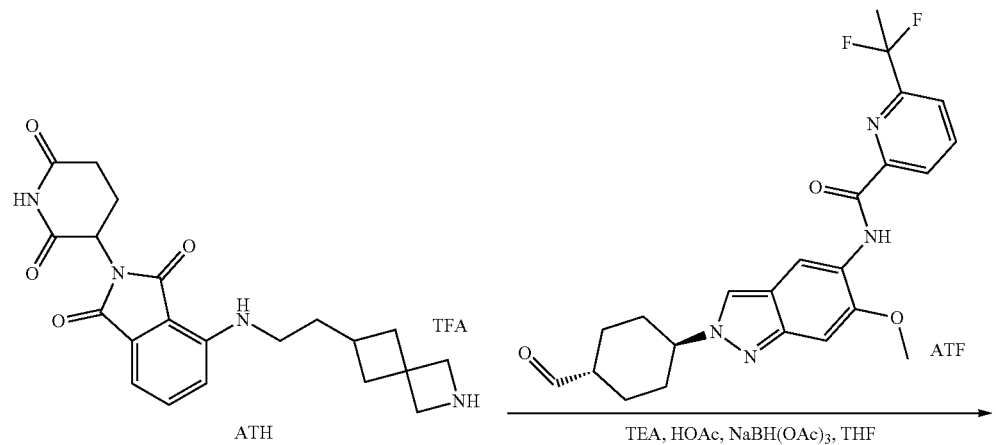

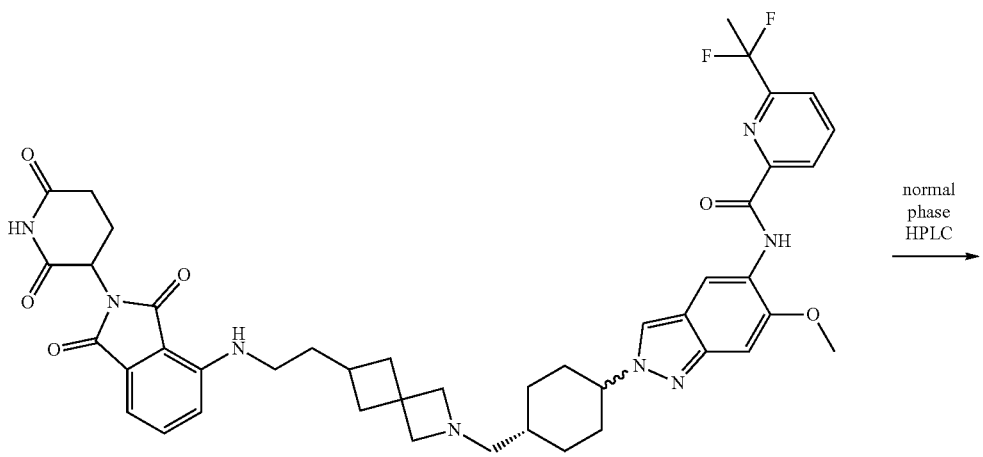

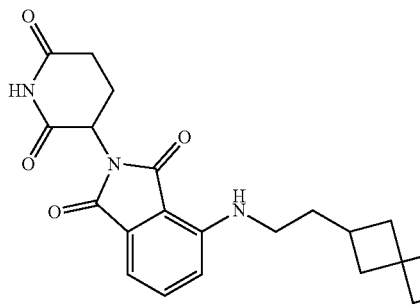
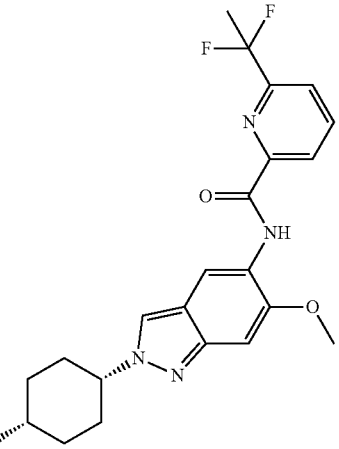

Step 1—6-(1,1-Difluoroethyl)-N-[2-[4-[[6-[2-[[2-(2, 6-dioxo-3-piperidyl)-1,3-dioxo-isoindolin-4-yl] amino]ethyl]-2-azaspiro[3.3]heptan-2-yl]methyl] cyclohexyl]-6-methoxy-indazol-5-yl]pyridine -2-carboxamide To a mixture of 4-[2-(2-azaspiro[3.3]heptan-6-yl)ethyl-amino]-2-(2,6-dioxo-3-piperidyl)isoindoline-1,3-dione (50 mg, 97.9 umol, TFA, Intermediate ATH) in THF (1 mL) was added TEA (19.8 mg, 195 umol) and the mixture was stirred at 25° C. for 6 mins. Then HOAc (11.7 mg, 195 umol) and 6-(1,1-difluoroethyl)-N-[2-(4-formylcyclohexyl)-6-methoxy-indazol-5-yl]pyridine-2-carboxamide (43.3 mg, 97.9 umol, Intermediate ATF) and NaBH(OAc)₃ (41.5 mg, 195 umol) was added and the mixture was stirred 50° C. for 16 hrs. On completion, the reaction mixture was quenched with water (1 mL) and extracted with DCM (3×5 mL). The combined organic lays was dried over Na₂SO₄, filtered and concentrated in vacuo to give the title compound (65.0 mg, crude) as yellow oil. The crude product contained some of cis-isomer. LC-MS (ESI⁺) m/z 823.5 (M+H)⁺.

Step 2—6-(1,1-Difluoroethyl)-N-[2-[4-[[6-[2-[[2-(2, 6-dioxo-3-piperidyl)-1,3-dioxo-isoindolin-4-yl] amino]ethyl]-2-azaspiro[3.3]heptan-2-yl]methyl] cyclohexyl]-6-methoxy-indazol-5-yl]pyridine-2-carboxamide 6-(1,1-difluoroethyl)-N-[2-[4-[[6-[2-[[2-(2,6-dioxo-3-piperidyl)-1,3-dioxo-isoindolin-4-yl]amino]ethyl]-2-azaspiro [3.3]heptan-2-yl]methyl]cyclohexyl]-6-methoxy-indazol-5-yl]pyridine-2-carboxamide (189 mg, 230 umol, containing some of cis-isomer) was purified by normal prep-HPLC (column: Waters Vinridis Silica 2-EP OBD 50*150 mm*5 um; mobile phase: [n-Heptane-IPA (0.1% TEA)]; B %: 15%-55%, 10 min) twice and then purified by Prep-HPLC (column: Unisil 3-100 C18 Ultra 150*50 mm*3 um; mobile phase: [water (0.225% FA)-ACN]; B %: 30%-50%, 10 min) to give the title compound (10.4 mg, 15% yield, FA) as yellow solid. ¹H NMR (400 MHz, DMSO-d₆) δ 11.09 (s, 1H), 10.66 (s, 1H), 8.66 (s, 1H), 8.34-8.27 (m, 3H), 8.03-7.99 (m, 1H), 7.62-7.54 (m, 1H), 7.18-7.14 (m, 1H), 7.06 (d, J=8.8 Hz, 1H), 7.02 (d, J=7.2 Hz, 1H), 6.47 (t, J=5.6 Hz, 1H), 5.08-5.02 (m, 1H), 4.48-4.36 (m, 1H), 3.99 (s, 3H), 3.24-3.20 (m, 2H), 3.17 (s, 2H), 3.07 (s, 2H), 2.94-2.83 (m, 1H), 2.63-2.53 (m, 2H), 2.42-2.35 (m, 2H), 2.26-2.06 (m, 8H), 2.06-1.98 (m, 1H), 1.90-1.80 (m, 2H), 1.80-1.72 (m, 2H), 1.68-1.61 (m, 2H), 1.58-1.55 (m, 4H); LC-MS (ESI⁺) m/z 823.5 (M+H)⁺.

Example 8: Synthesis of N-[2-[2-[[1-[1-(2,6-dioxo-3-piperidyl)-3-methyl-2-oxo-benzimidazol-4-yl]-4-piperidyl]-methyl-amino]ethyl]-6-fluoro-indazol-5-yl]-6-(trifluoromethyl)pyridine-2-carboxamide (I-19)

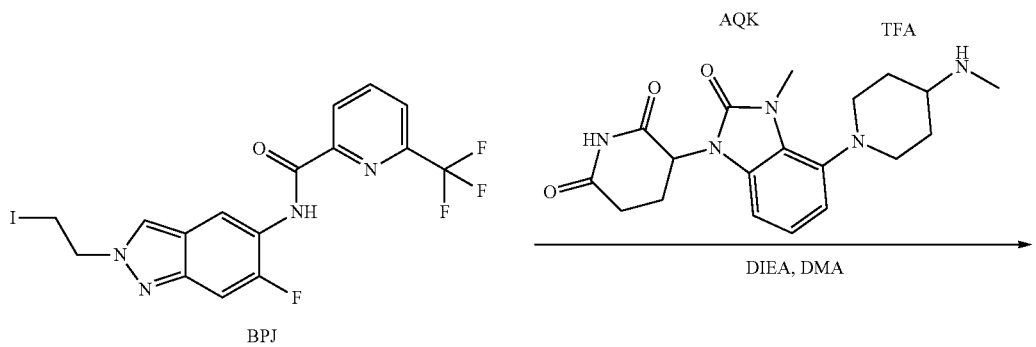

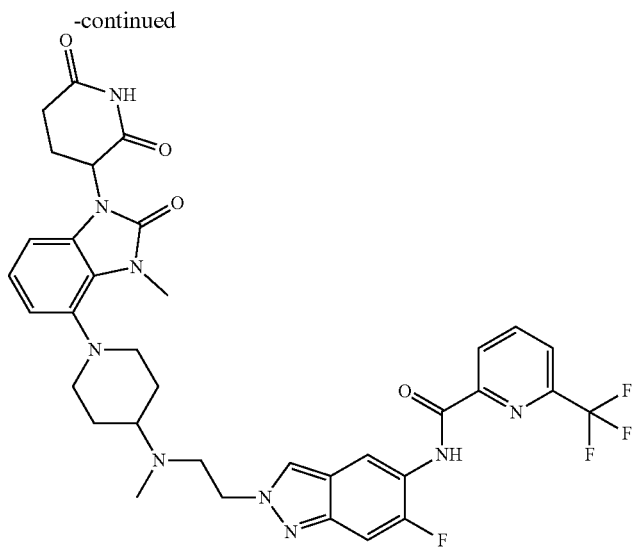

To a solution of 3-[3-methyl-4-[4-(methylamino)-1-piperidyl]-2-oxo-benzimidazol-1-yl]piperidine-2,6-dione (76.1 mg, 156 umol, TFA, Intermediate AQK) and N-[6-fluoro-2-(2-iodoethyl)indazol-5-yl]-6-(trifluoromethyl) pyridine-2-carboxamide (75.0 mg, 156 umol, Intermediate BPJ) in DMA (2.00 mL) was added DIEA (121 mg, 941 umol, 164 uL) at 25° C., and the mixture was stirred at 60° C. for 16 hr. On completion, the reaction mixture was quenched by addition water (0.25 mL), and then concentrated in vacuo to give a residue. The residue was purified by reversed phase (0.1% FA condition) to give the crude product which was re-purified by prep-HPLC (column: Phenomenex luna C18 150*25 mm*10 um; mobile phase: [water (0.225% FA)-ACN]; B %: 17%-47%, 10 min) to give the title compound (4.27 mg, 4% yield, FA) as a white solid. $^1$H NMR (400 MHz, DMSO-d$_6$) δ 11.08 (d, J=3.6 Hz, 1H), 10.23 (d, J=2.0 Hz, 1H), 8.49 (s, 1H), 8.47-8.37 (m, 3H), 8.22 (dd, J=1.2, 7.6 Hz, 1H), 7.55 (d, J=12.0 Hz, 1H), 7.00-6.91 (m, 1H), 6.91-6.80 (m, 2H), 5.39-5.27 (m, 1H), 4.49 (t, J=5.6 Hz, 2H), 3.60 (s, 3H), 3.13-3.05 (m, 2H), 2.99 (t, J=6.4 Hz, 2H), 2.92-2.82 (m, 1H), 2.73-2.64 (m, 3H), 2.63-2.59 (m, 1H), 2.46-2.42 (m, 1H), 2.31 (s, 3H), 2.02-1.94 (m, 1H), 1.74-1.65 (m, 2H), 1.64-1.47 (m, 2H); LC-MS (ESI$^+$) m/z 722.4 (M+H)$^+$.

Example 9: Synthesis of N-[2-[2-[[1-[1-(2,6-dioxo-3-piperidyl)-3-methyl-2-oxo-benzimidazol-4-yl]-4-piperidyl]-methyl-amino]ethyl]-6-methoxy-indazol-5-yl]-6-(trifluoromethyl)pyridine-2-carboxamide (I-20)

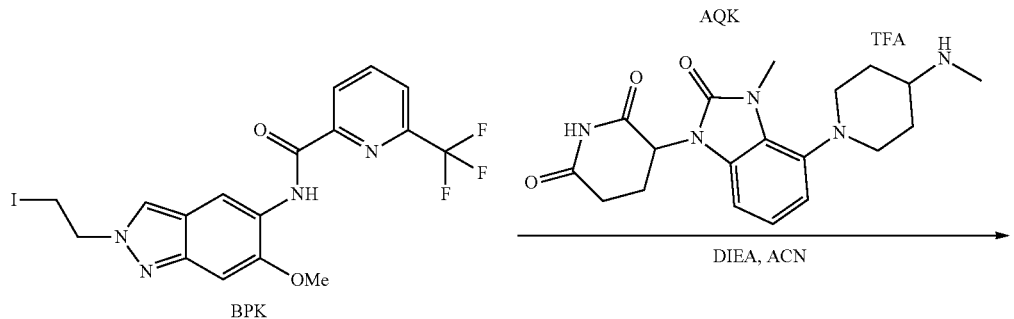

-continued

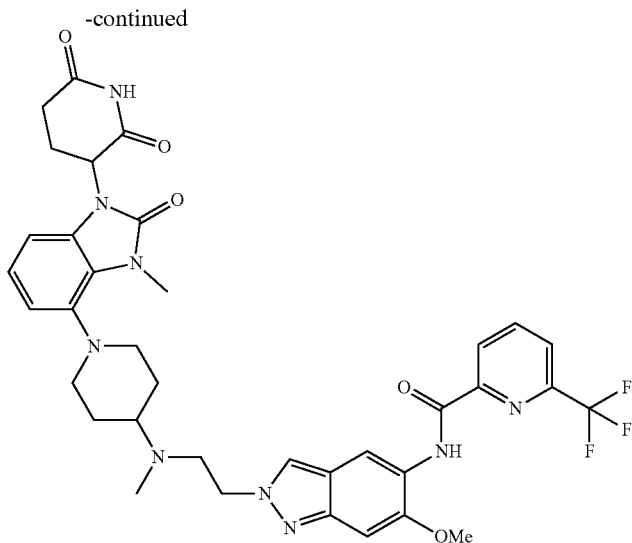

To a solution of N-[2-(2-iodoethyl)-6-methoxy-indazol-5-yl]-6-(trifluoromethyl)pyridine-2-carboxamide (110 mg, 224 umol, Intermediate BPK) and 3-[3-methyl-4-[4-(methylamino)-1-piperidyl]-2-oxo-benzimidazol-1-yl]piperidine-2,6-dione (108 mg, 224 umol, TFA salt, Intermediate AQK) in ACN (4 mL) was added DIEA (87.0 mg, 673 umol). The reaction mixture was stirred at 80° C. for 16 hrs. On completion, the reaction mixture was acidified with FA until the pH=6-7, and the solution was concentrated in vacuo. The residue was purified by Prep-HPLC (column: Phenomenex Synergi C18 150*25 mm*10 um; mobile phase: [water (0.225% FA)-ACN]) to give the title compound (50.0 mg, 28% yield, FA salt) as yellow solid. $^1$H NMR (400 MHz, DMSO-$d_6$) δ 11.07 (s, 1H), 10.50 (s, 1H), 8.69 (s, 1H), 8.49-8.45 (m, 1H), 8.43-8.38 (m, 1H), 8.33 (s, 1H), 8.22 (dd, J=0.8, 8.0 Hz, 1H), 7.16 (s, 1H), 7.00-6.81 (m, 3H), 5.33 (dd, J=5.2, 12.8 Hz, 1H), 4.43 (t, J=6.0 Hz, 2H), 3.98 (s, 3H), 3.60 (s, 3H), 3.14-3.05 (m, 2H), 2.98 (t, J=6.0 Hz, 2H), 2.93-2.82 (m, 1H), 2.70-2.58 (m, 4H), 2.46-2.44 (m, 1H), 2.30 (s, 3H), 2.04-1.92 (m, 1H), 1.77-1.68 (m, 2H), 1.65-1.51 (m, 2H); LC-MS (ESI$^+$) m/z 734.5 (M+H)$^+$.

Example 10: Synthesis of N-[2-[2-[[1-[1-(2,6-dioxo-3-piperidyl)-3-methyl-2-oxo-benzimidazol-4-yl]-4-piperidyl]-methyl-amino]ethyl]-6-methoxy-indazol-5-yl]pyrazolo[1,5-a]pyrimidine-3-carboxamide (I-21)

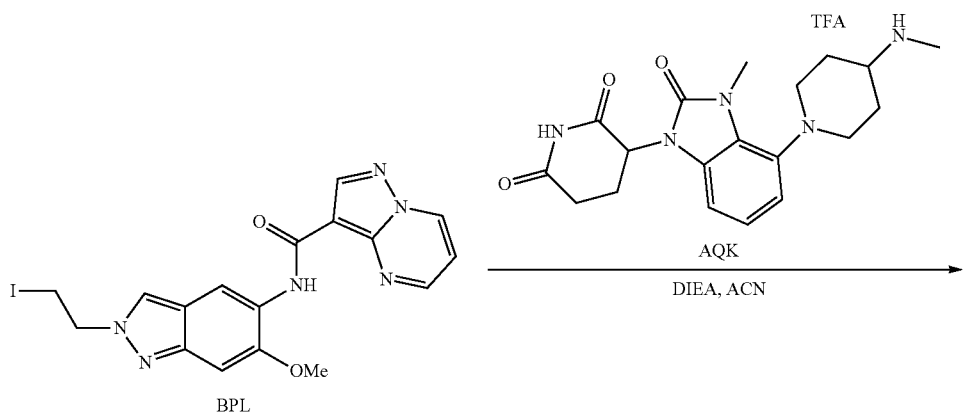

-continued

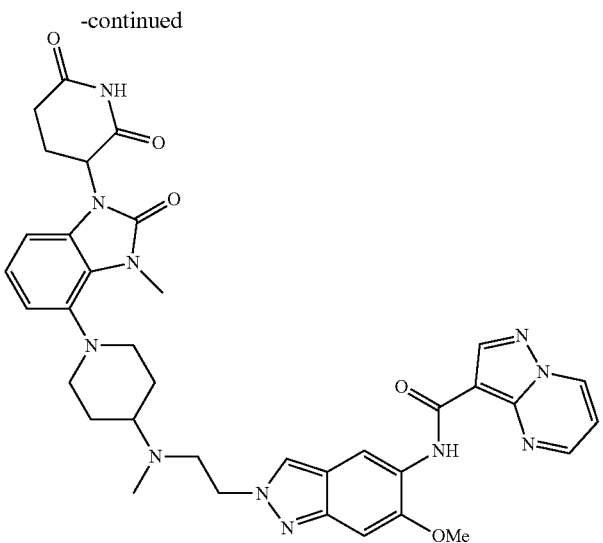

To a solution of 3-[3-methyl-4-[4-(methylamino)-1-piperidyl]-2-oxo-benzimidazol-1-yl] piperidine-2,6-dione (178 mg, 367 umol, TFA salt, Intermediate AQK) and DIEA (142 mg, 1.10 mmol) in ACN (5 mL) was added N-[2-(2-iodoethyl)-6-methoxy-indazol-5-yl]pyrazolo[1,5-a]pyrimidine-3-carboxamide (170 mg, 367 umol, Intermediate BPL). The reaction mixture was stirred at 80° C. for 16 hrs. On completion, the reaction mixture was acidified with FA until the pH=6~7, and the mixture was concentrated in vacuo. The residue was purified by Prep-HPLC (column: Phenomenex Synergi C18 150*25 mm*10 um; mobile phase: [water (0.225% FA)-ACN]) to give the title compound (33.4 mg, 11% yield, FA salt) as yellow solid. $^1$H NMR (400 MHz, DMSO-$d_6$) δ 11.07 (s, 1H), 10.53 (s, 1H), 9.38 (dd, J=1.6, 7.2 Hz, 1H), 8.96 (dd, J=1.6, 4.0 Hz, 1H), 8.77-8.64 (m, 2H), 8.27 (s, 1H), 7.35 (dd, J=4.0, 7.2 Hz, 1H), 7.11 (s, 1H), 7.01-6.77 (m, 3H), 5.33 (dd, J=4.8, 12.4 Hz, 1H), 4.42 (t, J=6.0 Hz, 2H), 4.03 (s, 3H), 3.60 (s, 3H), 3.14-3.06 (m, 2H), 2.98 (t, J=6.4 Hz, 2H), 2.91-2.82 (m, 1H), 2.75-2.60 (m, 4H), 2.60-2.53 (m, 1H), 2.31 (s, 3H), 2.05-1.90 (m, 1H), 1.79-1.68 (m, 2H), 1.67-1.52 (m, 2H); LC-MS (ESI$^+$) m/z 706.5 (M+H)$^+$.

Example 11: Synthesis of N-[2-[2-[[1-[1-(2,6-dioxo-3-piperidyl)-3-methyl-2-oxo-benzimidazol-4-yl]-4-piperidyl]-methyl-amino] ethyl]-6-fluoro-indazol-5-yl]pyrazolo[1,5-a] pyrimidine-3-carboxamide (I-22)

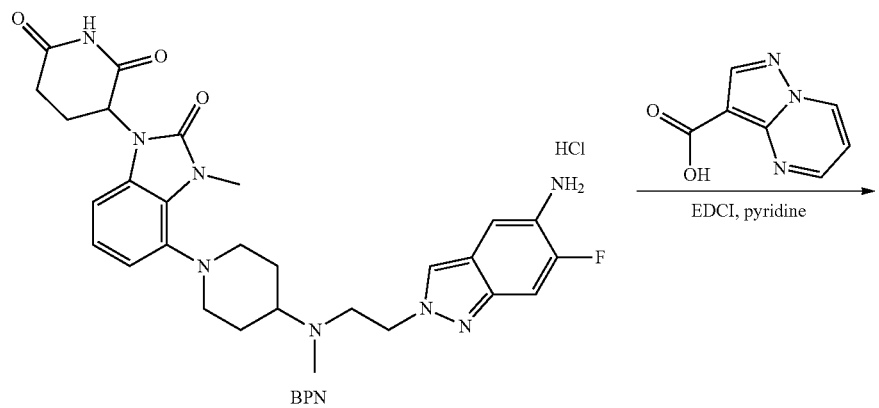

-continued

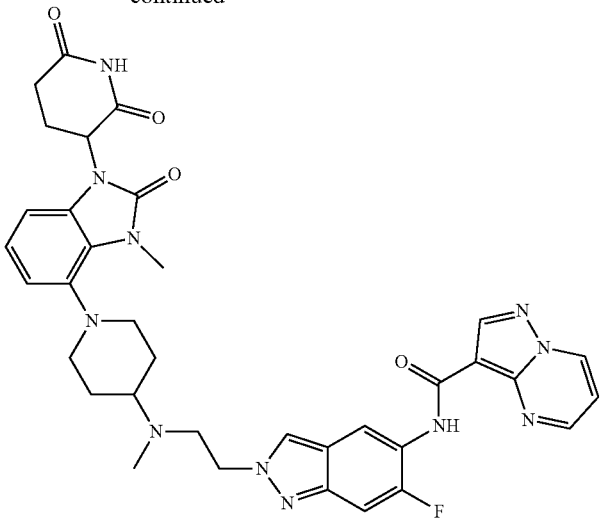

To a solution of 3-[4-[4-[2-(5-amino-6-fluoro-indazol-2-yl)ethyl-methyl-amino]-1-piperidyl]-3-methyl-2-oxo-benzimidazol-1-yl]piperidine-2,6-dione (10.0 mg, 17.1 umol, HCl, Intermediate BPN) and pyrazolo[1,5-a] pyrimidine-3-carboxylic acid (3.07 mg, 18.8 umol, CAS #25940-35-6) in pyridine (0.50 mL) was added EDCI (3.93 mg, 20.5 umol). The mixture was stirred at 25° C. for 1 hr. On completion, the reaction mixture was quenched with water (0.05 mL) and then concentrated in vacuo to give a residue. The residue was purified by prep-HPLC (column: Phenomenex luna C18 150*25 mm*10 um; mobile phase: [water (0.225% FA)-ACN]; B %: 10%-40%, 10 min) to give the title compound (4.46 mg, 35% yield, FA) as a white solid. $^1$H NMR (400 MHz, DMSO-$d_6$) δ$^1$H NMR (400 MHz, DMSO-$d_6$) δ=11.08 (s, 1H), 10.18 (d, J=3.2 Hz, 1H), 9.40 (dd, J=1.6, 7.2 Hz, 1H), 8.93 (dd, J=1.6, 4.4 Hz, 1H), 8.75 (s, 1H), 8.67 (d, J=7.6 Hz, 1H), 8.45 (s, 1H), 7.54 (d, J=12.0 Hz, 1H), 7.36 (dd, J=4.4, 7.0 Hz, 1H), 7.00-6.79 (m, 3H), 5.32 (dd, J=4.8, 12.4 Hz, 1H), 4.47 (t, J=6.4 Hz, 2H), 3.59 (s, 3H), 3.13-3.05 (m, 2H), 2.98 (t, J=6.4 Hz, 2H), 2.92-2.83 (m, 1H), 2.72-2.67 (m, 1H), 2.66-2.56 (m, 3H), 2.46-2.41 (m, 1H), 2.30 (s, 3H), 2.01-1.93 (m, 1H), 1.73-1.66 (m, 2H), 1.57 (dd, J=1.2, 10.8 Hz, 2H); LC-MS (ESI$^+$) m/z 694.2 (M+H)$^+$.

Examples 12: Syntheses of N-[2-[3-[[[1-[1-(2,6-dioxo-3-piperidyl)-3-methyl-2-oxo-benzimidazol-4-yl]-4-piperidyl]-methyl-amino]methyl]cyclobutyl]-6-methoxy-indazol-5-yl]-6-(trifluoromethyl)pyridine-2-carboxamide (I-31) and N-[2-[3-[[[1-[1-(2,6-dioxo-3-piperidyl)-3-methyl-2-oxo-benzimidazol-4-yl]-4-piperidyl]-methyl-amino]methyl]cyclobutyl]-6-methoxy-indazol-5-yl]-6-(trifluoromethyl)pyridine-2-carboxamide (I-32)

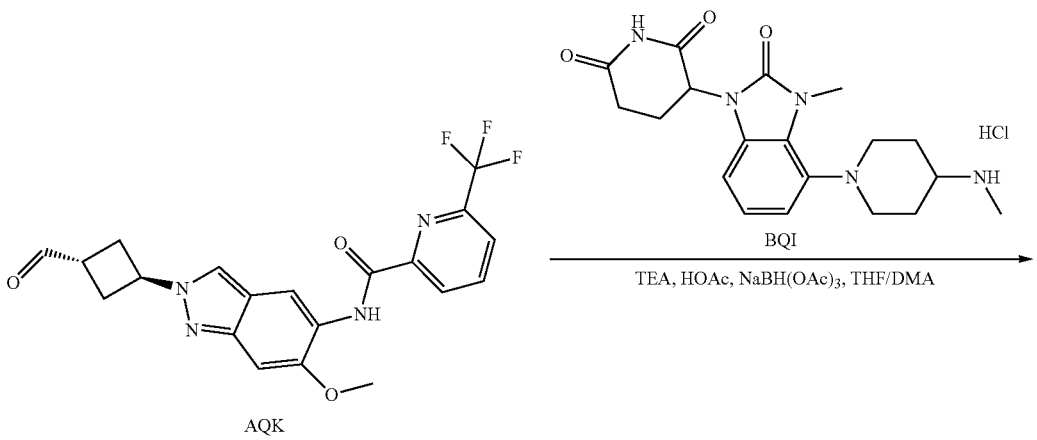

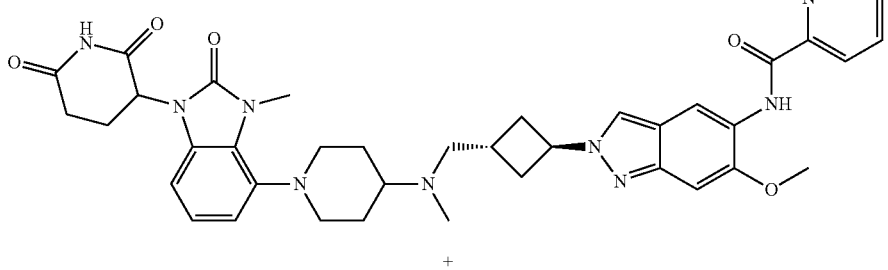

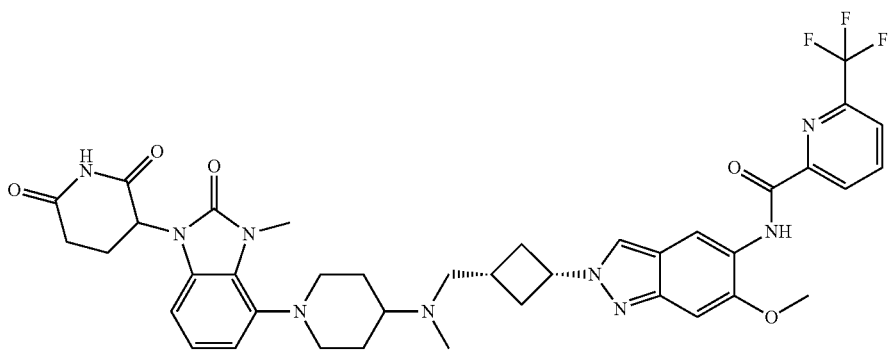

To a solution of 3-[3-methyl-4-[4-(methylamino)-1-piperidyl]-2-oxo-benzimidazol-1-yl]piperidine-2,6-dione (53.6 mg, 131 umol, HCl salt, Intermediate AQK) in THF (0.5 mL) and DMA (1 mL) was added TEA (13.3 mg, 131 umol), then the mixture stirred at 25° C. for 10 min. Next, HOAc (7.89 mg, 131 umol) and N-[2-(3-formylcyclobutyl)-6-methoxy-indazol-5-yl]-6-(trifluoromethyl)pyridine-2-carboxamide (55.0 mg, 131 umol, Intermediate BQI) was added to the mixture and was stirred at 25° C. for 20 minutes. Next, NaBH(OAc)$_3$ (55.7 mg, 262 umol) was added to the mixture at 0° C. and the reaction mixture was stirred at -20-0° C. for 2 hrs. On completion, H$_2$O (0.5 mL) was added to the reaction mixture, then the mixture was concentrated in vacuo. The residue was purified by prep-HPLC (column: Phenomenex Gemini-NX C18 75*30 mm*3 um; mobile phase: [water (0.225% FA)-ACN]; B %: 20%-50%, 7 min) and prep-HPLC (column: Welch Ultimate XB-SiOH 250*50*10 um; mobile phase: [Hexane-IPA]; B %: 50%-90%, 15 min) to give N-[2-[3-[[[1-[1-(2,6-dioxo-3-piperidyl)-3-methyl-2-oxo-benzimidazol-4-yl]-4-piperidyl]-methyl-amino]methyl]cyclobutyl]-6-methoxy-indazol-5-yl]-6-(trifluoromethyl)pyridine-2-carboxamide (4.51 mg, 11% yield) ($^1$H NMR (400 MHz, DMSO-d$_6$) δ 11.09 (s, 1H), 10.51 (s, 1H), 8.69 (s, 1H), 8.49-8.36 (m, 3H), 8.22 (d, J=7.6 Hz, 1H), 7.20 (s, 1H), 7.03-6.85 (m, 3H), 5.35 (dd, J=5.2, 13.2 Hz, 1H), 5.25-5.17 (m, 1H), 3.99 (s, 3H), 3.66 (s, 3H), 3.18 (d, J=11.2 Hz, 4H), 2.93-2.85 (m, 2H), 2.77-2.68 (m, 6H), 2.60 (s, 3H), 2.30-2.21 (m, 3H), 2.02-1.98 (m, 1H), 1.90-1.81 (m, 2H), 1.78-1.69 (m, 2H); LC-MS (ESI+) m/z 774.5 (M+H)$^+$) and N-[2-[3-[[[1-[1-(2,6-dioxo-3-piperidyl)-3-methyl-2-oxo-benzimidazol-4-yl]-4-piperidyl]-methyl-amino]methyl]cyclobutyl]-6-methoxy-indazol-5-yl]-6-(trifluoromethyl)pyridine-2-carboxamide (23.0 mg, 57% yield) ($^1$H NMR (400 MHz, DMSO-d$_6$) δ 11.08 (s, 1H), 10.51 (s, 1H), 8.68 (s, 1H), 8.49-8.36 (m, 3H), 8.22 (d, J=7.6 Hz, 1H), 7.19 (s, 1H), 7.00-6.85 (m, 3H), 5.39-5.30 (m, 1H), 5.02-4.90 (m, 1H), 3.99 (s, 3H), 3.65 (s, 3H), 3.17 (d, J=9.6 Hz, 4H), 2.96-2.84 (m, 2H), 2.78-2.68 (m, 4H), 2.65-2.57 (m, 5H), 2.30-2.24 (m, 3H), 2.03-1.96 (m, 1H), 1.90-1.79 (m, 2H), 1.75-1.61 (m, 2H); LC-MS (ESI+) m/z 774.5 (M+H)$^+$) as white solids. The structures of these two isomers were confirmed by 2D NMR.

Examples 13: Syntheses of N-[2-[3-[[3-[1-(2,6-dioxo-3-piperidyl)-3-methyl-2-oxo-benzimidazol-4-yl]azetidin-1-yl]methyl]cyclobutyl]-6-methoxy-indazol-5-yl]-6-(trifluoromethyl)pyridine-2-carboxamide (I-46) and N-[2-[3-[[3-[1-(2,6-dioxo-3-piperidyl)-3-methyl-2-oxo-benzimidazol-4-yl]azetidin-1-yl]methyl]cyclobutyl]-6-methoxy-indazol-5-yl]-6-(trifluoromethyl)pyridine-2-carboxamide (I-50)
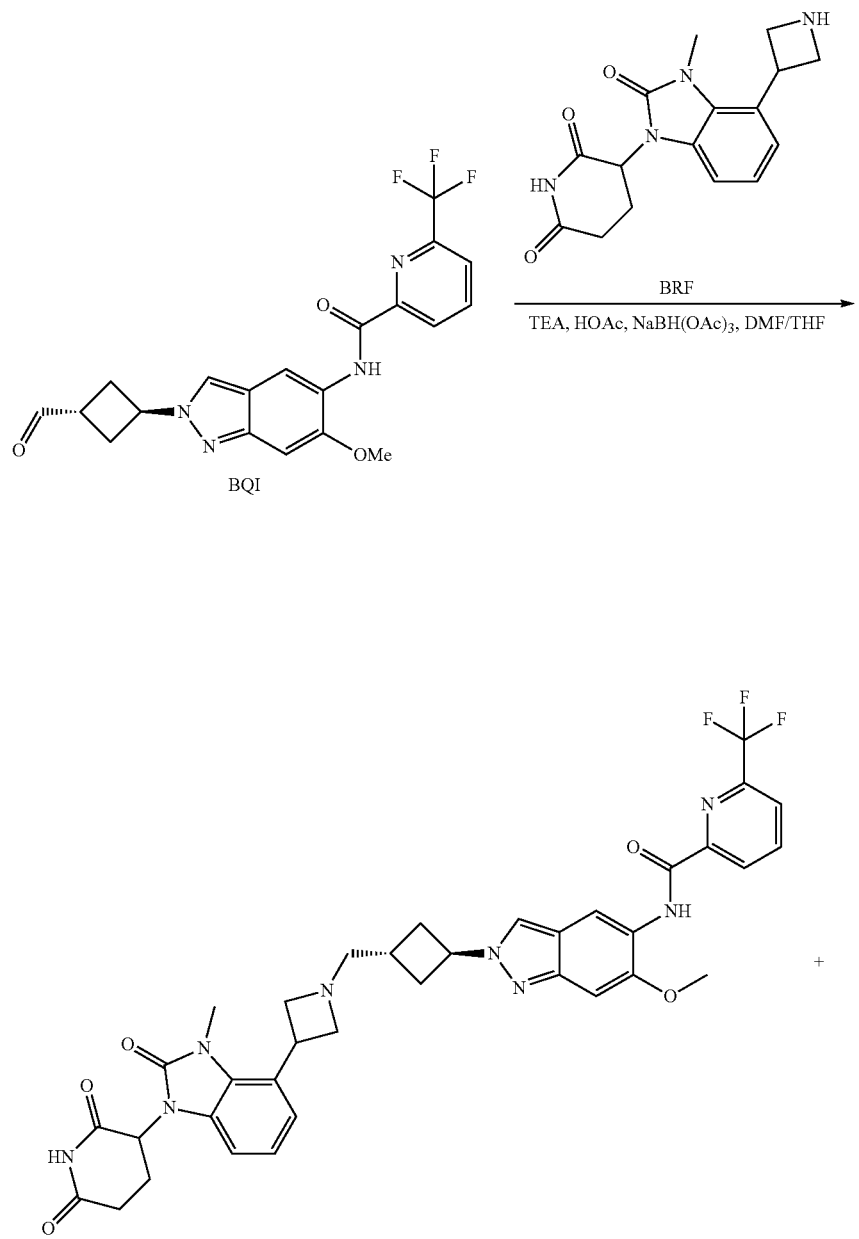

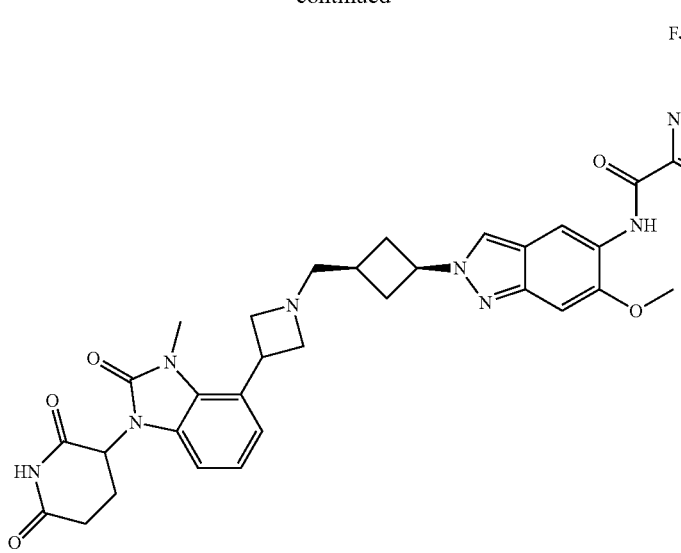

To a solution of 3-[4-(azetidin-3-yl)-3-methyl-2-oxo-benzimidazol-1-yl]piperidine-2,6-dione (50.0 mg, 116 umol, TFA, Intermediate BRF) in THF (1 mL) and DMF (1 mL) was added TEA (11.8 mg, 116 umol), and the reaction mixture was stirred at −10° C. for 10 mins. Then N-[2-(3-formylcyclobutyl)-6-methoxy-indazol-5-yl]-6-(trifluoromethyl)pyridine-2-carboxamide (45.0 mg, 107 umol, Intermediate BQI) and HOAc (14.0 mg, 233 umol) was added to the mixture at −10° C. and stirred for 20 mins. Next, NaBH(OAc)₃ (29.7 mg, 140 umol) was added to the mixture and the mixture was stirred at −10° C. for 1 hr. On completion, the reaction mixture was quenched with water (0.05 mL) and concentrated in vacuo to give a residue. The residue was purified by prep-HPLC(column: Phenomenex luna C18 150*25 mm*10 um; mobile phase: [water (0.225% FA)-ACN]; B %: 16%-46%, 11.5 min) and purified by prep-HPLC(column: Welch Ultimate XB SiO2 10 u 100*30 mm; mobile phase: [IPA-ACN]; B %: 85%-95%, 10 min). Then the residue was further purified by prep-HPLC(column: Phenomenex luna C18 150*25 mm*10 um; mobile phase: [water (0.225% FA)-ACN]; B %:20%-50%, 11 min) to give the title compound N-[2-[3-[[3-[1-(2,6-dioxo-3-piperidyl)-3-methyl-2-oxo-benzimidazol-4-yl]azetidin-1-yl] methyl] cyclobutyl]-6-methoxy-indazol-5-yl]-6-(trifluoromethyl)pyridine-2-carboxamide (13.98 mg, 15% yield, FA) ($^1$H NMR (400 MHz, DMSO-d₆) δ 11.09 (s, 1H), 10.51 (s, 1H), 8.69 (s, 1H), 8.49-8.44 (m, 1H), 8.41 (t, J=8.0 Hz, 1H), 8.36 (s, 1H), 8.22 (dd, J=0.9, 7.6 Hz, 1H), 7.23-7.17 (m, 2H), 7.10-7.04 (m, 1H), 7.04-6.99 (m, 1H), 5.37 (dd, J=5.2, 12.4 Hz, 1H), 5.24-5.11 (m, 1H), 4.32-4.19 (m, 1H), 3.99 (s, 3H), 3.69 (t, J=6.8 Hz, 2H), 3.53 (s, 3H), 3.27 (s, 4H), 2.93-2.84 (m, 1H), 2.77-2.67 (m, 3H), 2.66-2.57 (m, 2H), 2.35 (d, J=3.2 Hz, 1H), 2.31 (s, 1H), 2.04-1.95 (m, 1H); LC-MS (ESI⁺) m/z 717.2 (M+H)⁺) and N-[2-[3-[[3-[1-(2,6-dioxo-3-piperidyl)-3-methyl-2-oxo-benzimidazol-4-yl]azetidin-1-yl]methyl]cyclobutyl]-6-methoxy-indazol-5-yl]-6-(trifluoromethyl)pyridine-2-carboxamide (5.77 mg, 6.48% yield, FA) ($^1$H NMR (400 MHz, DMSO-d₆) δ 11.09 (s, 1H), 10.50 (s, 1H), 8.68 (s, 1H), 8.49-8.44 (m, 1H), 8.41 (t, J=7.6 Hz, 1H), 8.36 (s, 1H), 8.22 (d, J=7.6 Hz, 1H), 7.24-7.16 (m, 2H), 7.11-6.96 (m, 2H), 5.37 (dd, J=5.6, 12.8 Hz, 1H), 5.03-4.88 (m, 1H), 4.31-4.17 (m, 1H), 3.99 (s, 3H), 3.67 (t, J=7.2 Hz, 2H), 3.52 (s, 3H), 3.25 (s, 4H), 2.94-2.82 (m, 1H), 2.65-2.56 (m, 5H), 2.33 (s, 1H), 2.24-2.18 (m, 1H), 1.99 (dd, J=4.8, 6.8 Hz, 1H). LC-MS (ESI⁺) m/z 717.2 (M+H)⁺) as white solids.

Examples 14: Synthesis of N-[2-[4-[[3-[1-(2,6-di-oxo-3-piperidyl)-3-methyl-2-oxo-benzimidazol-4-yl]-3,6-diazabicyclo[3.1.1]heptan-6-yl]methyl]cyclo-hexyl]indazol-5-yl]-6-(trifluoromethyl)pyridine-2-carboxamide (I-157) & N-[2-[4-[[3-[1-(2,6-dioxo-3-piperidyl)-3-methyl-2-oxo-benzimidazol-4-yl]-3,6-diazabicyclo[3.1.1]heptan-6-yl]methyl]cyclohexyl]indazol-5-yl]-6-(trifluoromethyl)pyridine-2-carboxamide (I-156)
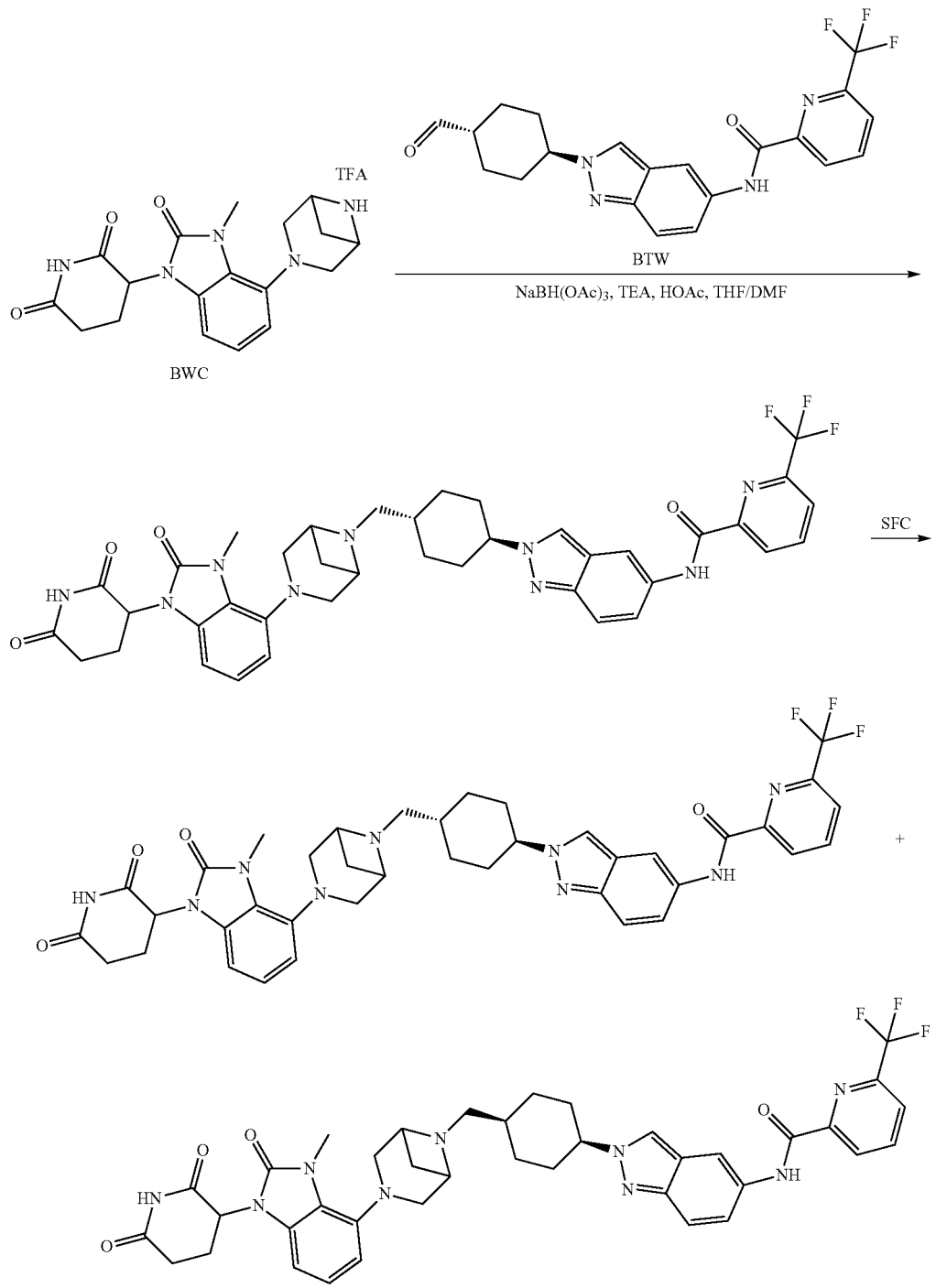

Step 1—N-[2-[4-[[3-[1-(2,6-dioxo-3-piperidyl)-3-methyl-2-oxo-benzimidazol-4-yl]-3,6-diazabicyclo[3.1.1]heptan-6-yl]methyl]cyclohexyl]indazol-5-yl]-6-(trifluoromethyl)pyridine-2-carboxamide To a mixture of 3-[4-(3,6-diazabicyclo[3.1.1]heptan-3-yl)-3-methyl-2-oxo-benzimidazol-1-yl]piperidine-2,6-dione (80.0 mg, 170 umol, TFA, Intermediate BWC) in THF (1 mL) and DMF (0.5 mL) was added TEA (17.2 mg, 170 umol, 23.7 uL), N-[2-(4-formylcyclohexyl)indazol-5-yl]-6-(trifluoromethyl)pyridine-2-carboxamide (70.9 mg, 170 umol, Intermediate BTW) and HOAc (10.2 mg, 170 umol, 9.75 uL) at −10° C. The reaction mixture was stirred at −10° C. for 0.5 hour, then NaBH(OAc)$_3$ (54.1 mg, 255 umol) was added to the mixture. The reaction mixture was then stirred at −10° C. for 3.5 hours. On completion, the reaction mixture was concentrated in vacuo. The residue was purified by prep-HPLC (column: Phenomenex luna C18 150*25 mm*10 um; mobile phase: [water (0.225% FA)-ACN]; B %: 18%-48%, 10 min) to give the title compound (31.0 mg, 22% yield, FA) as white solid. $^1$H NMR (400 MHz, DMSO-d$_6$) δ 11.11 (s, 1H), 10.36 (s, 1H), 8.49-8.28 (m, 4H), 8.20-8.15 (m, 1H), 7.65-7.53 (m, 2H), 7.49-7.29 (m, 1H), 7.12 (t, J=7.6 Hz, 1H), 7.01 (d, J=7.2 Hz, 1H), 5.43-5.34 (m, 1H), 4.54-4.43 (m, 1H), 3.79-3.64 (m, 2H), 3.57 (s, 3H), 3.19 (d, J=12.8 Hz, 2H), 2.94-2.85 (m, 1H), 2.78-2.58 (m, 4H), 2.52 (s, 2H), 2.20 (dd, J=1.6, 9.6 Hz, 2H), 2.06-1.94 (m, 5H), 1.93-1.88 (m, 1H), 1.76-1.76 (m, 1H), 1.79-1.66 (m, 1H), 1.40-1.22 (m, 2H); LC-MS (ESI$^+$) m/z 756.4 (M+H)$^+$.

Step 2—N-[2-[4-[[3-[1-(2,6-dioxo-3-piperidyl)-3-methyl-2-oxo-benzimidazol-4-yl]-3,6-diazabicyclo[3.1.1]heptan-6-yl]methyl]cyclohexyl]indazol-5-yl]-6-(trifluoromethyl)pyridine-2-carboxamide & N-[2-[4-[[3-[1-(2,6-dioxo-3-piperidyl)-3-methyl-2-oxo-benzimidazol-4-yl]-3,6-diazabicyclo[3.1.1]heptan-6-yl]methyl]cyclohexyl]indazol-5-yl]-6-(trifluoromethyl)pyridine-2-carboxamide N-[2-[4-[[3-[1-(2,6-dioxo-3-piperidyl)-3-methyl-2-oxo-benzimidazol-4-yl]-3,6-diazabicyclo[3.1.1]heptan-6-yl]methyl]cyclohexyl]indazol-5-yl]-6-(trifluoromethyl)pyridine-2-carboxamide (31.0 mg, 38.6 umol, FA) was separated by SFC (column: DAICEL CHIRALCEL OD (250 mm*50 mm, 10 um); mobile phase: [Hexane-IPA]; B %: 40%-40%, 11.5; 130 min) to give the compounds P1 and P2. The compound P1 was repurified by prep-HPLC (column: Phenomenex Synergi Polar-RP 100*25 mm*4 um; mobile phase: [water (0.225% FA)-ACN]; B %: 23%-53%, 8 min) to give N-[2-[4-[[3-[1-(2,6-dioxo-3-piperidyl)-3-methyl-2-oxo-benzimidazol-4-yl]-3,6-diazabicyclo[3.1.1]heptan-6-yl]methyl]cyclohexyl]indazol-5-yl]-6-(trifluoromethyl)pyridine-2-carboxamide (4.64 mg, 27% yield, 100% purity, FA) as white solid ($^1$H NMR (400 MHz, DMSO-d$_6$) δ 11.11 (s, 1H), 10.36 (s, 1H), 8.43-8.35 (m, 3H), 8.30 (s, 1H), 8.19-8.14 (m, 1H), 8.14-8.14 (m, 1H), 7.63-7.60 (m, 1H), 7.57-7.53 (m, 1H), 7.42-7.30 (m, 1H), 7.11 (t, J=8.0 Hz, 1H), 6.98 (d, J=7.2 Hz, 1H), 5.38 (dd, J=5.6, 12.8 Hz, 1H), 4.53-4.42 (m, 1H), 3.72-3.62 (m, 2H), 3.57 (s, 3H), 3.48-3.39 (m, 2H), 3.20-3.05 (m, 2H), 2.94-2.85 (m, 1H), 2.77-2.60 (m, 4H), 2.18 (d, J=11.2 Hz, 3H), 2.01 (d, J=13.6 Hz, 4H), 1.97-1.88 (m, 2H), 1.72-1.51 (m, 1H), 1.33-1.23 (m, 2H); LC-MS (ESI$^+$) m/z 756.3 (M+H)$^+$).$^+$). The compound P2 was repurified by prep-HPLC (column: Phenomenex Synergi Polar-RP 100*25 mm*4 um; mobile phase: [water (0.225% FA)-ACN]; B %: 23%-53%, 8 min) to give N-[2-[4-[[3-[1-(2,6-dioxo-3-piperidyl)-3-methyl-2-oxo-benzimidazol-4-yl]-3,6-diazabicyclo[3.1.1]heptan-6-yl]methyl]cyclohexyl]indazol-5-yl]-6-(trifluoromethyl)pyridine-2-carboxamide (1.00 mg, 5% yield, FA) as white solid ($^1$H NMR (400 MHz, DMSO-d$_6$) δ 11.14-11.05 (m, 1H), 10.36 (s, 1H), 8.47 (s, 1H), 8.41-8.38 (m, 1H), 8.35 (d, J=8.0 Hz, 1H), 8.29 (s, 1H), 8.17 (d, J=7.6 Hz, 1H), 7.65-7.61 (m, 1H), 7.57-7.53 (m, 1H), 7.32 (d, J=8.0 Hz, 1H), 7.09 (t, J=8.0 Hz, 1H), 6.95 (d, J=8.0 Hz, 1H), 5.37 (dd, J=5.6, 12.4 Hz, 1H), 4.57-4.50 (m, 1H), 3.60 (d, J=6.0 Hz, 4H), 3.57 (s, 3H), 3.03 (d, J=10.8 Hz, 2H), 2.94-2.84 (m, 2H), 2.75-2.70 (m, 1H), 2.60 (d, J=2.8 Hz, 1H), 2.25-2.18 (m, 2H), 2.02-1.97 (m, 2H), 1.96-1.90 (m, 2H), 1.79-1.69 (m, 6H), 1.28-1.05 (m, 2H); LC-MS (ESI$^+$) m/z 756.3 (M+H)$^+$). The absolute stereochemistry was arbitrarily assigned.

Example 15: Synthesis of cyano-N-[2-[4-[[4-[4-(2,4-dioxohexahydropyrimidin-1-yl)-7-isoquinolyl]-1-piperidyl]methyl]cyclohexyl]indazol-5-yl]pyrazolo[1,5-a]pyrimidine-3-carboxamide (I-170)

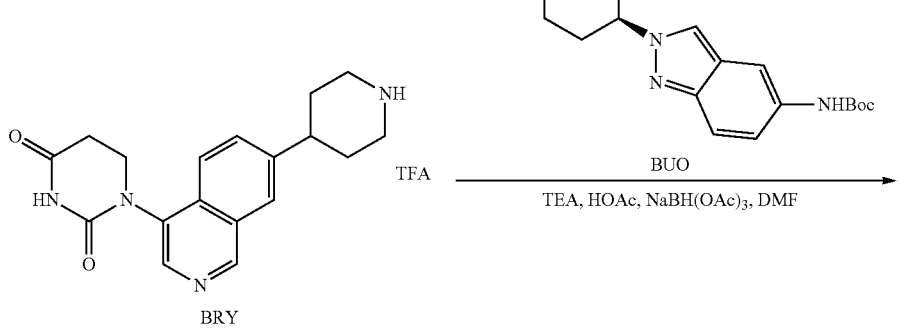

BRY

TFA

BUO

TEA, HOAc, NaBH(OAc)$_3$, DMF

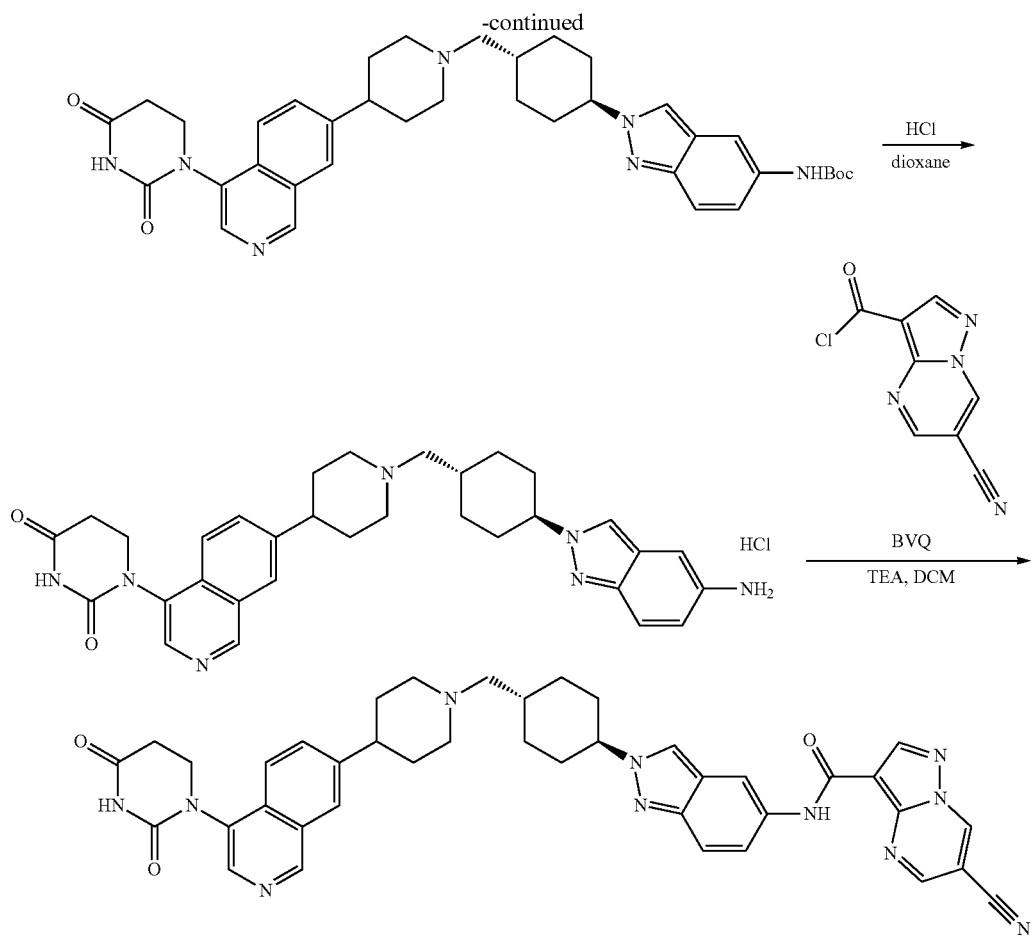

Step 1—Tert-butyl N-[2-[4-[[4-[4-(2,4-dioxohexahydropyrimidin-1-yl)-7-isoquinolyl]-1-piperidyl]methyl]cyclohexyl]indazol-5-yl]carbamate To a mixture of 1-[7-(4-piperidyl)-4-isoquinolyl]hexahydropyrimidine-2,4-dione (206 mg, 469 umol, TFA salt, Intermediate BRY) in DMF (2 mL) was added TEA (47.5 mg, 469 umol) at 25° C. until the pH stabilized at 8. The mixture was stirred at 25° C. for 10 mins, then HOAc (28.2 mg, 469 umol) was added at −15° C. until pH stabilized at 5~6. Then tert-butyl N-[2-(4-formylcyclohexyl)indazol-5-yl]carbamate (161 mg, 469 umol, Intermediate BUO) was added. The mixture was stirred at −15° C. for 20 mins. Subsequently, NaBH(OAc)₃ (129 mg, 610 umol) was added and the reaction mixture was stirred for another 0.5 hr. On completion, the mixture was quenched with H₂O (0.5 mL). The residue was purified by reverse phase (0.1% FA condition) to give the title compound (210 mg, 68% yield) as a pink solid. LC-MS (ESI+) m/z 652.3 (M+H)⁺.

Step 2—1-[7-[1-[[4-(5-Aminoindazol-2-yl)cyclohexyl]methyl]-4-piperidyl]-4-isoquinolyl]hexahydropyrimidine-2,4-dione Tert-butyl N-[2-[4-[[4-[4-(2,4-dioxohexahydropyrimidin-1-yl)-7-isoquinolyl]-1-piperidyl] methyl] cyclohexyl] indazol-5-yl]carbamate (60.0 mg, 92.0 umol) was dissolved in HCl/dioxane (4 M, 1.15 mL). The mixture was then stirred at 20° C. for 1 hr. On completion, the reaction mixture was concentrated in vacuo to give the title compound (50.0 mg, 98% yield) as a pink solid. LC-MS (ESI+) m/z 552.4 (M+H)⁺.

Step 3—6-Cyano-N-[2-[4-[[4-[4-(2,4-dioxohexahydropyrimidin-1-yl)-7-isoquinolyl]-1-piperidyl] methyl] cyclohexyl]indazol-5-yl]pyrazolo[1,5-a]pyrimidine-3-carboxamide To a mixture of 1-[7-[1-[[4-(5-aminoindazol-2-yl)cyclohexyl]methyl]-4-piperidyl]-4-isoquinolyl]hexahydropyrimidine-2,4-dione (50.0 mg, 85.0 umol, HCl salt) in DCM (2 mL) was added TEA (17.2 mg, 170 umol), then 6-cyanopyrazolo[1,5-a]pyrimidine-3-carbonyl chloride (17.5 mg, 85.0 umol, Intermediate BVQ) was added dropwise at 0° C. The mixture was then stirred at 0° C. for 0.5 hr. On completion, the reaction mixture was concentrated in vacuo. The residue was purified by prep-HPLC (column: Waters xbridge 150*25 mm 10 um; mobile phase: [water (10 mM NH₄HCO3)-ACN]; B %: 23%-53%, 11.5 min) to give the title compound (2.49 mg, 4.1% yield) as a yellow solid. ¹H NMR (400 MHz, DMSO-d₆) δ10.53 (s, 1H), 10.22 (d, J=2.0 Hz, 1H), 9.82 (s, 1H), 9.26 (s, 1H), 9.16 (d, J=2.0 Hz, 1H), 8.93 (s, 1H), 8.48 (s, 1H), 8.39 (s, 1H), 8.24 (d, J=1.2 Hz, 1H), 8.07 (s, 1H), 7.95-7.90 (m, 1H), 7.95-7.89 (m, 1H), 7.63 (d, J=9.2 Hz, 1H), 7.35 (dd, J=1.6, 9.2 Hz, 1H), 4.52-4.39 (m, 1H), 4.03-3.82 (m, 1H), 3.77-3.68 (m, 1H), 3.06-2.89 (m, 3H), 2.83-2.71 (m, 2H), 2.24-2.15 (m, 4H), 2.06-1.79 (m, 10H), 1.73-1.59 (m, 1H), 1.22-1.12 (m, 2H); LC-MS (ESI+) m/z 722.4 (M+H)⁺.

Example 16: Synthesis of 6-Cyano-N-[2-[4-[[4-[4-(2,4-dioxohexahydropyrimidin-1-yl)-8-isoquinolyl]-1-piperidyl] methyl]cyclohexyl]indazol-5-yl]pyrazolo[1,5-a]pyrimidine-3-carboxamide (I-204)

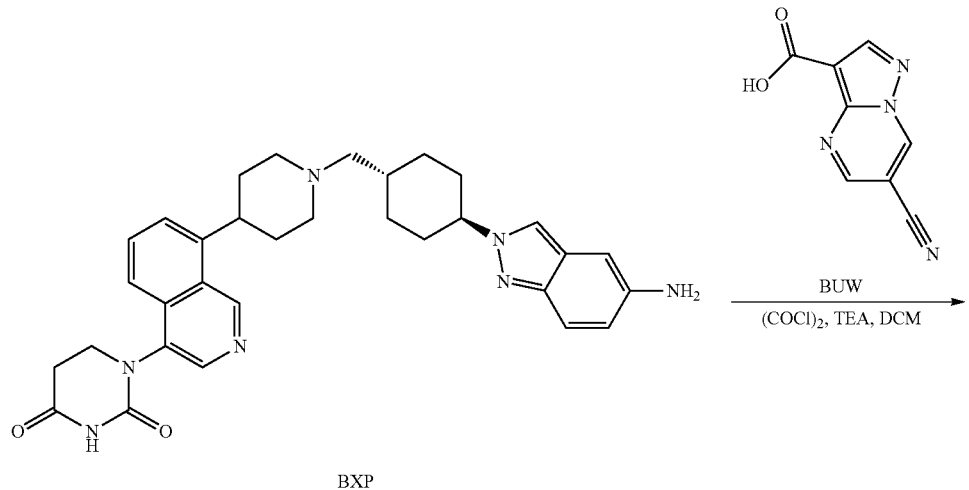

BXP

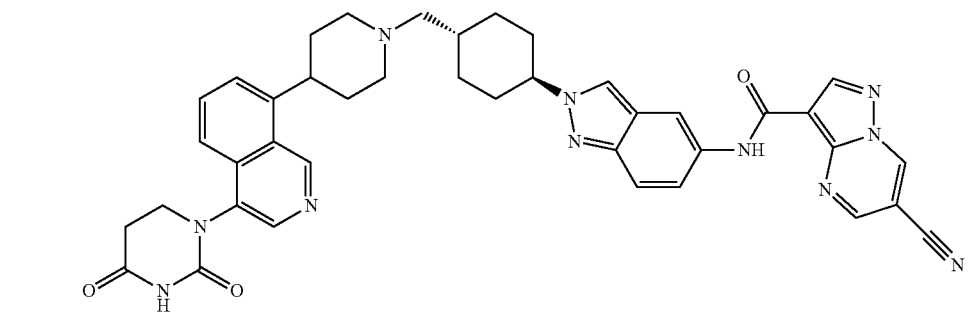

6-cyanopyrazolo[1,5-a]pyrimidine-3-carboxylic acid (13.0 mg, 69.1 umol, Intermediate BUW) was dissolved in DCM (1.5 mL) then TEA (20.9 mg, 207 umol) and $(COCl)_2$ (13.1 mg, 103 umol) was added dropwise to the solution at 0° C. The mixture was then stirred at 0° C. for 30 mins, then concentrated in vacuo to give crude acyl chloride. To a solution of 1-[8-[1-[[4-(5-aminoindazol-2-yl)cyclohexyl]methyl]-4-piperidyl]-4-isoquinolyl]hexahydropyrimidine-2,4-dione (46.0 mg, 69.1 umol, TFA, Intermediate BXP) in DCM (1.5 mL) was added TEA (13.9 mg, 138 umol) to adjust the pH to 8. Then the crude acyl chloride in DCM (1.5 mL) was added dropwise to the mixture and the reaction mixture was stirred at 0° C. for 30 mins. On completion, the mixture was quenched with $H_2O$ (0.5 mL) and purified by pre-HPLC (column: Waters xbridge 150*25 mm 10 um; mobile phase: [water (10 mM $NH_4HCO3$) -ACN]; B %: 19%-49%, 11 min) to give the title compound (1.30 mg, 3% yield) as light yellow solid. $^1$H NMR (400 MHz, DMSO-$d_6$) δ 10.53 (s, 1H), 10.21 (d, J=2.0 Hz, 1H), 9.82 (s, 1H), 9.61 (s, 1H), 9.16 (d, J=2.0 Hz, 1H), 8.93 (s, 1H), 8.57 (s, 1H), 8.39 (s, 1H), 8.23 (d, J=2.0 Hz, 1H), 7.88-7.83 (m, 1H), 7.78 (t, J=8.0 Hz, 1H), 7.69-7.60 (m, 2H), 7.35 (dd, J=2.0, 10.0 Hz, 1H), 4.51-4.39 (m, 1H), 3.94-3.89 (m, 1H), 3.7-3.67 (m, 1H), 3.62-3.56 (m, 1H), 3.06-2.93 (m, 3H), 2.78-2.73 (m, 1H), 2.26-2.16 (m, 4H), 2.05-1.79 (m, 10H), 1.76-1.65 (m, 1H), 1.23-1.16 (m, 2H); LC-MS (ESI$^+$) m/z 722.3 (M+H)$^+$.

Example 17: Synthesis of N-[2-[4-[[(1R,5S)-3-[1-(2,6-dioxo-3-piperidyl)-3-methyl-2-oxo-benzimidazol-4-yl]-8-azabicyclo[3.2.1]octan-8-yl]methyl]cyclohexyl]indazol-5-yl]-6-(trifluoromethyl)pyridine-2-carboxamide (I-251) & N-[2-[4-[[(1S,5R)-3-[1-(2,6-dioxo-3-piperidyl)-3-methyl-2-oxo-benzimidazol-4-yl]-8-azabicyclo[3.2.1]octan-8-yl]methyl]cyclohexyl]indazol-5-yl]-6-(trifluoromethyl)pyridine-2-carboxamide (I-250)
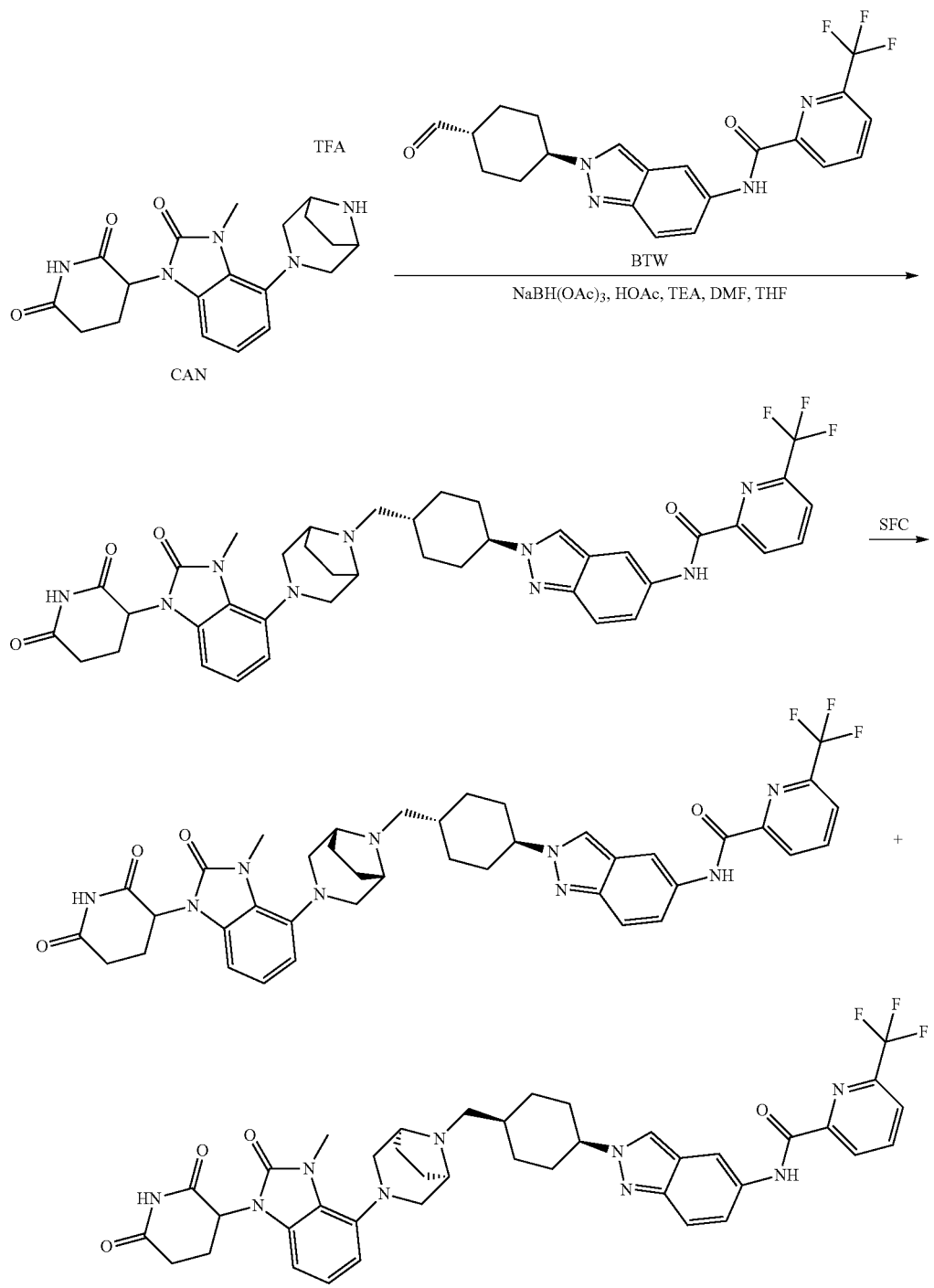

Step 1—N-[2-[4-[[3-[1-(2,6-dioxo-3-piperidyl)-3-methyl-2-oxo-benzimidazol-4-yl]-8-azabicyclo[3.2.1]octan-8-yl]methyl]cyclohexyl]indazol-5-yl]-6-(trifluoromethyl)pyridine-2-carboxamide To a solution of 3-[4-(8-azabicyclo[3.2.1]octan-3-yl)-3-methyl-2-oxo-benzimidazol-1-yl]piperidine-2,6-dione (44 mg, 91.2 umol, TFA, Intermediate CAN), TEA (9.23 mg, 91.2 umol, 12.6 uL) HOAc (10.9 mg, 182 umol, 10.4 uL) in DMF (0.5 mL) and THF (0.5 mL) was added N-[2-(4-formylcyclohexyl)indazol-5-yl]-6-(trifluoromethyl)pyridine-2-carboxamide (37.9 mg, 91.2 umol, Intermediate BTW) at −10° C. The reaction mixture was stirred at −10° C. for 0.5 hr. Then, to the above reaction mixture was added NaBH(OAc)$_3$ (28.9 mg, 136 umol) at −10° C. and the mixture was stirred for 1.5 hrs. On completion, the reaction mixture was quenched with water (0.2 mL) and concentrated in vacuo. The residue was purified by prep-HPLC(column: Phenomenex luna C18 150*25 mm*10 um; mobile phase: [water (0.225% FA)-ACN]; B %: 20%-50%, 10 min) to give title compound (52 mg, 70% yield, FA) as white solid. $^1$H NMR (400 MHz, DMSO-d$_6$) δ 11.11-11.07 (m, 1H), 10.36 (s, 1H), 8.44-8.33 (m, 3H), 8.32-8.29 (m, 1H), 8.19-8.13 (m, 1H), 7.64-7.59 (m, 1H), 7.57-7.53 (m, 1H), 7.17-6.92 (m, 3H), 5.40-5.33 (m, 1H), 4.52-4.40 (m, 1H), 3.88-3.78 (m, 1H), 3.59 (s, 3H), 2.93-2.83 (m, 1H), 2.76-2.67 (m, 1H), 2.65-2.59 (m, 1H), 2.45-2.37 (m, 2H), 2.29-2.17 (m, 4H), 2.12-1.86 (m, 9H), 1.65-1.14 (m, 7H).

Step 2—N-[2-[[4-[R1R,5S)-3-[1-(2,6-dioxo-3-piperidyl)-3-methyl-2-oxo-benzimidazol-4-yl]-8-azabicyclo[3.2.1]octan-8-yl]methyl]cyclohexyl]indazol-5-yl]-6-(trifluoromethyl)pyridine-2-carboxamide & N-[2-[4-[[(1S,5R)-3-[1-(2,6-dioxo-3-piperidyl)-3-methyl-2-oxo-benzimidazol-4-yl]-8-azabicyclo[3.2.1] octan-8-yl]methyl]cyclohexyl]indazol-5-yl]-6-(trifluoromethyl)pyridine-2-carboxamide N-(2-((1r,4r)-4-((3-(1-(2,6-dioxopiperidin-3-yl)-3-methyl-2-oxo-2,3-dihydro-1H-benzo[d]imidazol-4-yl)-8-azabicyclo[3.2.1] octan-8-yl)methyl)cyclohexyl)-2H-indazol-5-yl)-6-(trifluoromethyl)picolinamide (52 mg) was separated by SFC (column: REGIS (R,R)WHELK-O1 (250 mm*25 mm, 10 um); mobile phase: [0.1% NH3H2O ETOH]; B %: 60%-60%, 6; 60 min) to give N-[2-[4-[[(1R,5S)-3-[1-(2,6-dioxo-3-piperidyl)-3-methyl-2-oxo-benzimidazol-4-yl]-8-azabicyclo[3.2.1]octan-8-yl]methyl]cyclohexyl]indazol-5-yl]-6-(trifluoromethyl)pyridine-2-carboxamide (30.86 mg, $^1$H NMR (400 MHz, DMSO-d$_6$) δ 11.09 (s, 1H), 10.36 (s, 1H), 8.46-8.27 (m, 4H), 8.17 (d, J=7.6 Hz, 1H), 7.65-7.51 (m, 2H), 7.31-7.15 (m, 1H), 7.09-6.96 (m, 2H), 5.44-5.30 (m, 1H), 4.48 (d, J=3.6 Hz, 1H), 4.55-4.41 (m, 1H), 3.60 (s, 3H), 2.95-2.84 (m, 2H), 2.72-2.62 (m, 2H), 2.25-2.16 (m, 3H), 2.09-1.86 (m, 10H), 1.62-1.51 (m, 2H), 1.42-1.31 (m, 4H), 0.90-0.85 (m, 2H); LC-MS (ESI$^+$) m/z 769.3 (M+H)$^+$), the second of two peaks on SFC spectrogram) and N-[2-[4-[[(1S,5R)-3-[1-(2,6-dioxo-3-piperidyl)-3-methyl-2-oxo-benzimidazol-4-yl]-8-azabicyclo[3.2.1]octan-8-yl]methyl]cyclohexyl]indazol-5-yl]-6-(trifluoromethyl)pyridine-2-carboxamide (2.60 mg, $^1$H NMR (400 MHz, DMSO-d$_6$) δ 11.09 (s, 1H), 10.36 (s, 1H), 8.44-8.28 (m, 4H), 8.20-8.15 (m, 1H), 7.65-7.52 (m, 2H), 7.16-6.94 (m, 3H), 5.41-5.32 (m, 1H), 4.53-4.43 (m, 1H), 3.82-3.70 (m, 1H), 3.66 (s, 3H), 2.92-2.83 (m, 1H), 2.77-2.59 (m, 3H), 2.24-2.15 (m, 3H), 2.11-1.90 (m, 10H), 1.81-1.58 (m, 3H), 1.35-1.12 (m, 4H), 0.91-0.80 (m, 1H)); LC-MS (ESI$^+$) m/z 769.3 (M+H)$^+$(The first of two peaks on SFC spectrogram). Absolute stereochemistry of the diastereomers was assigned arbitrarily.

Example 18: Synthesis of N-[2-[4-[[4-[1-[(3S)-2,6-dioxo-3-piperidyl]-5-methoxy-3-methyl-2-oxo-benzimidazol-4-yl]-1-piperidyl]methyl]cyclohexyl]pyrazolo[3,4-c]pyridin-5-yl]-6-(trifluoromethyl)pyridine-2-carboxamide (I-275) & N-[2-[4-[[4-[1-[(3R)-2,6-dioxo-3-piperidyl]-5-methoxy-3-methyl-2-oxo-benzimidazol-4-yl]-1-piperidyl]methyl]cyclohexyl]pyrazolo[3,4-c]pyridine-5-yl]-6-(trifluoromethyl)pyridine-2-carboxamide (I-274)

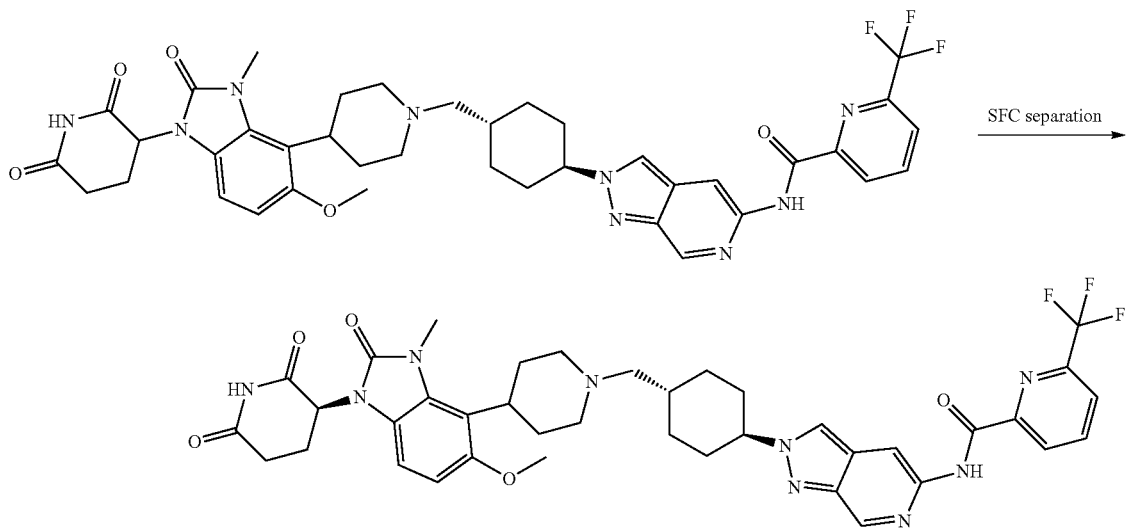

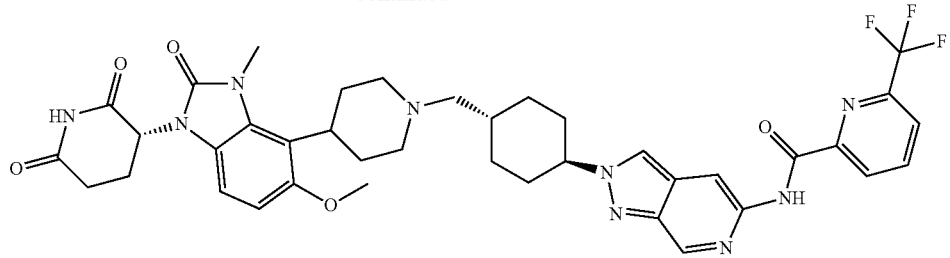

N-[2-[4-[[4-[1-[(3S)-2,6-dioxo-3-piperidyl]-5-methoxy-3-methyl-2-oxo-benzimidazol-4-yl]-1-piperidyl]methyl]cyclohexyl]pyrazolo[3,4-c]pyridin-5-yl]-6-(trifluoromethyl)pyridine-2-carboxamide (300 mg, 387 umol, Example 1-104 was separated by SFC (column: DAICEL CHIRALPAK IC (250 mm*30 mm, 10 um); mobile phase: [IPA-ACN]; B %: 80%-80%, 6.8; 30 min) to give N-[2-[4-[[4-[1-[(3S)-2,6-dioxo-3-piperidyl]-5-methoxy-3-methyl-2-oxo-benzimidazol-4-yl]-1-piperidyl]methyl]cyclohexyl]pyrazolo[3,4-c]pyridin-5-yl]-6-(trifluoromethyl)pyridine-2-carboxamide (peak 1, 23.3 mg, 7% yield, FA) as a white solid ($^1$H NMR (400 MHz, DMSO-$d_6$) δ 11.08 (s, 1H), 10.20 (s, 1H), 9.07 (s, 1H), 8.62 (s, 1H), 8.52-8.46 (m, 2H), 8.45-8.38 (m, 1H), 8.23 (d, J=7.6 Hz, 1H), 6.91 (d, J=8.4 Hz, 1H), 6.72 (d, J=8.4 Hz, 1H), 5.32 (dd, J=5.2, 13.2 Hz, 1H), 4.62-4.54 (m, 1H), 3.77 (s, 3H), 3.56 (s, 3H), 2.97 (d, J=10.0 Hz, 2H), 2.92-2.82 (m, 1H), 2.69 (s, 2H), 2.41 (d, J=12.0 Hz, 3H), 2.20 (d, J=6.4 Hz, 4H), 1.98 (t, J=10.0 Hz, 7H), 1.74-1.65 (m, 1H), 1.62-1.53 (m, 2H), 1.24-1.11 (m, 2H); LC-MS (ESI$^+$) m/z 774.2 (M+H)$^+$) and N-[2-[4-[[4-[1-[(3R)-2,6-dioxo-3-piperidyl]-5-methoxy-3-methyl-2-oxo-benzimidazol-4-yl]-1-piperidyl]methyl]cyclohexyl]pyrazolo[3,4-c]pyridine-5-yl]-6-(trifluoromethyl)pyridine-2-carboxamide (peak 2, 9.8 mg, 5% yield, FA) as a white solid ($^1$H NMR (400 MHz, DMSO-$d_6$) δ 11.08 (s, 1H), 10.20 (s, 1H), 9.07 (s, 1H), 8.61 (s, 1H), 8.52-8.46 (m, 2H), 8.45-8.38 (m, 1H), 8.23 (d, J=7.6 Hz, 1H), 6.91 (d, J=8.8 Hz, 1H), 6.72 (d, J=8.8 Hz, 1H), 5.32 (m, 1H), 4.66-4.51 (m, 1H), 3.76 (s, 3H), 3.56 (s, 3H), 2.97 (d, J=10.8 Hz, 2H), 2.92-2.80 (m, 1H), 2.71-2.58 (m, 4H), 2.41 (d, J=11.2 Hz, 2H), 2.20 (d, J=8.0 Hz, 4H), 1.99 (t, J=10.0 Hz, 6H), 1.75-1.64 (m, 1H), 1.57 (d, J=10.8 Hz, 2H), 1.24-1.08 (m, 2H); LC-MS (ESI$^+$) m/z 774.3 (M+H)$^+$).

Example 19: Synthesis of N-[2-[4-[[[2-(2,6-dioxo-3-piperidyl)-1,3-dioxo-isoindolin-4-yl]amino]methyl] cyclohexyl]-6-(1-hydroxy-1-methyl-ethyl)indazol-5-yl]-6-(trifluoromethyl)pyridine-2-carboxamide (I-338)

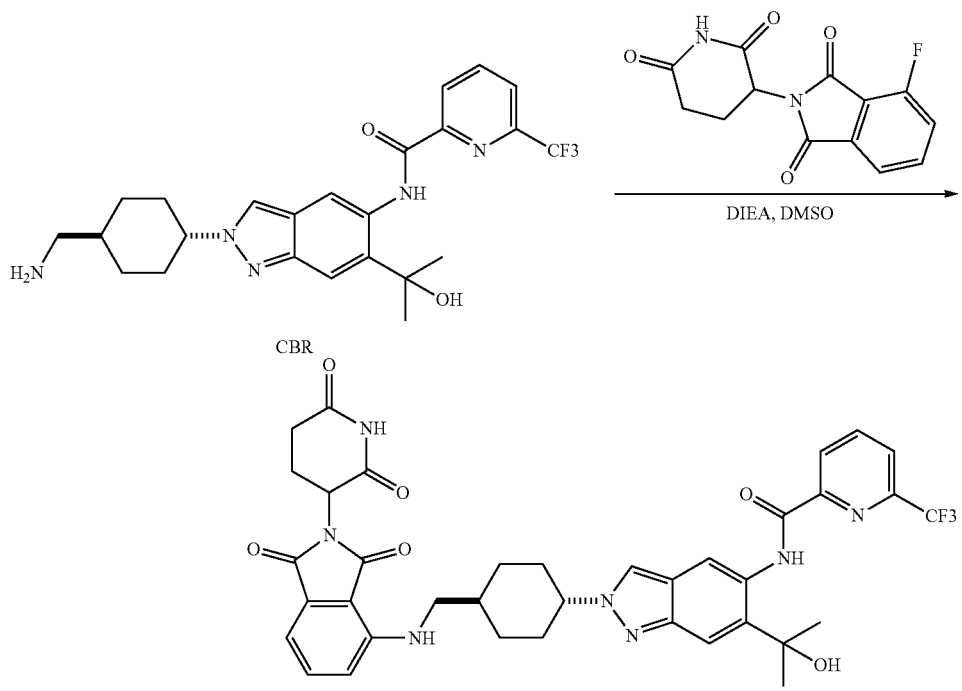

A mixture of N-[2-[4-(aminomethyl)cyclohexyl]-6-(1-hydroxy-1-methyl-ethyl)indazol-5-yl]-6-(trifluoromethyl)pyridine-2-carboxamide (15.0 mg, 31.5 umol, Intermediate CBR), 2-(2,6-dioxo-3-piperidyl)-4-fluoro-isoindoline-1,3-dione (7.26 mg, 26.2 umol, CAS #835616-60-9), DIEA (3.40 mg, 26.2 umol) in DMSO (2 mL) was degassed and purged with $N_2$ three times. Then the mixture was stirred at 100° C. for 1 hours under $N_2$ atmosphere. On completion, the crude product was purified by reversed-phase HPLC (column: Phenomenex Luna C18 100*30 mm*5 um; mobile phase: [water(FA)-ACN]; B %: 47%-77%, 8 min) to give the title compound (3.91 mg, 20% yield) as yellow solid. LC-MS (ESI$^+$) m/z 732.2 (M+H)$^{+1}$. 1H NMR (400 MHz, DMSO-d6) δ 12.36 (s, 1H), 11.18-11.02 (m, 1H), 8.71 (s, 1H), 8.49-8.43 (m, 1H), 8.41-8.33 (m, 2H), 8.16 (d, J=7.8 Hz, 1H), 7.66-7.54 (m, 2H), 7.19 (d, J=8.6 Hz, 1H), 7.05 (d, J=7.0 Hz, 1H), 6.69 (t, J=6.0 Hz, 1H), 5.94 (s, 1H), 5.07 (dd, J=5.4, 12.9 Hz, 1H), 4.53-4.39 (m, 1H), 2.96-2.82 (m, 1H), 2.62 (d, J=2.6 Hz, 1H), 2.57 (d, J=8.1 Hz, 1H), 2.53 (s, 2H), 2.53 (s, 4H), 2.17 (d, J=10.3 Hz, 2H), 2.09-2.03 (m, 1H), 1.98 (s, 1H), 1.94 (s, 2H), 1.92-1.87 (m, 1H), 1.81-1.70 (m, 1H), 1.62 (s, 6H), 1.37-1.11 (m, 3H).

Example 20: Synthesis of N-[2-[4-[[2-[[2-(2,6-dioxo-3-piperidyl)-1,3-dioxo-isoindolin-4-yl]amino]ethyl-methyl-amino] methyl]cyclohexyl]-6-(1-hydroxy-1-methyl-ethyl)indazol-5-yl]-6-(trifluoromethyl)pyridine-2-carboxamide (I-341)

Step 1—N-[2-[4-[[2-[[2-(2,6-dioxo-3-piperidyl)-1,3-dioxo-isoindolin-4-yl]amino]ethylamino]methyl]cyclohexyl]-6-(1-hydroxy-1-methyl-ethyl)indazol-5-yl]-6-(trifluoromethyl)pyridine-2-carboxamide To a mixture of 4-(2-aminoethylamino)-2-(2,6-dioxo-3-piperidyl)isoindoline-1,3-dione (113 mg, 357 umol Intermediate CBU) in a mixed solvent of THF (2.0 mL) and DMF (0.5 mL) was added Et3N (36.1 mg, 357 umol, 49.7 uL) at −10° C. until the pH stabilized at 8. The mixture was stirred at −10° C. for 2 minutes, then HOAc (21.4 mg, 357 umol, 20.4 uL) was added at −10° C. to solution until the pH stabilized at 5~6. Subsequently, N-[2-(4-formylcyclohexyl)-6-(1-hydroxy-1-methyl-ethyl)indazol-5-yl]-6-(trifluoromethyl)pyridine-2-carboxamide (135 mg, 285 umol, Intermediate CBN) was added and stirred for 1 hour. After that, NaBH(OAc)$_3$ (151 mg, 714 umol) was added in one portion. The resulting reaction mixture was stirred at −10° C. for 1 hour. On completion, the mixture was concentrated to give a residue. The residue was purified by prep-HPLC (column:

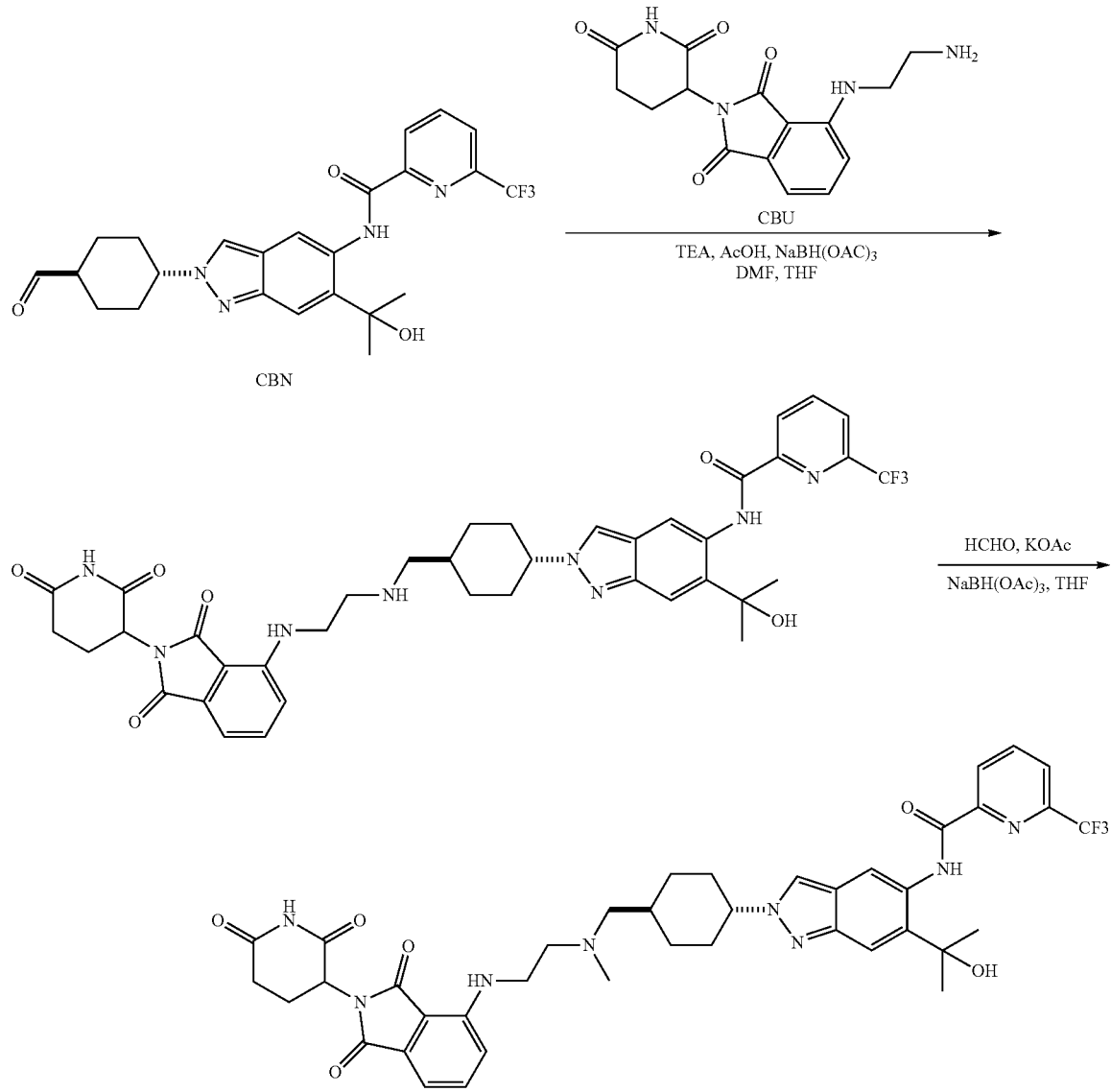

Phenomenex luna C18 150*25 mm*10 um; mobile phase: [water(FA)-ACN]; B %: 20%-50%, 10.5 min) to give the title compound (57.1 mg, 20% yield) as a yellow solid. $^1$H NMR (400 MHz, DMSO-$d_6$) δ 12.36 (s, 1H), 11.09 (s, 1H), 8.71 (s, 1H), 8.47-8.42 (m, 1H), 8.41-8.34 (m, 2H), 8.16 (d, J=8.0 Hz, 1H), 7.63 (t, J=8.0 Hz, 1H), 7.57 (s, 1H), 7.16 (d, J=8.8 Hz, 1H), 7.08 (d, J=7.2 Hz, 1H), 6.86 (t, J=5.2 Hz, 1H), 5.93 (s, 1H), 5.12-5.01 (m, 1H), 4.52-4.36 (m, 1H), 3.57-3.47 (m, 2H), 2.98 (s, 2H), 2.91-2.84 (m, 1H), 2.70 (d, J=1.2 Hz, 1H), 2.61 (d, J=2.0 Hz, 2H), 2.16 (d, J=12.0 Hz, 2H), 2.08-1.83 (m, 6H), 1.62 (s, 8H), 1.29-1.16 (m, 2H). LC-MS (ESI+) m/z 775.2 (M+H)$^+$.

Step 2—N-[2-[4-[[2-[[2-(2,6-dioxo-3-piperidyl)-1,3-dioxo-isoindolin-4-yl]amino]ethyl-methyl-amino]methyl]cyclohexyl]-6-(1-hydroxy-1-methyl-ethyl)indazol-5-yl]-6-(trifluoromethyl)pyridine-2-carboxamide To a solution of N-[2-[4-[[2-[[2-(2,6-dioxo-3-piperidyl)-1,3-dioxo-isoindolin-4-yl]amino]ethylamino]methyl]cyclohexyl]-6-(1-hydroxy-1-methyl-ethyl)indazol-5-yl]-6-(trifluoromethyl)pyridine-2-carboxamide (20.0 mg, 25.8 umol) in THF (0.5 mL) was added, and HCHO (13.9 mg, 464 umol, 12.8 uL) at 0° C. was stirred for 0.25 hours. Next, NaBH(OAc)$_3$ (10.9 mg, 51.6 umol) was added in portions at 0° C. The mixture was then stirred at 20° C. for 2 hours. On completion, the mixture was concentrated to give a residue. The residue was purified by prep-HPLC (column: Phenomenex luna C18 150*25 mm*10 um; mobile phase: [water (FA)-ACN]; B %: 18%-48%, 10.5 min) to give the title compound (11.3 mg, 55% yield) as a yellow solid. $^1$H NMR (400 MHz, DMSO-$d_6$) δ 12.36 (s, 1H), 11.06 (s, 1H), 8.72-8.67 (m, 1H), 8.48-8.43 (m, 1H), 8.39-8.28 (m, 2H), 8.16 (d, J=8.0 Hz, 1H), 7.64-7.54 (m, 2H), 7.11 (d, J=8.4 Hz, 1H), 7.04 (d, J=7.2 Hz, 1H), 6.79-6.72 (m, 1H), 5.95-5.92 (m, 1H), 5.06-4.99 (m, 1H), 4.40 (tt, J=4.0, 12.0 Hz, 1H), 3.36 (d, J=5.2 Hz, 2H), 2.89-2.78 (m, 1H), 2.59 (t, J=5.6 Hz, 2H), 2.56-2.52 (m, 2H), 2.24-2.21 (m, 4H), 2.11 (d, J=11.6 Hz, 2H), 2.04-1.92 (m, 3H), 1.90-1.81 (m, 2H), 1.62 (s, 8H), 1.16-1.02 (m, 2H); LC-MS (ESI+) m/z 789.3 (M+H)$^+$.

Examples 21: Syntheses of N-[2-[4-[[4-[1-[(3S)-2,6-dioxo-3-piperidyl]-3-methyl-2-oxo-benzimidazol-4-yl]-1-piperidyl]methyl]cyclohexyl]-6-methyl-indazol-5-yl]-6-(trifluoromethyl)pyridine-2-carboxamide (I-390) and N-[2-[4-[[4-[1-[(3R)-2,6-dioxo-3-piperidyl]-3-methyl-2-oxo-benzimidazol-4-yl]-1-piperidyl]methyl]cyclohexyl]-6-methyl-indazol-5-yl]-6-(trifluoromethyl)pyridine-2-carboxamide (I-394)

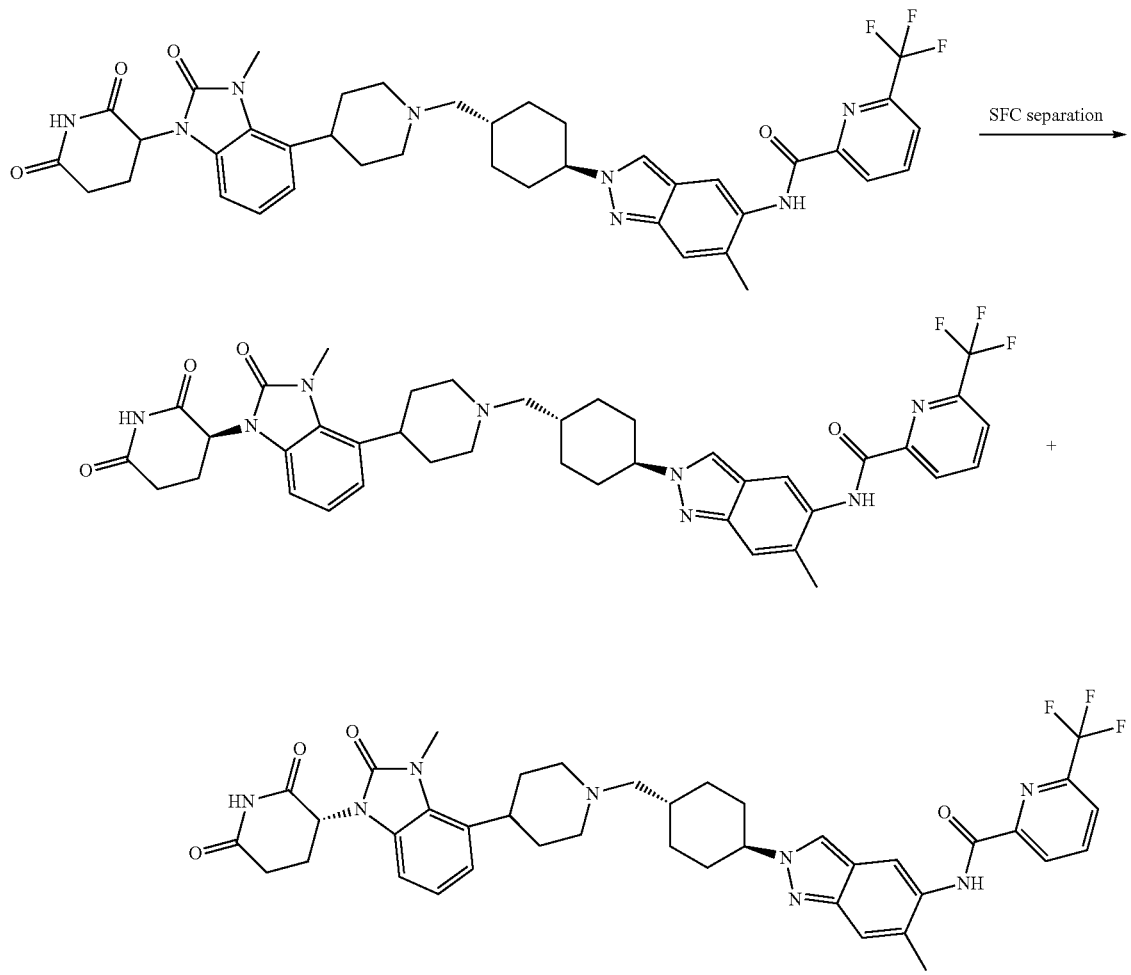

N-[2-[4-[[4-[1-(2,6-dioxo-3-piperidyl)-3-methyl-2-oxo-benzimidazol-4-yl]-1-piperidyl]methyl]cyclohexyl]-6-methyl-indazol-5-yl]-6-(trifluoromethyl)pyridine-2-carboxamide (500 mg, 660 umol, synthesized via Method 2 coupling Intermediate AZK with Intermediate BSC) was purified by SFC (column: Welch Ultimate C18 150*25 mm*5 um; mobile phase: [water (FA)-ACN]; B %: 18%-48%, 10 min) to give N-[2-[4-[[4-[1-[(3S)-2,6-dioxo-3-piperidyl]-3-methyl-2-oxo-benzimidazol-4-yl]-1-piperidyl]methyl]cyclohexyl]-6-methyl-indazol-5-yl]-6-(trifluoromethyl)pyridine-2-carboxamide (119 mg, 24% yield) as a white solid ($^1$H NMR (400 MHz, DMSO -d$_6$) δ 11.10 (s, 1H), 10.13 (s, 1H), 8.45-8.42 (m, 1H), 8.41-8.36 (m, 2H), 8.22-8.19 (m, 2H), 7.51 (s, 1H), 7.05-7.00 (m, 2H), 6.99-6.96 (m, 1H), 5.41-5.33 (m, 1H), 4.48-4.38 (m, 1H), 3.59 (s, 3H), 3.03-2.97 (m, 2H), 2.94-2.84 (m, 1H), 2.77-2.65 (m, 2H), 2.54 (s, 1H), 2.40 (s, 3H), 2.25-2.13 (m, 4H), 2.12-2.03 (m, 2H), 2.02-1.89 (m, 5H), 1.84-1.75 (m, 4H), 1.72-1.61 (m, 1H), 1.20-1.08 (m, 2H). LC-MS (ESI$^+$) m/z 757.3 (M+H)$^+$) and N-[2-[4-[[4-[1-[(3R)-2,6-dioxo-3-piperidyl]-3-methyl-2-oxo-benzimidazol-4-yl]-1-piperidyl]methyl]cyclohexyl]-6-methyl-indazol-5-yl]-6-(trifluoromethyl)pyridine-2-carboxamide (71.0 mg, 14% yield) as a white solid ($^1$H NMR (400 MHz, DMSO-d$_6$) δ 11.10 (s, 1H), 10.13 (s, 1H), 8.45-8.42 (m, 1H), 8.40 (d, J=7.6 Hz, 1H), 8.37 (s, 1H), 8.23-8.17 (m, 2H), 7.51 (s, 1H), 7.05-6.95 (m, 3H), 5.37-5.34 (m, 1H), 4.48-4.38 (m, 1H), 3.59 (s, 3H), 3.00-2.99 (m, 2H), 2.94-2.84 (m, 1H), 2.76-2.66 (m, 2H), 2.40 (s, 3H), 2.24-2.13 (m, 4H), 2.11-2.04 (m, 2H), 2.03-1.90 (m, 5H), 1.84-1.74 (m, 4H), 1.71-1.62 (m, 1H), 1.23 (s, 1H), 1.20-1.08 (m, 2H). LC-MS (ESI$^+$) m/z 757.3 (M+H)$^+$). The absolute stereochemistry was assigned arbitrarily.

Example 22: Syntheses of N-[2-[4-[[4-[1-[(3S)-2,6-dioxo-3-piperidyl]-3-methyl-2-oxo-benzimidazol-4-yl]piperazin-1-yl]methyl]cyclohexyl]-6-methyl-indazol-5-yl]-6-(trifluoromethyl)pyridine-2-carboxamide (I-399) and N-[2-[4-[[4-[1-[(3R)-2,6-dioxo-3-piperidyl]-3-methyl-2-oxo-benzimidazol-4-yl]piperazin-1-yl]methyl]cyclohexyl]-6-methyl-indazol-5-yl]-6-(trifluoromethyl)pyridine-2-carboxamide (I-400)

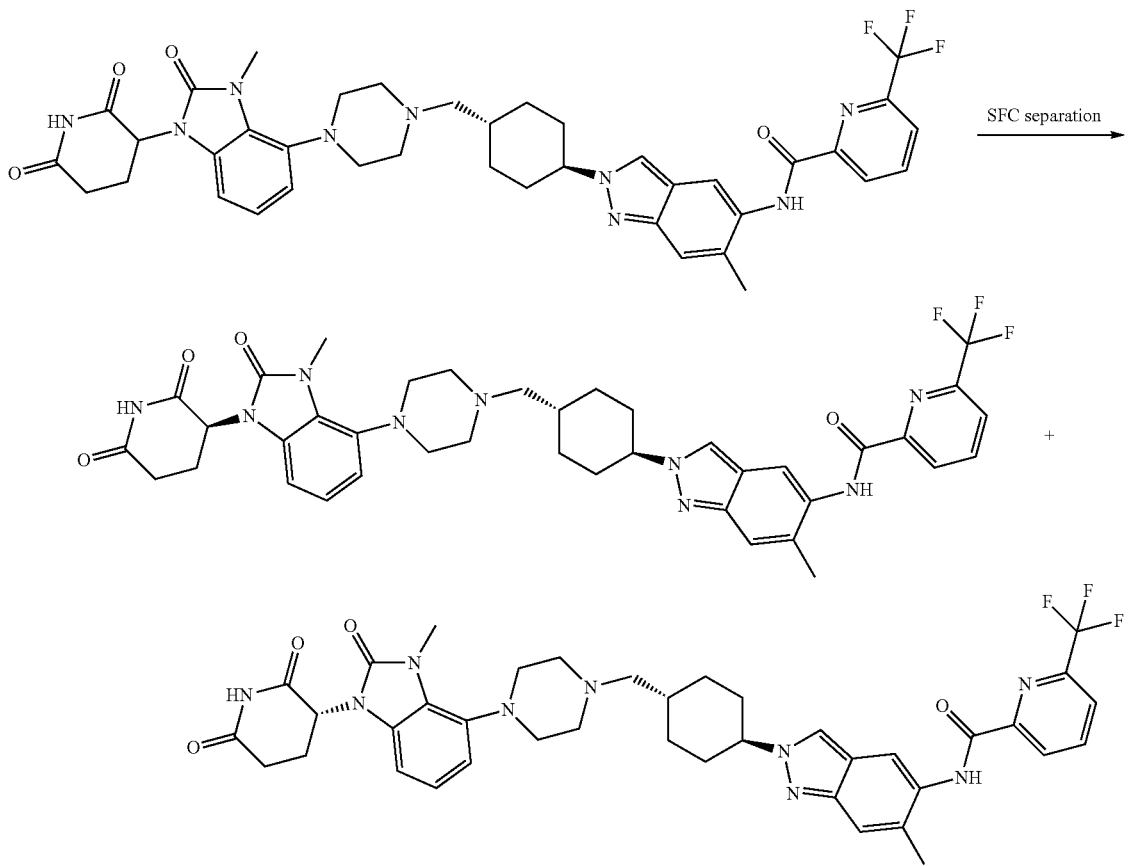

N-[2-[4-[[4-[1-(2,6-dioxo-3-piperidyl)-3-methyl-2-oxo-benzimidazol-4-yl]piperazin-1-yl]methyl]cyclohexyl]-6-methyl-indazol-5-yl]-6-(trifluoromethyl)pyridine-2-carboxamide (500 mg, 660 umol, Example 1-260) was separated by SFC (column: DAICEL CHIRALPAK AD (250 mm*30 mm, 10 um); mobile phase: [0.1% NH3H2O IPA]; B %: 60%-60%, 5; 80 min) to give N-[2-[4-[[4-[1-[(3S)-2,6-dioxo-3-piperidyl]-3-methyl-2-oxo -benzimidazol-4-yl]piperazin-1-yl]methyl]cyclohexyl]-6-methyl-indazol-5-yl]-6-(trifluoromethyl)pyridine -2-carboxamide (175 mg, 35% yield) as a yellow solid ($^1$H NMR (400 MHz, DMSO-d$_6$) δ 11.09 (s, 1H), 10.13 (s, 1H), 8.46-8.34 (m, 3H), 8.23-8.18 (m, 2H), 7.51 (s, 1H), 7.02-6.92 (m, 2H), 6.89 (d, J=7.6 Hz, 1H), 5.37-5.32 (m, 1H), 4.50-4.37 (m, 1H), 3.64 (s, 3H), 3.02-2.84 (m, 6H), 2.66-2.58 (m, 2H), 2.56-2.53 (m, 3H), 2.40 (s, 3H), 2.26-2.25 (m, 2H), 2.18-2.15 (m, 2H), 2.04-1.88 (m, 5H), 1.75-1.62 (m, 1H), 1.23-1.08 (m, 2H); LC-MS (ESI$^+$) m/z 758.3 (M+H)$^+$) and N-[2-[4-[[4-[1-[(3R)-2,6- dioxo-3-piperidyl]-3-methyl-2-oxo-benzimidazol-4-yl]piperazin-1-yl]methyl]cyclohexyl]-6-methyl-indazol-5-yl]-6-(trifluoromethyl)pyridine-2-carboxamide (175 mg, 35% yield) as a yellow solid ($^1$H NMR (400 MHz, DMSO-$d_6$) δ 11.09 (s, 1H), 10.13 (s, 1H), 8.46-8.35 (m, 3H), 8.23-8.18 (m, 2H), 7.51 (s, 1H), 7.02-6.92 (m, 2H), 6.89 (d, J=7.2 Hz, 1H), 5.37-5.32 (m, 1H), 4.49-4.38 (m, 1H), 3.64 (s, 3H), 3.01-2.82 (m, 6H), 2.67-2.56 (m, 2H), 2.52-2.51 (m, 3H), 2.40 (s, 3H), 2.26-2.24 (m, 2H), 2.17-2.15 (m, 2H), 2.03-1.87 (m, 5H), 1.74-1.62 (m, 1H), 1.24-1.08 (m, 2H). LC-MS (ESI$^+$) m/z 758.3 (M+H)$^+$).

Example 23: Synthesis of 2-[4-[[4-[1-(2,6-dioxo-3-piperidyl)-3-methyl-2-oxo-benzimidazol-4-yl]piperazin-1-yl]methyl]cyclohexyl]-5-[[6-(trifluoromethyl)pyridine-2-carbonyl]amino]indazole-6-carboxylic acid (I-415)

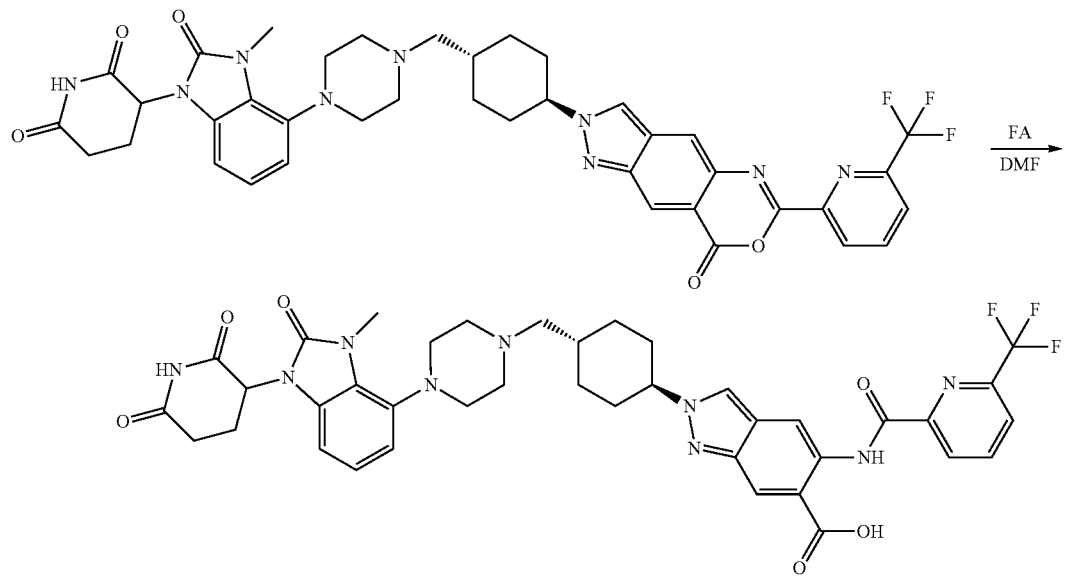

To a solution of 3-[3-methyl-2-oxo-4-[4-[[4-[8-oxo-6-[6-(trifluoromethyl)-2-pyridyl]pyrazolo[3,4-g][3,1]benzoxazin-2-yl]cyclohexyl]methyl]piperazin-1-yl]benzimidazol-1-yl]piperidine-2,6-dione (25.0 mg, 32.4 umol, Example 1-406) in DMF (0.5 mL) was added FA (0.2 mL) at 25° C. The reaction was then stirred at 25° C. for 48 hr. On completion, the reaction mixture was filtered and the filtrate was concentrated in vacuo. The crude product was purified by prep-HPLC (column: Phenomenex Luna C18 150*25 mm*10 um; mobile phase: [water (FA)-ACN]; B %: 15%-45%, 10.5 min) to give the title compound (8.7 mg, 34% yield) as white solid. $^1$H NMR (400 MHz, DMSO-$d_6$) δ 11.08 (s, 1H), 9.10 (s, 1H), 8.49 (s, 1H), 8.46-8.41 (m, 2H), 8.36 (t, J=8.0 Hz, 1H), 8.16 (d, J=7.6 Hz, 1H), 7.02-6.93 (m, 2H), 6.91-6.87 (m, 1H), 5.39-5.31 (m, 1H), 4.55-4.46 (m, 1H), 3.64 (s, 3H), 3.07-2.83 (m, 7H), 2.70 (s, 1H), 2.67-2.58 (m, 2H), 2.27 (d, J=6.8 Hz, 3H), 2.22-2.15 (m, 3H), 2.05-1.91 (m, 6H), 1.75-1.65 (m, 1H), 1.23-1.14 (m, 2H); LC-MS (ESI$^+$) m/z 788.3 (M+H)$^+$.

Example 24. IRAK4 MSD Degradation in OCI-LY10

Degradation of IRAK4 in OCI-LY10 was quantitatively measured using Meso Scale Discovery technology. OCI-LY10 cells were seeded in 96-well plates (Corning 3799) with a density of 300,000 cells per well in 100 μL fresh media. Compounds were then added to the assay plates with a final top concentration of 1 to 10 μM in a 1:3 dilution series with total of 8 doses. The assay plates were then incubated for 4 to 24 hours at 37° C. under 5% CO2. The assay plates were then centrifuged for 5 minutes and the cell pellets were treated with 100 μL/well RIPA lysis buffer (Boston Bio-Products BP-115D) with proteinase inhibitors. To prepare MSD assay plates (Meso Scale Discovery Catalog number L15XA-3), the plates were coated with 2 μg/mL capture antibody (mouse Anti-IRAK4 antibody [2H9], ab119942) in PBS, at 40 μL/well. The plates were then incubated overnight at 4° C., washed 3 times with 150 μL/well TBST buffer (Cell Signaling Technology, Catalog number 9997S) and blocked with 150 μL/well blocking buffer (Meso Scale Discovery Catalog number R93BA-4). Cell lysates were then added to MSD assay plates and the plates were incubated at room temperature for 1 hour. The plates were then washed 3 times with 150 μL/well TBST buffer and 254/well primary detection antibody (rabbit Anti-IRAK4 antibody [Y279], from Abcam. Catalog number ab32511, 1 μg/mL). The assay plates were then incubated at room temperature for 1 hour, washed 3 times with 150 μL/well TBST buffer and 254/well secondary detection antibody, SULFO-TAG anti-rabbit antibody were added (anti rabbit antibody from Meso Scale Discovery, Catalog number R32AB-1, 1 μg/mL). The assay plates were then incubated at room temperature for 1 hour, washed 3 times with 150 μL/well TBST buffer, and 150 μL/well MSD reading buffer (Meso Scale Discovery catalog number R92TC-2) was added. The plates were then analyzed by a MSD reader (Meso Scale Discovery, Model Quick Plex SQ 120). The data was then analyzed by software Prism 7.0 from GraphPad and the dose-depended IRAK4 degradation were fit using a three-parameter logistic equation to calculate $DC_{50}$.

IRAK4 MSD degradation results in OCI-LY10 cells for compounds of the invention are presented in Table 6. The letter codes for IRAK4 $DC_{50}$ include: A (<0.01 μM); B (0.01-0.05 μM); C (0.05-0.1 μM); D (0.1-0.2 μM); and E (>0.2 μM).

TABLE 6

IRAK4 MSD Degradation in OCI-LY10 Results

| I-# | IRAK4 degradation in OCI-LY10: $DC_{50}$ (μM) |
|---|---|
| I-1 | E |
| I-2 | E |
| I-3 | C |
| I-4 | C |
| I-5 | A |
| I-6 | A |
| I-7 | E |
| I-8 | B |
| I-9 | C |
| I-10 | C |
| I-11 | C |
| I-12 | B |
| I-13 | A |
| I-14 | C |
| I-15 | E |
| I-16 | B |
| I-17 | A |
| I-18 | E |
| I-19 | E |
| I-20 | E |
| I-21 | D |
| I-22 | E |
| I-23 | D |
| I-24 | B |
| I-25 | A |
| I-26 | A |
| I-27 | A |
| I-28 | B |
| I-29 | A |
| I-30 | B |
| I-31 | A |
| I-32 | A |
| I-33 | A |
| I-34 | E |
| I-35 | A |
| I-36 | A |
| I-37 | A |
| I-38 | A |
| I-39 | A |
| I-40 | B |
| I-41 | E |
| I-43 | E |
| I-44 | A |
| I-45 | A |
| I-46 | B |
| I-47 | B |
| I-48 | A |
| I-49 | E |
| I-50 | B |
| I-51 | A |
| I-52 | A |
| I-53 | B |
| I-54 | A |
| I-55 | B |
| I-56 | B |
| I-57 | A |
| I-58 | A |
| I-59 | E |
| I-60 | E |
| I-61 | E |
| I-62 | A |
| I-63 | A |
| I-64 | A |
| I-65 | A |
| I-66 | A |
| I-67 | B |
| I-68 | B |
| I-69 | A |
| I-70 | A |
| I-71 | A |
| I-72 | B |
| I-73 | B |
| I-74 | B |
| I-75 | B |
| I-76 | B |
| I-77 | A |
| I-78 | A |
| I-79 | E |
| I-80 | A |
| I-81 | A |
| I-82 | A |
| I-83 | A |
| I-84 | C |
| I-85 | C |
| I-86 | A |
| I-87 | A |
| I-88 | B |
| I-89 | B |
| I-90 | B |
| I-91 | B |
| I-92 | A |
| I-93 | A |
| I-94 | E |
| I-95 | A |
| I-96 | A |
| I-97 | A |
| I-98 | E |
| I-99 | A |
| I-100 | E |
| I-101 | A |
| I-102 | A |
| I-103 | B |
| I-104 | A |
| I-105 | C |
| I-106 | B |
| I-107 | A |
| I-108 | A |
| I-109 | A |
| I-110 | A |
| I-111 | A |
| I-112 | A |
| I-113 | A |
| I-114 | A |
| I-115 | E |
| I-116 | D |
| I-117 | C |
| I-118 | A |
| I-119 | E |
| I-120 | E |
| I-121 | B |
| I-122 | D |
| I-123 | B |
| I-125 | A |
| I-126 | B |
| I-127 | B |
| I-128 | A |
| I-129 | A |
| I-130 | A |
| I-131 | B |
| I-132 | A |
| I-134 | E |
| I-135 | E |
| I-136 | E |
| I-137 | A |
| I-138 | A |
| I-139 | B |
| I-140 | D |
| I-141 | B |
| I-142 | B |
| I-143 | C |
| I-144 | C |
| I-145 | B |
| I-147 | C |
| I-148 | D |
| I-149 | D |
| I-150 | D |
| I-151 | A |
| I-152 | B |
| I-154 | A |
| I-155 | B |
| I-156 | E |
| I-157 | C |

TABLE 6-continued

IRAK4 MSD Degradation in OCI-LY10 Results

| I-# | IRAK4 degradation in OCI-LY10: DC$_{50}$ (μM) |
|---|---|
| I-158 | A |
| I-159 | A |
| I-160 | E |
| I-161 | E |
| I-162 | E |
| I-163 | A |
| I-164 | A |
| I-165 | A |
| I-166 | E |
| I-167 | A |
| I-168 | A |
| I-169 | E |
| I-170 | E |
| I-171 | B |
| I-172 | E |
| I-173 | A |
| I-174 | A |
| I-175 | A |
| I-176 | A |
| I-177 | A |
| I-178 | E |
| I-179 | A |
| I-180 | E |
| I-181 | E |
| I-182 | A |
| I-183 | A |
| I-184 | A |
| I-185 | A |
| I-186 | A |
| I-187 | A |
| I-188 | E |
| I-189 | A |
| I-190 | A |
| I-191 | B |
| I-193 | E |
| I-194 | E |
| I-195 | B |
| I-196 | A |
| I-197 | A |
| I-198 | A |
| I-199 | B |
| I-200 | A |
| I-201 | E |
| I-202 | E |
| I-204 | B |
| I-205 | A |
| I-206 | A |
| I-207 | A |
| I-208 | A |
| I-209 | A |
| I-210 | E |
| I-211 | A |
| I-212 | E |
| I-213 | A |
| I-214 | A |
| I-215 | A |
| I-216 | A |
| I-217 | E |
| I-218 | A |
| I-219 | A |
| I-220 | A |
| I-221 | A |
| I-222 | A |
| I-223 | B |
| I-224 | A |
| I-225 | A |
| I-226 | A |
| I-227 | A |
| I-228 | A |
| I-229 | A |
| I-230 | A |
| I-231 | B |
| I-232 | A |
| I-233 | A |
| I-234 | A |
| I-235 | C |

TABLE 6-continued

IRAK4 MSD Degradation in OCI-LY10 Results

| I-# | IRAK4 degradation in OCI-LY10: DC$_{50}$ (μM) |
|---|---|
| I-237 | B |
| I-238 | A |
| I-239 | A |
| I-240 | A |
| I-241 | E |
| I-242 | A |
| I-243 | A |
| I-244 | D |
| I-245 | E |
| I-246 | B |
| I-247 | E |
| I-248 | A |
| I-249 | E |
| I-250 | B |
| I-251 | A |
| I-252 | B |
| I-253 | A |
| I-254 | A |
| I-255 | A |
| I-256 | A |
| I-257 | A |
| I-258 | E |
| I-259 | B |
| I-261 | B |
| I-262 | A |
| I-263 | B |
| I-266 | A |
| I-267 | E |
| I-268 | A |
| I-269 | A |
| I-271 | A |
| I-272 | A |
| I-273 | A |
| I-274 | B |
| I-275 | A |
| I-276 | A |
| I-277 | B |
| I-278 | A |
| I-279 | B |
| I-280 | B |
| I-281 | B |
| I-282 | A |
| I-283 | D |
| I-284 | B |
| I-285 | A |
| I-286 | B |
| I-287 | A |
| I-288 | B |
| I-289 | E |
| I-290 | B |
| I-291 | B |
| I-292 | A |
| I-293 | A |
| I-294 | B |
| I-295 | B |
| I-296 | B |
| I-297 | A |
| I-298 | A |
| I-299 | A |
| I-300 | B |
| I-301 | A |
| I-302 | B |
| I-303 | A |
| I-304 | B |
| I-305 | B |
| I-306 | B |
| I-307 | A |
| I-308 | A |
| I-309 | A |
| I-310 | E |
| I-311 | A |
| I-312 | E |
| I-313 | E |
| I-317 | D |
| I-318 | E |
| I-319 | B |

TABLE 6-continued

IRAK4 MSD Degradation in OCI-LY10 Results

| I-# | IRAK4 degradation in OCI-LY10: $DC_{50}$ (μM) |
|---|---|
| I-320 | A |
| I-321 | E |
| I-322 | A |
| I-323 | A |
| I-324 | B |
| I-325 | E |
| I-326 | A |
| I-327 | A |
| I-328 | B |
| I-329 | A |
| I-330 | E |
| I-331 | A |
| I-332 | B |
| I-353 | E |
| I-354 | E |
| I-355 | A |
| I-356 | A |
| I-357 | A |
| I-358 | B |
| I-359 | A |
| I-360 | B |
| I-361 | A |
| I-362 | A |
| I-363 | A |
| I-364 | A |
| I-365 | A |
| I-366 | A |
| I-367 | B |
| I-368 | E |
| I-369 | D |
| I-370 | B |
| I-371 | A |
| I-372 | A |
| I-373 | B |
| I-374 | E |
| I-375 | B |
| I-376 | B |
| I-377 | A |
| I-378 | A |
| I-379 | B |
| I-380 | B |
| I-382 | A |
| I-383 | A |
| I-384 | A |
| I-385 | B |
| I-386 | B |
| I-387 | B |
| I-388 | B |
| I-389 | B |
| I-390 | B |
| I-391 | B |
| I-392 | B |
| I-393 | D |
| I-394 | A |
| I-395 | A |
| I-396 | B |
| I-397 | A |
| I-398 | A |
| I-399 | B |
| I-400 | A |
| I-401 | A |
| I-402 | E |
| I-403 | E |
| I-404 | E |
| I-405 | B |
| I-406 | B |
| I-407 | A |
| I-408 | E |
| I-409 | B |
| I-410 | E |
| I-411 | B |
| I-412 | A |
| I-413 | A |
| I-414 | B |
| I-415 | B |
| I-416 | A |
| I-417 | A |
| I-418 | B |
| I-419 | A |
| I-420 | A |
| I-421 | C |
| I-422 | A |
| I-423 | A |
| I-424 | A |
| I-426 | A |
| I-427 | B |
| I-428 | A |
| I-430 | D |
| I-431 | E |
| I-432 | D |
| I-433 | B |
| I-434 | C |
| I-435 | B |
| I-436 | C |
| I-437 | B |
| I-438 | B |
| I-439 | B |
| I-440 | B |
| I-441 | B |
| I-442 | C |
| I-443 | B |
| I-444 | B |
| I-445 | A |
| I-446 | B |
| I-447 | A |
| I-448 | E |
| I-449 | E |
| I-450 | E |
| I-451 | C |
| I-452 | B |
| I-453 | D |
| I-454 | E |
| I-455 | E |
| I-456 | E |
| I-457 | D |
| I-458 | E |
| I-459 | E |
| I-460 | E |
| I-461 | B |
| I-462 | D |
| I-463 | B |
| I-464 | B |
| I-465 | A |
| I-466 | C |
| I-467 | B |
| I-468 | B |
| I-469 | D |
| I-470 | B |
| I-471 | E |
| I-472 | C |
| I-473 | D |
| I-474 | E |
| I-475 | A |
| I-476 | E |
| I-477 | D |
| I-478 | B |
| I-479 | E |
| I-480 | E |
| I-481 | E |
| I-482 | E |
| I-483 | E |
| I-484 | E |
| I-485 | B |
| I-486 | D |
| I-488 | D |
| I-489 | E |
| I-490 | E |
| I-491 | C |
| I-492 | B |
| I-493 | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

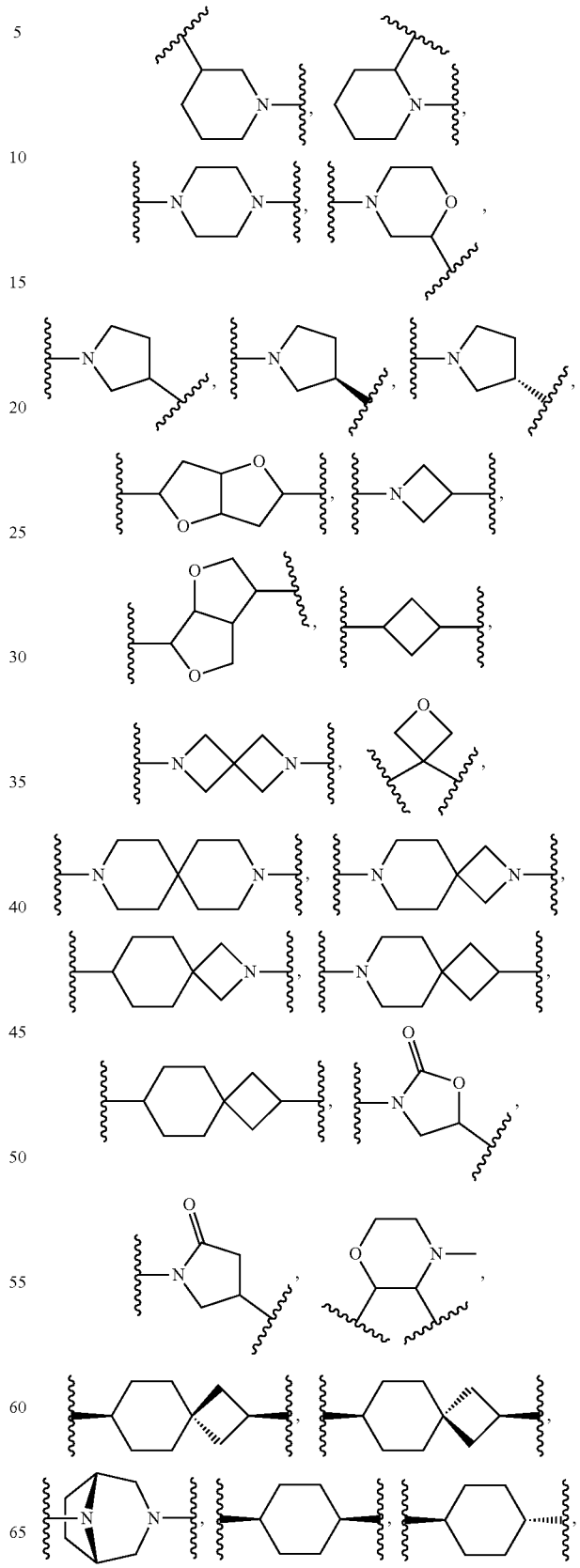

1415
-continued
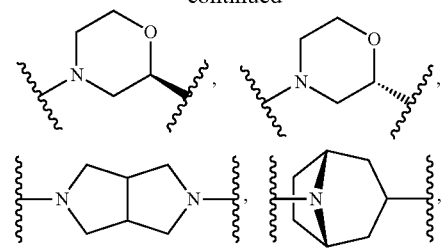
1416
-continued
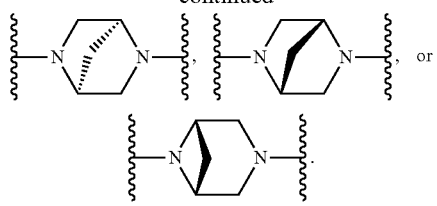
15. The compound of claim 1, wherein L is
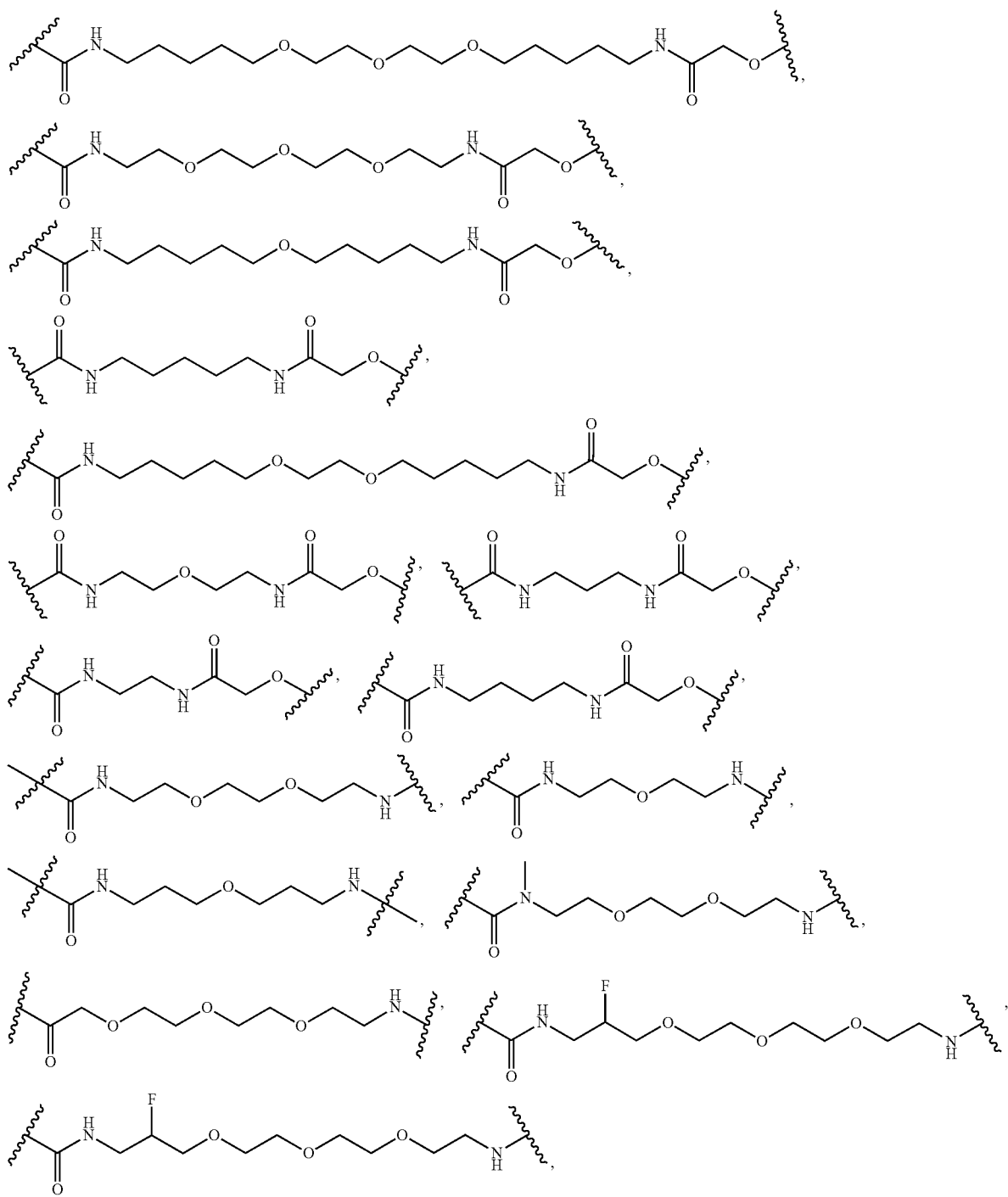

1417 1418
-continued
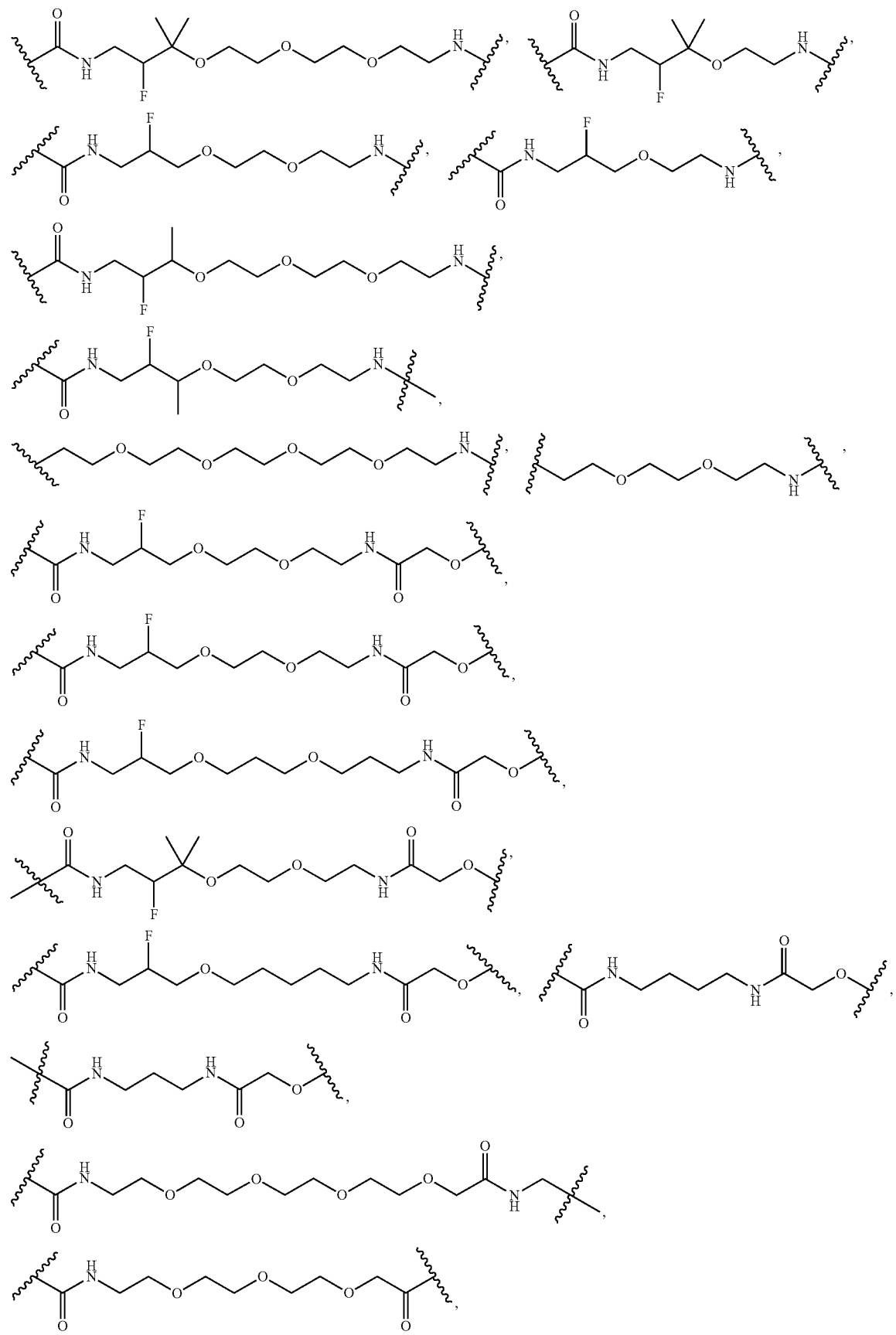

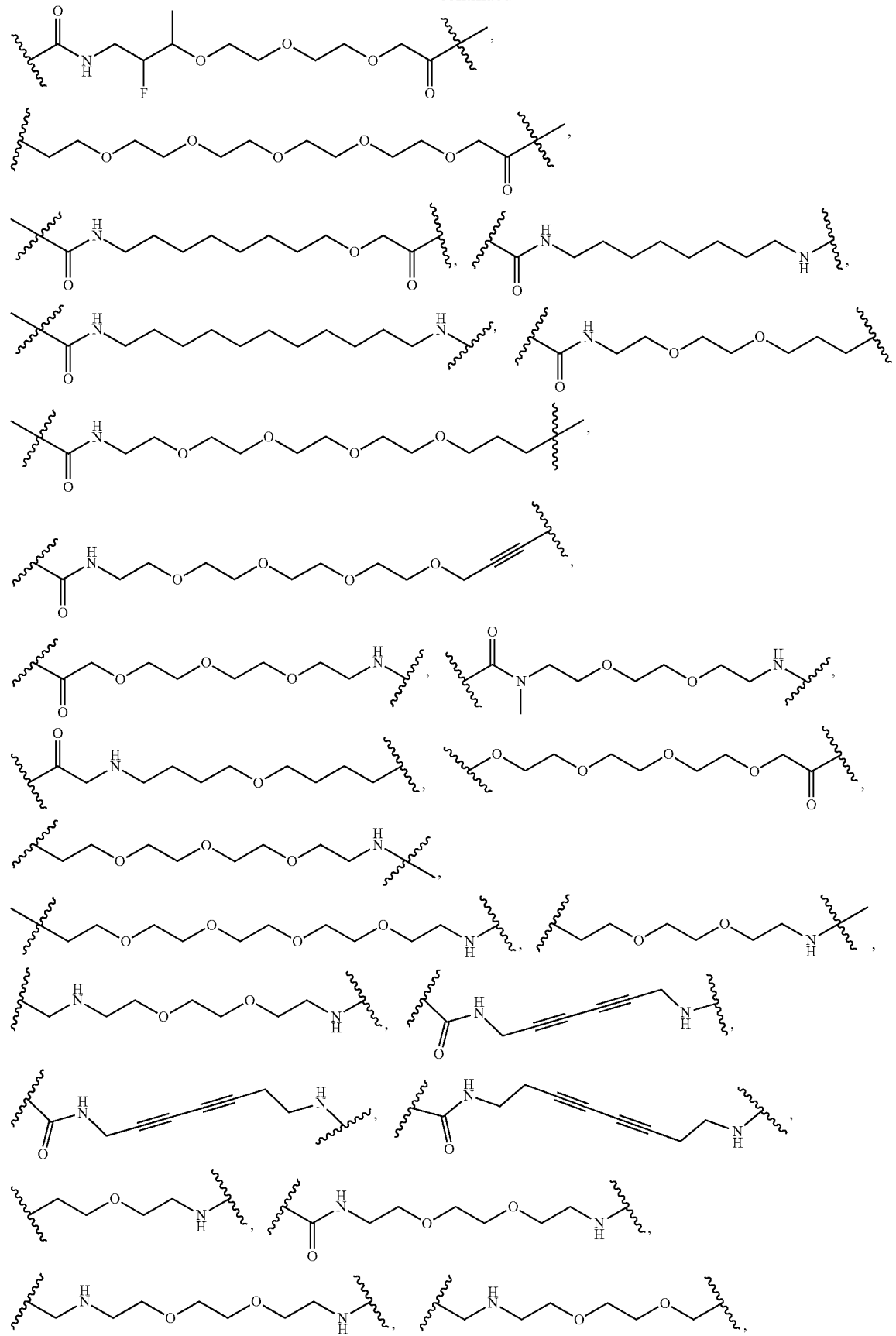

-continued
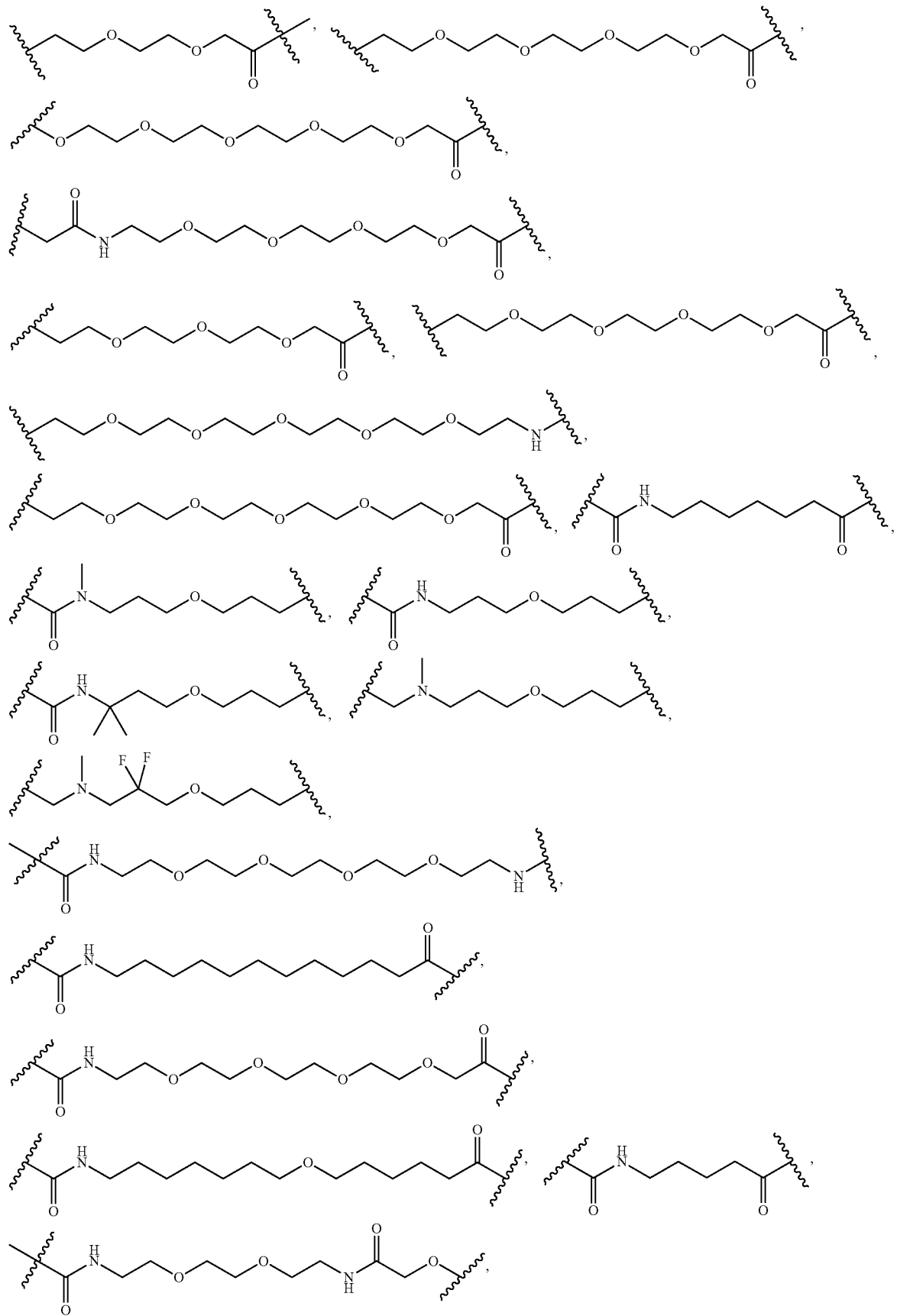

-continued
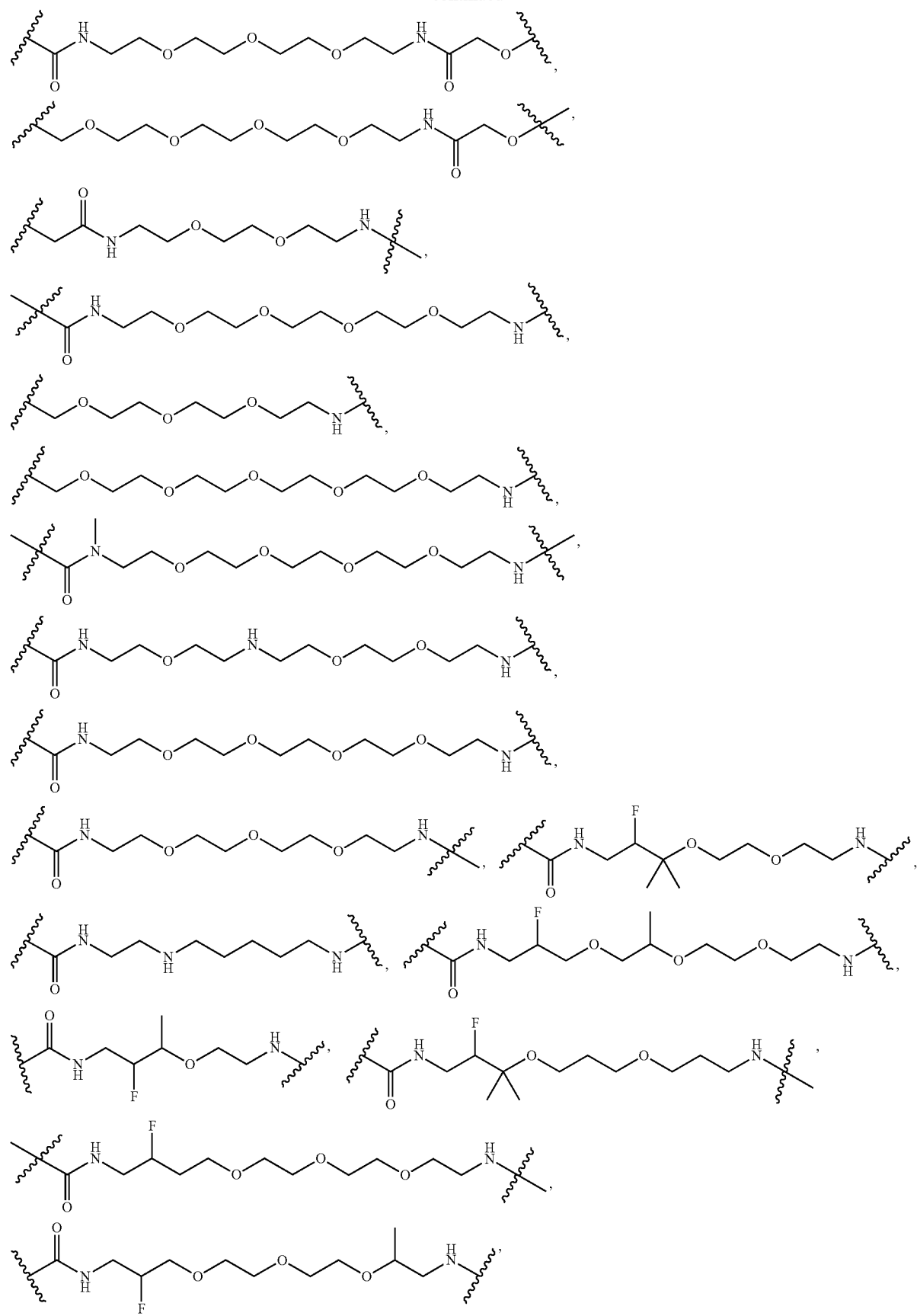

-continued
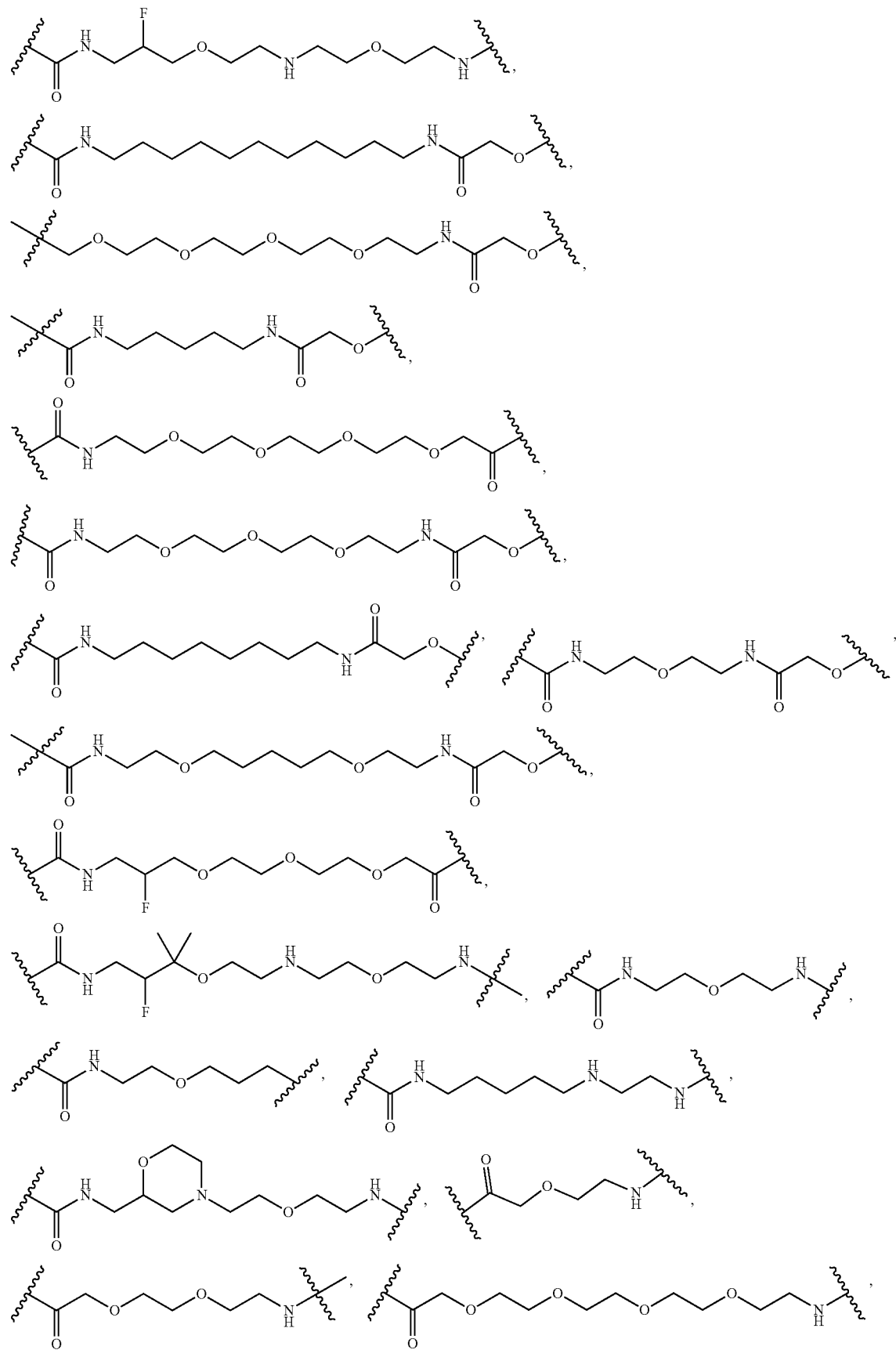

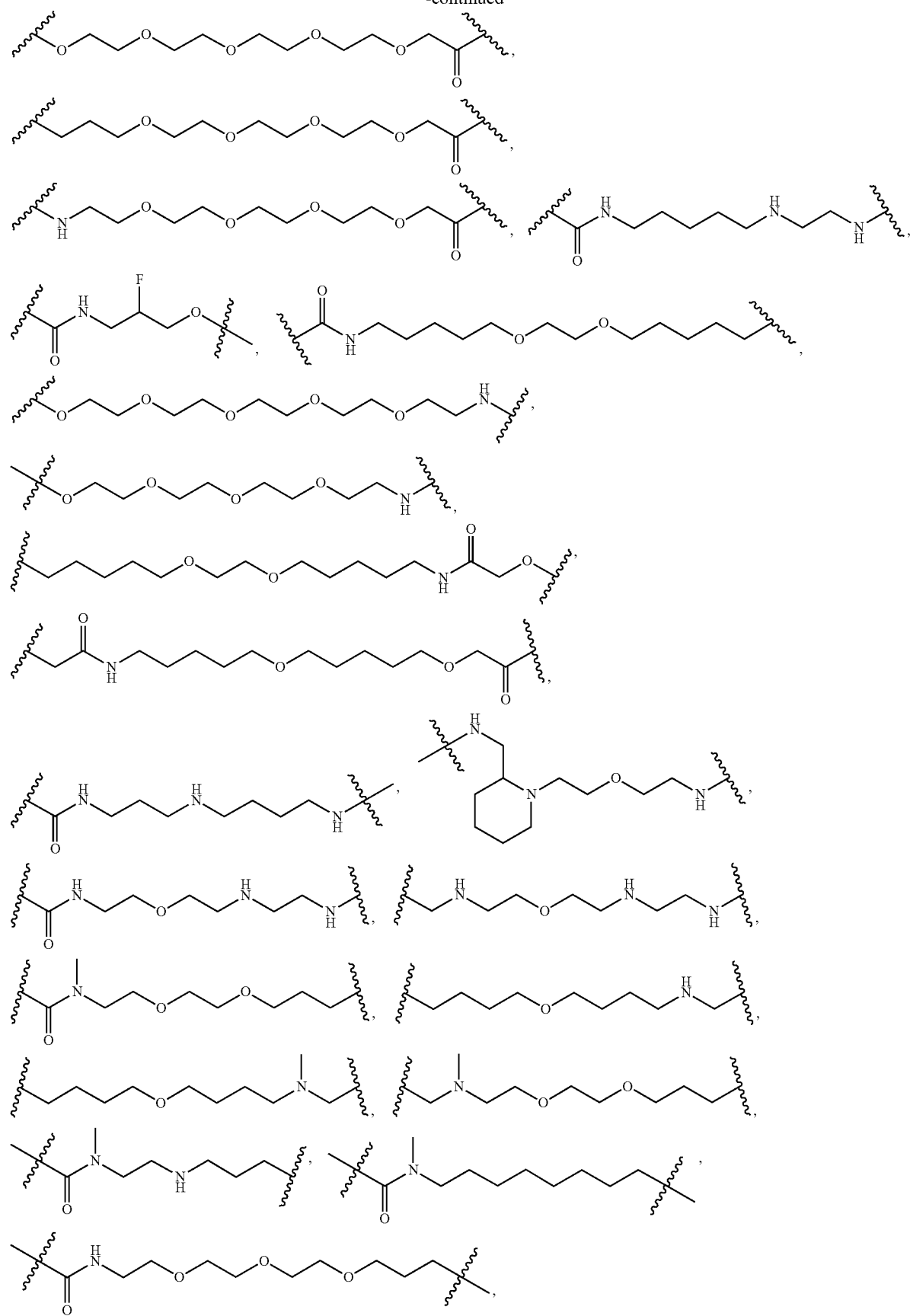

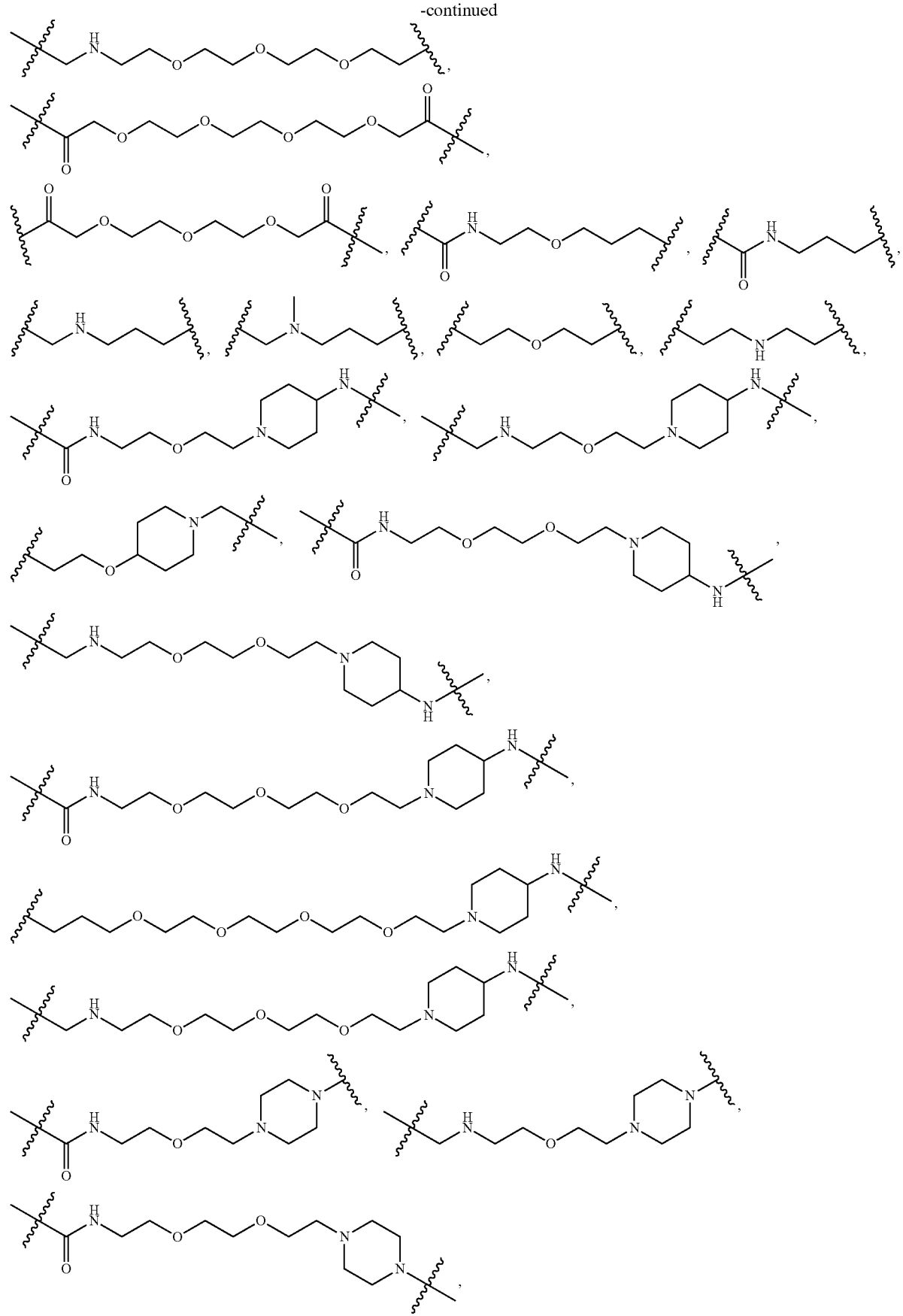

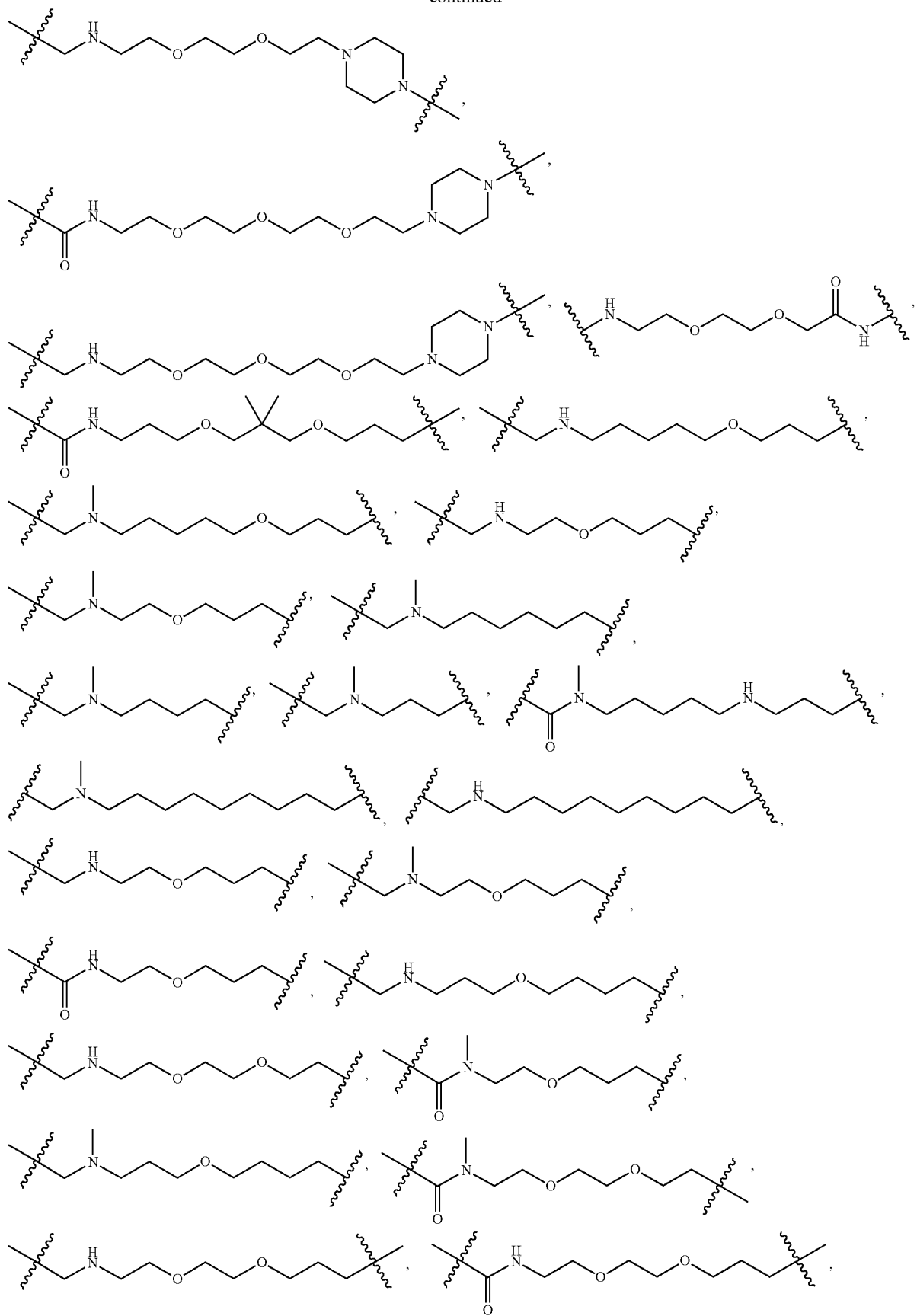

1433 1434
-continued
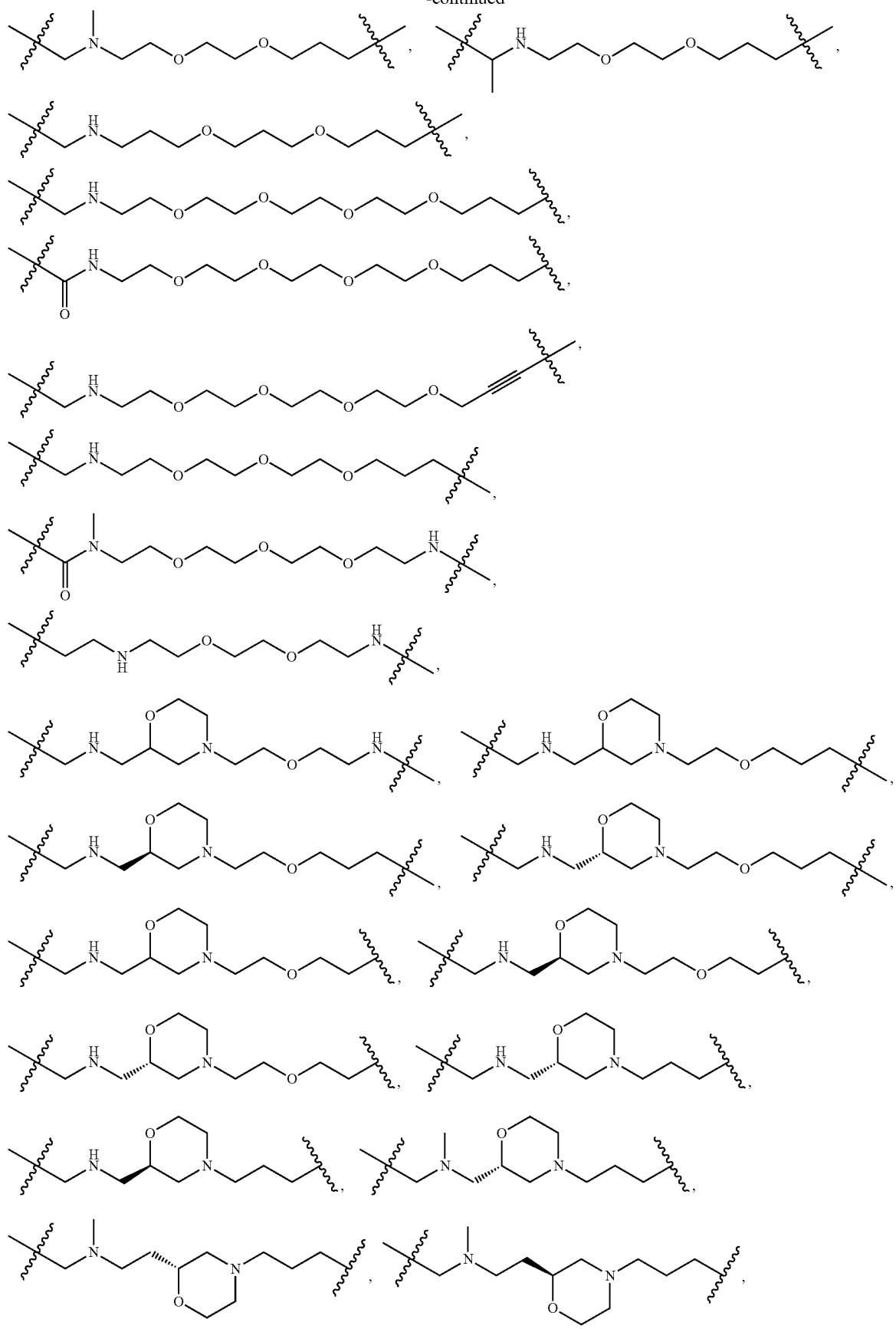

1435
1436
-continued
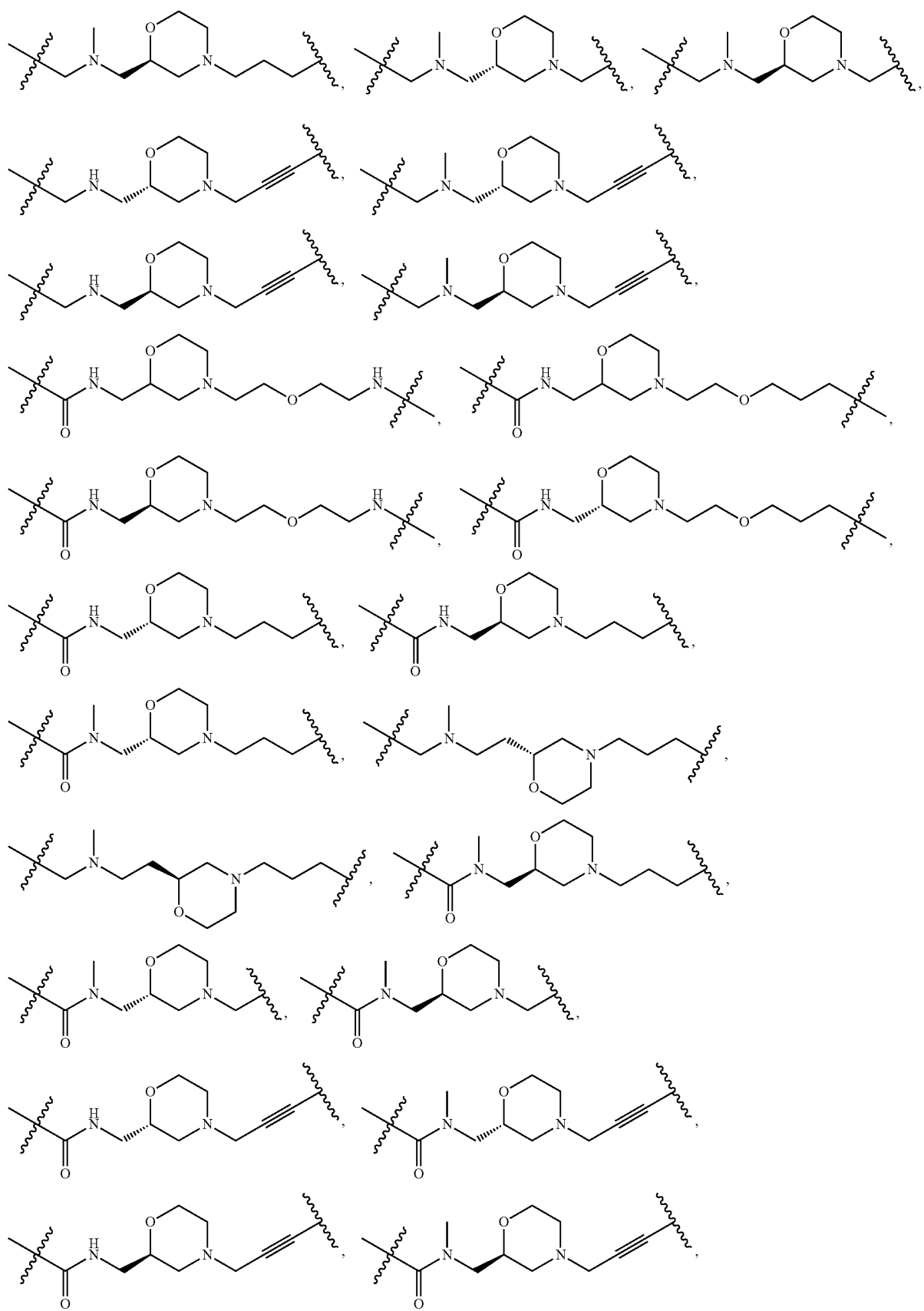

1437 1438
-continued
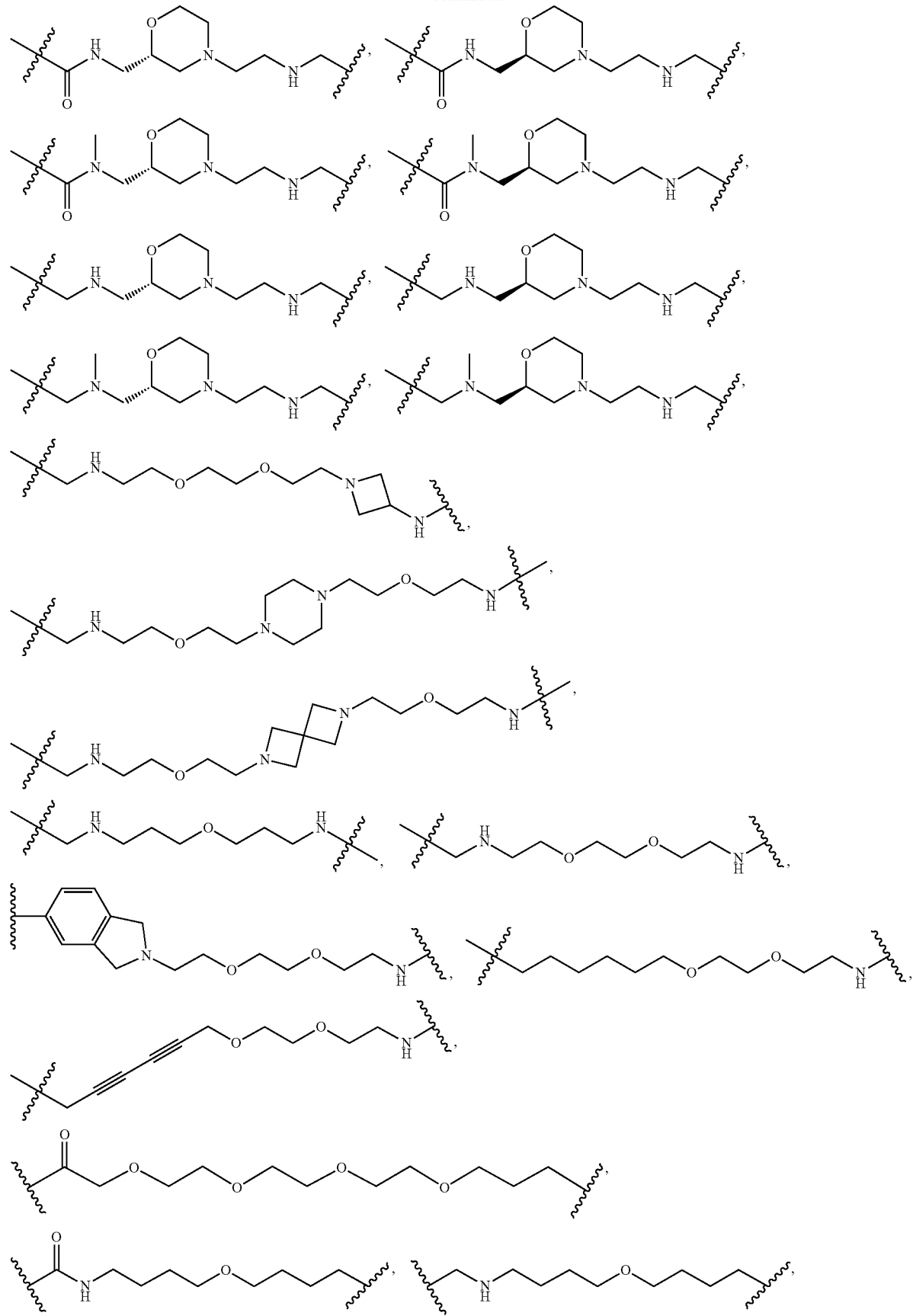

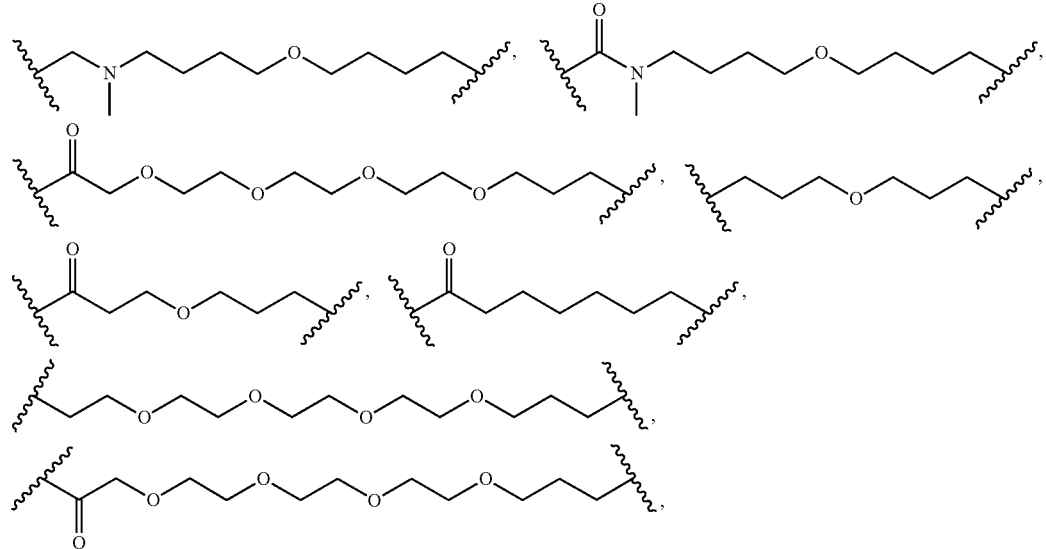
-continued
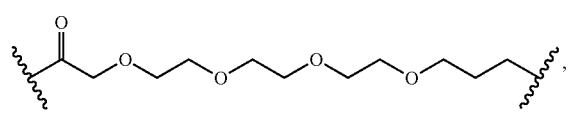
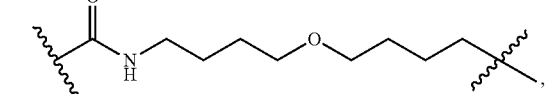
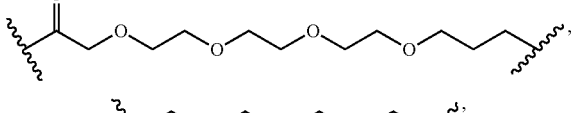
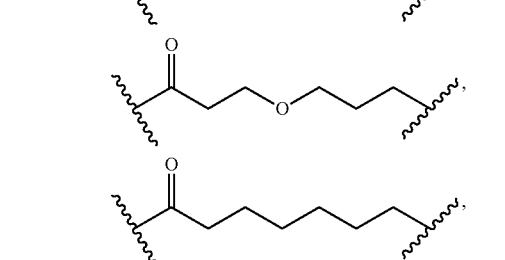
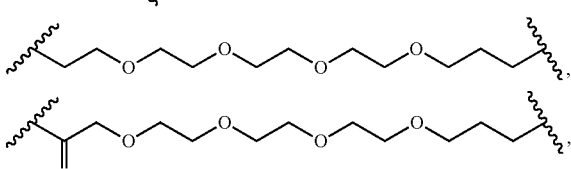
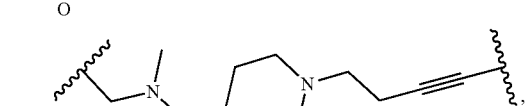
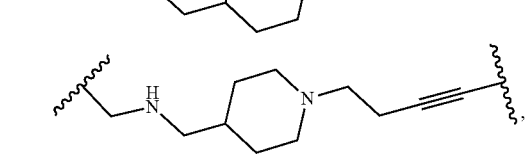
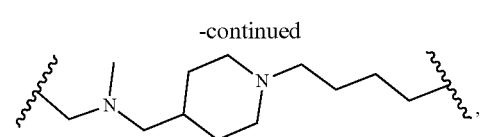
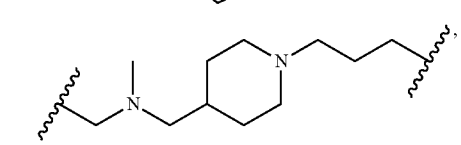
-continued
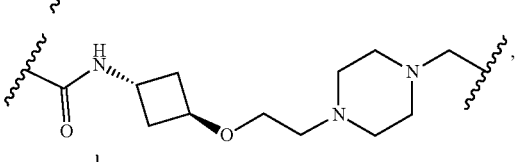
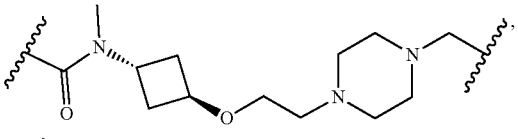
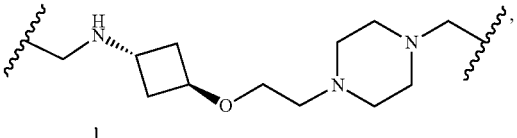
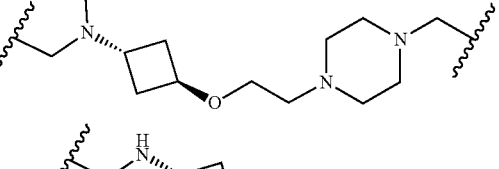
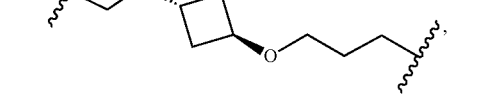
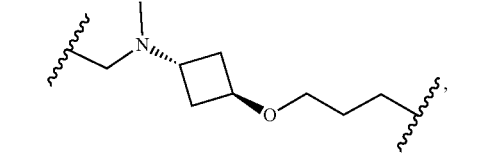

1441
-continued
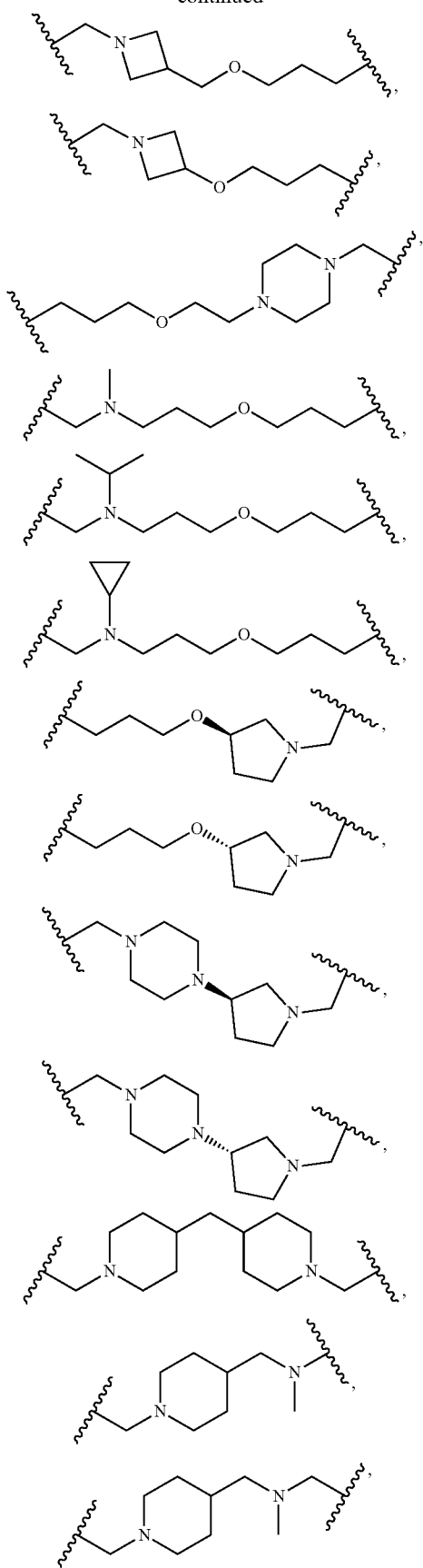
1442
-continued
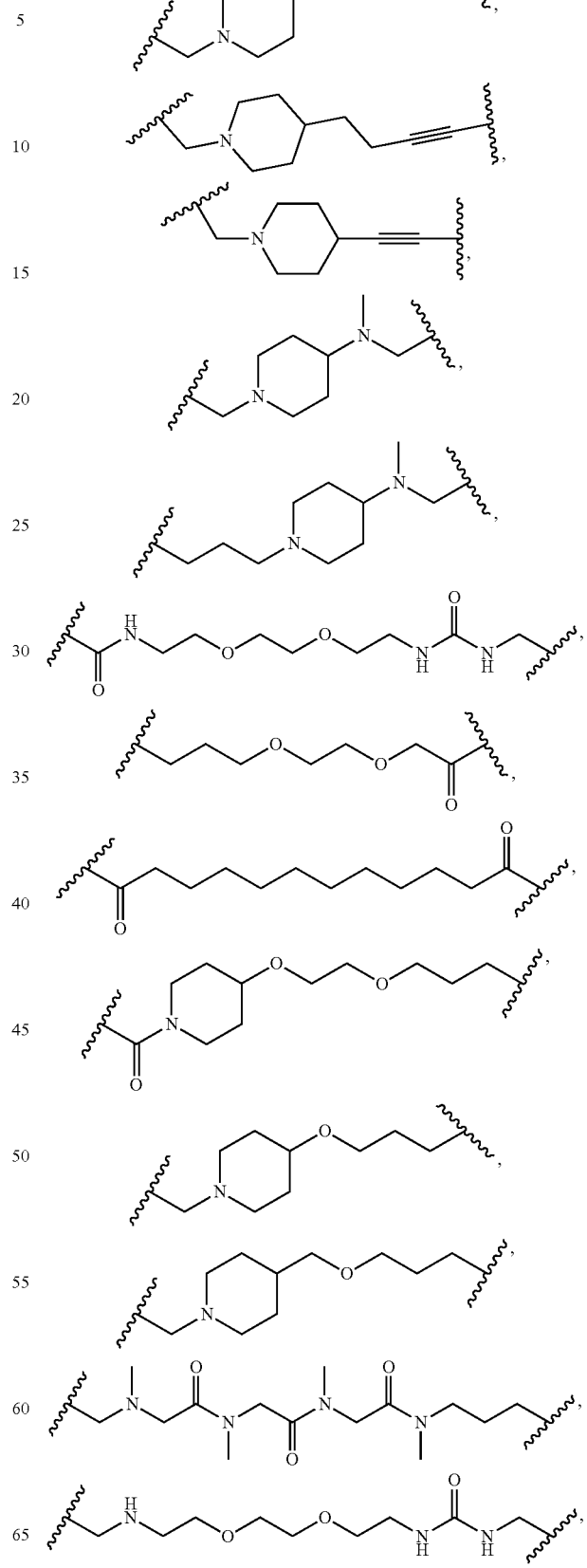

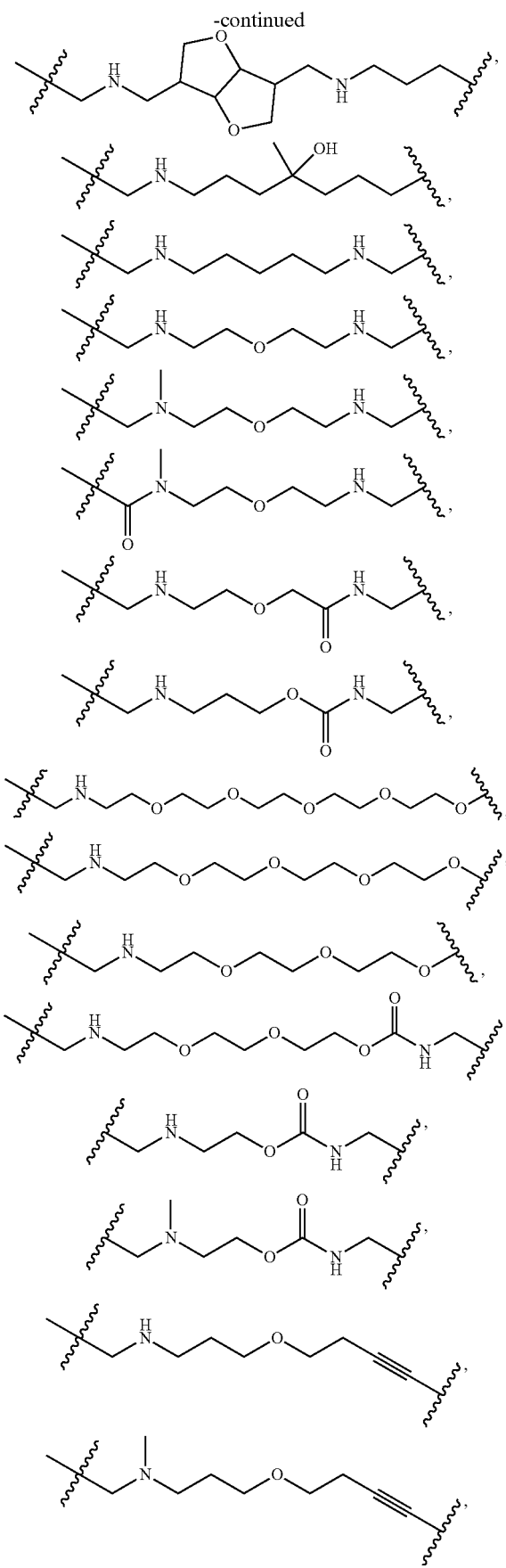
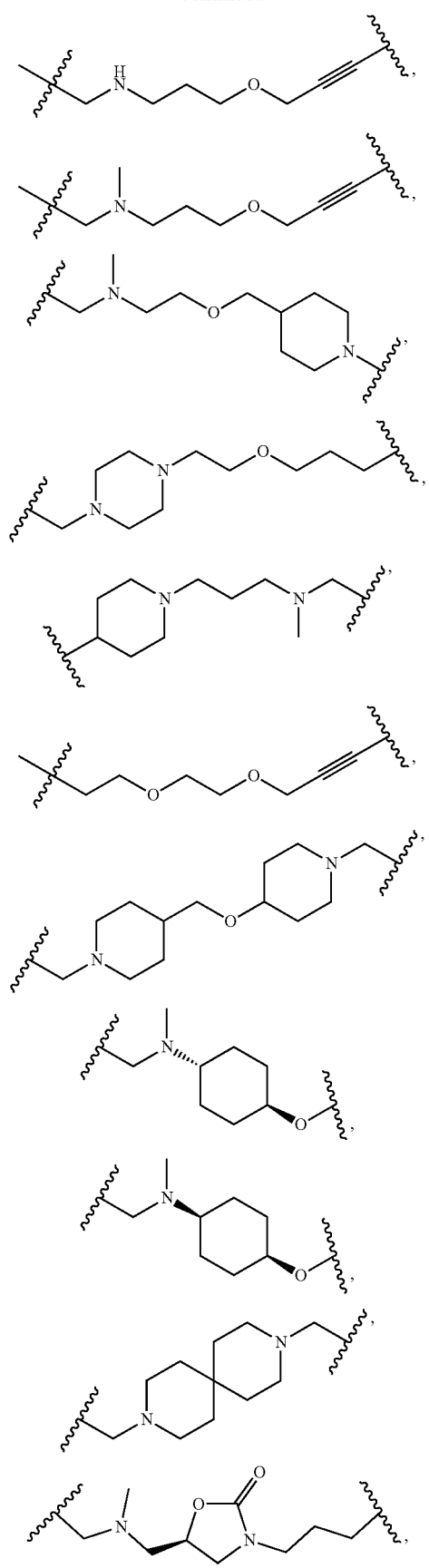

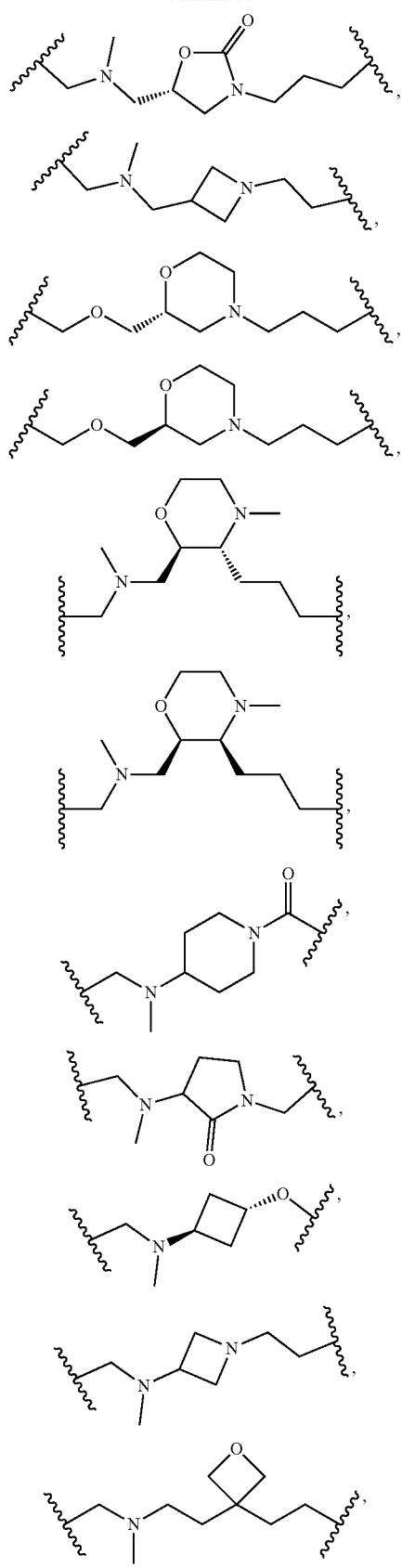
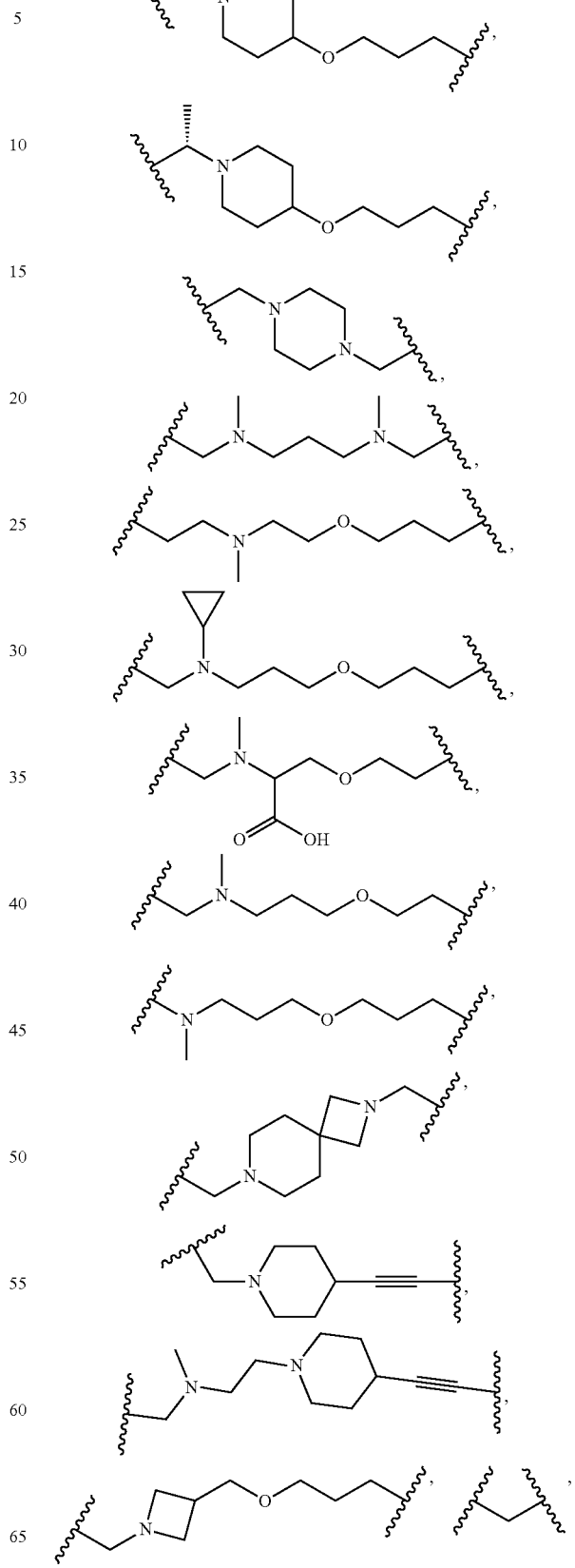

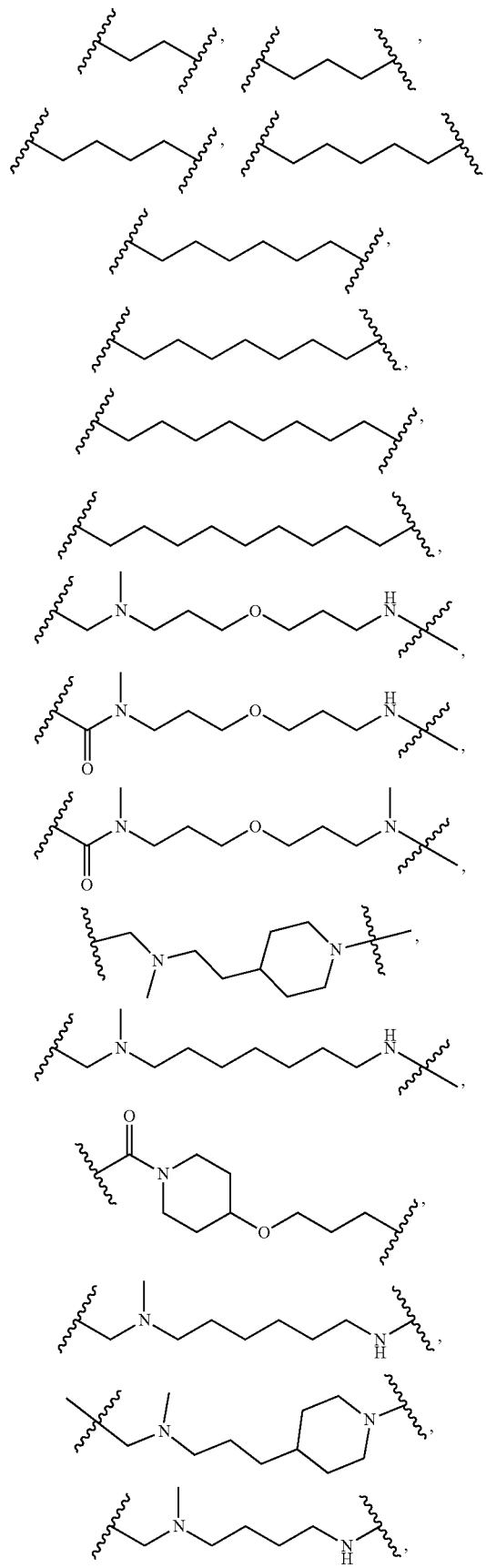
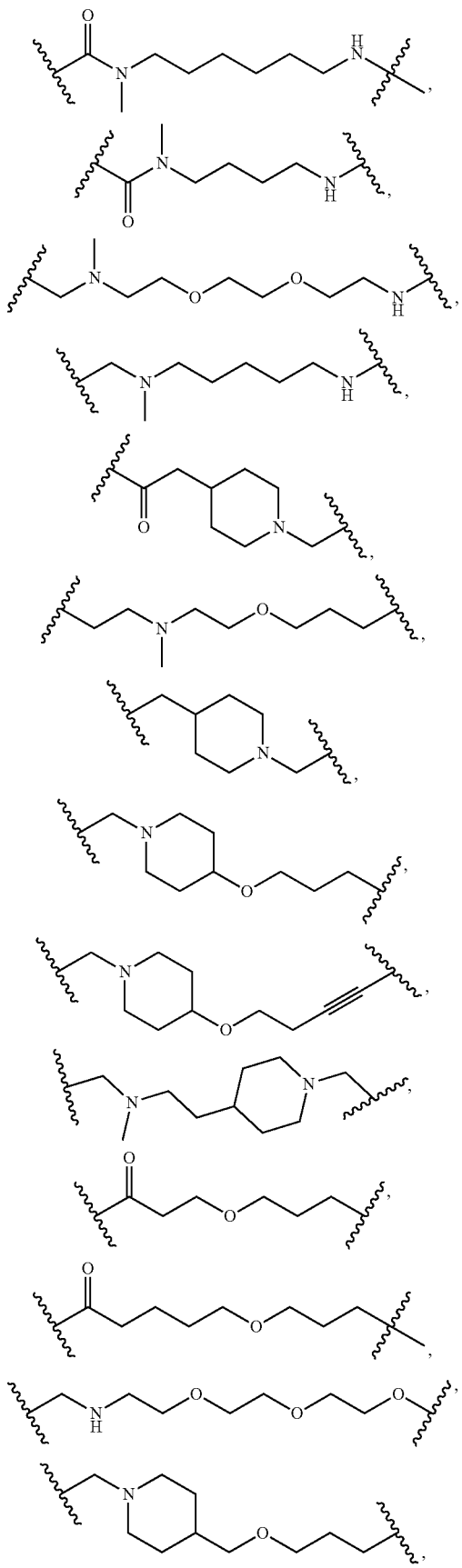

1449
-continued
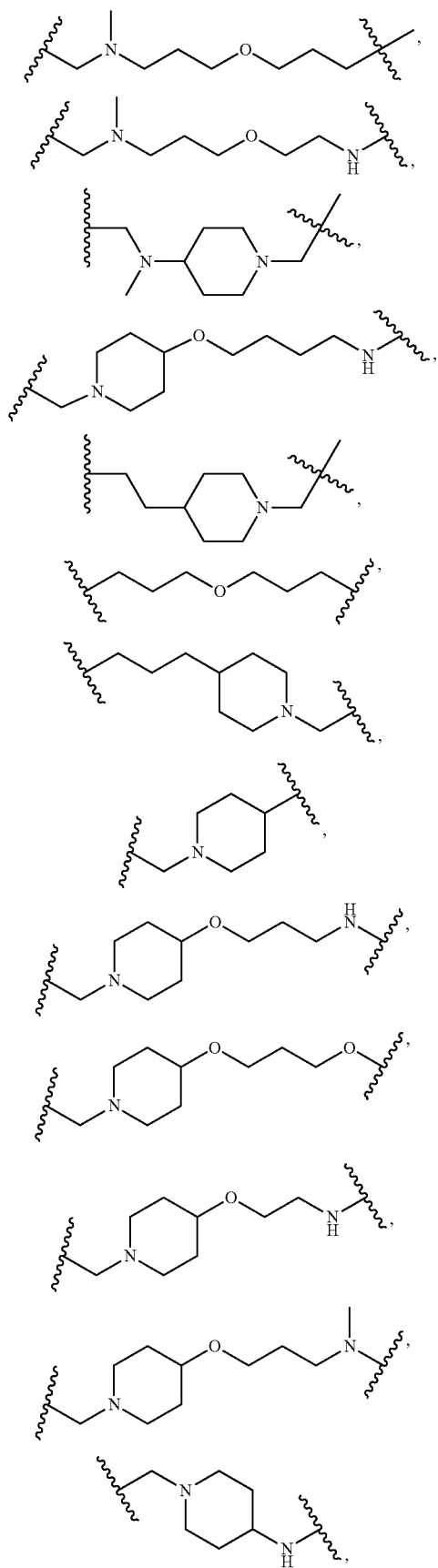
1450
-continued
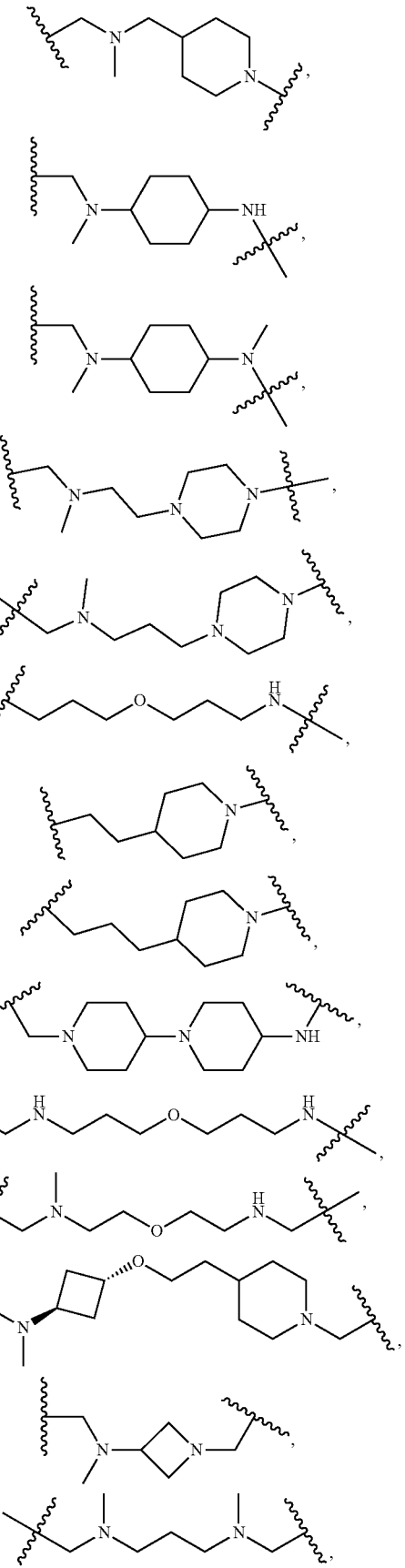

1451
-continued
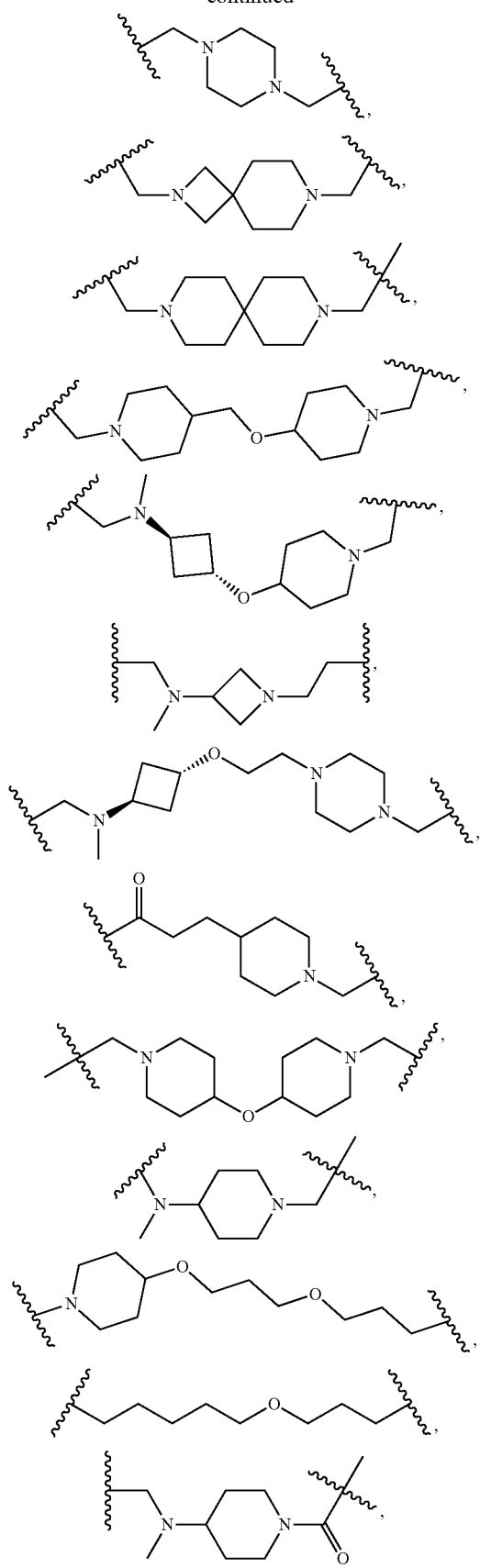
1452
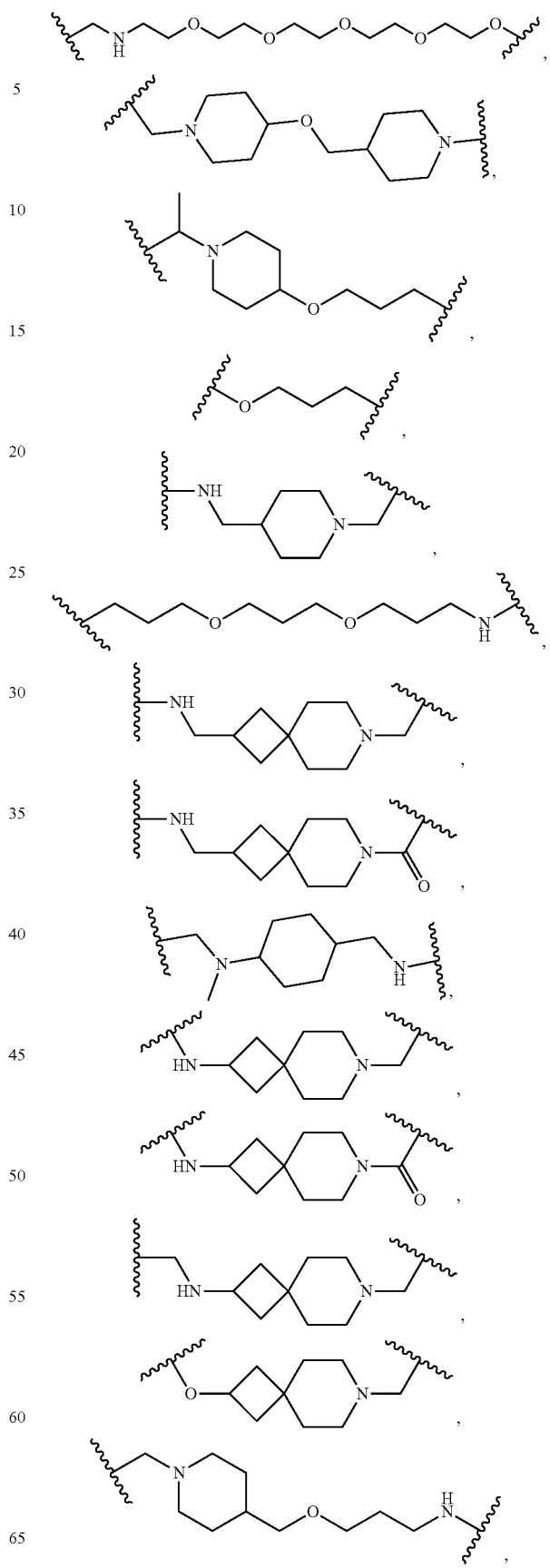

1453
-continued
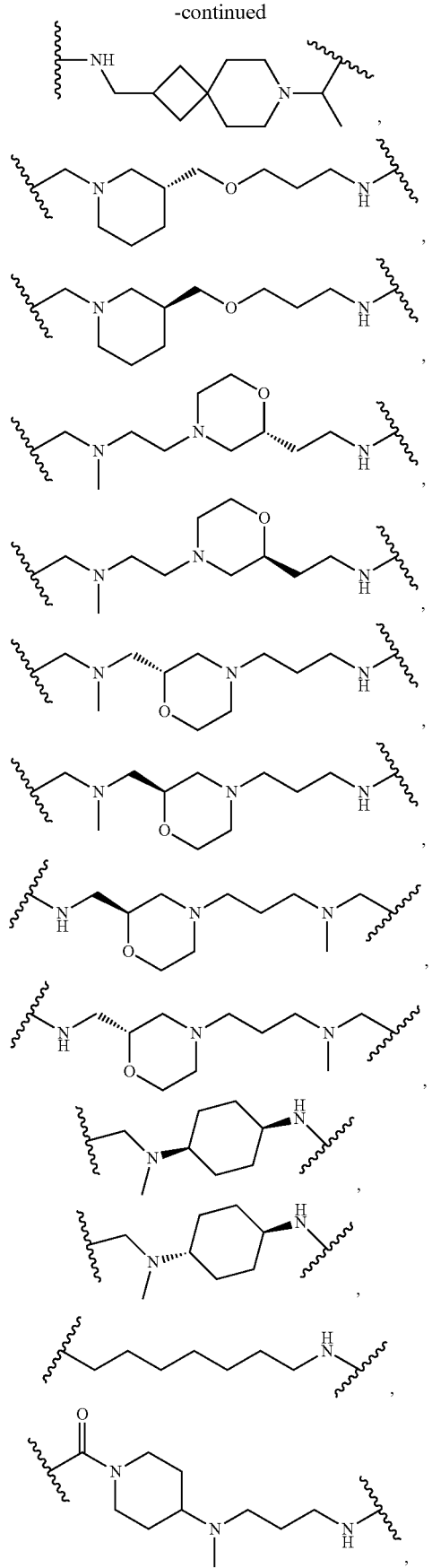
1454
-continued
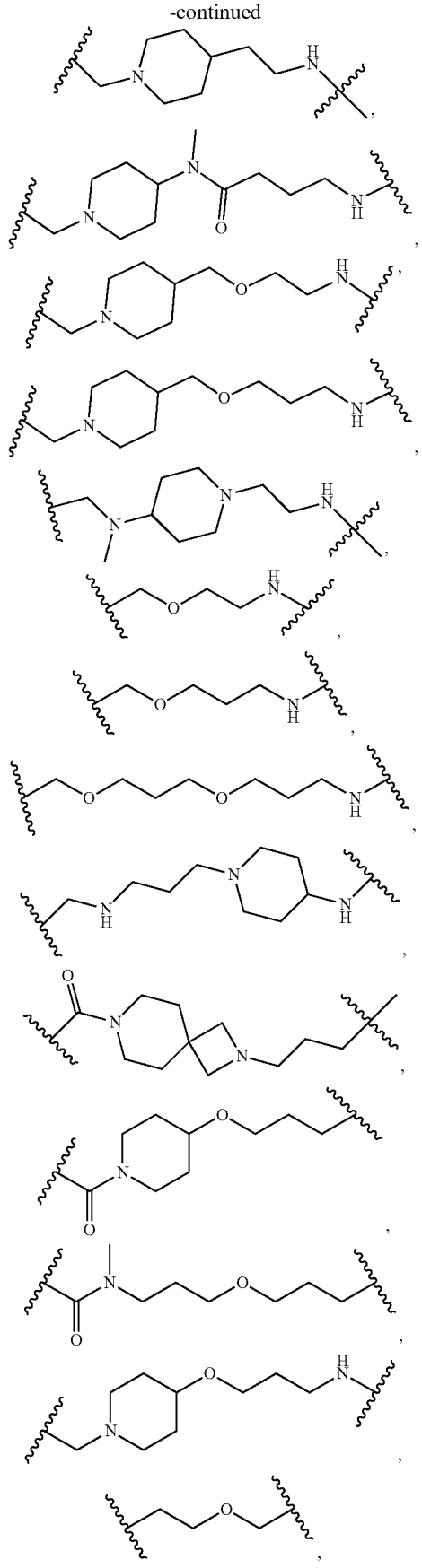

1455 1456
-continued -continued
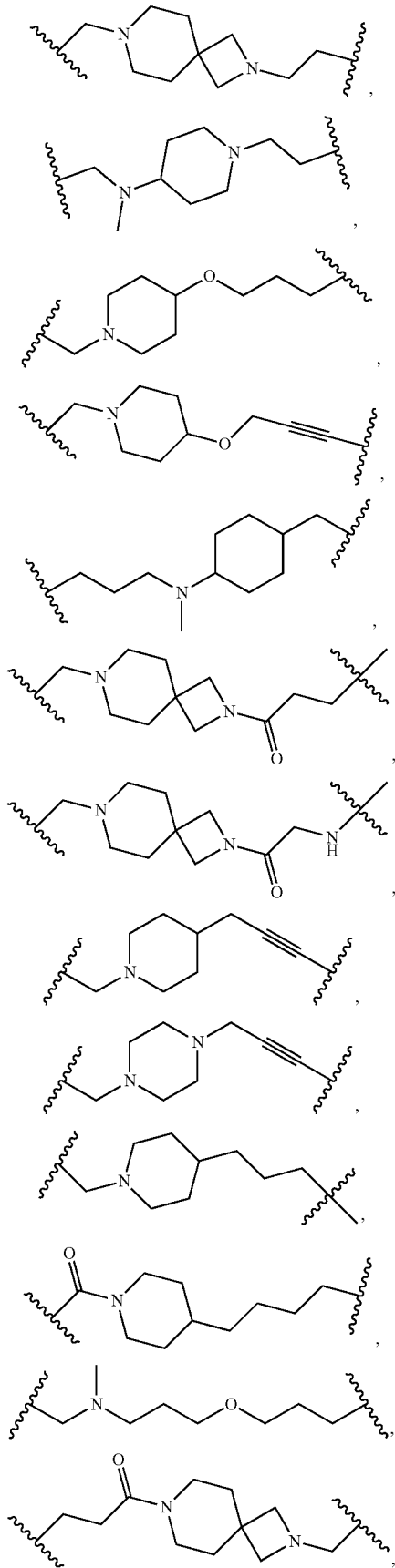
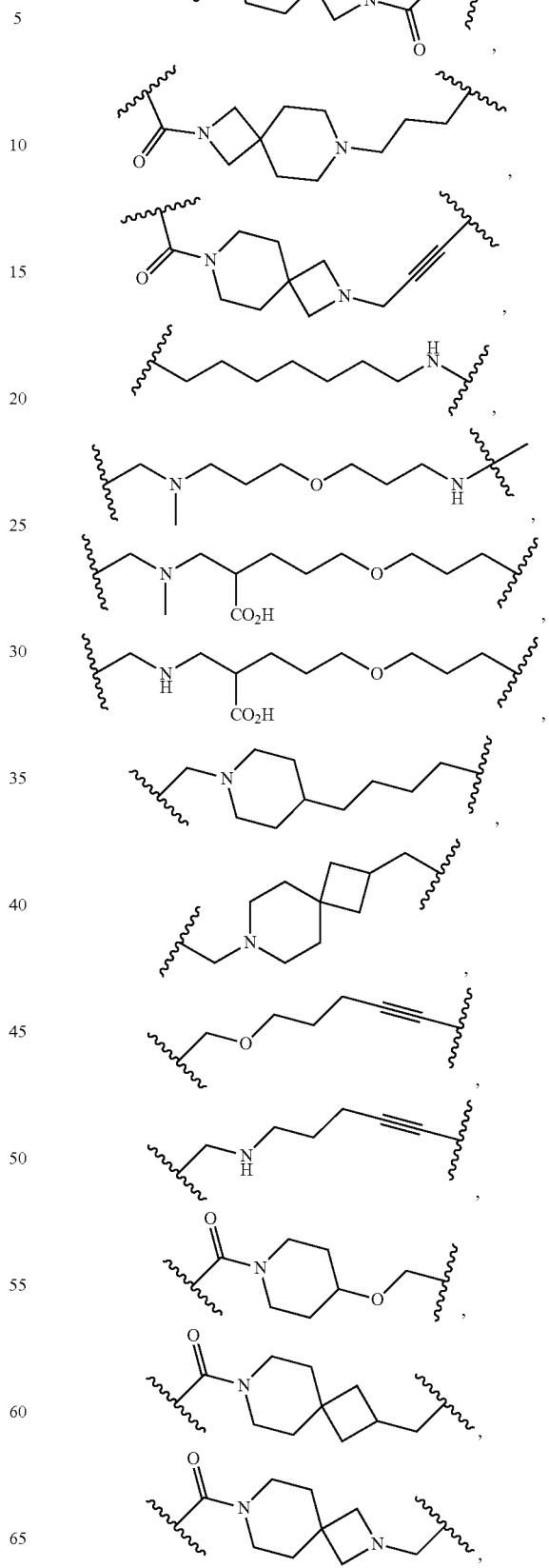

1457
-continued
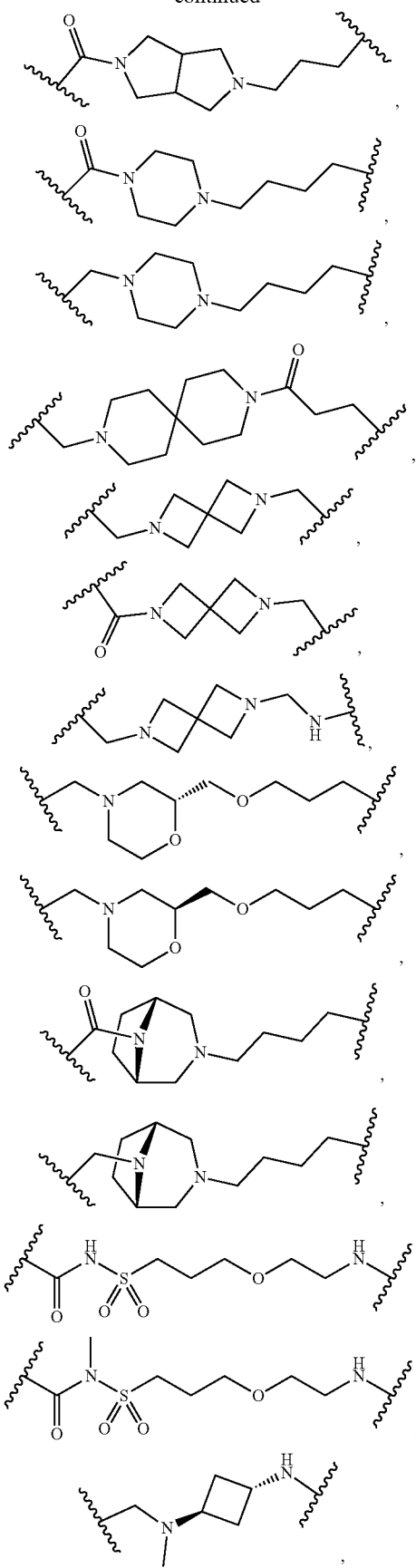
1458
-continued
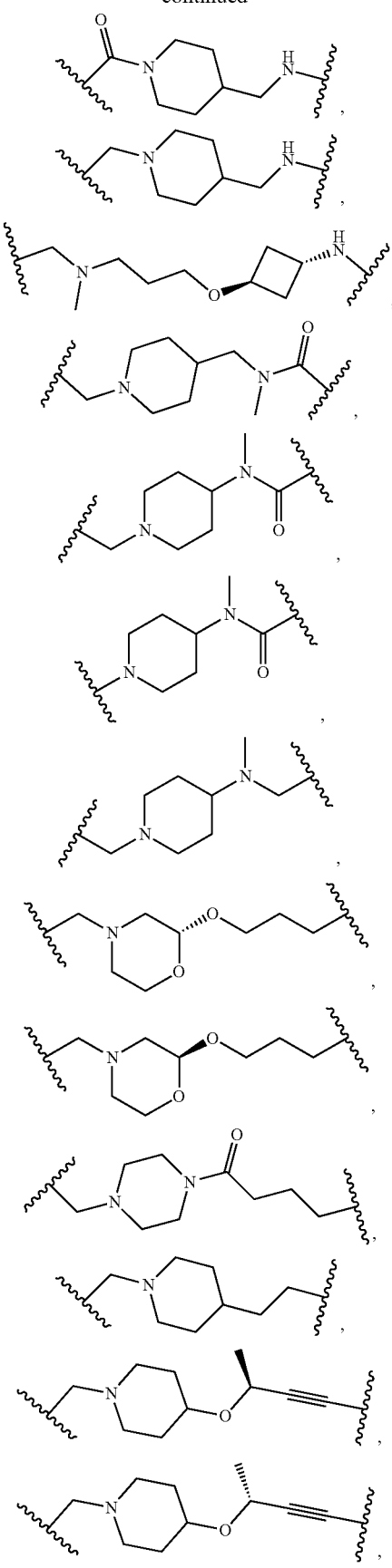

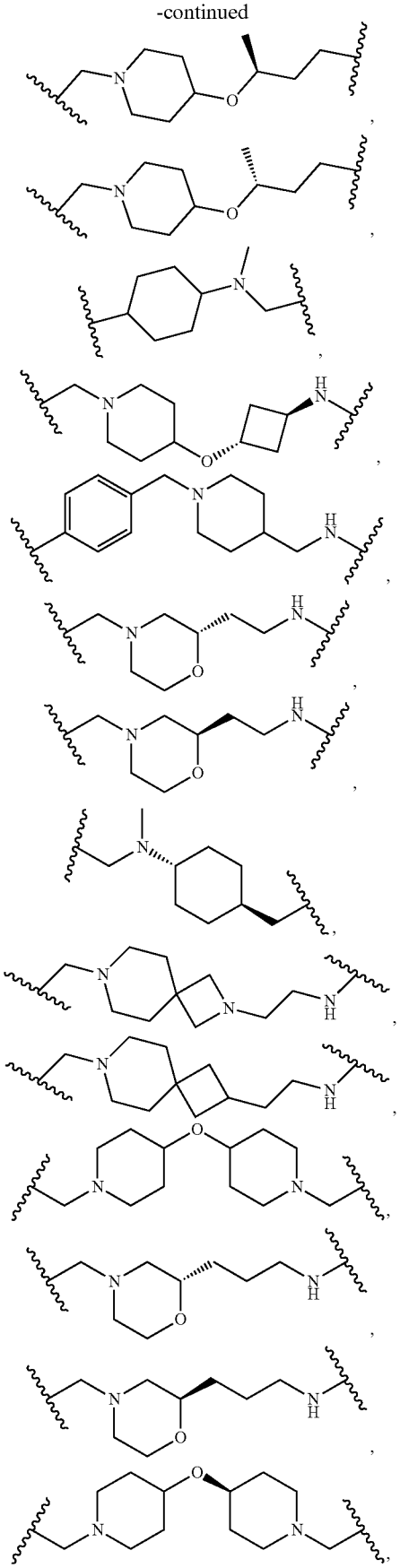
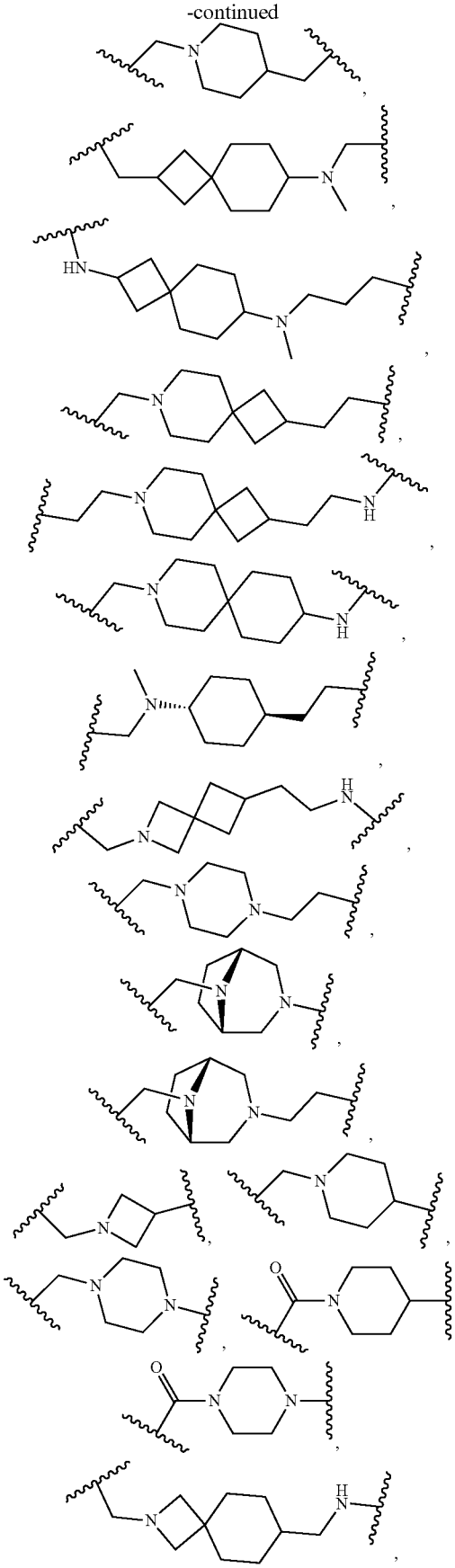

1461
-continued
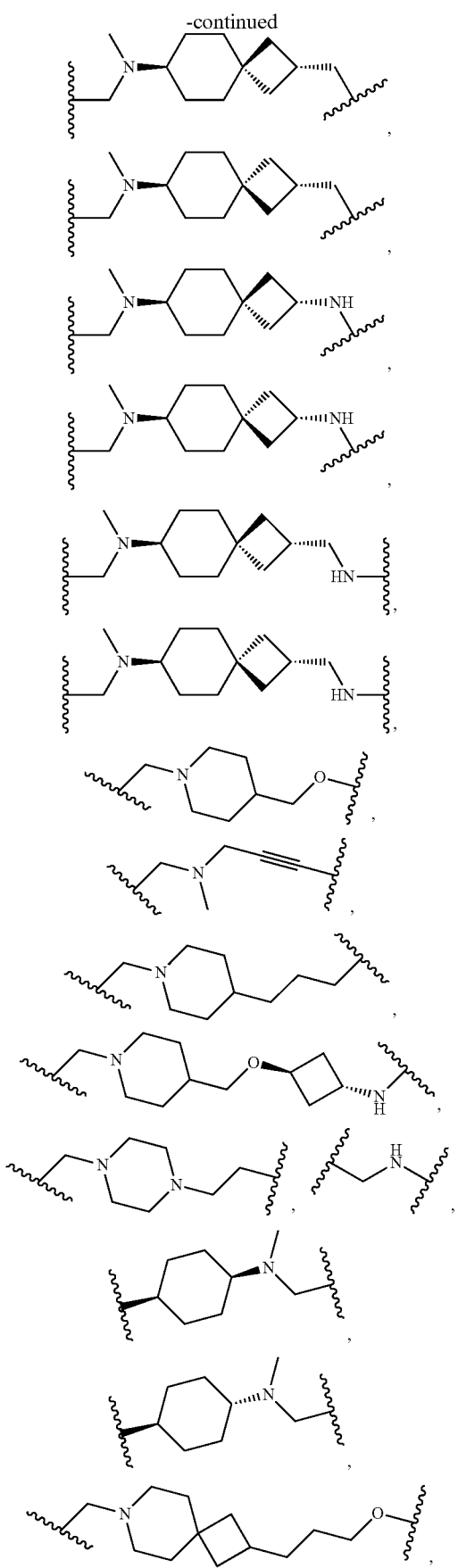
1462
-continued
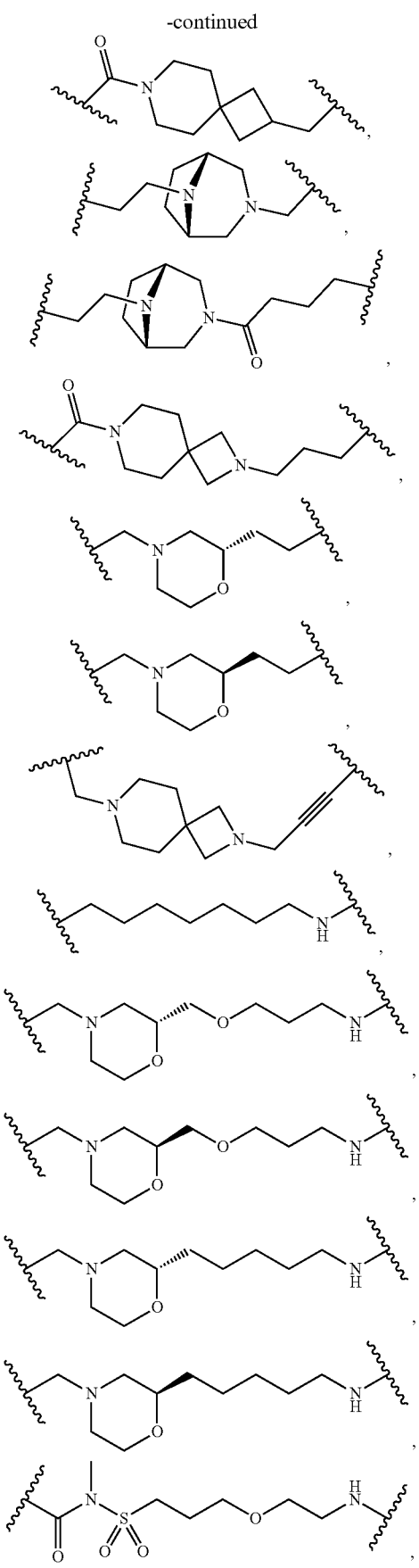

1463
-continued
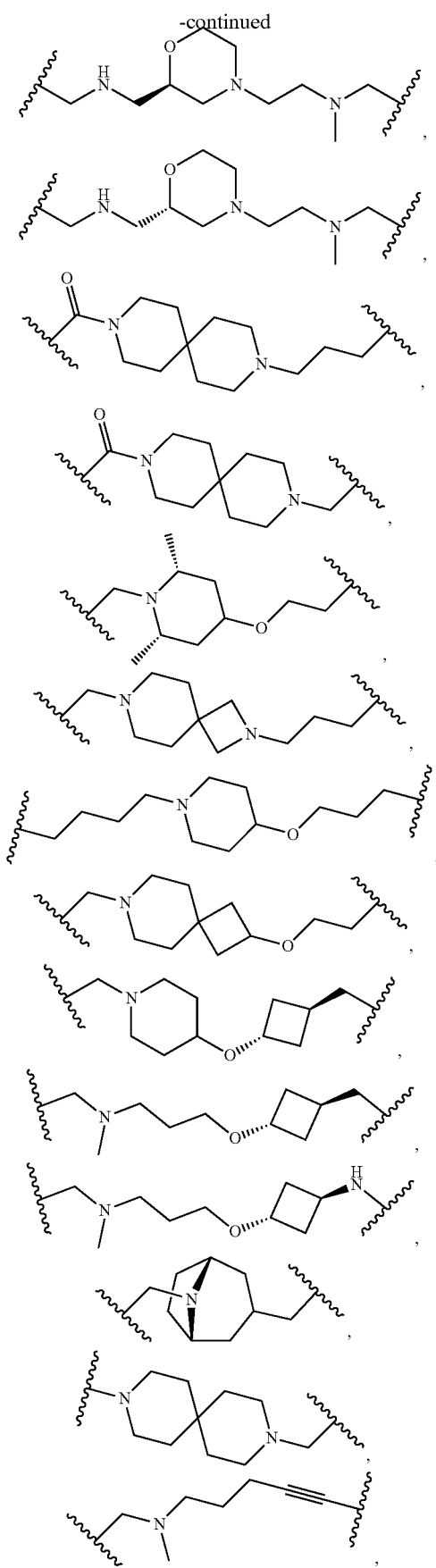
1464
-continued
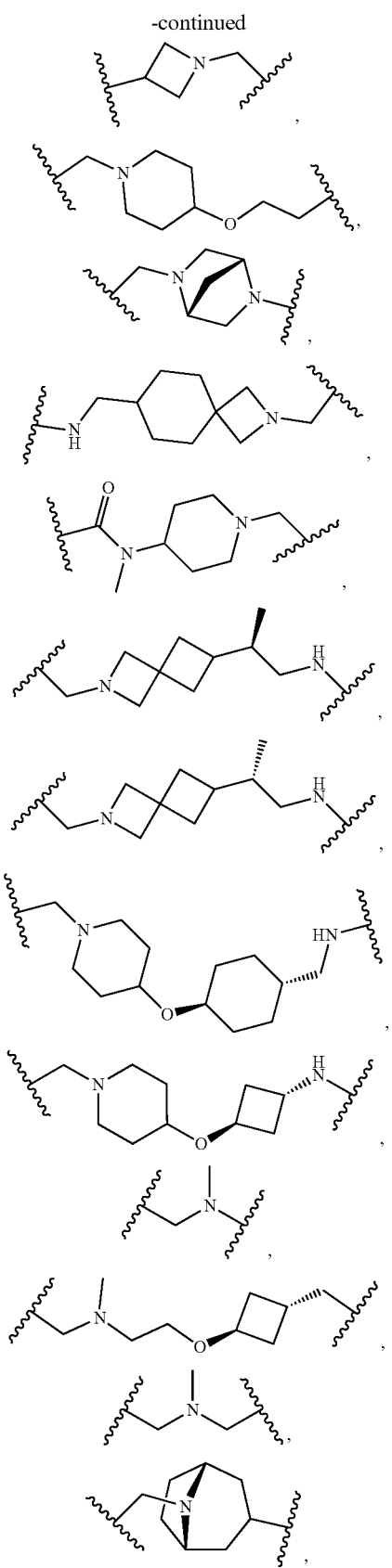

1465
-continued
1466
-continued
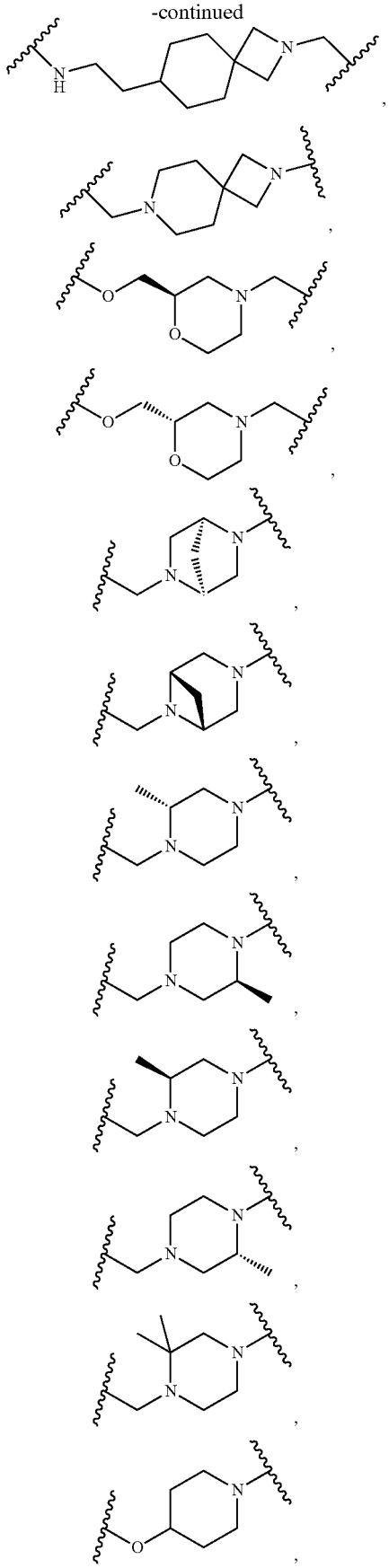
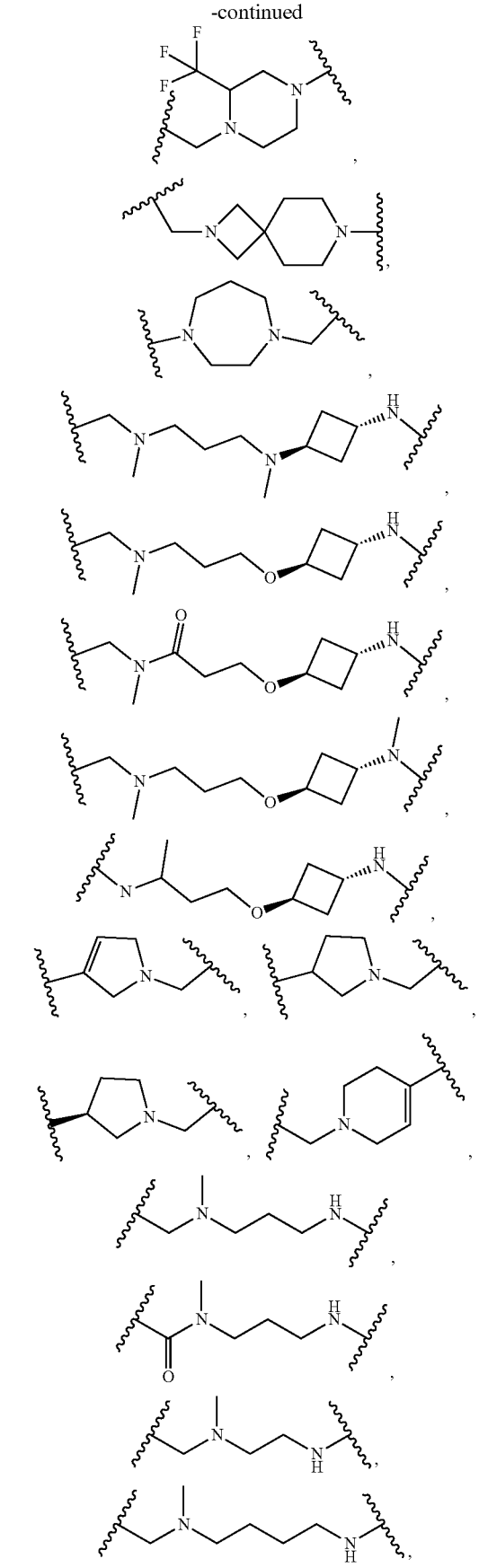

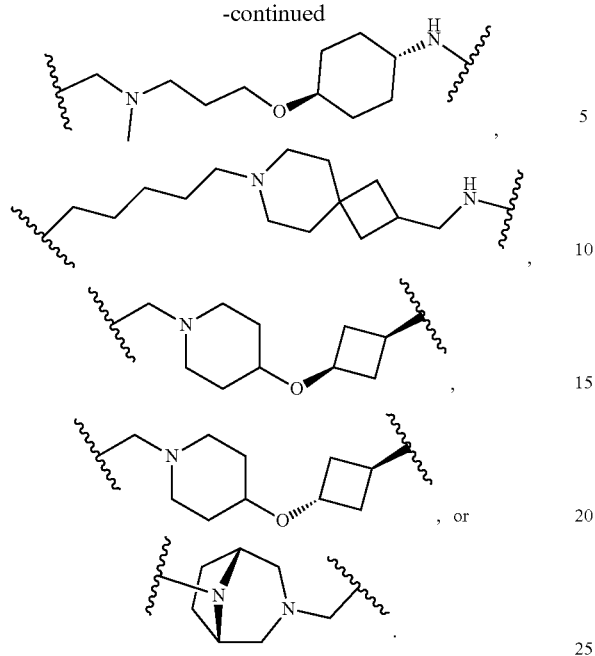

We claim:

1. A compound of formula I-d-5:

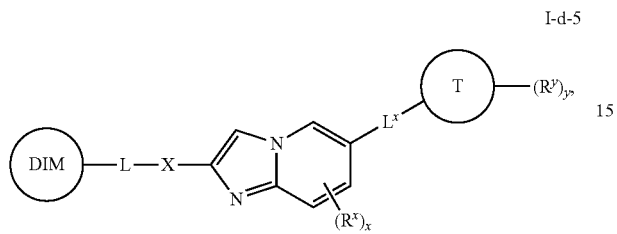

I-d-5 or a pharmaceutically acceptable salt thereof, wherein:
  each $R^x$ is independently —$OC_{1-6}$ aliphatic or —$CR_2$(OR);
  each R is independently hydrogen or $C_{1-6}$ aliphatic;
  each $R^y$ is independently $R^z$, fluoro, chloro, —CN, or —OR;
  each $R^z$ is a $C_{1-6}$ aliphatic optionally substituted with one or more fluoro;
  Ring T is selected from phenyl or a 5-9 membered mono- or bicyclic heteroaryl ring having 1-4 heteroatoms independently selected from nitrogen, oxygen, and sulfur, wherein Ring T is further optionally substituted with 1-2 oxo groups;
  $L^x$ is —C(O)N(H)—, wherein either the carbon or nitrogen atom of —C(O)N(H)— is attached to Ring T;
  X is a covalent bond

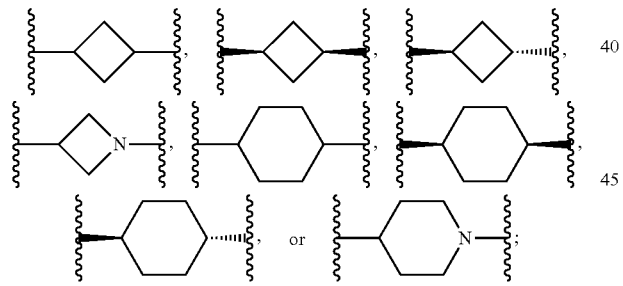

x is 0 or 1;
y is 0, 1, or 2;
L is a covalent bond or a bivalent, saturated or unsaturated, straight or branched $C_{1-30}$ hydrocarbon chain, wherein 0-6 methylene units of L are independently replaced by -Cy-, —CRF—, —$CF_2$—, —O—, —N(R)—, —OC(O)—, —C(O)O—, —C(O)—, —S(O)—, —$S(O)_2$—, —$N(R)S(O)_2$—, —$S(O)_2N(R)$—, —N(R)C(O)—, —C(O)N(R)—, —OC(O)N(R)—, —N(R)C(O)O—, wherein each -Cy- is independently an optionally substituted bivalent ring selected from a 4-7 membered saturated or partially unsaturated carbocyclylenyl, a 4-11 membered saturated or partially unsaturated spiro carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur, and DIM is a degradation inducing moiety selected from a cereblon E3 ubiquitin ligase binding moiety of formula I-ccc-1:

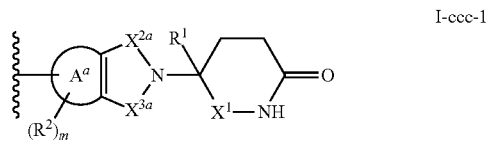

I-ccc-1 or a pharmaceutically acceptable salt thereof, wherein:
  $X^1$ is —C(O)—;
  $X^{2a}$ is —C(O)—;
  $X^{3a}$ is —$CH_2$— or —C(O)—;
  $R^1$ is hydrogen;
  each of $R^2$ is independently fluoro, chloro, $C_{1-4}$ aliphatic, or —$OC_{1-4}$ aliphatic;
  Ring $A^a$ is a fused 6-membered aryl containing 0-1 nitrogen atoms; and
  m is 0, or 1.

2. The compound of claim 1, wherein said compound is of formula I-j-4:

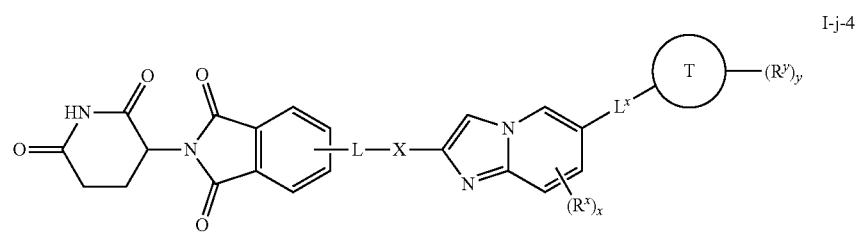

I-j-4

I-k-6
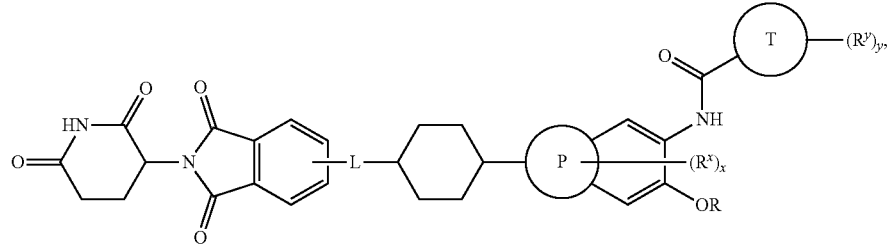
I-k-7
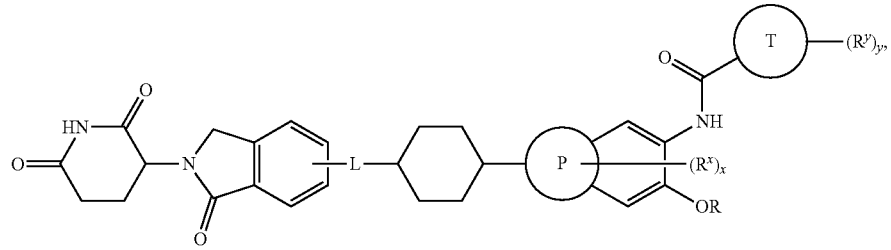
I-k-8
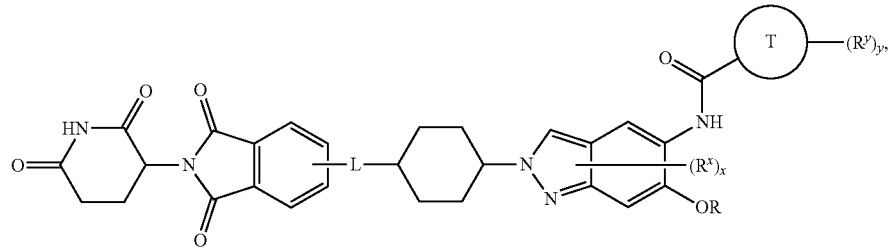
I-k-9
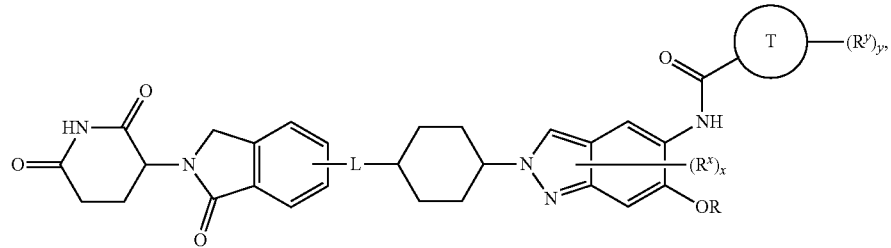
I-k-10
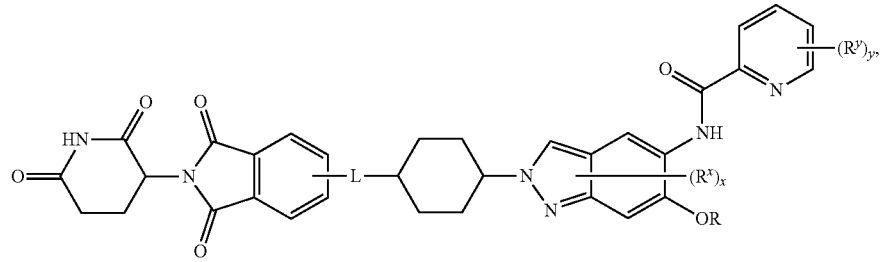
I-k-11
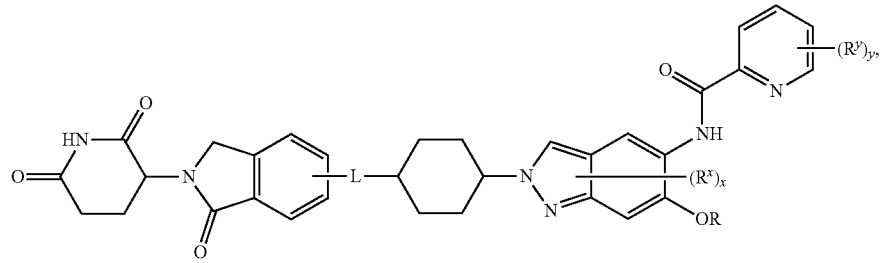

I-k-12

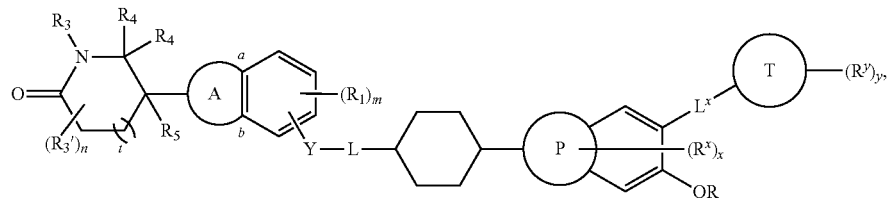

I-k-13

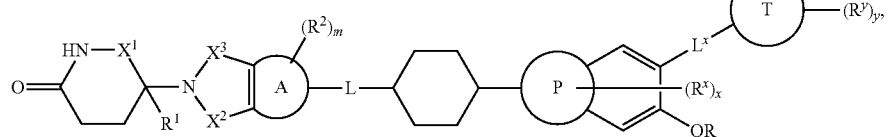

I-k-14

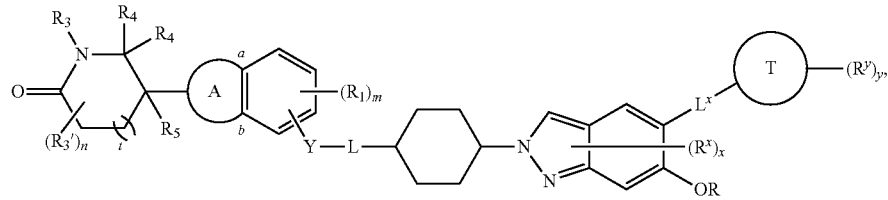

I-k-15

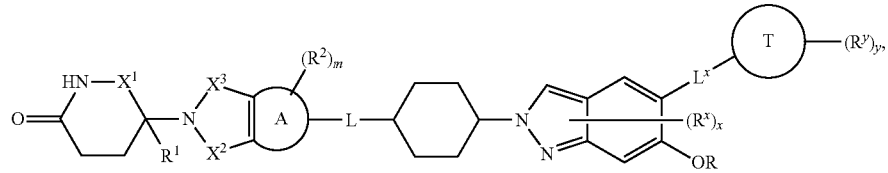

or a pharmaceutically acceptable salt thereof.

3. The compound of claim 1, wherein L is a bivalent, saturated or unsaturated, straight or branched $C_{1-20}$ hydrocarbon chain, wherein 0-6 methylene units of L are independently replaced by -Cy-, —O—, —N(R)—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, or —N(R)C(O)O—.

4. The compound of claim 1, wherein said compound is selected from any one of the following compounds:

I-10

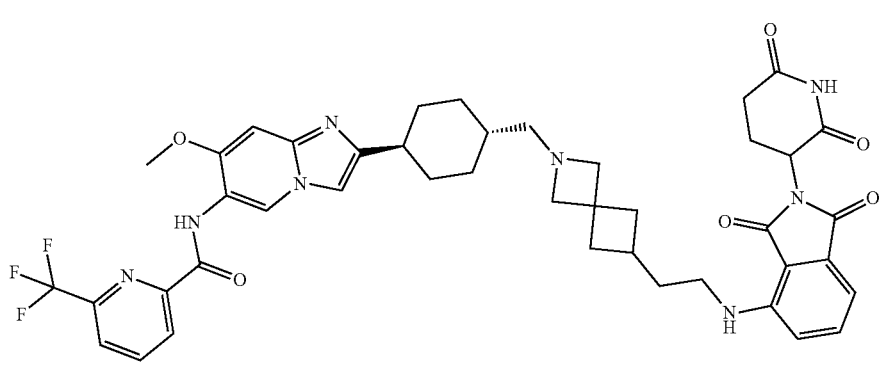

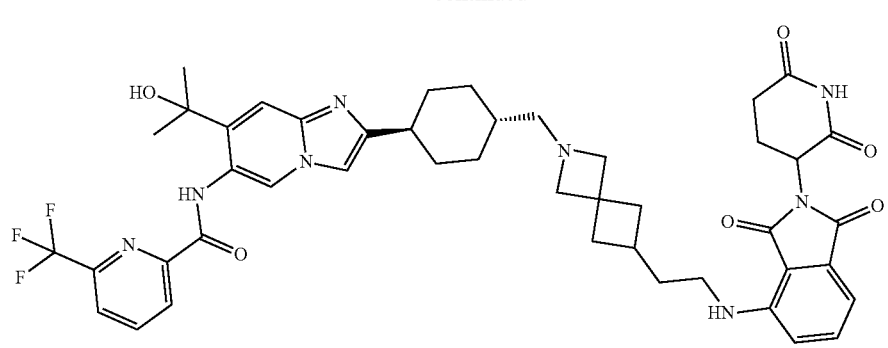

or a pharmaceutically acceptable salt thereof.

5. A pharmaceutical composition comprising a compound of claim 1, and a pharmaceutically acceptable carrier, adjuvant, or vehicle.

6. The compound of claim 1, wherein the cereblon E3 ubiquitin ligase binding moiety is

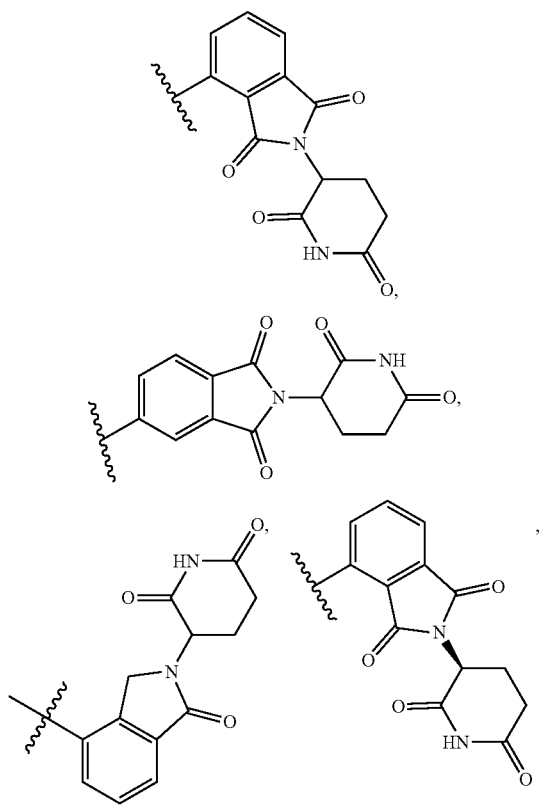

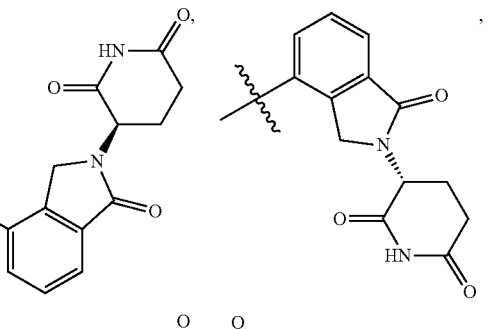

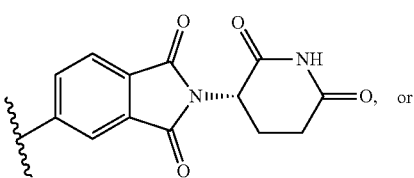

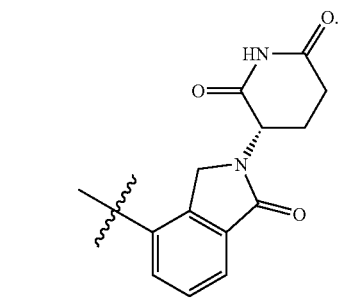 [SMILES: *c1cccc2c1CN([C@H]1CCC(=O)NC1=O)C2=O]

7. The compound of claim 1, wherein $R^x$ is

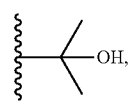

—OMe, —OEt, —OiPr, or

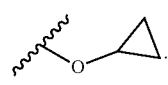

8. The compound of claim 1, wherein $R^y$ is $C_{1-6}$ aliphatic optionally substituted with one to three fluoro.

9. The compound of claim 1, wherein $R^y$ is —CN, —CF$_3$, fluoro, chloro, —CF$_2$Me, —CFMe$_2$, -Me, —OMe, or cyclopropyl.

10. The compound of claim 1, wherein Ring T is a 5-9 membered mono- or bicyclic heteroaryl ring having 1-4 heteroatoms independently selected from nitrogen, oxygen, and sulfur.

11. The compound of claim 1, wherein Ring T is phenyl,

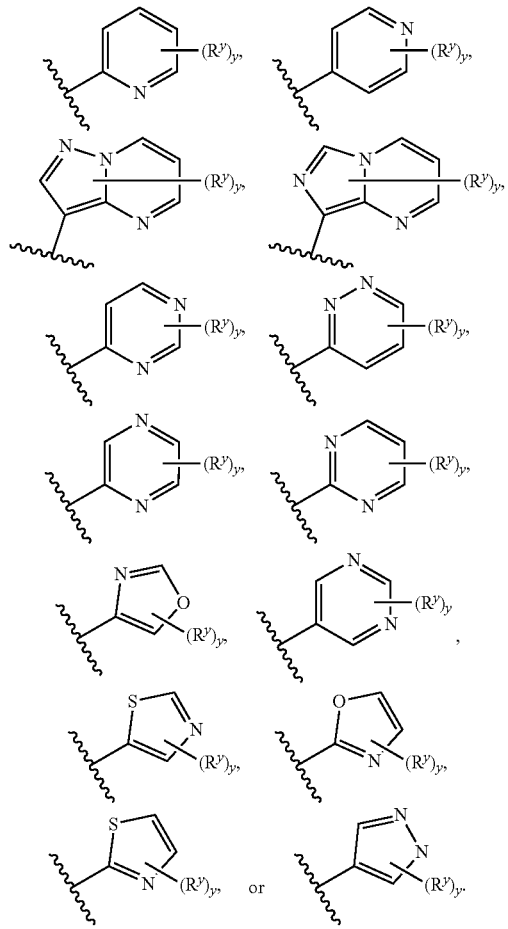

12. The compound of claim 1, wherein X is

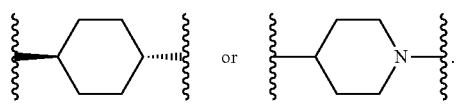

13. The compound of claim 1, wherein L is —NR—(CH$_2$)$_{1-10}$—, —(CH$_2$)$_{1-10}$—NR—(CH$_2$)$_{1-10}$—, —(CH$_2$)$_{1-10}$—Cy-NR—(CH$_2$)$_{1-10}$—, —Cy-(CH$_2$)$_{1-10}$—NR—, —Cy-(CH$_2$)$_{1-10}$—NR—(CH$_2$)$_{1-10}$—, —(CH$_2$)$_{1-10}$-Cy-NR—(CH$_2$)$_{1-10}$—, —(CH$_2$)$_{1-10}$-Cy-(CH$_2$)$_{1-10}$—NR—, —(CH$_2$)$_{1-10}$-Cy-(CH$_2$)$_{1-10}$—NR—(CH$_2$)$_{1-10}$—, —Cy-(CH$_2$)$_{1-10}$-Cy-NR—, —Cy-(CH$_2$)$_{1-10}$—NR-Cy-, —Cy-(CH$_2$)$_{1-10}$-Cy-NR—(CH$_2$)$_{1-10}$—, —Cy-(CH$_2$)$_{1-10}$—NR-Cy-(CH$_2$)$_{1-10}$—, —Cy-(CH$_2$)$_{1-10}$—, —(CH$_2$)$_{1-10}$-Cy-(CH$_2$)$_{1-10}$—, —(CH$_2$)$_{1-10}$-Cy-(CH$_2$CH$_2$O)$_{1-10}$CH$_2$CH$_2$—, —Cy-(CH$_2$)$_{1-10}$-Cy-, —Cy-(CH$_2$)$_{1-10}$-Cy-(CH$_2$)$_{1-10}$—, —Cy-(CH$_2$)$_{1-10}$-Cy-(CH$_2$)$_{1-10}$-Cy-, or —(CH$_2$)$_{1-10}$-Cy-(CH$_2$)$_{1-10}$-Cy-(CH$_2$)$_{1-10}$—.

14. The compound of claim 1, wherein -Cy- is